United States Patent
Ji et al.

(10) Patent No.: US 12,404,285 B2
(45) Date of Patent: Sep. 2, 2025

(54) KRAS G12D PROTEOLYSIS TARGETING CHIMERAS

(71) Applicant: PAQ Therapeutics Inc., Burlington, MA (US)

(72) Inventors: Nan Ji, Arlington, MA (US); Ning Yin, Lexington, MA (US); Hui Qiu, Acton, MA (US)

(73) Assignee: PAQ Therapeutics Inc., Burlington, MA (US)

( * ) Notice: Subject to any disclaimer, the term of this patent is extended or adjusted under 35 U.S.C. 154(b) by 13 days.

(21) Appl. No.: 18/436,995

(22) Filed: Feb. 8, 2024

(65) Prior Publication Data

US 2024/0247000 A1     Jul. 25, 2024

Related U.S. Application Data

(63) Continuation of application No. PCT/US2023/066709, filed on May 5, 2023.

(60) Provisional application No. 63/489,281, filed on Mar. 9, 2023, provisional application No. 63/485,640, filed on Feb. 17, 2023, provisional application No. 63/477,001, filed on Dec. 23, 2022, provisional application No. 63/382,959, filed on Nov. 9, 2022, provisional application No. 63/364,297, filed on May 6, 2022.

(51) Int. Cl.
    *C07D 519/00*     (2006.01)
    *A61K 31/519*     (2006.01)
    *A61P 35/00*     (2006.01)

(52) U.S. Cl.
    CPC .......... *C07D 519/00* (2013.01); *A61K 31/519* (2013.01)

(58) Field of Classification Search
    CPC ...... C07D 519/00; A61K 31/519; A61P 35/00
    See application file for complete search history.

(56) References Cited

U.S. PATENT DOCUMENTS

| | | | |
|---|---|---|---|
| 10,849,982 B2 | 12/2020 | Phillips et al. | |
| 11,352,350 B2 | 6/2022 | Mainolfi et al. | |
| 2020/0140456 A1 | 5/2020 | Phillips et al. | |
| 2020/0377469 A1 | 12/2020 | Mainolfi et al. | |
| 2024/0059712 A1* | 2/2024 | Lv | C07D 519/00 |

FOREIGN PATENT DOCUMENTS

| | | |
|---|---|---|
| WO | 2021041671 A1 | 3/2021 |
| WO | 2021127278 A1 | 6/2021 |
| WO | 2021173524 A1 | 9/2021 |
| WO | 2021207172 A1 | 10/2021 |
| WO | 2021222138 A1 | 11/2021 |
| WO | 2021249519 A1 | 12/2021 |
| WO | 2022002102 A1 | 1/2022 |
| WO | 2022015375 A1 | 1/2022 |
| WO | 20220031678 A1 | 2/2022 |
| WO | 2022066646 A1 | 3/2022 |
| WO | 2022105857 A1 | 5/2022 |
| WO | 2022105859 A1 | 5/2022 |
| WO | 2022132200 A1 | 6/2022 |
| WO | 2022148421 A1 | 7/2022 |
| WO | 2022184178 A1 | 9/2022 |
| WO | 2022194066 A1 | 9/2022 |
| WO | 2022194191 A1 | 9/2022 |
| WO | 2022221739 A1 | 10/2022 |
| WO | 2022228576 A1 | 11/2022 |
| WO | 2022256459 A1 | 12/2022 |
| WO | 2022262838 A1 | 12/2022 |
| WO | 2022266015 A1 | 12/2022 |
| WO | 2022266206 A1 | 12/2022 |
| WO | 2023001141 A1 | 1/2023 |
| WO | 2023283933 A1 | 1/2023 |
| WO | 2023284537 A1 | 1/2023 |
| WO | 2023018809 A1 | 2/2023 |
| WO | 2023018810 A1 | 2/2023 |
| WO | 2023018812 A1 | 2/2023 |
| WO | 2023051586 A1 | 4/2023 |
| WO | 2023072188 A1 | 5/2023 |
| WO | 2023077441 A1 | 5/2023 |
| WO | 2023081476 A1 | 5/2023 |
| WO | 2023097227 A1 | 6/2023 |
| WO | 2023099592 A1 | 6/2023 |
| WO | 2023099620 A1 | 6/2023 |
| WO | 2023099623 A1 | 6/2023 |
| WO | 2023114733 A1 | 6/2023 |
| WO | 2023133183 A1 | 7/2023 |

(Continued)

OTHER PUBLICATIONS

Bond, M.J., et al., Target degradation of oncogenic KRASG12C by VHL-recruiting PROTACs, ACS Cent. Sci., 2020, 6, 1367-1375.
Fang, G., et al., Small-Molecule Ligands Bind to a Distinct Pocket in RAS and Inhibit SOS-Mediated Nucleotide Exchange Activity, Proc. Natl. Acad. Sci., U.S.A., 2012, 109 (14), 5299-5304.
Fell, J.B., et al., Identification of the Clinical Development Candidate MRTX849, a Covalent KRASG12C Inhibitor for the Treatment of Cancer, J. Med. Chem, 2020, 63 (13), 6679-6693.

(Continued)

*Primary Examiner* — John M Mauro
(74) *Attorney, Agent, or Firm* — McNeill PLLC

(57) ABSTRACT

Provided herein are KRAS G12D proteolysis targeting chimeras (PROTACs), compositions comprising the KRAS G12D PROTACs, and methods of making and using the KRAS G12D PROTACs, e.g., to promote degradation of KRAS G12D and/or treat KRAS G12D-associated cancers. In an embodiment, the KRAS G12D PROTAC has the following structural formula:

[KRAS G12Di]-L'-[Degron], or a pharmaceutically acceptable salt thereof, wherein values for the variables (e.g., KRAS G12Di, L', Degron) are as described herein.

30 Claims, No Drawings

(56) References Cited

FOREIGN PATENT DOCUMENTS

| WO | 2023150284 | A2 | 8/2023 | |
| WO | 2023154766 | A1 | 8/2023 | |
| WO | 2023173016 | A1 | 9/2023 | |
| WO | 2023173017 | A1 | 9/2023 | |
| WO | WO-2023193085 | A1 * | 10/2023 | ............. A61K 45/06 |
| WO | 2023215906 | A1 | 11/2023 | |
| WO | 2024054625 | A2 | 3/2024 | |
| WO | WO2024118966 | A1 | 6/2024 | |
| WO | WO2024119278 | A1 | 6/2024 | |

OTHER PUBLICATIONS

Hallin, J., et al., The KRAS(G12C) inhibitor MRTX849 provides insight toward therapeutic susceptibility of KRAS-mutant cancers in mouse models and patients, Cancer Discov. 10, 54-71.

International Search Report corresponding to International Patent Application No. PCT/US2023/066709, mailed Jul. 25, 2023, 5 pages.

Kim D., et al., "Pan-KRAS inhibitor disables oncogenic signalling and tumour growth, "Nature vol. 619, 160, Jul. 6, 2023.

Lanman, B.A., et al., Discovery of a Covalent Inhibitor of KRASG12C (AMG 510) for the Treatment of Solid Tumors, J. Med. Chem., 2020, 63 (1), 52-65.

Lu, X., et al., Small-Molecule Inhibitors Directly Targeting KRAS as Anticancer Therapeutics, J. Med. Chem., 2020, 63 (23), 14404-14424.

Mao et al. "KRAS(G12D) can be targeted by potent inhibitors via formation of salt bridge," Cell Discovery, 2022, 8.

Sun, Q., et al., Discovery of Small Molecules that Bind to K-RAS and Inhibit SOS-Mediated Activation, Angew. Chem., Int. Ed. 2012, 51 (25), 6140-6143.

Wang Xiaolun, et al: "Identification of MRTX1133, a Noncovalent, Potent, and Selective KRAS G12D Inhibitor", Journal of Medicinal Chemistry, vol. 65, No. 4, Feb. 24, 2022 (Feb. 24, 2022), pp. 3123-3133.

* cited by examiner

KRAS G12D PROTEOLYSIS TARGETING CHIMERAS

RELATED APPLICATIONS

This application is a continuation application of PCT Application No. PCT/US2023/066709, filed on May 5, 2023, which claims the benefit of U.S. Provisional Application No. 63/364,297, filed on May 6, 2022, U.S. Provisional Application No. 63/382,959, filed on Nov. 9, 2022, U.S. Provisional Application No. 63/477,001, filed on Dec. 23, 2022, U.S. Provisional Application No. 63/485,640, filed on Feb. 17, 2023, and U.S. Provisional Application No. 63/489,281, filed on Mar. 9, 2023. The entire teachings of the above applications are incorporated herein by reference.

BACKGROUND

Kirsten rat sarcoma viral oncogene homolog (KRAS) is a group of genes responsible for making K-Ras proteins, which are important for cellular growth and proliferation. Many mutations of KRAS have been implicated in many different types of carcinomas. One mutation in particular, KRAS G12D, is a common oncogenic KRAS mutation and presents a promising target for the treatment of solid tumors associated with the KRAS pathway. Much work has been done in identifying binding pockets, such as the switch II pocket, for irreversible inhibition of KRAS having the corresponding KRAS G12C mutation (M. A., Marx et. al., Identification of the Clinical Development Candidate MRTX849, a Covalent KRASG12C Inhibitor for the Treatment of Cancer. *J. Med. Chem.* 2020, 63 (13), 6679-6693; V. J., Cee et. al., Discovery of a Covalent Inhibitor of KRASG12C (AMG 510) for the Treatment of Solid Tumors. *J. Med. Chem.* 2020, 63 (1), 52-65; X. Lu et. al., Small-Molecule Inhibitors Directly Targeting KRAS as Anticancer Therapeutics. *J. Med. Chem.* 2020, 63 (23), 14404-14424). However, KRAS G12D, lacks the reactive residue adjacent to the switch II pocket that is present in KRAS G12C. While some work has been done trying to develop a new class of drug that binds a shallow pocket between switch I and switch II of KRAS G12D (G. Fang, et. al., Small-Molecule Ligands Bind to a Distinct Pocket in RAS and Inhibit SOS-Mediated Nucleotide Exchange Activity. *Proc. Natl. Acad. Sci. U.S.A.,* 2012, 109 (14), 5299-5304; S. W., Fesik, et. al., Discovery of Small Molecules that Bind to K-RAS and Inhibit SOS-Mediated Activation. *Angew. Chem., Int. Ed.* 2012, 51 (25), 6140-6143), limited cellular activity was observed. Recently, a small molecule known as MRTX1133 has been discovered that binds to the switch II pocket of KRAS G12D. MRTX1133 is a potent, selective, noncovalent inhibitor of KRAS G12D, exhibiting picomolar binding affinity, low nanomolar activity in cellular assays, and in vivo efficacy in tumor models harboring KRAS G12D mutations (M. A. Marx et. al., Identification of MRTX1133, a Noncovalent, Potent, and Selective KRASG12D Inhibitor. *J. Med. Chem.,* 2022, 65 (4), 3123-3133).

Proteolysis targeting chimeras (PROTACs) are bifunctional molecules comprising two active domains, know colloquially as "warheads," covalently attached to one another by a linking moiety (Hodges et. al, Next-Generation Drugs and Probes for Chromatin Biology: From Targeted Protein Degradation to Phase Separation. *Molecules.* 23 (8), 1958). One such PROTAC, which targets KRAS G12C, is the molecule LC-2. LC-2 is based on the KRAS G12C inhibitor MRTX849, and can rapidly degrade KRAS G12C in homozygous and heterozygous tumor cells (M. J. Bond et. al., Target degradation of oncogenic KRASG12C by VHL-recruiting PROTACs, *ACS Cent. Sci.,* 2020, 6, 1367-1375; J. Halin et. al., The KRAS(G12C) inhibitor MRTX849 provides insight toward therapeutic susceptibility of KRAS-mutant cancers in mouse models and patients. *Cancer Discov.* 10, 54-71). However, because LC-2 is a covalent inhibitor of KRAS G12C, it remains bound to its target protein, which can affect the catalytic cycle of the PROTAC molecule and thereby limit its efficacy.

Thus, there remains a need for a PROTAC that is capable of binding to KRAS G12D, preferably in a non-covalent manner, and inducing degradation of the KRAS G12D.

SUMMARY

Provided herein is a compound of structural formula A:

$$[\text{KRAS G12Di}]\text{-L'-}[\text{Degron}] \quad (A),$$

or a pharmaceutically acceptable salt thereof, wherein values for the variables (e.g., KRAS G12Di, L', Degron) are as described herein.

Also provided herein is a compound of structural formula VII:

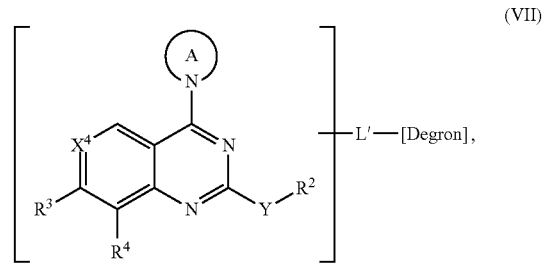

or a pharmaceutically acceptable salt thereof, wherein values for the variables (e.g., Ring A, $X^4$, Y, $R^2$, $R^3$, $R^4$, L', Degron) are as described herein.

Also provided herein is a compound of structural formula VI:

(VI)

or a pharmaceutically acceptable salt thereof, wherein values for the variables (e.g., $X^4$, Y, $R^1$, $R^2$, $R^3$, $R^4$, L', Degron) are as described herein.

Also provided herein is a compound of structural formula I:

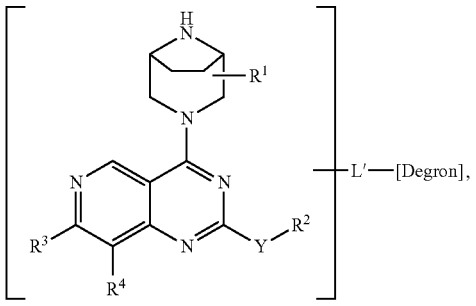

(I)

or a pharmaceutically acceptable salt thereof, wherein values for the variables (e.g., Y, $R^1$, $R^2$, $R^3$, $R^4$, L', Degron) are as described herein.

Also provided herein is a pharmaceutical composition comprising a compound of the disclosure (e.g., a compound of structural formula A and/or I and/or VI and/or VII, or a pharmaceutically acceptable salt thereof) and a pharmaceutically acceptable carrier.

Also provided herein is a pharmaceutical combination comprising a compound of the disclosure (e.g., a compound of structural formula A and/or I and/or VI and/or VII, or a pharmaceutically acceptable salt thereof) and at least one additional therapeutic agent.

Also provided herein is a method of reducing a level or activity of KRAS G12D in a cell expressing KRAS G12D, comprising contacting the cell with (e.g., an effective amount of) a compound of the disclosure (e.g., a compound of structural formula A and/or I and/or VI and/or VII, or a pharmaceutically acceptable salt thereof), e.g., in the form of a pharmaceutical composition.

Also provided herein is a method of reducing a level or activity of KRAS G12D in a subject in need thereof, comprising administering to the subject an effective amount of a compound of the disclosure (e.g., a compound of structural formula A and/or I and/or VI and/or VII, or a pharmaceutically acceptable salt thereof), e.g., in the form of a pharmaceutical composition.

Also provided herein a method for treating a KRAS G12D-associated cancer in a subject in need thereof, comprising administering to the subject a therapeutically effective amount of a compound of the disclosure (e.g., a compound of structural formula A and/or I and/or VI and/or VII, or a pharmaceutically acceptable salt thereof), e.g., in the form of a pharmaceutical composition.

Also provided herein is a compound of the disclosure (e.g., a compound of structural formula A and/or I and/or VI and/or VII, or a pharmaceutically acceptable salt thereof) or a pharmaceutical composition comprising a compound of the disclosure for a use described herein (e.g., reducing a level or activity of KRAS G12D; treating a KRAS G12D-associated cancer, e.g., in a subject). Also provided herein is a use of a compound of the disclosure (e.g., a compound of structural formula A and/or I and/or VI and/or VII, or a pharmaceutically acceptable salt thereof) for the manufacture of a medicament for a use described herein (e.g., reducing a level or activity of KRAS G12D; treating a KRAS G12D-associated cancer, e.g., in a subject).

DETAILED DESCRIPTION

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the relevant contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

When introducing elements disclosed herein, unless indicated otherwise, e.g., expressly or by context, the articles "a," "an," "the," and "said" are intended to mean that there are one or more of the elements. Further, the one or more elements may be the same or different.

"Aliphatic" refers to a saturated or unsaturated, branched- or straight-chain, hydrocarbon radical having the specified number of carbon atoms. Thus, "$(C_1-C_5)$aliphatic" refers to a radical having from 1-5 carbon atoms in a branched or linear arrangement. In some embodiments, aliphatic is $(C_1-C_{15})$aliphatic, e.g., $(C_1-C_{10})$aliphatic, $(C_1-C_6)$aliphatic, $(C_1-C_5)$aliphatic, $(C_1-C_4)$aliphatic or $(C_1-C_3)$aliphatic. In some embodiments, aliphatic is methylene or ethylene. Examples of aliphatic include alkyl, alkenyl and alkynyl. In some aspects, aliphatic is alkyl or alkynyl. In some aspects, aliphatic is alkyl or alkenyl.

"Alkenyl" refers to a branched- or straight-chain, hydrocarbon radical having the specified number of carbon atoms and at least one carbon-carbon double bond. Thus, "$(C_2-C_6)$ alkenyl" refers to a radical having from 2-6 carbon atoms and at least one carbon-carbon double bond in a branched or linear arrangement. In some embodiments, alkenyl is $(C_2-C_{15})$alkenyl, e.g., $(C_2-C_{10})$alkenyl, $(C_2-C_6)$alkenyl, $(C_2-C_5)$ alkenyl, $(C_2-C_4)$alkenyl or $(C_2-C_3)$alkenyl. Examples of alkenyl include vinyl and the like.

"Alkoxy" refers to an alkyl attached through an oxygen linking atom, wherein alkyl is as described herein. Examples of alkoxy include, but are not limited to, methoxy, ethoxy, propoxy, isopropoxy, tert-butoxy and the like.

"Alkyl" refers to a saturated, branched- or straight-chain, hydrocarbon radical having the specified number of carbon atoms. Thus, "$(C_1-C_6)$alkyl" refers to a radical having from 1-6 carbon atoms in a branched or linear arrangement. In some embodiments, alkyl is $(C_1-C_{15})$alkyl, e.g., $(C_1-C_{10})$ alkyl, $(C_1-C_6)$alkyl, $(C_1-C_5)$alkyl, $(C_1-C_4)$alkyl or $(C_1-C_3)$ alkyl. Examples of alkyl include methyl, ethyl, propyl (e.g., n-propyl, isopropyl), butyl (e.g., n-butyl, isobutyl, sec-butyl, t-butyl), pentyl (e.g., n-pentyl, isopentyl, neopentyl, 2-methylpentyl), hexyl (e.g., n-hexyl), and the like.

"Alkylene" refers to a divalent alkyl radical, wherein alkyl is as described herein. Examples of alkylene include methylene, ethylene, propylene, and the like.

"Alkynyl" refers to a branched- or straight-chain, hydrocarbon radical having the specified number of carbon atoms and at least one carbon-carbon triple bond. Thus, "($C_2$-$C_6$) alkynyl" refers to a radical having from 2-6 carbon atoms and at least one carbon-carbon triple bond in a branched or linear arrangement. In some embodiments, alkynyl is ($C_2$-$C_{15}$)alkynyl, e.g., ($C_2$-$C_{10}$)alkynyl, ($C_2$-$C_6$)alkynyl, ($C_2$-$C_5$) alkynyl, ($C_2$-$C_4$)alkynyl or ($C_2$-$C_3$)alkynyl. Examples of alkynyl include propargyl and the like.

"Aryl" refers to a monocyclic or polycyclic (e.g., bicyclic, tricyclic), aromatic, hydrocarbon ring radical having the specified number of ring atoms. Thus, "($C_6$-$C_{14}$)aryl" means an aromatic ring radical having from 6-14 ring atoms. In some embodiments, aryl is ($C_6$-$C_{14}$)aryl, e.g., ($C_6$-$C_{12}$)aryl, ($C_6$-$C_{10}$)aryl or ($C_6$)aryl. Examples of aryl include phenyl, naphthyl, anthracenyl and fluorenyl. In some embodiments, aryl is phenyl. "Aryl" includes bicyclic and tricyclic ring systems consisting of an aromatic ring fused to one or two non-aromatic rings or one non-aromatic ring system consisting of two non-aromatic rings. When the aromatic ring is fused to one non-aromatic ring system, the non-aromatic rings in the ring system may be fused or spirocyclic to one another.

"Arylalkyl" refers to an alkyl wherein one hydrogen of the alkyl is replaced with aryl, and alkyl and aryl are as described herein. Examples of arylalkyl include benzyl, phenethyl and napthylmethyl.

"Cyano" refers to —C≡N.

"Cyanoalkyl" refers to an alkyl wherein one hydrogen of the alkyl is replaced with cyano, and alkyl and cyano are as described herein. Examples of cyanoalkyl include cyanomethyl, cyanoethyl, cyanopropyl, and the like.

"Cycloalkyl" refers to a saturated or partially unsaturated, monocyclic or polycyclic (e.g., bicyclic, tricyclic), hydrocarbon ring radical having the specified number of ring atoms. Thus, "($C_3$-$C_6$)cycloalkyl" refers to a ring radical having from 3-6 ring atoms. A cycloalkyl can be monocyclic, fused bicyclic, bridged bicyclic or polycyclic, but is typically monocyclic. In some embodiments, cycloalkyl is ($C_3$-$C_{12}$)cycloalkyl, e.g., ($C_3$-$C_8$)cycloalkyl or ($C_3$-$C_6$)cycloalkyl. In some embodiments, cycloalkyl is saturated. Examples of cycloalkyl include cyclopropyl, cyclobutyl, cyclopentyl, cyclopentenyl, cyclohexyl, cyclohexenyl, cycloheptyl, cyclooctyl, bicyclo[1.1.1]pentanyl and the like.

The suffix "ene" or "enyl" is used herein to indicate that the group being modified with the suffix has two or more points of attachment (i.e., divalent, trivalent, or polyvalent) within the compound being described. For example, divalent alkyl groups are alkylene groups, divalent heteroalkyl groups are heteroalkylene, divalent aryl groups are arylene groups, divalent heteroaryl groups are heteroarylene groups, and so forth. Substituted groups having a single point of attachment to the compound being described are not referred to using the "ene" designation. Thus, e.g., a trifluoromethyl substituent is not referred to herein as trifluoromethylene.

"Halogen" and "halo" are used interchangeably herein and each refers to fluorine, chlorine, bromine, or iodine. In some embodiments, halogen is fluoro, chloro or bromo. In some embodiments, halogen is fluoro or chloro. In some embodiments, halogen is fluoro.

"Haloalkyl" refers to an alkyl wherein at least one hydrogen of the alkyl is replaced with a halo, and alkyl and halo are as described herein. Haloalkyl includes mono, poly, and perhaloalkyl groups, wherein each halogen is independently selected. In some embodiments, haloalkyl is perhaloalkyl (e.g., perfluoroalkyl). Haloalkyl includes, but is not limited to, fluoromethyl, difluoromethyl, trifluoromethyl, trifluoromethylethyl, pentafluoroethyl and the like.

"Hetero" refers to an atom that is not carbon or hydrogen. Examples of heteroatoms include, but are not limited to, nitrogen, oxygen, sulfur and the like. In some embodiments, hetero is independently selected from nitrogen, oxygen or sulfur. In some embodiments, hetero is independently selected from nitrogen or oxygen.

"Heteroaryl" refers to a monocyclic or polycyclic (e.g., bicyclic, tricyclic), aromatic, hydrocarbon ring radical having the specified number of ring atoms, wherein at least one carbon atom in the ring has been replaced with a heteroatom (e.g., a heteroatom independently selected from N, O or S). Thus, "($C_5$-$C_6$)heteroaryl" refers to an aromatic ring radical having 5 or 6 ring atoms consisting of carbon and one or more independently selected heteroatoms (e.g., selected from N, O or S). In some embodiments, heteroaryl contains 1, 2, 3 or 4 (e.g., 1, 2 or 3; 1 or 2) heteroatoms independently selected from N, S and O. In some embodiments, heteroaryl contains 1, 2, 3 or 4 (e.g., 1, 2 or 3; 1 or 2) independently selected heteroatoms, e.g., independently selected from N and O. In some embodiments, heteroaryl is ($C_5$-$C_{14}$)heteroaryl, e.g., ($C_5$-$C_{10}$)heteroaryl, ($C_5$-$C_6$)heteroaryl, ($C_6$) heteroaryl, ($C_5$)heteroaryl, ($C_9$-$C_{10}$)heteroaryl, ($C_9$)heteroaryl, ($C_{10}$)heteroaryl or ($C_{14}$)heteroaryl. Examples of heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a] imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl (e.g., 1,2,3-oxadiazolyl, 1,2,4-oxadiazolyl, 1,2,5-oxadiazolyl, 1,3,4-oxadiazolyl), oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl) and xanthenyl. "Heteroaryl" includes bicyclic ring systems consisting of a heteroaromatic ring fused to a non-aromatic ring.

"Heterocyclyl" or "heterocycloalkyl" refers to a saturated, monocyclic or polycyclic (e.g., bicyclic, tricyclic), hydrocarbon ring radical having the specified number of ring atoms, wherein at least one carbon atom in the ring has been replaced with a heteroatom. Thus, "($C_3$-$C_6$)heterocyclyl" means a heterocyclic ring system having from 3-6 ring atoms consisting of carbon and one or more independently selected heteroatoms. A heterocyclyl can be monocyclic, fused bicyclic, bridged bicyclic or polycyclic, but is typically monocyclic. In some embodiments, heterocyclyl contains 1, 2, 3 or 4 (e.g., 1, 2 or 3; 1 or 2) heteroatoms independently selected from N, S and O. In some embodiments, heterocyclyl contains 1, 2, 3 or 4 (e.g., 1, 2 or 3; 1 or 2) heteroatoms independently selected from N and O. When one heteroatom is S, it can be optionally mono- or di-oxygenated (i.e., —S(O)— or —S(O)$_2$). In some embodiments, heterocyclyl is $(C_3$-$C_{15})$heterocyclyl, e.g., $(C_3$-$C_{12})$heterocyclyl, $(C_4$-$C_8)$heterocyclyl, $(C_3$-$C_7)$heterocyclyl or $(C_3$-$C_6)$heterocyclyl. Examples of monocyclic heterocyclyls include, but are not limited to, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1-dioxide, morpholinyl, azepanyl, oxazepanyl, azabicyclohexanyl, azabicycloheptanyl, azabicyclooctanyl, azabicyclononanyl (e.g., octahydroindolizinyl), azaspiroheptanyl, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyl, oxaazaspirooctanyl, diazaspirononanyl, oxaazabiocycloheptanyl, hexahydropyrrolizinyl 4(1H)-oxide, tetrahydro-2H-thiopyranyl 1-oxide and tetrahydro-2H-thiopyranyl 1,1-dioxide.

"Hydroxy" refers to —OH.

"Hydroxyalkyl" refers to an alkyl wherein one hydrogen of the alkyl is replaced with hydroxy, and alkyl and hydroxy are as described herein. Examples of hydroxyalkyl include hydroxymethyl, hydroxyethyl, hydroxypropyl, and the like.

"Hydroxyalkynyl" refers to an alkynyl wherein one hydrogen of the alkynyl is replaced with hydroxy, and alkynyl and hydroxy are as described herein.

"Oxo" refers to =O.

The term "substituted" refers to replacement of a hydrogen atom with a suitable substituent. Typically, the suitable substituent replaces a hydrogen atom bound to a carbon atom, but a substituent may also replace a hydrogen bound to a heteroatom, such as a nitrogen atom. When two or more hydrogen atoms are each replaced with an independently selected substituent, the substituents can be the same or different. It will be understood that "substitution" or "substituted with" includes the implicit proviso that such substitution is in accordance with permitted valence of the substituted atom. It is also preferred that the substituent, and the substitution, result in a stable compound, e.g., which does not spontaneously undergo transformation such as by rearrangement, cyclization, elimination, etc.

The term "optionally substituted", as used herein, means that substitution is optional and, therefore, it is possible for the atom or moiety designated as "optionally substituted" to be unsubstituted or substituted. In some embodiments, an optionally substituted group is unsubstituted. In some embodiments, an optionally substituted group is substituted. An "optionally substituted" group is, in some embodiments, substituted with 0-5 (e.g., 1-5, 0-3, 1-3, 0, 1, 2, 3, 4, 5) substituents. Unless otherwise indicated, e.g., as with the terms "substituted" or "optionally substituted," a group designated herein is unsubstituted.

When a bond to a substituent is shown to cross a bond connecting two atoms in a ring (as, for example, the bonds to R$^1$, R$^6$ and R$^8$ in the structural formulas depicted herein) or to cross a circle denoting a ring, then such substituent may be bonded to any substitutable atom in the ring. Further, when the ring the bond to the substituent is shown to cross into is polycyclic (e.g., bicyclic, as, for example, the hexa-hydropyrrolizinyl ring system in structural formula II), the substituent may be bonded to any substitutable atom of the ring or ring system the bond to the substituent is shown to cross into.

When a substituent is listed or depicted without indicating the atom to which such substituent is bonded to the rest of the compound of a given formula, then such substituent may be bonded via any atom in such substituent, so long as the substitution results in a stable compound. Square brackets are used herein to depict a substituent without indicating the atom to which such substituent is bonded to the rest of the compound of a given formula. Thus, for example, in a compound of the following structural formula:


the portion of the compound in square brackets bonded to -L'-[Degron] can be bonded via the nitrogen atom of the secondary amine of the diazabicyclooctanyl moiety, so as to result in a compound of the following structural formula:

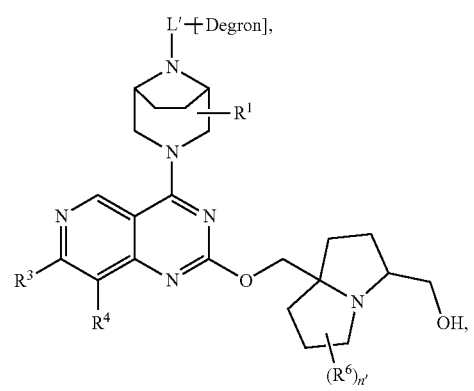

or via the oxygen atom of the hydroxyl, so as to result in a compound of the following structural formula:

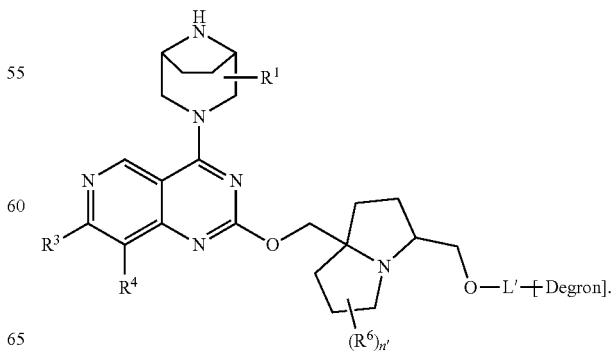

Similarly, in a compound of the following structural formula: [KRAS G12Di]-L'-[Degron], wherein Degron is

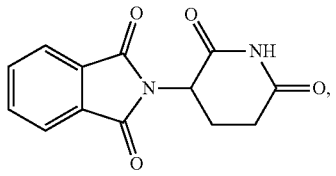 [SMILES: O=C1CCC(N2C(=O)c3ccccc3C2=O)C(=O)N1]

the Degron can be bonded to [KRAS G12Di]-L'- via the ortho carbon atom of the phthalimide, as in

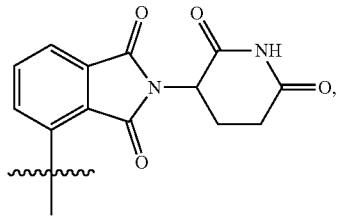 [SMILES: *c1cccc2c1C(=O)N(C1CCC(=O)NC1=O)C2=O]

or via the meta carbon atom of phthalimide, as in

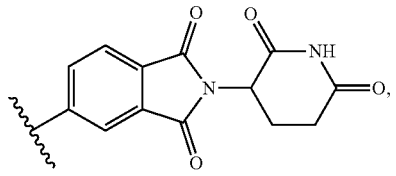 [SMILES: *c1ccc2c(c1)C(=O)N(C1CCC(=O)NC1=O)C2=O]

for examples. These examples are for illustration only, and are given without limitation to other binding sites in the portion of the compound in square brackets bonded to -L'-[Degron] and/or in Degron, all of which are contemplated by this disclosure.

Suitable substituents for use herein include halogen, hydroxyl, carbonyl (such as carboxyl, alkoxycarbonyl, formyl, or acyl), thiocarbonyl (such as thioester, thioacetate, or thioformate), alkyl, alkoxy, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, cycloalkyl, heterocyclyl, aralkyl, aryl or heteroaryl. It will be understood by those skilled in the art that substituents can themselves be substituted, if appropriate. Accordingly, substituents can further include an acetamide, for example.

When a bivalent substituent is listed without indicating directionality of such substituent (as, for example, variables L' and/or X), the bivalent substituent can be bonded in either direction. Thus, for example, a compound of structural formula (I):


wherein L' is —X—$(CH_2)_q$— includes compounds of both the following structural formula:

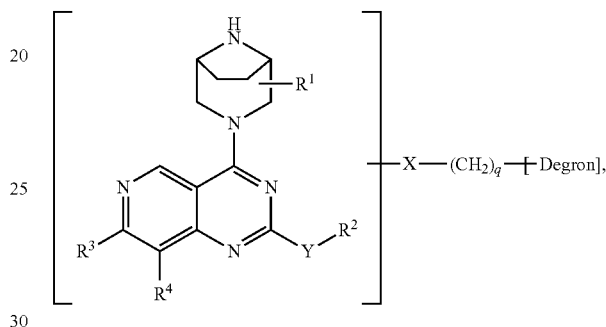

and the following structural formula:

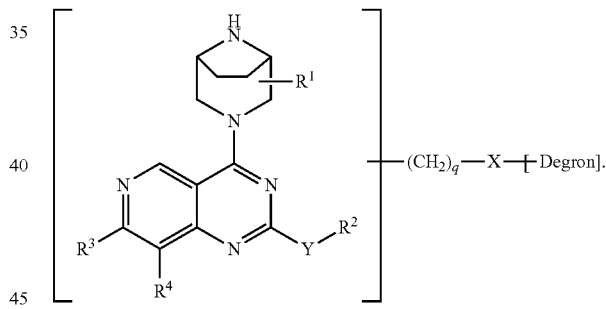

As used herein, the term "compound of the disclosure" refers to a compound of any structural formulas depicted herein (e.g., a compound of Structural Formula I or a subformula thereof, such as a compound of Structural Formula Ia, Ib, II, IIa, IIb, III, IIIa, IIIb, IV, IVa, IVb, V, Va, Vb, Table 1)), as well as isomers, such as stereoisomers (including diastereoisomers, enantiomers and racemates) and tautomers thereof, isotopologues thereof, and inherently formed moieties (e.g., polymorphs and/or solvates, such as hydrates) thereof. When a moiety is present that is capable of forming a salt, then salts are included as well, in particular, pharmaceutically acceptable salts.

Compounds of the disclosure may have asymmetric centers, chiral axes, and chiral planes (e.g., as described in: E. L. Eliel and S. H. Wiley, Stereo-chemistry of Carbon Compounds, John Wiley & Sons, New York, 1994, pages 1119-1190), and occur as racemic mixtures, individual isomers (e.g., diastereomers, enantiomers, geometrical isomers (including cis and trans double bond isomers), conformational isomers (including rotamers and atropisomers), tautomers and intermediate mixtures, with all possible isomers and mixtures thereof being included, unless otherwise indicated.

Unless indicated otherwise at the point of use herein, when a disclosed compound or moiety is depicted by structure without indicating the stereochemistry, and the compound or moiety has one or more chiral centers, it is to be understood that the structure encompasses one enantiomer or diastereomer of the compound or moiety separated or substantially separated from the corresponding optical isomer(s), a racemic mixture, and mixtures enriched in one enantiomer or diastereomer relative to its corresponding optical isomer(s). Unless indicated otherwise at the point of use herein, when a disclosed compound or moiety is depicted by a structure indicating stereochemistry using solid and/or broken wedges, and the compound or moiety has one or more chiral centers, the stereochemistry indicates absolute configuration of the substituents around the one or more chiral centers. Unless indicated otherwise as the point of use herein, when a disclosed compound or moiety is depicted by a structure indicating stereochemistry using solid and/or broken bolded lines, and the compound or moiety has one or more chiral centers, the stereochemistry indicates relative stereochemistry of unspecified absolute configuration of the substituents around the one or more chiral centers. "R" and "S" can also or alternatively be used to indicate the absolute configuration of substituents around one or more chiral centers (e.g., carbon atoms). D- and L- can also or alternatively be used to designate stereochemistry. Thus, for example, a single stereoisomer with known relative and absolute configuration of two chiral centers can be designated using the conventional RS system (e.g., (1S, 2S)); diastereomers in a racemic mixture can be designated using the RS system with two letters (e.g., (1RS,2RS) as a racemic mixture of (1R,2R) and (1S,2S); (1RS,2SR) as a racemic mixture of (1R,2S) and (1S,2R)).

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms.

"Racemate" or "racemic mixture," as used herein, refer to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left|\frac{R-S}{R+S}\right| \times 100\%,$$

where R and S represent the respective fractions of each enantiomer in a mixture, such that R+S=1. In some embodiments, an enantiomer is present in an ee of at least or about 50%, e.g., at least or about: 60%, 70%, 80%, 90%, 95%, 98%, 99% or 99.9%.

Percent diastereomeric excess (de) is defined as the absolute difference between the mole fraction of each diastereomer multiplied by 100% and can be represented by the following equation:

$$de = \left|\frac{D1-(D2+D3+D4\ldots)}{D1+(D2+D3+D4\ldots)}\right| \times 100\%,$$

where D1 and (D2+D3+D4 . . . ) represent the respective fractions of each diastereomer in a mixture, such that D1+(D2+D3+D4 . . . )=1. In some embodiments, a diastereomer is present in a de of at least or about 50%, e.g., at least or about: 60%, 70%, 80%, 90%, 95%, 98%, 99% or 99.9%.

Tautomers are isomers of a compound that differ in the position of one or more hydrogen atoms.

Unless otherwise indicated, all possible isomers and mixtures thereof, including optical isomers, rotamers, tautomers and cis- and trans-isomers, are included in the present invention.

The term "isotopologue" refers to a molecule that differs from a reference molecule only in its isotopic composition.

Certain atoms naturally occur in various isotopic forms. Natural isotopic abundance describes the relative abundance of the various naturally-occurring isotopes of a given atom. Thus, it will be understood that a population of molecules represented by a particular chemical structure will typically contain isotopologues of the particular chemical structure. The relative amount of such isotopologues will depend upon a number of factors, such as relative natural isotopic abundance, the isotopic purity of reagents used to make the compound and the efficiency of incorporation of isotopic atoms in the various synthetic steps used to prepare the compound. In certain embodiments, the amount of such isotopologues in toto will be less than 49.9%, for example, less than 47.5%, less than 40%, less than 32.5%, less than 25%, less than 17.5%, less than 10%, less than 5%, less than 3%, less than 1%, or less than 0.5%.

Structures depicted herein are meant to allow for such natural isotopic abundance, as well as replacement of one or more atoms in a structure with an isotope thereof or an isotopically enriched counterpart, e.g., at a non-natural isotopic abundance. For example, compounds produced by the replacement of a hydrogen with deuterium or tritium, or of a carbon with a $^{13}$C or $^{14}$C are within the scope of this disclosure. In some embodiments, a hydrogen atom in a compound of the disclosure is replaced or enriched with D. In some embodiments, a methyl group in a compound of the disclosure is replaced or enriched with —CD$_3$. Isotopologues can be useful, for example, as analytical tools, as probes in biological assays, or as therapeutic agents in accordance with the present disclosure.

The phrase "pharmaceutically acceptable" means that the substance or composition the phrase modifies is, within the scope of sound medical judgment, suitable for use in contact with the tissues of humans and lower animals without undue toxicity, irritation, allergic response and the like, and are commensurate with a reasonable benefit/risk ratio.

As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include pharmaceutically acceptable acid addition salts and pharmaceutically acceptable base addition salts.

Examples of pharmaceutically acceptable acid addition salts are salts of an amino group formed with inorganic acids such as hydrochloric acid, hydrobromic acid, phosphoric acid, sulfuric acid and perchloric acid, or with organic acids, such as acetic acid, oxalic acid, maleic acid, tartaric acid, citric acid, succinic acid or malonic acid or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Pharmaceutically acceptable base addition salts include salts formed with inorganic bases, such as alkali metal, alkaline earth metal, and ammonium bases, and salts formed with aliphatic, alicyclic or aromatic organic amines, such as methylamine, trimethylamine and picoline, or $N^+((C_1\text{-}C_4)\text{alkyl})_4$ salts. Representative alkali or alkaline earth metal salts include sodium, lithium, potassium, calcium, magnesium, barium and the like. Further pharmaceutically acceptable base addition salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Compounds described herein can also exist as "solvates" or "hydrates." A "hydrate" is a compound that exists in a composition with one or more water molecules. A hydrate can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared. The source of such solvate or hydrate can be from the solvent of crystallization, inherent in the solvent of preparation or crystallization, or adventitious to such solvent.

"Pharmaceutically acceptable carrier" refers to a nontoxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Treating," as used herein, refers to taking steps to deliver a therapy to a subject, such as a mammal, in need thereof (e.g., as by administering to a subject one or more therapeutic agents). "Treating" includes inhibiting a disease or condition (e.g., as by slowing or stopping its progression or causing regression of the disease or condition), and relieving the symptoms resulting from a disease or condition.

"KRAS G12D" refers to mammalian KRAS protein containing an aspartic acid substitution for glycine at amino acid position 12. The assignment of amino acid codon and residue positions for human KRAS is based on the amino acid sequence identified by UniProtKB/Swiss-Prot P01116: Variantp.Gly12Asp.

A "KRAS G12D-associated cancer" refers to a cancer associated with (e.g., mediated by) or having a KRAS G12D mutation. A person skilled in the art will know how to determine whether (e.g., diagnose) a cancer or subject has a KRAS G12D mutation, for example, using a kit or assay approved by a regulatory agency, such as U.S. Food and Drug Administration (FDA). Techniques that can be used to determine whether a cancer or subject has a KRAS G12D mutation include next generation sequencing, immunohistochemistry, fluorescence microscopy, break apart FISH analysis, Southern blotting, Western blotting, FACS analysis, Northern blotting and PCR-based amplification (e.g., RT-PCR).

A "binding moiety" is a portion of a compound that binds to an indicated target with measurable affinity. In the context of the instant disclosure, the target is typically a protein as, for example, KRAS G12D in a KRAS G12D binding moiety; ubiquitin E3 ligase in a ubiquitin E3 ligase binding moiety. In the compounds of the disclosure, binding of the compound of the disclosure to an indicated target is typically mediated by a binding moiety for that target. For example, binding to KRAS G12D in the compounds of the disclosure is typically mediated by a KRAS G12D binding moiety. For example, binding to a ubiquitin E3 ligase is typically mediated by a ubiquitin E3 ligase binding moiety.

Binding (of a binding moiety and/or a compound of the disclosure) to a target may result, for example, in inhibition and/or agonism (full or partial) of the target, such as a target protein. Thus, in some embodiments, a binding moiety and/or compound of the disclosure is an inhibitor. In certain embodiments, a binding moiety and/or compound of the disclosure has an $IC_{50}$ against its indicated target and/or binding constant with its indicated target of less than about 50 μM, e.g., less than about 10 μM, less than about 5 μM, less than about 1 μM, less than about 500 nM, less than about 100 nM, less than about 10 nM, or less than about 1 nM. Methods of measuring $IC_{50}$ and binding constants are described herein and/or within the abilities of a person skilled in the art.

An "effective amount" is an amount effective, at dosages and for periods of time necessary, to achieve a desired result (e.g., a desired therapeutic result, a desired in vitro result).

"A therapeutically effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual. A therapeutically effective amount of an agent to be administered can be determined by a clinician of ordinary skill using the guidance provided herein and other methods known in the art.

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some embodiments, a subject is a human.

Compounds

Provided herein in an embodiment is a KRAS G12D PROTAC of structural formula (A):

[KRAS G12Di]-L'-[Degron]    (A), or a pharmaceutically acceptable salt thereof, wherein:

KRAS G12Di is a KRAS G12D binding moiety, preferably, a KRAS G12D inhibitor;

L' is a bivalent linker connecting KRAS G12Di to Degron; and

Degron is a degron, preferably, a ubiquitin E3 ligase binding moiety. Alternative values for each of the variables in structural formula A are described in the following sections and throughout this disclosure. This disclosure contemplates all combinations of the values and alternative values for the variables set forth herein.

KRAS G12D Binding Moieties

KRAS G12D binding moieties and methods of making the same are disclosed in International Publication Nos. WO 2021/041671; WO 2022/031678; WO 2022/066646; and WO 2022/015375, the entire contents of which are incorporated herein by reference. In some aspects, a KRAS G12D binding moiety is a KRAS G12D inhibitor, e.g., a KRAS G12D inhibitor disclosed in WO 2021/041671; WO 2022/031678; WO 2022/066646; or WO 2022/015375. In some aspects, a KRAS G12D binding moiety is a KRAS G12D inhibitor disclosed in WO 2021/041671 or WO 2022/015375.

KRAS G12D binding moieties and methods of making the same are also disclosed in Mao et al. "KRAS(G12D) can be targeted by potent inhibitors via formation of salt bridge," Cell Discovery, 2022, 8, the entire content of which is incorporated herein by reference. See, in particular, FIGS. 1 and 2 therein. In some aspects, a KRAS G12D binding moiety is a KRAS G12D inhibitor disclosed in Mao et al.

KRAS G12D binding moieties and methods of making the same are disclosed in International Publication No. WO 2022/105857, the entire content of which is incorporated herein by reference. In some aspects, a KRAS G12D binding moiety is a KRAS G12D inhibitor disclosed in WO 2022/105857. KRAS G12D binding moieties and methods of making the same are also disclosed in International Publication No. WO 2022/105859, the entire content of which is incorporated herein by reference. In some aspects, a KRAS G12D binding moiety is a KRAS G12D inhibitor disclosed in WO 2022/105859.

In a first embodiment, provided is a compound of the following structural formula:

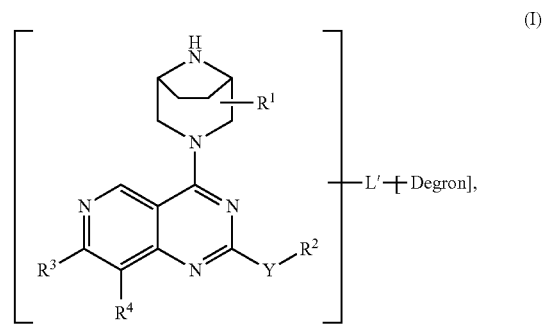

or a pharmaceutically acceptable salt thereof, wherein:

Y is a bond, O or $NR^5$;

$R^1$ is hydrogen, hydroxy, halogen, $(C_1-C_3)$alkyl, $(C_1-C_3)$cyanoalkyl, $(C_1-C_3)$hydroxyalkyl, —C(O)H, —$CO_2R^5$, —$CO_2N(R^5)_2$ or $(C_5-C_6)$heteroaryl;

$R^2$ is hydrogen, —$N(R)_2$, $(C_3-C_{12})$heterocyclyl, $(C_1-C_6)$alkyl, -L-$(C_3-C_{12})$heterocyclyl, -L-$(C_6-C_{14})$aryl, -L-$(C_5-C_{14})$heteroaryl, -L-$(C_3-C_{12})$cycloalkyl, -L-$N(R^5)_2$, -L-N(H)C(NH)$NH_2$, -L-C(O)N$(R^5)_2$, -L-$(C_1-C_6)$haloalkyl, -L-$OR^5$, -L-$NR^5$C(O)—$(C_6-C_{14})$aryl, -L-COOH or -L-C(O)O$(C_1-C_6)$alkyl, wherein the $(C_3-C_{12})$heterocyclyl, the $(C_6-C_{14})$aryl of -L-$NR^5$C(O)—$(C_6-C_{14})$aryl, the $(C_3-C_{12})$heterocyclyl of -L-$(C_3-C_{12})$heterocyclyl and the $(C_3-C_{12})$cycloalkyl of -L-$(C_3-C_{12})$cycloalkyl are optionally substituted with one or more $R^6$, and the aryl of -L-$(C_6-C_{14})$aryl and $(C_5-C_{14})$heteroaryl of -L-$(C_5-C_{14})$heteroaryl are optionally substituted with one or more $R^7$;

L is $(C_1-C_4)$alkylene optionally substituted with hydroxy, $(C_1-C_4)$hydroxyalkyl or $(C_5-C_{14})$heteroaryl;

$R^3$ is $(C_6-C_{14})$aryl or $(C_5-C_{14})$heteroaryl, wherein the $(C_6-C_{14})$aryl or $(C_5-C_{14})$heteroaryl is optionally substituted with one or more $R^8$;

$R^4$ is hydrogen, halogen or $(C_1-C_3)$alkyl;

each $R^5$ is independently hydrogen or $(C_1-C_3)$alkyl;

each $R^6$ is independently deutero, halogen, hydroxy, $(C_1-C_3)$hydroxyalkyl, $(C_1-C_3)$alkyl, $(C_1-C_3)$haloalkyl, $(C_1-C_3)$alkoxy, cyano, -Q-phenyl, -Q-phenyl-$SO_2F$, —N(H)C(O)-phenyl, —N(H)C(O)-phenyl-$SO_2F$, $(C_1-C_3)$alkyl-substituted pyrazole, $(C_6-C_{14})$aryl$(C_1-C_3)$alkyl, tert-butyldimethylsilyloxy-$CH_2$—, —$N(R^5)_2$, $(C_1-C_3)$alkoxy$(C_1-C_3)$alkyl, $(C_1-C_3)$alkyl-C(O)—, oxo, $(C_1-C_3)$haloalkyl-C(O)—, —$SO_2F$, $(C_1-C_3)$alkoxy$(C_1-C_3)$alkoxy, —$CH_2OC(O)N(R^5)_2$, —$CH_2N(H)C(O)O$—$(C_1-C_6)$alkyl, —$CH_2N(H)C(O)N(R^5)_2$, —$CH_2N(H)C(O)(C_1-C_6)$alkyl, —$CH_2$(pyrazolyl), —$CH_2N(H)S(O)_2(C_1-C_6)$alkyl, —$CH_2OC(O)(C_3-C_{12})$heterocyclyl, —$OC(O)N(R^5)_2$, —$OC(O)N(H)(C_1-C_3)$alkyl-O—$(C_1-C_3)$alkyl, —$OC(O)N(H)(C_1-C_3)$alkyl-O—$(C_1-C_3)$alkyl-phenyl-$(C_1-C_3)$alkyl-N$(CH_3)_2$, —$OC(O)N(H)(C_1-C_3)$alkyl-O—$(C_1-C_3)$alkyl-phenyl, —$OC(O)(C_3-C_{12})$heterocyclyl or —$CH_2$—$(C_3-C_{12})$heterocyclyl, wherein the phenyl of —N(H)C(O)phenyl and —OC(O)N(H)$(C_1-C_3)$alkyl-O—$(C_1-C_3)$alkyl-phenyl is optionally substituted with —C(O)H or —OH, and the $(C_3-C_{12})$heterocyclyl of —$CH_2$—$(C_3-C_{12})$heterocyclyl is optionally substituted with oxo;

Q is a bond or O;

each $R^7$ is independently halogen, hydroxy, —C(O)H, $(C_1-C_4)$alkyl, $(C_1-C_4)$alkoxy, $(C_1-C_4)$haloalkyl, $(C_1-C_4)$hydroxyalkyl or —$N(R^5)_2$;

each R⁸ is independently halogen, cyano, hydroxy, ($C_1$-$C_4$)alkyl, —S—($C_1$-$C_3$)alkyl, ($C_2$-$C_4$)alkenyl, ($C_2$-$C_4$)alkynyl, ($C_2$-$C_4$)hydroxyalkynyl, ($C_1$-$C_3$)cyanoalkyl, triazolyl, ($C_1$-$C_3$)haloalkyl, —O—($C_1$-$C_3$)haloalkyl, —S—($C_1$-$C_3$)haloalkyl, ($C_1$-$C_3$)alkoxy, ($C_1$-$C_3$)hydroxyalkyl, —CH₂C(O)N(R⁵)₂, ($C_3$-$C_4$)alkynyl-N(R⁵)₂, N(R⁵)₂, deutero($C_2$-$C_4$)alkynyl, ($C_1$-$C_3$)alkoxy($C_1$-$C_3$)haloalkyl or ($C_3$-$C_6$)cycloalkyl, wherein the ($C_3$-$C_6$)cycloalkyl is optionally substituted with halogen or ($C_1$-$C_3$)alkyl;

L' is a bivalent linker connecting

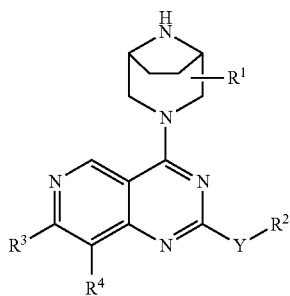

to Degron; and

Degron is a degron.

In a first aspect of the first embodiment, Y is O. Values for the remaining variables are as described in the first embodiment.

In a second aspect of the first embodiment, R¹ is hydrogen. Values for the remaining variables are as described in the first embodiment, or first aspect thereof.

In a third aspect of the first embodiment, R² is -L-($C_3$-$C_{12}$)heterocyclyl, wherein the ($C_3$-$C_{12}$)heterocyclyl of -L-($C_3$-$C_{12}$)heterocyclyl is optionally substituted with one or more R⁶. Values for the remaining variables are as described in the first embodiment, or first or second aspect thereof.

In a fourth aspect of the first embodiment, L is methylene. Values for the remaining variables are as described in the first embodiment, or first through third aspects thereof.

In a fifth aspect of the first embodiment, R³ is ($C_6$-$C_{14}$)aryl optionally substituted with one or more R⁸. Values for the remaining variables are as described in the first embodiment, or first through fourth aspects thereof.

In a sixth aspect of the first embodiment, R⁴ is halogen. Values for the remaining variables are as described in the first embodiment, or first through fifth aspects thereof.

In a seventh aspect of the first embodiment, R⁴ is fluoro. Values for the remaining variables are as described in the first embodiment, or first through sixth aspects thereof.

In an eighth aspect of the first embodiment, each R⁶ is independently halogen, hydroxy, ($C_1$-$C_3$)hydroxyalkyl, ($C_1$-$C_3$)alkyl, ($C_1$-$C_3$)haloalkyl, ($C_1$-$C_3$)alkoxy or cyano. Values for the remaining variables are as described in the first embodiment, or first through seventh aspects thereof.

In a ninth aspect of the first embodiment, each R⁸ is independently halogen, hydroxy, ($C_1$-$C_4$)alkyl, —S—($C_1$-$C_3$)alkyl, ($C_2$-$C_4$)alkenyl, ($C_2$-$C_4$)alkynyl, ($C_1$-$C_3$)alkoxy, ($C_1$-$C_3$)hydroxyalkyl or deutero($C_2$-$C_4$)alkynyl. Values for the remaining variables are as described in the first embodiment, or first through eighth aspects thereof.

In a tenth aspect of the first embodiment, each R⁸ is independently halogen, hydroxy, or ($C_2$-$C_4$)alkynyl. Values for the remaining variables are as described in the first embodiment, or first through ninth aspects thereof.

In an eleventh aspect of the first embodiment, R³ is

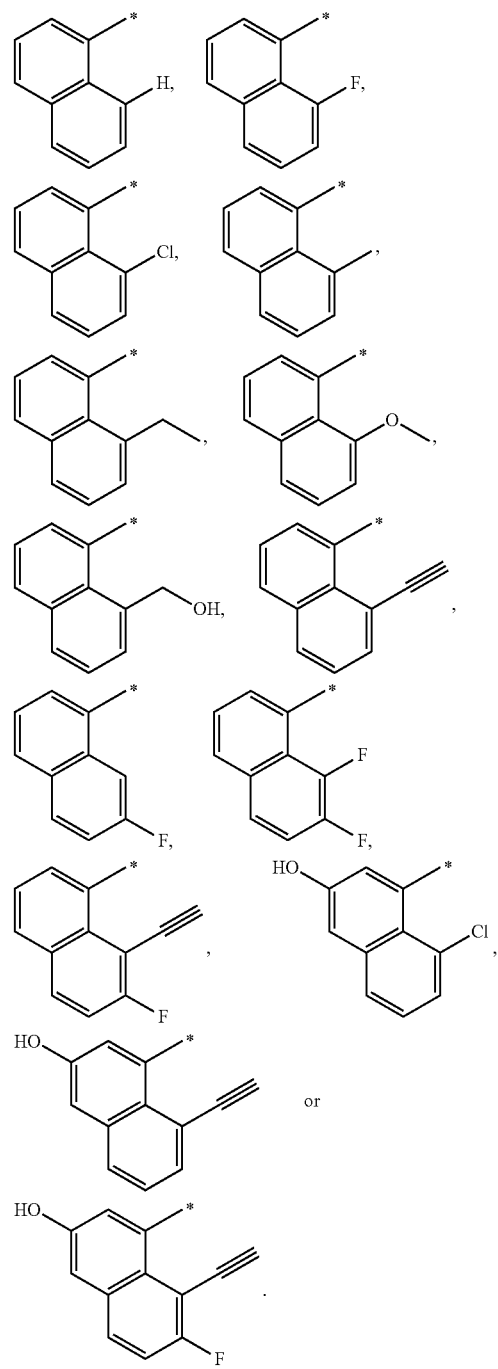

Values for the remaining variables are as described in the first embodiment, or first through tenth aspects thereof.

In a twelfth aspect of the first embodiment, Y—R² is

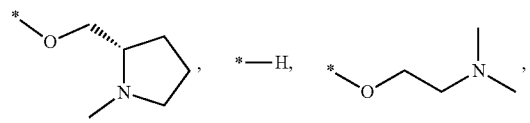

-continued

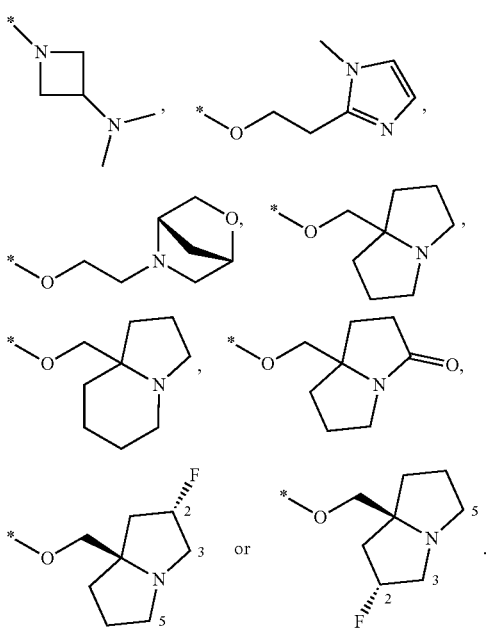

Values for the remaining variables are as described in the first embodiment, or first through eleventh aspects thereof.

In a thirteenth aspect of the first embodiment, $R^3$ is

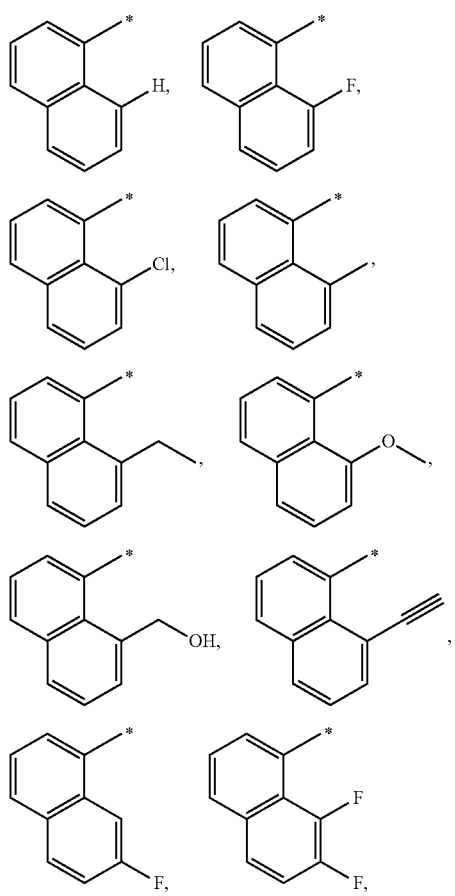

-continued

Values for the remaining variables are as described in the first embodiment, or first through twelfth aspects thereof.

In a fourteenth aspect of the first embodiment, each $R^6$ is independently deutero, halogen, hydroxy, $(C_1-C_3)$hydroxyalkyl, $(C_1-C_3)$alkyl, $(C_1-C_3)$haloalkyl, $(C_1-C_3)$alkoxy or cyano. Values for the remaining variables are as described in the first embodiment, or first through thirteenth aspects thereof.

In a fifteenth aspect of the first embodiment, each $R^6$ is independently halogen, hydroxy, $(C_1-C_3)$hydroxyalkyl, $(C_1-C_3)$alkyl, $(C_1-C_3)$haloalkyl, $(C_1-C_3)$alkoxy, cyano, -Q-phenyl, -Q-phenyl-$SO_2F$, —N(H)C(O)-phenyl, —N(H)C(O)-phenyl-$SO_2F$, $(C_1-C_3)$alkyl-substituted pyrazole, $(C_6-C_{14})$aryl$(C_1-C_3)$alkyl, tert-butyldimethylsilyloxy-$CH_2$—, —N($R^5$)$_2$, $(C_1-C_3)$alkoxy$(C_1-C_3)$alkyl, $(C_1-C_3)$alkyl-C(O)—, oxo, $(C_1-C_3)$haloalkyl-C(O)—, —$SO_2F$, $(C_1-C_3)$alkoxy$(C_1-C_3)$alkoxy, —$CH_2OC(O)N(R^5)_2$, —$CH_2N(H)C(O)O$—$(C_1-C_6)$alkyl, —$CH_2N(H)C(O)N(R^5)_2$, —$CH_2N(H)C(O)(C_1-C_6)$alkyl, —$CH_2$(pyrazolyl), —$CH_2N(H)S(O)_2(C_1-C_6)$alkyl, —$CH_2OC(O)(C_3-C_{12})$heterocyclyl, —OC(O)N($R^5$)$_2$, —OC(O)N(H)$(C_1-C_3)$alkyl-O—$(C_1-C_3)$alkyl, —OC(O)N(H)$(C_1-C_3)$alkyl-O—$(C_1-C_3)$alkyl-phenyl-$(C_1-C_3)$alkyl-N(CH$_3$)$_2$, —OC(O)N(H)$(C_1-C_3)$alkyl-O—$(C_1-C_3)$alkyl-phenyl, —OC(O)$(C_3-C_{12})$heterocyclyl or —$CH_2$—$(C_3-C_{12})$heterocyclyl, wherein the phenyl of —N(H)C(O)phenyl and —OC(O)N(H)$(C_1-C_3)$alkyl-O—$(C_1-C_3)$alkyl-phenyl is optionally substituted with —C(O)H or —OH, and the $(C_3-C_{12})$heterocyclyl of —$CH_2$—$(C_3-C_{12})$heterocyclyl is optionally substituted with oxo. Values for the remaining variables are as described in the first embodiment, or first through fourteenth aspects thereof.

A second embodiment provides a compound of the following structural formula:

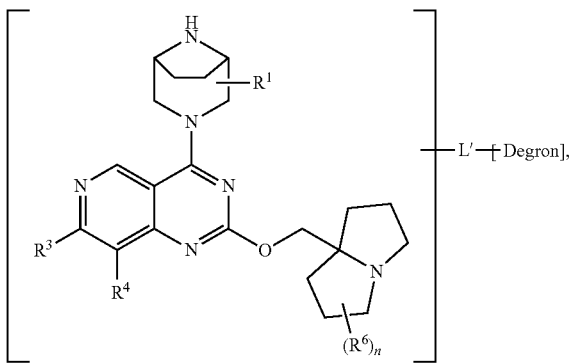

(II)

or a pharmaceutically acceptable salt thereof, wherein n is 0, 1 or 2 (and, in some aspects, 1 or 2; in further aspects, 1), and values for the remaining variables (e.g., $R^1$, $R^3$, $R^4$, $R^6$, L', Degron) are as described in the first embodiment, or any aspect thereof.

In a first aspect of the second embodiment, the compound is of the following structural formula:

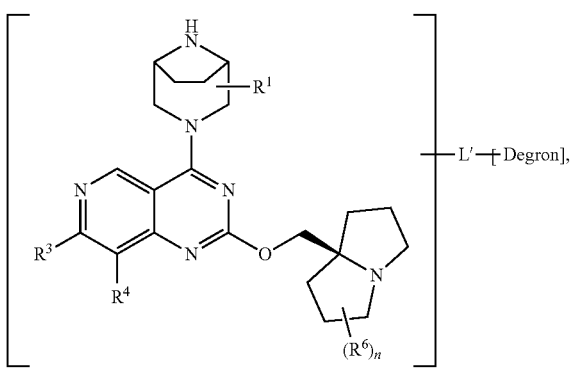

(IIa)

or a pharmaceutically acceptable salt thereof. Values for the variables (e.g., $R^1$, $R^3$, $R^4$, $R^6$, n, L', Degron) are as described in the first embodiment, or any aspect thereof, or the second embodiment.

In a second aspect of the second embodiment, the compound is of the following structural formula:

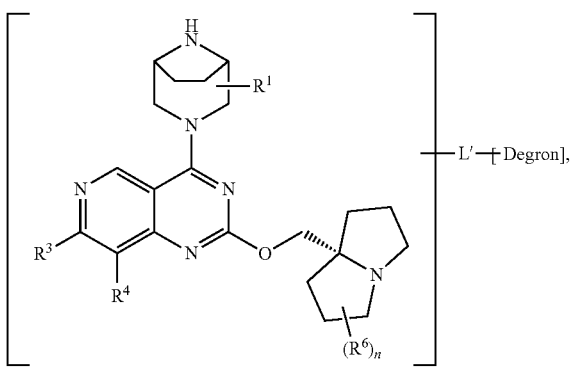

(IIb)

or a pharmaceutically acceptable salt thereof. Values for the variables (e.g., $R^1$, $R^3$, $R^4$, $R^6$, n, L', Degron) are as described in the first embodiment, or any aspect thereof, or the second embodiment.

A third embodiment is a compound of the following structural formula:

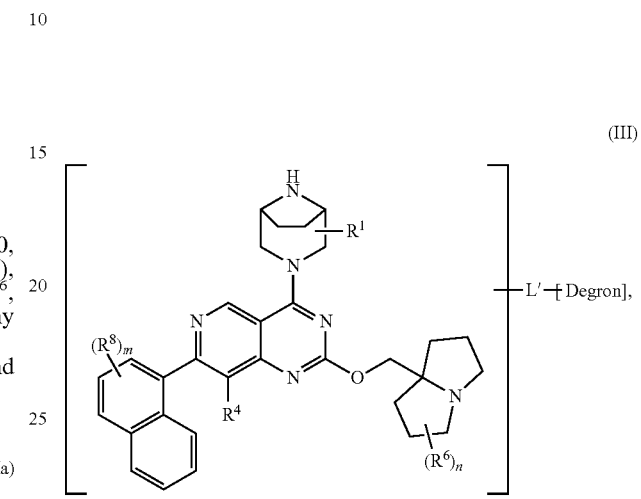

(III)

or a pharmaceutically acceptable salt thereof, wherein m is 0, 1, 2, 3, 4 or 5 (and, in some aspects, 1, 2 or 3; in further aspects, 2 or 3; in yet further aspects, 3), and values for the remaining variables (e.g., $R^1$, $R^4$, $R^6$, $R^8$, n, L', Degron) are as described in the first or second embodiment, or any aspect of the foregoing.

In a first aspect of the third embodiment, the compound is of the following structural formula:

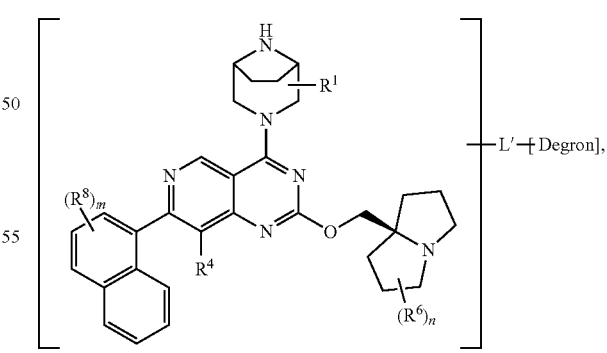

(IIIa)

or a pharmaceutically acceptable salt thereof. Values for the variables (e.g., $R^1$, $R^4$, $R^6$, $R^8$, n, m, L', Degron) are as described in the first or second embodiment, or any aspect of the foregoing.

In a second aspect of the third embodiment, the compound is of the following structural formula:

(IIIb)

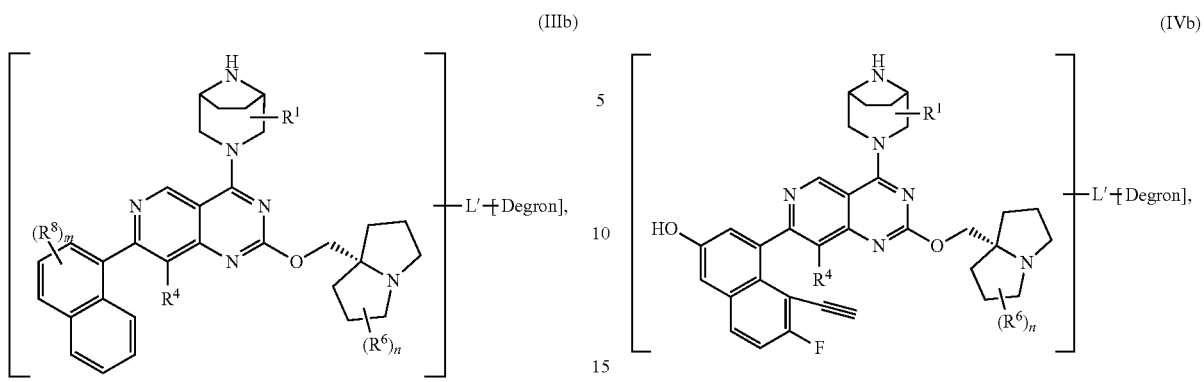

or a pharmaceutically acceptable salt thereof. Values for the variables (e.g., $R^1$, $R^4$, $R^6$, $R^8$, n, m, L', Degron) are as described in the first or second embodiment, or any aspect of the foregoing.

A fourth embodiment is a compound of the following structural formula:

(IV)

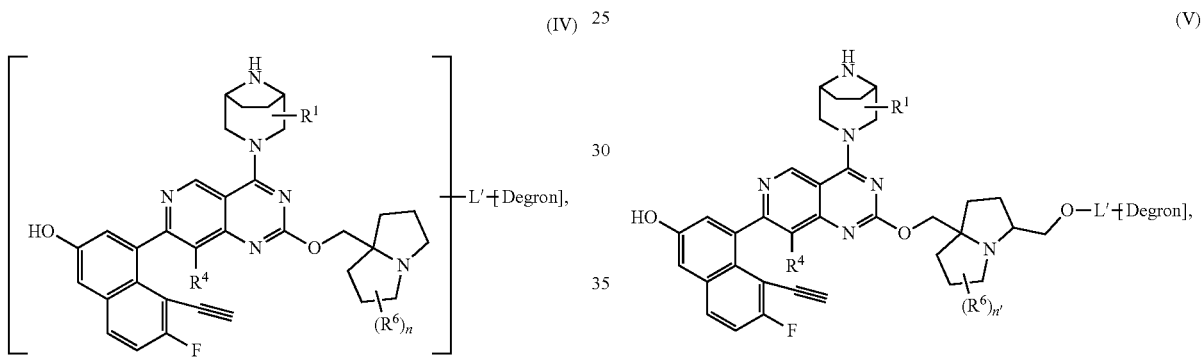

or a pharmaceutically acceptable salt thereof. Values for the variables (e.g., $R^1$, $R^4$, $R^6$, n, L', Degron) are as described in the first or second embodiment, or any aspect of the foregoing.

In a first aspect of the fourth embodiment, the compound is of the following structural formula:

(IVa)

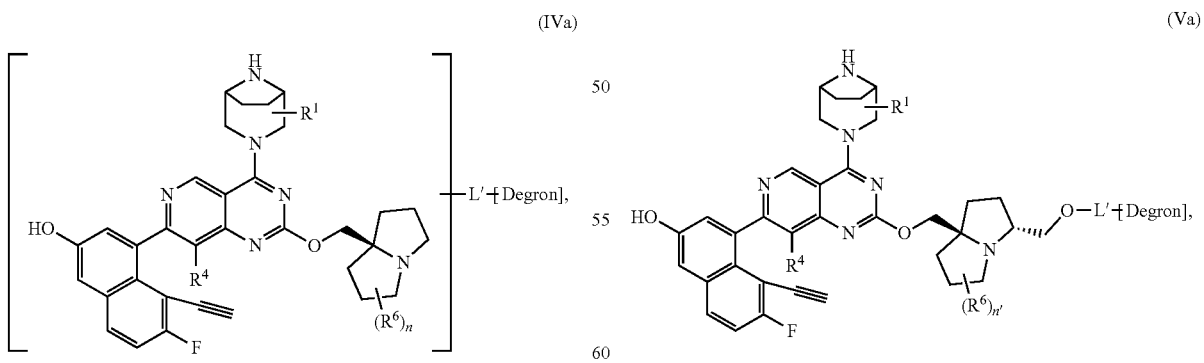

or a pharmaceutically acceptable salt thereof. Values for the variables (e.g., $R^1$, $R^4$, $R^6$, n, L', Degron) are as described in the first or second embodiment, or any aspect of the foregoing.

In a second aspect of the fourth embodiment, the compound is of the following structural formula:

(IVb)

or a pharmaceutically acceptable salt thereof. Values for the variables (e.g., $R^1$, $R^4$, $R^6$, n, L', Degron) are as described in the first or second embodiment, or any aspect of the foregoing.

A fifth embodiment is a compound of the following structural formula:

(V)

or a pharmaceutically acceptable salt thereof, wherein n' is 0 or 1 (and, in some aspects, 0), and values for the remaining variables (e.g., $R^1$, $R^4$, $R^6$, L', Degron) are as described in the first embodiment, or any aspect thereof.

In a first aspect of the fifth embodiment, the compound is of the following structural formula:

(Va)

or a pharmaceutically acceptable salt thereof. Values for the variables (e.g., $R^1$, $R^4$, $R^6$, n', L', Degron) are as described in the first embodiment, or any aspect thereof, or the fifth embodiment.

In a second aspect of the fifth embodiment, the compound is of the following structural formula:

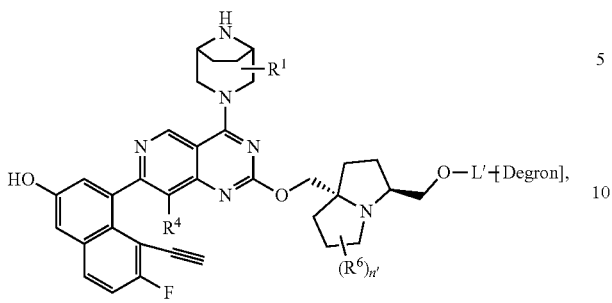

(Vb)

or a pharmaceutically acceptable salt thereof. Values for the variables (e.g., $R^1$, $R^4$, $R^6$, n', L', Degron) are as described in the first embodiment, or any aspect thereof, or the fifth embodiment.

A sixth embodiment is a compound of the following structural formula:

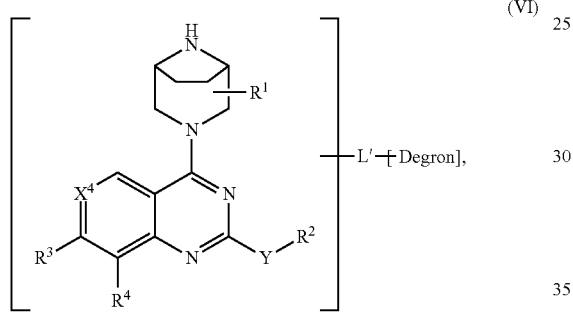

(VI)

or a pharmaceutically acceptable salt thereof, wherein:

$X^4$ is N or $C(R^{42})$;

$R^{42}$ is selected from hydrogen, halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —$NH(C_{1-6}$alkyl), —$N(C_{1-6}$alkyl)$_2$, —OH, —$O(C_{1-6}$alkyl), —SH, —$S(C_{1-6}$alkyl), —$S(haloC_{1-6}$alkyl), —$S(=O)(C_{1-6}$alkyl), —$S(=O)_2(C_{1-6}$alkyl), —$C(=O)(C_{1-6}$alkyl), —$C(=O)OH$, —$C(=O)(OC_{1-6}$alkyl), —$OC(=O)(C_{1-6}$ alkyl), —$C(=O)NH_2$, —$C(=O)NH(C_{1-6}$alkyl), —$C(=O)N(C_{1-6}$alkyl)$_2$, —$NHC(=O)(C_{1-6}$alkyl), —$N(C_{1-6}$alkyl)$C(=O)(C_{1-6}$alkyl), —$OC(=O)O(C_{1-6}$ alkyl), —$NHC(=O)(OC_{1-6}$alkyl), —$N(C_{1-6}$alkyl)$C(=O)(C_{1-6}$alkyl), —$OC(=O)NH(C_{1-6}$alkyl), —$OC(=O)N(C_{1-6}$alkyl)$_2$, —$NHC(=O)NH_2$, —$NHC(=O)NH(C_{1-6}$alkyl)$_2$, —$NHC(=O)N(C_{1-6}$alkyl)$_2$, —$N(C_{1-6}$alkyl)$C(=O)NH_2$, —$N(C_{1-6}$alkyl)$C(=O)NH(C_{1-6}$alkyl), —$N(C_{1-6}$alkyl)$C(=O)N(C_{1-6}$alkyl)$_2$, —$S(=O)(OC_{1-6}$alkyl), —$S(=O)(C_{1-6}$alkyl), —$S(=O)NH_2$, —$S(=O)NH(C_{1-6}$alkyl), —$S(=O)N(C_{1-6}$alkyl)$_2$, —$NHS(=O)(C_{1-6}$alkyl), —$N(C_{1-6}$alkyl)$S(=O)(C_{1-6}$alkyl), —$S(=O)_2(OC_{1-6}$alkyl), —$OS(=O)_2(C_{1-6}$alkyl), —$S(=O)_2NH_2$, —$S(=O)_2NH(C_{1-6}$alkyl), —$S(=O)_2N(C_{1-6}$alkyl)$_2$, —$NHS(=O)_2(C_{1-6}$alkyl), —$N(C_{1-6}$alkyl)$S(=O)_2(C_{1-6}$alkyl), —$OS(=O)_2O(C_{1-6}$ alkyl), —$NHS(=O)_2(C_{1-6}$alkyl), —$N(C_{1-6}$alkyl)$S(=O)_2O(C_{1-6}$alkyl), —$OS(=O)_2NH_2$, —$OS(=O)_2NH(C_{1-6}$alkyl), —$OS(=O)_2N(C_{1-6}$alkyl)$_2$, —$NHS(=O)_2NH_2$, —$NHS(=O)_2NH(C_{1-6}$alkyl), —$NHS(=O)_2N(C_{1-6}$alkyl)$_2$, —$N(C_{1-6}$alkyl)$S(=O)_2NH_2$, —$N(C_{1-6}$alkyl)$S(=O)_2NH(C_{1-6}$alkyl), —$N(C_{1-6}$alkyl)$S(=O)_2NH(C_{1-6}$alkyl), —$N(C_{1-6}$alkyl)$S(=O)_2N(C_{1-6}$alkyl)$_2$, —$PH(C_{1-6}$alkyl), —$P(C_{1-6}$alkyl)$_2$, —$P(=O)H(C_{1-6}$alkyl), —$P(=O)(C_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —$NH(C_{1-6}$alkyl), —$N(C_{1-6}$alkyl)$_2$, —OH, —$O(C_{1-6}$alkyl), —SH, —$S(C_{1-6}$alkyl), —$S(haloC_{1-6}$alkyl), —$S(=O)(C_{1-6}$alkyl), —$S(=O)_2(C_{1-6}$alkyl), —$C(=O)(C_{1-6}$alkyl), —$C(=O)OH$, —$C(=O)(OC_{1-6}$alkyl), —$OC(=O)(C_{1-6}$alkyl), —$C(=O)NH_2$, —$C(=O)NH(C_{1-6}$alkyl), —$C(=O)N(C_{1-6}$alkyl)$_2$, —$NHC(=O)(C_{1-6}$alkyl), —$N(C_{1-6}$alkyl)$C(=O)(C_{1-6}$alkyl), —$OC(=O)O(C_{1-6}$alkyl), —$NHC(=O)(OC_{1-6}$alkyl), —$N(C_{1-6}$alkyl)$C(=O)(OC_{1-6}$alkyl), —$OC(=O)NH(C_{1-6}$alkyl), —$OC(=O)N(C_{1-6}$alkyl)$_2$, —$NHC(=O)NH_2$, —$NHC(=O)NH(C_{1-6}$alkyl), —$NHC(=O)N(C_{1-6}$alkyl)$_2$, —$N(C_{1-6}$alkyl)$C(=O)NH_2$, —$N(C_{1-6}$alkyl)$C(=O)NH(C_{1-6}$alkyl), —$N(C_{1-6}$alkyl)$C(=O)N(C_{1-6}$alkyl)$_2$, —$S(=O)(OC_{1-6}$alkyl), —$OS(=O)(C_{1-6}$alkyl), —$S(=O)NH_2$, —$S(=O)NH(C_{1-6}$alkyl), —$S(=O)N(C_{1-6}$alkyl)$_2$, —$NHS(=O)(C_{1-6}$ alkyl), —$N(C_{1-6}$alkyl)$S(=O)(C_{1-6}$alkyl), —$S(=O)_2(OC_{1-6}$alkyl), —$OS(=O)_2(C_{1-6}$alkyl), —$S(=O)_2NH_2$, —$S(=O)_2NH(C_{1-6}$alkyl), —$S(=O)_2N(C_{1-6}$alkyl)$_2$, —$NHS(=O)_2(C_{1-6}$alkyl), —$N(C_{1-6}$alkyl)$S(=O)_2(C_{1-6}$alkyl), —$OS(=O)_2O(C_{1-6}$alkyl), —$NHS(=O)_2O(C_{1-6}$alkyl), —$N(C_{1-6}$alkyl)$S(=O)_2O(C_{1-6}$alkyl), —$OS(=O)_2NH_2$, —$OS(=O)_2NH(C_{1-6}$alkyl), —$OS(=O)_2N(C_{1-6}$alkyl)$_2$, —$NHS(=O)_2NH_2$, —$NHS(=O)_2NH(C_{1-6}$alkyl), —$NHS(=O)_2N(C_{1-6}$alkyl)$_2$, —$N(C_{1-6}$alkyl)$S(=O)_2NH_2$, —$N(C_{1-6}$alkyl)$S(=O)_2NH(C_{1-6}$alkyl), —$N(C_{1-6}$alkyl)$S(=O)_2N(C_{1-6}$alkyl)$_2$, —$PH(C_{1-6}$alkyl), —$P(C_{1-6}$alkyl)$_2$, —$P(=O)H(C_{1-6}$alkyl), —$P(=O)(C_{1-6}$alkyl)$_2$, 3-6 membered cycloalkyl, 3-6 membered heterocyclyl, 6-10 membered aryl or 5-10 membered heteroaryl; and values for the remaining variables (e.g., Y, $R^1$, $R^2$, $R^3$, $R^4$, L', Degron) are as described in the first through fifth embodiments, or any aspect of the foregoing.

In a first aspect of the sixth embodiment, $X^4$ is $C(R^{42})$. Values for the remaining variables are as described in the first through fifth embodiments, or any aspect of the foregoing, or the sixth embodiment.

In a second aspect of the sixth embodiment, $R^{42}$ is hydrogen, halogen, ($C_1$-$C_6$)alkyl, ($C_1$-$C_6$)haloalkyl, ($C_1$-$C_6$) haloalkoxy, ($C_2$-$C_6$)alkenyl, ($C_2$-$C_6$)alkynyl, —CN, ($C_1$-$C_6$) alkoxy, —S—($C_1$-$C_6$)alkyl or —S—($C_1$-$C_6$)haloalkyl. Values for the remaining variables are as described in the first through fifth embodiments, or any aspect of the foregoing, or the sixth embodiment, or first aspect thereof.

In a third aspect of the sixth embodiment, $R^{42}$ is hydrogen, fluoro, chloro, methyl, —$CF_3$, —$OCF_3$, —CN, —$OCH_3$, —$SCH_3$ or —$SCF_3$. Values for the remaining variables are as described in the first through fifth embodiments, or any aspect of the foregoing, or the sixth embodiment, or first or second aspect thereof.

A seventh embodiment is a compound of the following structural formula:

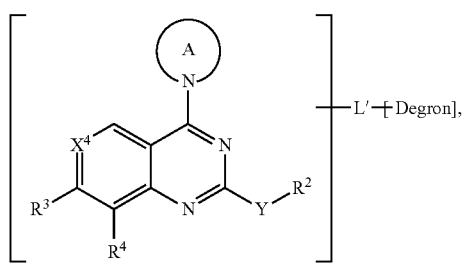

(VII)

or a pharmaceutically acceptable salt thereof, wherein:

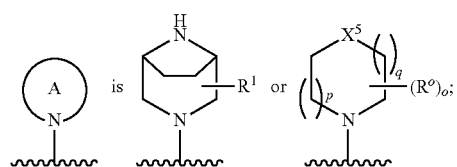

$X^5$ is O or $CH_2$;

two $R^o$, taken together with the same carbon atom, form a $C_{3-7}$ cycloalkyl or a 4-7-membered heterocyloalkyl, wherein each ($C_3$-$C_7$)cycloalkyl or 4-7-membered heterocyloalkyl is optionally substituted with 1, 2 or 3 substitutents independently selected from halogen, oxo, ($C_1$-$C_4$)alkyl, ($C_1$-$C_4$)alkoxy, ($C_1$-$C_4$)haloalkyl, hydroxyl, cyano, —S(O)$_2$($C_1$-$C_4$)alkyl, =NH, =N($C_1$-$C_4$)alkyl, —NH$_2$, —N(H)($C_1$-$C_4$)alkyl or —N(($C_1$-$C_4$)alkyl)$_2$, and when p is 3 or 4, each remaining $R^o$ is independently selected from hydroxyl, halogen, oxo, cyano, —N(($C_1$-$C_4$)alkyl)$_2$, ($C_1$-$C_4$)alkyl, ($C_1$-$C_4$)alkoxy, ($C_1$-$C_4$)haloalkyl or ($C_1$-$C_4$)haloalkoxy;

o is 2, 3 or 4;
p is 0, 1 or 2 (and, in some preferred aspects, 1);
q is 0, 1 or 2 (and, in some preferred aspects, 1); and
values for the remaining variables (e.g., $X^4$, Y, $R^1$, $R^2$, $R^3$, $R^4$, L', Degron) are as described in the first through sixth embodiments, or any aspect of the foregoing.

In a first aspect of the seventh embodiment,

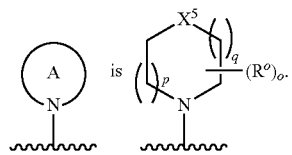

Values for the remaining variables are as described in the first through sixth embodiments, or any aspect of the foregoing, or the seventh embodiment.

In a second aspect of the seventh embodiment,

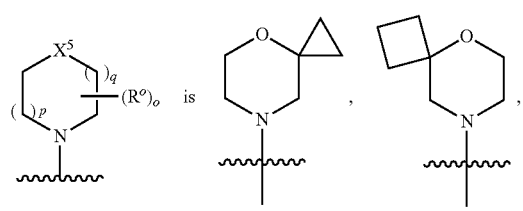

-continued

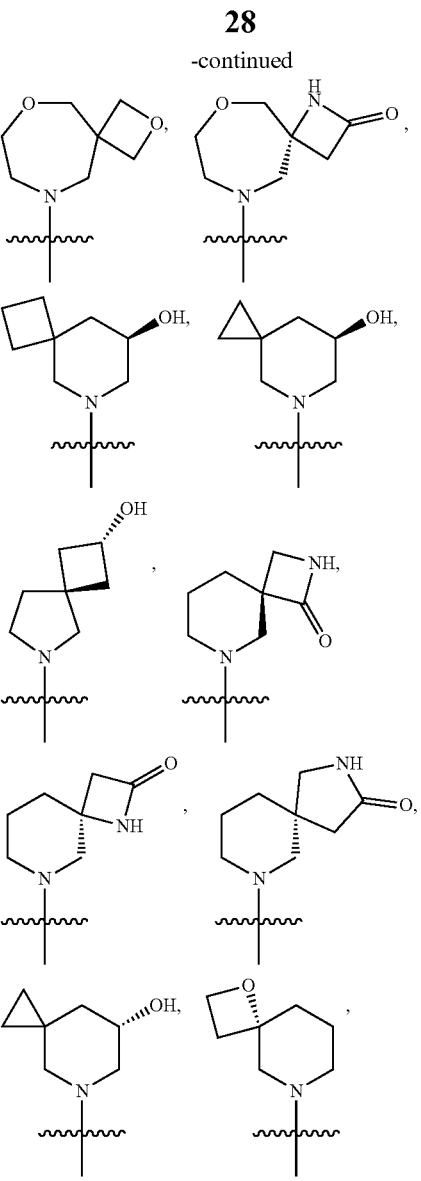

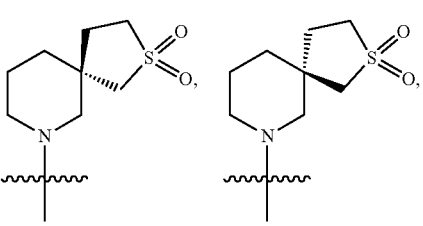

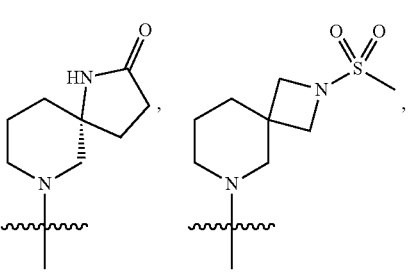

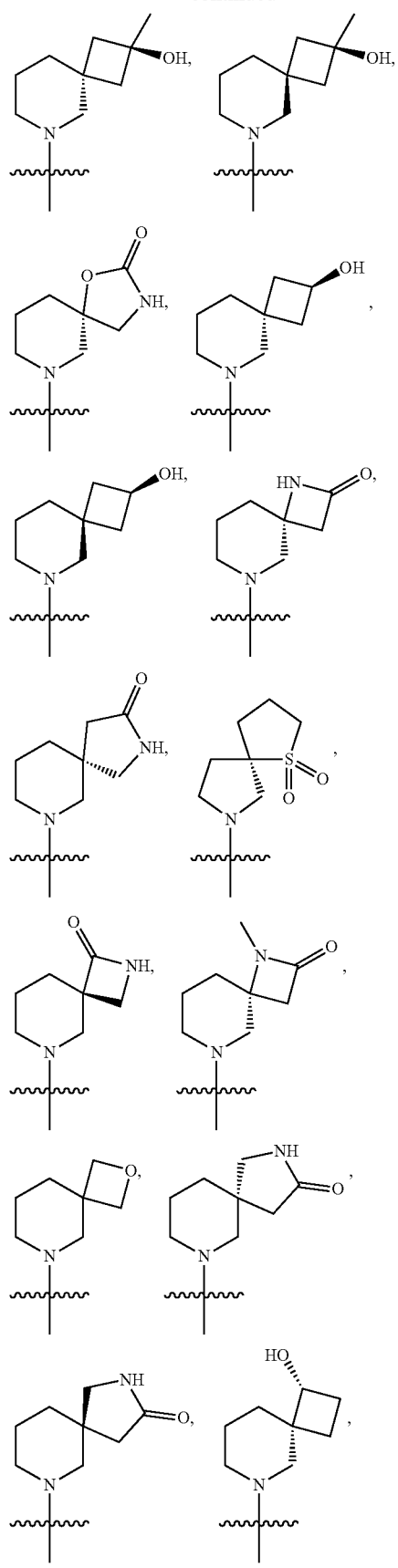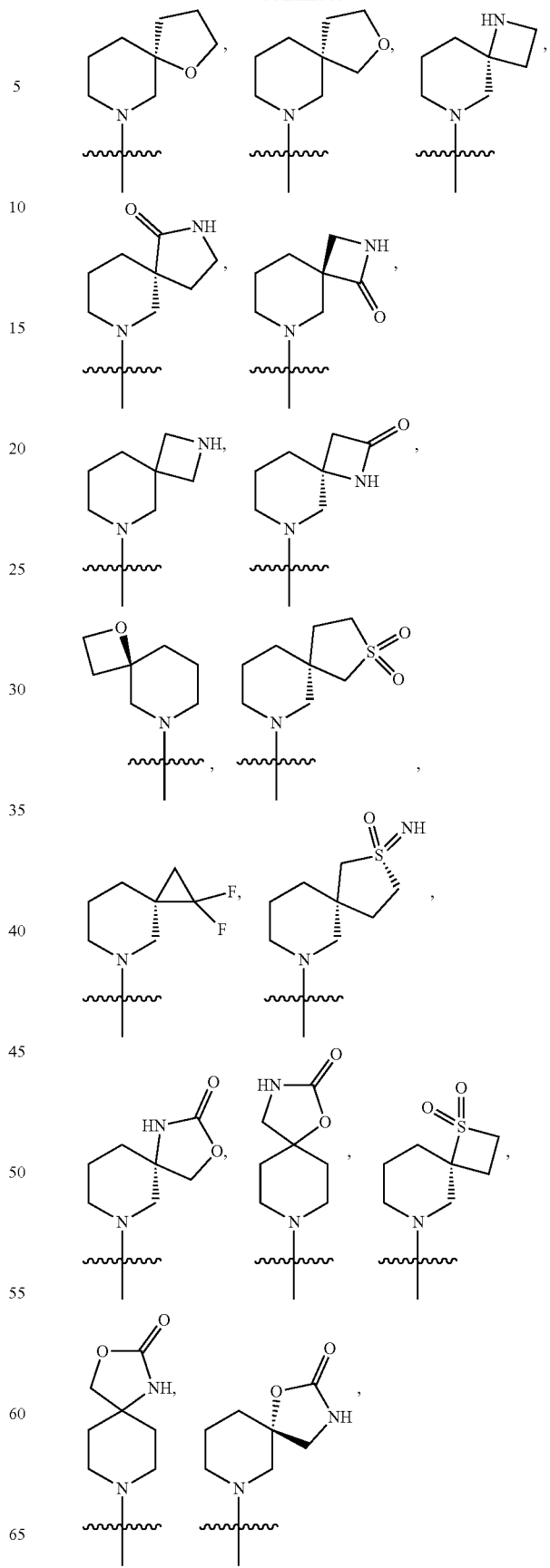

-continued

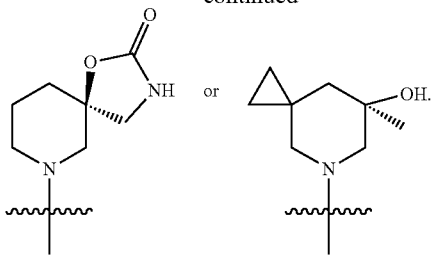

Values for the remaining variables are as described in the first through sixth embodiments, or any aspect of the foregoing, or the seventh embodiment, or first aspect thereof.

In a third aspect of the seventh embodiment,

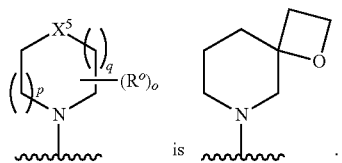

Values for the remaining variables are as described in the first through sixth embodiments, or any aspect of the foregoing, or the seventh embodiment, or first or second aspect thereof.

An eighth embodiment provides a compound of the following structural formula:

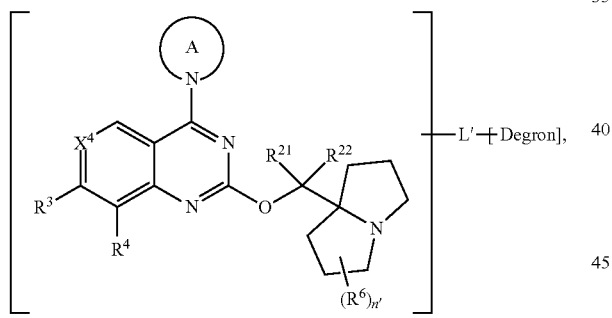
(VIII)

or a pharmaceutically acceptable salt thereof, wherein $R^{21}$ and $R^{22}$ are each independently H, D or F; n' is 0, 1, 2, 3, 4, 5, 6, 7, 8, 9, 10, 11 or 12 (and, in some aspects, 0, 1, 2, 3, 4, 5 or 6; in further aspects, 0, 1, 2, 3 or 4), and values for the remaining variables (e.g., Ring A, $X^4$, $R^3$, $R^4$, $R^6$, L', Degron) are as described in the first through seventh embodiments, or any aspect of the foregoing.

In a first aspect of the eighth embodiment, $R^{21}$ and $R^{22}$ are each D. Values for the remaining variables are as described in the first through seventh embodiments, or any aspect of the foregoing, or the eighth embodiment.

In a second aspect of the eighth embodiment, $R^{21}$ and $R^{22}$ are each H. Values for the remaining variables are as described in the first through seventh embodiments, or any aspect of the foregoing, or the eighth embodiment.

It will be understood that the moiety which is shown in square brackets in the compounds of structural formulas (I)-(VIII), corresponds to the KRAS G12D binding moiety in the compounds of structural formulas (I)-(VIII). In some embodiments, the KRAS G12D binding moiety is the moiety shown in square brackets in any one of structural formulas (I)-(VIII), wherein values for the variables (e.g., $X^4$, $X^5$, Y, $R^o$, $R^1$, $R^2$, $R^3$, $R^4$, $R^6$, $R^8$, n, m, o, p, q) are as described in the first through seventh embodiments, or any aspect of the foregoing.

In some aspects of the any of the aforementioned embodiments or aspects thereof, the KRAS G12D binding moiety is bonded to -L'-[Degron] via an atom of the group corresponding to $R^2$ or $R^6$ in structural formulas (I)-(VIII) as, for example, in the following structural formulas:

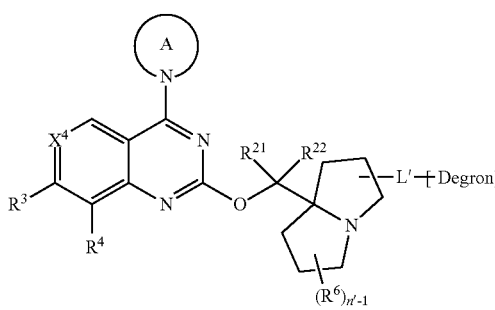
or

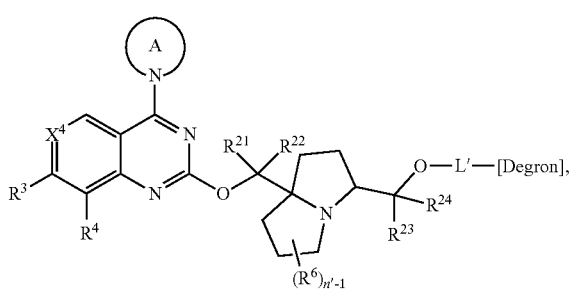

wherein $R^{23}$ and $R^{24}$ are each independently H, D or F and values for the remaining variables (e.g., Ring A, $X^4$, $R^3$, $R^4$, $R^6$, L', Degron) are as described in the first through eighth embodiments, or any aspect of the foregoing.

Specific examples of KRAS G12D binding moieties include:

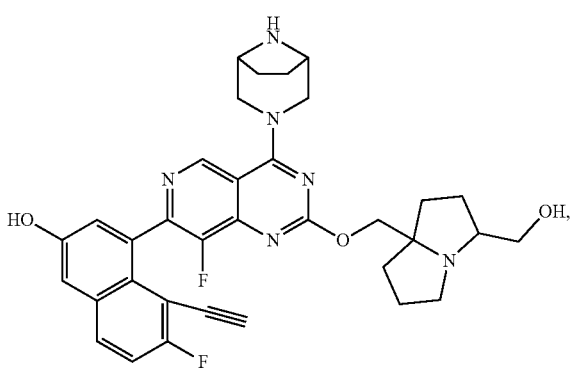 [SMILES: C#Cc1c(F)ccc2cc(O)cc(-c3ncc4c(N5CC6CCC(C5)N6)nc(OCC56CCCN5C(CO)CC6)nc4c3F)c12]

-continued
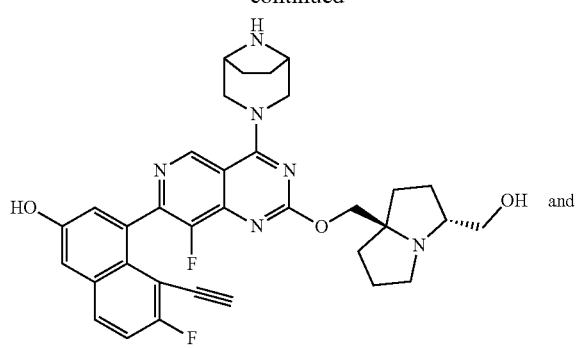
and
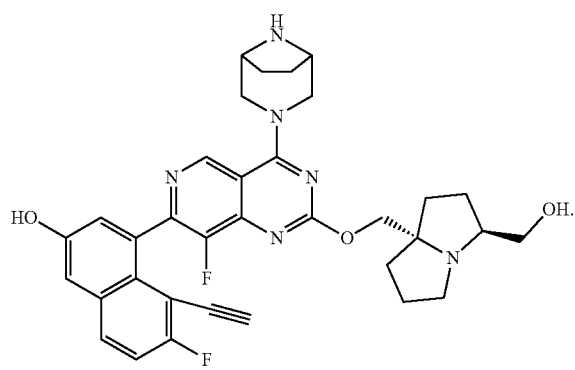
In some embodiments, the KRAS G12D binding moiety is
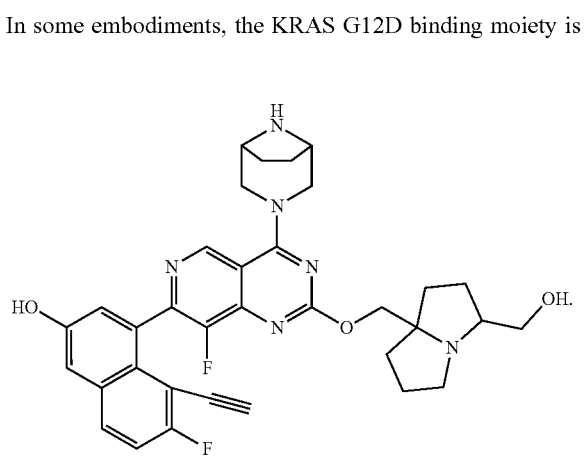
In some embodiments, the KRAS G12D binding moiety is
In some embodiments, the KRAS G12D binding moiety is
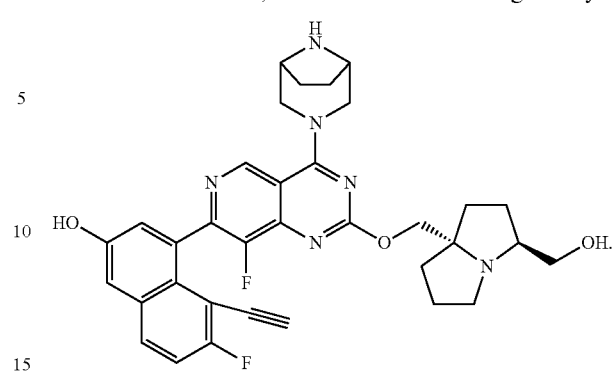
Other specific examples of KRAS G12D binding moieties include:
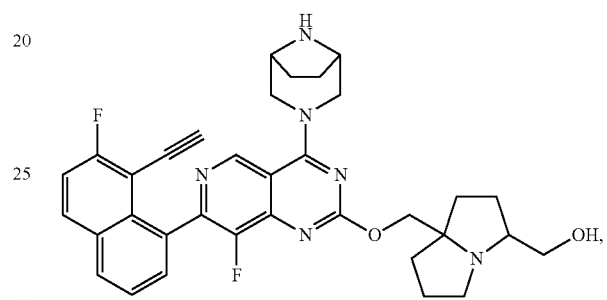
and
In some embodiments, the KRAS G12D binding moiety is
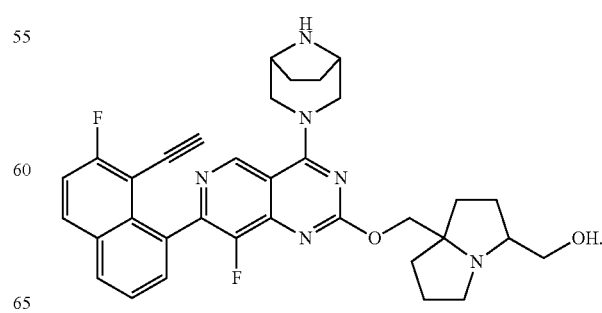

In some embodiments, the KRAS G12D binding moiety is

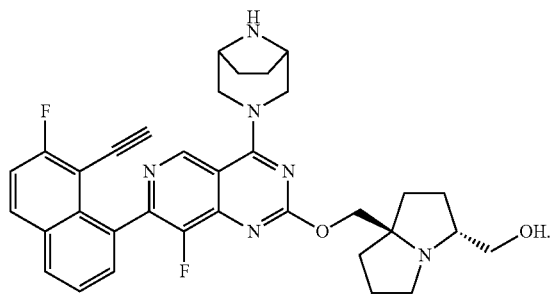 [SMILES: C#Cc1c(F)ccc2cccc(-c3ncc4c(N5CC6CCC(C5)N6)nc(OC[C@]56CCCN5[C@@H](CO)CC6)nc4c3F)c12]

In some embodiments, the KRAS G12D binding moiety is

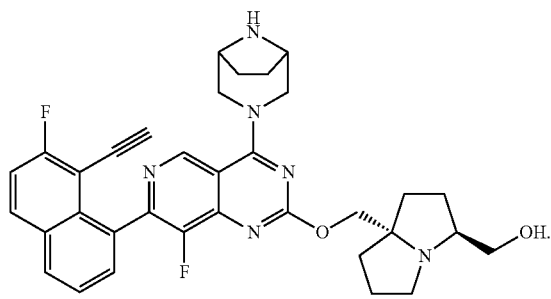 [SMILES: C#Cc1c(F)ccc2cccc(-c3ncc4c(N5CC6CCC(C5)N6)nc(OC[C@@]56CCCN5[C@H](CO)CC6)nc4c3F)c12]

Other specific examples of KRAS G12D binding moieties include those disclosed in Mao et al. Thus, in some embodiments, the KRAS G12D binding moiety has the following structural formula:

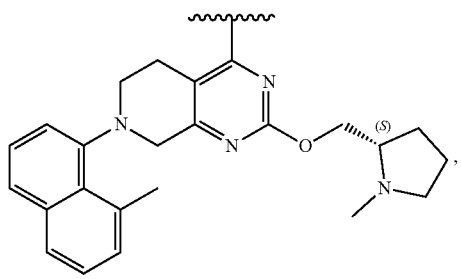

wherein

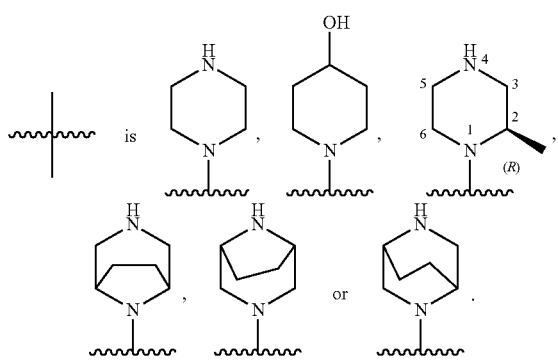

Yet other specific examples of KRAS G12D binding moieties include those disclosed in Wang, et al., "Identification of MRTX1133, a Noncovalent, Potent, and Selective KRAS$^{G12D}$ Inhibitor," *J. Med. Chem.*, https://doi.org/10.1021/acs.jmedchem.1c01688, the entire content of which is incorporated herein by reference. In some embodiments, the KRAS G12D binding moiety is a KRAS G12D inhibitor disclosed in Wang et al. For example, in some embodiments, a KRAS G12D binding moiety has the following structural formula:

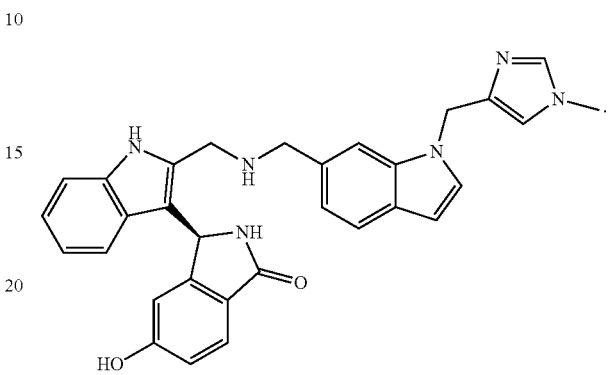

In some embodiments, a KRAS G12D binding moiety has the following structural formula:

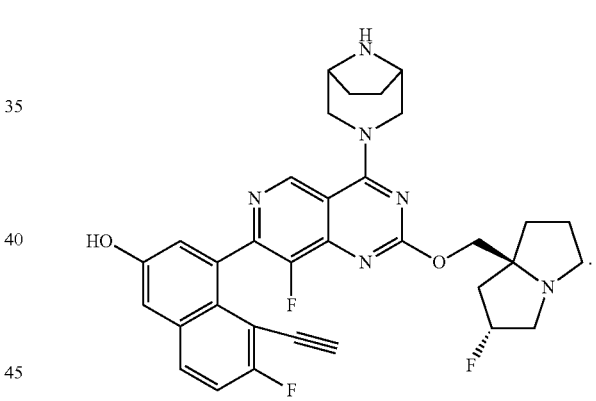

In some embodiments, a KRAS G12D binding moiety has the following structural formula:

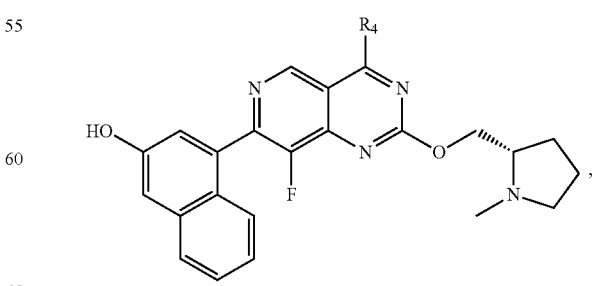

wherein $R_4$ is
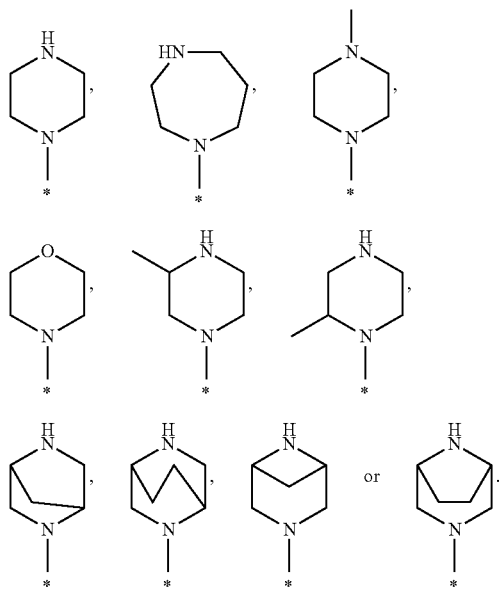
In some embodiments, a KRAS G12D binding moiety has the following structural formula:
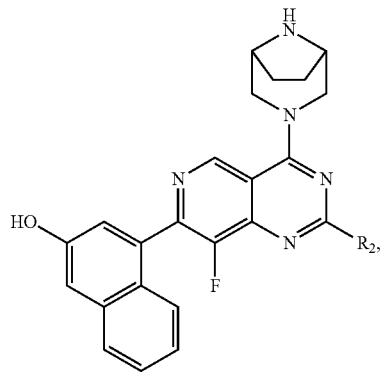
wherein $R_2$ is
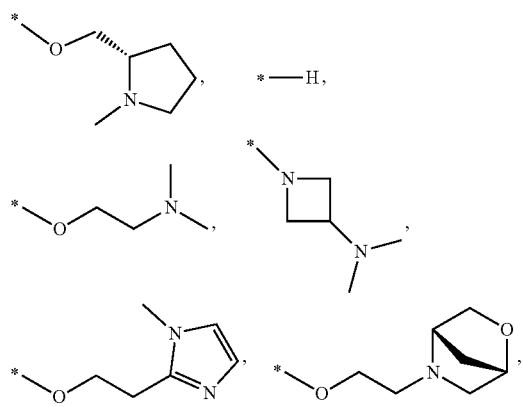
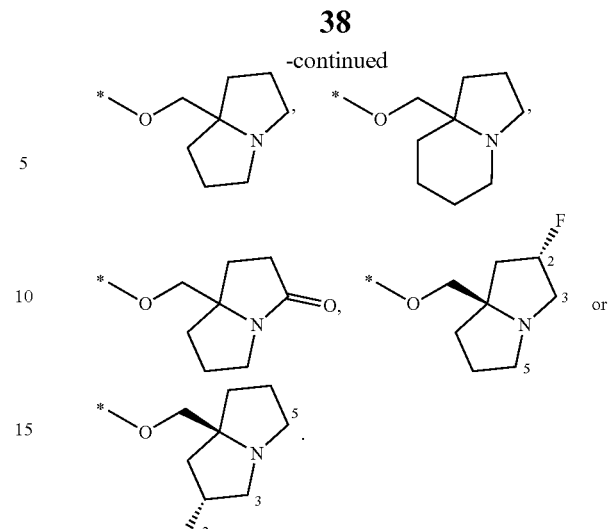
In some embodiments, a KRAS G12D binding moiety has the following structural formula:
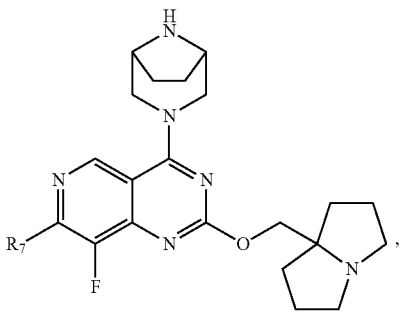
wherein $R_7$ is
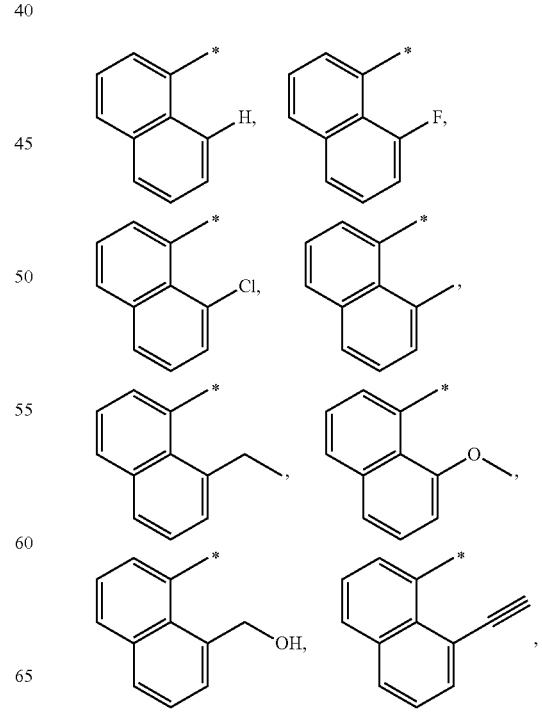

-continued

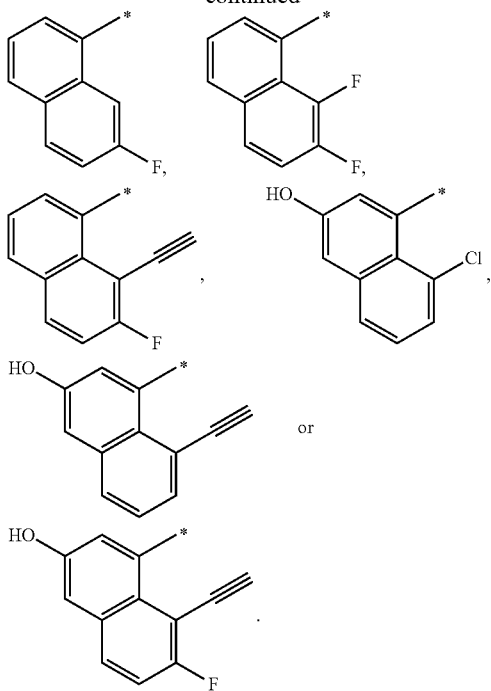

In some embodiments, the KRAS G12D binding moiety has the following structural formula:

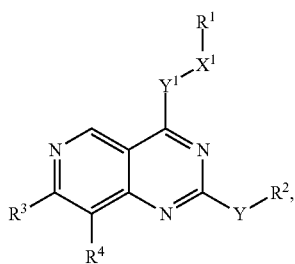

wherein:
X$^1$ is a bond or C$_1$-C$_4$alkylene;
Y and Y$^1$ are each independently a bond, O or NR$^5$;
R$^1$ is hydroxy, N(R$^5$)$_2$, (C$_3$-C$_{12}$)cycloalkyl, or (C$_3$-C$_{12}$)heterocyclyl, wherein the (C$_3$-C$_{12}$)cycloalkyl or (C$_3$-C$_{12}$)heterocyclyl is optionally substituted with one or more R$^X$;
 each R$^X$ is independently (C$_1$-C$_3$)alkyl, hydroxy, —N(R$^5$)$_2$, —CH$_2$N(R$^5$)$_2$, cyanomethyl, or (C$_3$-C$_{12}$)heterocyclyl;
R$^2$ is hydrogen, —N(R$^5$)$_2$, (C$_3$-C$_{12}$)heterocyclyl, (C$_1$-C$_6$) alkyl, -L-(C$_3$-C$_{12}$)heterocyclyl, -L-(C$_6$-C$_{14}$)aryl, -L-(C$_5$-C$_{14}$)heteroaryl, -L-(C$_3$-C$_{12}$)cycloalkyl, -L-N(R$^5$)$_2$, -L-N(H)C(NH)NH$_2$, -L-C(O)N(R$^5$)$_2$, -L-(C$_1$-C$_6$)haloalkyl, -L-OR$^5$, -L-(CH$_2$OR$^5$)(CH$_2$)$_{1-3}$OR$^5$, -L-NR$^5$C(O)—(C$_6$-C$_{14}$)aryl, or -L-COOH, wherein the (C$_3$-C$_{12}$) heterocyclyl, the (C$_6$-C$_{14}$)aryl of -L-NR$^5$C(O)—(C$_6$-C$_{14}$)aryl, the (C$_3$-C$_{12}$)heterocyclyl of -L-(C$_3$-C$_{12}$) heterocyclyl and the (C$_3$-C$_{12}$)cycloalkyl of -L-(C$_3$-C$_{12}$) cycloalkyl are optionally substituted with one or more R$^6$, and the aryl of -L-(C$_6$-C$_{14}$)aryl and (C$_5$-C$_{14}$)heteroaryl of -L-(C$_5$-C$_{14}$)heteroaryl are optionally substituted with one or more R$^7$;

each L is independently (C$_1$-C$_4$)alkylene optionally substituted with hydroxy, (C$_1$-C$_4$)hydroxyalkyl or (C$_5$-C$_{14}$)heteroaryl;
R$^3$ is (C$_6$-C$_{14}$)aryl or (C$_5$-C$_{14}$)heteroaryl, wherein the (C$_6$-C$_{14}$)aryl or (C$_5$-C$_{14}$)heteroaryl is optionally substituted with one or more R$^8$;
R$^4$ is hydrogen, halogen or (C$_1$-C$_3$)alkyl;
each R$^5$ is independently hydrogen or (C$_1$-C$_3$)alkyl;
each R$^6$ is independently halogen, hydroxy, (C$_1$-C$_3$)hydroxyalkyl, (C$_1$-C$_3$)alkyl, (C$_1$-C$_3$)haloalkyl, (C$_1$-C$_3$) alkoxy, -Q-phenyl, -Q-phenyl-SO$_2$F, —N(H)C(O)-phenyl, —N(H)C(O)-phenyl-SO$_2$F, (C$_1$-C$_3$)alkyl-substituted pyrazole, (C$_6$-C$_{14}$)aryl(C$_1$-C$_3$)alkyl, tert-butyldimethylsilyloxy-CH$_2$—, —N(R$^5$)$_2$, (C$_1$-C$_3$) alkoxy(C$_1$-C$_3$)alkyl, (C$_1$-C$_3$)alkyl-C(O)—, oxo, (C$_1$-C$_3$)haloalkyl-C(O)—, —SO$_2$F, (C$_1$-C$_3$)alkoxy(C$_1$-C$_3$) alkoxy, -L-OC(O)N(R$^5$)$_2$, or -L-OC(O)(C$_3$-C$_{12}$) heterocyclyl;
each Q is independently a bond or O;
each R$^7$ is independently halogen, hydroxy, —C(O)H, (C$_1$-C$_4$)alkyl, (C$_1$-C$_4$)alkoxy, (C$_1$-C$_4$)haloalkyl, (C$_1$-C$_4$)hydroxyalkyl or —N(R$^5$)$_2$; and
each R$^8$ is independently halogen, cyano, hydroxy, (C$_3$-C$_6$)cycloalkyl, (C$_1$-C$_3$)alkyl, —S—(C$_1$-C$_3$)alkyl, (C$_2$-C$_4$)alkenyl, (C$_2$-C$_4$)alkynyl, (C$_2$-C$_4$)hydroxyalkynyl, (C$_1$-C$_3$)cyanoalkyl, triazolyl, (C$_1$-C$_3$)haloalkyl, —O—(C$_1$-C$_3$)haloalkyl, or —S—(C$_1$-C$_3$)haloalkyl.

Alternative values for the variables are as described in the first, second or third embodiment, or any aspect of the foregoing.

In some embodiments, the KRAS G12D binding moiety is

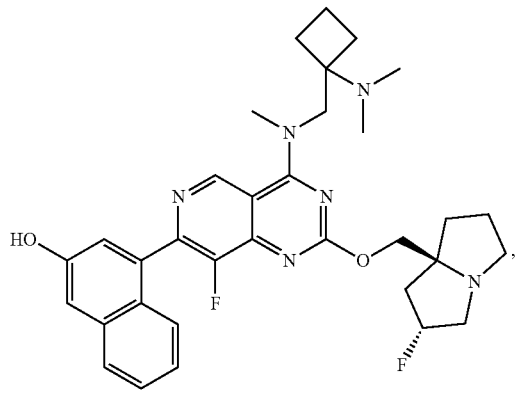

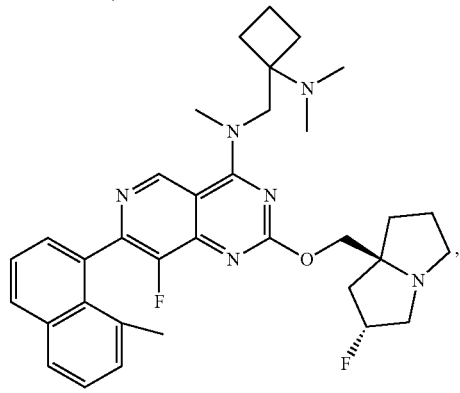

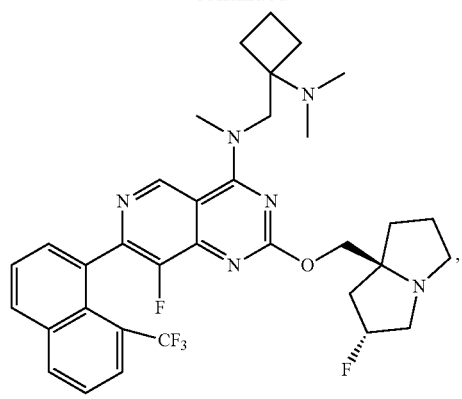
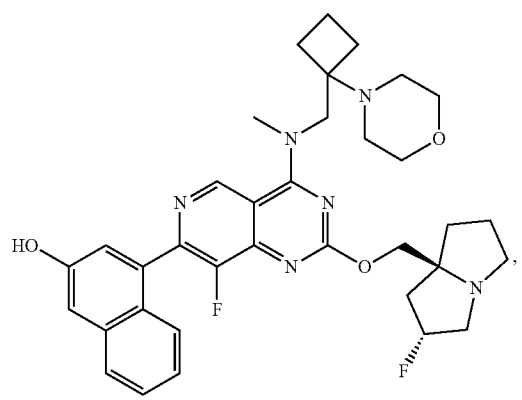
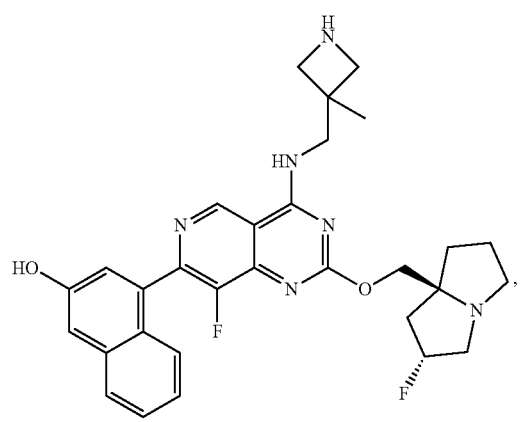
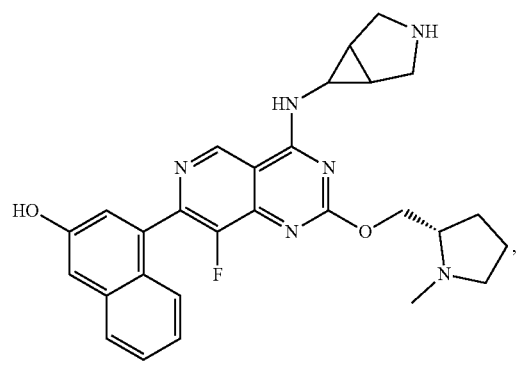
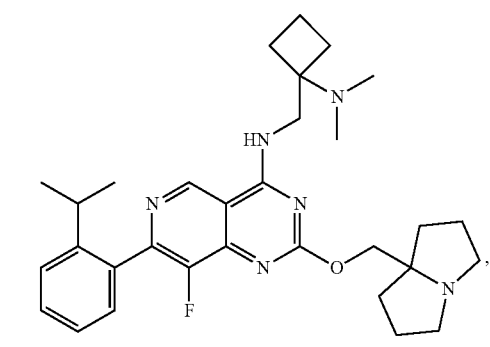
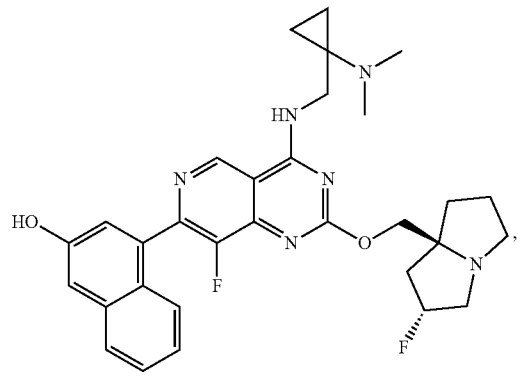
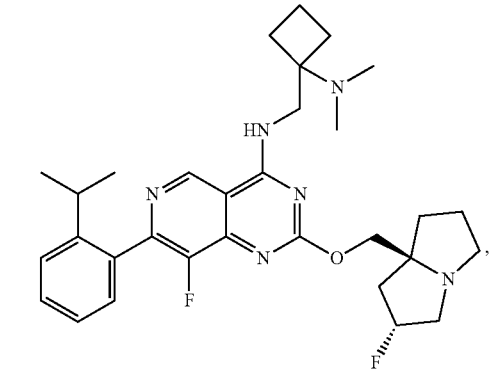

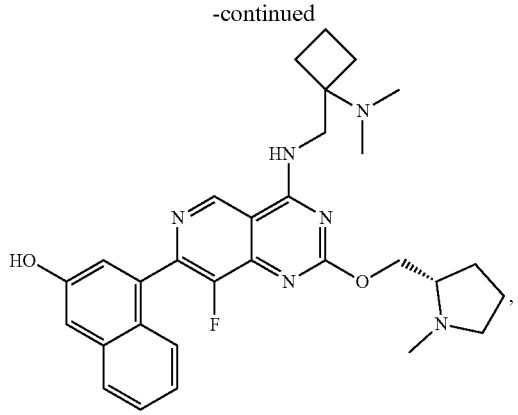
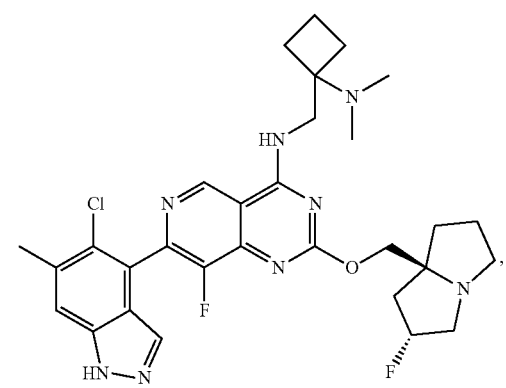
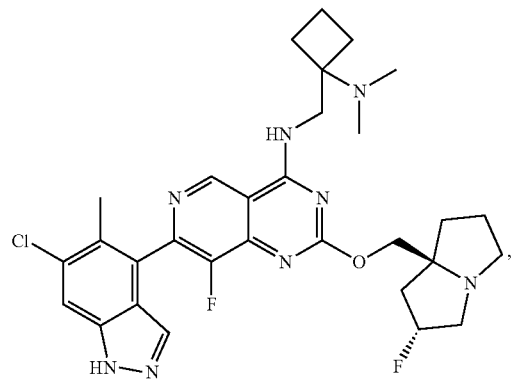
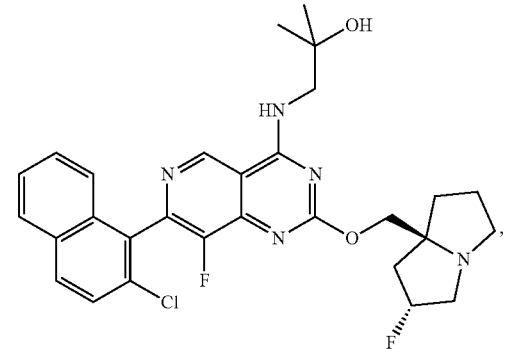
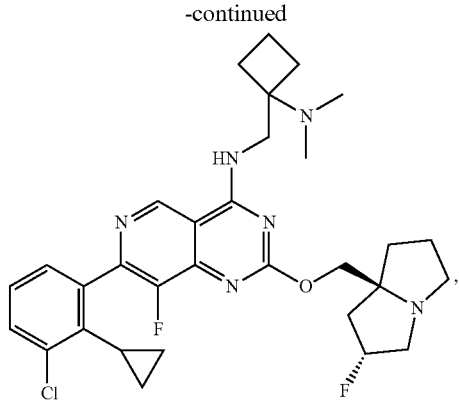
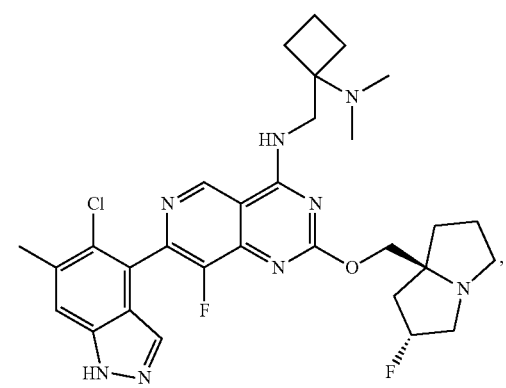
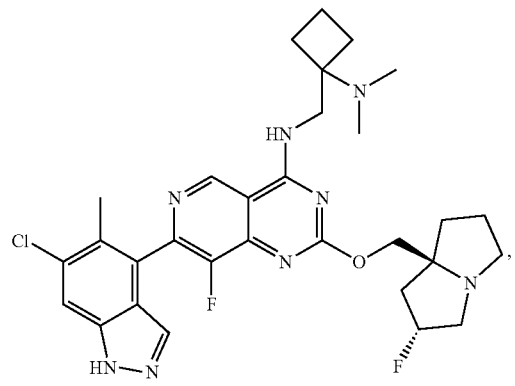
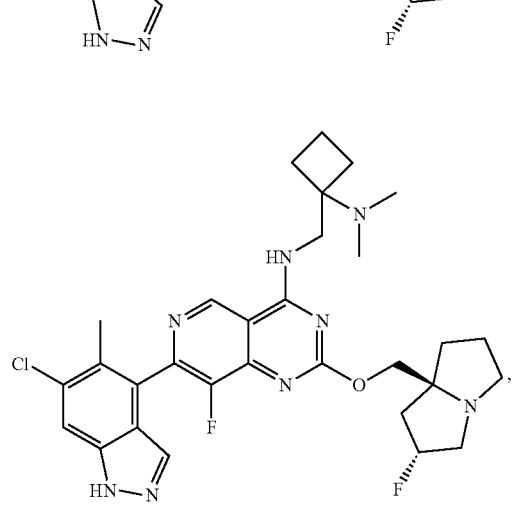

-continued
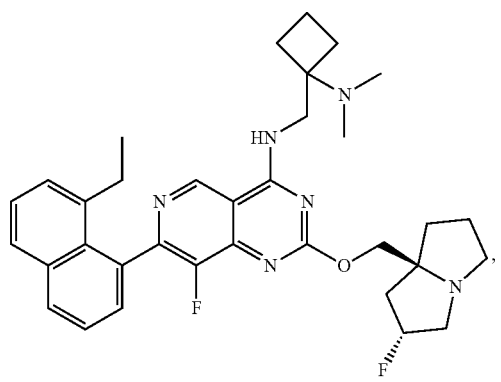
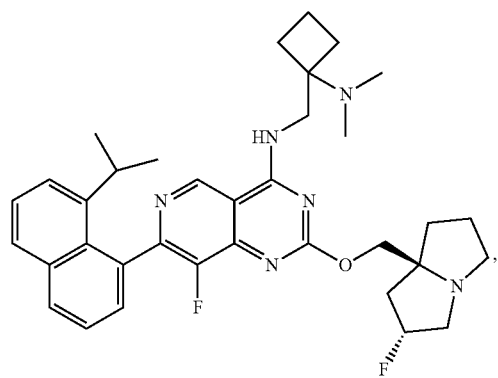
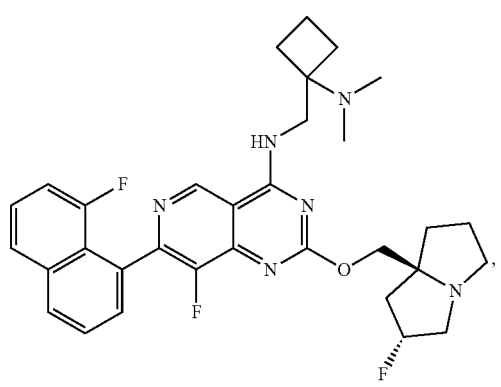
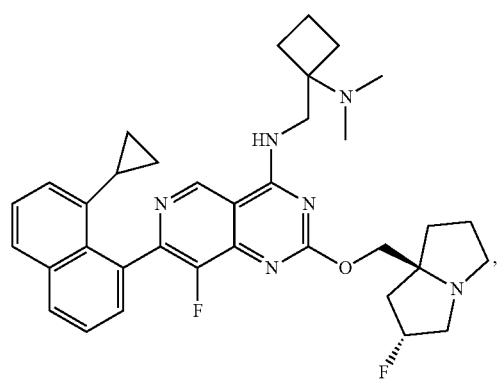
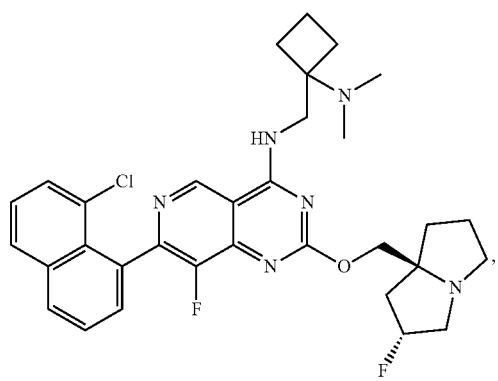
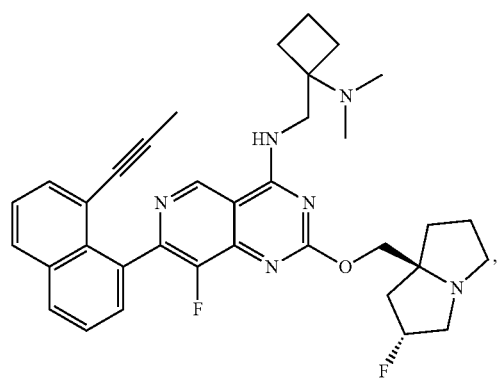

47
-continued
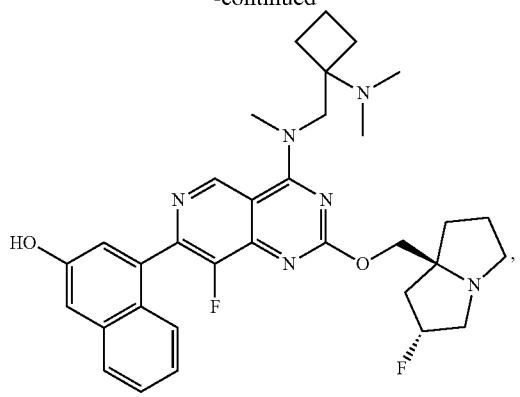
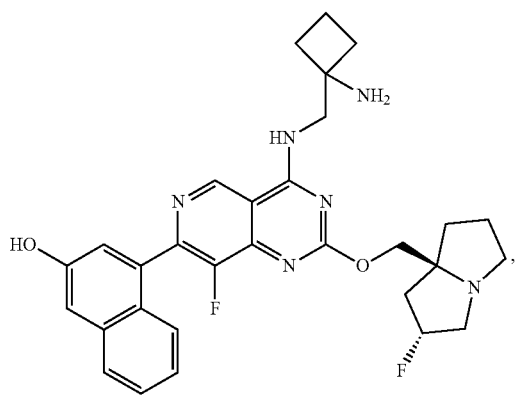
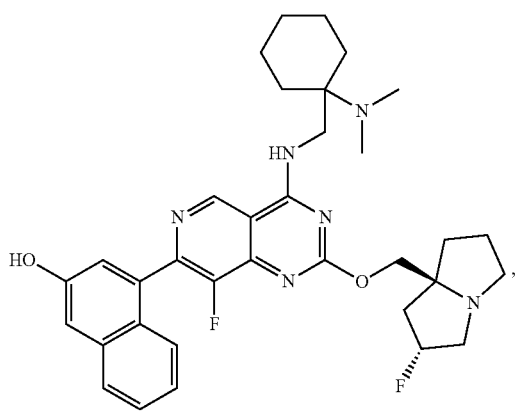
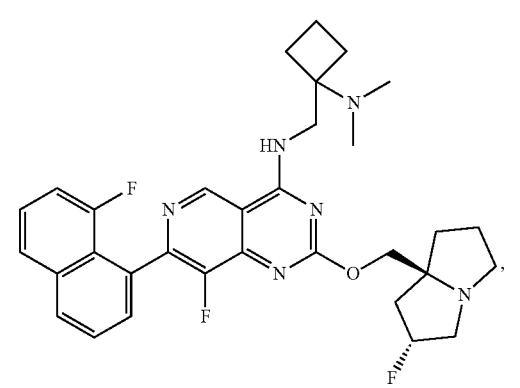
48
-continued
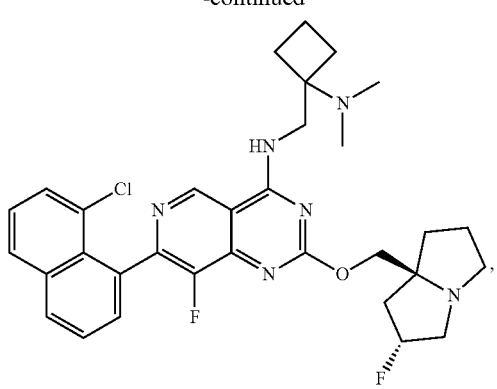
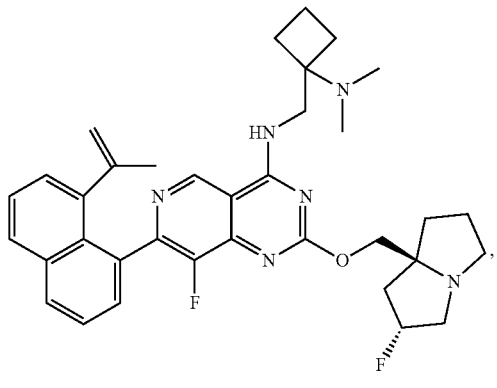
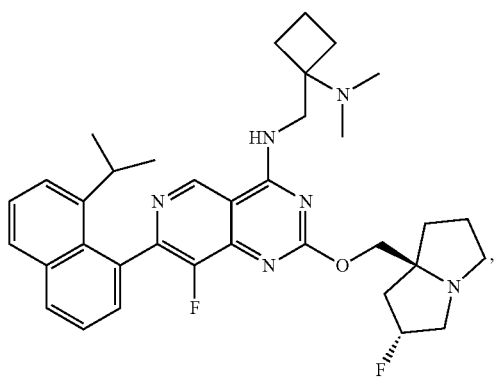
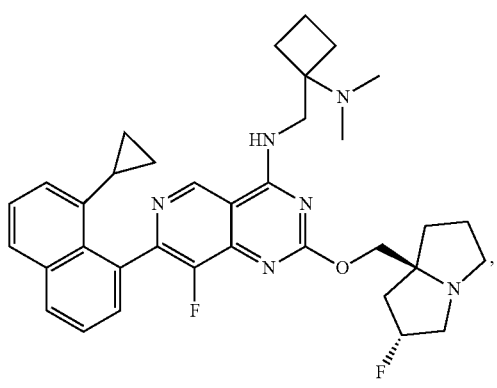

49
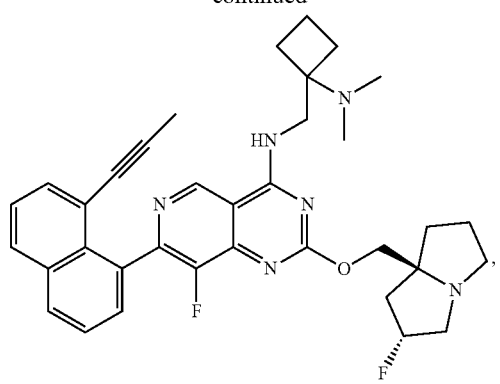
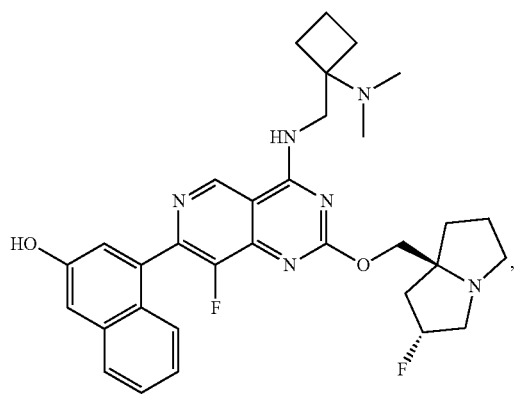
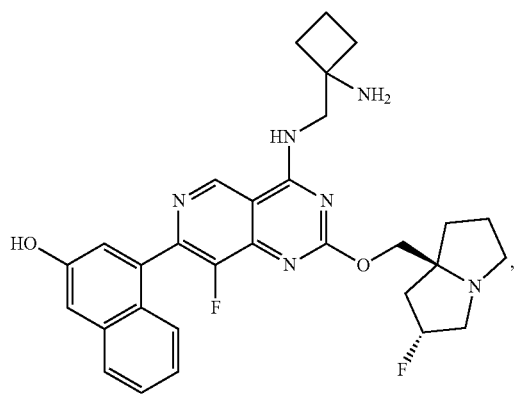
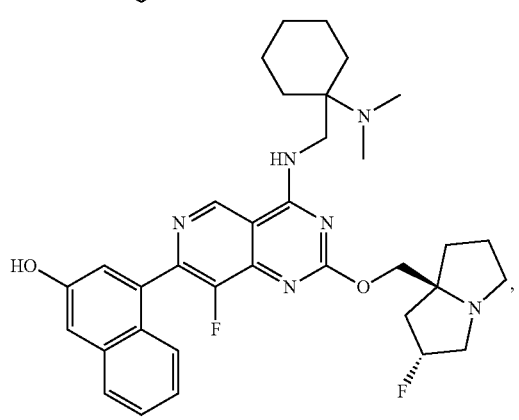
50
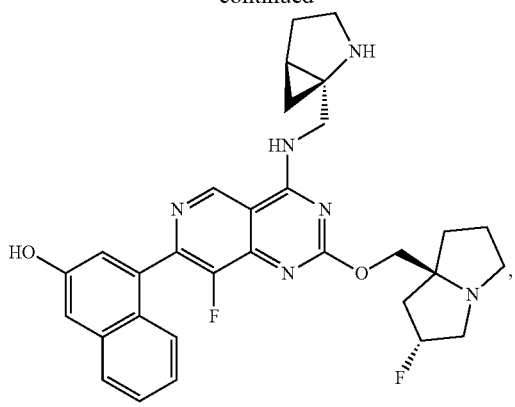
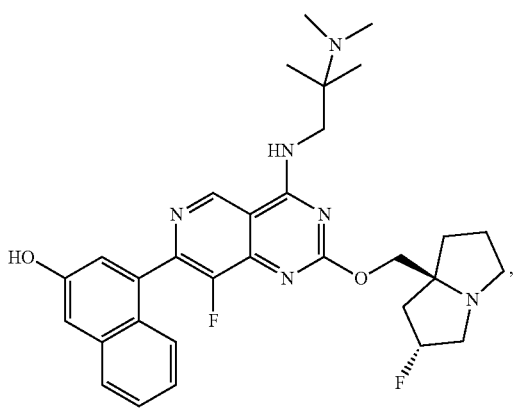
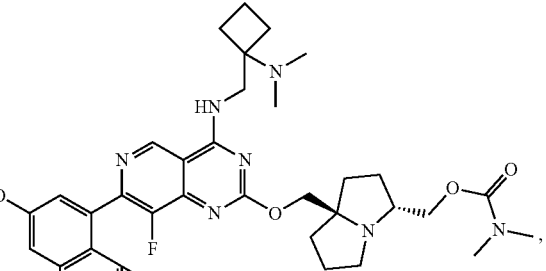

51 -continued
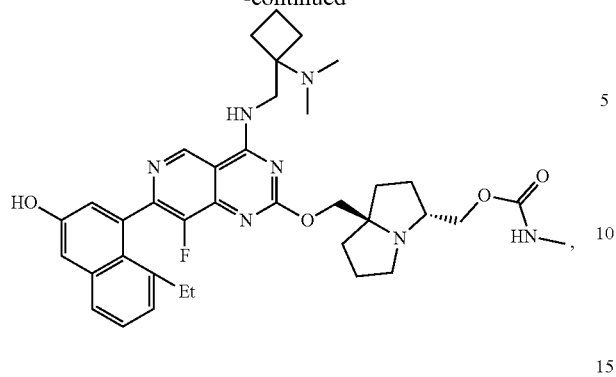
52 -continued
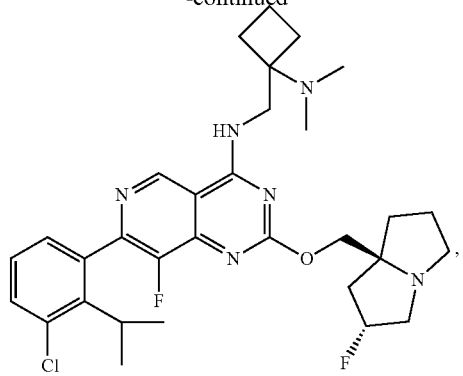
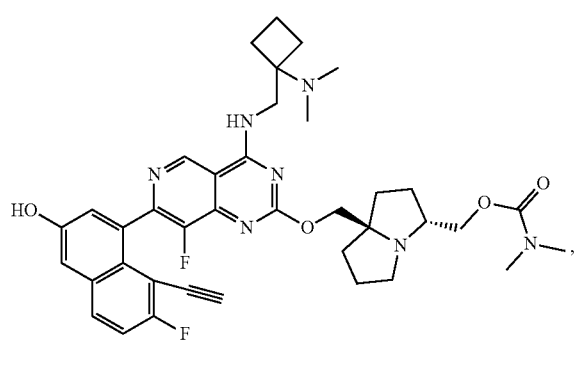
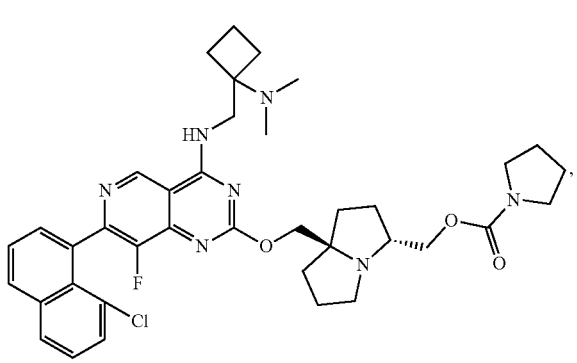
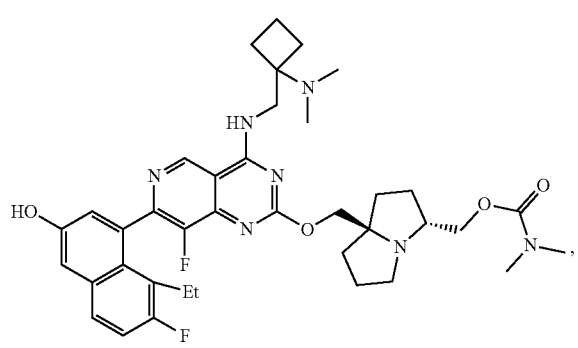
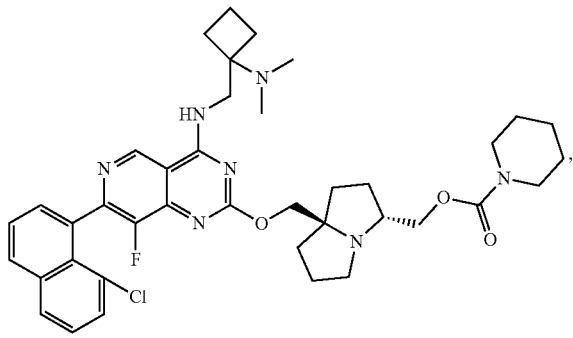
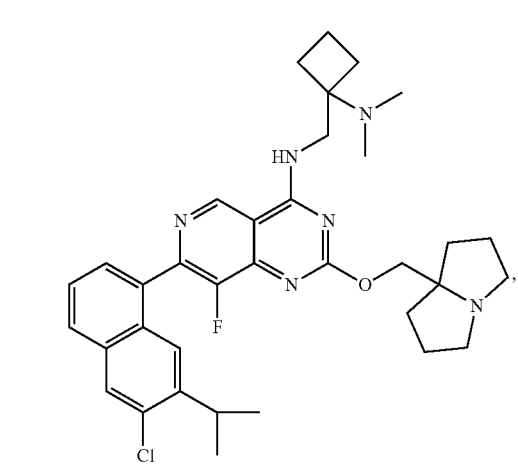
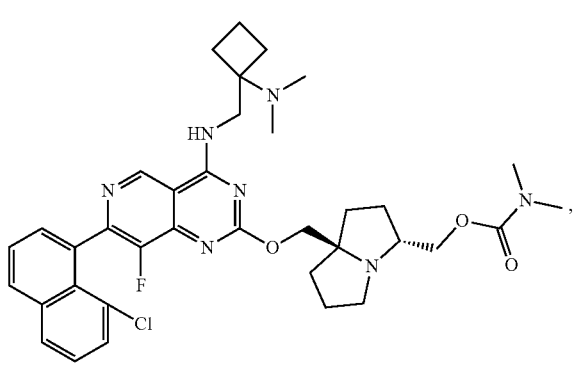

53
-continued
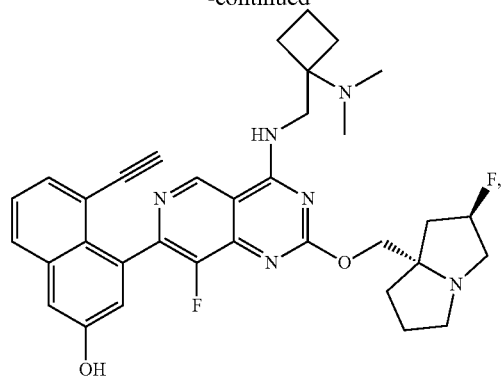
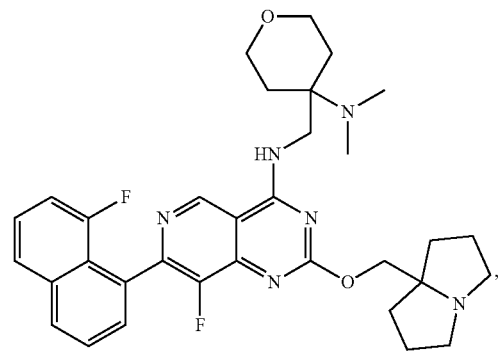
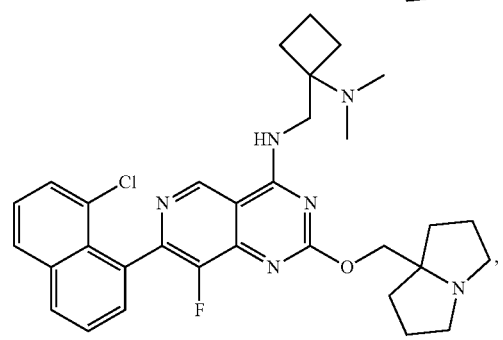
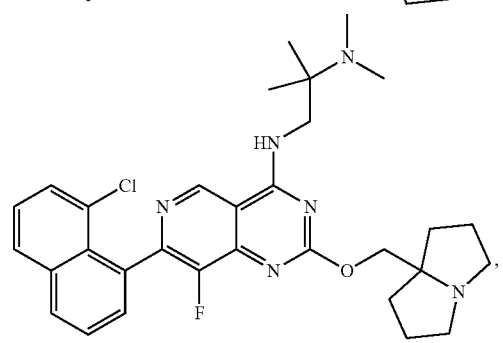
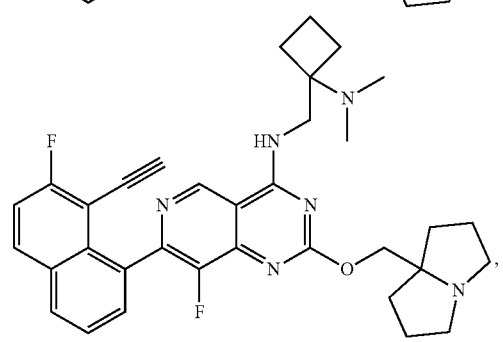
54
-continued
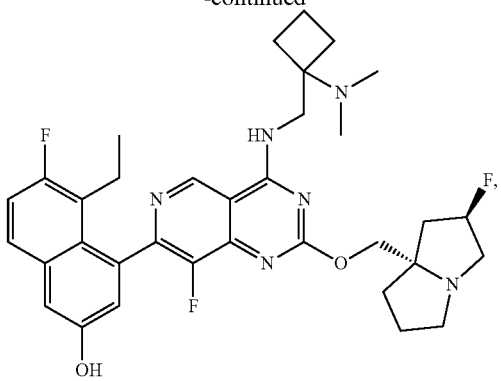
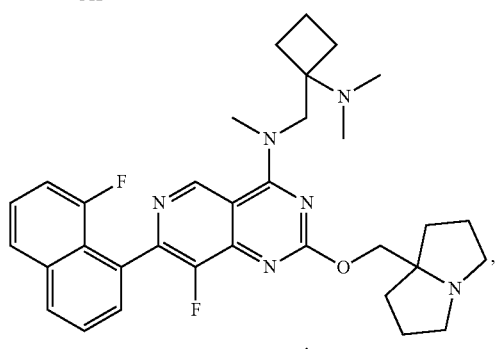
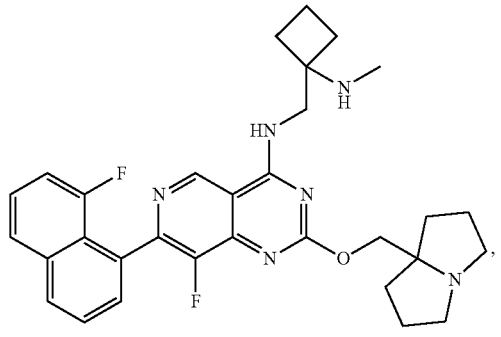
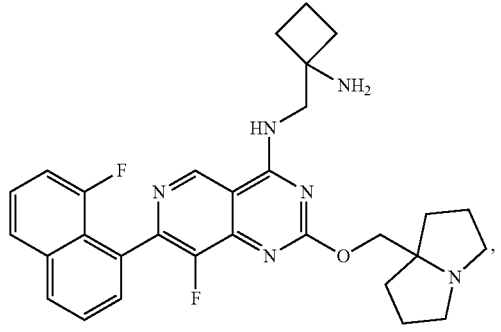
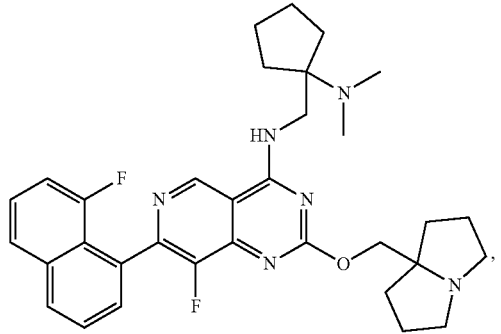

-continued

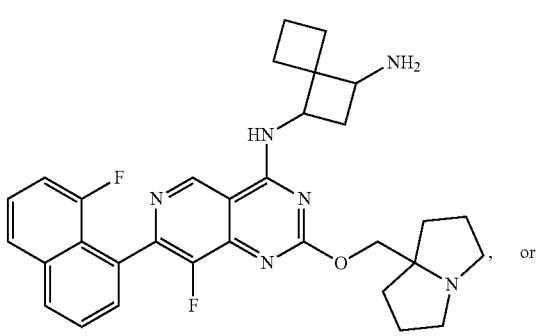

, or

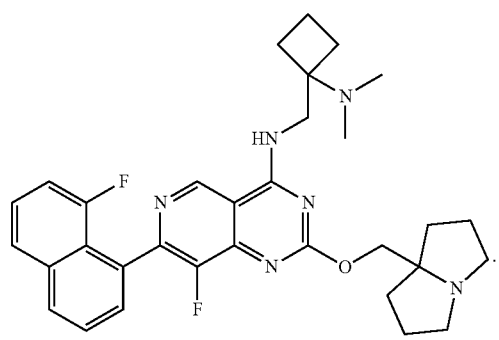

.

In some embodiments, the KRAS G12D binding moiety has the following structural formula:

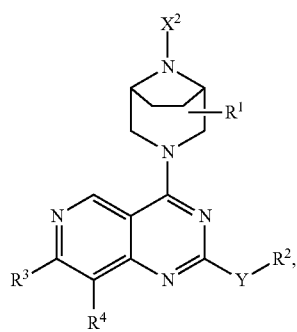

wherein:
X² is hydrogen, —C(O)—O—C(H)(R⁹)—O—C(O)—Z, —C(O)—O—(C₆-C₁₄)aryl, or —C(O)(C₁-C₆)alkyl;
Y is a bond, O or NR⁵;
Z is —(CH₂)₀₋₂₀—CH₃ or (C₁-C₃)alkyl;
R¹ is hydrogen, hydroxy, halogen, (C₁-C₃)alkyl, (C₁-C₃)cyanoalkyl, (C₁-C₃)hydroxyalkyl, —C(O)H, —CO₂R⁵, —CO₂N(R⁵)₂ or (C₅-C₆)heteroaryl;
R² is hydrogen, —N(R⁵)₂, (C₃-C₁₂)heterocyclyl, (C₁-C₆)alkyl, -L-(C₃-C₁₂)heterocyclyl, -L-(C₆-C₁₄)aryl, -L-(C₅-C₁₄)heteroaryl, -L-(C₃-C₁₂)cycloalkyl, -L-N(R⁵)₂, -L-N(H)C(NH)NH₂, -L-C(O)N(R⁵)₂, -L-(C₁-C₆)haloalkyl, -L-OR⁵, -L-(CH₂OR⁵)(CH₂)₁₋₃OR⁵, -L-NR⁵C(O)—(C₆-C₁₄)aryl, -L-COOH or -L-C(O)O(C₁-C₆)alkyl, wherein the (C₃-C₁₂)heterocyclyl, the (C₆-C₁₄)aryl of -L-NR⁵C(O)—(C₆-C₁₄)aryl, the (C₃-C₁₂)heterocyclyl of -L-(C₃-C₁₂)heterocyclyl and the (C₃-C₁₂)cycloalkyl of -L-(C₃-C₁₂)cycloalkyl are optionally substituted with one or more R⁶, and the aryl of -L-(C₆-C₁₄)aryl and (C₅-C₁₄)heteroaryl of -L-(C₅-C₁₄)heteroaryl are optionally substituted with one or more R⁷;
each L is independently (C₁-C₄)alkylene optionally substituted with hydroxy, (C₁-C₄)hydroxyalkyl (C₅-C₁₄)heteroaryl or 1-2 deuterium;
R³ is (C₆-C₁₄)aryl or (C₅-C₁₄)heteroaryl, wherein the (C₆-C₁₄)aryl or (C₅-C₁₄)heteroaryl is optionally substituted with one or more R⁸;
R⁴ is hydrogen, halogen or (C₁-C₃)alkyl;
each R⁵ is independently hydrogen or (C₁-C₃)alkyl;
each R⁶ is independently halogen, hydroxy, (C₁-C₃)hydroxyalkyl, (C₁-C₃)alkyl, (C₁-C₃)haloalkyl, (C₁-C₃)alkoxy, cyano, -Q-phenyl, -Q-phenyl-SO₂F, —N(H)C(O)-phenyl, —N(H)C(O)-phenyl-SO₂F, (C₁-C₃)alkyl-substituted pyrazole, (C₆-C₁₄)aryl(C₁-C₃)alkyl, tert-butyldimethylsilyloxy-CH₂—, —N(R⁵)₂, (C₁-C₃)alkoxy(C₁-C₃)alkyl, (C₁-C₃)alkyl-C(O)—, oxo, (C₁-C₃)haloalkyl-C(O)—, —SO₂F, (C₁-C₃)alkoxy(C₁-C₃)alkoxy, —CH₂OC(O)N(R⁵)₂, —CH₂N(H)C(O)O—(C₁-C₆)alkyl, —CH₂N(H)C(O)N(R⁵)₂, —CH₂N(H)C(O)(C₁-C₆)alkyl, —CH₂(pyrazolyl), —CH₂N(H)S(O)₂(C₁-C₆)alkyl, —CH₂OC(O)(C₃-C₁₂)heterocyclyl, —OC(O)N(R⁵)₂, —OC(O)N(H)(C₁-C₃)alkyl-O—(C₁-C₃)alkyl, —OC(O)N(H)(C₁-C₃)alkyl-O—(C₁-C₃)alkyl-phenyl-(C₁-C₃)alkyl-N(CH₃)₂, —OC(O)N(H)(C₁-C₃)alkyl-O—(C₁-C₃)alkyl-phenyl, —OC(O)(C₃-C₁₂)heterocyclyl, —CH₂—(C₃-C₁₂)heterocyclyl or deuterium, wherein the phenyl of —N(H)C(O)phenyl and —OC(O)N(H)(C₁-C₃)alkyl-O—(C₁-C₃)alkyl-phenyl is optionally substituted with —C(O)H or —OH, and the (C₃-C₁₂)heterocyclyl of —CH₂—(C₃-C₁₂)heterocyclyl is optionally substituted with oxo;
Q is a bond or O;
each R⁷ is independently halogen, hydroxy, —C(O)H, (C₁-C₄)alkyl, (C₁-C₄)alkoxy, (C₁-C₄)haloalkyl, (C₁-C₄)hydroxyalkyl or —N(R⁵)₂;
each R⁸ is independently halogen, cyano, hydroxy, (C₁-C₄)alkyl, —S—(C₁-C₄)alkyl, (C₂-C₄)alkenyl, (C₂-C₄)alkynyl, (C₂-C₄)hydroxyalkynyl, (C₁-C₃)cyanoalkyl, triazolyl, (C₁-C₃)haloalkyl, —O—(C₁-C₃)haloalkyl, —S—(C₁-C₃)haloalkyl, (C₁-C₃)alkoxy, (C₁-C₃)hydroxyalkyl, —CH₂C(O)N(R⁵)₂, (C₃-C₄)alkynyl-N(R⁵)₂, N(R⁵)₂, deutero(C₂-C₄)alkynyl, (C₁-C₃)alkoxy(C₁-C₃)haloalkyl, —O—C(O)—Z, or (C₃-C₆)cycloalkyl, wherein the (C₃-C₆)cycloalkyl is optionally substituted with halogen or (C₁-C₃)alkyl; and
R⁹ is hydrogen or (C₁-C₃)alkyl.

Alternative values for the variables are as described in the first, second or third embodiment, or any aspect of the foregoing.

In some embodiments, the KRAS G12D binding moiety is

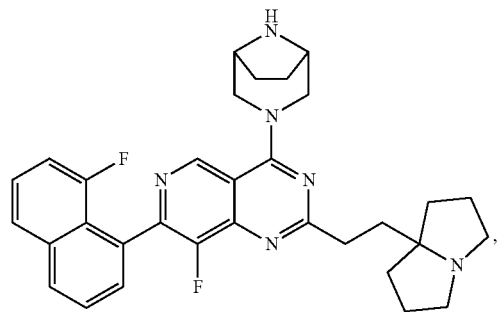
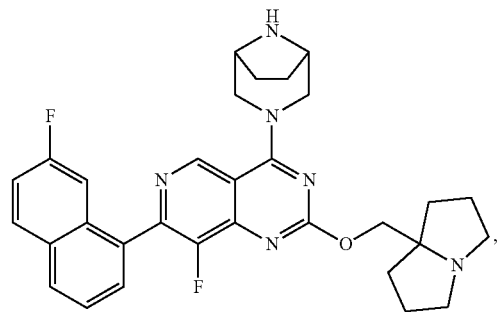
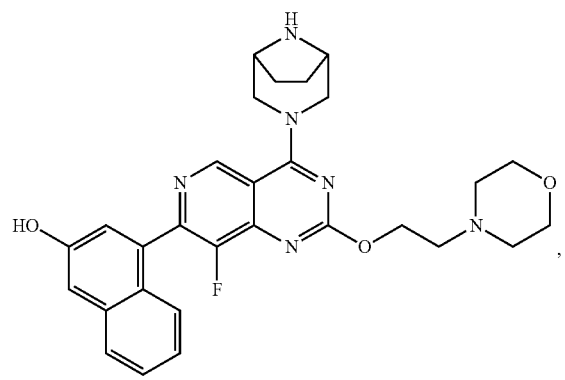
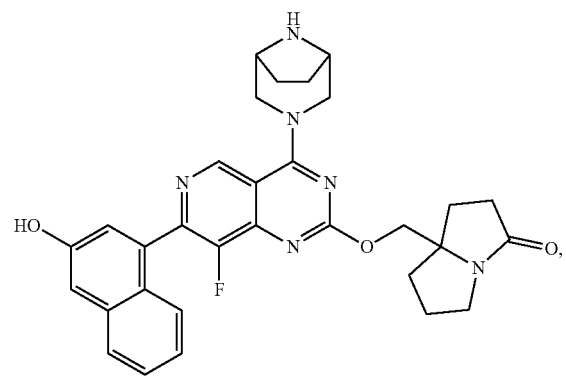
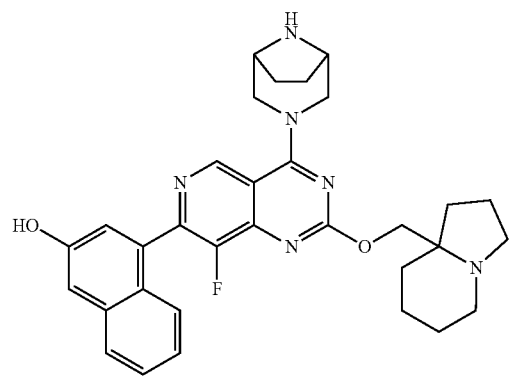
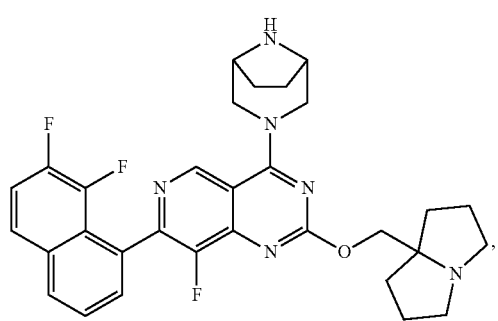
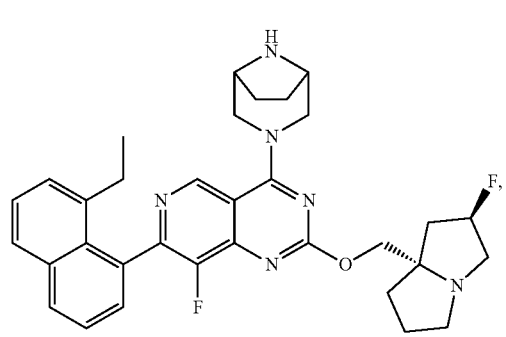
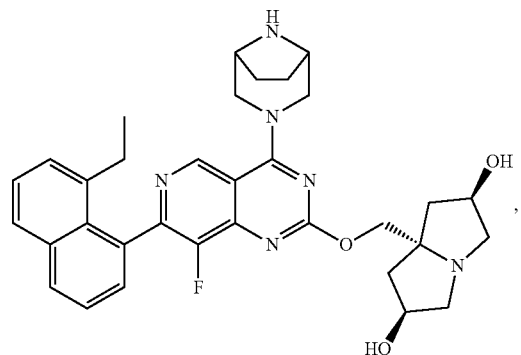

59
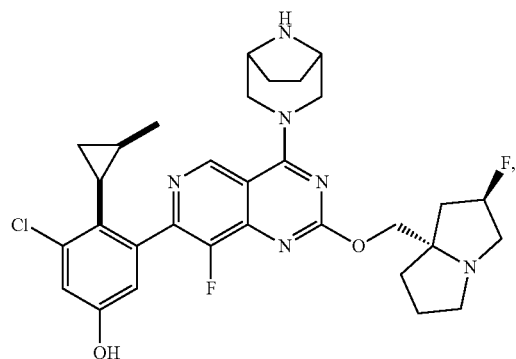
60
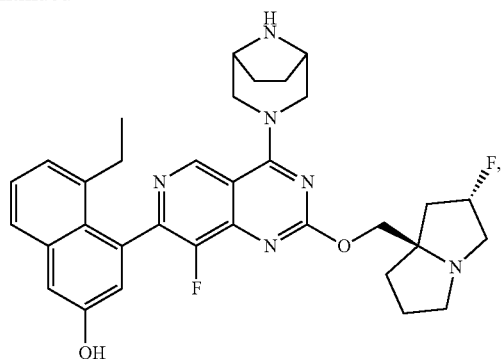
-continued
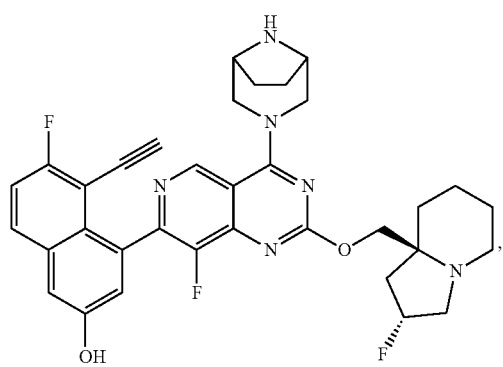
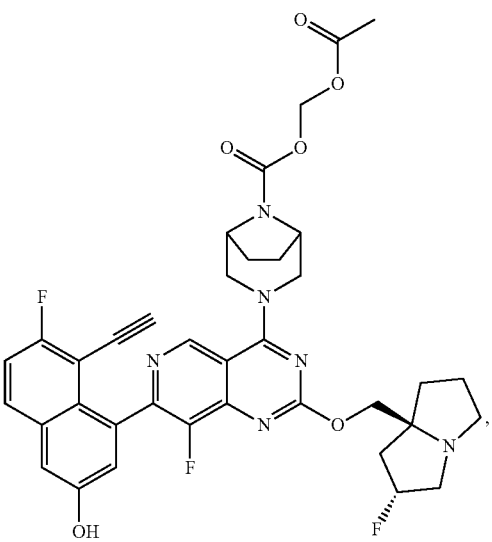
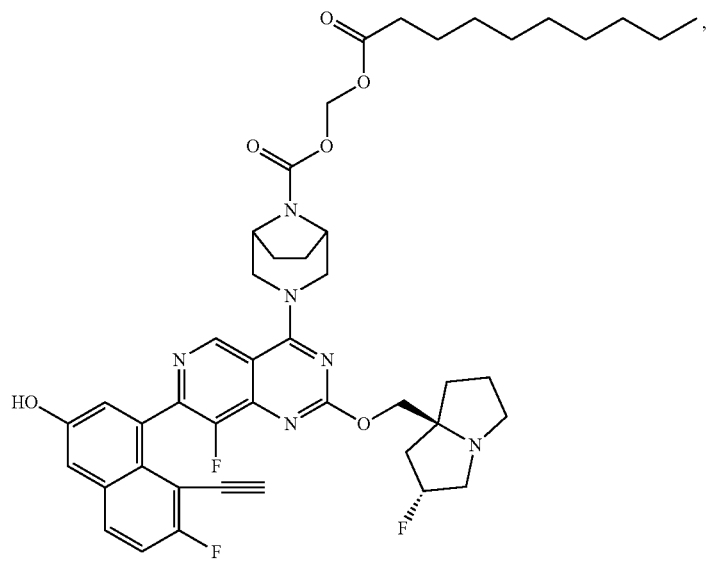

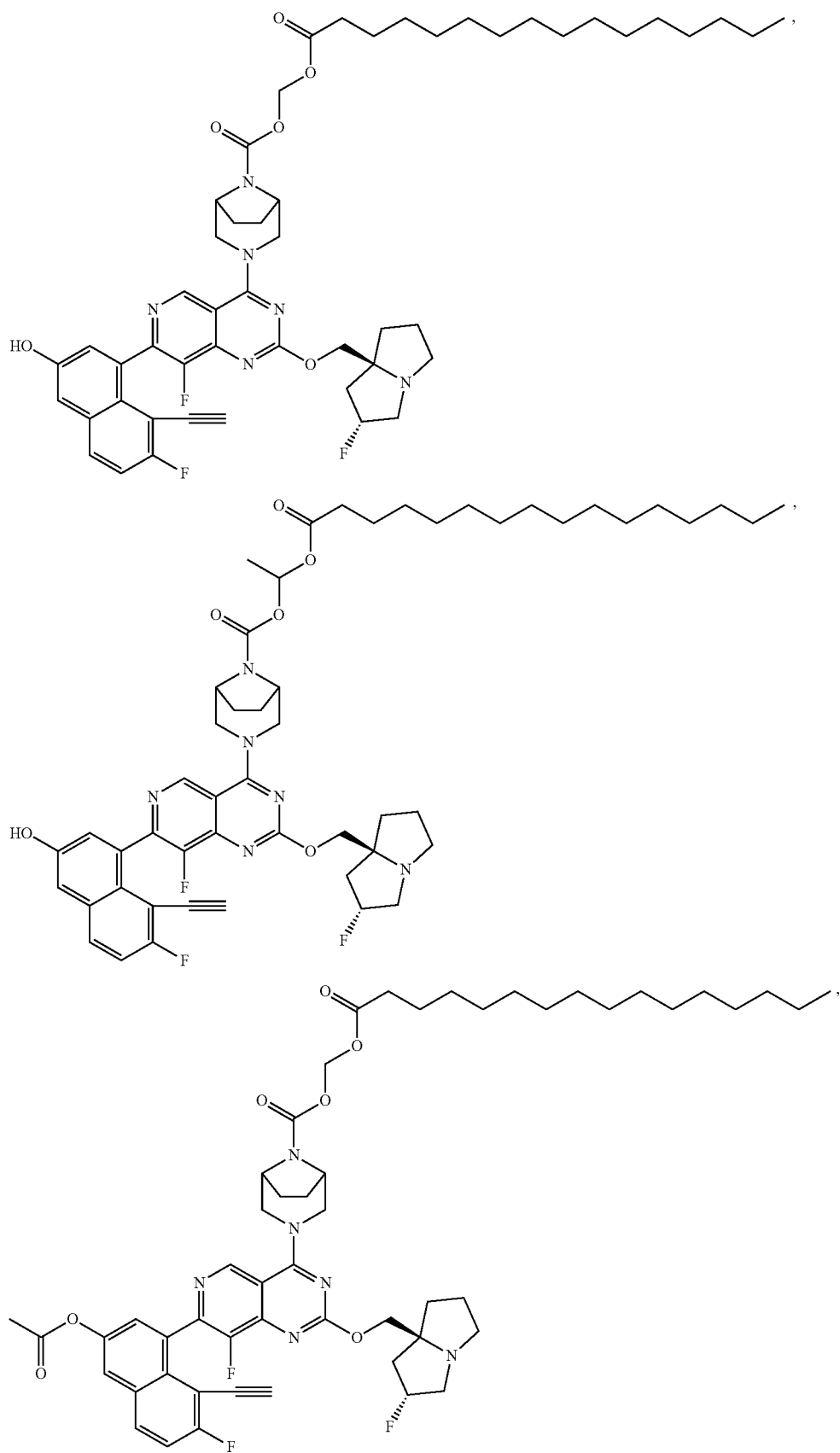

-continued

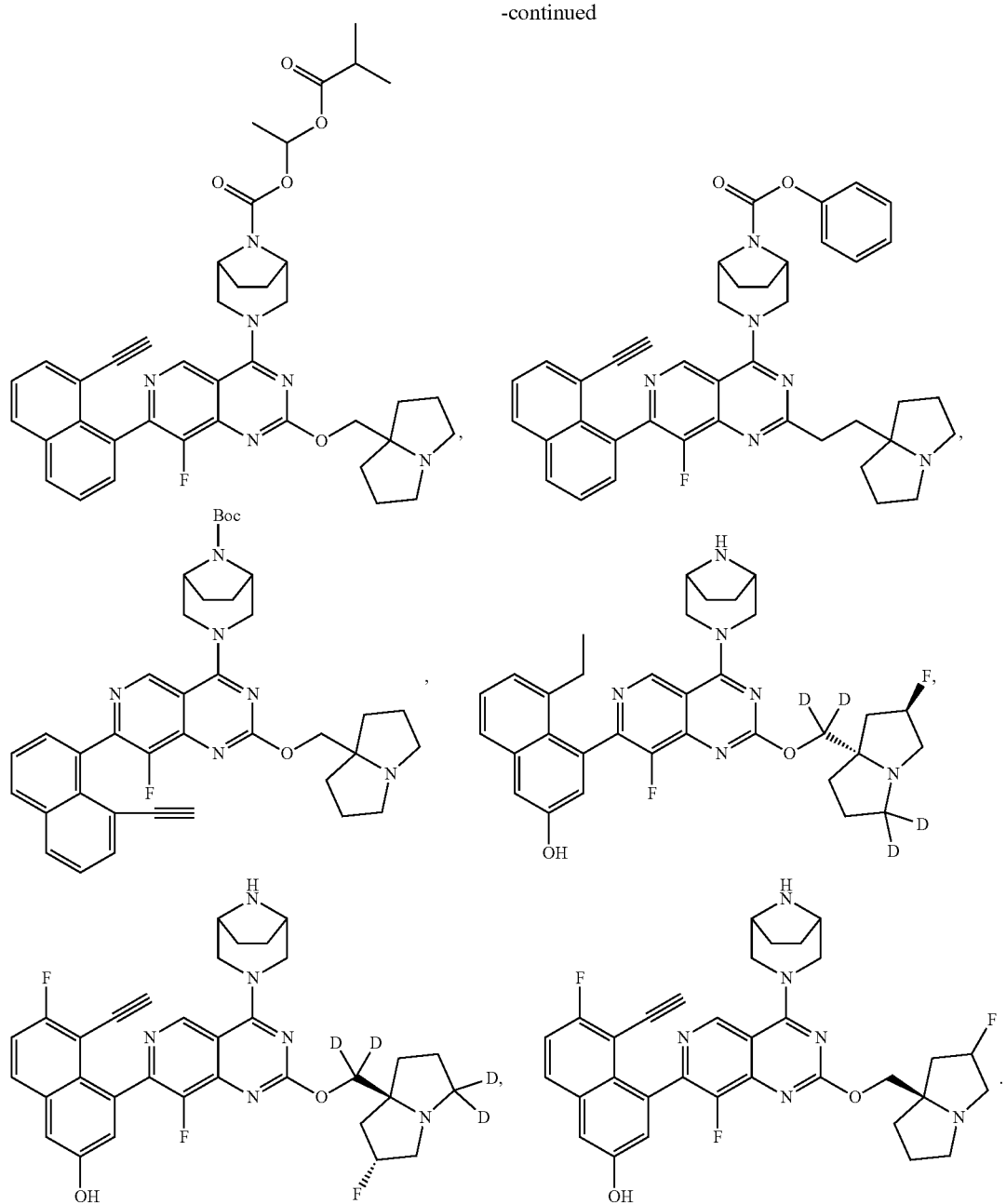

In some embodiments, the KRAS G12D binding moiety has the following structural formula:

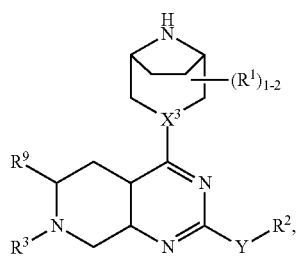

wherein:
$X^3$ is N or $CR^5$;
Y is a bond, O or $NR^5$;
Z is —$(CH_2)_{0-20}$—$CH_3$ or $(C_1$-$C_3)$alkyl;
each $R^1$ is independently hydrogen, hydroxy, halogen, $(C_1$-$C_3)$haloalkyl, $(C_1$-$C_3)$alkyl, $(C_1$-$C_3)$alkoxy, $(C_1$-$C_3)$alkoxy$(C_1$-$C_3)$alkyl, $(C_1$-$C_3)$alkyl-$N(R^5)_2$, cyano, $(C_1$-$C_3)$cyanoalkyl, $(C_2$-$C_4)$cyanoalkenyl, $(C_1$-$C_3)$hydroxyalkyl, —C(O)H, —$CO_2R^3$, or —$CO_2N(R^5)_2$;
$R^2$ is hydrogen, —$N(R^5)_2$, $(C_3$-$C_{12})$heterocyclyl, $(C_1$-$C_6)$alkyl, -L-$(C_3$-$C_{12})$heterocyclyl, -L-$(C_6$-$C_{14})$aryl, -L-$(C_5$-$C_{14})$heteroaryl, -L-$(C_3$-$C_{12})$cycloalkyl, -L-$N(R^5)_2$, -L-N(H)C(NH)$NH_2$, -L-C(O)$N(R^5)_2$, -L-$(C_1$-$C_6)$haloalkyl, -L-$OR^5$, -L-$(CH_2OR^5)(CH_2)_{1-3}OR^5$, -L-$NR^5$C (O)—(C$_6$-C$_{14}$)aryl, or -L-COOH, wherein the (C$_3$-C$_{12}$)heterocyclyl, the (C$_6$-C$_{14}$)aryl of -L-NR$^5$C(O)—(C$_6$-C$_{14}$)aryl, the (C$_3$-C$_{12}$)heterocyclyl of -L-(C$_3$-C$_{12}$)heterocyclyl and the (C$_3$-C$_{12}$)cycloalkyl of -L-(C$_3$-C$_{12}$)cycloalkyl are optionally substituted with one or more R$^6$, and the aryl of
-L-(C$_6$-C$_{14}$)aryl and (C$_5$-C$_{14}$)heteroaryl of -L-(C$_5$-C$_{14}$)heteroaryl are optionally substituted with one or more R$^7$;
each L is independently (C$_1$-C$_4$)alkylene optionally substituted with hydroxy, (C$_1$-C$_4$)hydroxyalkyl or (C$_5$-C$_{14}$)heteroaryl;
R$^3$ is -L-(C$_6$-C$_{14}$)aryl, (C$_6$-C$_{14}$)aryl, -L-(C$_5$-C$_{14}$)heteroaryl or (C$_5$-C$_{14}$)heteroaryl, wherein the (C$_6$-C$_{14}$)aryl or (C$_5$-C$_{14}$)heteroaryl is optionally substituted with one or more R$^8$;
each R$^5$ is independently hydrogen, (C$_1$-C$_3$)alkyl or (C$_1$-C$_3$)hydroxyalkyl, or two R$^5$ together with the atom to which they are both attached join to form a (C$_3$-C$_{12}$)heterocyclyl, wherein the (C$_3$-C$_{12}$)heterocyclyl formed by two R$^5$ is optionally substituted with one or more substituents independently selected from (C$_1$-C$_3$)alkyl, hydroxy or (C$_1$-C$_3$)alkoxy;
each R$^6$ is independently halogen, hydroxy, (C$_1$-C$_3$)hydroxyalkyl, (C$_1$-C$_3$)alkyl, (C$_1$-C$_3$)haloalkyl, (C$_1$-C$_3$)alkoxy, -Q-phenyl, -Q-phenyl-SO$_2$F, —N(H)C(O)-phenyl, —N(H)C(O)-phenyl-SO$_2$F, (C$_1$-C$_3$)alkyl-substituted pyrazole, (C$_6$-C$_{14}$)aryl(C$_1$-C$_3$)alkyl, tert-butyldimethylsilyloxy-CH$_2$—, —N(R$^5$)$_2$, (C$_1$-C$_3$)alkoxy(C$_1$-C$_3$)alkyl, (C$_1$-C$_3$)alkyl-C(O)—, oxo, (C$_1$-C$_3$)haloalkyl-C(O)—, —SO$_2$F, (C$_1$-C$_3$)alkoxy(C$_1$-C$_3$)alkoxy, —(C$_1$-C$_3$)alkyl-OC(O)N(R$^5$)$_2$, or —(C$_1$-C$_3$)alkyl-OC(O)N(OR$^5$)R$^5$;
Q is a bond or O;
each R$^7$ is independently halogen, hydroxy, —C(O)H, (C$_1$-C$_4$)alkyl, (C$_1$-C$_4$)alkoxy, (C$_1$-C$_4$)haloalkyl, (C$_1$-C$_4$)hydroxyalkyl or —N(R$^5$)$_2$;
each R$^8$ is independently halogen, cyano, hydroxy, (C$_1$-C$_4$)alkyl, —S—(C$_1$-C$_4$)alkyl, (C$_2$-C$_4$)alkenyl, (C$_2$-C$_4$)alkynyl, (C$_2$-C$_4$)hydroxyalkynyl, (C$_1$-C$_3$)cyanoalkyl, triazolyl, (C$_1$-C$_3$)haloalkyl, —O—(C$_1$-C$_3$)haloalkyl, cyclopropyl, N(R$^5$)$_2$, (C$_1$-C$_4$)hydroxyalkyl, —S—(C$_1$-C$_3$)haloalkyl or (C$_1$-C$_3$)alkoxy; and
R$^9$ is hydrogen or oxo.
Alternative values for the variables are as described in the first, second or third embodiment, or any aspect of the foregoing.

In some embodiments, the KRAS G12D binding moiety is

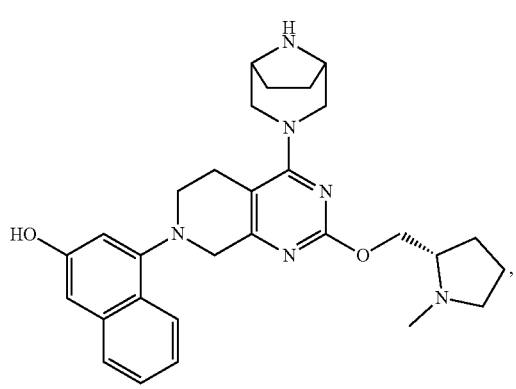

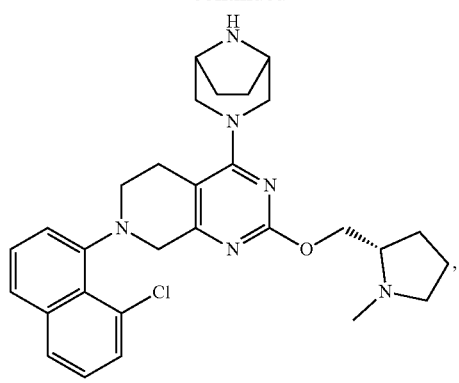

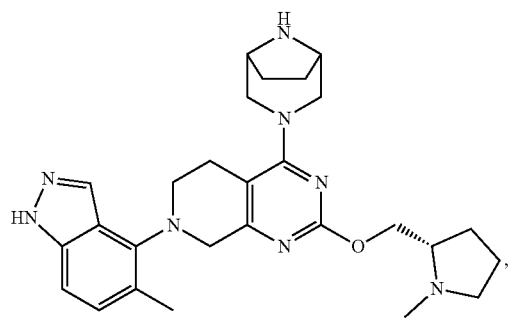

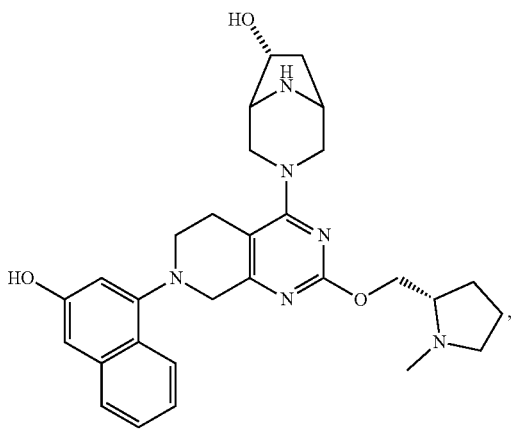

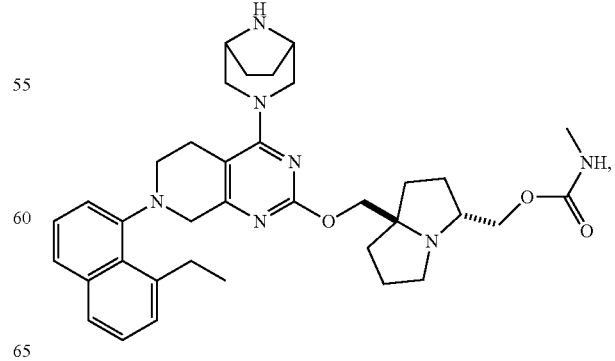

67
-continued
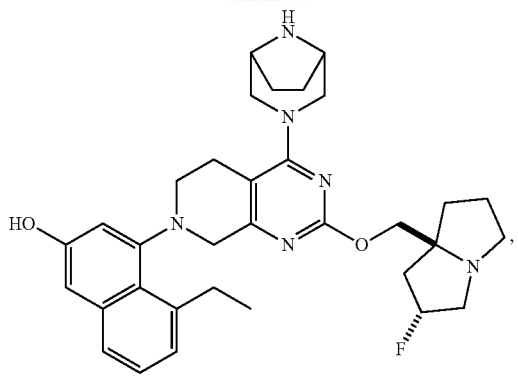
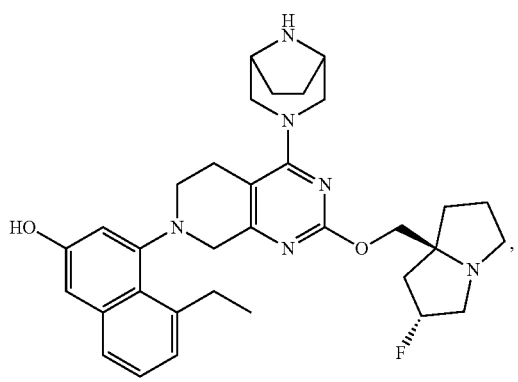
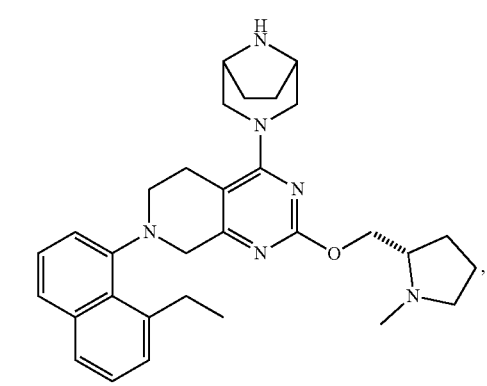
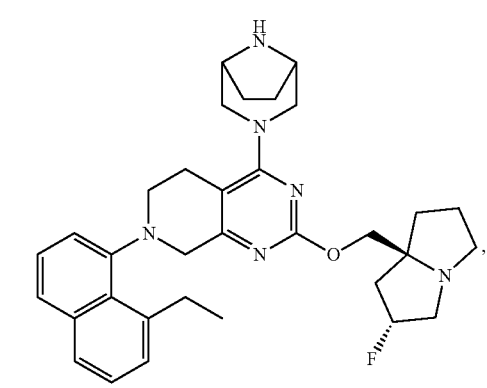
68
-continued
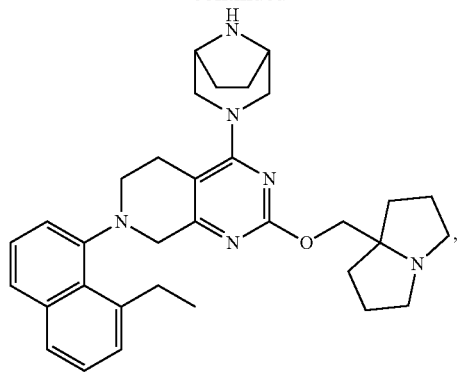
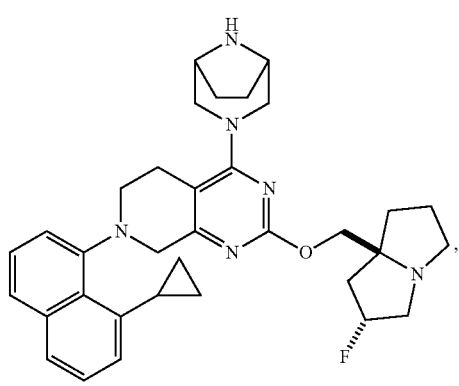
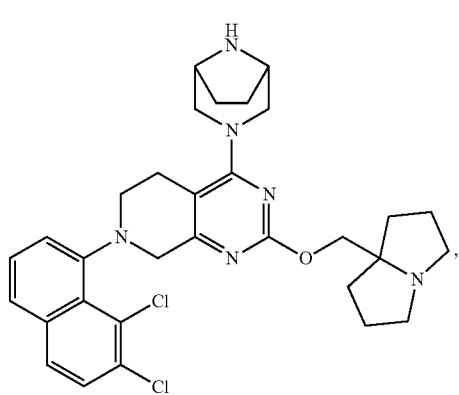
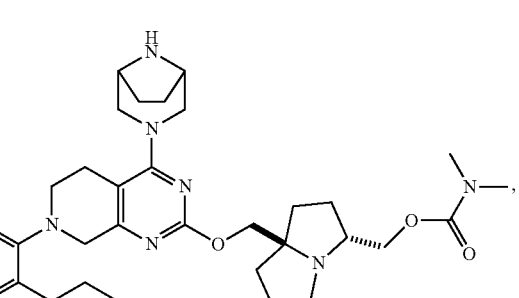

69
-continued
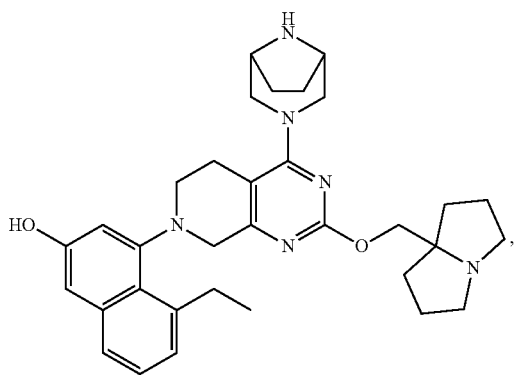
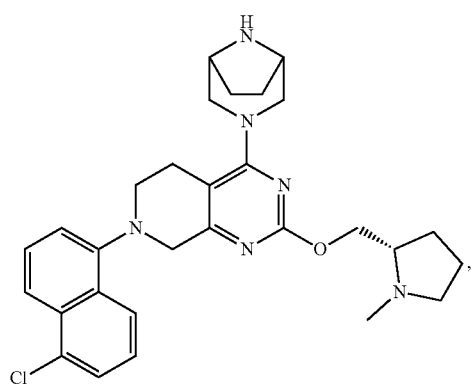
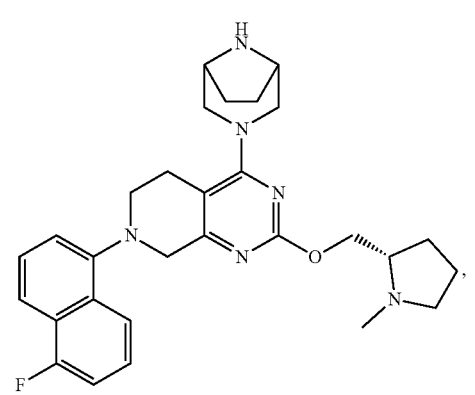
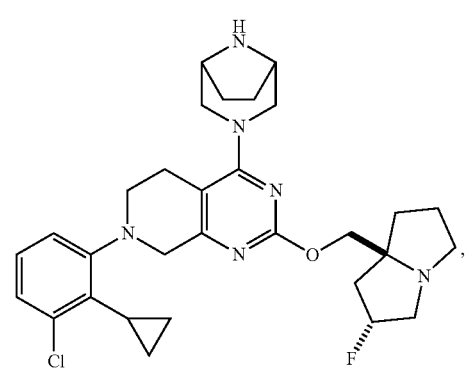
70
-continued
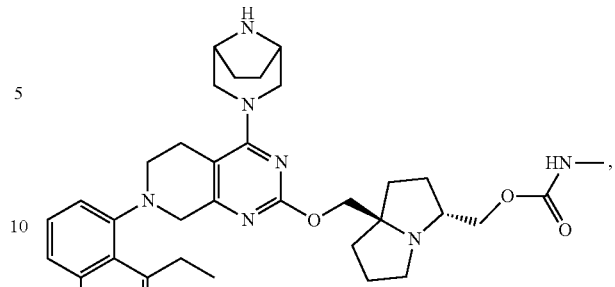
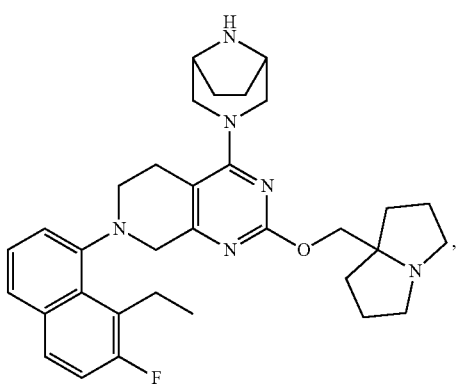
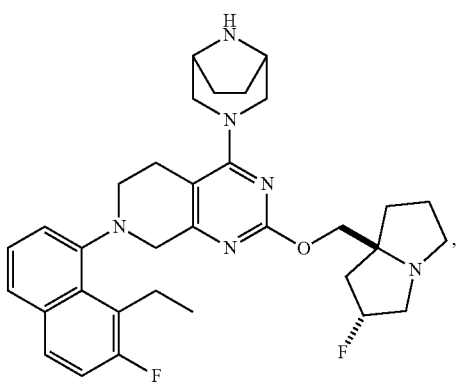
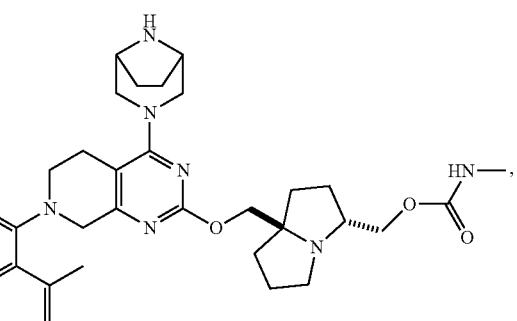

71
-continued
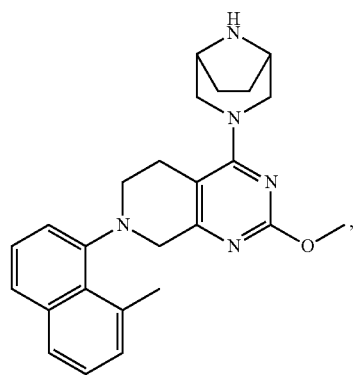
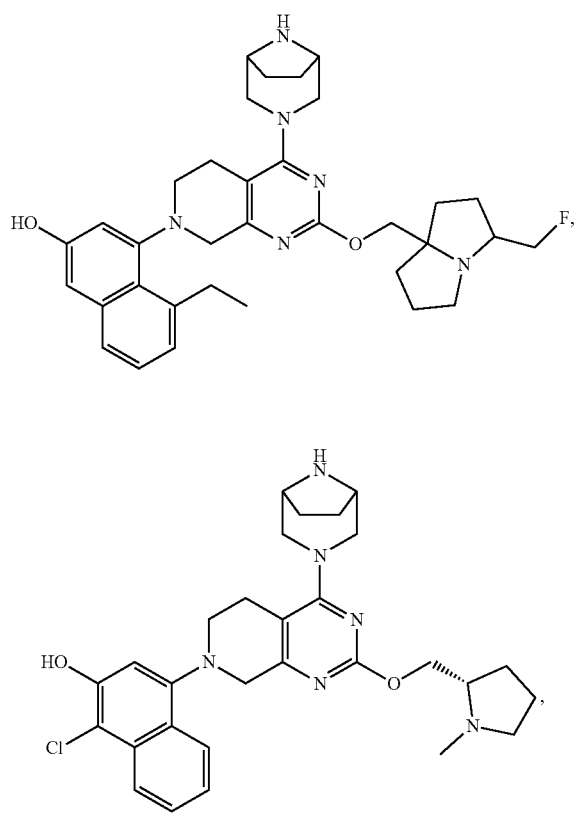
72
-continued
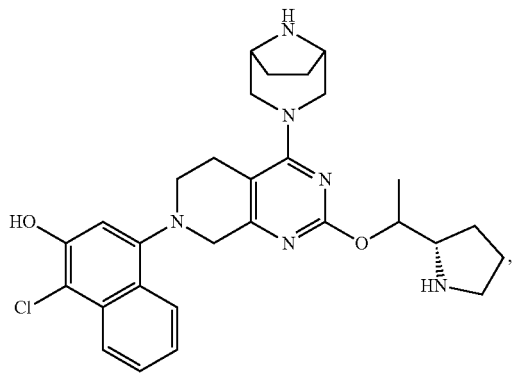
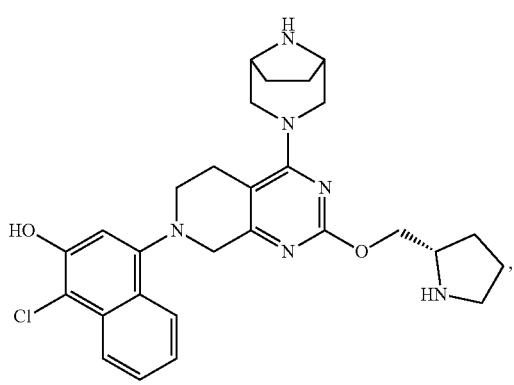
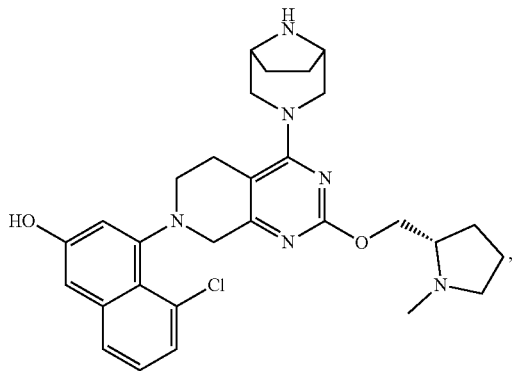
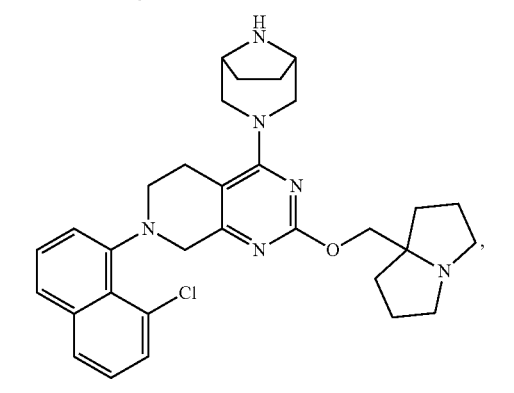

73
-continued
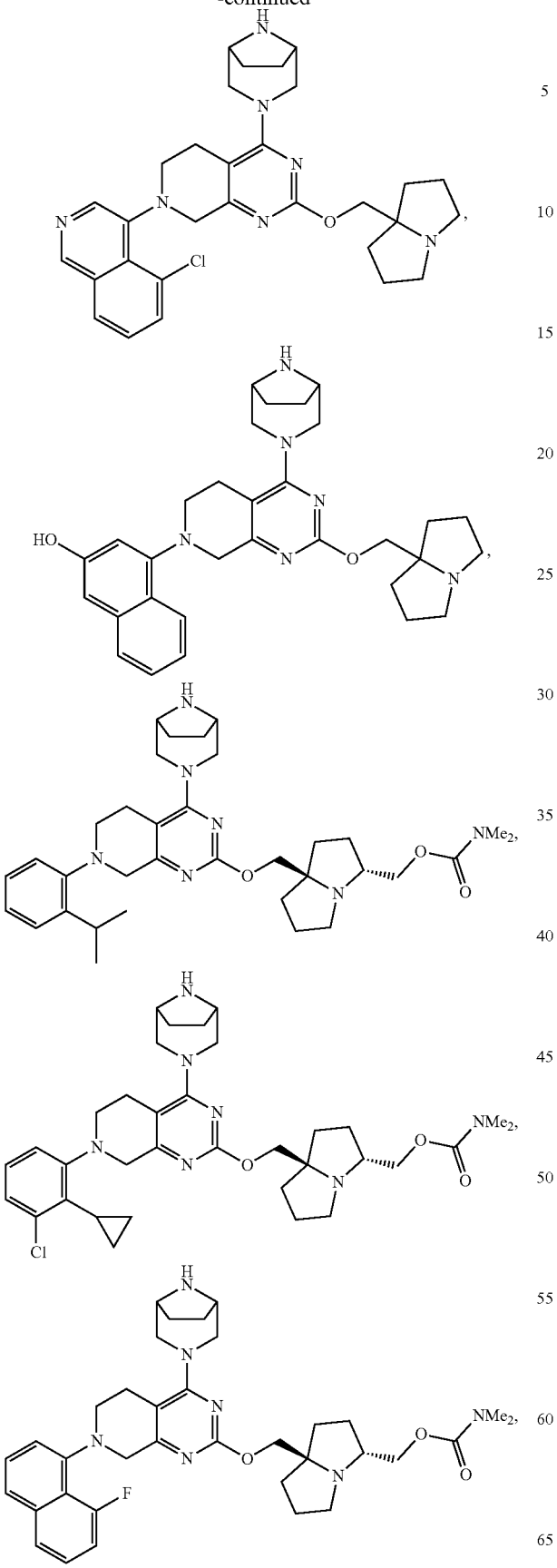
74
-continued
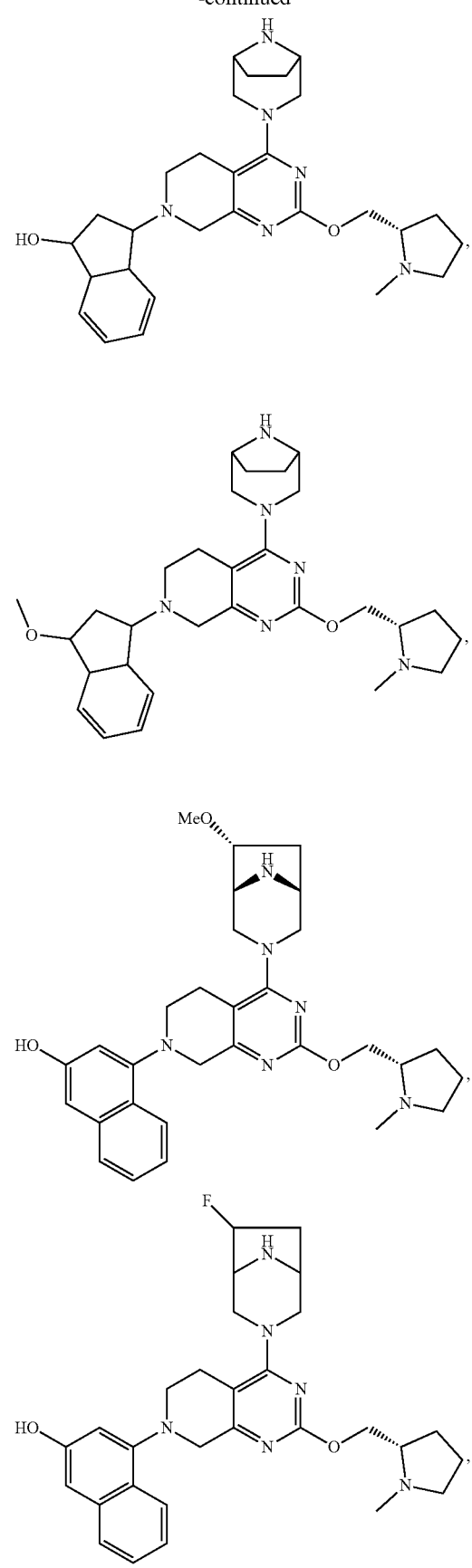

75
-continued
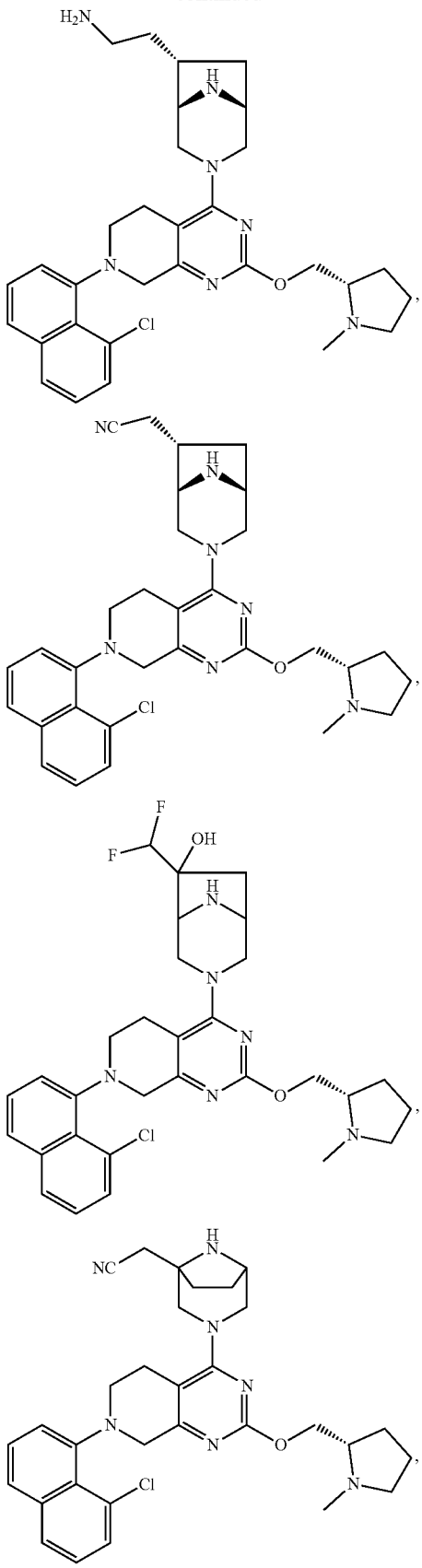
76
-continued
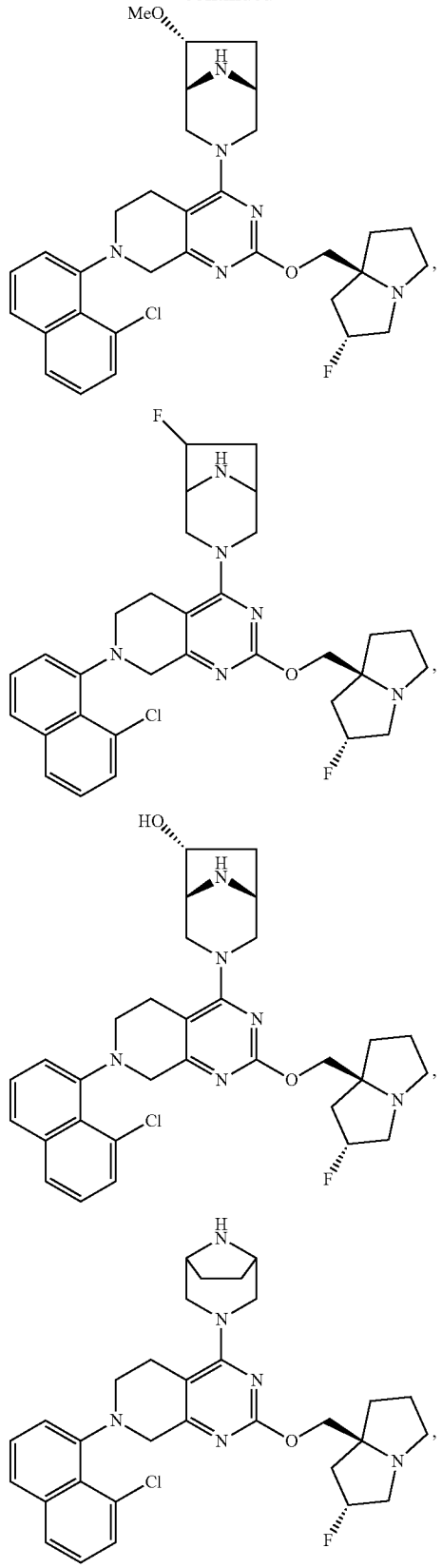

77
-continued
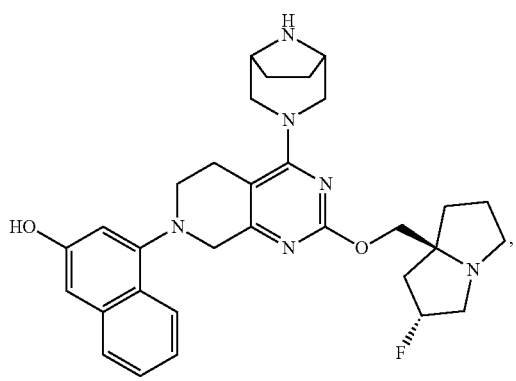
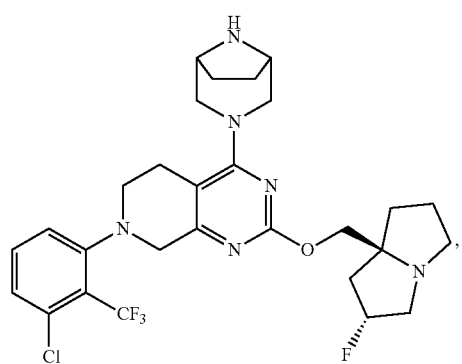
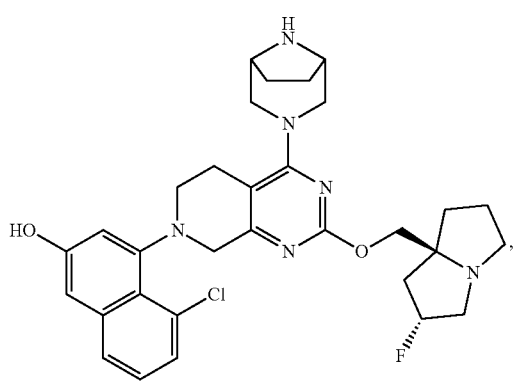
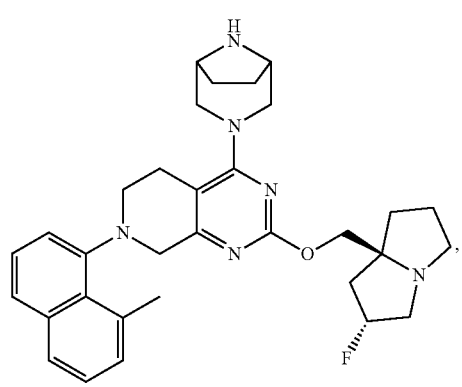
78
-continued
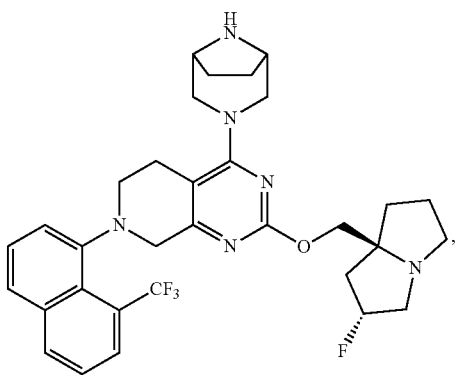
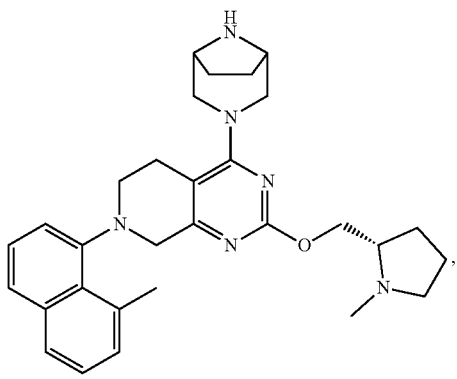
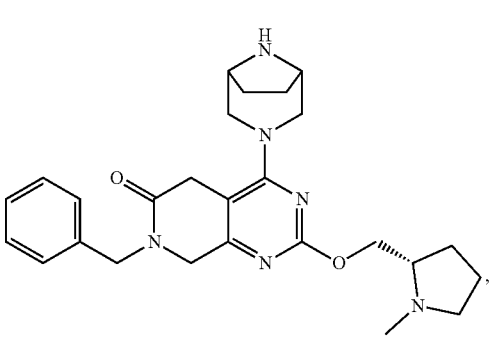
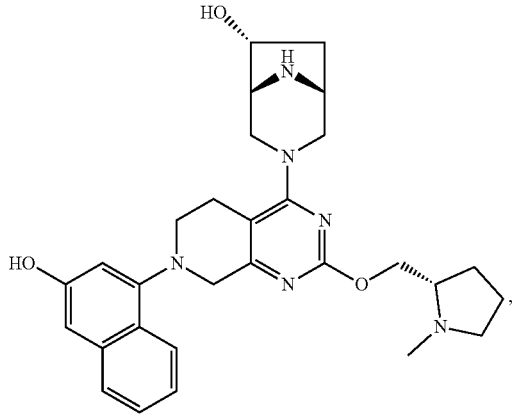

79
-continued
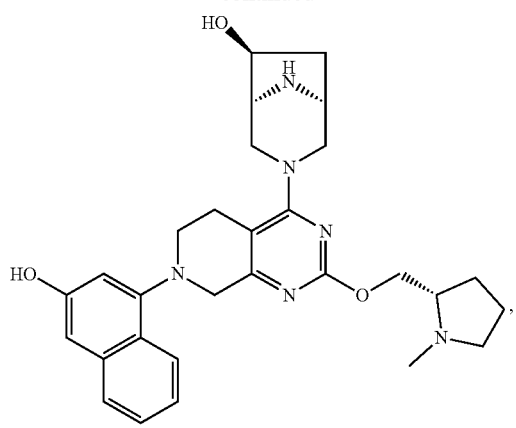
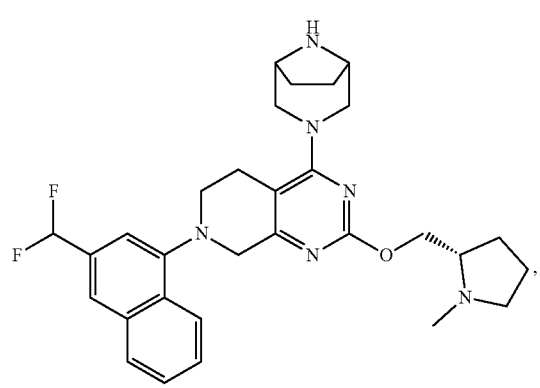
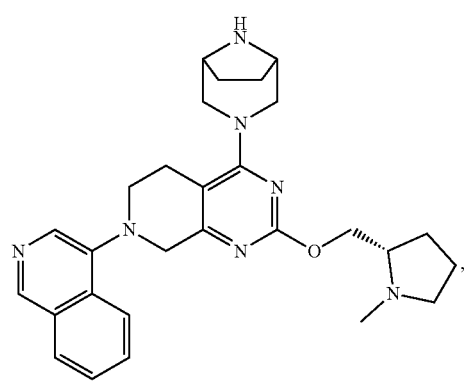
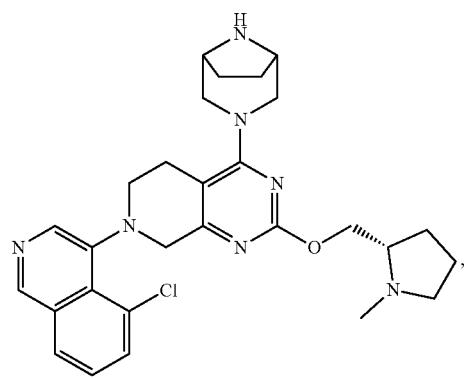
80
-continued
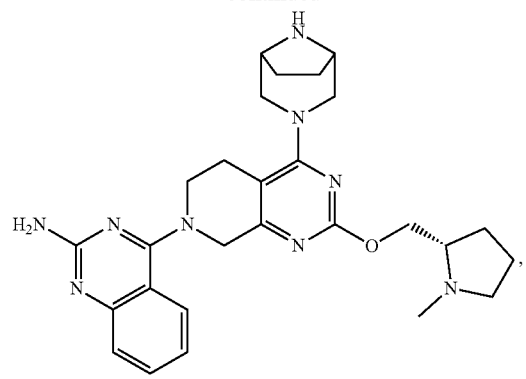
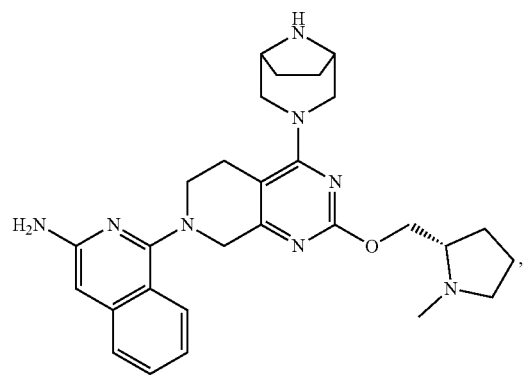
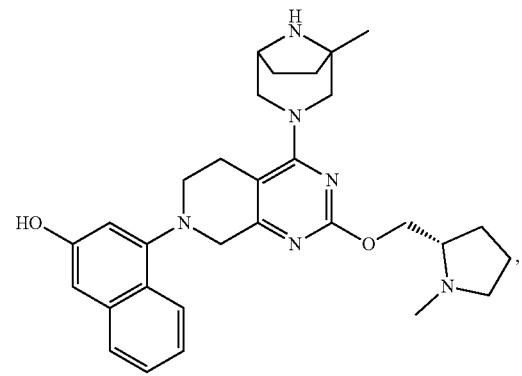
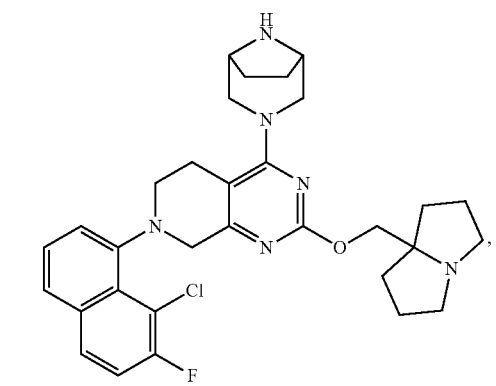

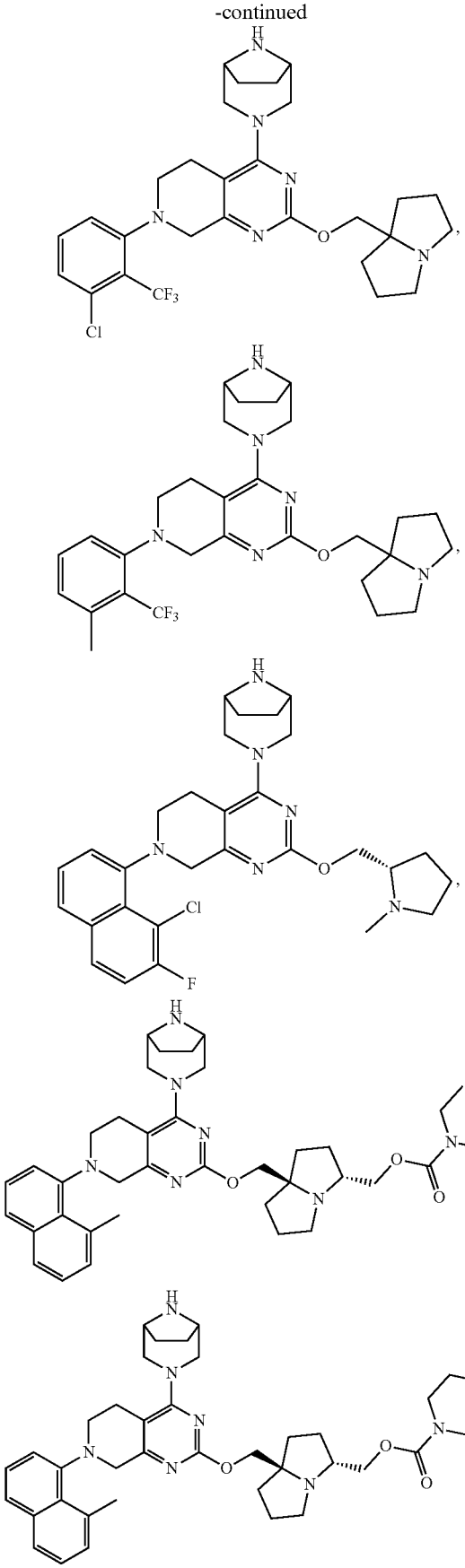
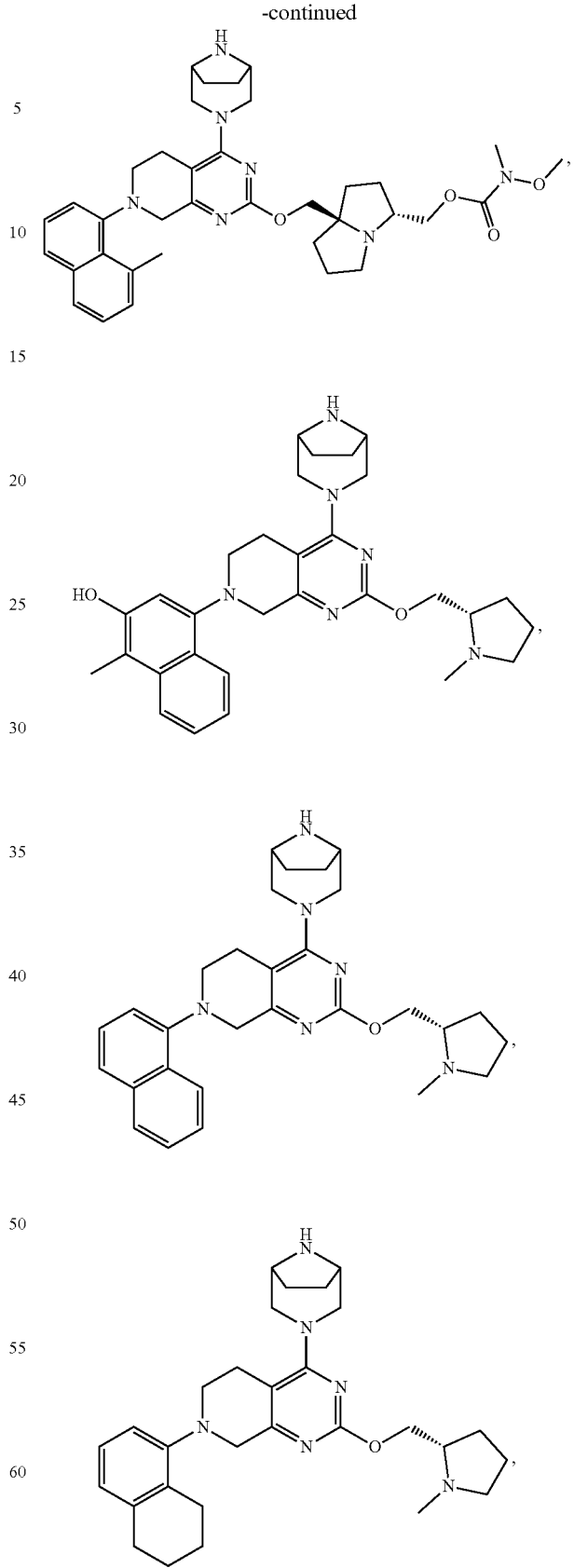

83
-continued
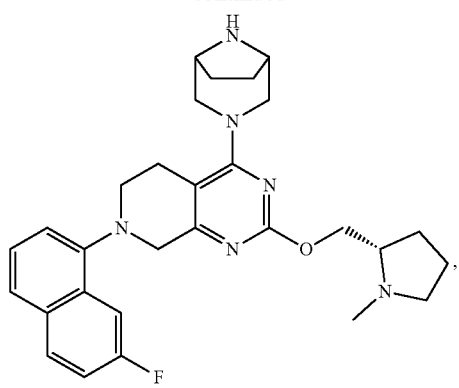
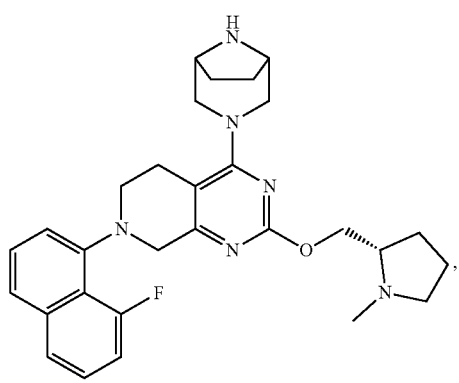
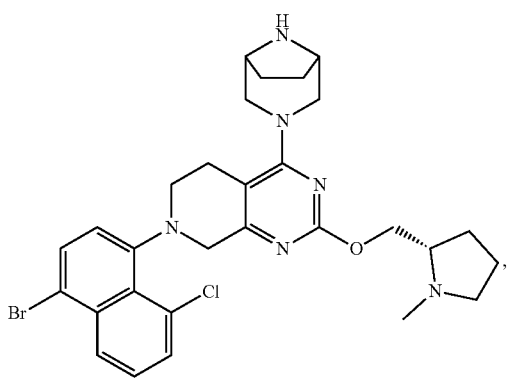
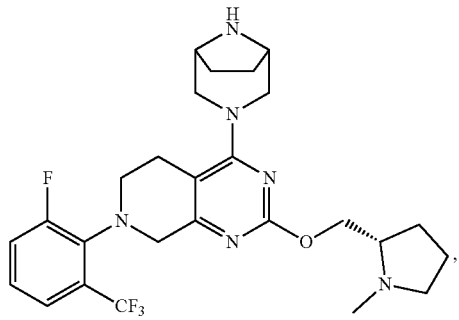
84
-continued
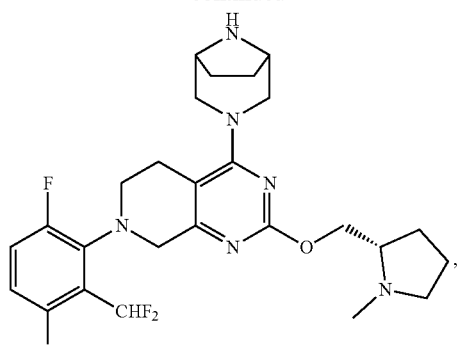
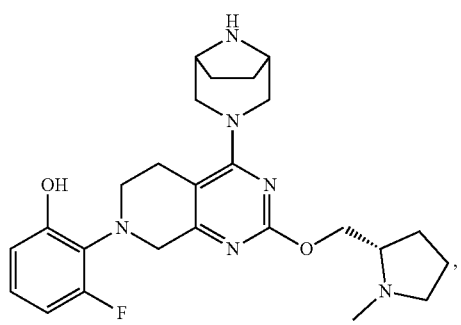
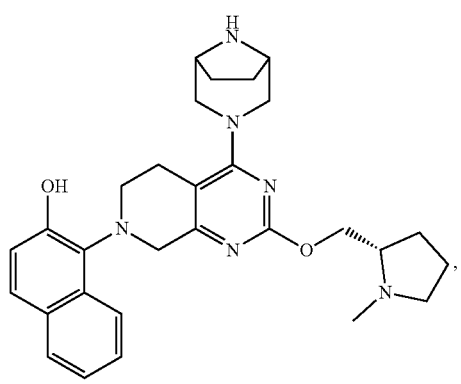
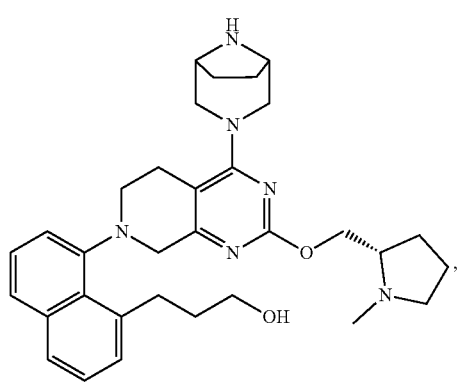

85
-continued
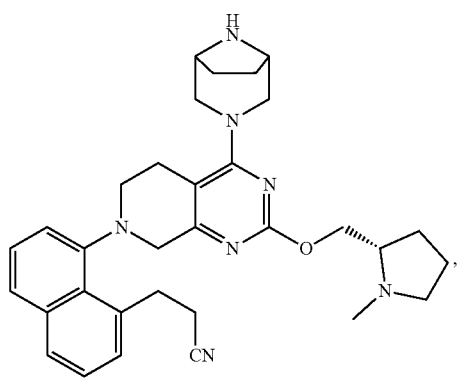
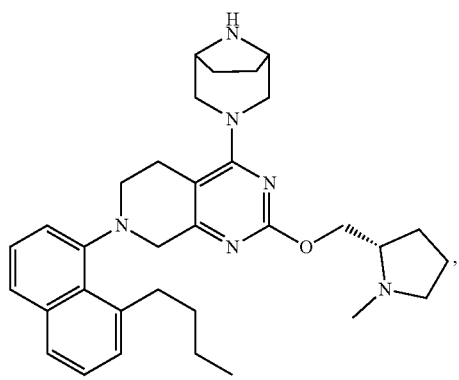
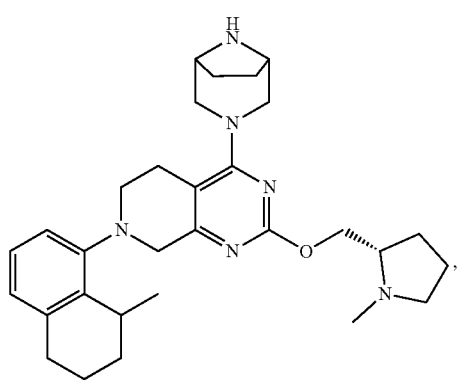
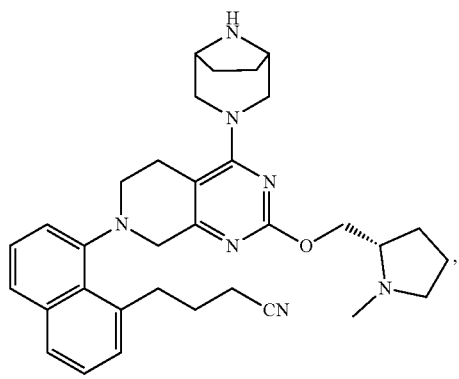
86
-continued
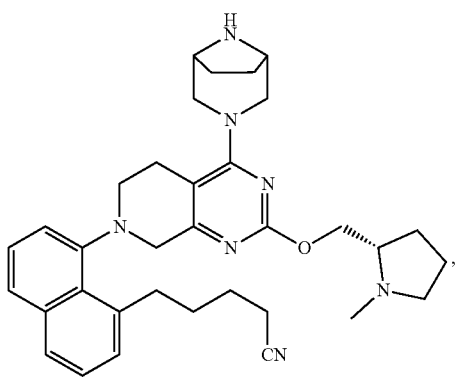
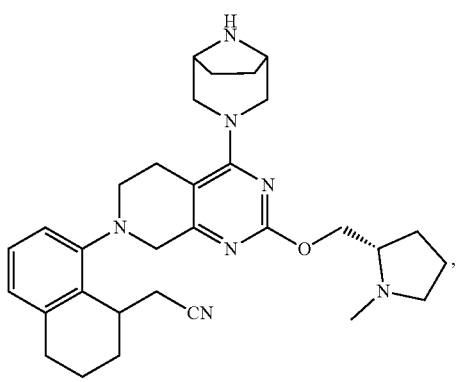
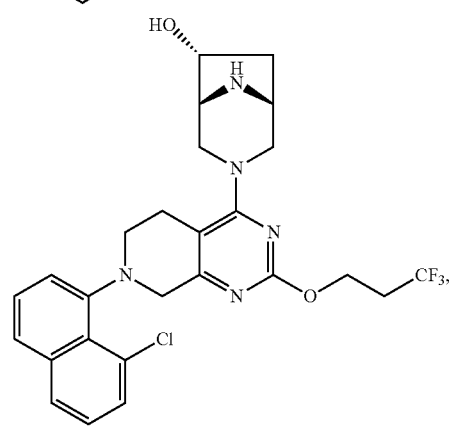
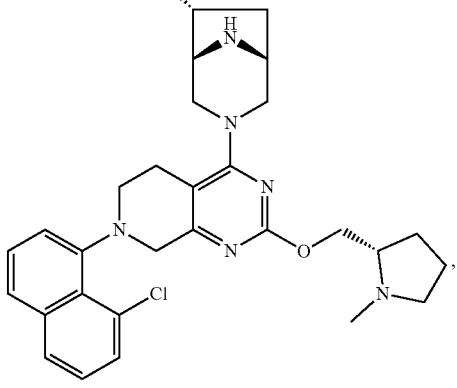

87
-continued
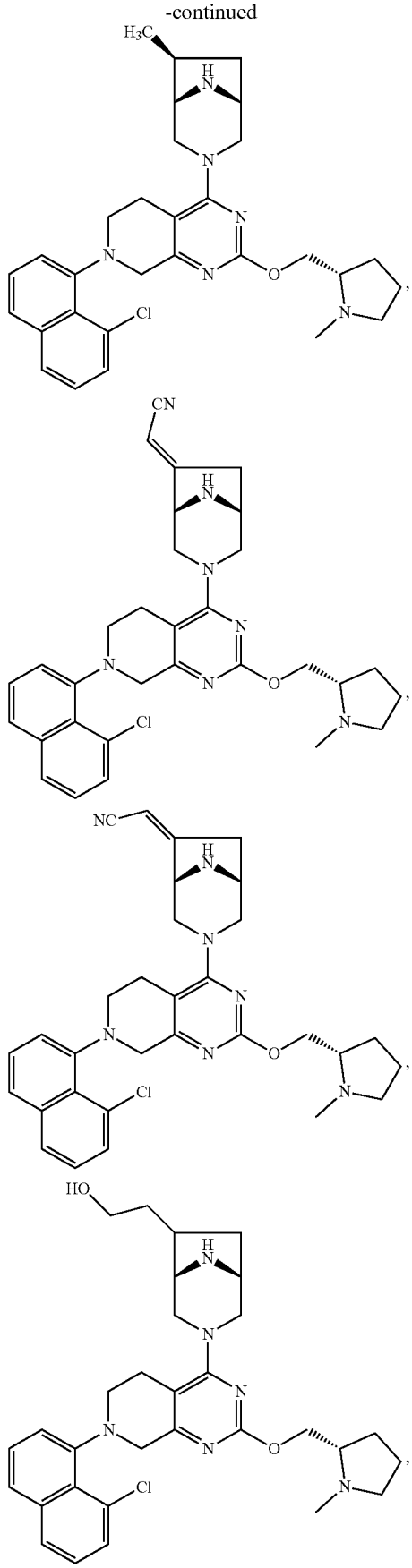
88
-continued
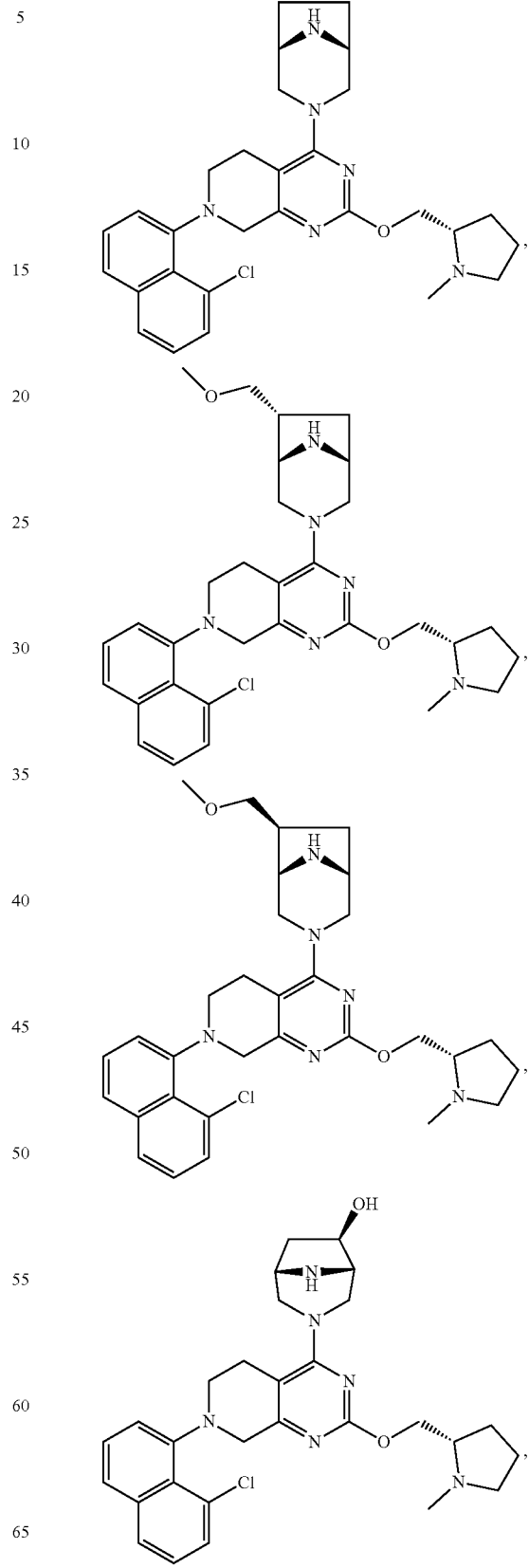

89
-continued
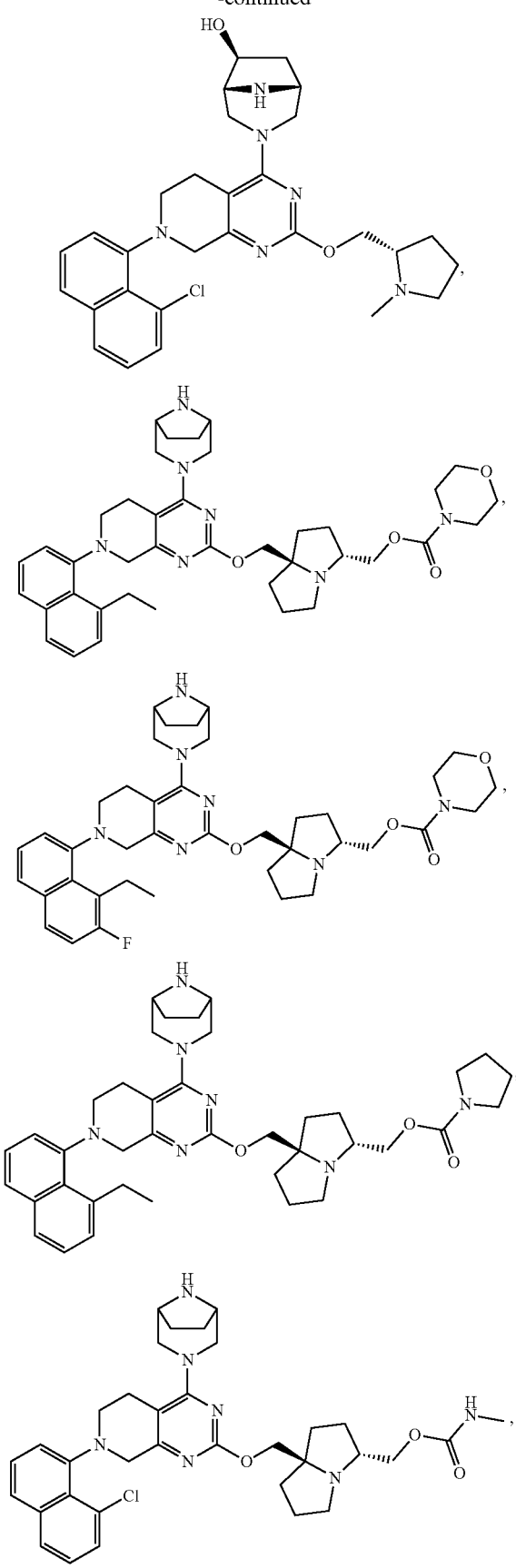
90
-continued
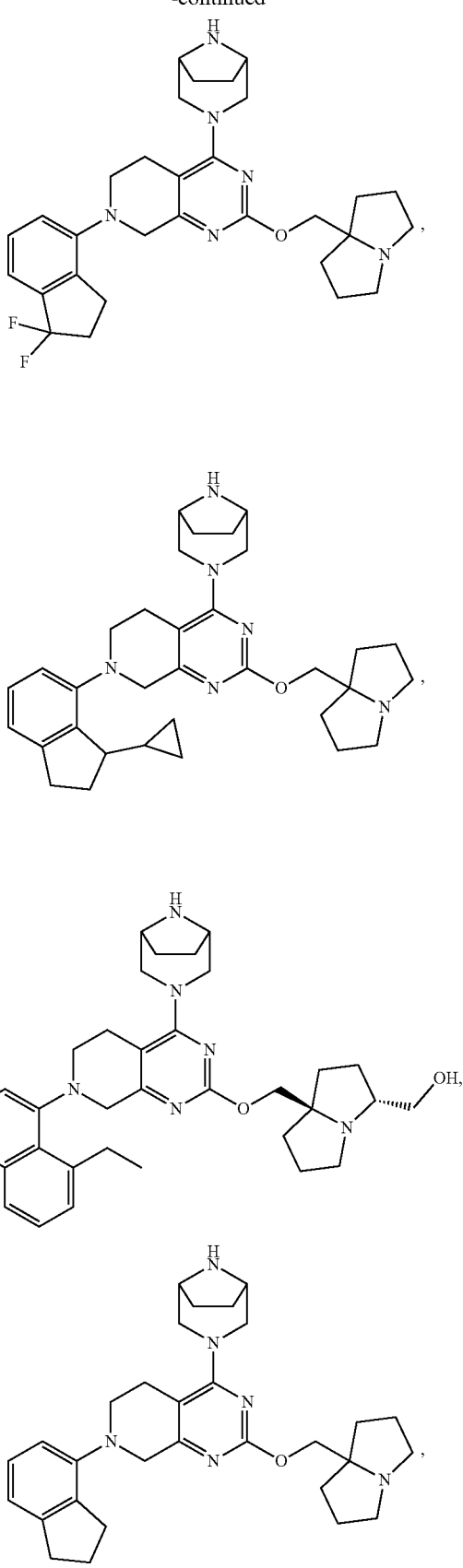

91
-continued
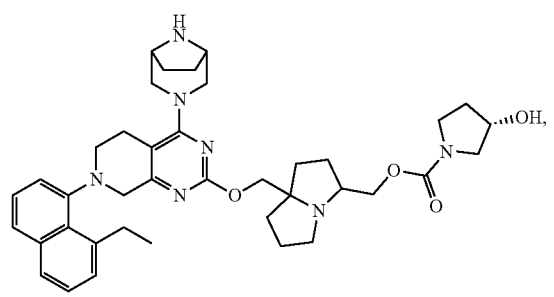
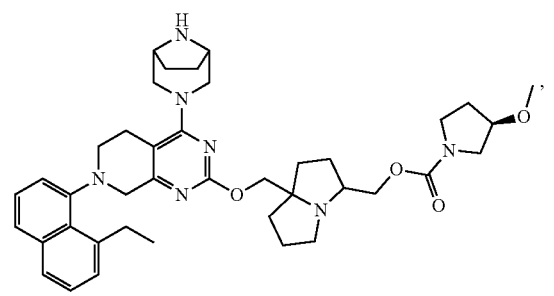
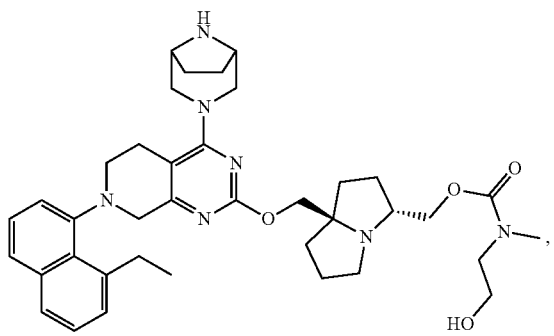
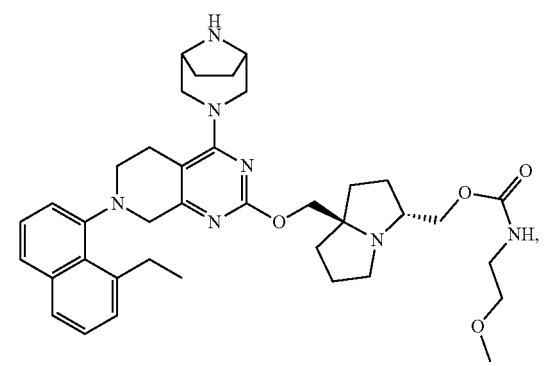
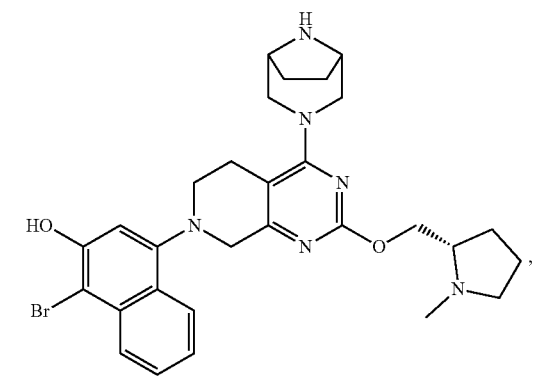
92
-continued
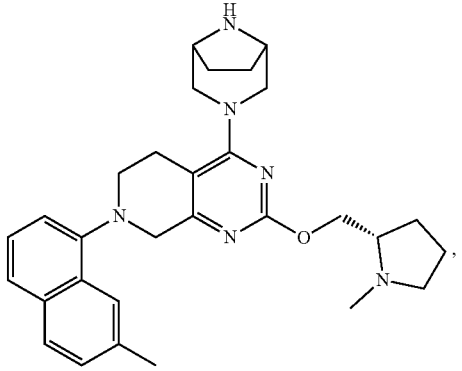
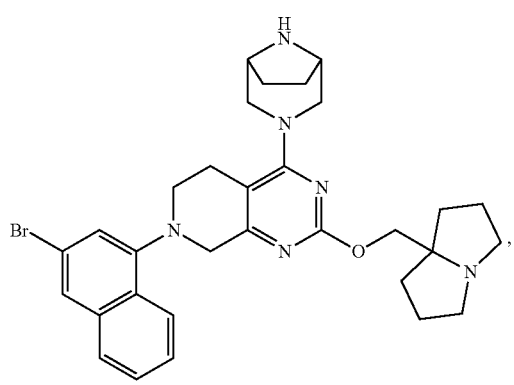
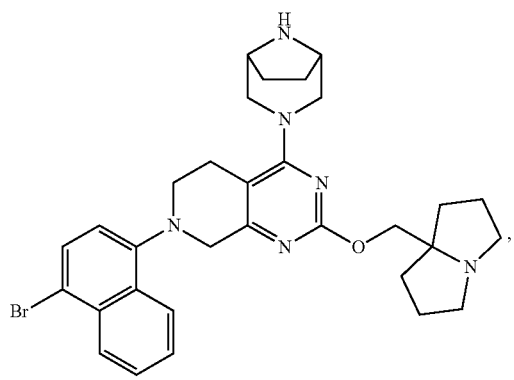
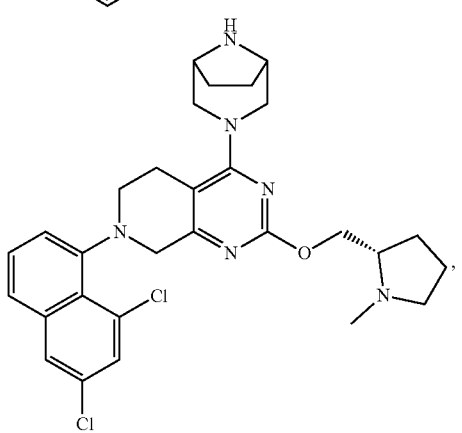

93
-continued
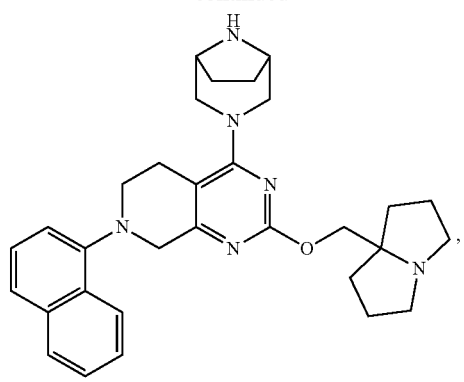
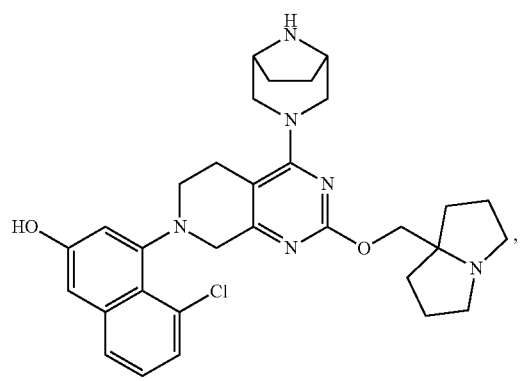
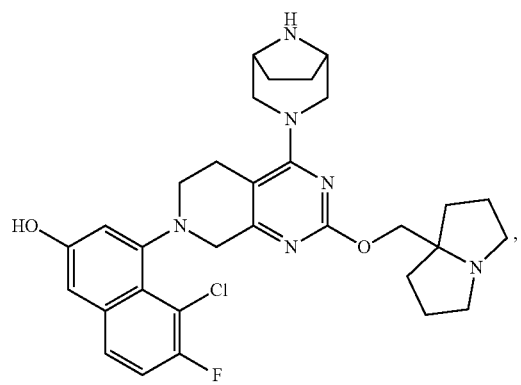
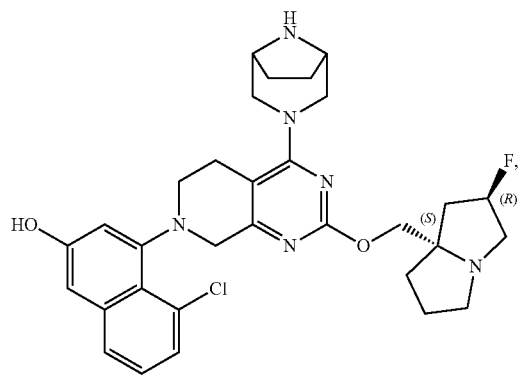
94
-continued
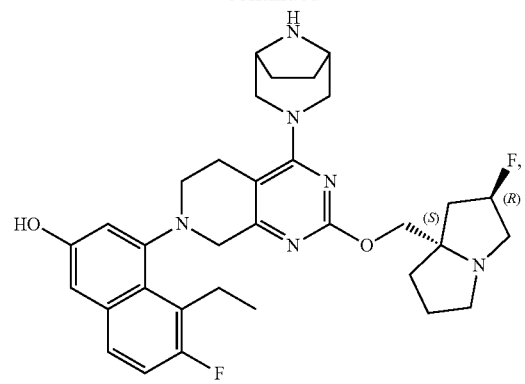
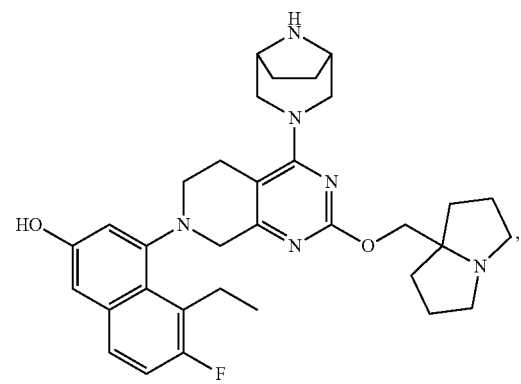
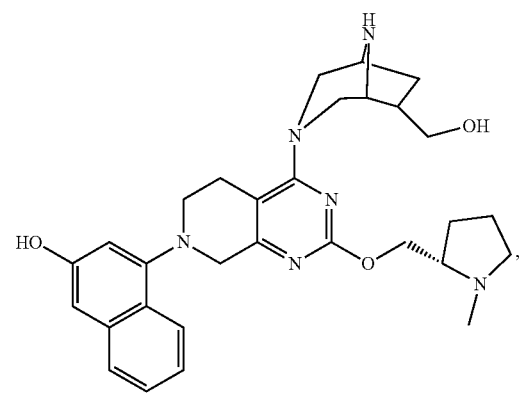
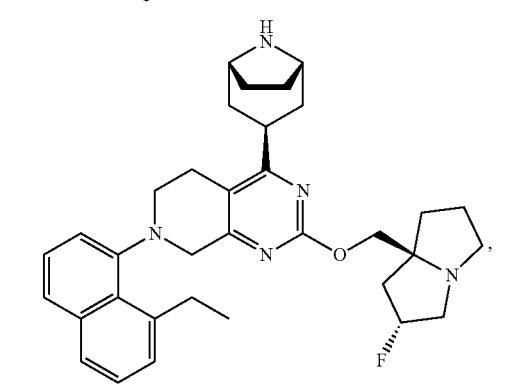

-continued

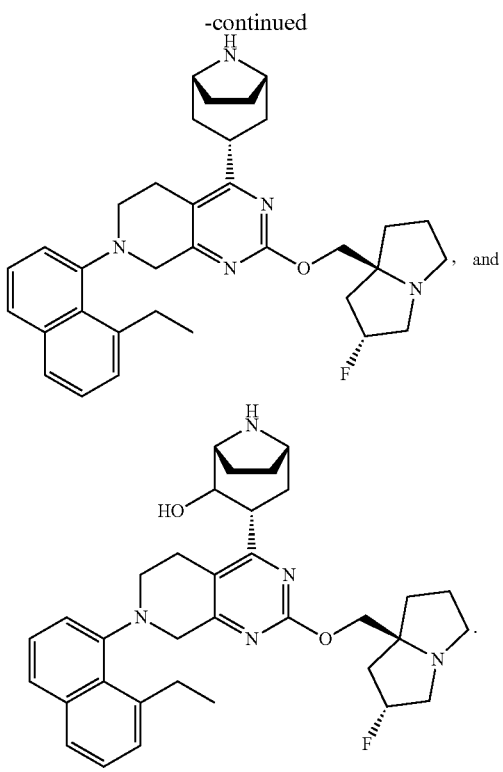

, and

In some embodiments, the KRAS G12D binding moiety has the following structural formula:

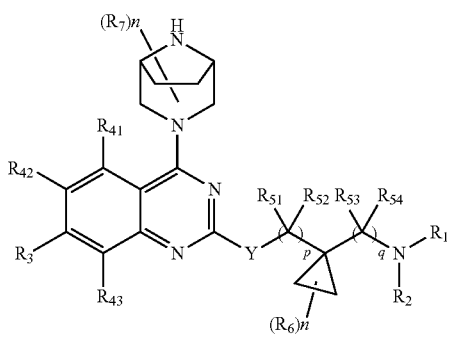

wherein:

Y is selected from a bond, O, NR$_{55}$, S, S=O, or S(=O)$_2$;

R$^1$ and R$^2$ together with the nitrogen atom to which they are both attached form a 5-20 membered spirocyclic heterocyclic ring, 5-20 membered fused heterocyclic ring, 5-20 membered bridged heterocyclic ring, 4 membered monocyclic heterocyclic ring, 7 membered monocyclic heterocyclic ring, or 8-20 membered monocyclic heterocyclic ring, said 5-20 membered spirocyclic heterocyclic ring, 5-20 membered fused heterocyclic ring, 5-20 membered bridged heterocyclic ring, 4 membered monocyclic heterocyclic ring, 7 membered monocyclic heterocyclic ring, or 8-20 membered monocyclic heterocyclic ring optionally further contains ring members selected from —O—, —S—, —S(=O)—, —S(=O)$_2$—, —C(=O)—, —NH—, —CH$_2$—, —CHF—, —CF$_2$—, —C(=O)NH—, —NHC(=O)—, —S(=O)NH—, —NHS(=O)—, —S(=O)$_2$NH— or —NHS(=O)$_2$—, and said 5-20 membered spirocyclic heterocyclic ring, 5-20 membered fused heterocyclic ring, 5-20 membered bridged heterocyclic ring, 4 membered monocyclic heterocyclic ring, 7 membered monocyclic heterocyclic ring, or 8-15 membered monocyclic heterocyclic is independently optionally substituted with one or more R$_8$;

R$_8$ at each occurrence is independently selected from halogen —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)O(C$_{1-6}$alkyl), —NHC(=O)(OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)$_2$(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O))$_2$O(C$_{1-6}$alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, wherein said —C$_{1-6}$alkyl, —C$_{1-6}$haloalkyl, —C$_{1-6}$haloalkoxy, —C$_{2-6}$alkenyl, —C$_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)O(C$_{1-6}$alkyl), —NHC(=O) (OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$ alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O)$_2$O(C$_{1-6}$alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, R$^3$ is selected from phenyl, naphthyl, 5 membered heteroaryl, 6 membered heteroaryl, 8 membered heteroaryl, 9 membered heteroaryl or 10 membered heteroaryl; each of which is independently optionally substituted with one or more R$^{31}$;

R$^{31}$ at each occurrence is independently selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)O(C$_{1-6}$alkyl), —NHC(=O)(OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O)$_2$O(C$_{1-6}$alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl), —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)O(C$_{1-6}$alkyl), —NHC(=O)(OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O)$_2$O(C$_{1-6}$alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl;

R$^{41}$, R$^{42}$ or R$^{43}$ at each occurrence is independently selected from hydrogen, halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)O(C$_{1-6}$alkyl), —NHC(=O)(OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O)$_2$O(C$_{1-6}$alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)C$_{1-6}$alkyl), —N(C$_{1-6}$alkyl)C(=O)(C$_{1-6}$alkyl), —OC(=O)O(C$_{1-6}$alkyl), —NHC(=O)(OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N (C$_{1-6}$ alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)N(C$_{1-6}$alkyl, —NHS(=O)$_2$(C$_{1-6}$alkyl), —N(C$_{1-6}$alkyl)S(=O)$_2$(C$_{1-6}$ alkyl), —OS(=O)O(C$_{1-6}$alkyl), —NHS(=O)$_2$O(C$_{1-6}$ alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$ N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$ alkyl)S(=O)$_2$NH$_2$, —N(C$_{1-6}$alkyl)S(=O)$_2$NH(C$_{1-6}$ alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, R$^{51}$, R$^{52}$, R$^{53}$, R$^{54}$ or R$^{55}$ at each occurrence is independently selected from hydrogen, halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$ alkyl), —S(haloC$_{1-6}$alkyl), —S(=O)(C$_{1-6}$alkyl), —S(=O)(C$_{1-6}$alkyl), —C(=O)(C$_{1-6}$alkyl), —C(=O)OH, —C(=O)(OC$_{1-6}$alkyl), —OC(=O)(C$_{1-6}$ alkyl), —C(=O)NH$_2$, —C(=O)NH(C$_{1-6}$alkyl), —C(=O)N(C$_{1-6}$alkyl), —NHC(=O)(C$_{1-6}$alkyl), —N(C$_{1-6}$alkyl)C(=O)(C$_{1-6}$alkyl), —SC(=O)O(C$_{1-6}$alkyl), —NHC(=O) (OC$_{1-6}$alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$ alkyl), —S(=Ok)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$alkyl), —OS(=O)$_2$O(C$_{1-6}$ alkyl), —NHS(=O)$_2$O(C$_{1-6}$alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$alkyl), —N(C$_{1-6}$alkyl)S(=O)$_2$N(C$_{1-6}$alkyl)$_2$, —PH(C$_{1-6}$alkyl), —P(C$_{1-6}$ alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$ alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$ alkyl), —OC(=O)(OC$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$ alkyl), —OC(=O)O(C$_{1-6}$alkyl), —NHC(=O)(C$_{1-6}$ alkyl), —N(C$_{1-6}$alkyl)C(=O)(OC$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$ alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$ alkyl), —OS(=O)$_2$O(C$_{1-6}$alkyl), —NHS(=O)$_2$O(C$_{1-6}$ alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$ N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$ alkyl)S(=O)$_2$NH$_2$, —N(C$_{1-6}$alkyl)S(=O)$_2$NH(C$_{1-6}$ alkyl), —N(C$_{1-6}$alkyl)S(=O))$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl;

R$^6$ at each occurrence is independently selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$ alkyl), —S(=O)(C$_{1-6}$alkyl), —S(=O)$_2$(C$_{1-6}$alkyl), —C(=O)(C$_{1-6}$alkyl), —C(=O)OH, —C(=O)(OC$_{1-6}$ alkyl), —OC(=O)(C$_{1-6}$alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$ alkyl), —OC(=O)O(C$_{1-6}$alkyl), —NHC(=O) (OC$_{1-6}$ alkyl), —N(C$_{1-6}$alkyl)C(=O)(C$_{1-6}$alkyl), —OC(=O)NH(C$_{1-6}$alkyl), —OC(=O)N(C$_{1-6}$alkyl)$_2$, —NHC(=O)NH$_2$, —NHC(=O)NH(C$_{1-6}$alkyl), —NHC(=O)N(C$_{1-6}$alkyl)$_2$, —N(C$_{1-6}$alkyl)C(=O)NH$_2$, —N(C$_{1-6}$alkyl)C(=O)NH(C$_{1-6}$alkyl), —N(C$_{1-6}$alkyl)C(=O)N(C$_{1-6}$alkyl)$_2$, —S(=O)(OC$_{1-6}$alkyl), —OS(=O)(C$_{1-6}$ alkyl), —S(=O)NH$_2$, —S(=O)NH(C$_{1-6}$alkyl), —S(=O)N(C$_{1-6}$alkyl)$_2$, —NHS(=O)(C$_{1-6}$alkyl), —N(C$_{1-6}$alkyl)S(=O)(C$_{1-6}$alkyl), —S(=O)$_2$(OC$_{1-6}$alkyl), —OS(=O)$_2$(C$_{1-6}$alkyl), —S(=O)$_2$NH$_2$, —S(=O)$_2$NH(C$_{1-6}$alkyl), —S(=O)$_2$N(C$_{1-6}$alkyl)$_2$, —NHS(=O)$_2$(C$_{1-6}$alkyl), —N(C$_{1-6}$alkyl)S(=O)$_2$(C$_{1-6}$ alkyl), —OS(=O)$_2$O(C$_{1-6}$alkyl), —NHS(=O)$_2$O(C$_{1-6}$ alkyl), —N(C$_{1-6}$alkyl)S(=O)$_2$O(C$_{1-6}$alkyl), —OS(=O)$_2$NH$_2$, —OS(=O)$_2$NH(C$_{1-6}$alkyl), —OS(=O)$_2$ N(C$_{1-6}$alkyl)$_2$, —NHS(=O)$_2$NH$_2$, —NHS(=O)$_2$NH(C$_{1-6}$alkyl), —NHS(=O)$_2$N(C$_{1-6}$alkyl)$_2$, —N(C$_{1-6}$alkyl)S(=O)$_2$NH$_2$, —N(C$_{1-6}$alkyl)S(=O)$_2$NH(C$_{1-6}$ alkyl), —N(C$_{1-6}$alkyl)S(=O)$_2$N(C$_{1-6}$alkyl)$_2$, —PH(C$_{1-6}$alkyl), —P(C$_{1-6}$alkyl)$_2$, —P(=O)H(C$_{1-6}$alkyl), —P(=O)(C$_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —C$_{1-6}$alkyl, —C$_{1-6}$haloalkyl, —C$_{1-6}$haloalkoxy, —C$_{2-6}$alkenyl, —C$_{2-6}$alkynyl, —CN, oxo, —NH$_2$, —NH(C$_{1-6}$alkyl), —N(C$_{1-6}$alkyl)$_2$, —OH, —O(C$_{1-6}$alkyl), —SH, —S(C$_{1-6}$alkyl), —S(haloC$_{1-6}$alkyl), —S(=O)(C$_{1-6}$alkyl), —S(=O)$_2$(C$_{1-6}$alkyl), —C(=O)(C$_{1-6}$alkyl), —C(=O)OH, —C(=O)O(C$_{1-6}$alkyl), —OC(=O)(C$_{1-6}$ alkyl), —C(=O)NH$_2$, —C(=O)NH(C$_{1-6}$alkyl), —C(=O)N(C$_{1-6}$alkyl)$_2$, —NHC(=O)(C$_{1-6}$alkyl), —N(C$_{1-6}$alkyl)C(=O)(C$_{1-6}$alkyl), —OC(=O)NH ($C_{1-6}$ alkyl), —NHC(=O)(O$C_{1-6}$alkyl), —N($C_{1-6}$alkyl)C(=O)(O$C_{1-6}$alkyl), —OC(=O)NH($C_{1-6}$alkyl), —OC(=O)N($C_{1-6}$alkyl)$_2$, —NHC(=O)NH$_2$, —NHC(=O)NH($C_{1-6}$alkyl), —NHC(=O)N($C_{1-6}$alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N($C_{1-6}$alkyl)$_2$, —S(=O)(O$C_{1-6}$alkyl), —OS(=O)($C_{1-6}$alkyl), —S(=O)NH$_2$, —S(=O)NH($C_{1-6}$alkyl), —S(=O)N($C_{1-6}$alkyl)$_2$, —NHS(=O)($C_{1-6}$alkyl), —N($C_{1-6}$alkyl)S(=O)($C_{1-6}$alkyl), —S(=O)$_2$(O$C_{1-6}$alkyl), —OS(=O)$_2$($C_{1-6}$alkyl), —S(=O)$_2$NH$_2$, —S(=O)$_2$NH($C_{1-6}$ alkyl), —S(=O)$_2$N($C_{1-6}$alkyl)$_2$, —NHS(=O)$_2$($C_{1-6}$ alkyl), —N($C_{1-6}$alkyl)S(=O)$_2$($C_{1-6}$alkyl), —OS(=O)$_2$O($C_{1-6}$alkyl), —NHS(=O)$_2$O($C_{1-6}$alkyl), —N($C_{1-6}$alkyl)S(=O)$_2$O($C_{1-6}$alkyl), —OS(=O)$_2$NH$_2$, —OS(O)$_2$NH($C_{1-6}$alkyl), —OS(=O)$_2$N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$N($C_{1-6}$alkyl)$_2$, —PH($C_{1-6}$alkyl), —P($C_{1-6}$alkyl)$_2$, —P(=O)H($C_{1-6}$alkyl), —P(=O)($C_{1-6}$alkyl)$_2$, 3-6 membered cycloalkyl, 3-6 membered heterocyclyl, 6-10 membered aryl or 5-10 membered heteroaryl;

$R^7$ at each occurrence is independently selected from halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —NH$_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(=O)($C_{1-6}$alkyl), —S(=O)$_2$($C_{1-6}$alkyl), —C(=O)($C_{1-6}$alkyl), —C(=O)OH, —C(=O)(O$C_{1-6}$alkyl), —OC(=O)($C_{1-6}$alkyl), —C(=O)NH$_2$, —C(=O)NH($C_{1-6}$alkyl), —C(=O)N($C_{1-6}$alkyl)$_2$, —NHC(=O)($C_{1-6}$alkyl), —N($C_{1-6}$alkyl)C(=O)($C_{1-6}$alkyl), —OC(=O)O($C_{1-6}$alkyl), —NHC(=O) (O$C_{1-6}$alkyl), —N($C_{1-6}$alkyl)C(=O)(O$C_{1-6}$alkyl), —OC(=O)NH($C_{1-6}$alkyl), —OC(=O)N($C_{1-6}$alkyl)$_2$, —NHC(=O)NH$_2$, —NHC(=O)NH($C_{1-6}$alkyl), —NHC(=O)N($C_{1-6}$alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N($C_{1-6}$alkyl)$_2$, —S(=O)(O$C_{1-6}$alkyl), —OS(=O)($C_{1-6}$alkyl), —S(=O)NH$_2$, —S(=O)NH($C_{1-6}$alkyl), —S(=O)N($C_{1-6}$alkyl)$_2$, —NHS(=O)($C_{1-6}$ alkyl), —N($C_{1-6}$alkyl)S(=O)($C_{1-6}$alkyl), —S(=O)$_2$(O$C_{1-6}$alkyl), —OS(=O)$_2$($C_{1-6}$alkyl), —S(=O)$_2$NH$_2$, —S(=O)$_2$NH($C_{1-6}$alkyl), —S(=O)$_2$N($C_{1-6}$alkyl)$_2$, —NHS(=O)$_2$($C_{1-6}$alkyl), —N($C_{1-6}$alkyl)S(=O)$_2$($C_{1-6}$ alkyl), —OS(=O)$_2$O($C_{1-6}$alkyl), —NHS(=O)$_2$O($C_{1-6}$ alkyl), —N($C_{1-6}$alkyl)S(=O)$_2$O($C_{1-6}$alkyl), —OS(=O)$_2$NH$_2$, —OS(=O)$_2$NH($C_{1-6}$alkyl), —OS(=O)$_2$ N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$N($C_{1-6}$alkyl)$_2$, —PH($C_{1-6}$alkyl), —P($C_{1-6}$alkyl)$_2$, —P(=O)H($C_{1-6}$alkyl), —P(=O)($C_{1-6}$alkyl)$_2$, 3-6 membered cycloalkyl, 3-6 membered heterocyclyl, 6-10 membered aryl or 5-10 membered heteroaryl, wherein each of which is independently optionally substituted with 1, 2, 3, 4, 5 or 6 substituents selected from halogen, —$C_{1-6}$alkyl, —$C_{1-6}$haloalkyl, —$C_{1-6}$haloalkoxy, —$C_{2-6}$ alkenyl, —$C_{2-6}$alkynyl, —CN, oxo, —NH$_2$, —N($C_{1-6}$ alkyl), —N($C_{1-6}$alkyl)$_2$, —OH, —O($C_{1-6}$alkyl), —SH, —S($C_{1-6}$alkyl), —S(halo$C_{1-6}$alkyl), —S(OX$C_{1-6}$alkyl), —S(=O)$_2$($C_{1-6}$alkyl), —C(=O)($C_{1-6}$alkyl), —C(=O)OH, —C(=O)(O$C_{1-6}$alkyl), —OC(=O)($C_{1-6}$alkyl), —C(=O)NH$_2$, —C(=O)NH ($C_{1-6}$alkyl), —C(=O)N($C_{1-6}$alkyl)$_2$, —NHC(=O) ($C_{1-6}$ alkyl), —N($C_{1-6}$alkyl)C(=O)($C_{1-6}$alkyl), —OC(=O)O($C_{1-6}$alkyl), —NHC(=O) (O$C_{1-6}$alkyl), —N($C_{1-6}$alkyl)C(=O)($C_{1-6}$alkyl), —OC(=O)NH ($C_{1-6}$ alkyl), —OC(=O)N($C_{1-6}$alkyl)$_2$, —NHC(=O)NH$_2$, —NHC(=O)NH($C_{1-6}$alkyl), —NHC(=O)N ($C_{1-6}$ alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N ($C_{1-6}$alkyl)$_2$, —S(=O)(O$C_{1-6}$alkyl), —OS(=O)($C_{1-6}$ alkyl), —S(=O)NH$_2$, —S(=O)N($C_{1-6}$alkyl), —S(=O)N($C_{1-6}$alkyl)$_2$, —NHS(=O)($C_{1-6}$alkyl), —N($C_{1-6}$alkyl)S(=O)($C_{1-6}$alkyl), —S(=O)$_2$(O$C_{1-6}$alkyl), —OS(=O)$_2$($C_{1-6}$alkyl), —S(=O)$_2$NH$_2$, —S(=O)$_2$NH($C_{1-6}$ alkyl), —S(=O)$_2$N($C_{1-6}$alkyl)$_2$, —NHS(=O)$_2$($C_{1-6}$ alkyl), —N($C_{1-6}$alkyl)S(=O)$_2$($C_{1-6}$ alkyl), —OS(=O)$_2$O($C_{1-6}$alkyl), —NHS(=O)$_2$O($C_{1-6}$ alkyl), —N($C_{1-6}$alkyl)S(=O)$_2$O($C_{1-6}$alkyl), —OS(=O)$_2$ NH$_2$, —OS(=O)$_2$NH($C_{1-6}$alkyl), —OS(=O)$_2$ N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$($C_{1-6}$alkyl)$_2$, —PH($C_{1-6}$alkyl), —P($C_{1-6}$alkyl)$_2$, —P(=O)H($C_{1-6}$alkyl), —P(=O)($C_{1-6}$alkyl)$_2$, 3-6 membered cycloalkyl, 3-6 membered heterocyclyl, 6-10 membered aryl or 5-10 membered heteroaryl;

m, n, p and q are independently selected from 0, 1, 2, 3, 4, 5, 6, 7, 8, 9 or 10;

said heterocyclyl, heterocyclic, or heteroaryl at each occurrence contains 1, 2, 3, 4, or 5 ring members selected from N, O, S, S(=O) or S(=O)$_2$.

In some embodiments, the KRAS G12D binding moiety is:

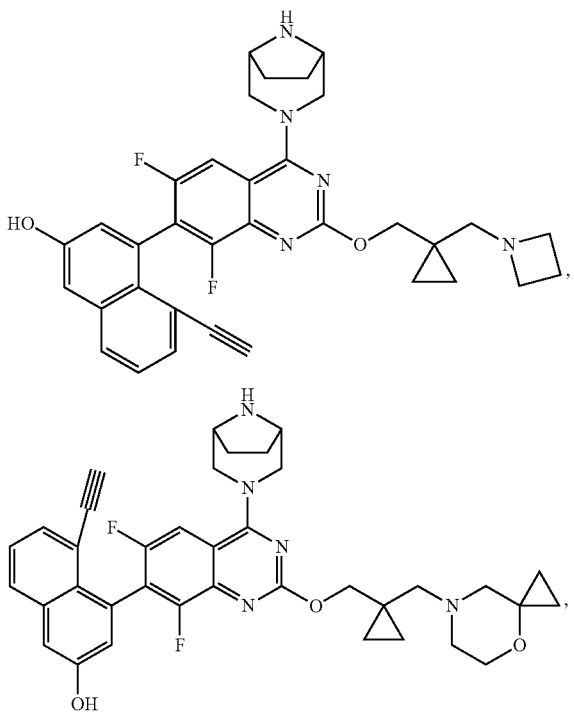

103
-continued
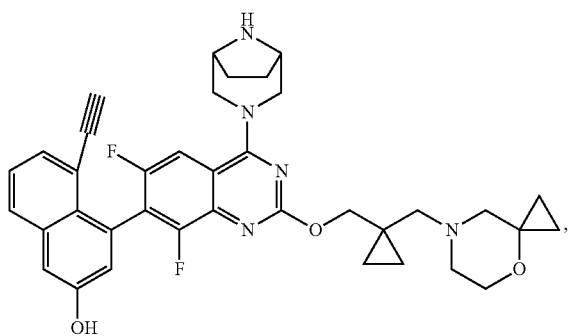
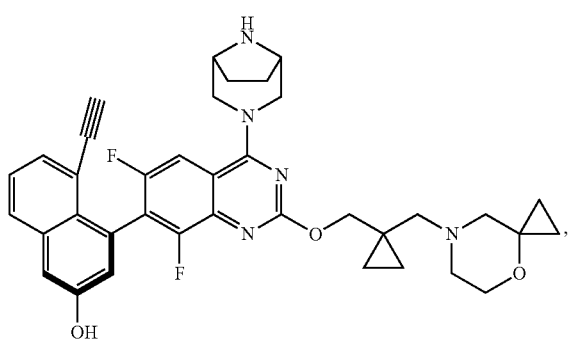
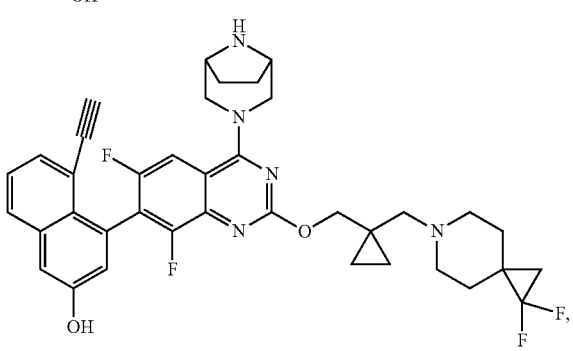
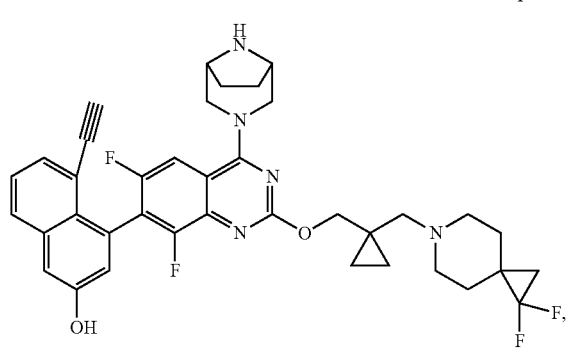
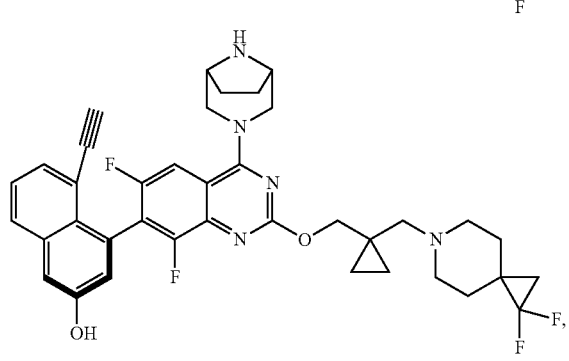
104
-continued
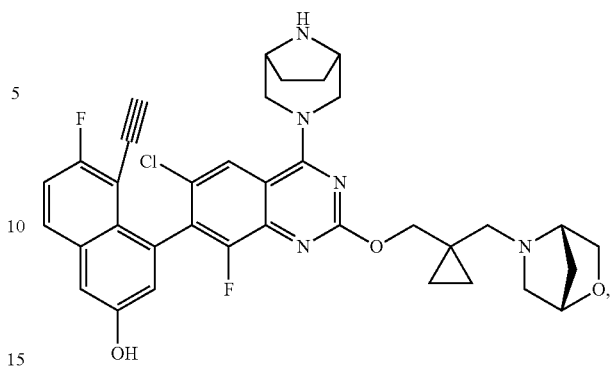
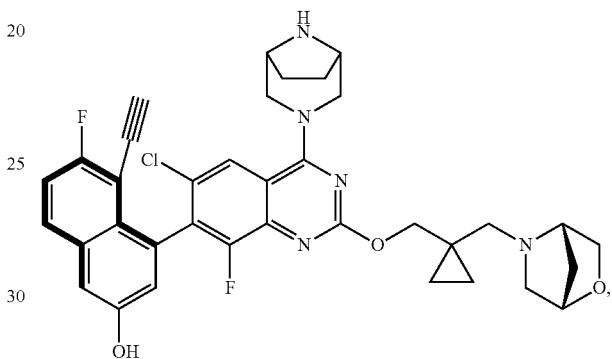
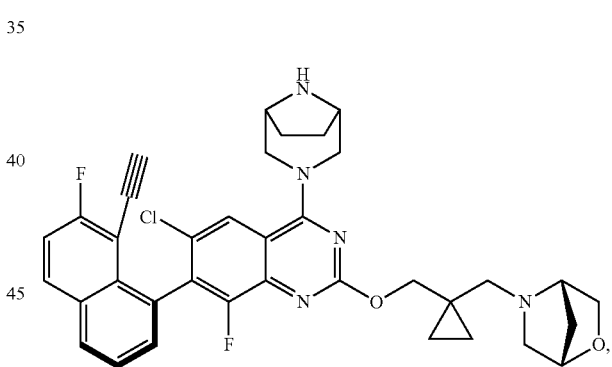
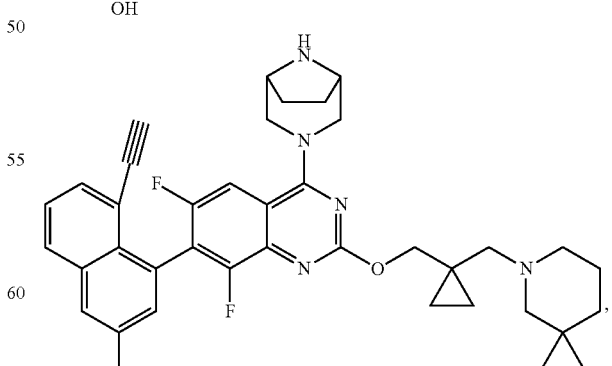
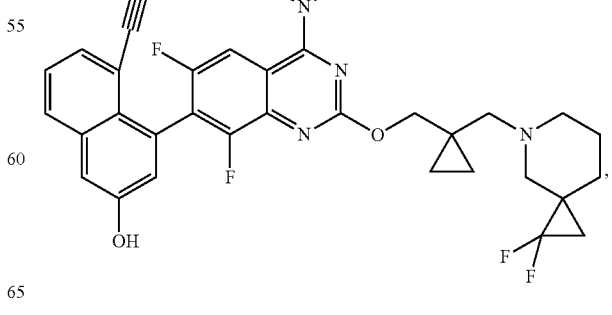

105
-continued
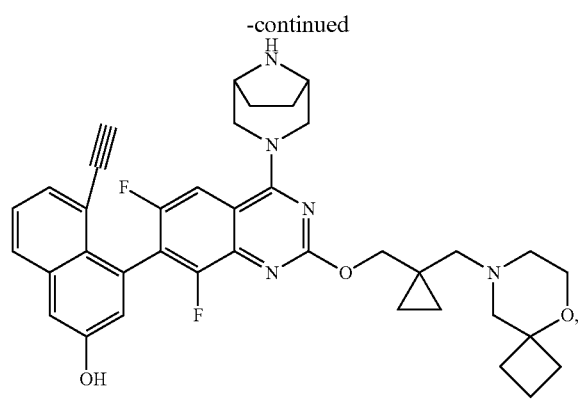
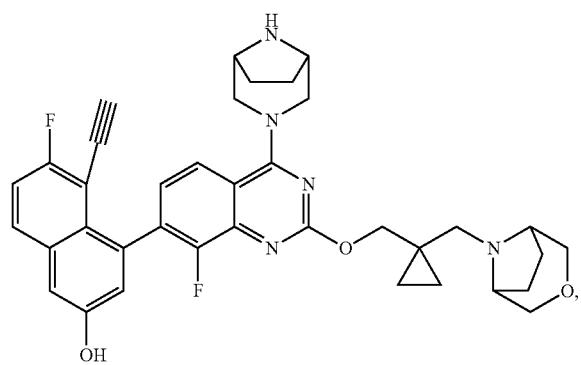
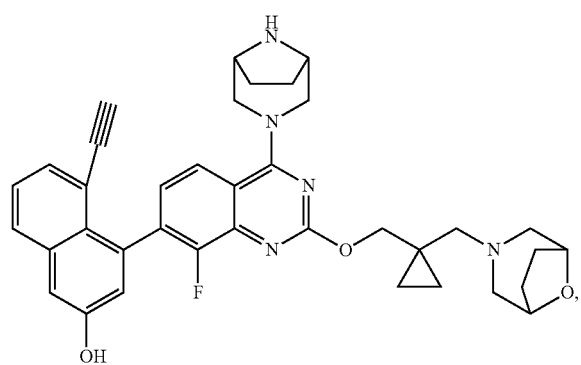
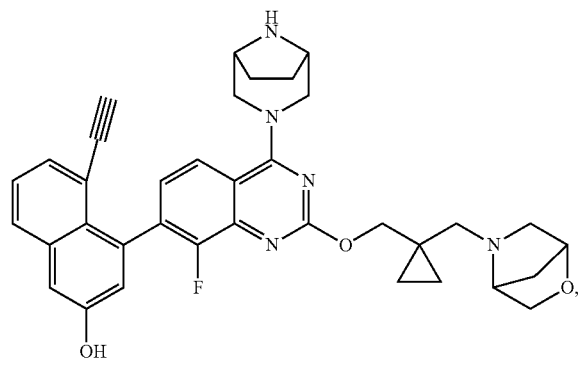
106
-continued
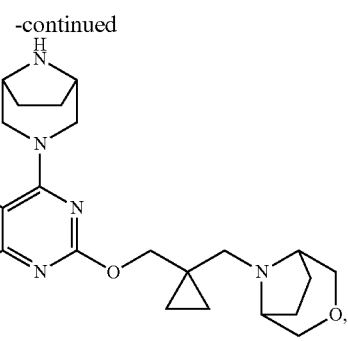
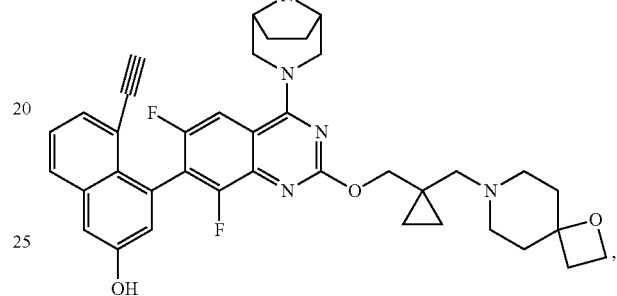
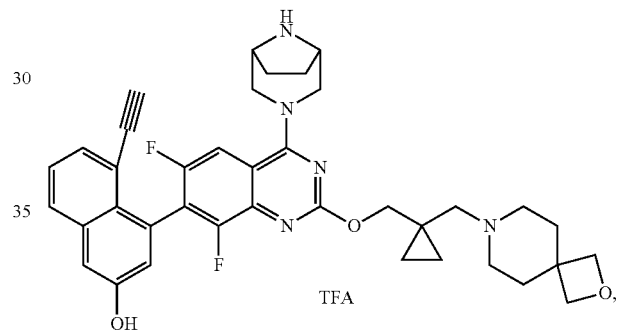
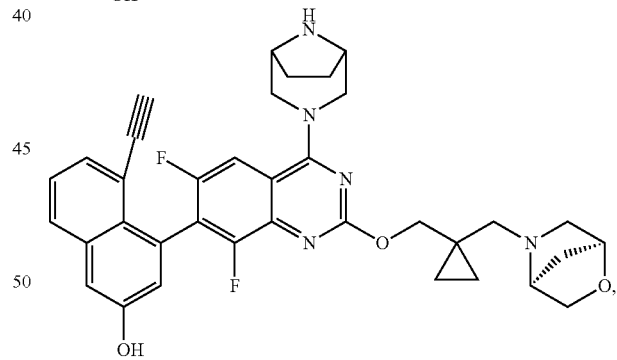
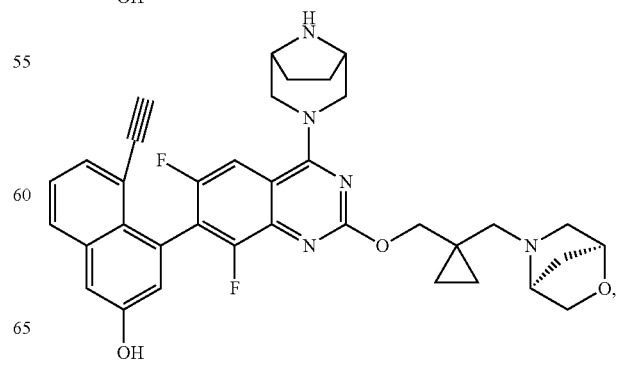

107
-continued
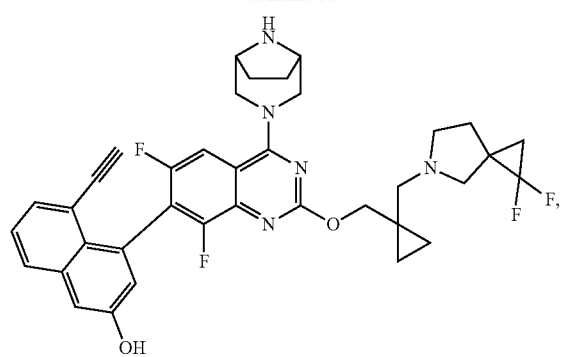
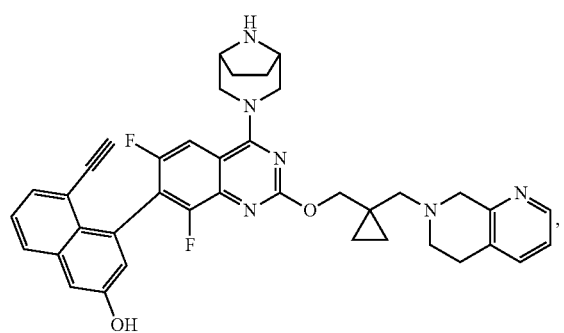
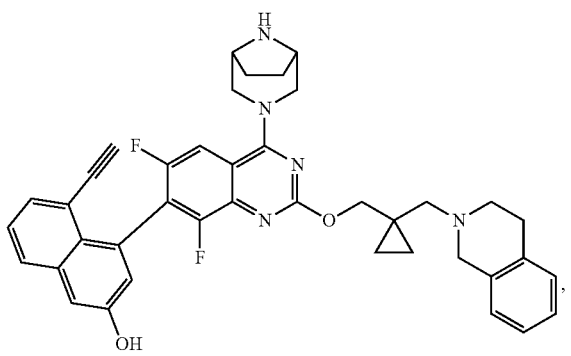
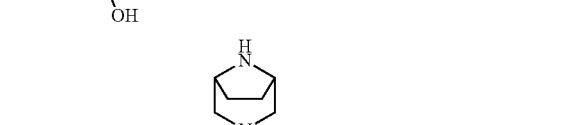
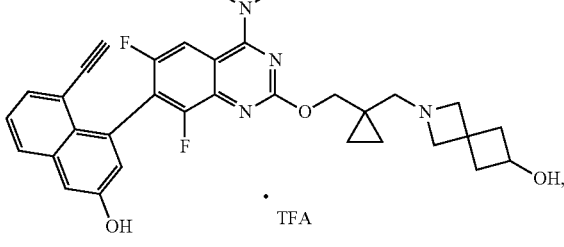
108
-continued
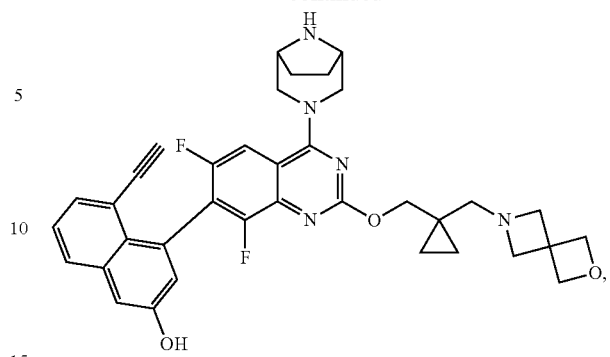
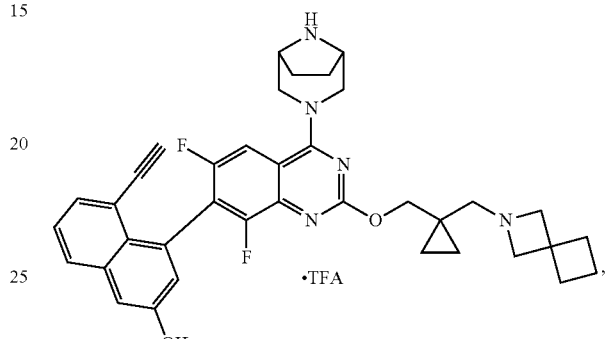

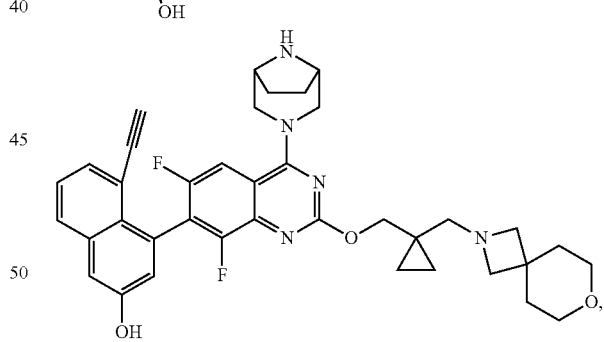
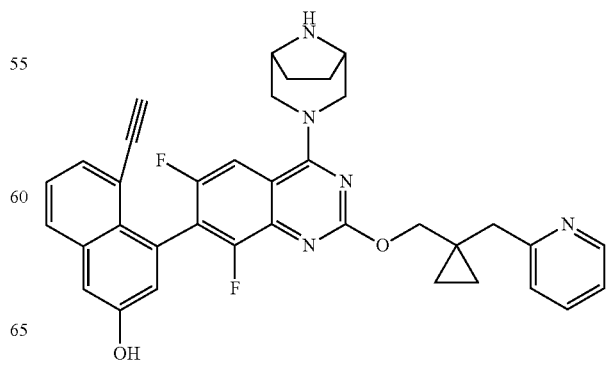

-continued
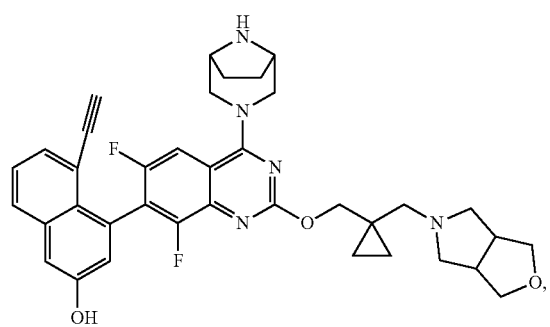
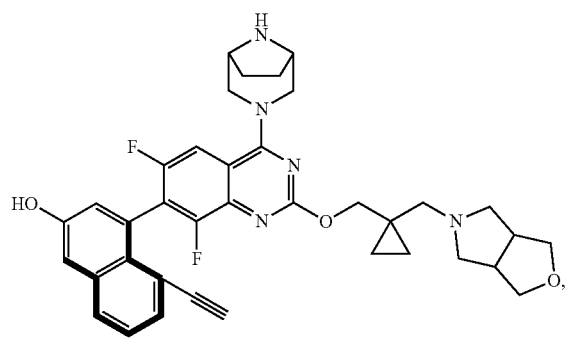
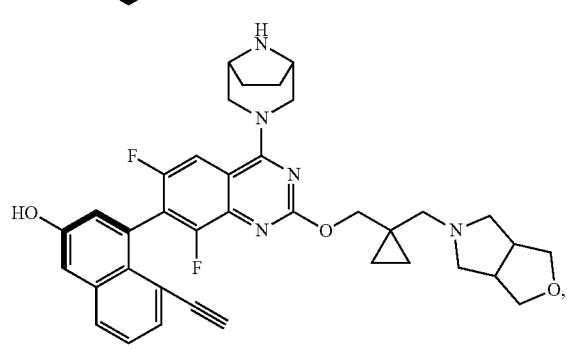
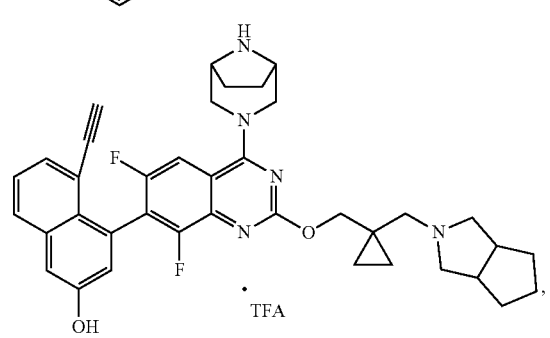
·TFA
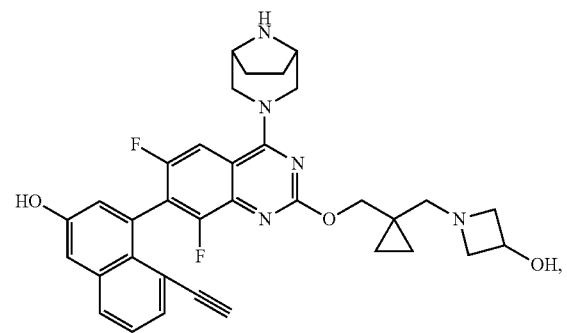
-continued
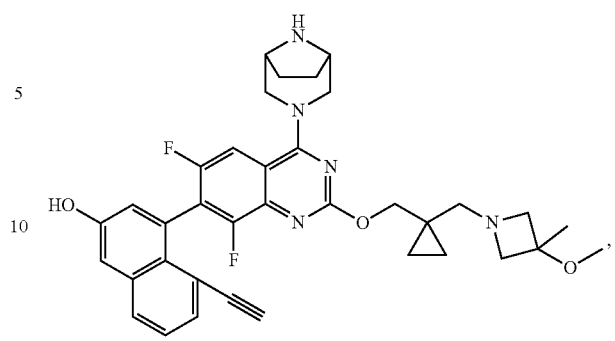
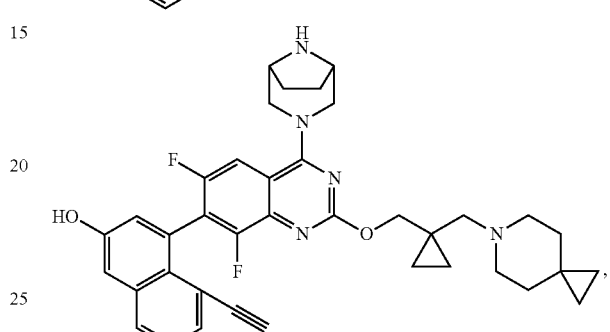

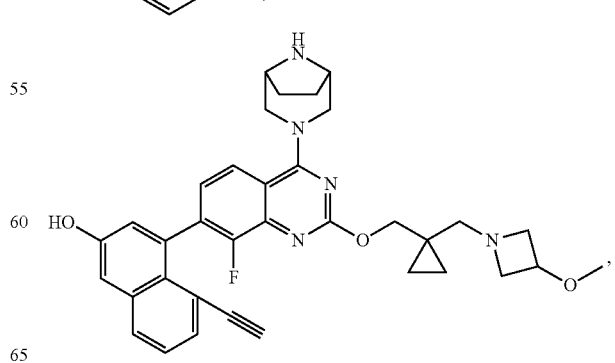

111
-continued
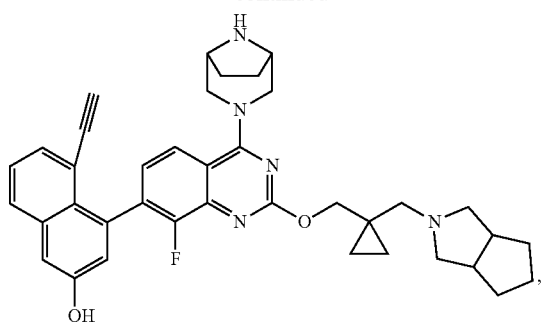
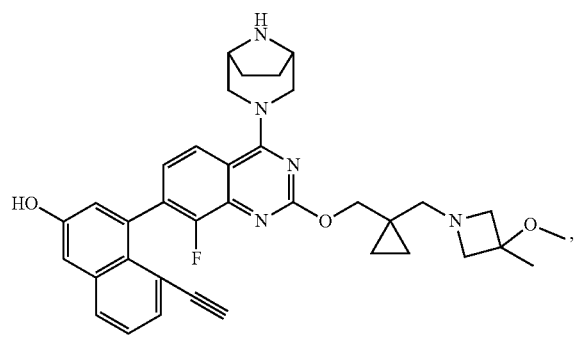
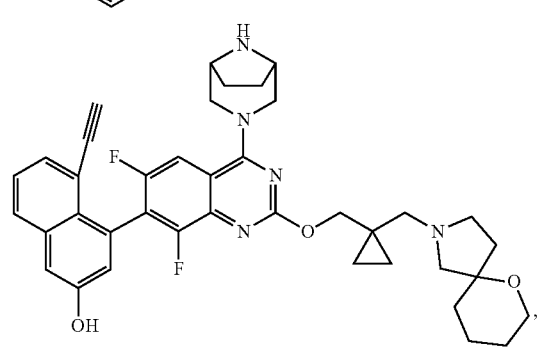
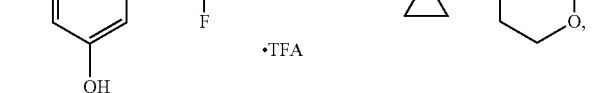
112
-continued
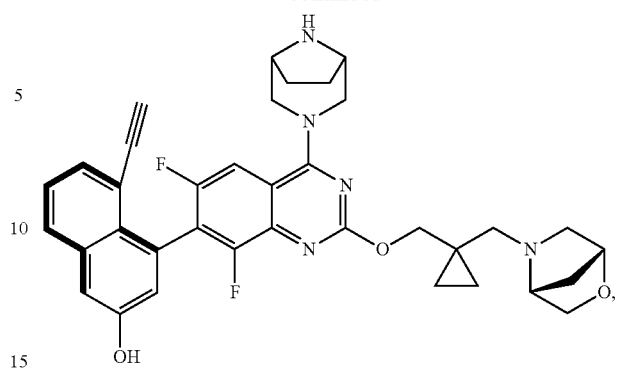
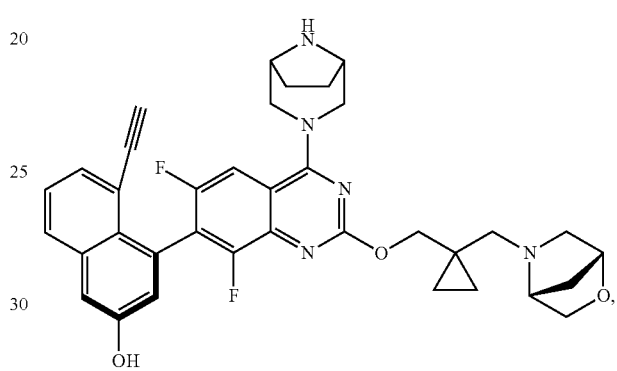
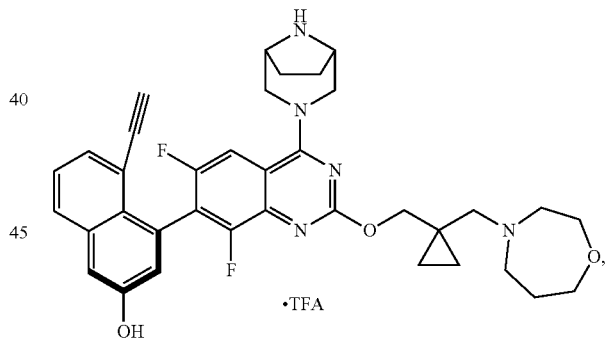
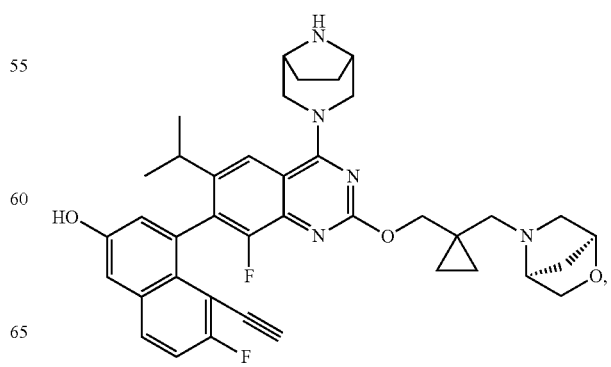

113
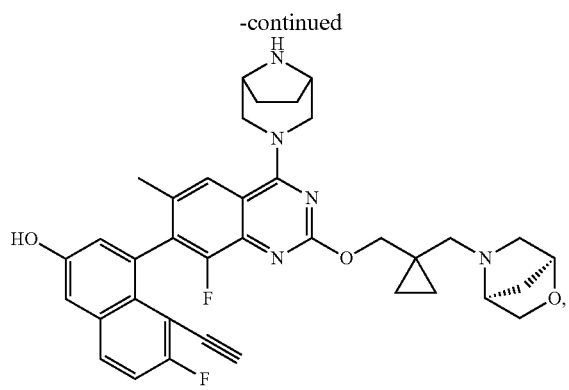
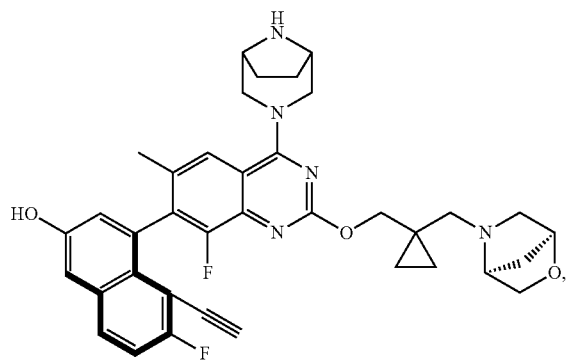
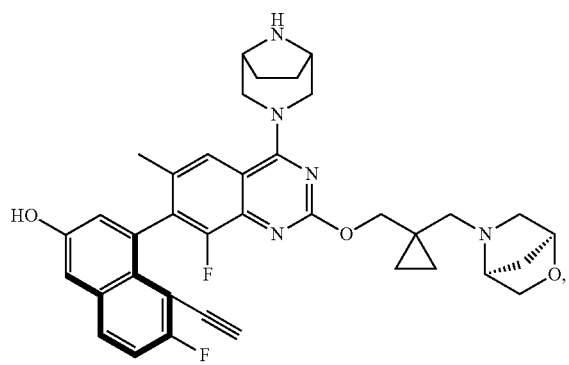
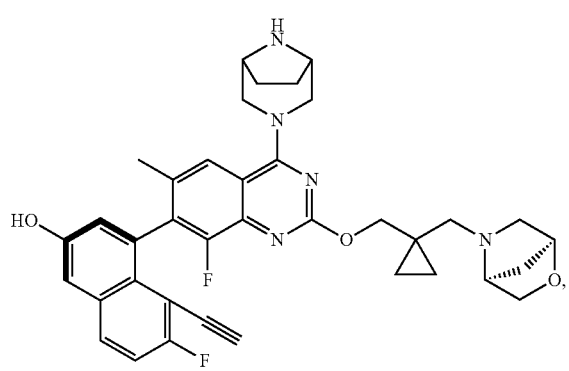
114
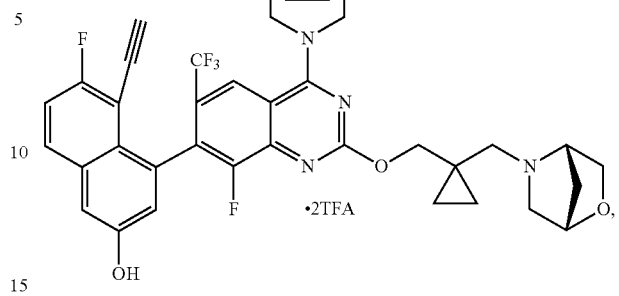
·2TFA
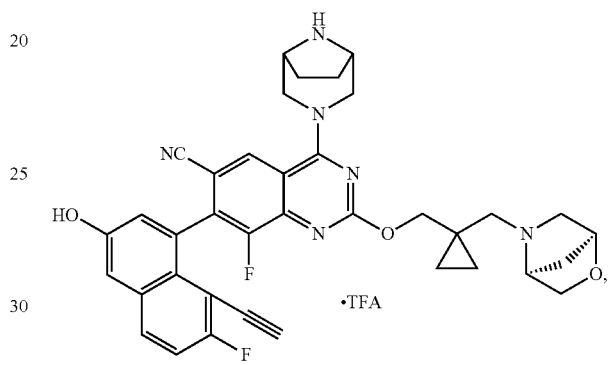
·TFA
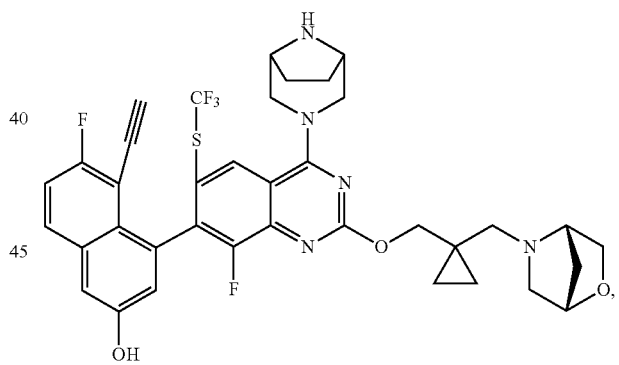
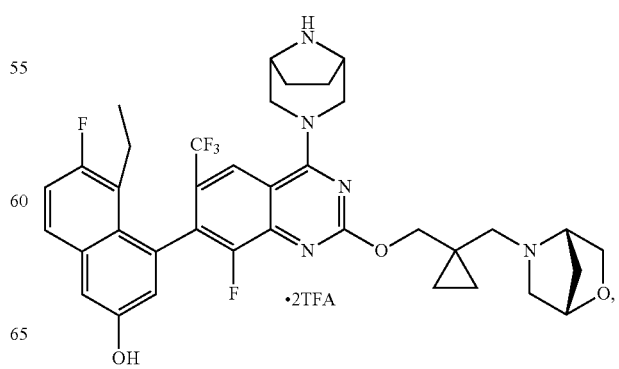
·2TFA 115
-continued
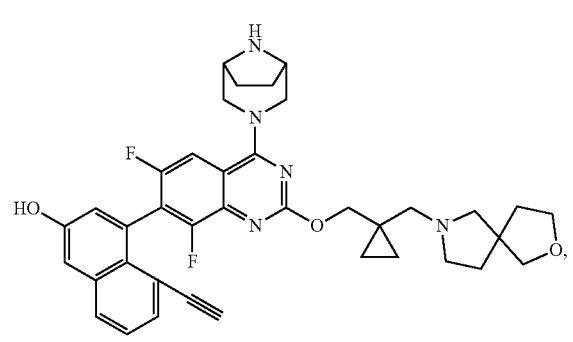
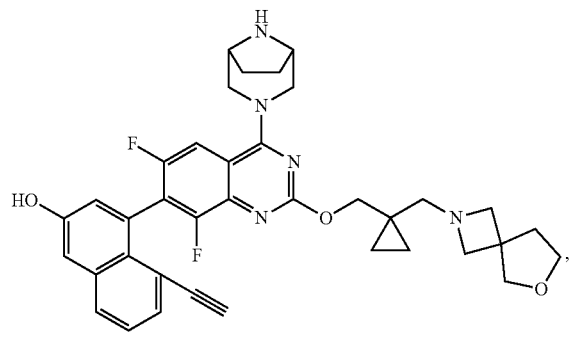
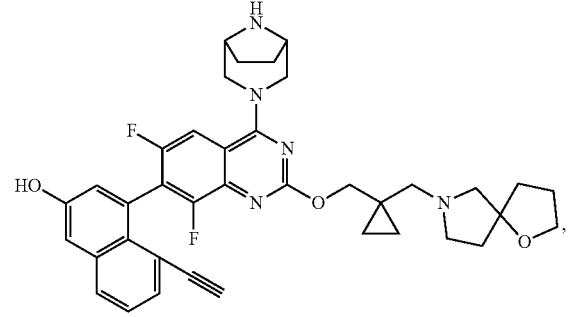
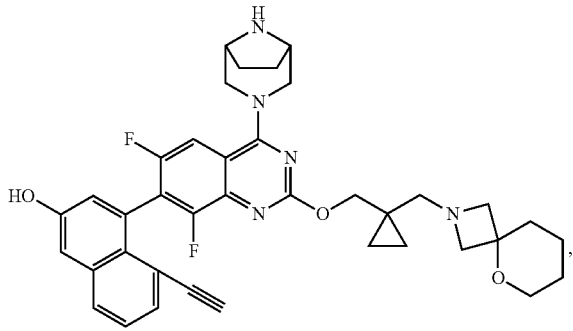
116
-continued
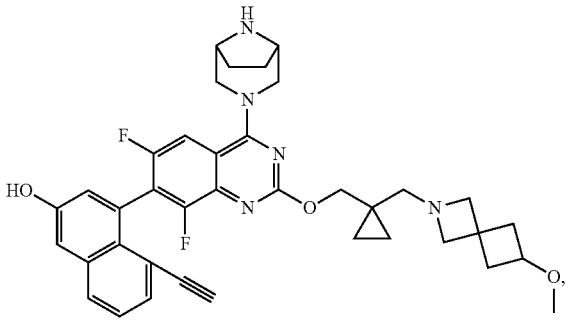
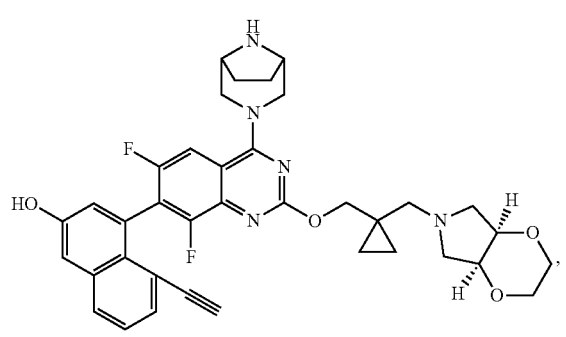
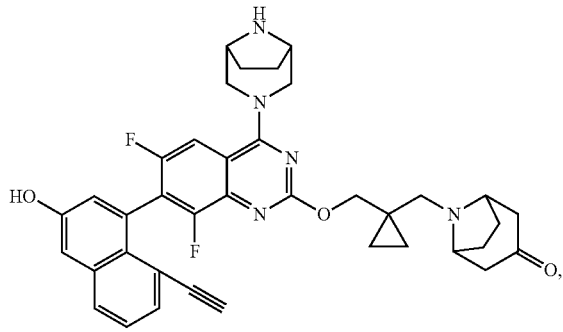
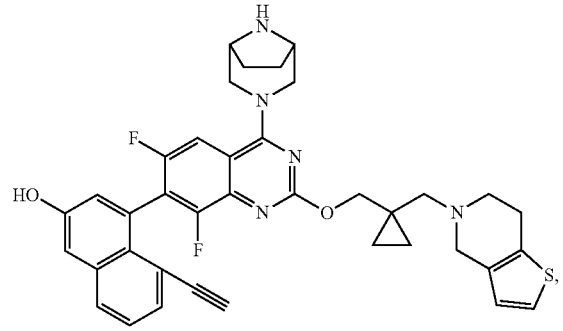
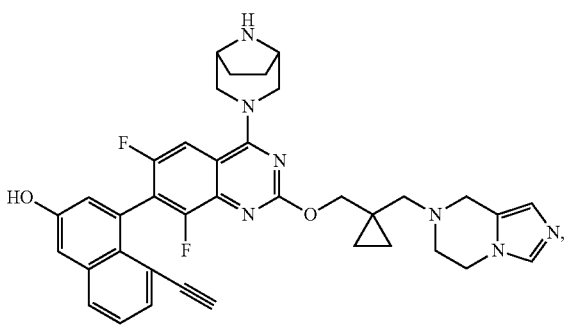

-continued

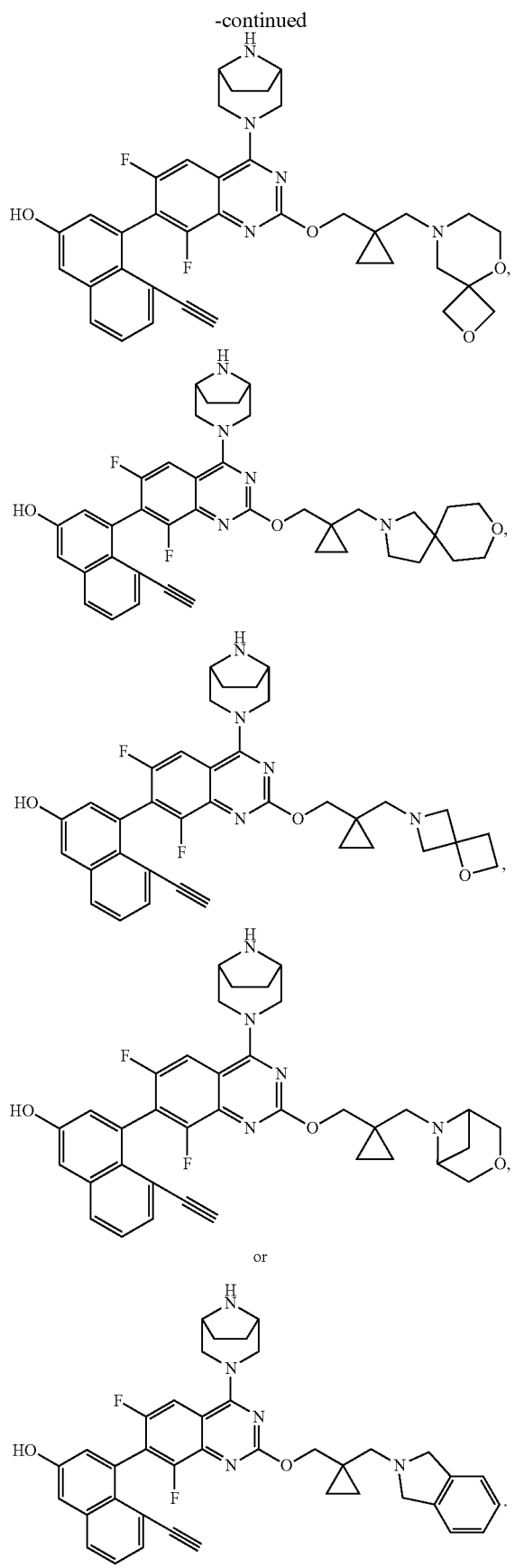

or

In some embodiments, the KRAS G12D binding moiety has the following structural formula:

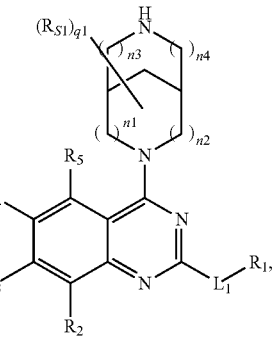

wherein:
$n_1$ is selected from 0, 1, 2, 3, 4, 5, or 6;
$n_2$ is selected from 0, 1, 2, 3, 4, 5, or 6;
$n_3$ is selected from 0, 1, 2, 3, 4, 5, or 6;
$n_4$ is selected from 0, 1, 2, 3, 4, 5, or 6;
$n_5$ is selected from 0, 1, 2, 3, 4, 5, or 6;
each of $R_{S1}$ at each occurrence is independently selected from halogen, —$C_{1-10}$alkyl, halo$C_{1-10}$alkyl, halo$C_{1-10}$alkoxy, —$C_{2-10}$alkenyl, halo$C_{2-10}$alkenyl, —$C_{2-10}$alkynyl, halo$C_{2-10}$alkynyl, —CN, oxo, —N($R_{61}$)$_2$, —O$R_{61}$, —S$R_{61}$, —S(=O)$R_{62}$, —S(=O)$_2R_{62}$, —C(=O)$R_{62}$, —C(=O)O$R_{61}$, —OC(=O)$R_{62}$, —C(=O)N($R_{61}$)$_2$, —N$R_{61}$C(=O)$R_{62}$, —OC(=O)O$R_{61}$, —N$R_{61}$C(=O)O$R_{61}$, —OC(=O)N($R_{61}$)$_2$, —N$R_{61}$C(=O)N($R_{61}$)$_2$, —S(=O)O$R_{61}$, —OS(=O)$R_{62}$, —S(=O)N($R_{61}$)$_2$, —N$R_{61}$S(=O)$R_{62}$, —S(=O)$_2$O$R_{61}$, —OS(=O)$_2R_{62}$, —S(=O)$_2$N($R_{61}$)$_2$, —N$R_{61}$S(=O)$_2R_{62}$, —OS(=O)$_2$O$R_{61}$, —N$R_{61}$S(=O)$_2$O$R_{61}$, —OS(=O)$_2$N($R_{61}$)$_2$, —N$R_{61}$S(=O)$_2$N($R_{61}$)$_2$, —P($R_{61}$)$_2$, —P(=O)($R_{62}$)$_2$, 3-10 membered cycloalkyl, 3-10 membered cycloalkenyl, 3-10 membered cycloalkynyl, 3-10 membered heterocyclyl, 6-10 membered aryl or 5-10 membered heteroaryl; wherein, said —$C_{1-10}$alkyl, halo$C_{1-10}$alkyl, halo$C_{1-10}$alkoxy, —$C_{2-10}$alkenyl, halo$C_{2-10}$alkenyl, —$C_{2-10}$alkynyl, halo$C_{2-10}$alkynyl, 3-10 membered cycloalkyl, 3-10 membered cycloalkenyl, 3-10 membered cycloalkynyl, 3-10 membered heterocyclyl, 6-10 membered aryl or 5-10 membered heteroaryl is optionally independently substituted with one or more substituents selected from halogen, —$C_{1-6}$alkyl, halo$C_{1-6}$alkyl, halo$C_{1-6}$alkoxy, —$C_{2-6}$alkenyl, halo$C_{2-6}$alkenyl, —$C_{2-6}$alkynyl, halo$C_{2-6}$alkynyl, —CN, —N($R_{63}$)$_2$, —O$R_{63}$, —S$R_{63}$, —S(=O)$R_{64}$, —S(=O)$_2R_{64}$, —C(=O)$R_{64}$, —C(=O)O$R_{63}$, —OC(=O)$R_{64}$, —C(=O)N($R_{63}$)$_2$, —N$R_{63}$C(=O)$R_{64}$, —OC(=O)O$R_{63}$, —N$R_{63}$C(=O)O$R_{63}$, —OC(=O)N($R_{63}$)$_2$, —N$R_{63}$C(=O)N($R_{63}$)$_2$, —S(=O)O$R_{63}$, —OS(=O)$R_{64}$, —S(=O)N($R_{63}$)$_2$, —N$R_{63}$S(=O)$R_4$, —S(=O)$_2$O$R_{63}$, —OS(=O)$_2R_{64}$, —S(=O)$_2$N($R_{63}$)$_2$, —N$R_{63}$S(=O)$_2R_{64}$, —OS(=O)$_2$O$R_{63}$, —N$R_{63}$S(=O)$_2$O$R_{63}$, —OS(=O)$_2$N($R_{63}$)$_2$, —N$R_{63}$S(=O)$_2$N($R_{63}$)$_2$, —P($R_{63}$)$_2$, —P(=O)($R_{64}$)$_2$, 3-10 membered cycloalkyl, 3-10 membered cycloalkenyl, 3-10 membered cycloalkynyl, 3-10 membered heterocyclyl, 6-10 membered aryl or 5-10 membered heteroaryl;

optionally, two $R_{S1}$ together with the carbon atom to which they are both attached form a 3-10 membered carbocyclic ring or a 3-10 heterocyclic ring; wherein, said 3-10 membered carbocylic ring or 3-10 heterocyclic ring is optionally substituted with one or more $R_{6b}$;

optionally, two adjacent $R_{S1}$ together with the carbon atoms to which they are respectively attached form a 3-10 membered carbocyclic ring, a 3-10 membered heterocyclic ring, a 6-10 membered aryl ring or a 5-10 membered heteroaryl ring, wherein, each of rings is independently optionally substituted with one or more $R_{6c}$;

each of $q_1$ is independently selected from 0, 1, 2, 3, 4, 5 or 6;

$L_1$ is a bond, O, S, S(=O), S(=O)$_2$ or $NR_{6a}$;

$R_1$ is selected from

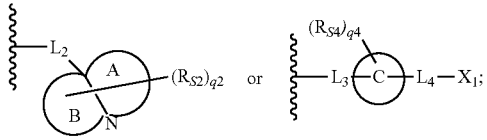

$L_2$ is selected from a bond or $C_{1-10}$ alkylene optionally substituted with one or more $R_{6d}$;

$L_3$ is selected from a bond or $C_{1-10}$ alkylene optionally substituted with one or more $R_{6e}$;

$L_4$ is selected from a bond or $C_{1-10}$ alkylene optionally substituted with one or more $R_{6f}$;

Ring A or ring B is independently selected from a 3-10 membered heterocyclic ring which optionally further contains 1, 2, or 3 heteroatoms selected from N, O or S;

Ring C is selected from a 3-10 membered carbocyclic ring or a 3-10 membered heterocyclic ring; wherein the moiety of -$L_3$- and -$L_4 X_1$ are attached to the same atom or different atoms of the ring C;

$X_1$ is selected from —N($R_{65}$)$_2$, —O$R_{65}$, —S$R_{65}$, 3-10 membered heterocyclyl, or 5-10 membered heteroaryl, wherein said 3-10 membered heterocyclyl or 5-10 membered heteroaryl is optionally independently substituted with one or more $R_{S3}$, each of ($R_{S2}$ and $R_{S3}$) at each occurrence is independently selected from halogen, —$C_{1-6}$alkyl, halo$C_{1-6}$alkyl, halo$C_{1-6}$alkoxy, —$C_{2-6}$alkenyl, halo$C_{2-6}$alkenyl, —$C_{2-6}$ alkynyl, halo$C_{2-6}$alkynyl, —CN, oxo, —N($R_{66}$)$_2$, —O$R_{66}$, —S$R_{66}$, —S(=O)$R_{67}$, —S(=O)$_2 R_{67}$, —C(=O)$R_{67}$, —C(=O)O$R_{67}$, —OC(=O)$R_{67}$, —C(=O)N($R_{66}$)$_2$, —N$R_{66}$C(=O)$R_{67}$, —OC(=O)O$R_{66}$, —N$R_{66}$C(=O)O$R_{66}$, —N$R_{66}$C(=S)O$R_{66}$, —OC(=O)N($R_{66}$)$_2$, —N$R_{66}$C(=O)N($R_{66}$)$_2$, —S(=O)O$R_{66}$, —OS(=O)$R_{67}$, —S(=O)N($R_{66}$)$_2$, —N$R_{66}$S(=O)$R_{67}$, —S(=O)$_2$O$R_{66}$, —OS(=O)$_2 R_{67}$, —S(=O)$_2$N($R_{66}$)$_2$, —N$R_{66}$S(=O)$_2 R_{67}$, —OS(=O)$_2$ O$R_{66}$, —N$R_{66}$S(=O)$_2$O$R_{66}$, —OS(=O)$_2$N($R_{66}$)$_2$, —N$R_{66}$S(=O)$_2$N($R_{66}$)$_2$, —P($R_{66}$)$_2$, —P(=O)($R_{67}$)$_2$, 3-8 membered cycloalkyl, 3-8 membered cycloalkenyl, 3-8 membered cycloalkynyl, 4-8 membered heterocyclyl, 6-10 membered aryl, 5-10 membered heteroaryl; wherein said —$C_{1-6}$alkyl, halo$C_{1-6}$alkyl, halo$C_{1-6}$ alkoxy, —$C_{2-6}$alkenyl, halo$C_{2-6}$alkenyl, —$C_{2-6}$alkynyl, halo$C_{2-6}$alkynyl, 3-8 membered cycloalkyl, 3-8 membered cycloalkenyl, 3-8 membered cycloalkynyl, 3-8 membered heterocyclyl, 6-10 membered aryl or 5-10 membered heteroaryl is optionally independently substituted with one or more substituents selected from halogen, —$C_{1-6}$alkyl, halo$C_{1-6}$alkyl, halo$C_{1-6}$alkoxy, —$C_{2-6}$alkenyl, halo$C_{2-6}$alkenyl, —$C_{2-6}$alkynyl, halo$C_{2-6}$alkynyl, —CN, —N($R_{68}$)$_2$, —O$R_{68}$, —S$R_{68}$, —S(=O)$R_{69}$, —S(=O)$_2 R_{69}$, —C(=O)$R_{69}$, —C(=O)O$R_{68}$, —OC(=O)$R_{69}$, —C(=O)N($R_{68}$)$_2$, —N$R_{68}$C(=O)$R_{69}$, —OC(=O)O$R_{68}$, —N$R_{68}$C(=O) O$R_{68}$, —N$R_{68}$C(=S)O$R_{68}$, —OC(=O)N($R_{68}$)$_2$, —N$R_{68}$C(=O)N($R_{68}$)$_2$, —S(=O)O$R_{68}$, —OS(=O) $R_{69}$, —S(=O)N($R_{68}$)$_2$, —N$R_{68}$S(=O)$R_{69}$, —S(=O)$_2$ O$R_{68}$, —OS(=O)$_2 R_{69}$, —S(=O)$_2$N($R_{68}$)$_2$, —N$R_{68}$S (=O)$_2 R_{69}$, —OS(=O)$_2$O$R_{68}$, —N$R_{68}$S(=O)$_2$O$R_{68}$, —OS(=O)$_2$N($R_{68}$)$_2$, —N$R_{68}$S(=O)$_2$N($R_{68}$)$_2$, —P($R_{68}$)$_2$, —P(=O)($R_{69}$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

optionally, two $R_{S2}$ together with the carbon atom to which they are both attached or two $R_{S3}$ together with the carbon atom to which they are both attached form a 3-10 membered carbocyclic ring or a 3-10 heterocyclic ring; wherein, said 3-10 membered carbocylic ring or 3-10 heterocyclic ring is optionally substituted with one or more $R_{6h}$;

optionally, two adjacent $R_{S2}$ together with the carbon atoms to which they are respectively attached or two adjacent $R_{S3}$ together with the carbon atoms to which they are respectively attached form a 3-10 membered carbocyclic ring, a 3-10 membered heterocyclic ring, a 6-10 membered aryl ring or a 5-10 membered heteroaryl ring, wherein, each of rings is independently optionally substituted with one or more $R_{6i}$;

optionally, two nonadjacent $R_{S2}$ or two nonadjacent $R_{S3}$ are connected together to form a bridge containing 0, 1, 2, 3, 4, 5 or 6 carbon atoms, wherein, each of the carbon atoms in the bridge is optionally replaced by 1 or 2 heteroatoms selected from N, O, S, S=O or S(=O)$_2$; the hydrogen on the each of carbon atoms or N atoms is optionally independently substituted with $R_{6j}$;

$q_2$ is selected from 0, 1, 2, 3, 4, 5 or 6;

each of $R_{S4}$ at each occurrence is independently selected from halogen, —$C_{1-6}$alkyl, halo$C_{1-6}$alkyl, halo$C_{1-6}$ alkoxy, —$C_{2-6}$alkenyl, halo$C_{2-6}$alkenyl, —$C_{2-6}$alkynyl, halo$C_{2-6}$alkynyl, —CN, oxo, —N($R_{71}$)$_2$, —O$R_{71}$, —S$R_{71}$, —S(=O)$R_{72}$, —S(=O)$_2 R_{71}$, —C(=O)$R_{72}$, —C(=O)O$R_{71}$, —OC(=O)$R_{72}$, —C(=O)N($R_{71}$)$_2$, —N$R_{71}$C(=O)$R_{72}$, —OC(=O)O$R_{71}$, —N$R_{71}$C(=O) O$R_{71}$, —OC(=O)N($R_{71}$)$_2$, —N$R_{71}$C(=O)N($R_{71}$)$_2$, —S(=O)O$R_{71}$, —OS(=O)$R_{71}$, —S(=O)N($R_{71}$)$_2$, —N$R_{71}$S(=O)$R_{72}$, —S(=O)$_2$O$R_{71}$, —OS(=O)$_2 R_{72}$, —S(O)$_2$N($R_{71}$)$_2$, —N$R_{71}$S(=O)$_2 R_{72}$, —OS(=O)$_2$ O$R_{71}$, —N$R_{71}$S(=O)$_2$O$R_{72}$, —OS(=O)$_2$N($R_{71}$)$_2$, —N$R_{71}$S(=O)$_2$N($R_{71}$)$_2$, —P($R_{71}$)$_2$, —P(O)($R_{72}$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl; wherein said —$C_{1-6}$alkyl, halo$C_{1-6}$alkyl, halo$C_{1-6}$alkoxy, —$C_{2-6}$alkenyl, halo$C_{2-6}$alkenyl, —$C_{2-6}$alkynyl, halo$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is optionally independently substituted with one or more substituents selected from halogen, —$C_{1-6}$alkyl, halo$C_{1-6}$alkyl, halo$C_{1-6}$alkoxy, —$C_{2-6}$alkenyl, halo$C_{2-6}$alkenyl, —$C_{2-6}$alkynyl, halo$C_{2-6}$alkynyl, —CN, —N($R_{73}$)$_2$, —O$R_{73}$, —S$R_{73}$, —S(=O)$R_{74}$, —S(=O)$_2 R_{73}$, —C(=O)$R_{74}$, —C(=O)O$R_{73}$, —OC(=O)$R_{74}$, —C(=O)N($R_{73}$)$_2$, —N$R_{73}$C(=O)$R_{74}$, —OC(=O)O$R_{73}$, —N$R_{73}$C(=O) O$R_{73}$, —OC(=O)N($R_{73}$)$_2$, —N$R_{73}$C(=O)N($R_{73}$)$_2$, —S(=O)OR$_{73}$, —OS(=O)R$_{74}$, —S(=O)N(R$_{73}$)$_2$, —NR$_{73}$S(=O)R$_{74}$, —S(=O)$_2$OR$_{73}$, —OS(=O)$_2$R$_{74}$, —S(=O)$_2$N(R$_{73}$)$_2$, —NR$_{73}$S(=O)$_2$R$_{74}$, —OS(=O)$_2$OR$_{73}$, —NR$_{73}$S(=O)$_2$OR$_{74}$, —OS(=O)$_2$N(R$_{73}$)$_2$, —NR$_{73}$S(=O)$_2$N(R$_{73}$)$_2$, —P(R$_{73}$)$_2$, —P(=O)(R$_{74}$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

q$_4$ is selected from 0, 1, 2, 3, 4, 5 or 6;

R$_3$ is selected from 6-10 membered aryl or 5-10 membered heteroaryl, wherein said 6-10 membered aryl or 5-10 membered heteroaryl is optionally independently substituted with one or more R$_{31}$;

R$_{31}$ at each occurrence is independently selected from halogen, —C$_{1-10}$alkyl, haloC$_{1-10}$alkyl, haloC$_{1-10}$alkoxy, —C$_{2-10}$alkenyl, haloC$_{2-10}$alkenyl, —C$_{2-10}$alkynyl, haloC$_{2-10}$alkynyl, —CN, oxo, —N(R$_{75}$)$_2$, —OR$_{75}$, —SR$_{75}$, —S(=O)R$_{76}$, —S(=O)$_2$R$_{76}$, —C(=O)R$_{76}$, —C(=O)OR$_{75}$, —OC(=O)R$_{76}$, —C(=O)N(R$_{75}$)$_2$, —NR$_{75}$C(=O)R$_{76}$, —OC(=O)OR$_{75}$, —NR$_{75}$C(=O)OR$_{75}$, —OC(=O)N(R$_{75}$)$_2$, —NR$_{75}$C(=O)N(R$_{75}$)$_2$, —S(=O)OR$_{75}$, —OS(=O)R$_{76}$, —S(=O)N(R$_{75}$)$_2$, —NR$_{75}$S(O)R$_{76}$, —S(=O)$_2$OR$_{75}$, —OS(=O)$_2$R$_{76}$, —S(=O)$_2$N(R$_{75}$)$_2$, —NR$_{75}$S(=O)$_2$R$_{76}$, —OS(=O)$_2$OR$_{75}$, —NR$_{75}$S(=O)$_2$OR$_{75}$, —OS(=O)$_2$N(R$_{75}$)$_2$, —NR$_{75}$S(=O)$_2$N(R$_{75}$)$_2$, —P(R$_{75}$)$_2$, —P(=O)(R$_{75}$)$_2$, 3-10 membered cycloalkyl, 3-10 membered cycloalkenyl, 3-10 membered cycloalkynyl, 3-10 membered heterocyclyl, 6-10 membered aryl or 5-10 membered heteroaryl, wherein said —C$_{1-10}$alkyl, haloC$_{1-10}$alkyl, haloC$_{1-10}$alkoxy, —C$_{2-10}$alkenyl, haloC$_{2-10}$alkenyl, —C$_{2-10}$alkynyl, haloC$_{2-10}$alkynyl, 3-10 membered cycloalkyl, 3-10 membered cycloalkenyl, 3-10 membered cycloalkynyl, 3-10 membered heterocyclyl, 6-10 membered aryl or 5-10 membered heteroaryl is optionally independently substituted with one or more substituents selected from halogen, —C$_{1-6}$alkyl, haloC$_{1-6}$alkyl, haloC$_{1-6}$alkoxy, —C$_{2-6}$alkenyl, haloC$_{2-6}$alkenyl, —C$_{2-6}$alkynyl, haloC$_{2-6}$alkynyl, —CN, —N(R$_{77}$)$_2$, —OR$_{77}$, —SR$_{77}$, —S(=O)R$_{78}$, —S(=O)$_2$R$_{78}$, —C(=O)R$_{78}$, —C(=O)OR$_{77}$, —OC(=O)R$_{78}$, —C(=O)N(R$_{77}$)$_2$, —NR$_{77}$C(=O)R$_{78}$, —OC(=O)OR$_{77}$, —NR$_{77}$C(=O)OR$_{77}$, —OC(=O)N(R$_{77}$)$_2$, —NR$_{77}$C(=O)N(R$_{77}$)$_2$, —S(=O)OR$_{77}$, —OS(=O)R$_{78}$, —S(=O)N(R$_{77}$)$_2$, —NR$_{77}$S(=O)R$_{78}$, —S(=O)$_2$OR$_{77}$, —OS(=O)$_2$R$_{78}$, —S(=O)$_2$N(R$_{77}$)$_2$, —NR$_{77}$S(=O)$_2$R$_{78}$, —OS(=O)$_2$OR$_{77}$, —NR$_{77}$S(=O)$_2$OR$_{77}$, —OS(=O)$_2$N(R$_{77}$)$_2$, —NR$_{77}$S(=O)$_2$N(R$_{77}$)$_2$, —P(R$_{77}$)$_2$, —P(=O)(R$_{78}$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

each of R$_2$, R$_4$ and R$_5$ is independently selected from hydrogen, halogen, —C$_{1-10}$alkyl, haloC$_{1-10}$alkyl, haloC$_{1-10}$alkoxy, —C$_{2-10}$alkenyl, haloC$_{2-10}$alkenyl, —C$_{2-10}$alkynyl, haloC$_{2-10}$alkynyl, —CN, oxo, —N(R$_{81}$)$_2$, —OR$_{81}$, —SR$_{81}$, —S(=O)R$_{82}$, —S(=O)$_2$R$_{82}$, —C(=O)R$_{82}$, —C(=O)OR$_{81}$, —OC(=O)R$_{82}$, —C(=O)N(R$_{81}$)$_2$, —NR$_{81}$C(=O)R$_{82}$, —OC(=O)OR$_{81}$, —NR$_{81}$C(=O)OR$_{81}$, —OC(=O)N(R$_{81}$)$_2$, —NR$_{81}$C(=O)NR$_{81}$)$_2$, —S(=O)OR$_{81}$, —OS(=O)R$_{82}$, —S(=O)N(R$_{81}$)$_2$, —NR$_{81}$S(=O)R$_{82}$, —S(=O)$_2$OR$_{81}$, —OS(=O)$_2$R$_{82}$, —S(=O)$_2$N(R$_{81}$)$_2$, —NR$_{81}$S(=O)$_2$R$_{82}$, —OS(=O)$_2$OR$_{81}$, —NR$_{81}$S(=O)$_2$OR$_{81}$, —OS(=O)$_2$N(R$_{81}$)$_2$, —NR$_{81}$S(=O)$_2$N(R$_{81}$)$_2$, —P(R$_{81}$)$_2$, —P(=O)(R$_{82}$)$_2$, 3-10 membered cycloalkyl, 3-10 membered cycloalkenyl, 3-10 membered cycloalkynyl, 3-10 membered heterocyclyl, 6-10 membered aryl or 5-10 membered heteroaryl; wherein said —C$_{1-10}$alkyl, haloC$_{1-10}$alkyl, haloC$_{1-10}$alkoxy, —C$_{2-10}$alkenyl, haloC$_{2-10}$alkenyl, —C$_{2-10}$alkynyl, haloC$_{2-10}$alkynyl, 3-10 membered cycloalkyl, 3-10 membered cycloalkenyl, 3-10 membered cycloalkynyl, 3-10 membered heterocyclyl, 6-10 membered aryl or 5-10 membered heteroaryl is optionally independently substituted with one or more substituents selected from halogen, —C$_{1-6}$alkyl, haloC$_{1-6}$alkyl, haloC$_{1-6}$alkoxy, —C$_{2-6}$alkenyl, haloC$_{2-6}$alkenyl, —C$_{2-6}$alkynyl, haloC$_{2-6}$alkynyl, —CN, —N(R$_{83}$)$_2$, —OR$_{83}$, —SR$_{83}$, —S(=O)R$_{84}$, —S(=O)$_2$R$_{84}$, —C(=O)R$_{84}$, —C(=O)OR$_{83}$, —OC(=O)R$_{83}$, —C(=O)N(R$_{83}$)$_2$, —NR$_{83}$C(=O)R$_{84}$, —OC(=O)OR$_{83}$, —NR$_{83}$C(=O)OR$_{83}$, —OC(=O)N(R$_{83}$)$_2$, —NR$_{83}$C(=O)N(R$_{84}$)$_2$, —S(=O)OR$_{83}$, —OS(=O)R$_{84}$, —S(=O)N(R$_{83}$)$_2$, —NR$_{83}$S(=O)R$_{84}$, —S(=O)$_2$OR$_{83}$, —OS(=O)$_2$R$_{84}$, —S(=O)$_2$N(R$_{83}$)$_2$, —NR$_{83}$S(=O)$_2$R$_{84}$, —OS(=O)$_2$OR$_{83}$, —NR$_{83}$S(=O)$_2$OR$_{83}$, —OS(=O)$_2$N(R$_{83}$)$_2$, —NR$_{83}$S(=O)$_2$N(R$_{83}$)$_2$, —P(R$_{83}$)$_2$, —P(=O)(R$_{84}$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

each of R$_{6a}$, R$_{61}$, R$_{63}$, R$_{65}$, R$_{66}$, R$_{68}$, R$_{71}$, R$_{73}$, R$_{75}$, R$_{77}$, R$_{81}$ and R$_{83}$ at each occurrence is independently selected from hydrogen, halogen, —C$_{1-10}$alkyl, haloC$_{1-10}$alkyl, —C$_{2-10}$alkenyl, —C$_{2-10}$alkynyl, —S(=O)R$_a$, —S(=O)$_2$R$_a$, —C(=O)R$_a$, —C(=O)OR$_a$, —C(=O)NR$_a$)$_2$, —S(=O)OR$_a$, —S(=O)N(R$_a$)$_2$, —S(=O)$_2$OR$_a$, —S(=O)$_2$N(R$_a$)$_2$, —P(=O)(R$_a$)$_2$, 3-10 membered cycloalkyl, 3-10 membered cycloalkenyl, 3-10 membered cycloalkynyl, 3-10 membered heterocyclyl, 6-10 membered aryl or 5-10 membered heteroaryl; wherein said —C$_{1-10}$alkyl, haloC$_{1-10}$alkyl, —C$_{2-10}$alkenyl, —C$_{2-10}$alkynyl, 3-10 membered cycloalkyl, 3-10 membered cycloalkenyl, 3-10 membered cycloalkynyl, 3-10 membered heterocyclyl, 6-10 membered aryl or 5-10 membered heteroaryl is optionally independently substituted with one or more substituents selected from halogen, —C$_{1-6}$alkyl, haloC$_{1-6}$alkyl, haloC$_{1-6}$alkoxy, —C$_{2-6}$alkenyl, —C$_{2-6}$alkynyl, —CN, —N(R$_c$)$_2$, —OR$_c$, —SR$_c$, —S(=O) R$_d$, —S(=O)$_2$R$_d$, —C(=O) R$_d$, —C(=O)OR$_c$, —OC(=O)R$_d$, —C(=O)N(R$_c$)$_2$, —NR$_c$C(=O)R$_d$, —OC(=O)OR$_c$, —NR$_c$C(=O)OR$_c$, —OC(=O)N(R$_c$)$_2$, —NR$_c$C(=O)N(R$_c$)$_2$, —S(=O)OR$_c$, —OS(=O)R$_d$, —S(=O)N(R$_c$)$_2$, —NR$_c$S(=O)R$_d$, —S(=O)$_2$OR$_c$, —OS(=O)$_2$R$_d$, —S(=O)$_2$N(R$_c$)$_2$, —NR$_c$S(=O)$_2$R$_d$, —OS(=O)$_2$OR$_c$, —NR$_c$S(=O)$_2$OR$_c$, —OS(=O)$_2$NR$_c$, —NR$_c$S(=O)$_2$N(R$_c$)$_2$, —P(R$_c$)$_2$, —P(=O)(R$_d$)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

optionally, each of two R$_{61}$, two R$_{63}$, two R$_{65}$, two R$_{66}$, two R$_{68}$, two R$_{71}$, two R$_{73}$, two R$_{75}$, two R$_{77}$, two R$_{81}$, and two R$_{83}$) independently together with the nitrogen atom to which they are both attached forms a 3-20 membered heterocyclic ring or a 5-10 membered heteroaryl ring, wherein said 3-20 membered heterocyclic ring or 5-10 membered heteroaryl ring is optionally independently substituted with one or more R$_{6k}$;

each of R$_{62}$, R$_{64}$, R$_{67}$, R$_{69}$, R$_{72}$, R$_{74}$, R$_{76}$, R$_{78}$, R$_{82}$ and R$_{84}$ at each occurrence is independently selected from hydrogen, —C$_{1-10}$alkyl, haloC$_{1-10}$alkyl, haloC$_{1-10}$alkoxy, —C$_{2-10}$alkenyl, haloC$_{2-10}$alkenyl, —C$_{2-10}$alkynyl, haloC$_{2-10}$alkynyl, —N(R$_b$)$_2$, —OR$_b$, —SR$_b$, 3-10 membered cycloalkyl, 3-10 membered cycloalkenyl, 3-10 membered cycloalkynyl, 3-10 membered heterocyclyl, 6-10 membered aryl or 5-10 membered heteroaryl; wherein said —$C_{1-10}$alkyl, halo$C_{1-10}$alkyl, halo$C_{1-10}$alkoxy, —$C_{2-10}$alkenyl, —$C_{2-10}$alkynyl, 3-10 membered cycloalkyl, 3-10 membered cycloalkenyl, 3-10 membered cycloalkynyl, 3-10 membered heterocyclyl, 6-10 membered aryl or 5-10 membered heteroaryl is optionally independently substituted with one or more substituents selected from halogen, —$C_{1-6}$ alkyl, halo$C_{1-6}$alkyl, halo$C_{1-6}$alkoxy, —$C_{2-6}$alkenyl, —$C_{2-6}$alkynyl, —CN, —N($R_c$)$_2$, —O$R_c$, —S$R_c$, —S(=O)$R_d$, —S(=O)$_2R_d$, —C(=O)$R_d$, —C(=O)O$R_c$, —OC(=O)$R_d$, —C(=O)N($R_c$)$_2$, —N$R_c$C(=O)$R_d$, —OC(=O)O$R_c$, —N$R_c$C(=O)O$R_d$, —OC(=O)N($R_c$)$_2$, —N$R_c$C(=O)N($R_c$)$_2$, —S(=O)O$R_c$, —OS(=O)$R_d$, —S(=O)N($R_c$)$_2$, —N$R_c$S(=O)$R_d$, —S(=O)$_2$O$R_c$, —OS(=O)$_2R_d$, —S(=O)$_2$N($R_c$)$_2$, —N$R_c$S(=O)$_2R_d$, —OS(=O)$_2$O$R_c$, —N$R_c$S(=O)$_2$O$R_c$, —OS(=O)$_2$N$R_c$, —N$R_c$S(=O)$_2$N($R_c$)$_2$, —P($R_c$)$_2$, —P(=O)($R_d$)$_2$, 3-6 membered cycloalkyl, 3-6 membered cycloalkenyl, 3-6 membered cycloalkynyl, 3-10 membered heterocyclyl, 6-10 membered aryl or 5-10 membered heteroaryl;

each of $R_a$, $R_b$, $R_c$ and $R_d$ at each occurrence is independently selected from hydrogen, —$C_{1-6}$alkyl, halo$C_{1-6}$alkyl, halo$C_{1-6}$alkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl; wherein said —$C_{1-6}$alkyl, halo$C_{1-6}$alkyl, halo$C_{1-6}$alkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is optionally independently substituted with one or more $R_{6i}$;

optionally, each of two $R_a$, two $R_b$ and two $R_c$ independently together with the atom to which they are both attached forms a 3-6 membered heterocyclic ring, wherein said 3-6 membered heterocyclic ring is independently optionally substituted with one or more $R_{6m}$;

each of $R_{6b}$, $R_{6c}$, $R_{6d}$, $R_{6e}$, $R_{6f}$, $R_{6h}$, $R_{6i}$, $R_{6j}$, $R_{6k}$, $R_{6l}$ and $R_{6m}$ at each occurrence is independently selected from halogen, —$C_{1-6}$alkyl, halo$C_{1-6}$alkyl, halo$C_{1-6}$alkoxy, —$C_{2-6}$alkenyl, —$C_{2-6}$alkynyl, —CN, oxo, —NH$_2$, —NH($C_{1-6}$alkyl), —N($C_{1-6}$alkyl)$_2$, —OH, —O($C_{1-6}$alkyl), —SH, —S($C_{1-6}$alkyl), —S(=O)($C_{1-6}$alkyl), —S(=O)$_2$($C_{1-6}$alkyl), —C(=O)($C_{1-6}$alkyl), —C(=O)OH, —C(=O)(O$C_{1-6}$alkyl), —OC(=O)($C_{1-6}$ alkyl), —C(=O)NH$_2$, —C(=O)NH($C_{1-6}$alkyl), —C(=O)N($C_{1-6}$alkyl)$_2$, —NHC(=O)($C_{1-6}$alkyl), —N($C_{1-6}$alkyl)C(=O)($C_{1-6}$alkyl), —OC(=O)O($C_{1-6}$ alkyl), —NHC(=O)(O$C_{1-6}$alkyl), —N($C_{1-6}$alkyl)C(=O)(O$C_{1-6}$alkyl), —OC(=O)NH($C_{1-6}$alkyl), —OC(=O)N($C_{1-6}$alkyl)$_2$, —NHC(=O)NH$_2$, —NHC(=O)NH($C_{1-6}$alkyl), —NHC(=O)N($C_{1-6}$alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N($C_{1-6}$alkyl)$_2$, —S(=O)(O$C_{1-6}$alkyl), —OS(=O)($C_{1-6}$alkyl), —S(=O)NH$_2$, —S(=O)NH($C_{1-6}$alkyl), —S(=O)N($C_{1-6}$alkyl)$_2$, —NHS(=O)($C_{1-6}$alkyl), —N($C_{1-6}$alkyl)S(=O)($C_{1-6}$ alkyl), —S(=O)(O$C_{1-6}$alkyl), —OS(=O)$_2$ ($C_{1-6}$alkyl), —S(=O)$_2$NH$_2$, —S(=O)$_2$NH($C_{1-6}$alkyl), —S(=O)$_2$N($C_{1-6}$alkyl)$_2$, —NHS(=O)$_2$($C_{1-6}$alkyl), —N($C_{1-6}$alkyl)S(=O)$_2$($C_{1-6}$alkyl), —OS(=O)$_2$O($C_{1-6}$ alkyl), —NHS(=O)$_2$O($C_{1-6}$alkyl), —N($C_{1-6}$alkyl)S(=O)$_2$O($C_{1-6}$alkyl), —OS(=O)$_2$NH$_2$, —OS(=O)$_2$NH($C_{1-6}$alkyl), —OS(=O)$_2$N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$N($C_{1-6}$alkyl)$_2$, —PH($C_{1-6}$alkyl), —P($C_{1-6}$ alkyl)$_2$, —P(=O)H($C_{1-6}$alkyl), —P(=O)($C_{1-6}$ alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl; wherein, said —$C_{1-6}$alkyl, halo$C_{1-6}$alkyl, halo$C_{1-6}$alkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is optionally substituted with one or more substituents selected from halogen, —$C_{1-3}$alkyl, halo$C_{1-3}$alkyl, halo$C_{1-3}$alkoxy, —$C_{2-3}$alkenyl, —$C_{2-3}$alkynyl, —CN, —NH$_2$, —NH($C_{1-3}$alkyl), —N($C_{1-3}$alkyl)$_2$, —OH, —O($C_{1-3}$alkyl), —SH, —S($C_{1-3}$alkyl), —S(=O)($C_{1-3}$ alkyl), —S(=O)$_2$($C_{1-3}$alkyl), —C(=O)($C_{1-3}$alkyl), —C(=O)OH, —C(=O)(O$C_{1-3}$alkyl), —OC(=O)($C_{1-3}$ alkyl), —C(=O)NH$_2$, —C(=O)NH($C_{1-3}$alkyl), —C(=O)N($C_{1-3}$alkyl)$_2$, —NHC(=O)($C_{1-3}$alkyl), —N($C_{1-3}$alkyl)C(=O)($C_{1-3}$alkyl), —OC(=O)O($C_{1-3}$ alkyl), —NHC(=O)(O$C_{1-3}$alkyl), —N($C_{1-3}$alkyl)C(=O)(O$C_{1-3}$alkyl), —OC(=O)NH($C_{1-3}$alkyl), —OC(=O)N($C_{1-3}$alkyl)$_2$, —NHC(=O)NH$_2$, —NHC(=O)NH($C_{1-3}$alkyl), —NHC(=O)N($C_{1-3}$alkyl)$_2$, —N($C_{1-3}$ alkyl)C(=O)NH$_2$, —N($C_{1-3}$alkyl)C(=O)NH($C_{1-3}$alkyl), —N($C_{1-3}$alkyl)C(=O)N($C_{1-3}$alkyl)$_2$, —S(=O)(O$C_{1-3}$alkyl), —OS(=O)($C_{1-3}$alkyl), —S(=O)NH$_2$—, —S(=O)NH($C_{1-3}$alkyl), —S(=O)N($C_{1-3}$ alkyl)$_2$, —NHS(=O)($C_{1-3}$alkyl), —N($C_{1-3}$alkyl)S(=O)($C_{1-3}$alkyl), —S(=O)$_2$(O$C_{1-3}$alkyl), —OS(=O)$_2$ ($C_{1-3}$alkyl), —S(=O)$_2$NH$_2$, —S(=O)$_2$NH ($C_{1-3}$ alkyl), —S(=O)$_2$N($C_{1-3}$alkyl)$_2$, —NHS(=O)$_2$ ($C_{1-3}$alkyl), —N($C_{1-3}$alkyl)S(=O)$_2$($C_{1-3}$alkyl), —OS(=O)$_2$O($C_{1-3}$alkyl), —NHS(=O)$_2$O($C_{1-3}$alkyl), —N($C_{1-3}$alkyl)S(=O)$_2$O($C_{1-3}$alkyl), —OS(=O)$_2$NH$_2$, —OS(=O)$_2$NH($C_{1-3}$alkyl), —OS(=O)$_2$N($C_{1-3}$ alkyl)$_2$, —NHS(=O)$_2$NH$_2$, —NHS(=O)$_2$NH($C_{1-3}$alkyl), —NHS(=O)$_2$N($C_{1-3}$alkyl)$_2$, —N($C_{1-3}$alkyl)S(=O)$_2$NH$_2$, —N($C_{1-3}$alkyl)S(=O)$_2$NH($C_{1-3}$alkyl), —N($C_{1-3}$alkyl)S(=O)$_2$N($C_{1-3}$alkyl)$_2$, —PH($C_{1-3}$alkyl), —P($C_{1-3}$alkyl)$_2$, —P(=O)H($C_{1-3}$alkyl), —P(=O)($C_{1-3}$alkyl)$_2$, 3-6 membered cycloalkyl, 3-6 membered cycloalkenyl, 3-6 membered cycloalkynyl, 3-6 membered heterocyclyl, 6 membered aryl or 5-6 membered heteroaryl;

each of heterocyclyl and heteroaryl at each occurrence is independently contain 1, 2, 3 or 4 heteroatoms selected from N, O, S, S(=O) or S(=O)$_2$.

In some embodiments, the KRAS G12D binding moiety is:

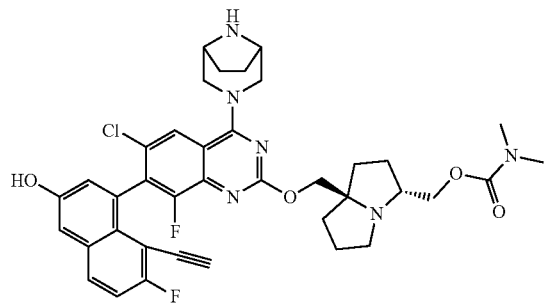

,

125
-continued
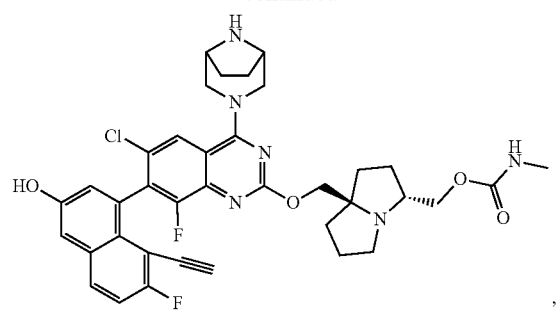
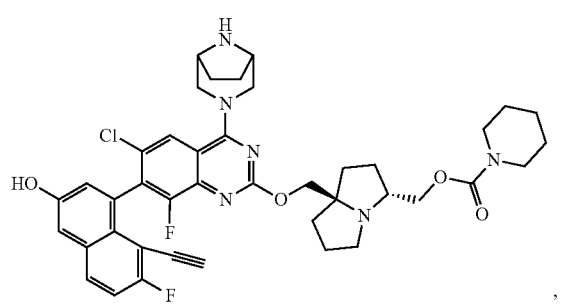
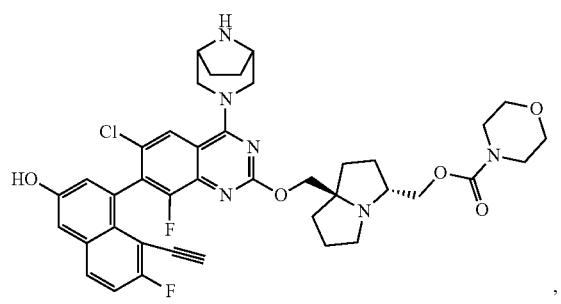
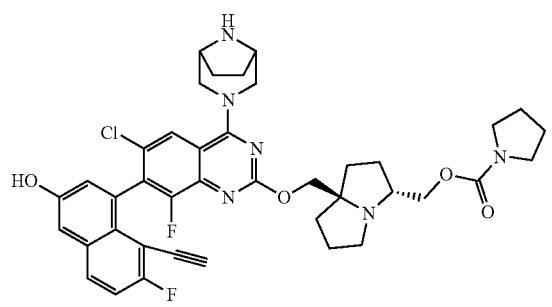
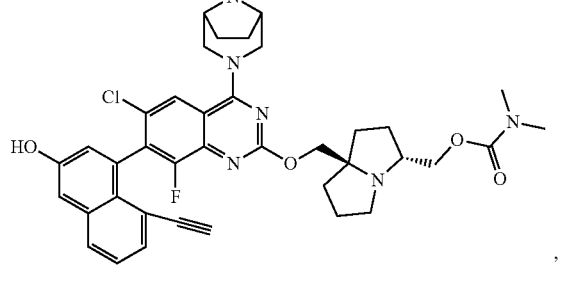
126
-continued
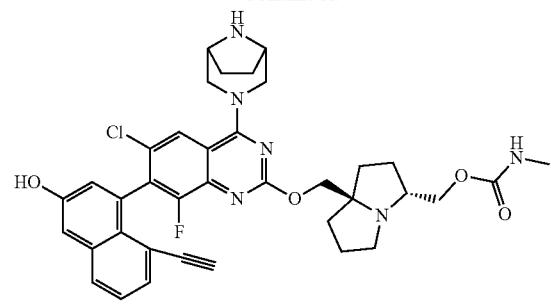
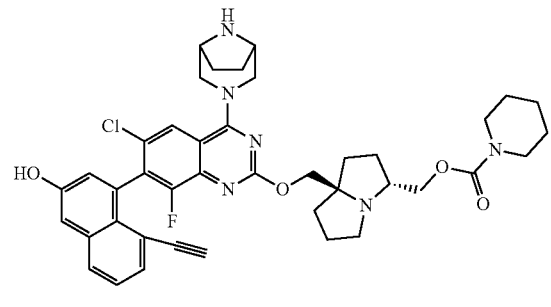
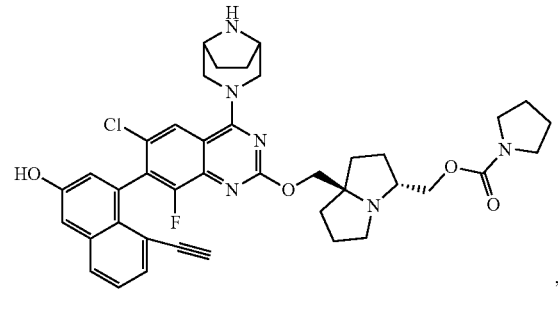
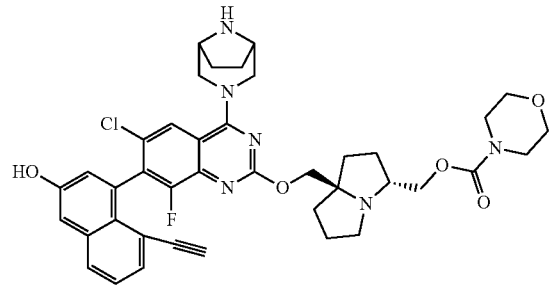
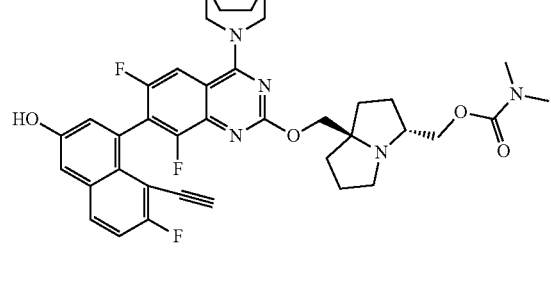

127
-continued
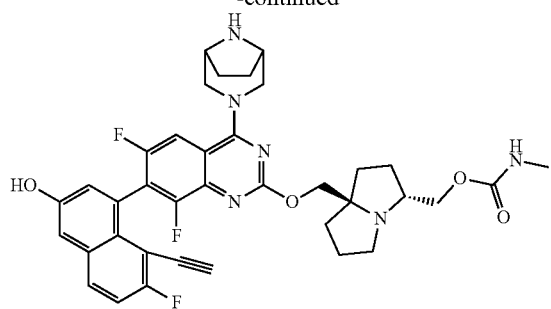
,
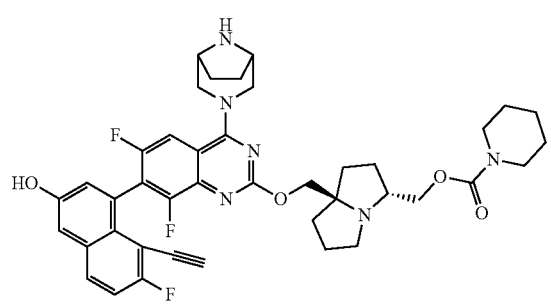
,
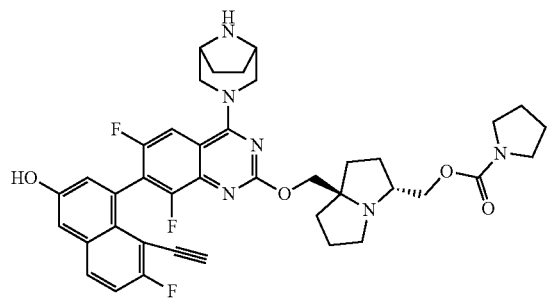
,

,

,
128
-continued
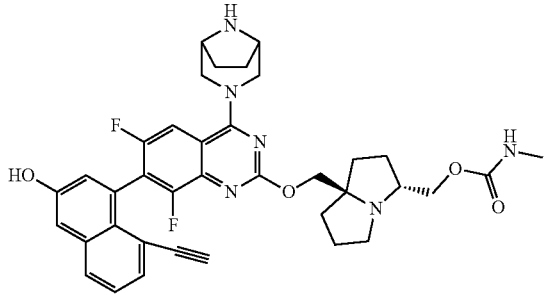
,
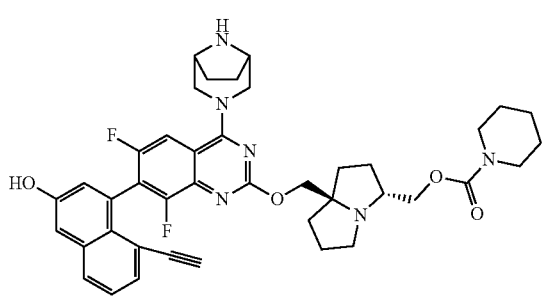
,
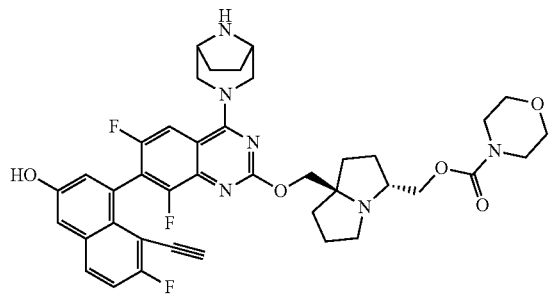
,
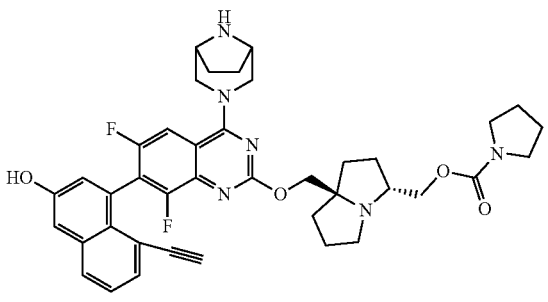
,
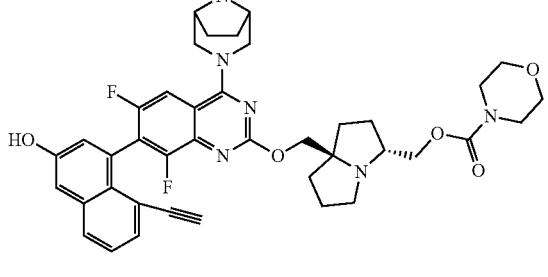
, 129
-continued 130
-continued 131
-continued
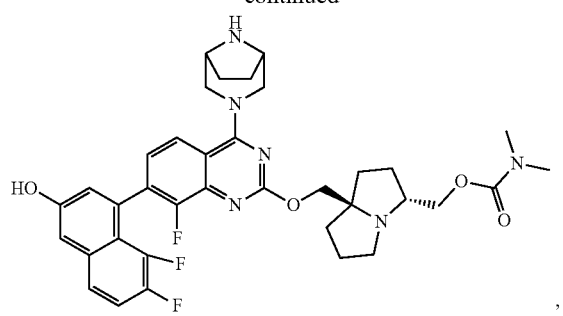
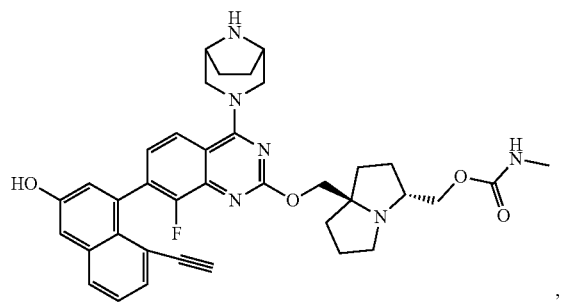
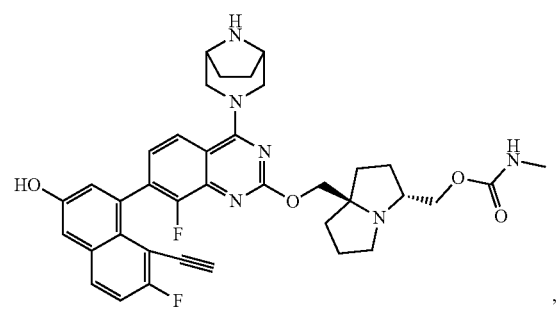
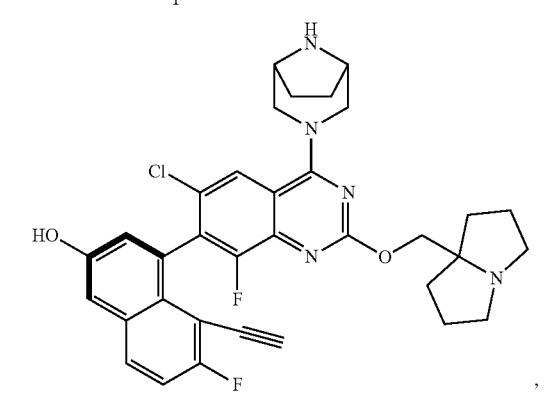
132
-continued
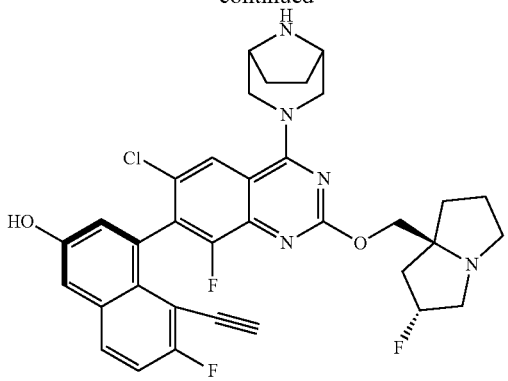
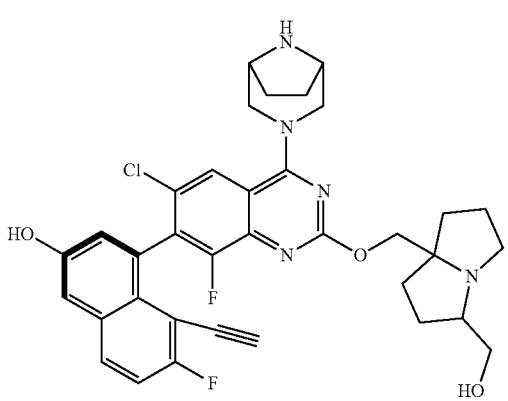
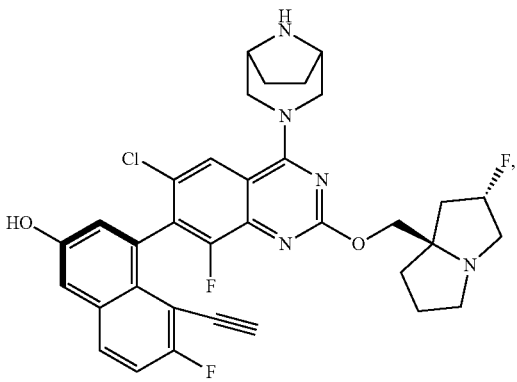
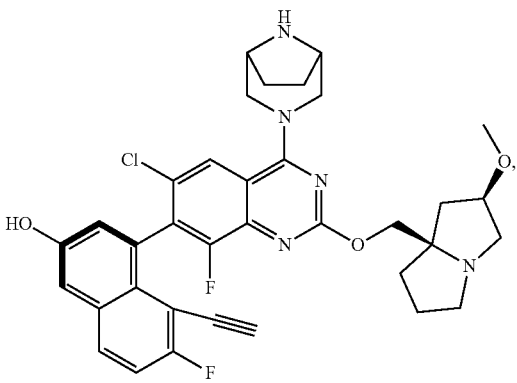

133
-continued
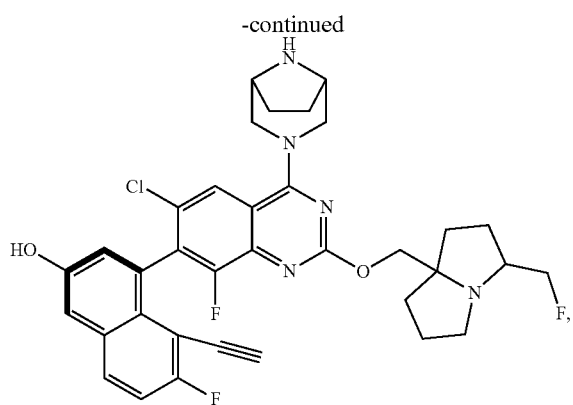
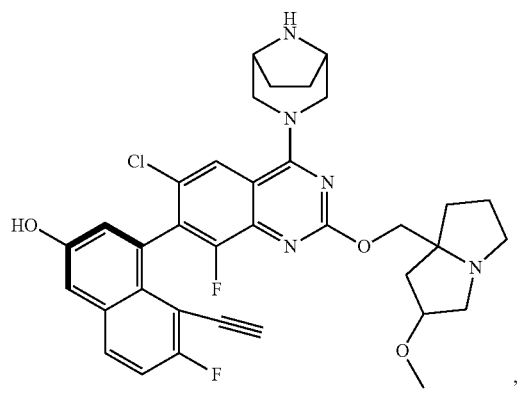
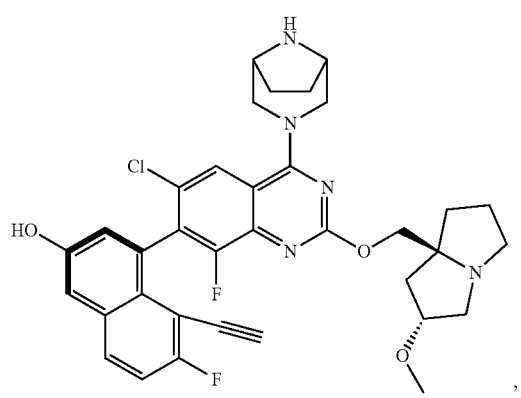
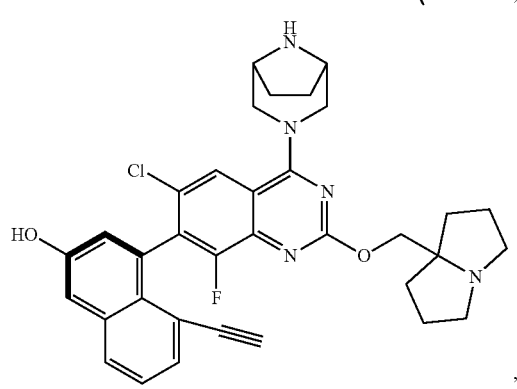
134
-continued
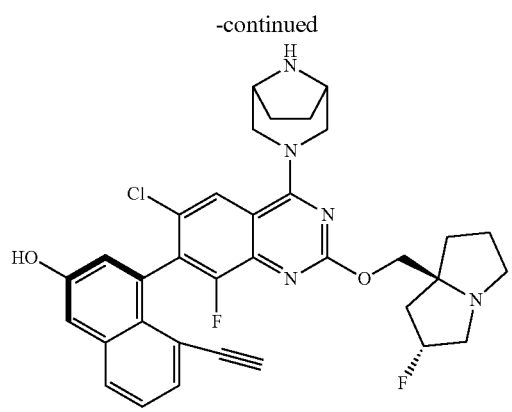
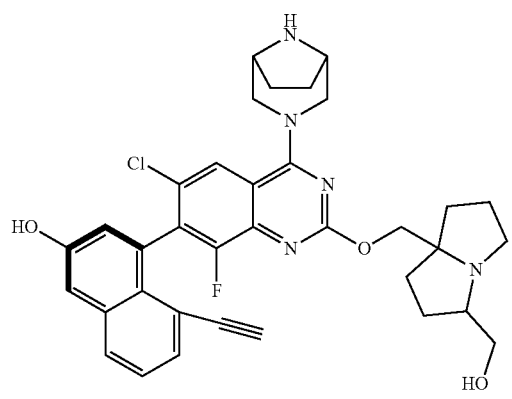
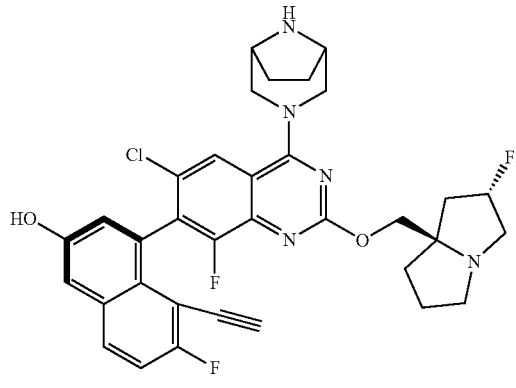
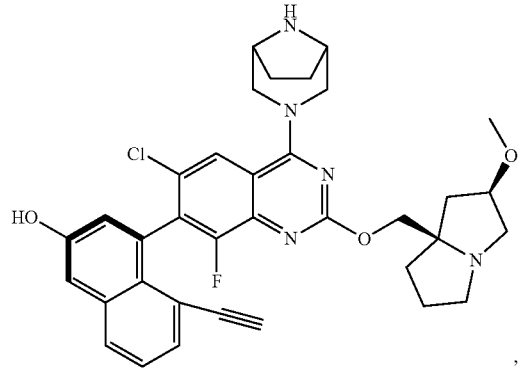

135 -continued
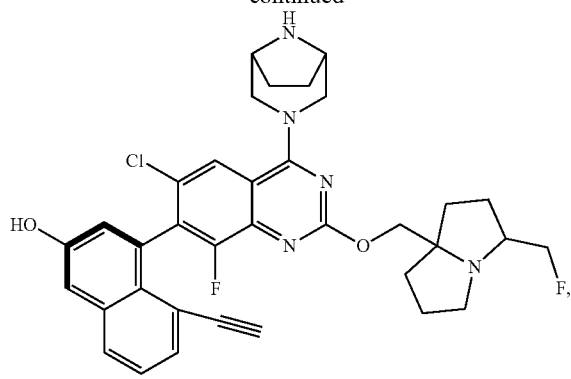
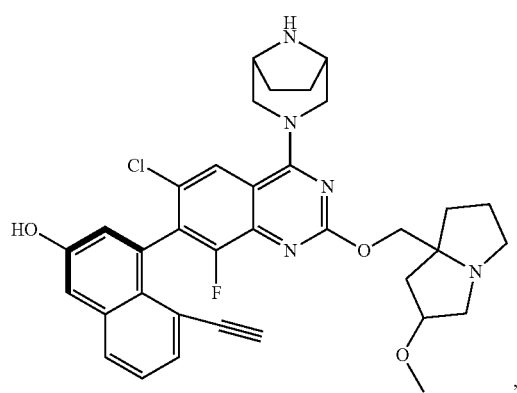
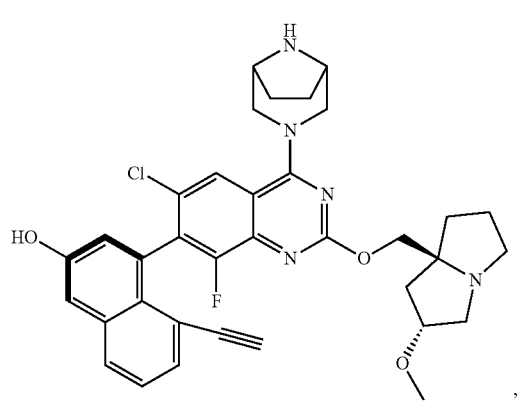
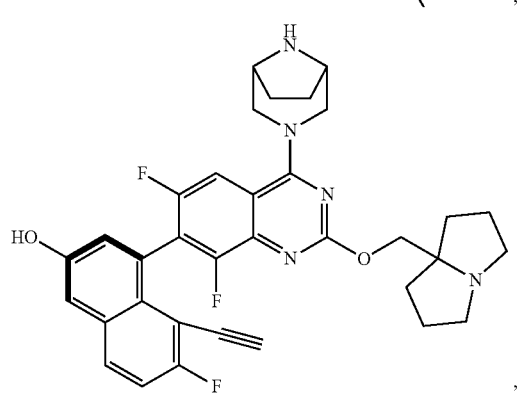
136 -continued
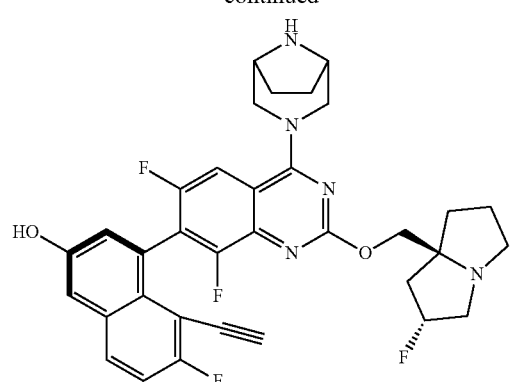
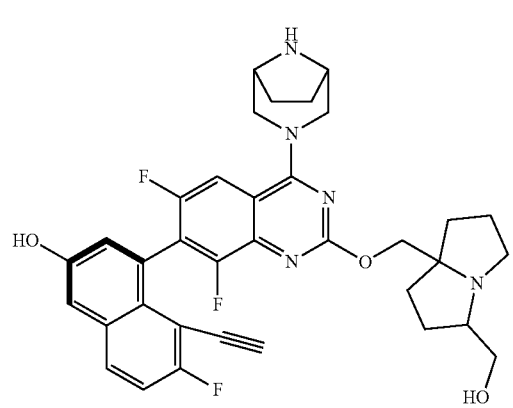
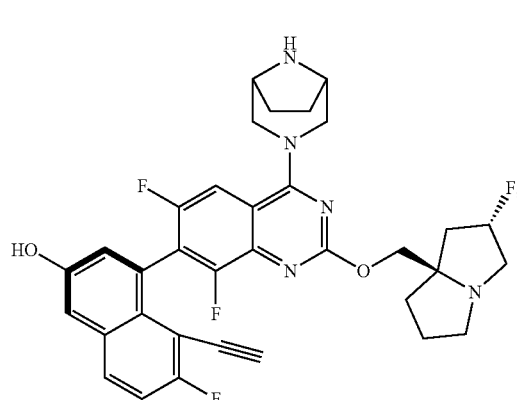
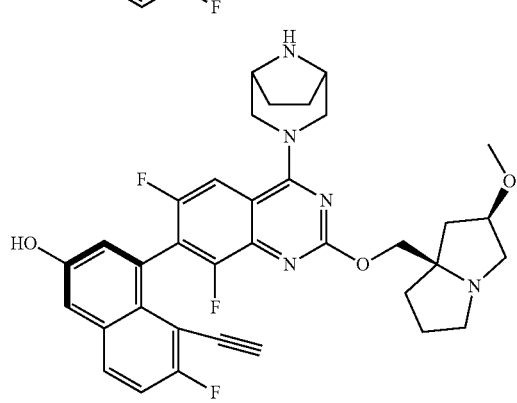

137
-continued
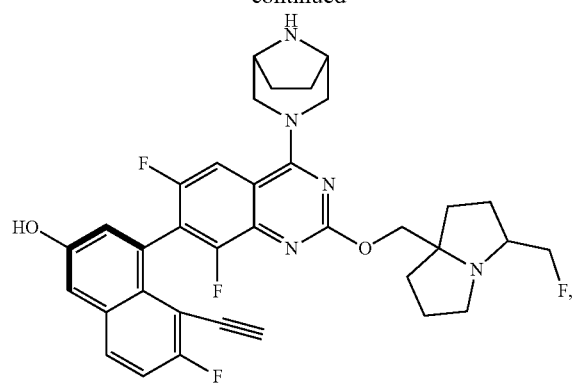
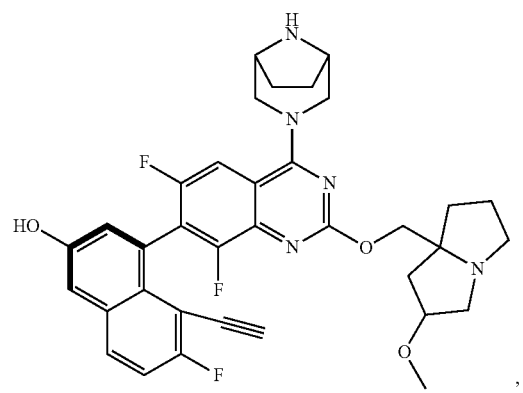
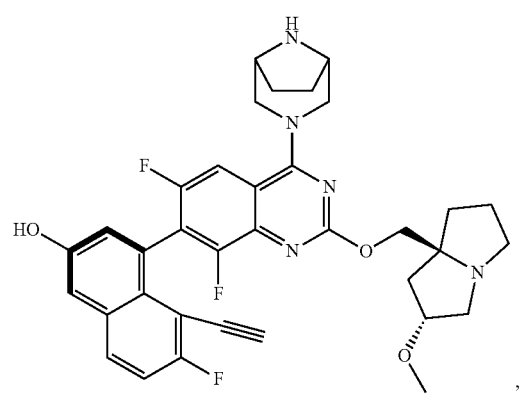
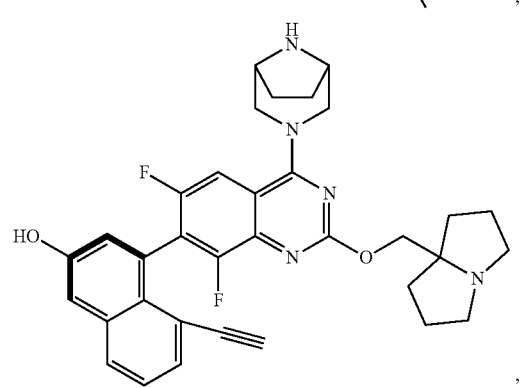
138
-continued
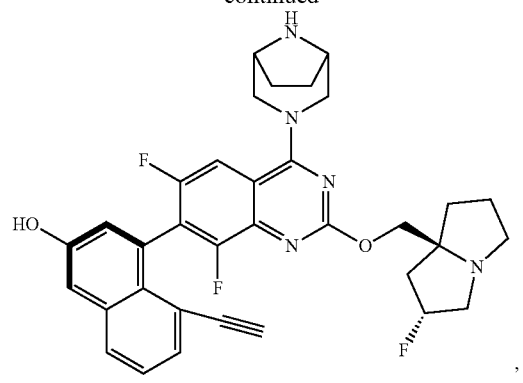
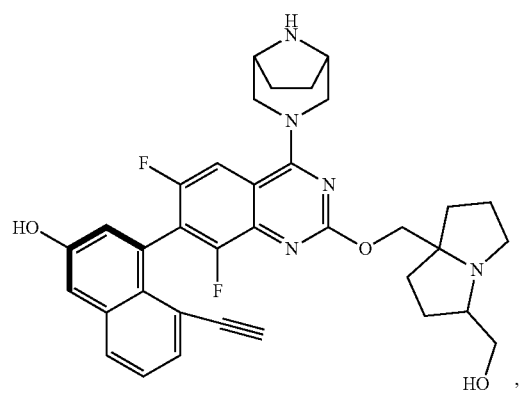
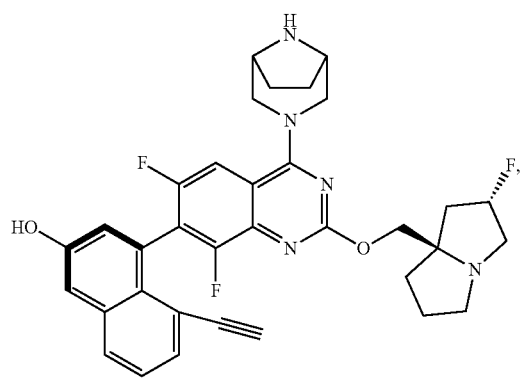
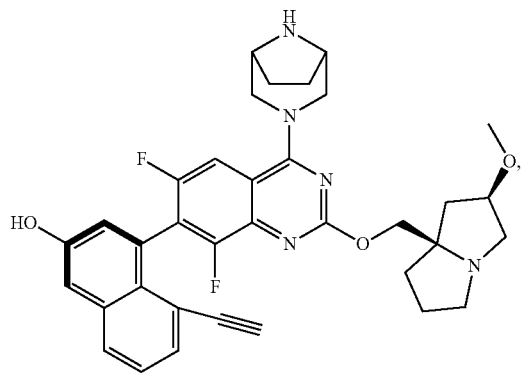

139
-continued
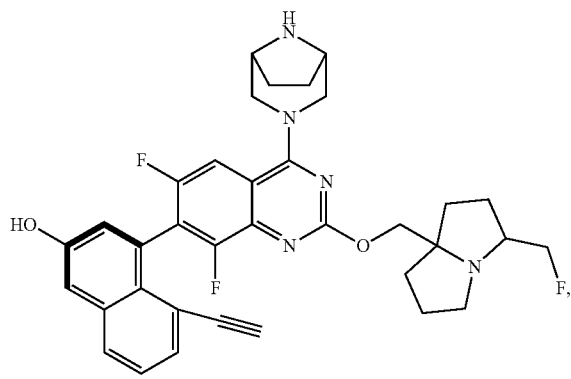
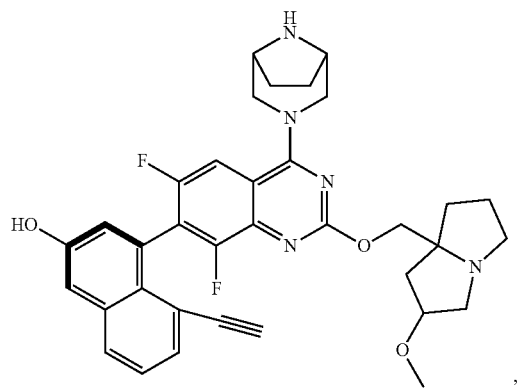
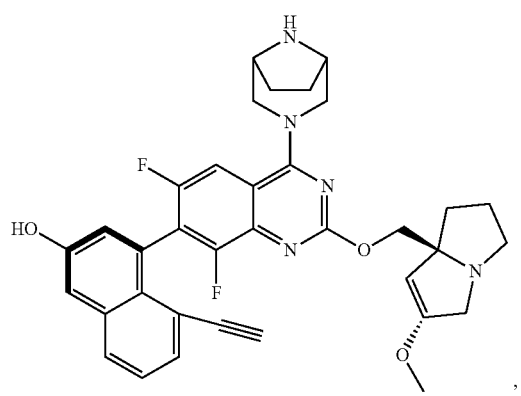
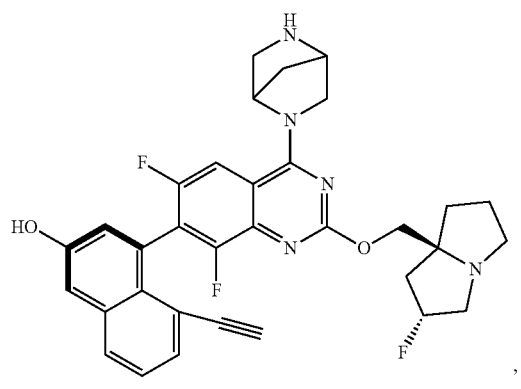
140
-continued
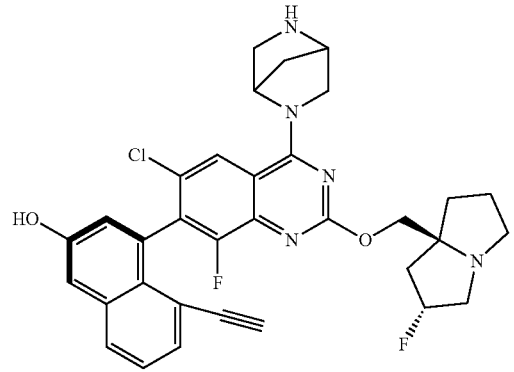
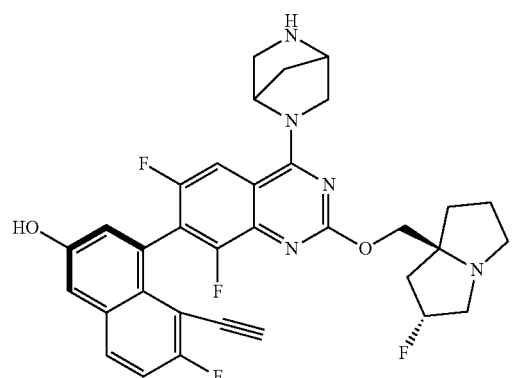
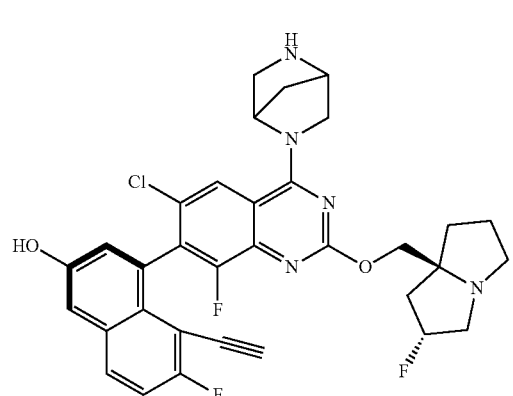
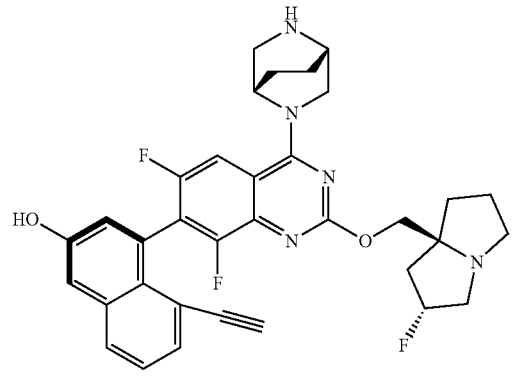

141
-continued
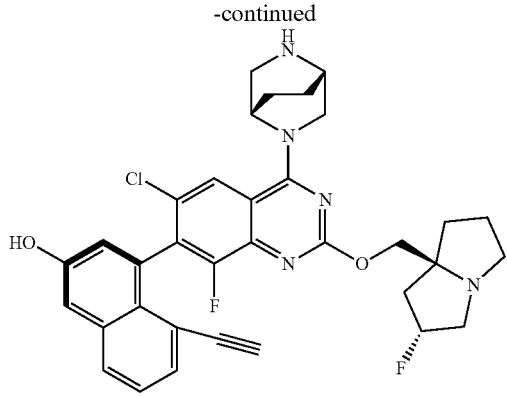
142
-continued
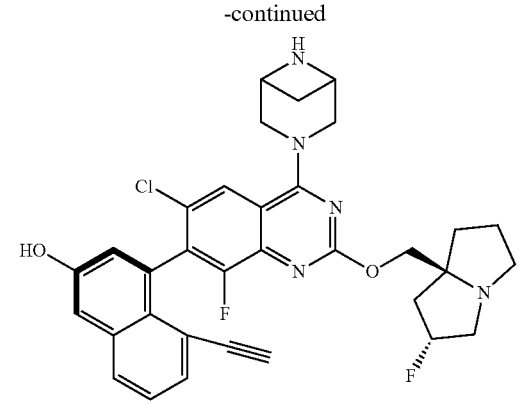
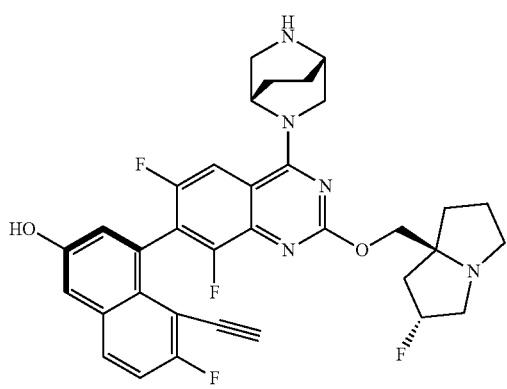
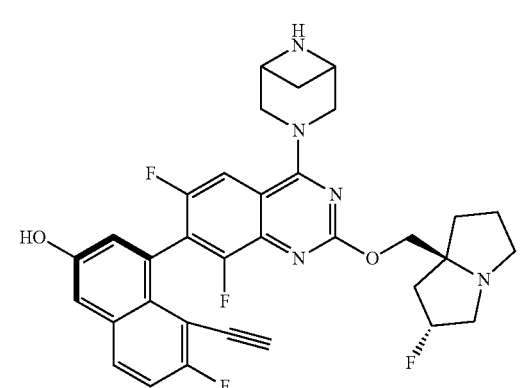
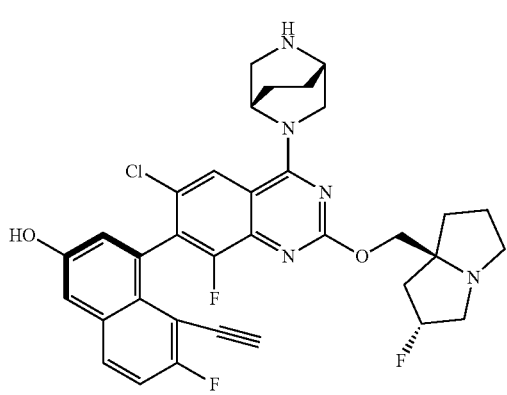
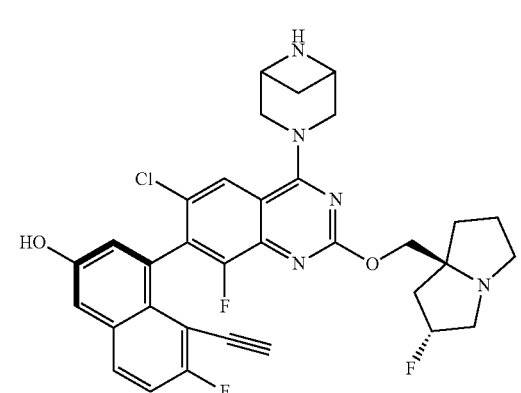
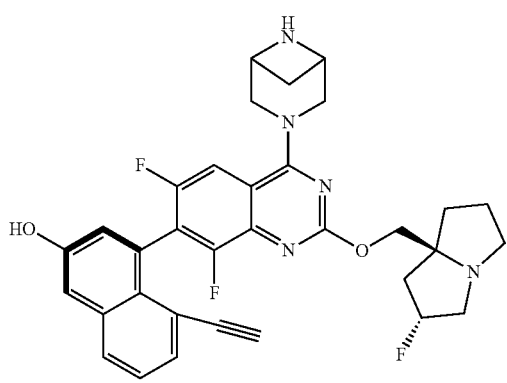
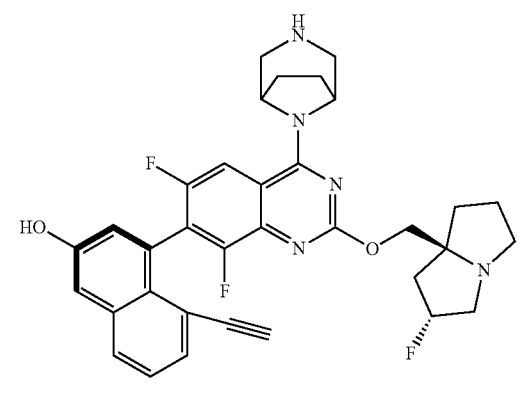

143
-continued
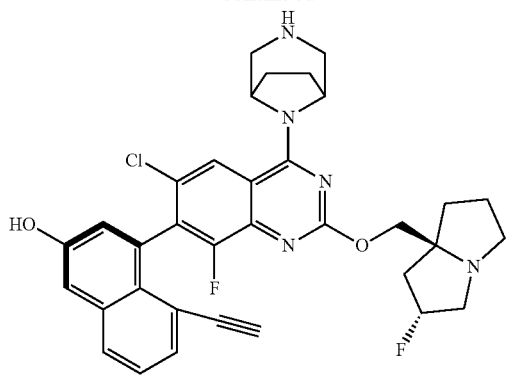
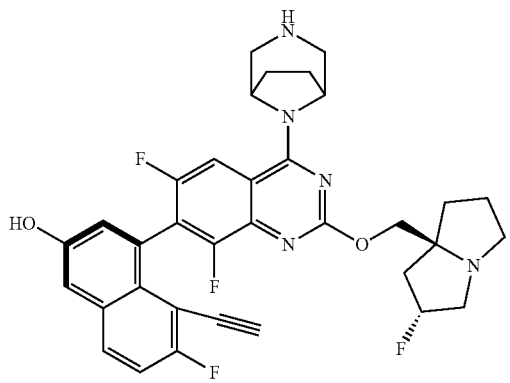
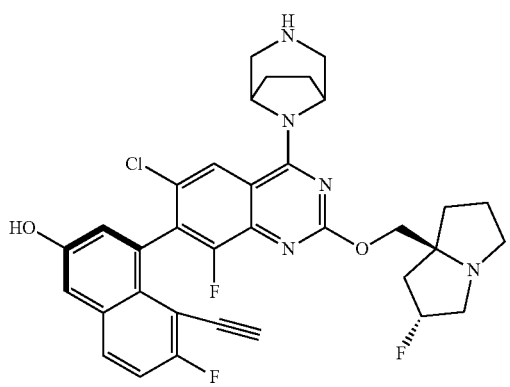
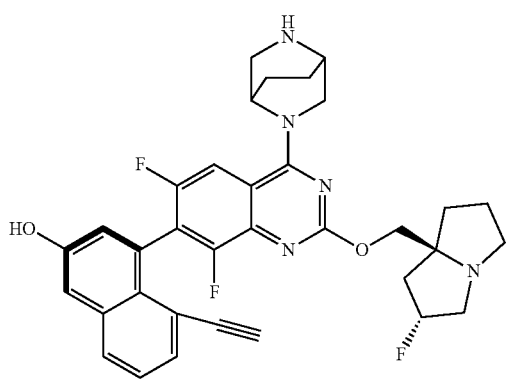
144
-continued
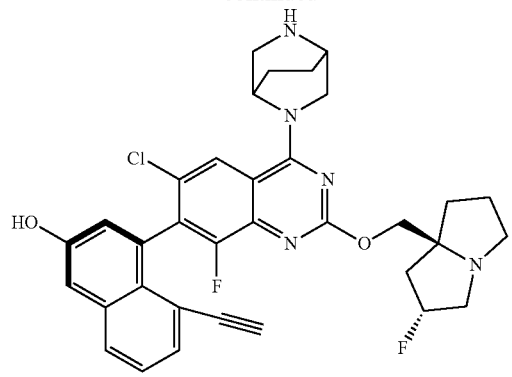
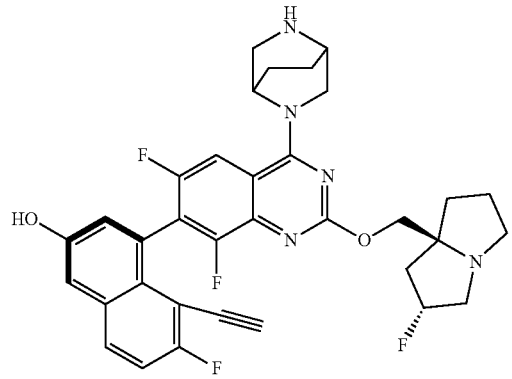
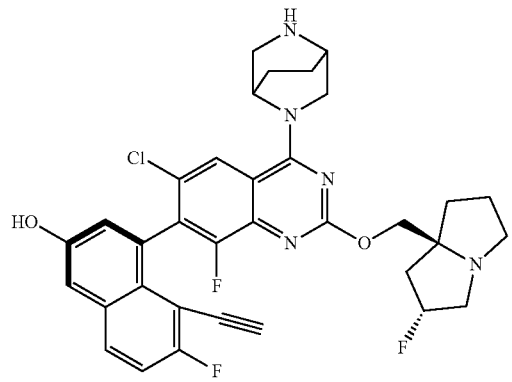
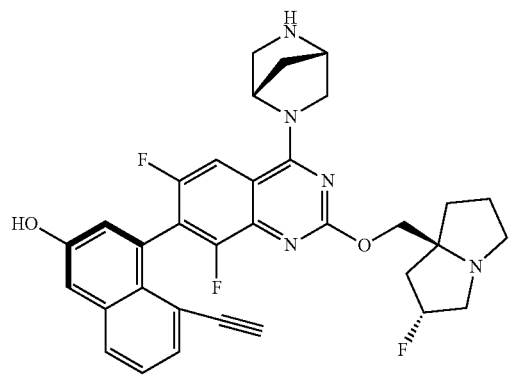

145
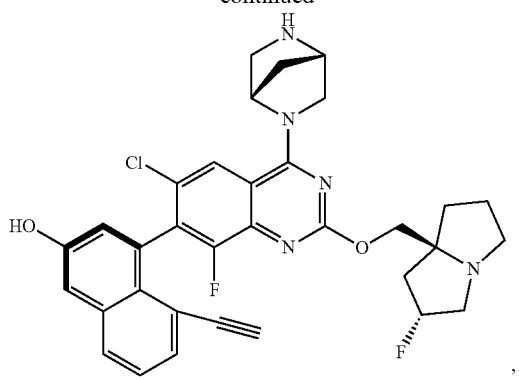
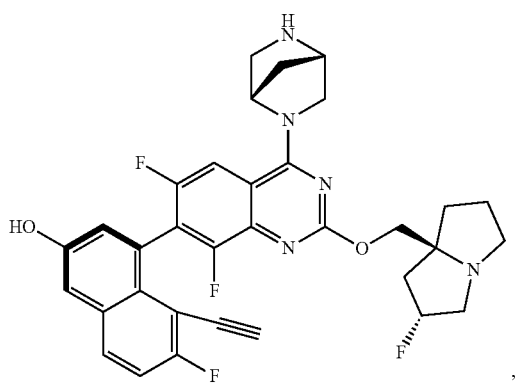
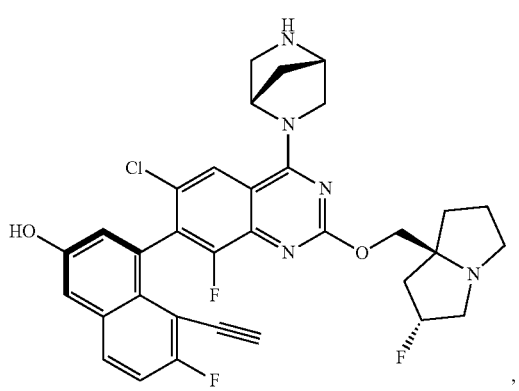
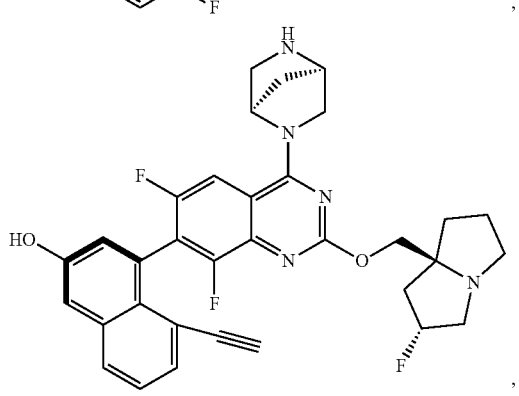
146
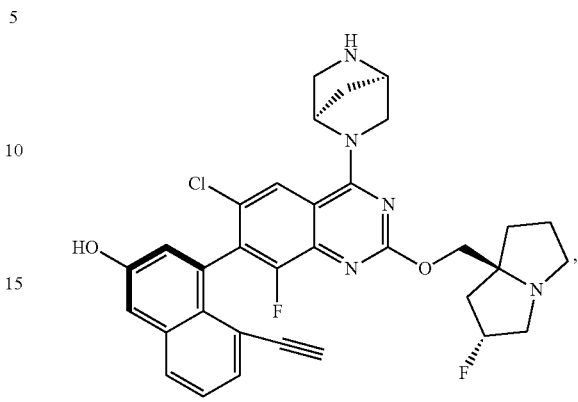
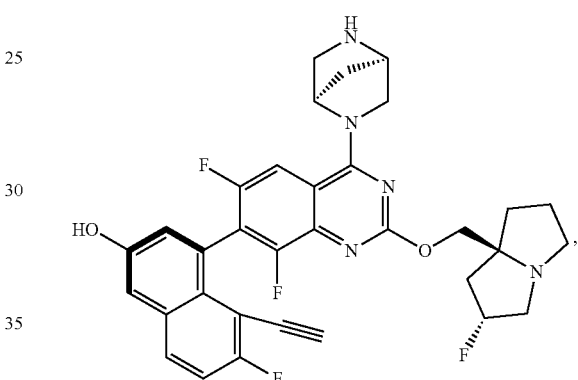
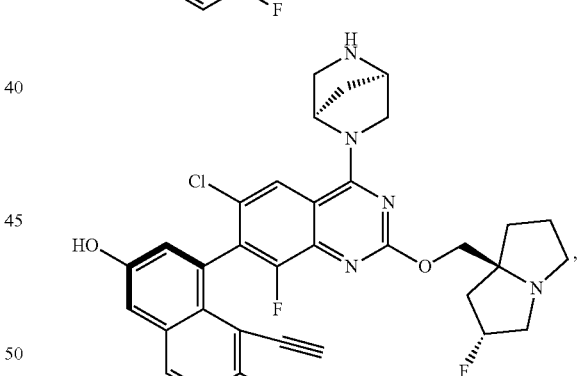
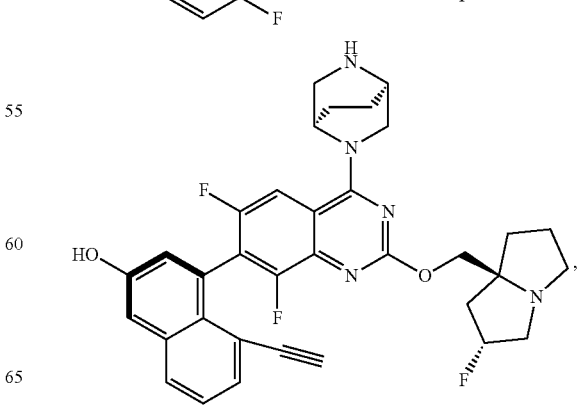

147
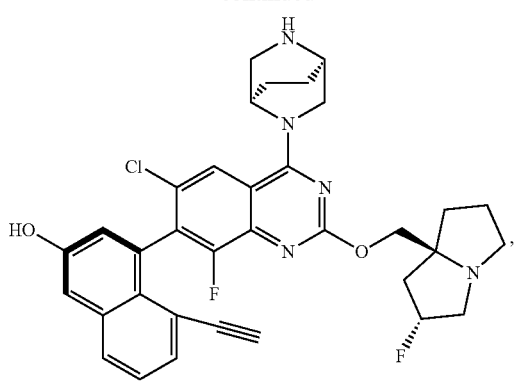
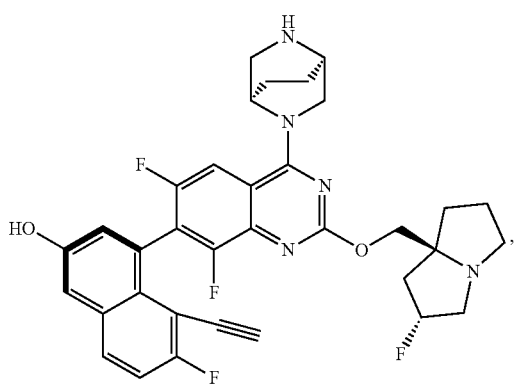
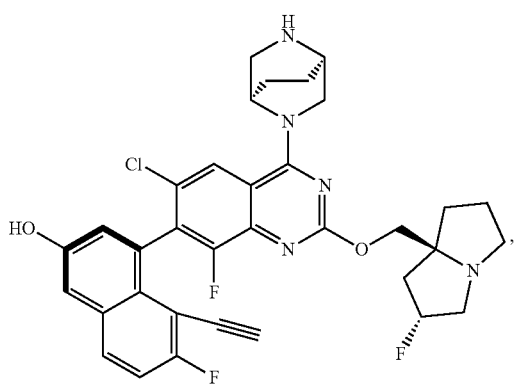
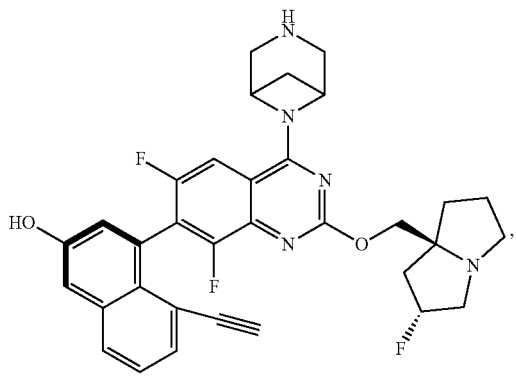
148
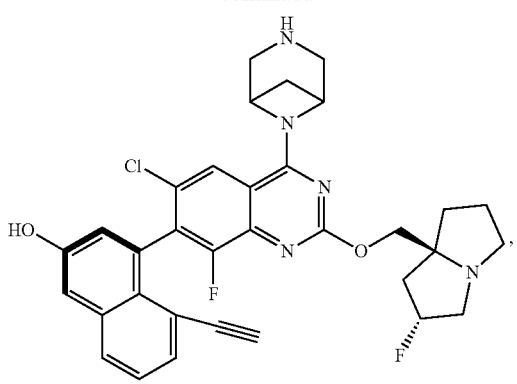
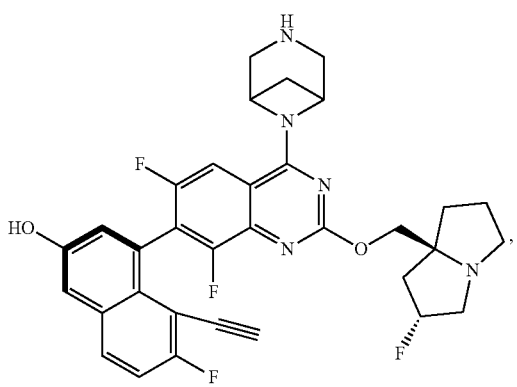
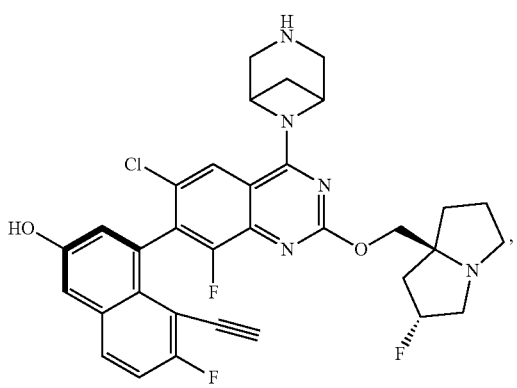
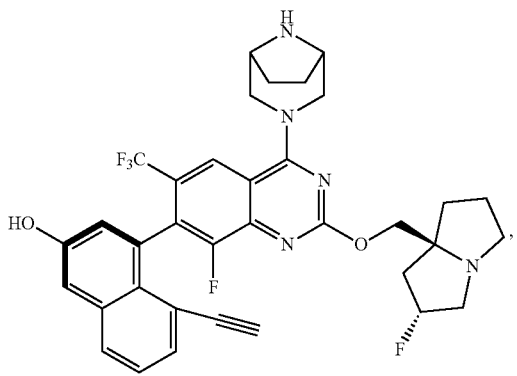

149
-continued
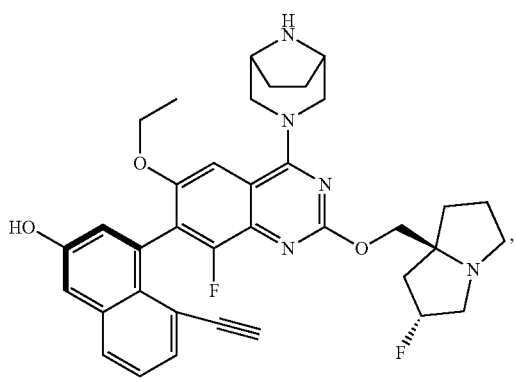
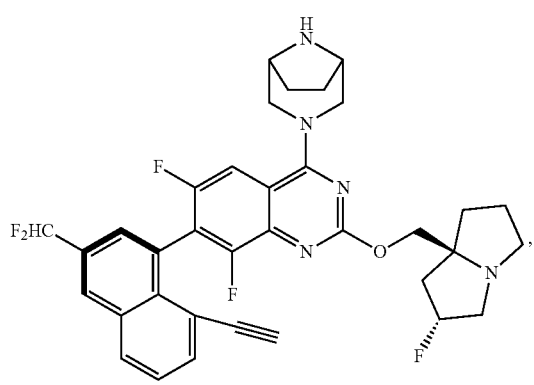
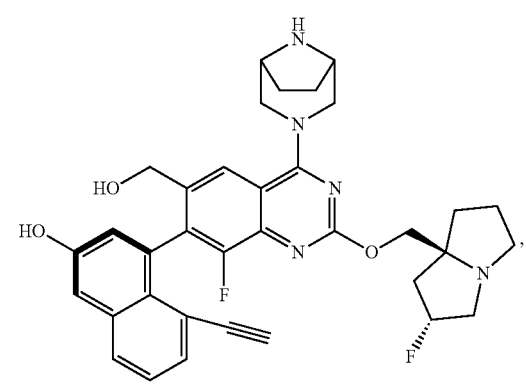
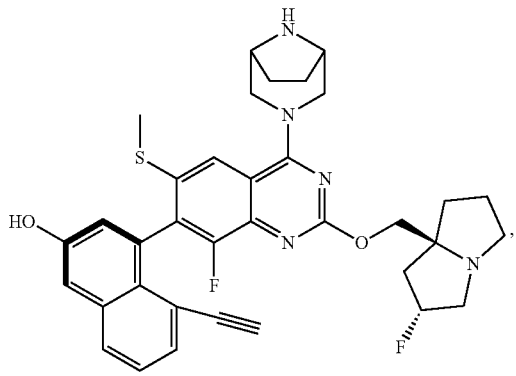
150
-continued
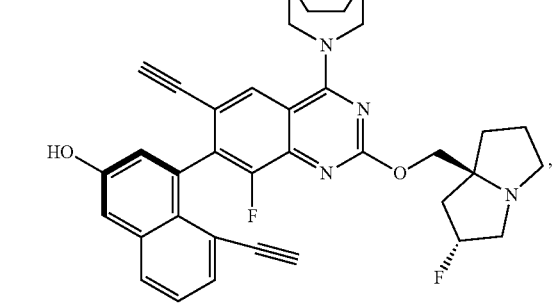
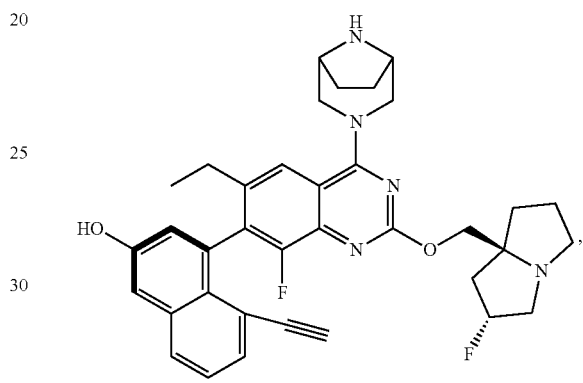
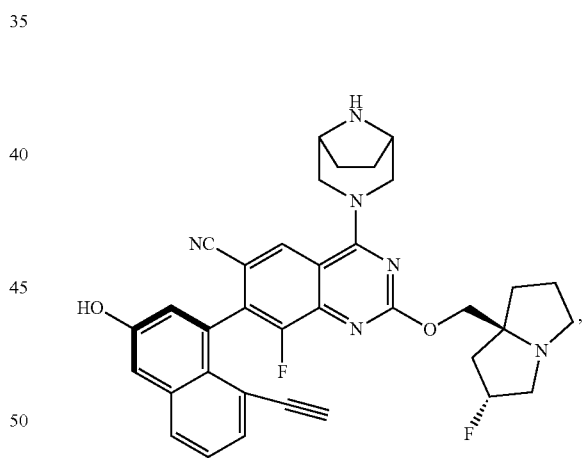
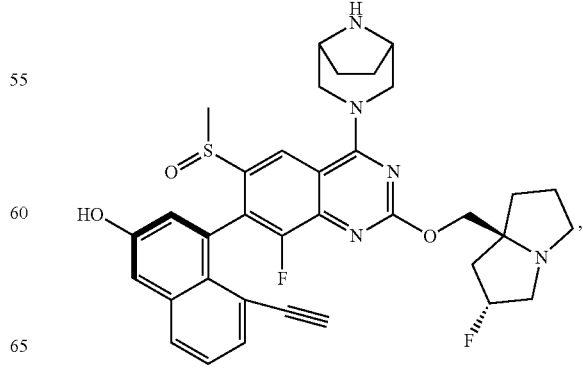

151
-continued
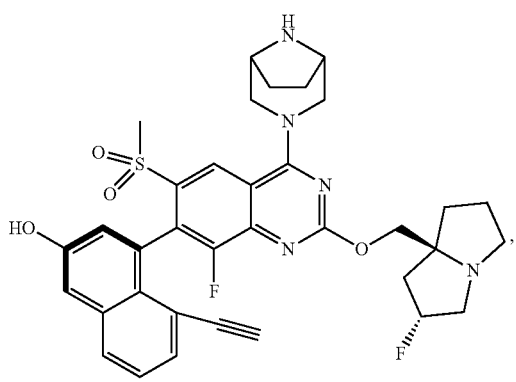

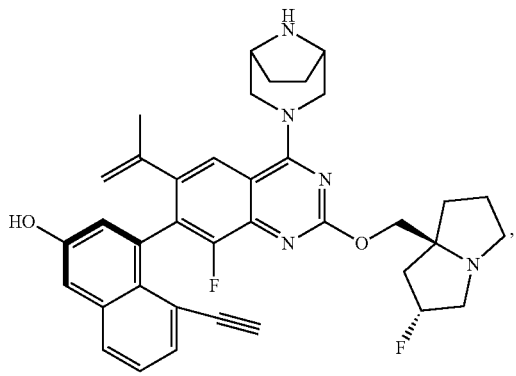
152
-continued
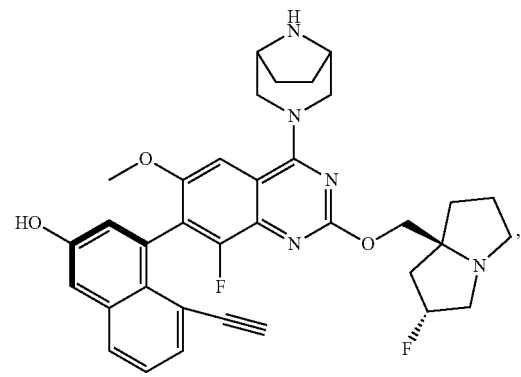
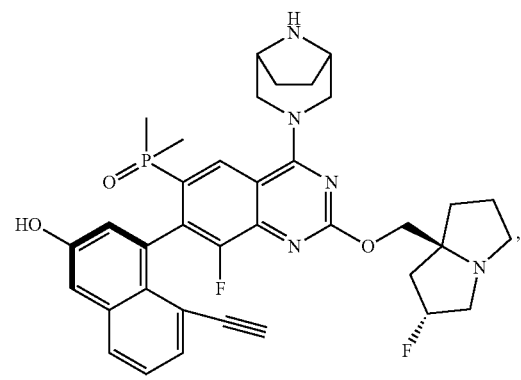
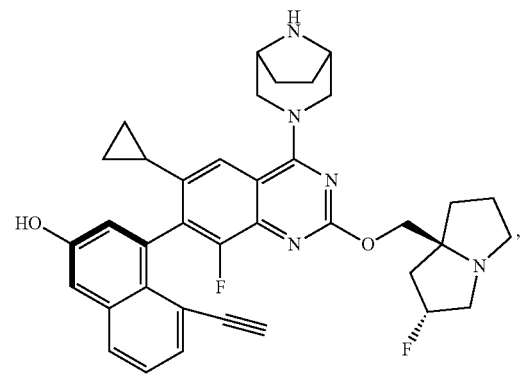
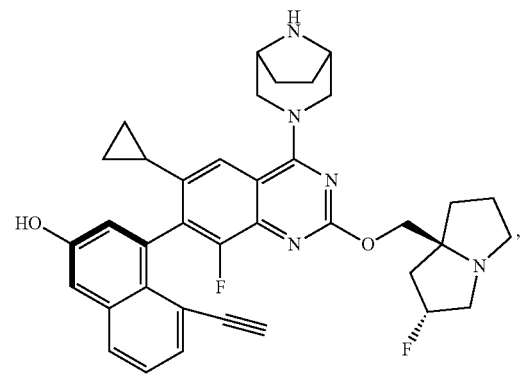

153
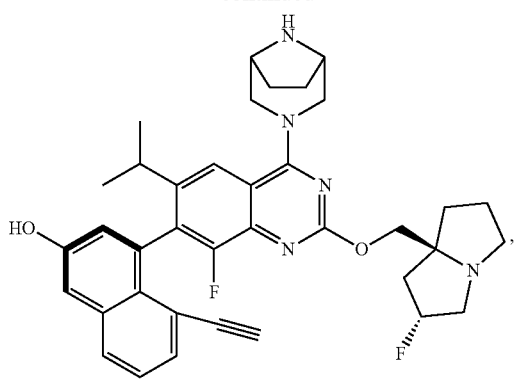
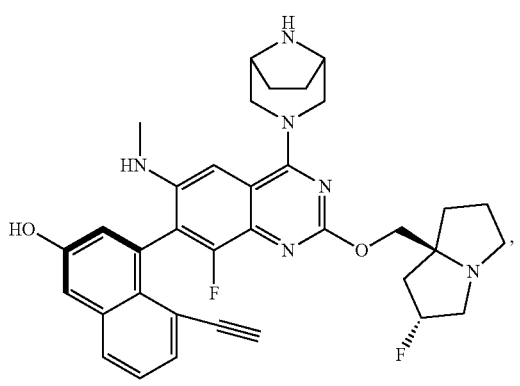
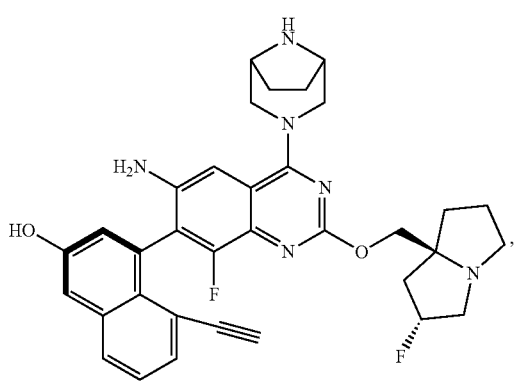
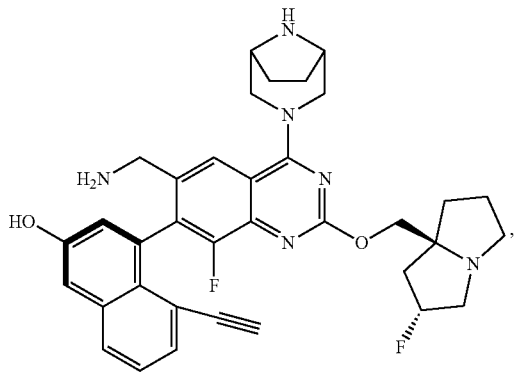
154
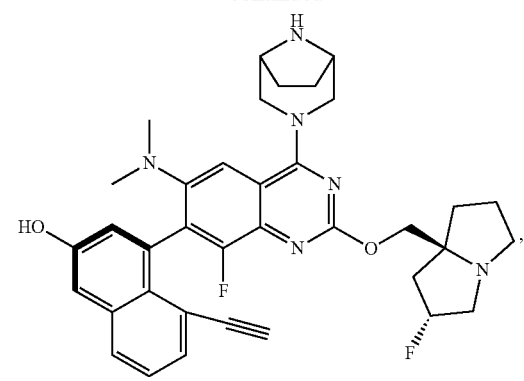
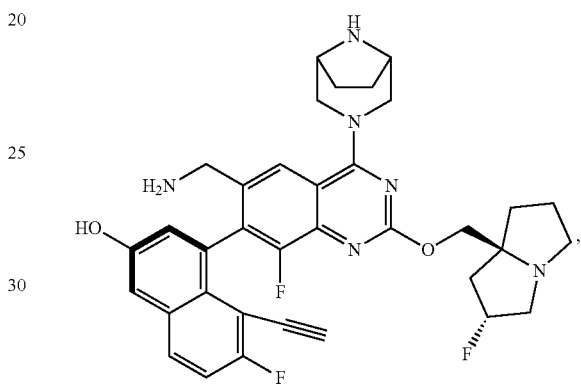
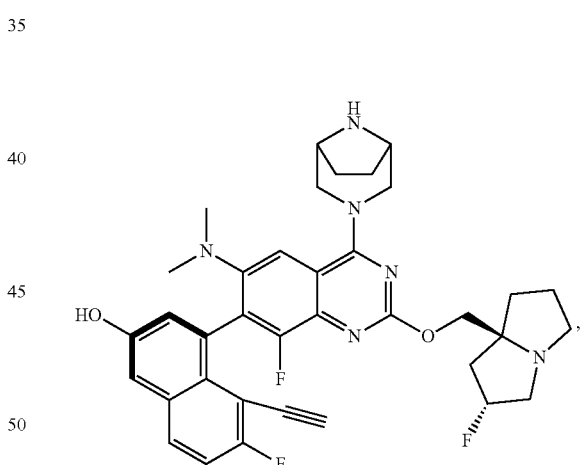
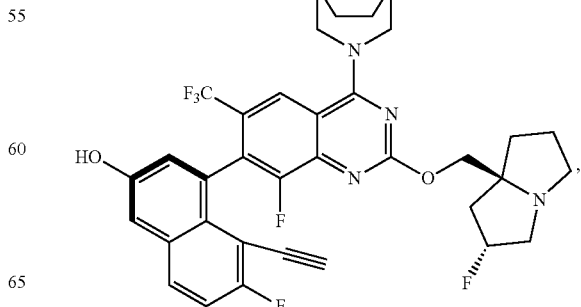

155
-continued
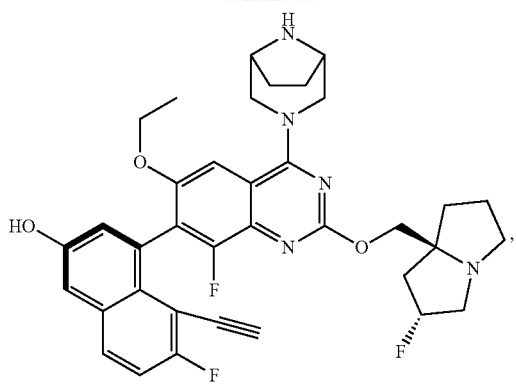
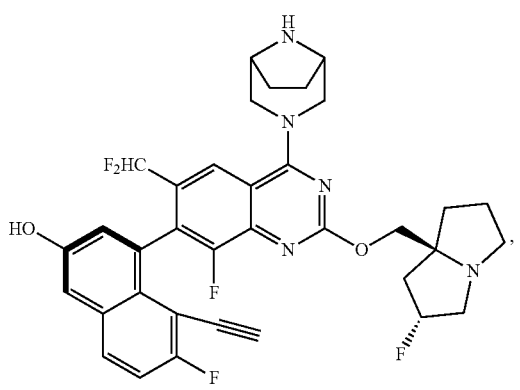
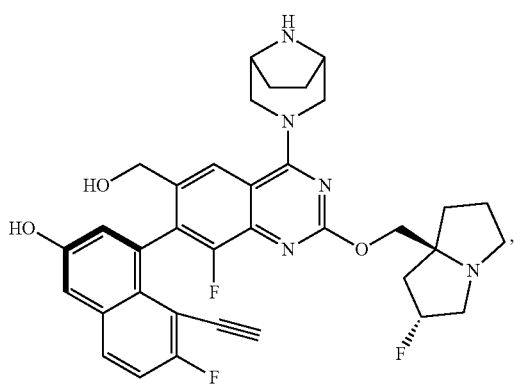
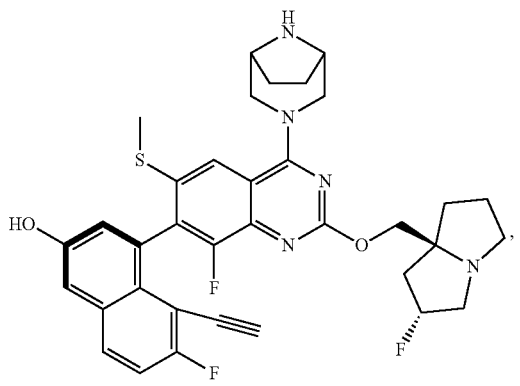
156
-continued
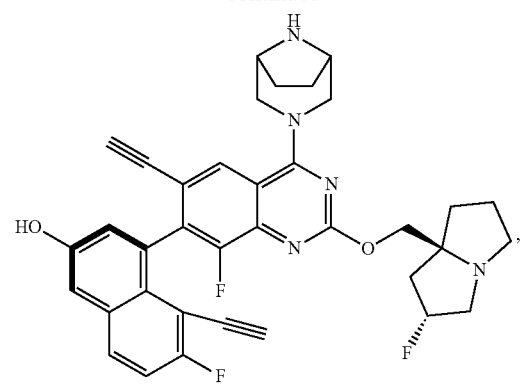
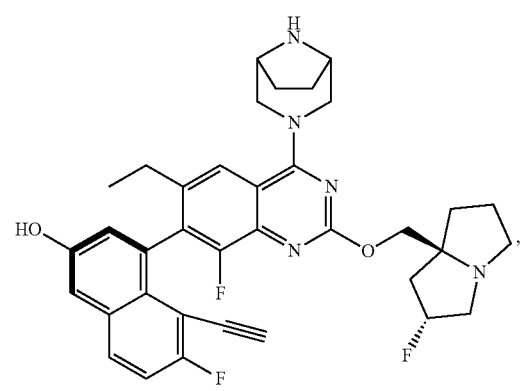
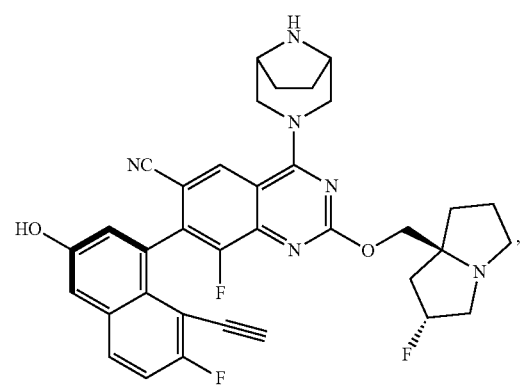
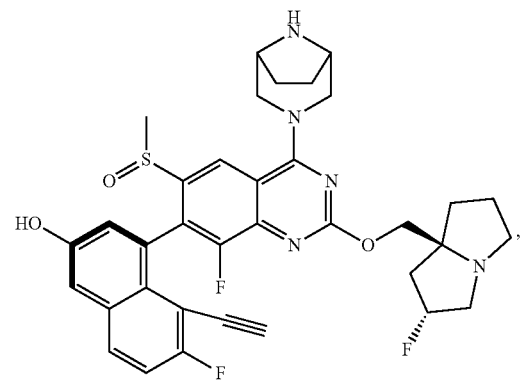

157
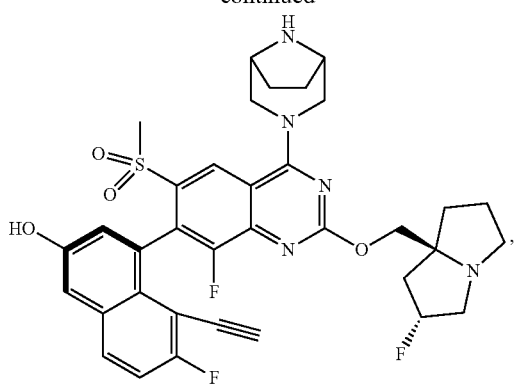
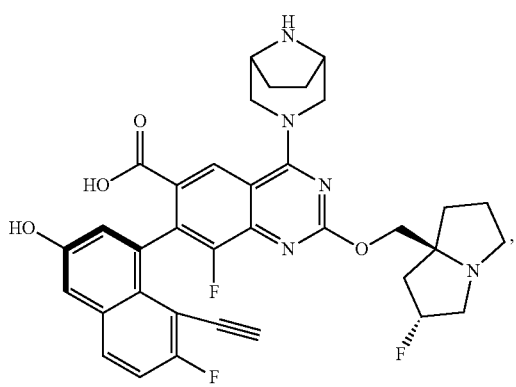
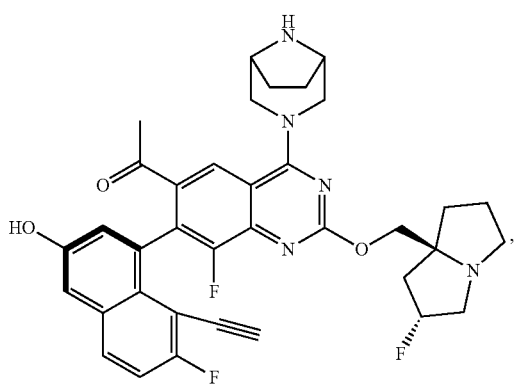
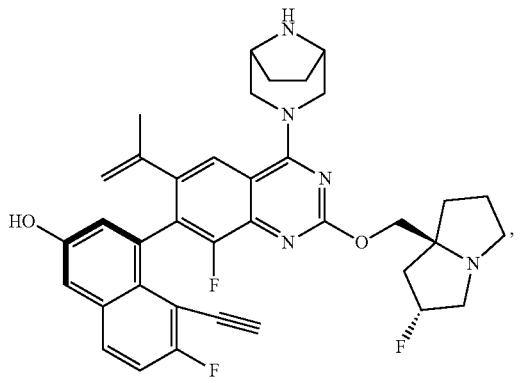
158
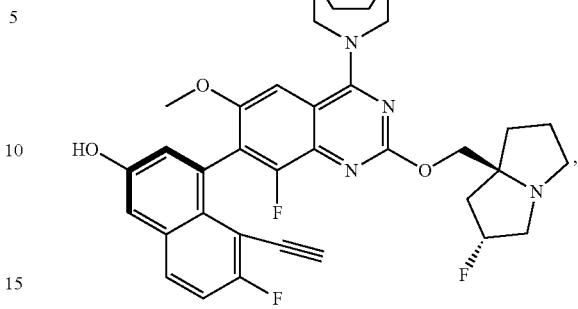

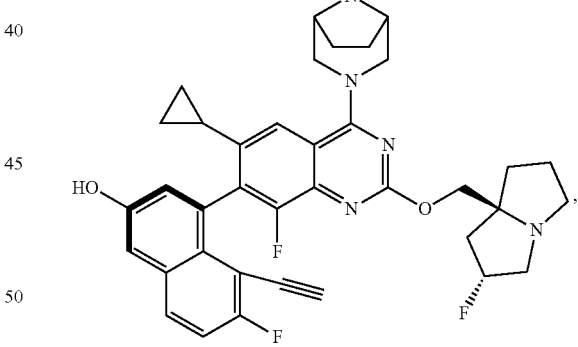
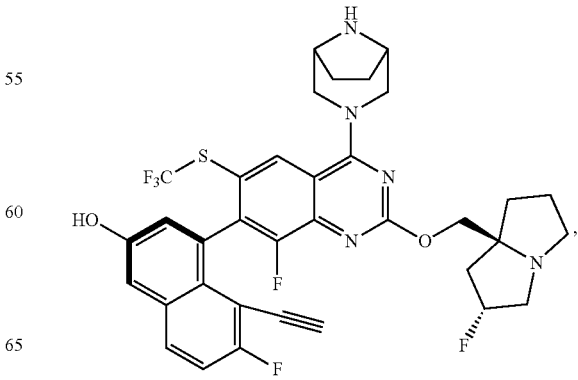

159
-continued
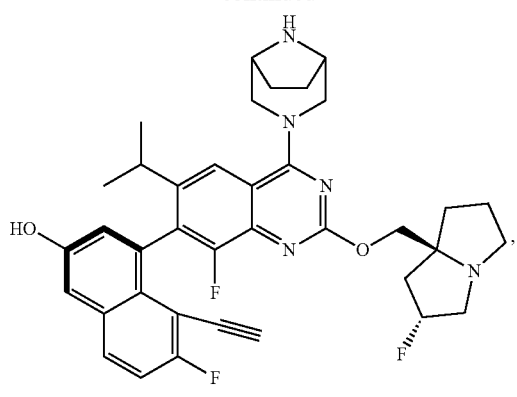
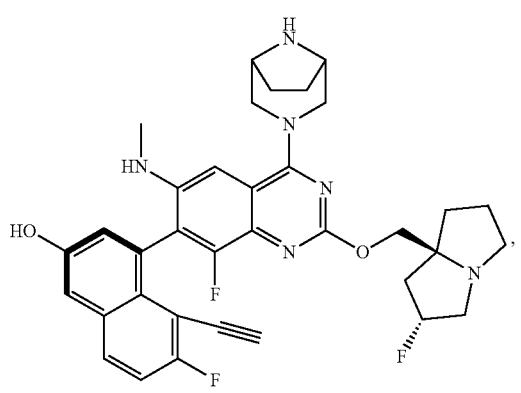
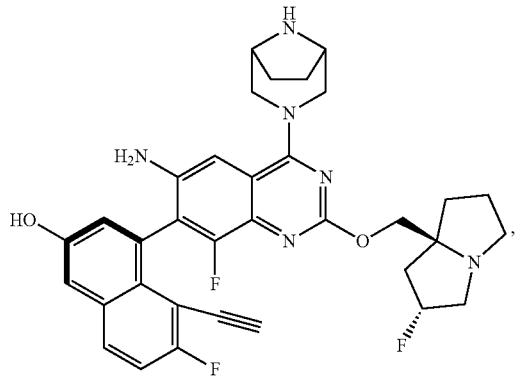
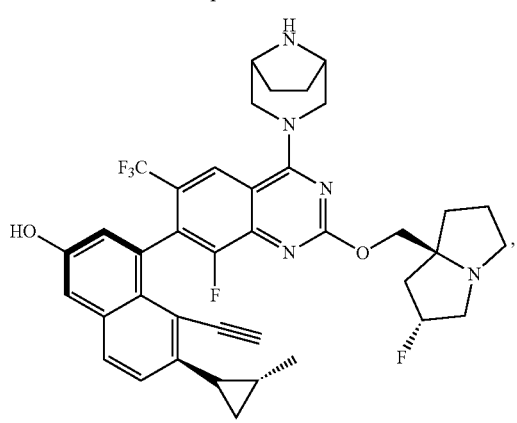
160
-continued
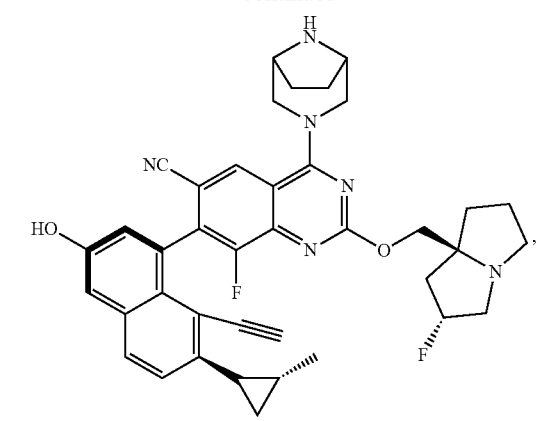
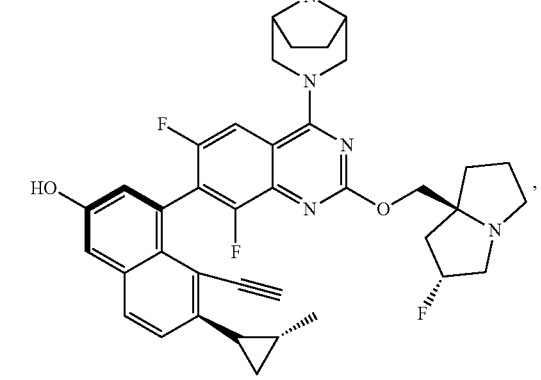
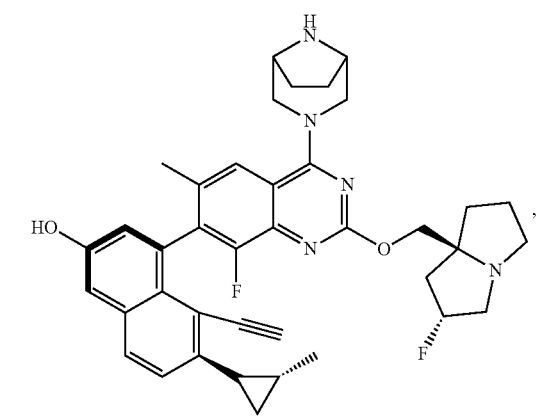
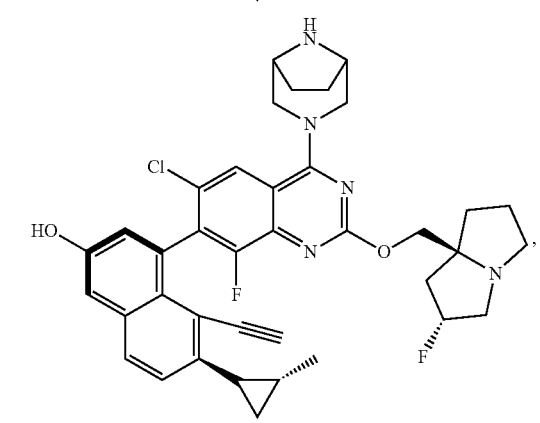

161
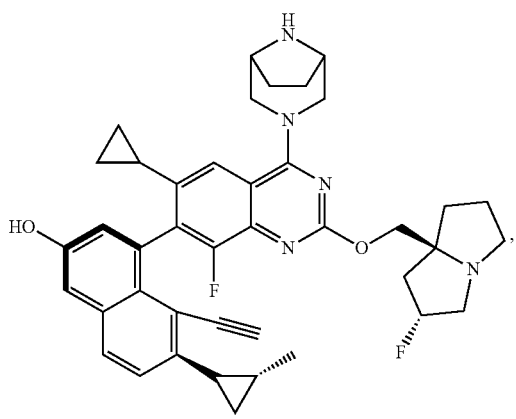
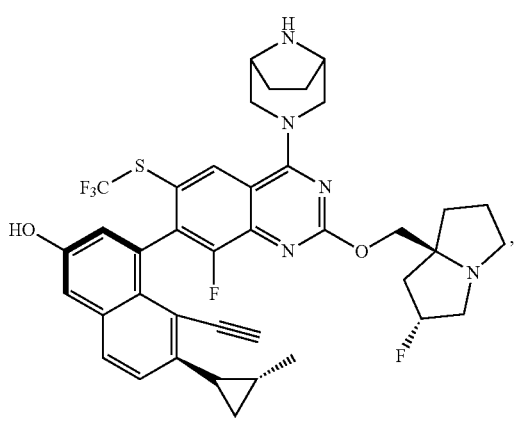
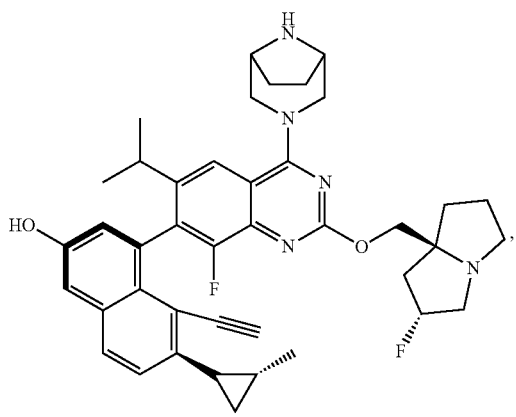
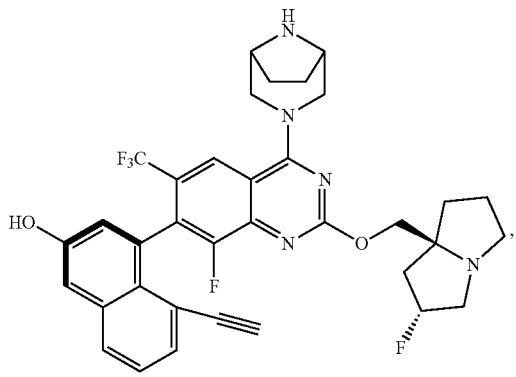
162
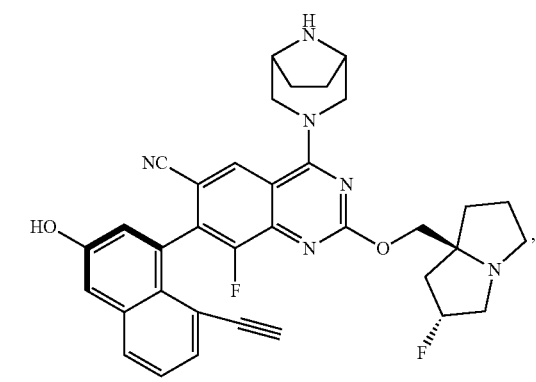
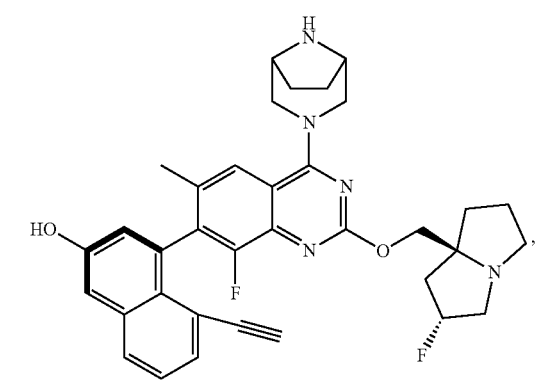
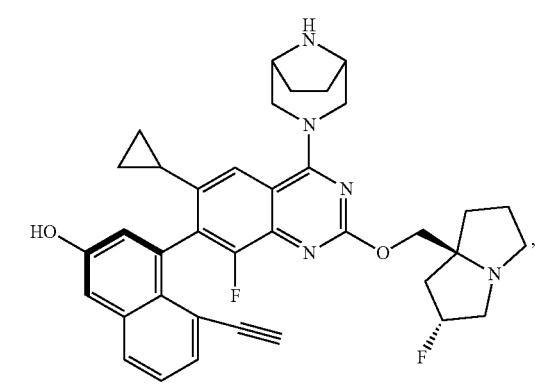
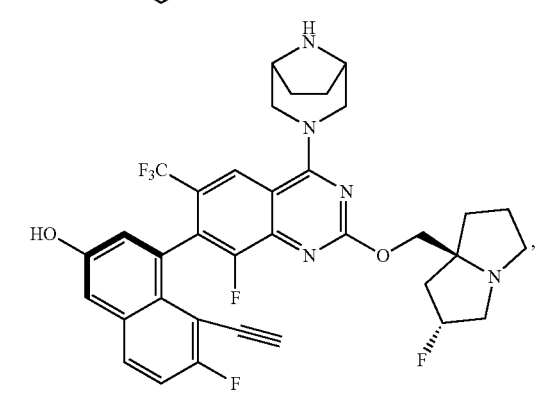

163
-continued
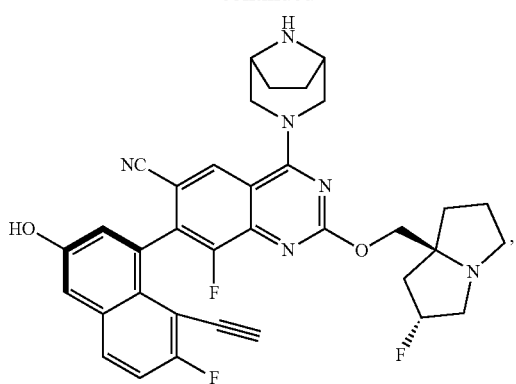
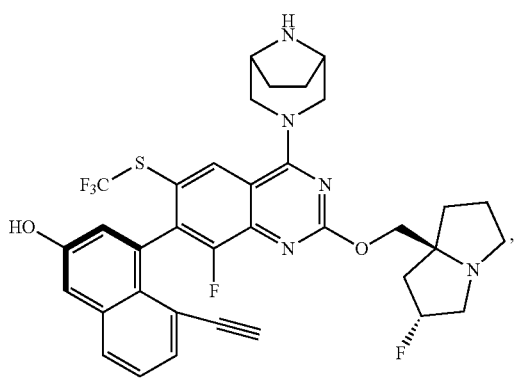
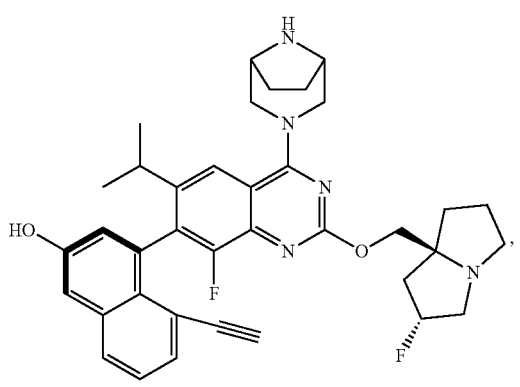
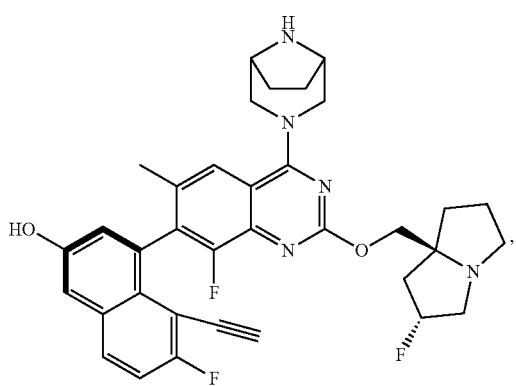
164
-continued
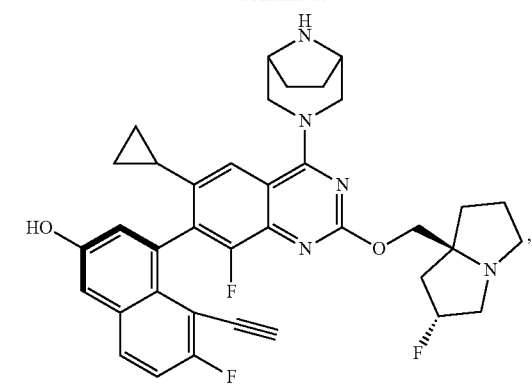
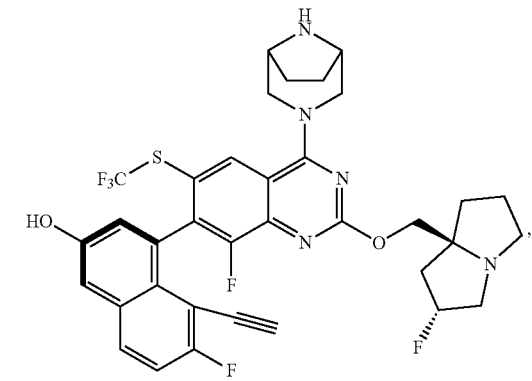
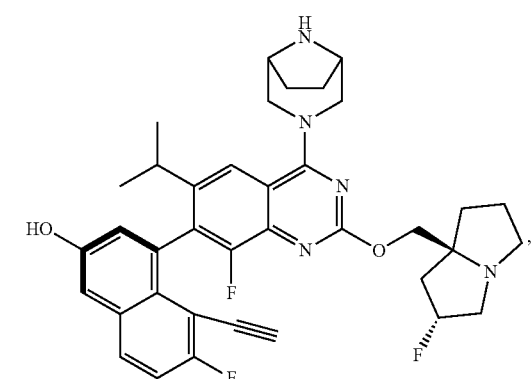
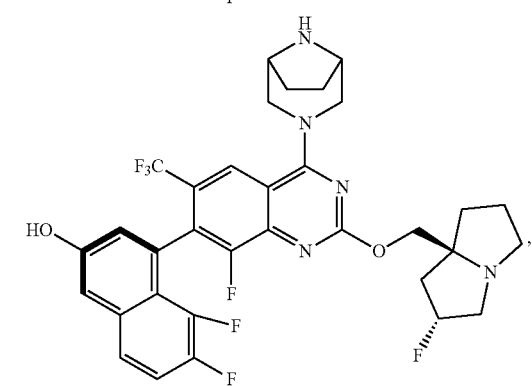

165
-continued
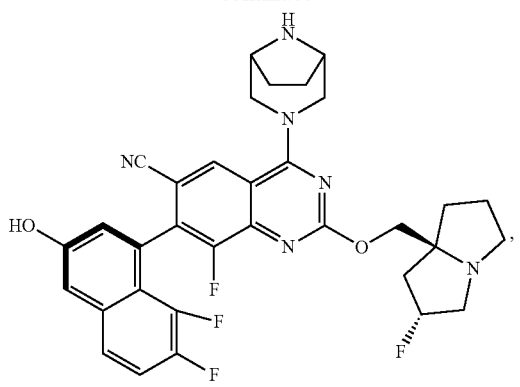
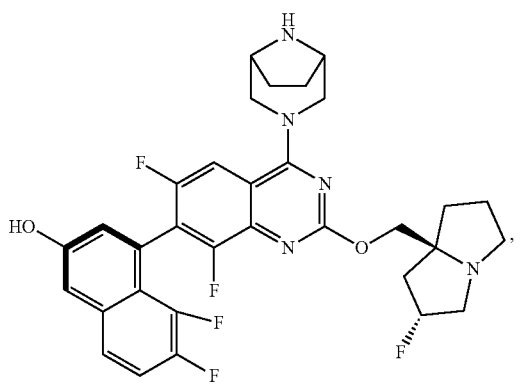
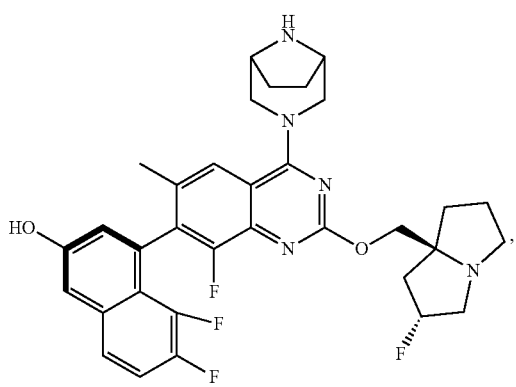
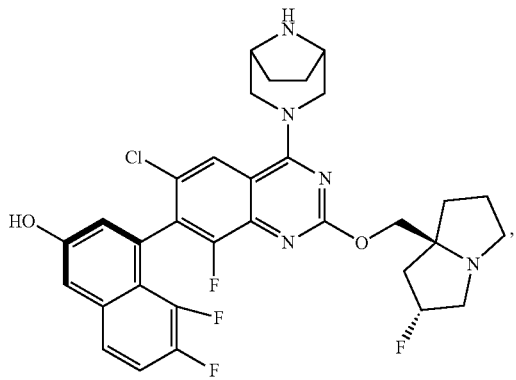
166
-continued
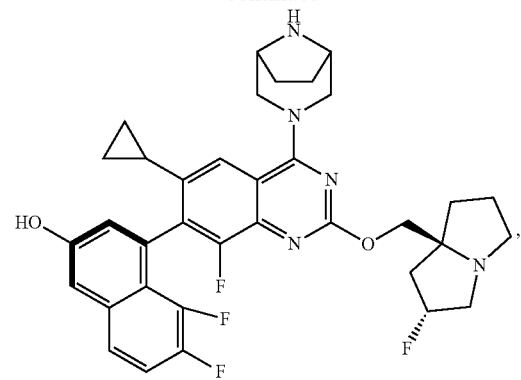
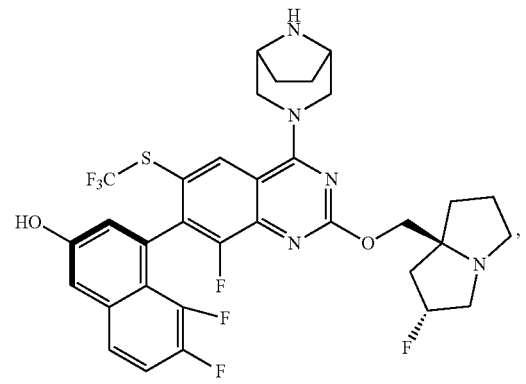
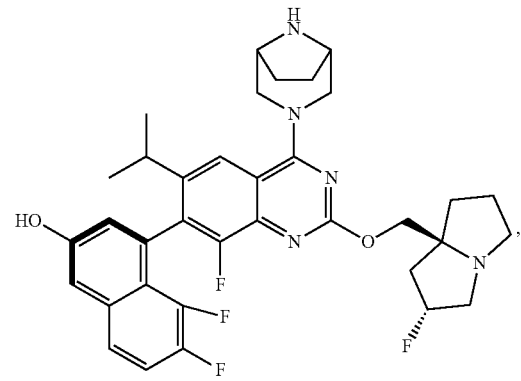
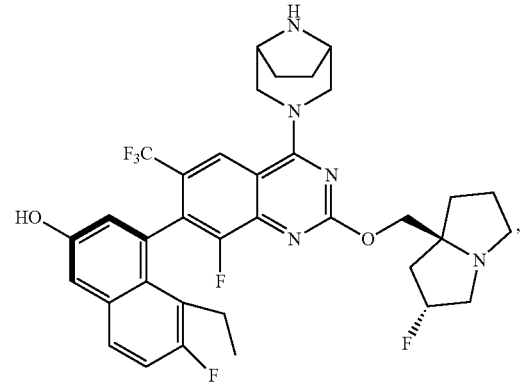

167
-continued
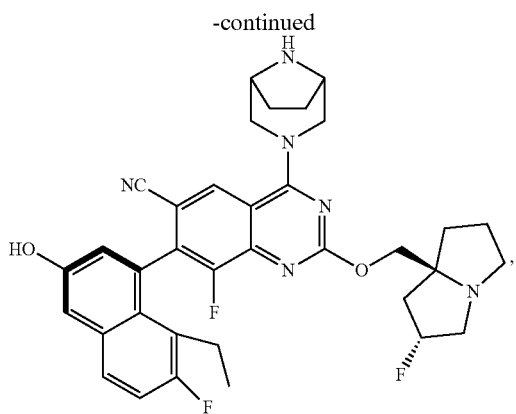
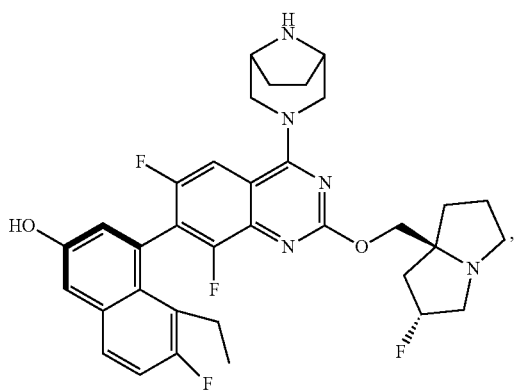
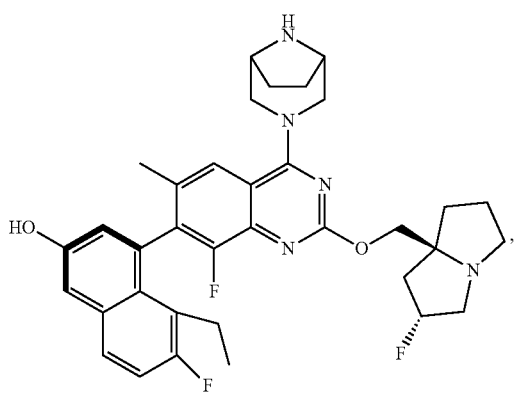
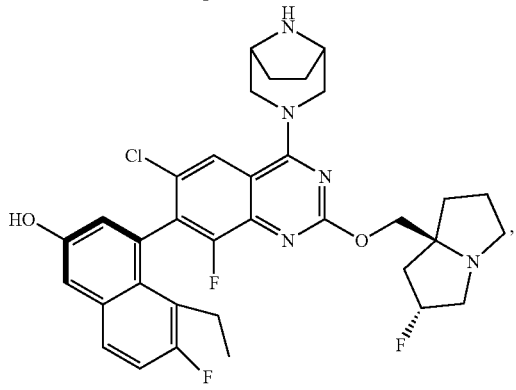
168
-continued
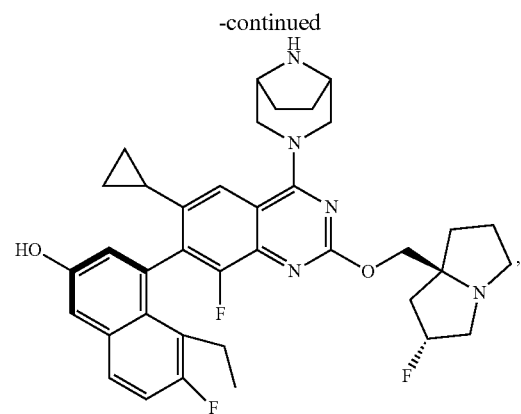
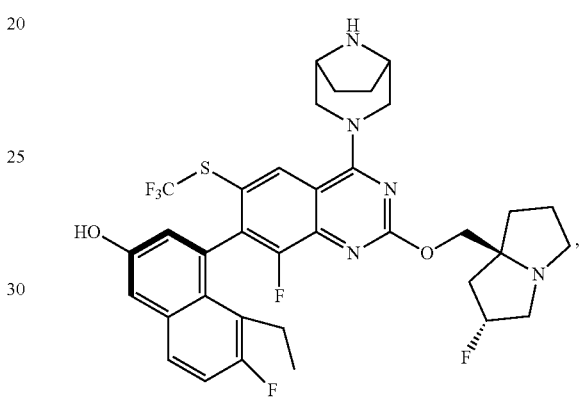

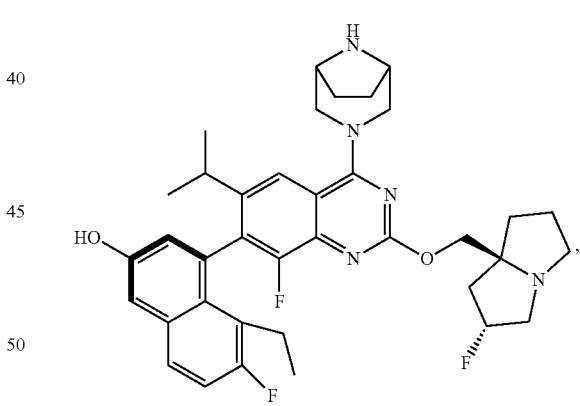

169
-continued
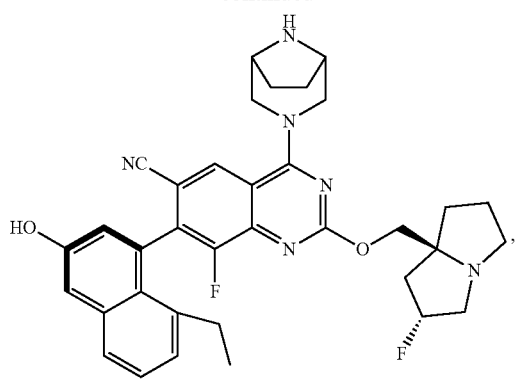
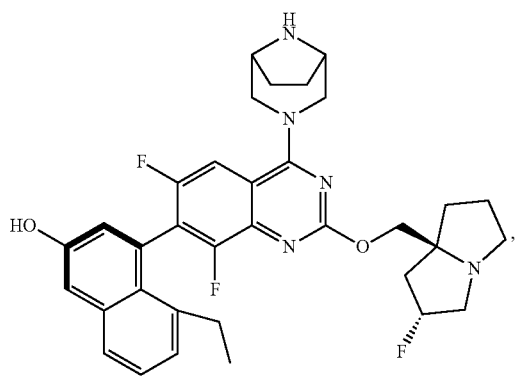
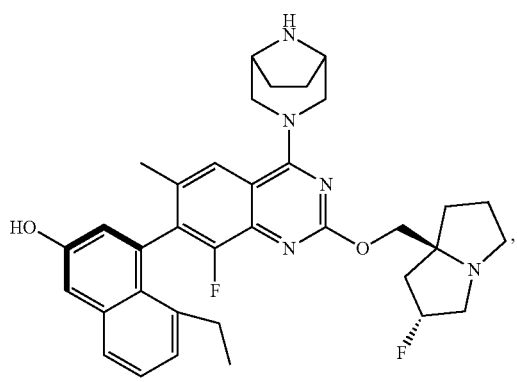
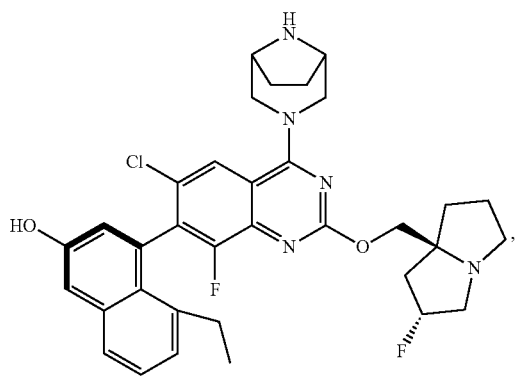
170
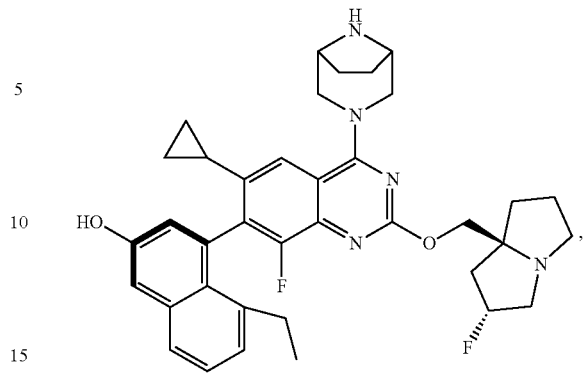
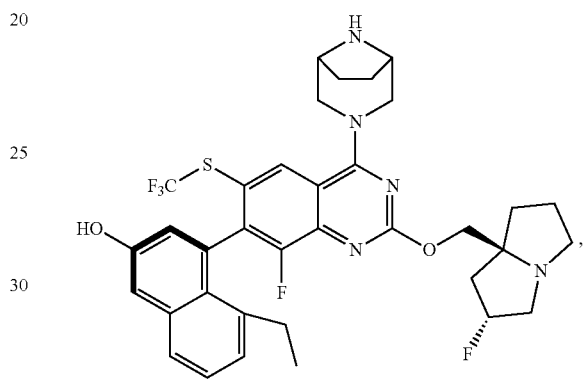
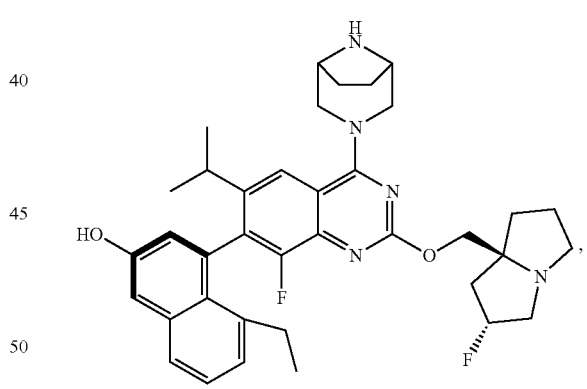
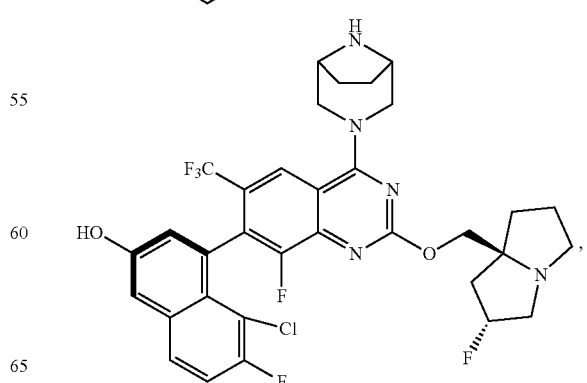

171
-continued
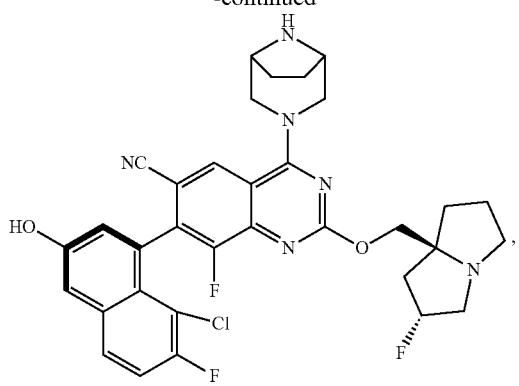
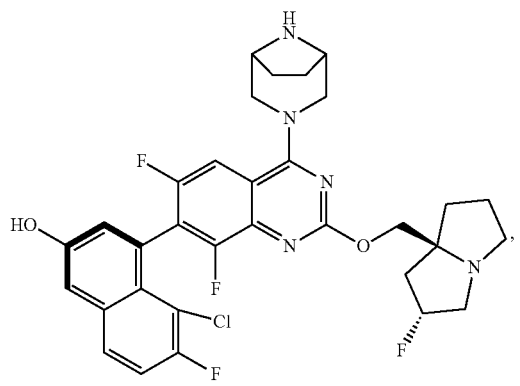
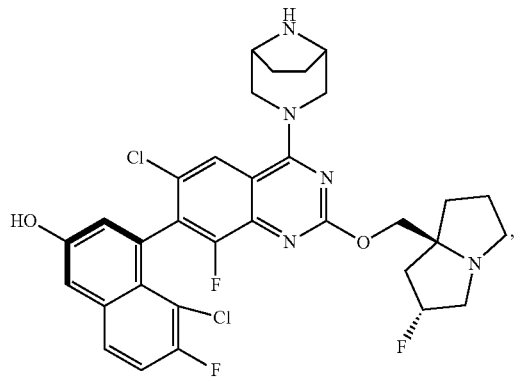
172
-continued
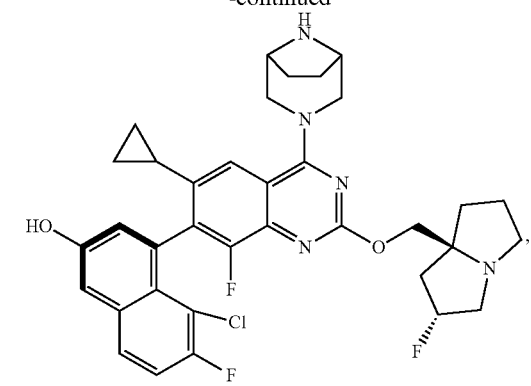
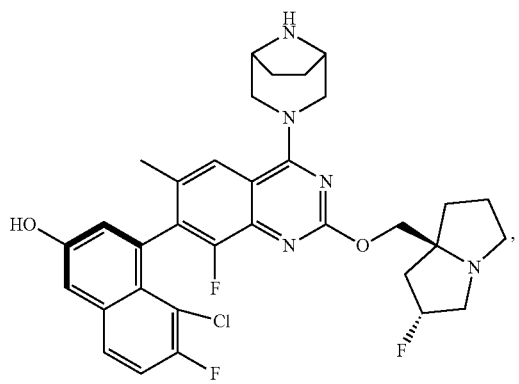
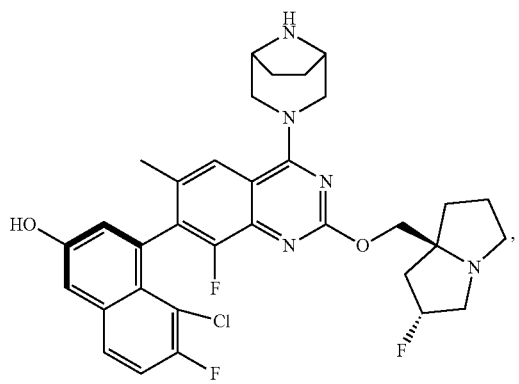
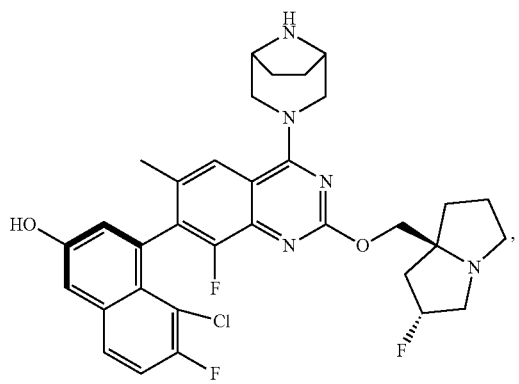

173
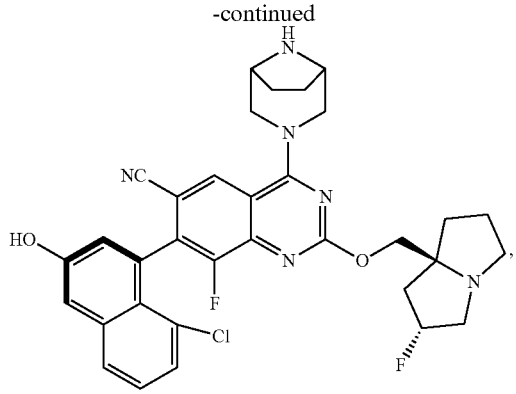
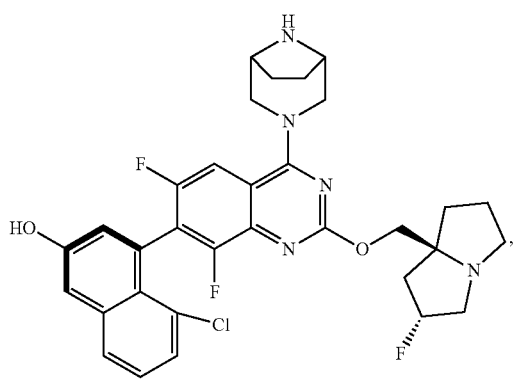
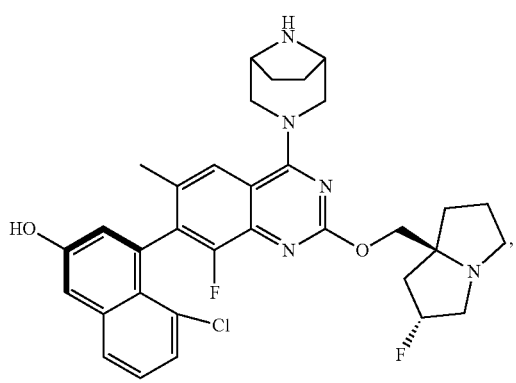
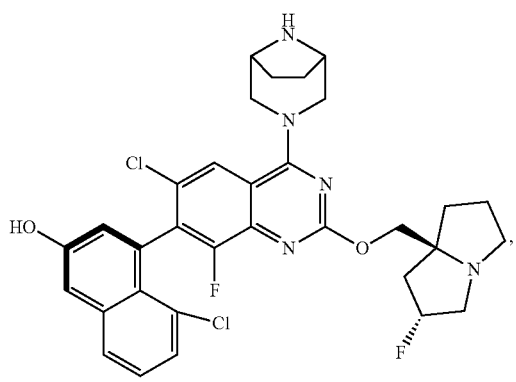
174
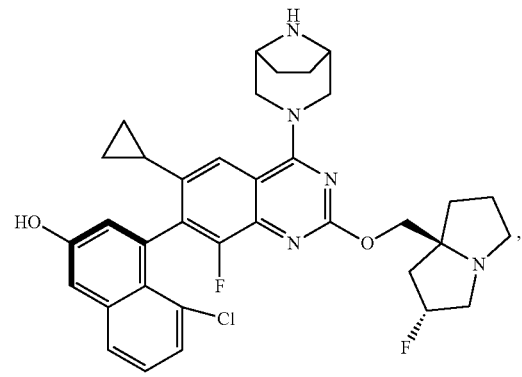
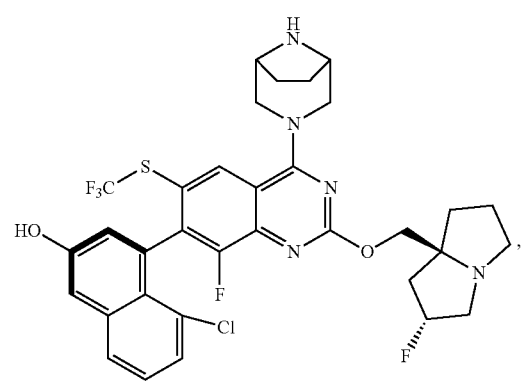
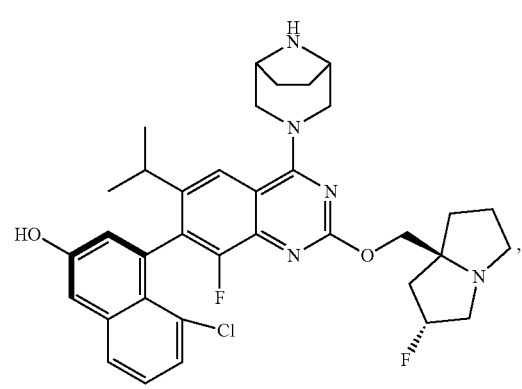
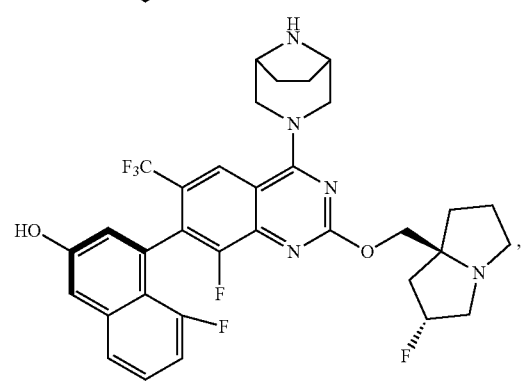

175
-continued
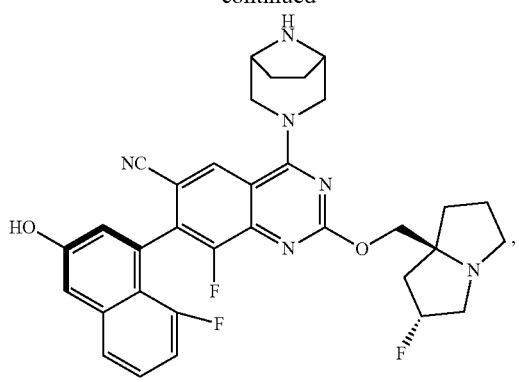
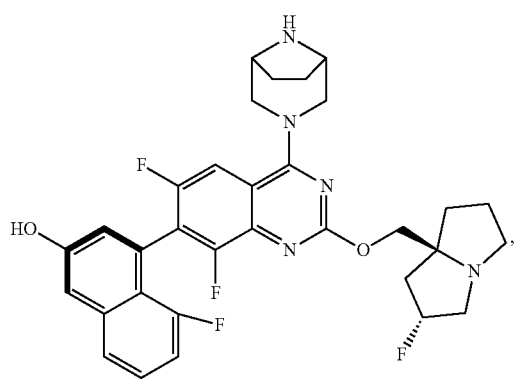
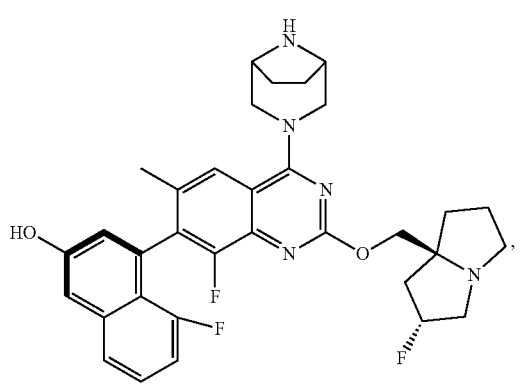
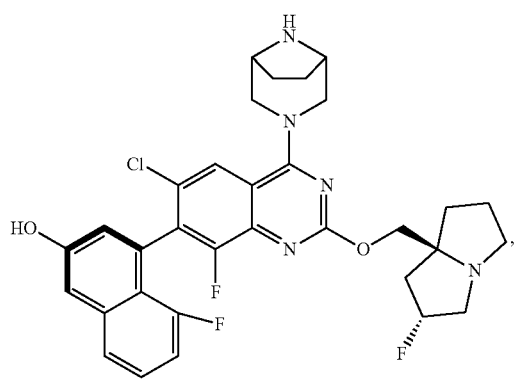
176
-continued
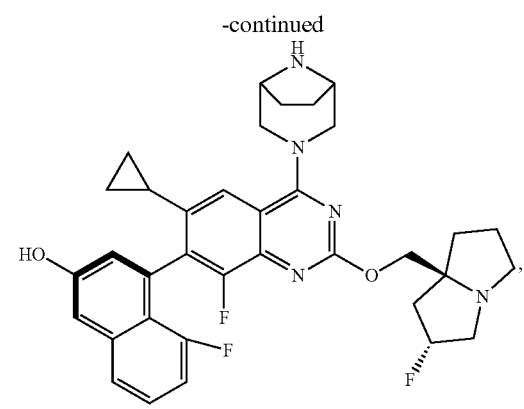
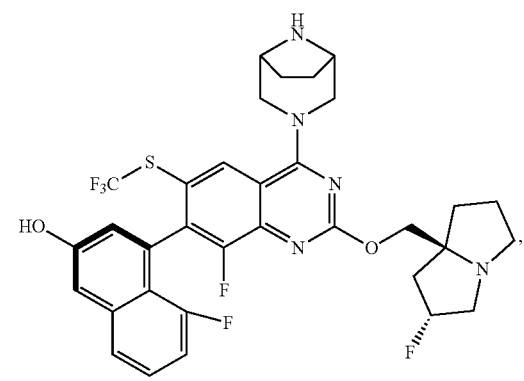
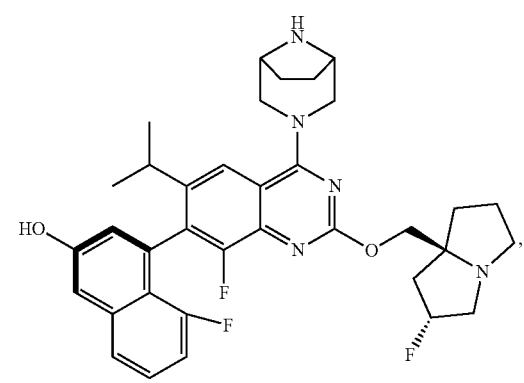
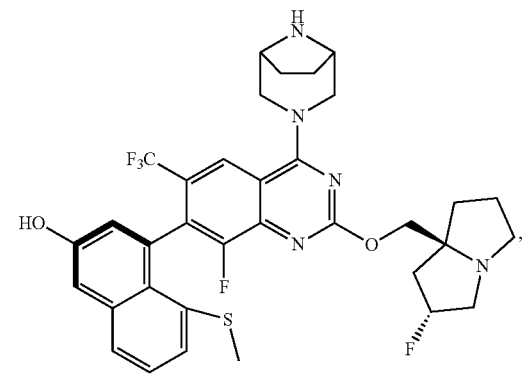

177
-continued
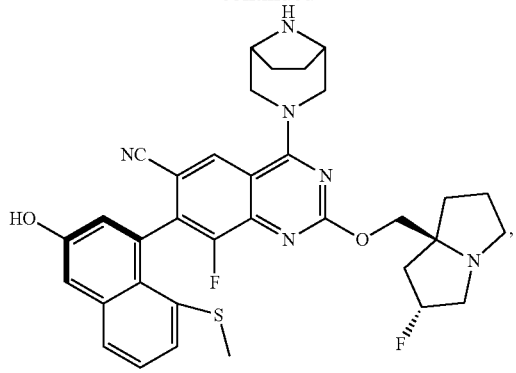
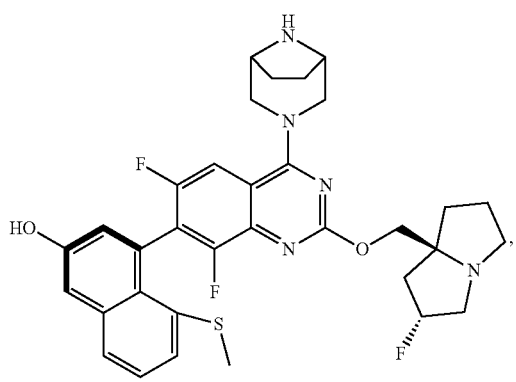
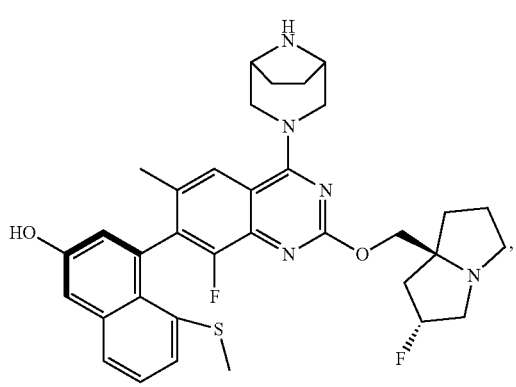
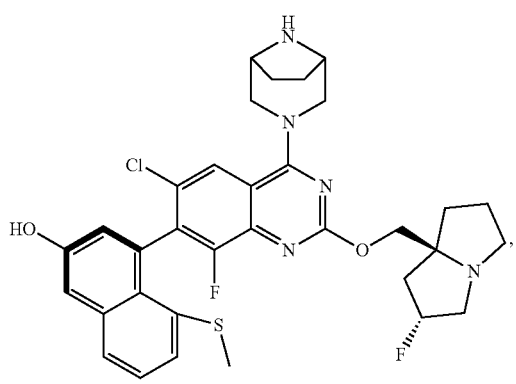
178
-continued
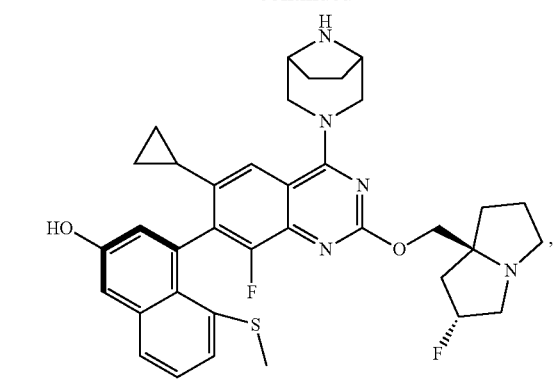
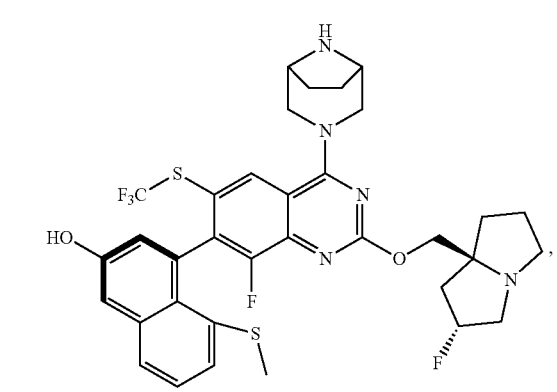
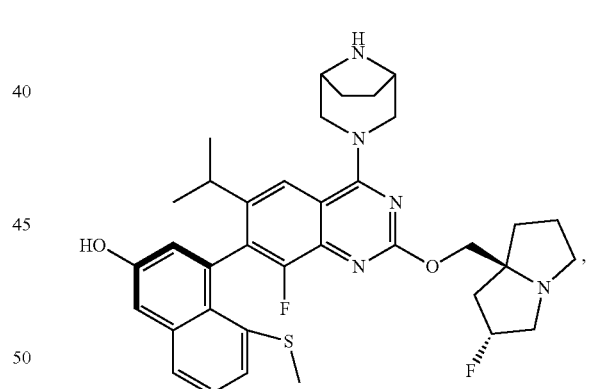
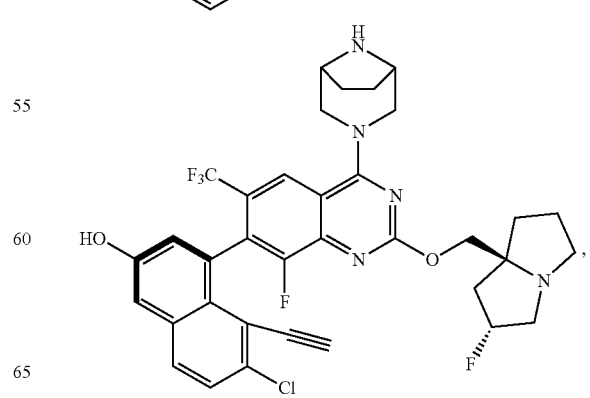

179
-continued
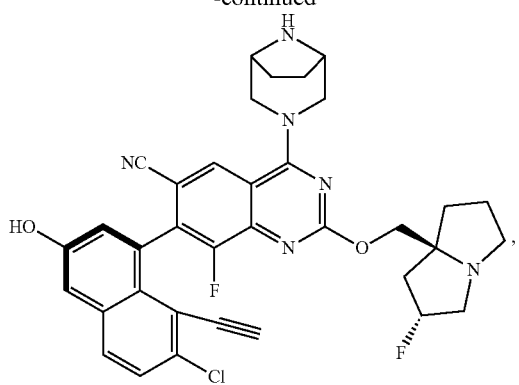
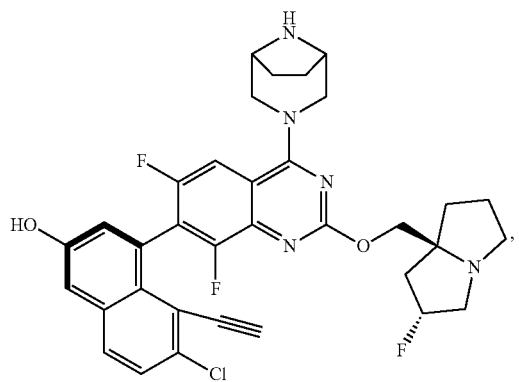
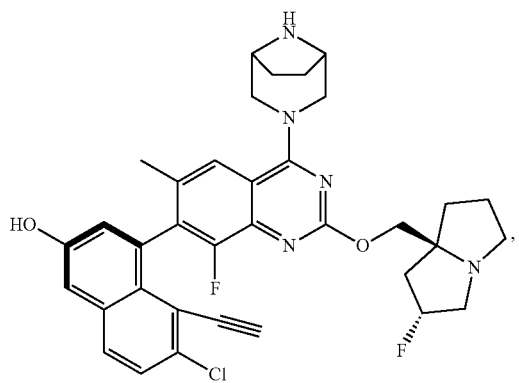
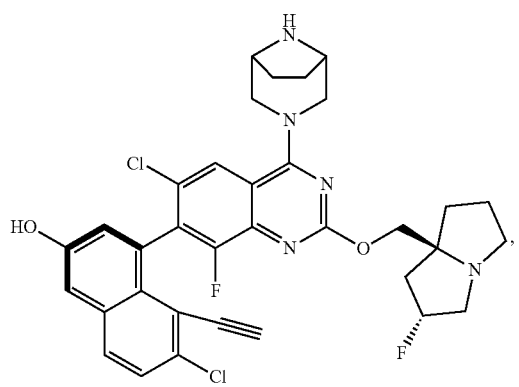
180
-continued
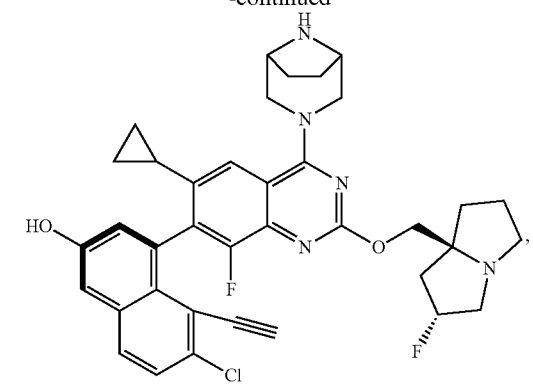
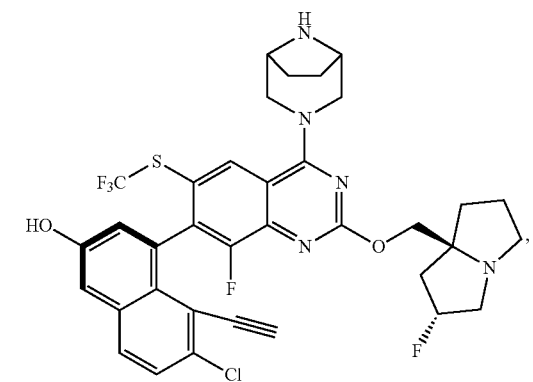
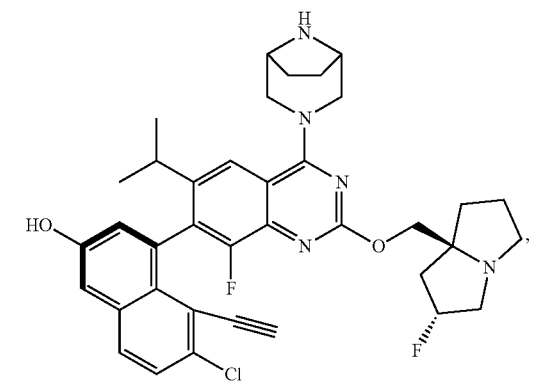
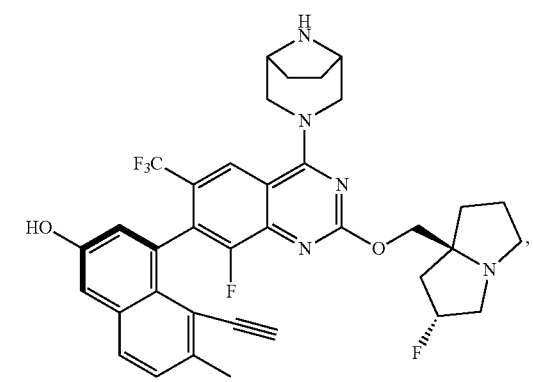

181
-continued
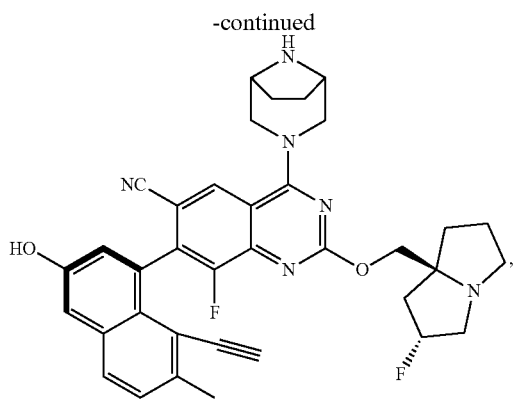
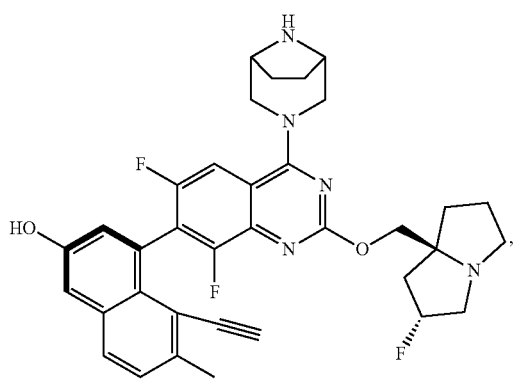
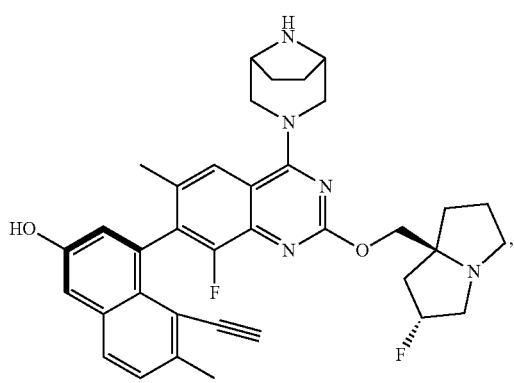
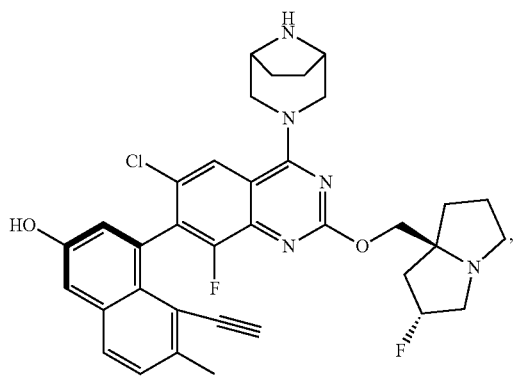
182
-continued
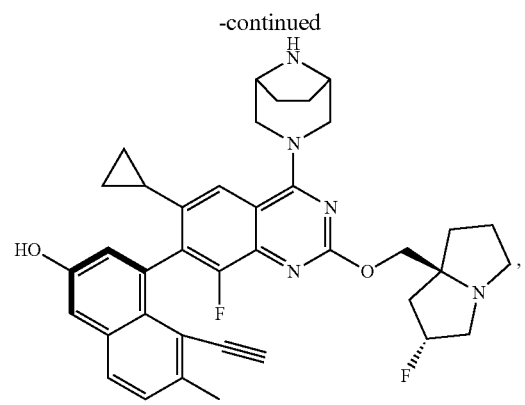
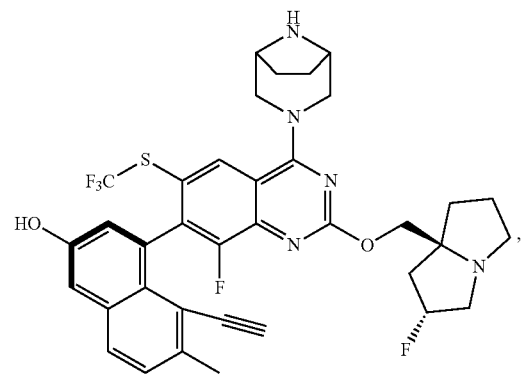
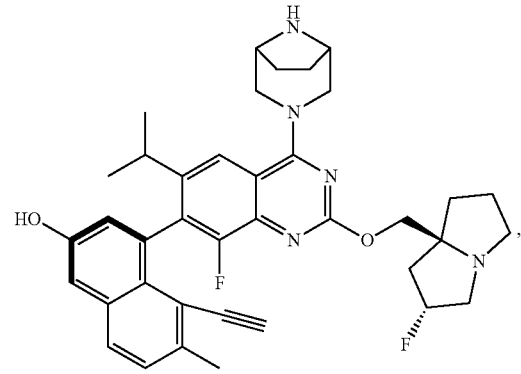
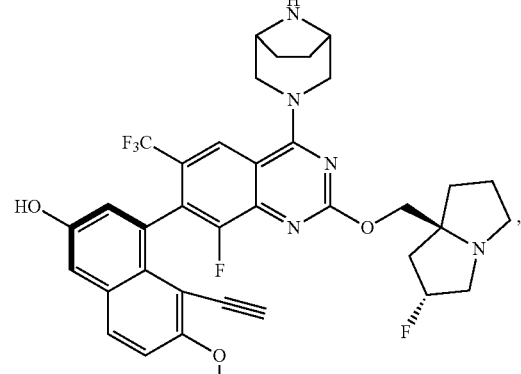

183
-continued
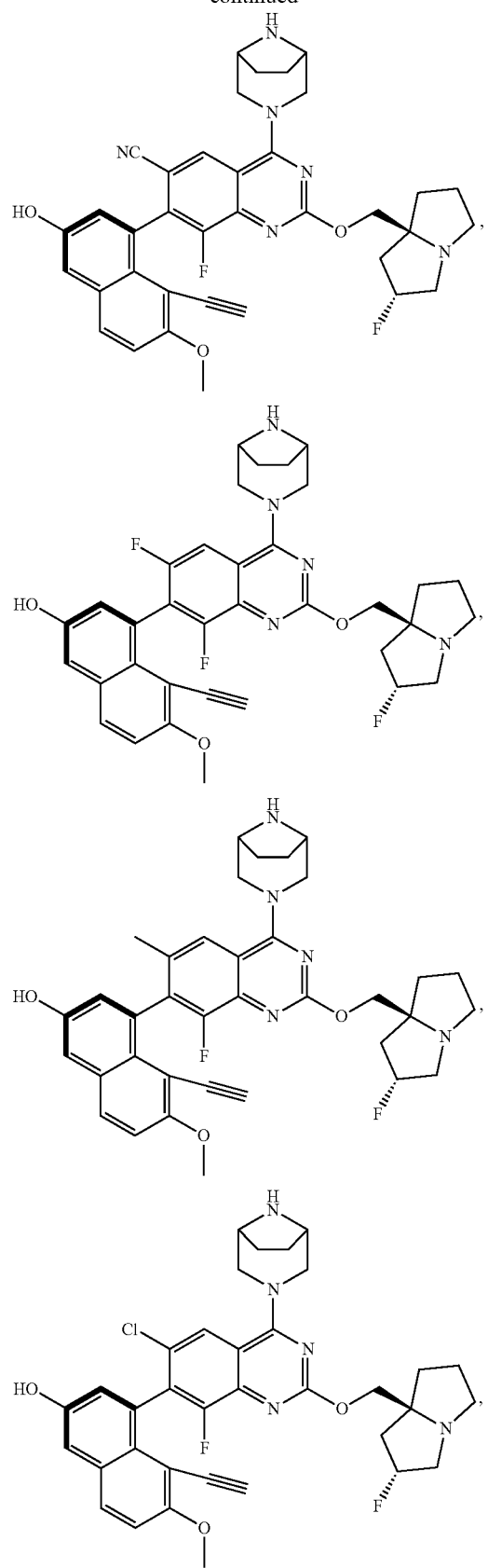
184
-continued
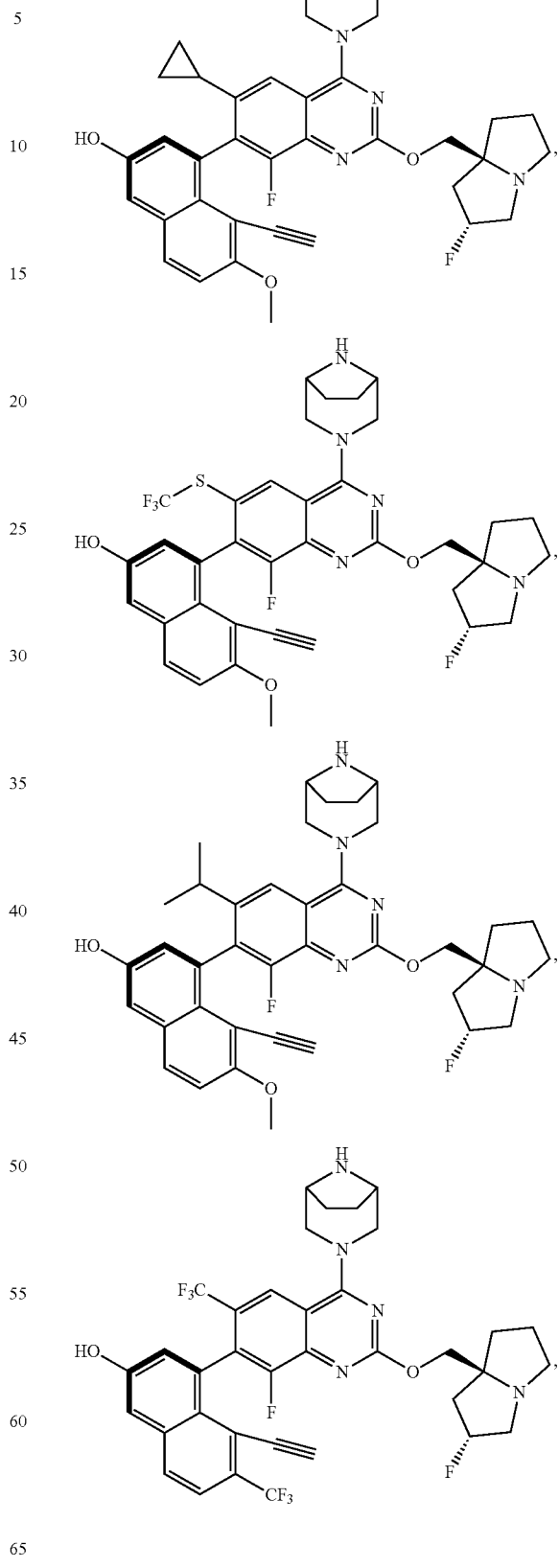

185
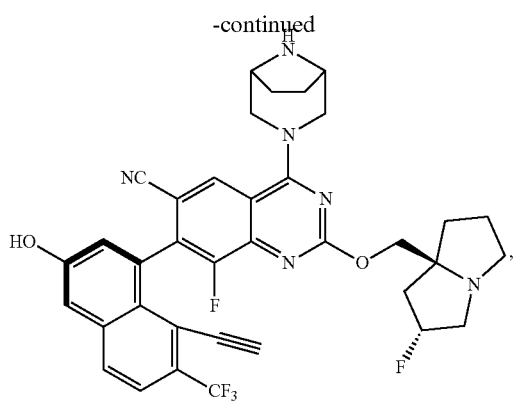
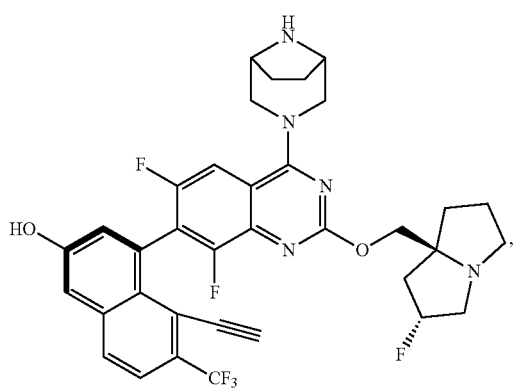
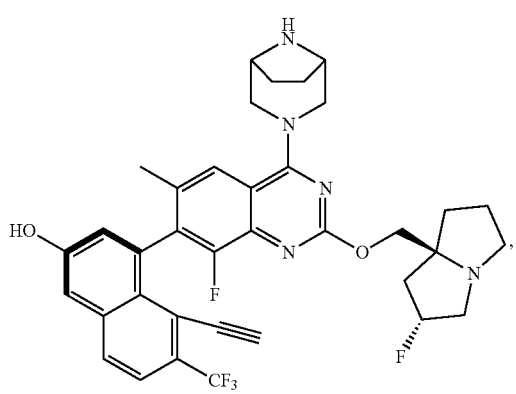
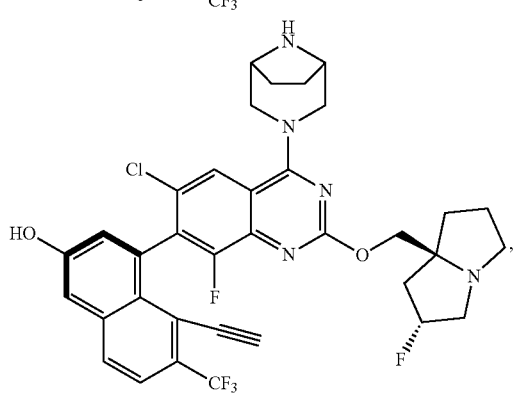
186
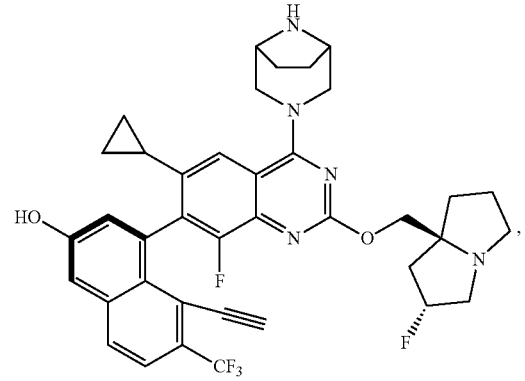
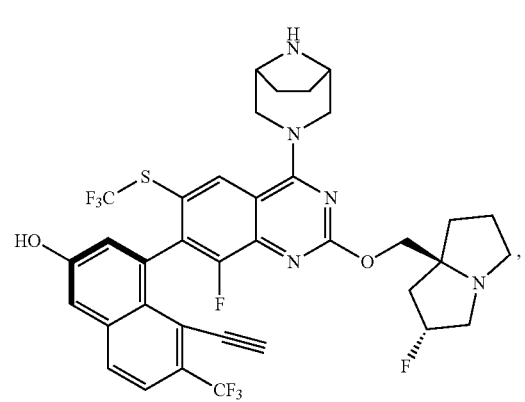
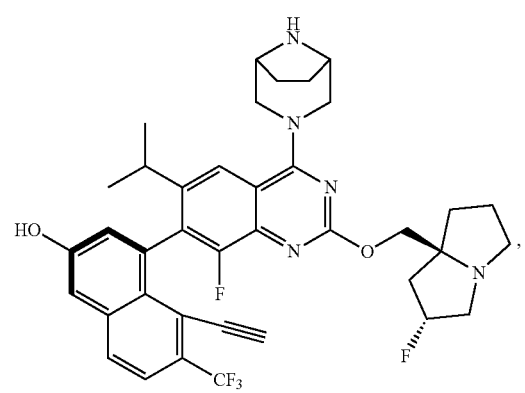
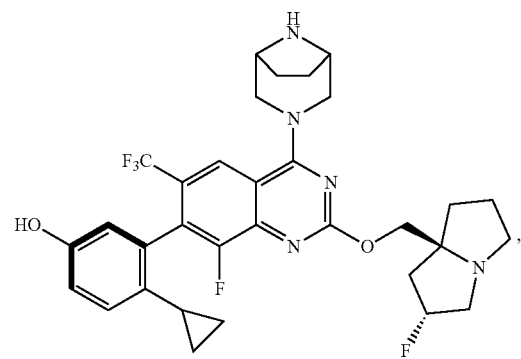

187
-continued
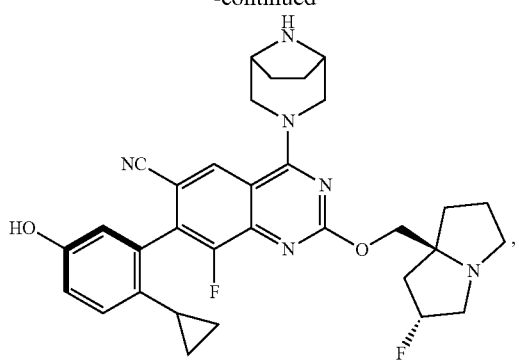
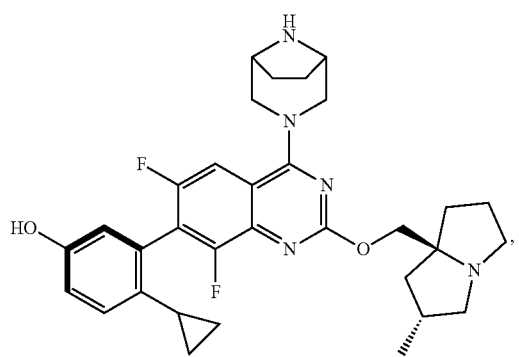
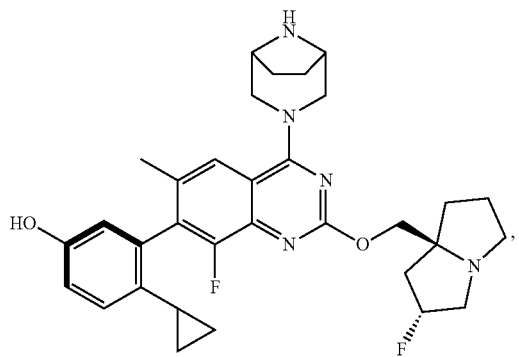
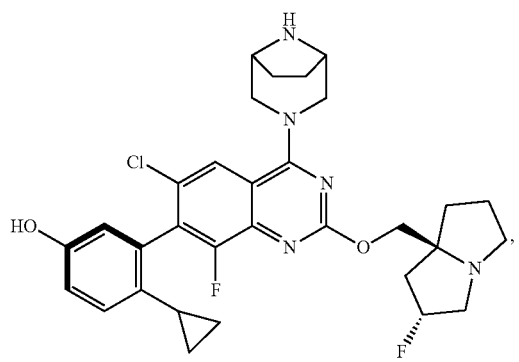
188
-continued
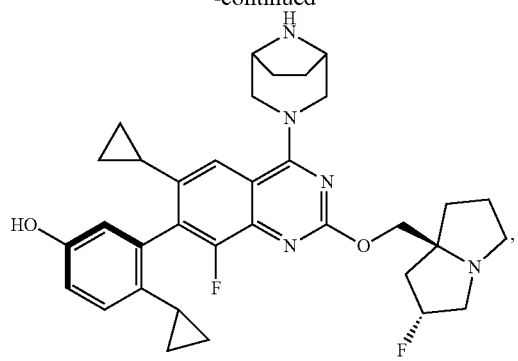
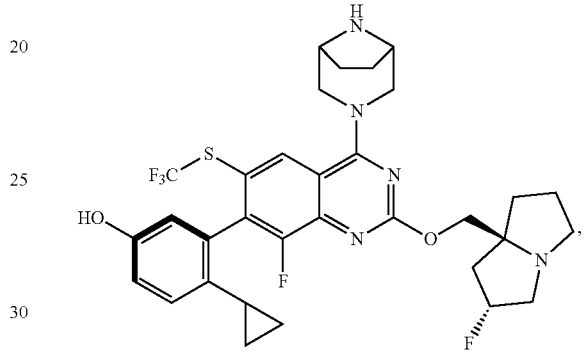
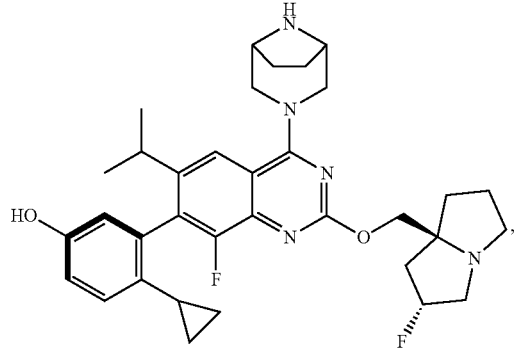
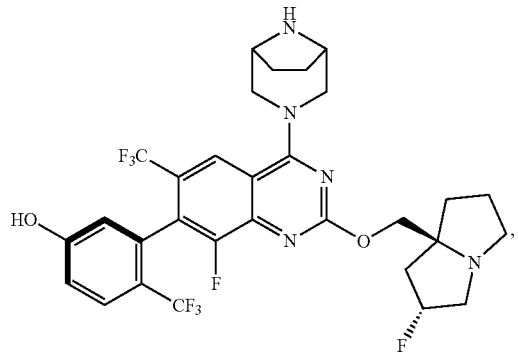

189
-continued
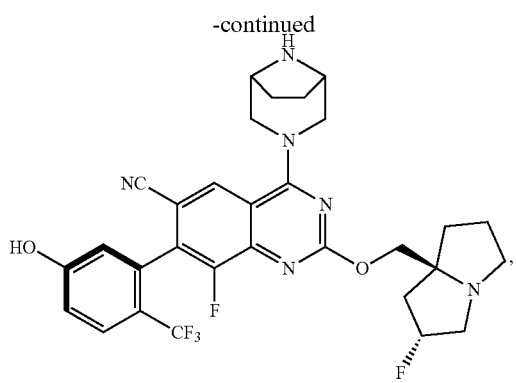
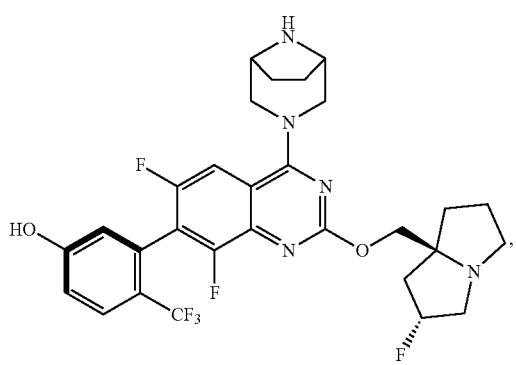
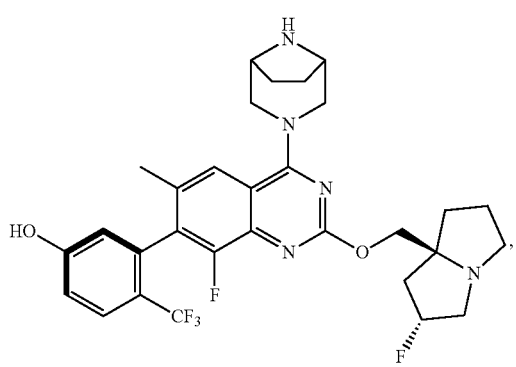
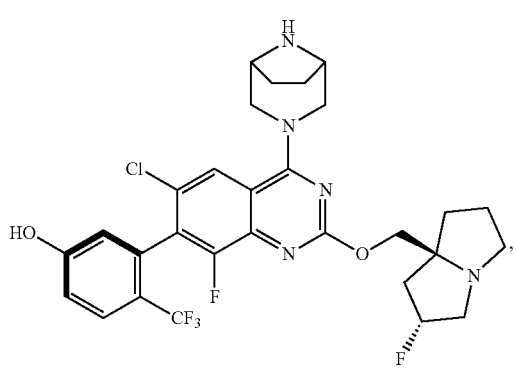
190
-continued
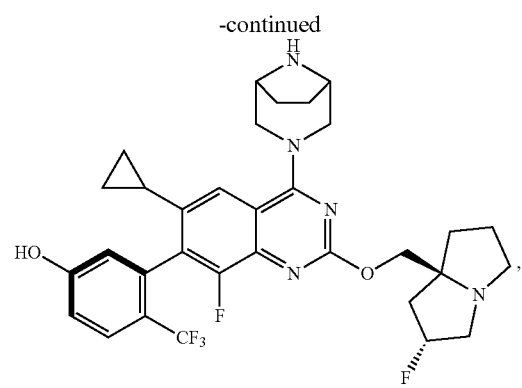
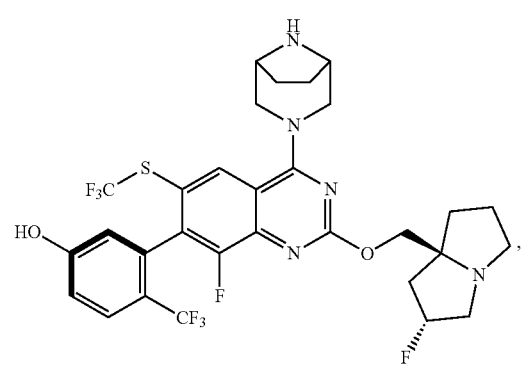
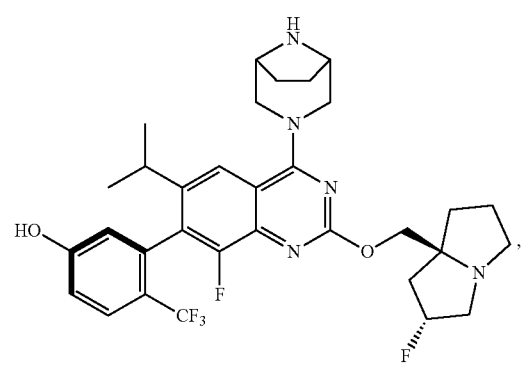
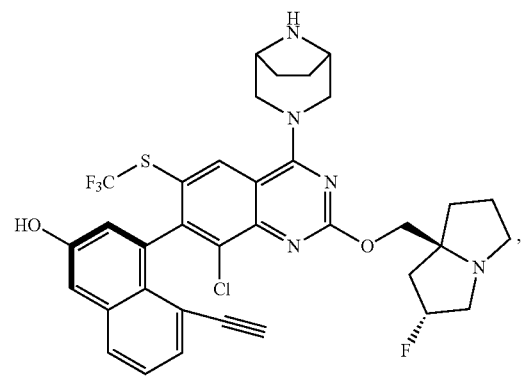

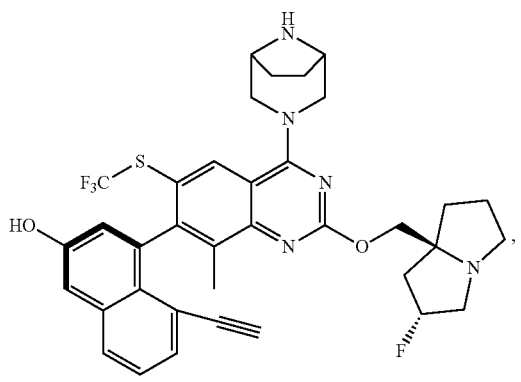
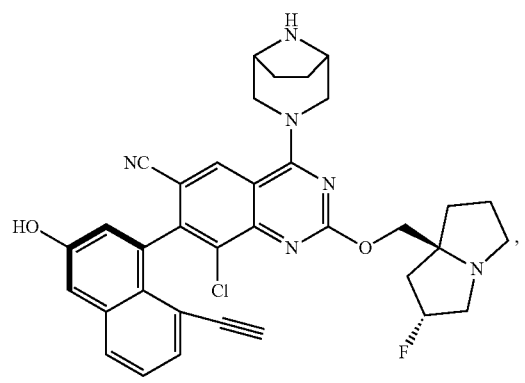
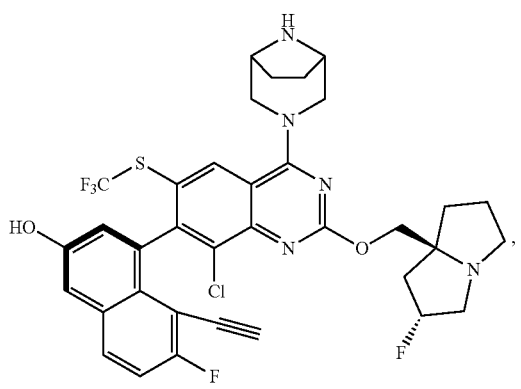
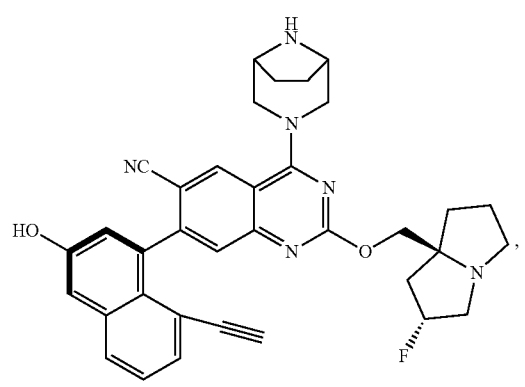
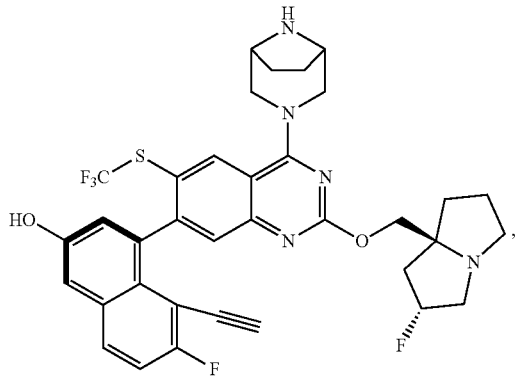
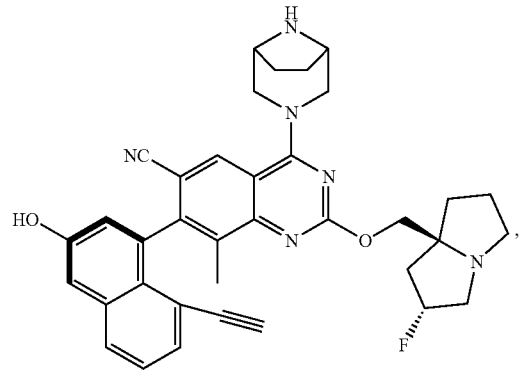

193
-continued
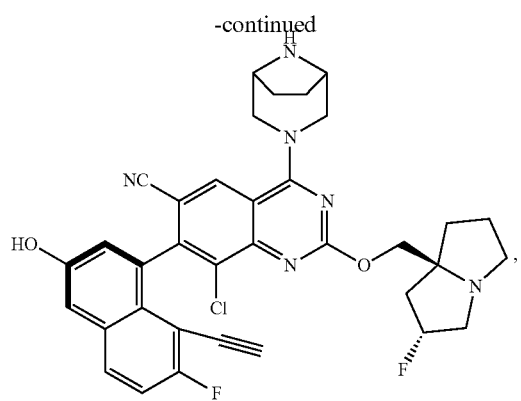
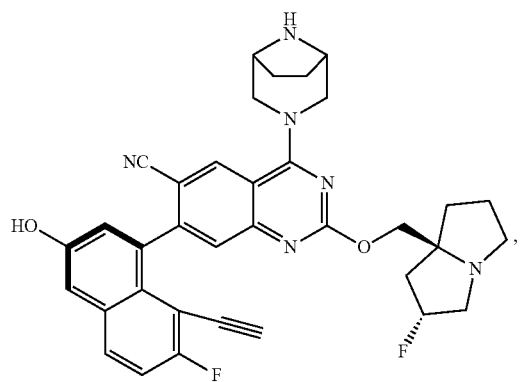
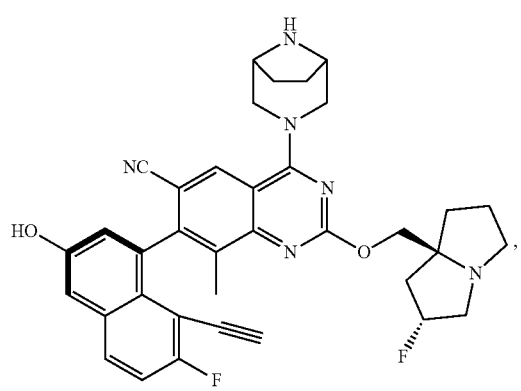
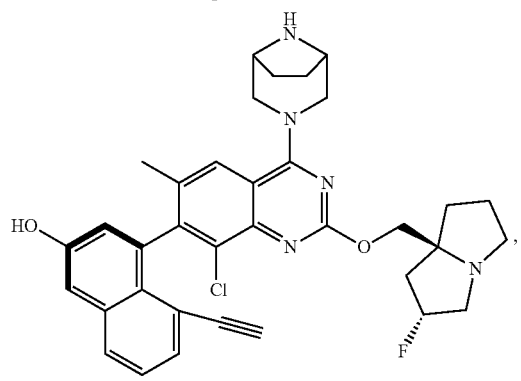
194
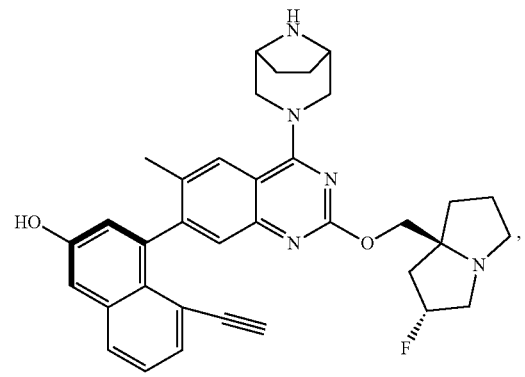
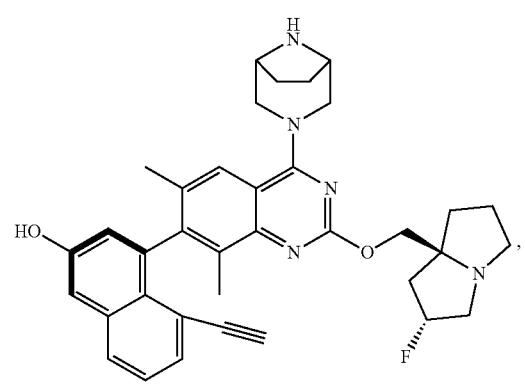
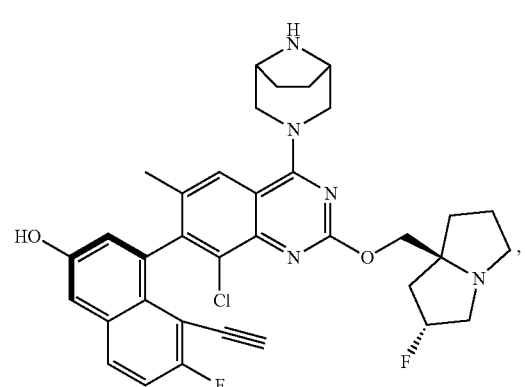
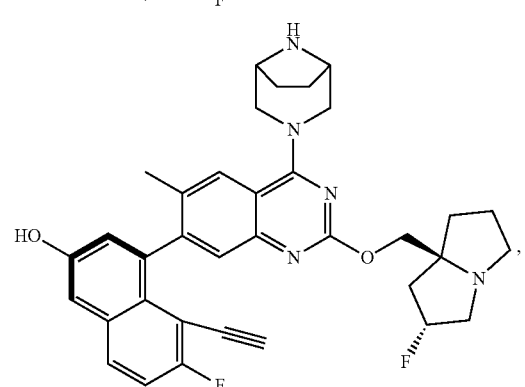

195
-continued
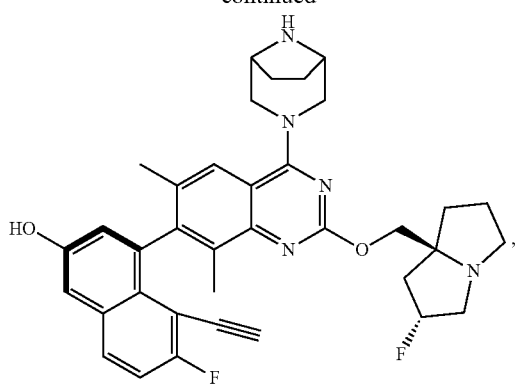
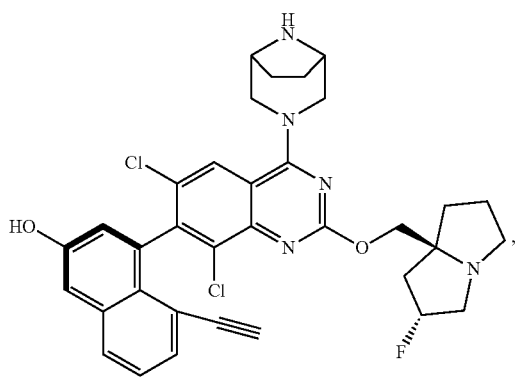
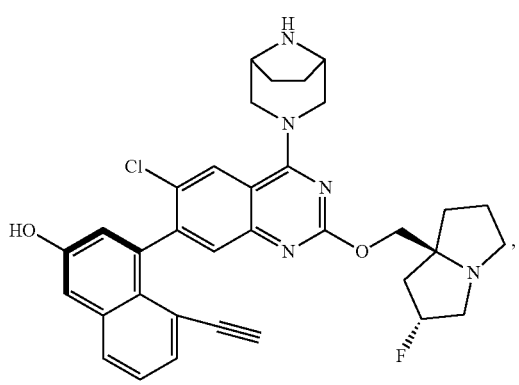
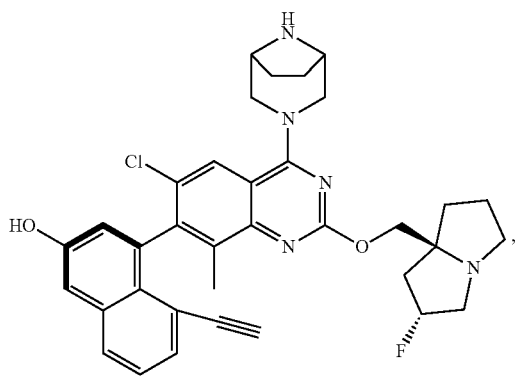
196
-continued
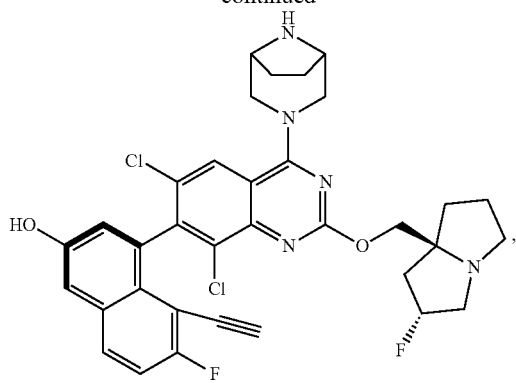
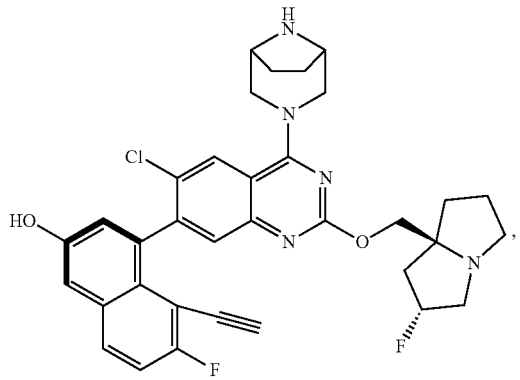
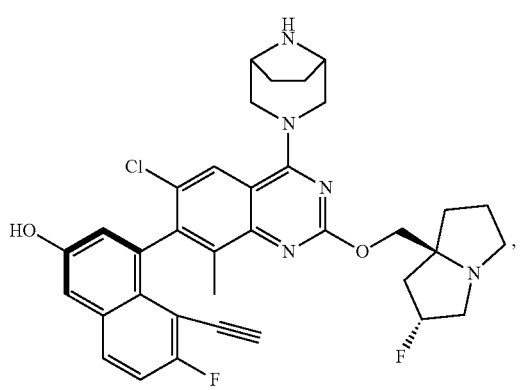
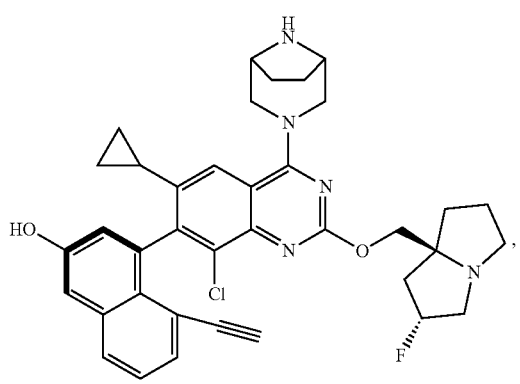

197
-continued
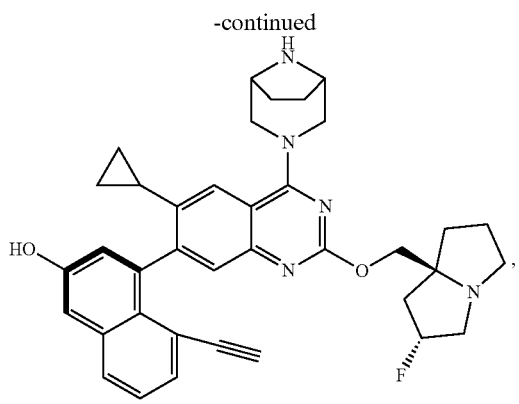
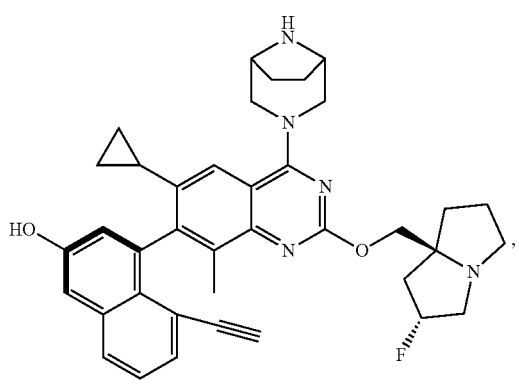
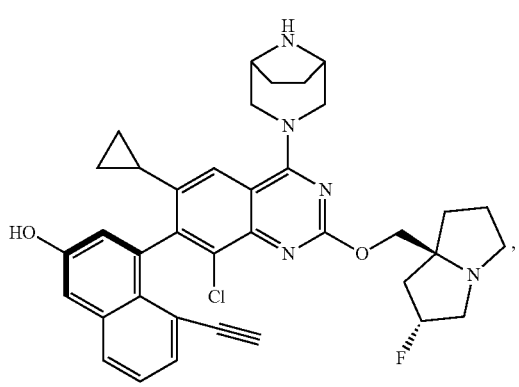
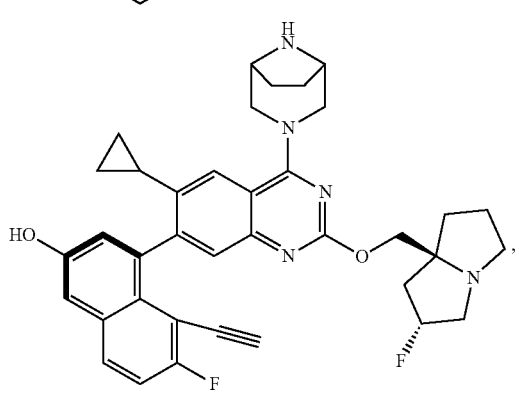
198
-continued
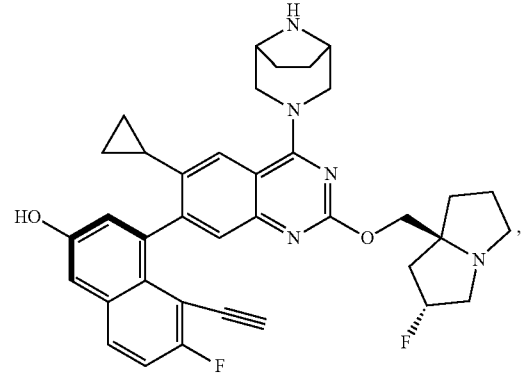
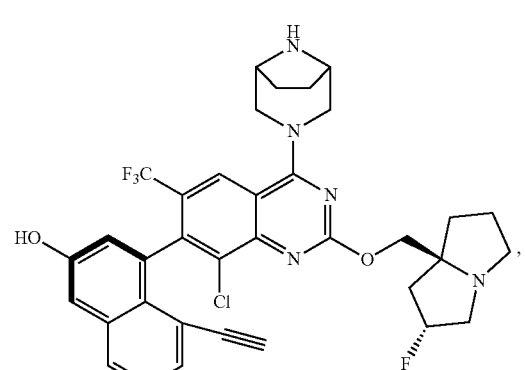
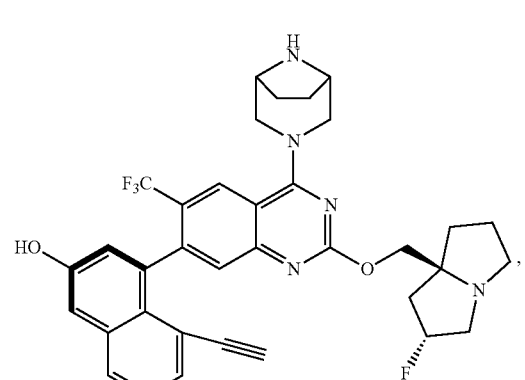
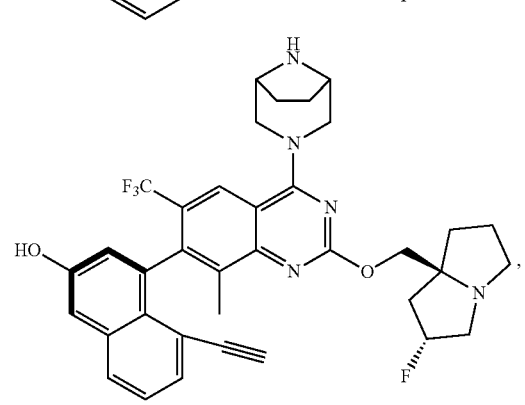

199
-continued
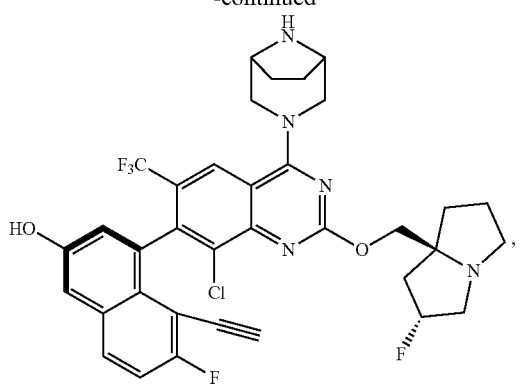
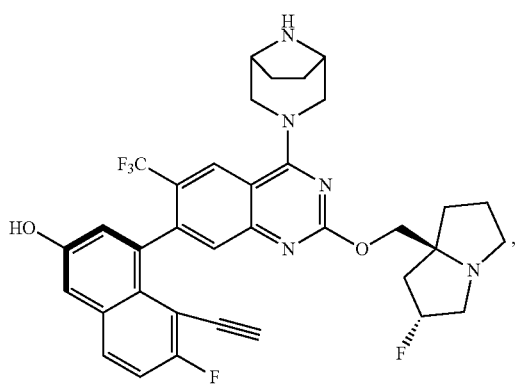
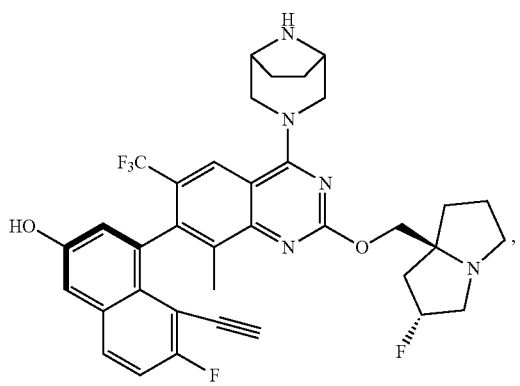
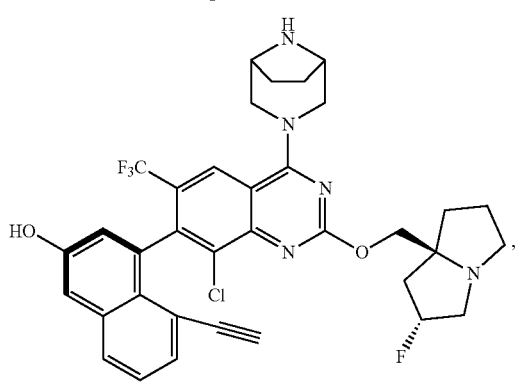
200
-continued
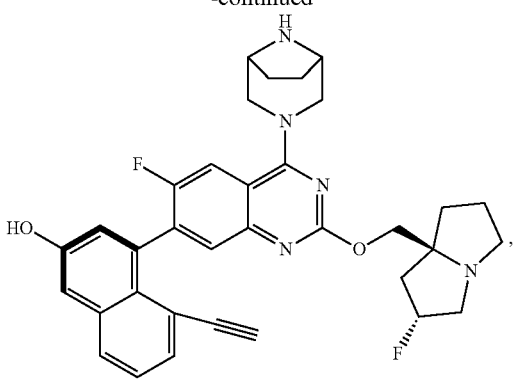

201
-continued
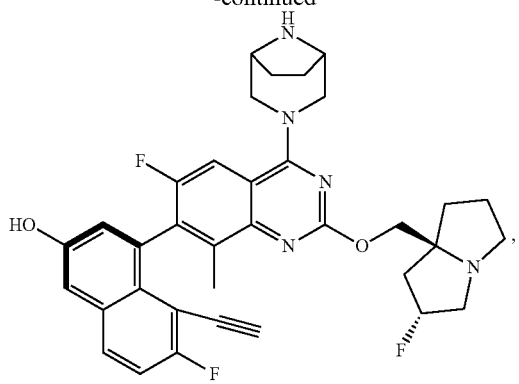
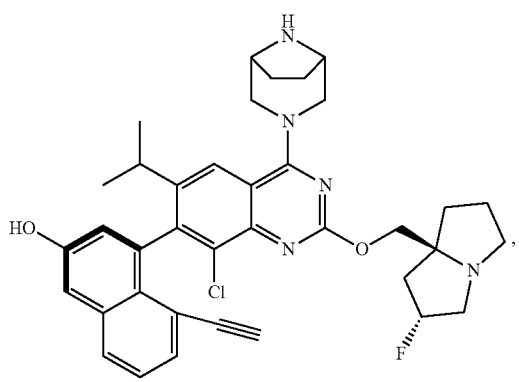
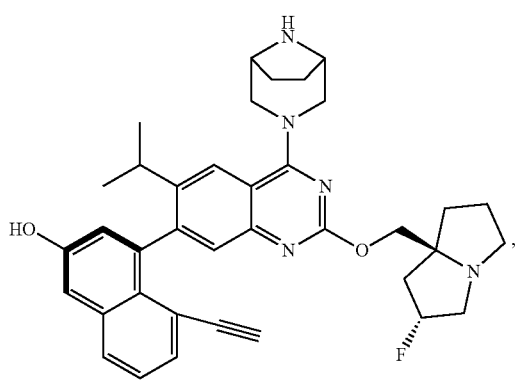
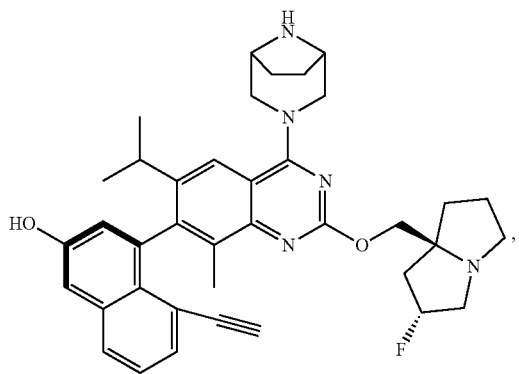
202
-continued
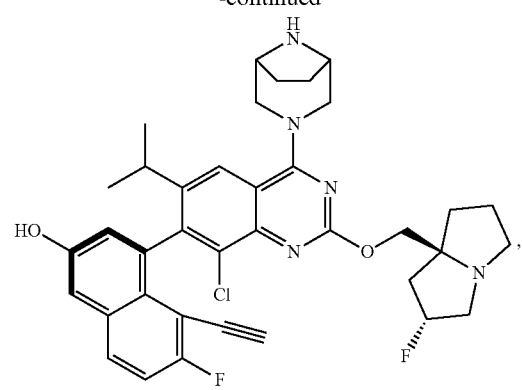
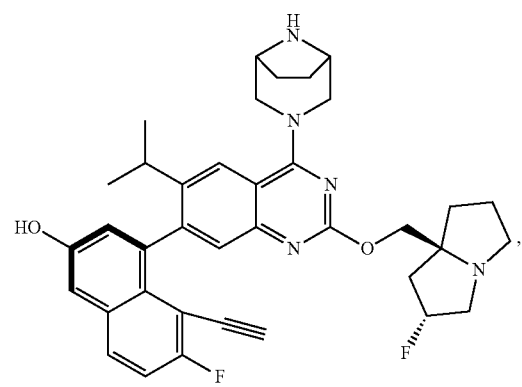
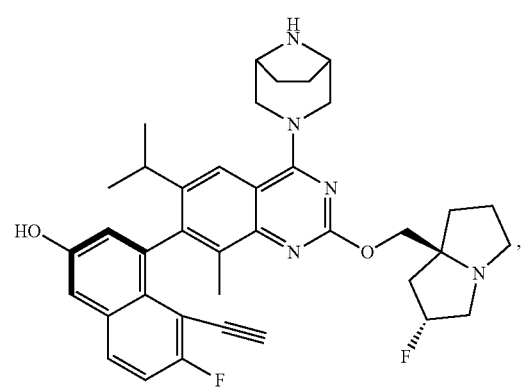
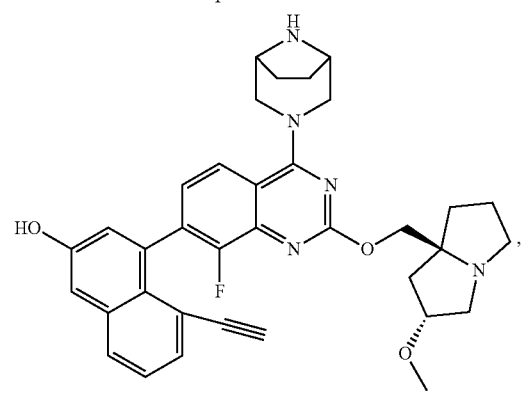

203
-continued
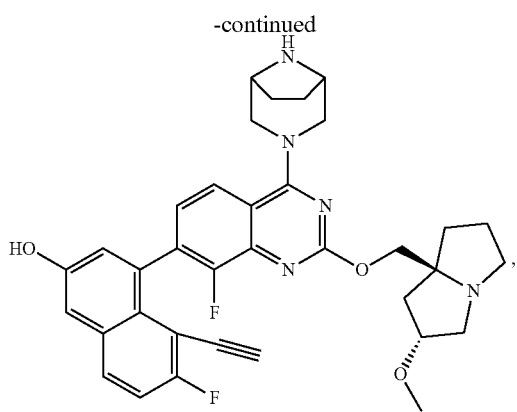
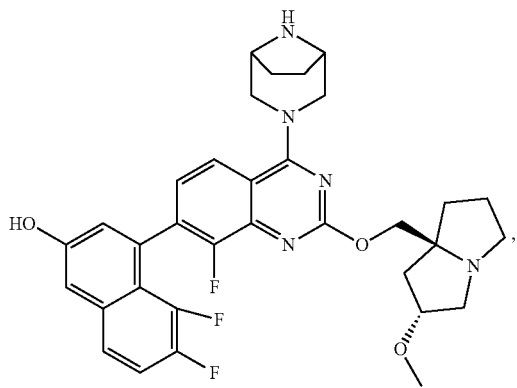
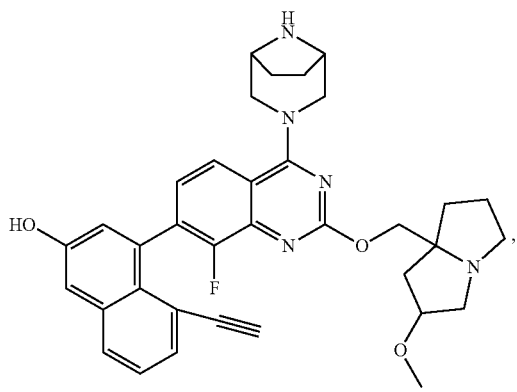
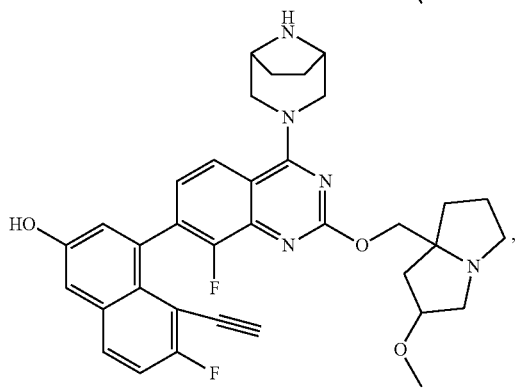
204
-continued
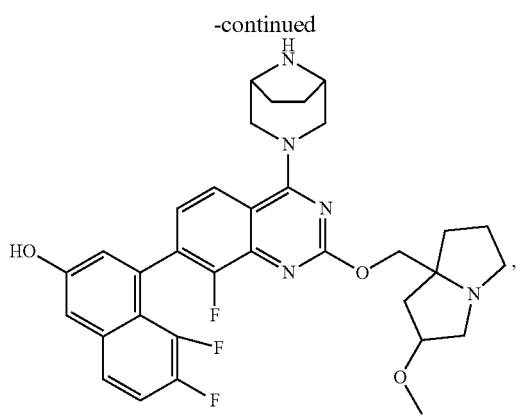
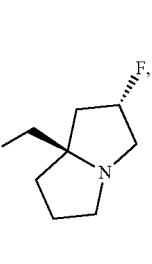

-continued

207
-continued
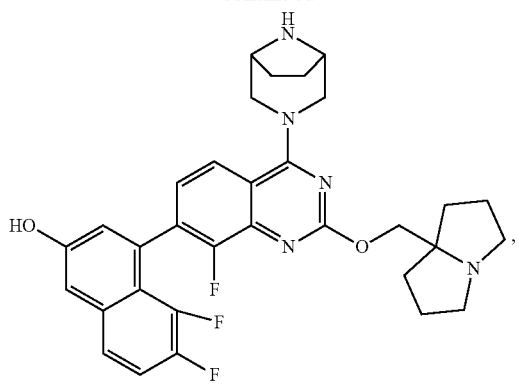
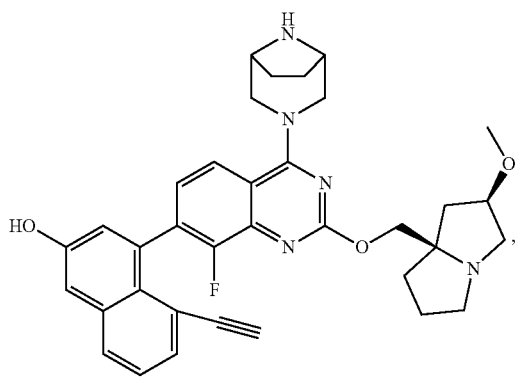
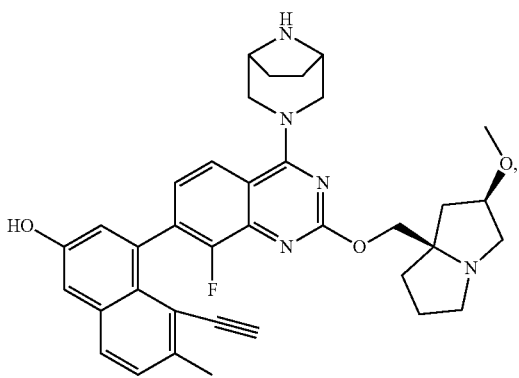
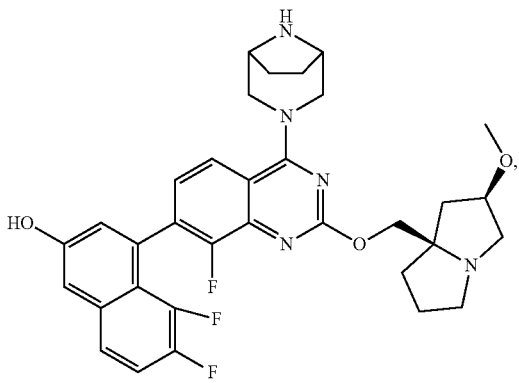
208
-continued
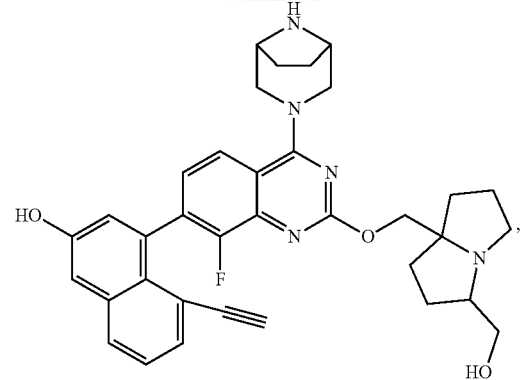
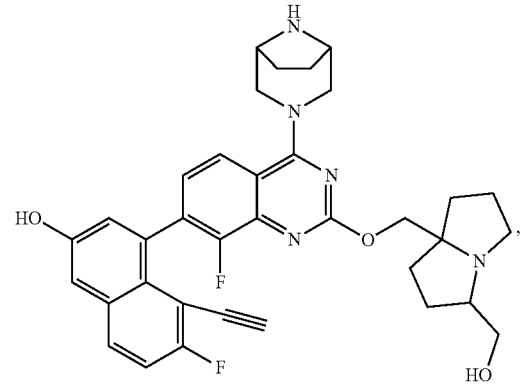
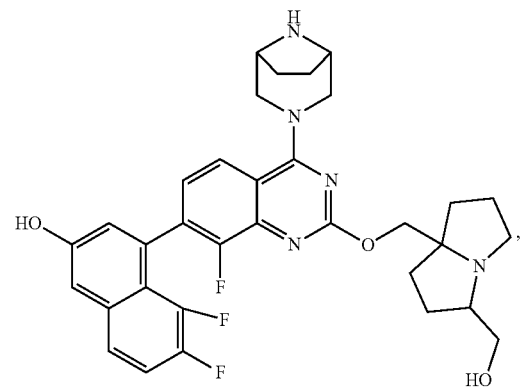
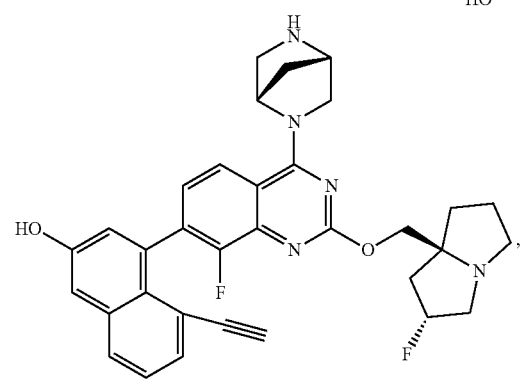

209
-continued
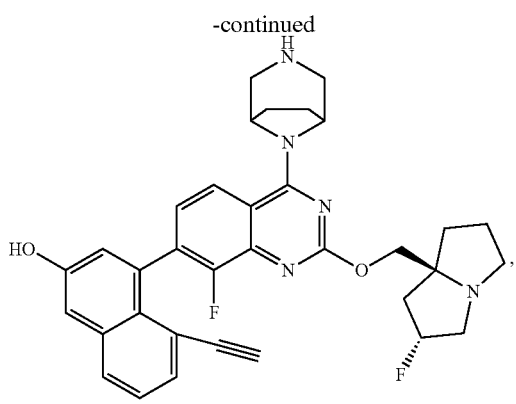
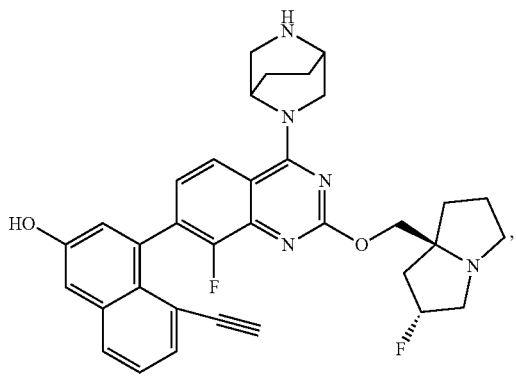
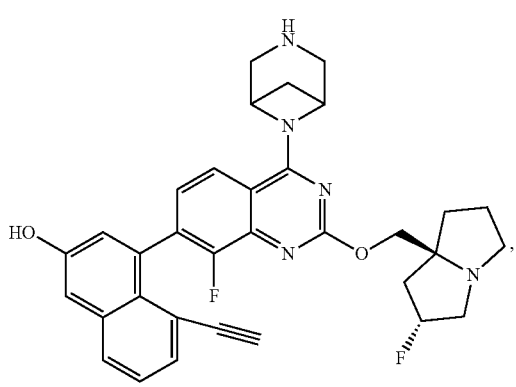
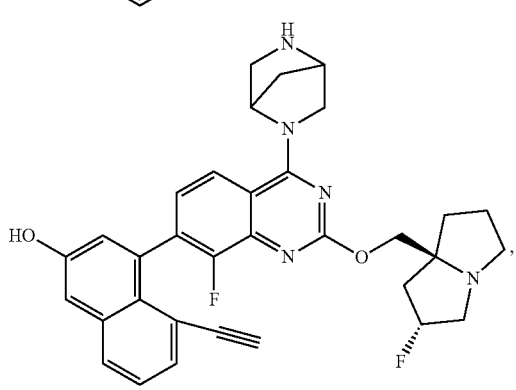
210
-continued
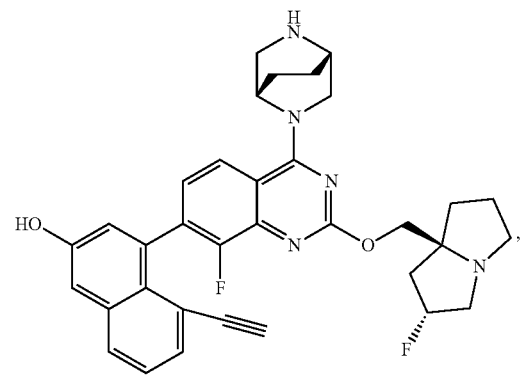
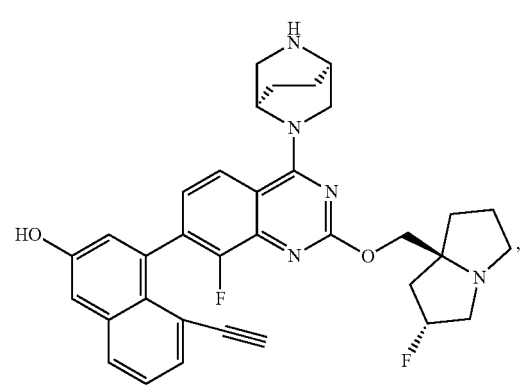
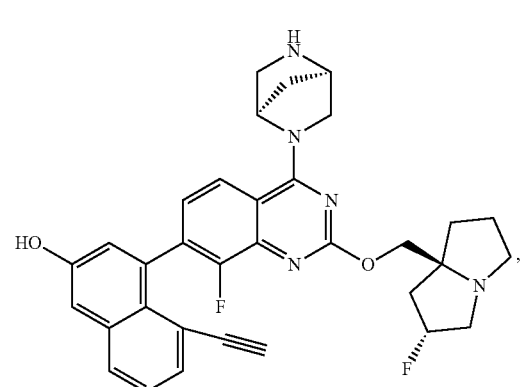
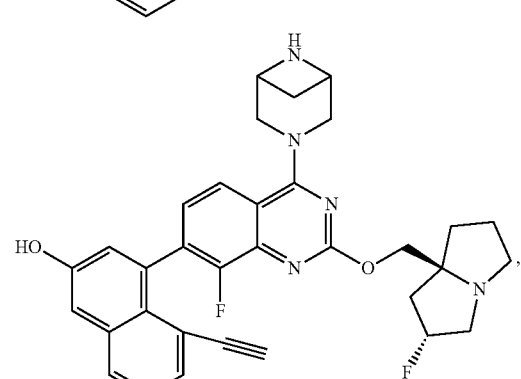

211
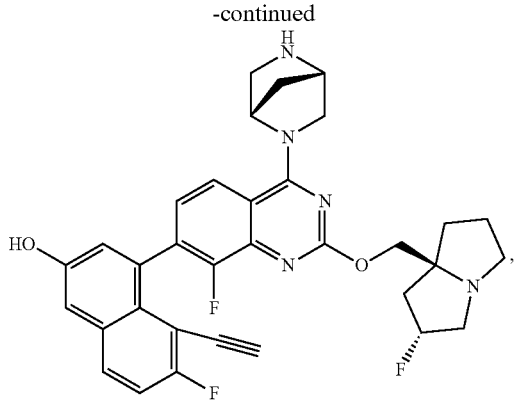
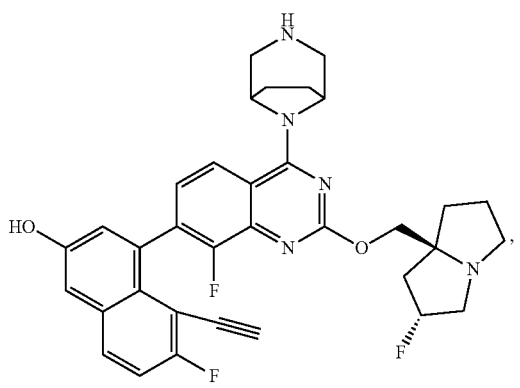
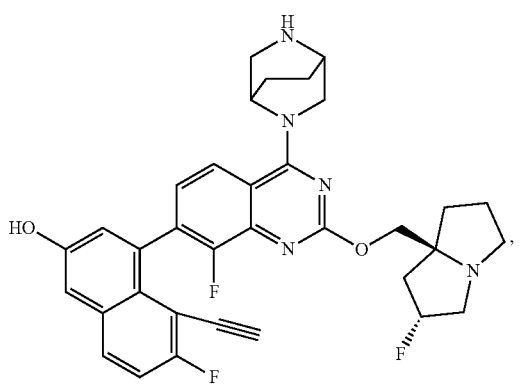
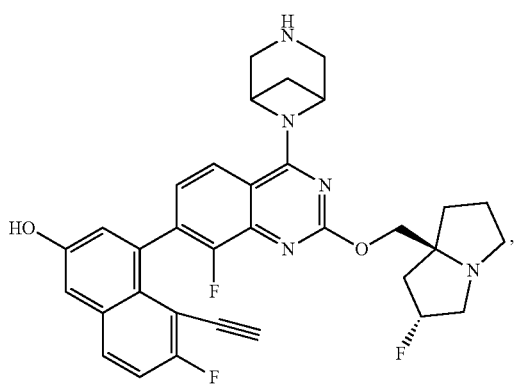
212
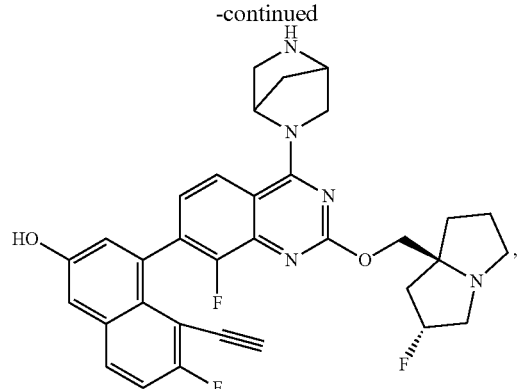
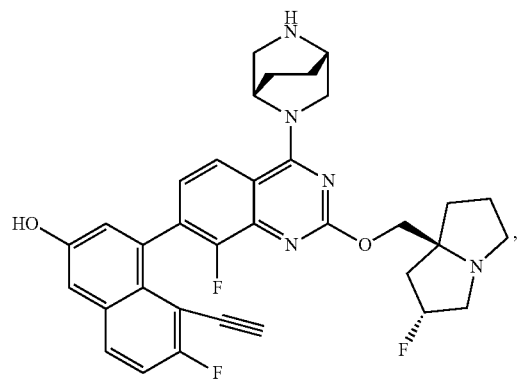
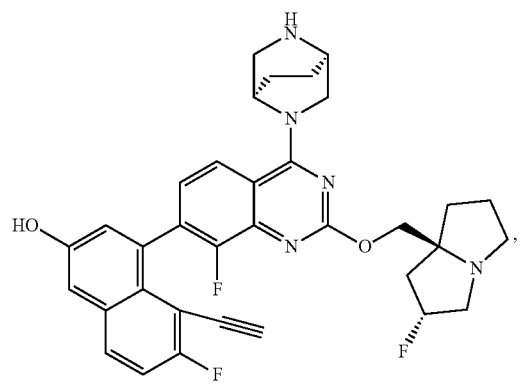
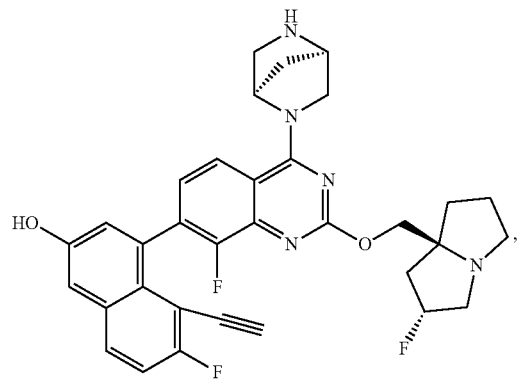

213
-continued
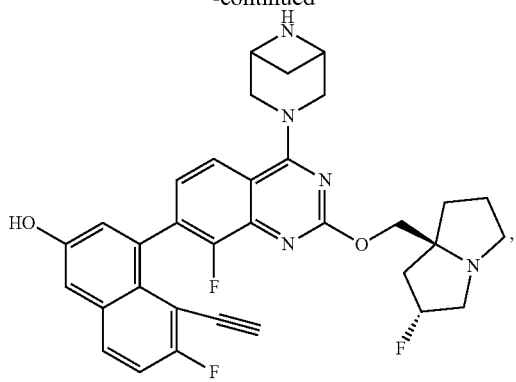
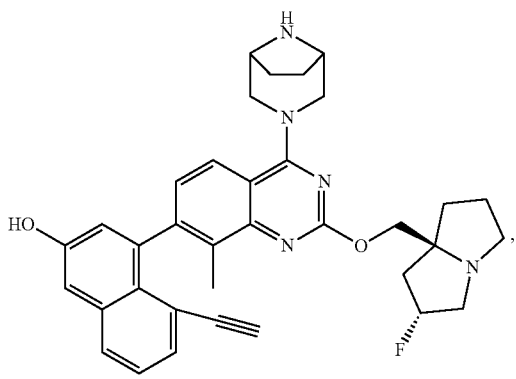
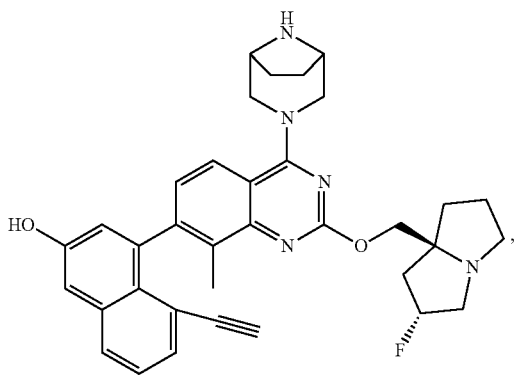
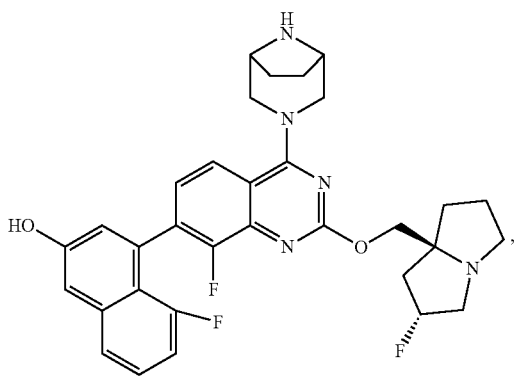
214
-continued
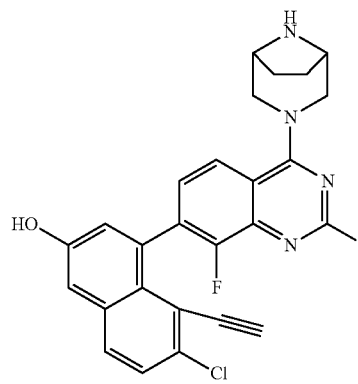
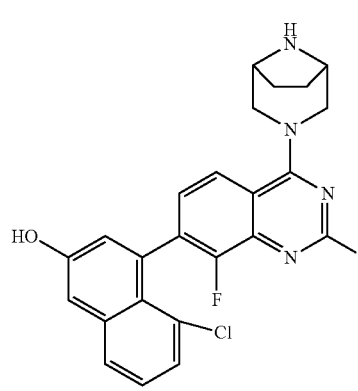
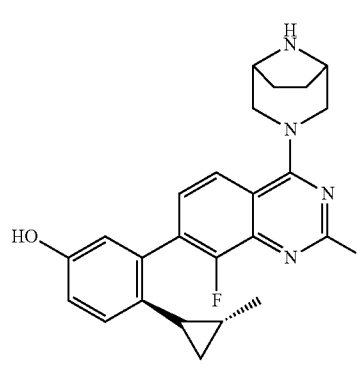
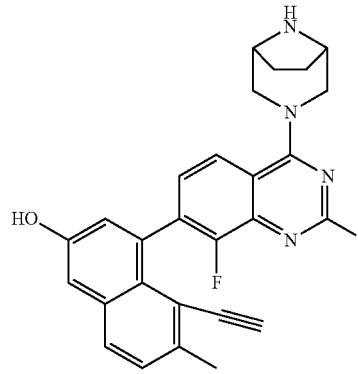

215
-continued
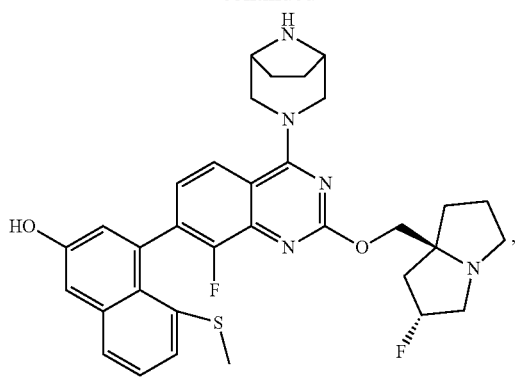
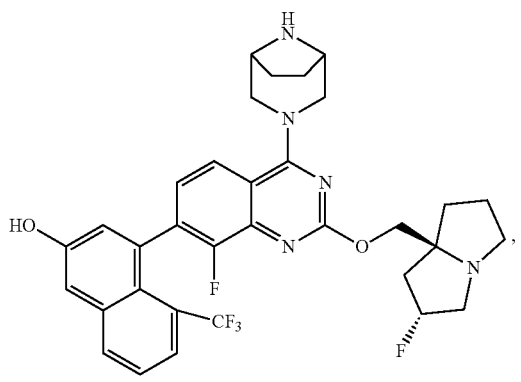
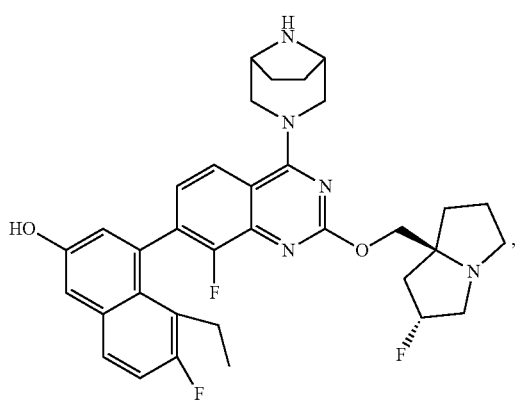
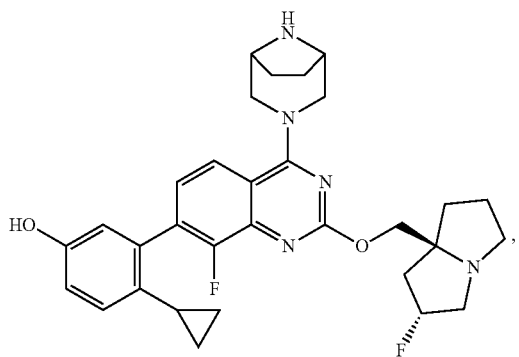
216
-continued
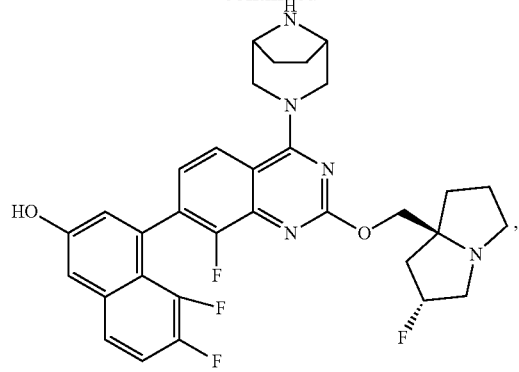
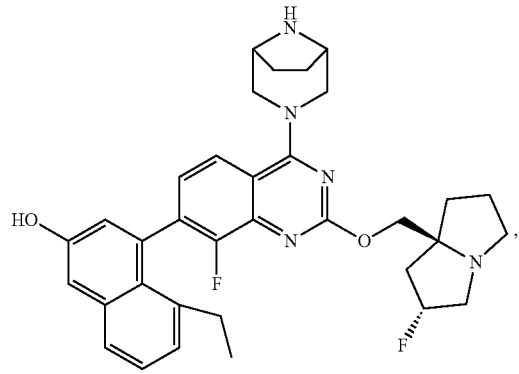

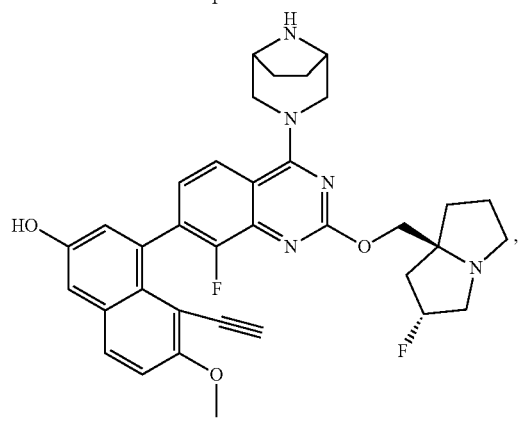

217
-continued
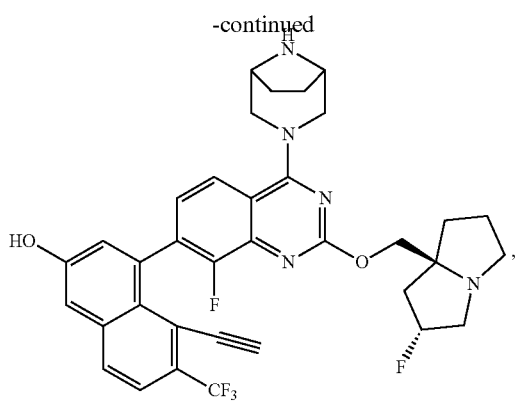
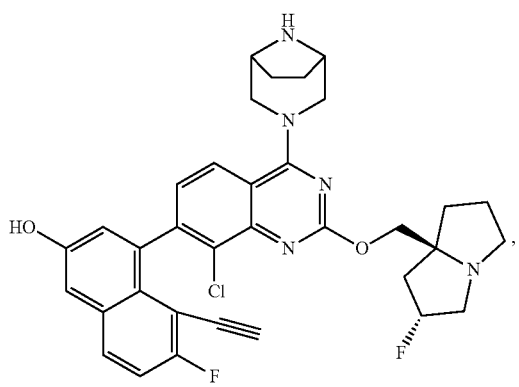
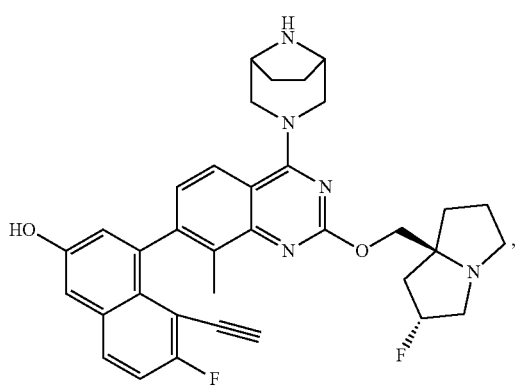
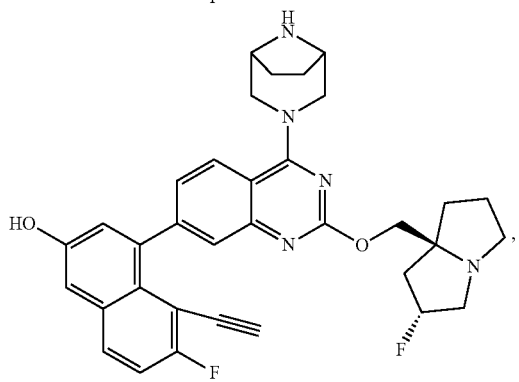
218
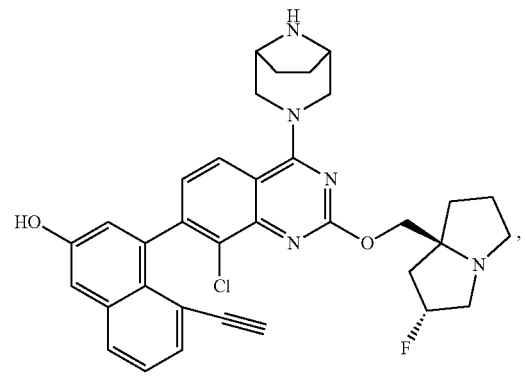
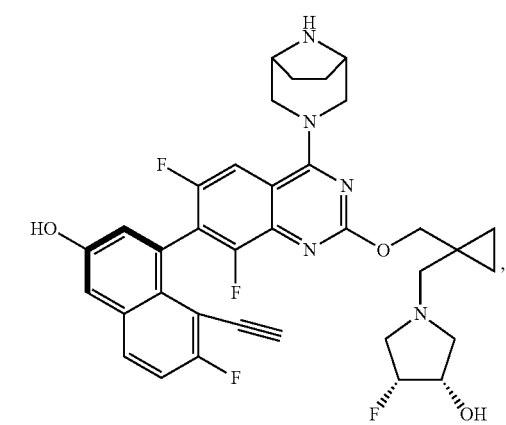
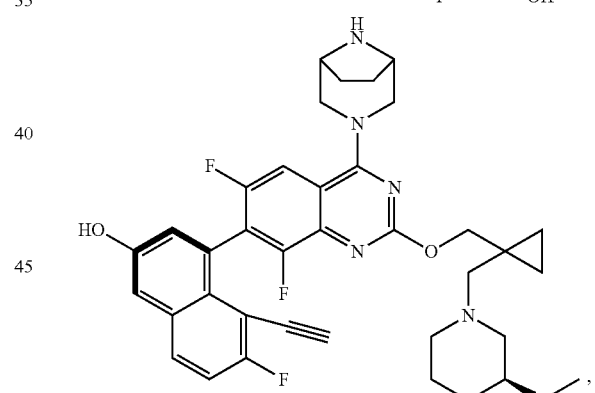
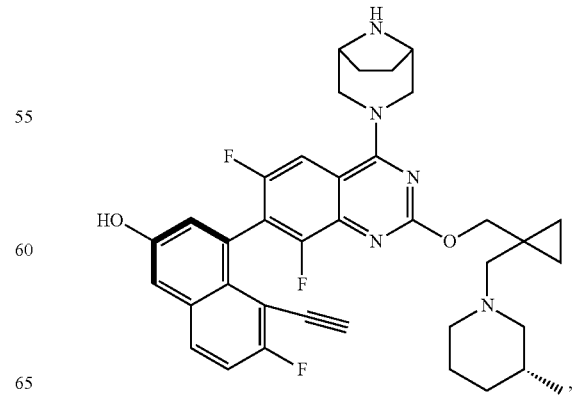

219
-continued
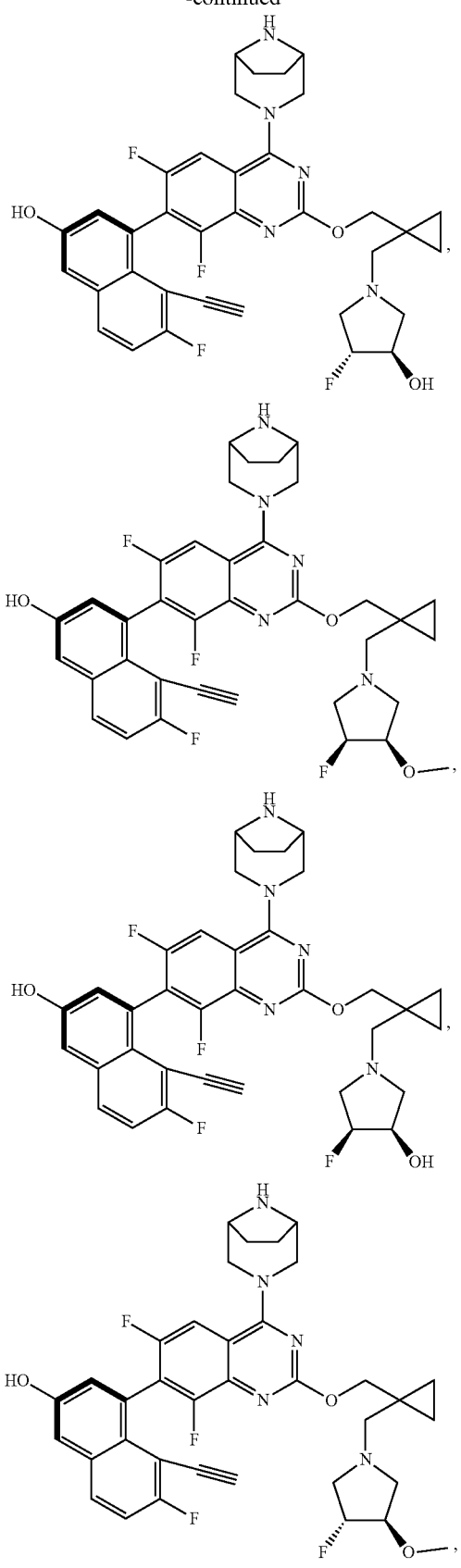
220
-continued
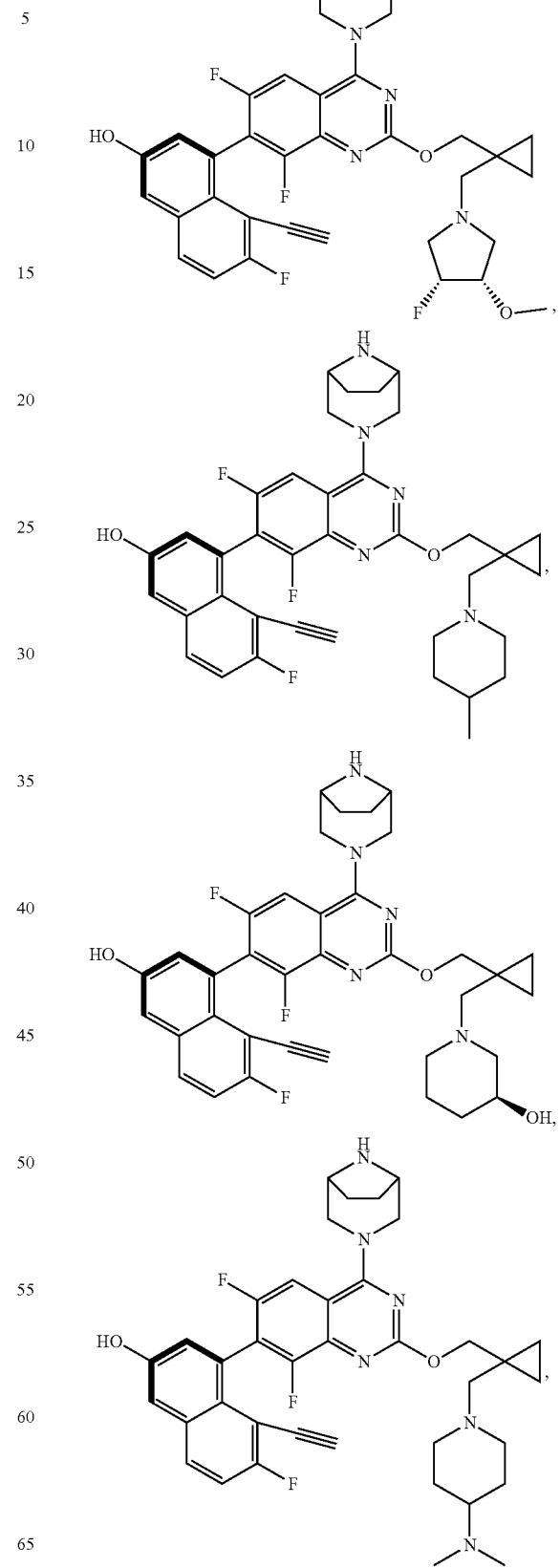

221
-continued
222
-continued
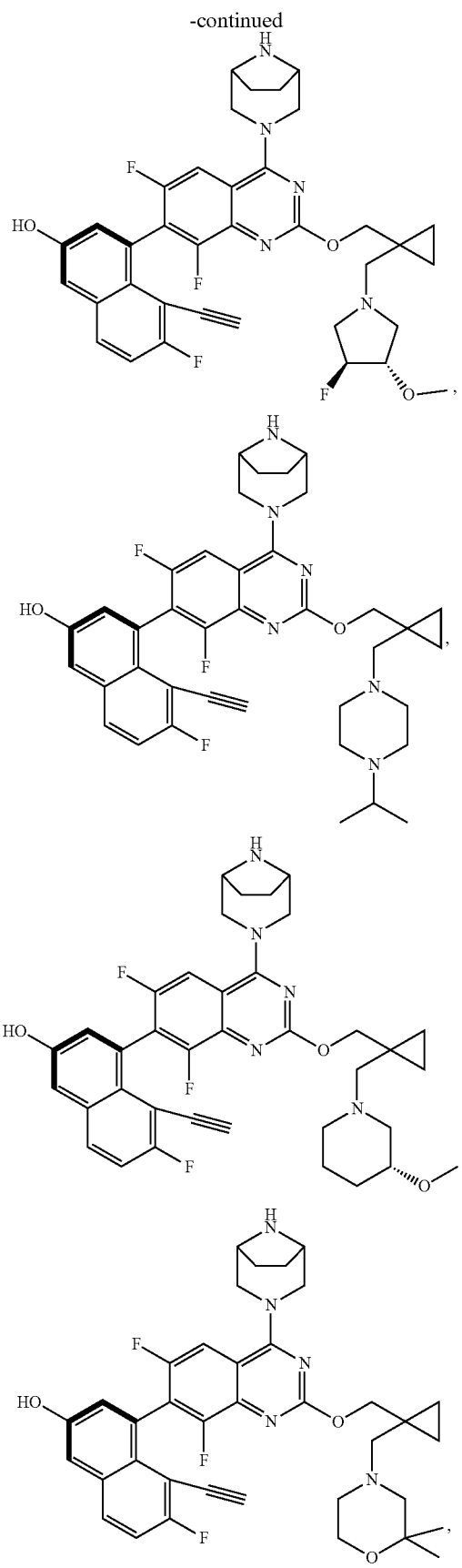
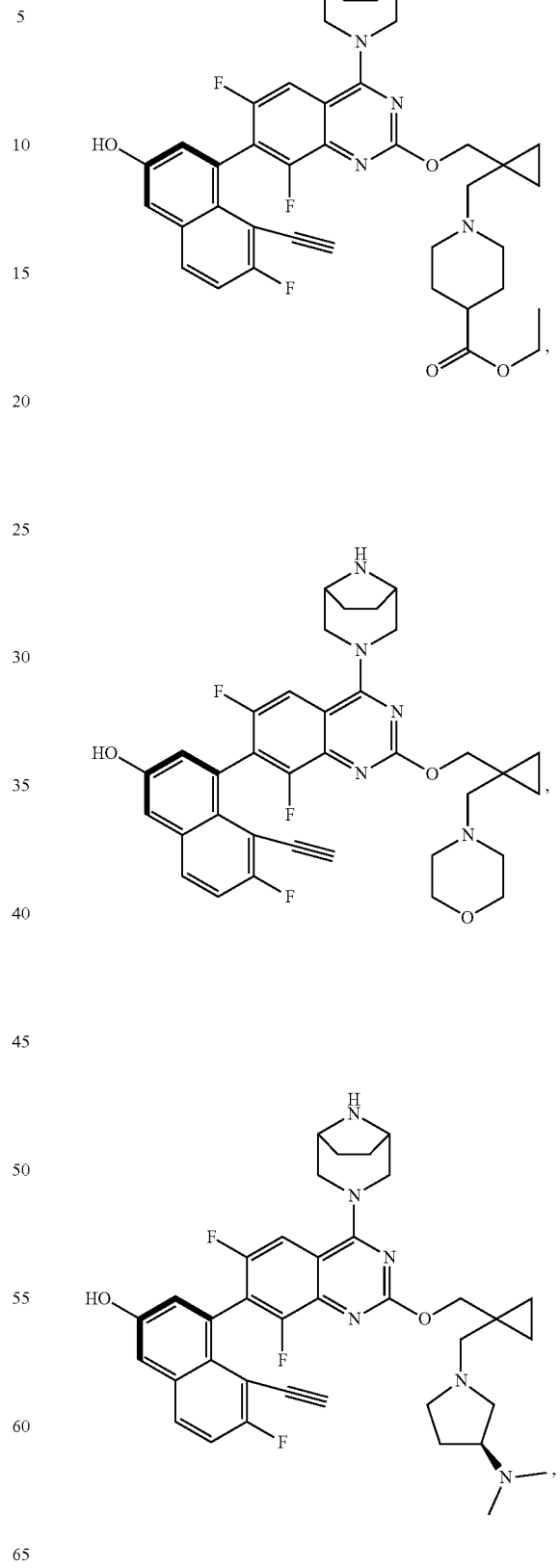

223
-continued
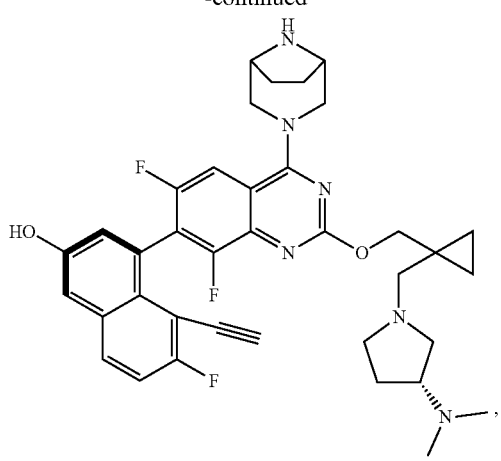
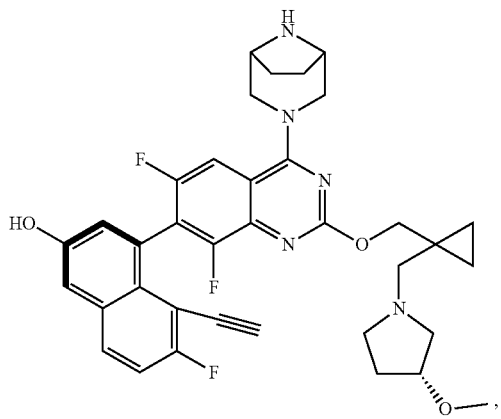
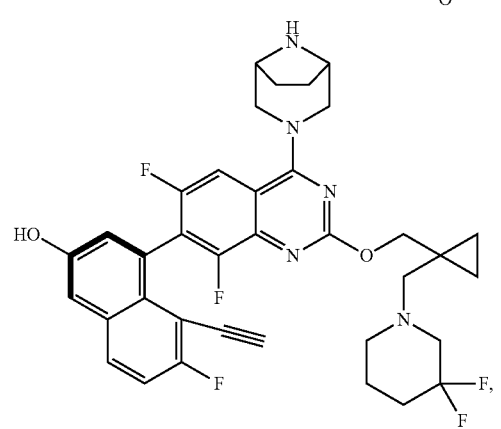
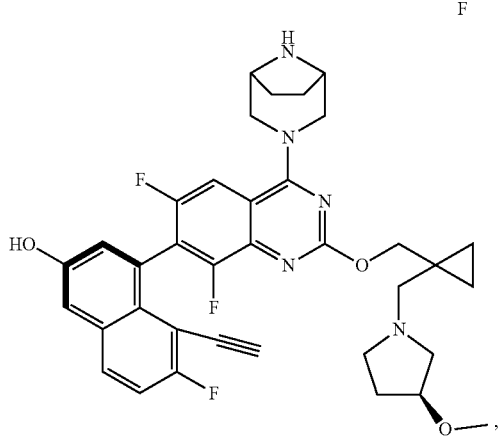
224
-continued
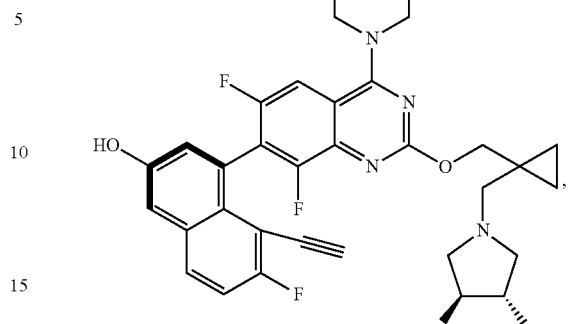
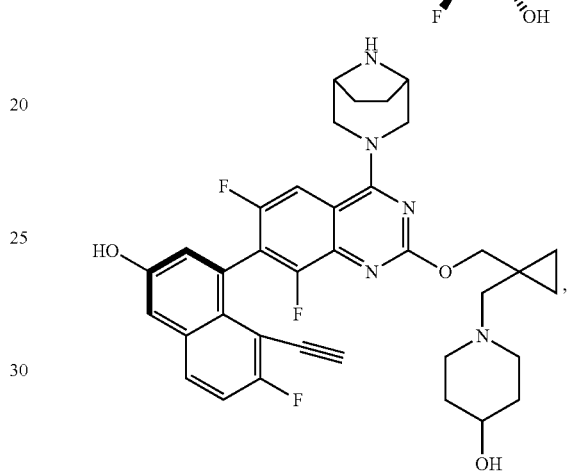

225
-continued
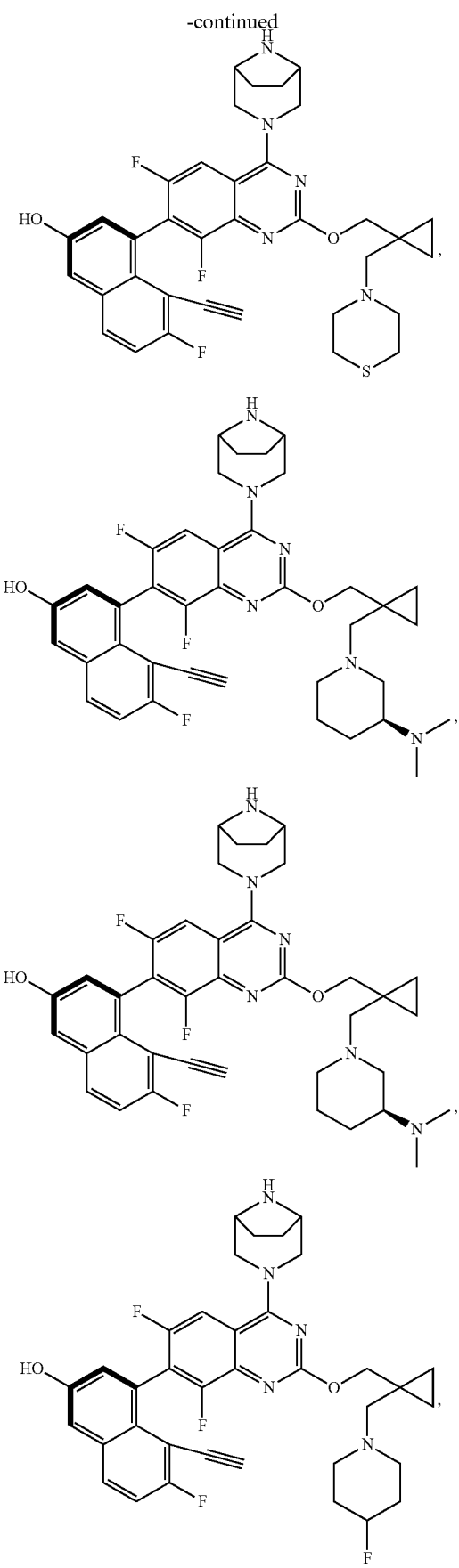
226
-continued
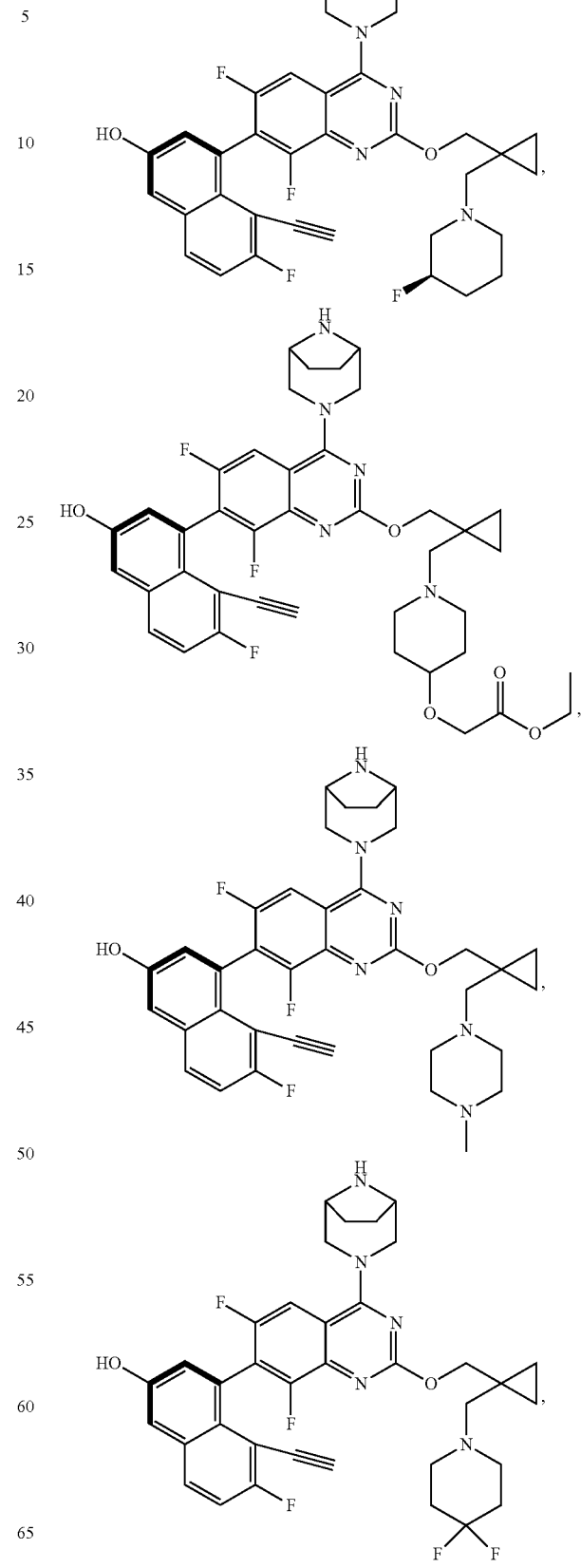

227
-continued
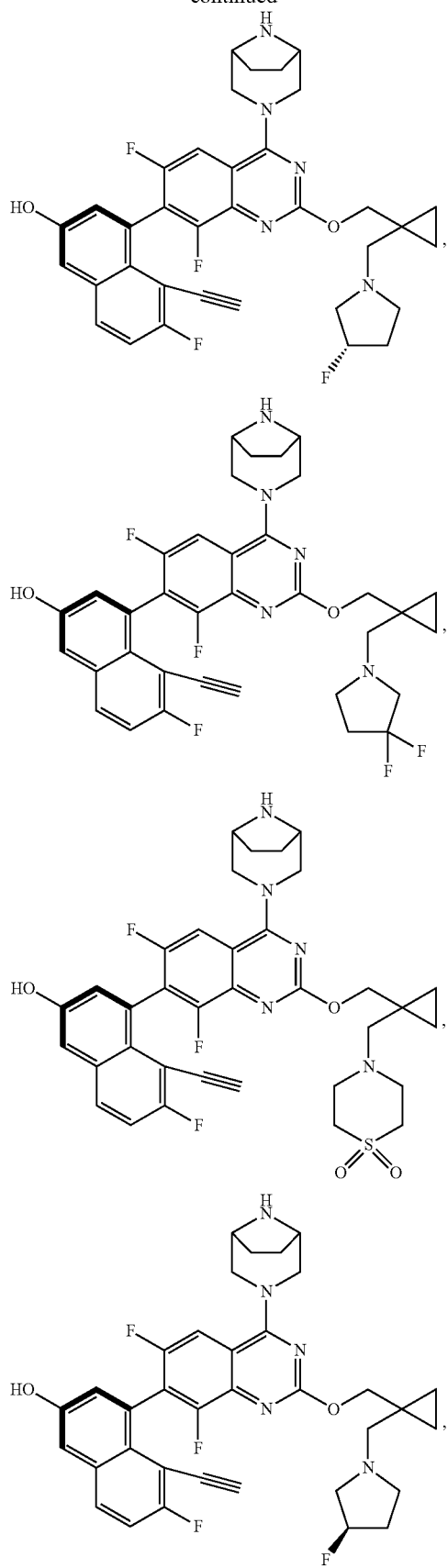
228
-continued
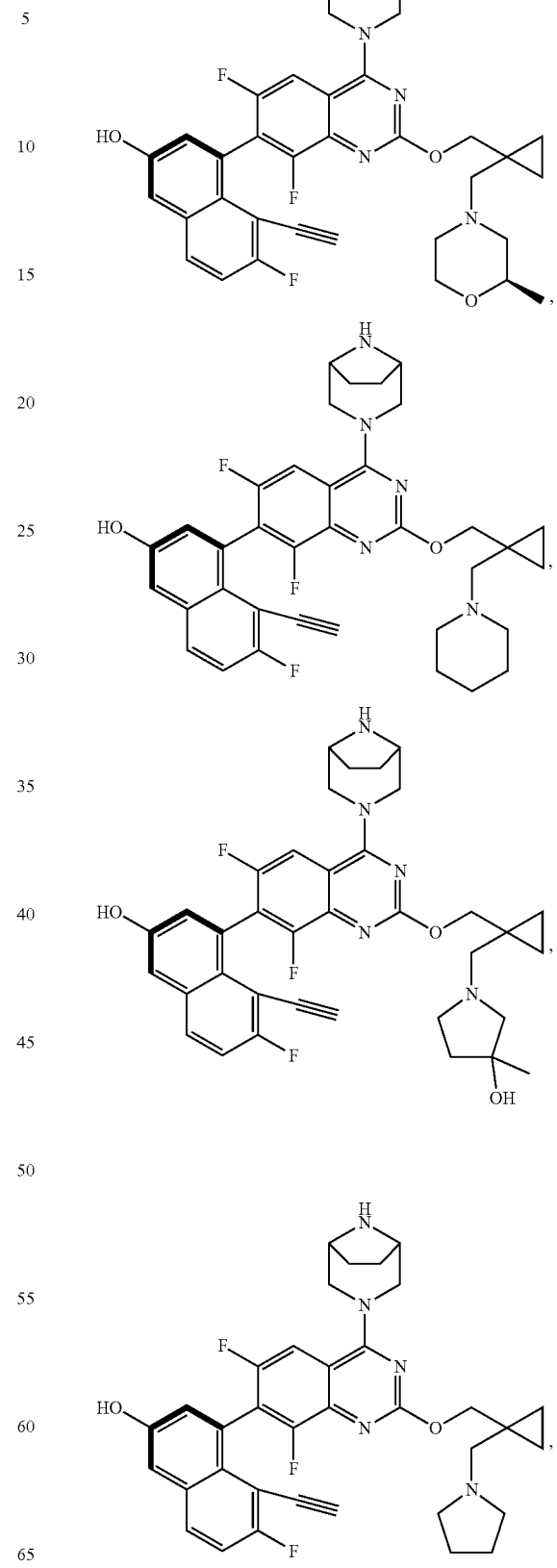

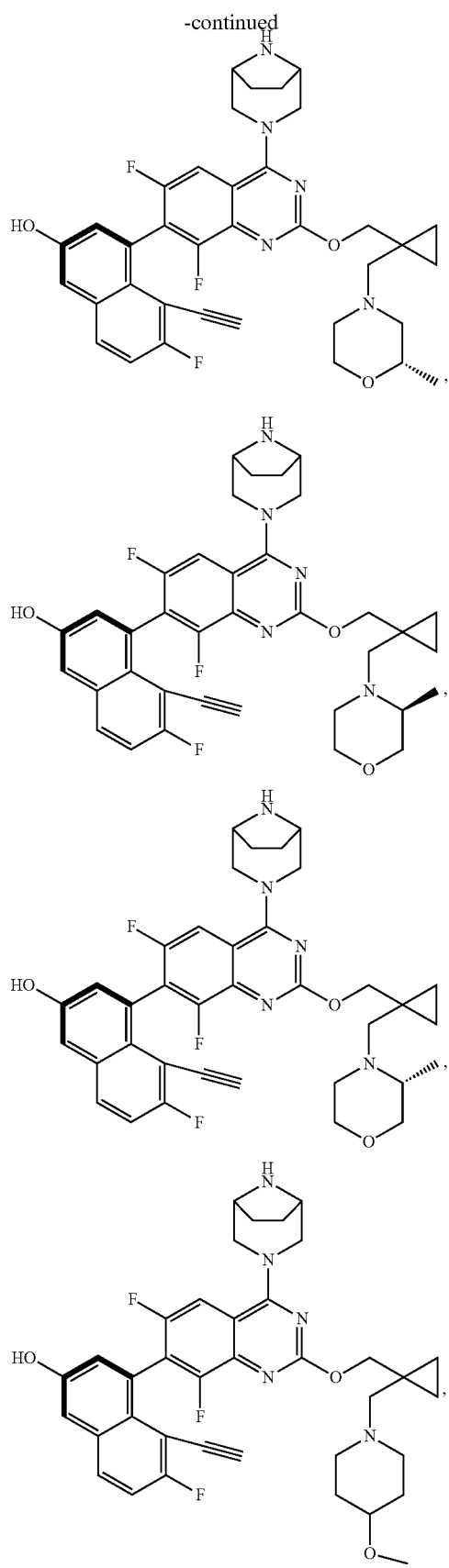
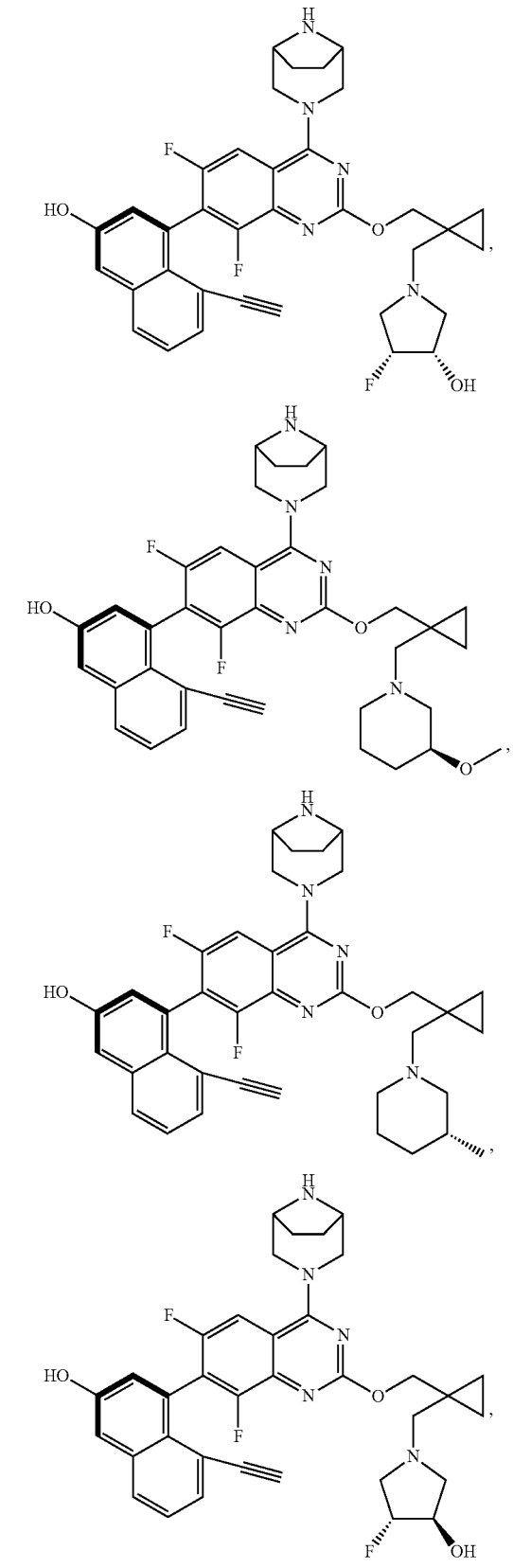

-continued
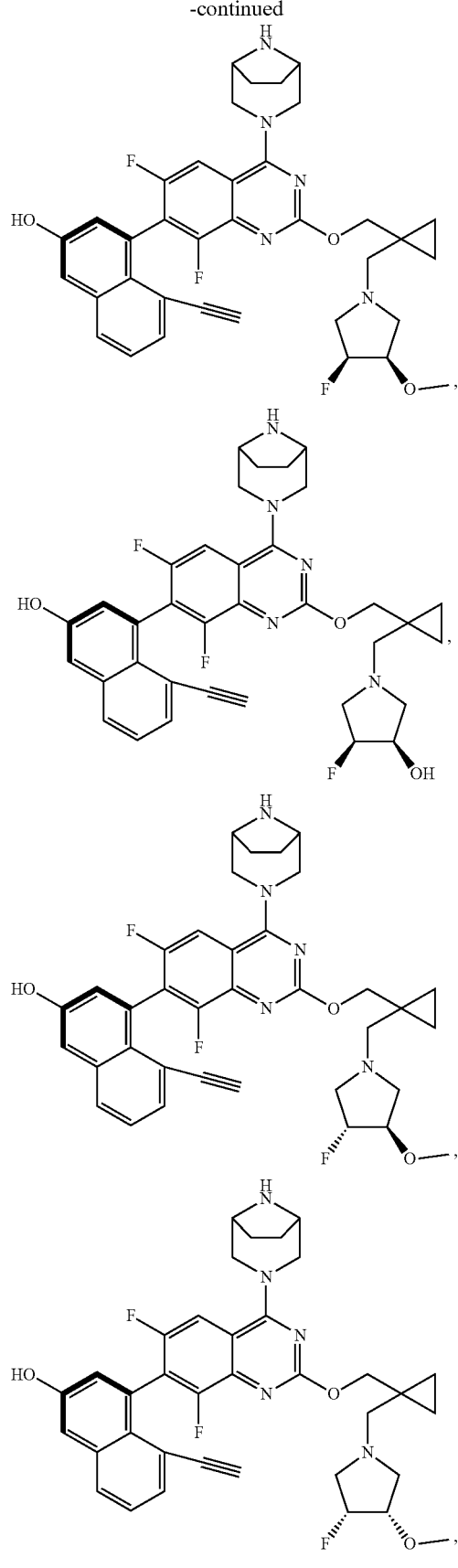
-continued
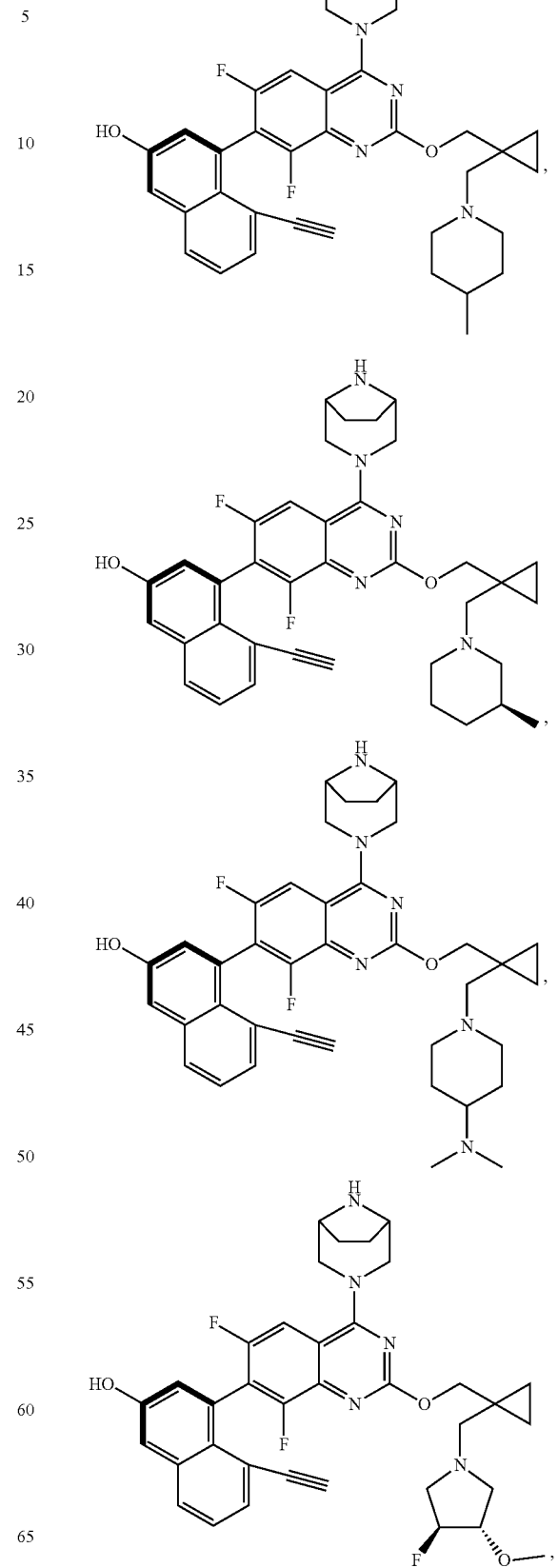

233
-continued
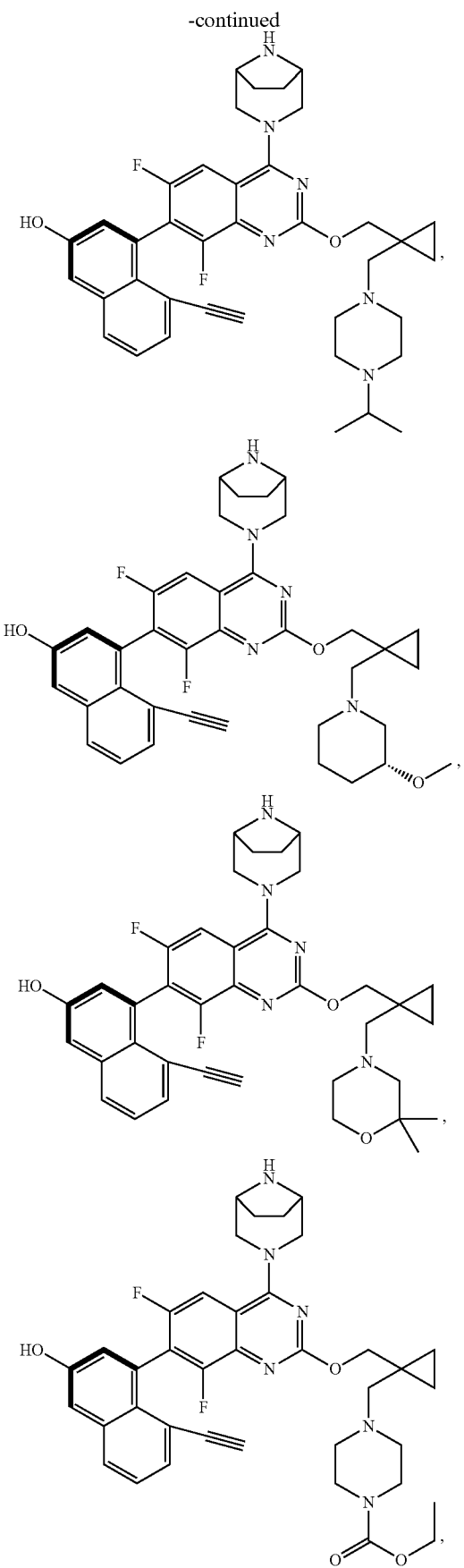
234
-continued
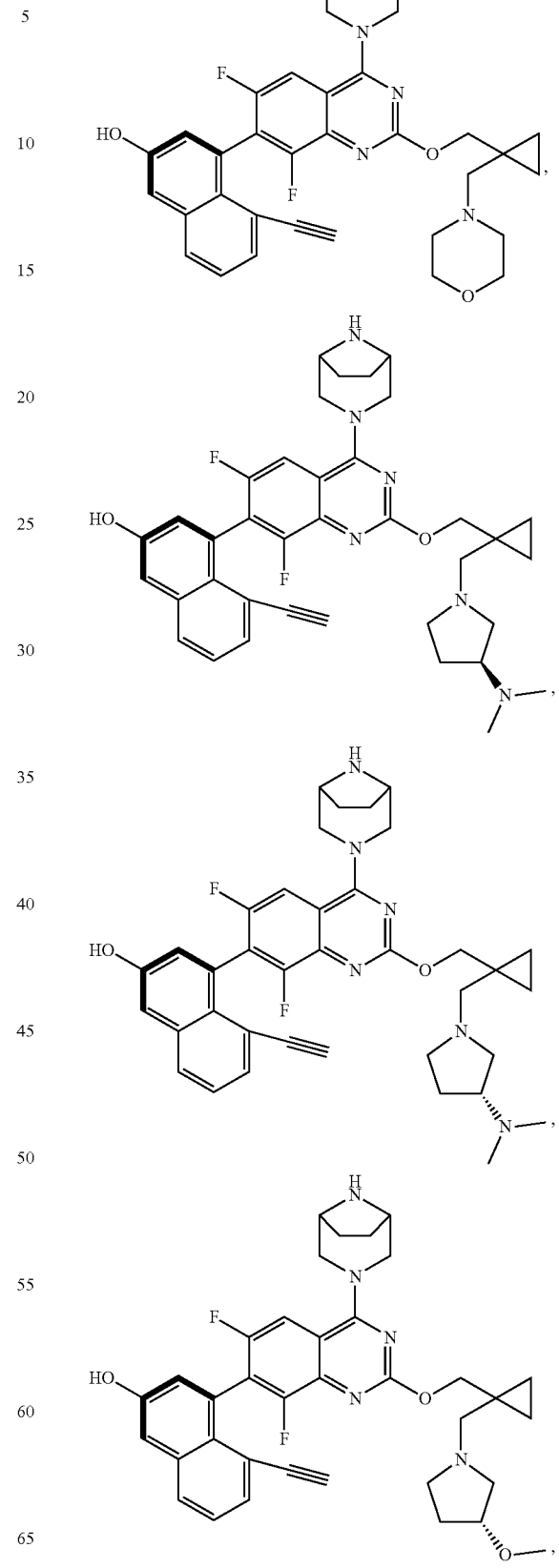

235
-continued
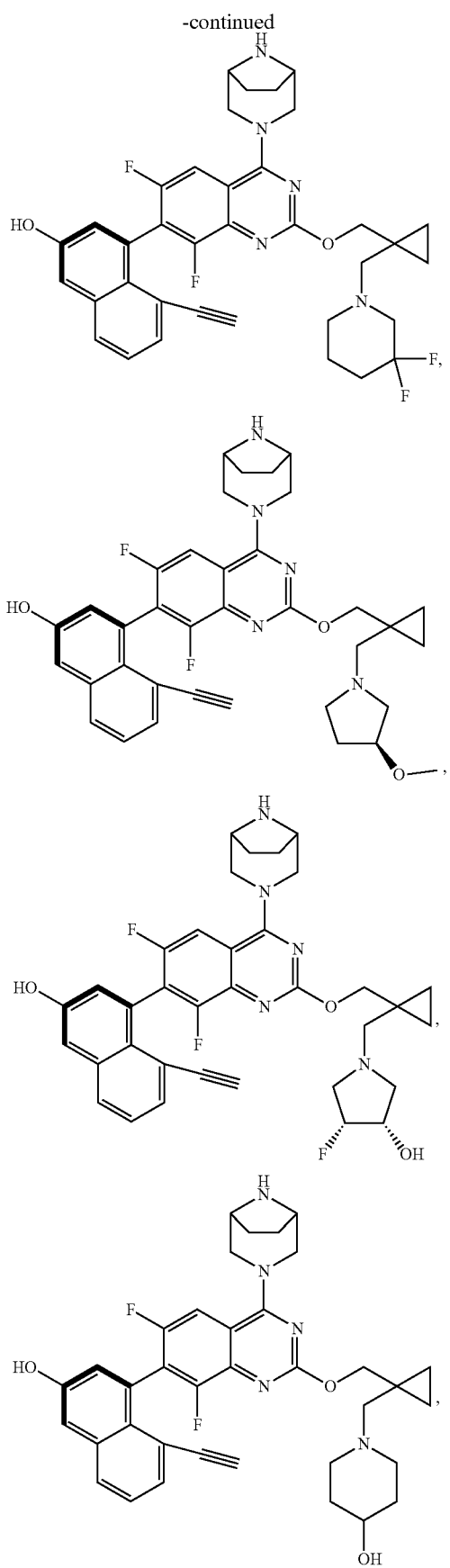
236
-continued
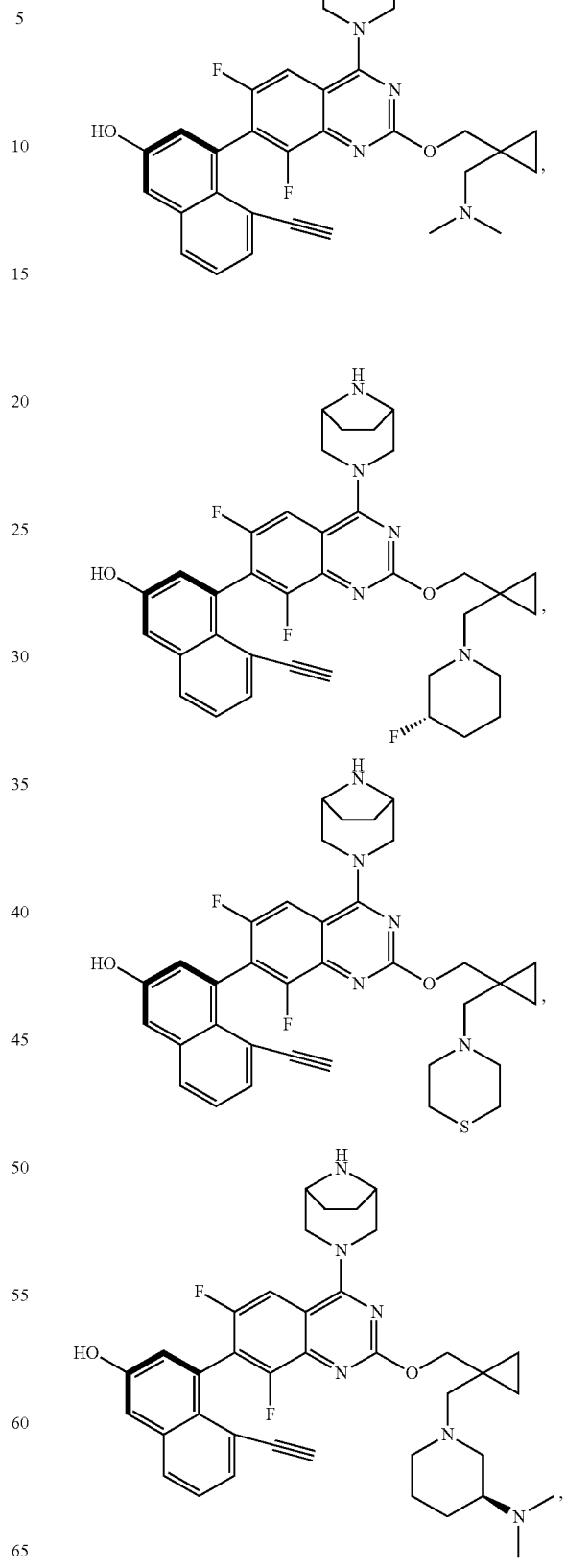

237
-continued
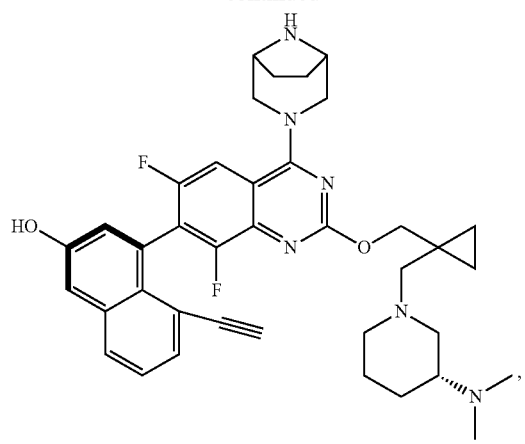
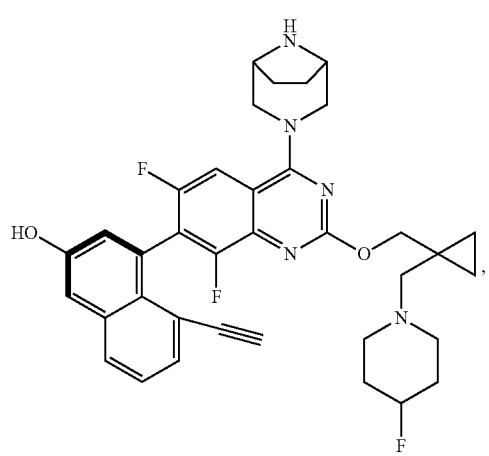
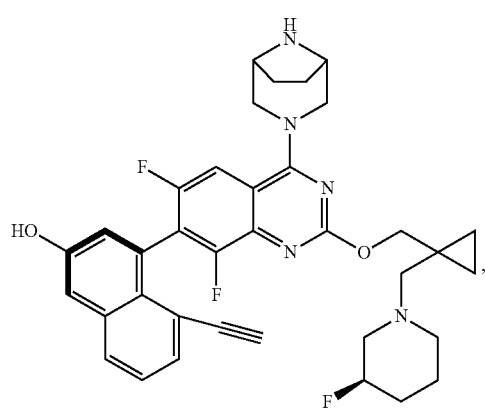
238
-continued
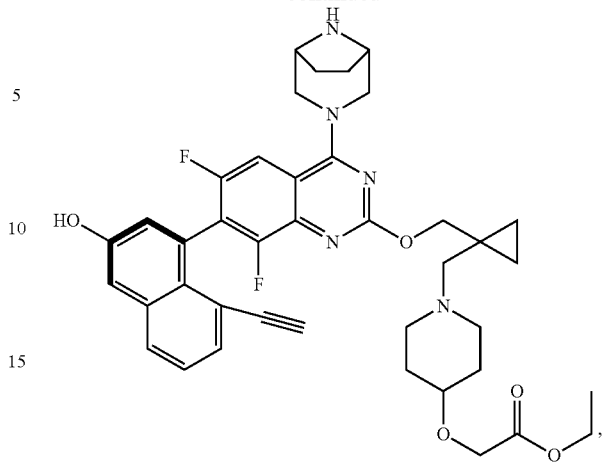
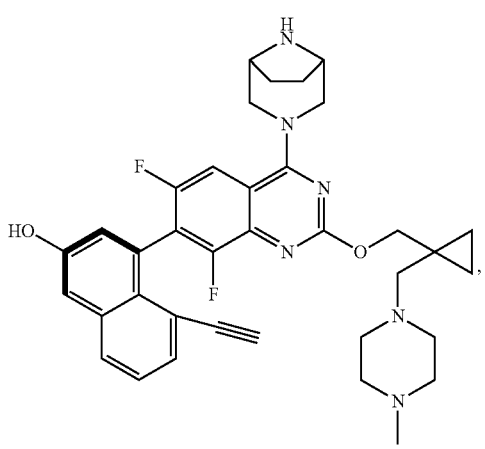
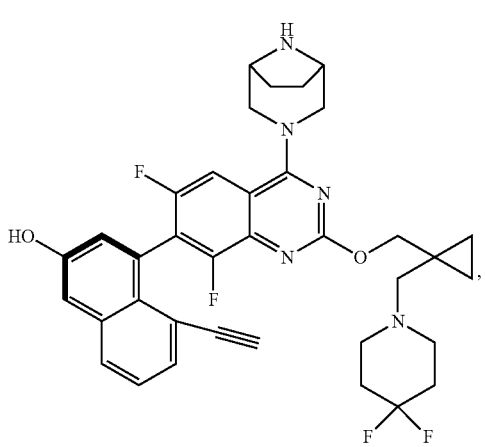

239 240
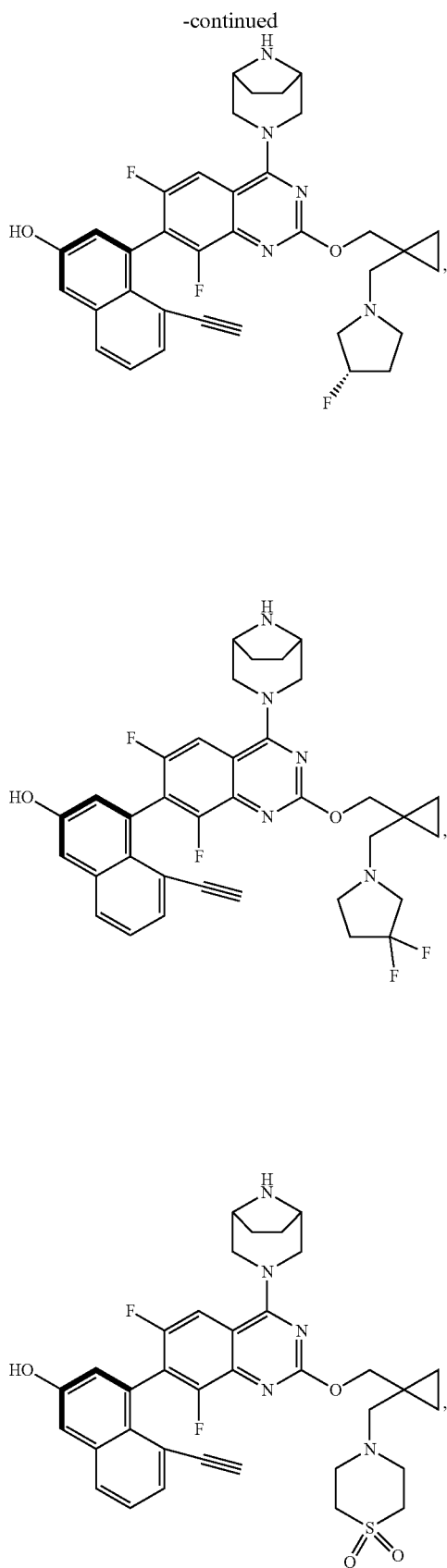
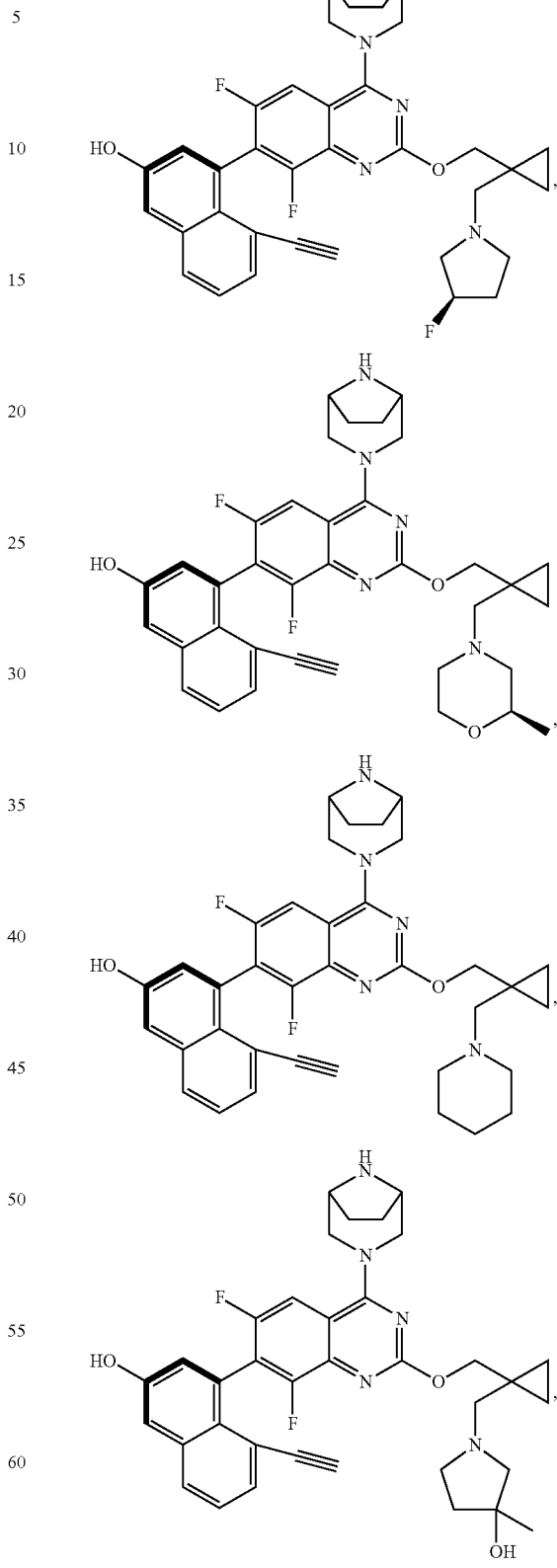

241
-continued
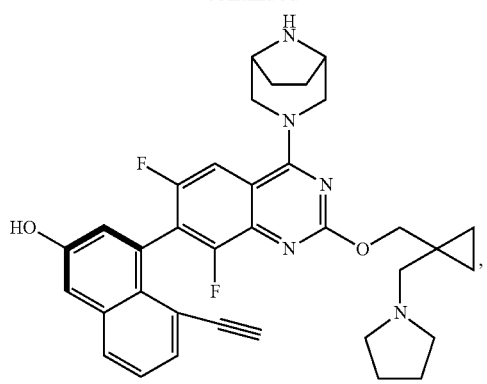
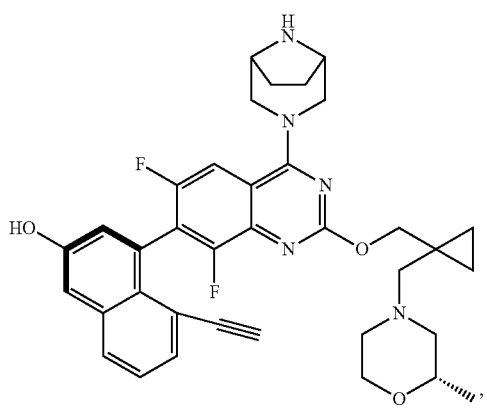
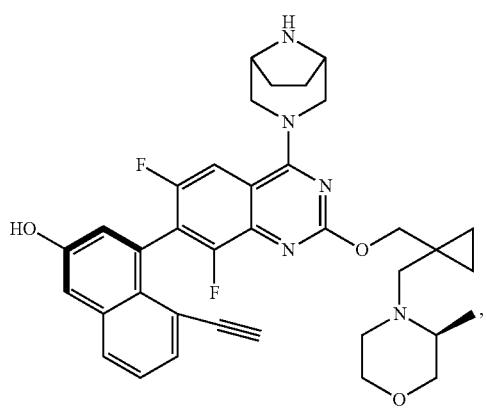
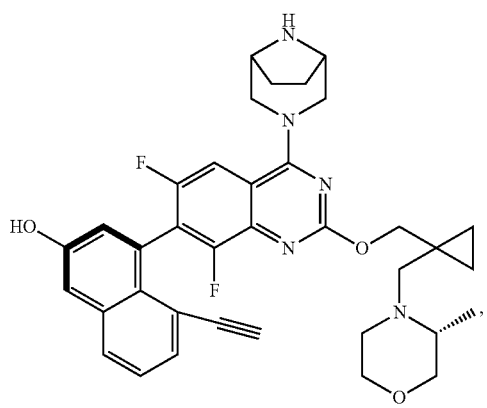
242
-continued
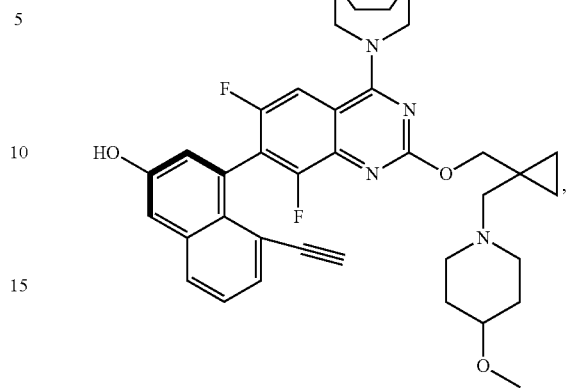
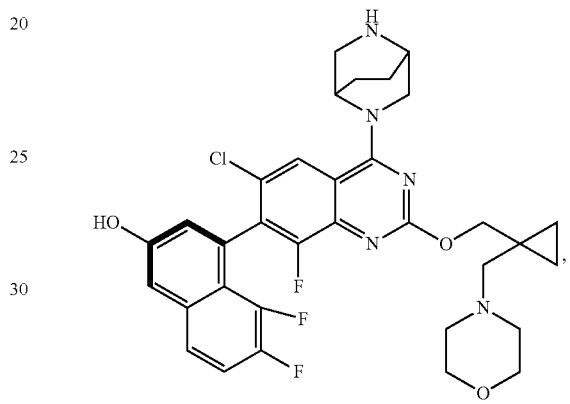
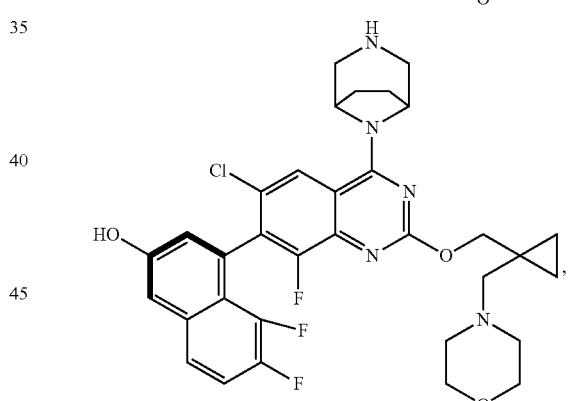
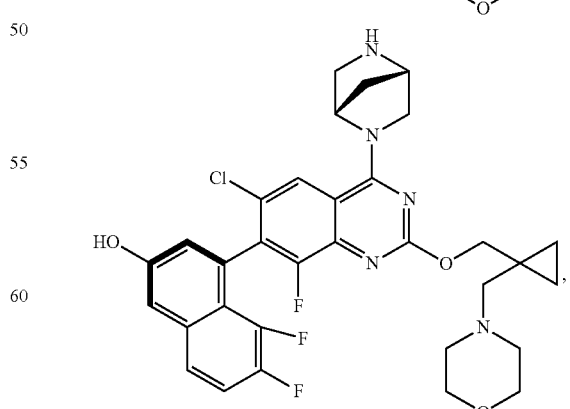

243
-continued
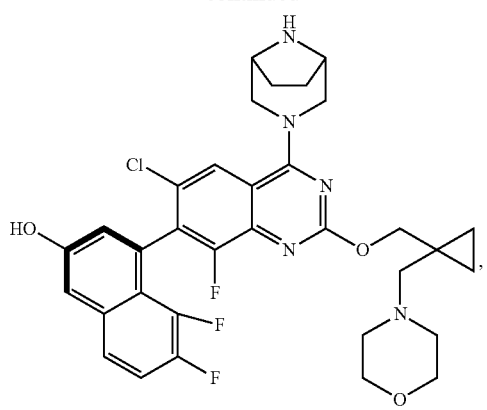
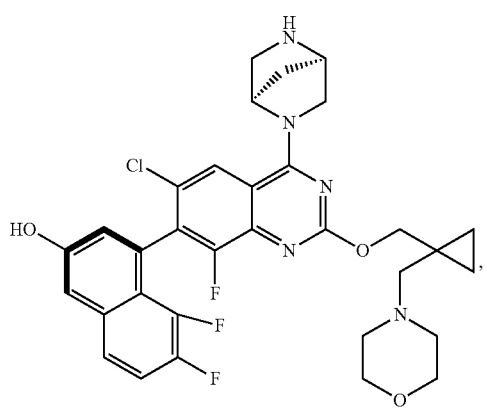
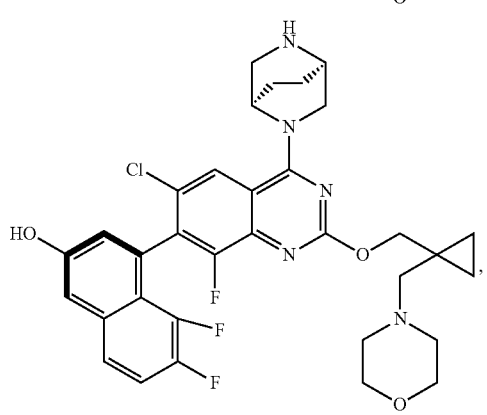
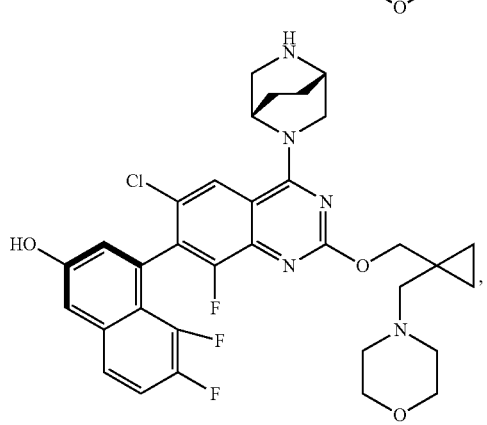
244
-continued
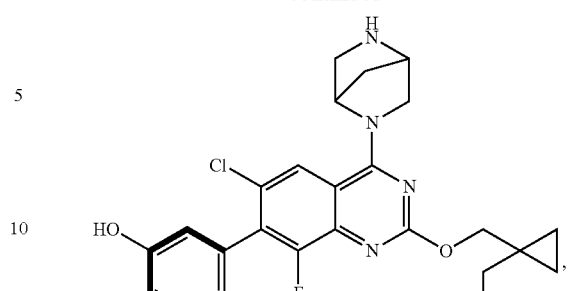
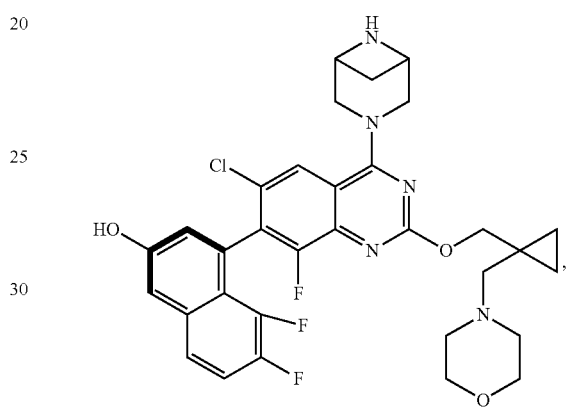
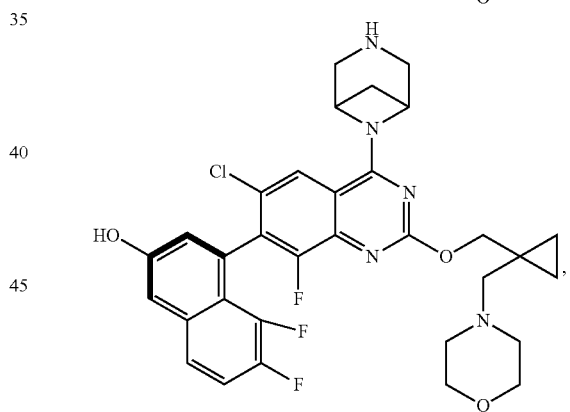
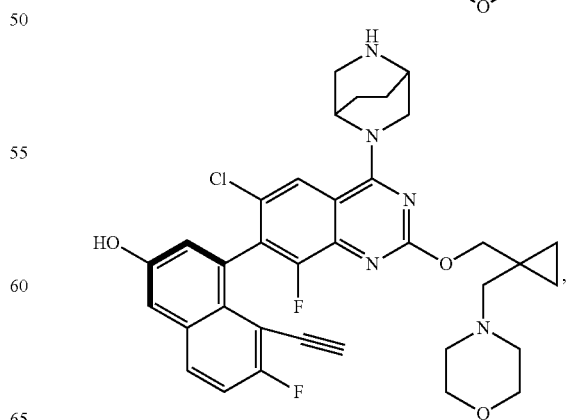

245
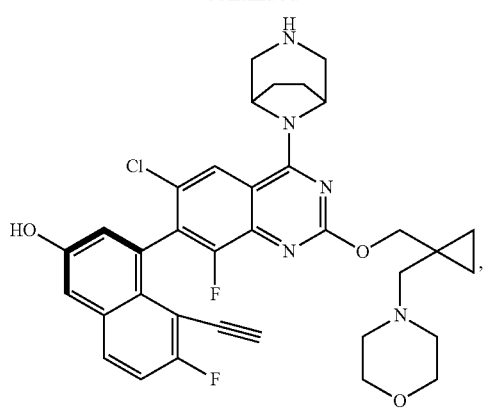
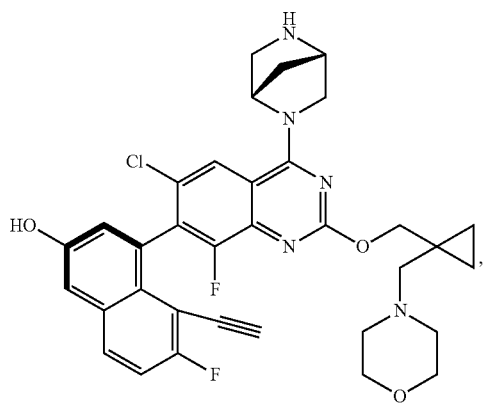
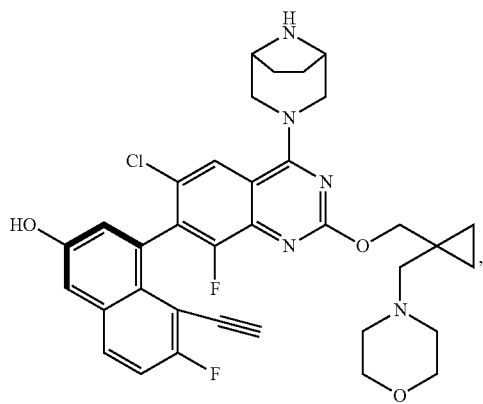
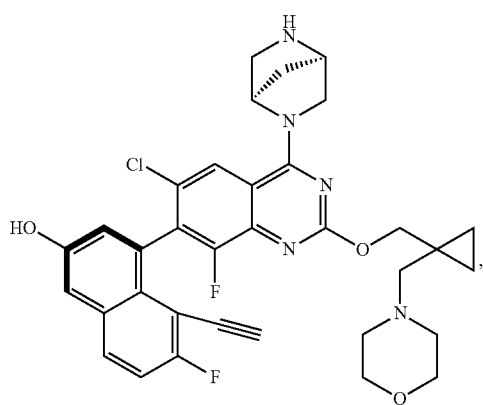
246
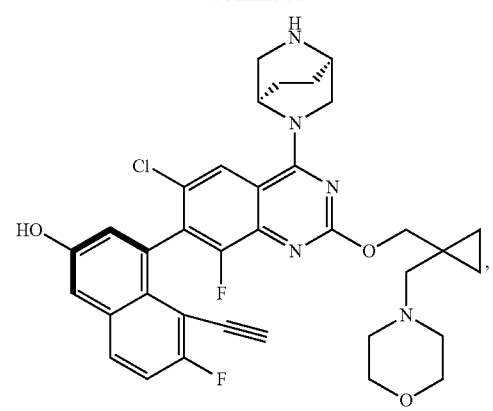
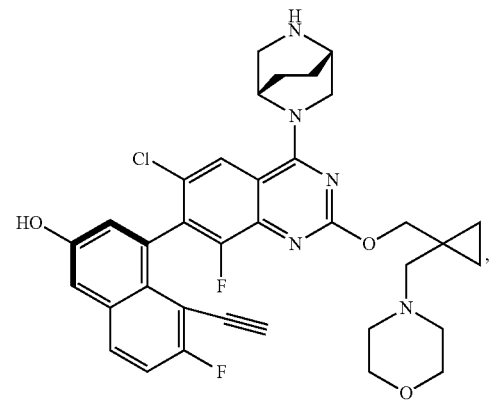
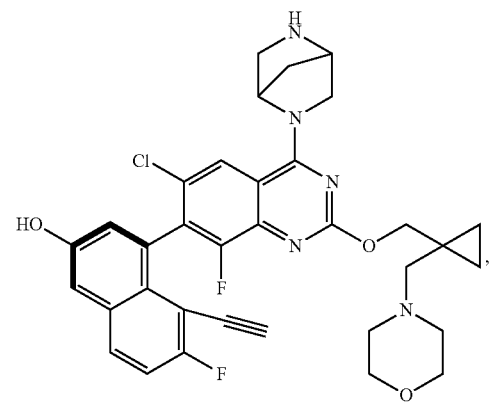
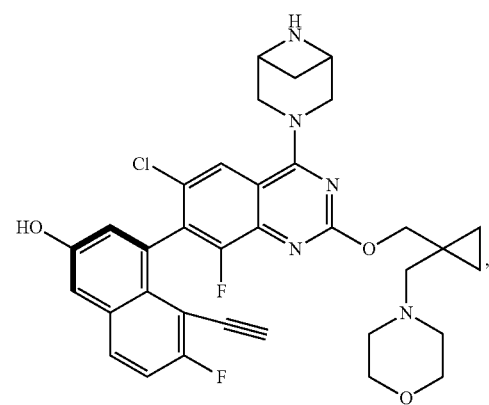

247
-continued
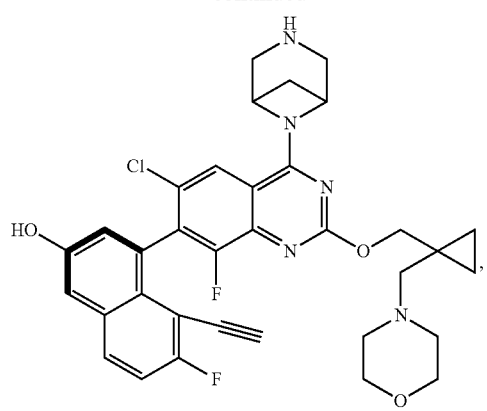
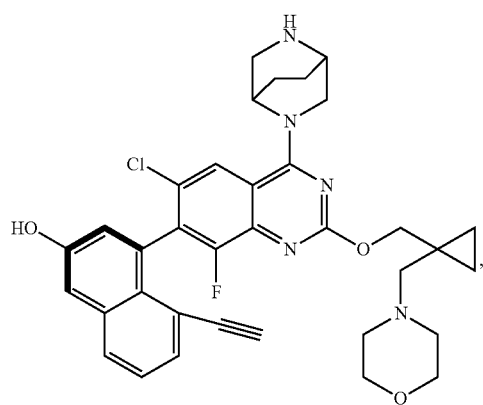
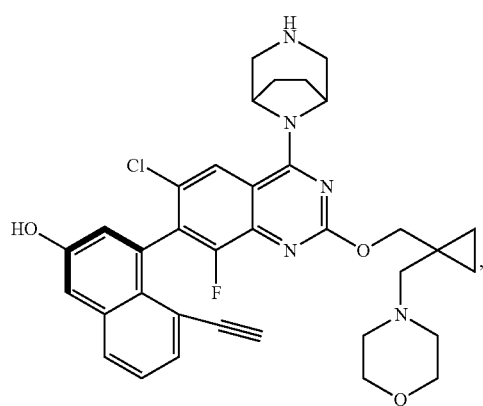
248
-continued
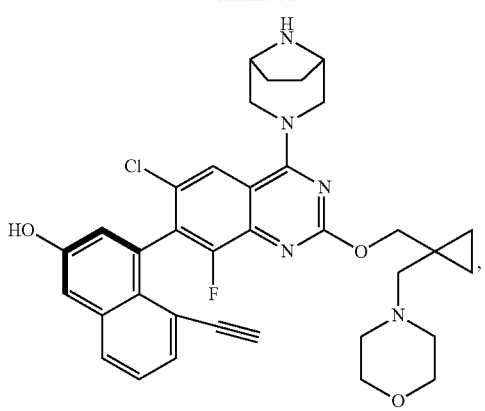
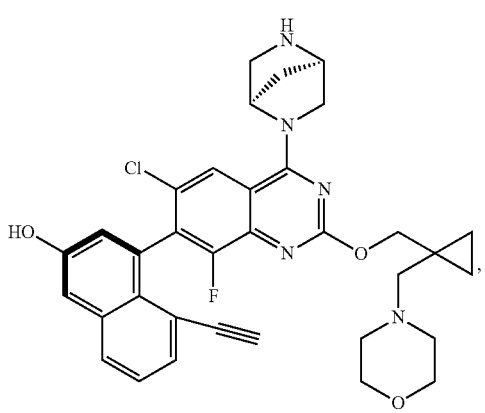
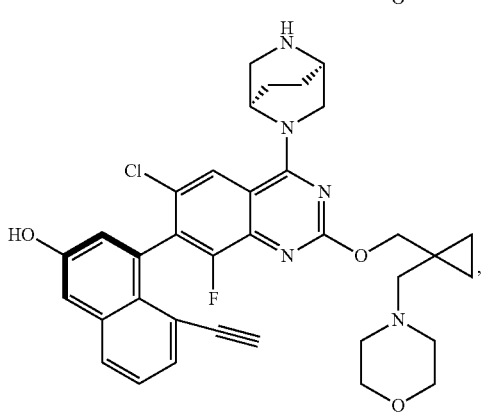

249
-continued
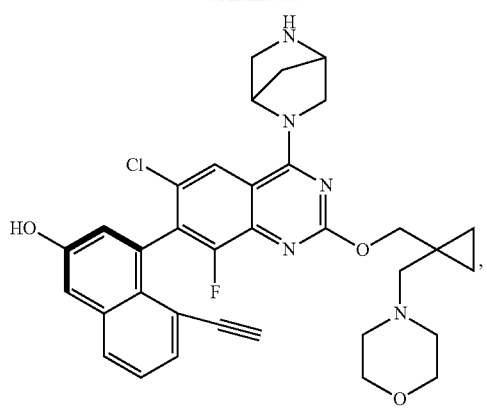
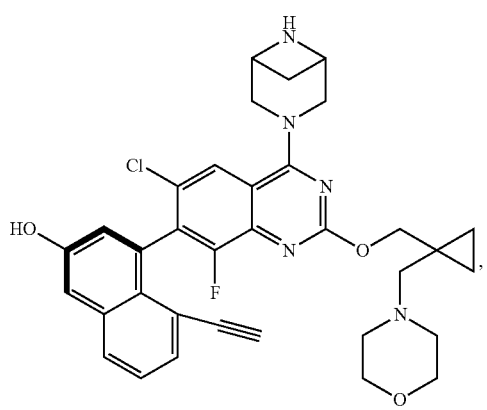
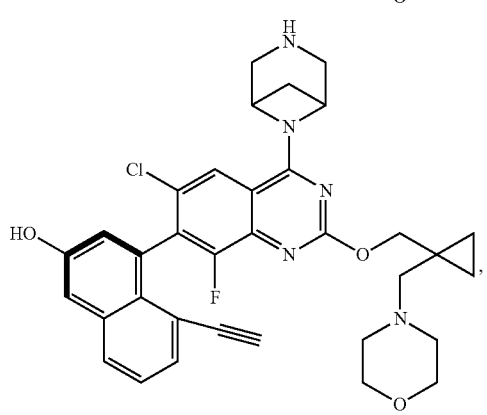
250
-continued
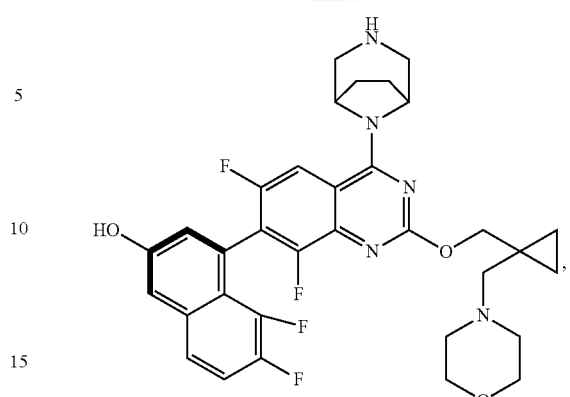
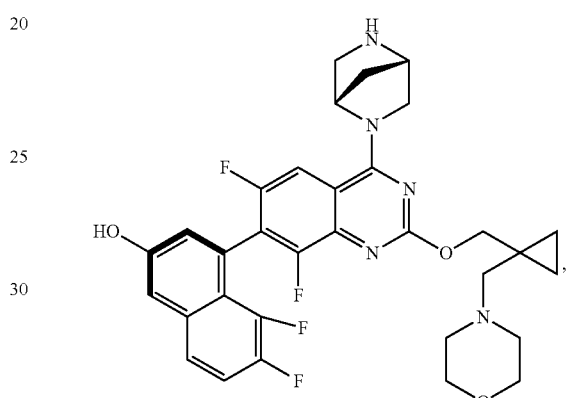
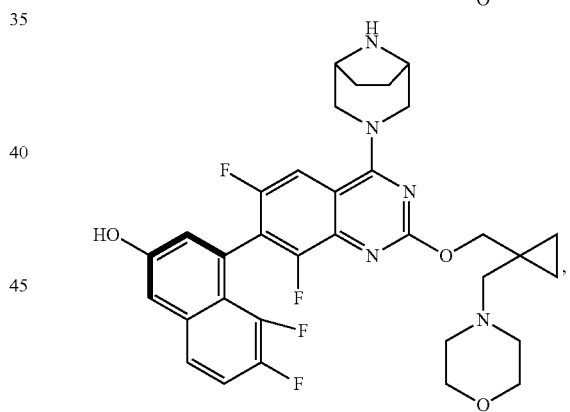
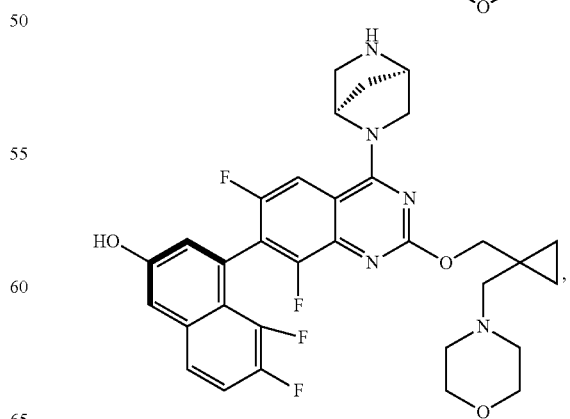

251
-continued
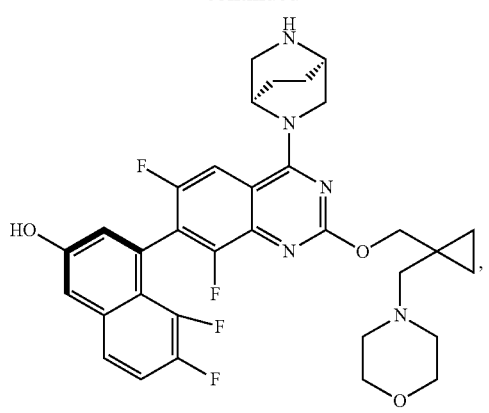
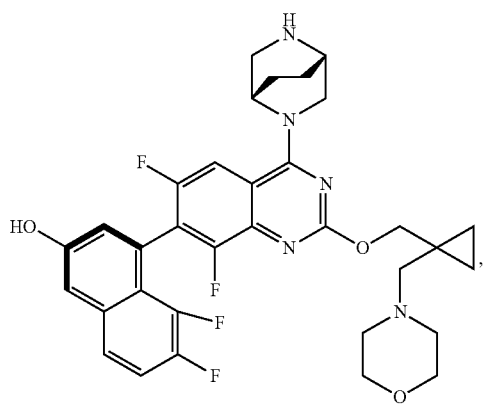
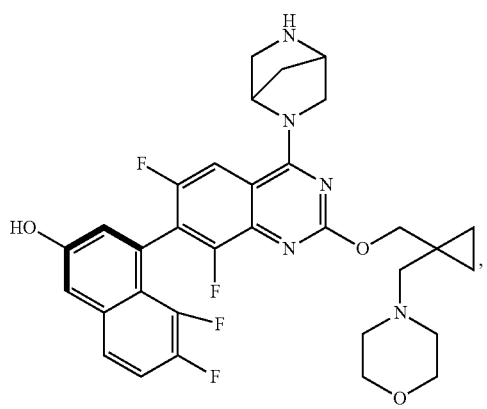
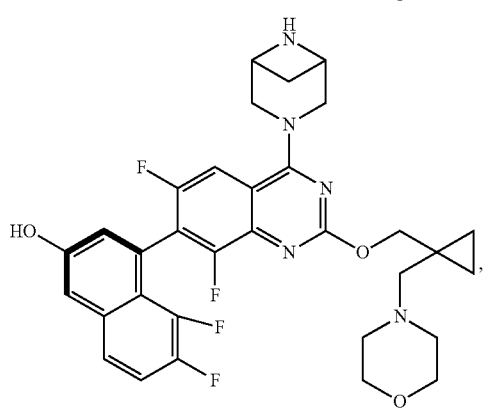
252
-continued
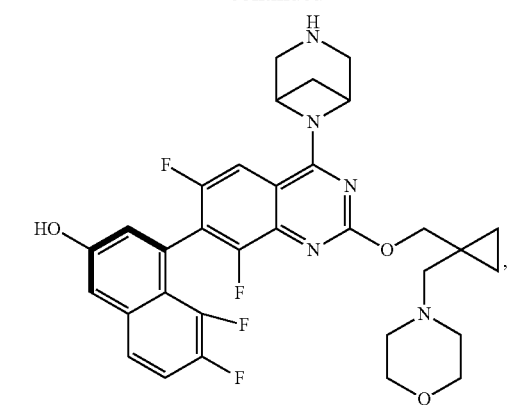
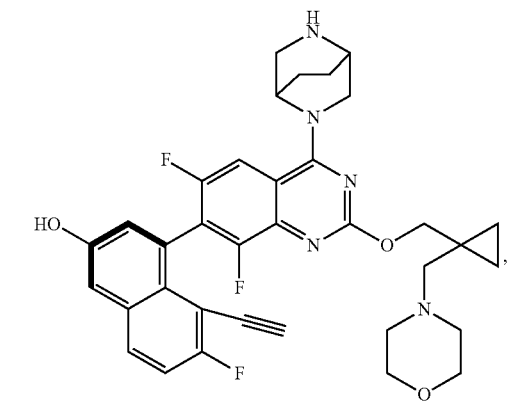
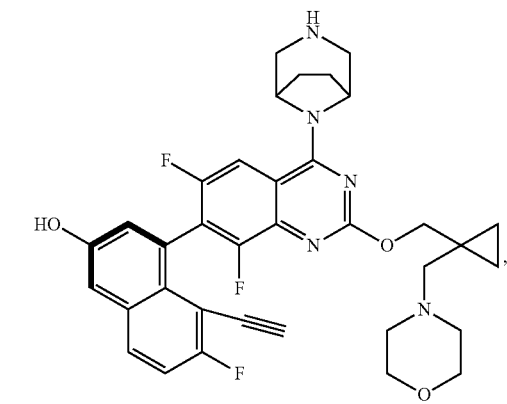
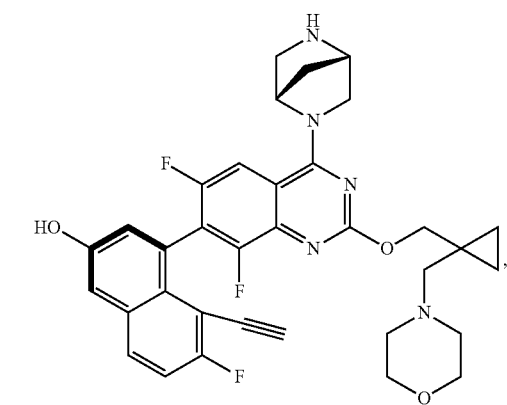

253
-continued
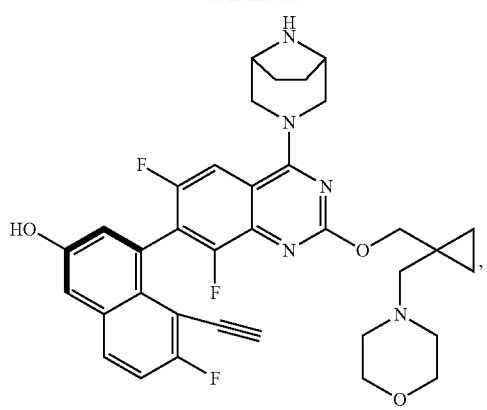
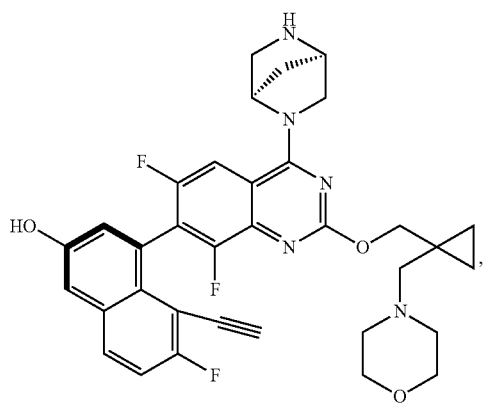
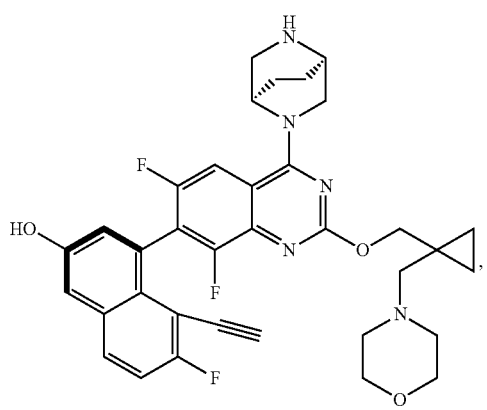
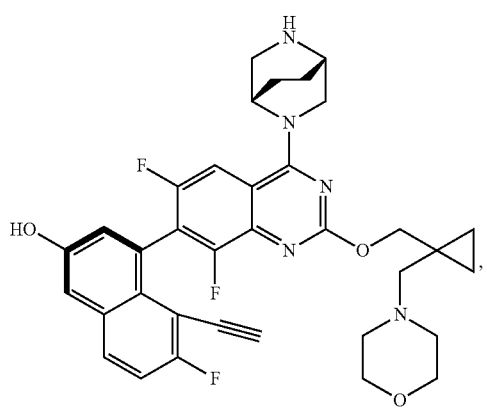
254
-continued
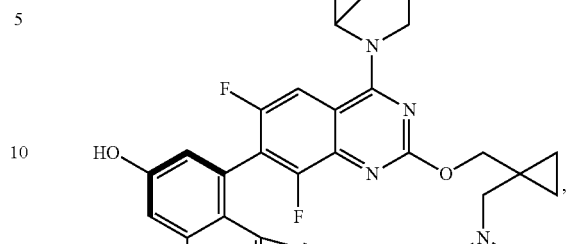
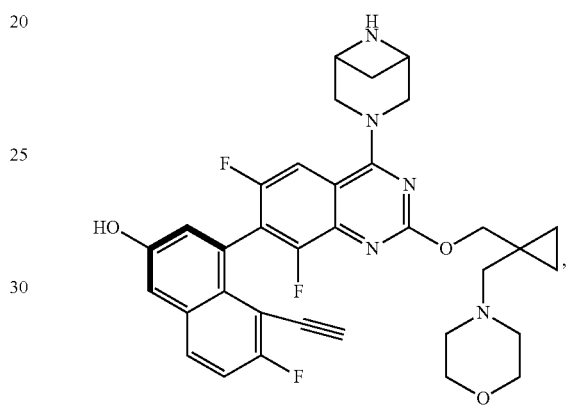
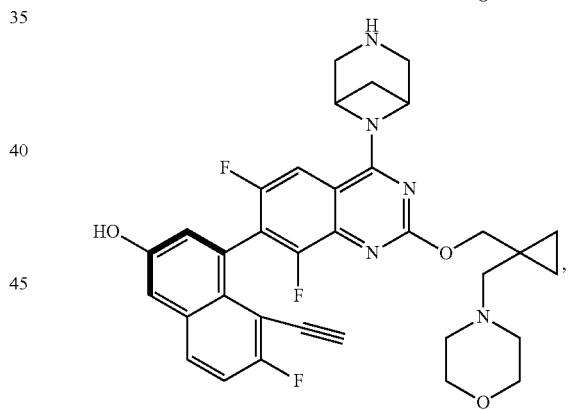
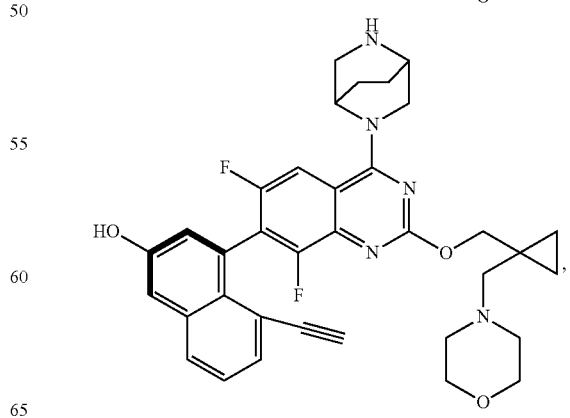

255
-continued
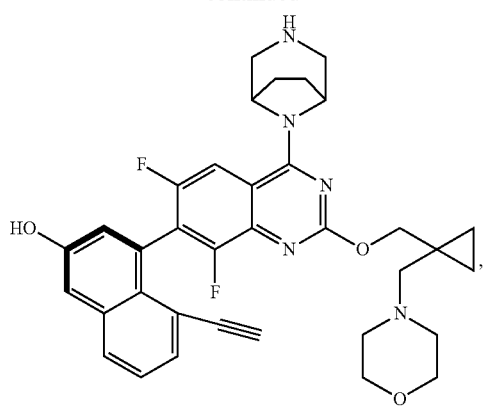
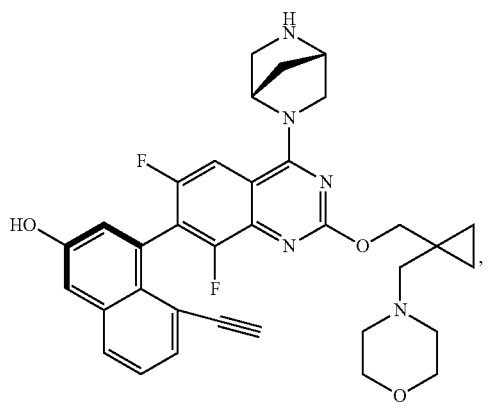
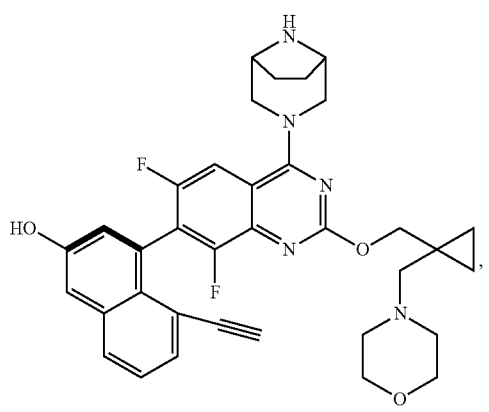
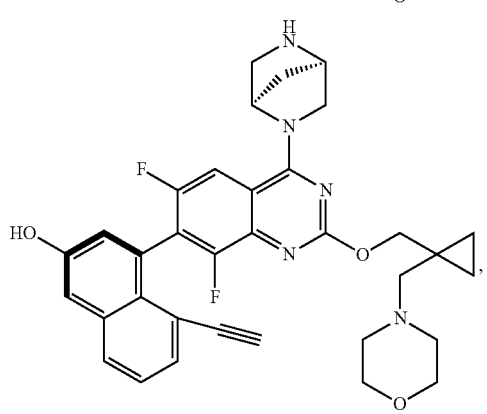
256
-continued
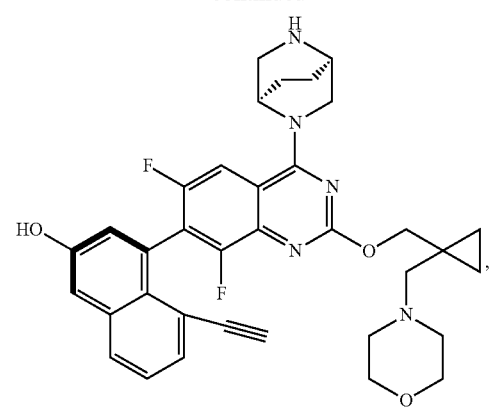
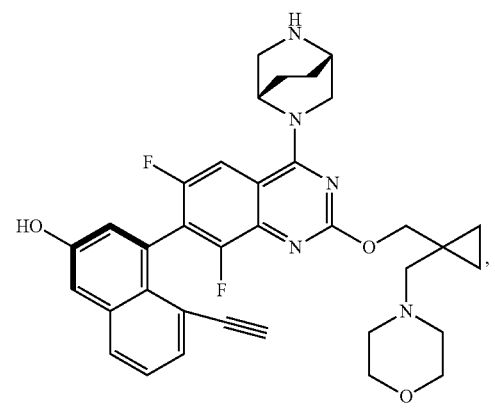
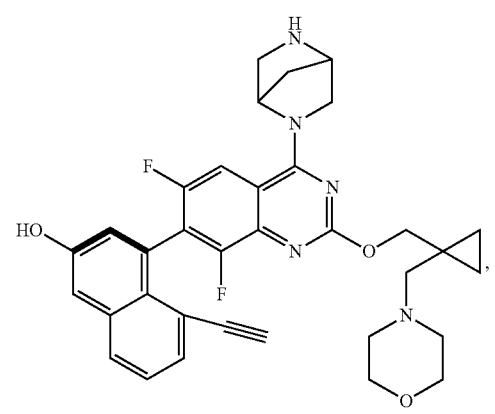
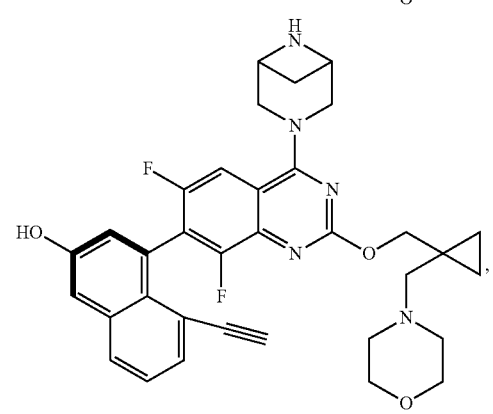

257
-continued
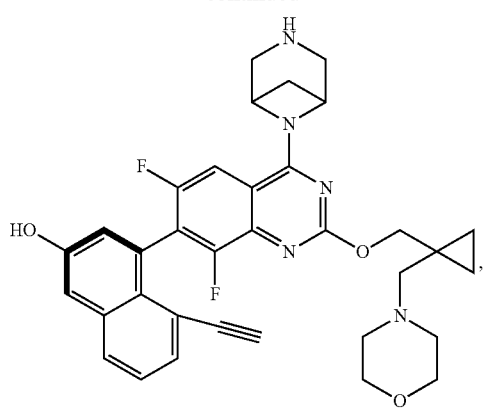
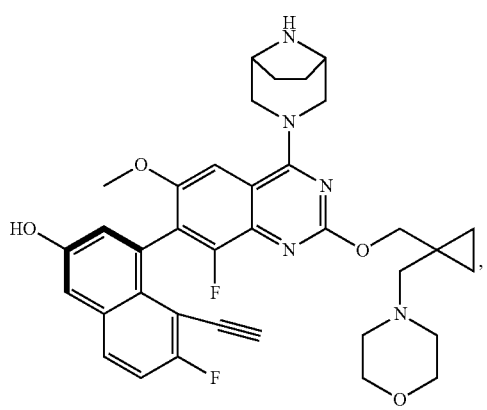
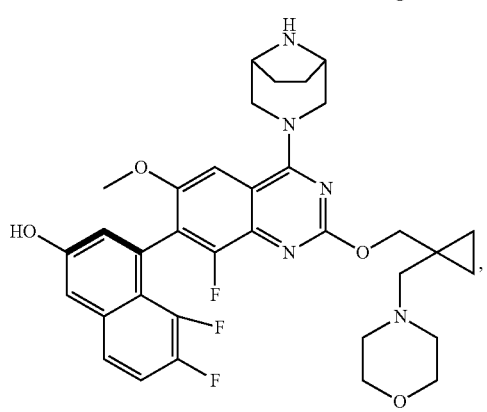
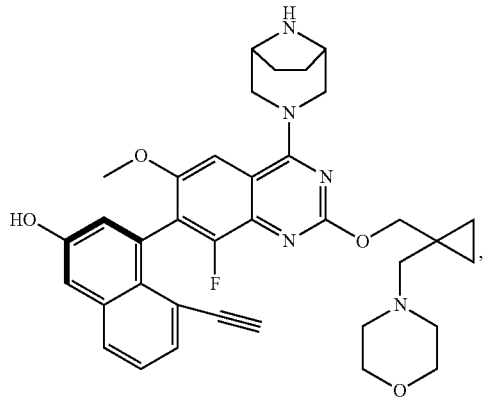
258
-continued
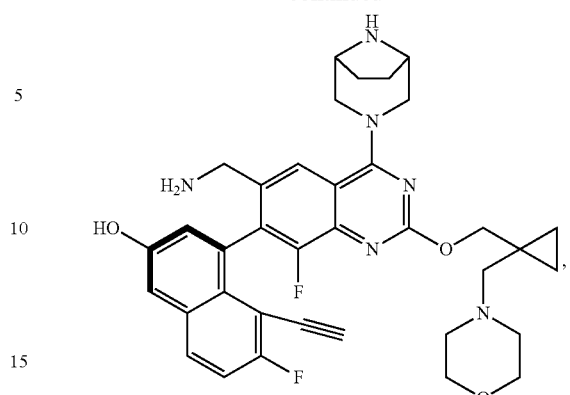

259
-continued
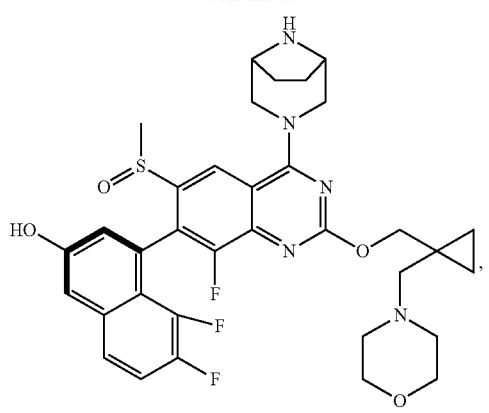
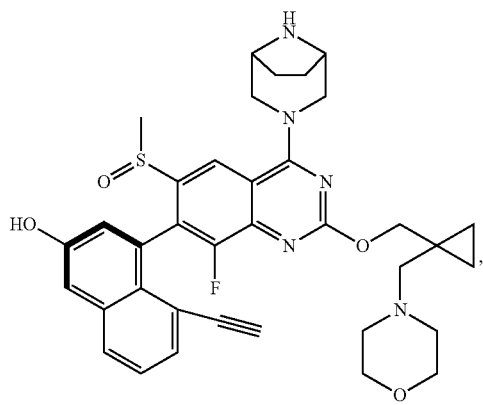
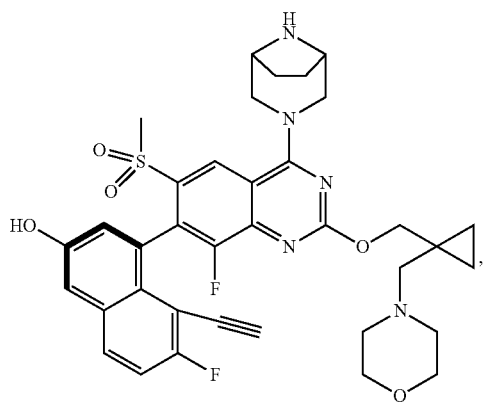

260
-continued
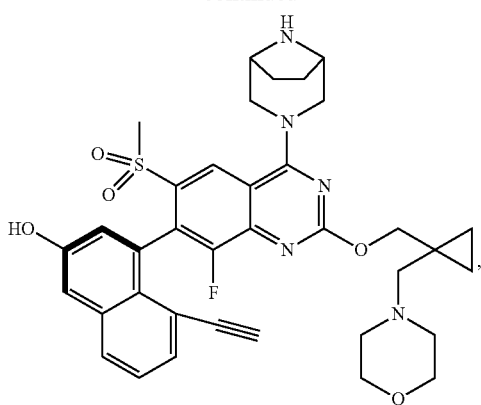
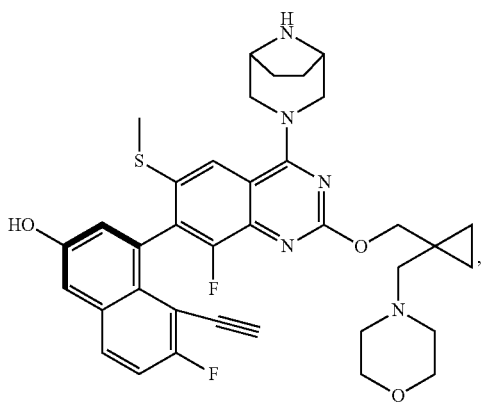
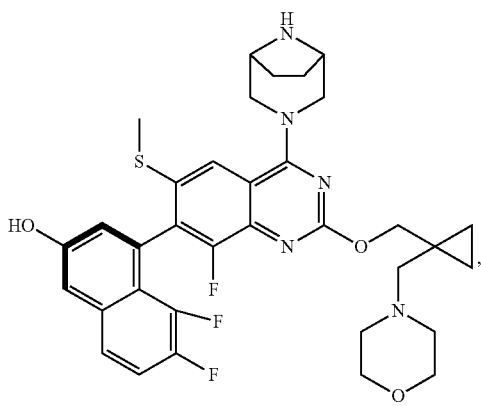
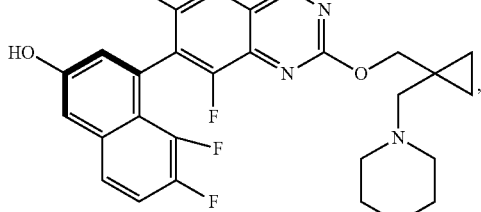

261
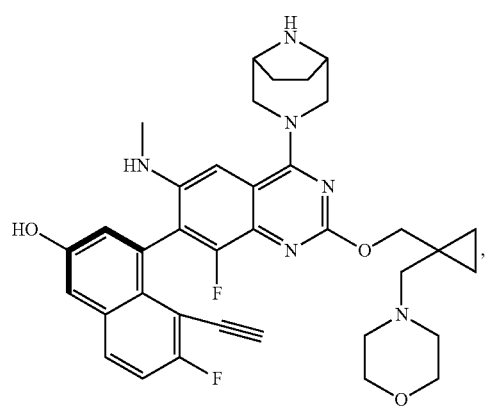
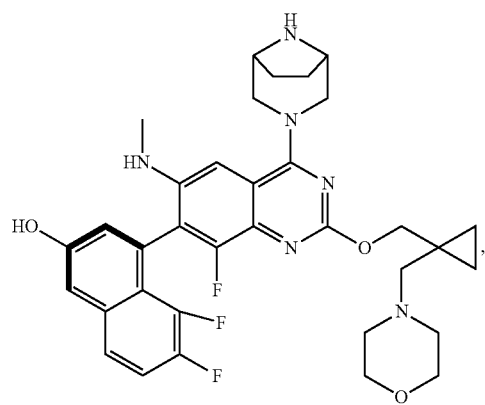
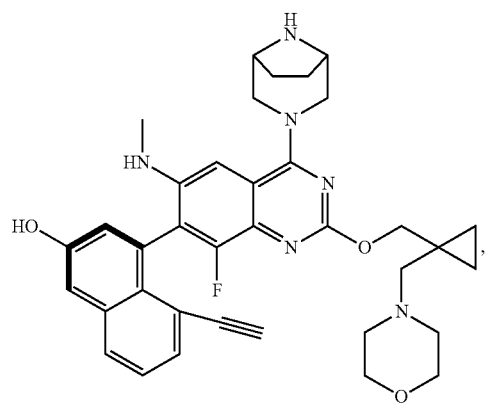
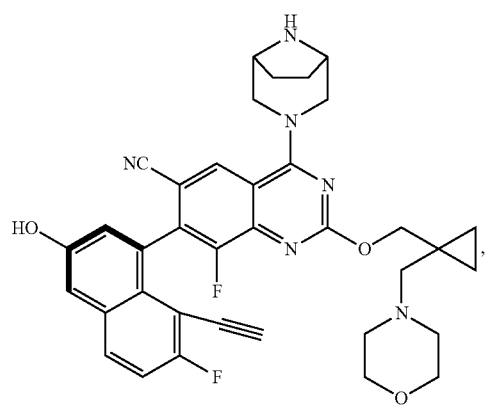
262
-continued
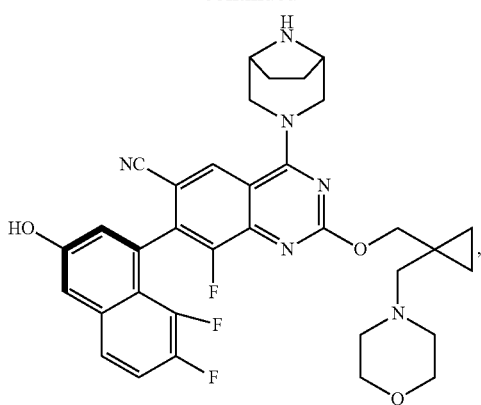
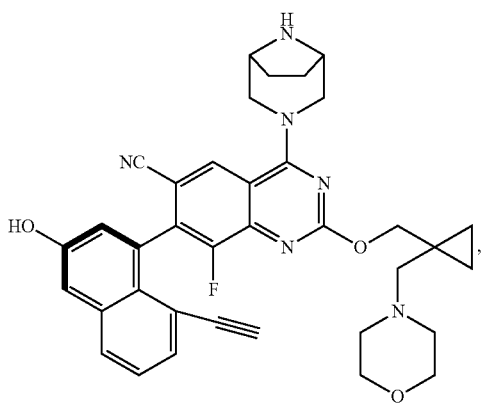
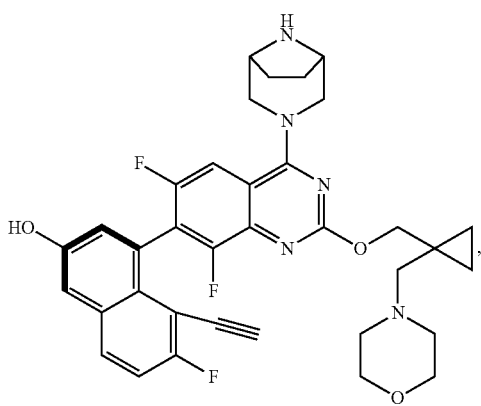
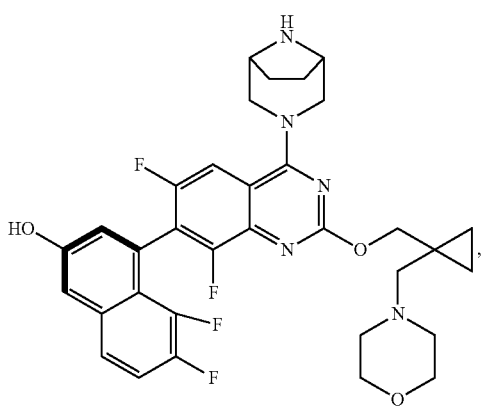

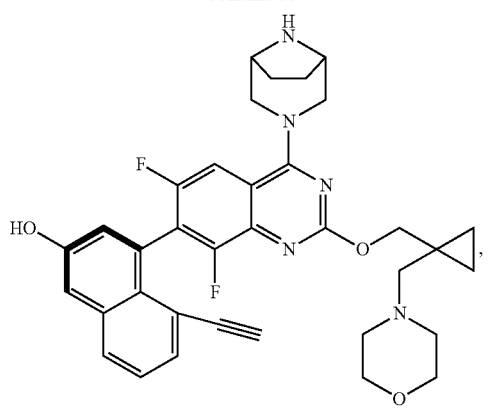
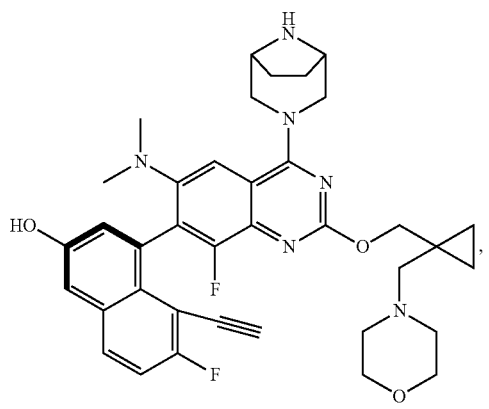
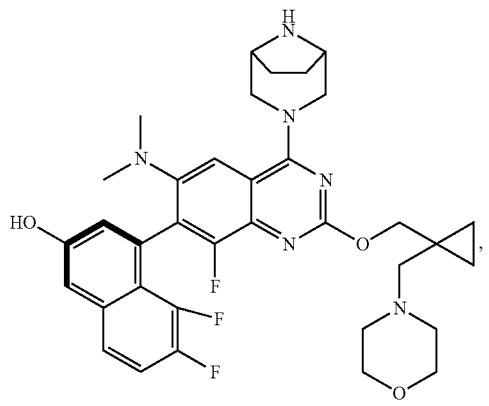
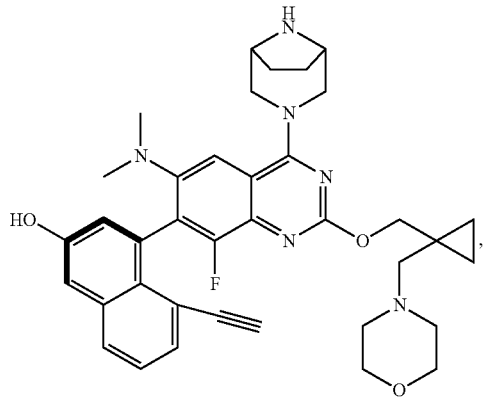
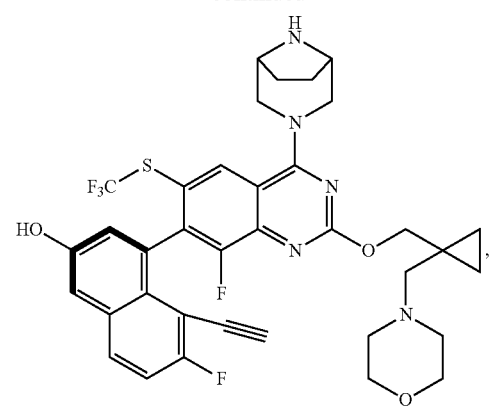
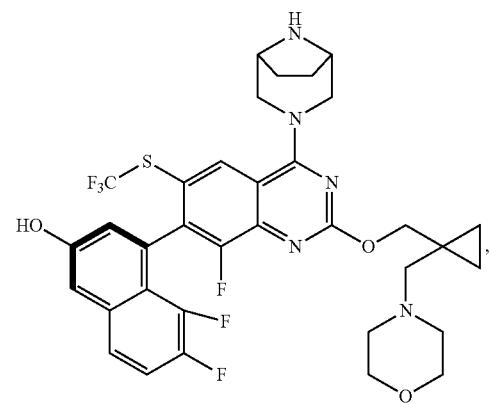
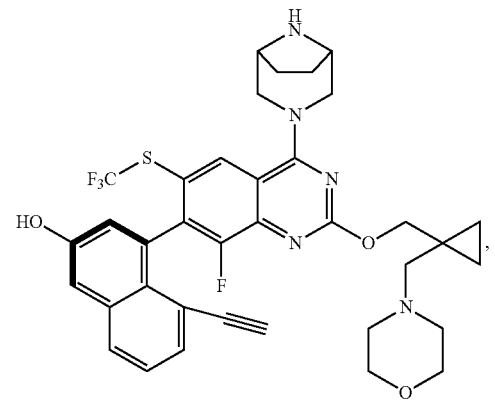
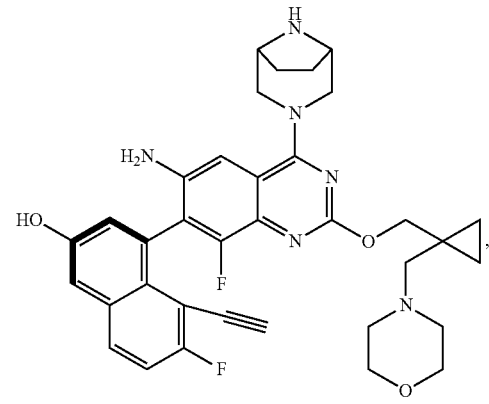

265
-continued
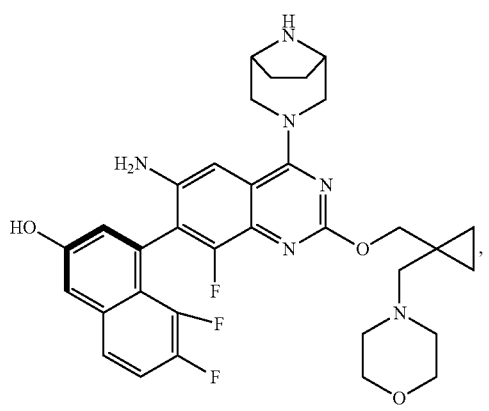
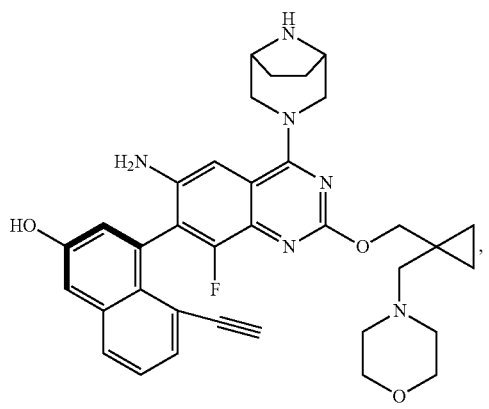
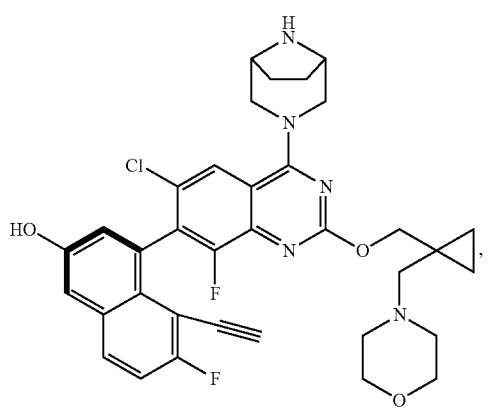
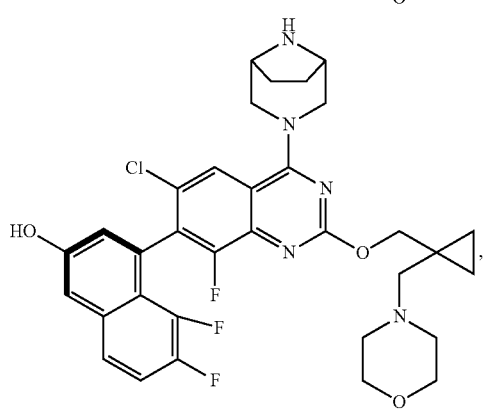
266
-continued
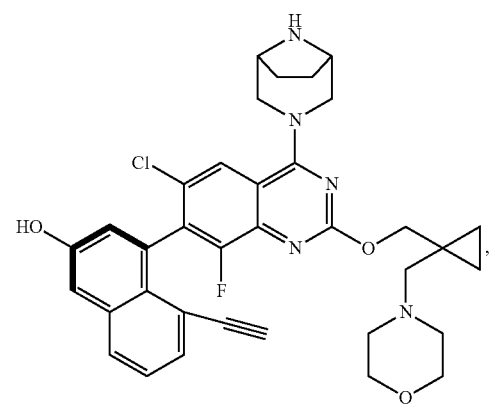
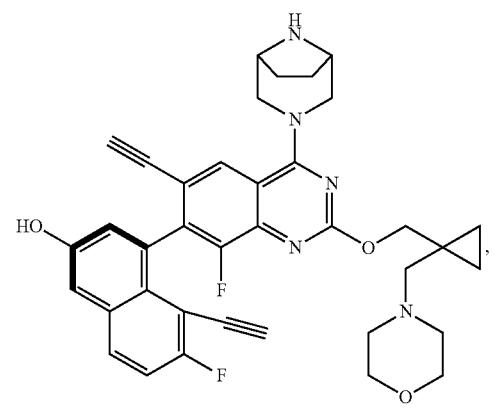
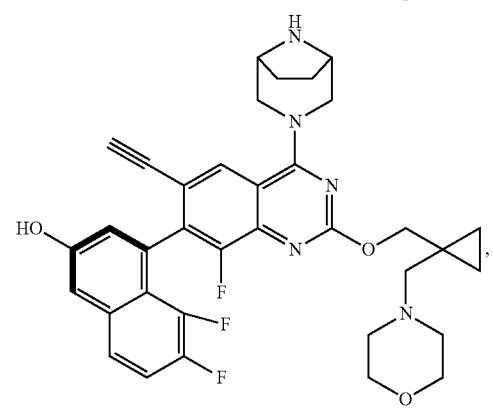
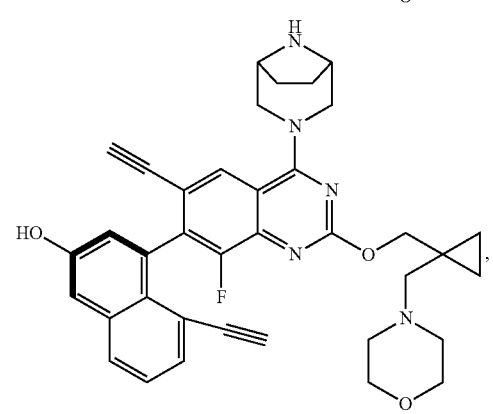

267
-continued
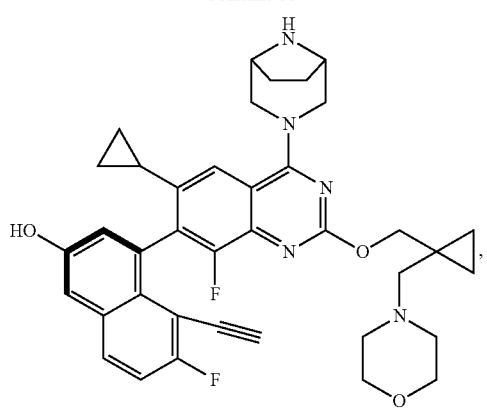
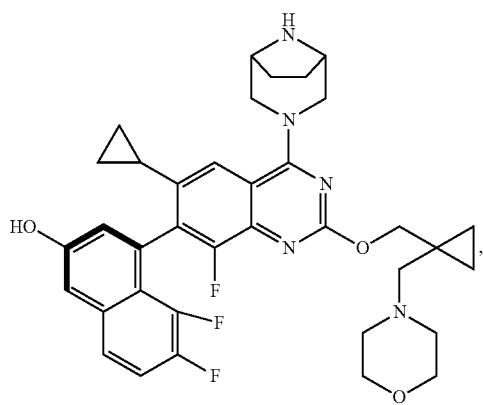
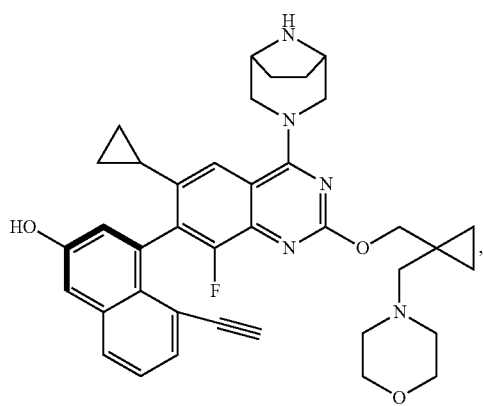
268
-continued
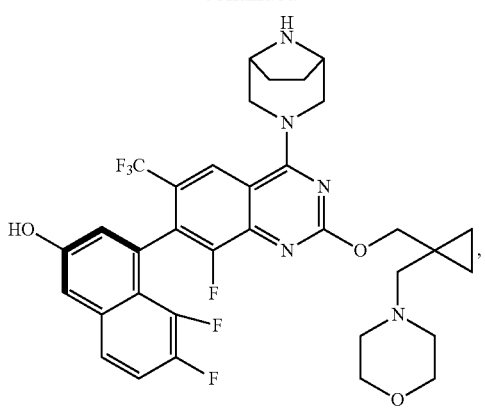
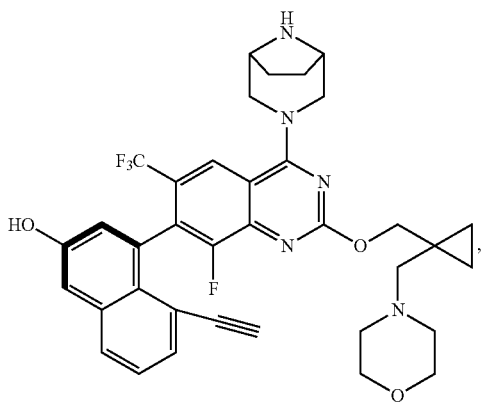
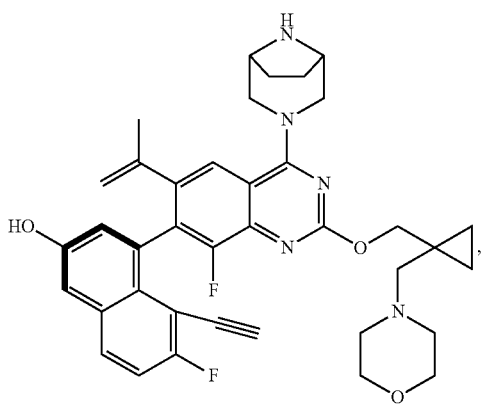

269
-continued
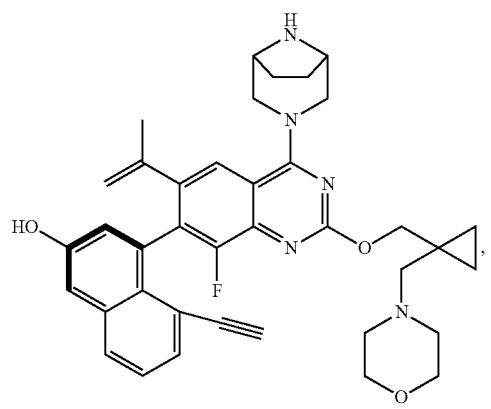
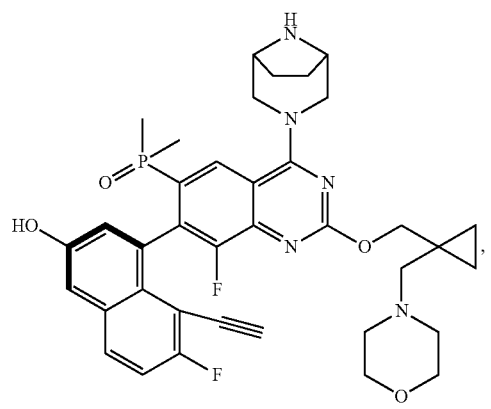
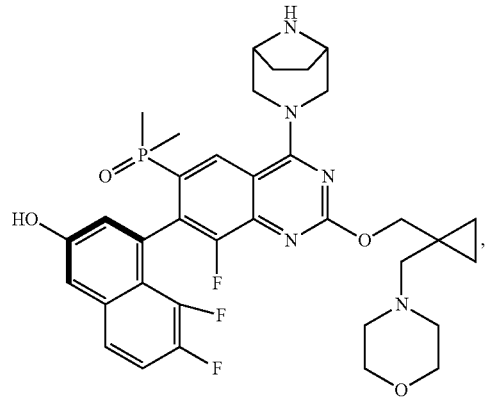
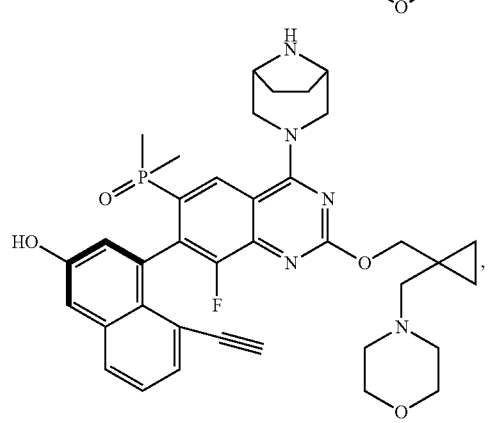
270
-continued
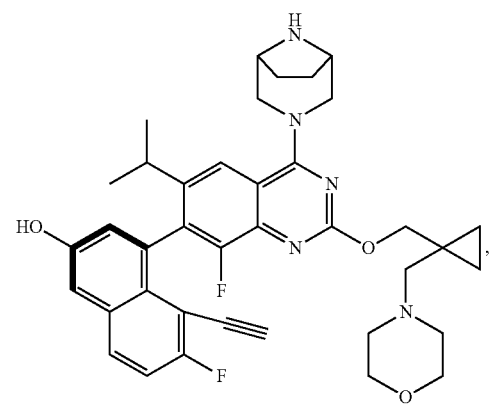
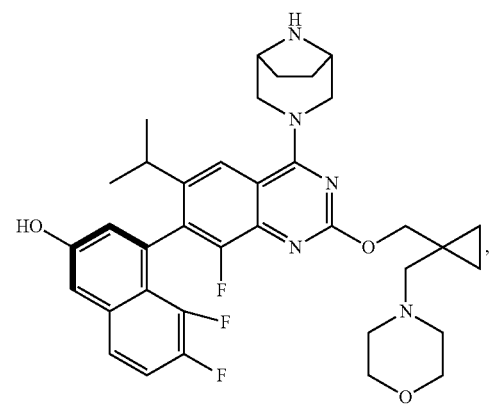
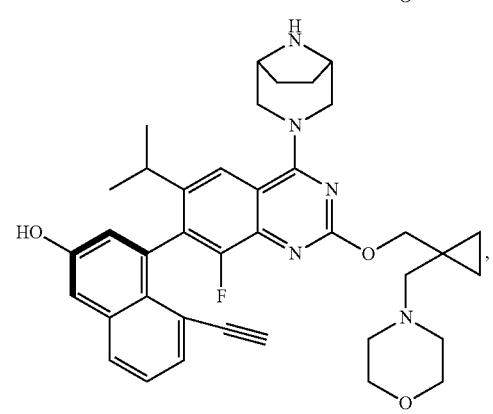
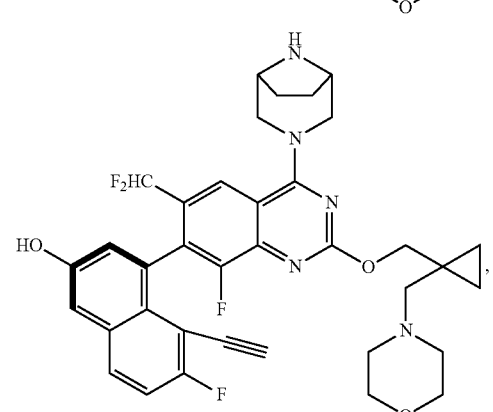

271
-continued
272
-continued
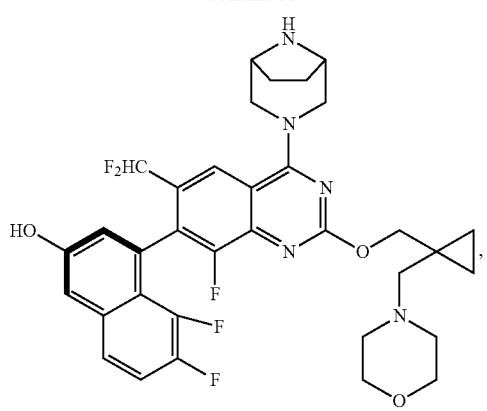
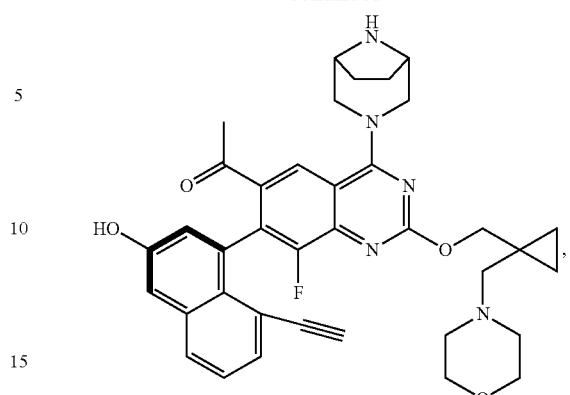
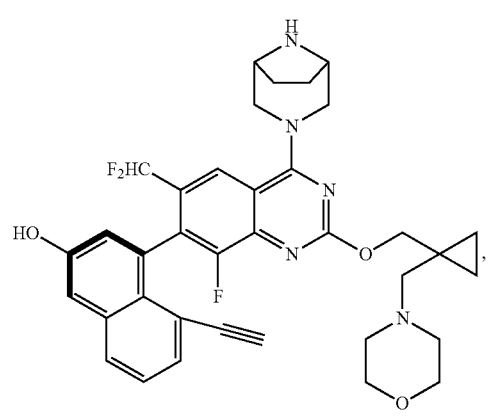
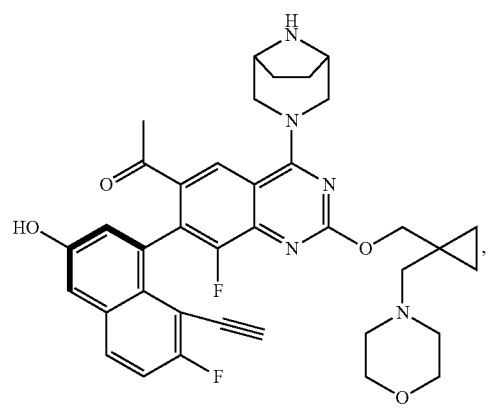
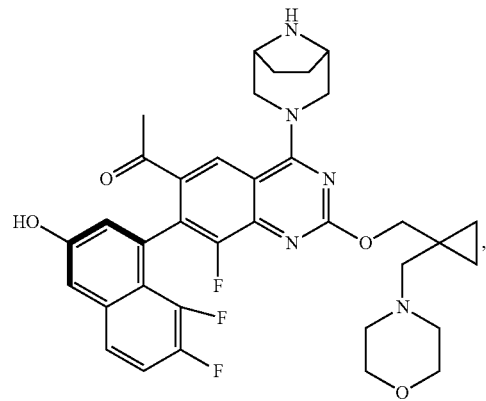

273
-continued
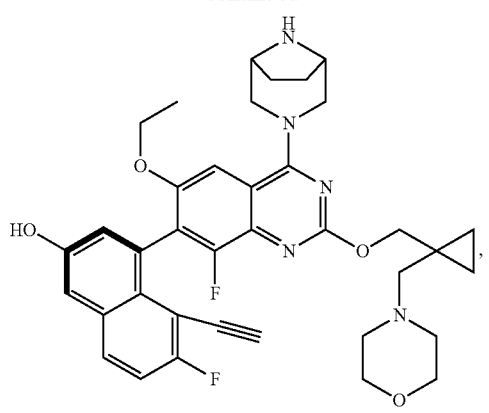
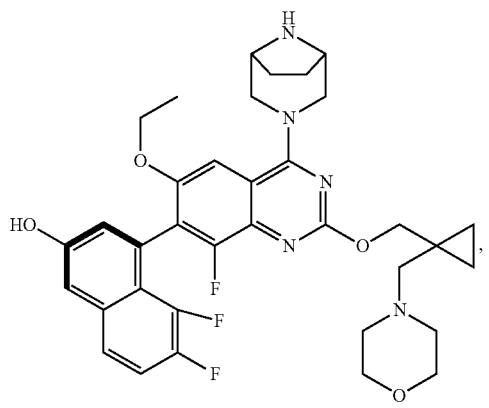
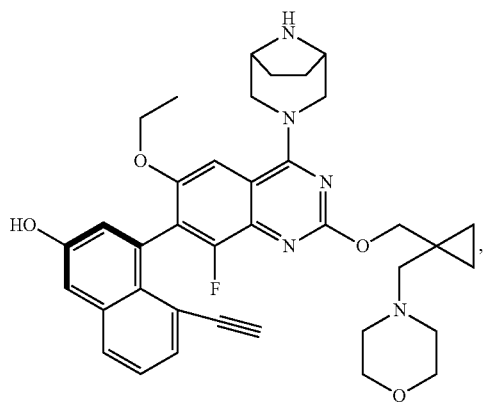
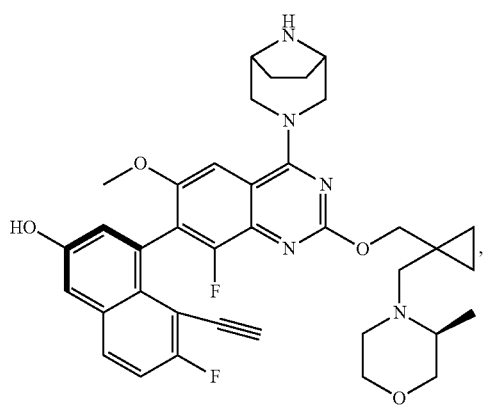
274
-continued
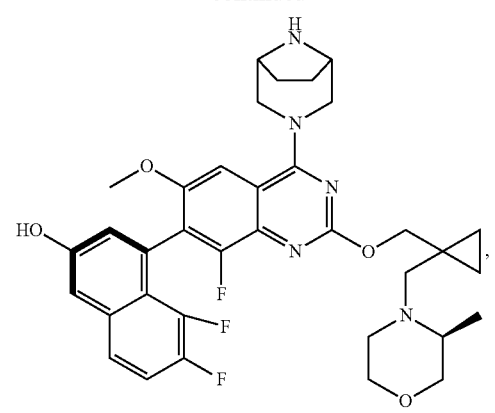
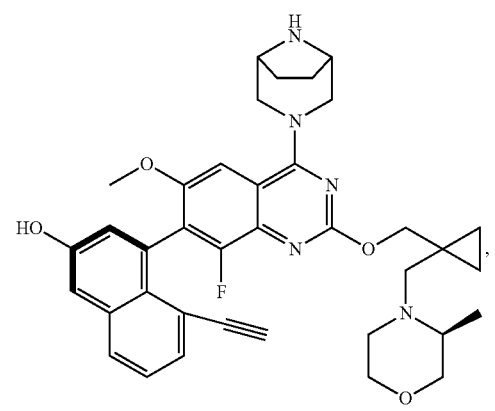
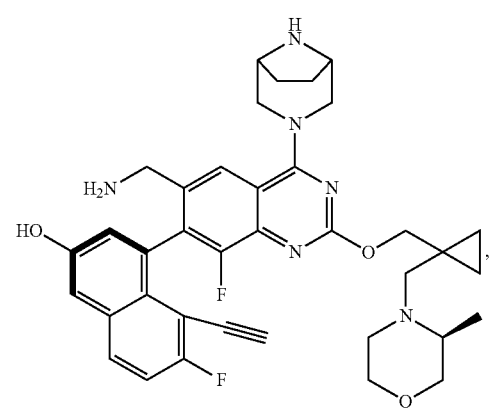
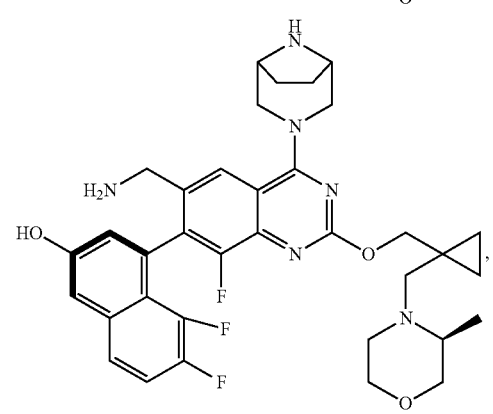

275
-continued
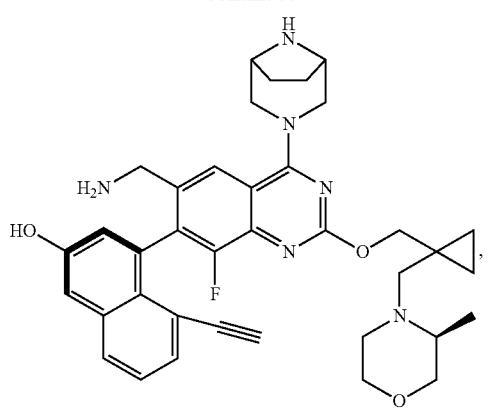
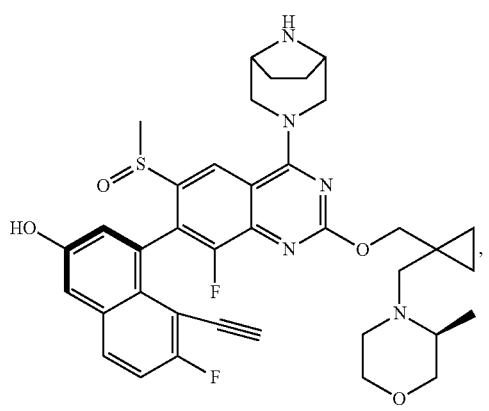
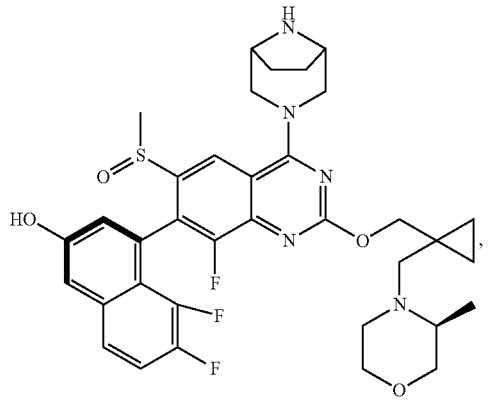
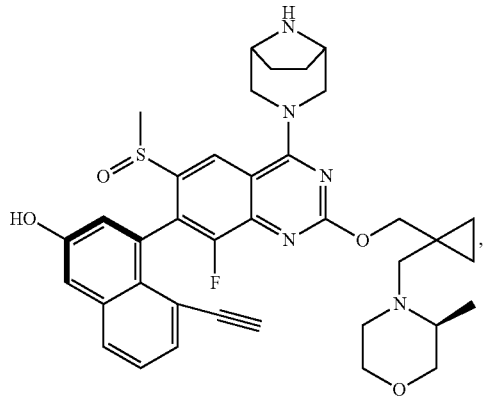
276
-continued
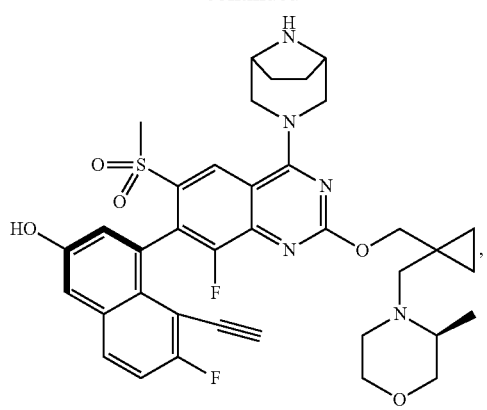
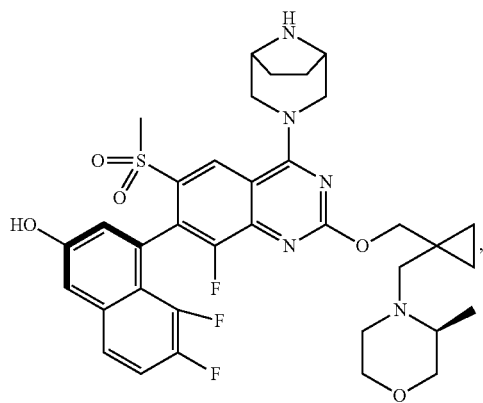
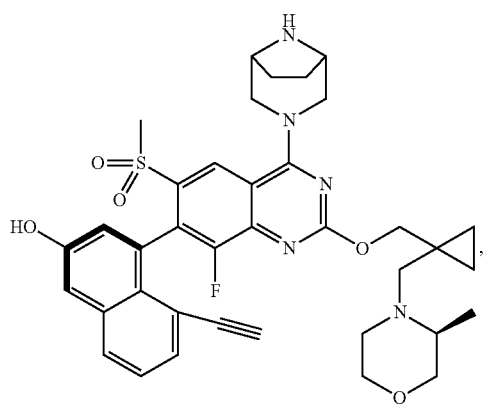
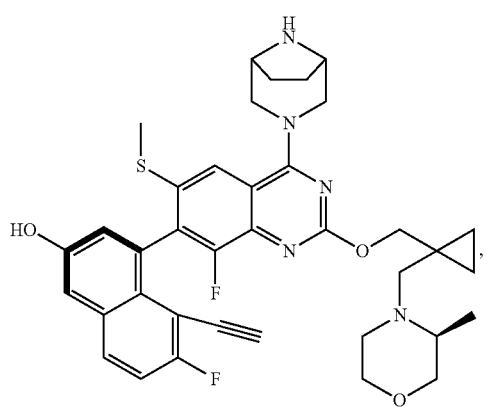

277
-continued
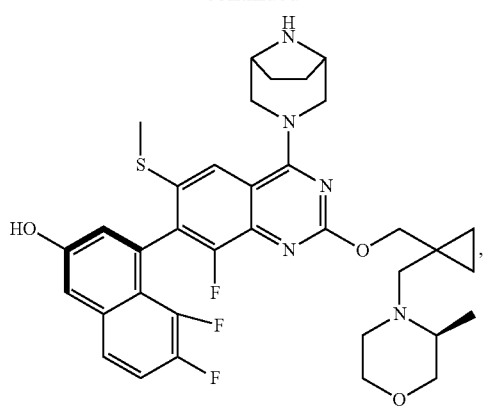
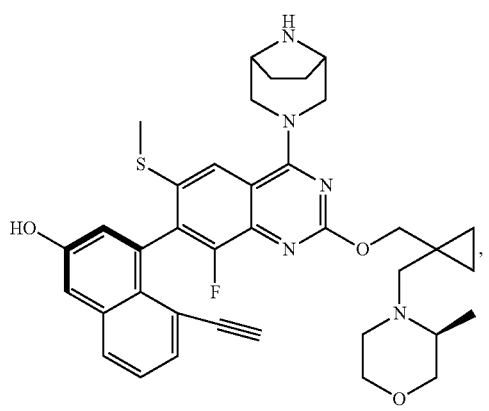
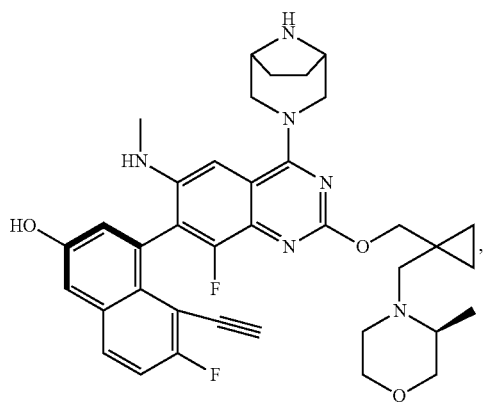
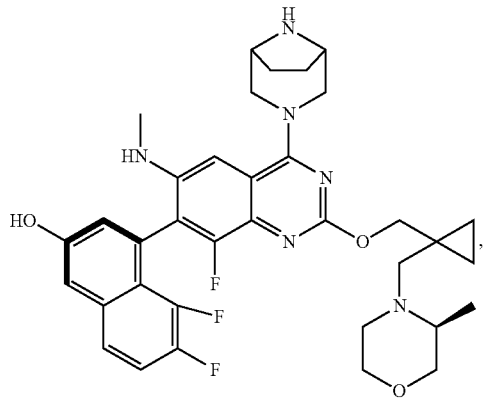
278
-continued
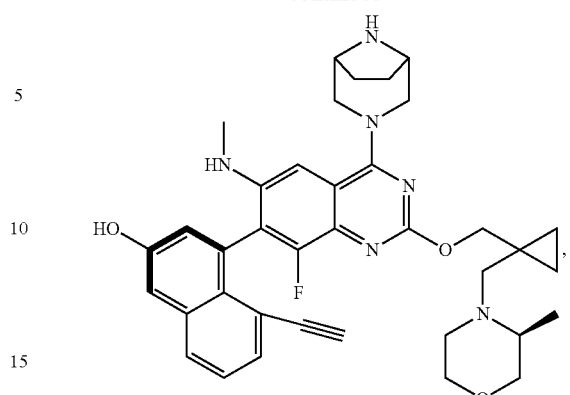
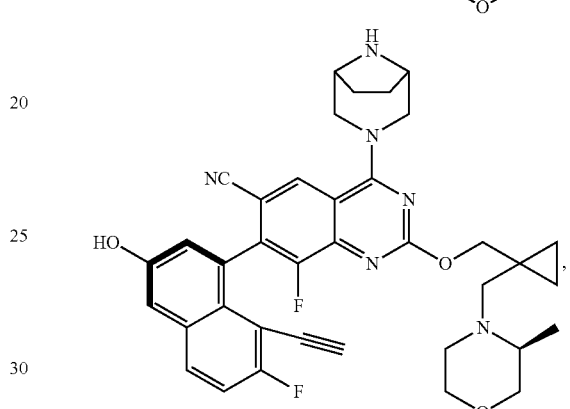
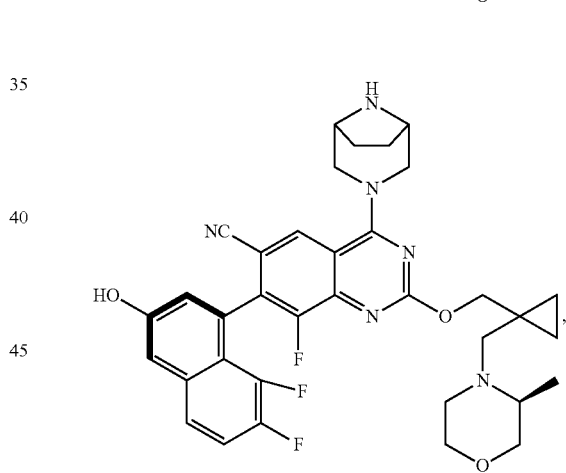
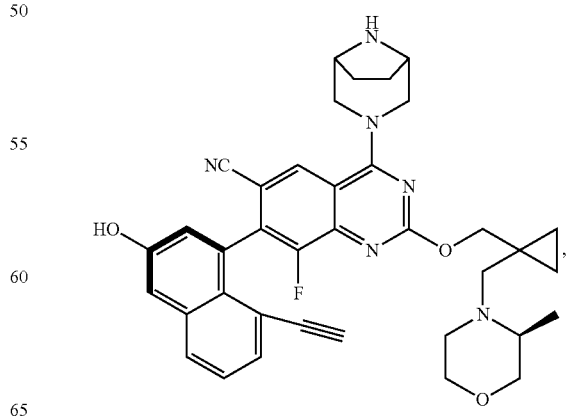

279
-continued
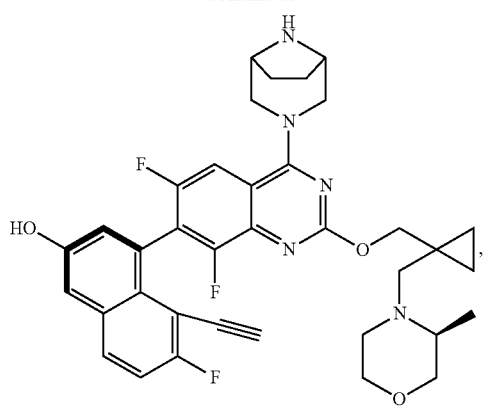
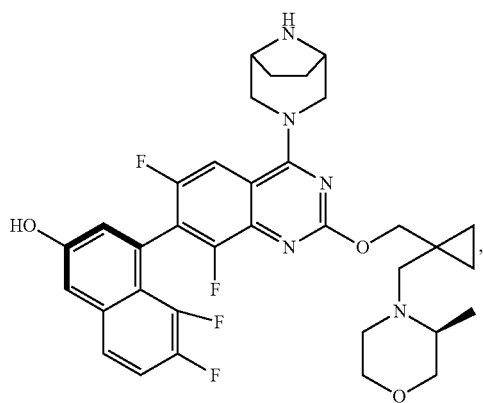
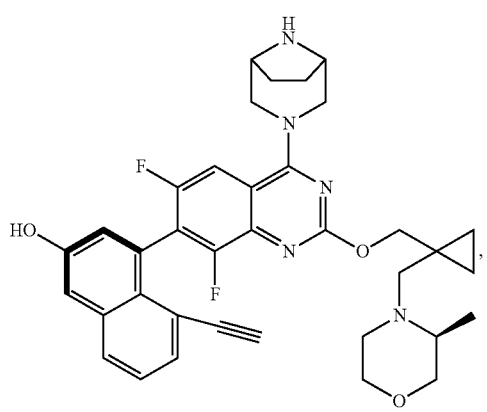
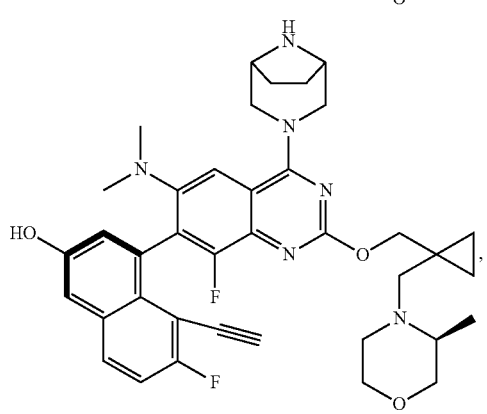
280
-continued
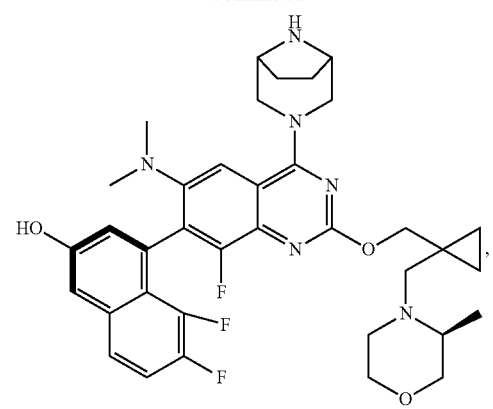
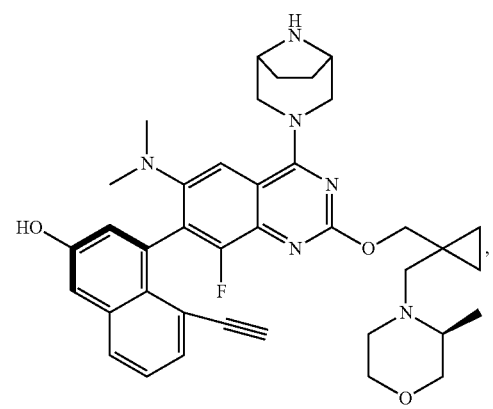
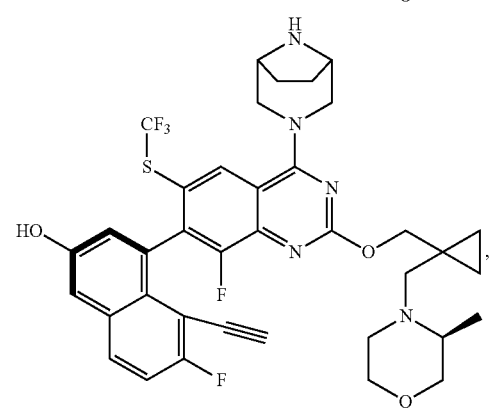
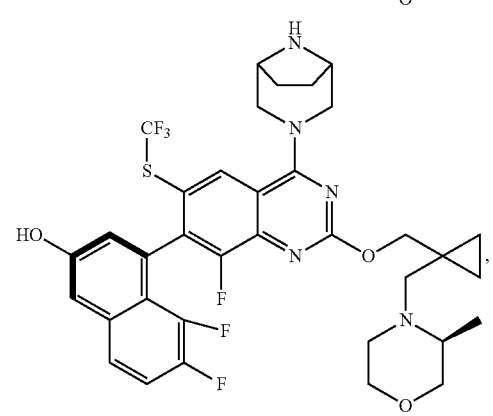

281
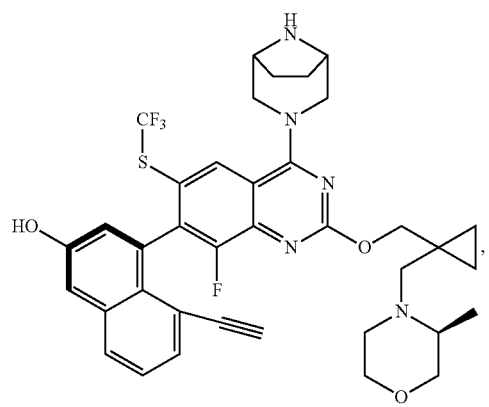
282
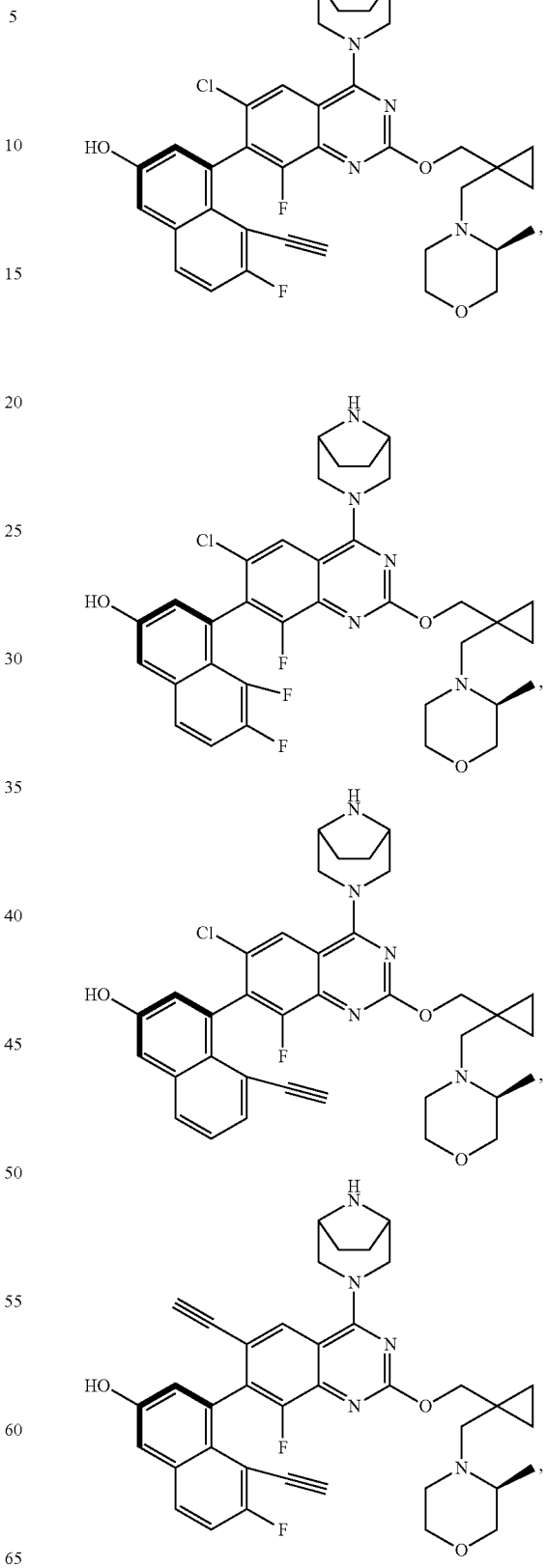

283
-continued
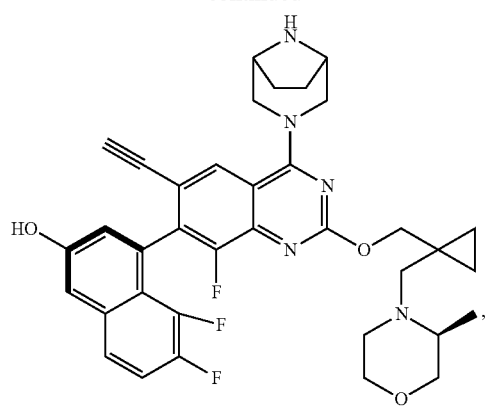
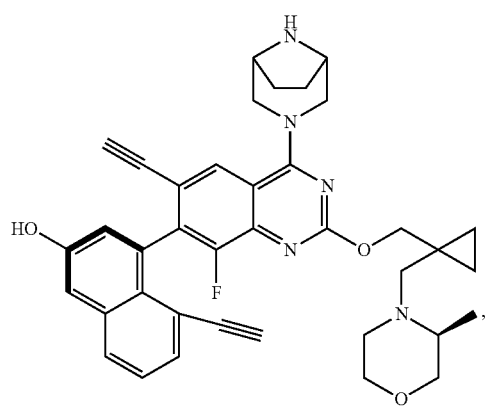
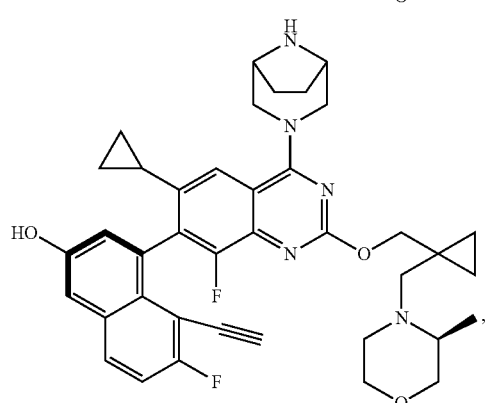
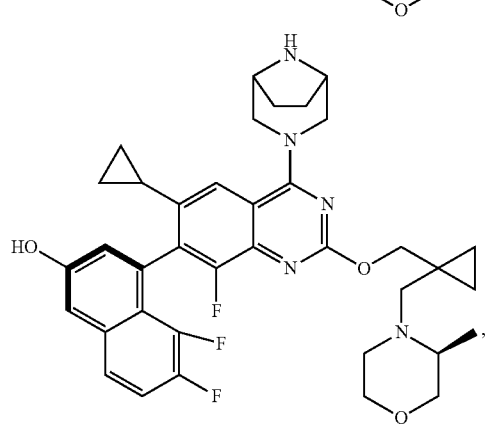
284
-continued
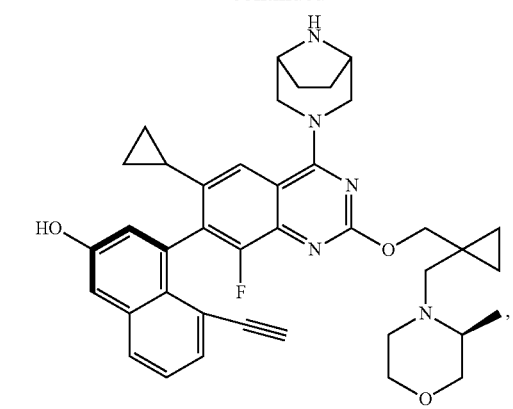
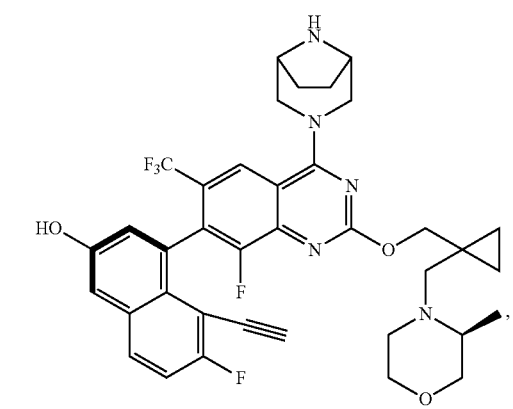
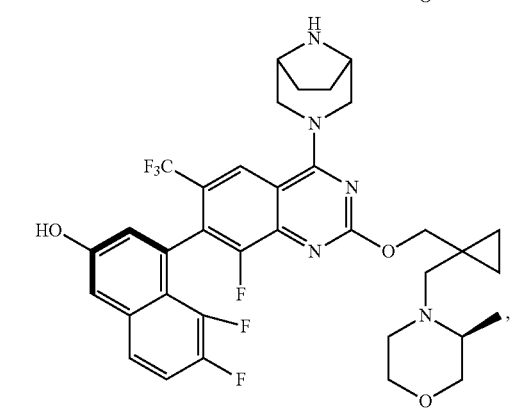
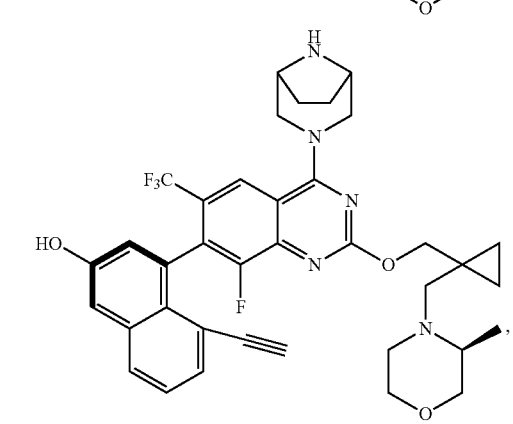

285
-continued
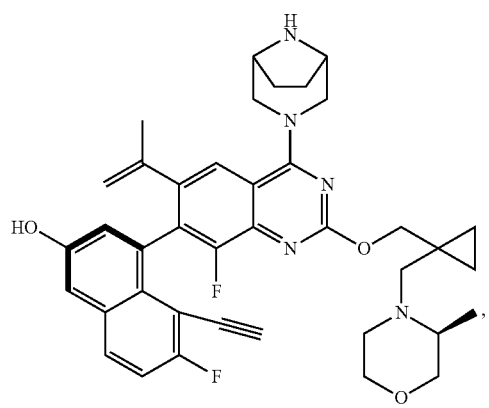
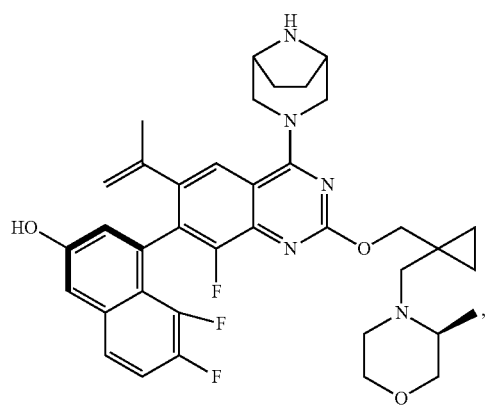
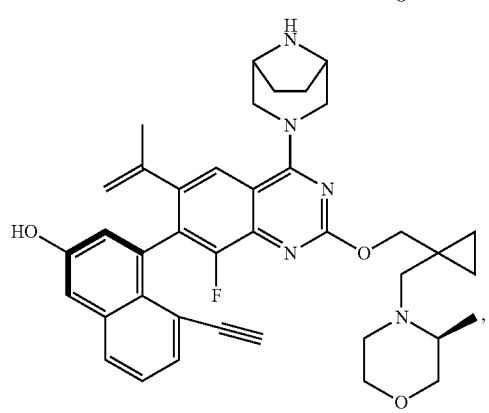
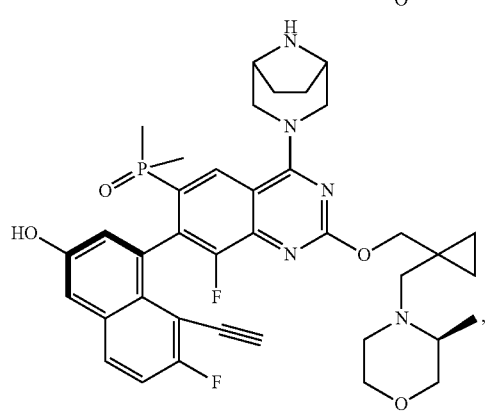
286
-continued
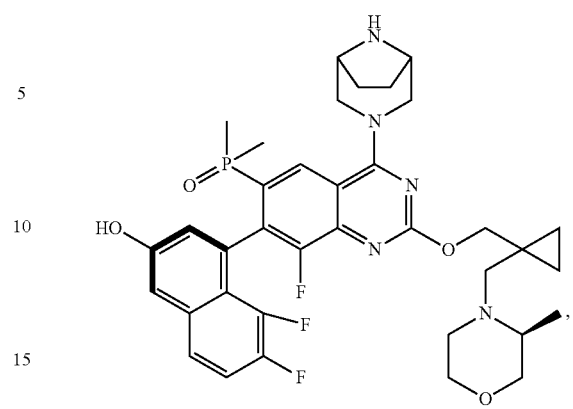
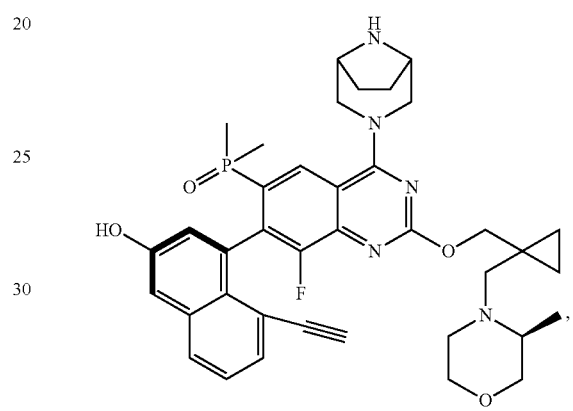
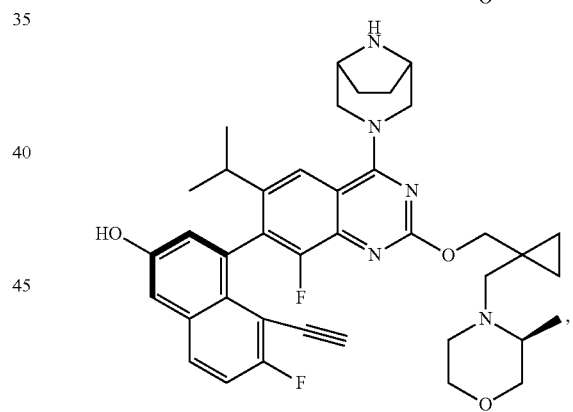
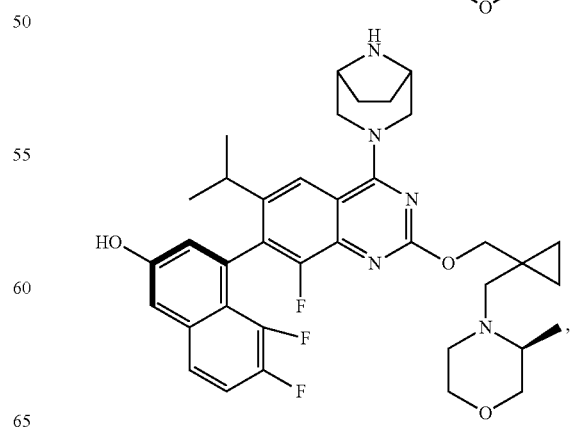

287
-continued
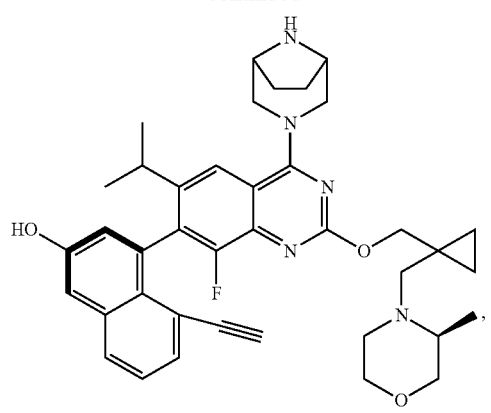
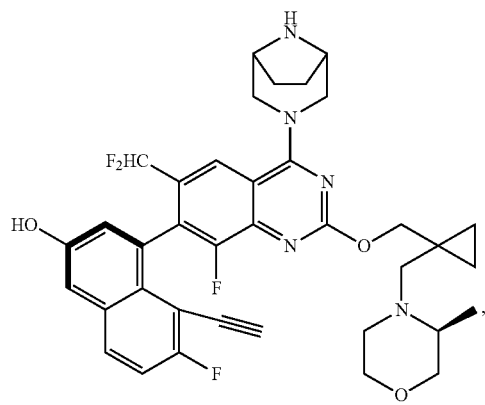
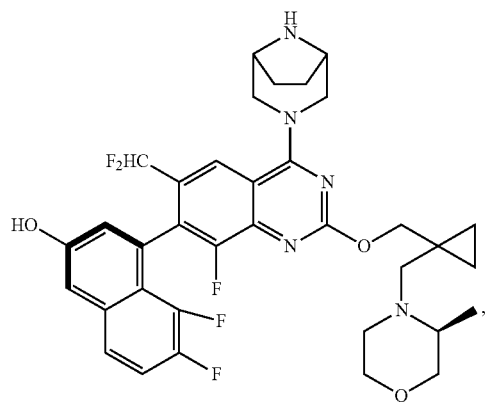
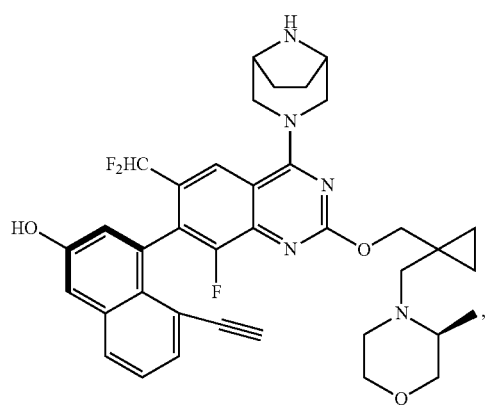
288
-continued
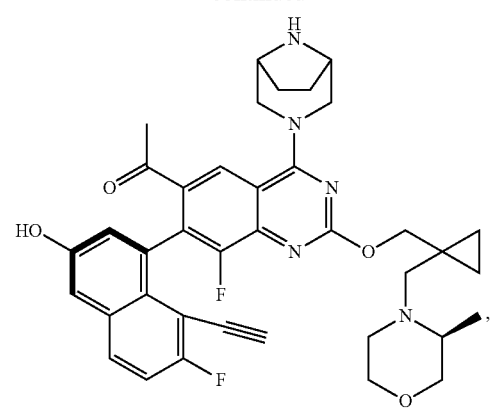
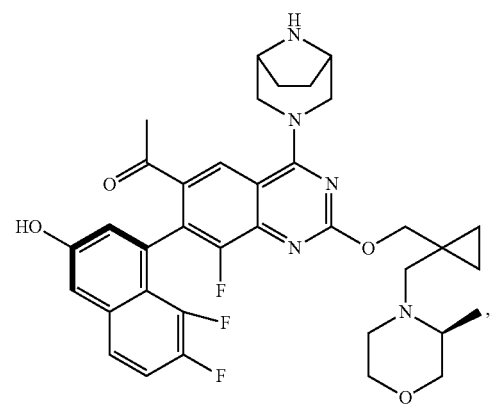
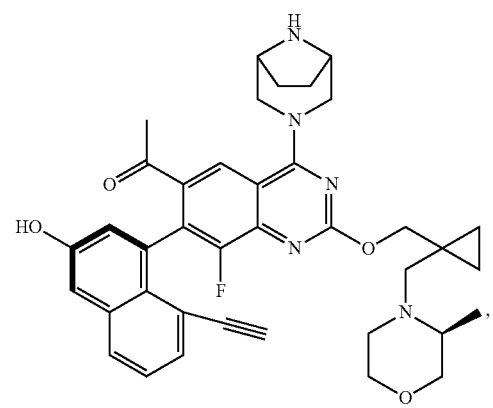
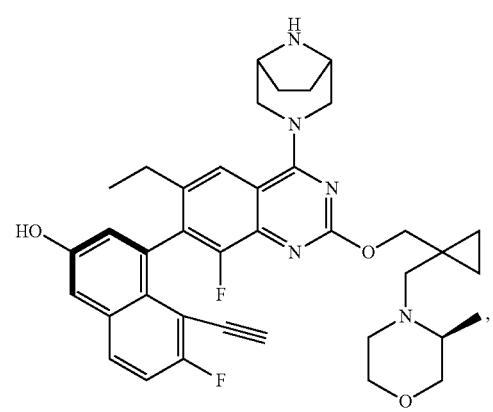

289
-continued
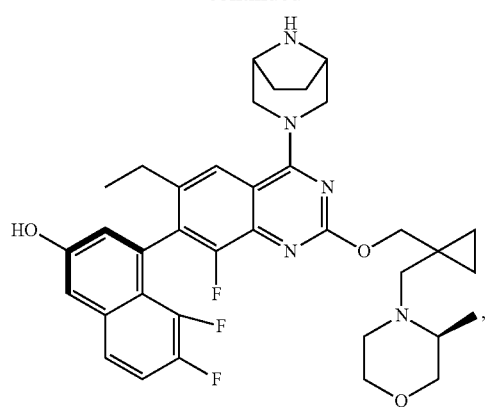
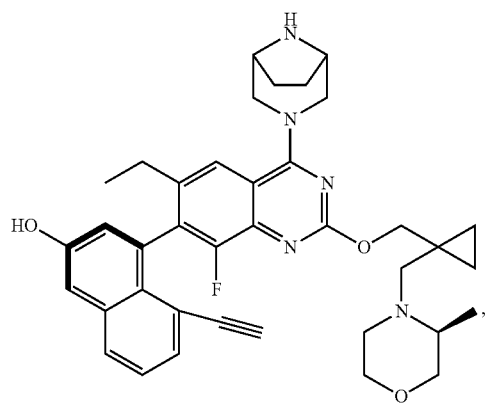
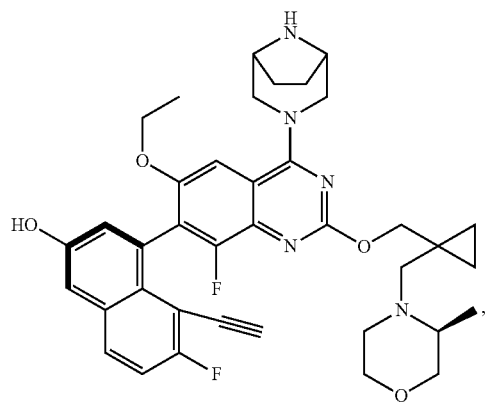
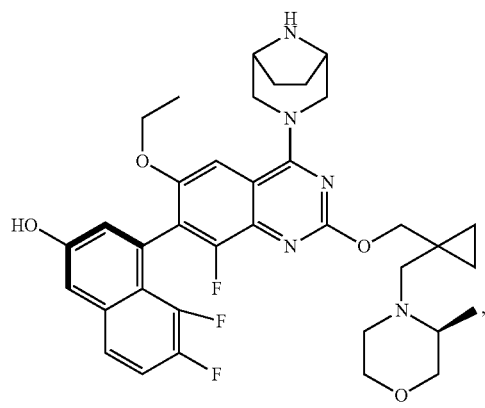
290
-continued
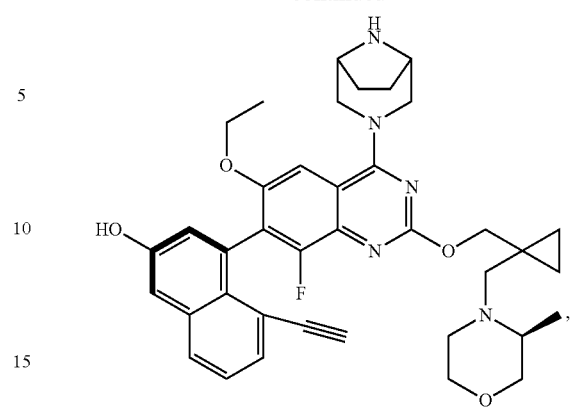
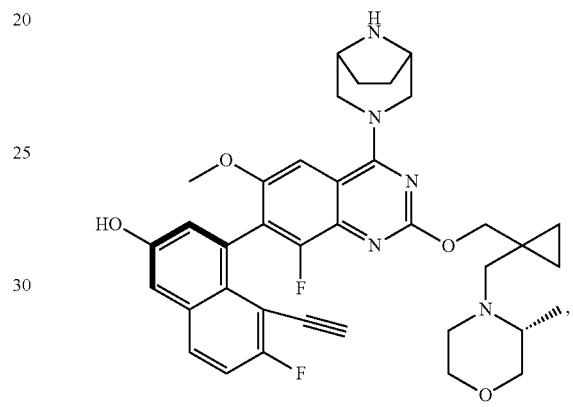
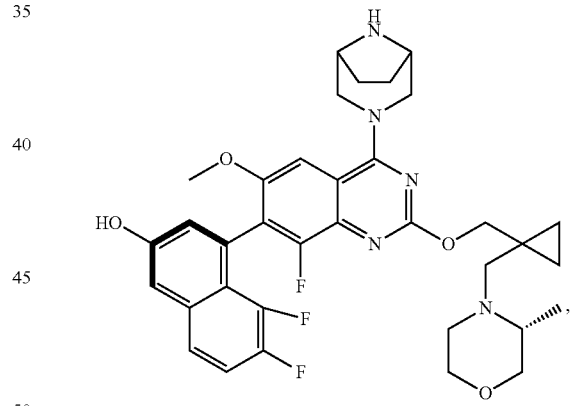
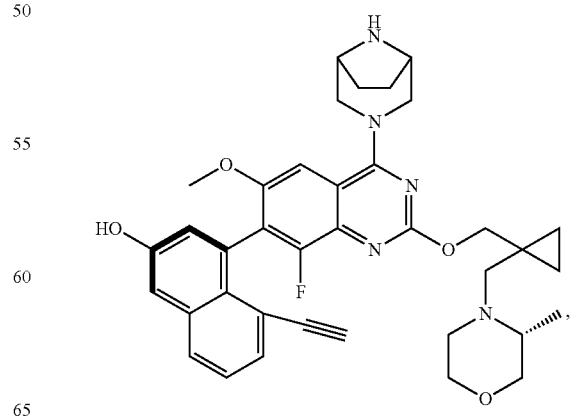

291
-continued
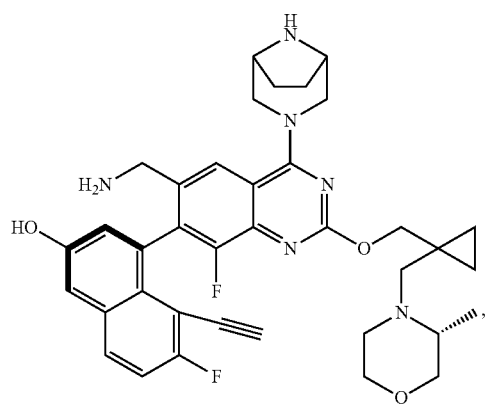
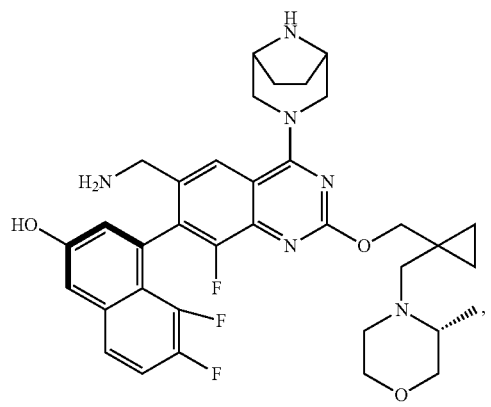
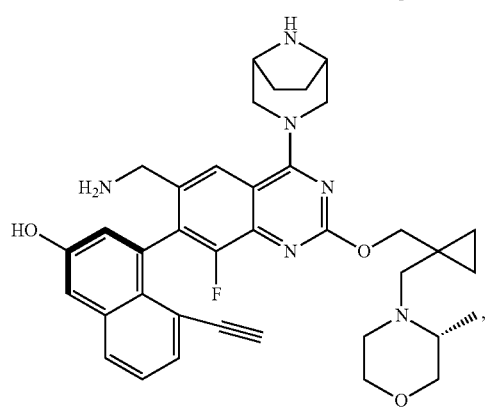
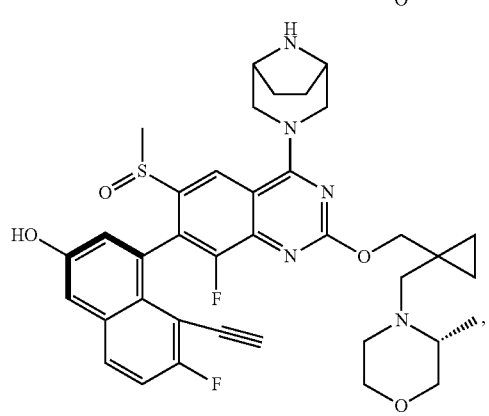
292
-continued
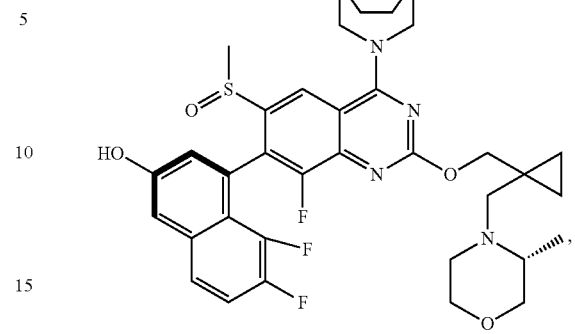
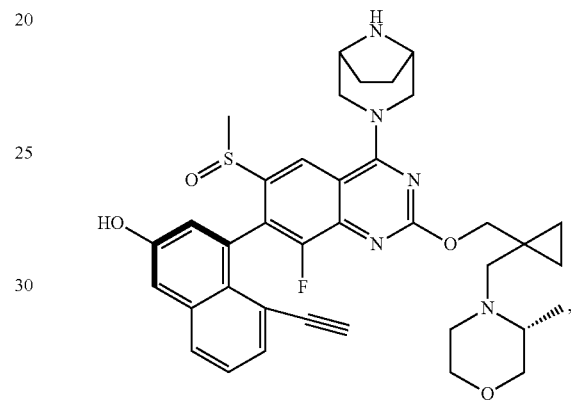

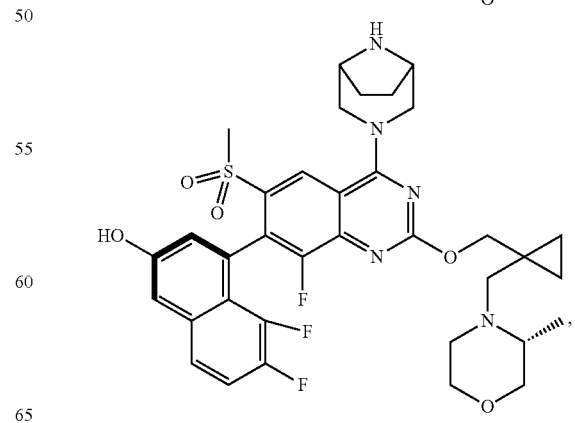

293
-continued
294
-continued
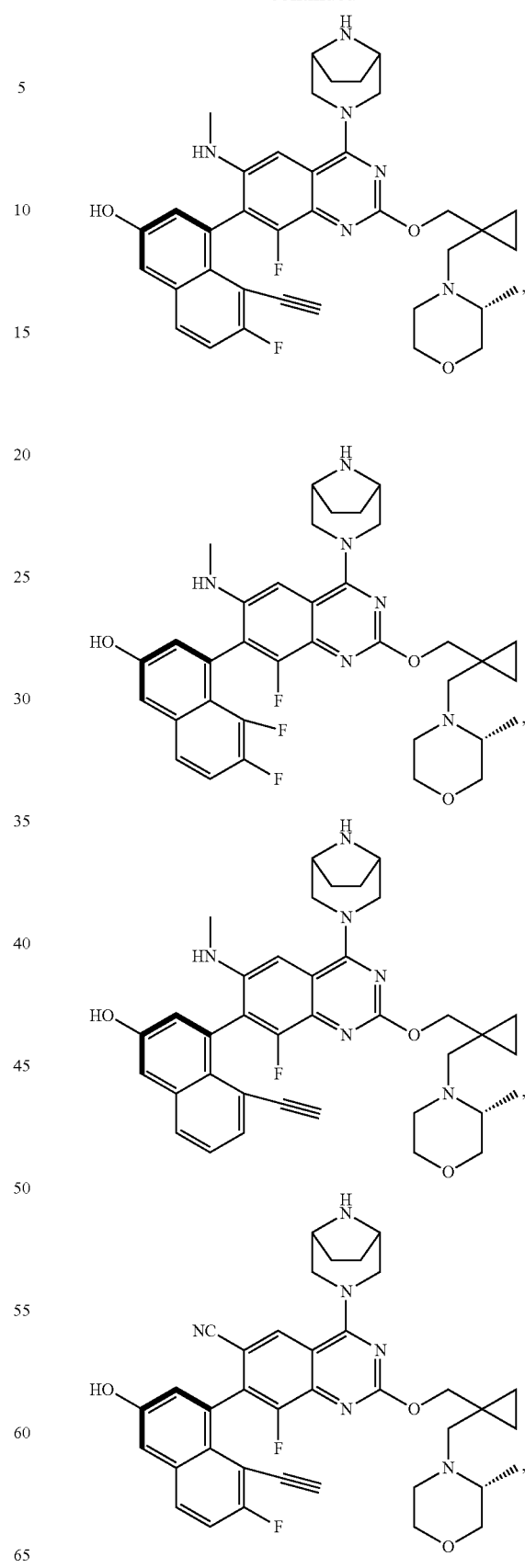

295
-continued
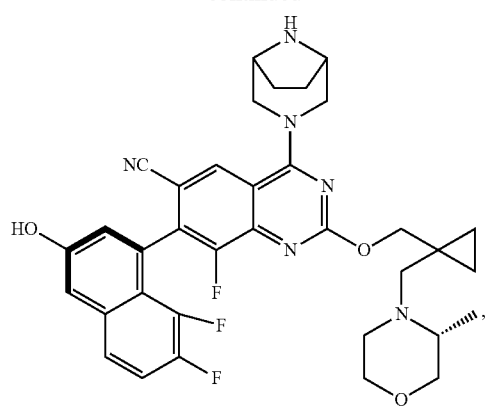
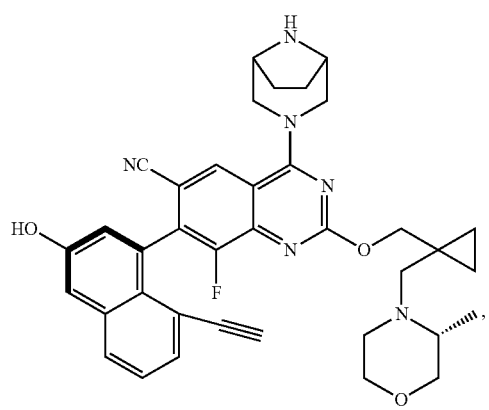
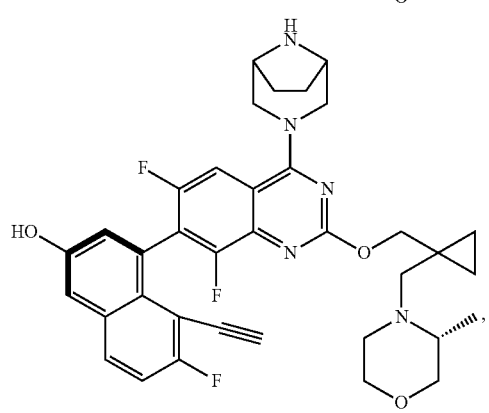
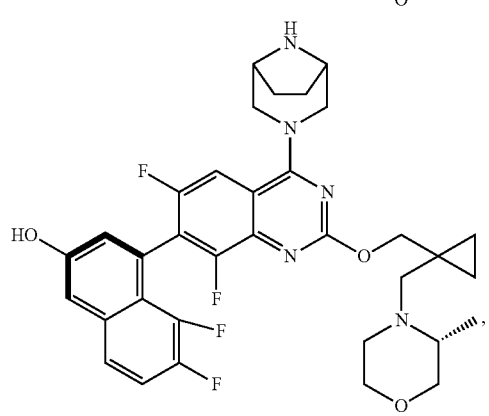
296
-continued
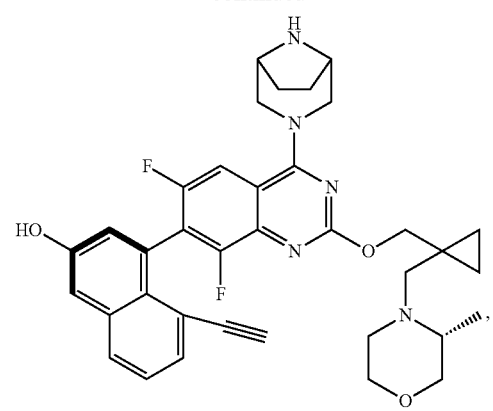
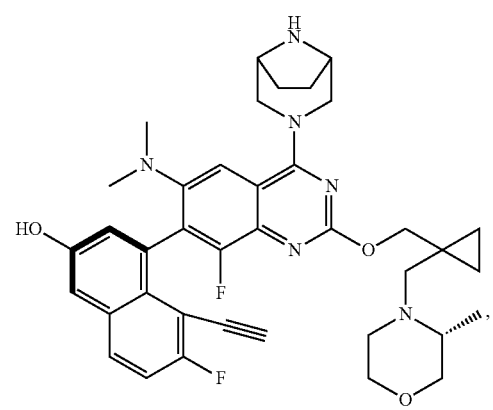
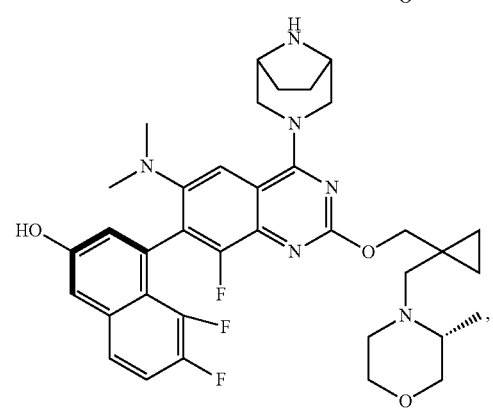
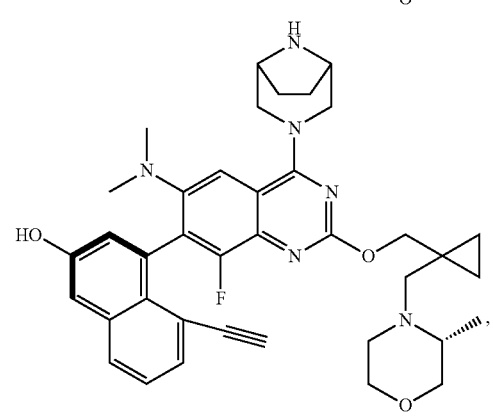

297
-continued
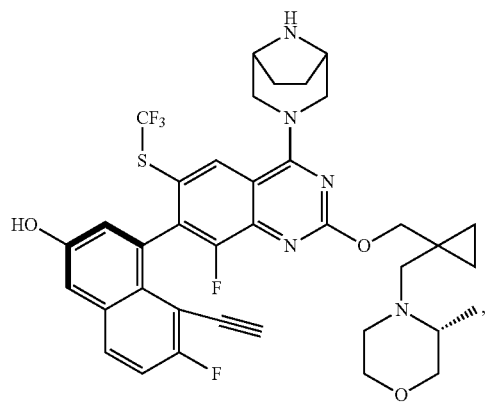
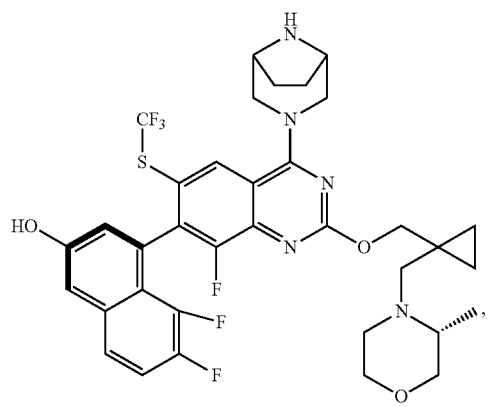
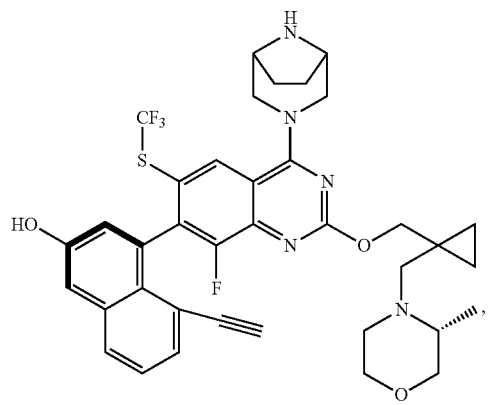
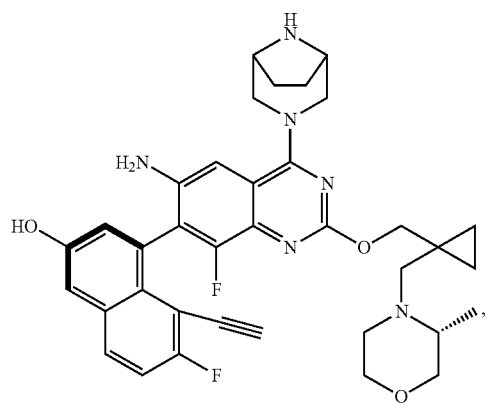
298
-continued
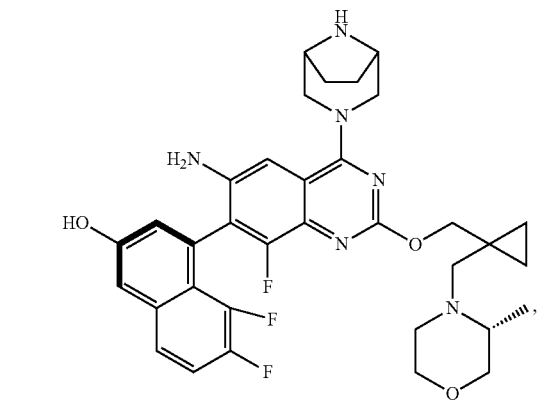
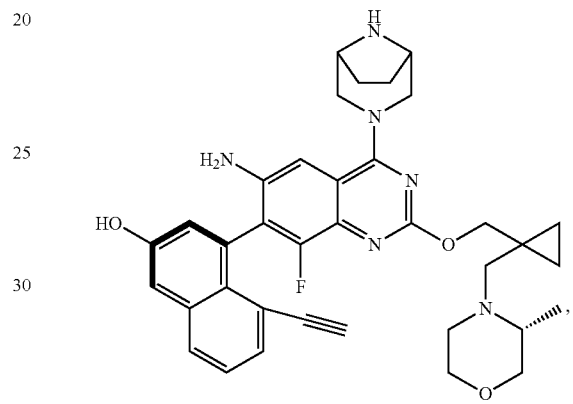
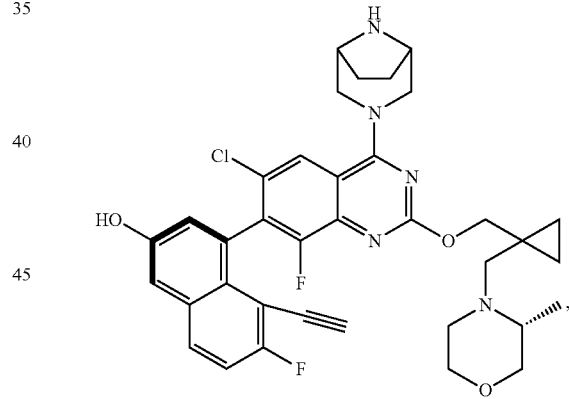
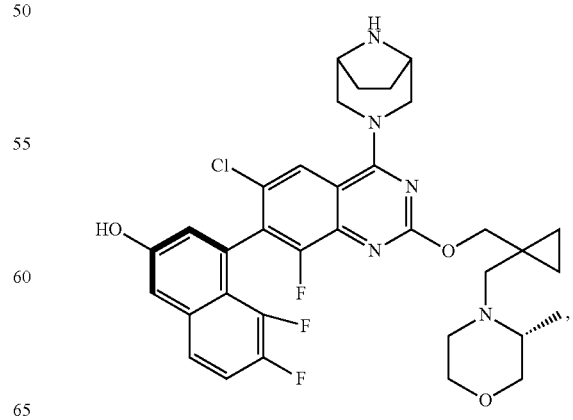

299
-continued
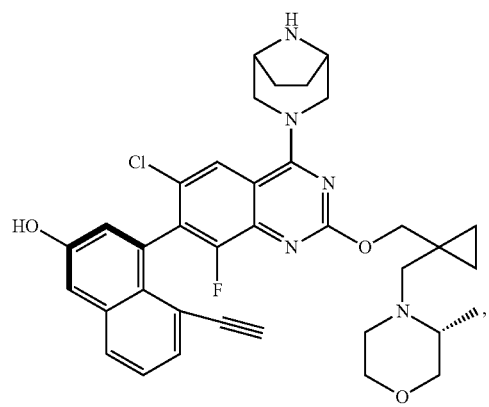
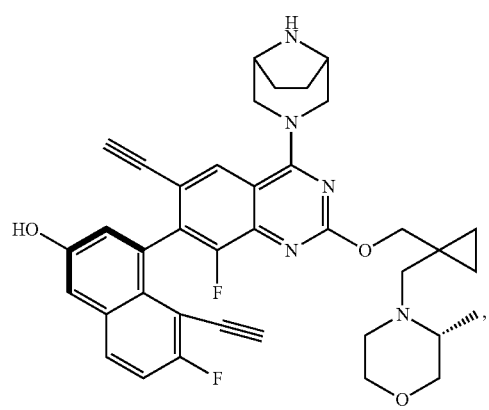
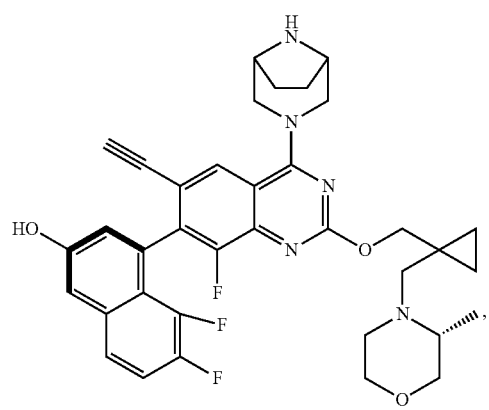
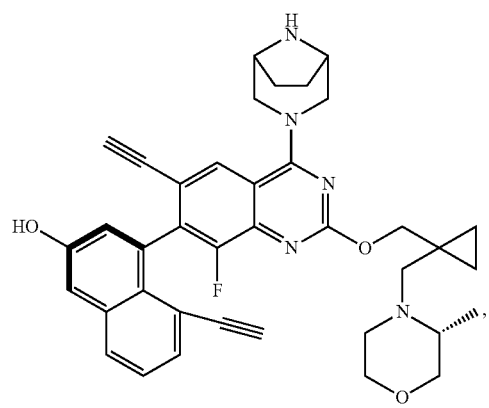
300
-continued
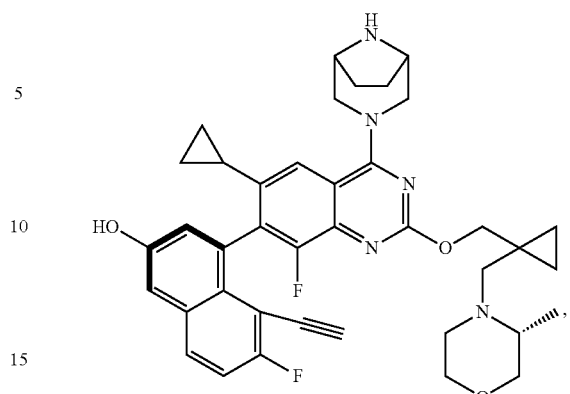
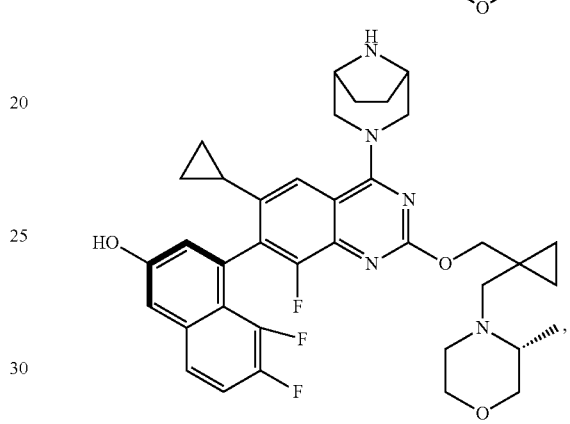
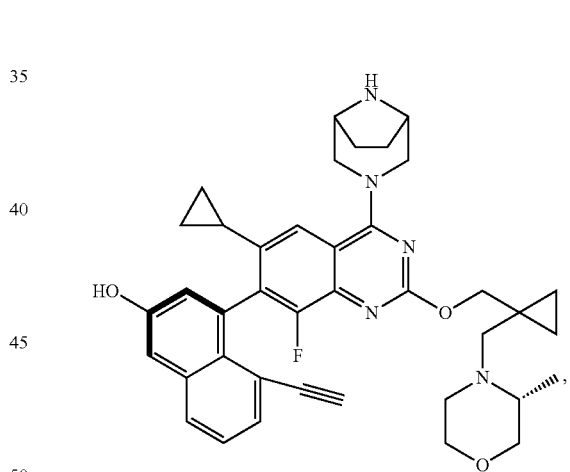
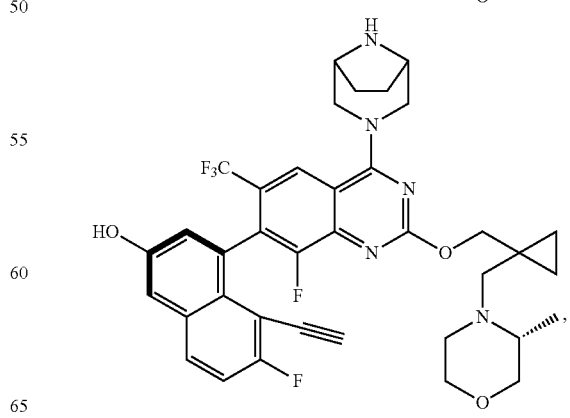

301
-continued
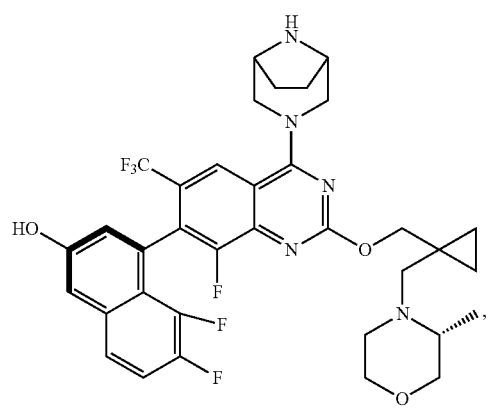
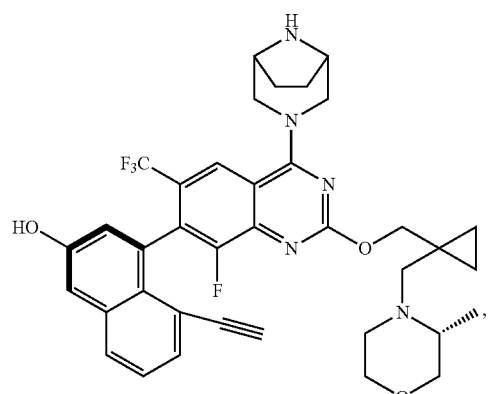
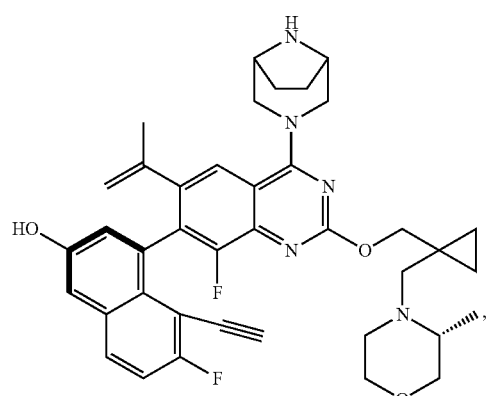
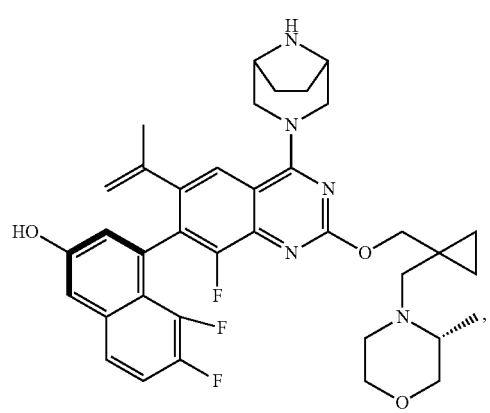
302
-continued
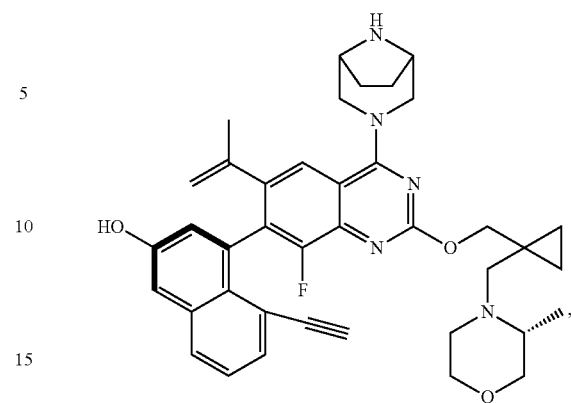
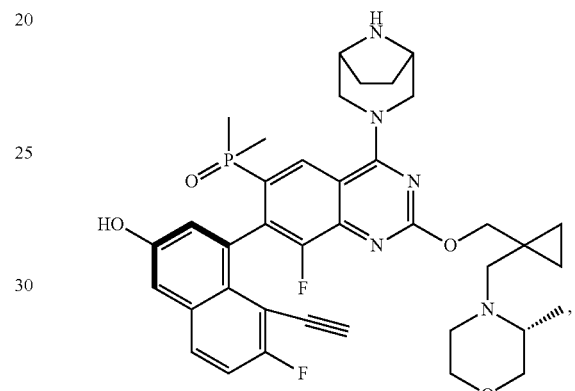
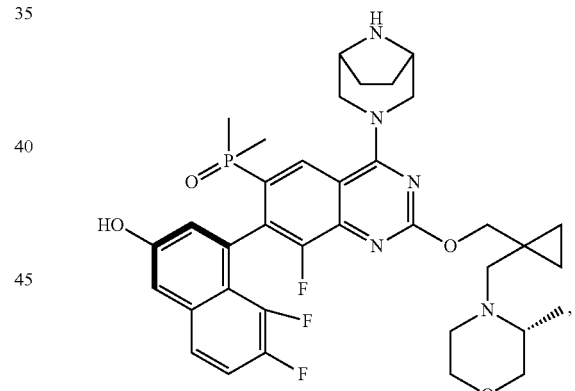
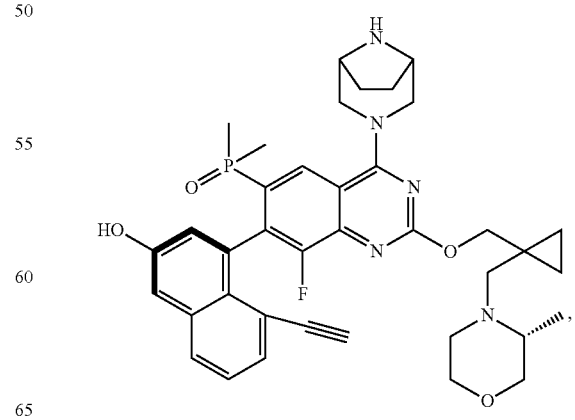

303
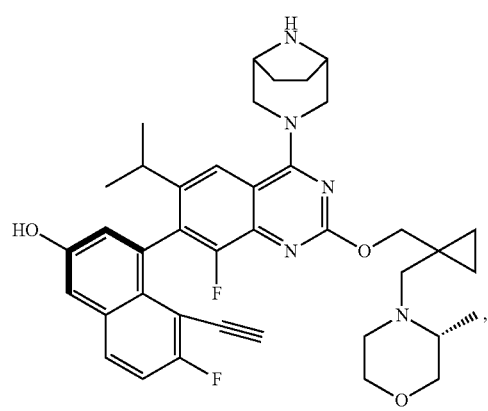
304
-continued
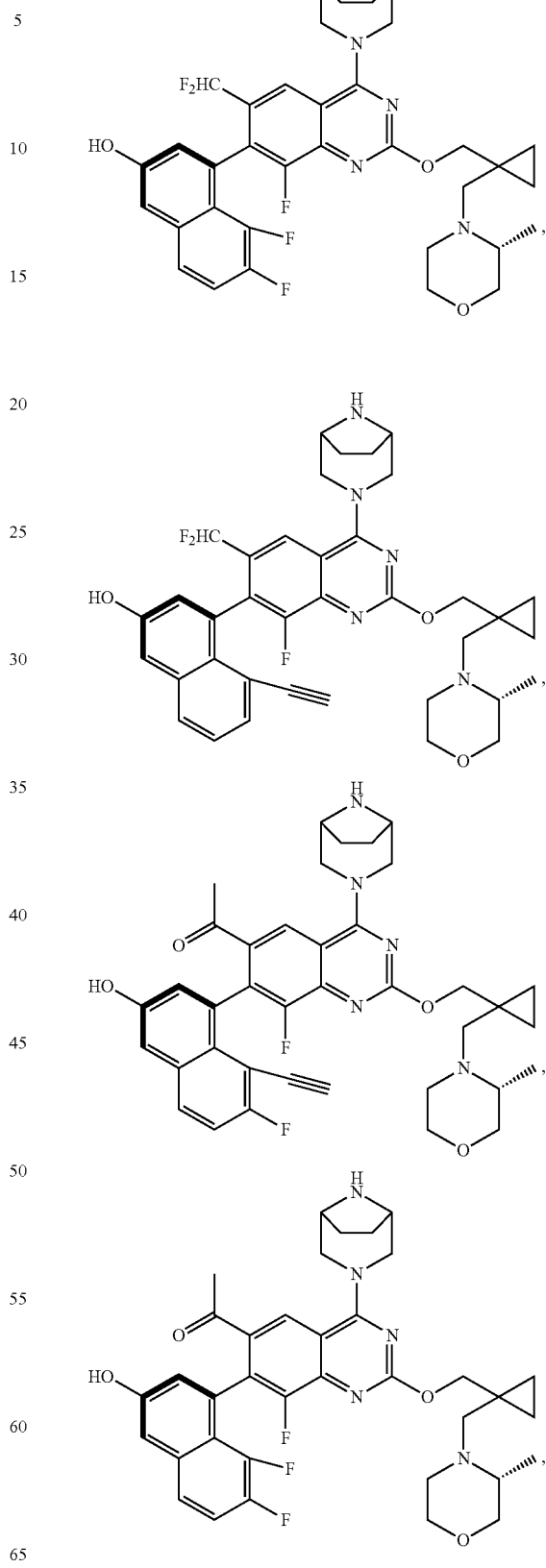

305
-continued
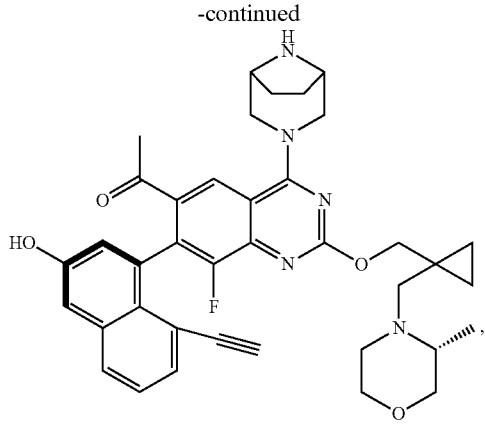
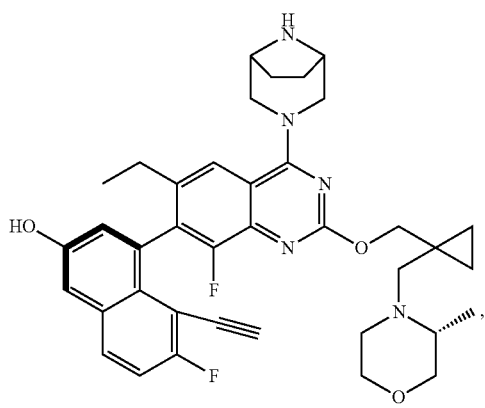
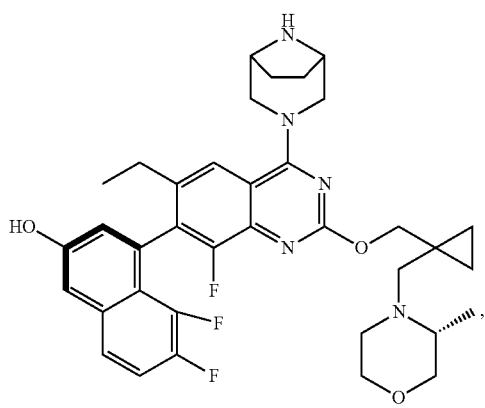
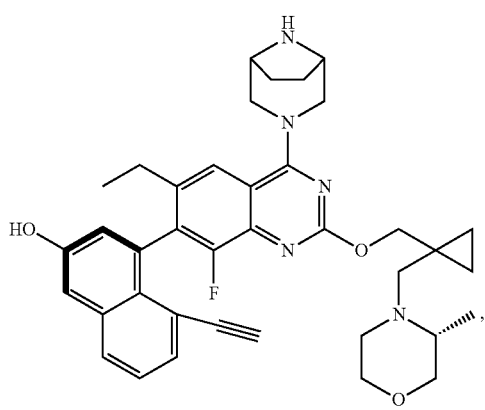
306
-continued
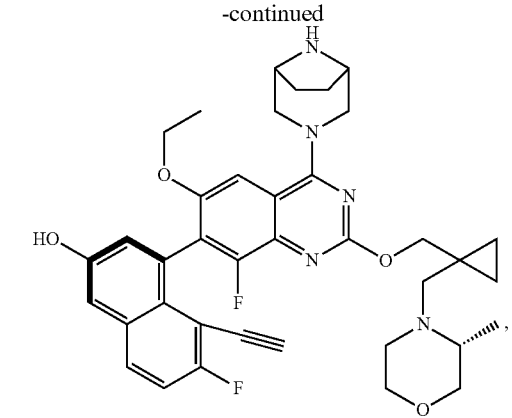

307
-continued
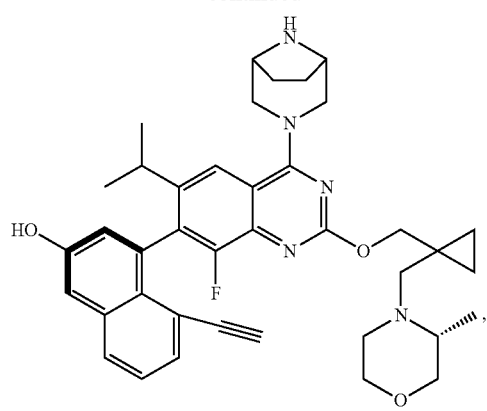
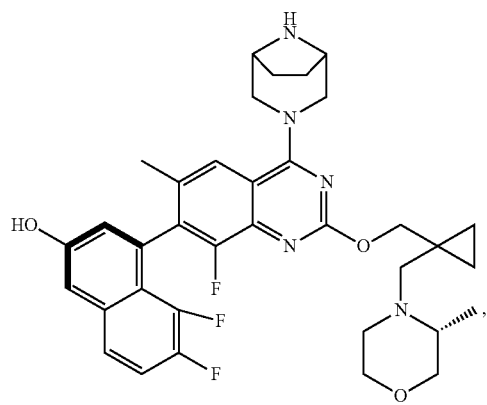
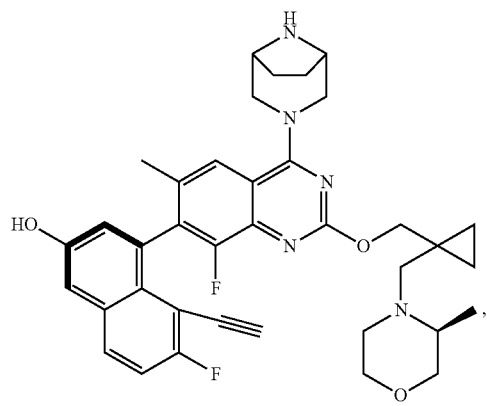
308
-continued
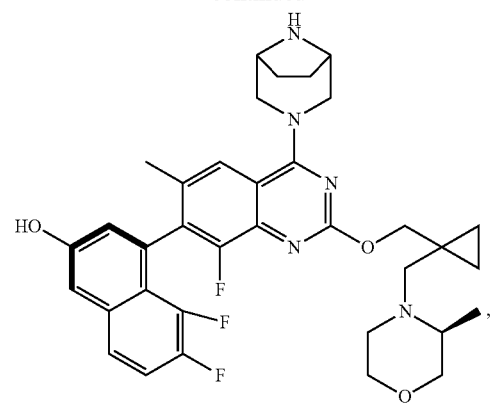
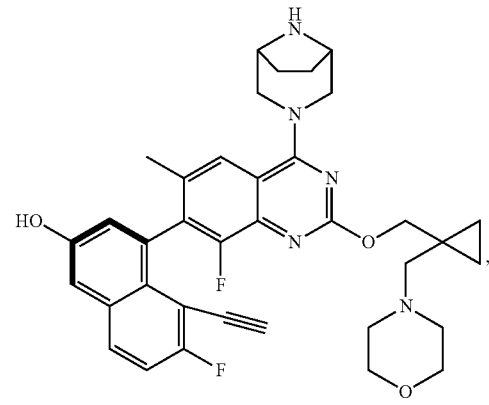
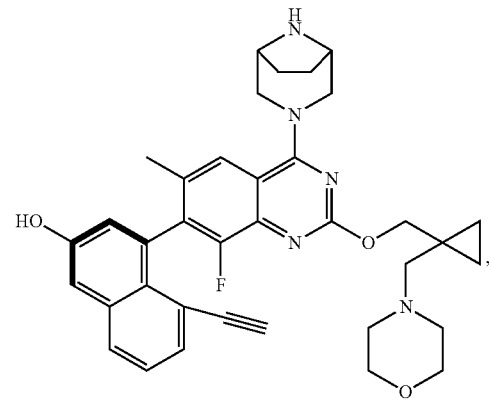

309
-continued

310
-continued
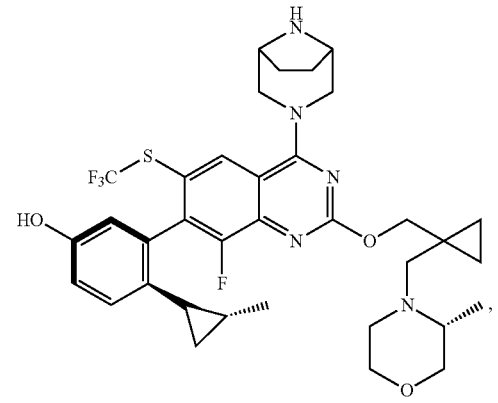
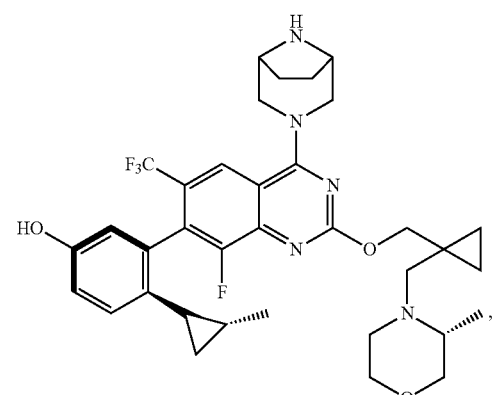
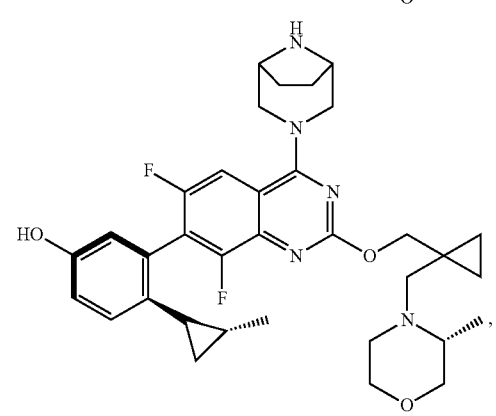
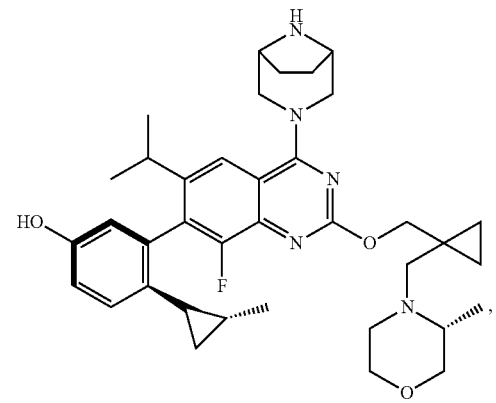

311
-continued
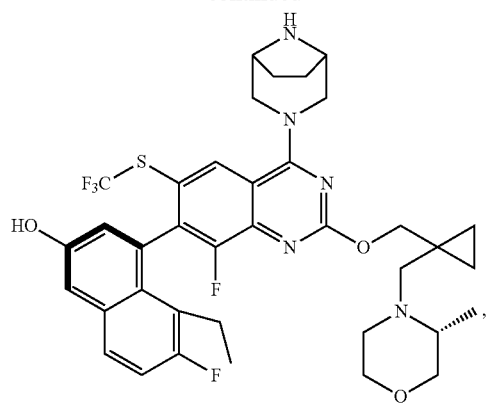
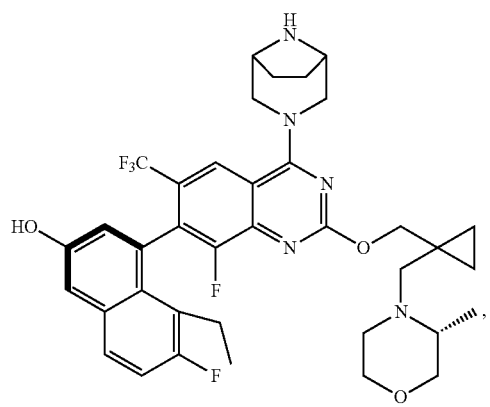
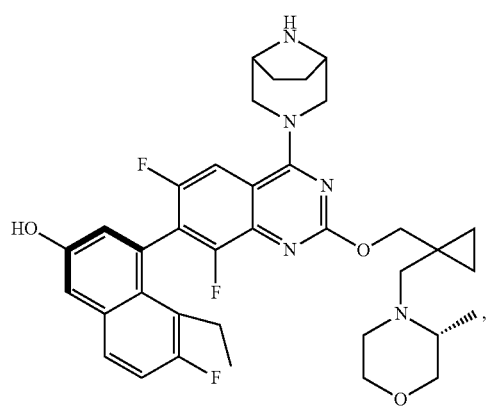
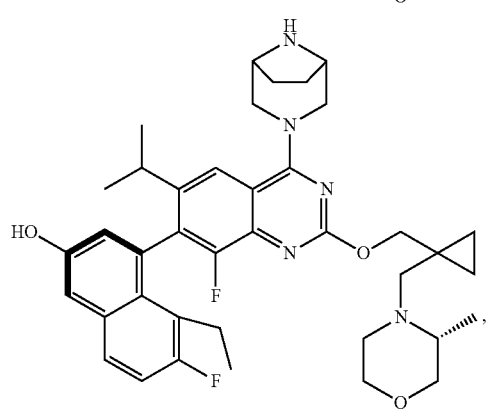
312
-continued
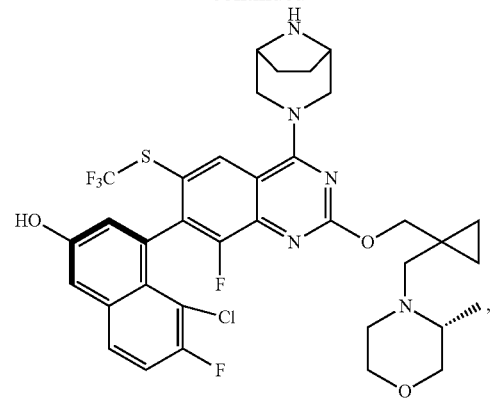
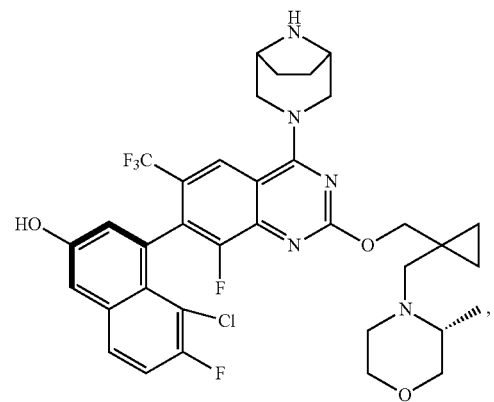
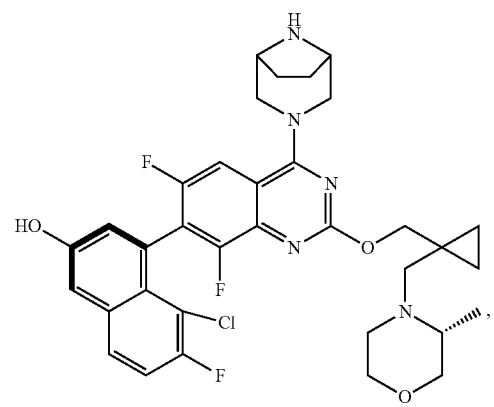
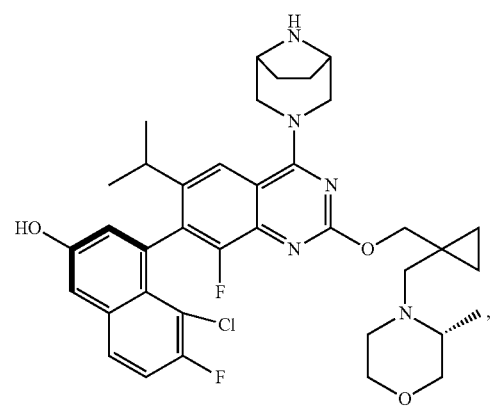

313
-continued
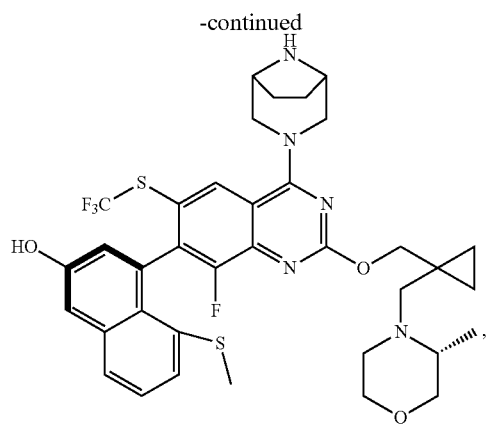
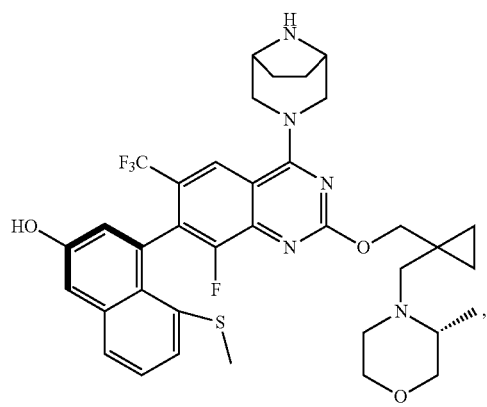
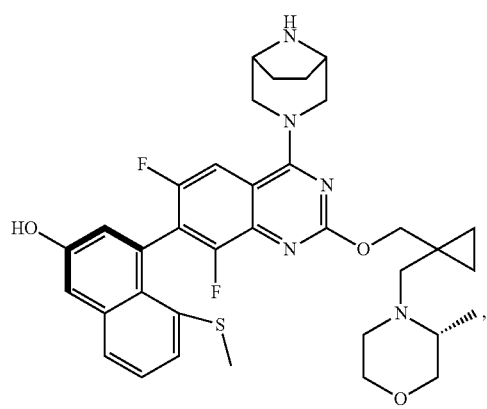
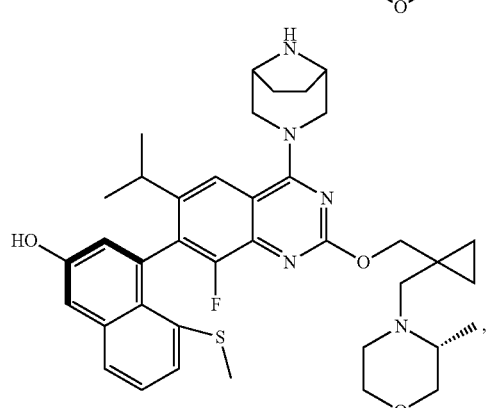
314
-continued
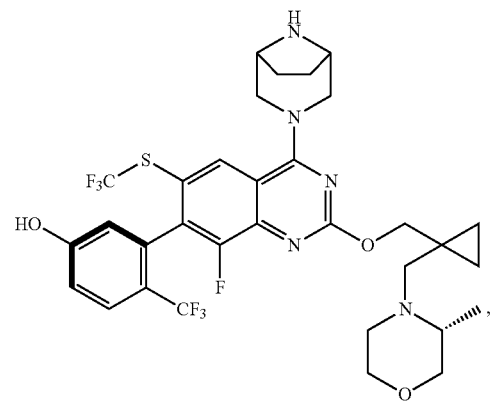
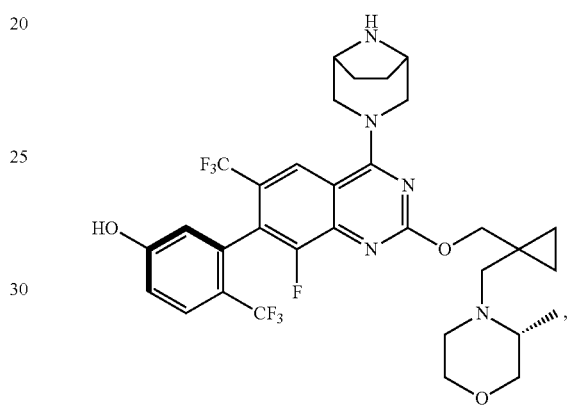
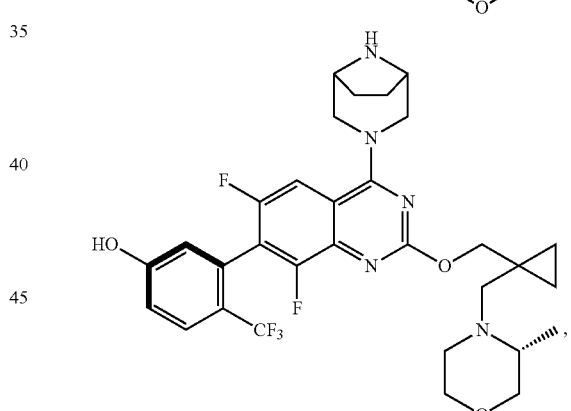
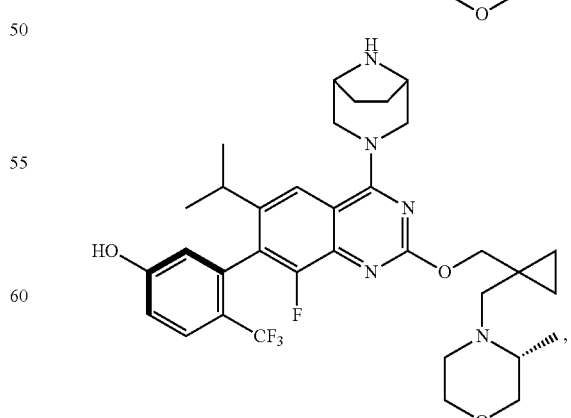

315
-continued
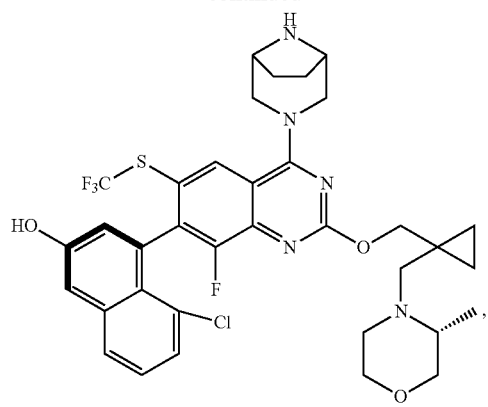
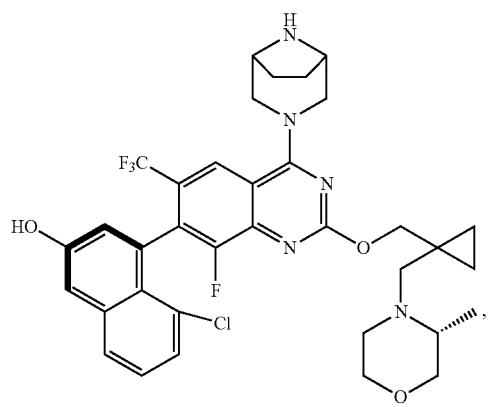
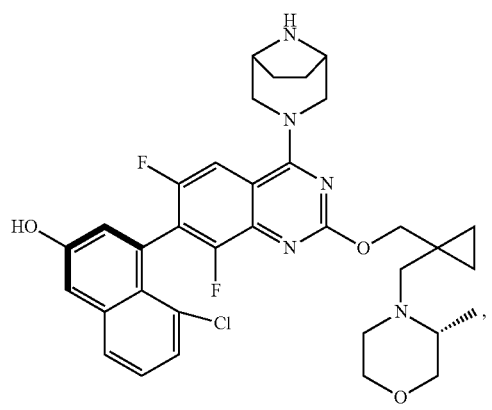
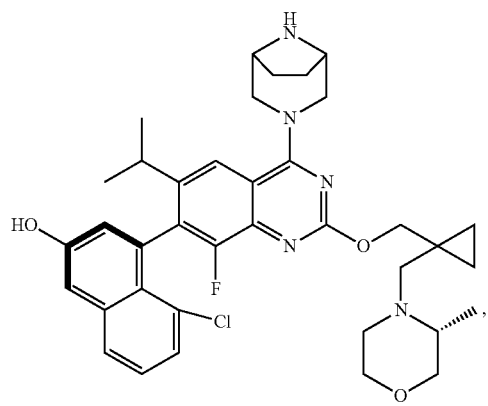
316
-continued
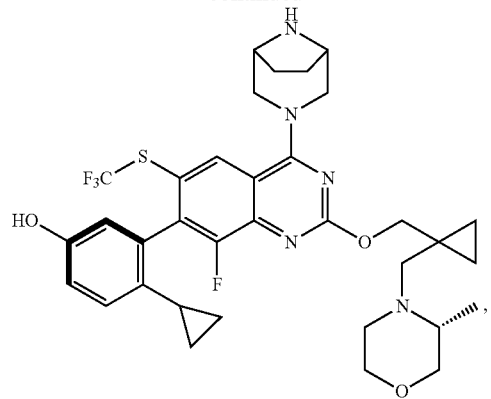
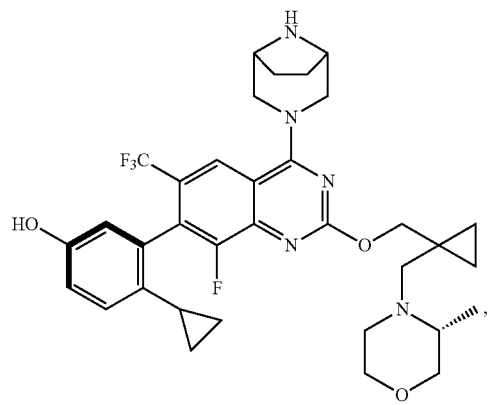
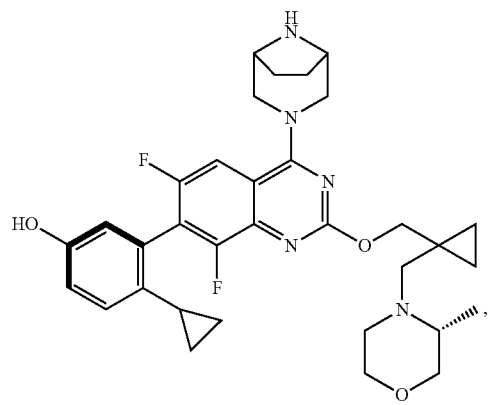
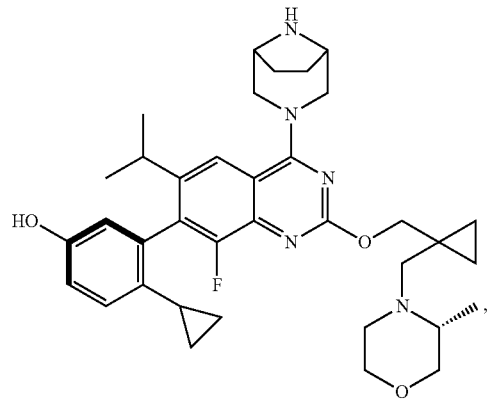

317
-continued
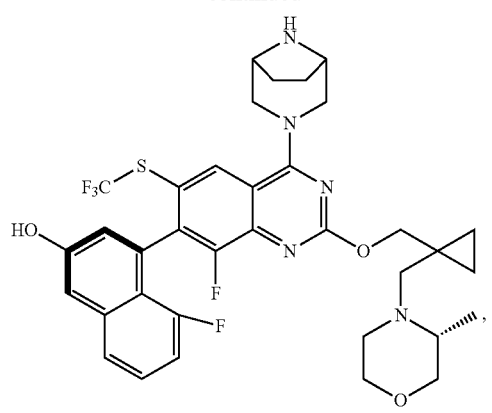
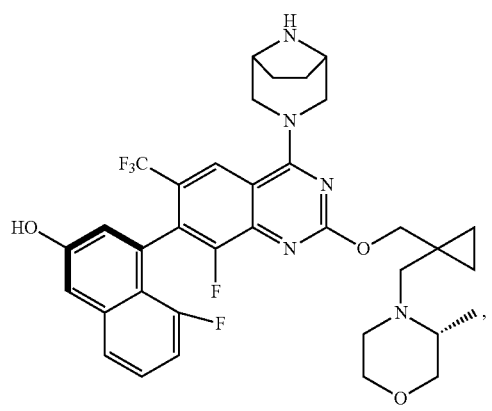
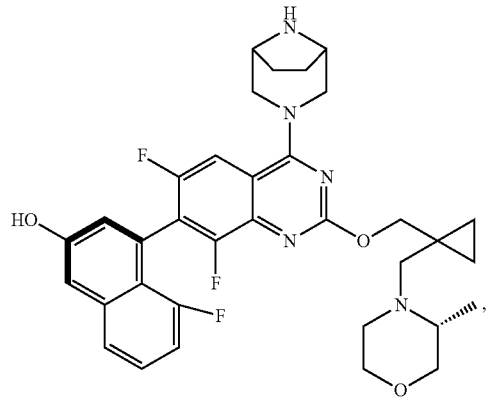
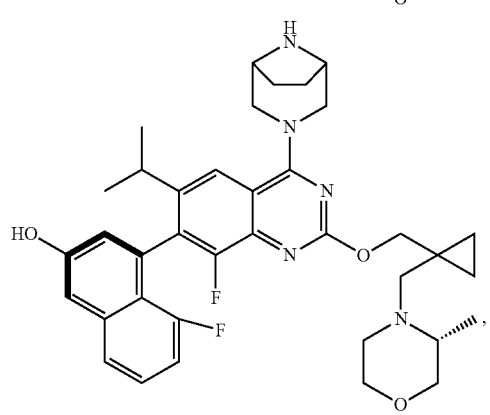
318
-continued
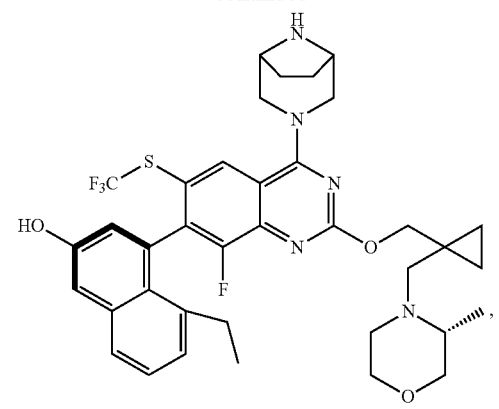
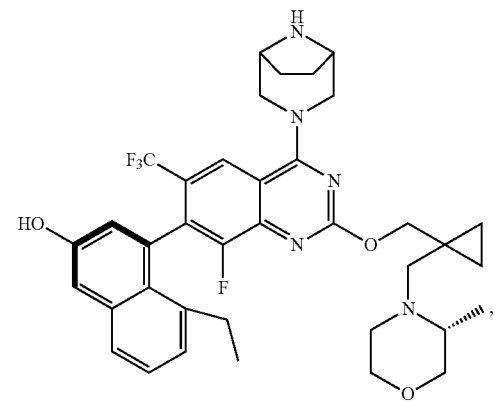
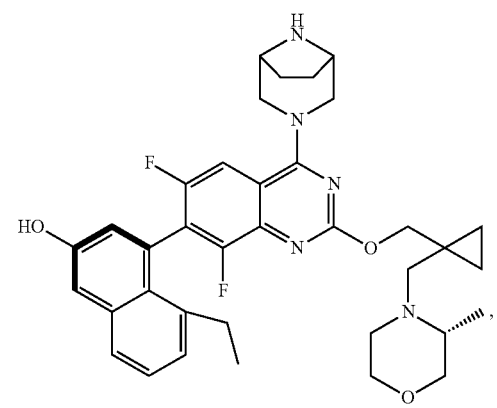
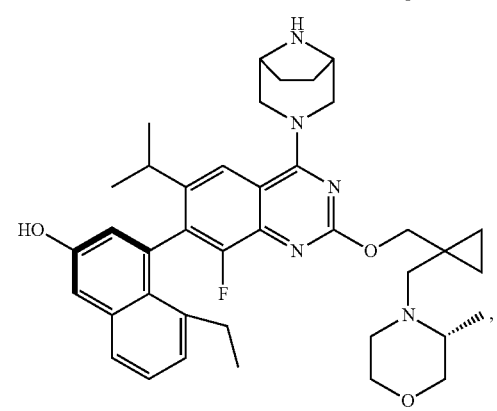

319
-continued
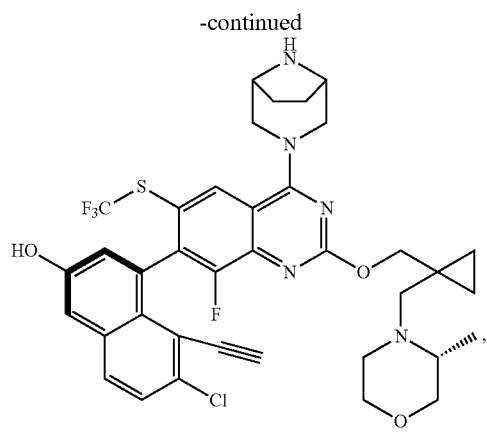
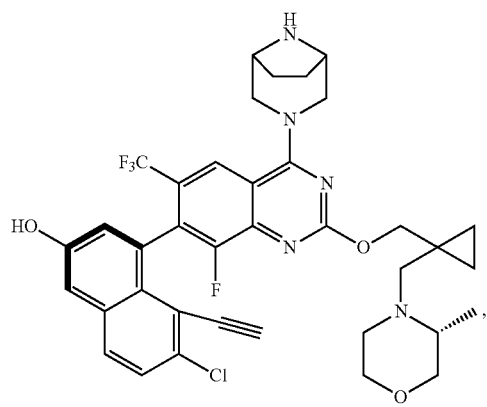
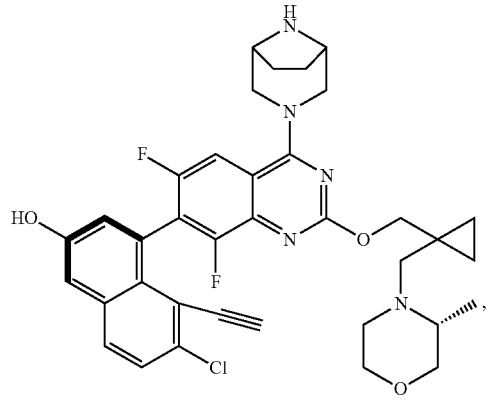
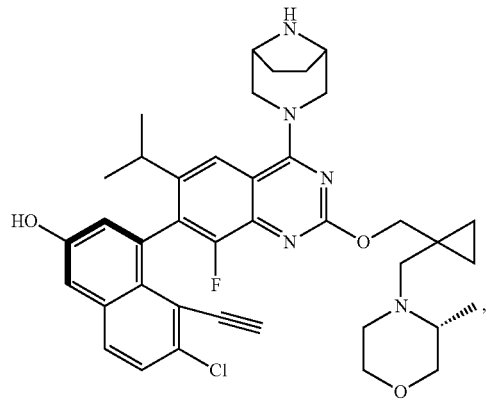
320
-continued
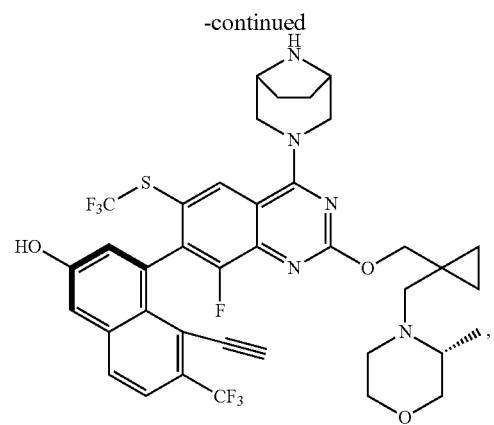
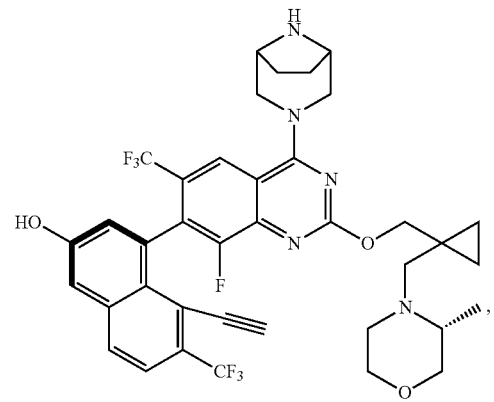
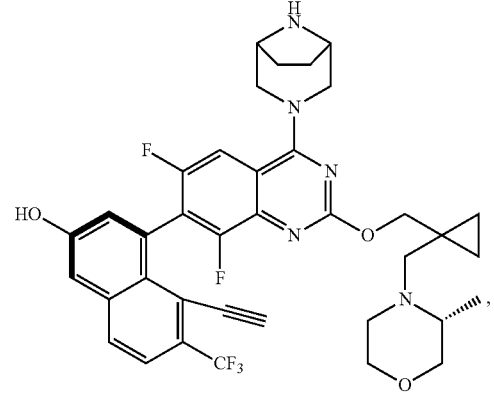
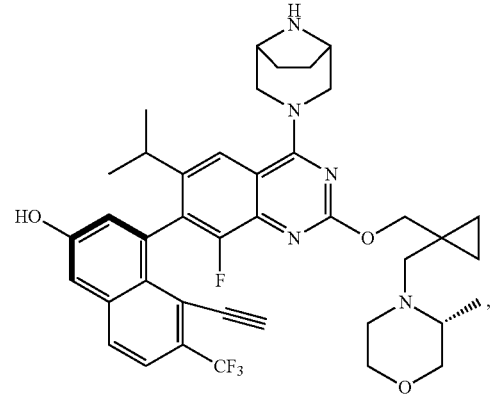

321
-continued
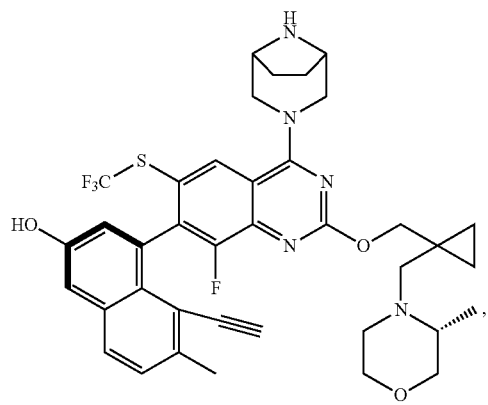
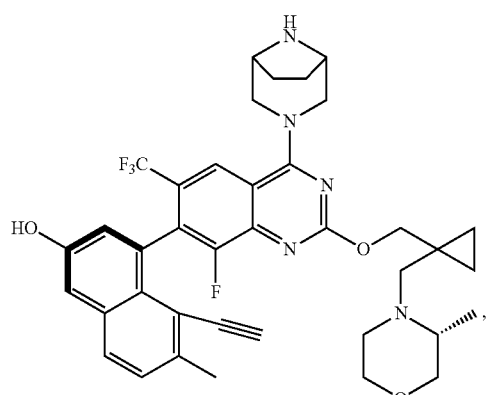
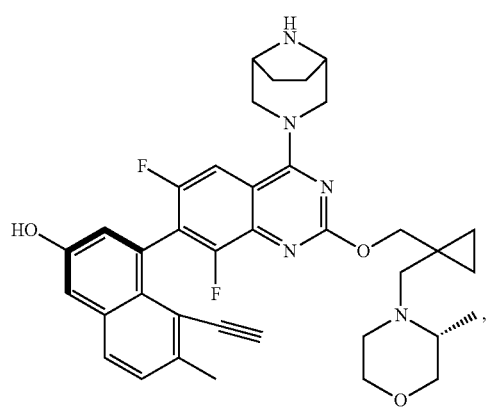
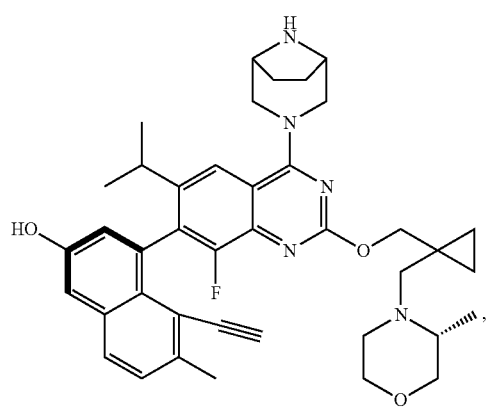
322
-continued
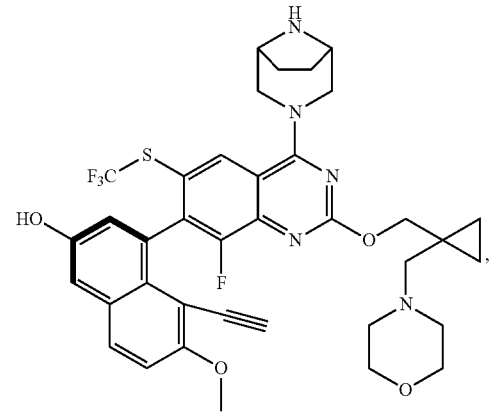
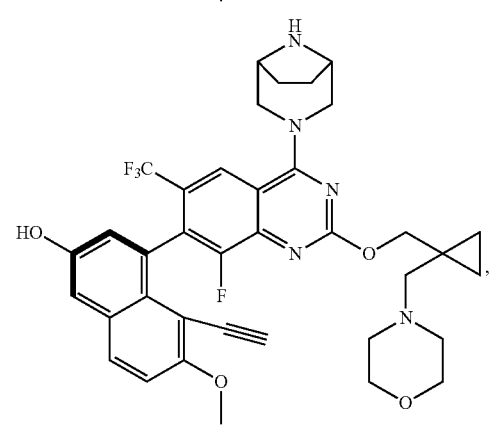
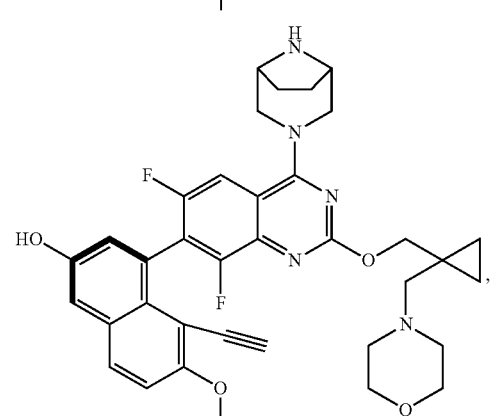
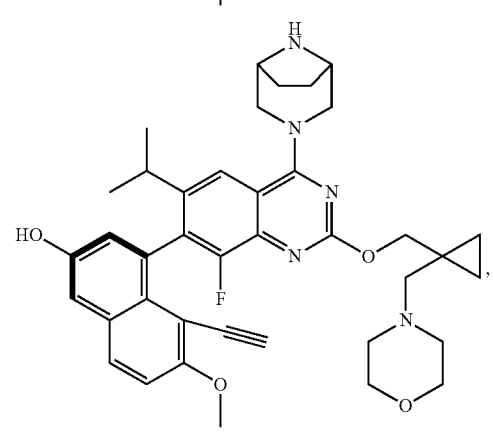

323
-continued
,
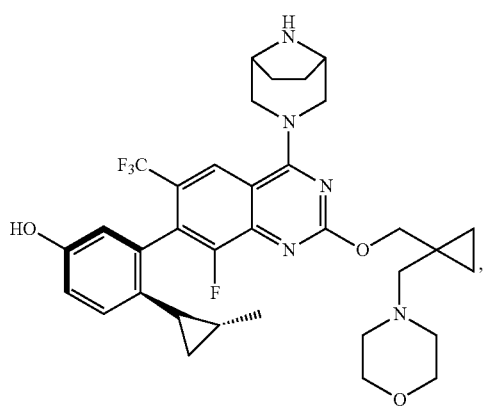
,
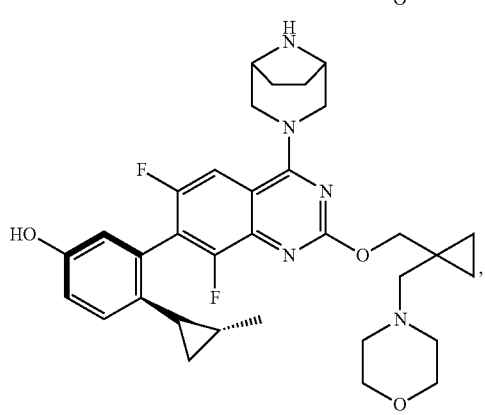
,
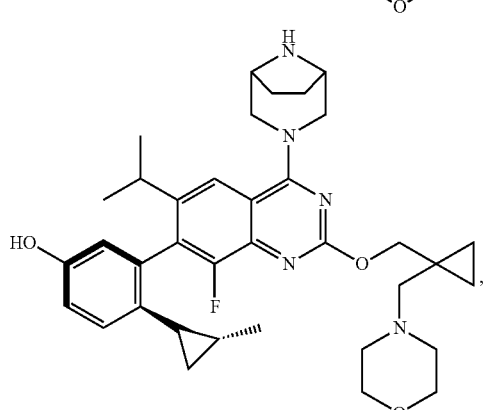
,
324
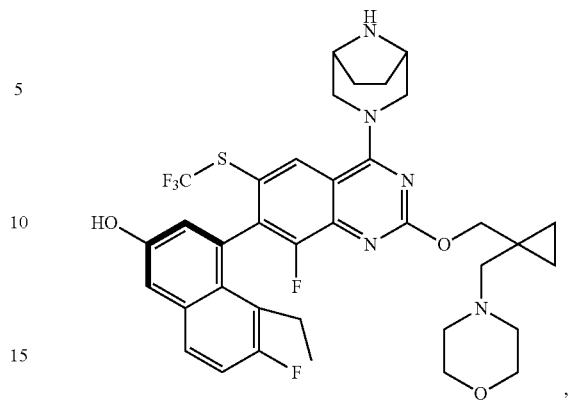
,
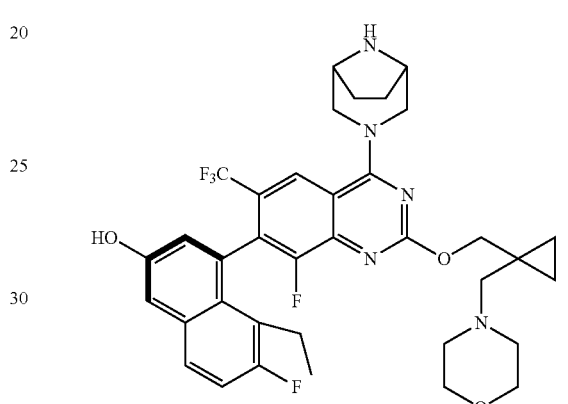
,
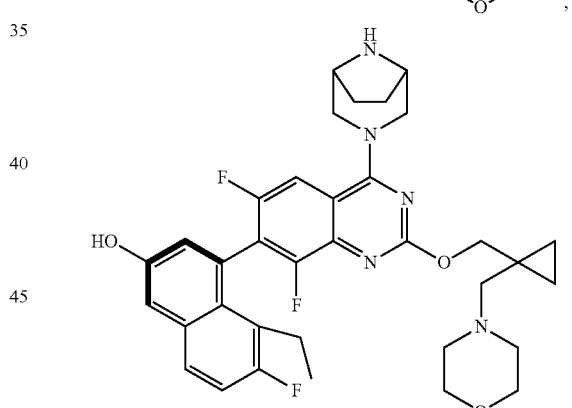
,
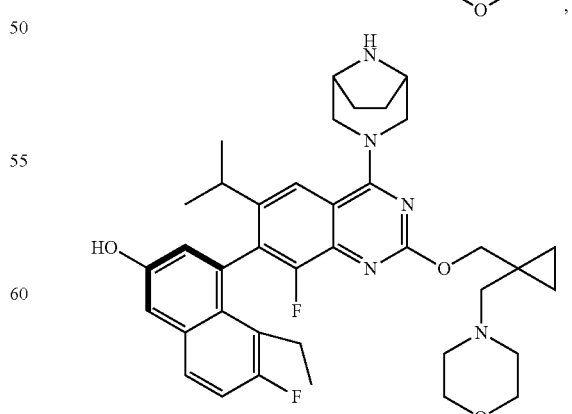
, 325
-continued
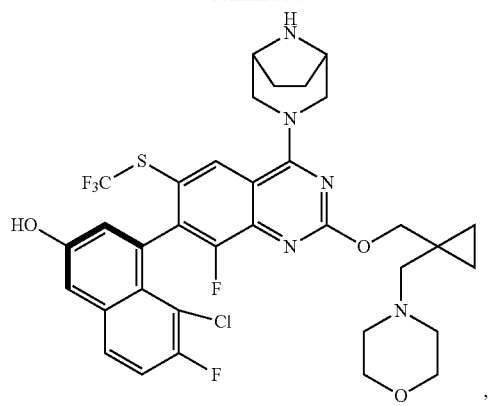
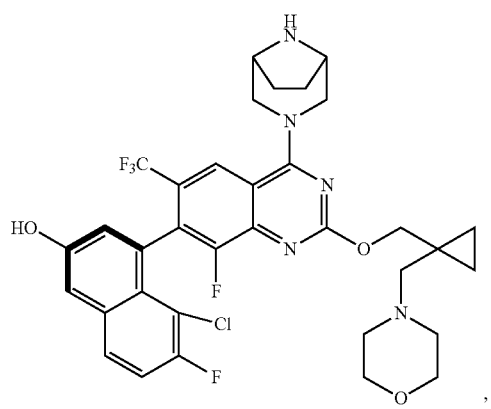
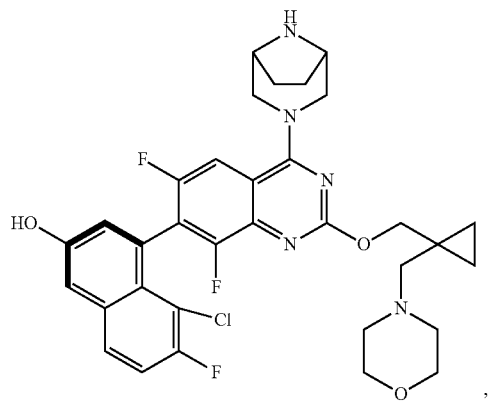
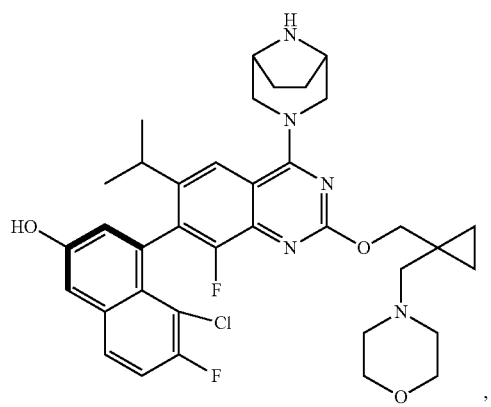
326
-continued
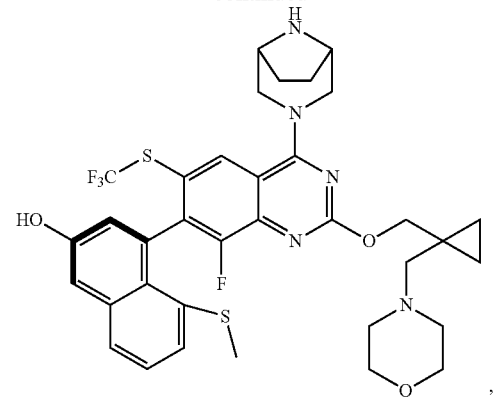
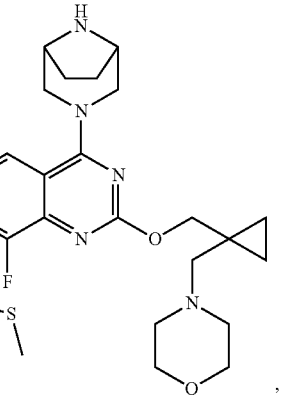
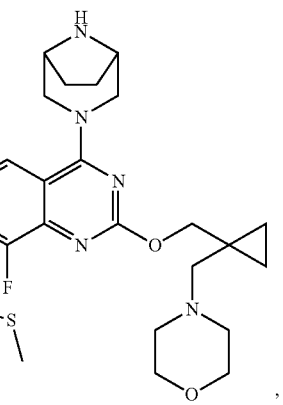

327
-continued
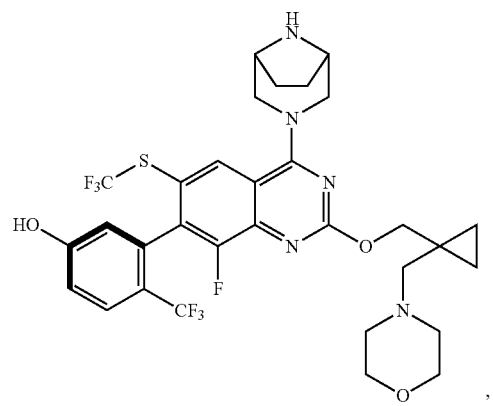
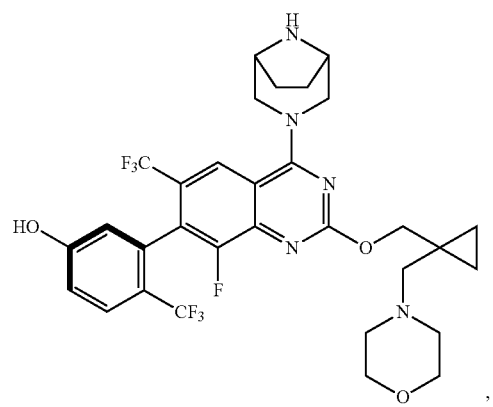
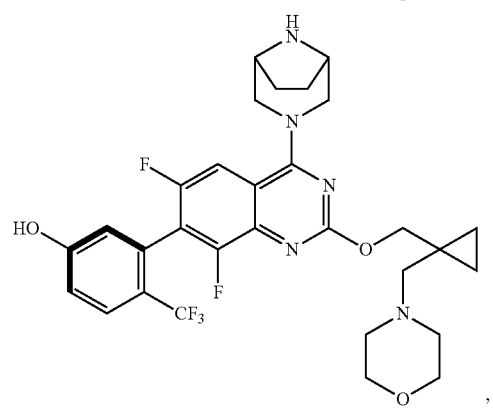
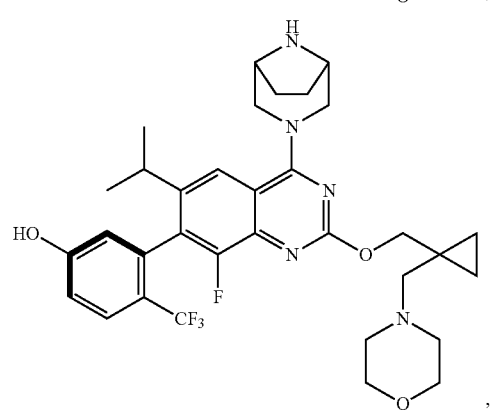
328
-continued
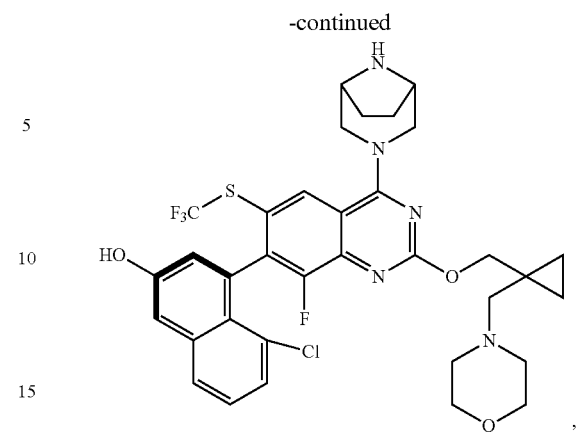
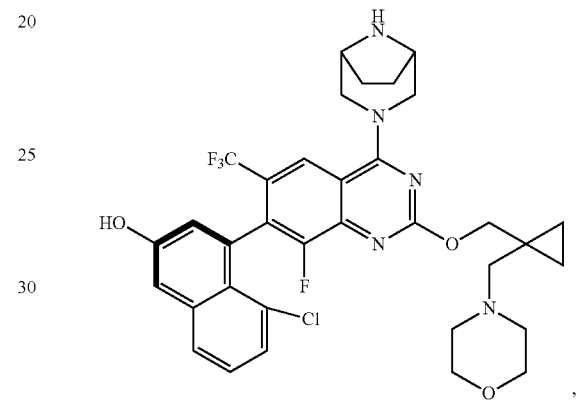
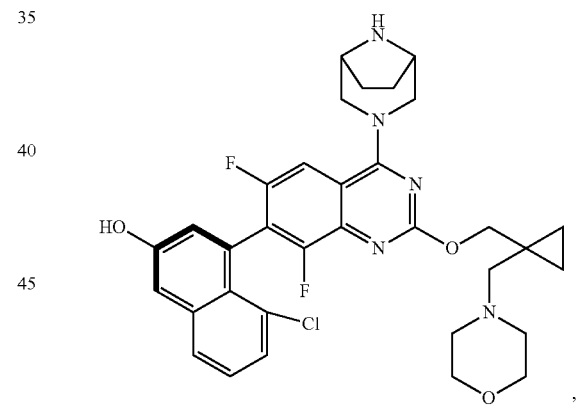
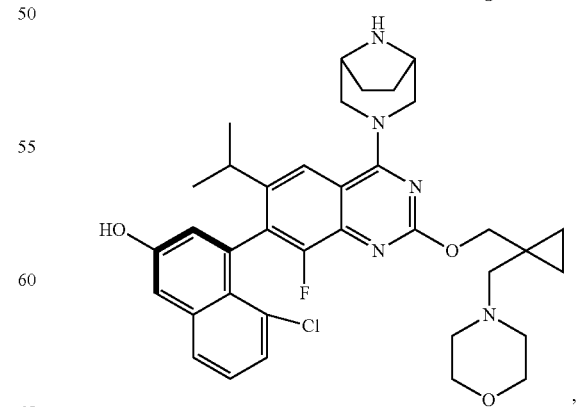

329
-continued
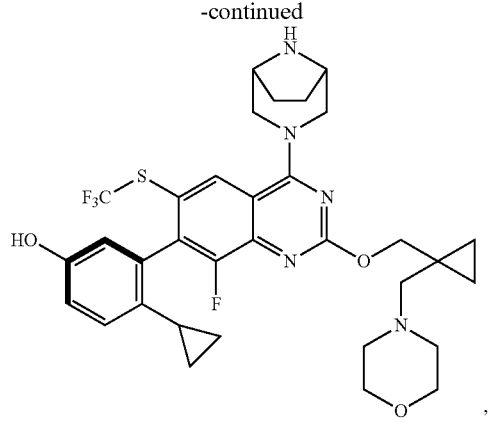
330
-continued
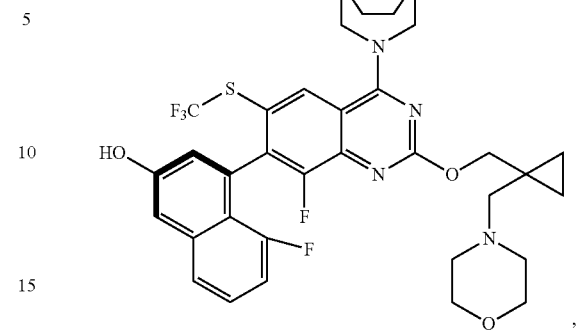
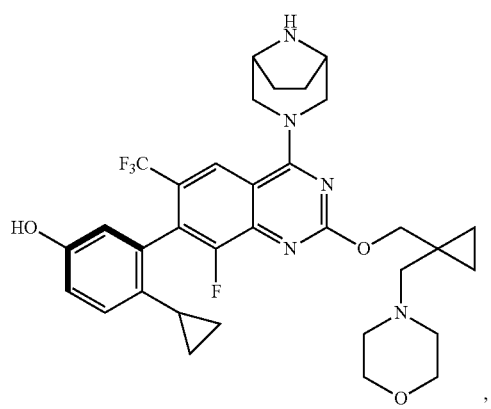
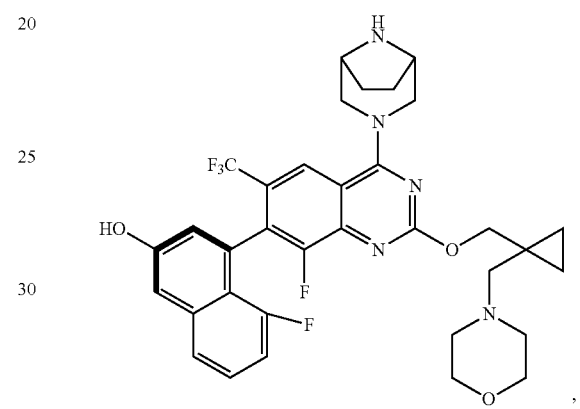

331
-continued
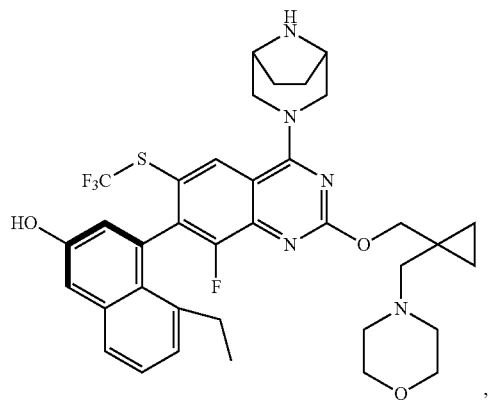
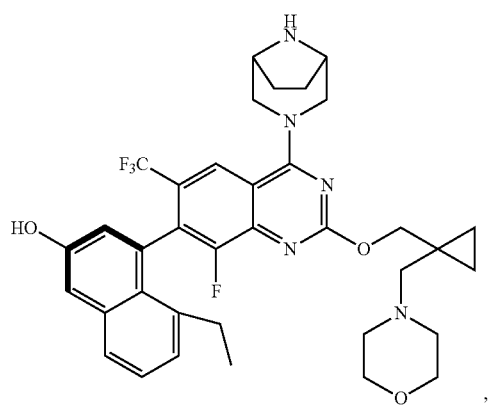
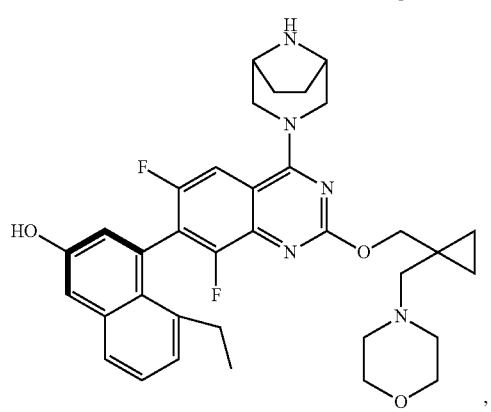
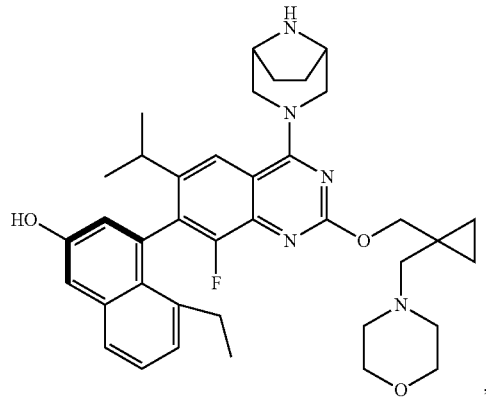
332
-continued
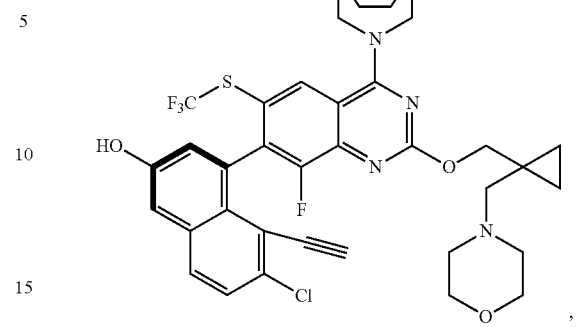
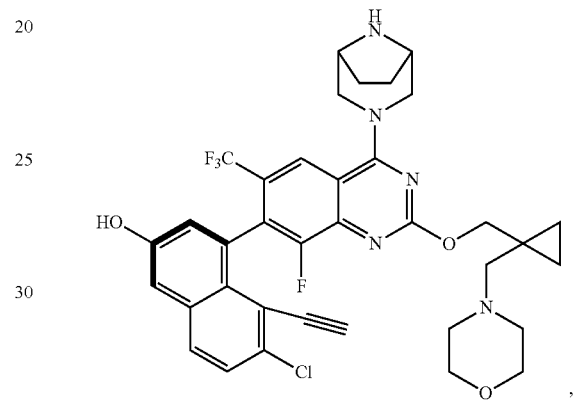

333
-continued
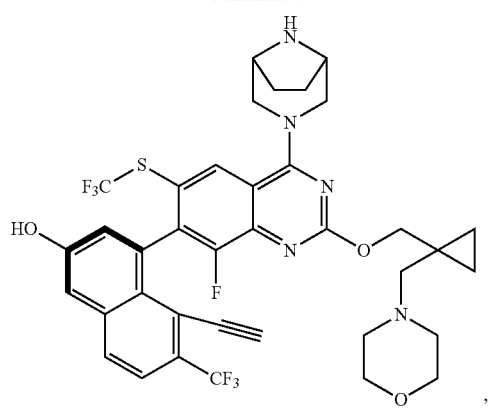
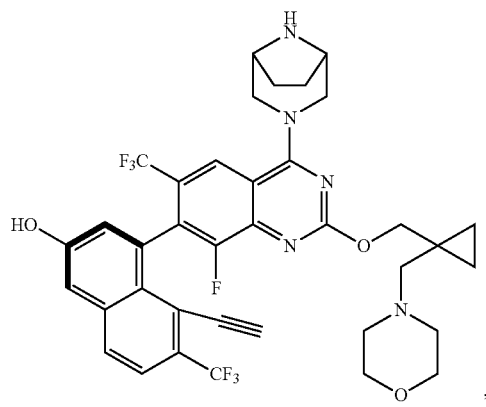
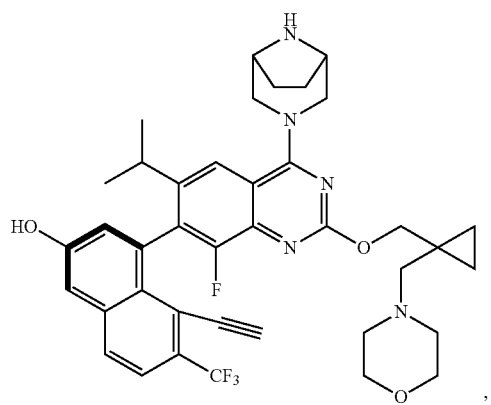
334
-continued
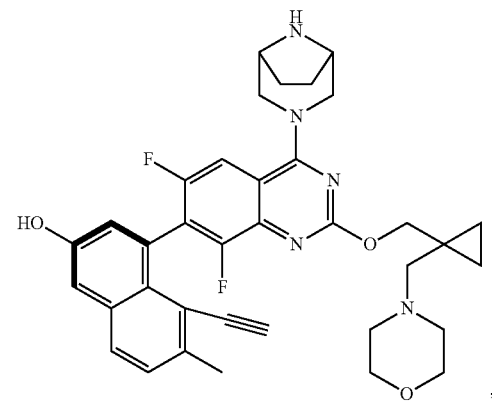
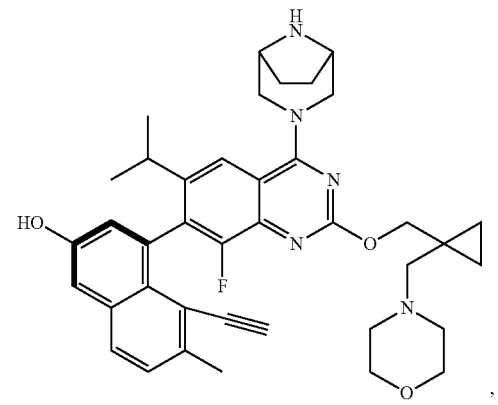

335
-continued
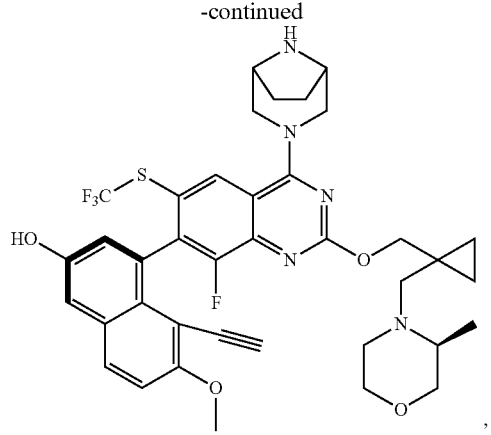
,
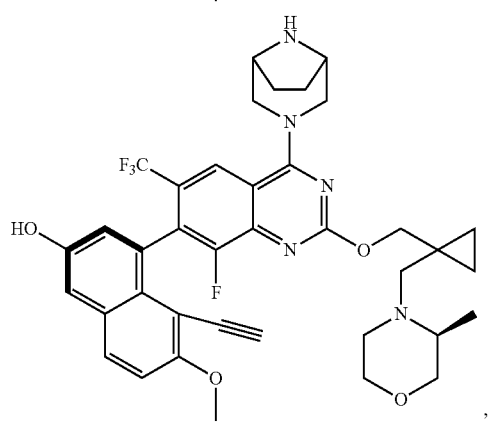
,
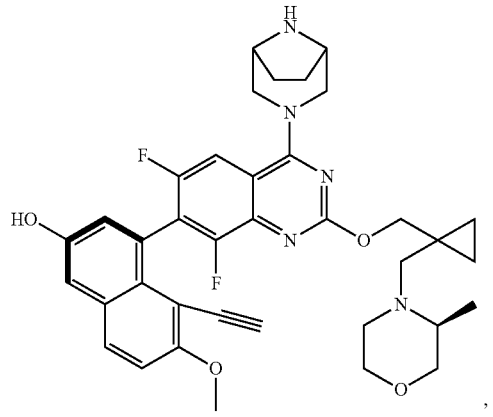
,
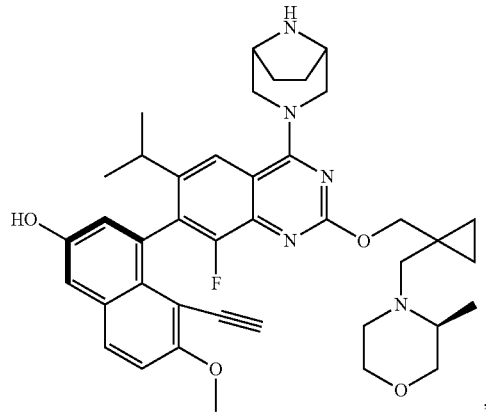
,
336
-continued
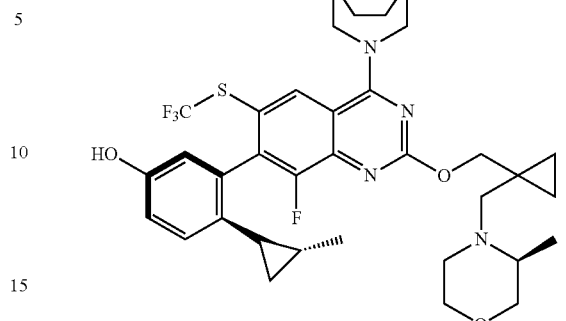
,
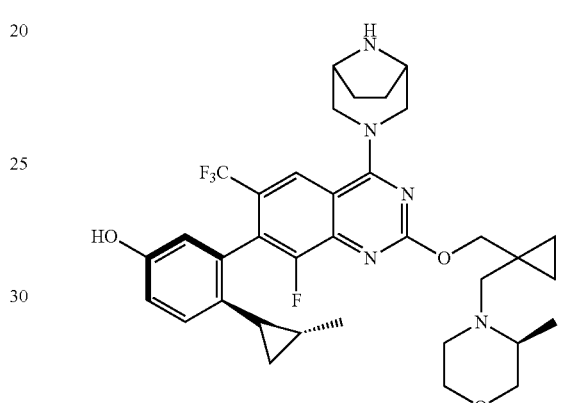
,
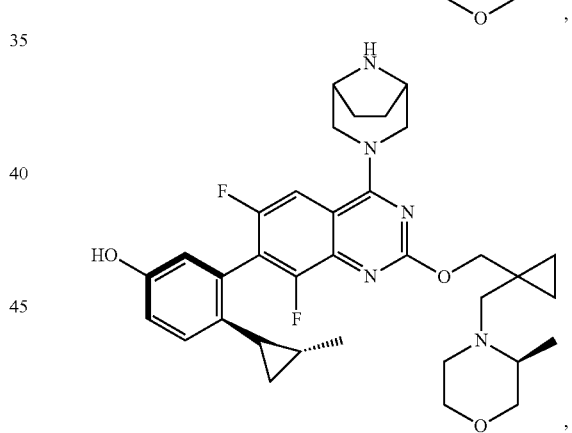
,
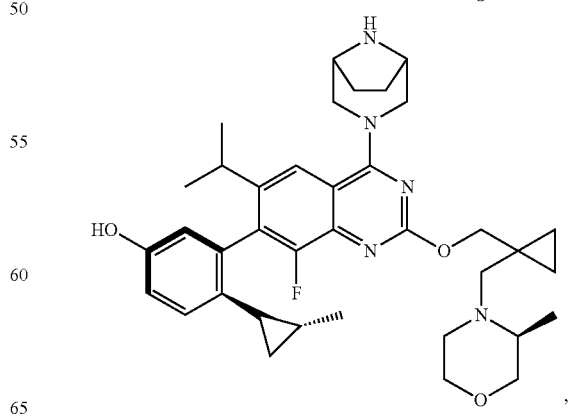
, 337
-continued
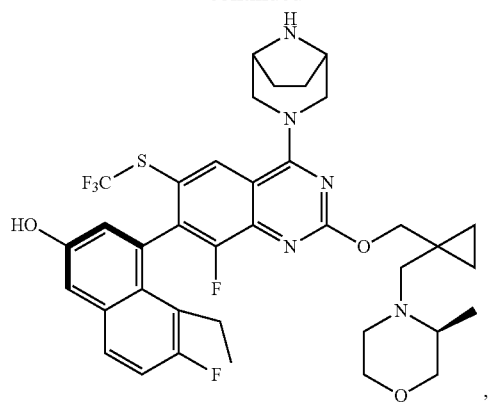
338
-continued
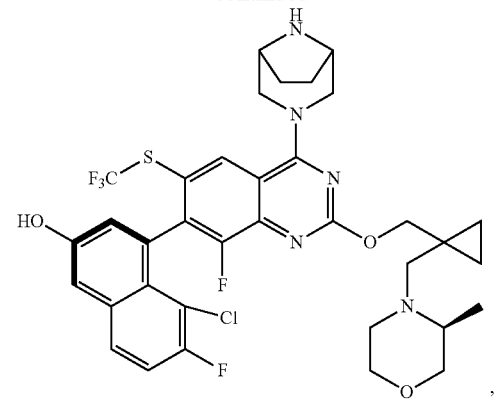
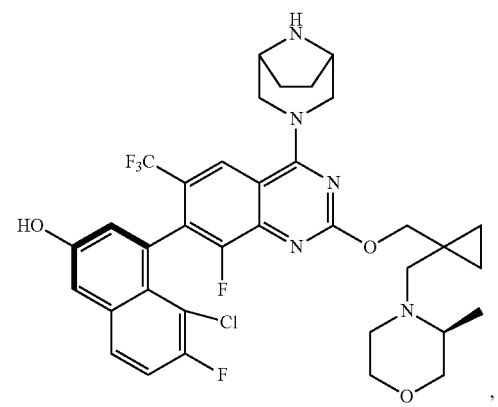
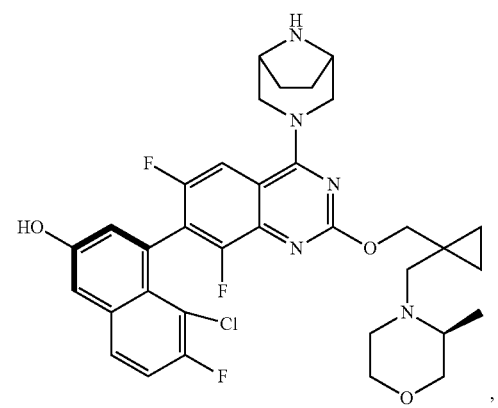
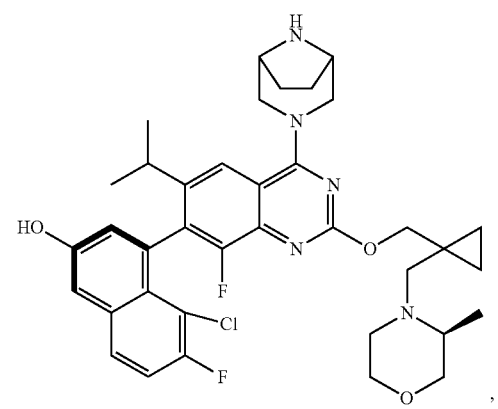

339
-continued
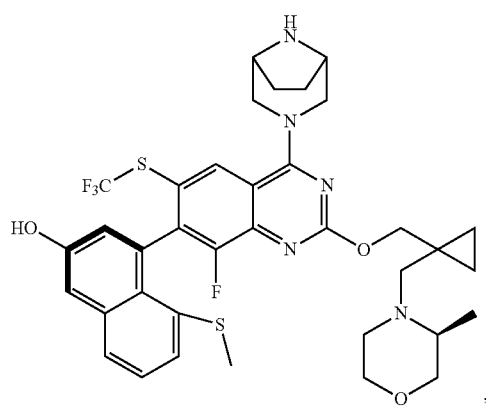
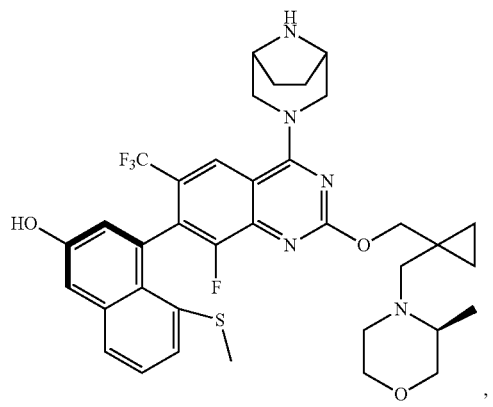
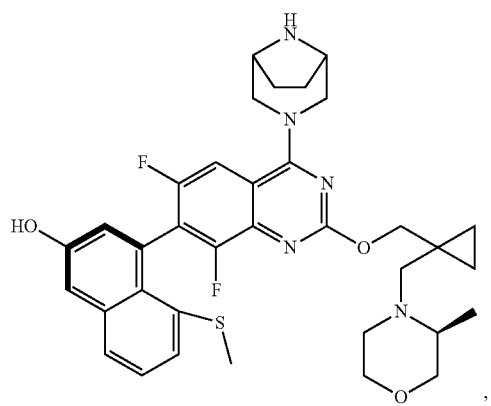
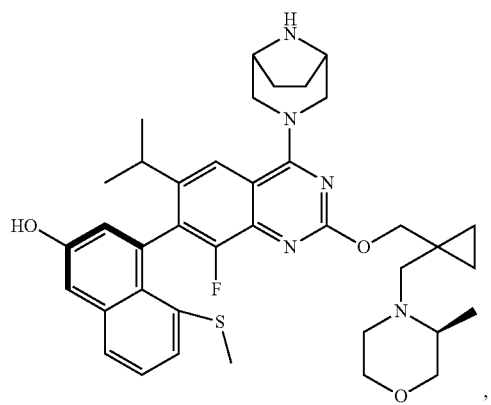
340
-continued
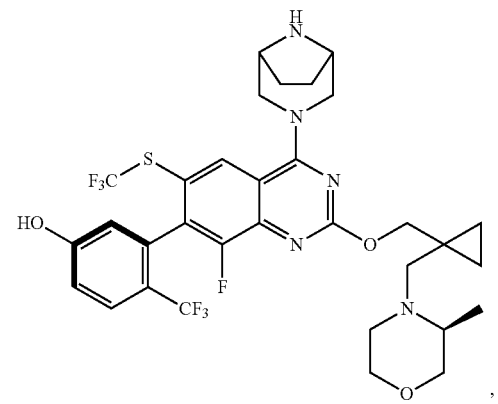
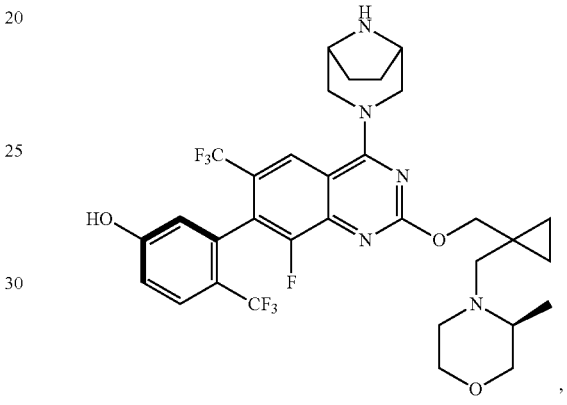
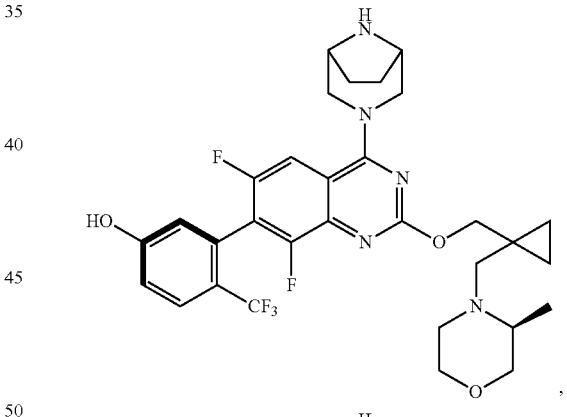
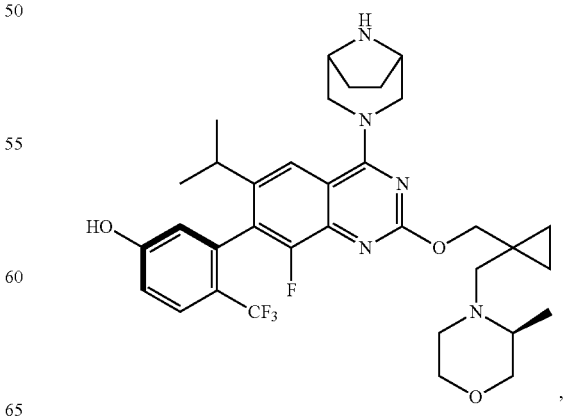

341
-continued
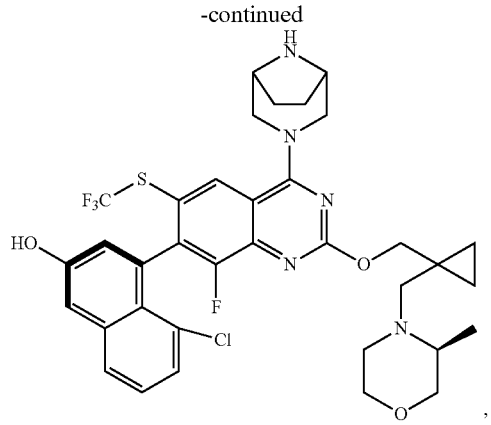
,
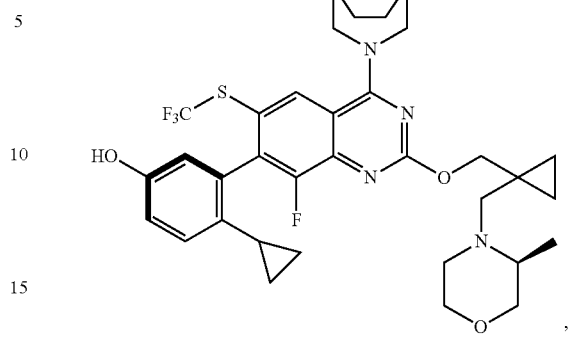
,
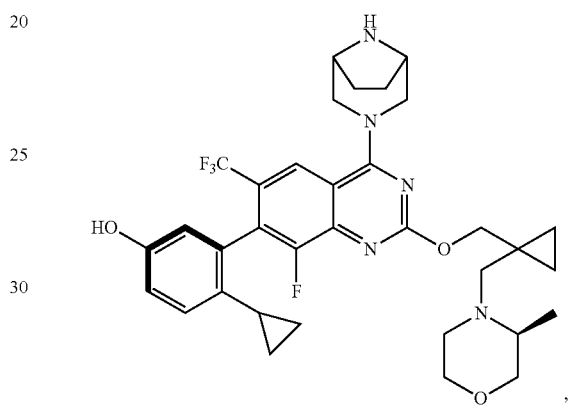
,
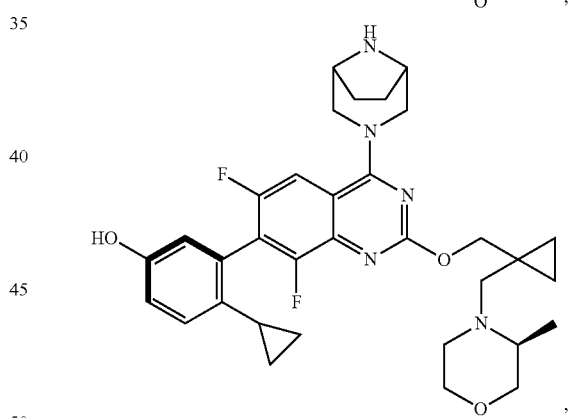
,

, 343
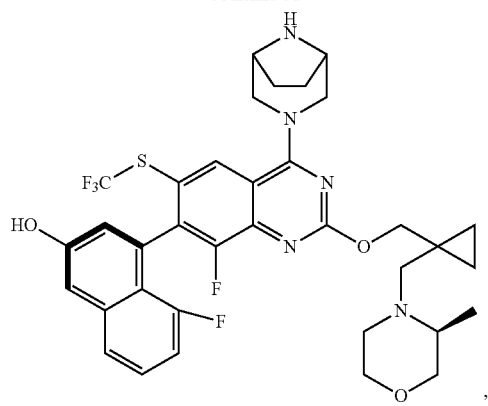
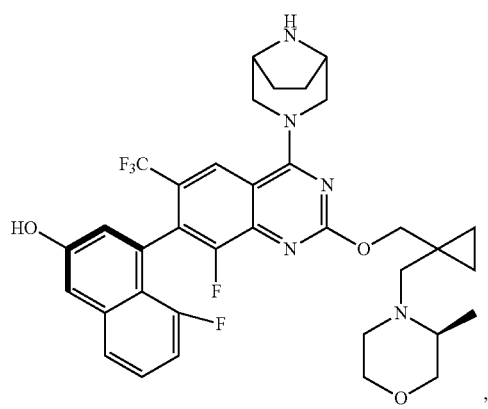
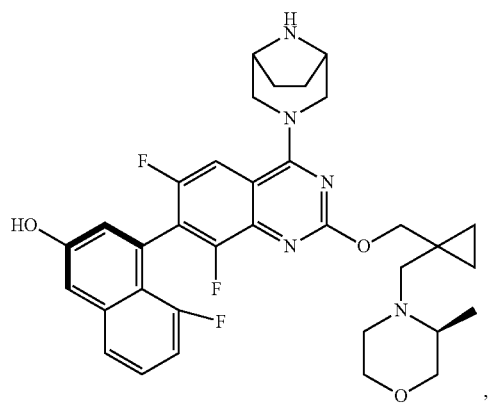
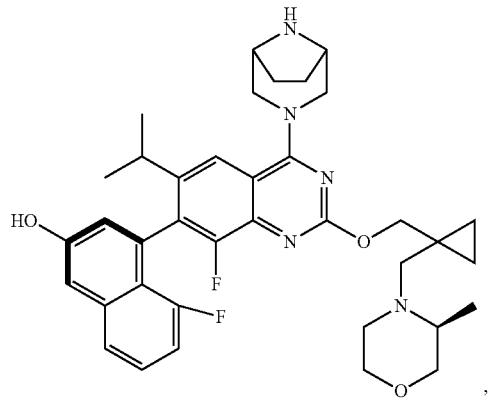
344
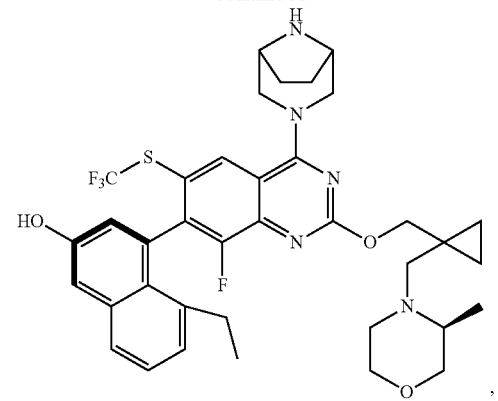
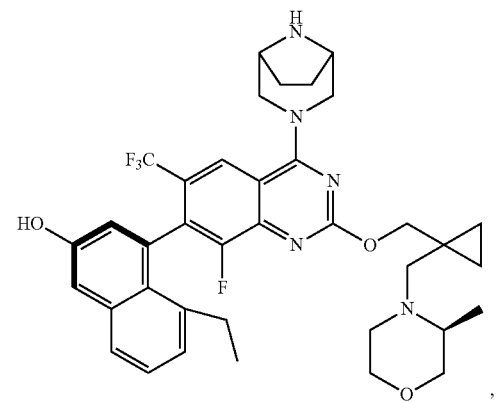
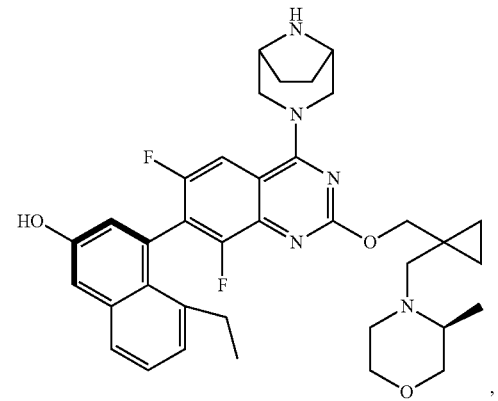
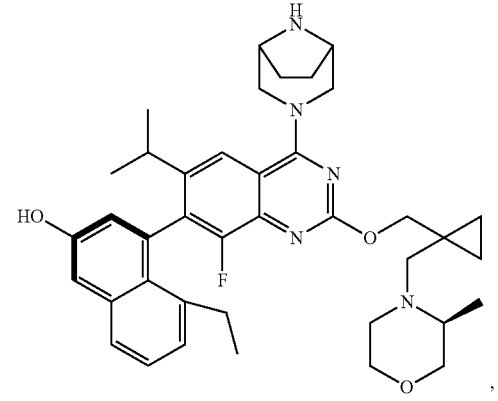

345
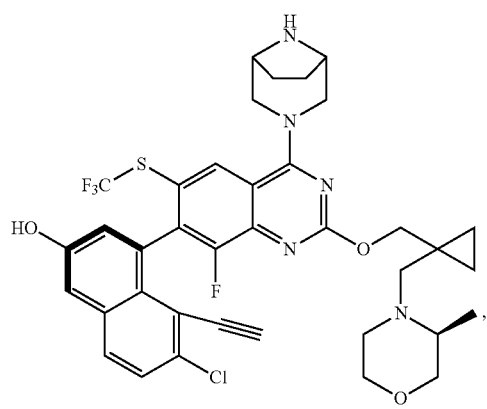
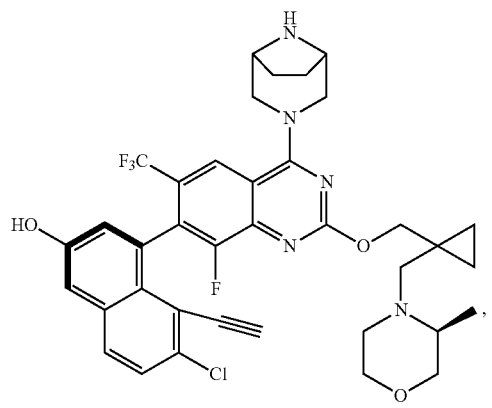
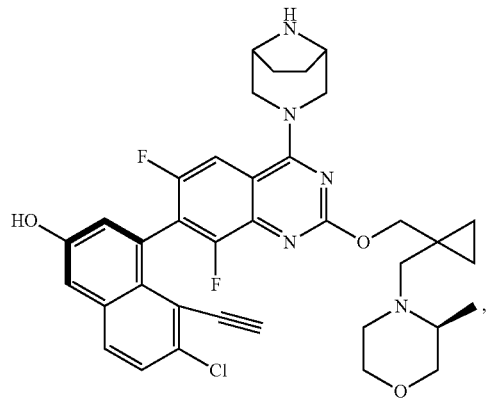
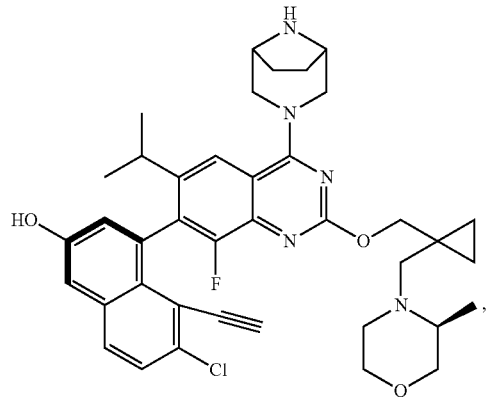
346
-continued
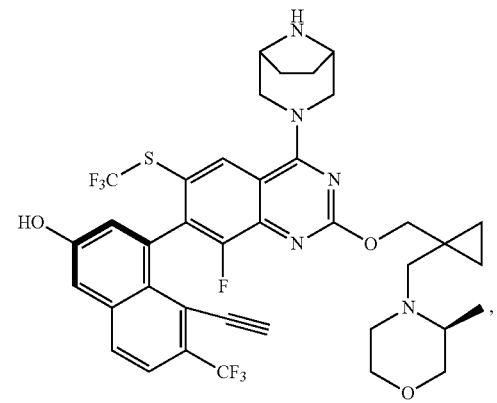
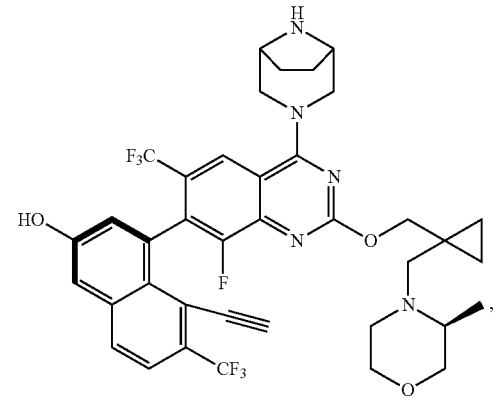
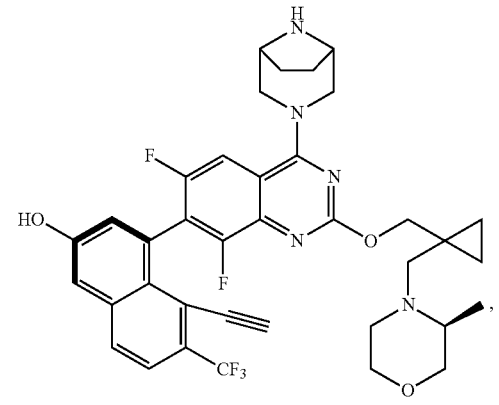
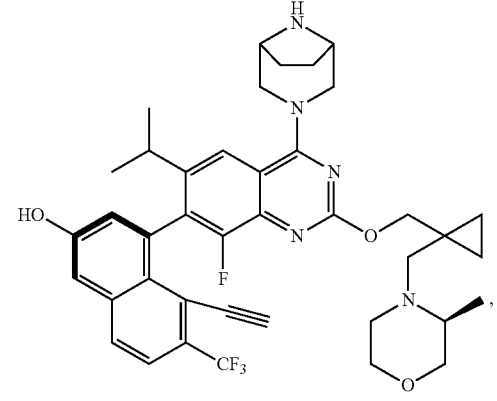

347
-continued

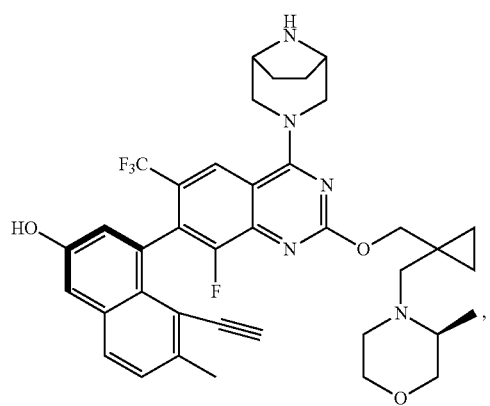
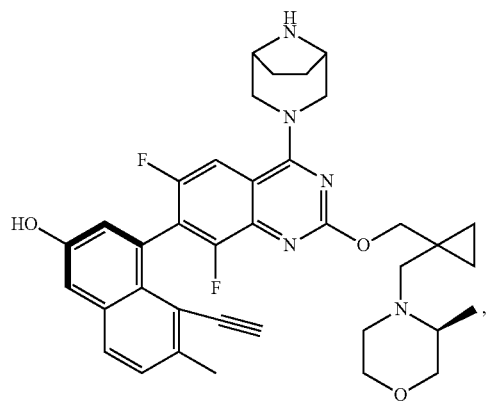
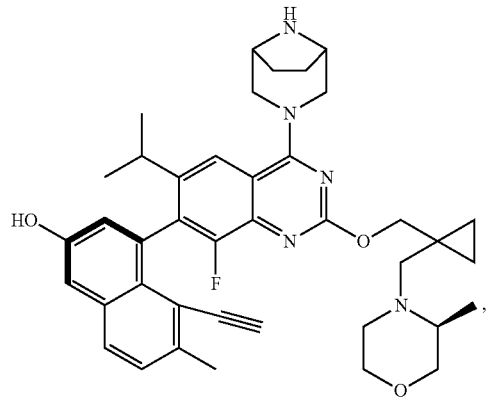
348
-continued
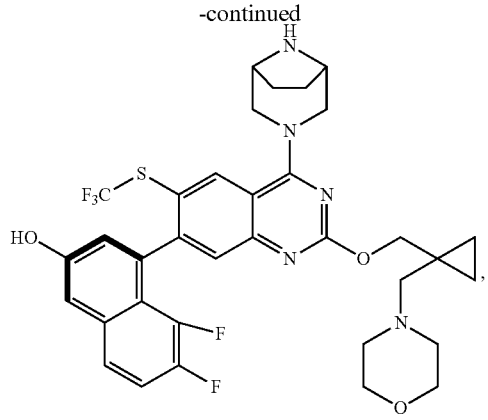
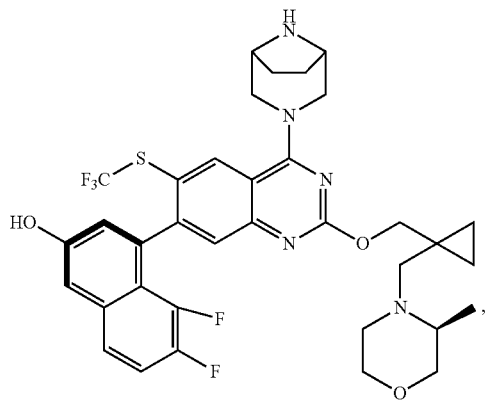
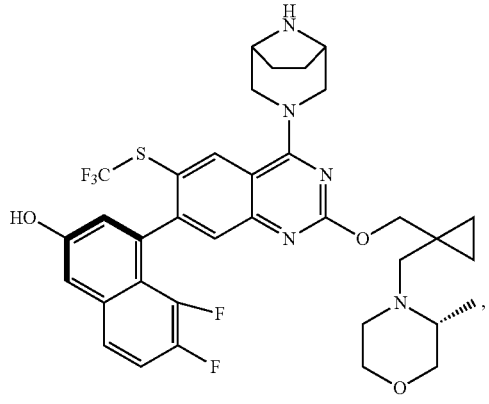
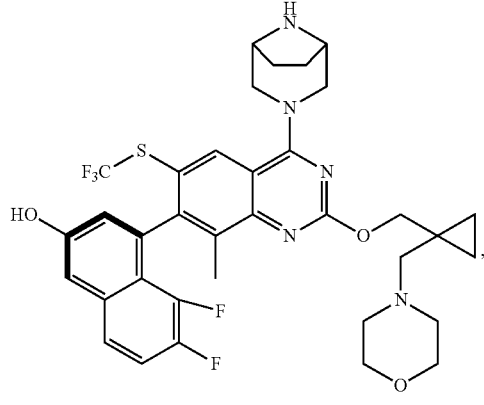

349
-continued
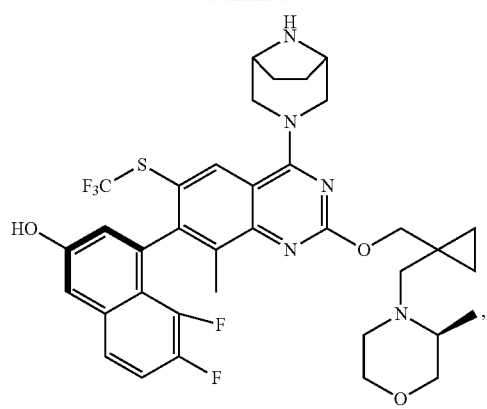
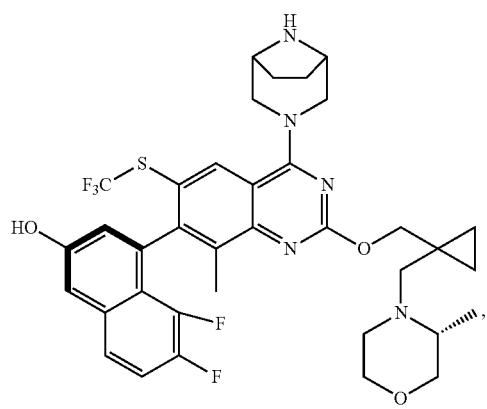
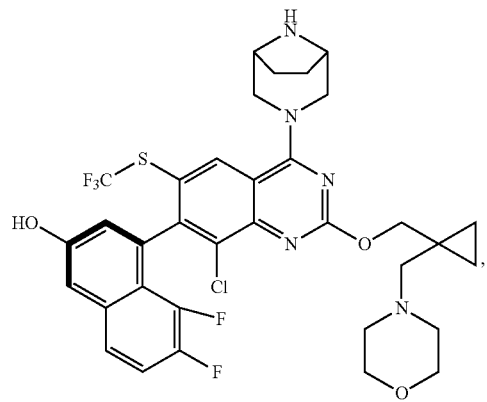
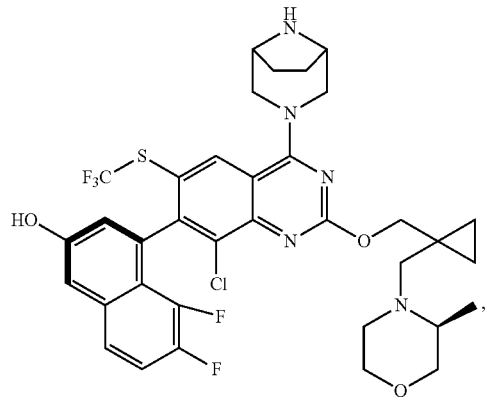
350
-continued
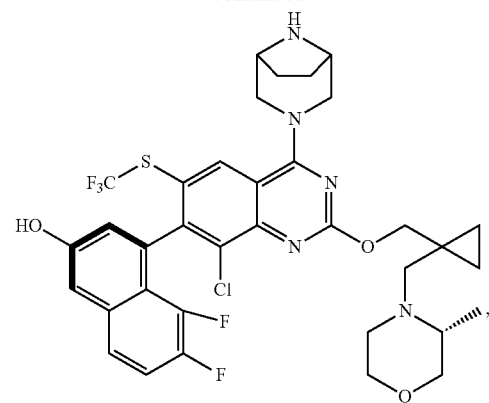
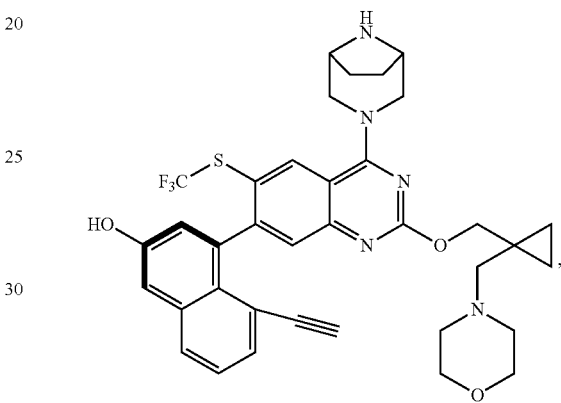
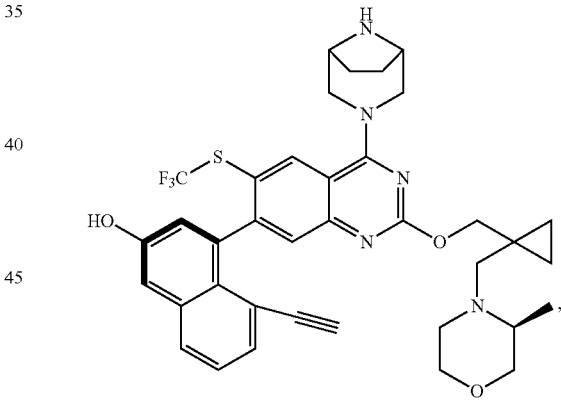
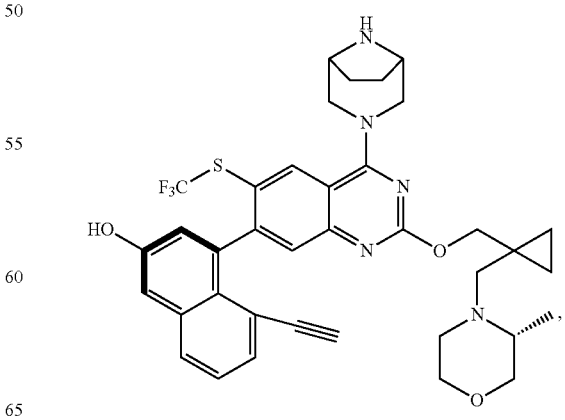

351
-continued
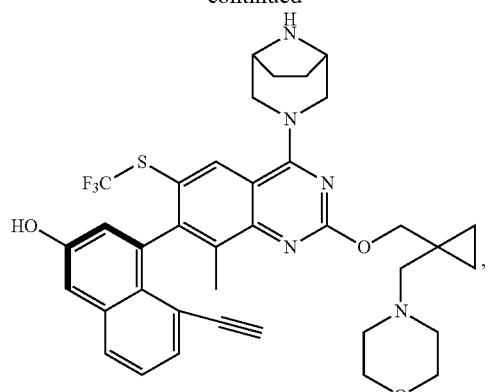
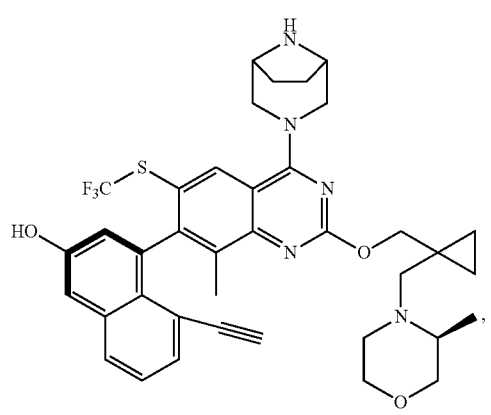
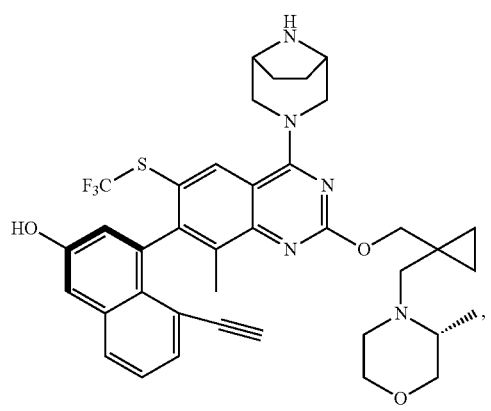
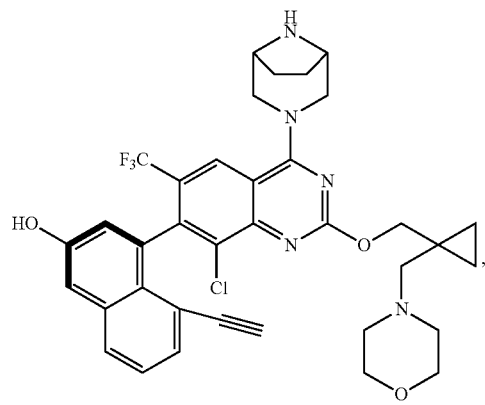
352
-continued
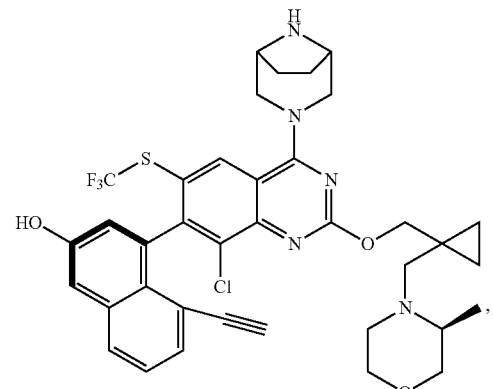
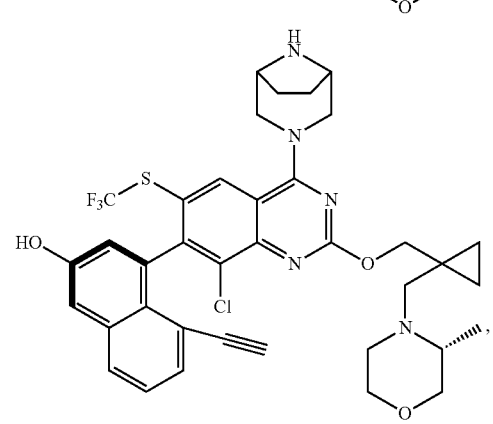
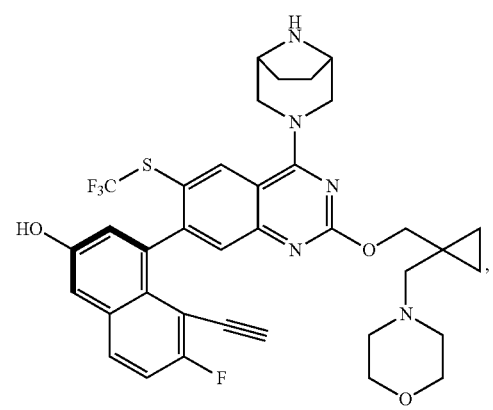
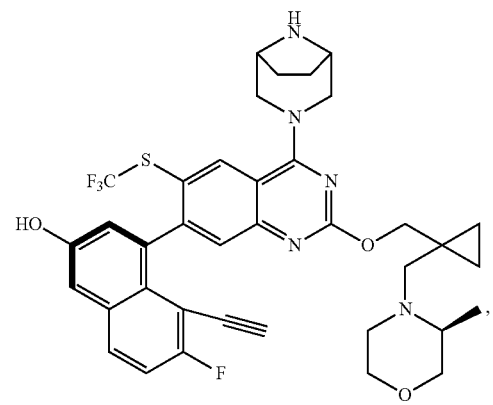

353
-continued
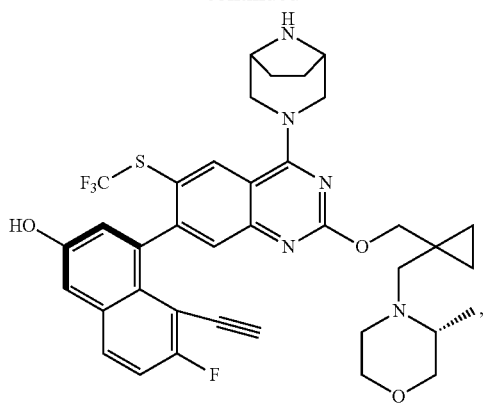
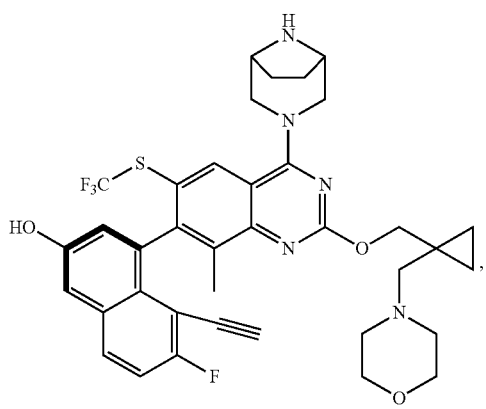
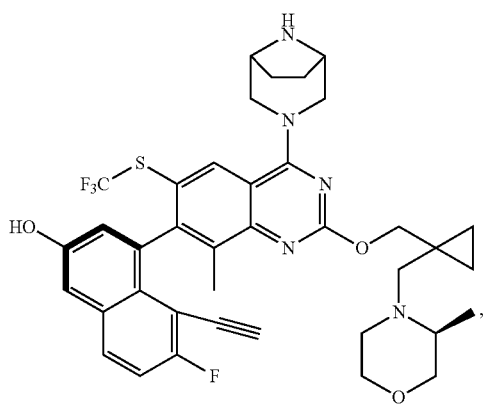
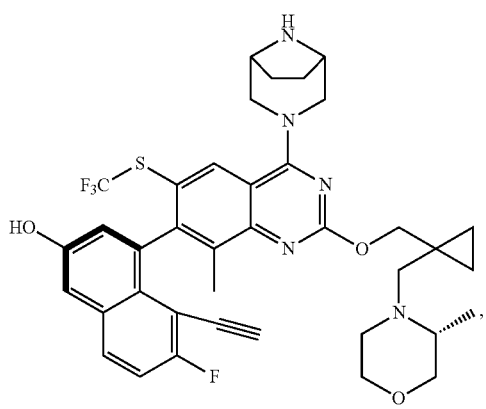
354
-continued
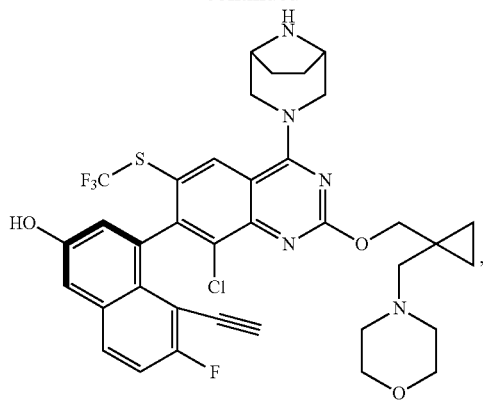
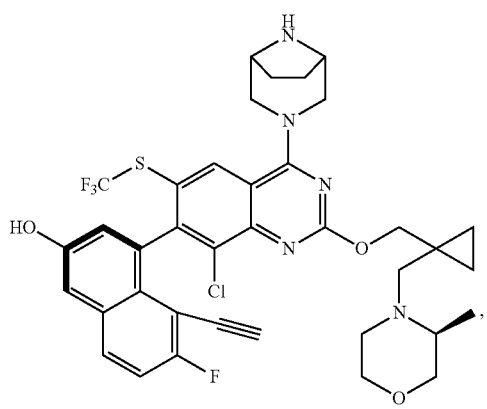
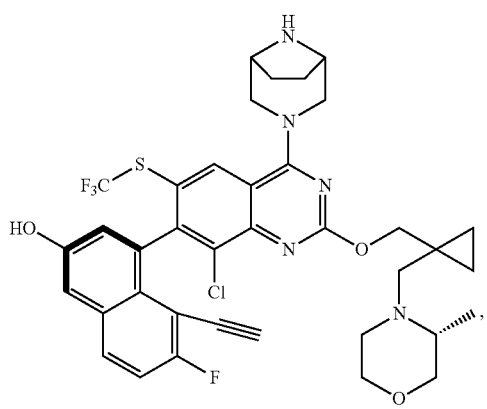
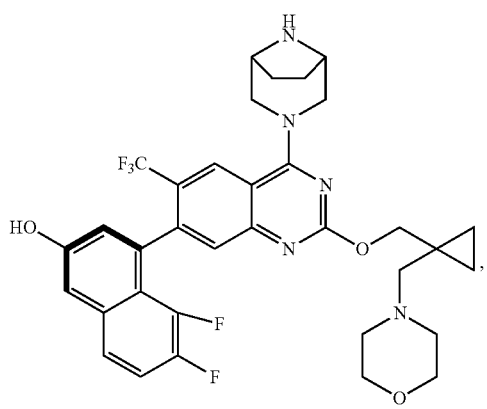

355
-continued
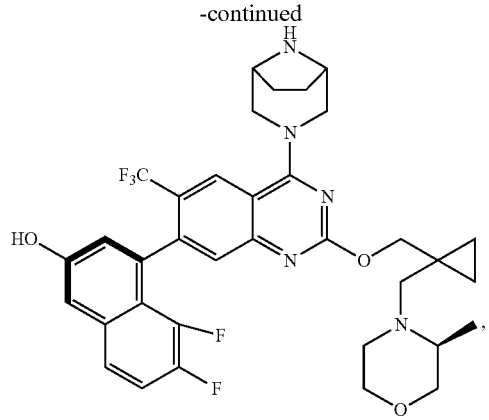
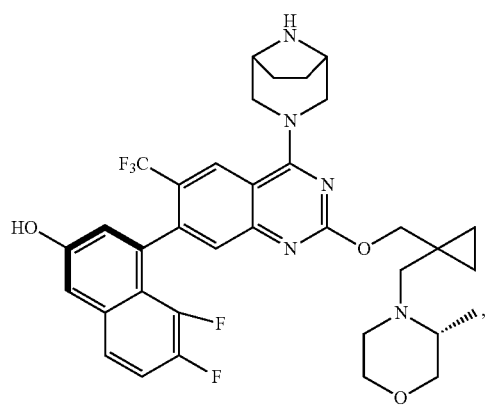
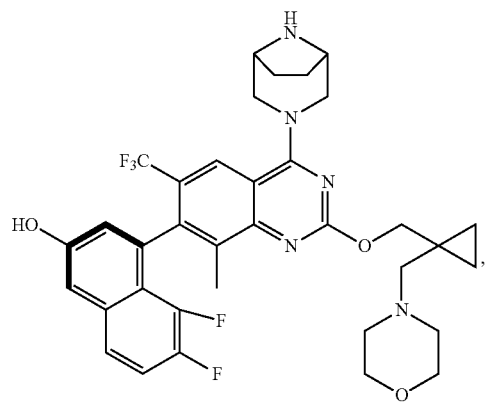
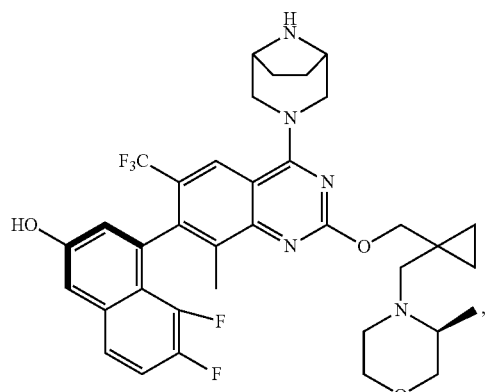
356
-continued
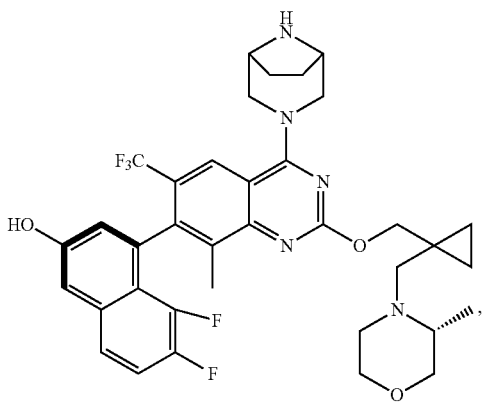
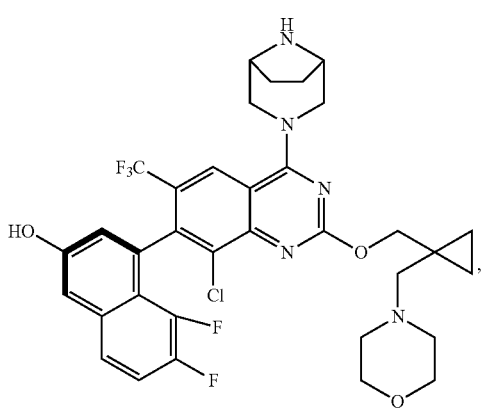
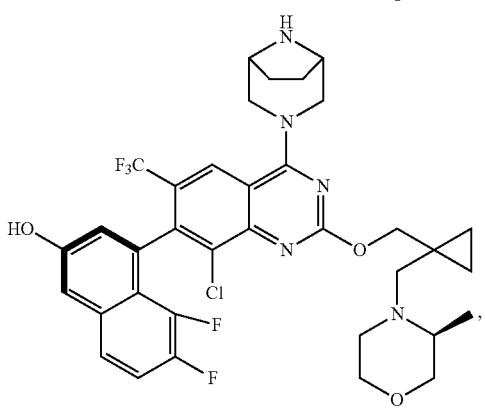
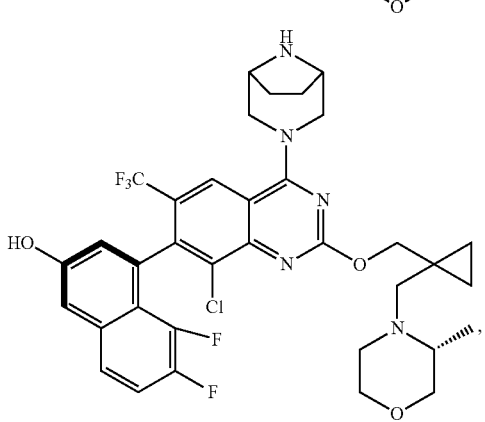

357
-continued
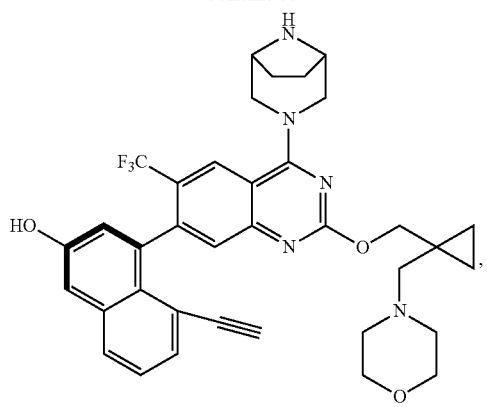
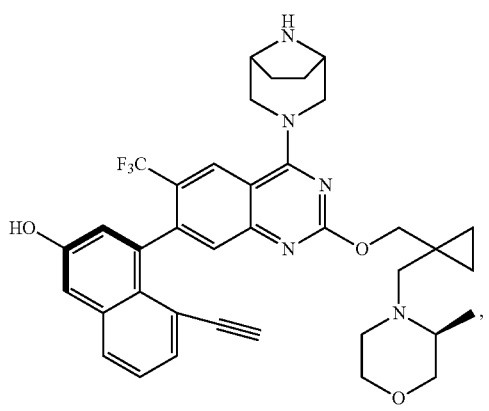
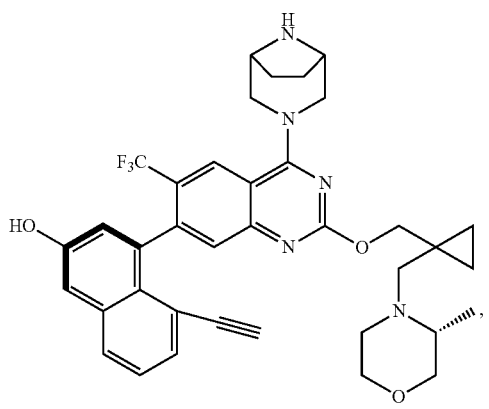
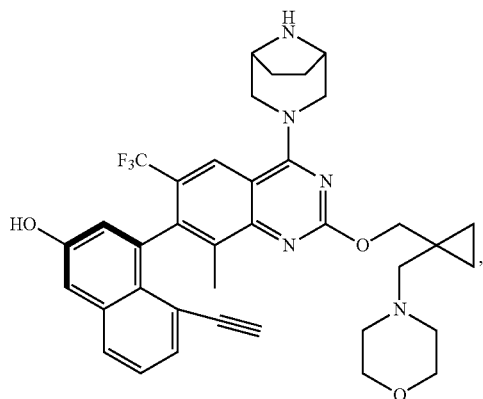
358
-continued
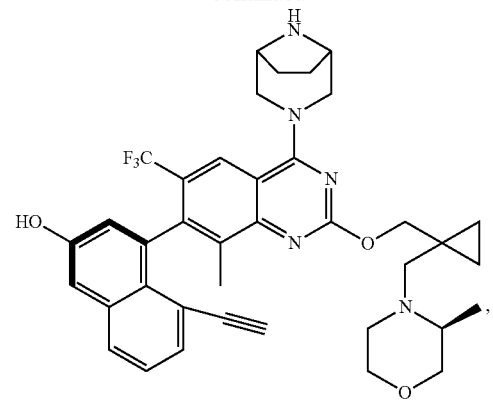
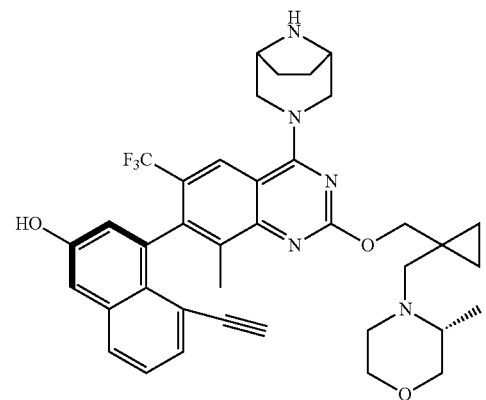
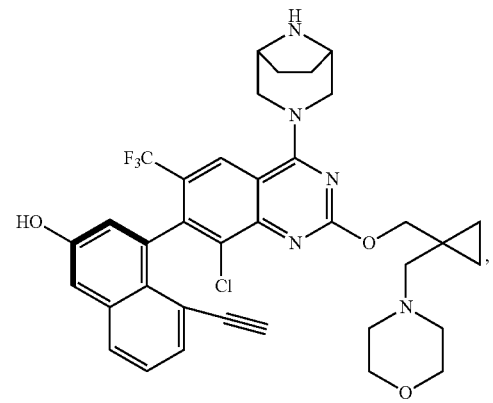
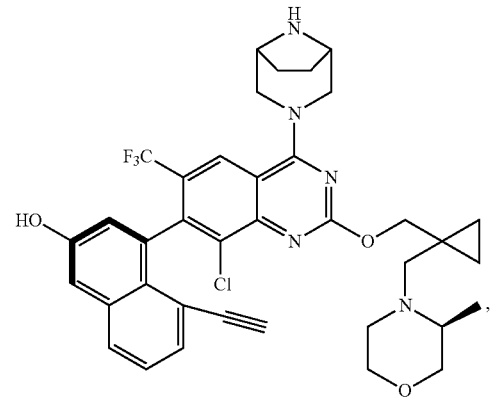

359
-continued
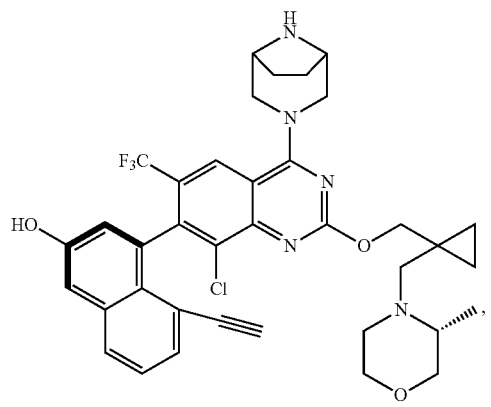
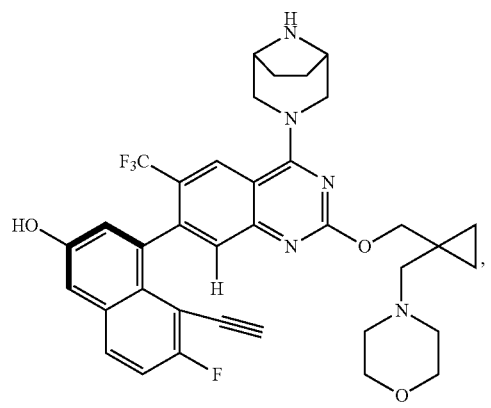
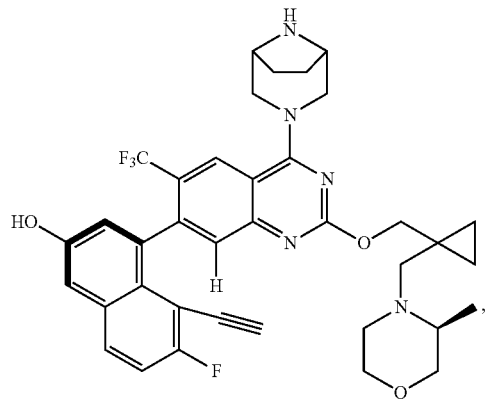
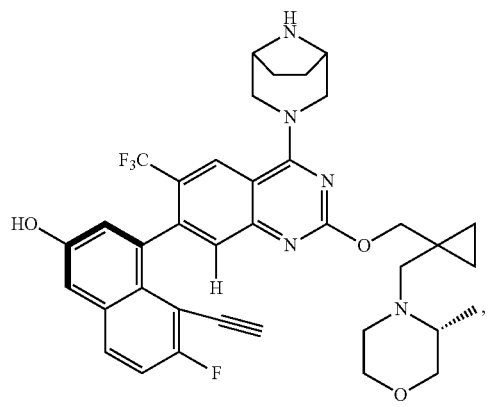
360
-continued
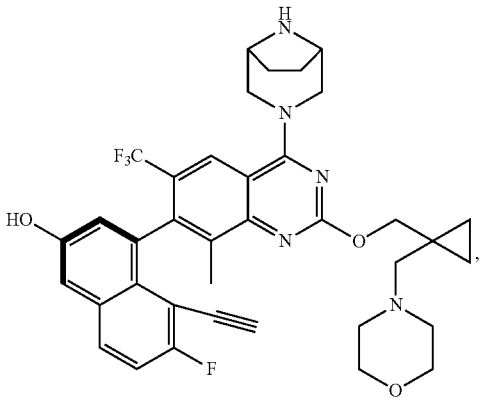
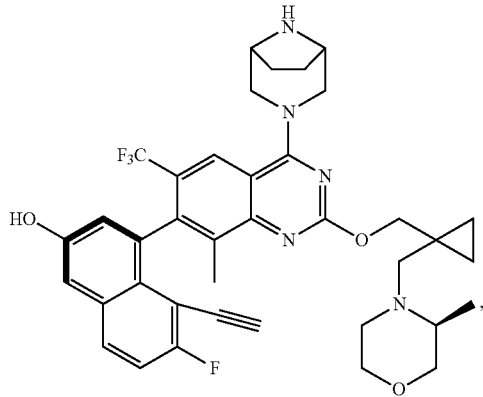

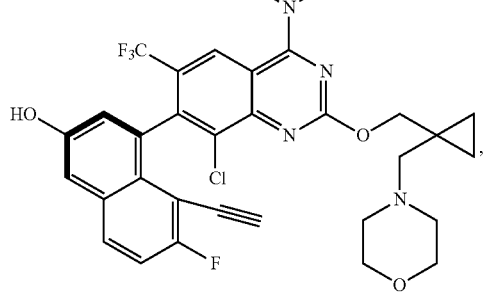

361
-continued
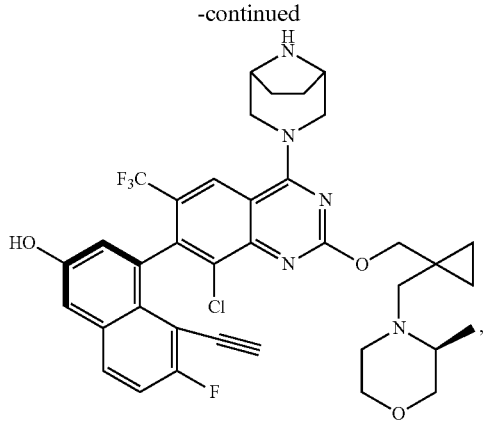
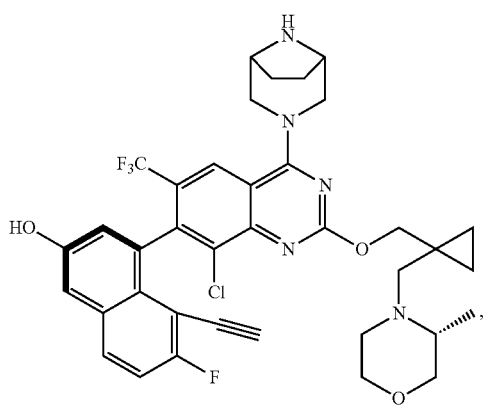
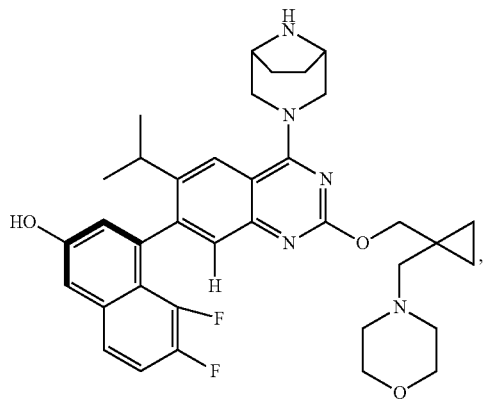
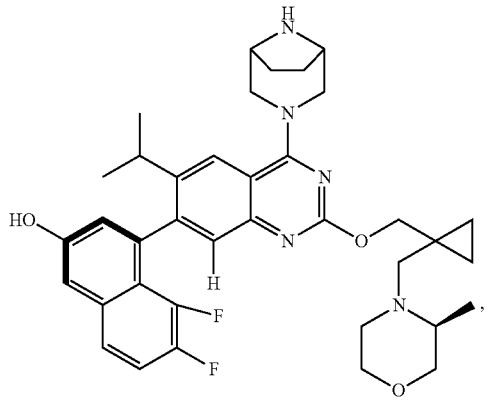
362
-continued
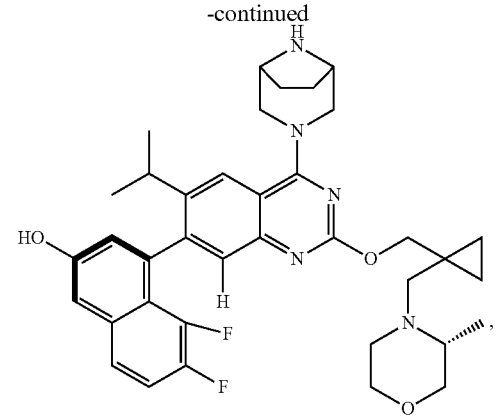
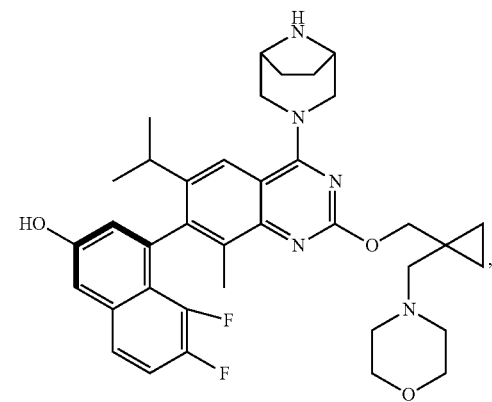
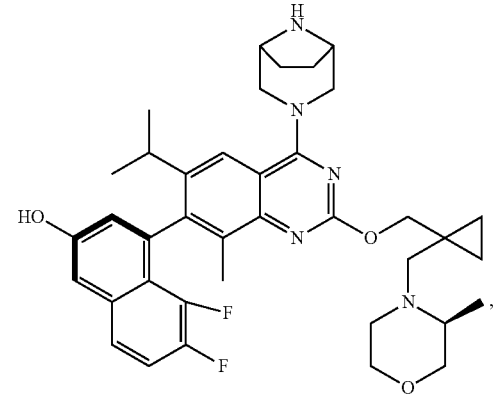
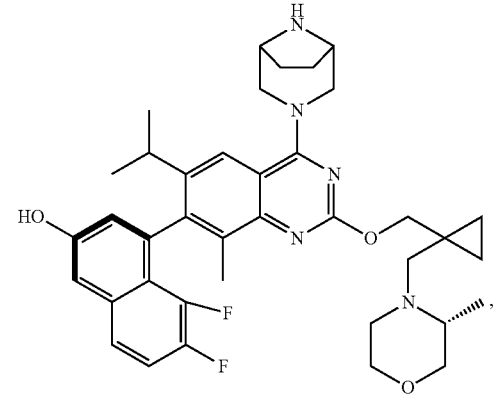

363
-continued
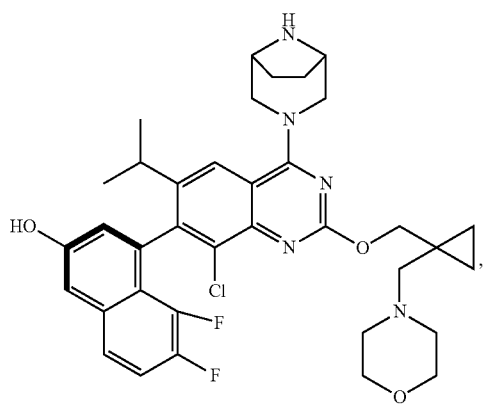
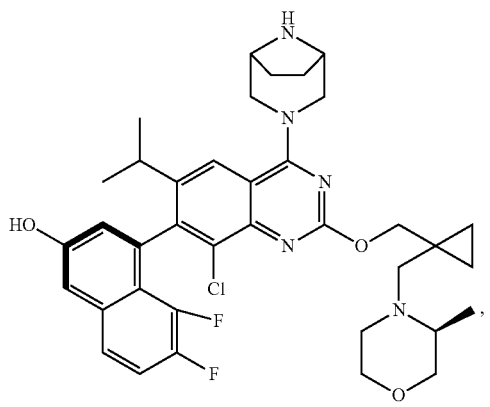
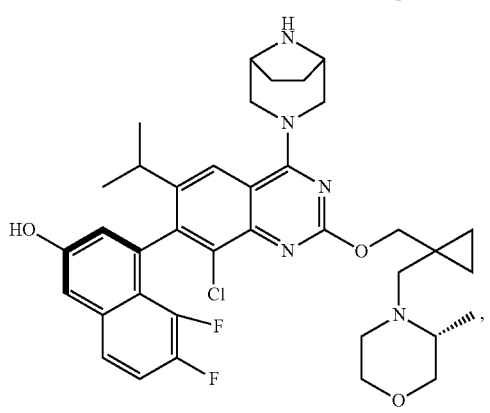
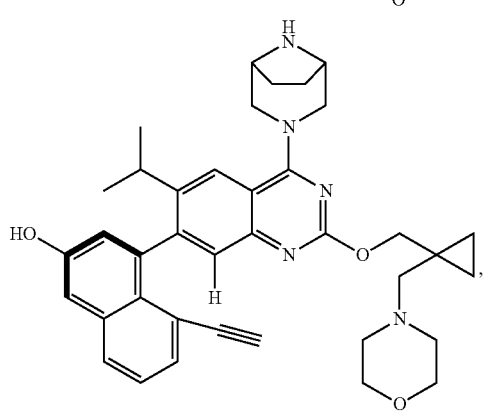
364
-continued
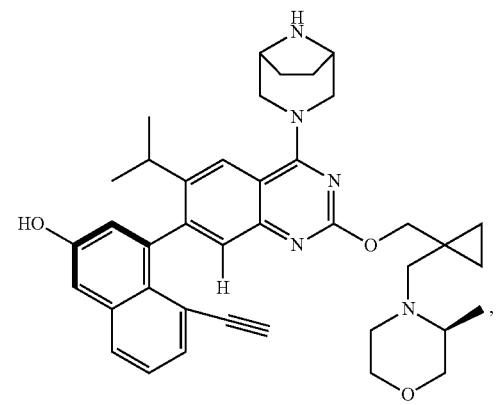
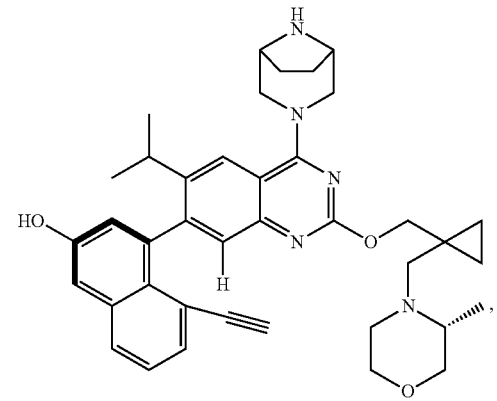
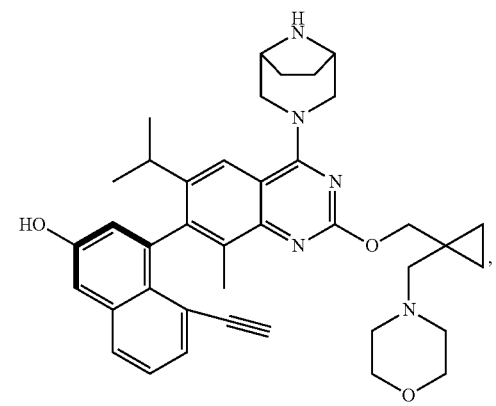
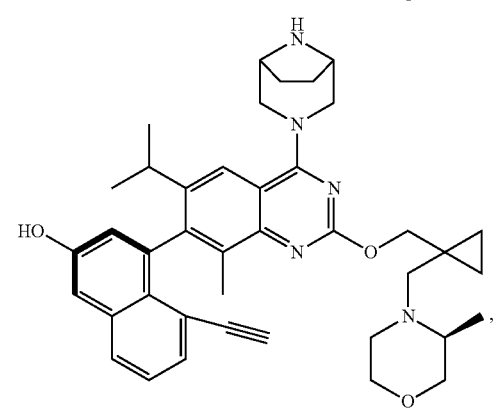

365
-continued
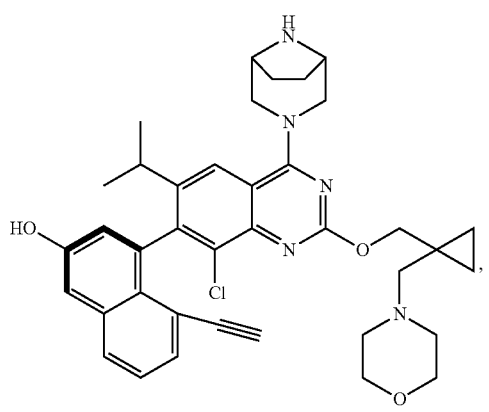
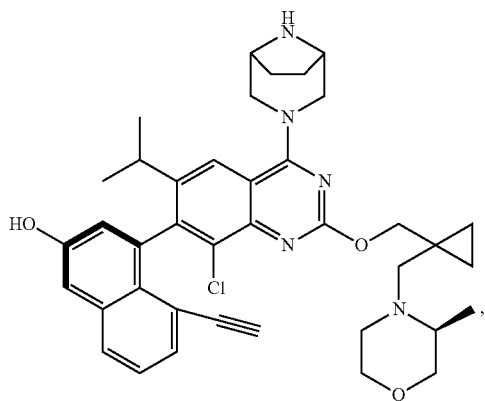
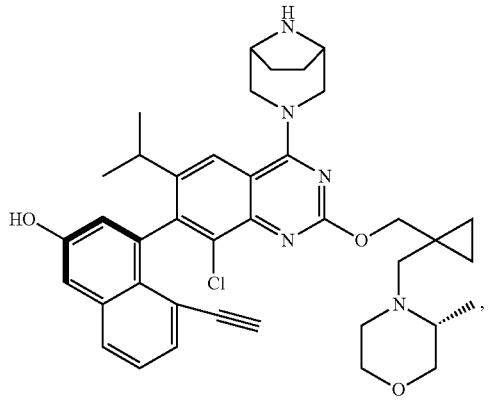
366

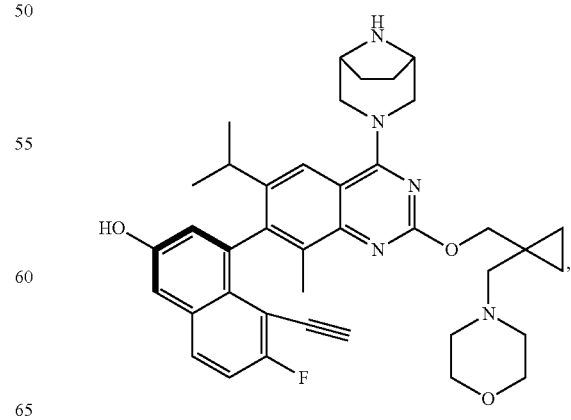

367
-continued
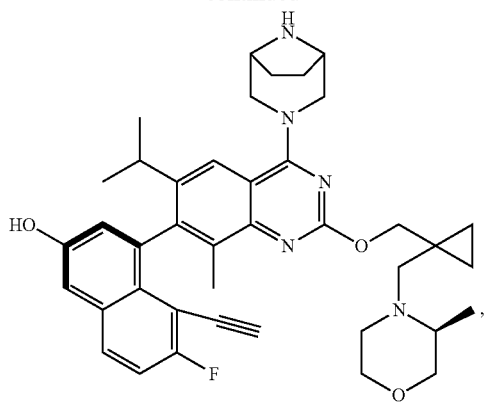
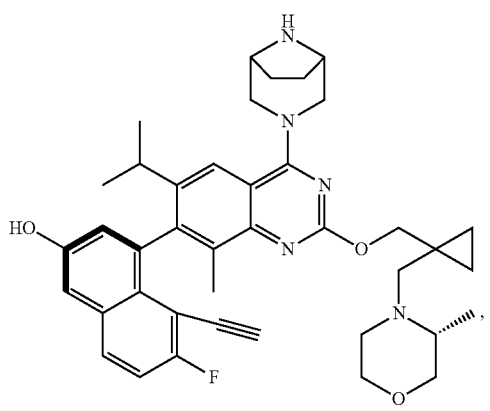
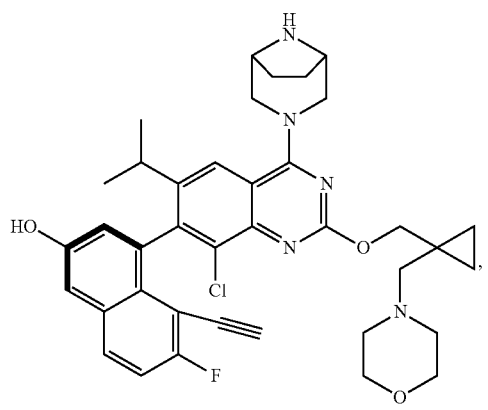
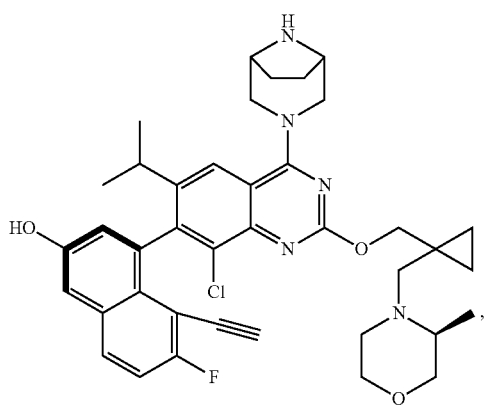
368
-continued

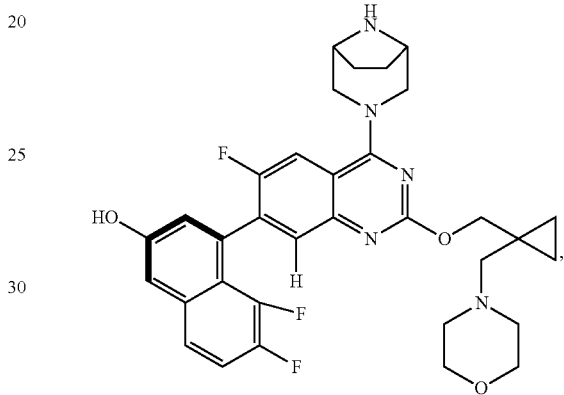
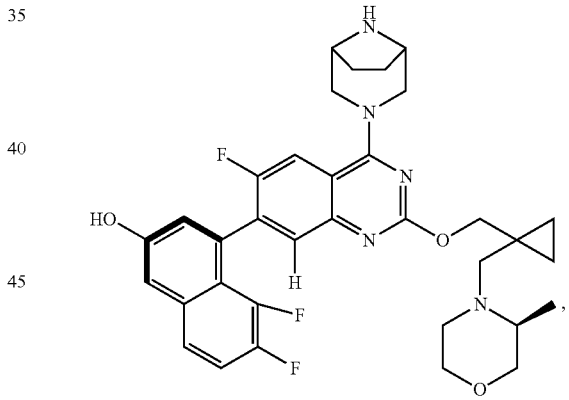
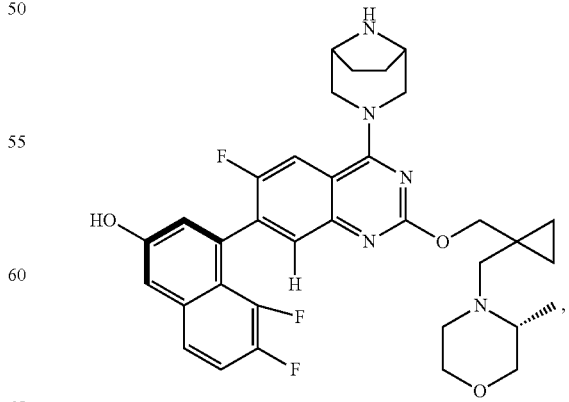

369
-continued
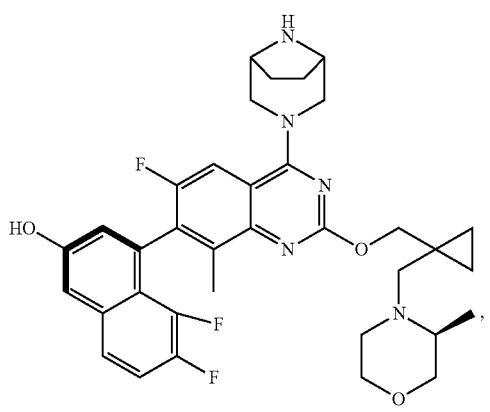
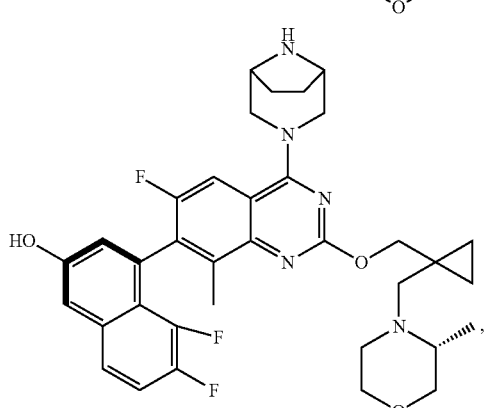
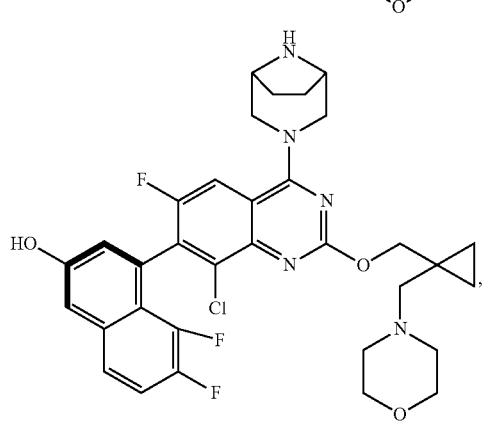
370
-continued
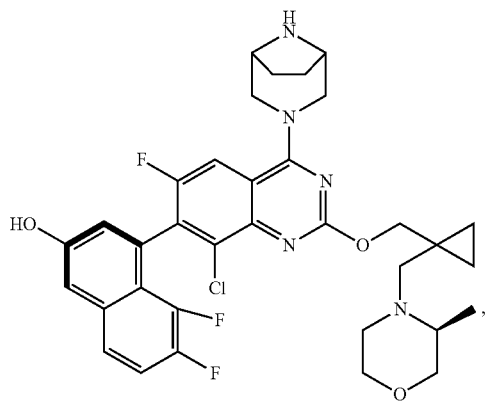
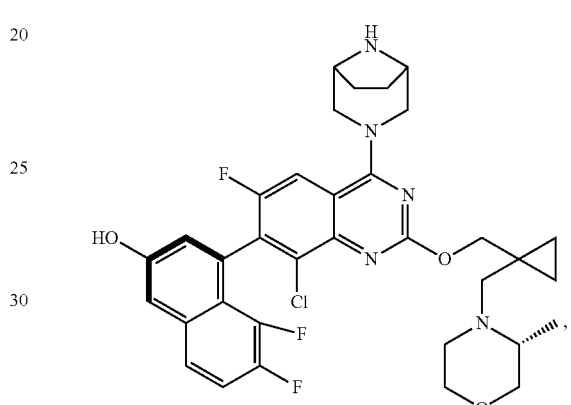

371
-continued
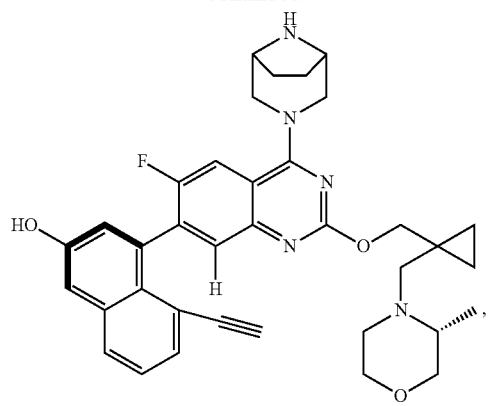
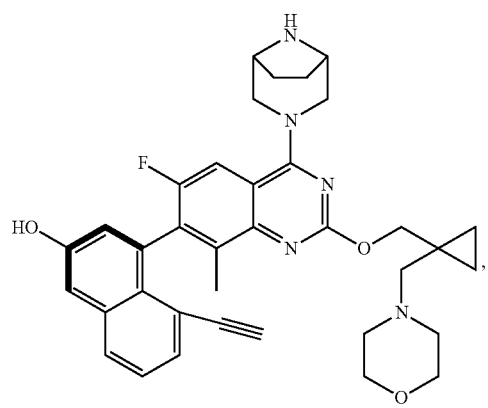
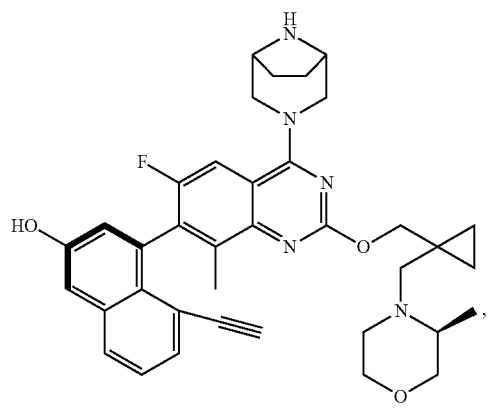
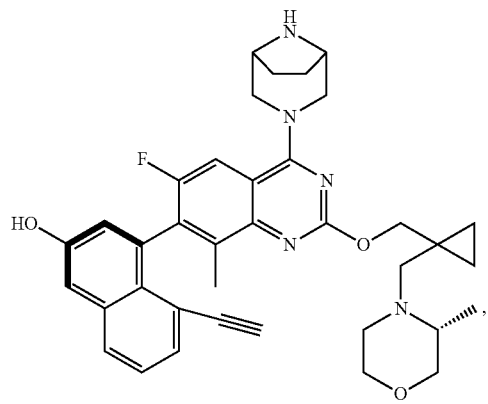
372
-continued
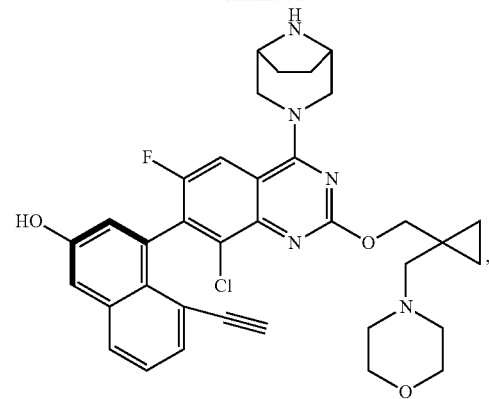
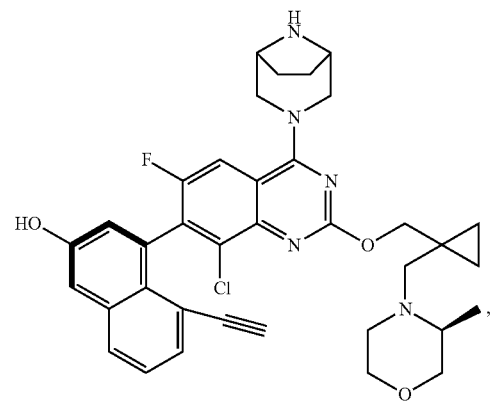
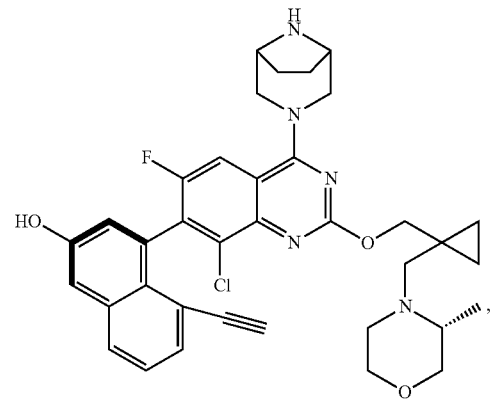
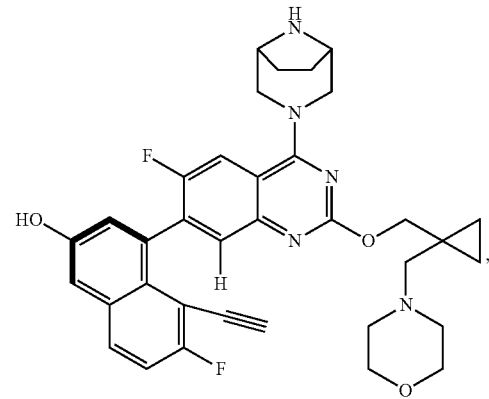

373
-continued
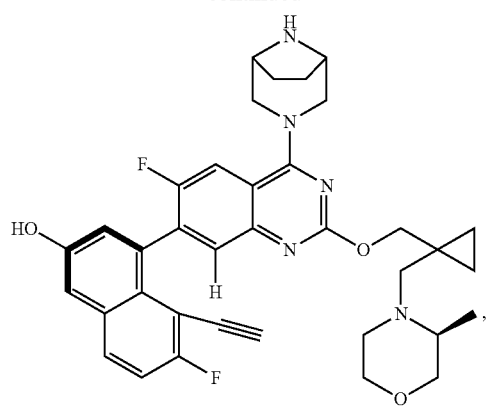
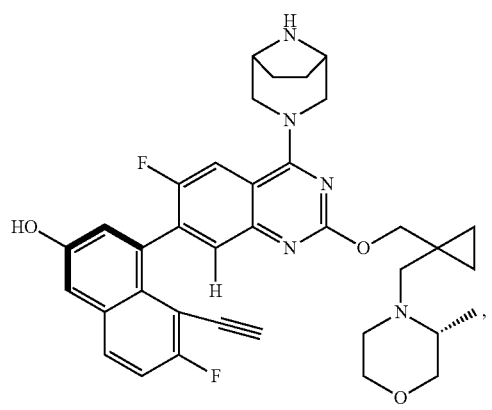
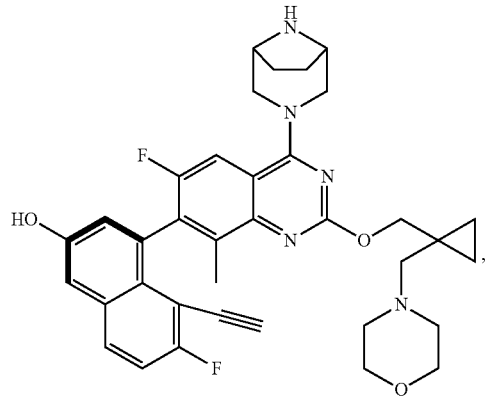
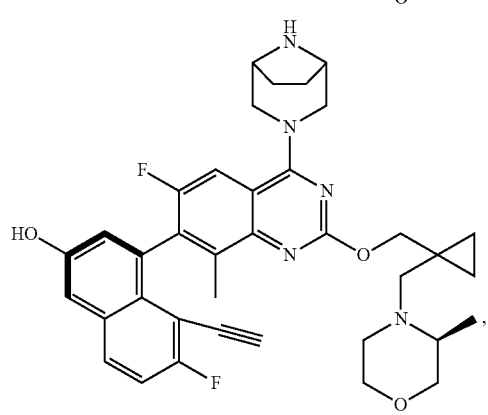
374
-continued
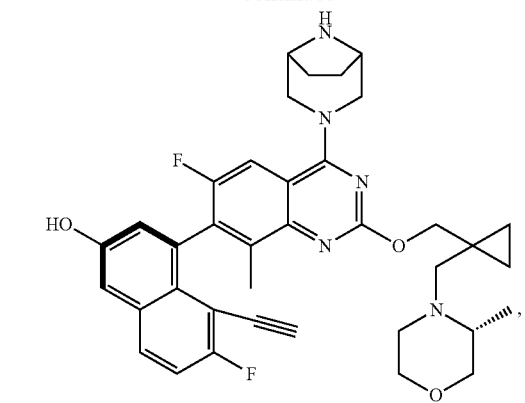
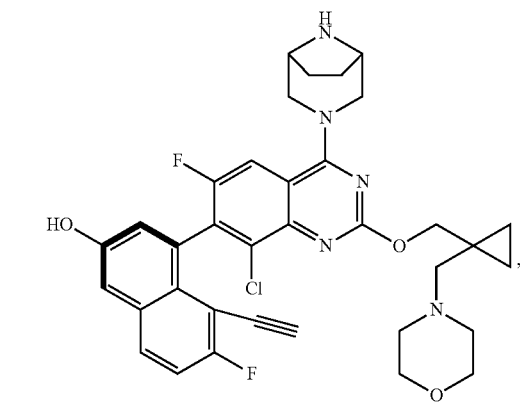
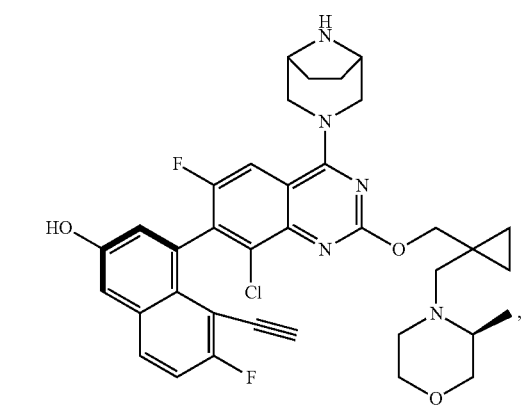
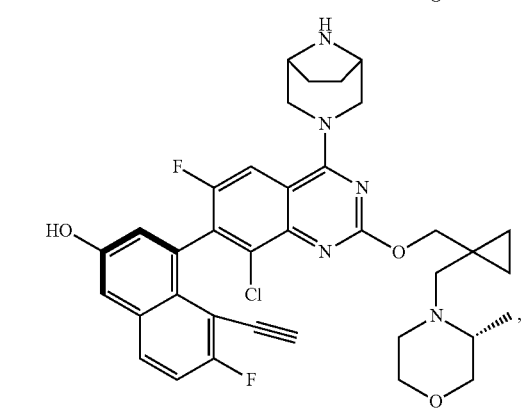

375
-continued
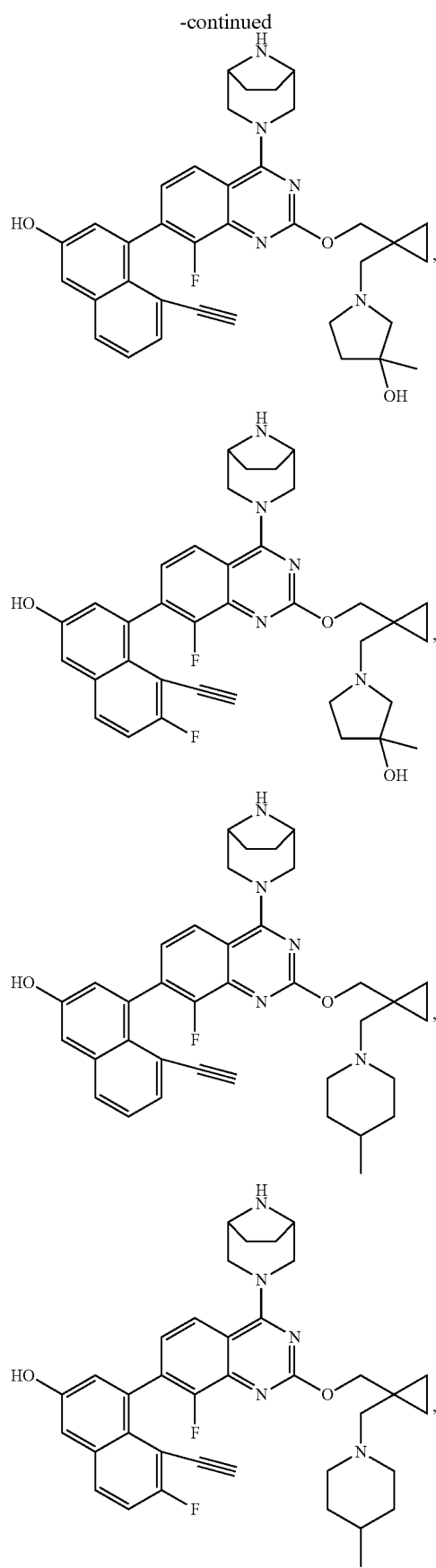
376
-continued
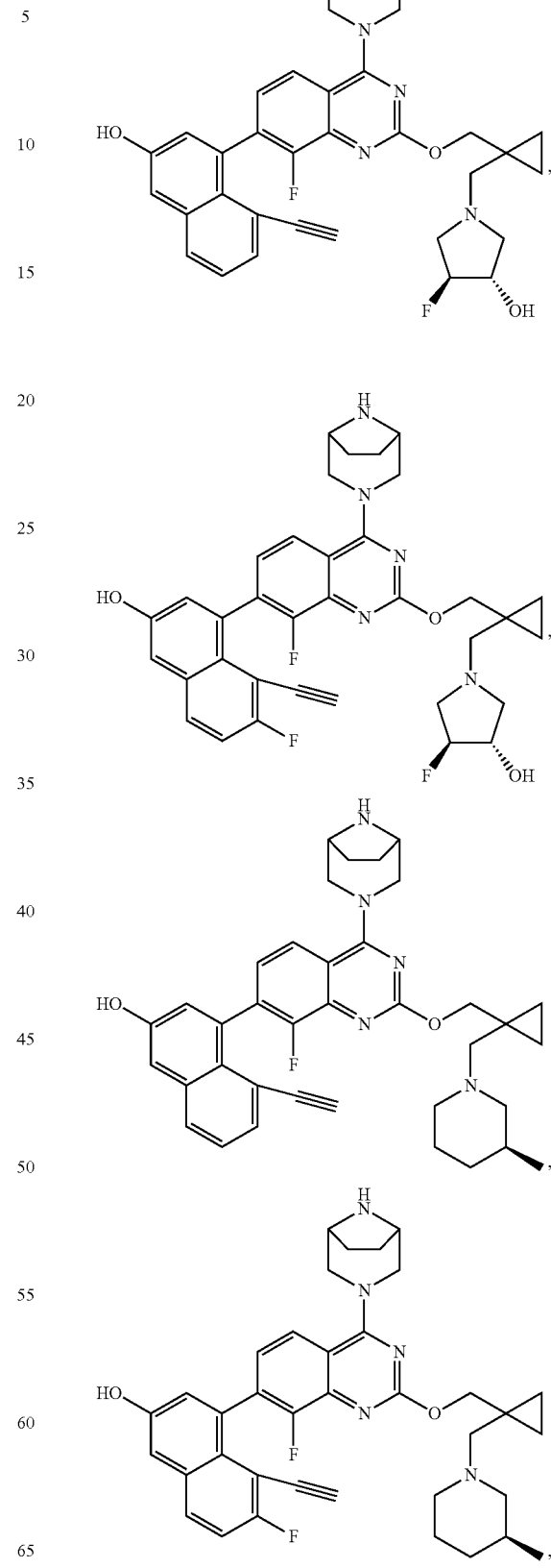

377
-continued
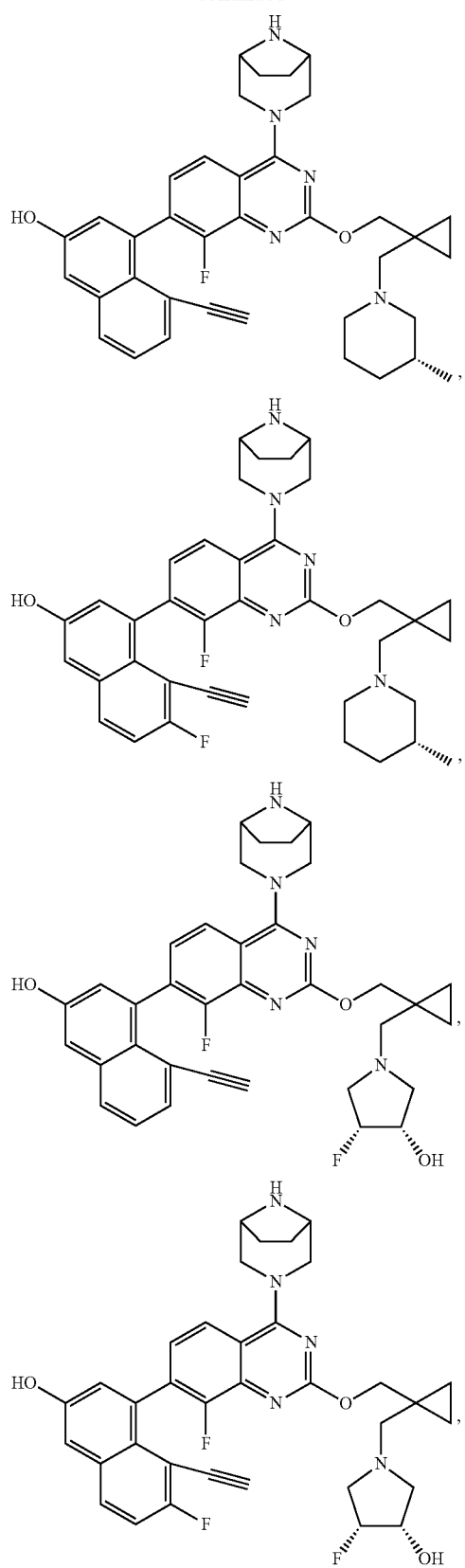
378
-continued
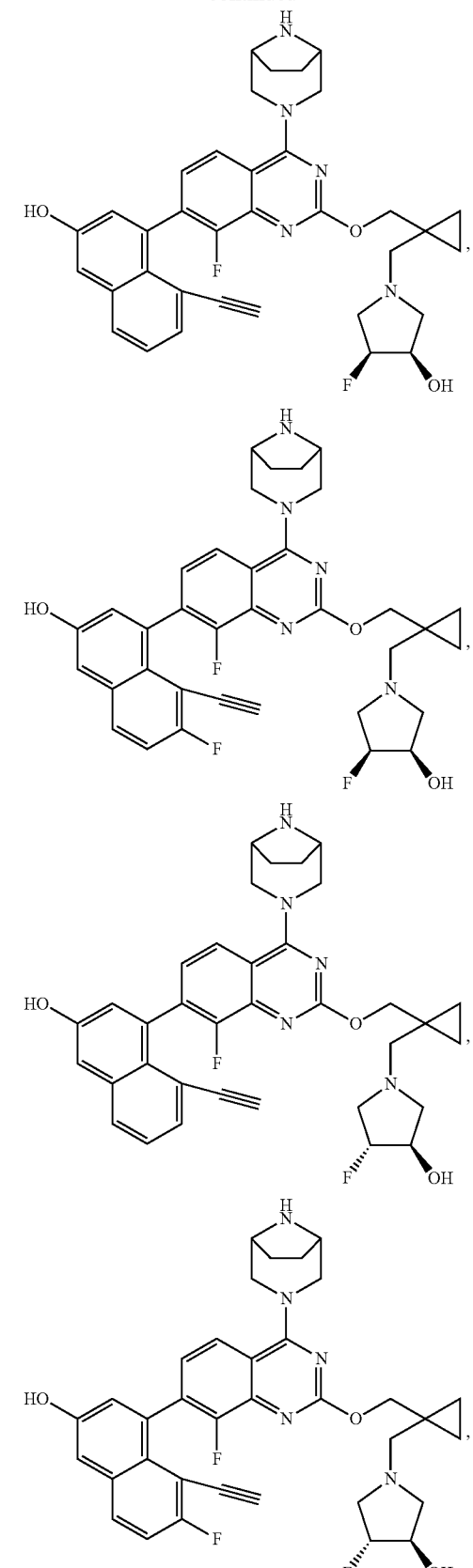

379
-continued
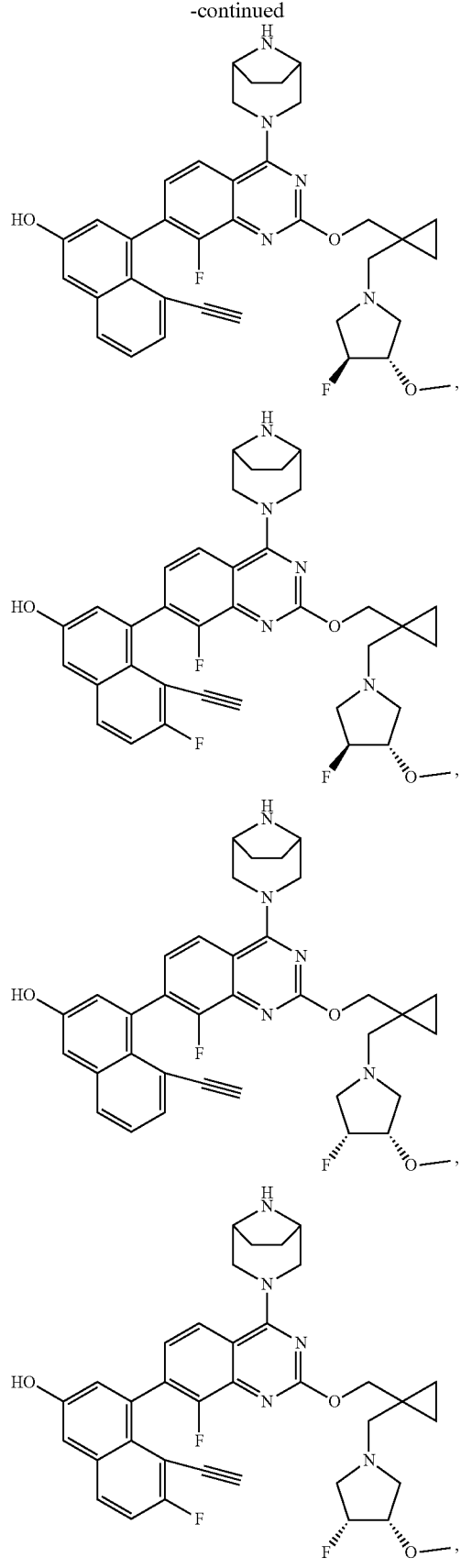
380
-continued
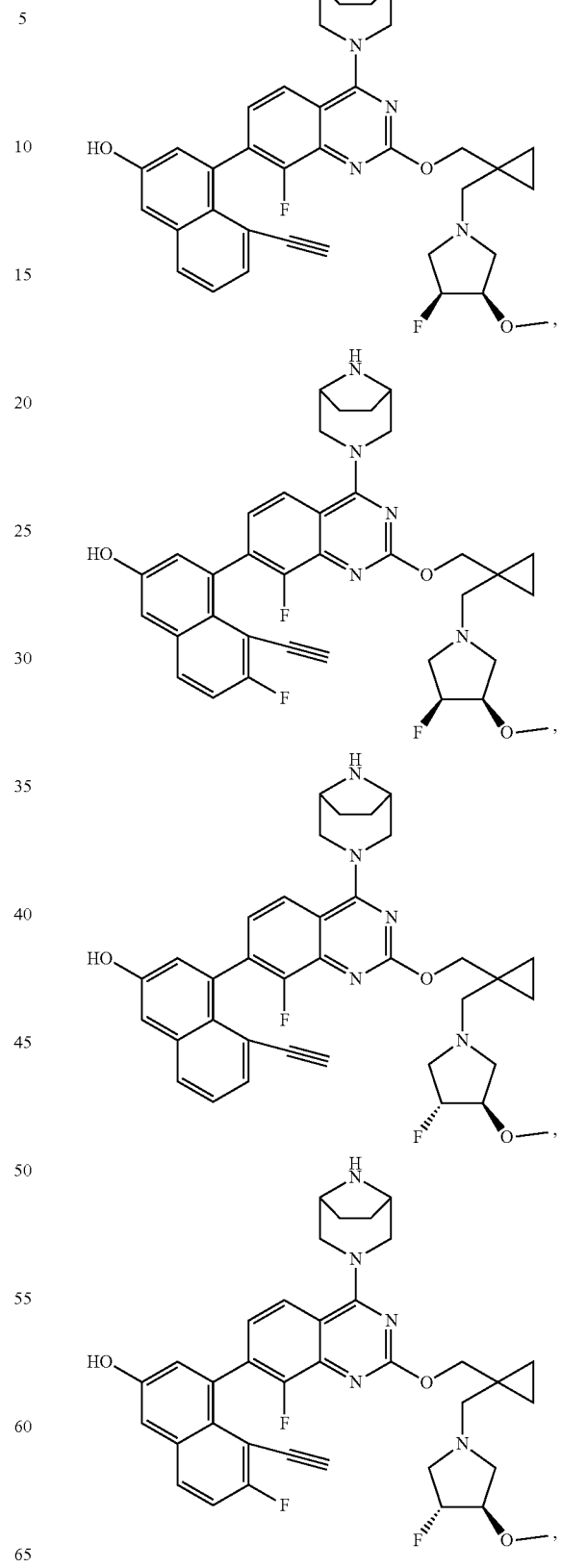

381
-continued
382
-continued
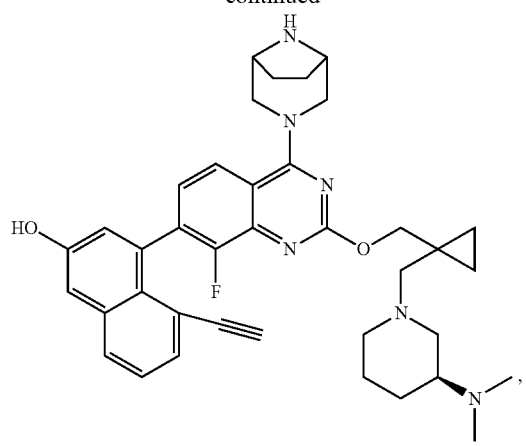
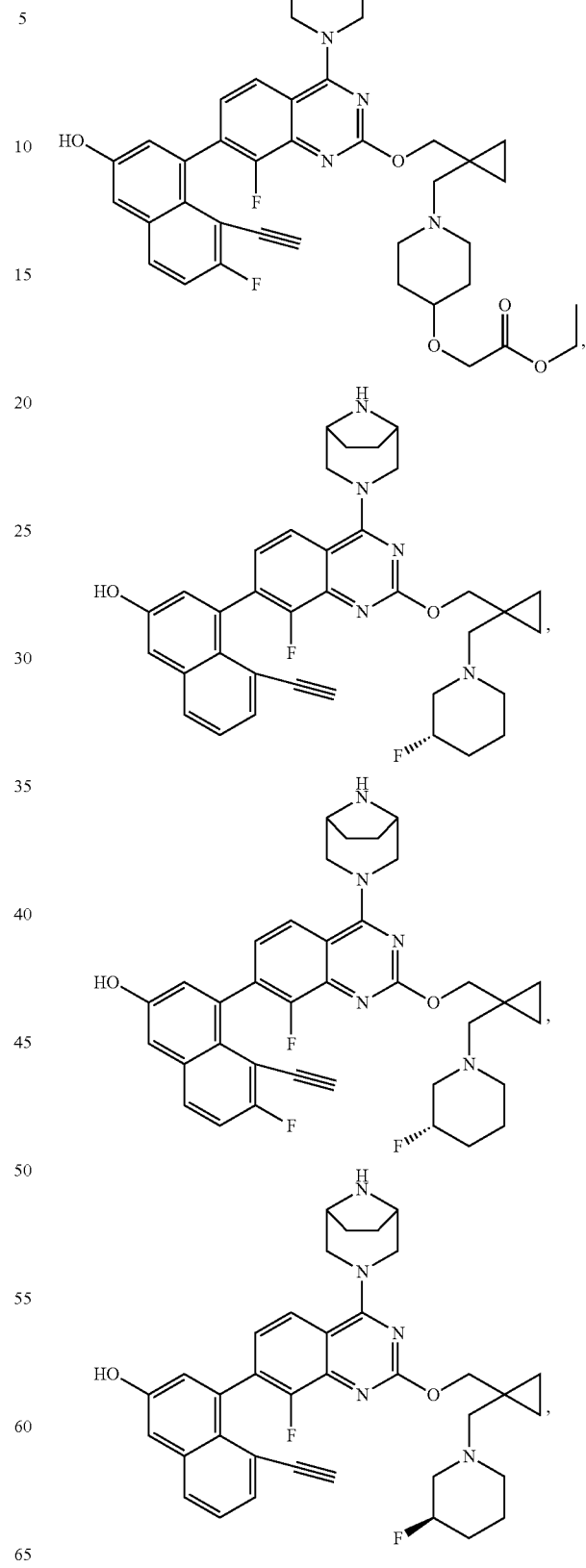

383
-continued
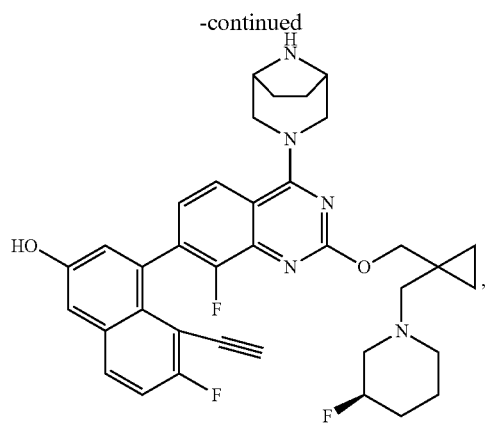
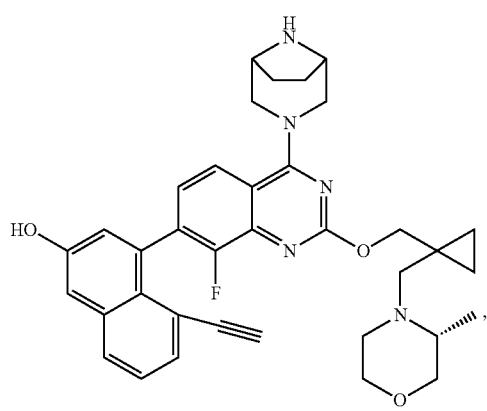
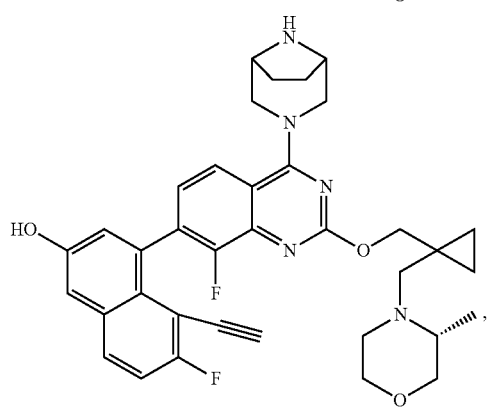
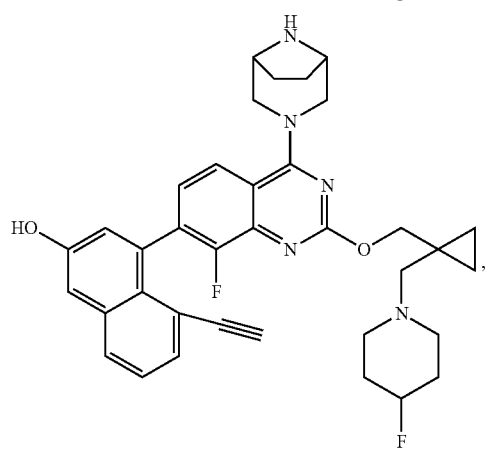
384
-continued
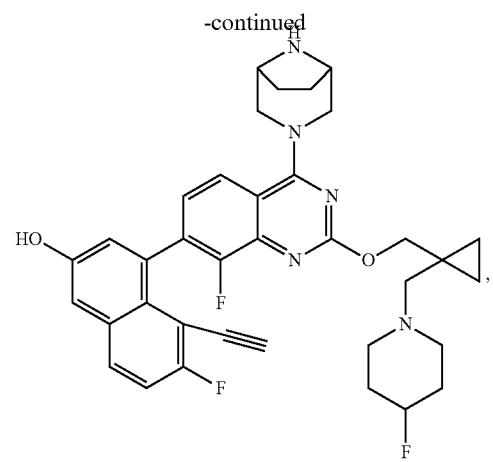
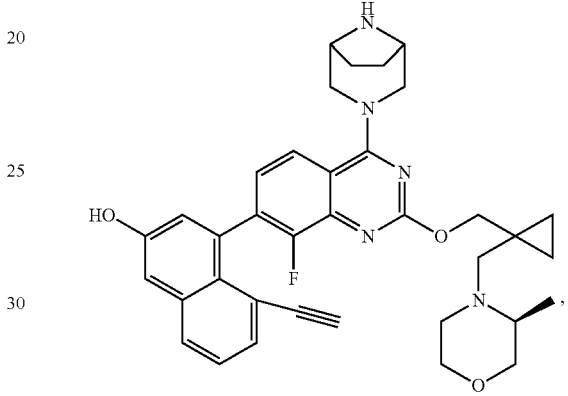
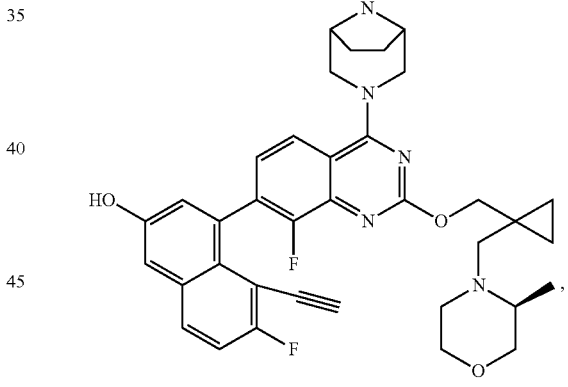
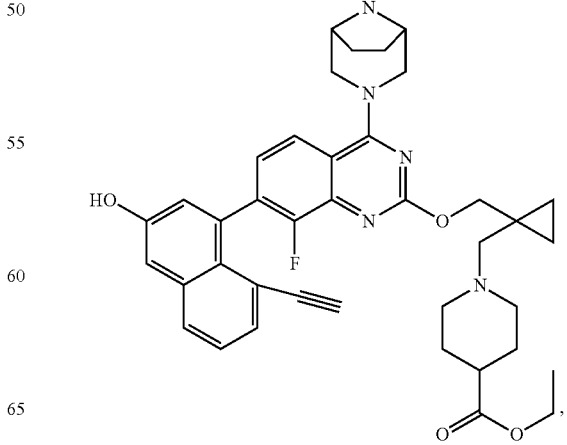

385
-continued
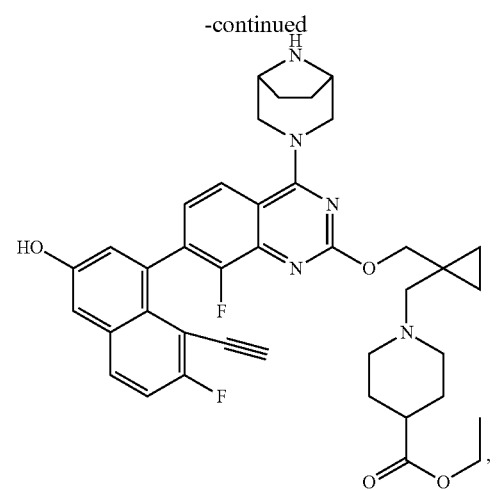
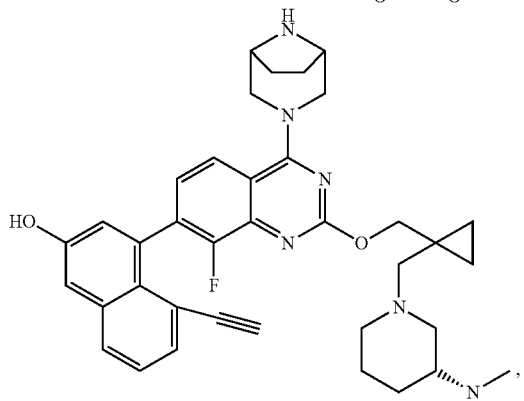
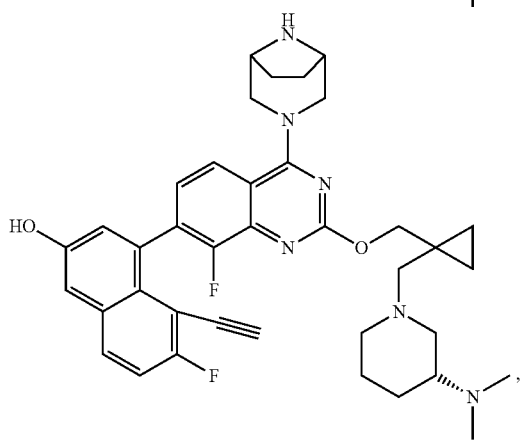
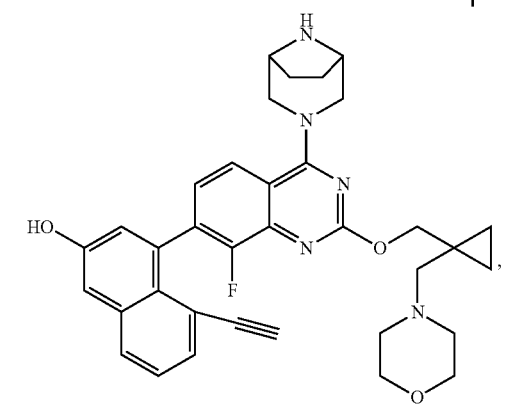
386
-continued
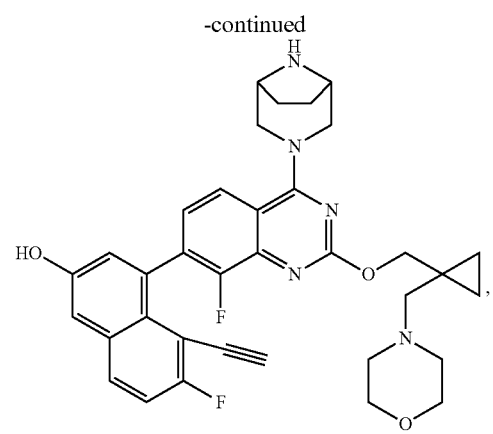
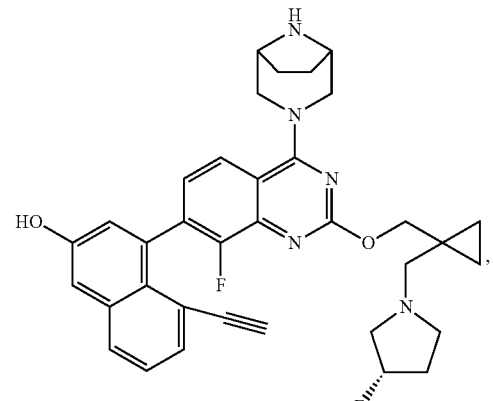
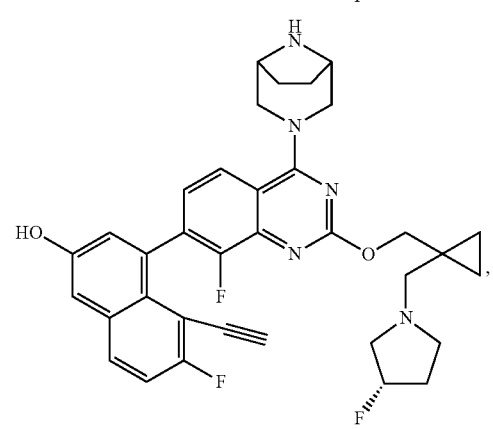
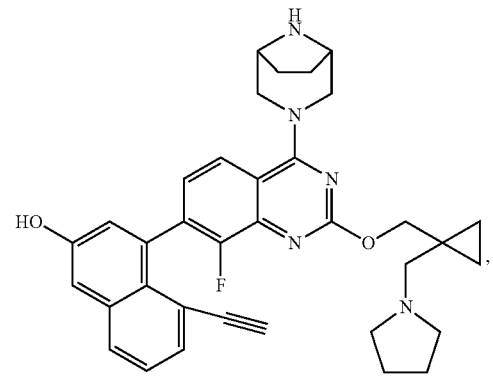

387
-continued
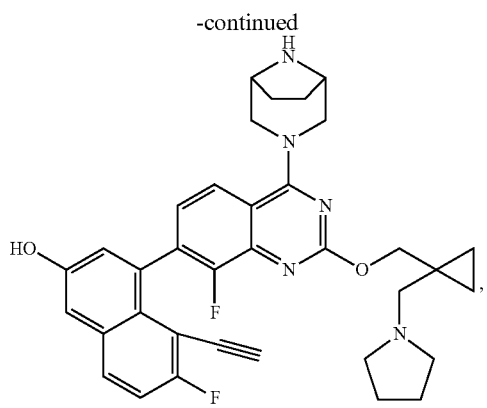
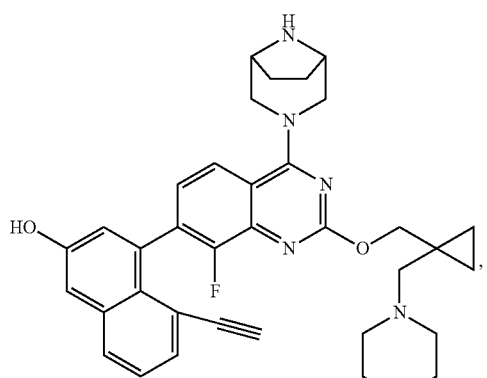
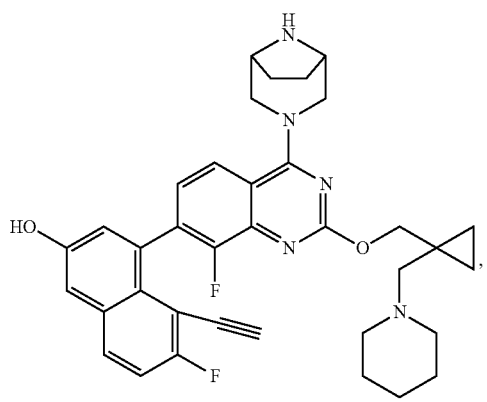
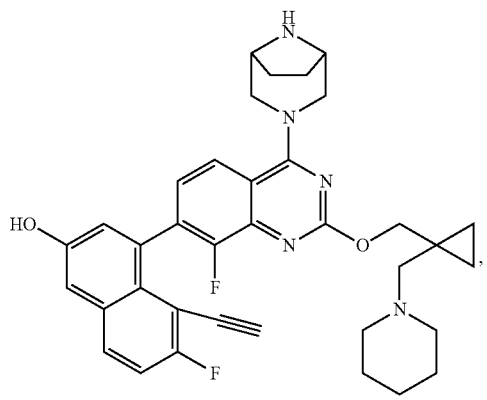
388
-continued
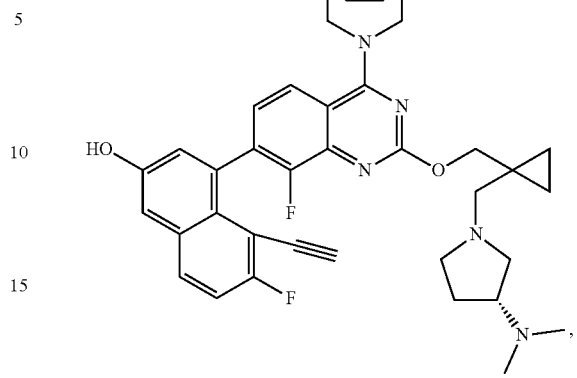
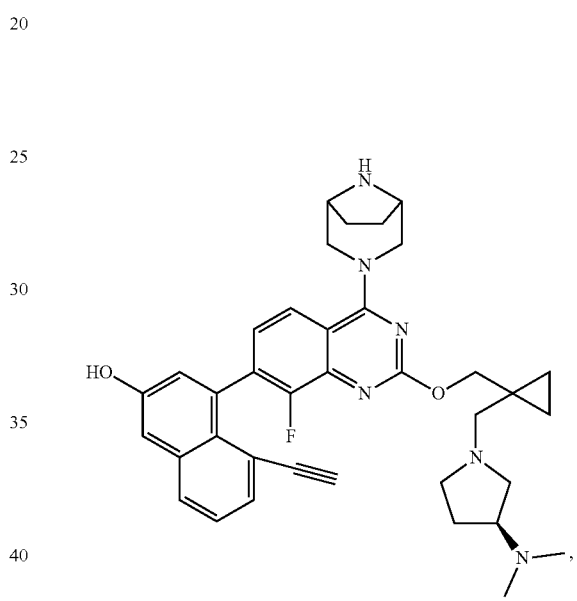
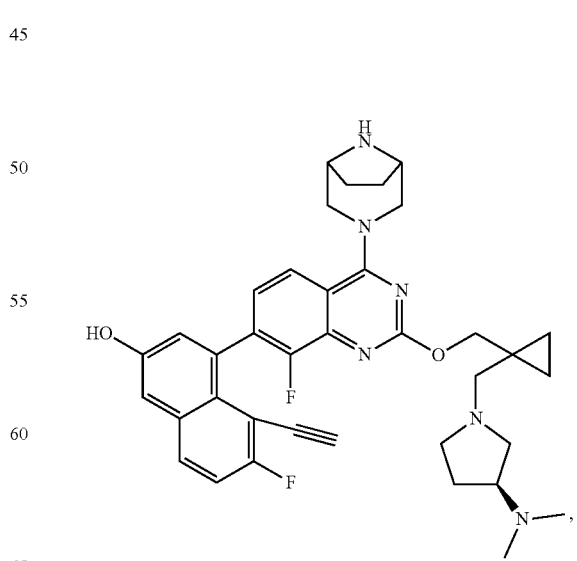

389
-continued
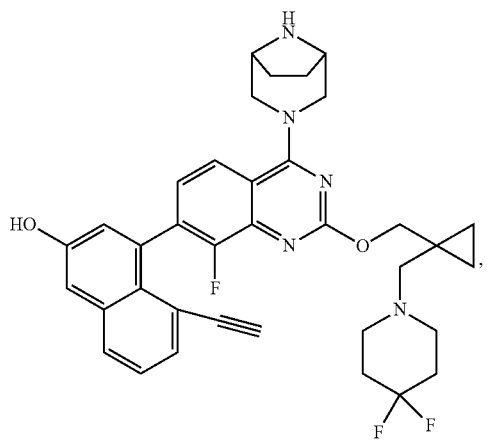
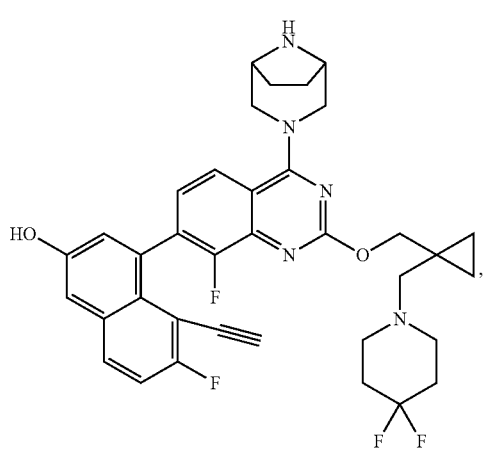
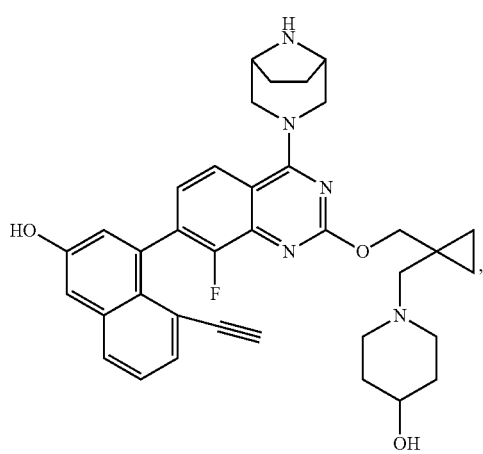
390
-continued
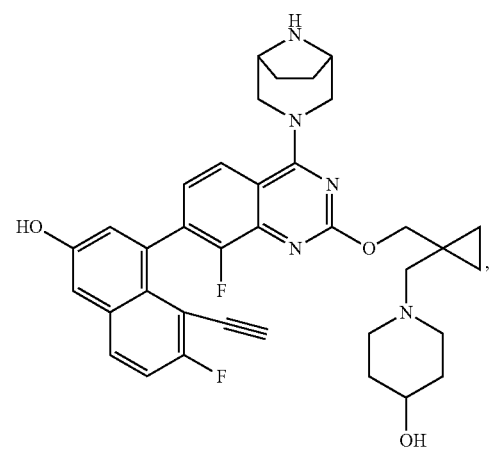
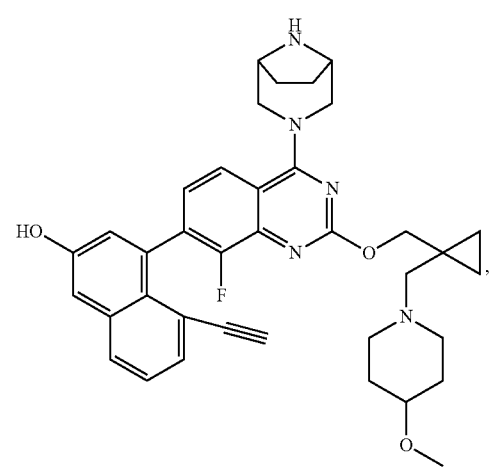
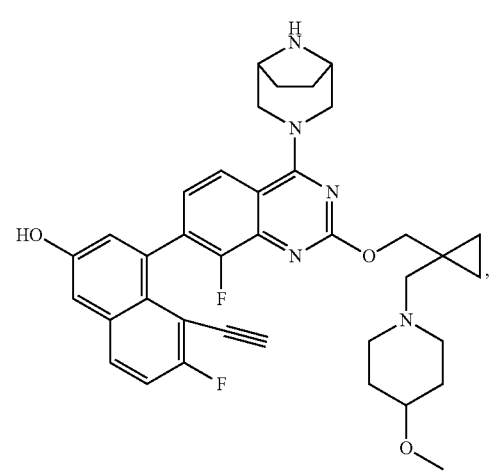

391
-continued
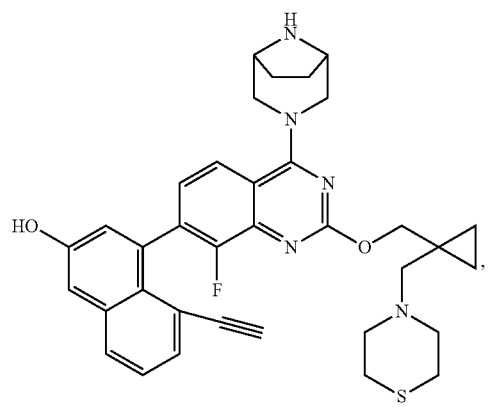
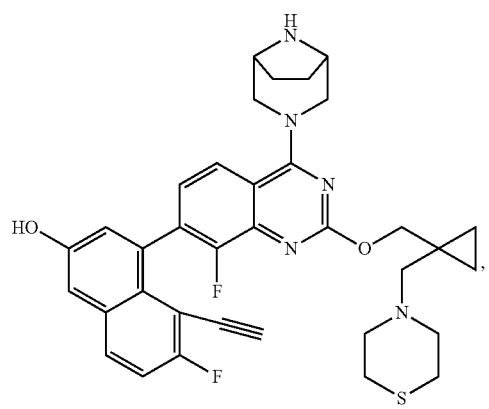
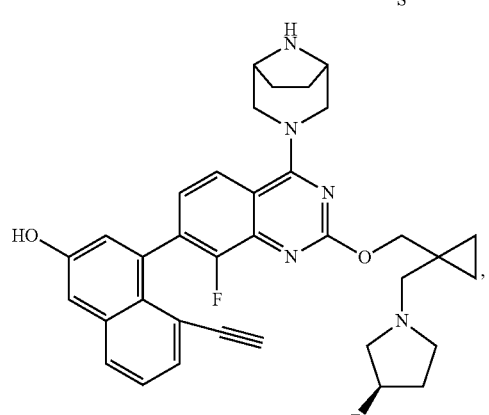
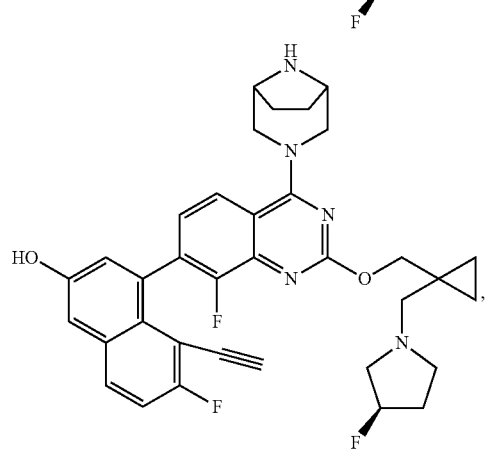
392
-continued
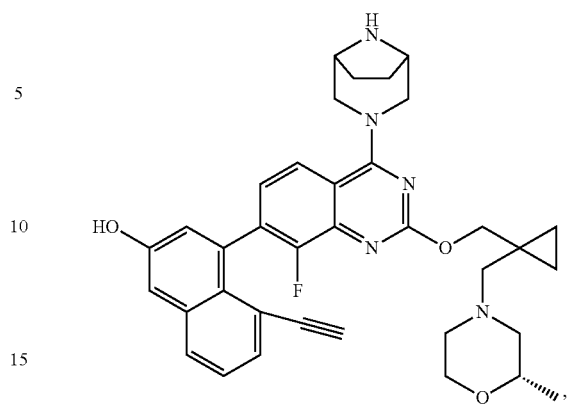
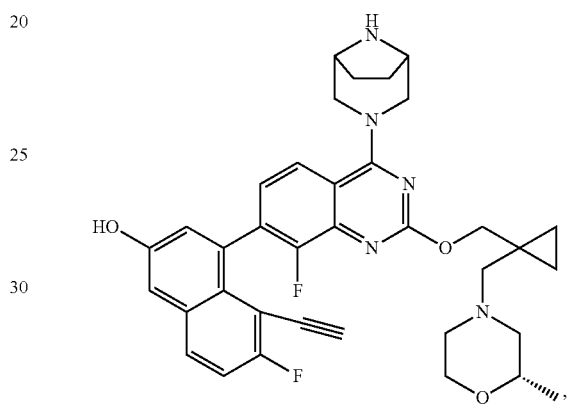
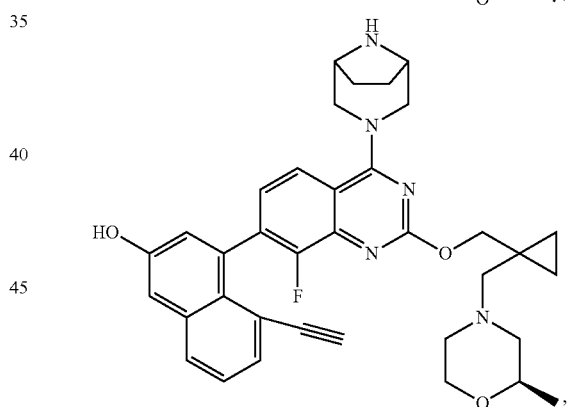
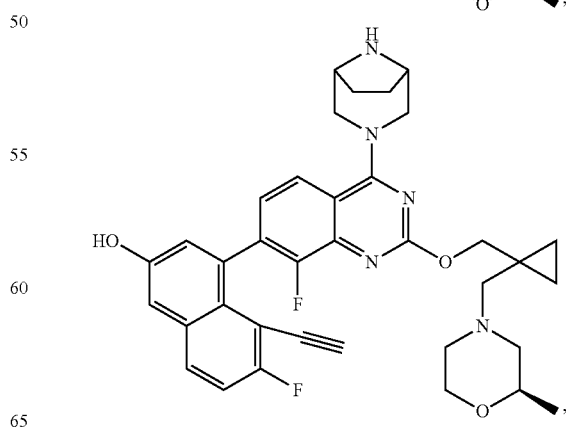

393
-continued
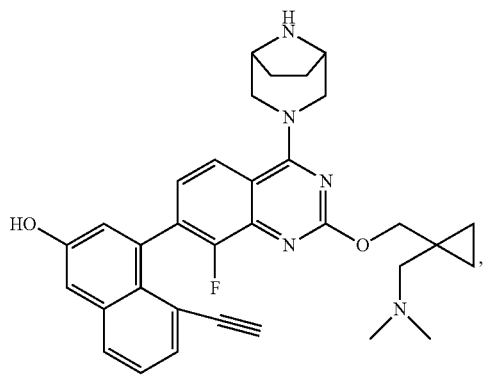
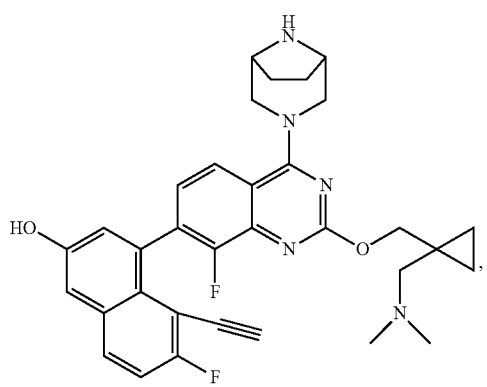
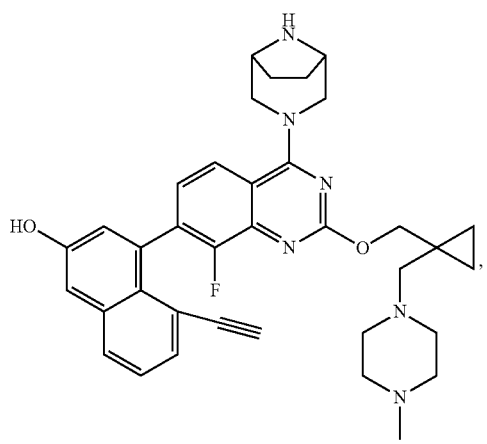
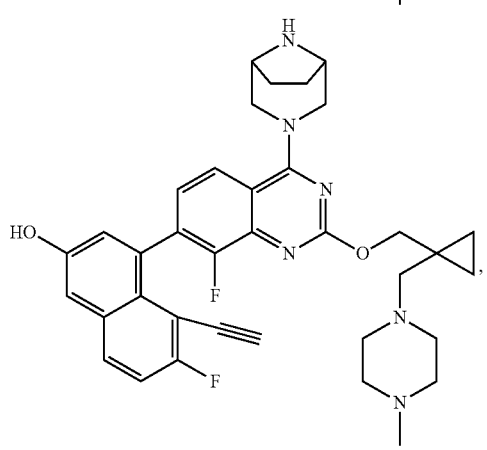
394
-continued
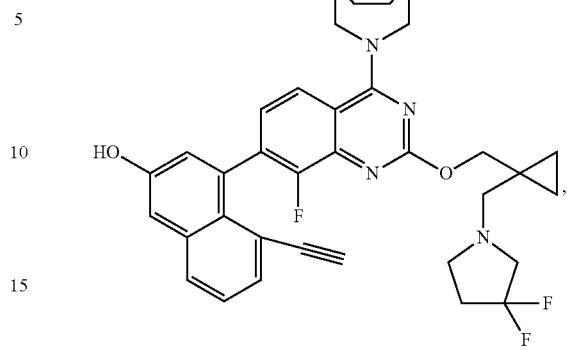
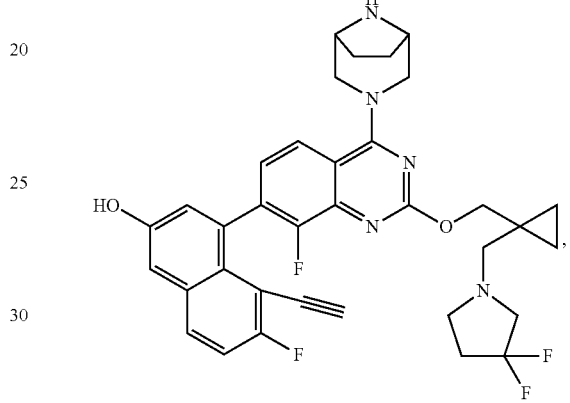
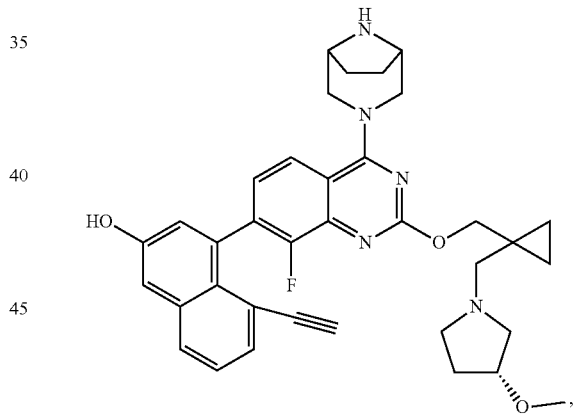
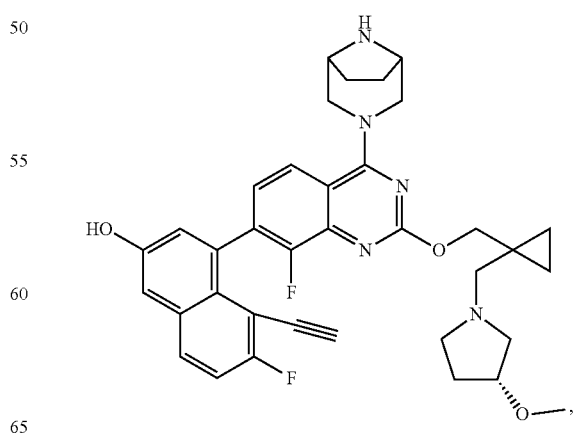

395
-continued
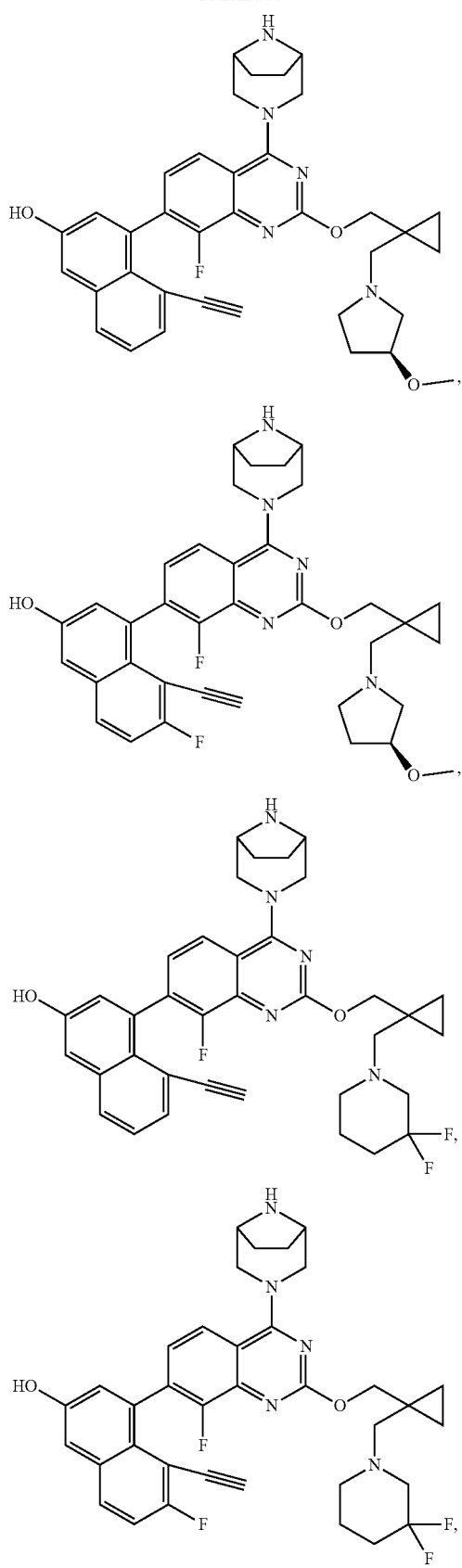
396
-continued
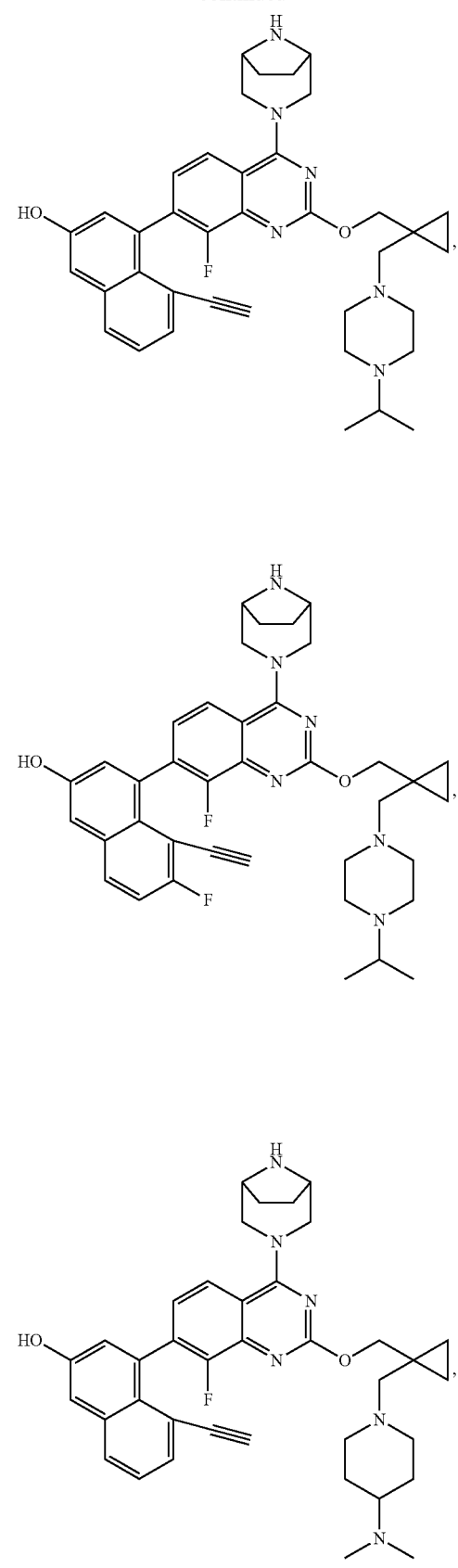

397
-continued
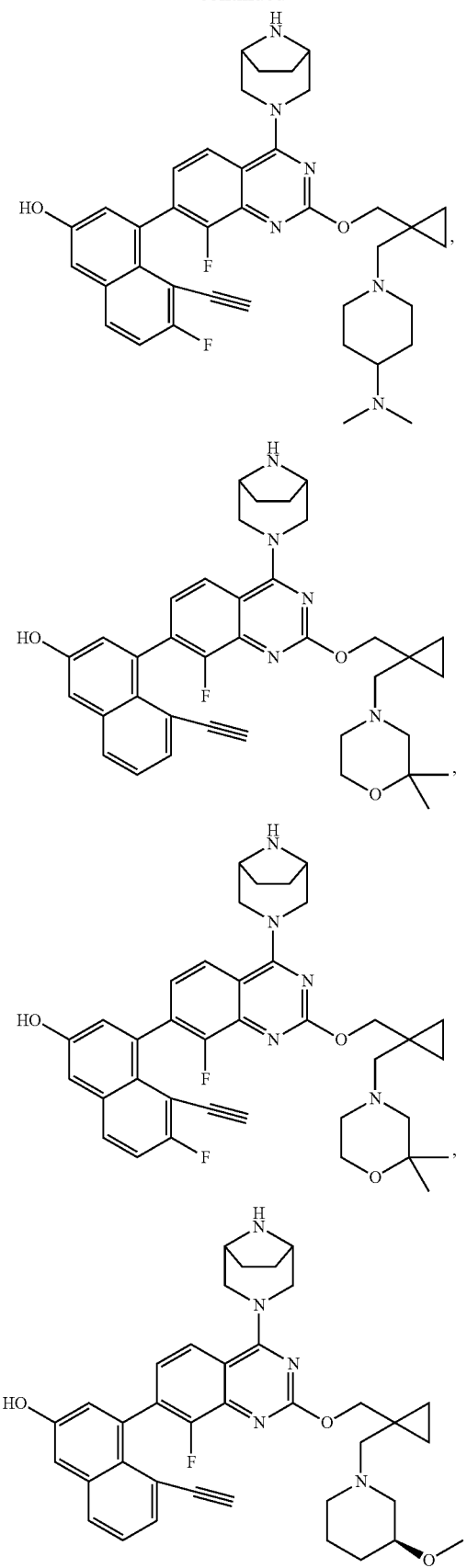
398
-continued
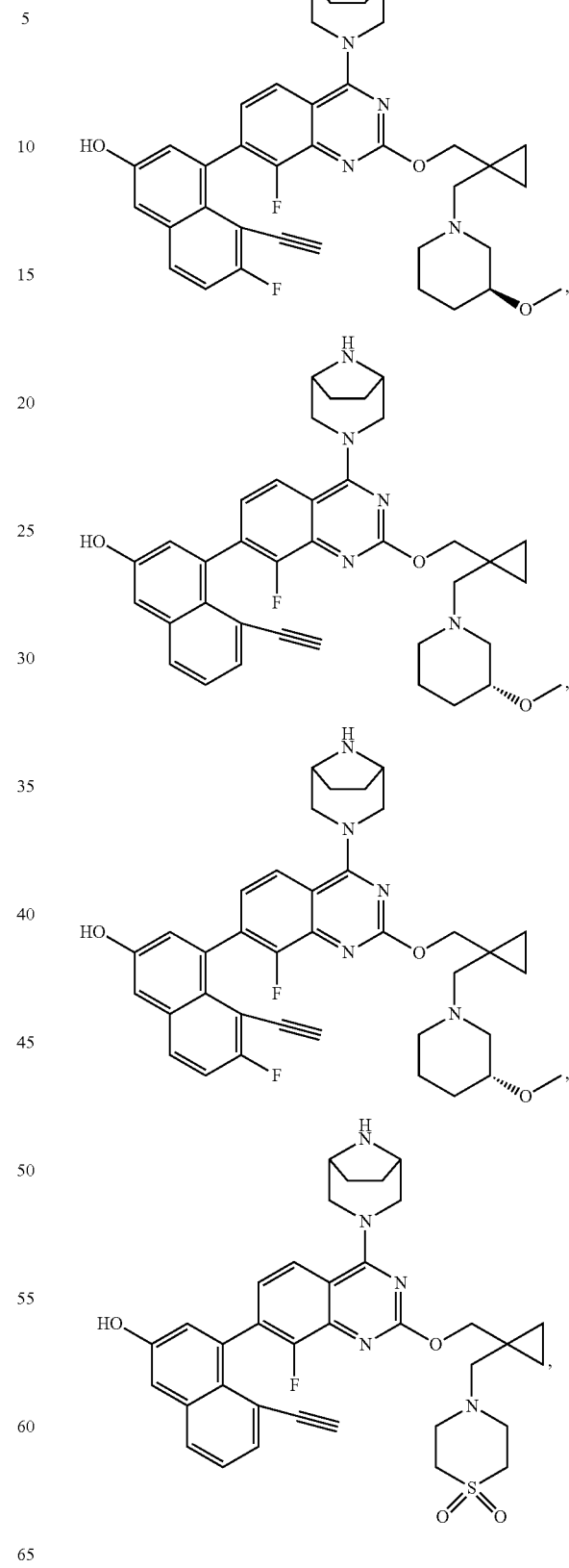

399
-continued
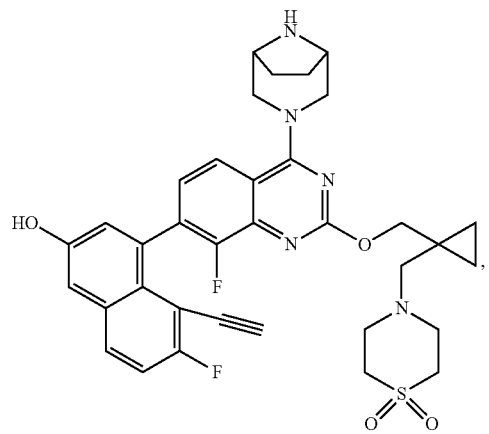
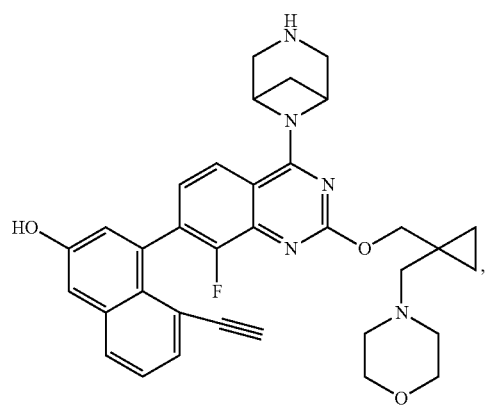
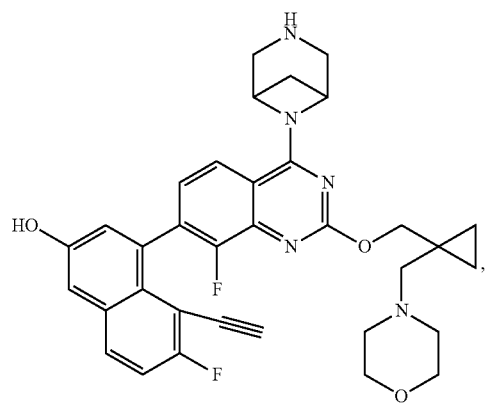
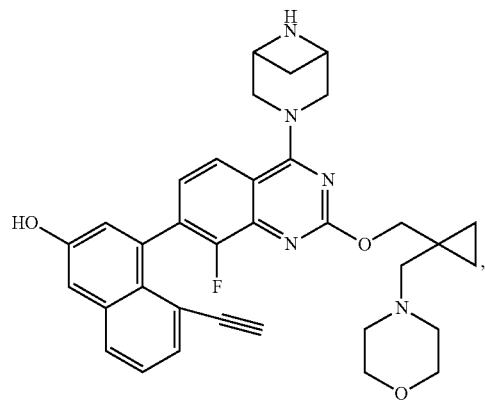
400
-continued
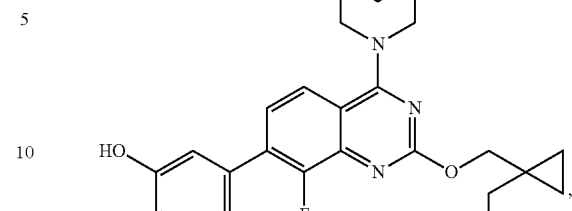

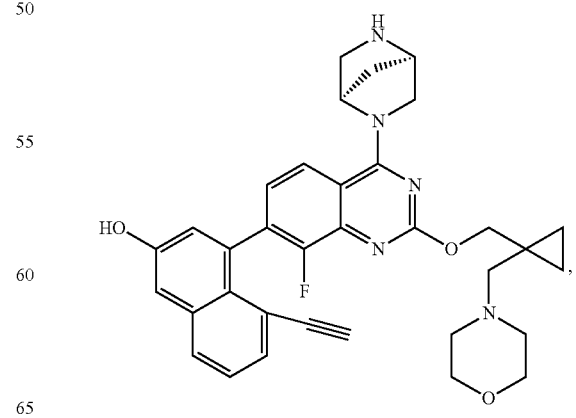

401
-continued
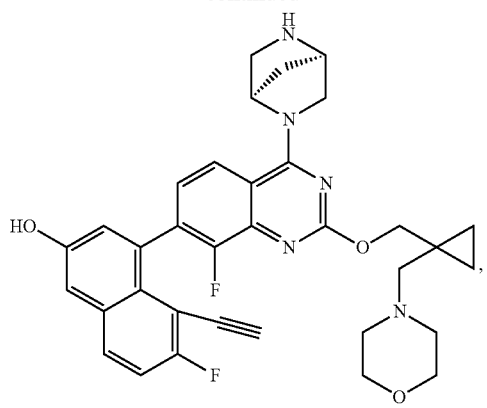
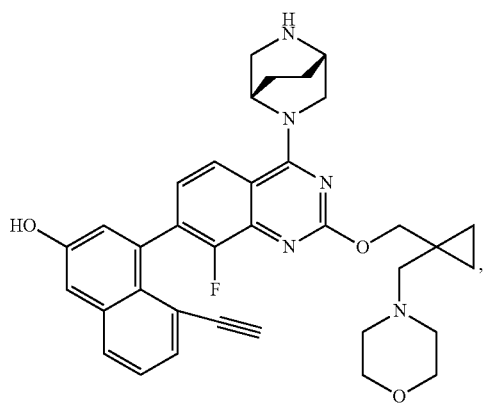
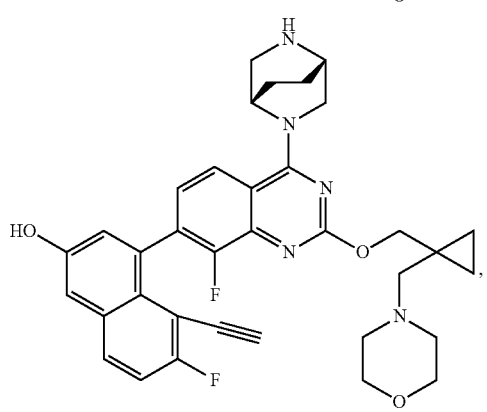
402
-continued
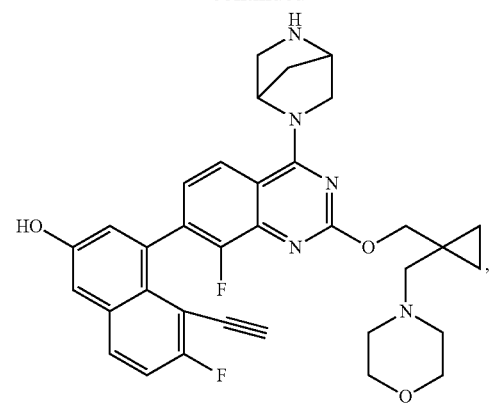
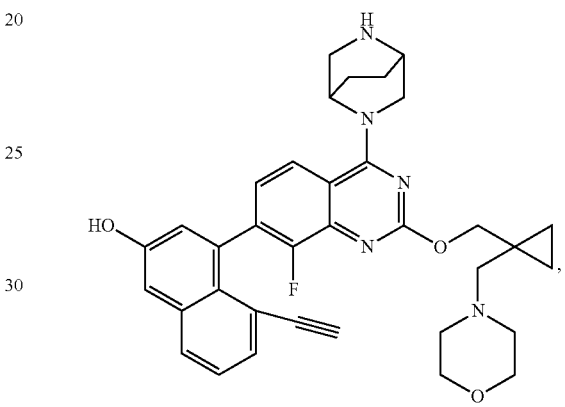
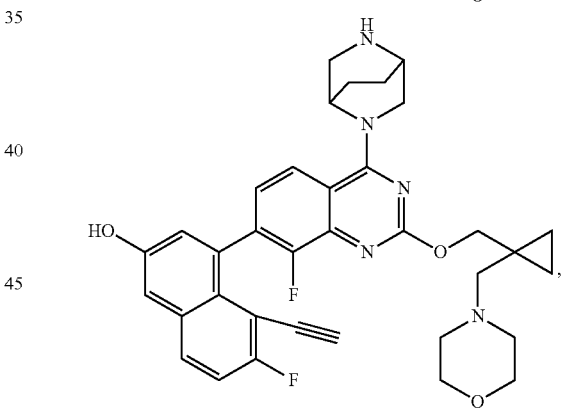

403
-continued
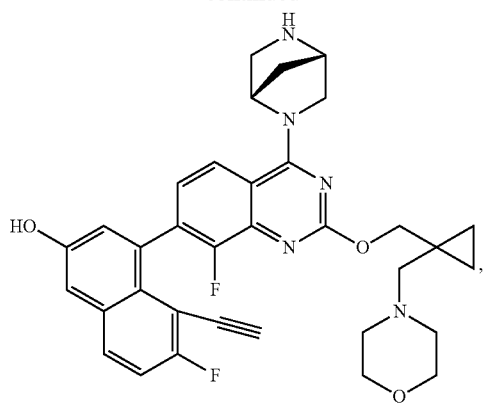
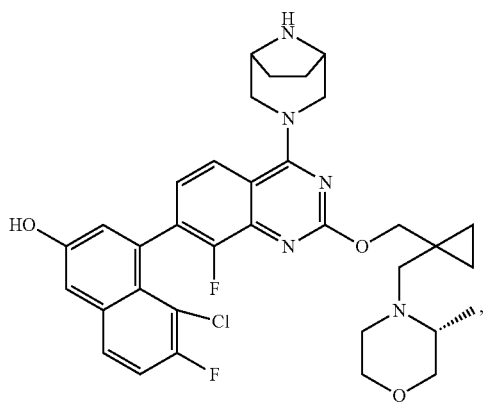
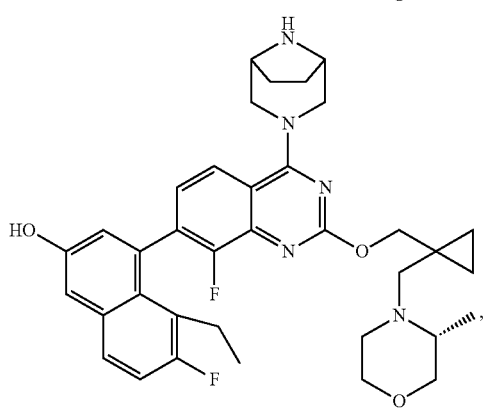
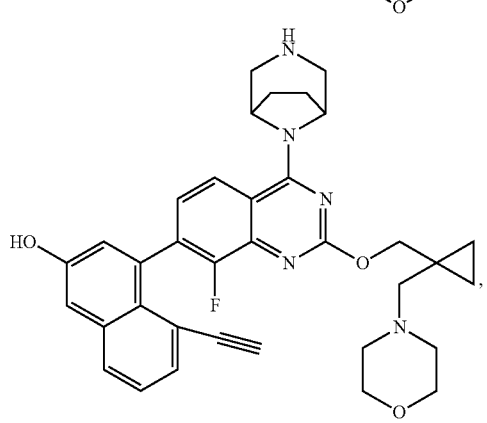
404
-continued
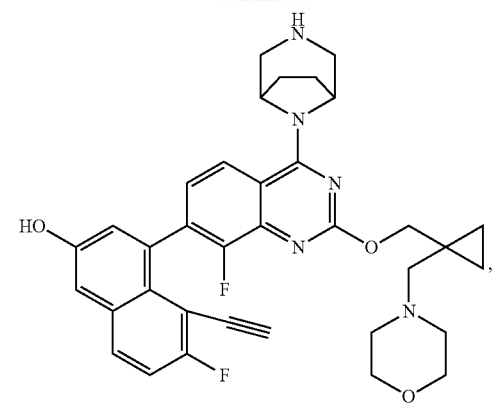
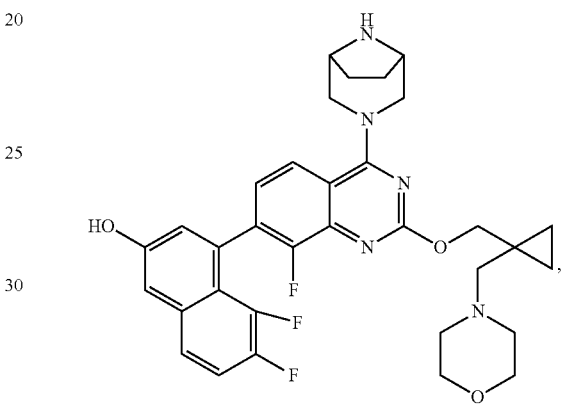
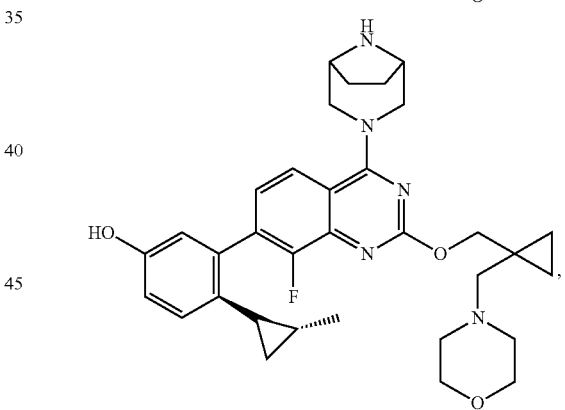
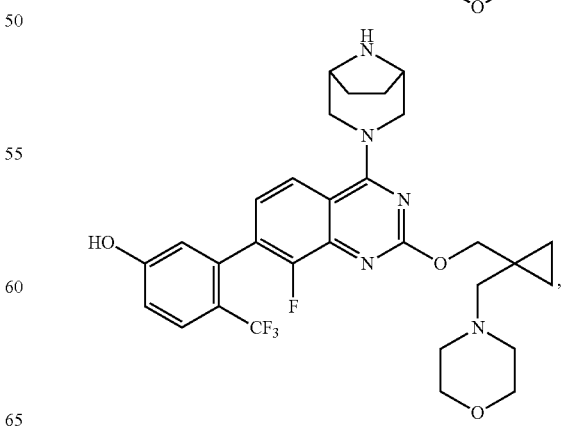

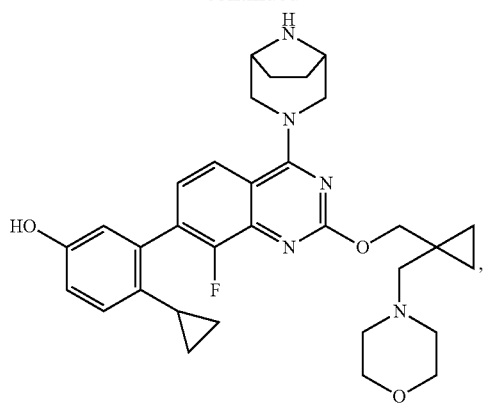
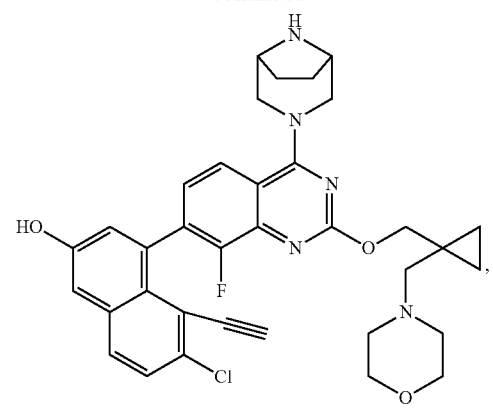
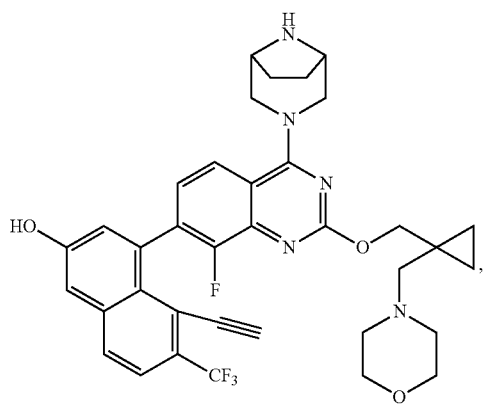
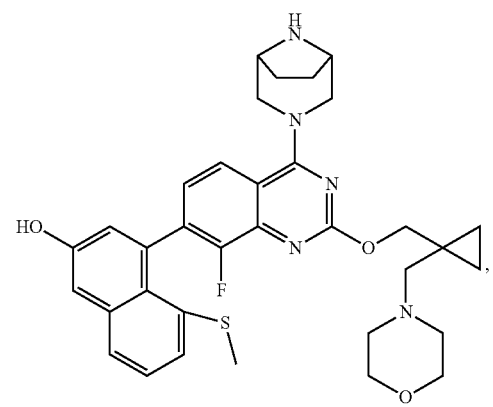
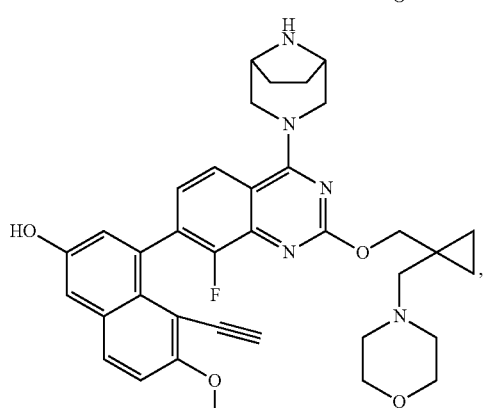
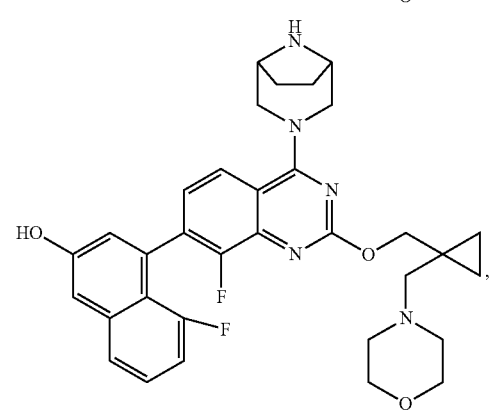
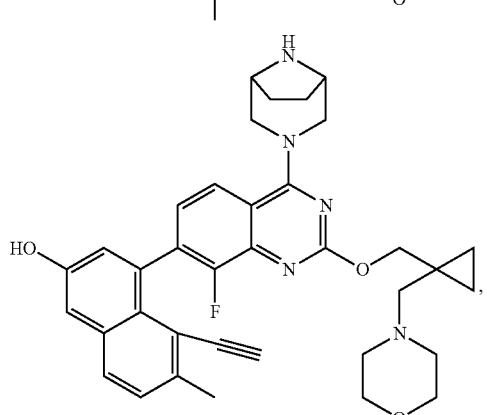
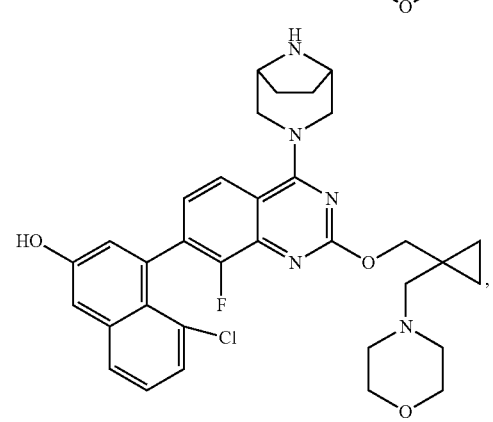

407
-continued
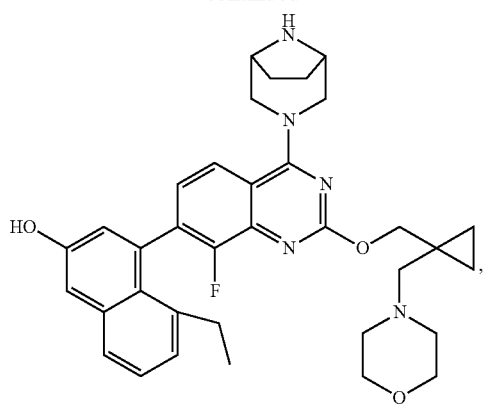
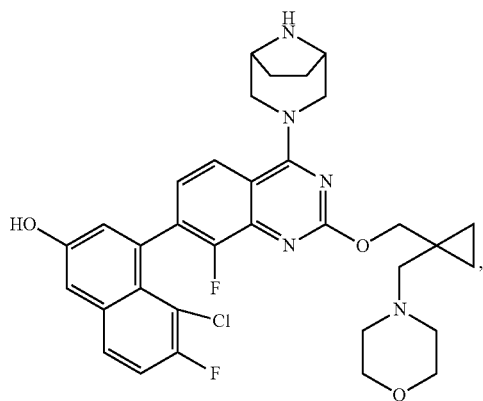
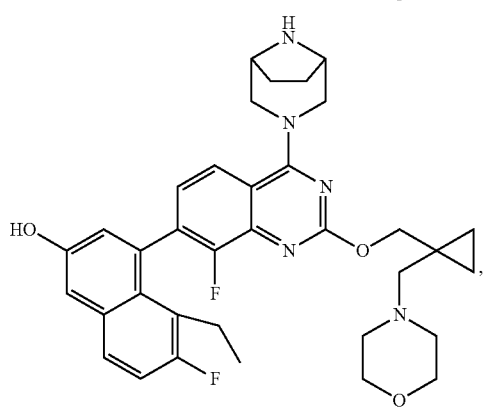

408
-continued
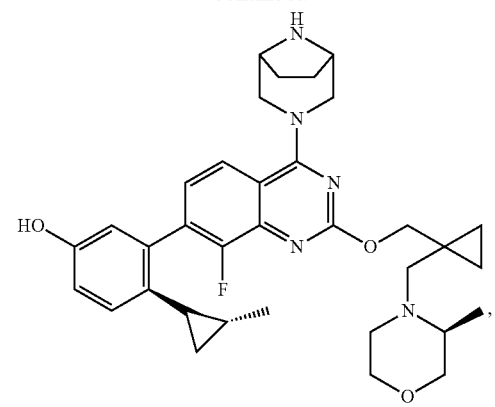
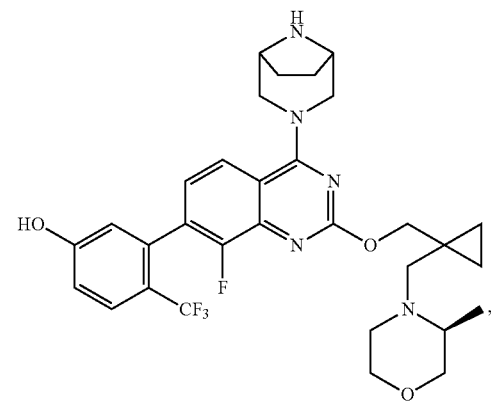
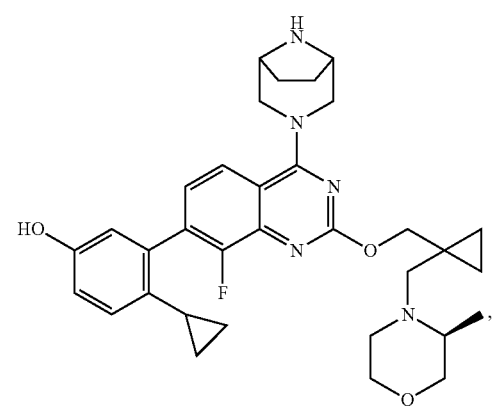
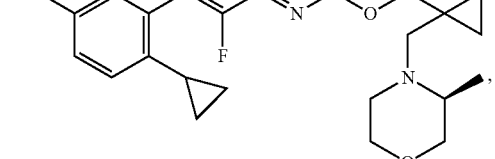

409
-continued
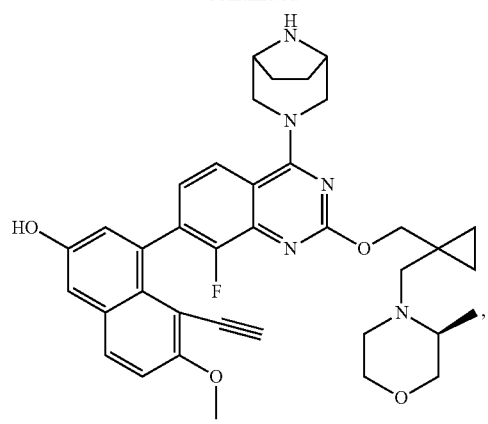
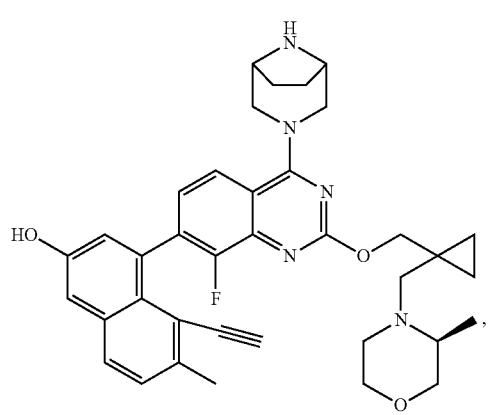
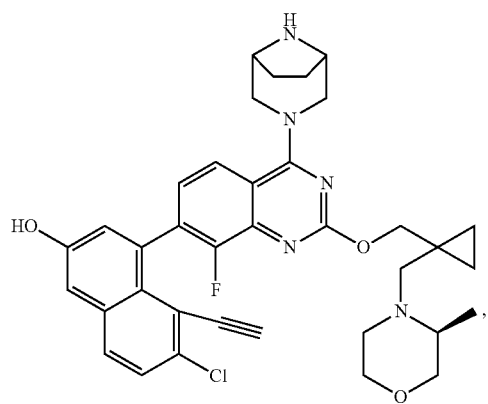
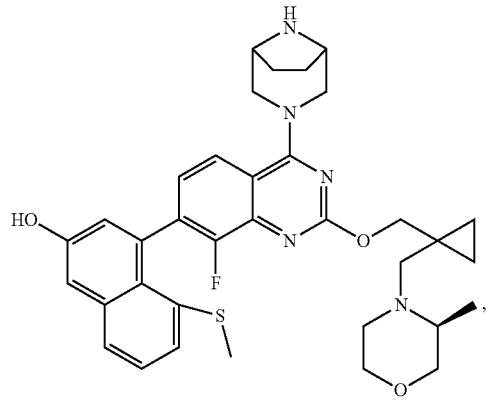
410
-continued
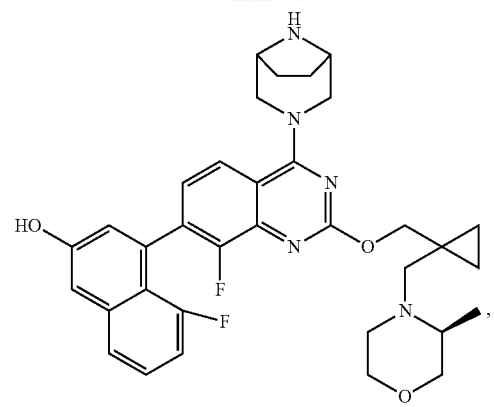
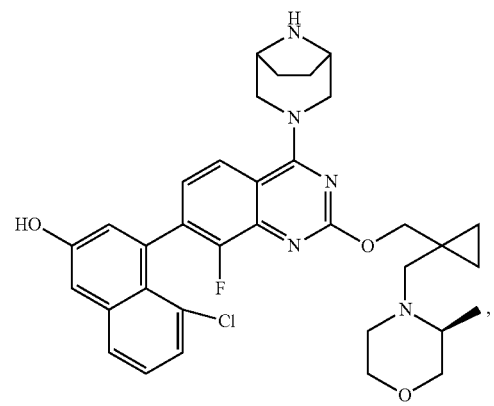
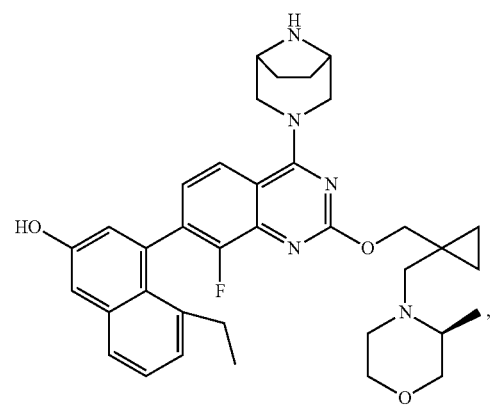
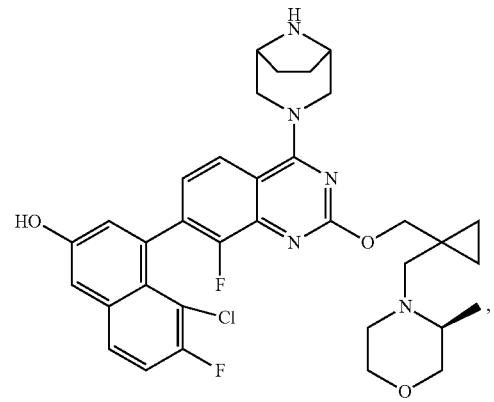

411
-continued
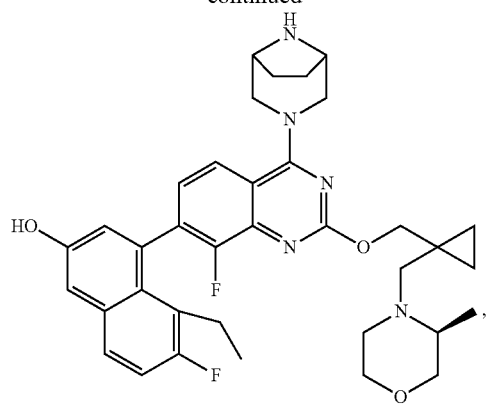
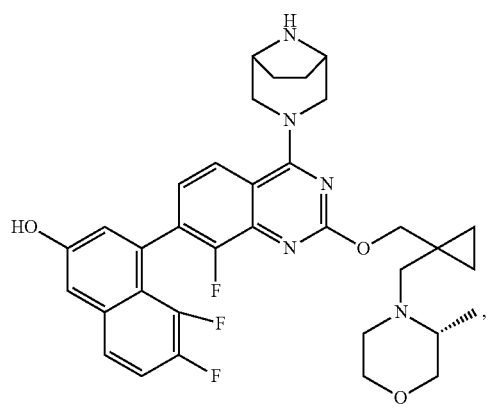
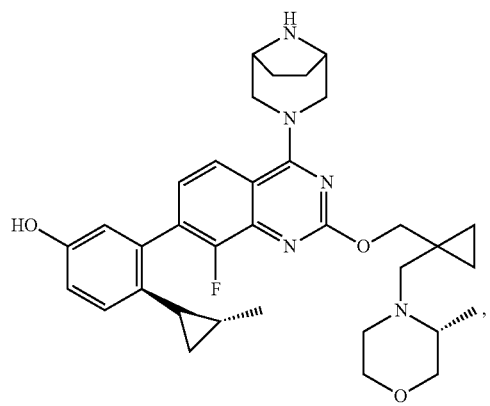
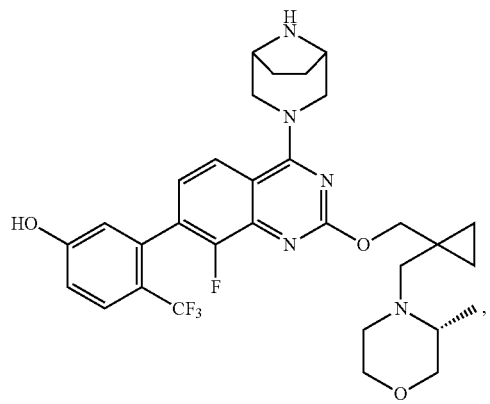
412
-continued
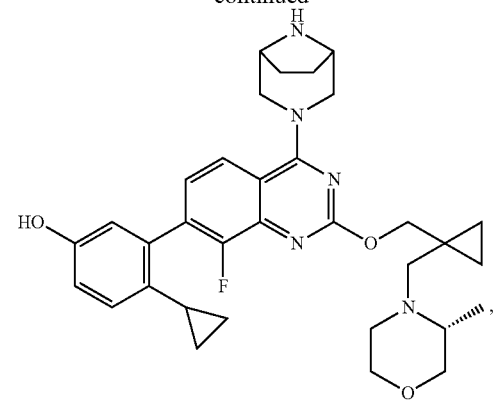
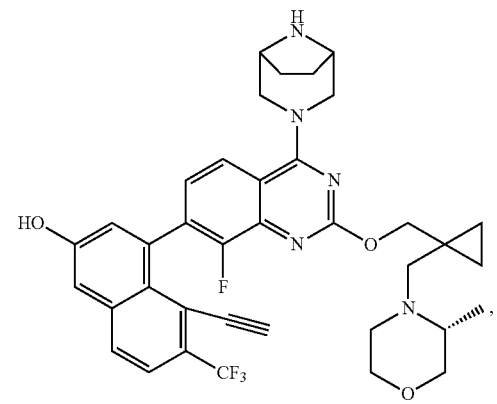
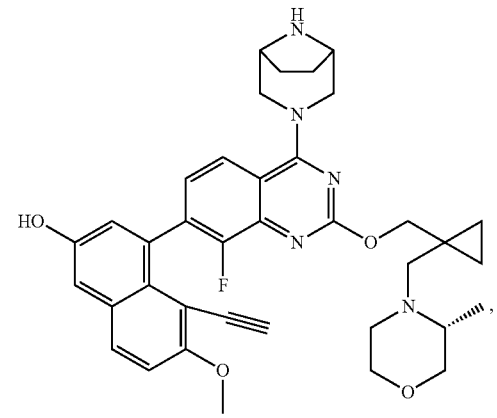
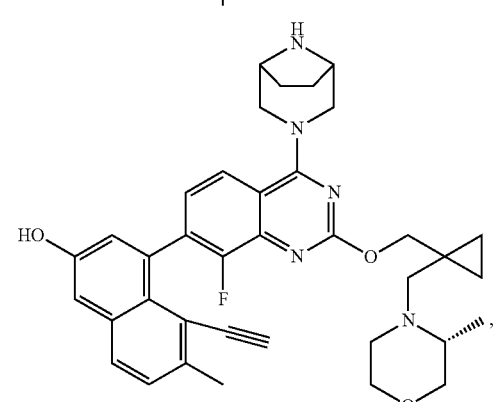

413
-continued
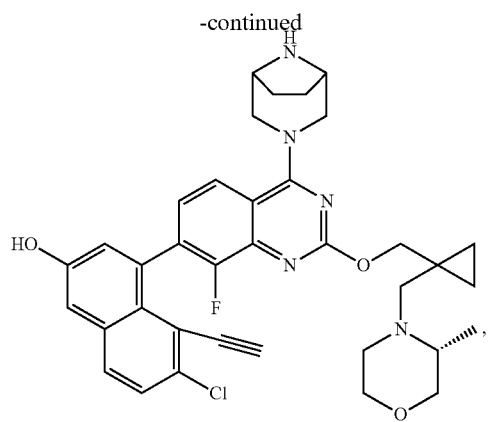
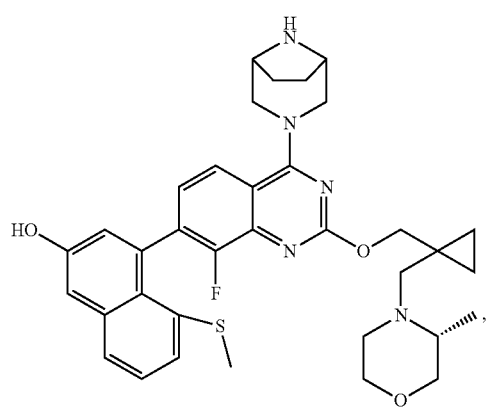
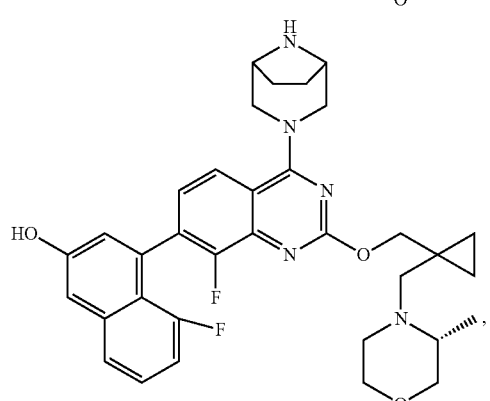
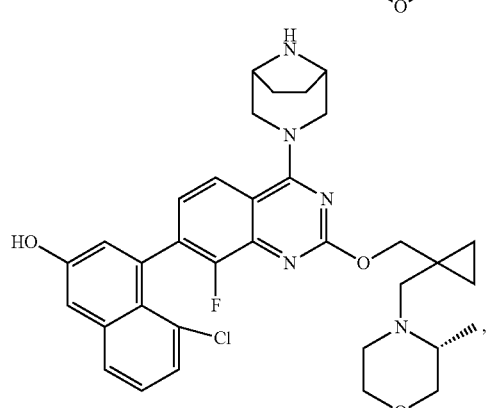
414
-continued
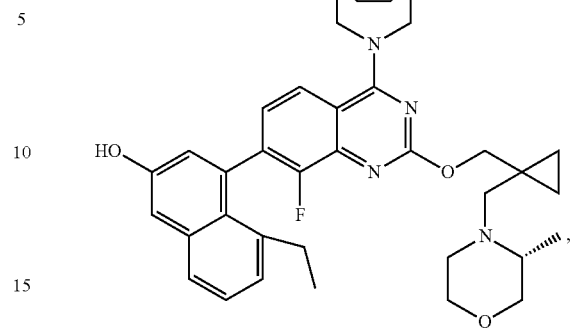
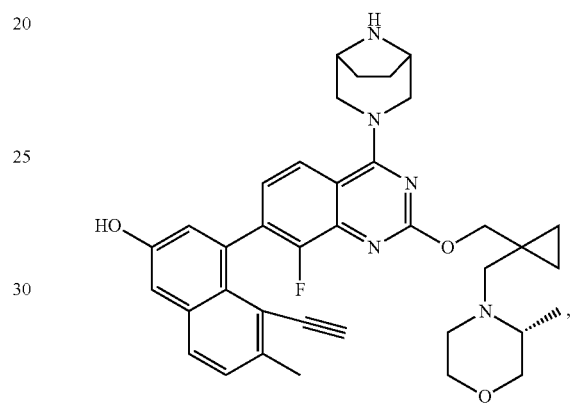
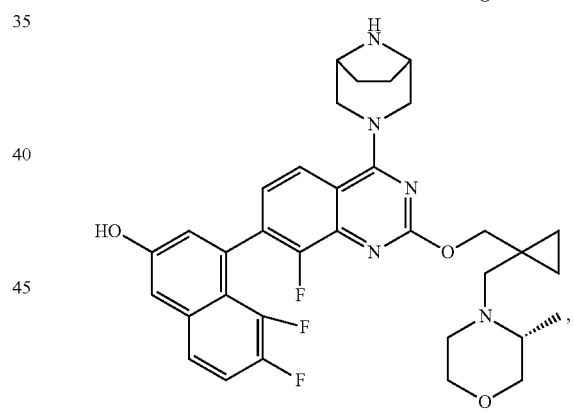
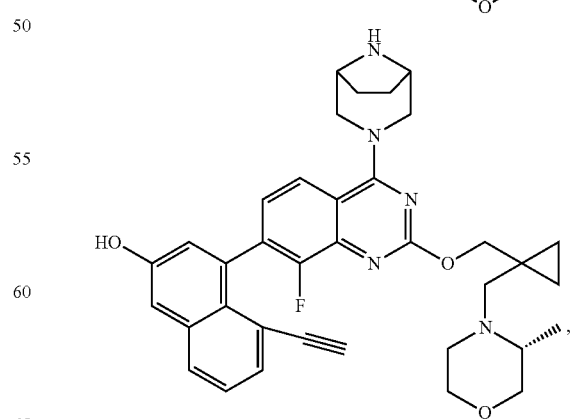

415
-continued
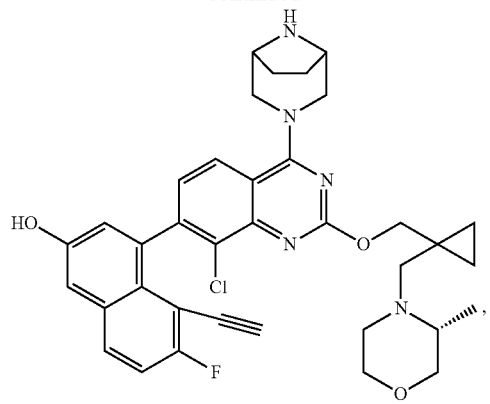
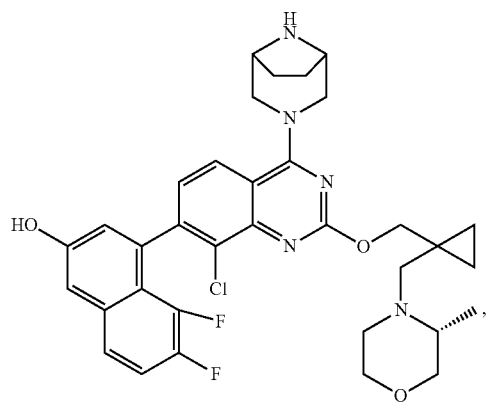
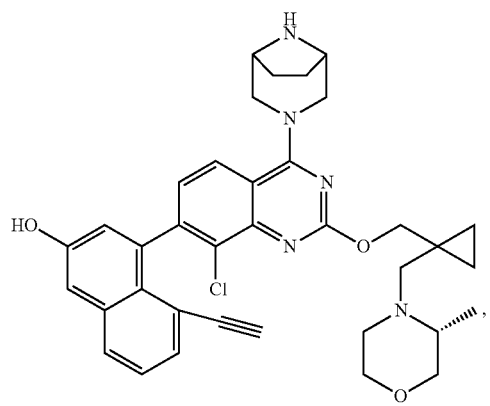
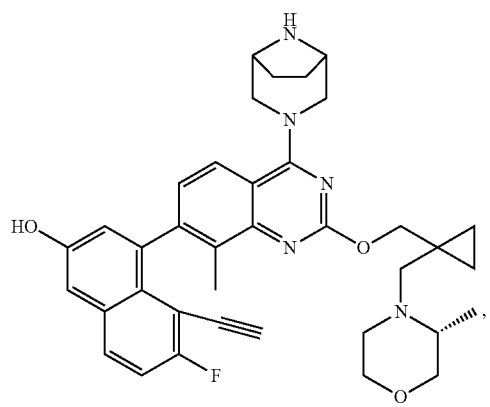
416
-continued
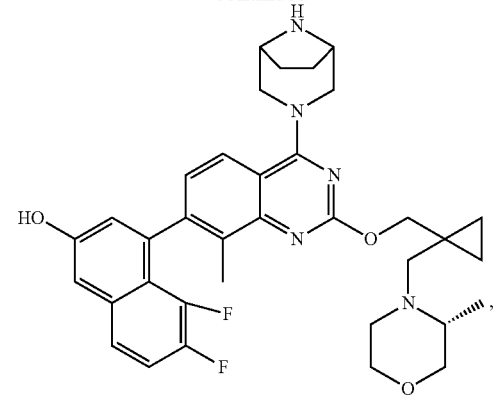
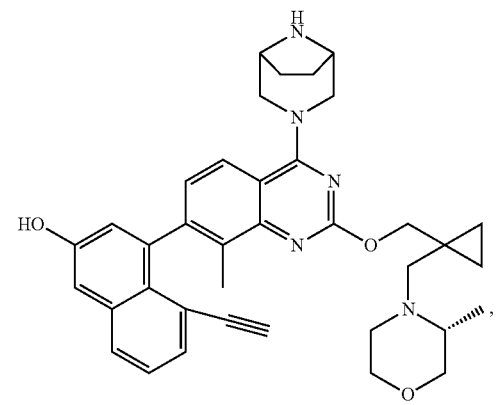
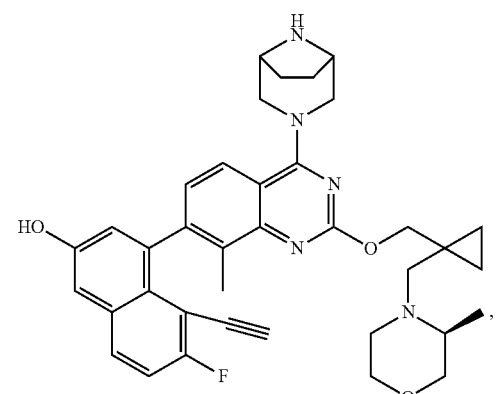
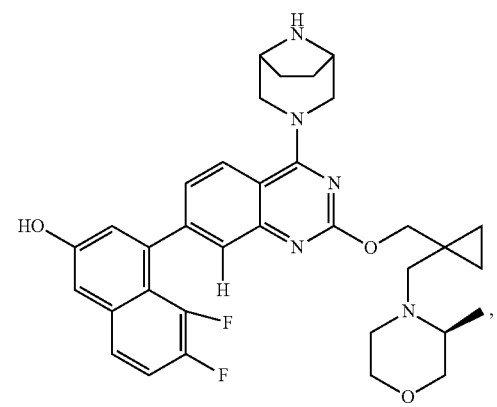

417
-continued
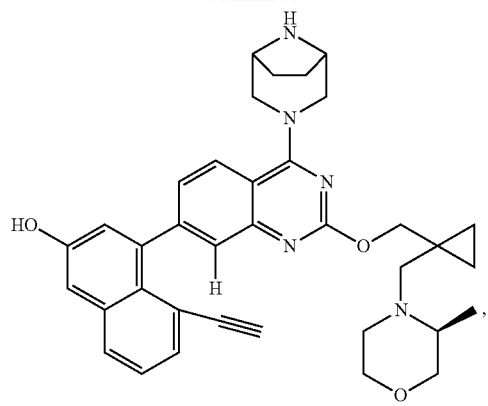
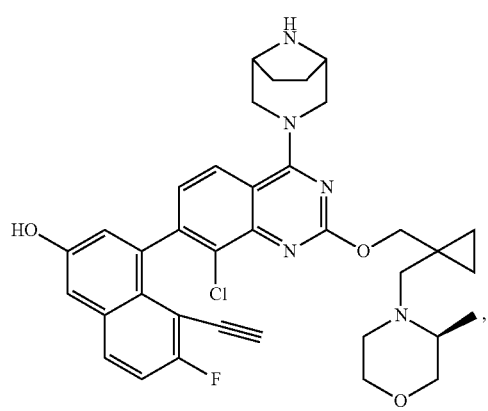
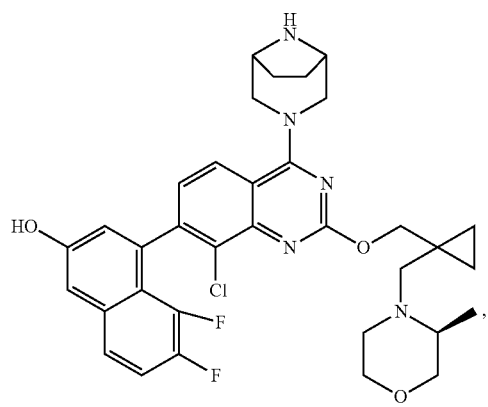
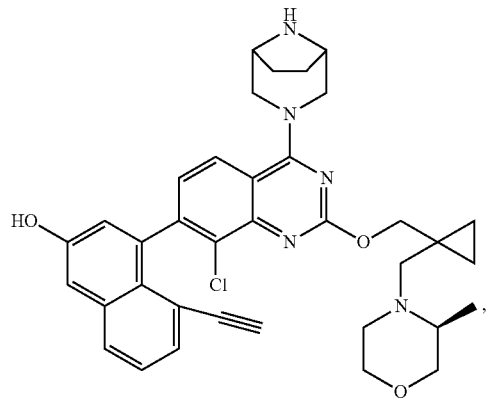
418
-continued
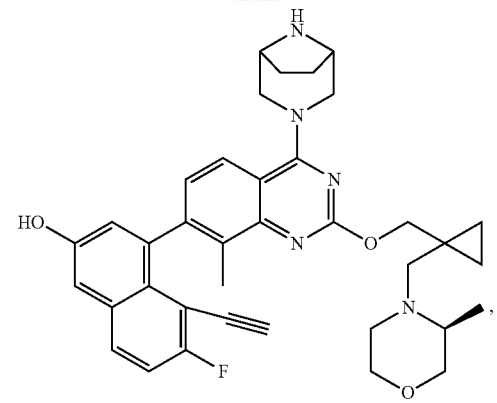
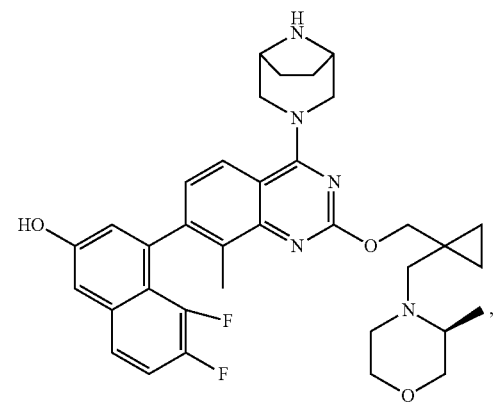
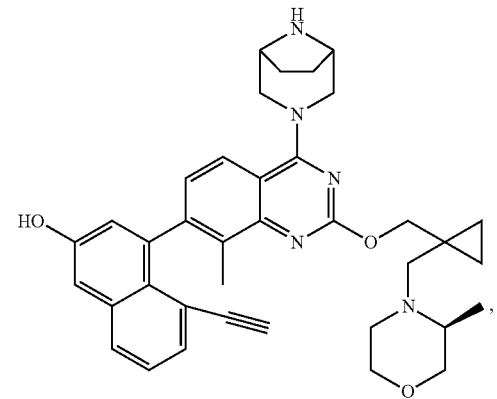
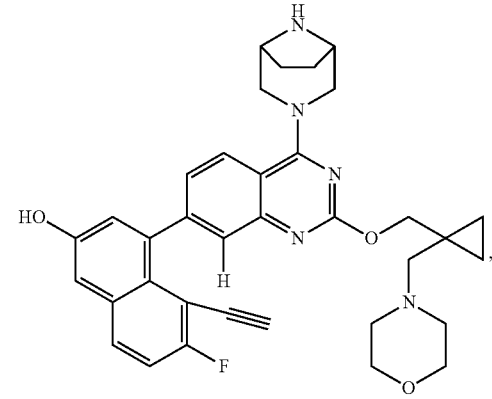

419
-continued
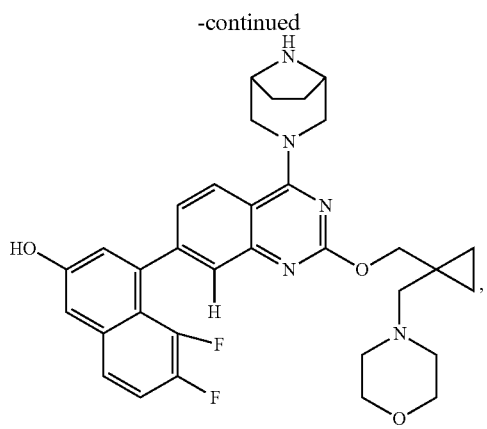
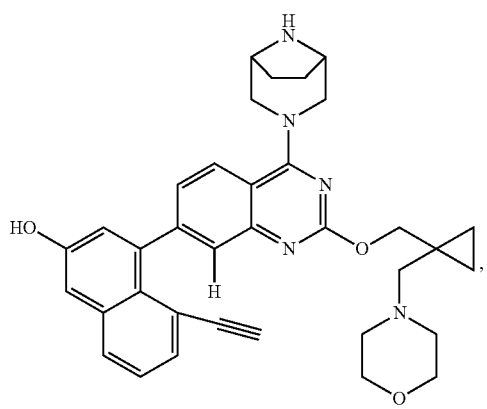
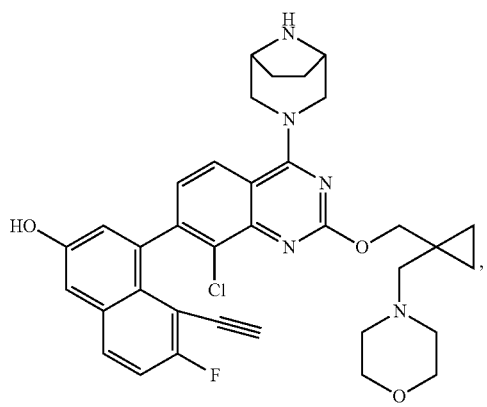
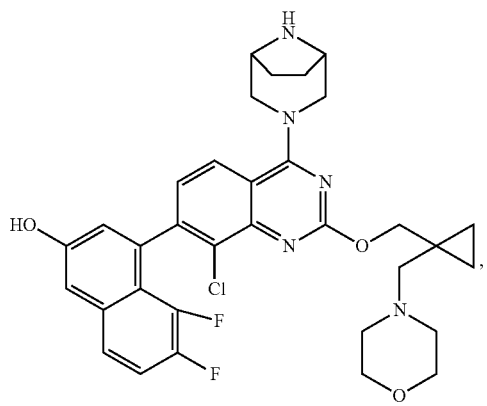
420
-continued
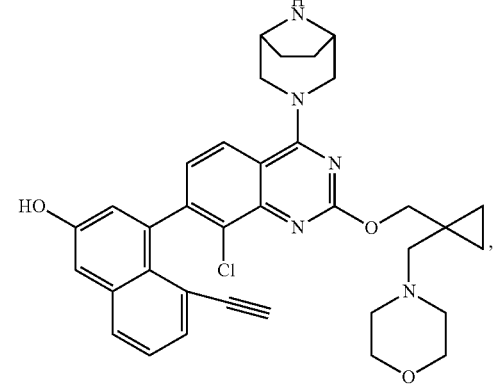
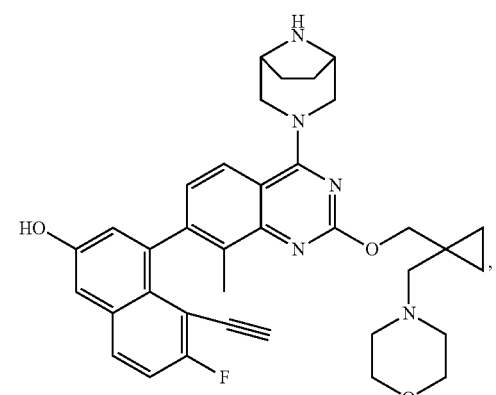
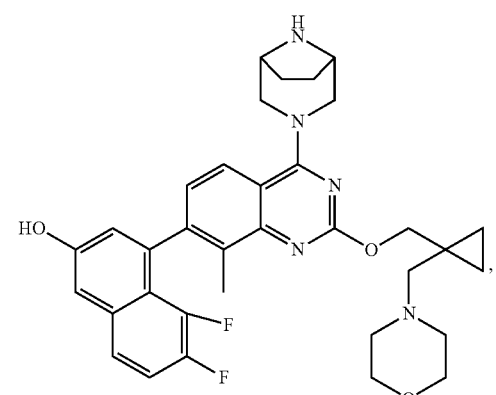
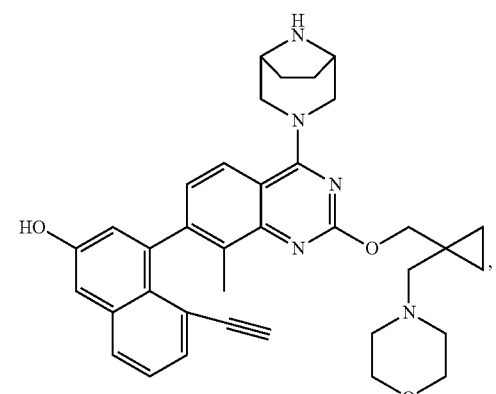

421
-continued
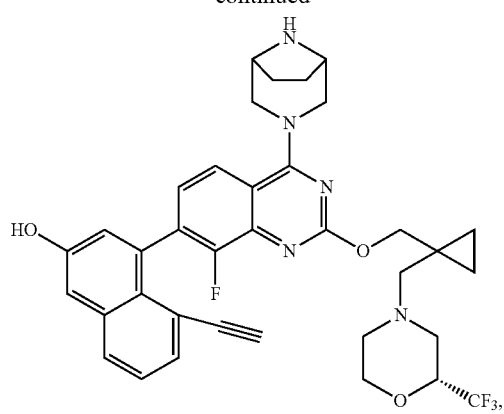
422
-continued
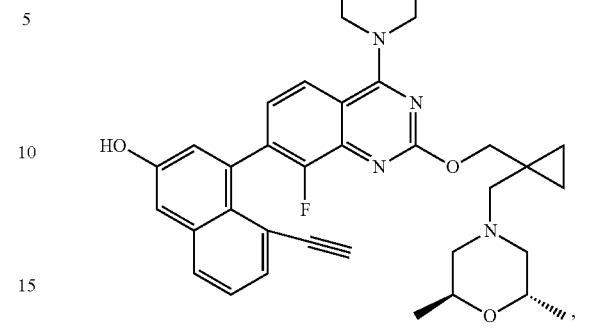
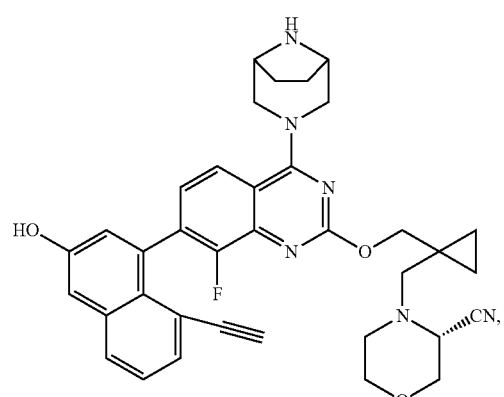
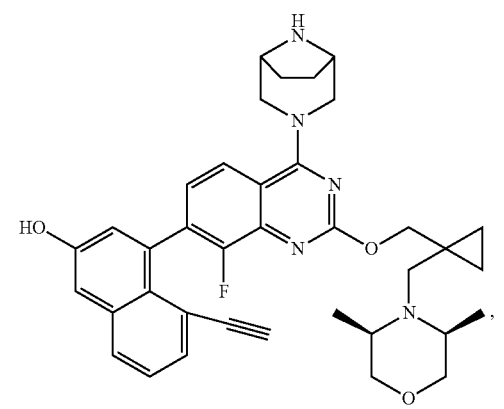
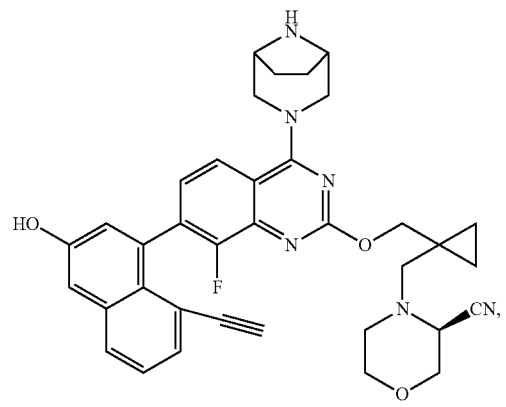
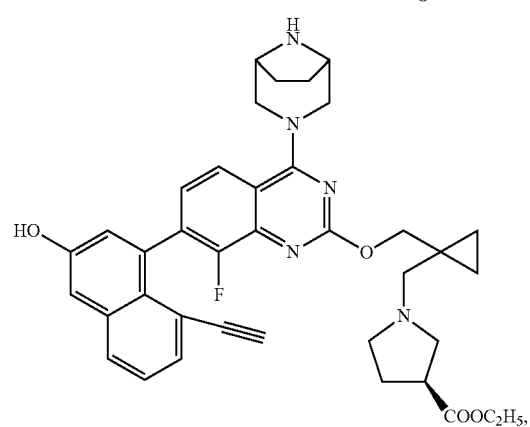

423
-continued
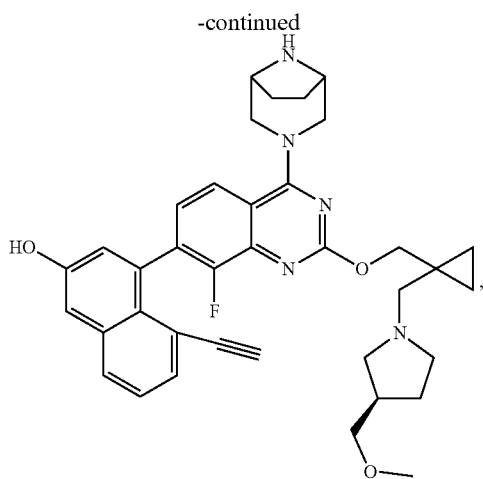
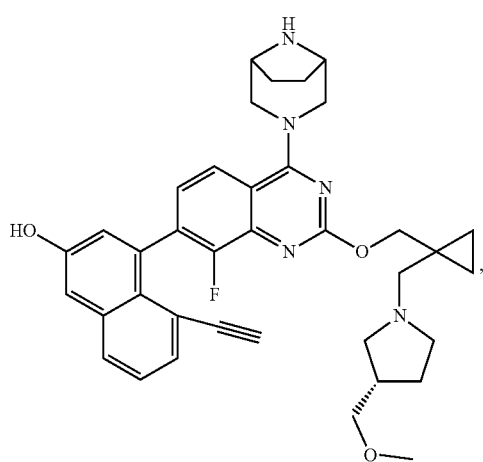
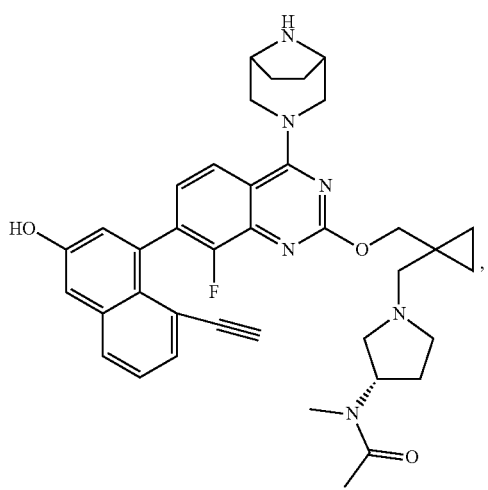
424
-continued
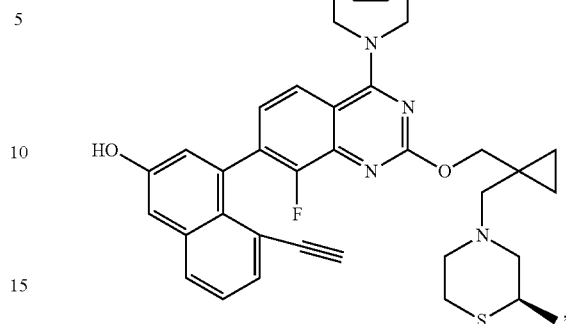

425
-continued
426
-continued
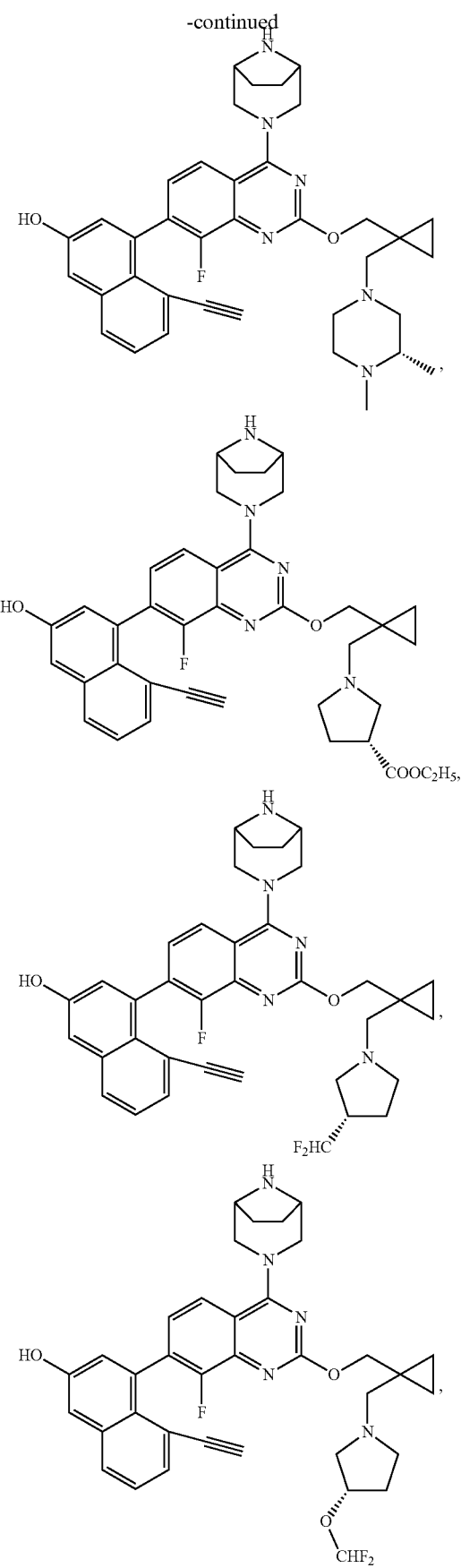
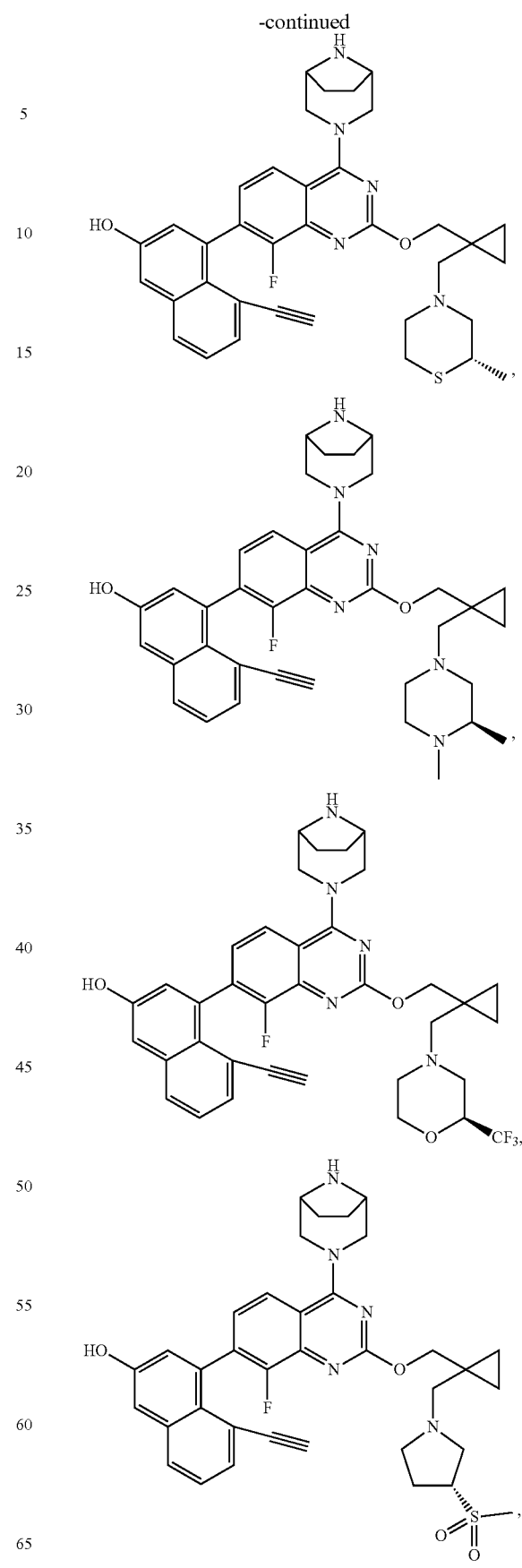

427
-continued
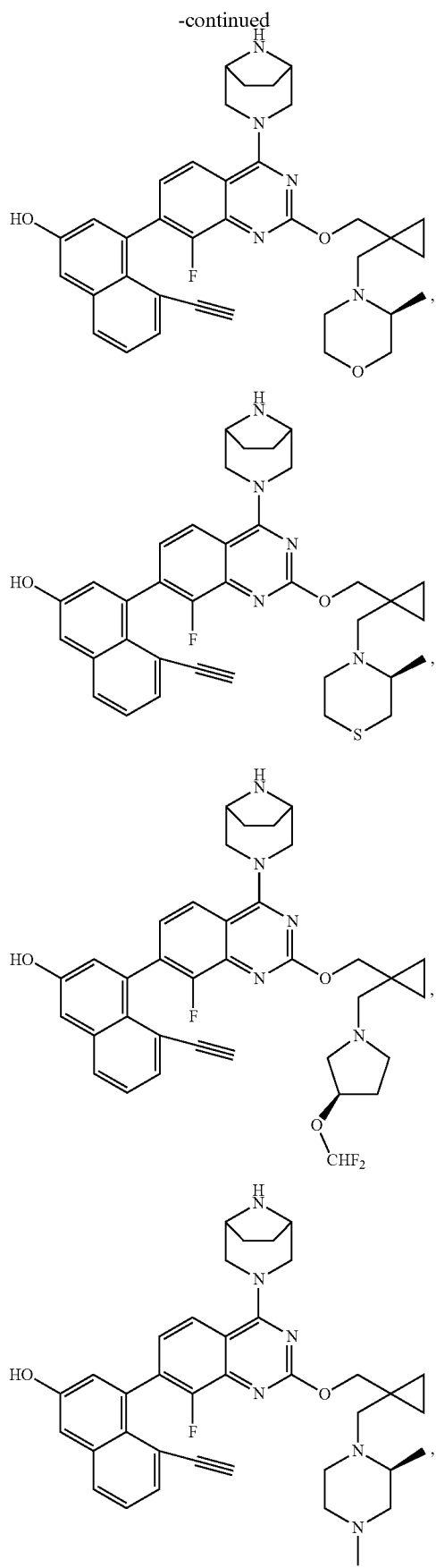
428
-continued
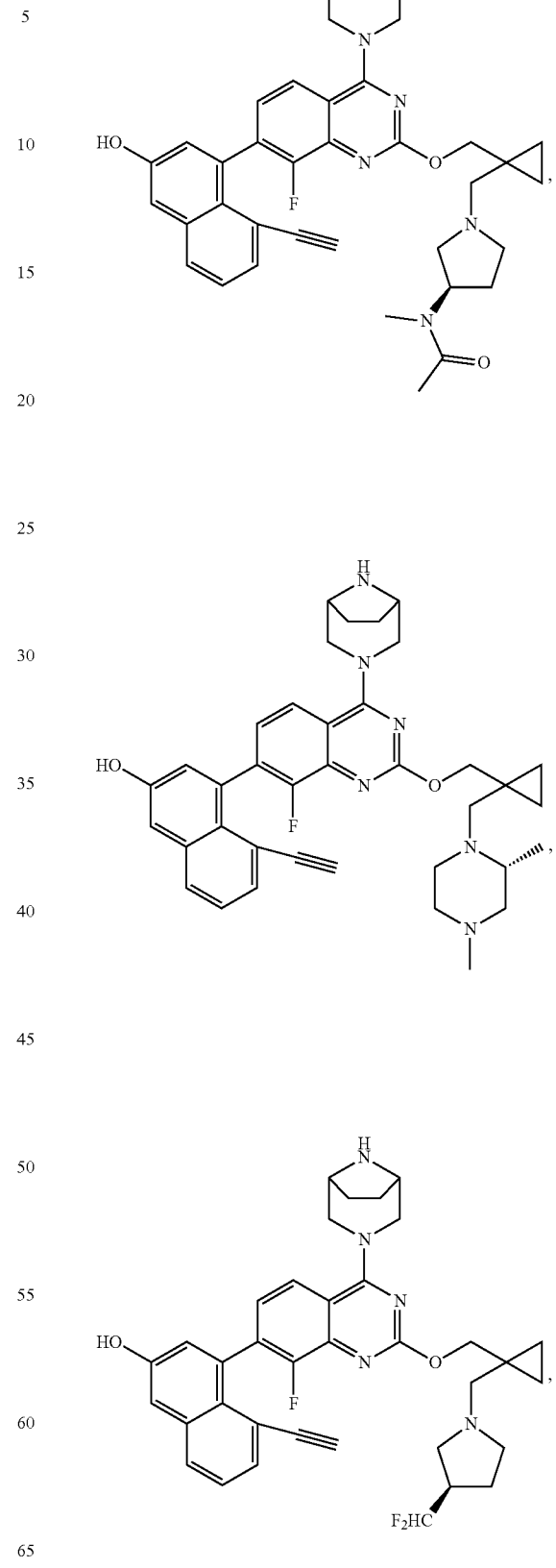

429
-continued
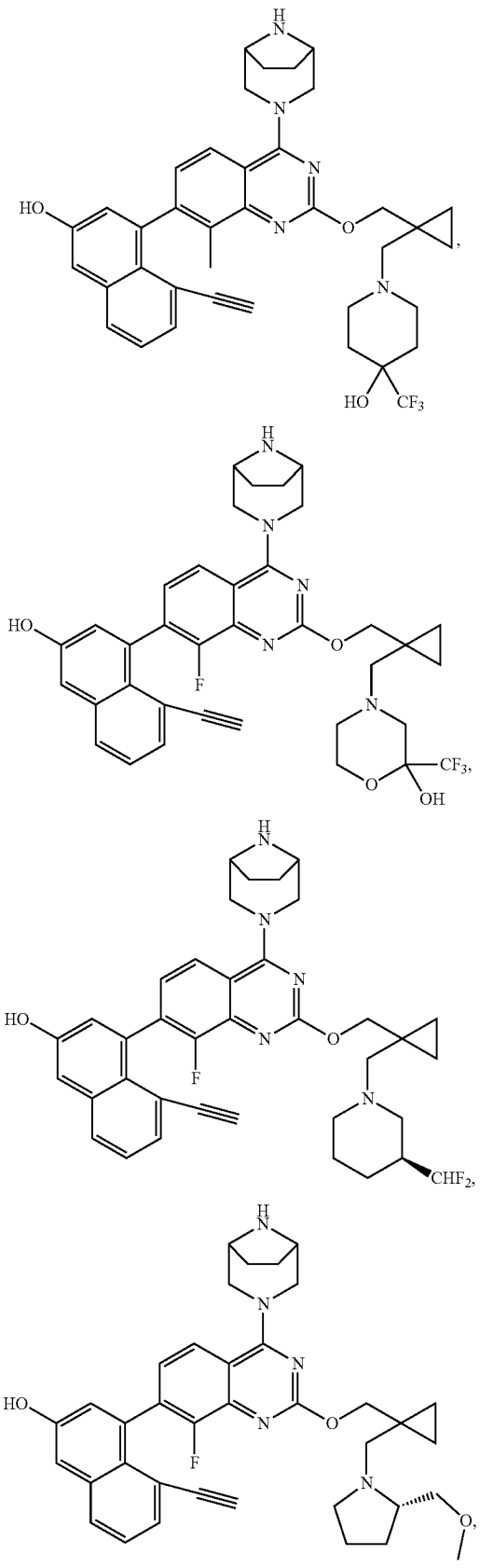
430
-continued
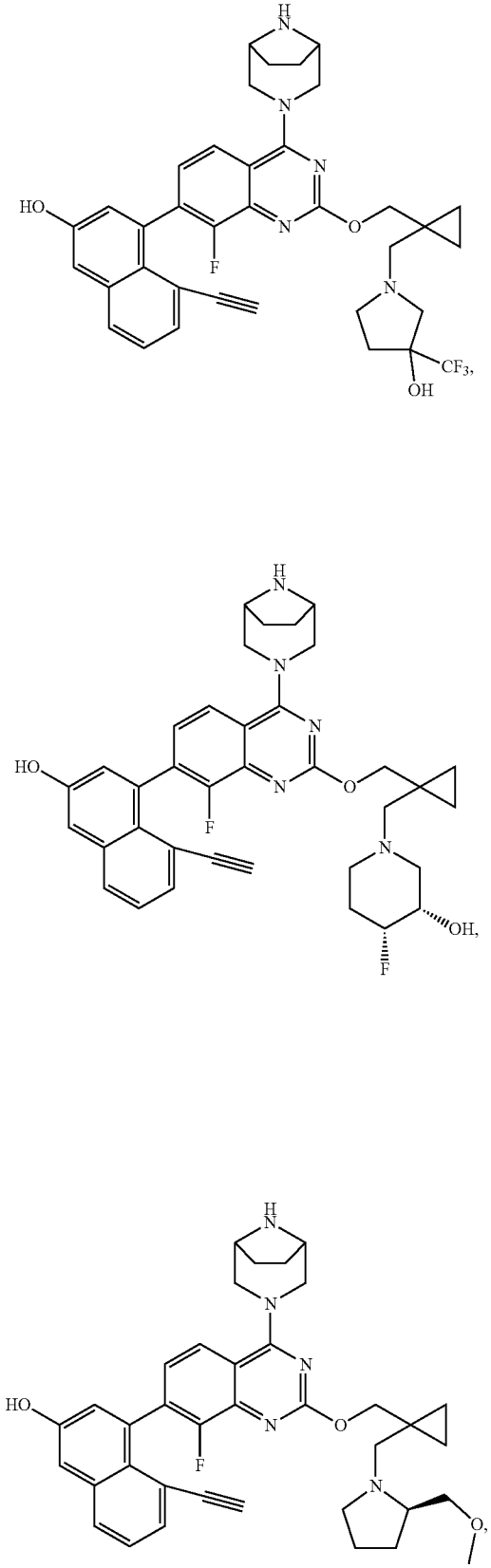

431
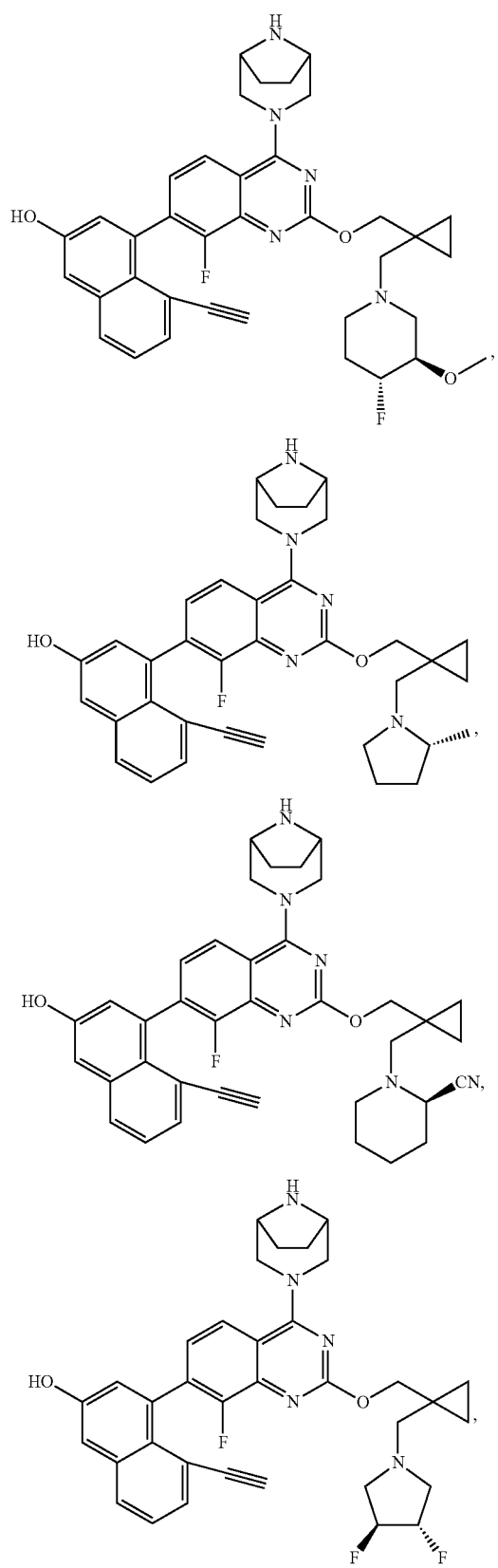 [SMILES: C#Cc1cccc2cc(O)cc(-c3ccc4c(N5CC6CCC(C5)N6)nc(OCC5(CN6CC[C@@H](F)[C@H](OC)C6)CC5)nc4c3F)c12 ; C#Cc1cccc2cc(O)cc(-c3ccc4c(N5CC6CCC(C5)N6)nc(OCC5(CN6CCC[C@H]6C)CC5)nc4c3F)c12 ; C#Cc1cccc2cc(O)cc(-c3ccc4c(N5CC6CCC(C5)N6)nc(OCC5(CN6CCCC[C@@H]6C#N)CC5)nc4c3F)c12 ; C#Cc1cccc2cc(O)cc(-c3ccc4c(N5CC6CCC(C5)N6)nc(OCC5(CN6C[C@H](F)[C@@H](F)C6)CC5)nc4c3F)c12]
432
-continued
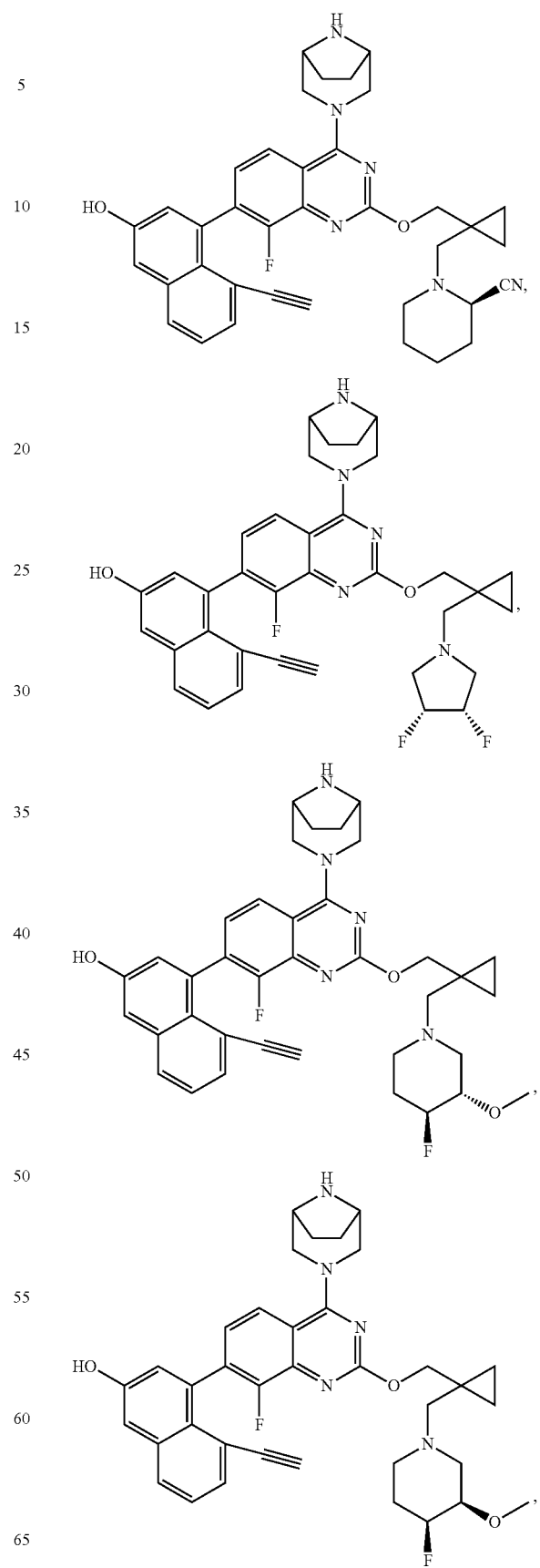

433
-continued
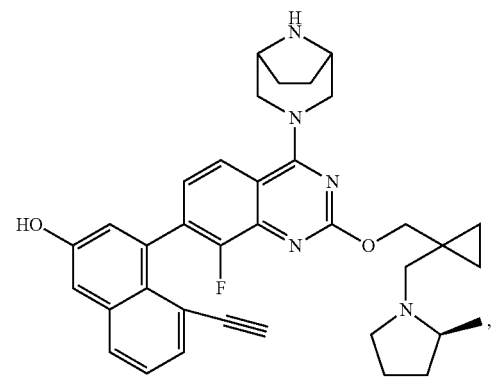
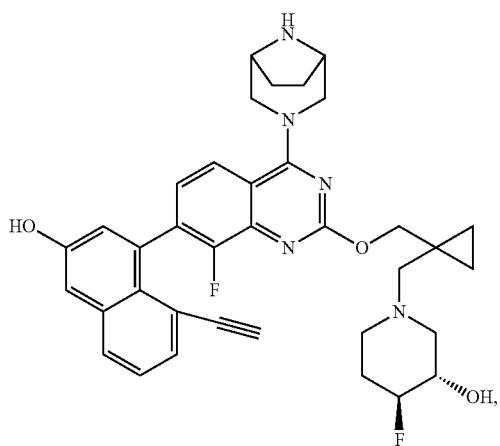
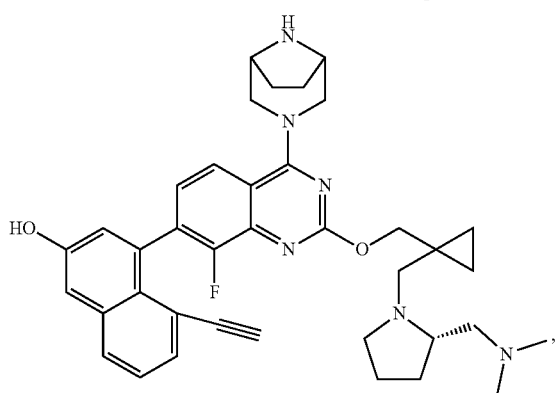
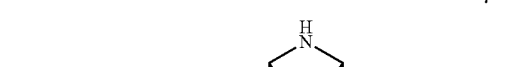
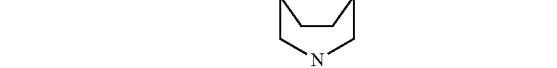
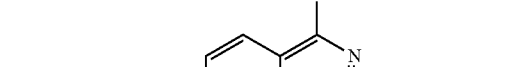
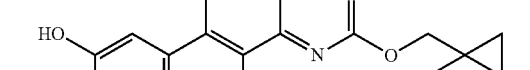
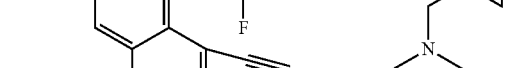

434
-continued
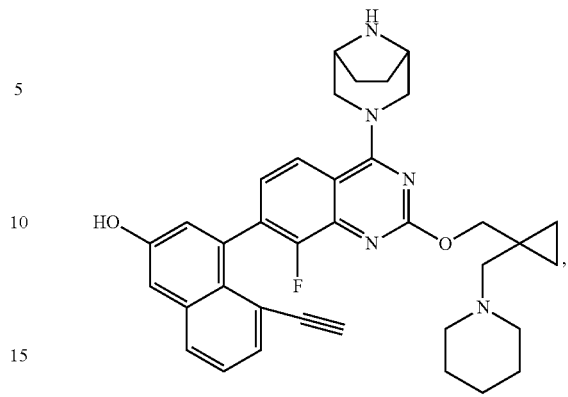
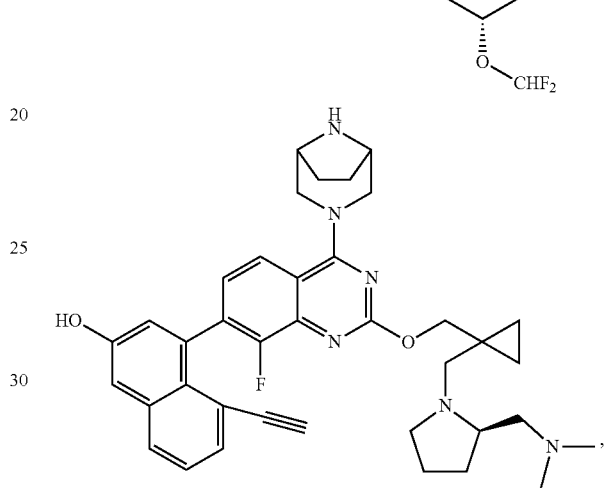
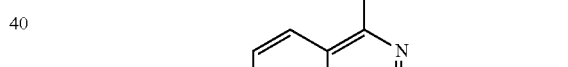
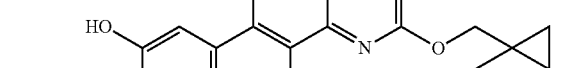
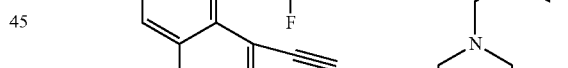
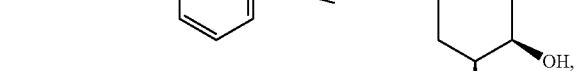
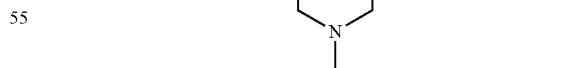
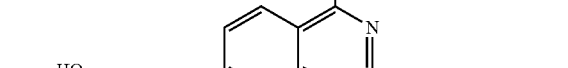
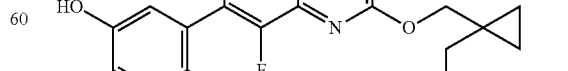

435
-continued
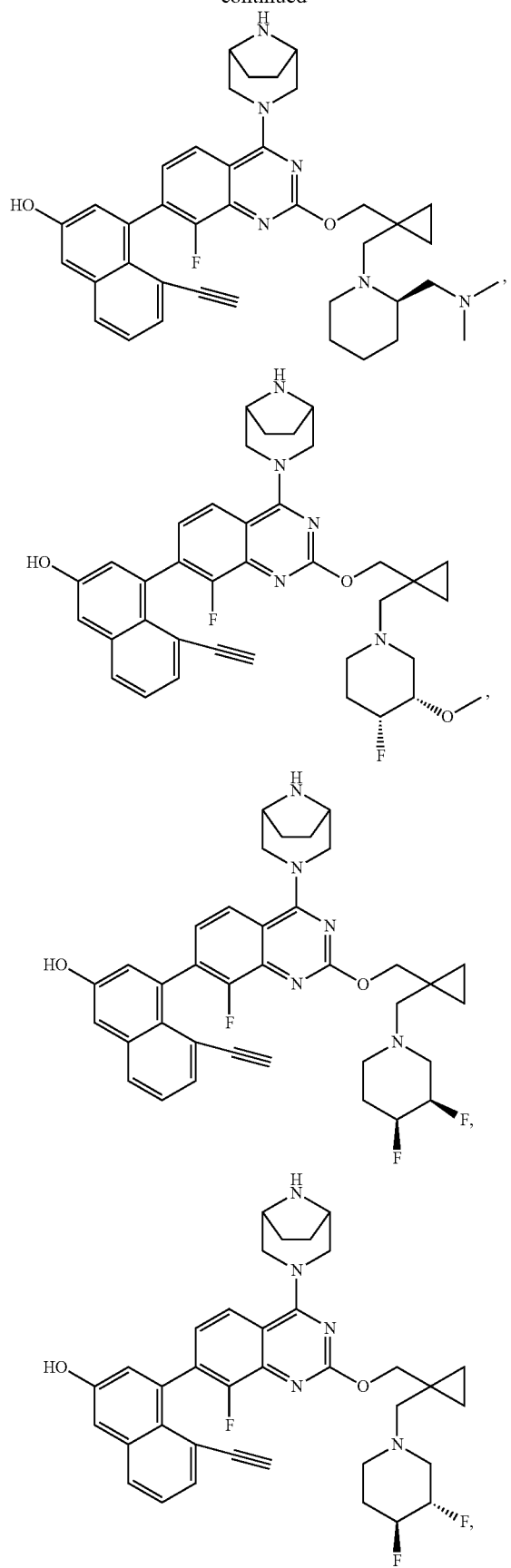
436
-continued
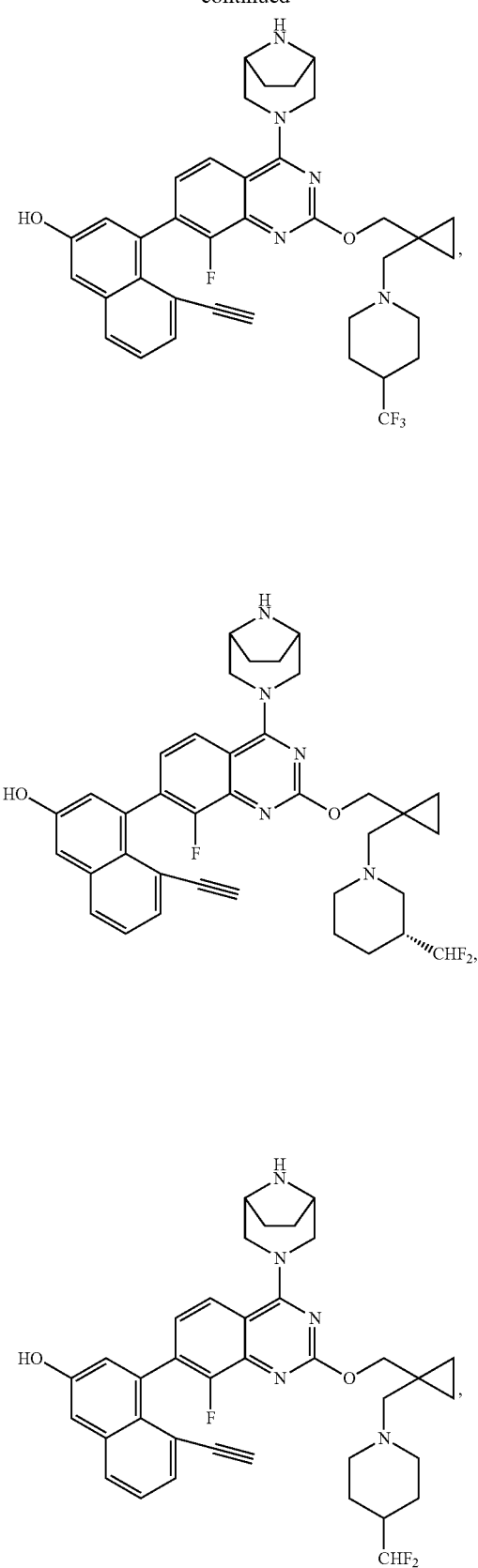

437
-continued
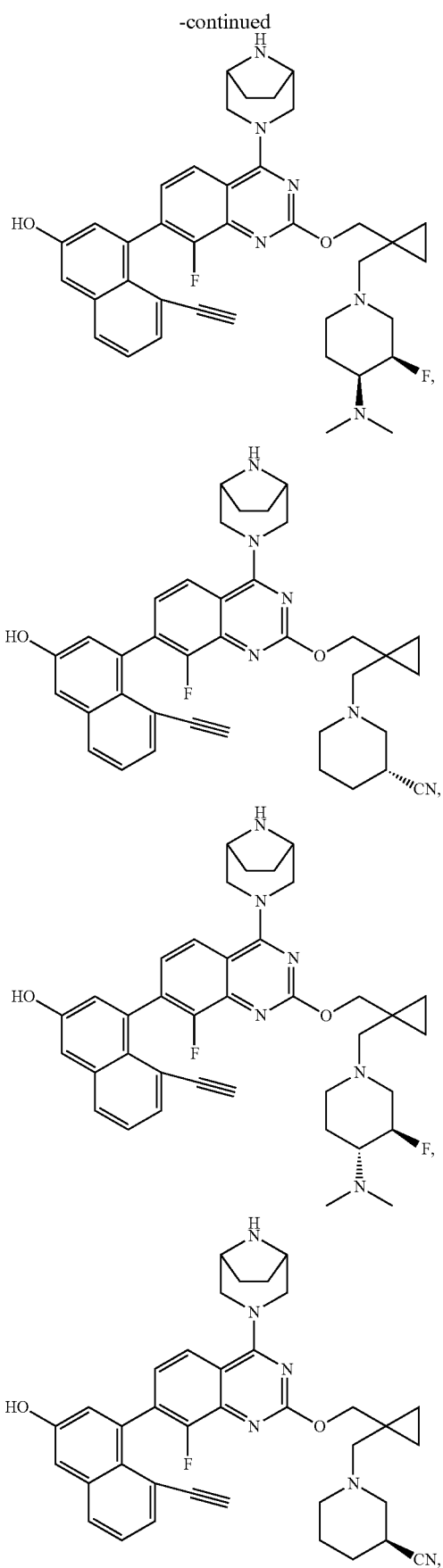
438
-continued
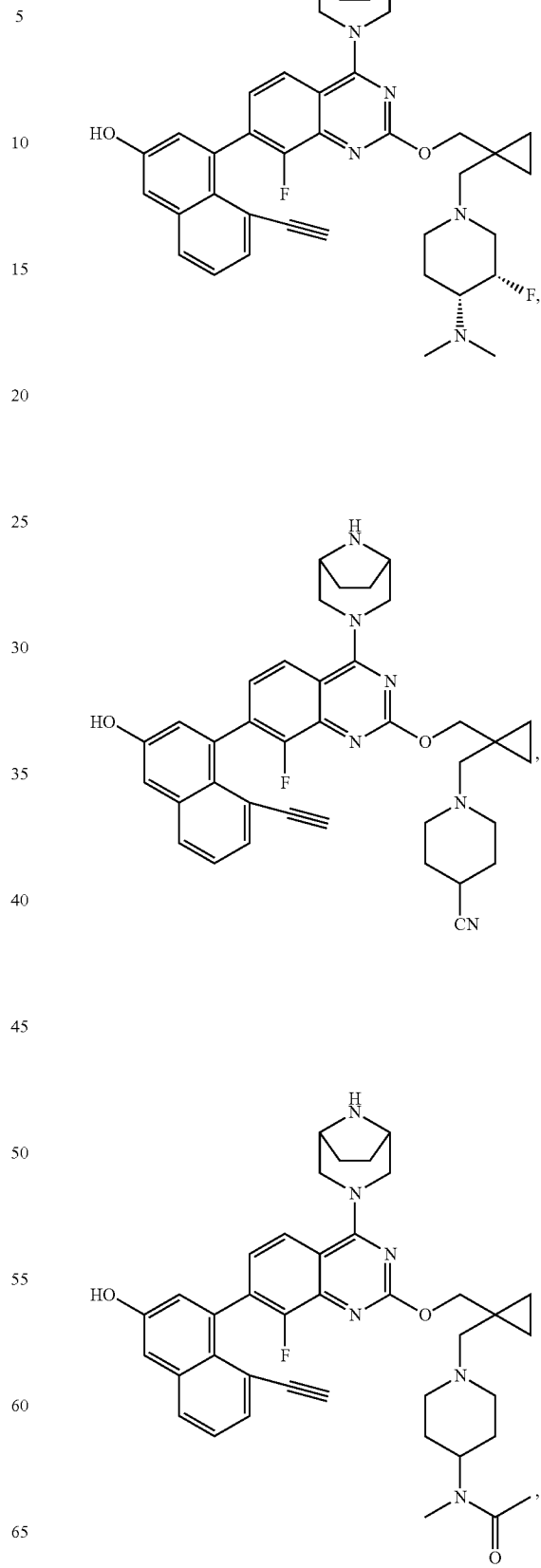

439
-continued
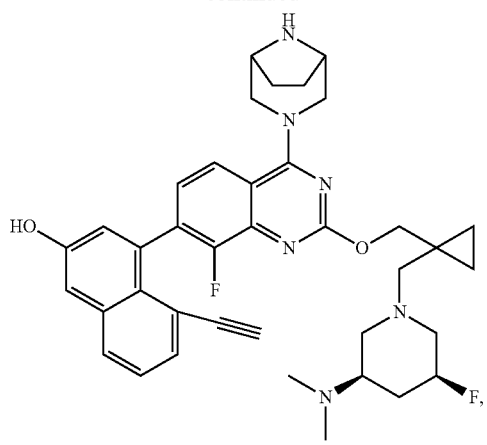
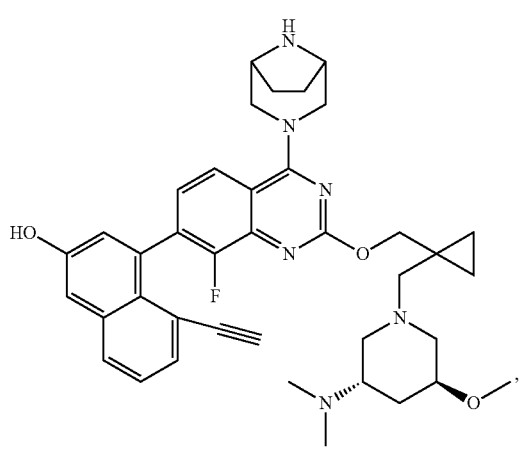
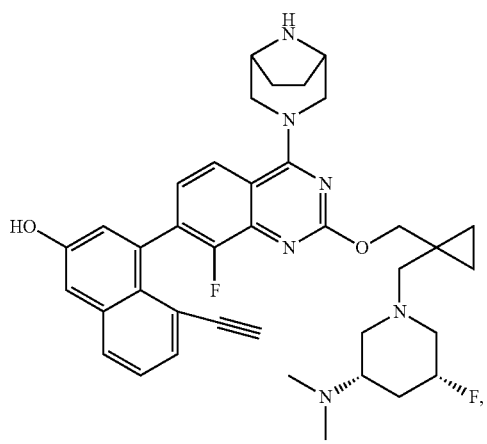
440
-continued
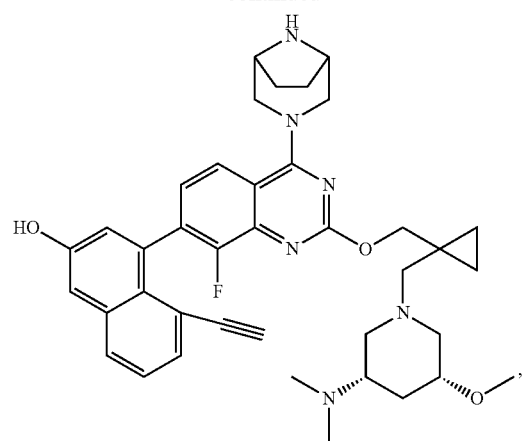
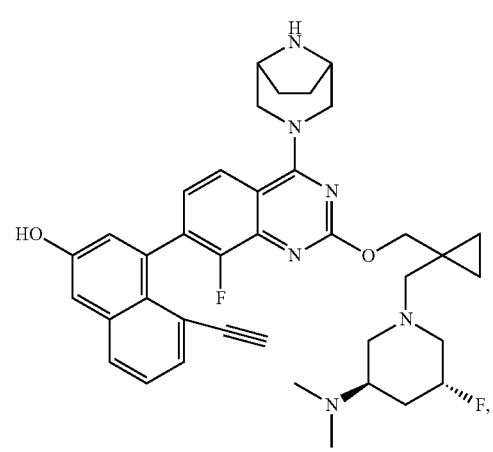
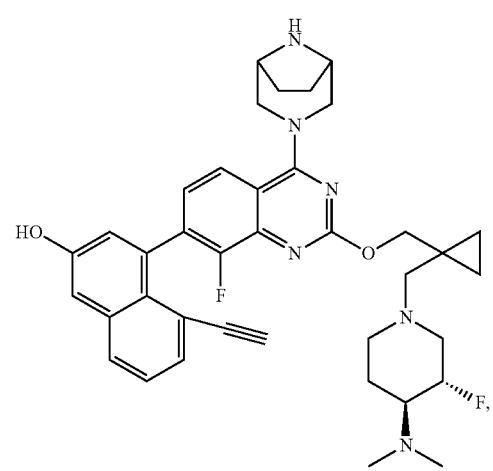

441
-continued
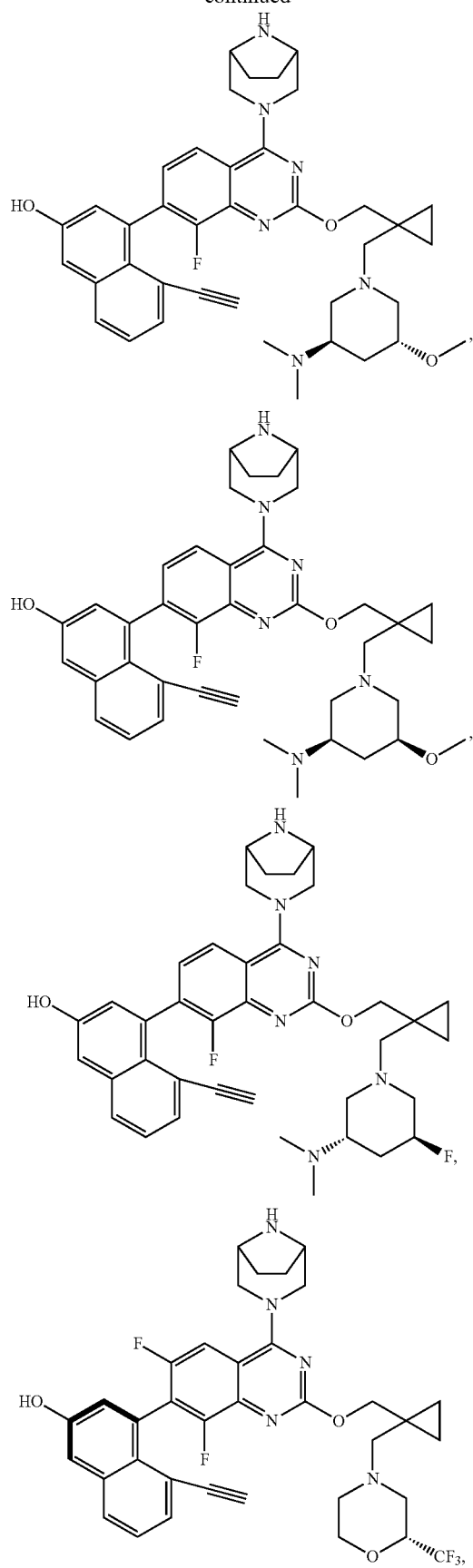
442
-continued
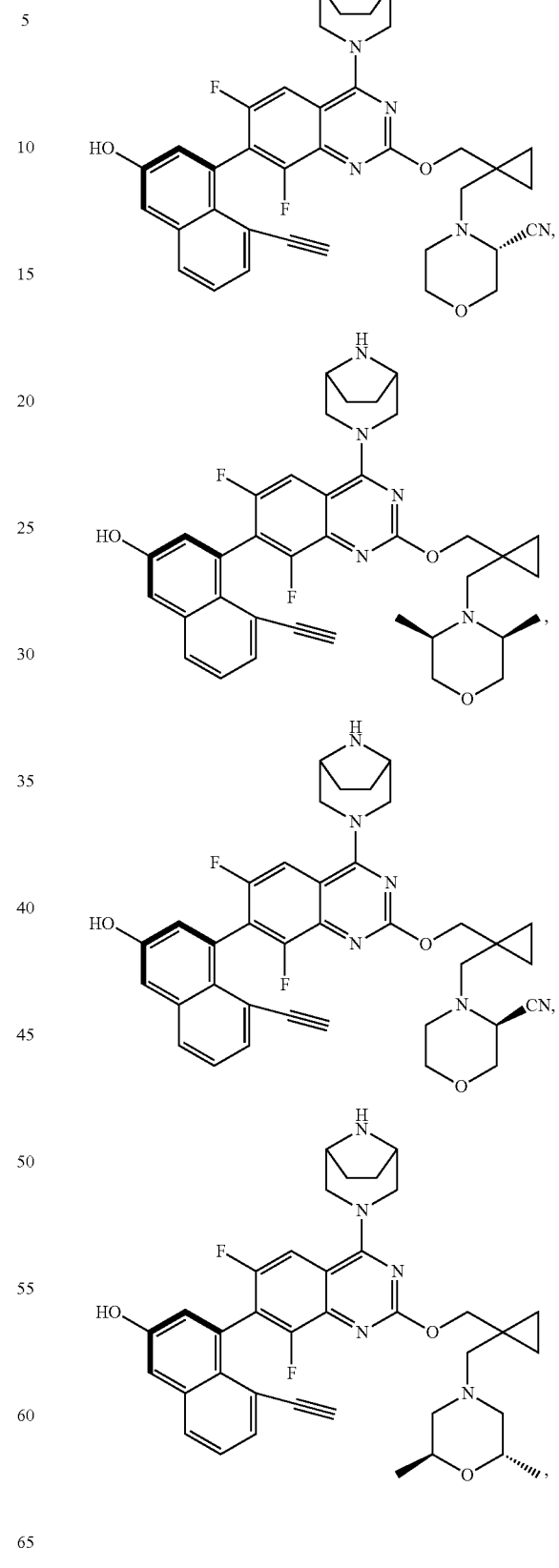

443
-continued
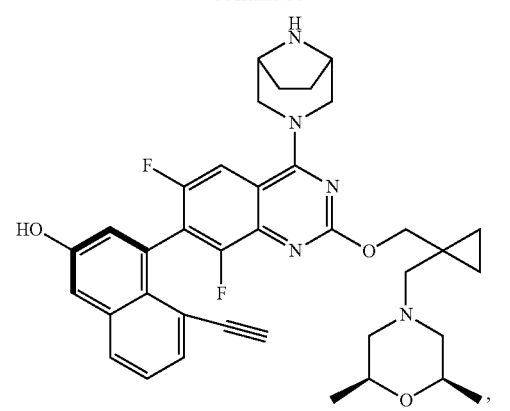
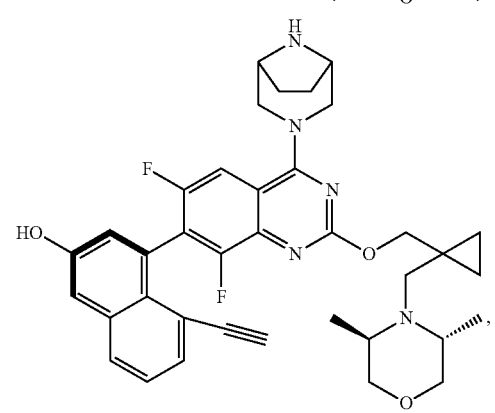
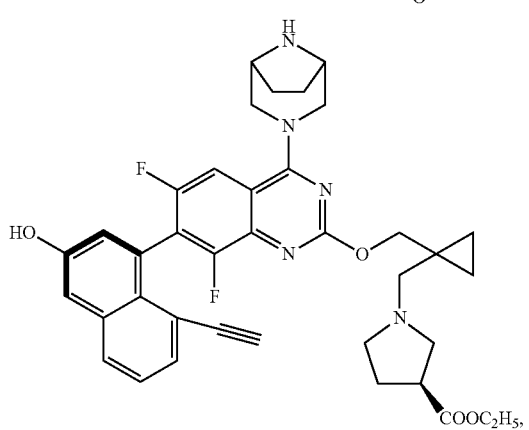
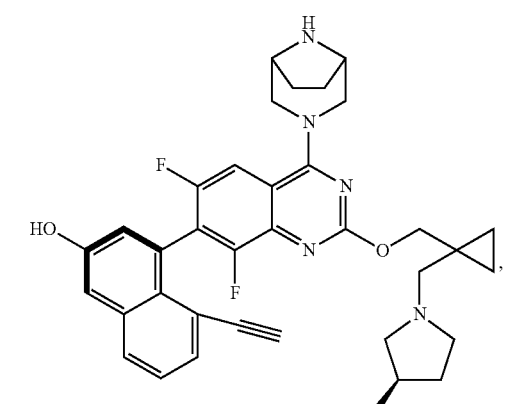
444
-continued
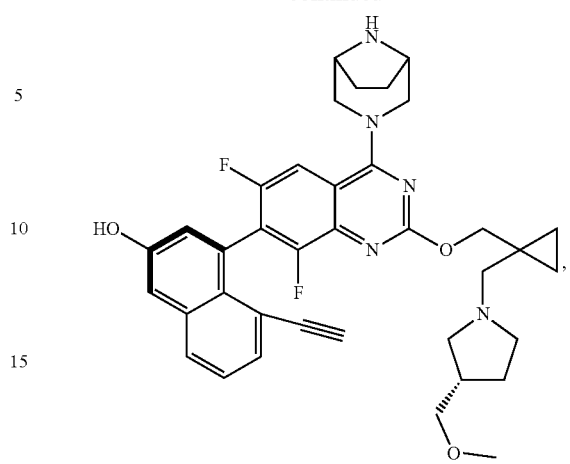
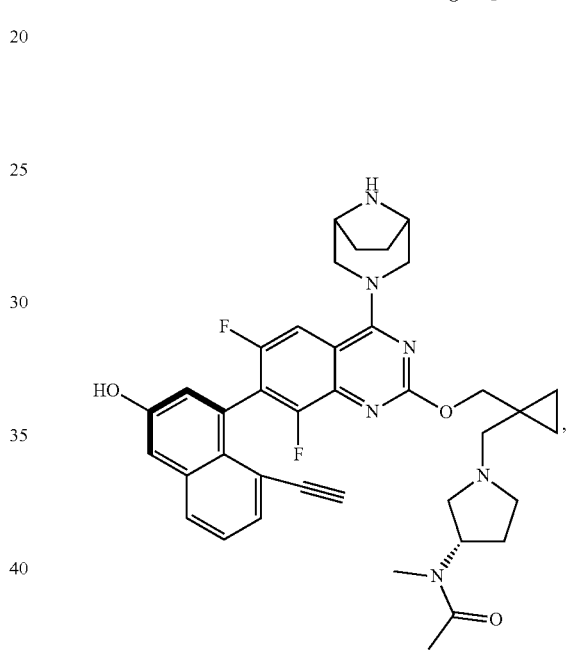
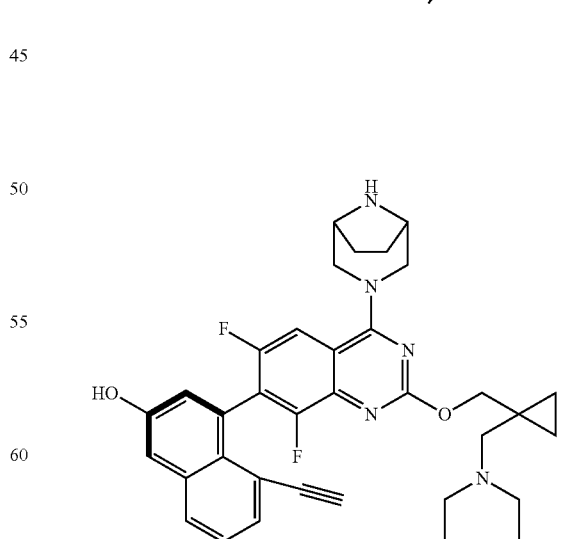

445
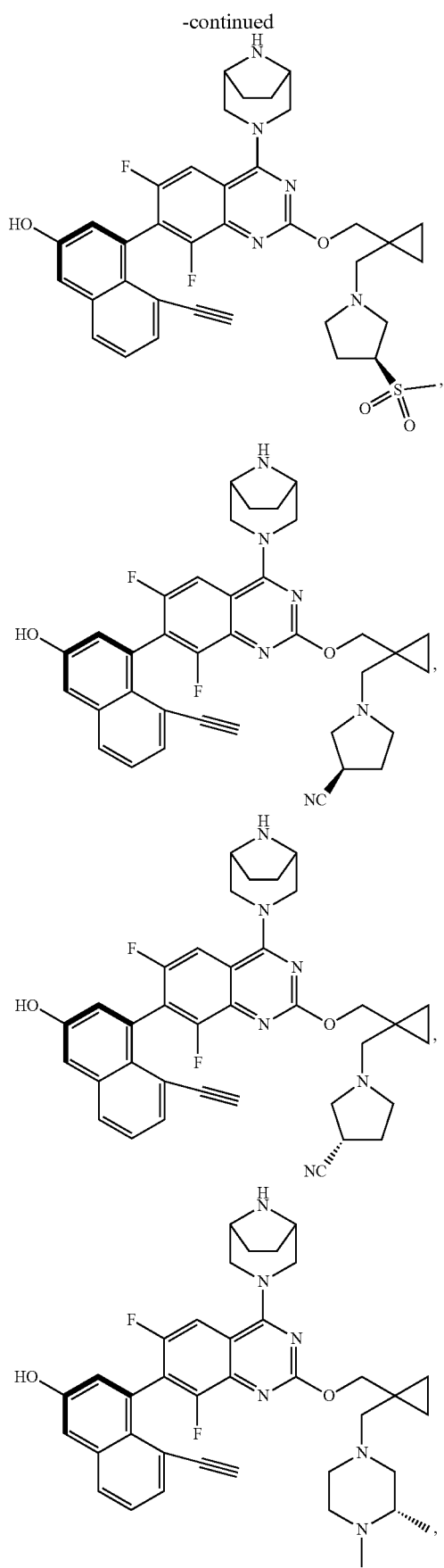
446
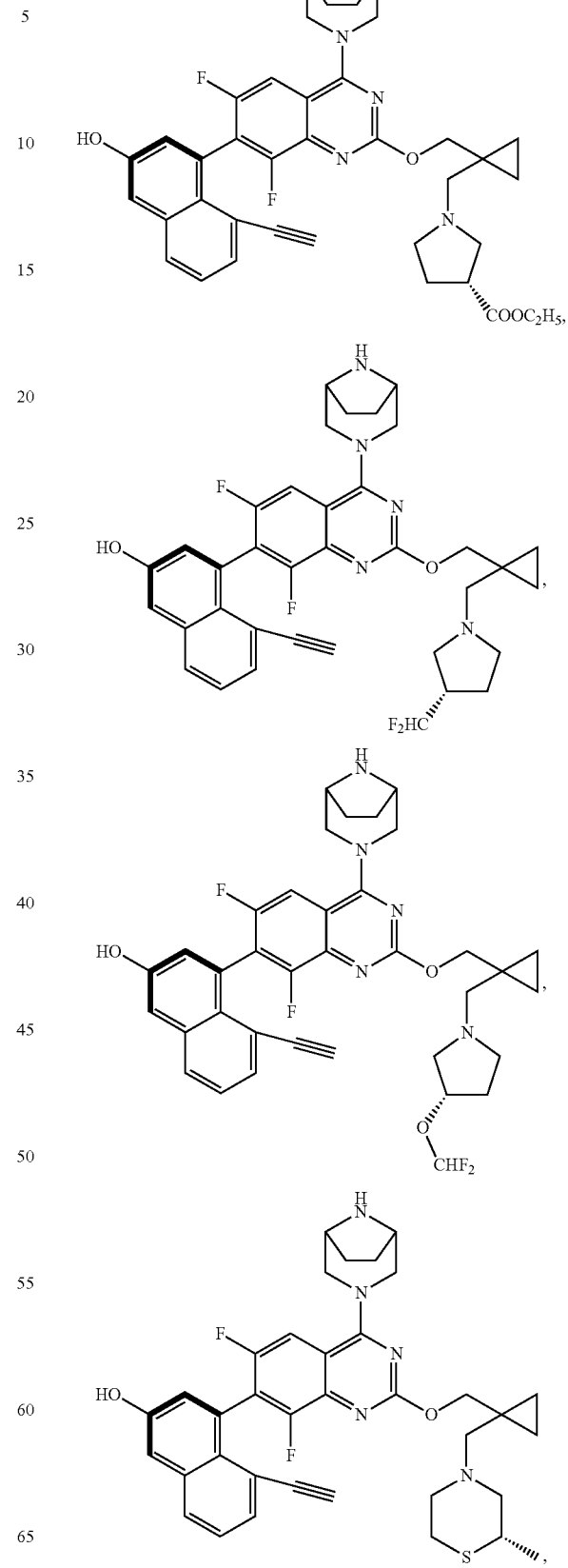

447
-continued
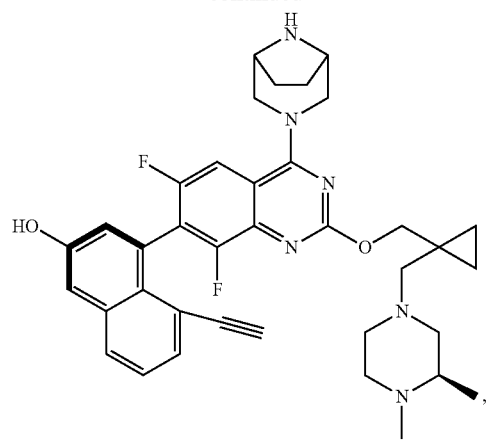
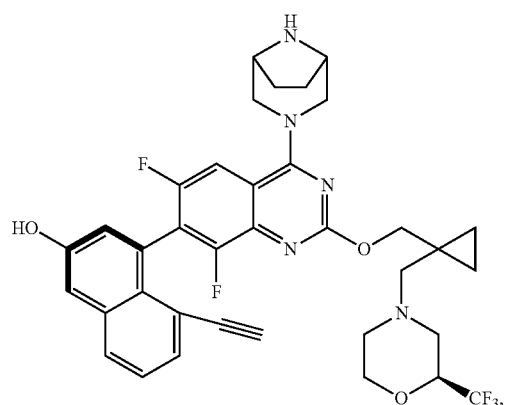
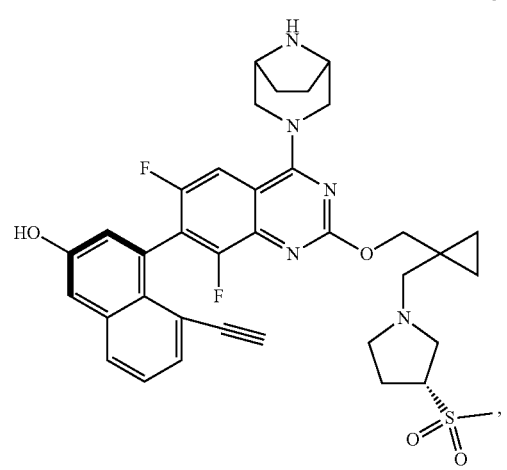
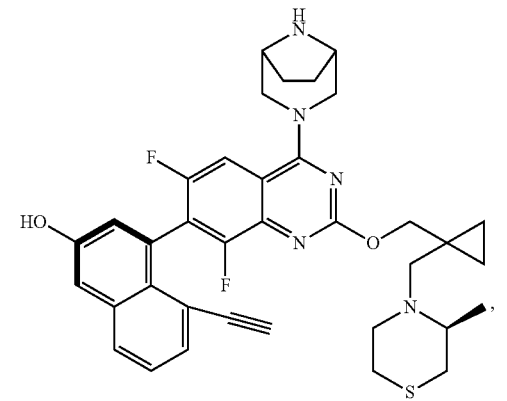
448
-continued
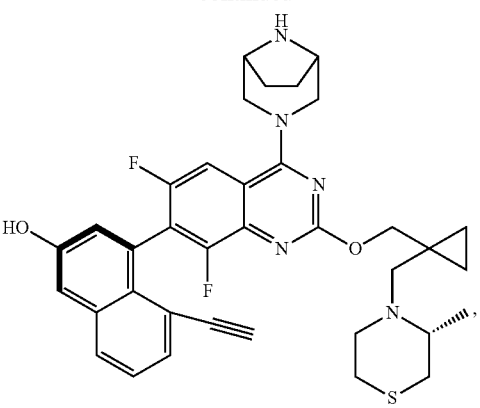
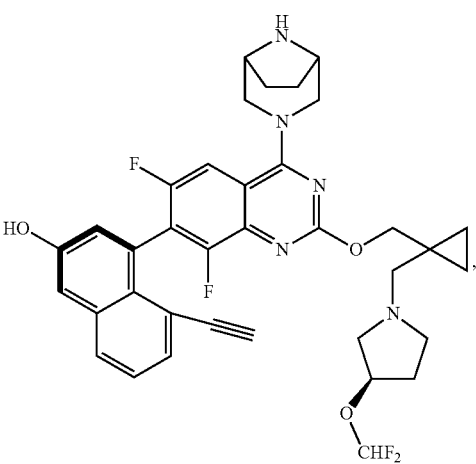

449
-continued
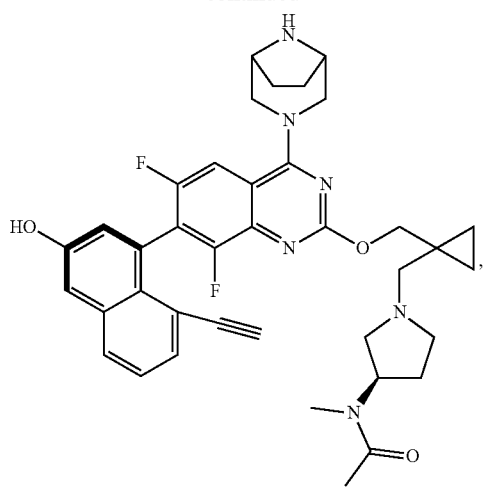
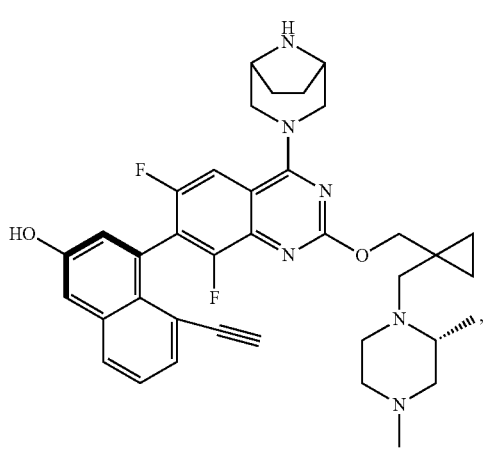
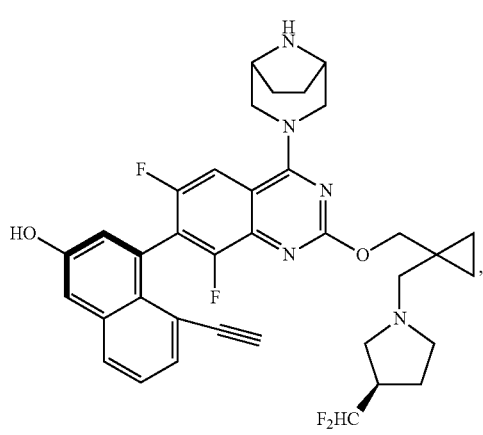
450
-continued
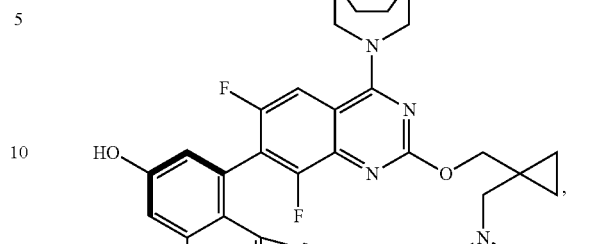
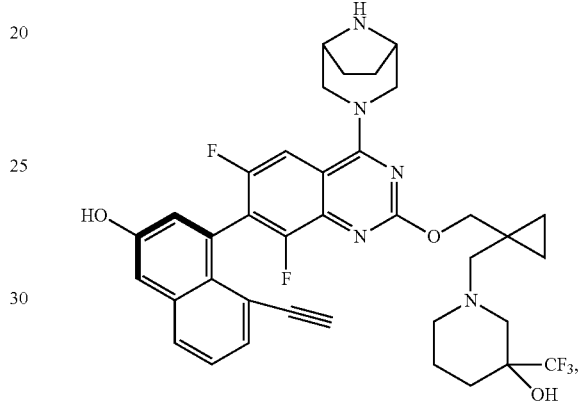
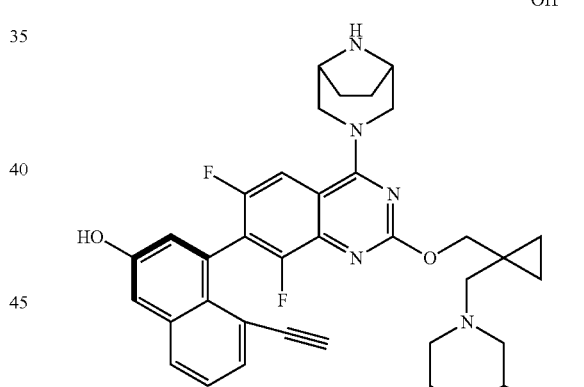
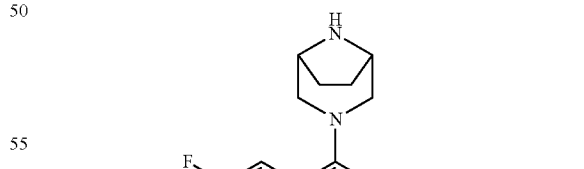

451
-continued
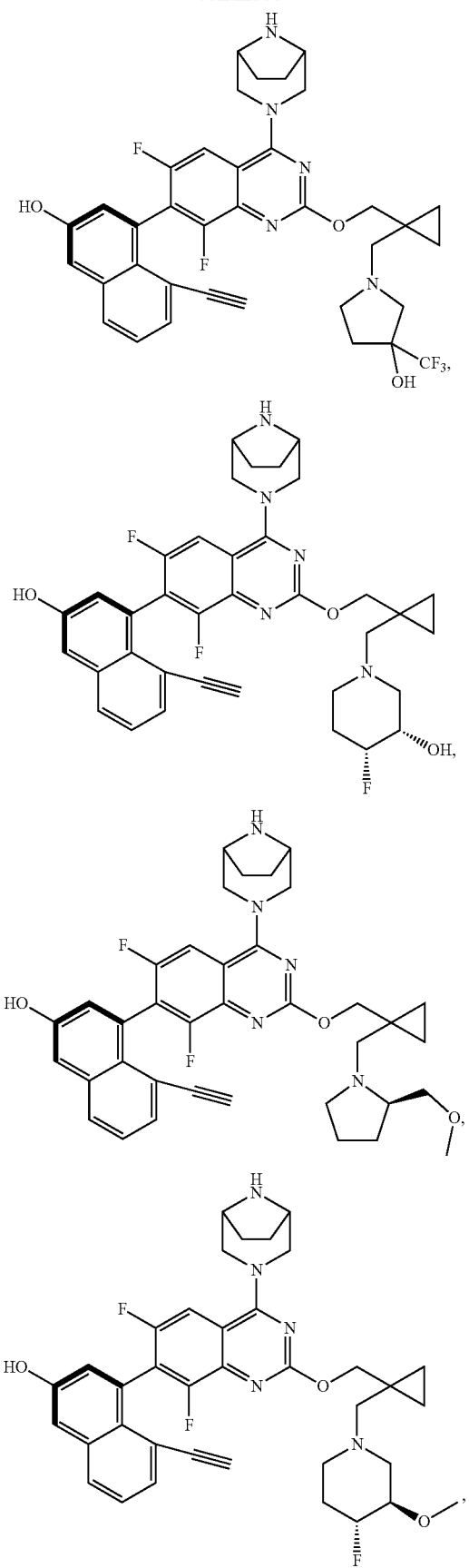
452
-continued
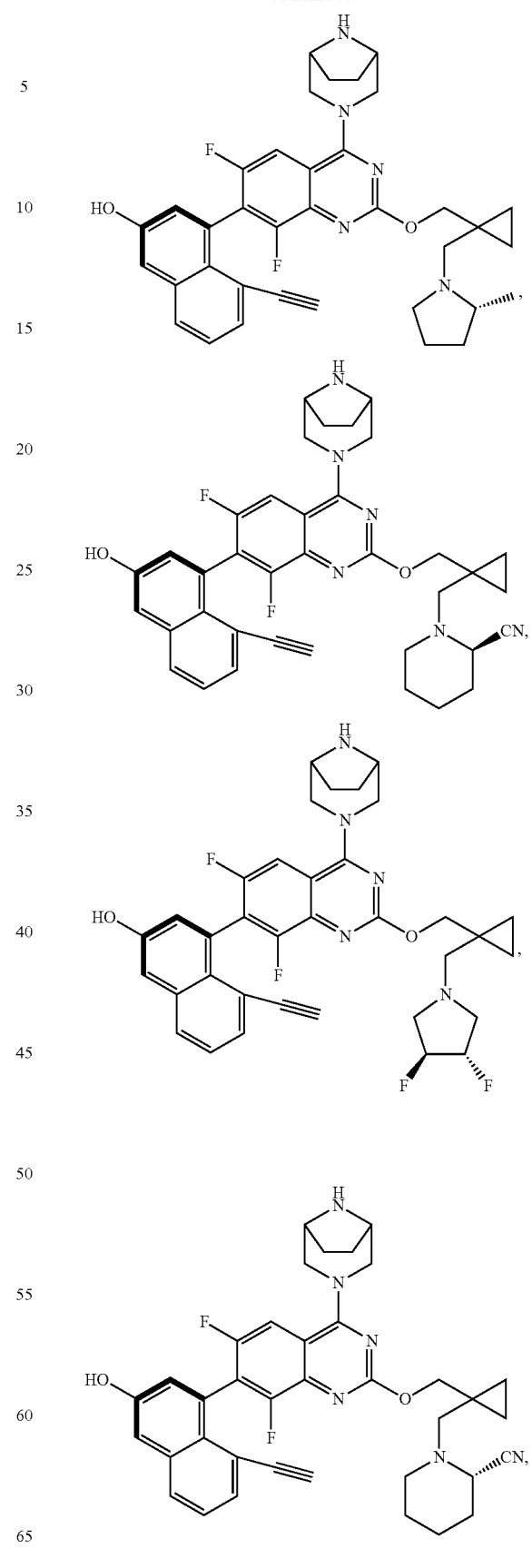

453
-continued
454
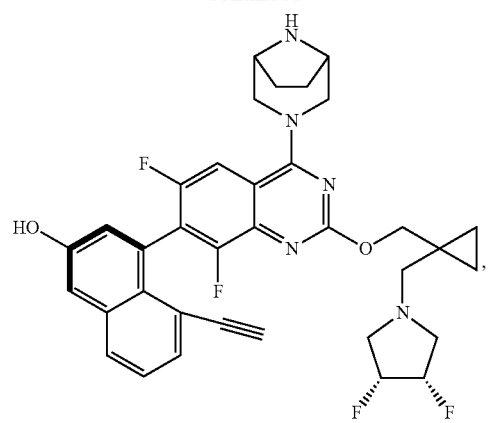
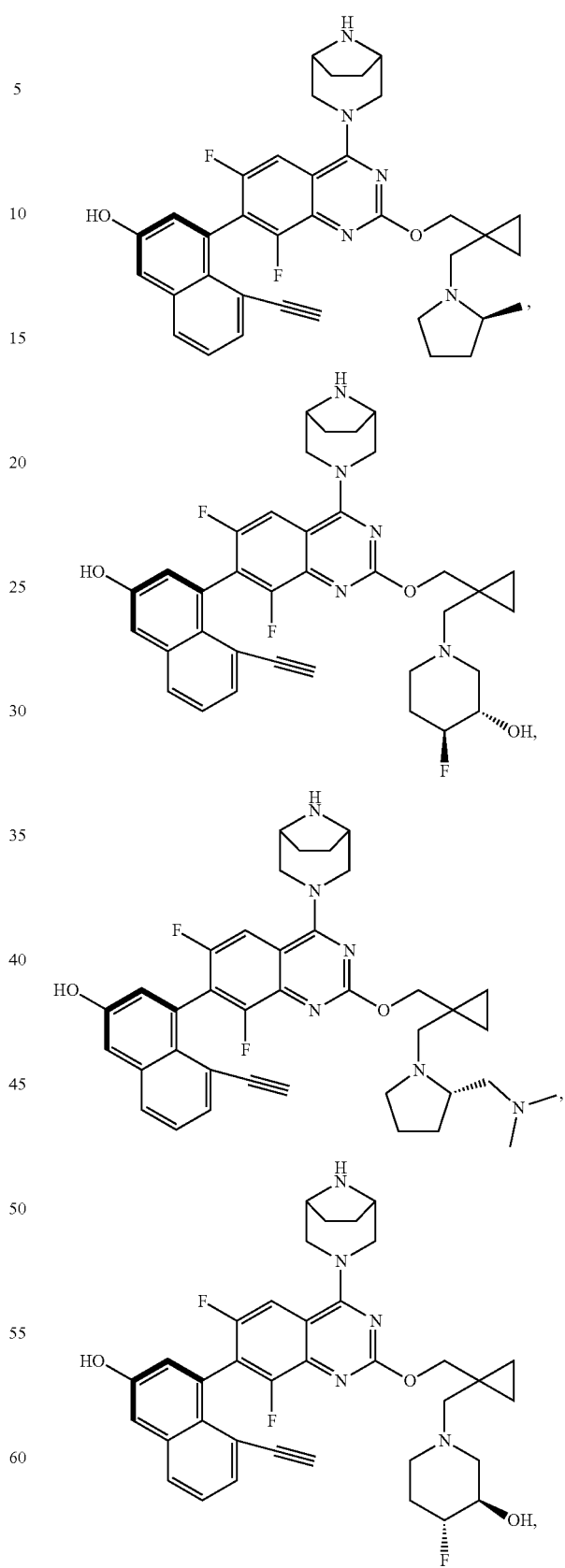

455
-continued
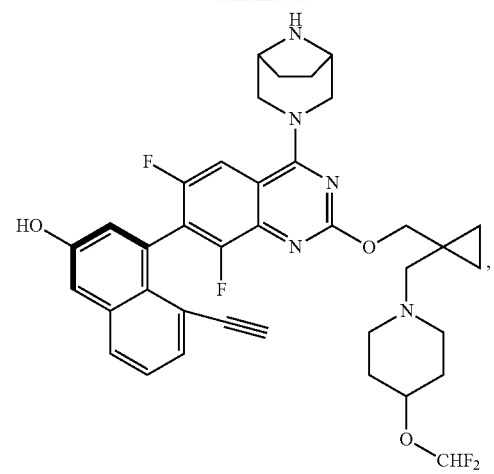
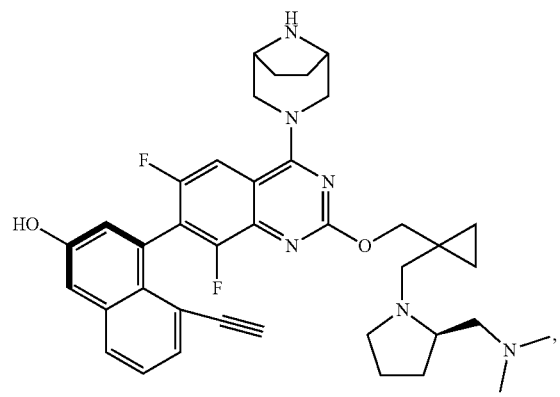
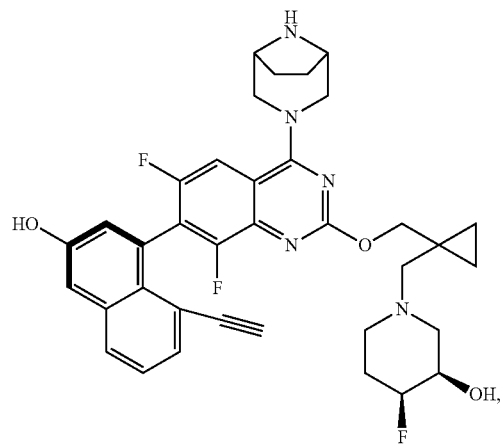
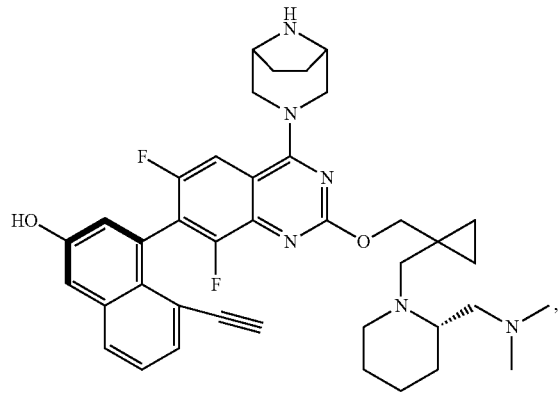
456
-continued
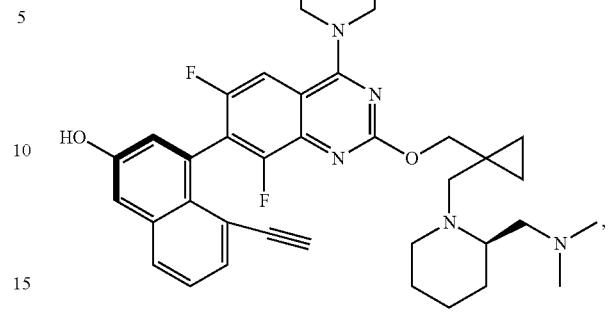
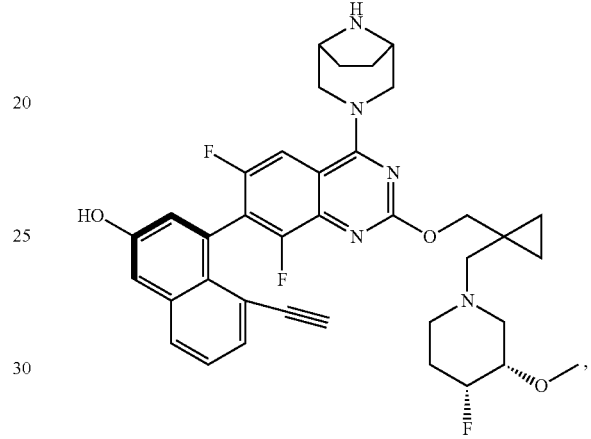
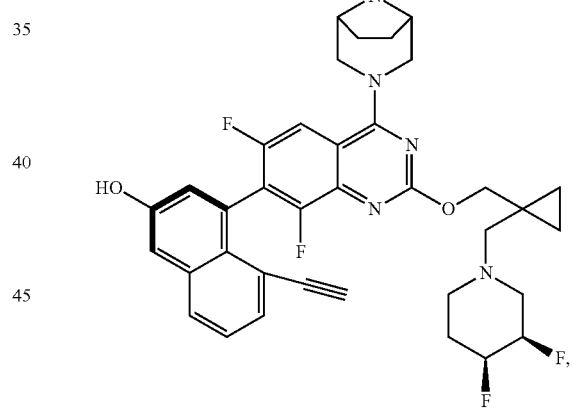
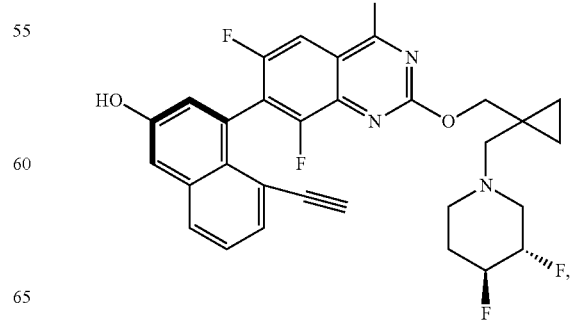

457
-continued
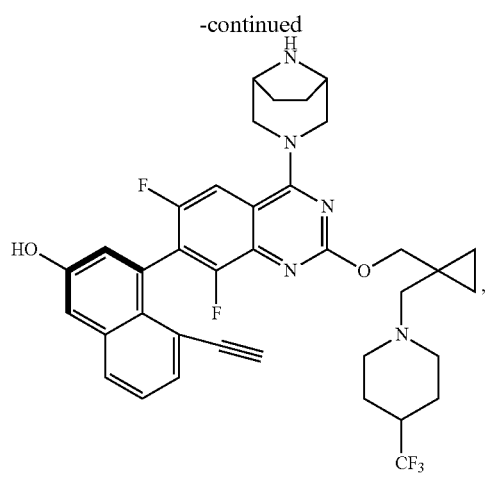
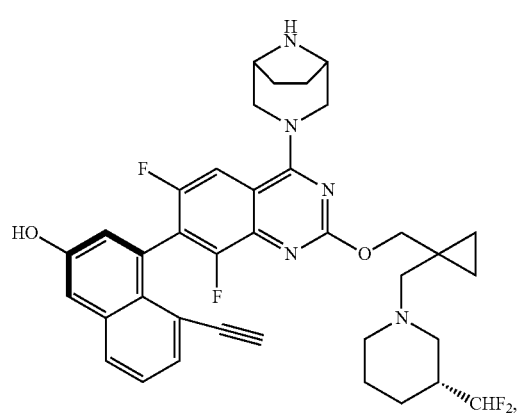
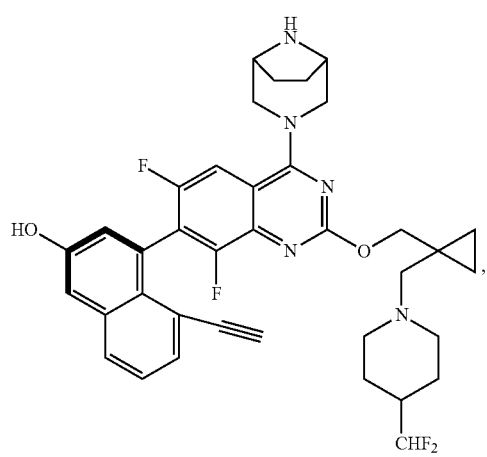
458
-continued
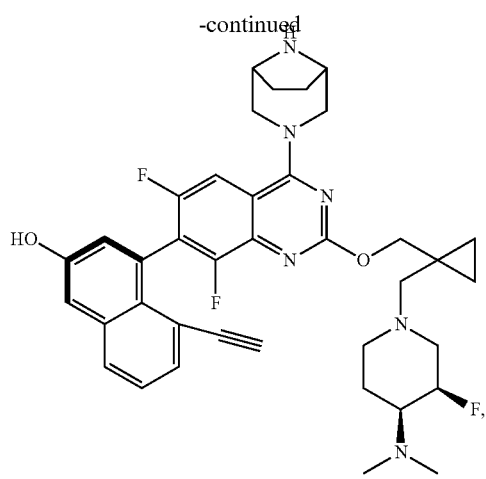
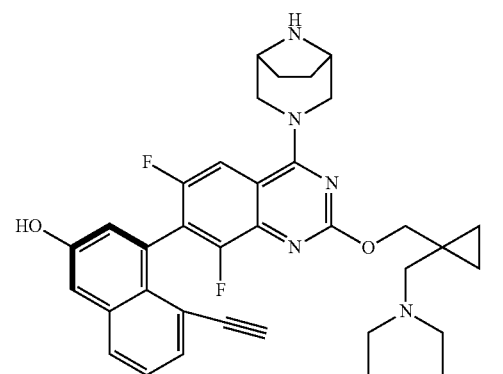
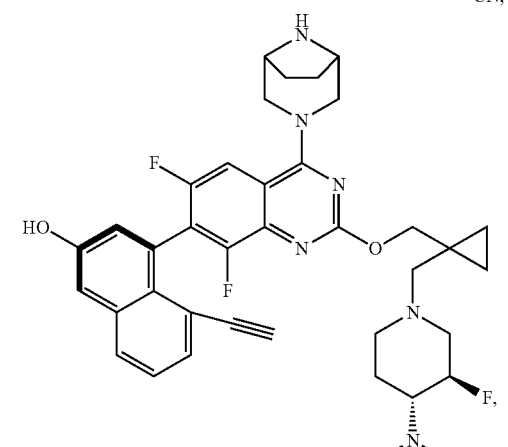
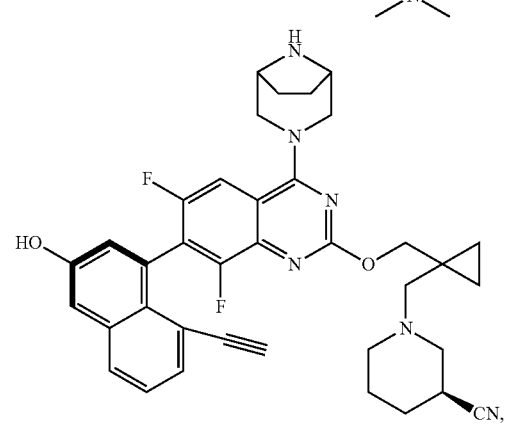

459
-continued
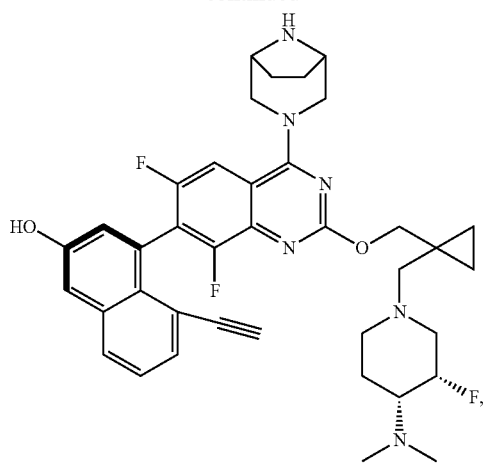
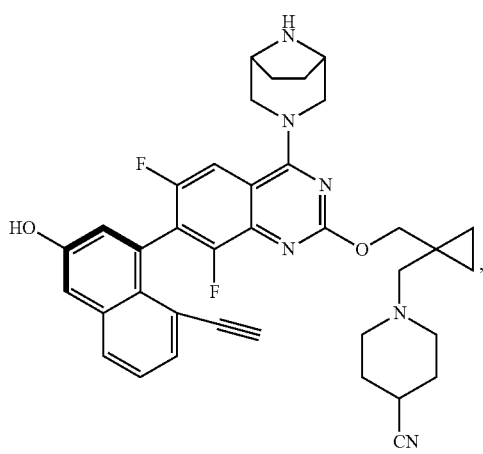
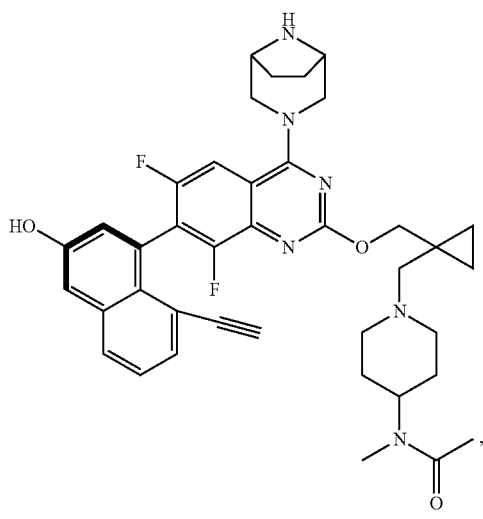
460
-continued
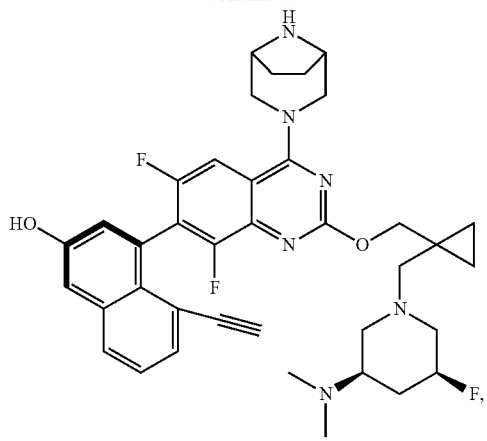
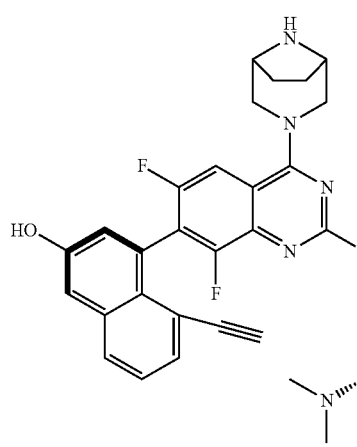
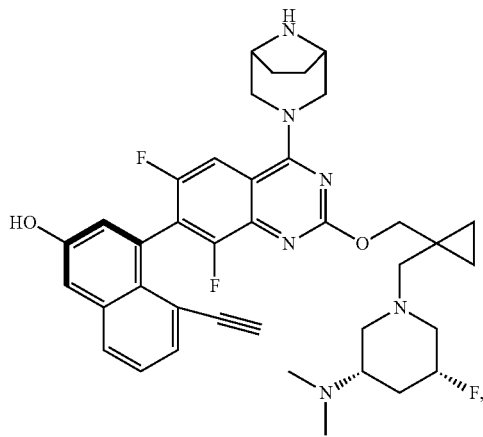

461
-continued

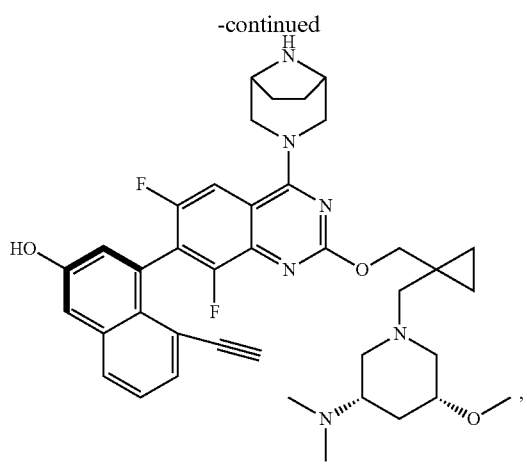

462
-continued

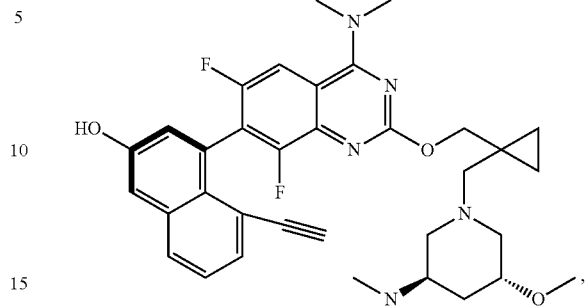

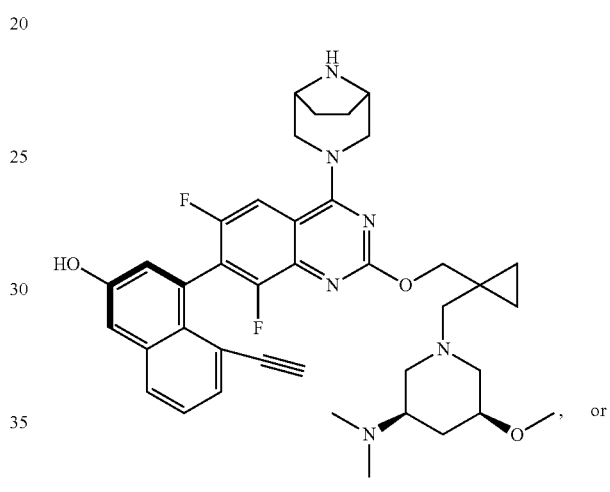

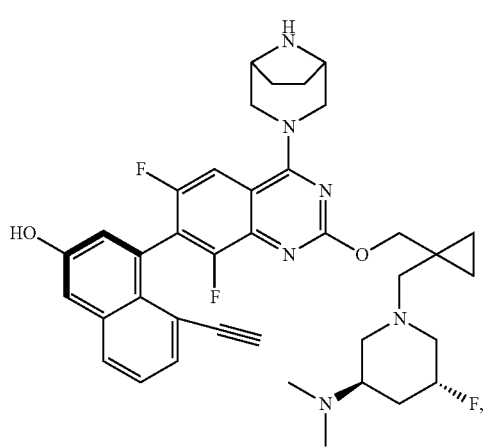

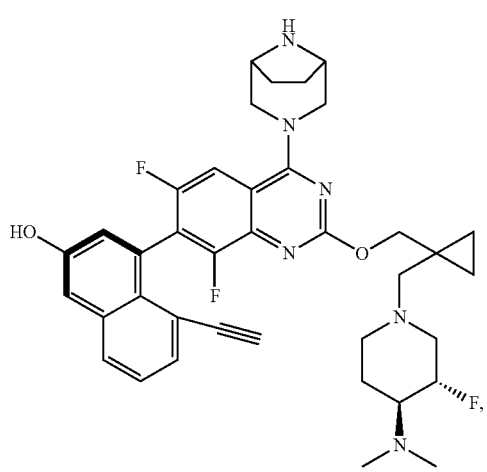

Yet other specific examples of KRAS G12D binding moieties are disclosed in International Publication No. WO 2021/249519, the entire content of which is incorporated herein by reference. In some embodiments, a KRAS G12 binding moiety is a KRAS G12D inhibitor binding moiety (e.g., inhibitor) disclosed in WO 2021/249519. For example, in some embodiments, a KRAS G12D binding moiety has the following structural formula:

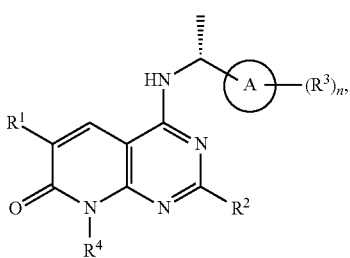

wherein:
Ring A is aryl or heteroaryl;
R¹ is selected from hydrogen, alkyl, alkoxy, haloalkyl, haloalkoxy, hydroxyalkyl, cycloalkyloxy, heterocyclyloxy, alkenyl, alkynyl, hydroxyl, cyano, amino, —NR⁵R⁶, nitro, cycloalkyl, heterocyclic, aryloxy, heteroaryloxy, aryl or heteroaryl, wherein the alkyl, alkoxy, cycloalkyloxy, heterocyclyloxy, cycloalkyl, heterocyclyl, aryloxy, heteroaryloxy, aryl and heteroaryl are each optionally and independently substituted by one or more substituents independently selected from halogen, alkyl, alkoxy, haloalkoxy, hydroxyl, amino, oxo, —C(O)(CH₂)$_q$OR⁷, —NHC(=O)R⁸, —C(O)R⁸, —NR⁹R¹⁰, —C(O)(CH₂)$_p$NR⁹R¹⁰, nitro, cyano, cycloalkyl, heterocyclic, aryl or heteroaryl;
R² is selected from hydrogen, halogen, alkyl, haloalkyl, alkoxy, haloalkoxy, hydroxyalkyl, cyano, amino or cycloalkyl;
R³ are the same or different, each independently selected from hydrogen, halogen, alkyl, alkoxy, haloalkyl, haloalkoxy, hydroxyalkyl, alkenyl, alkynyl, hydroxyl, cyano, amino,
—(CH₂)$_r$NR⁵R⁶, cycloalkyl, heterocyclyl, aryl or heteroaryl, wherein the alkyl, haloalkyl, cycloalkyl, heterocyclyl, aryl and heteroaryl are each optionally and independently substituted with one or more substituents independently selected from halogen, alkyl, alkoxy, haloalkyl, haloalkoxy, hydroxy, nitro, amino, —(CH₂)$_s$NR⁹R¹⁰, cyano, cycloalkyl or heterocyclyl;
R⁴ is selected from a hydrogen, alkyl or cycloalkyl; wherein the alkyl and cycloalkyl are each optionally and independently substituted with one or more substituents independently selected from halogen, alkyl, alkoxy, haloalkyl, haloalkoxy, hydroxy, nitro, amino, cyano, cycloalkyl, heterocyclyl, aryl or heteroaryl;
R⁵ and R⁶ are the same or different, and are each independently selected from a hydrogen, alkyl, haloalkyl, hydroxyalkyl, hydroxyl, amino, cycloalkyl or heterocyclyl;
R⁷ is selected from a hydrogen, alkyl, haloalkyl, hydroxyalkyl, cycloalkyl or heterocyclyl;
R⁸ is the same or different, and each is independently selected from a hydrogen, alkyl, haloalkyl, hydroxyalkyl, hydroxyl, amino, cycloalkyl, or heterocyclyl; wherein the alkyl, haloalkyl, cycloalkyl and heterocyclyl are each optionally and independently substituted with one or more substitutents independently selected from halogen, alkyl, alkoxy, haloalkyl, haloalkoxy, hydroxy, nitro, amino, cyano, cycloalkyl, heterocyclyl, aryl or heteroaryl;
R⁹ and R¹⁰ are the same or different, and are each independently selected from a hydrogen, alkyl, haloalkyl, hydroxyalkyl, hydroxyl, amino, cycloalkyl, or heterocyclyl;

n is 1, 2, 3 or 4;
p is 0, 1, 2 or 3;
q is 0, 1, 2 or 3;
r is 0, 1, 2 or 3; and
s is 0, 1, 2, or 3.

In some embodiments, the KRAS G12D binding moiety is:

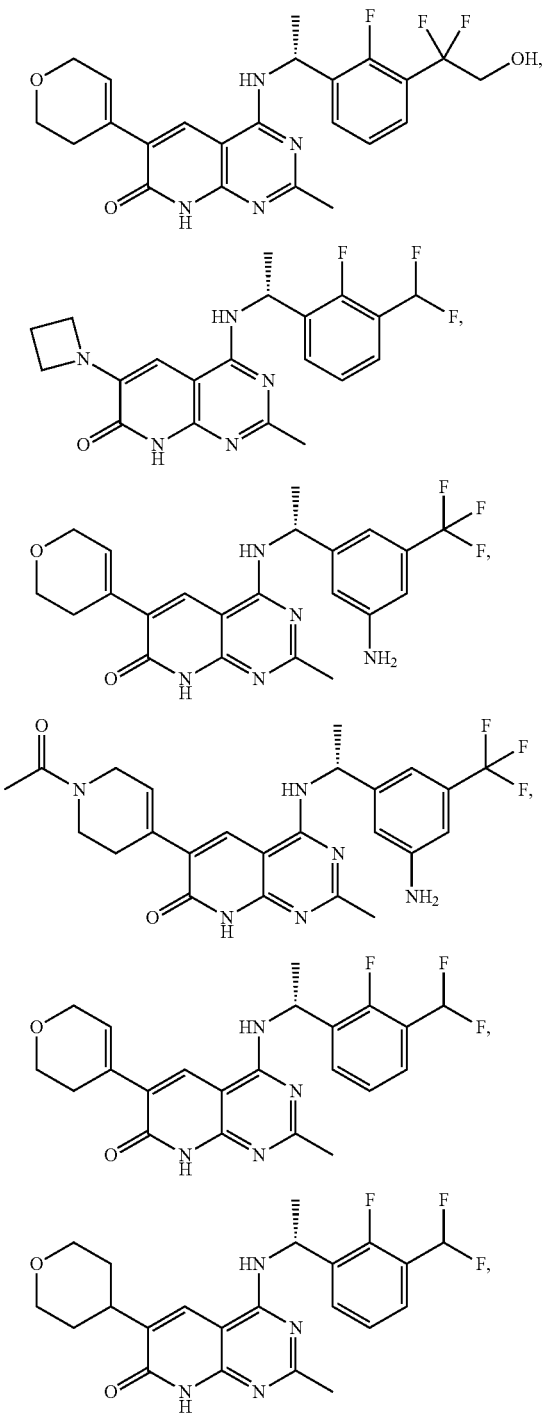

465
-continued
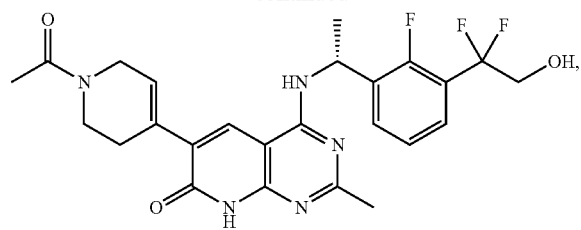
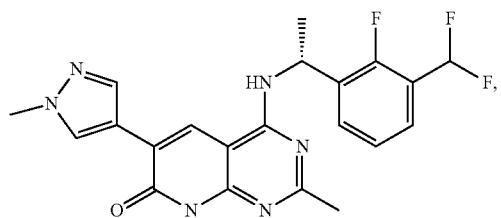
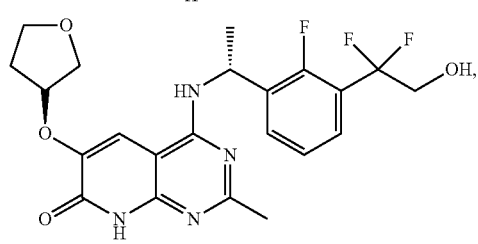
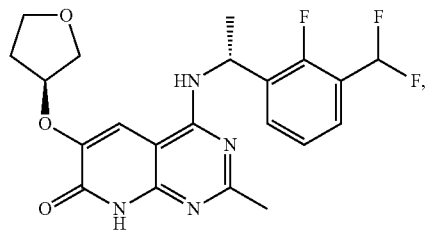
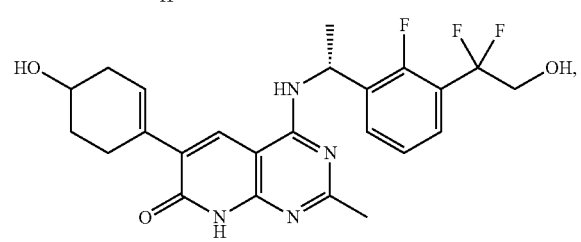
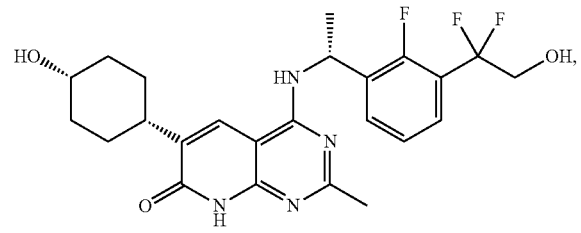
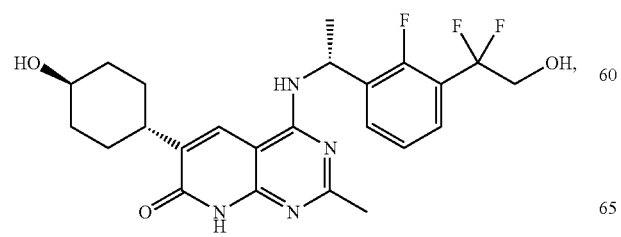
466
-continued
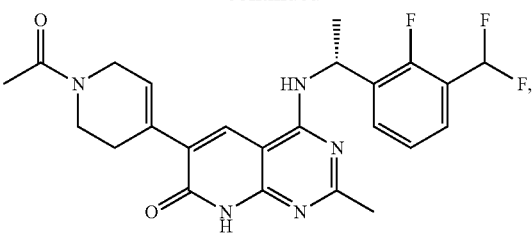
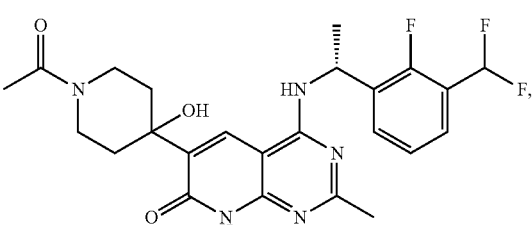
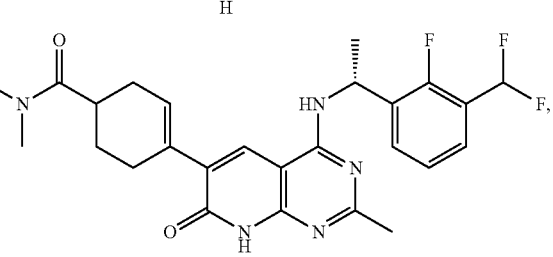
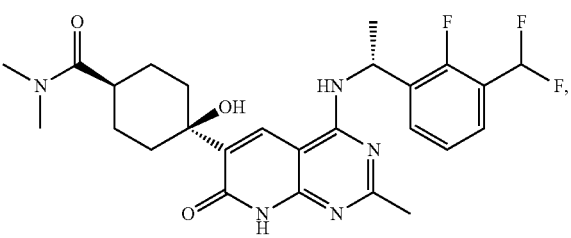
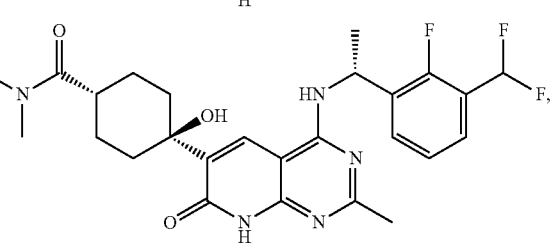
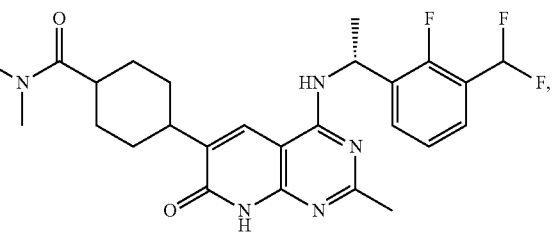
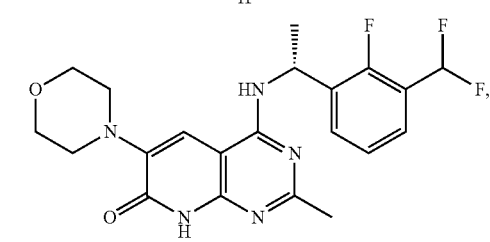

467
-continued
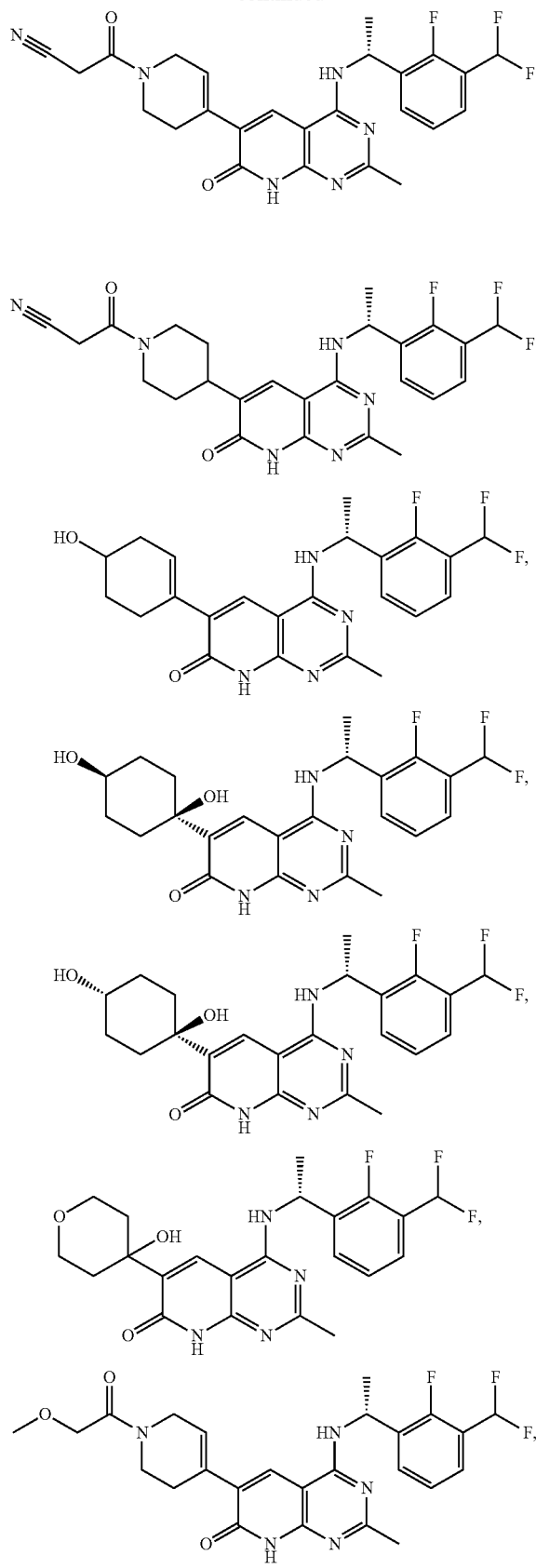
468
-continued
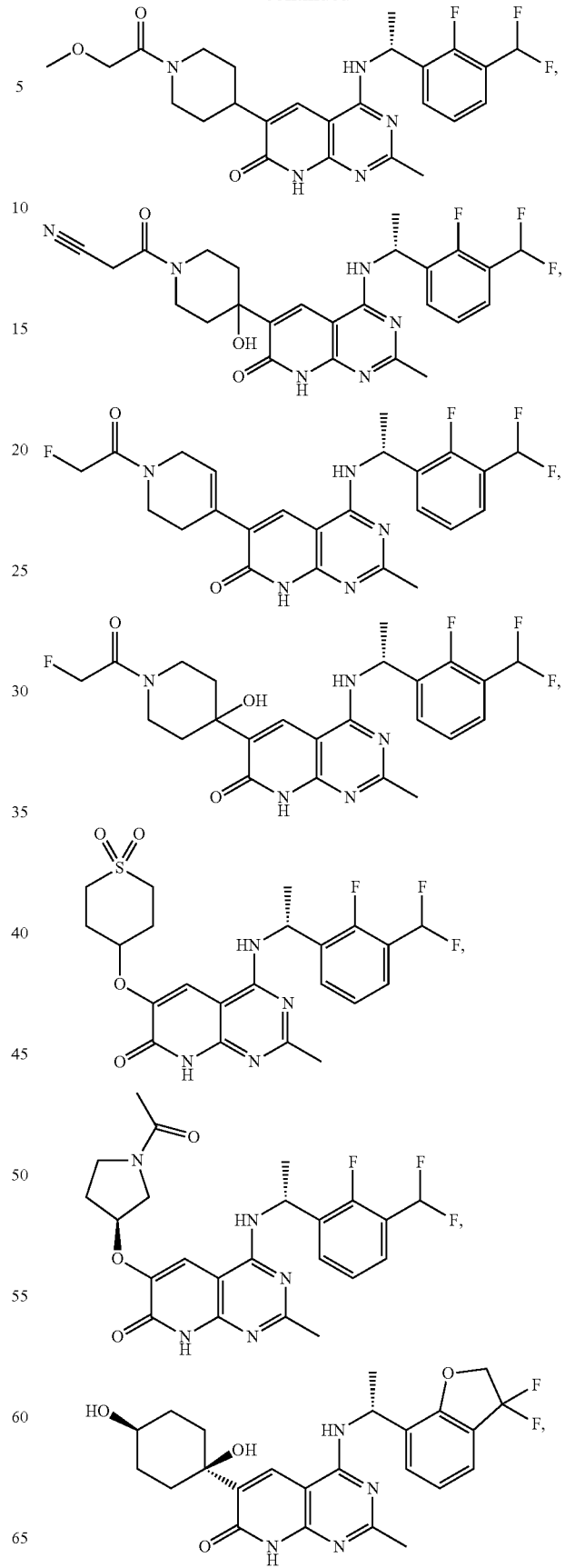

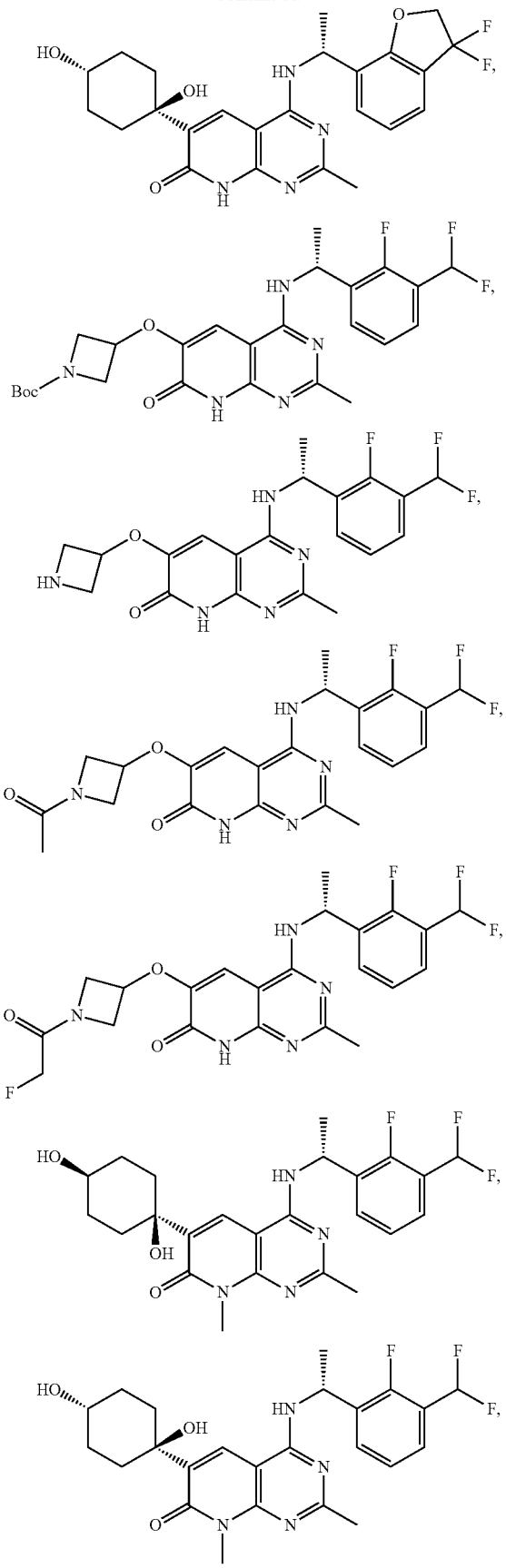

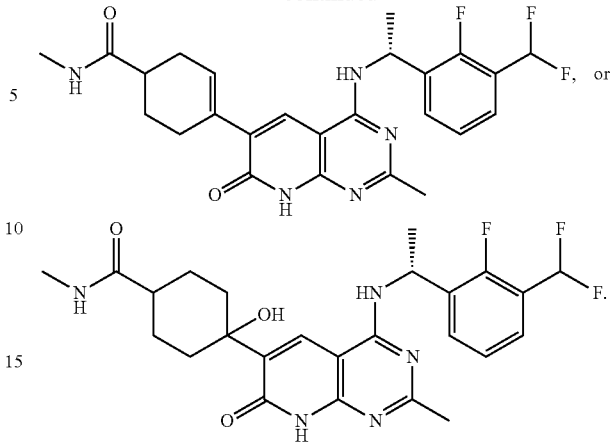

Yet other specific examples of KRAS G12D binding moieties are disclosed in International Publication No. WO 2022/221739, the entire content of which is incorporated herein by reference. In some embodiments, a KRAS G12 binding moiety is a KRAS G12D inhibitor binding moiety (e.g., inhibitor) disclosed in WO 2022/221739. For example, in some embodiments, a KRAS G12D binding moiety has the following structural formula:

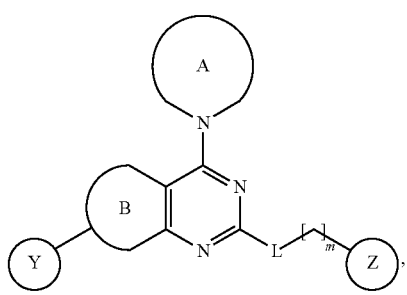

wherein:
Ring A is a saturated or partially unsaturated 8- to 10-membered N-containing bridged ring which contains at least one further heteroatom selected from the group consisting of N, S and O;
wherein Ring A is unsubstituted or substituted by 1 to 3 $R^A$ substituents independently selected from the group consisting of $C_1$-$C_3$ alkyl, $C_2$-$C_4$ alkenyl, $C_1$-$C_3$ alkoxy, $C_1$-$C_3$ alkoxy($C_1$-$C_3$)alkyl, halo, $C_1$-$C_3$ fluoroalkyl, hydroxy, $C_1$-$C_3$ hydroxyalkyl, $CF_3$—C(H)(OH)—, C(H)($F_2$)—C(H)(OH)—, cyano, and $C_1$-$C_3$ cyanoalkyl;
Ring B is a 5- or 6-membered partially unsaturated or aromatic ring having 0, 1 or 2 heteroatoms selected from the group consisting of N, S, and O, and wherein Ring B is fused with the illustrated pyrimidine ring;
wherein Ring B is unsubstituted or substituted by 1 to 2 $R^B$ substituents independently selected from the group consisting of halo, hydroxy, oxo, cyano, $C_1$-$C_3$ alkyl, $C_1$-$C_3$ fluoroalkyl, and $C_1$-$C_3$ alkoxy;
Ring Y is a 6-membered mono-, a 9- to 10-membered bicyclic-, or a 13- to 14-membered tricyclic ring system, wherein said ring system is partially unsaturated or aromatic, and wherein Ring Y contains 0 to 3 heteroatoms selected from the group consisting of N, S, and O;

wherein Ring Y is unsubstituted or substituted by 1 to 4 $R^Y$ substituents independently selected from the group consisting of halo, hydroxy, oxo, $C_1$-$C_3$ alkyl, $C_2$-$C_3$ alkynyl, $C_1$-$C_3$ fluoroalkyl, $C_1$-$C_3$ alkoxy, $C_1$-$C_3$ fluoroalkoxy, $C_1$-$C_3$ alkylthio, $C_1$-$C_3$ fluoroalkylthio, amino, $C_1$-$C_3$ alkylamino, $C_1$-$C_3$ dialkylamino, $C_3$-$C_{12}$ cycloalkyl, tri($C_1$-$C_3$ alkyl)silyl, and cyano;

Ring Z is
- (i) a 3- to 10-membered mono- or bicyclic cycloalkyl;
- (ii) a 3- to 10-membered mono- or bicyclic-heterocycloalkyl, wherein said heterocycloalkyl is saturated and contains 1 to 2 heteroatoms selected from the group consisting of N, S, and O; or
- (iii) a 3- to 8-membered spiroheterocycloalkyl, wherein said spiroheterocycloalkyl is saturated and contains 1 to 2 heteroatoms selected from the group consisting of N, S, and O;

wherein Ring Z is unsubstituted or substituted by 1 to 4 $R^Z$ substituents independently selected from the group consisting of halo, hydroxy, $C_1$-$C_6$ alkyl, $C_1$-$C_3$ alkoxy, $C_1$-$C_3$ hydroxyalkyl, $C_1$-$C_6$ fluoroalkyl, carboxy, carbamoyl, methoxy($C_1$-$C_3$)alkyl, amino($C_1$-$C_3$)alkyl, $C_1$-$C_3$ alkylamino($C_1$-$C_3$)alkyl, $C_1$-$C_3$ dialkylamino, and $C_1$-$C_3$ dialkylamino($C_1$-$C_3$)alkyl;

Ring Z is optionally substituted by 1 -M-$R^{ZC}$, wherein

M is —$CH_2$— or absent; and $R^{ZC}$ is a 5- to 6-membered mono- or a 9- to 10-membered bicyclic saturated heterocycloalkyl which contains 1 to 3 heteroatoms selected from the group consisting of N, S, and O, wherein Ru is unsubstituted or substituted by a substituent selected from the group consisting of $C_1$-$C_3$ alkyl, $C_1$-$C_3$ alkylcarbonylalkyl, $C_1$-$C_3$ hydroxyalkyl, fluoro, cyano, amino, $C_1$-$C_3$ alkylamino, $C_1$-$C_3$ dialkylamino, $C_1$-$C_3$ alkoxyalkyl, and $C_1$-$C_3$ cyanoalkyl;

L is O or absent; and m is 0, 1, or 2.

In some embodiments, the KRAS G12D binding moiety is:

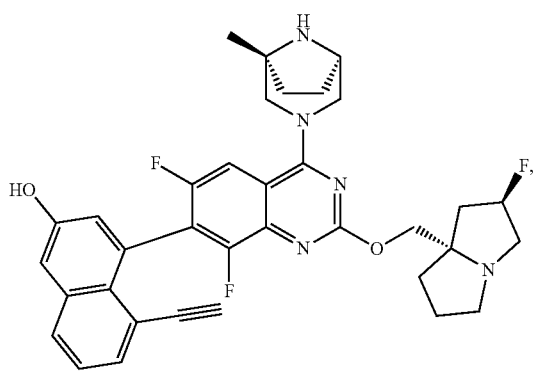

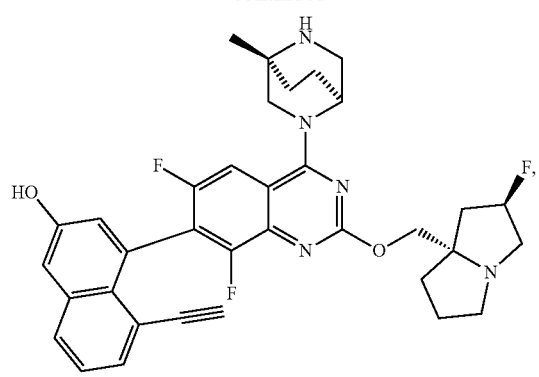

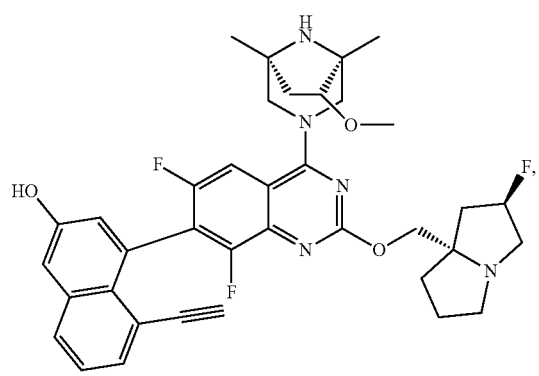

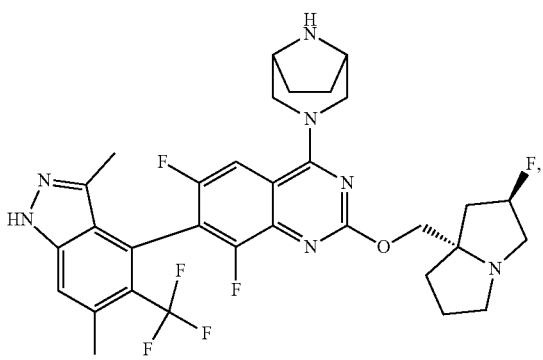

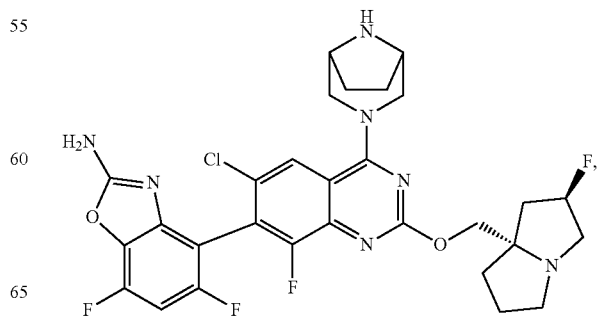

473
-continued
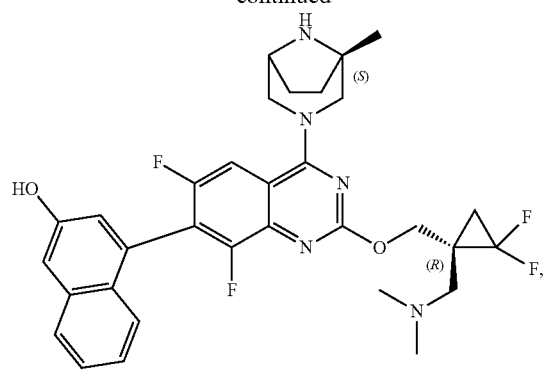
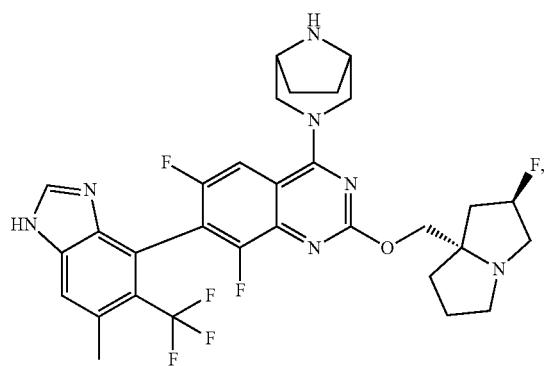
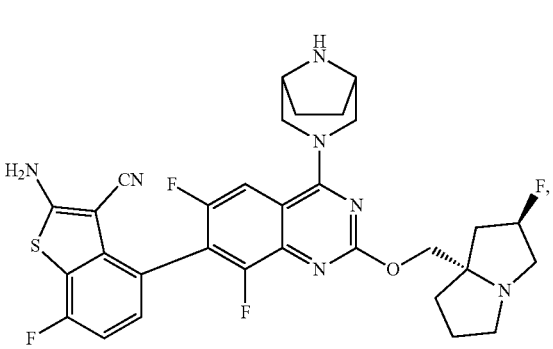
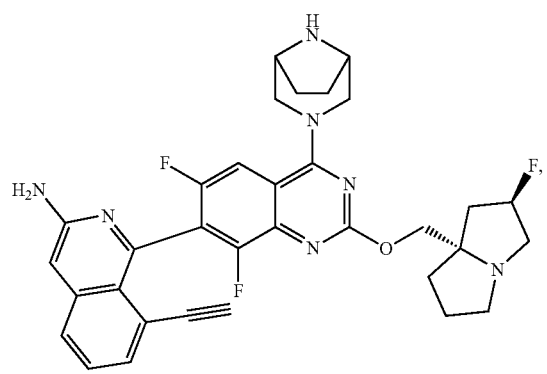
474
-continued
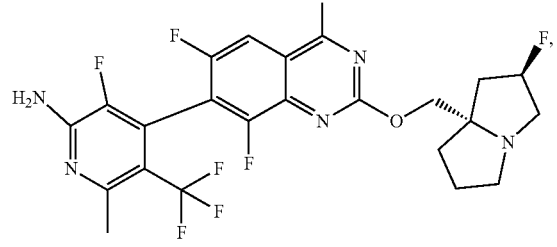
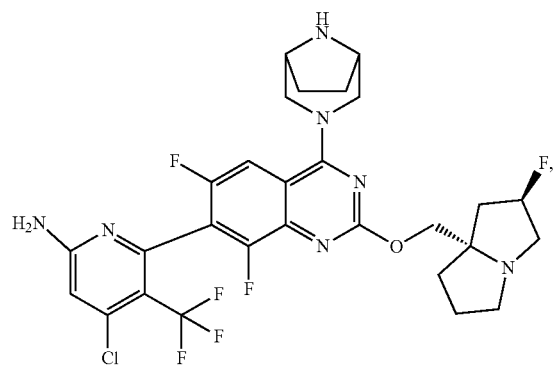
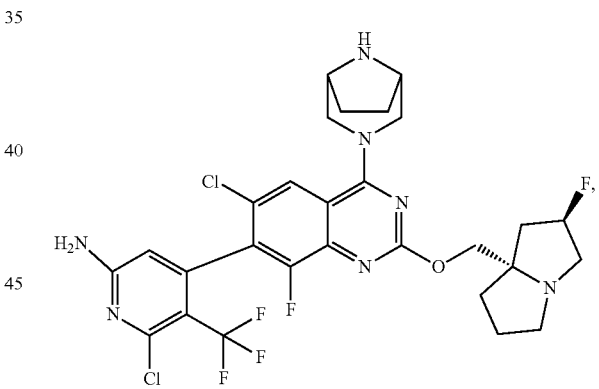
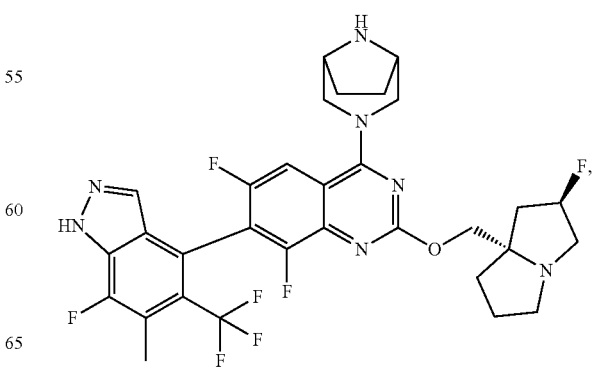

475
-continued
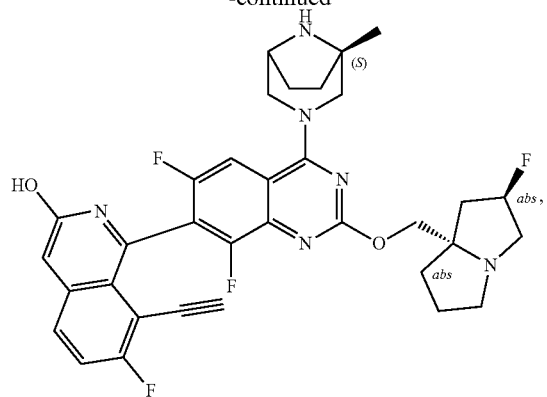
476
-continued
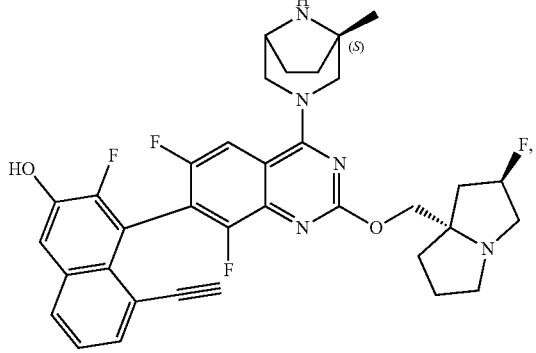
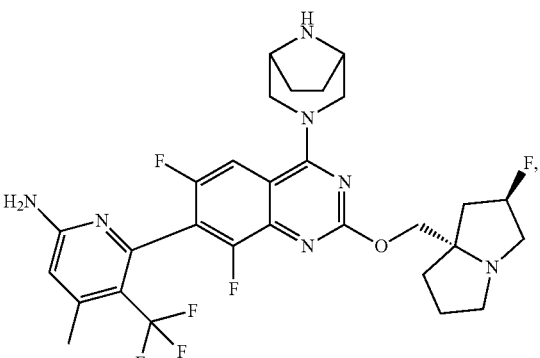
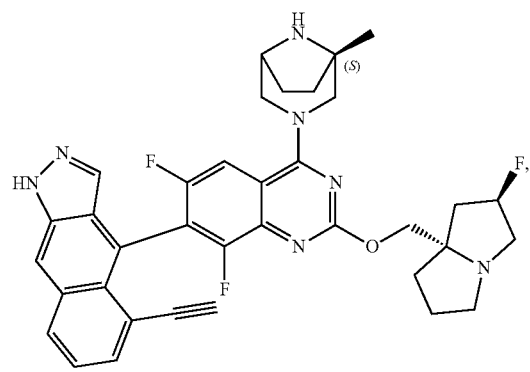
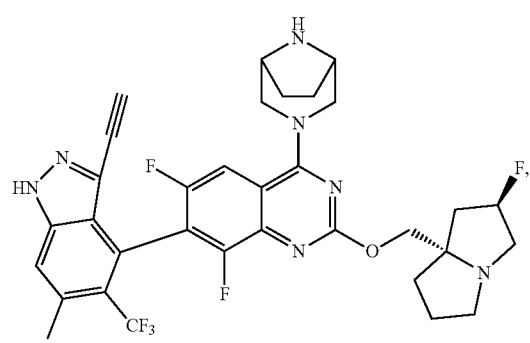

477
-continued
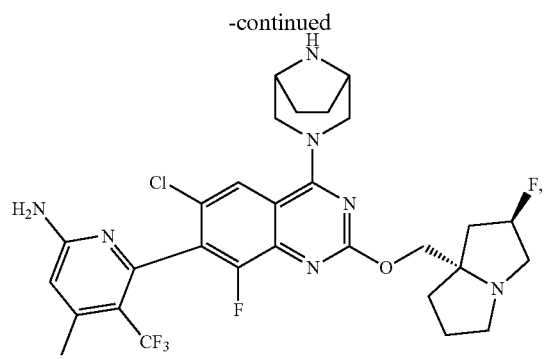
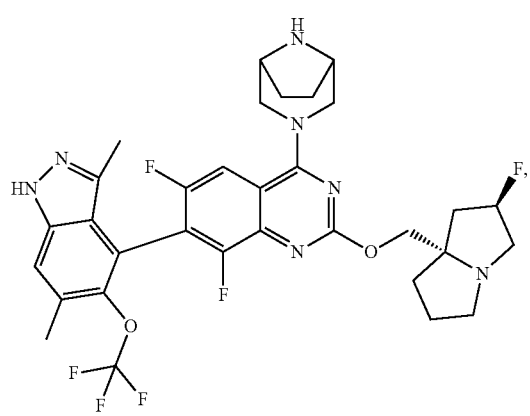
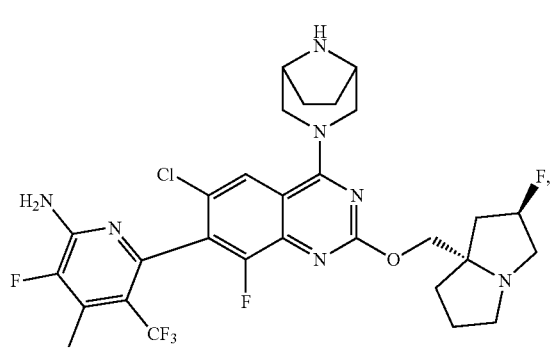
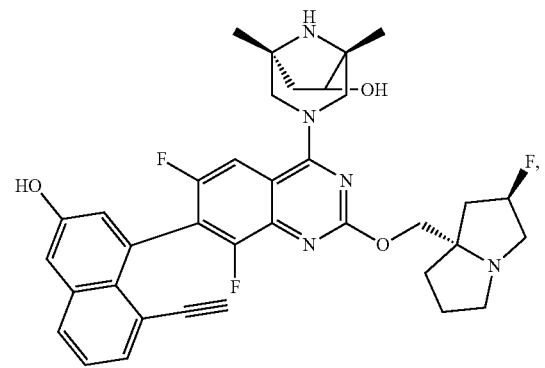
478
-continued
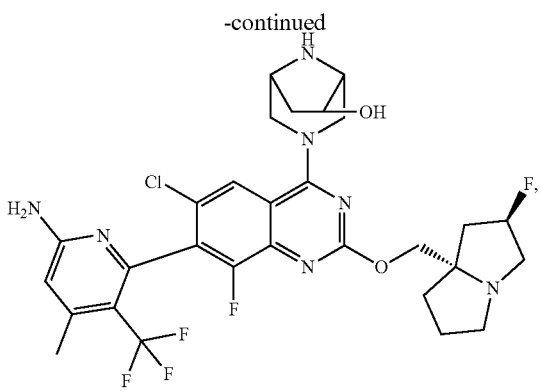
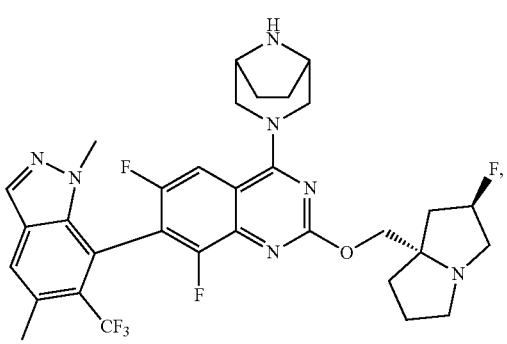
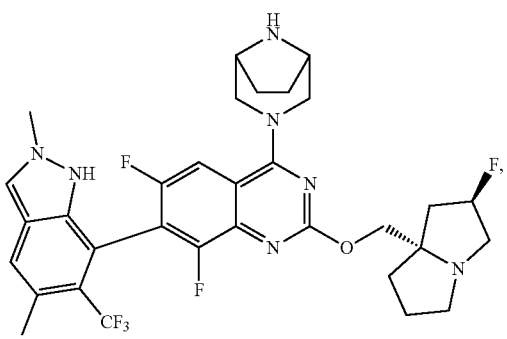
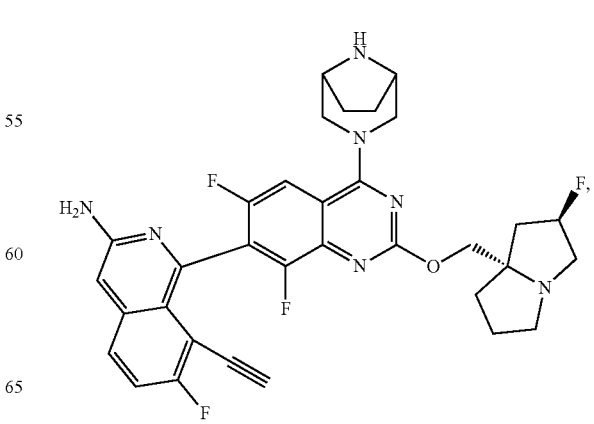

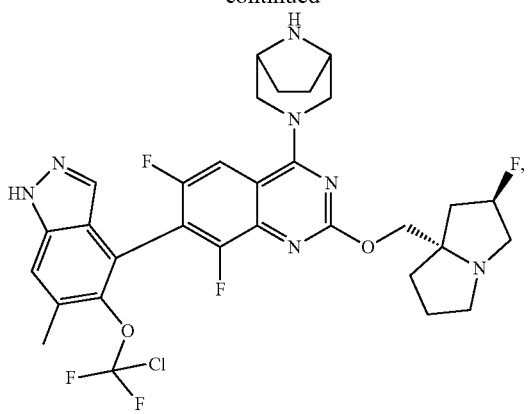

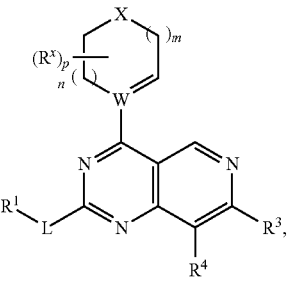

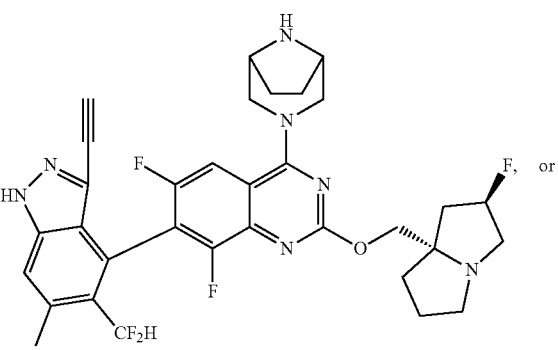

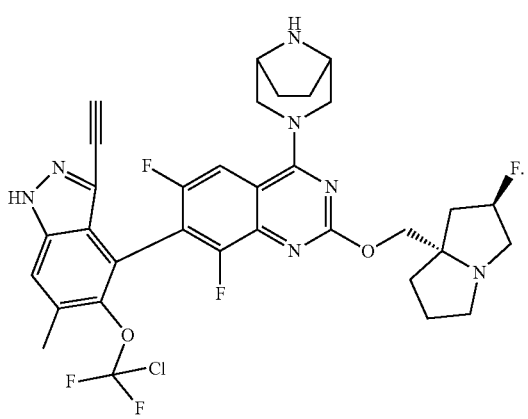

Yet other specific examples of KRAS G12D binding moieties are disclosed in International Publication No. WO 2023/018810, the entire content of which is incorporated herein by reference. In some embodiments, a KRAS G12D binding moiety is a KRAS G12D binding moiety (e.g., inhibitor) disclosed in WO 2023/018810. For example, in some embodiments, a KRAS G12D moiety has the following structural formula:

wherein:
 ═ is a single bond or a double bond;
 W is C, CH or N, wherein when W is CH or N, ═ is a single bond;
 X is O, S, S(O), S(O)(NR$^z$), S(O)$_2$, CH$_2$ or CH═CH;
 n is 0, 1 or 2;
 m is 0, 1 or 2;
 p is 2, 3 or 4;
 two R$^x$ taken together with the same carbon atom form a C$_{3-7}$ cycloalkyl or a 4-7 membered heterocycloalkyl, wherein each C$_{3-7}$ cycloalkyl or 4-7 membered heterocycloalkyl is further substituted with 0-3 occurrences of R$^y$ and when p is 3 or 4, each remaining R$^x$ is hydroxyl, halogen, oxo, cyano, —N(R$^z$)$_2$, C$_{1-4}$ alkyl, C$_{1-4}$ alkoxy, C$_{1-4}$ haloalkyl, C$_{1-4}$ haloalkoxy, C$_{3-6}$ cycloalkyl, 5-7 membered heteroaryl;
 L is C$_{1-6}$ alkylene, —O—C$_{1-6}$ alkylene, —S—C$_{1-6}$ alkylene, NR$_z$, O or S, wherein each C$_{1-6}$ alkylene, —O—C$_{1-6}$ alkylene and —S—C$_{1-6}$ alkylene chain is substituted with 0-2 occurrences of R$^2$;
 R$^1$ is hydroxyl, aryl, heteroaryl, C$_{3-8}$ cycloalkyl or heterocycloalkyl substituted with 0-3 occurrences of R$^5$;
 R$^2$ is halogen, hydroxyl, C$_{1-4}$ alkyl or two R$^2$ on the same or adjacent carbon atoms can be taken together to form a C$_{3-7}$ cycloalkyl;
 R$^3$ is aryl or heteroaryl substituted with 0-3 occurrences of R$^6$;
 R$^4$ is hydrogen, hydroxyl, halogen, C$_{1-4}$ alkyl, C$_{1-4}$ alkoxy, C$_{1-4}$ haloalkyl, C$_{2-4}$ alkenyl, C$_{2-4}$ alkynyl, C$_{3-7}$ cycloalkylo or cyano;
 each R$^5$ is halogen, oxo, hydroxyl, cyano, amino or C$_{1-4}$ alkyl;
 each R$^6$ is halogen, hydroxyl, cyano, —N(R$^z$)$_2$, C$_{1-4}$ alkyl, C$_{1-4}$ alkoxy, C$_{1-4}$ haloalkyl, C$_{1-4}$ haloalkoxy, C$_{2-4}$ alkynyl or C$_{3-6}$ cycloalkyl;
 T is C$_{1-4}$ alkylene, —S(O)$_2$—, —C(O)—, —C$_{1-4}$ alkylene-C(O)—, —N(H)—C(O)—, —N(H)—S(O)$_2$—, C$_{1-4}$ alkylene-S(O)$_2$— or —S—;
 R$^y$ is halogen, oxo, C$_{1-4}$ alkyl, C$_{1-4}$ alkoxy, C$_{1-4}$ haloalkyl, hydroxyl, cyano, —S(O)$_2$—C$_{1-4}$ alkyl, ═NR$^z$ or —N(R$^z$)$_2$; and
 R$^z$ is hydrogen or C$_{1-4}$ alkyl.

In some embodiments, the KRAS G12D binding moiety is:
5,6-Difluoro-4-(8-fluoro-2-(((2R,7aS)-2-fluorotetrahydro-1H-pyrrolizin-7a(5H)-yl)methoxy)-4-(1-oxa-6-azaspiro[3.5]nonan-6-yl)pyrido[4,3-d]pyrimidin-7-yl)naphthalen-2-ol;
6-(7-(8-Ethyl-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol;
7-(7-(8-Ethyl-7-fluoro-3-hydroxynaphthalen-1-yl)-8-fluoro-2-(((2R,7aS)-2-fluorotetrahydro-1H-pyrrolizin-7a (5H)-yl)methoxy)pyrido[4,3-d]pyrimidin-4-yl)-1-oxa-3,7-diazaspiro[4.5]decan-2-one;

6-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,6-diazaspiro[3.5]nonan-2-one;

3-Chloro-4-cyclopropyl-5-(8-fluoro-2-(((2R,7aS)-2-fluorotetrahydro-1H-pyrrolizin-7a(5H)-yl)methoxy)-4-(1-oxa-6-azaspiro[3.5]nonan-6-yl)pyrido[4,3-d]pyrimidin-7-yl)phenol;

6-(7-(7,8-Difluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol;

6-(7-(7,8-Difluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol;

7-(7-(8-Ethynyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1-oxa-3,7-diazaspiro[4.5]decan-2-one;

6-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-methyl-6-azaspiro[3.5]nonan-2-ol;

6-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.5]nonan-1-one;

6-(7-(3-Chloro-2-cyclopropyl-5-hydroxyphenyl)-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol;

9-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-oxa-1,9-diazaspiro[3.6]decan-2-one;

5-Ethyl-6-fluoro-4-(8-fluoro-2-(((2R,7aS)-2-fluorotetrahydro-1H-pyrrolizin-7a(5H)-yl)methoxy)-4-(1-oxa-6-azaspiro[3.5]nonan-6-yl)pyrido[4,3-d]pyrimidin-7-yl)naphthalen-2-ol;

7-(7-(7,8-Difluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1-oxa-3,7-diazaspiro[4.5]decan-2-one;

7-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1,7-diazaspiro[4.5]decan-2-one;

7-(7-(8-Ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one;

7-(7-(8-Ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,7-diazaspiro[4.5]decan-3-one;

7-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-thia-7-azaspiro[4.5]decane 2,2-dioxide;

6-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1-methyl-1,6-diazaspiro[3.5]nonan-2-one;

7-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-imino-2l6-thia-7-azaspiro[4.5]decane 2-oxide;

7-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-3-oxa-1,7-diazaspiro[4.5]decan-2-one;

8-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1-oxa-3,8-diazaspiro[4.5]decan-2-one;

5-Ethyl-6-fluoro-4-(8-fluoro-2-(((2R,7aS)-2-fluorotetrahydro-1H-pyrrolizin-7a(5H)-yl)methoxy)-4-(1-oxa-6-azaspiro[3.5]nonan-6-yl)pyrido[4,3-d]pyrimidin-7-yl)naphthalen-2-ol;

6-(7-(8-Ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-6-azaspiro[3.5]nonan-2-ol; or 5-Ethyl-4-(8-fluoro-2-(((2R,7aS)-2-fluorotetrahydro-1H-pyrrolizin-7a(5H)-yl)methoxy)-4-(1-oxa-6-azaspiro[3.5]nonan-6-yl)pyrido[4,3-d]pyrimidin-7-yl)naphthalen-2-ol.

Yet other specific examples of KRAS G12D binding moieties are disclosed in International Publication No. WO 2022/194191, the entire content of which is incorporated herein by reference. In some embodiments, a KRAS G12D binding moiety is a KRAS G12D binding moiety (e.g., inhibitor) disclosed in WO 2022/194191. For example, in some embodiments, a KRAS G12D moiety has the following structural formula:

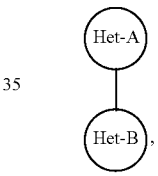

on the condition that the compound does not have the following structural formula:

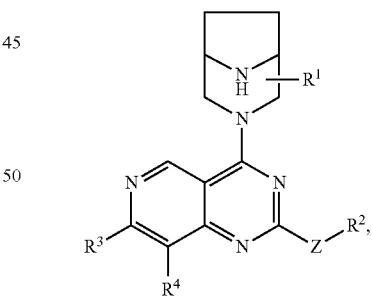

wherein:

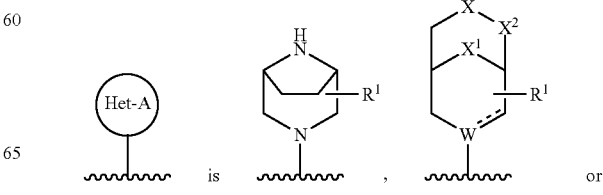

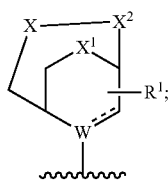
is a single bond or double bond;
X and $X^1$ are independently selected from a bond, O, S, $S(O)_2$, $CH_2$, CHF, $CF_2$ or $NR^x$ provided that at least one of X and $X^1$ is $NR^x$;
$X^2$ is $CH_2$ or absent;
W is C, CH, $C(C_{1-6}alkyl)$ or N;
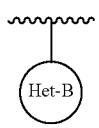
is selected from one of the following moieties:
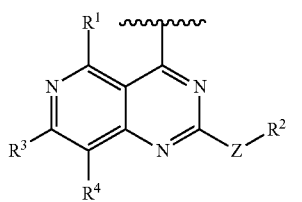
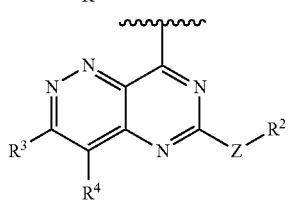
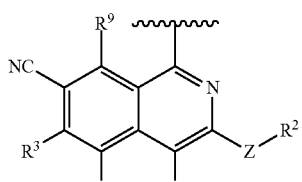
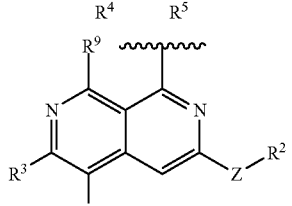
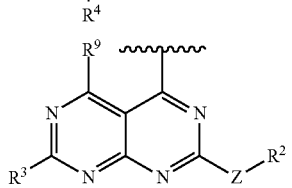
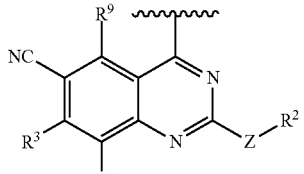
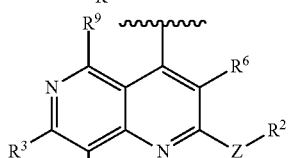
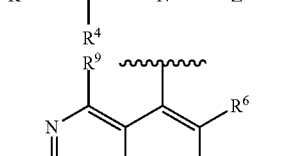
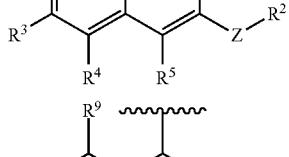
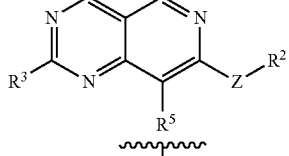
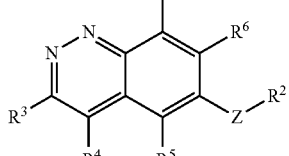
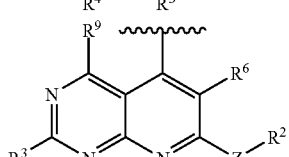
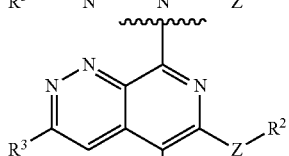
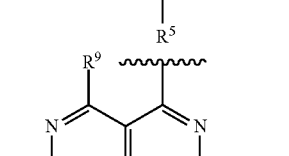
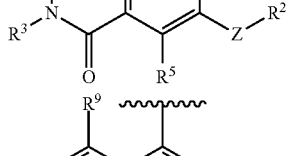
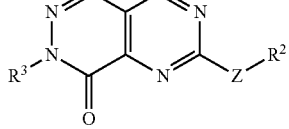

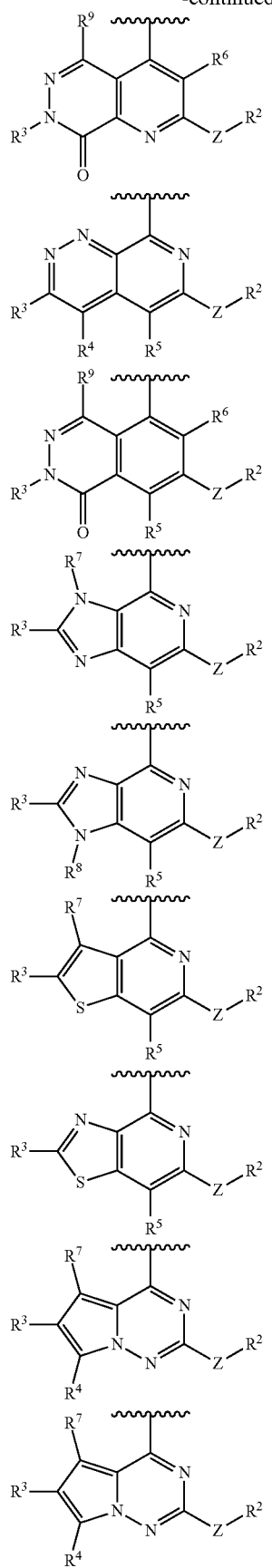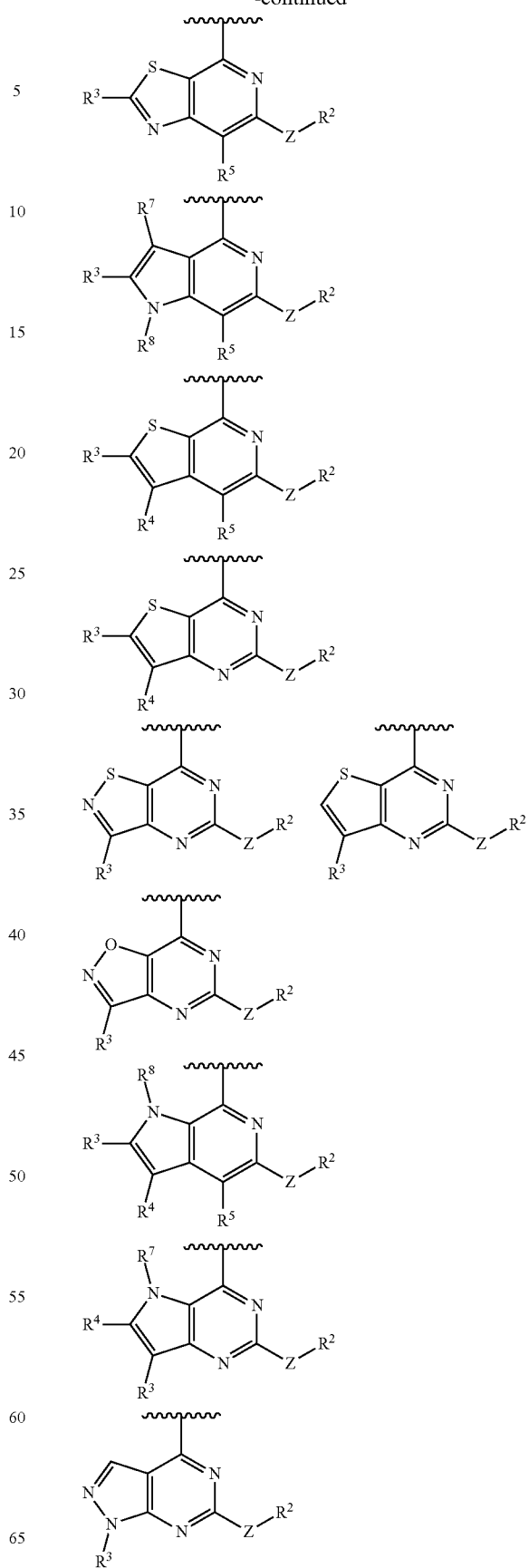

487
-continued
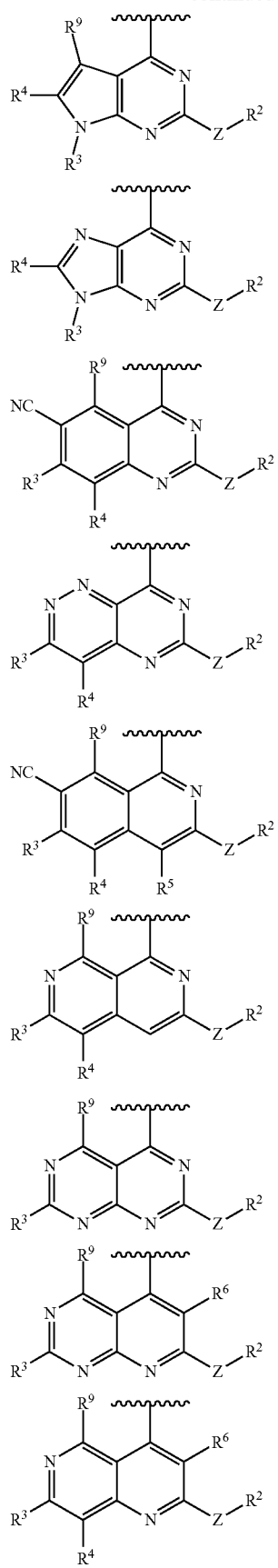
488
-continued
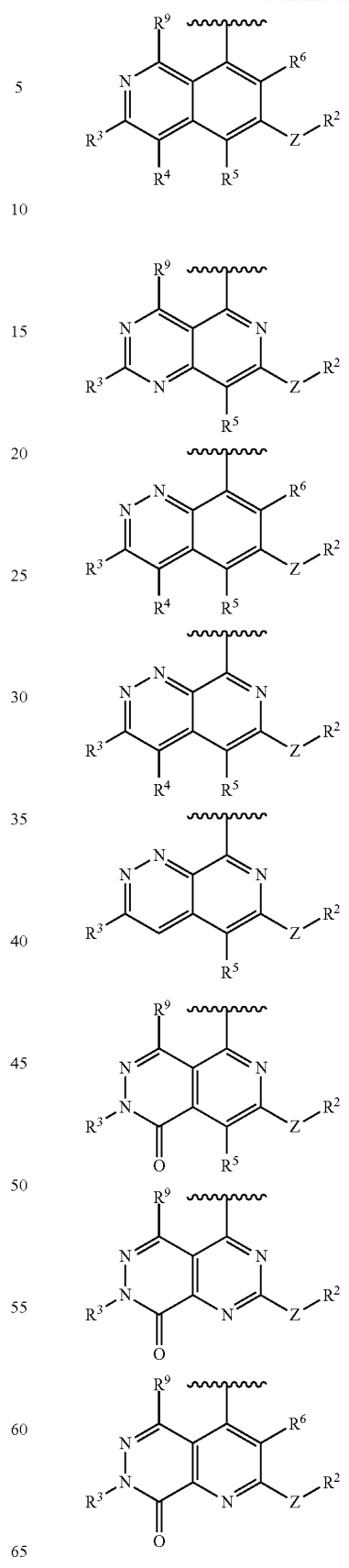

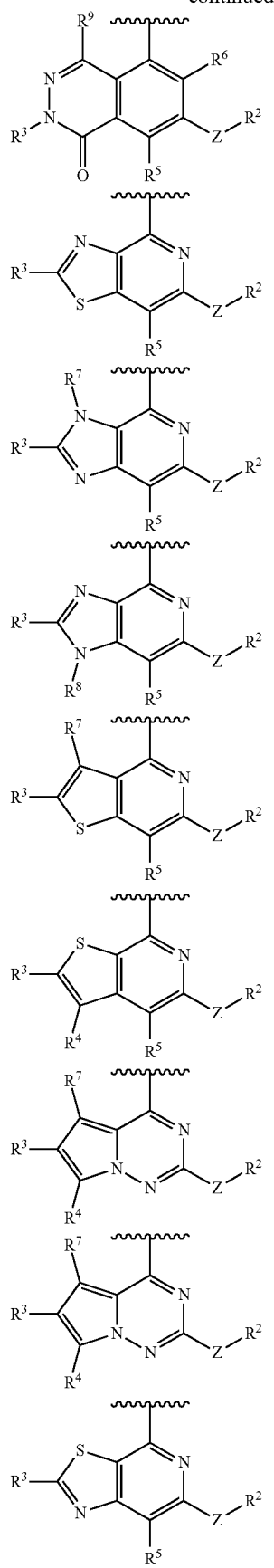
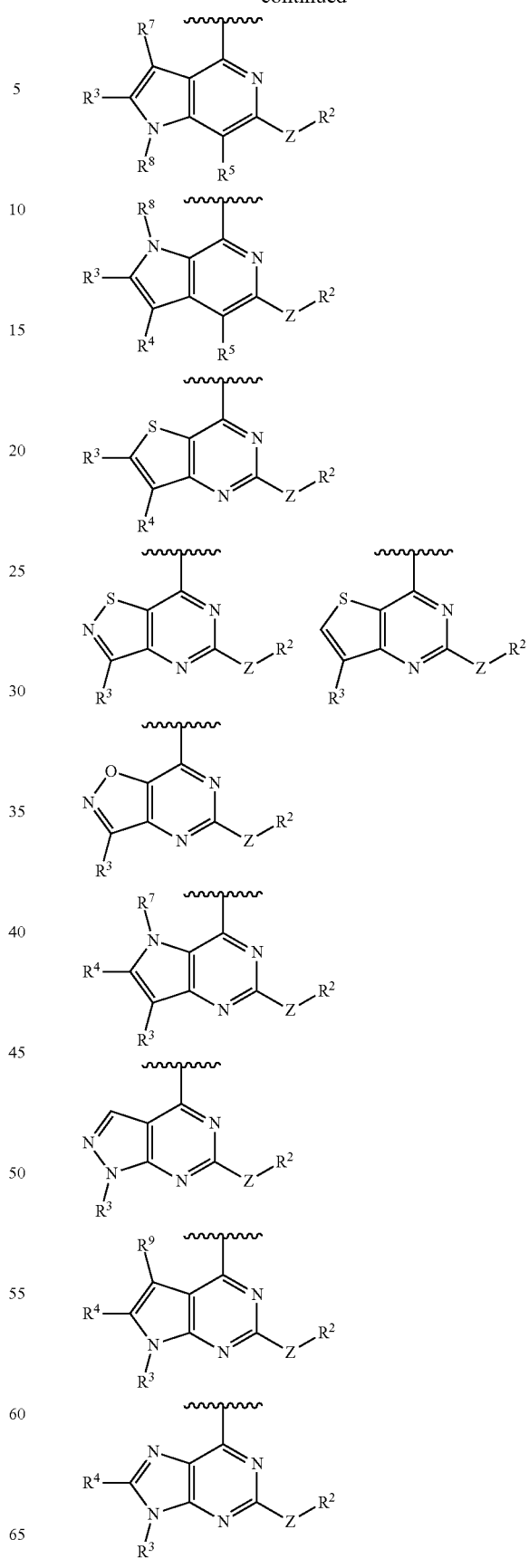

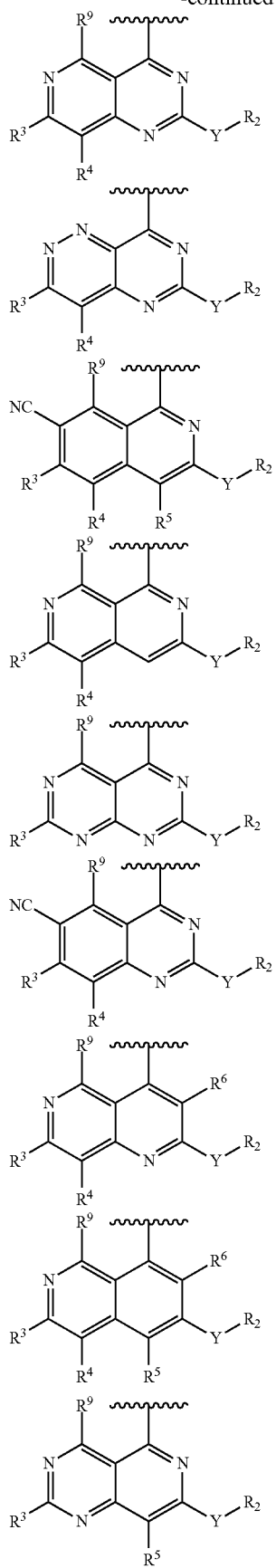
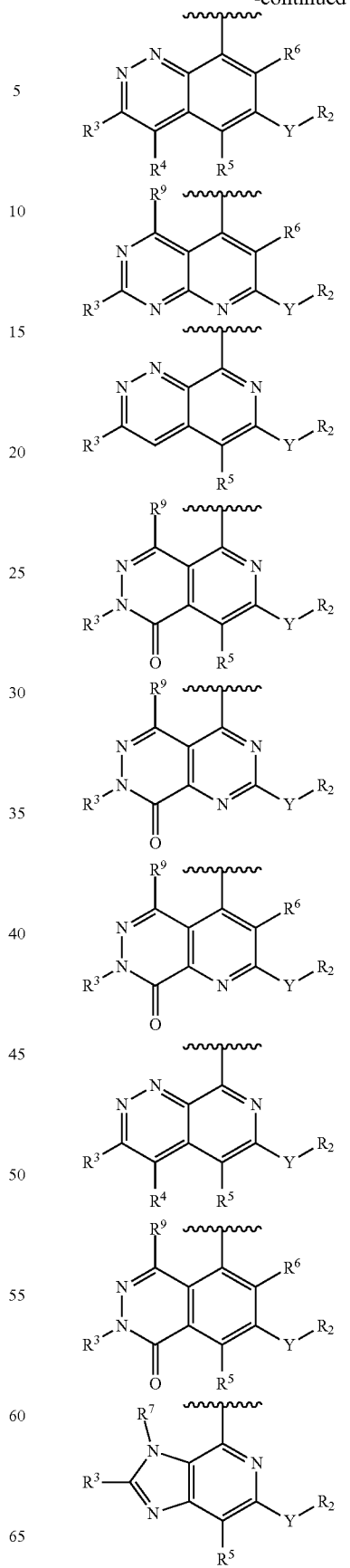

-continued

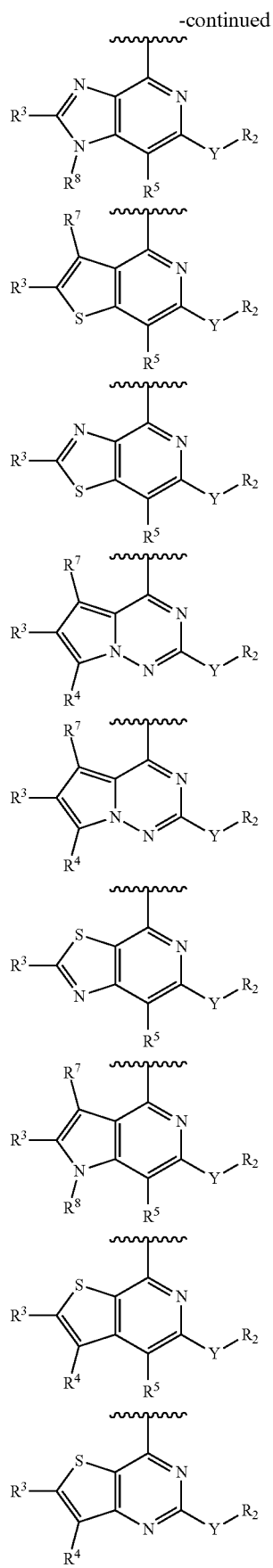

-continued

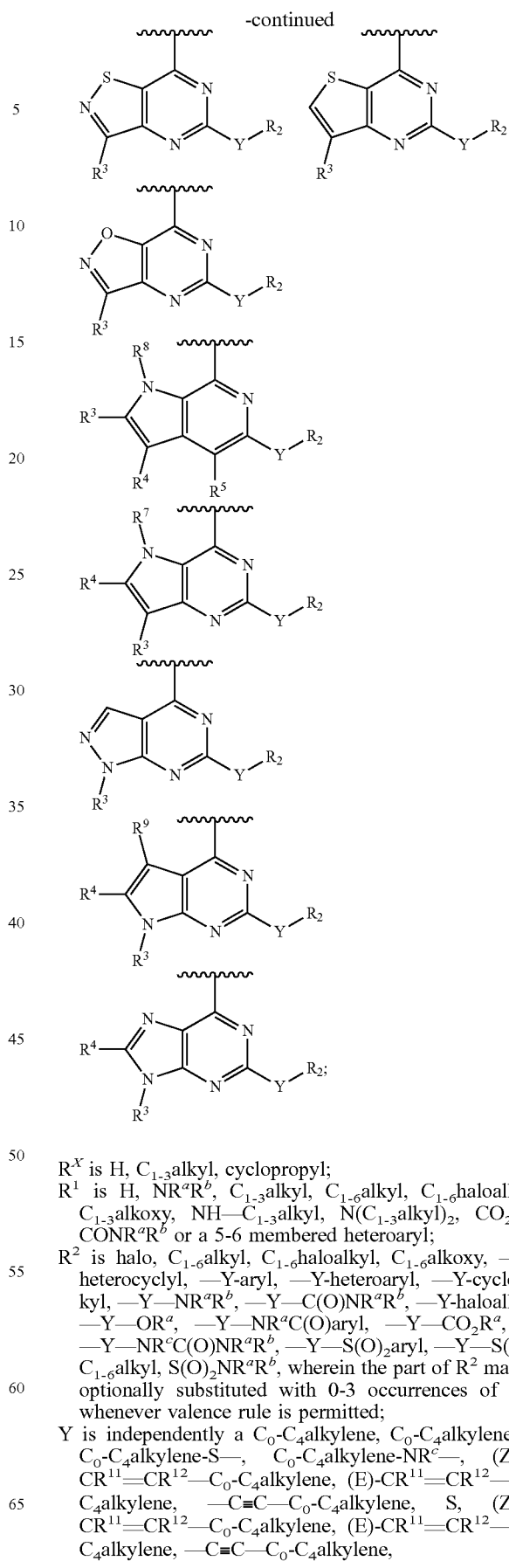

$R^X$ is H, $C_{1-3}$alkyl, cyclopropyl;
$R^1$ is H, $NR^aR^b$, $C_{1-3}$alkyl, $C_{1-6}$alkyl, $C_{1-6}$haloalkyl, $C_{1-3}$alkoxy, NH—$C_{1-3}$alkyl, $N(C_{1-3}alkyl)_2$, $CO_2R^8$, $CONR^aR^b$ or a 5-6 membered heteroaryl;
$R^2$ is halo, $C_{1-6}$alkyl, $C_{1-6}$haloalkyl, $C_{1-6}$alkoxy, —Y-heterocyclyl, —Y-aryl, —Y-heteroaryl, —Y-cycloalkyl, —Y—$NR^aR^b$, —Y—$C(O)NR^aR^b$, —Y-haloalkyl, —Y—$OR^a$, —Y—$NR^aC(O)$aryl, —Y—$CO_2R^a$, or —Y—$NR^cC(O)NR^aR^b$, —Y—$S(O)_2$aryl, —Y—$S(O)_2$ $C_{1-6}$alkyl, $S(O)_2NR^aR^b$, wherein the part of $R^2$ maybe optionally substituted with 0-3 occurrences of $R^{10}$ whenever valence rule is permitted;
Y is independently a $C_0$-$C_4$alkylene, $C_0$-$C_4$alkylene-O, $C_0$-$C_4$alkylene-S—, $C_0$-$C_4$alkylene-$NR^c$—, (Z)—$CR^{11}$=$CR^{12}$—$C_0$-$C_4$alkylene, (E)-$CR^{11}$=$CR^{12}$—$C_0$-$C_4$alkylene, —C≡C—$C_0$-$C_4$alkylene, S, (Z)—$CR^{11}$=$CR^{12}$—$C_0$-$C_4$alkylene, (E)-$CR^{11}$=$CR^{12}$—$C_0$-$C_4$alkylene, —C≡C—$C_0$-$C_4$alkylene,

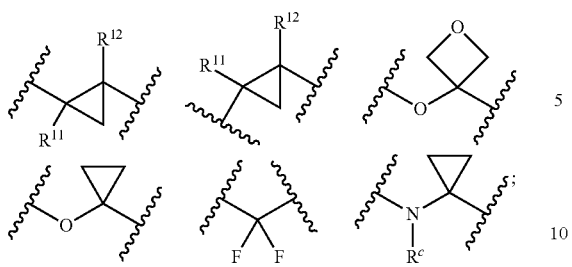

Z is a bond, O, S, or $NR^c$;

$R^3$ is an aryl or heteroaryl, wherein the aryl or heteroaryl is optionally substituted with 0-4 occurrences of $R^{10}$;

$R^4$, $R^5$, $R^6$ and $R^7$ are independently selected from H, halogen, —CN, $C_1$-$C_3$ alkyl, $C_{3-6}$cycloalkyl, $C_{3-6}$halocycloalkyl or $C_1$-$C_3$haloalkyl;

$R^8$ and $R^9$ are independently selected from H, $C_1$-$C_3$ alkyl, $C_{3-6}$cycloalkyl;

$R^a$, $R^b$ and $R^c$ are independently hydrogen or $C_{1-6}$ alkyl, —$C_{0-6}$alkylene-$C_{6-10}$ aryl, —$C_{0-6}$alkylene-5-10 membered heteroaryl or 5-10 membered heterocyclyl (preferably, hydrogen or $C_{1-6}$ alkyl, $C_{6-10}$ aryl, 5-10 membered heteroaryl or 5-10 membered heterocyclyl); or $R^a$ and $R^b$ are taken together with the atom(s) to which they are attached to form an optionally substituted 5-10 membered carbocyclyl, or heterocyclyl which is optionally substituted with 0-5 occurrences of $R^{10}$; $R^b$, $R^c$ and $R^e$ are independently substituted with 0-5 occurrences of $R^{10}$;

$R^{10}$ is independently selected from $C_{1-6}$ alkyl, $C_{1-6}$ alkoxy, halo, hydroxy, oxo, amino, $N(C_{1-6}alkyl)_2$, cyano, $C_{0-6}$alkylene-$NR^bR^a$, $C_{0-6}$alkylene-$NR^bR^a$, $C_{0-6}$alkylene-C(O)$NR^bR^a$, $C_{0-6}$alkylene-$NR^aC(O)R^b$, $C_{0-6}$alkylene-S(O)$_2R^b$, $C_{0-6}$alkylene-S(O)$_2NR^aR^b$, $C_{0-6}$alkylene-$NR^cS(O)_2R^b$, $C_{0-6}$alkylene-$NR^cS(O)_2NR^aR^b$, $C_{0-6}$alkylene-P(O)$R^aR^b$, $C_{0-6}$alkylene-P(O)(O$R^c$)(O$R^b$), $C_{0-6}$alkylene-cyano, $C_{0-6}$akylene-$C_{3-8}$ cycloalkyl and 5-10 membered heterocyclyl, $C_{6-10}$ aryl, 5-10 membered heteroaryl (preferably, selected from $C_{1-6}$ alkyl, $C_{1-6}$ alkoxy, halo, hydroxy, oxo, amino, $C_{0-6}$alkylene-$NR^bR^a$, $C_{0-6}$alkylene-$NR^bR^a$, $C_{0-6}$alkylene-C(O)$NR^bR^a$, $C_{0-6}$alkylene-$NR^aC(O)R^b$, $C_{0-6}$alkylene-S(O)$_2R^b$, $C_{0-6}$alkylene-S(O)$_2NR^aR^b$, $C_{0-6}$alkylene-$NR^aS(O)_2R^b$, $C_{0-6}$alkylene-$NR^cS(O)_2NR^aR^b$, $C_{0-6}$alkylene-P(O)$R^aR^b$, $C_{0-6}$alkylene-P(O)(O$R^c$)(O$R^b$), $C_{0-6}$alkylene-cyano, $C_{0-6}$alkylene-$C_{3-8}$ cycloalkyl and 5-10 membered heterocyclyl, $C_{6-10}$ aryl, 5-10 membered heteroaryl; two adjacent $R^{10}$, for example, two $R^{10}$ attached to adjacent two atoms (the two atoms attached each other only through a bond), or two $R^{10}$ attached to the same atom are taken together with the atom to which they are attached to form an optionally substituted 5-10 membered cyclyl or 5-10 membered heterocyclyl which contains 0-3 heteroatoms;

$R^{11}$ and $R^{12}$ are independently selected from H, F, $C_1$-$C_3$ alkyl, $C_{3-6}$cycloalkyl, $C_1$-$C_3$haloalkyl or cyclopropyl;

each alkyl, alkenyl, alkynyl, cycloalkyl, heterocyclyl, aryl, heteroaryl can be substituted with one or more substituents.

In some embodiments, the KRAS G12D binding moiety is:

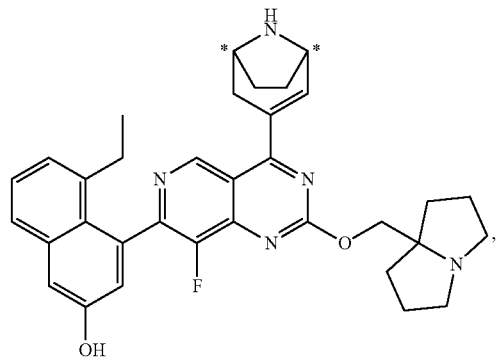

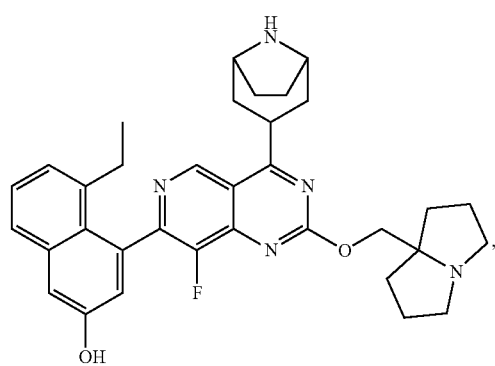

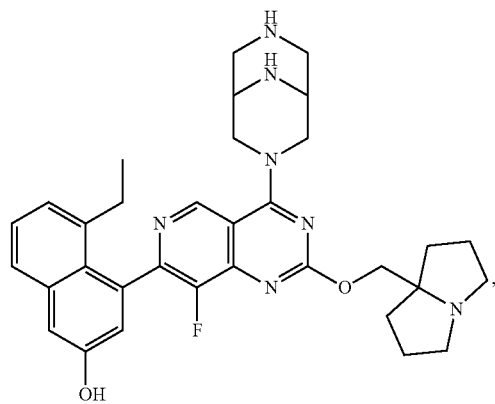

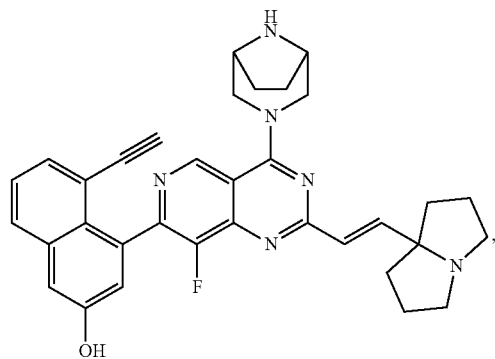

497
-continued
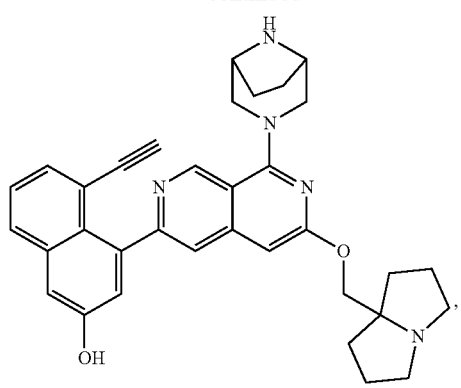
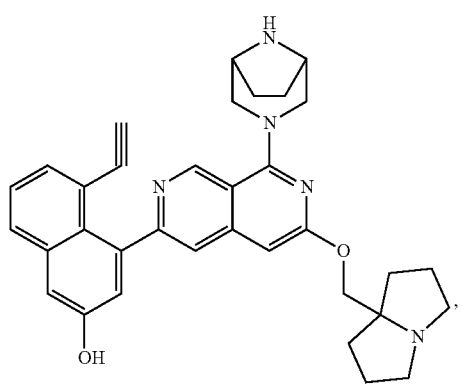
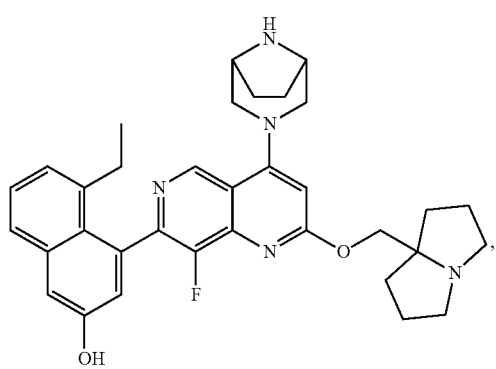
7-1
7-2
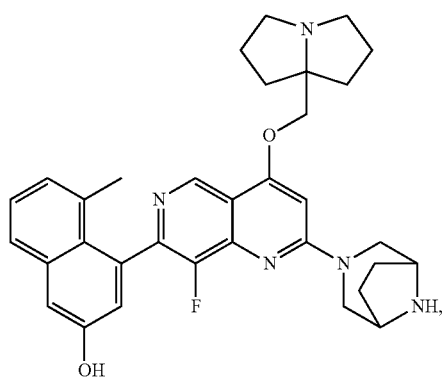
498
-continued
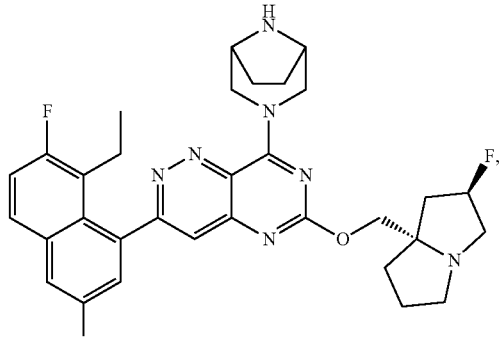
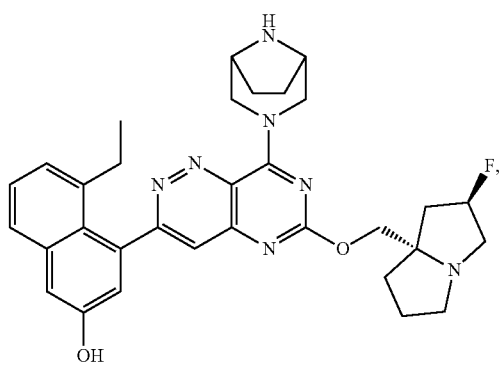
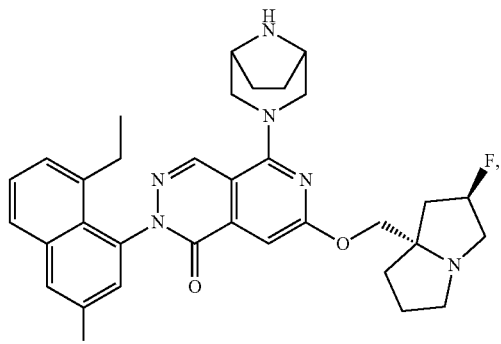
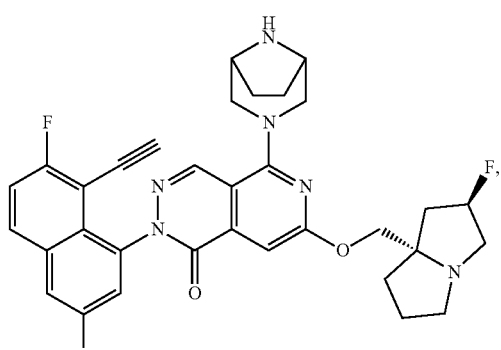

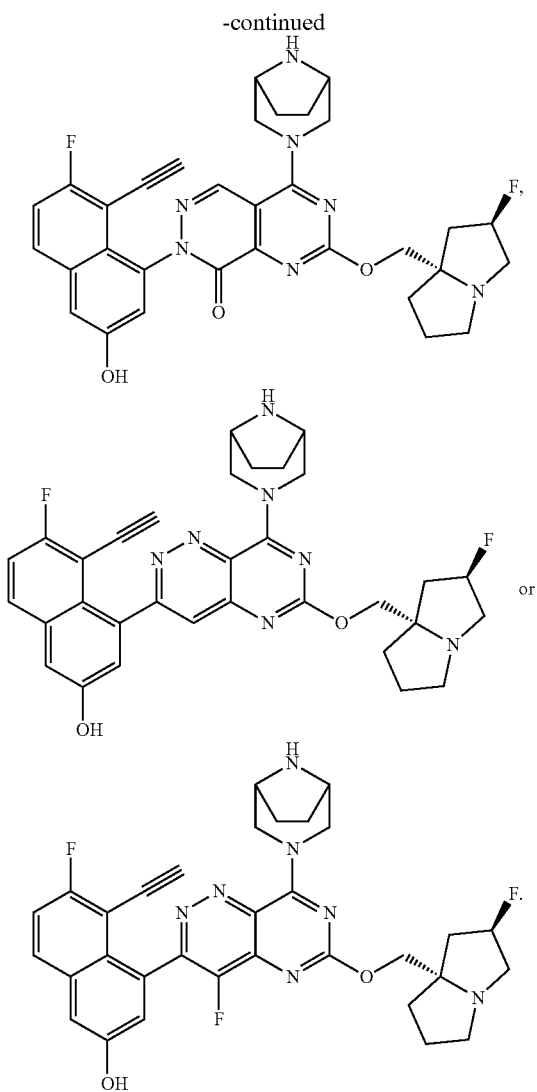

Yet other specific examples of KRAS G12D binding moieties are disclosed in International Publication No. WO 2022/194066, the entire content of which is incorporated herein by reference. In some embodiments, a KRAS G12D binding moiety is a KRAS G12D binding moiety (e.g., inhibitor) disclosed in WO 2022/194066. For example, in some embodiments, a KRAS G12D binding moiety has the following structural formula:

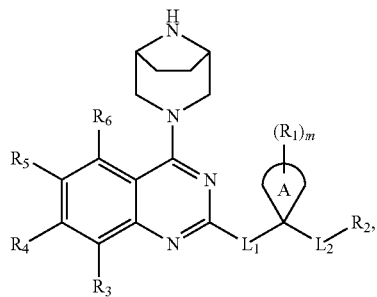

(I)

wherein:
Ring A is selected from $C_{3-6}$ cycloalkyl or 3-6 membered heterocyclyl;
$L_1$ is selected from —O—$(CH_2)_{0-3}$, —S—$(CH_2)_{0-3}$, —NH—$(CH_2)_{0-3}$ or $C_{1-3}$ alkylene;
$L_2$ is selected from a bond or a $C_{1-3}$ alkylene group;
$R_1$ is independently selected from H, halogen, alkyl, alkoxy, haloalkyl, hydroxy, and hydroxyalkyl;
$R_2$ is selected from $C_{3-14}$ cycloalkyl, 3-14-membered heterocyclyl, $C_{6-14}$ aryl and 5-14-membered heteroaryl, the $C_{3-14}$ cycloalkyl, 3-14-membered heteroaryl, $C_{6-14}$ aryl and 5-14 membered heteroaryl are optionally further substituted with 1-4 substitutents selected from halogen, $C_{1-6}$ alkyl, $C_{1-6}$ alkoxy, $C_{1-6}$ haloalkyl, cyano, amino, nitro, hydroxyl, $C_{1-6}$ hydroxyalkyl, $C_{0-3}$ alkylene-N$(R_a)_2$, cycloalkyl, heterocyclyl, aryl and heteroaryl, and the $R_a$ is independently selected from H or $C_{1-6}$ alkyl;
$R_3$ is selected from H, halogen, $C_{1-6}$ alkyl or —$OR_{2a}$, and $R_{2a}$ is selected from $C_{1-6}$ alkyl, $C_{3-8}$ cycloalkyl or haloalkyl;
$R_4$ is selected from cycloalkyl, heterocyclyl, aryl or heteroaryl optionally further substituted with one or more $R_{3a}$; each $R_{3a}$ is independently selected from H, =O, =S, acyl, hydroxy, cyano, halogen, nitro, $C_{1-6}$ alkyl, $C_{3-6}$ cycloalkyl, $C_{1-6}$ haloalkyl, —$C_{0-3}$ alkylene-$OR_b$, —OC(=O)$C_{1-6}$ alkyl, —$C_{0-3}$ alkylene-$SR_b$, —$C_{0-3}$ alkylene-N$(R_b)_2$, —$C_{0-3}$ alkylene-S(=O)$R_b$, —$C_{0-3}$ alkylene-S(=O)$_2R_b$, —$C_{0-3}$ alkylene-$SR_b$, —$C_{0-3}$ alkylene-S$(R_b)_5$, —$C_{0-3}$alkylene-C(=O)$R_b$, —$C_{0-3}$ alkylene-C(=O)$OR_b$, —$C_{0-3}$ alkylene-C(=O)N$(R_b)_2$, substituted or unsubstituted $C_{2-6}$ alkenyl, substituted or unsubstituted $C_{2-6}$ alkynyl, substituted or unsubstituted —$C_{0-3}$ alkylene-$C_{3-14}$ cycloalkyl, substituted or unsubstituted —$C_{0-3}$ alkylene-(3-14 membered heterocycloalkyl), substituted or unsubstituted —$C_{0-3}$ alkylene-$C_{6-14}$ aryl or substituted or unsubstituted —$C_{0-3}$ alkylene-(5-14-membered heteroaryl, each $R_b$ is independently H, $C_{1-6}$ alkyl, $C_{3-6}$ cycloalkyl or $C_{1-6}$ haloalkyl;
$R_5$ is selected from H, amino, substituted amino, $C_{1-6}$ alkyl, substituted $C_{1-6}$ alkyl, halogen, $C_{2-6}$ alkenyl, substituted $C_{2-6}$ alkenyl, $C_{3-6}$ cycloalkyl or substituted $C_{3-6}$ cycloalkyl;
$R_6$ is selected from H, halogen or $C_{1-6}$ alkyl; and
m is selected from 0, 1, 2, 3 or 4.
In some embodiments, the KRAS G12D binding moiety is:

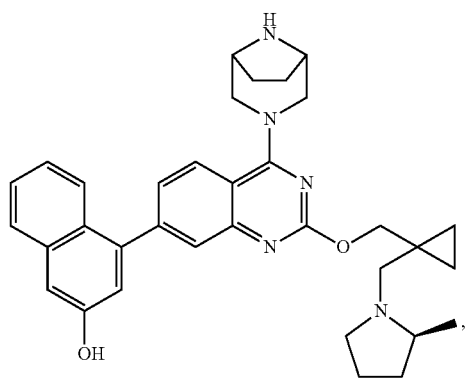

501
-continued
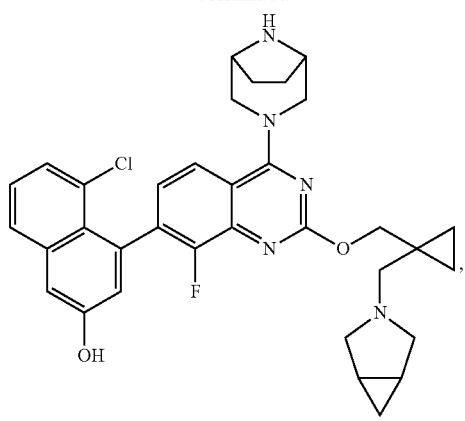
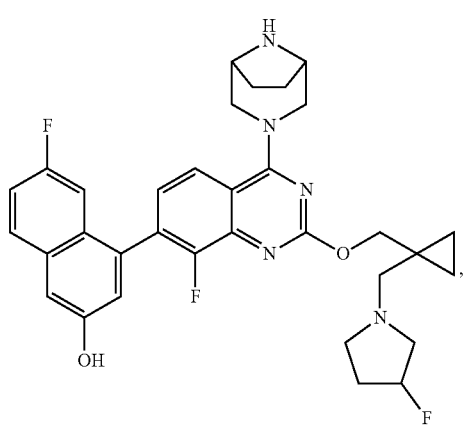
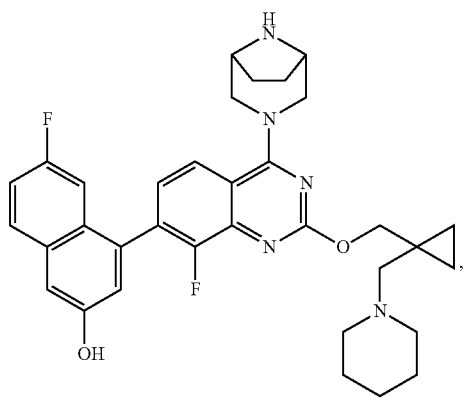
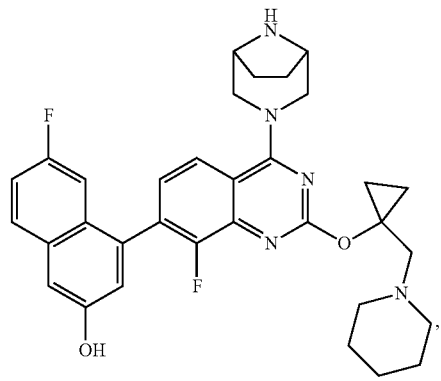
502
-continued
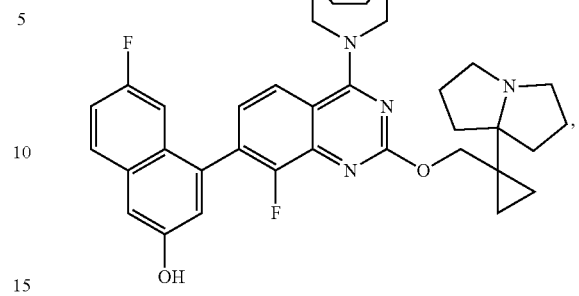
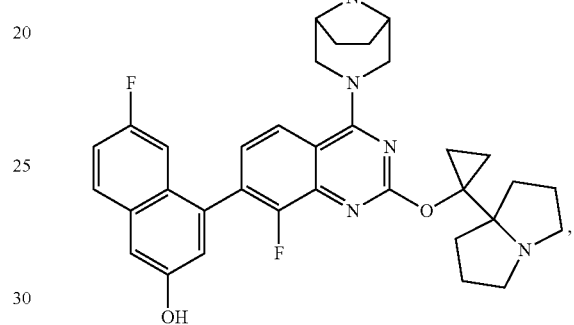
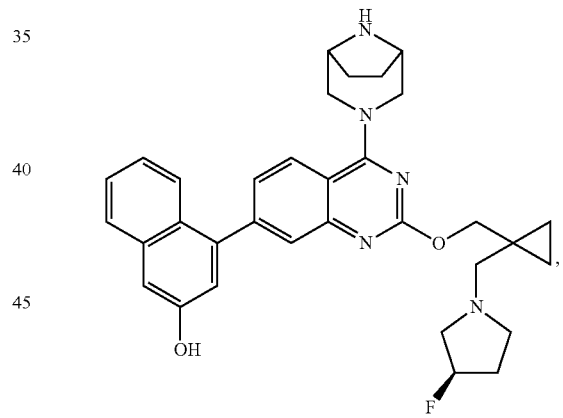
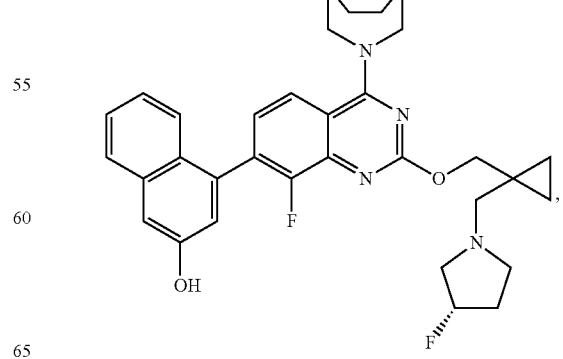

503
-continued
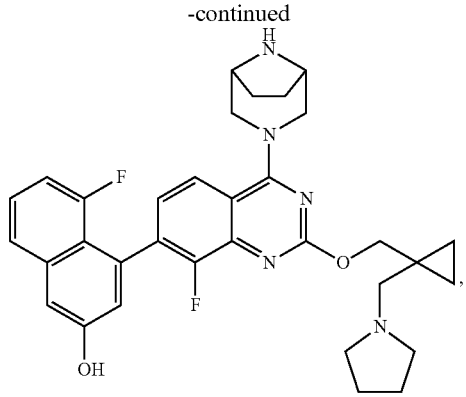
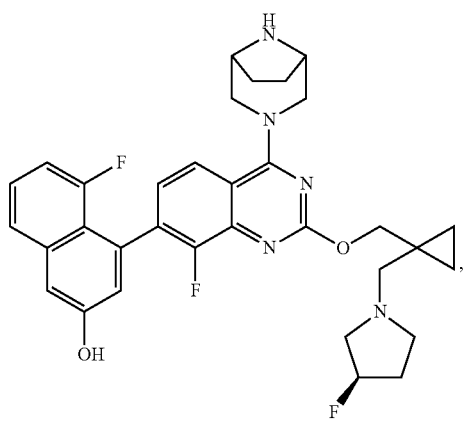
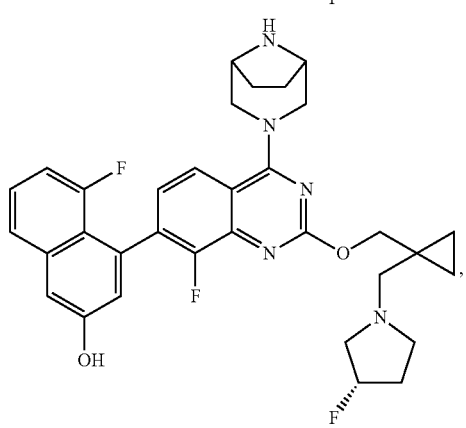
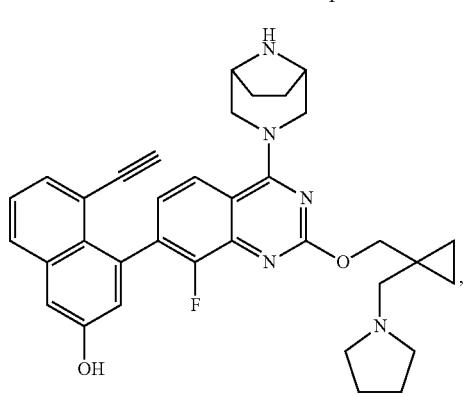
504
-continued
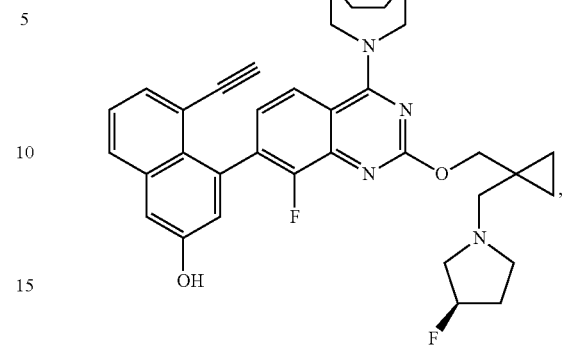
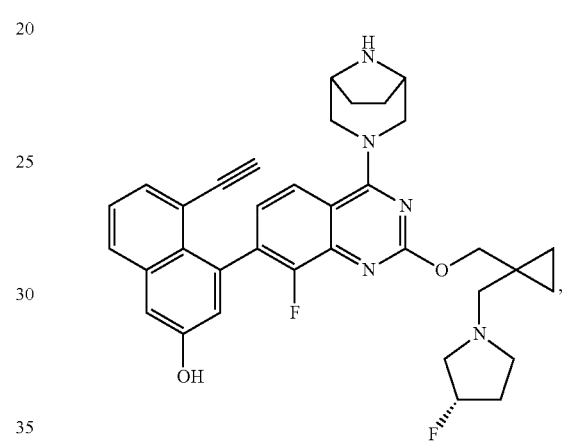
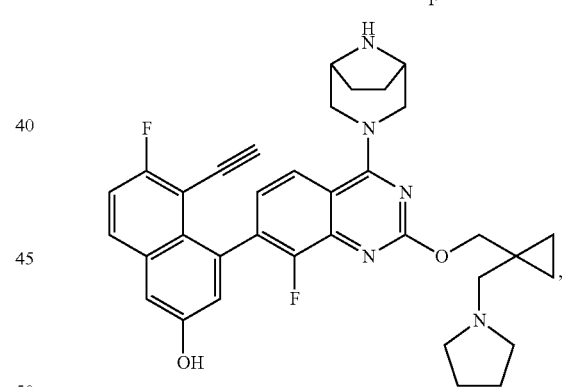
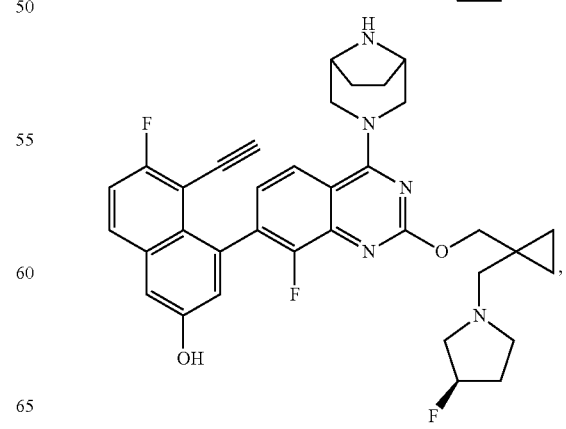

| 505 -continued | 506 -continued |
|---|---|
| 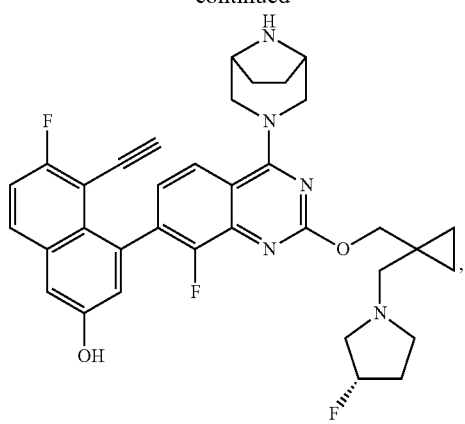 | 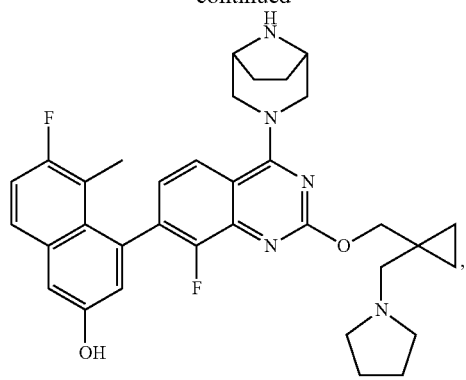 |
| 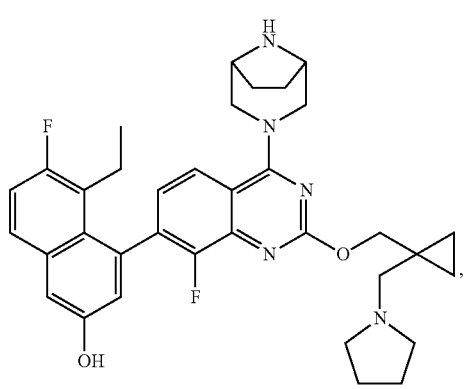 | 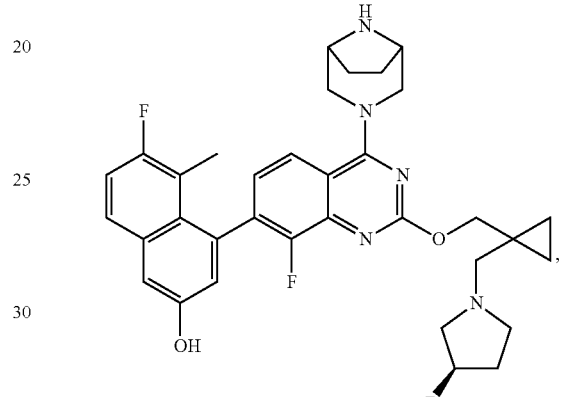 |
| 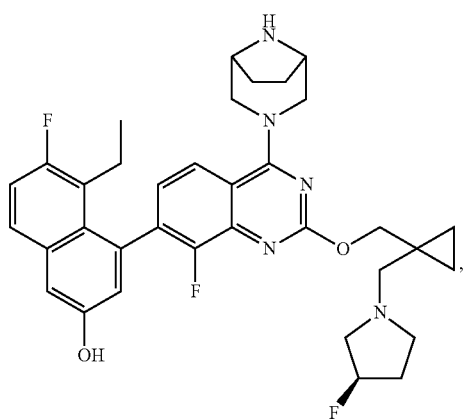 | 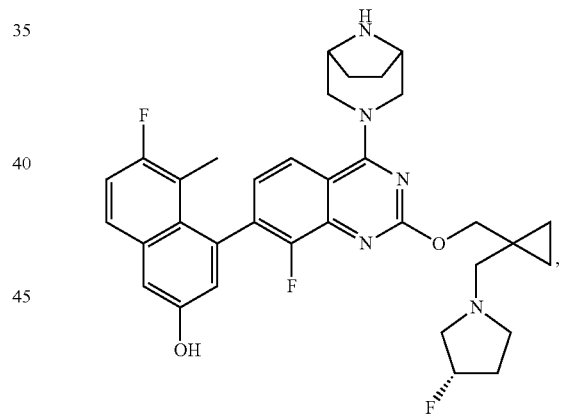 |
| 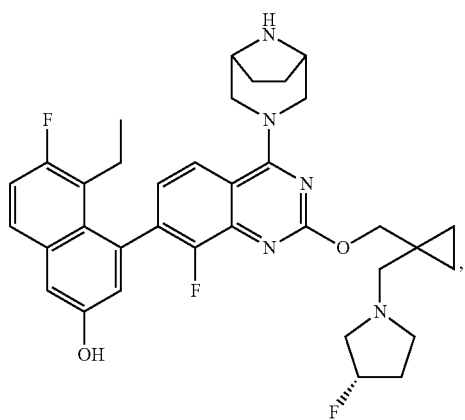 | 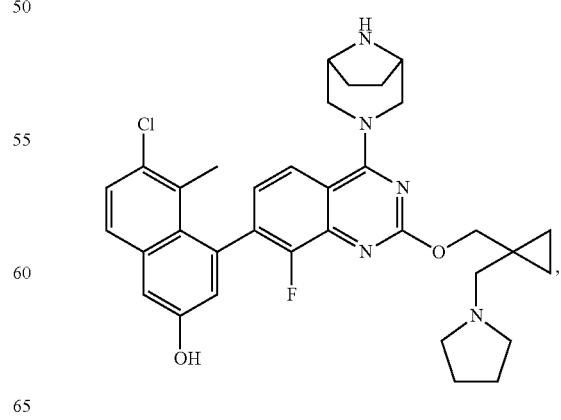 |

507
-continued
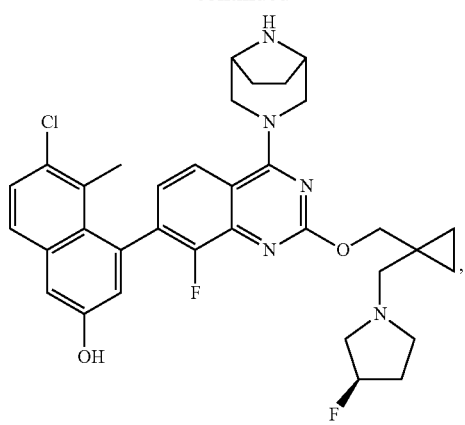
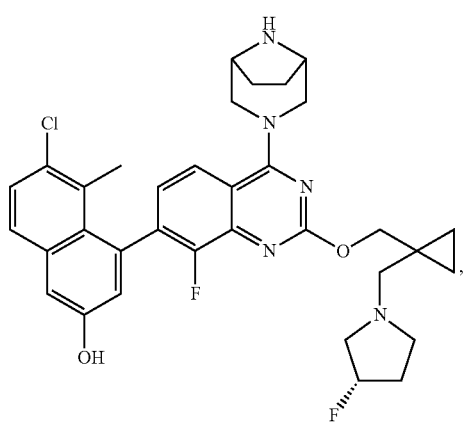
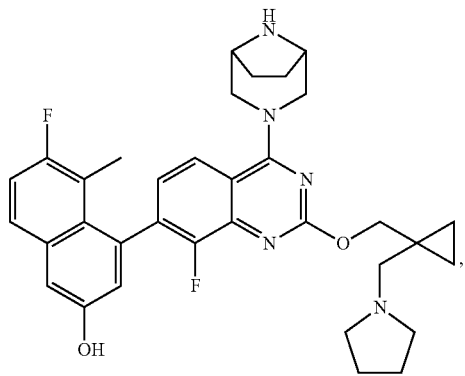
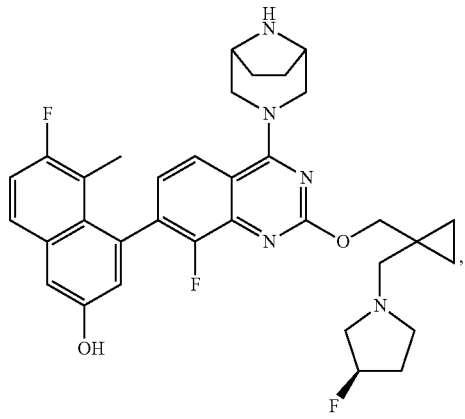
508
-continued
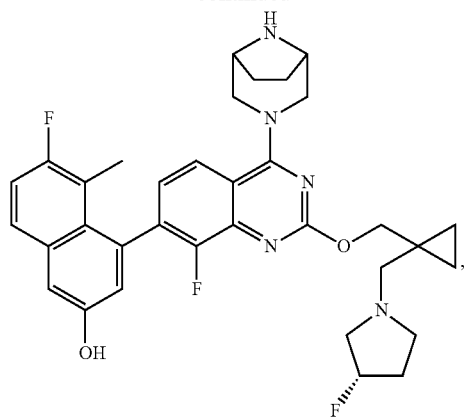
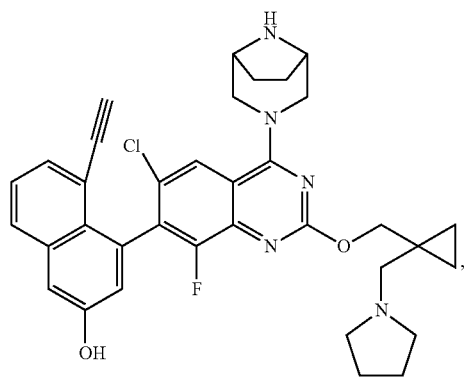
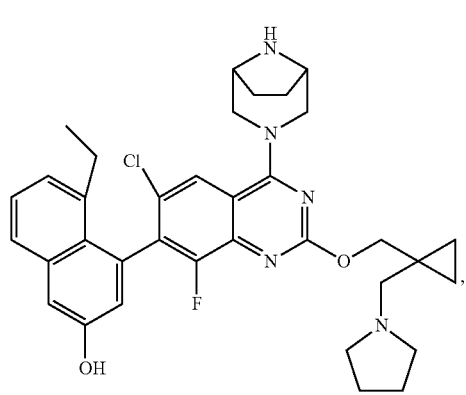
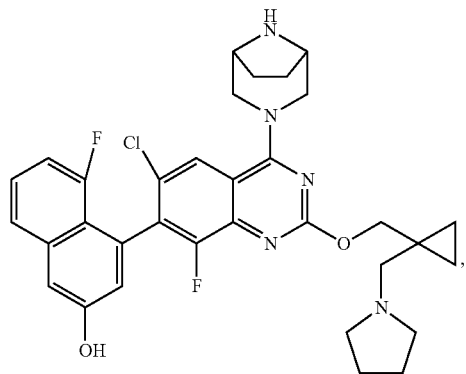

509
-continued
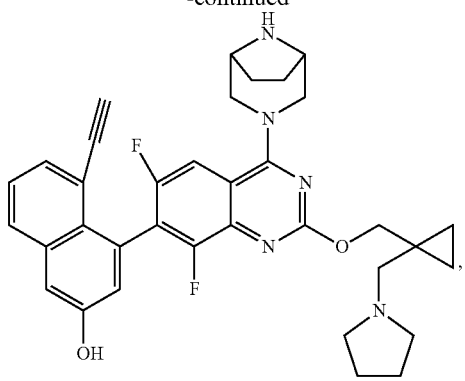
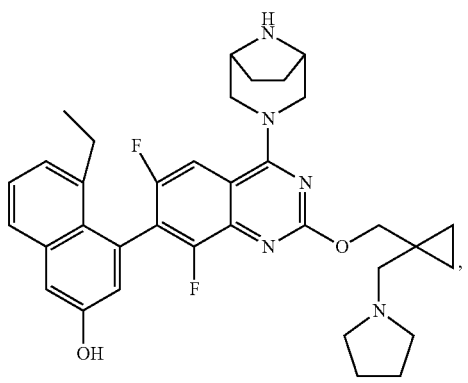
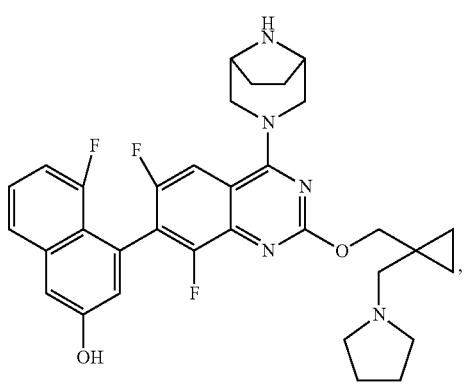
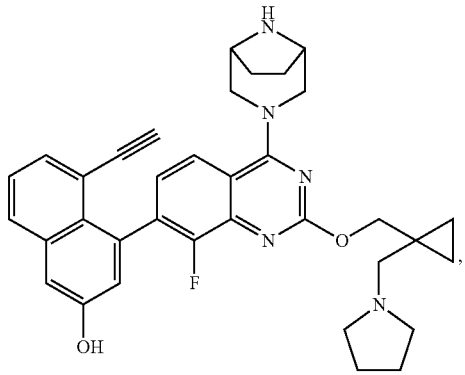
510
-continued
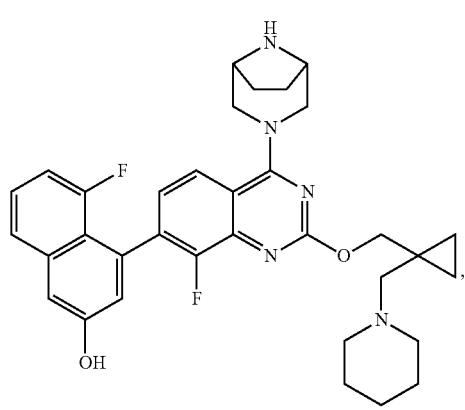
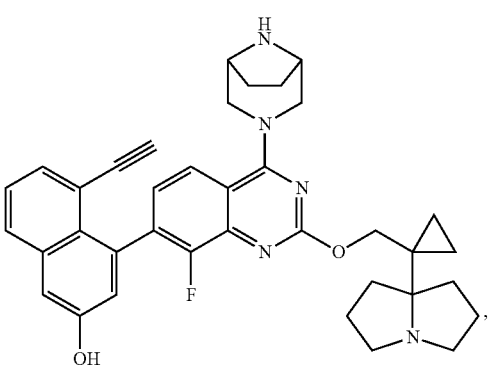
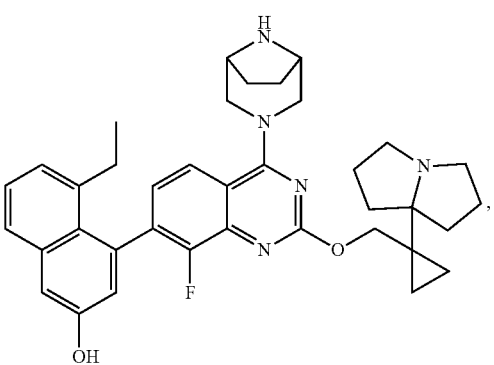

511
-continued
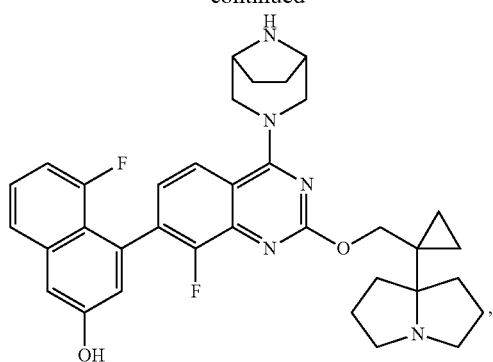
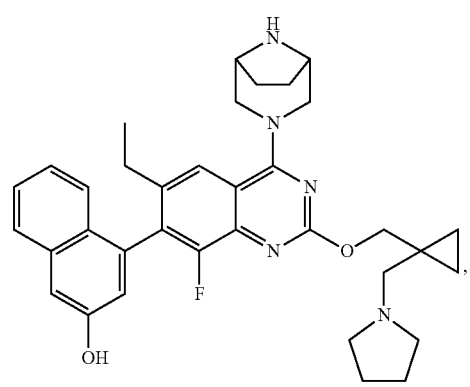
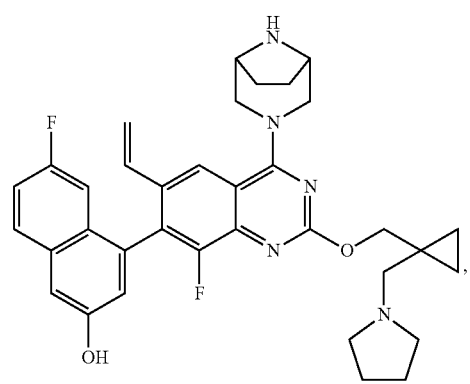
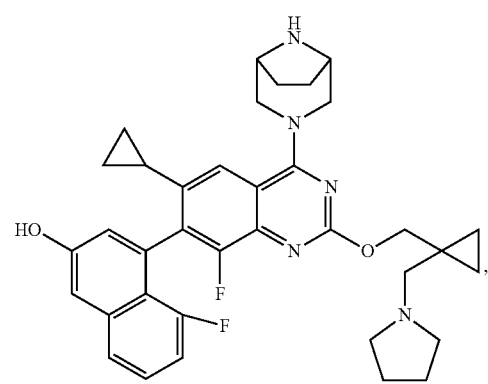
512
-continued
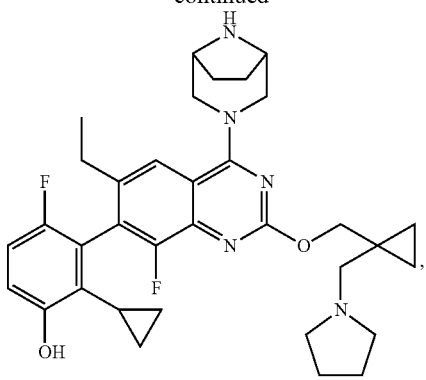
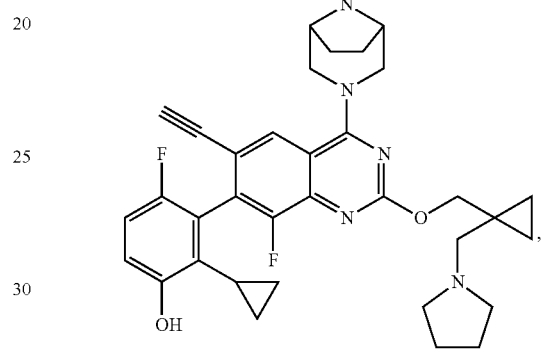
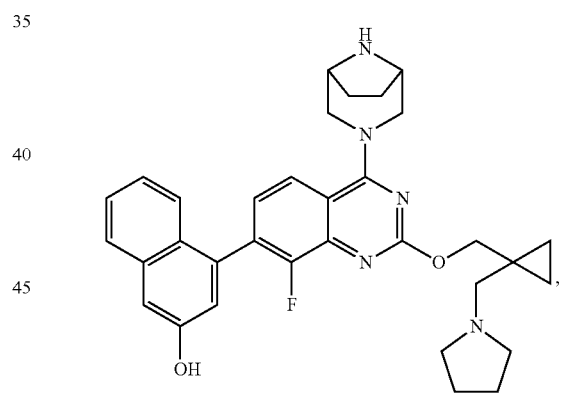
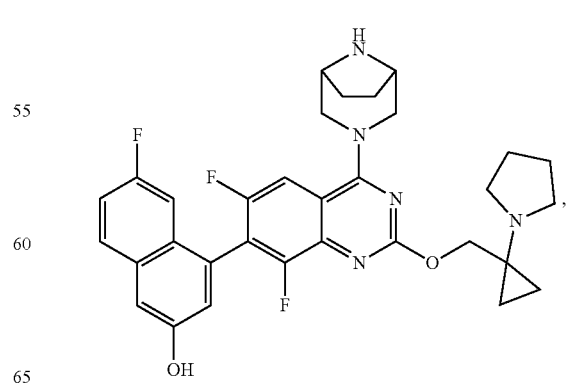

513
-continued
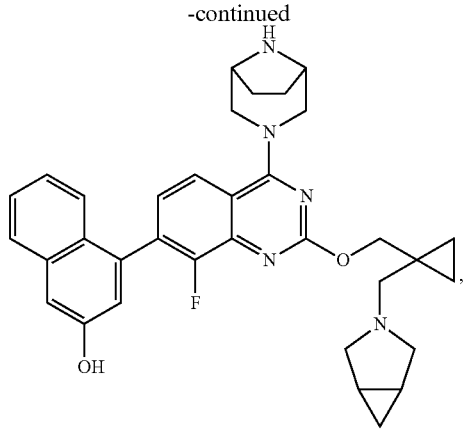
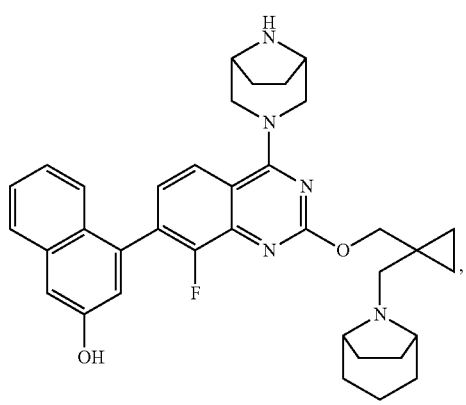
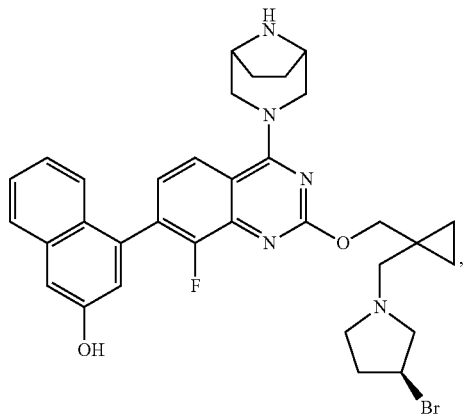
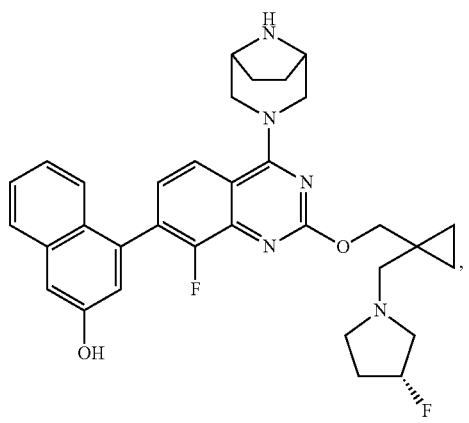
514
-continued
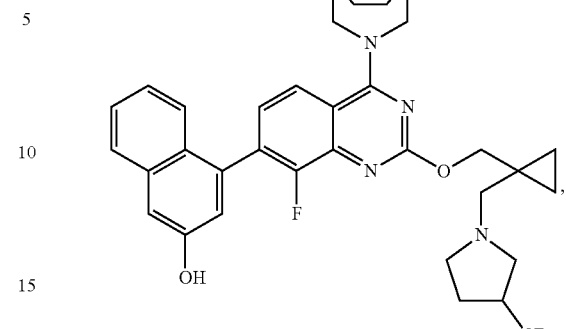

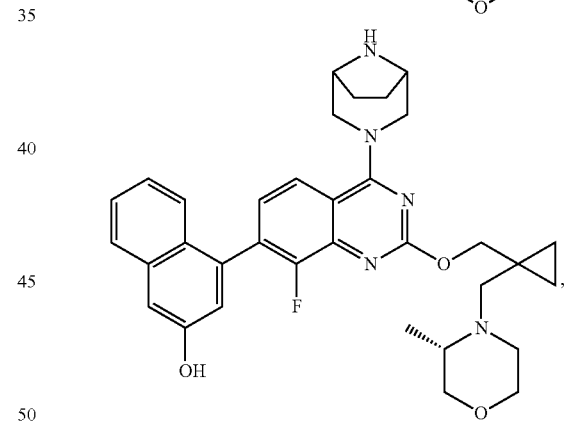
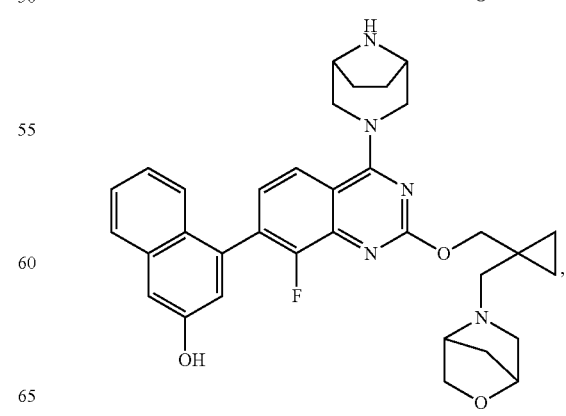

515
-continued
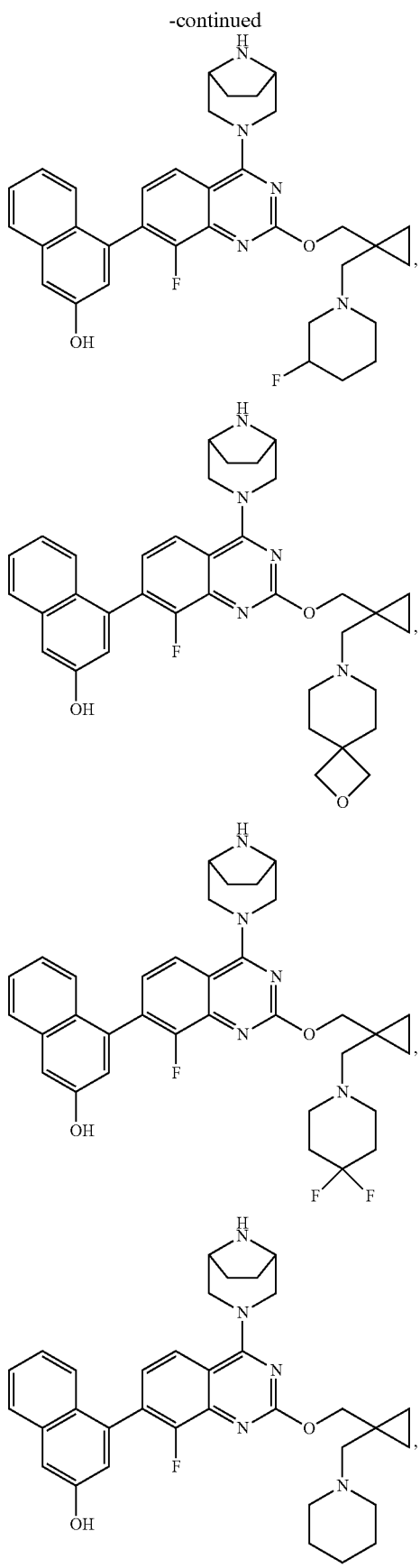
516
-continued
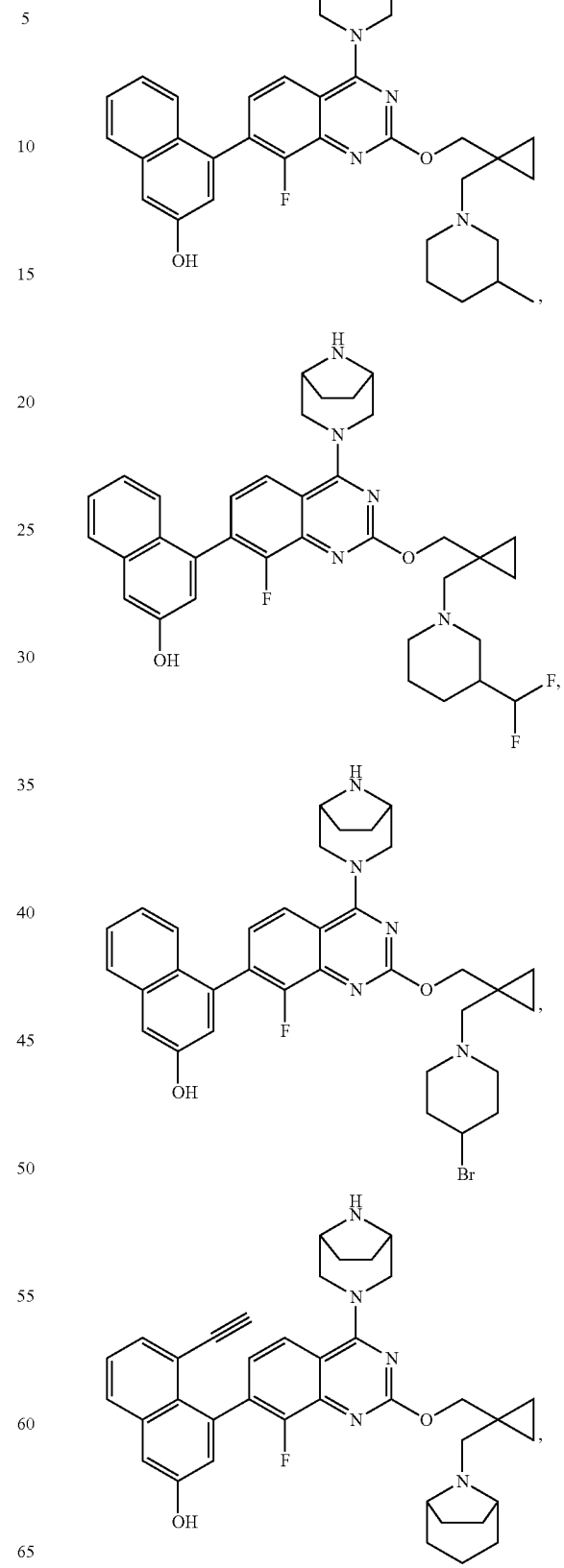

517
-continued
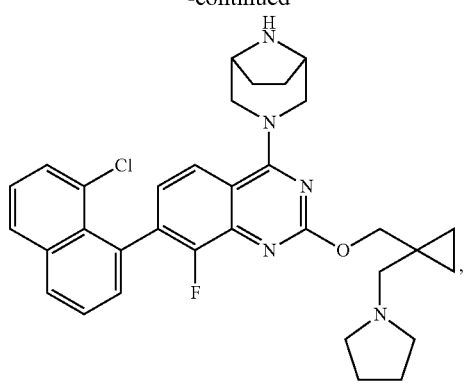
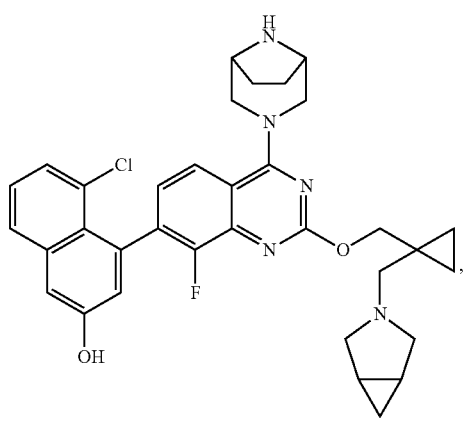
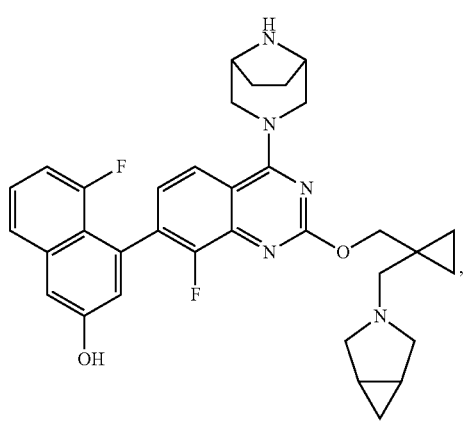
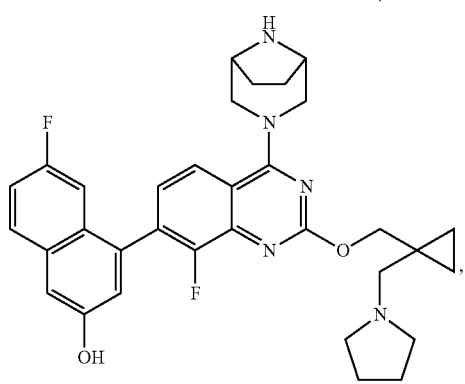
518
-continued
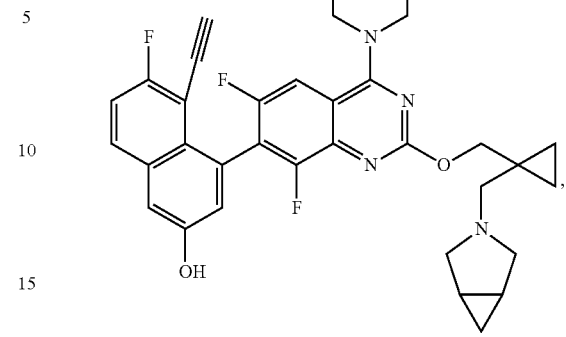
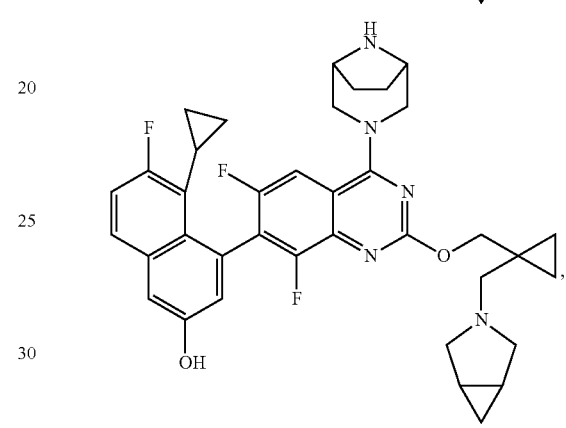
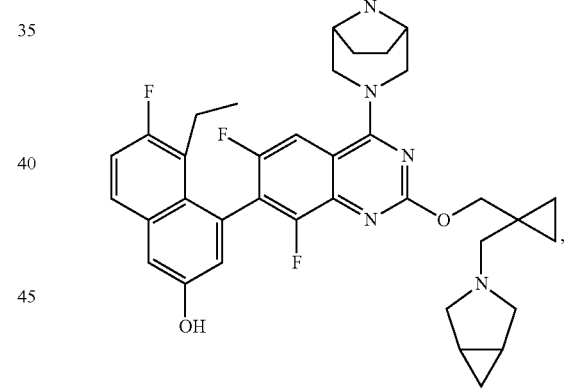
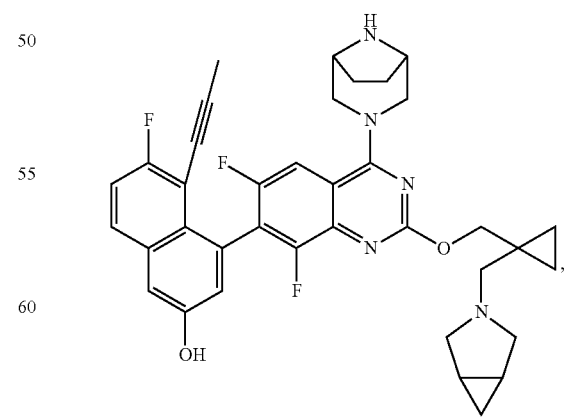

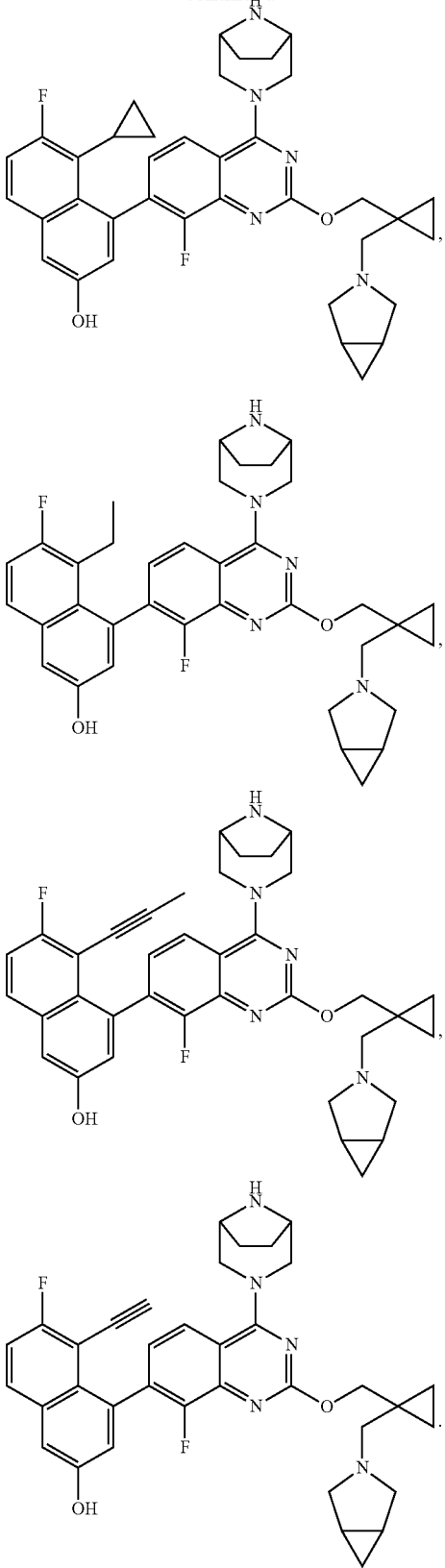

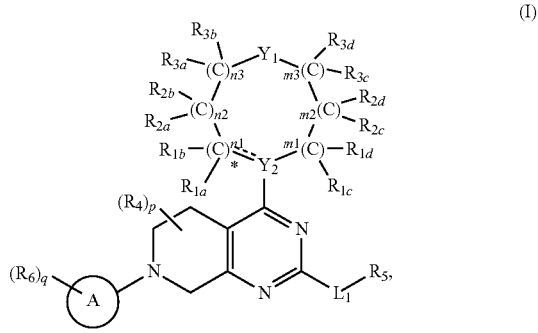

reference. In some embodiments, a KRAS G12D binding moiety is a KRAS G12D binding moiety (e.g., inhibitor) disclosed in WO 2022/148421. For example, in some embodiments, a KRAS G12D binding moiety has the following structural formula:

(I)

wherein:
Ring A is an aryl group or a 5- to 7-membered monocyclic heteroaryl or 8- to 12-membered bicyclic heteroaryl group;

═ is each independently a single bond or double bond;

$Y_1$ is —NH— or —C($R_{Y1a}$)(NH$R_{Y1b}$)—;

$Y_2$ is N or CR$_{Y2}$ in the case that ═ is a single bond; or $Y_2$ is C and $R_{1b}$ is absent in the case that ═ is a double bond;

n1, n2, n3, m1, m2, and m3 are each independently 0 or 1, provided that at least one of n1, n2 and n3 is 1; and at least one of m1, m2 and m3 is 1;

p is 0, 1, 2, 3, 4, 5 or 6;

q is 0, 1, 2, 3, 4, 5, 6 or 7 provided that the valence theory is met;

$R_{1a}$, $R_{1b}$, $R_{2a}$, $R_{2b}$, $R_{3a}$, $R_{3b}$, $R_{1c}$, $R_{1d}$, $R_{2c}$, $R_{2d}$, $R_{3c}$, $R_{3d}$, $R_{Y1a}$, $R_{Y1b}$ and $R_{Y2}$, if present, are each independently hydrogen, halogen, —$C_{1-8}$alkyl, $C_3$-$C_8$cycloalkyl, 3- to 8-membered heterocyclyl, $C_6$-$C_{12}$aryl, 5- to 12-membered heteroaryl, —CN, —OR$_{1e}$, —NR$_{1e}$R$_{1f}$; wherein each of —$C_{1-8}$alkyl, $C_3$-$C_8$cycloalkyl, 3- to 8-membered heterocyclyl, $C_6$-$C_{12}$aryl or 5- to 12-membered heteroaryl is optionally substituted with at least one substituent $R_{1g}$;

at least one pair of ($R_{1a}$ and $R_{1c}$), ($R_{1a}$ and $R_{2c}$), ($R_{1a}$ and $R_{3c}$), ($R_{2a}$ and $R_{1c}$), ($R_{2a}$ and $R_{2c}$), ($R_{2a}$ and $R_{3c}$), ($R_{3a}$ and $R_{1c}$), ($R_{3a}$ and $R_{2c}$), ($R_{3a}$ and $R_{3c}$), ($R_{Y1a}$ and $R_{Y2}$), ($R_{Y1a}$ and $R_{1a}$), ($R^{Y1a}$ and $R_{2a}$), ($R_{Y1a}$ and $R_{1c}$), ($R_{Y1a}$ and $R_{2c}$), ($R_{Y1b}$ and $R_{1a}$), ($R_{Y1b}$ and $R_{2a}$), ($R_{Y1b}$ and $R_{1c}$), ($R_{Y1b}$ and $R_{2c}$), and ($R_{Y1b}$ and $R_{Y2}$) form a bridge containing one, two, three, or four —CH$_2$-moieties in addition to the two bridgeheads, wherein one of the —CH$_2$-moiety is optionally replaced with —O—, —S— or —NH— and wherein said bridge is optionally substituted with at least one substituent $R_{1g}$;

optionally, ($R_{Y1a}$ and $R_{Y1b}$), ($R_{Y1a}$ and $R_{3c}$), ($R_{Y1b}$ and $R_{3c}$), ($R_{Y1b}$ and $R_{3a}$), or ($R_{Y1b}$ and $R_{3c}$) form 3- to 12-membered ring, the said ring comprises 0-3 heteroatoms selected from nitrogen, sulfur and oxygen and the said bridge is optionally substituted with at least one substituent $R_{1g}$;

$R_{1e}$ and $R_{1f}$ are each independently selected from hydrogen, —$C_{1-8}$alkyl, —$C_{2-8}$alkenyl, —$C_{2-8}$alkynyl, Other specific examples of KRAS G12D binding moieties are disclosed in International Publication No. WO 2022/148421, the entire content of which is incorporated herein by $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl;

$R_{1g}$, at each occurrence, is independently halogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl, —$C_{1-8}$haloalkyl, $C_{1-8}$alkoxy-$C_{1-8}$alkyl-, —CN, —OH, —$NH_2$, —$C_{1-8}$alkoxyl, —COOH, -or CO—$C_{1-8}$alkyl;

$R_6$ is hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, oxo, —$OR_{6a}$, —$SR_{6a}$, —$SO_2R_{6a}$, —$SO_2NR_{6a}R_{6b}$, —$COR_{6a}$, —$CO_2R_{6a}$, —$CONR_{6a}R_{6b}$, —$NR_{6a}R_{6b}$, —$NR_{6a}COR_{6b}$, —$NR_{6a}CO_2R_{6b}$, or —$NR_{6a}SO_2R_{6b}$; each of —$C_{1-8}$alkyl, $C_3$-$C_8$cycloalkyl, 3- to 8-membered heterocyclyl, $C_6$-$C_{12}$aryl or 5- to 12-membered heteroaryl is optionally substituted with at least one substituent $R_{6c}$;

$R_{6a}$ and $R_{6b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$ aryl or 5- to 12-membered heteroaryl, each of —$C_{1-8}$alkyl, $C_3$-$C_8$cycloalkyl, 3- to 8-membered heterocyclyl, $C_6$-$C_{12}$ aryl or 5- to 12-membered heteroaryl is optionally substituted with at least one substituent $R_{6d}$;

$R_{6c}$, at each occurrence, is independently halogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$ aryl, or 5- to 12-membered heteroaryl; or two $R_6$ together with the atoms to which they are attached, form a 5, 6, 7, or 8-membered unsaturated (preferably aromatic) or saturated ring, said ring comprising 0-3 heteroatoms independently selected from nitrogen, oxygen or sulfur; said ring is optionally substituted with at least one substituent $R_{6d}$;

$R_{6d}$ is hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, oxo, —$OR_{6e}$, —$SO_2R_{6e}$, —$SO_2NR_{6e}R_{6f}$, —$COR_{6e}$, —$CO_2R_{6e}$, —$CONR_{6e}R_{6f}$, —$NR_{6e}R_{6f}$, —$NR_{6e}COR_{6f}$, —$NR_{6e}CO_2R_{6f}$, or —$NR_{6e}SO_2R_{6f}$; each of $C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R_{6g}$;

$R_{6e}$ and $R_{6f}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl, $R_{6g}$, at each occurrence, is independently halogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R_4$ is hydrogen, halogen, —$C_{1-8}$alkyl, $C_3$-$C_8$cycloalkyl, —$C_{2-8}$alkenyl, —$C_{2-8}$alkynyl, 3- to 8-membered heterocyclyl, $C_6$-$C_{12}$aryl, 5- to 12-membered heteroaryl, —CN, oxo, —$OR_{4a}$, —$SR_{4a}$, —$SO_2R_{4a}$, —$SO_2NR_{4a}R_{4b}$, —$COR_{4a}$, —$CO_2R_{4a}$, —$CONR_{4a}R_{4b}$, —$NR_{4a}R_{4b}$, —$NR_{4a}COR_{4b}$, —$NR_{4a}CO_2R_{4b}$, or —$NR_{4a}SO_2R_{4b}$; each of —$C_{1-8}$alkyl, $C_3$-$C_8$cycloalkyl, —$C_{2-8}$alkenyl, —$C_{2-8}$alkynyl, 3- to 8-membered heterocyclyl, $C_6$-$C_{12}$aryl or 5- to 12-membered heteroaryl is optionally substituted with at least one substituent $R_{4c}$, or two $R_4$ join each other to form spiro cycle or bicycle;

$R_{4a}$ and $R_{4b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl; each of —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl is optionally substituted with at least one substituent $R_{4d}$;

$R_{4c}$ and $R_{4d}$, at each occurrence, are each independently halogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$L_1$ is selected from a single bond, —O—, —$NR^{L1a}$—, —C(O)—, —$C_{1-8}$alkylene-, $*^{L1}$—O—$C_{1-8}$alkylene-$**^{L1}$, —$C_3$-$C_8$cycloalkylene-, $*^{L1}$—O—$C_3$-$C_8$cycloalkylene-$**^{L1}$, $*^{L1}$—O—$C_{1-8}$alkylene-$NR^{L1a}$—$**^{L1}$, $*^{L1}$—O—$C_{1-8}$alkylene-CO—$**^{L1}$, $*^{L1}$—$C_{1-8}$alkylene-O—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$,

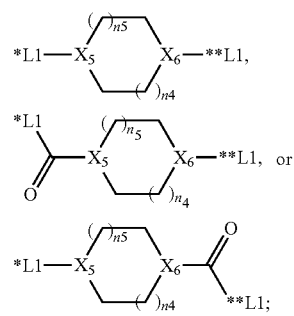

each of said —$C_{1-8}$alkylene-, $*^{L1}$—O—$C_{1-8}$alkylene-$**^{L1}$, —$C_3$-$C_8$cycloalkylene-, $*^{L1}$—O—$C_3$-$C_8$cycloalkylene-$**^{L1}$, $*^{L1}$—O—$C_{1-8}$alkylene-$NR^{L1a}$—$**^{L1}$, $*^{L1}$—O—$C_{1-8}$alkylene-CO—$**^{L1}$, $*^{L1}$—$C_{1-8}$alkylene-O—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$,

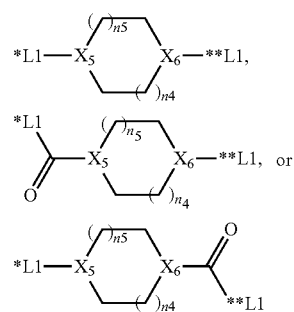

are optionally substituted with at least one $R^{L1b}$;

wherein **$*^{L1}$ refers to the position attached to the

moiety, and $*^{L1}$ refers to the position attached to the other side;

$R^{L1a}$ is selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L1c}$;

each of said $R^{L1b}$ and $R^{L1c}$ are independently halogen, hydroxy, —$C_{1-8}$alkyl, —$C_{1-8}$alkoxy, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl; or two $R^{L1b}$ or two $R^{L1c}$ together with the atoms to which they are attached, form a 3- to 6-membered unsaturated or saturated ring, said ring comprising 0-3 heteroatoms independently selected from nitrogen, oxygen or sulfur; said ring is optionally substituted with at least one substituent halogen, hydroxy, —$C_{1-8}$alkyl, —$C_{1-8}$alkoxy, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

each of $X_5$ and $X_6$ are selected from CH or N;

n4 and n5 are each independently 0, 1 or 2;

$R_5$ is hydrogen, halogen, —$C_{1-8}$alkyl, $C_3$-$C_8$cycloalkyl, 3- to 12-membered heterocyclyl, $C_6$-$C_{12}$aryl, 5- to 12-membered heteroaryl, oxo, —CN, —$OR_{5a}$, —$COR_{5a}$, —$CO_2R_{5a}$, —$CONR_{5a}R_{5b}$, —$NR_{5a}R_{5b}$, —$NR_{5a}COR_{5b}$ or —$NR_{5a}CO_2R_{5b}$; wherein each of —$C_{1-8}$alkyl, $C_3$-$C_8$cycloalkyl, 3- to 12-membered heterocyclyl, $C_6$-$C_{12}$aryl or 5- to 12-membered heteroaryl is optionally substituted with at least one substituent $R_{5c}$;

$R_{5a}$ and $R_{5b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl, 5- to 12-membered heteroaryl or oxo, wherein each of said —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl, 5- to 12-membered heteroaryl is optionally substituted with at least one substituent $R_{5d}$; or $R_{5a}$ and $R_{5b}$ together with the carbon atoms to which they are attached, form a 3- to 8-membered unsaturated or saturated ring, said ring comprising 0-3 heteroatoms independently selected from nitrogen, oxygen or sulfur; said ring is optionally substituted with at least one substituent $R_{5e}$;

$R_{5c}$, at each occurrence, is independently halogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, oxo, —CN, —$OR_{5e}$, —$COR_{5e}$, —$CO_2R_{5e}$, —$CONR_{5e}R_{5f}$, —$NR_{5e}R_{5f}$, —$NR_{5e}COR_{5f}$ or —$NR_{5e}CO_2R_{5f}$, wherein each of said —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl is optionally substituted with at least one substituent $R_{5d}$; or two $R_{5e}$ together with the carbon atoms to which they are attached, form a 3- to 8-membered unsaturated or saturated ring, said ring comprising 0-3 heteroatoms independently selected from nitrogen, oxygen or sulfur; said ring is optionally substituted with at least one substituent $R_{5d}$; $R_{5d}$ is hydrogen, halogen, —$C_{1-8}$alkyl, $C_3$-$C_8$cycloalkyl, 3- to 8-membered heterocyclyl, $C_6$-$C_{12}$aryl, 5- to 12-membered heteroaryl, oxo, —CN, —$OR_{5g}$, —$COR_{5g}$, —$CO_2R_{5g}$, —$CONR_{5g}R_{5h}$, —$NR_{5g}R_{5h}$, —$NR_{5g}COR_{5h}$ or —$NR_{5g}CO_2R_{5h}$; wherein each of —$C_{1-8}$alkyl, $C_3$-$C_8$cycloalkyl, 3- to 8-membered heterocyclyl, $C_6$-$C_{12}$aryl or 5- to 12-membered heteroaryl is optionally substituted with at least one substituent $R_{5i}$; $R_{5e}$, $R_{5f}$, $R_{5g}$, $R_{5h}$ and $R_{5i}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl.

In some embodiments, the KRAS G12D binding moiety is:

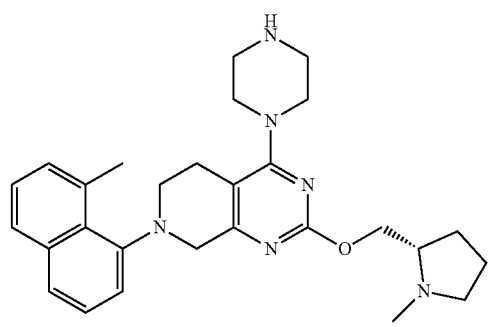

E1

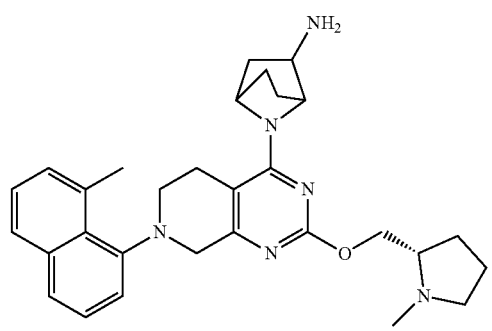

E2

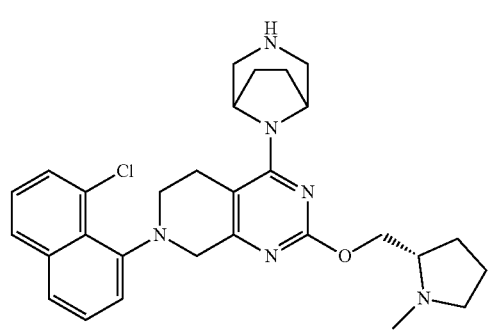

E3

E4
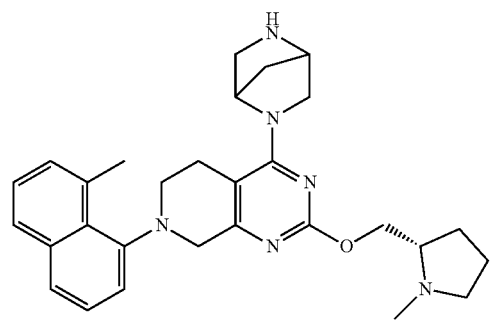
E5
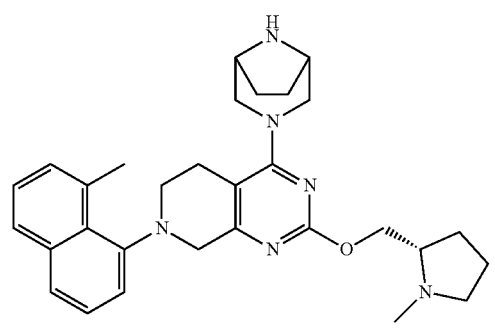
E6
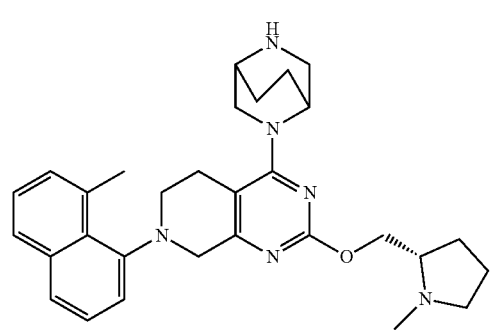
E7
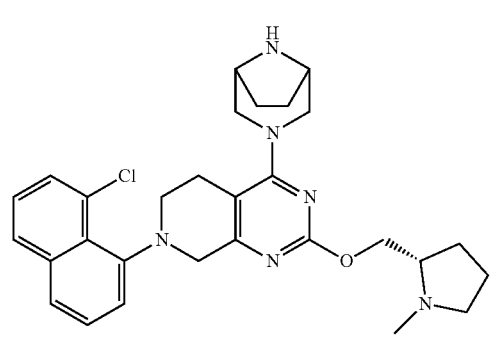
E8
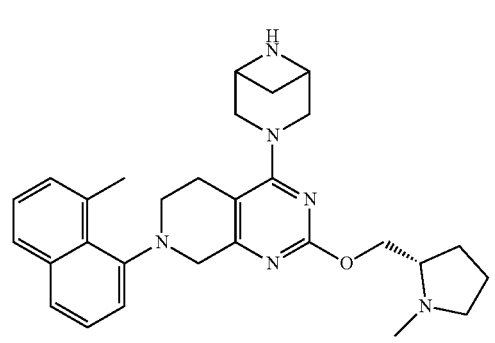
E9
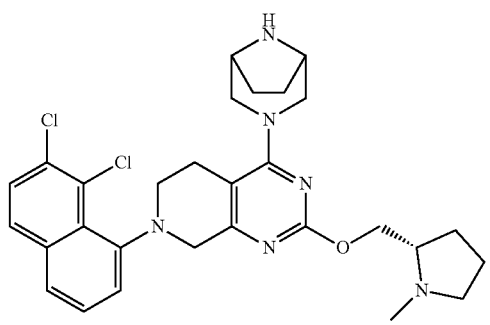
E10
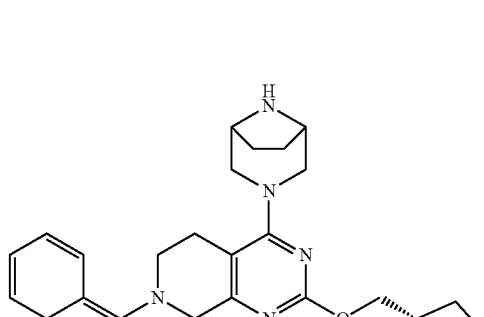
E11
E12
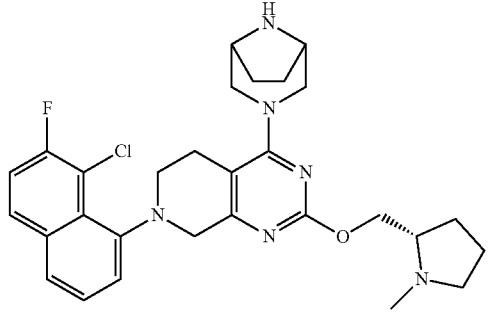

527 -continued
E13
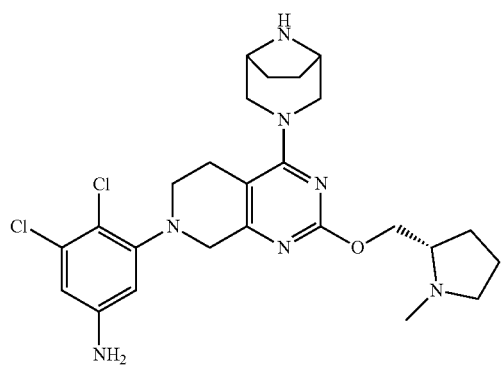
E14
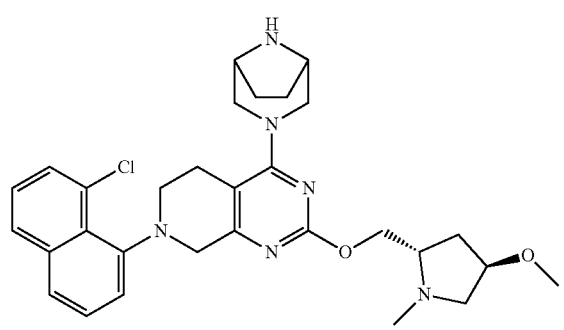
E15
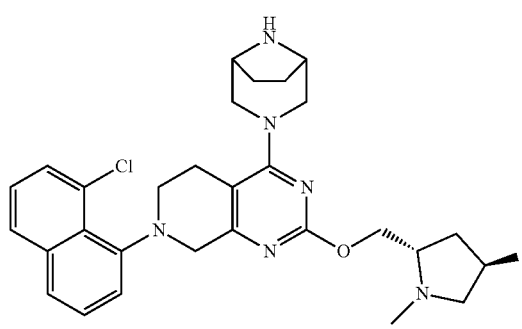
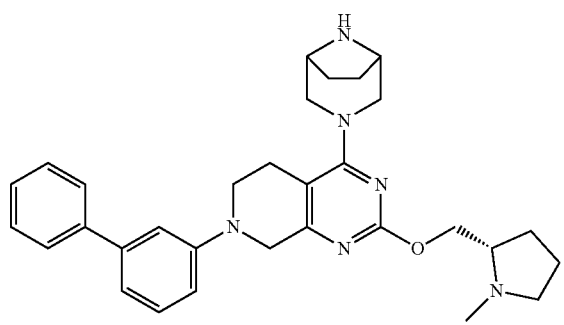
528 -continued
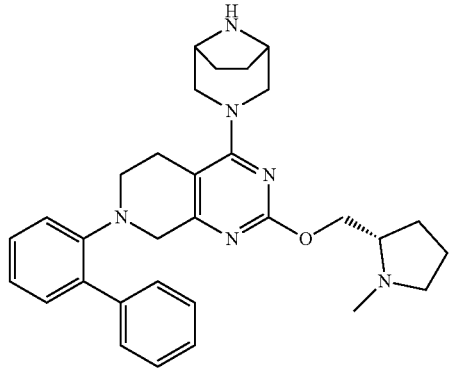
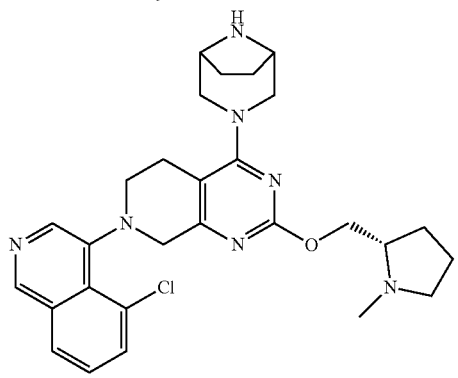
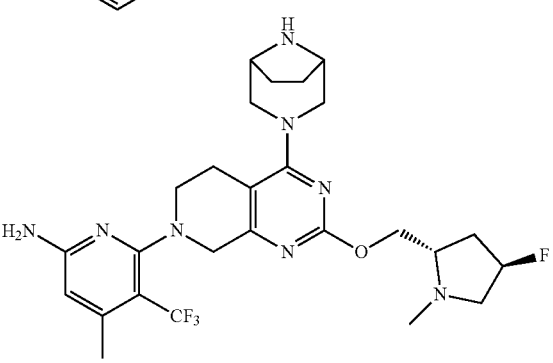
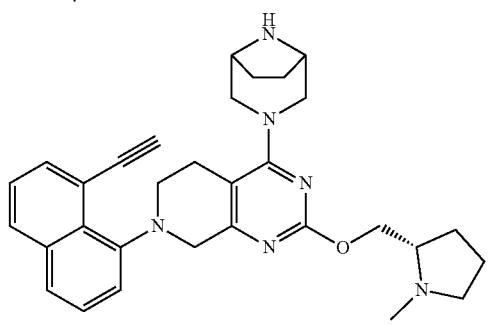
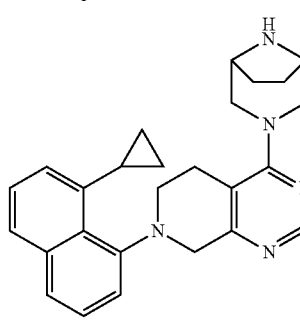

529
-continued
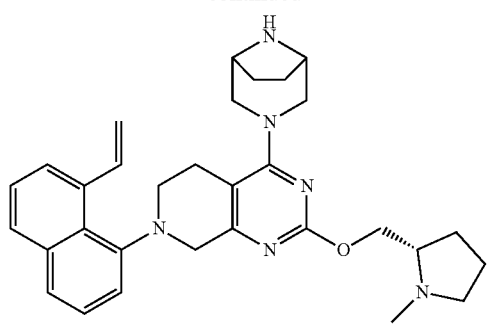
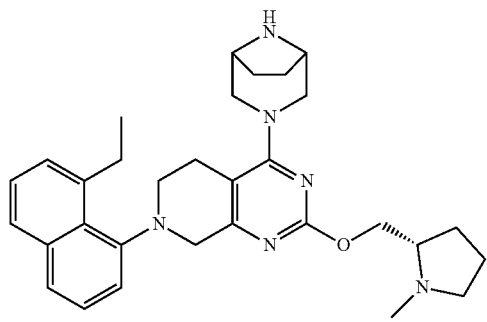
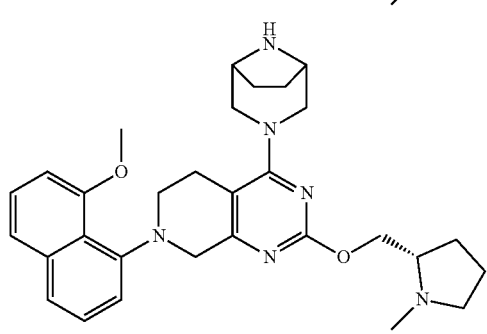
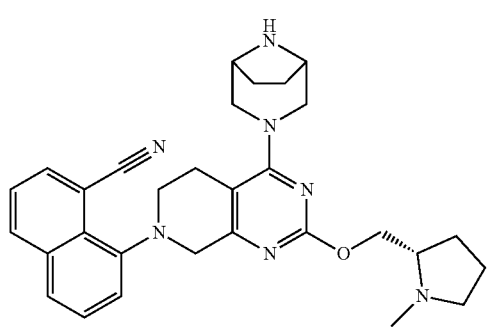
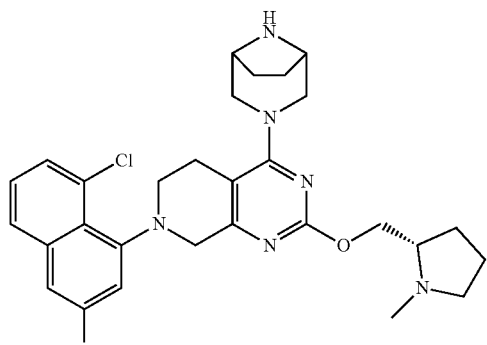
530
-continued
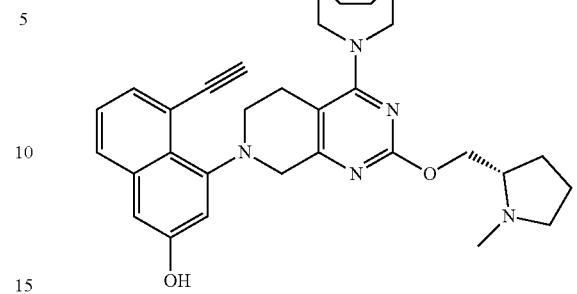
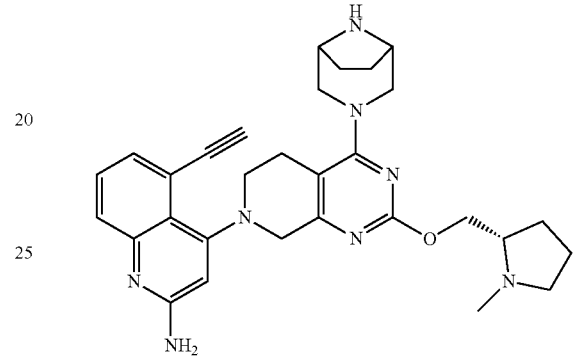
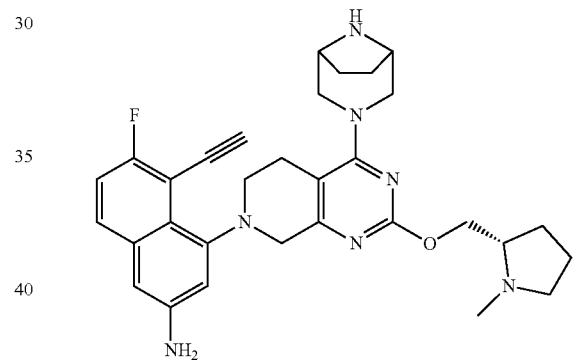
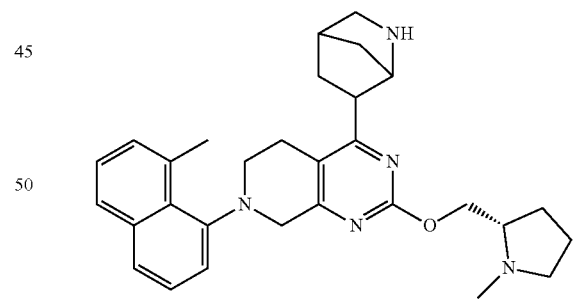
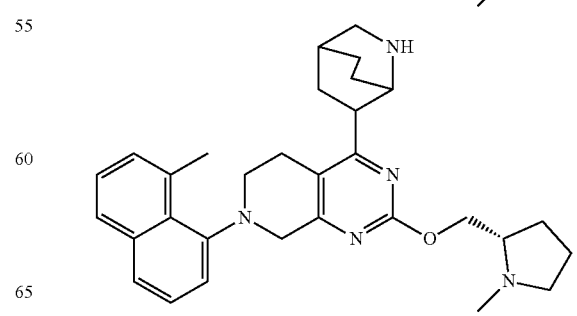

531
-continued
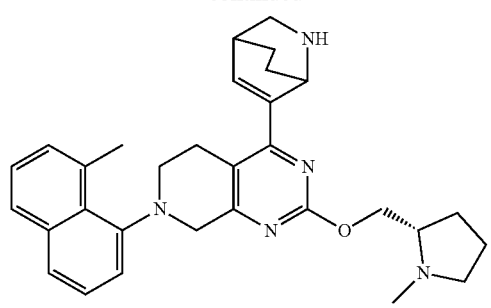
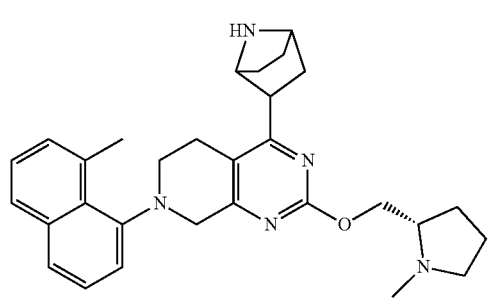
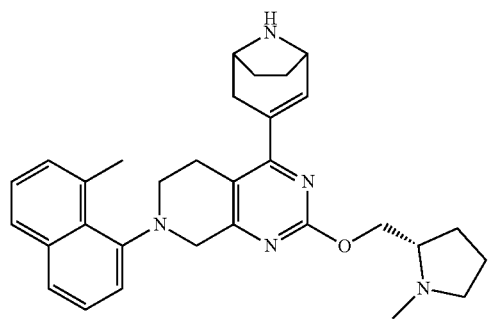
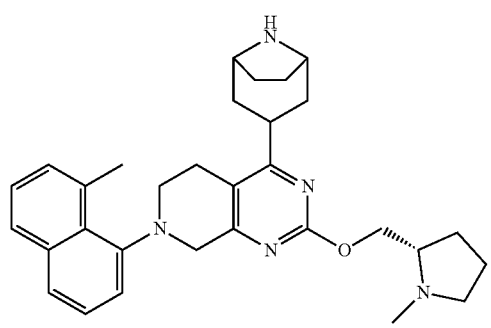
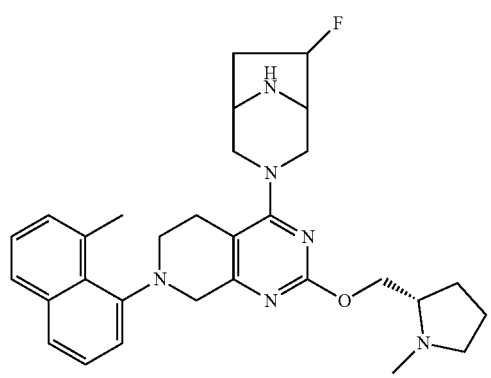
532
-continued
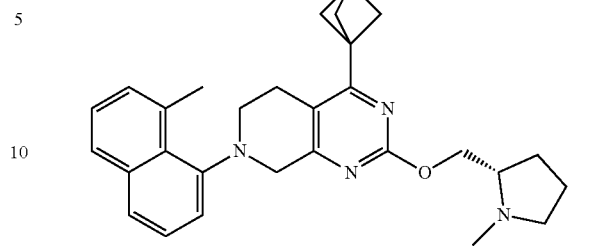
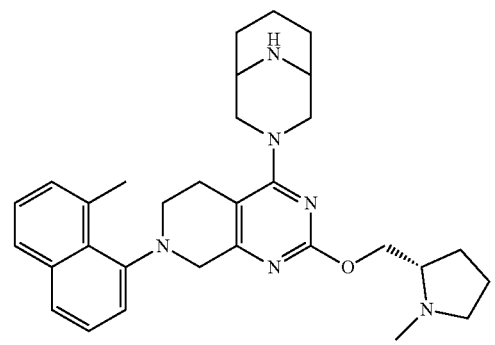
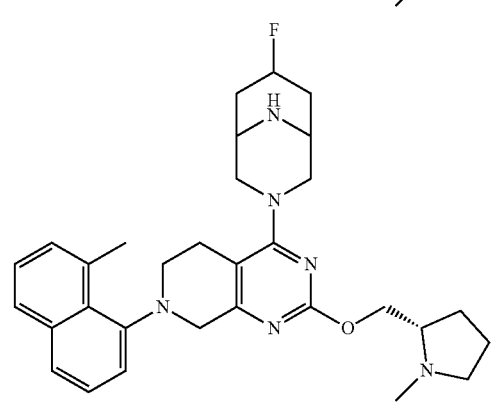
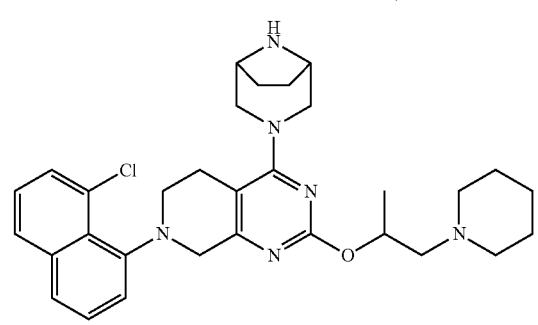
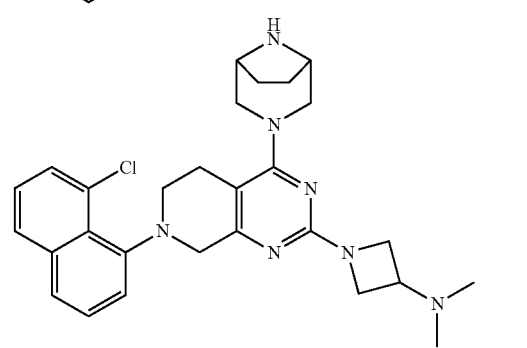

533
-continued

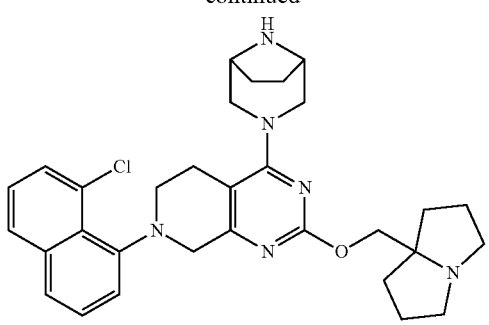

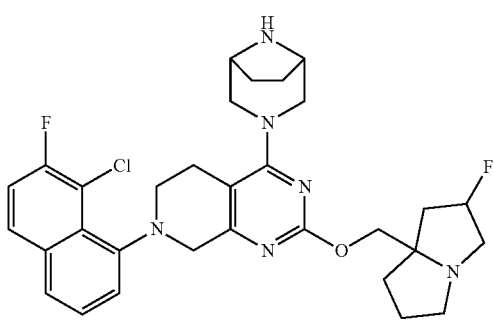

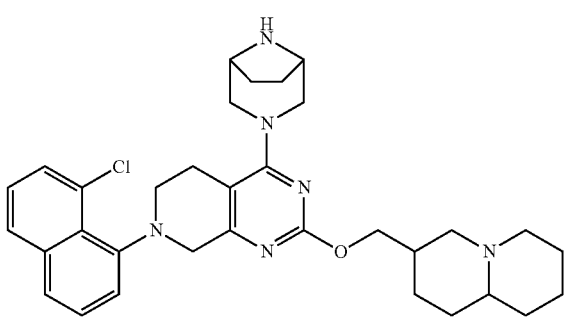

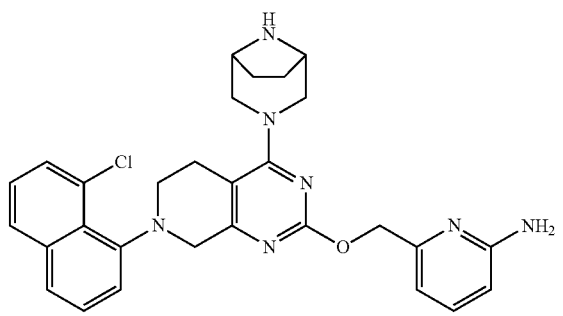

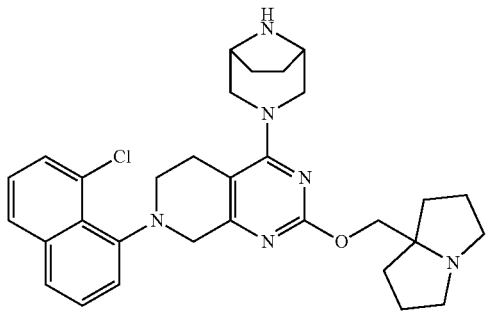

534
-continued

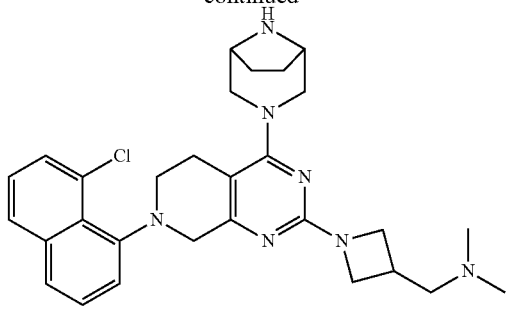

Other specific examples of KRAS G12D binding moieties are disclosed in International Publication No. WO 2023/284537, the entire content of which is incorporated herein by reference. In some embodiments, a KRAS G12D binding moiety is a KRAS G12D binding moiety (e.g., inhibitor) disclosed in WO 2023/284537. For example, in some embodiments a KRAS G12D binding moiety has one of the following structural formulas:

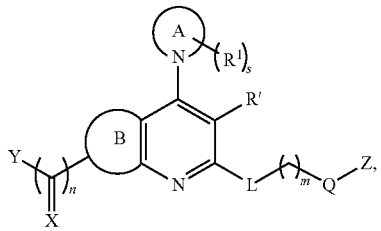

(I)

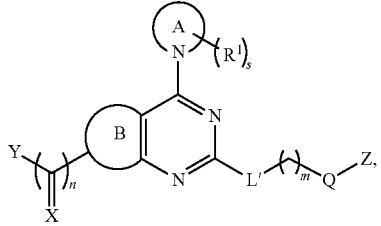

(II)

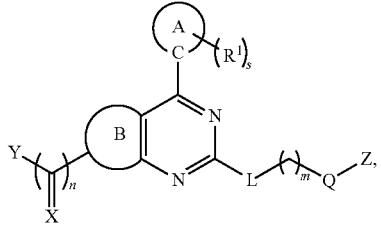

(III)

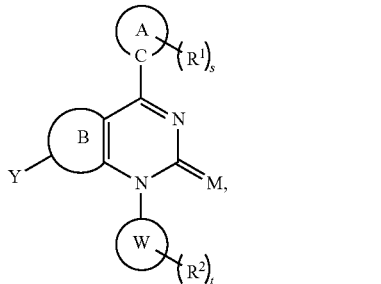

(IV)

wherein:
Ring A is heterocyclyl or heteroaryl, wherein

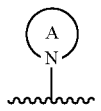

represents N-linked Ring A, and

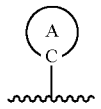

represents C-linked Ring A;
- each $R^1$ is independently selected from oxo, hydroxyl, halogen, cyano, alkyl, alkenyl, alkynyl, heteroalkyl, —C(O)OR$^a$, —C(O)N(R$^a$)$_2$, —N(R$^a$)$_2$ or heteroaryl, wherein the alkyl, alkenyl, alkynyl and heteroaryl are optionally substituted with one or more groups independently selected from cyano, hydroxyl, halogen, —OR$^b$, or —N(R$^b$)$_2$;
- each $R^a$ and $R^b$ is independently hydrogen, alkyl, alkenyl or alkynyl;
- Ring B is cycloalkyl, heterocyclyl, aryl, or heteroaryl optionally substituted with one or more R$^c$;
- each $R^c$ is independently selected from the group consisting of oxo, hydroxyl, halogen, cyano, amino, alkyl, alkenyl, alkynyl, heteroalkyl, heteroalkenyl, heteroalkynyl, heteroaryl, wherein alkyl, alkenyl, alkynyl, heteroalkyl, heteroalkenyl, heteroalkynyl and heteroaryl are optionally substituted with one or more group independently consisting of hydroxyl, halogen, cyano, —OR$^a$, —N(R$^a$)$_2$, and heteroaryl;
- Ring W is cycloalkyl, heterocyclyl, aryl or heteroaryl;
- R' is selected from hydrogen, hydroxyl, halogen, cyano, alkyl, alkenyl, alkynyl, heteroalkyl, —C(O)OR$^a$, —C(O)N(R$^a$)$_2$, —N(R$^a$)$_2$ or heteroaryl, wherein the alkyl, alkenyl, alkynyl and heteroaryl are optionally substituted with one or more groups independently selected from cyano, hydroxyl, halogen, —OR$^b$, or —N(R$^b$)$_2$;
- each $R^2$ is independently selected from the group consisting of hydrogen, oxo, hydroxyl, halogen, cyano, amino, nitro, alkyl, alkenyl, alkynyl, alkoxy, heteroalkyl, heteroalkenyl, heteroalkynyl, cycloalkyl, heterocyclyl, aryl, and heteroaryl, wherein alkyl, alkenyl, alkynyl, alkoxy, heteroalkyl, heteroalkenyl, heteroalkynyl, cycloalkyl, heterocyclyl, aryl, and heteroaryl are optionally substituted with one or more group independently consisting of hydroxyl, halogen, cyano, amino, nitro, alkyl, alkoxy, haloalkyl, hydroxyalkyl, cycloalkyl, heterocyclyl, aryl and heteroaryl;
- X is O or S;
- M is O or S;
- Y is aryl or heteroaryl, wherein aryl or heteroaryl is optionally substituted with one or more R$^c$;
- L is a bond, —O—, —S—, —N(R$^a$)—, alkenyl, cycloalkyl or alkynyl;
- L' is a bond, —S—, —N(R$^a$)—, alkenyl, cycloalkyl or alkynyl, provided that when ring B is

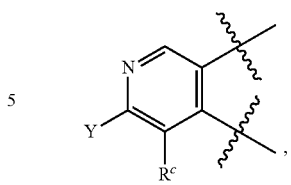

L' is alkenyl, cycloalkyl or alkynyl; and when B is not

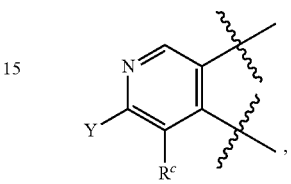

L' is a bond, —S—, —N(R$^a$)—, alkenyl or cycloalkyl;

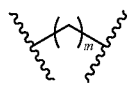

is optionally substituted with hydroxyl, halogen, cyano or amino;
- Q is a bond, alkyl, cycloalkyl, heterocyclyl, aryl or heteroaryl, wherein the cycloalkyl, heterocyclyl, aryl and heteroaryl are optionally substituted with one or more groups independently selected from hydroxyl, halogen, cyano, amino, alkyl, hydroxyalkyl or heteroaryl;
- Z is selected from the group consisting of hydrogen, —N(R$^a$)$_2$, alkyl, haloalkyl, cycloalkyl, heterocyclyl, aryl, heteroaryl, —COOH, —NHC(=NH)NH$_2$, —C(O)N(R$^a$)$_2$, —OR$^a$, —(CH$_2$OR$^a$)(CH$_2$)$_p$OR$^a$, —N(R$^a$)C(O)-aryl and —(CH$_2$)$_p$-heterocyclyl, wherein the cycloalkyl, heterocyclyl, aryl, and heteroaryl are optionally substituted with one or more R$^d$, and the aryl portion in —N(R$^a$)C(O)-aryl and the heterocyclyl portion in —(CH$_2$)$_p$-heterocyclyl are optionally substituted with one or more R$^e$;
- each $R^d$ is independently selected from hydroxyl, halogen, —C(O)H, alkyl, alkoxy, haloalkyl, hydroxyalkyl, or —N(R$^a$)$_2$;
- each $R^e$ is independently selected from oxo, hydroxyl, halogen, alkyl, heteroalkyl, hydroxyalkyl, haloalkyl, alkoxy, -T-phenyl, -T-phenylSO$_2$F, —N(R$^a$)$_2$, —SO$_2$F, —C(O)(alkyl), or —C(O)(haloalkyl), wherein the alkyl, heteroalkyl, hydroxyalkyl, haloalkyl, and alkoxy are optionally substituted with one or more groups independently selected from aryl, heteroaryl, or tert-butyldimethylsilyloxy;
- T is a bond, —O—, or —N—C(O)—;
- m is 0 or 1;
- n is 0 or 1;
- s is an integer from 0 to 5;
- t is an integer from 0 to 4; and
- p is an integer from 0 to 4.

In some embodiments, the KRAS G12D binding moiety is:

537
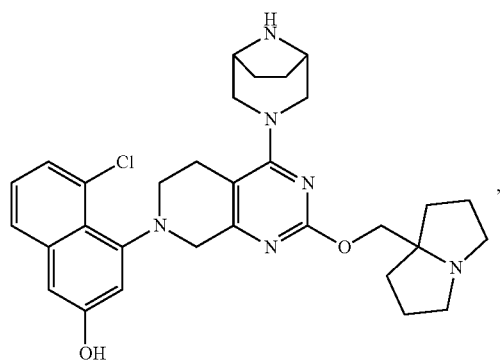
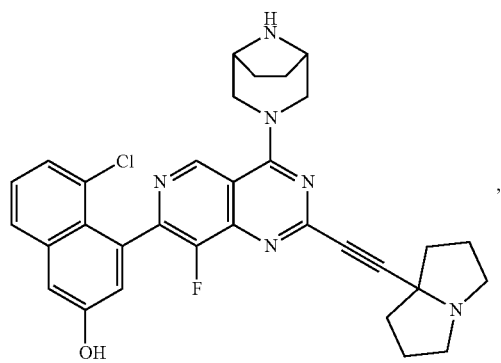
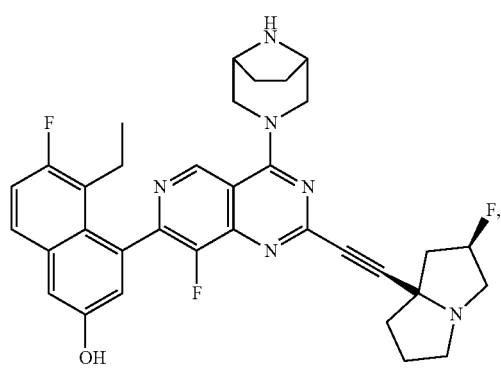
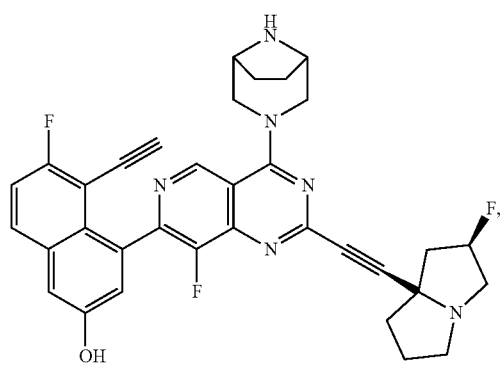
538
-continued
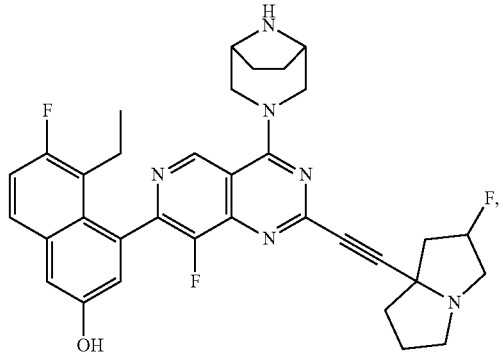
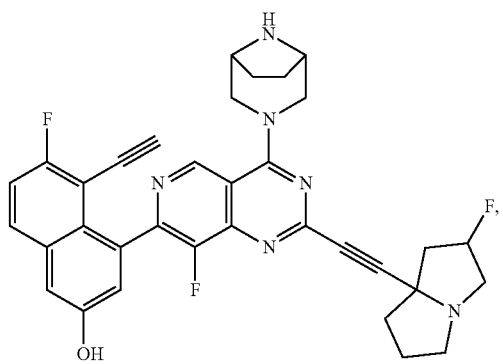
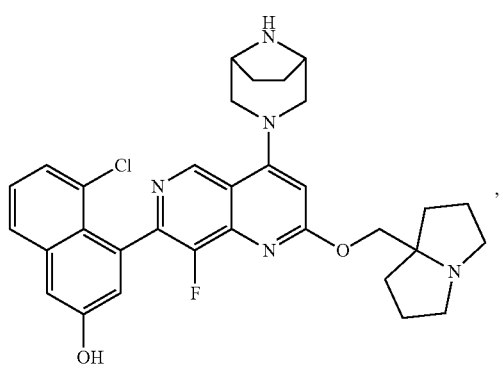

-continued
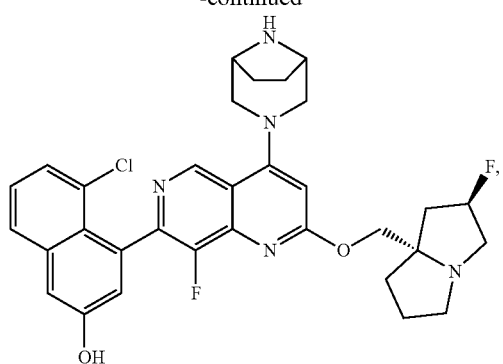
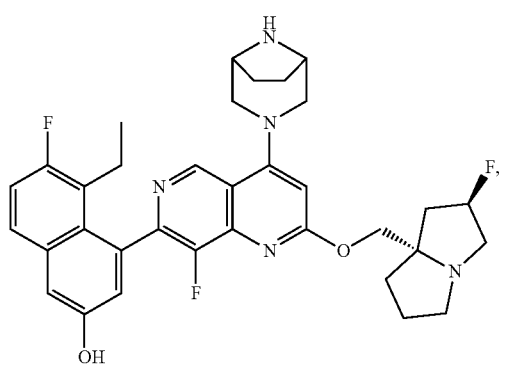
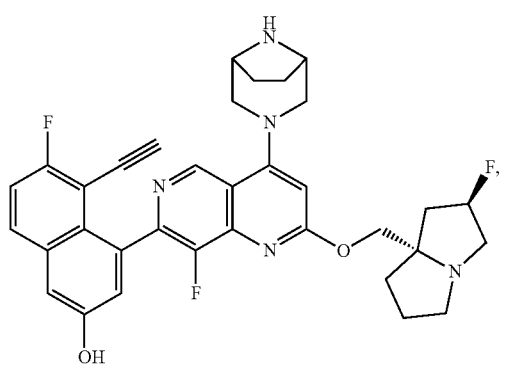
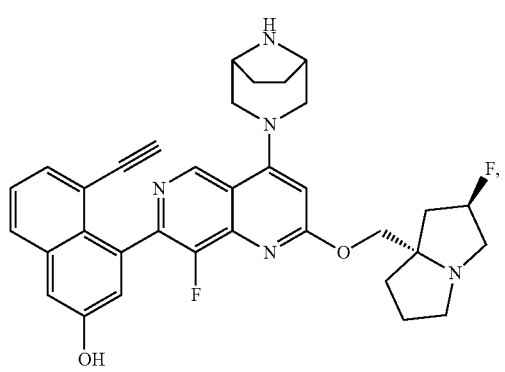
-continued
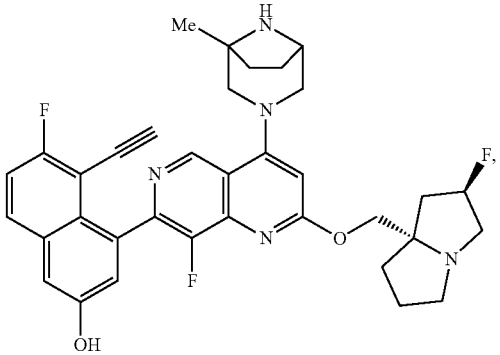
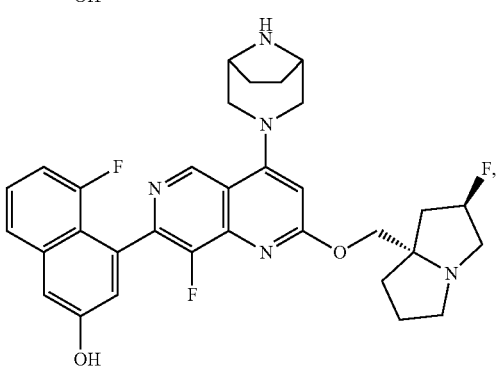
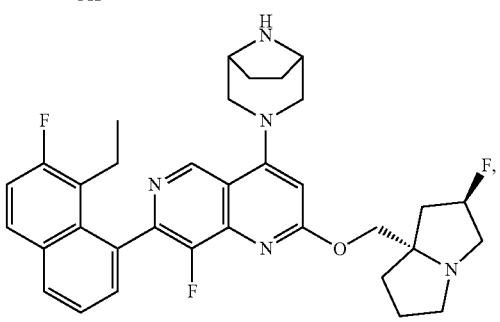
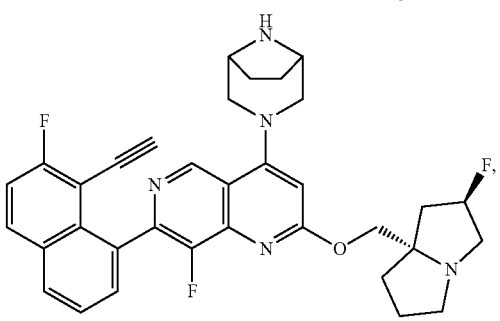
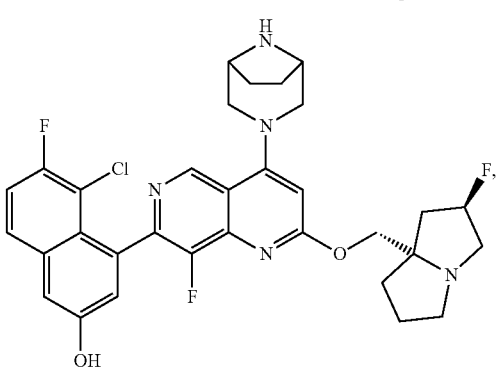

541
-continued
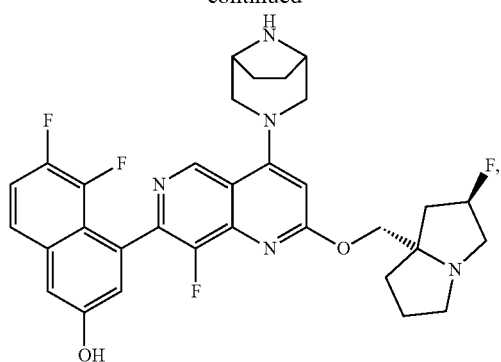
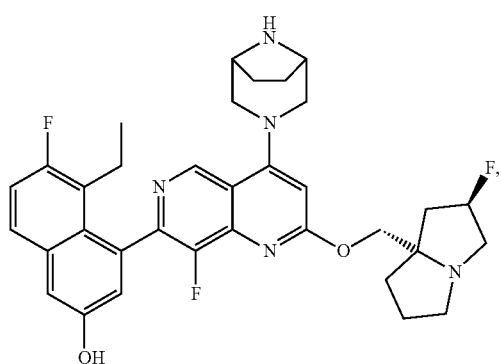
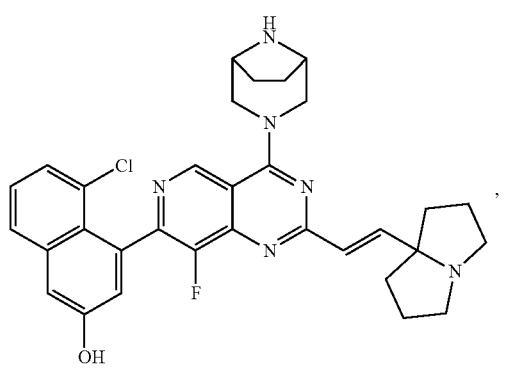
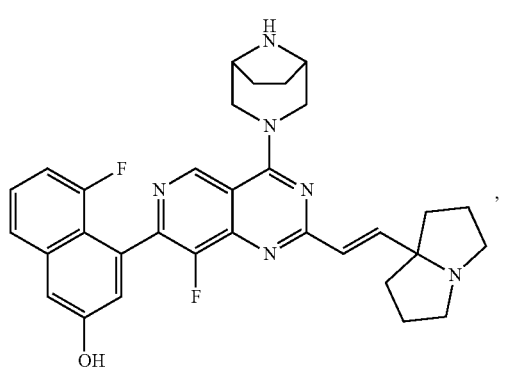
542
-continued
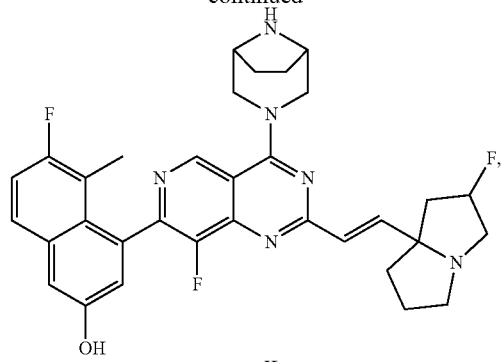
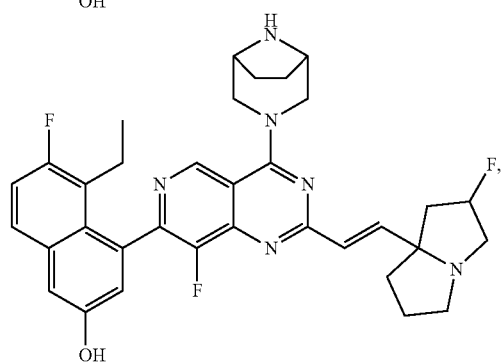
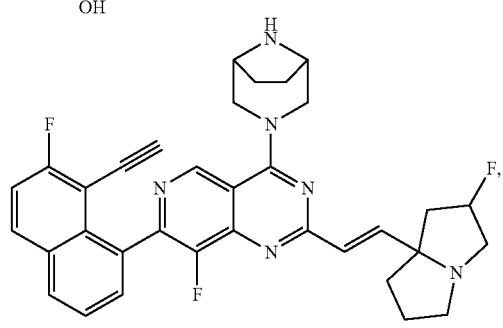
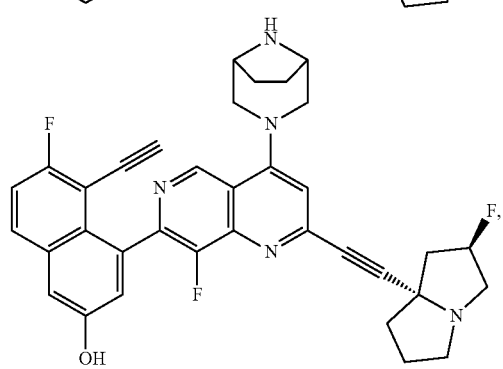
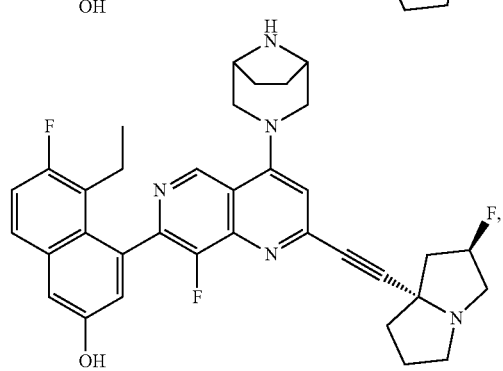

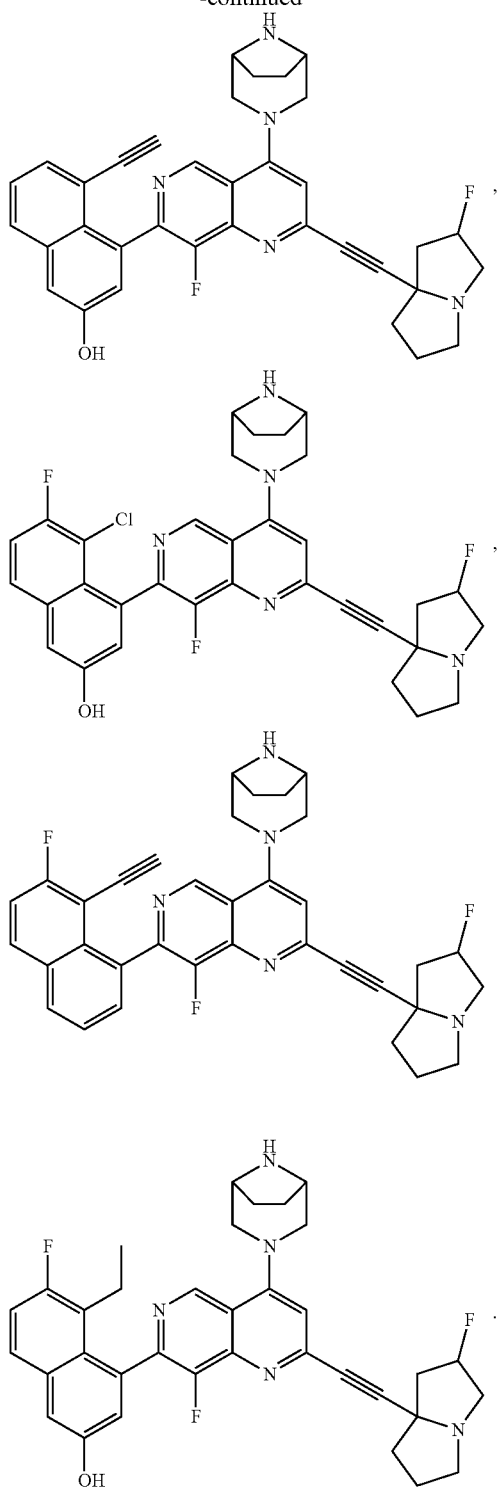

Other specific examples of KRAS G12D binding moieties are disclosed in International Publication No. WO 2023/001141, the entire content of which is incorporated herein by reference. In some embodiments, a KRAS G12D binding moiety is a KRAS G12D binding moiety (e.g., inhibitor) disclosed in WO 2023/001141. For example, in some embodiments a KRAS G12D binding moiety has one of the following structural formulas:

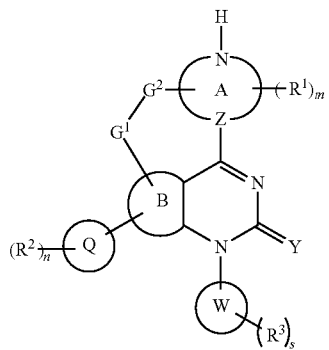
(I)

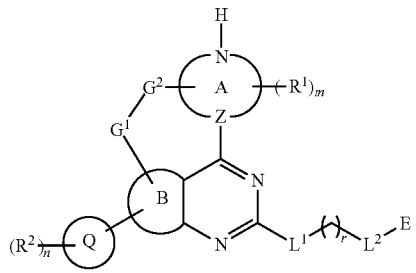
(II)

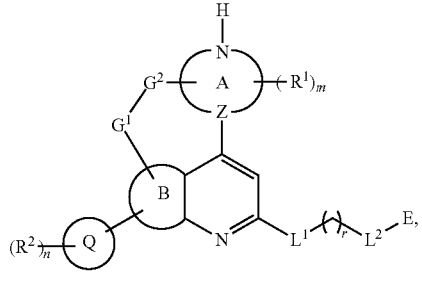
(II')

wherein:
Y is O or S;
Ring A is heterocyclyl or heteroaryl,
each $R^1$ is independently selected from the group consisting of oxo, hydroxyl, halogen, cyano, alkyl, alkenyl, alkynyl, heteroalkyl, heteroaryl, —C(O)R*, —C(O)OR*, —C(O)N($R^a$)$_2$, —N($R^a$)$_2$, —P(O)OR*OR**, and —C(O)OC($R^a$)$_2$—$Z^1$—$Z^2$, wherein the alkyl, alkenyl, alkynyl and heteroaryl are optionally substituted with one or more groups independently selected from cyano, hydroxyl, halogen, —$OR^b$, or —N($R^b$)$_2$;
each $R^a$ and $R^b$ is independently hydrogen, alkyl, alkenyl or alkynyl;
R* is selected from hydrogen, alkyl, alkylaryl or aryl;
R** is selected from hydrogen, alkyl, alkenyl or alkynyl; or
R* and R** together with the oxygen atoms to which they are attached form a heterocyclyl optionally substituted with aryl or haloaryl;
$Z^1$ is —OC(O)— #, —OP(=O)(OR***)O— #, or —OP(=O(OR*))N($R^a$)— #, wherein #end is connected to $Z^2$;
$Z^2$ is hydrogen or alkyl optionally substituted with aryl or —C(O)$OR^a$;
R*** is independently selected from hydrogen, alkyl, alkenyl or alkynyl; or
R*** and $Z^2$ together with the oxygen atoms to which they are attached form a heterocyclyl optionally substituted with aryl or haloaryl;

Ring B is selected from cycloalkyl, heterocyclyl, aryl, or heteroaryl, each of which is optionally substituted with one or more R';

each R' is independently selected from the group consisting of oxo, hydroxyl, halogen, cyano, amino, alkyl, alkenyl, alkynyl, heteroalkyl, heteroalkenyl, heteroalkynyl, heteroaryl, wherein alkyl, alkenyl, alkynyl, heteroalkyl, heteroalkenyl, heteroalkynyl and heteroaryl are optionally substituted with one or more group independently consisting of hydroxyl, halogen, cyano, —OR$^a$, —N(R$^a$)$_2$, and heteroaryl;

Ring Q is selected from cycloalkyl, heterocyclyl, aryl or heteroaryl;

each R$^2$ is independently selected from the group consisting of hydrogen, oxo, hydroxyl, halogen, cyano, amino, nitro, alkyl, alkenyl, alkynyl, alkoxy, heteroalkyl, heteroalkenyl, heteroalkynyl, cycloalkyl, heterocyclyl, aryl, heteroaryl and —C(O)R*, wherein alkyl, alkenyl, alkynyl, alkoxy, heteroalkyl, heteroalkenyl, heteroalkynyl, cycloalkyl, heterocyclyl, aryl, and heteroaryl are optionally substituted with one or more group independently consisting of hydroxyl, halogen, cyano, amino, nitro, alkyl, alkoxy, haloalkyl, hydroxyalkyl, cycloalkyl, heterocyclyl, aryl and heteroaryl;

Ring W is selected from cycloalkyl, heterocyclyl, aryl and heteroaryl;

each R$^3$ is independently selected from the group consisting of hydrogen, oxo, hydroxyl, halogen, cyano, amino, nitro, alkyl, alkenyl, alkynyl, alkoxy, heteroalkyl, heteroalkenyl, heteroalkynyl, cycloalkyl, heterocyclyl, aryl, and heteroaryl, wherein alkyl, alkenyl, alkynyl, alkoxy, heteroalkyl, heteroalkenyl, heteroalkynyl, cycloalkyl, heterocyclyl, aryl, and heteroaryl are optionally substituted with one or more group independently consisting of hydroxyl, halogen, cyano, amino, nitro, alkyl, alkoxy, haloalkyl, hydroxyalkyl, cycloalkyl, heterocyclyl, aryl and heteroaryl;

G$^1$ is a bond, —O—, —S(O)$_p$—, —S—S—, —N(R$^c$), or —C(R$^d$)═C(R$^d$)—;

G$^2$ is a bond, —[C(R$^d$)$_2$]$_u$—, —C(O)— or —C(O)C(R$^d$)$_2$—;

R$^c$ is selected from the group consisting of hydrogen, alkyl, haloalkyl, hydroxyalkyl, heteroalkyl, cycloalkyl and heterocyclyl;

each R$^d$ is independently selected from the group consisting of hydrogen, hydroxyl, halogen, cyano, amino, nitro, alkyl, alkenyl, alkynyl, alkoxy, heteroalkyl, heteroalkenyl, heteroalkynyl, cycloalkyl, and heterocyclyl, wherein alkyl, alkenyl, alkynyl, alkoxy, heteroalkyl, heteroalkenyl, heteroalkynyl, cycloalkyl, and heterocyclyl are optionally substituted with one or more group independently consisting of hydroxyl, halogen, cyano, amino, nitro, alkyl, alkoxy, haloalkyl, and hydroxyalkyl; or two R$^d$ together with the carbon atom to which they are both attached form cycloalkyl or heterocyclyl, wherein cycloalkyl and heterocyclyl are optionally substituted with cyano, halogen, hydroxyl, amino, nitro, alkoxy, haloalkyl, hydroxyalkyl and alkyl;

Z is C(R$^e$) or N;

R$^e$ is absent or hydrogen;

L$^1$ is selected from a bond, —O—, —S—, —N(R$^a$)—, —C(O)N(R$^a$)—, alkenyl, alkynyl or cycloalkyl is optionally substituted with hydroxyl, halogen, cyano or amino;

L$^2$ is a bond, alkyl, cycloalkyl, heterocyclyl, aryl or heteroaryl, wherein the cycloalkyl, heterocyclyl, aryl and heteroaryl are optionally substituted with one or more groups independently selected from hydroxyl, halogen, cyano, amino, alkyl, hydroxyalkyl or heteroaryl;

E is selected from the group consisting of hydrogen, hydroxyl, halogen, —N(R$^a$)$_2$, alkyl, haloalkyl, heteroalkyl, cycloalkyl, heterocyclyl, aryl, heteroaryl, —COOH, —CH$_2$OC(O)-heterocyclyl, —CH$_2$OC(O)N(R$^a$)$_2$, —NHC(═NH)NH$_2$, —C(O)N(R$^a$)$_2$, —OR$^a$, —(CH$_2$OR$^a$)(CH$_2$)$_p$OR$^a$, —N(R$^a$)C(O)-aryl and —(CH$_2$)$_u$-heterocyclyl, wherein the cycloalkyl, heterocyclyl, aryl, and heteroaryl are optionally substituted with one or more R", and the aryl portion in —N(R$^a$)C(O)-aryl and the heterocyclyl portion in —(CH$_2$)$_u$-heterocyclyl and —CH$_2$OC(O)-heterocyclyl is optionally substituted with one or more R'";

each R'" is independently selected from hydroxyl, halogen, —C(O)H, alkyl, alkoxy, haloalkyl, hydroxyalkyl, or —N(R$^a$)$_2$;

each R'" is independently selected from oxo, hydroxyl, halogen, alkyl, heteroalkyl, hydroxyalkyl, haloalkyl, alkoxy, -T-phenyl, -T-phenylSO$_2$F, —N(R$^a$)$_2$, —SO$_2$F, —C(O)(alkyl), or —C(O)(haloalkyl), wherein the alkyl, heteroalkyl, hydroxyalkyl, haloalkyl, and alkoxy are optionally substituted with one or more groups independently selected from aryl, heteroaryl, or tert-butyldimethylsilyloxy;

T is a bond, —O—, or —NHC(═O)—;

m is an integer from 0 to 6;

n is an integer from 0 to 5;

r is an integer from 0 to 4;

s is an integer from 0 to 5;

p is an integer from 0 to 2; and u is an integer from 0 to 4.

In some embodiments, the KRAS G12D binding moiety is:

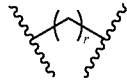

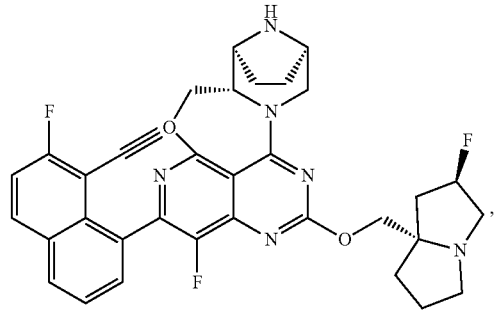

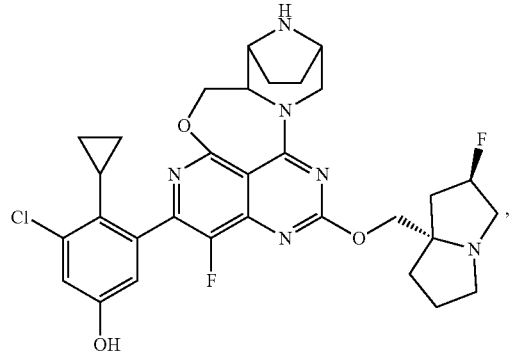

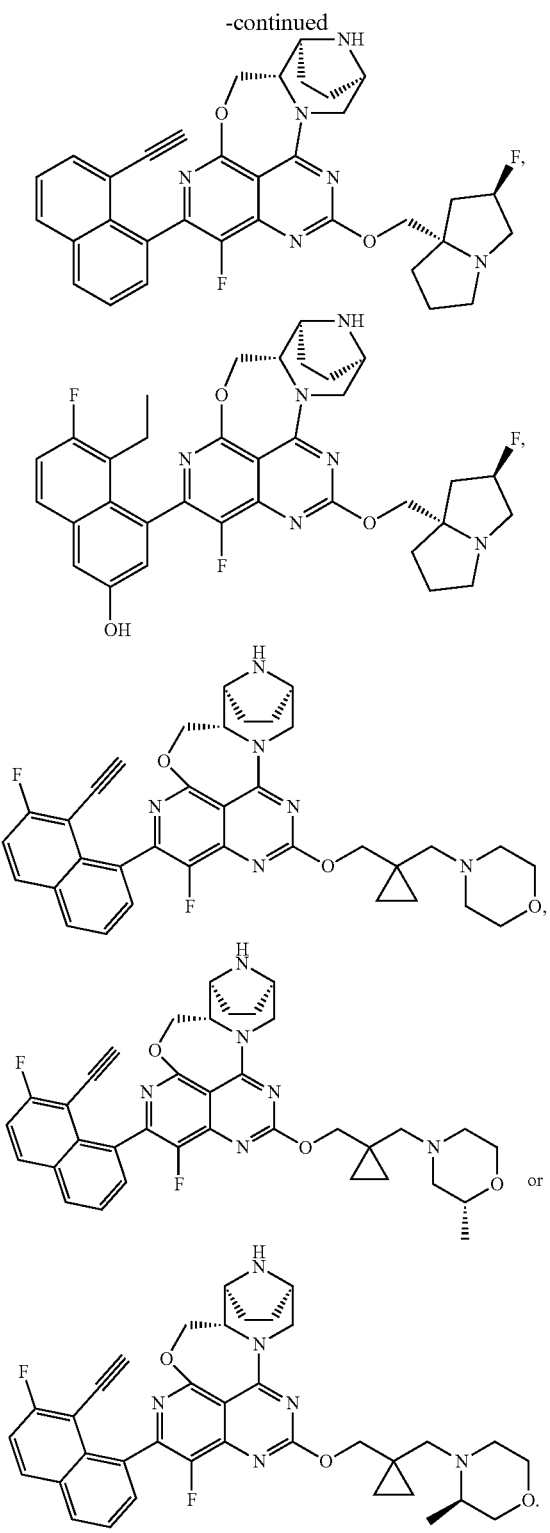

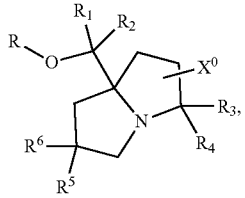
(I)

$X^0$ is H, deuterium, halo, OH, $NH_2$, CN, $C_{1-6}$alkyl, $C_{1-6}$hydroxyalkyl, or $C_{1-6}$alkoxyl, each of which can be independently optionally unsubstituted or substituted by a 3- to 7-membered heterocycle with one or more heteroatoms independently selected from N, O or S, and at least one of the heteroatoms is N which is directly connected to one of the C atoms of the $C_{1-6}$alkyl or $C_{1-6}$hydroxyalkyl; the 3- to 7-membered heterocycle is further optionally substituted by a —$CH_3$ or —$N(CH_3)_2$;

each of $R^1$ and $R^2$ is independently selected from H, deuterium, halogen, —$NH_2$, —CN, —OH, —$C_{1-6}$alkyl, or —$C_{1-6}$alkoxy, each of which is independently optionally unsubstituted or substituted by deuterium, halogen, —$NH_2$, —CN, —OH, —$C_{1-6}$alkyl, or —$C_{1-6}$ alkoxy;

each of $R^3$ and $R^4$ is independently selected from H, deuterium, halogen, —$NH_2$, —CN, —OH, —$C_{1-4}$alkyl, or —$C_{1-4}$alkoxy, and each of which is independently optionally unsubstituted or substituted by deuterium, halogen, —$NH_2$, —CN, —OH, —NHC(=O)NHC$_{1-6}$alkyl, —NHC(=O)N($C_{1-6}$alkyl)$_2$, —OH, —OC(O)NHC$_{1-6}$alkyl, —OC(O)N($C_{1-6}$alkyl)$_2$,

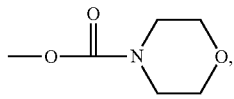

—$C_{1-6}$alkyl, or —$C_{1-6}$alkoxy;

each of $R^5$ and $R^6$ is independently selected from H, deuterium, halogen, —$NH_2$, —CN, —OH, —$C_{1-6}$alkyl, or —$C_{1-6}$alkoxy, each of which is independently optionally unsubstituted or substituted by deuterium, halogen, —$NH_2$, —CN, —OH, —$C_{1-6}$alkyl, or —$C_{1-6}$alkoxy; and at least one of $R^1$, $R^2$, $R^3$, $R^4$, $R^5$ and $R^6$ is deuterium;

R is independently:

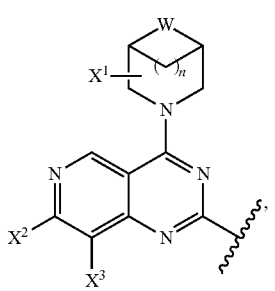

Yet other specific examples of KRAS G12D binding moieties are disclosed in International Publication No. WO 2022/262838, the entire content of which is incorporated herein by reference. In some embodiments, a KRAS G12D binding moiety is a KRAS G12D binding moiety (e.g., inhibitor) disclosed in WO 2022/262838. For example, in some embodiments, a KRAS G12D binding moiety has the following structural formula:

-continued

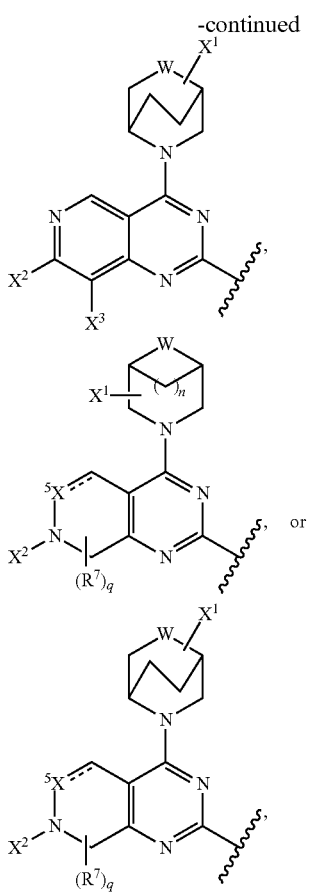

wherein:
n is 0, 1, 2, or 3;
q is 0, 1, 2, or 3;
$X^1$ is H, —CH$_2$CN, C$_{1-6}$alkyl, or C$_{1-6}$alkoxy;
$X^2$ is a 6- to 10-membered aryl, or 5- to 10-membered heteroaryl; and each of the 6- to 10-membered aryl, or the 5- to 10-membered heteroaryl is independently optionally unsubstituted or substituted by one or more $R^{2x}$;
each of $R^{2x}$ is independently selected from halogen, —OH, —NH$_2$, —CN, C$_{1-6}$alkyl, C$_{1-6}$hydroxyalkyl, C$_{1-6}$alkoxy, C$_{1-6}$haloalkyl, C$_{2-6}$alkenyl, C$_{2-6}$alkynyl, C$_{2-6}$deuterated alkynyl, cyano, (C$_{1-6}$alkoxy)C$_{1-6}$alkyl, (C$_{1-6}$alkoxy)C$_{1-6}$alkoxy, (C$_{1-6}$hydroxyalkoxy)C$_{1-6}$alkoxy, 3- to 7-membered cycloalkyl, or 3- to 7-membered heterocycloalkyl, each of which is independently optionally unsubstituted or substituted by one or more —NH$_2$, halogen, deuterium, —CN, —OH, —C$_{1-6}$alkyl, or —C$_{1-6}$alkoxy;
$X^3$ is independently selected from H, halogen, C$_{1-6}$alkyl, or C$_{1-6}$alkoxy;
" " is a single bond or a double bond;
$^5X$ is N or CR$^7$, wherein:
when $^5X$ is N or $^5X$ is CR$^7$, "- - -" is a double bond; and
when $^5X$ is C(R$^7$)$_2$, or $^5X$ is NR$^7$, "- - -" is a single bond;
each of R$^7$ is independently H, halogen, —C$_{1-6}$alkyl, or —C$_{1-6}$alkyl substituted by one or more halogen, deuterium, —OH or NH$_2$; or
two R$^7$ together with the C atom to which the two R$^7$ are both attached form an oxo (=O), and the oxo together with the N atom to which the $X^2$ is attached form a lactam; or R$^7$ and R$^7$ together with the C atom to which they are respectively attached form 3- to 6-membered cycloalkyl or 3- to 6-membered heterocycle; or W is O or NR$^w$, and R$^w$ is H, deuterium, or C$_{1-6}$alkyl.

In some embodiments, the KRAS G12D binding moiety is:

EX. 1

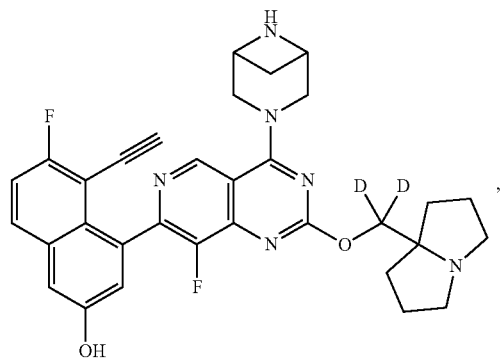

EX. 2

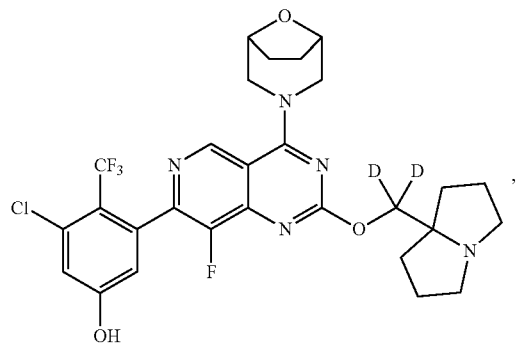

EX. 3

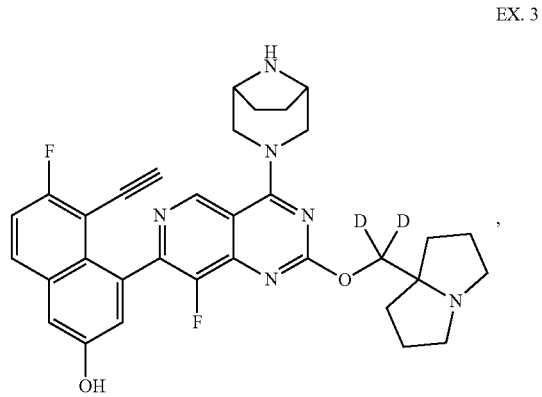

-continued
EX. 4
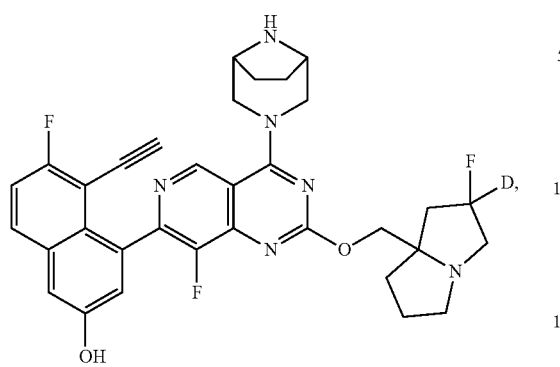
EX. 5
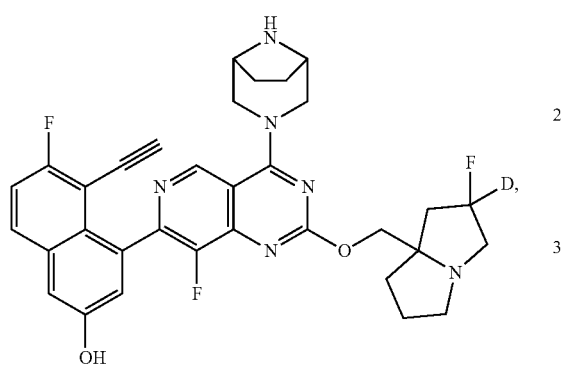
EX. 6
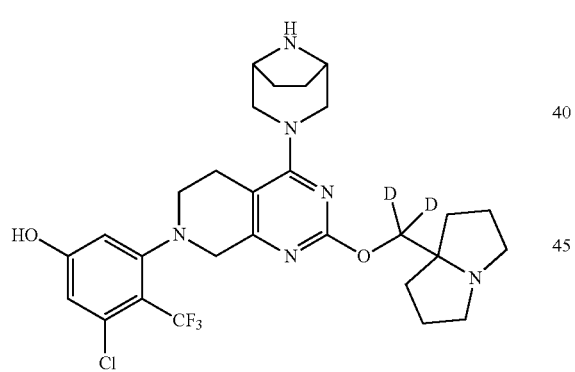
EX. 7
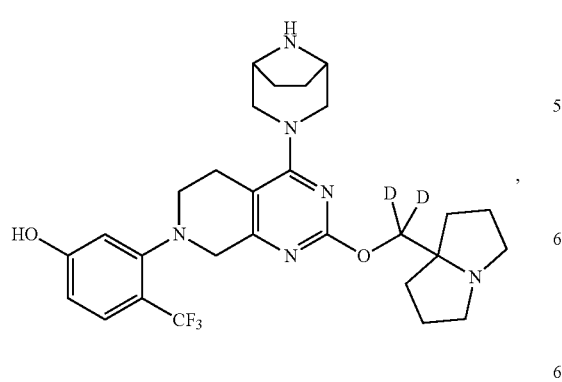
-continued
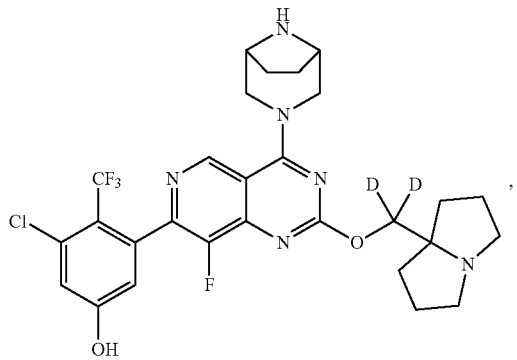
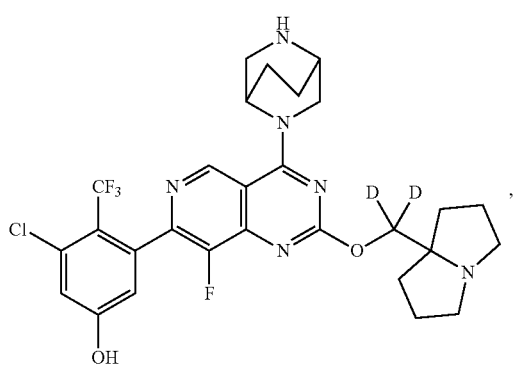
EX. 10
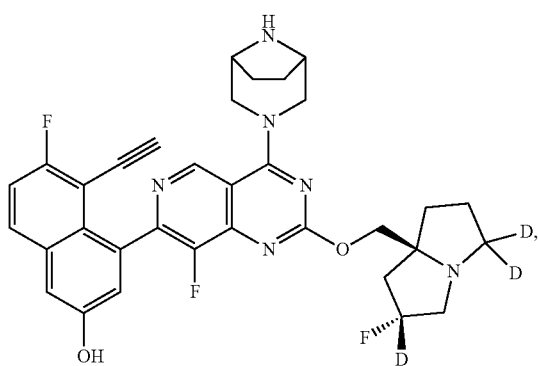
EX. 11
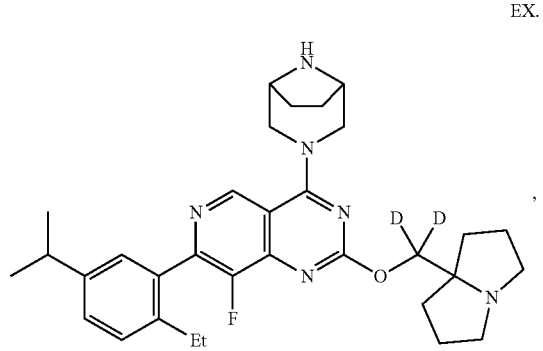

553
-continued
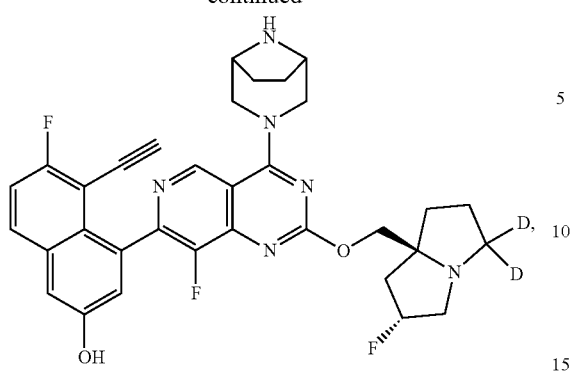
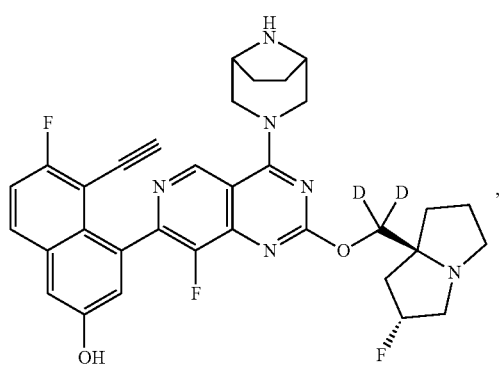
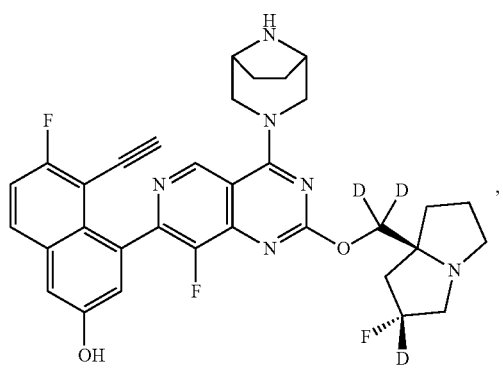
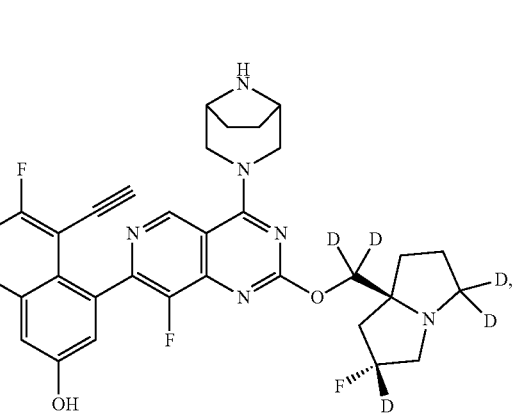
554
-continued
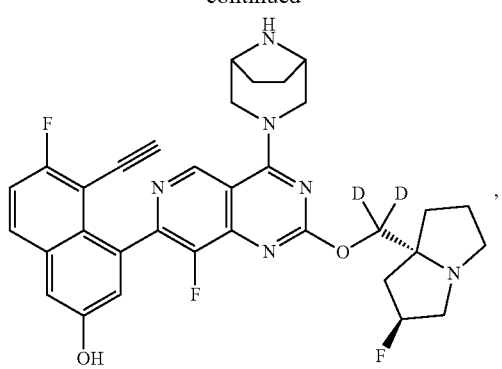
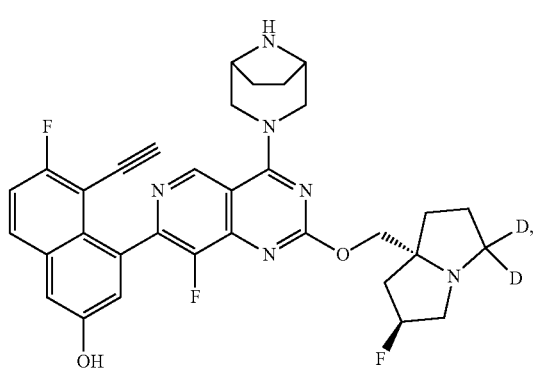
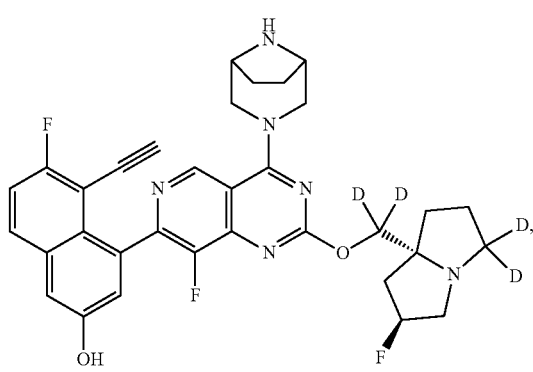
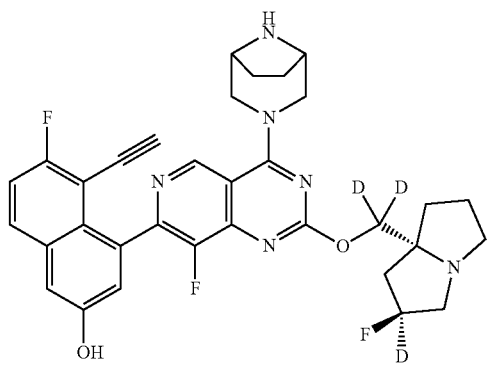

555
-continued
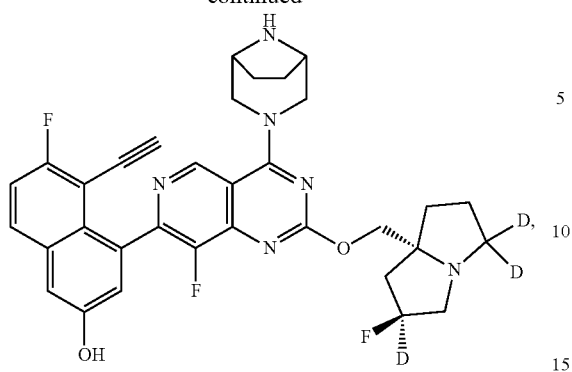
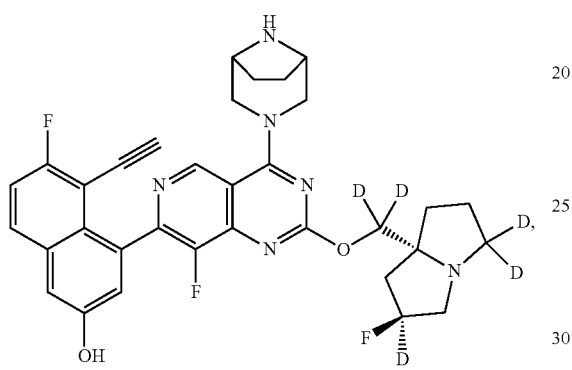
EX. 22
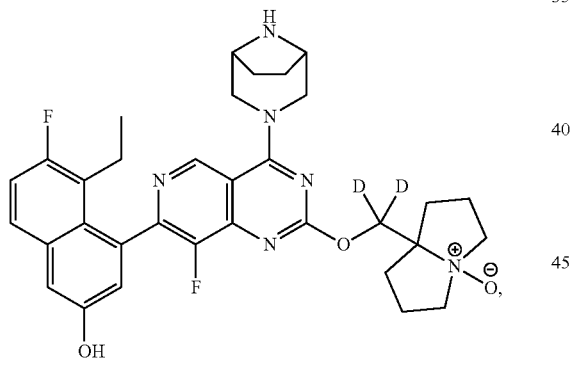
EX. 23
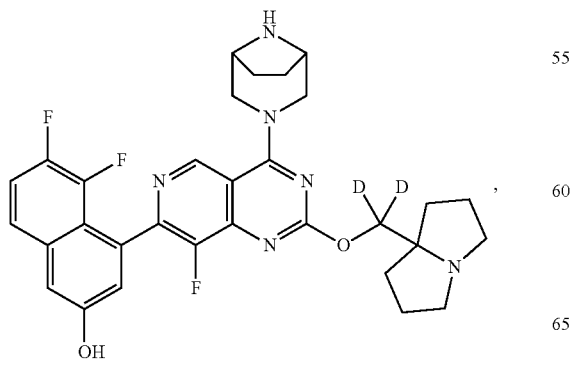
556
-continued
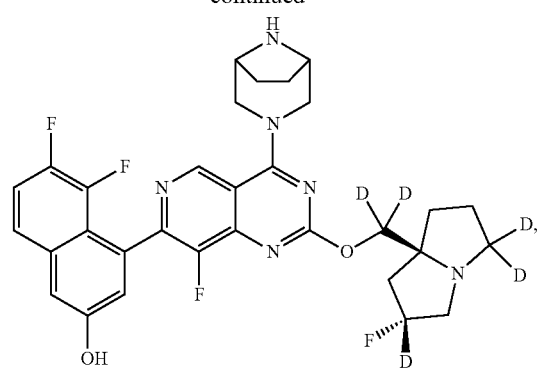
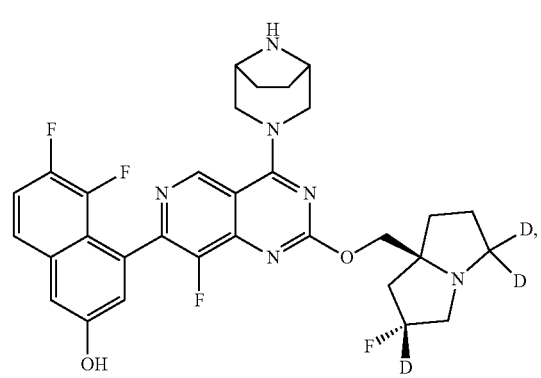
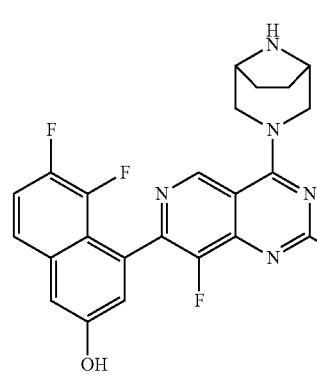
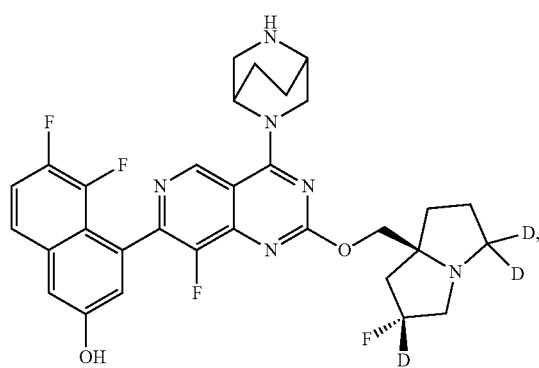

EX. 28
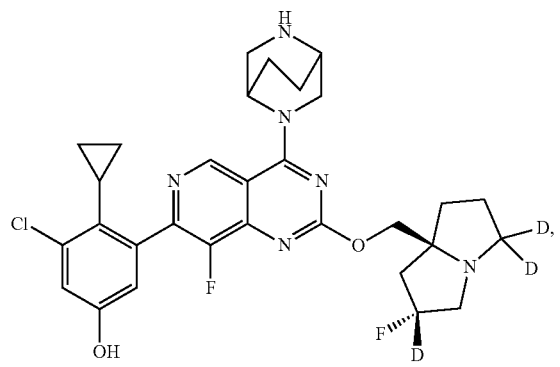
EX. 29
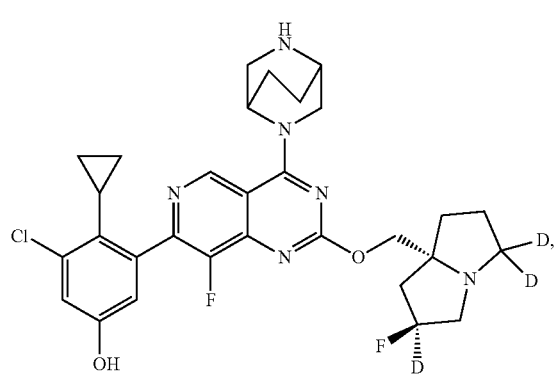
EX. 30
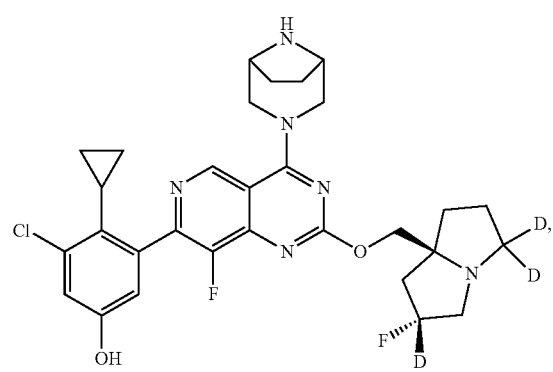
EX. 31
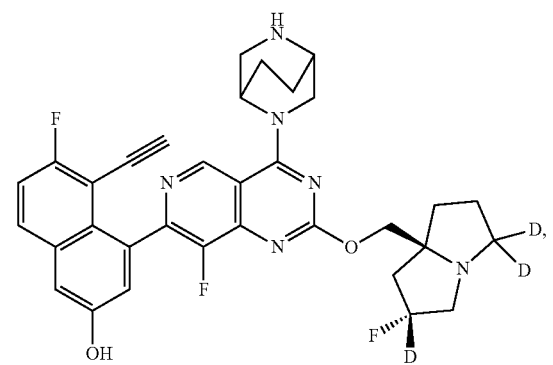
EX. 32
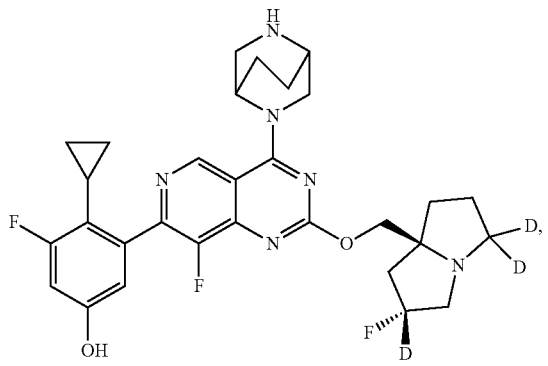
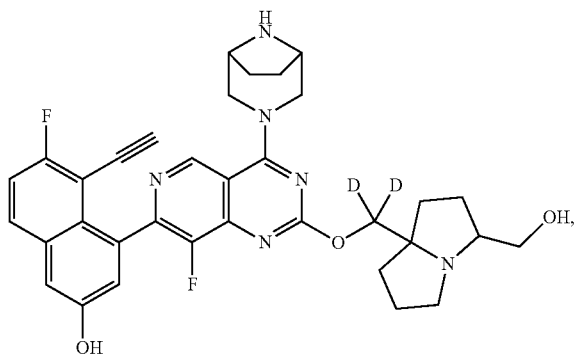
EX. 35
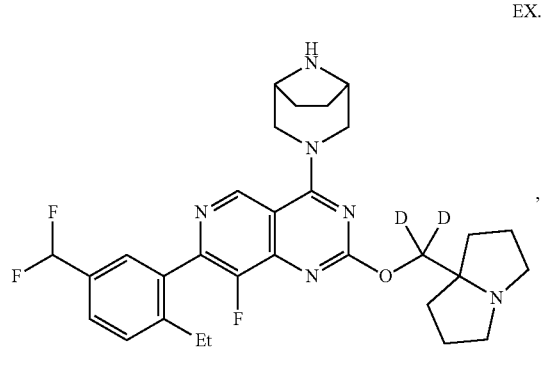
EX. 36
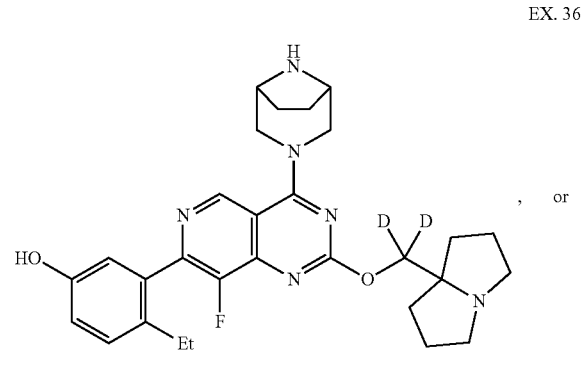

EX. 37

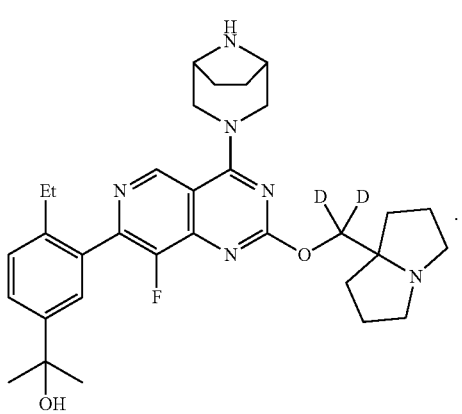

Linkers (L')

A linker is a bivalent moiety that connects KRAS G12Di to Degron. Linkers are disclosed, for example, in International Publication No. WO 2021/127278, the entire content of which is incorporated herein by reference, and are referred to therein by variable L. See, in particular, paragraphs [00491]-[00501] and Table B therein. In some aspects (e.g., of any of the foregoing embodiments, aspects or combinations of aspects), L' is a linker disclosed in WO 2021/127278. Linkers are also disclosed, for example, in U.S. Pat. No. 11,352,350, the entire content of which is incorporated herein by reference, and are referred to therein by variable L. See, in particular, columns 408-409 and 2573-2574 therein. In some aspects (e.g., of any of the foregoing embodiments, aspects of combinations of aspects, L' is a linker disclosed in U.S. Pat. No. 11,352,350.

Linkers are also disclosed in U.S. Patent Application Publication No. US 2020/0140456, the entire content of which is incorporated herein by reference. See, in particular, paragraphs [0491]-[0508] therein. In some aspects (e.g., of any of the foregoing embodiments, aspects or combinations of aspects), L' is a linker disclosed in US 2020/0140456.

In some aspects (e.g., of any of the foregoing embodiments, aspects or combinations of aspects), L' is a covalent bond or a bivalent, saturated or unsaturated, straight or branched $C_{1-50}$ hydrocarbon chain, wherein 0-10 methylene units of L' are independently replaced by X, wherein:
each X is independently —C(D)(H)—, —C(D)$_2$-, —C(H)(F)—, —C(F)$_2$—, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)—, —S(O)—, —S(O)$_2$—, —N(R)S(O)$_2$—, —N(R)C(O)—, —OC(O)N(R)—, —N(R)C(O)N(R)—,

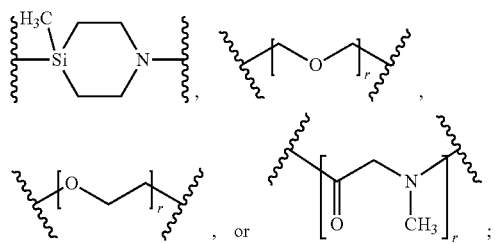

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur; or two R on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and r is 0, 1, 2, 3, 4, 5, 6, 7, 8, 9, or 10.

In some aspects (e.g., of any of the foregoing embodiments, aspects or combinations of aspects), L' is a covalent bond or a bivalent, saturated or unsaturated, straight or branched
$C_1$-$C_{25}$ hydrocarbon chain wherein 0-10 methylenes of L' are replaced by X, wherein: each X is independently —O—, —N(R)—, —S—, —OC(O)—, —C(O)—, —C(H)(F)—, —C(F)$_2$—, -Cy-, —S(O)—, —S(O)$_2$—, —N(R)S(O)$_2$—, —N(R)C(O)—, —OC(O)N(R)—, —N(R)C(O)N(R)—,

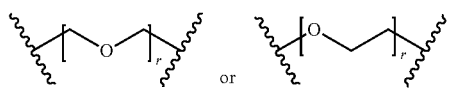

(and, in some further aspects, —O—, —N(R)—, —S—, —OC(O)—, —C(O)—, —C(H)(F)—, —C(F)$_2$—, -Cy-, —S(O)—, —S(O)$_2$—, —N(R)S(O)$_2$—, —N(R)C(O)—, —OC(O)N(R)— or —N(R)C(O)N(R)—);

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur; and each R is independently hydrogen or $(C_1-C_3)$alkyl.

In further aspects, L' is a bivalent, saturated or unsaturated, straight or branched $C_1-C_{25}$ hydrocarbon chain wherein 0-10 methylenes of L' are replaced by X. In yet further aspects, L' is a bivalent, saturated or unsaturated, straight or branched $C_1-C_{15}$ hydrocarbon chain wherein 0-10 methylenes of L' are replaced by X.

In some aspects (e.g., of any of the foregoing embodiments, aspects or combinations of aspects), L' is a covalent bond or a bivalent, saturated or unsaturated, straight or branched $C_1-C_{25}$ hydrocarbon chain wherein 0-10 methylenes of L' are replaced by X, wherein:

each -Cy- is independently an optionally substituted bivalent ring selected from a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur (and, in some further aspects, each -Cy- is independently an optionally substituted (e.g., unsubstituted) bivalent ring selected from a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur);

each X is independently —O—, —N(R)—, —S—, —OC(O)—, —C(O)—, —C(H)(F)—, —C(F)$_2$—, —S(O)—, —S(O)$_2$—, —N(R)S(O)$_2$—, —N(R)C(O)—, —OC(O)N(R)— or —N(R)C(O)N(R)—; and each R is independently hydrogen or $(C_1-C_3)$alkyl.

In further aspects, L' is a bivalent, saturated or unsaturated, straight or branched $C_1-C_{25}$ hydrocarbon chain wherein 0-10 methylenes of L' are replaced by X. In yet further aspects, L' is a bivalent, saturated or unsaturated, straight or branched $C_1-C_{15}$ hydrocarbon chain wherein 0-10 methylenes of L' are replaced by X.

In some aspects (e.g., of any of the foregoing embodiments, aspects or combinations of aspects), L' is a bivalent, saturated or unsaturated, straight or branched $C_1-C_{15}$ hydrocarbon chain wherein 1, 2 or 3 (e.g., 1 or 2; 1; 2) methylenes of L' are replaced by Cy and 0-5 (e.g., 0-3, 1-3, 1 or 2) methylenes of L' are replaced by X, wherein Cy, X and R are as described in any of the aspects herein. In some further aspects, 1 or 2 methylenes of L' are replaced by Cy. In some yet further aspects, 1 methylene of L' is replaced by Cy. In some yet further aspects, 2 methylenes of L' are replaced by Cy.

In some aspects, L' is saturated. In some aspects, L' is straight-chain. In some aspects, L' is saturated and straight-chain.

In some aspects, 0-8 methylenes of L' are replaced by X, e.g., 0-7, 1-8, 2-8 or 1-5 methylenes of L' are replaced by X.

In some aspects, each -Cy- is independently an optionally substituted bivalent ring selected from a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur. In some aspects, each -Cy- is independently an optionally substituted (e.g., unsubstituted) bivalent ring selected from a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur. In further aspects, each -Cy- is independently an optionally substituted (e.g., unsubstituted) bivalent 4-7 membered saturated or partially unsaturated (e.g., saturated) heterocyclylenyl having 1-2 heteroatoms independently selected from nitrogen, oxygen, and sulfur, or 4-11 membered saturated or partially unsaturated (e.g., saturated) spiro heterocyclylenyl having 1-3 (and, in some aspects, 1-2) heteroatoms independently selected from nitrogen, oxygen, and sulfur. In yet further aspects, each -Cy- is independently an optionally substituted (e.g., unsubstituted) bivalent 4-7 membered saturated or partially unsaturated (e.g., saturated) heterocyclylenyl having 1-2 heteroatoms independently selected from nitrogen, oxygen, and sulfur. In some aspects, each -Cy- is independently selected from cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, 3,9-diazaspiro[5.5]undecanylene, or triazinylene.

In some aspects, each -Cy- is independently optionally substituted with halo, alkyl or haloalkyl.

In some aspects (e.g., of any of the foregoing embodiments, aspects or combinations of aspects), L' is —X—$(C_1-C_5)$aliphatic-X—, —X—$(C_1-C_5)$aliphatic-, —X—X—$(C_1-C_5)$aliphatic-X—, —X—X—X—$(C_1-C_5)$aliphatic-, —X—X—$(C_1-C_5)$aliphatic-, —X—X—$(C_1-C_5)$aliphatic-X—$(C_1-C_5)$aliphatic-, —X—X—X—X—$(C_1-C_5)$aliphatic-, —X—X—X—$(C_1-C_5)$aliphatic-X—$(C_1-C_5)$aliphatic-, —X—$(C_1-C_5)$aliphatic-X—X—$(C_1-C_5)$aliphatic-, —X—X—$(C_1-C_5)$aliphatic-X—X—, —X—X—X—$(C_1-C_5)$aliphatic-X—, —X—X—X—X—, —X—X—X— or —X—X—, wherein X is as defined herein. For example, in some aspects, L' is —X—($C_1$-$C_5$)aliphatic-X—, —X—($C_1$-$C_5$)aliphatic-*, —X—X—($C_1$-$C_5$)aliphatic-X—*, *—X—X—($C_1$-$C_5$)aliphatic-X—, —X—X—($C_1$-$C_5$)aliphatic-*, —X—X—($C_1$-$C_5$)aliphatic-*, —X—X—($C_1$-$C_5$)aliphatic-X—($C_1$-$C_5$)aliphatic-*, —X—X—X—($C_1$-$C_5$)aliphatic-*, —X—X—X—($C_1$-$C_5$)aliphatic-X—($C_1$-$C_5$)aliphatic-*, —X—X—($C_1$-$C_5$)aliphatic-X—($C_1$-$C_5$)aliphatic-*, —X—X—($C_1$-$C_5$)aliphatic-X—, —X—X—X—($C_1$-$C_5$)aliphatic-X—*, —X—X—X—X—, —X—X—X— or —X—X—, wherein X is as defined herein and * indicates the point of attachment of L' to Degron.

In some aspects (e.g., of any of the foregoing embodiments, aspects or combinations of aspects):

L' is —X—($C_1$-$C_{15}$)aliphatic-X—*, —X—($C_1$-$C_{15}$)aliphatic-*, —X-Cy-($C_1$-$C_5$)aliphatic-Cy-*, —X-Cy-($C_1$-$C_5$)aliphatic-Cy-($C_1$-$C_5$)aliphatic-*, —X-Cy-X—($C_1$-$C_{10}$)aliphatic-*, —X-Cy-Cy-($C_1$-$C_5$)aliphatic-*, —X—($C_1$-$C_5$)aliphatic-X-Cy-*, —X-Cy-($C_1$-$C_5$)aliphatic-*, —X-Cy-($C_1$-$C_5$)aliphatic-Cy-($C_1$-$C_5$)aliphatic-*, —X-Cy-X-Cy-($C_1$-$C_5$)aliphatic-*, —X-Cy-X—($C_1$-$C_5$)aliphatic-Cy-*, —X-Cy-Cy-($C_1$-$C_5$)aliphatic-X—($C_1$-$C_5$)aliphatic-*, —X-Cy-X—($C_1$-$C_5$)aliphatic-Cy-($C_1$-$C_5$)aliphatic-*, —X-Cy-X—($C_1$-$C_5$)aliphatic-Cy-*, —X—($C_1$-$C_5$)aliphatic-X-Cy-*, —X—($C_1$-$C_5$)aliphatic-X-Cy-($C_1$-$C_5$)aliphatic-*, —X-Cy-($C_1$-$C_5$)aliphatic-X—($C_1$-$C_5$)aliphatic-*, —X-Cy-($C_1$-$C_5$)aliphatic-X—($C_1$-$C_5$)aliphatic-*, —X-Cy-($C_1$-$C_5$)aliphatic-Cy-X—*, —X—($C_1$-$C_5$)aliphatic-X—($C_1$-$C_5$)aliphatic-Cy-*, —X—($C_1$-$C_5$)aliphatic-Cy-($C_1$-$C_5$)aliphatic-*, —X-Cy-Cy-X—*, —X-Cy-X-Cy-*, —X-Cy-Cy-* or —X-Cy-*, wherein * indicates the point of attachment of L' to Degron;

each X is independently —O—, —C(O)—, —N(R)— or —N(R)C(O)—; and each -Cy- is independently selected from any of the values for -Cy- described herein, e.g., cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, 3,9-diazaspiro[5.5]undecanylene, or triazinylene.

In some further aspects, L' is —X-Cy-($C_1$-$C_5$)aliphatic-Cy-*, —X-Cy-($C_1$-$C_5$)aliphatic-Cy-($C_1$-$C_5$)aliphatic-*, —X-Cy-X—($C_1$-$C_{10}$)aliphatic-*, —X-Cy-Cy-($C_1$-$C_5$)aliphatic-*, —X—($C_1$-$C_5$)aliphatic-X-Cy-*, —X-Cy-($C_1$-$C_5$)aliphatic-*, —X-Cy-($C_1$-$C_5$)aliphatic-Cy-($C_1$-$C_5$)aliphatic-*, —X-Cy-X-Cy-($C_1$-$C_5$)aliphatic-*, —X-Cy-X—($C_1$-$C_5$)aliphatic-Cy-*, —X-Cy-Cy-($C_1$-$C_5$)aliphatic-X—($C_1$-$C_5$)aliphatic-*, —X-Cy-X—($C_1$-$C_5$)aliphatic-Cy-($C_1$-$C_5$)aliphatic-*, —X-Cy-($C_1$-$C_5$)aliphatic-X-Cy-*, —X—($C_1$-$C_5$)aliphatic-X-Cy-*, —X-Cy-($C_1$-$C_5$)aliphatic-X-Cy-($C_1$-$C_5$)aliphatic-*, —X-Cy-($C_1$-$C_5$)aliphatic-X-Cy-($C_1$-$C_5$)aliphatic-*, —X-Cy-($C_1$-$C_5$)aliphatic-Cy-X—*, —X—($C_1$-$C_5$)aliphatic-X—($C_1$-$C_5$)aliphatic-Cy-*, —X—($C_1$-$C_5$)aliphatic-Cy-($C_1$-$C_5$)aliphatic-*, —X-Cy-Cy-X—*, —X-Cy-X-Cy-*, —X-Cy-Cy-* or —X-Cy-*. In some further aspects, L' is —X-Cy-($C_1$-$C_5$)aliphatic-Cy-*, —X-Cy-($C_1$-$C_5$)aliphatic-Cy-($C_1$-$C_5$)aliphatic-*, —X-Cy-X—($C_1$-$C_{10}$)aliphatic-*, —X-Cy-Cy-($C_1$-$C_5$)aliphatic-*, —X—($C_1$-$C_5$)aliphatic-X-Cy-*, —X-Cy-($C_1$-$C_5$)aliphatic-Cy-($C_1$-$C_5$)aliphatic-*, —X-Cy-X-Cy-($C_1$-$C_5$)aliphatic-*, —X-Cy-X—($C_1$-$C_5$)aliphatic-Cy-*, —X-Cy-Cy-($C_1$-$C_5$)aliphatic-X—($C_1$-$C_5$)aliphatic-*, —X-Cy-X—($C_1$-$C_5$)aliphatic-Cy-($C_1$-$C_5$)aliphatic-*, —X-Cy-($C_1$-$C_5$)aliphatic-X-Cy-*, —X-Cy-($C_1$-$C_5$)ali-phatic-X-Cy-($C_1$-$C_5$)aliphatic-*, —X-Cy-($C_1$-$C_5$)aliphatic-X—($C_1$-$C_5$)aliphatic-*, —X-Cy-($C_1$-$C_5$)aliphatic-Cy-X—*, —X-Cy-X-Cy-*, —X-Cy-Cy-* or —X-Cy-*.

In some aspects of L', L' is linked to KRAS G12Di via —X-Cy-. In some aspects, when —X-Cy- links L' to KRAS G12Di, —X-Cy- is —C(O)-Cy-, wherein Cy is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 (and, in some aspects, 1) additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked to the —C(O)— via the nitrogen atom, for example, -Cy- is piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, or 3,9-diazaspiro[5.5]undecanylene. In some further aspects, —X-Cy-, when —X-Cy- links L' to KRAS G12Di, is

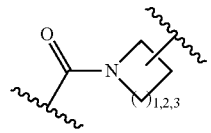

In some yet further aspects, —X-Cy-, when —X-Cy- links L' to KRAS G12Di, is

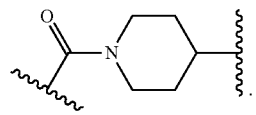 [SMILES: *C(=O)N1CCC(*)CC1]

In some aspects of L', L' includes -$Cy^1$-$(CH_2)_{0-1}$—X—$(CH_2)_{0-1}$-$Cy^2$-, wherein: $Cy^1$ and $Cy^2$ are independently selected from any of the values for Cy described herein; and X is absent or selected from any of the values for X described herein.

For example, in some aspects, $Cy^1$ is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 (and, in some aspects, 1) additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked (e.g., to the rest of L' (if present), KRAS G12Di or Degron) via a nitrogen atom, for example, $Cy^1$ is piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]

octanylene, 2,7-diazaspiro[3.5]nonanylene, or 3,9-diazaspiro[5.5]undecanylene. In some further aspects, Cy¹ is

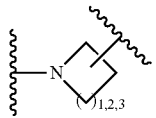

In some yet further aspects, Cy¹ is

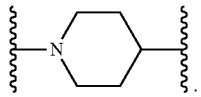

In some preferred aspects, Cy¹ represents the terminus of -Cy¹-(CH₂)₀₋₁—X—(CH₂)₀₋₁-Cy²- nearer KRAS G12Di in the compounds of the disclosure. In some further or alternative aspects, Cy² is cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, 3,9-diazaspiro[5.5]undecanylene, or triazinylene. In some preferred aspects, Cy² represents the terminus of -Cy¹-(CH₂)₀₋₁—X—(CH₂)₀₋₁-Cy²- nearer Degron in the compounds of the disclosure. In some aspects, X is C(O), O or N(R), wherein R is as described herein. In some further aspects, X is O or N(R). In some aspects, Cy¹ is linked to KRAS G12Di via X, wherein X is as described herein, e.g., —C(O)— or —C(O)O—. In some aspects wherein Cy¹ is linked to KRAS G12Di via —C(O)— or —C(O)O—, Cy¹ is linked to the carbonyl carbon of —C(O)— or —C(O)O— via a nitrogen atom of Cy¹.

In some aspects (e.g., of any of the foregoing embodiments, aspects or combinations of aspects), L' is —X—(C₀-C₁₅)aliphatic-X—, —X—(C₀-C₁₅)aliphatic-, —X—X—(C₀-C₁₅)aliphatic-X—, —X—X—X—(C₁-C₁₅)aliphatic- or —X—X—(C₁-C₁₅)aliphatic-. For example, in some aspects, L' is —X—(C₀-C₁₅)aliphatic-X—*, —X—(C₀-C₁₅)aliphatic-*, —X—X—(C₀-C₁₅)aliphatic-X—*, —X—X—X—(C₁-C₁₅)aliphatic-* or —X—X—(C₁-C₁₅)aliphatic-*, wherein * indicates the point of attachment of L' to Degron. In some aspects, L' is —X—(C₁-C₁₅)aliphatic-X—, —X—(C₁-C₁₅)aliphatic-, —X—X—(C₁-C₁₅)aliphatic-X—, —X—X—X—(C₁-C₁₅)aliphatic- or —X—X—(C₁-C₁₅)aliphatic-. In some aspects, L' is —X—(C₁-C₁₅)aliphatic-X—*, —X—(C₁-C₁₅)aliphatic-*, —X—X—(C₁-C₁₅)aliphatic-X—*, —X—X—X—(C₁-C₁₅)aliphatic-* or —X—X—(C₁-C₁₅)aliphatic-*, wherein * indicates the point of attachment of L' to Degron. In some aspects, L' is —C(O)-Cy-O—(C₁-C₁₀)aliphatic or —C(O)-Cy-(C₁-C₁₀)aliphatic, e.g., —C(O)-Cy-O—(C₁-C₁₀)aliphatic* or —C(O)-Cy-(C₁-C₁₀)aliphatic*, wherein * indicates the point of attachment of L' to Degron.

In some aspects (e.g., of any of the foregoing embodiments, aspects or combinations of aspects), L' is —X—(CH₂)$_p$—X—, —X—(CH₂)$_q$— or —X—(CH₂CH₂O)$_r$CH₂CH₂—X—, wherein p is an integer from 0 to 15; q is an integer from 0 to 15; and r is an integer from 1 to 5. For example, in some aspects, L' is —X—(CH₂)$_p$—X—*, —X—(CH₂)$_q$—* or —X—(CH₂CH₂O)$_r$CH₂CH₂—X—*, wherein * indicates the point of attachment of L' to Degron.

In some aspects, L' is —C(O)N(H)—(CH₂)$_p$—N(H)—, —C(O)N(H)—(CH₂)$_p$— or —C(O)N(H)—(CH₂CH₂O)$_r$CH₂CH₂—N(H)—. In further aspects, L' is —C(O)N(H)—(CH₂)$_p$—N(H)—*, —C(O)N(H)—(CH₂)$_p$—* or —C(O)N(H)—(CH₂CH₂O)$_r$CH₂CH₂—N(H)—*, wherein * indicates the point of attachment of L' to Degron.

In some aspects, p is an integer from 2 to 10, e.g., 3 to 10; 6 to 10; or 9 or 10.

In some aspects, q is an integer from 2 to 11, e.g., 3 to 11; 5 to 11; or 9, 10 or 11. In some aspects, q is an integer from 6 to 15, e.g., from 8 to 12.

In some aspects, r is 1, 2, 3, 4, or 5. In some aspects, r is 1, 2 or 3, e.g., 2 or 3; 2; or 3.

In some aspects, each X is independently —O—, —N(R)—, —S—, —OC(O)—, —C(O)—, —C(H)(F)—, —C(F)₂-, -Cy-, —S(O)—, —S(O)₂—, —N(R)S(O)₂—, —N(R)C(O)—, —OC(O)N(R)—, —N(R)C(O)N(R)—,

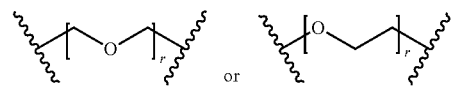

In some aspects, each X is independently —O—, —C(O)—, —N(R)—, —S—, —OC(O)—, -Cy-, —N(R)C(O)—, —OC(O)N(R)— or —N(R)C(O)N(R)—. In some aspects, each X is independently —O—, —N(R)—, —S—, —OC(O), —N(R)C(O)—, —OC(O)N(R)— or —N(R)C(O)N(R)—. In some aspects, each X is independently —O—, —N(R)—, —S—, —OC(O), —N(R)C(O)— or —OC(O)N(R)—. In some aspects, each X is independently —O—, —C(O)—, —N(R)—, -Cy- or —N(R)C(O)—. In some aspects, each X is independently —O—, —C(O)—, —N(R)—, or —N(R)C(O)—. In some aspects, each X is independently —O—, —N(R)— or —N(R)C(O)—.

In some aspects, each R is independently hydrogen or methyl. In further aspects, each R is hydrogen.

Specific examples of L' include —C(O)N(H)—(CH₂)$_{3,4,6,8,9,10}$—N(H)—*, —C(O)N(H)—(CH₂)$_{2,3,4,5,8,9,10,11}$—* and —C(O)N(H)—(CH₂CH₂O)$_{2,3}$CH₂CH₂—N(H)—*, wherein * indicates the point of attachment of L' to Degron. Other specific examples of L' include

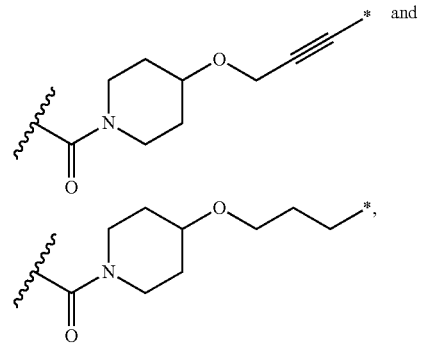

wherein ⸹ indicates the point of attachment to KRAS G12Di and * indicates the point of attachment of L' to Degron.

Other specific examples of L' include the linkers depicted in Table A. In some aspects, L' is a linker in Table A.

TABLE A
Linkers (L')
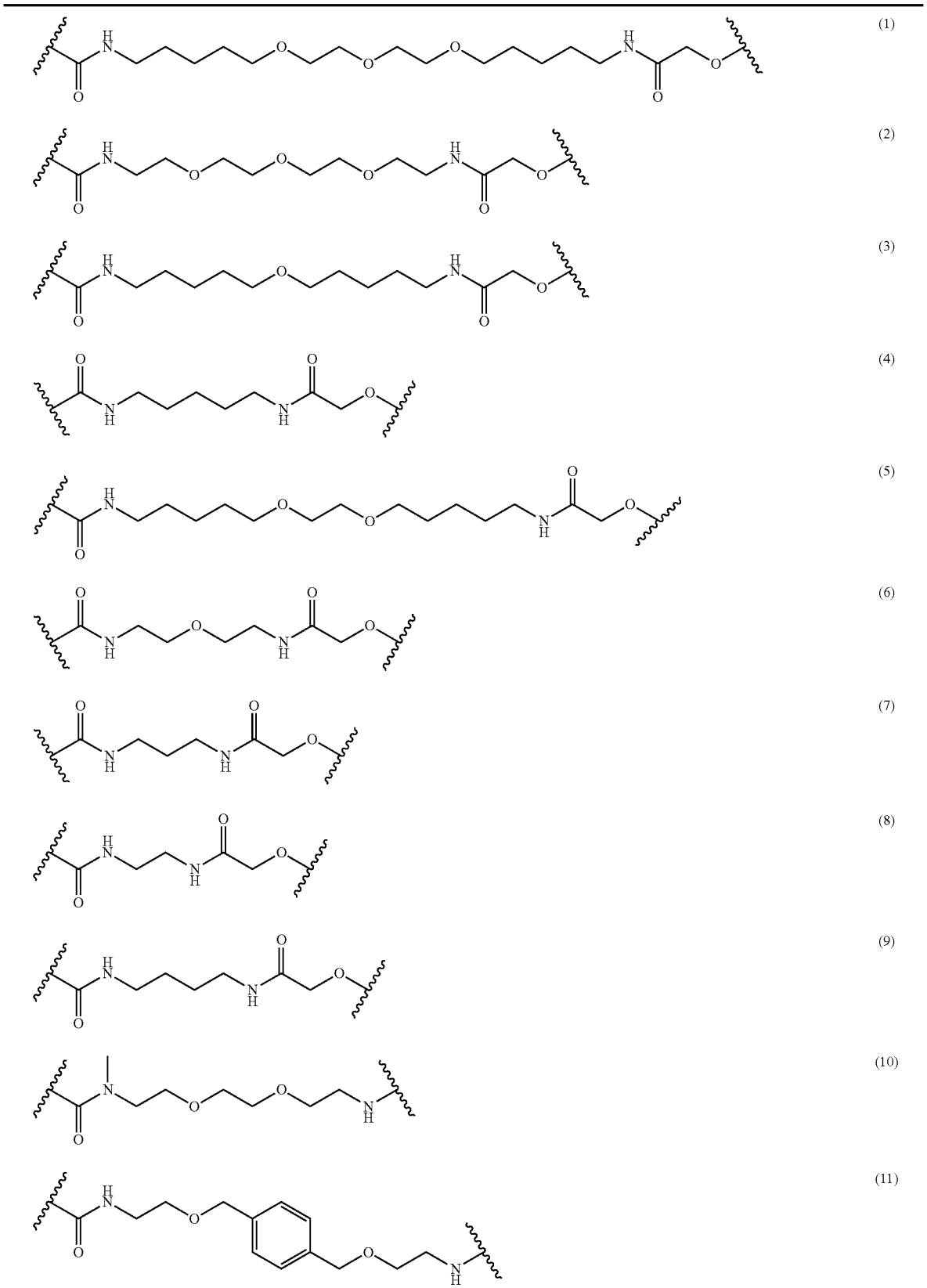

TABLE A-continued

| Linkers (L') | |
|---|---|
| (chemical structure) | (12) |
| (chemical structure) | (13) |
| (chemical structure) | (14) |
| (chemical structure) | (15) |
| (chemical structure) | (16) |
| (chemical structure) | (17) |
| (chemical structure) | (18) |
| (chemical structure) | (19) |
| (chemical structure) | (20) |
| (chemical structure) | (21) |
| (chemical structure) | (22) |

TABLE A-continued

Linkers (L')

(23)-(33) [chemical structures]

TABLE A-continued

Linkers (L')

(34)–(44) [chemical structures]

TABLE A-continued

Linkers (L')

TABLE A-continued

Linkers (L')

(57) — (67): chemical structures

TABLE A-continued

Linkers (L')

(68) — (78) [Chemical structures not transcribable as text]

TABLE A-continued
Linkers (L')
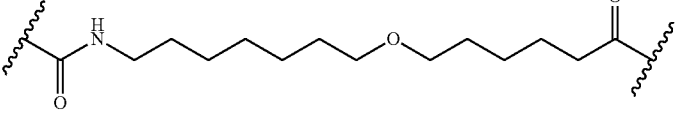 (79)
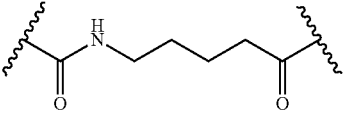 [SMILES: *C(=O)CCCCNC(*)=O] (80)
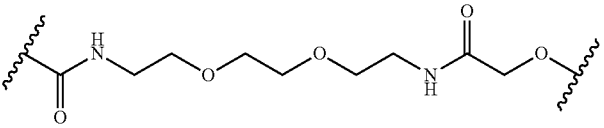 [SMILES: *OCC(=O)NCCOCCOCCNC(*)=O] (81)
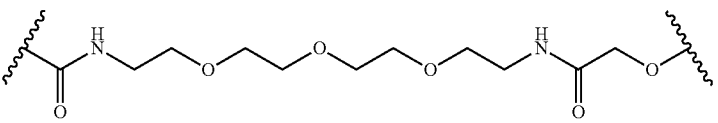 [SMILES: *OCC(=O)NCCOCCOCCOCCNC(*)=O] (82)
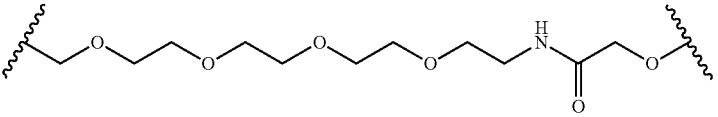 [SMILES: *COCCOCCOCCOCCNC(=O)CO*] (83)
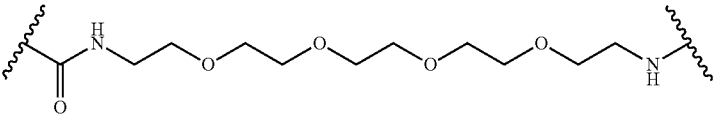 [SMILES: *NCCOCCOCCOCCOCCNC(*)=O] (84)
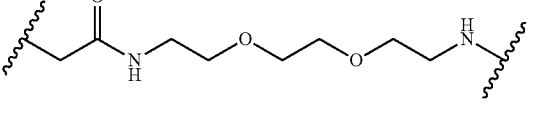 (85)
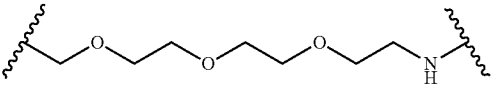 [SMILES: *COCCOCCOCCN*] (86)
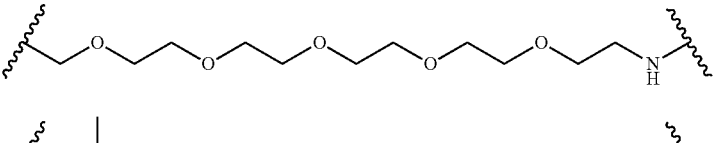 (87)
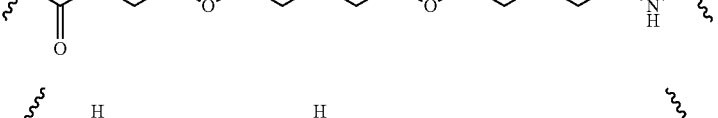 (88)
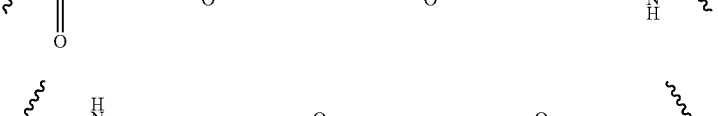 (89)
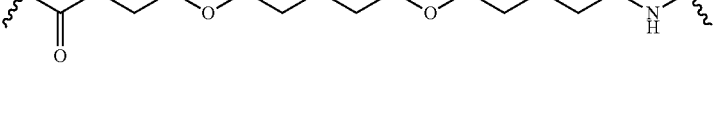 (90)

TABLE A-continued

Linkers (L')

(91) – (101): chemical structure images not extracted.

TABLE A-continued
Linkers (L')
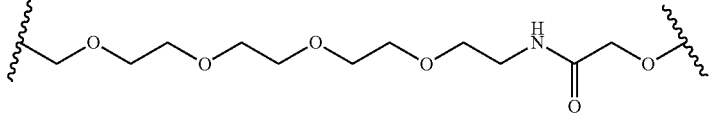 [SMILES: *COCCOCCOCCOCCNC(=O)CO*] (103)
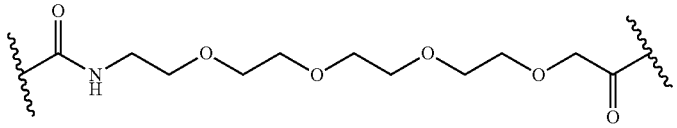 [SMILES: *C(=O)COCCOCCOCCOCCNC(*)=O] (104)
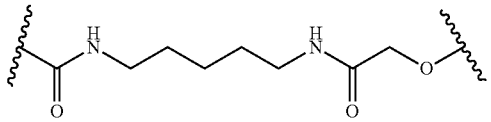 [SMILES: *OCC(=O)NCCCCCNC(*)=O] (105)
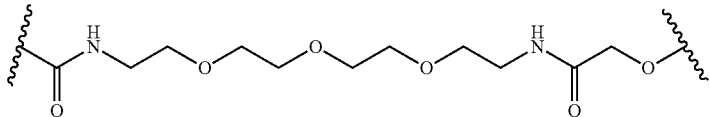 [SMILES: *OCC(=O)NCCOCCOCCOCCNC(*)=O] (106)
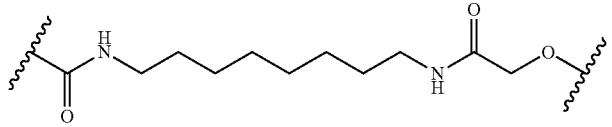 [SMILES: *OCC(=O)NCCCCCCCCNC(*)=O] (107)
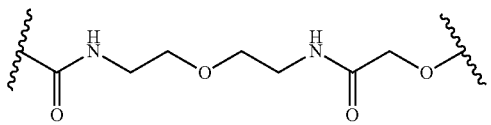 [SMILES: *OCC(=O)NCCOCCNC(*)=O] (108)
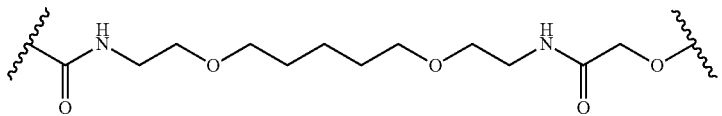 [SMILES: *OCC(=O)NCCOCCCCCOCCNC(*)=O] (109)
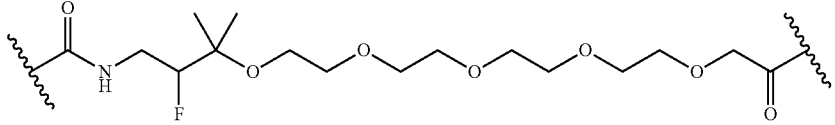 [SMILES: *C(=O)COCCOCCOCCOCCOC(C)(C)C(F)CNC(*)=O] (110)
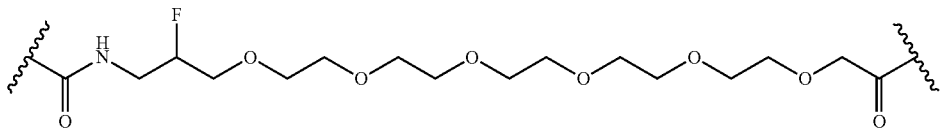 [SMILES: *C(=O)COCCOCCOCCOCCOCCOCC(F)CNC(*)=O] (111)
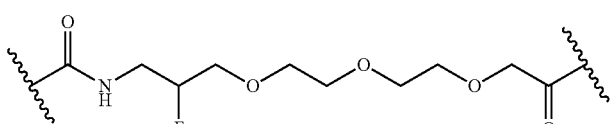 (112)
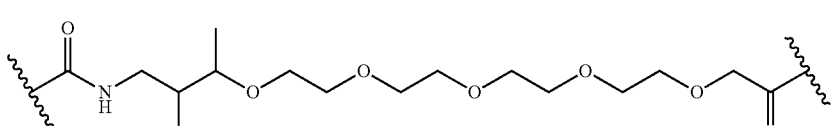 (113)

TABLE A-continued
Linkers (L')
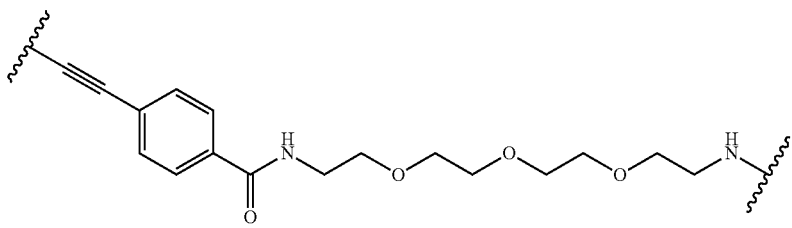 [SMILES: *C#Cc1ccc(C(=O)NCCOCCOCCOCCN*)cc1] (114)
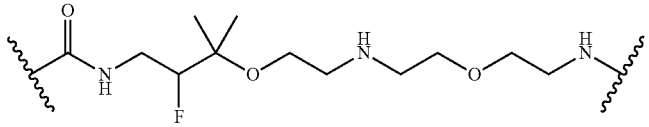 [SMILES: *NCCOCCNCCOC(C)(C)C(F)CNC(*)=O] (115)
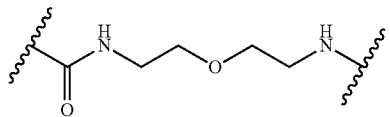 [SMILES: *NCCOCCNC(*)=O] (116)
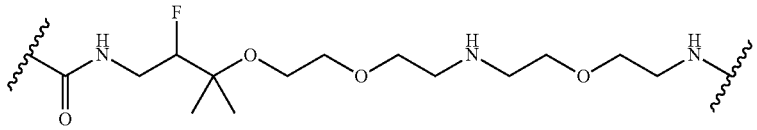 [SMILES: *NCCOCCNCCOCCOC(C)(C)C(F)CNC(*)=O] (117)
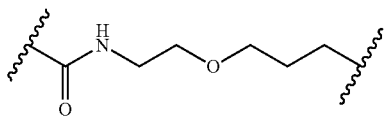 [SMILES: *CCCOCCNC(*)=O] (118)
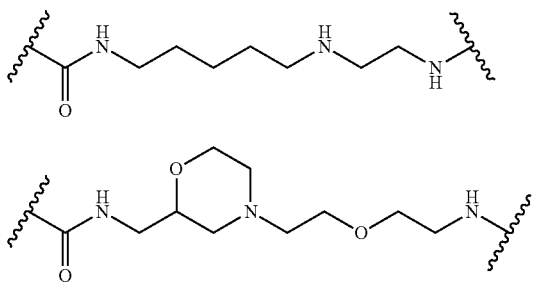 (119)
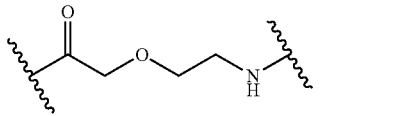 [SMILES: *NCCOCC(*)=O] (120)
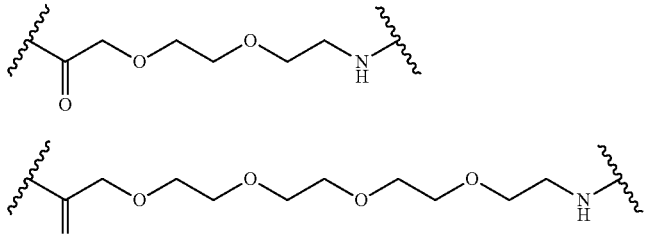 (121)
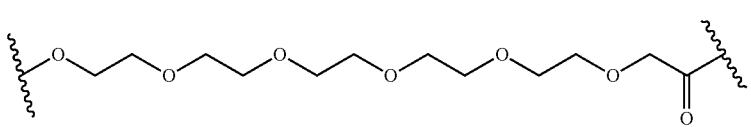 [SMILES: *OCCOCCOCCOCCOCCOCC(*)=O] (122)

TABLE A-continued
Linkers (L')
 (123)
 (124)
 (125)
 (126)
 (127)
 (128)
 (129)
 (130)
(131)

TABLE A-continued
Linkers (L')
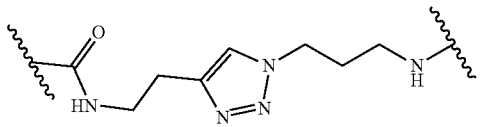 [SMILES: *NCCCn1cc(CCNC(*)=O)nn1] (132)
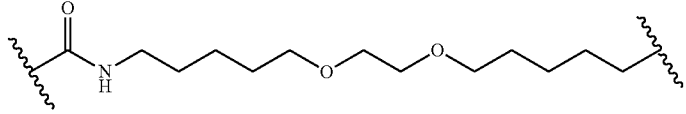 [SMILES: *CCCCCOCCOCCCCCNC(*)=O] (133)
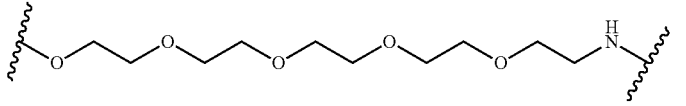 [SMILES: *NCCOCCOCCOCCOCCO*] (134)
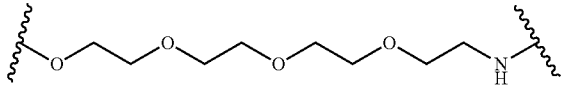 [SMILES: *NCCOCCOCCOCCO*] (135)
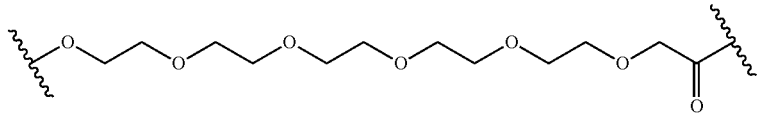 [SMILES: *OCCOCCOCCOCCOCCOCC(*)=O] (136)
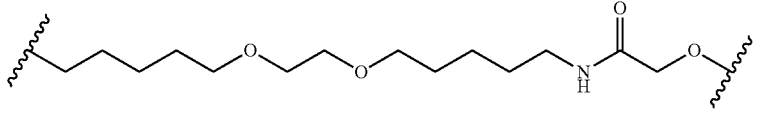 [SMILES: *CCCCCOCCOCCCCCNC(=O)CO*] (137)
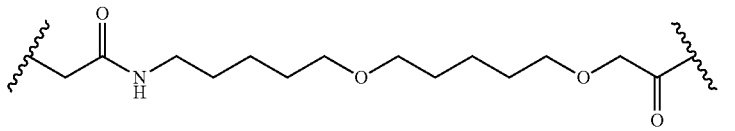 [SMILES: *CC(=O)NCCCCCOCCCCCOCC(*)=O] (138)
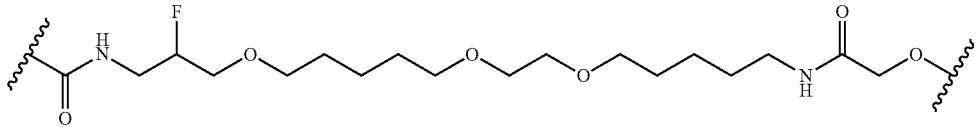 [SMILES: *OCC(=O)NCCCCCOCCOCCCCCOCC(F)CNC(*)=O] (139)
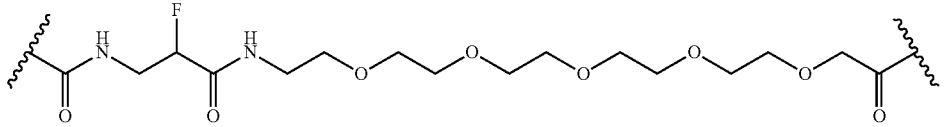 [SMILES: *C(=O)COCCOCCOCCOCCOCCNC(=O)C(F)CNC(*)=O] (140)
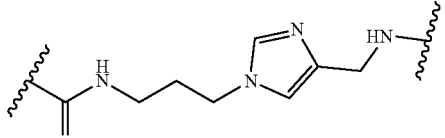 (141)
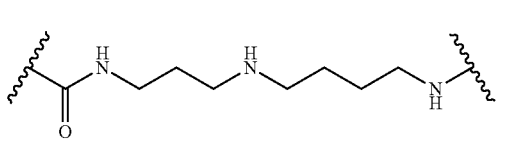 [SMILES: *NCCCCNCCCNC(*)=O] (142)

TABLE A-continued
Linkers (L')
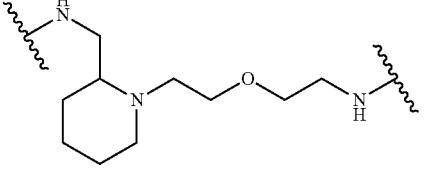 (143)
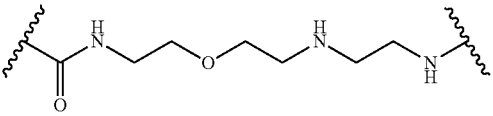 (144)
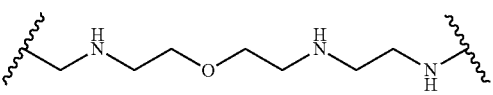 [SMILES: *CNCCOCCNCCN*] (145)
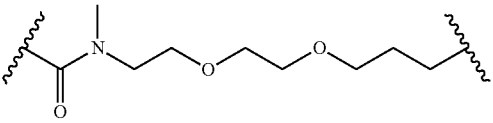 [SMILES: *CCCOCCOCCN(C)C(*)=O] (146)
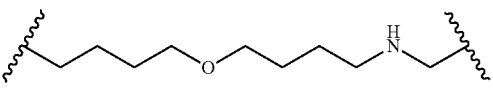 [SMILES: *CCCCOCCCCNC*] (147)
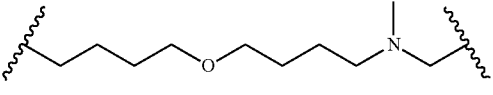 [SMILES: *CCCCOCCCCN(C)C*] (148)
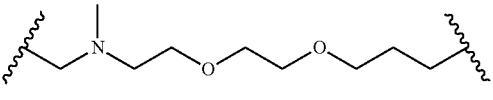 [SMILES: *CCCOCCOCCN(C)C*] (149)
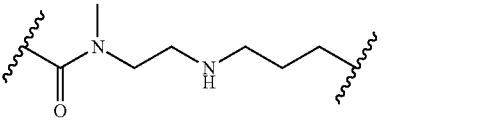 [SMILES: *CCCNCCN(C)C(*)=O] (150)
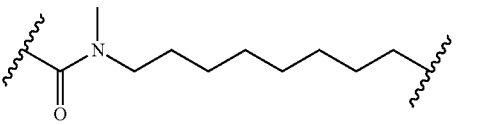 [SMILES: *CCCCCCCCN(C)C(*)=O] (151)
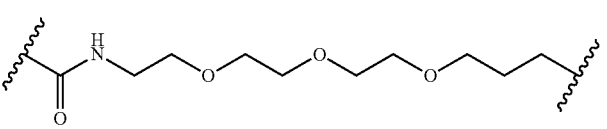 [SMILES: *CCCOCCOCCOCCNC(*)=O] (152)
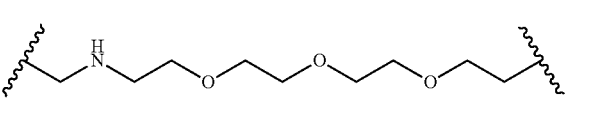 [SMILES: *CCOCCOCCOCCNC*] (153)
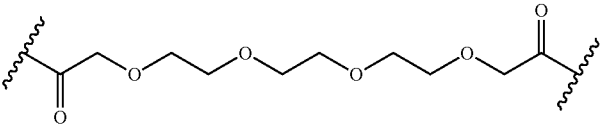 [SMILES: *C(=O)COCCOCCOCCOCC(*)=O] (154)

TABLE A-continued

| Linkers (L') | |
|---|---|
| (structure) | (155) |
| (structure) | (156) |
| (structure) | (157) |
| (structure) | (158) |
| (structure) | (159) |
| (structure) | (160) |
| (structure) | (161) |
| (structure) | (162) |
| (structure) | (163) |
| (structure) | (164) |
| (structure) | (165) |
| (structure) | (166) |

TABLE A-continued
Linkers (L')
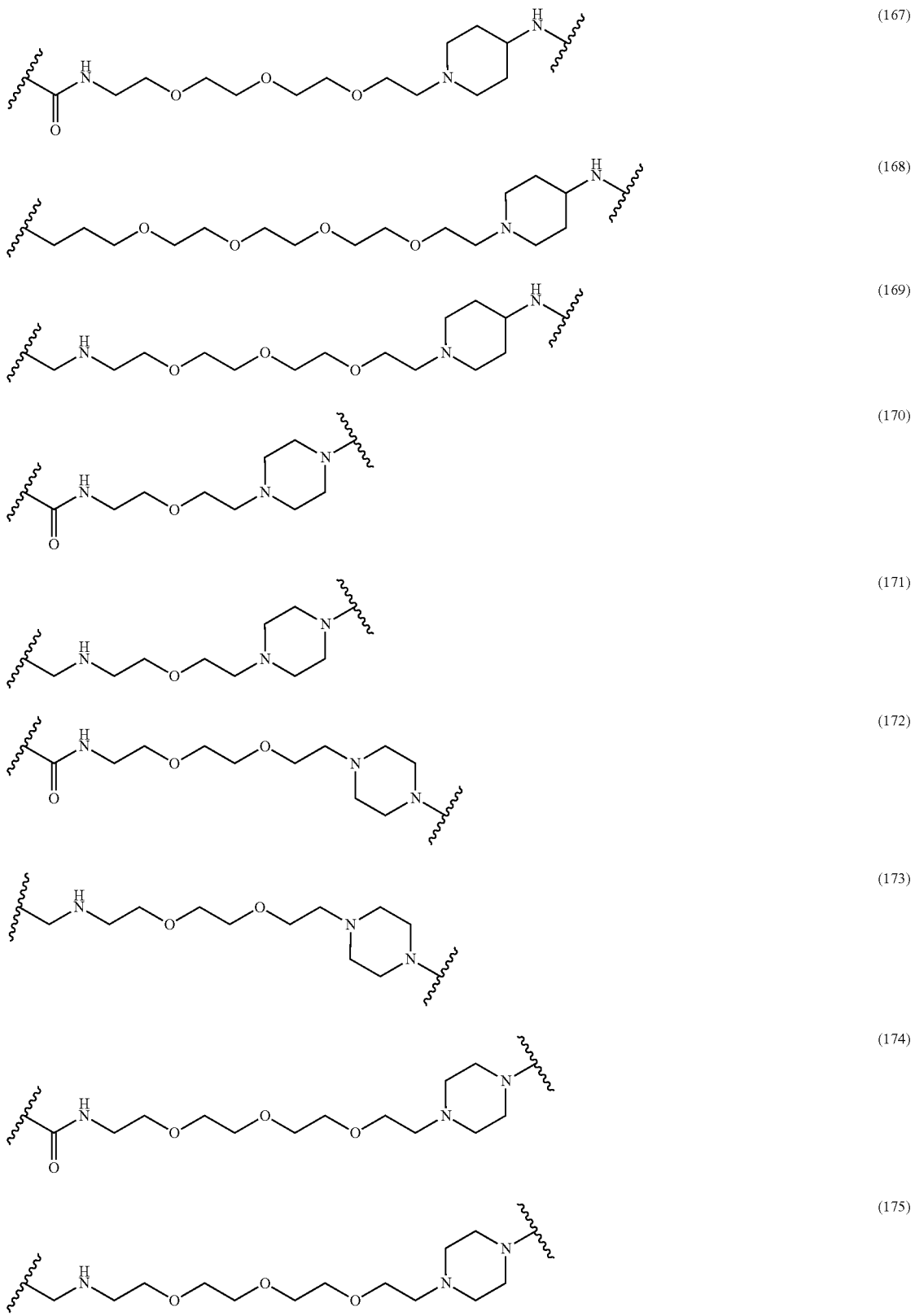

TABLE A-continued
Linkers (L')
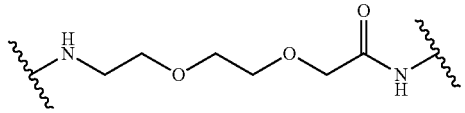 [SMILES: *NCCOCCOCC(=O)N*] (176)
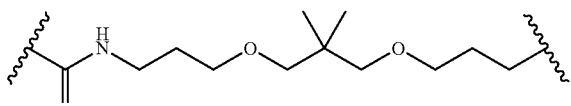 (177)
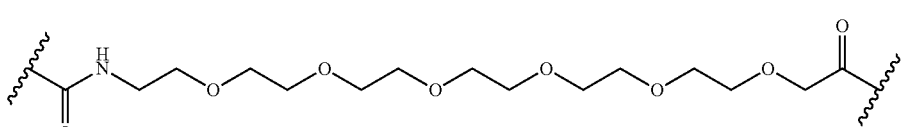 (178)
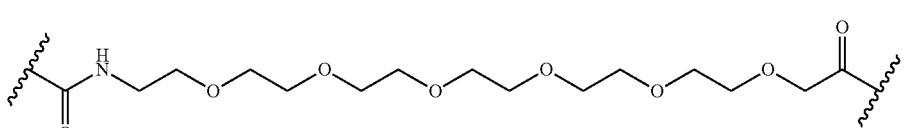 (179)
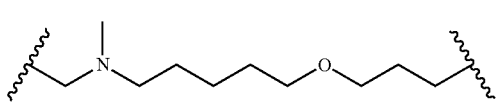 [SMILES: *CCCOCCCCCN(C)C*] (180)
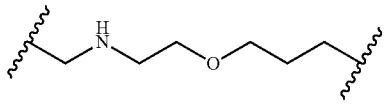 [SMILES: *CCCOCCNC*] (181)
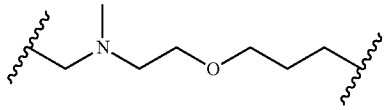 [SMILES: *CCCOCCN(C)C*] (182)
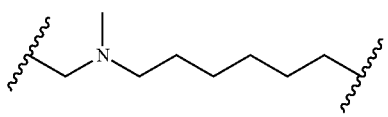 [SMILES: *CCCCCCN(C)C*] (183)
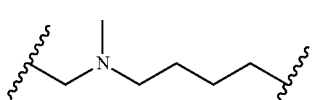 (184)
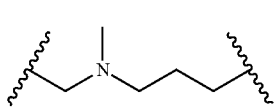 [SMILES: *CCCN(C)C*] (185)
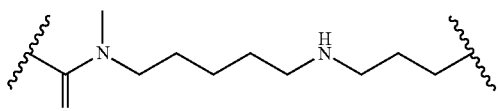 (186)
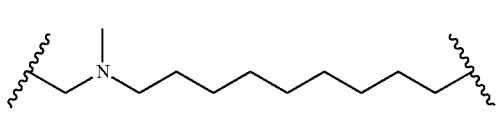 [SMILES: *CCCCCCCCCN(C)C*] (187)
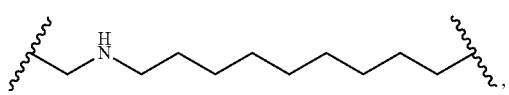 [SMILES: *CCCCCCCCCNC*] (188)

TABLE A-continued
Linkers (L')
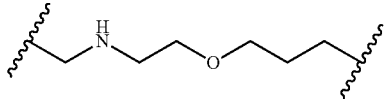 [SMILES: *CCCOCCNC*] (189)
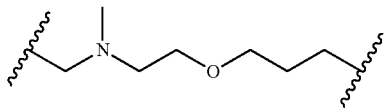 [SMILES: *CCCOCCN(C)C*] (190)
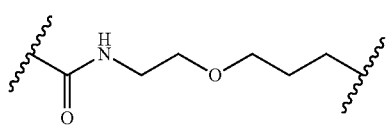 [SMILES: *CCCOCCNC(*)=O] (191)
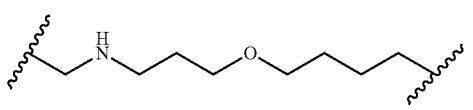 [SMILES: *CCCCOCCCNC*] (192)
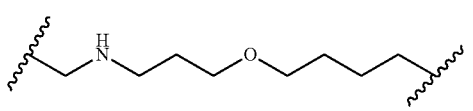 [SMILES: *CCCCOCCCNC*] (193)
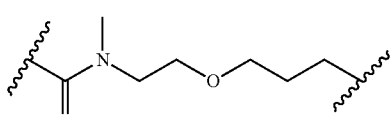 (194)
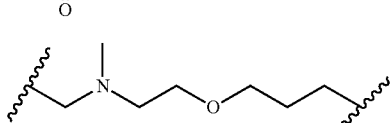 (195)
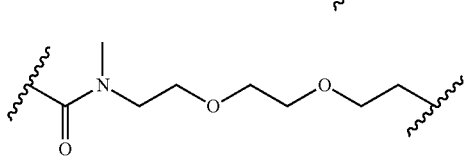 (196)
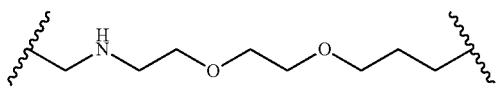 [SMILES: *CCCOCCOCCNC*] (197)
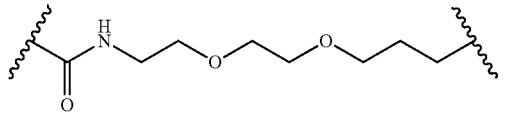 [SMILES: *CCCOCCOCCNC(*)=O] (198)
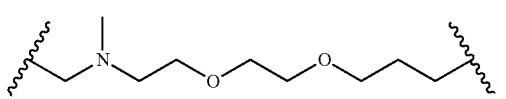 [SMILES: *CCCOCCOCCN(C)C*] (199)
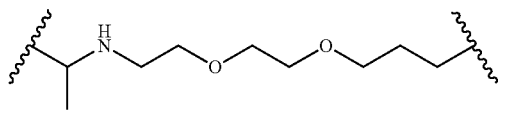 [SMILES: *CCCOCCOCCNC(*)C] (200)
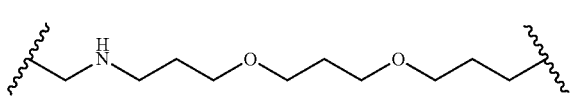 [SMILES: *CCCOCCCOCCCNC*] (201)

TABLE A-continued

| Linkers (L') | |
|---|---|
| [structure] | (202) |
| [structure] | (203) |
| [structure] | (204) |
| [structure] | (205) |
| [structure] | (206) |
| [structure] | (207) |
| [structure] | (208) |
| [structure] | (209) |
| [structure] | (210) |
| [structure] | (211) |
| [structure] | (212) |
| [structure] | (213) |

TABLE A-continued

Linkers (L')

(214)
(215)
(216)
(217)
(218)
(219)
(220)
(221)
(222)
(223)
(224)

TABLE A-continued
Linkers (L')
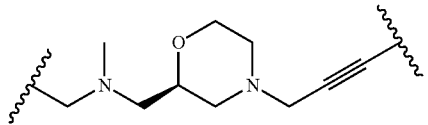 [SMILES: *C#CCN1CCO[C@H](CN(C)C*)C1] (225)
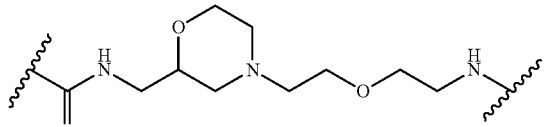 (226)
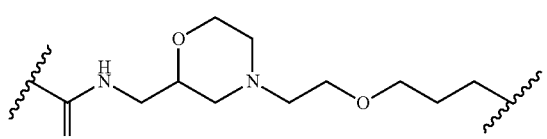 (227)
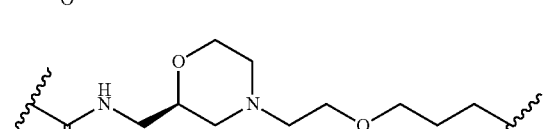 (228)
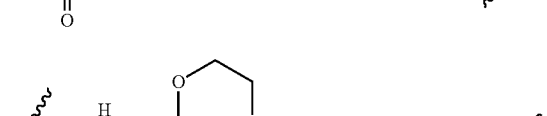 (229)
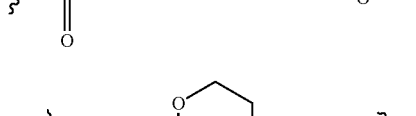 (230)
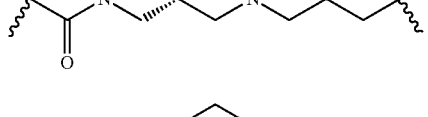 (231)
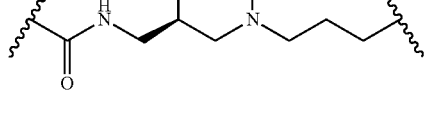 (232)
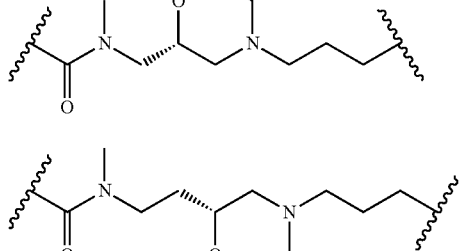 (233)
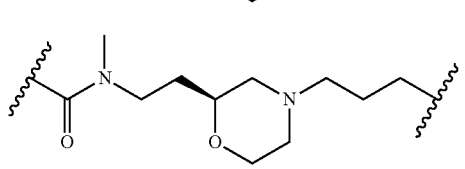 (234)

TABLE A-continued
Linkers (L')
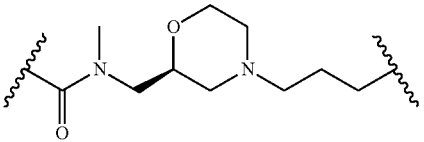 [SMILES: *CCCN1CCO[C@H](CN(C)C(*)=O)C1] (235)
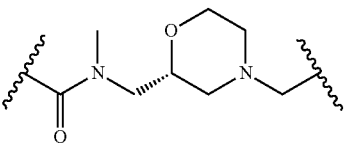 [SMILES: *CN1CCO[C@@H](CN(C)C(*)=O)C1] (236)
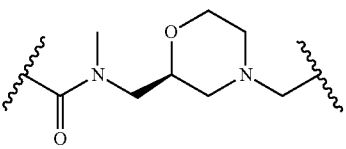 [SMILES: *CN1CCO[C@H](CN(C)C(*)=O)C1] (237)
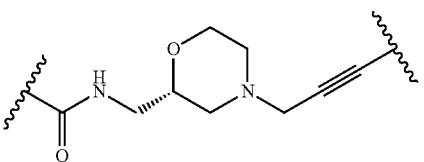 [SMILES: *C#CCN1CCO[C@@H](CNC(*)=O)C1] (238)
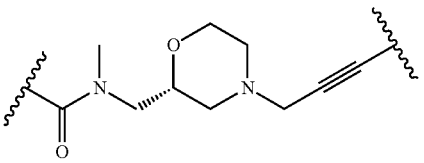 [SMILES: *C#CCN1CCO[C@@H](CN(C)C(*)=O)C1] (239)
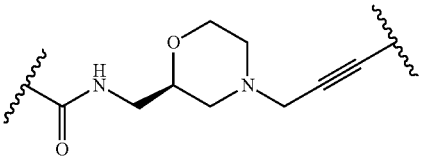 [SMILES: *C#CCN1CCO[C@H](CNC(*)=O)C1] (240)
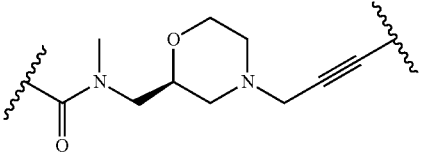 [SMILES: *C#CCN1CCO[C@H](CN(C)C(*)=O)C1] (241)
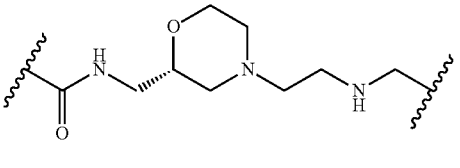 [SMILES: *CNCCN1CCO[C@@H](CNC(*)=O)C1] (242)
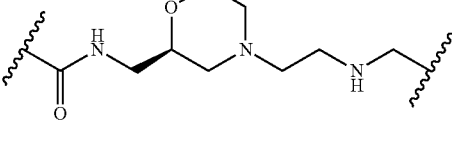 (243)

TABLE A-continued

Linkers (L')

(244) – (254): chemical structures

TABLE A-continued
Linkers (L')
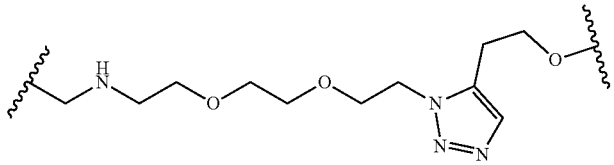 [SMILES: *CNCCOCCOCCn1nncc1CCO*] (255)
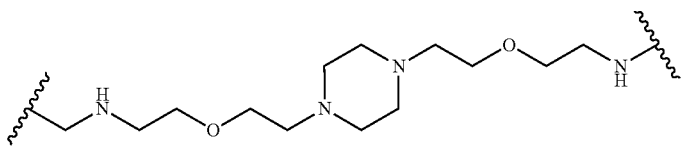 [SMILES: *CNCCOCCN1CCN(CCOCCN*)CC1] (256)
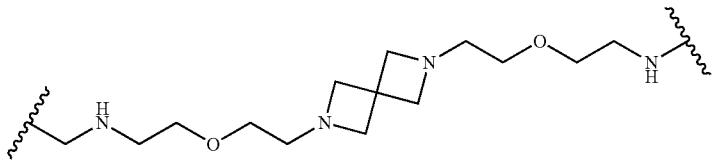 [SMILES: *CNCCOCCN1CC2(CN(CCOCCN*)C2)C1] (257)
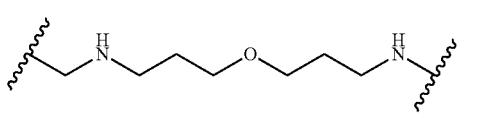 [SMILES: *CNCCCOCCCN*] (258)
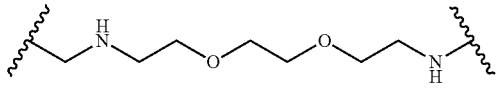 [SMILES: *CNCCOCCOCCN*] (259)
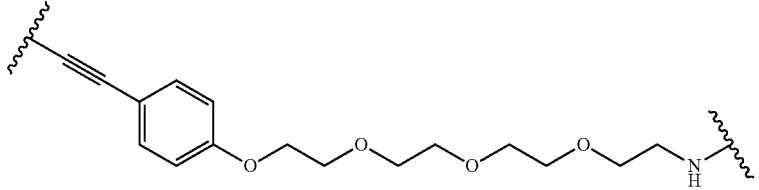 [SMILES: *C#Cc1ccc(OCCOCCOCCOCCN*)cc1] (260)
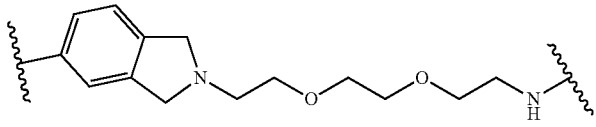 [SMILES: *NCCOCCOCCN1Cc2ccc(*)cc2C1] (261)
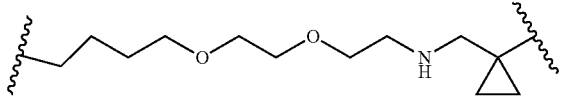 [SMILES: *CCCCOCCOCCNCC1(*)CC1] (262)
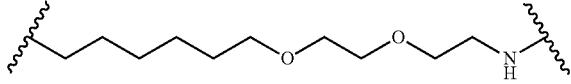 [SMILES: *CCCCCCOCCOCCN*] (263)
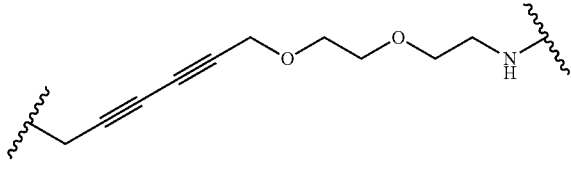 [SMILES: *CC#CC#CCOCCOCCN*] (264)

TABLE A-continued
Linkers (L')
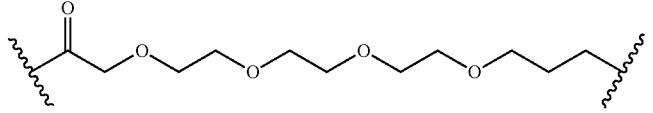 [SMILES: *CCCOCCOCCOCCOCC(*)=O] (265)
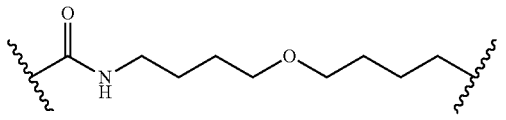 [SMILES: *CCCCOCCCCNC(*)=O] (266)
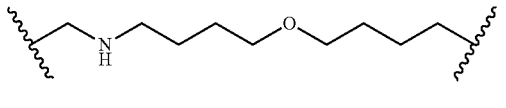 [SMILES: *CCCCOCCCCNC*] (267)
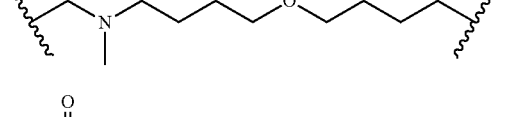 (268)
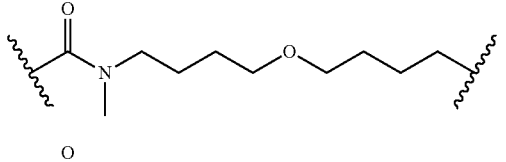 (269)
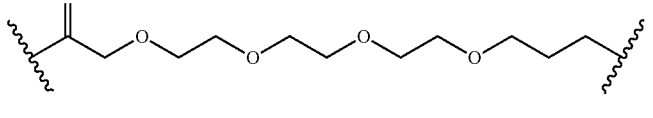 (270)
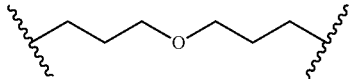 [SMILES: *CCCOCCC*] (271)
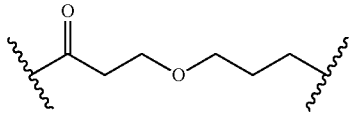 [SMILES: *CCCOCCC(*)=O] (272)
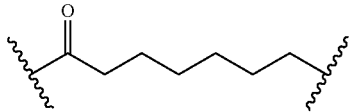 [SMILES: *CCCCCCC(*)=O] (273)
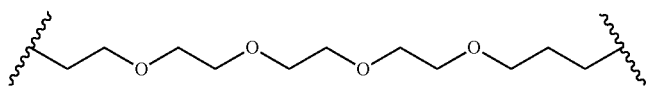 [SMILES: *CCCOCCOCCOCCOCC*] (274)
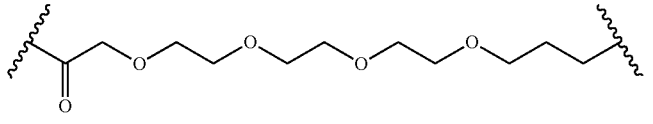 [SMILES: *CCCOCCOCCOCCOCC(*)=O] (275)
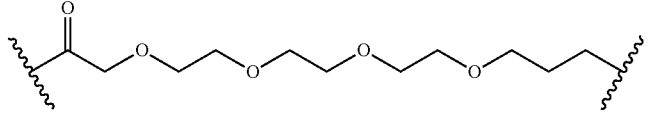 [SMILES: *CCCOCCOCCOCCOCC(*)=O] (276)
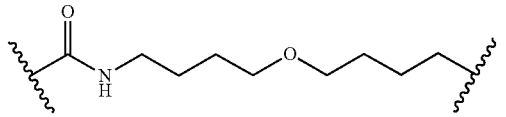 [SMILES: *CCCCOCCCCNC(*)=O] (277)

TABLE A-continued
Linkers (L')
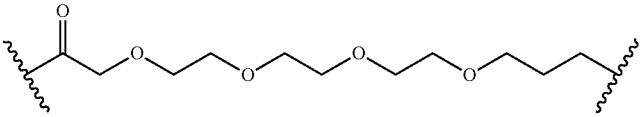 [SMILES: *CCCOCCOCCOCCOCC(*)=O] (278)
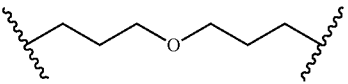 [SMILES: *CCCOCCC*] (279)
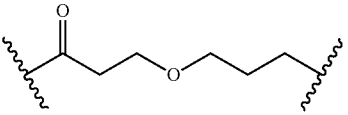 [SMILES: *CCCOCCC(*)=O] (280)
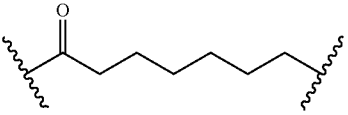 [SMILES: *CCCCCCC(*)=O] (281)
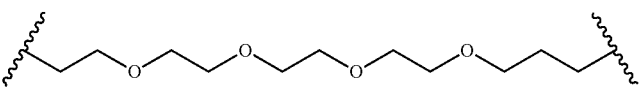 [SMILES: *CCCOCCOCCOCCOCC*] (282)
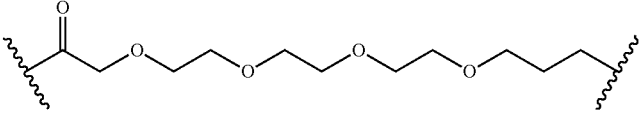 [SMILES: *CCCOCCOCCOCCOCC(*)=O] (283)
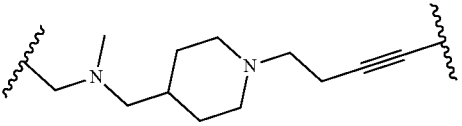 [SMILES: *C#CCCN1CCC(CN(C)C*)CC1] (284)
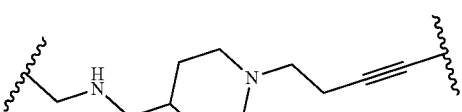 (285)
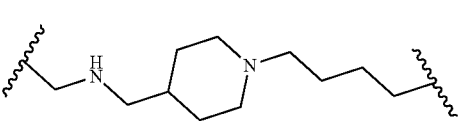 [SMILES: *CCCCN1CCC(CNC*)CC1] (286)
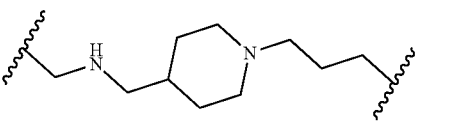 [SMILES: *CCCN1CCC(CNC*)CC1] (287)
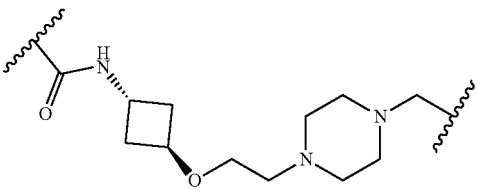 [SMILES: *CN1CCN(CCO[C@H]2C[C@H](NC(*)=O)C2)CC1] (288)

TABLE A-continued

Linkers (L')

(289)

(290)

(291)

(292)

(294)

(295)

(296)

(297)

(298)

TABLE A-continued
Linkers (L')
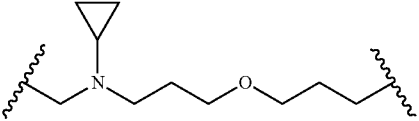 [SMILES: *CCCOCCCN(C*)C1CC1] (299)
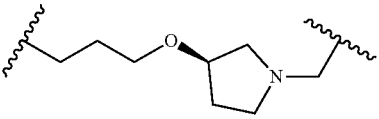 [SMILES: *CCCO[C@@H]1CCN(C*)C1] (300)
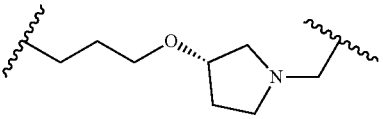 [SMILES: *CCCO[C@H]1CCN(C*)C1] (301)
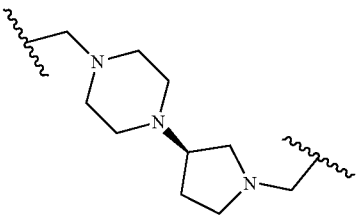 [SMILES: *CN1CCN([C@@H]2CCN(C*)C2)CC1] (302)
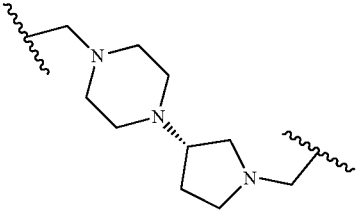 [SMILES: *CN1CCN([C@H]2CCN(C*)C2)CC1] (303)
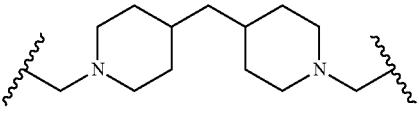 [SMILES: *CN1CCC(CC2CCN(C*)CC2)CC1] (304)
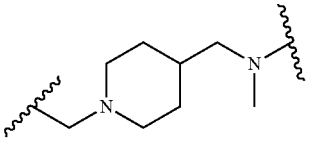 [SMILES: *CN1CCC(CN(*)C)CC1] (305)
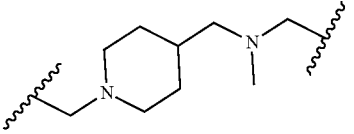 [SMILES: *CN(C)CC1CCN(C*)CC1] (306)
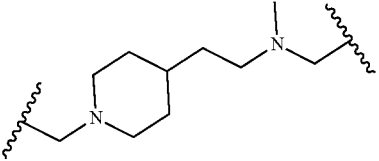 [SMILES: *CN(C)CCC1CCN(C*)CC1] (307)

TABLE A-continued
Linkers (L')
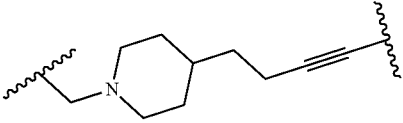 [SMILES: *C#CCCC1CCN(C*)CC1] (308)
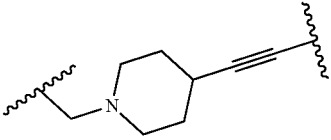 [SMILES: *C#CC1CCN(C*)CC1] (309)
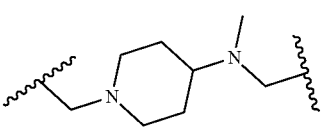 [SMILES: *CN1CCC(N(C)C*)CC1] (310)
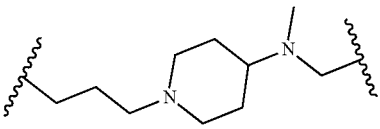 [SMILES: *CCCN1CCC(N(C)C*)CC1] (311)
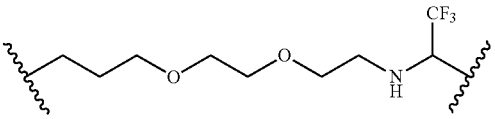 [SMILES: *CCCOCCOCCNC(*)C(F)(F)F] (312)
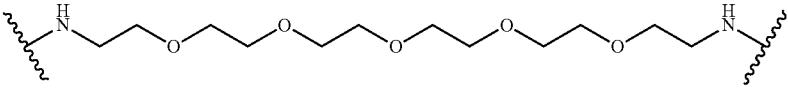 [SMILES: *NCCOCCOCCOCCOCCOCCN*] (313)
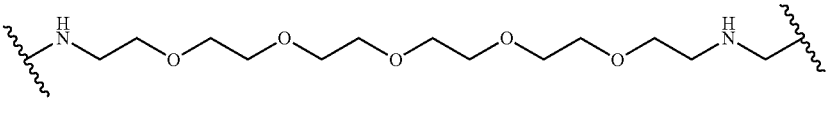 [SMILES: *CNCCOCCOCCOCCOCCOCCN*] (314)
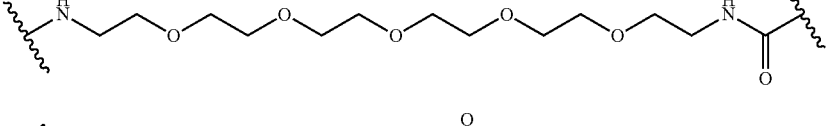 (315)
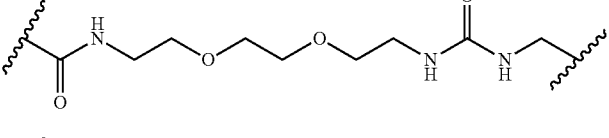 (316)
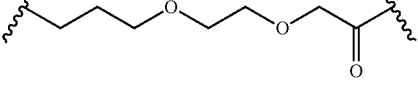 (317)
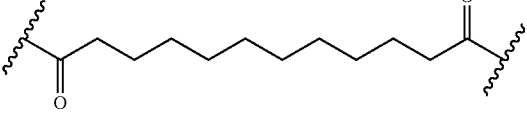 (318)
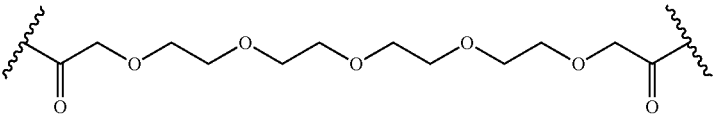 [SMILES: *C(=O)COCCOCCOCCOCCOCC(*)=O] (319)

TABLE A-continued

Linkers (L')

(320) — (331): chemical structures

TABLE A-continued
Linkers (L')
 (332)
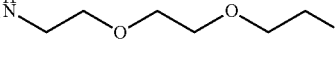 (333)
 (334)
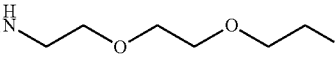 (335)
 (336)
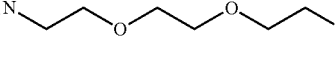 (337)
 (338)
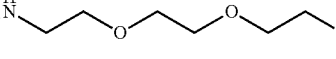 (339)
 (340)
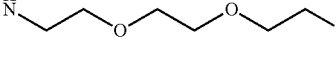 (341)
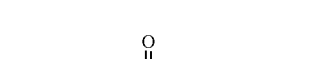 (342)
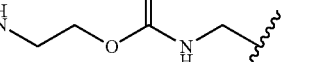 (343)

TABLE A-continued
Linkers (L')
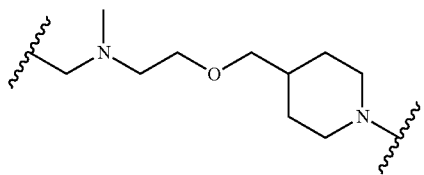 [SMILES: *CN(C)CCOCC1CCN(*)CC1]
(344)
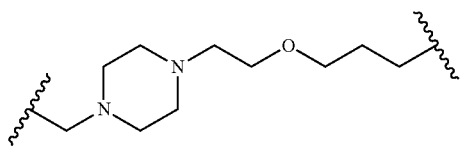 [SMILES: *CCCOCCN1CCN(C*)CC1]
(345)
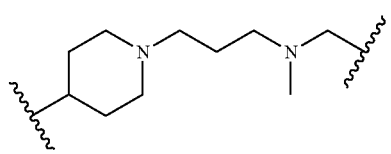 [SMILES: *CN(C)CCCN1CCC(*)CC1]
(346)
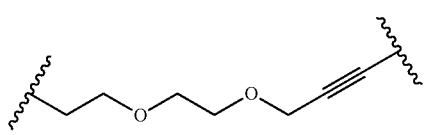 [SMILES: *C#CCOCCOCC*]
(347)
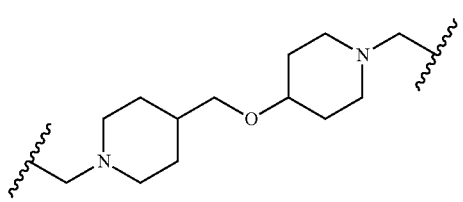 [SMILES: *CN1CCC(COC2CCN(C*)CC2)CC1]
(348)
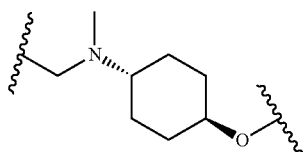 [SMILES: *CN(C)[C@H]1CC[C@H](O*)CC1]
(349)
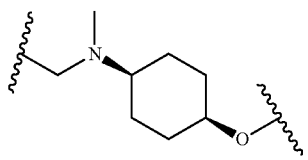 [SMILES: *CN(C)[C@H]1CC[C@@H](O*)CC1]
(350)
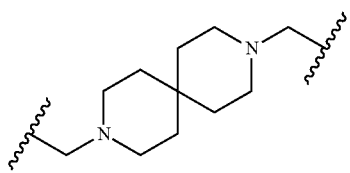 [SMILES: *CN1CCC2(CC1)CCN(C*)CC2]
(351)
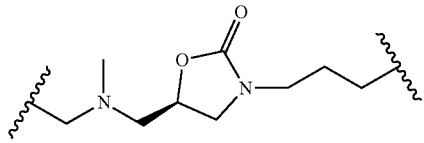 [SMILES: *CCCN1C[C@@H](CN(C)C*)OC1=O]
(352)

TABLE A-continued
Linkers (L')
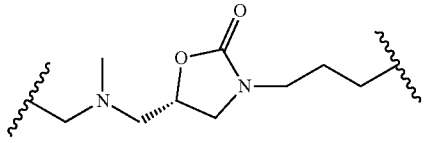 [SMILES: *CCCN1C[C@H](CN(C)C*)OC1=O] (353)
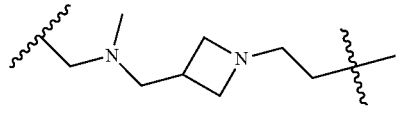 [SMILES: *CCN1CC(CN(C)C*)C1] (354)
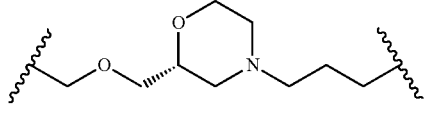 [SMILES: *CCCN1CCO[C@@H](COC*)C1] (355)
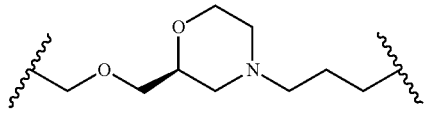 [SMILES: *CCCN1CCO[C@H](COC*)C1] (356)
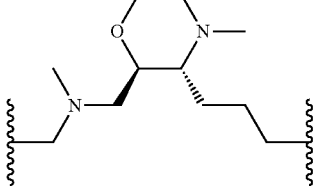 (357)
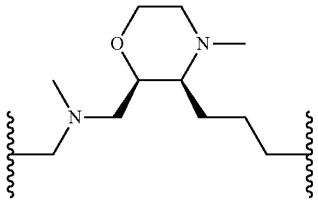 [SMILES: *CCC[C@H]1[C@@H](CN(C)C*)OCCN1C] (358)
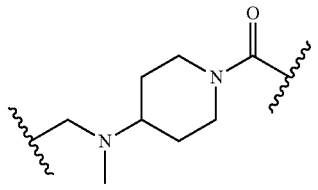 (359)
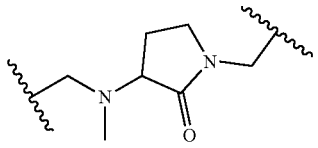 [SMILES: *CN1CCC(N(C)C*)C1=O] (360)
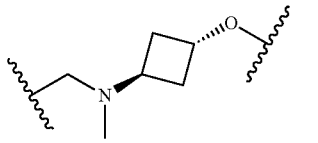 [SMILES: *CN(C)[C@H]1C[C@H](O*)C1] (361)

TABLE A-continued
Linkers (L')
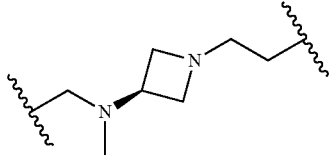 (362)
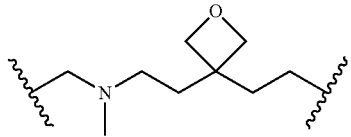 [SMILES: *CCC1(CCN(C)C*)COC1] (363)
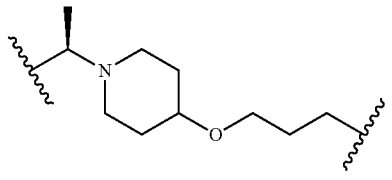 [SMILES: *CCCOC1CCN([C@@H](*)C)CC1] (364)
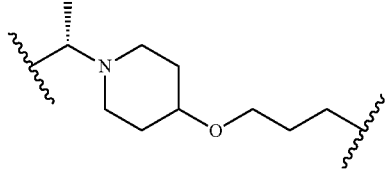 [SMILES: *CCCOC1CCN([C@H](*)C)CC1] (365)
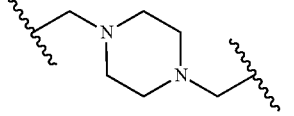 [SMILES: *CN1CCN(C*)CC1] (366)
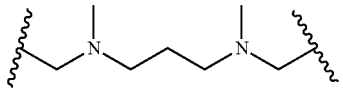 [SMILES: *CN(C)CCCN(C)C*] (367)
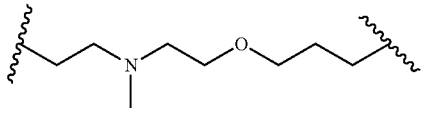 [SMILES: *CCCOCCN(C)CC*] (368)
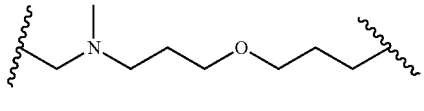 [SMILES: *CCCOCCCN(C)C*] (369)
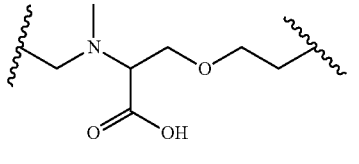 [SMILES: *CCOCC(C(=O)O)N(C)C*] (370)
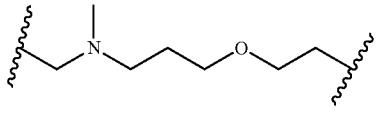 [SMILES: *CCOCCCN(C)C*] (371)
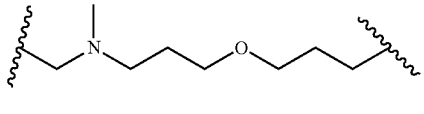 [SMILES: *CCCOCCCN(C)C*] (372)

TABLE A-continued

Linkers (L')

(373)

(374)

(375)

(376)

(377)

(378)

(379)

(380)

(381)

(382)

(383)

TABLE A-continued

Linkers (L')

(384)–(396) Chemical structure diagrams of linker groups.

TABLE A-continued
Linkers (L')
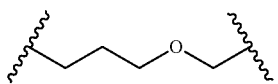 [SMILES: *CCCOC*] (397)
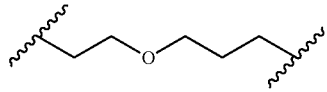 [SMILES: *CCCOCC*] (398)
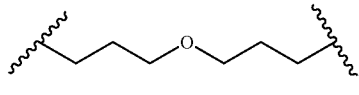 [SMILES: *CCCOCCC*] (399)
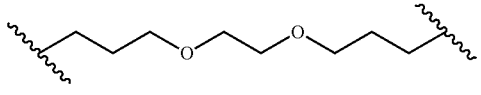 [SMILES: *CCCOCCOCCC*] (400)
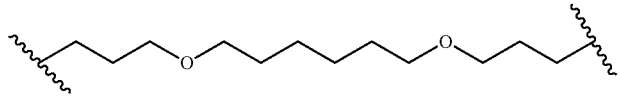 [SMILES: *CCCOCCCCCCOCCC*] (401)
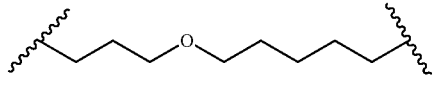 [SMILES: *CCCCCOCCC*] (402)
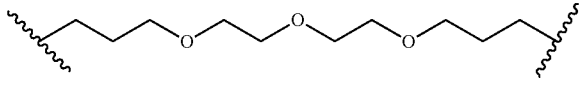 [SMILES: *CCCOCCOCCOCCC*] (403)
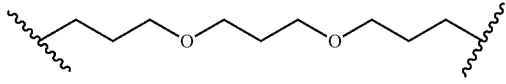 [SMILES: *CCCOCCCOCCC*] (404)
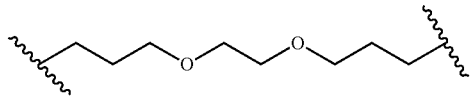 [SMILES: *CCCOCCOCCC*] (405)
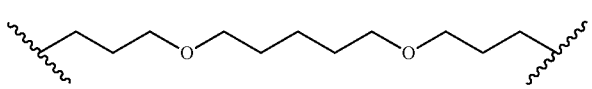 [SMILES: *CCCOCCCCCOCCC*] (406)
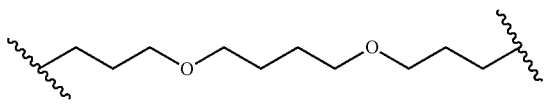 [SMILES: *CCCOCCCCOCCC*] (407)
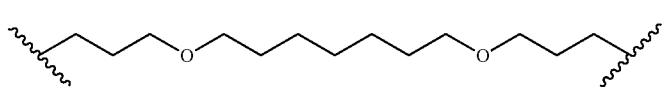 [SMILES: *CCCOCCCCCCCOCCC*] (408)
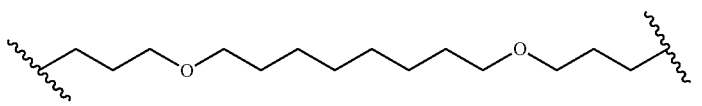 [SMILES: *CCCOCCCCCCCCOCCC*] (409)
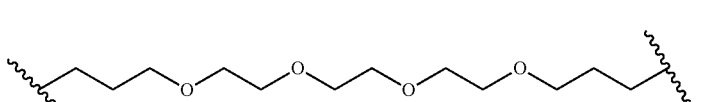 (410)
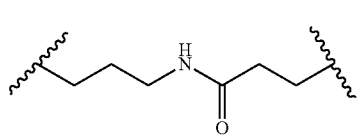 [SMILES: *CCCNC(=O)CC*] (411)

TABLE A-continued
Linkers (L')
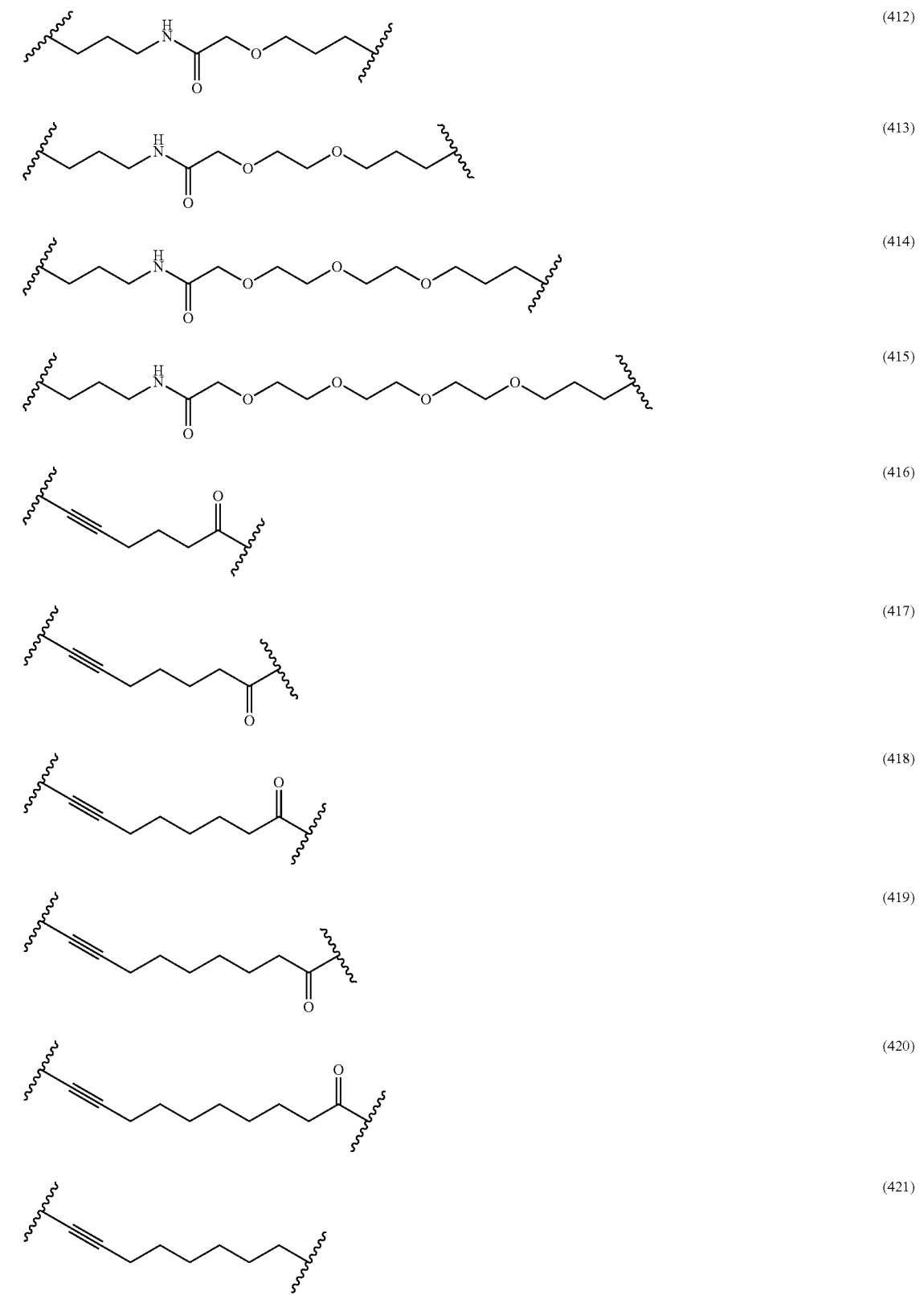

TABLE A-continued
Linkers (L')
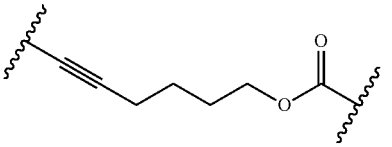 [SMILES: *C#CCCCCOC(*)=O] (422)
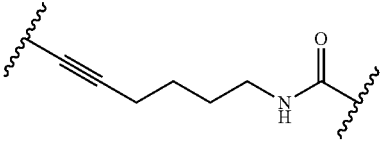 [SMILES: *C#CCCCCNC(*)=O] (423)
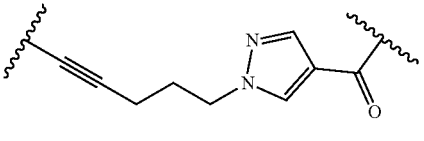 [SMILES: *C#CCCCn1cc(C(*)=O)cn1] (424)
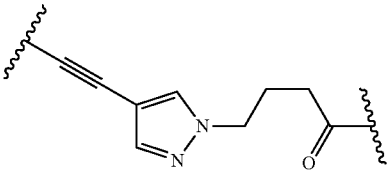 [SMILES: *C#Cc1cnn(CCCC(*)=O)c1] (425)
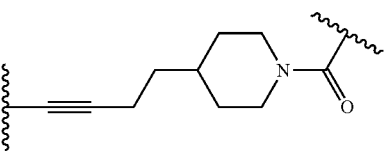 [SMILES: *C#CCCC1CCN(C(*)=O)CC1] (426)
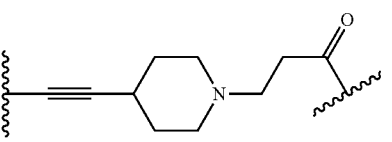 [SMILES: *C#CC1CCN(CCC(*)=O)CC1] (427)
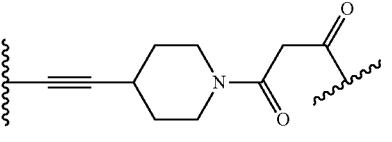 [SMILES: *C#CC1CCN(C(=O)CC(*)=O)CC1] (428)
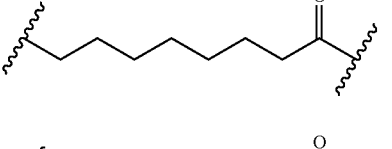 (429)
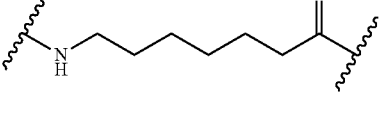 (430)
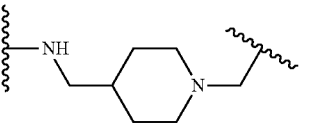 [SMILES: *CN1CCC(CN*)CC1] (431)

TABLE A-continued

Linkers (L')

(432)

(433)

(434)

(435)

(436)

(437)

(438)

(438)

(439)

(440)

TABLE A-continued

Linkers (L')

(441)

(442)

(443)

(444)

(445)

(446)

(447)

(448)

(449)

(450)

TABLE A-continued

Linkers (L')

(451) – (460) [chemical structures]

TABLE A-continued
Linkers (L')
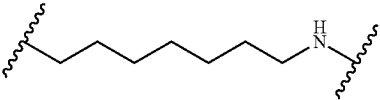 [SMILES: *CCCCCCCN*] (461)
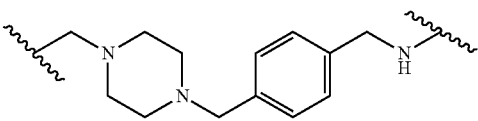 [SMILES: *CN1CCN(Cc2ccc(CN*)cc2)CC1] (462)
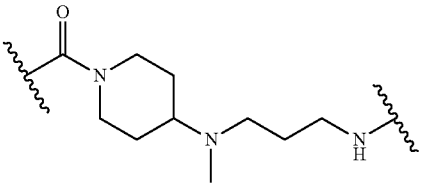 [SMILES: *NCCCN(C)C1CCN(C(*)=O)CC1] (463)
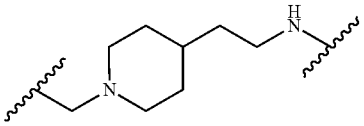 [SMILES: *CN1CCC(CCN*)CC1] (464)
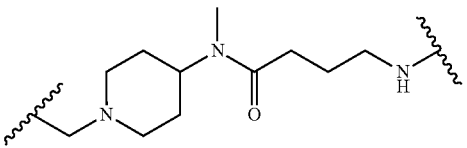 [SMILES: *CN1CCC(N(C)C(=O)CCCN*)CC1] (465)
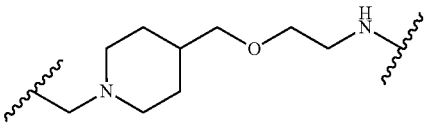 [SMILES: *CN1CCC(COCCN*)CC1] (466)
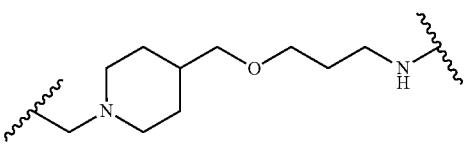 [SMILES: *CN1CCC(COCCCN*)CC1] (467)
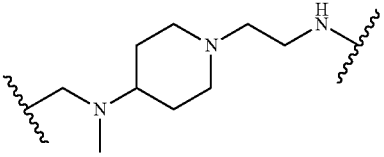 [SMILES: *CN(C)C1CCN(CCN*)CC1] (468)
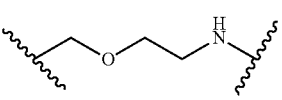 [SMILES: *COCCN*] (469)
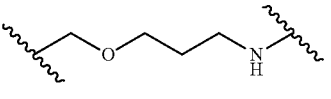 [SMILES: *COCCCN*] (470)
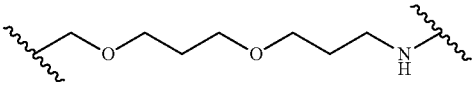 [SMILES: *COCCCOCCCN*] (471)

TABLE A-continued

Linkers (L')

(472)

(473)

(474)

(475)

(475)

(476)

(477)

(478)

(479)

TABLE A-continued
Linkers (L')
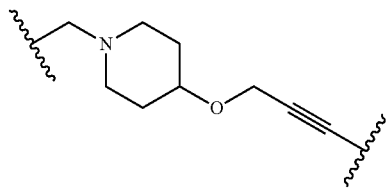 [SMILES: *C#CCOC1CCN(C*)CC1] (480)
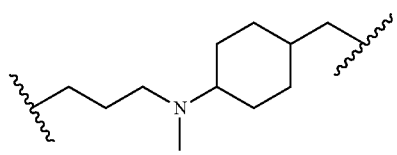 [SMILES: *CCCN(C)C1CCC(C*)CC1] (481)
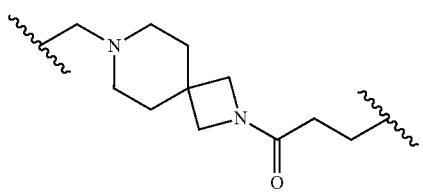 [SMILES: *CCC(=O)N1CC2(CCN(C*)CC2)C1] (482)
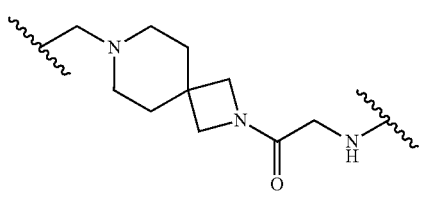 [SMILES: *CN1CCC2(CC1)CN(C(=O)CN*)C2] (483)
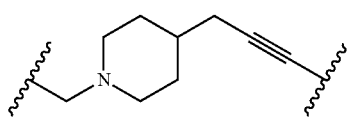 [SMILES: *C#CCC1CCN(C*)CC1] (484)
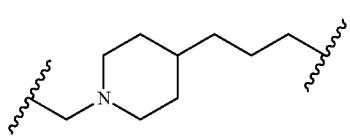 [SMILES: *CCCC1CCN(C*)CC1] (485)
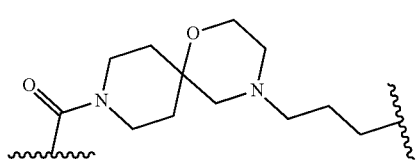 [SMILES: *CCCN1CCOC2(CCN(C(*)=O)CC2)C1] (486)
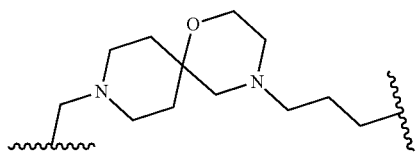 [SMILES: *CCCN1CCOC2(CCN(C*)CC2)C1] (487)
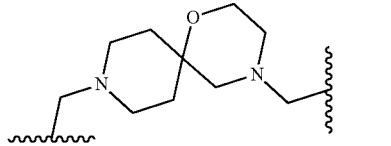 [SMILES: *CN1CCC2(CC1)CN(C*)CCO2] (488)

TABLE A-continued
| Linkers (L') | |
|---|---|
| 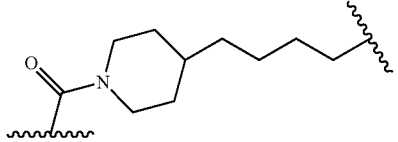 [SMILES: *CCCCC1CCN(C(*)=O)CC1] | (489) |
| 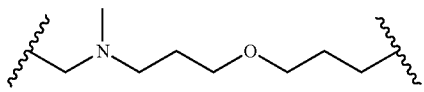 [SMILES: *CCCOCCCN(C)C*] | (490) |
| 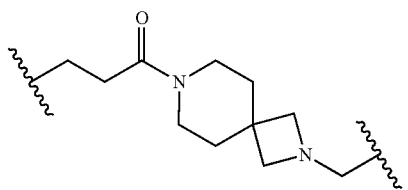 [SMILES: *CCC(=O)N1CCC2(CC1)CN(C*)C2] | (491) |
| 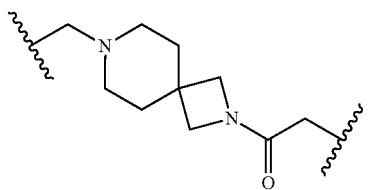 [SMILES: *CC(=O)N1CC2(CCN(C*)CC2)C1] | (492) |
| 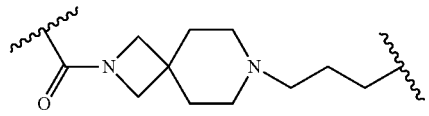 [SMILES: *CCCN1CCC2(CC1)CN(C(*)=O)C2] | (493) |
| 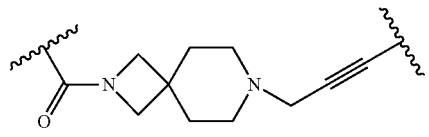 [SMILES: *C#CCN1CCC2(CC1)CN(C(*)=O)C2] | (494) |
| 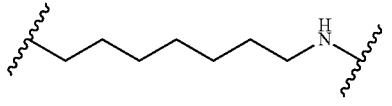 [SMILES: *CCCCCCCN*] | (495) |
| 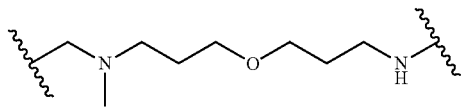 [SMILES: *CN(C)CCCOCCCN*] | (496) |
| 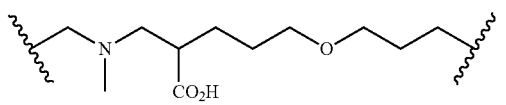 [SMILES: *CCCOCCCC(CN(C)C*)C(=O)O] | (497) |
| 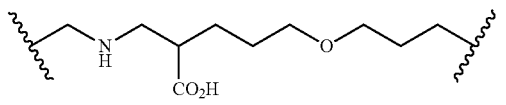 | (498) |
| 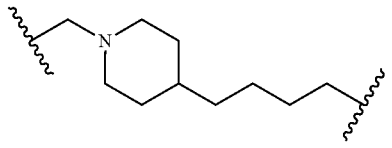 [SMILES: *CCCCC1CCN(C*)CC1] | (499) |

TABLE A-continued
Linkers (L')
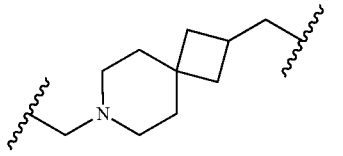 [SMILES: *CC1CC2(CCN(C*)CC2)C1]
(500)
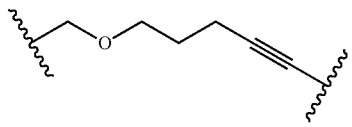 [SMILES: *C#CCCCOC*]
(501)
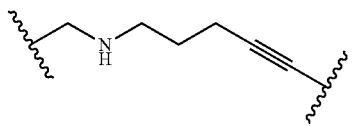 [SMILES: *C#CCCCNC*]
(502)
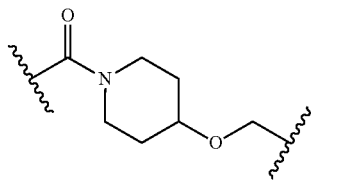 [SMILES: *COC1CCN(C(*)=O)CC1]
(503)
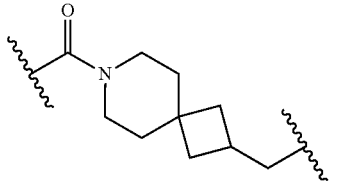 [SMILES: *CC1CC2(CCN(C(*)=O)CC2)C1]
(504)
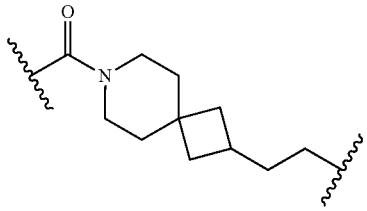 [SMILES: *CCC1CC2(CCN(C(*)=O)CC2)C1]
(505)
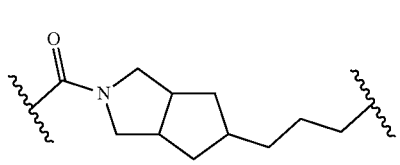 [SMILES: *CCCC1CC2CN(C(*)=O)CC2C1]
(506)
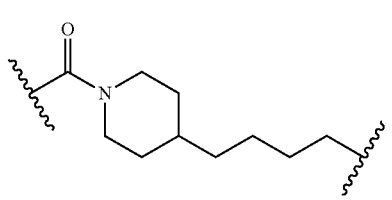 [SMILES: *CCCCC1CCN(C(*)=O)CC1]
(507)
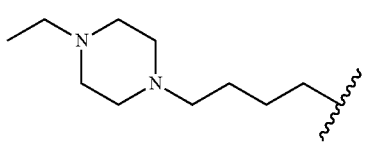 [SMILES: *CCCCN1CCN(CC)CC1]
(508)

TABLE A-continued

Linkers (L')

(509)

(510)

(511)

(512)

(513)

(514)

(515)

(516)

(517)

(518)

(519)

TABLE A-continued

Linkers (L')

(520)

(521)

(522)

(523)

(524)

(525)

(526)

(527)

(528)

(529)

(530)

TABLE A-continued
Linkers (L')
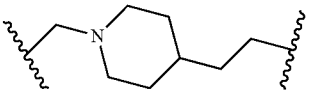 [SMILES: *CCC1CCN(C*)CC1] (531)
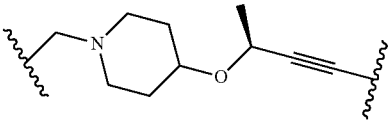 [SMILES: *C#C[C@H](C)OC1CCN(C*)CC1] (532)
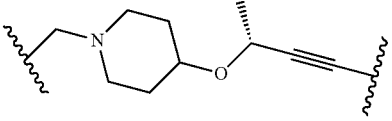 [SMILES: *C#C[C@@H](C)OC1CCN(C*)CC1] (533)
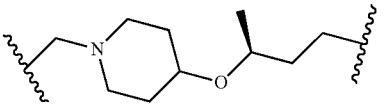 [SMILES: *CC[C@H](C)OC1CCN(C*)CC1] (534)
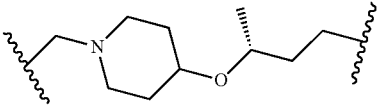 [SMILES: *CC[C@@H](C)OC1CCN(C*)CC1] (535)
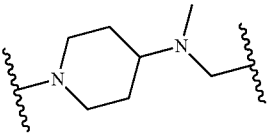 [SMILES: *CN(C)C1CCN(*)CC1] (536)
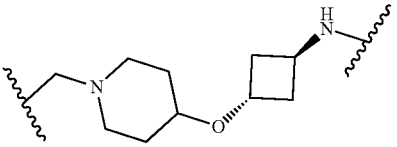 [SMILES: *CN1CCC(O[C@H]2C[C@H](N*)C2)CC1] (537)
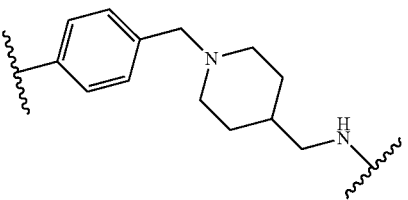 [SMILES: *NCC1CCN(Cc2ccc(*)cc2)CC1] (538)
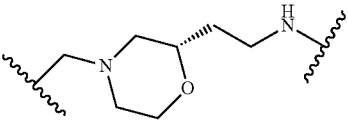 [SMILES: *CN1CCO[C@@H](CCN*)C1] (539)
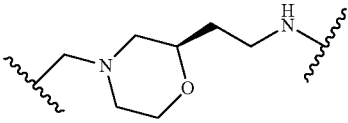 [SMILES: *CN1CCO[C@H](CCN*)C1] (540)
 (541)

TABLE A-continued

Linkers (L')

(542)

(543)

(544)

(545)

(546)

(547)

(548)

(549)

(550)

(551)

TABLE A-continued

Linkers (L')

| | |
|---|---|
| [structure] | (553) |
| [structure] | (554) |
| [structure] | (554) |
| [structure] | (555) |
| [structure] | (556) |
| [structure] | (557) |
| [structure] | (558) |
| [structure] | (559) |
| [structure] | (560) |
| [structure] | (561) |

TABLE A-continued
Linkers (L')
 (562)
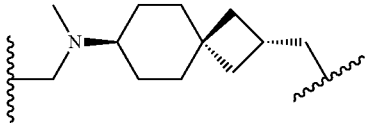 (563)
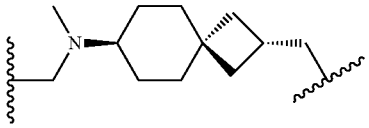 (564)
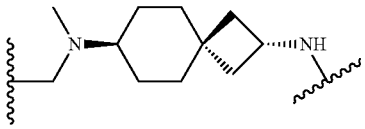 (565)
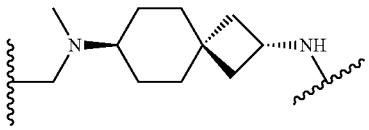 (566)
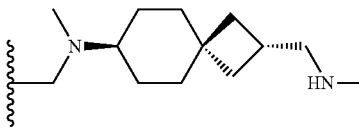 (567)
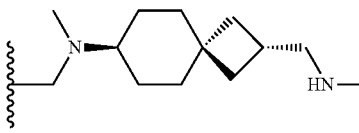 (568)
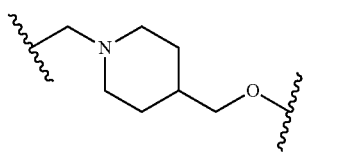 [SMILES: *CN1CCC(CO*)CC1] (569)
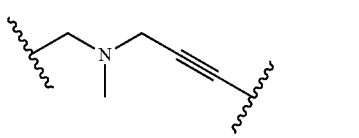 [SMILES: *C#CCN(C)C*] (570)
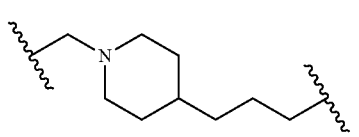 [SMILES: *CCCC1CCN(C*)CC1] (571)
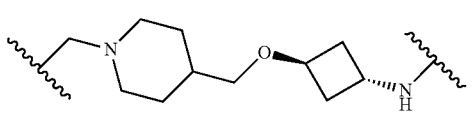 [SMILES: *CN1CCC(CO[C@H]2C[C@H](N*)C2)CC1] (572)

TABLE A-continued
Linkers (L')
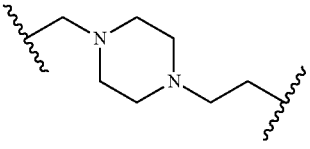 [SMILES: *CCN1CCN(C*)CC1] (573)
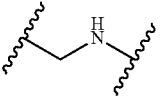 (574)
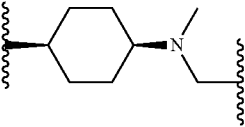 [SMILES: *CN(C)[C@H]1CC[C@@H](*)CC1] (575)
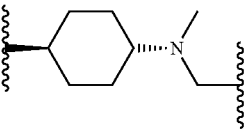 (576)
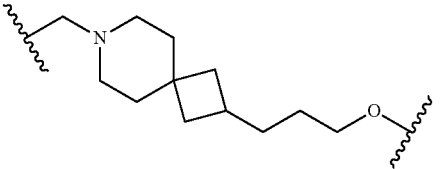 [SMILES: *CN1CCC2(CC1)CC(CCCO*)C2] (577)
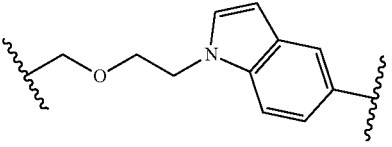 [SMILES: *COCCn1ccc2cc(*)ccc21] (578)
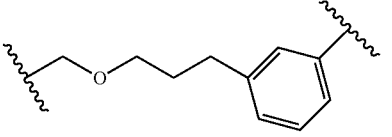 [SMILES: *COCCCc1cccc(*)c1] (579)
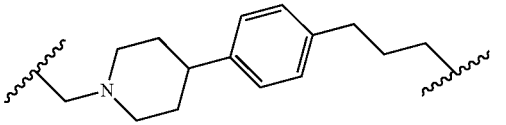 [SMILES: *CCCc1ccc(C2CCN(C*)CC2)cc1] (580)
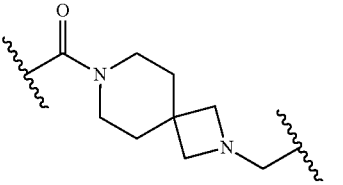 [SMILES: *CN1CC2(CCN(C(*)=O)CC2)C1] (581)
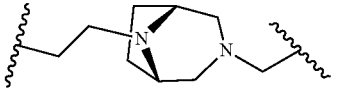 [SMILES: *CCN1[C@@H]2CC[C@H]1CN(C*)C2] (582)

TABLE A-continued

Linkers (L')

(583)
(584)
(585)
(586)
(587)
(588)
(589)
(590)
(591)
(592)

TABLE A-continued

Linkers (L')

TABLE A-continued
Linkers (L')
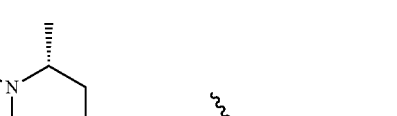 (603)
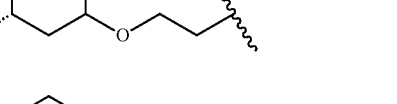 (604)
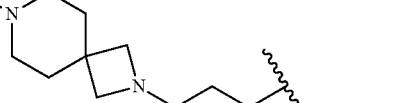 (605)
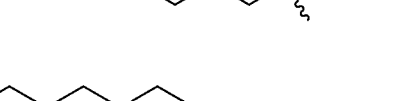 (606)
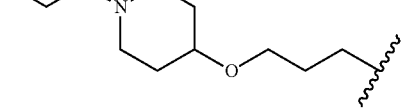 (607)
 (608)
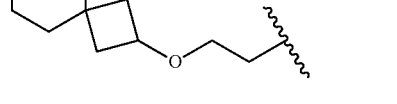 (609)
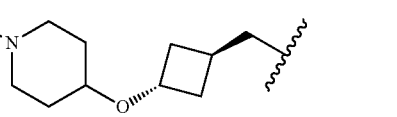 (610)
 (612)
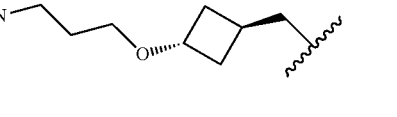 (612)
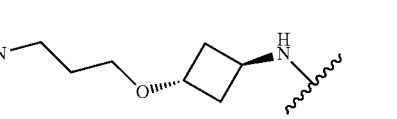 (613)

TABLE A-continued

Linkers (L')

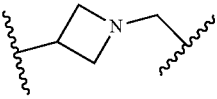 [SMILES: *CN1CC(*)C1]
(614)

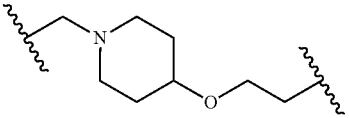 [SMILES: *CCOC1CCN(C*)CC1]
(615)

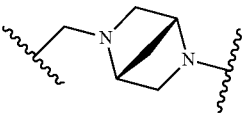 [SMILES: *CN1C[C@H]2C[C@@H]1CN2*]
(616)

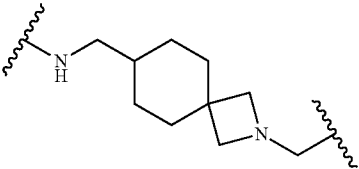 [SMILES: *CN1CC2(CCC(CN*)CC2)C1]
(617)

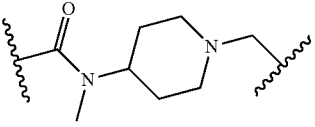 [SMILES: *CN1CCC(N(C)C(*)=O)CC1]
(618)

From the foregoing, it will be understood that, unless specified, as for example by "*", when a value for L' is asymmetric (e.g., —C(O)N(H)—, —C(O)N(H)—(CH$_2$)$_{3,4,6,8,9,10}$—N(H)—, —C(O)N(H)—(CH$_2$)$_{2,3,4,5,9,10,11}$—, —C(O)N(H)—(CH$_2$CH$_2$O)$_{2,3}$CH$_2$CH$_2$—N(H)—), the value can be oriented between KRASG12Di and Degron in either direction. Thus, for example, unless specified, —C(O)N(H)— can be oriented so as to produce a compound of either of the following structural formulas: [KRASG12Di]-C(O)N(H)-[Degron] or [KRASG12Di]-N(H)C(O)-[Degron]. Recitation of —C(O)N(H)—*, wherein * indicates the point of attachment of L' to Degron, on the other hand, can be used to describe a compound of the following structural formula: [KRASG12Di]-C(O)N(H)-[Degron].

Degrons

Degrons bring the ligase enzyme into close contact with the target protein, enabling the protein to be labelled with a ubiquitin tag and targeted for degradation by the ubiquitin-proteasome system "Degron," as used herein, refers to a moiety that is capable, under suitable conditions (e.g., in vitro, in vivo), of promoting degradation of a target protein, such as KRAS G12D, via the ubiquitin proteasome pathway (UPP). Typically, in a PROTAC, such as a compound of the disclosure, a degron is capable of binding an ubiquitin E3 ligase, thereby recruiting the ubiquitin E3 ligase into the vicinity of the PROTAC and, by extension, the target protein, which, under suitable conditions, binds to the KRAS G12Di in a compound of the disclosure. Formation of the ternary ligase-PROTAC-target protein complex leads to ubiquitination and degradation of the target protein, for example, by the 26S proteasome, a component of the UPP. Examples of degrons therefore include ubiquitin E3 ligase binding moieties, which bind to an ubiquitin E3 ligase. Examples of E3 ligases include cereblon (CRBN), von Hippel-Lindau (VHL), inhibitors of apoptosis proteins (IAP), mouse double minute 2 homolog (MDM2), DDB1- and CUL4-associated factor 16 (DCAF16) and ring finger protein 114 (RNF114). Other examples of degrons include hydrogen atoms and lysine mimetics, both of which are disclosed in International Publication No. WO 2021/127278, the entire content of which is incorporated herein.

In some aspects (e.g., of any of the foregoing embodiments, aspects or combinations of aspects), Degron is a ubiquitin E3 ligase binding moiety (e.g., a cereblon binding moiety). In further aspects, the ubiquitin E3 ligase is CRBN, VHL, IAP, MDM2, DCAF16 or RNF114. In yet further aspects, the ubiquitin E3 ligase is CRBN, as when the ubiquitin E3 ligase binding moiety is a cereblon binding moiety. Thus, in some aspects, Degron is a cereblon binding moiety.

Ubiquitin E3 ligase binding moieties, including cereblon binding moieties, are disclosed in International Publication No. WO 2021/127278. See, for example, Table A therein. In some aspects (e.g., of any of the foregoing embodiments, aspects or combinations of aspects), Degron is a ubiquitin E3 ligase binding moiety (e.g., cereblon binding moiety) disclosed in WO 2021/127278.

Cereblon binding moieties are also disclosed in U.S. Pat. No. 10,849,982; and U.S. Patent Application Publication Nos. US 2020/0140456 and US 2020/0377469. In some aspects (e.g., of any of the foregoing embodiments, aspects or combinations of aspects), Degron is a cereblon binding moiety disclosed in U.S. Pat. No. 10,849,982, or U.S. Patent Application Publication No. US 2020/0140456 or US 2020/0377469.

In some aspects (e.g., of any of the foregoing embodiments, aspects or combinations of aspects), Degron is
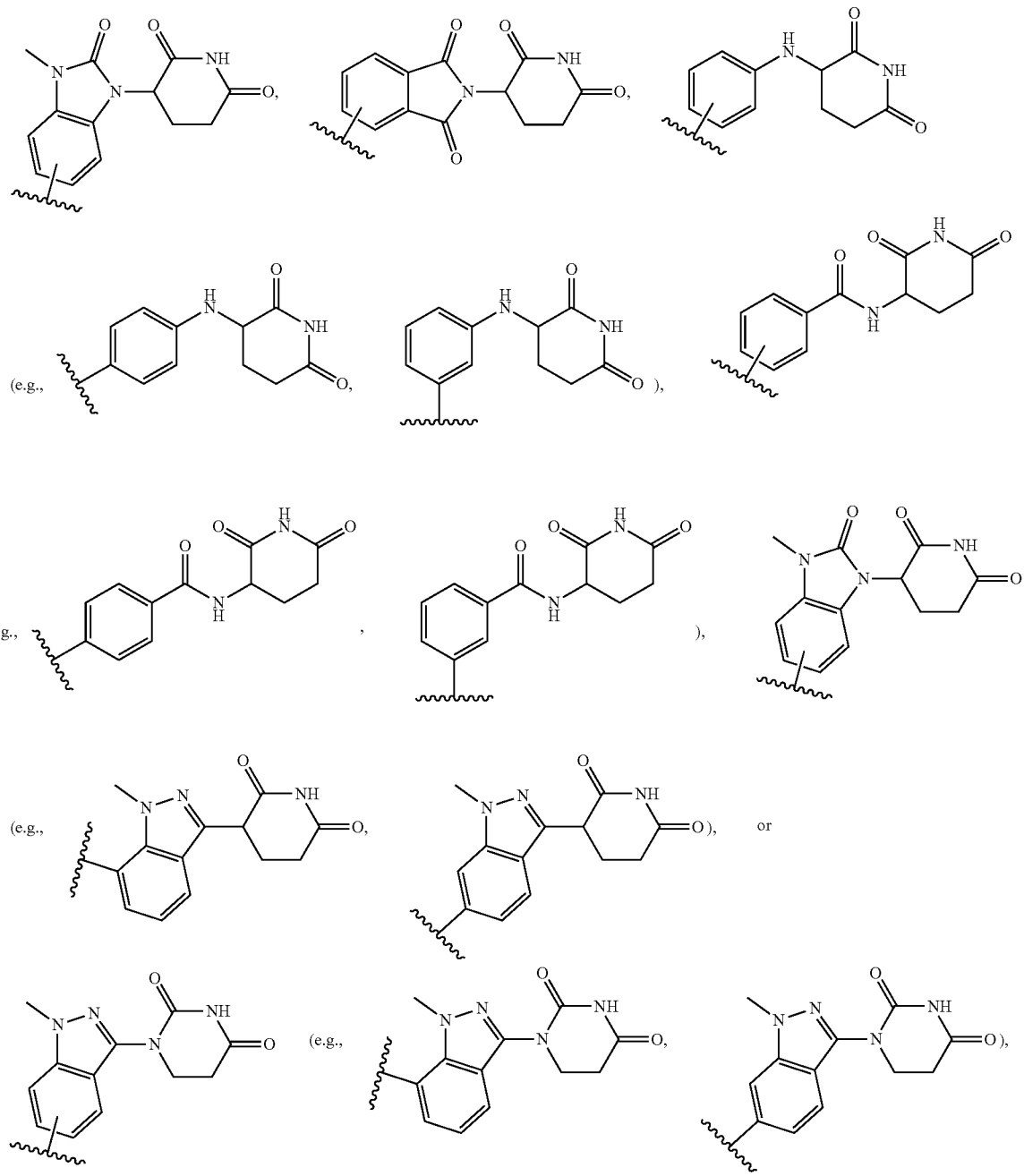
In some aspects (e.g., of any of the foregoing embodiments, aspects or combinations of aspects), Degron is
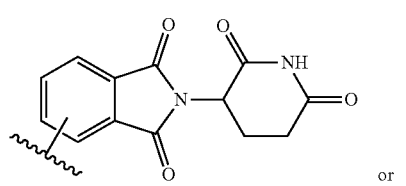
or
-continued
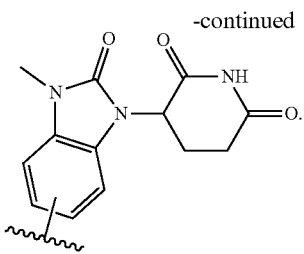

In further aspects, Degron is
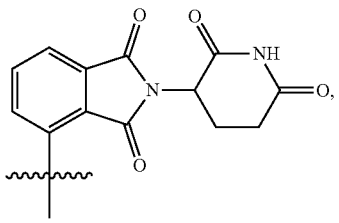
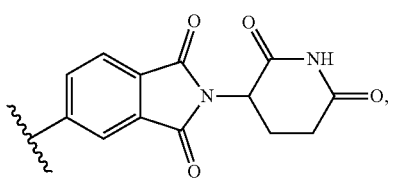
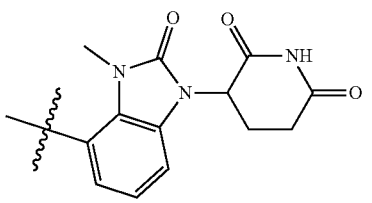
or
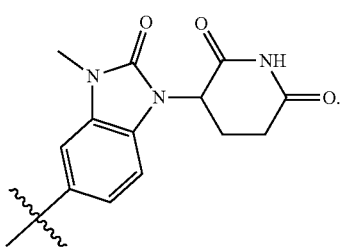
In some aspects (e.g., of any of the foregoing embodiments, aspects or combination of aspects), Degron is
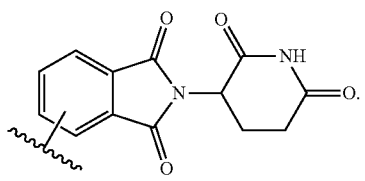
In further aspects, Degron is
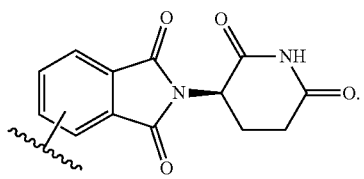
In yet further aspects, Degron is
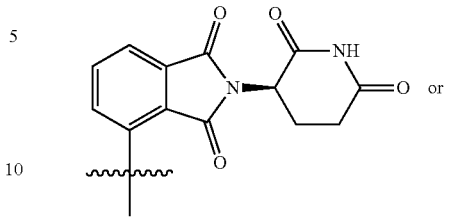 or
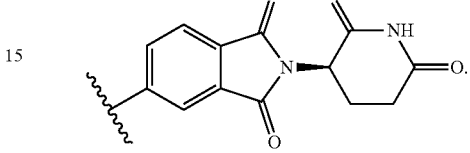
In other aspects, Degron is
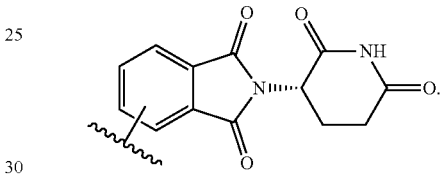
In further aspects, Degron is
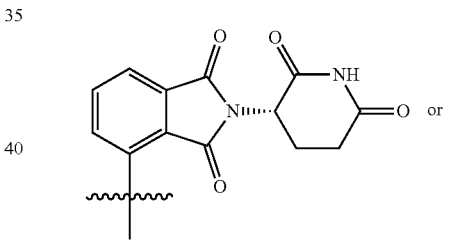 or
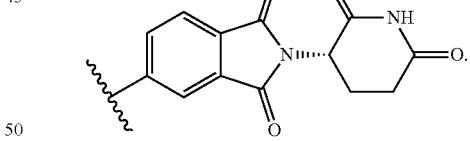
In some aspects (e.g., of any of the foregoing embodiments, aspects or combination of aspects), Degron is
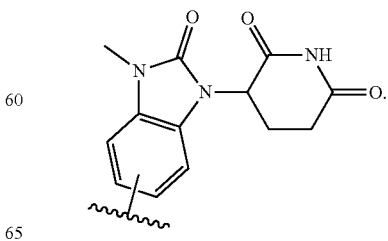

In further aspects, Degron is

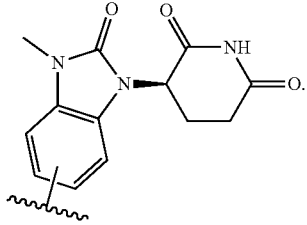

In yet further aspects, Degron is

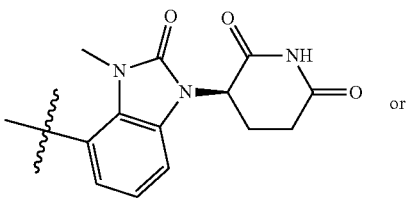

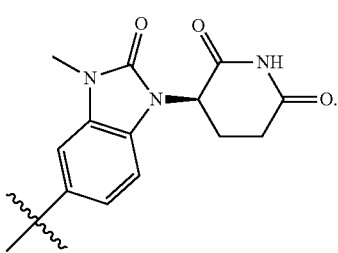

In other aspects, Degron is

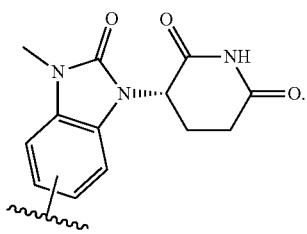

In further aspects, Degron is

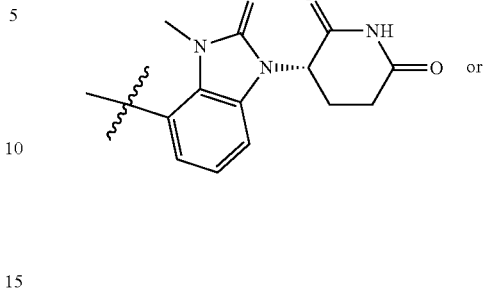 or

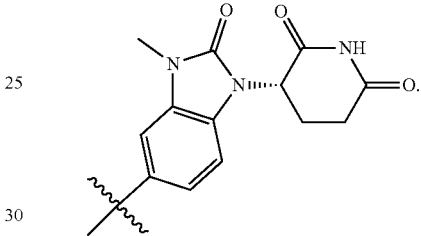

In any of the Degron structures containing a benzene ring (e.g., any of the foregoing Degron structures), it will be appreciated that one or more hydrogen atoms of the benzene ring may be substituted, as, for example, in the following structural formula:

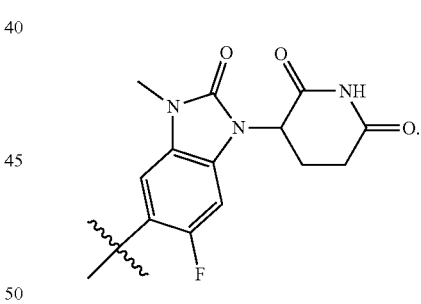

Where indicated, such substitutions are encompassed by this disclosure. Thus, in some aspects, one or more hydrogen atoms (e.g., 1-4; 1-3; 1 or 2) on the benzene ring of Degron is optionally replaced with a fluorine atom. In some aspects, one hydrogen atom on the benzene ring of Degron is replaced with a fluorine atom. In some aspects, two hydrogen atoms on the benzene ring of Degron are replaced with a fluorine atom. In some aspects, three fluorine atoms on the benzene ring of Degron are replaced with a fluorine atom. In some aspects, the benzene ring of Degron is perfluorinated. In some aspects, the benzene ring of Degron is unsubstituted.

Other specific examples of ubiquitin E3 ligase binding moieties include those depicted in Table B. In some aspects, Degron is a ubiquitin E3 ligase binding moiety in Table B.

TABLE B
Ubiquitin E3 ligase binding moieties
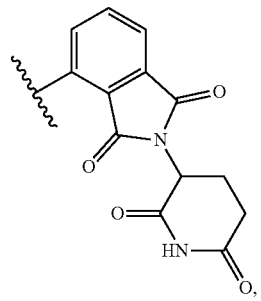 [SMILES: *c1cccc2c1C(=O)N(C1CCC(=O)NC1=O)C2=O]
(a)
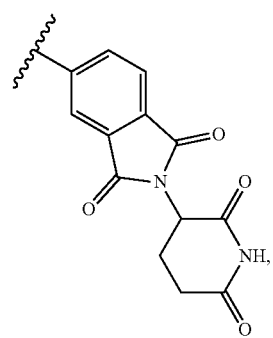 [SMILES: *c1ccc2c(c1)C(=O)N(C1CCC(=O)NC1=O)C2=O]
(b)
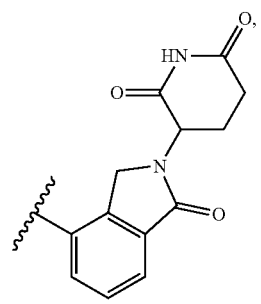 [SMILES: *c1cccc2c1CN(C1CCC(=O)NC1=O)C2=O]
(c)
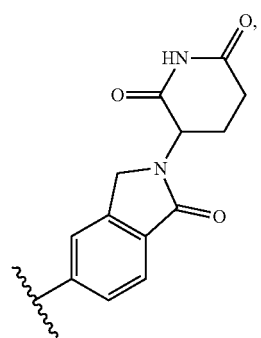 [SMILES: *c1ccc2c(c1)CN(C1CCC(=O)NC1=O)C2=O]
(d)

TABLE B-continued
Ubiquitin E3 ligase binding moieties
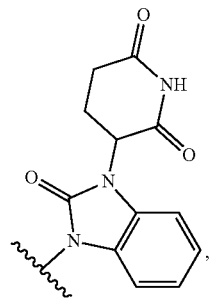 [SMILES: *n1c(=O)n(C2CCC(=O)NC2=O)c2ccccc21] (e)
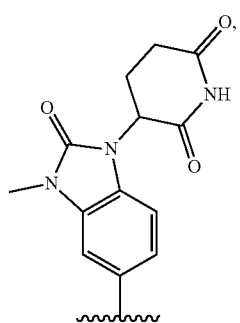 [SMILES: *c1ccc2c(c1)n(C)c(=O)n2C1CCC(=O)NC1=O] (f)
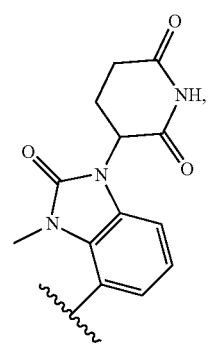 [SMILES: *c1cccc2c1n(C)c(=O)n2C1CCC(=O)NC1=O] (g)
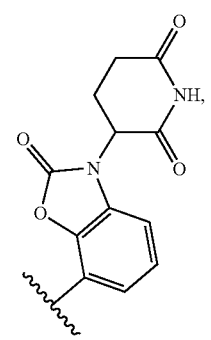 [SMILES: *c1cccc2c1oc(=O)n2C1CCC(=O)NC1=O] (h)

TABLE B-continued
Ubiquitin E3 ligase binding moieties
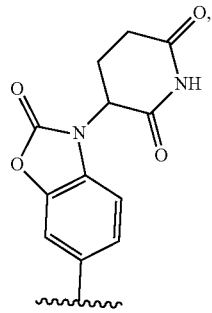 [SMILES: *c1ccc2c(c1)oc(=O)n2C1CCC(=O)NC1=O]
(i)
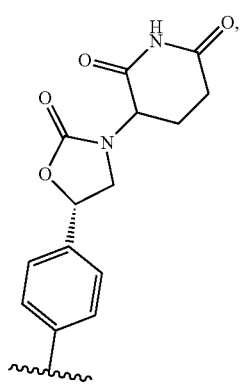 [SMILES: *c1ccc([C@H]2CN(C3CCC(=O)NC3=O)C(=O)O2)cc1]
(j)
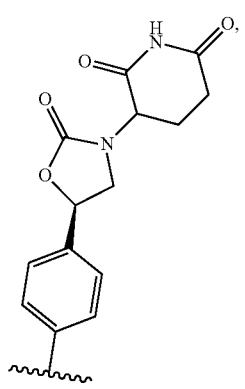 [SMILES: *c1ccc([C@@H]2CN(C3CCC(=O)NC3=O)C(=O)O2)cc1]
(k)
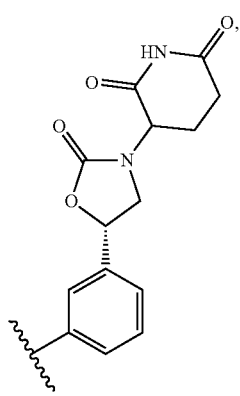 [SMILES: *c1cccc([C@H]2CN(C3CCC(=O)NC3=O)C(=O)O2)c1]
(l)

TABLE B-continued
Ubiquitin E3 ligase binding moieties
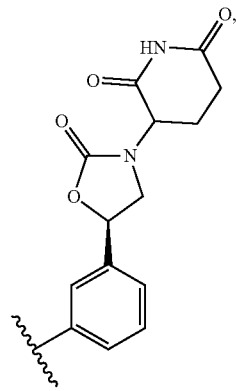 [SMILES: *c1cccc([C@@H]2CN(C3CCC(=O)NC3=O)C(=O)O2)c1]
(m)
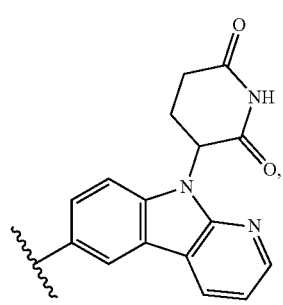 [SMILES: *c1ccc2c(c1)c1cccnc1n2C1CCC(=O)NC1=O]
(n)
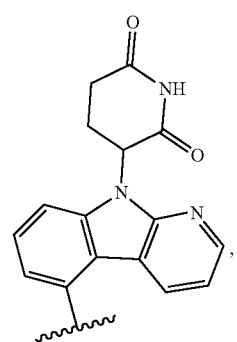 [SMILES: *c1cccc2c1c1cccnc1n2C1CCC(=O)NC1=O]
(o)
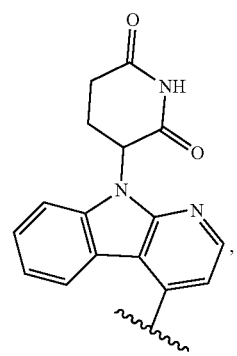 [SMILES: *c1ccnc2c1c1ccccc1n2C1CCC(=O)NC1=O]
(p)

TABLE B-continued
Ubiquitin E3 ligase binding moieties
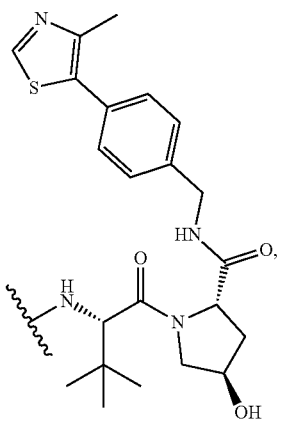 [SMILES: *N[C@H](C(=O)N1C[C@H](O)C[C@H]1C(=O)NCc1ccc(-c2scnc2C)cc1)C(C)(C)C]
(q)
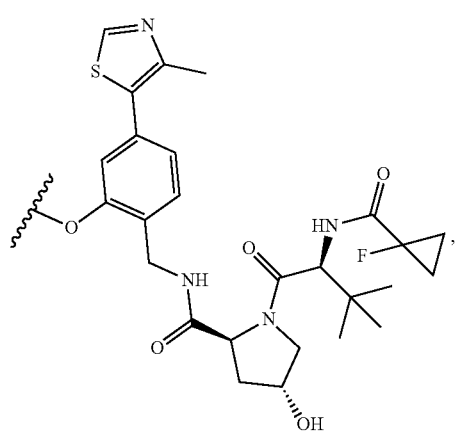 [SMILES: *Oc1cc(-c2scnc2C)ccc1CNC(=O)[C@@H]1C[C@@H](O)CN1C(=O)[C@@H](NC(=O)C1(F)CC1)C(C)(C)C]
(n)
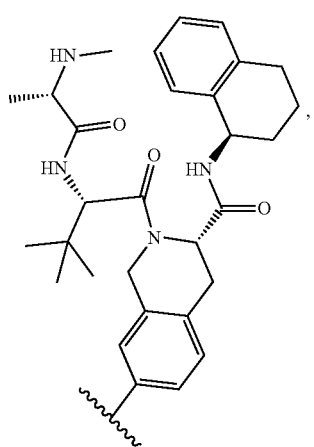 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
(o)

TABLE B-continued
Ubiquitin E3 ligase binding moieties
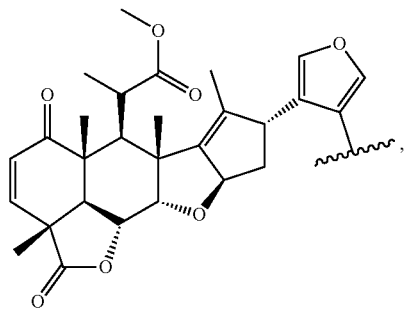 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45]
(p)
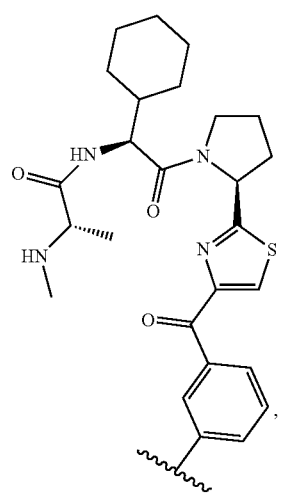 [SMILES: *c1cccc(C(=O)c2csc([C@@H]3CCCN3C(=O)[C@@H](NC(=O)[C@H](C)NC)C3CCCCC3)n2)c1]
(q)
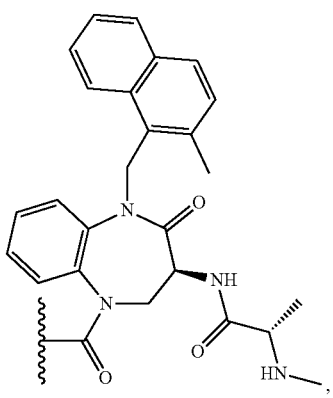 [SMILES: *C(=O)N1C[C@H](NC(=O)[C@H](C)NC)C(=O)N(Cc2c(C)ccc3ccccc23)c2ccccc21]
(r)

TABLE B-continued
Ubiquitin E3 ligase binding moieties
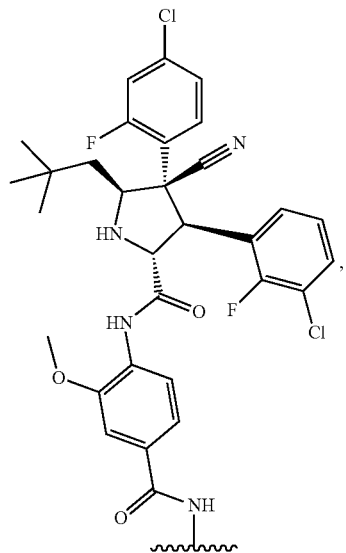 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
(s)
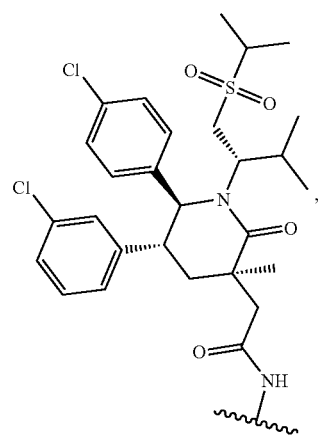 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O]
(t)
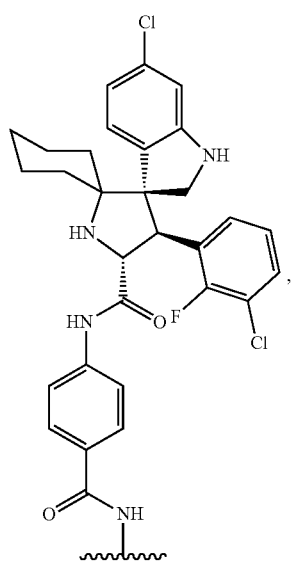 [SMILES: *NC(=O)c1ccc(NC(=O)[C@@H]2NC3(CCCCC3)[C@@]3(CNc4cc(Cl)ccc43)[C@H]2c2cccc(Cl)c2F)cc1]
(u)

TABLE B-continued
Ubiquitin E3 ligase binding moieties
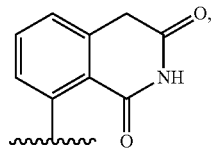 [SMILES: *c1cccc2c1C(=O)NC(=O)C2] (v)
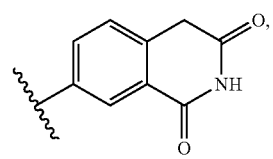 [SMILES: *c1ccc2c(c1)C(=O)NC(=O)C2] (w)
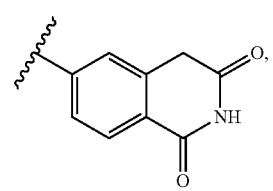 [SMILES: *c1ccc2c(c1)CC(=O)NC2=O] (x)
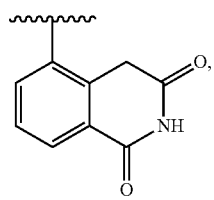 [SMILES: *c1cccc2c1CC(=O)NC2=O] (y)
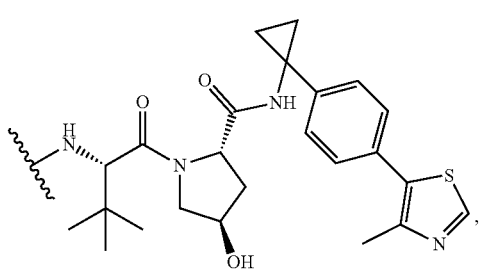 [SMILES: *N[C@H](C(=O)N1C[C@H](O)C[C@H]1C(=O)NC1(c2ccc(-c3scnc3C)cc2)CC1)C(C)(C)C] (z)
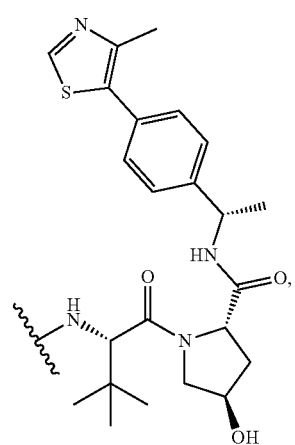 [SMILES: *N[C@H](C(=O)N1C[C@H](O)C[C@H]1C(=O)N[C@@H](C)c1ccc(-c2scnc2C)cc1)C(C)(C)C] (aa)

TABLE B-continued
Ubiquitin E3 ligase binding moieties
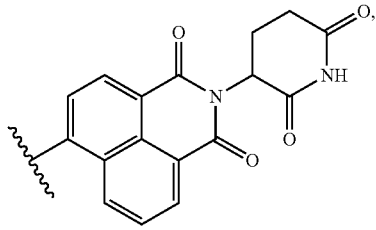 [SMILES: *c1ccc2c3c(cccc13)C(=O)N(C1CCC(=O)NC1=O)C2=O] (bb)
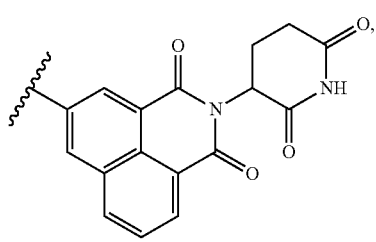 [SMILES: *c1cc2c3c(cccc3c1)C(=O)N(C1CCC(=O)NC1=O)C2=O] (cc)
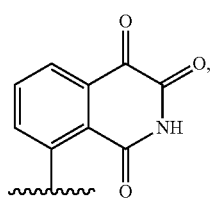 [SMILES: *c1cccc2c1C(=O)NC(=O)C2=O] (dd)
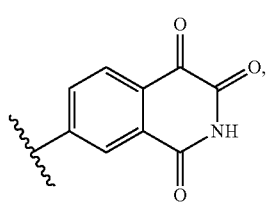 [SMILES: *c1ccc2c(c1)C(=O)NC(=O)C2=O] (ee)
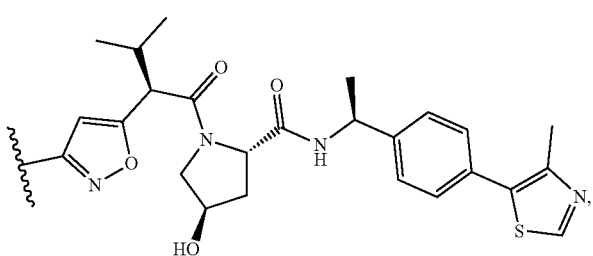 [SMILES: *c1cc([C@H](C(=O)N2C[C@H](O)C[C@H]2C(=O)N[C@@H](C)c2ccc(-c3scnc3C)cc2)C(C)C)on1] (ff)
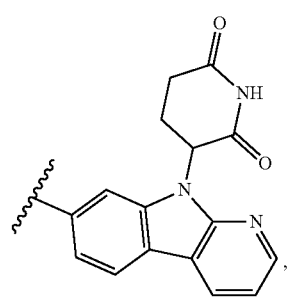 [SMILES: *c1ccc2c3cccnc3n(C3CCC(=O)NC3=O)c2c1] (gg)

TABLE B-continued
Ubiquitin E3 ligase binding moieties
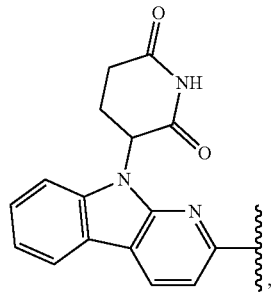 [SMILES: *c1ccc2c3ccccc3n(C3CCC(=O)NC3=O)c2n1]
(hh)
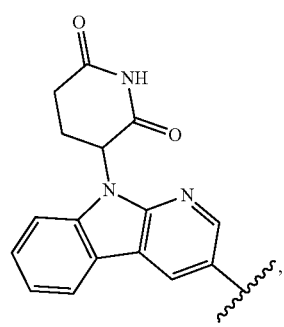 [SMILES: *c1cnc2c(c1)c1ccccc1n2C1CCC(=O)NC1=O]
(ii)
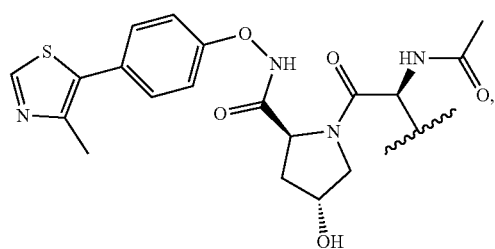 [SMILES: *[C@H](NC(C)=O)C(=O)N1C[C@H](O)C[C@H]1C(=O)NOc1ccc(-c2scnc2C)cc1]
(jj)
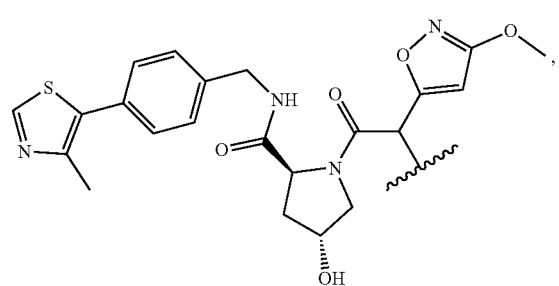 [SMILES: *C(C(=O)N1C[C@H](O)C[C@H]1C(=O)NCc1ccc(-c2scnc2C)cc1)c1cc(OC)no1]
(kk)
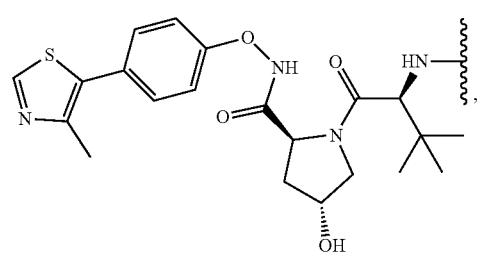 [SMILES: *N[C@H](C(=O)N1C[C@H](O)C[C@H]1C(=O)NOc1ccc(-c2scnc2C)cc1)C(C)(C)C]
(ll)

TABLE B-continued
Ubiquitin E3 ligase binding moieties
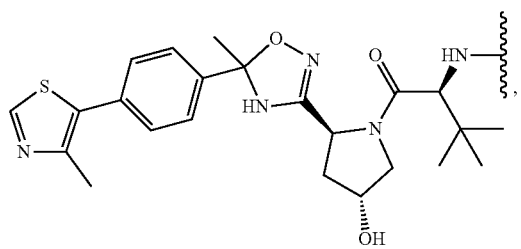 [SMILES: *N[C@H](C(=O)N1C[C@H](O)C[C@H]1C1=NOC(C)(c2ccc(-c3scnc3C)cc2)N1)C(C)(C)C]
(mm)
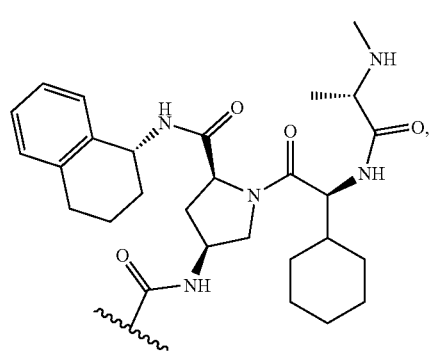 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]
(nn)
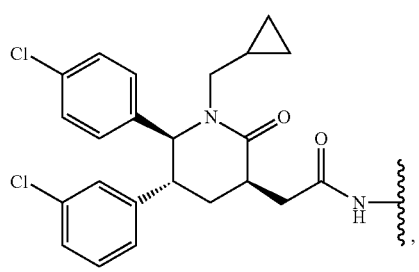 [SMILES: *NC(=O)C[C@H]1C[C@H](c2cccc(Cl)c2)[C@@H](c2ccc(Cl)cc2)N(CC2CC2)C1=O]
(oo)
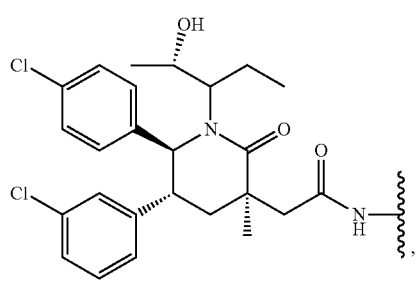 [SMILES: *NC(=O)C[C@@]1(C)C[C@H](c2cccc(Cl)c2)[C@@H](c2ccc(Cl)cc2)N(C(CC)[C@H](C)O)C1=O]
(pp)
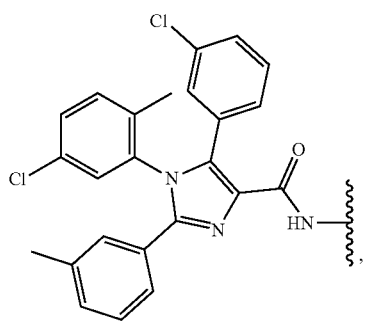 [SMILES: *NC(=O)c1nc(-c2cccc(C)c2)n(-c2cc(Cl)ccc2C)c1-c1cccc(Cl)c1]
(qq)

TABLE B-continued
Ubiquitin E3 ligase binding moieties
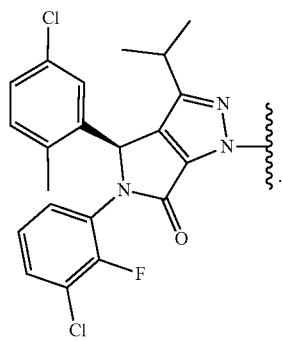 [SMILES: *n1nc(C(C)C)c2c1C(=O)N(c1cccc(Cl)c1F)[C@H]2c1cc(Cl)ccc1C]
(rr)
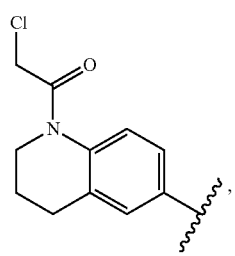 [SMILES: *c1ccc2c(c1)CCCN2C(=O)CCl]
(ss)
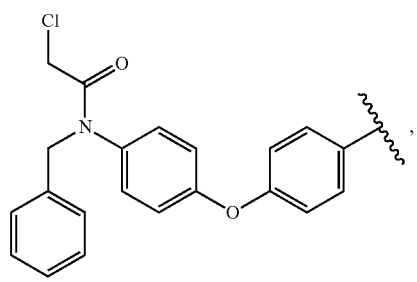 [SMILES: *c1ccc(Oc2ccc(N(Cc3ccccc3)C(=O)CCl)cc2)cc1]
(tt)
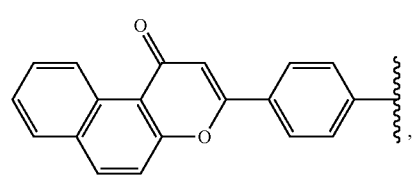 [SMILES: *c1ccc(-c2cc(=O)c3c(ccc4ccccc43)o2)cc1]
(uu)
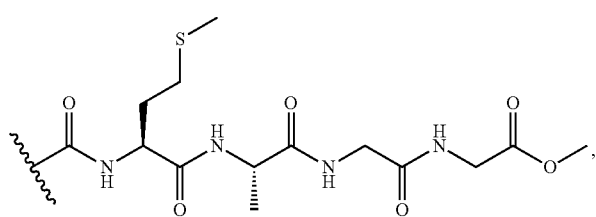 [SMILES: *C(=O)N[C@@H](CCSC)C(=O)N[C@@H](C)C(=O)NCC(=O)NCC(=O)OC]
(vv)
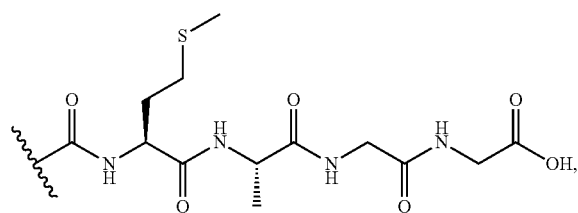 [SMILES: *C(=O)N[C@@H](CCSC)C(=O)N[C@@H](C)C(=O)NCC(=O)NCC(=O)O]
(ww)

TABLE B-continued
Ubiquitin E3 ligase binding moieties
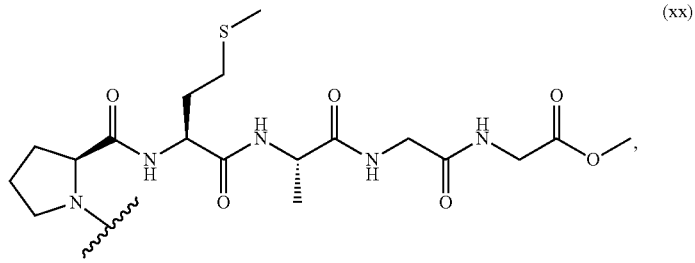
(xx)
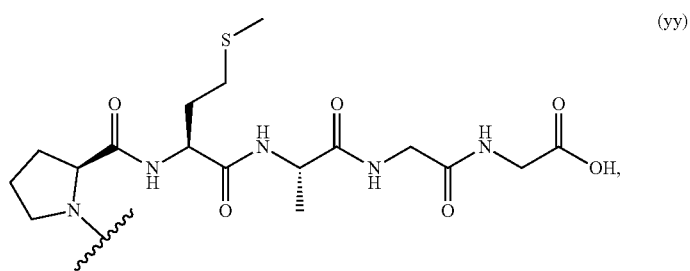
(yy)
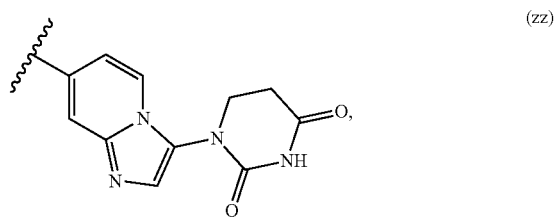
(zz)
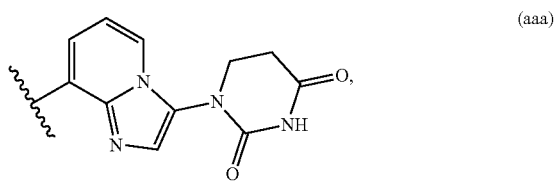
(aaa)
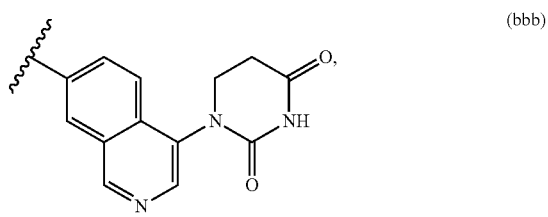
(bbb)
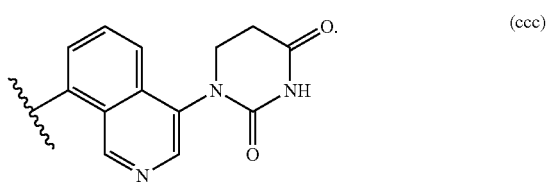
(ccc)

In some aspects (e.g., of any of the foregoing embodiments, aspects or combination of aspects), Degron is

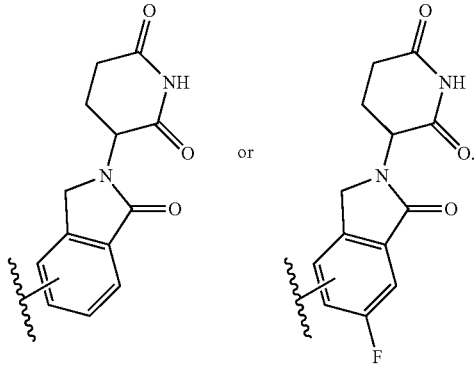

In some aspects (e.g., of any of the foregoing embodiments, aspects or combination of aspects), Degron is not

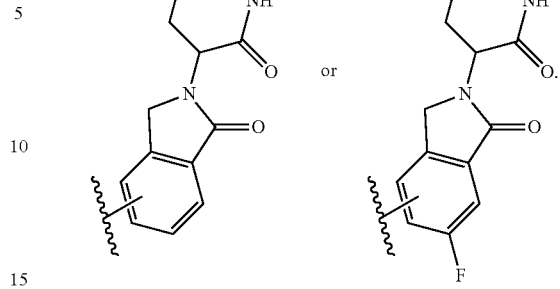

Specific examples of compounds of the disclosure are listed in Table 1. One embodiment provides a compound of Table 1, or a pharmaceutically acceptable salt thereof.

In some aspects (e.g., of any of the foregoing embodiments, aspects or combination of aspects), the compound is not:

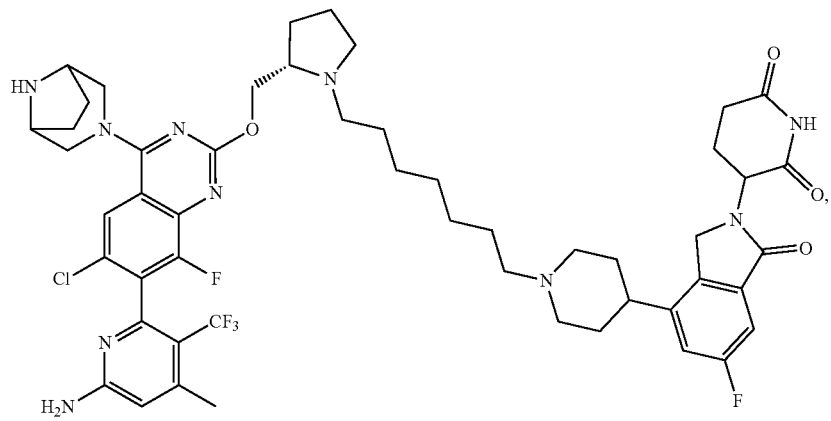

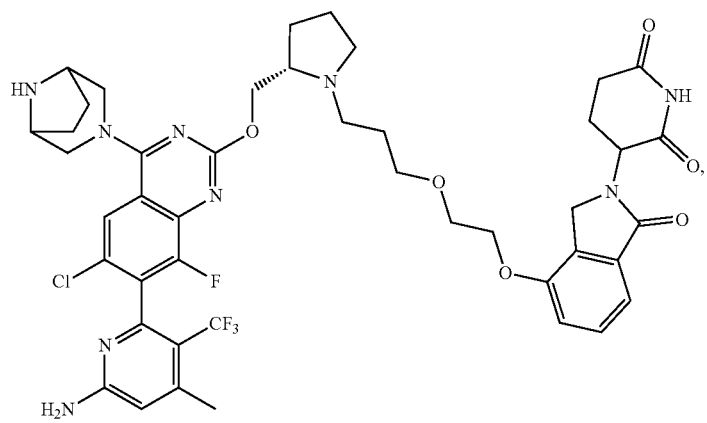

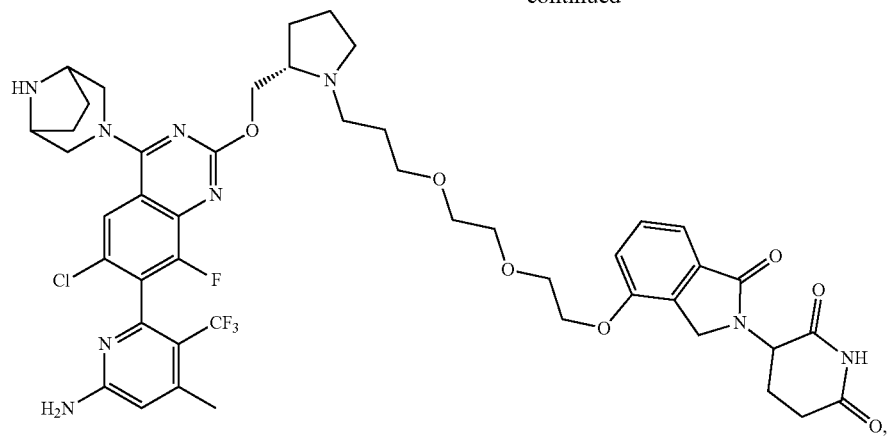
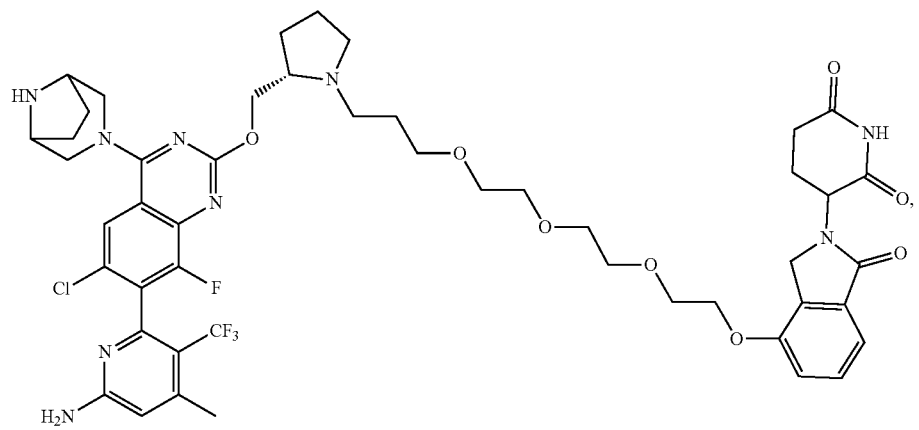
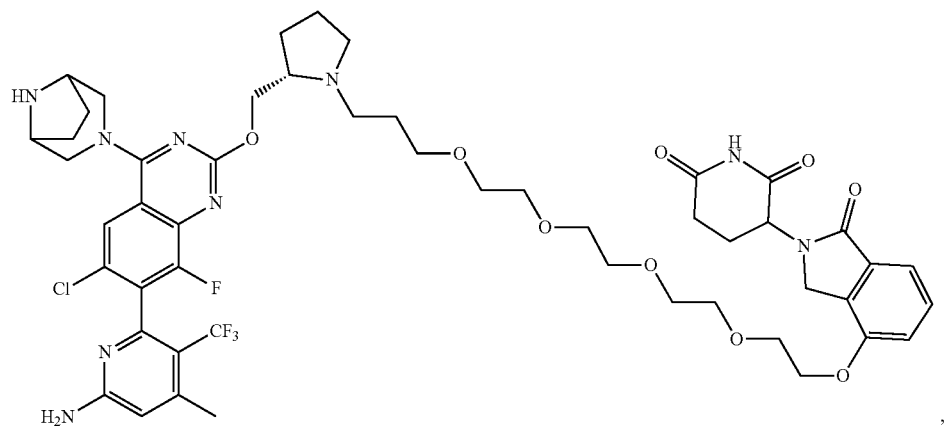
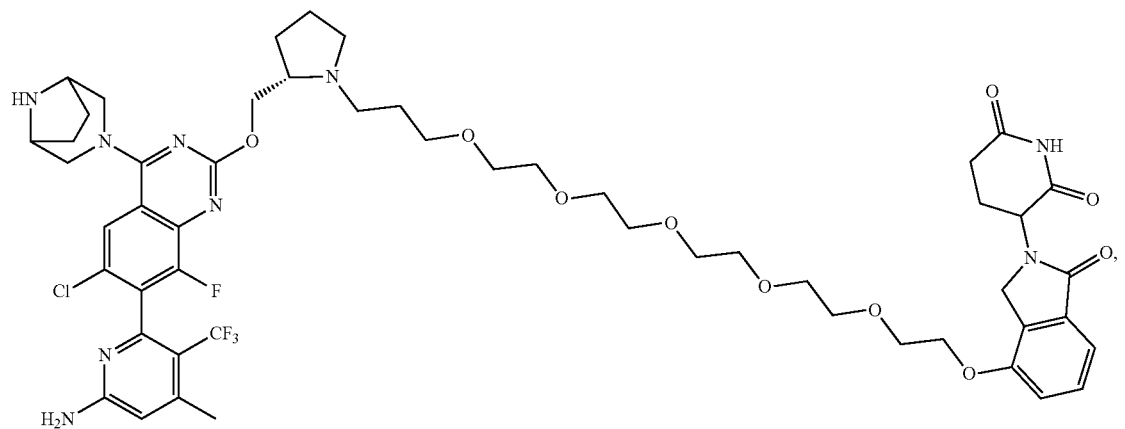

-continued
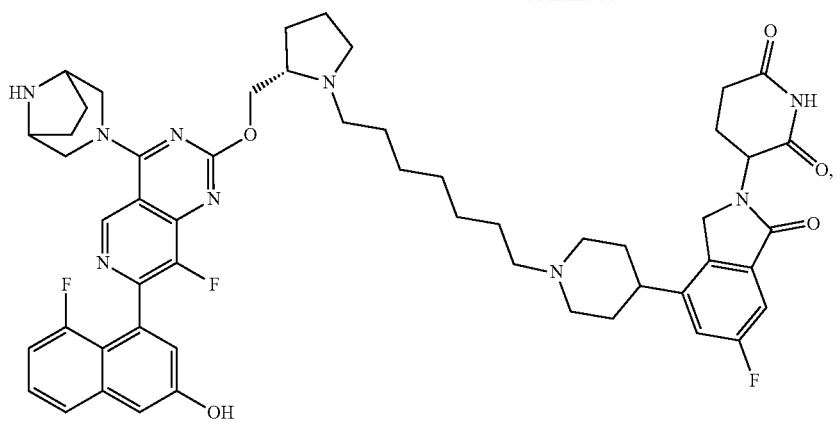
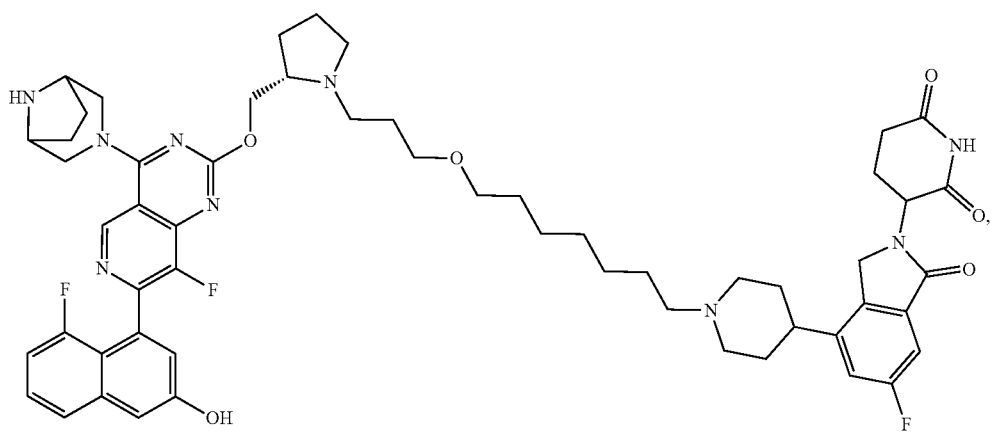
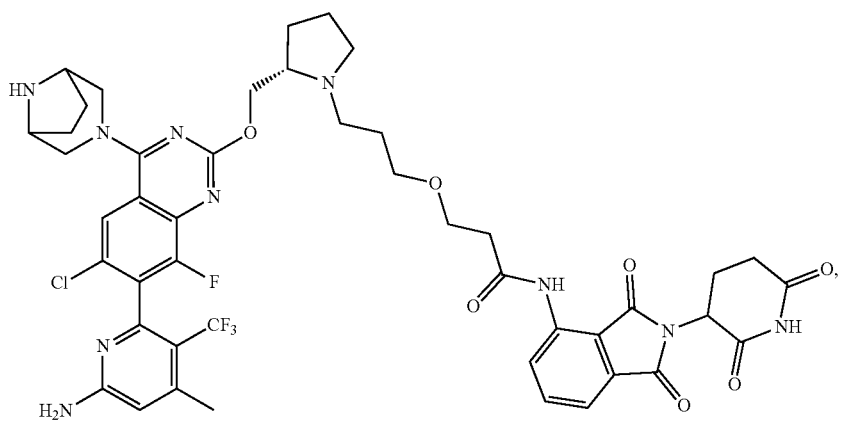
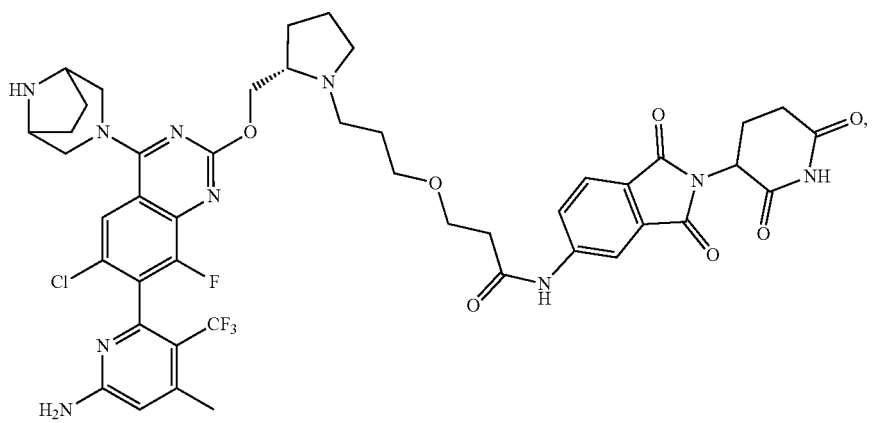

721 722
-continued
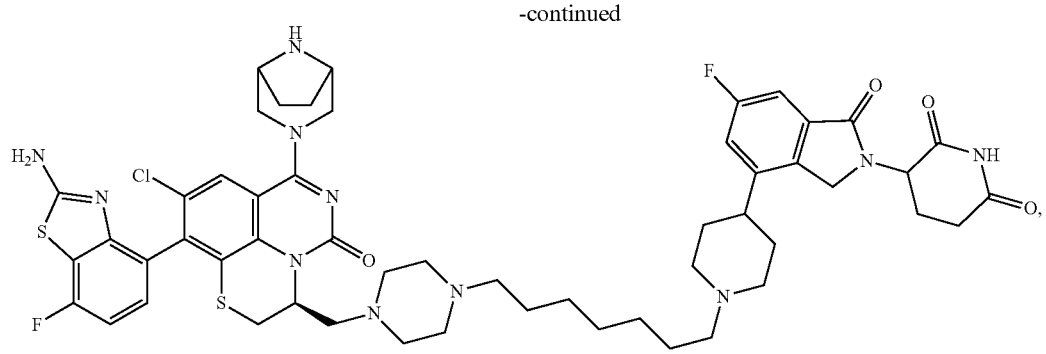
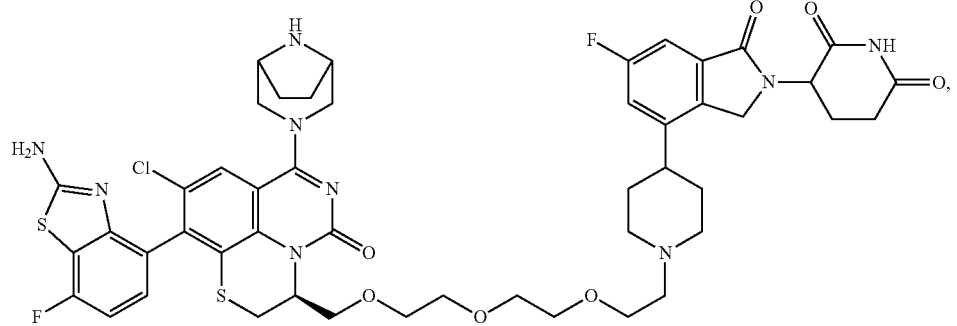
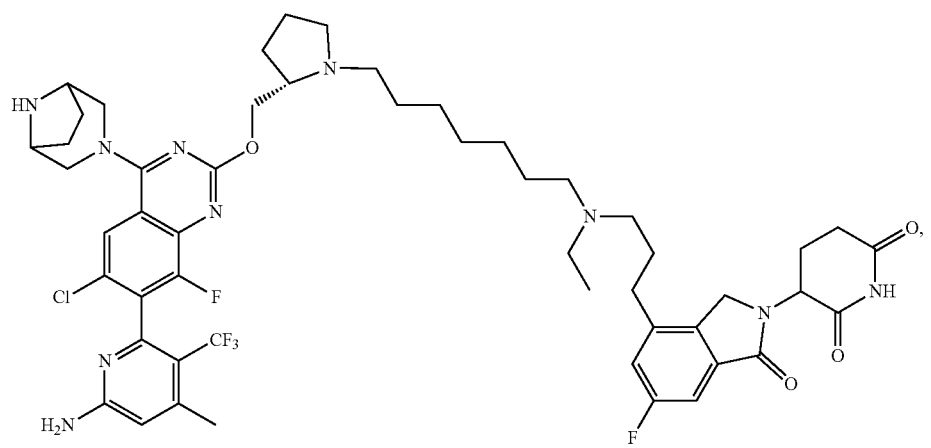
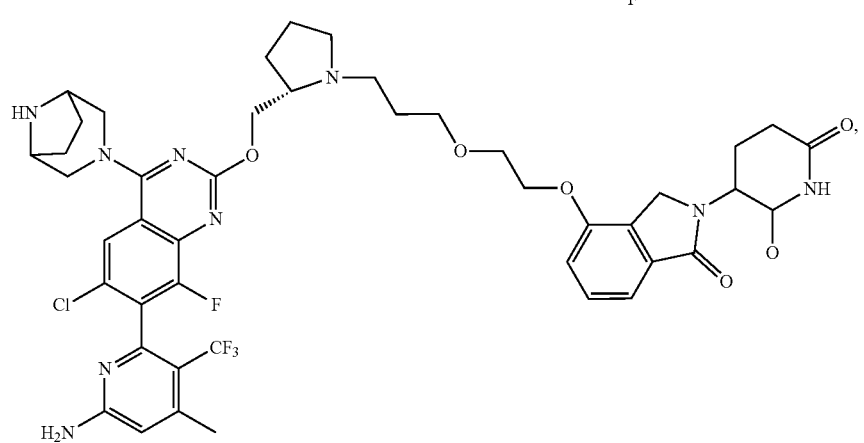

723
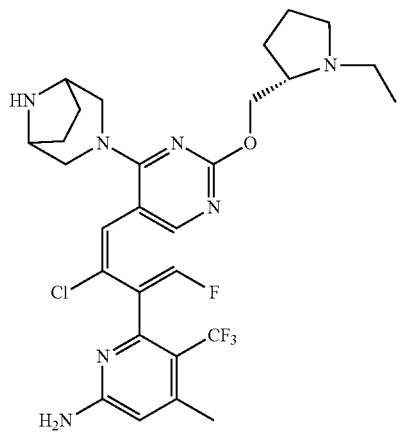
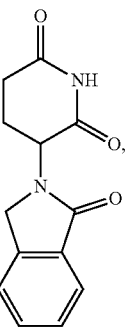
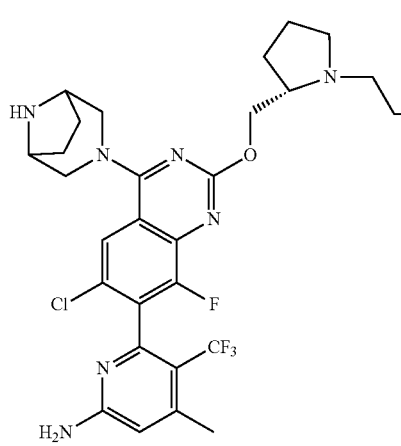
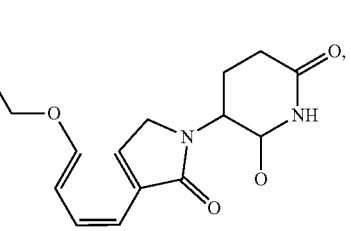
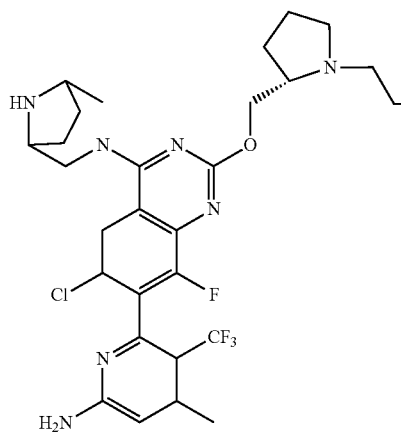
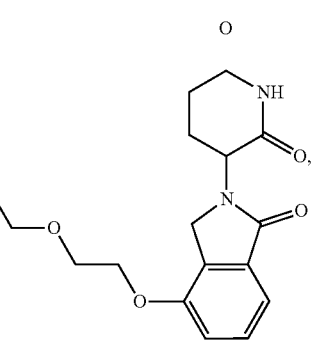
724
-continued 725
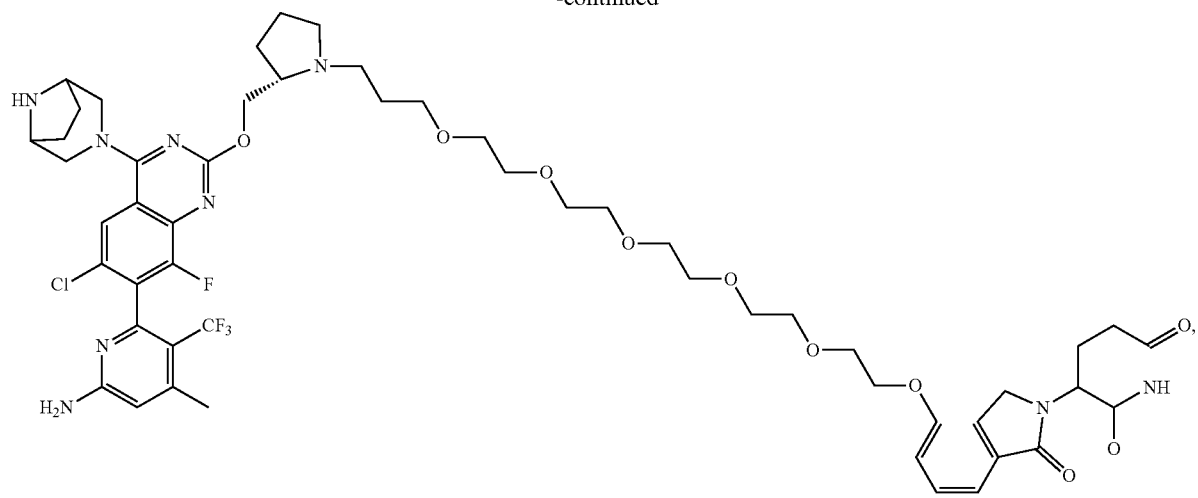
726
-continued
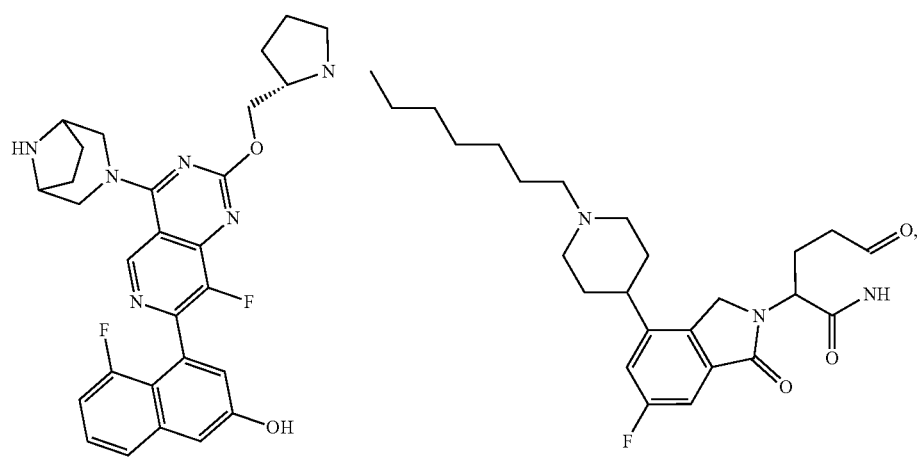
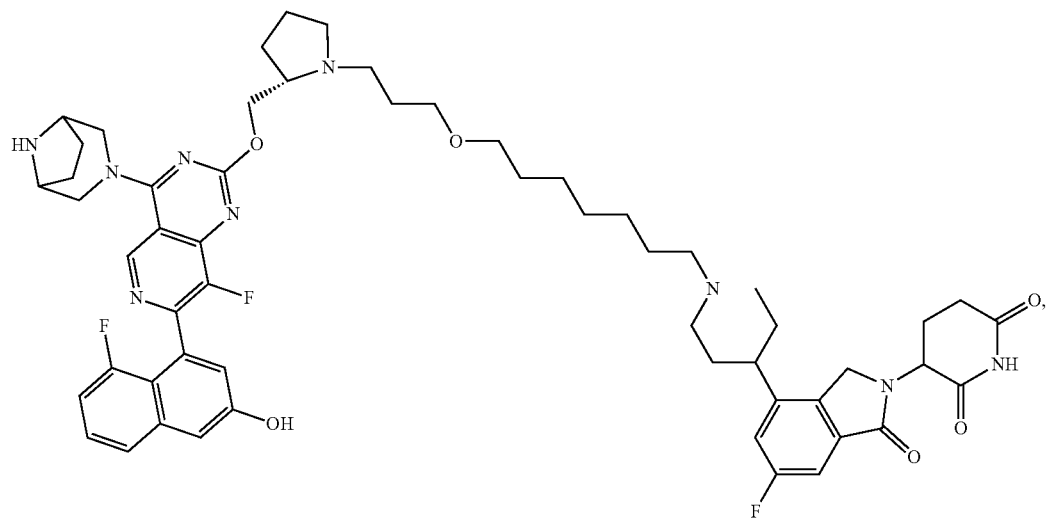

-continued
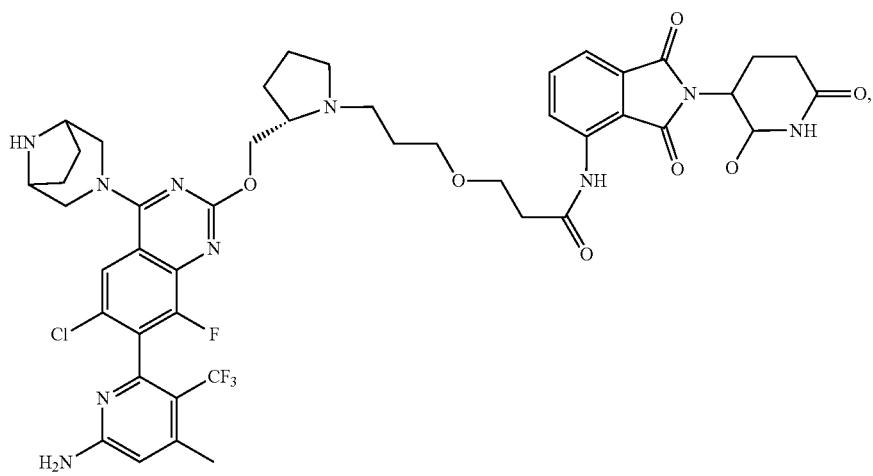
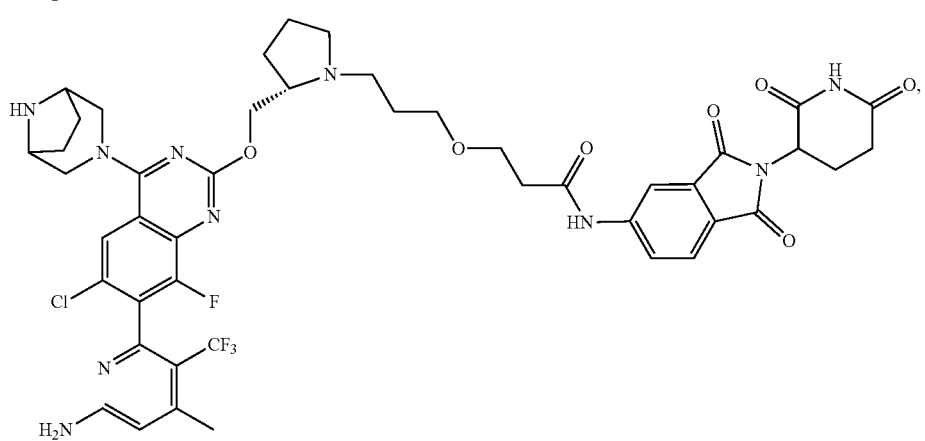
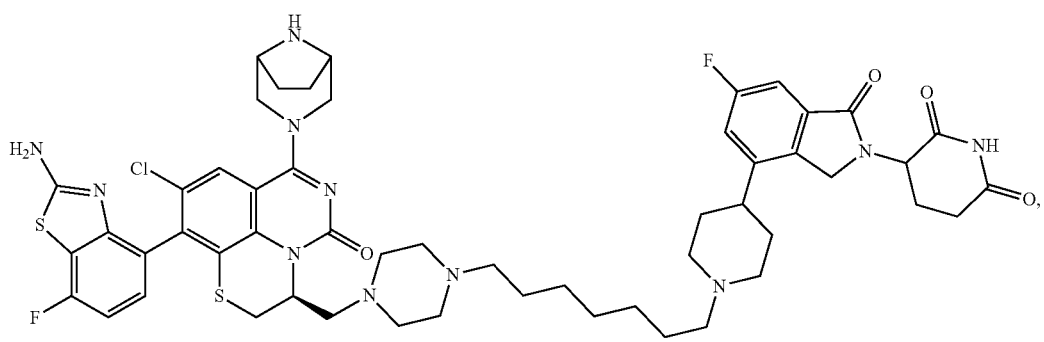
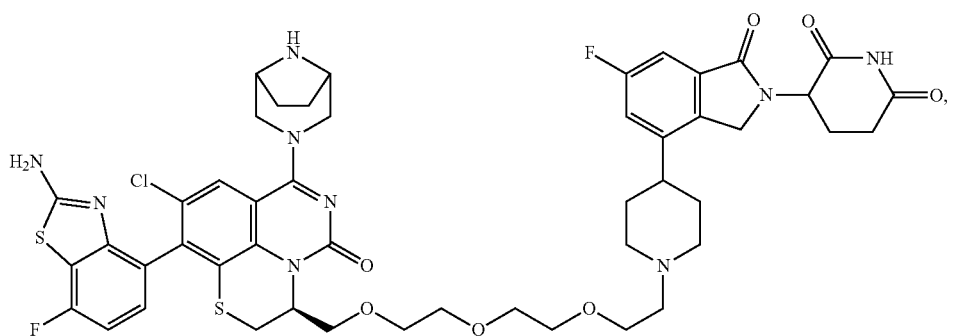

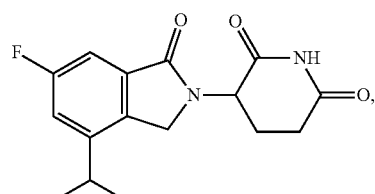
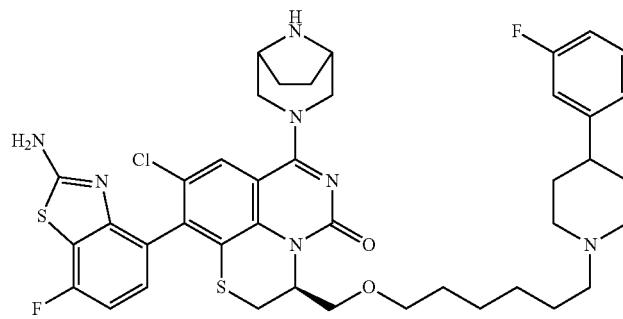
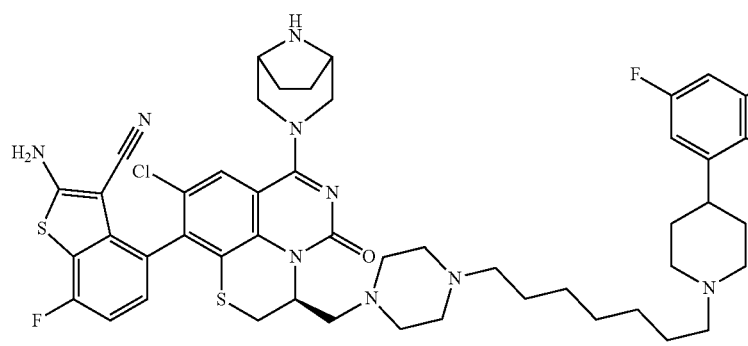
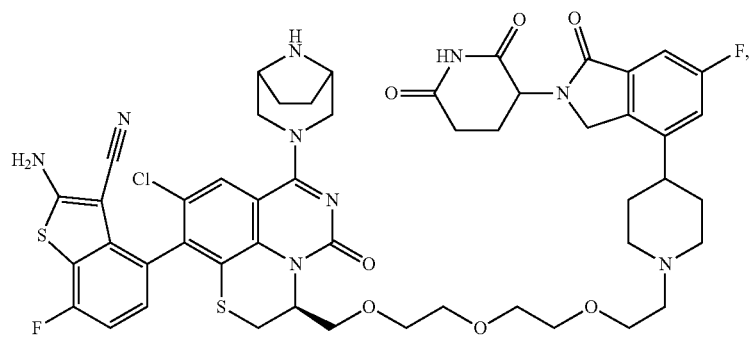
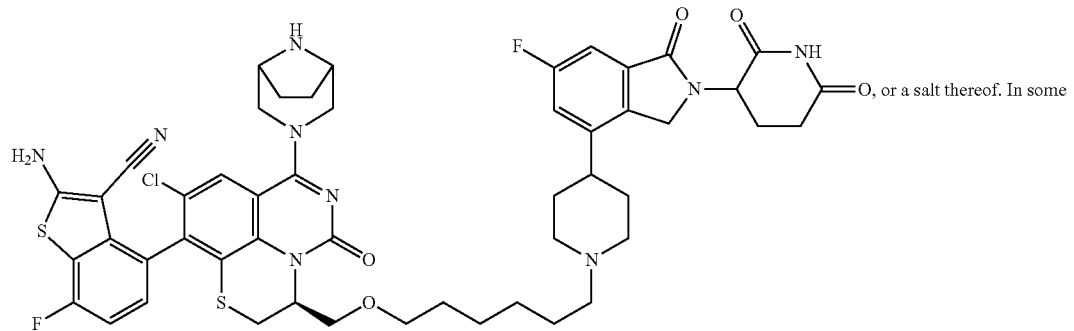
O, or a salt thereof. In some aspects, the compound is not:
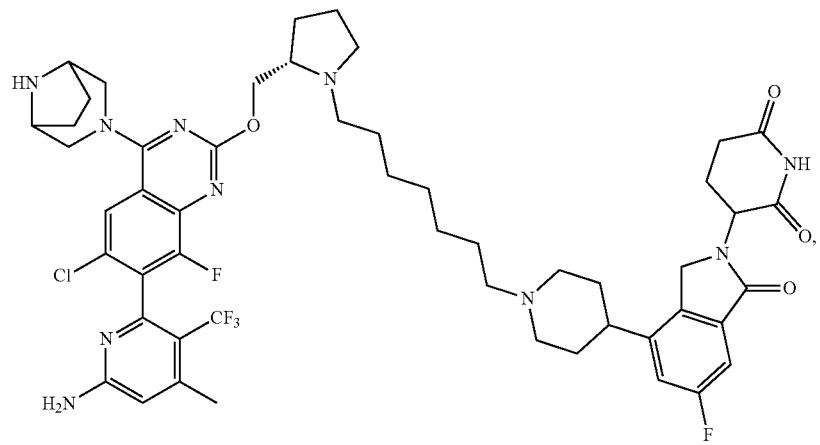
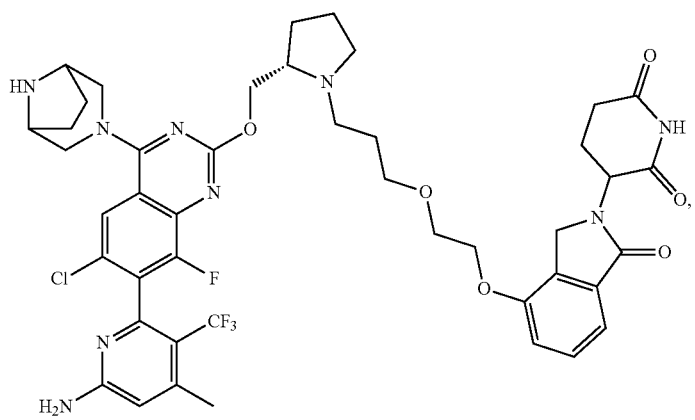
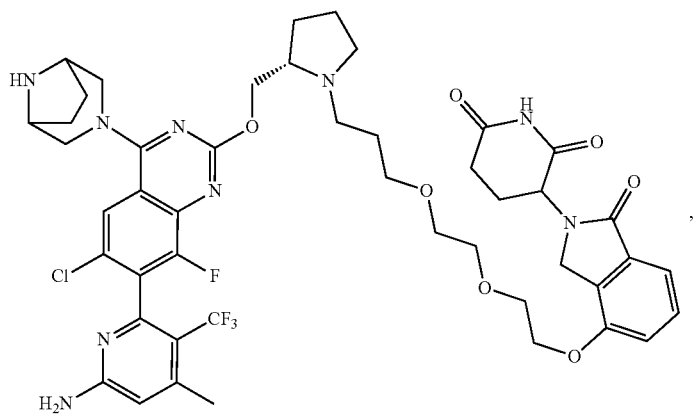
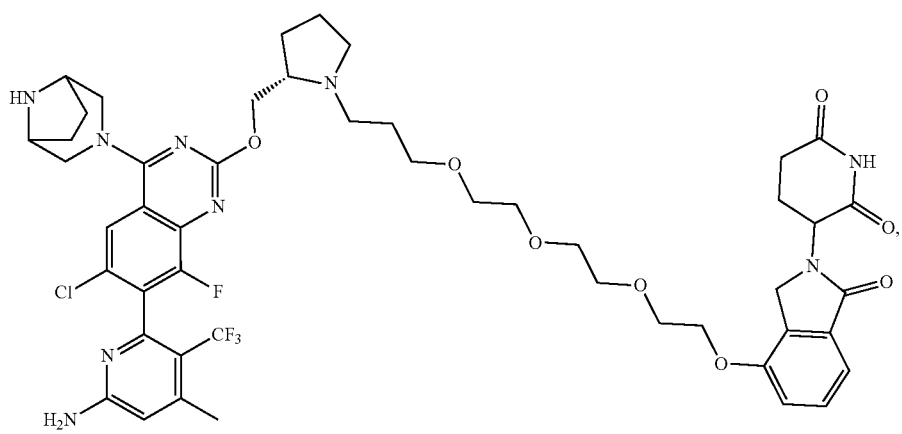

733
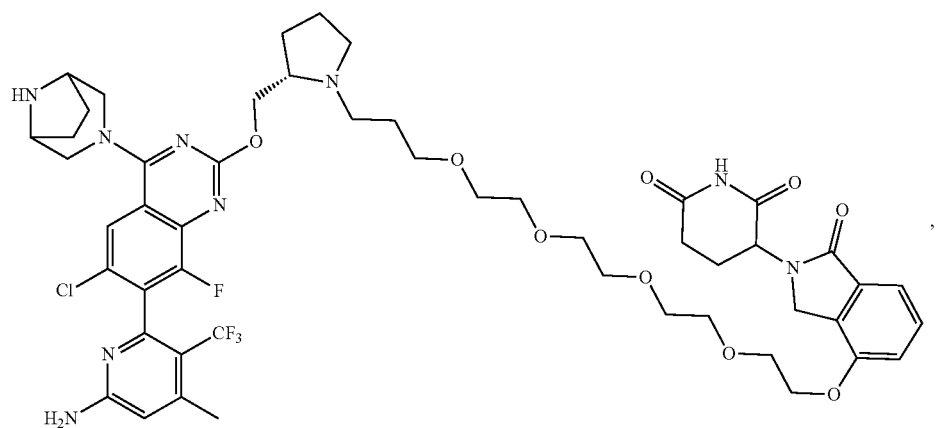
734
-continued
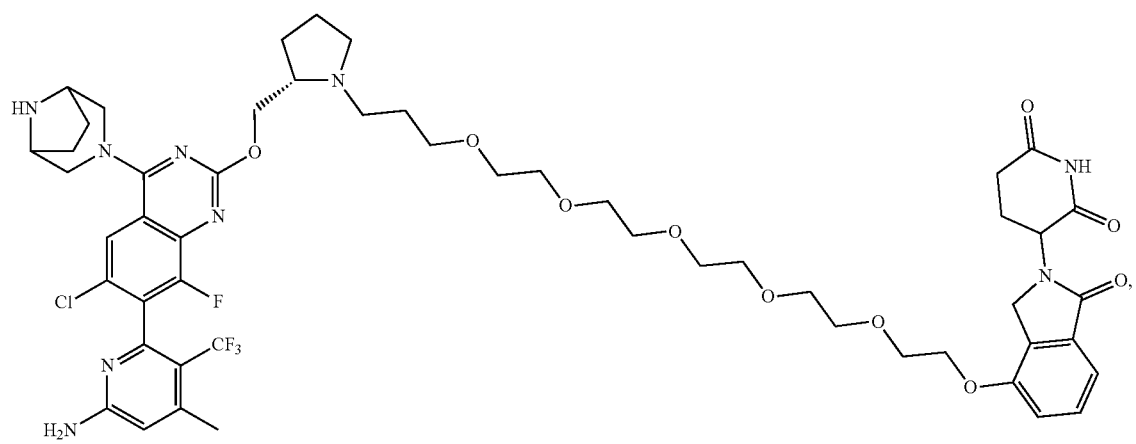
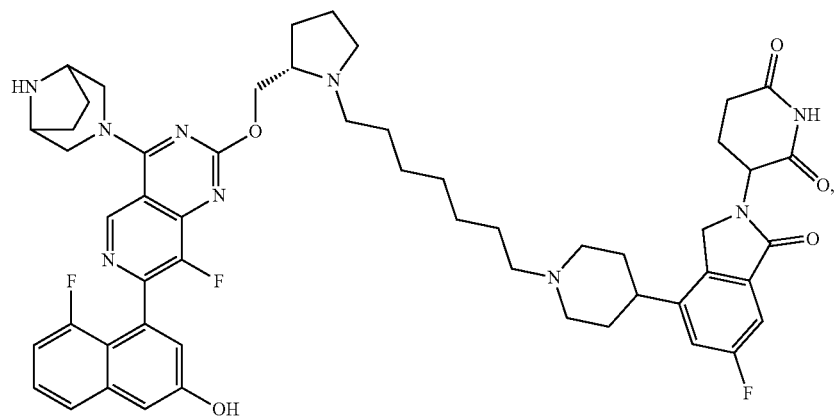

or a salt thereof. In some aspects, the compound is not:
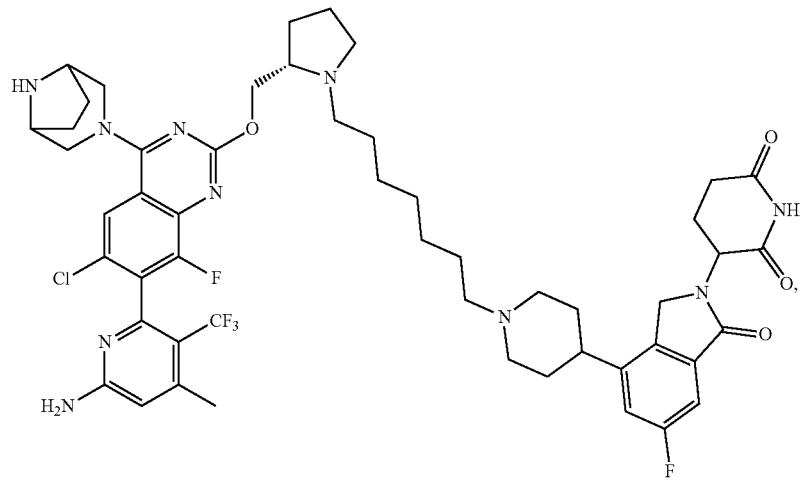 [SMILES: Cc1cc(N)nc(-c2c(Cl)cc3c(N4CC5CCC(C4)N5)nc(OC[C@@H]4CCCN4CCCCCCCN4CCC(c5cc(F)cc6c5CN(C5CCC(=O)NC5=O)C6=O)CC4)nc3c2F)c1C(F)(F)F]
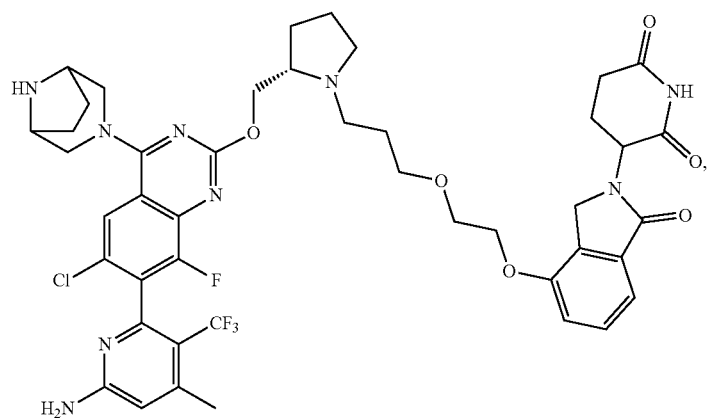
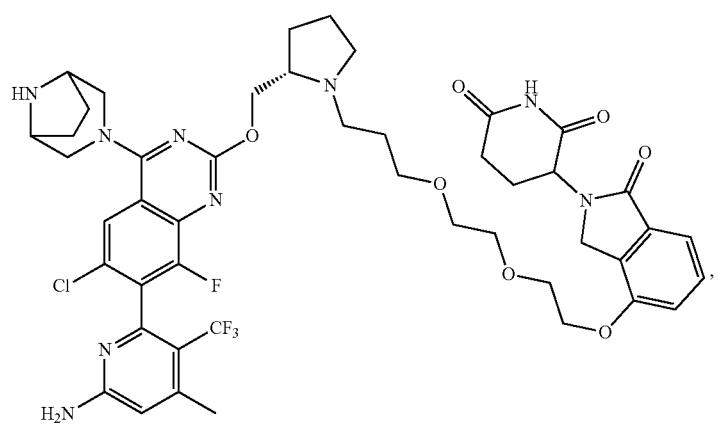

737
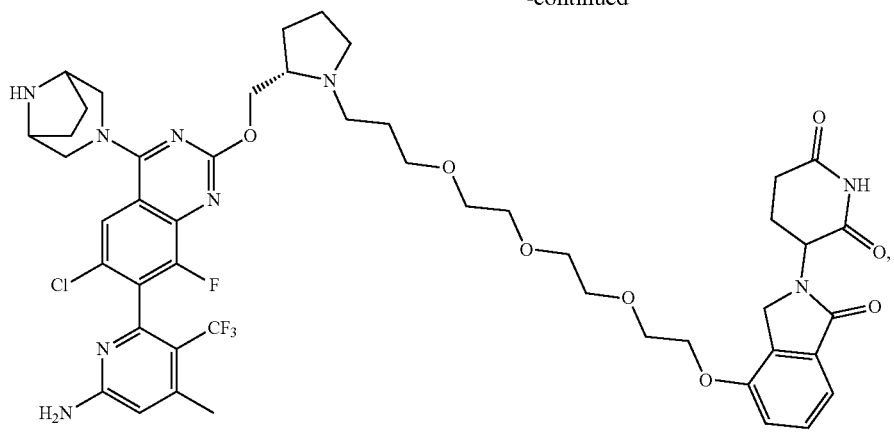
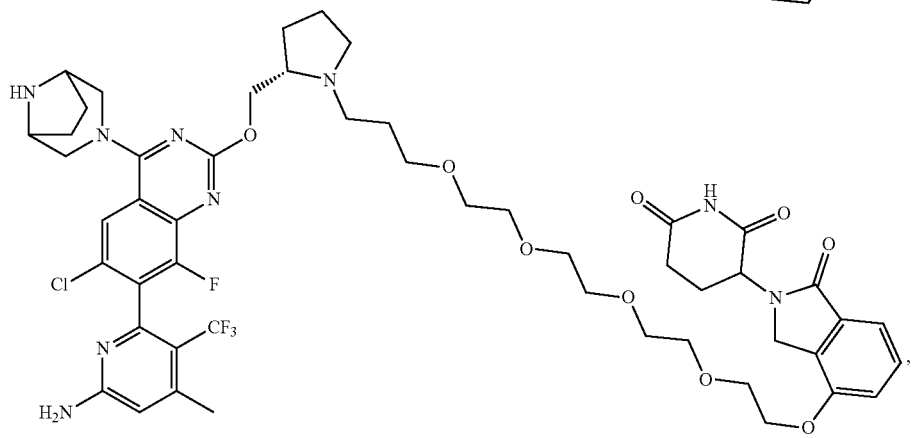
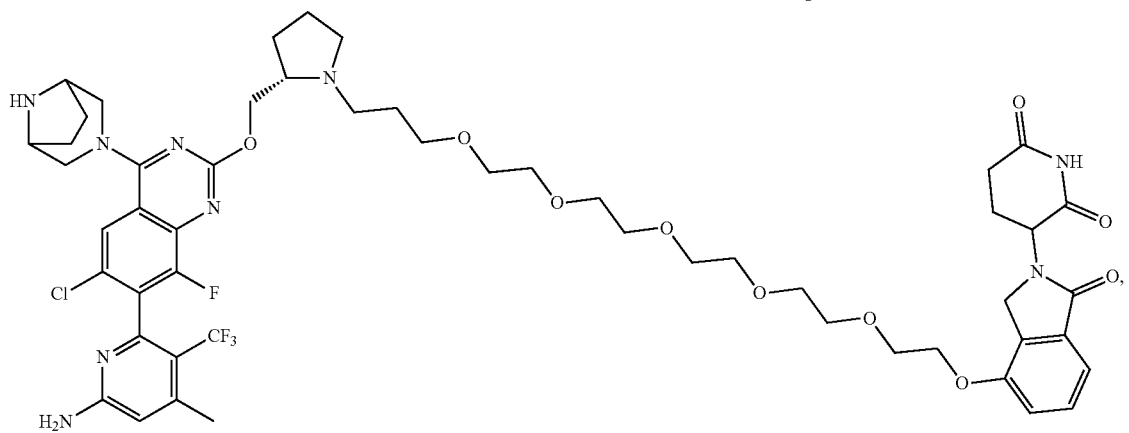
738
-continued
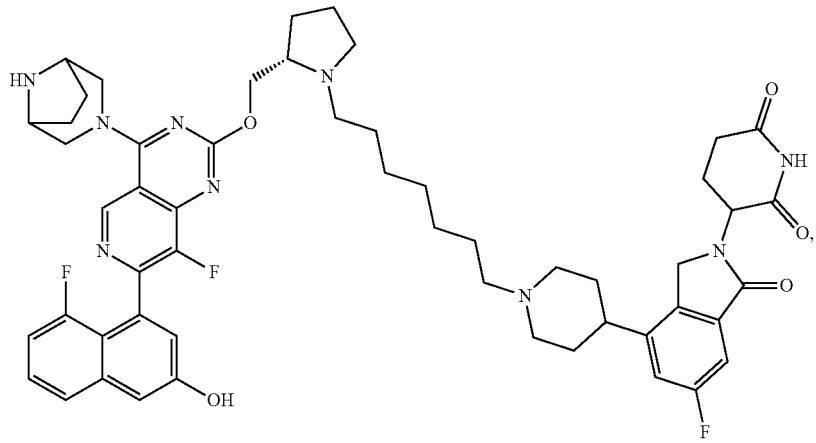

739
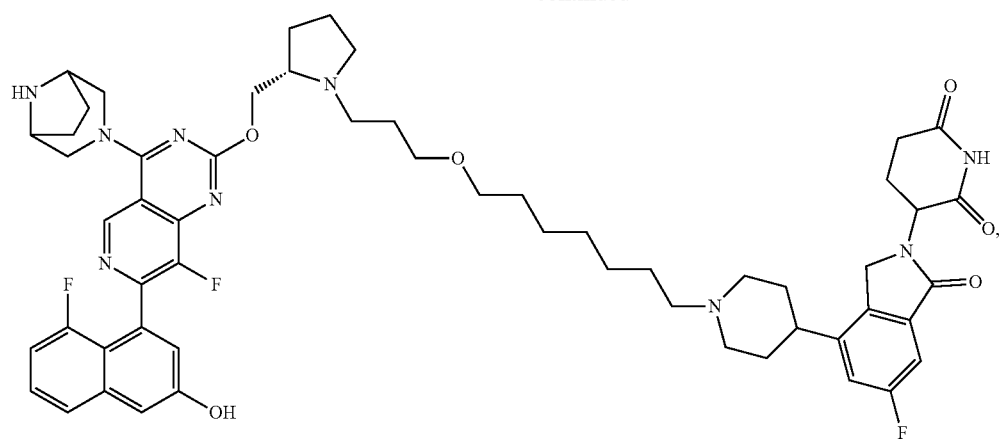
740
-continued
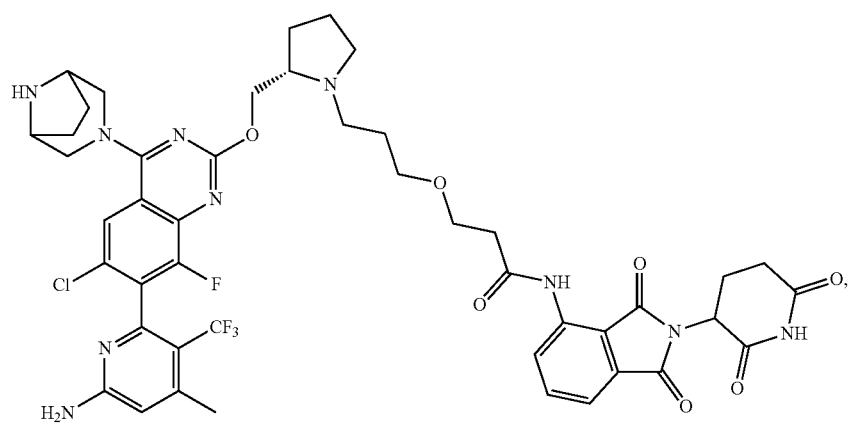
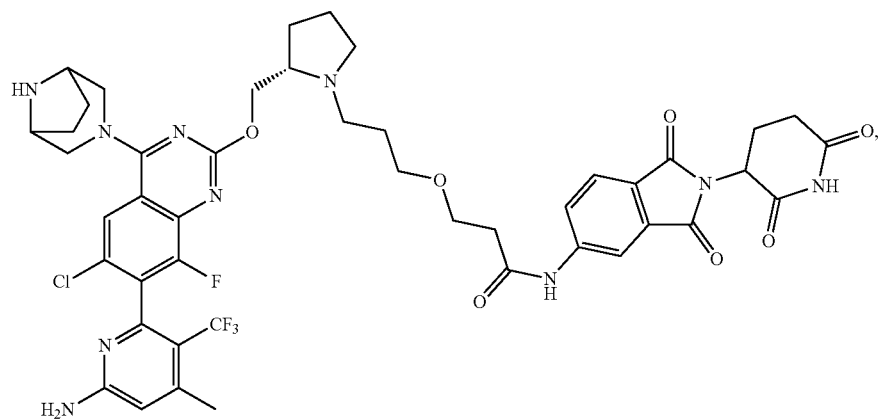

or a salt thereof. In some aspects, the compound is not:
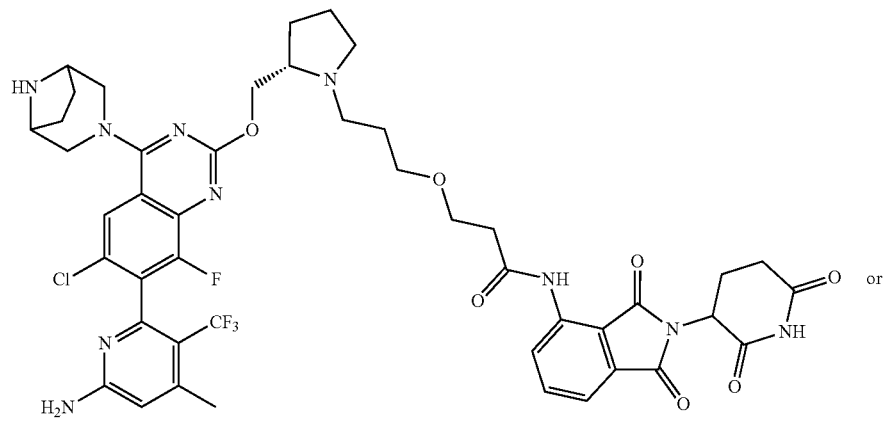
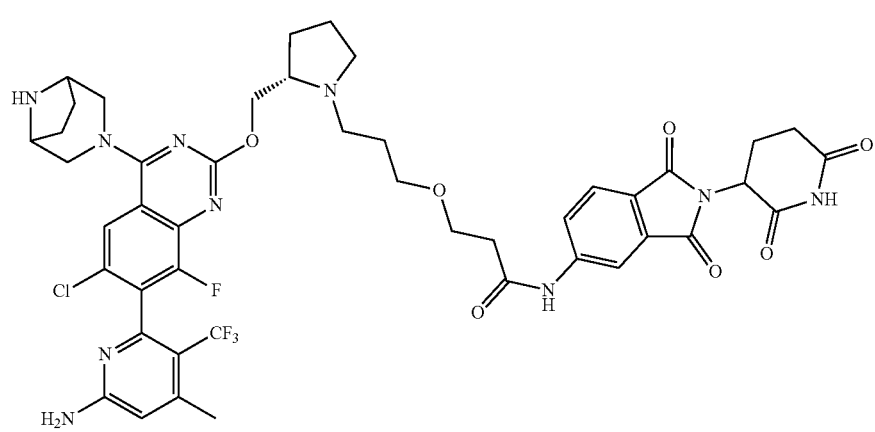
40
or a salt thereof.
TABLE 1
Example Compounds of the Disclosure
| Compound No. | Compound Structure |
|---|---|
| 001 | 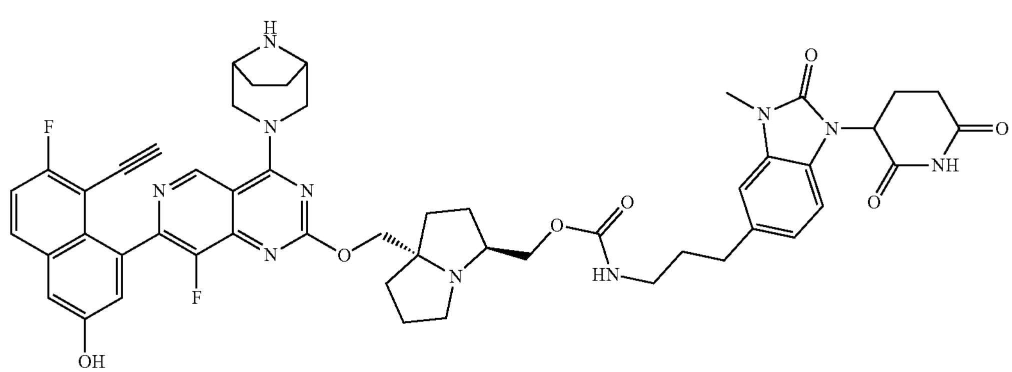 [SMILES: C#Cc1c(F)ccc2cc(O)cc(-c3ncc4c(N5CC6CCC(C5)N6)nc(OC[C@@]56CCCN5[C@H](COC(=O)NCCCc5ccc7c(c5)n(C)c(=O)n7C5CCC(=O)NC5=O)CC6)nc4c3F)c12] |

TABLE 1-continued

Example Compounds of the Disclosure

| Compound No. | Compound Structure |
| --- | --- |
| 002 | 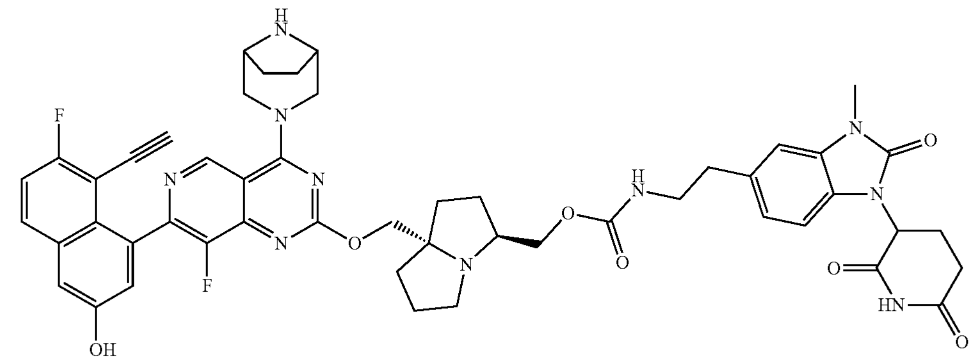 [SMILES: C#Cc1c(F)ccc2cc(O)cc(-c3ncc4c(N5CC6CCC(C5)N6)nc(OC[C@@]56CCCN5[C@H](COC(=O)NCCc5ccc7c(c5)n(C)c(=O)n7C5CCC(=O)NC5=O)CC6)nc4c3F)c12] |
| 003 | 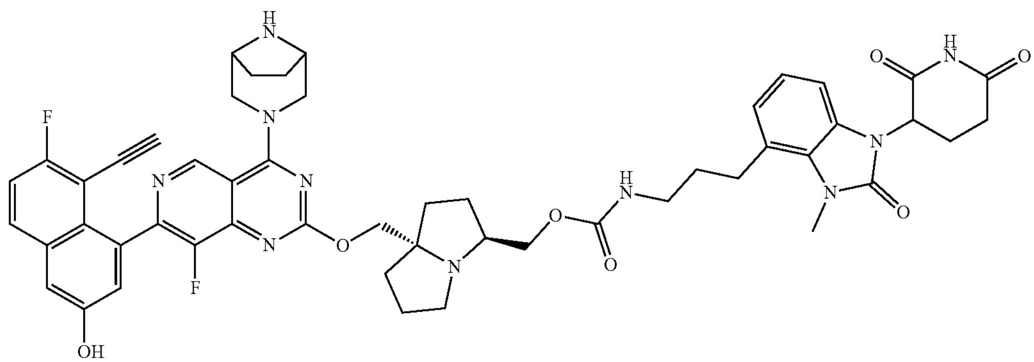 [SMILES: C#Cc1c(F)ccc2cc(O)cc(-c3ncc4c(N5CC6CCC(C5)N6)nc(OC[C@@]56CCCN5[C@H](COC(=O)NCCCc5cccc7c5n(C)c(=O)n7C5CCC(=O)NC5=O)CC6)nc4c3F)c12] |
| 004 | 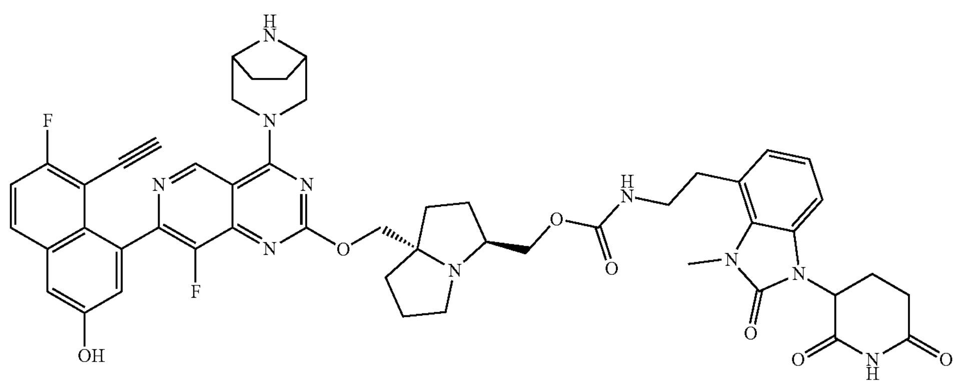 [SMILES: C#Cc1c(F)ccc2cc(O)cc(-c3ncc4c(N5CC6CCC(C5)N6)nc(OC[C@@]56CCCN5[C@H](COC(=O)NCCc5cccc7c5n(C)c(=O)n7C5CCC(=O)NC5=O)CC6)nc4c3F)c12] |
| 005 | 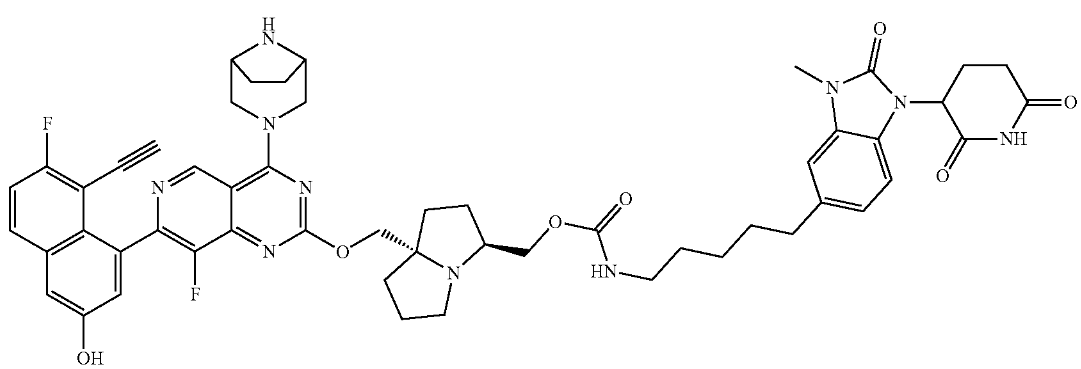 [SMILES: C#Cc1c(F)ccc2cc(O)cc(-c3ncc4c(N5CC6CCC(C5)N6)nc(OC[C@@]56CCCN5[C@H](COC(=O)NCCCCCc5ccc7c(c5)n(C)c(=O)n7C5CCC(=O)NC5=O)CC6)nc4c3F)c12] |

TABLE 1-continued

Example Compounds of the Disclosure

| Compound No. | Compound Structure |
| --- | --- |
| 006 | 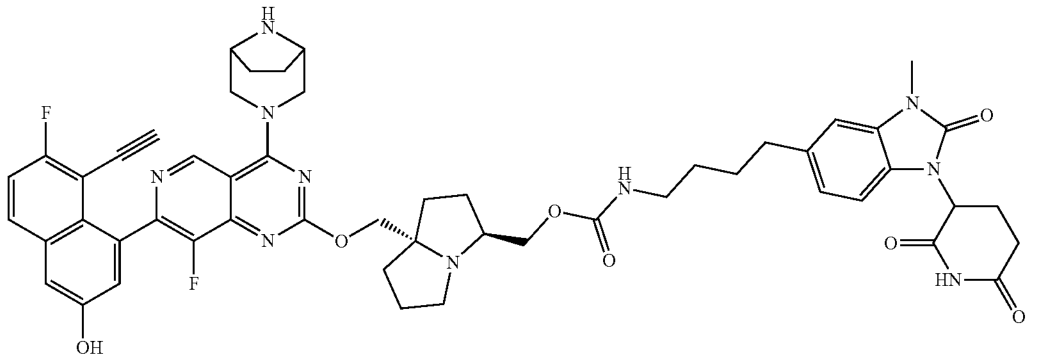 [SMILES: C#Cc1c(F)ccc2cc(O)cc(-c3ncc4c(N5CC6CCC(C5)N6)nc(OC[C@@]56CCCN5[C@H](COC(=O)NCCCCc5ccc7c(c5)n(C)c(=O)n7C5CCC(=O)NC5=O)CC6)nc4c3F)c12] |
| 007 | 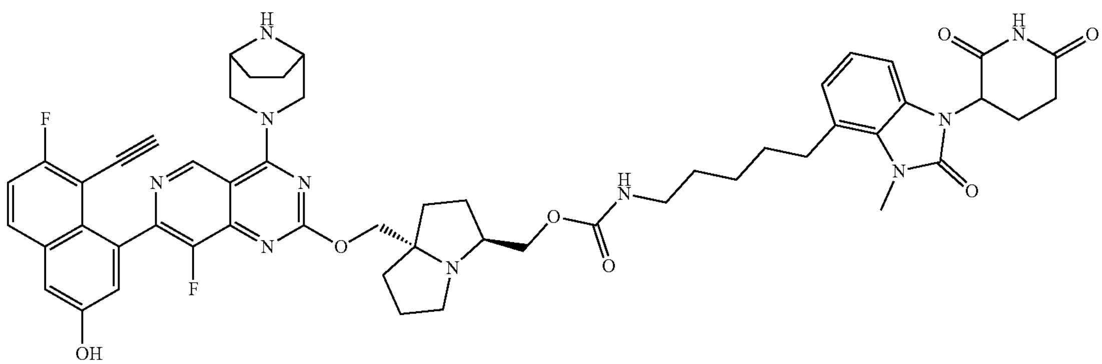 [SMILES: C#Cc1c(F)ccc2cc(O)cc(-c3ncc4c(N5CC6CCC(C5)N6)nc(OC[C@@]56CCCN5[C@H](COC(=O)NCCCCCc5cccc7c5n(C)c(=O)n7C5CCC(=O)NC5=O)CC6)nc4c3F)c12] |
| 008 | 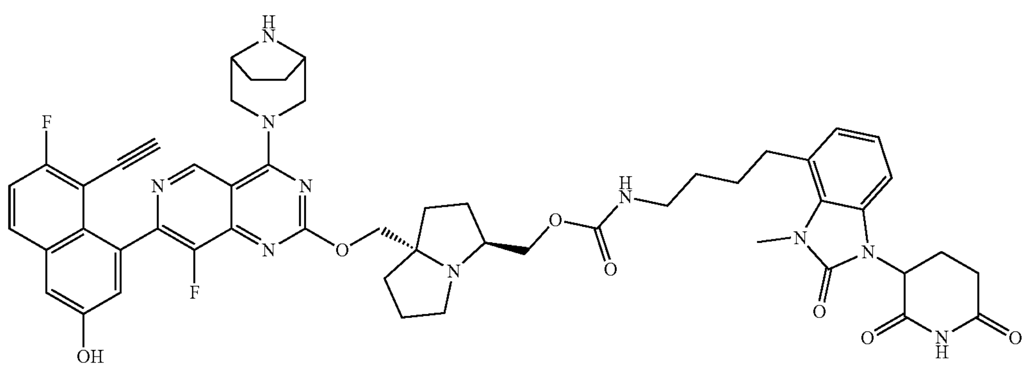 [SMILES: C#Cc1c(F)ccc2cc(O)cc(-c3ncc4c(N5CC6CCC(C5)N6)nc(OC[C@@]56CCCN5[C@H](COC(=O)NCCCCc5cccc7c5n(C)c(=O)n7C5CCC(=O)NC5=O)CC6)nc4c3F)c12] |
| 009 | 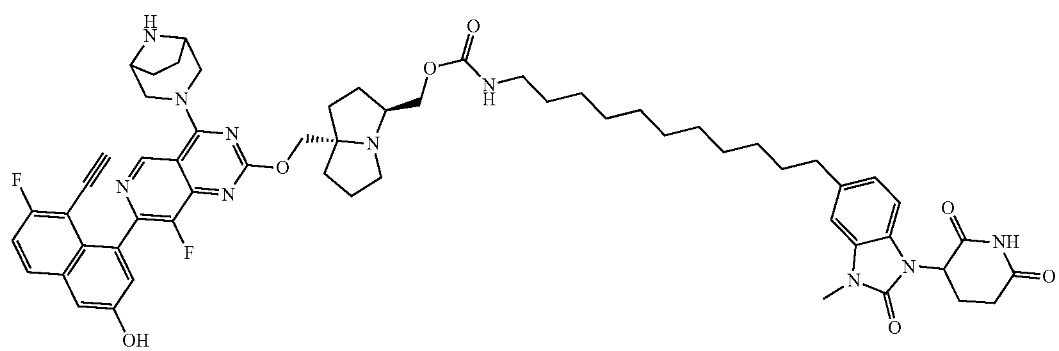 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCCCc5ccc7c(c5)n(C)c(=O)n7C5CCC(=O)NC5=O)CC6)nc4c3F)c12] |

TABLE 1-continued
Example Compounds of the Disclosure
| Compound No. | Compound Structure |
|---|---|
| 010 | 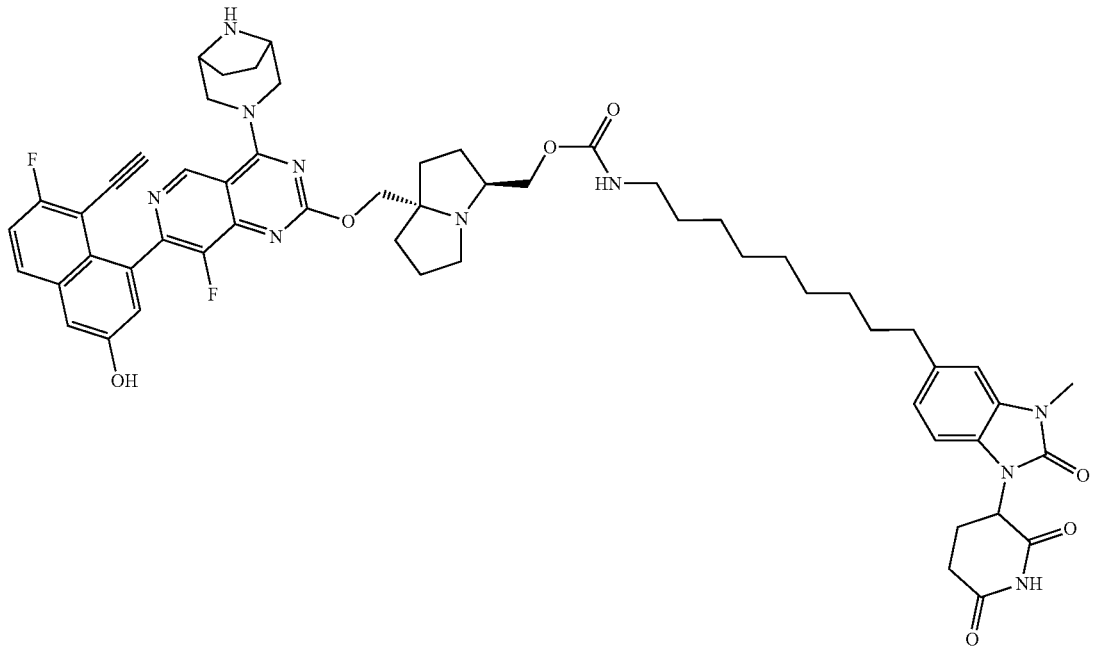 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCc5ccc7c(c5)n(C)c(=O)n7C5CCC(=O)NC5=O)CC6)nc4c3F)c12] |
| 011 | 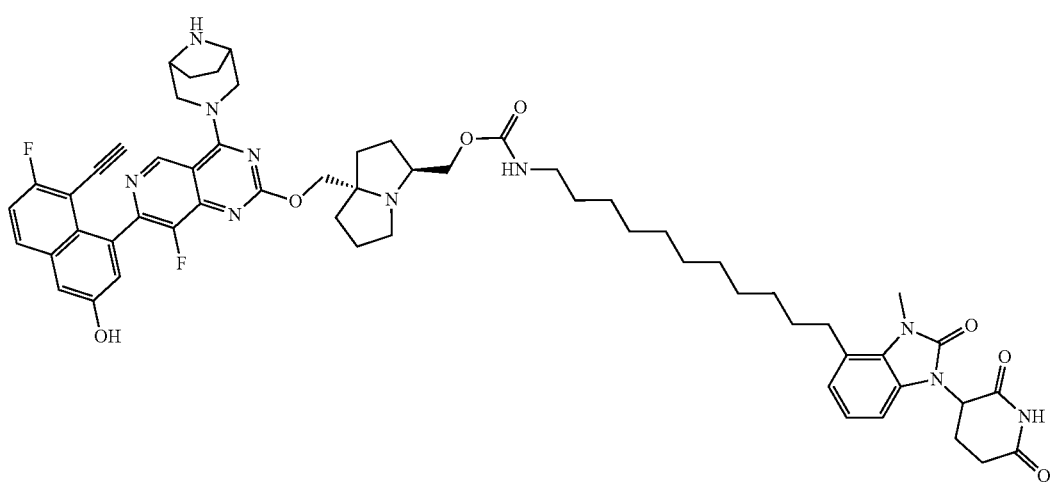 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCCCc5cccc7c5n(C)c(=O)n7C5CCC(=O)NC5=O)CC6)nc4c3F)c12] |

TABLE 1-continued

Example Compounds of the Disclosure

| Compound No. | Compound Structure |
|---|---|
| 012 | 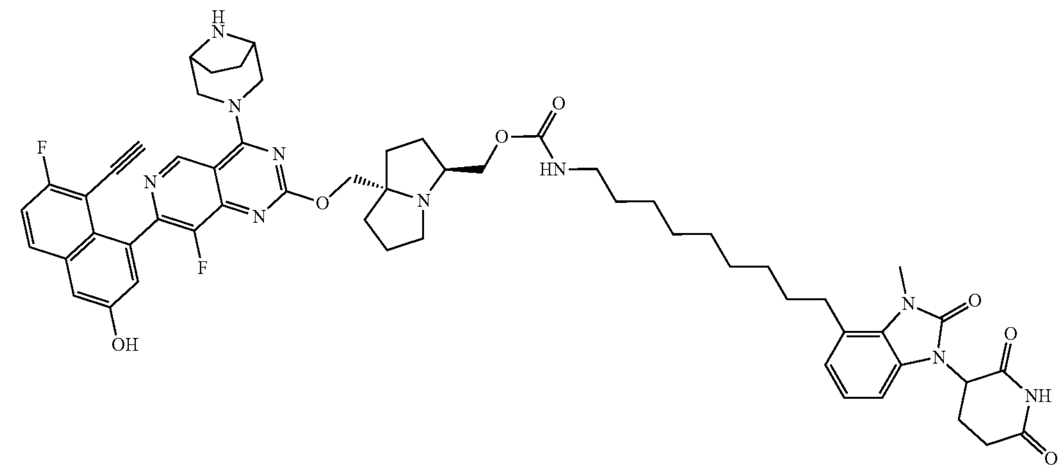 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCc5cccc7c5n(C)c(=O)n7C5CCC(=O)NC5=O)CC6)nc4c3F)c12] |
| 013 | 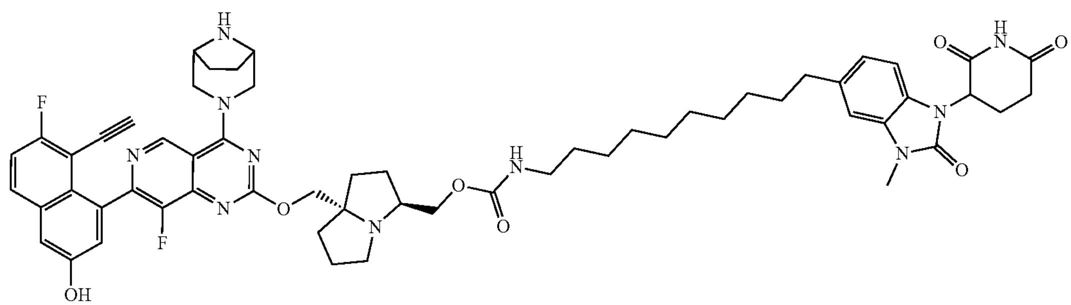 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCCc5ccc7c(c5)n(C)c(=O)n7C5CCC(=O)NC5=O)CC6)nc4c3F)c12] |
| 014 | 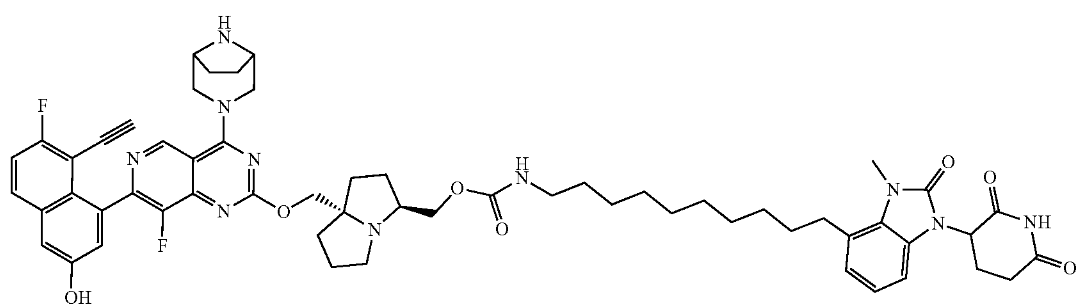 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCCc5cccc7c5n(C)c(=O)n7C5CCC(=O)NC5=O)CC6)nc4c3F)c12] |
| 015 | 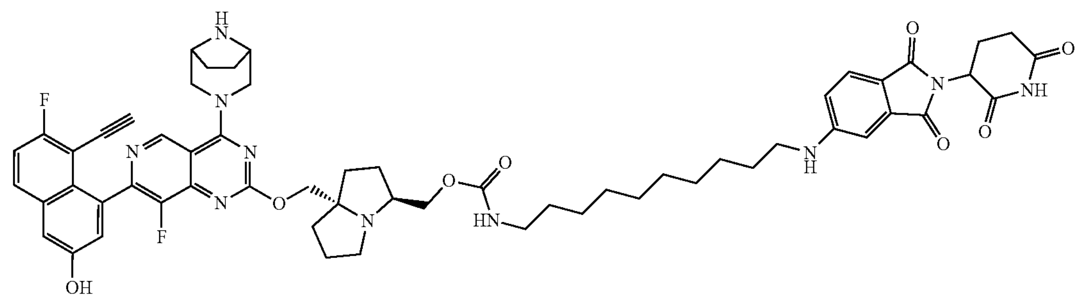 [SMILES: C#Cc1c(F)ccc2cc(O)cc(-c3ncc4c(N5CC6CCC(C5)N6)nc(OC[C@@]56CCCN5[C@H](COC(=O)NCCCCCCCCCCNc5ccc7c(c5)C(=O)N(C5CCC(=O)NC5=O)C7=O)CC6)nc4c3F)c12] |

TABLE 1-continued
Example Compounds of the Disclosure
| Compound No. | Compound Structure |
|---|---|
| 016 | 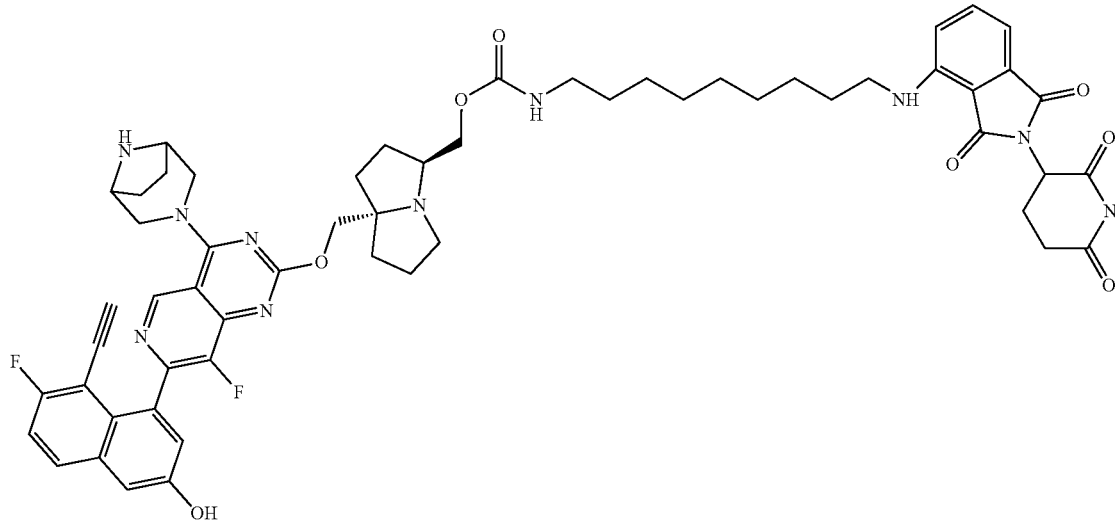 |
| 017 | 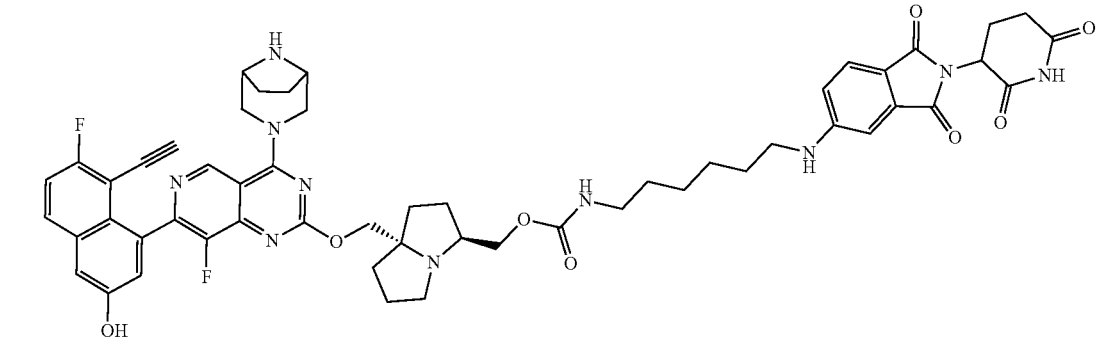 [SMILES: C#Cc1c(F)ccc2cc(O)cc(-c3ncc4c(N5CC6CCC(C5)N6)nc(OC[C@@]56CCCN5[C@H](COC(=O)NCCCCCCNc5ccc7c(c5)C(=O)N(C5CCC(=O)NC5=O)C7=O)CC6)nc4c3F)c12] |
| 018 | 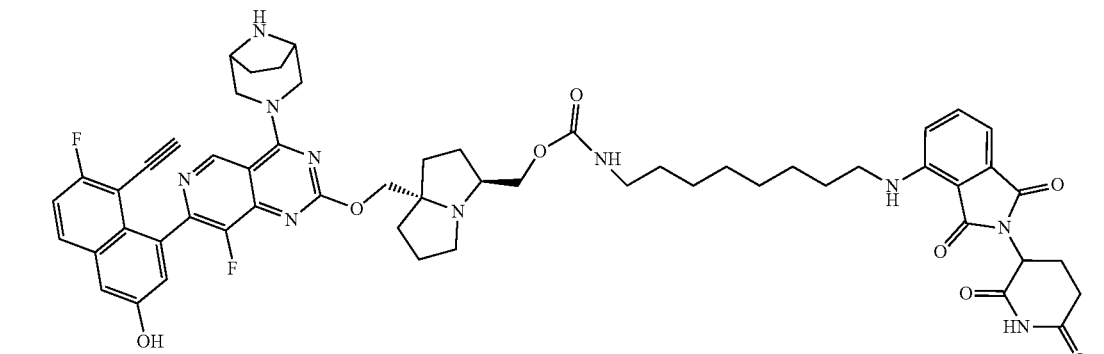 |

TABLE 1-continued

Example Compounds of the Disclosure

| Compound No. | Compound Structure |
|---|---|
| 019 | 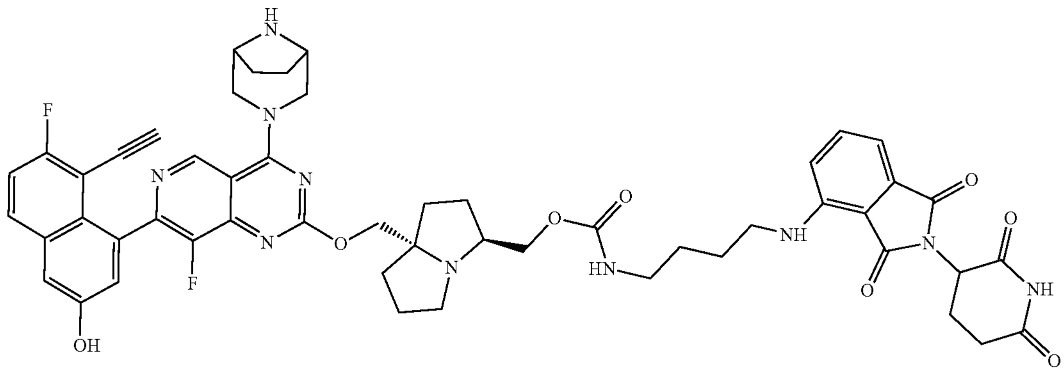 [SMILES: C#Cc1c(F)ccc2cc(O)cc(-c3ncc4c(N5CC6CCC(C5)N6)nc(OC[C@@]56CCCN5[C@H](COC(=O)NCCCCNc5cccc7c5C(=O)N(C5CCC(=O)NC5=O)C7=O)CC6)nc4c3F)c12] |
| 020 | 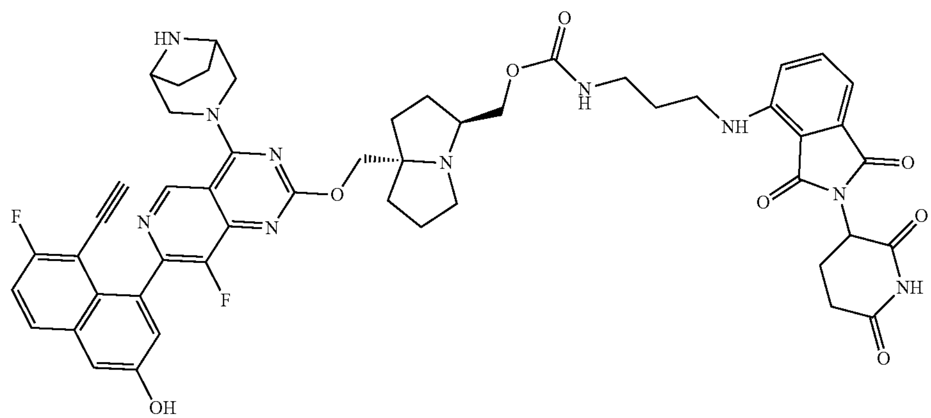 [SMILES: C#Cc1c(F)ccc2cc(O)cc(-c3ncc4c(N5CC6CCC(C5)N6)nc(OC[C@@]56CCCN5[C@H](COC(=O)NCCCNc5cccc7c5C(=O)N(C5CCC(=O)NC5=O)C7=O)CC6)nc4c3F)c12] |
| 021 | 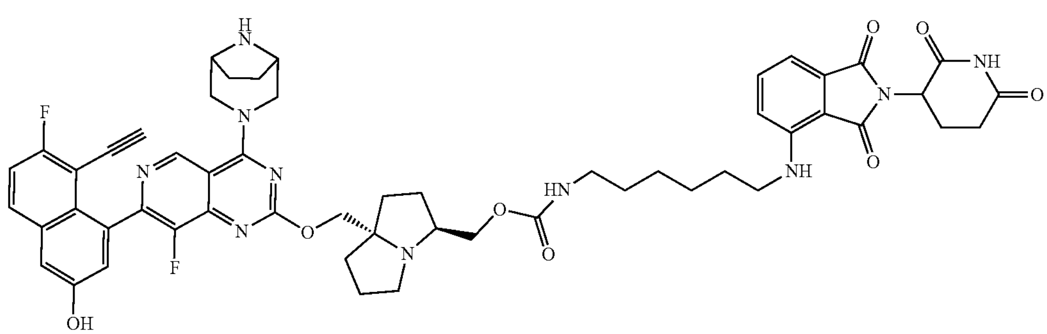 [SMILES: C#Cc1c(F)ccc2cc(O)cc(-c3ncc4c(N5CC6CCC(C5)N6)nc(OC[C@@]56CCCN5[C@H](COC(=O)NCCCCCCNc5cccc7c5C(=O)N(C5CCC(=O)NC5=O)C7=O)CC6)nc4c3F)c12] |
| 022 | 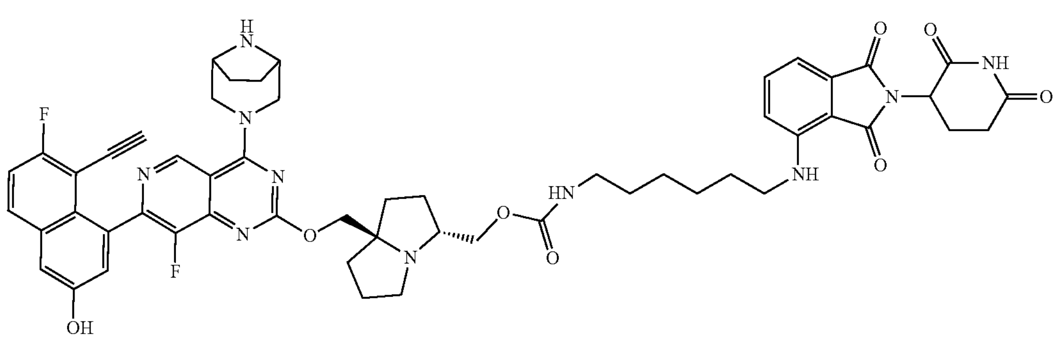 [SMILES: C#Cc1c(F)ccc2cc(O)cc(-c3ncc4c(N5CC6CCC(C5)N6)nc(OC[C@]56CCCN5[C@@H](COC(=O)NCCCCCCNc5cccc7c5C(=O)N(C5CCC(=O)NC5=O)C7=O)CC6)nc4c3F)c12] |

TABLE 1-continued

Example Compounds of the Disclosure

| Compound No. | Compound Structure |
|---|---|
| 023 | 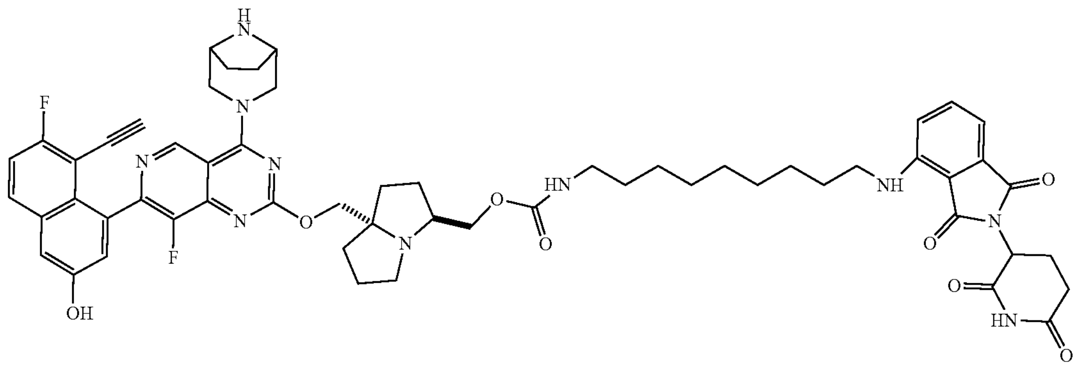 |
| 024 | 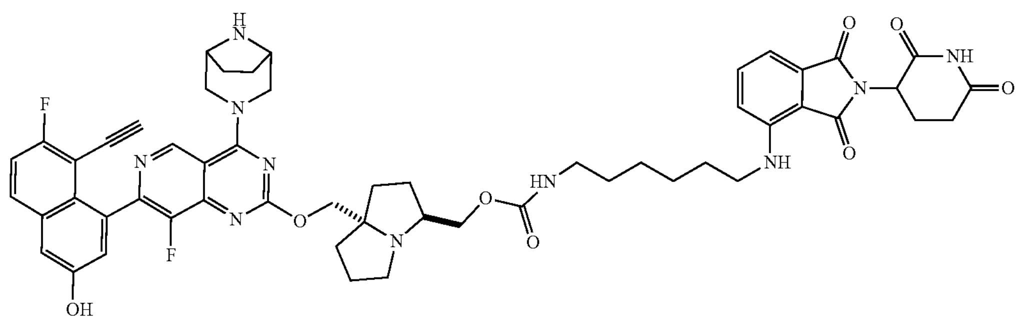 |
| 025 | 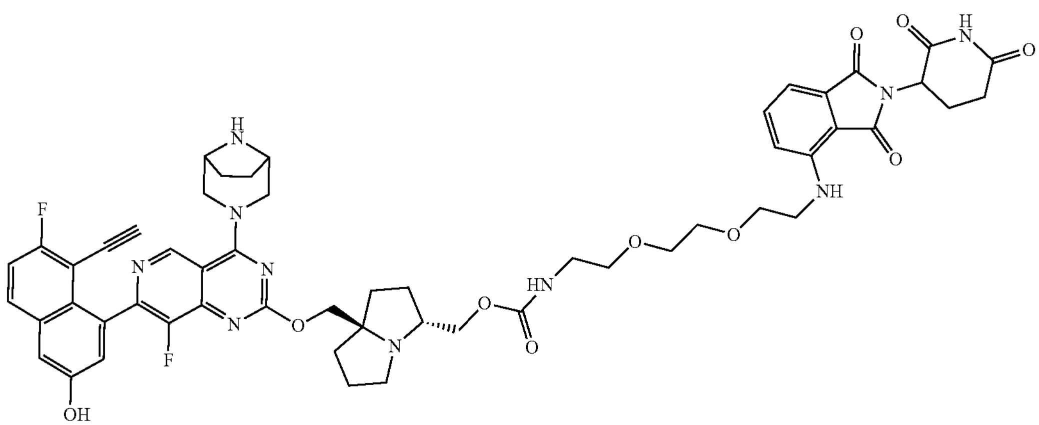 [SMILES: C#Cc1c(F)ccc2cc(O)cc(-c3ncc4c(N5CC6CCC(C5)N6)nc(OC[C@]56CCCN5[C@@H](COC(=O)NCCOCCOCCNc5cccc7c5C(=O)N(C5CCC(=O)NC5=O)C7=O)CC6)nc4c3F)c12] |
| 026 | 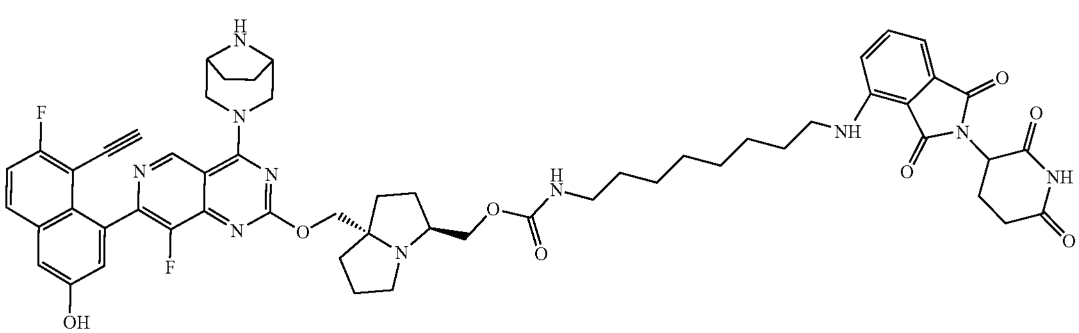 [SMILES: C#Cc1c(F)ccc2cc(O)cc(-c3ncc4c(N5CC6CCC(C5)N6)nc(OC[C@@]56CCCN5[C@H](COC(=O)NCCCCCCCCNc5cccc7c5C(=O)N(C5CCC(=O)NC5=O)C7=O)CC6)nc4c3F)c12] |

TABLE 1-continued

Example Compounds of the Disclosure

| Compound No. | Compound Structure |
|---|---|
| 027 | 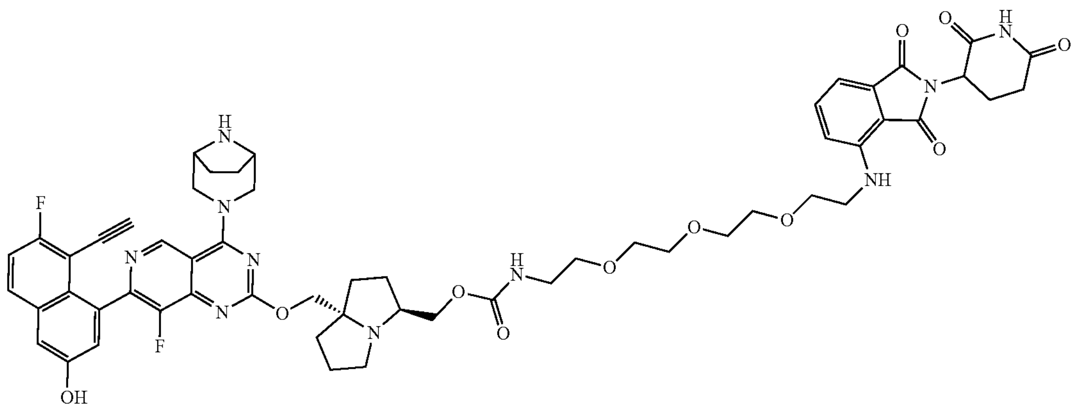 [SMILES: C#Cc1c(F)ccc2cc(O)cc(-c3ncc4c(N5CC6CCC(C5)N6)nc(OC[C@@]56CCCN5[C@H](COC(=O)NCCOCCOCCOCCNc5cccc7c5C(=O)N(C5CCC(=O)NC5=O)C7=O)CC6)nc4c3F)c12] |
| 028 | 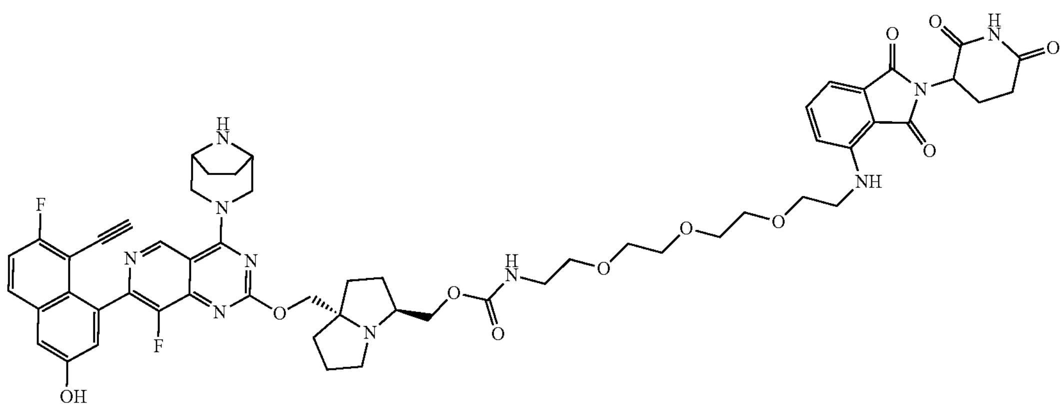 [SMILES: C#Cc1c(F)ccc2cc(O)cc(-c3ncc4c(N5CC6CCC(C5)N6)nc(OC[C@@]56CCCN5[C@H](COC(=O)NCCOCCOCCOCCNc5cccc7c5C(=O)N(C5CCC(=O)NC5=O)C7=O)CC6)nc4c3F)c12] |
| 029 | 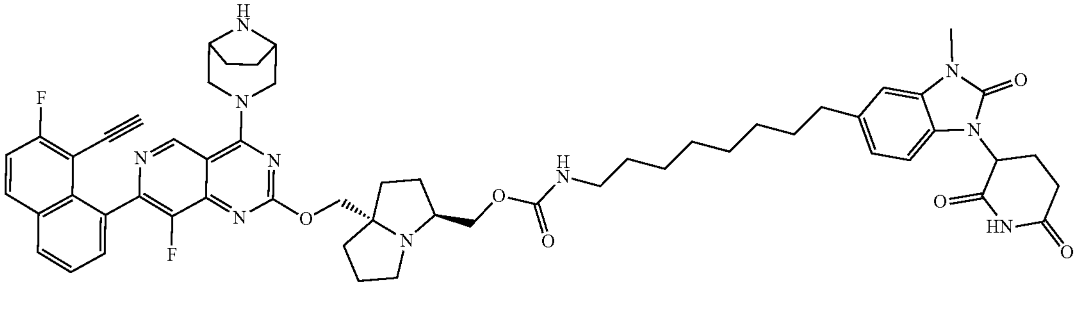 [SMILES: C#Cc1c(F)ccc2cccc(-c3ncc4c(N5CC6CCC(C5)N6)nc(OC[C@@]56CCCN5[C@H](COC(=O)NCCCCCCCCc5ccc7c(c5)n(C)c(=O)n7C5CCC(=O)NC5=O)CC6)nc4c3F)c12] |

TABLE 1-continued
Example Compounds of the Disclosure
| Compound No. | Compound Structure |
|---|---|
| 030 | 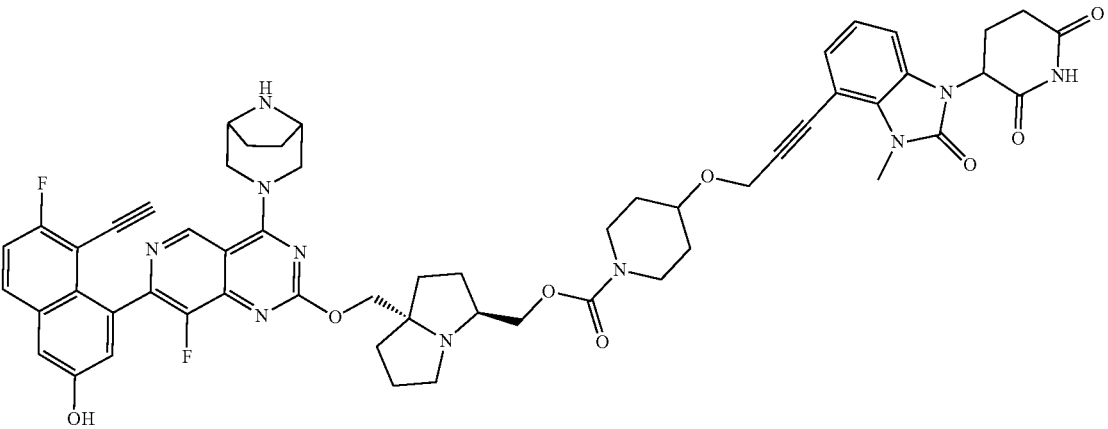 [SMILES: C#Cc1c(F)ccc2cc(O)cc(-c3ncc4c(N5CC6CCC(C5)N6)nc(OC[C@@]56CCCN5[C@H](COC(=O)N5CCC(OCC#Cc7cccc8c7n(C)c(=O)n8C7CCC(=O)NC7=O)CC5)CC6)nc4c3F)c12] |
| 031 | 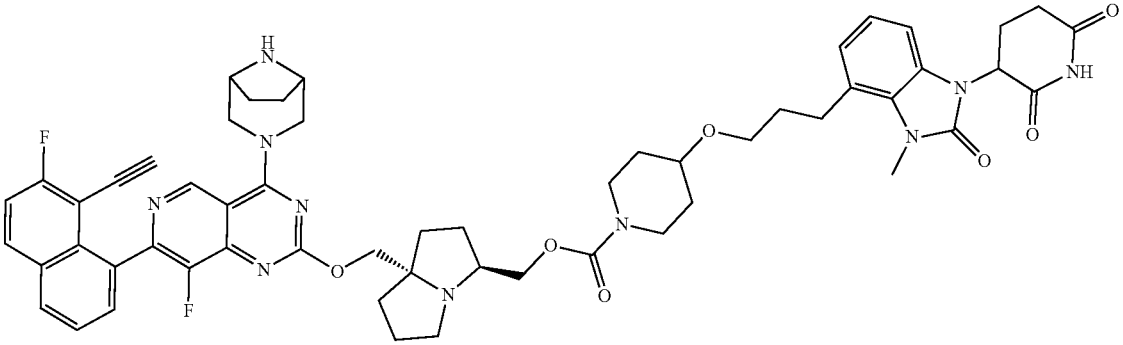 [SMILES: C#Cc1c(F)ccc2cccc(-c3ncc4c(N5CC6CCC(C5)N6)nc(OC[C@@]56CCCN5[C@H](COC(=O)N5CCC(OCCCc7cccc8c7n(C)c(=O)n8C7CCC(=O)NC7=O)CC5)CC6)nc4c3F)c12] |
| 032 | 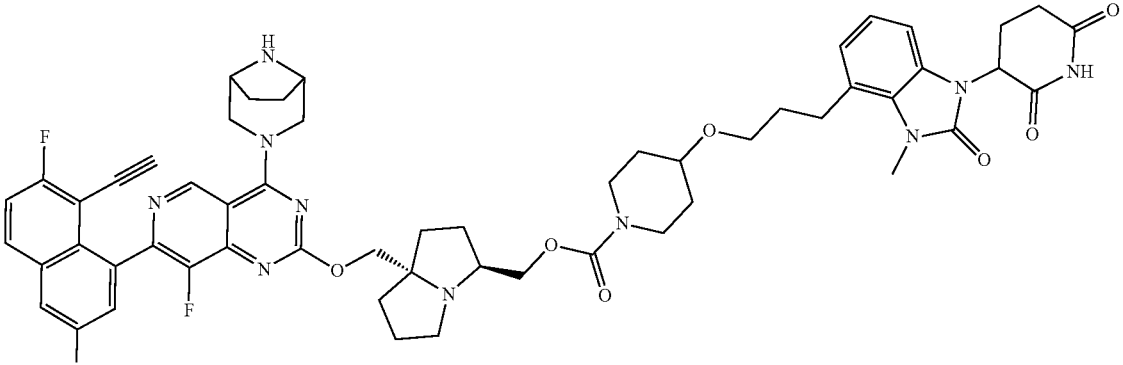 |

TABLE 1-continued

Example Compounds of the Disclosure

| Compound No. | Compound Structure |
|---|---|
| 033 | 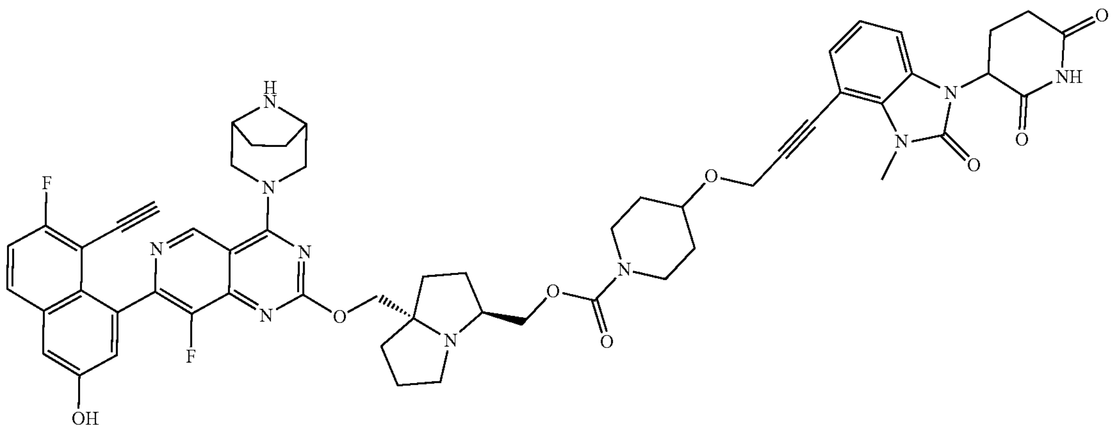 [SMILES: C#Cc1c(F)ccc2cc(O)cc(-c3ncc4c(N5CC6CCC(C5)N6)nc(OC[C@@]56CCCN5[C@H](COC(=O)N5CCC(OCC#Cc7cccc8c7n(C)c(=O)n8C7CCC(=O)NC7=O)CC5)CC6)nc4c3F)c12] |
| 034 | 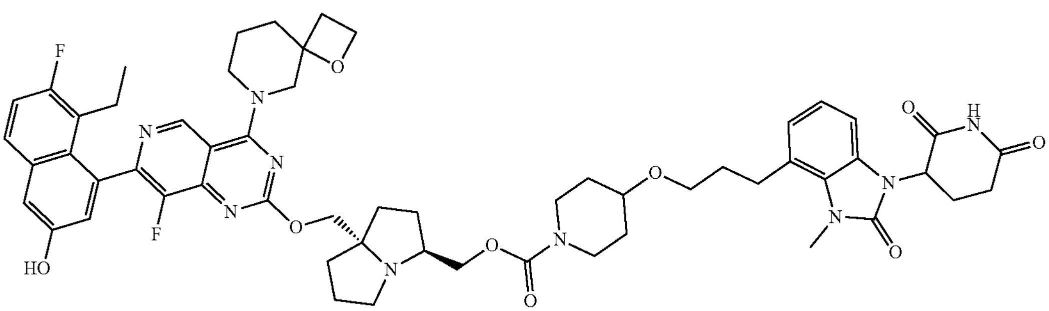 [SMILES: CCc1c(F)ccc2cc(O)cc(-c3ncc4c(N5CCCC6(CCO6)C5)nc(OC[C@@]56CCCN5[C@H](COC(=O)N5CCC(OCCCc7cccc8c7n(C)c(=O)n8C7CCC(=O)NC7=O)CC5)CC6)nc4c3F)c12] |
| 035 | 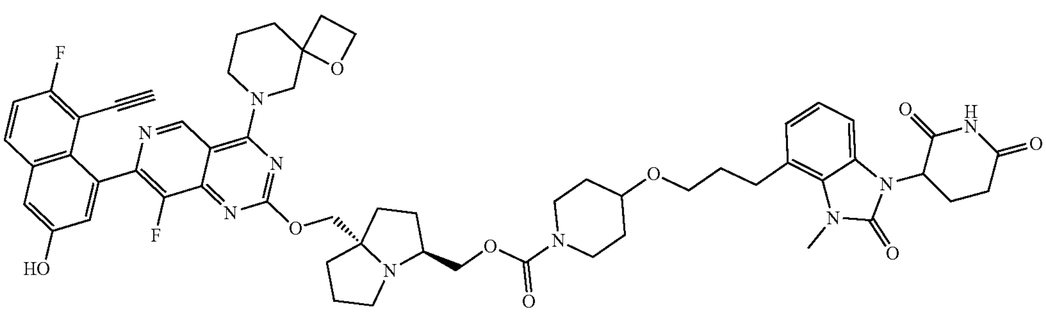 [SMILES: C#Cc1c(F)ccc2cc(O)cc(-c3ncc4c(N5CCCC6(CCO6)C5)nc(OC[C@@]56CCCN5[C@H](COC(=O)N5CCC(OCCCc7cccc8c7n(C)c(=O)n8C7CCC(=O)NC7=O)CC5)CC6)nc4c3F)c12] |
| 036 | 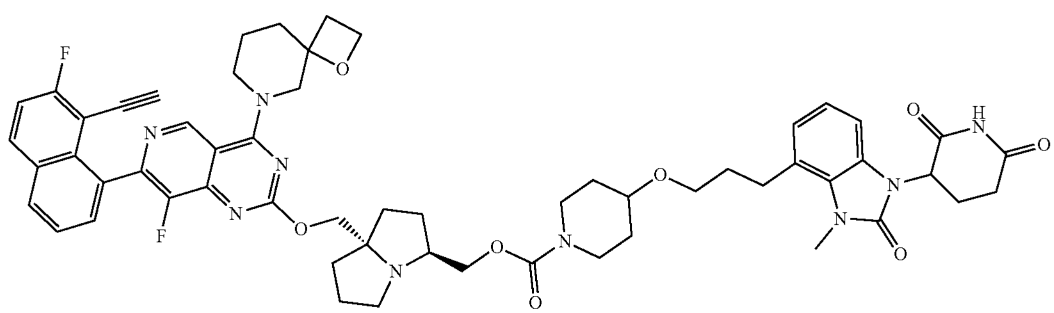 [SMILES: C#Cc1c(F)ccc2cccc(-c3ncc4c(N5CCCC6(CCO6)C5)nc(OC[C@@]56CCCN5[C@H](COC(=O)N5CCC(OCCCc7cccc8c7n(C)c(=O)n8C7CCC(=O)NC7=O)CC5)CC6)nc4c3F)c12] |

TABLE 1-continued

Example Compounds of the Disclosure

| Compound No. | Compound Structure |
| --- | --- |
| 037 | 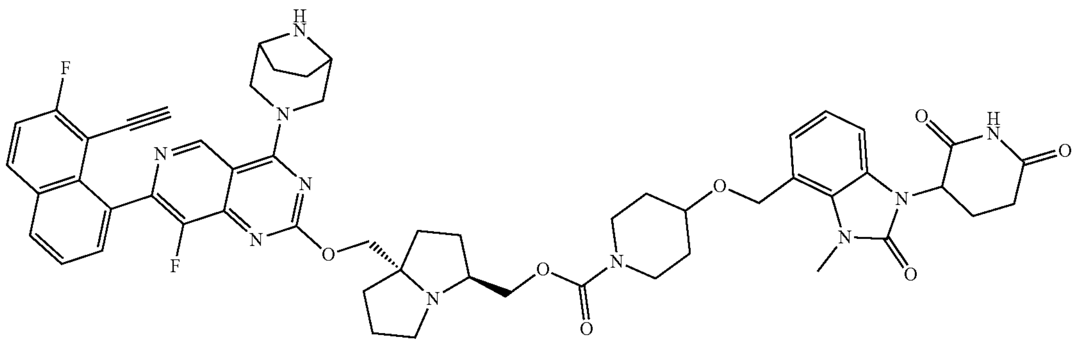 [SMILES: C#Cc1c(F)ccc2cccc(-c3ncc4c(N5CC6CCC(C5)N6)nc(OC[C@@]56CCCN5[C@H](COC(=O)N5CCC(OCc7cccc8c7n(C)c(=O)n8C7CCC(=O)NC7=O)CC5)CC6)nc4c3F)c12] |
| 038 | 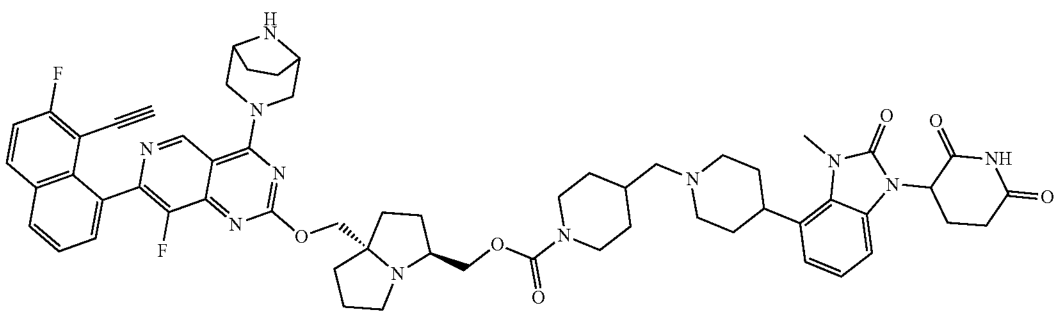 [SMILES: C#Cc1c(F)ccc2cccc(-c3ncc4c(N5CC6CCC(C5)N6)nc(OC[C@@]56CCCN5[C@H](COC(=O)N5CCC(CN7CCC(c8cccc9c8n(C)c(=O)n9C8CCC(=O)NC8=O)CC7)CC5)CC6)nc4c3F)c12] |
| 039 | 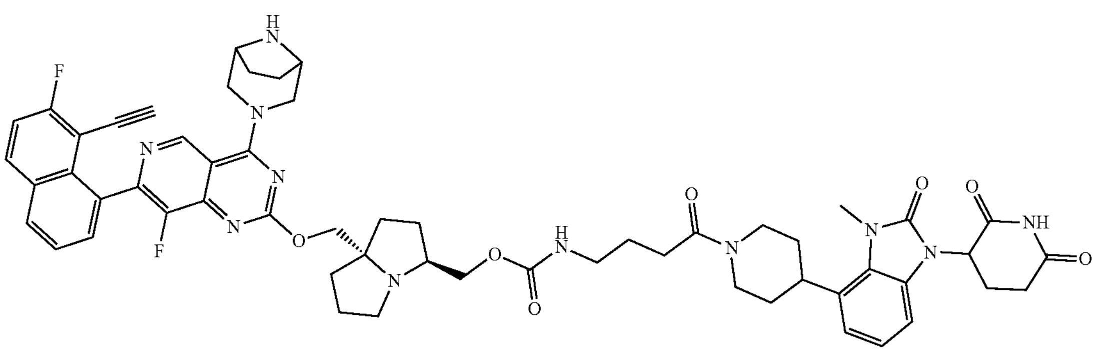 [SMILES: C#Cc1c(F)ccc2cccc(-c3ncc4c(N5CC6CCC(C5)N6)nc(OC[C@@]56CCCN5[C@H](COC(=O)NCCCC(=O)N5CCC(c7cccc8c7n(C)c(=O)n8C7CCC(=O)NC7=O)CC5)CC6)nc4c3F)c12] |
| 040 | 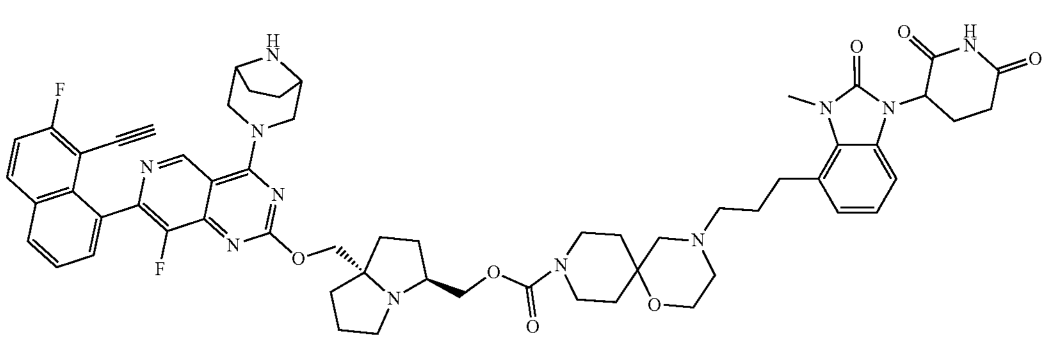 [SMILES: C#Cc1c(F)ccc2cccc(-c3ncc4c(N5CC6CCC(C5)N6)nc(OC[C@@]56CCCN5[C@H](COC(=O)N5CCC7(CC5)CN(CCCc5cccc8c5n(C)c(=O)n8C5CCC(=O)NC5=O)CCO7)CC6)nc4c3F)c12] |

TABLE 1-continued

Example Compounds of the Disclosure

| Compound No. | Compound Structure |
|---|---|
| 041 | 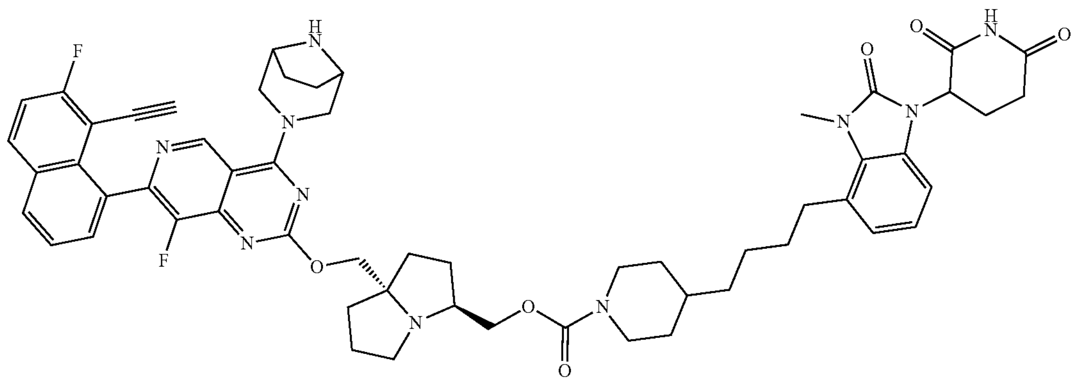 [SMILES: C#Cc1c(F)ccc2cccc(-c3ncc4c(N5CC6CCC(C5)N6)nc(OC[C@@]56CCCN5[C@H](COC(=O)N5CCC(CCCCc7cccc8c7n(C)c(=O)n8C7CCC(=O)NC7=O)CC5)CC6)nc4c3F)c12] |
| 042 | 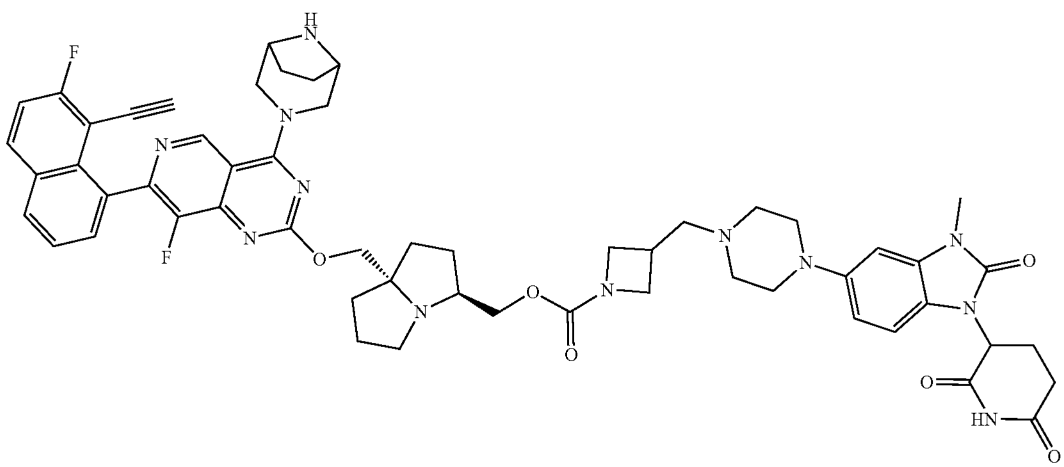 [SMILES: C#Cc1c(F)ccc2cccc(-c3ncc4c(N5CC6CCC(C5)N6)nc(OC[C@@]56CCCN5[C@H](COC(=O)N5CC(CN7CCN(c8ccc9c(c8)n(C)c(=O)n9C8CCC(=O)NC8=O)CC7)C5)CC6)nc4c3F)c12] |
| 043 | 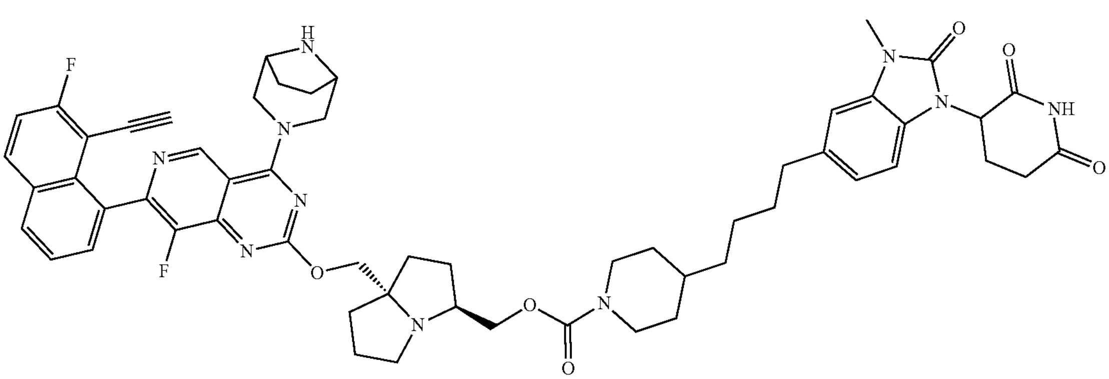 [SMILES: C#Cc1c(F)ccc2cccc(-c3ncc4c(N5CC6CCC(C5)N6)nc(OC[C@@]56CCCN5[C@H](COC(=O)N5CCC(CCCCc7ccc8c(c7)n(C)c(=O)n8C7CCC(=O)NC7=O)CC5)CC6)nc4c3F)c12] |

TABLE 1-continued

Example Compounds of the Disclosure

| Compound No. | Compound Structure |
| --- | --- |
| 044 | 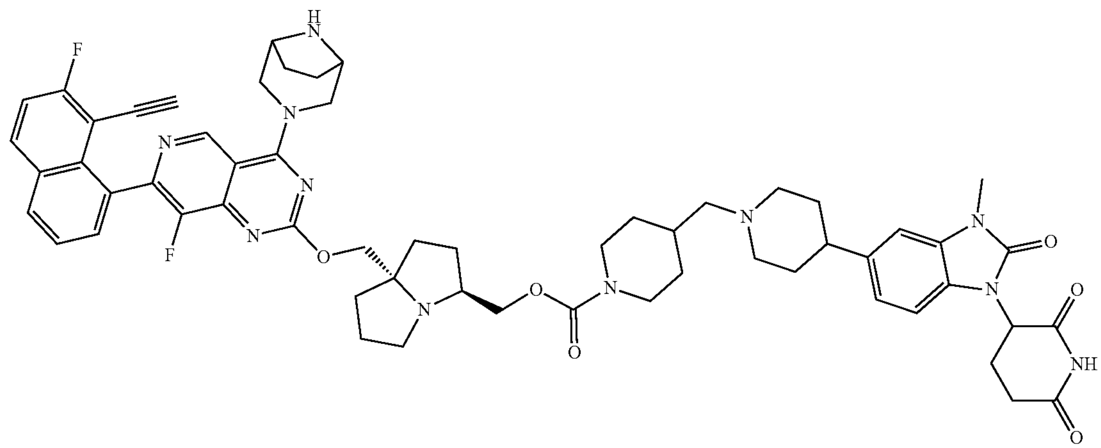 [SMILES: C#Cc1c(F)ccc2cccc(-c3ncc4c(N5CC6CCC(C5)N6)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 045 | 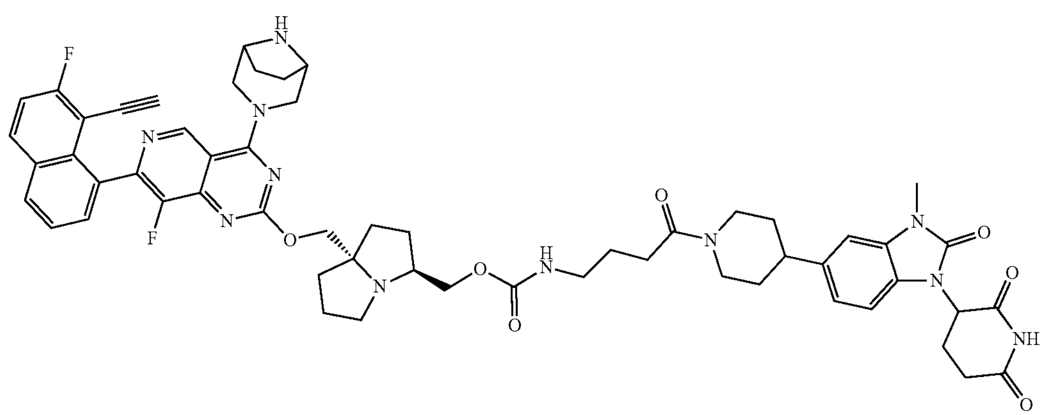 [SMILES: C#Cc1c(F)ccc2cccc(-c3ncc4c(N5CC6CCC(C5)N6)nc(OC[C@@]56CCCN5[C@H](COC(=O)NCCCC(=O)N5CCC(c7ccc8c(c7)n(C)c(=O)n8C7CCC(=O)NC7=O)CC5)CC6)nc4c3F)c12] |
| 046 | 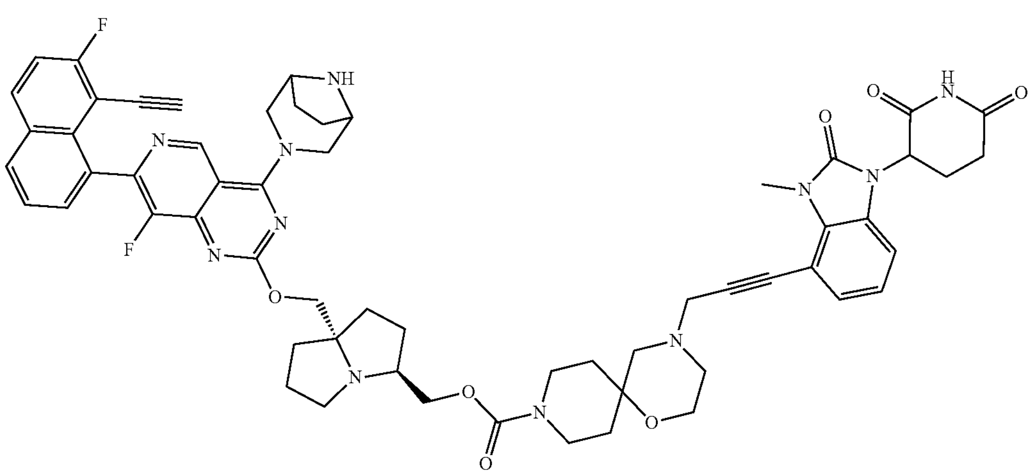 [SMILES: C#Cc1c(F)ccc2cccc(-c3ncc4c(N5CC6CCC(C5)N6)nc(OC[C@@]56CCCN5[C@H](COC(=O)N5CCC7(CC5)CN(CC#Cc5cccc8c5n(C)c(=O)n8C5CCC(=O)NC5=O)CCO7)CC6)nc4c3F)c12] |

TABLE 1-continued
Example Compounds of the Disclosure
| Compound No. | Compound Structure |
|---|---|
| 047 | 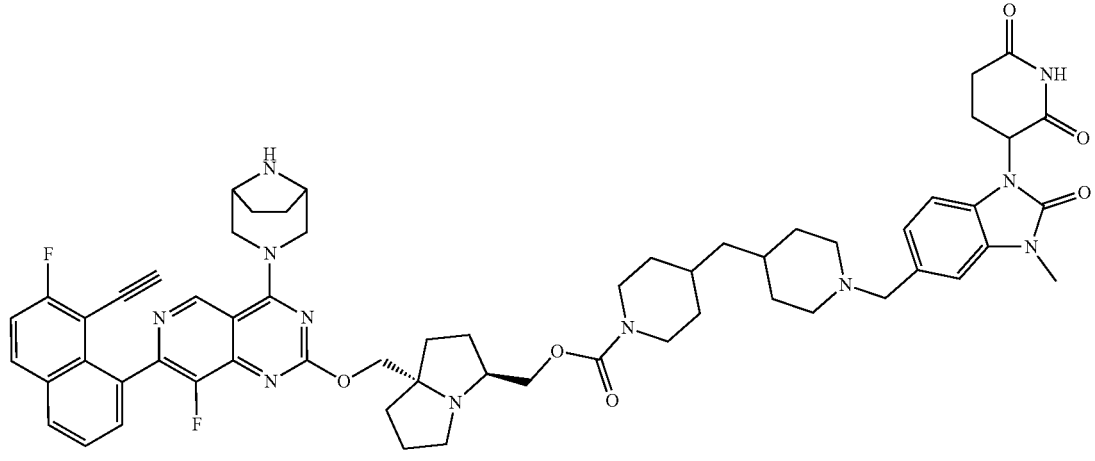 [SMILES: C#Cc1c(F)ccc2cccc(-c3ncc4c(N5CC6CCC(C5)N6)nc(OC[C@@]56CCCN5[C@H](COC(=O)N5CCC(CC7CCN(Cc8ccc9c(c8)n(C)c(=O)n9C8CCC(=O)NC8=O)CC7)CC5)CC6)nc4c3F)c12] |
| 048 | 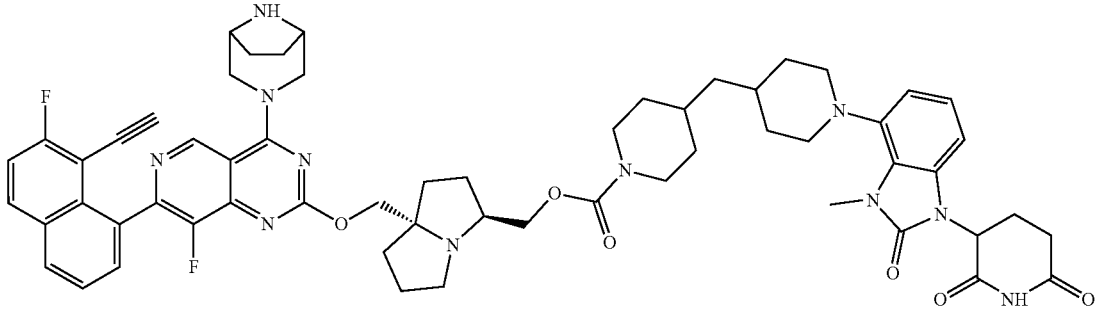 [SMILES: C#Cc1c(F)ccc2cccc(-c3ncc4c(N5CC6CCC(C5)N6)nc(OC[C@@]56CCCN5[C@H](COC(=O)N5CCC(CC7CCN(c8cccc9c8n(C)c(=O)n9C8CCC(=O)NC8=O)CC7)CC5)CC6)nc4c3F)c12] |
| 049 | 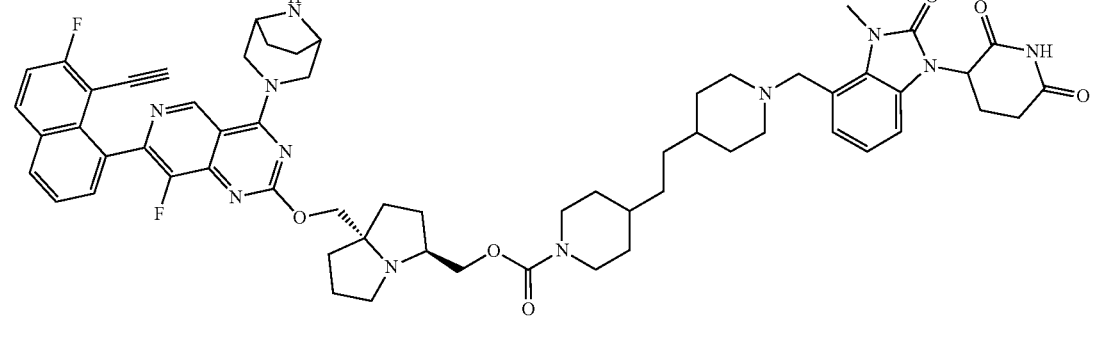 |
| 050 | 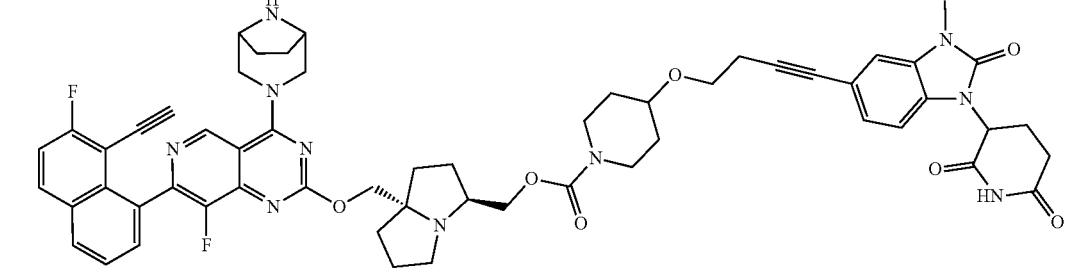 |

TABLE 1-continued
Example Compounds of the Disclosure
| Compound No. | Compound Structure |
|---|---|
| 051 | 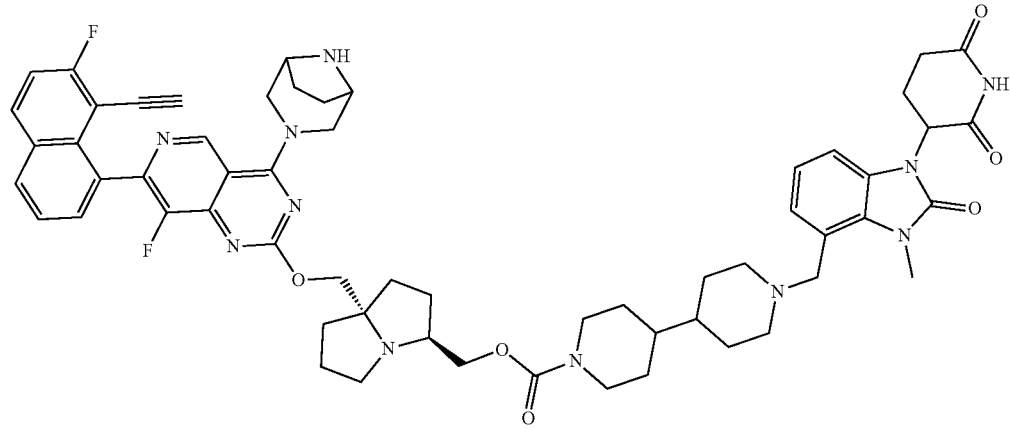 [SMILES: C#Cc1c(F)ccc2cccc(-c3ncc4c(N5CC6CCC(C5)N6)nc(OC[C@@]56CCCN5[C@H](COC(=O)N5CCC(C7CCN(Cc8cccc9c8n(C)c(=O)n9C8CCC(=O)NC8=O)CC7)CC5)CC6)nc4c3F)c12] |
| 052 | 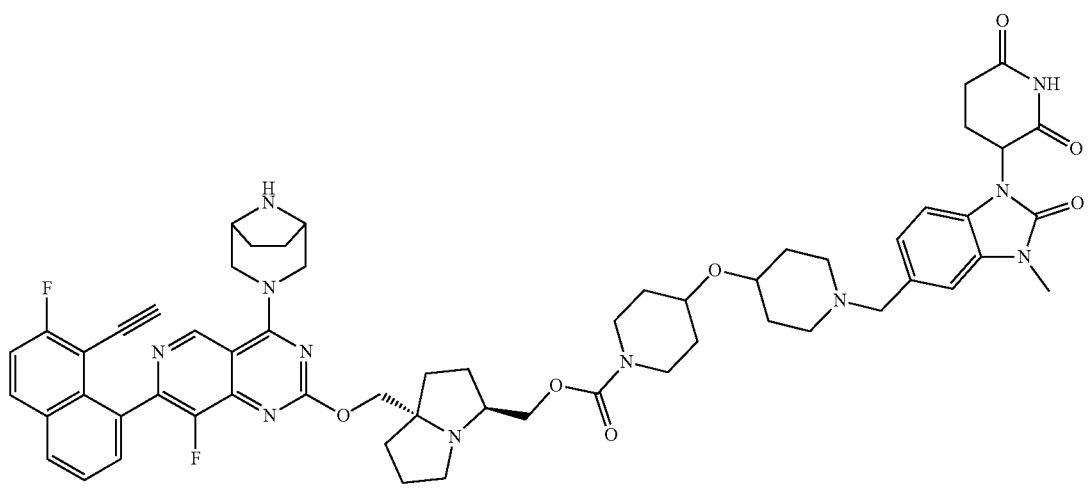 [SMILES: C#Cc1c(F)ccc2cccc(-c3ncc4c(N5CC6CCC(C5)N6)nc(OC[C@@]56CCCN5[C@H](COC(=O)N5CCC(OC7CCN(Cc8ccc9c(c8)n(C)c(=O)n9C8CCC(=O)NC8=O)CC7)CC5)CC6)nc4c3F)c12] |
| 053 | 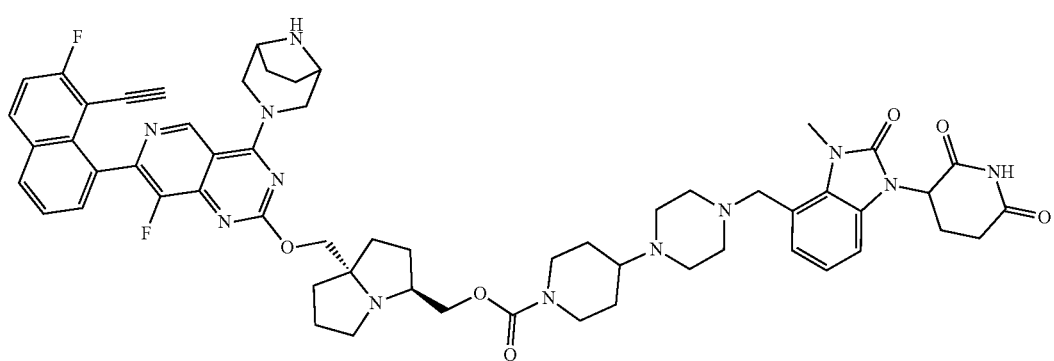 [SMILES: C#Cc1c(F)ccc2cccc(-c3ncc4c(N5CC6CCC(C5)N6)nc(OC[C@@]56CCCN5[C@H](COC(=O)N5CCC(N7CCN(Cc8cccc9c8n(C)c(=O)n9C8CCC(=O)NC8=O)CC7)CC5)CC6)nc4c3F)c12] |

TABLE 1-continued

Example Compounds of the Disclosure

| Compound No. | Compound Structure |
| --- | --- |
| 054 | 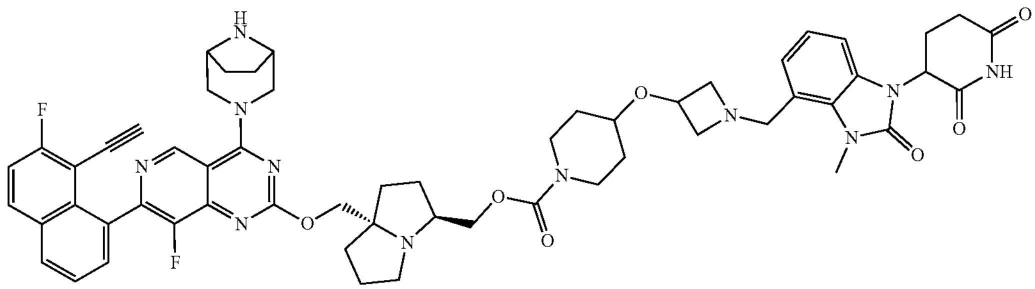 [SMILES: C#Cc1c(F)ccc2cccc(-c3ncc4c(N5CC6CCC(C5)N6)nc(OC[C@@]56CCCN5[C@H](COC(=O)N5CCC(OC7CN(Cc8cccc9c8n(C)c(=O)n9C8CCC(=O)NC8=O)C7)CC5)CC6)nc4c3F)c12] |
| 055 | 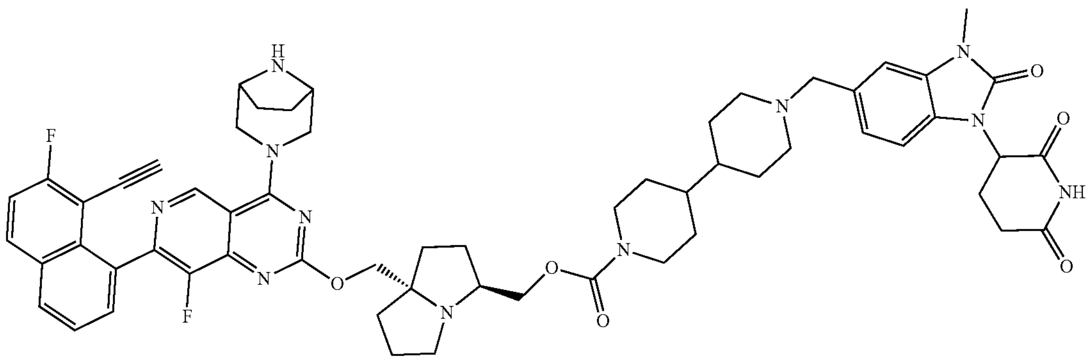 [SMILES: C#Cc1c(F)ccc2cccc(-c3ncc4c(N5CC6CCC(C5)N6)nc(OC[C@@]56CCCN5[C@H](COC(=O)N5CCC(C7CCN(Cc8ccc9c(c8)n(C)c(=O)n9C8CCC(=O)NC8=O)CC7)CC5)CC6)nc4c3F)c12] |
| 056 | 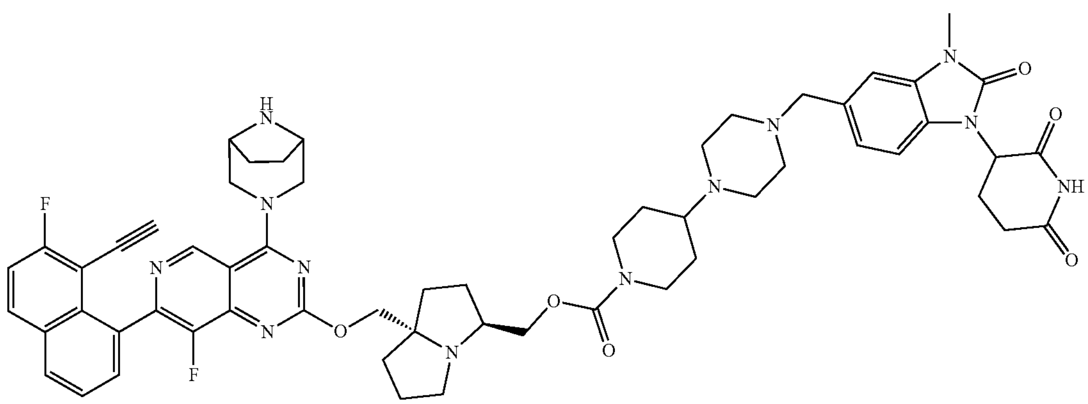 [SMILES: C#Cc1c(F)ccc2cccc(-c3ncc4c(N5CC6CCC(C5)N6)nc(OC[C@@]56CCCN5[C@H](COC(=O)N5CCC(N7CCN(Cc8ccc9c(c8)n(C)c(=O)n9C8CCC(=O)NC8=O)CC7)CC5)CC6)nc4c3F)c12] |
| 057 | 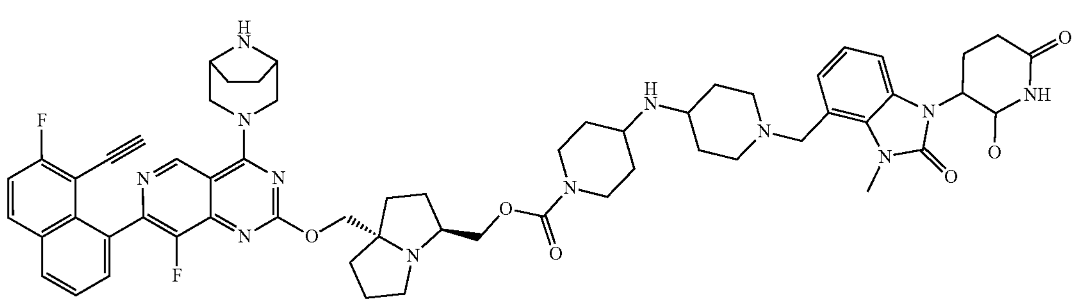 [SMILES: C#Cc1c(F)ccc2cccc(-c3ncc4c(N5CC6CCC(C5)N6)nc(OC[C@@]56CCCN5[C@H](COC(=O)N5CCC(NC7CCN(Cc8cccc9c8n(C)c(=O)n9C8CCC(=O)NC8O)CC7)CC5)CC6)nc4c3F)c12] |

TABLE 1-continued
Example Compounds of the Disclosure
| Compound No. | Compound Structure |
|---|---|
| 058 | 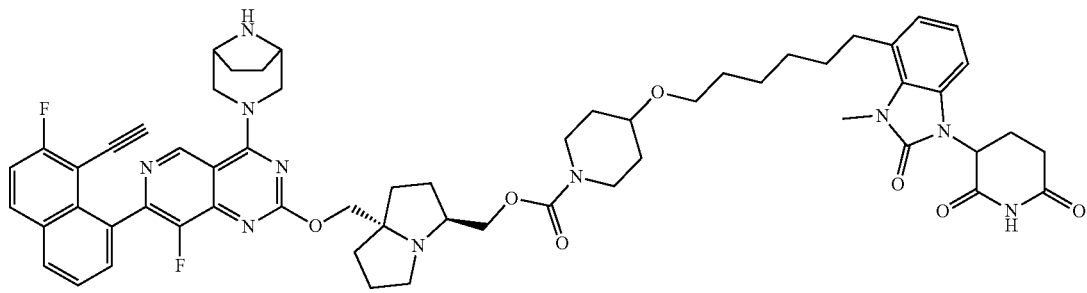 [SMILES: C#Cc1c(F)ccc2cccc(-c3ncc4c(N5CC6CCC(C5)N6)nc(OC[C@@]56CCCN5[C@H](COC(=O)N5CCC(OCCCCCCc7cccc8c7n(C)c(=O)n8C7CCC(=O)NC7=O)CC5)CC6)nc4c3F)c12] |
| 059 | 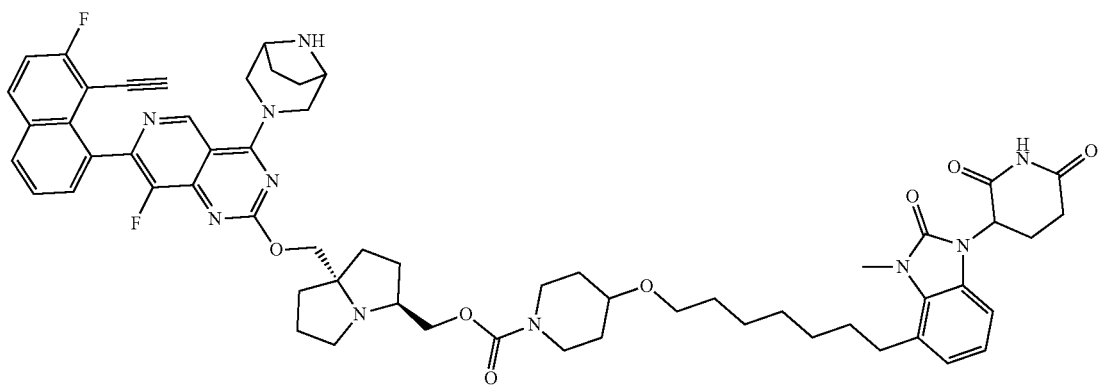 [SMILES: C#Cc1c(F)ccc2cccc(-c3ncc4c(N5CC6CCC(C5)N6)nc(OC[C@@]56CCCN5[C@H](COC(=O)N5CCC(OCCCCCCCc7cccc8c7n(C)c(=O)n8C7CCC(=O)NC7=O)CC5)CC6)nc4c3F)c12] |
| 060 | 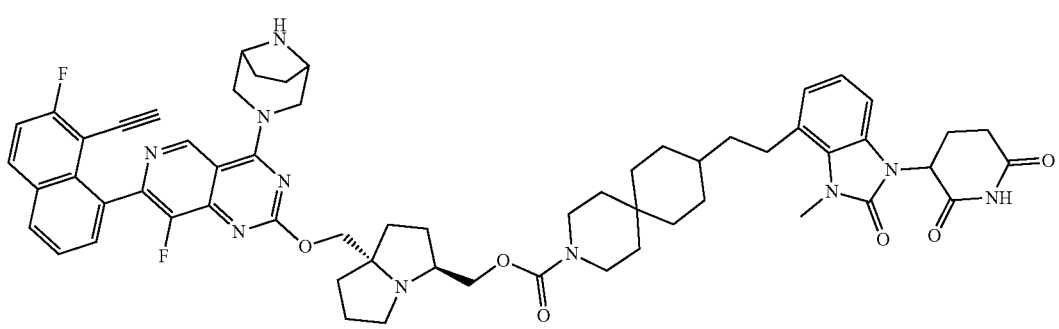 [SMILES: C#Cc1c(F)ccc2cccc(-c3ncc4c(N5CC6CCC(C5)N6)nc(OC[C@@]56CCCN5[C@H](COC(=O)N5CCC7(CCC(CCc8cccc9c8n(C)c(=O)n9C8CCC(=O)NC8=O)CC7)CC5)CC6)nc4c3F)c12] |
| 061 | 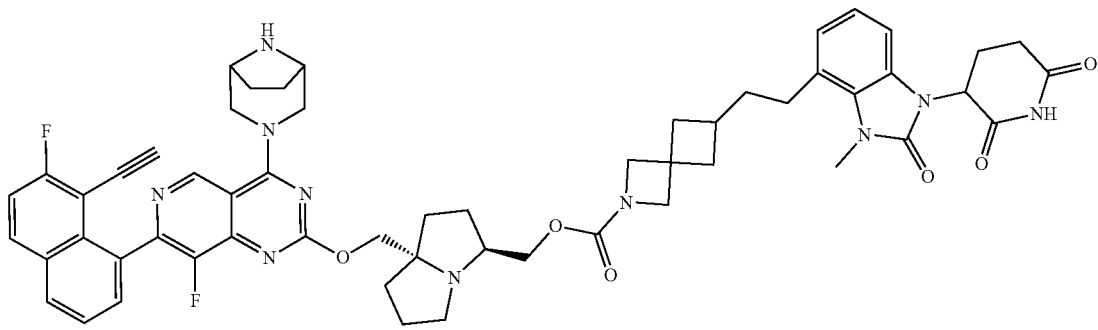 [SMILES: C#Cc1c(F)ccc2cccc(-c3ncc4c(N5CC6CCC(C5)N6)nc(OC[C@@]56CCCN5[C@H](COC(=O)N5CC7(CC(CCc8cccc9c8n(C)c(=O)n9C8CCC(=O)NC8=O)C7)C5)CC6)nc4c3F)c12] |

TABLE 1-continued

Example Compounds of the Disclosure

| Compound No. | Compound Structure |
|---|---|
| 062 | 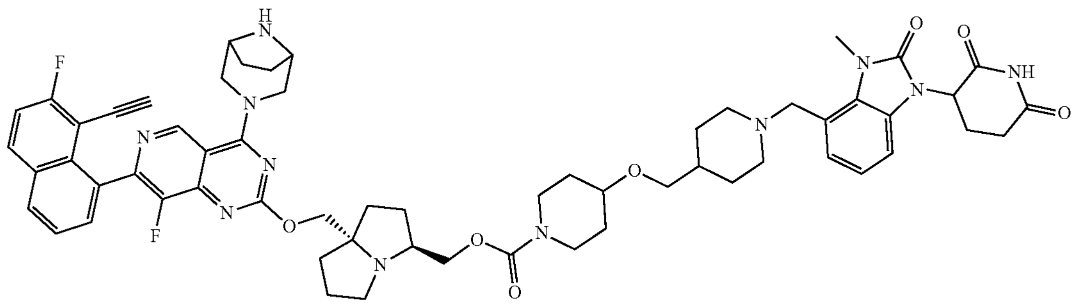 [SMILES: C#Cc1c(F)ccc2cccc(-c3ncc4c(N5CC6CCC(C5)N6)nc(OC[C@@]56CCCN5[C@H](COC(=O)N5CCC(OCC7CCN(Cc8cccc9c8n(C)c(=O)n9C8CCC(=O)NC8=O)CC7)CC5)CC6)nc4c3F)c12] |
| 063 | 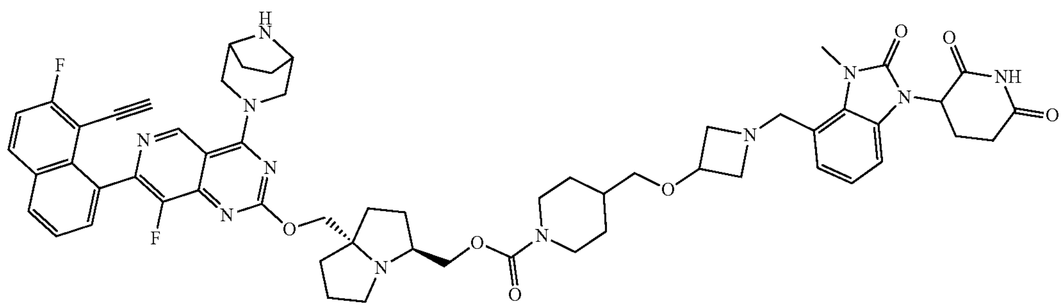 [SMILES: C#Cc1c(F)ccc2cccc(-c3ncc4c(N5CC6CCC(C5)N6)nc(OC[C@@]56CCCN5[C@H](COC(=O)N5CCC(COC7CN(Cc8cccc9c8n(C)c(=O)n9C8CCC(=O)NC8=O)C7)CC5)CC6)nc4c3F)c12] |
| 064 | 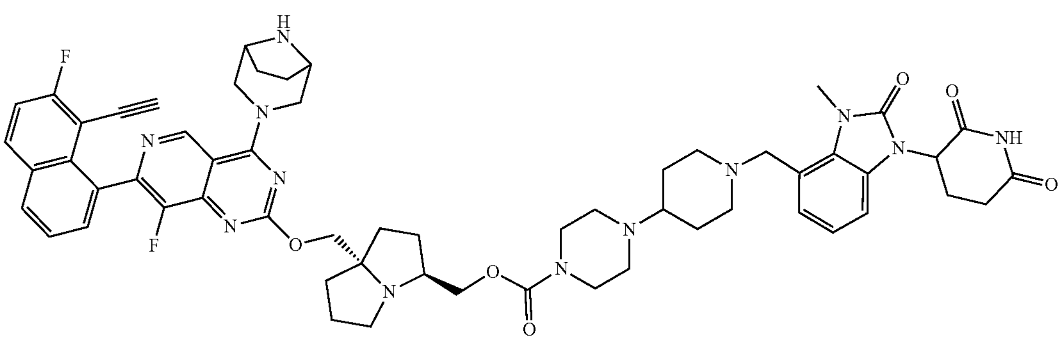 [SMILES: C#Cc1c(F)ccc2cccc(-c3ncc4c(N5CC6CCC(C5)N6)nc(OC[C@@]56CCCN5[C@H](COC(=O)N5CCN(C7CCN(Cc8cccc9c8n(C)c(=O)n9C8CCC(=O)NC8=O)CC7)CC5)CC6)nc4c3F)c12] |
| 065 | 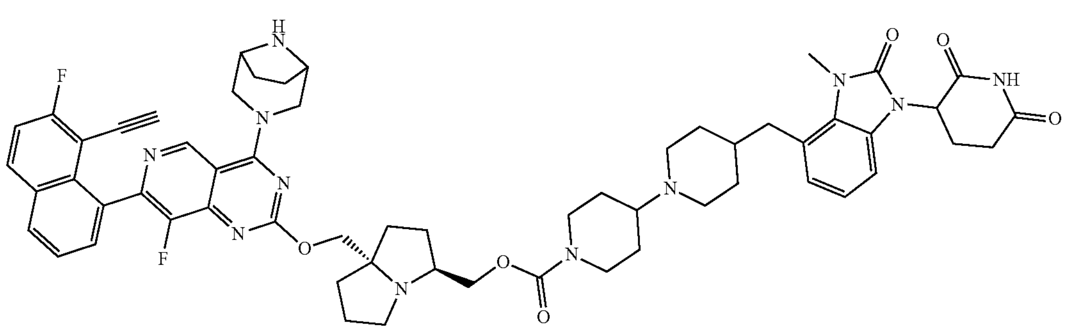 [SMILES: C#Cc1c(F)ccc2cccc(-c3ncc4c(N5CC6CCC(C5)N6)nc(OC[C@@]56CCCN5[C@H](COC(=O)N5CCC(N7CCC(Cc8cccc9c8n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 066 | 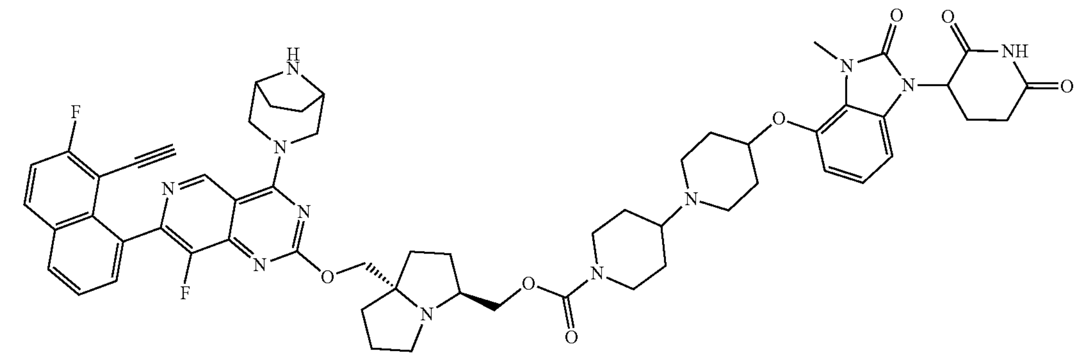 [SMILES: C#Cc1c(F)ccc2cccc(-c3ncc4c(N5CC6CCC(C5)N6)nc(OC[C@@]56CCCN5[C@H](COC(=O)N5CCC(N7CCC(Oc8cccc9c8n(C)c(=O)n9C8CCC(=O)NC8=O)CC7)CC5)CC6)nc4c3F)c12] |
| 067 | 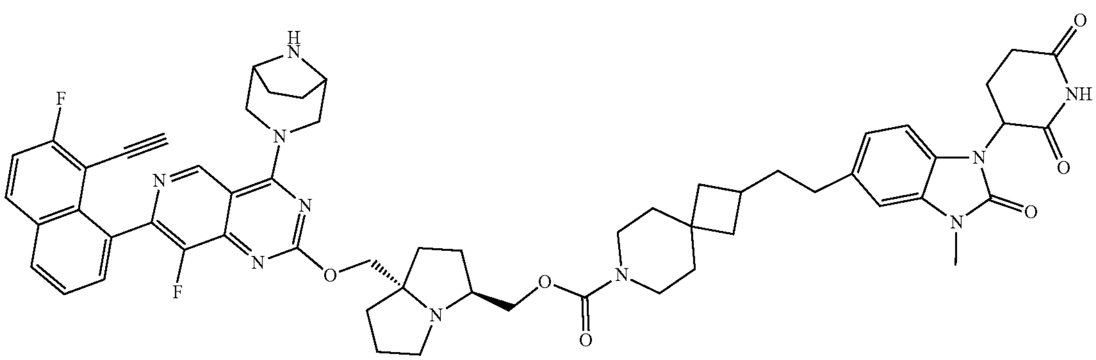 [SMILES: C#Cc1c(F)ccc2cccc(-c3ncc4c(N5CC6CCC(C5)N6)nc(OC[C@@]56CCCN5[C@H](COC(=O)N5CCC7(CC5)CC(CCc5ccc8c(c5)n(C)c(=O)n8C5CCC(=O)NC5=O)C7)CC6)nc4c3F)c12] |
| 068 | 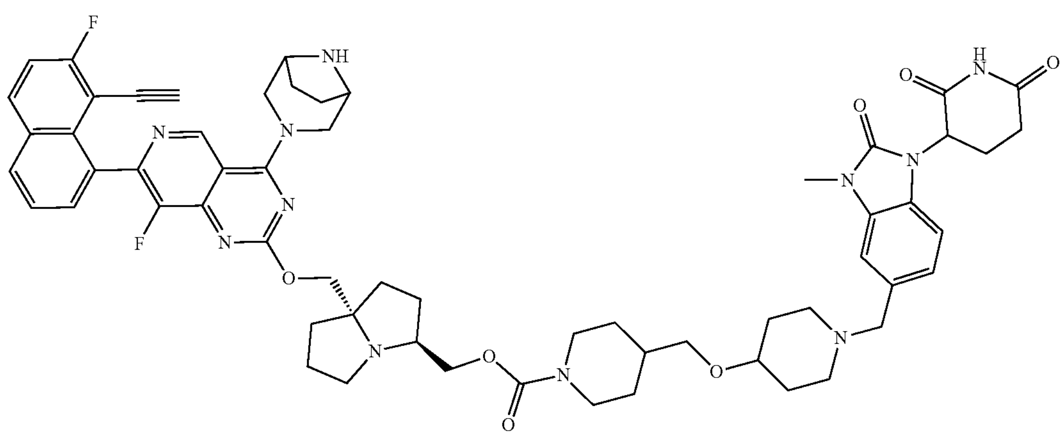 [SMILES: C#Cc1c(F)ccc2cccc(-c3ncc4c(N5CC6CCC(C5)N6)nc(OC[C@@]56CCCN5[C@H](COC(=O)N5CCC(COC7CCN(Cc8ccc9c(c8)n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 069 | 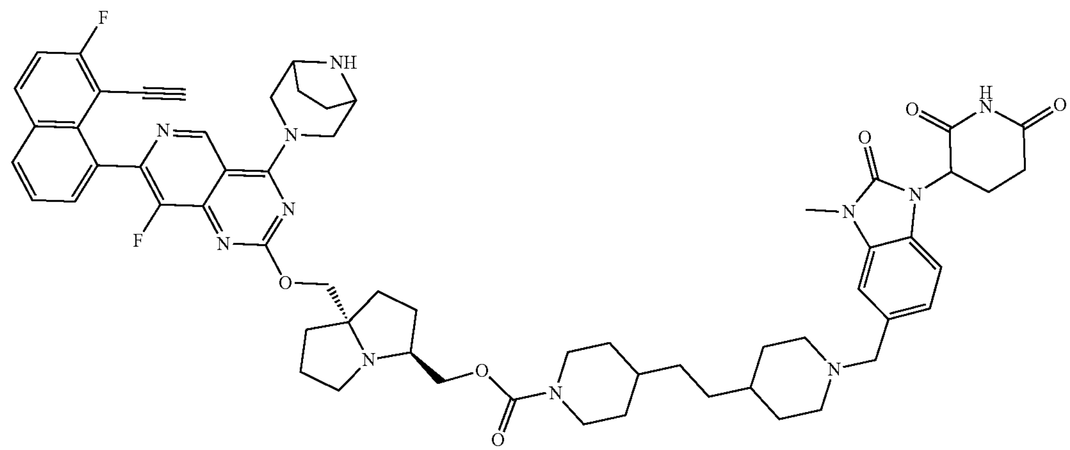 [SMILES: C#Cc1c(F)ccc2cccc(-c3ncc4c(N5CC6CCC(C5)N6)nc(OC[C@@]56CCCN5[C@H](COC(=O)N5CCC(CCC7CCN(Cc8ccc9c(c8)n(C)c(=O)n9C8CCC(=O)NC8=O)CC7)CC5)CC6)nc4c3F)c12] |
| 070 | 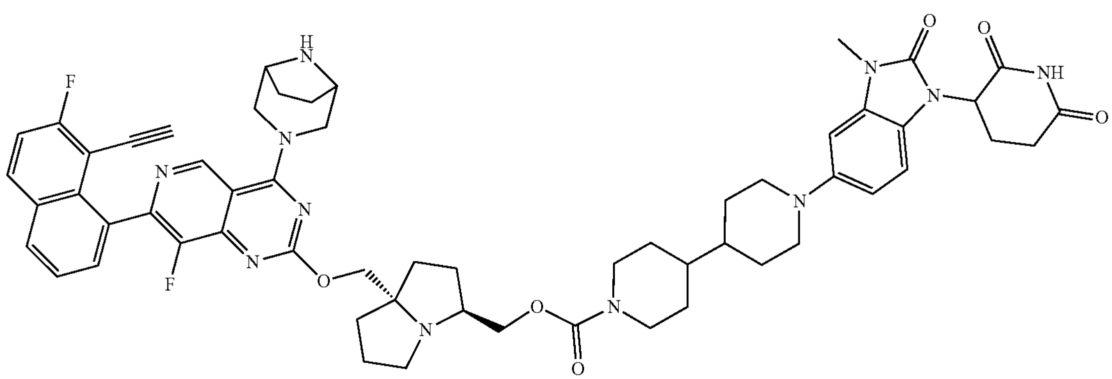 [SMILES: C#Cc1c(F)ccc2cccc(-c3ncc4c(N5CC6CCC(C5)N6)nc(OC[C@@]56CCCN5[C@H](COC(=O)N5CCC(C7CCN(c8ccc9c(c8)n(C)c(=O)n9C8CCC(=O)NC8=O)CC7)CC5)CC6)nc4c3F)c12] |
| 071 | 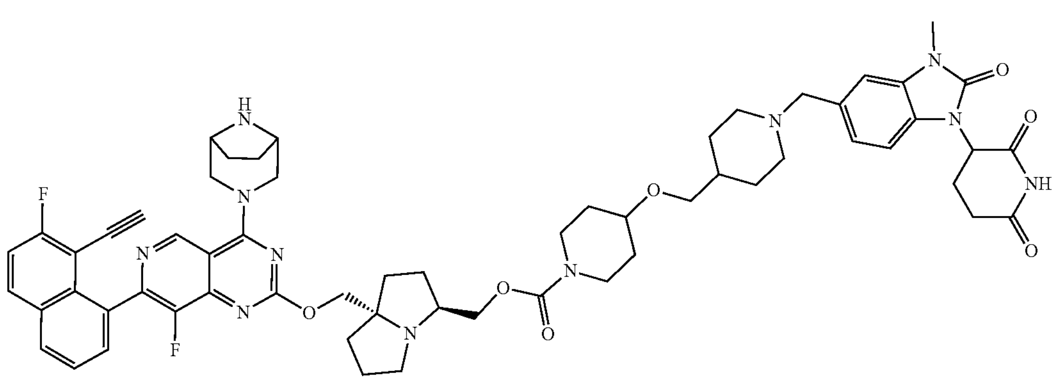 [SMILES: C#Cc1c(F)ccc2cccc(-c3ncc4c(N5CC6CCC(C5)N6)nc(OC[C@@]56CCCN5[C@H](COC(=O)N5CCC(OCC7CCN(Cc8ccc9c(c8)n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 072 | 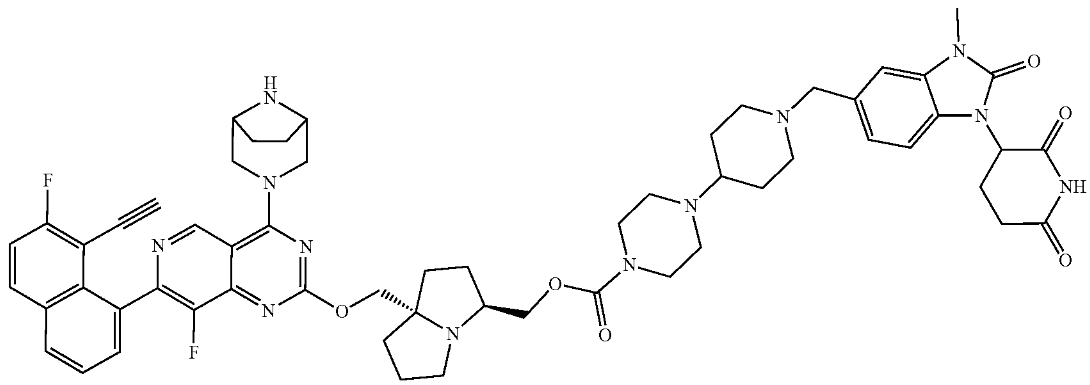 [SMILES: C#Cc1c(F)ccc2cccc(-c3ncc4c(N5CC6CCC(C5)N6)nc(OC[C@@]56CCCN5[C@H](COC(=O)N5CCN(C7CCN(Cc8ccc9c(c8)n(C)c(=O)n9C8CCC(=O)NC8=O)CC7)CC5)CC6)nc4c3F)c12] |
| 073 | 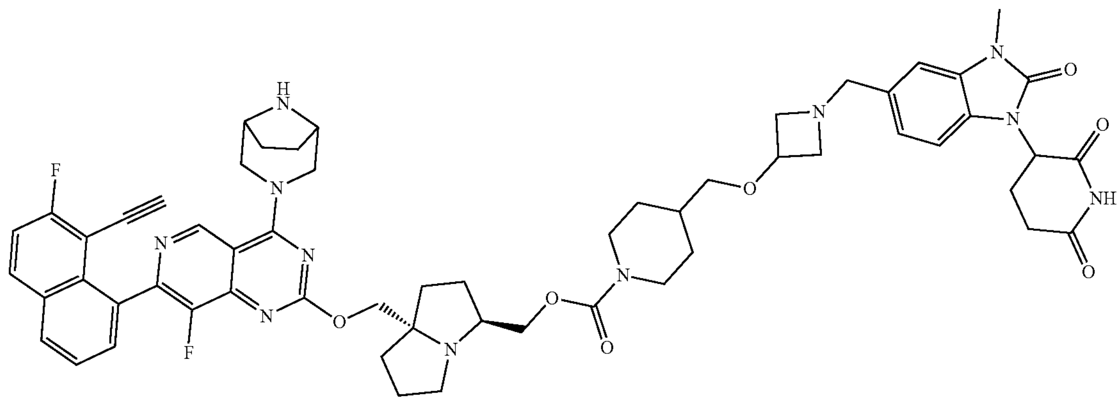 [SMILES: C#Cc1c(F)ccc2cccc(-c3ncc4c(N5CC6CCC(C5)N6)nc(OC[C@@]56CCCN5[C@H](COC(=O)N5CCC(COC7CN(Cc8ccc9c(c8)n(C)c(=O)n9C8CCC(=O)NC8=O)C7)CC5)CC6)nc4c3F)c12] |
| 074 | 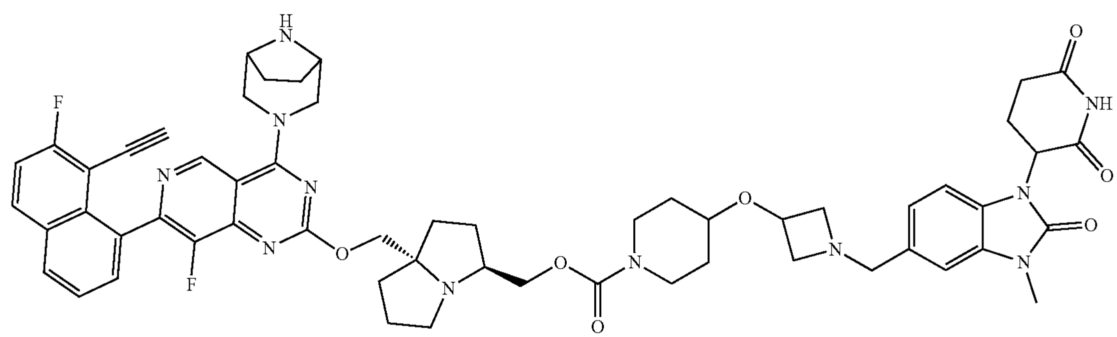 [SMILES: C#Cc1c(F)ccc2cccc(-c3ncc4c(N5CC6CCC(C5)N6)nc(OC[C@@]56CCCN5[C@H](COC(=O)N5CCC(OC7CN(Cc8ccc9c(c8)n(C)c(=O)n9C8CCC(=O)NC8=O)C7)CC5)CC6)nc4c3F)c12] |
| 075 | 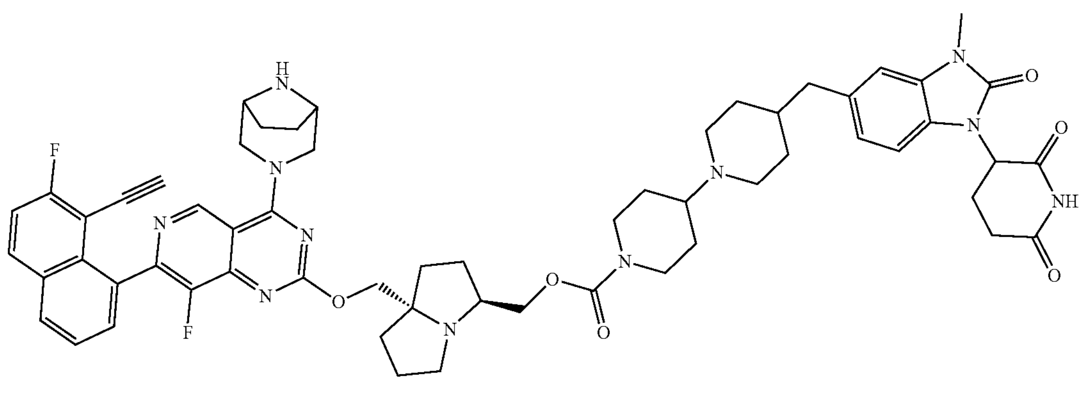 [SMILES: C#Cc1c(F)ccc2cccc(-c3ncc4c(N5CC6CCC(C5)N6)nc(OC[C@@]56CCCN5[C@H](COC(=O)N5CCC(N7CCC(Cc8ccc9c(c8)n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 076 | 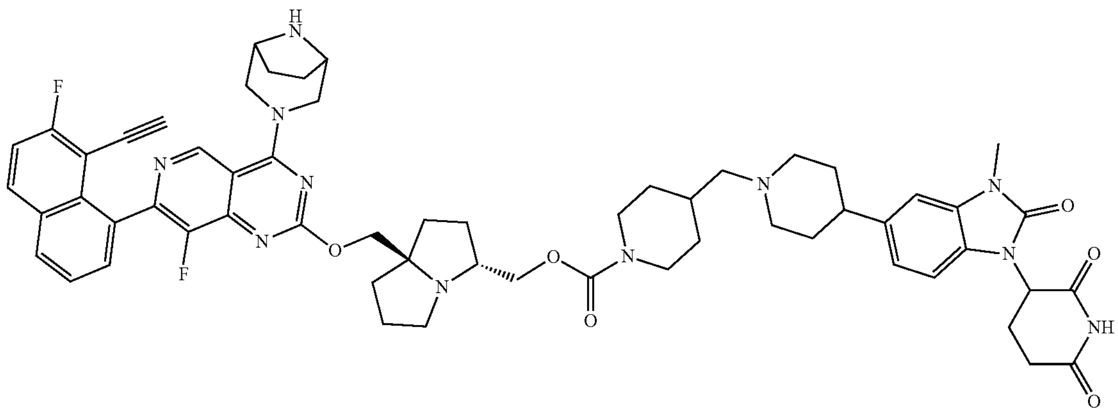 [SMILES: C#Cc1c(F)ccc2cccc(-c3ncc4c(N5CC6CCC(C5)N6)nc(OC[C@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |
| 077 | 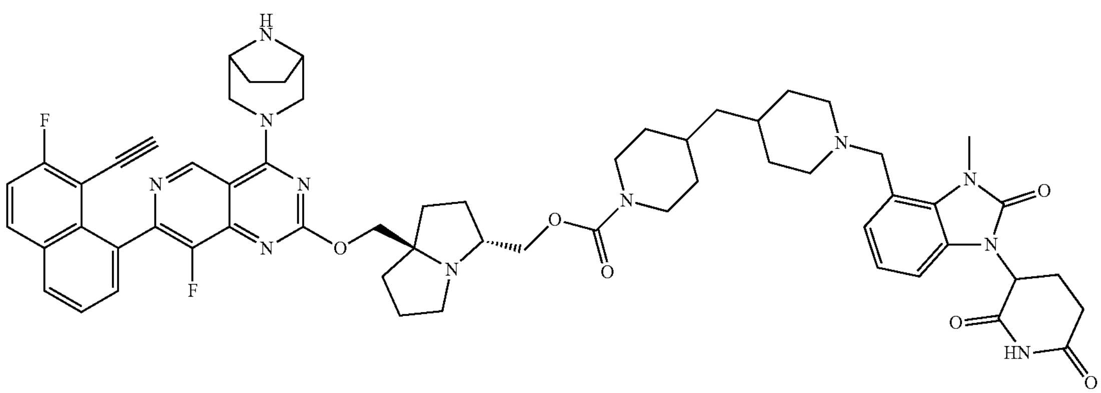 [SMILES: C#Cc1c(F)ccc2cccc(-c3ncc4c(N5CC6CCC(C5)N6)nc(OC[C@]56CCCN5[C@@H](COC(=O)N5CCC(CC7CCN(Cc8cccc9c8n(C)c(=O)n9C8CCC(=O)NC8=O)CC7)CC5)CC6)nc4c3F)c12] |
| 078 | 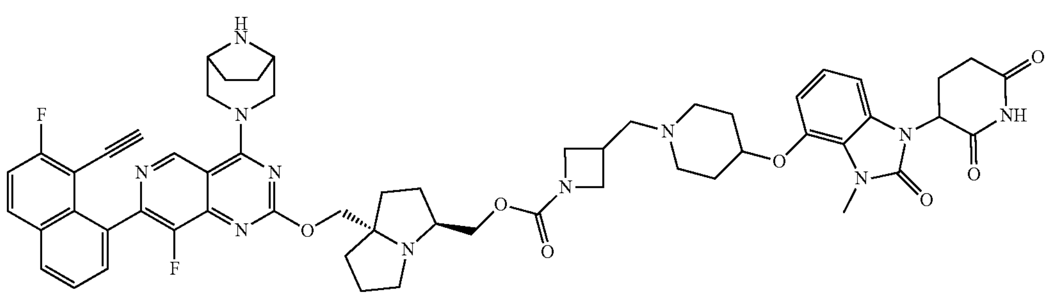 [SMILES: C#Cc1c(F)ccc2cccc(-c3ncc4c(N5CC6CCC(C5)N6)nc(OC[C@@]56CCCN5[C@H](COC(=O)N5CC(CN7CCC(Oc8cccc9c8n(C)c(=O)n9C8CCC(=O)NC8=O)CC7)C5)CC6)nc4c3F)c12] |
| 079 | 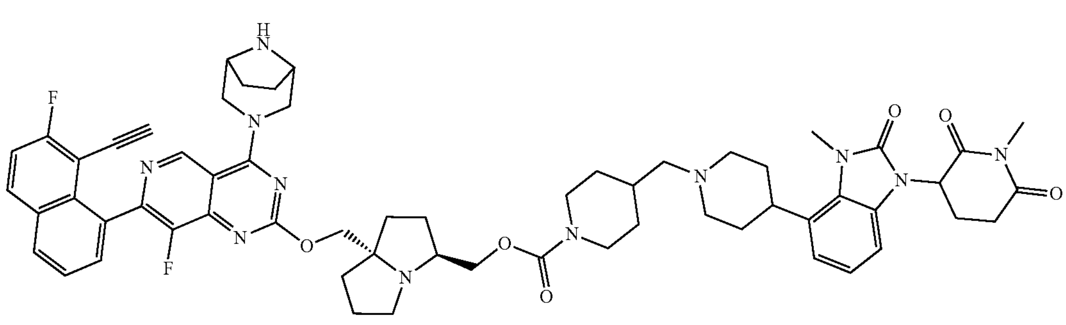 [SMILES: C#Cc1c(F)ccc2cccc(-c3ncc4c(N5CC6CCC(C5)N6)nc(OC[C@@]56CCCN5[C@H](COC(=O)N5CCC(CN7CCC(c8cccc9c8n(C)c(=O)n9C8CCC(=O)N(C)C8=O)CC7)CC5)CC6)nc4c3F)c12] |

TABLE 1-continued

Example Compounds of the Disclosure

| Compound No. | Compound Structure |
|---|---|
| 080 | 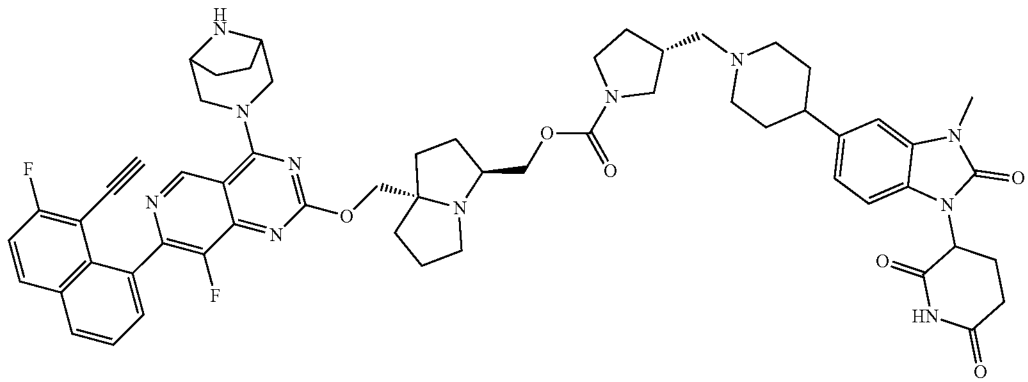 [SMILES: C#Cc1c(F)ccc2cccc(-c3ncc4c(N5CC6CCC(C5)N6)nc(OC[C@@]56CCCN5[C@H](COC(=O)N5CC[C@H](CN7CCC(c8ccc9c(c8)n(C)c(=O)n9C8CCC(=O)NC8=O)CC7)C5)CC6)nc4c3F)c12] |
| 081 | 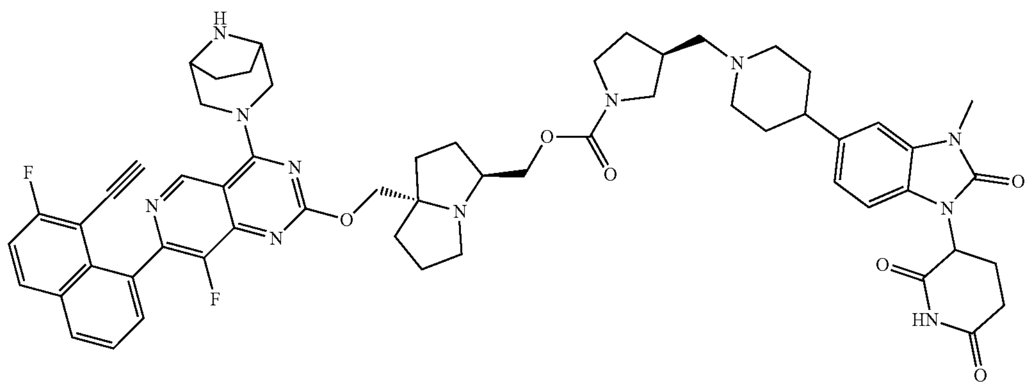 [SMILES: C#Cc1c(F)ccc2cccc(-c3ncc4c(N5CC6CCC(C5)N6)nc(OC[C@@]56CCCN5[C@H](COC(=O)N5CC[C@@H](CN7CCC(c8ccc9c(c8)n(C)c(=O)n9C8CCC(=O)NC8=O)CC7)C5)CC6)nc4c3F)c12] |
| 082 | 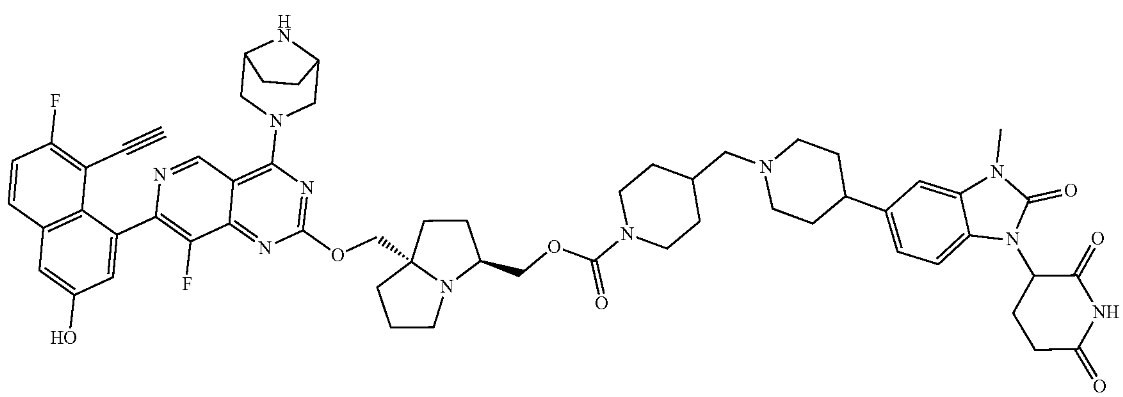 [SMILES: C#Cc1c(F)ccc2cc(O)cc(-c3ncc4c(N5CC6CCC(C5)N6)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 083 | 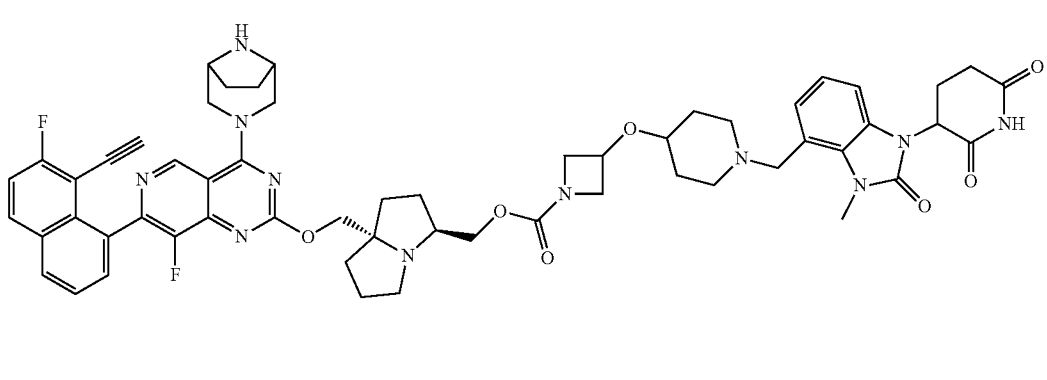 [SMILES: C#Cc1c(F)ccc2cccc(-c3ncc4c(N5CC6CCC(C5)N6)nc(OC[C@@]56CCCN5[C@H](COC(=O)N5CC(OC7CCN(Cc8cccc9c8n(C)c(=O)n9C8CCC(=O)NC8=O)CC7)C5)CC6)nc4c3F)c12] |

TABLE 1-continued

Example Compounds of the Disclosure

| Compound No. | Compound Structure |
|---|---|
| 084 | 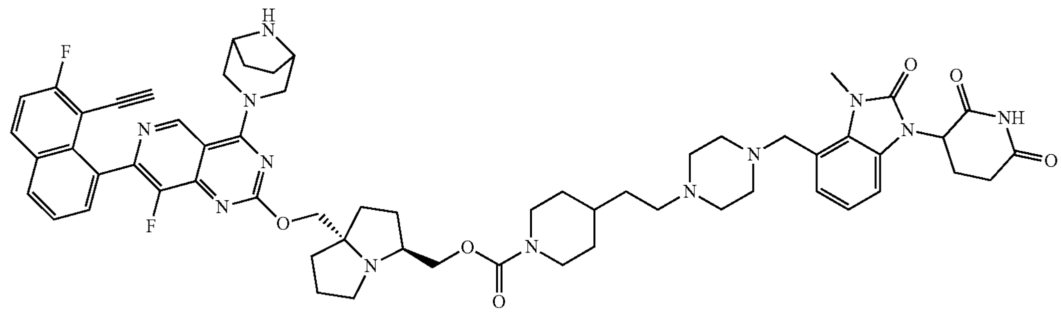 [SMILES: C#Cc1c(F)ccc2cccc(-c3ncc4c(N5CC6CCC(C5)N6)nc(OC[C@@]56CCCN5[C@H](COC(=O)N5CCC(CCN7CCN(Cc8cccc9c8n(C)c(=O)n9C8CCC(=O)NC8=O)CC7)CC5)CC6)nc4c3F)c12] |
| 085 | 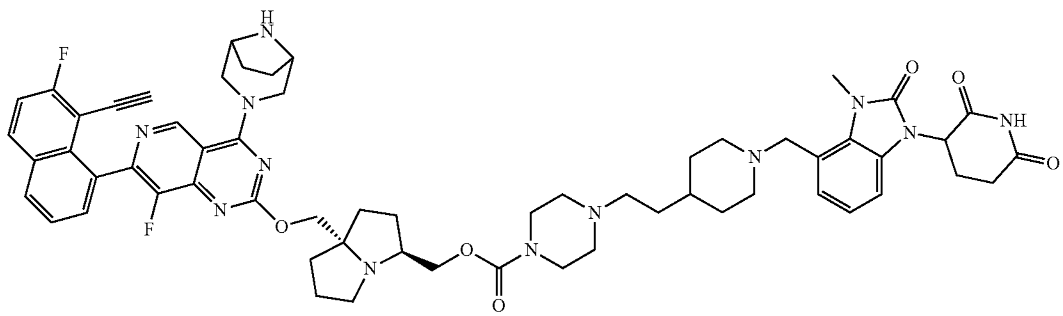 [SMILES: C#Cc1c(F)ccc2cccc(-c3ncc4c(N5CC6CCC(C5)N6)nc(OC[C@@]56CCCN5[C@H](COC(=O)N5CCN(CCC7CCN(Cc8cccc9c8n(C)c(=O)n9C8CCC(=O)NC8=O)CC7)CC5)CC6)nc4c3F)c12] |
| 087 | 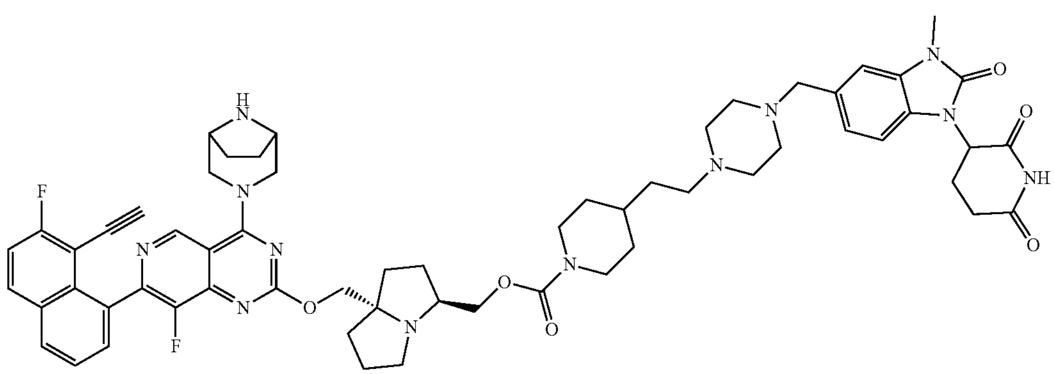 [SMILES: C#Cc1c(F)ccc2cccc(-c3ncc4c(N5CC6CCC(C5)N6)nc(OC[C@@]56CCCN5[C@H](COC(=O)N5CCC(CCN7CCN(Cc8ccc9c(c8)n(C)c(=O)n9C8CCC(=O)NC8=O)CC7)CC5)CC6)nc4c3F)c12] |
| 088 | 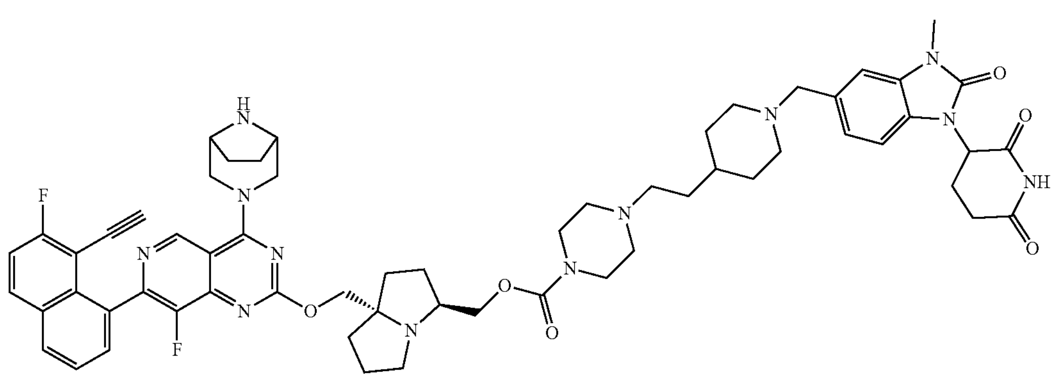 [SMILES: C#Cc1c(F)ccc2cccc(-c3ncc4c(N5CC6CCC(C5)N6)nc(OC[C@@]56CCCN5[C@H](COC(=O)N5CCN(CCC7CCN(Cc8ccc9c(c8)n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 089 | 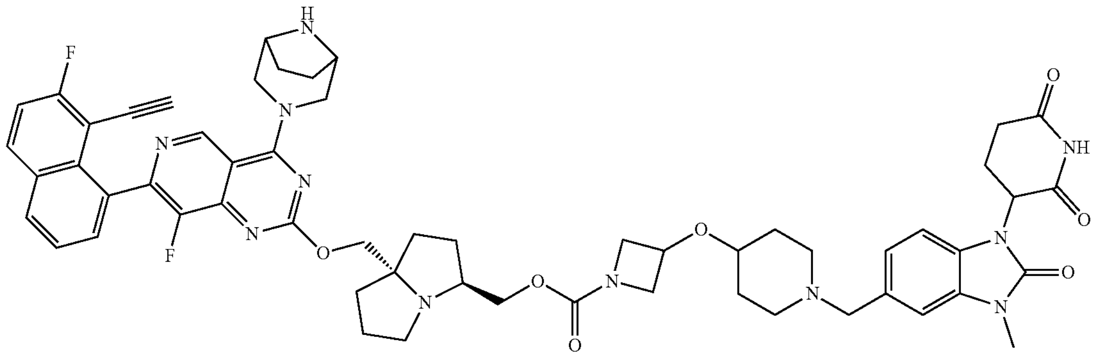 [SMILES: C#Cc1c(F)ccc2cccc(-c3ncc4c(N5CC6CCC(C5)N6)nc(OC[C@@]56CCCN5[C@H](COC(=O)N5CC(OC7CCN(Cc8ccc9c(c8)n(C)c(=O)n9C8CCC(=O)NC8=O)CC7)C5)CC6)nc4c3F)c12] |
| 090 | 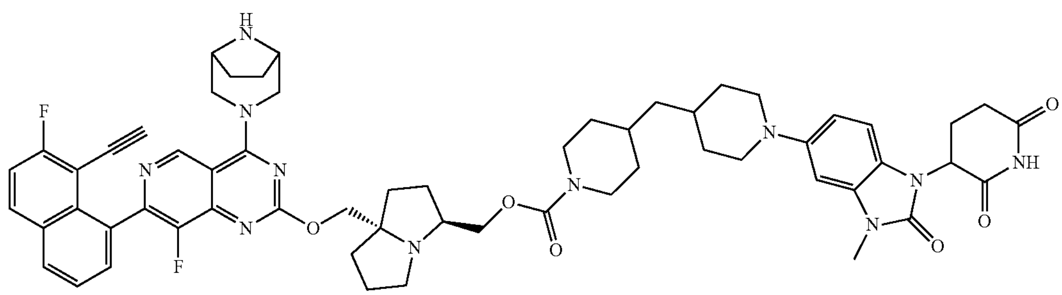 [SMILES: C#Cc1c(F)ccc2cccc(-c3ncc4c(N5CC6CCC(C5)N6)nc(OC[C@@]56CCCN5[C@H](COC(=O)N5CCC(CC7CCN(c8ccc9c(c8)n(C)c(=O)n9C8CCC(=O)NC8=O)CC7)CC5)CC6)nc4c3F)c12] |
| 091 | 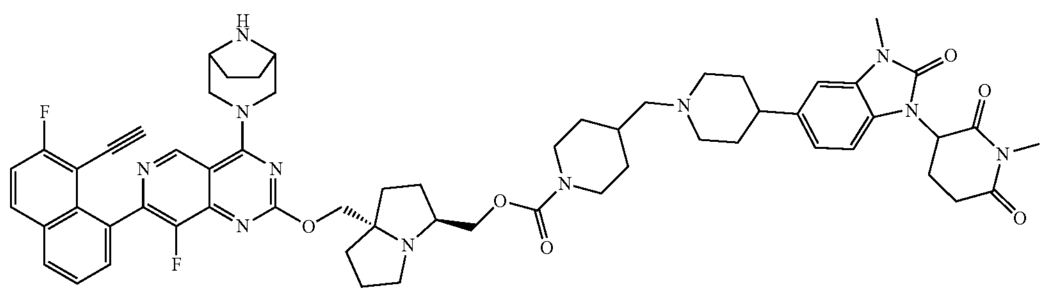 [SMILES: C#Cc1c(F)ccc2cccc(-c3ncc4c(N5CC6CCC(C5)N6)nc(OC[C@@]56CCCN5[C@H](COC(=O)N5CCC(CN7CCC(c8ccc9c(c8)n(C)c(=O)n9C8CCC(=O)N(C)C8=O)CC7)CC5)CC6)nc4c3F)c12] |
| 092 | 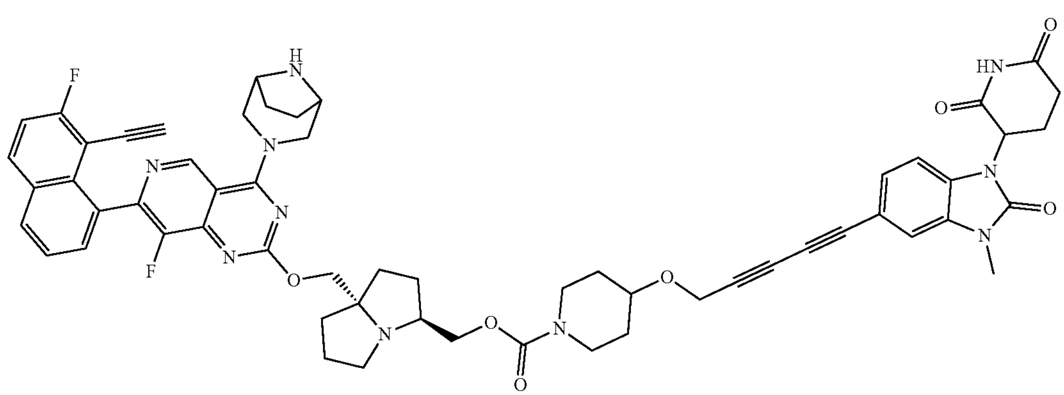 [SMILES: C#Cc1c(F)ccc2cccc(-c3ncc4c(N5CC6CCC(C5)N6)nc(OC[C@@]56CCCN5[C@H](COC(=O)N5CCC(OCC#CC#Cc7ccc8c(c7)n(C)c(=O)n8C7CCC(=O)NC7=O)CC5)CC6)nc4c3F)c12] |

TABLE 1-continued

Example Compounds of the Disclosure

| Compound No. | Compound Structure |
|---|---|
| 093 | 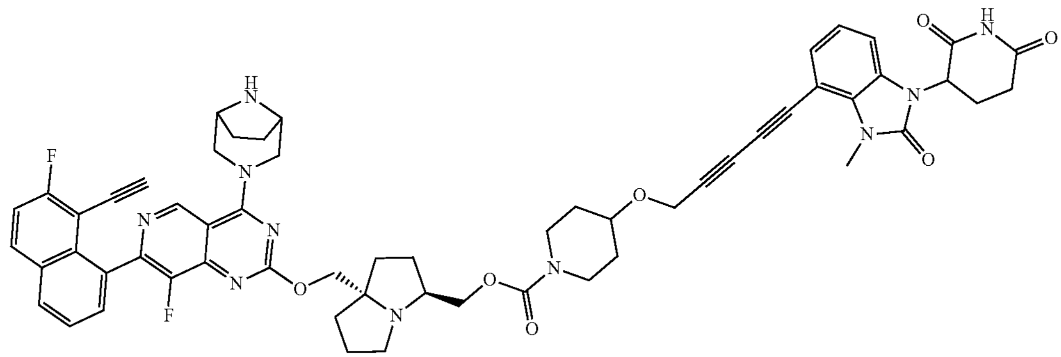 [SMILES: C#Cc1c(F)ccc2cccc(-c3ncc4c(N5CC6CCC(C5)N6)nc(OC[C@@]56CCCN5[C@H](COC(=O)N5CCC(OCC#CC#Cc7cccc8c7n(C)c(=O)n8C7CCC(=O)NC7=O)CC5)CC6)nc4c3F)c12] |
| 094 | 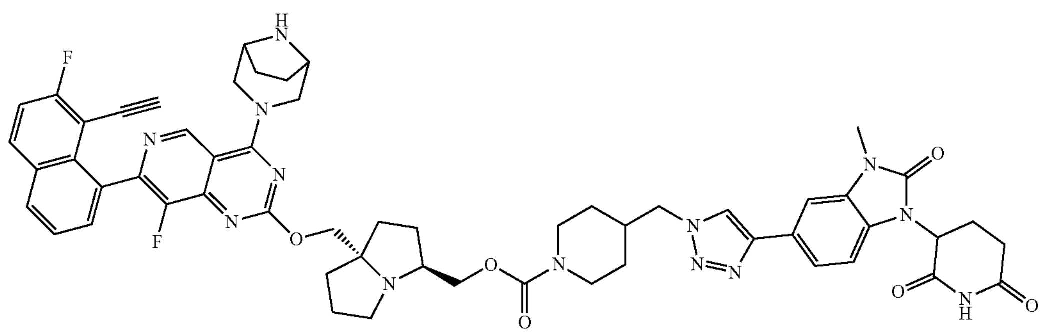 [SMILES: C#Cc1c(F)ccc2cccc(-c3ncc4c(N5CC6CCC(C5)N6)nc(OC[C@@]56CCCN5[C@H](COC(=O)N5CCC(Cn7cc(-c8ccc9c(c8)n(C)c(=O)n9C8CCC(=O)NC8=O)nn7)CC5)CC6)nc4c3F)c12] |
| 095 | 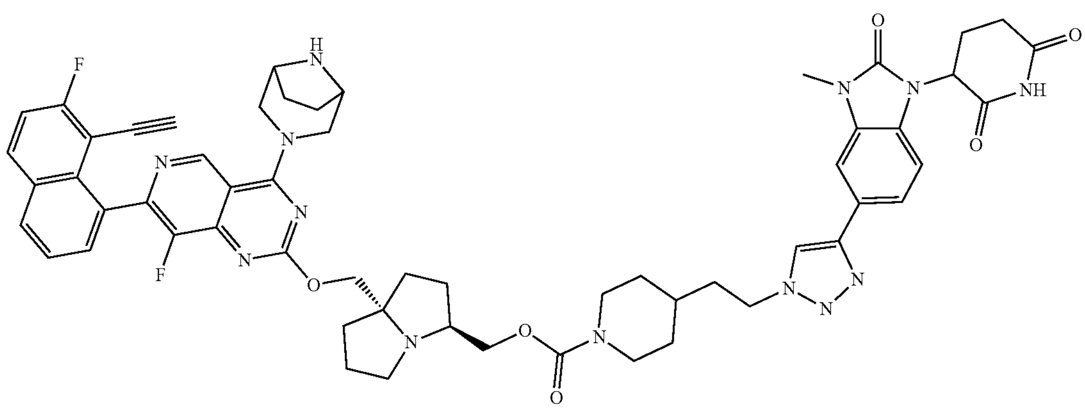 [SMILES: C#Cc1c(F)ccc2cccc(-c3ncc4c(N5CC6CCC(C5)N6)nc(OC[C@@]56CCCN5[C@H](COC(=O)N5CCC(CCN7C=C(c8ccc9c(c8)n(C)c(=O)n9C8CCC(=O)NC8=O)NN7)CC5)CC6)nc4c3F)c12] |
| 096 | 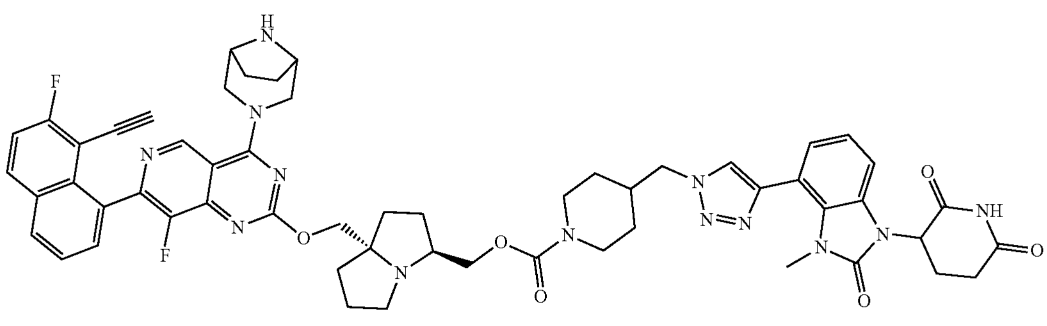 [SMILES: C#Cc1c(F)ccc2cccc(-c3ncc4c(N5CC6CCC(C5)N6)nc(OC[C@@]56CCCN5[C@H](COC(=O)N5CCC(Cn7cc(-c8cccc9c8n(C)c(=O)n9C8CCC(=O)NC8=O)nn7)CC5)CC6)nc4c3F)c12] |

TABLE 1-continued

Example Compounds of the Disclosure

| Compound No. | Compound Structure |
| --- | --- |
| 097 | 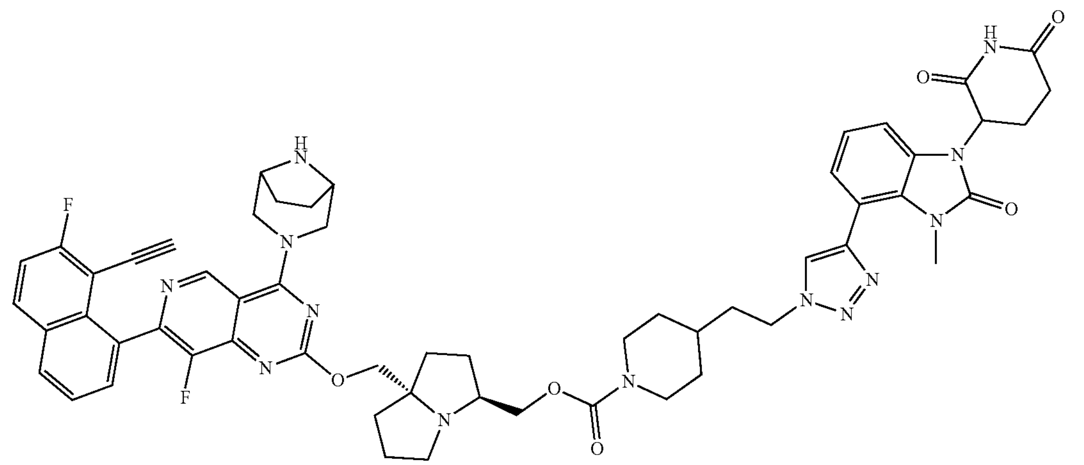 [SMILES: C#Cc1c(F)ccc2cccc(-c3ncc4c(N5CC6CCC(C5)N6)nc(OC[C@@]56CCCN5[C@H](COC(=O)N5CCC(CCn7cc(-c8cccc9c8n(C)c(=O)n9C8CCC(=O)NC8=O)nn7)CC5)CC6)nc4c3F)c12] |
| 098 | 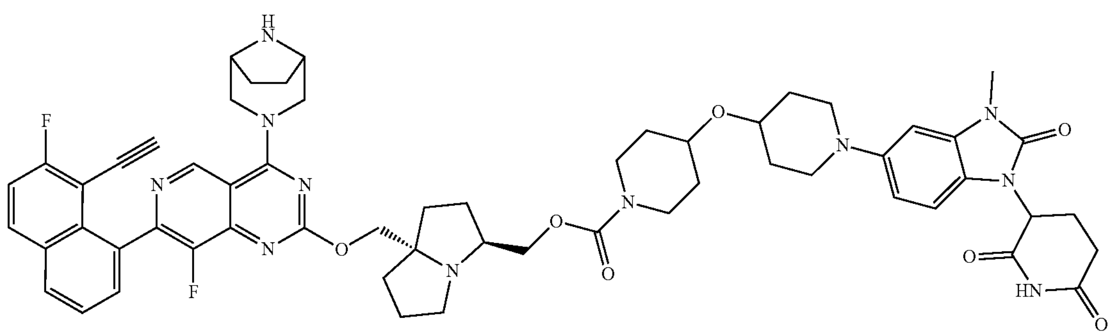 [SMILES: C#Cc1c(F)ccc2cccc(-c3ncc4c(N5CC6CCC(C5)N6)nc(OC[C@@]56CCCN5[C@H](COC(=O)N5CCC(OC7CCN(c8ccc9c(c8)n(C)c(=O)n9C8CCC(=O)NC8=O)CC7)CC5)CC6)nc4c3F)c12] |
| 099 | 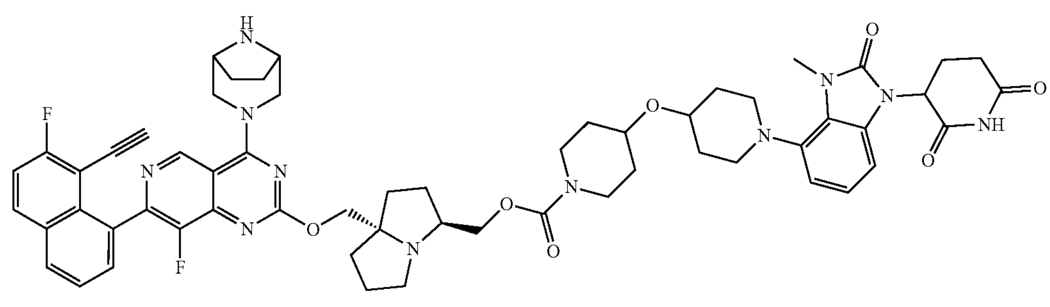 [SMILES: C#Cc1c(F)ccc2cccc(-c3ncc4c(N5CC6CCC(C5)N6)nc(OC[C@@]56CCCN5[C@H](COC(=O)N5CCC(OC7CCN(c8cccc9c8n(C)c(=O)n9C8CCC(=O)NC8=O)CC7)CC5)CC6)nc4c3F)c12] |
| 100 | 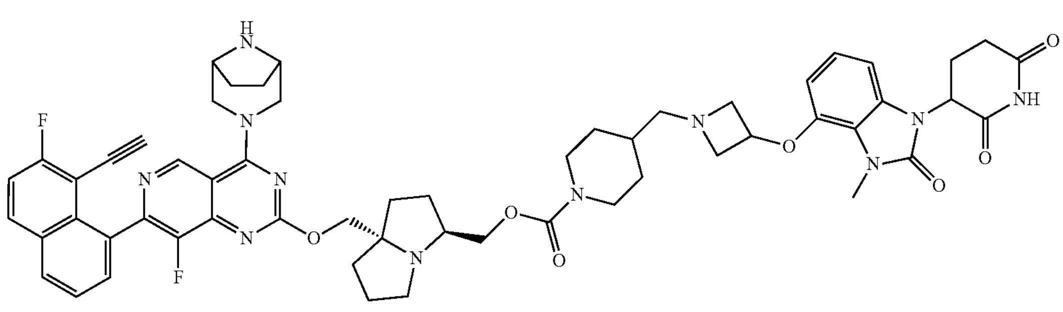 [SMILES: C#Cc1c(F)ccc2cccc(-c3ncc4c(N5CC6CCC(C5)N6)nc(OC[C@@]56CCCN5[C@H](COC(=O)N5CCC(CN7CC(Oc8cccc9c8n(C)c(=O)n9C8CCC(=O)NC8=O)C7)CC5)CC6)nc4c3F)c12] |

TABLE 1-continued
Example Compounds of the Disclosure
| Compound No. | Compound Structure |
|---|---|
| 101 | 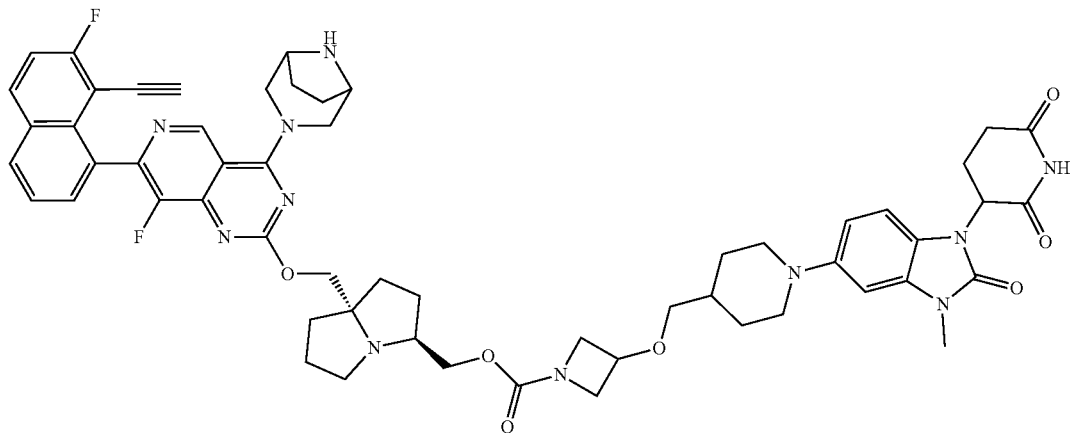 [SMILES: C#Cc1c(F)ccc2cccc(-c3ncc4c(N5CC6CCC(C5)N6)nc(OC[C@@]56CCCN5[C@H](COC(=O)N5CC(OCC7CCN(c8ccc9c(c8)n(C)c(=O)n9C8CCC(=O)NC8=O)CC7)C5)CC6)nc4c3F)c12] |
| 102 | 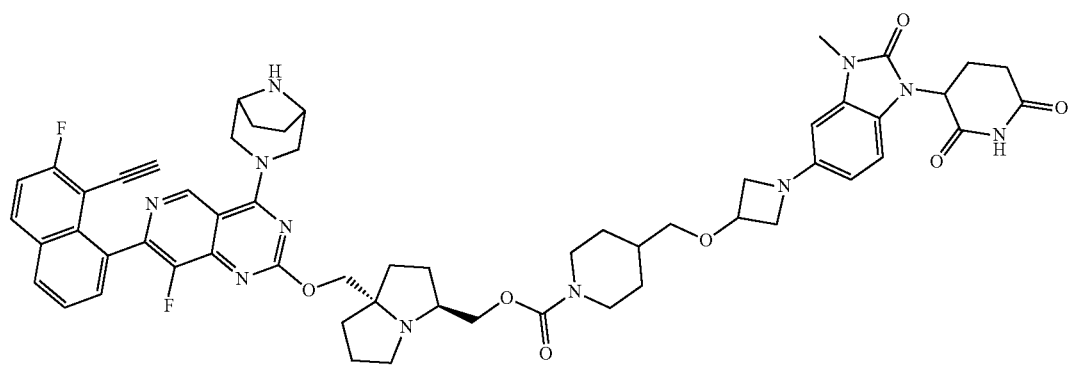 [SMILES: C#Cc1c(F)ccc2cccc(-c3ncc4c(N5CC6CCC(C5)N6)nc(OC[C@@]56CCCN5[C@H](COC(=O)N5CCC(COC7CN(c8ccc9c(c8)n(C)c(=O)n9C8CCC(=O)NC8=O)C7)CC5)CC6)nc4c3F)c12] |
| 103 | 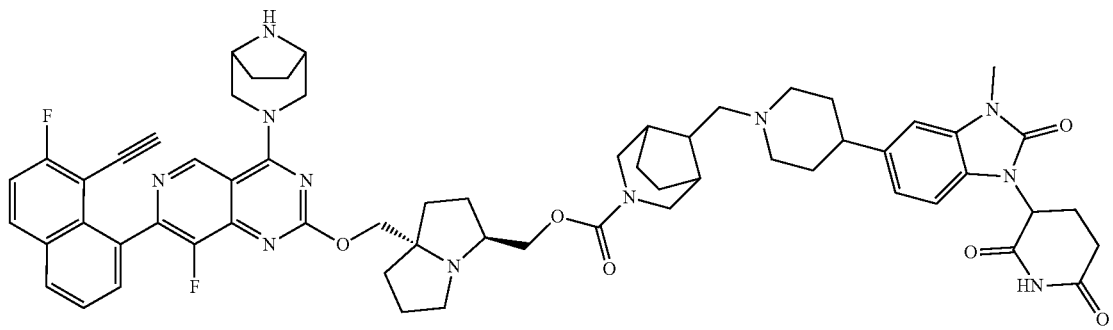 [SMILES: C#Cc1c(F)ccc2cccc(-c3ncc4c(N5CC6CCC(C5)N6)nc(OC[C@@]56CCCN5[C@H](COC(=O)N5CC7CCC(C5)C7CN5CCC(c7ccc8c(c7)n(C)c(=O)n8C7CCC(=O)NC7=O)CC5)CC6)nc4c3F)c12] |

TABLE 1-continued

Example Compounds of the Disclosure

| Compound No. | Compound Structure |
| --- | --- |
| 104 | 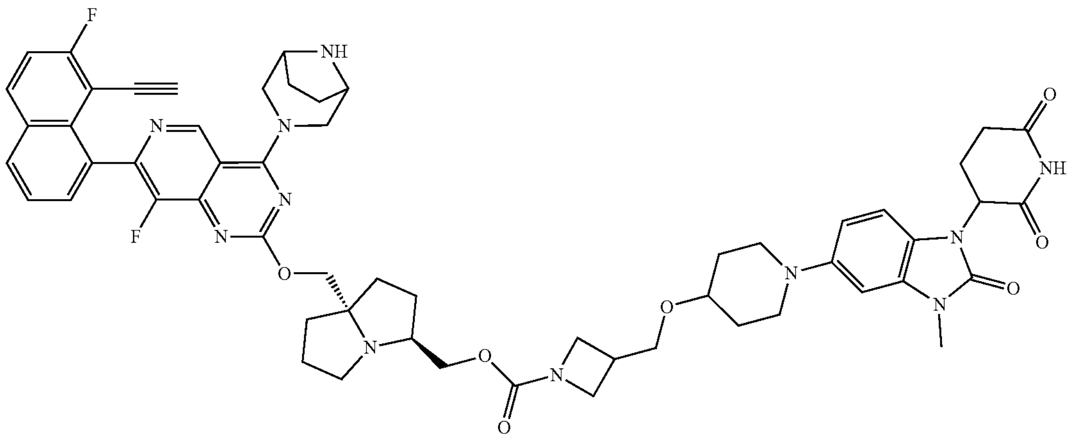 [SMILES: C#Cc1c(F)ccc2cccc(-c3ncc4c(N5CC6CCC(C5)N6)nc(OC[C@@]56CCCN5[C@H](COC(=O)N5CC(COC7CCN(c8ccc9c(c8)n(C)c(=O)n9C8CCC(=O)NC8=O)CC7)C5)CC6)nc4c3F)c12] |
| 105 | 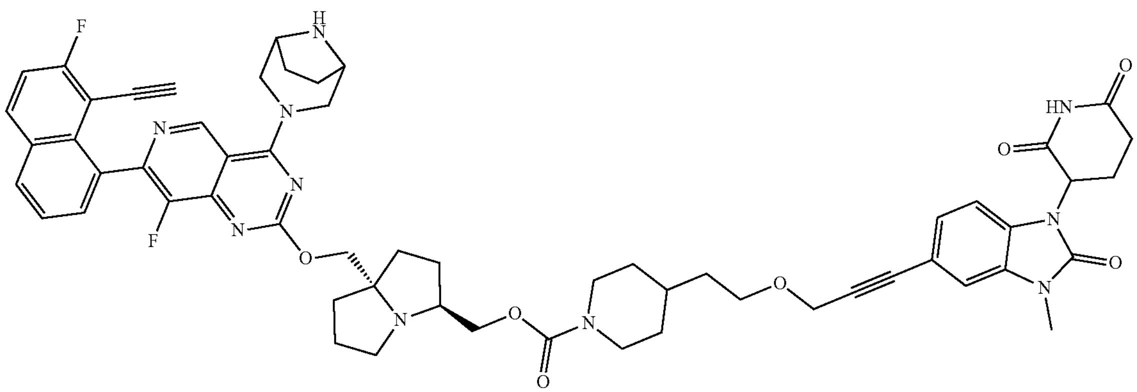 [SMILES: C#Cc1c(F)ccc2cccc(-c3ncc4c(N5CC6CCC(C5)N6)nc(OC[C@@]56CCCN5[C@H](COC(=O)N5CCC(CCOCC#Cc7ccc8c(c7)n(C)c(=O)n8C7CCC(=O)NC7=O)CC5)CC6)nc4c3F)c12] |
| 106 | 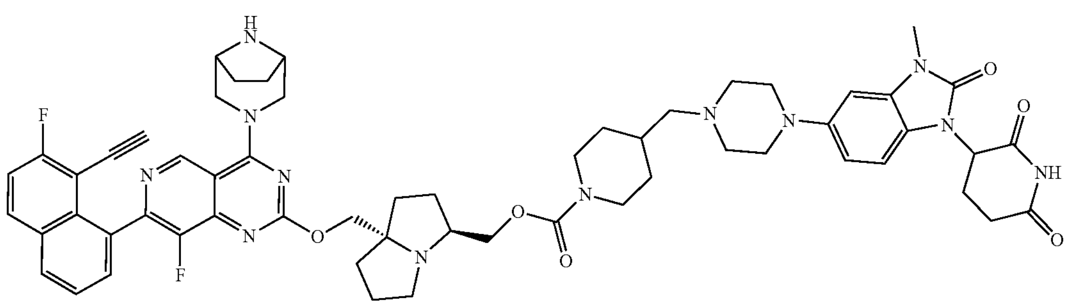 [SMILES: C#Cc1c(F)ccc2cccc(-c3ncc4c(N5CC6CCC(C5)N6)nc(OC[C@@]56CCCN5[C@H](COC(=O)N5CCC(CN7CCN(c8ccc9c(c8)n(C)c(=O)n9C8CCC(=O)NC8=O)CC7)CC5)CC6)nc4c3F)c12] |
| 107 | 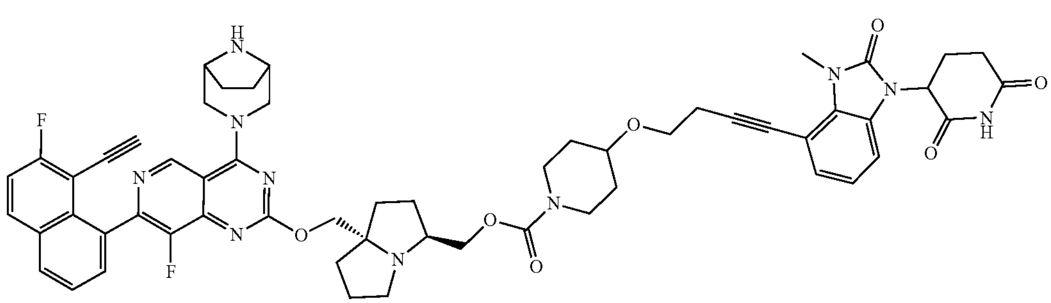 [SMILES: C#Cc1c(F)ccc2cccc(-c3ncc4c(N5CC6CCC(C5)N6)nc(OC[C@@]56CCCN5[C@H](COC(=O)N5CCC(OCCC#Cc7cccc8c7n(C)c(=O)n8C7CCC(=O)NC7=O)CC5)CC6)nc4c3F)c12] |

TABLE 1-continued

Example Compounds of the Disclosure

| Compound No. | Compound Structure |
| --- | --- |
| 108 | 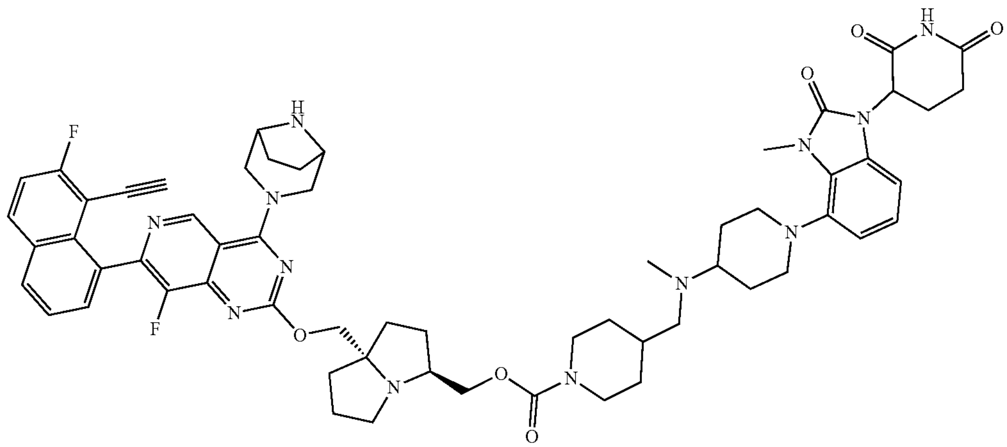 [SMILES: C#Cc1c(F)ccc2cccc(-c3ncc4c(N5CC6CCC(C5)N6)nc(OC[C@@]56CCCN5[C@H](COC(=O)N5CCC(CN(C)C7CCN(c8cccc9c8n(C)c(=O)n9C8CCC(=O)NC8=O)CC7)CC5)CC6)nc4c3F)c12] |
| 109 | 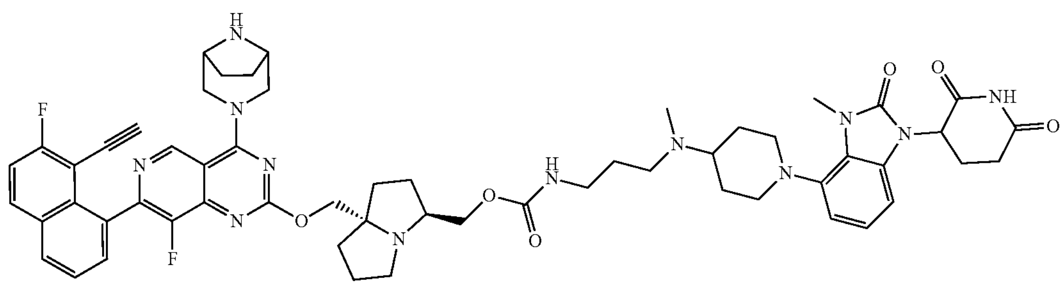 [SMILES: C#Cc1c(F)ccc2cccc(-c3ncc4c(N5CC6CCC(C5)N6)nc(OC[C@@]56CCCN5[C@H](COC(=O)NCCCN(C)C5CCN(c7cccc8c7n(C)c(=O)n8C7CCC(=O)NC7=O)CC5)CC6)nc4c3F)c12] |
| 110 | 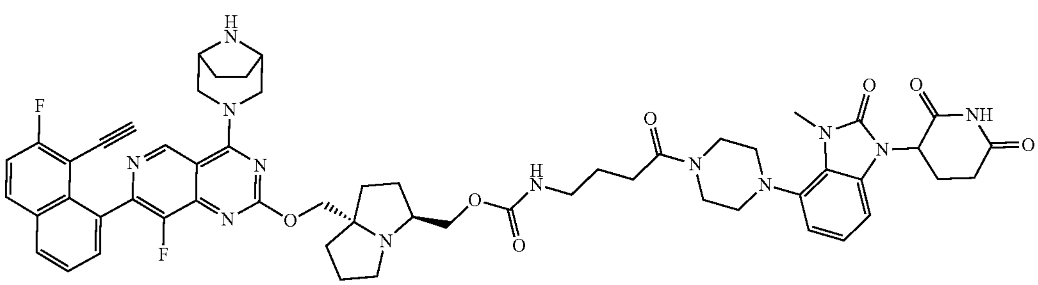 [SMILES: C#Cc1c(F)ccc2cccc(-c3ncc4c(N5CC6CCC(C5)N6)nc(OC[C@@]56CCCN5[C@H](COC(=O)NCCCC(=O)N5CCN(c7cccc8c7n(C)c(=O)n8C7CCC(=O)NC7=O)CC5)CC6)nc4c3F)c12] |
| 111 | 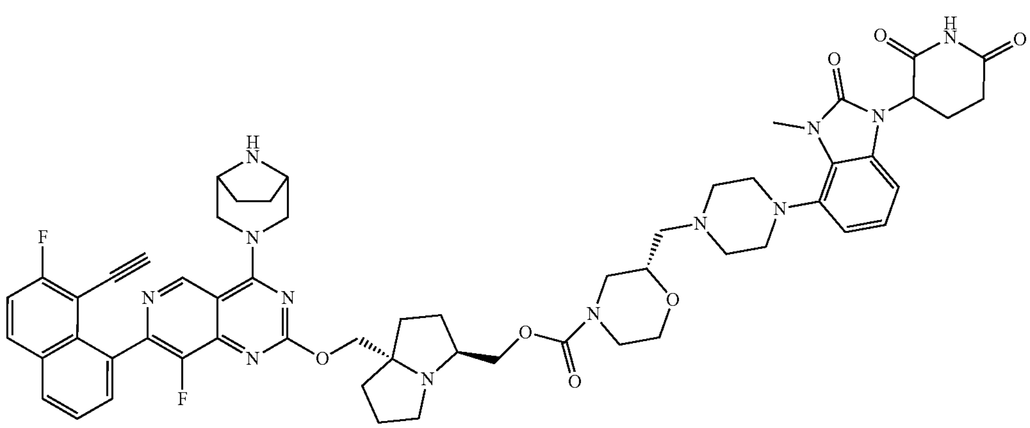 [SMILES: C#Cc1c(F)ccc2cccc(-c3ncc4c(N5CC6CCC(C5)N6)nc(OC[C@@]56CCCN5[C@H](COC(=O)N5CCO[C@@H](CN7CCN(c8cccc9c8n(C)c(=O)n9C8CCC(=O)NC8=O)CC7)C5)CC6)nc4c3F)c12] |

TABLE 1-continued

Example Compounds of the Disclosure

| Compound No. | Compound Structure |
|---|---|
| 112 | 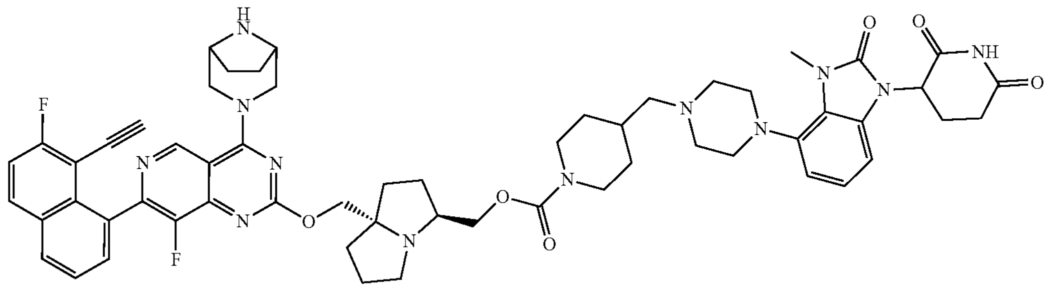 [SMILES: C#Cc1c(F)ccc2cccc(-c3ncc4c(N5CC6CCC(C5)N6)nc(OC[C@@]56CCCN5[C@H](COC(=O)N5CCC(CN7CCN(c8cccc9c8n(C)c(=O)n9C8CCC(=O)NC8=O)CC7)CC5)CC6)nc4c3F)c12] |
| 113 | 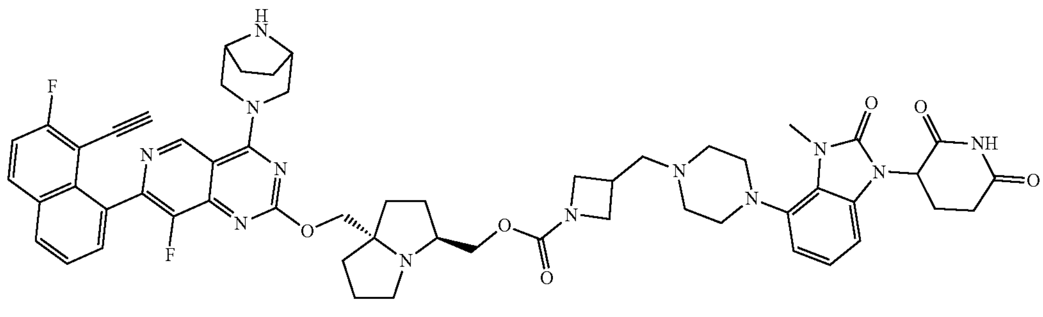 [SMILES: C#Cc1c(F)ccc2cccc(-c3ncc4c(N5CC6CCC(C5)N6)nc(OC[C@@]56CCCN5[C@H](COC(=O)N5CC(CN7CCN(c8cccc9c8n(C)c(=O)n9C8CCC(=O)NC8=O)CC7)C5)CC6)nc4c3F)c12] |
| 114 | 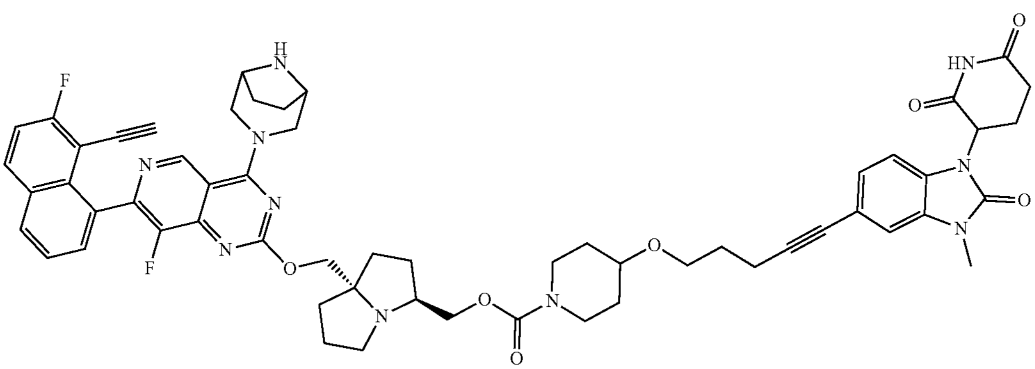 [SMILES: C#Cc1c(F)ccc2cccc(-c3ncc4c(N5CC6CCC(C5)N6)nc(OC[C@@]56CCCN5[C@H](COC(=O)N5CCC(OCCCC#Cc7ccc8c(c7)n(C)c(=O)n8C7CCC(=O)NC7=O)CC5)CC6)nc4c3F)c12] |
| 115 | 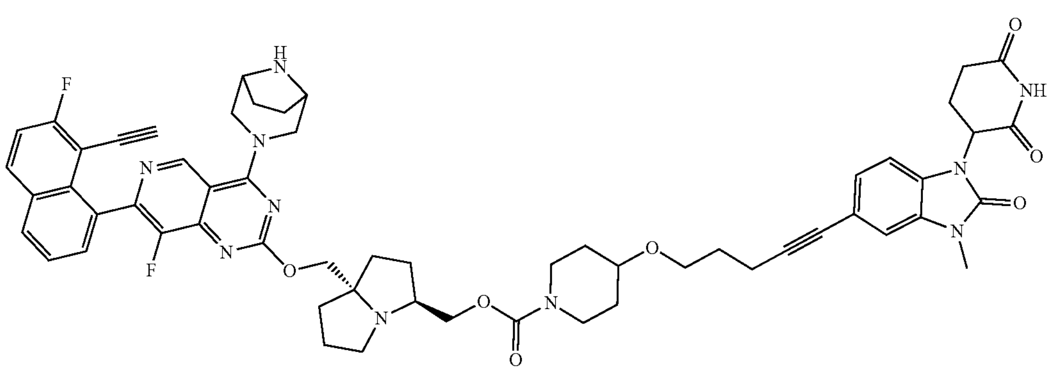 [SMILES: C#Cc1c(F)ccc2cccc(-c3ncc4c(N5CC6CCC(C5)N6)nc(OC[C@@]56CCCN5[C@H](COC(=O)N5CCC(OCCCC#Cc7ccc8c(c7)n(C)c(=O)n8C7CCC(=O)NC7=O)CC5)CC6)nc4c3F)c12] |

TABLE 1-continued

Example Compounds of the Disclosure

| Compound No. | Compound Structure |
|---|---|
| 116 | 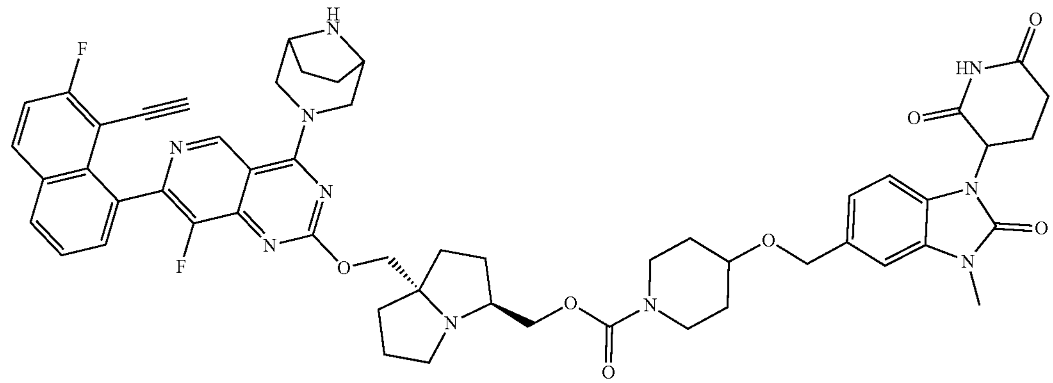 [SMILES: C#Cc1c(F)ccc2cccc(-c3ncc4c(N5CC6CCC(C5)N6)nc(OC[C@@]56CCCN5[C@H](COC(=O)N5CCC(OCc7ccc8c(c7)n(C)c(=O)n8C7CCC(=O)NC7=O)CC5)CC6)nc4c3F)c12] |
| 117 | 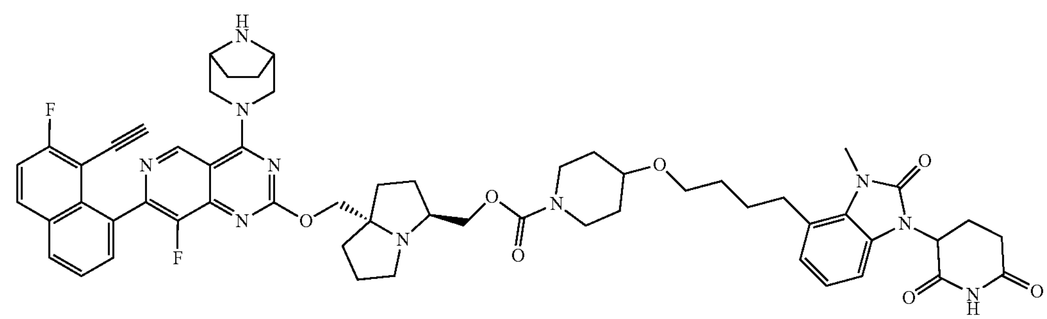 [SMILES: C#Cc1c(F)ccc2cccc(-c3ncc4c(N5CC6CCC(C5)N6)nc(OC[C@@]56CCCN5[C@H](COC(=O)N5CCC(OCCCCc7cccc8c7n(C)c(=O)n8C7CCC(=O)NC7=O)CC5)CC6)nc4c3F)c12] |
| 118 | 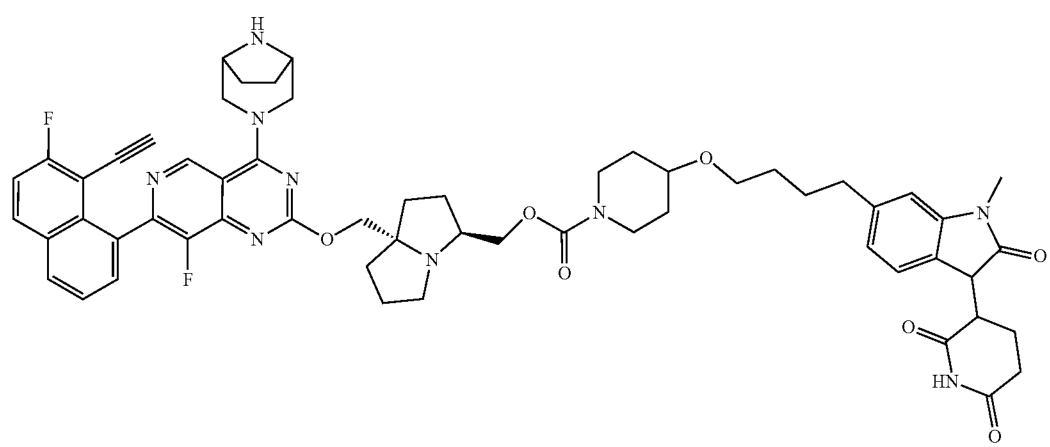 [SMILES: C#Cc1c(F)ccc2cccc(-c3ncc4c(N5CC6CCC(C5)N6)nc(OC[C@@]56CCCN5[C@H](COC(=O)N5CCC(OCCCCc7ccc8c(c7)N(C)C(=O)C8C7CCC(=O)NC7=O)CC5)CC6)nc4c3F)c12] |
| 119 | 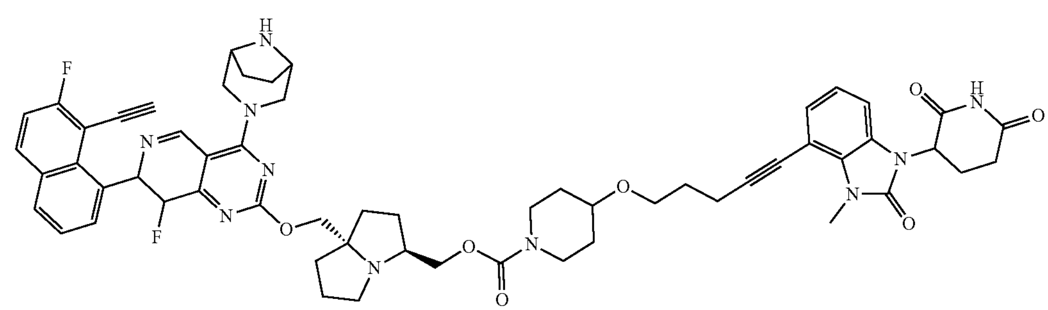 [SMILES: C#Cc1c(F)ccc2cccc(C3N=Cc4c(nc(OC[C@@]56CCCN5[C@H](COC(=O)N5CCC(OCCCC#Cc7cccc8c7n(C)c(=O)n8C7CCC(=O)NC7=O)CC5)CC6)nc4N4CC5CCC(C4)N5)C3F)c12] |

TABLE 1-continued

Example Compounds of the Disclosure

| Compound No. | Compound Structure |
|---|---|
| 120 | 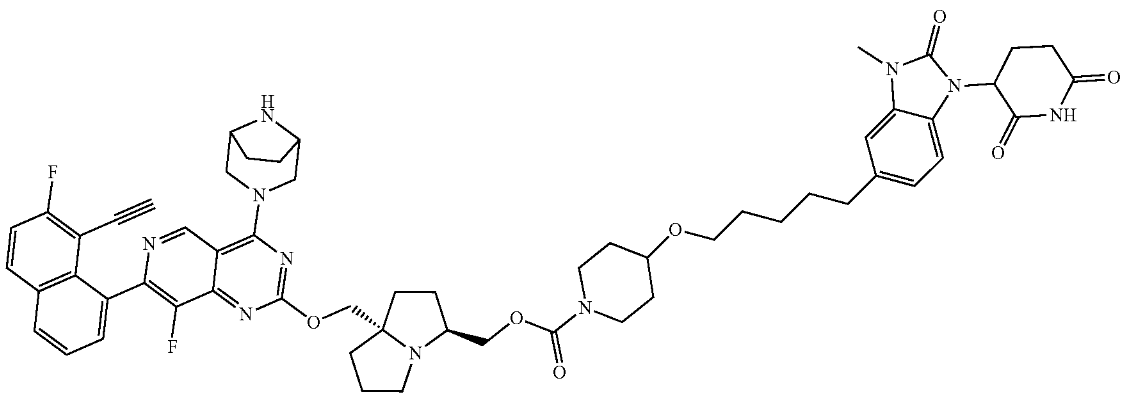 [SMILES: C#Cc1c(F)ccc2cccc(-c3ncc4c(N5CC6CCC(C5)N6)nc(OC[C@@]56CCCN5[C@H](COC(=O)N5CCC(OCCCCCc7ccc8c(c7)n(C)c(=O)n8C7CCC(=O)NC7=O)CC5)CC6)nc4c3F)c12] |
| 121 | 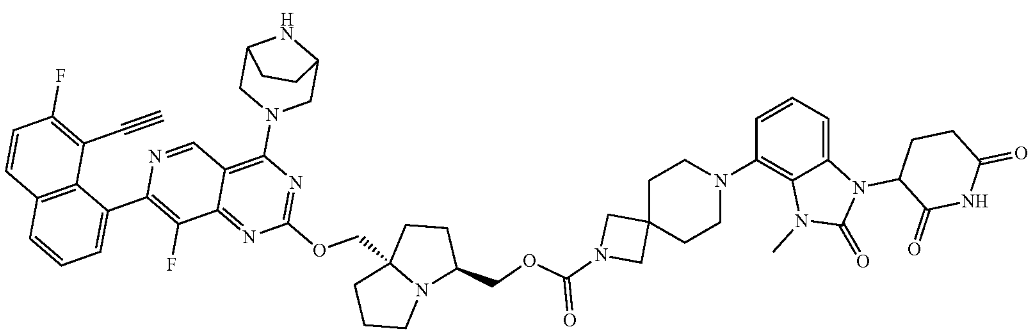 [SMILES: C#Cc1c(F)ccc2cccc(-c3ncc4c(N5CC6CCC(C5)N6)nc(OC[C@@]56CCCN5[C@H](COC(=O)N5CC7(CCN(c8cccc9c8n(C)c(=O)n9C8CCC(=O)NC8=O)CC7)C5)CC6)nc4c3F)c12] |
| 122 | 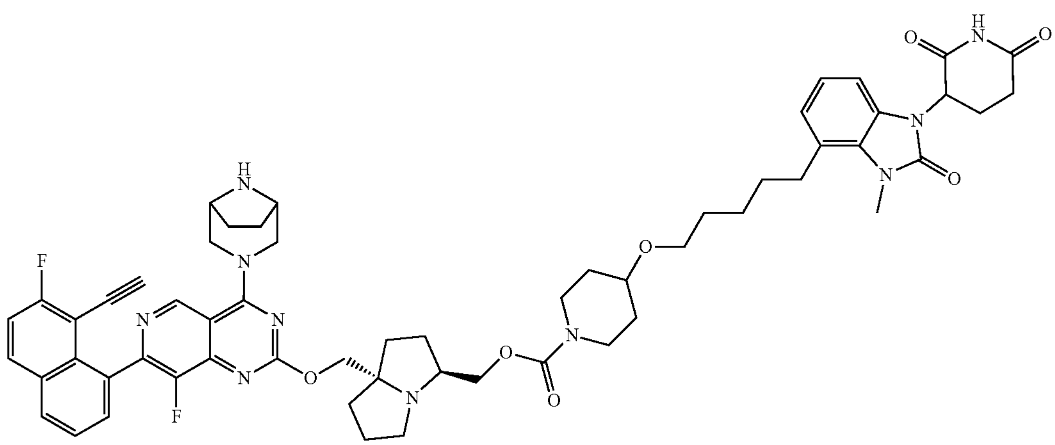 [SMILES: C#Cc1c(F)ccc2cccc(-c3ncc4c(N5CC6CCC(C5)N6)nc(OC[C@@]56CCCN5[C@H](COC(=O)N5CCC(OCCCCCc7cccc8c7n(C)c(=O)n8C7CCC(=O)NC7=O)CC5)CC6)nc4c3F)c12] |
| 123 | 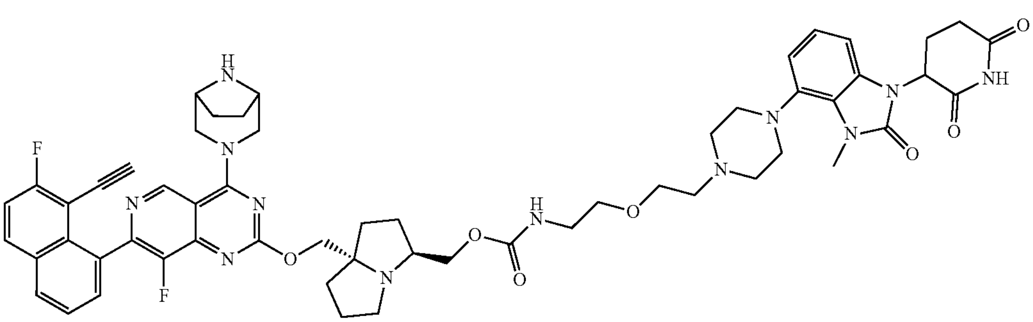 [SMILES: C#Cc1c(F)ccc2cccc(-c3ncc4c(N5CC6CCC(C5)N6)nc(OC[C@@]56CCCN5[C@H](COC(=O)NCCOCCN5CCN(c7cccc8c7n(C)c(=O)n8C7CCC(=O)NC7=O)CC5)CC6)nc4c3F)c12] |

TABLE 1-continued

Example Compounds of the Disclosure

| Compound No. | Compound Structure |
|---|---|
| 124 | 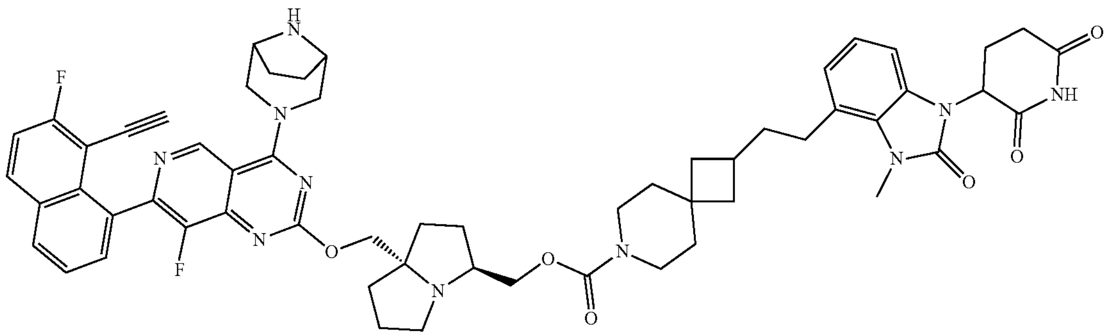 [SMILES: C#Cc1c(F)ccc2cccc(-c3ncc4c(N5CC6CCC(C5)N6)nc(OC[C@@]56CCCN5[C@H](COC(=O)N5CCC7(CC5)CC(CCc5cccc8c5n(C)c(=O)n8C5CCC(=O)NC5=O)C7)CC6)nc4c3F)c12] |
| 125 | 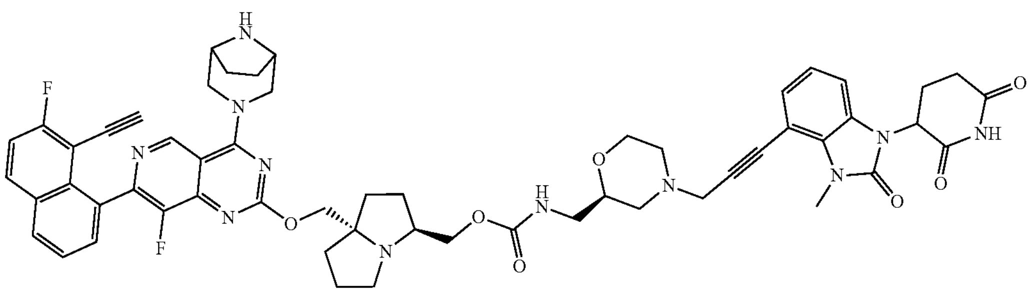 [SMILES: C#Cc1c(F)ccc2cccc(-c3ncc4c(N5CC6CCC(C5)N6)nc(OC[C@@]56CCCN5[C@H](COC(=O)NC[C@@H]5CN(CC#Cc7cccc8c7n(C)c(=O)n8C7CCC(=O)NC7=O)CCO5)CC6)nc4c3F)c12] |
| 126 | 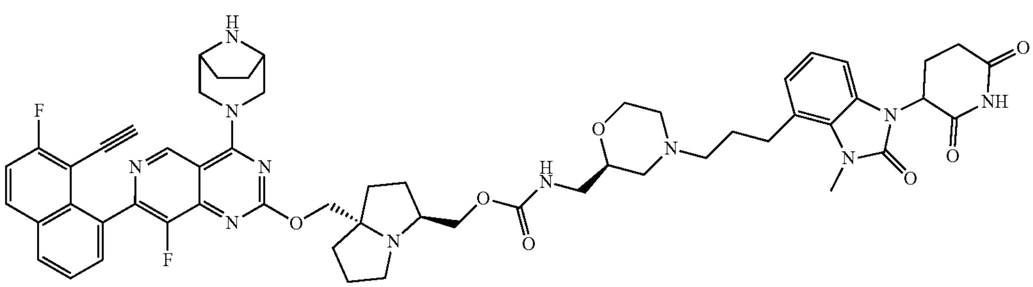 [SMILES: C#Cc1c(F)ccc2cccc(-c3ncc4c(N5CC6CCC(C5)N6)nc(OC[C@@]56CCCN5[C@H](COC(=O)NC[C@@H]5CN(CCCc7cccc8c7n(C)c(=O)n8C7CCC(=O)NC7=O)CCO5)CC6)nc4c3F)c12] |
| 127 | 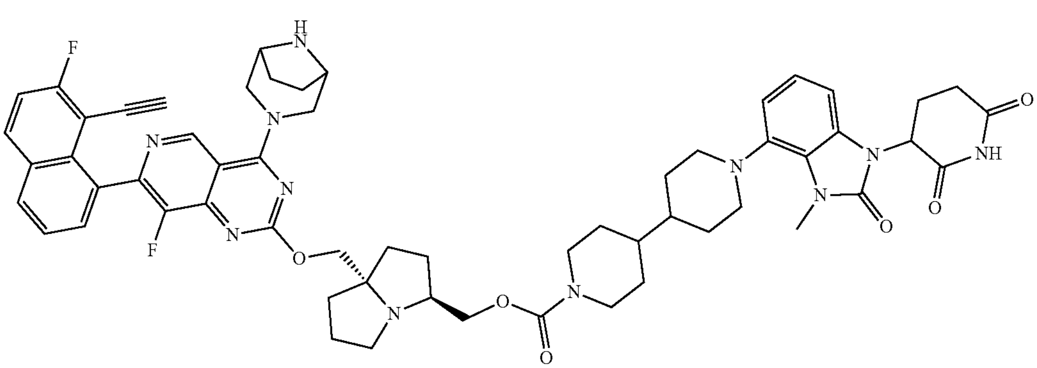 [SMILES: C#Cc1c(F)ccc2cccc(-c3ncc4c(N5CC6CCC(C5)N6)nc(OC[C@@]56CCCN5[C@H](COC(=O)N5CCC(C7CCN(c8cccc9c8n(C)c(=O)n9C8CCC(=O)NC8=O)CC7)CC5)CC6)nc4c3F)c12] |

TABLE 1-continued
Example Compounds of the Disclosure
| Compound No. | Compound Structure |
|---|---|
| 128 | 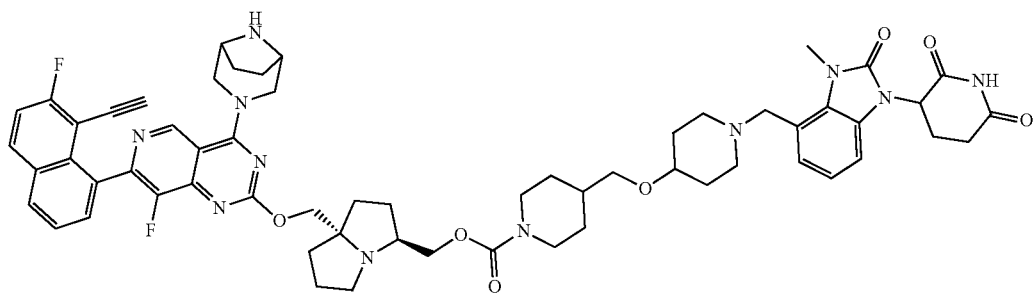 [SMILES: C#Cc1c(F)ccc2cccc(-c3ncc4c(N5CC6CCC(C5)N6)nc(OC[C@@]56CCCN5[C@H](COC(=O)N5CCC(COC7CCN(Cc8cccc9c8n(C)c(=O)n9C8CCC(=O)NC8=O)CC7)CC5)CC6)nc4c3F)c12] |
| 129 | 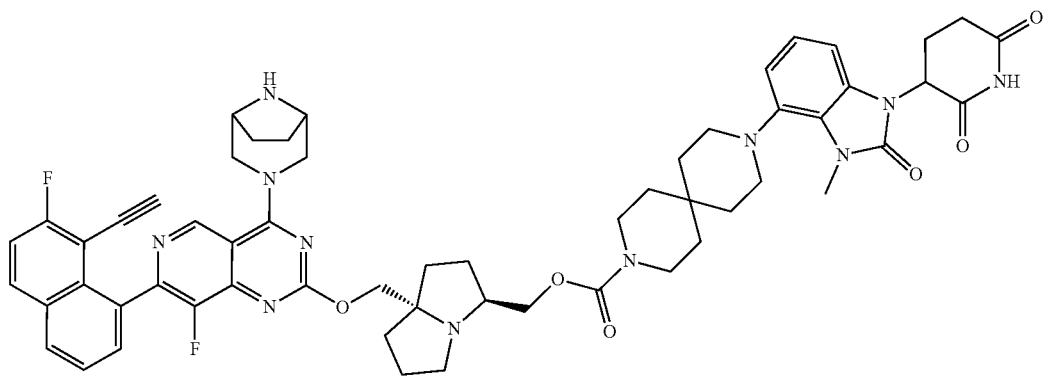 [SMILES: C#Cc1c(F)ccc2cccc(-c3ncc4c(N5CC6CCC(C5)N6)nc(OC[C@@]56CCCN5[C@H](COC(=O)N5CCC7(CC5)CCN(c5cccc8c5n(C)c(=O)n8C5CCC(=O)NC5=O)CC7)CC6)nc4c3F)c12] |
| 130 | 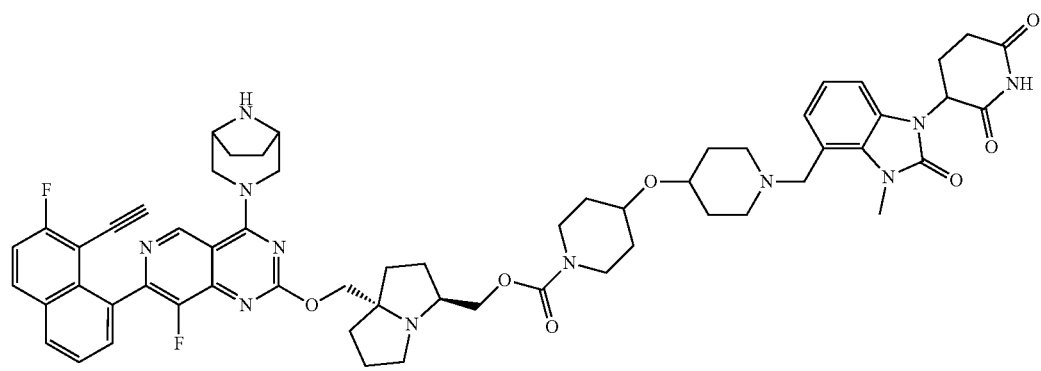 [SMILES: C#Cc1c(F)ccc2cccc(-c3ncc4c(N5CC6CCC(C5)N6)nc(OC[C@@]56CCCN5[C@H](COC(=O)N5CCC(OC7CCN(Cc8cccc9c8n(C)c(=O)n9C8CCC(=O)NC8=O)CC7)CC5)CC6)nc4c3F)c12] |
| 131 | 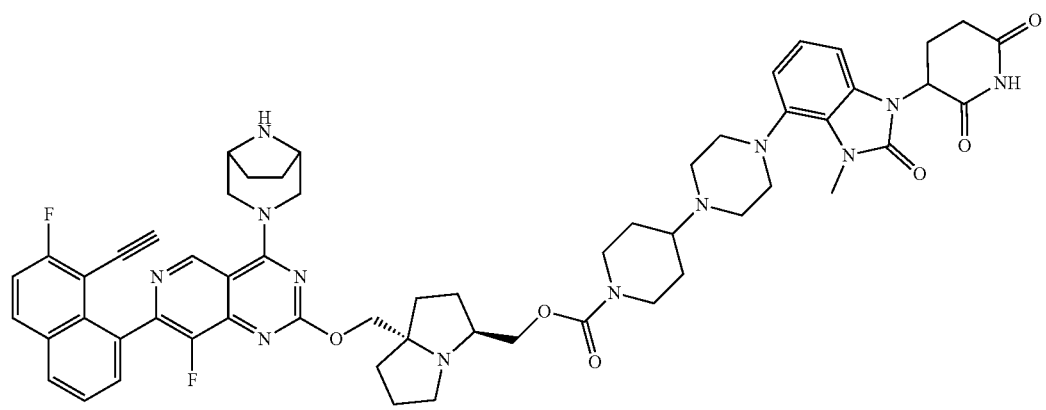 [SMILES: C#Cc1c(F)ccc2cccc(-c3ncc4c(N5CC6CCC(C5)N6)nc(OC[C@@]56CCCN5[C@H](COC(=O)N5CCC(N7CCN(c8cccc9c8n(C)c(=O)n9C8CCC(=O)NC8=O)CC7)CC5)CC6)nc4c3F)c12] |

TABLE 1-continued

Example Compounds of the Disclosure

| Compound No. | Compound Structure |
|---|---|
| 132 | 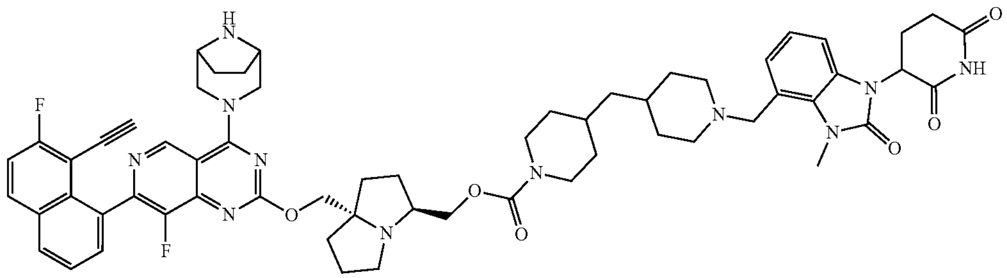 [SMILES: C#Cc1c(F)ccc2cccc(-c3ncc4c(N5CC6CCC(C5)N6)nc(OC[C@@]56CCCN5[C@H](COC(=O)N5CCC(CC7CCN(Cc8cccc9c8n(C)c(=O)n9C8CCC(=O)NC8=O)CC7)CC5)CC6)nc4c3F)c12] |
| 133 | 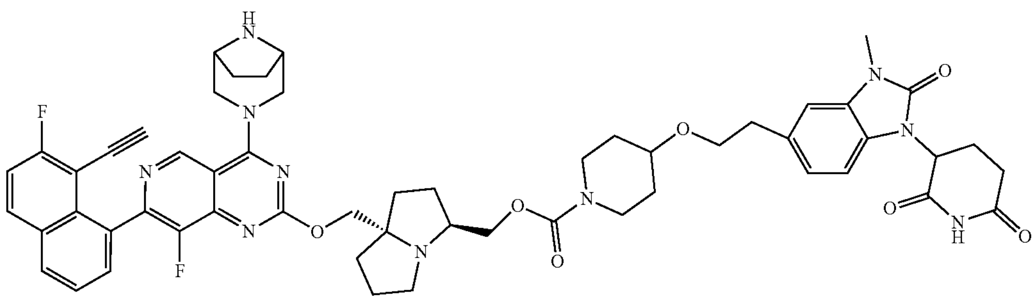 [SMILES: C#Cc1c(F)ccc2cccc(-c3ncc4c(N5CC6CCC(C5)N6)nc(OC[C@@]56CCCN5[C@H](COC(=O)N5CCC(OCCc7ccc8c(c7)n(C)c(=O)n8C7CCC(=O)NC7=O)CC5)CC6)nc4c3F)c12] |
| 134 | 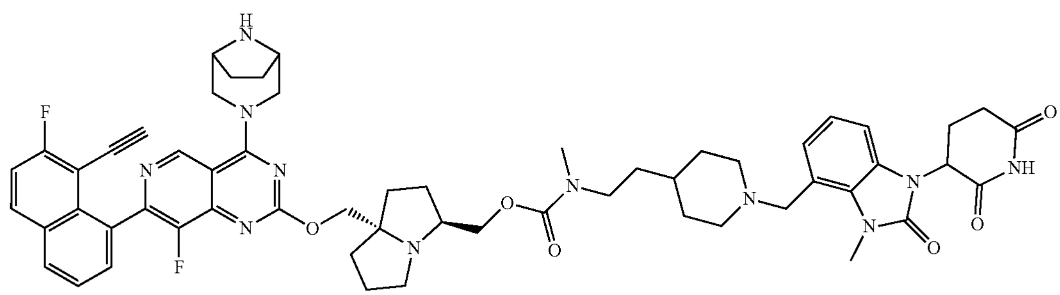 [SMILES: C#Cc1c(F)ccc2cccc(-c3ncc4c(N5CC6CCC(C5)N6)nc(OC[C@@]56CCCN5[C@H](COC(=O)N(C)CCC5CCN(Cc7cccc8c7n(C)c(=O)n8C7CCC(=O)NC7=O)CC5)CC6)nc4c3F)c12] |
| 135 | 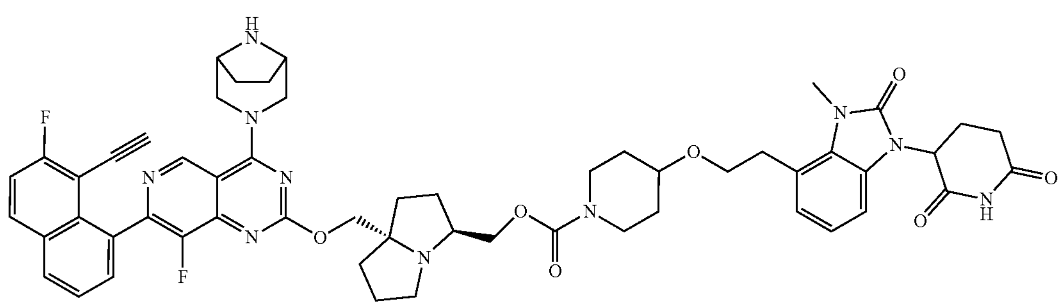 [SMILES: C#Cc1c(F)ccc2cccc(-c3ncc4c(N5CC6CCC(C5)N6)nc(OC[C@@]56CCCN5[C@H](COC(=O)N5CCC(OCCc7cccc8c7n(C)c(=O)n8C7CCC(=O)NC7=O)CC5)CC6)nc4c3F)c12] |
| 136 | 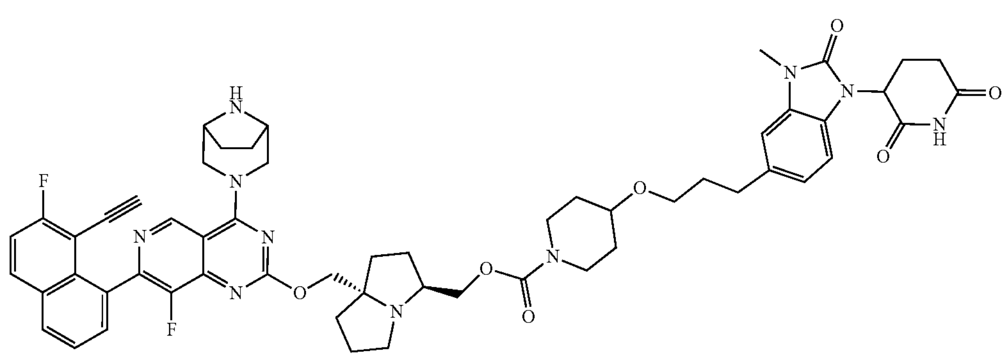 [SMILES: C#Cc1c(F)ccc2cccc(-c3ncc4c(N5CC6CCC(C5)N6)nc(OC[C@@]56CCCN5[C@H](COC(=O)N5CCC(OCCCc7ccc8c(c7)n(C)c(=O)n8C7CCC(=O)NC7=O)CC5)CC6)nc4c3F)c12] |

TABLE 1-continued
Example Compounds of the Disclosure
| Compound No. | Compound Structure |
|---|---|
| 138 | 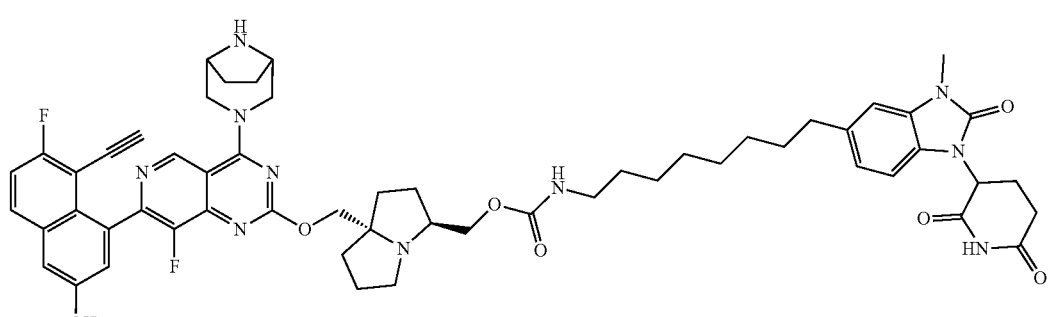 |
| 139 | 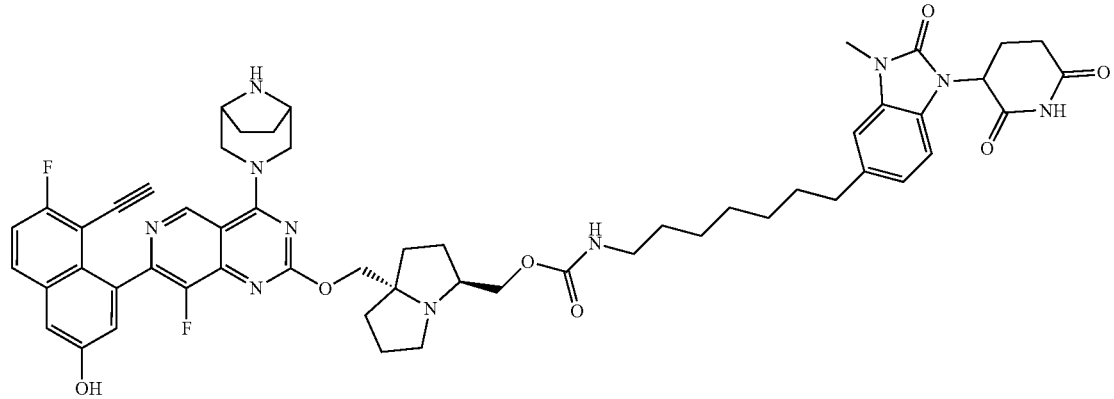 [SMILES: C#Cc1c(F)ccc2cc(O)cc(-c3ncc4c(N5CC6CCC(C5)N6)nc(OC[C@@]56CCCN5[C@H](COC(=O)NCCCCCCCc5ccc7c(c5)n(C)c(=O)n7C5CCC(=O)NC5=O)CC6)nc4c3F)c12] |
| 140 | 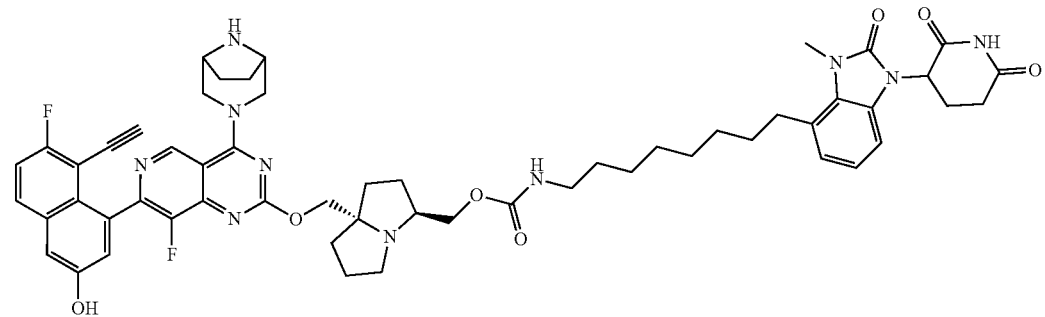 [SMILES: C#Cc1c(F)ccc2cc(O)cc(-c3ncc4c(N5CC6CCC(C5)N6)nc(OC[C@@]56CCCN5[C@H](COC(=O)NCCCCCCCCc5cccc7c5n(C)c(=O)n7C5CCC(=O)NC5=O)CC6)nc4c3F)c12] |
| 141 | 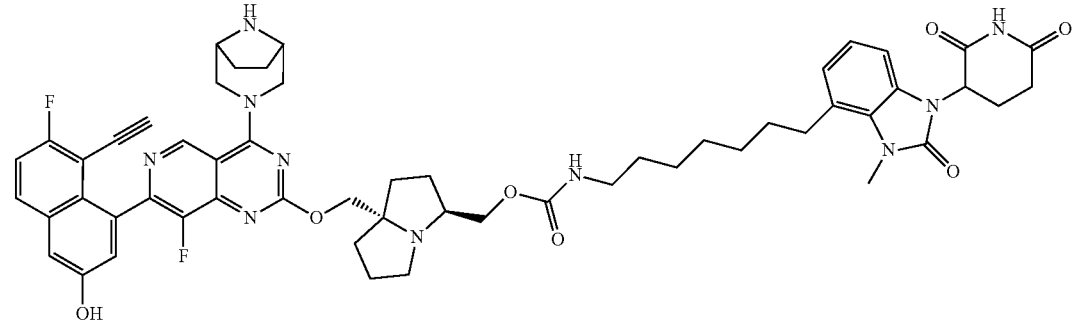 [SMILES: C#Cc1c(F)ccc2cc(O)cc(-c3ncc4c(N5CC6CCC(C5)N6)nc(OC[C@@]56CCCN5[C@H](COC(=O)NCCCCCCCc5cccc7c5n(C)c(=O)n7C5CCC(=O)NC5=O)CC6)nc4c3F)c12] |

TABLE 1-continued

Example Compounds of the Disclosure

| Compound No. | Compound Structure |
|---|---|
| 142 | 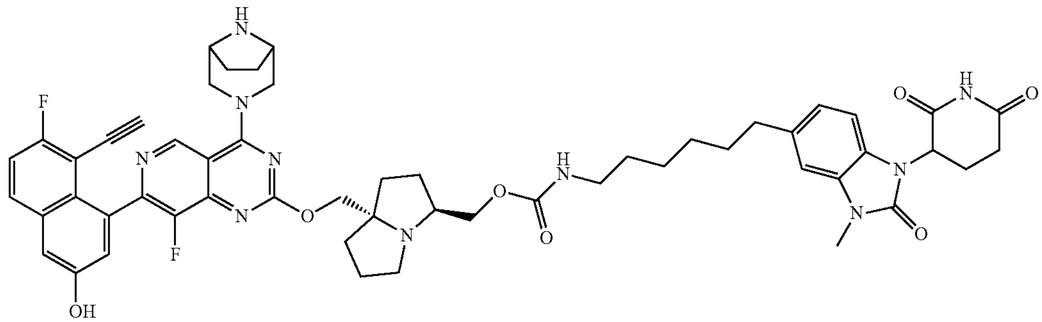 [SMILES: C#Cc1c(F)ccc2cc(O)cc(-c3ncc4c(N5CC6CCC(C5)N6)nc(OC[C@@]56CCCN5[C@H](COC(=O)NCCCCCCc5ccc7c(c5)n(C)c(=O)n7C5CCC(=O)NC5=O)CC6)nc4c3F)c12] |
| 143 | 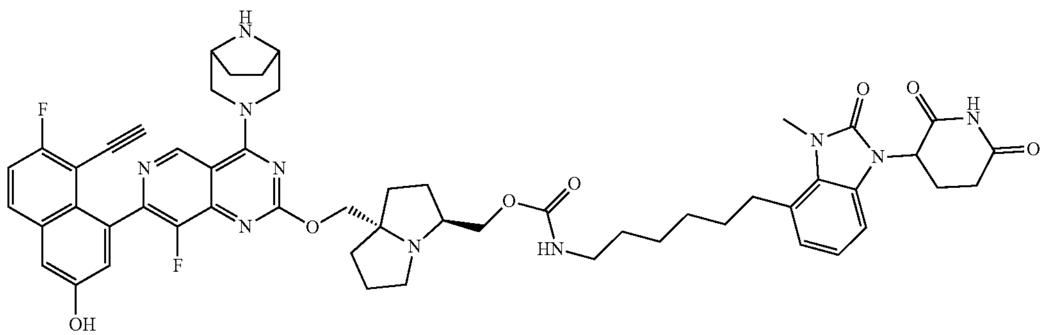 [SMILES: C#Cc1c(F)ccc2cc(O)cc(-c3ncc4c(N5CC6CCC(C5)N6)nc(OC[C@@]56CCCN5[C@H](COC(=O)NCCCCCCc5cccc7c5n(C)c(=O)n7C5CCC(=O)NC5=O)CC6)nc4c3F)c12] |
| 144 | 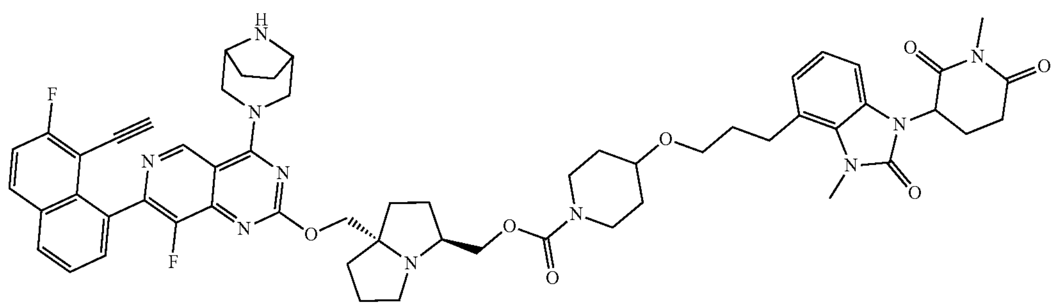 [SMILES: C#Cc1c(F)ccc2cccc(-c3ncc4c(N5CC6CCC(C5)N6)nc(OC[C@@]56CCCN5[C@H](COC(=O)N5CCC(OCCCc7cccc8c7n(C)c(=O)n8C7CCC(=O)N(C)C7=O)CC5)CC6)nc4c3F)c12] |
| 145 | 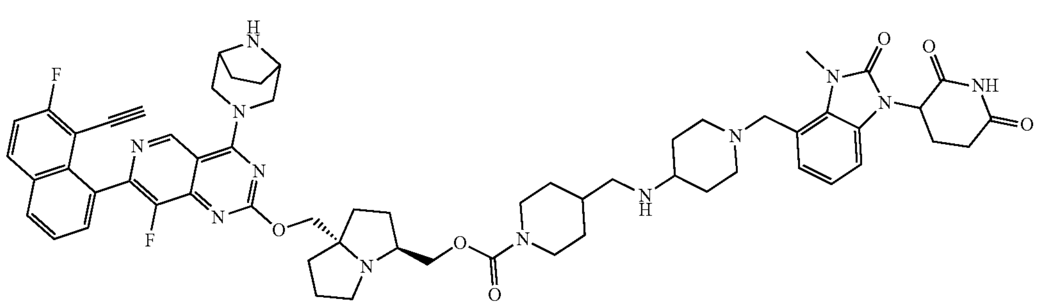 [SMILES: C#Cc1c(F)ccc2cccc(-c3ncc4c(N5CC6CCC(C5)N6)nc(OC[C@@]56CCCN5[C@H](COC(=O)N5CCC(CNC7CCN(Cc8cccc9c8n(C)c(=O)n9C8CCC(=O)NC8=O)CC7)CC5)CC6)nc4c3F)c12] |

TABLE 1-continued
Example Compounds of the Disclosure
| Compound No. | Compound Structure |
|---|---|
| 146 | 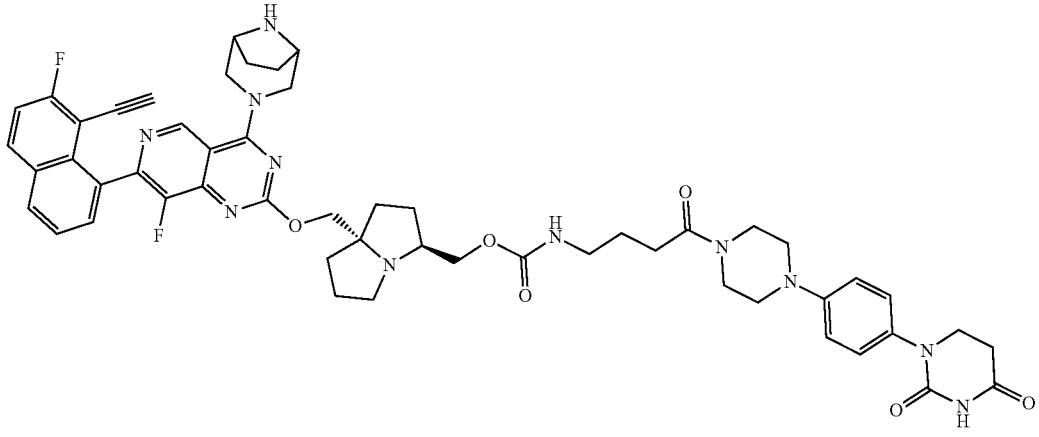 [SMILES: C#Cc1c(F)ccc2cccc(-c3ncc4c(N5CC6CCC(C5)N6)nc(OC[C@@]56CCCN5[C@H](COC(=O)NCCCC(=O)N5CCN(c7ccc(N8CCC(=O)NC8=O)cc7)CC5)CC6)nc4c3F)c12] |
| 147 | 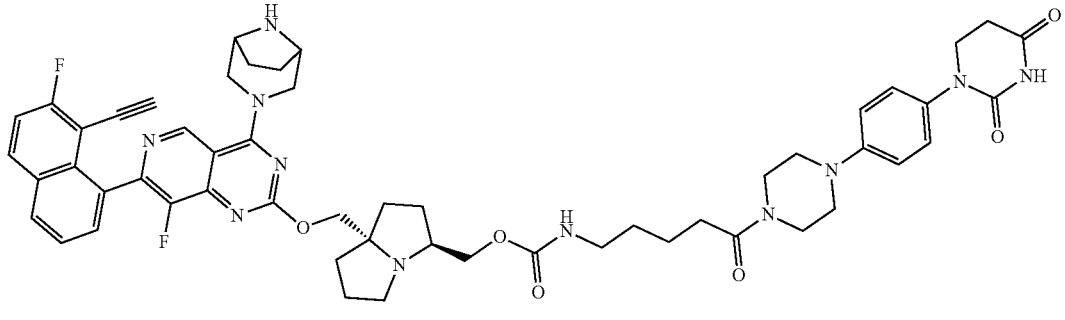 [SMILES: C#Cc1c(F)ccc2cccc(-c3ncc4c(N5CC6CCC(C5)N6)nc(OC[C@@]56CCCN5[C@H](COC(=O)NCCCCC(=O)N5CCN(c7ccc(N8CCC(=O)NC8=O)cc7)CC5)CC6)nc4c3F)c12] |
| 148 | 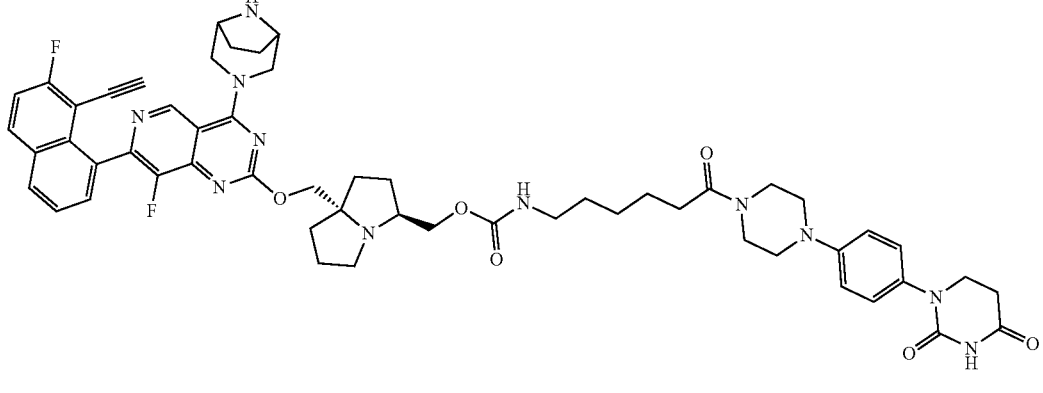 |
| 149 | 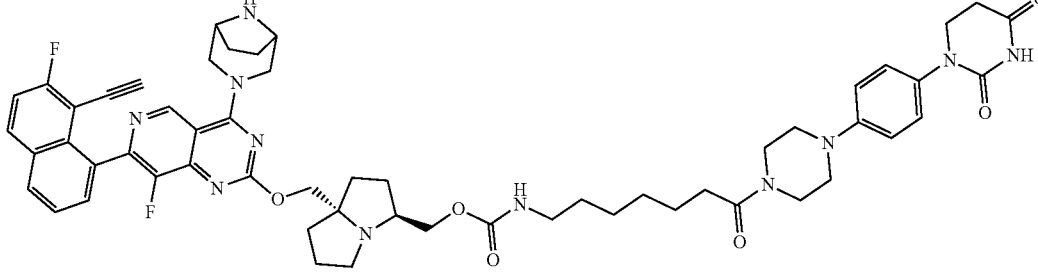 |

Methods of making compounds of the disclosure are described herein in the Exemplification.

Compositions, Combinations, Kits

Typically, for administration to a subject, a compound of the disclosure is formulated with one or more pharmaceutically acceptable carriers. The disclosure provides such compositions, including pharmaceutical compositions. Thus, one embodiment is a composition (e.g., pharmaceutical composition) comprising a compound of the disclosure and a pharmaceutically acceptable carrier. The compositions described herein can be used in accordance with the uses and/or methods described herein, e.g., to supply a compound of the disclosure for administration to a subject.

Compositions described herein and, hence, compounds of the disclosure, may be administered orally, parenterally (including subcutaneously, intramuscularly, intravenously and intradermally), by inhalation spray, topically, rectally, nasally, buccally, vaginally or via an implanted reservoir. The terms "parenteral" and "parenterally," as used herein, include subcutaneous, intracutaneous, intravenous, intramuscular, intraocular, intravitreal, intra-articular, intra-arterial, intra-synovial, intrasternal, intrathecal, intralesional, intrahepatic, intraperitoneal, intralesional and intracranial injection or infusion techniques. In some aspects, a composition described herein is administrable intravenously and/or intraperitoneally. In some aspects, a composition described herein is administrable orally. Preferably, a composition described herein is administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some aspects, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. In addition to the compound of the disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the disclosure can also be in microencapsulated form with one or more excipients, as noted above. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose. Compositions for oral administration may be designed to protect the active ingredient against degradation as it passes through the alimentary tract, for example, by an outer coating of the formulation on a tablet or capsule.

In another aspect, a compound of the disclosure can be provided in an extended (or "delayed" or "sustained") release composition. This delayed-release composition comprises the compound of the disclosure and a delayed-release component. Such a composition allows targeted release of the compound, for example, into the lower gastrointestinal tract, for example, into the small intestine, the large intestine, the colon and/or the rectum. In certain aspects, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition can provide controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/ or by acrylic acid linked to azoaromatic bonds coatings.

Compositions described herein can also be administered subcutaneously, intraperitoneally or intravenously, e.g., in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, dextrose, water, Ringer's solution, lactated Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Compositions described herein can also be administered in the form of suppositories for rectal administration. These can be prepared by mixing a compound of the disclosure with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topical transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. Suitable carriers also include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition, for example, consequences for red blood cells.

Other pharmaceutically acceptable carriers that can be used in the compositions described herein include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

In some aspects, a composition described herein further includes one or more additional therapeutic agents, e.g., for use in combination with a compound of the disclosure.

Some embodiments provide a combination (e.g., pharmaceutical combination) comprising a compound of the disclosure (e.g., a composition described herein comprising a compound of the disclosure) and one or more additional therapeutic agents (e.g., one or more compositions comprising one or more additional therapeutic agents). Such combinations are particularly useful as, for example, when the compound of the disclosure and the one or more additional therapeutic agents are to be administered separately. In a combination provided herein, the compound of the disclosure and the one or more additional therapeutic agents can be administrable by the same route of administration or by different routes of administration.

Some embodiments provide a kit comprising a compound of the disclosure (e.g., a composition described herein comprising a compound of the disclosure) and an additional therapeutic agent(s) (e.g., a composition comprising an additional therapeutic agent(s)). In one embodiment, the kit comprises a therapeutically effective amount of the compound of the disclosure to treat a disease, disorder or condition described herein, and a therapeutically effective amount of the one or more additional therapeutic agents to treat the disease, disorder or condition. In some aspects, the kit further comprises written instructions for administering the compound of the disclosure and/or the additional agent (s) to a subject to treat a disease, disorder or condition described herein.

Additional therapeutic agents for use in the compositions, combinations and/or kits provided herein include any of those discussed herein with respect to combination therapies.

The compositions described herein are, in some aspects, provided in unit dosage form. Thus, some embodiments provide a unit dosage form comprising a compound of the disclosure, e.g., and a pharmaceutically acceptable carrier. The amount of a compound of the disclosure or other therapeutic agent that can be combined with carrier material (s) to produce a composition in a unit dosage form will vary depending, for example, upon the subject treated, the particular mode of administration and the activity of the agent employed. Preferably, compositions and/or unit dosage forms should be formulated so that a compound of the disclosure or other therapeutic agent can be administered to a subject receiving the composition and/or unit dosage form at a dose and/or frequency consistent with those described herein. Typically, a unit dosage form will contain from about 1 mg to about 5,000 mg, from about 10 mg to about 2,500 mg, from about 100 mg to about 1,000 mg, from about 1 mg to about 1000 mg, from about 1 mg to about 500 mg, from about 1 mg to about 250 mg, from about 1 mg to about 150 mg, from about 0.5 mg to about 100 mg, or from about 1 mg to about 50 mg of active ingredient(s).

In some embodiments, the concentration of a therapeutic agent (e.g., a compound of the disclosure) in a composition is less than 100%, 90%, 80%, 70%, 60%, 50%, 40%, 30%, 20%, 15%, 10%, 9%, 8%, 7%, 6%, 5%, 4%, 3%, 2%, 1%, 0.5%, or 0.1% w/w, w/v or v/v; and/or greater than 90%, 80%, 70%, 60%, 50%, 40%, 30%, 20%, 15%, 10%, 9%, 8%, 7%, 6%, 5%, 4%, 3%, 2%, 1%, 0.5%, or 0.1% w/w, w/v, or v/v. In some embodiments, the concentration of a therapeutic agent (e.g., a compound of the disclosure) in a composition is in the range from about 0.001% to about 50%, about 0.001% to about 25%, about 0.01% to about 20%, about 0.05% to about 15%, about 0.1% to about 10%, or about 1% to about 10% w/w, w/v or v/v. In some embodiments, the concentration of a therapeutic agent (e.g., a compound of the disclosure) in a composition is in the range from about 0.001% to about 10%, about 0.01% to about 5%, or about 0.1% to about 1% w/w, w/v or v/v.

Uses

It has been found the various compounds of the disclosure exhibit effects consistent with degradation of KRAS G12D. Accordingly, provided herein in one embodiment is a method of reducing a level or activity of KRAS G12D in a cell (e.g., a cell expressing KRAS G12D), comprising contacting the cell with (e.g., an effective amount of) a compound of the disclosure or a composition comprising a compound of the disclosure. In some aspects, the method is conducted in vitro. In some aspects, the method is conducted ex vivo. In some aspects, the method is conducted in vivo. In some aspects, the cell is in a subject, such as a subject having a KRAS G12D-associated cancer.

Thus, provided herein in another embodiment is a method of reducing a level or activity of KRAS G12D in a subject in need thereof, comprising administering to the subject an effective amount (e.g., a therapeutically effective amount) of a compound of the disclosure or a composition comprising a compound of the disclosure.

KRAS G12D level or activity can be reduced in accordance with the methods described herein by, e.g., promoting degradation of KRAS G12D, via the UPP, for example, and/or inhibiting activity of KRASG12D. In some aspects, the method of reducing a level or activity of KRAS G12D is a method of promoting (e.g., inducing) degradation of KRAS G12D. Additionally or alternatively, in some aspects, the method of reducing a level or activity of KRAS G12D is a method of inhibiting activity of KRAS G12D.

Also provided herein in an embodiment is a method for treating a cancer (e.g., a KRAS G12D-associated cancer) in a subject in need thereof, comprising administering to the subject a therapeutically effective amount of a compound of the disclosure or a composition comprising a compound of the disclosure. The cancer can be a solid tumor cancer or a hematological cancer (e.g., a leukemia, a lymphoma or a myeloma). In some aspects, the cancer is a solid tumor cancer. In some aspects, the cancer is a hematologic cancer.

Cancers (e.g., KRAS G12D cancers) that may be treated in accordance with the methods described herein include, but are not limited to, astrocytic, breast, cervical, skin, colorectal, endometrial, esophageal, gastric, head and neck, hepatocellular, laryngeal, lung, oral, ovarian, testicular and prostate cancers, thyroid carcinomas and sarcomas. For example, the following cancers (e.g., KRAS G12D cancers) are treatable in accordance with the methods described herein: cardiac cancers, such as sarcoma (e.g., angiosarcoma, fibrosarcoma, rhabdomyosarcoma, liposarcoma), myxoma, rhabdomyoma, fibroma, lipoma and teratoma; lung cancers, such as bronchogenic carcinoma (e.g., squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal cancers, such as cancers of the esophagus (e.g., squamous cell carcinoma, adenocarcinoma, leiomyosarcoma, lymphoma), stomach (e.g., carcinoma, lymphoma, leiomyosarcoma), pancreas (e.g., ductal adenocarcinoma, insulinoma, glucagonoma, gastrinoma, carcinoid tumors, vipoma), small bowel (e.g., adenocarcinoma, lymphoma, carcinoid tumors, Kaposi's sarcoma, leiomyoma, hemangioma, lipoma, neurofibroma, fibroma), large bowel (e.g., adenocarcinoma, tubular adenoma, villous adenoma, hamartoma, leiomyoma); genitourinary tract cancers, such as cancers of the kidney (e.g., adenocarcinoma, Wilm's tumor (nephroblastoma), lymphoma, leukemia), bladder and urethra (e.g., squamous cell carcinoma, transitional cell carcinoma, adenocarcinoma), prostate (e.g., adenocarcinoma, sarcoma), testis (e.g., seminoma, teratoma, embryonal carcinoma, teratocarcinoma, choriocarcinoma, sarcoma, interstitial cell carcinoma, fibroma, fibroadenoma, adenomatoid tumors, lipoma); liver cancers, such as hepatoma (e.g., hepatocellular carcinoma), cholangiocarcinoma, hepatoblastoma, angiosarcoma, hepatocellular adenoma, hemangioma; biliary tract cancers, such as gall bladder carcinoma, ampullary carcinoma, cholangiocarcinoma; bone cancers, such as osteogenic sarcoma (e.g., osteosarcoma), fibrosarcoma, malignant fibrous histiocytoma, chondrosarcoma, Ewing's sarcoma, malignant lymphoma (e.g., reticulum cell sarcoma), multiple myeloma, malignant giant cell tumor chordoma, osteochronfroma (e.g., osteocartilaginous exostoses), benign chondroma, chondroblastoma, chondromyxofibroma, osteoid osteoma and giant cell tumors; nervous system cancers, such as cancers of the skull (e.g., osteoma, hemangioma, granuloma, xanthoma, osteitis deformans), meninges (e.g., meningioma, meningiosarcoma, gliomatosis), brain (e.g., astrocytoma, medulloblastoma, glioma, ependymoma, germinoma (e.g., pinealoma), glioblastoma multiform, oligodendroglioma, schwannoma, retinoblastoma, congenital tumors), spinal cord (e.g., neurofibroma, meningioma, glioma, sarcoma); gynecological cancers, such as cancers of the uterus (e.g., endometrial carcinoma), cervix (e.g., cervical carcinoma, pre-tumor cervical dysplasia), ovaries (e.g., ovarian carcinoma (e.g., serous cystadenocarcinoma, mucinous eysiadenocarcinoma, unclassified carcinoma), granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma (e.g., embryonal rhabdomyosarcoma), fallopian tubes (e.g., carcinoma); hematologic cancers, such as cancers of the blood (e.g., myeloid leukemia (e.g., acute, chronic), acute lymphoblastic leukemia, chronic lymphocytic leukemia, myeloproliferative diseases, multiple myeloma, myelodysplastic syndrome), Hodgkin's disease, non-Hodgkin's lymphoma (e.g., malignant lymphoma); skin cancers, such as malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, such as neuroblastoma.

Other examples of cancer treatable according to the methods described herein include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor, Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer, Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some aspects, the cancer is a metastatic cancer.

In some aspects, the cancer is a cardiac cancer, gastrointestinal cancer, genitourinary tract cancer, liver cancer, biliary tract cancer, bone cancer, nervous system cancer, gynecological cancer, hematologic cancer, skin cancer or adrenal gland cancer. In some aspects, the cancer is non-small cell lung cancer, small cell lung cancer, colorectal cancer, rectal cancer or pancreatic cancer.

In some aspects, the method further comprises determining whether the cell and/or subject has a KRAS G12D mutation. In some aspects, the method comprises determining whether a subject (e.g., a subject in need thereof, such as a subject having cancer) has a KRAS G12D-associated cancer, and administering to a subject having a KRAS G12D-associated cancer a therapeutically effective amount of a compound of the disclosure or a composition comprising a compound of the disclosure. Common KRAS G12D-associated cancers are known in the art. Methods for determining whether a subject has a KRAS G12D mutation and, hence, a KRAS G12D-associated cancer, are known in the art and described herein.

A compound of the disclosure can also be administered in combination with one or more other therapies (e.g., radiation therapy, a chemotherapy, such as a chemotherapeutic agent; an immunotherapy, such as an immunotherapeutic agent) to treat a disease, disorder or condition described herein (e.g., cancer, an autoimmune disease). When administered "in combination," the compound of the disclosure can be administered before, after or concurrently with the other therapy(ies) (e.g., radiation therapy, an additional therapeutic agent(s)). When co-administered simultaneously (e.g., concurrently), the compound of the disclosure and another therapeutic agent can be in separate formulations or the same formulation. Alternatively, the compound of the disclosure and another therapeutic agent can be administered sequentially, either at approximately the same time or at different times, as separate compositions. When the compound of the disclosure and the other therapy (e.g., therapeutic agent) are administered as separate formulations or compositions, the compound of the disclosure and the other therapy can be administered by the same route of administration or by different routes of administration. A skilled clinician can determine appropriate timing for administration of each therapy being used in combination (e.g., timing sufficient to allow an overlap of the pharmaceutical effects of the therapies).

In some aspects, a method described herein further comprises administering to the subject (e.g., a therapeutically effective amount of) an additional therapy(ies) (e.g., radiation therapy; additional therapeutic agent(s), such as a chemotherapeutic agent, an immunotherapeutic agent, an antibody, such as a monoclonal antibody; a vaccine), e.g., in combination with the compound of the disclosure. In some aspects, the compound of the disclosure is administered before the additional therapy(ies). In some aspects, the compound of the disclosure is administered after the additional therapy(ies). In some aspects, the compound of the disclosure is administered concurrently with the additional therapy(ies).

In some aspects, a method further comprises administering to the subject radiation therapy (e.g., a therapeutically effective amount of radiation therapy), e.g., proton beam therapy.

In some aspects, a method further comprises administering to the subject hormone therapy (e.g., a therapeutically effective amount of hormone therapy), e.g., anti-estrogen therapy, androgen deprivation therapy (ADT), such as flutamide, nilutamide, bicalutamide, leuprolide or goserelin, a luteinizing hormone-releasing hormone (LHRH) agonist, an aromatase inhibitor (AI), such as anastrozole, exemestane or letrozole, an estrogen receptor modulator, such as tamoxifen, raloxifene or toremifene.

In some aspects, a method further comprises administering to the subject an epidermal growth factor receptor (EGFR) inhibitor (e.g., a therapeutically effective amount of an EGFR inhibitor), such as cetuximab. Other examples of EGFR inhibitors include the pan-EGFR inhibitors dacomitinib and mefatinib.

In some aspects, a method further comprises administering to the subject (e.g., a therapeutically effective amount of) a cyclin-dependent kinase (CDK) inhibitor (e.g., a CDK4/6 inhibitor). Examples of CDK inhibitors include abemaciclib, alvocidib, palbociclib, and ribociclib.

In some aspects, a method further comprises administering to the subject (e.g., a therapeutically effective amount of) a son of sevenless (SOS), e.g., SOS1, inhibitor. SOS1 inhibitors are disclosed, for example, in International Publication No. WO 2021/173524.

In some aspects, a method further comprises administering to the subject (e.g., a therapeutically effective amount of) a small heterodimer partner (SHP), e.g., SHP2, inhibitor. Examples of SHP2 inhibitors include SHP-099, RMC-4550, RMC4360 and TNO155.

In some aspects, a method further comprises administering to the subject an immunotherapy (e.g., a therapeutically effective amount of an immunotherapy). Immunotherapy agents include antibodies that inhibit proteins expressed by cancer cells, vaccines and immune cell (e.g., T-cell) infusions. Antibody agents useful for promoting anti-tumor responses include anti-CTLA-4 antibodies (e.g., ipilimumab, tremelimumab), anti-PD-1 antibodies (e.g., pembrolizumab, nivolumab, cemiplimab), anti-PD-L1 antibodies (e.g., atezolizumab, avelumab, durvalumab), anti-PD-L2 antibodies, anti-TIM-3 antibodies, anti-LAG-3 antibodies (e.g., relatlimab), anti-OX40 antibodies and anti-GITR antibodies. In some aspects, the immunotherapy is an immune checkpoint inhibitor (e.g., a therapeutically effective amount of an immune checkpoint inhibitor), e.g., for treating a solid tumor cancer. Examples of immune checkpoint inhibitors include inhibitors of CTLA-4 (e.g., ipilimumab, tremelimumab), PD-1 (e.g., nivolumab, pembrolizumab), PD-L1 (e.g., avelumab), PD-L2, TIM-3, LAG-3 (e.g., relatlimab), OX40 and GITR. In some aspects, the immune checkpoint inhibitor (e.g., for treating a solid tumor cancer) is an inhibitor of CTLA-4, PD-1, PD-L1 or LAG-3. In some aspects, the immune checkpoint inhibitor (e.g., for treating a solid tumor cancer) is an inhibitor of PD-1 or PD-L1. In some aspects, the immune checkpoint inhibitor (e.g., for treating a solid tumor cancer) is an inhibitor of PD-1, such as pembrolizumab.

In some aspects, a method further comprises administering to the subject a chemotherapy (e.g., a therapeutically effective amount of a chemotherapy), e.g., comprising one or more chemotherapeutic agents. Examples of chemotherapeutic agents include, for example, antimetabolites (e.g., folic acid, nucleotide analogs, in particular, purine and pyrimidine derivatives); alkylating agents (e.g., cyclophosphamide, mechlorethamine, chlorambucil, melphalan, dacarbazine, temozolomide, thiotepa); anthracyclines (e.g., daunorubicin, doxorubicin, epirubicin, idarubicin, mitoxantrone, valrubicin); taxanes (e.g., paclitaxel, docetaxel, abraxane, taxotere); epothilones; histone deacetylase inhibitors (e.g., vorinostat, romidepsin); topoisomerase inhibitors (e.g., irinotecan, topotecan, etoposide, teniposide, tafluposide); kinase inhibitors (e.g., bortezomib, erlotinib, gefitinib, imatinib, vemurafenib, vismodegib); nucleotide analogs (e.g., azacitidine, azathioprine, capecitabine, cytarabine, doxifluridine, fluorouracil, gemcitabine, hydroxyurea, mercaptopurine, methotrexate, tioguanine); peptide antibiotics (e.g., bleomycin, actinomycin); platinum-based agents (e.g., carboplatin, cisplatin, oxaliplatin); retinoids (e.g., tretinoin, alitretinoin, bexarotene); and vinca alkaloids (e.g., vinblastine, vincristine, vindesine, vinorelbine), as well as their pharmaceutically acceptable salts. Further examples of chemotherapeutic agents include alkylating agents, such as thiotepa and cyclophosphamide (CYTOXAN™); alkyl sulfonates, such as busulfan, improsulfan and piposulfan; aziridines, such as benzodopa, carboquone, meturedopa, and uredopa; ethylenimines and methylamelamines, such as altretamine, triethylenemelamine, trietylenephosphoramide, triethylenethiophosphaoramide and trimethylolomelamine; acetogenins, such as bullatacin and bullatacinone; camptothecins, including the synthetic analogue topotecan; bryostatin; callystatin; CC-1065, including its adozelesin, carzelesin and bizelesin analogues; cryptophycins, such as cryptophycin 1 and cryptophycin 8; dolastatin; duocarmycin, including the synthetic analogues, KW-2189 and CBI-TMI; eleutherobin; pancratistatin; sarcodictyins; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosoureas, such as carmustine, chlorozotocin, fotemustine, lomustine, nimustine, and ranimustine; antibiotics, such as the enediyne antibiotics (e.g., calicheamicin, especially calicheamicin gamma 1 and calicheamicin theta I, see, e.g., *Angew Chem. Intl. Ed. Engl.* 33:183-186 (1994); dynemicin, such as dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, methotrexate, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, floxuridine, and 5-FU; androgens, such as calusterone, dromostanolone propionate, epitiostanol, mepitiostane, and testolactone; anti-adrenals, such as aminoglutethimide, mitotane, and trilostane; folic acid replenishers, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilones; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2′,2″-trichlorotriethylamine; trichothecenes, such as T-2 toxin, verracurin A, roridin A and anguidine; urethan; vindesine; dacarbazine; mannomustine; mitobronitol; mitolactol; pipobroman; gacytosine; arabinoside ("Ara-C"); cyclophosphamide; thiotepa; taxoids, such as paclitaxel (e.g., TAXOL™, Bristol-Myers Squibb Oncology, Princeton, N.J.; nab-paclitaxel, such as the nanoparticle albumin-bound form of paclitaxel sold as ABRAXANE®) and doxetaxel (TAXOTERE®, Rhone-Poulenc Rorer, Antony, France); chlorambucil; gemcitabine; 6-thioguanine; mercaptopurine; methotrexate; folinic acid; platinum analogs such as cisplatin, oxaliplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitors, such as irinotecan and RFS 2000; difluoromethylomithine (DFMO); retinoic acid; and capecitabine; as well as their pharmaceutically acceptable salts.

Specific examples of chemotherapeutic agents include aclarubicin, actinomycin, alitretinon, altretamine, aminopterin, aminolevulinic acid, amrubicin, amsacrine, anagrelide, arsenic trioxide, asparaginase, atrasentan, belotecan, bexarotene, bendamustine, bleomycin, bortezomib, busulfan, camptothecin, capecitabine, carboplatin, carboquone, carmofur, carmustine, celecoxib, chlorambucil, chlormethine, cisplatin, cladribine, clofarabine, crisantaspase, cyclophosphamide, cytarabine, dacarbazine, dactinomycin, daunorubicin, decitabine, demecolcine, docetaxel, doxorubicin, efaproxiral, elesclomol, elsamitrucin, enocitabine, epirubicin, estramustine, etoglucid, etoposide, floxuridine, fludarabine, fluorouracil (5FU), fotemustine, gemcitabine, gliadel implants, hydroxycarbamide, hydroxyurea, idarubicin, ifosfamide, irinotecan, irofulven, ixabepilone, larotaxel, leucovorin, liposomal doxorubicin, liposomal daunorubicin, lonidamine, lomustine, lucanthone, mannosulfan, masoprocol, melphalan, mercaptopurine, mesna, methotrexate, methyl aminolevulinate, mitobronitol, mitoguazone, mitotane, mitomycin, mitoxantrone, nedaplatin, nimustine, oblimersen, omacetaxine, ortataxel, oxaliplatin, paclitaxel, pegaspargase, pemetrexed, pentostatin, pirarubicin, pixantrone, plicamycin, porfimer sodium, prednimustine, procarbazine, raltitrexed, ranimustine, rubitecan, sapacitabine, semustine, sitimagene ceradenovec, strataplatin, streptozocin, talaporfin, tegafur-uracil, temoporfin, temozolomide, teniposide, tesetaxel, testolactone, tetranitrate, thiotepa, tiazofurine, tioguanine, tipifarnib, topotecan, trabectedin, triaziquone, triethylenemelamine, triplatin, tretinoin, treosulfan, trofosfamide, uramustine, valrubicin, verteporfin, vinblastine, vincristine, vindesine, vinflunine, vinorelbine, vorinostat and zorubicin, or a pharmaceutically acceptable salt of the foregoing.

Numerous other therapies can also be administered during treatment (e.g., cancer treatment, treatment of an autoimmune disease) to mitigate the effects of the disease and/or side effects of the treatment, including therapies to manage pain (e.g., narcotics, acupuncture), gastric discomfort (e.g., antacids), dizziness (e.g., anti-vertigo medications), nausea (e.g., anti-nausea medications), infection (e.g., medications to increase red/white blood cell counts) and the like, all of which are readily appreciated by the person skilled in the art.

A compound of the disclosure or other therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. In some aspects, administration (e.g., of a compound of the disclosure) is oral. In some aspects, administration (e.g., of a compound of the disclosure) is intravenous. In some aspects, administration (e.g., of a compound of the disclosure) is by injection or infusion. The preferred mode of administration can vary depending on the particular compound or agent.

Typically, a compound of the disclosure or other therapeutic agent will be administered from about 1 to about 6

(e.g., 1, 2, 3, 4, 5 or 6) times per day, also or alternatively, as an infusion (e.g., a continuous infusion). In some embodiments, a compound of the disclosure or other therapeutic agent is administered once daily (QD) or twice daily (BID). In some embodiments, a compound of the disclosure or other therapeutic agent is administered BID.

A compound of the disclosure or other therapeutic agent can be administered in a dosage ranging from about 0.001 mg/kg to about 100 mg/kg of body weight or, alternatively, in a dosage ranging from about 1 mg/dose to about 5,000 mg/dose, every 4 to 120 hours, or according to the requirements of the particular agent. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages can be from about 1 mg/dose to about 5,000 mg/dose, from about 10 mg/dose to about 2,500 mg/dose or from about 100 mg/dose to about 1,000 mg/dose.

Doses lower or higher than those recited above may be required. Specific dosage and treatment regimens for any particular patient will depend, for example, upon a variety of factors, such as the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. Determining the dosage for a particular agent, subject and disease, disorder or condition is within the abilities of one of skill in the art.

EXEMPLIFICATION

The compounds of the disclosure can be prepared in a number of ways known to one skilled in the art in view of the methods, reaction schemes and examples provided herein. The compounds of the disclosure can be synthesized using the methods described below, together with synthetic methods known in the art of synthetic organic chemistry, or by variations thereon, as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound.

The starting materials are generally available from commercial sources such as Sigma Aldrich or other commercial vendors, or are prepared as described herein, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, 2$^{nd}$ ed., Wiley-VCH Weinheim, Germany (1999), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the disclosure as well as intermediates. Those skilled in the art will appreciate that other synthetic routes may be used to synthesize the compounds of the present disclosure. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the disclosure, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007). Protecting groups incorporated in making of the compounds of the present disclosure, such as the trityl protecting group, may be shown as one regioisomer but may also exist as a mixture of regioisomers.

The following abbreviations used hereinbelow have the corresponding meanings:
ACN acetonitrile;
Boc tert-butyloxycarbonyl;
C Celsius;
d doublet;
dd doublet of doublets;
DCM dichloromethane;
DMAP 4-dimethylaminopyridine;
DIEA N,N-diisopropylethylamine;
DMSO dimethylsulfoxide;
Dtbbpy 4,4'-di-tert-butyl-2,2'-dipyridyl;
DME dimethoxyethane;
EtOAc/EA ethyl acetate;
EtOH ethanol;
FA formic acid;
g gram(s);
h/hr hour(s);
HPLC high pressure liquid chromatography;
HCl hydrochloric acid
L liter;
LC liquid chromatography;
LCMS liquid chromatography and mass spectrometry;
LiAlH$_4$ lithium aluminum hydride;
LiHMDS lithium bis(trimethylsilyl)amine;
MeOH methanol;
MS mass spectrometry;
M molar;
m multiplet;
Me methyl;
min/min. minute(s);
mL milliliter(s);
µM micromolar;
m/z mass to charge ratio;
nM nanomolar;
NMP N-methylpyrrolidone;
NMR nuclear magnetic resonance;
NaH sodium hydride;
NaHCO$_3$ sodium bicarbonate;
Pd/C palladium on carbon;
PG protecting group;
PE petroleum ether;
POCl$_3$ phosphoryl chloride;
rt room temperature
s singlet;
sat. saturated;

SFC supercritical fluid chromatography;
t triplet;
t-Bu tert-butyl;
TEA triethylamine;
TBAF Tetra-n-butylammonium fluoride;
TTMSS tris(trimethylsilyl)silane;
TFA trifluoroacetic acid;
THF tetrahydrofuran;
TLC thin layer chromatography;

Example 1. Synthesis of Int. B a) Synthesis of O1-benzyl O2-methyl 2-but-3-enylpyrrolidine-1,2-dicarboxylate

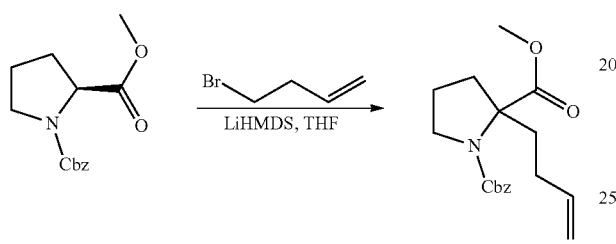

A solution of O1-benzyl O2-methyl (2S)-pyrrolidine-1,2-dicarboxylate (120 g, 455 mmol, CAS #182210-00-0) in THF (200 mL) was added dropwise to a solution of LiHMDS (1 M, 546 mL) at −78° C. for 1 hr. To the mixture was added 4-bromobut-1-ene (123 g, 911 mmol, CAS #5162-44-7) and was stirred at 25° C. for 16 hrs under $N_2$ atmosphere. Upon completion, the reaction mixture was concentrated in vacuo to provide a residue. The residue was purified via column chromatography (SiO₂, PE:EA=0:1 to 5:1) to afford the title compound (120 g, 66% yield) as white oil. LC-MS (ESI+) m/z 318.0 (M+H)+.

b) Synthesis of O1-benzyl O2-methyl 2-[2-(oxiran-2-yl)ethyl]pyrrolidine-1,2-dicarboxylate

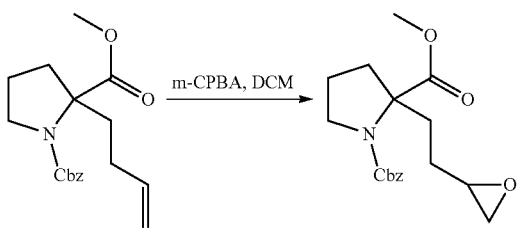 [SMILES: C=CCCC1(C(=O)OC)CCCN1C(=O)OCc1ccccc1 ; COC(=O)C1(CCC2CO2)CCCN1C(=O)OCc1ccccc1]

A solution of O1-benzyl O2-methyl 2-but-3-enylpyrrolidine-1, 2-dicarboxylate (146 g, 460 mmol) and m-CPBA (233 g, 1.15 mol, 85% purity) in DCM (1500 mL) was stirred at 20° C. for 16 hrs. Upon completion, the reaction mixture was extracted with EA (3×400 mL). The combined organic layers were washed with brine (300 mL), dried over anhydrous $Na_2SO_4$, filtered and the filtrate was concentrated in vacuo to give a residue. The residue was purified via column chromatography (SiO₂, PE:EA=0:1 to 3:1) to afford the title compound (110 g, 45% yield) as white oil. $^1$H NMR (400 MHz, CDCl₃) δ 7.40-7.27 (m, 5H), 5.18-5.07 (m, 2H), 3.78-3.70 (m, 3H), 3.50-3.46 (m, 2H), 2.73-2.71 (m, 2H), 2.43-2.42 (m, 2H), 2.13-1.85 (m, 5H), 1.53-1.45 (m, 2H); LC-MS (ESI⁺) m/z 334.1 (M+H)⁺.

c) Synthesis of Methyl 3-(hydroxymethyl)-1,2,3,5,6,7-hexahydropyrrolizine-8-carboxylate

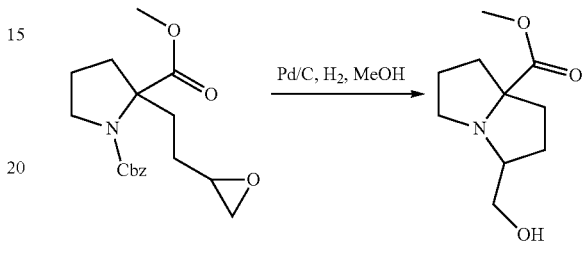

To a solution of O1-benzyl O2-methyl 2-[2-(oxiran-2-yl)ethyl]pyrrolidine-1,2-dicarboxylate (110 g, 329 mmol) in MeOH (1000 mL) was added Pd/C (10.0 g, 330 mmol, 10% purity) under $N_2$ atmosphere. The suspension was degassed and purged with hydrogen gas for 3 times. The reaction mixture was stirred under hydrogen (50 psi) at 20° C. for 16 hrs. Upon completion, the reaction mixture was filtered and the filtrate was concentrated in vacuo to afford the title compound (62.0 g, 94% yield) as a yellow oil. LC-MS (ESI⁺) m/z 200.0 (M+H)⁺.

d) Synthesis of Methyl 3-[[tert-butyl(diphenyl)silyl]oxymethyl]-1,2,3,5,6,7-hexahydropyrrolizine-8-carboxylate

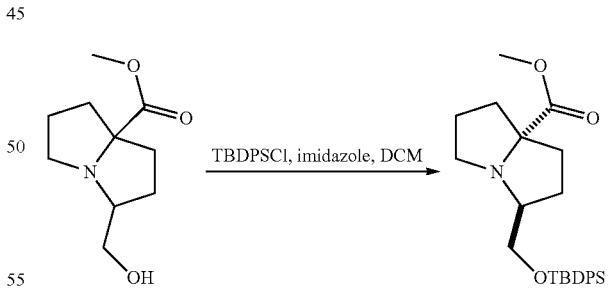

To a solution of methyl 3-(hydroxymethyl)-1,2,3,5,6,7-hexahydropyrrolizine-8-carboxylate (54.0 g, 271 mmol), tert-butyl-chloro-diphenyl-silane (111 g, 406 mmol) and imidazole (55.3 g, 813 mmol) in DCM (500 mL) was stirred at 20° C. for 16 hrs. Upon completion, the mixture was filtered and the filtrate was concentrated in vacuo to afford a residue. The residue was purified by column chromatography (SiO₂, PE:EA=0:1 to 3:1) to afford the title compound (trans racemic) (61.0 g, 41% yield) as a yellow oil. LC-MS (ESI⁺) m/z 438.7 (M+H)⁺.

e) Synthesis of [3-[[Tert-butyl(diphenyl)silyl]oxymethyl]-1,2,3,5,6,7-hexahydropyrrolizin-8-yl]methanol

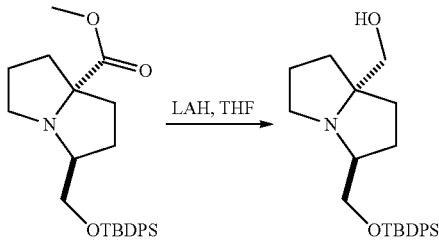

To a solution of methyl 3-[[tert-butyl(diphenyl)silyl]oxymethyl]-1,2,3,5,6,7-hexahydropyrrolizine-8-carboxylate (10.4 g, 23.0 mmol) in THF (100 mL) was added LiAlH$_4$ (1.80 g, 47.0 mmol). The mixture was stirred at −20° C. for 2 hrs. Upon completion, to the mixture was added H$_2$O (2.2 mL) and 15% NaOH (2.2 mL). The mixture was then dried over anhydrous sodium sulfate, filtered and the filtrate was concentrated in vacuo to give a residue. The residue was purified by reverse phase (0.1% FA condition) to afford the title compound (trans racemic) (7.10 g 73% yield) as white solid. LC-MS (ESI$^+$) m/z 410.3 (M+H)$^+$.

[(3S,8S)-3-[[tert-butyl(diphenyl)silyl]oxymethyl]-1,2,3,5,6,7-hexahydropyrrolizin-8-yl]methanol (40.0 g, 97.6 mmol) was separated by SFC (column: REGIS (s,s) WHELK-O1 (250 mm*50 mm, 10 μm); mobile phase: [0.1% NH$_3$—H$_2$O EtOH]; B %: 50%-50%, B2.95; 300 min) to afford Int. A (15.0 g, 37% yield) (retention time: 2.088 min) as yellow oil and Int. B (15.0 g, 37% yield) (retention time: 1.823 min) as yellow oil.

Int. A: $^1$H NMR (400 MHz, CDCl$_3$) δ 8.38 (s, 1H), 7.58-7.53 (m, 4H), 7.41-7.30 (m, 6H), 3.93-3.88 (m, 1H), 3.81 (d, J=13.2 Hz, 1H), 3.76-3.64 (m, 2H), 3.57-3.48 (m, 2H), 3.39 (s, 1H), 3.22-3.12 (m, 1H), 2.32-2.22 (m, 1H), 2.08-1.83 (m, 5H), 1.75-1.61 (m, 2H), 1.00 (s, 9H); LC-MS (ESI$^+$) m/z 410.6 (M+H)$^+$.

Int. B: $^1$H NMR (400 MHz, CDCl$_3$) δ 7.70-7.65 (m, 4H), 7.46-7.37 (m, 6H), 3.95-3.88 (m, 1H), 3.81-3.75 (m, 1H), 3.48 (s, 1H), 3.31 (s, 2H), 3.26-3.16 (m, 1H), 2.93-2.84 (m, 1H), 2.81-2.68 (m, 1H), 2.02-1.93 (m, 1H), 1.80-1.62 (m, 6H), 1.59-1.51 (m, 1H), 1.07 (s, 9H); LC-MS (ESI$^+$) m/z 410.6 (M+H)$^+$.

Initially, absolute structures were assigned to Int. A and Int. B randomly, with Int. A being assigned as [(3R,8R)-3-[[tert-butyl(diphenyl)silyl]oxymethyl]-1,2,3,5,6,7-hexahydropyrrolizin-8-yl]methanol, and Int. B being assigned as [(3S,8S)-3-[[tert-butyl(diphenyl)silyl]oxymethyl]-1,2,3,5,6,7-hexahydropyrrolizin-8-yl]methanol.

Subsequently, x-ray crystallographic analysis revealed that Int. A corresponded to [(3S,8S)-3-[[tert-butyl(diphenyl)silyl]oxymethyl]-1,2,3,5,6,7-hexahydropyrrolizin-8-yl]methanol, and Int. B corresponded to [(3R,8R)-3-[[tert-butyl(diphenyl)silyl]oxymethyl]-1,2,3,5,6,7-hexahydropyrrolizin-8-yl]methanol. Briefly, 10 mg Int. A and 25 μL HCl (1 mol/L) were dissolved in 600 μL heptane and kept in a sealed, 4-mL vial. In a separate sealed, 4-mL vial, 10 mg Int. B and 25 μL HCl (1 mol/L) were dissolved in 600 μL heptane and kept. The solutions were evaporated slowly at room temperature. The resulting crystals were analyzed using a Rigaku Oxford Diffraction XtaLAB Synergy-S four-circle diffractometer equipped with a HyPix-6000HE area detector, and the following equipment:

Cryogenic system: Oxford Cryostream 800
Cu: λ=1.54184 Å, 50 W, Micro focus source with multilayer mirror (μ-CMF).
Distance from the crystal to the CCD detector: d=35 mm
Tube Voltage: 50 kV
Tube Current: 1 mA.

The resulting Int. A HCl crystal was a colorless block with the following dimensions: 0.30×0.30×0.20 mm$^3$. The symmetry of the crystal structure was assigned the monoclinic space group P2$_1$ with the following parameters: a=10.9303(10) Å, b=7.80050(10) Å, c=15.03770(10) Å, α=90°, β=103.4170(10)°, γ=90°, V=1247.15(2) Å$^3$, Z=2, Dc=1.188 g/cm3, F(000)=480.0, μ(Cu Kα)=1.966 mm$^{-1}$, and T=293 (2)K. The resulting Int. B HCl crystal was a colorless block with the following dimensions: 0.30×0.30×0.20 mm$^3$. The symmetry of the crystal structure was assigned the monoclinic space group P2$_1$ with the following parameters: a=10.9653(3) Å, b=7.7994(2) Å, c=15.0838(3) Å, α=90°, β=103.489(2)°, γ=90°, V=1254.42(5) Å$^3$, Z=2, Dc=1.181 g/cm3, F(000)=480.0, μ(Cu Kα)=1.955 mm$^{-1}$, and T=293 (2)K.

The initial, randomly-assigned absolute configurations of Int. A and Int. B were revised on the basis of these and other data collected and analyzed in connection with the x-ray crystallographic analysis of Int. A and Int. B.

Example 2. Synthesis of Int. C a) Synthesis of 2,4,7-Trichloro-8-fluoro-pyrido[4,3-d]pyrimidine

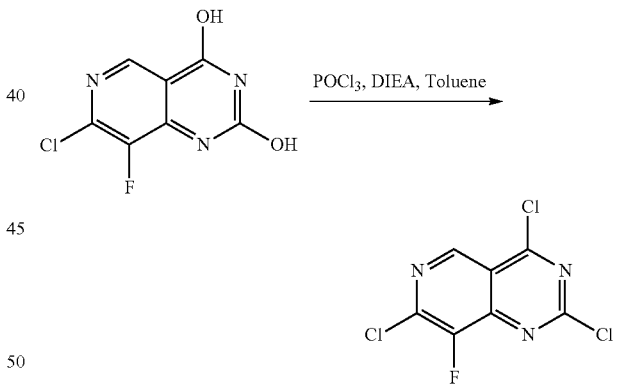

To a solution of 7-chloro-8-fluoro-pyrido[4,3-d]pyrimidine-2,4-diol (5.00 g, 23.2 mmol, CAS #2454397-75-0) in toluene (300 mL) was added DIEA (14.9 g, 115 mmol) and POCl$_3$ (10.6 g, 69.5 mmol) at 0° C. The mixture was stirred at 110° C. for 2 hrs. Upon completion, the mixture was concentrated in vacuo to provide a residue. Then the residue was diluted with EA (200 mL) and dropwise added to H$_2$O (300 mL). Then pH was adjusted to 7-8 with saturated NaHCO$_3$ solution and the mixture was extracted with EA (3×200 mL). The organic layer was dried over anhydrous Na$_2$SO$_4$, filtered and the filtrate was concentrated in vacuo to provide a residue. The residue was purified by column chromatography (SiO$_2$, PE:EA=50:1 to 5:1) to provide the title compound (8.00 g, 68% yield) as yellow solid. $^1$H NMR (400 MHz, DMSO-d$_6$) δ 8.91 (s, 1H).

b) Synthesis of Tert-butyl 3-(2,7-dichloro-8-fluoro-pyrido[4,3-d]pyrimidin-4-yl)-3,8-diazabicyclo[3.2.1]octane-8-carboxylate

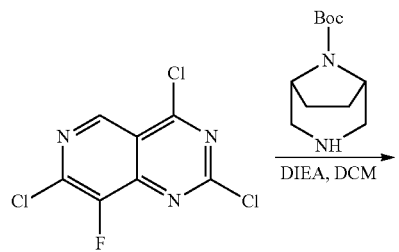

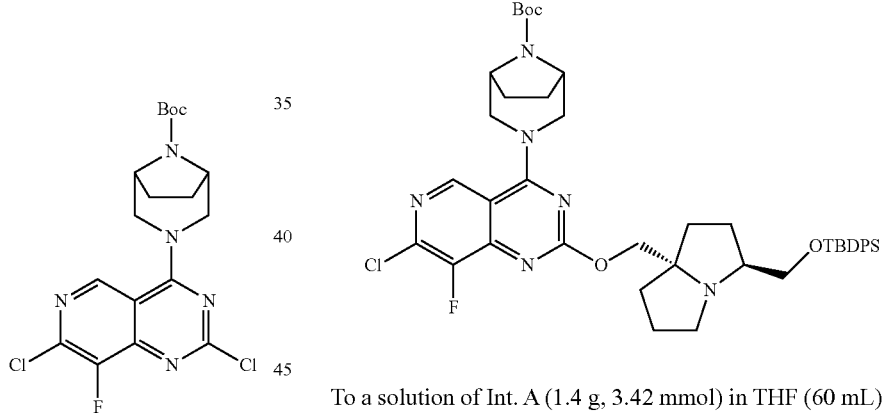

To a solution of 2,4,7-trichloro-8-fluoro-pyrido[4,3-d]pyrimidine (2.1 g, 8.32 mmol) in DCM (120 mL) was added DIEA (7.53 g, 58.2 mmol) at 25° C. Then a solution of tert-butyl (1S,5R)-3,8-diazabicyclo[3.2.1]octane-8-carboxylate (1.24 g, 5.82 mmol, CAS #149771-44-8) in DCM (120 mL) was added to the mixture was stirred at −40° C. The mixture was stirred at −40° C. for 1 hr. Upon completion, the reaction mixture was diluted by H$_2$O (100 mL) at 25° C., and then extracted with DCM (3×100 mL). The combined organic layers were washed with brine (2×200 mL), dried over anhydrous Na$_2$SO$_4$, filtered and concentrated under in vacuo to give a residue. The residue was purified by column chromatography (SiO$_2$, PE:EA=20:1 to 4:1) to afford the title compound (4.40 g, 62% yield) as yellow solid. $^1$H NMR (400 MHz, CDCl$_3$) δ 8.85 (s, 1H), 4.70-4.27 (m, 4H), 3.90-3.54 (m, 2H), 2.04-1.94 (m, 2H), 1.68 (d, J=7.2 Hz, 2H), 1.53 (s, 9H); LC-MS (ESI$^+$) m/z 428.0 (M+H)$^+$.

c) Synthesis of Tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate

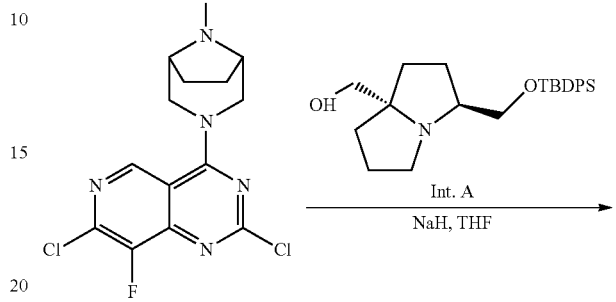

To a solution of Int. A (1.4 g, 3.42 mmol) in THF (60 mL) was added NaH (410 mg, 10.2 mmol, 60% purity) at 0° C. The mixture was stirred at 0° C. for 0.5 hr. Then tert-butyl 3-(2,7-dichloro-8-fluoro-pyrido[4,3-d]pyrimidin-4-yl)-3,8-diazabicyclo[3.2.1]octane-8-carboxylate (1.61 g, 3.76 mmol) was added to the mixture. The mixture was stirred at 25° C. for 12 hrs. Upon completion, the residue was quenched by H$_2$O (30 mL) and extracted with EA (2×100 mL). The combined organic layers were washed with brine (80 mL), dried over anhydrous Na$_2$SO$_4$, filtered and concentrated in vacuo to provide a residue. The residue was purified by prep-HPLC (column: Welch Ultimate XB-SiOH 250*50*10 μm; mobile phase: [Hexane-EtOH]; B %: 0%-26%, 25 min) to afford the title compound (1.50 g, 55% yield) as yellow solid. $^1$H NMR (400 MHz, CDCl$_3$) δ 8.72 (s, 1H), 7.75-7.58 (m, 4H), 7.53-7.34 (m, 6H), 4.62-4.30 (m, 4H), 4.29-4.08 (m, 2H), 3.99 (dd, J=4.8, 10.4 Hz, 1H), 3.81 (dd, J=7.2, 10.0 Hz, 1H), 3.77-3.34 (m, 3H), 3.29 (s, 1H), 2.89-2.73 (m, 2H), 2.25-2.15 (m, 1H), 2.00-1.89 (m, 4H), 1.88-1.73 (m, 4H), 1.69 (d, J=7.6 Hz, 2H), 1.52 (s, 9H), 1.06 (s, 9H); LC-MS (ESI$^+$) m/z 801.4 (M+H)$^+$.

d) Synthesis of Tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

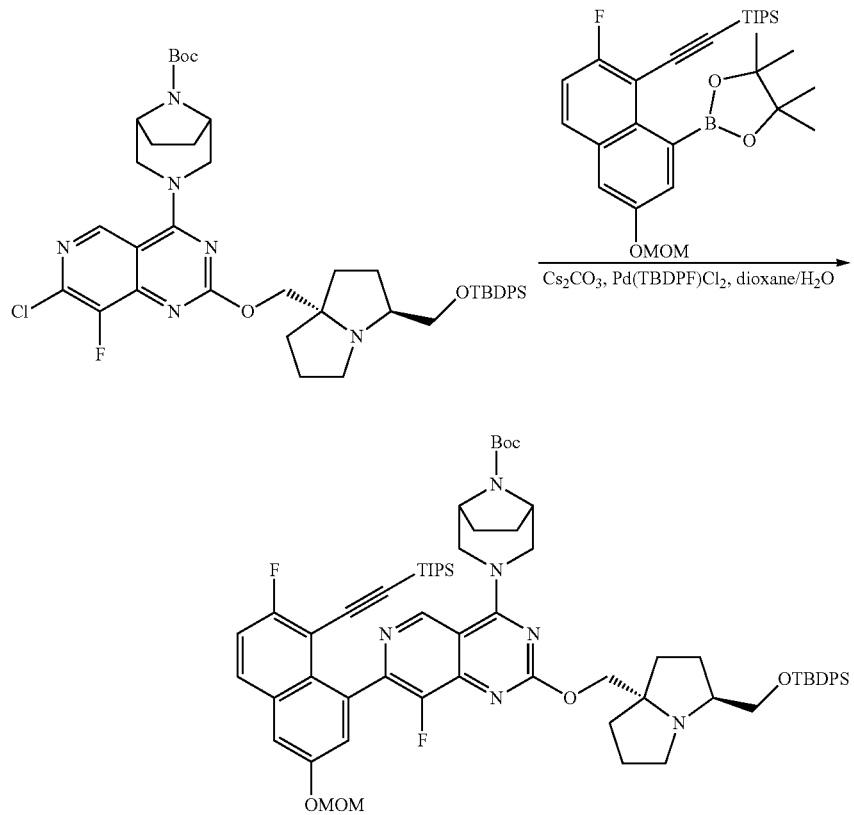

A solution of tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (569 mg, 709 μmol), 2-[2-fluoro-6-(methoxymethoxy)-8-(4,4,5,5-tetramethyl-1,3,2-dioxaborolan-2-yl)-1-naphthyl]ethynyl-triisopropyl-silane (727 mg, 1.42 mmol, CAS #2621932-37-2), ditert-butyl(cyclopentyl)phosphane; dichloropalladium; iron (92.5 mg, 141 μmol) and Cs$_2$CO$_3$ (693 mg, 2.13 mmol) in dioxane (24 mL) and H$_2$O (4.8 mL) was degassed and purged with N$_2$ atmosphere for 3 times. The mixture was stirred at 100° C. for 0.5 hr under N$_2$ atmosphere. On completion, the reaction mixture was concentrated in vacuo to provide a residue. The residue was purified by column chromatography (SiO$_2$, PE:EA=1:0 to 0:1) to afford the title compound (562 mg, 69% yield) as yellow solid. $^1$H NMR (400 MHz, CDCl$_3$) δ 9.08-9.03 (m, 1H), 7.79 (dd, J=5.6, 9.2 Hz, 1H), 7.70-7.67 (m, 3H), 7.64 (d, J=4.0 Hz, 1H), 7.51 (d, J=2.4 Hz, 1H), 7.41 (d, J=7.2 Hz, 6H), 7.30 (d, J=10.4 Hz, 2H), 5.32-5.28 (m, 2H), 4.87-4.83 (m, 1H), 4.49-4.34 (m, 2H), 4.28-4.06 (m, 4H), 4.01 (dd, J=4.4, 10.0 Hz, 1H), 3.82 (s, 2H), 3.51 (s, 3H), 3.46-3.17 (m, 2H), 2.93-2.73 (m, 2H), 2.32-2.16 (m, 2H), 2.05-1.71 (m, 12H), 1.65-1.60 (m, 6H), 1.53 (s, 9H), 1.47-1.15 (m, 9H), 1.15-1.00 (m, 12H); LC-MS (ESI$^+$) m/z 1151.6 (M+H)$^+$.

e) Synthesis of Tert-butyl 3-[7-[8-ethynyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

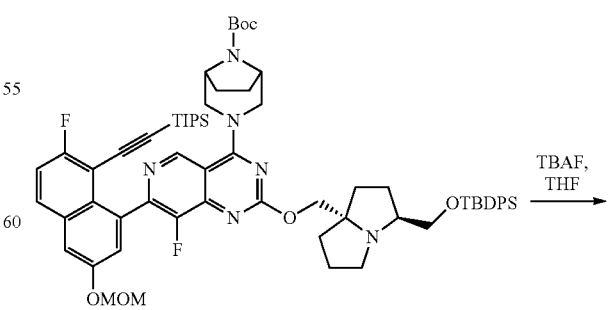

843

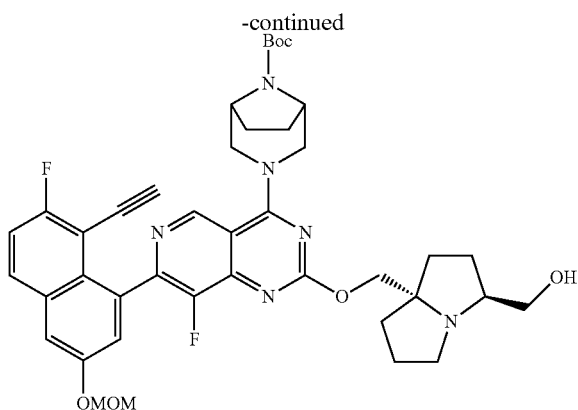

To a solution of tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (560 mg, 486 μmol) in THF (5 mL) was added TBAF (1 M, 1.46 mL) at 0° C. The mixture was stirred at 25° C. for 16 hrs under $N_2$ atmosphere. Upon completion, the mixture was concentrated in vacuo to give a residue. The residue was diluted with $H_2O$ (15 mL), and then extracted with EA (3×15 mL). The combined organic was washed with brine (2×15 mL), dried over anhydrous $Na_2SO_4$, filtered and concentrated in vacuo to provide a residue. The residue was purified by column chromatography (SiO$_2$, PE:EA=50:1 to 1:1) to afford the title compound (220 mg, 59% yield) as yellow solid. LC-MS (ESI$^+$) m/z 757.4 (M+H)$^+$.

f) Synthesis of Tert-butyl 3-[7-[8-ethynyl-7-fluoro-3-(methoxymethoxy)-1-naphthyl]-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (Int. C)

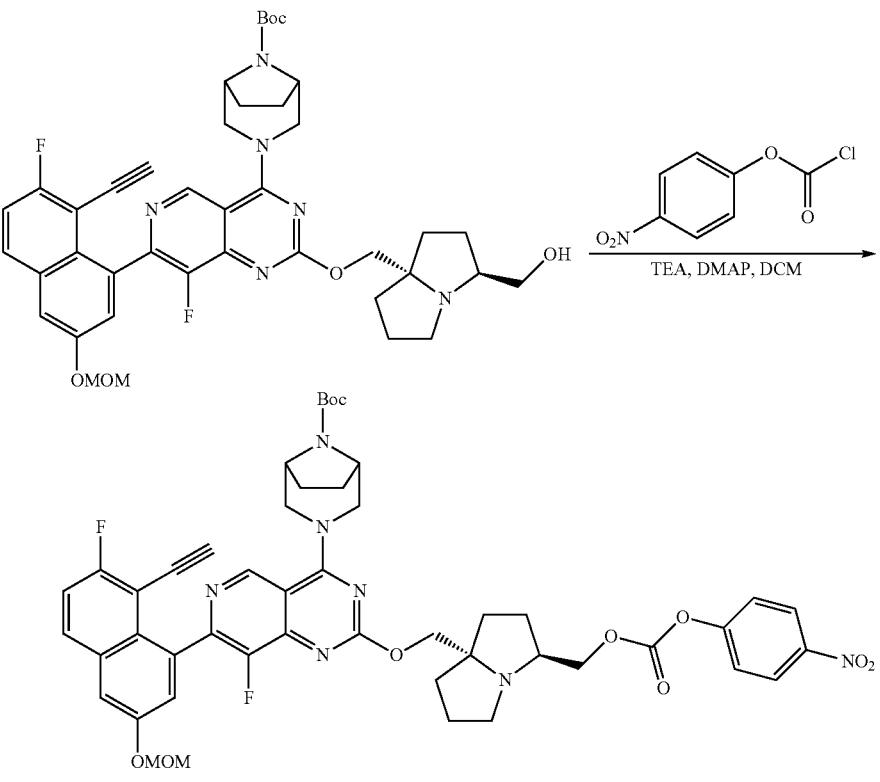

Int. C

To a solution of tert-butyl 3-[7-[8-ethynyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (20.0 mg, 26.4 μmol) in DCM (2 mL) was added DMAP (322 ug, 2.64 μmol) and TEA (8.02 mg, 79.2 μmol) at 25° C. Then (4-nitrophenyl) carbonochloridate (15.9 mg, 79.2 μmol) was added to the mixture. The mixture was stirred at 25° C. for 2 hrs. Upon completion, the reaction mixture was concentrated in vacuo to give a residue. The residue was diluted with $H_2O$ (5 mL) and extracted with DCM (2×10 mL). The combined organic layers were dried over anhydrous $Na_2SO_4$, filtered and concentrated in vacuo to afford the title compound (24 mg, 98% yield) as yellow oil. LC-MS (ESI$^+$) m/z 922.3 (M+H)$^+$.

Example 3. Synthesis of Compound 028 a) Synthesis of Tert-butyl N-[2-[2-[2-[2-[[2-(2,6-dioxo-3-piperidyl)-1,3-dioxo-isoindolin-4-yl]amino]ethoxy]ethoxy]ethoxy]ethyl]carbamate

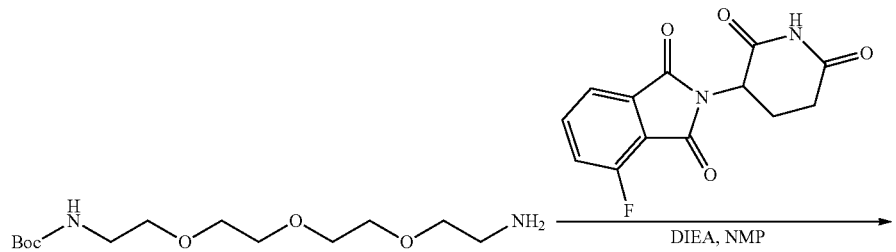

To a solution of tert-butyl N-[2-[2-[2-(2-aminoethoxy)ethoxy]ethoxy]ethyl]carbamate (2.00 g, 6.84 mmol, CAS #101187-40-0) and 2-(2,6-dioxo-3-piperidyl)-4-fluoro-isoindoline-1,3-dione (1.70 g, 6.16 mmol, CAS #835616-60-9) in NMP (2 mL) was added DIEA (1.77 g, 13.6 mmol). The mixture was stirred at 90° C. for 16 hrs. On completion, the reaction mixture was extracted with EA (3×20 mL). The combined organic layers were washed with brine (20 mL), dried over anhydrous $Na_2SO_4$, filtered and the filtrate was concentrated in vacuo to provide a residue. The crude product was purified by reverse phase (0.1% FA condition) to afford the title compound (1.5 g, 39% yield) as yellow solid. $^1$H NMR (400 MHz, DMSO-$d_6$) δ 11.09 (s, 1H), 7.62-7.54 (m, 1H), 7.15 (d, J=8.4 Hz, 1H), 7.04 (d, J=7.2 Hz, 1H), 6.78-6.69 (m, 1H), 6.61-6.58 (m, 1H), 5.05 (dd, J=5.2, 12.8 Hz, 1H), 3.64-3.60 (m, 2H), 3.56-3.46 (m, 10H), 3.37-3.33 (m, 2H), 3.29 (s, 1H), 3.06-3.02 (m, 2H), 2.93-2.83 (m, 1H), 2.55 (d, J=9.2 Hz, 1H), 2.06-1.99 (m, 1H), 1.36 (s, 9H); LC-MS (ESI$^+$) m/z 549.1 (M+H)$^+$.

b) Synthesis of -4-[2-[2-[2-(2-Aminoethoxy)ethoxy]ethoxy]ethylamino]-2-(2,6-dioxo-3-piperidyl) isoindoline-1,3-dione

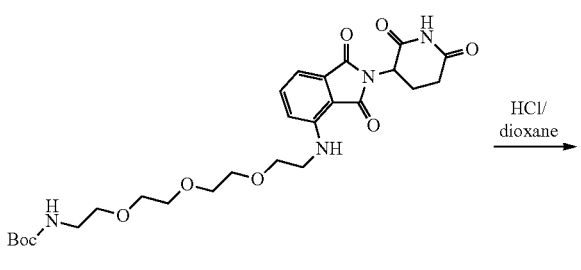

847
-continued

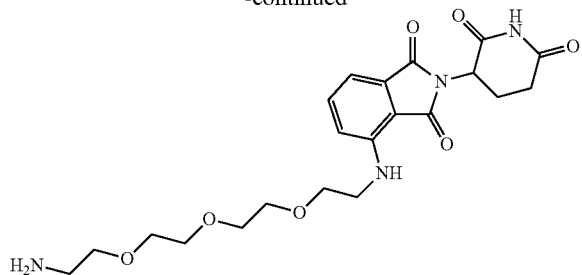

To a solution of tert-butyl N-[2-[2-[2-[2-[[2-(2,6-dioxo-3-piperidyl)-1,3-dioxo-isoindolin-4-yl]amino] ethoxy]ethoxy]ethoxy] ethyl]carbamate (150 mg, 273 μmol) in

848

DCM (1.5 mL) was added HCl/dioxane (4 M, 0.75 mL). The mixture was stirred at 25° C. for 4 hrs. Upon completion, the reaction mixture was concentrated in vacuo to afford the title compound (130 mg, 95% yield, HCl salt) as green solid. LC-MS (ESI$^+$) m/z 449.0 (M+H)$^+$.

c) Synthesis of Tert-butyl 3-[2-[[(3S,8S)-3-[2-[2-[2-[2-[[2-(2,6-dioxo-3-piperidyl)-1,3-dioxo-isoindolin-4-yl] amino]ethoxy]ethoxy]ethoxy]ethylcarbamoyloxymethyl]-1,2,3,5,6,7-hexahydropyrrolizin-8-yl] methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

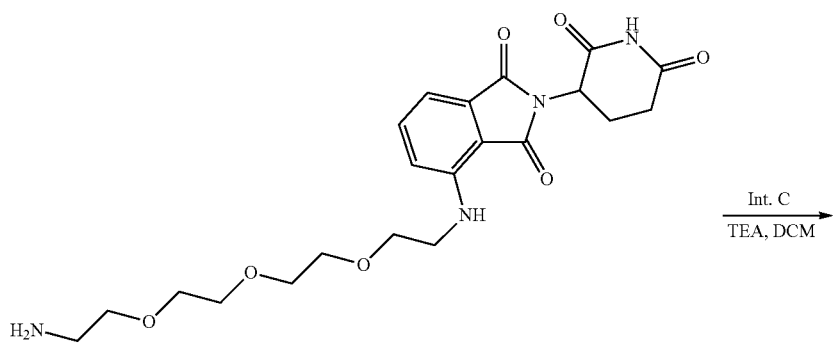

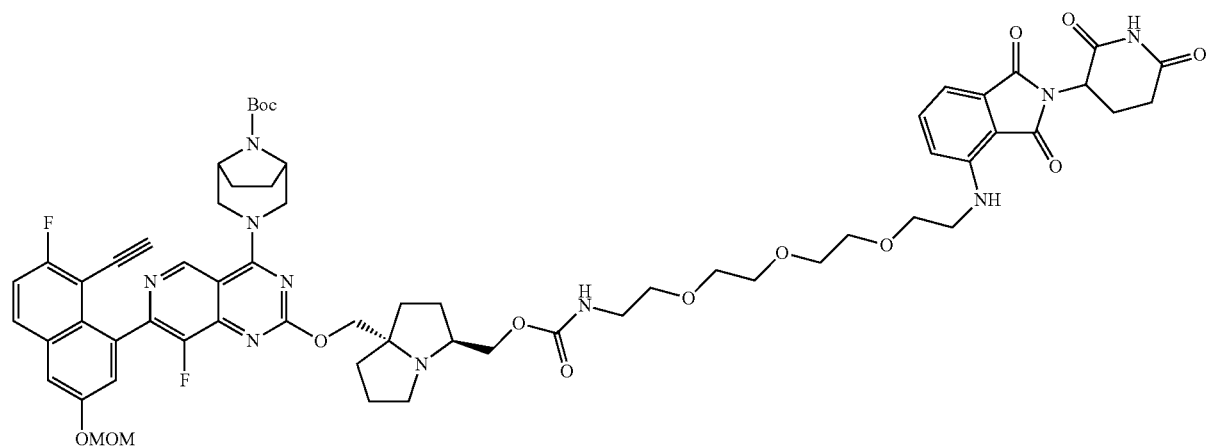

To a solution of 4-[2-[2-[2-(2-aminoethoxy)ethoxy]ethoxy]ethylamino]-2-(2,6-dioxo-3-piperidyl) isoindoline-1,3-dione (18.9 mg, 39.0 μmol, HCl salt) and Int. C (24.0 mg, 26.0 μmol) in THF (1 mL) was added TEA (7.90 mg, 78.1 μmol). The mixture was stirred at 25° C. for 1 hr. Upon completion, the reaction mixture was concentrated in vacuo to give a residue. The residue was purified by prep-HPLC (column: Phenomenex luna C18 150*25 mm*10 μm; mobile phase: [water (FA)-ACN]; B %: 28%-58%, 15 min) to afford the title compound (20 mg, 62% yield) as yellow solid. LC-MS (ESI$^+$) m/z 1231.2 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methylN-[2-[2-[2-[2-[[2-(2,6-dioxo-3-piperidyl)-1,3-dioxo-isoindolin-4-yl]amino]ethoxy]ethoxy]ethoxy]ethyl]carbamate (028)

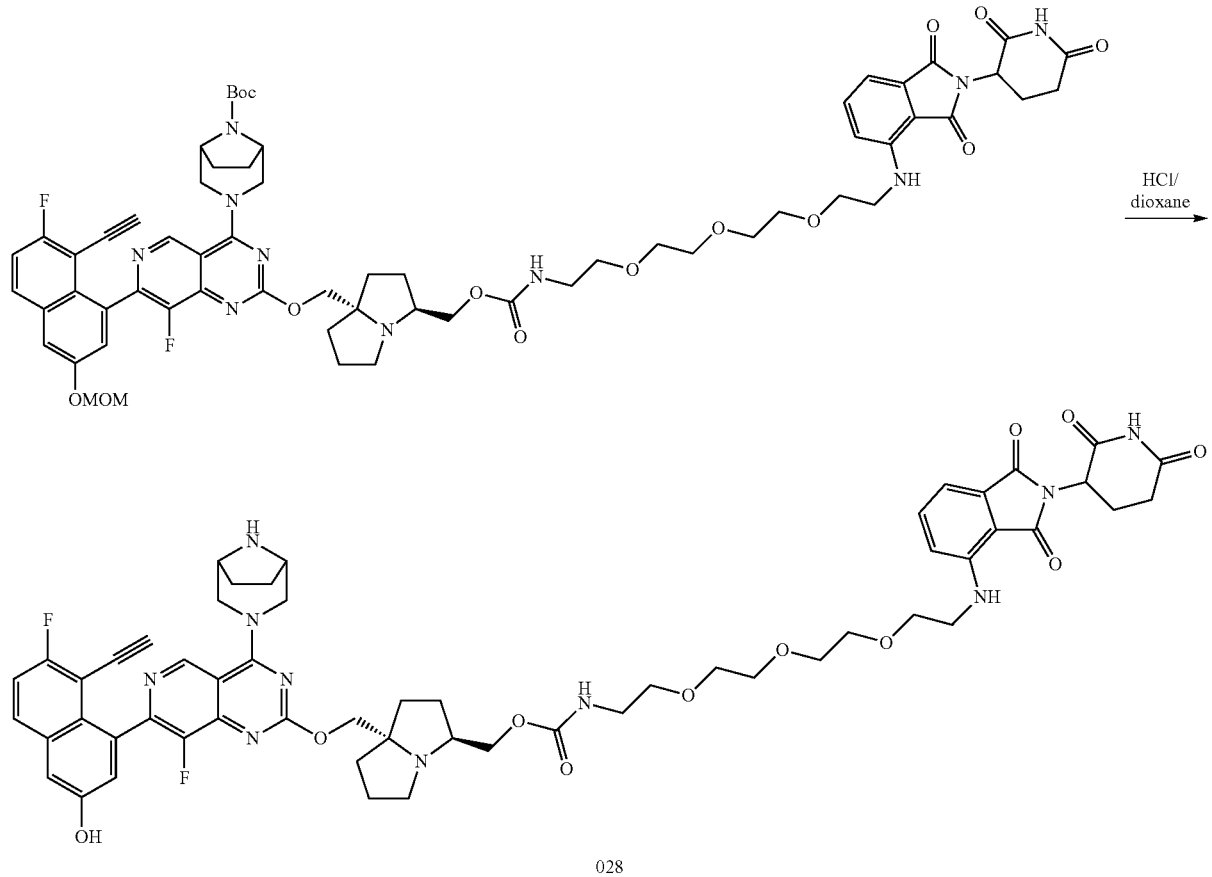

To a solution of tert-butyl 3-[2-[[(3S,8S)-3-[2-[2-[2-[2-[[2-(2,6-dioxo-3-piperidyl)-1,3-dioxo-isoindolin-4-yl]amino]ethoxy]ethoxy]ethoxy]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (20.0 mg, 16.2 μmol) in DCM (1 mL) was added HCl/dioxane (4 M, 0.25 mL). The reaction mixture was stirred at 25° C. for 0.5 hr. On completion, the reaction mixture was concentrated in vacuo to provide a residue. The residue was purified by prep-HPLC (column: Phenomenex luna C18 150*25 mm*10 μm; mobile phase: [water (FA)-ACN]; B %: 9%-38%, 15 min) to afford the title compound (6.80 mg, 38% yield) as yellow solid. $^1$H NMR (400 MHz, DMSO-$d_6$) δ 11.20-10.99 (m, 1H), 9.03 (s, 1H), 8.23 (s, 1H), 7.97 (dd, J=6.0, 9.2 Hz, 1H), 7.61-7.53 (m, 1H), 7.46 (t, J=9.2 Hz, 1H), 7.38 (d, J=2.4 Hz, 1H), 7.17 (d, J=2.4 Hz, 2H), 7.13 (d, J=8.4 Hz, 1H), 7.03 (d, J=7.2 Hz, 1H), 6.60-6.57 (m, 1H), 5.05 (dd, J=5.2, 12.8 Hz, 1H), 4.47 (d, J=11.2 Hz, 1H), 4.30 (d, J=11.2 Hz, 1H), 4.19-4.00 (m, 4H), 3.93 (s, 1H), 3.66-3.59 (m, 4H), 3.58-3.51 (m, 8H), 3.50-3.46 (m, 9H), 3.11-3.07 (m, 2H), 2.94-2.81 (m, 2H), 2.76-2.71 (m, 1H), 2.63-2.54 (m, 2H), 2.07-1.99 (m, 2H), 1.78-1.69 (m, 4H), 1.68-1.64 (m, 4H), 1.63-1.56 (m, 1H), 1.53-1.45 (m, 1H); LC-MS (ESI$^+$) m/z 1087.3 (M+H)$^+$.

Example 4. Synthesis of Int. D a) Synthesis of Tert-butyl 3-[2-[[(3R,8R)-3-[[tert-butyl(diphenyl)silyl]oxymethyl]-1,2,3,5,6,7-hexahydro pyrrolizin-8-yl]methoxy]-7-chloro-8-fluoro-pyrido[4,3-d]pyrimidin-4-yl]-3,8-diazabicyclo[3.2.1]octane-8-carboxylate

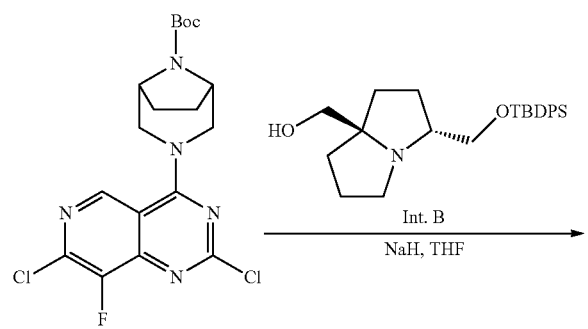

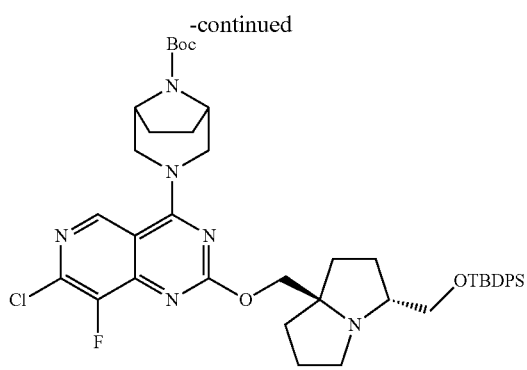

To a solution of Int. B (300 mg, 732 μmol) in THF (20 mL) was added NaH (87.8 mg, 2.20 mmol, 60% purity) at 0° C. The mixture was stirred at 25° C. for 0.5 hr, and then tert-butyl 3-(2,7-dichloro-8-fluoro-pyrido[4,3-d]pyrimidin-4-yl)-3,8-diazabicyclo[3.2.1]octane-8-carboxylate (345 mg, 805 μmol) was added to the mixture at 25° C. The mixture was stirred at 25° C. for 15.5 hrs under $N_2$ atmosphere. Upon completion, the reaction was quenched with $H_2O$ (10 mL) and dissolved with DCM (30 mL). The aqueous layer was separated and extracted with DCM (2×30 mL). The combined organic layers were washed with brine (30 mL), dried over anhydrous $Na_2SO_4$, filtered and concentrated in vacuo to provide a residue. The residue was purified by column chromatography ($SiO_2$, DCM:MeOH=10:1). The residue was purified by pre-NPLC (column: Welch Ultimate XB-CN 250*50*10 μm; mobile phase: [Hexane-EtOH]; B %: 5%-35%, 30 min) to afford the title compound (320 mg, 51% yield) as yellow solid. $^1$H NMR (400 MHz, $CDCl_3$) δ 8.72 (s, 1H), 7.73-7.60 (m, 4H), 7.49-7.35 (m, 6H), 4.56-4.32 (m, 4H), 4.29-4.12 (m, 2H), 4.03-3.95 (m, 1H), 3.87-3.78 (m, 1H), 3.77-3.46 (m, 3H), 3.38-3.21 (m, 1H), 2.95-2.71 (m, 2H), 2.24-2.17 (m, 1H), 2.00-1.91 (m, 4H), 1.89-1.79 (m, 4H), 1.69 (d, J=7.6 Hz, 2H), 1.52 (s, 8H), 1.11-1.01 (m, 9H); LC-MS (ESI$^+$) m/z 801.3 (M+H)$^+$.

b) Synthesis of Tert-butyl 3-[2-[[(3R,8R)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

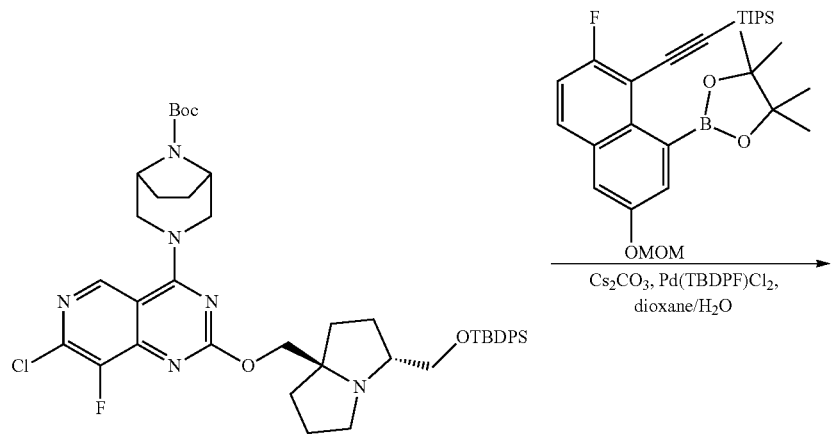

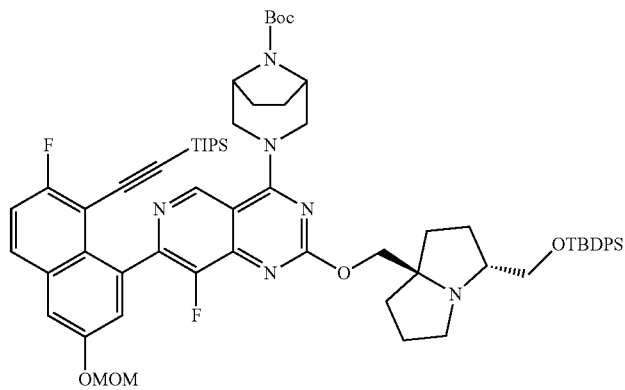

A solution of tert-butyl 3-[2-[[(3R,8R)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (200 mg, 249 μmol), 2-[2-fluoro-6-(methoxymethoxy)-8-(4,4,5,5-tetramethyl-1,3,2-dioxaborolan-2-yl)-1-naphthyl]ethynyl-triisopropyl-silane (255 mg, 499 μmol, CAS #2621932-37-2), ditert-butyl(cyclopentyl)phosphane; dichloropalladium; iron (32.5 mg, 49.9 μmol) and $Cs_2CO_3$ (243 mg, 748 μmol) in dioxane (8 mL) and $H_2O$ (1.6 mL) was degassed and purged with $N_2$ for 3 times, and then the mixture was stirred at 100° C. for 0.5 hr under $N_2$ atmosphere. Upon completion, the reaction was concentrated in vacuo to give a residue. The residue was purified by prep-TLC ($SiO_2$, DCM:MeOH=10:1) to afford the title compound (270 mg, 88% yield) as brown solid. $^1$H NMR (400 MHz, $CDCl_3$) δ 9.12-8.99 (m, 1H), 7.78 (dd, J=5.6, 9.2 Hz, 1H), 7.69 (t, J=6.4 Hz, 2H), 7.62 (s, 2H), 7.51 (d, J=2.4 Hz, 1H), 7.45-7.37 (m, 6H), 7.32-7.31 (m, 2H), 5.31 (s, 2H), 4.93-4.80 (m, 1H), 4.59-4.30 (m, 3H), 4.28-4.22 (m, 1H), 4.22-4.13 (m, 2H), 4.40 (dd, J=4.8, 10.8 Hz, 1H), 3.87-3.78 (m, 2H), 3.76-3.52 (m, 2H), 3.51 (s, 3H), 3.48-3.37 (m, 1H), 3.34-3.26 (m, 1H), 2.84-2.83 (m, 2H), 2.42-2.03 (m, 4H), 2.02-1.66 (m, 14H), 1.53 (s, 9H), 1.25 (s, 9H), 1.15-0.99 (m, 12H); LC-MS (ESI$^+$) m/z 1152.2 (M+H)$^+$.

c) Synthesis of Tert-butyl 3-[7-[8-ethynyl-7-fluoro-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

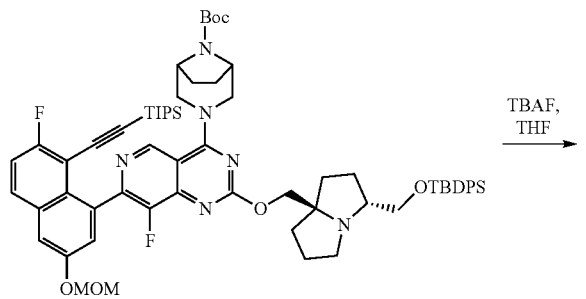

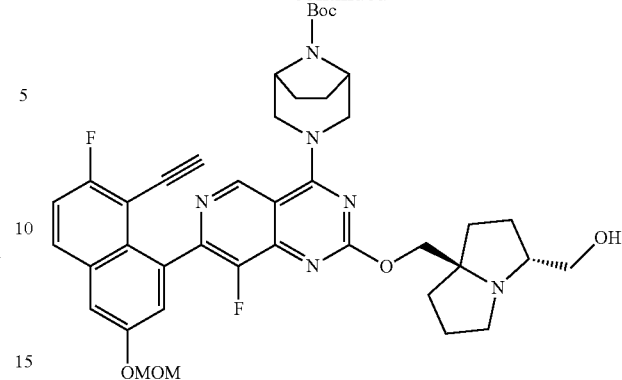

To a solution of tert-butyl 3-[2-[[(3R,8R)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (270 mg, 234 μmol) in THF (3 mL) was added TBAF (1.00 M, 703 uL) at 0° C. The mixture was stirred at 25° C. for 2 hrs under $N_2$ atmosphere. Upon completion, the reaction mixture was diluted with $H_2O$ (5 mL) and extracted with EA (3×5 mL). The combined organic layers were washed with brine (2×5 mL), dried over anhydrous $Na_2SO_4$, filtered and the filtrate was concentrated in vacuo to give a residue. The residue was purified by column chromatography ($SiO_2$, DCM:MeOH=100:1 to 10:1) to afford the title compound (110 mg, 60% yield) as brown solid. $^1$H NMR (400 MHz, $CDCl_3$) δ 9.01 (s, 1H), 7.80-7.84 (m, 1H), 7.57-7.51 (m, 1H), 7.38 (dd, J=2.4, 8.0 Hz, 1H), 7.32-7.28 (m, 1H), 5.35-5.30 (m, 2H), 4.77-4.69 (m, 1H), 4.66-4.56 (m, 2H), 4.42-4.41 (m, 1H), 4.40-3.97 (m, 1H), 3.88-3.60 (m, 5H), 3.53 (s, 3H), 3.25-3.01 (m, 2H), 2.51-2.41 (m, 1H), 2.39-2.30 (m, 1H), 2.26-2.19 (m, 1H), 2.12-2.10 (m, 2H), 2.05-1.94 (m, 4H), 1.93-1.71 (m, 6H), 1.53 (s, 9H); LC-MS (ESI$^+$) m/z 757.0 (M+H)$^+$.

d) Synthesis of Tert-butyl 3-[7-[8-ethynyl-7-fluoro-3-(methoxymethoxy)-1-naphthyl]-8-fluoro-2-[[(3R,8R)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (Int. D)

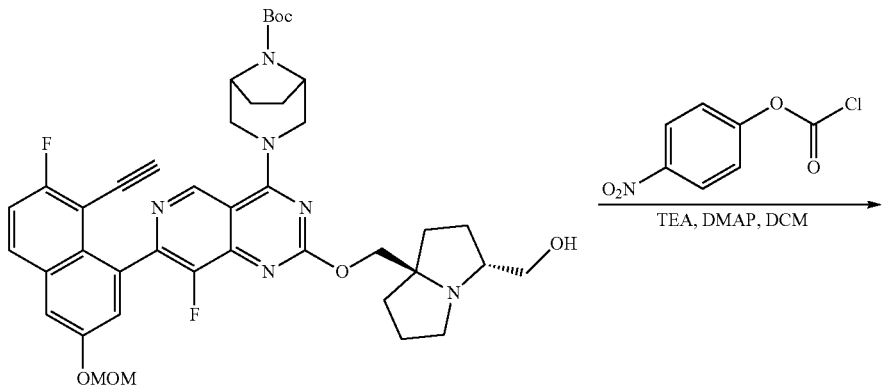

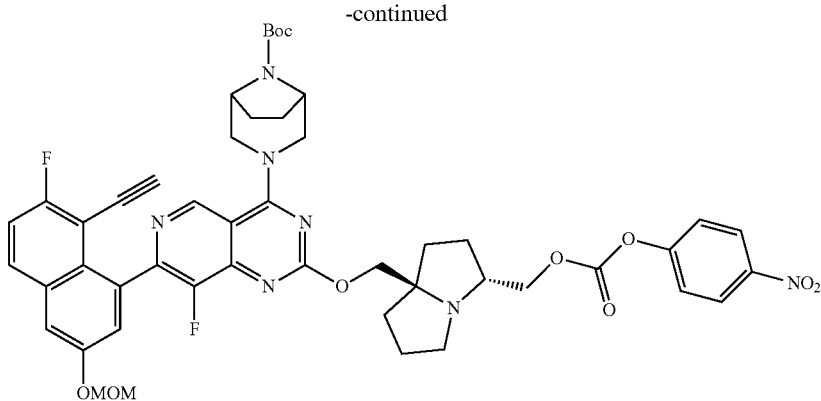

Int. D

To a solution of tert-butyl 3-[7-[8-ethynyl-7-fluoro-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (10.0 mg, 13.2 μmol), TEA (4.01 mg, 39.6 μmol) and DMAP (161 ug, 1.32 μmol) in DCM (2 mL) was added (4-nitrophenyl) carbonochloridate (7.99 mg, 39.6 μmol, CAS #7693-46-1). The mixture was stirred at 25° C. for 12 hrs under $N_2$ atmosphere. Upon completion, the mixture was diluted with DCM (10 mL) and extracted with $H_2O$ (3×10 mL). The organic layer was washed with brine (2×10 mL), dried over anhydrous $Na_2SO_4$, filtered and the filtrate was concentrated in vacuo to afford the title compound (12.0 mg, 57% yield) as brown solid. LC-MS (ESI$^+$) m/z 922.3 (M+H)$^+$.

Example 5. Synthesis of Compound 027 a) Synthesis of Tert-butyl 3-[2-[[(3S,8S)-3-[2-[2-[2-[2-[[2-(2,6-dioxo-3-piperidyl)-1,3-dioxo-isoindolin-4-yl] amino]ethoxy]ethoxy]ethoxy]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

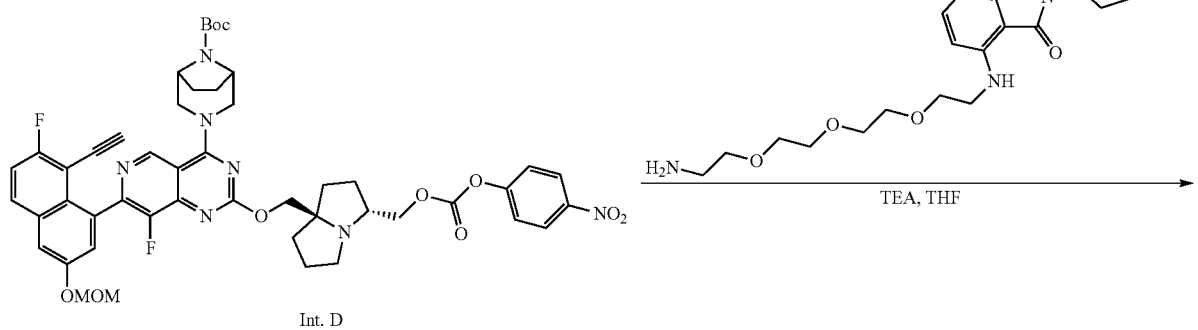

-continued

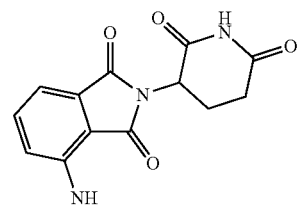
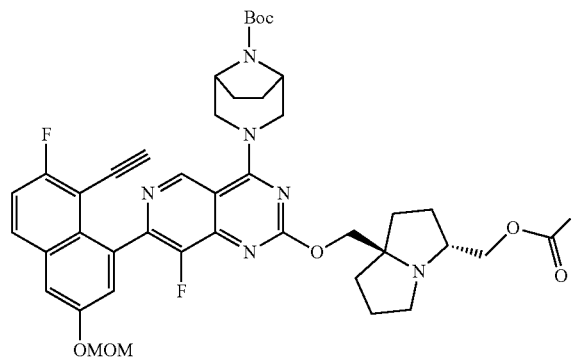

To a solution of Int. D (12.0 mg, 13.0 μmol) and 4-[2-[2-[2-(2-aminoethoxy)ethoxy]ethoxy]ethylamino]-2-(2,6-dioxo-3-piperidyl)isoindoline-1,3-dione (9.47 mg, 19.5 μmol, HCl salt, from Example 3) in THF (1 mL) was added TEA (3.95 mg, 39.0 μmol). The mixture was stirred at 25° C. for 2 hrs. Upon completion, the reaction mixture was concentrated in vacuo to give a residue. The residue was purified by prep-HPLC (column: Phenomenex luna C18 150*25 mm*10 μm; mobile phase: [water (FA)-ACN]; B %: 31%-61%, 10 min) to afford the title compound (7.00 mg, 43% yield) as yellow solid. LC-MS (ESI$^+$) m/z 1232.0 (M+H)$^+$.

b) Synthesis of [(3R,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[2-[2-[2-[2-[[2-(2,6-dioxo-3-piperidyl)-1,3-dioxo-isoindolin-4-yl]amino]ethoxy]ethoxy]ethoxy] ethyl]carbamate (O27)

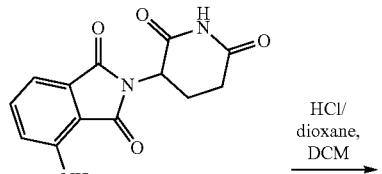
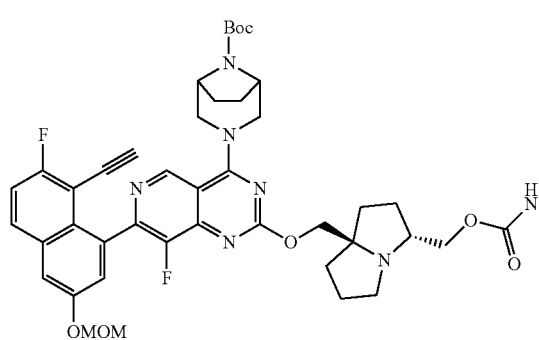

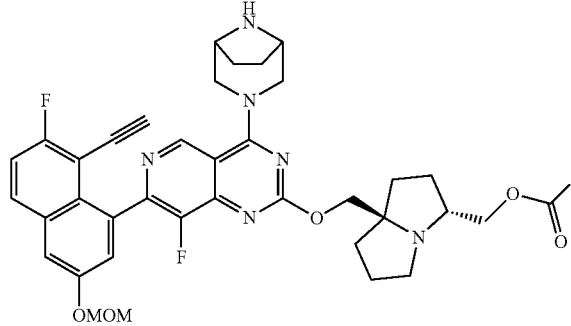

To a solution of tert-butyl 3-[2-[[(3R,8R)-3-[2-[2-[2-[2-[[2-(2,6-dioxo-3-piperidyl)-1,3-dioxo-isoindolin-4-yl]amino]ethoxy]ethoxy]ethoxy]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (7.00 mg, 5.69 μmol) in DCM (1 mL) was added HCl/dioxane (4.00 M, 0.500 mL). The mixture was stirred at 25° C. for 0.5 hr. Upon completion, the mixture was concentrated in vacuo to provide a residue and the residue was purified by prep-HPLC (column: Welch Xtimate C18 150*25 mm*5 μm; mobile phase: [water (HCl)-ACN]; B %: 11%-41%, 8 min) to afford the title compound (720 μg, 11% yield) as yellow solid. $^1$H NMR (400 MHz, DMSO-$d_6$) δ 11.09 (s, 1H), 10.59-10.48 (m, 1H), 10.24 (s, 1H), 9.76-9.65 (m, 1H), 9.38-9.29 (m, 1H), 9.16 (s, 1H), 7.99 (dd, J=6.0, 9.2 Hz, 1H), 7.60-7.55 (m, 1H), 7.47 (t, J=9.2 Hz, 1H), 7.41 (d, J=2.4 Hz, 1H), 7.26-7.17 (m, 2H), 7.13 (d, J=8.4 Hz, 1H), 7.04 (d, J=6.8 Hz, 1H), 6.62-6.55 (m, 1H), 5.05 (dd, J=5.2, 12.8 Hz, 1H), 4.68 (d, J=13.2 Hz, 1H), 4.64-4.52 (m, 3H), 4.32 (d, J=5.6 Hz, 2H), 4.21 (s, 2H), 3.99-3.88 (m, 4H), 3.62-3.59 (m, 2H), 3.56-3.53 (m, 2H), 3.53-3.51 (m, 2H), 3.50-3.46 (m, 7H), 3.17-3.12 (m, 2H), 2.95-2.79 (m, 3H), 2.60 (s, 2H), 2.15 (m, 2H), 2.05-1.90 (m, 10H); LC-MS (ESI$^+$) m/z 1187.2 (M+H)$^+$.

Example 6. Synthesis of Compound 025 a) Synthesis of Tert-butyl N-[2-[2-[2-[[2-(2,6-dioxo-3-piperidyl)-1,3-dioxo-isoindolin-5-yl]amino]ethoxy] ethoxy]ethyl]carbamate To a solution of tert-butyl N-[2-[2-(2-aminoethoxy)ethoxy]ethyl]carbamate (2.00 g, 8.05 mmol, CAS #153086-78-3) and 2-(2,6-dioxo-3-piperidyl)-5-fluoro-isoindoline-1,3-dione (2.22 g, 8.05 mmol, CAS #835616-60-9) in NMP (30 mL) was added DIEA (2.08 g, 16.1 mmol). The mixture was stirred at 135° C. for 4 hrs. Upon completion, to the reaction mixture was added H$_2$O (50 mL) and extracted with EA (3×60 mL). The combined organic layers were washed with brine (40 mL), dried over anhydrous Na$_2$SO$_4$, filtered and concentrated in vacuo to give a residue. The residue was purified by reversed-phase HPLC (0.1% FA condition) to afford the title compound (1.00 g, 24% yield) as yellow solid. $^1$H NMR (400 MHz, DMSO-$d_6$) δ 11.05 (s, 1H), 7.56 (d, J=8.4 Hz, 1H), 7.15 (t, J=5.2 Hz, 1H), 7.00 (d, J=2.0 Hz, 1H), 6.90 (dd, J=2.0, 8.4 Hz, 1H), 6.74 (t, J=5.6 z, 1H), 5.03 (J=5.2, 12.8 Hz, 1H), 3.59 (t, J=5.6 Hz, 2H), 3.55-3.53 (m, 2H), 3.53-3.50 (m, 2H), 3.38-3.34 (m, 4H), 3.05 (q, J=6.0 Hz, 2H), 2.55 (s, 4H), 1.36 (s, 10H); LC-MS (ESI$^+$) m/z 504.9 (M+H)$^+$.

b) Synthesis of 4-[2-[2-(2-Aminoethoxy)ethoxy]ethylamino]-2-(2,6-dioxo-3-piperidyl)isoindoline-1,3-dione

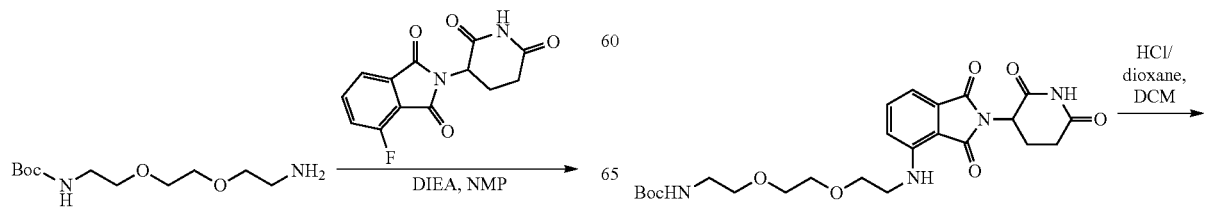

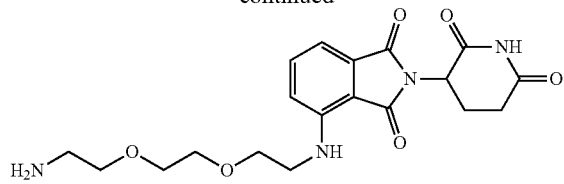

To a solution of tert-butyl N-[2-[2-[2-[[2-(2,6-dioxo-3-piperidyl)-1,3-dioxo-isoindolin-4-yl] amino] ethoxy] ethoxy]ethyl]carbamate (200 mg, 396 μmol) in DCM (2 mL) was added HCl/dioxane (4.00 M, 1.00 mL). The mixture was stirred at 25° C. for 3 hrs. Upon completion, the reaction mixture was concentrated in vacuo to afford the title compound (174 mg, 99% yield, HCl salt) as yellow solid. LC-MS (ESI+) m/z 405.0 (M+H)+.

c) Synthesis of Tert-butyl 3-[2-[[(3R 8R)-3-[2-[2-[2-[[2-(2,6-dioxo-3-piperidyl)-1,3-dioxo-isoindolin-4-yl]amino]ethoxy]ethoxy]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

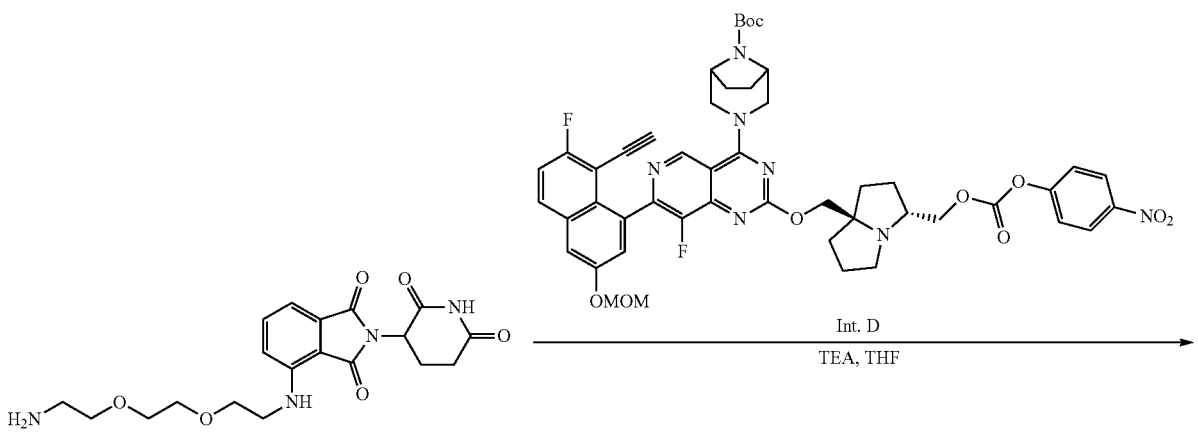

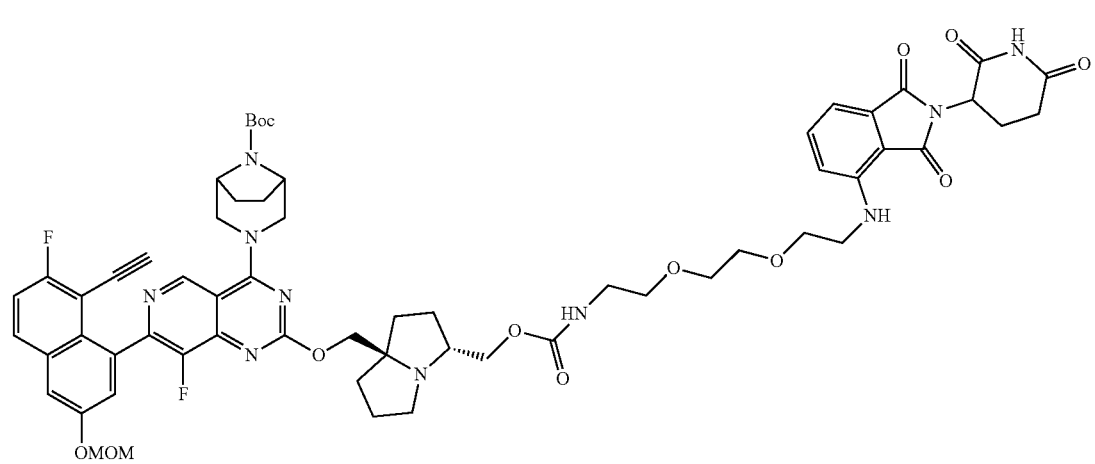

To a solution of Int. D (120 mg, 130 μmol) and 4-[2-[2-(2-aminoethoxy)ethoxy]ethylamino]-2-(2,6-dioxo-3-piperidyl)isoindoline-1,3-dione (86.1 mg, 195 μmol, HCl salt) in THF (12 mL) was added TEA (39.5 mg, 390 μmol). The mixture was stirred at 25° C. for 2 hrs. Upon completion, the reaction mixture was concentrated in vacuo to afford the title compound (154 mg, 64% yield) as yellow oil. LC-MS (ESI+) m/z 1187.3 (M+H)+.

d) Synthesis of Tert-butyl 3-[2-[[(3R 8R)-3-[2-[2-[2-[[2-(2,6-dioxo-3-piperidyl)-1,3-dioxo-isoindolin-4-yl]amino] ethoxy]ethoxy]ethylcarbamoyloxymethyl]-1,2,3,5,6,7-hexahydropyrrolizin-8-yl] methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (025)

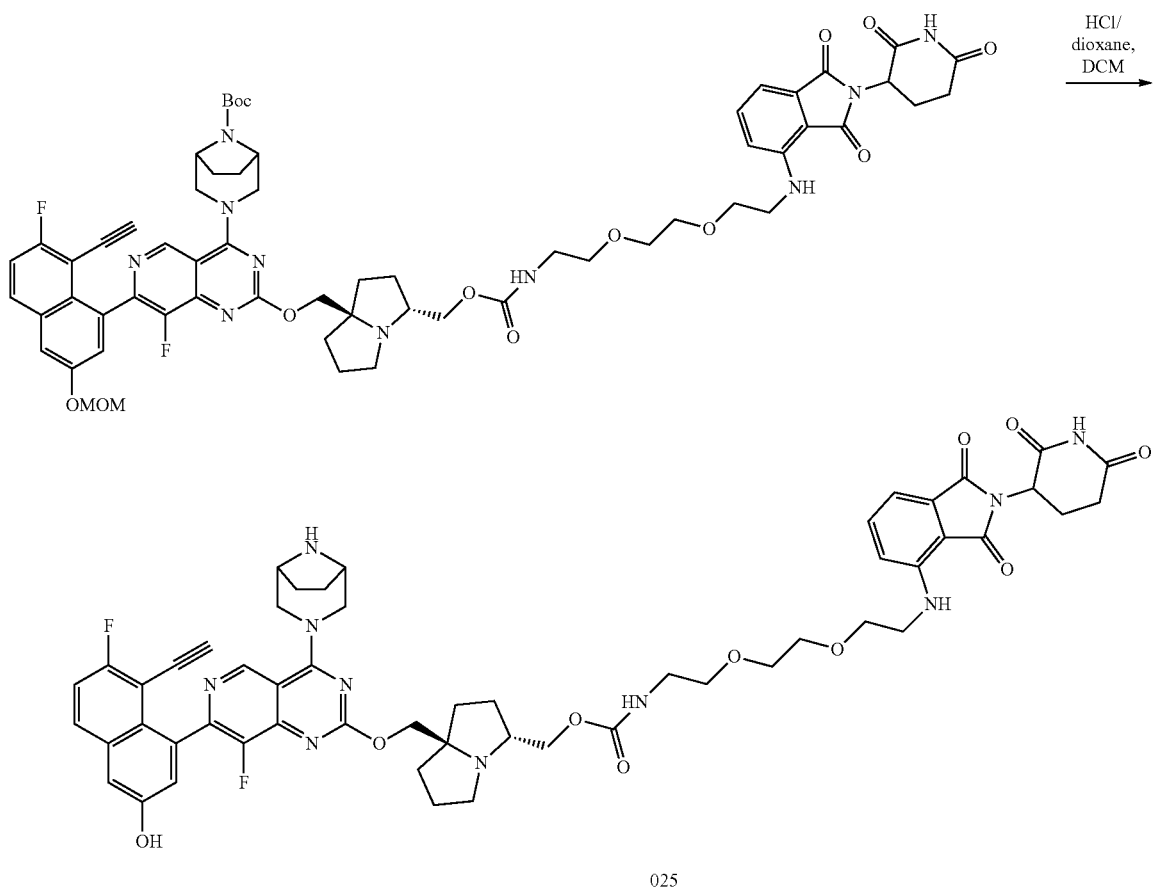

025

To a solution of tert-butyl 3-[2-[[(3R,8R)-3-[2-[2-[2-[[2-(2,6-dioxo-3-piperidyl)-1,3-dioxo-isoindolin-4-yl] amino] ethoxy]ethoxy]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d] pyrimidin-4-yl]-3,8-diazabicyclo[3.2.1]octane-8-carboxylate (154 mg, 83.0 μmol) in DCM (2 mL) was added HCl/dioxane (4.00 M, 1.00 mL). The mixture was stirred at 25° C. for 0.5 hr. Upon completion, the reaction mixture was concentrated in vacuo to give a residue. The residue was purified by prep-HPLC (column: Phenomenex luna C18 150*25 mm*10 μm; mobile phase: [water (FA)-ACN]; B %: 17%-47%, 15 min) to afford the title compound (4.71 mg, 5.3% yield) as brown solid. $^1$H NMR (400 MHz, DMSO-$d_6$) δ 11.15-11.07 (m, 1H), 9.03 (s, 1H), 8.21 (s, 1H), 7.97 (dd, J=6.0, 9.6 Hz, 1H), 7.57 (t, J=8 Hz, 1H), 7.46 (t, J=9.2 Hz, 1H), 7.38 (d, J=2.0 Hz, 1H), 7.17 (d, J=2.4 Hz, 1H), 7.13 (br d, J=8.0 Hz, 1H), 7.02 (d, J=7.2 Hz, 1H), 6.62-6.56 (m, 1H), 5.09-5.00 (m, 1H), 4.51-4.43 (m, 1H), 4.34-4.26 (m, 1H), 4.16-4.07 (m, 3H), 4.04-3.98 (m, 1H), 3.92 (s, 1H), 3.67-3.64 (m, 1H), 3.61 (m, 2H), 3.57 (m, 2H), 3.55-3.54 (m, 2H), 3.52-3.50 (m, 2H), 3.45 (s, 2H), 3.41-3.38 (m, 4H), 3.13-3.10 (m, 2H), 2.95-2.81 (m, 2H), 2.77-2.72 (m, 1H), 2.61-2.55 (m, 2H), 2.03 (m, 3H), 1.76-1.70 (m, 4H), 1.66 (s, 6H), 1.62 (m, 1H), 1.54-1.47 (m, 1H); LC-MS (ESI$^+$) m/z 1043.7 (M+H)$^+$.

Example 7. Synthesis of Compound 020 a) Synthesis of N-[3-[[2-(2,6-dioxo-3-piperidyl)-1,3-dioxo-isoindolin-4-yl]amino]propyl] carbamate

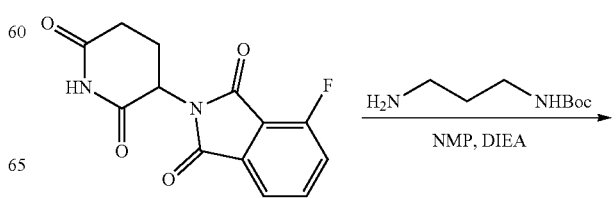

-continued

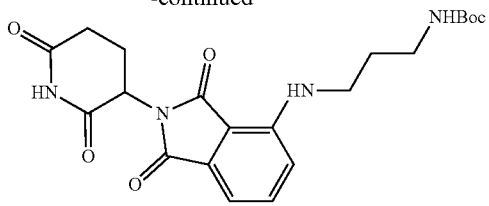

To a solution of 2-(2,6-dioxo-3-piperidyl)-4-fluoro-isoindoline-1,3-dione (713 mg, 2.58 mmol, CAS #835616-60-9) and tert-butyl N-(3-aminopropyl)carbamate (500 mg, 2.87 mmol, CAS #75178-96-0) in NMP (12 mL) was added DIEA (741 mg, 5.74 mmol). The mixture was stirred at 135° C. for 2 hrs. Upon completion, the reaction mixture was filtered and concentrated in vacuo to provide a residue. The residue was diluted with H$_2$O (50 mL) and extracted with EA (2×100 mL). The combined organic layers were dried over anhydrous Na$_2$SO$_4$, filtered and concentrated in vacuo to provide a residue. The residue was purified by prep-HPLC (column: UniSil 10-120 C18 50×250 mm; mobile phase: [water (FA)-ACN]; B %: 30%-60%, 22 min) to afford the title compound (760 mg, 61% yield) as yellow solid. $^1$H NMR (400 MHz, DMSO-d$_6$) δ 11.08 (s, 1H), 7.57 (dd, J=7.2, 8.4 Hz, 1H), 7.08 (d, J=8.8 Hz, 1H), 7.02 (d, J=7.2 Hz, 1H), 6.93-6.90 (m, 1H), 6.67-6.64 (m, 1H), 5.05 (dd, J=5.2, 12.8 Hz, 1H), 3.32-3.26 (m, 2H), 3.02-2.97 (m, 2H), 2.94-2.82 (m, 1H), 2.62-2.54 (m, 2H), 2.07-1.97 (m, 1H), 1.68-1.62 (m, 2H), 1.38 (s, 9H); LC-MS (ESI$^+$) m/z 330.8 (M+H−100)$^+$.

a) Synthesis of 4-(3-Aminopropylamino)-2-(2,6-dioxo-3-piperidyl)isoindoline-1,3-dione

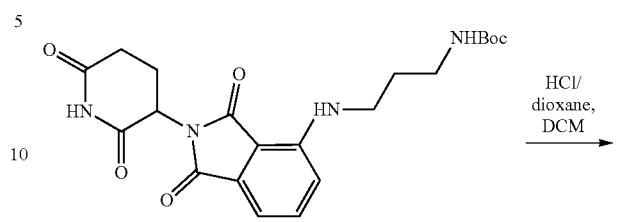

To a solution of tert-butyl N-[3-[[2-(2,6-dioxo-3-piperidyl)-1,3-dioxo-isoindolin-4-yl]amino] propyl]carbamate (100 mg, 232 μmol) in DCM (1 mL) was added HCl/dioxane (4 M, 0.5 mL). The mixture was stirred at 25° C. for 0.5 hr. Upon completion, the reaction mixture was concentrated in vacuo to afford the title compound (85 mg, 99% yield, HCl salt) as yellow solid. LC-MS (ESI$^+$) m/z 330.8 (M+H)$^+$.

a) Synthesis of Tert-butyl 3-[2-[[(3S,8S)-3-[3-[[2-(2,6-dioxo-3-piperidyl)-1,3-dioxo-isoindolin-4-yl] amino] propylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1] octane-8-carboxylate

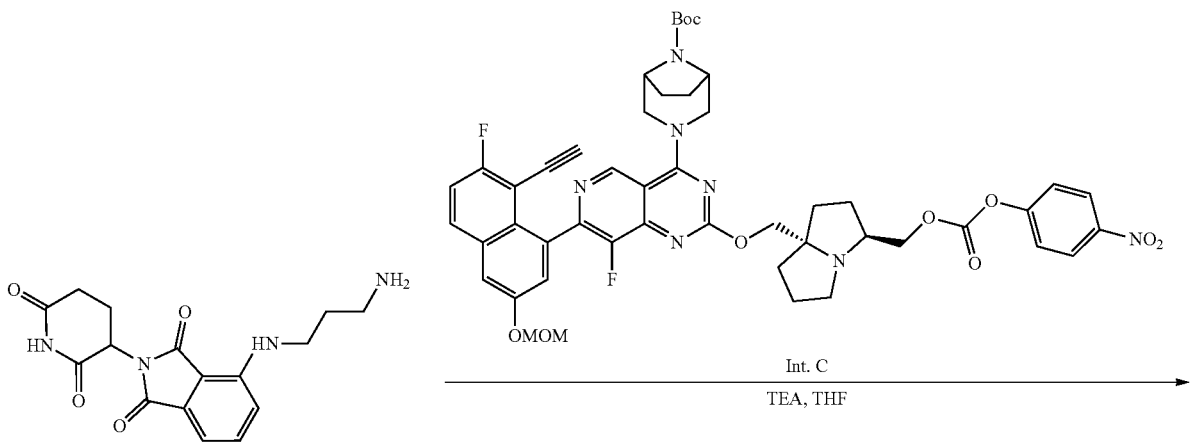

-continued

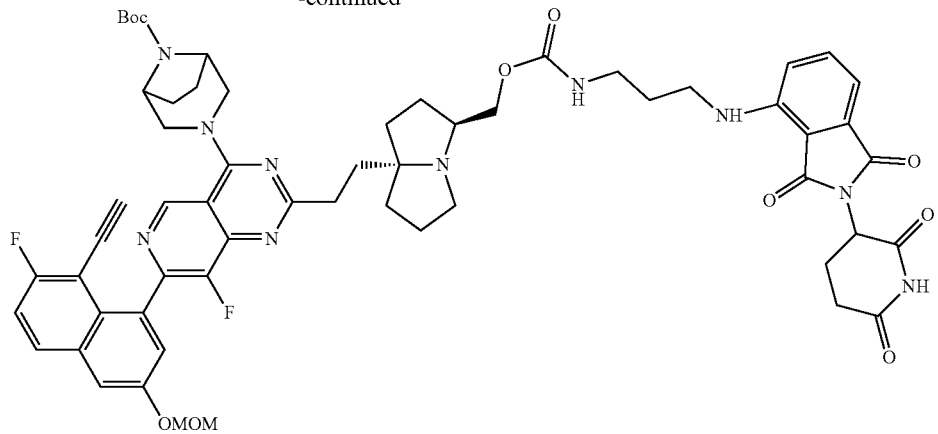

To a solution of Int. C (60.0 mg, 65.0 μmol) and 4-(3-aminopropylamino)-2-(2,6-dioxo-3-piperidyl)isoindoline-1,3-dione (35.8 mg, 97.6 μmol, HCl salt) in THF (2 mL) was added TEA (19.7 mg, 195 μmol). The mixture was stirred at 25° C. for 1.5 hrs. Upon completion, the mixture was concentrated in vacuo to give a residue. The residue was purified by prep-HPLC (column: Waters xbridge 150*25 mm 10 μm; mobile phase: [water (NH$_4$HCO$_3$)-ACN]; B %: 30%-60%, 8 min) to afford the title compound (55.0 mg, 75% yield) as yellow solid. LC-MS (ESI$^+$) m/z 1113.4 (M+H)$^+$.

a) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methylN-[3-[[2-(2,6-dioxo-3-piperidyl)-1,3-dioxo-isoindolin-4-yl]amino]propyl]carbamate (020)

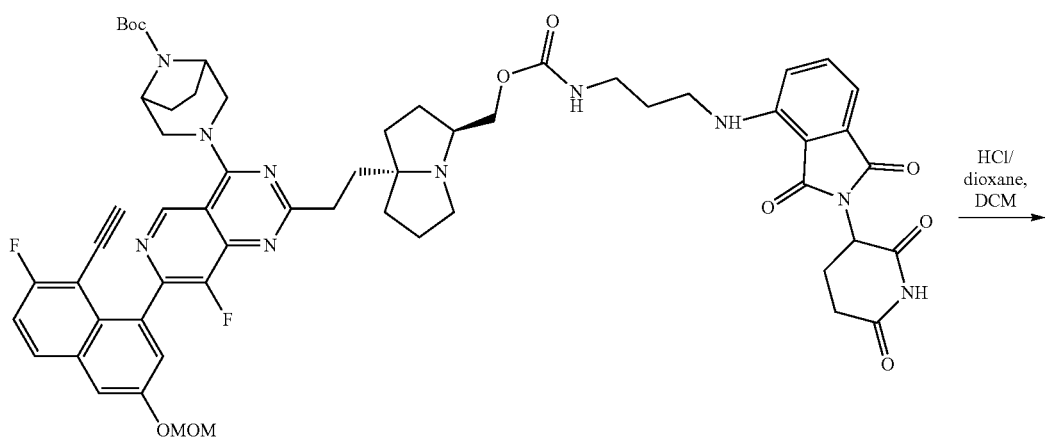

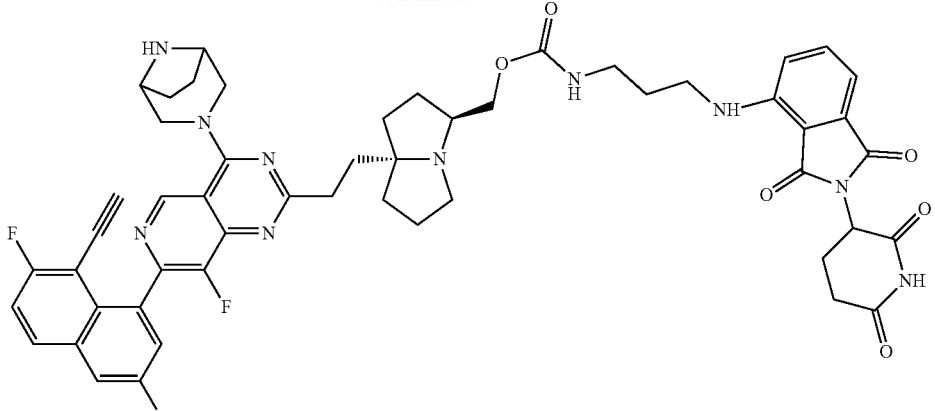

020

To a solution of tert-butyl 3-[2-[[(3S,8S)-3-[3-[[2-(2,6-dioxo-3-piperidyl)-1,3-dioxo-isoindolin-4-yl]amino]propylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (55.0 mg, 49.4 μmol) in DCM (1 mL) was added HCl/dioxane (4 M, 550 uL). The mixture was stirred at 25° C. for 0.5 hr. Upon completion, the reaction mixture was concentrated in vacuo to provide a residue. The residue was purified by prep-HPLC (column: Waters xbridge 150*25 mm 10 μm; mobile phase: [water (TFA)-ACN]; B %: 10%-40%, 8 min) to afford the title compound (12.5 mg, 22% yield, TFA salt) as yellow solid. $^1$H NMR (400 MHz, DMSO-$d_6$) δ 11.09 (s, 1H), 10.48-10.31 (m, 1H), 10.23 (s, 1H), 9.41-9.30 (m, 1H), 9.17 (s, 1H), 9.11-9.01 (m, 1H), 8.00 (dd, J=5.6, 9.2 Hz, 1H), 7.59-7.55 (m, 1H), 7.50-7.45 (m, 1H), 7.42 (d, J=2.4 Hz, 1H), 7.33 (d, J=6.0 Hz, 1H), 7.18 (d, J=2.0 Hz, 1H), 7.10-7.07 (m, 1H), 7.03 (d, J=7.2 Hz, 1H), 6.65 (t, J=5.2 Hz, 1H), 5.04 (dd, J=5.2, 12.8 Hz, 1H), 4.70 (d, J=15.6 Hz, 1H), 4.64-4.52 (m, 3H), 4.38-4.29 (m, 2H), 4.25-4.21 (m, 2H), 3.97-3.83 (m, 4H), 3.33 (d, J=6.0 Hz, 2H), 3.10-3.08 (m, 2H), 2.95-2.81 (m, 2H), 2.61 (d, J=2.4 Hz, 2H), 2.31-2.25 (m, 1H), 2.12-2.00 (m, 6H), 1.98-1.90 (m, 6H), 1.75-1.67 (m, 2H); LC-MS (ESI$^+$) m/z 969.4 (M+H)$^+$.

Example 8. Synthesis of Compound 019 a) Synthesis of Tert-butyl N-[4-[[2-(2,6-dioxo-3-piperidyl)-1,3-dioxo-isoindolin-4-yl]amino]butyl]carbamate

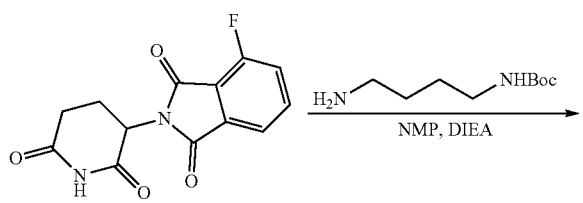

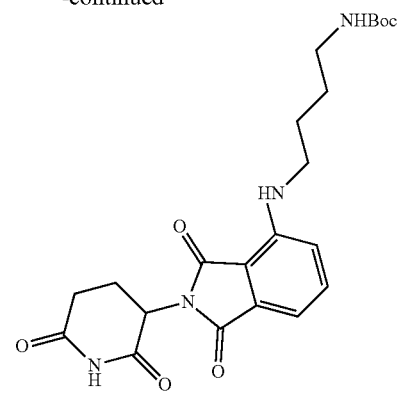

To a solution of 2-(2,6-dioxo-3-piperidyl)-4-fluoro-isoindoline-1,3-dione (660 mg, 2.39 mmol, CAS #835616-60-9) and tert-butyl N-(4-aminobutyl)carbamate (500 mg, 2.66 mmol, CAS #33545-98-1) in NMP (12 mL) was added DIEA (686 mg, 5.31 mmol). The mixture was stirred at 135° C. for 1.5 hrs. Upon completion, the reaction mixture was filtered and concentrated in vacuo to provide a residue. The residue was diluted with H$_2$O (50 mL) and extracted with EA (2×100 mL). The combined organic layers were dried over anhydrous Na$_2$SO$_4$, filtered and concentrated in vacuo to provide a residue. The residue was purified by prep-HPLC (column: UniSil 10-120 C18 50×250 mm; mobile phase: [water (FA)-ACN]; B %: 32%-62%, 25 min) to afford the title compound (812 mg, 68% yield) as yellow solid. $^1$H NMR (400 MHz, DMSO-$d_6$) δ 11.08 (s, 1H), 7.57 (dd, J=7.2, 8.4 Hz, 1H), 7.10 (d, J=8.8 Hz, 1H), 7.02 (d, J=7.2 Hz, 1H), 6.84-6.81 (m, 1H), 6.56-6.53 (m, 1H), 5.05 (dd, J=5.6, 12.8 Hz, 1H), 3.31-3.25 (m, 2H), 2.96-2.92 (m, 2H), 2.90-2.82 (m, 1H), 2.60 (d, J=2.8 Hz, 1H), 2.55 (d, J=10.0 Hz, 1H), 2.07-1.97 (m, 1H), 1.59-1.50 (m, 2H), 1.49-1.41 (m, 2H), 1.36 (s, 9H); LC-MS (ESI$^+$) m/z 345.1 (M+H–100)$^+$.

b) Synthesis of 4-(4-Aminobutylamino)-2-(2,6-dioxo-3-piperidyl)isoindoline-1,3-dione

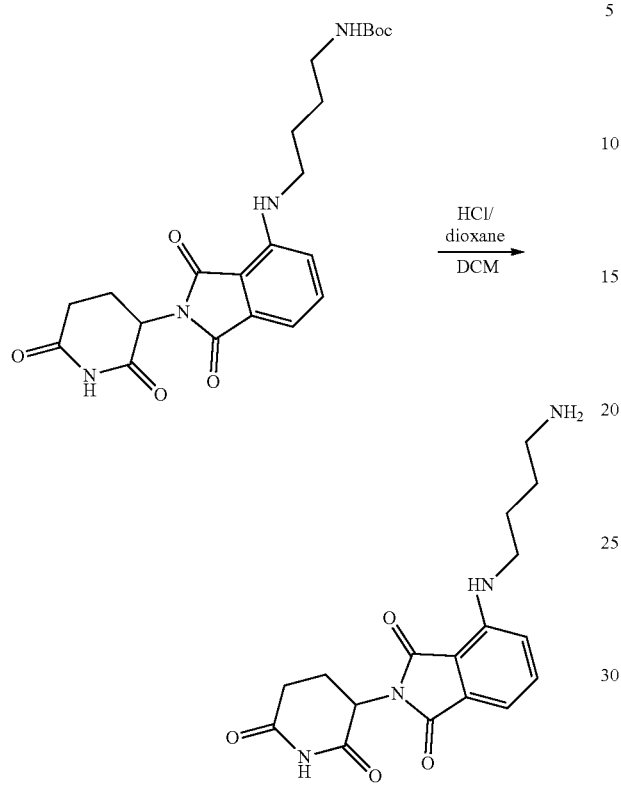

To a solution of tert-butyl N-[4-[[2-(2,6-dioxo-3-piperidyl)-1,3-dioxo-isoindolin-4-yl]amino]butyl] carbamate (100 mg, 224 μmol) in DCM (1 mL) was added HCl/dioxane (4 M, 0.5 mL). The mixture was stirred at 25° C. for 0.5 hr. Upon completion, the reaction mixture was concentrated in vacuo to afford the title compound (85.0 mg, 99% yield, HCl salt) as yellow solid. LC-MS (ESI$^+$) m/z 344.8 (M+H)$^+$.

c) Synthesis of Tert-butyl 3-[2-[[(3S,8S)-3-[4-[[2-(2,6-dioxo-3-piperidyl)-1,3-dioxo-isoindolin-4-yl]amino]butylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

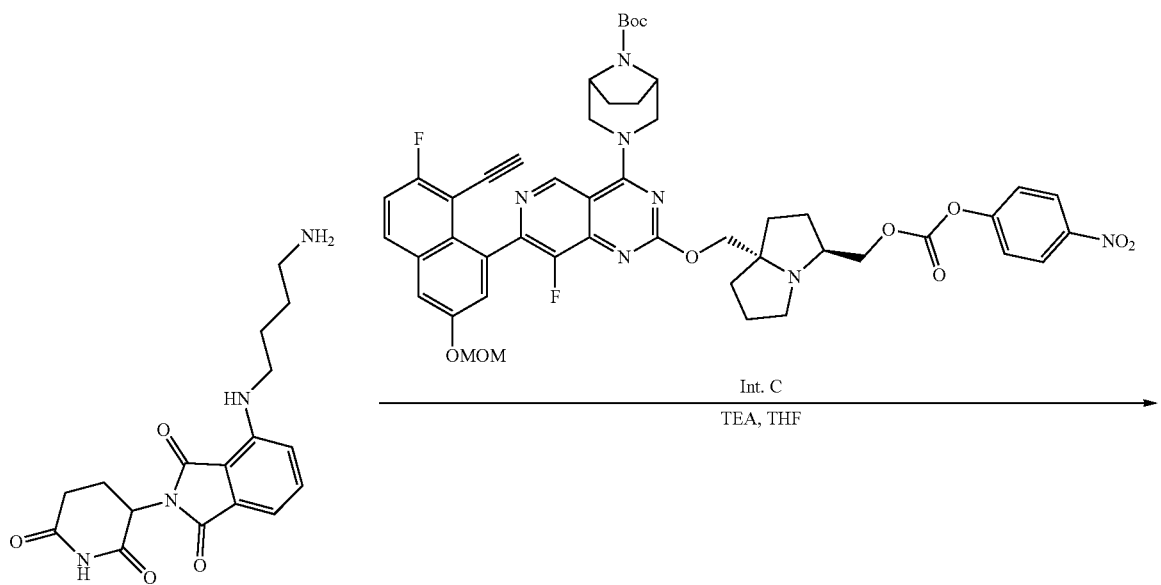

873

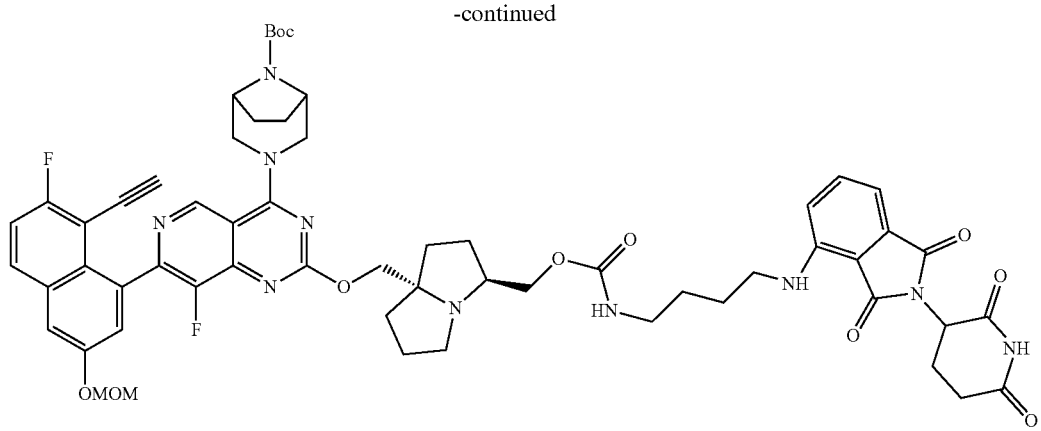

To a solution of Int. C (60.0 mg, 65.0 μmol) and 4-(4-aminobutylamino)-2-(2,6-dioxo-3-piperidyl)isoindoline-1,3-dione (37.1 mg, 97.6 μmol, HCl salt) in THF (2 mL) was added TEA (19.7 mg, 195 μmol). The mixture was stirred at 25° C. for 1.5 hrs. Upon completion, the mixture was concentrated in vacuo to provide a residue. The residue was purified by prep-HPLC (column: Waters xbridge 150*25 mm 10 μm; mobile phase: [water (FA)-ACN]; B %: 30%-

874

-continued

60%, 8 min) to afford the title compound (52.0 mg, 70% yield) as yellow solid. LC-MS (ESI$^+$) m/z 1127.5 (M+H)$^+$.

d) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methyl-N-[4-[[2-(2,6-dioxo-3-piperidyl)-1,3-dioxo-isoindolin-4-yl]amino]butyl]carbamate (019)

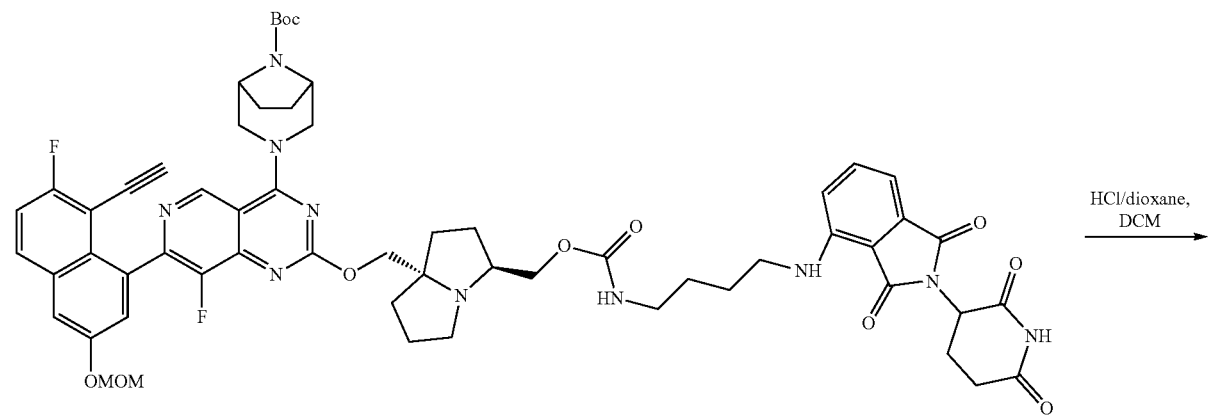

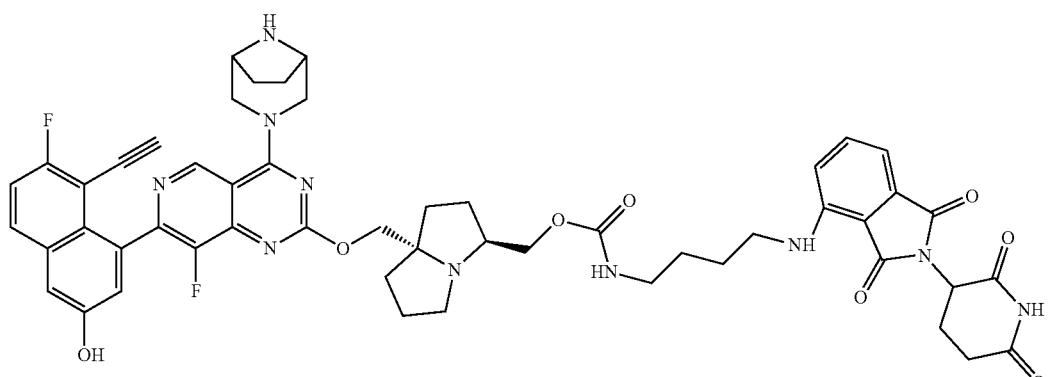

019

To a solution of tert-butyl 3-[2-[[(3S,8S)-3-[4-[[2-(2,6-dioxo-3-piperidyl)-1,3-dioxo-isoindolin-4-yl]amino]butyl-carbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (50.0 mg, 44.3 μmol) in DCM (1 mL) was added HCl/dioxane (4 M, 0.5 mL). The mixture was stirred at 25° C. for 0.5 hr. Upon completion, the reaction mixture was concentrated in vacuo to give a residue. The residue was purified by prep-HPLC (column: Waters xbridge 150*25 mm 10 μm; mobile phase: [water (TFA)-ACN]; B %: 12%-42%, 10 min) to afford the title compound (14.8 mg, 29% yield, TFA salt) as yellow solid. $^1$H NMR (400 MHz, DMSO-$d_6$) δ 11.13-11.03 (m, 1H), 10.46-10.33 (m, 1H), 10.29-10.14 (m, 1H), 9.45-9.26 (m, 1H), 9.17 (s, 1H), 9.11-9.01 (m, 1H), 8.00 (dd, J=6.0, 9.2 Hz, 1H), 7.61-7.53 (m, 1H), 7.50-7.45 (m, 1H), 7.42 (d, J=2.4 Hz, 1H), 7.26 (d, J=1.6 Hz, 1H), 7.18 (s, 1H), 7.12-7.05 (m, 1H), 7.02 (d, J=7.2 Hz, 1H), 6.60-6.47 (m, 1H), 5.04 (dd, J=5.6, 12.8 Hz, 1H), 4.75-4.66 (m, 1H), 4.64-4.49 (m, 3H), 4.37-4.27 (m, 2H), 4.25-4.21 (m, 2H), 3.95-3.83 (m, 4H), 3.30 (d, J=6.0 Hz, 2H), 3.09-2.99 (m, 2H), 2.95-2.79 (m, 2H), 2.65-2.58 (m, 2H), 2.32-2.25 (m, 1H), 2.15-1.86 (m, 12H), 1.63-1.42 (m, 4H); LC-MS (ESI$^+$) m/z 983.1 (M+H)$^+$.

Example 9. Synthesis of Compound 024 a) Synthesis of N-[6-[[2-(2,6-dioxo-3-piperidyl)-1,3-dioxo-isoindolin-4-yl]amino]hexyl] carbamate

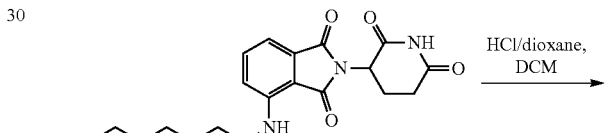

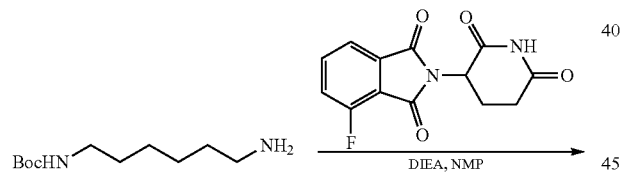

To a solution of tert-butyl N-(6-aminohexyl)carbamate (2.00 g, 9.25 mmol, CAS #51857-17-1) and 2-(2,6-dioxo-3-piperidyl)-4-fluoro-isoindoline-1,3-dione (2.30 g, 8.32 mmol, CAS #835616-60-9) in NMP (30 mL) was added DIEA (2.39 g, 18.4 mmol). The mixture was stirred at 135° C. for 4 hrs. Upon completion, the reaction mixture was extracted with EA (3×20 mL). The combined organic layers were washed with brine (20 mL), dried over anhydrous Na$_2$SO$_4$, filtered and the filtrate was concentrated in vacuo to give a residue. The residue was purified by reversed-phase HPLC (0.1% FA condition) to afford the title compound (1.50 g, 34% yield) as yellow solid. $^1$H NMR (400 MHz, DMSO-$d_6$) δ 11.08 (s, 1H), 7.58 (t, J=7.6 Hz, 1H), 7.08 (d, J=8.4 Hz, 1H), 7.02 (d, J=7.2 Hz, 1H), 6.76 (t, J=5.2 Hz, 1H), 6.53 (t, J=5.6 Hz, 1H), 5.05 (J=5.2, 12.8 Hz, 1H), 3.28 (d, J=6.4 Hz, 2H), 2.83 (s, 4H), 2.63-2.51 (m, 2H), 1.59-1.52 (m, 2H), 1.36 (s, 9H), 1.35-1.18 (m, 6H). LC-MS (ESI$^+$) m/z 373.1 (M−100+H)$^+$.

b) Synthesis of 4-(6-Aminohexylamino)-2-(2,6-dioxo-3-piperidyl)isoindoline-1,3-dione

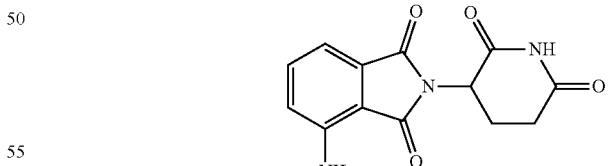

To a solution of tert-butyl N-[6-[[2-(2,6-dioxo-3-piperidyl)-1,3-dioxo-isoindolin-4-yl]amino] hexyl]carbamate (200 mg, 423 μmol) in DCM (4 mL) was added HCl/dioxane (4.00 M, 2.00 mL). The mixture was stirred at 25° C. for 2 hrs. Upon completion, the mixture was concentrated in vacuo to afford the title compound (150 mg, 86% yield, HCl salt) as yellow solid. LC-MS (ESI$^+$) m/z 373.1 (M+H)$^+$.

c) Synthesis of Tert-butyl 3-[2-[[(3RS,8RS)-3-[6-[[2-(2,6-dioxo-3-piperidyl)-1,3-dioxo-isoindolin-4-yl]amino] hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

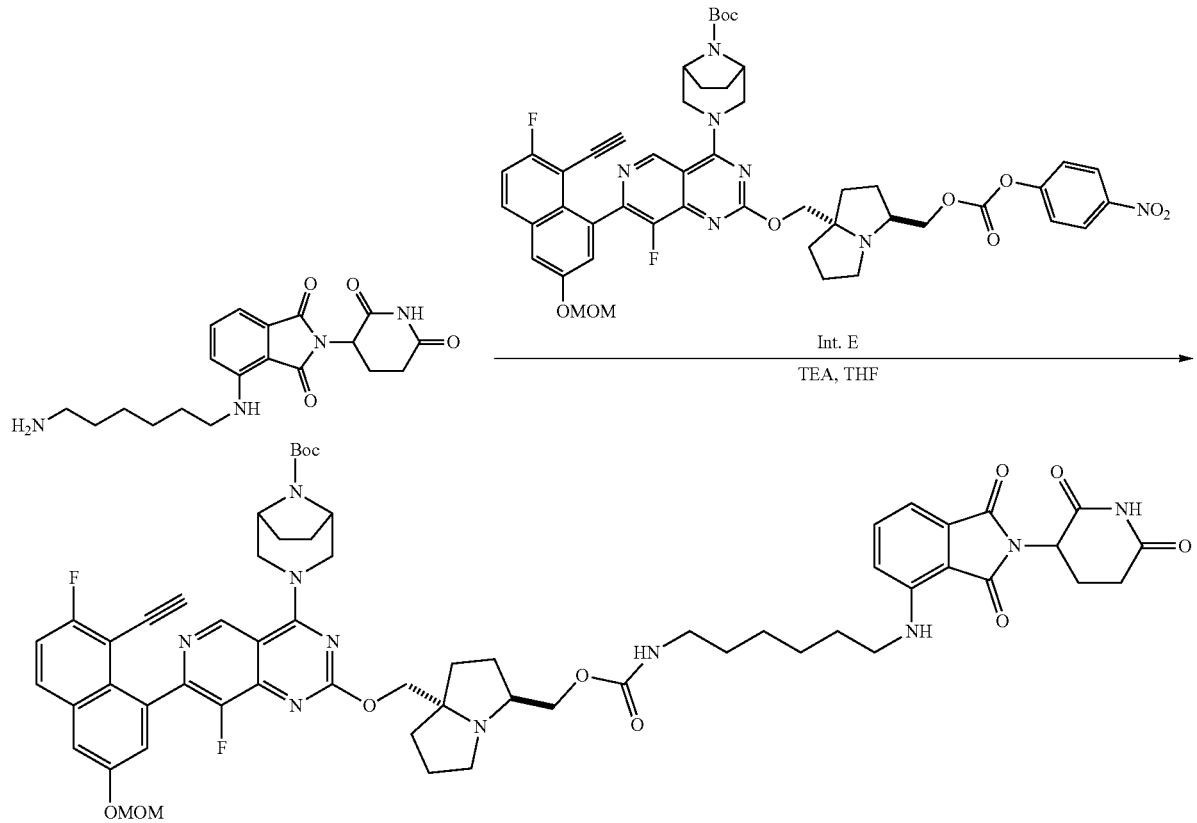

To a solution of 4-(6-aminohexylamino)-2-(2,6-dioxo-3-piperidyl)isoindoline-1,3-dione (43.9 mg, 85.9 µmol, HCl salt) and Int. E (trans racemic) (80.0 mg, 57.2 µmol) in THF (4 mL) was added TEA (17.3 mg, 171 µmol). The mixture was stirred at 25° C. for 2 hrs under $N_2$ atmosphere. Upon completion, the mixture was concentrated in vacuo to afford the title compound (trans racemic) (100 mg, 74% yield) as yellow oil. LC-MS (ESI$^+$) m/z 1155.8 (M+H)$^+$.

d) Synthesis of (3RS,8RS)-[8-[[4-(3,8-Diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methylN-[6-[[2-(2,6-dioxo-3-piperidyl)-1,3-dioxo-isoindolin-4-yl]amino]hexyl]carbamate (024)

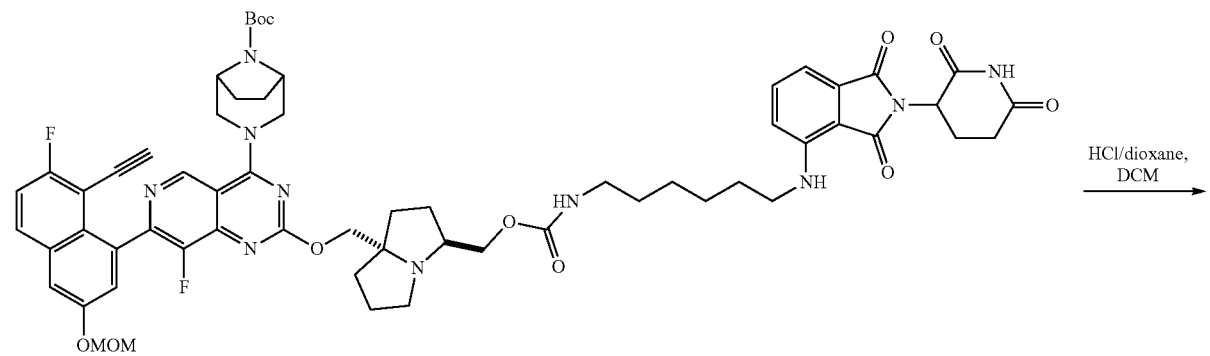

-continued

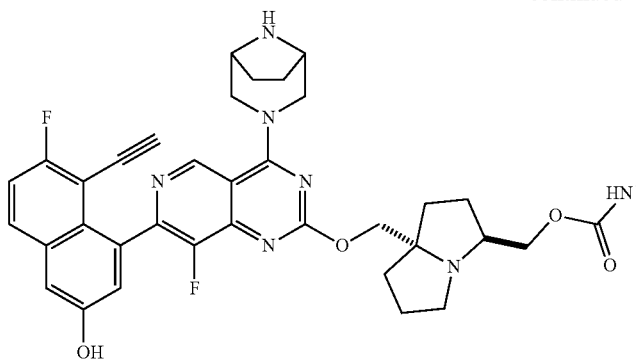
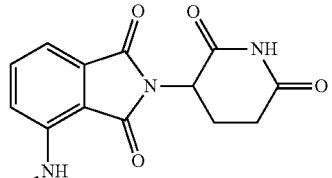

024

To a solution of tert-butyl 3-[2-[[3-[6-[[2-(2,6-dioxo-3-piperidyl)-1,3-dioxo-isoindolin-4-yl]amino] hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (trans racemic) (100 mg, 42.4 μmol) in DCM (5 mL) was added HCl/dioxane (4.00 M, 3.00 mL). The mixture was stirred at 25° C. for 1 hr. Upon completion, the mixture was concentrated in vacuo to provide a residue. The residue was purified by prep-HPLC (column: Phenomenex luna C18 150*25 mm*10 μm; mobile phase: [water (FA)-ACN]; B %: 14%-44%, 10 min) to afford the title compound (trans racemic) (22.05 mg, 50% yield) as yellow solid. $^1$H NMR (400 MHz, DMSO-$d_6$) δ 11.08 (s, 1H), 10.29-10.02 (m, 1H), 9.06 (s, 1H), 8.15 (s, 1H), 8.00-7.94 (m, 1H), 7.60-7.52 (m, 1H), 7.46 (t, J=8.8 Hz, 1H), 7.39 (d, J=2.4 Hz, 1H), 7.20-7.14 (m, 2H), 7.07 (d, J=8.6 Hz, 1H), 7.00 (d, J=7.2 Hz, 1H), 6.55-6.48 (m, 1H), 5.08-5.01 (m, 1H), 4.59-4.51 (m, 1H), 4.42-4.34 (m, 1H), 4.19-4.04 (m, 4H), 3.93 (s, 1H), 3.84 (s, 2H), 3.76-3.65 (m, 2H), 3.29-3.25 (m, 4H), 2.99-2.93 (m, 2H), 2.89-2.83 (m, 1H), 2.81-2.68 (m, 2H), 2.61-2.53 (m, 2H), 2.08-2.00 (m, 2H), 1.81-1.65 (m, 10H), 1.57-1.53 (m, 2H), 1.42-1.35 (m, 2H), 1.33-1.22 (m, 4H); LC-MS (ESI$^+$) m/z 1011.7 (M+H)$^+$.

Example 10. Synthesis of Compound 022 a) Synthesis of Tert-butyl 3-[2-[[(3R,8R)-3-[6-[[2-(2,6-dioxo-3-piperidyl)-1,3-dioxo-isoindolin-4-yl]amino] hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

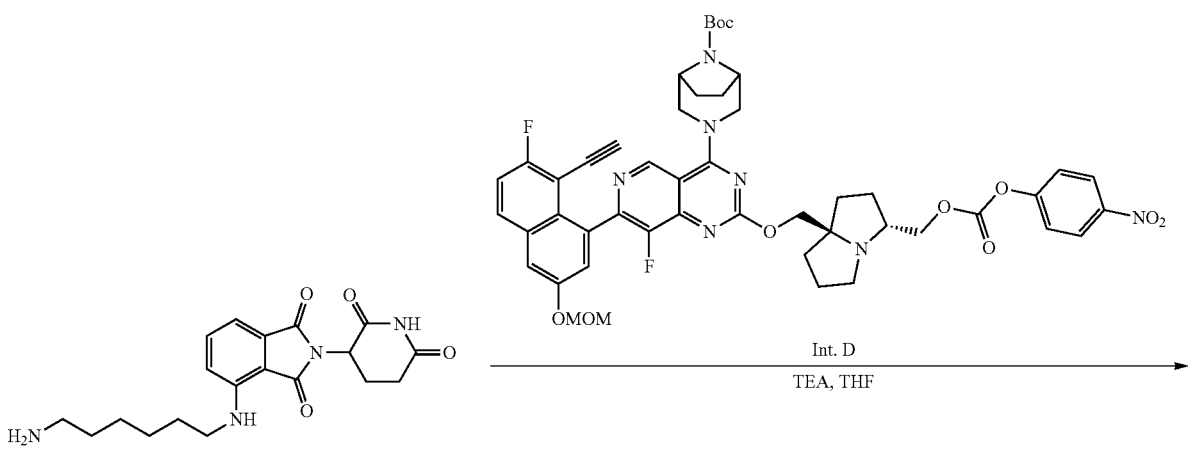

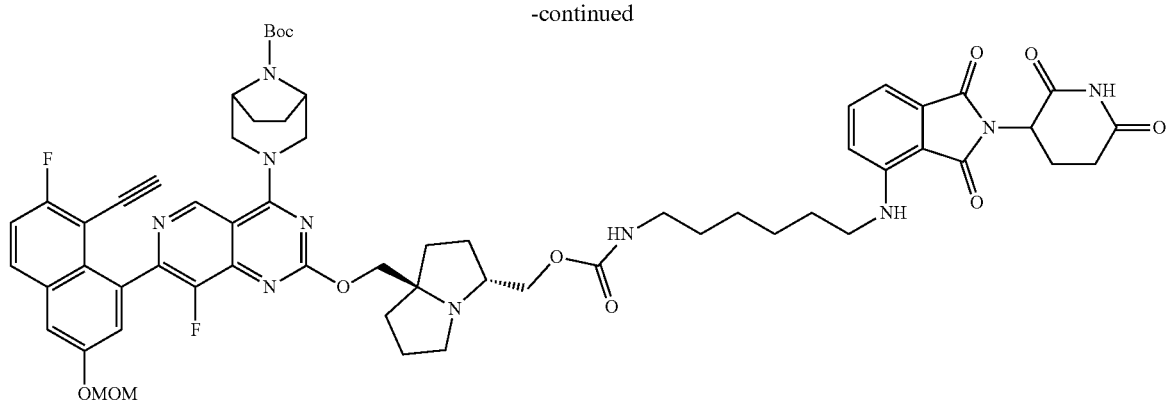

To a solution of 4-(6-aminohexylamino)-2-(2,6-dioxo-3-piperidyl)isoindoline-1,3-dione (39.9 mg, 97.6 μmol, HCl salt) and Int. D (60.0 mg, 65.0 μmol) in THF (6 mL) was added TEA (19.7 mg, 195 μmol). The mixture was stirred at 25° C. for 3 hrs. Upon completion, the mixture was concentrated in vacuo to give a residue. The residue was purified by prep-HPLC (column: Welch Ultimate C18 150*25 mm*5 μm; mobile phase: [water (TFA)-ACN]; B %: 38%-68%, 10 min) to afford the title compound (40.0 mg, 50% yield) as brown solid. $^1$H NMR (400 MHz, DMSO-d$_6$) δ 11.09 (s, 1H), 10.32 (s, 1H), 9.16 (s, 1H), 8.12 (J=6.0, 9.2 Hz, 1H), 7.77 (d, J=2.8 Hz, 1H), 7.62-7.54 (m, 2H), 7.37 (s, 1H), 7.22 (s, 1H), 7.10-7.06 (m, 1H), 7.02 (d, J=6.8 Hz, 1H), 6.58-6.48 (m, 1H), 5.38 (s, 2H), 5.09-5.00 (m, 1H), 4.71-4.42 (m, 4H), 4.39-4.26 (m, 4H), 3.97-3.88 (m, 2H), 3.45 (s, 3H), 3.41-3.32 (m, 4H), 3.31-3.27 (m, 2H), 3.04-2.96 (m, 2H), 2.90-2.83 (m, 1H), 2.61-2.56 (m, 2H), 2.16-2.00 (m, 6H), 1.96-1.83 (m, 4H), 1.76-1.68 (m, 2H), 1.59-1.54 (m, 2H), 1.47 (s, 9H), 1.44-1.40 (m, 2H), 1.35-1.29 (m, 4H); LC-MS (ESI$^+$) m/z 1155.5 (M+H)$^+$.

b) Synthesis of [(3R,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[6-[[2-(2,6-dioxo-3-piperidyl)-1,3-dioxo-isoindolin-4-yl]amino]hexyl]carbamate (022)

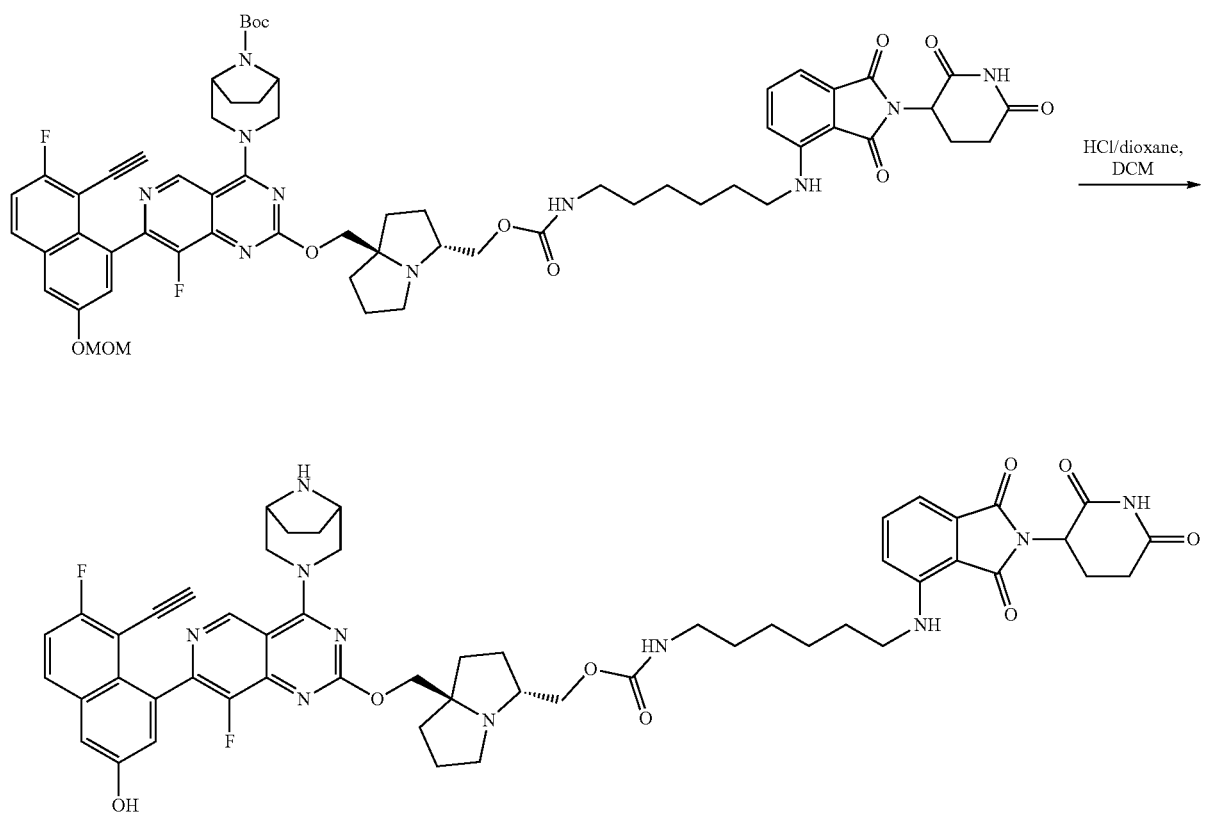

To a solution of tert-butyl 3-[2-[[(3R,8R)-3-[6-[[2-(2,6-dioxo-3-piperidyl)-1,3-dioxo-isoindolin-4-yl] amino]hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (40.0 mg, 34.6 μmol) in DCM (0.5 mL) was added HCl/dioxane (4.00 M, 0.100 mL). The mixture was stirred at 25° C. for 0.5 hr. Upon completion, the mixture was concentrated in vacuo to give a residue. The residue was purified by prep-HPLC (column: Welch Ultimate C18 150*25 mm*5 μm; mobile phase: [water (TFA)-ACN]; B %: 20%-50%, 10 min) to afford the title compound (7.25 mg, 20% yield, TFA salt) as yellow solid. $^1$H NMR (400 MHz, DMSO-$d_6$) δ 11.09 (s, 1H), 10.46-10.35 (m, 1H), 10.32-10.14 (m, 1H), 9.38-3.35 (m, 1H), 9.17 (s, 1H), 9.12-9.03 (m, 1H), 7.99 (dd, J=6.0, 9.2 Hz, 1H), 7.61-7.54 (m, 1H), 7.48 (t, J=8.4 Hz, 1H), 7.41 (d, J=2.4 Hz, 1H), 7.26-7.15 (m, 2H), 7.07 (d, J=8.8 Hz, 1H), 7.02 (d, J=7.2 Hz, 1H), 6.55-6.48 (m, 1H), 5.04 (dd, J=5.2, 12.8 Hz, 1H), 4.75-4.67 (m, 1H), 4.63-4.51 (m, 3H), 4.36-4.28 (m, 2H), 4.23 (s, 2H), 3.97-3.91 (m, 1H), 3.89-3.88 (m, 2H), 3.86-3.84 (m, 1H), 3.45-3.36 (m, 4H), 3.30-3.25 (m, 2H), 3.03-2.95 (m, 2H), 2.93-2.83 (m, 1H), 2.63-2.55 (m, 2H), 2.32-2.27 (m, 1H), 2.13-1.91 (m, 12H), 1.59-1.52 (m, 2H), 1.45-1.38 (m, 2H), 1.36-1.27 (m, 4H); LC-MS (ESI$^+$) m/z 1011.4 (M+H)$^+$.

Example 11. Synthesis of Compound 021 a) Synthesis of Tert-butyl 3-[2-[[(3S,8S)-3-[6-[[2-(2,6-dioxo-3-piperidyl)-1,3-dioxo-isoindolin-4-yl] amino] hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1] octane-8-carboxylate

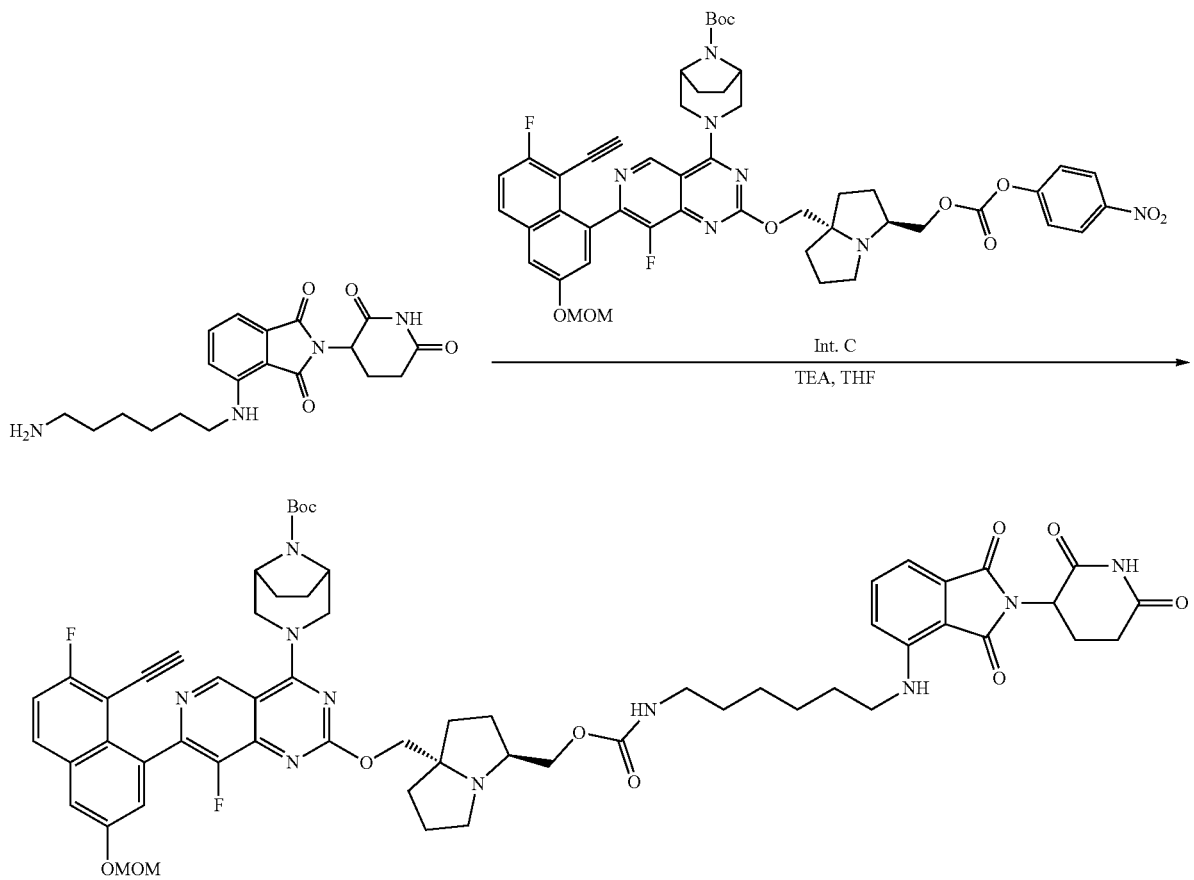

To a solution of Int. C (50.0 mg, 54.2 μmol), 4-(6-aminohexylamino)-2-(2,6-dioxo-3-piperidyl) isoindoline-1,3-dione (33.2 mg, 81.3 μmol, HCl salt) in THF (2 mL) was added TEA (16.4 mg, 162 μmol). The mixture was degassed and purged with N$_2$ for 3 times, and then the mixture was stirred at 25° C. for 2 hrs under N$_2$ atmosphere. Upon completion, the mixture was concentrated in vacuo. The residue was purified by prep-HPLC (column: Welch Xtimate C18 150*25 mm*5 μm; mobile phase: [water (TFA)-ACN]; B %: 36%-66%, 10 min) to afford the title compound (37.0 mg, 59% yield) as yellow solid. LC-MS (ESI$^+$) m/z 1155.6 (M+H)$^+$.

b) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methylN-[6-[[2-(2,6-dioxo-3-piperidyl)-1,3-dioxo-isoindolin-4-yl]amino]hexyl]carbamate (021)

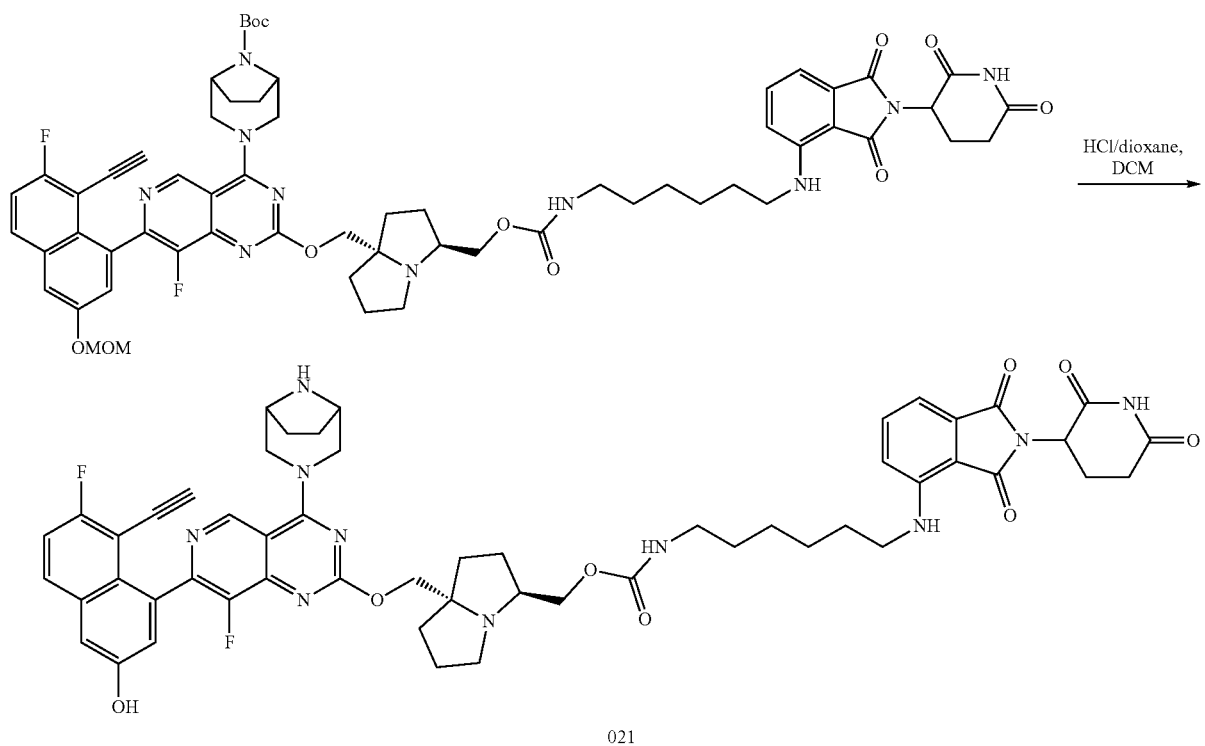

To a solution of tert-butyl 3-[2-[[(3S,8S)-3-[6-[[2-(2,6-dioxo-3-piperidyl)-1,3-dioxo-isoindolin-4-yl]amino]hexyl-carbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (37.0 mg, 32.0 µmol) in DCM (0.5 mL) was added HCl/dioxane (4 M, 1.00 mL). The mixture was stirred at 25° C. for 1 hr. Upon completion, the mixture was concentrated in vacuo. The residue was purified by prep-HPLC (column: Phenomenex luna C18 150*25 mm*10 µm; mobile phase: [water (HCl)-ACN]; B %: 15%-45%, 10 min) to afford the title compound (9.86 mg, 27% yield, HCl salt) as yellow solid. $^1$H NMR (400 MHz, DMSO-$d_6$) δ 11.08 (s, 1H), 10.16-10.09 (m, 1H), 9.77 (d, J=7.6 Hz, 1H), 9.15 (s, 1H), 7.98 (dd, J=6.4, 9.2 Hz, 1H), 7.59-7.54 (m, 1H), 7.49-7.44 (m, 1H), 7.42 (d, J=2.4 Hz, 1H), 7.33-7.25 (m, 1H), 7.25-7.22 (m, 1H), 7.08 (d, J=8.4 Hz, 1H), 7.01 (d, J=7.2 Hz, 1H), 5.04 (dd, J=5.2, 12.8 Hz, 1H), 4.69-4.55 (m, 4H), 4.34-4.26 (m, 2H), 4.23-4.15 (m, 2H), 4.07-3.99 (m, 2H), 3.98-3.95 (m, 1H), 3.95-3.88 (m, 1H), 3.47-3.32 (m, 4H), 3.27 (t, J=6.8 Hz, 2H), 3.03-2.95 (m, 2H), 2.93-2.85 (m, 1H), 2.62-2.54 (m, 2H), 2.55-2.51 (m, 2H), 2.13-1.97 (m, 10H), 1.57-1.52 (m, 2H), 1.44-1.38 (m, 2H), 1.34-1.26 (m, 4H); LC-MS (ESI$^+$) m/z 1011.6 (M+H)$^+$.

Example 12. Synthesis of Compound 026 a) Synthesis of Tert-butyl N-[8-[[2-(2,6-dioxo-3-piperidyl)-1,3-dioxo-isoindolin-4-yl]amino]octyl]carbamate

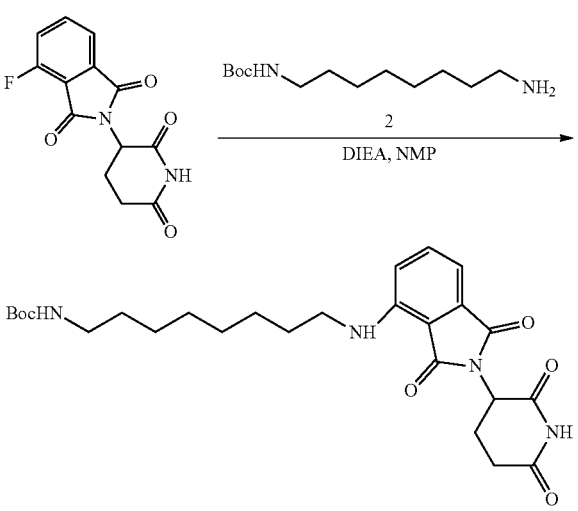

To a solution of tert-butyl N-(8-aminooctyl)carbamate (1.20 g, 4.91 mmol, CAS #88829-82-7) and 2-(2,6-dioxo-3-piperidyl)-4-fluoroisoindoline-1,3-dione (1.36 g, 4.91 mmol, CAS #835616-60-9) in NMP (30 mL) was added DIEA (1.27 g, 9.82 mmol). The mixture was stirred at 135° C. for 3 hrs. Upon completion, to the reaction mixture was added H₂O (100 mL) and extracted with EA (3×50 mL). The combined organic layers were washed with brine (50 mL), dried over anhydrous Na₂SO₄, filtered and the filtrate was concentrated in vacuo to provide a residue. The residue was purified by reverse phase (0.1% FA condition) to afford the title compound (1.10 g, 45% yield) as yellow solid. $^1$H NMR (400 MHz, DMSO-d$_6$) δ 11.08 (s, 1H), 7.59-7.55 (m, 1H), 7.08 (d, J=8.6 Hz, 1H), 7.01 (d, J=7.2 Hz, 1H), 6.73 (s, 1H), 6.52-6.50 (m, 1H), 5.04 (dd, J=5.2, 12.8 Hz, 1H), 3.00-2.76 (m, 4H), 2.62-2.53 (m, 4H), 1.59-1.53 (m, 2H), 1.36 (s, 9H), 1.33-1.17 (m, 10H); LC-MS (ESI$^+$) m/z 401.0 (M+H−100)$^+$.

b) Synthesis of 4-(8-Aminooctylamino)-2-(2,6-dioxo-3-piperidyl)isoindoline-1,3-dione

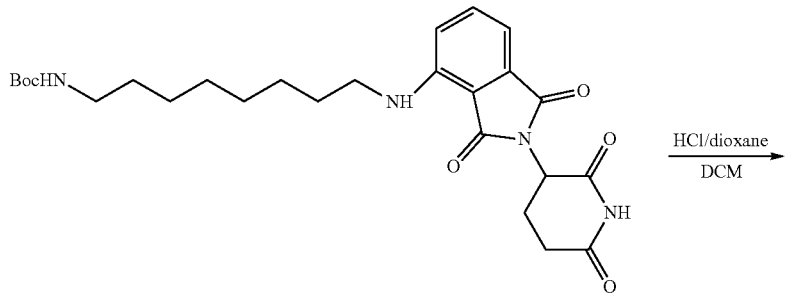

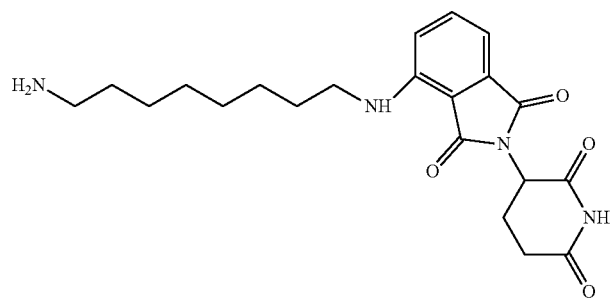

To a solution of tert-butyl N-[8-[[2-(2,6-dioxo-3-piperidyl)-1,3-dioxo-isoindolin-4-yl]amino]octyl] carbamate (50.0 mg, 99.8 μmol) in DCM (1 mL) was added HCl/dioxane (4 M, 0.5 mL). The mixture was stirred at 25° C. for 0.5 hr. Upon completion, the reaction mixture was concentrated in vacuo to afford the title compound (43.6 mg, 100% yield, HCl salt) as yellow oil. LC-MS (ESI$^+$) m/z 400.8 (M+H)$^+$.

c) Synthesis of Tert-butyl 3-[2-[[(3S,8S)-3-[8-[[2-(2,6-dioxo-3-piperidyl)-1,3-dioxo-isoindolin-4-yl]amino] octylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

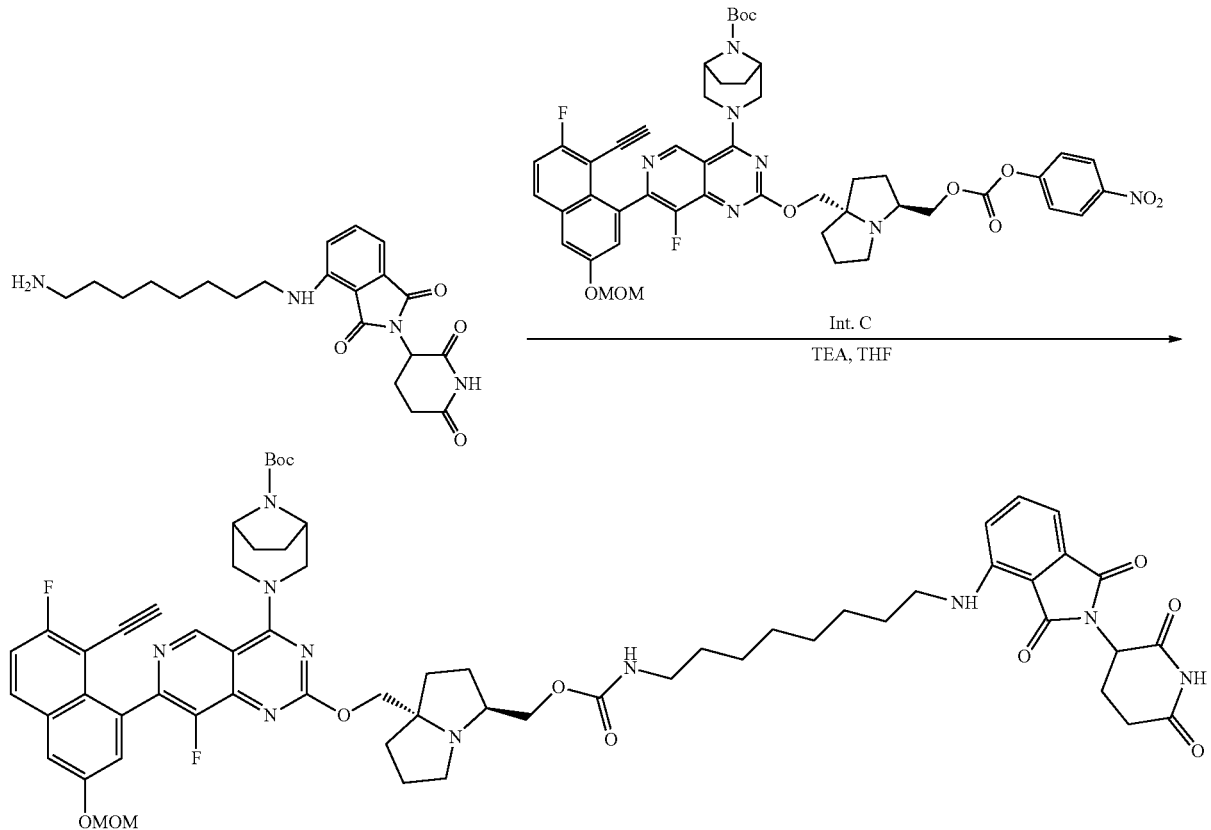

To a solution of 4-(8-aminooctylamino)-2-(2,6-dioxo-3-piperidyl)isoindoline-1,3-dione (17.1 mg, 39.0 μmol, HCl salt) and Int. C (24.0 mg, 26.0 μmol) in THF (1 mL) was added TEA (7.90 mg, 78.1 μmol). The mixture was stirred at 25° C. for 1 hr. Upon completion, the reaction mixture was concentrated in vacuo to give a residue. The residue was purified by prep-HPLC (column: Phenomenex luna C18 150*25 mm*10 μm; mobile phase: [water (FA)-ACN]; B %: 34%-64%, 15 min) to afford the title compound (10.0 mg, 32% yield) as yellow solid. LC-MS (ESI$^+$) m/z 1183.5 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[8-[[2-(2,6-dioxo-3-piperidyl)-1,3-dioxo-isoindolin-4-yl]amino]octyl]carbamate (026)

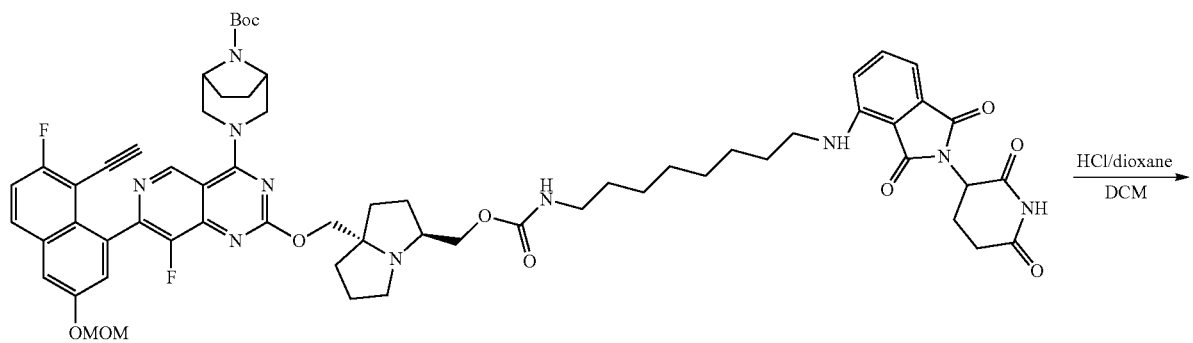

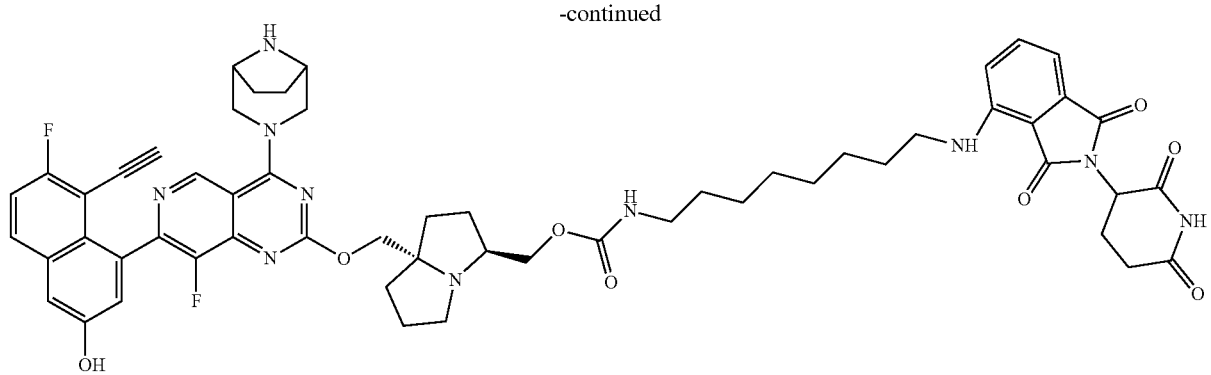

026

To a solution of tert-butyl 3-[2-[[(3S,8S)-3-[8-[[2-(2,6-dioxo-3-piperidyl)-1,3-dioxo-isoindolin-4-yl]amino]octyl-carbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (10.0 mg, 8.45 μmol) in DCM (1 mL) was added HCl/dioxane (4 M, 2.11 uL). The mixture was stirred at 25° C. for 0.5 hr. Upon completion, the reaction mixture was concentrated in vacuo to give a residue. The residue was purified by prep-HPLC (column: Phenomenex luna C18 150*25 mm*10 μm; mobile phase: [water (FA)-ACN]; B %: 25%-55%, 10 min) to afford the title compound (3.74 mg, 42% yield) as yellow solid. $^1$H NMR (400 MHz, DMSO-$d_6$) δ 11.16-11.01 (m, 1H), 10.33-9.96 (m, 1H), 9.07-8.98 (m, 1H), 8.24 (s, 1H), 7.97 (dd, J=6.0, 9.2 Hz, 1H), 7.60-7.53 (m, 1H), 7.47-7.43 (m, 1H), 7.38 (d, J=2.4 Hz, 1H), 7.20-7.12 (m, 2H), 7.10-7.05 (m, 1H), 7.01 (d, J=7.2 Hz, 1H), 6.51-6.48 (m, 1H), 5.12-4.95 (m, 1H), 4.47 (d, J=11.6 Hz, 1H), 4.35-4.25 (m, 1H), 4.17-4.05 (m, 3H), 4.04-3.99 (m, 1H), 3.95-3.90 (m, 1H), 3.67-3.60 (m, 2H), 3.58-3.54 (m, 4H), 2.98-2.82 (m, 4H), 2.77-2.69 (m, 2H), 2.08-1.95 (m, 3H), 1.77-1.63 (m, 10H), 1.55 (d, J=6.4 Hz, 2H), 1.39-1.23 (m, 12H); LC-MS (ESI$^+$) m/z 1039.5 (M+H)$^+$.

Example 13. Synthesis of Compound 023 a) Synthesis of Tert-butyl 3-[2-[[3-[9-[[2-(2,6-dioxo-3-piperidyl)-1,3-dioxo-isoindolin-4-yl]amino]nonylcarbamoyloxymethyl]-1,2,3,5,6,7-hexahydro-pyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

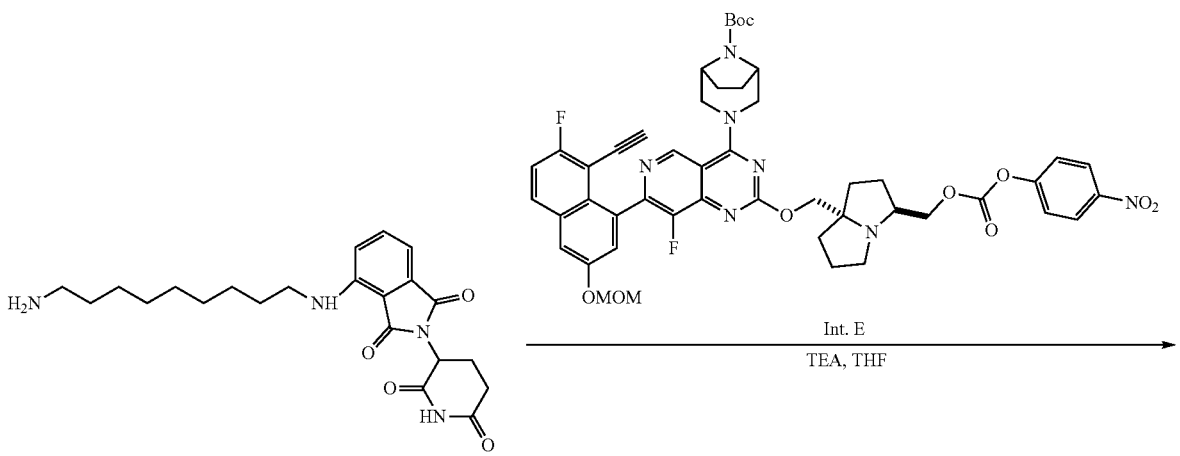

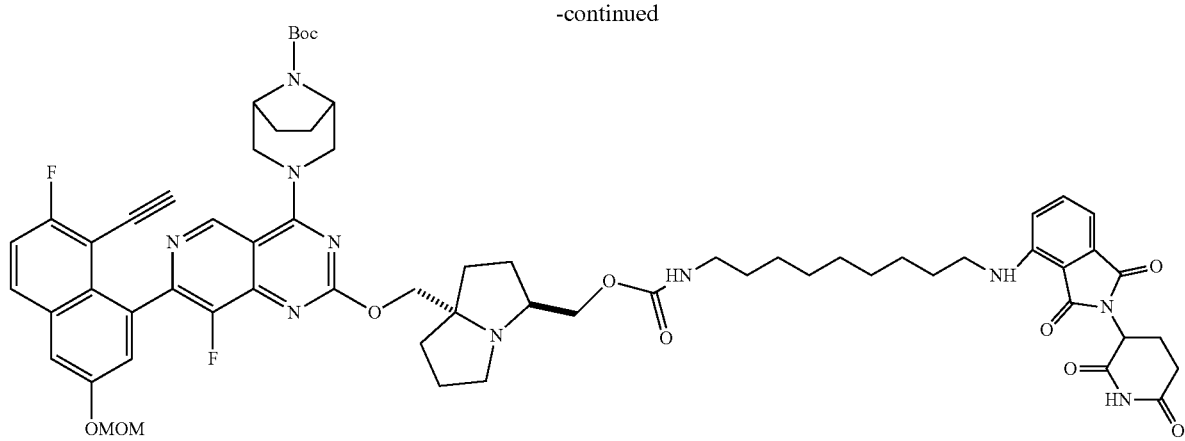

To a solution of Int. E (90.0 mg, 97.6 μmol) and 4-(9-aminononylamino)-2-(2,6-dioxo-3-piperidyl)isoindoline-1,3-dione (66.0 mg, 146 μmol, HCl salt) in THF (10 mL) was TEA (29.6 mg, 292 μmol). The mixture was stirred at 25° C. for 2 hrs. Upon completion, the reaction mixture was concentrated in vacuo to give a residue. The residue was purified by prep-HPLC (column: Welch Xtimate C18 150*25 mm*5 μm; mobile phase: [water (HCl)-ACN]; B %: 40%-70%, 8 min) to afford the title compound (trans racemic) (40.0 mg, 30% yield) as yellow solid. $^1$H NMR (400 MHz, DMSO-$d_6$) δ 11.09 (s, 1H), 10.48-10.29 (m, 1H), 9.25-9.08 (m, 1H), 8.11 (dd, J=6.0, 9.2 Hz, 1H), 7.76 (d, J=2.4 Hz, 1H), 7.60-7.52 (m, 2H), 7.37 (s, 1H), 7.24-7.15 (m, 1H), 7.07 (d, J=8.4 Hz, 1H), 7.01 (d, J=6.8 Hz, 1H), 6.56-6.46 (m, 1H), 5.37 (s, 2H), 5.11-5.01 (m, 1H), 4.65-4.44 (m, 4H), 4.32-4.31 (m, 3H), 4.00-3.85 (m, 2H), 3.74-3.65 (m, 2H), 3.44 (s, 3H), 3.30-3.26 (m, 2H), 3.02-2.94 (m, 2H), 2.92-2.84 (m, 1H), 2.60-2.59 (m, 2H), 2.56 (s, 4H), 2.30-2.29 (m, 1H), 2.08-2.00 (m, 4H), 1.95-1.82 (m, 4H), 1.75-1.68 (m, 2H), 1.57-1.53 (m, 2H), 1.47 (s, 9H), 1.42-1.22 (m, 14H); LC-MS (ESI$^+$) m/z 1197.4 (M+H)$^+$.

a) Synthesis of (3RS,8RS)-[8-[[4-(3,8-Diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[9-[[2-(2,6-dioxo-3-piperidyl)-1,3-dioxo-isoindolin-4-yl]amino]nonyl]carbamate (023)

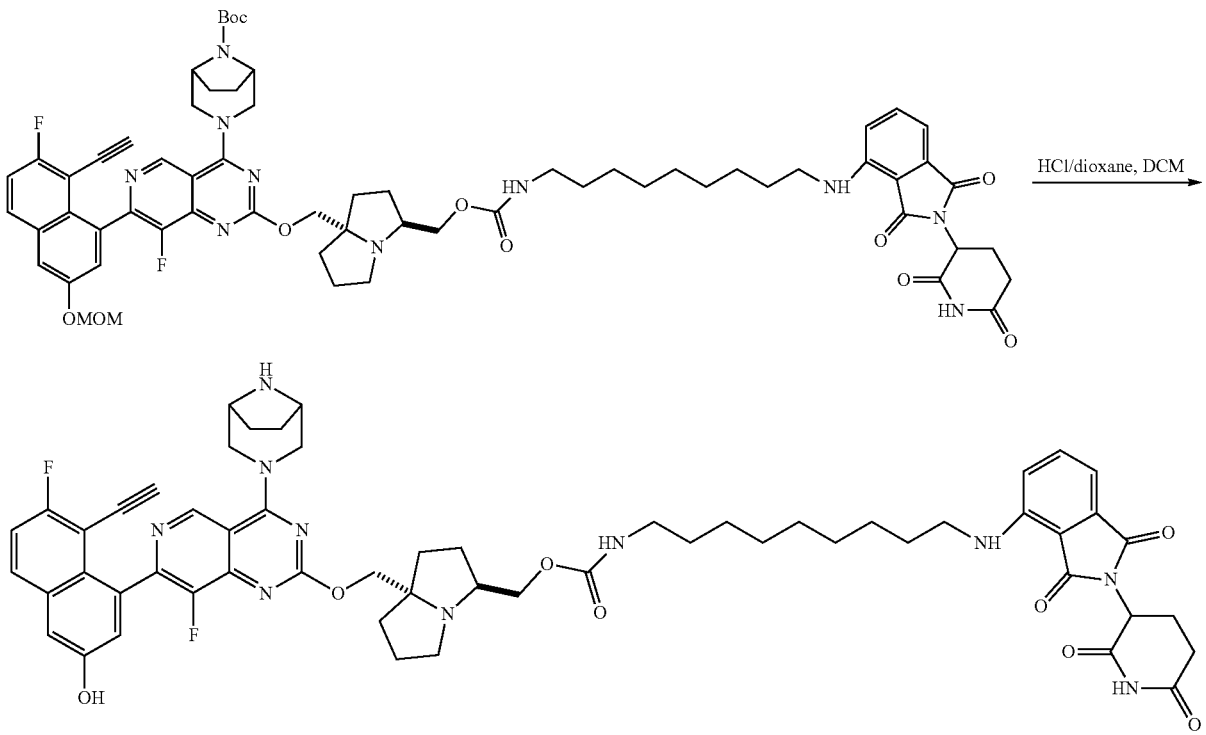

To a solution of tert-butyl 3-[2-[[(3RS,8RS)-3-[9-[[2-(2,6-dioxo-3-piperidyl)-1,3-dioxo-isoindolin-4-yl]amino]nonylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (40.0 mg, 33.4 µmol) in DCM (1 mL) was added HCl/dioxane (4.00 M, 0.500 mL). The mixture was stirred at 25° C. for 0.5 hr. Upon completion, the reaction mixture was concentrated in vacuo to give a residue. The residue was purified by prep-HPLC (column: Welch Ultimate C18 150*25 mm*5 µm; mobile phase: [water (TFA)-ACN]; B %: 25%-55%, 10 min) to afford the title compound (trans racemic) (8.83 mg, 22% yield, TFA salt) as yellow solid. $^1$H NMR (400 MHz, DMSO-$d_6$) δ 11.08 (s, 1H), 10.42-10.32 (m, 1H), 10.26-10.16 (m, 1H), 9.38-9.30 (m, 1H), 9.17 (s, 1H), 9.11-8.99 (m, 1H), 7.99 (dd, J=6.0, 9.2 Hz, 1H), 7.60-7.55 (m, 1H), 7.47 (t, J=9.2 Hz, 1H), 7.41 (d, J=2.8 Hz, 1H), 7.18 (s, 2H), 7.07 (d, J=8.4 Hz, 1H), 7.02 (d, J=7.2 Hz, 1H), 6.53-6.48 (m, 1H), 5.04 (J=6.0, 12.8 Hz, 1H), 4.75-4.67 (m, 1H), 4.61-4.52 (m, 3H), 4.31 (d, J=5.6 Hz, 2H), 4.23 (s, 2H), 3.98-3.91 (m, 1H), 3.88 (d, J=4.8 Hz, 2H), 3.85 (d, J=7.2 Hz, 1H), 3.28-3.26 (m, 2H), 3.00-2.95 (m, 2H), 2.92-2.85 (m, 1H), 2.60-2.56 (m, 2H), 2.56 (s, 4H), 2.31-2.27 (m, 1H), 2.04-1.95 (m, 8H), 1.59-1.53 (m, 2H), 1.41-1.37 (m, 2H), 1.34-1.17 (m, 14H); LC-MS (ESI$^+$) m/z 1053.3 (M+H)$^+$.

Example 14. Synthesis of Compound 016 a) Synthesis of Tert-butyl (9-((2-(2,6-dioxopiperidin-3-yl)-1,3-dioxoisoindolin-4-yl)amino)nonyl)carbamate To a solution of tert-butyl N-(9-aminononyl)carbamate (1.20 g, 4.64 mmol, CAS #510754-90-21) and 2-(2,6-dioxo-3-piperidyl)-4-fluoroisoindoline-1,3-dione (1.05 g, 3.80 mmol, CAS #835616-60-9) in NMP (30 mL) was added DIEA (1.09 g, 8.44 mmol). The mixture was stirred at 135° C. for 3 hrs. Upon completion, the reaction mixture was added H$_2$O (100 mL) and extracted with EA (3×50 mL). The combined organic layers were washed with brine (50 mL), dried over anhydrous Na$_2$SO$_4$, filtered and the filtrate was concentrated in vacuo. The reaction mixture was filtered and concentrated in vacuo, then the residue was purified by prep-HPLC (0.1% FA condition) to afford the title compound (1.20 g, 55% yield) as white solid. $^1$H NMR (400 MHz, DMSO-$d_6$) δ 11.09 (s, 1H), 7.58 (dd, J=7.2, 8.4 Hz, 1H), 7.09 (d, J=8.4 Hz, 1H), 7.01 (d, J=7.2 Hz, 1H), 6.74 (t, J=5.6 Hz, 1H), 6.52 (t, J=5.6 Hz, 1H), 5.05 (dd, J=5.2, 12.8 Hz, 1H), 2.95-2.81 (m, 4H), 2.63-2.52 (m, 4H), 1.59-1.54 (m, 2H), 1.36 (s, 10H), 1.32 (d, J=7.2 Hz, 2H), 1.24 (s, 9H); LC-MS (ESI$^+$) m/z 415.1 (M−100+H)$^+$.

b) Synthesis of 4-((9-Aminononyl)amino)-2-(2,6-dioxopiperidin-3-yl)isoindoline-1,3-dione

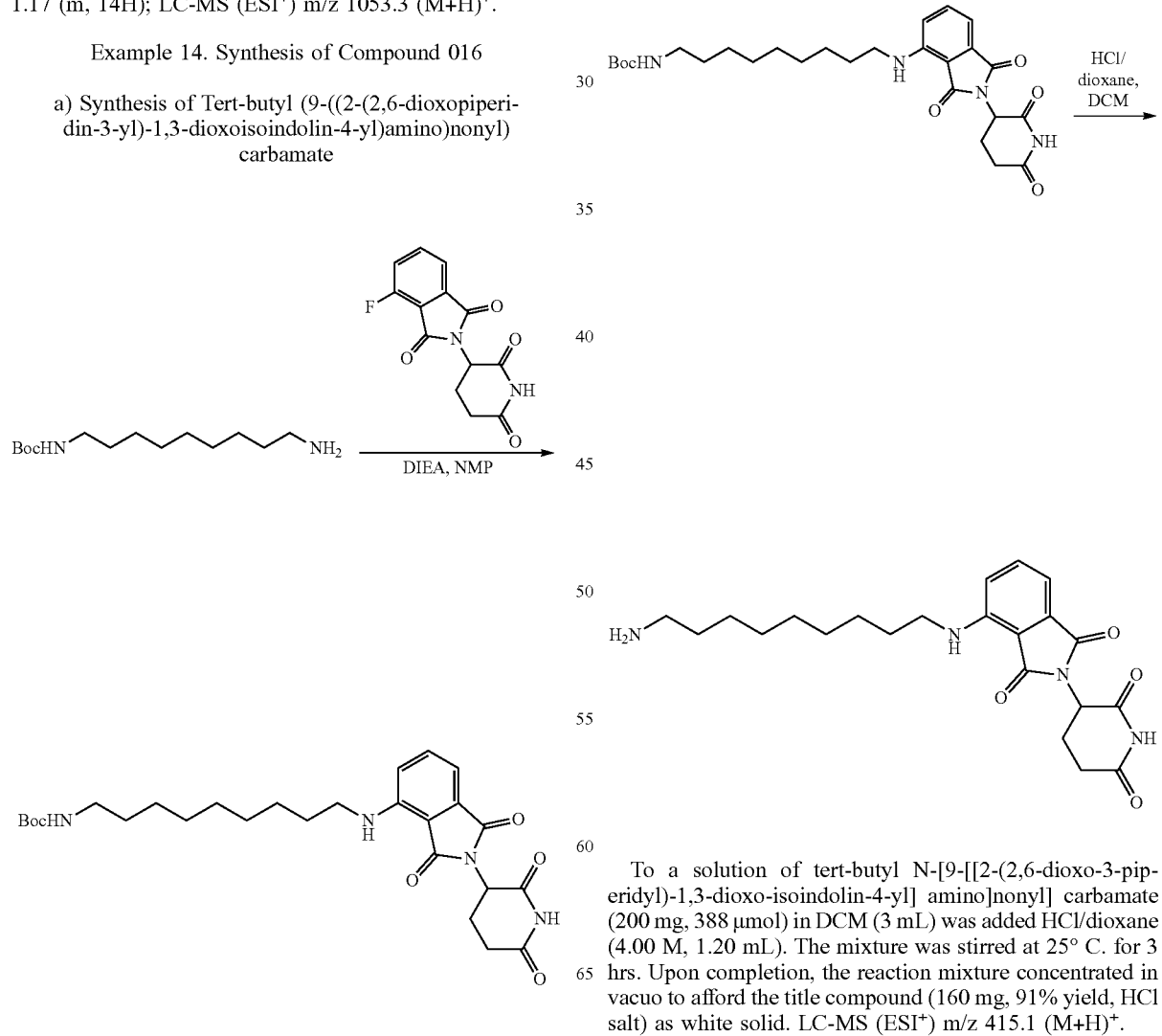

To a solution of tert-butyl N-[9-[[2-(2,6-dioxo-3-piperidyl)-1,3-dioxo-isoindolin-4-yl]amino]nonyl] carbamate (200 mg, 388 µmol) in DCM (3 mL) was added HCl/dioxane (4.00 M, 1.20 mL). The mixture was stirred at 25° C. for 3 hrs. Upon completion, the reaction mixture concentrated in vacuo to afford the title compound (160 mg, 91% yield, HCl salt) as white solid. LC-MS (ESI$^+$) m/z 415.1 (M+H)$^+$.

c) Synthesis of Tert-butyl 3-(2-(((3S,7aS)-3-((((9-((2-(2,6-dioxopiperidin-3-yl)-1,3-dioxoisoindolin-4-yl) amino)nonyl)carbamoyl)oxy)methyl)hexahydro-1H-pyrrolizin-7a-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

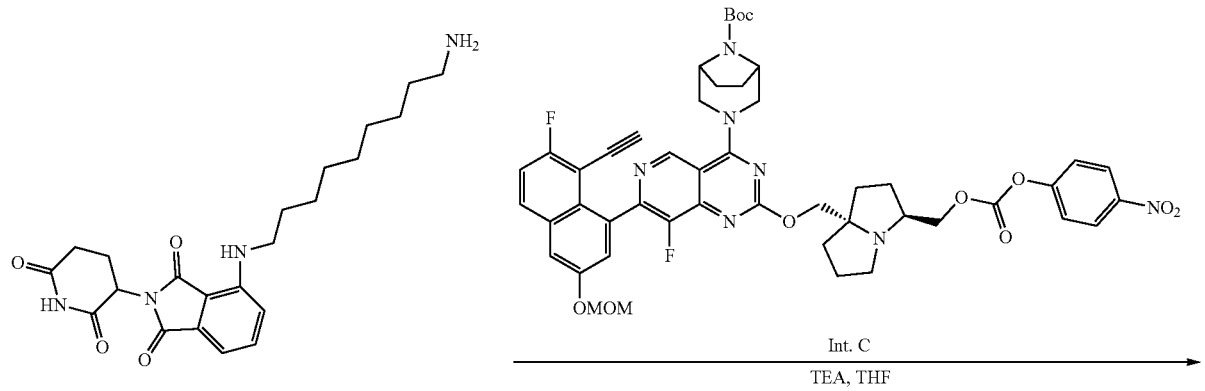

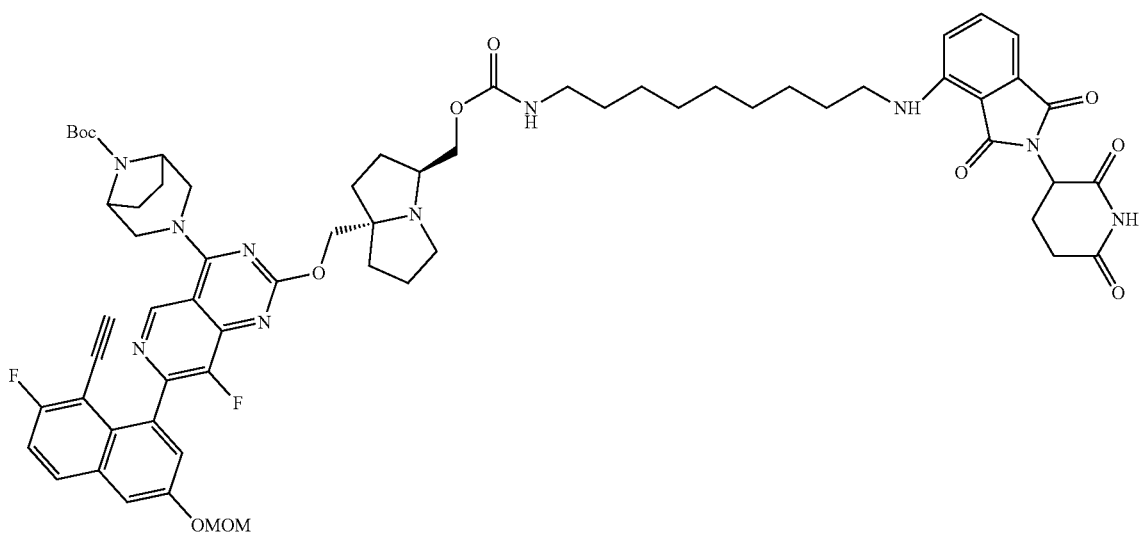

To a solution of 4-(9-aminononylamino)-2-(2,6-dioxo-3-piperidyl)isoindoline-1,3-dione (53.9 mg, 130 µmol) in THF (5 mL) was added TEA (19.7 mg, 195 µmol) and Int. C (60.0 mg, 65.0 µmol). The mixture was stirred at 25° C. for 3 hrs. Upon completion, the reaction mixture was concentrated in vacuo to give a residue, then the residue was purified by prep-HPLC (column: Phenomenex luna C18 150*25 mm*10 µm; mobile phase: [water (FA)-ACN]; B %: 35%-65%, 0 min) to afford the title compound (25.0 mg, 32% yield) as white solid. LC-MS (ESI$^+$) m/z 1198.5 (M+H)$^+$.

d) Synthesis of ((3S,7aS)-7a-(((4-(3,8-diazabicyclo [3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl) methyl (9-((2-(2,6-dioxopiperidin-3-yl)-1,3-dioxoisoindolin-4-yl)amino)nonyl)carbamate (O16)

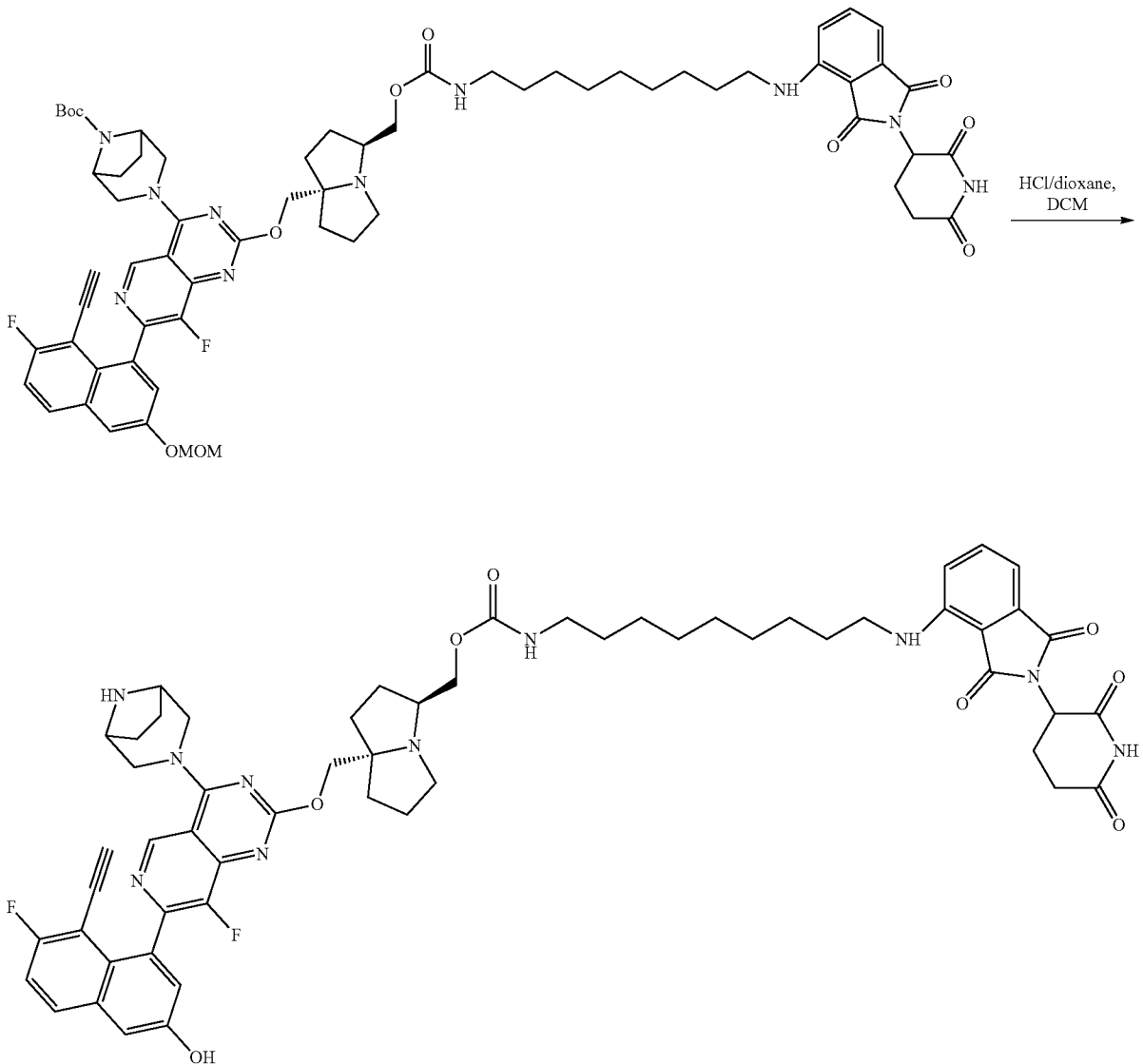

O16

To a solution of tert-butyl 3-[2-[[(3S,8S)-3-[9-[[2-(2,6-dioxo-3-piperidyl)-1,3-dioxo-isoindolin-4-yl] amino]nonyl-carbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (25.0 mg, 20.8 μmol) in DCM (5 mL) was added HCl/dioxane (4.00 M, 5.20 uL). The mixture was stirred at 25° C. for 2 hrs. Upon completion, the reaction mixture was concentrated in vacuo to produce a residue and the residue was purified by prep-HPLC (column: Phenomenex luna C18 150*25 mm*10 μm; mobile phase: [water (FA)-ACN]; B %: 18%-48%, 0 min) to afford the title compound (10.0 mg, 43% yield, FA salt) as white solid. $^1$H NMR (400 MHz, DMSO-$d_6$) δ 11.25-10.93 (m, 1H), 9.04 (s, 1H), 7.97 (dd, J=6.0, 9.2 Hz, 1H), 7.57 (t, J=7.6 Hz, 1H), 7.46 (t, J=9.2 Hz, 1H), 7.39 (d, J=2.4 Hz, 1H), 7.17 (d, J=2.4 Hz, 2H), 7.08 (d, J=8.4 Hz, 1H), 7.01 (d, J=6.8 Hz, 1H), 6.52 (t, J=5.6 Hz, 1H), 5.05 (dd, J=5.2, 12.8 Hz, 1H), 4.49 (d, J=11.2 Hz, 1H), 4.32 (d, J=12.4 Hz, 1H), 4.19-4.06 (m, 4H), 4.03 (d, J=10.4 Hz, 1H), 3.94 (s, 1H), 3.67-3.63 (m, 4H), 3.28 (s, 2H), 2.97-2.92 (m, 2H), 2.88 (dd, J=3.2, 5.2 Hz, 1H), 2.84 (d, J=5.6 Hz, 1H), 2.78-2.71 (m, 2H), 2.60 (d, J=2.4 Hz, 1H), 2.07-1.99 (m, 2H), 1.80-1.65 (m, 10H), 1.61-1.48 (m, 4H), 1.38-1.22 (m, 12H); LC-MS (ESI$^+$) m/z 1053.6 (M+H)$^+$.

Example 15. Synthesis of Compound 017 a) Synthesis of N-[6-[[2-(2,6-dioxo-3-piperidyl)-1,3-dioxo-isoindolin-5-yl]amino]hexyl] carbamate

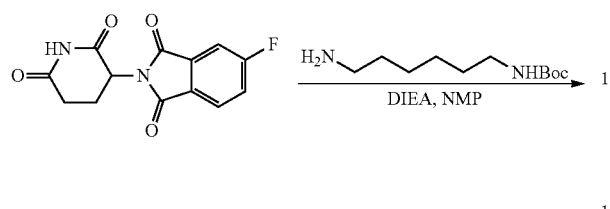

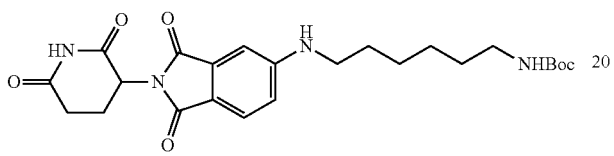

To a solution of 2-(2,6-dioxo-3-piperidyl)-5-fluoro-isoindoline-1,3-dione (4.00 g, 14.4 mmol, CAS #835616-61-0) and tert-butyl N-(6-aminohexyl)carbamate (3.45 g, 15.9 mmol, CAS #51857-17-1) in NMP (40 mL) was added DIEA (3.74 g, 28.9 mmol). The mixture was degassed and purged with $N_2$ for 3 times, and then the mixture was stirred at 90° C. for 18 hrs under $N_2$ atmosphere. On completion, the reaction mixture was diluted with $H_2O$ (60 mL) and extracted with EA (3×50 mL). The combined organic phase was washed with brine (30 mL), dried over anhydrous $Na_2SO_4$ and concentrated in vacuo to provide the residue. The residue was purified by column chromatography ($SiO_2$, PE:EA=10:1 to 2:1) to afford the title compound (2.85 g, 40% yield) as green solid. $^1$H NMR (400 MHz, DMSO-$d_6$) δ 11.05 (s, 1H), 7.55 (d, J=8.4 Hz, 1H), 6.94 (d, J=1.2 Hz, 1H), 6.84 (dd, J=1.6, 8.4 Hz, 1H), 6.80-6.70 (m, 1H), 5.02 (dd, J=5.2, 12.8 Hz, 1H), 3.98-3.66 (m, 1H), 3.30 (t, J=7.2 Hz, 2H), 3.18-3.10 (m, 2H), 2.93-2.86 (m, 2H), 2.65-2.50 (m, 2H), 2.16 (d, J=8.0 Hz, 2H), 1.95-1.84 (m, 2H), 1.60-1.51 (m, 2H), 1.36 (s, 9H), 1.31-1.23 (m, 2H); LC-MS (ESI$^+$) m/z 416.8 (M+H−56)$^+$.

b) Synthesis of 5-(6-Aminohexylamino)-2-(2,6-dioxo-3-piperidyl)isoindoline-1,3-dione

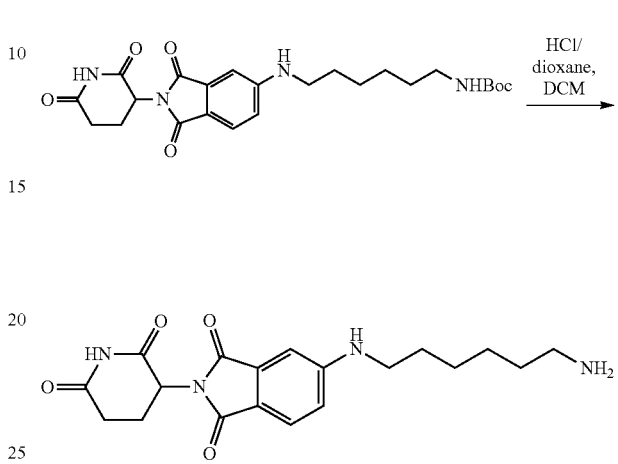

To a solution of tert-butyl N-[6-[[2-(2,6-dioxo-3-piperidyl)-1,3-dioxo-isoindolin-5-yl]amino]hexyl] carbamate (200 mg, 423 μmol) in DCM (1 mL) was added HCl/dioxane (4 M, 2.00 mL). The mixture was stirred at 25° C. for 1 hr. Upon completion, the mixture was filtered and concentrated in vacuo to afford the title compound (150 mg, 95% yield, HCl salt) as faint yellow solid. LC-MS (ESI$^+$) m/z 372.8 (M+H)$^+$.

c) Synthesis of Tert-butyl 3-[2-[[(3S,8S)-3-[6-[[2-(2,6-dioxo-3-piperidyl)-1,3-dioxo-isoindolin-5-yl]amino] hexylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

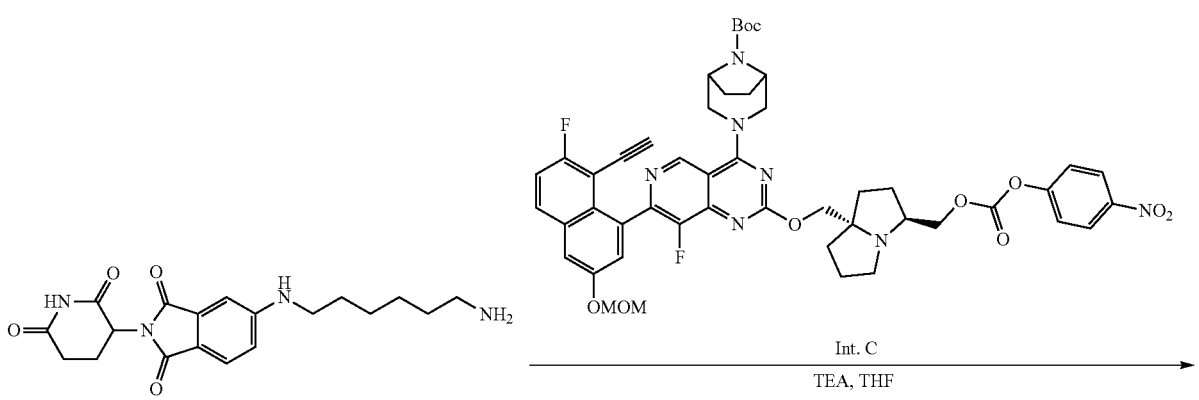

903 904

-continued

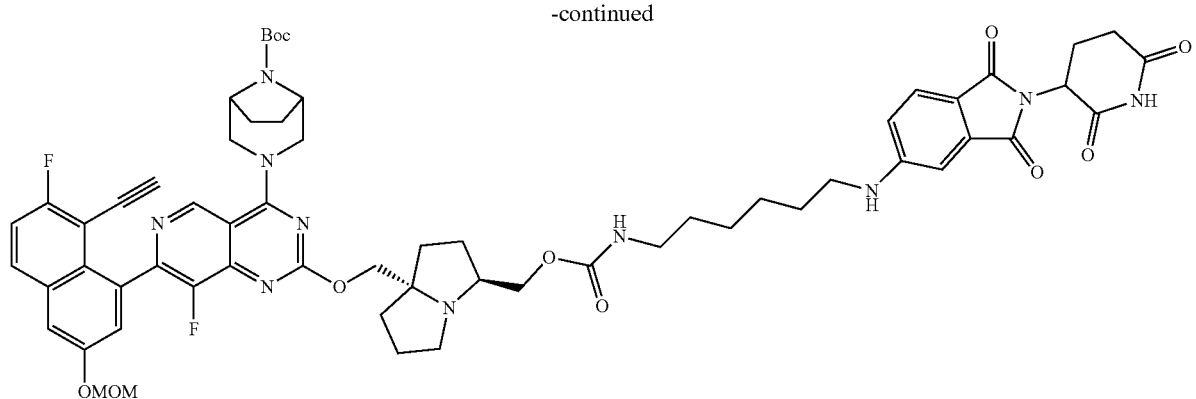

To a solution of Int. C (64.0 mg, 69.4 μmol), 5-(6-aminohexylamino)-2-(2,6-dioxo-3-piperidyl)isoindoline-1,3-dione (42.5 mg, 104 μmol, HCl salt) in THF (1 mL) was added TEA (21.0 mg, 208 μmol). The mixture was degassed and purged with N₂ for 3 times. The mixture was stirred at 25° C. for 2 hrs under N₂ atmosphere. Upon completion, the mixture was concentrated in vacuo. The residue was purified by prep-HPLC (column: Phenomenex luna C18 150*25 mm*10 μm; mobile phase: [water (FA)-ACN]; B %: 38%-68%, 15 min) to afford the title compound (27.0 mg, 33% yield) as yellow solid; LC-MS (ESI⁺) m/z 1155.6 (M+H)⁺.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[6-[[2-(2,6-dioxo-3-piperidyl)-1,3-dioxo-isoindolin-5-yl]amino]hexyl]carbamate (017)

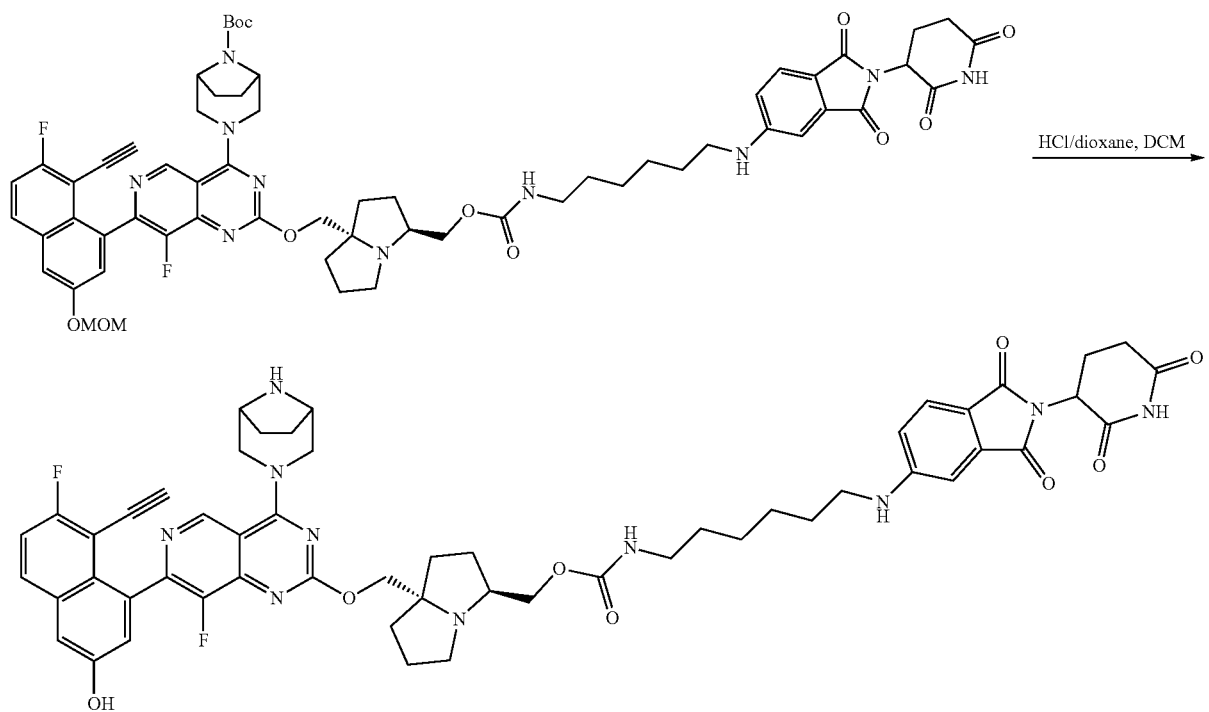

017

To a solution of tert-butyl 3-[2-[[(3S,8S)-3-[6-[[2-(2,6-dioxo-3-piperidyl)-1,3-dioxo-isoindolin-5-yl] amino]hexyl-carbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (27.0 mg, 23.3 μmol) in DCM (0.5 mL) was added HCl/dioxane (4 M, 1.00 mL). The mixture was stirred at 25° C. for 0.1 hr. Upon completion, the mixture was concentrated in vacuo. The residue was purified by prep-HPLC (column: Welch Xtimate C18 150*25 mm*5 μm; mobile phase: [water (FA)-ACN]; B %: 13%-43%, 9 min) to afford the title compound (6.48 mg, 27% yield) as yellow solid. $^1$H NMR (400 MHz, DMSO-d$_6$) δ 11.1 (s, 1H), 9.04 (s, 1H), 8.20 (s, 1H), 7.98 (dd, J=6.0, 9.2 Hz, 1H), 7.55 (d, J=8.4 Hz, 1H), 7.47 (t, J=9.2 Hz, 1H), 7.40 (d, J=2.4 Hz, 1H), 7.18 (d, J=2.4 Hz, 1H), 7.09 (t, J=5.2 Hz, 1H), 6.95-6.90 (m, 1H), 6.84 (d, J=6.8 Hz, 1H), 5.03 (dd, J=5.2, 13.2 Hz, 1H), 4.54-4.43 (m, 1H), 4.32 (d, J=12.4 Hz, 1H), 4.10 (dd, J=5.2, 11.2 Hz, 2H), 4.03 (d, J=10.8 Hz, 1H), 3.94 (s, 1H), 3.70-3.65 (m, 2H), 3.58-3.56 (m, 2H), 3.17-3.12 (m, 4H), 2.95-2.95 (m, 2H), 2.90-2.86 (m, 1H), 2.78-2.72 (m, 2H), 2.62-2.58 (m, 2H), 2.10-1.91 (m, 3H), 1.80-1.66 (m, 10H), 1.60-1.48 (m, 4H), 1.43-1.28 (m, 6H); LC-MS (ESI$^+$) m/z 1011.6 (M+H)$^+$.

Example 16. Synthesis of Compound 015 a) Synthesis of Tert-butyl N-[10-[[2-(2,6-dioxo-3-piperidyl)-1,3-dioxo-isoindolin-5-yl]amino]decyl] carbamate

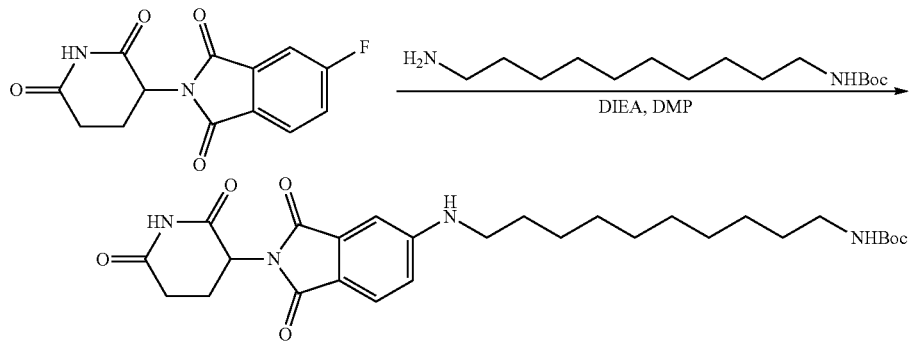

A solution of tert-butyl N-(10-aminodecyl)carbamate (3.00 g, 11.0 mmol, CAS #216931-31-4) and 2-(2,6-dioxo-3-piperidyl)-5-fluoroisoindoline-1,3-dione (2.77 g, 10.0 mmol, CAS #835616-61-0) and DIEA (2.59 g, 20.0 mmol) in NMP (30 mL) was stirred at 135° C. for 4 hrs. Upon completion, to the reaction mixture was added H$_2$O (50 mL) and extracted with EA (3×60 mL). The combined organic layers were washed with brine (50 mL), dried over anhydrous sodium sulfate, filtered and the filtrate was concentrated in vacuo. The crude product was purified by reversed-phase HPLC (0.1% FA condition) to afford the title compound (1.10 g, 21% yield) as green solid. $^1$H NMR (400 MHz, DMSO-d$_6$) δ 11.05 (s, 1H), 7.55 (d, J=8.4 Hz, 1H), 7.09 (t, J=5.2 Hz, 1H), 6.93 (d, J=2.0 Hz, 1H), 6.86-6.81 (m, 1H), 6.74 (t, J=5.6 Hz, 1H), 5.05-4.99 (m, 1H), 3.18-4.11 (m, 2H), 2.88 (d, J=6.0 Hz, 2H), 2.61-2.52 (m, 4H), 1.59-1.51 (m, 2H), 1.36 (s, 9H), 1.36-1.34 (m, 2H), 1.33-1.18 (m, 12H).

b) Synthesis of 5-(10-Aminodecylamino)-2-(2,6-dioxo-3-piperidyl)isoindoline-1,3-dione

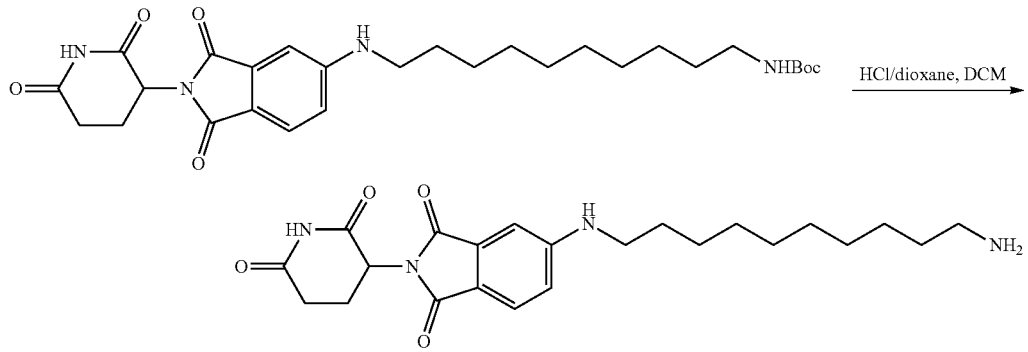

A solution of tert-butyl N-[10-[[2-(2,6-dioxo-3-piperidyl)-1,3-dioxo-isoindolin-5-yl]amino]decyl] carbamate (100 mg, 189 μmol) and HCl/dioxane (4 M, 1.00 mL) in DCM (3 mL) was stirred at 25° C. for 1 hr. Upon completion, the mixture was concentrated in vacuo to afford the title compound (80.0 mg, 98% yield, HCl salt) as green solid. LC-MS (ESI$^+$) m/z 429.2 (M+H)$^+$.

c) Synthesis of Tert-butyl 3-[2-[[(3S,8S)-3-[10-[[2-(2,6-dioxo-3-piperidyl)-1,3-dioxo-isoindolin-5-yl]amino] decylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

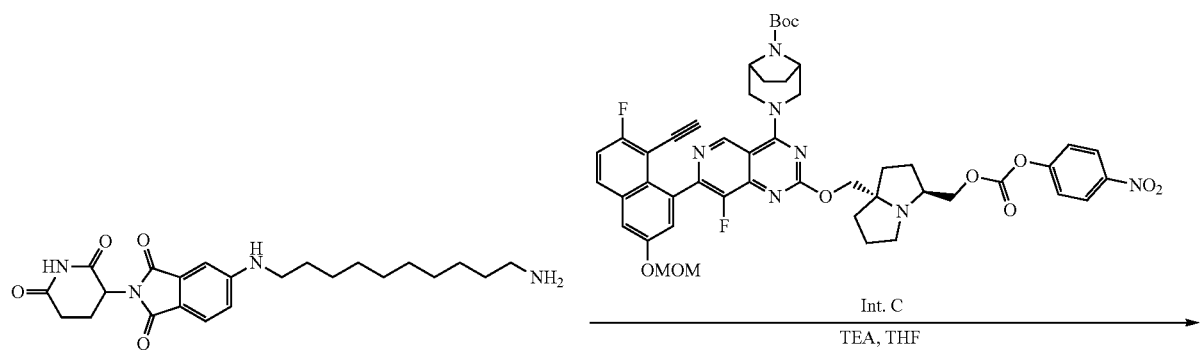

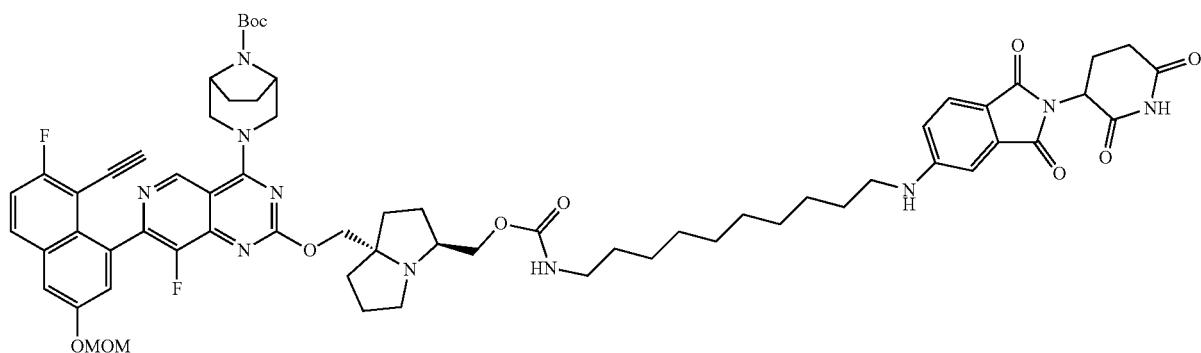

A solution of 5-(10-aminodecylamino)-2-(2,6-dioxo-3-piperidyl)isoindoline-1,3-dione (32.7 mg, 76.3 μmol, HCl salt) TEA (21.0 mg, 208 μmol) and Int. C (64.0 mg, 69.4 μmol) in THF (6 mL) was stirred at 25° C. for 16 hrs. Upon completion, the mixture was concentrated in vacuo. The mixture was purified by prep-HPLC (column: Phenomenex luna C18 150*25 mm*10 μm; mobile phase: [water (FA)-ACN]; B %: 38%-68%, 9 min) to afford the title compound (100 mg, 91% yield) as green solid. LC-MS (ESI$^+$) m/z 1212.5 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[10-[[2-(2,6-dioxo-3-piperidyl)-1,3-dioxo-isoindolin-5-yl]amino]decyl]carbamate (015)

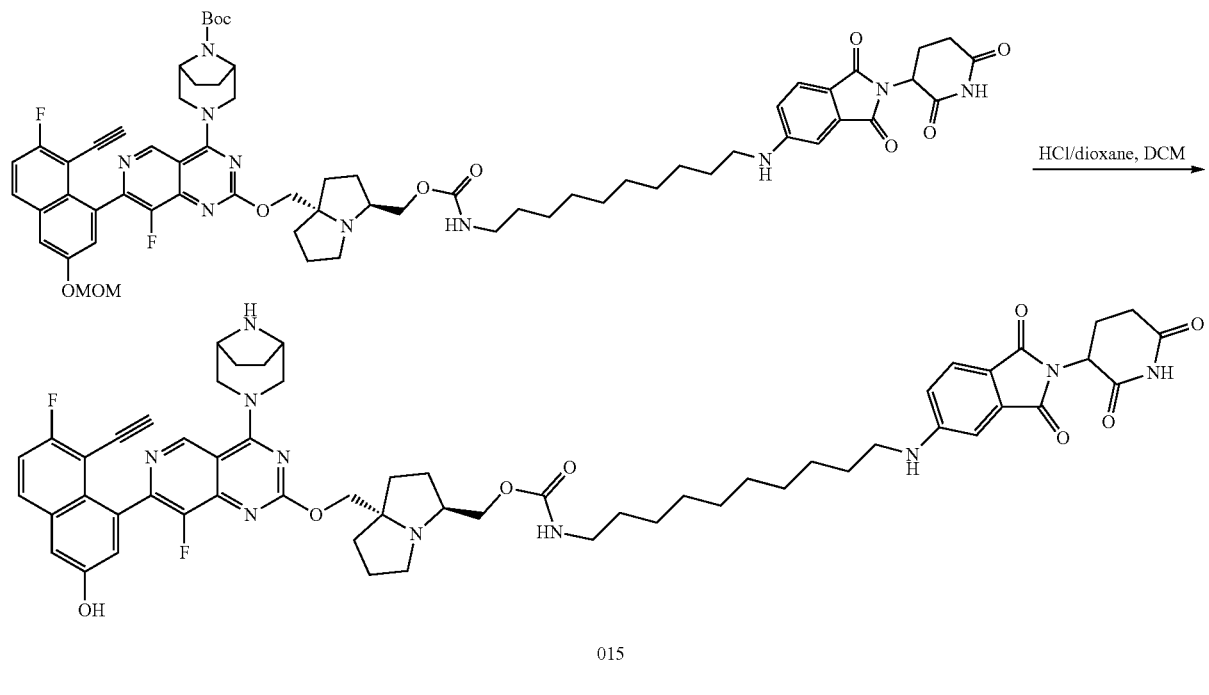

015

A solution of tert-butyl 3-[2-[[(3S,8S)-3-[10-[[2-(2,6-dioxo-3-piperidyl)-1,3-dioxo-isoindolin-5-yl] amino]decylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 24.7 µmol) and HCl/dioxane (4 M, 1.00 mL) in DCM (5 mL) was stirred at 25° C. for 1 hr. Upon completion, the mixture was concentrated in vacuo. The mixture was purified by prep-HPLC (column: Phenomenex luna C18 150*25 mm*10 µm; mobile phase: [water (FA)-ACN]; B %: 20%-50%, 9 min) to afford the title compound (6.50 mg, 24% yield, FA salt) as yellow solid. $^1$H NMR (400 MHz, DMSO-$d_6$) δ 11.06 (s, 1H), 9.03 (s, 1H), 8.02-7.92 (m, 1H), 7.54 (d, J=8.4 Hz, 1H), 7.46 (t, J=8.8 Hz, 1H), 7.39 (d, J=2.4 Hz, 1H), 7.21-7.12 (m, 2H), 7.11-7.06 (m, 1H), 6.95-6.89 (m, 1H), 6.85-6.79 (m, 1H), 5.02 (dd, J=5.2, 12.8 Hz, 1H), 4.53-4.44 (m, 1H), 4.34-4.21 (m, 1H), 4.17-4.06 (m, 3H), 4.05-4.00 (m, 1H), 3.93 (s, 1H), 3.67-3.55 (m, 6H), 3.13 (d, J=6.0 Hz, 2H), 2.97-2.91 (m, 2H), 2.89-2.82 (m, 1H), 2.78-2.68 (m, 2H), 2.59-2.57 (m, 1H), 2.06-1.96 (m, 2H), 1.77-1.64 (m, 10H), 1.60-1.47 (m, 4H), 1.38-1.22 (m, 14H); LC-MS (ESI$^+$) m/z 1067.8 (M+H)$^+$.

Example 17. Synthesis of Compound 002 a) Synthesis of Tert-butyl N-[2-[1-(2,6-dioxo-3-piperidyl)-3-methyl-2-oxo-benzimidazol-5-yl] ethyl] carbamate

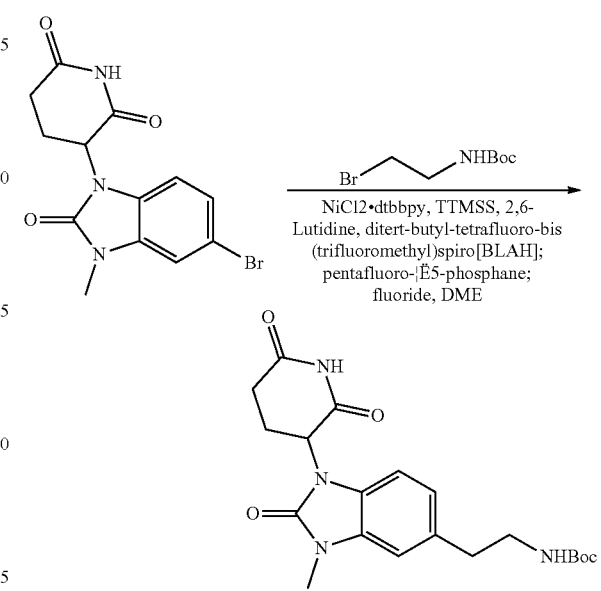

911

To an 40 mL vial equipped with a stir bar was added 3-(5-bromo-3-methyl-2-oxo-benzimidazol-1-yl)piperidine-2,6-dione (500 mg, 1.48 mmol), tert-butyl N-(2-bromoethyl)carbamate (430 mg, 1.92 mmol, CAS #39684-80-5), ditert-butyl-tetrafluoro-bis(trifluoromethyl)spiro[BLAH]; pentafluoro-λ$^5$-phosphane; fluoride (16.5 mg, 14.7 μmol), NiCl$_2$·dtbbpy (8.83 mg, 22.1 μmol), TTMSS (367 mg, 1.48 mmol) and 2,6-lutidine (316 mg, 2.96 mmol) in DME (25 mL). The vial was sealed and placed under nitrogen was added. The reaction mixture was stirred and irradiated with a 10 W blue LED lamp (3 cm away), with cooling water to keep the reaction temperature at 25° C. for 14 hrs. Upon completion, the reaction mixture was filtered and concentrated in vacuo to provide a residue. The residue was purified by prep-HPLC (column: YMC Triart C18 250*50 mm*7 ditert-butyl-tetrafluoro-bis(trifluoromethyl)spiro[BLAH]; pentafluoro-λ$^5$-phosphane; fluoride m; mobile phase: [water (FA)-ACN]; B %: 18%-48%, 20 min) to afford the title compound (385 mg, 64% yield) as white solid. $^1$H NMR (400 MHz, CDCl$_3$) δ 8.10 (s, 1H), 6.98-6.84 (m, 2H), 6.74 (d, J=8.0 Hz, 1H), 5.22 (dd, J=5.2, 12.4 Hz, 1H), 4.57 (s, 1H), 3.44 (s, 3H), 3.38 (d, J=6.8 Hz, 2H), 3.02-2.92 (m, 1H), 2.90-2.66 (m, 4H), 2.30-2.20 (m, 1H), 1.45 (s, 9H); LC-MS (ESI$^+$) m/z 346.9 (M+H−56)$^+$.

b) Synthesis of 3-[5-(2-Aminoethyl)-3-methyl-2-oxo-benzimidazol-1-yl]piperidine-2,6-dione

912

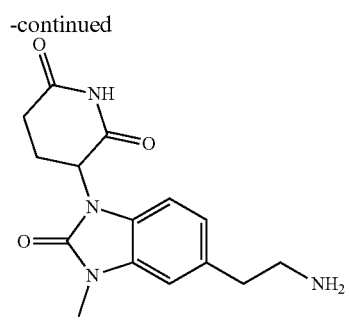

To a solution of tert-butyl N-[2-[1-(2,6-dioxo-3-piperidyl)-3-methyl-2-oxo-benzimidazol-5-yl]ethyl]carbamate (200 mg, 496 μmol) in DCM (1 mL) was added HCl/dioxane (4 M, 1.00 mL). The mixture was stirred at 25° C. for 0.5 hr. Upon completion, the reaction mixture was concentrated in vacuo to afford the title compound (168 mg, 99% yield, HCl salt) as white solid. LC-MS (ESI$^+$) m/z 302.9 (M+H)$^+$

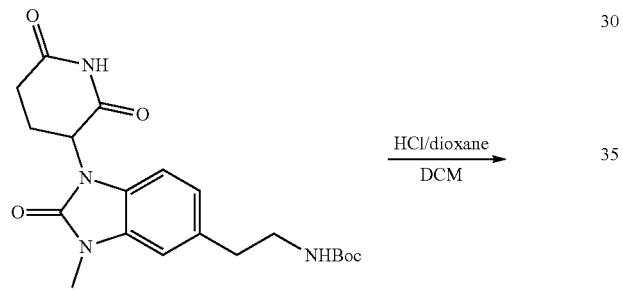

c) Synthesis of Tert-butyl 3-[2-[[(3S,8S)-3-[2-[1-(2,6-dioxo-3-piperidyl)-3-methyl-2-oxo-benzimidazol-5-yl] ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

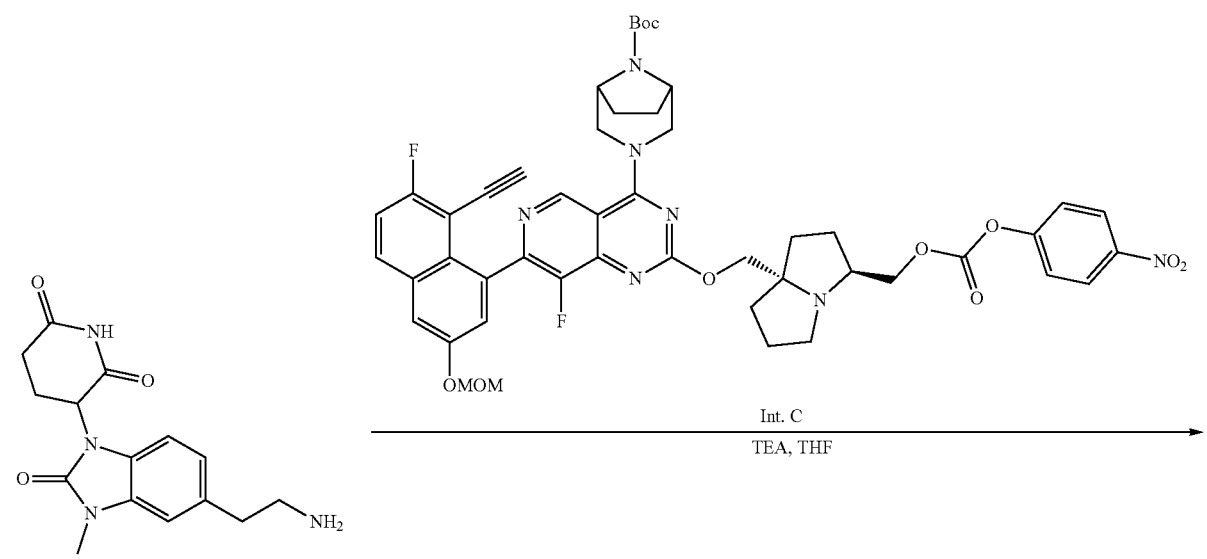

913 914

-continued

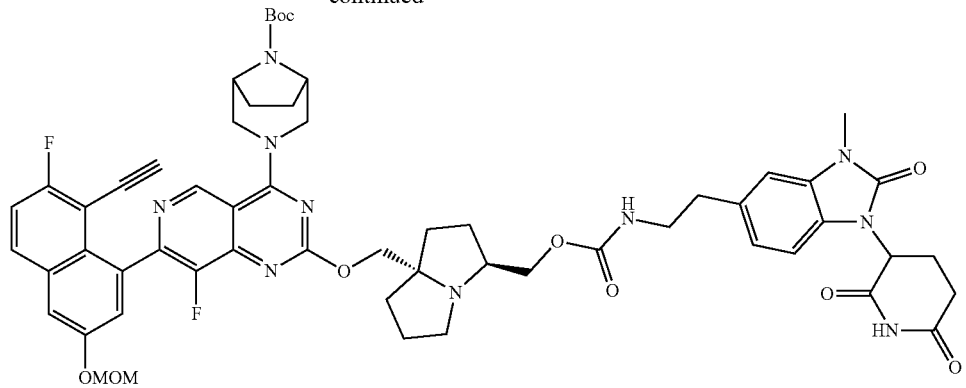

To a solution of 3-[5-(2-aminoethyl)-3-methyl-2-oxo-benzimidazol-1-yl]piperidine-2,6-dione (33.0 mg, 97.6 µmol, HCl salt) in THF (2 mL) was added TEA (19.7 mg, 195 µmol) and Int. C (60.0 mg, 65.0 µmol). The mixture was stirred at 25° C. for 12 hrs. Upon completion, the reaction mixture was concentrated in vacuo to provide a residue. The residue was purified by prep-HPLC (column: Welch Ultimate C18 150*25 mm*5 µm; mobile phase: [water (FA)-ACN]; B %: 30%-50%, 10 min) to afford the title compound (40.0 mg, 56% yield) as yellow solid. $^1$H NMR (400 MHz, DMSO-d$_6$) δ 11.17-11.01 (m, 1H), 9.19-8.98 (m, 1H), 8.10 (dd, J=6.0, 9.2 Hz, 1H), 7.74 (d, J=2.4 Hz, 1H), 7.57-7.52 (m, 1H), 7.46 (s, 1H), 7.38 (d, J=2.4 Hz, 1H), 7.03-6.92 (m, 2H), 6.85 (dd, J=2.4, 6.4 Hz, 1H), 5.37 (s, 2H), 4.62-4.49 (m, 1H), 4.46-4.35 (m, 1H), 4.34-4.28 (m, 2H), 4.20-4.04 (m, 4H), 4.00-3.96 (m, 1H), 3.70-3.62 (m, 2H), 3.58 (s, 3H), 3.44 (s, 3H), 3.22-3.19 (m, 2H), 3.07-3.01 (m, 2H), 2.98-2.77 (m, 2H), 2.76-2.66 (m, 3H), 2.60-2.58 (m, 1H), 2.07-1.96 (m, 2H), 1.89-1.81 (m, 2H), 1.78-1.50 (m, 10H), 1.46 (s, 9H); LC-MS (ESI$^+$) m/z 1085.6 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[2-[1-(2,6-dioxo-3-piperidyl)-3-methyl-2-oxo-benzimidazol-5-yl]ethyl]carbamate (002)

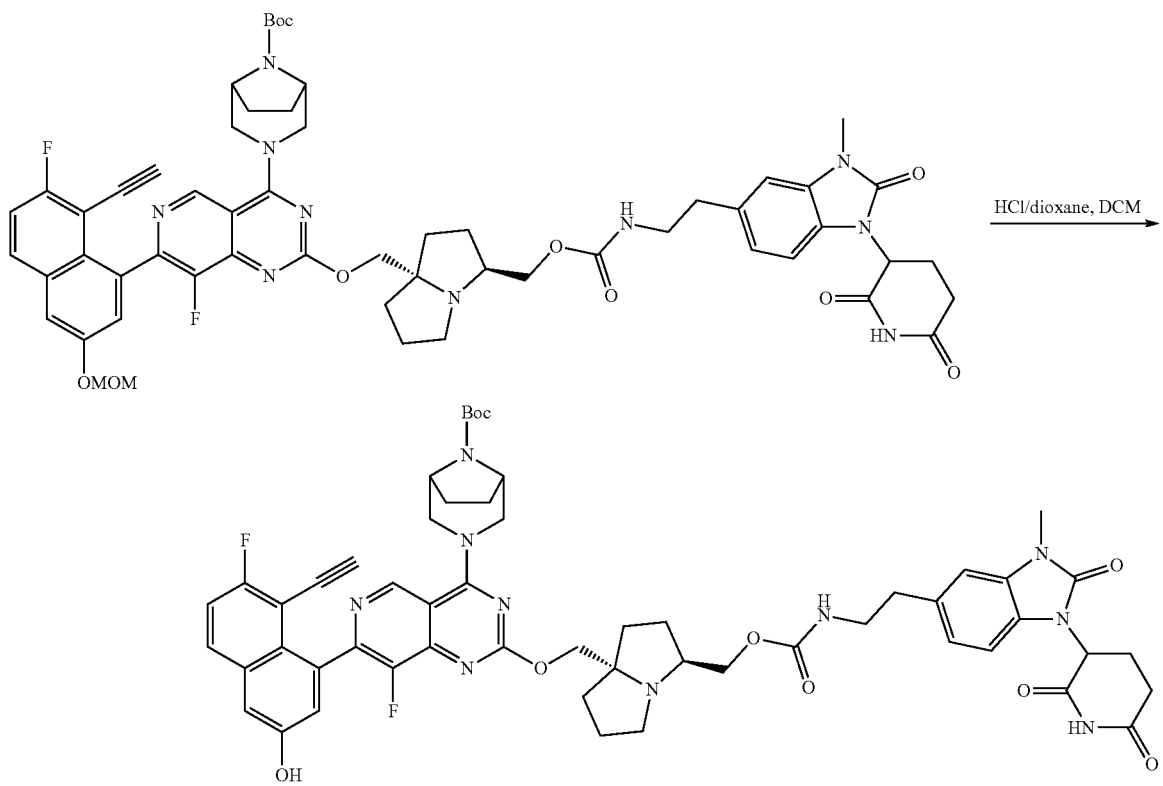

002

To a solution of tert-butyl 3-[2-[[(3S,8S)-3-[2-[1-(2,6-dioxo-3-piperidyl)-3-methyl-2-oxo-benzimidazol-5-yl]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (40.0 mg, 36.8 μmol) in DCM (1 mL) was added HCl/dioxane (4 M, 400 uL). The reaction mixture was stirred at 25° C. for 0.5 hr. Upon completion, the reaction mixture was concentrated in vacuo to provide a residue. The residue was purified by prep-HPLC (column: Waters xbridge 150*25 mm 10 μm; mobile phase: [water (FA)-ACN]; B %: 6%-36%, 9 min) to afford the title compound (8.27 mg, 22% yield, FA salt) as yellow solid. $^1$H NMR (400 MHz, DMSO-$d_6$) δ 11.28-10.92 (m, 1H), 10.38-9.96 (m, 1H), 9.06 (s, 1H), 7.98 (dd, J=6.0, 9.2 Hz, 1H), 7.52-7.43 (m, 2H), 7.39 (d, J=2.4 Hz, 1H), 7.17 (d, J=2.4 Hz, 1H), 7.02-6.93 (m, 2H), 6.89-6.82 (m, 1H), 5.46-5.26 (m, 1H), 4.53 (d, J=13.2 Hz, 1H), 4.37 (d, J=11.6 Hz, 1H), 4.23-4.02 (m, 4H), 3.93 (s, 1H), 3.77 (s, 2H), 3.72-3.64 (m, 2H), 3.58 (s, 3H), 3.22 (d, J=6.8 Hz, 2H), 3.07-3.01 (m, 2H), 2.94-2.83 (m, 2H), 2.79-2.66 (m, 3H), 2.61-2.56 (m, 1H), 2.07-1.95 (m, 2H), 1.81-1.51 (m, 12H); LC-MS (ESI$^+$) m/z 941.0 (M+H)$^+$.

Example 18. Synthesis of Compound 001 a) Synthesis of Tert-butyl N-[3-[1-(2,6-dioxo-3-piperidyl)-3-methyl-2-oxo-benzimidazol-5-yl]propyl]carbamate

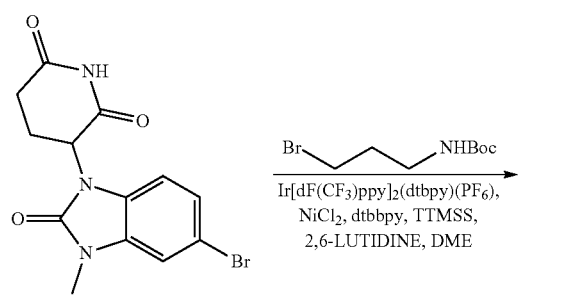

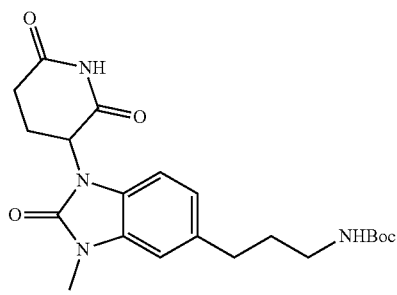

To an 250 mL vial equipped with a stir bar was added 3-(5-bromo-3-methyl-2-oxo-benzimidazol-1-yl) piperidine-2,6-dione (1.00 g, 2.96 mmol), tert-butyl N-(3-bromopropyl)carbamate (704 mg, 2.96 mmol, CAS #83948-53-2), Ir[dF(CF$_3$)ppy]$_2$(dtbpy)(PF$_6$) (66.3 mg, 59.1 μmol), NiCl$_2$·dtbbpy (35.3 mg, 88.7 μmol), TTMSS (735 mg, 2.96 mmol), 2,6-lutidine (633 mg, 5.91 mmol) in DME (100 mL). The vial was sealed and placed under nitrogen. The reaction was stirred and irradiated with a 10 W blue LED lamp (3 cm away), with cooling water to keep the reaction temperature at 25° C. for 14 hrs. Upon completion, the mixture was concentrated in vacuo. The mixture was purified by prep-HPLC (column: Phenomenex luna C18 150*25 mm*10 μm; mobile phase: [water (FA)-ACN]; B %: 25%-55%, 10 min) to afford the title compound (400 mg, 32% yield) as yellow solid. LC-MS (ESI$^+$) m/z 361.0 (M−56)$^+$.

b) Synthesis of 3-[5-(3-Aminopropyl)-3-methyl-2-oxo-benzimidazol-1-yl]piperidine-2,6-dione

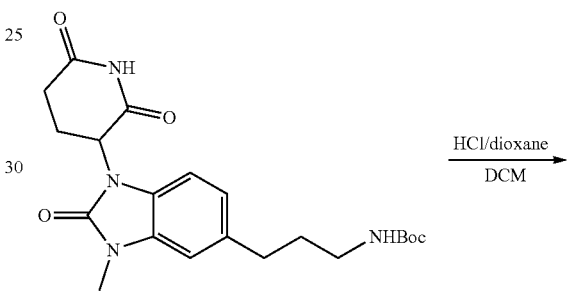

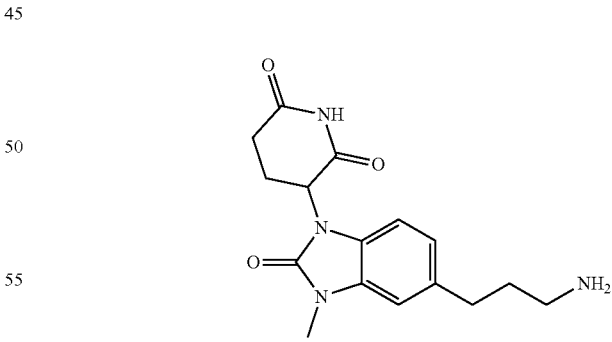

To a solution of tert-butyl N-[3-[1-(2,6-dioxo-3-piperidyl)-3-methyl-2-oxo-benzimidazol-5-yl] propyl]carbamate (50.0 mg, 120 μmol) in DCM (5 mL) was added HCl/dioxane (4 M, 1.00 mL) and the mixture was stirred at 25° C. for 1 hr. Upon completion, the mixture was concentrated in vacuo to afford the title compound (35.0 mg, 82% yield, HCl salt) as yellow solid. LC-MS (ESI$^+$) m/z 317.0 (M+H)$^+$.

c) Synthesis of Tert-butyl 3-[2-[[(3S,8S)-3-[3-[1-(2,6-dioxo-3-piperidyl)-3-methyl-2-oxo-benzimidazol-5-yl] propylcarbamoyloxymethyl]-1,2,3,5,6,7-hexa-hydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

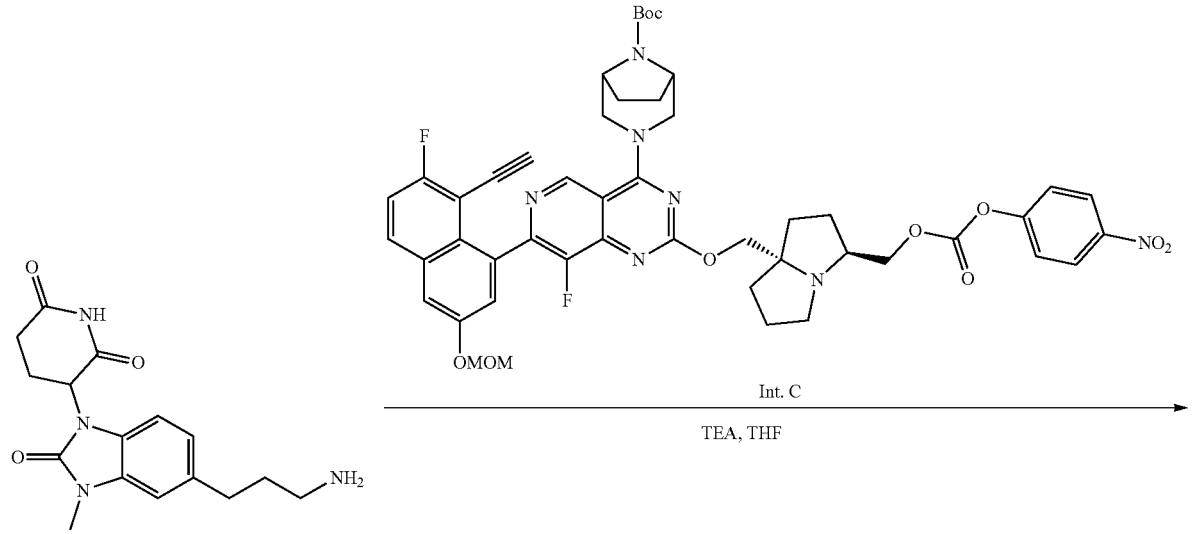

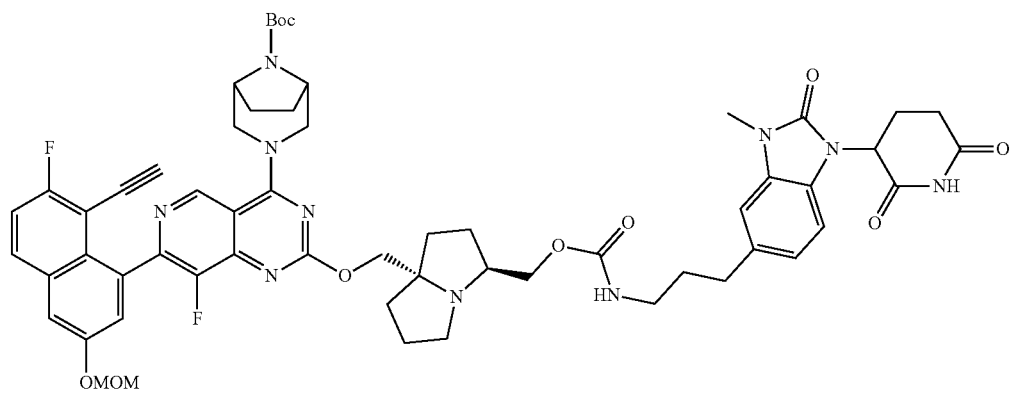

To a solution of 3-[5-(3-aminopropyl)-3-methyl-2-oxo-benzimidazol-1-yl]piperidine-2,6-dione (25.2 mg, 71.6 μmol, HCl salt) and TEA (19.7 mg, 195 μmol) in THF (8 mL) was added Int. C (60.0 mg, 65.0 μmol). The mixture was stirred at 25° C. for 16 hrs. Upon completion, the mixture was concentrated in vacuo and purified by prep-HPLC (column: Phenomenex luna C18 150*25 mm*10 μm; mobile phase: [water (FA)-ACN]; B %: 28%-58%, 9 min) to afford the title compound (50.0 mg, 54% yield) as yellow solid. LC-MS (ESI$^+$) m/z 1099.9 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[3-[1-(2,6-dioxo-3-piperidyl)-3-methyl-2-oxo-benzimidazol-5-yl]propyl]carbamate (001)

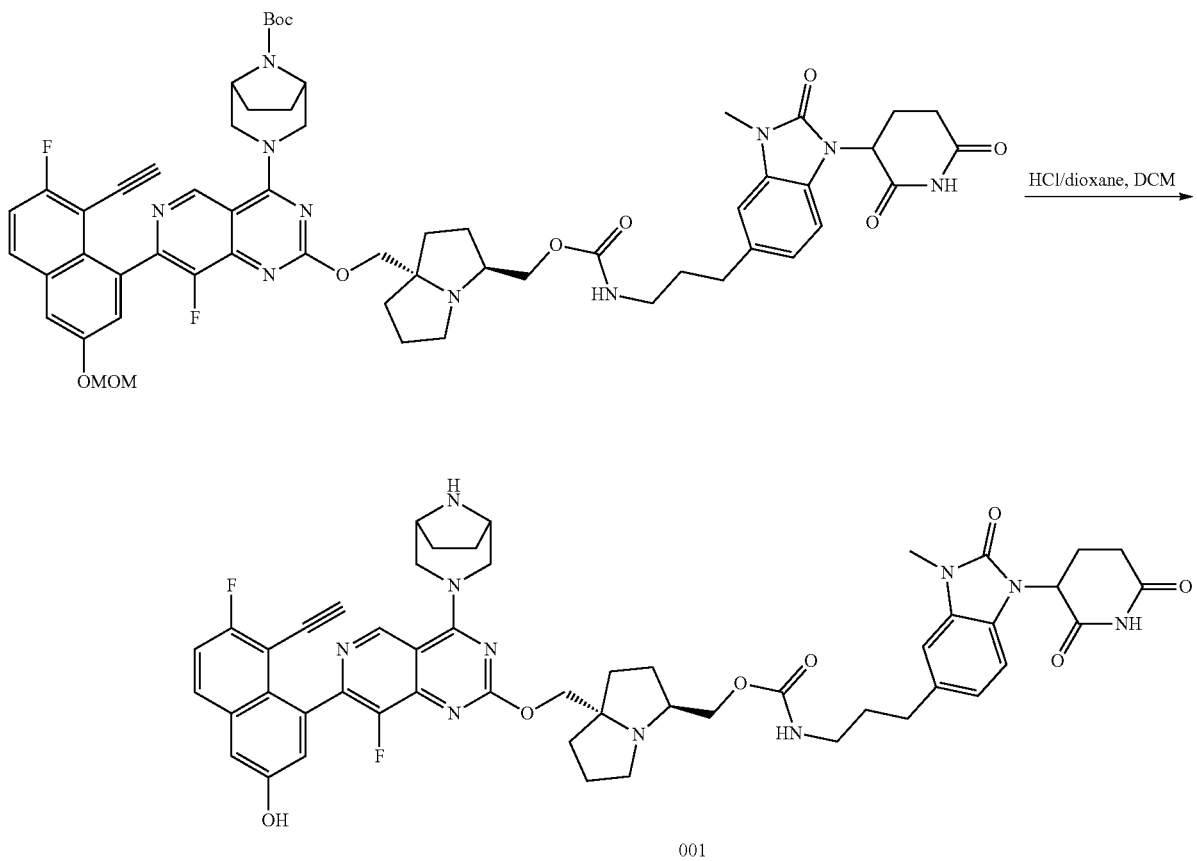

To a solution of tert-butyl 3-[2-[[(3S,8S)-3-[3-[1-(2,6-dioxo-3-piperidyl)-3-methyl-2-oxo-benzimidazol-5-yl]propylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (50.0 mg, 45.5 µmol) in DCM (5 mL) was added HCl/dioxane (4 M, 1.00 mL) and the mixture was stirred at 25° C. for 1 hr. Upon completion, the mixture was concentrated in vacuo. The mixture was purified by prep-HPLC (column: Welch Ultimate C18 150*25 mm*5 µm; mobile phase: [water (TFA)-ACN]; B %: 18%-38%, 10 min) to afford the title compound (10.0 mg, 22% yield, TFA salt) as yellow solid. $^1$H NMR (400 MHz, DMSO-$d_6$) δ 11.08 (s, 1H), 10.44 (d, J=4.4 Hz, 1H), 10.28-10.18 (m, 1H), 9.40 (d, J=9.6 Hz, 1H), 9.16 (s, 1H), 9.14-9.09 (m, 1H), 8.00 (dd, J=6.0, 9.2 Hz, 1H), 7.48 (t, J=9.2 Hz, 1H), 7.42 (d, J=2.4 Hz, 1H), 7.34-7.26 (m, 1H), 7.18 (d, J=2.4 Hz, 1H), 7.04-6.97 (m, 2H), 6.86 (d, J=7.6 Hz, 1H), 5.33 (dd, J=5.2, 12.8 Hz, 1H), 4.74-4.67 (m, 1H), 4.64-4.52 (m, 3H), 4.38-4.29 (m, 2H), 4.23 (s, 2H), 3.89 (d, J=4.4 Hz, 2H), 3.85 (d, J=5.6 Hz, 1H), 3.31 (s, 3H), 3.07-2.99 (m, 2H), 2.95-2.85 (m, 1H), 2.76-2.57 (m, 7H), 2.31 (d, J=1.6, 8.8 Hz, 1H), 2.18-1.89 (m, 14H), 1.78-1.69 (m, 2H); LC-MS (ESI$^+$) m/z 955.3 (M+H)$^+$.

Example 19. Synthesis of Compound 006 a) Synthesis of Tert-butyl (4-(1-(2,6-dioxopiperidin-3-yl)-3-methyl-2-oxo-2,3-dihydro-1H-benzo[d]imidazole-5-yl)butyl)carbamate

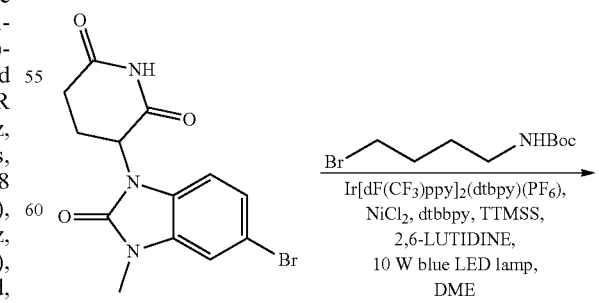

921

-continued

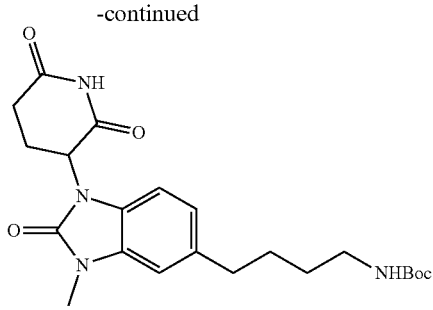

To a 15 mL vial equipped with a stirred bar was added 3-(5-bromo-3-methyl-2-oxo-benzimidazol-1-yl)piperidine-2,6-dione (450 mg, 1.33 mmol), tert-butylN-(4-bromobutyl) carbamate (436 mg, 1.73 mmol, CAS #164365-88-2), Ir[dF (CF$_3$)ppy]$_2$(dtbpy) (PF$_6$) (29.8 mg, 26.6 μmol), NiCl$_2$·dtbbpy (15.8 mg, 39.9 μmol), TTMSS (330 mg, 1.33 mmol), 2,6-Lutidine (285 mg, 2.66 mmol) in DME (5 mL). The vial was sealed and placed under N$_2$. The reaction was stirred and irradiated with a 10 W blue LED lamp (3 cm away), with cooling water to keep the reaction temperature at 25° C. for 14 hrs. Upon completion, the reaction mixture was filtered and concentrated in vacuo to give a residue. The residue was purified by prep-HPLC (column: Phenomenex luna C18 250*50 mm*10 μm; mobile phase: [water (FA)-ACN]; B %: 35%-65%, 30 min) to afford the title compound (400 mg, 69% yield) as white solid. LC-MS (ESI$^+$) m/z 374.9 (M−56+H)$^+$.

b) Synthesis of 3-(5-(4-Aminobutyl)-3-methyl-2-oxo-2,3-dihydro-1H-benzo[d]imidazol-1-yl)piperidine-2,6-dione

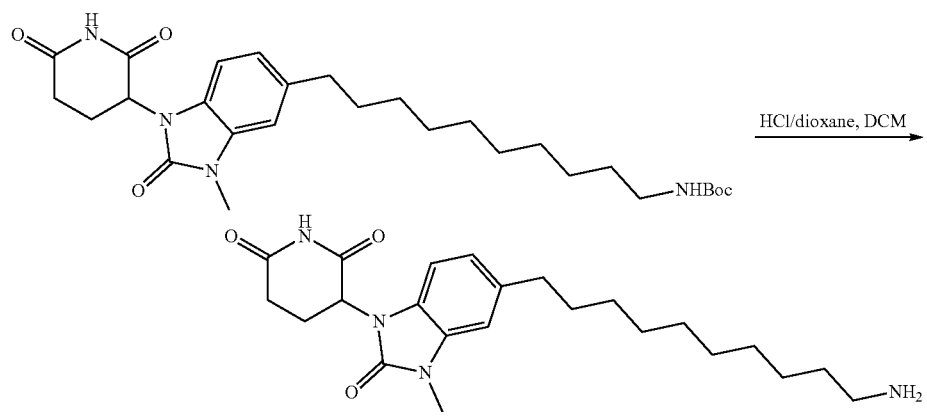

To a solution of tert-butyl N-[4-[1-(2,6-dioxo-3-piperidyl)-3-methyl-2-oxo-benzimidazol-5-yl]butyl] carbamate (200 mg, 464 μmol) in DCM (5 mL) was added HCl/dioxane (4.00 M, 1.00 mL). The mixture was stirred at 25° C. for 3 hrs. Upon completion, the reaction mixture concentrated in vacuo to afford the title compound (140 mg, 91% yield, HCl salt) as white solid. LC-MS (ESI$^+$) m/z 330.9 (M+H)$^+$.

c) Synthesis of (1R,5S)-tert-butyl 3-(2-(((3R,7aR)-3-((((4-(1-(2,6-dioxopiperidin-3-yl)-3-methyl-2-oxo-2,3-dihydro-1H-benzo[d]imidazol-5-yl)butyl)carbamoyl)oxy)methyl)hexahydro-1H-pyrrolizin-7a-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

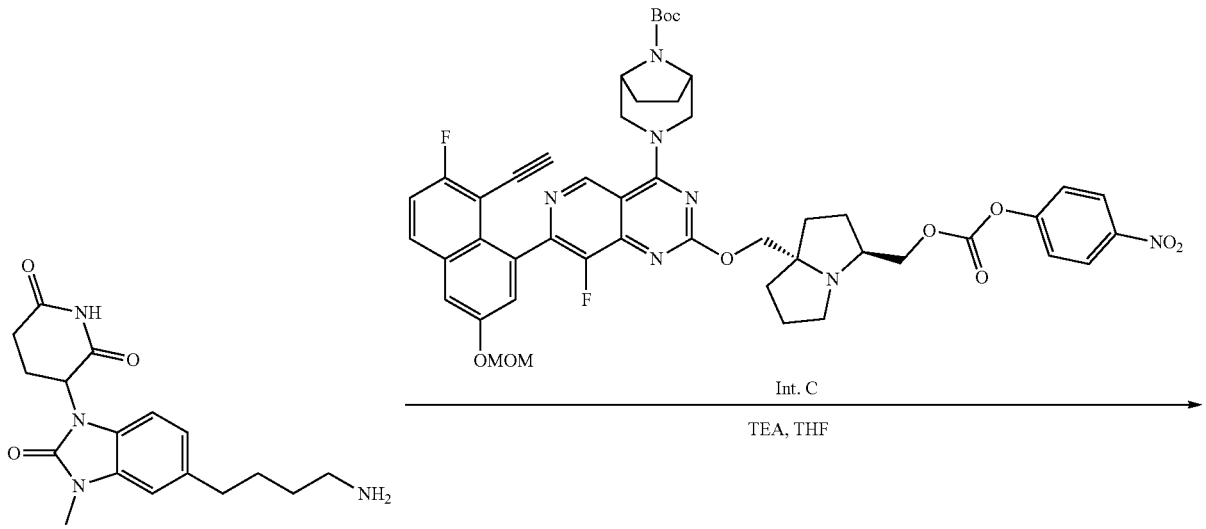

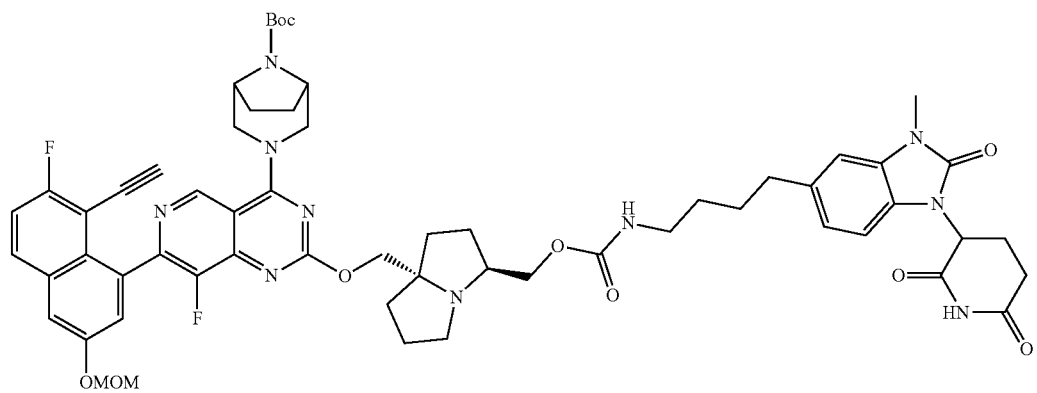

To a solution of 3-[5-(4-aminobutyl)-3-methyl-2-oxo-benzimidazol-1-yl]piperidine-2,6-dione (43.0 mg, 117 μmol, HCl salt) in THF (5 mL) was added TEA (32.9 mg, 325 μmol) and Int. C (60.0 mg, 65.0 μmol). The mixture was stirred at 25° C. for 2 hrs. Upon completion, the reaction mixture was concentrated in vacuo to afford the title compound (30.0 mg, 41% yield) as white solid. LC-MS (ESI$^+$) m/z 1114.4 (M+H)$^+$.

d) Synthesis of ((3S,7aS)-7a-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl (4-(1-(2,6-dioxopiperidin-3-yl)-3-methyl-2-oxo-2,3-dihydro-1H-benzo[d]imidazol-5-yl) butyl)carbamate (006)

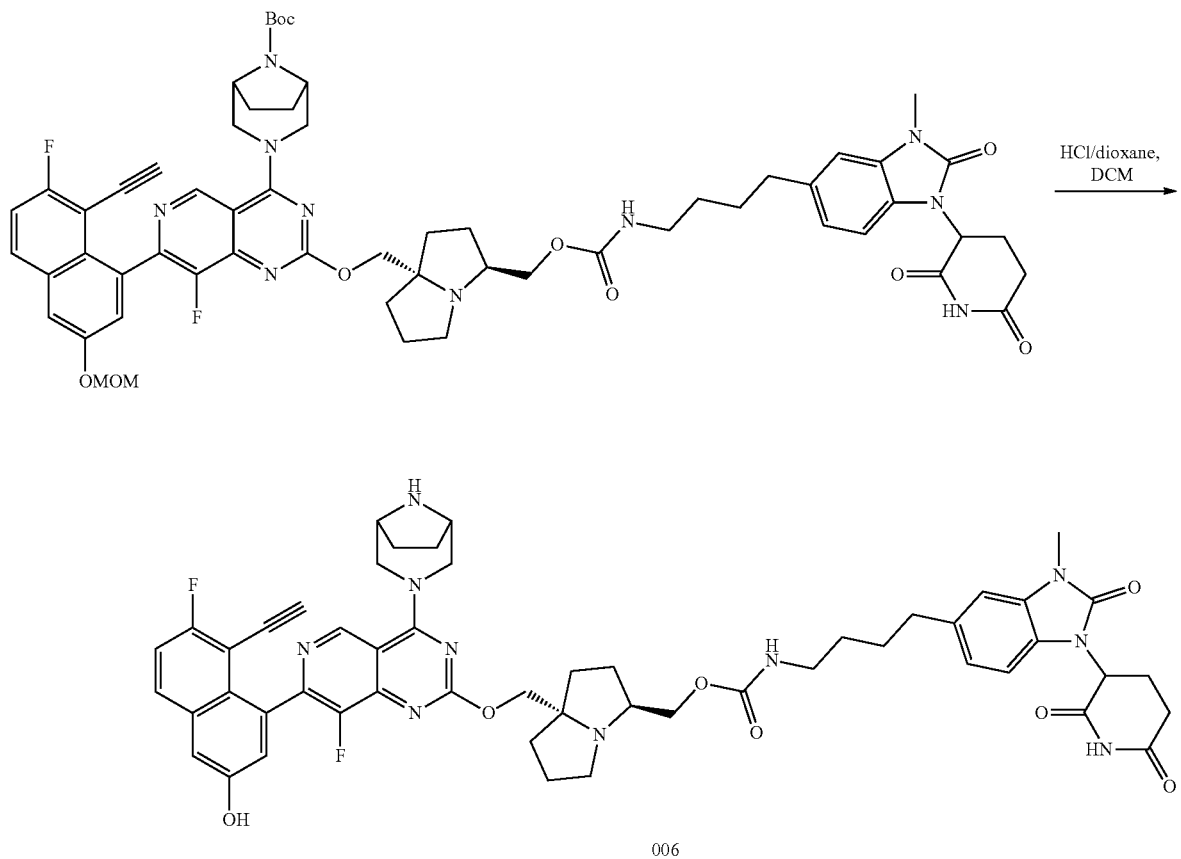

To a solution of tert-butyl 3-[2-[[(3S,8S)-3-[4-[1-(2,6-dioxo-3-piperidyl)-3-methyl-2-oxo-benzimidazol-5-yl]butylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 26.9 µmol) in DCM (3 mL) was added HCl/dioxane (4.00 M, 1.00 mL). The mixture was stirred at 25° C. for 2 hrs. Upon completion, the reaction mixture was concentrated in vacuo to give a residue and the residue was purified by prep-HPLC (column: Phenomenex luna C18 150*25 mm*10 µm; mobile phase: [water (FA)-ACN]; B %: 6%-36%, 10 min) to afford the title compound (10.8 mg, 41% yield) as yellow solid. $^1$H NMR (400 MHz, DMSO-$d_6$) δ 11.19-10.98 (m, 1H), 9.03 (s, 1H), 7.97 (dd, J=6.0, 9.2 Hz, 1H), 7.46 (t, J=9.2 Hz, 1H), 7.39 (d, J=2.4 Hz, 1H), 7.23-7.14 (m, 2H), 7.03-6.95 (m, 2H), 6.85 (d, J=8.4 Hz, 1H), 5.37-5.27 (m, 1H), 4.47 (d, J=10.8 Hz, 1H), 4.31 (d, J=12.4 Hz, 1H), 4.13-4.08 (m, 2H), 4.03-3.99 (m, 1H), 3.93 (s, 1H), 3.66-3.57 (m, 6H), 3.31 (s, 3H), 2.99 (d, J=6.4 Hz, 2H), 2.94-2.82 (m, 2H), 2.75-2.69 (m, 2H), 2.62-2.58 (m, 2H), 2.00 (dd, J=4.8, 12.0 Hz, 2H), 1.77-1.64 (m, 10H), 1.59-1.51 (m, 3H), 1.49-1.37 (m, 3H); LC-MS (ESI$^+$) m/z 969.4 (M+H)$^+$.

Example 20. Synthesis of Compound 005 a) Synthesis of Tert-butyl N-[5-[1-(2,6-dioxo-3-piperidyl)-3-methyl-2-oxo-benzimidazol-5-yl]pentyl]carbamate

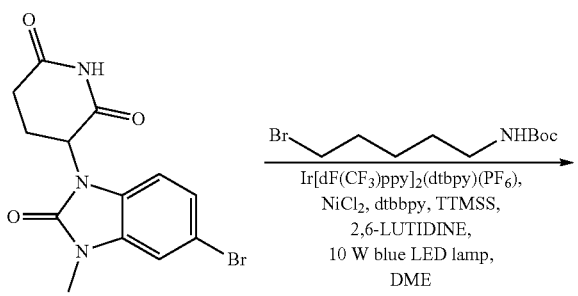

927

-continued

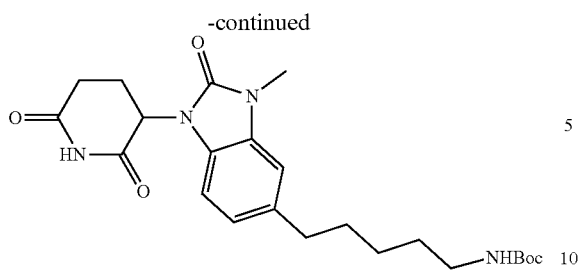

928

-continued

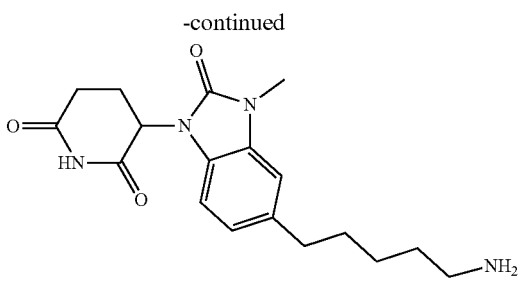

To a 15 mL vial equipped with a stir bar was added 3-(5-bromo-3-methyl-2-oxo-benzimidazol-1-yl)piperidine-2,6-dione (450 mg, 1.33 mmol), tert-butyl N-(5-bromopentyl)carbamate (461 mg, 1.73 mmol, CAS #83948-54-3), Ir[dF(CF$_3$)ppy]$_2$(dtbpy)(PF$_6$) (30.0 mg, 26.6 μmol), NiCl$_2$·dtbbpy (16.0 mg, 39.9 μmol), TTMSS (331 mg, 1.33 mmol), 2,6-Lutidine (285 mg, 2.66 mmol) in DME (5 mL). The vial was sealed and placed under N$_2$. The reaction was stirred and irradiated with a 10 W blue LED lamp (3 cm away), with cooling water to keep the reaction temperature at 25° C. for 14 hrs. Upon completion, the mixture was concentrated in vacuo to give a residue. The residue was purified by prep-HPLC (column: Phenomenex luna C18 250*50 mm*10 μm; mobile phase: [water (FA)-ACN]; B %: 35%-65%, 30 min) to afford the title compound (500 mg, 84% yield) as white solid. LC-MS (ESI$^+$) m/z 344.9 (M+H)$^+$.

b) Synthesis of 3-[5-(5-Aminopentyl)-3-methyl-2-oxo-benzimidazol-1-yl]piperidine-2,6-dione

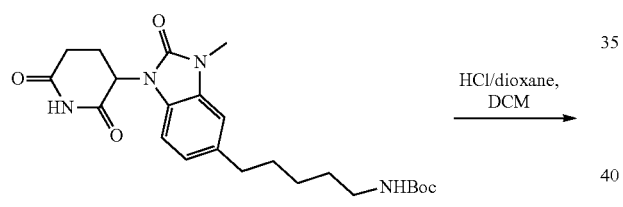

HCl/dioxane, DCM

To a solution of tert-butyl N-[5-[1-(2,6-dioxo-3-piperidyl)-3-methyl-2-oxo-benzimidazol-5-yl]penty-l]carbamate (200 mg, 450 μmol) in DCM (5 mL) was added HCl/dioxane (4 M, 1.5 mL). The mixture was stirred at 25° C. for 6 hrs. Upon completion, the mixture was concentrated in vacuo to afford the title compound (148 mg, 84% yield, HCl salt) as white solid. $^1$H NMR (400 MHz, DMSO-d$_6$) δ 11.08 (s, 1H), 8.00 (s, 2H), 7.04 (s, 1H), 7.02 (d, J=8.0 Hz, 1H), 6.87-6.85 (m, 1H), 5.37-5.32 (m, 1H), 3.61-3.57 (m, 1H), 3.32 (s, 3H), 2.95-2.85 (m, 1H), 2.77-2.70 (m, 2H), 2.64-2.59 (m, 2H), 2.03-1.96 (m, 1H), 1.77-1.73 (m, 1H), 1.64-1.55 (m, 4H), 1.38-1.29 (m, 2H); LC-MS (ESI+) m/z 344.9 (M+H)$^+$.

c) Synthesis of Tert-butyl 3-[2-[[(3S,8S)-3-[5-[1-(2,6-dioxo-3-piperidyl)-3-methyl-2-oxo-benzimidazol-5-yl]pentylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

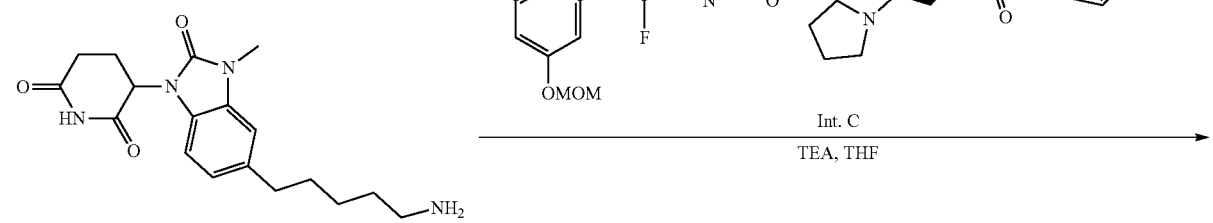

Int. C
TEA, THF

929

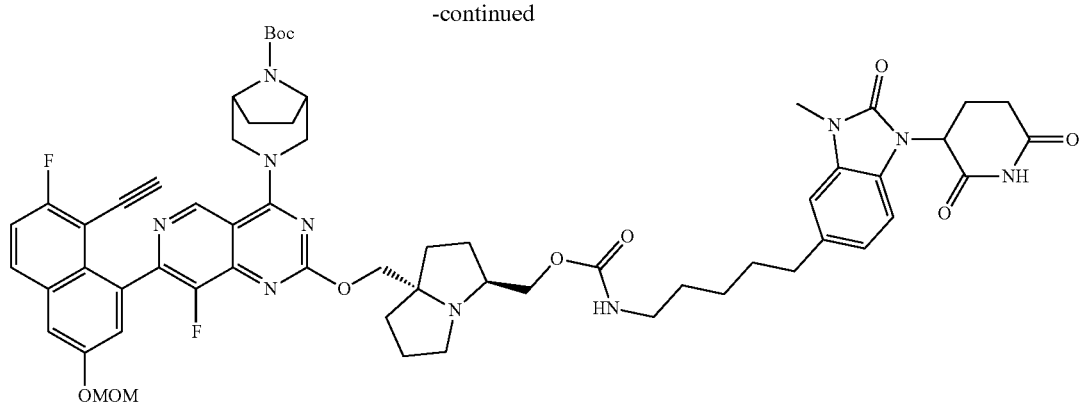

-continued

A solution of 3-[5-(5-aminopentyl)-3-methyl-2-oxo-benzimidazol-1-yl]piperidine-2,6-dione (67.8 mg, 178 μmol, HCl salt) in THF (5 mL) was adjusted to pH hold on 8 with TEA. Then a solution of Int. C (82.0 mg, 88.9 μmol) in THF (3 mL) was added to the mixture, and then the mixture was stirred at 25° C. for 3 hrs under $N_2$ atmosphere. Upon completion, the mixture was concentrated in vacuo to give a residue. The residue was purified by prep-HPLC (column: Waters Xbridge C18 150*50 mm*10 μm; mobile phase: [water ($NH_4HCO_3$)-ACN]; B %: 48%-78%, 9 min) to afford the title compound (28.0 mg, 27% yield) as white solid. LC-MS (ESI$^+$) m/z 564.4 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-napht-hyl)-8-fluoro-pyrido[4,3-d]pyrimidin-2-yl]oxymethyl]-1,2,3,5,6,7-hexahydropyrrolizin-3-yl]methyl N-[5-[1-(2,6-dioxo-3-piperidyl)-3-methyl-2-oxo-benzimidazol-5-yl]pentyl]carbamate (005)

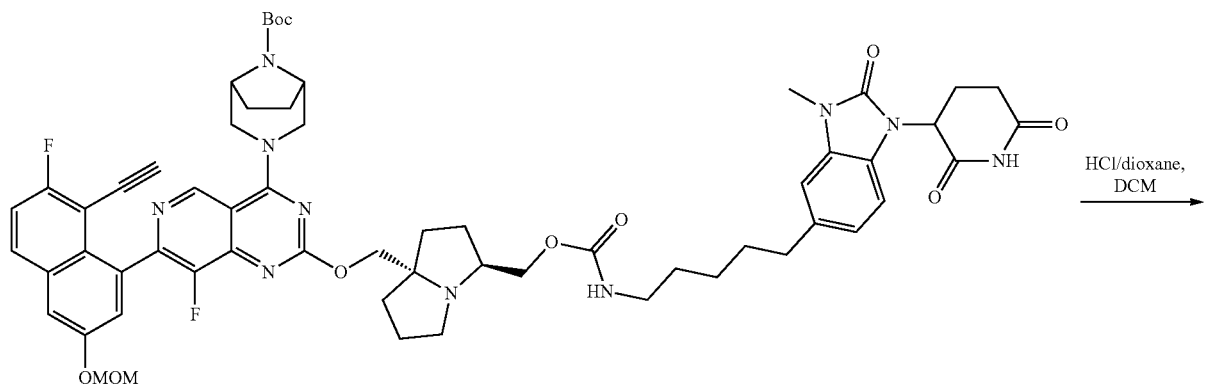

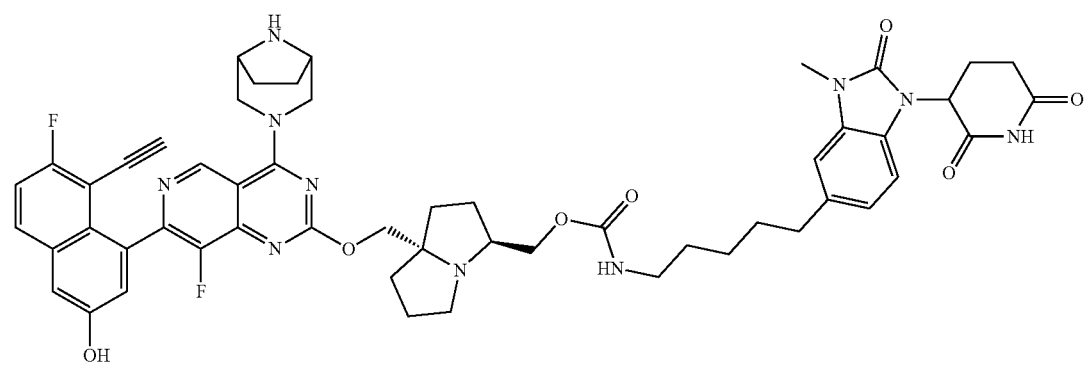

005

To a solution of tert-butyl 3-[2-[[(3S,8S)-3-[5-[1-(2,6-dioxo-3-piperidyl)-3-methyl-2-oxo-benzimidaz-ol-5-yl]pentylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (25.0 mg, 22.2 μmol) in DCM (3 mL) was added HCl/dioxane (4.00 M, 1.50 mL). The mixture was stirred at 25° C. for 0.25 hr. Upon completion, the mixture was concentrated in vacuo to give a residue. The residue was purified by prep-HPLC (column: Welch Ultimate C18 150*25 mm*5 μm; mobile phase: [water (FA)-ACN]; B %: 10%-40%, 10 min) to afford the title compound (13.6 mg, 60% yield) as yellow solid. $^1$H NMR (400 MHz, DMSO-$d_6$) δ 11.07 (s, 1H), 9.03 (s, 1H), 7.98-7.94 (m, 1H), 7.47-7.43 (m, 1H), 7.39 (d, J=2.4 Hz, 1H), 7.17 (d, J=2.4 Hz, 2H), 7.04-6.93 (m, 2H), 6.84 (d, J=8.0 Hz, 1H), 5.34-5.29 (m, 1H), 4.48 (d, J=11.2 Hz, 1H), 4.31 (d, J=12.0 Hz, 1H), 4.18-4.00 (m, 4H), 3.92 (s, 1H), 3.66-3.55 (m, 5H), 3.31 (s, 3H), 3.26-3.21 (m, 2H), 2.98-2.92 (m, 2H), 2.91-2.84 (m, 1H), 2.74-2.67 (m, 2H), 2.63-2.56 (m, 3H), 2.09-1.96 (m, 2H), 1.77-1.64 (m, 9H), 1.60-1.49 (m, 3H), 1.46-1.38 (m, 2H), 1.31-1.23 (m, 2H); LC-MS (ESI+) m/z 983.2 (M+H)$^+$.

Example 21. Synthesis of Compound 010 a) Synthesis of Tert-butyl N-[9-[1-(2,6-dioxo-3-piperidyl)-3-methyl-2-oxo-benzimidazol-5-yl]nonyl]carbamate

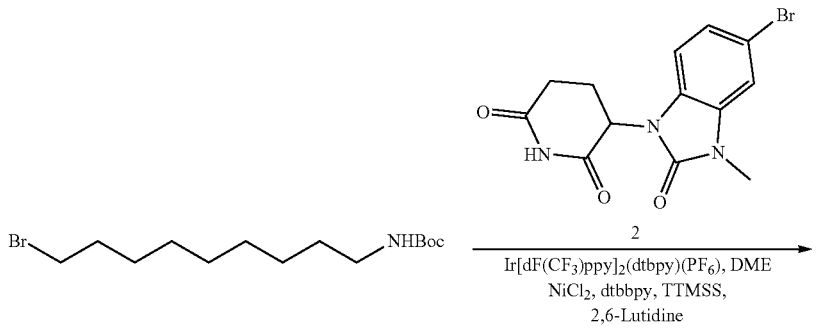

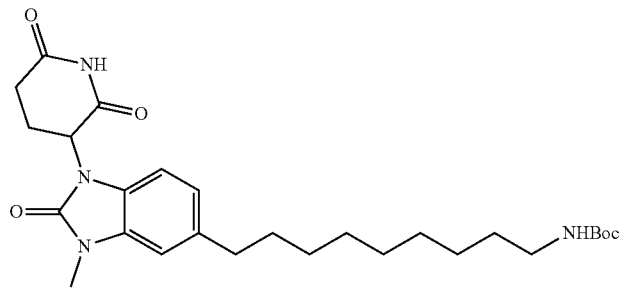

To a 15 mL vial equipped with a stir bar was added 3-(5-bromo-3-methyl-2-oxo-benzimidazol-1-yl) piperidine-2,6-dione (670 mg, 1.98 mmol), tert-butyl N-(9-bromononyl)carbamate (830 mg, 2.58 mmol), Ir[dF(CF$_3$)ppy]$_2$(dtbpy)(PF$_6$) (22.2 mg, 19.8 μmol), NiCl$_2$·dtbbpy (11.8 mg, 29.7 μmol), TTMSS (492 mg, 1.98 mmol), 2,6-Lutidine (424 mg, 3.96 mmol) in DME (30 mL). The vial was sealed and placed under N$_2$ atmosphere. The reaction was stirred and irradiated with a purple 10 W LED lamp (3 cm away), with cooling water to keep the reaction temperature at 25° C. for 14 hrs. Upon completion, the mixture was filtered and concentrated in vacuo. The residue was purified by reversed phase (0.1% FA) to afford the title compound (500 mg, 50% yield) as yellow solid. $^1$H NMR (400 MHz, DMSO-$d_6$) δ 11.08 (s, 1H), 7.05-6.96 (m, 2H), 6.85 (dd, J=1.2, 8.0 Hz, 1H), 6.74 (t, J=5.6 Hz, 1H), 5.33 (dd, J=5.6, 12.4 Hz, 1H), 3.32 (s, 3H), 2.90-2.85 (m, 2H), 2.75-2.61 (m, 3H), 2.60-2.57 (m, 2H), 2.03-1.96 (m, 1H), 1.61-1.53 (m, 2H), 1.36 (s, 9H), 1.35-1.32 (m, 2H), 1.31-1.20 (m, 10H); LC-MS (ESI$^+$) m/z 501.1 (M+H)$^+$.

b) Synthesis of 3-[5-(9-Aminononyl)-3-methyl-2-oxo-benzimidazol-1-yl]piperidine-2,6-dione

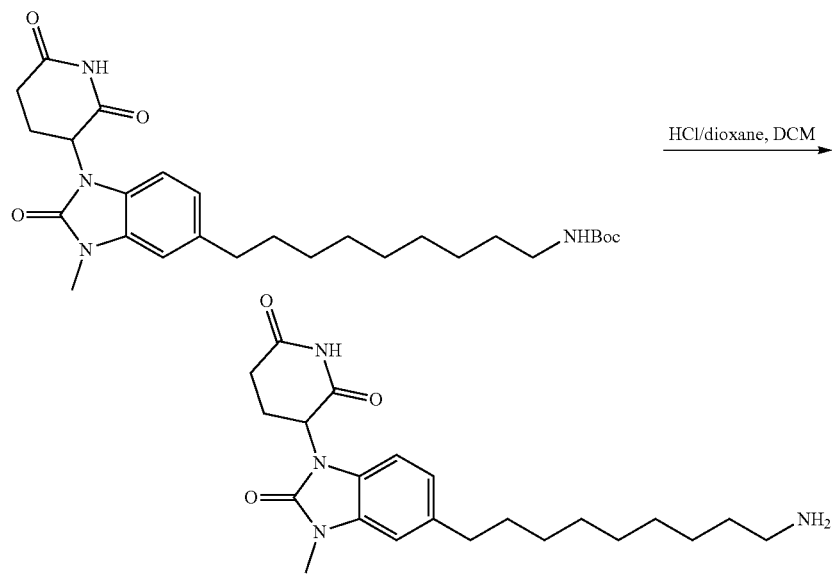

To a solution of tert-butyl N-[9-[1-(2,6-dioxo-3-piperidyl)-3-methyl-2-oxo-benzimidazol-5-yl] nonyl]carbamate (60.0 mg, 119 μmol) in DCM (1 mL) was added HCl/dioxane (4 M, 600 uL). The mixture was stirred at 25° C. for 2 hrs. Upon completion, the mixture was concentrated in vacuo to afford the title compound (50.0 mg, 95% yield, HCl salt) as yellow oil. LC-MS (ESI$^+$) m/z 401.0 (M+H)$^+$.

c) Synthesis of Tert-butyl 3-[2-[[(3S,8S)-3-[9-[1-(2,6-dioxo-3-piperidyl)-3-methyl-2-oxo-benzimidazol-5-yl] nonylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

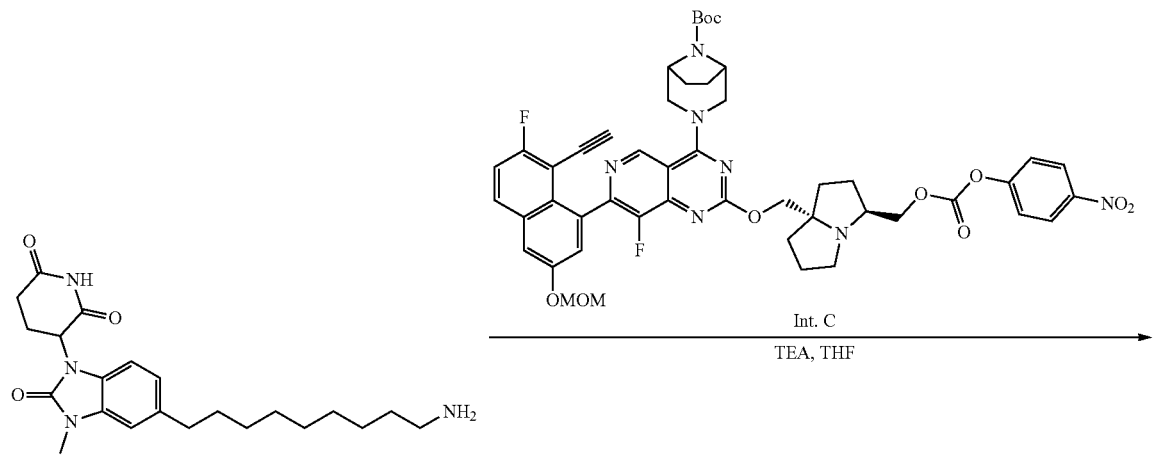

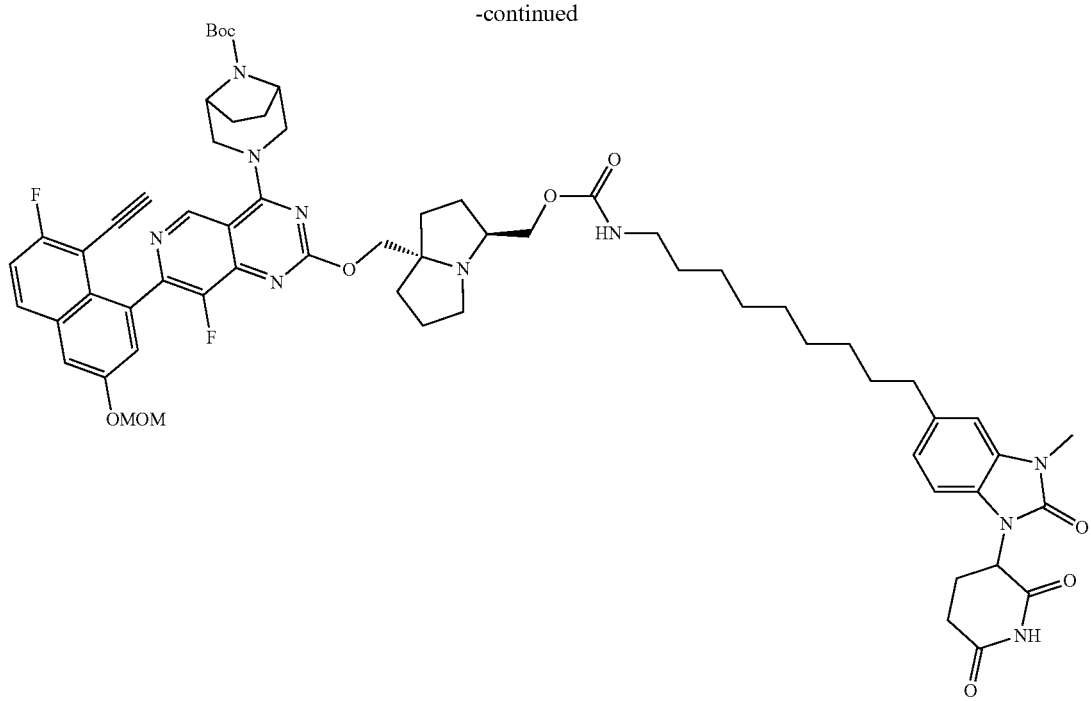

To a solution of Int. C (60.0 mg, 65.0 μmol) in THF (5 mL) was added TEA (19.7 mg, 195 μmol), the mixture was stirred at 25° C. for 0.5 hr, then the solution of 3-[5-(9-aminononyl)-3-methyl-2-oxo-benzimidazol-1-yl] piperidine-2,6-dione (42.6 mg, 97.6 μmol, HCl salt) in THF (5 mL) was added to the above solution. The mixture was stirred at 25° C. for 2 hrs. Upon completion, the mixture was concentrated in vacuo. The residue was purified by prep-HPLC (column: Welch Xtimate C18 150*25 mm*5 μm; mobile phase: [water (FA)-ACN]; B %: 35%-65%, 9 min) to afford the title compound (50.0 mg, 64% yield) as yellow solid. LC-MS (ESI$^+$) m/z 1183.8 (M+H)$^+$.

d) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methyl N-[9-[1-(2,6-dioxo-3-piperidyl)-3-methyl-2-oxo-benzimidazol-5-yl]nonyl]carbamate (O10)

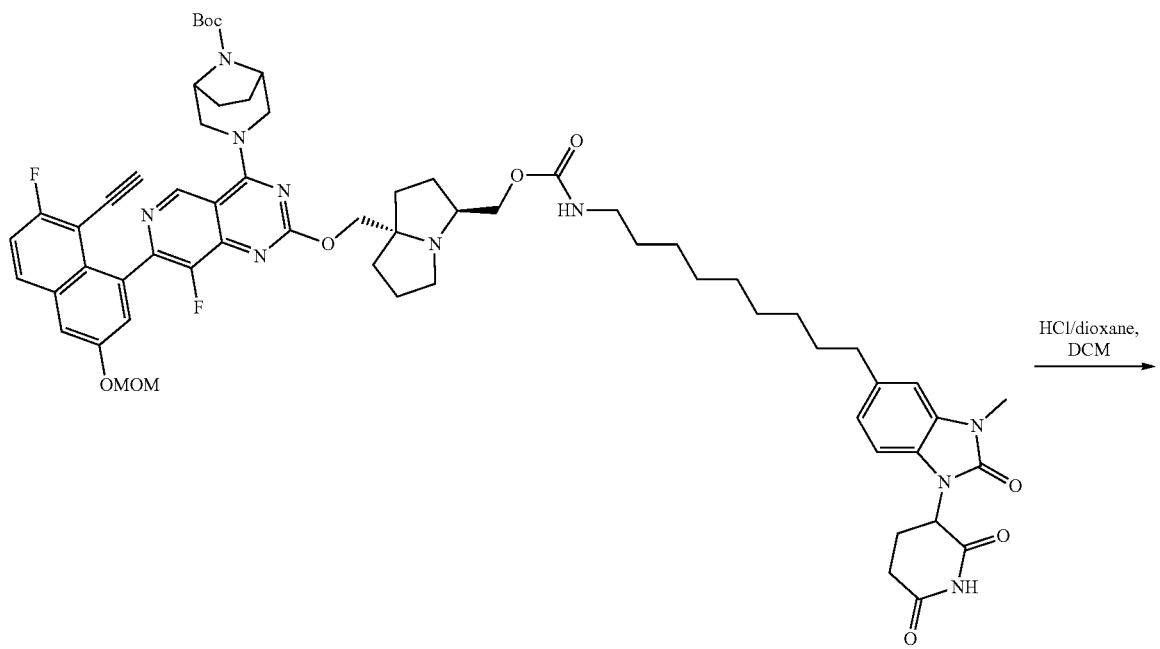

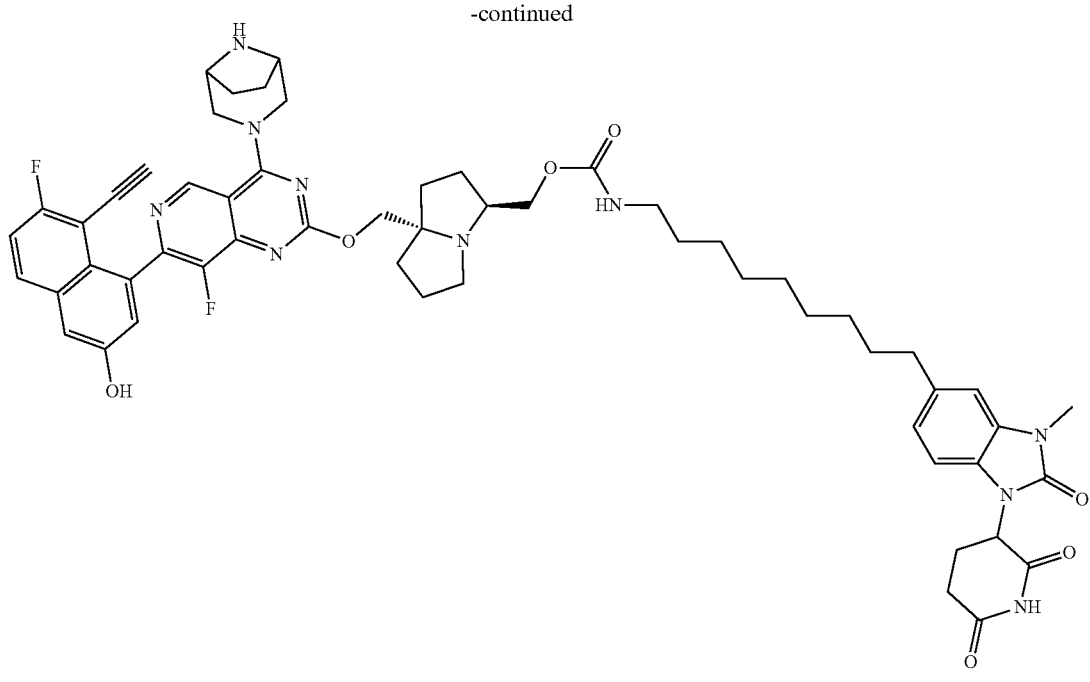

To a solution of tert-butyl 3-[2-[[(3S,8S)-3-[9-[1-(2,6-dioxo-3-piperidyl)-3-methyl-2-oxo-benzimidazol-5-yl]nonylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (50.0 mg, 42.2 μmol) in DCM (3 mL) was added HCl/dioxane (4 M, 2.00 mL). The mixture was stirred at 25° C. for 0.5 hr. Upon completion, the mixture was concentrated in vacuo. The residue was purified by prep-HPLC (column: Phenomenex luna C18 150*25 mm*10 μm; mobile phase: [water (FA)-ACN]; B %: 18%-48%, 15 min) to afford the title compound (20.2 mg, 45% yield) as yellow solid. $^1$H NMR (400 MHz, DMSO-$d_6$) δ 11.0 (s, 1H), 9.03 (s, 1H), 8.21 (s, 1H), 7.97 (dd, J=6.0, 9.2 Hz, 1H), 7.49-7.42 (m, 1H), 7.39 (d, J=2.4 Hz, 1H), 7.17 (d, J=2.0 Hz, 2H), 7.02-6.94 (m, 2H), 6.84 (d, J=8.0 Hz, 1H), 5.32 (dd, J=5.2, 12.4 Hz, 1H), 4.48 (d, J=12.0 Hz, 1H), 4.32 (d, J=12.4 Hz, 1H), 4.12-4.07 (m, 2H), 4.05-4.00 (m, 1H), 3.63-3.59 (m, 4H), 3.31 (s, 3H), 3.25-3.16 (m, 4H), 2.96-2.91 (m, 2H), 2.90-2.84 (m, 1H), 2.75-2.69 (m, 2H), 2.61-2.55 (m, 3H), 2.06-1.97 (m, 2H), 1.76-1.63 (m, 10H), 1.59-1.45 (m, 4H), 1.40-1.33 (m, 2H), 1.28-1.19 (m, 10H); LC-MS (ESI$^+$) m/z 1039.6 (M+H)$^+$.

Example 22. Synthesis of Compound 013 a) Synthesis of 3-(5-(10-Aminodecyl)-3-methyl-2-oxo-2,3-dihydro-1H-benzo[d]imidazol-1-yl)piperidine-2,6-dione Hydrochloride

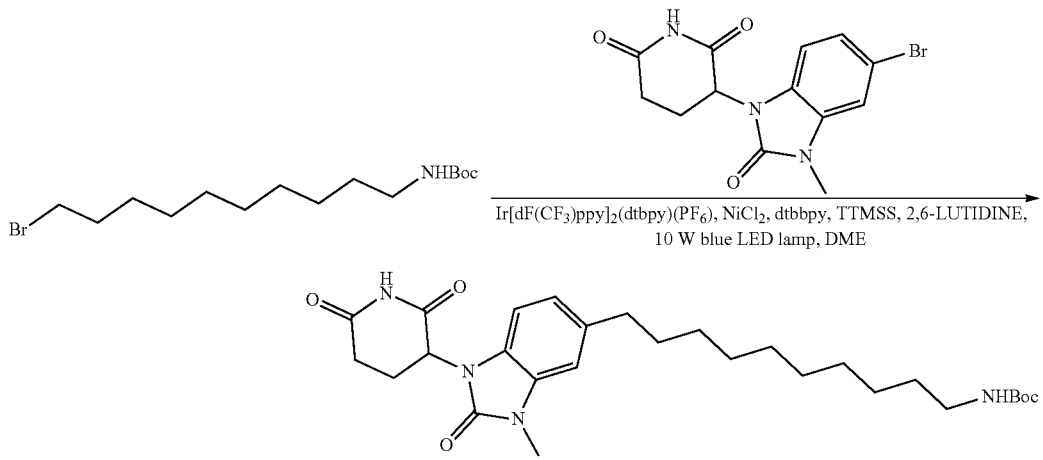

To an 15 mL vial equipped with a stirred bar was added 3-(5-bromo-3-methyl-2-oxo-benzimidazol-1-yl)piperidine-2,6-dione (500 mg, 1.48 mmol), tert-butyl N-(10-bromodecyl) carbamate (646 mg, 1.92 mmol, CAS #887353-29-9), Ir[dF(CF$_3$)ppy]$_2$(dtbpy)(PF$_6$) (16.5 mg, 14.7 μmol), NiCl$_2$·dtbbpy (8.83 mg, 22.1 μmol), TTMSS (367 mg, 1.48 mmol) and 2,6-LUTIDINE (316 mg, 2.96 mmol) in DME (10 mL). The vial was sealed and placed under N$_2$. The reaction was stirred and irradiated with a 10 W blue LED lamp (3 cm away), with cooling water to keep the reaction temperature at 25° C. for 14 hrs. Upon completion, the reaction mixture was filtered and concentrated in vacuo, then the residue was purified by prep-HPLC (column: UniSil 10-120 C18 50×250 mm; mobile phase: [water (FA)-ACN]; B %: 45%-80%, 22 min) to afford the title compound (400 mg, 52% yield) as yellow solid. $^1$H NMR (400 MHz, CDCl$_3$) δ 8.10 (s, 1H), 6.89 (d, J=8.0 Hz, 1H), 6.85 (s, 1H), 6.71 (d, J=8.0 Hz, 1H), 5.21 (dd, J=5.2, 12.4 Hz, 1H), 4.50 (s, 1H), 3.44 (s, 3H), 3.11 (d, J=6.0 Hz, 2H), 3.00-2.81 (m, 2H), 2.79-2.69 (m, 1H), 2.65 (t, J=7.6 Hz, 2H), 2.28-2.19 (m, 1H), 1.61 (d, J=7.2 Hz, 2H), 1.45 (s, 14H), 1.28 (s, 9H); LC-MS (ESI$^+$) m/z 515.2 (M+H)$^+$.

b) Synthesis of 3-(5-(10-Aminodecyl)-3-methyl-2-oxo-2,3-dihydro-1H-benzo[d]imidazol-1-yl)piperidine-2,6-dione

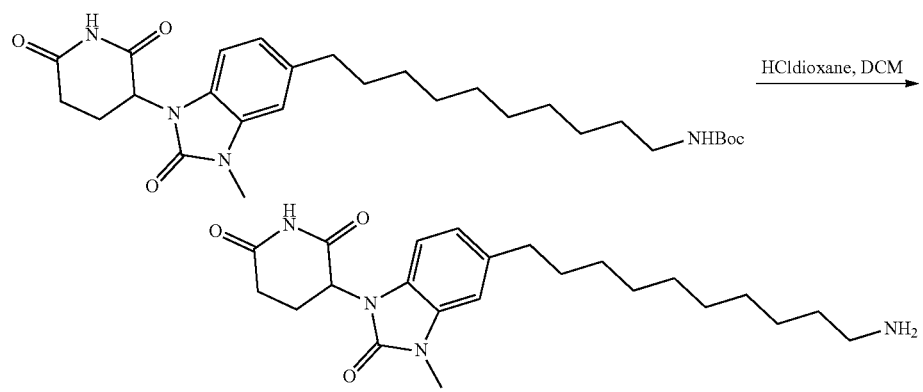

To a solution of tert-butyl N-[10-[1-(2,6-dioxo-3-piperidyl)-3-methyl-2-oxo-benzimidazol-5-yl] decyl]carbamate (200 mg, 388 μmol) in DCM (5 mL) was added HCl/dioxane (4.00 M, 97.1 uL). The mixture was stirred at 25° C. for 4 hrs. Upon completion, the reaction mixture concentrated in vacuo to afford the title compound (170 mg, 97% yield, HCl salt) as white solid. LC-MS (ESI$^+$) m/z 415.2 (M+H)$^+$.

c) Synthesis of (1R,5S)-tert-butyl 3-(2-(((3S,7aS)-3-(((((10-(1-(2,6-dioxopiperidin-3-yl)-3-methyl-2-oxo-2,3-dihydro-1H-benzo[d]imidazol-5-yl)decyl)carbamoyl)oxy)methyl)hexahydro-1H-pyrrolizin-7a-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

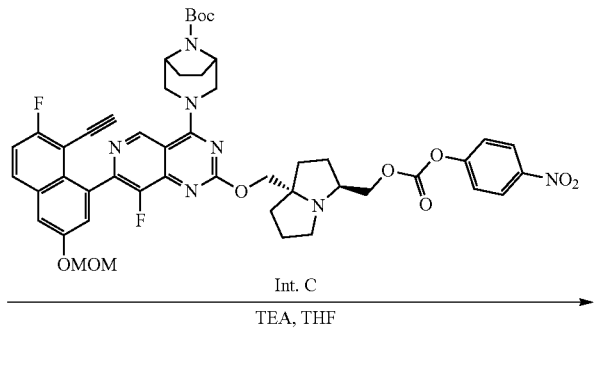

-continued

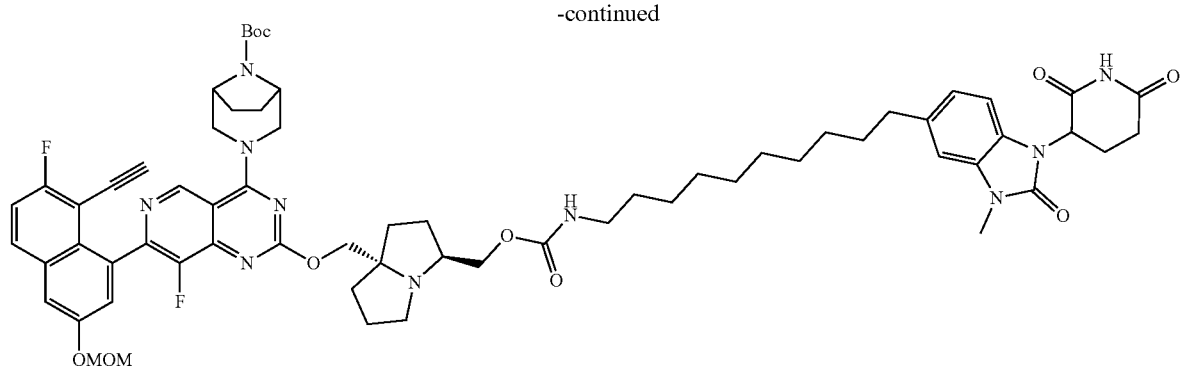

To a solution of 3-[5-(10-aminodecyl)-3-methyl-2-oxo-benzimidazol-1-yl]piperidine-2,6-dione (58.4 mg, 141 μmol) in THF (5 mL) was added TEA (21.4 mg, 211 μmol) and Int. C (65.0 mg, 70.5 μmol). The mixture was stirred at 25° C. for 0.5 hr. Upon completion, the reaction mixture was concentrated in vacuo to afford the title compound (80.0 mg 94% yield) as white solid. LC-MS (ESI$^+$) m/z 599.4 (M/2+H)$^+$.

d) Synthesis of ((3S,7aS)-7a-(((4-(((1R,5S)-3,8-diaz-abicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl (10-(1-(2,6-dioxopiperidin-3-yl)-3-methyl-2-oxo-2,3-dihydro-1H-benzo[d]imidazol-5-yl)decyl) carbamate (O13)

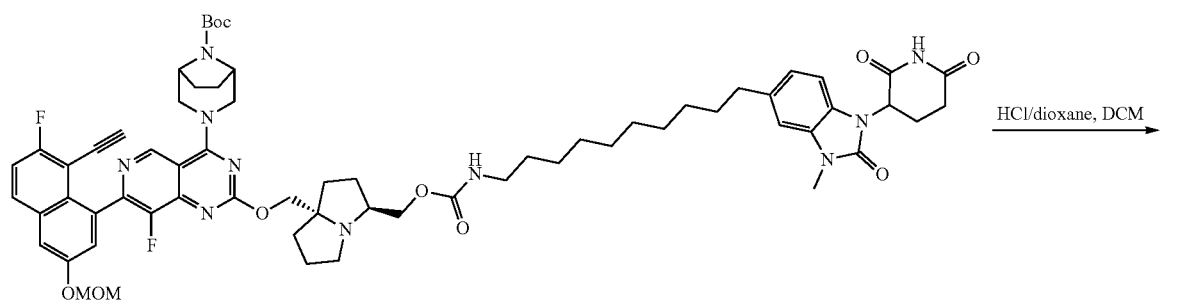

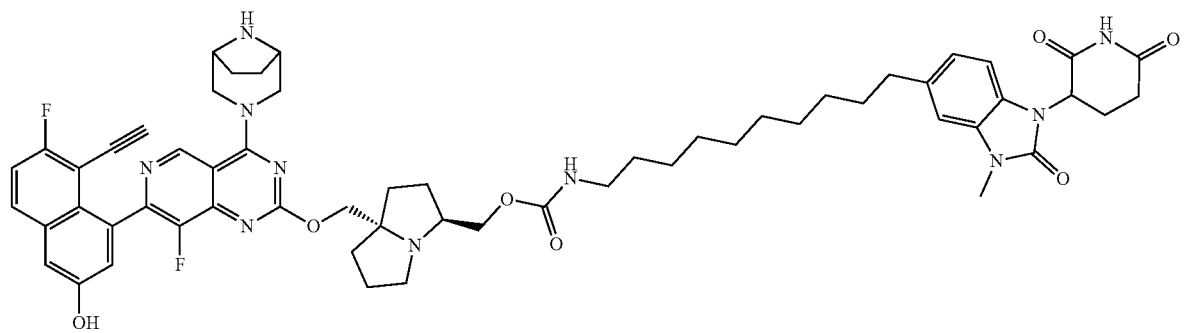

O13

To a solution of tert-butyl 3-[2-[[(3S,8S)-3-[10-[1-(2,6-dioxo-3-piperidyl)-3-methyl-2-oxo-benzimidazol-5-yl]decylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (80.0 mg, 66.8 μmol) in DCM (5 mL) was added HCl/dioxane (4.00 M, 1.00 mL). The mixture was stirred at 25° C. for 3 hrs. Upon completion, the reaction mixture was concentrated in vacuo to give a residue and the residue was purified by prep-HPLC (column: Welch Ultimate C18 150*25 mm*5 μm; mobile phase: [water (TFA)-ACN]; B %: 25%-55%, 10 min) to afford the title compound (10.0 mg, 14% yield) as yellow solid. $^1$H NMR (400 MHz, DMSO-$d_6$) δ 11.08 (s, 1H), 10.44 (d, J=4.0 Hz, 1H), 9.57-9.33 (m, 1H), 9.16 (s, 1H), 7.99 (dd, J=6.0, 9.2 Hz, 1H), 7.52-7.40 (m, 2H), 7.18 (s, 1H), 7.02-6.96 (m, 2H), 6.84 (d, J=8.0 Hz, 1H), 5.33 (dd, J=5.2, 12.8 Hz, 1H), 4.71 (dd, J=1.6, 14.4 Hz, 1H), 4.63-4.53 (m, 3H), 4.31 (d, J=5.6 Hz, 2H), 4.23 (s, 2H), 3.89 (d, J=5.2 Hz, 2H), 3.86 (d, J=6.8 Hz, 1H), 3.39 (d, J=11.2 Hz, 2H), 3.31 (s, 3H), 3.02-2.86 (m, 3H), 2.75-2.68 (m, 1H), 2.64-2.55 (m, 4H), 2.13-1.87 (m, 12H), 1.56 (s, 2H), 1.38 (s, 2H), 1.30-1.19 (m, 12H); LC-MS (ESI$^+$) m/z 1053.5 (M+H)$^+$.

Example 23. Synthesis of Compound 009 a) Synthesis of Tert-butyl N-[11-[1-(2,6-dioxo-3-piperidyl)-3-methyl-2-oxo-benzimidazol-5-yl]undecyl] carbamate

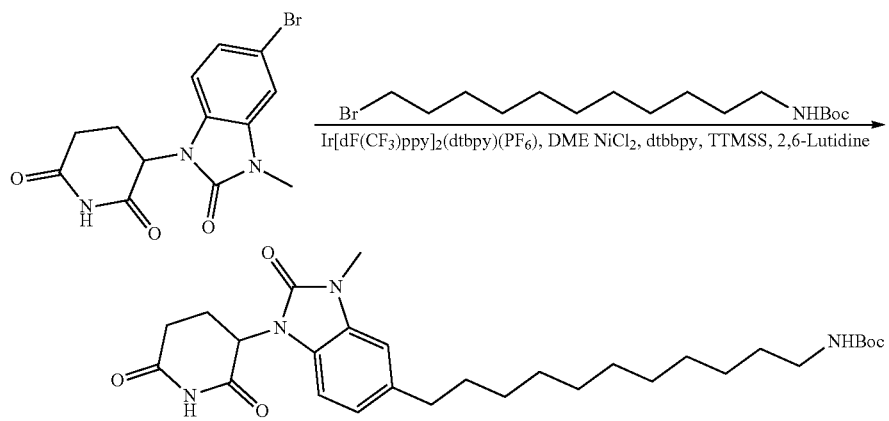

To an 15 mL vial equipped with a stir bar was added tert-butyl N-(11-bromoundecyl)carbamate (2.00 g, 5.71 mmol, CAS #463930-53-2), 3-(5-bromo-3-methyl-2-oxo-benzimidazol-1-yl)piperidine-2,6-dione (1.93 g, 5.71 mmol), Ir[dF(CF$_3$)ppy]$_2$(dtbpy)(PF$_6$) (640 mg, 570 μmol), NiCl$_2$·dtbbpy (34.1 mg, 85.6 μmol), TTMSS (1.42 g, 5.71 mmol), 2,6-Lutidine (1.22 g, 11.4 mmol) in DME (30 mL). The vial was sealed and placed under nitrogen. The reaction was stirred and irradiated with a purple 10 W LED lamp (3 cm away) with cooling water to keep the reaction temperature at 25° C. for 14 hrs. Upon completion, the mixture was concentrated in vacuo. The crude product was purified by reversed-phase HPLC (0.1% FA condition) to afford the title compound (2.00 g, 66% yield) as faint brown solid. $^1$H NMR (400 MHz, DMSO-$d_6$) δ 11.07 (s, 1H), 7.04-6.95 (m, 2H), 6.85 (dd, J=1.2, 8.0 Hz, 1H), 6.74 (t, J=5.2 Hz, 1H), 5.33 (dd, J=5.2, 12.8 Hz, 1H), 3.32 (s, 3H), 2.95-2.84 (m, 3H), 2.76-2.66 (m, 1H), 2.62-2.57 (m, 2H), 2.51-2.50 (m, 2H), 1.63-1.50 (m, 2H), 1.36 (s, 9H), 1.35-1.31 (m, 2H), 1.29-1.18 (m, 14H).

b) Synthesis of 3-[5-(11-Aminoundecyl)-3-methyl-2-oxo-benzimidazol-1-yl]piperidine-2,6-dione

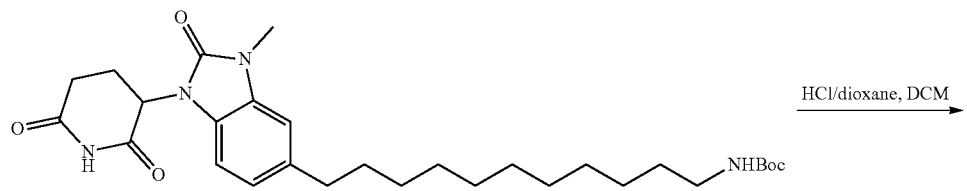

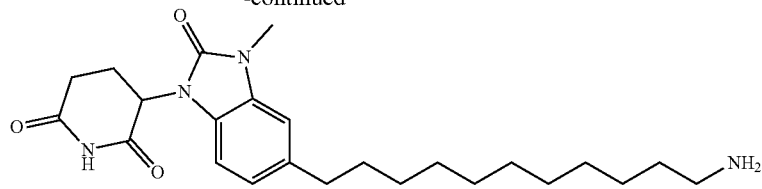

To a solution of tert-butyl N-[11-[1-(2,6-dioxo-3-piperidyl)-3-methyl-2-oxo-benzimidazol-5-yl]undecyl]carbamate (200 mg, 378 μmol) in DCM (1 mL) was added HCl/dioxane (4 M, 2.00 mL). The mixture was stirred at 25° C. for 1 hr. Upon completion, the mixture was filtered and concentrated in vacuo to afford the title compound (130 mg, 80% yield, HCl salt) as faint brown solid. LC-MS (ESI+) m/z 429.3 (M+H)+.

c) Synthesis of Tert-butyl 3-[2-[[(3S,8S)-3-[11-[1-(2,6-dioxo-3-piperidyl)-3-methyl-2-oxo-benzimidazol-8-yl] undecylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

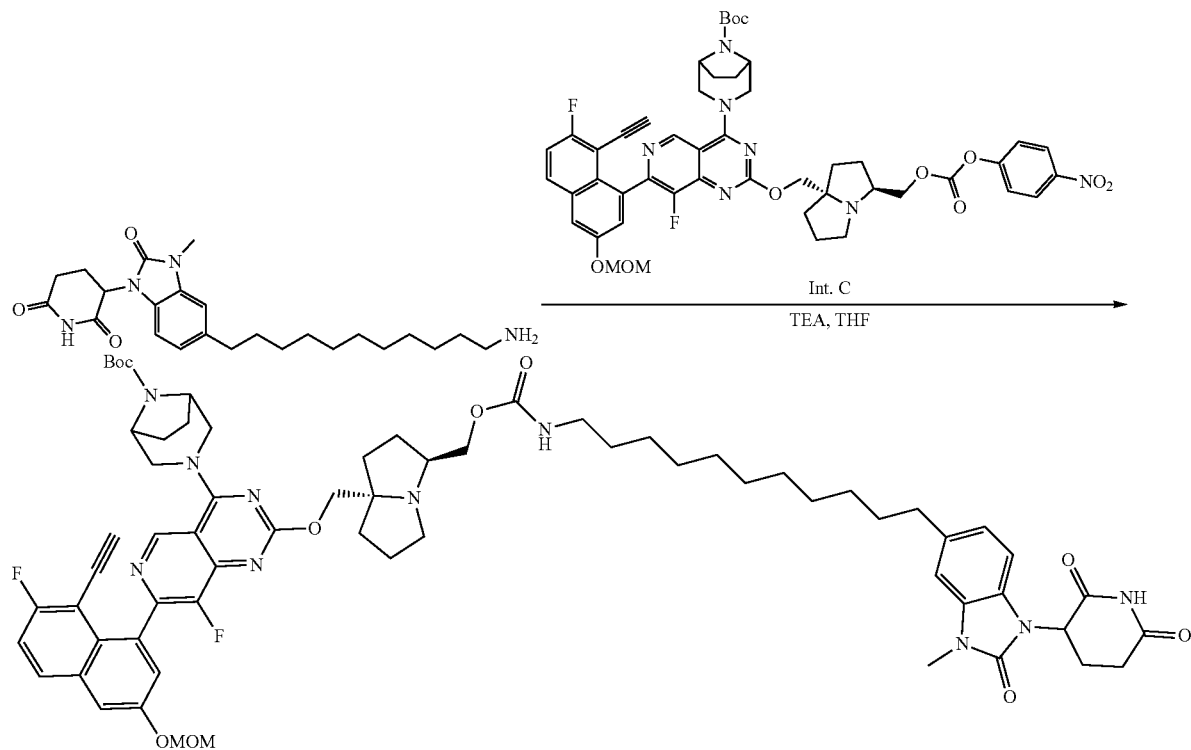

To a solution of Int. C (64.0 mg, 69.4 μmol), 3-[5-(11-aminoundecyl)-3-methyl-2-oxo-benzimidazol-1-yl]piperidine-2,6-dione (29.7 mg, 69.4 μmol, HCl salt) in THF (1 mL) was added TEA (7.02 mg, 69.4 μmol). The mixture was degassed and purged with $N_2$ for 3 times. And then the mixture was stirred at 25° C. for 2 hrs under $N_2$ atmosphere. Upon completion, the mixture was concentrated in vacuo. The residue was purified by prep-HPLC (column: Phenomenex luna C18 150*25 mm*10 μm; mobile phase: [water (FA)-ACN]; B %: 29%-59%, 15 min) to afford the title compound (30.0 mg, 35% yield) as faint brown solid. LC-MS (ESI+) m/z 606.3 (M+2H)/2+.

d) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methyl N-[11-[1-(2,6-dioxo-3-piperidyl)-3-methyl-2-oxo-benzimidazol-5-yl]undecyl]carbamate (009)

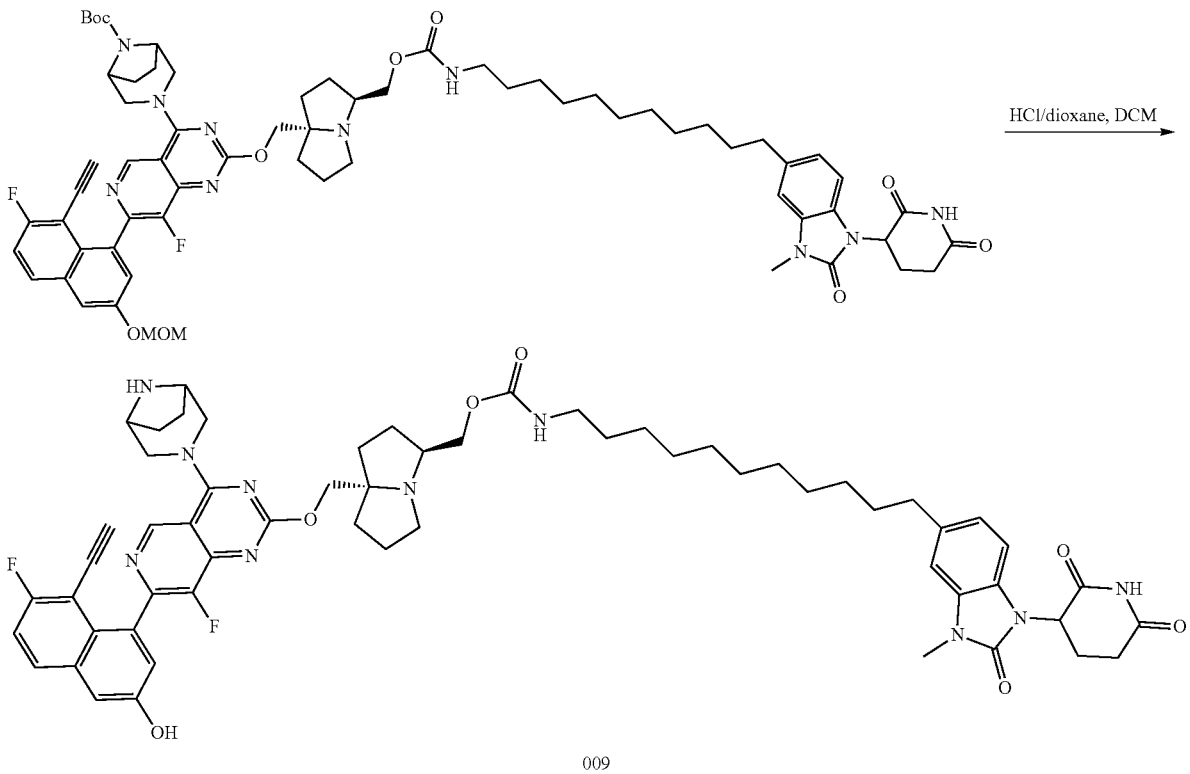

To a solution of tert-butyl 3-[2-[[(3S,8S)-3-[11-[1-(2,6-dioxo-3-piperidyl)-3-methyl-2-oxo-benzimidazol-5-yl]undecylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 24.7 μmol) in DCM (0.5 mL) was added HCl/dioxane (4 M, 1.00 mL). The mixture was stirred at 25° C. for 1 hr. Upon completion, the mixture was concentrated in vacuo. The residue was purified by prep-HPLC (column: Phenomenex luna C18 150*25 mm*10 μm; mobile phase: [water (FA)-ACN]; B %: 17%-47%, min) to afford the title compound (12.4 mg, 47% yield) as yellow solid. $^1$H NMR (400 MHz, DMSO-$d_6$) δ 11.09 (s, 1H), 9.03 (s, 1H), 8.2-8.22 (m, 1H), 7.97 (dd, J=6.0, 9.2 Hz, 1H), 7.46 (t, J=8.8 Hz, 1H), 7.39 (d, J=2.4 Hz, 1H), 7.23-7.13 (m, 2H), 7.03-6.94 (m, 2H), 6.84 (d, J=7.6 Hz, 1H), 5.33 (dd, J=5.2, 12.8 Hz, 1H), 4.47 (d, J=11.6 Hz, 1H), 4.31 (d, J=12.4 Hz, 1H), 4.11-4.05 (m, 2H), 4.04-3.96 (m, 1H), 3.93 (s, 1H), 3.67-3.60 (m, 2H), 3.31 (s, 3H), 2.97-2.92 (m, 2H), 2.89-2.82 (m, 1H), 2.72-2.67 (m, 2H), 2.65-2.61 (m, 2H), 2.60-2.56 (m, 4H), 2.12-1.92 (m, 3H), 1.77-1.63 (m, 10H), 1.60-1.47 (m, 4H), 1.41-1.31 (m, 3H), 1.28-1.18 (m, 14H); LC-MS (ESI$^+$) m/z 1067.8 (M+H)$^+$.

Example 24. Synthesis of Compound 004 a) Synthesis of Tert-butyl N-[2-[1-(2,6-dioxo-3-piperidyl)-3-methyl-2-oxo-benzimidazol-4-yl]ethyl]carbamate

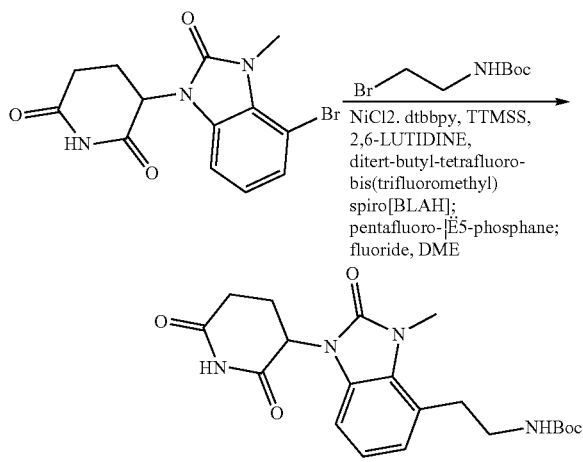

To an 40 mL vial equipped with a stir bar was added 3-(4-bromo-3-methyl-2-oxo-benzimidazol-1-yl)piperidine-2,6-dione (450 mg, 1.33 mmol), tert-butyl N-(2-bromoethyl)carbamate (387 mg, 1.73 mmol, CAS #39684-80-5), ditert-butyl-tetrafluoro-bis(trifluoromethyl)spiro[BLAH]; pentafluoro-$\lambda^5$-phosphane; fluoride (29.8 mg, 26.6 µmol), NiCl$_2$·dtbbpy (15.8 mg, 39.9 µmol), TTMSS (330 mg, 1.33 mmol), 2,6-LUTIDINE (285 mg, 2.66 mmol) in DME (20 mL). The vial was sealed and placed under N$_2$ atmosphere. The reaction mixture was stirred and irradiated with a 10 W blue LED lamp (3 cm away), with cooling water to keep the reaction temperature at 25° C. for 14 hrs. Upon completion, the reaction mixture was filtered and concentrated in vacuo to give a residue. The residue was purified by prep-HPLC (column: YMC Triart C18 250*50 mm*7 µm; mobile phase: [water (FA)-ACN]; B %: 20%-50%, 20 min) to afford the title compound (380 mg, 70% yield) as white solid. $^1$H NMR (400 MHz, CDCl$_3$) δ 8.07 (s, 1H), 7.06-6.98 (m, 1H), 6.91 (d, J=7.6 Hz, 1H), 6.70 (d, J=8.0 Hz, 1H), 5.22 (dd, J=5.2, 12.4 Hz, 1H), 4.68 (d, J=6.4 Hz, 1H), 3.70 (s, 3H), 3.44-3.39 (m, 2H), 3.15-3.12 (m, 2H), 3.01-2.90 (m, 1H), 2.89-2.69 (m, 2H), 2.31-2.17 (m, 1H), 1.45 (s, 9H); LC-MS (ESI$^+$) m/z 303.0 (M+H−100)$^+$.

b) Synthesis of 3-[4-(2-Aminoethyl)-3-methyl-2-oxo-benzimidazol-1-yl]piperidine-2,6-dione

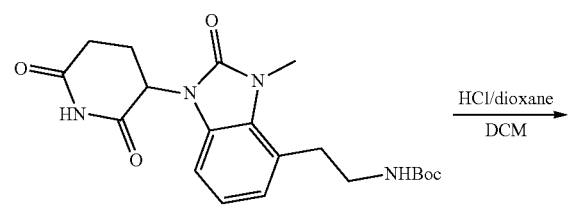

HCl/dioxane
DCM

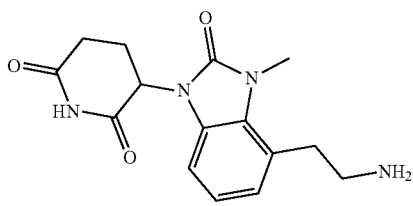

To a solution of tert-butyl N-[2-[1-(2,6-dioxo-3-piperidyl)-3-methyl-2-oxo-benzimidazol-4-yl] ethyl]carbamate (200 mg, 496 µmol) in DCM (1 mL) was added HCl/dioxane (4 M, 1.00 mL). The mixture was stirred at 25° C. for 0.5 hr. Upon completion, the reaction mixture was concentrated in vacuo to afford the title compound (168 mg, 99% yield, HCl salt) as white solid. LC-MS (ESI$^+$) m/z 302.9 (M+H)$^+$.

c) Synthesis of Tert-butyl 3-[2-[[(3S,8S)-3-[2-[1-(2,6-dioxo-3-piperidyl)-3-methyl-2-oxo-benzimidazol-4-yl]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

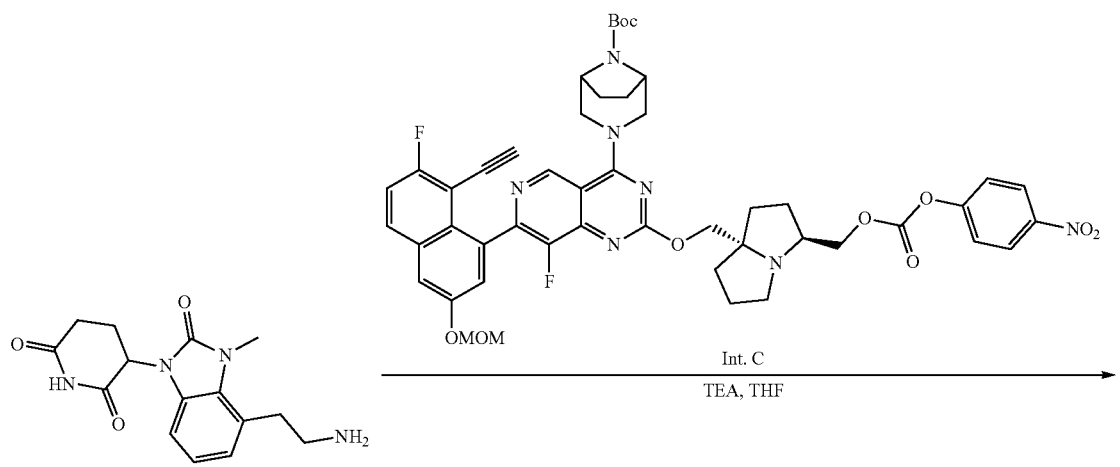


To a solution of 3-[4-(2-aminoethyl)-3-methyl-2-oxo-benzimidazol-1-yl]piperidine-2,6-dione (33.0 mg, 97.6 μmol, HCl salt) in THF (2 mL) was added TEA (19.7 mg, 195 μmol) and Int. C (60.0 mg, 65.0 μmol). The mixture was stirred at 25° C. for 12 hrs. Upon completion, the mixture was concentrated in vacuo to give a residue. The residue was purified by prep-HPLC (column: Welch Ultimate C18 150*25 mm*5 μm; mobile phase: [water (FA)-ACN]; B %: 30%-50%, 10 min) to afford the title compound (45.0 mg, 63% yield) as yellow solid. $^1$H NMR (400 MHz, DMSO-d$_6$) δ 11.08 (s, 1H), 9.08 (s, 1H), 8.12-8.08 (m, 1H), 7.74 (d, J=2.4 Hz, 1H), 7.57-7.52 (m, 1H), 7.50-7.42 (m, 1H), 7.38 (d, J=2.4 Hz, 1H), 7.04-6.93 (m, 2H), 6.90-6.85 (m, 1H), 5.37 (s, 2H), 4.61-4.50 (m, 1H), 4.46-4.35 (m, 1H), 4.35-4.29 (m, 2H), 4.20-4.03 (m, 4H), 3.99 (s, 1H), 3.68-3.60 (m, 2H), 3.58 (s, 3H), 3.44 (s, 3H), 3.23-3.19 (m, 2H), 3.08-2.99 (m, 2H), 2.95-2.65 (m, 5H), 2.58-2.56 (m, 1H), 2.08-1.95 (m, 2H), 1.89-1.81 (m, 2H), 1.80-1.50 (m, 10H), 1.46 (s, 9H); LC-MS (ESI$^+$) m/z 1085.6 (M+H)$^+$.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl N-[2-[1-(2,6-dioxo-3-piperidyl)-3-methyl-2-oxo-benzimidazol-4-yl]ethyl]carbamate (004)

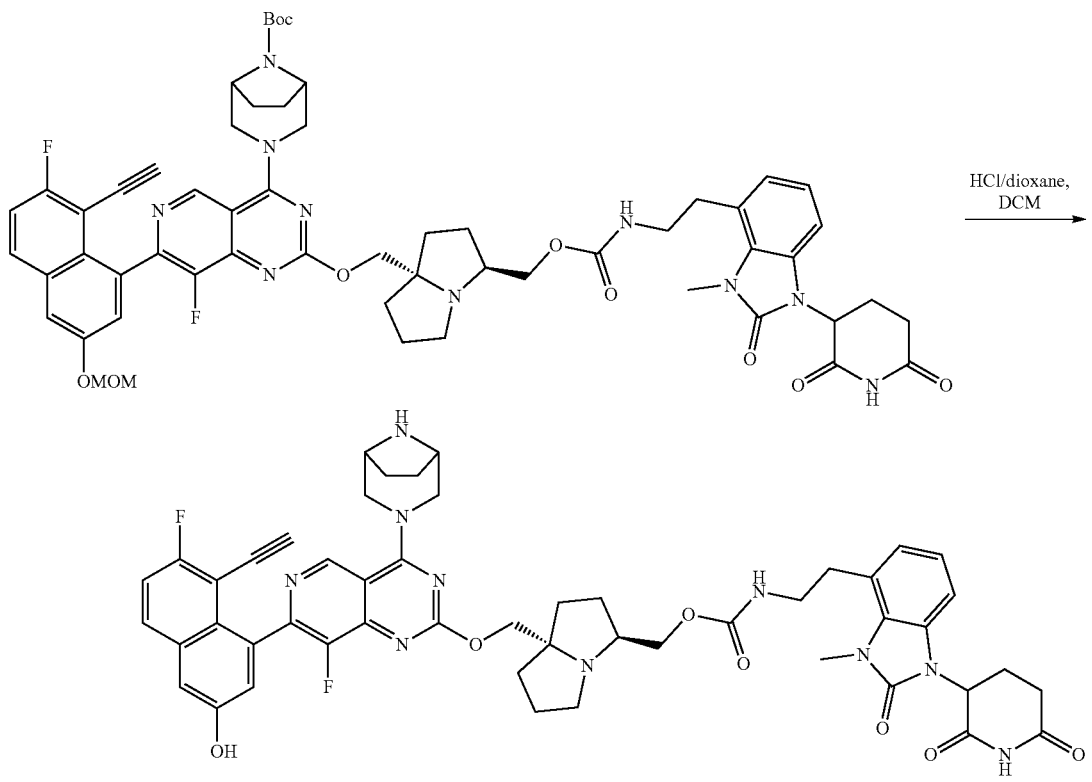

004

To a solution of tert-butyl 3-[2-[[(3S,8S)-3-[2-[1-(2,6-dioxo-3-piperidyl)-3-methyl-2-oxo-benzimidazol-4-yl]ethylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (45.0 mg, 41.4 μmol) in DCM (1 mL) was added HCl/dioxane (4 M, 450 uL). The reaction mixture was stirred at 25° C. for 0.5 hr. Upon completion, the reaction mixture was concentrated in vacuo to give a residue. The residue was purified by prep-HPLC (column: Waters xbridge 150*25 mm 10 μm; mobile phase: [water (FA)-ACN]; B %: 6%-36%, 9 min) to afford the title compound (13.6 mg, 33% yield, FA salt) as yellow solid. $^1$H NMR (400 MHz, DMSO-$d_6$) δ 11.23-10.94 (m, 1H), 9.11-8.95 (m, 1H), 7.97 (dd, J=6.0, 9.2 Hz, 1H), 7.51-7.42 (m, 2H), 7.39 (d, J=2.4 Hz, 1H), 7.17 (d, J=2.4 Hz, 1H), 6.97 (d, J=6.8 Hz, 2H), 6.90-6.82 (m, 1H), 5.36 (dd, J=5.2, 12.8 Hz, 1H), 4.48 (d, J=11.2 Hz, 1H), 4.32 (d, J=12.0 Hz, 1H), 4.20-4.09 (m, 3H), 4.07-4.01 (m, 1H), 3.96-3.91 (m, 1H), 3.67-3.60 (m, 4H), 3.58 (s, 3H), 3.56-3.54 (m, 1H), 3.22-3.18 (m, 2H), 3.07-3.00 (m, 2H), 2.94-2.81 (m, 2H), 2.77-2.67 (m, 3H), 2.61-2.59 (m, 1H), 2.08-1.95 (m, 2H), 1.85-1.41 (m, 12H); LC-MS (ESI$^+$) m/z 941.3 (M+H)$^+$.

Example 25. Synthesis of Compound 003 a) Synthesis of Tert-butyl N-[3-[1-(2,6-dioxo-3-piperidyl)-3-methyl-2-oxo-benzimidazol-4-yl]propyl] carbamate


To an 40 mL vial equipped with a stir bar was added 3-(4-bromo-3-methyl-2-oxo-benzimidazol-1-yl) piperidine-2,6-dione (400 mg, 1.18 mmol), tert-butyl N-(3-bromopropyl)carbamate (366 mg, 1.54 mmol, CAS #83948-53-2), Ir[dF(CF$_3$)ppy]$_2$(dtbpy)(PF$_6$) (26.5 mg, 23.6 μmol), NiCl$_2$·dtbbpy (14.1 mg, 35.5 μmol), TTMSS (294 mg, 1.18 mmol), 2,6-LUTIDINE (253 mg, 2.37 mmol) in DME (30 mL). The vial was sealed and placed under nitrogen. The reaction was stirred and irradiated with a 10 W blue LED lamp (3 cm away), with cooling water to keep the reaction temperature at 25° C. for 14 hrs. Upon completion, the mixture was concentrated in vacuo. The mixture was purified by prep-HPLC (column: Phenomenex luna C18 150*25 mm*10 μm; mobile phase: [water (FA)-ACN]; B %: 25%-55%, 10 min) to afford the title compound (150 mg, 30% yield) as green solid. LC-MS (ESI$^+$) m/z 317.0 (M–100)$^+$.

b) Synthesis of 3-[4-(3-Aminopropyl)-3-methyl-2-oxo-benzimidazol-1-yl]piperidine-2,6-dione


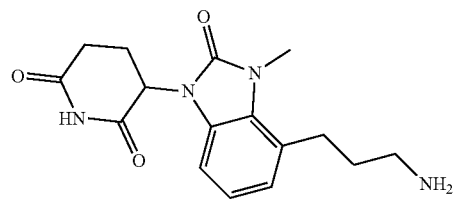

To a solution of tert-butyl N-[3-[1-(2,6-dioxo-3-piperidyl)-3-methyl-2-oxo-benzimidazol-4-yl]propyl] carbamate (50.0 mg, 120 μmol) in DCM (5 mL) was added HCl/dioxane (4 M, 1.00 mL) and the mixture was stirred at 25° C. for 1 hr. Upon completion, the mixture was concentrated in vacuo to afford the title compound (35.0 mg, 82% yield, HCl salt) as yellow solid. LC-MS (ESI$^+$) m/z 317.0 (M+H)$^+$.

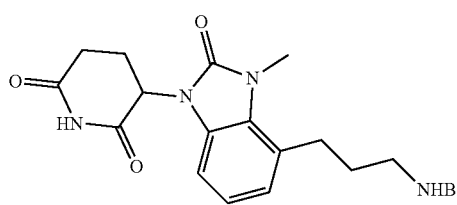

c) Synthesis of Tert-butyl 3-[2-[[(3S,8S)-3-[3-[1-(2,6-dioxo-3-piperidyl)-3-methyl-2-oxo-benzimidazol-4-yl] propylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate



To a solution of 3-[4-(3-aminopropyl)-3-methyl-2-oxo-benzimidazol-1-yl]piperidine-2,6-dione (25.2 mg, 71.6 μmol, HCl salt) and TEA (19.7 mg, 195 μmol) in THF (8 mL) was added Int. C (60.0 mg, 65.0 μmol) and the mixture was stirred at 25° C. for 16 hrs. Upon completion, the mixture was concentrated in vacuo. The mixture was purified by prep-HPLC (column: Phenomenex luna C18 150*25 mm*10 μm; mobile phase: [water (FA)-ACN]; B %: 28%-58%, 9 min) to afford the title compound (50.0 mg, 58% yield) as yellow solid. LC-MS (ESI$^+$) m/z 1099.9 (M+H)$^+$.

d) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methylN-[3-[1-(2,6-dioxo-3-piperidyl)-3-methyl-2-oxo-benzimidazol-4-yl]propyl]carbamate (003)

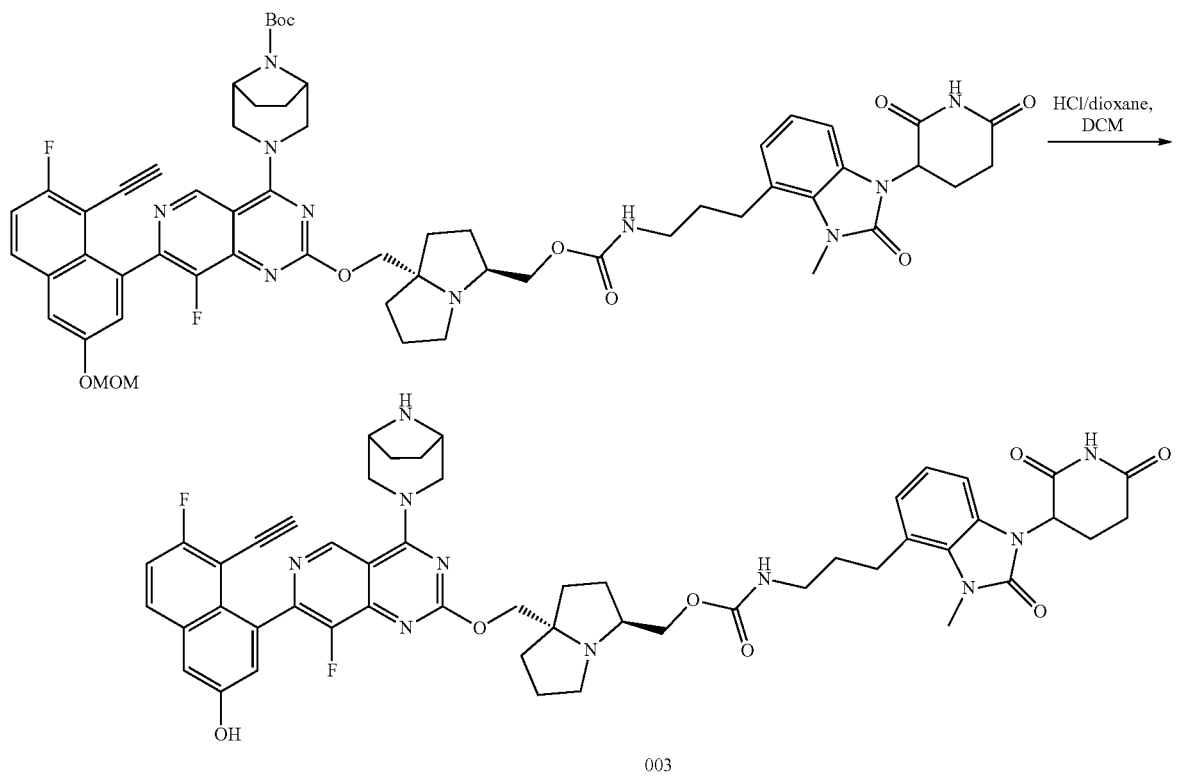

003

To a solution of tert-butyl 3-[2-[[(3S,8S)-3-[3-[1-(2,6-dioxo-3-piperidyl)-3-methyl-2-oxo-benzimidazol-4-yl]propylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (45.0 mg, 40.9 μmol) in DCM (5 mL) was added HCl/dioxane (4 M, 900 uL) and the mixture was stirred at 25° C. for 1 hr. Upon completion, the mixture was concentrated in vacuo. The mixture was purified by prep-HPLC (column: Welch Ultimate C18 150*25 mm*5 μm; mobile phase: [water (TFA)-ACN]; B %: 18%-38%, 10 min) to afford the title compound (12.0 mg, 26% yield, TFA salt) as yellow solid. H NMR (400 MHz, DMSO-$d_6$) δ 11.08 (s, 1H), 10.44 (d, J=4.4 Hz, 1H), 10.28-10.18 (m, 1H), 9.40 (d, J=9.6 Hz, 1H), 9.16 (s, 1H), 9.14-9.09 (m, 1H), 8.00 (dd, J=6.0, 9.2 Hz, 1H), 7.48 (t, J=9.2 Hz, 1H), 7.42 (d, J=2.4 Hz, 1H), 7.34-7.26 (m, 1H), 7.18 (d, J=2.4 Hz, 1H), 7.04-6.97 (m, 2H), 6.86 (d, J=7.6 Hz, 1H), 5.33 (dd, J=5.2, 12.8 Hz, 1H), 4.74-4.67 (m, 1H), 4.64-4.52 (m, 3H), 4.38-4.29 (m, 2H), 4.23 (s, 2H), 3.89 (d, J=4.4 Hz, 2H), 3.85 (d, J=5.6 Hz, 1H), 3.31 (s, 3H), 3.07-2.99 (m, 2H), 2.95-2.85 (m, 1H), 2.76-2.57 (m, 7H), 2.31 (d, J=1.6, 8.8 Hz, 1H), 2.18-1.89 (m, 14H), 1.78-1.69 (m, 2H); LC-MS (ESI$^+$) m/z 955.3 (M+H)$^+$.

Example 26. Synthesis of Compound 008 a) Synthesis of Tert-butyl (4-(1-(2,6-dioxopiperidin-3-yl)-3-methyl-2-oxo-2,3-dihydro-1H-benzo[d]imidazol-4-yl)butyl)carbamate

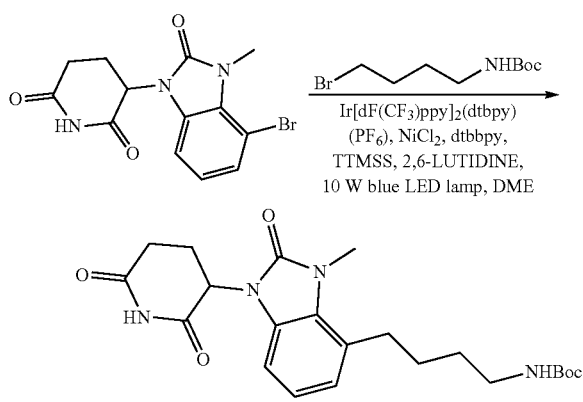

To a 15 mL vial equipped with a stirred bar was added 3-(4-bromo-3-methyl-2-oxo-benzimidazol-1-yl)piperidine-2,6-dione (500 mg, 1.48 mmol) tert-butyl N-(4-bromobutyl)

carbamate (484 mg, 1.92 mmol, CAS #164365-88-2), Ir[dF(CF₃)ppy]₂(dtbpy)(PF₆) (33.1 mg, 29.5 μmol), TTMSS (49.7 mg, 199 μmol), NiCl₂·dtbbpy (17.6 mg, 44.3 μmol), 2,6-Lutidine (316 mg, 2.96 mmol) in DME (5 mL). The vial was sealed and placed under N₂. The reaction was stirred and irradiated with a 10 W blue LED lamp (3 cm away), with cooling water to keep the reaction temperature at 25° C. for 14 hrs. Upon completion, the reaction mixture was filtered and concentrated in vacuo and the residue was purified by prep-HPLC (column: Phenomenex luna C18 250*50 mm*10 μm; mobile phase: [water (FA)-ACN]; B %: 35%-65%, 30 min) to afford the title compound (400 mg, 62% yield) as white solid. LC-MS (ESI⁺) m/z 374.9 (M−56+H)⁺.

b) Synthesis of 3-(4-(4-Aminobutyl)-3-methyl-2-oxo-2,3-dihydro-1H-benzo[d]imidazol-1-yl)piperidine-2,6-dione

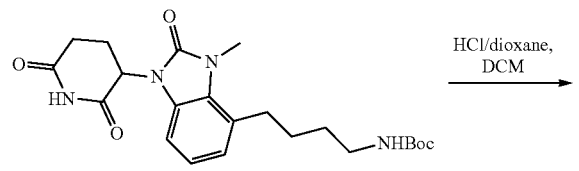

To a solution of tert-butyl N-[4-[1-(2,6-dioxo-3-piperidyl)-3-methyl-2-oxo-benzimidazol-4-yl]butyl] carbamate (200 mg, 464 μmol) in DCM (5 mL) was added HCl/dioxane (4.00 M, 1.00 mL). The mixture was stirred at 25° C. for 3 hrs. Upon completion, the reaction mixture concentrated in vacuo to afford the title compound (160 mg, 93% yield, HCl salt) as white solid. LC-MS (ESI⁺) m/z 330.9 (M+H)⁺.

c) Synthesis of (1R,5S)-tert-butyl 3-(2-(((3S,7aS)-3-((((4-(1-(2,6-dioxopiperidin-3-yl)-3-methyl-2-oxo-2,3-dihydro-1H-benzo[d]imidazol-4-yl)butyl)carbamoyl)oxy)methyl)hexahydro-1H-pyrrolizin-7a-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

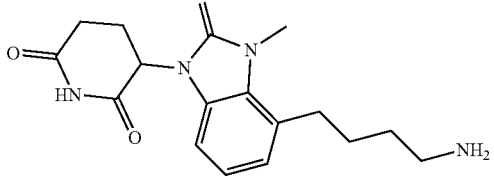

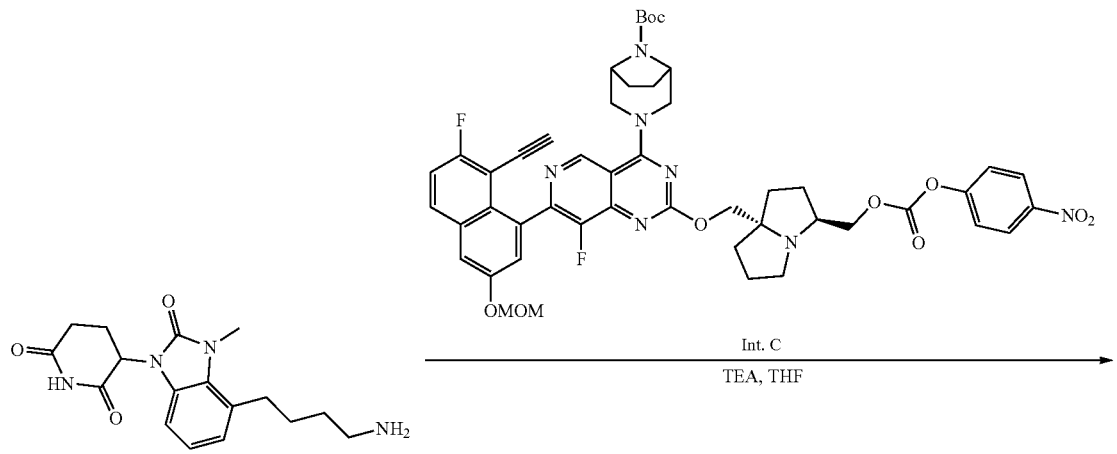

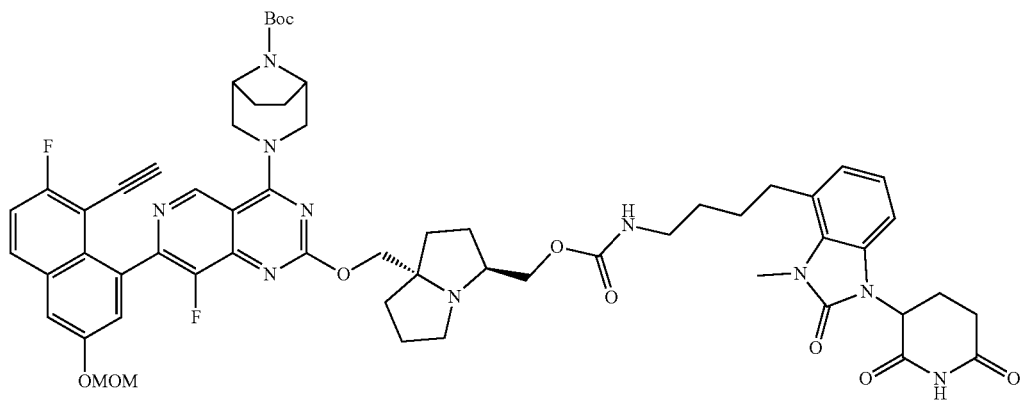

To a solution of 3-[4-(4-aminobutyl)-3-methyl-2-oxo-benzimidazol-1-yl]piperidine-2,6-dione (47.7 mg, 130 μmol, HCl salt) in THF (5 mL) was added TEA (32.9 mg, 325 μmol) and Int. C (60.0 mg, 65.0 μmol). The mixture was stirred at 25° C. for 2 hrs. Upon completion, the reaction mixture concentrated in vacuo, then the residue was purified by prep-HPLC (column: Phenomenex luna C18 150*25 mm*10 μm; mobile phase: [water (FA)-ACN]; B %: 27%-57%, 15 min) to afford the title compound (30.0 mg, 41% yield) as white solid. LC-MS (ESI$^+$) m/z 1113.5 (M+H)$^+$.

d) Synthesis of ((3S,7aS)-7a-(((4-(((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl (4-(1-(2,6-dioxopiperidin-3-yl)-3-methyl-2-oxo-2,3-dihydro-1H-benzo[d]imidazol-4-yl) butyl)carbamate (008)

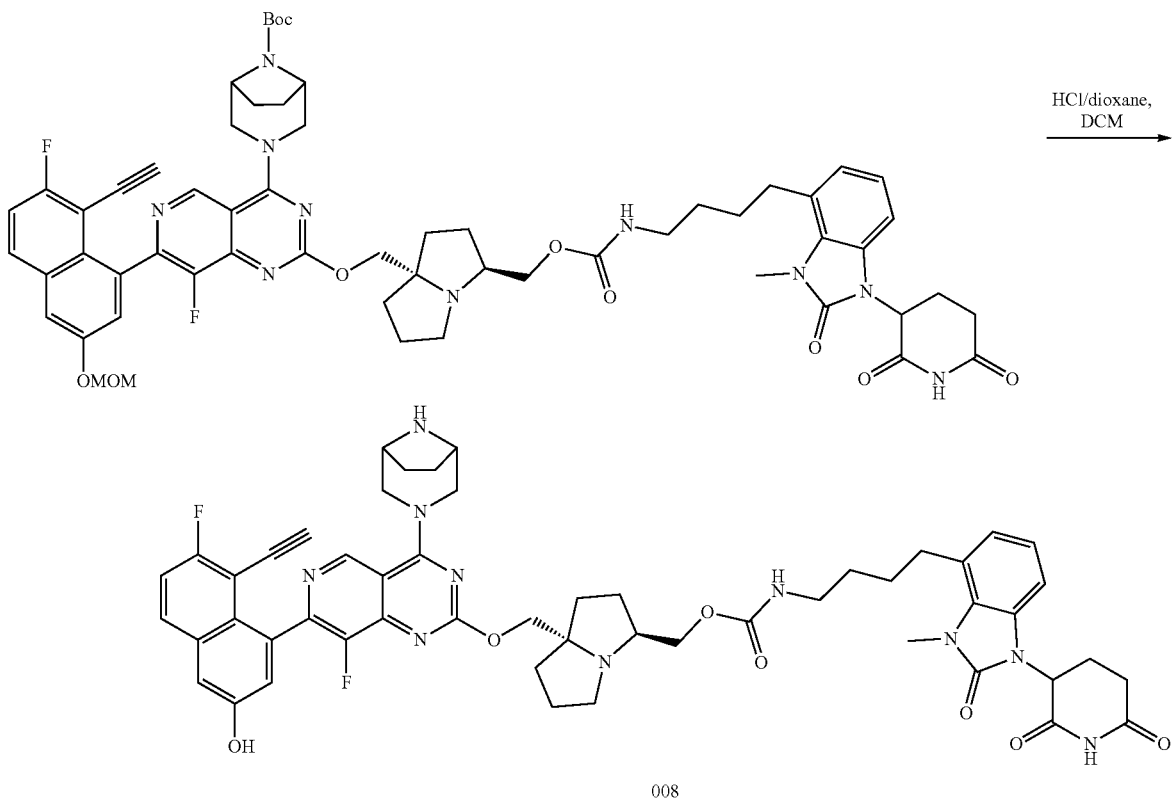

008

To a solution of tert-butyl 3-[2-[[(3S,8S)-3-[4-[1-(2,6-dioxo-3-piperidyl)-3-methyl-2-oxo-benzimidazol-4-yl]butylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 26.9 μmol) in DCM (5 mL) was added HCl/dioxane (4.00 M, 1.00 mL). The mixture was stirred at 25° C. for 2 hrs. Upon completion, the reaction mixture concentrated in vacuo, then the residue was purified by prep-HPLC (column: Phenomenex Luna C18 150*25 mm*10 μm; mobile phase: [water (FA)-ACN]; B %: 5%-35%, 8 min) to afford the title compound (6.22 mg, 22% yield, FA salt) as yellow solid. $^1$H NMR (400 MHz, DMSO-$d_6$) δ 11.08 (dt, J=3.6, 5.6 Hz, 1H), 9.03 (s, 1H), 7.97 (dd, J=6.0, 9.2 Hz, 1H), 7.46 (t, J=9.2 Hz, 1H), 7.39 (d, J=2.4 Hz, 1H), 7.28-7.20 (m, 1H), 7.17 (d, J=2.0 Hz, 1H), 6.99-6.90 (m, 2H), 6.85 (dd, J=3.2, 5.2 Hz, 1H), 5.35 (dd, J=5.2, 12.4 Hz, 1H), 4.48 (d, J=11.2 Hz, 1H), 4.31 (d, J=12.0 Hz, 1H), 4.17-4.07 (m, 3H), 4.03 (s, 1H), 3.93 (s, 1H), 3.66-3.59 (m, 6H), 3.53 (s, 3H), 3.02 (d, J=6.4 Hz, 2H), 2.86 (d, J=8.8 Hz, 2H), 2.74-2.69 (m, 2H), 2.59 (d, J=2.4 Hz, 1H), 2.08-1.96 (m, 2H), 1.77-1.48 (m, 16H); LC-MS (ESI$^+$) m/z 969.3 (M+H)$^+$.

Example 27. Synthesis of Compound 007 a) Synthesis of Tert-butyl N-[5-[1-(2,6-dioxo-3-piperidyl)-3-methyl-2-oxo-benzimidazol-4-yl]pentyl] carbamate

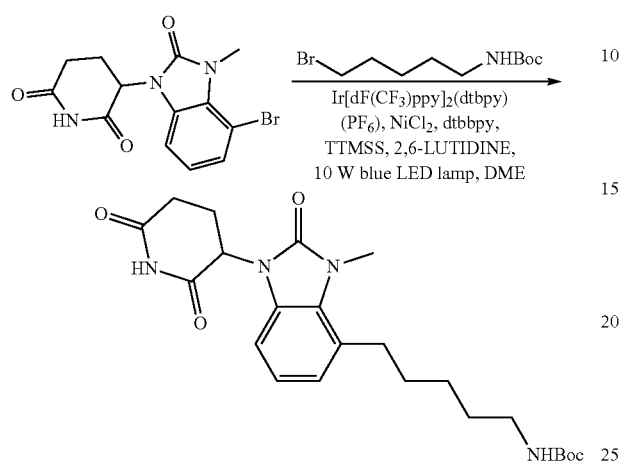

To an 15 mL vial equipped with a stir bar was added 3-(4-bromo-3-methyl-2-oxo-benzimidazol-1-yl)piperidine-2,6-dione (500 mg, 1.48 mmol), tert-butyl N-(5-bromopentyl)carbamate (511 mg, 1.92 mmol, CAS #83948-54-3), Ir[dF(CF$_3$)ppy]$_2$(dtbpy)(PF$_6$) (33.1 mg, 29.5 μmol), NiCl$_2$·dtbbpy (17.6 mg, 44.3 μmol), TTMSS (367 mg, 1.48 mmol), 2,6-Lutidine (316 mg, 2.96 mmol) in DME (5 mL). The vial was sealed and placed under N$_2$. The reaction was stirred and irradiated with a 10 W blue LED lamp (3 cm away), with cooling water to keep the reaction temperature at 25° C. for 14 hrs. Upon completion, the reaction mixture was filtered and concentrated in vacuo to produce a residue. The residue was purified by prep-HPLC (column: Phenomenex luna C18 250*50 mm*10 μm; mobile phase: [water (FA)-ACN]; B %: 35%-65%, 30 min) to afford the title compound (430 mg, 65% yield) as white solid. LC-MS (ESI$^+$) m/z 345.1 (M−100+H)$^+$.

b) Synthesis of 3-[4-(5-Aminopentyl)-3-methyl-2-oxo-benzimidazol-1-yl]piperidine-2,6-dione

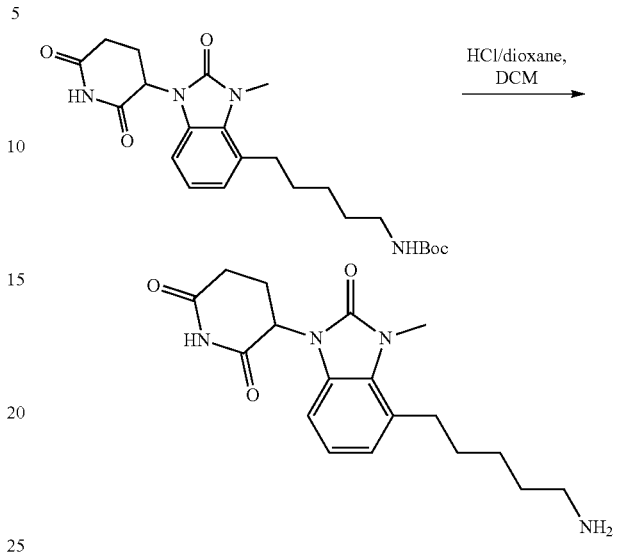

To a solution of tert-butyl N-[5-[1-(2,6-dioxo-3-piperidyl)-3-methyl-2-oxo-benzimidazol-4-yl]pentyl] carbamate (200 mg, 449 μmol) in DCM (5 mL) was added HCl/dioxane (4.00 M, 3.00 mL). The mixture was stirred at 25° C. for 1 hr. Upon completion, the mixture was concentrated in vacuo to afford the title compound (150 mg, 87% yield, HCl salt) as yellow solid. LC-MS (ESI$^+$) m/z 344.9 (M+H)$^+$.

c) Synthesis of Tert-butyl 3-[2-[[(3S,8S)-3-[5-[1-(2,6-dioxo-3-piperidyl)-3-methyl-2-oxo-benzimidazol-4-yl] pentylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

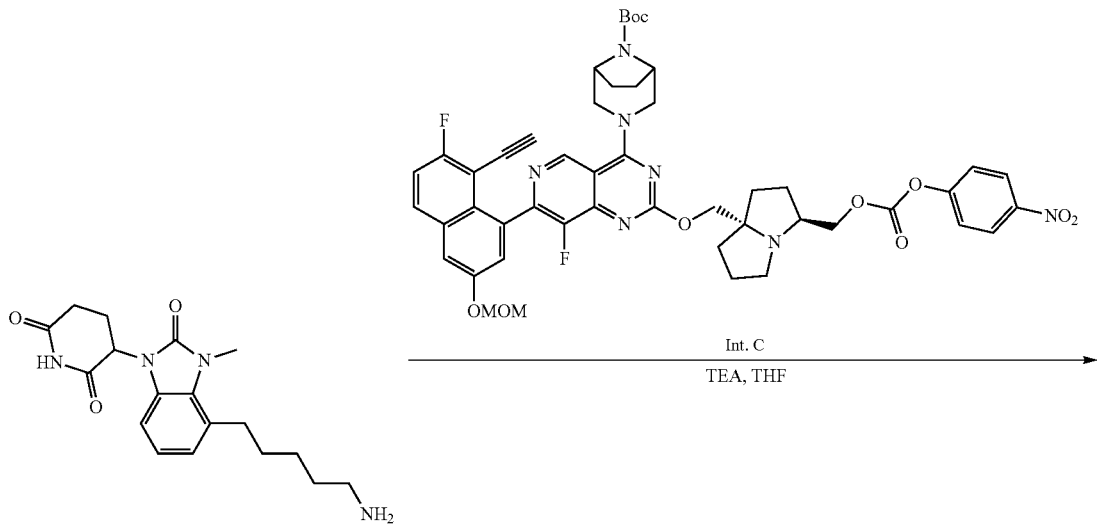

965

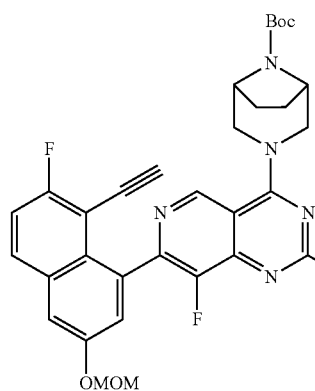

-continued

966

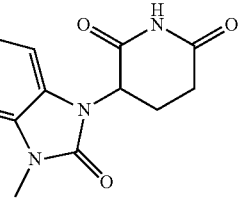

To a solution of Int. C (60.0 mg, 65.0 μmol) and 3-[4-(5-aminopentyl)-3-methyl-2-oxo-benzimidazol-1-yl]piperidine-2,6-dione (49.5 mg, 130 μmol, HCl salt) in THF (4 mL) was added TEA (46.1 mg, 455 μmol). The mixture was stirred at 25° C. for 1 hr under N₂ atmosphere. Upon completion, the mixture was concentrated in vacuo to give a residue. The residue was purified by prep-HPLC (column: Welch Ultimate C18 150*25 mm*5 μm; mobile phase: [water (FA)-ACN]; B %: 25%-55%, 10 min) to afford the title compound (13.0 mg, 17% yield) as yellow solid. LC-MS (ESI⁺) m/z 1128.7 (M+H)⁺.

d) Synthesis of [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl] methyl N-[5-[1-(2,6-dioxo-3-piperidyl)-3-methyl-2-oxo-benzimidazol-4-yl]pentyl]carbamate (007)

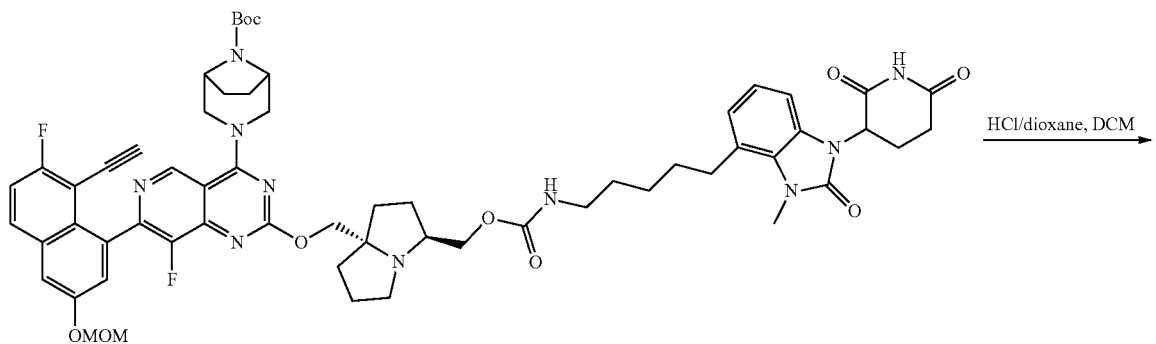

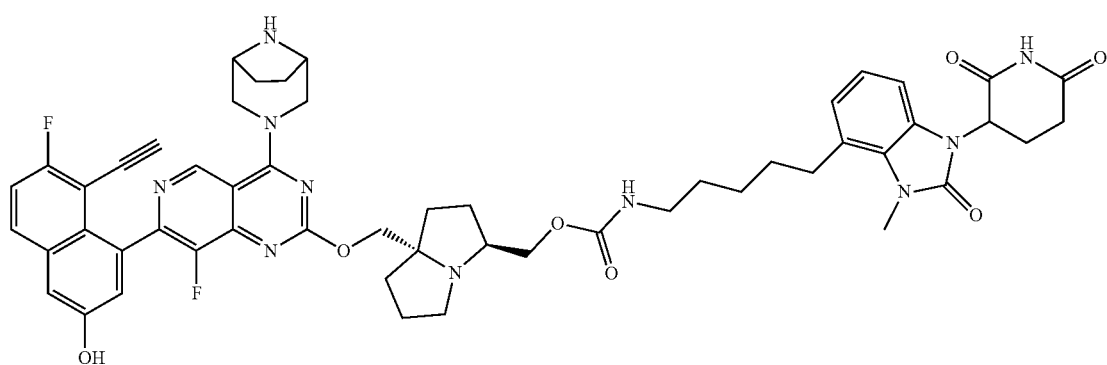

007

To a solution of tert-butyl 3-[2-[[(3S,8S)-3-[5-[1-(2,6-dioxo-3-piperidyl)-3-methyl-2-oxo-benzimidazol-4-yl]pentylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (15.0 mg, 11.3 μmol) in DCM (1 mL) was added HCl/dioxane (4.00 M, 1.27 mL). The mixture was stirred at 25° C. for 1 hr. Upon completion, the mixture was concentrated in vacuo to give a residue. The residue was purified by prep-HPLC (column: Phenomenex Luna C18 150*25 mm*0 μm; mobile phase: [water (FA)-ACN]; B %: 7%-37%, 8 min) to afford the title compound (10.8 mg, 97% yield) as white solid. ¹H NMR (400 MHz, DMSO-d₆) δ 11.10 (s, 1H), 9.04 (s, 1H), 8.01-7.93 (m, 1H), 7.46 (t, J=9.2 Hz, 1H), 7.39 (d, J=2.4 Hz, 1H), 7.21 (s, 1H), 7.17 (d, J=2.4 Hz, 1H), 6.97-6.90 (m, 2H), 6.88-6.81 (m, 1H), 5.39-5.31 (m, 1H), 4.48 (br d, J=11.6 Hz, 1H), 4.32 (d, J=12.0 Hz, 1H), 4.15-4.01 (m, 4H), 3.93 (s, 1H), 3.63-3.57 (m, 6H), 3.54 (s, 3H), 3.25-3.22 (m, 2H), 3.00-2.95 (m, 2H), 2.88-2.84 (m, 2H), 2.77-2.70 (m, 2H), 2.67-2.56 (m, 2H), 2.08-1.95 (m, 2H), 1.77-1.67 (m, 8H), 1.65-1.49 (m, 4H), 1.48-1.41 (m, 2H), 1.40-1.31 (m, 2H); LC-MS (ESI⁺) m/z 983.3 (M+H)⁺.

Example 28. Synthesis of Compound 012 a) Synthesis of Tert-butyl N-(9-bromononyl)carbamate

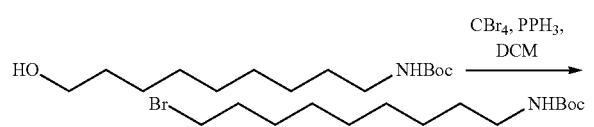

To a solution of tert-butyl N-(9-hydroxynonyl)carbamate (3.00 g, 11.5 mmol, CAS #1397043-36-5) in DCM (15 mL) was added PPh₃ (4.55 g, 17.3 mmol) and CBr₄ (5.75 g, 17.3 mmol). The mixture was stirred at 25° C. for 16 hrs. Upon completion, the mixture was concentrated in vacuo. The residue was purified by column chromatography (SiO₂, PE:EA=20:1) to afford the title compound (1.71 g, 45% yield) as white solid. ¹H NMR (400 MHz, CDCl₃) δ 4.50 (s, 1H), 3.56-3.39 (m, 2H), 3.15-3.08 (m, 2H), 1.90-1.73 (m, 2H), 1.48-1.42 (m, 12H), 1.30 (s, 9H).

b) Synthesis of Tert-butyl N-[9-[1-(2,6-dioxo-3-piperidyl)-3-methyl-2-oxo-benzimidazol-4-yl]nonyl]carbamate

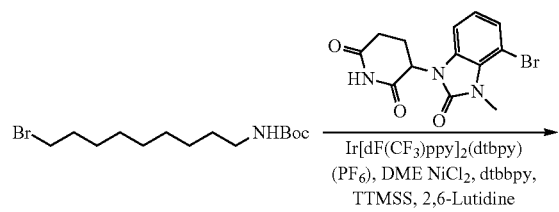

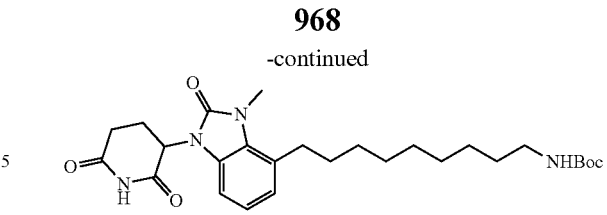

To an 15 mL vial equipped with a stir bar was added 3-(4-bromo-3-methyl-2-oxo-benzimidazol-1-yl) piperidine-2,6-dione (670 mg, 1.98 mmol), tert-butyl N-(9-bromononyl)carbamate (830 mg, 2.58 mmol), Ir[dF(CF₃)ppy]₂(dtbpy)(PF₆) (22.2 mg, 19.8 μmol), NiCl₂·dtbbpy (15.7 mg, 39.6 μmol), TTMSS (492 mg, 1.98 mmol), 2,6-Lutidine (424 mg, 3.96 mmol) in DME (40 mL). The vial was sealed and placed under N₂ atmosphere. The reaction was stirred and irradiated with a 10 W blue LED lamp (3 cm away), with cooling water to keep the reaction temperature at 25° C. for 14 hrs. Upon completion, the mixture was filtered and concentrated in vacuo. The residue was purified by reversed phase (0.1% FA) to afford the title compound (350 mg, 35% yield) as yellow solid. ¹H NMR (400 MHz, DMSO-d₆) δ 11.08 (s, 1H), 6.98-6.92 (m, 2H), 6.88-6.83 (m, 1H), 6.74 (t, J=5.6 Hz, 1H), 5.36 (dd, J=5.6, 12.4 Hz, 1H), 3.54 (s, 3H), 2.91-2.85 (m, 4H), 2.76-2.56 (m, 3H), 2.03-1.96 (m, 1H), 1.63-1.54 (m, 2H), 1.43-1.38 (m, 2H), 1.36 (s, 9H), 1.35-1.18 (m, 10H); LC-MS (ESI⁺) m/z 501.2 (M+H)⁺.

c) Synthesis of 3-[4-(9-Aminononyl)-3-methyl-2-oxo-benzimidazol-1-yl]piperidine-2,6-dione

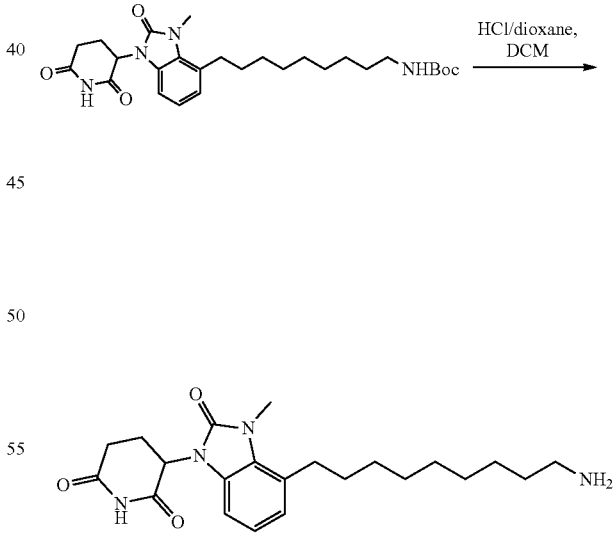

To a solution of tert-butyl N-[9-[1-(2,6-dioxo-3-piperidyl)-3-methyl-2-oxo-benzimidazol-4-yl] nonyl] carbamate (60.0 mg, 119 μmol) in DCM (1 mL) was added HCl/dioxane (4 M, 1.00 mL). The mixture was stirred at 25° C. for 2 hrs. On completion, the mixture was concentrated in vacuo to afford the title compound (52.0 mg, 99% yield, HCl salt) as yellow solid. LC-MS (ESI⁺) m/z 401.1 (M+H)⁺.

d) Synthesis of Tert-butyl 3-[2-[[(3S,8S)-3-[9-[1-(2,6-dioxo-3-piperidyl)-3-methyl-2-oxo-benzimidazol-4-yl] nonylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

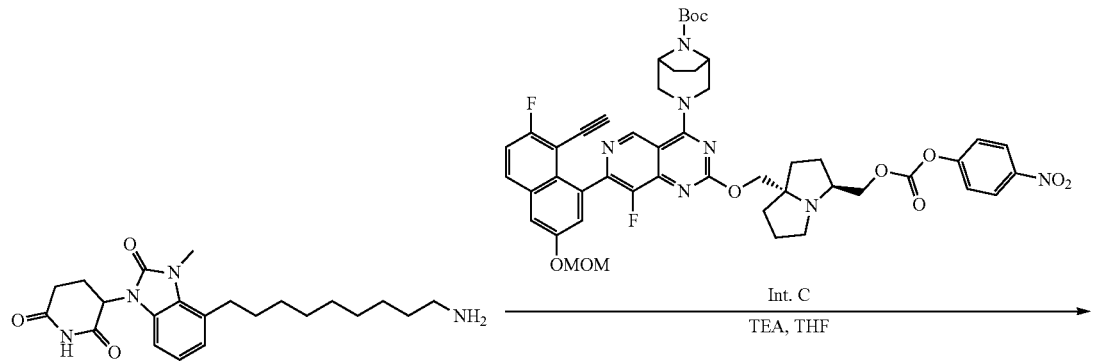

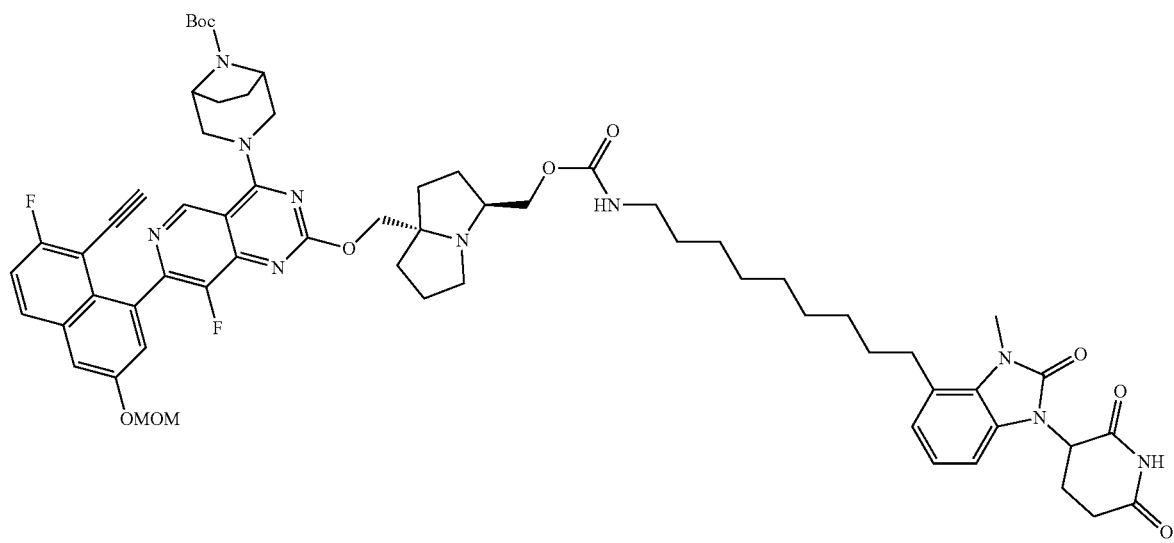

To a solution of 3-[4-(9-aminononyl)-3-methyl-2-oxo-benzimidazol-1-yl]piperidine-2,6-dione (42.6 mg, 97.6 μmol, HCl salt) in THF (5 mL) was added TEA (19.7 mg, 195 μmol), the mixture was stirred at 25° C. for 0.5 hr, then the solution of Int. C (60.0 mg, 65.0 μmol) in THF (5 mL) was added to above solution. The mixture was stirred at 25° C. for 16 hrs. Upon completion, the mixture was concentrated in vacuo. The residue was purified by prep-HPLC (column: Phenomenex luna C18 150*25 mm*10 μm; mobile phase: [water (FA)-ACN]; B %: 34%-64%, 15 min) to afford the title compound (47.0 mg, 61% yield) as off-white solid. LC-MS (ESI$^+$) m/z 1183.5 (M+H)$^+$.

e) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methyl N-[5-[1-(2,6-dioxo-3-piperidyl)-3-methyl-2-oxo-benzimidazol-4-yl]pentyl]carbamate (007)

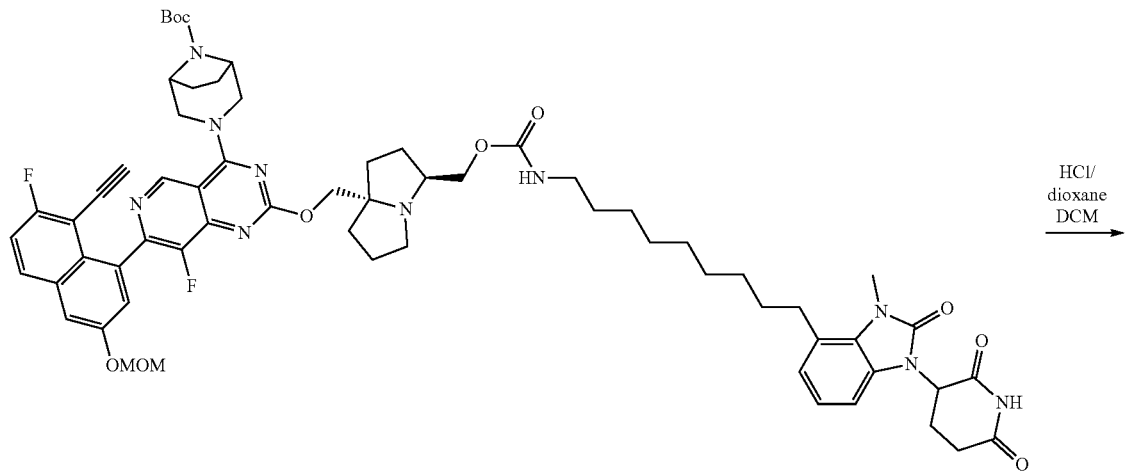

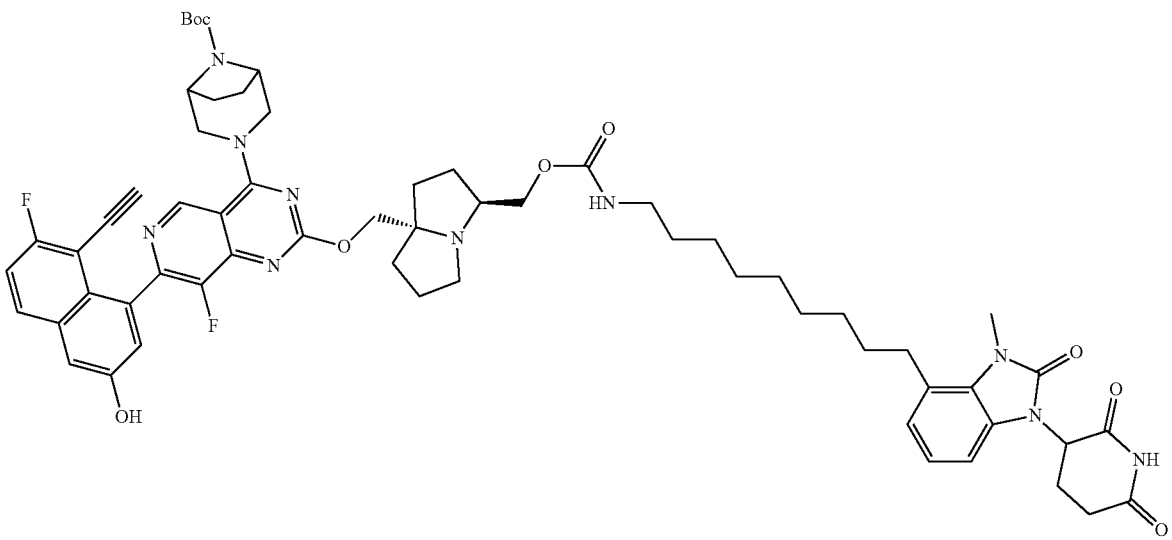

007

To a solution of tert-butyl 3-[2-[[(3S,8S)-3-[9-[1-(2,6-dioxo-3-piperidyl)-3-methyl-2-oxo-benzimidazol-4-yl]nonylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (47.0 mg, 39.7 μmol) in DCM (3 mL) was added HCl/dioxane (4 M, 1.88 mL). The mixture was stirred at 25° C. for 0.5 hr. Upon completion, the mixture was concentrated in vacuo. The residue was purified by prep-HPLC (column: Phenomenex luna C18 150*25 mm*10 μm; mobile phase: [water (FA)-ACN]; B %: 17%-47%, 15 min) to afford the title compound (19.7 mg, 45% yield) as yellow solid. $^1$H NMR (400 MHz, DMSO-$d_6$) δ 11.09 (s, 1H), 9.03 (s, 1H), 8.21 (s, 1H), 7.97 (dd, J=6.0, 8.8 Hz, 1H), 7.46 (t, J=9.2 Hz, 1H), 7.39 (d, J=2.4 Hz, 1H), 7.17 (d, J=2.0 Hz, 2H), 6.97-6.90 (m, 2H), 6.87-6.81 (m, 1H), 5.35 (dd, J=5.2, 12.4 Hz, 1H), 4.49 (d, J=12.4 Hz, 1H), 4.33 (d, J=12.0 Hz, 1H), 4.13-4.07 (m, 2H), 4.04-4.00 (m, 1H), 3.66-3.62 (m, 4H), 3.53 (s, 3H), 3.28-3.18 (m, 4H), 2.96-2.92 (m, 1H), 2.89-2.84 (m, 2H), 2.77-2.61 (m, 5H), 2.07-1.96 (m, 2H), 1.77-1.64 (m, 10H), 1.60-1.46 (m, 4H), 1.38-1.34 (m, 2H), 1.32-1.13 (m, 10H); LC-MS (ESI$^+$) m/z 1039.5 (M+H)$^+$.

Example 29. Synthesis of Compound 014 a) Synthesis of Tert-butyl N-(10-bromodecyl)carbamate

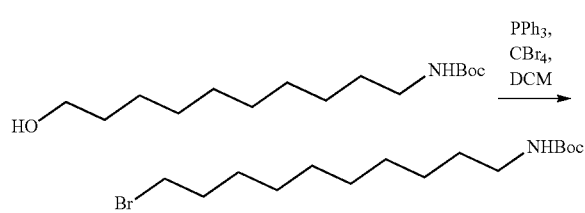

To a solution of tert-butyl N-(10-hydroxydecyl)carbamate (3.50 g, 12.8 mmol, CAS #173606-54-7) in DCM (150 mL) was added PPh$_3$ (4.36 g, 16.6 mmol) and CBr$_4$ (5.52 g, 16.6 mmol) under N$_2$ atmosphere. Then the mixture was stirred at 25° C. for 2.5 hrs under N$_2$ atmosphere. On completion, the mixture was concentrated in vacuo to provide a residue. The residue was purified by column chromatography (SiO$_2$, PE/EA=20/1 to 10/1) to afford the title compound (3.60 g, 83% yield) as yellow solid. $^1$H NMR (400 MHz, CDCl$_3$) δ 4.50 (s, 1H), 3.41 (t, J=6.8 Hz, 2H), 3.17-3.02 (m, 2H), 1.90-1.81 (m, 2H), 1.55-1.32 (m, 14H), 1.31-1.27 (m, 9H).

b) Synthesis of Tert-butyl N-[10-[1-(2,6-dioxo-3-piperidyl)-3-methyl-2-oxo-benzimidazol-4-yl]decyl]carbamate

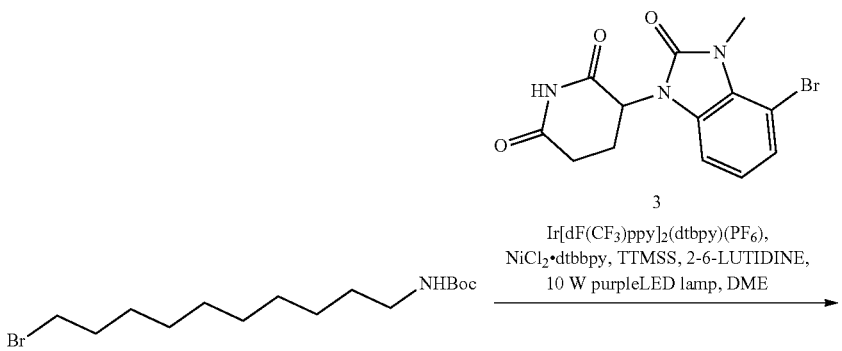

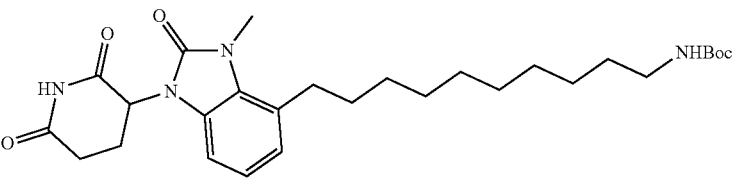

To an 15 mL vial equipped with a stir bar was added 3-(4-bromo-3-methyl-2-oxo-benzimidazol-1-yl)piperidine-2,6-dione (600 mg, 1.77 mmol), tert-butyl N-(10-bromodecyl)carbamate (775 mg, 2.31 mmol), Ir[dF(CF$_3$)ppy]$_2$(dtbpy)(PF$_6$) (39.8 mg, 35.4 μmol), NiCl$_2$·dtbbpy (21.1 mg, 53.2 μmol), TTMSS (441 mg, 1.77 mmol) and 2,6-lutidine (380 mg, 3.55 mmol) in DME (30 mL). The vial was sealed and placed under nitrogen. The reaction was stirred and irradiated with a purple 10 W LED lamp (3 cm away), with cooling water to keep the reaction temperature at 25° C. for 14 hrs. Upon completion, the mixture was concentrated in vacuo to provide a residue. The residue was purified by prep-HPLC (column: UniSil 10-120 C18 50×250 mm; mobile phase: [water (FA)-ACN]; B %: 45%-80%, 22 min) to afford the title compound (500 mg, 54% yield) as yellow solid. $^1$H NMR (400 MHz, CDCl$_3$) δ 8.11 (s, 1H), 7.03-6.96 (m, 1H), 6.90 (d, J=7.6 Hz, 1H), 6.66 (d, J=8.0 Hz, 1H), 5.25-5.16 (m, 1H), 4.50 (s, 1H), 3.67 (s, 3H), 3.15-3.05 (m, 2H), 2.99-2.88 (m, 3H), 2.87-2.69 (m, 2H), 2.26-2.17 (m, 1H), 1.70-1.61 (m, 2H), 1.45 (s, 12H), 1.41-1.35 (m, 2H), 1.29 (s, 9H).

c) Synthesis of 3-[4-(10-Aminodecyl)-3-methyl-2-oxo-benzimidazol-1-yl]piperidine-2,6-dione

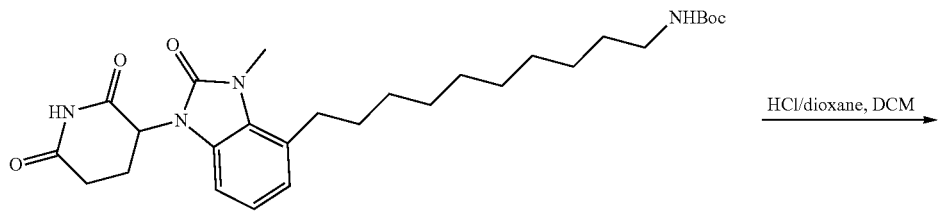

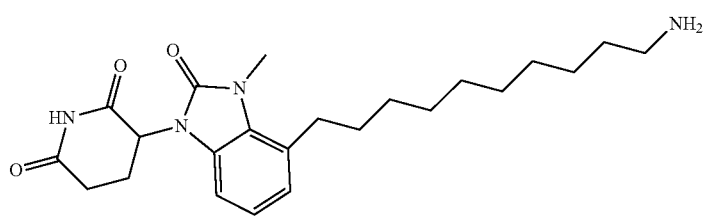

To a solution of tert-butyl N-[10-[1-(2,6-dioxo-3-piperidyl)-3-methyl-2-oxo-benzimidazol-4-yl]decyl]carbamate (215 mg, 417 μmol) in DCM (5 mL) was added HCl (4.00 M, 3.58 mL) and the mixture was stirred at 25° C. for 2 hrs. Upon completion, the mixture was concentrated in vacuo to afford the title compound (180 mg, 95% yield, HCl salt) as white solid. LC-MS (ESI$^+$) m/z 415.0 (M+H)$^+$.

d) Synthesis of Tert-butyl 3-[2-[[(3S,8S)-3-[10-[1-(2,6-dioxo-3-piperidyl)-3-methyl-2-oxo-benzimidazol-4-yl] decylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

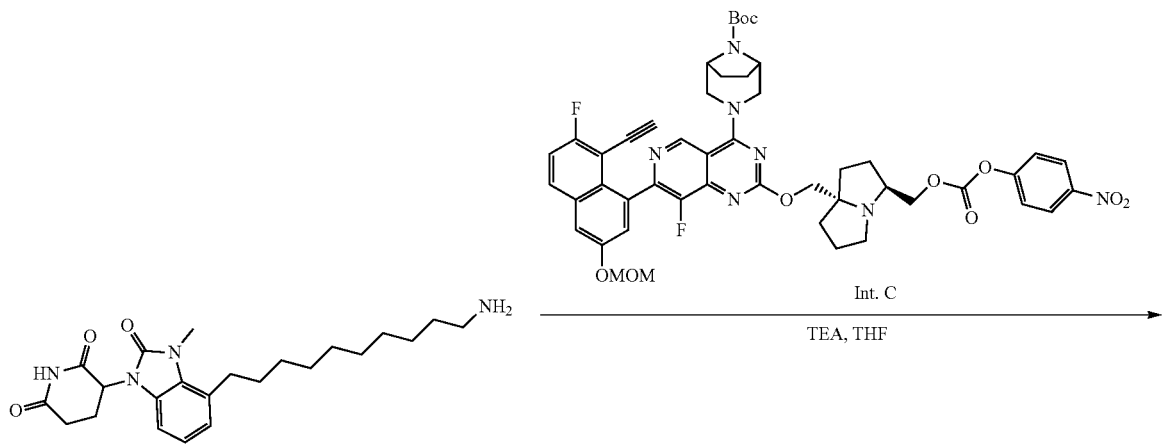

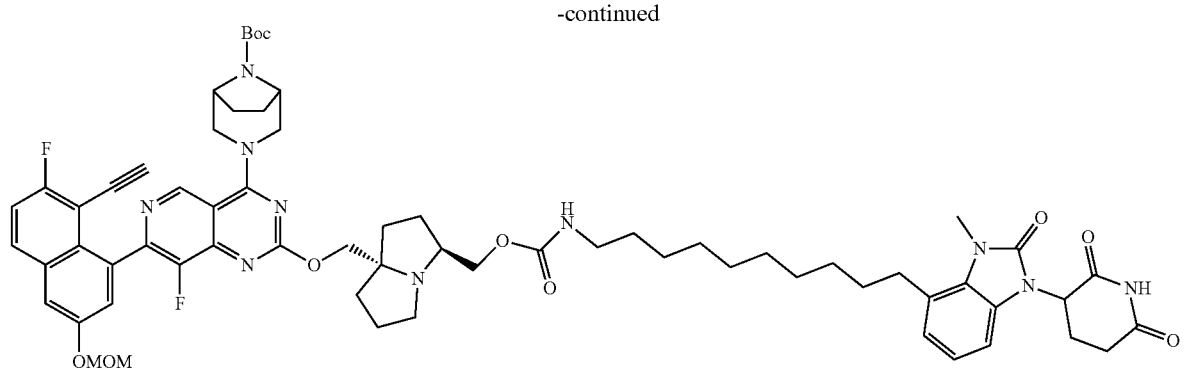

To a solution of 3-[4-(10-aminodecyl)-3-methyl-2-oxo-benzimidazol-1-yl]piperidine-2,6-dione (62.6 mg, 138 μmol, HCl salt) and Int. C (64.0 mg, 69.4 μmol) in THF (4 mL) was added TEA (49.1 mg, 485 μmol). The mixture was stirred at 25° C. for 2 hrs under N₂ atmosphere. Upon completion, the mixture was concentrated in vacuo to afford the title compound (45.0 mg, 54% yield) as yellow oil. LC-MS (ESI⁺) m/z 1197.6 (M+H)⁺.

e) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methyl N-[10-[1-(2,6-dioxo-3-piperidyl)-3-methyl-2-oxo-benzimidazol-4-yl]decyl]carbamate (014)

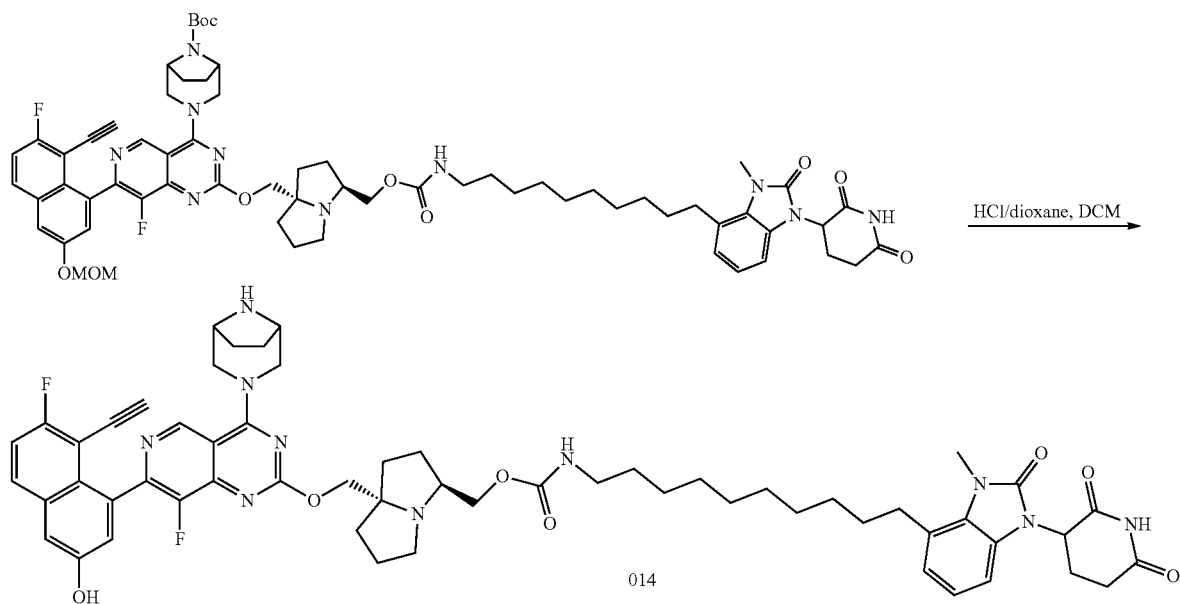

To a solution of tert-butyl 3-[2-[[(3S,8S)-3-[10-[1-(2,6-dioxo-3-piperidyl)-3-methyl-2-oxo-benzimidazol-4-yl] decylcarbamoyloxymethyl]-1,2,3,5,6,7-hexahydropyr-rolizin-8-yl]methoxy]-7-[8-ethynyl-7-fluoro-3-(methoxymethoxy)-1-naphthyl]-8-fluoro-pyrido[4,3-d] pyrimidin-4-yl]-3,8-diazabicyclo[3.2.1]octane-8-carboxylate (35.0 mg, 14.3 μmol) in DCM (5 mL) was added HCl/dioxane (4.00 M, 1.75 mL). The mixture was stirred at 25° C. for 1 hr. Upon completion, the mixture was concentrated in vacuo to give a residue. The residue was purified by prep-HPLC (column: Welch Ultimate C18 150*30 mm*5 μm; mobile phase: [water (TFA)-ACN]; B %: 27%-57%, 10 min) to afford the title compound (11.1 mg, 64% yield, TFA salt) as yellow solid. ¹H NMR (400 MHz, DMSO-d₆) δ 11.09 (s, 1H), 10.45-10.36 (m, 1H), 10.23 (s, 1H), 9.43-9.33 (m, 1H), 9.17 (s, 1H), 9.13-9.04 (m, 1H), 8.04-7.95 (m, 1H), 7.41 (d, J=2.4 Hz, 1H), 7.26-7.15 (m, 2H), 7.01-6.91 (m, 2H), 6.88-6.81 (m, 1H), 5.39-5.32 (m, 1H), 4.77-4.66 (m, 1H), 4.62-4.52 (m, 2H), 4.36-4.28 (m, 2H), 4.23 (s, 2H), 3.94-3.83 (m, 3H), 3.53 (s, 3H), 3.01-2.94 (m, 2H), 2.90-2.83 (m, 3H), 2.77-2.63 (m, 4H), 2.59 (s, 3H), 2.32-2.27 (m, 1H), 2.18-1.87 (m, 12H), 1.62-1.53 (m, 2H), 1.43-1.21 (m, 14H); LC-MS (ESI$^+$) m/z 1053.4 (M+H)$^+$.

Example 30. Synthesis of Compound 011 a) Synthesis of Tert-butyl N-[11-[1-(2,6-dioxo-3-piperidyl)-3-methyl-2-oxo-benzimidazol-4-yl]undecyl] carbamate

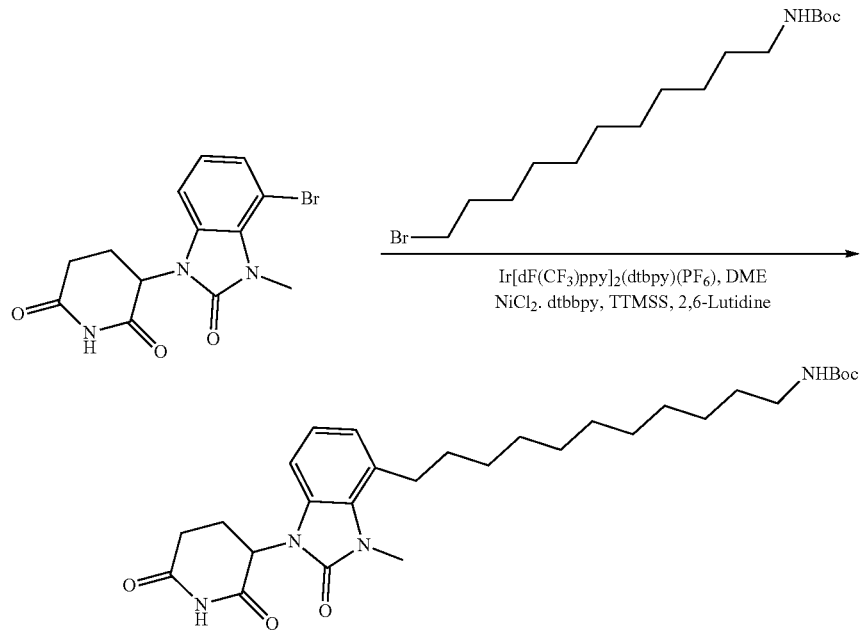

To an 15 mL vial equipped with a stir bar was added 3-(4-bromo-3-methyl-2-oxo-benzimidazol-1-yl) piperidine-2,6-dione (742 mg, 2.20 mmol), tert-butyl N-(11-bromoundecyl)carbamate (1.00 g, 2.85 mmol, CAS #463930-53-2), Ir[dF(CF$_3$)ppy]$_2$(dtbpy)(PF$_6$) (49.2 mg, 43.9 µmol) NiCl$_2$·dtbbpy (26.2 mg, 65.8 µmol), TTMSS (545 mg, 2.20 mmol), 2,6-Lutidine (235 mg, 2.20 mmol) in DME (5 mL). The vial was sealed and placed under nitrogen. The reaction was stirred and irradiated with a 10 W blue LED lamp (3 cm away), with cooling water to keep the reaction temperature at 25° C. for 14 hrs. Upon completion, the mixture was concentrated in vacuo. The crude product was purified by reversed-phase HPLC (0.1% FA condition) to afford the title compound (600 mg, 51% yield) as faint yellow solid. $^1$H NMR (400 MHz, DMSO-d$_6$) δ 11.08 (s, 1H), 6.98-6.91 (m, 2H), 6.88-6.82 (m, 1H), 6.74 (t, J=5.2 Hz, 1H), 5.36 (dd, J=5.2, 12.4 Hz, 1H), 3.54 (s, 3H), 2.88 (dd, J=5.2, 10.8 Hz, 4H), 2.77-2.54 (m, 3H), 2.04-1.95 (m, 1H), 1.65-1.53 (m, 2H), 1.36 (s, 9H), 1.35-1.20 (m, 14H).

b) Synthesis of 3-[4-(11-Aminoundecyl)-3-methyl-2-oxo-benzimidazol-1-yl]piperidine-2,6-dione

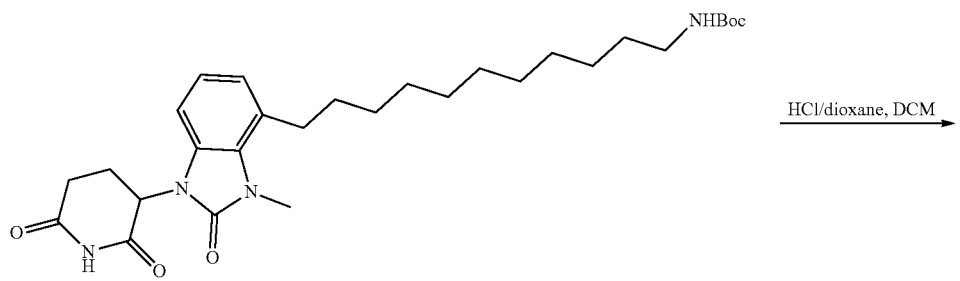

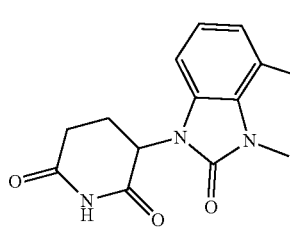

To a solution of tert-butyl N-[11-[1-(2,6-dioxo-3-piperidyl)-3-methyl-2-oxo-benzimidazol-4-yl] undecyl]carbamate (200 mg, 378 μmol) in DCM (1 mL) was added HCl/dioxane (4 M, 2.00 mL). The mixture was stirred at 25° C. for 1 hr. Upon completion, the mixture was concentrated in vacuo to afford the title compound (140 mg, 86% yield, HCl salt) as faint brown solid. LC-MS (ESI+) m/z 429.2 (M+H)+.

c) Synthesis of Tert-butyl 3-[2-[[(3S,8S)-3-[1-[1-(2,6-dioxo-3-piperidyl)-3-methyl-2-oxo-benzimidazol-4-yl]undecylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoropyrido[4,3-d]pyrimidin-4-yl]-3,8-diazabicyclo[3.2.1]octane-8-carboxylate

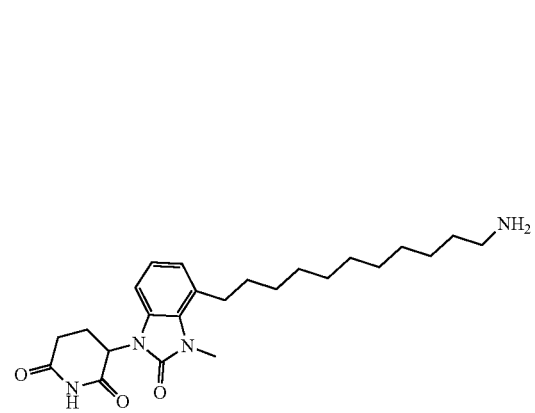

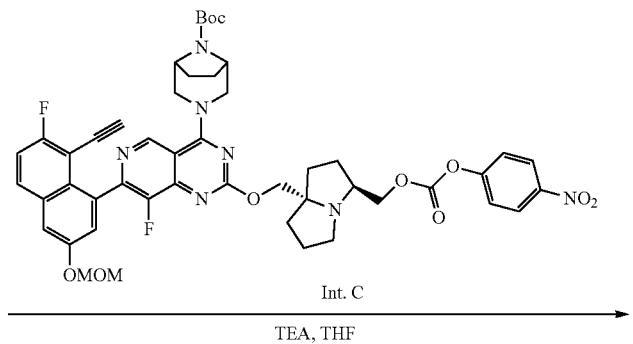

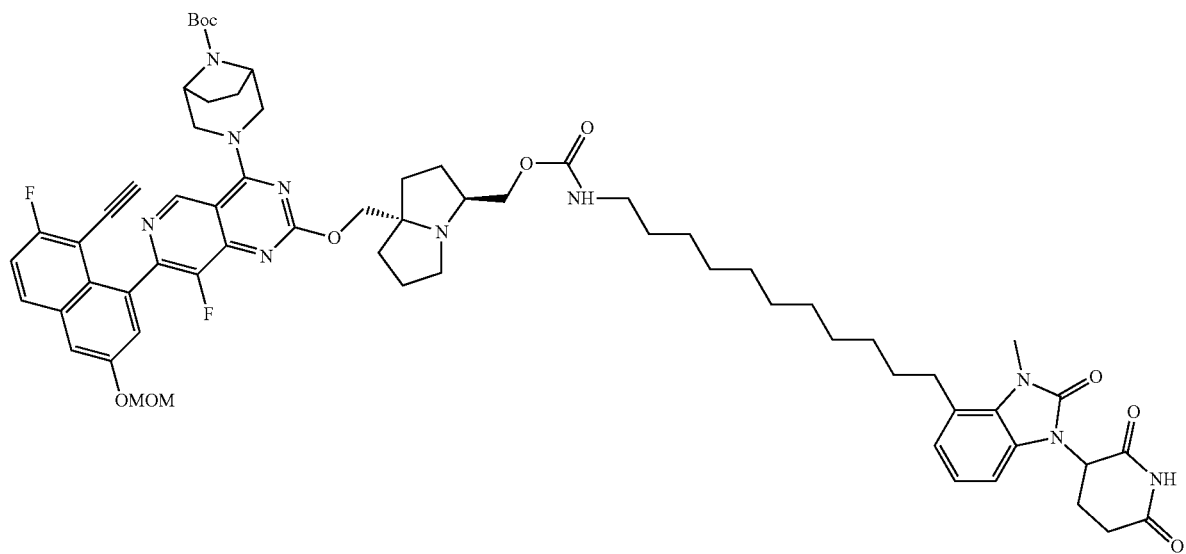

To a solution of Int. C (64.0 mg, 69.4 μmol), 3-[4-(11-aminoundecyl)-3-methyl-2-oxo-benzimidazol-1-yl]piperidine-2,6-dione (44.9 mg, 96.5 μmol, HCl salt) in THF (1 mL) was added TEA (21.1 mg, 208 μmol). The mixture was degassed and purged with $N_2$ for 3 times, and then the mixture was stirred at 25° C. for 2 hrs under $N_2$ atmosphere. Upon completion, the mixture was concentrated in vacuo. The residue was purified by prep-HPLC (column: Phenomenex luna C18 150*25 mm*10 μm; mobile phase: [water (FA)-ACN]; B %: 38%-68%, 15 min) to afford the title compound (30.0 mg, 35% yield) as faint brown solid. LC-MS (ESI$^+$) m/z 606.2 (M+2H)/2$^+$.

d) Synthesis of [(3S,8S)-8-[[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl] oxymethyl]-1,2,3,5,6,7-hexahydropyrrolizin-3-yl] methylN-[11-[1-(2,6-dioxo-3-piperidyl)-3-methyl-2-oxo-benzimidazol-4-yl]undecyl]carbamate (011)

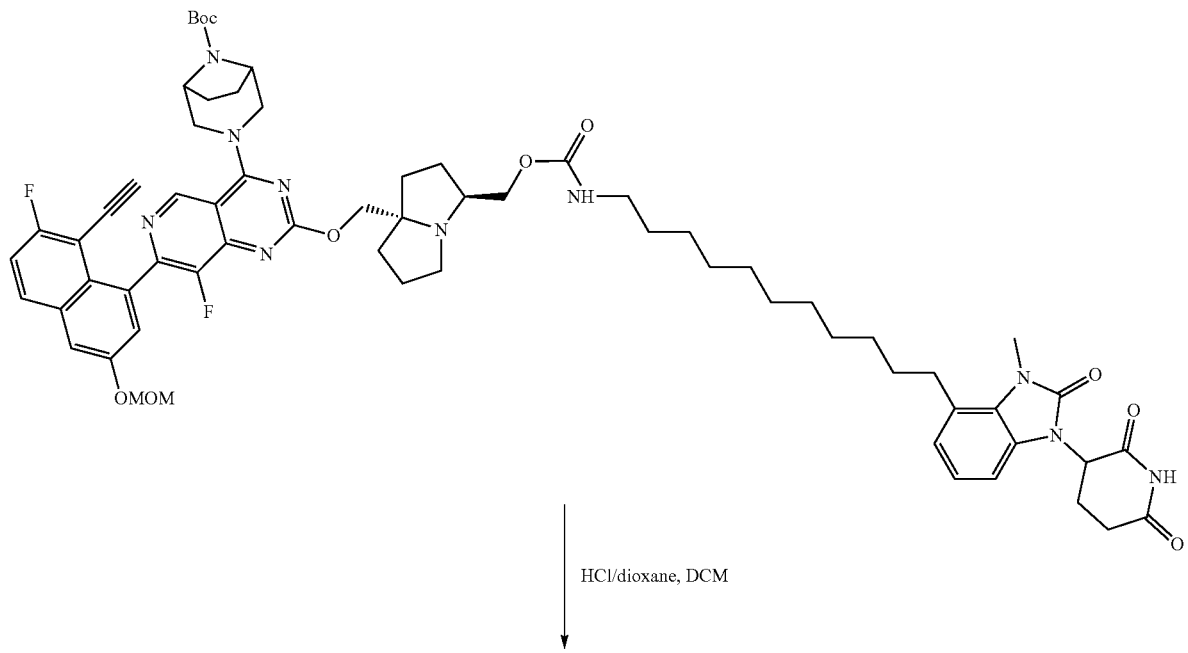

HCl/dioxane, DCM

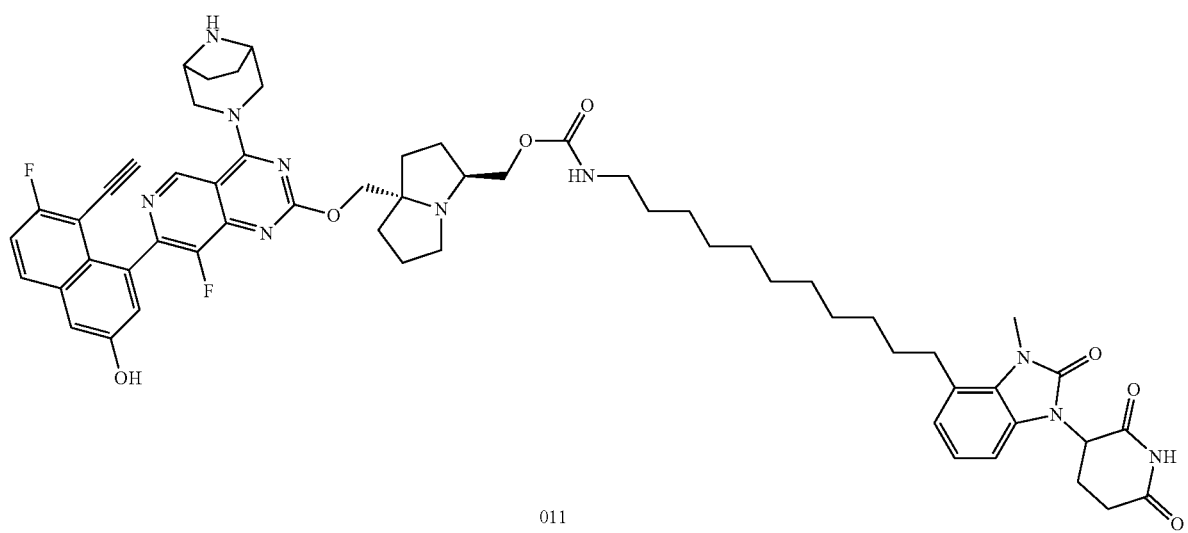

011

To a solution of tert-butyl 3-[2-[[(3S,8S)-3-[11-[1-(2,6-dioxo-3-piperidyl)-3-methyl-2-oxo-benzimidazol-4-yl]undecylcarbamoyloxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 24.7 μmol) in DCM (0.5 mL) was added HCl/dioxane (4 M, 1.00 mL). The mixture was stirred at 25° C. for 1 hr. On completion, the mixture was concentrated in vacuo. The residue was purified by prep-HPLC (column: Phenomenex luna C18 150*25 mm*10 μm; mobile phase: [water (FA)-ACN]; B %: 21%-51%, min) to afford the title compound (25.7 mg, 97% yield) as yellow solid. $^1$H NMR (400 MHz, DMSO-$d_6$) δ 11.10 (s, 1H), 9.04 (s, 1H), 8.21 (s, 1H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 2H), 7.00-6.91 (m, 2H), 6.84 (dd, J=3.2, 5.6 Hz, 1H), 5.36 (dd, J=5.2, 12.0 Hz, 1H), 4.54-4.44 (m, 1H), 4.36-4.29 (m, 1H), 4.13-4.07 (m, 2H), 4.02 (d, J=9.6 Hz, 1H), 3.95-3.91 (m, 1H), 3.65-3.62 (m, 2H), 3.53 (s, 3H), 2.94 (d, J=6.0 Hz, 2H), 2.88-2.85 (m, 1H), 2.78-2.69 (m, 4H), 2.65-2.61 (m, 2H), 2.61-2.58 (m, 2H), 2.07-1.98 (m, 2H), 1.78-1.64 (m, 11H), 1.60-1.48 (m, 4H), 1.40-1.33 (m, 4H), 1.33-1.15 (m, 14H); LC-MS (ESI$^+$) m/z 1067.7 (M+H)$^+$.

Example 32. Synthesis of Int. F

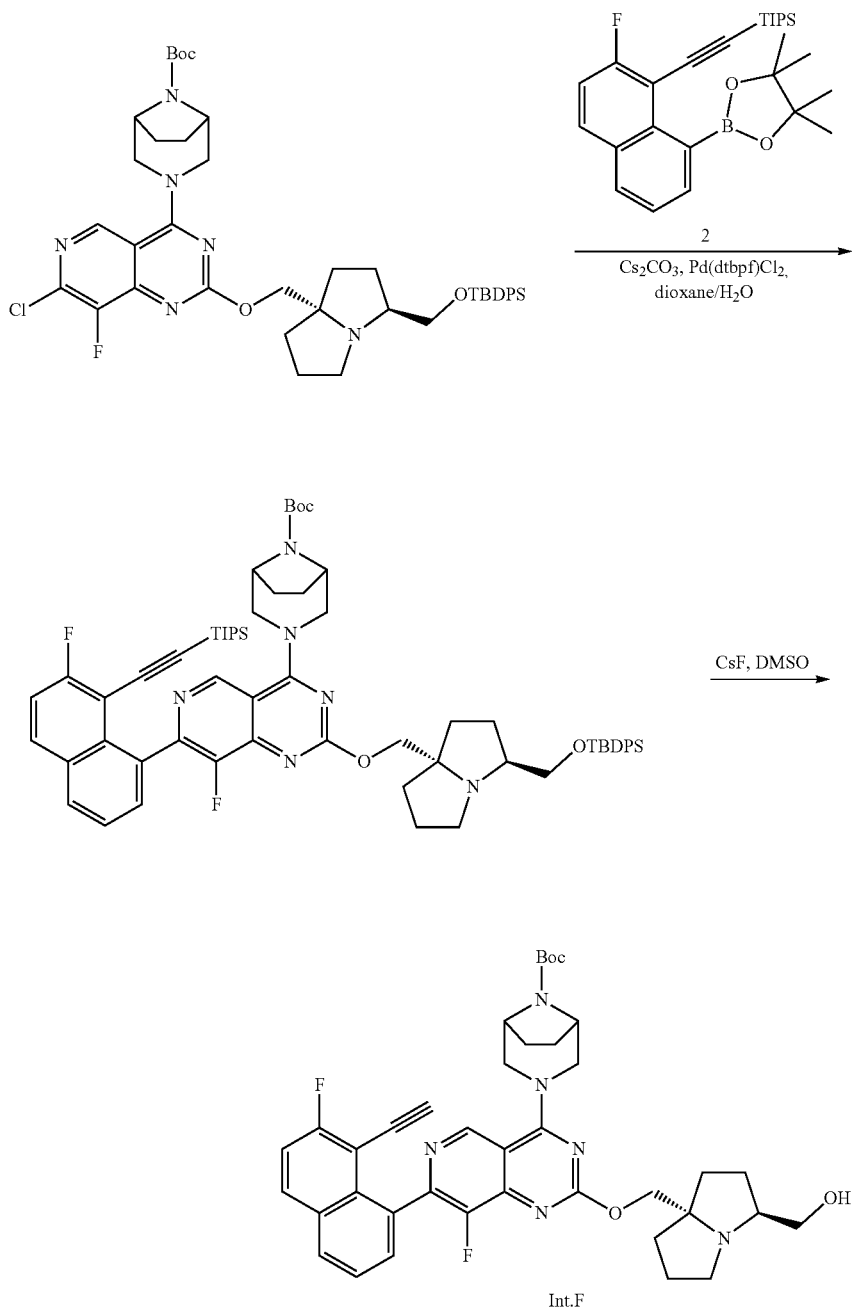

To a solution of 2-[2-fluoro-8-(4,4,5,5-tetramethyl-1,3,2-dioxaborolan-2-yl)-1-naphthyl]ethynyl-triisopropyl-silane (1.69 g, 3.74 mmol, CAS #2503307-87-5) and tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (2.00 g, 2.50 mmol) in dioxane (40 mL) and H₂O (8 mL) was added Cs₂CO₃ (2.44 g, 7.49 mmol) and ditert-butyl(cyclopentyl)phosphane; dichloropalladium; iron (325 mg, 499 μmol). The mixture was stirred at 100° C. for 1 hr under N₂ atmosphere. On completion, the mixture was concentrated in vacuo to give a residue and the residue was purified by column chromatography (SiO₂, DCM/MeOH=50/1 to 10/1) to give tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate (2.50 g, 86% yield) as brown solid. LC-MS (ESI⁺) m/z 1092.1 (M+H)⁺.

To a solution of tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate (2.50 g, 2.29 mmol) in DMSO (35 mL) was added CsF (1.04 g, 6.87 mmol). The mixture was stirred at 25° C. for 16 hrs. On completion, the reaction was quenched with H₂O (40 mL), extracted with ethyl acetate (3×100 mL), dried over anhydrous Na₂SO₄, filtered and the filtrate was concentrated in vacuo to give a residue. The residue was purified by column chromatography (SiO₂, DCM/MeOH=50/1 to 10/1) to give the title compound (1.30 g, 79% yield) as brown solid. ¹H NMR (400 MHz, CDCl₃) δ 8.99 (s, 1H), 8.01-7.91 (m, 2H), 7.66-7.55 (m, 2H), 7.34 (t, J=8.8 Hz, 1H), 4.65-4.50 (m, 2H), 4.41 (s, 2H), 4.38-4.32 (m, 10.4 Hz, 1H), 4.27-4.22 (m, 1H), 3.95-3.87 (m, 1H), 3.85-3.78 (m, 1H), 3.77-3.60 (m, 2H), 3.47-3.36 (m, 1H), 3.08-3.02 (m, 1H), 2.86 (d, J=4.4 Hz, 1H), 2.80-2.71 (m, 1H), 2.31-2.25 (m, 1H), 2.01-1.97 (m, 2H), 1.89-1.81 (m, 6H), 1.77-1.68 (m, 2H), 1.67-1.57 (m, 2H), 1.53 (s, 9H); LC-MS (ESI⁺) m/z 697.3 (M+H)⁺.

Example 33. Synthesis of Compound 033

(a) Tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

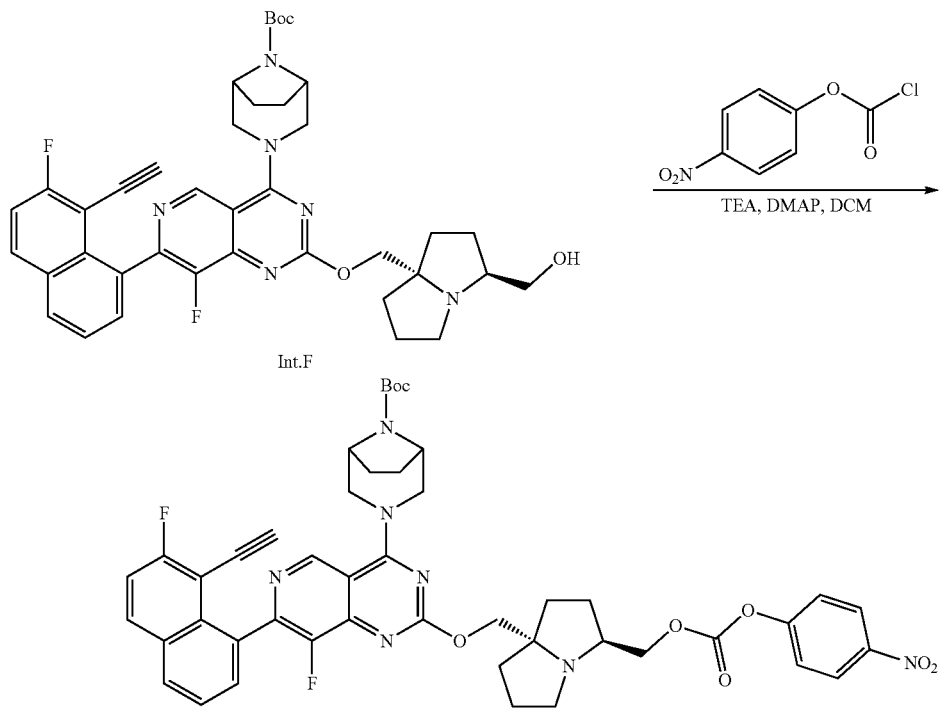

To a solution of Int. F (60.0 mg, 86.1 μmol) in DCM (10 mL) was added triethylamine (TEA, 26.1 mg, 258 μmol) and 4-dimethylaminopyridine (DMAP, 1.05 mg, 8.61 μmol). Then, (4-nitrophenyl) carbonochloridate (52.0 mg, 258 μmol, CAS #7693-46-1) was added to the mixture and the mixture was stirred at 25° C. for 16 hrs. On completion, the mixture was extracted with dichloromethane (DCM, 3×50 mL), the organic layer was dried over anhydrous Na₂SO₄, filtered and the filtrate was concentrated in vacuo to give the title compound (70.0 mg, 94% yield) as yellow solid. LC-MS (ESI⁺) m/z 862.3 (M+H)⁺.

(b) Tert-butyl N-[8-[1-(2,6-dioxo-3-piperidyl)-3-methyl-2-oxo-benzimidazol-5-yl]octyl] carbamate

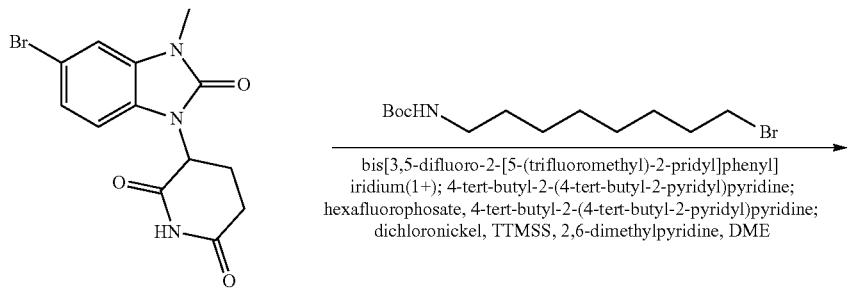

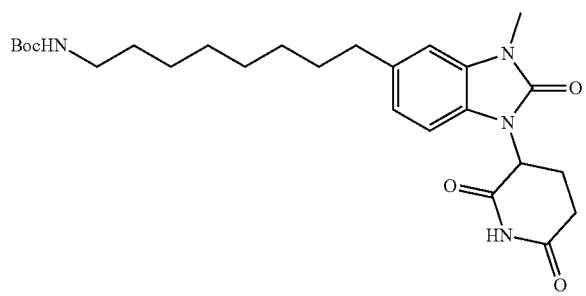

To a mixture of 3-(5-bromo-3-methyl-2-oxo-benzimidazol-1-yl)piperidine-2,6-dione (1.00 g, 2.96 mmol, CAS #2300099-98-1) and tert-butyl N-(8-bromooctyl)carbamate (911 mg, 2.96 mmol, CAS #142356-35-2) in dimethoxyethane (DME, 30 mL) was added bis[3,5-difluoro-2-[5-(trifluoromethyl)-2-pyridyl] phenyl]iridium(1+); 4-tert-butyl-2-(4-tert-butyl-2-pyridyl)pyridine; hexafluorophosphate (33.1 mg, 29.5 μmol), 4-tert-butyl-2-(4-tert-butyl-2-pyridyl) pyridine; dichloronickel (17.6 mg, 44.3 μmol), tris(trimethylsilyl)silane (TTMSS, 882 mg, 3.55 mmol) and 2,6-dimethylpyridine (2.85 g, 26.6 mmol). The vial was sealed and placed under nitrogen. The reaction was stirred and irradiated with a 10 W [455 nm] blue LED lamp (3 cm away), with cooling water to keep the reaction temperature at 25° C. for 14 hrs. On completion, the residue was diluted with water (30 mL) and extracted with EA (2×30 mL). The combined organic layers were dried over $Na_2SO_4$, filtered and concentrated in vacuo to give a residue. The residue was purified by reverse phase (0.1% formic acid (FA) condition) to give the title compound (670 mg, 1.38 mmol, 46% yield) as white solid. $^1$H NMR (400 MHz, DMSO-$d_6$) δ 10.96 (s, 1H), 6.92-6.85 (m, 2H), 6.74 (dd, J=1.2, 8.0 Hz, 1H), 6.63 (t, J=5.2 Hz, 1H), 5.21 (dd, J=5.2, 12.8 Hz, 1H), 3.20 (s, 3H), 2.82-2.72 (m, 3H), 2.63-2.55 (m, 1H), 2.53-2.45 (m, 3H), 1.93-1.84 (m, 1H), 1.52-1.40 (m, 2H), 1.25 (s, 9H), 1.19-1.09 (m, 8H). LC-MS (ESI$^+$) m/z 387.2 (M+H−100)$^+$.

(c) 3-[5-(8-Aminooctyl)-3-methyl-2-oxo-benzimidazol-1-yl] piperidine-2,6-dione

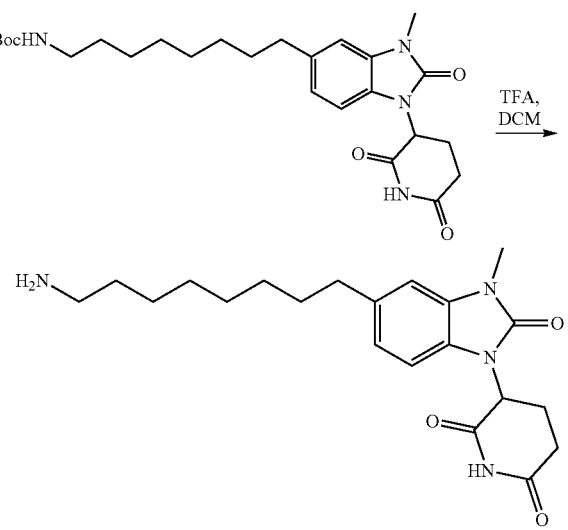

To a mixture of tert-butyl N-[8-[1-(2,6-dioxo-3-piperidyl)-3-methyl-2-oxo-benzimidazol-5-yl]octyl] carbamate (200 mg, 411 μmol) in DCM (1 mL) was added HCl/dioxane (4 M, 3.33 mL). The reaction mixture was stirred at 25° C. for 1 hour. On completion, the reaction mixture was concentrated to give the title compound (150 mg, 94% yield) as white solid. LC-MS (ESI$^+$) m/z 387.2 (M+H)$^+$.

(d) Tert-butyl 3-[2-[[(3S,8S)-3-[8-[1-(2,6-dioxo-3-piperidyl)-3-methyl-2-oxo-benzimidazol-5-yl] octyl-carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

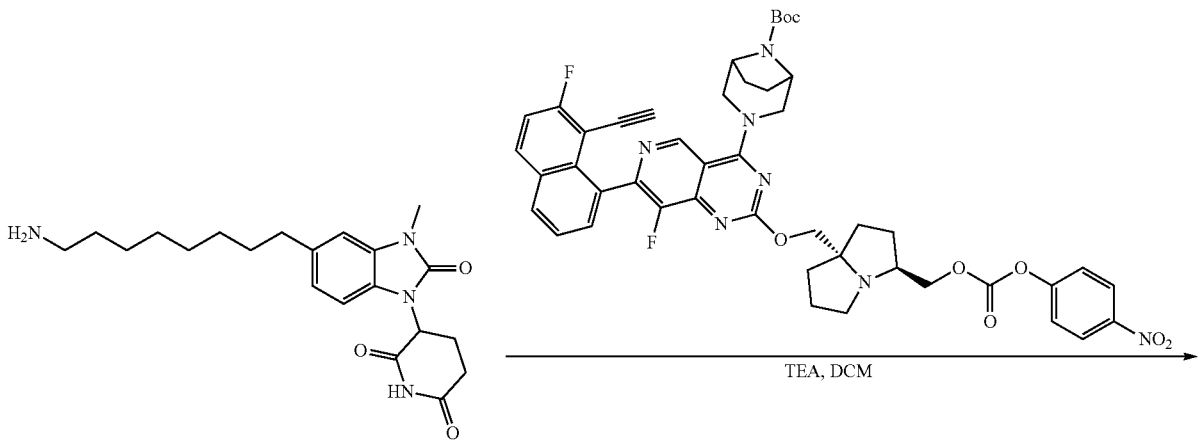

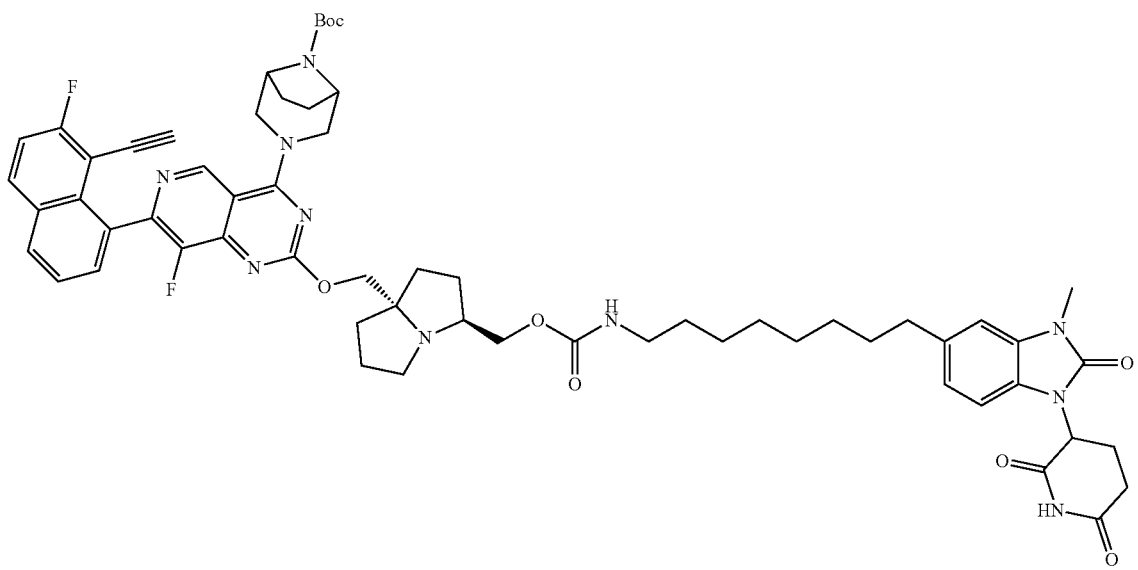

To a mixture of 3-[5-(8-aminooctyl)-3-methyl-2-oxo-benzimidazol-1-yl]piperidine-2,6-dione (62.7 mg, 162 μmol) in tetrahydrofuran (THF, 2 mL) was added tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol) and triethylamine (TEA, 8.22 mg, 81.2 μmol). The reaction mixture was stirred at 25° C. for 2 hrs. On completion, the reaction mixture was concentrated in vacuo. The residue was purified by prep-HPLC (column: Phenomenex luna C18 150*25 mm*10 μm; mobile phase: [water (FA)-ACN]; gradient: 37%-67% B over 11 minutes) to give the title compound (60.0 mg, 66% yield) as white solid. $^1$H NMR (400 MHz, Acetone) δ 8.96 (s, 1H), 8.09-7.99 (m, 2H), 7.60-7.52 (m, 2H), 7.37 (t, J=9.2 Hz, 1H), 6.89-6.82 (m, 2H), 6.73 (d, J=8.4 Hz, 1H), 6.11 (dd, J=4.0, 6.0 Hz, 1H), 5.14 (d, J=2.4 Hz, 1H), 4.64-4.55 (m, 1H), 4.41-4.32 (m, 1H), 4.30-4.24 (m, 2H), 4.15-4.01 (m, 4H), 3.73-3.64 (m, 1H), 3.58-3.49 (m, 1H), 3.48-3.43 (m, 1H), 3.23 (s, 4H), 3.02-2.92 (m, 3H), 2.71-2.61 (m, 4H), 2.50 (t, J=7.6 Hz, 2H), 2.10-2.00 (m, 3H), 1.84-1.63 (m, 10H), 1.54-1.45 (m, 3H), 1.38 (s, 9H), 1.33 (s, 2H), 1.19 (s, 8H). LC-MS (ESI$^+$) m/z 555.4 (½M+H)$^+$.

(e) [(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl N-[8-[1-(2,6-dioxo-3-piperidyl)-3-methyl-2-oxo-benzimidazol-5-yl]octyl]carbamate

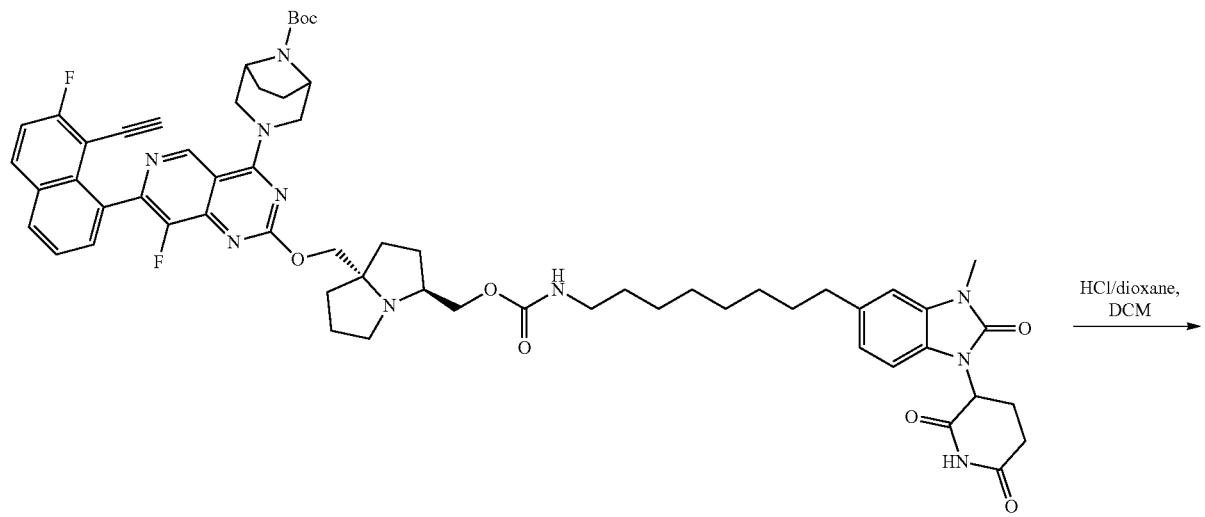

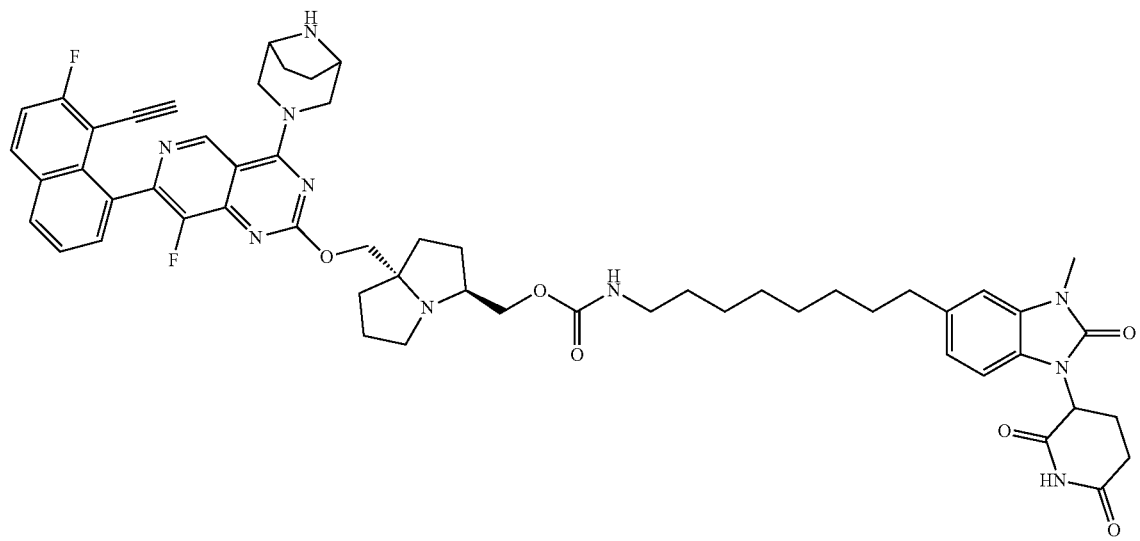

029

To a mixture of tert-butyl 3-[2-[[(3S,8S)-3-[8-[1-(2,6-dioxo-3-piperidyl)-3-methyl-2-oxo-benzimidazol-5-yl]octylcarbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (60.0 mg, 54.0 µmol) in DCM (2 mL) was added HCl/dioxane (4 M, 1 mL). The reaction mixture was stirred at 25° C. for 1 hours. On completion, the reaction mixture was concentrated in vacuo. The residue was purified by prep-HPLC (column: Phenomenex C18 150*25 mm*10 µm; mobile phase: [water (NH$_4$HCO$_3$)-ACN]; gradient: 53%-83% B over 14 minutes) to give the title compound (28.4 mg, 48% yield, 98% purity, FA) as yellow solid. $^1$H NMR (400 MHz, DMSO-d$_6$) δ 11.09 (s, 1H), 9.06 (s, 1H), 8.26-8.21 (m, 1H), 8.19 (s, 2H), 7.74-7.57 (m, 3H), 7.21-7.15 (m, 1H), 7.03-6.96 (m, 2H), 6.84 (d, J=8.4 Hz, 1H), 5.33 (dd, J=5.6, 12.8 Hz, 1H), 4.49 (d, J=11.6 Hz, 1H), 4.39-4.29 (m, 1H), 4.17-4.08 (m, 3H), 4.06-4.00 (m, 2H), 3.64 (s, 4H), 2.99-2.90 (m, 3H), 2.74 (d, J=4.4 Hz, 2H), 2.68 (d, J=1.9 Hz, 2H), 2.63 (d, J=4.9 Hz, 2H), 2.58 (s, 3H), 2.07-1.96 (m, 2H), 1.84-1.65 (m, 10H), 1.62-1.52 (m, 3H), 1.41-1.35 (m, 2H), 1.26 (d, J=12.4 Hz, 9H). LC-MS (ESI$^+$) m/z 1009.5 (M+H)$^+$.

Example 34. Synthesis of Compound 031

(a) Tert-butyl 3-[2-[[(3S,8S)-3-[[4-[3-[1-(2,6-dioxo-3-piperidyl)-3-methyl-2-oxo-benzimidazol-4-yl]propoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

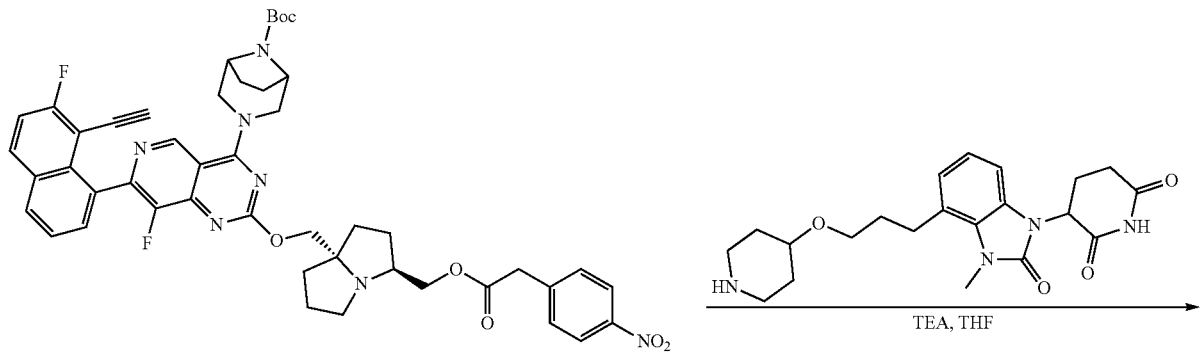

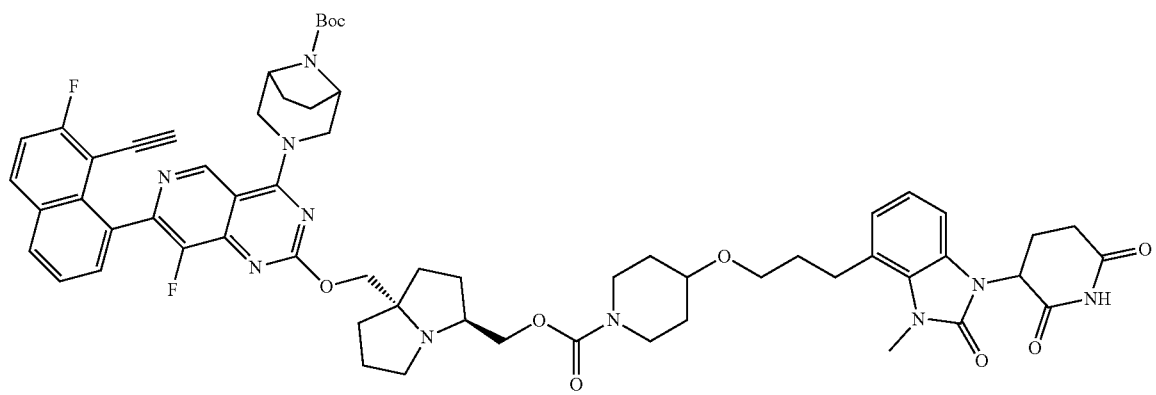

To a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol) and 3-[3-methyl-2-oxo-4-[3-(4-piperidyloxy)propyl]benzimidazol-1-yl]piperidine-2,6-dione (70.9 mg, 162 μmol, HCl salt) in THF (3 mL) was added TEA (24.6 mg, 243 μmol). The mixture was stirred at 25° C. for 4 hrs. On completion, the reaction mixture was filtered and concentrated in vacuo to give a residue. The residue was purified by prep-HPLC (column: Phenomenex luna C18 150*25 mm*10 μm; mobile phase: [water (FA)-ACN]; gradient: 32%-62% B over 10 minutes) to give the title compound (35.0 mg, 38% yield) as yellow solid. LC-MS (ESI$^+$) m/z 1123.5 (M+H)$^+$.

(b) [(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate

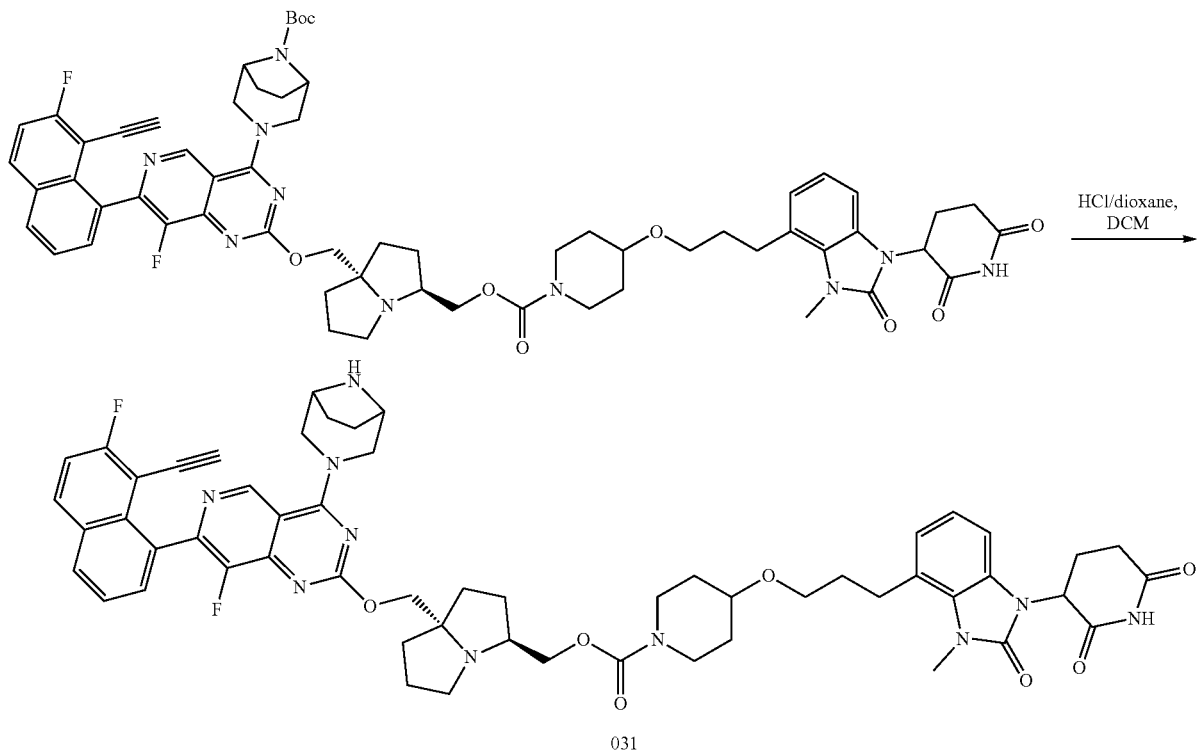

To a solution of tert-butyl 3-[2-[[(3S,8S)-3-[[4-[3-[1-(2,6-dioxo-3-piperidyl)-3-methyl-2-oxo-benzimidazol-4-yl]propoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35.0 mg, 31.1 μmol) in DCM (2 mL) was added HCl/dioxane (4 M, 0.4 mL). The mixture was stirred at 25° C. for 0.5 hr. On completion, the mixture was concentrated in vacuo to give a residue. The residue was purified by prep-HPLC (column: Phenomenex luna C18 150*25 mm*10 μm; mobile phase: [water (FA)-ACN]; gradient: 12%-42% B over 8 minutes) to give the title compound (30.1 mg, 94% yield) as yellow solid. $^1$H NMR (400 MHz, DMSO-$d_6$) δ 11.10 (s, 1H), 9.05 (s, 1H), 8.25-8.21 (m, 1H), 8.21-8.17 (m, 1H), 7.72-7.66 (m, 1H), 7.65-7.56 (m, 2H), 7.00-6.90 (m, 2H), 6.89-6.82 (m, 1H), 5.36 (dd, J=5.2, 12.8 Hz, 1H), 4.48 (d, J=11.6 Hz, 1H), 4.34 (d, J=11.6 Hz, 1H), 4.25-4.19 (m, 1H), 4.17-4.11 (m, 2H), 4.07-4.03 (m, 1H), 4.02 (s, 1H), 3.67-3.61 (m, 5H), 3.55 (s, 3H), 3.46 (t, J=6.0 Hz, 4H), 3.30-3.24 (m, 1H), 3.15-3.07 (m, 2H), 2.97-2.92 (m, 2H), 2.91-2.83 (m, 1H), 2.78-2.57 (m, 5H), 2.07-1.96 (m, 2H), 1.86-1.61 (m, 14H), 1.55-1.46 (m, 1H), 1.41-1.32 (m, 2H); LC-MS (ESI$^+$) m/z 1023.5 (M+H)$^+$.

Example 35. Synthesis of Compound 030

(a) 3-[3-Methyl-2-oxo-4-[3-(4-piperidyloxy)prop-1-ynyl]benzimidazol-1-yl]piperidine-2,6-dione

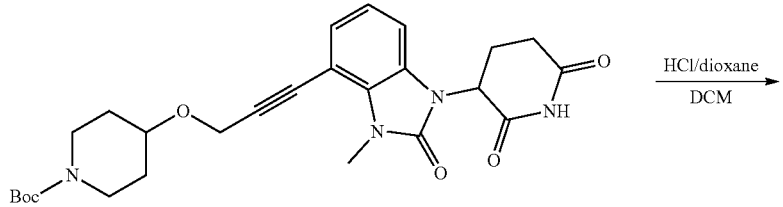

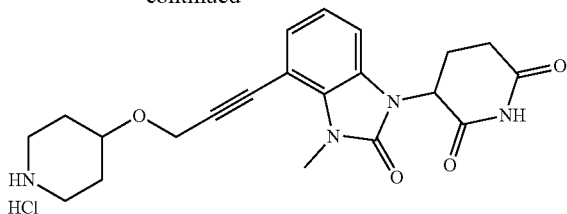

To a solution of tert-butyl 4-[3-[1-(2,6-dioxo-3-piperidyl)-3-methyl-2-oxo-benzimidazol-4-yl]prop-2-ynoxy]piperidine-1-carboxylate (50.0 mg, 100 μmol) in DCM (2.5 mL) was added HCl/dioxane (4 M, 0.5 mL). The mixture was stirred at 25° C. for 2 hrs. On completion, the reaction mixture concentrated in vacuo to give the title compound (43.0 mg, 98% yield, HCl salt) as yellow solid. LC-MS (ESI+) m/z 397.2 (M+H)+.

(b) Tert-butyl 3-[2-[[(3S,8S)-3-[[4-[3-[1-(2,6-dioxo-3-piperidyl)-3-methyl-2-oxo-benzimidazol-4-yl]prop-2-ynoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

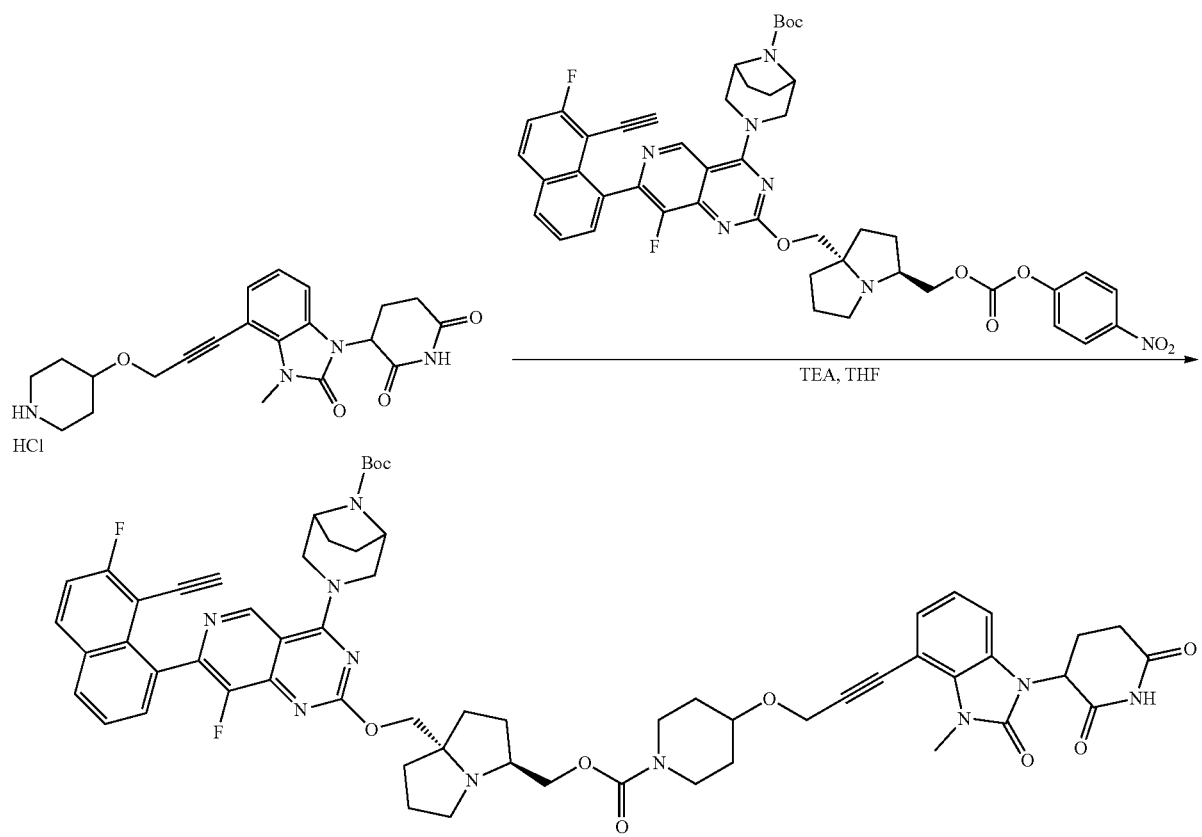

To a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (43.0 mg, 50.4 μmol) in THF (2 mL) was added TEA (20.4 mg, 201 μmol). Then the 3-[3-methyl-2-oxo-4-[3-(4-piperidyloxy)prop-1-ynyl]benzimidazol-1-yl]piperidine-2,6-dione (40.0 mg, 100 μmol) was added and stirred at 25° C. for 16 hrs. On completion, the mixture was concentrated in vacuo to give a residue and the residue was purified by prep-HPLC (column: Phenomenex luna C18 150*25 mm*10 μm; mobile phase: [water (FA)-ACN]; gradient: 36%-56% B over 8 minutes) to give the title compound (25.0 mg, 21% yield) as white solid. LC-MS (ESI+) m/z 1119.5 (M+H)+.

(c) [(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]prop-2-ynoxy]piperidine-1-carboxylate

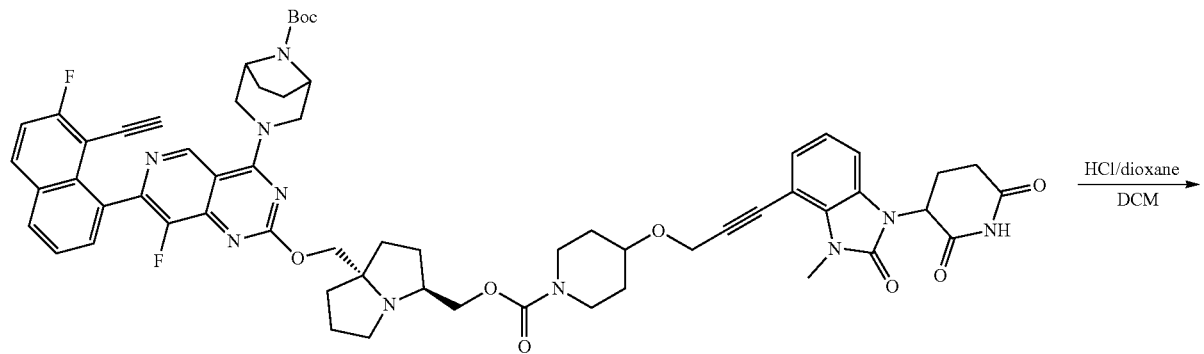

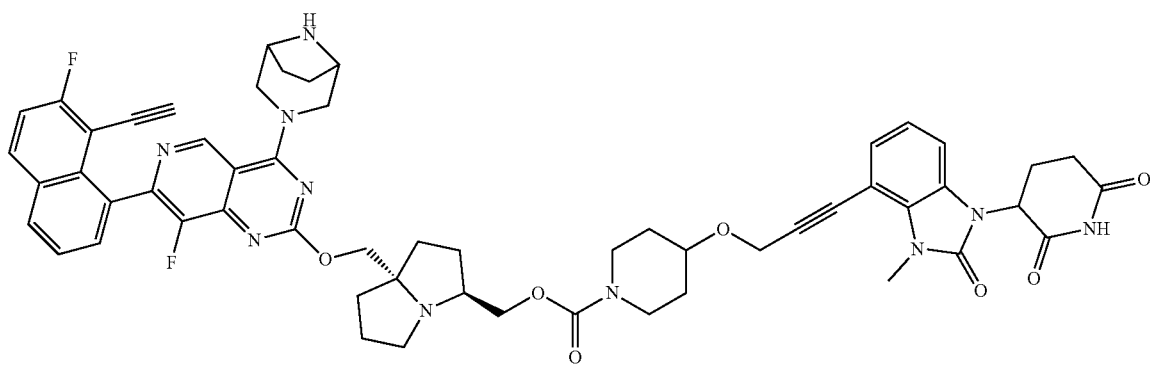

030

To a solution of tert-butyl 3-[2-[[(3S,8S)-3-[[4-[3-[1-(2,6-dioxo-3-piperidyl)-3-methyl-2-oxo-benzimidazol-4-yl]prop-2-ynoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (25.0 mg, 22.3 μmol) in DCM (2.5 mL) was added HCl/dioxane (4 M, 0.5 mL). The mixture was stirred at 25° C. for 15 mins. On completion, the reaction mixture was concentrated in vacuo to give a residue and the residue was purified by prep-HPLC (column: Phenomenex luna C18 150*25 mm*10 μm; mobile phase: [water (FA)-ACN]; gradient: 15%-45% B over 8 minutes) to give the title compound (8.20 mg, 36% yield) as yellow solid. $^1$H NMR (400 MHz, DMSO-$d_6$) δ 11.12 (s, 1H), 9.04 (s, 1H), 8.24-8.17 (m, 2H), 7.72-7.57 (m, 3H), 7.17 (d, J=7.6 Hz, 1H), 7.11 (d, J=7.2 Hz, 1H), 7.02 (t, J=1.6 Hz 1H), 5.42-5.37 (m, 1H), 4.51-4.43 (m, 3H), 4.32 (d, J=11.2 Hz, 1H), 4.26-4.19 (m, 1H), 4.16-4.09 (m, 2H), 4.07-4.00 (m, 2H), 3.77-3.72 (m, 1H), 3.70-3.60 (m, 6H), 3.59-3.54 (m, 3H), 3.28-3.25 (m, 1H), 3.15-3.10 (m, 2H), 2.96-2.83 (m, 1H), 2.77-2.63 (m, 4H), 2.06-1.98 (m, 2H), 1.88-1.84 (m, 2H), 1.81-1.59 (m, 11H), 1.54-1.47 (m, 1H), 1.45-1.36 (m, 2H); LC-MS (ESI$^+$) m/z 1019.5 (M+H)$^+$.

Example 36. Synthesis of Compound 032

(a) Tert-butyl 3-[2-[[(3S,8S)-3-[[4-[3-[1-(2,6-dioxo-3-piperidyl)-3-methyl-2-oxo-benzimidazol-4-yl]propoxy]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

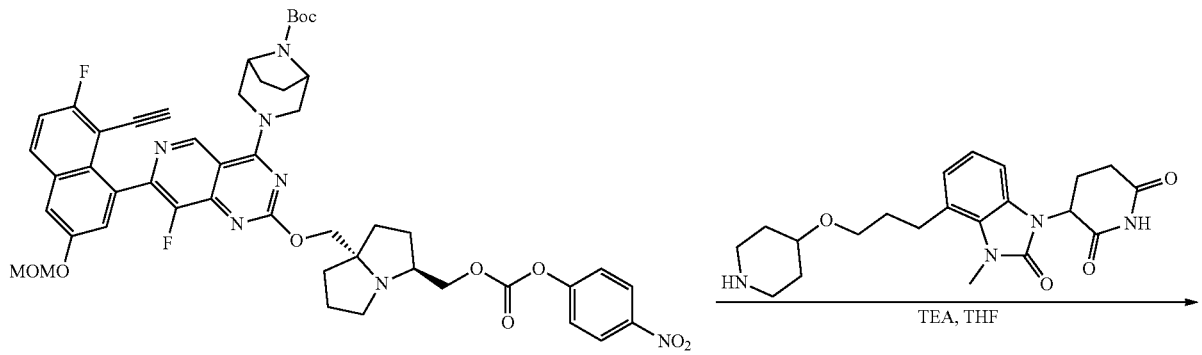

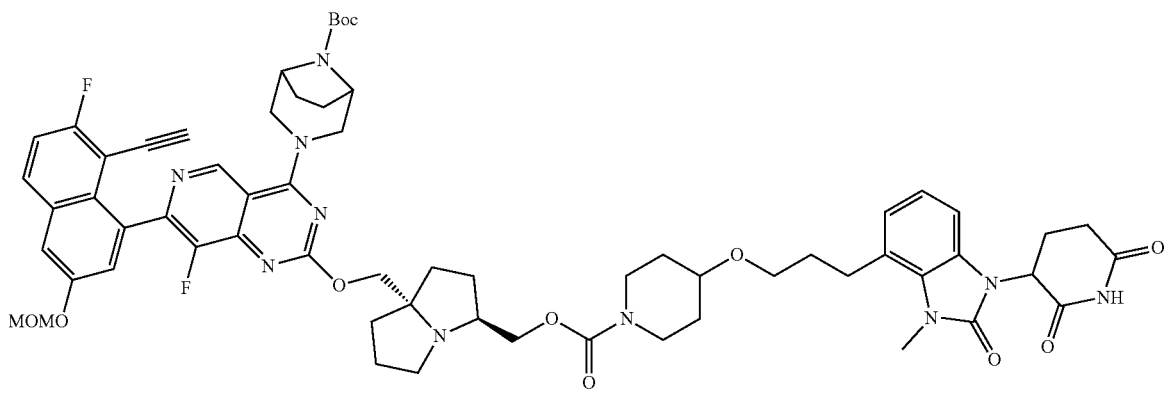

To a solution of 3-[3-methyl-2-oxo-4-[3-(4-piperidyloxy)propyl]benzimidazol-1-yl]piperidine-2,6-dione (47.3 mg, 108 μmol) in THF (10 mL) was added TEA (38.4 mg, 379 μmol) and tert-butyl-3-[7-[8-ethynyl-7-fluoro-3-(methoxymethoxy)-1-naphthyl]-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (50.0 mg, 54.2 μmol). The mixture was stirred at 25° C. for 1 hr. On completion, the mixture was concentrated in vacuo to give a residue and the residue was purified by prep-HPLC (column: Phenomenex luna C18 150*25 mm*10 μm; mobile phase: [water (FA)-ACN]; gradient: 25%-55% B over 8 minutes) to give the title compound (35.0 mg, 47% yield) as yellow solid. LC-MS (ESI$^+$) m/z 1183.6 (M+H)$^+$.

(b) [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propoxy]piperidine-1-carboxylate (032)

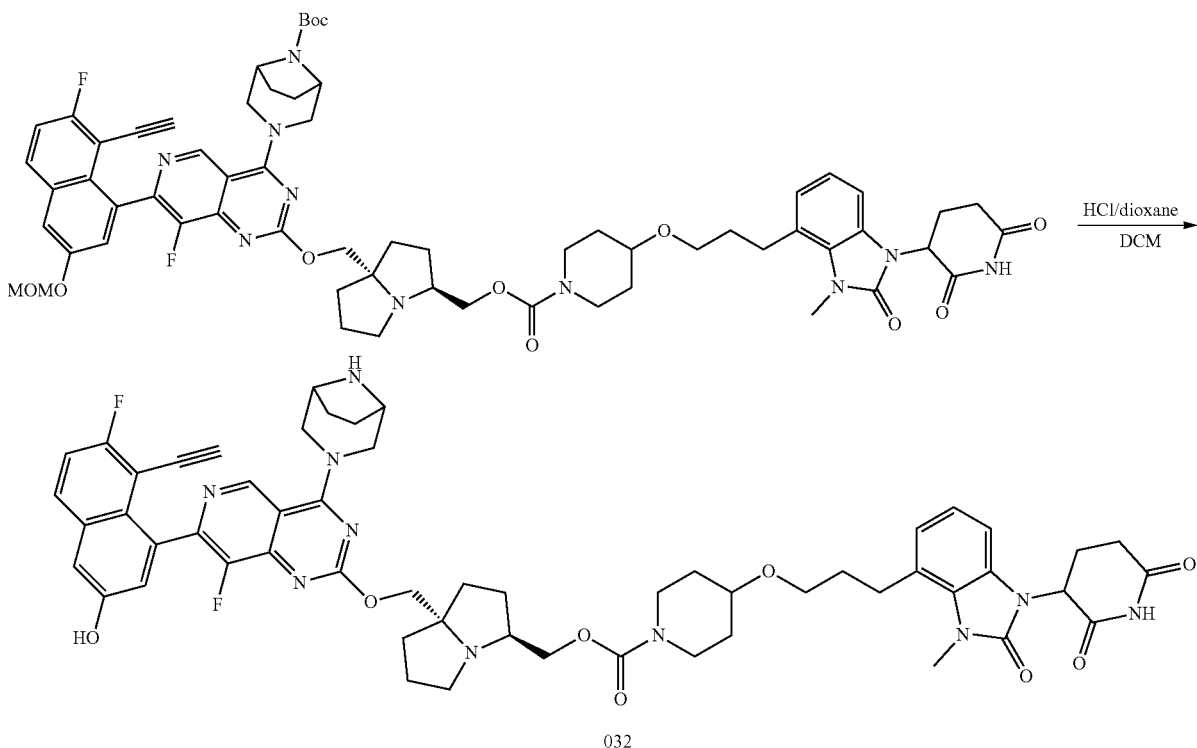

To a solution of tert-butyl 3-[2-[[(3S,8S)-3-[[4-[3-[1-(2,6-dioxo-3-piperidyl)-3-methyl-2-oxo-benzimidazol-4-yl]propoxy]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (35.0 mg, 29.5 μmol) in DCM (4 mL) was added HCl/dioxane (4 M, 2.33 mL). The mixture was stirred at 25° C. for 20 mins. On completion, the mixture was concentrated in vacuo to give a residue and the residue was purified by prep-HPLC (column: Phenomenex luna C18 150*25 mm*10 μm; mobile phase: [water (FA)-ACN]; gradient: 10%-40% B over 8 minutes) to give the title compound (27.0 mg, 86% yield) as yellow solid. $^1$H NMR (400 MHz, DMSO-$d_6$) δ 11.10 (s, 1H), 9.04 (s, 1H), 8.22 (s, 1H), 8.00-7.93 (m, 1H), 7.49-7.42 (m, 1H), 7.38 (d, J=2.4 Hz, 1H), 7.17 (d, J=2.4 Hz, 1H), 6.99-6.91 (m, 2H), 6.89-6.82 (m, 1H), 5.39-5.32 (m, 1H), 4.52-4.46 (m, 1H), 4.35-4.30 (m, 1H), 4.25-4.20 (m, 1H), 4.16-4.11 (m, 2H), 4.07-4.03 (m, 1H), 3.93 (s, 1H), 3.66-3.61 (m, 5H), 3.55 (s, 3H), 3.49-3.44 (m, 4H), 3.29-3.26 (m, 1H), 3.13-3.08 (m, 2H), 2.97-2.93 (m, 2H), 2.77-2.73 (m, 2H), 2.72-2.70 (m, 1H), 2.65-2.62 (m, 1H), 2.59 (s, 1H), 2.04-1.96 (m, 2H), 1.82-1.65 (m, 15H), 1.55-1.49 (m, 1H), 1.41-1.33 (m, 2H); LC-MS (ESI$^+$) m/z 1039.4 (M+H)$^+$.

Example 37. Synthesis of Compound 033

(a) Step 1—3-[3-Methyl-2-oxo-4-[3-(4-piperidyloxy)prop-1-ynyl]benzimidazol-1-yl]piperidine-2,6-dione

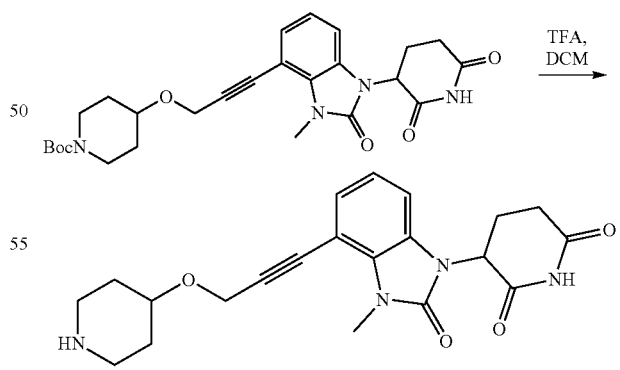

A solution of tert-butyl 4-[3-[1-(2,6-dioxo-3-piperidyl)-3-methyl-2-oxo-benzimidazol-4-yl] prop-2-ynoxy]piperidine-1-carboxylate (50.0 mg, 100 μmol) and trifluoroacetic acid (TFA, 767 mg, 6.73 mmol) in DCM (2 mL) was stirred at 20° C. for 1 hr. On completion, the mixture was concentrated in vacuo to give the title compound (39.0 mg, 97% yield) as yellow solid. LC-MS (ESI$^+$) m/z 397.1 (M+H)$^+$.

(b) Tert-butyl 3-[2-[[(3S,8S)-3-[[4-[3-[1-(2,6-dioxo-3-piperidyl)-3-methyl-2-oxo-benzimidazol-4-yl]prop-2-ynoxy]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

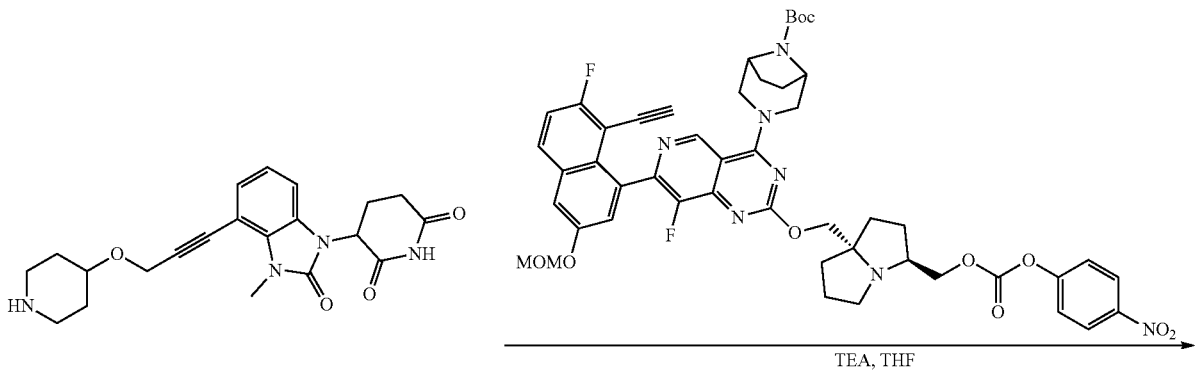

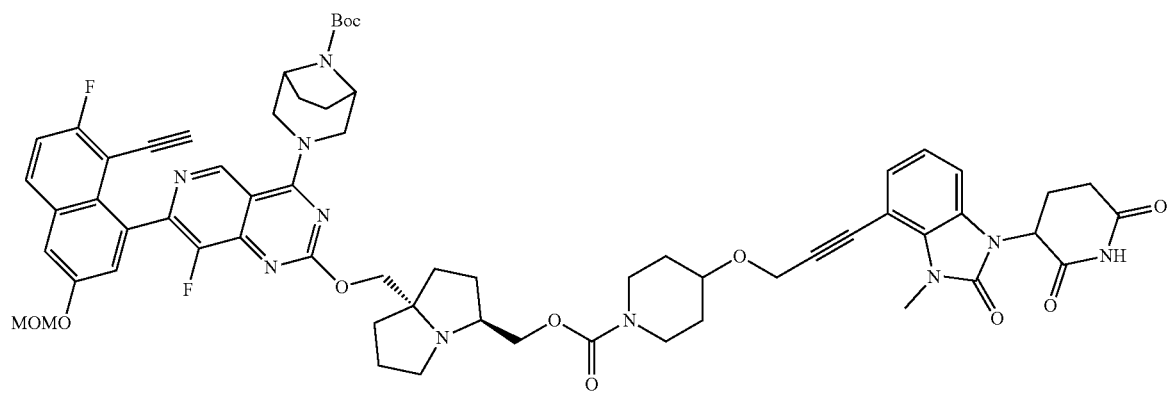

A solution of 3-[3-methyl-2-oxo-4-[3-(4-piperidyloxy)prop-1-ynyl]benzimidazol-1-yl]piperidine-2,6-dione (39.0 mg, 98.3 μmol), tert-butyl 3-[7-[8-ethynyl-7-fluoro-3-(methoxymethoxy)-1-naphthyl]-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (72.5 mg, 78.7 μmol) and TEA (29.8 mg, 295 μmol) in THF (3 mL) was stirred at 25° C. for 16 hrs. On completion, the reaction mixture was concentrated in vacuo to give a residue and the residue was purified by prep-HPLC (column: Phenomenex luna C18 150*25 mm*10 μm; mobile phase: [water (FA)-ACN]; gradient: 33%-63% B over 10 minutes) to give the title compound (25.0 mg, 18% yield) as yellow solid. LC-MS (ESI+) m/z 1179.5 (M+H)+.

(c) [(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]prop-2-ynoxy]piperidine-1-carboxylate (033)

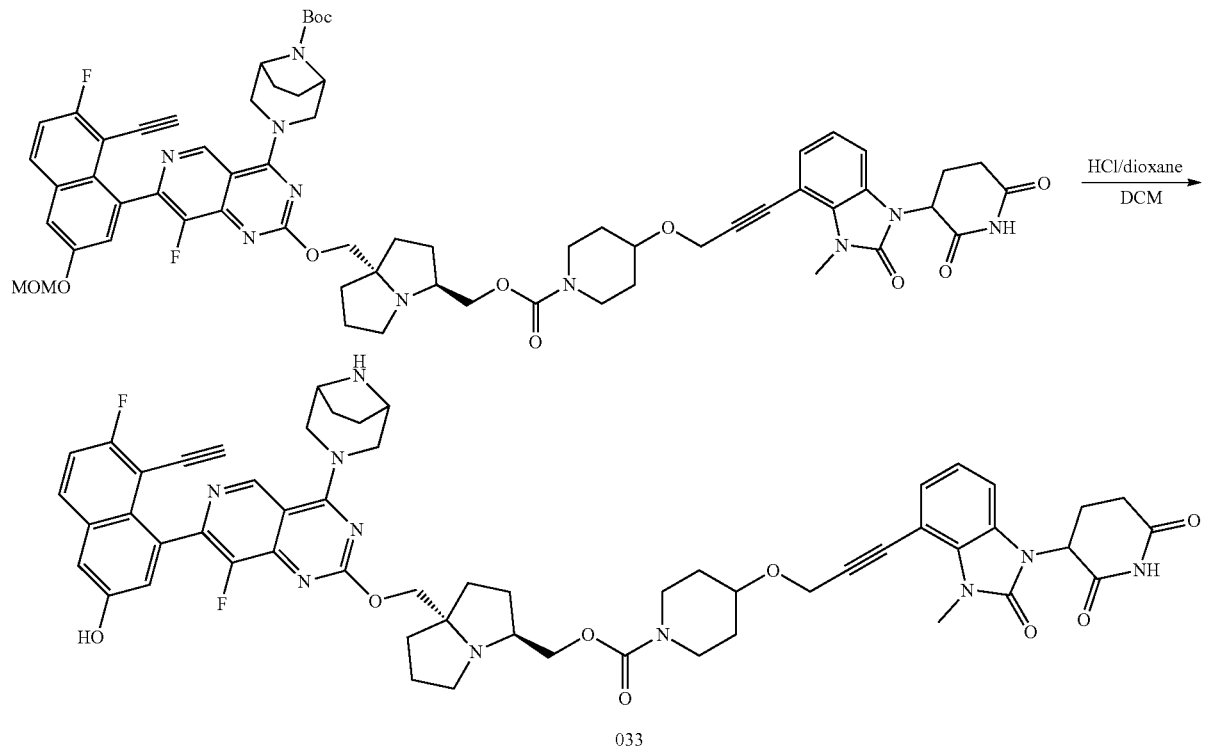

A solution of tert-butyl 3-[2-[[(3S,8S)-3-[[4-[3-[1-(2,6-dioxo-3-piperidyl)-3-methyl-2-oxo-benzimidazol-4-yl]prop-2-ynoxy]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (25.0 mg, 21.2 μmol) and HCl/dioxane (4 M, 416 μL) in DCM (2 mL) was stirred at 20° C. for 10 mins. On completion, the reaction mixture was concentrated in vacuo to give a residue and the residue was purified by prep-HPLC (column: Phenomenex luna C18 150*25 mm*10 μm; mobile phase: [water (FA)-ACN]; gradient: 10%-40% B over 8 minutes) to give the title compound (6.00 mg, 25% yield) as white solid. $^1$H NMR (400 MHz, DMSO-$d_6$) δ 11.13 (s, 1H), 9.03 (s, 1H), 8.23 (s, 1H), 8.00-7.92 (m, 1H), 7.46 (t, J=9.0 Hz, 1H), 7.40-7.37 (m, 1H), 7.20-7.14 (m, 2H), 7.13-7.10 (m, 1H), 7.04-6.99 (m, 1H), 5.45-5.30 (m, 1H), 4.52-4.45 (m, 3H), 4.35-4.29 (m, 1H), 4.26-4.20 (m, 1H), 4.17-4.10 (m, 2H), 4.07-4.02 (d, J=10.5 Hz, 1H), 3.93 (s, 1H), 3.78-3.72 (m, 2H), 3.70-3.66 (m, 3H), 3.64-3.60 (m, 6H), 3.17-3.08 (m, 3H), 2.93-2.84 (m, 1H), 2.79-2.63 (m, 4H), 2.07-1.99 (m, 2H), 1.90-1.83 (m, 2H), 1.79-1.64 (m, 10H), 1.55-1.48 (m, 1H), 1.46-1.36 (m, 2H); LC-MS (ESI$^+$) m/z 1035.4 (M+H)$^+$.

Example 38. Synthesis of Compound 037

(a) Step 1—3-(3-Methyl-2-oxo-4-vinyl-benzimidazol-1-yl)piperidine-2,6-dione

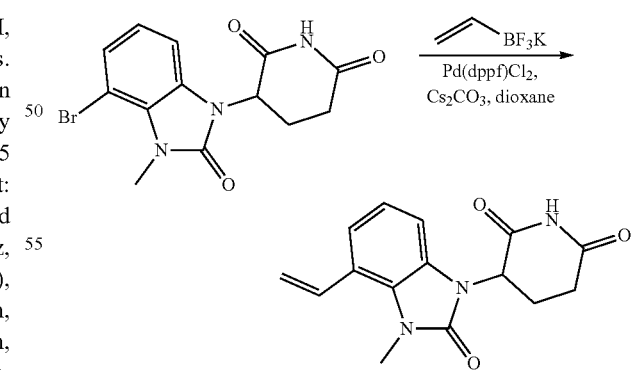

To a solution of 3-(4-bromo-3-methyl-2-oxo-benzimidazol-1-yl)piperidine-2,6-dione (10.0 g, 29.5 mmol, CSA #2304754-51-4) and potassium; trifluoro(vinyl)boranuide (11.8 g, 88.7 mmol, CSA #13682-77-4) in dioxane (20 mL) was added Cs$_2$CO$_3$ (19.2 g, 59.1 mmol) and Pd(dppf)Cl$_2$ (2.16 g, 2.96 mmol). The mixture was stirred at 80° C. for 6 hrs under N₂ atmosphere. On completion, the mixture was filtered and the filtrate was concentrated in vacuo. The residue was purified by column chromatography (SiO₂, EA:DCM=1:1) to give the title compound (3.50 g, 40% yield) as orange solid. ¹H NMR (400 MHz, DMSO-d₆) δ 11.11 (s, 1H), 7.40 (dd, J=11.2, 16.4 Hz, 1H), 7.19 (d, J=6.8 Hz, 1H), 7.12-6.98 (m, 2H), 5.77-5.66 (m, 1H), 5.50-5.24 (m, 2H), 3.54 (s, 3H), 2.97-2.82 (m, 1H), 2.77-2.56 (m, 2H), 2.10-2.00 (m, 1H); LC-MS (ESI⁺) m/z 286.0 (M+H)⁺.

(b) Step 2—1-(2,6-Dioxo-3-piperidyl)-3-methyl-2-oxo-benzimidazole-4-carbaldehyde

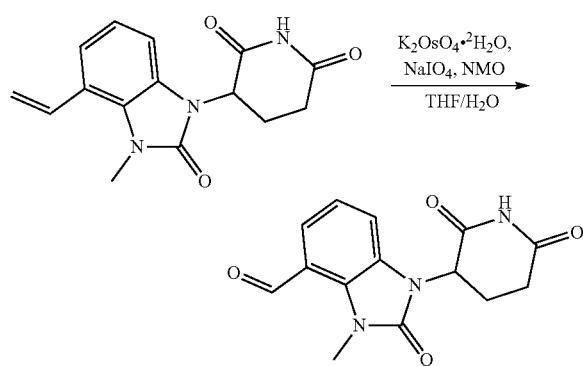

To a solution of 3-(3-methyl-2-oxo-4-vinyl-benzimidazol-1-yl)piperidine-2,6-dione (3.00 g, 10.5 mmol) in THF (30 mL) and H₂O (6 mL) was added K₂OsO₄·2H₂O (193 mg, 525 μmol) and NMO (2.09 g, 17.8 mmol). The mixture was stirred at 25° C. for 16 hours, then NaIO₄ (15.7 g, 73.6 mmol) was added into above solution, the mixture was stirred at 25° C. for 1 hr. On completion, the mixture was filtered. The filtrate was quenched with Na₂SO₃ (50 mL) and extracted with DCM (3×50 mL). The combined organic layers were washed with brine (30 mL), the water liquor was filtered and the filter cake was dried in vacuo to give the title compound (6.60 g, crude) as white solid. ¹H NMR (400 MHz, DMSO-d₆) δ 11.15 (s, 1H), 10.40 (s, 1H), 7.60 (d, J=8.0 Hz, 1H), 7.45 (d, J=8.0 Hz, 1H), 7.21 (t, J=8.0 Hz, 1H), 5.45 (dd, J=5.6, 12.4 Hz, 1H), 3.67 (s, 3H), 2.95-2.83 (m, 1H), 2.79-2.69 (m, 1H), 2.67-2.60 (m, 1H), 2.09-2.02 (m, 1H); LC-MS (ESI⁺) m/z 288.0 (M+H)⁺.

(c) Step 3—3-[4-(Hydroxymethyl)-3-methyl-2-oxo-benzimidazol-1-yl]piperidine-2,6-dione

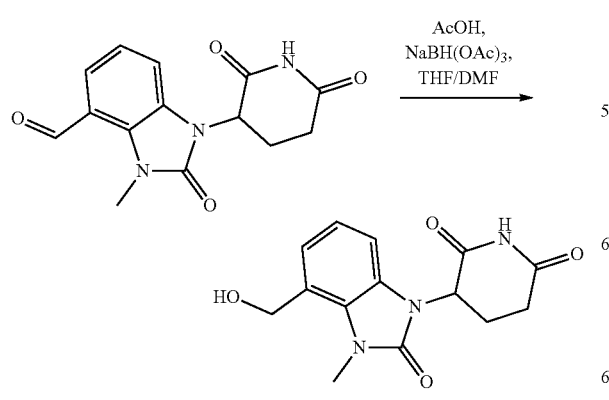

To a solution of 1-(2,6-dioxo-3-piperidyl)-3-methyl-2-oxo-benzimidazole-4-carbaldehyde (2.00 g, 6.96 mmol) in DMF (10 mL) and THF (10 mL) was added AcOH (1.25 g, 20.8 mmol) and NaBH₃CN (1.75 g, 27.8 mmol). The mixture was stirred at 60° C. for 16 hrs. On completion, the mixture was filtrated and the filtrate was concentrated in vacuo. The residue was purified by prep-HPLC (column: Phenomenex Luna C8 250*50 mm*10 μm; mobile phase: [water (FA)-ACN]; gradient: 10%-35% B over 11 min) to give the title compound (1.10 g, 54% yield) as white solid. ¹H NMR (400 MHz, DMSO-d₆) δ 11.10 (s, 1H), 7.10-6.95 (m, 3H), 5.38 (dd, J=5.2, 12.8 Hz, 1H), 4.73 (s, 2H), 3.61 (s, 3H), 2.95-2.84 (m, 1H), 2.77-2.58 (m, 2H), 2.05-1.96 (m, 1H); LC-MS (ESI⁺) m/z 290.0 (M+H)⁺.

(d) Step 4—3-[4-(Chloromethyl)-3-methyl-2-oxo-benzimidazol-1-yl]piperidine-2,6-dione

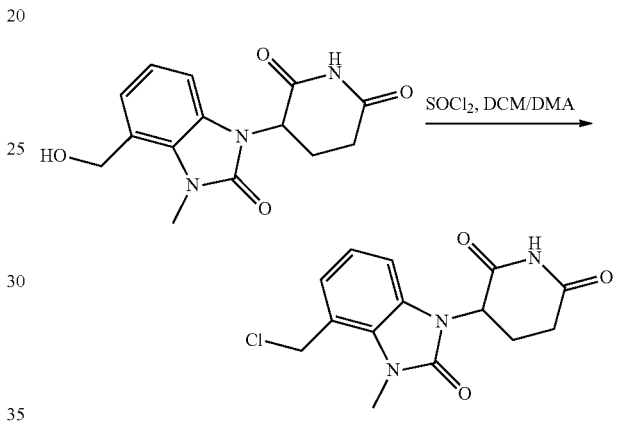

To a solution of 3-[4-(hydroxymethyl)-3-methyl-2-oxo-benzimidazol-1-yl]piperidine-2,6-dione (1.10 g, 3.80 mmol) in DCM (10 mL) and DMA (10 mL) was added SOCl₂ (904 mg, 7.60 mmol) at 0° C. The mixture was stirred at 25° C. for 2 hrs. On completion, the mixture was quenched with H₂O (0.5 mL) at 0° C., then diluted with H₂O (5 mL), extracted with DCM (3×15 mL), the organic layer was washed with brine (10 mL), dried with anhydrous Na₂SO₄, filter and the filtrate was concentrated in vacuo. The residue was purified by reversed phase (0.1% FA) to give the title compound (200 mg, 22% yield) as white solid. ¹H NMR (400 MHz, DMSO-d₆) δ 11.12 (s, 1H), 7.19-7.10 (m, 2H), 7.06-7.02 (m, 1H), 5.41 (dd, J=5.2, 12.4 Hz, 1H), 5.10 (s, 2H), 3.68 (s, 3H), 2.95-2.84 (m, 2H), 2.75-2.70 (m, 1H), 2.05-2.00 (m, 1H); LC-MS (ESI⁺) m/z 308.0 (M+H)⁺.

(e) Step 5—Tert-butyl 4-[[1-(2,6-dioxo-3-piperidyl)-3-methyl-2-oxo-benzimidazol-4-yl]methoxy]piperidine-1-carboxylate

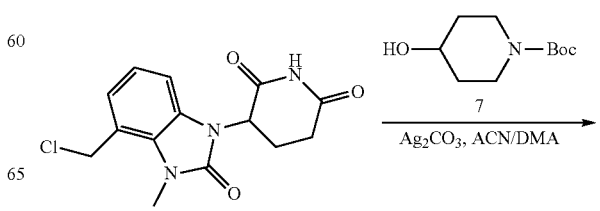

1013

-continued

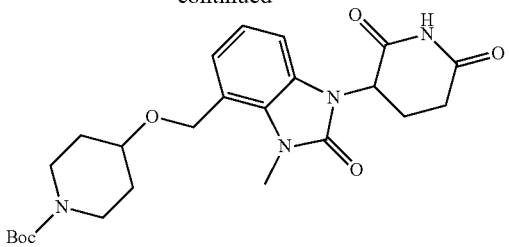

To a solution of 3-[4-(chloromethyl)-3-methyl-2-oxo-benzimidazol-1-yl]piperidine-2,6-dione (200 mg, 649 µmol) and tert-butyl 4-hydroxypiperidine-1-carboxylate (392 mg, 1.95 mmol, CAS #109384-19-2) in ACN (4 mL) and DMA (0.8 mL) was added argentiooxycarbonyloxysilver (537 mg, 1.95 mmol). The mixture was stirred at 60° C. for 16 hrs. On completion, the mixture was filtrated and the filtrate was concentrated in vacuo. The residue was purified by reversed phase (0.1% FA) to give the title compound (30.9 mg, 9% yield) as white solid. LC-MS (ESI$^+$) m/z 417.2 (M-t-Bu+H)$^+$.

(f) Step 6—3-[3-Methyl-2-oxo-4-(4-piperidyloxymethyl)benzimidazol-1-yl]piperidine-2,6-dione

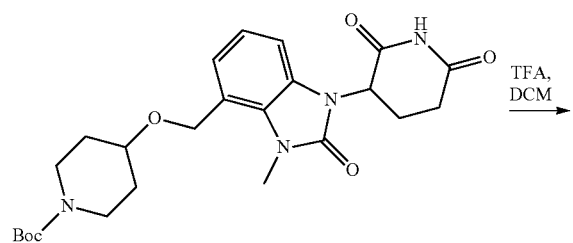

1014

-continued

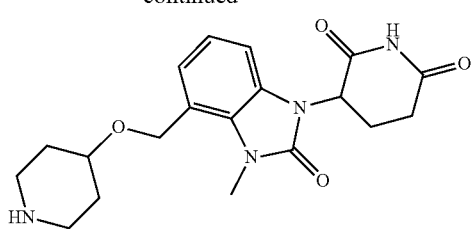

To a solution of tert-butyl 4-[[1-(2,6-dioxo-3-piperidyl)-3-methyl-2-oxo-benzimidazol-4-yl] methoxy]piperidine-1-carboxylate (80.0 mg, 169 µmol) in DCM (1 mL) was added TFA (1.23 g, 10.7 mmol, 800 µL). The mixture was stirred at 25° C. for 0.5 hr. On completion, the mixture was concentrated in vacuo to give the title compound (82.0 mg, 99% yield, TFA salt) as yellow oil. LC-MS (ESI$^+$) m/z 373.1 (M+H)$^+$.

(g) Step 7—Tert-butyl 3-[2-[[(3S,8S)-3-[[4-[[1-(2,6-dioxo-3-piperidyl)-3-methyl-2-oxo-benzimidazol-4-yl] methoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

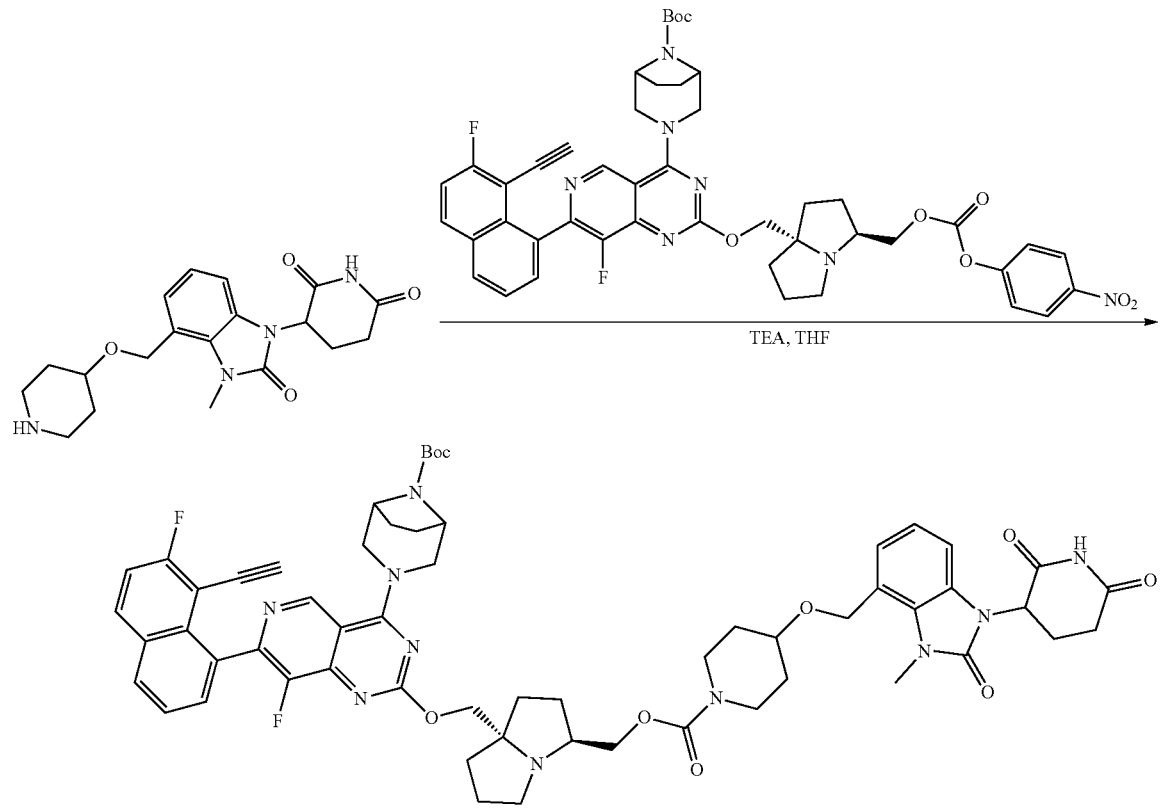

To a solution of 3-[3-methyl-2-oxo-4-(4-piperidyloxymethyl)benzimidazol-1-yl]piperidine-2,6-dione (51.9 mg, 106 µmol, TFA) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (46.0 mg, 53.3 µmol) in THF (1 mL) and H₂O (0.1 mL) was added TEA (16.2 mg, 160 µmol). The mixture was stirred at 25° C. for 1 hr. On completion, the mixture was concentrated in vacuo. The residue was purified by prep-HPLC (column: Phenomenex luna C18 150*25 mm*10 µm; mobile phase: [water (FA)-ACN]; gradient: 55%-85% B over 8 min) to give the title compound (50.0 mg, 85% yield) as yellow solid. LC-MS (ESI⁺) m/z 1095.7 (M+H)⁺.

(h) Step 8—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[[1-(2,6-dioxo-3-piperidyl)-3-methyl-2-oxo-benzimidazol-4-yl]methoxy]piperidine-1-carboxylate (037)

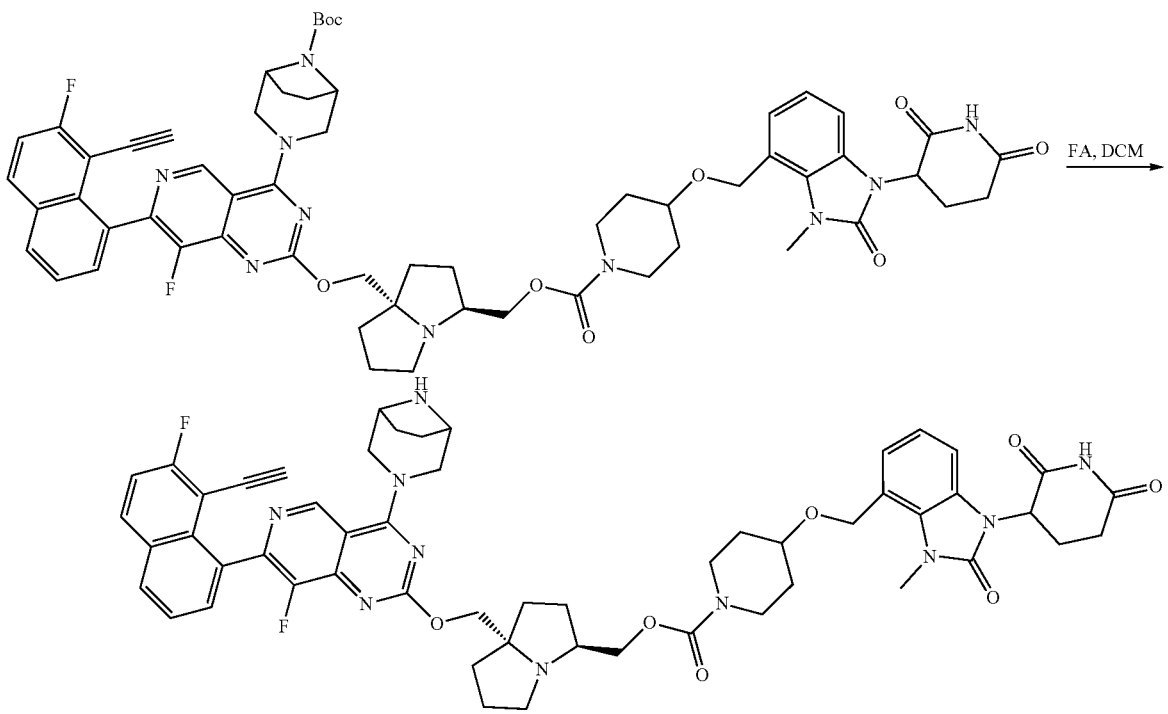

37

To a solution of tert-butyl 3-[2-[[(3S,8S)-3-[[4-[[1-(2,6-dioxo-3-piperidyl)-3-methyl-2-oxo-benzimidazol-4-yl]methoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 36.5 µmol) in DCM (1 mL) was added HCOOH (1.75 mg, 36.5 µmol, 1 mL). The mixture was stirred at 35° C. for 5 hrs. On completion, the mixture was concentrated in vacuo. The residue was purified by prep-HPLC (column: Phenomenex luna C18 150*25 mm*10 µm; mobile phase: [water (FA)-ACN]; gradient: 10%-40% B over 8 min) to give the title compound (14.9 mg, 38% yield, FA salt) as yellow solid. ¹H NMR (400 MHz, DMSO-d₆) δ 11.04 (s, 1H), 9.04 (s, 1H), 8.24-8.16 (m, 2H), 7.71-7.57 (m, 3H), 7.10 (d, J=8.0 Hz, 1H), 7.05-6.95 (m, 2H), 5.38 (dd, J=5.6, 12.8 Hz, 1H), 4.74 (s, 2H), 4.46 (d, J=11.6 Hz, 1H), 4.33 (d, J=12.4 Hz, 1H), 4.25-4.18 (m, 1H), 4.16-4.09 (m, 2H), 4.07-4.00 (m, 2H), 3.72-3.62 (m, 4H), 3.57 (s, 3H), 3.52-3.47 (m, 2H), 3.30-3.22 (m, 3H), 3.13-3.04 (m, 2H), 2.94-2.84 (m, 1H), 2.80-2.65 (m, 4H), 2.09-1.98 (m, 2H), 1.92-1.83 (m, 2H), 1.79-1.60 (m, 10H), 1.54-1.47 (m, 1H), 1.46-1.37 (m, 2H); LC-MS (ESI⁺) m/z 995.5 (M+H)⁺.

Example 39. Synthesis of Compound 038

(a) Step 1—Tert-butyl 4-[1-(2,6-dioxo-3-piperidyl)-3-methyl-2-oxo-benzimidazol-4-yl]-3,6-dihydro-2H-pyridine-1-carboxylate

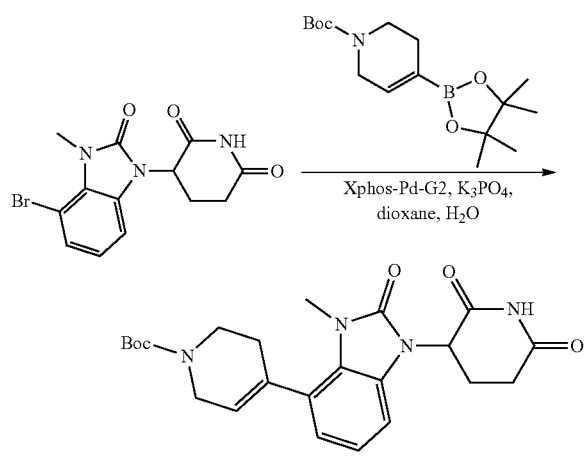

To a mixture of 3-(4-bromo-3-methyl-2-oxo-benzimidazol-1-yl)piperidine-2,6-dione (5.10 g, 15.0 mmol) and tert-butyl 4-(4,4,5,5-tetramethyl-1,3,2-dioxaborolan-2-yl)-3,6-dihydro-2H-pyridine-1-carboxylate (6.06 g, 19.6 mmol) in dioxane (60 mL) and H₂O (2.5 mL) was added K₃PO₄ (9.60 g, 45.2 mmol) and XPhos-Pd-G₂ (593 mg, 754 μmol). The reaction mixture was stirred at 80° C. under N₂ for 12 hrs. On completion, the residue was diluted with water (80 mL) and extracted with EA (2×80 mL). The combined organic layers was dried over Na₂SO₄, filtered and the filtrate was concentrated in vacuo to give the title compound (3.50 g, 52% yield) as yellow solid. ¹H NMR (400 MHz, DMSO-d₆) δ 11.10 (s, 1H), 7.08-6.98 (m, 2H), 7.08-6.98 (m, 1H), 5.70 (s, 1H), 5.39 (dd, J=5.4, 12.6 Hz, 1H), 4.04-3.97 (m, 2H), 3.61-3.53 (m, 3H), 3.32 (s, 2H), 2.77-2.60 (m, 2H), 2.39 (s, 2H), 1.99 (s, 2H), 1.44 (s, 9H), LC-MS (ESI⁺) m/z 441.0 (M+H)⁺.

(b) Step 2—Tert-butyl 4-[1-(2,6-dioxo-3-piperidyl)-3-methyl-2-oxo-benzimidazol-4-yl]piperidine-1-carboxylate

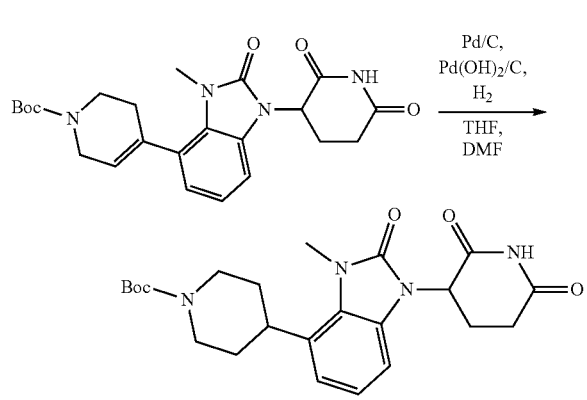

To a mixture of tert-butyl 4-[1-(2,6-dioxo-3-piperidyl)-3-methyl-2-oxo-benzimidazol-4-yl]-3,6-dihydro-2H-pyridine-1-carboxylate (3.50 g, 7.95 mmol) in THF (80 mL) and DMF (20 mL) was added Pd(OH)₂/C (700 mg, 20% purity) and Pd/C (700 mg, 657 μmol, 10% purity). The reaction mixture was stirred at 50° C. for 24 hrs under H₂ (50 psi). On completion, the reaction mixture was filtered and the filtrate was concentrated in vacuo to give the title compound (1.60 g, 45% yield) as white solid. ¹H NMR (400 MHz, DMSO-d₆) δ 11.10 (s, 1H), 6.98 (s, 3H), 5.38 (dd, J=5.2, 12.4 Hz, 1H), 4.15-4.01 (m, 2H), 3.60 (s, 3H), 3.48-3.38 (m, 1H), 3.33-3.23 (m, 1H), 2.86 (s, 2H), 2.69-2.58 (m, 2H), 2.02-1.96 (m, 1H), 1.81 (d, J=12.0 Hz, 2H), 1.58 (d, J=12.0 Hz, 2H), 1.42 (s, 9H), LC-MS (ESI⁺) m/z 387.0 (M+H)⁺.

(c) Step 3—3-[3-Methyl-2-oxo-4-(4-piperidyl)benzimidazol-1-yl]piperidine-2,6-dione

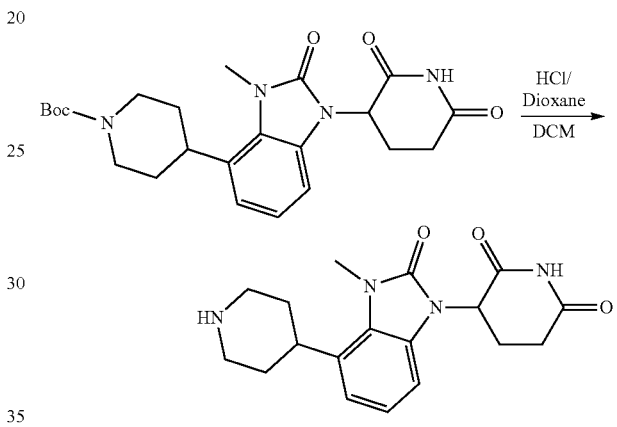

To a mixture of tert-butyl 4-[1-(2,6-dioxo-3-piperidyl)-3-methyl-2-oxo-benzimidazol-4-yl]piperidine-1-carboxylate (200 mg, 451 μmol) in DCM (2 mL) was added HCl/dioxane (2.5 M, 2.00 mL). The reaction mixture was stirred at 25° C. for 1 hr. On completion, the reaction mixture was concentrated in vacuo to give the title compound (150 mg, 96% yield, HCl salt) as white solid.

(d) Step 4—Tert-butyl 4-[[4-[1-(2,6-dioxo-3-piperidyl)-3-methyl-2-oxo-benzimidazol-4-yl]-1-piperidyl]methyl]piperidine-1-carboxylate

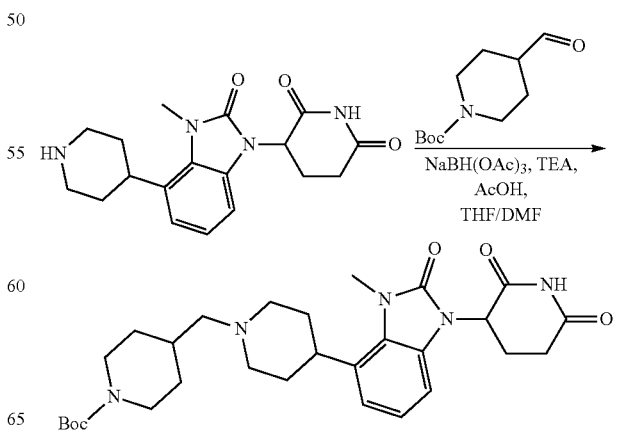

1019

To a mixture of 3-[3-methyl-2-oxo-4-(4-piperidyl)benzimidazol-1-yl]piperidine-2,6-dione (150 mg, 438 μmol, HCl salt) in THF (2 mL) and DMF (1 mL) was added TEA (132 mg, 1.31 mmol) and HOAc (78.9 mg, 1.31 mmol), tert-butyl 4-formylpiperidine-1-carboxylate (102 mg, 481 μmol). The reaction mixture was stirred at 0° C. for 0.5 hr. Then added NaBH(OAc)$_3$ (139 mg, 657 μmol). The reaction mixture was stirred at 25° C. for 2.5 hrs. On completion, the residue was diluted with water (30 mL) and extracted with EA (2×20 mL). The water was extracted with DCM (2×20 mL). The combined organic layers was dried over Na$_2$SO$_4$, filtered and the filtrate was concentrated in vacuo to give the title compound (126 mg, 53% yield) as white solid. $^1$H NMR (400 MHz, DMSO-d$_6$) δ 11.10 (s, 1H), 7.15-6.87 (m, 3H), 5.39 (dd, J=5.6, 12.8 Hz, 1H), 4.04-3.85 (m, 2H), 3.66-3.52 (m, 6H), 3.21-3.09 (m, 2H), 3.03-2.95 (m, 2H), 2.92-2.84 (m, 1H), 2.82-2.71 (m, 2H), 2.70-2.62 (m, 2H), 2.28-2.14 (m, 2H), 2.10-1.95 (m, 4H), 1.85-1.76 (m, 2H), 1.40 (s, 9H), 1.17-1.05 (m, 2H), LC-MS (ESI$^+$) m/z 540.2 (M+H)$^+$.

(e) Step 5—3-[3-Methyl-2-oxo-4-[1-(4-piperidylmethyl)-4-piperidyl]benzimidazol-1-yl]piperidine-2,6-dione

1020

-continued

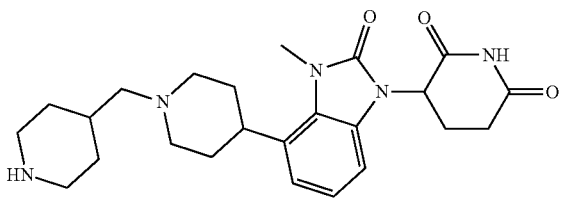

To a mixture of tert-butyl 4-[[4-[1-(2,6-dioxo-3-piperidyl)-3-methyl-2-oxo-benzimidazol-4-yl]-1-piperidyl]methyl]piperidine-1-carboxylate (126 mg, 259 μmol) in DCM (1 mL) was added HCl/dioxane (2.5 M, 103 μL). The reaction mixture was stirred at 25° C. for 1.5 hrs. On completion, the reaction mixture was concentrated in vacuo to give the title compound (114 mg, 99% yield, HCl salt) as white solid. LC-MS (ESI$^+$) m/z 440.2 (M+H)$^+$.

(f) Step 6—Tert-butyl 3-[2-[[(3S,8S)-3-[[4-[[4-[1-(2,6-dioxo-3-piperidyl)-3-methyl-2-oxo-benzimidazol-4-yl]-1-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

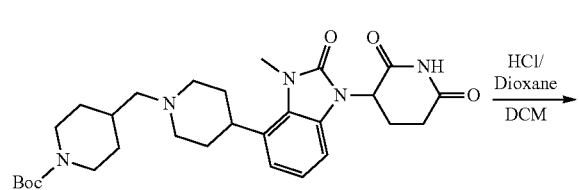

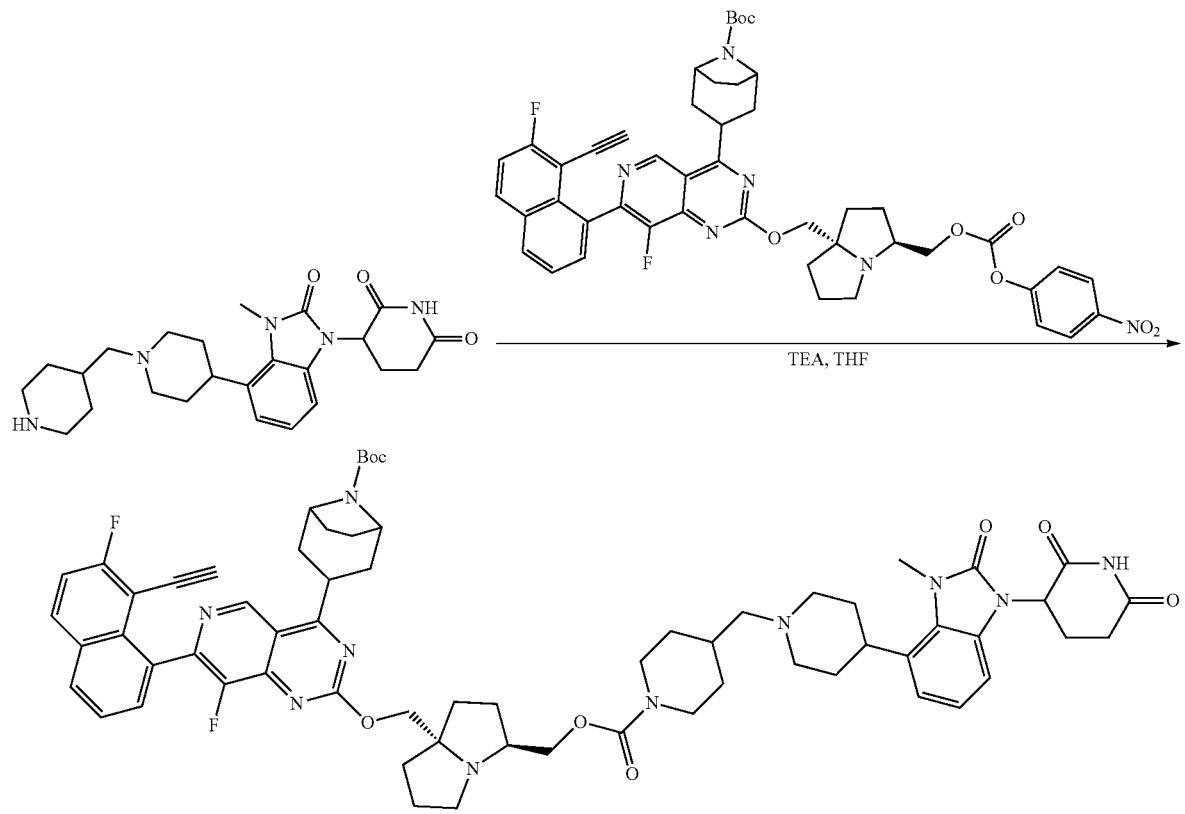

To a mixture of 3-[3-methyl-2-oxo-4-[1-(4-piperidylmethyl)-4-piperidyl]benzimidazol-1-yl] piperidine-2,6-dione (70.0 mg, 159 μmol, HCl salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (68.6 mg, 79.6 μmol) in THF (1 mL) was added TEA (16.1 mg, 159 μmol). The reaction mixture was stirred at 25° C. for 4 hrs. On completion, the reaction mixture was concentrated in vacuo. The residue was purified by prep-HPLC (column: Phenomenex luna C18 150*25 mm*10 μm; mobile phase: [water (FA)-ACN]; gradient: 21%-51% B over 10 min) to give the title compound (40.0 mg, 21% yield) as yellow solid. $^1$H NMR (400 MHz, DMSO-$d_6$) δ 11.10 (s, 1H), 9.09 (s, 1H), 8.30 (s, 1H), 8.26-8.17 (m, 2H), 7.71-7.58 (m, 3H), 7.02-6.94 (m, 3H), 5.43-5.33 (m, 1H), 4.60-4.50 (m, 1H), 4.45-4.36 (m, 1H), 4.35-4.28 (m, 2H), 4.23-4.18 (m, 1H), 4.17-4.11 (m, 2H), 4.08-4.01 (m, 2H), 3.99-3.91 (m, 2H), 3.70-3.62 (m, 2H), 3.59-3.55 (m, 3H), 2.95-2.90 (m, 2H), 2.78-2.70 (m, 4H), 2.65-2.62 (m, 1H), 2.17-2.12 (m, 2H), 2.08-1.96 (m, 5H), 1.87-1.82 (m, 2H), 1.80-1.61 (m, 18H), 1.56-1.50 (m, 2H), 1.46 (s, 9H), LC-MS (ESI$^+$) m/z 1162.3 (M+H)$^+$.

(g) Step 7—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-4-yl]-1-piperidyl]methyl]piperidine-1-carboxylate (038)

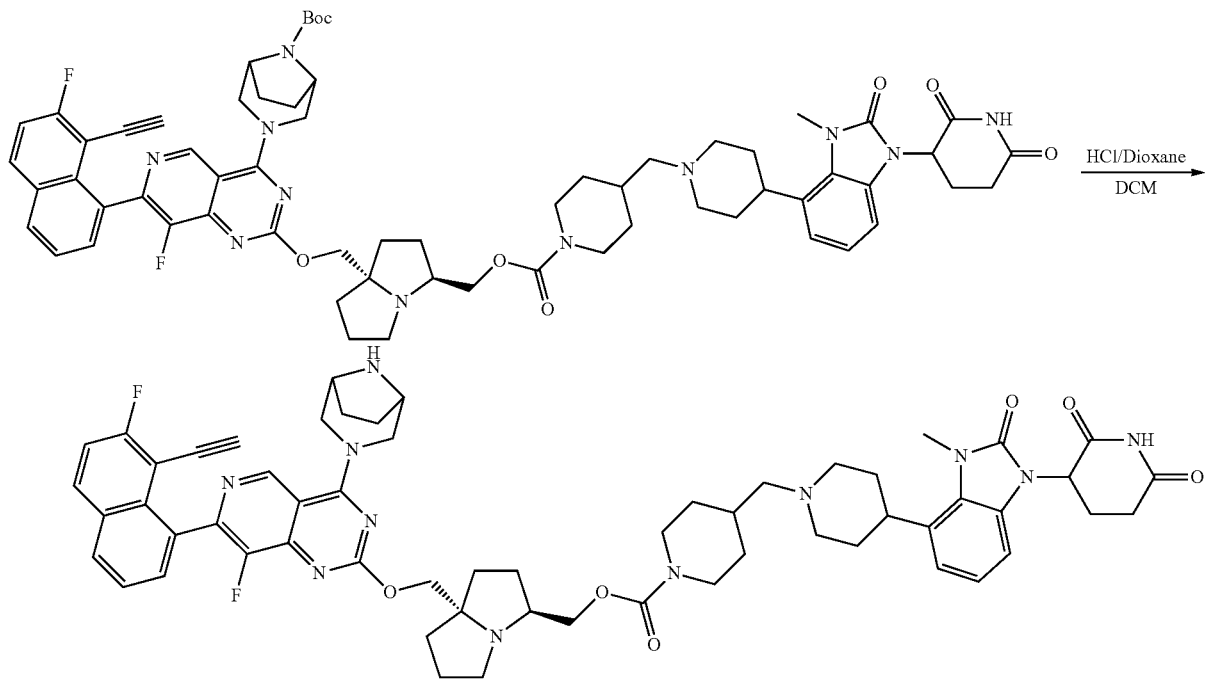

038

To a mixture of tert-butyl 3-[2-[[(3S,8S)-3-[[4-[[4-[1-(2,6-dioxo-3-piperidyl)-3-methyl-2-oxo benzimidazol-4-yl]-1-piperidyl] methyl] piperidine-1-carbonyl] oxymethyl]-1,2,3,5,6,7-hexahydropyrrolizin-8-yl] methoxy]-7-(8-ethynyl-7-fluoro-1-naphthyl)-8-fluoro-pyrido [4,3-d] pyrimidin-4-yl]-3,8-diazabicyclo[3.2.1]octane-8-carboxylate (40.0 mg, 34.4 μmol) in DCM (1 mL) was added HCl/dioxane (2.5 M, 800 μL). The reaction mixture was stirred at 25° C. for 0.5 hr. On completion, the residue was lyophilized to give the title compound (30.9 mg, 78% yield, HCl) as yellow solid. $^1$H NMR (400 MHz, DMSO-$d_6$) δ 11.11 (s, 2H), 10.46 (d, J=7.6 Hz, 1H), 10.06 (d, J=8.4 Hz, 1H), 9.72 (s, 1H), 9.17 (s, 1H), 8.28-8.20 (m, 2H), 7.75-7.60 (m, 3H), 7.12-6.97 (m, 3H), 5.40 (dd, J=5.2, 12.8 Hz, 1H), 4.74-4.64 (m, 3H), 4.62-4.53 (m, 1H), 4.42-4.35 (m, 1H), 4.21 (s, 4H), 4.07 (d, J=5.2 Hz, 1H), 4.05-3.95 (m, 4H), 3.38 (s, 4H), 3.21-3.08 (m, 2H), 2.96 (s, 2H), 2.92-2.75 (m, 4H), 2.72-2.64 (m, 2H), 2.44-2.35 (m, 2H), 2.35-2.26 (m, 2H), 2.17-1.84 (m, 20H), 1.75 (s, 1H), LC-MS (ESI$^+$) m/z 1062.2 (M+H)$^+$.

Example 40. Synthesis of Compound 039

(a) Step 1—Tert-butyl N-[4-[4-[1-(2,6-dioxo-3-piperidyl)-3-methyl-2-oxo-benzimidazol-4-yl]-1-piperidyl]-4-oxo-butyl]carbamate

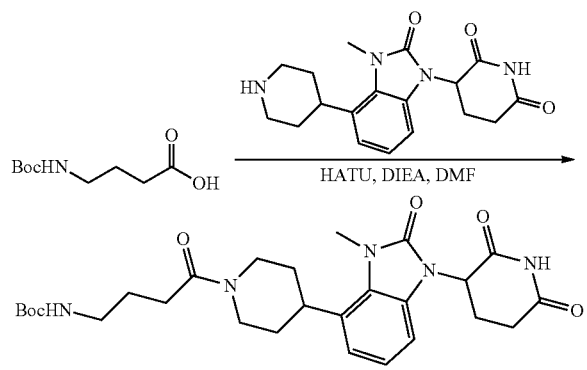

To a mixture of 4-(tert-butoxycarbonylamino)butanoic acid (112 mg, 554 μmol, CAS #57294-38-9) in DMF (1 mL) was added DIEA (215 mg, 1.66 mmol, 289 μL) and HATU (253 mg, 665 μmol). The reaction mixture was stirred at 25° C. for 0.5 hr. Then the 3-[3-methyl-2-oxo-4-(4-piperidyl)benzimidazol-1-yl]piperidine-2,6-dione (190 mg, 554 μmol) was added into above solution. The reaction mixture was stirred at 25° C. for 1 hr. On completion, the reaction mixture was quenched with water (0.5 mL) and concentrated in vacuo. The residue was purified by reverse phase (0.1% FA condition) to give the title compound (180 mg, 61% yield) as white solid. $^1$H NMR (400 MHz, DMSO-$d_6$) δ 11.10 (s, 1H), 6.99 (s, 3H), 6.85-6.80 (m, 1H), 5.38 (dd, J=5.2, 12.4 Hz, 1H), 4.56 (d, J=13.2 Hz, 1H), 3.97 (d, J=12.4 Hz, 1H), 3.62 (s, 3H), 3.54-3.48 (m, 1H), 3.18 (t, J=12.4 Hz, 1H), 2.95 (dd, J=4.4, 6.0 Hz, 2H), 2.89 (d, J=5.2 Hz, 1H), 2.71-2.60 (m, 3H), 2.34 (q, J=7.2 Hz, 2H), 2.01-1.97 (m, 1H), 1.83 (d, J=7.6 Hz, 2H), 1.68-1.55 (m, 4H), 1.38 (s, 9H). LC-MS (ESI$^+$) m/z 528.1 (M+H)$^+$.

(b) Step 2—3-[4-[1-(4-Aminobutanoyl)-4-piperidyl]-3-methyl-2-oxo-benzimidazol-1-yl]piperidine-2,6-dione

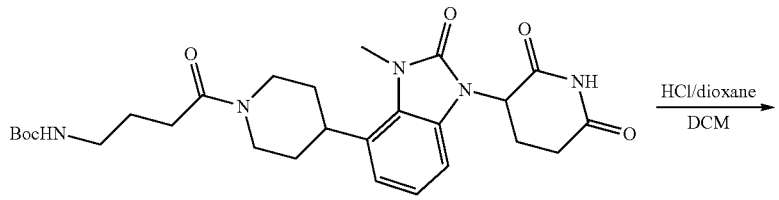

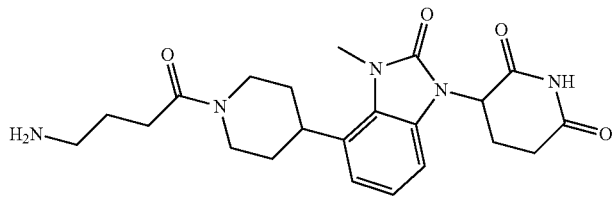

To a solution of tert-butyl N-[4-[4-[1-(2,6-dioxo-3-piperidyl)-3-methyl-2-oxo-benzimidazol-4-yl]-1-piperidyl]-4-oxo-butyl]carbamate (70.0 mg, 132 μmol) in DCM (1 mL) was added HCl/dioxane (4 M, 2 mL), the reaction mixture was stirred at 25° C. for 1 hr. On completion, the reaction mixture was concentrated in vacuo to give the title compound (55.0 mg, 96% yield, HCl salt) as white solid. LC-MS (ESI$^+$) m/z 428.0 (M+H)$^+$.

(c) Step 3—Tert-butyl 3-[2-[[(3S,8S)-3-[[4-[4-[1-(2, 6-dioxo-3-piperidyl)-3-methyl-2-oxo-benzimidazol-4-yl]-1-piperidyl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

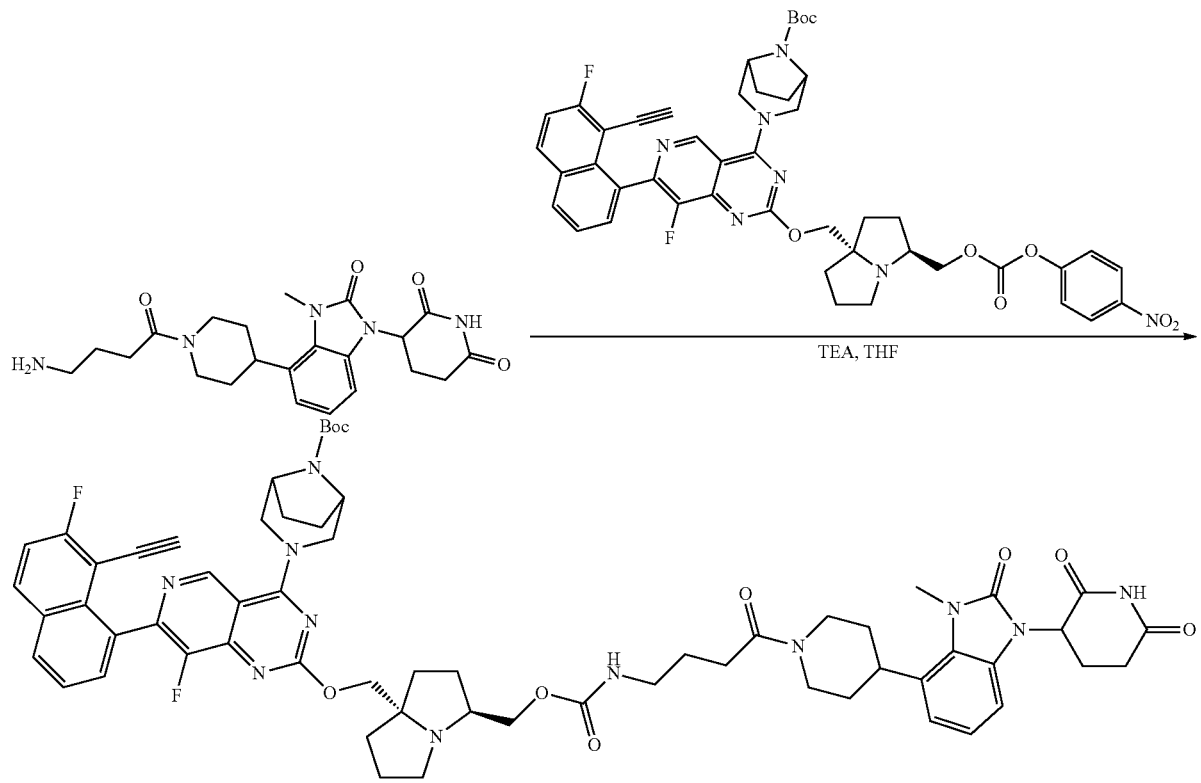

To a mixture of 3-[4-[1-(4-aminobutanoyl)-4-piperidyl]-3-methyl-2-oxo-benzimidazol-1-yl]piperidine-2,6-dione (45.0 mg, 105 µmol, HCl salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido [4,3-d]pyrimidin-4-yl]-3,8-diazabicyclo[3.2.1]octane-8-carboxylate (69.7 mg, 80.9 µmol) in THF (1 mL) was added TEA (24.5 mg, 242 µmol), the reaction mixture was stirred at 25° C. for 1 hr. On completion, the reaction mixture was concentrated in vacuo. The residue was purified by prep-HPLC (column: Welch Ultimate C18 150*25 mm*5 µm; mobile phase: [water (FA)-ACN]; gradient: 22%-52% B over 10 min) to give the title compound (40.0 mg, 42% yield) as white solid. LC-MS (ESI⁺) m/z 1150.5 (M+H)⁺.

(d) Step 4—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl N-[4-[4-[1-(2,6-dioxo-3-piperidyl)-3-methyl-2-oxo-benzimidazol-4-yl]-1-piperidyl]-4-oxo-butyl]carbamate (039)

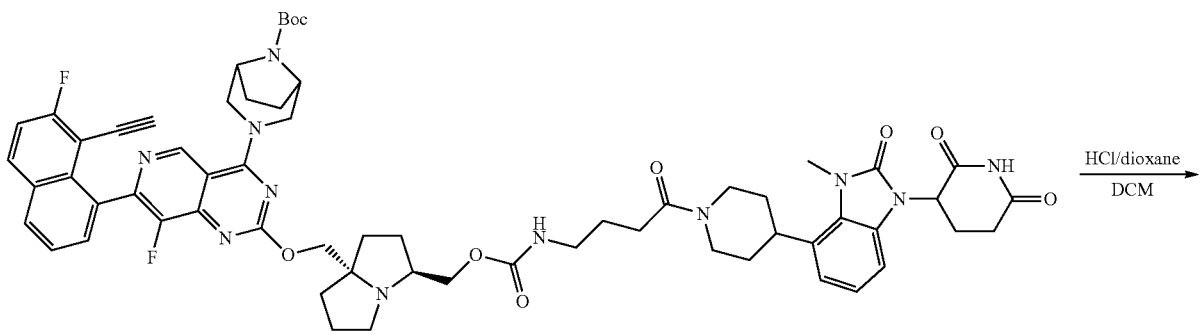

-continued

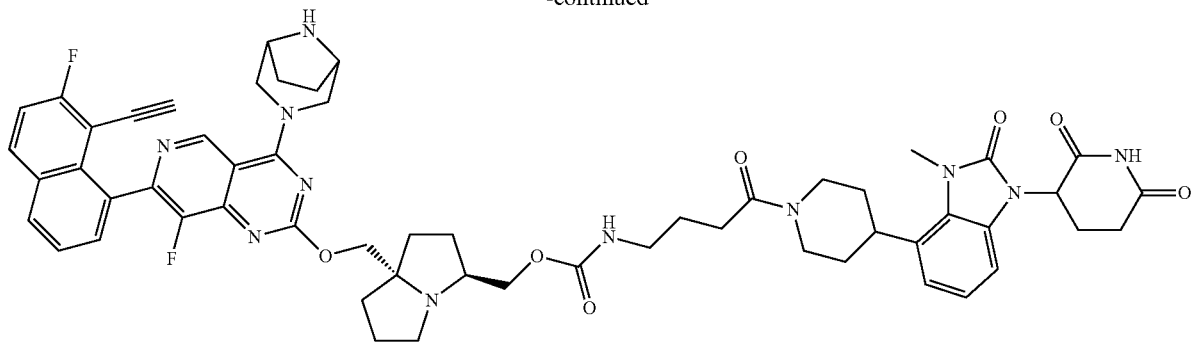

039

To a solution of tert-butyl 3-[2-[[(3S,8S)-3-[[4-[4-[1-(2,6-dioxo-3-piperidyl)-3-methyl-2-oxo-benzimidazol-4-yl]-1-piperidyl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 34.7 μmol) in DCM (1 mL) was added HCl/dioxane (4 M, 8.69 μL), the reaction mixture was stirred at 25° C. for 0.3 hr. On completion, the reaction mixture was concentrated in vacuo. The residue was purified by prep-HPLC (column: Welch Ultimate C18 150*25 mm*5 μm; mobile phase: [water (FA)-ACN]; gradient: 10%-40% B over 10 min) to give the title compound (14.3 mg, 36% yield, FA) as yellow solid. $^1$H NMR (400 MHz, DMSO-$d_6$) δ 11.09 (s, 1H), 9.05 (s, 1H), 8.22-8.16 (m, 2H), 7.70-7.50 (m, 3H), 7.23 (t, J=5.2 Hz, 1H), 6.98 (s, 3H), 5.37 (dd, J=5.2, 12.4 Hz, 1H), 4.59-4.44 (m, 2H), 4.33 (d, J=11.6 Hz, 1H), 4.18-4.07 (m, 3H), 4.04-3.94 (m, 3H), 3.66 (s, 1H), 3.64-3.62 (m, 2H), 3.60 (s, 3H), 3.58 (s, 1H), 3.52-3.46 (m, 3H), 3.23 (d, J=3.2, 17.6 Hz, 3H), 3.04-2.98 (m, 2H), 2.93-2.84 (m, 1H), 2.78-2.57 (m, 5H), 2.33 (dd, J=2.4, 4.4 Hz, 2H), 2.05-1.97 (m, 2H), 1.85-1.79 (m, 2H), 1.72 (s, 3H), 1.72-1.66 (m, 5H), 1.65-1.60 (m, 3H), 1.54-1.47 (m, 2H). LC-MS (ESI$^+$) m/z 1050.6 (M+H)$^+$.

Example 41. Synthesis of Compound 040

(a) Step 1—Tert-butyl 4-prop-2-ynyl-1-oxa-4,9-diazaspiro[5.5]undecane-9-carboxylate

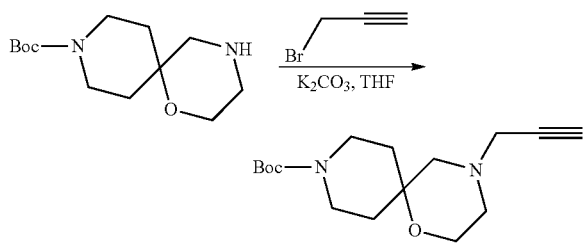

To a solution of tert-butyl-1-oxa-4,9-diazaspiro[5.5]undecane-9-carboxylate (1.00 g, 3.90 mmol, CAS #930785-40-3) and 3-bromoprop-1-yne (464 mg, 3.90 mmol, CAS #106-96-7) in THF (20 mL) was added K$_2$CO$_3$ (1.08 g, 7.80 mmol). The mixture was stirred at 25° C. for 12 hrs. On completion, the mixture was diluted with H$_2$O (50 mL) and extracted with DCM (3×100 mL). The combined organic layer were washed with brine (3×50 mL), dried over anhydrous Na$_2$SO$_4$, filtered and the filtrate was concentrated in vacuo. The residue was purified by column chromatography (SiO$_2$, Petroleum ether/Ethyl acetate=10/0 to 2/1) to give the title compound (600 mg, 52% yield) as white solid. $^1$H NMR (400 MHz, CDCl$_3$) δ 3.79-3.74 (m, 2H), 3.73-3.65 (m, 1H), 3.26 (s, 2H), 3.16 (t, J=11.4 Hz, 2H), 2.52 (s, 2H), 2.36 (s, 2H), 2.27 (s, 1H), 1.93 (d, J=11.4 Hz, 2H), 1.69-1.56 (m, 1H), 1.49-1.47 (m, 1H), 1.46 (s, 9H), 1.45-1.41 (d, J=4.4 Hz, 1H).

(b) Step 2—Tert-butyl 4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate

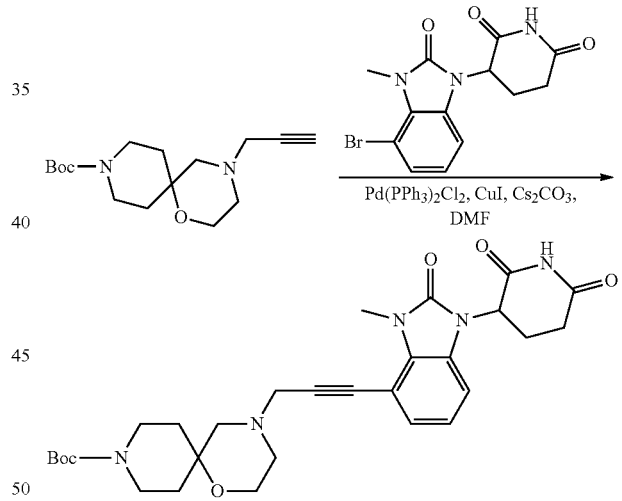

To a solution of tert-butyl 4-prop-2-ynyl-1-oxa-4,9-diazaspiro[5.5]undecane-9-carboxylate (261 mg, 887 μmol) and 3-(4-bromo-3-methyl-2-oxo-benzimidazol-1-yl)piperidine-2,6-dione (100 mg, 295 μmol, CAS #191732-76-0) in DMF (10 mL) was added Cs$_2$CO$_3$ (192 mg, 591 μmol), CuI (5.63 mg, 29.5 μmol) and dichloropalladium; triphenylphosphane (20.7 mg, 29.5 μmol). The mixture was stirred at 80° C. for 2 hrs under N$_2$ atmosphere. On completion, the mixture was filtered and the filtrate was concentrated in vacuo to give a crude. The crude product was purified by reversed-phase HPLC (0.1% FA condition) to give the title compound (70.0 mg, 42% yield) as white solid. $^1$H NMR (400 MHz, DMSO-$d_6$) δ 11.19-11.06 (m, 1H), 7.21-7.09 (m, 2H), 7.21-7.06 (m, 1H), 7.05-6.96 (m, 1H), 5.45-5.35 (m, 1H), 3.74-3.61 (m, 4H), 3.61-3.48 (m, 4H), 3.30 (s, 2H), 3.13-2.94 (m, 2H), 2.93-2.83 (m, 1H), 2.78-2.57 (m, 3H), 2.42-2.29 (m, 2H), 2.08-1.95 (m, 1H), 1.81 (d, J=13.4 Hz, 1H), 1.50-1.26 (m, 10H); LC-MS (ESI$^+$) m/z 552.2 (M+H)$^+$.

(c) Step 3—Tert-butyl 4-[3-[1-(2,6-dioxo3-piperidyl)-3-methyl-2-oxo-benzimidazol-4 yl]propyl]-1-oxa 4,9-diazaspiro[5.5]undecane-9-carboxylate

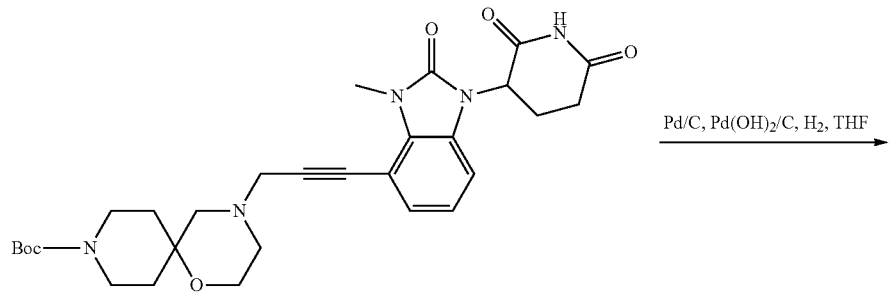

Pd/C, Pd(OH)₂/C, H₂, THF

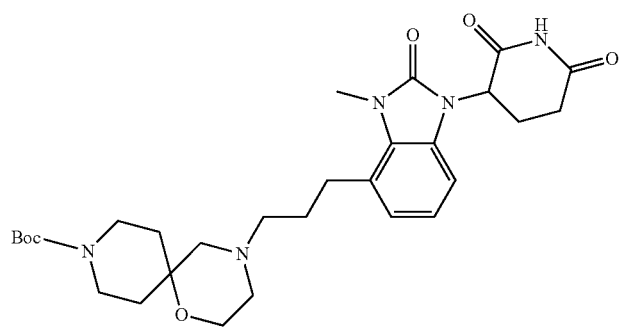

A mixture of Pd/C (30.0 mg, 28.1 μmol, 10% purity) and Pd(OH)₂ (30.0 mg, 42.7 μmol, 20% purity) in THF (5 mL), the solution of tert-butyl 4-[3-[1-(2,6-dioxo-3-piperidyl)-3-methyl 2-oxo benzimidazol-4-yl]prop-2-ynyl]-1-oxa-4,9-diazaspiro[5.5]undecane-9-carboxylate (132 mg, 239 μmol) in THF (5 mL) was added into above mixture. The suspension was degassed and purged with H₂ for 3 times. The mixture was stirred under H₂ (15 Psi) at 25° C. for 1 hr under H₂ atmosphere. On completion, the reaction mixture was filtered and the filtrate was concentrated in vacuo. The residue was purified by prep-HPLC (column: Welch Xtimate C18 150*25 mm*5 μm; mobile phase: [water (TFA)-ACN]; gradient: 17%-47% B over 10 min) to give the title compound (24.0 mg, 18% yield) as white solid. LC-MS (ESI⁺) m/z 556.4 (M+H)⁺.

(d) Step 4—3-[3-Methyl-4-[3-(1-oxa-4,9 diazaspiro[5.5]undecan-4-yl)propyl]-2-oxo-benzimidazol-1 yl]piperidine-2,6-dione

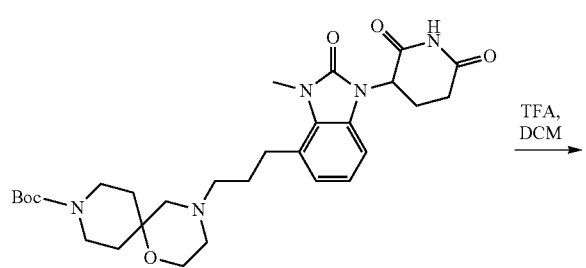

TFA, DCM

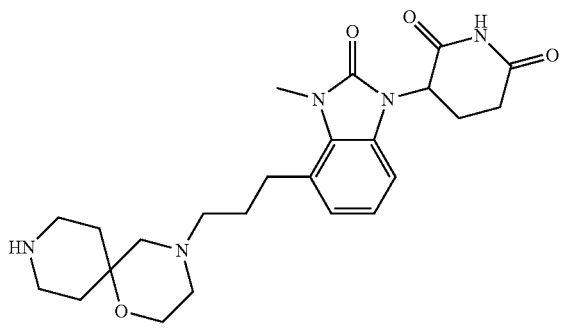

To a solution of tert-butyl 4-[3-[1-(2,6-dioxo-3-piperidyl)-3methyl-2-oxo-benzimidazol-4 yl]propyl]-1-oxa-4,9-diazaspiro[5.5]undecane-9-carboxylate (78.0 mg, 140 μmol) in DCM (1 mL) was added TFA (1.25 g, 10.9 mmol). The mixture was stirred at 25° C. for 0.5 hr. On completion, the mixture was concentrated in vacuo to give the title compound (60.0 mg, 93% yield, TFA salt) as white solid. LC-MS (ESI⁺) m/z 456.1 (M+H)⁺.

(e) Step 5—[(3S,8S)-8 [[4-(8-Tert-butoxycarbonyl-3,8-diazabicyclo[3.2.1]octan 3-yl)-7 (8-ethynyl 7-fluoro-1naphthyl)-8-fluoro-pyrido[4,3-d]pyrimidin-2yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propyl]-1-oxa-4,9-diazaspiro[5.5]undecane-9-carboxylate

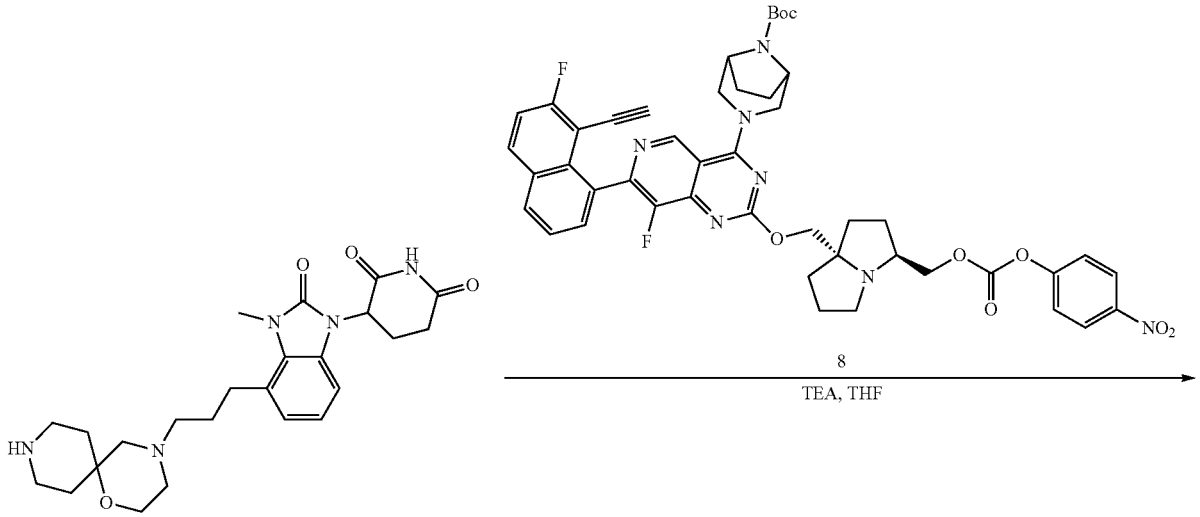

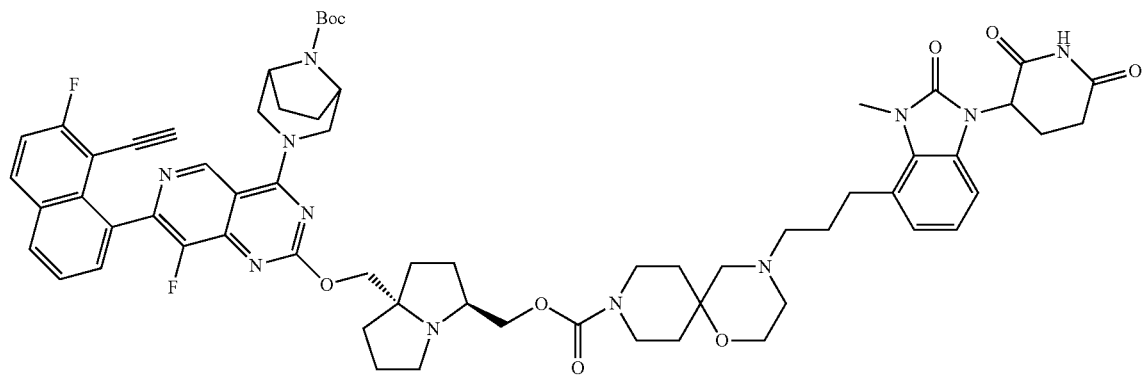

To a solution of 3-[3-methyl-4 [3(1-oxa-4,9-diazaspiro[5.5]undecan4-yl)propyl]2-oxo-benzimidazol-1 yl]piperidine 2,6-dione (58.6 mg, 128 μmol, TFA salt) in THF (3 mL) was added TEA (26.0 mg, 257 μmol) and tert-butyl3-[7-(8-ethynyl7fluoro1-naphthyl)-8-fluoro2-[[(3S,8S)3[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74.0 mg, 85.8 μmol). The mixture was stirred at 25° C. for 0.5 hr. On completion, the mixture was concentrated in vacuo The residue was purified by prep-HPLC (column: Phenomenex luna C18 150*25 mm*10 μm; mobile phase: [water (FA)-ACN]; gradient: 20%-50% B over 10 minutes) to give the title compound (15.0 mg, 14% yield) as white solid. $^1$H NMR (400 MHz, CDCl$_3$) δ 9.18-9.09 (m, 1H), 8.2-7.7 (s, 2H), 7.73-7.54 (m, 2H), 7.37-7.29 (m, 1H), 7.03-6.90 (m, 1H), 6.87-6.76 (m, 1H), 6.73-6.65 (m, 1H), 5.26-5.15 (m, 1H), 4.65-4.27 (m, 6H), 4.02-3.89 (m, 2H), 3.67-3.58 (m, 3H), 3.34-2.87 (m, 10H), 2.85-2.63 (m, 4H), 2.57-2.33 (m, 4H), 2.29-2.15 (m, 6H), 2.00 (s, 14H), 1.68-1.38 (m, 13H); LC-MS (ESI$^+$) m/z 1178.2 (M+H)$^+$.

(f) Step 6—[(3S,8S)8-[[4-(3,8-Diazabicyclo[3.2.1]
octan3-yl)7(8-ethynyl-7-fluoro-1-naphthyl)-8fluoro-
pyrido[4,3-d]pyrimidin-2-yl]oxymethyl]1,2,3,5,6,7-
hexahydropyrrolizin-3-yl]methyl4-[3-[1-(2,6-dioxo-
3-piperidyl)-3-methyl-2-oxo-benzimidazol-4-yl]
propyl]-1-oxa-4,9-diazaspiro[5.5]undecane-9-
carboxylate (040)

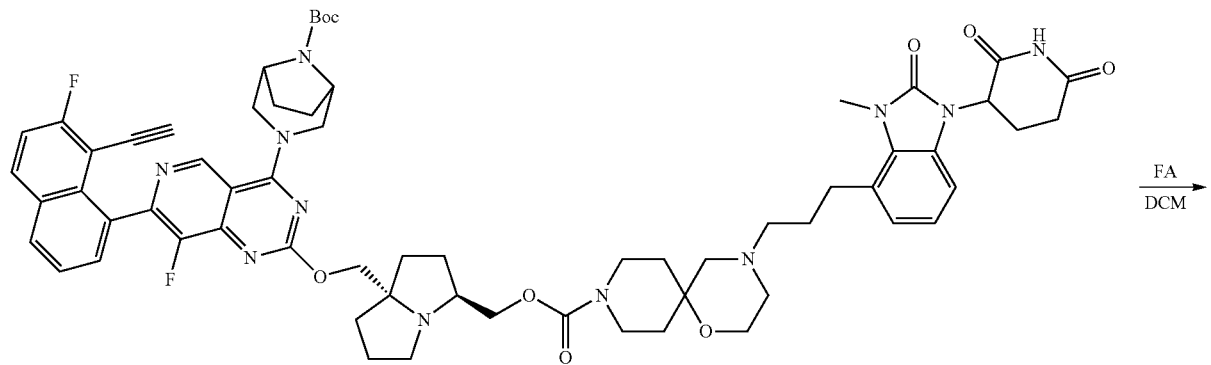

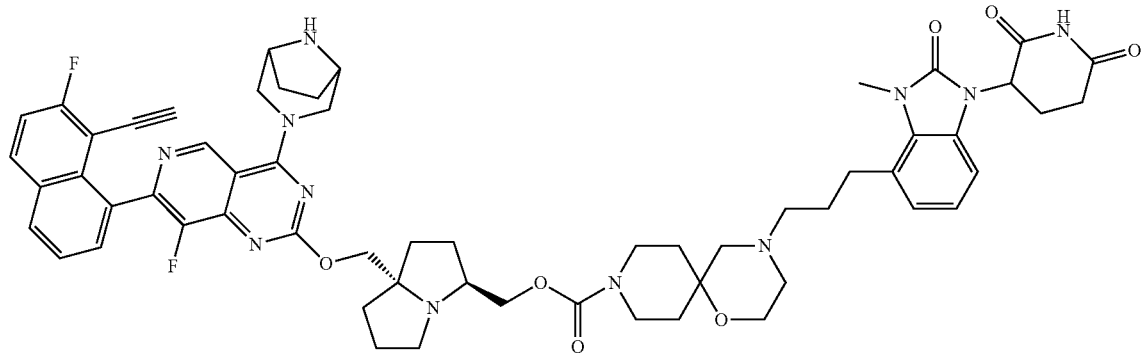

040

To a solution of [(3S,8S)-8-[[4-(8-tert-butoxycarbonyl-3,8-diazabicyclo[3.2.1]octan-3-yl) 7-(8-ethynyl 7-fluoro-1-naphthyl)-8-fluoro-pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propyl]-1-oxa-4,9-diazaspiro[5.5]undecane-9-carboxylate (10.0 mg, 8.49 µmol) in DCM (1 mL) was added HCOOH (407 µg, 8.49 µmol). The mixture was stirred at 25° C. for 0.5 hr. On completion, the residue was lyophilized to give the title compound (9.08 mg, 98% yield, FA) as white solid.

$^1$H NMR (400 MHz, DMSO-$d_6$) δ 11.15 (s, 1H), 9.08 (s, 1H), 8.28-8.10 (m, 3H), 7.71-7.57 (m, 2H), 7.06-6.75 (m, 3H), 5.45-5.25 (m, 1H), 4.63-4.47 (m, 1H), 4.46-4.33 (m, 1H), 4.27-4.06 (m, 4H), 3.98 (s, 1H), 3.80 (s, 2H), 3.73-3.67 (m, 2H), 3.62-3.58 (m, 4H), 3.54 (s, 3H), 3.35-3.31 (m, 2H), 3.11-3.03 (m, 2H), 2.90 (s, 2H), 2.82 (s, 1H), 2.71-2.63 (m, 1H), 2.54-2.22 (m, 2H), 2.34-2.23 (m, 4H), 2.22-2.13 (m, 2H), 2.11-1.92 (m, 3H), 1.77 (s, 13H), 1.59-1.49 (m, 1H), 1.46-1.35 (m, 2H); LC-MS (ESI$^+$) m/z 1078.2 (M+H)$^+$.

Example 42. Synthesis of Compound 041

(a) Step 1—Tert-butyl 4-[4-[1-(2,6-dioxo-3-piperidyl)-3-methyl-2-oxo-benzimidazol-4-yl]butyl]piperidine-1-carboxylate

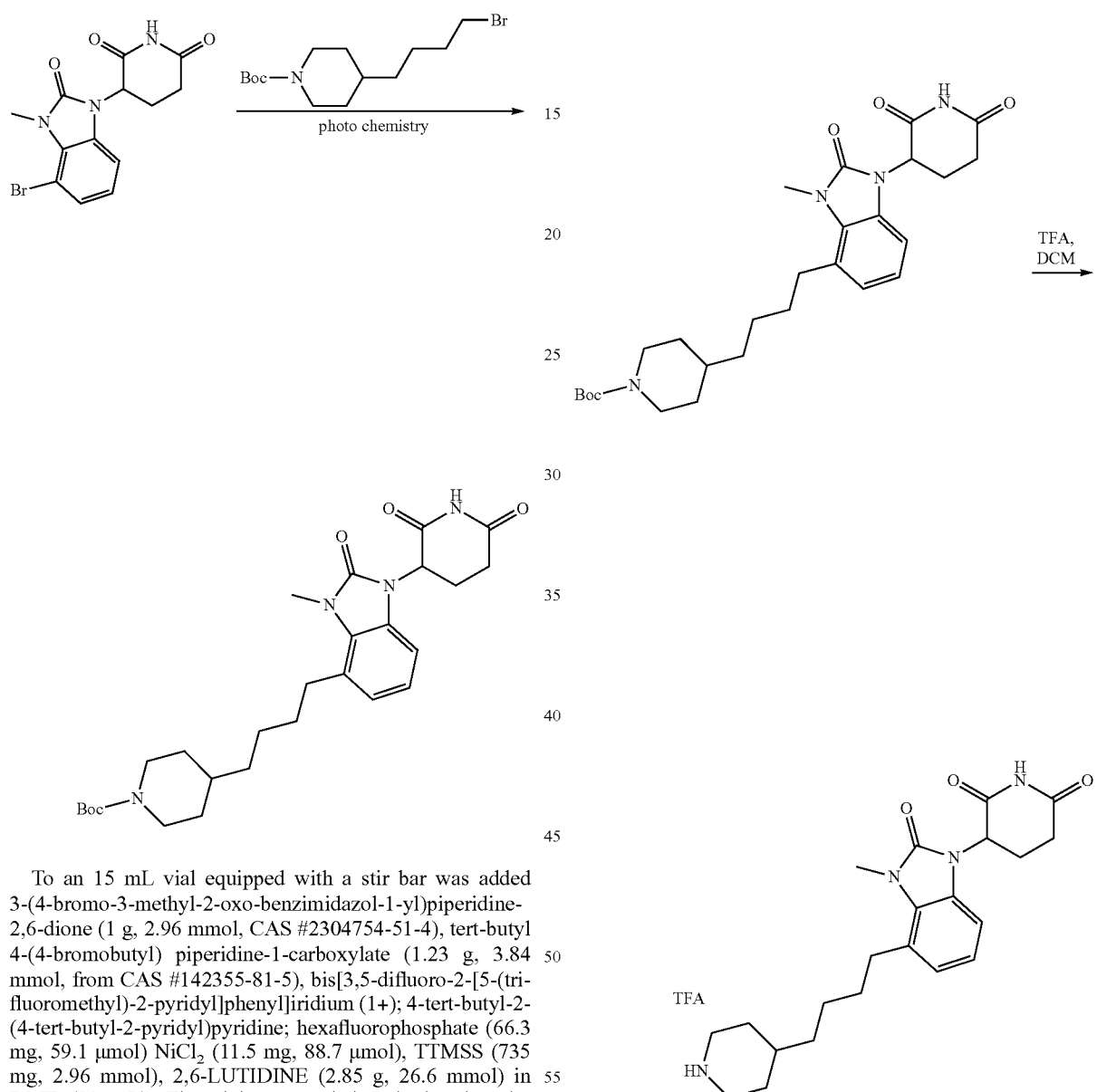

To an 15 mL vial equipped with a stir bar was added 3-(4-bromo-3-methyl-2-oxo-benzimidazol-1-yl)piperidine-2,6-dione (1 g, 2.96 mmol, CAS #2304754-51-4), tert-butyl 4-(4-bromobutyl) piperidine-1-carboxylate (1.23 g, 3.84 mmol, from CAS #142355-81-5), bis[3,5-difluoro-2-[5-(trifluoromethyl)-2-pyridyl]phenyl]iridium (1+); 4-tert-butyl-2-(4-tert-butyl-2-pyridyl)pyridine; hexafluorophosphate (66.3 mg, 59.1 μmol) NiCl$_2$ (11.5 mg, 88.7 μmol), TTMSS (735 mg, 2.96 mmol), 2,6-LUTIDINE (2.85 g, 26.6 mmol) in DME (20 mL). The vial was sealed and placed under nitrogen was added. The reaction was stirred and irradiated with a 10 W blue LED lamp (3 cm away), with cooling water to keep the reaction temperature at 25° C. for 14 hrs. On completion, the mixture was filtered and concentrated in vacuo to give a residue. The mixture was quenched with H$_2$O (50 mL) and extracted with dichloromethane (25 mL×3), the combined organic phase was dried over anhydrous sodium sulfate, filtered and concentrated to give a residue. The residue was purified by reversed phase flash (0.1% FA condition) to give the title compound (500 mg, 33% yield) as a yellow solid. $^1$H NMR (400 MHz, DMSO-d$_6$) δ 11.09 (s, 1H), 6.95 (d, J=5.2 Hz, 2H), 6.88-6.83 (m, 1H), 5.36 (J=5.2, 12.4 Hz, 1H), 3.90 (d, J=11.2 Hz, 2H), 3.54 (s, 3H), 3.40-3.18 (m, 2H), 2.96-2.80 (m, 3H), 2.77-2.53 (m, 5H), 2.10-1.89 (m, 1H), 1.66-1.49 (m, 4H), 1.38 (s, 9H), 1.31-1.18 (m, 2H), 1.08-0.84 (m, 2H); LC-MS (ESI$^+$) m/z 399.1 (M+H−100)$^+$.

(b) Step 2—3-[3-Methyl-2-oxo-4-[4-(4-piperidyl)butyl]benzimidazol-1-yl]piperidine-2,6-dione

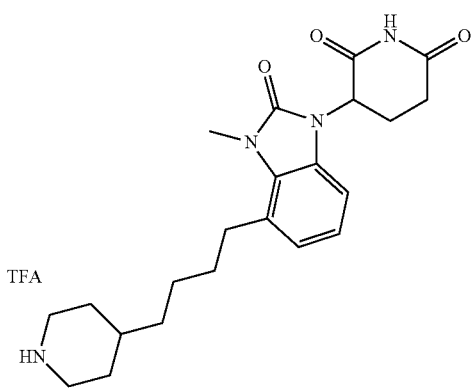

To a solution of tert-butyl 4-[4-[1-(2,6-dioxo-3-piperidyl)-3-methyl-2-oxo-benzimidazol-4-yl]butyl]piperidine-1-carboxylate (80.0 mg, 160 μmol) in DCM (1 mL) was added TFA (0.2 mL). The mixture was stirred at 25° C. for 1 hr. On completion, the reaction mixture was concentrated in vacuo to give the title compound (80.0 mg, 98% yield, TFA salt) as brown oil. LC-MS (ESI$^+$) m/z 399.1 (M+H)$^+$.

(c) Step 3—Tert-butyl 3-[2-[[(3S,8S)-3-[[4-[4-[1-(2, 6-dioxo-3-piperidyl)-3-methyl-2-oxo-benzimidazol-4-yl]butyl]piperidine-1-carbonyl]oxymethyl]-1,2,3,5, 6,7-hexahydropyrrolizin-8-yl]methoxy]-7-(8-ethynyl-7-fluoro-1-naphthyl)-8-fluoro-pyrido[4,3-d] pyrimidin-4-yl]-3,8-diazabicyclo[3.2.1]octane-8-carboxylate

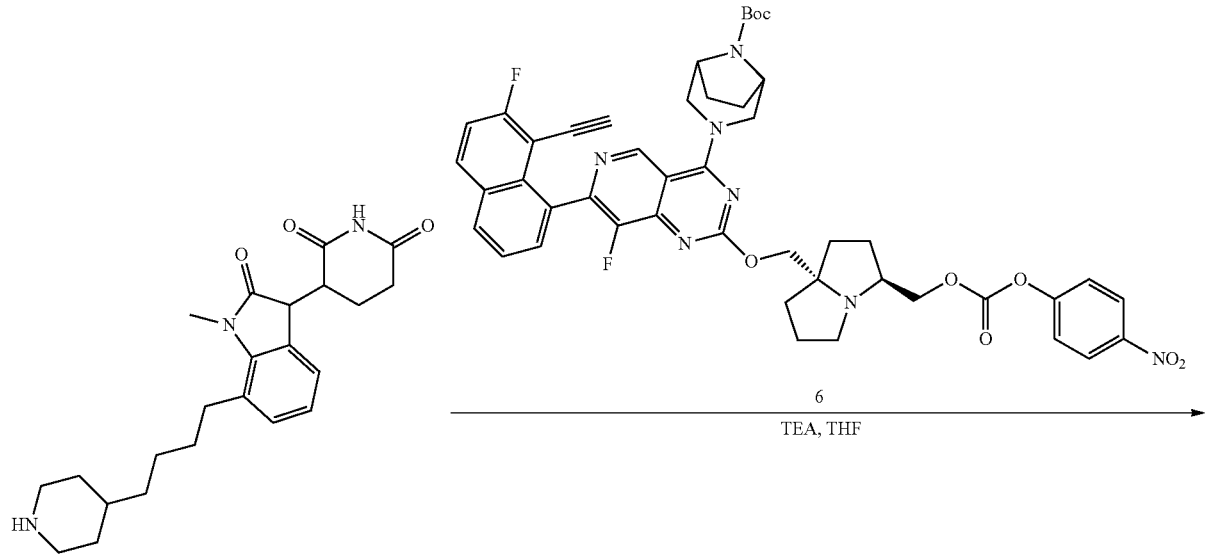

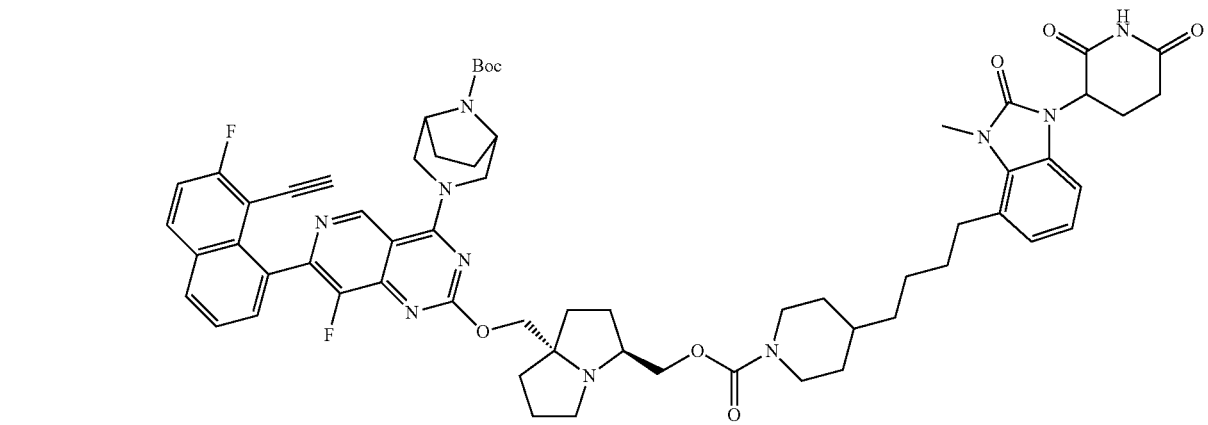

To a solution of 3-[3-methyl-2-oxo-4-[4-(4-piperidyl) butyl]benzimidazol-1-yl]piperidine-2,6-dione (60.0 mg, 117 μmol, TFA salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl] methoxy]pyrido[4,3-d]pyrimidin-4-yl]-3,8-diazabicyclo [3.2.1]octane-8-carboxylate (67.2 mg, 78.0 μmol) in THF (4 mL) was added TEA (7.90 mg, 78.0 μmol) until pH stabilized at 8. The mixture was stirred at 25° C. for 1 hr. On completion, the reaction mixture was concentrated in vacuo to give a residue. Then, the residue was purified by prep-HPLC (column: Phenomenex luna C18 150*25 mm*10 μm; mobile phase: [water (FA)-ACN]; gradient: 30%-60% B over 10 min) to give the title compound (50.0 mg, 54% yield, FA salt) as a white solid. 1H NMR (400 MHz, DMSO-d6) δ 11.10 (s, 1H), 9.09 (s, 1H), 8.30-8.16 (m, 2H), 7.76-7.54 (m, 3H), 6.94 (d, J=6.0 Hz, 2H), 6.84 (dd, J=2.8, 6.0 Hz, 1H), 5.36 (dd, J=5.2, 12.4 Hz, 1H), 4.55 (d, J=12.4 Hz, 1H), 4.45-4.37 (m, 1H), 4.30 (s, 2H), 4.24-4.10 (m, 3H), 4.05-4.01 (m, 1H), 4.00-3.88 (m, 2H), 3.64 (t, J=12.4 Hz, 2H), 3.52 (s, 3H), 2.91-2.82 (m, 3H), 2.77-2.66 (m, 5H), 2.61 (d, J=18.4 Hz, 3H), 2.08-1.94 (m, 2H), 1.89-1.81 (m, 2H), 1.80-1.69 (m, 7H), 1.65-1.51 (m, 6H), 1.46 (s, 9H), 1.39 (d, J=6.4 Hz, 3H), 1.28-1.20 (m, 2H), 1.03-0.88 (m, 2H); LC-MS (ESI+) m/z 1121.8 (M+H)+.

(d) Step 4—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[4-[1-(2,
6-dioxo-3-piperidyl)-3-methyl-2-oxo-benzimidazol-
4-yl]butyl]piperidine-1-carboxylate (041)

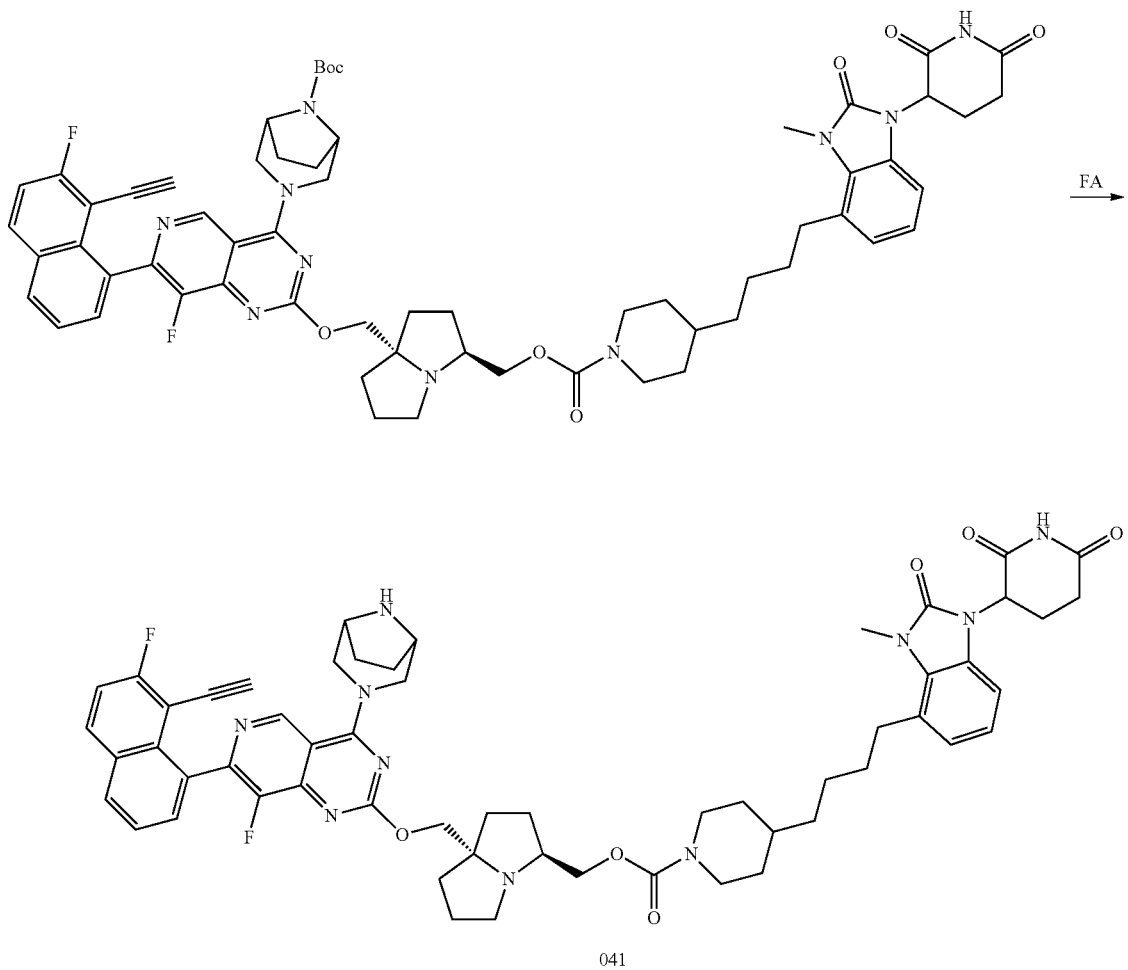

041

Tert-butyl 3-[2-[[(3S,8S)-3-[[4-[4-[1-(2,6-dioxo-3-piperidyl)-3-methyl-2-oxo-benzimidazol-4-yl]butyl] piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 34.2 μmol, FA salt) was dissolved in FA (1 mL). The mixture was stirred at 30° C. for 1 hrs. On completion, mixture was concentrated in vacuo to give the title compound (29.8 mg, 81% yield, FA salt) as a yellow solid. $^1$H NMR (400 MHz, DMSO-$d_6$) δ 11.10 (s, 1H), 9.05 (s, 1H), 8.22 (s, 2H), 7.74-7.55 (m, 3H), 6.98-6.90 (m, 2H), 6.84 (dd, J=2.8, 6.0 Hz, 1H), 5.36 (dd, J=5.2, 12.8 Hz, 1H), 4.49 (d, J=12.4 Hz, 1H), 4.35 (d, J=12.4 Hz, 1H), 4.19 (d, J=6.4 Hz, 1H), 4.16-4.11 (m, 2H), 4.07 (s, 1H), 4.02 (s, 1H), 3.94 (d, J=12.0 Hz, 3H), 3.68-3.64 (m, 4H), 3.62-3.58 (m, 1H), 3.53 (s, 3H), 2.91-2.82 (m, 3H), 2.81-2.61 (m, 7H), 2.01-1.93 (m, 1H), 1.79-1.73 (m, 4H), 1.71 (s, 4H), 1.66-1.49 (m, 6H), 1.43-1.33 (m, 3H), 1.31-1.18 (m, 3H), 1.02-0.89 (m, 2H); LC-MS (ESI$^+$) m/z 1021.4 (M+H)$^+$.

Example 43. Synthesis of Compound 042

(a) Step 1—Tert-butyl 4-(1-(2,6-dioxopiperidin-3-yl)-3-methyl-2-oxo-2,3-dihydro-1H-benzo[d]imidazol-5-yl)piperazine-1-carboxylate

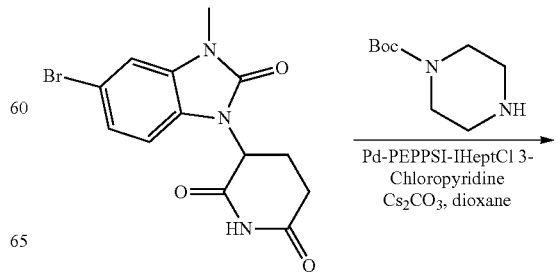

-continued

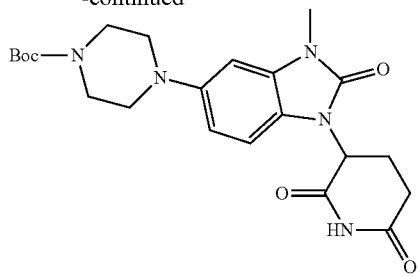

A mixture of 3-(5-bromo-3-methyl-2-oxo-benzimidazol-1-yl)piperidine-2,6-dione (1.50 g, 4.44 mmol, CAS #2300099-98-1), tert-butyl piperazine-1-carboxylate; hydrochloride (1.48 g, 6.65 mmol CAS #57260-71-6), Cs$_2$CO$_3$ (4.34 g, 13.3 mmol), 4 A MS (1.00 g, 4.44 mmol) and 1,3-bis[2,6-bis(1-propylbutyl)phenyl]-4,5-dichloro-2H-imidazol-1-ium-2-ide; 3-chloropyridine; dichloropalladium (215 mg, 221 µmol) in dioxane (20 mL) was degassed and purged with N$_2$ for 3 times, and then the mixture was stirred at 80° C. for 4 hrs under N$_2$ atmosphere. On completion, the reaction mixture was filtered and the filtrate was concentrated in vacuo to give a residue. The residue was purified by reverse phase (0.1% FA) to give the title compound (600 mg, 30% yield) as purple solid. $^1$H NMR (400 MHz, DMSO-d$_6$) δ 6.96 (d, J=8.4 Hz, 1H), 6.88 (d, J=2.0 Hz, 1H), 6.65 (dd, J=2.0, 8.4 Hz, 1H), 5.30 (dd, J=5.2, 12.8 Hz, 1H), 3.46 (d, J=4.8 Hz, 4H), 3.30 (s, 3H), 3.07-3.00 (m, 4H), 2.93-2.84 (m, 1H), 2.73-2.60 (m, 2H), 2.01-1.95 (m, 1H), 1.42 (s, 9H); LC-MS (ESI$^+$) m/z 444.1 (M+H)$^+$.

(b) Step 2—3-(3-Methyl-2-oxo-5-(piperazin-1-yl)-2,3-dihydro-1H-benzo[d]imidazol-1-yl)piperidine-2,6-dione

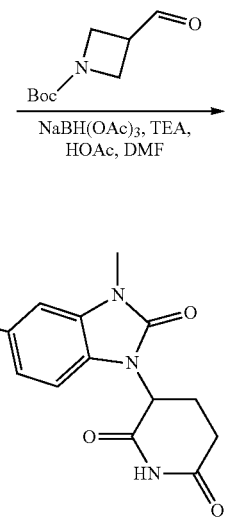

To a solution of tert-butyl 4-[1-(2,6-dioxo-3-piperidyl)-3-methyl-2-oxo-benzimidazol-5-yl]piperazine-1-carboxylate (300 mg, 676 µmol) in DCM (2 mL) was added TFA (1.84 g, 16.1 mmol). The mixture was stirred at 25° C. for 0.5 hr. On completion, the reaction mixture was concentrated in vacuo to give the title compound (300 mg, 96% yield, TFA salt) as brown oil. LC-MS (ESI$^+$) m/z 344.0 (M+H)$^+$.

(c) Step 3—Tert-butyl 3-((4-(1-(2,6-dioxopiperidin-3-yl)-3-methyl-2-oxo-2,3-dihydro-1H-benzo[d]imidazol-5-yl)piperazin-1-yl)methyl)azetidine-1-carboxylate

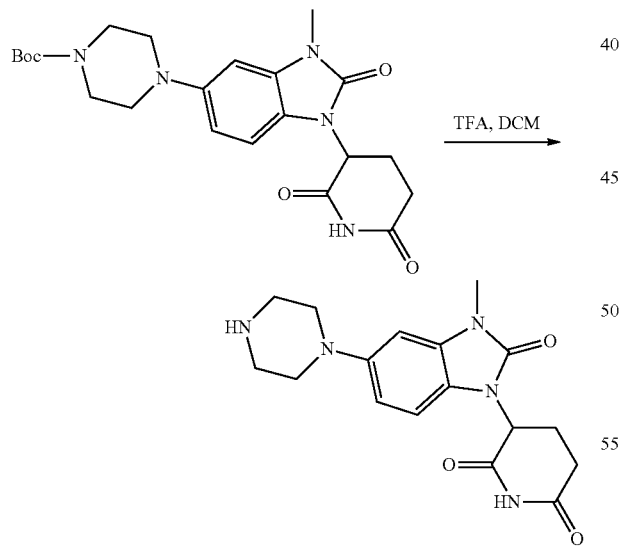

To a solution of 3-(3-methyl-2-oxo-5-piperazin-1-yl-benzimidazol-1-yl)piperidine-2,6-dione (300 mg, 873 µmol, TFA salt) in DMF (2 mL) was added TEA (265 mg, 2.62 mmol). The mixture was stirred at 25° C. for 10 min. HOAc (157 mg, 2.62 mmol) and tert-butyl 3-formylazetidine-1-carboxylate (210 mg, 1.14 mmol, CAS #177947-96-5) were added to the above mixture. The reaction mixture was stirred at 25° C. for 20 min. Then NaBH(OAc)$_3$ (370 mg, 1.75 mmol) was added to the mixture. The reaction mixture was stirred at 25° C. for 30 min. On completion, the reaction mixture was quenched by H$_2$O (0.2 mL). The mixture was purified by reverse phase (0.1% FA) to give the title compound (230 mg, 51% yield) as yellow solid. $^1$H NMR (400 MHz, DMSO-d$_6$) δ 11.07 (s, 1H), 6.94 (d, J=8.4 Hz, 1H), 6.84 (d, J=2.0 Hz, 1H), 6.62 (dd, J=2.0, 8.4 Hz, 1H), 5.29 (dd, J=5.2, 12.8 Hz, 1H), 3.93-3.91 (m, 3H), 3.51 (s, 2H), 3.44-3.40 (m, 1H), 3.30 (s, 3H), 3.08 (s, 4H), 2.94-2.83 (m, 1H), 2.82-2.73 (m, 1H), 2.72-2.53 (m, 6H), 2.03-1.90 (m, 1H), 1.37 (s, 9H); LC-MS (ESI$^+$) m/z 513.2 (M+H)$^+$.

(d) Step 4—3-(5-(4-(Azetidin-3-ylmethyl)piperazin-1-yl)-3-methyl-2-oxo-2,3-dihydro-1H-benzo[d] imidazol-1-yl)piperidine-2,6-dione

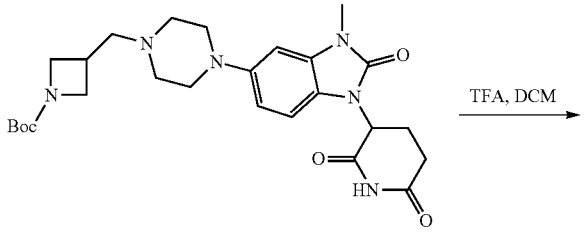

1043

-continued

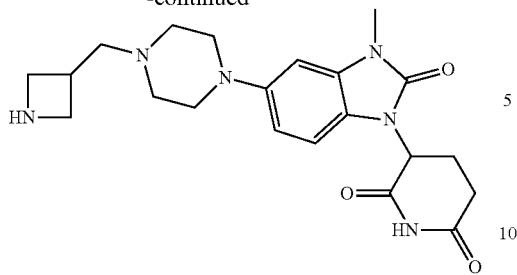

To a solution of tert-butyl 3-[[4-[1-(2,6-dioxo-3-piperidyl)-3-methyl-2-oxo-benzimidazol-5-yl] piperazin-1-yl]methyl]azetidine-1-carboxylate (70.0 mg, 136 μmol) in

1044

DCM (3 mL) was added TFA (921 mg, 8.08 mmol). The mixture was stirred at 25° C. for 0.5 hr. On completion, the mixture was concentrated in vacuo to give the title compound (70.0 mg, 97% yield, TFA salt) as yellow oil. LC-MS (ESI$^+$) m/z 413.0 (M+H)$^+$.

(e) Step 5—Tert-butyl 3-(2-(((3S,7aS)-3-(((3-((4-(1-(2,6-dioxopiperidin-3-yl)-3-methyl-2-oxo-2,3-dihydro-1H-benzo[d]imidazol-5-yl)piperazin-1-yl)methyl)azetidine-1-carbonyl)oxy)methyl)tetrahydro-1H-pyrrolizin-7a(5H)-yl)methoxy)-7-(8-ethynyl-7-fluoronaphthalen-1-yl)-8-fluoropyrido[4,3-d]pyrimidin-4-yl)-3,8-diazabicyclo[3.2.1]octane-8-carboxylate

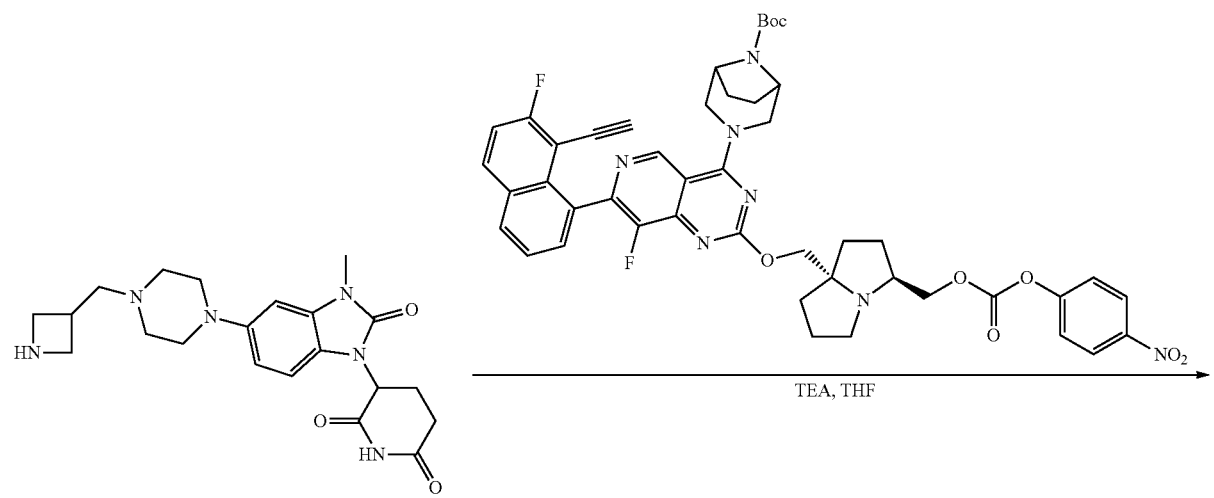

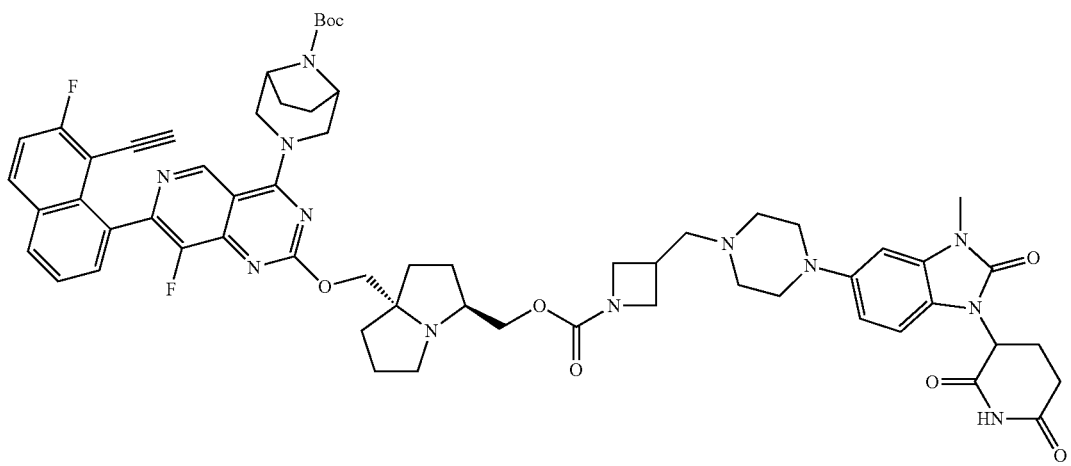

To a solution of 3-[5-[4-(azetidin-3-ylmethyl)piperazin-1-yl]-3-methyl-2-oxo-benzimidazol-1-yl] piperidine-2,6-dione (67.8 mg, 128 μmol, TFA salt) in THF (5 mL) was added TEA (26.0 mg, 257 μmol) and tert-butyl 3-(7-(8-ethynyl-7-fluoronaphthalen-1-yl)-8-fluoro-2-(((3S,7aS)-3-((((4-nitrophenoxy)carbonyl)oxy)methyl)tetrahydro-1H-pyrrolizin-7a(5H)-yl)methoxy)pyrido[4,3-d]pyrimidin-4-yl)-3,8-diazabicyclo[3.2.1]octane-8-carboxylate (74.0 mg, 85.8 μmol). The mixture was stirred at 25° C. for 1 hr. On completion, the mixture was concentrated in vacuo to give a residue. The residue was purified by prep-HPLC (column: Phenomenex luna C18 150*25 mm*10 μm; mobile phase: [water (FA)-ACN]; gradient: 15%-45% B over 8 min) to give the title compound (15.0 mg, 15% yield) as yellow solid. $^1$H NMR (400 MHz, DMSO-d$_6$) δ 11.08 (s, 1H), 9.17 (s, 1H), 8.32-8.16 (m, 2H), 7.74-7.68 (m, 1H), 7.68-7.58 (m, 2H), 6.99 (d, J=8.4 Hz, 1H), 6.90 (s, 1H), 6.68 (d, J=7.6 Hz, 1H), 5.38-5.25 (m, 1H), 4.66-4.51 (m, 3H), 4.32 (s, 3H), 4.18-4.06 (m, 2H), 3.97 (d, J=5.2 Hz, 1H), 3.83-3.65 (m, 6H), 3.50-3.46 (m, 2H), 3.31 (s, 3H), 3.22-3.06 (m, 4H), 2.99-2.85 (m, 4H), 2.76-2.59 (m, 8H), 2.33 (s, 1H), 2.15-1.92 (m, 8H), 1.90-1.84 (m, 2H), 1.72 (d, J=8.4 Hz, 1H), 1.51-1.44 (m, 9H); LC-MS (ESI$^+$) m/z 1135.3 (M+H)$^+$.

(f) Step 6—((3S,7aS)-7a-(((4-(3,8-Diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl 3-((4-(1-(2,6-dioxopiperidin-3-yl)-3-methyl-2-oxo-2,3-dihydro-1H-benzo[d]imidazol-5-yl)piperazin-1-yl)methyl)azetidine-1-carboxylate (042)

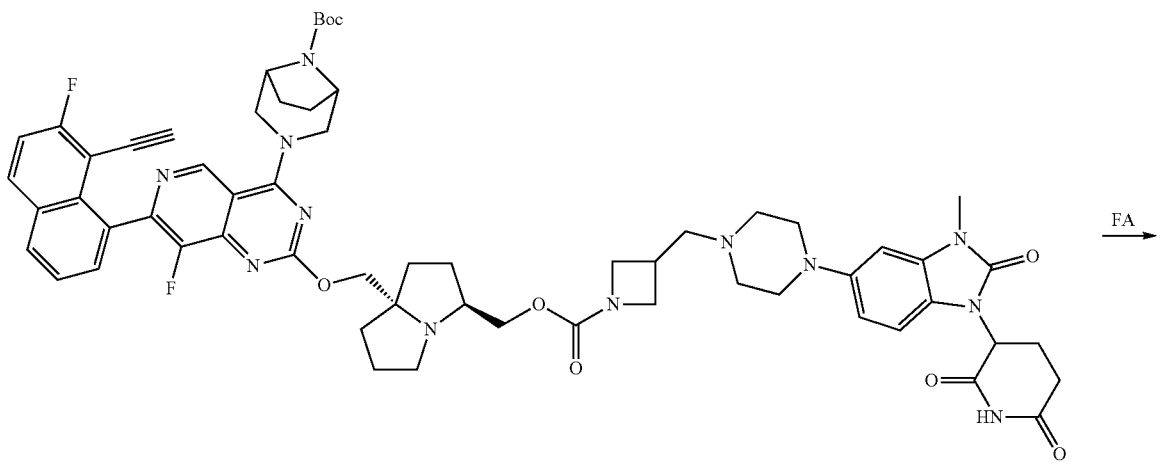

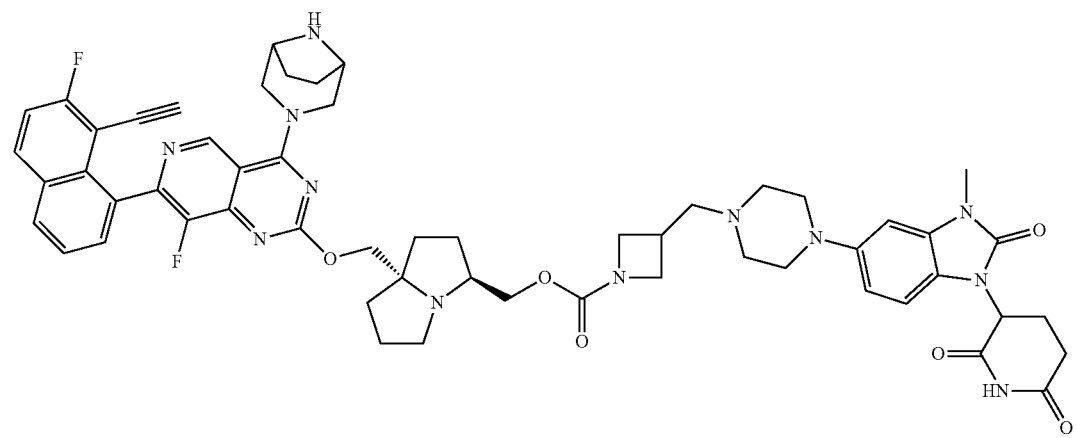

A solution of tert-butyl 3-[2-[[(3S,8S)-3-[[3-[[4-[1-(2,6-dioxo-3-piperidyl)-3-methyl-2-oxo-benzimidazol-5-yl]piperazin-1-yl]methyl]azetidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (15 mg, 13.2 μmol) in FA (3 mL) was stirred at 25° C. for 1 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 3%-33% B over 8 min) to give the title compound (8.41 mg, 58% yield, FA salt) as yellow solid. $^1$H NMR (400 MHz, DMSO-d$_6$) δ 11.07 (s, 1H), 9.05 (s, 1H), 8.24-8.21 (m, 1H), 8.20-8.17 (m, 1H), 7.74-7.56 (m, 3H), 6.93 (d, J=8.4 Hz, 1H), 6.82 (d, J=1.6 Hz, 1H), 6.60 (d, J=8.4 Hz, 1H), 5.32-5.25 (m, 1H), 4.48 (d, J=11.6 Hz, 1H), 4.34 (d, J=12.4 Hz, 1H), 4.22-3.97 (m, 8H), 3.66-3.60 (m, 6H), 3.29 (s, 3H), 3.24 (s, 2H), 3.05 (s, 4H), 2.92-2.62 (m, 8H), 2.56 (d, J=7.6 Hz, 2H), 2.41-2.18 (m, 1H), 2.09-1.94 (m, 2H), 1.80-1.61 (m, 10H), 1.56-1.46 (m, 1H); LC-MS (ESI$^+$) m/z 1035.6 (M+H)$^+$.

Example 44. Synthesis of Compound 043

(a) Step 1—Tert-butyl 4-[4-[1-(2,6-dioxo-3-piperidyl)-3-methyl-2-oxo-benzimidazol-5-yl]butyl]piperidine-1-carboxylate

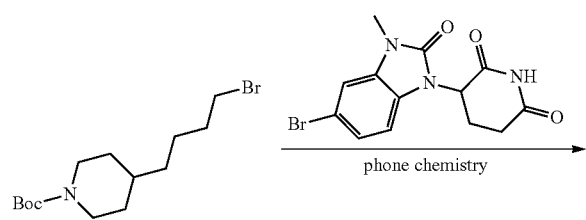

phone chemistry

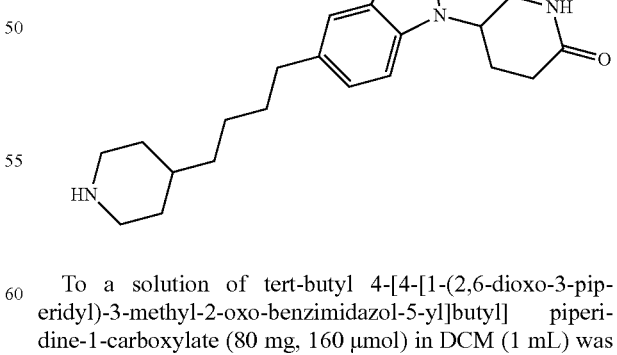

To an 40 mL vial equipped with a stir bar was added 3-(5-bromo-3-methyl-2-oxo-benzimidazol-1-yl)piperidine-2,6-dione (1 g, 2.96 mmol, CAS #2300099-98-1), tert-butyl4-(4-bromobutyl) piperidine-1-carboxylate (1.23 g, 3.84 mmol, CAS #142355-81-5), Ir[dF(CF$_3$)ppy]$_2$(dtbpy)(PF$_6$) (33.1 mg, 29.5 μmol), NiCl$_2$·dtbbpy (17.6 mg, 44.3 μmol), TTMSS (735 mg, 2.96 mmol), 2,6-dimethylpyridine (2.85 g, 26.6 mmol) in DME (30 mL). The vial was sealed and placed under nitrogen was added. The reaction was stirred and irradiated with a 4×50 W [455 nm] blue LED lamp (3 cm away), with cooling water to keep the reaction temperature at 25° C. for 14 hrs. On completion, the reaction mixture was filtered and the filtrate was concentrated in vacuo to give a residue. The residue was purified by reverse phase (0.1% FA condition) to give the title compound (750 mg, 50% yield) as a white solid. $^1$H NMR (400 MHz, DMSO-d$_6$) δ 11.09 (s, 1H), 7.10-6.94 (m, 2H), 6.86 (dd, J=1.2, 8.0 Hz, 1H), 5.34 (dd, J=5.4, 12.8 Hz, 1H), 3.99-3.79 (m, 2H), 3.34 (s, 3H), 2.96-2.83 (m, 1H), 2.76-2.66 (m, 2H), 2.66-2.54 (m, 5H), 2.04-1.95 (m, 1H), 1.65-1.52 (m, 4H), 1.38 (s, 9H), 1.33-1.18 (m, 4H), 0.94-0.93 (m, 2H); LC-MS (ESI$^+$) m/z 399.1 (M+H−100)$^+$.

(b) Step 2—3-[3-Methyl-2-oxo-5-[4-(4-piperidyl)butyl]benzimidazol-1-yl]piperidine-2,6-dione

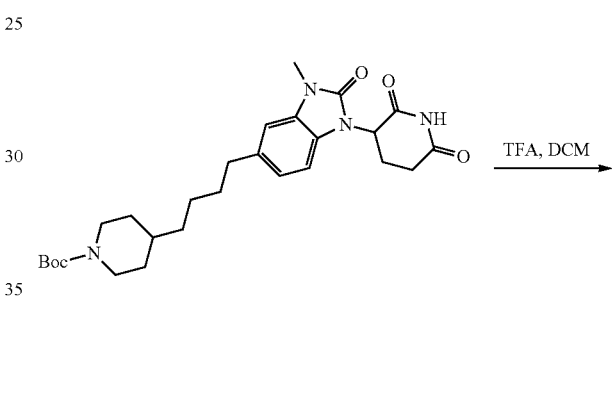

To a solution of tert-butyl 4-[4-[1-(2,6-dioxo-3-piperidyl)-3-methyl-2-oxo-benzimidazol-5-yl]butyl] piperidine-1-carboxylate (80 mg, 160 μmol) in DCM (1 mL) was added TFA (460 mg, 4.04 mmol). The reaction mixture was stirred at 25° C. for 1 hr. On completion, the resulting mixture was concentrated in vacuo to give the title compound (80 mg, 97% yield) as brown oil. LC-MS (ESI$^+$) m/z 399.1 (M+H)$^+$.

(c) Step 3—Tert-butyl 3-[2-[[(3S,8S)-3-[[4-[4-[1-(2,6-dioxo-3-piperidyl)-3-methyl-2-oxo-benzimidazol-5-yl]butyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

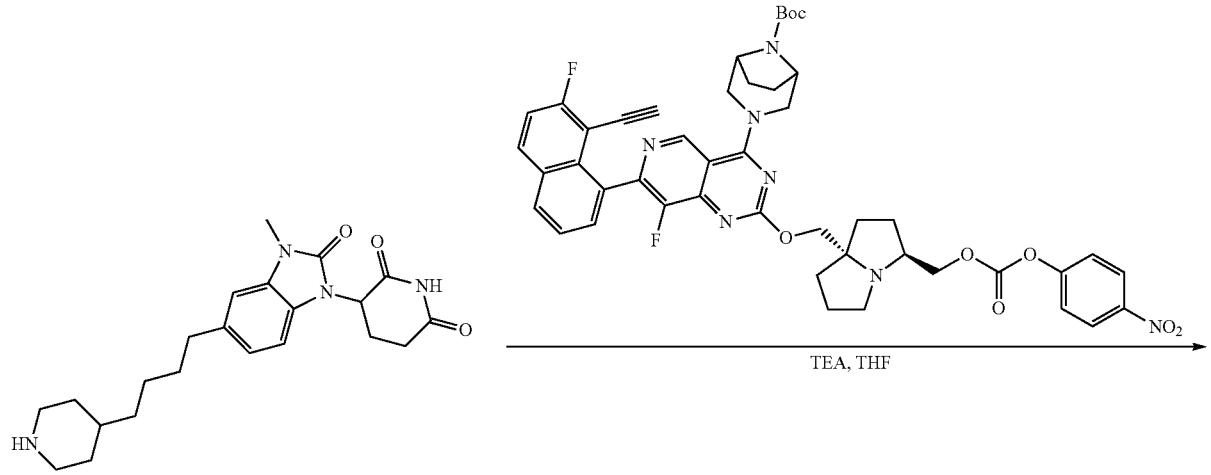

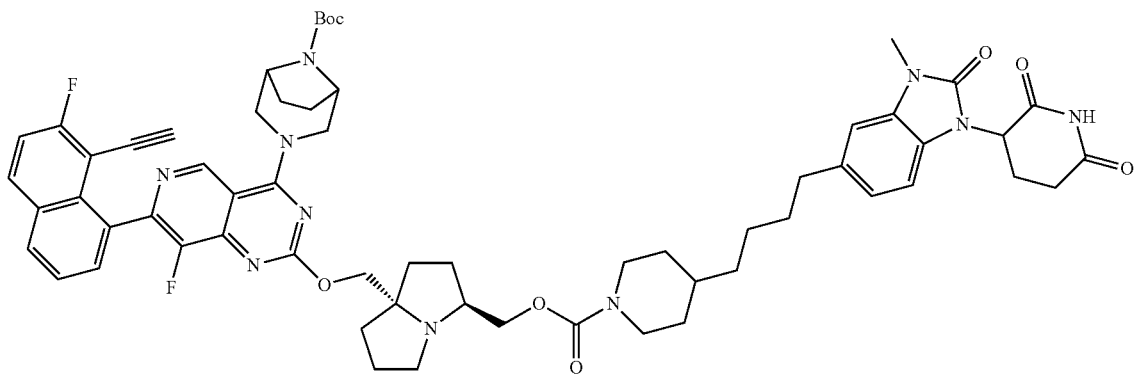

To a solution of 3-[3-methyl-2-oxo-5-[4-(4-piperidyl)butyl]benzimidazol-1-yl]piperidine-2,6-dione (74.9 mg, 146 μmol, TFA) in THF (3 mL) was added TEA (24.6 mg, 243 μmol) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70 mg, 81.2 μmol). The mixture was stirred at 25° C. for 2 hrs. On completion, the mixture was concentrated in vacuo to give a residue. The residue was purified by prep-HPLC (column: Phenomenex luna C18 150*25 mm*10 μm; mobile phase: [water (FA)-ACN]; gradient: 30%-60% B over 10 min) to give the title compound (45 mg, 47% yield, FA) as a brown solid. LC-MS (ESI$^+$) m/z 1122.5 (M+H)$^+$.

(d) Step 4—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl4-[4-[1-(2,
6-dioxo-3-piperidyl)-3-methyl-2-oxo-benzimidazol-
5-yl]butyl]piperidine-1-carboxylate (043)

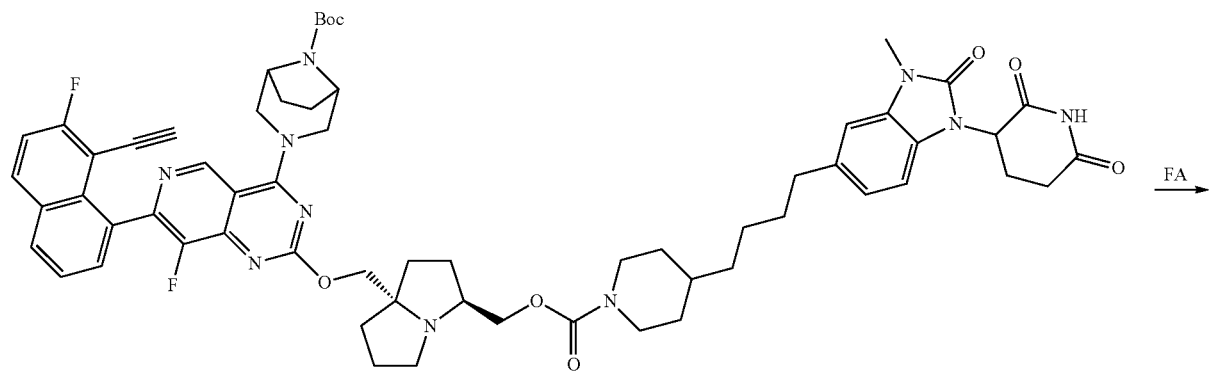

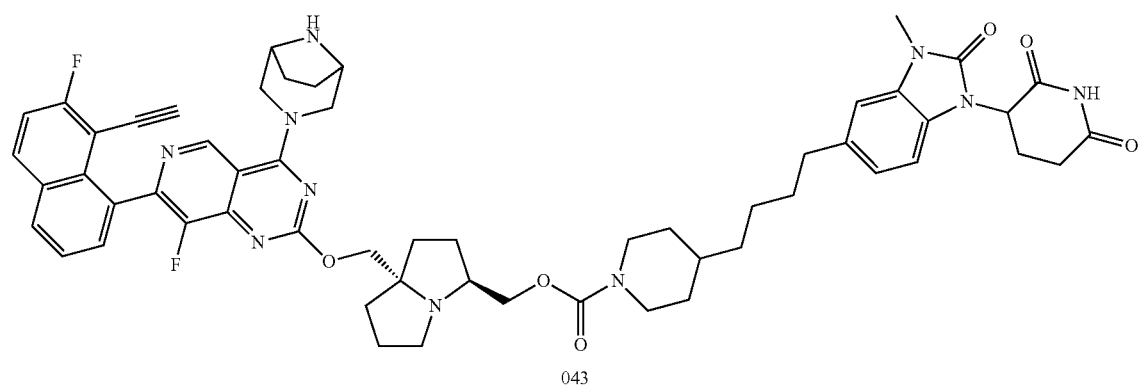

043

A solution of tert-butyl 3-[2-[[(3S,8S)-3-[[4-[4-[1-(2,6-dioxo-3-piperidyl)-3-methyl-2-oxo-benzimidazol-5-yl]butyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40 mg, 35.6 μmol) in FA (1 mL) was stirred at 25° C. for 2 hrs. On completion, the reaction mixture was concentrated in vacuo to give the title compound (23.5 mg, 62% yield, FA) as a white solid. ¹H NMR (400 MHz, DMSO-$d_6$) δ 11.09 (s, 1H), 9.06 (s, 1H), 8.26-8.22 (m, 1H), 8.18 (d, J=1.2 Hz, 1H), 7.72-7.66 (m, 1H), 7.64 (d, J=7.2 Hz, 1H), 7.61-7.54 (m, 1H), 7.03-6.93 (m, 2H), 6.87-6.80 (m, 1H), 5.33 (dd, J=5.2, 12.8 Hz, 1H), 4.49 (d, J=12.8 Hz, 1H), 4.35 (d, J=12.0 Hz, 1H), 4.19 (d, J=6.8 Hz, 1H), 4.16-4.10 (m, 2H), 4.06 (d, J=10.4 Hz, 1H), 4.02 (s, 1H), 3.93 (d, J=11.2 Hz, 2H), 3.66 (s, 4H), 3.60 (s, 1H), 3.31 (s, 3H), 3.30-3.26 (m, 1H), 2.94-2.84 (m, 1H), 2.81-2.55 (m, 8H), 2.09-1.95 (m, 2H), 1.82-1.66 (m, 8H), 1.66-1.47 (m, 6H), 1.46-1.15 (m, 6H), 1.03-0.87 (m, 2H); LC-MS (ESI⁺) m/z 1021.4 (M+H)⁺.

Example 45. Synthesis of Compound 044

(a) Step 1—3-[3-Methyl-2-oxo-5-(4-piperidyl)benzimidazol-1-yl]piperidine-2,6-dione

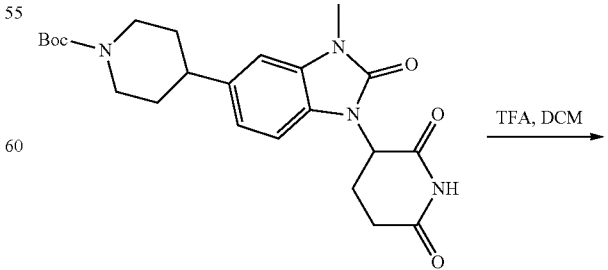

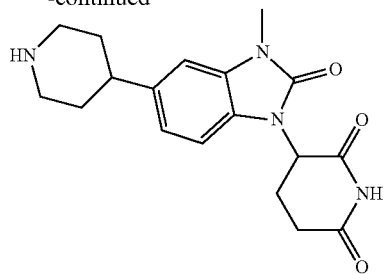

To a solution of tert-butyl 4-[1-(2,6-dioxo-3-piperidyl)-3-methyl-2-oxo-benzimidazol-5-yl] piperidine-1-carboxylate (300 mg, 677 μmol) in DCM (5 mL) was added TFA (1.54 g, 13.4 mmol, 1.00 mL). The mixture was stirred at 25° C. for 5 min. On completion, the mixture was concentrated in vacuo to give the title compound (300 mg, 96% yield, TFA salt) as white solid. LC-MS (ESI⁺) m/z 343.0 (M+H)⁺.

(b) Step 2—Tert-butyl 4-[[4-[1-(2,6-dioxo-3-piperidyl)-3-methyl-2-oxo-benzimidazol-5-yl]-1-piperidyl]methyl]piperidine-1-carboxylate

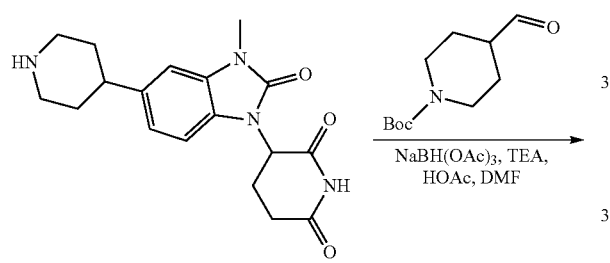

To a solution of 3-[3-methyl-2-oxo-5-(4-piperidyl)benzimidazol-1-yl]piperidine-2,6-dione (300 mg, 876 μmol, TFA salt) in DMF (5 mL) was added TEA (265 mg, 2.63 mmol) and HOAc (210 mg, 3.50 mmol), tert-butyl 4-formylpiperidine-1-carboxylate (186 mg, 876 μmol, CAS #137076-22-3), NaBH(OAc)₃ (278 mg, 1.31 mmol). The mixture was stirred at 25° C. for 0.5 hr. On completion, the mixture was filtered and the filtrate was concentrated in vacuo. The residue was purified by reversed-phase HPLC (0.1% FA condition) to give the title compound (287 mg, 59% yield) as white solid. ¹H NMR (400 MHz, DMSO-d₆) δ 7.10-6.99 (m, 2H), 6.93-6.90 (m, 1H), 5.36-5.32 (m, 1H), 3.93 (d, J=12.0 Hz, 2H), 3.33 (s, 3H), 3.25-3.22 (m, 2H), 2.95-2.85 (m, 1H), 2.81-2.52 (m, 8H), 2.05-1.96 (m, 2H), 1.90-1.80 (m, 5H), 1.71 (d, J=12.0 Hz, 2H), 1.39 (s, 9H), 1.05-0.95 (m, 2H); LC-MS (ESI⁺) m/z 540.2 (M+H)⁺.

(c) Step 3—3-[3-Methyl-2-oxo-5-[1-(4-piperidylmethyl)-4-piperidyl]benzimidazol-1-yl]piperidine-2,6-dione

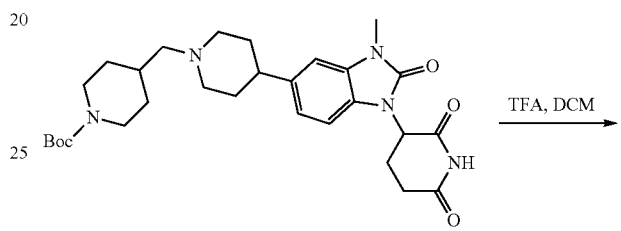

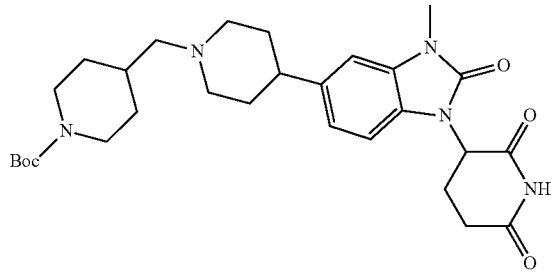

To a solution of tert-butyl 4-[[4-[1-(2,6-dioxo-3-piperidyl)-3-methyl-2-oxo-benzimidazol-5-yl]-1-piperidyl]methyl]piperidine-1-carboxylate (100 mg, 185 μmol) in DCM (5 mL) was added TFA (1.54 g, 13.4 mmol, 1.00 mL). The mixture was stirred at 25° C. for 5 mins. On completion, the mixture was concentrated in vacuo to give the title compound (89.0 mg, 98% yield, TFA salt) as white solid. LC-MS (ESI⁺) m/z 440.2 (M+H)⁺.

(d) Step 4—Tert-butyl 3-[2-[[(3S,8S)-3-[[4-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

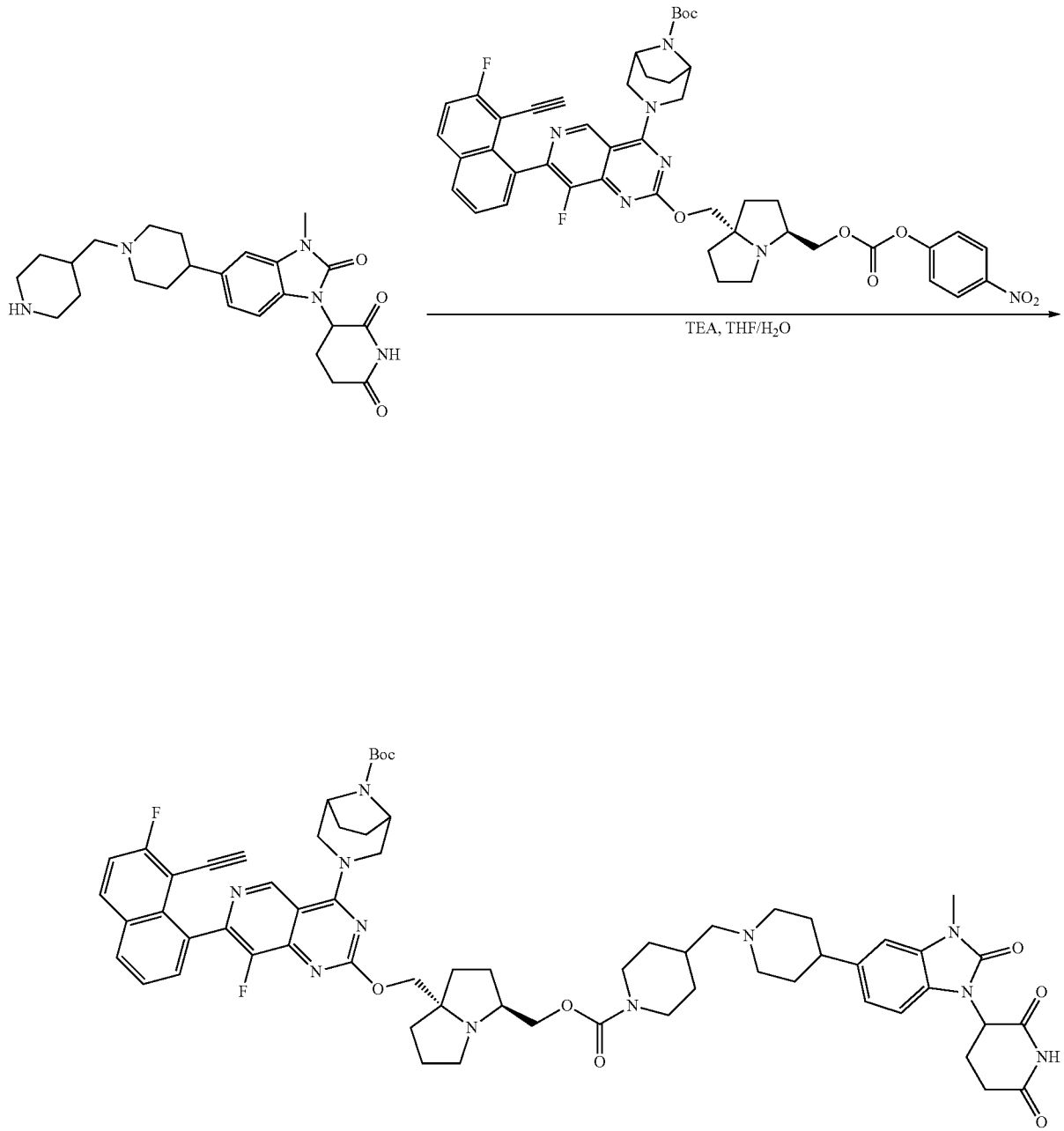

To a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 69.6 μmol) in THF (2 mL) and H₂O (2 mL) was added TEA (21.1 mg, 208 μmol, 29.0 μL) and 3-[3-methyl-2-oxo-5-[1-(4-piperidylmethyl)-4-piperidyl]benzimidazol-1-yl]piperidine-2,6-dione (45.9 mg, 104 μmol, TFA salt). The mixture was stirred at 25° C. for 0.5 hr. On completion, the mixture was concentrated in vacuo. The crude product was purified by reversed-phase HPLC (0.1% FA condition) to give the title compound (40.0 mg, 49% yield) as white solid. LC-MS (ESI⁺) m/z 1162.8 (M+H)⁺.

(e) Step 5—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[[4-[1-(2,
6-dioxo-3-piperidyl)-3-methyl-2-oxo-benzimidazol-
5-yl]-1-piperidyl]methyl]piperidine-1-carboxylate
(044)

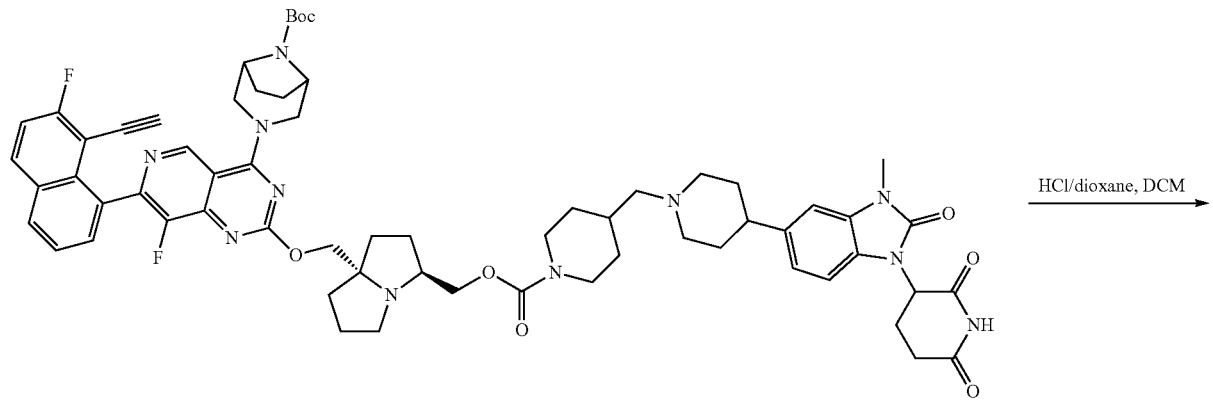

To a solution of tert-butyl 3-[2-[[(3S,8S)-3-[[4-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 34.4 μmol) in DCM (3 mL) was added HCl/dioxane (4 M, 1.00 mL). The mixture was stirred at 25° C. for 0.5 hr. On completion, the mixture was concentrated in vacuo. The reaction mixture was lyophilized to give the title compound (26.7 mg, 69% yield, HCl salt) as yellow solid. $^1$H NMR (400 MHz, DMSO-$d_6$) δ 11.11 (s, 2H), 10.21 (s, 1H), 10.02 (s, 1H), 9.68 (s, 1H), 9.16 (s, 1H), 8.30-8.18 (m, 2H), 7.74-7.69 (m, 1H), 7.68-7.59 (m, 2H), 7.11-7.03 (m, 2H), 6.93 (d, J=7.2 Hz, 1H), 5.43-5.32 (m, 1H), 4.73-4.54 (m, 4H), 4.43-4.33 (m, 1H), 4.29-4.17 (m, 4H), 4.10-3.96 (m, 5H), 3.44-3.38 (m, 2H), 3.35-3.33 (m, 3H), 3.08-2.61 (m, 11H), 2.32-2.16 (m, 4H), 2.10-1.85 (m, 17H), 1.20-1.10 (m, 2H); LC-MS (ESI$^+$) m/z 1062.6 (M+H)$^+$.

Example 46. Synthesis of Compound 046

(a) Step 1—Tert-butyl 4-[1-(2,6-dioxo-3-piperidyl)-3-methyl-2-oxo-benzimidazol-5-yl]-3,6-dihydro-2H-pyridine-1-carboxylate

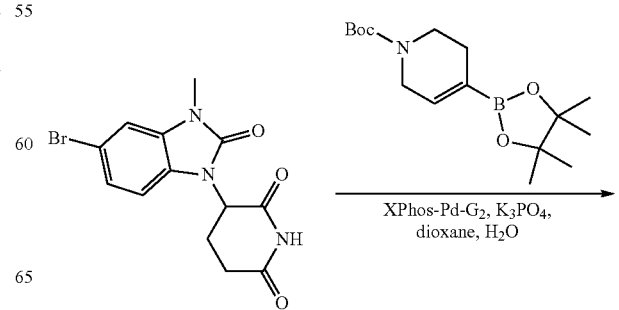

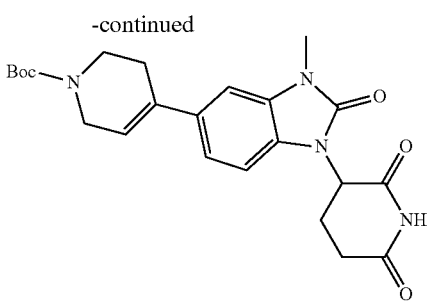

To a solution of 3-(5-bromo-3-methyl-2-oxo-benzimidazol-1-yl)piperidine-2,6-dione (500 mg, 1.47 mmol, CAS #2300099-98-1) and tert-butyl 4-(4,4,5,5-tetramethyl-1,3,2-dioxaborolan-2-yl)-3,6-dihydro-2H-pyridine-1-carboxylate (548 mg, 1.53 mmol, CAS #286961-14-6) in dioxane (10 mL) and $H_2O$ (0.5 mL) was added XPhos-Pd-$G_2$ (116 mg, 147 μmol) and $K_3PO_4$ (627 mg, 2.94 mmol). The mixture was stirred at 80° C. for 4 hrs under $N_2$ atmosphere. On completion, the reaction mixture concentrated in vacuo to give a residue and the residue was purified by prep-HPLC (0.1% FA condition) to give the title compound (365 mg, 56% yield) as white solid. $^1$H NMR (400 MHz, DMSO-$d_6$) δ 11.09 (s, 1H), 7.27 (s, 1H), 7.14-7.05 (m, 2H), 6.11 (s, 1H), 5.36 (dd, J=5.4, 12.8 Hz, 1H), 4.00 (s, 2H), 3.57-3.53 (m, 2H), 3.35 (s, 3H), 3.33-3.29 (m, 2H), 2.96-2.84 (m, 1H), 2.77-2.68 (m, 1H), 2.66-2.59 (m, 1H), 2.06-1.98 (m, 1H), 1.43 (s, 9H); LC-MS (ESI$^+$) m/z 441.1 (M+H)$^+$.

(b) Step 2—Tert-butyl 4-[1-(2,6-dioxo-3-piperidyl)-3-methyl-2-oxo-benzimidazol-5-yl]piperidine-1-carboxylate

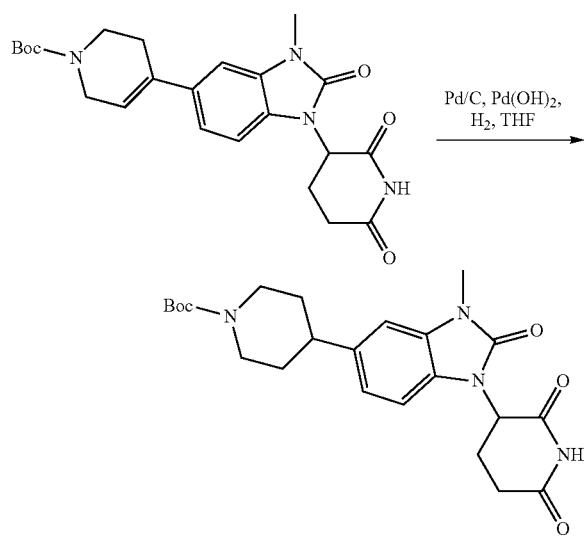

A mixture of tert-butyl 4-[1-(2,6-dioxo-3-piperidyl)-3-methyl-2-oxo-benzimidazol-5-yl]-3,6-dihydro-2H-pyridine-1-carboxylate (365 mg, 828 μmol), Pd/C (100 mg, 93.9 μmol, 10% purity) and Pd(OH)$_2$ (100 mg, 142 μmol, 20% purity) in THF (10 mL) was degassed and purged with $H_2$ for 3 times, then the mixture was stirred at 25° C. for 2 hrs under $H_2$ atmosphere (15 Psi). On completion, the reaction mixture was filtered and the filtrate was concentrated in vacuo to give the title compound (321 mg, 87% yield) as white solid. $^1$H NMR (400 MHz, DMSO-d) δ 11.09 (s, 1H), 7.11 (s, 1H), 7.01 (d, J=8.0 Hz, 1H), 6.91 (dd, J=1.2, 8.0 Hz, 1H), 5.34 (dd, J=5.2, 12.8 Hz, 1H), 4.14-4.03 (m, 2H), 3.64-3.55 (m, 1H), 3.33 (s, 3H), 3.33 (s, 2H), 2.93-2.86 (m, 1H), 2.73-2.67 (m, 1H), 2.63-2.59 (m, 1H), 2.02-1.95 (m, 1H), 1.77-1.75 (m, 1H), 1.73 (s, 1H), 1.60-1.55 (m, 1H), 1.54-1.49 (m, 1H), 1.42 (s, 9H); LC-MS (ESI$^+$) m/z 387.1 (M-t-Bu+H)$^+$.

(c) Step 3—3-[3-Methyl-2-oxo-5-(4-piperidyl)benzimidazol-1-yl]piperidine-2,6-dione

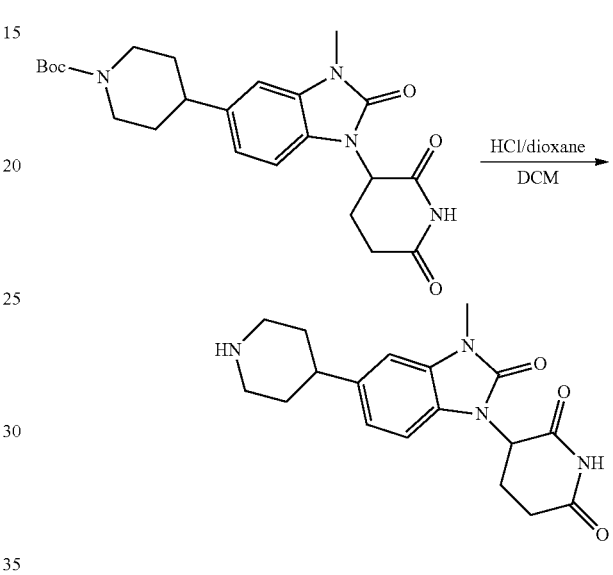

To a solution of tert-butyl 4-[1-(2,6-dioxo-3-piperidyl)-3-methyl-2-oxo-benzimidazol-5-yl]piperidine-1-carboxylate (321 mg, 725 μmol) in DCM (6 mL) was added HCl/dioxane (4 M, 2 mL). The mixture was stirred at 25° C. for 2 hrs. On completion, the reaction mixture concentrated in vacuo to give the title compound (270 mg, 98% yield, HCl salt) as white solid. LC-MS (ESI$^+$) m/z 343.0 (M+H)$^+$.

(d) Step 4—Tert-butyl N-[4-[4-[1-(2,6-dioxo-3-piperidyl)-3-methyl-2-oxo-benzimidazol-5-yl]-1-piperidyl]-4-oxo-butyl]carbamate

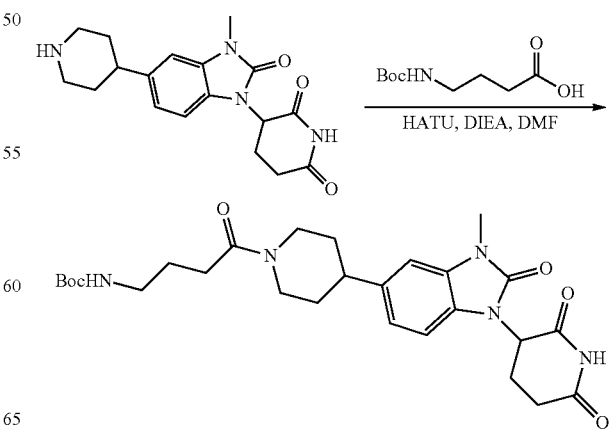

To a solution of 3-[3-methyl-2-oxo-5-(4-piperidyl)benzimidazol-1-yl]piperidine-2,6-dione (190 mg, 554 μmol, HCl salt) and 4-(tert-butoxycarbonylamino)butanoic acid (112 mg, 554 μmol, CAS #57294-38-9) in DMF (6 mL) was added DIEA (143 mg, 1.10 mmol). Then HATU (316 mg, 831 μmol) was added and the mixture was stirred at 25° C. for 1 hr. On completion, the mixture was concentrated in vacuo to give a residue and the residue was purified by prep-HPLC (column: Phenomenex Luna C18 150*25 mm*10 μm; mobile phase: [water (FA)-ACN]; gradient: 23%-53% B over 10 min) to give the title compound (156 mg, 56% yield) as yellow solid. $^1$H NMR (400 MHz, CDCl$_3$) 8.26 (s, 1H), 6.91 (d, J=8.0 Hz, 1H), 6.87 (s, 1H), 6.75 (d, J=8.0 Hz, 1H), 5.22 (dd, J=5.2, 12.8 Hz, 1H), 4.81 (d, J=12.8 Hz, 1H), 3.99 (d, J=13.2 Hz, 1H), 3.44 (s, 3H), 3.21 (t, J=6.8 Hz, 2H), 3.18-3.10 (m, 1H), 2.95 (d, J=17.2 Hz, 1H), 2.89-2.82 (m, 1H), 2.81-2.69 (m, 2H), 2.68-2.61 (m, 1H), 2.44 (t, J=7.2 Hz, 2H), 2.28-2.19 (m, 1H), 1.93-1.84 (m, 4H), 1.70-1.59 (m, 2H), 1.45 (s, 9H); LC-MS (ESI$^+$) m/z 528.2 (M+H)$^+$.

(e) Step 5—3-[5-[1-(4-Aminobutanoyl)-4-piperidyl]-3-methyl-2-oxo-benzimidazol-1-yl]piperidine-2,6-dione

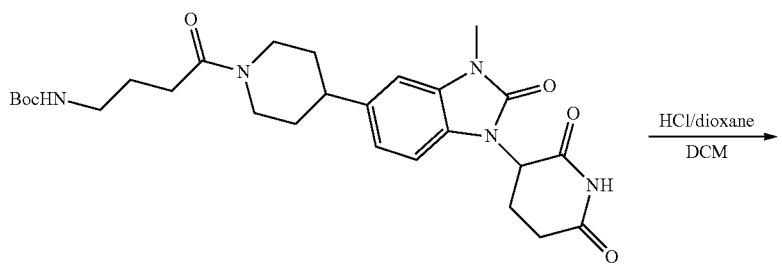

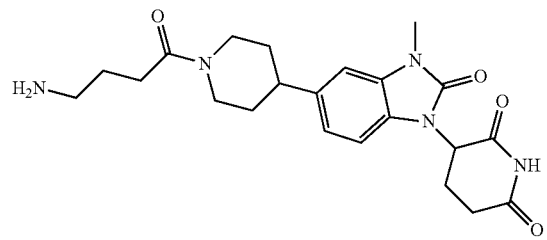

To a solution of tert-butyl N-[4-[4-[1-(2,6-dioxo-3-piperidyl)-3-methyl-2-oxo-benzimidazol-5-yl]-1-piperidyl]-4-oxo-butyl]carbamate (156 mg, 295 μmol) in DCM (6 mL) was added HCl/dioxane (4 M, 2 mL). The mixture was stirred at 25° C. for 3 hrs. On completion, the reaction mixture concentrated in vacuo to give the title compound (137 mg, 99% yield, HCl salt) as white solid. LC-MS (ESI$^+$) m/z 428.1 (M+H)$^+$.

(f) Step 6—Tert-butyl 3-[2-[[(3S,8S)-3-[[4-[4-[1-(2,6-dioxo-3-piperidyl)-3-methyl-2-oxo-benzimidazol-5-yl]-1-piperidyl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

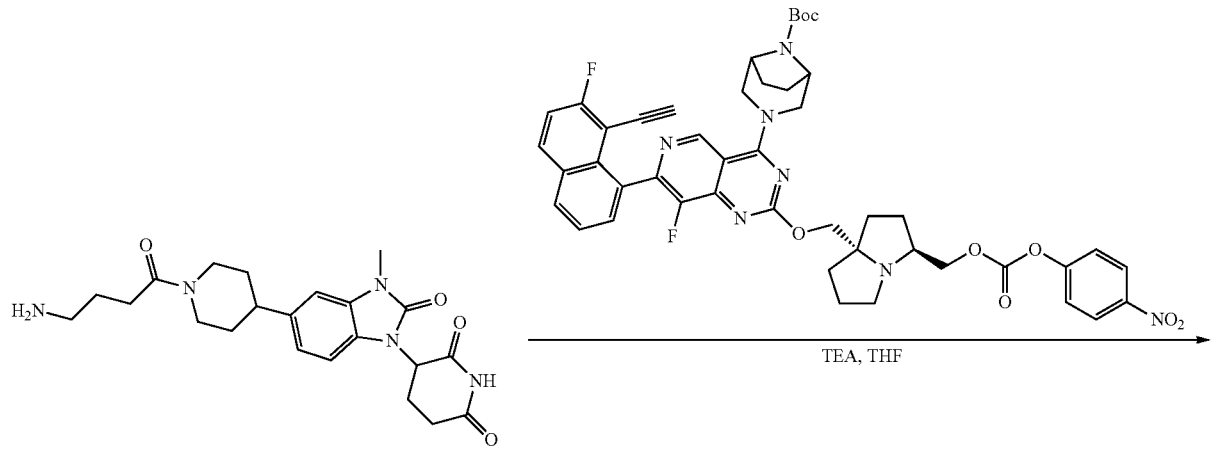

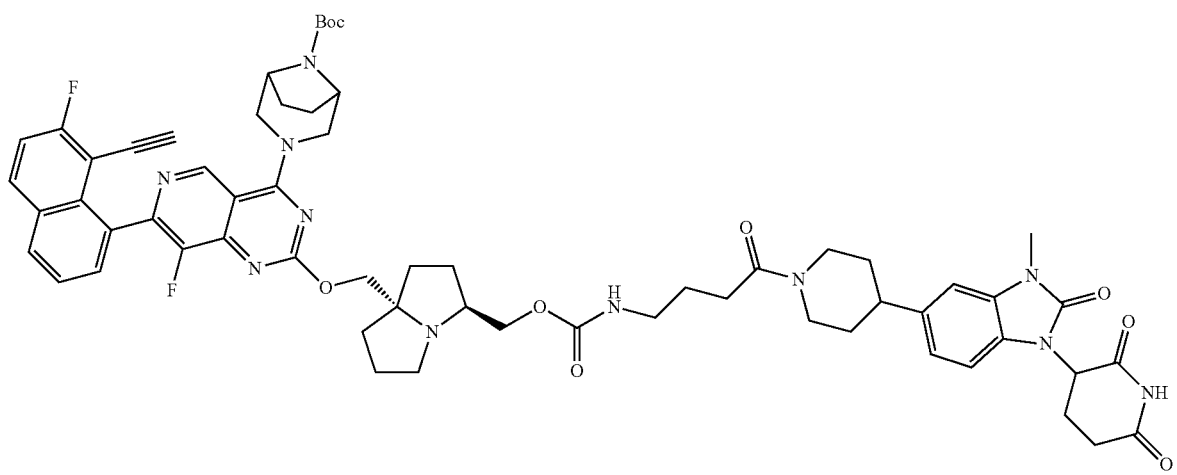

To a solution of 3-[5-[1-(4-aminobutanoyl)-4-piperidyl]-3-methyl-2-oxo-benzimidazol-1-yl]piperidine-2,6-dione (64.6 mg, 139 μmol, HCl salt) in THF (2 mL) was added TEA (21.1 mg, 208 μmol). Then a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 69.6 μmol) in THF (1 mL) was added and the mixture was stirred at 25° C. for 1 hr. On completion, the mixture was concentrated in vacuo to give a residue and the residue was purified by prep-HPLC (column: Phenomenex luna C18 150*25 mm*10 μm; mobile phase: [water (FA)-ACN]; gradient: 15%-45% B over 8 min) to give the title compound (38.0 mg, 44% yield) as yellow solid. LC-MS (ESI$^+$) m/z 1150.3 (M+H)$^+$.

(g) Step 7—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl N-[4-[4-[1-
(2,6-dioxo-3-piperidyl)-3-methyl-2-oxo-
benzimidazol-5-yl]-1-piperidyl]-4-oxo-butyl]
carbamate (045)

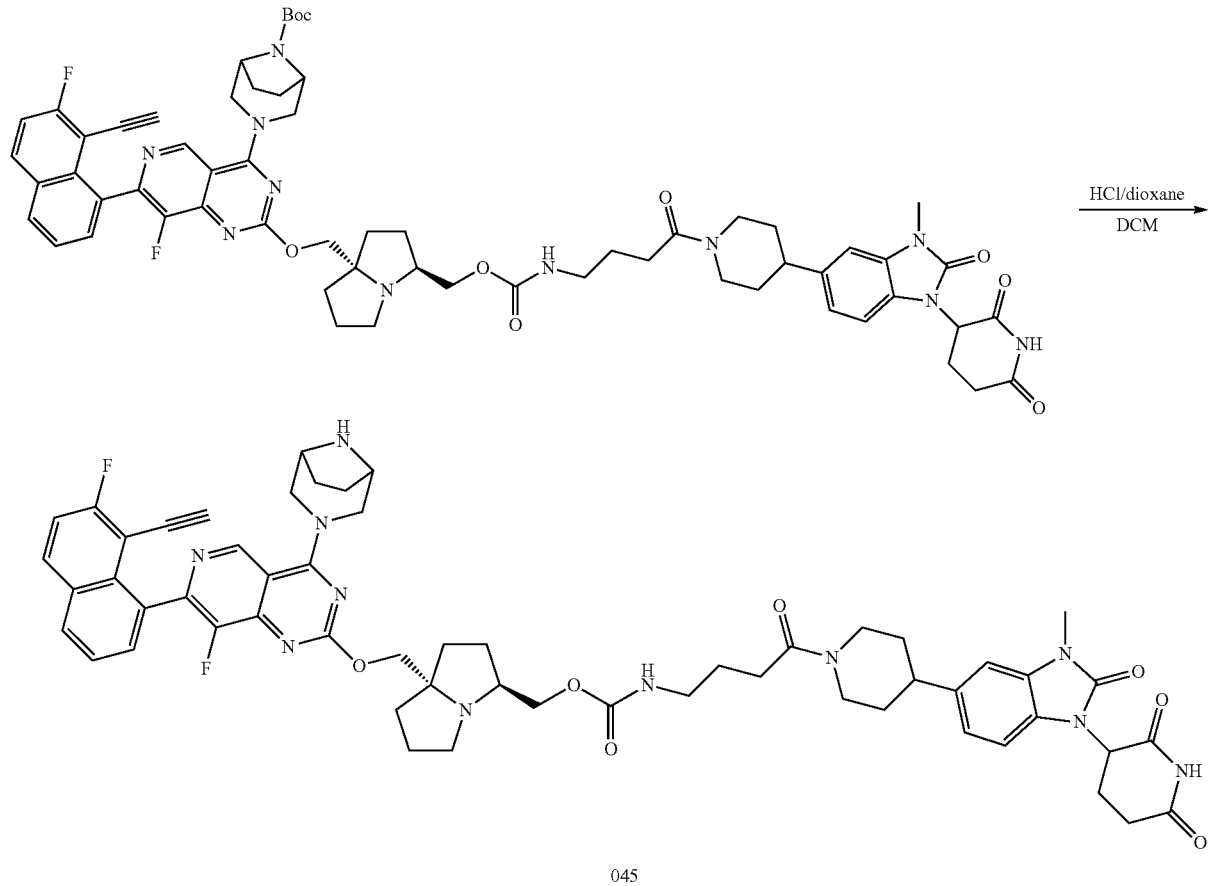

045

To a solution of tert-butyl 3-[2-[[(3S,8S)-3-[[4-[4-[1-(2,6-dioxo-3-piperidyl)-3-methyl-2-oxo-benzimidazol-5-yl]-1-piperidyl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (38.0 mg, 33.0 μmol) in DCM (5 mL) was added HCl/dioxane (4 M, 1 mL). The mixture was stirred at 25° C. for 0.5 hr. On completion, the mixture was concentrated in vacuo to give a residue and the residue was purified by prep-HPLC (column: Phenomenex luna C18 150*25 mm*10 um; mobile phase: [water (FA)-ACN]; gradient: 10%-40% B over 8 min) to give the title compound (26.0 mg, 73% yield, FA Salt) as yellow solid. $^1$H NMR (400 MHz, DMSO-$d_6$) δ 11.09 (s, 1H), 9.06 (s, 1H), 8.26-8.19 (m, 2H), 7.73-7.56 (m, 3H), 7.24 (s, 1H), 7.09 (s, 1H), 7.00 (d, J=8.0 Hz, 1H), 6.90 (d, J=7.6 Hz, 1H), 5.33 (dd, J=5.2, 12.8 Hz, 1H), 4.58-4.48 (m, 2H), 4.36 (d, J=12.0 Hz, 1H), 4.16-4.08 (m, 3H), 4.06-4.02 (m, 2H), 3.95 (d, J=12.0 Hz, 1H), 3.70 (s, 2H), 3.66 (d, J=6.0 Hz, 1H), 3.31 (s, 3H), 3.24 (s, 1H), 3.11-2.97 (m, 4H), 2.93-2.85 (m, 1H), 2.79-2.72 (m, 2H), 2.72-2.65 (m, 2H), 2.64-2.60 (m, 1H), 2.58-2.56 (m, 1H), 2.34 (t, J=7.2 Hz, 2H), 2.07-1.95 (m, 2H), 1.82-1.56 (m, 16H), 1.55-1.47 (m, 2H); LC-MS (ESI$^+$) m/z 1050.3 (M+H)$^+$.

Example 47. Synthesis of Compound 036

(a) Step 1—8-(2,7-Dichloro-8-fluoro-pyrido[4,3-d]
pyrimidin-4-yl)-1-oxa-8-azaspiro[3.5]nonane

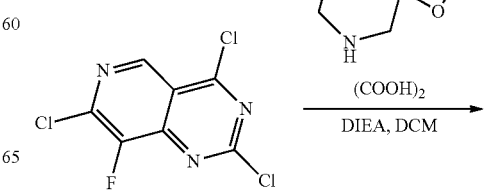

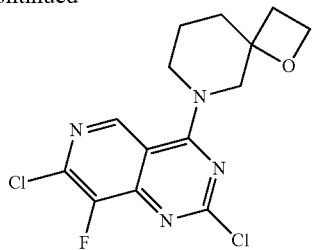

To a solution of 1-oxa-8-azaspiro[3.5]nonane (3.44 g, 15.8 mmol, oxalic acid, CAS #1523606-44-1) in DCM (100 mL) was added DIEA (12.2 g, 95.0 mmol) the mixture was stirred at −40° C. for 10 mins. Then 2,4,7-trichloro-8-fluoro-pyrido[4,3-d]pyrimidine (4 g, 15.8 mmol, CAS #2454396-80-4) was added and the reaction was stirred for 0.5 hr. On completion, the stirring reaction mixture was quenched with saturated $Na_2S_2O_3$ solution (50 mL) and $NaHCO_3$ solution (50 mL). The residue was diluted with water (200 mL) and extracted with EA (100 mL×3). The combined organic layer was dried over $Na_2SO_4$, filtered and concentrated in vacuo to give a residue. The residue was purified by flash silica gel chromatography ($SiO_2$, DCM/Ethyl acetate=3/1, P1: Rf=0.4) to give the title compound (2.58 g, 47% yield) as light yellow solid. $^1$H NMR (400 MHz, DMSO-$d_6$) δ 9.18 (s, 1H), 4.48-4.36 (m, 3H), 4.25 (d, J=12.8 Hz, 1H), 3.88 (d, J=13.2 Hz, 1H), 3.48 (t, J=10.0 Hz, 1H), 2.47-2.42 (m, 1H), 2.38-2.32 (m, 1H), 2.15-2.08 (m, 1H), 1.92-1.84 (m, 1H), 1.83-1.76 (m, 1H), 1.75-1.67 (m, 1H); LC-MS (ESI$^+$) m/z 342.9 (M+H)$^+$.

(b) Step 2—Tert-butyl-[[(3S,8S)-8-[[7-chloro-8-fluoro-4-(1-oxa-8-azaspiro[3.5]nonan-8-yl)pyrido[4,3-d] pyrimidin-2-yl]oxymethyl]-1,2,3,5,6,7-hexahydropyrrolizin-3-yl]methoxy]-diphenyl-silane

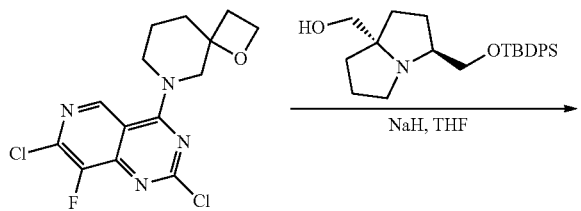

To a solution of [(3S,8S)-3-[[tert-butyl(diphenyl)silyl]oxymethyl]-1,2,3,5,6,7-hexahydropyrrolizin-8-yl] methanol (2.98 g, 7.28 mmol) in THF (100 mL) was added NaH (437.08 mg, 10.9 mmol, 60% purity) dropwised at 0° C. and the mixture was stirred at 25° C. for 2 hrs. Then tert-butyl 8-(2,7-dichloro-8-fluoro-pyrido[4,3-d]pyrimidin-4-yl)-1-oxa-8-azaspiro[3.5]nonane (2.50 g, 7.28 mmol) in THF (50 mL) was added to the mixture and the mixture was stirred at 25° C. for 15 hrs. On completion, the stirring reaction mixture was quenched with $NH_4Cl$ (50 mL). The residue was diluted with water (50 mL) and extracted with EA (100 mL×3). The combined organic layer was dried over $Na_2SO_4$, filtered and concentrated in vacuo to give a residue. The residue was purified by flash silica gel chromatography ($SiO_2$, DCM/Ethyl acetate=3/1, P1: Rf=0.4) to give the title compound (1.5 g, 29% yield) as light yellow solid. $^1$H NMR (400 MHz, DMSO-$d_6$) δ 9.01 (s, 1H), 7.66-7.62 (m, 4H), 7.48-7.43 (m, 6H), 4.40-4.36 (m, 2H), 4.16 (d, J=10.4 Hz, 2H), 4.07 (d, J=10.4 Hz, 1H), 3.90-3.78 (m, 2H), 3.74 (dd, J=6.4, 10.4 Hz, 1H), 3.45-3.37 (m, 1H), 3.25-3.16 (m, 1H), 2.75-2.67 (m, 2H), 2.42 (d, J=7.2, 10.8 Hz, 1H), 2.37-2.29 (m, 1H), 2.14-2.06 (m, 1H), 2.02 (d, J=4.0 Hz, 1H), 1.87-1.66 (m, 10H), 1.53-1.43 (m, 1H), 0.99 (s, 9H); LC-MS (ESI$^+$) m/z 716.2 (M+H)$^+$.

(c) Step 3—Tert-butyl-[[(3S,8S)-8-[[8-fluoro-7-[7-fluoro-8-(2-triisopropylsilylethynyl)-1-naphthyl]-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methoxy]-diphenyl-silane

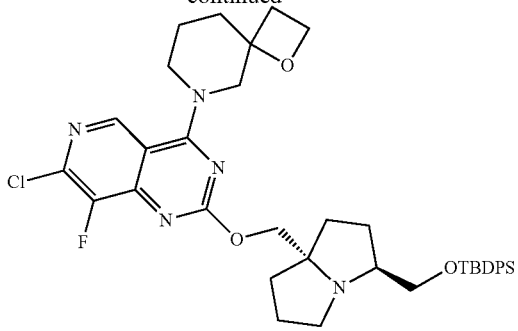

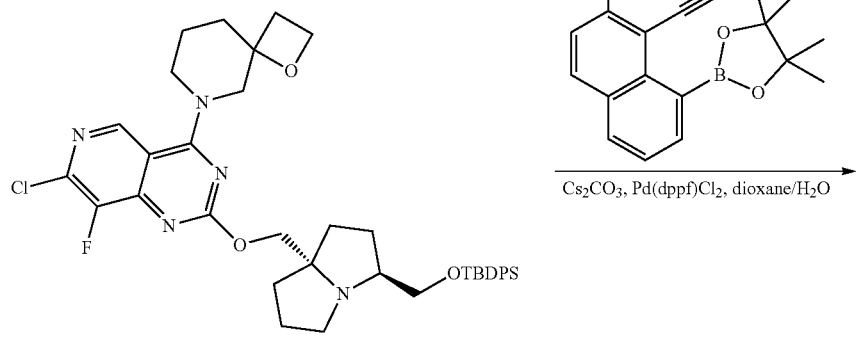

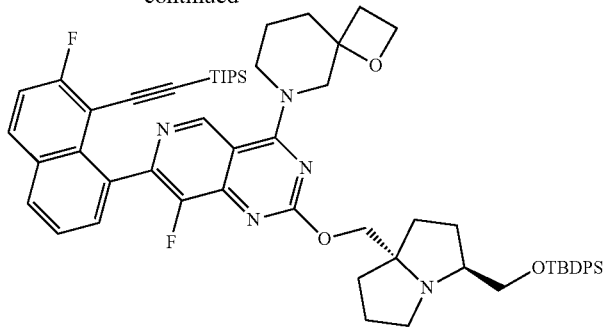

To a solution of tert-butyl-[[(3S,8S)-8-[[7-chloro-8-fluoro-4-(1-oxa-8-azaspiro[3.5]nonan-8-yl)pyrido [4,3-d] pyrimidin-2-yl]oxymethyl]-1,2,3,5,6,7-hexahydropyrrolizin-3-yl]methoxy]-diphenyl-silane (1.3 g, 1.81 mmol, CAS #2503307-87-5), 2-[2-fluoro-8-(4,4,5,5-tetramethyl-1,3,2-dioxaborolan-2-yl)-1-naphthyl] ethynyl-triisopropyl-silane (985 mg, 2.18 mmol), ditert-butyl (cyclopentyl) phosphane; dichloropalladium; iron (236 mg, 362 µmol), Cs₂CO₃ (1.77 g, 5.44 mmol) in dioxane (15 mL) was added H₂O (2.5 mL) dropwise at 25° C., then the reaction mixture was stirred at 100° C. for 3 hrs under N₂. On completion, the reaction mixture was concentrated in vacuo to give a residue. The residue was purified by column chromatography (SiO₂, DCM: EtOAc, P1: Rf=0.5) to give the title compound (600 mg, 33% yield) as light yellow solid. ¹H NMR (400 MHz, DMSO-d₆) δ 9.36 (s, 1H), 9.13 (s, 1H), 9.02 (s, 1H), 8.27-8.18 (m, 2H), 7.72-7.58 (m, 6H), 7.45 (m, 6H), 4.48 (m, 1H), 4.43-4.30 (m, 2H), 4.29-4.19 (m, 1H), 4.18-4.00 (m, 3H), 3.92-3.86 (m, 1H), 3.80-3.71 (m, 2H), 3.50-3.40 (m, 1H), 3.20 (m, 1H), 2.80-2.65 (m, 2H), 2.46-2.27 (m, 2H), 2.19-1.99 (m, 2H), 1.93-1.64 (m, 9H), 1.57-1.44 (m, 1H), 1.41-1.22 (m, 1H), 1.21-1.07 (m, 1H), 1.00 (m, 9H), 0.88-0.79 (m, 15H), 0.54-0.42 (m, 2H); LC-MS (ESI⁺) m/z 1006.4 (M+H)⁺.

(d) Step 4—[(3S,8S)-8-[[7-(8-ethynyl-7-fluoro-1-naphthyl)-8-fluoro-4-(1-oxa-8-azaspiro[3.5]nonan-8-yl) pyrido[4,3-d]pyrimidin-2-yl]oxymethyl]-1,2,3,5,6,7-hexahydropyrrolizin-3-yl]methanol

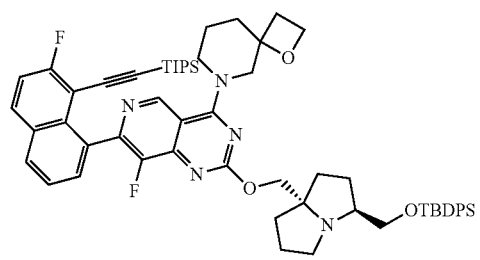

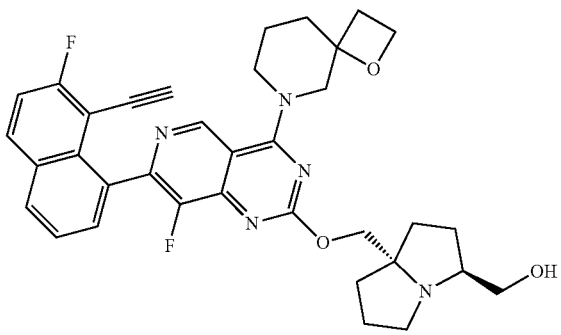

To a solution of tert-butyl-[[(3S,8S)-8-[[8-fluoro-7-[7-fluoro-8-(2-triisopropylsilylethynyl)-1-naphthyl]-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methoxy]-diphenyl-silane (260 mg, 258 µmol) in DMSO (2 mL) was added CsF (117 mg, 775 µmol). The mixture was stirred at 30° C. for 16 hrs. On completion, the stirring reaction mixture was quenched with H₂O (5 mL). The residue was diluted with water (10 mL) and extracted with EA (10 mL×6). The combined organic layer was dried over Na₂SO₄, filtered and concentrated in vacuo to give a residue. The residue was purified by reverse phase (0.1% FA condition) to give the title compound (140 mg, 88% yield) as light yellow solid. ¹H NMR (400 MHz, DMSO-d₆) δ 9.25-9.14 (m, 1H), 8.28-8.21 (m, 2H), 7.74-7.68 (m, 2H), 7.63-7.58 (m, 1H), 4.50-4.37 (m, 3H), 4.33-4.15 (m, 5H), 3.74-3.65 (m, 6H), 2.39-2.32 (m, 2H), 2.15-2.07 (m, 2H), 1.93-1.71 (m, 11H); LC-MS (ESI⁺) m/z 612.1 (M+H)⁺.

(e) Step 5—[(3S,8S)-8-[[7-(8-ethynyl-7-fluoro-1-naphthyl)-8-fluoro-4-(1-oxa-8-azaspiro[3.5]nonan-8-yl) pyrido[4,3-d]pyrimidin-2-yl]oxymethyl]-1,2,3,5,6,7-hexahydropyrrolizin-3-yl]methyl (4-nitrophenyl) carbonate

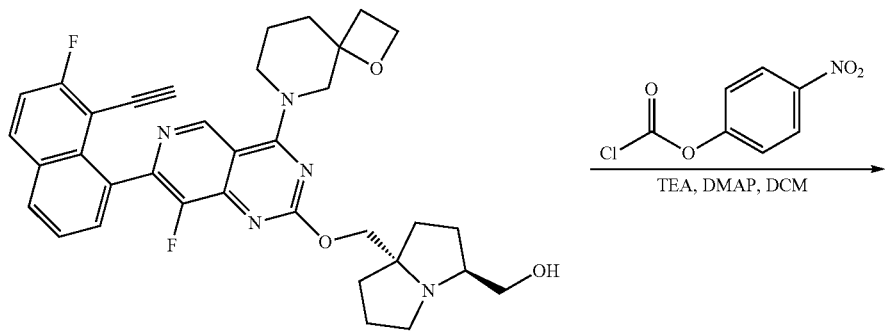

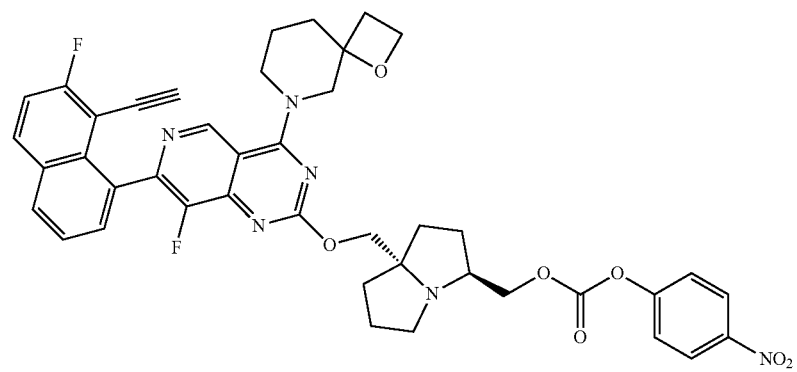

To a solution of [(3S,8S)-8-[[7-(8-ethynyl-7-fluoro-1-naphthyl)-8-fluoro-4-(1-oxa-8-azaspiro[3.5] nonan-8-yl) pyrido[4,3-d]pyrimidin-2-yl]oxymethyl]-1,2,3,5,6,7-hexahydropyrrolizin-3-yl]methanol (80 mg, 130 μmol) in DCM (6 mL) was added TEA (39.7 mg, 392 μmol) and DMAP (1.60 mg, 13.0 μmol). Then (4-nitrophenyl) carbonochloridate (92.2 mg, 457 μmol, CAS #7693-46-1) was added to the mixture was stirred at 25° C. for 1 hr. On completion, the stirring reaction mixture was quenched with H$_2$O (5 mL). The residue was diluted with water (10 mL) and extracted with EA (5 mL×5). The combined organic layer was dried over Na$_2$SO$_4$, filtered and concentrated in vacuo to give the title compound (100 mg, 98% yield) as light yellow solid. LC-MS (ESI$^+$) m/z 777.1 (M+H)$^+$.

(f) Step 6—[(3S,8S)-8-[[7-(8-ethynyl-7-fluoro-1-naphthyl)-8-fluoro-4-(1-oxa-8-azaspiro[3.5]nonan-8-yl) pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propoxy]piperidine-1-carboxylate (036)

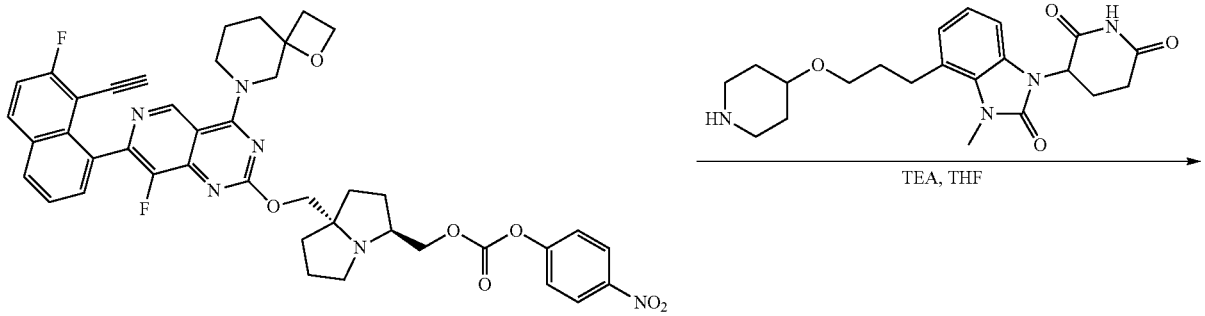

-continued

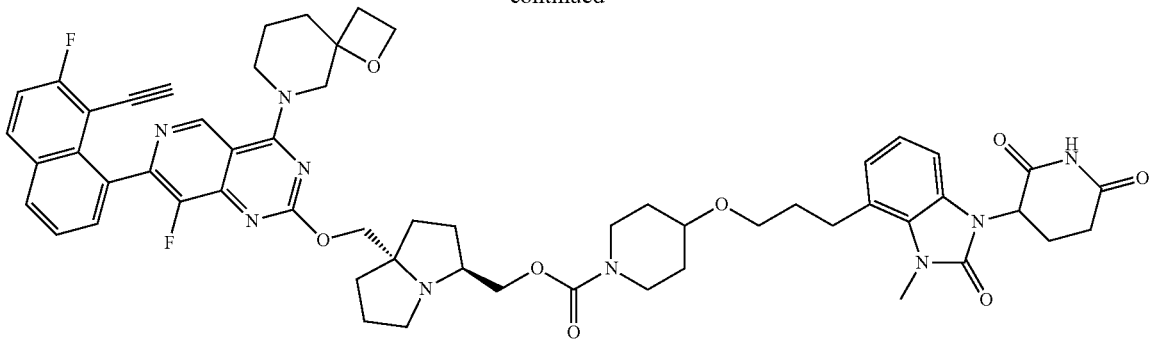

A mixture of 3-[3-methyl-2-oxo-4-[3-(4-piperidyloxy)propyl]benzimidazol-1-yl]piperidine-2,6-dione (67.5 mg, 154 μmol, HCl), TEA (23.4 mg, 231 μmol) in THF (3 mL) was stirred at 25° C., then [(3S,8S)-8-[[7-(8-ethynyl-7-fluoro-1-naphthyl)-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl(4-nitrophenyl)carbonate (60 mg, 77.2 μmol) in THF (3 mL) was added. The mixture was stirred at 25° C. for 16 hrs. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 22%-52% B over 10 min) to give the title compound (20.8 mg, 26% yield) as yellow solid. $^1$H NMR (400 MHz, DMSO-$d_6$) δ 11.11 (s, 1H), 9.21-9.14 (m, 1H), 8.23 (d, J=6.4, 9.6 Hz, 2H), 7.73-7.67 (m, 2H), 7.62 (t, J=9.2 Hz, 1H), 6.99-6.94 (m, 2H), 6.89-6.84 (m, 1H), 5.37 (dd, J=4.8, 12.4 Hz, 1H), 4.46-4.40 (m, 2H), 4.23-4.09 (m, 5H), 3.91 (s, 1H), 3.89-3.77 (m, 1H), 3.69-3.61 (m, 3H), 3.56 (s, 3H), 3.48 (d, J=5.2 Hz, 3H), 3.15-3.09 (m, 2H), 2.98-2.92 (m, 2H), 2.92-2.85 (m, 1H), 2.78-2.68 (m, 4H), 2.62 (d, J=17.2 Hz, 3H), 2.41-2.33 (m, 1H), 2.16-1.98 (m, 4H), 1.87-1.73 (m, 12H), 1.56-1.47 (m, 1H), 1.41-1.32 (m, 2H); LC-MS (ESI$^+$) m/z 1038.5 (M+H)$^+$.

Example 48. Synthesis of Compound 046

(a) Step 1—Tert-butyl 4-prop-2-ynyl-1-oxa-4,9-diazaspiro[5.5]undecane-9-carboxylate

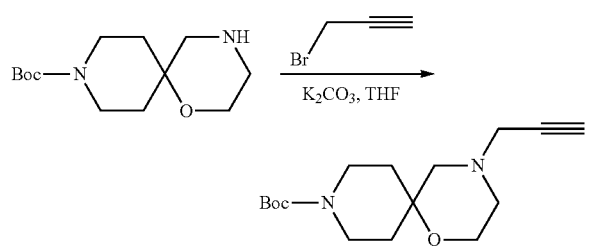

To a solution of tert-butyl 1-oxa-4,9-diazaspiro[5.5]undecane-9-carboxylate (3.00 g, 11.70 mmol, CAS #930785-40-3) and 3-bromoprop-1-yne (1.39 g, 11.7 mmol, CAS #106-96-7) in THF (60 mL) was added $K_2CO_3$ (3.23 g, 23.4 mmol). The mixture was stirred at 25° C. for 16 hrs. On completion, the reaction mixture was added $H_2O$ (100 mL) and extracted with ethyl acetate (3×80 mL). The combined organic layers were washed with brine (60 mL), dried over anhydrous sodium sulfate, filter and the filtrate was concentrated in vacuo. The residue was purified by column chromatography ($SiO_2$, Petroleum ether/Ethyl acetate=10/1 to 2/1) to give the title compound (3.10 g, 89% yield) as colorless oil. $^1$H NMR (400 MHz, CDCl$_3$) δ 3.85-3.74 (m, 2H), 3.74-3.61 (m, 2H), 3.26 (d, J=2.0 Hz, 2H), 3.16 (t, J=11.2 Hz, 2H), 2.56-2.48 (m, 2H), 2.36 (s, 2H), 2.26 (t, J=2.0 Hz, 1H), 1.99-1.88 (m, 2H), 1.62 (d, J=3.2 Hz, 1H), 1.53-1.49 (m, 1H), 1.46 (s, 9H).

(b) Step 2—Tert-butyl 4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate

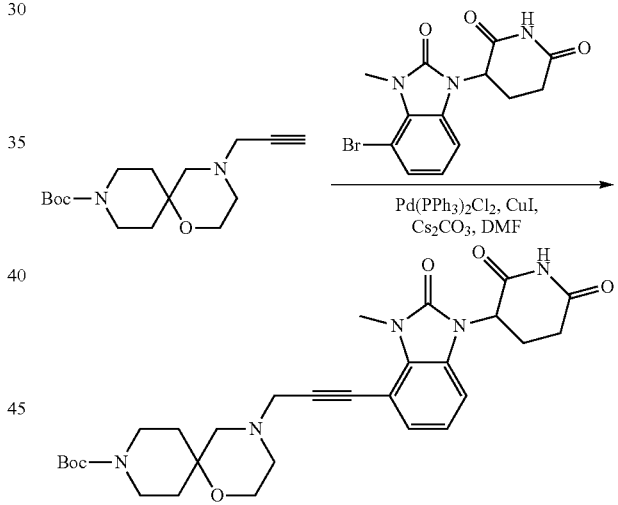

To a solution of tert-butyl 4-prop-2-ynyl-1-oxa-4,9-diazaspiro[5.5]undecane-9-carboxylate (900 mg, 3.06 mmol) and 3-(4-bromo-3-methyl-2-oxo-benzimidazol-1-yl)piperidine-2,6-dione (689 mg, 2.04 mmol, CAS #191732-76-0) in DMF (10 mL) was added $Cs_2CO_3$ (1.33 g, 4.08 mmol), CuI (38.8 mg, 203 μmol) and dichloropalladium; triphenylphosphane (143 mg, 203 μmol). The mixture was stirred at 80° C. for 2 hrs under $N_2$ atmosphere. On completion, the mixture was filtered, the filtrate was concentrated in vacuo. The crude product was purified by reversed-phase HPLC (0.1% FA condition), and then the crude product was re-purified by reverse-phase HPLC (0.1% NH$_4$HCO$_3$) to give the title compound (140 mg, 11% yield) as yellow solid. $^1$H NMR (400 MHz, DMSO-$d_6$) δ 7.19-7.08 (m, 2H), 7.06-7.00 (m, 1H), 5.44-5.36 (m, 1H), 3.69-3.66 (m, 2H), 3.64 (s, 3H), 3.62-3.58 (m, 2H), 3.58-3.53 (m, 4H), 3.12-2.96 (m, 4H), 2.95-2.82 (m, 2H), 2.76-2.64 (m, 2H), 2.06-1.98 (m, 2H), 1.84-1.79 (m, 2H), 1.39 (s, 9H). $^1$LC-MS (ESI$^+$) m/z 552.3 (M+H)$^+$.

1075

(c) Step 3—3-[3-Methyl-4-[3-(1-oxa-4,9-diazaspiro[5.5]undecan-4-yl)prop-1-ynyl]-2-oxo-benzimidazol-1-yl]piperidine-2,6-dione

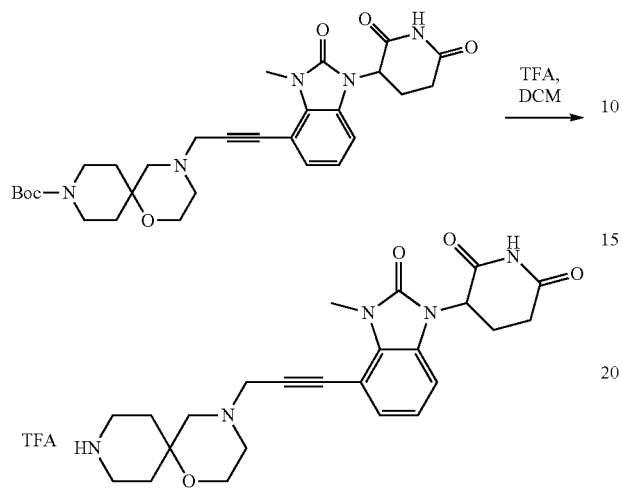

1076

To a solution of tert-butyl 4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate (65.0 mg, 117 μmol) in DCM (1 mL) was added TFA (391 mg, 3.43 mmol). The mixture was stirred at 25° C. for 0.5 hr. On completion, the mixture was concentrated in vacuo to give the title compound (63.0 mg, 94% yield, TFA salt) as faint yellow solid. LC-MS (ESI+) m/z 452.1 (M+H)$^+$.

(d) Step 4—[(3S,8S)-8-[[4-(8-Tert-butoxycarbonyl-3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-yl]prop-2-ynyl]-1-oxa-4,9-diazaspiro[5.5]undecane-9-carboxylate

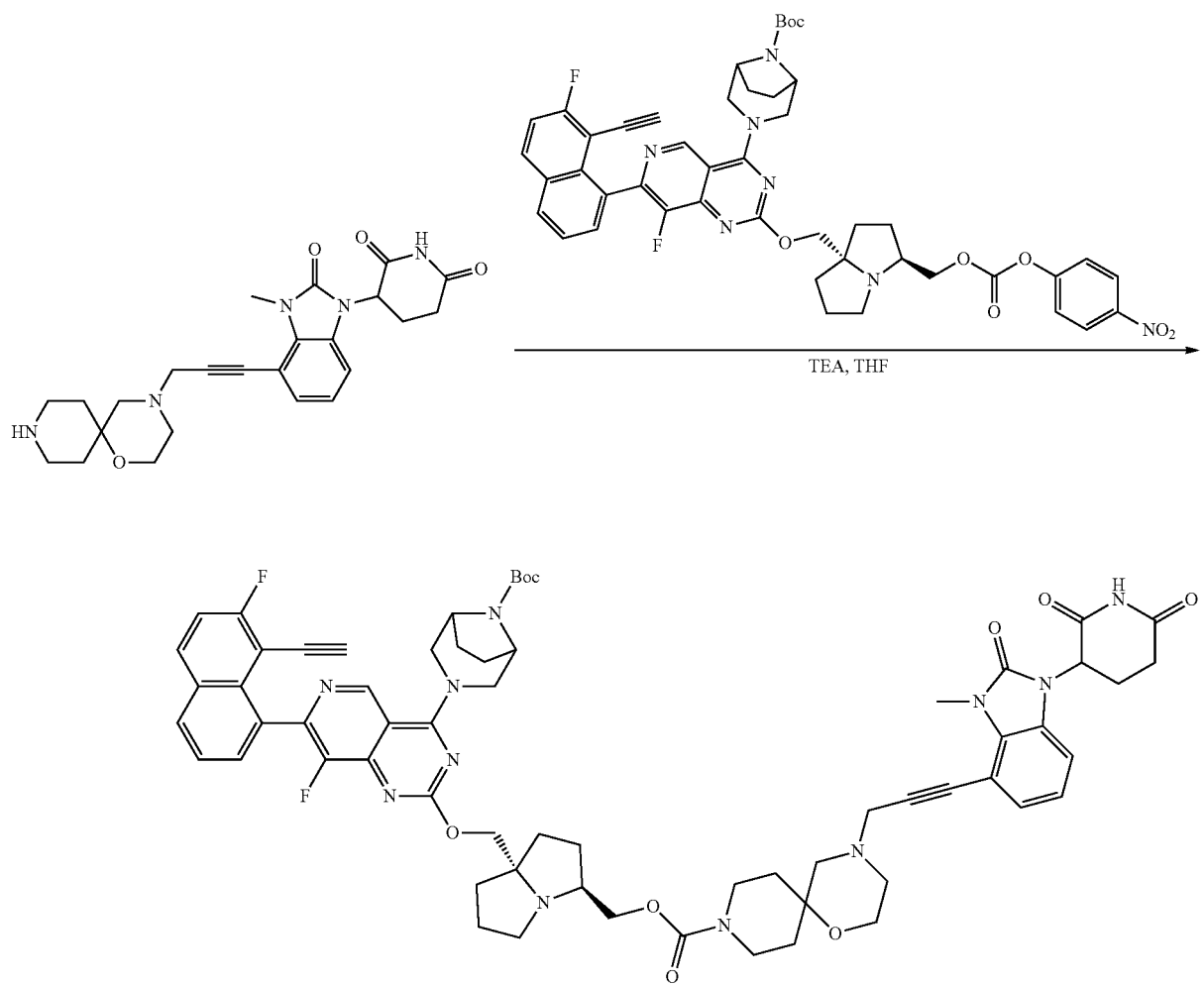

To a solution of 3-[3-methyl-4-[3-(1-oxa-4,9-diazaspiro[5.5]undecan-4-yl)prop-1-ynyl]-2-oxo-benzimidazol-1-yl]piperidine-2,6-dione (62.9 mg, 111 μmol, TFA salt) in THF (2 mL) was added TEA (15.0 mg, 148 μmol). A solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (64.0 mg, 74.2 μmol) in THF (1 mL) was added the reaction. The mixture was stirred at 25° C. for 0.5 hr. On completion, the mixture was concentrated in vacuo. The residue was purified by prep-HPLC (column: Waters xbridge 150*25 mm 10 μm; mobile phase: [water (NH₄HCO₃)-ACN]; gradient: 51%-81% B over 10 min) to give the title compound (25.0 mg, 27% yield) as faint brown solid; LC-MS (ESI+) m/z 1174.3 (M+H)⁺.

(e) Step 5—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate (046)

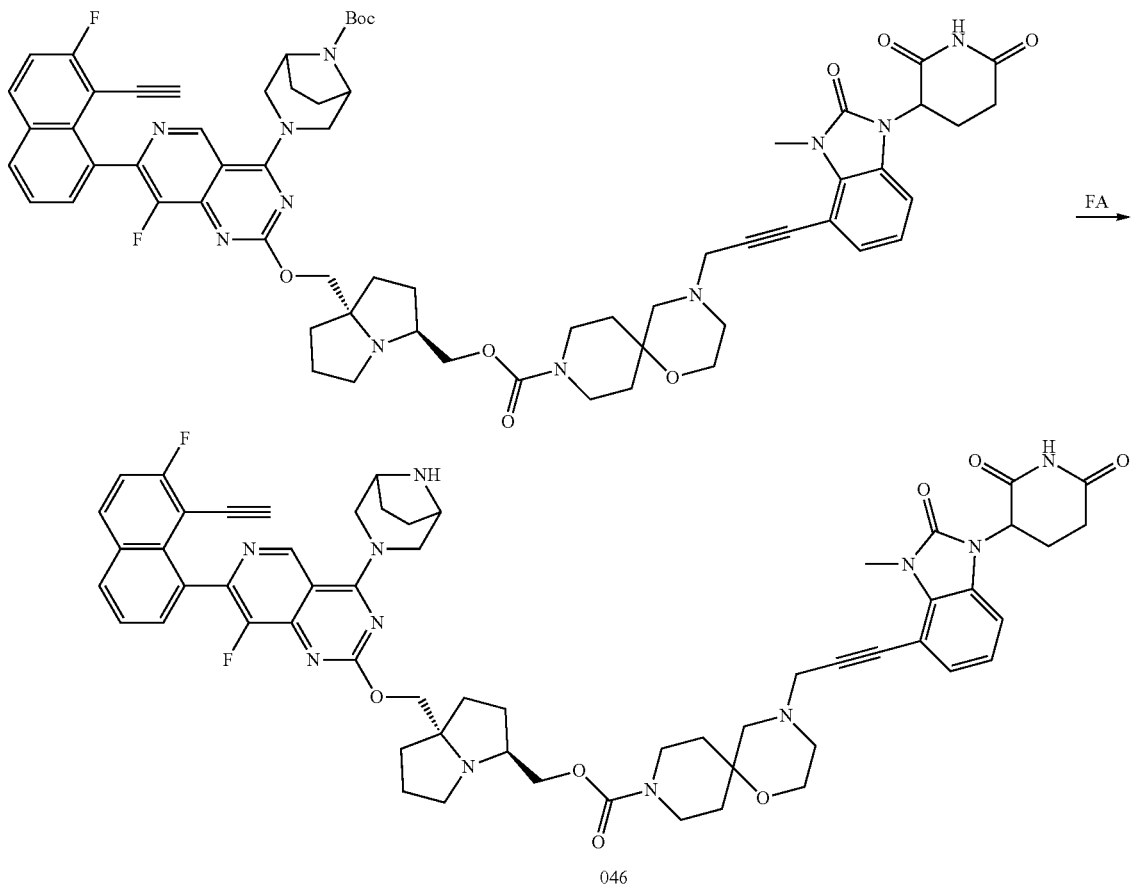

046

To a solution of [(3S,8S)-8-[[4-(8-tert-butoxycarbonyl-3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate (25.0 mg, 21.2 μmol) in DCM (1 mL) was added HCOOH (1.02 mg, 21.2 μmol). The mixture was stirred at 25° C. for 0.5 hr. On completion, the mixture was concentrated in vacuo. The residue was purified by prep-HPLC (column: Phenomenex luna C18 150*25 mm*10 um; mobile phase: [water (FA)-ACN]; gradient: 6%-36% B over 10 min) to give the title compound (10.0 mg, 43% yield, FA salt) as yellow solid. ¹H NMR (400 MHz, DMSO-d₆) δ 11.13 (s, 1H), 9.04 (s, 1H), 8.26-8.16 (m, 2H), 7.72-7.66 (m, 1H), 7.66-7.63 (m, 1H), 7.60 (t, J=9.2 Hz, 1H), 7.15 (d, J=7.6 Hz, 1H), 7.10 (d, J=8.0 Hz, 1H), 7.03-6.98 (m, 1H), 5.43-5.36 (m, 1H), 4.46 (d, J=11.2 Hz, 1H), 4.32 (d, J=11.6 Hz, 1H), 4.25-4.18 (m, 1H), 4.16-4.08 (m, 2H), 4.06-3.99 (m, 2H), 3.69-3.65 (m, 2H), 3.63 (s, 3H), 3.62-3.58 (m, 2H), 3.56-3.52 (m, 4H), 3.49-3.44 (m, 2H), 3.27-3.22 (m, 2H), 3.12-3.03 (m, 2H), 2.92-2.84 (m, 1H), 2.76-2.70 (m, 2H), 2.70-2.63 (m, 2H), 2.41-2.37 (m, 2H), 2.06-1.98 (m, 2H), 1.88-1.79 (m, 2H), 1.78-1.71 (m, 4H), 1.70-1.65 (m, 4H), 1.65-1.57 (m, 2H), 1.57-1.43 (m, 2H), 1.43-1.28 (m, 2H); LC-MS (ESI$^+$) m/z 1074.3 (M+H)$^+$.

Example 49. Synthesis of Compound 047

(a) Step 1—Tert-butyl 4-[[1-[[1-(2,6-dioxo-3-piperidyl)-3-methyl-2-oxo-benzimidazol-5-yl]methyl]-4-piperidyl]methyl]piperidine-1-carboxylate

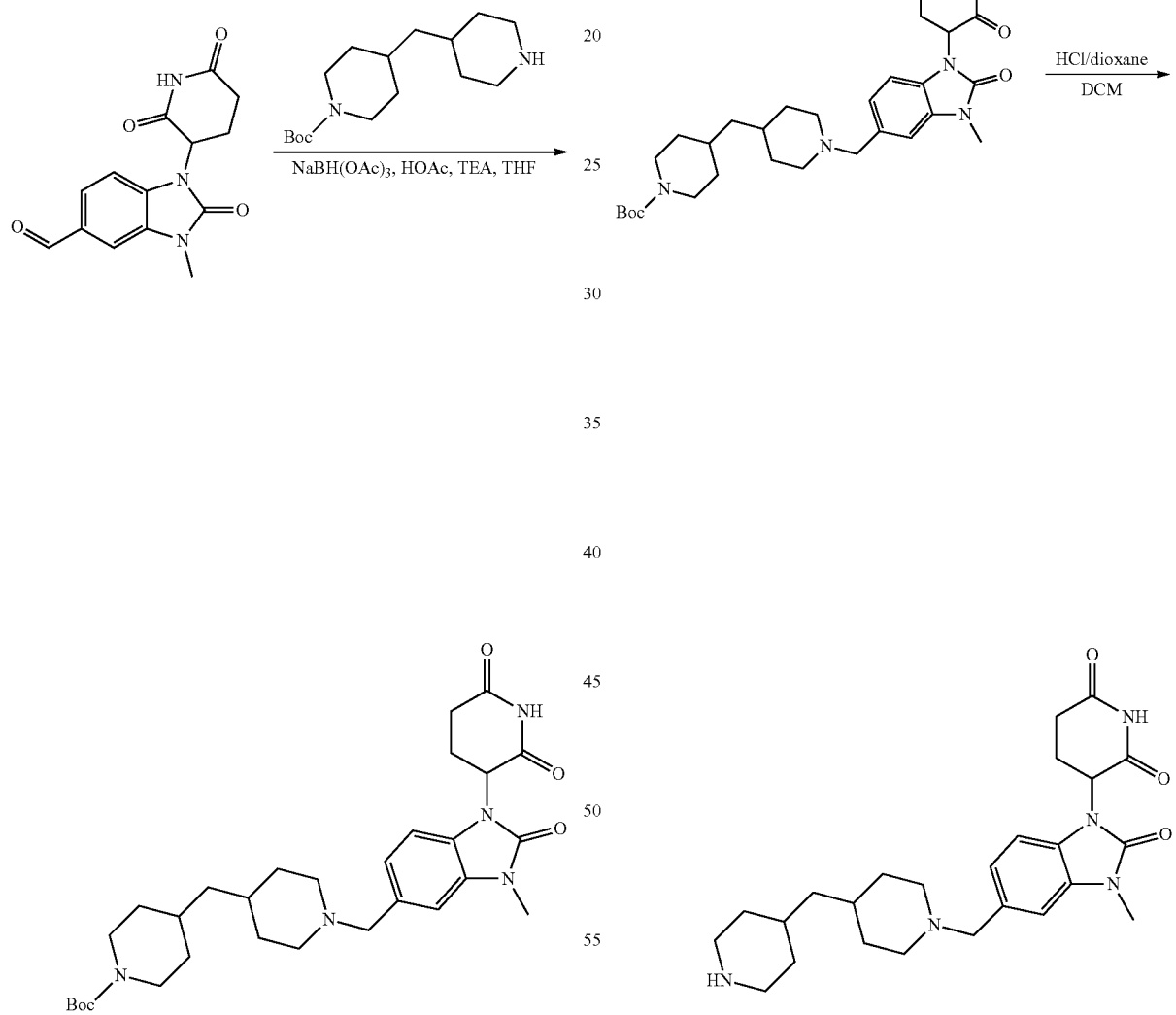

(b) Step 2—3-[3-Methyl-2-oxo-5-[[4-(4-piperidylmethyl)-1-piperidyl]methyl]benzimidazol-1-yl]piperidine-2,6-dione To a solution of tert-butyl 4-(4-piperidylmethyl)piperidine-1-carboxylate (157 mg, 556 μmol, CAS #879883-54-2) in THF (10 mL) was added TEA (84.5 mg, 835 μmol) at 25° C. until pH stabilized at 8. The mixture was stirred at 25° C. for 0.5 hr. Then HOAc (50.1 mg, 835 μmol) was added at 25° C. to the solution until pH stabilized at 5~6. Subsequently, 1-(2,6-dioxo-3-piperidyl)-3-meth yl-2-oxo-benzimidazole-5-carbaldehyde (160 mg, 556 μmol) was added and stirred for 0.5 hr at 25° C. After that, NaBH$_3$CN (52.5 mg, 835 μmol) was added one portion. The resulting reaction mixture was stirred at 25° C. for 11 hrs. On completion, the reaction mixture was concentrated in vacuo to give a residue. The residue was purified by reversed phase (0.1% FA condition) to give the title compound (140 mg, 45% yield) as white solid. LC-MS (ESI$^+$) m/z 554.3 (M+H)$^+$.

To a solution of tert-butyl 4-[[1-[[1-(2,6-dioxo-3-piperidyl)-3-methyl-2-oxo-benzimidazol-5-yl]methyl]-4-piperidyl]methyl]piperidine-1-carboxylate (140 mg, 252 μmol) in DCM (3 mL) was added HCl/dioxane (4 M, 1.40 mL). The mixture was stirred at 25° C. for 0.5 hr. On completion, the mixture was concentrated in vacuo to give the title compound (110 mg, 95% yield, HCl salt) as white solid; LC-MS (ESI$^+$) m/z 454.2 (M+H)$^+$.

(c) Step 3—Tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

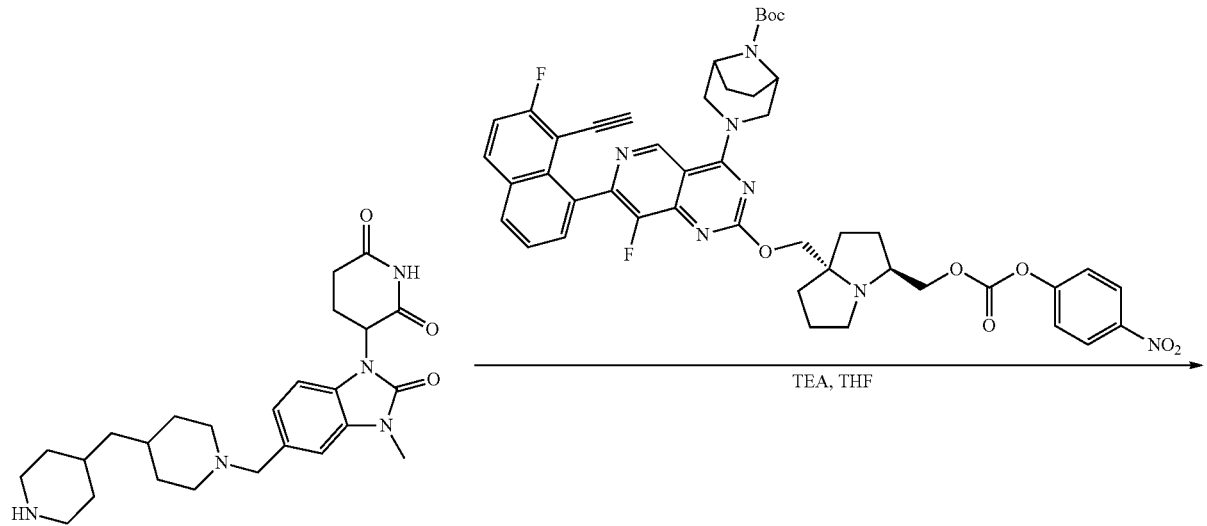

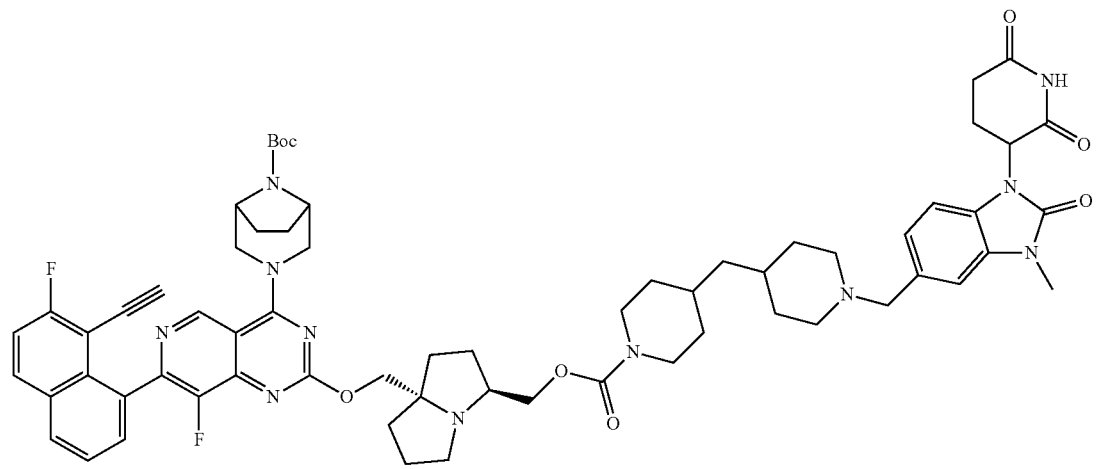

To a solution of 3-[3-methyl-2-oxo-5-[[4-(4-piperidylmethyl)-1-piperidyl]methyl]benzimidazol-1-yl]piperidine-2,6-dione (73.6 mg, 162 μmol, HCl salt) in THF (2 mL) was added TEA (57.5 mg, 568 μmol) and tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol). The mixture was stirred at 25° C. for 1 hr. On completion, the mixture was concentrated in vacuo to give a residue. The residue was purified by prep-HPLC (column: Welch Xtimate C18 150*25 mm*5 μm; mobile phase: [water (FA)-ACN]; gradient: 16%-46% B over 10 min) to give the title compound (30.0 mg, 31% yield) as white solid. LC-MS (ESI$^+$) m/z 1177.6 (M+H)$^+$.

Step 4—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[[1-[[1-
(2,6-dioxo-3-piperidyl)-3-methyl-2-oxo-
benzimidazol-5-yl]methyl]-4-piperidyl]methyl]
piperidine-1-carboxylate (047)

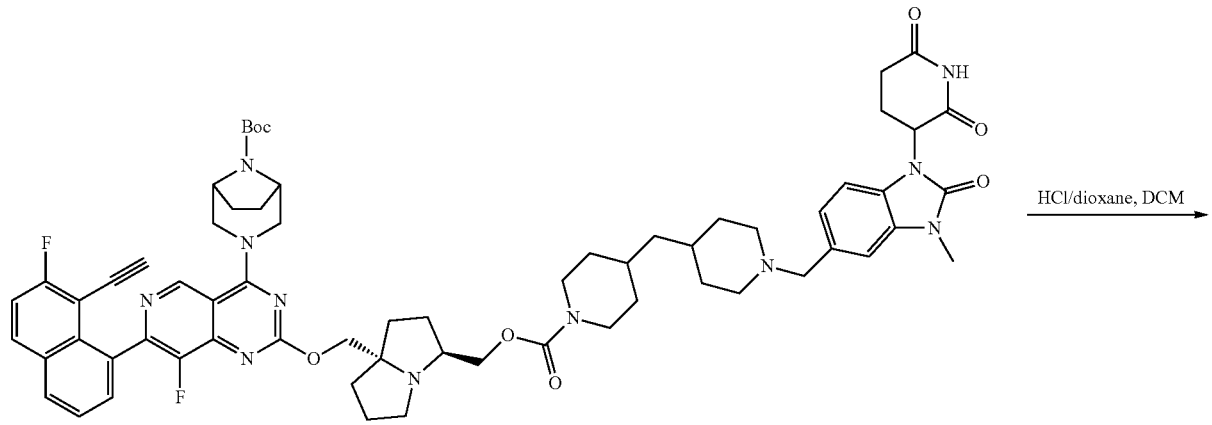

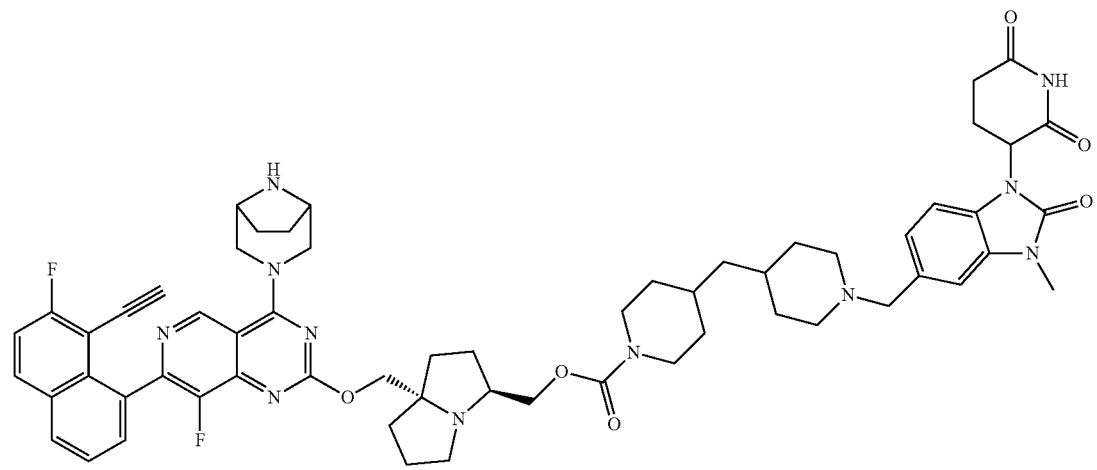

047

To a solution of tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30.0 mg, 25.5 μmol) in DCM (3 mL) was added HCl/dioxane (4 M, 0.5 mL). The mixture was stirred at 25° C. for 0.5 hr. On completion, the mixture was concentrated in vacuo to give a residue. The residue was purified by prep-HPLC (column: Welch Xtimate C18 150*25 mm*5 μm; mobile phase: [water (FA)-ACN]; gradient: 8%-38% B over 10 min) to give the title compound (12.4 mg, 43% yield, FA salt) as yellow solid. $^1$H NMR (400 MHz, DMSO-$d_6$) δ 11.10 (s, 1H), 9.05 (s, 1H), 8.27-8.20 (m, 1H), 8.18 (s, 1H), 7.74-7.55 (m, 3H), 7.08 (s, 1H), 7.06-7.01 (m, 1H), 6.95 (d, J=8.0 Hz, 1H), 5.35 (dd, J=5.2, 12.8 Hz, 1H), 4.53-4.43 (m, 1H), 4.35 (d, J=10.8 Hz, 1H), 4.18 (d, J=7.2 Hz, 1H), 4.16-4.08 (m, 2H), 4.08-4.01 (m, 2H), 3.99-3.87 (m, 3H), 3.64 (s, 5H), 3.45 (s, 2H), 3.32 (s, 3H), 3.28 (s, 1H), 2.88 (dd, J=5.2, 16.4 Hz, 1H), 2.81-2.58 (m, 9H), 2.07-1.95 (m, 2H), 1.89 (t, J=11.2 Hz, 2H), 1.76-1.67 (m, 8H), 1.57 (d, J=7.6 Hz, 6H), 1.32-1.22 (m, 1H), 1.15-1.00 (m, 4H), 0.98-0.83 (m, 2H); LC-MS (ESI$^+$) m/z 1077.6 (M+H)$^+$.

Example 50. Synthesis of Compound 048

(a) Step 1—Tert-butyl 4-[[1-[1-(2,6-dioxo-3-piperidyl)-3-methyl-2-oxo-benzimidazol-4-yl]-4-piperidyl]methyl]piperidine-1-carboxylate

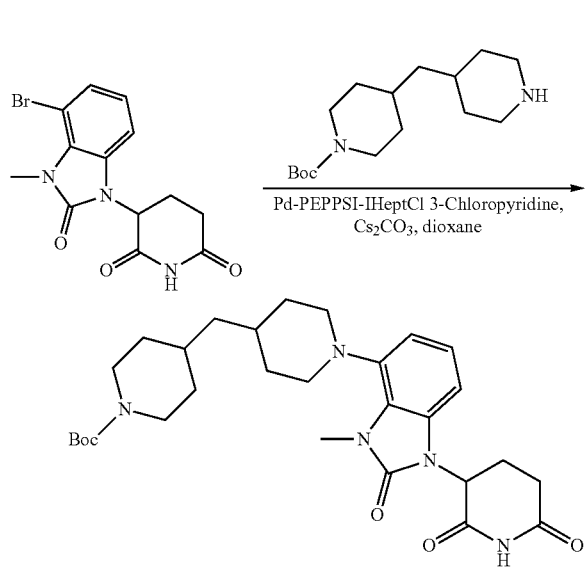

To a solution of 3-(4-bromo-3-methyl-2-oxo-benzimidazol-1-yl)piperidine-2,6-dione (159 mg, 472 μmol, CAS #2304754-51-4) and tert-butyl 4-(4-piperidylmethyl)piperidine-1-carboxylate (200 mg, 708 μmol, CAS #879883-54-2) in dioxane (5 mL) was added Cs$_2$CO$_3$ (461 mg, 1.42 mmol), 4 Å MS (100 mg) and 1,3-bis[2,6-bis(1-propylbutyl)phenyl]-4,5-dichloro-2H-imidazol-1-ium-2-ide; 3-chloropyridine; dichloropalladium (91.8 mg, 94.4 μmol). The mixture was degassed with N$_2$ for 3 times, the mixture was stirred at 110° C. for 32 hrs under N$_2$. On completion, the reaction mixture was filtered and the filtrate was concentrated in vacuo to give a residue. The residue was purified by reverse phase (0.1% FA condition) to give the title compound (85 mg, 33% yield) as a brown solid. LC-MS (ESI$^+$) m/z 540.3 (M+H)$^+$.

(b) Step 2—3-[3-Methyl-2-oxo-4-[4-(4-piperidylmethyl)-1-piperidyl]benzimidazol-1-yl]piperidine-2,6-dione

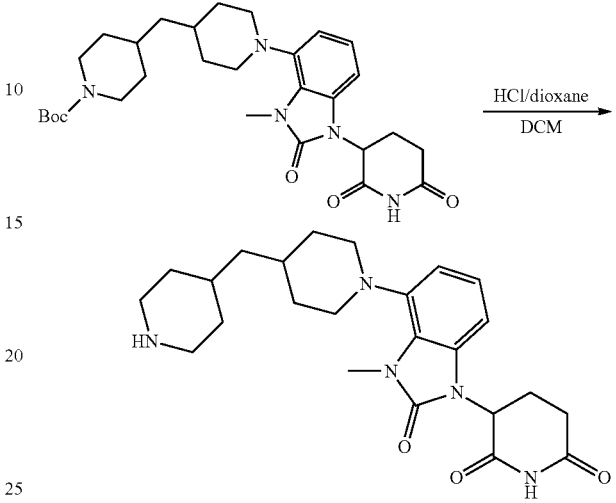

To a solution of tert-butyl4-[[1-[1-(2,6-dioxo-3-piperidyl)-3-methyl-2-oxo-benzimidazol-4-yl]-4-piperidyl]methyl]piperidine-1-carboxylate (70 mg, 129 μmol) in DCM (1 mL) was added HCl/dioxane (4 M, 1 mL). The mixture was stirred at 25° C. for 1 hr. On completion, the reaction mixture was concentrated in vacuo to give the title compound (60 mg, 97% yield, HCl) as a yellow solid. LC-MS (ESI$^+$) m/z 440.3 (M+H)$^+$.

(c) Step 3—Tert-butyl 3-[2-[[(3S,8S)-3-[[4-[[1-[1-(2,6-dioxo-3-piperidyl)-3-methyl-2-oxo-benzimidazol-4-yl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

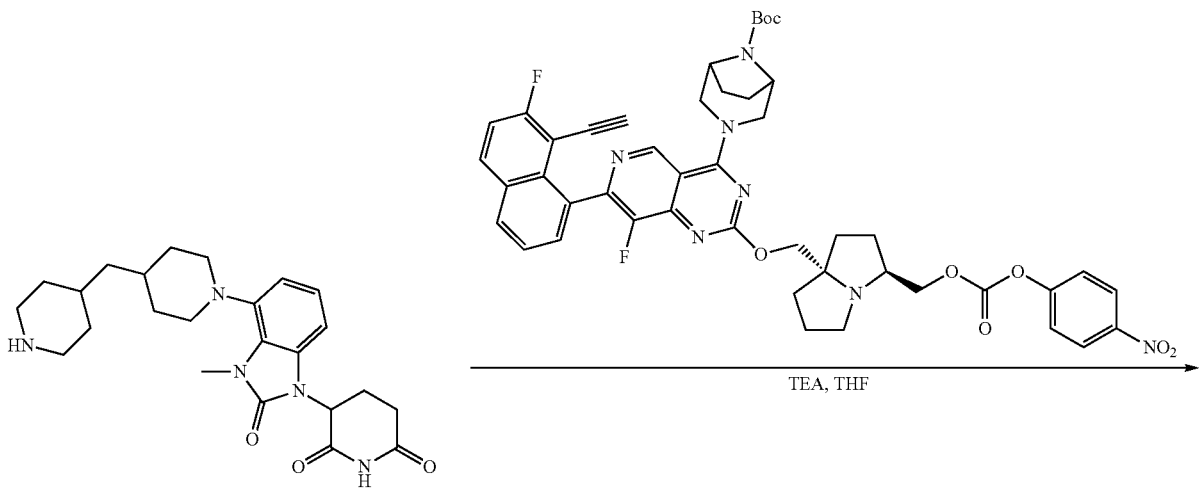

1087

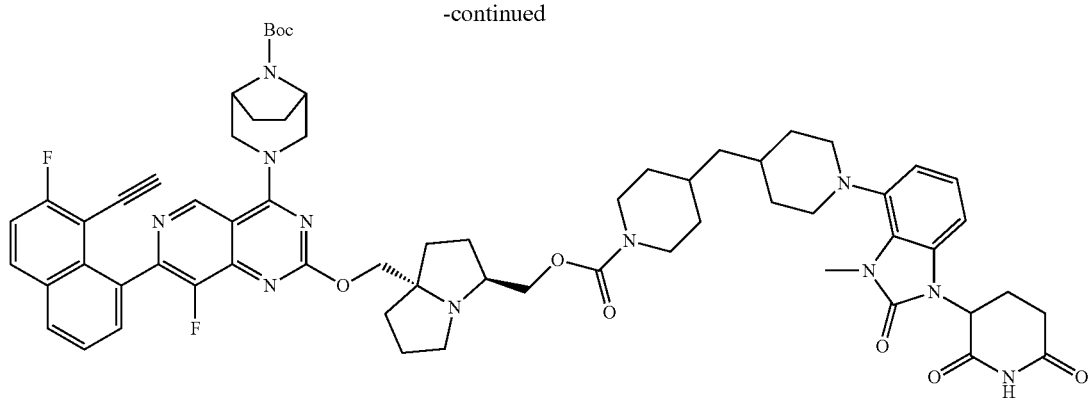

To a solution of 3-[3-methyl-2-oxo-4-[4-(4-piperidylmethyl)-1-piperidyl]benzimidazol-1-yl] piperidine-2,6-dione (40.8 mg, 85.8 μmol, HCl) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74 mg, 85.8 μmol) in THF (2 mL) was added TEA (8.69 mg, 85.8 μmol, 11.9 μL). The mixture was stirred at 25° C. for 0.5 hr. On completion, the reaction mixture was filtered and the filtrate was concentrated in vacuo to give the title compound (40 mg, 40% yield) as a white solid. $^1$H NMR (400 MHz, DMSO-d$_6$) δ 11.09 (s, 1H), 9.09 (s, 1H), 8.33-8.09 (m, 2H), 7.77-7.52 (m, 3H), 7.01-6.93 (m, 1H), 6.90-6.80 (m, 2H), 5.42-5.23 (m, 1H), 4.60-4.49 (m, 1H), 4.47-4.36 (m, 1H),

1088

-continued 4.34-4.26 (m, 2H), 4.25-4.08 (m, 4H), 4.07 (s, 1H), 4.03-4.00 (m, 1H), 3.99-3.88 (m, 2H), 3.69-3.63 (m, 2H), 3.60 (s, 3H), 3.10-3.01 (m, 2H), 2.93-2.86 (m, 1H), 2.81-2.72 (m, 4H), 2.70-2.62 (m, 5H), 2.09-1.94 (m, 2H), 1.93-1.80 (m, 3H), 1.80-1.68 (m, 9H), 1.67-1.59 (m, 3H), 1.46 (s, 9H), 1.37-1.22 (m, 3H), 1.21-1.12 (m, 2H), 1.04-0.89 (m, 2H). LC-MS (ESI$^+$) m/z 582.0 (M/2+H)$^+$.

(d) Step 4 [(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-4-yl]-4-piperidyl]methyl]piperidine-1-carboxylate (048)

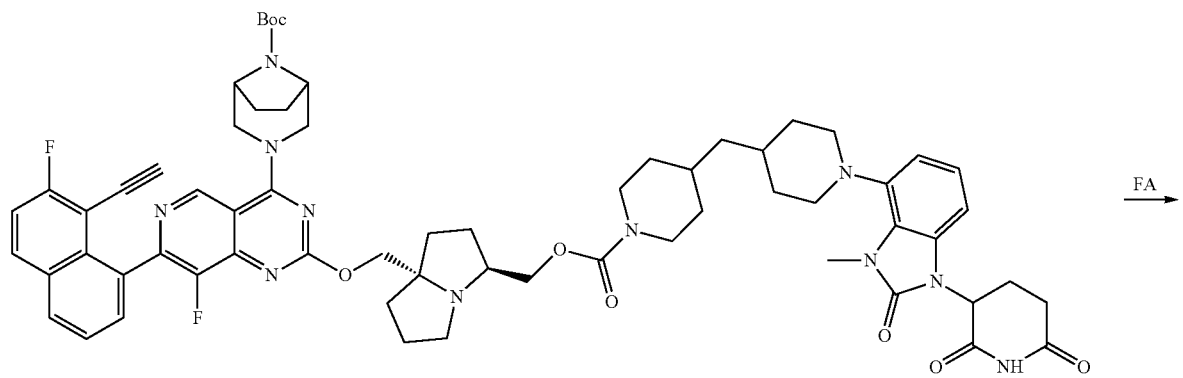

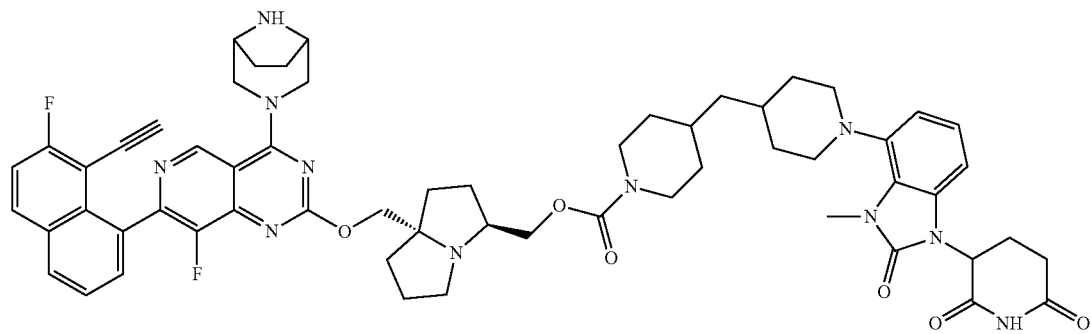

048

Tert-butyl3-[2-[[(3S,8S)-3-[[4-[[1-[1-(2,6-dioxo-3-piperidyl)-3-methyl-2-oxo-benzimidazol-4-yl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35 mg, 30.1 µmol) was dissolved in FA (1 mL). The reaction was stirred at 25° C. for 0.5 hr. On completion, the reaction mixture was dried with N₂ to give the title compound (8.36 mg, 24% yield, 99% purity, FA) as yellow solid. ¹H NMR (400 MHz, DMSO-d₆) δ 11.09 (s, 1H), 9.05 (s, 1H), 8.26-8.21 (m, 1H), 8.20-8.16 (m, 1H), 7.74-7.54 (m, 3H), 7.03-6.92 (m, 1H), 6.90-6.80 (m, 2H), 5.34 (dd, J=5.6, 12.8 Hz, 1H), 4.47 (d, J=10.4 Hz, 1H), 4.34 (d, J=10.8 Hz, 1H), 4.28-4.15 (m, 2H), 4.14-4.10 (m, 2H), 4.08-4.00 (m, 2H), 3.99-3.91 (m, 2H), 3.62-3.58 (m, 5H), 3.29-3.24 (m, 1H), 3.09-3.02 (m, 2H), 2.93-2.85 (m, 1H), 2.81-2.74 (m, 2H), 2.73-2.67 (m, 3H), 2.65-2.57 (m, 3H), 2.08-1.95 (m, 2H), 1.83-1.60 (m, 14H), 1.58-1.40 (m, 4H), 1.35-1.21 (m, 3H), 1.20-1.10 (m, 2H), 1.04-0.89 (m, 2H), LC-MS (ESI⁺) m/z 1062.6 (M+H)⁺.

Example 51. Synthesis of Compound 049

(a) Step 1—Tert-butyl 4-[2-[1-[[1-(2,6-dioxo-3-piperidyl)-3-methyl-2-oxo-benzimidazol-4-yl]methyl]-4-piperidyl]ethyl]piperidine-1-carboxylate

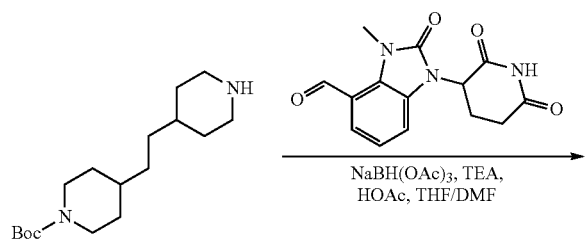

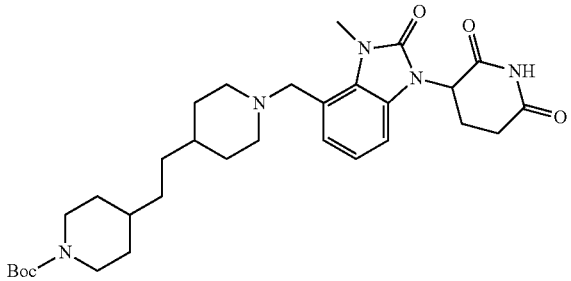

To a solution of tert-butyl 4-[2-(4-piperidyl)ethyl]piperidine-1-carboxylate (100 mg, 337 µmol, CAS #775288-40-9) in DMF (3 mL) was added TEA (102 mg, 1.01 mmol) was stirred at 25° C. for 0.1 hr, then AcOH (20.2 mg, 337 µmol), 1-(2,6-dioxo-3-piperidyl)-3-methyl-2-oxo-benzimidazole-4-carbaldehyde (193 mg, 674 µmol) was added at 25° C. and the mixture was stirred at 25° C. for 0.5 hr. Then NaBH(OAc)₃ (85.7 mg, 404 µmol) was added. The reaction mixture was stirred at 25° C. for 12 hrs. On completion, the stirring reaction mixture was quenched with H₂O (5 mL). The residue was diluted with water (10 mL) and extracted with EA (10 mL×3). The combined organic layer was dried over Na₂SO₄, filtered and concentrated in vacuo to give a residue. The residue was purified by reverse phase (0.1% FA condition) to give the title compound (67 mg, 35% yield) as light yellow solid. LC-MS (ESI⁺) m/z 568.2 (M+H)⁺.

(b) Step 2—3-[3-Methyl-2-oxo-4-[[4-[2-(4-piperidyl)ethyl]-1-piperidyl]methyl]benzimidazol-1-yl]piperidine-2,6-dione

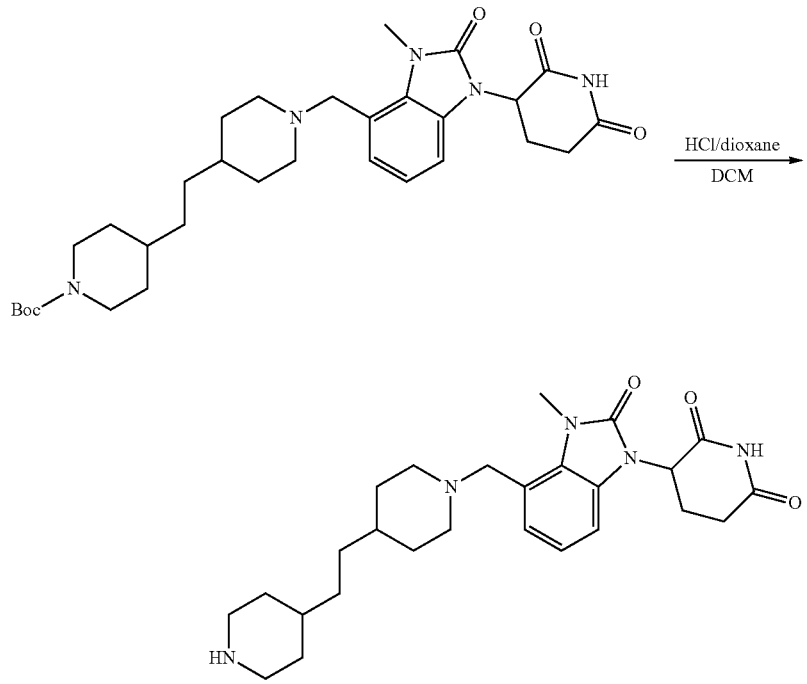

To a solution of tert-butyl 4-[2-[1-[[1-(2,6-dioxo-3-piperidyl)-3-methyl-2-oxo-benzimidazol-4-yl] methyl]-4-piperidyl]ethyl]piperidine-1-carboxylate (60 mg, 105 μmol) in DCM (2 mL) was added HCl/dioxane (4 M, 1 mL) dropwise at 0° C., then the reaction mixture was stirred at 25° C. for 2 hrs. On completion, the reaction mixture was concentrated in vacuo to give the title compound (52 mg, 97% yield, HCl) as light yellow solid. LC-MS (ESI⁺) m/z 468.5 (M+H)⁺.

(c) Step 3—Tert-butyl 3-[2-[[(3S,8S)-3-[[4-[2-[1-[[1-(2,6-dioxo-3-piperidyl)-3-methyl-2-oxo-benzimidazol-4-yl]methyl]-4-piperidyl]ethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

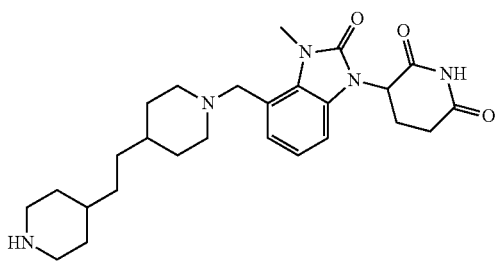

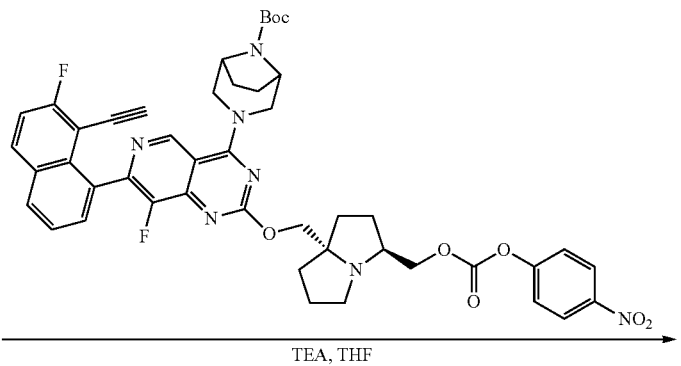

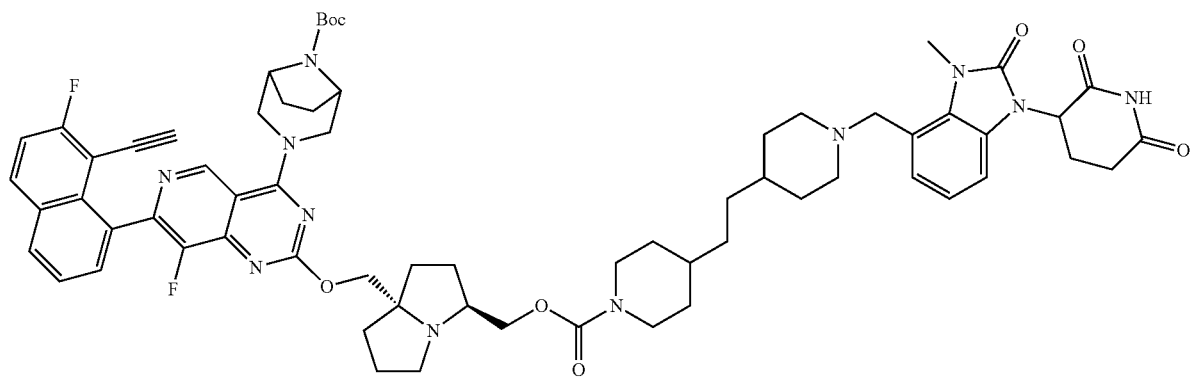

A mixture of 3-[3-methyl-2-oxo-4-[[4-[2-(4-piperidyl)ethyl]-1-piperidyl]methyl]benzimidazol-1-yl] piperidine-2,6-dione (49 mg, 97.2 μmol, HCl), TEA (29.5 mg, 291 μmol) in THF (4 mL) was stirred at 25° C., then tert-butyl 3-[7-(8-ethynyl-7-fluoro-1-naphthyl)-8-fluoro-2-[[(3S,8S)-3-[(4-nitrophenoxy) carbonyl oxy methyl]-1,2,3,5,6,7-hexahydropyrrolizin-8-yl] methoxy]pyrido[4,3-d] pyrimidin-4-yl]-3,8-diazabicyclo[3.2.1]octane-8-carboxylate (67.0 mg, 77 μmol) in THF (4 mL) was added. The mixture was stirred at 25° C. for 2 hrs. On completion, the reaction mixture was concentrated in vacuo to give a residue. The residue was purified by prep-HPLC (column: Phenomenex Luna C18 150*25 mm*10 μm; mobile phase: [water (0.225% FA)-ACN]; B %: 80%-100%, 10 min) to give the title compound (40 mg, 34% yield) as light yellow solid. LC-MS (ESI⁺) m/z 1190.4 (M+H)⁺.

(d) Step 4—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl4-[2-[1-[[1-
(2,6-dioxo-3-piperidyl)-3-methyl-2-oxo-
benzimidazol-4-yl]methyl]-4-piperidyl]ethyl]
piperidine-1-carboxylate (049)

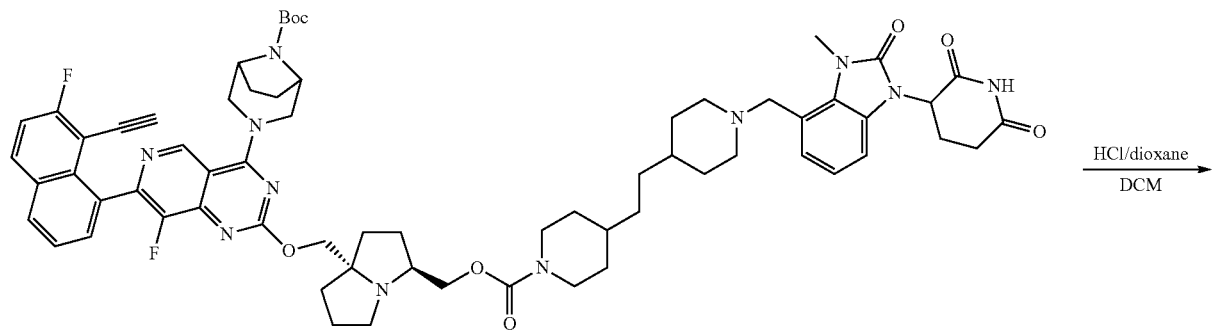

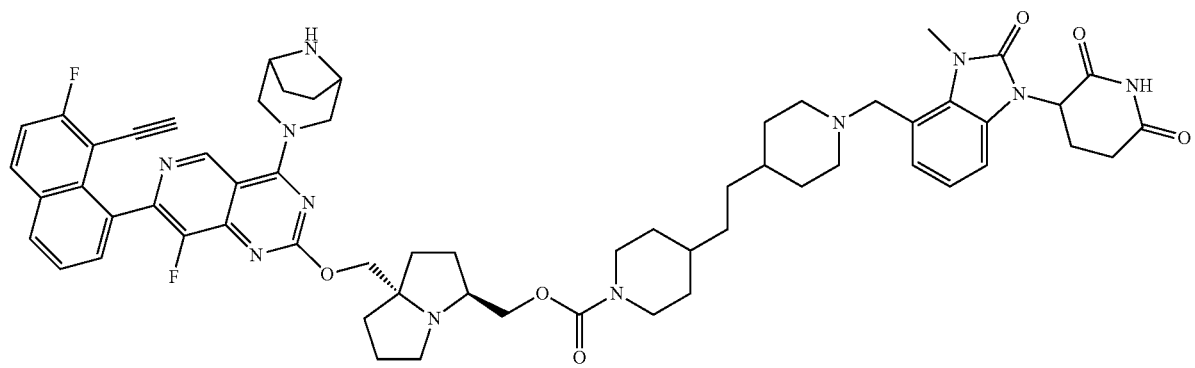

To a solution of tert-butyl 3-[2-[[(3S,8S)-3-[[4-[2-[1-[[1-(2,6-dioxo-3-piperidyl)-3-methyl-2-oxo-benzimidazol-4-yl]methyl]-4-piperidyl]ethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30 mg, 25.2 μmol) in DCM (1.5 mL) was added HCl/dioxane (4 M, 0.5 mL) dropwise at 0° C., then the reaction mixture was stirred at 25° C. for 1 hr. On completion, the reaction mixture was concentrated in vacuo to give the title compound (13.07 mg, 45% yield, FA) as yellow solid. $^1$H NMR (400 MHz, DMSO-$d_6$) δ 11.10 (s, 1H), 9.06 (s, 1H), 8.25-8.22 (m, 1H), 7.73-7.57 (m, 4H), 7.07 (d, J=7.2 Hz, 1H), 6.95 (t, J=7.6 Hz, 1H), 6.86 (d, J=7.2 Hz, 1H), 5.41-5.35 (m, 1H), 4.49 (d, J=12.4 Hz, 1H), 4.38-4.33 (m, 1H), 4.25-4.17 (m, 2H), 4.16-4.12 (m, 2H), 4.08-4.07 (m, 1H), 4.06-4.05 (m, 1H), 4.03-4.01 (m, 1H), 3.93 (dd, J=2.0, 11.6 Hz, 4H), 3.66 (s, 3H), 3.64-3.60 (m, 2H), 3.60-3.58 (m, 2H), 2.75 (d, J=18.0 Hz, 4H), 2.09-1.97 (m, 4H), 1.96-1.88 (m, 3H), 1.78-1.73 (m, 5H), 1.72-1.68 (m, 5H), 1.62-1.57 (m, 5H), 1.39-1.28 (m, 2H), 1.20-1.15 (m, 6H), 1.06-1.01 (m, 2H), 0.97-0.91 (m, 2H); LC-MS (ESI$^+$) m/z 1090.2 (M+H)$^+$.

Example 52. Synthesis of Compound 050

(a) Step 1—3-[3-Methyl-2-oxo-5-[4-(4-piperidyloxy)but-1-ynyl]benzimidazol-1-yl]piperidine-2,6-dione

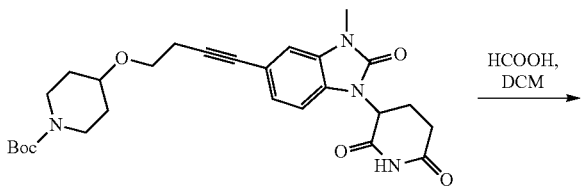

1095
-continued

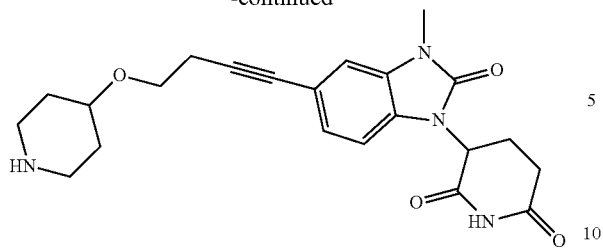

To a solution of tert-butyl 4-[4-[1-(2,6-dioxo-3-piperidyl)-3-methyl-2-oxo-benzimidazol-5-yl]but-3-ynoxy]piperidine-1-carboxylate (80.0 mg, 156 μmol) in DCM (1 mL)

1096 was added HCOOH (7.53 mg, 156 μmol). The reaction mixture was stirred at 30° C. for 2 hrs. On completion, the reaction mixture was concentrated in vacuo to give the title compound (71.0 mg, 99% yield, FA salt) as yellow oil. LC-MS (ESI$^+$) m/z 411.0 (M+H)$^+$.

(b) Step 2—Tert-butyl 3-[2-[[(3S,8S)-3-[[4-[4-[1-(2,6-dioxo-3-piperidyl)-3-methyl-2-oxo-benzimidazol-5-yl]but-3-ynoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

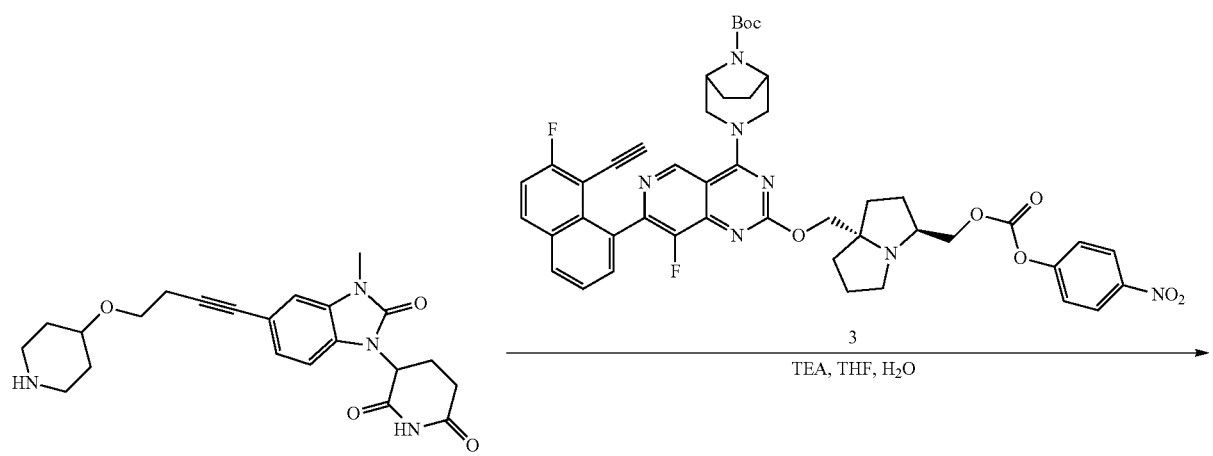

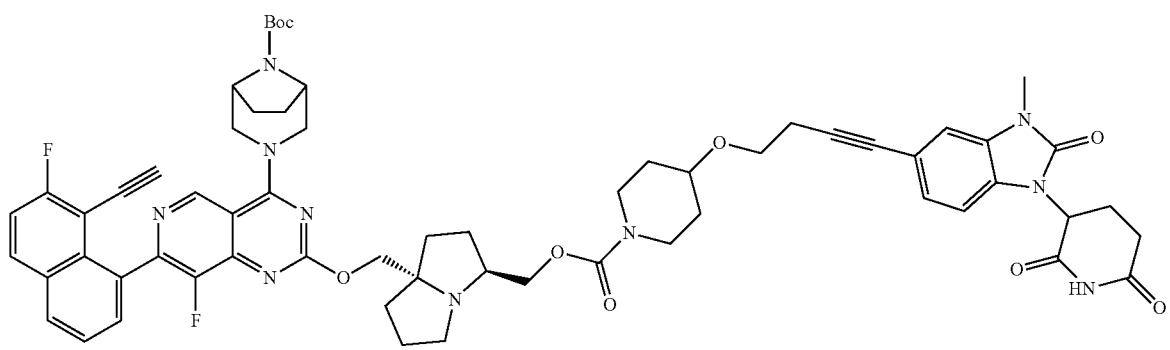

To a solution of 3-[3-methyl-2-oxo-5-[4-(4-piperidyloxy)but-1-ynyl]benzimidazol-1-yl] piperidine-2,6-dione (58.7 mg, 128 μmol, FA salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74.0 mg, 85.8 μmol) in THF (2 mL) and H$_2$O (0.4 mL) was added TEA (26.0 mg, 257 μmol). The reaction mixture was stirred at 25° C. for 1 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 40%-70% B over 10 min) to give title compound (20.0 mg, 20% yield) as yellow solid. LC-MS (ESI$^+$) m/z 1133.3 (M+H)$^+$.

(c) Step 3—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[4-[1-(2,6-dioxo-3-piperidyl)-3-methyl-2-oxo-benzimidazol-5-yl]but-3-ynoxy]piperidine-1-carboxylate (050)

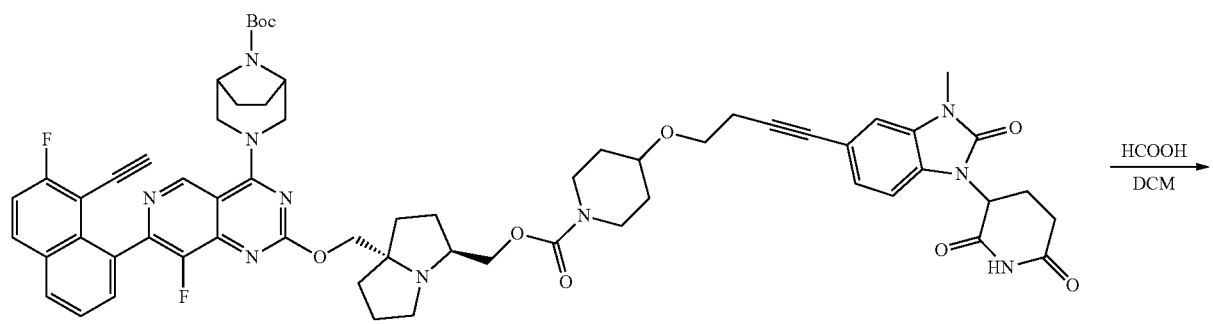

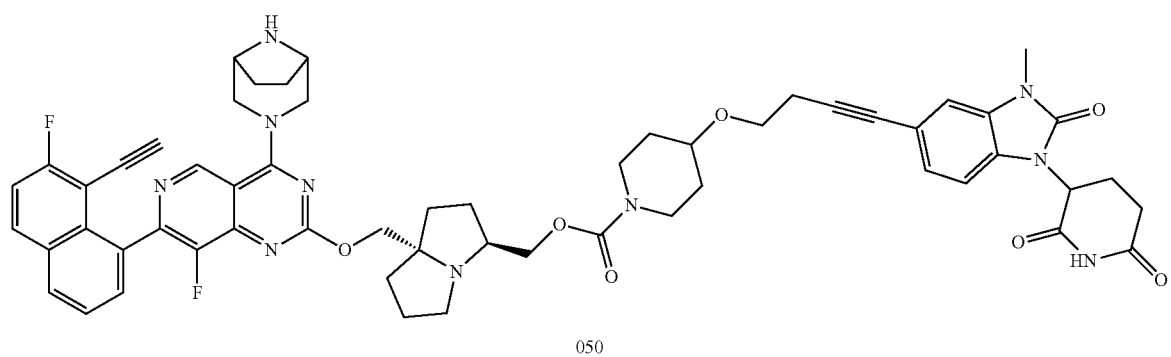

050

To a solution of tert-butyl 3-[2-[[(3S,8S)-3-[[4-[4-[1-(2,6-dioxo-3-piperidyl)-3-methyl-2-oxo-benzimidazol-5-yl]but-3-ynoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (20.0 mg, 17.6 μmol) in DCM (1 mL) was added HCOOH (847 μg, 17.6 μmol). The reaction mixture was stirred at 30° C. for 5 hrs. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 21%-41% B over 10 min) to give title compound (8.56 mg, 44% yield, FA salt) as yellow solid. $^1$H NMR (400 MHz, DMSO-$d_6$) δ 11.11 (s, 1H), 9.05 (s, 1H), 8.25-8.16 (m, 2H), 7.73-7.56 (m, 3H), 7.22 (s, 1H), 7.13-7.03 (m, 2H), 5.37 (dd, J=5.2, 12.8 Hz, 1H), 4.47 (d, J=11.6 Hz, 1H), 4.33 (d, J=11.6 Hz, 1H), 4.24-4.18 (m, 1H), 4.12 (d, J=10.4 Hz, 1H), 4.07-4.00 (m, 2H), 3.66 (d, J=8.0 Hz, 2H), 3.62 (s, 2H), 3.59 (d, J=6.8 Hz, 6H), 3.32 (s, 3H), 3.27-3.24 (m, 1H), 3.15-3.08 (m, 2H), 2.92-2.83 (m, 1H), 2.72 (dd, J=5.2, 17.2 Hz, 2H), 2.68-2.61 (m, 3H), 2.07-1.98 (m, 2H), 1.84-1.62 (m, 12H), 1.56-1.32 (m, 4H); LC-MS (ESI$^+$) m/z 1033.3 (M+H)$^+$.

Example 53. Synthesis of Compound 051

(a) Step 1—3-(3-Methyl-2-oxo-5-piperazin-1-yl-benzimidazol-1-yl)piperidine-2,6-dione

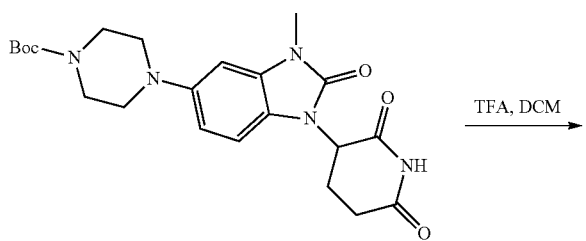

-continued

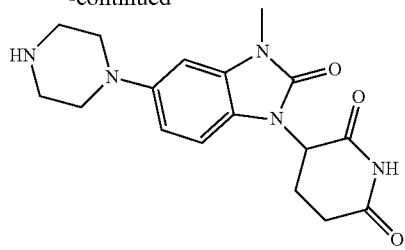

To a mixture of tert-butyl 4-[1-(2,6-dioxo-3-piperidyl)-3-methyl-2-oxo-benzimidazol-5-yl] piperazine-1-carboxylate (250 mg, 563 μmol) in DCM (2 mL) was added TFA (3.07 g, 26.9 mmol, 2.00 mL), the reaction mixture was stirred at 25° C. for 1 hr. On completion, the reaction mixture was concentrated in vacuo to give the title compound (240 mg, crude, TFA salt) as yellow solid. LC-MS (ESI+) m/z 343.9 (M+H)+.

(b) Step 2—Tert-butyl 4-[[4-[1-(2,6-dioxo-3-piperidyl)-3-methyl-2-oxo-benzimidazol-5-yl]piperazin-1-yl]methyl]piperidine-1-carboxylate

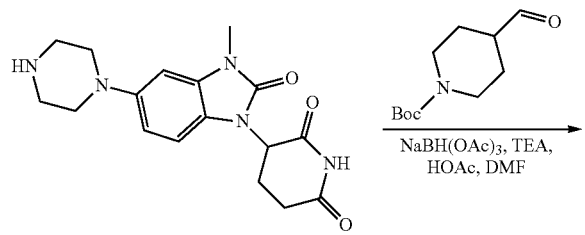

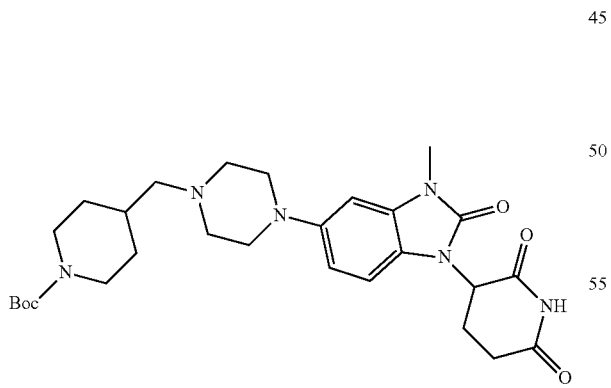

To a mixture of 3-(3-methyl-2-oxo-5-piperazin-1-yl-benzimidazol-1-yl)piperidine-2,6-dione (240 mg, 698 μmol, TFA salt) in DMF (1 mL) was added AcOH (83.9 mg, 1.40 mmol, 80.0 μL) and TEA (212 mg, 2.10 mmol, 291 μL), then tert-butyl 4-formylpiperidine-1-carboxylate (149 mg, 698 μmol, CAS #137076-22-3) was added to the reaction mixture, the reaction mixture was stirred at 25° C. for 0.5 hr, finally NaBH(OAc)$_3$ (222 mg, 1.05 mmol) was added, the reaction mixture was stirred at 25° C. for 2 hrs. On completion, the reaction mixture was quenched with water (0.05 mL) and concentrated in vacuo. The residue was purified by reverse phase to give the title compound (190 mg, 50% yield) as yellow solid. $^1$H NMR (400 MHz, DMSO-d$_6$) δ 11.07 (s, 1H), 6.96 (d, J=8.4 Hz, 1H), 6.65 (d, J=8.0 Hz, 1H), 5.30 (dd, J=5.2, 12.8 Hz, 1H), 3.93 (d, J=10.8 Hz, 2H), 3.35-3.32 (m, 3H), 3.25-2.94 (m, 6H), 2.94-2.84 (m, 2H), 2.83-2.65 (m, 5H), 2.64-2.57 (m, 2H), 2.57-2.51 (m, 2H), 2.02-1.95 (m, 1H), 1.85-1.62 (m, 4H), 1.39 (s, 9H).

(c) Step 3—3-[3-Methyl-2-oxo-5-[4-(4-piperidylmethyl) piperazin-1-yl] benzimidazol-1-yl] piperidine-2,6-dione

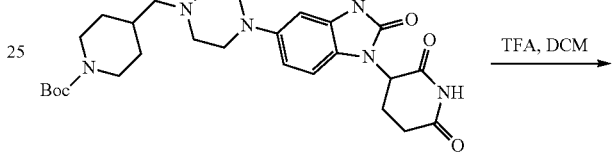

To a mixture of tert-butyl 4-[[4-[1-(2,6-dioxo-3-piperidyl)-3-methyl-2-oxo-benzimidazol-5-yl] piperazin-1-yl] methyl]piperidine-1-carboxylate (80.0 mg, 147 μmol) in DCM (1 mL) was added TFA (1.54 g, 13.4 mmol, 1.00 mL), the reaction mixture was stirred at 25° C. for 1 hr. On completion, the mixture was concentrated in vacuo to give the title compound (70.0 mg, crude, TFA salt) as yellow solid. LC-MS (ESI+) m/z 441.1 (M+H)+.

(d) Step 4—Tert-butyl 3-[2-[[(3S,8S)-3-[[4-[[4-[1-(2,6-dioxo-3-piperidyl)-3-methyl-2-oxo-benzimidazol-5-yl]piperazin-1-yl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

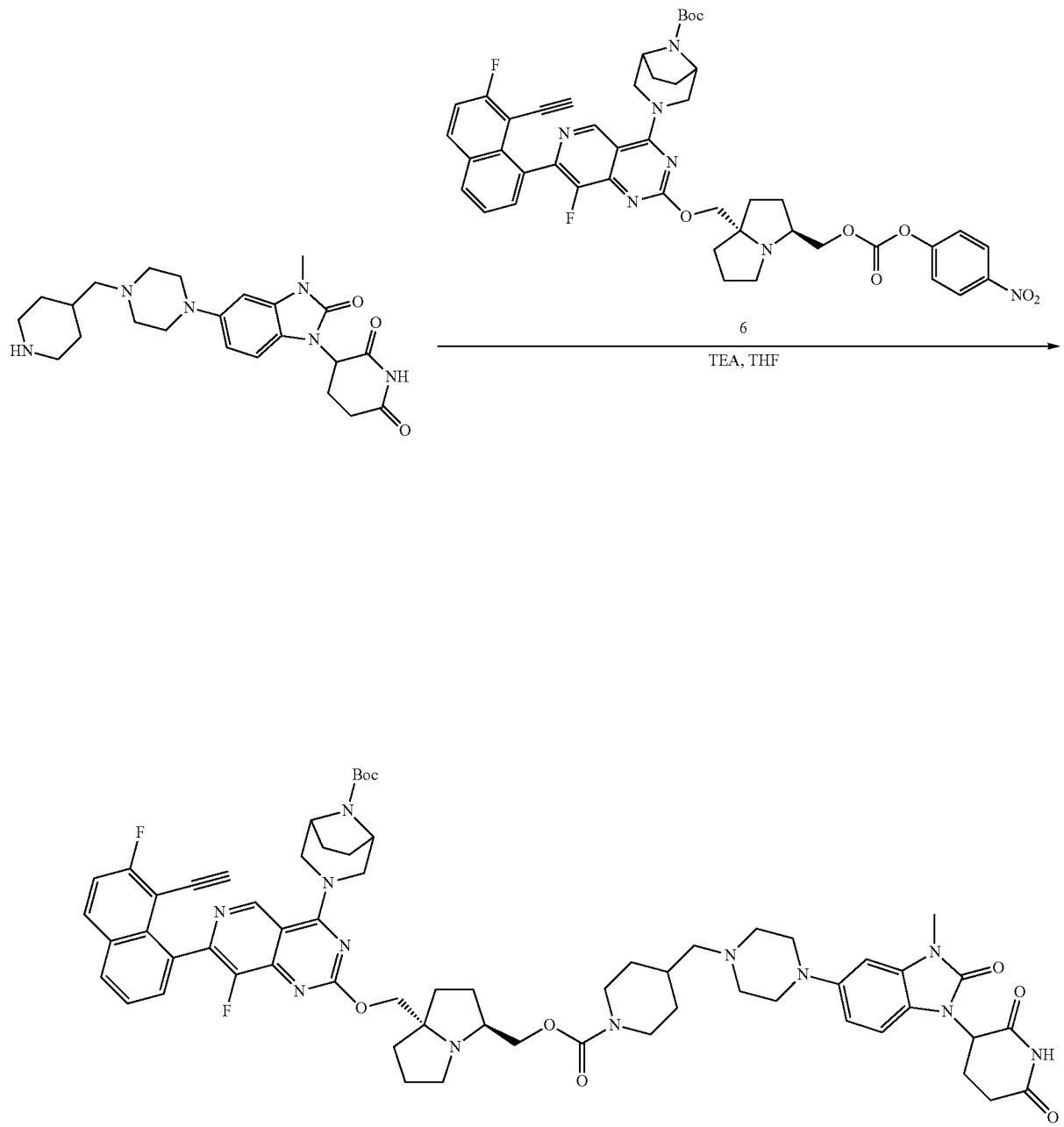

To a mixture of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (68.4 mg, 79.4 μmol, TFA salt) in THF (1 mL) was added 3-[3-methyl-2-oxo-5-[4-(4-piperidylmethyl)piperazin-1-yl]benzimidazol-1-yl]piperidine-2,6-dione (70.0 mg, 158 μmol) and TEA (48.2 mg, 476 μmol, 66.3 μL), the reaction mixture was stirred at 25° C. for 4 hrs. On completion, the residue was concentrated in vacuo to give a residue. The residue was purified by prep-HPLC (column: Phenomenex luna C18 150*25 mm*10 um; mobile phase: [water (FA)-ACN]; gradient: 18%-48% B over 11 min) to give the title compound (36.0 mg, 19% yield, HCl) as yellow solid. LC-MS (ESI$^+$) m/z 1163.3 (M+H)$^+$.

(e) Step 5—[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[1-[[1-(2,6-dioxo-3-piperidyl)-3-methyl-2-oxo-benzimidazol-4-yl]methyl]-4-piperidyl]piperidine-1-carboxylate (051)

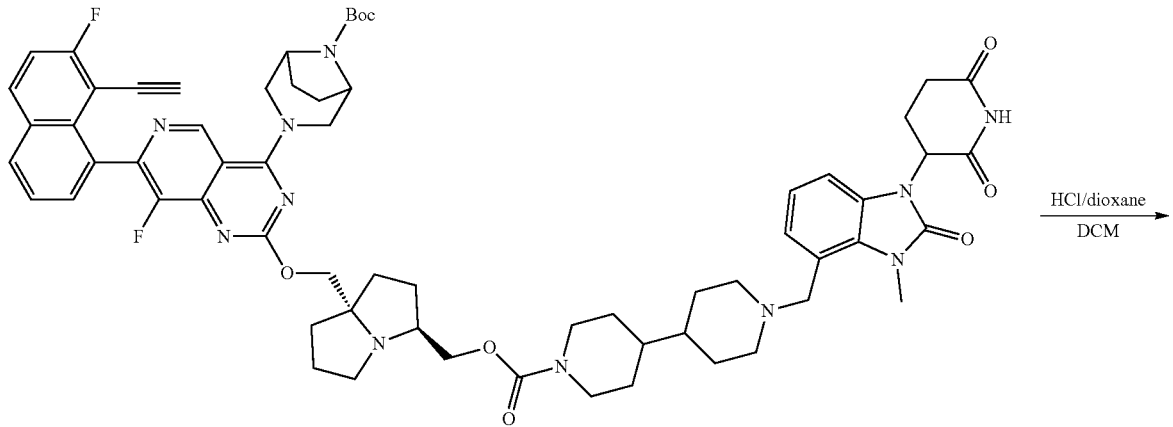

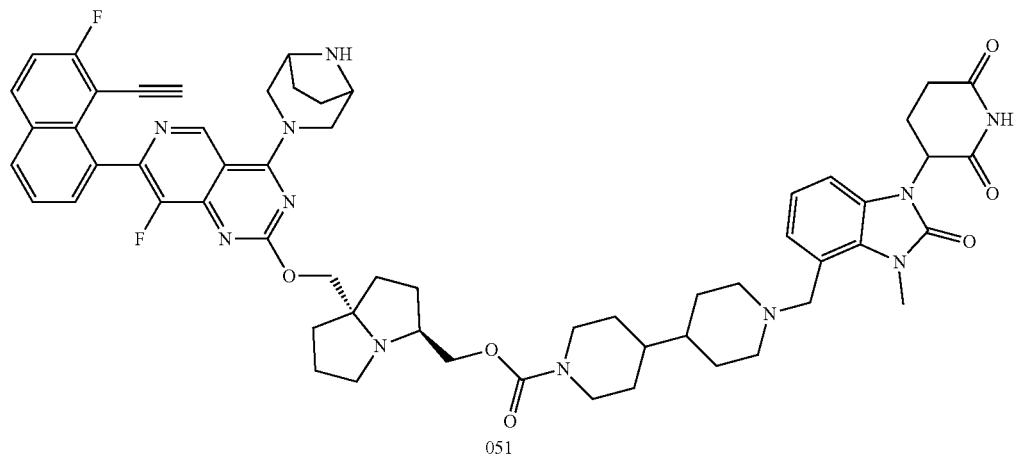

051

To a mixture of tert-butyl 3-[2-[[(3S,8S)-3-[[4-[1-(2,6-dioxo-3-piperidyl)-3-methyl-2-oxo-benzimidazol-5-yl]piperazin-1-yl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (20.0 mg, 17.1 μmol, HCl) in DCM (1 mL) was added HCl/dioxane (4 M, 1.00 mL), the reaction mixture was stirred at 25° C. for 1 hr. On completion, the residue was concentrated in vacuo to give the title compound (18.8 mg, 95% yield, HCl) as yellow solid. $^1$H NMR (400 MHz, DMSO-$d_6$) δ 11.10-11.05 (m, 1H), 11.04-10.93 (m, 1H), 10.39 (d, J=6.4 Hz, 1H), 10.02-9.83 (m, 1H), 9.66-9.51 (m, 1H), 9.17 (s, 1H), 8.28-8.19 (m, 2H), 7.75-7.68 (m, 1H), 7.68-7.58 (m, 2H), 7.04-6.96 (m, 1H), 6.91 (d, J=1.6 Hz, 1H), 6.73-6.61 (m, 1H), 5.34-5.29 (m, 1H), 4.73-4.64 (m, 2H), 4.63-4.53 (m, 1H), 4.45-4.34 (m, 1H), 4.26-4.15 (m, 3H), 4.05 (d, J=5.6 Hz, 1H), 4.03-3.93 (m, 3H), 3.57-3.53 (m, 3H), 3.45-3.38 (m, 2H), 3.32 (s, 3H), 3.29-3.20 (m, 2H), 3.20-3.09 (m, 2H), 3.08-2.97 (m, 2H), 2.96-2.77 (m, 3H), 2.75-2.55 (m, 3H), 2.34-2.27 (m, 1H), 2.17-1.92 (m, 13H), 1.90-1.81 (m, 2H), 1.29-1.11 (m, 6H); LC-MS (ESI$^+$) m/z 1063.6 (M+H)$^+$.

Example 54. Synthesis of Compound 034

(a) Step 1—[(3S,8S)-8-[[7-[8-Ethyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl (4-nitrophenyl) carbonate

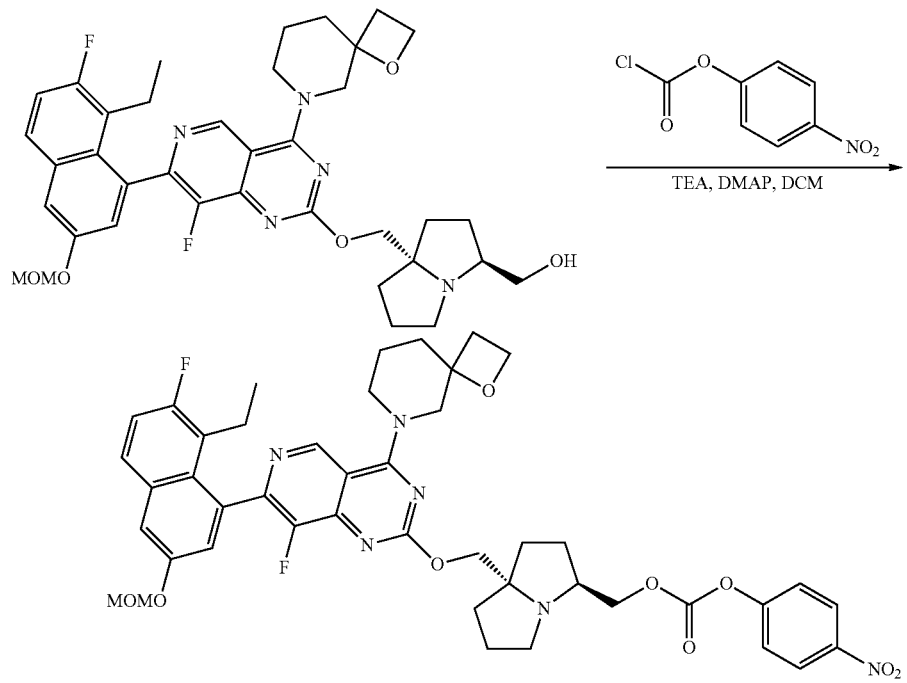

To a solution of [(3S,8S)-8-[[7-[8-ethyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methanol (60.0 mg, 88.7 μmol) in DCM (5 mL) was added TEA (26.9 mg, 266 μmol, 37.0 μL) and DMAP (1.08 mg, 8.88 μmol), (4-nitrophenyl) carbonochloridate (53.6 mg, 266 μmol, CAS #7693-46-1), The mixture was stirred at 25° C. for 3 hrs. On completion, the residue was diluted with water (30 mL) and extracted with DCM (2×30 mL). The combined organic layers was dried over Na$_2$SO$_4$, filtered and the filtrate was concentrated in vacuo to give the title compound (74.0 mg, 99% yield) as yellow solid. LC-MS (ESI$^+$) m/z 841.3 (M+H)$^+$.

(b) Step 2—[(3S,8S)-8-[[7-[8-Ethyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate

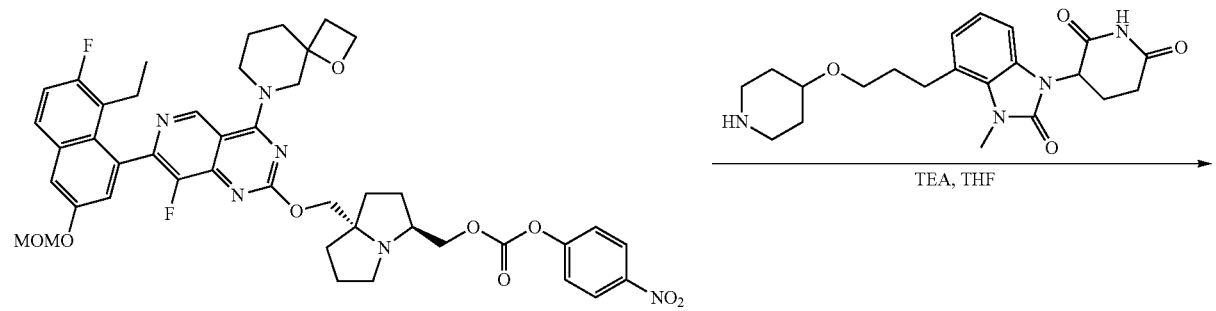

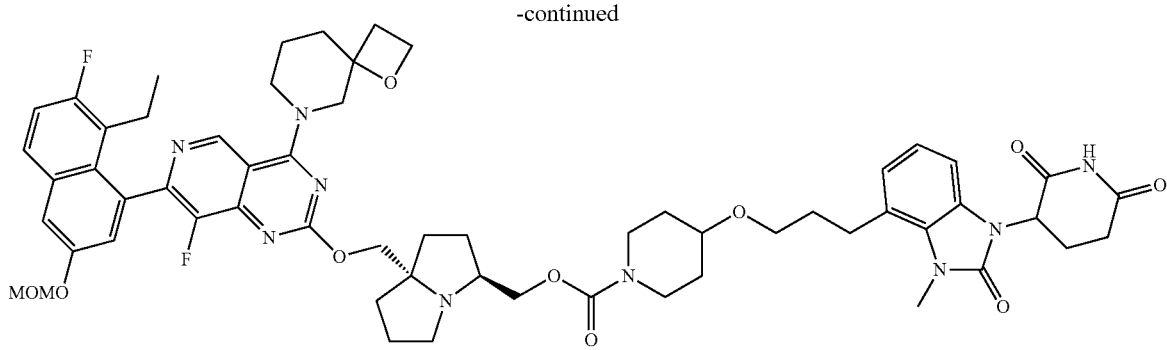

To a solution of [(3S,8S)-8-[[7-[8-ethyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl (4-nitrophenyl) carbonate (60.0 mg, 71.3 μmol) in THF (5 mL) was added TEA (21.6 mg, 214 μmol, 29.8 μL), 3-[3-methyl-2-oxo-4-[3-(4-piperidyloxy)propyl]benzimidazol-1-yl]piperidine-2,6-dione (57.1 mg, 142.7 μmol, HCl salt). The mixture was stirred at 25° C. for 0.5 hr. On completion, the reaction mixture was concentrated in vacuo. The residue was purified by prep-HPLC (column: Phenomenex luna C18 150*25 mm*10 um; mobile phase: [water (FA)-ACN]; gradient: 25%-55% B over 8 min) to give the title compound (78.0 mg, 99% yield) as white solid. LC-MS (ESI$^+$) m/z 1102.4 (M+H)$^+$.

(c) Step 3—[(3S,8S)-8-[[7-(8-Ethyl-7-fluoro-3-hydroxy-1-naphthyl)-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate (034)

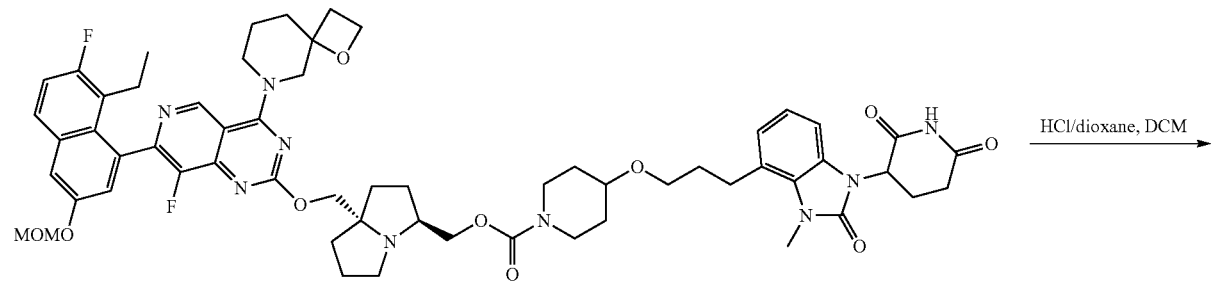

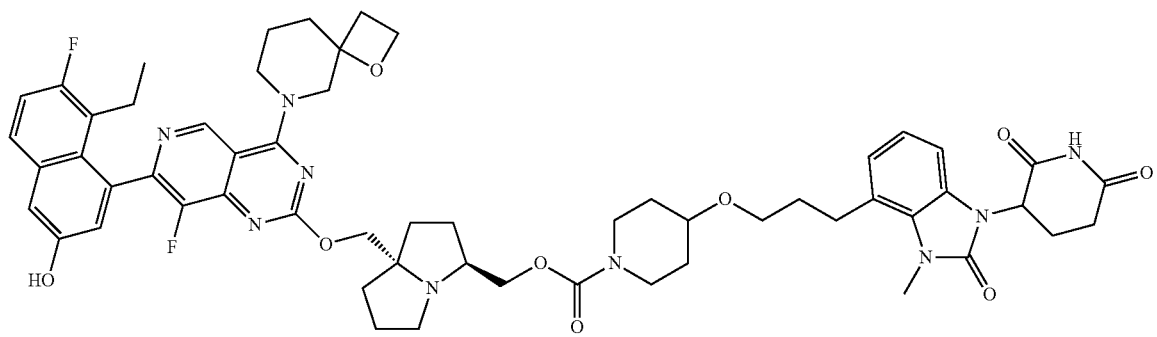

034

To a solution of [(3S,8S)-8-[[7-[8-ethyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propoxy]piperidine-1-carboxylate (25.0 mg, 22.6 µmol) in DCM (5 mL) was added TFA (3.07 g, 26.9 mmol, 2.00 mL) and the mixture was stirred at 25° C. for 0.5 hr. On completion, the reaction mixture was concentrated in vacuo. The residue was purified by prep-HPLC (column: Phenomenex luna C18 150*25 mm*10 um; mobile phase: [water (FA)-ACN]; gradient: 20%-50% B over 8 min) to give the title compound (9.81 mg, 48% yield, FA salt) as white solid. $^1$H NMR (400 MHz, DMSO-d$_6$) δ 11.10 (s, 1H), 10.09-9.86 (m, 1H), 9.22 (d, J=4.8 Hz, 1H), 7.84-7.73 (m, 1H), 7.40-7.30 (m, 2H), 7.09-7.03 (m, 1H), 7.00-6.92 (m, 2H), 6.91-6.82 (m, 1H), 5.38-5.38 (m, 1H), 4.52-4.28 (m, 3H), 4.28-4.09 (m, 5H), 3.98-3.80 (m, 1H), 3.68-3.60 (m, 2H), 3.56 (s, 3H), 3.48-3.45 (m, 4H), 3.15-3.08 (m, 2H), 2.99-2.92 (m, 2H), 2.71-2.74 (m, 1H), 2.76-2.60 (m, 4H), 2.45-2.33 (m, 3H), 2.14-1.98 (m, 4H), 1.94-1.62 (m, 14H), 1.54-1.44 (m, 1H), 1.43-1.29 (m, 2H), 0.74 (q, J=7.2 Hz, 3H) LC-MS (ESI$^+$) m/z 1058.2 (M+H)$^+$.

Example 55. Synthesis of Compound 035

(a) Step 1—8-(2,7-Dichloro-8-fluoro-pyrido[4,3-d]pyrimidin-4-yl)-1-oxa-8-azaspiro[3.5]nonane

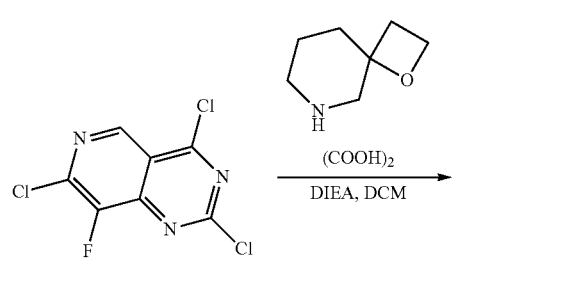

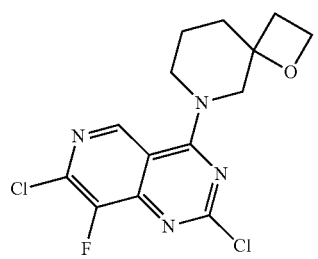

To a solution of 2,4,7-trichloro-8-fluoro-pyrido[4,3-d]pyrimidine (3.40 g, 17.4 mmol, CAS #2454396-80-4) in DCM (100 mL) was added DIEA (17.9 g, 138 mmol) at 25° C. And then 1-oxa-8-azaspiro[3.5]nonane; oxalic acid (4.80 g, 13.7 mmol, CAS #1523606-44-1) in DCM (100 mL) was added at −40° C. The mixture was stirred at −40° C. for 1 hr. On completion, the mixture was cooled to room temperature and used directly for purification. The residue was purified by column chromatography (SiO$_2$, DCM/MeOH=100/0) to give the title compound (4.30 g, 71% yield) as yellow solid. $^1$H NMR (400 MHz, CDCl$_3$) δ 9.13 (s, 1H), 4.67-4.54 (m, 2H), 4.51 (d, J=13.6 Hz, 1H), 4.44-4.34 (m, 1H), 3.70 (d, J=13.2 Hz, 1H), 3.45-3.35 (m, 1H), 2.47 (t, J=8.0 Hz, 2H), 2.39-2.28 (m, 1H), 2.14-1.97 (m, 1H), 1.95-1.76 (m, 2H); LC-MS (ESI+) m/z 342.9 (M+H)$^+$.

(b) Step 2—Tert-butyl-[[(3S,8S)-8-[[7-chloro-8-fluoro-4-(1-oxa-8-azaspiro[3.5]nonan-8-yl)pyrido[4,3-d] pyrimidin-2-yl]oxymethyl]-1,2,3,5,6,7-hexahydropyrrolizin-3-yl]methoxy]-diphenyl-silane

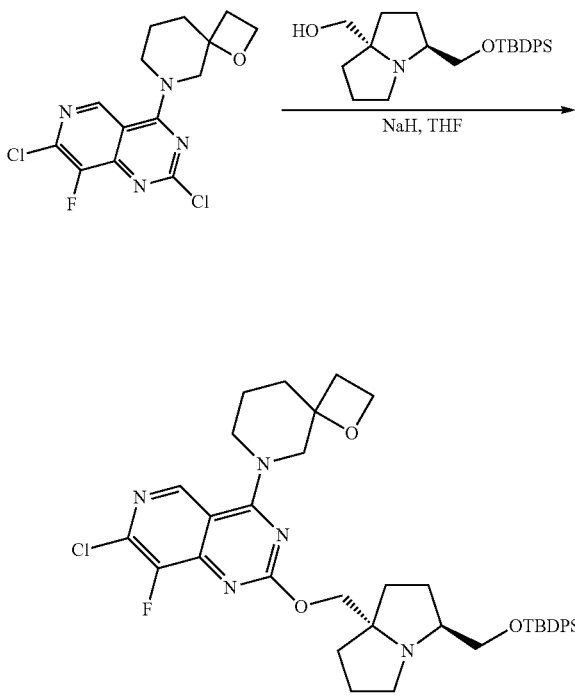

To a solution of [(3S,8S)-3-[[tert-butyl(diphenyl)silyl]oxymethyl]-1,2,3,5,6,7-hexahydropyrrolizin-8-yl]methanol (1.41 g, 3.44 mmol) in THF (50 mL) was added NaH (413 mg, 60% purity) at 0° C. The mixture was stirred at 25° C. for 0.5 hr. And then 8-(2,7-dichloro-8-fluoro-pyrido[4,3-d]pyrimidin-4-yl)-1-oxa-8-azaspiro[3.5]nonane (1.30 g, 3.79 mmol) was added at 25° C. The mixture was stirred at 25° C. for 23.5 hrs. On completion, the reaction mixture was dropwise into aq. NH$_4$Cl (50 mL) at 0° C. and dissolved with EA (100 mL). The aqueous layer was separated and extracted with EA (2×100 mL). The combined organic layer was washed with brine (100 mL), dried over anhydrous Na$_2$SO$_4$, filtered and the filtrate was concentrated in vacuo to give a residue. The residue was purified by column chromatography (SiO$_2$, DCM/EA=10/1 to 1/3) to give the title compound (2.00 g, 79% yield) as yellow solid. $^1$H NMR (400 MHz, DMSO-d$_6$) δ 9.01 (s, 1H), 7.69-7.59 (m, 4H), 7.51-7.39 (m, 6H), 4.43-4.29 (m, 3H), 4.21-4.05 (m, 3H), 3.92-3.71 (m, 3H), 3.44-3.38 (m, 1H), 3.26-3.15 (m, 1H), 2.75-2.65 (m, 2H), 2.41 (td, J=7.6, 11.2 Hz, 1H), 2.36-2.28 (m, 1H), 2.13-2.00 (m, 2H), 1.88-1.47 (m, 10H), 0.99 (s, 9H); LC-MS (ESI+) m/z 716.2 (M+H)$^+$.

(c) Step 3—Tert-butyl-[[(3S,8S)-8-[[8-fluoro-7-[7-fluoro-3-(methoxymethoxy)-8-(2-triisopropylsilyl-ethynyl)-1-naphthyl]-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methoxy]-diphenyl-silane

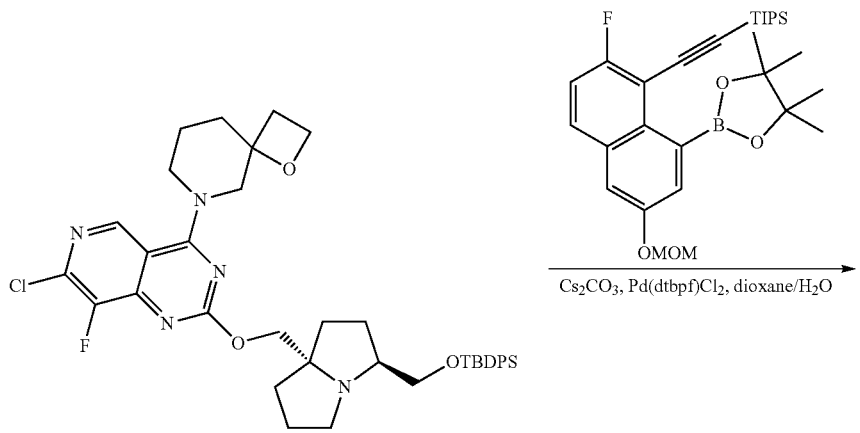

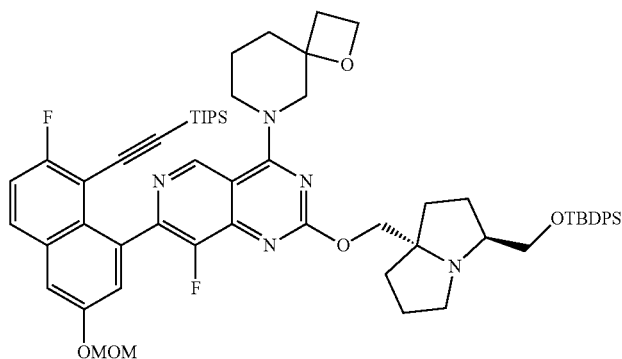

A mixture of tert-butyl-[[(3S,8S)-8-[[7-chloro-8-fluoro-4-(1-oxa-8-azaspiro[3.5]nonan-8-yl) pyrido[4,3-d]pyrimidin-2-yl]oxymethyl]-1,2,3,5,6,7-hexahydropyrrolizin-3-yl] methoxy]-diphenyl-silane (900 mg, 1.26 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (965 mg, 1.88 mmol, CAS #2621932-37-2), ditert-butyl (cyclopentyl)phosphane; dichloropalladium; iron (163 mg, 251 μmol), and Cs$_2$CO$_3$ (1.23 g, 3.77 mmol) in dioxane (18 mL) and H$_2$O (3.6 mL) was degassed and purged with N$_2$ for 3 times, and then the mixture was stirred at 100° C. for 2 hrs under N$_2$ atmosphere. On completion, the reaction mixture was dissolved in EA (100 mL) and H$_2$O (100 mL), separated, extracted with EA (100 mL×2). The combined organic layer was washed with brine (100 mL×2), dried over anhydrous Na$_2$SO$_4$, filtered and the filtrate was concentrated in vacuo to give a residue The residue was purified by column chromatography (SiO$_2$, DCM/MeOH=100/1 to 10/1) to give the title compound (1.25 g, 1.04 mmol, 83% yield) as brown solid. $^1$H NMR (400 MHz, CDCl$_3$) δ 9.37-9.16 (m, 1H), 7.78 (dd, J=5.6, 9.2 Hz, 1H), 7.73-7.59 (m, 4H), 7.51 (d, J=2.4 Hz, 1H), 7.41 (s, 6H), 7.36-7.29 (m, 2H), 5.34-5.27 (m, 2H), 4.77-4.61 (m, 1H), 4.59-4.43 (m, 2H), 4.39-4.16 (m, 3H), 4.01-3.79 (m, 3H), 3.69-3.58 (m, 1H), 3.51 (s, 3H), 3.48-3.21 (m, 2H), 2.86-2.79 (m, 1H), 2.58-2.41 (m, 2H), 2.35-2.14 (m, 3H), 2.01-1.70 (m, 12H), 1.27-1.24 (m, 18H), 1.11-1.04 (m, 9H); LC-MS (ESI+) m/z 1066.3 (M+H)$^+$.

(d) Step 4—[(3S,8S)-8-[[7-[8-Ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl] methanol

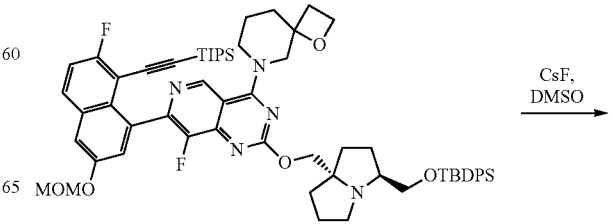

-continued

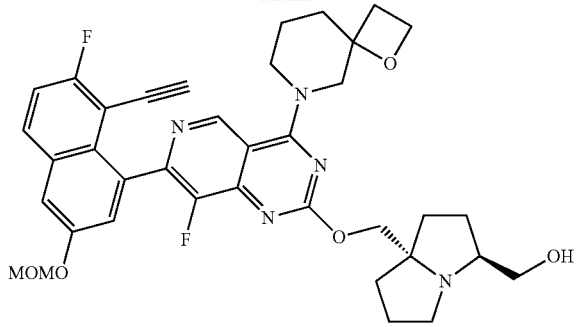

To a solution of tert-butyl-[[(3S,8S)-8-[[8-fluoro-7-[7-fluoro-3-(methoxymethoxy)-8-(2-triisopropylsilylethynyl)-1-naphthyl]-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methoxy]-diphenyl-silane (1.25 g, 1.17 mmol) in DMSO (13 mL) was added CsF (534 mg, 3.52 mmol). The mixture was stirred at 30° C. for 12 hrs. On completion, the reaction mixture was diluted with H$_2$O (20 mL) and extracted with EA (100 mL×3). The combined organic layers were washed with brine (200 mL×2), dried over anhydrous Na$_2$SO$_4$, filtered and the filtrate was concentrated in vacuo to give a residue. The residue was purified by column chromatography (SiO$_2$, DCM/MeOH=100/1 to 10/1) to give the title compound (380 mg, 47% yield) as brown solid. $^1$H NMR (400 MHz, CDCl$_3$) δ 9.31-9.14 (m, 1H), 7.87-7.78 (m, 1H), 7.55 (d, J=1.6 Hz, 1H), 7.44-7.37 (m, 1H), 7.33-7.27 (m, 1H), 5.36-5.30 (m, 2H), 4.84-4.76 (m, 1H), 4.72-4.63 (m, 2H), 4.60-4.51 (m, 2H), 4.48-4.35 (m, 1H), 4.34-4.18 (m, 1H), 4.02 (t, J=12.4 Hz, 1H), 3.88 (d, J=11.2 Hz, 1H), 3.83-3.70 (m, 2H), 3.53 (d, J=3.2 Hz, 3H), 3.49-3.40 (m, 1H), 3.25-3.14 (m, 1H), 2.56-2.50 (m, 1H), 2.49-2.20 (m, 6H), 2.20-2.10 (m, 2H), 2.03 (s, 2H), 1.86 (t, J=11.2 Hz, 4H); LC-MS (ESI$^+$) m/z 672.1 (M+H)$^+$.

(e) Step 5—[(3S,8S)-8-[[7-[8-Ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl (4-nitrophenyl) carbonate

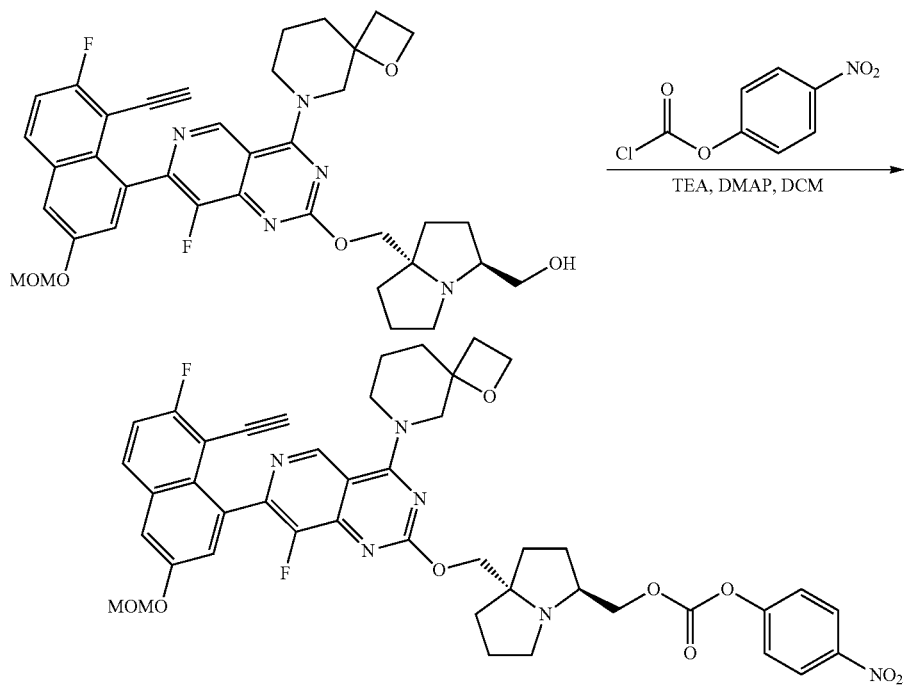

To a solution of [(3S,8S)-8-[[7-[8-ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methanol (60.0 mg, 89.3 μmol), TEA (27.0 mg, 267 μmol) and DMAP (1.09 mg, 8.93 μmol) in DCM (6 mL) was added (4-nitrophenyl) carbonochloridate (54.0 mg, 267 μmol, CAS #7693-46-1). The mixture was stirred at 25° C. for 16 hrs. On completion, the mixture was diluted with DCM (30 mL), and extracted with H$_2$O (3×50 mL). The organic layer was washed with brine (2×50 mL), dried over anhydrous Na$_2$SO$_4$, filtered and the filtrate was concentrated in vacuo to give the title compound (74.0 mg, 59% yield) as brown solid. LC-MS (ESI$^+$) m/z 837.1 (M+H)$^+$.

(f) Step 6—[(3S,8S)-8-[[7-[8-Ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate

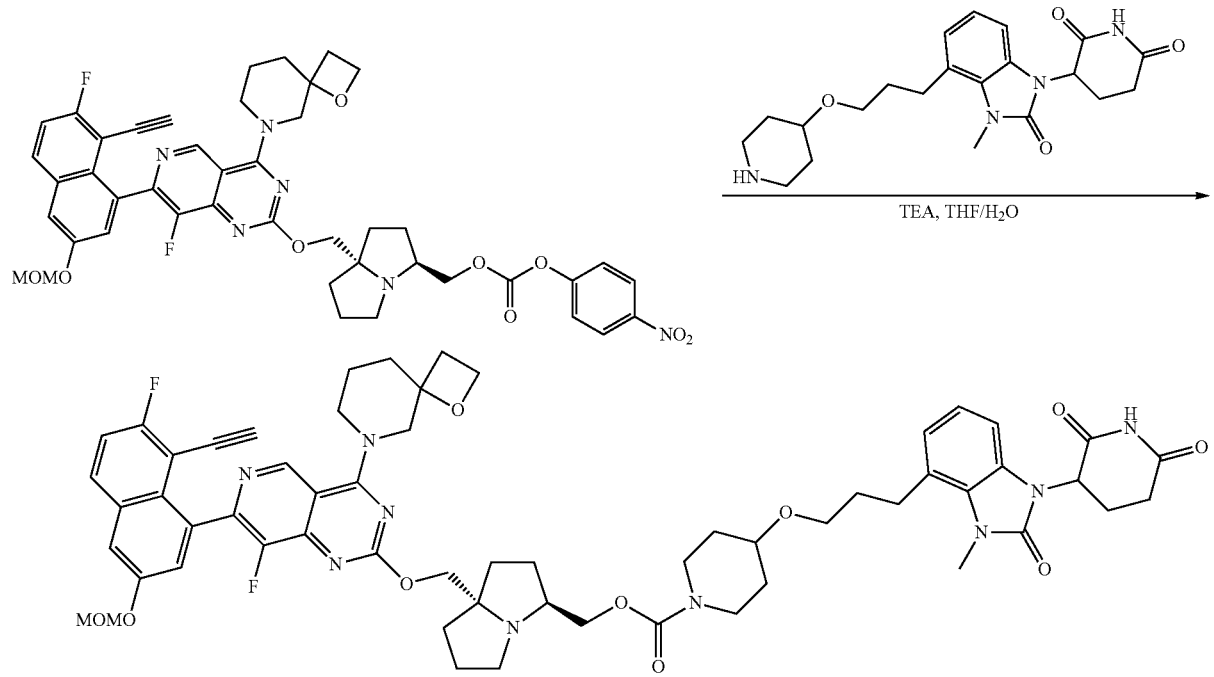

To a solution of [(3S,8S)-8-[[7-[8-ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl (4-nitrophenyl) carbonate (50.0 mg, 59.7 µmol) and 3-[3-methyl-2-oxo-4-[3-(4-piperidyloxy)propyl]benzimidazol-1-yl]piperidine-2,6-dione (52.2 mg, 119 µmol, HCl salt) in THF (5 mL) was added TEA (18.1 mg, 179 µmol) and H$_2$O (0.5 mL). The mixture was stirred at 25° C. for 0.5 hr. On completion, the reaction mixture was concentrated in vacuo to give a residue. The residue was purified by prep-HPLC (column: Phenomenex luna C18 150*25 mm*10 µm; mobile phase: [water (FA)-ACN]; gradient: 22%-52% B over 10 min) to give the title compound (30.0 mg, 38% yield) as yellow solid. LC-MS (ESI$^+$) m/z 1098.2 (M+H)$^+$.

(g) Step 7—[(3S,8S)-8-[[7-(8-Ethynyl-7-fluoro-3-hydroxy-1-naphthyl)-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propoxy]piperidine-1-carboxylate (035)

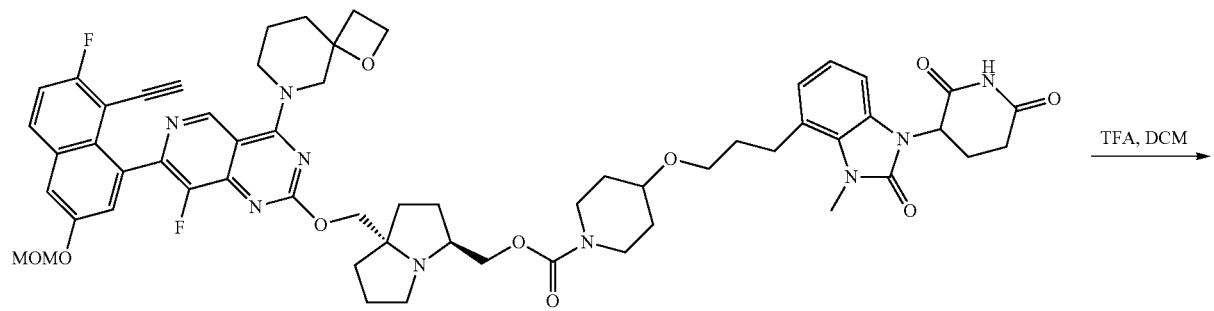

-continued

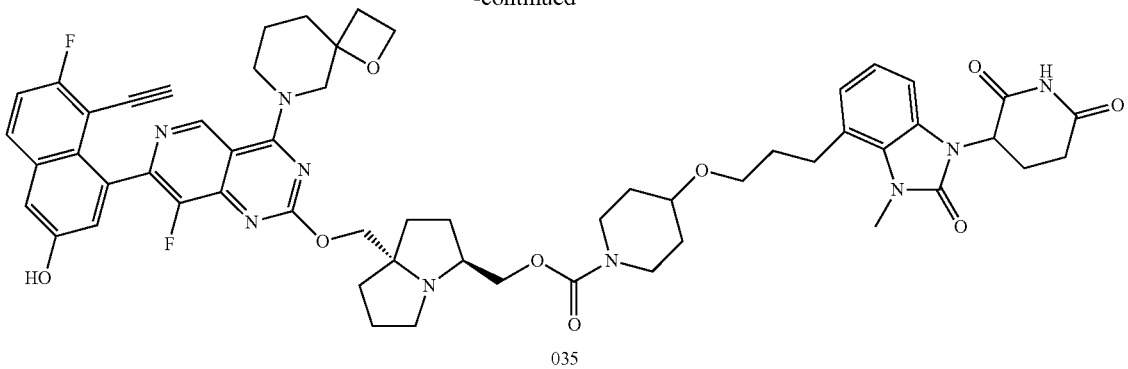

035

To a solution of [(3S,8S)-8-[[7-[8-ethynyl-7-fluoro-3-(methoxymethoxy)-1-naphthyl]-8-fluoro-4-(1-oxa-8-azaspiro[3.5]nonan-8-yl)pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy] piperidine-1-carboxylate (30.0 mg, 27.3 μmol) in DCM (2 mL) was added TFA (13.4 mmol, 1 mL). The mixture was stirred at 25° C. for 2 hrs. On completion, the reaction mixture was adjusted with TEA to pH=7-8 and then concentrated in vacuo to give a residue. The residue was purified by prep-HPLC (column: Waters xbridge 150*25 mm 10 μm; mobile phase: [water (NH$_4$HCO$_3$)-ACN]; gradient: 34%-64% B over 15 min) to give the title compound (9.74 mg, 32% yield) as yellow solid. $^1$H NMR (400 MHz, DMSO-d$_6$) δ 11.08 (s, 1H), 10.15 (s, 1H), 9.23-9.01 (m, 1H), 8.06-7.90 (m, 1H), 7.46 (t, J=9.2 Hz, 1H), 7.39 (d, J=3.2 Hz, 1H), 7.21 (dd, J=2.4, 4.4 Hz, 1H), 6.95 (d, J=5.6 Hz, 2H), 6.86 (dd, J=3.6, 5.2 Hz, 1H), 5.42-5.31 (m, 1H), 4.45-4.36 (m, 2H), 4.26-4.04 (m, 5H), 4.02-3.73 (m, 2H), 3.69-3.60 (m, 2H), 3.55 (s, 3H), 3.47 (t, J=6.0 Hz, 4H), 3.15-3.07 (m, 2H), 2.98-2.92 (m, 2H), 2.91-2.84 (m, 1H), 2.80-2.54 (m, 6H), 2.46-2.35 (m, 2H), 2.17-1.93 (m, 4H), 1.88-1.66 (m, 12H), 1.56-1.47 (m, 1H), 1.42-1.32 (m, 2H); LC-MS (ESI$^+$) m/z 1054.1 (M+H)$^+$.

Example 56. Synthesis of Compound 052

(a) Step 1—1-(2,6-Dioxo-3-piperidyl)-3-methyl-2-oxo-benzimidazole-5-carbaldehyde To a solution of 3-[5-(hydroxymethyl)-3-methyl-2-oxo-benzimidazol-1-yl]piperidine-2,6-dione (775 mg, 2.68 mmol) in DCM (10 mL) was added DMP (1.70 g, 4.02 mmol) at 0° C. The mixture was stirred at 25° C. for 0.5 hr. On completion, the reaction mixture was quenched with Na$_2$S$_2$O$_3$ (15 mL). The mixture was diluted with H$_2$O (10 mL), extracted with DCM (3×35 mL), and the organic layer was washed with NaHCO$_3$ (2×35 mL) and brine (2×35 mL), dried with anhydrous Na$_2$SO$_4$, filtered and the filtrate was concentrated in vacuo to give a residue. The residue was purified by column chromatography (SiO$_2$, PE/EA=100/1 to 0/1) to give the title compound (335 mg, 37% yield) as red solid. $^1$H NMR (400 MHz, CDCl$_3$) δ 9.95 (s, 1H), 8.68 (s, 1H), 7.63-7.56 (m, 2H), 6.96 (d, J=8.0 Hz, 1H), 5.27 (dd, J=5.2, 12.8 Hz, 1H), 3.49 (s, 3H), 2.93 (s, 1H), 2.87 (dd, J=4.8, 13.2 Hz, 1H), 2.79-2.72 (m, 1H), 2.29-2.23 (m, 1H); LC-MS (ESI$^+$) m/z 288.0 (M+H)$^+$.

(b) Step 2—Tert-butyl 4-[[1-[[1-(2,6-dioxo-3-piperidyl)-3-methyl-2-oxo-benzimidazol-5-yl]methyl]-4-piperidyl]oxy]piperidine-1-carboxylate (c) Step 3—3-[3-Methyl-2-oxo-5-[[4-(4-piperidyloxy)-1-piperidyl]methyl]benzimidazol-1-yl]piperidine-2,6-dione

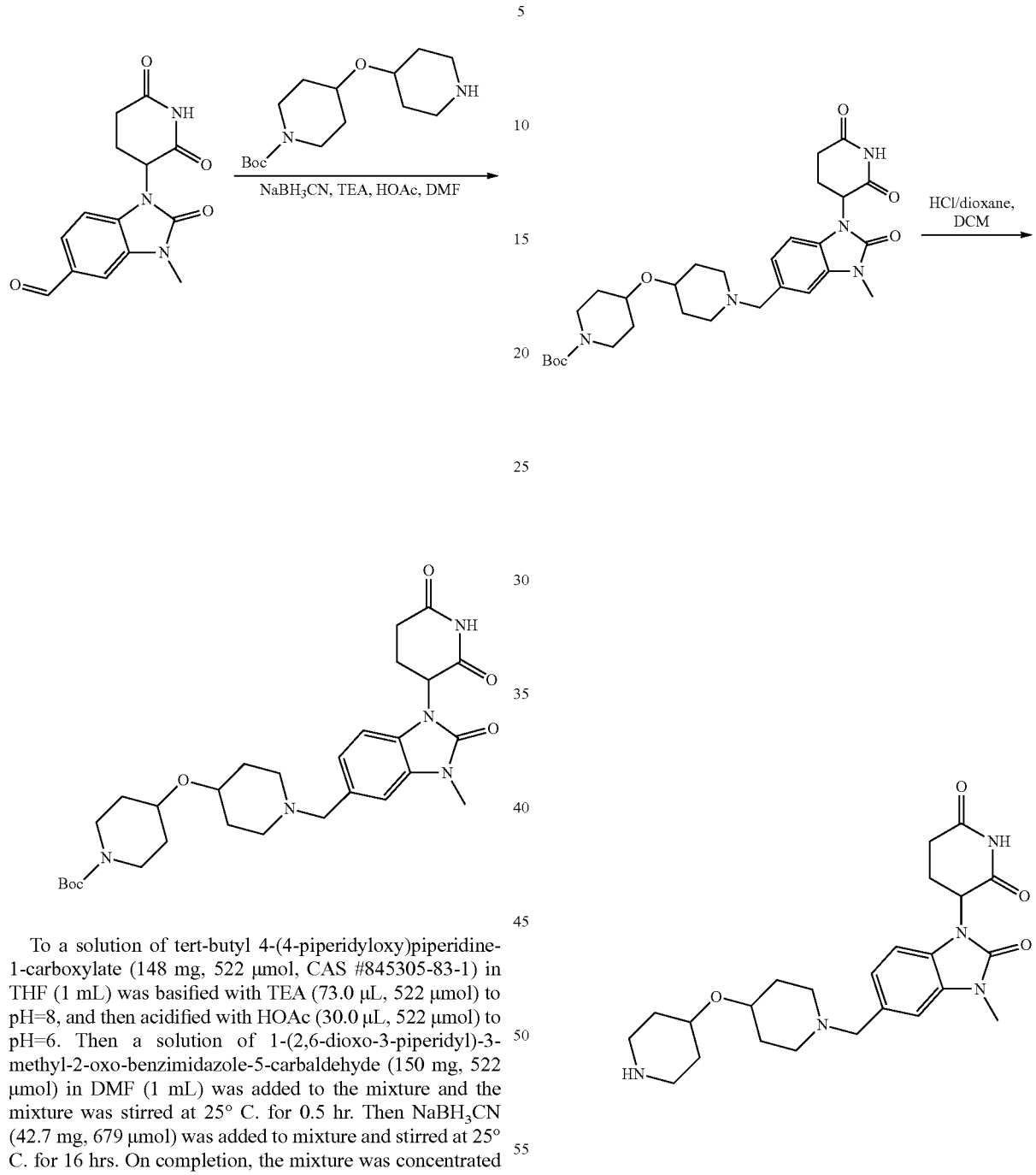

To a solution of tert-butyl 4-(4-piperidyloxy)piperidine-1-carboxylate (148 mg, 522 μmol, CAS #845305-83-1) in THF (1 mL) was basified with TEA (73.0 μL, 522 μmol) to pH=8, and then acidified with HOAc (30.0 μL, 522 μmol) to pH=6. Then a solution of 1-(2,6-dioxo-3-piperidyl)-3-methyl-2-oxo-benzimidazole-5-carbaldehyde (150 mg, 522 μmol) in DMF (1 mL) was added to the mixture and the mixture was stirred at 25° C. for 0.5 hr. Then NaBH₃CN (42.7 mg, 679 μmol) was added to mixture and stirred at 25° C. for 16 hrs. On completion, the mixture was concentrated in vacuo to give a residue. The residue was purified by reversed phase (0.1% FA condition) to give the title compound (130 mg, 42% yield) as white solid. ¹H NMR (400 MHz, DMSO-d₆) δ 11.10 (s, 1H), 7.15 (s, 1H), 7.09 (d, J=8.0 Hz, 1H), 7.02 (d, J=8.0 Hz, 1H), 5.37 (dd, J=5.2, 12.4 Hz, 1H), 3.74-3.67 (m, 1H), 3.65-3.59 (m, 2H), 3.56 (dd, J=4.0, 8.0 Hz, 1H), 3.51 (d, J=2.8 Hz, 1H), 3.34 (s, 3H), 3.03-2.93 (m, 2H), 2.92-2.80 (m, 4H), 2.74-2.59 (m, 3H), 2.35-2.29 (m, 1H), 2.03-1.97 (m, 1H), 1.80 (s, 2H), 1.76-1.70 (m, 2H), 1.57-1.44 (m, 2H), 1.38 (s, 9H), 1.33-1.23 (m, 2H); LC-MS (ESI⁺) m/z 556.2 (M+H)⁺.

To a solution of tert-butyl 4-[[1-[[1-(2,6-dioxo-3-piperidyl)-3-methyl-2-oxo-benzimidazol-5-yl]methyl]-4-piperidyl]oxy]piperidine-1-carboxylate (80.0 mg, 144 μmol) in DCM (1 mL) was added HCl/dioxane (4 M, 1 mL). The mixture was stirred at 25° C. for 1 hr. On completion, the mixture was concentrated in vacuo to give the title compound (70.0 mg, 96% yield, HCl salt) as white solid. LC-MS (ESI⁺) m/z 456.2 (M+H)⁺.

(d) Step 4—Tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]oxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

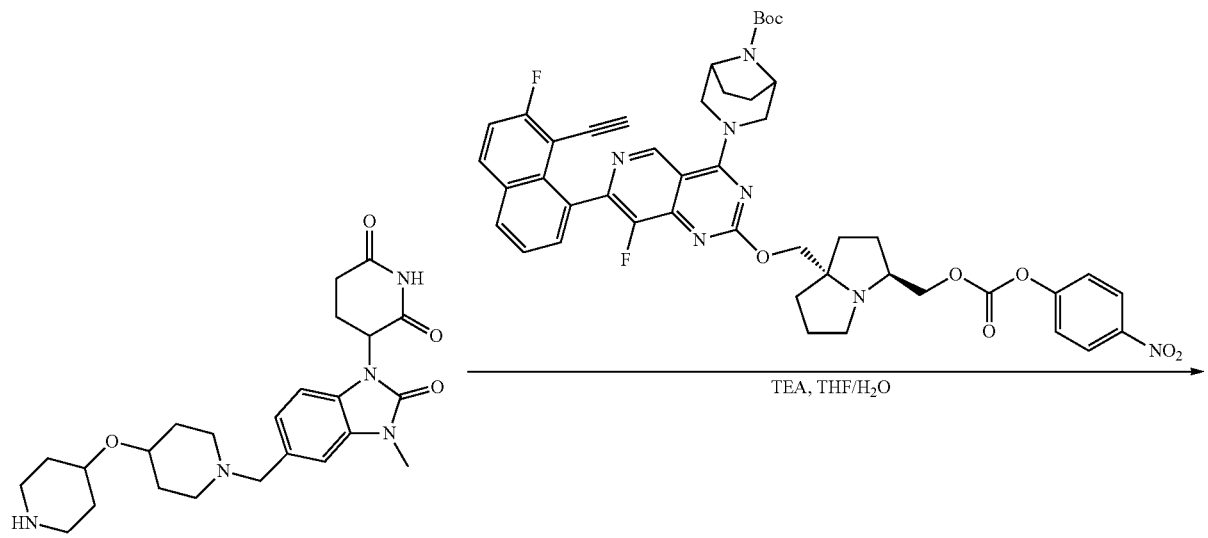

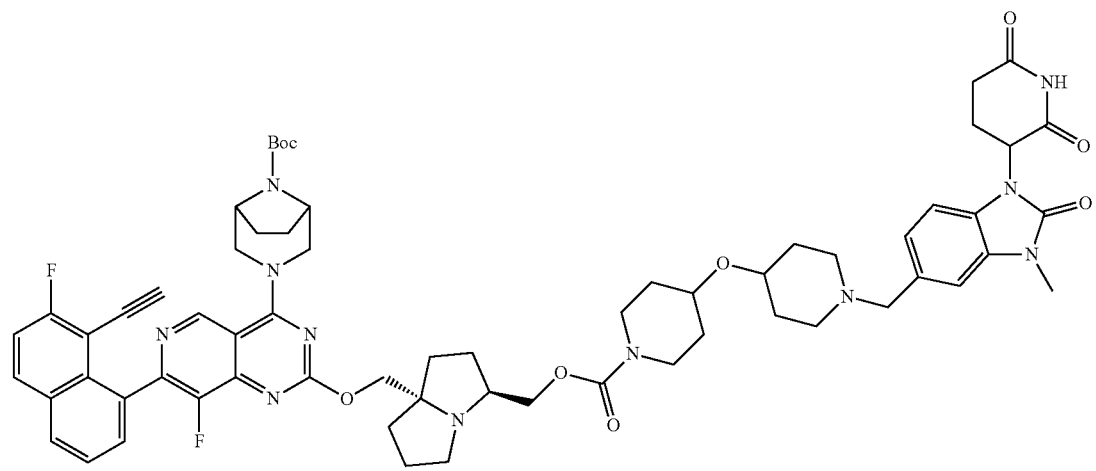

A solution of 3-[3-methyl-2-oxo-5-[[4-(4-piperidyloxy)-1-piperidyl]methyl]benzimidazol-1-yl]piperidine-2,6-dione (70.0 mg, 142 μmol, HCl salt) in THF (1 mL) and H₂O (0.3 mL) was basified with TEA (70.0 μL, 498 μmol) to pH=8. Then a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (61.3 mg, 71.1 μmol) in THF (1 mL) was added to the mixture, and then the mixture was stirred at 25° C. for 0.5 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 19%-49% B over 15 min) to give the title compound (25.0 mg, 27% yield) as yellow solid. LC-MS (ESI⁺) m/z 1178.5 (M+H)⁺.

(e) Step 5—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[[1-[[1-
(2,6-dioxo-3-piperidyl)-3-methyl-2-oxo-
benzimidazol-5-yl]methyl]-4-piperidyl]oxy]
piperidine-1-carboxylate (052)

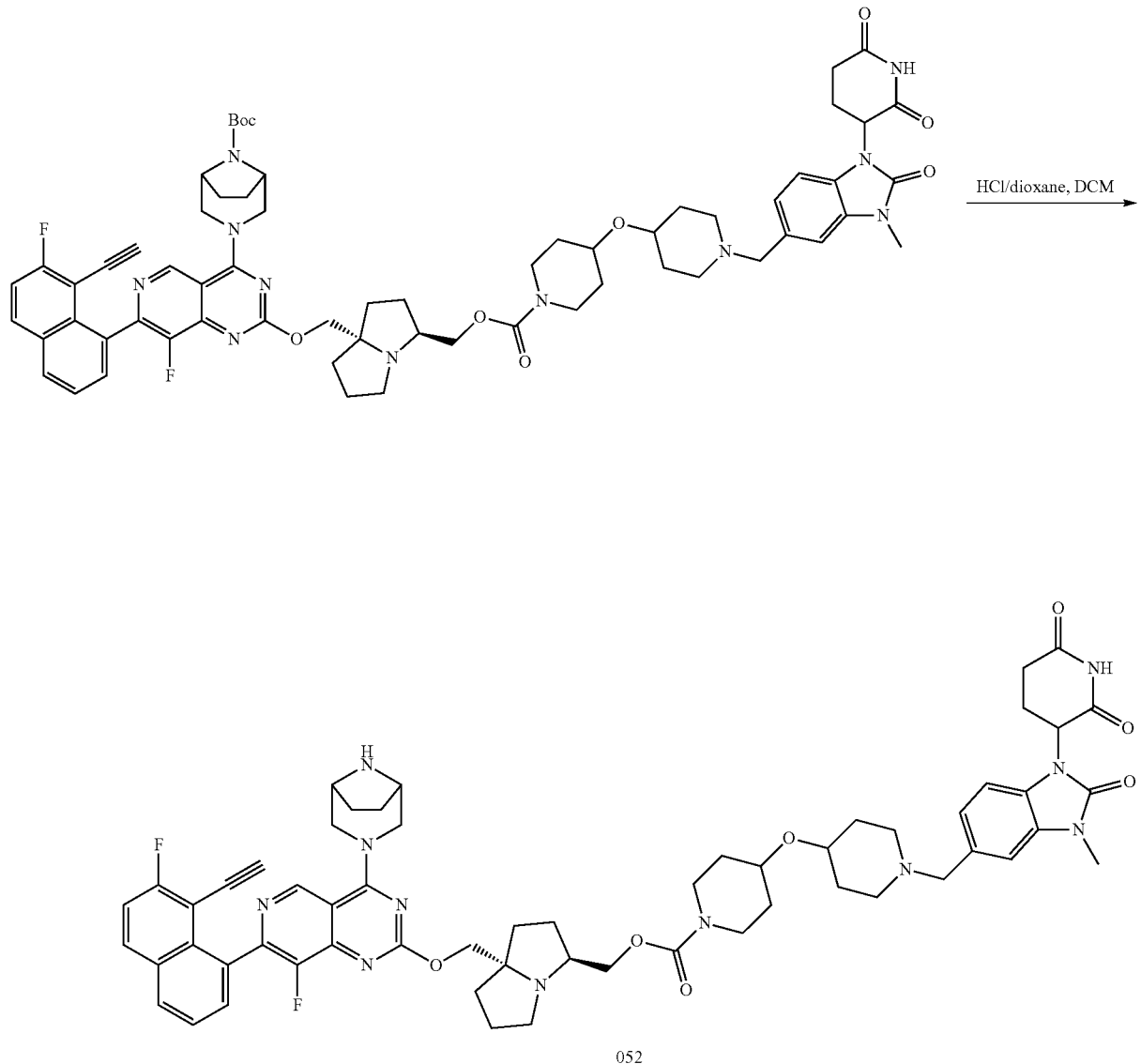

052

To a solution of tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]oxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (25.0 mg, 21.2 μmol) in DCM (1 mL) was added HCl/dioxane (4 M, 1 mL). The mixture was stirred at 25° C. for 1 hr. On completion, the mixture was concentrated in vacuo to give a residue. The residue was purified by prep-HPLC (column: Welch Xtimate C18 150*25 mm*5 μm; mobile phase: [water (FA)-ACN]; gradient: 9%-29% B over 10 min) to give the title compound (18.3 mg, 76% yield) as yellow solid. $^1$H NMR (400 MHz, DMSO-$d_6$) δ 11.10 (s, 1H), 9.07 (s, 1H), 8.25-8.23 (m, 1H), 8.21-8.18 (m, 1H), 7.73-7.56 (m, 3H), 7.10 (s, 1H), 7.04 (d, J=8.0 Hz, 1H), 6.99-6.93 (m, 1H), 5.35 (dd, J=5.2, 12.8 Hz, 1H), 4.53 (d, J=12.4 Hz, 2H), 4.39 (d, J=12.4 Hz, 2H), 4.24-4.19 (m, 2H), 4.17 (s, 1H), 4.10 (d, J=10.8 Hz, 1H), 4.03 (s, 1H), 3.80 (s, 2H), 3.72 (d, J=12.4 Hz, 1H), 3.69-3.62 (m, 2H), 3.58-3.55 (m, 1H), 3.48 (s, 2H), 3.42 (s, 1H), 3.32 (s, 3H), 3.07 (s, 2H), 2.95-2.88 (m, 1H), 2.88-2.73 (m, 3H), 2.73-2.63 (m, 3H), 2.60 (s, 1H), 2.15-1.97 (m, 4H), 1.77 (s, 14H), 1.58-1.49 (m, 1H), 1.47-1.36 (m, 2H), 1.35-1.22 (m, 2H); LC-MS (ESI$^+$) m/z 1078.3 (M+H)$^+$.

Example 57. Synthesis of Compound 053

(a) Step 1—Tert-butyl 4-[4-[[1-(2,6-dioxo-3-piperidyl)-3-methyl-2-oxo-benzimidazol-4-yl]methyl]piperazin-1-yl]piperidine-1-carboxylate

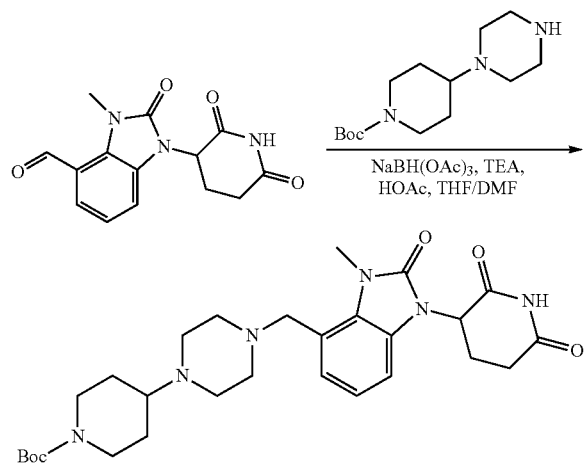

To a mixture of tert-butyl 4-piperazin-1-ylpiperidine-1-carboxylate (312 mg, 1.16 mmol) in DMF (5 mL) was added TEA (351 mg, 3.47 mmol, 483 µL) and HOAc (139 mg, 2.32 mmol, 132 µL), then 1-(2,6-dioxo-3-piperidyl)-3-methyl-2-oxo-benzimidazole-4-carbaldehyde (499 mg, 1.74 mmol, CAS #177276-41-4) was added to the reaction mixture, the reaction mixture was stirred at 25° C. for 0.5 hr, finally NaBH(OAc)$_3$ (368 mg, 1.74 mmol) was added, the reaction mixture was stirred at 25° C. for 12 hrs. On completion, the reaction mixture was filtered and the filtrate was concentrated in vacuo to give a residue. The residue was purified by reverse phase to give the title compound (60 mg, 9% yield) as yellow solid. $^1$H NMR (400 MHz, DMSO-d$_6$) δ 11.15-11.05 (m, 1H), 7.07 (d, J=8.0 Hz, 1H), 6.95 (t, J=7.6 Hz, 1H), 6.87 (d, J=7.2 Hz, 1H), 5.41-5.33 (m, 1H), 4.00-3.90 (m, 4H), 3.66 (s, 3H), 3.62 (s, 2H), 2.91 (d, J=4.8 Hz, 2H), 2.74-2.63 (m, 6H), 2.32-2.26 (m, 3H), 2.05-1.97 (m, 2H), 1.69 (d, J=11.6 Hz, 4H), 1.38 (s, 9H).

(b) Step 2—3-[3-Methyl-2-oxo-4-[[4-(4-piperidyl)piperazin-1-yl] methyl]benzimidazol-1-yl]piperidine-2,6-dione

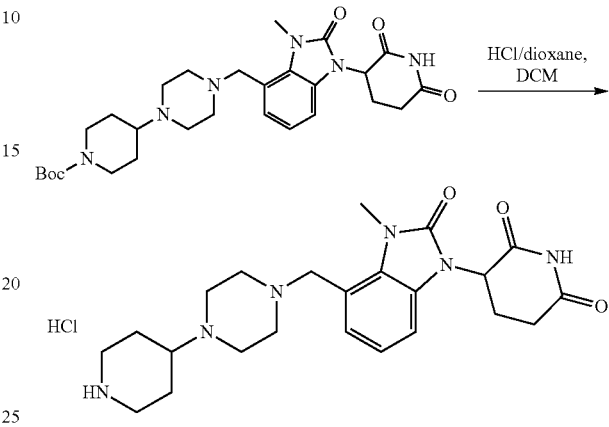

To a mixture of tert-butyl 4-[4-[[1-(2,6-dioxo-3-piperidyl)-3-methyl-2-oxo-benzimidazol-4-yl] methyl]piperazin-1-yl]piperidine-1-carboxylate (50.0 mg, 92.4 µmol) in DCM (1 mL) was added HCl/dioxane (4 M, 1 mL), the reaction mixture was stirred at 25° C. for 1 hr. On completion, the reaction mixture was concentrated in vacuo to give the title compound (40 mg, 98% yield, HCl salt) as yellow solid. LC-MS (ESI$^+$) m/z 441.1 (M+H)$^+$.

(c) Step 3—Tert-butyl 3-[2-[[(3S,8S)-3-[[4-[4-[[1-(2,6-dioxo-3-piperidyl)-3-methyl-2-oxo-benzimidazol-4-yl]methyl]piperazin-1-yl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

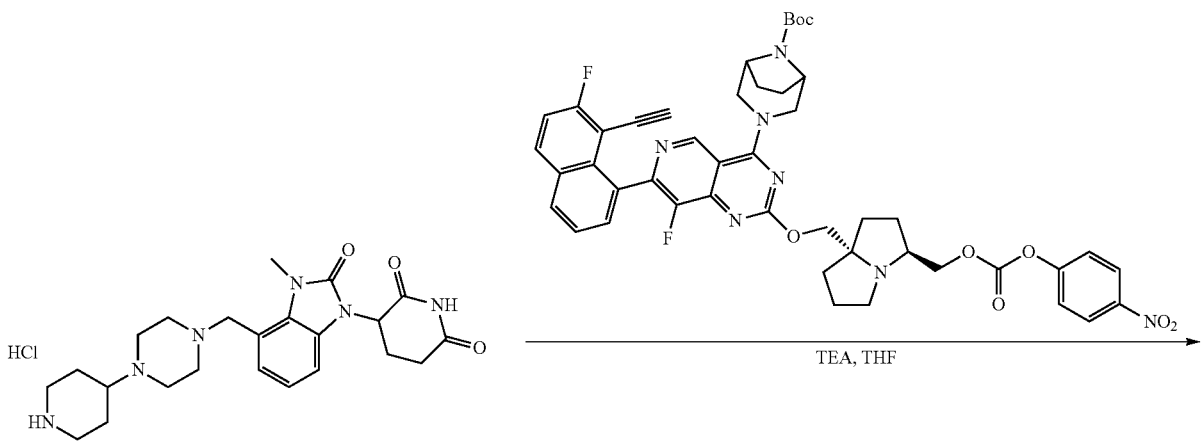

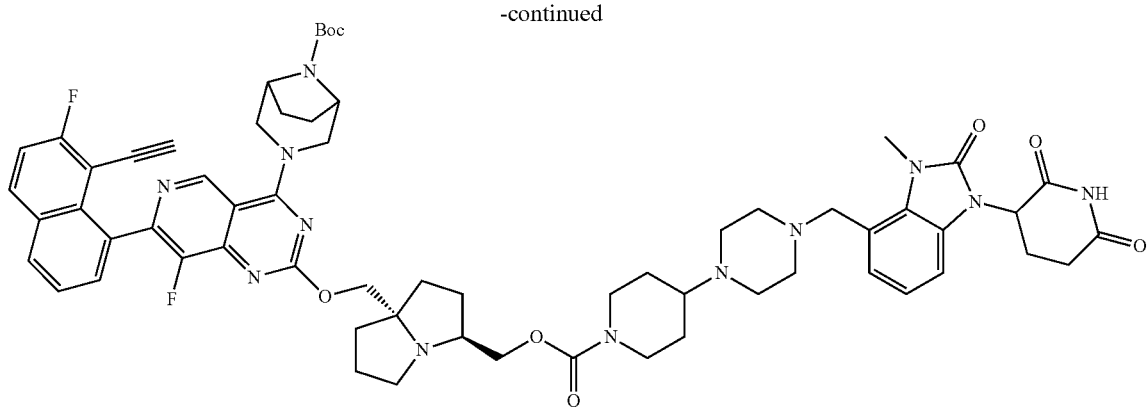

To a mixture of 3-[3-methyl-2-oxo-4-[[4-(4-piperidyl)piperazin-1-yl]methyl]benzimidazol-1-yl]piperidine-2,6-dione (40.0 mg, 90.8 μmol, HCl salt) in THF (1 mL) was added TEA (363 mg, 3.59 mmol, 0.5 mL) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (39.1 mg, 45.4 μmol), the reaction mixture was stirred at 25° C. for 4 hrs. On completion, the mixture was concentrated in vacuo to give a residue. The residue was purified by prep-HPLC (column: Welch Ultimate C18 150*25 mm*5 μm; mobile phase: [water (FA)-ACN]; gradient: 22%-42% B over 10 min) to give the title compound (20.0 mg, 18% yield) as yellow solid. LC-MS (ESI+) m/z 1163.3 (M+H)+.

(d) Step 4—[(3S,8S)-8-[[4-(3,8-diazabicyclo [3.2.1] octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[4-[[1-(2,6-dioxo-3-piperidyl)-3-methyl-2-oxo-benzimidazol-4-yl]methyl]piperazin-1-yl]piperidine-1-carboxylate (053)

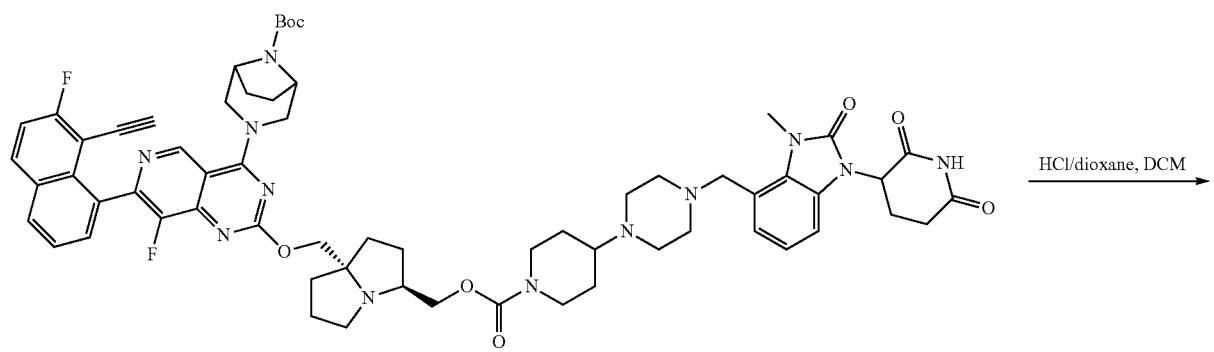

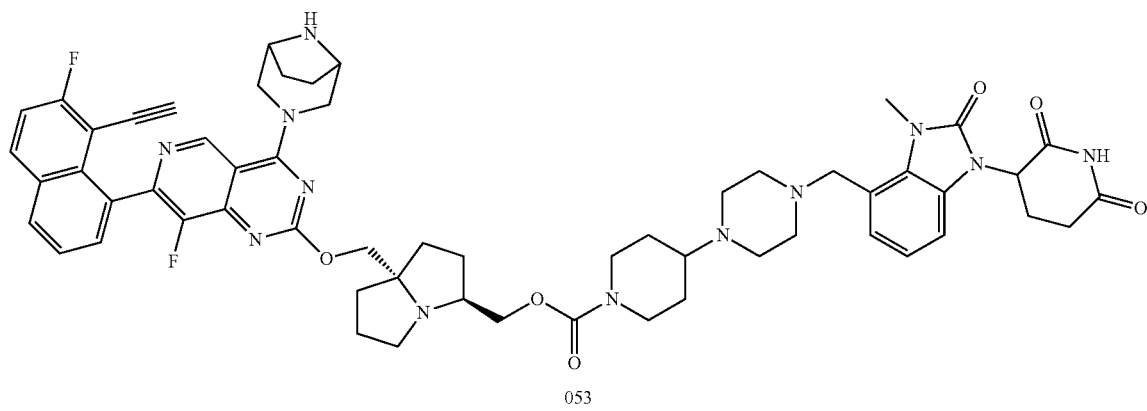

053

To a mixture of tert-butyl 3-[2-[[(3S,8S)-3-[[4-[4-[[1-(2,6-dioxo-3-piperidyl)-3-methyl-2-oxo-benzimidazol-4-yl]methyl]piperazin-1-yl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (10.0 mg, 8.60 μmol) in DCM (0.5 mL) was added HCl/dioxane (4 M, 1.00 mL), the reaction mixture was stirred at 25° C. for 0.5 hr. On completion, the residue was concentrated in vacuo to give the title compound (7.61 mg, 79% yield, HCl) as yellow solid. $^1$H NMR (400 MHz, DMSO-$d_6$) δ 11.10 (s, 1H), 11.08-11.02 (m, 1H), 9.96-9.88 (m, 1H), 9.60-9.51 (m, 1H), 9.16 (s, 1H), 8.29-8.17 (m, 2H), 7.74-7.68 (m, 1H), 7.65 (d, J=8.0 Hz, 1H), 7.63-7.59 (m, 1H), 7.18-6.93 (m, 3H), 5.44-5.36 (m, 1H), 4.73-4.64 (m, 3H), 4.63-4.54 (m, 2H), 4.43-4.34 (m, 2H), 4.20 (s, 4H), 4.05 (d, J=4.4 Hz, 1H), 4.01-3.94 (m, 3H), 3.65 (s, 3H), 3.39 (s, 2H), 2.89 (s, 2H), 2.82-2.75 (m, 2H), 2.74-2.69 (m, 2H), 2.66 (dd, J=4.0, 12.4 Hz, 2H), 2.34-2.28 (m, 2H), 2.16-1.91 (m, 18H), 1.67-1.56 (m, 2H), 1.28-1.21 (m, 2H); LC-MS (ESI$^+$) m/z 1063.4 (M+H)$^+$.

Example 58. Synthesis of Compound 054

(a) Step 1—Benzyl 3-(trifluoromethylsulfonyloxy)azetidine-1-carboxylate

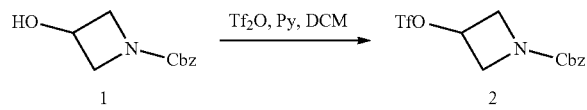 [SMILES: O=C(OCc1ccccc1)N1CC(O)C1 ; "Tf2O, Py, DCM" ; O=C(OCc1ccccc1)N1CC(OS(=O)(=O)C(F)(F)F)C1]

To a stirring solution of benzyl 3-hydroxyazetidine-1-carboxylate (10.0 g, 48.2 mmol, CAS #128117-22-6), pyridine (Py, 7.62 g, 96.3 mmol), and DCM (240 mL) was added Tf$_2$O (16.6 g, 59.0 mmol) dropwise at −20° C. The reaction was allowed to gradually warm to 25° C. for 1 hr. On completion, the reaction was allowed to gradually warm to room temperature while stirring. The reaction mixture was concentrated, and then dissolved in EA (200 mL×3). The organic solution was washed with water, sat aq NaHCO$_3$ (100 mL×3), and then brine before drying with anhydrous MgSO$_4$, filtered and concentrated in vacuo to give the title compound (16.0 g, 97% yield) as yellow oil. LC-MS (ESI$^+$) m/z 296.0 (M−42+H)$^+$.

(b) Step 2—Tert-butyl 4-(1-benzyloxycarbonylazetidin-3-yl)oxypiperidine-1-carboxylate

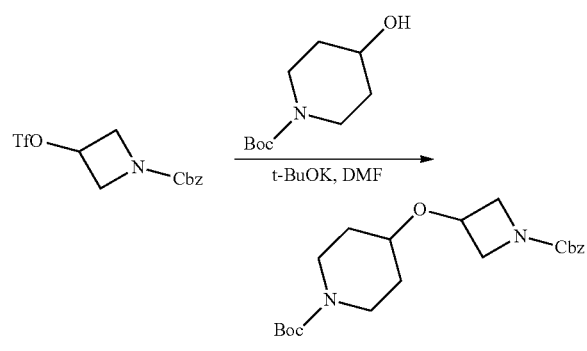

To a solution of tert-butyl 4-hydroxypiperidine-1-carboxylate (9.49 g, 47.1 mmol, CAS #109384-19-2) in DMF (100 mL) was added t-BuOK (10.5 g, 94.3 mmol) at −10° C. for 0.5 hr, then benzyl 3-(trifluoromethylsulfonyloxy)azetidine-1-carboxylate (16.0 g, 47.1 mmol) and KI (1.57 g, 9.43 mmol) were added to the solution. The mixture was stirred at −10° C. for 2 hrs. On completion, the reaction mixture was concentrated in vacuo to give a residue. The residue was purified by column chromatography (SiO$_2$, PE/EA=100/1 to 1/1) to give the title compound (3.20 g, 15.6% yield) as yellow oil. $^1$H NMR (400 MHz, CDCl$_3$) δ 7.40-7.29 (m, 5H), 5.10 (s, 2H), 4.41-4.32 (m, 1H), 4.21-4.14 (m, 2H), 3.92 (dd, J=4.4, 9.6 Hz, 2H), 3.78 (d, J=12.4 Hz, 2H), 3.41-3.47 (m, 1H), 3.08-3.01 (m, 2H), 1.81-1.73 (m, 2H), 1.54-1.47 (m, 2H), 1.46 (s, 9H); LC-MS (ESI$^+$) m/z 291.1 (M-Boc+H)$^+$.

(c) Step 3—Tert-butyl 4-(azetidin-3-yloxy)piperidine-1-carboxylate

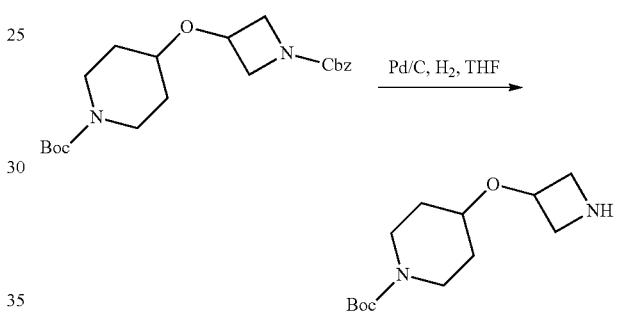

To a solution of tert-butyl 4-(1-benzyloxycarbonylazetidin-3-yl)oxypiperidine-1-carboxylate (500 mg, 1.28 mmol) in THF (5 mL) was added Pd/C (250 mg, 234 μmol, 10% purity). The suspension was degassed and purged with H$_2$ for 3 times. The mixture was stirred under H$_2$ atmosphere (15 Psi) at 25° C. for 12 hrs. On completion, the reaction mixture was filtered to remove Pd/C and concentrated in vacuo to give the title compound (328 mg, 1.28 mmol, 99% yield) as gray oil. $^1$H NMR (400 MHz, CDCl$_3$) δ 4.45-4.35 (m, 1H), 4.24-3.60 (m, 8H), 3.50-3.40 (m, 1H), 2.08 (s, 1H), 1.81-1.71 (m, 2H), 1.63-1.48 (m, 2H), 1.45 (s, 9H); LC-MS (ELSD) m/z 256.9 (M+H)$^+$.

(d) Step 4—Tert-butyl 4-[1-[[1-(2,6-dioxo-3-piperidyl)-3-methyl-2-oxo-benzimidazol-4-yl] methyl]azetidin-3-yl]oxypiperidine-1-carboxylate

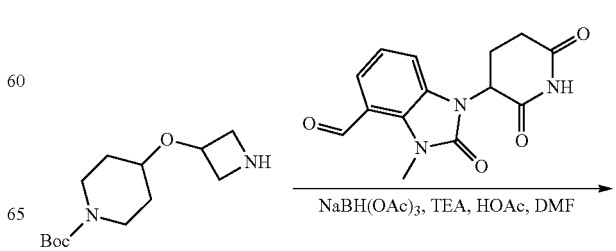

-continued

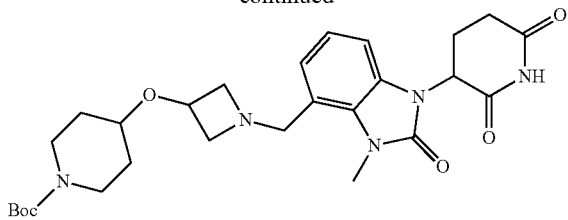

To a solution of tert-butyl 4-(azetidin-3-yloxy)piperidine-1-carboxylate (328 mg, 1.33 mmol) in DMF (10 mL) was added TEA (259 mg, 2.56 mmol) to pH=7-8. The mixture was stirred at 25° C. for 0.5 hr. And then HOAc (230 mg, 3.84 mmol) was added to pH=6-7. At last 1-(2,6-dioxo-3-piperidyl)-3-methyl-2-oxo-benzimidazole-4-carbaldehyde (367 mg, 1.33 mmol) and NaBH(OAc)$_3$ (325 mg, 1.54 mmol) was added. The mixture was stirred at 25° C. for 12 hrs. On completion, the residue was quenched by H$_2$O (1 mL), filtered and the filtrate was concentrated in vacuo to give a residue. The residue was purified by prep-HPLC (column: Phenomenex luna C18 150*25 mm*10 um; mobile phase: [water (FA)-ACN]; gradient: 8%-38% B over 10 min) to give the title compound (50.0 mg, 7.4% yield) as colorless oil. $^1$H NMR (400 MHz, DMSO-d$_6$) δ 11.10 (s, 1H), 7.05 (t, J=4.4 Hz, 1H), 6.94 (d, J=4.8 Hz, 2H), 5.36 (dd, J=5.2, 12.8 Hz, 1H), 4.16-4.10 (m, 1H), 3.80 (s, 2H), 3.65 (s, 2H), 3.62 (s, 3H), 3.50-3.43 (m, 4H), 3.01-2.89 (m, 4H), 2.73-2.63 (m, 2H), 2.05-1.94 (m, 1H), 1.72 (dd, J=4.0, 8.8 Hz, 2H), 1.38 (s, 9H), 1.30-1.21 (m, 2H); LC-MS (ESI$^+$) m/z 528.2 (M+H)$^+$.

(e) Step 5—3-[3-Methyl-2-oxo-4-[[3-(4-piperidyloxy)azetidin-1-yl]methyl]benzimidazol-1-yl]piperidine-2,6-dione

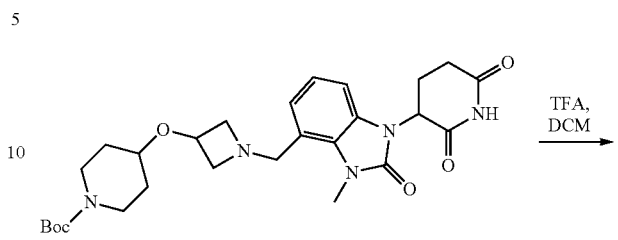

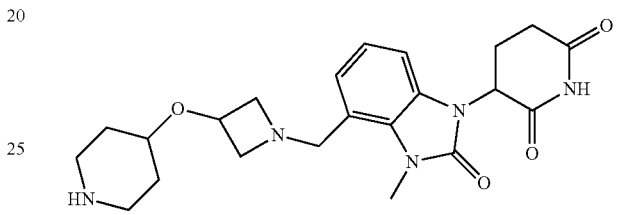

To a solution of tert-butyl 4-[1-[[1-(2,6-dioxo-3-piperidyl)-3-methyl-2-oxo-benzimidazol-4-yl]methyl] azetidin-3-yl]oxypiperidine-1-carboxylate (50.0 mg, 94.7 µmol) in DCM (1 mL) was added TFA (307 mg, 0.2 mL). The mixture was stirred at 25° C. for 1 hr. On completion, the reaction mixture was concentrated in vacuo to give the title compound (50.0 mg, 97% yield, TFA salt) as yellow oil. LC-MS (ESI$^+$) m/z 428.2 (M+H)$^+$.

(f) Step 6—Tert-butyl 3-[2-[[(3S,8S)-3-[[4-[1-[[1-(2,6-dioxo-3-piperidyl)-3-methyl-2-oxo-benzimidazol-4-yl]methyl]azetidin-3-yl]oxypiperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

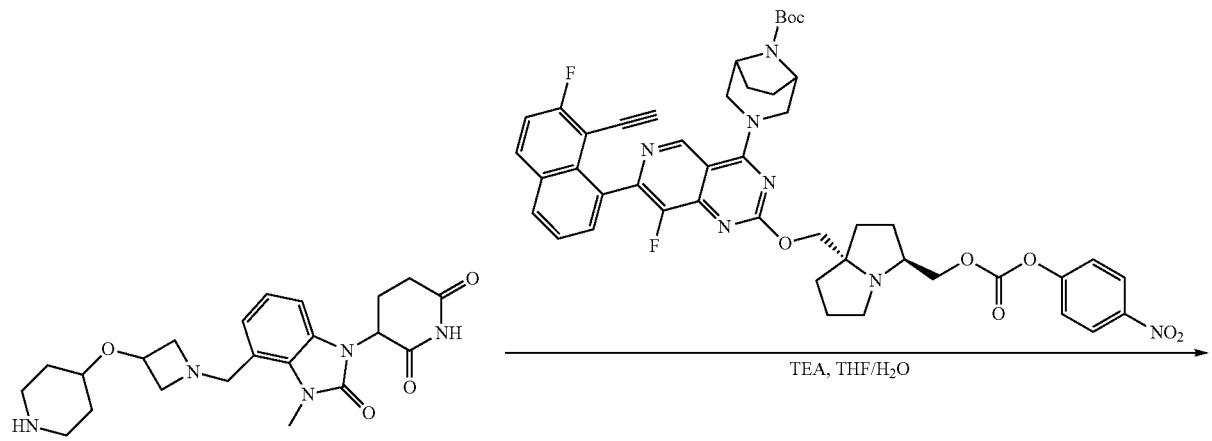

1133

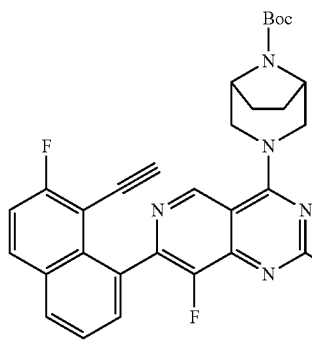

-continued

1134

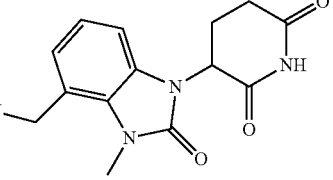

To a solution of 3-[3-methyl-2-oxo-4-[[3-(4-piperidyloxy)azetidin-1-yl]methyl]benzimidazol-1-yl] piperidine-2,6-dione (50.0 mg, 92.3 μmol, TFA salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (53.0 mg, 61.5 μmol) in THF (2 mL) was added TEA (17.7 mg, 183 μmol) and H$_2$O (0.4 mL). The mixture was stirred at 25° C. for 0.5 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 15%-45% B over 10 min) to give the title compound (35.0 mg, 49% yield) as yellow solid. $^1$H NMR (400 MHz, DMSO-d$_6$) δ 11.12 (s, 1H), 9.16 (s, 1H), 8.28-8.20 (m, 2H), 7.71 (t, J=7.6 Hz, 1H), 7.67-7.58 (m, 2H), 7.19 (d, J=4.0 Hz, 2H), 7.07 (d, J=1.2 Hz, 1H), 5.49-5.35 (m, 1H), 4.66-4.53 (m, 4H), 4.43-4.35 (m, 2H), 4.32 (s, 2H), 4.26-4.22 (m, 1H), 3.97 (d, J=6.4 Hz, 2H), 3.79-3.66 (m, 4H), 3.58 (s, 3H), 3.48-3.38 (m, 4H), 3.19-2.91 (m, 5H), 2.66-2.59 (m, 4H), 1.95 (s, 10H), 1.87-1.70 (m, 6H), 1.47 (s, 9H), 1.40-1.31 (m, 2H); LC-MS (ESI$^+$) m/z 1150.2 (M+H)$^+$.

(g) Step 7—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[1-[[1-(2,6-dioxo-3-piperidyl)-3-methyl-2-oxo-benzimidazol-4-yl]methyl]azetidin-3-yl]oxypiperidine-1-carboxylate (054)

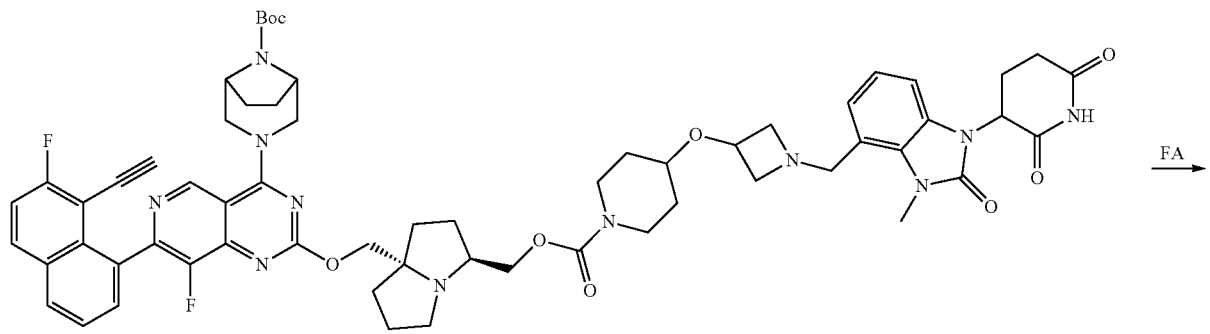

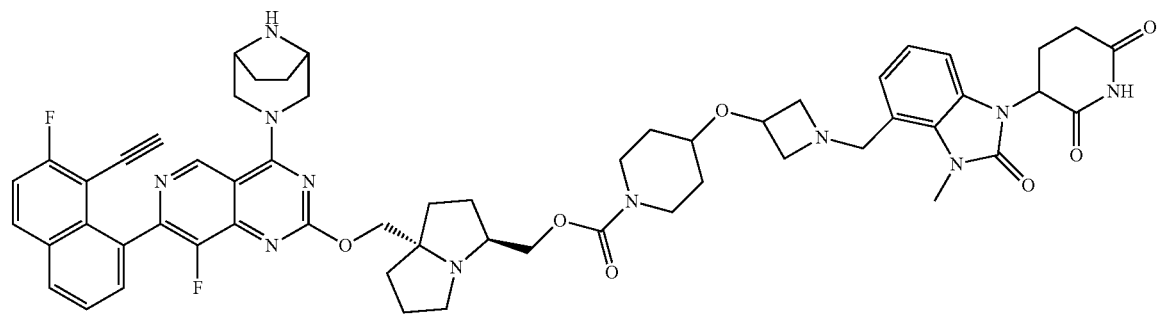

054

A solution of tert-butyl 3-[2-[[(3S,8S)-3-[[4-[1-[[1-(2,6-dioxo-3-piperidyl)-3-methyl-2-oxo-benzimidazol-4-yl]methyl]azetidin-3-yl]oxypiperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35.0 mg, 30.4 μmol) in HCOOH (2 mL) was stirred at 25° C. for 2 hrs. On completion, the reaction mixture was concentrated in vacuo to give a residue. The residue was dissolved in ACN (1 mL) and $H_2O$ (5 mL) and lyophilized to give the title compound (27.1 mg, 78% yield, FA salt) as yellow solid. $^1$H NMR (400 MHz, DMSO-$d_6$) δ 11.09 (s, 1H), 9.12 (s, 1H), 8.28-8.18 (m, 2H), 7.75-7.57 (m, 3H), 7.04 (d, J=2.8 Hz, 1H), 6.98-6.90 (m, 2H), 5.36 (dd, J=5.2, 12.4 Hz, 1H), 4.63 (d, J=14.4 Hz, 1H), 4.51-4.45 (m, 1H), 4.30 (d, J=15.6 Hz, 1H), 4.22 (d, J=6.4 Hz, 2H), 4.16-4.11 (m, 1H), 4.07 (s, 2H), 4.02 (s, 1H), 3.86-3.78 (m, 4H), 3.71-3.66 (m, 2H), 3.61 (s, 3H), 3.48 (s, 4H), 3.09-3.02 (m, 3H), 2.88 (t, J=6.0 Hz, 2H), 2.74-2.59 (m, 4H), 2.16-2.12 (m, 1H), 2.03-1.96 (m, 2H), 1.93-1.63 (m, 14H), 1.34-1.27 (m, 2H); LC-MS (ESI$^+$) m/z 1050.2 (M+H)$^+$.

Example 59. Synthesis of Compound 055

(a) Step 1—3-(3-Methyl-2-oxo-5-vinyl-benzimidazol-1-yl)piperidine-2,6-dione

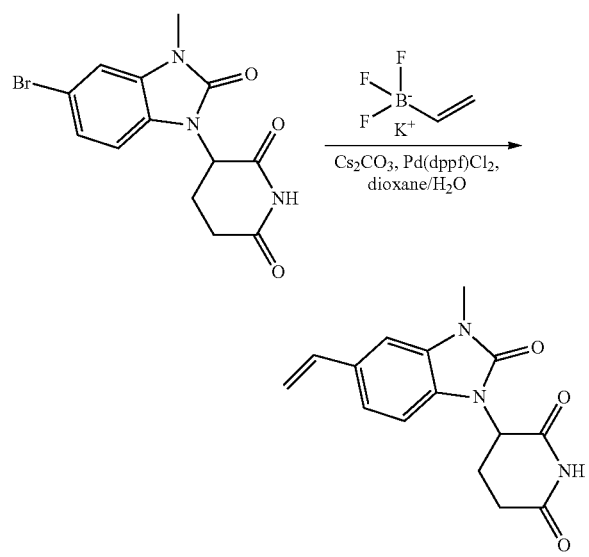

To a solution of 3-(5-bromo-3-methyl-2-oxo-benzimidazol-1-yl)piperidine-2,6-dione (10.0 g, 29.6 mmol, CAS #2300099-98-1) and potassium; trifluoro(vinyl)boranuide (11.9 g, 88.7 mmol, CAS #13682-77-4) in dioxane (100 mL) and $H_2O$ (20 mL) was added $Cs_2CO_3$ (28.9 g, 88.7 mmol) and Pd(dppf)Cl$_2$ (2.16 g, 2.96 mmol) at 25° C. The mixture was stirred at 80° C. for 16 hrs under $N_2$ atmosphere. On completion, the mixture was filtered and the filtrate was concentrated in vacuo to give a residue. The residue was purified by column chromatography (SiO$_2$, PE/EA=100/1 to 0/1) to give the title compound (6.00 g, 68% yield) as white solid. $^1$H NMR (400 MHz, CDCl$_3$) δ 8.32 (s, 1H), 7.14-7.07 (m, 2H), 6.79-6.69 (m, 2H), 5.71 (d, J=17.6 Hz, 1H), 5.26-5.19 (m, 2H), 3.46 (s, 3H), 2.98-2.90 (m, 1H), 2.88-2.78 (m, 1H), 2.77-2.68 (m, 1H), 2.28-2.20 (m, 1H); LC-MS (ESI$^+$) m/z 286.0 (M+H)$^+$.

(b) Step 2—1-(2,6-Dioxo-3-piperidyl)-3-methyl-2-oxo-benzimidazole-5-carbaldehyde

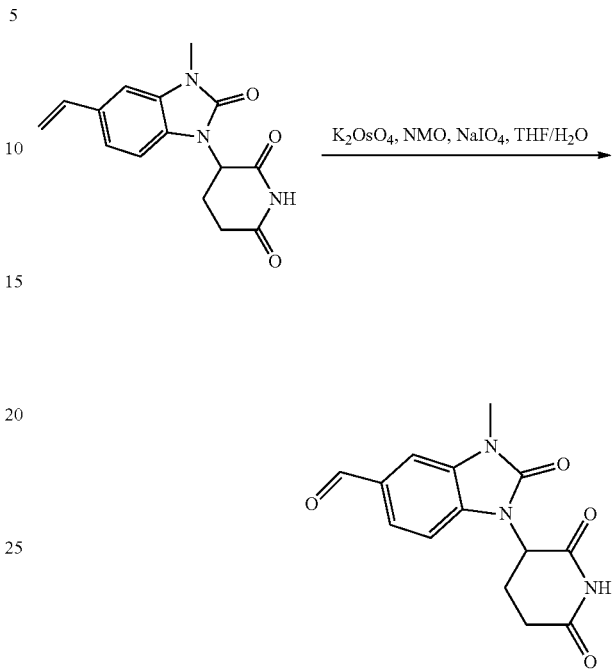

To a solution of 3-(3-methyl-2-oxo-5-vinyl-benzimidazol-1-yl)piperidine-2,6-dione (6.00 g, 21.0 mmol) in THF (60 mL) and $H_2O$ (12 mL) was added $K_2OsO_4$ (387 mg, 1.05 mmol) and NMO (4.19 g, 35.8 mmol). The mixture was stirred at 25° C. for 12 hrs. Then NaIO$_4$ (31.5 g, 147 mmol) was added to the mixture and the mixture was stirred at 25° C. for 1 hr. On completion, the reaction mixture was diluted with $H_2O$ (150 mL). The mixture was extracted with DCM (3×150 mL), and the organic layer was washed with brine (2×100 mL), dried over anhydrous Na$_2$SO$_4$, filtered and the filtrate was concentrated in vacuo to give the title compound (6.00 g, 97% yield) as white solid. $^1$H NMR (400 MHz, DMSO-$d_6$) δ 11.18 (s, 1H), 9.94 (s, 1H), 7.73-7.66 (m, 2H), 7.40-7.35 (m, 1H), 5.48 (dd, J=5.2, 12.8 Hz, 1H), 3.42 (s, 3H), 2.96-2.87 (m, 1H), 2.80-2.71 (m, 1H), 2.70-2.62 (m, 1H), 2.12-2.04 (m, 1H); LC-MS (ESI$^+$) m/z 287.9 (M+H)$^+$.

(c) Step 3—Tert-butyl 4-[1-[[1-(2,6-dioxo-3-piperidyl)-3-methyl-2-oxo-benzimidazol-5-yl]methyl]-4-piperidyl]piperidine-1-carboxylate

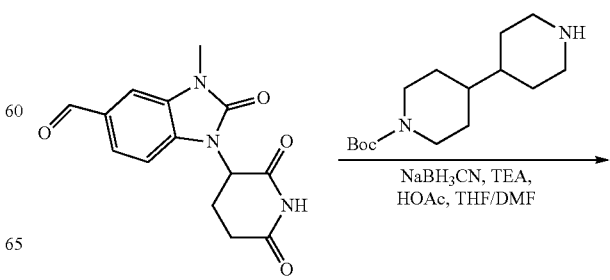

-continued

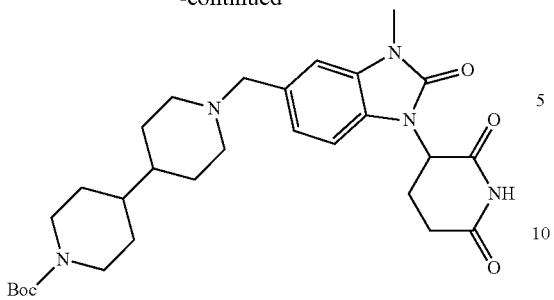

To a solution of tert-butyl 4-(4-piperidyl)piperidine-1-carboxylate (208 mg, 774 μmol, CAS #171049-35-7) in THF (3 mL) was basified with TEA (108 μL, 774 μmol) to PH=8, and then acidified with HOAc (44.0 μL, 774 μmol) to PH=6. Then a solution of 1-(2,6-dioxo-3-piperidyl)-3-methyl-2-oxo-benzimidazole-5-carbaldehyde (400 mg, 1.39 mmol) in DMF (3 mL) was added to the mixture and the mixture was stirred at 35° C. for 0.5 hr. Then NaBH$_3$CN (63.2 mg, 1.01 mmol) was added to mixture and stirred at 35° C. for 16 hrs. On completion, the mixture was concentrated in vacuo to give a residue. The residue was purified by prep-HPLC (column: Phenomenex luna C18 150*25 mm*10 μm; mobile phase: [water (FA)-ACN]; gradient: 10%-40% B over 10 min) to give the title compound (250 mg, 58% yield) as white solid. $^1$H NMR (400 MHz, DMSO-d$_6$) δ 11.13 (s, 1H), 7.29 (s, 1H), 7.24-7.20 (m, 1H), 7.19-7.13 (m, 1H), 5.41 (dd, J=5.2, 12.8 Hz, 1H), 4.29 (s, 2H), 3.95 (d, J=10.4 Hz, 2H), 3.37 (s, 3H), 2.87 (s, 2H), 2.72 (dd, J=3.6, 13.2 Hz, 2H), 2.66 (s, 2H), 2.07-1.98 (m, 2H), 1.85 (d, J=11.2 Hz, 2H), 1.80 (s, 1H), 1.75 (s, 1H), 1.60 (d, J=12.0 Hz, 2H), 1.38 (s, 9H), 1.32 (s, 2H), 1.27-1.16 (m, 2H), 1.03-0.94 (m, 2H); LC-MS (ESI$^+$) m/z 540.2 (M+H)$^+$.

(d) Step 4—3-[3-Methyl-2-oxo-5-[[4-(4-piperidyl)-1-piperidyl]methyl]benzimidazol-1-yl]piperidine-2,6-dione

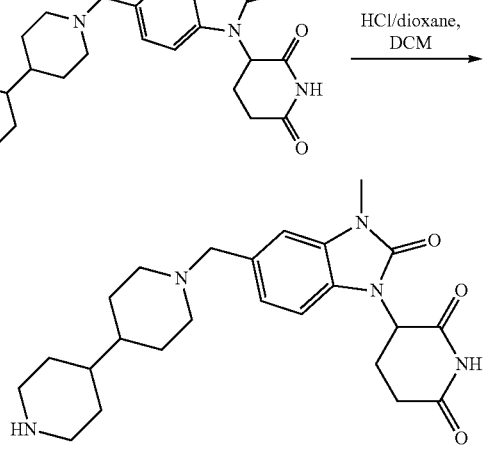

To a solution of tert-butyl 4-[1-[[1-(2,6-dioxo-3-piperidyl)-3-methyl-2-oxo-benzimidazol-5-yl]methyl]-4-piperidyl]piperidine-1-carboxylate (100 mg, 185 μmol) in DCM (1 mL) was added HCl/dioxane (4 M, 1 mL). The mixture was stirred at 25° C. for 0.5 hr. On completion, the mixture was concentrated in vacuo to give the title compound (80.0 mg, 71% yield, HCl salt) as white solid. LC-MS (ESI$^+$) m/z 440.2 (M+H)$^+$.

(e) Step 5—Tert-butyl 3-[2-[[(3S,8S)-3-[[4-[1-[[1-(2,6-dioxo-3-piperidyl)-3-methyl-2-oxo-benzimidazol-5-yl]methyl]-4-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

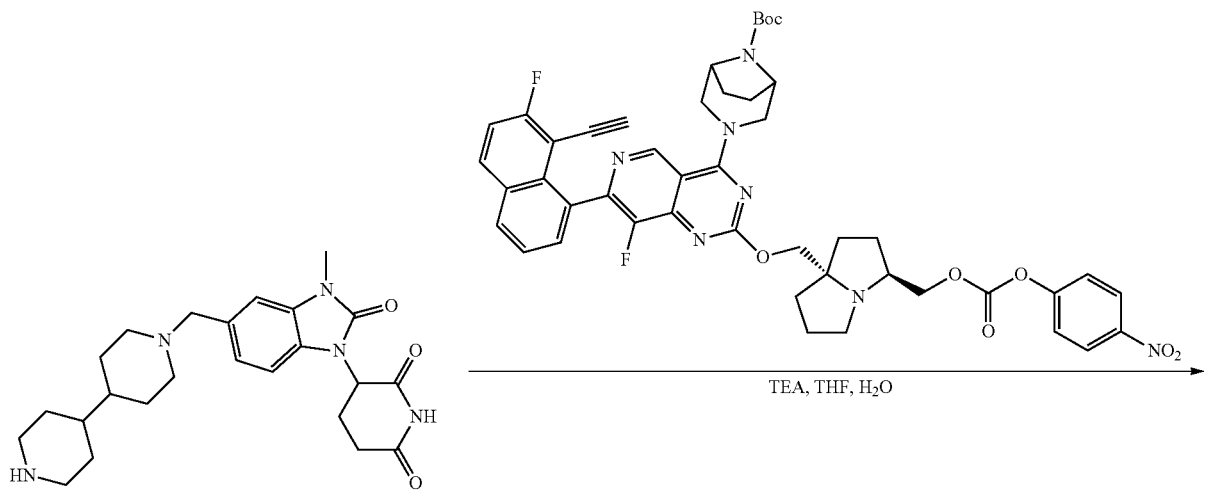

-continued

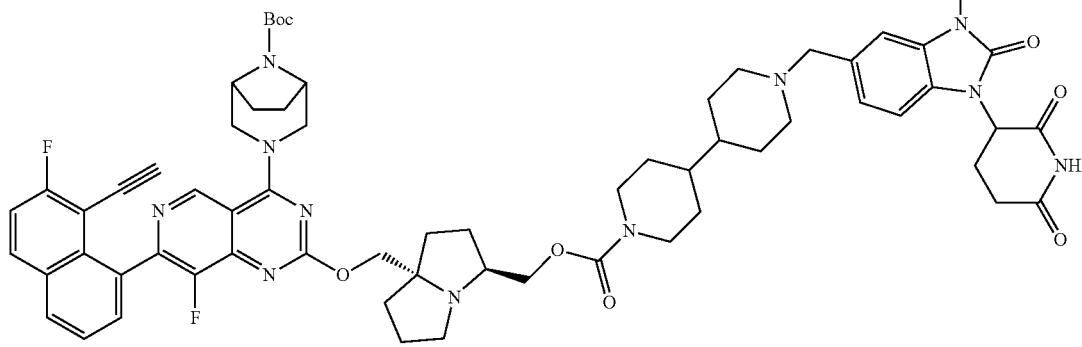

A solution of 3-[3-methyl-2-oxo-5-[[4-(4-piperidyl)-1-piperidyl]methyl]benzimidazol-1-yl]piperidine-2,6-dione (80.0 mg, 168 μmol, HCl salt) in THF (0.5 mL) and H$_2$O (0.5 mL) was basified with TEA (82.0 μL, 588 μmol) to pH=8. Then a solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (72.4 mg, 84.0 μmol) in THF (0.5 mL) was added to the mixture, then the mixture was stirred at 25° C. for 0.5 hr. On completion, the mixture was concentrated in vacuo to give a residue. The residue was purified by prep-HPLC (column: Welch Xtimate C18 150*25 mm*5 um; mobile phase: [water (FA)-ACN]; gradient: 19%-49% B over 10 min) to give the title compound (30.0 mg, 30% yield) as yellow solid. LC-MS (ESI$^+$) m/z 1162.3 (M+H)$^+$.

(f) Step 6—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[1-[[1-(2,6-dioxo-3-piperidyl)-3-methyl-2-oxo-benzimidazol-5-yl]methyl]-4-piperidyl]piperidine-1-carboxylate (055)

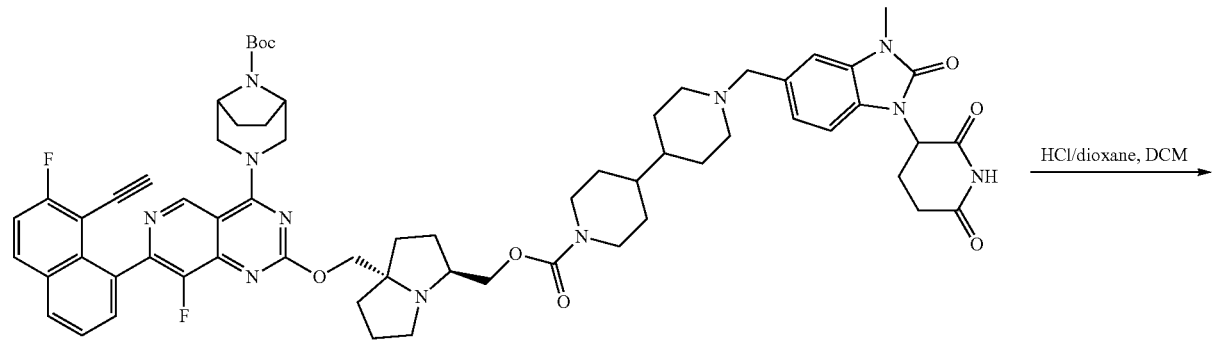

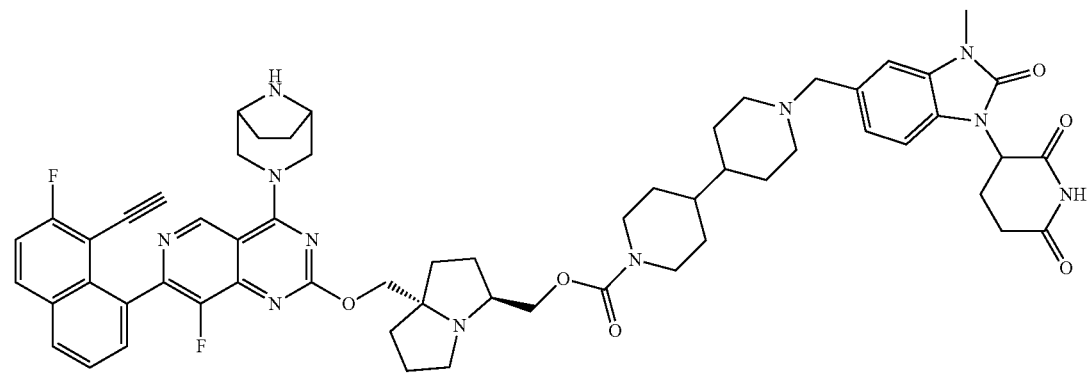

055

To a solution of tert-butyl 3-[2-[[(3S,8S)-3-[[4-[1-[[1-(2,6-dioxo-3-piperidyl)-3-methyl-2-oxo-benzimidazol-5-yl]methyl]-4-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30.0 mg, 25.8 μmol) in DCM (1 mL) was added HCl/dioxane (4 M, 1 mL). The mixture was stirred at 25° C. for 0.5 hr. On completion, the mixture was concentrated in vacuo to give a residue. Then residue was dissolved in deionized water (5 mL) and ACN (1 mL), and the mixture was lyophilized to give the title compound (25.8 mg, 90% yield, HCl salt) as yellow solid. $^1$H NMR (400 MHz, DMSO-$d_6$) δ 11.12 (s, 1H), 11.10-11.04 (m, 1H), 10.66-1063 (m, 1H), 10.14-10.05 (m, 1H), 9.83-9.71 (m, 1H), 9.16 (s, 1H), 8.28-8.19 (m, 2H), 7.75-7.68 (m, 1H), 7.68-7.59 (m, 2H), 7.53 (s, 1H), 7.27-7.22 (m, 1H), 7.22-7.17 (m, 1H), 5.42 (dd, J=5.2, 12.8 Hz, 1H), 4.71-4.62 (m, 3H), 4.61-4.52 (m, 1H), 4.35 (d, J=9.2 Hz, 1H), 4.28-4.16 (m, 6H), 4.07 (d, J=3.6 Hz, 1H), 4.01-3.96 (m, 2H), 3.89-3.86 (m, 4H), 3.35 (s, 3H), 3.30 (s, 2H), 2.99-2.59 (m, 8H), 2.31-2.24 (m, 1H), 2.22-2.10 (m, 2H), 2.10-1.86 (m, 12H), 1.78 (d, J=12.4 Hz, 2H), 1.59 (d, J=10.0 Hz, 4H), 1.03 (d, J=10.4 Hz, 2H); LC-MS (ESI$^+$) m/z 1062.2 (M+H)$^+$.

Example 60. Synthesis of Compound 056

(a) Step 1—Tert-butyl 4-[4-[[1-(2,6-dioxo-3-piperidyl)-3-methyl-2-oxo-benzimidazol-5-yl]methyl]piperazin-1-yl]piperidine-1-carboxylate

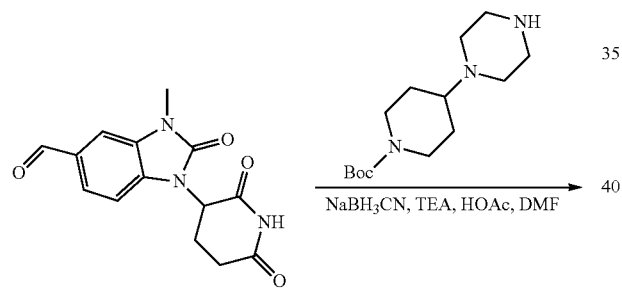

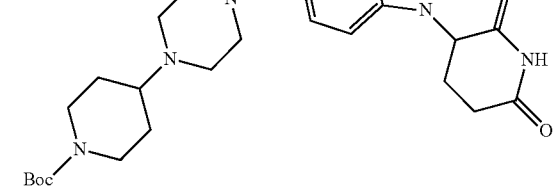

To a solution of tert-butyl 4-piperazin-1-ylpiperidine-1-carboxylate (187 mg, 696 μmol, CAS #143238-38-4) in DMF (8 mL) was added TEA (281 mg, 2.78 mmol) to pH=7-8 and HOAc (250 mg, 4.18 mmol) was added to pH=6-7, And then 1-(2,6-dioxo-3-piperidyl)-3-methyl-2-oxo-benzimidazole-5-carbaldehyde (400 mg, 1.39 mmol) was added. The mixture was stirred at 25° C. for 1 hr. At last NaBH$_3$CN (105 mg, 1.67 mmol) was added. The mixture was stirred at 25° C. for 12 hrs. On completion, the reaction mixture was quenched by added H$_2$O (1 mL) and concentrated in vacuo to give a residue. The crude product was purified by reversed-phase HPLC (0.1% FA condition) to give the title compound (160 mg, 20% yield) as white solid. $^1$H NMR (400 MHz, DMSO-$d_6$) δ 11.09 (s, 1H), 7.09 (d, J=0.8 Hz, 1H), 7.06-7.02 (m, 1H), 6.95 (dd, J=1.2, 8.0 Hz, 1H), 5.35 (dd, J=5.6, 12.8 Hz, 1H), 3.92 (d, J=11.2 Hz, 2H), 3.33 (s, 3H), 3.01-2.82 (m, 3H), 2.75-2.61 (m, 5H), 2.52 (d, J=1.6 Hz, 2H), 2.37-2.31 (m, 4H), 2.07-1.95 (m, 1H), 1.70 (d, J=10.0 Hz, 3H), 1.38-1.38 (m, 9H), 1.27-1.16 (m, 3H); LC-MS (ESI$^+$) m/z 541.2 (M+H)$^+$.

(b) Step 2—3-[3-Methyl-2-oxo-5-[[4-(4-piperidyl)piperazin-1-yl]methyl]benzimidazol-1-yl]piperidine-2,6-dione

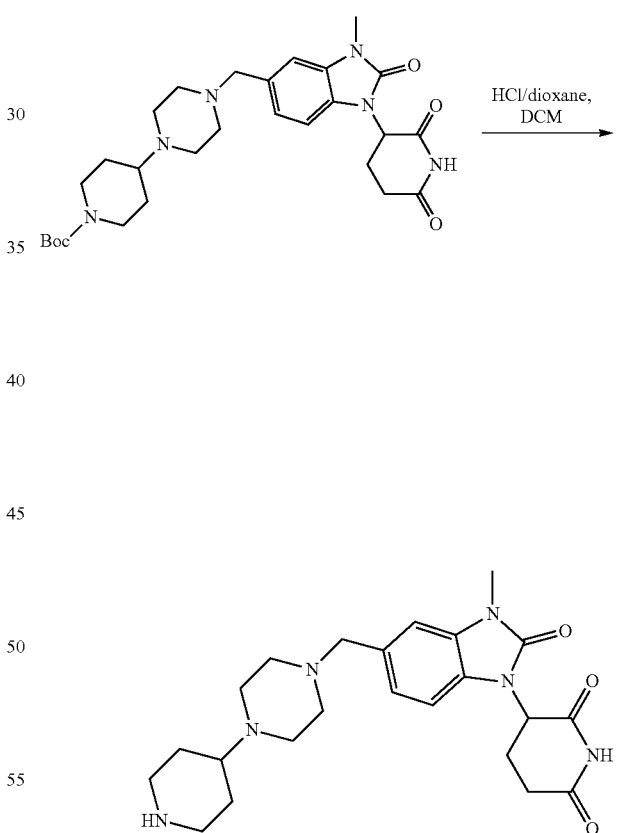

To a solution of tert-butyl 4-[4-[[1-(2,6-dioxo-3-piperidyl)-3-methyl-2-oxo-benzimidazol-5-yl]methyl] piperazin-1-yl]piperidine-1-carboxylate (80.0 mg, 148 μmol) in DCM (2 mL) was added HCl/dioxane (4 M, 2 mL). The mixture was stirred at 25° C. for 1 hr. On completion, the reaction mixture was concentrated in vacuo to give a residue to give the title compound (70.0 mg, 99% yield, HCl salt) as white solid. LC-MS (ESI$^+$) m/z 441.1 (M+H)$^+$.

(c) Step 3—Tert-butyl 3-[2-[[(3S,8S)-3-[[4-[4-[[1-(2,6-dioxo-3-piperidyl)-3-methyl-2-oxo-benzimidazol-5-yl]methyl]piperazin-1-yl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

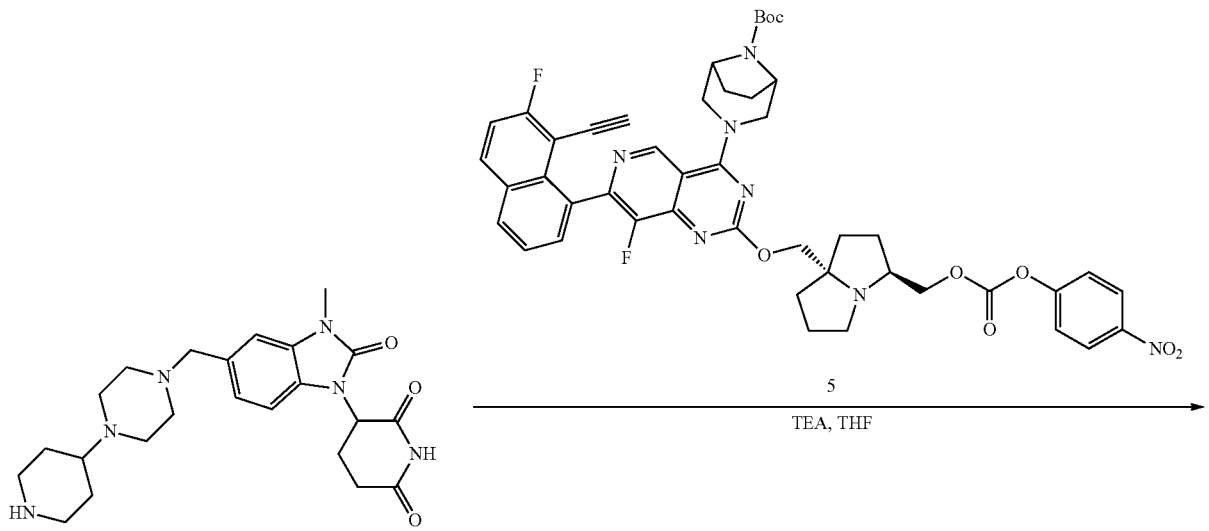

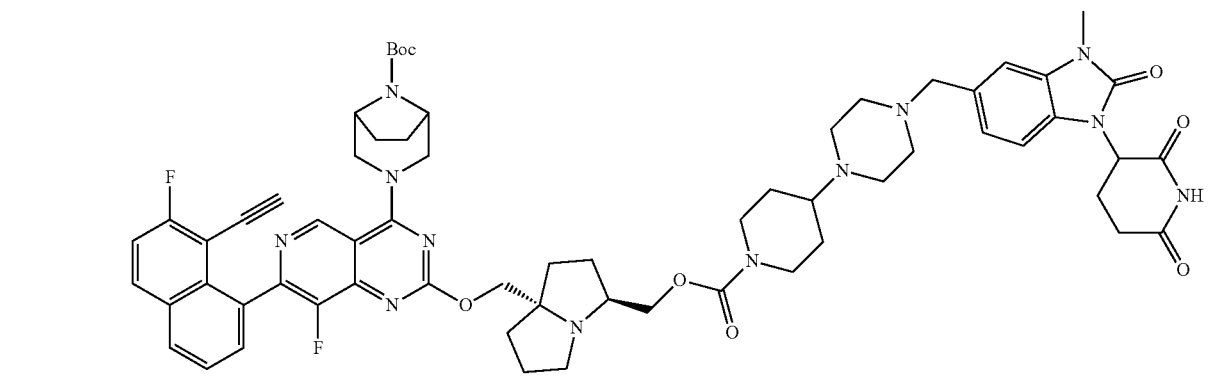

To a solution of 3-[3-methyl-2-oxo-5-[[4-(4-piperidyl)piperazin-1-yl]methyl]benzimidazol-1-yl] piperidine-2,6-dione (69.7 mg, 146 μmol, HCl salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol) in THF (3 mL) was added TEA (24.6 mg, 24.0 μmol) and H₂O (0.3 mL). The mixture was stirred at 25° C. for 0.5 hr. On completion, the reaction mixture was concentrated in vacuo to give a residue. The residue was purified by prep-HPLC (column: Welch Ultimate C18 150*25 mm*5 μm; mobile phase: [water (FA)-ACN]; gradient: 13%-43% B over 10 min) to give the title compound (30.0 mg, 31% yield) as yellow solid. $^1$H NMR (400 MHz, DMSO-$d_6$) δ 11.09 (s, 1H), 9.09 (s, 1H), 8.24-8.18 (m, 2H), 7.77-7.49 (m, 3H), 7.11-6.90 (m, 3H), 5.35 (dd, J=5.2, 12.8 Hz, 1H), 4.55 (d, J=13.2 Hz, 1H), 4.46-4.35 (m, 1H), 4.31 (s, 2H), 4.24-4.17 (m, 1H), 4.16-4.09 (m, 2H), 4.05 (d, J=10.8 Hz, 1H), 4.01 (s, 1H), 3.99-3.90 (m, 2H), 3.64 (t, J=13.6 Hz, 2H), 3.44-3.42 (s, 2H), 3.32 (s, 3H), 2.93-2.85 (m, 1H), 2.78-2.68 (m, 4H), 2.65-2.59 (m, 2H), 2.54-2.52 (m, 4H), 2.48-2.45 (m, 6H), 2.07-1.97 (m, 2H), 1.83 (d, J=8.4 Hz, 2H), 1.78-1.60 (m, 10H), 1.54-1.48 (m, 1H), 1.46 (s, 9H), 1.30-1.18 (m, 2H); LC-MS (ESI⁺) m/z 1163.2 (M+H)⁺.

(d) Step 4—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[4-[[1-(2,
6-dioxo-3-piperidyl)-3-methyl-2-oxo-benzimidazol-
5-yl]methyl]piperazin-1-yl]piperidine-1-carboxylate
(056)

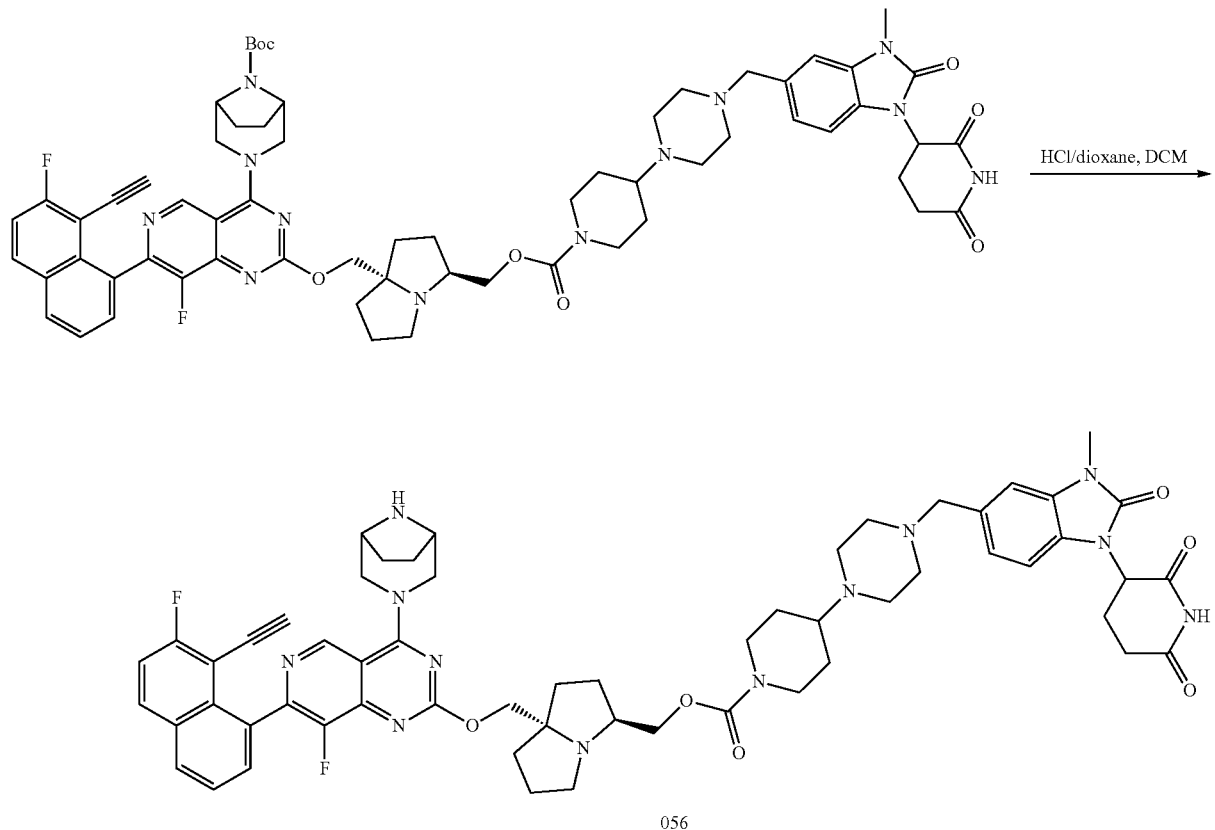

To a solution of tert-butyl 3-[2-[[(3S,8S)-3-[[4-[4-[[1-(2,
6-dioxo-3-piperidyl)-3-methyl-2-oxo-benzimidazol-5-yl]
methyl]piperazin-1-yl]piperidine-1-carbonyl]oxymethyl]-1,
2,3,5,6,7-hexahydropyrrolizin-8-yl]methoxy]-7-(8-ethynyl-
7-fluoro-1-naphthyl)-8-fluoro-pyrido[4,3-d]pyrimidin-4-
yl]-3,8-diazabicyclo[3.2.1]octane-8-carboxylate (30.0 mg,
25.7 µmol) in DCM (2 mL) was added HCl/dioxane (4 M,
2 mL). The mixture was stirred at 25° C. for 0.5 hr. On
completion, the reaction mixture was concentrated in vacuo
to give a residue. The residue was dissolved in ACN (1 mL)
and H$_2$O (5 mL) and lyophilized to give the title compound
(23.5 mg, 79% yield, HCl salt) as a yellow solid. $^1$H NMR
(400 MHz, DMSO-d$_6$) δ 12.38-12.15 (m, 1H), 11.31-11.17
(m, 1H), 11.12 (s, 1H), 10.06 (dd, J=1.2, 9.2 Hz, 1H),
9.82-9.65 (m, 1H), 9.16 (s, 1H), 8.30-8.19 (m, 2H), 7.73-
7.56 (m, 4H), 7.34-7.19 (m, 2H), 5.52-5.37 (m, 1H), 4.71-
4.62 (m, 3H), 4.60-4.53 (m, 1H), 4.40 (d, J=8.4 Hz, 4H),
4.20 (s, 4H), 4.16-3.87 (m, 5H), 3.58-3.39 (m, 10H), 3.35 (s,
3H), 2.96-2.60 (m, 6H), 2.32-2.26 (m, 1H), 2.15 (d, J=14.8
Hz, 2H), 2.09-1.94 (m, 12H), 1.69-1.57 (m, 2H); LC-MS
(ESI$^+$) m/z 1063.3 (M+H)$^+$.

Example 61. Synthesis of Compound 057

(a) Step 1—1-(2,6-Dioxo-3-piperidyl)-3-methyl-2-
oxo-benzimidazole-4-carbaldehyde

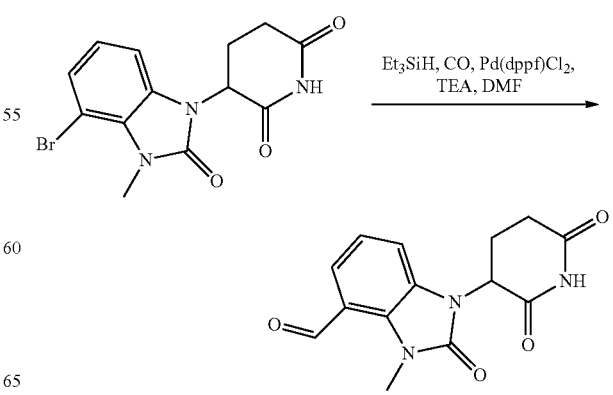

To a solution of 3-(4-bromo-3-methyl-2-oxo-benzimidazol-1-yl)piperidine-2,6-dione (10.0 g, 29.5 mmol, CAS #2304754-51-4) in DMF (100 mL) was added Et₃SiH (10.3 g, 88.7 mmol, 14.1 mL) and Pd(dppf)Cl₂ (2.16 g, 2.96 mmol) and TEA (8.98 g, 88.7 mmol, 12.3 mL), the reaction was stirred at 80° C. for 16 hrs on CO (15 Psi) atmosphere. On completion, the residue was diluted with water (80 mL), then the residue was extracted with EA (3×100 mL). The combined organic layers was dried over Na₂SO₄, filtered and the solid dried in vacuo to give the title compound (3.50 g, 41% yield) as yellow solid. ¹H NMR (400 MHz, DMSO-d₆) δ 11.15 (s, 1H), 10.40 (s, 1H), 7.60 (d, J=7.6 Hz, 1H), 7.46 (d, J=7.6 Hz, 1H), 7.21 (t, J=7.6 Hz, 1H), 5.47 (dd, J=5.2, 12.8 Hz, 1H), 3.67 (s, 3H), 2.89 (d, J=5.2, 11.2 Hz, 1H), 2.78-2.72 (m, 1H), 2.65 (d, J=14.4 Hz, 1H), 2.10-2.01 (m, 1H); LC-MS (ESI⁺) m/z 288.0 (M+H)⁺.

(b) Step 2—Tert-butyl N-[1-[[1-(2,6-dioxo-3-piperidyl)-3-methyl-2-oxo-benzimidazol-4-yl]methyl]-4-piperidyl]carbamate

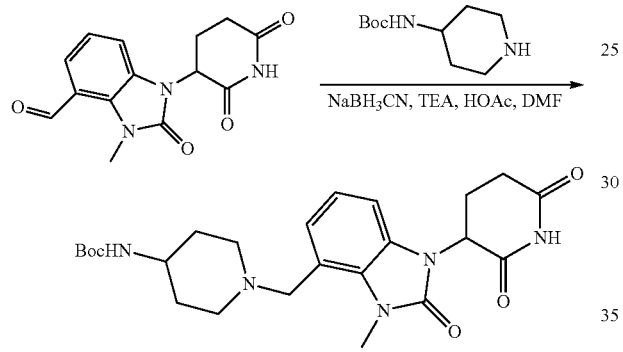

To a mixture of tert-butyl N-(4-piperidyl)carbamate (348 mg, 1.74 mmol) in DMF (5 mL) was added TEA (176 mg, 1.74 mmol, 242 μL), then was added 1-(2,6-dioxo-3-piperidyl)-3-methyl-2-oxo-benzimidazole-4-carbaldehyde (500 mg, 1.74 mmol) and HOAc (104 mg, 1.74 mmol, 99.6 μL), the reaction mixture was stirred at 40° C. for 0.5 hr, then was added NaBH₃CN (142 mg, 2.26 mmol) and stirred at 40° C. for 3.5 hrs. On completion, the reaction mixture was filtered and concentrated in vacuo. The residue was purified by reverse phase (0.1% FA condition) to give the title compound (65.0 mg, 98% yield) as white solid. ¹H NMR (400 MHz, DMSO-d₆) δ 11.11 (s, 1H), 7.10 (d, J=2.8 Hz, 1H), 7.04-6.88 (m, 2H), 6.81 (s, 1H), 5.39 (dd, J=5.2, 12.4 Hz, 1H), 3.64 (s, 3H), 3.33 (s, 2H), 3.16-2.97 (m, 1H), 2.97-2.83 (m, 2H), 2.77-2.57 (m, 3H), 2.54-2.51 (m, 1H), 2.07 (s, 2H), 2.06-1.95 (m, 2H), 1.79-1.68 (m, 2H), 1.39-1.36 (m, 9H); LC-MS (ESI⁺) m/z 472.2 (M+H)⁺.

(c) Step 3—3-[4-[(4-Amino-1-piperidyl)methyl]-3-methyl-2-oxo-benzimidazol-1-yl]piperidine-2,6-dione

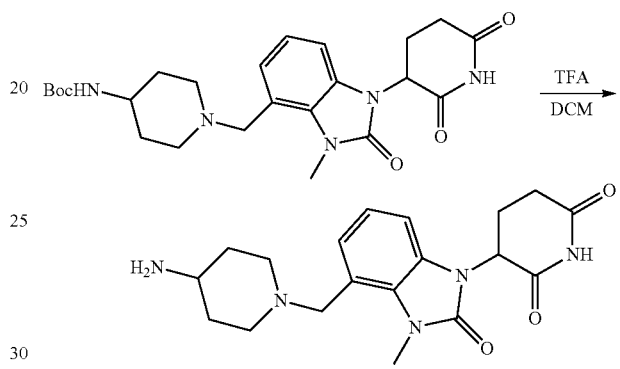

To a solution of tert-butyl N-[1-[[1-(2,6-dioxo-3-piperidyl)-3-methyl-2-oxo-benzimidazol-4-yl]methyl]-4-piperidyl]carbamate (50.0 mg, 106 μmol) in DCM (1 mL) was added TFA (12.0 mg, 106 μmol, 7.88 μL), the reaction mixture was stirred at 25° C. for 0.5 hr. On completion, the reaction mixture was concentrated in vacuo to give the title compound (38.0 mg, 96% yield, TFA salt) as brown oil.

(d) Step 4—Tert-butyl 3-[7-(8-ethynyl-7-fluoro-1-naphthyl)-8-fluoro-2-[[(3S,8S)-3-[(4-oxopiperidine-1-carbonyl)oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

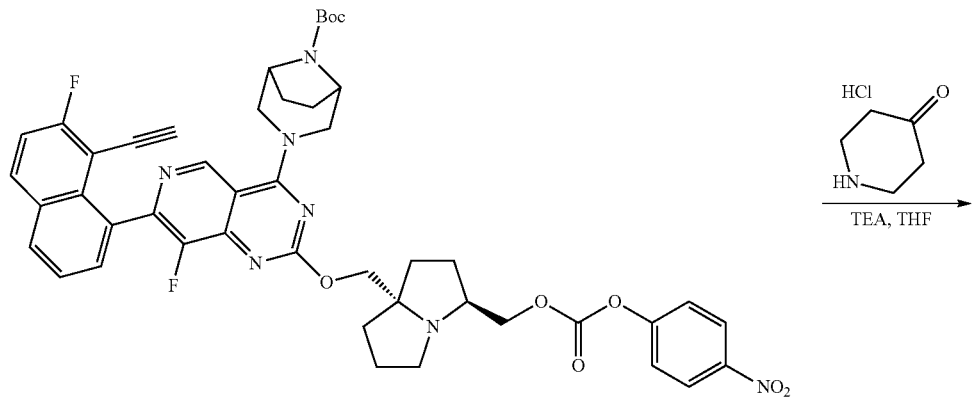

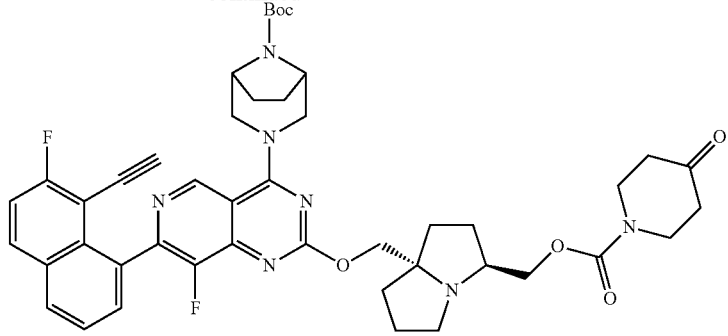

To a solution of tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (120 mg, 139 μmol) in THF (1 mL) was added TEA (14.0 mg, 139 μmol, 19.3 μL) and piperidin-4-one; hydrochloride (28.3 mg, 208 μmol, CAS #41979-39-9), the reaction mixture was stirred at 25° C. for 0.5 hr. On completion, the reaction mixture was concentrated in vacuo. The residue was purified by prep-HPLC (column: Phenomenex luna C18 150*25 mm*10 um; mobile phase: [water (FA)-ACN]; gradient: 25%-55% B over 10 min) to give the title compound (80.0 mg, 69% yield) as yellow solid. $^1$H NMR (400 MHz, CDCl$_3$) δ 8.99 (s, 1H), 8.08 (d, J=9.2 Hz, 1H), 8.01-7.92 (m, 2H), 7.66-7.56 (m, 2H), 7.37-7.30 (m, 1H), 6.86 (d, J=9.2 Hz, 1H), 4.61-4.52 (m, 2H), 4.44-4.34 (m, 4H), 3.84-3.73 (m, 4H), 3.72-3.59 (m, 2H), 2.86 (s, 1H), 2.46 (s, 4H), 2.38-2.28 (m, 2H), 2.00 (d, J=7.2 Hz, 9H), 1.84-1.72 (m, 4H), 1.53 (s, 9H). LC-MS (ESI$^+$) m/z 822.3 (M+H)$^+$.

(e) Step 5—Tert-butyl 3-[2-[[(3S,8S)-3-[[4-[[1-[[1-(2,6-dioxo-3-piperidyl)-3-methyl-2-oxo-benzimidazol-4-yl]methyl]-4-piperidyl]amino]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

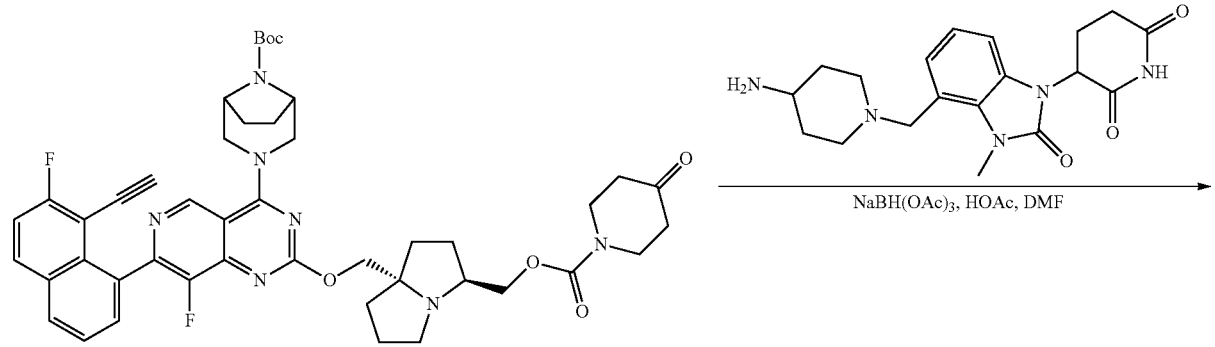

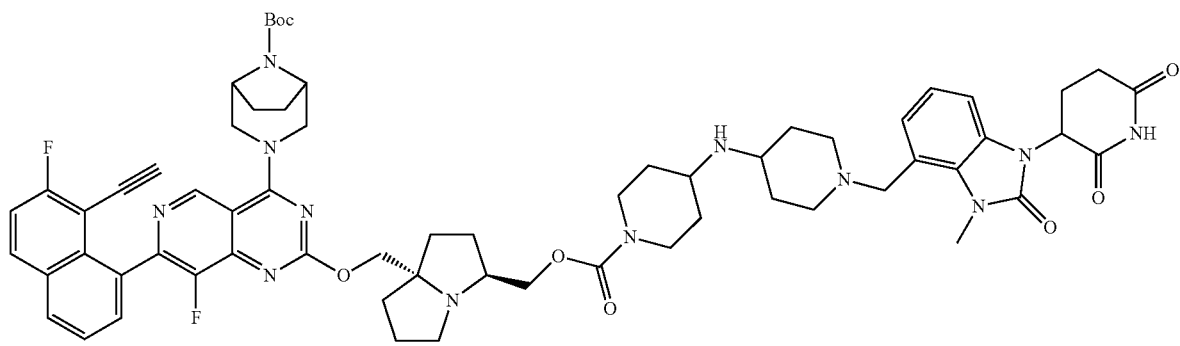

To a mixture of 3-[4-[(4-amino-1-piperidyl)methyl]-3-methyl-2-oxo-benzimidazol-1-yl]piperidine-2,6-dione (30.0 mg, 80.7 μmol, TFA salt) in DMF (1 mL) was added TEA (4.09 mg, 40.3 μmol, 5.62 μL) and HOAc (2.43 mg, 40.3 μmol, 2.31 μL), then tert-butyl 3-[7-(8-ethynyl-7-fluoro-1-naphthyl)-8-fluoro-2-[[(3S,8S)-3-[(4-oxopiperidine-1-carbonyl)oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (33.1 mg, 40.3 μmol) was added, then NaBH₃CN (3.81 mg, 60.5 μmol) was added the mixture, the reaction mixture was stirred at 25° C. for 1 hr. On completion, the reaction mixture was quenched with water (0.5 mL) and concentrated in vacuo. The residue was purified by prep-HPLC (column: Phenomenex luna C18 150*25 mm*10 um; mobile phase: [water (FA)-ACN]; gradient: 20%-40% B over 10 min) to give the title compound (20.0 mg, 42% yield) as white solid. LC-MS (ESI⁺) m/z 1177.6 (M+H)⁺.

(f) Step 6—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[[1-[1(2,6-dioxo-3-piperidyl)-3-methyl-2-oxo-benzimidazol-4-yl]methyl]-4-piperidyl]amino]piperidine 1-carboxylate (057)

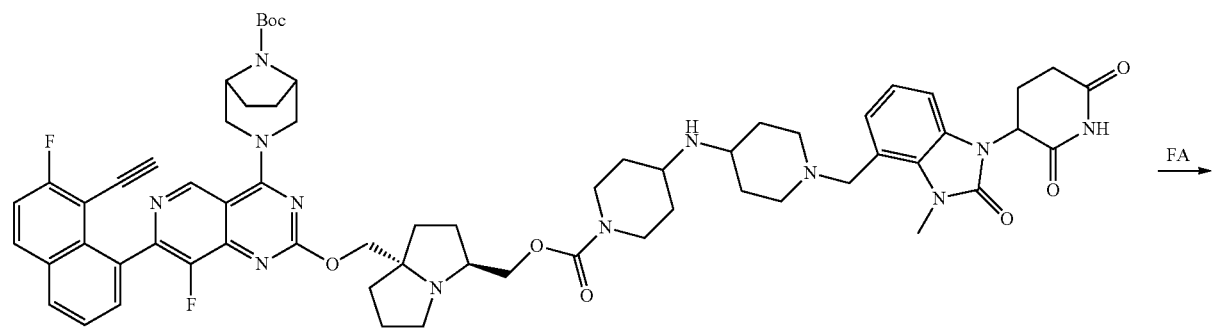

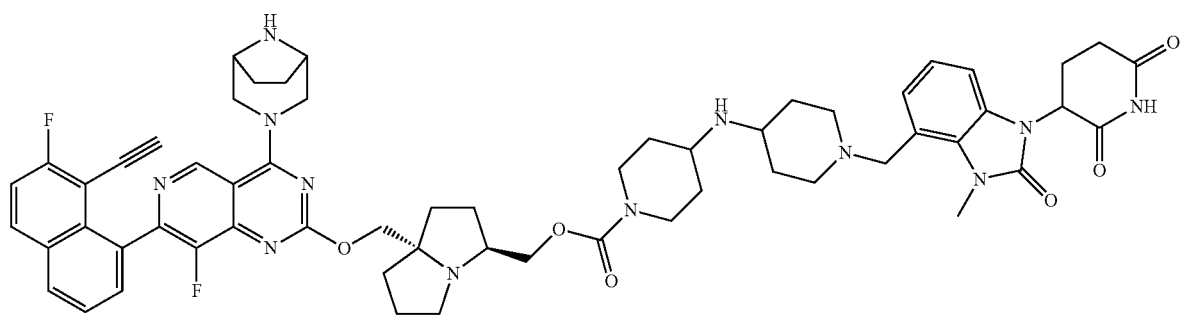

057

Tert-butyl 3-[2-[[(3S,8S)-3-[[4-[[1-[[1-(2,6-dioxo-3-piperidyl)-3-methyl-2-oxo-enzimidazol-yl] methyl]-4-piperidyl]amino]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (20.0 mg, 16.9 μmol) was dissolved in HCOOH (816 μg, 16.9 μmol) stirred at 25° C. for 2 hrs. On completion, the reaction mixture was concentrated in vacuo. Then ACN (2 mL) and H₂O (2 mL) was added, the solution was lyophilized to give the title compound (15.8 mg, 82% yield, 100% purity, FA) as yellow solid. ¹H NMR (400 MHz, DMSO-d₆) 11.11 (d, J=1.2 Hz, 1H), 9.06 (s, 1H), 8.22 (s, 4H), 7.70-7.58 (m, 3H), 7.07 (d, J=7.2 Hz, 1H), 6.96 (t, J=7.6 Hz, 1H), 6.86 (d, J=7.2 Hz, 1H), 5.38 (dd, J=4.8, 12.8 Hz, 1H), 4.50 (d, J=11.2 Hz, 1H), 4.36 (d, J=11.2 Hz, 1H), 4.24-4.19 (m, 2H), 4.14 (s, 2H), 4.07 (d, J=10.8 Hz, 2H), 4.02 (s, 1H), 3.95 (s, 3H), 3.70 (s, 2H), 3.66 (s, 3H), 3.62 (s, 2H), 3.30 (d, J=3.6 Hz, 1H), 3.07-3.03 (m, 1H), 2.89-2.78 (m, 7H), 2.72 (d, J=4.4 Hz, 1H), 2.66 (d, J=10.0 Hz, 2H), 2.08-1.98 (m, 4H), 1.85 (s, 4H), 1.73 (s, 8H), 1.56-1.50 (m, 1H), 1.38-1.19 (m, 5H). LC-MS (ESI⁺) m/z 1077.5 (M+H)⁺.

Example 62. Synthesis of Compound 058

(a) Step 1—Hex-5-ynyl 4-methylbenzenesulfonate

To a solution hex-5-yn-1-ol (1 g, 10.1 mmol, CAS #928-90-5) in DCM (10 mL) was added TosCl (2.33 g, 12.2 mmol), TEA (3.09 g, 30.5 mmol) and DMAP (62.2 mg, 509 μmol). The reaction was stirred at 25° C. for 24 hrs. On completion, the residue was diluted with water (50 mL) and extracted with DCM (2×25 mL). The combined organic layers was washed with brine (50 mL) and dried over Na$_2$SO$_4$, filtered and the filtrate was concentrated in vacuo to give a residue. The residue was purified by column chromatography (SiO$_2$, PE=90%) to give the title compound (2 g, 77% yield) as colorless oil. $^1$H NMR (400 MHz, DMSO-d$_6$) δ 7.79 (d, J=8.4 Hz, 2H), 7.48 (d, J=8.4 Hz, 2H), 4.04 (t, J=6.4 Hz, 2H), 2.76 (t, J=2.8 Hz, 1H), 2.42 (s, 3H), 2.15-2.08 (m, 2H), 1.70-1.58 (m, 2H), 1.47-1.35 (m, 2H).

(b) Step 2—Tert-butyl 4-hex-5-ynoxypiperidine-1-carboxylate

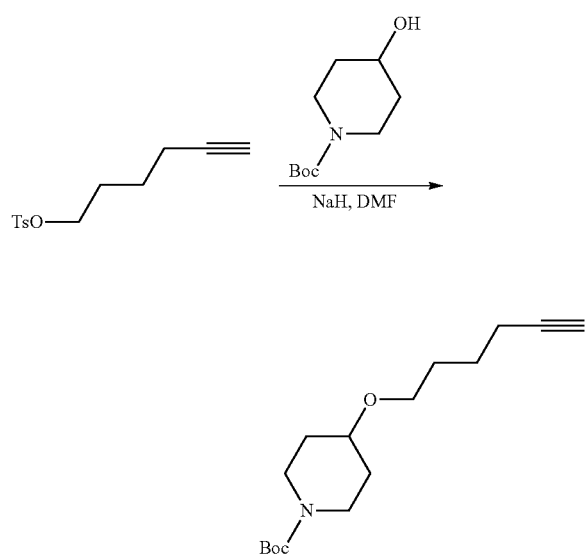

To a solution of tert-butyl 4-hydroxypiperidine-1-carboxylate (1.14 g, 5.66 mmol, CAS #109384-19-2) in DMF (15 mL) was added NaH (452 mg, 11.3 mmol, 60% purity) at 0° C. The reaction mixture was stirred at 0° C. for 1 hr. Then hex-5-ynyl 4-methylbenzenesulfonate (1 g, 3.96 mmol) was added to the mixture. The reaction mixture was stirred at 25° C. for 12 hrs. On completion, the resulting mixture was quenched with H$_2$O (10 mL). The residue was diluted with water (50 mL) and extracted with EA (2×25 mL). The combined organic layers was washed with brine (50 mL) and dried over Na$_2$SO$_4$, filtered and the filtrate was concentrated in vacuo to give a residue. The residue was purified by column chromatography (SiO$_2$, PE=92%) to give the title compound (1 g, 62% yield) as a colorless oil. $^1$H NMR (400 MHz, DMSO-d$_6$) δ 3.67-3.53 (m, 2H), 3.47-3.36 (m, 3H), 3.01 (t, J=9.6 Hz, 2H), 2.75 (t, J=2.8 Hz, 1H), 2.18-2.14 (m, 2H), 1.83-1.66 (m, 2H), 1.62-1.44 (m, 4H), 1.38 (s, 9H), 1.34-1.23 (m, 2H).

(c) Step 3—Tert-butyl 4-[6-[1-(2,6-dioxo-3-piperidyl)-3-methyl-2-oxo-benzimidazol-4-yl]hex-5-ynoxy] piperidine-1-carboxylate

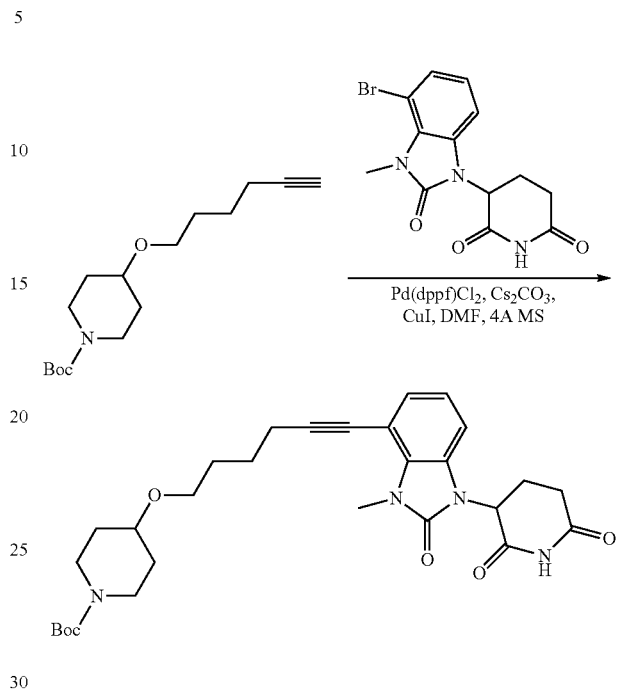

To a solution of tert-butyl 4-hex-5-ynoxypiperidine-1-carboxylate (400 mg, 1.42 mmol) and 3-(4-bromo-3-methyl-2-oxo-benzimidazol-1-yl)piperidine-2,6-dione (240 mg, 710 μmol, CAS #2304754-51-4) in DMF (4 mL) was added CuI (13.5 mg, 71.0 μmol), Cs$_2$CO$_3$ (694 mg, 2.13 mmol), Pd(PPh$_3$)$_2$Cl$_2$ (49.8 mg, 71.0 μmol) and 4 A MS (20 mg) under N$_2$. The mixture was stirred at 115° C. for 4 hrs. On completion, the mixture was filtered and the filtrate was concentrated in vacuo to give a residue. The residue was diluted with EA (20 mL) and washed with H$_2$O (100 mL×2). The combined organic phase was washed with brine 100 mL (50 mL×2), dried over Na$_2$SO$_4$, filtered and concentrated to give the title compound (300 mg, 78% yield) as a white solid. $^1$H NMR (400 MHz, DMSO-d$_6$) δ 11.10 (s, 1H), 7.14-6.90 (m, 3H), 5.38 (dd, J=5.2, 12.8 Hz, 1H), 3.63 (s, 3H), 3.61-3.55 (m, 2H), 3.50-3.39 (m, 3H), 3.01 (t, J=10.0 Hz, 2H), 2.94-2.83 (m, 1H), 2.77-2.59 (m, 2H), 2.06-1.97 (m, 3H), 1.81-1.72 (m, 2H), 1.64 (s, 4H), 1.38 (s, 9H), 1.33 (dt, J=4.4, 8.8 Hz, 2H); LC-MS (ESI$^+$) m/z 439.0 (M+H–100)$^+$.

(d) Step 4—Tert-butyl 4-[6-[1-(2,6-dioxo-3-piperidyl)-3-methyl-2-oxo-benzimidazol-4-yl]hexoxy] piperidine-1-carboxylate

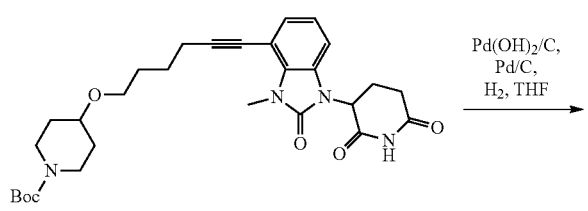

1155
-continued

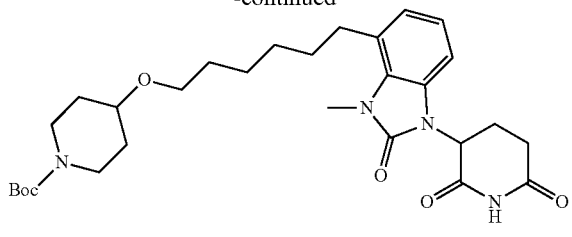

To a solution of tert-butyl 4-[6-[1-(2,6-dioxo-3-piperidyl)-3-methyl-2-oxo-benzimidazol-4-yl]hex-5-ynoxy]piperidine-1-carboxylate (300 mg, 556 μmol) in THF (10 mL) was added Pd/C (150 mg, 140 μmol) and Pd(OH)$_2$ (150 mg, 1.07 mmol). The reaction mixture was stirred at 25° C. for 16 hrs under H$_2$ (15 psi). On completion, the resulting mixture was concentrated in vacuo to give the title compound (150 mg, 49% yield) as a white solid. LC-MS (ESI$^+$) m/z 443.1 (M+H−100)$^+$.

(e) Step 5—3-[3-Methyl-2-oxo-4-[6-(4-piperidyloxy)hexyl]benzimidazol-1-yl]piperidine-2,6-dione

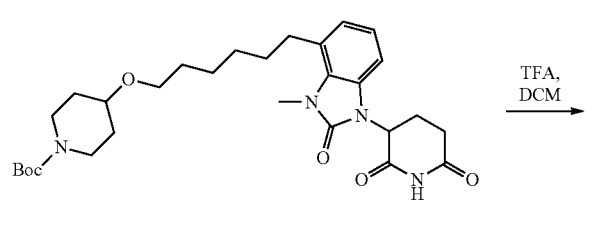

1156
-continued

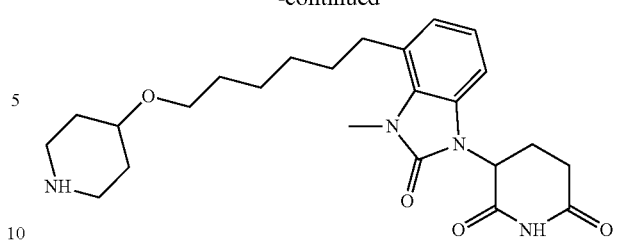

To a solution of tert-butyl 4-[6-[1-(2,6-dioxo-3-piperidyl)-3-methyl-2-oxo-benzimidazol-4-yl]hexoxy] piperidine-1-carboxylate (100 mg, 184 μmol) in DCM (2 mL) was added TFA (767 mg, 6.73 mmol). The reaction mixture was stirred at 25° C. for 1 hr. On completion, the reaction mixture was concentrated to give the title compound (100 mg, 97% yield, TFA) as colorless oil. LC-MS (ESI$^+$) m/z 443.3 (M+H)$^+$.

(f) Step 6—Tert-butyl 3-[2-[[(3S,8S)-3-[[4-[6-[1-(2,6-dioxo-3-piperidyl)-3-methyl-2-oxo-benzimidazol-4-yl]hexoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

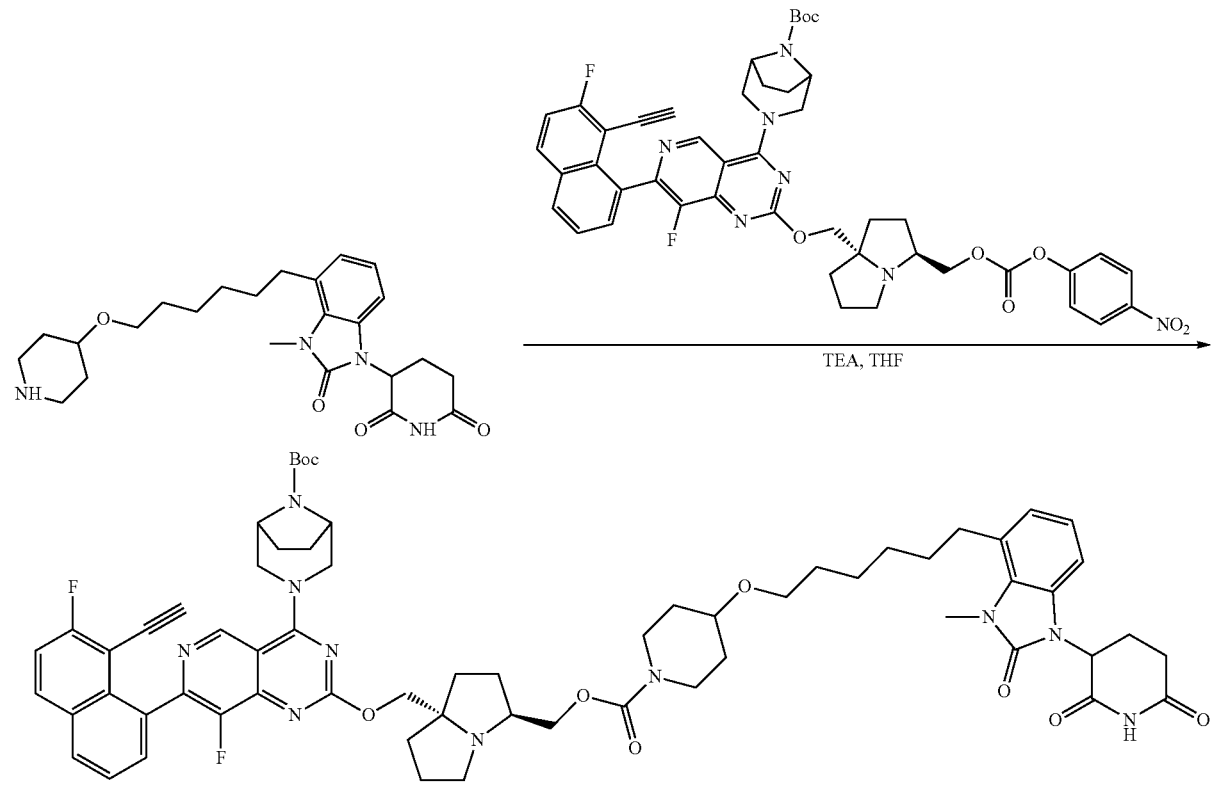

To a solution of 3-[3-methyl-2-oxo-4-[6-(4-piperidyloxy)hexyl]benzimidazol-1-yl]piperidine-2,6-dione (81.3 mg, 146 μmol, TFA) in THF (3 mL) was added TEA (24.6 mg, 243 μmol) and tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70 mg, 81.2 μmol). The mixture was stirred at 25° C. for 2 hrs. On completion, the mixture was concentrated in vacuo to give a residue. The residue was purified by prep-HPLC (column: Phenomenex luna C18 150*25 mm*10 um; mobile phase: [water (FA)-ACN]; gradient: 31%-61% B over 10 min) give the title compound (45 mg, 45% yield, FA) as a white solid. $^1$H NMR (400 MHz, DMSO-d$_6$) δ 11.09 (s, 1H), 9.09 (s, 1H), 8.28-8.14 (m, 2H), 7.74-7.55 (m, 3H), 6.99-6.89 (m, 2H), 6.88-6.78 (m, 1H), 5.36 (dd, J=5.2, 12.4 Hz, 1H), 4.61-4.51 (m, 1H), 4.47-4.36 (m, 1H), 4.30-4.28 (m, 2H), 4.25-4.18 (m, 1H), 4.13 (d, J=9.6 Hz, 2H), 4.08-4.01 (m, 2H), 3.74-3.57 (m, 4H), 3.53 (s, 3H), 3.40-3.37 (m, 3H), 3.15-3.01 (m, 2H), 2.93-2.82 (m, 3H), 2.78-2.62 (m, 5H), 2.10-1.94 (m, 2H), 1.83 (d, J=5.2 Hz, 2H), 1.79-1.69 (m, 9H), 1.64-1.53 (m, 3H), 1.52-1.48 (m, 2H), 1.46 (s, 9H), 1.43-1.26 (m, 7H); LC-MS (ESI$^+$) m/z 1165.4 (M+H)$^+$.

(g) Step 7—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[6-[1-(2,6-dioxo-3-piperidyl)-3-methyl-2-oxo-benzimidazol-4-yl]hexoxy]piperidine-1-carboxylate (058)

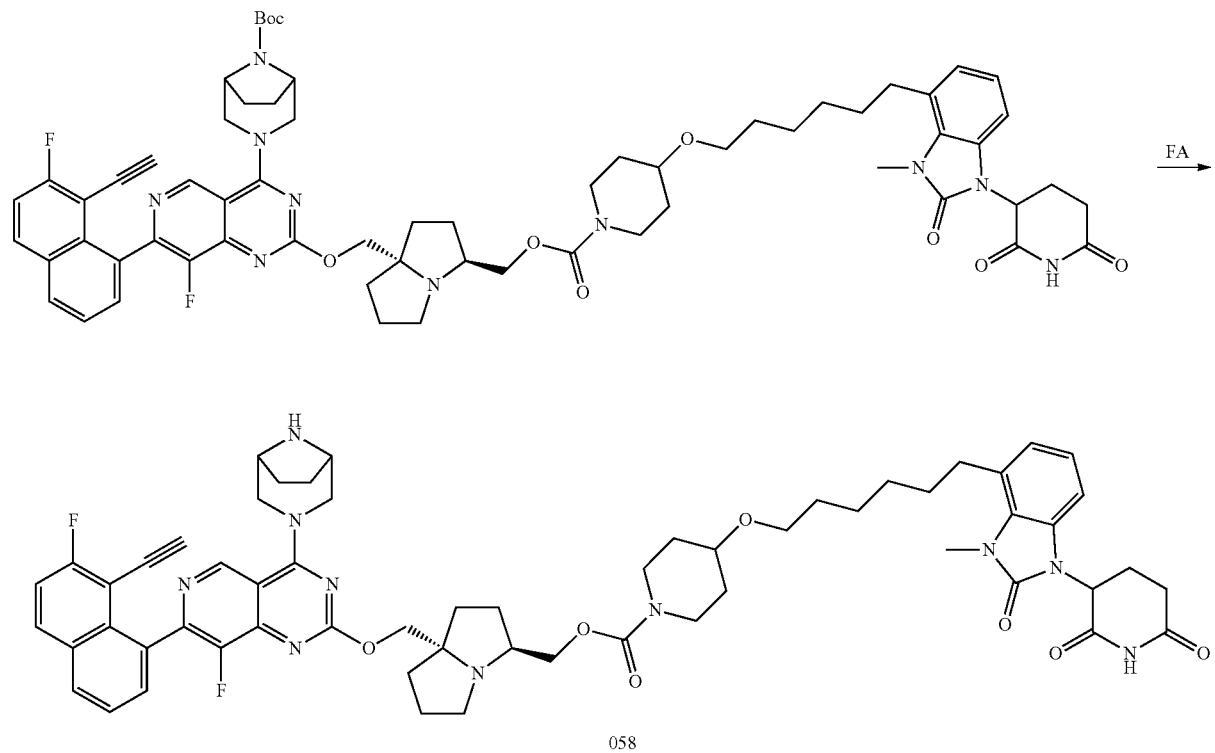

058

A solution of tert-butyl 3-[2-[[(3S,8S)-3-[[4-[6-[1-(2,6-dioxo-3-piperidyl)-3-methyl-2-oxo-benzimidazol-4-yl]hexoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40 mg, 34.3 μmol) in FA (1 mL) was stirred at 25° C. for 10 mins. On completion, the reaction mixture was concentrated in vacuo to give the title compound (20.3 mg, 53% yield, FA) as a yellow solid. $^1$H NMR (400 MHz, DMSO-d$_6$) δ 11.10 (s, 1H), 9.06 (s, 1H), 8.24 (s, 1H), 8.18 (s, 1H), 7.78-7.45 (m, 3H), 7.04-6.88 (m, 2H), 6.84 (dd, J=2.8, 5.6 Hz, 1H), 5.41-5.30 (m, 1H), 4.51 (d, J=11.6 Hz, 1H), 4.37 (d, J=12.0 Hz, 1H), 4.24-4.13 (m, 4H), 4.07 (d, J=10.6 Hz, 1H), 4.02 (s, 1H), 3.72 (s, 3H), 3.68-3.58 (m, 4H), 3.53 (s, 3H), 3.42-3.35 (m, 3H), 3.33-3.26 (m, 1H), 3.07 (d, J=7.6 Hz, 2H), 2.94-2.82 (m, 3H), 2.80-2.57 (m, 4H), 2.10-1.93 (m, 2H), 1.84-1.64 (m, 11H), 1.61-1.44 (m, 5H), 1.42-1.26 (m, 6H); LC-MS (ESI$^+$) m/z 1065.4 (M+H)$^+$.

Example 63. Synthesis of Compound 059

(a) Step 1—Hept-6-ynyl 4-methylbenzenesulfonate

To a solution of hept-6-yn-1-ol (1 g, 8.92 mmol, CAS #63478-76-2) in DCM (20 mL) was added TEA (2.71 g, 26.7 mmol), DMAP (54.4 mg, 445 μmol) and TosCl (2.04 g, 10.7 mmol). The mixture was stirred at 25° C. for 4 hrs. On completion, the mixture was diluted with saturated $H_2O$ (50 mL) and extracted with DCM (20 mL×3). The combined organic layers were washed with brine 50 mL, dried over $Na_2SO_4$, filtered and concentrated in vacuo to give a residue. The residue was purified by column chromatography (PE/EA=1/0 to 4/1) to give the title compound (2 g, 84% yield) as colorless oil. $^1$H NMR (400 MHz, DMSO-$d_6$) δ 7.86-7.72 (m, 2H), 7.48 (d, J=8.0 Hz, 2H), 4.00 (t, J=6.4 Hz, 2H), 2.73 (t, J=2.4 Hz, 1H), 2.42 (s, 3H), 2.08-2.07 (m, 2H), 1.64-1.49 (m, 2H), 1.39-1.26 (m, 4H).

(b) Step 2—Tert-butyl 4-hept-6-ynoxypiperidine-1-carboxylate

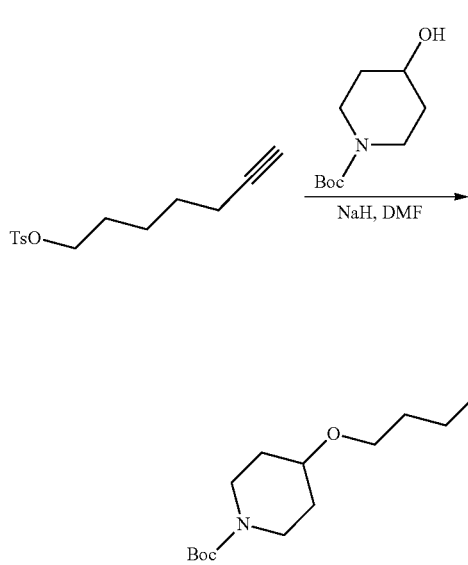

To a solution of tert-butyl 4-hydroxypiperidine-1-carboxylate (906 mg, 4.51 mmol, CAS #109384-19-2) in DMF (10 mL) was added NaH (240 mg, 6.01 mmol, 60% purity) in batches at 0° C. The reaction mixture was stirred at 0° C. for 0.5 hr. Next, hept-6-ynyl 4-methylbenzenesulfonate (0.80 g, 3.00 mmol) was added to the mixture at 25° C., the mixture was stirred at 25° C. for 13.5 hrs. On completion, the reaction mixture was quenched with $H_2O$ (2 mL). The residue was diluted with $H_2O$ (15 mL) and extracted with EA (2×30 mL). The combined organic layers was washed with brine (50 mL) and dried over $Na_2SO_4$, and the filtrate was concentrated in vacuo to give a residue. The residue was purified by column chromatography ($SiO_2$, PE/EA=1:0 to 5:1) to give the title compound (550 mg, 61% yield) as white oil. $^1$H NMR (400 MHz, DMSO-$d_6$) δ 3.66-3.52 (m, 2H), 3.41-3.37 (m, 2H), 3.31 (s, 1H), 3.01 (t, J=9.6 Hz, 2H), 2.73 (t, J=2.4 Hz, 1H), 2.16-2.12 (m, 2H), 1.81-1.68 (m, 2H), 1.54-1.39 (m, 6H), 1.38 (s, 9H), 1.35-1.24 (m, 2H).

(c) Step 3—Tert-butyl 4-[7-[1-(2,6-dioxo-3-piperidyl)-3-methyl-2-oxo-benzimidazol-4-yl]hept-6-ynoxy]piperidine-1-carboxylate

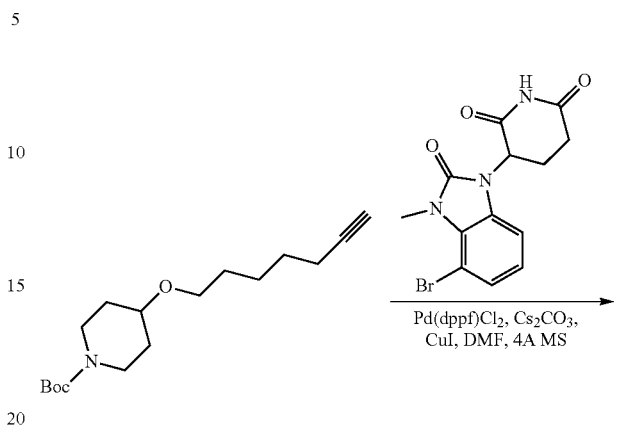

To a solution of tert-butyl 4-hept-6-ynoxypiperidine-1-carboxylate (550 mg, 1.86 mmol) and 3-(4-bromo-3-methyl-2-oxo-benzimidazol-1-yl)piperidine-2,6-dione (314 mg, 930 μmol, CAS #2304754-51-4) in DMF (5 mL) was added CuI (17.7 mg, 93.0 μmol), $Cs_2CO_3$ (909 mg, 2.79 mmol), Pd(PPh$_3$)$_2$Cl$_2$ (65.3 mg, 93.0 μmol) and 4 A MS (93.0 mg) and purged with $N_2$ for 3 times. The mixture was stirred at 115° C. for 4 hrs under $N_2$ atmosphere. On completion, the mixture was quenched with water (10 mL) at 0° C. and extracted with ethyl acetate (10 mL×3), the combined organic phase was dried over brine, filtered and concentrated to give a residue. The residue was purified by reversed phase flash (0.1% FA condition) to give the title compound (200 mg, 38% yield) as a white solid. $^1$H NMR (400 MHz, DMSO-$d_6$) δ 11.10 (s, 1H), 7.14-7.08 (m, 1H), 7.07-7.02 (m, 1H), 6.99 (d, J=8.0 Hz, 1H), 5.38 (dd, J=5.2, 12.4 Hz, 1H), 3.63 (s, 2H), 3.62-3.57 (m, 2H), 3.56-3.54 (m, 1H), 3.42 (t, J=6.0 Hz, 3H), 3.04-2.95 (m, 2H), 2.93-2.83 (m, 1H), 2.77-2.68 (m, 1H), 2.66-2.59 (m, 1H), 2.09-1.96 (m, 1H), 1.78-1.71 (m, 2H), 1.65-1.57 (m, 2H), 1.56-1.39 (m, 6H), 1.38 (s, 9H), 1.35-1.21 (m, 3H). LC-MS (ESI$^+$) m/z 453.2 (M−100+H)$^+$.

(d) Step 4—Tert-butyl 4-[7-[1-(2,6-dioxo-3-piperidyl)-3-methyl-2-oxo-benzimidazol-4-yl]heptoxy]piperidine-1-carboxylate

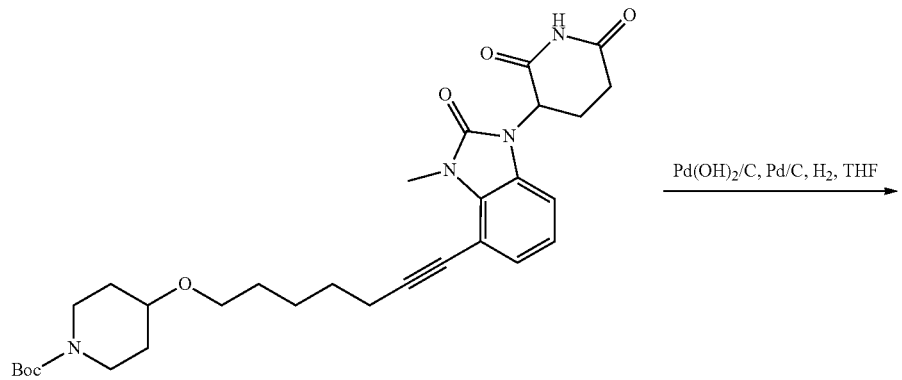

To a solution of tert-butyl 4-[7-[1-(2,6-dioxo-3-piperidyl)-3-methyl-2-oxo-benzimidazol-4-yl]hept-6-ynoxy]piperidine-1-carboxylate (200 mg, 361 μmol) in THF (5 mL) was added Pd/C (1.00 g, 939 μmol, 10% purity) and Pd(OH)$_2$ (100 mg, 712 μmol) under N$_2$. The suspension was degassed under vacuo and purged with H$_2$ several times. The mixture was stirred under H$_2$ (15 psi) at 25° C. for 5 hrs. On completion, the mixture was filtered and concentrated in vacuo to give the title compound (120 mg, 59% yield) was obtained as a brown solid. $^1$H NMR (400 MHz, DMSO-d$_6$) δ 11.08 (s, 1H), 6.99-6.90 (m, 2H), 6.88-6.84 (m, 1H), 5.36 (dd, J=5.2, 12.6 Hz, 1H), 3.60-3.58 (m, 3H), 3.54 (s, 3H), 3.47 (s, 1H), 3.41-3.36 (m, 4H), 3.00 (t, J=10.0 Hz, 3H), 2.93-2.82 (m, 4H), 2.03-1.95 (m, 1H), 1.76 (d, J=3.6 Hz, 1H), 1.60-1.55 (m, 2H), 1.51-1.44 (m, 3H), 1.38 (s, 9H), 1.35 (s, 2H), 1.31 (d, J=3.6 Hz, 3H); LC-MS (ESI$^+$) m/z 557.3 (M+H)$^+$.

(e) Step 5—3-[3-Methyl-2-oxo-4-[7-(4-piperidyloxy)heptyl]benzimidazol-1-yl]piperidine-2,6-dione

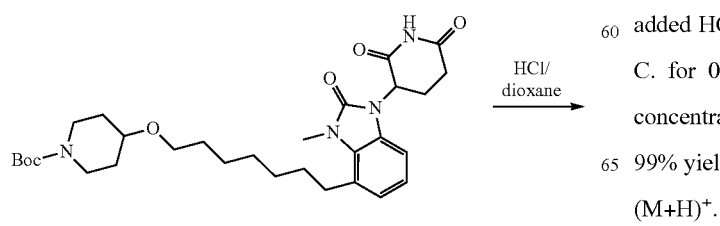

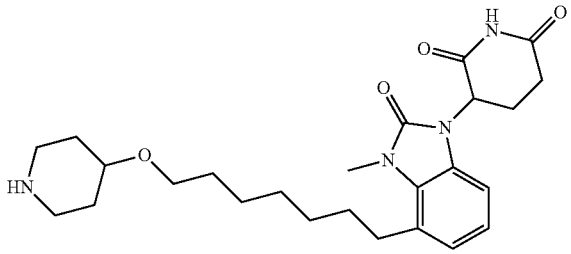

To a solution of tert-butyl 4-[7-[1-(2,6-dioxo-3-piperidyl)-3-methyl-2-oxo-benzimidazol-4-yl]heptoxy]piperidine-1-carboxylate (100 mg, 179 μmol) in DCM (1 mL) was added HCl/dioxane (1 mL). The mixture was stirred at 25° C. for 0.5 hr. On completion, the reaction mixture was concentrated in vacuo to give the title compound (88 mg, 99% yield, HCl) as a brown solid. LC-MS (ESI$^+$) m/z 457.3 (M+H)$^+$.

(f) Step 6—Tert-butyl 3-[2-[[(3S,8S)-3-[[4-[7-[1-(2,6-dioxo-3-piperidyl)-3-methyl-2-oxo-benzimidazol-4-yl]heptoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

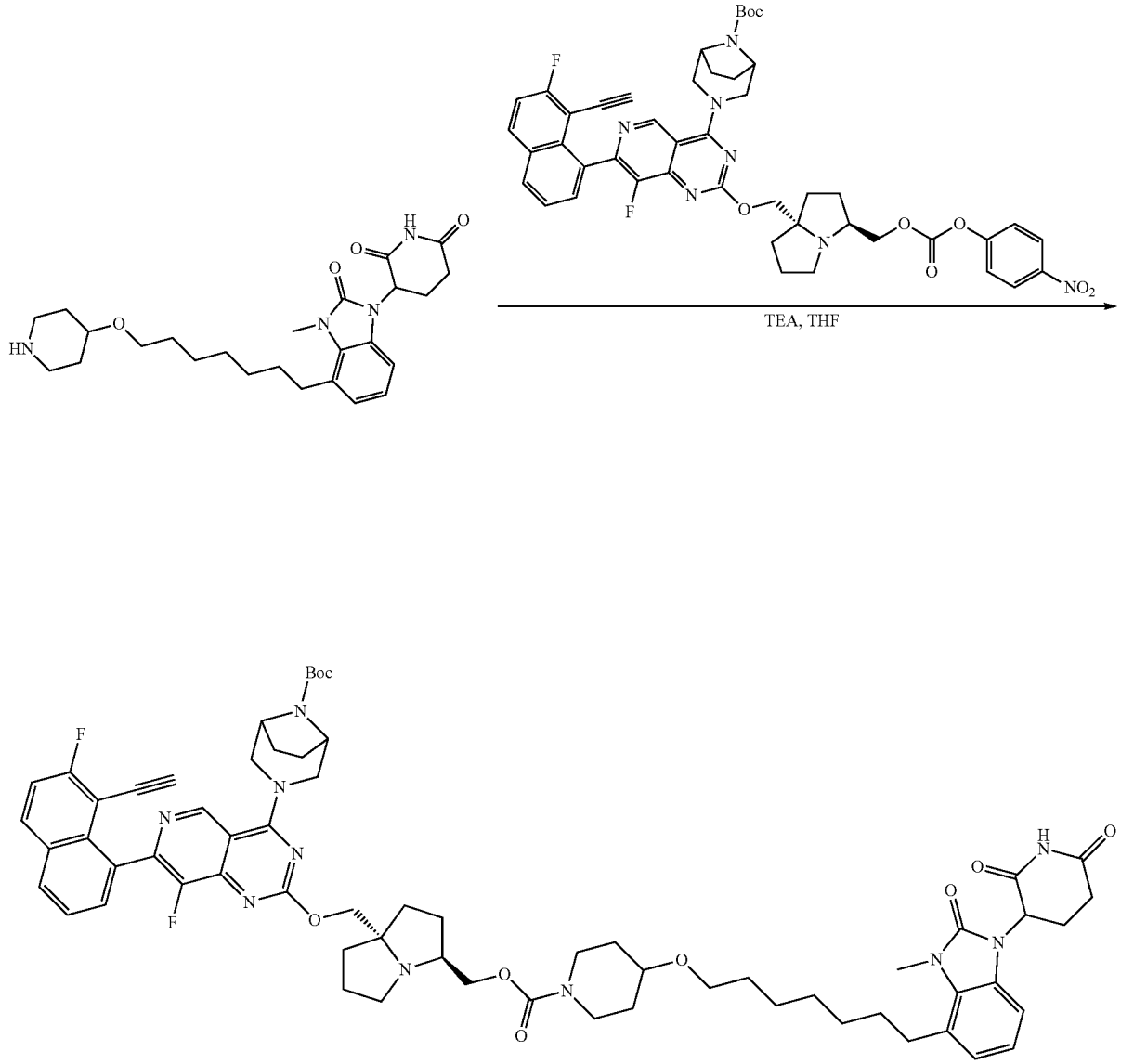

To a solution of 3-[3-methyl-2-oxo-4-[7-(4-piperidyloxy)heptyl]benzimidazol-1-yl]piperidine-2,6-dione (84.6 mg, 171 µmol, HCl) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74.0 mg, 85.8 µmol) in THF (5 mL) was added TEA (8.69 mg, 85.8 µmol) until pH stabilized at 8. The mixture was stirred at 25° C. for 2 hrs. On completion, the reaction mixture was concentrated in vacuo. The residue was purified by prep-HPLC (column: Phenomenex luna C18 150*25 mm*10 um; mobile phase: [water (FA)-ACN]; gradient: 33%-63% B over 10 min) to give the title compound (40 mg, 39% yield) as a yellow solid. $^1$H NMR (400 MHz, DMSO-d$_6$) δ 11.08 (s, 1H), 9.08 (s, 1H), 8.32-8.11 (m, 2H), 7.73-7.54 (m, 3H), 6.96-6.92 (m, 2H), 6.84 (dd, J=3.2, 5.6 Hz, 1H), 5.35 (dd, J=5.2, 12.6 Hz, 1H), 4.55 (d, J=12.4 Hz, 1H), 4.44-4.36 (m, 1H), 4.30-4.35 (m, 2H), 4.25-4.17 (m, 1H), 4.16-4.09 (m, 2H), 4.08-4.02 (m, 1H), 4.01 (s, 1H), 3.70-3.57 (m, 5H), 3.53 (s, 3H), 3.14-3.03 (m, 3H), 2.91-2.82 (m, 3H), 2.78-2.63 (m, 5H), 2.59 (s, 2H), 2.36-2.31 (m, 1H), 2.08-1.95 (m, 2H), 1.91-1.78 (m, 3H), 1.78-1.68 (m, 9H), 1.63-1.53 (m, 3H), 1.46 (s, 9H), 1.39-1.26 (m, 9H); LC-MS (ESI$^+$) m/z 1179.6 (M+H)$^+$.

(g) Step 7—Tert-butyl 3-[2-[[(3S,8S)-3-[[4-[7-[1-(2,6-dioxo-3-piperidyl)-3-methyl-2-oxo-benzimidazol-4-yl]heptoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (059)

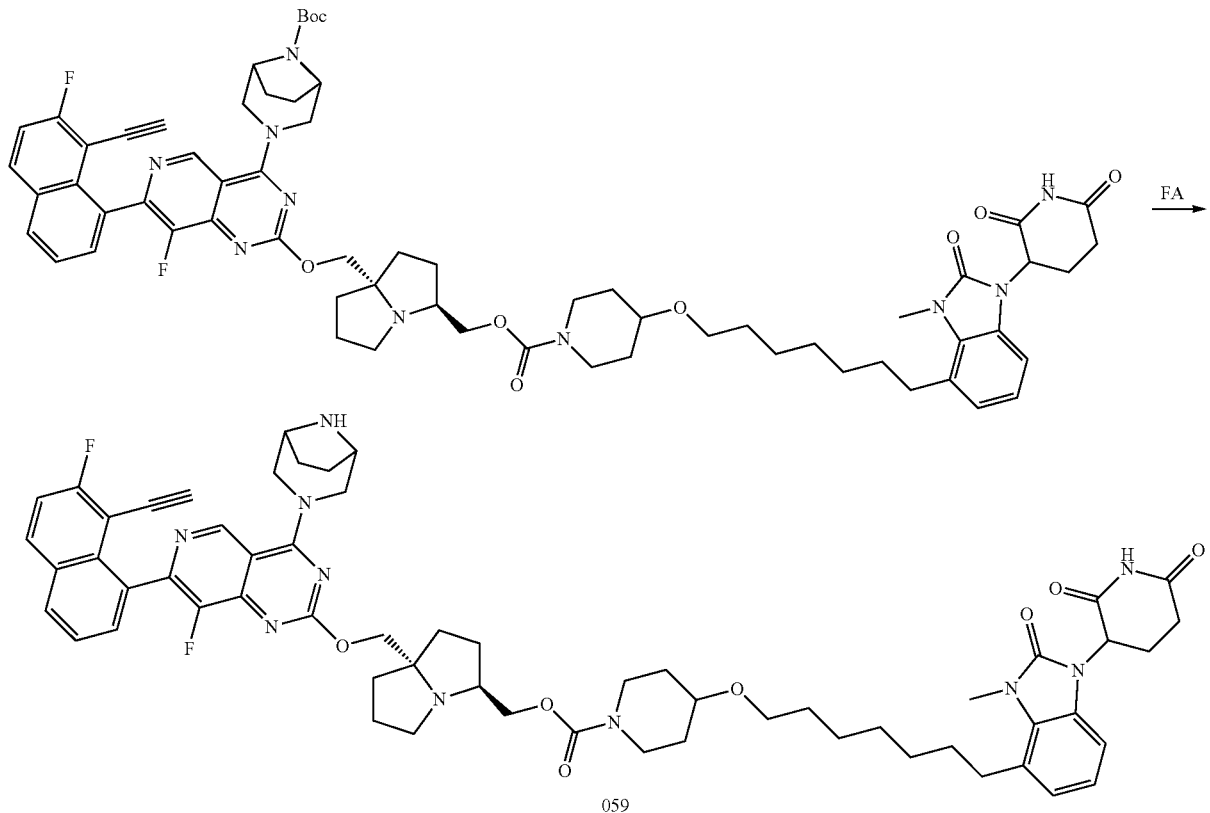

To a solution of tert-butyl 3-[2-[[(3S,8S)-3-[[4-[7-[1-(2,6-dioxo-3-piperidyl)-3-methyl-2-oxo-benzimidazol-4-yl]heptoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (20 mg, 16.3 µmol, FA) in FA (2 mL). The mixture was stirred at 25° C. for 4 hrs. On completion, the reaction mixture was concentrated in vacuo to give the title compound (15.9 mg, 86% yield, FA) as a yellow solid. $^1$H NMR (400 MHz, DMSO-$d_6$) δ 11.09 (s, 1H), 9.05 (s, 1H), 8.25-8.19 (m, 3H), 7.78-7.52 (m, 3H), 7.01-6.89 (m, 2H), 6.84 (dd, J=3.2, 5.6 Hz, 1H), 5.35 (dd, J=5.2, 12.6 Hz, 1H), 4.49 (d, J=11.2 Hz, 1H), 4.38-4.31 (m, 1H), 4.20 (d, J=7.2 Hz, 2H), 4.14 (d, J=10.0 Hz, 2H), 4.06 (d, J=10.4 Hz, 2H), 4.01 (s, 1H), 3.67-3.63 (m, 7H), 3.53 (s, 3H), 3.42-3.35 (m, 4H), 3.15-3.00 (m, 3H), 2.90-2.83 (m, 3H), 2.71-2.62 (m, 2H), 2.09-1.97 (m, 2H), 1.82-1.66 (m, 11H), 1.60-1.54 (m, 2H), 1.50-1.44 (m, 2H), 1.32 (m, 8H); LC-MS (ESI$^+$) m/z 1079.5 (M+H)$^+$.

Example 64. Synthesis of Compound 060

(a) Step 1—Tert-butyl 9-(2-ethoxy-2-oxo-ethylidene)-3-azaspiro[5.5]undecane-3-carboxylate

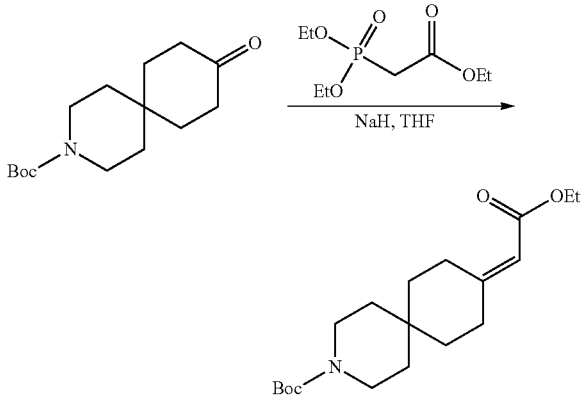

A mixture of ethyl 2-diethoxyphosphorylacetate (6.29 g, 28.0 mmol, 5.57 mL, CAS #867-13-0) and NaH (1.87 g, 46.7 mmol, 60% purity) in THF (65 mL) was stirred at 0° C. for 30 mins. Then a solution of tert-butyl 9-oxo-3-azaspiro[5.5]undecane-3-carboxylate (5 g, 18.7 mmol, CAS #873924-08-4) was added. The reaction mixture was stirred at 25° C. for 1.5 hours. On completion, the reaction mixture was diluted with EA 100 mL and extracted with water 100 mL (20 mL×5). The combined organic layers were dried over Na$_2$SO$_4$, filtered and concentrated under reduced pressure to give a residue. The residue was purified by column chromatography (SiO$_2$, PE:EA=50:1 to PE:EA=10:1) to give the title compound (5.9 g, 98% yield) as colorless oil. $^1$H NMR (400 MHz, DMSO-d$_6$) δ 5.63 (s, 1H), 4.14 (q, J=6.8 Hz, 2H), 3.46-3.33 (m, 4H), 2.91-2.77 (m, 2H), 2.27-2.17 (m, 2H), 1.59-1.51 (m, 4H), 1.47-1.46 (m, 13H), 1.28 (t, J=6.8 Hz, 3H).

(b) Step 2—Tert-butyl 9-(2-ethoxy-2-oxo-ethyl)-3-azaspiro[5.5]undecane-3-carboxylate

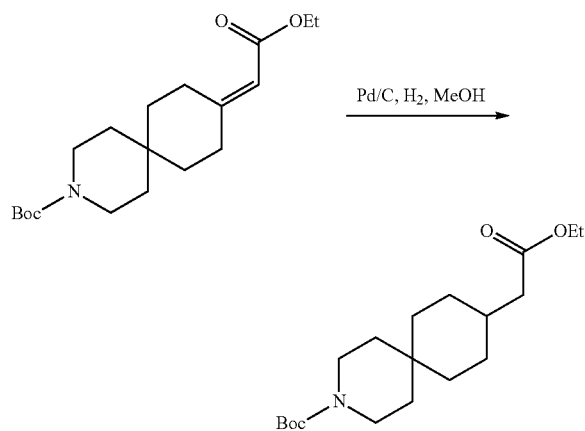

To a solution of tert-butyl 9-(2-ethoxy-2-oxo-ethylidene)-3-azaspiro[5.5]undecane-3-carboxylate (1 g, 2.96 mmol) in MeOH (10 mL) was added Pd/C (0.5 g, 10% purity). The mixture was stirred at 25° C. for 16 hrs under H$_2$ (15 psi). On completion, the reaction mixture was filtered and the filtrate was concentrated in vacuo to give the title compound (1 g, 99% yield) as colorless oil. $^1$H NMR (400 MHz, DMSO-d$_6$) δ 4.13 (q, J=7.2 Hz, 2H), 3.38-3.32 (m, 4H), 2.21 (d, J=7.2 Hz, 2H), 1.82-1.73 (m, 1H), 1.69-1.63 (m, 2H), 1.62-1.53 (m, 2H), 1.47-1.45 (m, 11H), 1.32-1.23 (m, 5H), 1.20-1.12 (m, 4H).

(c) Step 3—Tert-butyl 9-(2-hydroxyethyl)-3-azaspiro[5.5]undecane-3-carboxylate

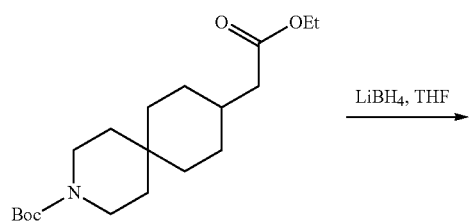

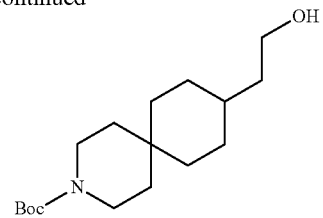

Tert-butyl 9-(2-ethoxy-2-oxo-ethyl)-3-azaspiro[5.5]undecane-3-carboxylate (1 g, 2.95 mmol) in THF (20 mL) was added LiBH$_4$ (2 M, 2.95 mL) at 0° C. The mixture was stirred at 60° C. for 2 hrs. On completion, the reaction mixture was quenched with NH$_4$Cl (20 mL) and concentrated in vacuo. The residue was diluted with water (20 mL) and extracted with DCM (2×40 mL). The combined organic layers was washed with brine (2×30 mL) and dried over Na$_2$SO$_4$, filtered and the filtrate was concentrated in vacuo to give a residue. The residue was purified by column chromatography (SiO$_2$, PE:EA=50:1 to PE:EA=5:1) to give the title compound (800 mg, 91% yield) as colorless oil. $^1$H NMR (400 MHz, DMSO-d$_6$) δ 3.68 (t, J=6.8 Hz, 2H), 3.40-3.27 (m, 4H), 1.69-1.62 (m, 2H), 1.62-1.53 (m, 3H), 1.52-1.46 (m, 4H), 1.45 (s, 9H), 1.41-1.34 (m, 1H), 1.31-1.25 (m, 2H), 1.17-1.03 (m, 4H).

(d) Step 4—Tert-butyl 9-(2-bromoethyl)-3-azaspiro[5.5]undecane-3-carboxylate

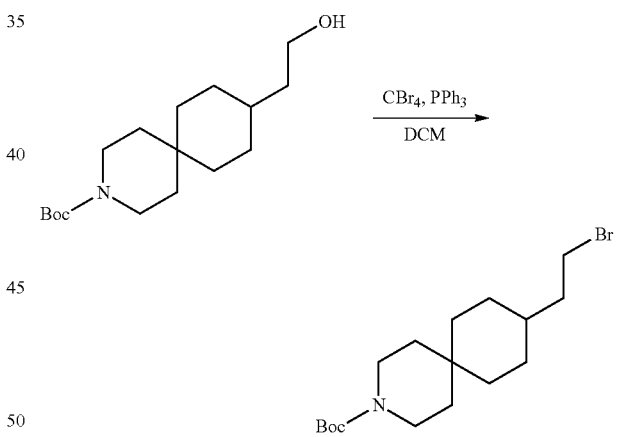

To a solution of tert-butyl 9-(2-hydroxyethyl)-3-azaspiro[5.5]undecane-3-carboxylate (0.8 g, 2.69 mmol) in DCM (10 mL) was added CBr$_4$ (1.34 g, 4.03 mmol) and PPh$_3$ (1.06 g, 4.03 mmol). The mixture was stirred at 25° C. for 16 hrs under N$_2$. On completion, the residue was diluted with water (30 mL) and extracted with DCM (2×20 mL). The combined organic layers was washed with brine (20 mL) and dried over Na$_2$SO$_4$, filtered and the filtrate was concentrated in vacuo to give a residue. The residue was purified by column chromatography (SiO$_2$, PE:EA=100:1 to PE:EA=30:1) to give the title compound (0.7 g, 72% yield) was obtained as a white solid. $^1$H NMR (400 MHz, DMSO-d$_6$) δ 3.44 (t, J=7.2 Hz, 2H), 3.35 (td, J=6.0, 12.0 Hz, 4H), 1.79 (q, J=7.2 Hz, 2H), 1.72-1.64 (m, 2H), 1.60-1.52 (m, 2H), 1.50-1.40 (m, 12H), 1.32-1.27 (m, 2H), 1.18-1.03 (m, 4H).

(e) Step 5—Tert-butyl9-[2-[1-(2,6-dioxo-3-piperidyl)-3-methyl-2-oxo-benzimidazol-4-yl]ethyl]-3-azaspiro[5.5]undecane-3-carboxylate (f) Step 6—3-[4-[2-(3-Azaspiro[5.5]undecan-9-yl)ethyl]-3-methyl-2-oxo-benzimidazol-1-yl] piperidine-2,6-dione

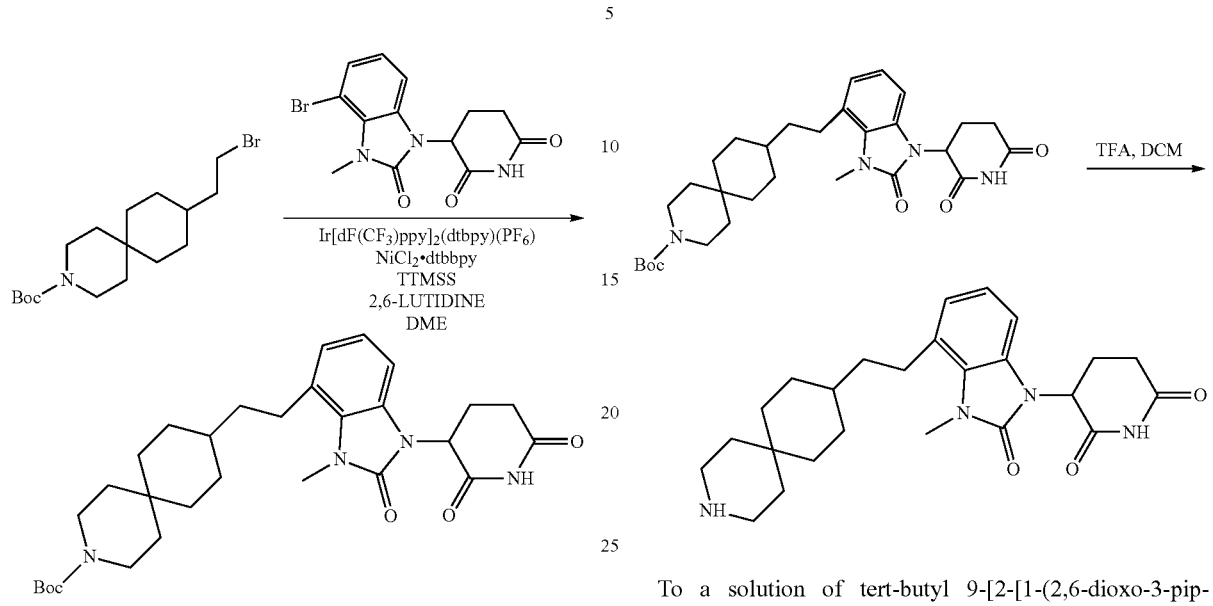

To an 15 mL vial equipped with a stir bar was added tert-butyl 9-(2-bromoethyl)-3-azaspiro[5.5]undecane-3-carboxylate (72.0 mg, 0.2 mmol), 3-(4-bromo-3-methyl-2-oxo-benzimidazol-1-yl)piperidine-2,6-dione (87.9 mg, 260 μmol, CAS #2304754-51-4), Ir[dF(CF$_3$)ppy]$_2$(dtbpy)(PF$_6$) (4.49 mg, 4.00 μmol), NiCl$_2$·dtbbpy (2.39 mg, 6.00 μmol), TTMSS (49.7 mg, 200 μmol), 2,6-LUTIDINE (192 mg, 1.80 mmol, 209 μL) in DME (5 mL). The vial was sealed and placed under nitrogen was added. The reaction was stirred and irradiated with a 10 W blue LED lamp (3 cm away), with cooling water to keep the reaction temperature at 25° C. for 14 hrs. On completion, the reaction mixture was filtered and concentrated in vacuo to give a residue. The residue was purified by reverse phase (0.1% FA condition) to give the title compound (50 mg, 46% yield) as white solid; LC-MS (ESI$^+$) m/z 439.2 (M-Boc+H)$^+$.

To a solution of tert-butyl 9-[2-[1-(2,6-dioxo-3-piperidyl)-3-methyl-2-oxo-benzimidazol-4-yl] ethyl]-3-azaspiro[5.5]undecane-3-carboxylate (50 mg, 92.8 μmol) in DCM (2 mL) was added TFA (614 mg, 0.4 mL). The mixture was stirred at 25° C. for 1 hr. On completion, the reaction mixture was concentrated in vacuo to give the title compound (50 mg, 97% yield, TFA) as brown oil. LC-MS (ESI$^+$) m/z 439.2 (M+H)$^+$.

(g) Step 7—[(3S,8S)-8-[[4-(8-Tert-butoxycarbonyl-3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl9-[2-[1-(2,6-dioxo-3-piperidyl)-3-methyl-2-oxo-benzimidazol-4-yl]ethyl]-3-azaspiro [5.5] undecane-3-carboxylate

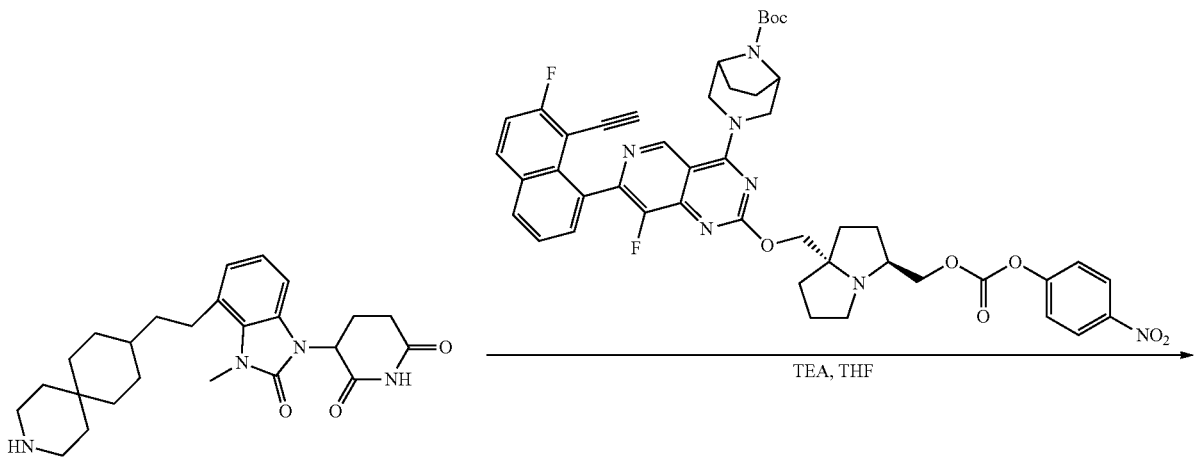

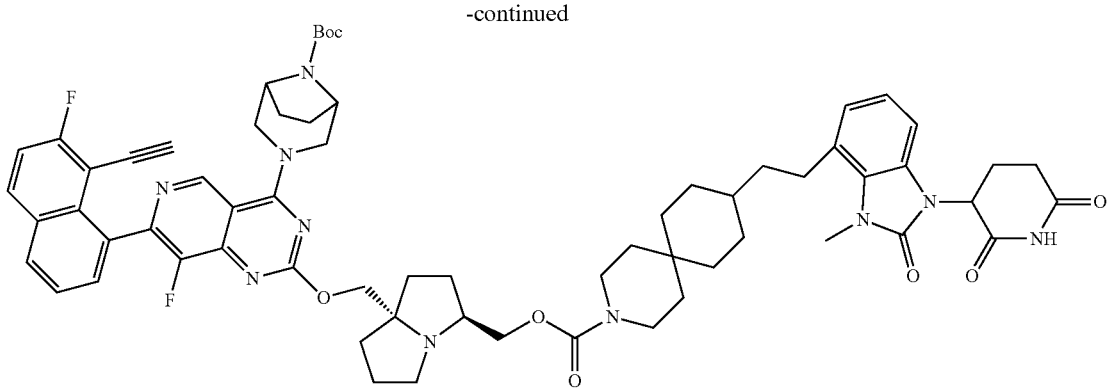

To a solution of 3-[4-[2-(3-azaspiro[5.5]undecan-9-yl)ethyl]-3-methyl-2-oxo-benzimidazol-1-yl] piperidine-2,6-dione (47.4 mg, 85.8 μmol, TFA) and tert-butyl3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74 mg, 85.8 μmol) in THF (2 mL) was added TEA (26.0 mg, 257 μmol, 35.8 μL). The mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 34%-64% B over 11 min) to give the title compound (40 mg, 40% yield) as white solid. $^1$H NMR (400 MHz, DMSO-$d_6$) δ 11.08 (s, 1H), 9.09 (s, 1H), 8.26-8.14 (m, 2H), 7.76-7.54 (m, 3H), 6.94 (d, J=4.8 Hz, 2H), 6.87-6.80 (m, 1H), 5.36 (dd, J=5.6, 12.8 Hz, 1H), 4.61-4.50 (m, 1H), 4.47-4.37 (m, 1H), 4.31 (s, 2H), 4.25-4.17 (m, 1H), 4.16-4.09 (m, 2H), 4.09-4.03 (m, 1H), 4.01 (d, J=2.4 Hz, 1H), 3.70-3.59 (m, 2H), 3.53 (s, 3H), 3.30-3.20 (m, 7H), 2.91-2.83 (m, 3H), 2.80-2.68 (m, 3H), 2.66-2.58 (m, 1H), 2.09-1.96 (m, 2H), 1.89-1.80 (m, 2H), 1.78-1.70 (m, 6H), 1.69-1.49 (m, 7H), 1.46 (s, 9H), 1.44-1.38 (m, 2H), 1.35-1.28 (m, 1H), 1.27-1.19 (m, 2H), 1.18-1.00 (m, 4H), LC-MS (ESI$^+$) m/z 1162.0 (M+H)$^+$.

(h) Step 8—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 9-[2-[1-(2,6-dioxo-3-piperidyl)-3-methyl-2-oxo-benzimidazol-4-yl]ethyl]-3-azaspiro[5.5]undecane-3-carboxylate (060)

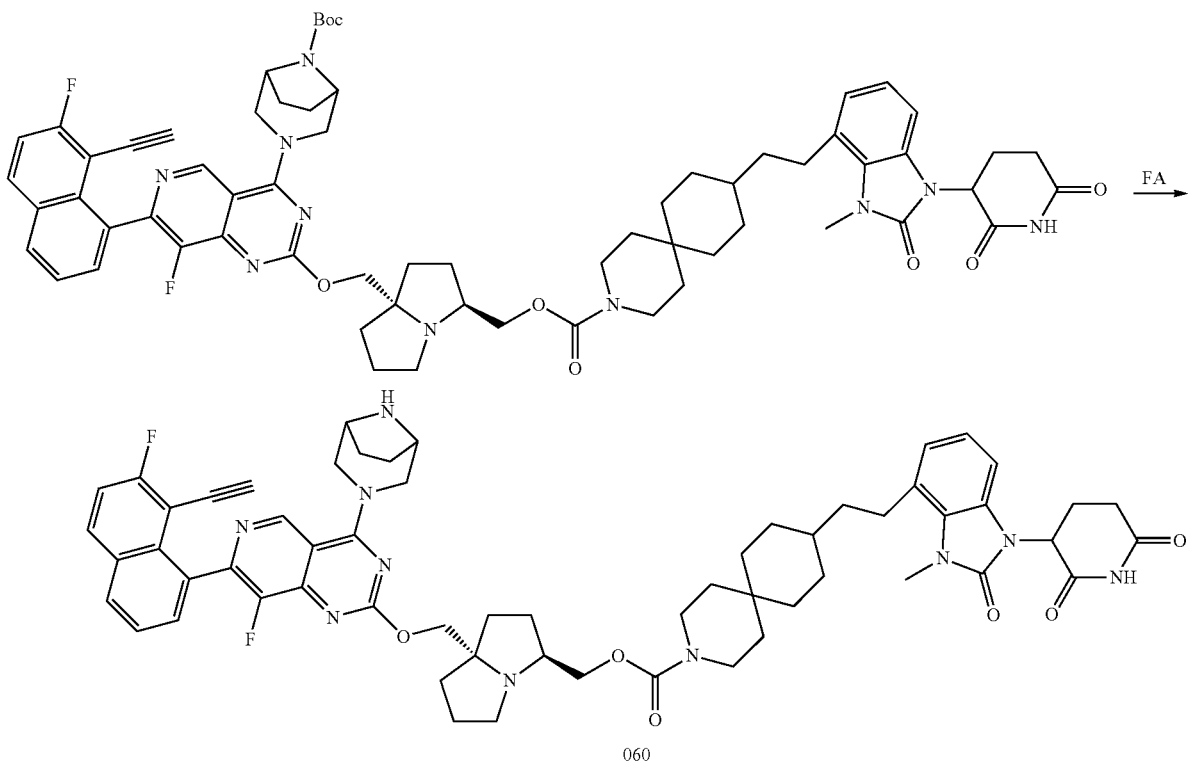

A mixture of [(3S,8S)-8-[[4-(8-tert-butoxycarbonyl-3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 9-[2-[1-(2,6-dioxo-3-piperidyl)-3-methyl-2-oxo-benzimidazol-4-yl]ethyl]-3-azaspiro[5.5]undecane-3-carboxylate (40 mg, 34.4 μmol) in FA (34.4 μmol, 2 mL). The reaction was stirred at 25° C. for 0.5 hr. On completion, the reaction mixture was dried with $N_2$ to give the title compound (34.6 mg, 86% yield, FA) as yellow solid. $^1$H NMR (400 MHz, DMSO-$d_6$) δ 11.09 (s, 1H), 9.05 (s, 1H), 8.22-8.13 (m, 2H), 7.72-7.55 (m, 3H), 6.94 (d, J=4.8 Hz, 2H), 6.87-6.77 (m, 1H), 5.36 (dd, J=4.8, 12.4 Hz, 1H), 4.48 (d, J=11.2 Hz, 1H), 4.34 (d, J=11.6 Hz, 1H), 4.25-4.11 (m, 3H), 4.08-4.00 (m, 2H), 3.67-3.60 (m, 7H), 3.60-3.55 (m, 3H), 3.53 (s, 3H), 2.92-2.81 (m, 3H), 2.79-2.67 (m, 3H), 2.65-2.57 (m, 1H), 2.09-1.95 (m, 2H), 1.81-1.61 (m, 12H), 1.59-1.44 (m, 5H), 1.43-1.38 (m, 2H), 1.36-1.26 (m, 1H), 1.25-1.19 (m, 2H), 1.17-1.00 (m, 4H); LC-MS (ESI$^+$) m/z 1061.0 (M+H)$^+$.

Example 65. Synthesis of Compound 61

(a) Step 1—Tert-butyl 6-(2-ethoxy-2-oxo-ethylidene)-2-azaspiro[3.3]heptane-2-carboxylate

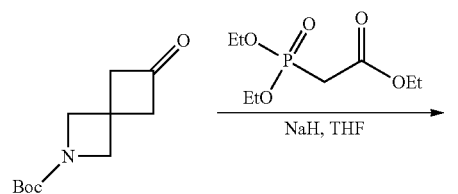

To a solution of ethyl 2-diethoxyphosphorylacetate (7.96 g, 35.5 mmol, CAS #867-13-0) in THF (25 mL) was added NaH (1.5 g, 37.5 mmol, 60% purity) at 0° C., the reaction mixture was stirred at 0° C. for 30 mins, then tert-butyl 6-oxo-2-azaspiro[3.3]heptane-2-carboxylate (5 g, 23.6 mmol, CAS #1181816-12-5) in THF (25 mL) was added, the reaction mixture was stirred at 25° C. for 1 hr. On completion, the reaction mixture was quenched by addition $H_2O$ (1.5 mL), and extracted with ethyl acetate (15 mL×3), the combined organic phase was dried over anhydrous sodium sulfate, filtered and concentrated to give a residue. The residue was purified by column chromatography (SiO$_2$, PE/EA=20:1 to 8:1) to give the title compound (6 g, 90% yield) as a white oil. $^1$H NMR (400 MHz, CDCl$_3$) δ 5.66-5.64 (m, 1H), 4.15 (q, J=7.2 Hz, 2H), 4.02-3.92 (m, 4H), 3.29 (d, J=2.0 Hz, 2H), 3.01 (s, 2H), 1.44 (s, 9H), 1.27 (t, J=7.2 Hz, 3H).

(b) Step 2—Tert-butyl 6-(2-ethoxy-2-oxo-ethyl)-2-azaspiro[3.3]heptane-2-carboxylate

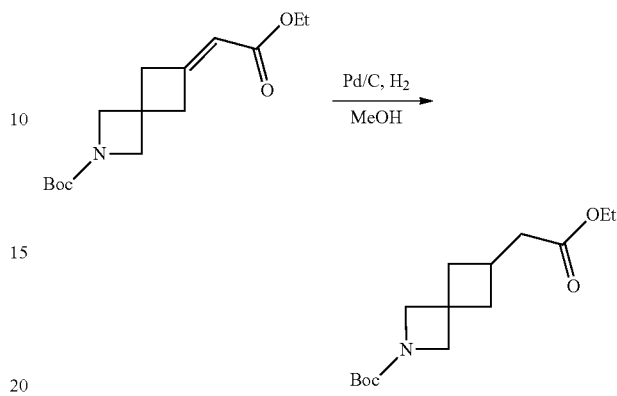

To a solution of tert-butyl 6-(2-ethoxy-2-oxo-ethylidene)-2-azaspiro[3.3]heptane-2-carboxylate (500 mg, 1.78 mmol) in MeOH (5 mL) was added Pd/C (250 mg, 234. μmol, 10% purity) under $H_2$ (15 Psi). The mixture was stirred at 25° C. for 12 hrs. On completion, the mixture was filtered gave filtrate and concentrated in vacuo to give the title compound (450 mg, 82% yield) as a white oil. LC-MS (ESI$^+$) m/z 228.0 (M+H−56)$^+$.

(c) Step 3—Tert-butyl 6-(2-hydroxyethyl)-2-azaspiro[3.3]heptane-2-carboxylate

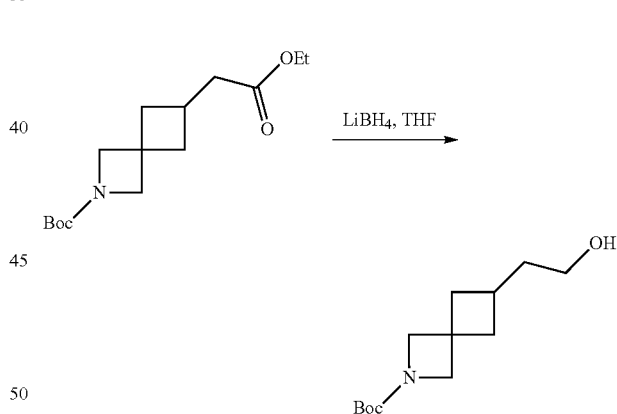

To a solution of tert-butyl 6-(2-ethoxy-2-oxo-ethyl)-2-azaspiro[3.3]heptane-2-carboxylate (450 mg, 1.59 mmol) and in THF (3 mL) was added LiBH$_4$ (2 M, 1.75 mL) slowly at 0° C. under $N_2$. The mixture was stirred at 25° C. for 6 hours. The mixture was stirred at 60° C. for 2 hours. On completion, the reaction mixture was quenched by NH$_4$Cl (10 mL) at 0° C., and then extracted with EA 30 mL (10 mL×3). The combined organic phase was washed with saturated sodium chloride solution 40 mL (20 mL×2), dried over anhydrous sodium sulfate, filtered and concentrated to give the title compound (370 mg, 96% yield) as a white oil. $^1$H NMR (400 MHz, CDCl$_3$) δ 3.93 (s, 2H), 3.80 (s, 2H), 3.58 (t, J=6.8 Hz, 2H), 2.35-2.20 (m, 3H), 1.85-1.77 (m, 2H), 1.64 (q, J=6.8 Hz, 2H), 1.43 (s, 9H).

(d) Step 4—Tert-butyl 6-(2-bromoethyl)-2-azaspiro[3.3]heptane-2-carboxylate

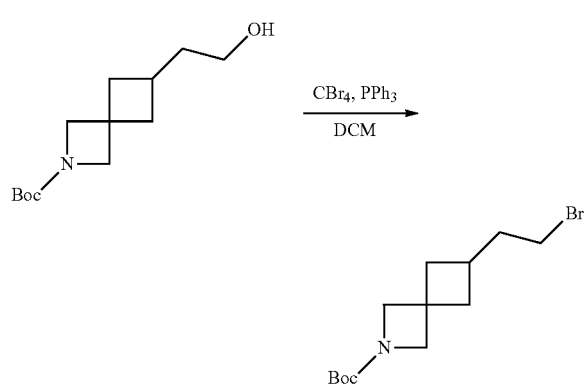

To a solution of tert-butyl 6-(2-hydroxyethyl)-2-azaspiro[3.3]heptane-2-carboxylate (320 mg, 1.33 mmol) in DCM (4 mL) was added PPh$_3$ (695 mg, 2.65 mmol) and CBr$_4$ (879 mg, 2.65 mmol) at 0° C. The mixture was stirred at 25° C. for 6 hrs. On completion, the mixture was diluted with water (50 mL) at 0° C. and extracted with DCM (5 mL×3), the combined organic phase was dried over anhydrous sodium sulfate, filtered and concentrated to give a residue. The residue was purified by column chromatography (SiO$_2$, PE/EA=0 to 5%) to give the title compound (160 mg, 37% yield) as white oil. $^1$H NMR (400 MHz, CDCl$_3$) δ 3.94 (s, 2H), 3.80 (s, 2H), 3.30 (t, J=6.8 Hz, 2H), 2.37-2.25 (m, 3H), 1.93 (q, J=6.8 Hz, 2H), 1.86-1.76 (m, 2H), 1.43 (s, 9H).

(e) Step 5—Tert-butyl 6-[2-[1-(2,6-dioxo-3-piperidyl)-3-methyl-2-oxo-benzimidazol-4-yl]ethyl]-2-azaspiro[3.3]heptane-2-carboxylate

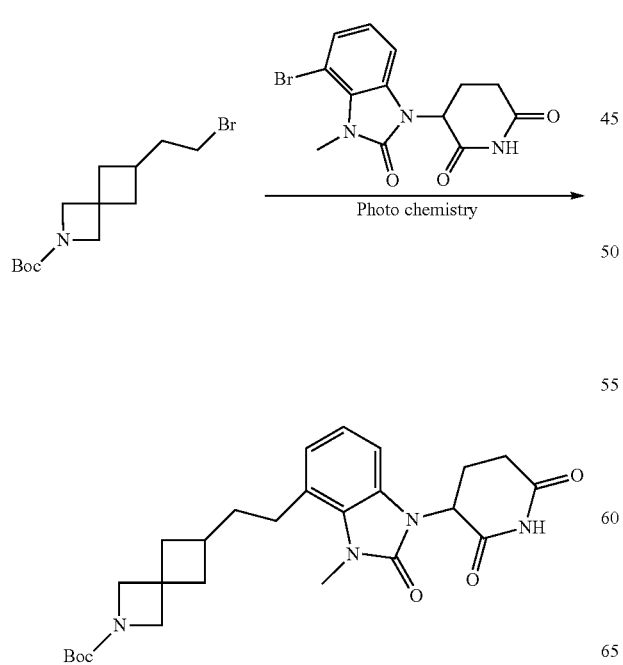

To an 15 mL vial equipped with a stir bar was added 3-(4-bromo-3-methyl-2-oxo-benzimidazol-1-yl) piperidine-2,6-dione (94.0 mg, 278 μmol, CAS #2304754-51-4), tert-butyl6-(2-bromoethyl)-2-azaspiro[3.3]heptane-2-carboxylate (110 mg, 361 μmol), Ir[dF(CF$_3$)ppy]$_2$(dtbpy)(PF$_6$) (6.24 mg, 5.56 μmol), NiCl$_2$·dtbbpy (3.32 mg, 8.34 μmol), TTMSS (69.1 mg, 278 μmol), 2,6-Lutidine (268 mg, 2.50 mmol) in DME (5 mL). The vial was sealed and placed under nitrogen was added. The reaction was stirred and irradiated with a 10 W blue LED lamp (3 cm away), with cooling water to keep the reaction temperature at 25° C. for 14 hrs. On completion, the mixture was filtered gave filtrate and concentrated in vacuo to give a residue. The residue was purified by reversed phase flash chromatography (0.1% FA condition) to give the title compound (45 mg, 33% yield) as a yellow solid. LC-MS (ESI$^+$) m/z 383.1 (M−100+H)$^+$.

(f) Step 6—3-[4-[2-(2-Azaspiro[3.3]heptan-6-yl)ethyl]-3-methyl-2-oxo-benzimidazol-1-yl]piperidine-2,6-dione

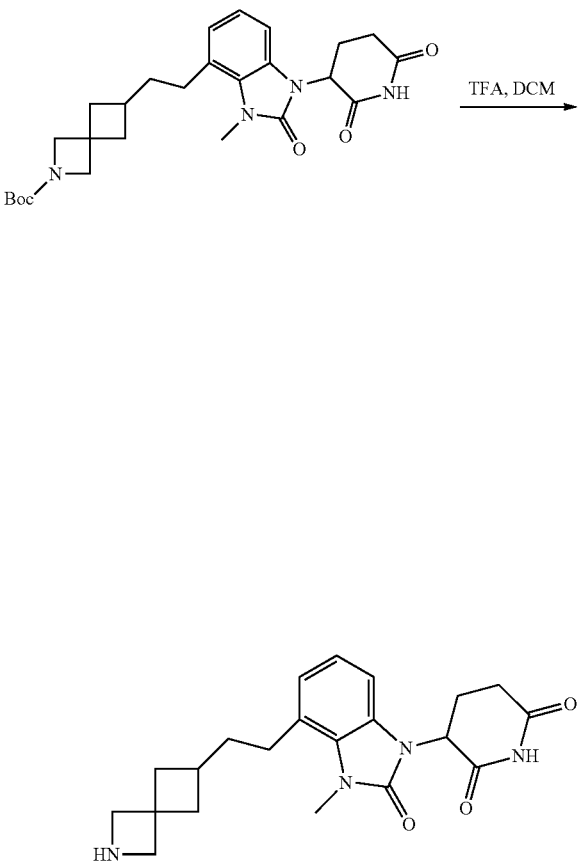

To a solution of tert-butyl 6-[2-[1-(2,6-dioxo-3-piperidyl)-3-methyl-2-oxo-benzimidazol-4-yl]ethyl]-2-azaspiro[3.3]heptane-2-carboxylate (40 mg, 82.8 μmol) in DCM (1 mL) was added TFA (280 mg, 2.46 mmol). The mixture was stirred at 25° C. for 0.5 hr. On completion, the reaction mixture was concentrated in vacuo to give the title compound (41 mg, 99% yield, TFA) as a yellow oil. LC-MS (ESI$^+$) m/z 383.1 (M+H)$^+$.

(g) Step 7—3-[2-[[(3S,8S)-3-[[6-[2-[1-(2,6-dioxo-3-piperidyl)-3-methyl-2-oxo-benzimidazol-4-yl]ethyl]-2-azaspiro[3.3]heptane-2-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

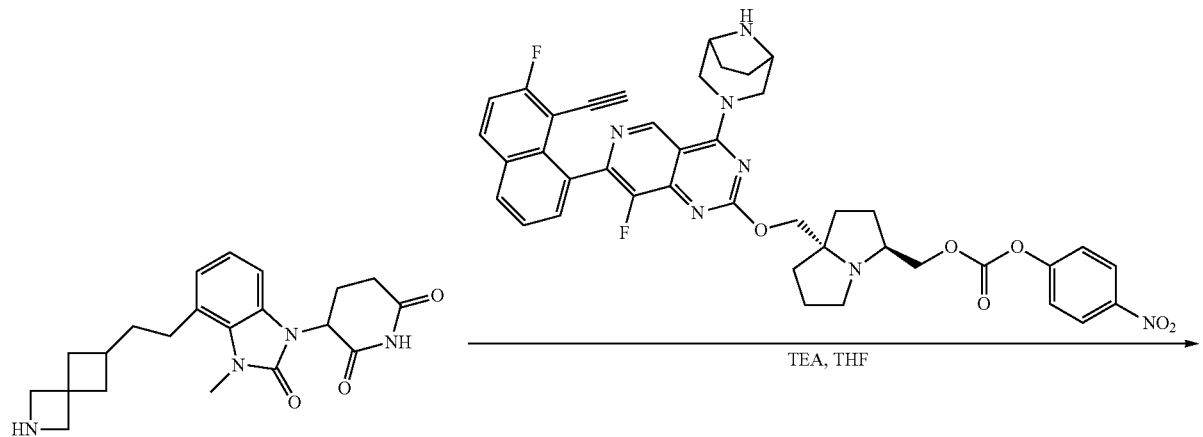

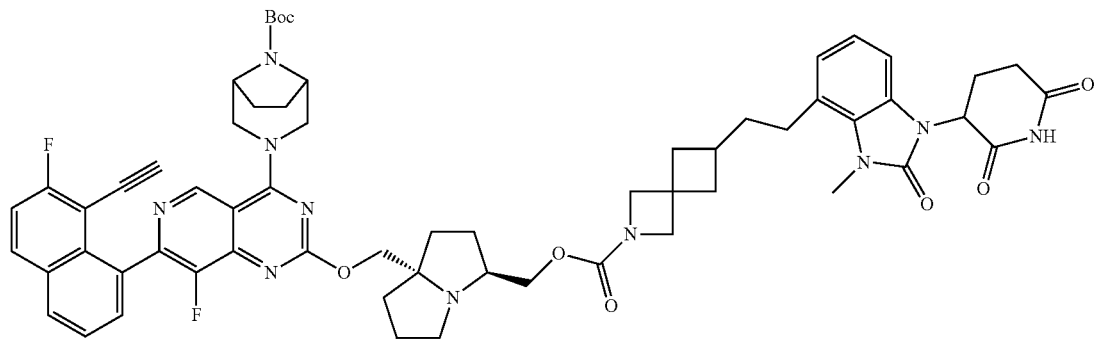

To a solution of 3-[4-[2-(2-azaspiro[3.3]heptan-6-yl)ethyl]-3-methyl-2-oxo-benzimidazol-1-yl] piperidine-2,6-dione (40.3 mg, 81.2 μmol, TFA) in THF (2 mL) was added TEA (16.4 mg, 162 μmol) and tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (46.6 mg, 54.1 μmol). The mixture was stirred at 25° C. for 3 hrs. On completion, the reaction mixture was concentrated in vacuo. The residue was purified by prep-HPLC (Phenomenex luna C18 150*25 mm*10 um; mobile phase: [water (FA)-ACN]; gradient: 31%-61% B over 10 min) to give the title compound (15 mg, 24% yield) as a yellow solid. LC-MS (ESI$^+$) m/z 1105.4 (M+H)$^+$.

(h) Step 8—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 6-[2-[1-(2,
6-dioxo-3-piperidyl)-3-methyl-2-oxo-benzimidazol-
4-yl]ethyl]-2-azaspiro[3.3]heptane-2-carboxylate
(061)

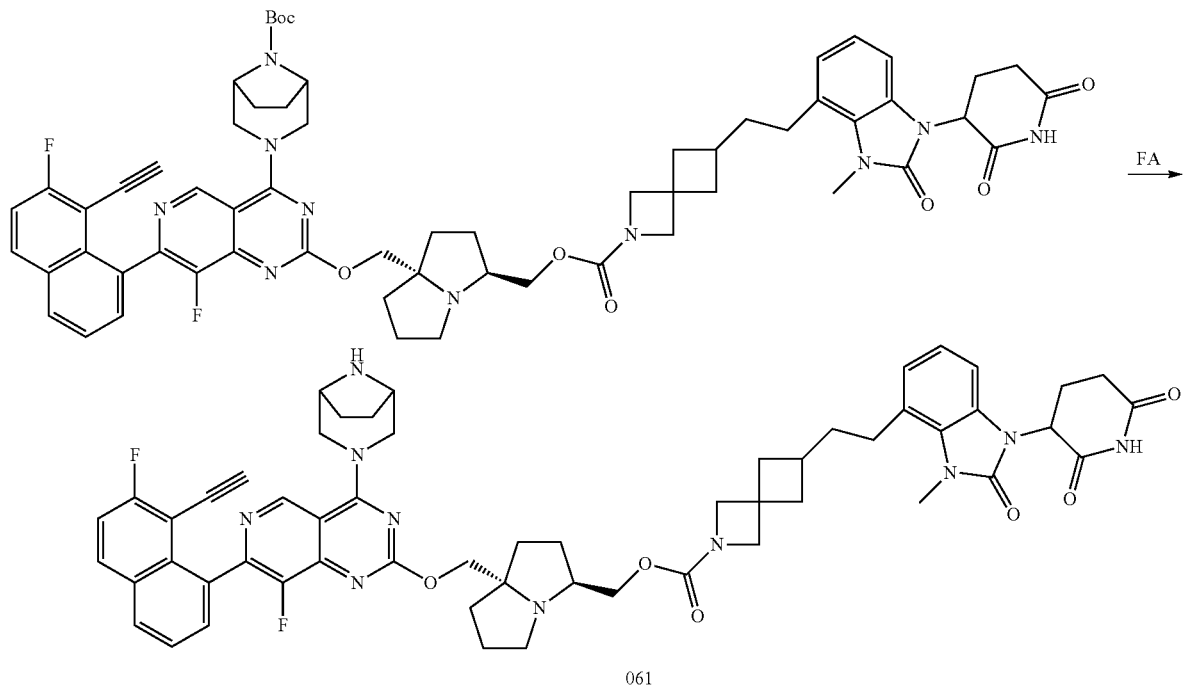

A mixture of tert-butyl 3-[2-[[(3S,8S)-3-[[6-[2-[1-(2,6-dioxo-3-piperidyl)-3-methyl-2-oxo-benzimidazol-4-yl]ethyl]-2-azaspiro[3.3]heptane-2-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (15 mg, 13.5 µmol) in FA (0.5 mL) was stirred at 25° C. for 0.5 hr. On completion, the reaction mixture was concentrated in vacuo. The residue was purified by prep-HPLC (Welch Xtimate C18 150*25 mm*5 µm; mobile phase: [water (FA)-ACN]; gradient: 11%-41% B over 15 min) to give the title compound (6.98 mg, 48% yield, FA) as a white solid. $^1$H NMR (400 MHz, DMSO-$d_6$) δ 11.09 (s, 1H), 9.05 (s, 1H), 8.29-8.13 (m, 3H), 7.73-7.55 (m, 3H), 6.97-6.90 (m, 2H), 6.82 (dd, J=3.2, 5.8 Hz, 1H), 5.35 (dd, J=5.2, 12.4 Hz, 1H), 4.47 (d, J=11.6 Hz, 1H), 4.34 (d, J=12.4 Hz, 1H), 4.21-3.99 (m, 5H), 3.91 (s, 2H), 3.80 (s, 2H), 3.66-3.57 (m, 6H), 3.25-3.19 (m, 2H), 2.92-2.83 (m, 1H), 2.79-2.61 (m, 6H), 2.31-2.23 (m, 2H), 2.19-2.09 (m, 1H), 2.08-1.93 (m, 2H), 1.84-1.61 (m, 14H), 1.55-1.45 (m, 1H); LC-MS (ESI$^+$) m/z 1005.1 (M+H)$^+$.

Example 66. Synthesis of Compound 062

(a) Step 1—Benzyl 4-(methylsulfonyloxymethyl)
piperidine-1-carboxylate

To a solution of benzyl 4-(hydroxymethyl)piperidine-1-carboxylate (10.0 g, 40.1 mmol) in DCM (100 mL) was added methylsulfonyl methanesulfonate (10.4 g, 60.1 mmol) and TEA (12.1 g, 120 mmol) at 0° C. The mixture was stirred at 25° C. for 2 hrs. On completion, the reaction mixture was diluted with H$_2$O (100 ml) and extracted with DCM (3×200 mL). The combined organic layers were washed with brine (100 mL), dried over Na$_2$SO$_4$, filtered and the filtrate was concentrated under reduced pressure to give the title compound (14.0 g, crude) was obtained as yellow oil. LC-MS (ESI$^+$) m/z 327.9 (M+H)$^+$.

(b) Step 2—Benzyl 4-[(1-tert-butoxycarbonyl-4-
piperidyl)oxymethyl]piperidine-1-carboxylate

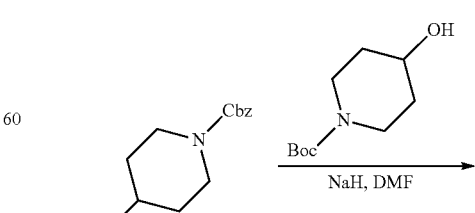

-continued

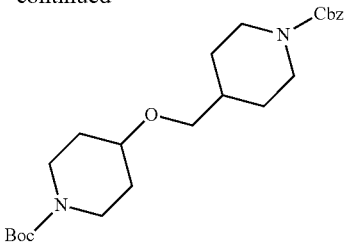

To a solution of tert-butyl 4-hydroxypiperidine-1-carboxylate (8.61 g, 42.7 mmol, CAS #109384-19-2) in DMF (140 mL) was added NaH (2.57 g, 64.1 mmol, 60% purity) at 0° C. for 30 min, then added benzyl 4-(methylsulfonyloxymethyl)piperidine-1-carboxylate (14.0 g, 42.7 mmol). The mixture was stirred at 25° C. for 15 mins, then the mixture was stirred at 60° C. for 16 hrs. On completion, the mixture was diluted with H$_2$O (30 mL) and extracted with EA (3×50 mL). The combined organic layers were washed with brine (3×20 mL), dried over anhydrous Na$_2$SO$_4$, filtered and the filtrate was concentrated in vacuo. The residue was purified by column chromatography (SiO$_2$, Petroleum ether/Ethyl acetate=50/1 to 20/1) to give the title compound (3.50 g, 18% yield) as white solid. $^1$H NMR (400 MHz, CDCl$_3$) δ 7.27 (s, 5H), 5.11-4.98 (m, 2H), 4.23-4.03 (m, 2H), 3.75-3.52 (m, 2H), 3.41-3.29 (m, 1H), 3.26-3.16 (m, 2H), 3.12-2.90 (m, 2H), 2.79-2.59 (m, 2H), 1.84-1.59 (m, 5H), 1.54 (d, J=5.2 Hz, 1H), 1.47-1.41 (m, 1H), 1.40-1.34 (m, 9H), 1.15-1.02 (m, 2H); LC-MS (ESI$^+$) m/z 333.1 (M+H-Boc)$^+$.

(c) Step 3—Tert-butyl 4-(4-piperidylmethoxy)piperidine-1-carboxylate

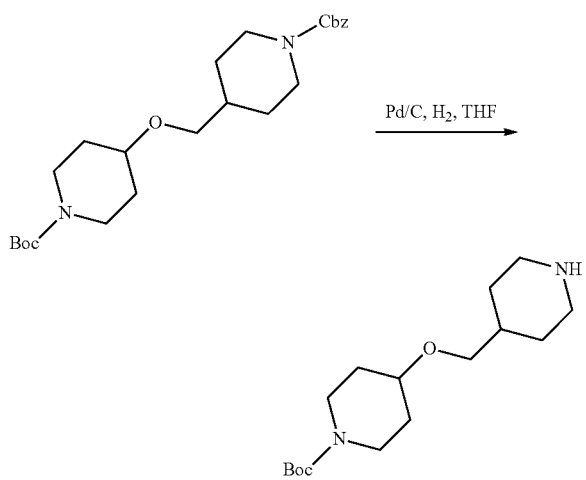

To a solution of benzyl 4-[(1-tert-butoxycarbonyl-4-piperidyl)oxymethyl]piperidine-1-carboxylate (1.50 g, 3.47 mmol) in MeOH (15 mL) was added Pd/C (700 mg, 657 μmol, 10% purity) and Pd(OH)$_2$/C (700 mg, 20% purity). The mixture was stirred at 25° C. for 2 hrs. The suspension was degassed and purged with H$_2$ for 3 times. The mixture was stirred at 25° C. for 1 hr under H$_2$ (15 Psi) atmosphere. On completion, the reaction mixture was filtered and the filtrate was concentrated to give the title compound (800 mg, 77% yield) as white solid. $^1$H NMR (400 MHz, CDCl$_3$) δ 3.79-3.64 (m, 2H), 3.44-3.37 (m, 1H), 3.32-3.25 (m, 2H), 3.15-3.04 (m, 4H), 1.86-1.64 (m, 9H), 1.54-1.50 (m, 1H), 1.47-1.45 (m, 9H), 1.19-1.08 (m, 2H); LC-MS (ESI$^+$) m/z 299.2 (M+H)$^+$.

(d) Step 4—Tert-butyl 4-[[1-[[1-(2,6-dioxo-3-piperidyl)-3-methyl-2 oxo-benzimidazol-4-yl]methyl]4-piperidyl]methoxy]piperidine-1-carboxylate

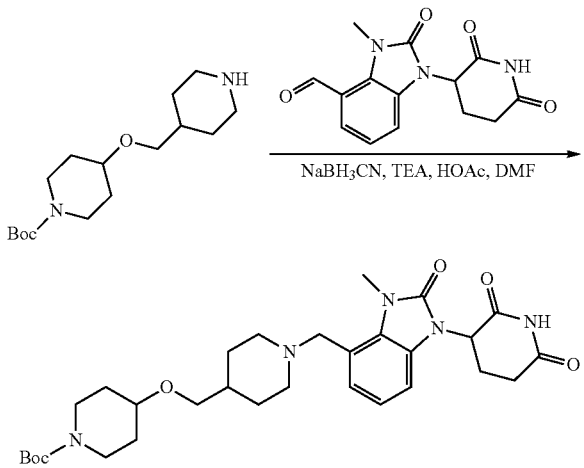

To a solution of tert-butyl 4-(4-piperidylmethoxy)piperidine-1-carboxylate (540 mg, 1.81 mmol) in DMF (5 mL) was added TEA (70.4 mg, 696 μmol) and HOAc (41.8 mg, 696 μmol). Then added 1-(2,6-dioxo-3-piperidyl)-3-methyl-2 oxo-benzimidazole-4-carbaldehyde (400 mg, 1.39 mmol) and NaBH$_3$CN (131 mg, 2.09 mmol). The mixture was stirred at 40° C. for 1 hr. On completion, the mixture was concentrated in vacuo. The crude product was purified by reversed-phase HPLC (column: Daisogel SP ODS RPS 150*25 mm*5 um; mobile phase: [water (NH4HCO3)-ACN]; gradient: 47%-77% B over 10 min) to give the title compound (75.0 mg, 7% yield) as white solid. $^1$H NMR (400 MHz, DMSO-d$_6$) δ 11.16-11.01 (m, 1H), 7.10-7.03 (m, 1H), 6.98-6.92 (m, 1H), 6.91-6.82 (m, 1H), 5.43-5.31 (m, 1H), 3.66 (s, 3H), 3.63-3.52 (m, 4H), 3.27-3.20 (m, 3H), 3.08-2.96 (m, 2H), 2.91-2.78 (m, 3H), 2.73-2.59 (m, 3H), 2.05-1.90 (m, 3H), 1.78-1.59 (m, 4H), 1.56-1.45 (m, 1H), 1.43-1.24 (m, 10H), 1.18-1.04 (m, 2H).

(e) Step 5—3-[3-Methyl-2-oxo-4-[[4-(4piperidyloxymethyl)-1-piperidyl]methyl]benzimidazol-1yl] piperidine-2,6-dione

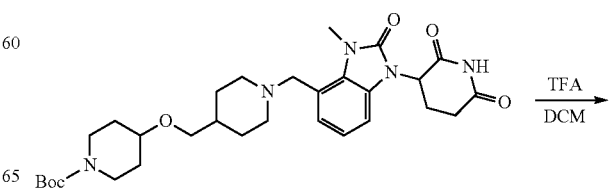

-continued

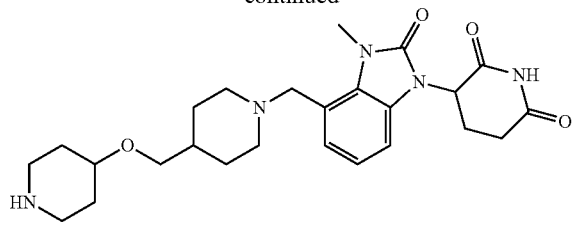

To a solution of tert-butyl 4-[[1-[[1-(2,6-dioxo-3-piperidyl)-3-methyl-2-oxo-benzimidazol-4 yl]methyl]-4-piperidyl]methoxy]piperidine-1-carboxylate (75.0 mg, 131 µmol) in DCM (2 mL) was added TFA (575 mg, 5.05 mmol). The mixture was stirred at 25° C. for 0.5 hr. On completion, the mixture was concentrated in vacuo to give the title compound (61.0 mg, 98% yield, TFA salt) as white solid. LC-MS (ESI+) m/z 470.2 (M+H)+.

(f) Step 6—Tert-butyl-3-[2-[[(3S,8S)-3-[[4-[[1-[[1-(2,6-dioxo-3-piperidyl)-3-methyl-2-oxo benzimidazol 4-yl]methyl]-4-piperidyl]methoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

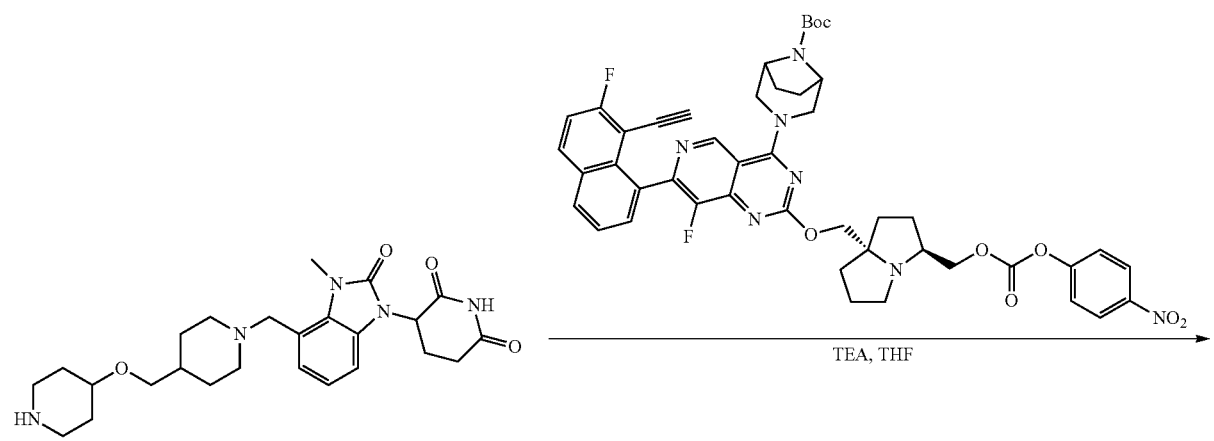

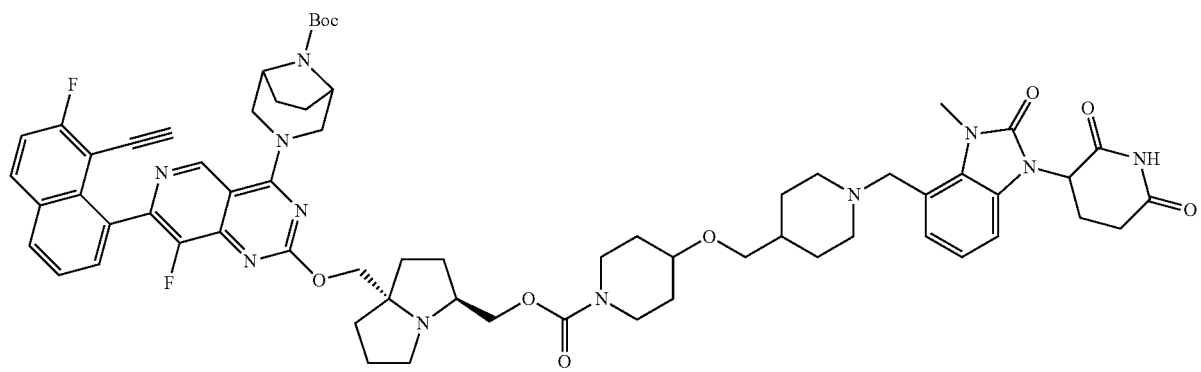

To a solution of 3-[3-methyl-2-oxo-4 [[4-(4-piperidyloxymethyl)-1-piperidyl]methyl]benzimidazol-1 yl]piperidine-2,6-dione (60.4 mg, 128 µmol) and tert-butyl 3-[7-(8-ethynyl-7-fluoro-1 naphthyl) 8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74.0 mg, 85.8 µmol) in THF was added TEA (8.69 mg, 85.8 µmol). The mixture was stirred at 25° C. for 0.5 hr. On completion, the mixture was concentrated in vacuo. The residue was purified by prep-HPLC (column: Welch Ultimate C18 150*25 mm*5 µm; mobile phase: [water (FA)-ACN]; gradient: 26%-46% B over 2 min) to give the title compound (50.0 mg, 48% yield) as white solid. LC-MS (ESI+) m/z 1192.1 (M+H)+.

(g) Step 7—[(3S,8S)-8-[[4-(3,8-Diazabicyclo[3.2.1]
octan-3-yl)-7-(8-ethynyl-7-fluoro-1-naphthyl)
8-fluoro-pyrido[4,3-d]pyrimidin-2-yl]oxymethyl]-1,
2,3,5,6,7-hexahydropyrrolizin-3-yl]methyl4-[[1-[[1-
(2,6-dioxo-3-piperidyl)-3-methyl-2-oxo-benzimida-
zol-4-yl]methyl]-4-piperidyl]methoxy]piperidine-1-
carboxylate (062)

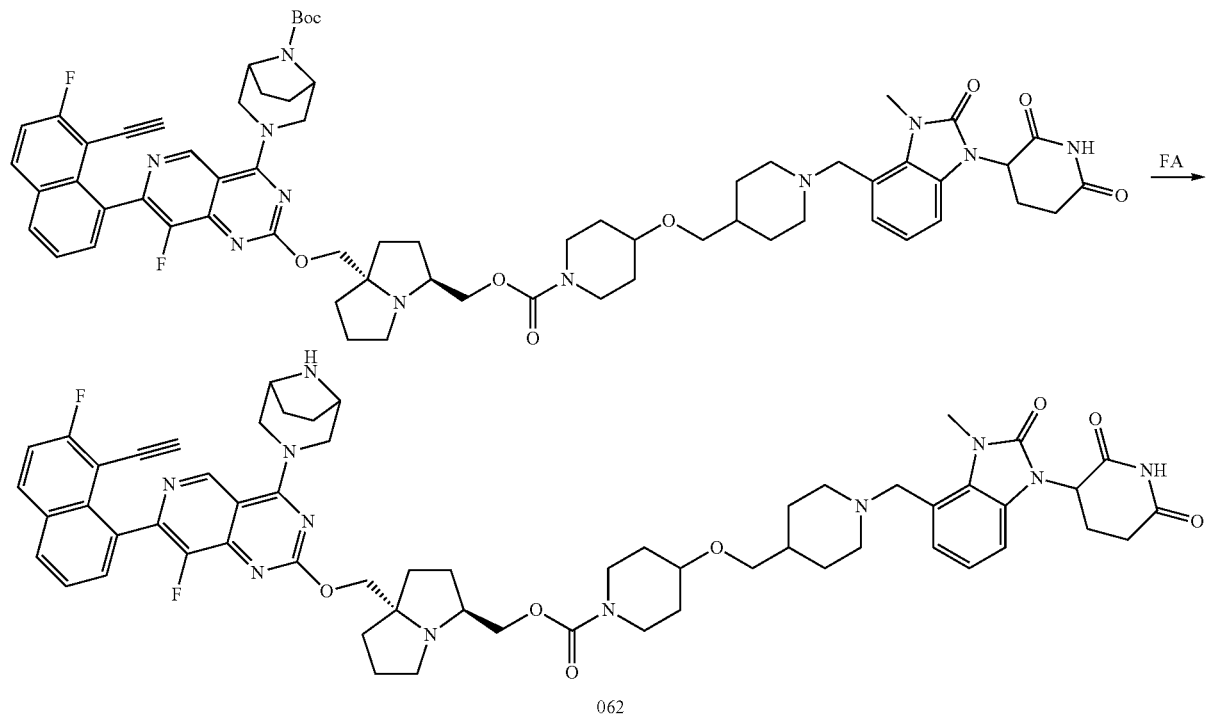

062

Tert-butyl-3-[2-[[(3S,8S)-3-[[4-[[1-[[1-(2,6-dioxo-3-piperidyl)-3-methyl-2-oxobenzimidazol-4-yl]methyl]-4-piperidyl]methoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (50.0 mg, 41.9 µmol) dissolved in HCOOH (2.01 mg, 41.9 µmol) and stirred at 25° C. for 0.5 hr. On completion, the mixture was concentrated in vacuo and then lyophilized to give the compound (39.6 mg, 86% yield, FA salt) as yellow solid. $^1$H NMR (400 MHz, DMSO-d$_6$) δ 11.16-11.05 (m, 1H), 9.09 (s, 1H), 8.26-8.18 (m, 2H), 7.73-7.56 (m, 3H), 7.10-7.03 (m, 1H), 6.95 (t, J=7.8 Hz, 1H), 6.86 (d, J=8.0 Hz, 1H), 5.43-5.30 (m, 1H), 4.61-4.53 (m, 1H), 4.46-4.38 (m, 1H), 4.27-4.09 (m, 4H), 3.95-3.84 (m, 2H), 3.76-3.68 (m, 2H), 3.66-3.64 (m, 3H), 3.62-3.57 (m, 4H), 3.22 (d, J=6.8 Hz, 4H), 3.14-3.06 (m, 3H), 2.95-2.76 (m, 6H), 2.73-2.57 (m, 4H), 2.03-1.89 (m, 4H), 1.86-1.69 (m, 12H), 1.63 (s, 2H), 1.50-1.45 (m, 1H), 1.37-1.28 (m, 2H), 1.23 (s, 1H); LC-MS (ESI$^+$) m/z 1092.6 (M+H)$^+$.

Example 67. Synthesis of Compound 063

(a) Step 1—Tert-butyl 4-(methylsulfonyloxymethyl)piperidine-1-carboxylate

To a solution of tert-butyl 4-(hydroxymethyl)piperidine-1-carboxylate (5.00 g, 23.2 mmol, CAS #123855-51-6) in DCM (60 mL) was added TEA (5.88 g, 58.0 mmol) and methylsulfonyl methanesulfonate (6.07 g, 34.8 mmol) at 0° C. The mixture was stirred at 25° C. for 2 hrs. On completion, the reaction mixture was added H$_2$O (100 mL) and extracted with DCM (3×60 mL). The combined organic layers were washed with brine (60 mL), dried over anhydrous sodium sulfate, filtered and the filtrate was concentrated in vacuo to give the title compound (5.90 g, 85% yield) as white solid. $^1$H NMR (400 MHz, CDCl$_3$) δ 4.24-4.10 (m, 2H), 4.07 (d, J=6.4 Hz, 2H), 3.02 (s, 3H), 2.71 (t, J=12.0 Hz, 2H), 1.97-1.87 (m, 1H), 1.75 (d, J=13.2 Hz, 2H), 1.46 (s, 9H), 1.27-1.17 (m, 2H); LC-MS (ESI$^+$) m/z 238.1 (M+H-t-Bu)$^+$.

(b) Step 2—Tert-butyl 4-[(1-benzyloxycarbonylazetidin-3-yl)oxymethyl]piperidine-1-carboxylate

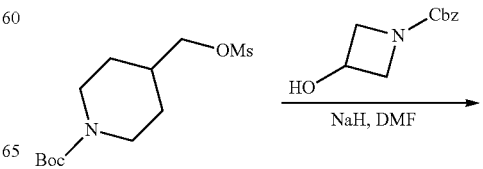

-continued

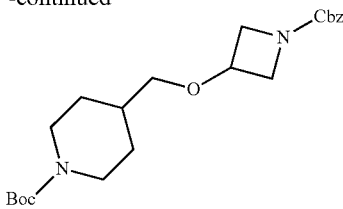

A mixture of benzyl 3-hydroxyazetidine-1-carboxylate (3.00 g, 14.4 mmol, CAS #128117-22-6) in DMF (35 mL) was added NaH (868 mg, 21.7 mmol, 60% purity) at 0° C., then the mixture was stirred at 0° C. for 0.5 hr under $N_2$ atmosphere. After that, a solution of tert-butyl 4-(methylsulfonyloxymethyl) piperidine-1-carboxylate (4.25 g, 14.4 mmol) was added to the reaction. The mixture was stirred at 60° C. for 16 hrs. On completion, the reaction mixture was added $H_2O$ (50 mL) and extracted with ethyl acetate (3×40 mL). The combined organic layers were washed with brine (30 mL), dried over anhydrous sodium sulfate, filtered and the filtrate was concentrated in vacuo. The residue was purified by column chromatography (SiO$_2$, Petroleum ether/Ethyl acetate=10/1 to 6/1) to give the title compound (3.00 g, 48% yield) as faint yellow oil. $^1$H NMR (400 MHz, CDCl$_3$) δ 7.41-7.33 (m, 5H), 5.10 (s, 2H), 4.24-4.19 (m, 1H), 4.19-4.06 (m, 4H), 3.89 (dd, J=4.0, 9.2 Hz, 2H), 3.19 (d, J=5.6 Hz, 2H), 2.70 (t, J=12.4 Hz, 2H), 1.73-1.69 (m, 2H), 1.61 (s, 1H), 1.46 (s, 9H), 1.20-1.10 (m, 2H); LC-MS (ESI$^+$) m/z 305.2 (M+H-Boc)$^+$.

(c) Step 3—Tert-butyl 4-(azetidin-3-yloxymethyl)piperidine-1-carboxylate

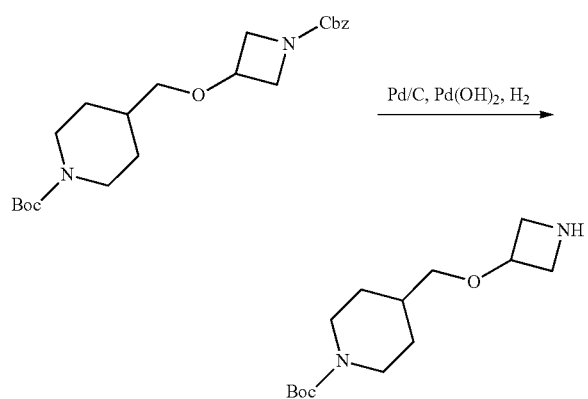

To a solution of tert-butyl 4-[(1-benzyloxycarbonylazetidin-3-yl) oxymethyl]piperidine-1-carboxylate (300 mg, 741 µmol) in MeOH (5 mL) was added Pd/C (150 mg, 140 µmol, 10% purity) and Pd(OH)$_2$/C (75.0 mg, 103 µmol, 20% purity) under N$_2$ atmosphere. The suspension was degassed and purged with H$_2$ for 3 times. The mixture was stirred under H$_2$ (15 Psi.) at 25° C. for 2 hrs. On completion, the mixture was filtered by diatomite to obtain the filtrate and concentrated in vacuo to give the title compound (230 mg, 91% yield) as white solid. $^1$H NMR (400 MHz, CDCl$_3$) δ 4.32-4.25 (m, 1H), 4.15-4.06 (m, 2H), 3.77-3.52 (m, 4H), 3.18 (d, J=6.4 Hz, 2H), 2.70 (t, J=12.4 Hz, 2H), 1.75-1.71 (m, 2H), 1.69-1.68 (m, 1H), 1.46 (s, 9H), 1.20-1.09 (m, 2H); LC-MS (ESI$^+$) m/z 271.3 (M+H)$^+$.

(d) Step 4—Tert-butyl4-[[1-[[1-(2,6-dioxo-3-piperidyl)-3-methyl-2-oxo-benzimidazol-4-yl]methyl]azetidin-3-yl]oxymethyl]piperidine-1-carboxylate

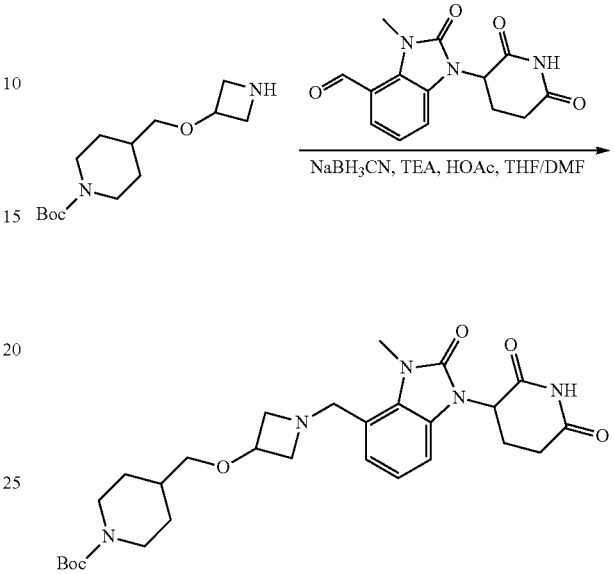

To a solution of tert-butyl 4-(azetidin-3-yloxymethyl) piperidine-1-carboxylate (200 mg, 739 µmol) and 1-(2,6-dioxo-3-piperidyl)-3-methyl-2-oxo-benzimidazole-4-carbaldehyde (212 mg, 739 µmol) in DMF (0.5 mL) was added TEA (89.8 mg, 887 µmol) for 10 min at 0° C. Then AcOH (88.8 mg, 1.48 mmol) was added to the reaction and stirred for 20 min. Finally, the NaBH$_3$CN (69.7 mg, 1.11 mmol) was added to the reaction. The mixture was stirred at 25° C. for 2 hrs. On completion, the mixture was concentrated in vacuo. The crude product was purified by reversed-phase HPLC (0.1% FA condition) to give the title compound (140 mg, 31% yield) as white solid. $^1$H NMR (400 MHz, DMSO-d$_6$) δ 11.17-10.98 (m, 1H), 7.09-7.01 (m, 1H), 7.00-6.89 (m, 2H), 5.44-5.29 (m, 1H), 4.11-4.03 (m, 1H), 3.99-3.84 (m, 4H), 3.84-3.77 (m, 2H), 3.62 (s, 3H), 3.45 (t, J=6.4 Hz, 2H), 3.25-3.18 (m, 2H), 3.14 (d, J=6.4 Hz, 2H), 2.89-2.85 (m, 2H), 2.71-2.66 (m, 2H), 2.04-1.96 (m, 1H), 1.66-1.58 (m, 4H), 1.38 (s, 9H); LC-MS (ESI$^+$) m/z 542.3 (M+H)$^+$.

(e) Step 5—3-[3-Methyl-2-oxo-4-[[3-(4-piperidylmethoxy)azetidin-1-yl]methyl]benzimidazol-1-yl]piperidine-2,6-dione

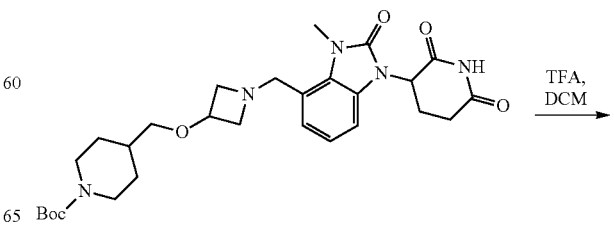

1189

-continued

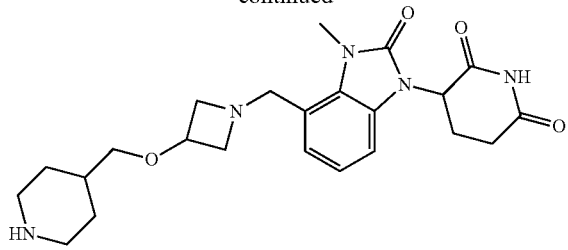

To a solution of tert-butyl 4-[[1-[[1-(2,6-dioxo-3-piperidyl)-3-methyl-2-oxo-benzimidazol-4-yl]methyl] azetidin-3-yl]oxymethyl]piperidine-1-carboxylate (100 mg, 184

μmol) in DCM (1 mL) was added TFA (307 mg, 2.69 mmol). The mixture was stirred at 25° C. for 0.5 hr. On completion, the mixture was concentrated in vacuo to give the title compound (86.0 mg, 83% yield, TFA salt) as yellow oil. LC-MS (ESI+) m/z 442.1 (M+H)+.

(f) Step 6—Tert-butyl 3-[2-[[(3S,8S)-3-[[4-[[1-[[1-(2,6-dioxo-3-piperidyl)-3-methyl-2-oxo-benzimidazol-4-yl]methyl]azetidin-3-yl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

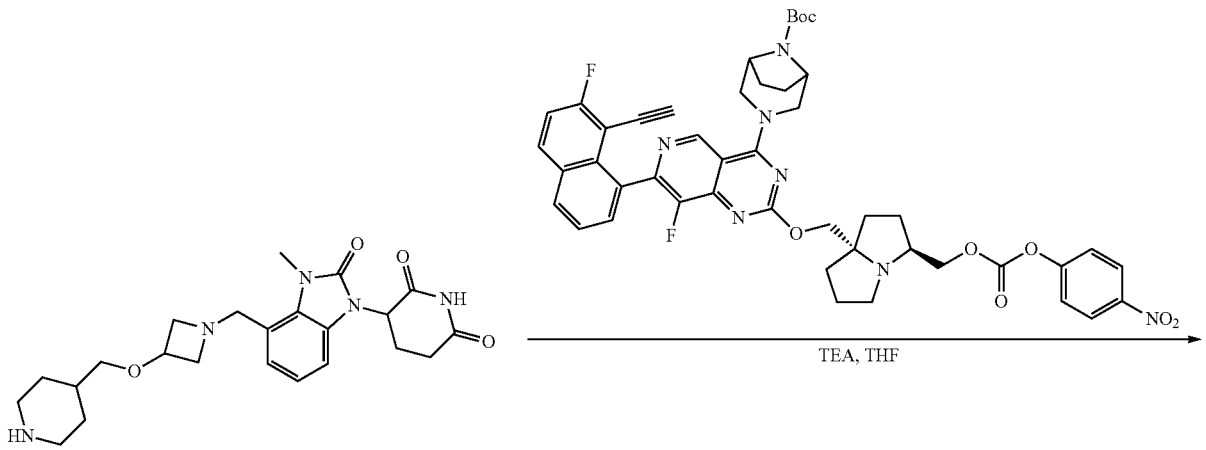

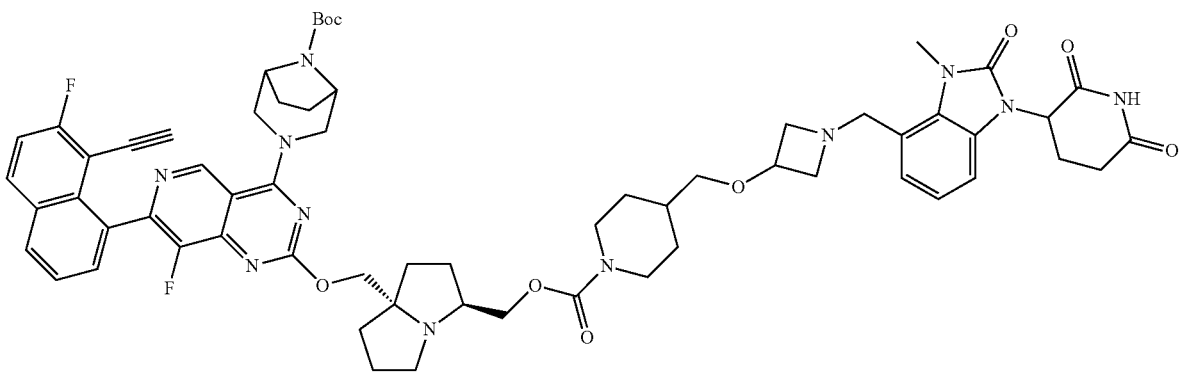

To a solution of 3-[3-methyl-2-oxo-4-[[3-(4-piperidylmethoxy)azetidin-1-yl]methyl]benzimidazol-1-yl]piperidine-2,6-dione (50.0 mg, 113 μmol, TFA salt) in THF (1 mL) was added TEA (15.2 mg, 150 μmol). To a solution of tert-butyl3-[7-(8-ethynyl-7-fluoro-1-naphthyl)8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (51.7 mg, 60.0 μmol) in THF (1 mL) was added to the reaction. The mixture was stirred at 25° C. for 0.5 hr. On completion, the mixture was concentrated in vacuo. The residue was purified by prep-HPLC (column: Welch Xtimate C18 150*25 mm*5 um; mobile phase: [water (FA)-ACN]; gradient: 14%-44% B over 15 min) to give the title compound (25.0 mg, 28% yield) as white solid. LC-MS (ESI+) m/z 1164.3 (M+H)+.

(g) Step 6—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl4-[[1-[[1-(2,
6-dioxo-3-piperidyl)-3-methyl-2-oxo-benzimidazol-
4-yl]methyl]azetidin-3-yl]oxymethyl]piperidine-1-
carboxylate (063)

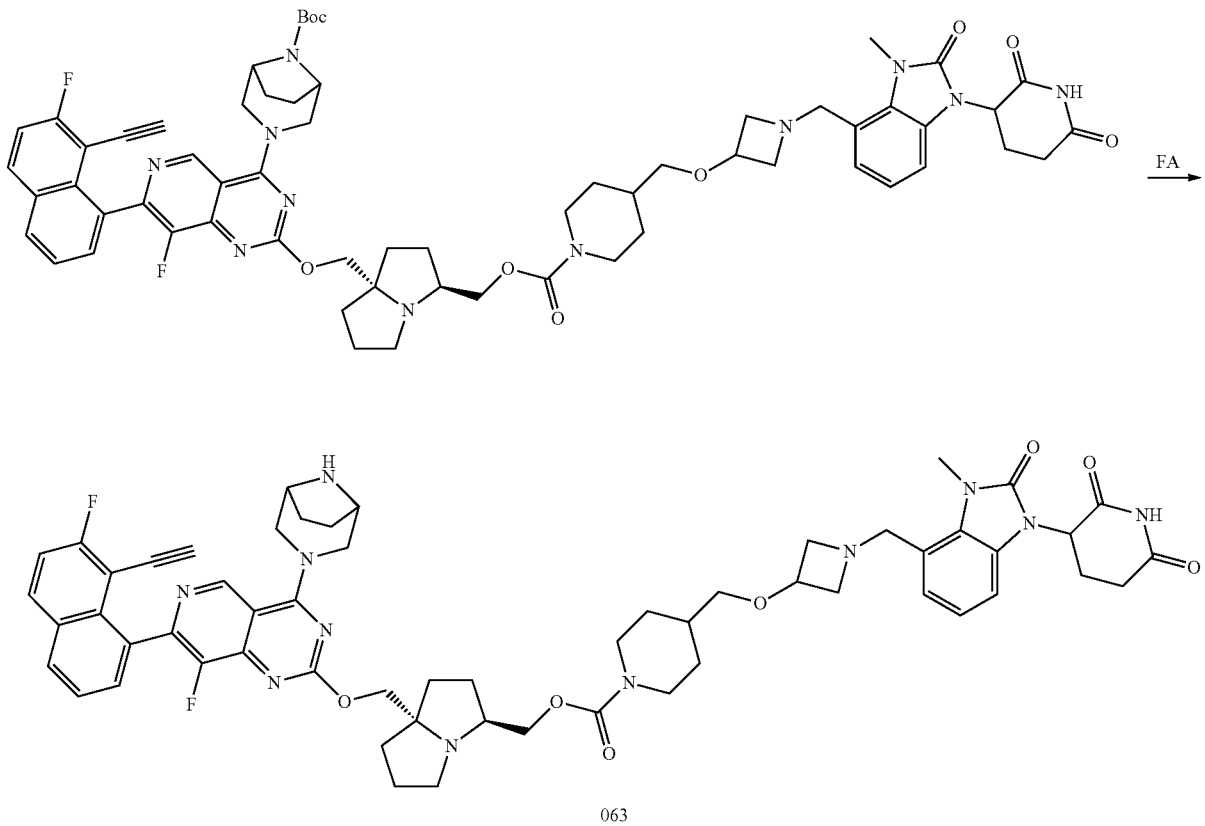

A solution of tert-butyl 3-[2-[[(3S,8S)-3-[[4-[[1-[[1-(2,6-dioxo-3-piperidyl)-3-methyl-2-oxo-benzimidazol-4-yl]methyl]azetidin-3-yl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (25.0 mg, 21.4 μmol) in HCOOH (1 mL) was stirred at 25° C. for 2 hrs. On completion, the mixture was concentrated in vacuo, then the mixture was added the H$_2$O (2 mL) and ACN (1 mL) to dissolve. Finally, the mixture was under lyophilized to give the title compound (13.8 mg, 57% yield, FA salt) as yellow solid. $^1$H NMR (400 MHz, DMSO-d$_6$) δ 11.09 (s, 1H), 9.06 (s, 1H), 8.21-8.17 (m, 2H), 7.70-7.56 (m, 3H), 7.07-7.01 (m, 1H), 6.98-6.88 (m, 2H), 5.39-5.32 (m, 1H), 4.52 (d, J=12.4 Hz, 1H), 4.38 (d, J=12.4 Hz, 1H), 4.21-4.17 (m, 1H), 4.15-4.08 (m, 2H), 4.02 (s, 1H), 4.01-3.91 (m, 4H), 3.78 (s, 2H), 3.75-3.69 (m, 4H), 3.67-3.65 (m, 1H), 3.61 (s, 3H), 3.45-3.42 (m, 2H), 3.34-3.27 (m, 2H), 3.12 (d, J=5.6 Hz, 2H), 2.86 (t, J=5.6 Hz, 2H), 2.81-2.76 (m, 2H), 2.75-2.60 (m, 4H), 2.08-1.98 (m, 2H), 1.83-1.76 (m, 4H), 1.75-1.73 (m, 4H), 1.68-1.58 (m, 4H), 1.58-1.51 (m, 1H), 1.11-0.97 (m, 2H); LC-MS (ESI+) m/z 1064.3 (M+H)$^+$.

Example 68. Synthesis of Compound 064

(a) Step 1—Tert-butyl 4-[1-[[1-(2,6-dioxo-3-piperidyl)-3-methyl-2-oxo-benzimidazol-4-yl]methyl]-4-piperidyl]piperazine-1-carboxylate To a solution of tert-butyl 4-(4-piperidyl)piperazine-1-carboxylate (200 mg, 742 μmol, CAS #205059-24-1) in DMF (15 mL) was added TEA (112 mg, 1.11 mmol) at 25° C. until pH stabilized at 8. The mixture was stirred at 25° C. for 0.5 hr. Then HOAc (66.8 mg, 1.11 mmol) was added at 25° C. to the solution until pH stabilized at 5~6. Subsequently, 1-(2,6-dioxo-3-piperidyl)-3-methyl-2-oxo-benzimidazole-4-carbaldehyde (319 mg, 1.11 mmol) was added and stirred for 0.5 hr at 25° C. After that, NaBH$_3$CN (69.9 mg, 1.11 mmol) was added one portion. The resulting reaction mixture was stirred at 25° C. for 11 hrs. On completion, the reaction mixture was quenched by addition H$_2$O (0.1 mL) at 25° C. The reaction mixture was filtered to give a residue. The above residue was purified by reversed phase flash (0.1% FA condition) to give the title compound (100 mg, 24% yield) was obtained as white solid. LC-MS (ESI$^+$) m/z 541.3 (M+H)$^+$.

1193

(b) Step 2—3-[3-Methyl-2-oxo-4-[(4-piperazin-1-yl-1-piperidyl)methyl]benzimidazol-1-yl]piperidine-2,6-dione

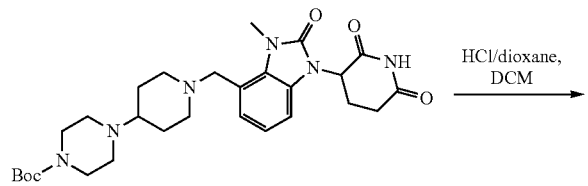

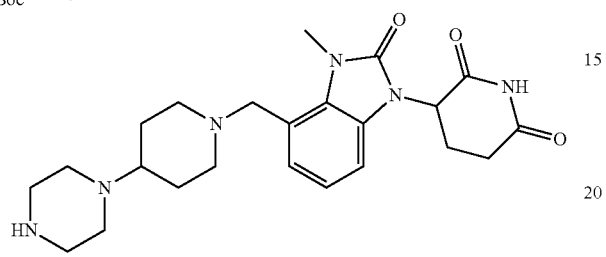

1194

To a solution of tert-butyl 4-[1-[[1-(2,6-dioxo-3-piperidyl)-3-methyl-2-oxo-benzimidazol-4-yl]methyl]-4-piperidyl]piperazine-1-carboxylate (100 mg, 184 μmol) in DCM (3 mL) was added HCl/dioxane (4 M, 1 mL). The mixture was stirred at 25° C. for 1 hr. On completion, the reaction mixture was concentrated in vacuo to give the title compound (80.0 mg, 98% yield, HCl salt) as white solid. LC-MS (ESI$^+$) m/z 441.2 (M+H)$^+$.

(c) Step 3—Tert-butyl 3-[2-[[[(3S,8S)-3-[[4-[1-[[1-(2,6-dioxo-3-piperidyl)-3-methyl-2-oxo-benzimidazol-4-yl]methyl]-4-piperidyl]piperazine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

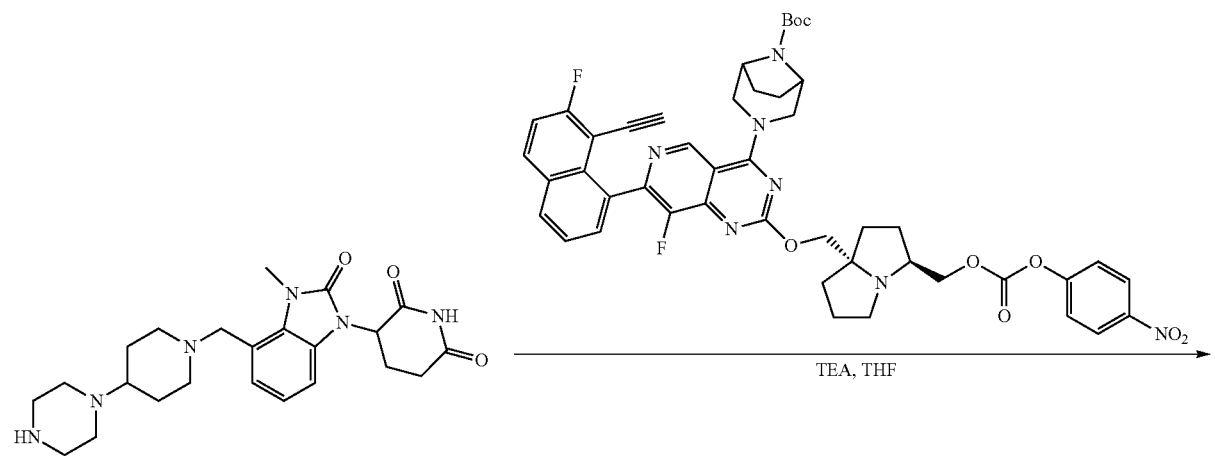

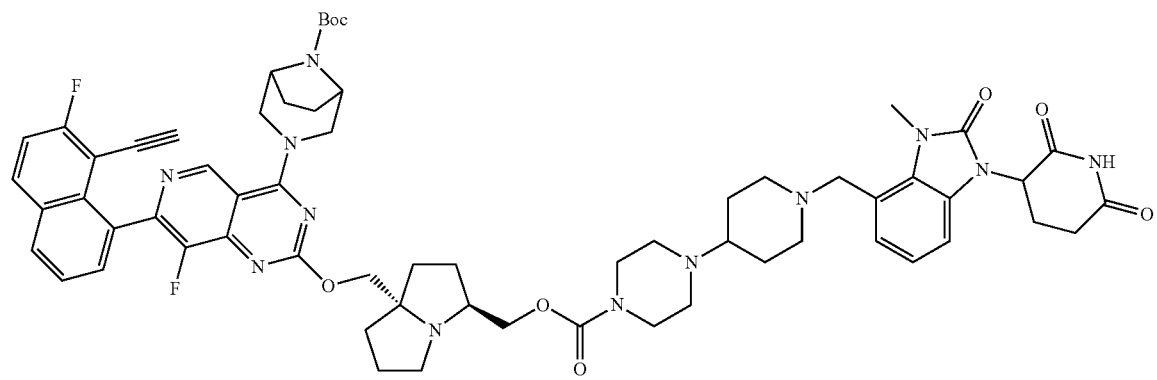

To a solution of 3-[3-methyl-2-oxo-4-[(4-piperazin-1-yl-1-piperidyl)methyl]benzimidazol-1-yl]piperidine-2,6-dione (70.0 mg, 158 μmol, HCl salt) in THF (3 mL) was added TEA (8.04 mg, 79.4 μmo) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (68.4 mg, 79.4 μmol). The mixture was stirred at 25° C. for 1 hr. On completion, the reaction mixture was quenched by addition H₂O (0.1 mL) at 25° C. The reaction mixture was filtered to give a residue. The above residue was purified by prep-HPLC (column: Phenomenex luna C18 150*25 mm*10 μm; mobile phase: [water (FA)-ACN]; gradient: 15%-45% B over 10 min) to give the title compound (45.0 mg, 48% yield) as yellow solid. LC-MS (ESI⁺) m/z 1163.5 (M+H)⁺.

(d) Step 4 [(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[1-[[1-(2,6-dioxo-3-piperidyl)-3-methyl-2-oxo-benzimidazol-4-yl]methyl]-4-piperidyl]piperazine-1-carboxylate (064)

MHz, DMSO-d₆) δ 12.04-11.44 (m, 2H), 11.12 (s, 1H), 10.91-10.55 (m, 1H), 10.37-10.07 (m, 1H), 9.99-9.70 (m, 1H), 9.15 (s, 1H), 8.32-8.17 (m, 2H), 7.79-7.56 (m, 3H), 7.33 (d, J=5.6 Hz, 1H), 7.26 (t, J=6.0 Hz, 1H), 7.25-7.09 (m, 1H), 5.46 (dd, J=4.8, 12.0 Hz, 1H), 4.70 (d, J=8.4 Hz, 3H), 4.60 (s, 3H), 4.45 (d, J=2.8 Hz, 2H), 4.27-4.14 (m, 3H), 4.09 (d, J=8.8 Hz, 2H), 4.05-3.97 (m, 2H), 3.74-3.69 (m, 3H), 3.64 (d, J=2.0 Hz, 2H), 3.60-3.42 (m, 6H), 3.39 (s, 3H), 3.28-3.07 (m, 4H), 3.00-2.84 (m, 1H), 2.71 (d, J=13.2 Hz, 1H), 2.63 (d, J=17.6 Hz, 1H), 2.37-2.12 (m, 7H), 1.91 (s, 10H); LC-MS (ESI⁺) m/z 1063.3 (M+H)⁺.

Example 69. Synthesis of Compound 065

(a) Step 1—Tert-butyl 4-[[1-(2,6-dioxo-3-piperidyl)-3-methyl-2-oxo-benzimidazol-4-yl]methyl]piperidine-1-carboxylate To a solution of tert-butyl 4-(bromomethyl)piperidine-1-carboxylate (411 mg, 1.48 mmol, CAS #158407-04-6) and 3-(4-bromo-3-methyl-2-oxo-benzimidazol-1-yl)piperidine-2,6-dione (500 mg, 1.48 mmol, CAS #2304754-51-4) in DME (50 mL) was added Ir[dF(CF₃)ppy]₂(dtbpy)(PF₆) (16.5 mg, 14.7 μmol), NiCl₂·dtbbpy (8.83 mg, 22.1 μmol), TTMSS (367 mg, 1.48 mmol) and Na₂CO₃ (313 mg, 2.96

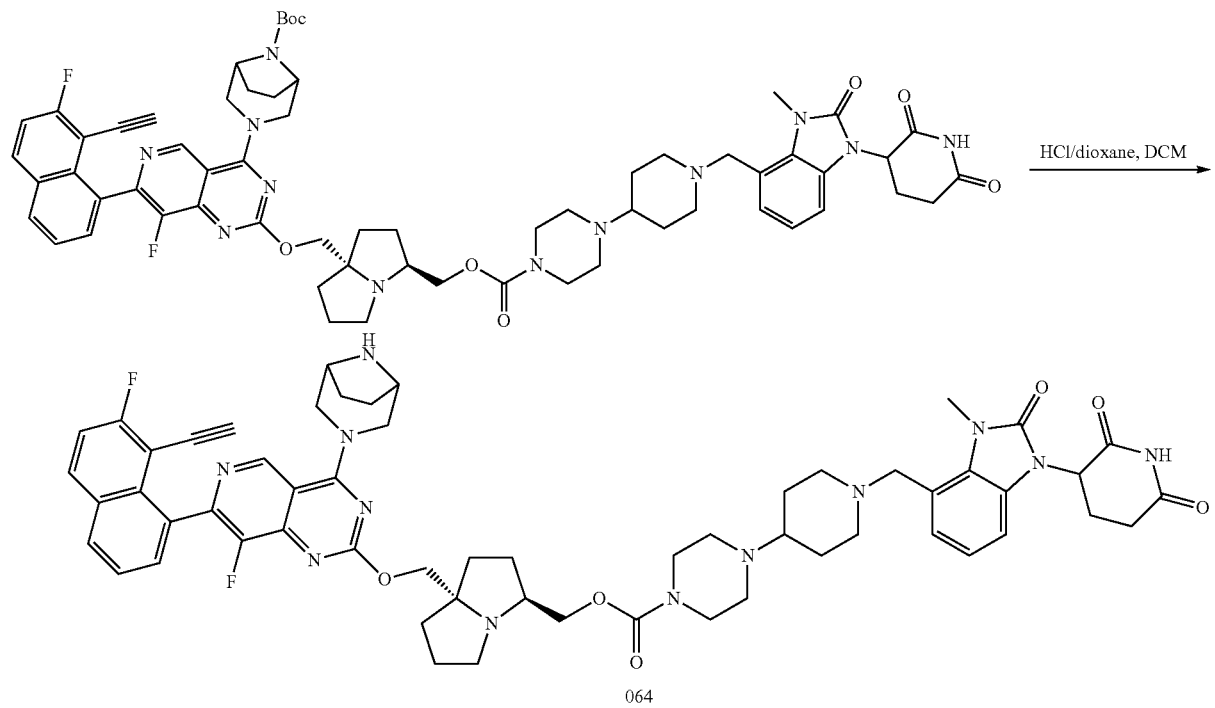

064

To a solution of tert-butyl 3-[2-[[(3S,8S)-3-[[4-[1-[[1-(2,6-dioxo-3-piperidyl)-3-methyl-2-oxo-benzimidazol-4-yl]methyl]-4-piperidyl]piperazine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (25.0 mg, 21.4 μmol) in DCM (3 mL) was added HCl/dioxane (4 M, 833 μL). The reaction mixture was stirred at 25° C. for 0.25 hr. The reaction mixture was concentrated in vacuo to give a residue. On completion, deionized water was added and the mixture was lyophilized to give the title compound (29.5 mg, 75% yield, HCl salt) as yellow solid. ¹H NMR (400 mmol). The vial was sealed and placed under nitrogen was added. The reaction was stirred and irradiated with a 10 W blue LED lamp (3 cm away), with cooling water to keep the reaction at 25° C. for 14 hrs. On completion, the reaction mixture was concentrated in vacuo to give a residue and the residue was purified by prep-HPLC (column: Phenomenex luna C18 150*25 mm*10 μm; mobile phase: [water (FA)-ACN]; gradient: 37%-67% B over 10 min) to give the title compound (302 mg, 44% yield) as white solid. ¹H NMR (400 MHz, CDCl₃) δ 8.23 (s, 1H), 6.98 (t, J=7.6 Hz, 1H), 6.83 (d, J=7.6 Hz, 1H), 6.69 (d, J=8.0 Hz, 1H), 5.26-5.16 (m, 1H), 4.12 (s, 2H), 3.66 (s, 3H), 2.98-2.90 (m, 1H), 2.88-2.83

(m, 2H), 2.83-2.70 (m, 2H), 2.64 (t, J=12.4 Hz, 2H), 2.27-2.18 (m, 1H), 1.66 (s, 2H), 1.47 (s, 9H), 1.31-1.16 (m, 2H); LC-MS (ESI⁺) m/z 357.0 (M-Boc+H)⁺.

(b) Step 2—3-[3-Methyl-2-oxo-4-(4-piperidylmethyl)benzimidazol-1-yl]piperidine-2,6-dione

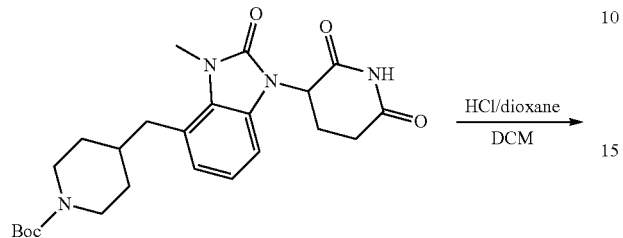

To a solution of tert-butyl 4-[[1-(2,6-dioxo-3-piperidyl)-3-methyl-2-oxo-benzimidazol-4-yl]methyl]piperidine-1-carboxylate (292 mg, 639 μmol) in DCM (5 mL) was added HCl/dioxane (4 M, 2.5 mL). The mixture was stirred at 25° C. for 2 hrs. On completion, the reaction mixture was concentrated in vacuo to give the title compound (250 mg, 99% yield, HCl salt) as white solid. LC-MS (ESI⁺) m/z 357.0 (M+H)⁺.

(c) Step 3—Tert-butyl 4-[4-[[1-(2,6-dioxo-3-piperidyl)-3-methyl-2-oxo-benzimidazol-4-yl]methyl]-1-piperidyl]piperidine-1-carboxylate To a solution of 3-[3-methyl-2-oxo-4-(4-piperidylmethyl)benzimidazol-1-yl]piperidine-2,6-dione (230 mg, 645 μmol, HCl salt) in DMF (5 mL) was added TEA (97.5 mg, 967 μmol) to adjust pH to 10, then HOAc (77.5 mg, 1.29 mmol) was added to adjust pH to 6. A solution of tert-butyl 4-oxopiperidine-1-carboxylate (128 mg, 645 μmol, CAS #79099-07-3) in DMF (1 mL) was added to mixture at 25° C. Finally, NaBH₃CN (81.1 mg, 1.29 mmol) was added to mixture and stirred at 50° C. for 4 hrs. On completion, the reaction mixture was added H₂O (0.5 mL) and concentrated in vacuo to give a residue and the residue was purified by prep-HPLC (0.1% FA condition) to give the title compound (108 mg, 28% yield) as white solid. ¹H NMR (400 MHz, DMSO-d₆) δ 11.10 (s, 1H), 7.01-6.91 (m, 2H), 6.81 (d, J=7.6 Hz, 1H), 5.36 (dd, J=5.2, 12.4 Hz, 1H), 3.95 (d, J=11.2 Hz, 2H), 3.53 (s, 3H), 2.92-2.79 (m, 5H), 2.75-2.55 (m, 5H), 2.23 (t, J=10.8 Hz, 2H), 2.03-1.95 (m, 1H), 1.72-1.62 (m, 4H), 1.56-1.46 (m, 1H), 1.38 (s, 9H), 1.32-1.23 (m, 4H); LC-MS (ESI⁺) m/z 540.1 (M+H)⁺.

(d) Step 4—3-[3-Methyl-2-oxo-4-[[1-(4-piperidyl)-4-piperidyl]methyl]benzimidazol-1-yl]piperidine-2,6-dione

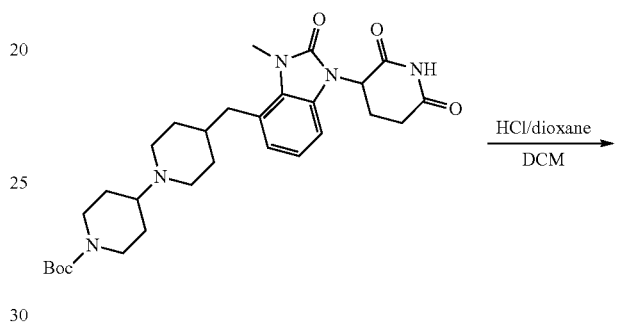

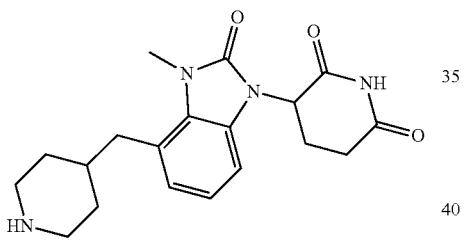

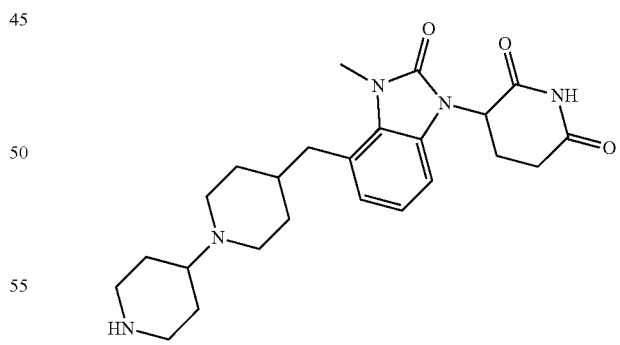

To a solution of tert-butyl 4-[4-[[1-(2,6-dioxo-3-piperidyl)-3-methyl-2-oxo-benzimidazol-4-yl]methyl]-1-piperidyl]piperidine-1-carboxylate (108 mg, 200 μmol) in DCM (5 mL) was added HCl/dioxane (4 M, 2.5 mL). The mixture was stirred at 25° C. for 1 hr. On completion, the reaction mixture was concentrated in vacuo to give the title compound (86.0 mg, 90% yield, HCl salt) as white solid. LC-MS (ESI⁺) m/z 440.1 (M+H)⁺.

(e) Step 5—Tert-butyl 3-[2-[[(3S,8S)-3-[[4-[4-[[1-(2,6-dioxo-3-piperidyl)-3-methyl-2-oxo-benzimidazol-4-yl]methyl]-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

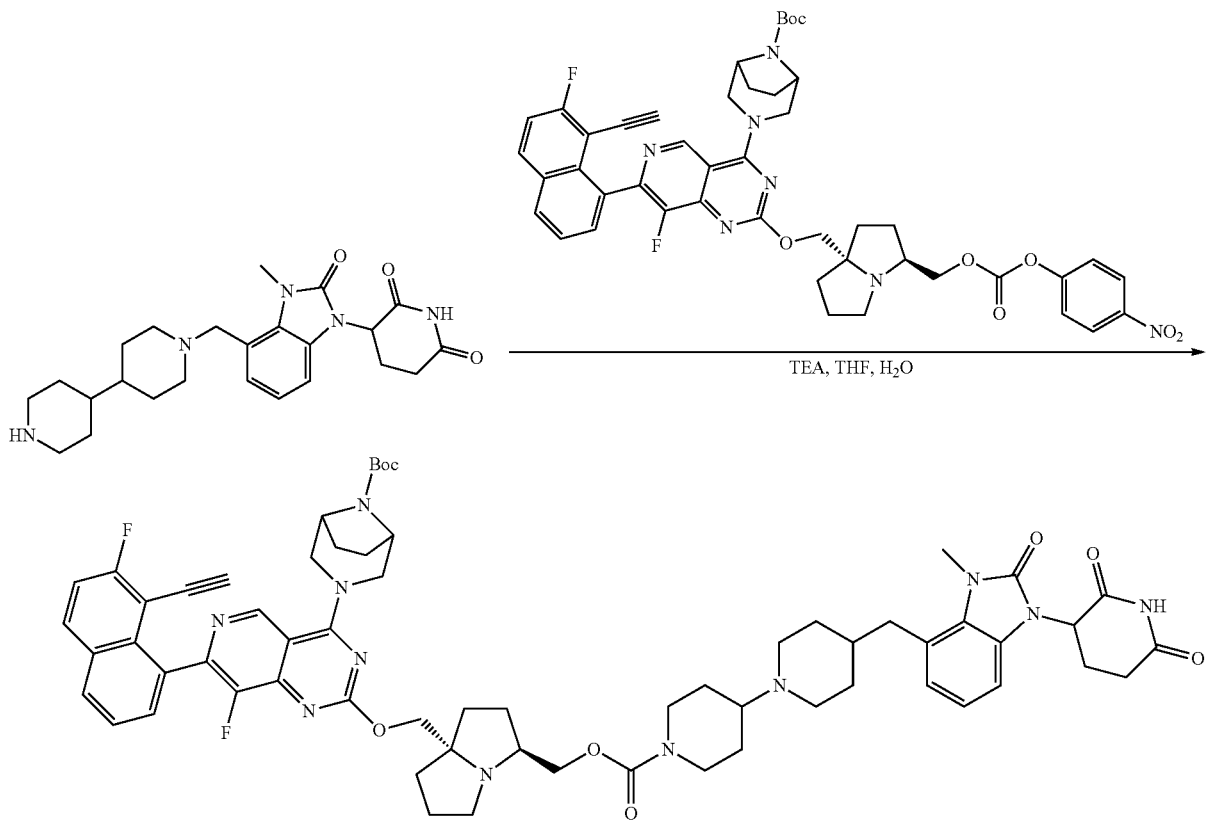

To a solution of 3-[3-methyl-2-oxo-4-[[1-(4-piperidyl)-4-piperidyl]methyl]benzimidazol-1-yl] piperidine-2,6-dione (66.2 mg, 139 μmol, HCl salt) in THF (2 mL) and H₂O (0.2 mL) was added TEA (21.1 mg, 208 μmol). Then tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 69.6 μmol) was added to mixture and stirred at 25° C. for 1 hr. On completion, the mixture was concentrated in vacuo to give a residue and the residue was purified by prep-HPLC (column: Phenomenex luna C18 150*25 mm*10 μm; mobile phase: [water (FA)-ACN]; gradient: 18%-48% B over 8 min) to give the title compound (22.0 mg, 26% yield) as yellow solid. LC-MS (ESI⁺) m/z 1162.3 (M+H)⁺.

(f) Step 7—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[4-[[1-(2,6-dioxo-3-piperidyl)-3-methyl-2-oxo-benzimidazol-4-yl]methyl]-1-piperidyl]piperidine-1-carboxylate (065)

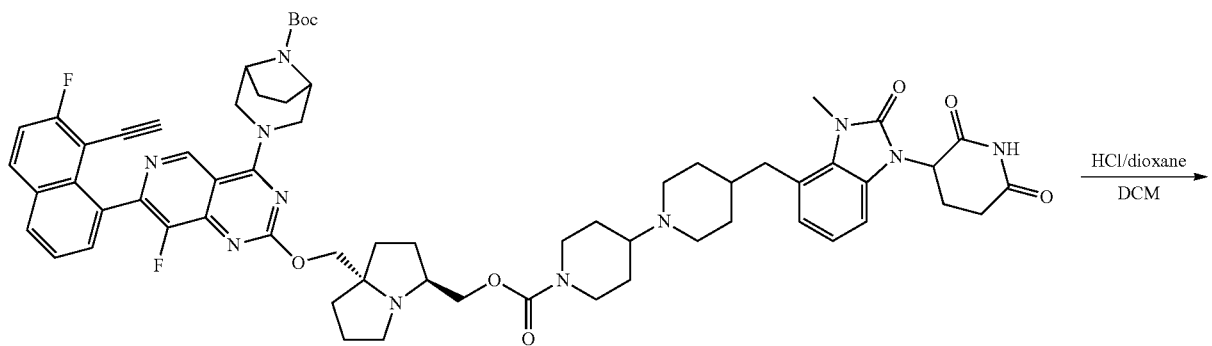

-continued

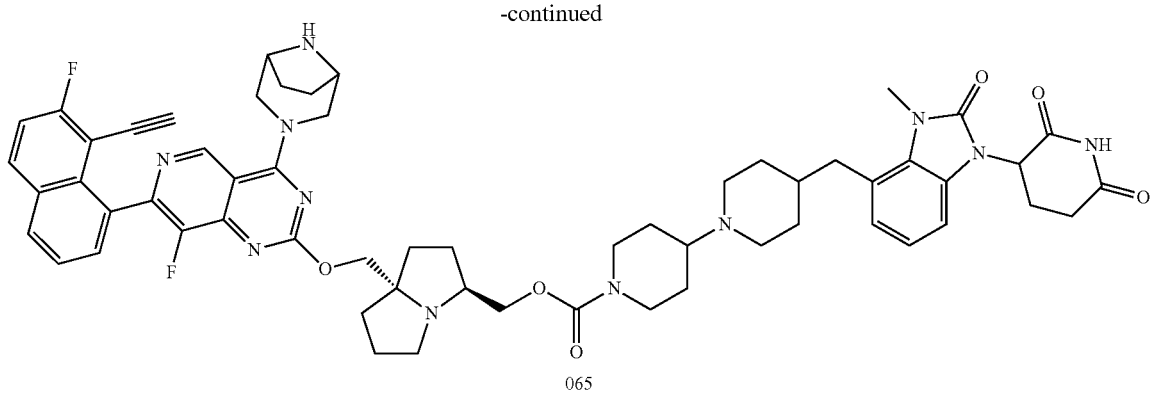

065

To a solution of tert-butyl 3-[2-[[(3S,8S)-3-[[4-[4-[[1-(2,6-dioxo-3-piperidyl)-3-methyl-2-oxo-benzimidazol-4-yl]methyl]-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (22.0 mg, 18.9 µmol) in DCM (5 mL) was added HCl/dioxane (4 M, 1 mL). The mixture was stirred at 25° C. for 20 min. On completion, the reaction mixture was concentrated in vacuo and lyophilized to give the title compound (14.7 mg, 68% yield, HCl salt) as yellow solid. $^1$H NMR (400 MHz, DMSO-$d_6$) δ 11.39-11.18 (m, 1H), 11.09 (s, 1H), 10.78-10.61 (m, 1H), 10.07 (d, J=9.2 Hz, 1H), 9.75-9.73 (m, 1H), 9.15 (s, 1H), 8.30-8.17 (m, 2H), 7.76-7.57 (m, 3H), 7.06-6.92 (m, 2H), 6.81 (d, J=7.6 Hz, 1H), 5.38 (dd, J=5.6, 12.4 Hz, 1H), 4.73-4.53 (m, 4H), 4.38 (d, J=9.2 Hz, 2H), 4.20 (s, 3H), 4.07 (d, J=6.0 Hz, 1H), 4.06-3.95 (m, 3H), 3.55 (s, 3H), 3.47-3.24 (m, 6H), 2.95-2.79 (m, 6H), 2.73-2.58 (m, 2H), 2.34-2.24 (m, 1H), 2.19-1.73 (m, 20H), 1.66-1.52 (m, 2H); LC-MS (ESI$^+$) m/z 1062.3 (M+H)$^+$.

Example 70. Synthesis of Compound 066

(a) Step 1—1-[(4-Methoxyphenyl)methyl]-3-[3-methyl-2-oxo-4-(4,4,5,5-tetramethyl-1,3,2-dioxaborolan-2-yl)benzimidazol-1-yl]piperidine-2,6-dione To a solution of 3-(4-bromo-3-methyl-2-oxo-benzimidazol-1-yl)-1-[(4-methoxyphenyl) methyl]piperidine-2,6-dione (500 mg, 1.09 mmol) in dioxane (10 mL) was added Pd(dppf)Cl$_2$ (159 mg, 218 µmol), KOAc (214 mg, 2.18 mmol), 4,4,5,5-tetramethyl-2-(4,4,5,5-tetramethyl-1,3,2-dioxaborolan-2-yl)-1,3,2-dioxaborolane (554 mg, 2.18 mmol) at 25° C., then the reaction mixture was stirred at 80° C. for 6 hrs under N$_2$. On completion, the reaction mixture was filtered and filtrate in vacuo to give a residue. The residue was purified by reverse phase (0.1% FA condition) to give the title compound (400 mg, 72% yield) as brown solid. LC-MS (ESI$^+$) m/z 506.2 (M+H)$^+$.

(b) Step 2—3-(4-Hydroxy-3-methyl-2-oxo-benzimidazol-1-yl)-1-[(4-methoxyphenyl) methyl] piperidine-2,6-dione

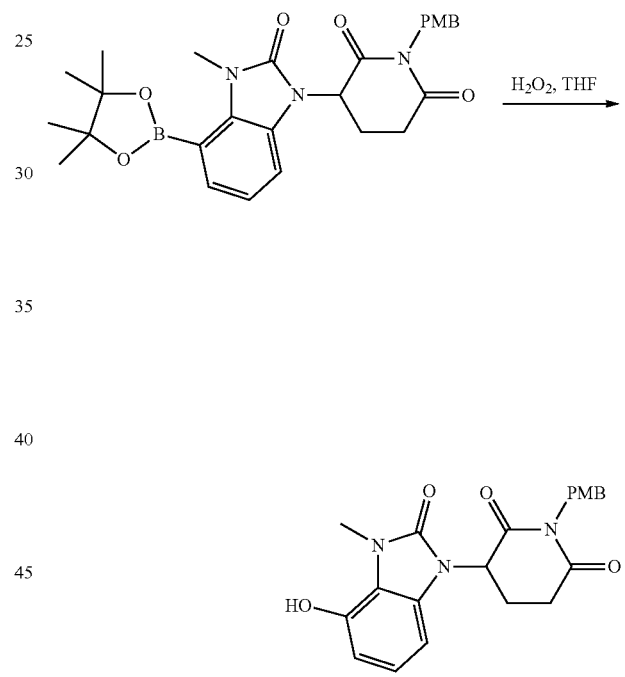

To a solution of 1-[(4-methoxyphenyl)methyl]-3-[3-methyl-2-oxo-4-(4,4,5,5-tetramethyl-1,3,2-dioxaborolan-2-yl)benzimidazol-1-yl]piperidine-2,6-dione (350 mg, 692 µmol) in THF (10 mL) was added H$_2$O$_2$ (314 mg, 2.77 mmol, 30% purity) dropwise at 0° C., then the reaction mixture was stirred at 25° C. for 2 hrs. On completion, the stirring reaction mixture was quenched with sat. Na$_2$S$_2$O$_3$ solution (5 mL) at 0° C. The residue was diluted with water (5 mL) and extracted with EA (5 mL×3). The combined organic layer was dried over Na$_2$SO$_4$, filtered and concentrated in vacuo to give the title compound (270 mg, 98% yield) as light yellow solid. $^1$H NMR (400 MHz, DMSO-$d_6$) δ 9.82 (s, 1H), 7.24-7.19 (m, 3H), 6.86 (d, J=8.8 Hz, 3H), 6.80-6.75 (m, 1H), 6.55 (d, J=8.4 Hz, 1H), 5.46 (dd, J=5.2, 13.2 Hz, 1H), 3.73 (s, 3H), 3.53 (s, 3H), 3.09-3.02 (m, 1H), 2.83-2.71 (m, 2H), 2.08-2.00 (m, 2H); LC-MS (ESI$^+$) m/z 396.0 (M+H)$^+$.

(c) Step 3—Tert-butyl 4-[1-[1-[(4-methoxyphenyl)methyl]-2,6-dioxo-3-piperidyl]-3-methyl-2-oxo-benzimidazol-4-yl]oxypiperidine-1-carboxylate

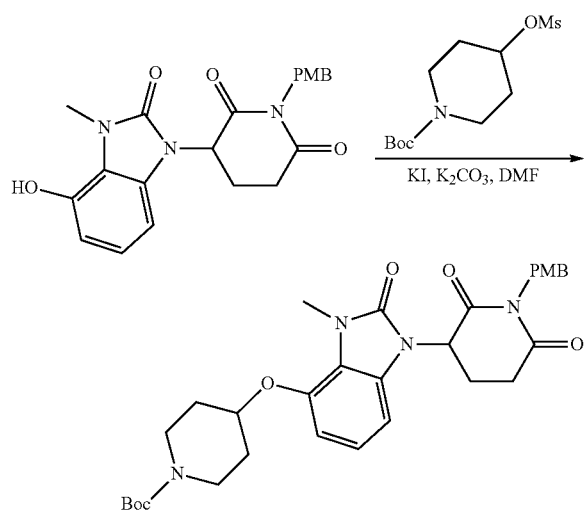

To a solution of 3-(4-hydroxy-3-methyl-2-oxo-benzimidazol-1-yl)-1-[(4-methoxyphenyl)methyl] piperidine-2,6-dione (270 mg, 682 μmol), tert-butyl 4-methylsulfonyloxypiperidine-1-carboxylate (381 mg, 1.37 mmol, CAS #141699-59-4), K₂CO₃ (188 mg, 1.37 mmol) in DMF (10 mL) was added KI (22.6 mg, 136 μmol) at 25° C., then the reaction mixture was stirred at 80° C. for 16 hrs. On completion, the stirring reaction mixture was quenched with H₂O (20 mL). The residue was diluted with water (20 mL) and extracted with EA (30 mL×3). The combined organic layer was dried over Na₂SO₄, filtered and concentrated in vacuo to give a residue. The residue was purified by column chromatography (SiO₂, DCM:EA=3:1) to give the title compound (350 mg, 88% yield) as light yellow solid. LC-MS (ESI⁺) m/z 579.2 (M+H)⁺.

(d) Step 4—3-[3-Methyl-2-oxo-4-(4-piperidyloxy)benzimidazol-1-yl]piperidine-2,6-dione

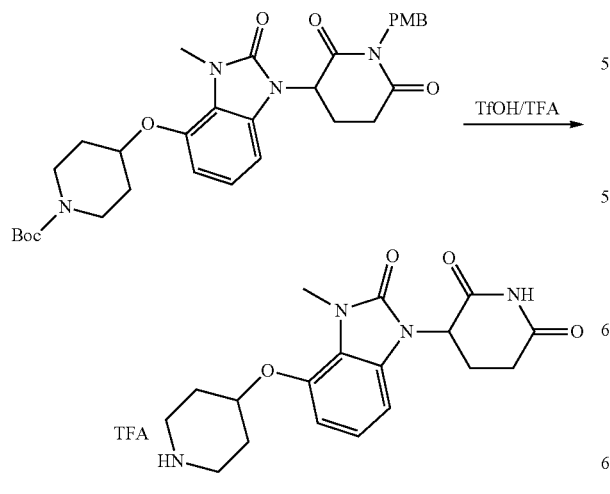

To a solution of tert-butyl 4-[1-[1-[(4-methoxyphenyl)methyl]-2,6-dioxo-3-piperidyl]-3-methyl-2-oxo-benzimidazol-4-yl]oxypiperidine-1-carboxylate (300 mg, 518 μmol) in TFA (3 mL) was added TfOH (1.70 g, 11.3 mmol) dropwise at 25° C., then the reaction mixture was stirred at 70° C. for 2 hrs. On completion, the reaction mixture was concentrated in vacuo to give (240 mg, 97% yield, TFA) as brown oil. LC-MS (ESI⁺) m/z 359.1 (M+H)⁺.

(e) Step 5—Tert-butyl 4-[1-(2,6-dioxo-3-piperidyl)-3-methyl-2-oxo-benzimidazol-4-yl]oxy piperidine-1-carboxylate

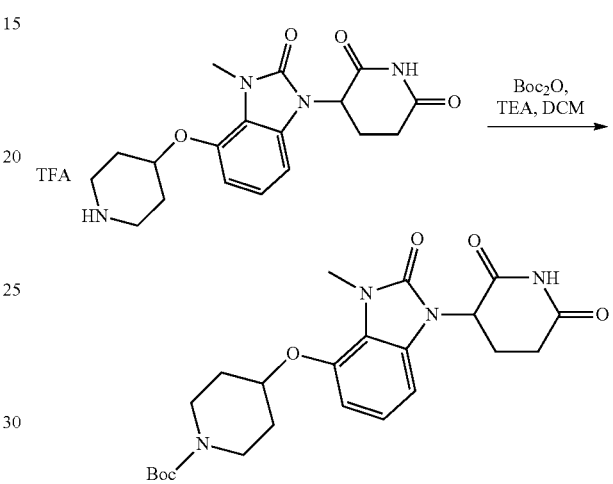

To a solution of 3-[3-methyl-2-oxo-4-(4-piperidyloxy)benzimidazol-1-yl]piperidine-2,6-dione (240 mg, 508 μmol TFA) in DCM (5 mL) was added TEA (154 mg, 1.52 mmol), (Boc)₂O (166 mg, 762 μmol) dropwise at 0° C., then the reaction mixture was stirred at 25° C. for 0.5 hr. On completion, the stirring reaction mixture was quenched with H₂O (5 mL) and the residue was diluted with water (20 mL) and extracted with EA (10 mL×3). The combined organic layer was dried over Na₂SO₄, filtered and concentrated in vacuo to give a residue. The residue was purified by reverse phase (0.1% FA condition) to give the title compound (200 mg, 86% yield) as light yellow solid. ¹H NMR (400 MHz, DMSO-d₆) δ 11.13 (s, 1H), 7.03-6.98 (m, 1H), 6.87 (d, J=8.4 Hz, 1H), 6.79 (d, J=8.0 Hz, 1H), 5.38 (dd, J=5.2, 12.8 Hz, 1H), 4.76-4.71 (m, 1H), 3.71-3.61 (m, 2H), 3.59 (s, 3H), 3.31-3.30 (m, 1H), 3.00-2.88 (m, 1H), 2.80-2.62 (m, 3H), 2.09-1.93 (m, 3H), 1.75-1.65 (m, 2H), 1.46 (s, 9H); LC-MS (ESI⁺) m/z 481.1 (M+Na)⁺.

(f) Step 6—3-[3-Methyl-2-oxo-4-(4-piperidyloxy)benzimidazol-1-yl]piperidine-2,6-dione

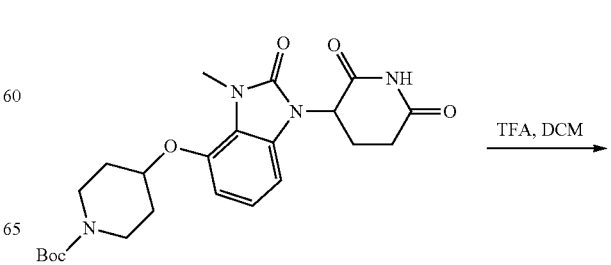

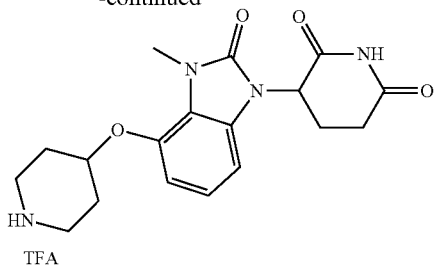

TFA

To a solution of tert-butyl 4-[1-(2,6-dioxo-3-piperidyl)-3-methyl-2-oxo-benzimidazol-4-yl]oxypiperidine-1-carboxylate (200 mg, 436 μmol) in DCM (3 mL) was added TFA (1.54 g, 13.4 mmol) dropwise at 0° C., then the reaction mixture was stirred at 25° C. for 0.1 hr. On completion, the reaction mixture was concentrated in vacuo to give the title compound (200 mg, 97% yield, TFA) as light yellow oil. LC-MS (ESI⁺) m/z 359.1 (M+H)⁺.

(g) Step 7—Tert-butyl 4-[4-[1-(2,6-dioxo-3-piperidyl)-3-methyl-2-oxo-benzimidazol-4-yl]oxy-1-piperidyl] piperidine-1-carboxylate

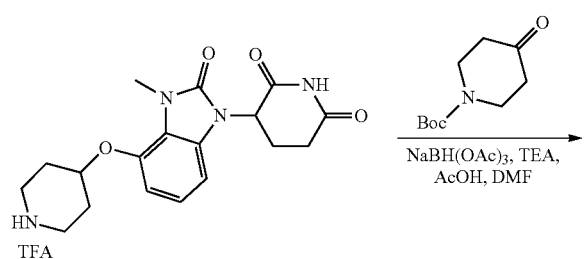

To a solution of 3-[3-methyl-2-oxo-4-(4-piperidyloxy)benzimidazol-1-yl]piperidine-2,6-dione (150 mg, 317 μmol, TFA) in DMF (10 mL) was added TEA (32.1 mg, 317 μmol) was stirred at 25° C. for 0.1 hr, then tert-butyl 4-oxopiperidine-1-carboxylate (63 mg, 317 μmol, CAS #79099-07-3), AcOH (19.0 mg, 317 μmol) was added at 25° C. and the mixture was stirred at 25° C. for 0.5 hr. Then NaBH(OAc)₃ (100 mg, 476 μmol) was added. The reaction was stirred at 25° C. for 0.2 hr. On completion, the stirring reaction mixture was quenched with H₂O (5 mL). The residue was diluted with water (10 mL) and extracted with EA (10 mL×3). The combined organic layer was dried over Na₂SO₄, filtered and concentrated in vacuo to give a residue. The residue was purified by reverse phase (0.1% FA condition) to give the title compound (150 mg, 87% yield) as light yellow solid. ¹H NMR (400 MHz, DMSO-d₆) δ 11.09 (s, 1H), 6.98-6.93 (m, 1H), 6.80 (d, J=8.4 Hz, 1H), 6.75 (d, J=8.0 Hz, 1H), 5.34 (dd, J=5.2, 12.8 Hz, 1H), 4.63-4.45 (m, 1H), 4.00-3.92 (m, 1H), 3.61 (t, J=6.4 Hz, 3H), 3.56 (s, 3H), 3.00-2.84 (m, 3H), 2.78-2.59 (m, 6H), 2.35 (t, J=6.4 Hz, 3H), 1.84-1.63 (m, 4H), 1.40 (s, 9H); LC-MS (ESI⁺) m/z 542.1 (M+H)⁺.

(h) Step 8—3-[3-Methyl-2-oxo-4-[[1-(4-piperidyl)-4-piperidyl]oxy]benzimidazol-1-yl]piperidine-2,6-dione

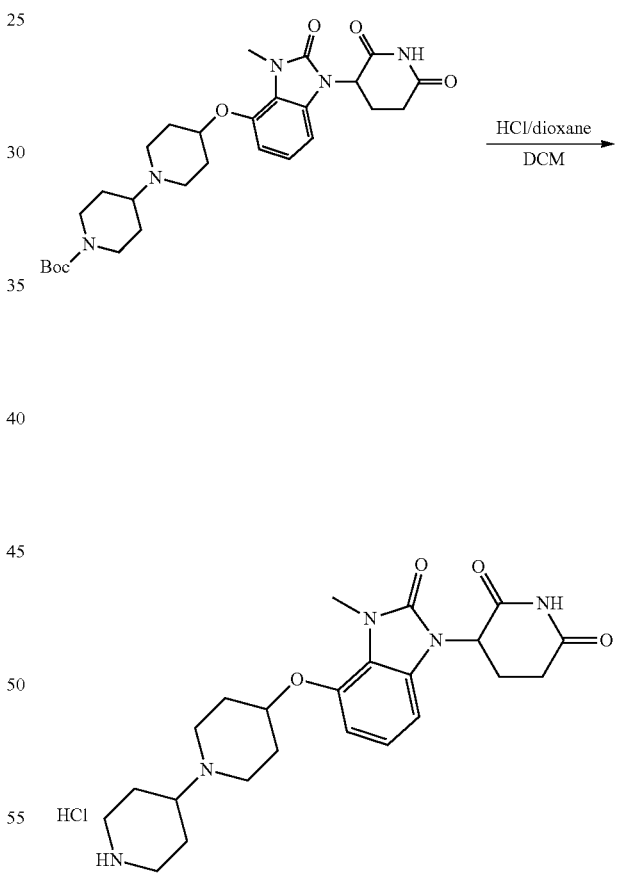

To a solution of tert-butyl 4-[4-[1-(2,6-dioxo-3-piperidyl)-3-methyl-2-oxo-benzimidazol-4-yl]oxy-1-piperidyl]piperidine-1-carboxylate (150 mg, 276 μmol) in DCM (3 mL) was added HCl/dioxane (4 M, 1 mL) dropwise at 0° C., then the reaction mixture was stirred at 25° C. for 0.1 hr. On completion, the reaction mixture was concentrated in vacuo to give the title compound (122 mg, 92% yield, HCl) was obtained as white solid. LC-MS (ESI⁺) m/z 442.0 (M+H)⁺.

(i) Step 9—Tert-butyl 3-[2-[[(3S,8S)-3-[[4-[4-[1-(2,6-dioxo-3-piperidyl)-3-methyl-2-oxo-benzimidazol-4-yl]oxy-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

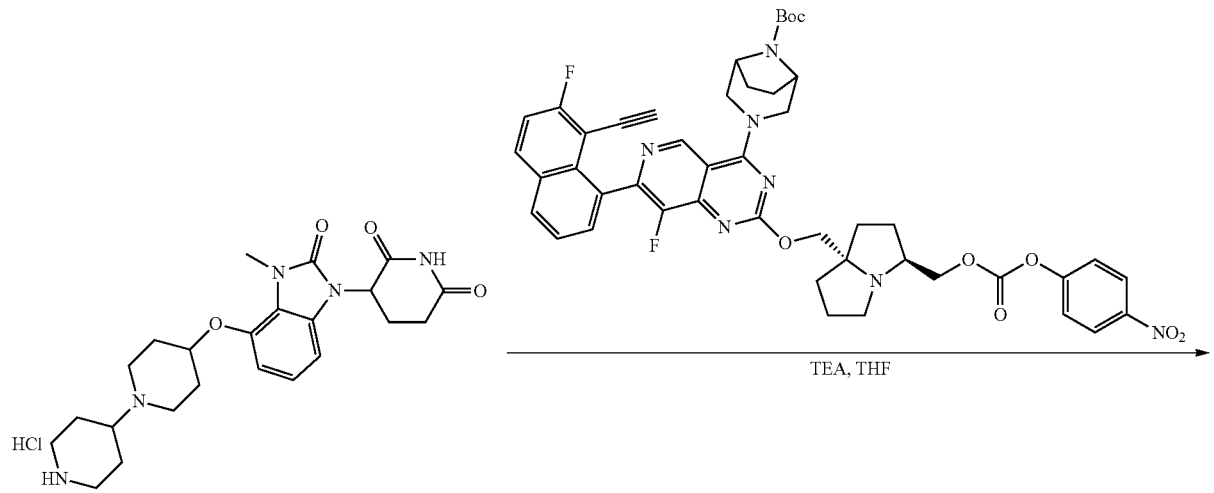

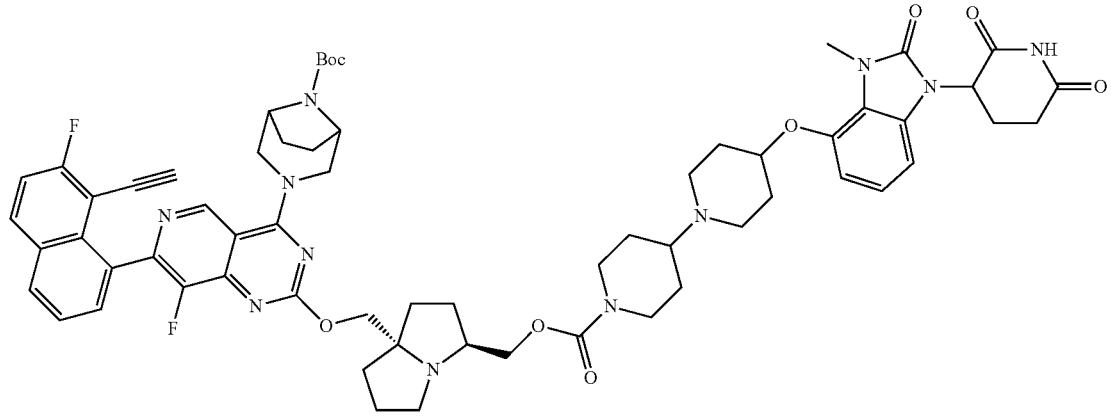

A mixture of 3-[3-methyl-2-oxo-4-[[1-(4-piperidyl)-4-piperidyl]oxy]benzimidazol-1-yl]piperidine-2,6-dione (77.6 mg, 162 μmol HCl), TEA (24.6 mg, 243 μmol) in THF (4 mL) was stirred at 25° C., then, tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70 mg, 81.2 μmol) in THF (4 mL) was added. The mixture was stirred at 25° C. for 0.15 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 19%-49% B over 10 min) to give the title compound (48 mg, 51% yield) was obtained as light yellow solid. LC-MS (ESI$^+$) m/z 1164.1 (M+H)$^+$.

(j) Step 10—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[4-[1-(2,
6-dioxo-3-piperidyl)-3-methyl-2-oxo-benzimidazol-
4-yl]oxy-1-piperidyl]piperidine-1-carboxylate (066)

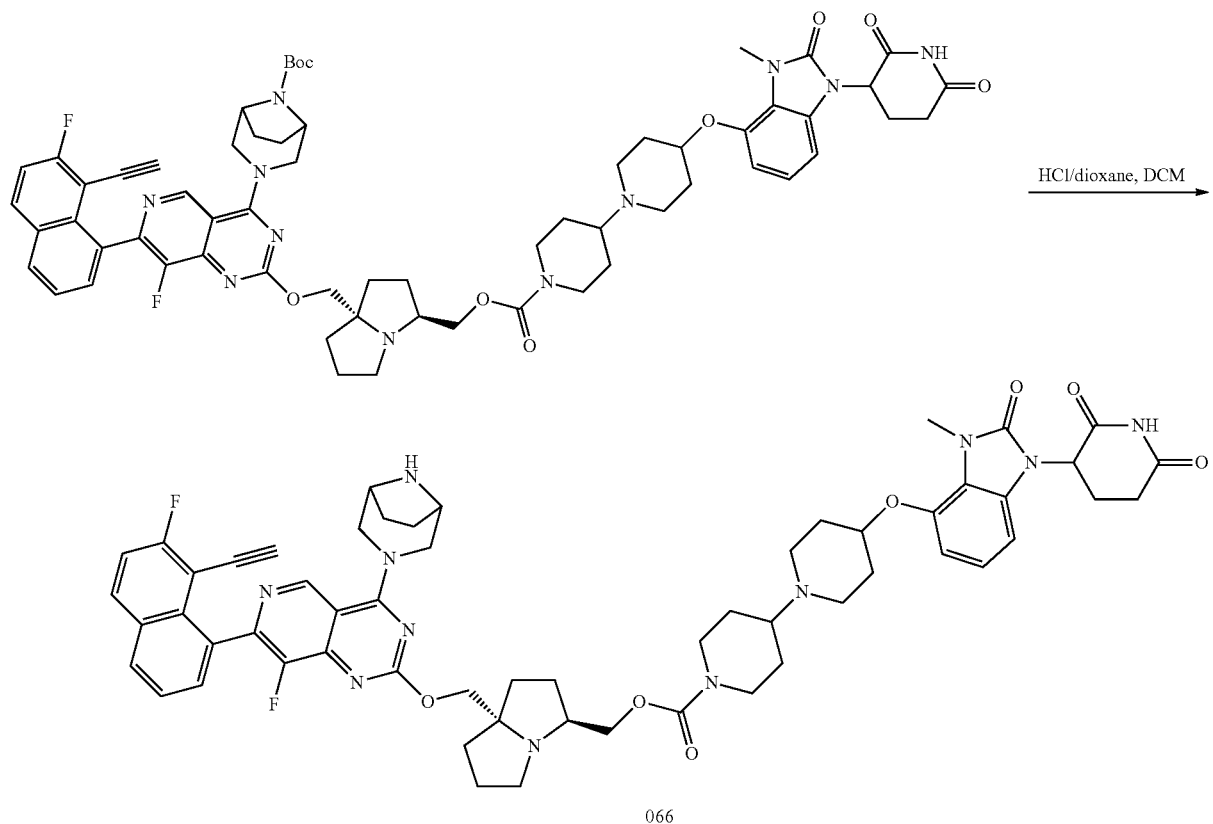

To a solution of tert-butyl 3-[2-[[(3S,8S)-3-[[4-[4-[1-(2,6-dioxo-3-piperidyl)-3-methyl-2-oxo-benzimidazol-4-yl]oxy-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40 mg, 34.3 µmol) in DCM (2 mL) was added HCl/dioxane (4 M, 0.5 mL) dropwise at 0° C., then the reaction mixture was stirred at 0° C. for 0.1 hr. On completion, the reaction mixture was concentrated in vacuo to give title compound (32.2 mg, 85% yield, HCl) as light yellow solid. $^1$H NMR (400 MHz, DMSO-$d_6$) δ 11.29-11.19 (m, 1H), 11.17-11.12 (m, 1H), 11.09 (s, 1H), 11.03-10.92 (m, 1H), 10.02-9.92 (m, 1H), 9.68-9.56 (m, 1H), 9.17 (s, 1H), 8.28-8.20 (m, 2H), 7.75-7.69 (m, 1H), 7.68-7.59 (m, 2H), 7.01-6.94 (m, 1H), 6.88-6.82 (m, 1H), 6.80 (d, J=8.4 Hz, 1H), 5.36 (dd, J=5.2, 12.8 Hz, 1H), 4.91 (s, 1H), 4.74-4.66 (m, 3H), 4.66-4.56 (m, 2H), 4.41 (d, J=10 Hz, 2H), 4.30-4.18 (m, 4H), 4.09-4.06 (m, 1H), 4.03-3.96 (m, 2H), 3.59 (s, 3H), 3.52-3.50 (m, 2H), 3.35-3.32 (m, 1H), 3.16-3.08 (m, 2H), 2.92-2.79 (m, 3H), 2.76-2.59 (m, 3H), 2.21-1.93 (m, 19H), 1.75-1.63 (m, 2H), 1.32-1.23 (m, 2H); LC-MS (ESI$^+$) m/z 1064.1 (M+H)$^+$.

Example 71. Synthesis of Compound 067

(a) Step 1—Tert-butyl 2-(2-bromoethyl)-7-azaspiro[3.5]nonane-7-carboxylate

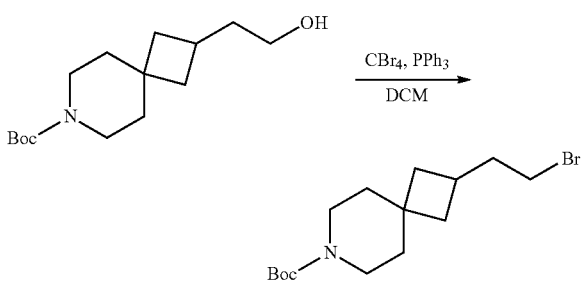

To a solution of tert-butyl 2-(2-hydroxyethyl)-7-azaspiro[3.5]nonane-7-carboxylate (2.00 g, 7.42 mmol) and PPh$_3$ (5.84 g, 22.2 mmol) in DCM (20 mL) was added CBr$_4$ (7.39 g, 22.2 mmol) at 0° C. The mixture was stirred at 25° C. for 14 hrs. On completion, the reaction mixture was filtered and the filtrated was concentrated in vacuo. The residue was purified by column chromatography (SiO$_2$, Petroleum ether/Ethyl acetate=100/1 to 20/1) to give the title compound (1.36 g, 55% yield) as white solid. ¹H NMR (400 MHz, CDCl₃) δ 3.38-3.29 (m, 4H), 3.28-3.21 (m, 2H), 2.46-2.33 (m, 1H), 2.04-1.92 (m, 4H), 1.60-1.54 (m, 2H), 1.50-1.36 (m, 13H).

(b) Step-2—Tert-butyl-2-[2-[1-(2,6-dioxo-3piperidyl)-3-methyl-2-oxo-benzimidazol-5-yl]ethyl]-7-azaspiro[3.5]nonane-7-carboxylate

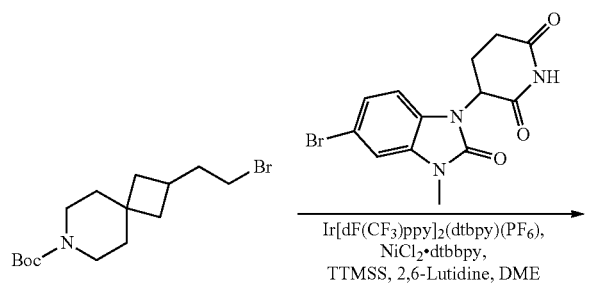

A mixture of tert-butyl 2-(2-bromoethyl)-7-azaspiro[3.5]nonane-7-carboxylate (255 mg, 768 μmol), 3-(5-bromo-3-methyl-2-oxo-benzimidazol-1-yl)piperidine-2,6-dione (200 mg, 591 μmol, CAS #23000-98-1), TTMSS (147 mg, 591 μmol), 4-tert-butyl-2-(4-tert-butyl-2pyridyl) pyridine; dichloronickel (3.53 mg, 8.87 μmol), 2,6-dimethylpyridine (570 mg, 5.32 mmol) and Ir[dF(CF₃)ppy]₂(dtbpy)(PF₆) (6.64 mg, 5.91 μmol) in DME (2 mL). The vial was sealed and placed under nitrogen was added. The reaction was stirred and irradiated with a blue 10 W LED lamp (3 cm away), with cooling water to keep the reaction temperature at 25° C. for 14 hrs. On completion, the mixture was filtered and the filtrate was concentrated in vacuo. The residue was purified by prep-HPLC (column: Phenomenex luna C18 150*25 mm*10 um; mobile phase: [water (FA)-ACN]; gradient: 50%-80% B over 10 min) to give the title compound (130 mg, 43% yield) as white solid. ¹H NMR (400 MHz, DMSO-d₆) δ 11.08 (s, 1H), 7.04-6.95 (m, 2H), 6.84 (dd, J=1.2, 8.0 Hz, 1H), 5.39-5.27 (m, 1H), 3.30 (s, 3H), 3.28-3.21 (m, 2H), 3.20-3.13 (m, 2H), 2.95-2.84 (m, 1H), 2.79-2.55 (m, 3H), 2.24-2.14 (m, 1H), 2.05-1.88 (m, 3H), 1.69 (q, J=7.2 Hz, 2H), 1.50-1.43 (m, 2H), 1.43-1.34 (m, 13H); LC-MS (ESI⁺) m/z 411.1 (M+H-Boc)⁺.

(c) Step-3—3-[5-[2-(7-Azaspiro-[3.5]nonan-2-yl)-ethyl]3-methyl-2oxo-benzimidazol-1-yl]-piperidine-2,6-dione

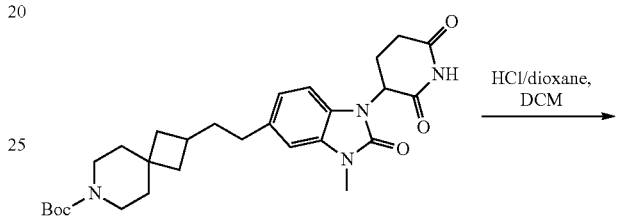

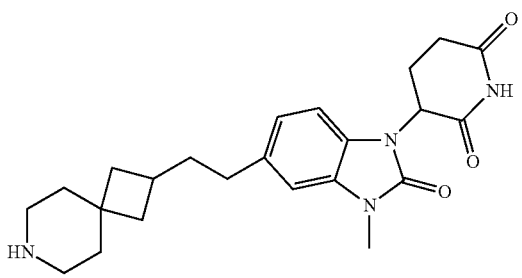

To a solution of tert-butyl 2-[2-[1-(2,6-dioxo-3-piperidyl)-3 methyl-2-oxo-benzimidazol-5-yl]ethyl] 7-azaspiro [3.5]nonane-7-carboxylate (65.0 mg, 127 μmol) in DCM (2 mL) was added HCl/dioxane (4 M, 31.8 μL). The mixture was stirred at 25° C. for 0.5 hr. On completion, the mixture was concentrated in vacuo to give the title compound (52.0 mg, 99% yield, HCl salt). LC-MS (ESI⁺) m/z 411.1 (M+H)⁺.

(d) Step-4—[(3S,8S)-8-[[4-(8-Tert-butoxycarbonyl-3,8-diazabicyclo[3.2.1]octan-3-yl)7-(8-ethynyl-7-fluoro-1-naphthyl)8-fluoro-pyrido[4,3-d]pyrimidin-2-yl]oxymethyl]-1,2,3,5,6,7-hexahydropyrrolizin-3-yl]methyl2-[2-[1-(2,6-dioxo-3-piperidyl)3-methyl-2-oxo-benzimidazol-5-yl]ethyl]-7-azaspiro[3.5]nonane-7-carboxylate

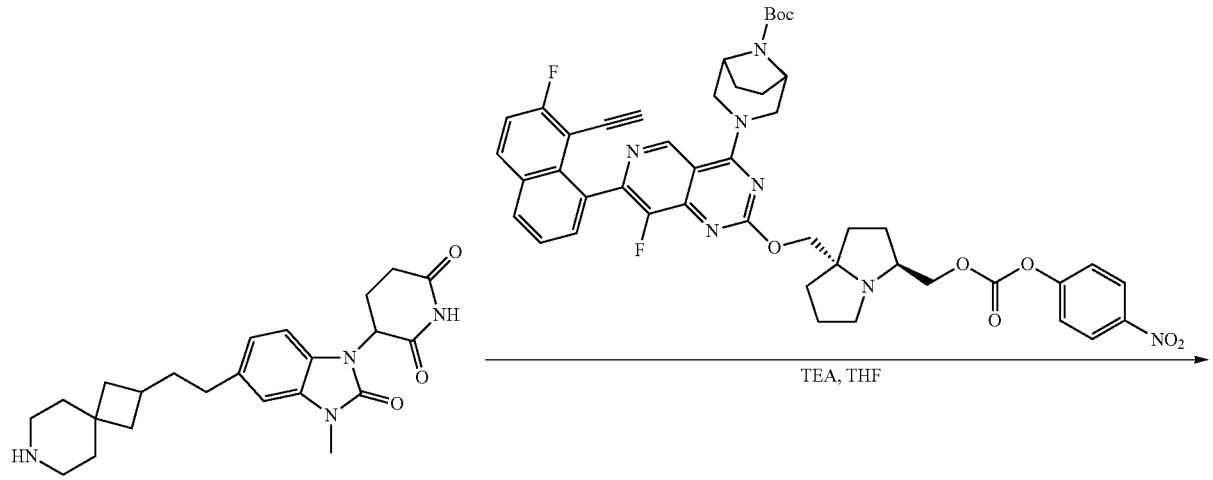

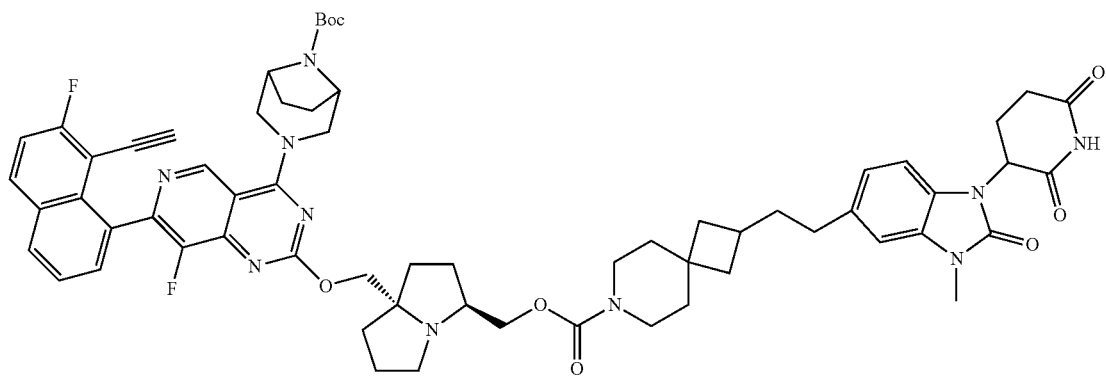

To a solution of 3-[5-[2-(7-azaspiro[3.5]nonan-2-yl)ethyl] 3-methyl 2-oxo-benzimidazol-1yl] piperidine-2,6-dione (50.0 mg, 121 μmol, HCl salt) in THF (3 mL) was added TEA (24.6 mg, 243 μmol)-and-tert-butyl-3-[7-(8ethynyl-7-fluoro-1-naphthyl)8-fluoro-2-[[(3S,8S)3-[(4-nitrophenoxy) carbonyloxymethyl]-1,2,3,5,6,7hexahydropyrrolizin-8-yl] methoxy]pyrido[4,3-d]pyrimidin-4-yl]-3,8-diazabicyclo [3.2.1]octane-8-carboxylate (70.0 mg, 81.2 μmol). The mixture was stirred at 25° C. for 1 hr. On completion, the mixture was concentrated in vacuo. The residue was purified by prep-HPLC (column: Phenomenex luna C18 150*25 mm*10 μm; mobile phase: [water (FA)-ACN]; gradient: 32%-62% B over 20 min) to give the title compound (53.0 mg, 57% yield) as white solid. LC-MS (ESI$^+$) m/z 1133.2 (M+H)$^+$.

(e) Step-5—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl2-[2-[1-(2,
6-dioxo-3-piperidyl)-3-methyl-2-oxo-benzimidazol-
5-yl]ethyl]-7-azaspiro[3.5]nonane-7-carboxylate
(067)

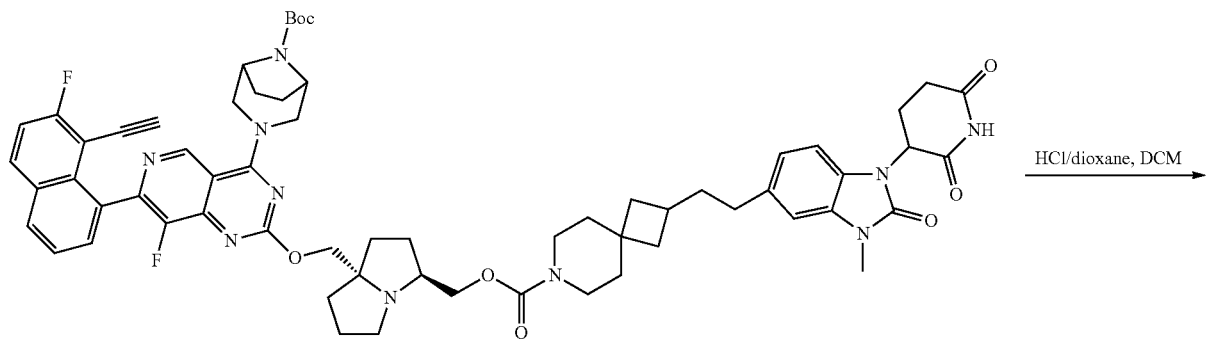

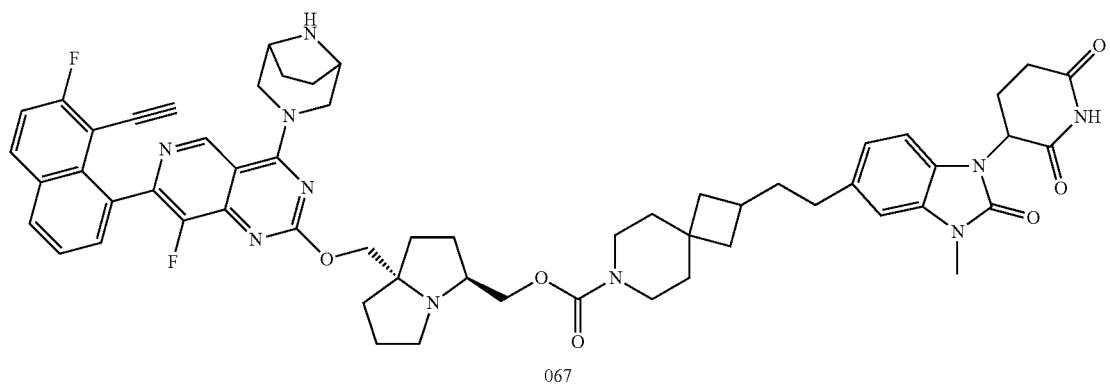

067

To a solution of [(3S,8S)-8-[[4-(8-tert-butoxycarbonyl-3, 8-diazabicyclo[3.2.1]octan-3-yl) 7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl-2-[2-[1-(2,6-dioxo-3-piperidyl)3-methyl-2-oxo-benzimidazol-5-yl] ethyl]-7-azaspiro[3.5]nonane-7-carboxylate (53.0 mg, 46.7 µmol) in DCM (2 mL) was added HCl/dioxane (4 M, 500 µL). The mixture was stirred at 25° C. for 0.5 hr. On completion, the mixture was concentrated then lyophilized to give the title compound (40.8 mg, 77% yield, HCl salt) as white solid. $^1$H NMR (400 MHz, DMSO-$d_6$) δ 11.11 (dd, J=2.0, 6.4 Hz, 1H), 10.69 (s, 1H), 9.82-9.72 (m, 1H), 9.46-9.35 (m, 1H), 9.17 (s, 1H), 8.31-8.19 (m, 2H), 7.76-7.69 (m, 1H), 7.68-7.58 (m, 2H), 7.04 (d, J=3.2 Hz, 2H), 6.88-6.79 (m, 1H), 5.39-5.28 (m, 1H), 4.77 (d, J=2.0 Hz, 4H), 4.42-4.33 (m, 1H), 4.29-4.14 (m, 3H), 4.08-3.86 (m, 4H), 3.42-3.33 (m, 4H), 3.30-3.20 (m, 2H), 2.98-2.83 (m, 1H), 2.71-2.58 (m, 2H), 2.36-2.24 (m, 2H), 2.24-2.06 (m, 4H), 2.05-1.86 (m, 12H), 1.73-1.65 (m, 2H), 1.53-1.47 (m, 2H), 1.45-1.36 (m, 4H), 1.28-1.21 (m, 2H); LC-MS (ESI+) m/z 1033.5 (M+H)$^+$.

Example 72. Synthesis of Compound 068

(a) Step 1—Tert-butyl 4-(4-piperidyloxymethyl)piperidine-1-carboxylate

To a mixture of tert-butyl 4-[(1-benzyloxycarbonyl-4-piperidyl)oxymethyl]piperidine-1-carboxylate (800 mg, 1.85 mmol) in MeOH (10 mL) was added Pd(OH)$_2$/C (200 mg, 1.42 mmol, 20% purity) and Pd/C (400 mg, 375 µmol, 10% purity), the reaction mixture was stirred at 25° C. for 12 hrs under H$_2$ (15 Psi) atmosphere. On completion, the reaction mixture was filtered and the filtrate was concentrated in vacuo to give the title compound (550 mg, crude) as yellow solid. $^1$H NMR (400 MHz, DMSO-$d_6$) δ 3.92 (d, J=11.2 Hz, 2H), 3.31-3.27 (m, 1H), 3.27-3.18 (m, 3H), 3.18-3.07 (m, 1H), 2.90-2.73 (m, 2H), 2.73-2.63 (m, 2H), 2.44-2.34 (m, 1H), 2.14-1.96 (m, 1H), 1.80-1.71 (m, 2H), 1.66-1.58 (m, 3H), 1.38 (s, 9H), 1.06-0.92 (m, 2H).

(b) Step 2—Tert-butyl 4-[[1-[[1-(2,6-dioxo-3-piperidyl)-3-methyl-2-oxo-benzimidazol-5-yl]methyl]-4-piperidyl]oxymethyl]piperidine-1-carboxylate

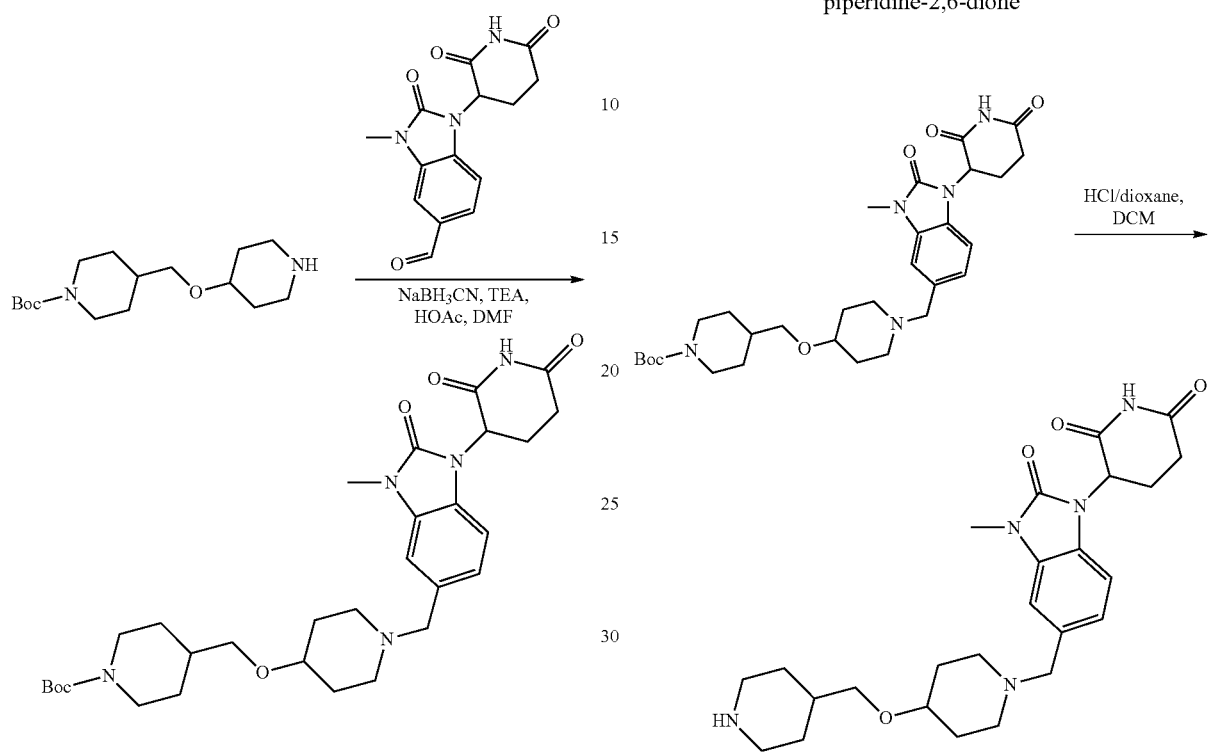

To a mixture of tert-butyl 4-(4-piperidyloxymethyl)piperidine-1-carboxylate (533 mg, 1.79 mmol) in DMF (2.5 mL) was added TEA (542 mg, 5.36 mmol, 745 μL) and HOAc (214 mg, 3.57 mmol, 204 μL), then 1-(2,6-dioxo-3-piperidyl)-3-methyl-2-oxo-benzimidazole-5-carbaldehyde (615 mg, 2.14 mmol) in DMF (2.5 mL) was added, the reaction mixture was stirred at 25° C. for 0.5 hr, finally NaBH3CN (168 mg, 2.68 mmol) was added, the reaction mixture was stirred at 30° C. for 12 hrs. On completion, the reaction mixture was quenched with water (0.5 mL) and then concentrated in vacuo to give a residue. The residue was purified by reverse phase (0.1% FA condition) to give the title compound (300 mg, 29% yield) as yellow solid. $^1$H NMR (400 MHz, DMSO-$d_6$) δ 11.12 (s, 1H), 7.38-7.08 (m, 3H), 5.40 (dd, J=4.8, 12.4 Hz, 1H), 4.38-4.29 (m, 1H), 3.97-3.89 (m, 2H), 3.37 (s, 3H), 3.30-3.20 (m, 4H), 3.24 (d, J=5.2 Hz, 2H), 3.10-3.01 (m, 1H), 3.00-2.88 (m, 2H), 2.78-2.69 (m, 2H), 2.66-2.56 (m, 2H), 2.13-1.90 (m, 3H), 1.86-1.71 (m, 2H), 1.70-1.57 (m, 4H), 1.54-1.43 (m, 1H), 1.38 (s, 9H).

(c) Step 3—3-[3-Methyl-2-oxo-5-[[4-(4-piperidylmethoxy)-1-piperidyl]methyl]benzimidazol-1-yl]piperidine-2,6-dione

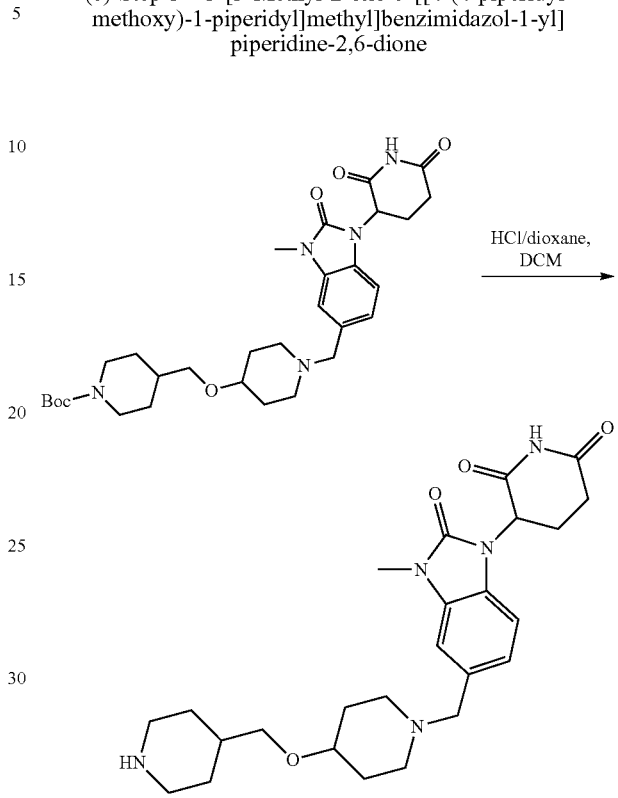

To a mixture of tert-butyl 4-[[1-[[1-(2,6-dioxo-3-piperidyl)-3-methyl-2-oxo-benzimidazol-5-yl]methyl]-4-piperidyl]oxymethyl]piperidine-1-carboxylate (90.0 mg, 157 μmol) in DCM (1 mL) was added HCl/dioxane (4 M, 1 mL), the reaction mixture was stirred at 25° C. for 1 hr. On completion, the mixture was concentrated in vacuo to give the title compound (70.0 mg, 94% yield, HCl salt) as yellow solid. LC-MS (ESI$^+$) m/z 470.0 (M+H)$^+$.

(d) Step 4—Tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

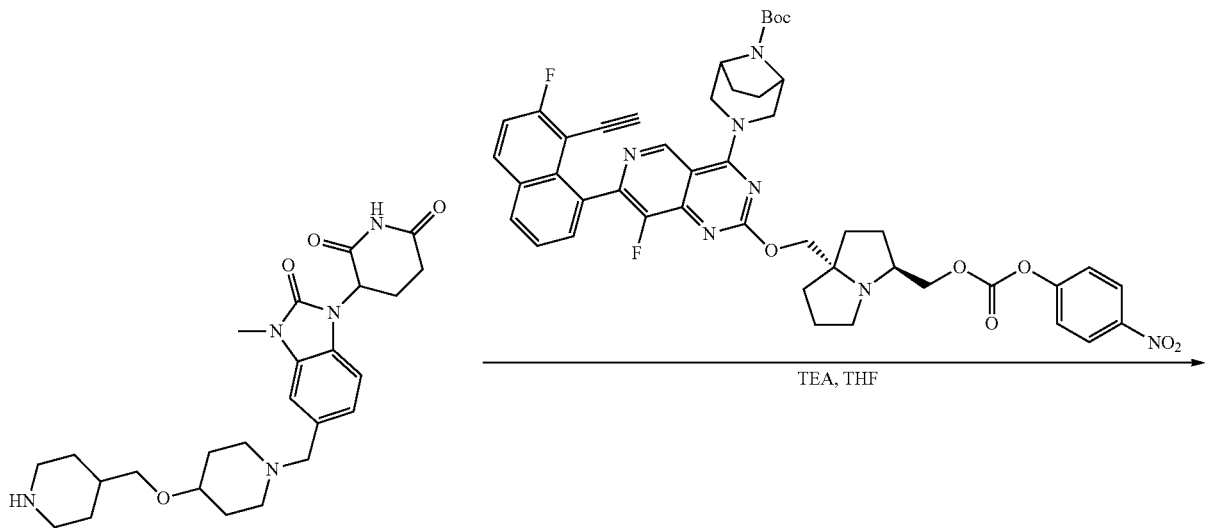

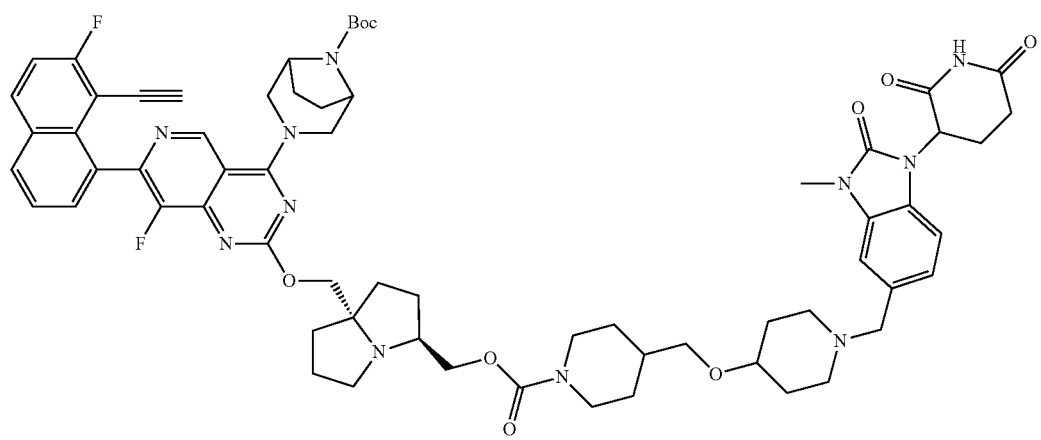

To a mixture of 3-[3-methyl-2-oxo-5-[[4-(4-piperidyl-methoxy)-1-piperidyl]methyl]benzimidazol-1-yl]piperidine-2,6-dione (70.0 mg, 149 μmol, HCl salt) in THF (1 mL) was added TEA (45.2 mg, 447 μmol, 62.2 μL) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (64.2 mg, 74.5 μmol), the reaction mixture was stirred at 25° C. for 12 hrs. On completion, the residue was concentrated in vacuo to give a residue. The residue was purified by prep-HPLC (column: Phenomenex luna C18 150*25 mm*10 um; mobile phase: [water (FA)-ACN]; gradient: 18%-48% B over 11 min) to give the title compound (45.0 mg, 25% yield) as yellow solid. LC-MS (ESI$^+$) m/z 1192.2 (M+H)$^+$.

(e) Step 5—[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[[1-[[1-(2,6-dioxo-3-piperidyl)-3-methyl-2-oxo-benzimidazol-5-yl]methyl]-4-piperidyl]oxymethyl]piperidine-1-carboxylate (068)

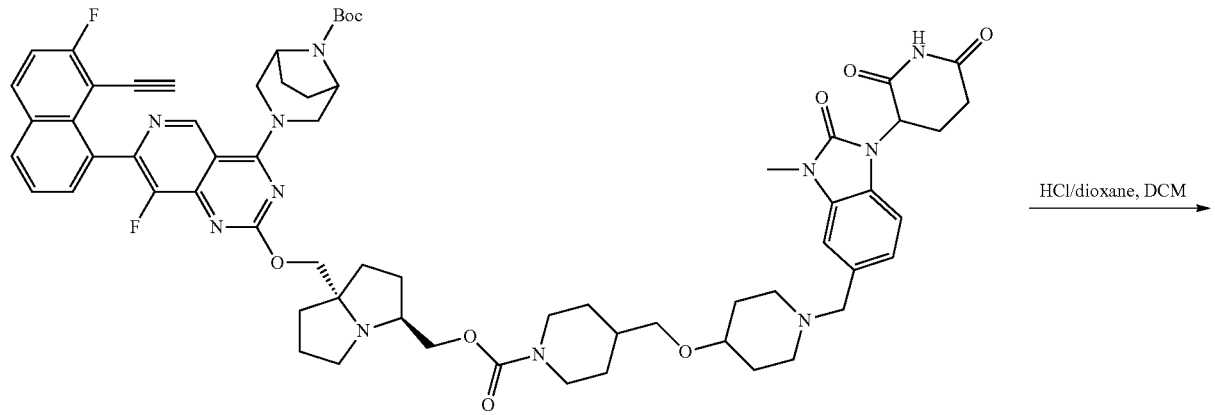

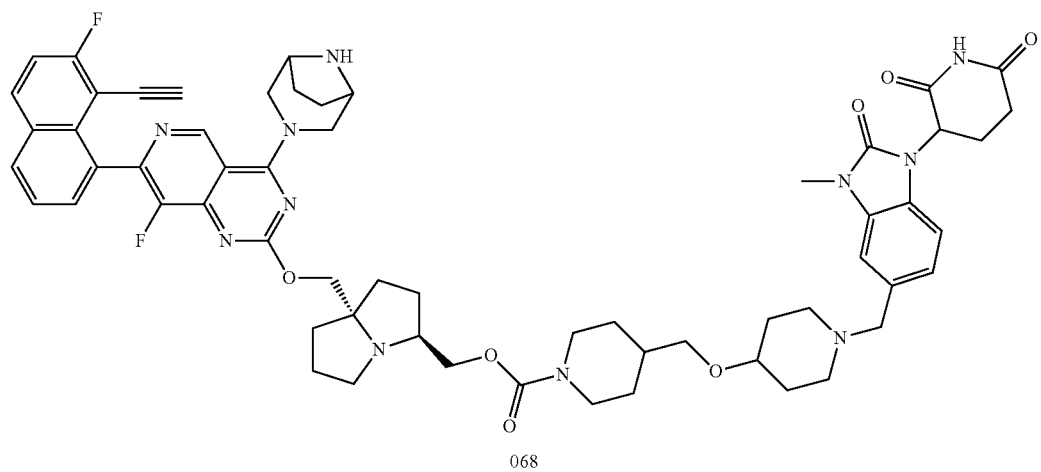

068

To a mixture of tert-butyl 3-[2-[[(3S,8S)-3-[[4-[[1-[[1-(2,6-dioxo-3-piperidyl)-3-methyl-2-oxo-benzimidazol-5-yl]methyl]-4-piperidyl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35.0 mg, 29.3 μmol) in DCM (2 mL) was added HCl/dioxane (4 M, 3.50 mL), the reaction mixture was stirred at 25° C. for 1 hr. On completion, the residue was concentrated in vacuo to give a residue. The residue was purified by prep-HPLC (column: Phenomenex luna C18 150*25 mm*10 μm; mobile phase: [water (FA)-ACN]; gradient: 0%-30% B over 11 min) to give the title compound (30.3 mg, 89% yield, FA) as yellow solid. $^1$H NMR (400 MHz, DMSO-$d_6$) δ 11.09 (s, 1H), 9.05 (s, 1H), 8.24-8.21 (m, 2H), 8.19 (dd, J=1.6, 8.0 Hz, 1H), 7.71-7.66 (m, 1H), 7.65-7.63 (m, 1H), 7.62 (s, 1H), 7.08 (s, 1H), 7.05-7.01 (m, 1H), 6.96-6.93 (m, 1H), 5.35 (dd, J=5.2, 12.8 Hz, 1H), 4.49 (d, J=12.0 Hz, 1H), 4.35 (d, J=11.6 Hz, 1H), 4.25-4.17 (m, 2H), 4.16-4.08 (m, 3H), 4.06 (d, J=10.4 Hz, 1H), 4.01 (s, 1H), 3.95 (d, J=12.4 Hz, 3H), 3.66 (s, 3H), 3.62 (d, J=12.8 Hz, 2H), 3.44 (s, 2H), 3.30-3.23 (m, 2H), 3.21 (d, J=5.6 Hz, 2H), 2.95-2.85 (m, 1H), 2.80-2.70 (m, 4H), 2.65-2.58 (m, 3H), 2.11-1.97 (m, 4H), 1.81-1.68 (m, 12H), 1.62-1.55 (m, 4H), 1.54-1.46 (m, 1H), 1.45-1.34 (m, 2H), 1.08-0.95 (m, 2H); LC-MS (ESI$^+$) m/z 1092.2 (M+H)$^+$.

Example 73. Synthesis of Compound 069

(a) Step 1—Tert-butyl 4-[2-[1-[[1-(2,6-dioxo-3-piperidyl)-3-methyl-2-oxo-benzimidazol-5-yl]methyl]-4-piperidyl]ethyl]piperidine-1-carboxylate To a mixture of 1-(2,6-dioxo-3-piperidyl)-3-methyl-2-oxo-benzimidazole-5-carbaldehyde (170 mg, 591 μmol, CAS #775288-40-9) in DMF (2 mL) was added TEA (59.8 mg, 591 μmol, 82.3 μL), then tert-butyl 4-[2-(4-piperidyl)ethyl]piperidine-1-carboxylate (175 mg, 591 μmol) and HOAc (35.5 mg, 591 μmol, 33.8 μL) was added, the reaction mixture was stirred at 25° C. for 0.5 hr, then NaBH₃CN (55.7 mg, 887 μmol) was added and stirred at 25° C. for 0.5 hr. On completion, the reaction mixture was quenched with water (0.5 mL) and concentrated in vacuo. The residue was purified by reverse phase (0.1% FA condition) to give the title compound (100 mg, 29% yield) as white solid. $^1$H NMR (400 MHz, CDCl$_3$) δ 8.55 (s, 1H), 7.32 (s, 1H), 7.04 (d, J=8.0 Hz, 1H), 6.77 (d, J=8.0 Hz, 1H), 5.23 (dd, J=5.2, 12.8 Hz, 1H), 3.46 (s, 3H), 3.26 (d, J=11.6 Hz, 2H), 2.96-2.91 (m, 2H), 2.83 (dd, J=4.8, 17.2 Hz, 2H), 2.72-2.62 (m, 4H), 2.35 (t, J=11.6 Hz, 2H), 1.77 (d, J=12.8 Hz, 2H), 1.63 (d, J=12.4 Hz, 4H), 1.57-1.51 (m, 2H), 1.45 (s, 9H), 1.31 (d, J=3.2 Hz, 4H), 1.11-1.00 (m, 4H). LC-MS (ESI$^+$) m/z 568.2 (M+H)$^+$.

(b) Step 2—3-[3-Methyl-2-oxo-5-[[4-[2-(4-piperidyl)ethyl]-1-piperidyl]methyl]benzimidazol-1-yl]piperidine-2,6-dione

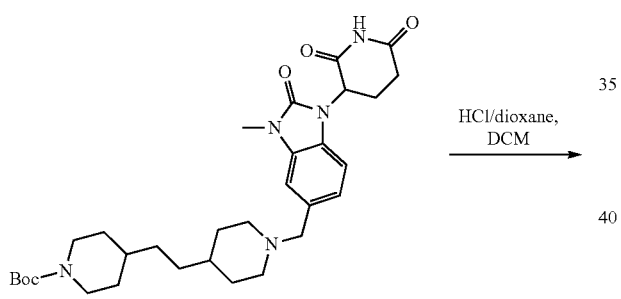

HCl/dioxane, DCM
⟶

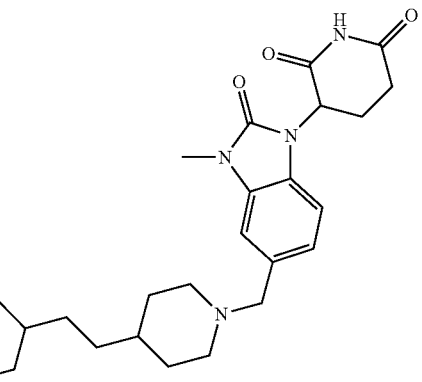

To a solution of tert-butyl 4-[2-[1-[[1-(2,6-dioxo-3-piperidyl)-3-methyl-2-oxo-benzimidazol-5-yl] methyl]-4-piperidyl]ethyl]piperidine-1-carboxylate (80.0 mg, 140 μmol) in DCM (1 mL) was added HCl/dioxane (4 M, 35.2 μL), the reaction mixture was stirred at 25° C. for 0.5 hr. On completion, the reaction mixture was concentrated in vacuo to give the title compound (65.0 mg, 98% yield, HCl salt) as white solid. LC-MS (ESI$^+$) m/z 468.1 (M+H)$^+$.

(c) Step 3—Tert-butyl 3-[2-[[(3S,8S)-3-[[4-[2-[1-[[1-(2,6-dioxo-3-piperidyl)-3-methyl-2-oxo-benzimidazol-5-yl]methyl]-4-piperidyl]ethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

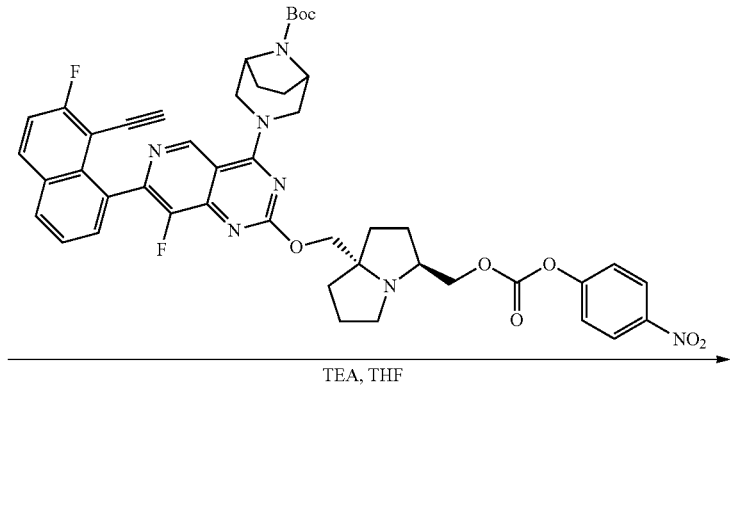

TEA, THF
⟶

-continued

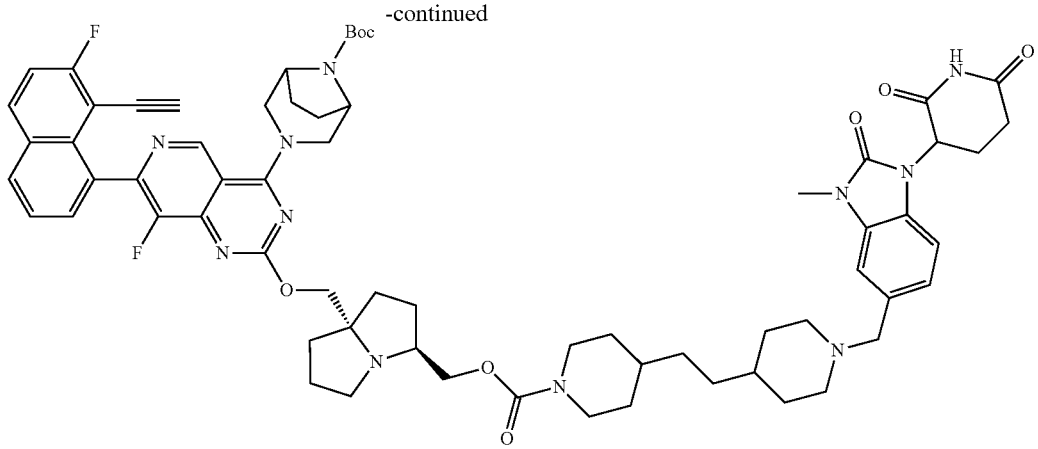

To a solution of 3-[3-methyl-2-oxo-5-[[4-[2-(4-piperidyl)ethyl]-1-piperidyl]methyl]benzimidazol-1-yl]piperidine-2,6-dione (48.8 mg, 104 μmol, HCl salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 69.6 μmol) in THF (1 mL) was added TEA (7.04 mg, 69.6 μmol, 9.69 μL), the reaction mixture was stirred at 25° C. for 0.5 hr. On completion, the reaction mixture was concentrated in vacuo. The residue was purified by prep-HPLC (column: Welch Ultimate C18 150*25 mm*5 μm; mobile phase: [water (FA)-ACN]; gradient: 20%-50% B over 12 min) and column: Phenomenex luna C18 150*25 mm*10 μm; mobile phase: [water (FA)-ACN]; gradient: 20%-50% B over 10 min to give the title compound (40.0 mg, 48% yield) as yellow solid. LC-MS (ESI$^+$) m/z 1190.6 (M+H)$^+$.

(d) Step 4—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[2-[1-[[1-(2,6-dioxo-3-piperidyl)-3-methyl-2-oxo-benzimidazol-5-yl]methyl]-4-piperidyl]ethyl]piperidine-1-carboxylate (069)

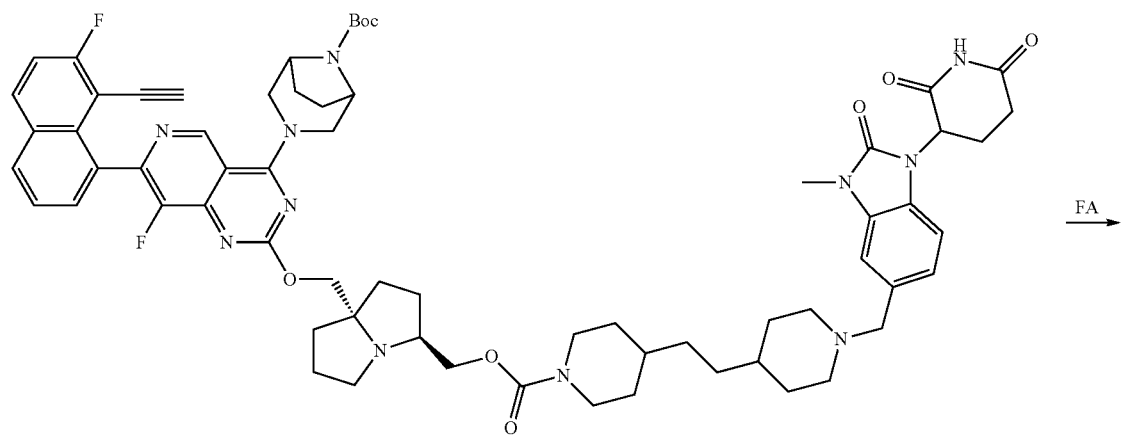

-continued

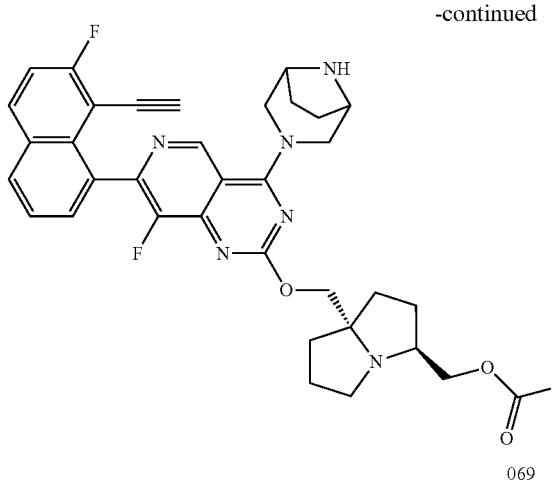

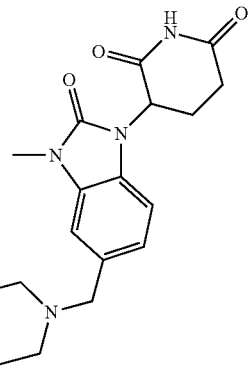

069

To a solution of tert-butyl 3-[2-[[(3S,8S)-3-[[4-[2-[1-[[1-(2,6-dioxo-3-piperidyl)-3-methyl-2-oxo-benzimidazol-5-yl]methyl]-4-piperidyl]ethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30.0 mg, 25.2 μmol) in FA (25.2 μmol, 1 mL), the reaction mixture was stirred at 25° C. for 0.2 hr. On completion, the reaction mixture was concentrated in vacuo. The residue was purified by prep-HPLC (column: Welch Xtimate C18 150*25 mm*5 μm; mobile phase: [water (FA)-ACN]; gradient: 3%-33% B over 10 min) to give the title compound (12.4 mg, 42% yield, FA) as white solid. $^1$H NMR (400 MHz, DMSO-$d_6$) δ 11.09 (s, 1H), 9.05 (s, 1H), 8.22-8.17 (m, 2H), 7.72-7.56 (m, 3H), 7.08 (s, 1H), 7.05-7.01 (m, 1H), 6.96-6.92 (m, 1H), 5.35 (dd, J=5.2, 12.4 Hz, 1H), 4.48 (d, J=11.6 Hz, 1H), 4.34 (d, J=11.6 Hz, 1H), 4.20 (dd, J=7.2, 11.2 Hz, 2H), 4.15-4.13 (m, 1H), 4.05 (d, J=10.4 Hz, 1H), 4.01 (s, 1H), 3.93 (d, J=11.2 Hz, 2H), 3.64 (s, 4H), 3.45 (s, 2H), 3.32 (s, 3H), 3.27 (dd, J=3.6, 5.2 Hz, 2H), 2.94-2.86 (m, 1H), 2.82-2.74 (m, 4H), 2.70 (dd, J=4.4, 12.8 Hz, 3H), 2.65-2.58 (m, 1H), 2.06-1.97 (m, 2H), 1.92-1.84 (m, 2H), 1.75 (d, J=6.0 Hz, 4H), 1.70 (s, 4H), 1.63-1.56 (m, 4H), 1.52-1.45 (m, 1H), 1.35-1.27 (m, 1H), 1.17 (s, 4H), 1.11 (d, J=5.6 Hz, 3H), 0.99-0.86 (m, 2H). LC-MS (ESI$^+$) m/z 1090.5 (M+H)$^+$.

Example 74. Synthesis of Compound 070

(a) Step 1—Tert-butyl 4-[1-[1-(2,6-dioxo-3-piperidyl)-3-methyl-2-oxo-benzimidazol-5-yl]-4-piperidyl] piperidine-1-carboxylate To a mixture of 3-(5-bromo-3-methyl-2-oxo-benzimidazol-1-yl)piperidine-2,6-dione (500 mg, 1.48 mmol, CAS #2300099-98-1) and tert-butyl 4-(4-piperidyl)piperidine-1-carboxylate (595 mg, 2.22 mmol, CAS #171049-35-7) in toluene (5 mL) was added RuPhos Pd G$_3$ (123 mg, 147 μmol) and RuPhos (69.0 mg, 147 μmol), LiHMDS (1 M, 5.91 mL) at 0° C. under N$_2$ atmosphere. The reaction mixture was stirred at 80° C. for 1.2 hrs. On completion, the residue was diluted with water (40 mL) and extracted with EA (2×30 mL). The combined organic layers was dried over Na$_2$SO$_4$, filtered and the filtrate concentrated in vacuo to give a residue. On completion, the residue was purified by reverse phase (0.1% FA condition) to give the title compound (400 mg, 51% yield) as brown solid. $^1$H NMR (400 MHz, DMSO-$d_6$) δ 11.07 (s, 1H), 6.92 (d, J=8.8 Hz, 1H), 6.82 (d, J=2.0 Hz, 1H), 6.62 (dd, J=2.0, 8.8 Hz, 1H), 5.28 (dd, J=5.2, 12.8 Hz, 1H), 4.06-3.90 (m, 2H), 3.61 (d, J=12.0 Hz, 2H), 3.30 (s, 3H), 2.92-2.84 (m, 2H), 2.73 (s, 1H), 2.68-2.62 (m, 3H), 2.02-1.94 (m, 1H), 1.79-1.65 (m, 4H), 1.39 (s, 9H), 1.34-1.12 (m, 5H), 1.10-1.00 (m, 2H). LC-MS (ESI$^+$) m/z 526.1 (M+H)$^+$.

(b) Step 2—3-[3-Methyl-2-oxo-5-[4-(4-piperidyl)-1-piperidyl]benzimidazol-1-yl]piperidine-2,6-dione

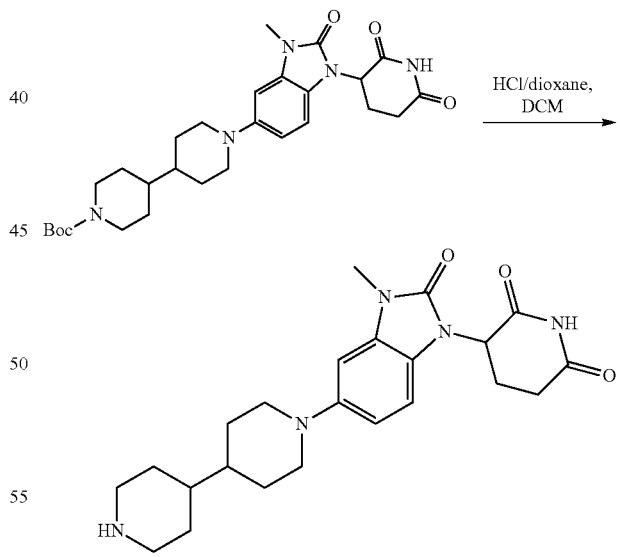

To a mixture of tert-butyl 4-[1-[1-(2,6-dioxo-3-piperidyl)-3-methyl-2-oxo-benzimidazol-5-yl]-4-piperidyl]piperidine-1-carboxylate (100 mg, 190 μmol) in DCM (1 mL) was added HCl/dioxane (2.5 M, 3.33 mL). The reaction mixture was stirred at 25° C. for 1 hr. On completion, the reaction mixture was concentrated in vacuo to give the title compound (80.0 mg, 98% yield, HCl salt) as white solid. LC-MS (ESI$^+$) m/z 426.1 (M+H)$^+$.

(c) Step 3—Tert-butyl 3-[2-[[(3S,8S)-3-[[4-[1-[1-(2,6-dioxo-3-piperidyl)-3-methyl-2-oxo-benzimidazol-5-yl]-4-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

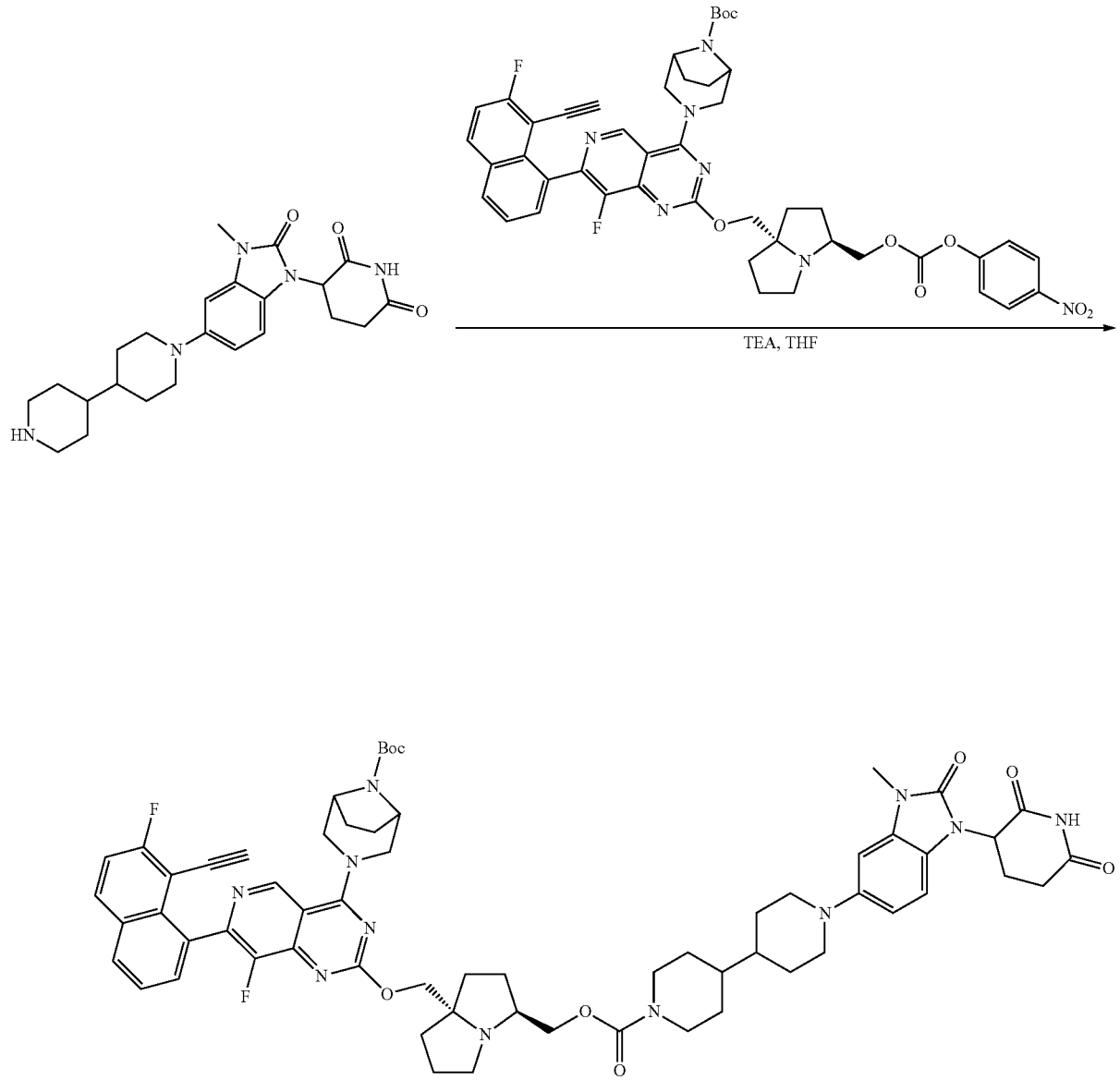

To a mixture of 3-[3-methyl-2-oxo-5-[4-(4-piperidyl)-1-piperidyl]benzimidazol-1-yl]piperidine-2,6-dione (75.0 mg, 176 μmol, HCl salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (75.9 mg, 88.1 μmol) in THF (1 mL) was added TEA (1.82 g, 17.9 mmol, 2.50 mL). The reaction mixture was stirred at 25° C. for 2 hrs. On completion, the reaction mixture was concentrated in vacuo. The residue was purified by prep-HPLC (column: Welch Ultimate C18 150*25 mm*5 μm; mobile phase: [water (FA)-ACN]; gradient: 19%-49% B over 12 min) to give the title compound (40.0 mg, 19% yield) as yellow solid. $^1$H NMR (400 MHz, DMSO-$d_6$) δ 11.05 (s, 1H), 9.09 (s, 1H), 8.30-8.16 (m, 3H), 7.72-7.57 (m, 2H), 6.94-6.88 (m, 1H), 6.84-6.78 (m, 1H), 6.65-6.57 (m, 1H), 5.28 (dd, J=5.2, 13.2 Hz, 1H), 4.61-4.51 (m, 1H), 4.47-4.36 (m, 1H), 4.35-4.26 (m, 2H), 4.25-4.18 (m, 1H), 4.17-3.97 (m, 5H), 3.73-3.53 (m, 3H), 3.30 (s, 2H), 3.29 (s, 3H), 2.94-2.83 (m, 1H), 2.80-2.69 (m, 3H), 2.63 (s, 1H), 2.57 (s, 4H), 2.07-1.95 (m, 2H), 1.91-1.61 (m, 14H), 1.46 (s, 9H), 1.40-1.24 (m, 4H), 1.23-0.96 (m, 4H); LC-MS (ESI$^+$) m/z 1148.6 (M+H)$^+$.

(d) Step 4—[(3S,8S)-8-[[4-(3,8-Diazabicyclo[3.2.1]
octan-3-yl)-7-(8-ethynyl-7-fluoro-1-naphthyl)-8-
fluoropyrido[4,3-d]pyrimidin-2-yl]oxymethyl]-1,2,3,
5,6,7-hexahydropyrrolizin-3-yl]methyl 4-[1-[1-(2,6-
dioxo-3-piperidyl)-3-methyl-2-oxo-benzimidazol-5-
yl]-4-piperidyl]piperidine-1-carboxylate (070)

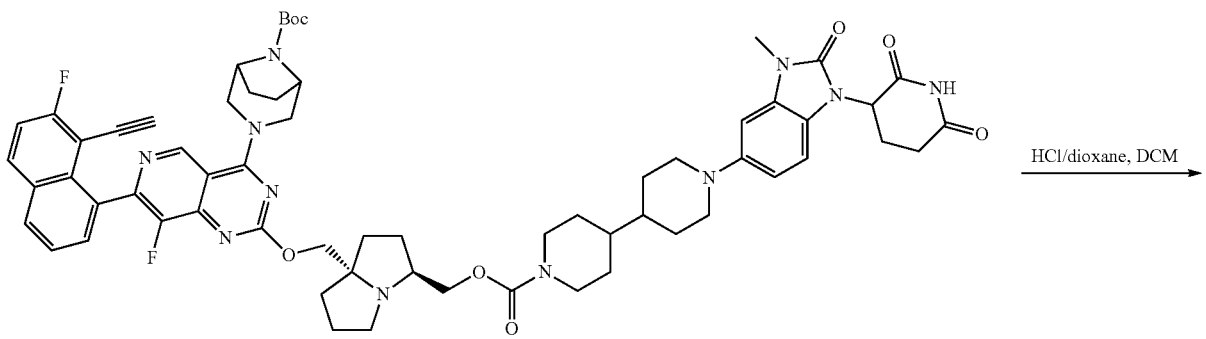

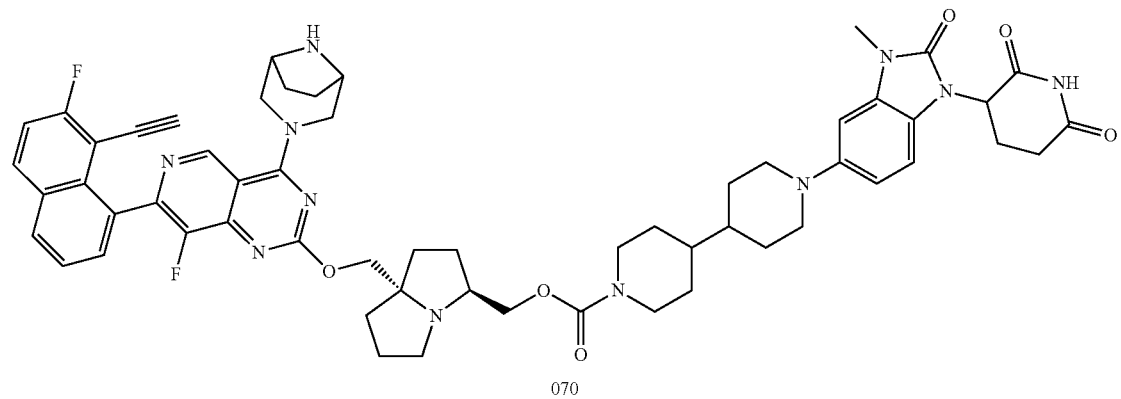

070

To a mixture of tert-butyl 3-[2-[[(3S,8S)-3-[[4-[1-[1-(2,
6-dioxo-3-piperidyl)-3-methyl-2-oxo-benzimidazol-5-yl]-4-
piperidyl]piperidine-1-carbonyl]oxymethyl]-1,2,3,5,6,7-
hexahydropyrrolizin-8-yl]methoxy]-7-(8-ethynyl-7-fluoro-
1-naphthyl)-8-fluoro-pyrido[4,3-d]pyrimidin-4-yl]-3,8-
diazabicyclo[3.2.1]octane-8-carboxylate (30.0 mg, 26.1 µmol) in DCM (1 mL) was added HCl/dioxane (2.5 M, 3.00 mL). The reaction mixture was stirred at 25° C. for 0.5 hr. On completion, the reaction mixture was concentrated in vacuo. The residue was purified by prep-HPLC (column: Phenomenex luna C18 150*25 mm*10 µm; mobile phase: [water (FA)-ACN]; gradient: 2%-32% B over 10 min) to give the title compound (8.48 mg, 28% yield, FA) as yellow solid. $^1$H NMR (400 MHz, DMSO-$d_6$) δ 11.06 (s, 1H), 9.05 (s, 1H), 8.26-8.16 (m, 3H), 7.72-7.57 (m, 3H), 6.91 (d, J=8.6 Hz, 1H), 6.80 (s, 1H), 6.60 (dd, J=1.6, 8.4 Hz, 1H), 5.32-5.23 (m, 1H), 4.50-4.43 (m, 1H), 4.36-4.30 (m, 1H), 4.25-4.18 (m, 1H), 4.16-4.10 (m, 2H), 4.07-3.97 (m, 4H), 3.67-3.54 (m, 8H), 2.94-2.82 (m, 2H), 2.77-2.70 (m, 4H), 2.62 (dd, J=1.6, 3.2 Hz, 4H), 2.09-1.93 (m, 2H), 1.80-1.61 (m, 14H), 1.54-1.47 (m, 1H), 1.37-1.18 (m, 4H), 1.17-1.00 (m, 3H); LC-MS (ESI$^+$) m/z 1048.4 (M+H)$^+$.

Example 75. Synthesis of Compound 071

(a) Step 1—Tert-butyl4-[[1-[[1-(2,6-dioxo-3-pip-
eridyl)-3-methyl2-oxo-benzimidazol-5-yl]methyl]-4-
piperidyl]methoxy]piperidine-1-carboxylate To a solution of tert-butyl 4-(4-piperidylmethoxy)piperidine-1-carboxylate (342 mg, 1.15 mmol) in DMF (5 mL) was added TEA (52.8 mg, 522 µmol) and HOAc (31.3 mg, 522 µmol). Then 1-(2,6-dioxo-3-piperidyl)-3-methyl-2 oxo-benzimidazole-5-carbaldehyde (300 mg, 1.04 mmol) and NaBH$_3$CN (98.4 mg, 1.57 mmol) was added. The mixture was stirred at 40° C. for 1 hr. On completion, the mixture was concentrated in vacuo. The crude product was purified by reversed-phase (0.1% FA condition) to give the title compound (100 mg, 16% yield) as white solid. $^1$H NMR (400 MHz, DMSO-$d_6$) δ 11.12 (s, 1H), 7.39-7.09 (m, 3H), 5.48 (s, 1H), 4.46-4.07 (m, 2H), 3.62-3.52 (m, 2H), 3.47-3.38 (m, 2H), 3.37 (s, 3H), 3.29 (s, 3H), 3.06-2.86 (m, 4H), 2.76-2.62 (m, 2H), 2.07-1.98 (m, 1H), 1.90-1.59 (m, 6H), 1.42-1.27 (m, 13H); LC-MS (ESI$^+$) m/z 570.2 (M+H)$^+$.

1233

(b) Step 2—3-[3-Methyl-2-oxo-5-[[4-(4-piperidyloxymethyl)-1-piperidyl]methyl]benzimidazol-1-yl]piperidine-2,6-dione

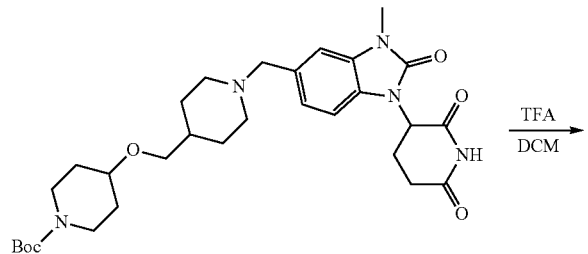

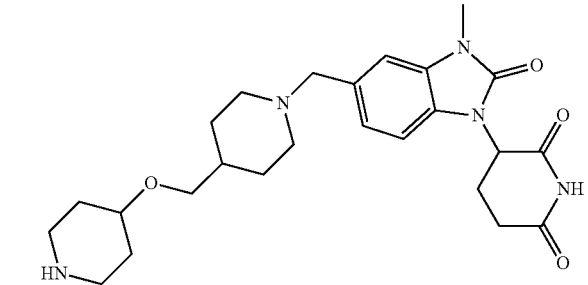

1234

To a solution of tert-butyl-4-[[1-[[1-(2,6-dioxo-3-piperidyl)-3-methyl-2-oxo-benzimidazol 5-yl]methyl]-4-piperidyl]methoxy]piperidine-1-carboxylate (75.0 mg, 131 μmol) in DCM (4 mL) was added TFA (100 μl). The mixture was stirred at 25° C. for 0.5 hr. On completion, the mixture was concentrated in vacuo to give the title compound (61.0 mg, 98% yield, TFA salt) as white solid. LC-MS (ESI$^+$) m/z 470.2 (M+H)$^+$.

(c) Step 3—Tert-butyl-3-[2-[[(3S,8S)-3-[[4-[[1-[[1-(2,6-dioxo-3-piperidyl)-3-methyl-2-oxo-benzimidazol-5-yl]methyl]-4-piperidyl]methoxy]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

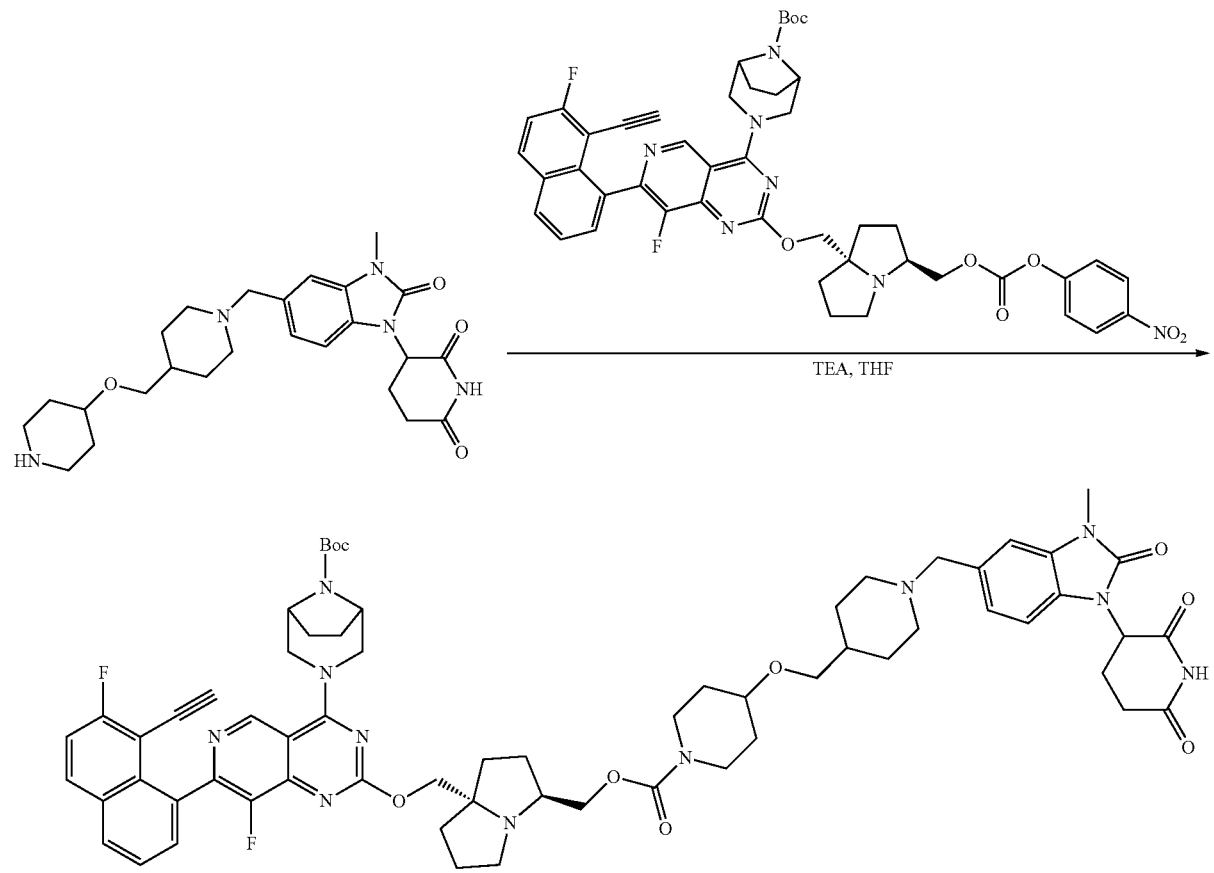

1235

To a solution of 3-[3-methyl-2-oxo-5-[[4(4-piperidyloxymethyl) 1-piperidyl]methyl]benzimidazol-1 yl]piperidine-2,6-dione (60.4 mg, 128 μmol, TFA salt) and tert-butyl-3-[7-(8-ethynyl-7-fluoro-1 naphthyl)-8fluoro-2[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74.0 mg, 85.8 μmol) in THF (3 mL) was added TEA (26.0 mg, 257 μmol). The mixture was stirred at 25° C. for 1 hr. On completion, the mixture was concentrated in vacuo. The residue was purified by prep-HPLC (column: Phenomenex Luna C18 150*25 mm*10 um; mobile phase: [water (FA)-ACN]; gradient: 16%-46% B over 10 min) to give the title compound (38.0 mg, 37% yield). LC-MS (ESI+) m/z 1192.5 (M+H)+.

(d) Step 4—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[[1-[[1-(2,6-dioxo-3-piperidyl)-3-methyl2-oxo-benzimidazol-5-yl]methyl]-4-piperidyl]methoxy]piperidine-1-carboxylate (071)

give the title compound (20.5 mg, 59% yield) as yellow solid. ¹H NMR (400 MHz, DMSO-d₆) δ 11.20-11.00 (m, 1H), 9.17-8.96 (m, 1H), 8.26-8.20 (m, 2H), 8.18 (s, 1H), 7.72-7.56 (m, 2H), 7.09 (s, 1H), 7.06-7.01 (m, 1H), 6.95 (d, J=8.0 Hz, 1H), 5.40-5.30 (m, 1H), 4.51 (d, J=12.4 Hz, 1H), 4.37 (d, J=12.0 Hz, 1H), 4.29-3.94 (m, 8H), 3.82-3.54 (m, 8H), 3.48 (s, 2H), 3.40 (td, J=4.0, 7.6 Hz, 1H), 3.32 (s, 3H), 3.24 (d, J=6.4 Hz, 2H), 3.15-3.04 (m, 2H), 2.97-2.57 (m, 7H), 2.13-1.85 (m, 4H), 1.80-1.69 (m, 8H), 1.67-1.58 (m, 2H), 1.57-1.41 (m, 2H), 1.40-1.25 (m, 2H), 1.25-1.09 (m, 2H); LC-MS (ESI+) m/z 1092.1 (M+H)+.

Example 76. Synthesis of Compound 072

(a) Step 1—Tert-butyl 4-[1-[[1-(2,6-dioxo-3-piperidyl)-3-methyl-2-oxo-benzimidazol-5-yl]methyl]-4-piperidyl]piperazine-1-carboxylate To a solution of tert-butyl 4-(4-piperidyl)piperazine-1-carboxylate (300 mg, 1.11 mmol, CAS #205059-24-1) in DMF (15 mL) was added HOAc (100 mg, 1.67 mmol) at 30° C. until pH stabilized at 6. Then 1-(2,6-dioxo-3-piperidyl)-3-methyl-2-oxo-benzimidazole-5-carbaldehyde (479 mg,

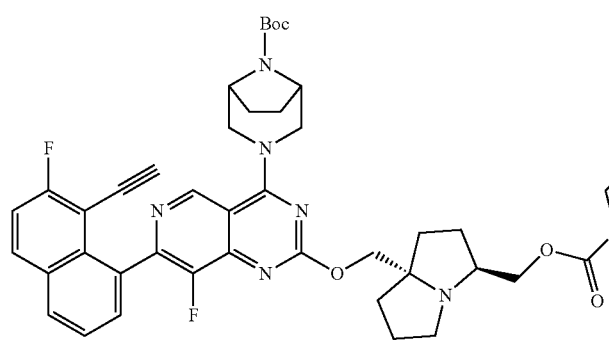

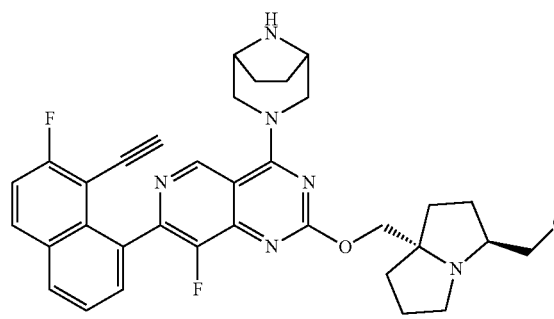

071

Tert-butyl-3-[2-[[(3S,8S)-3-[[4-[[1-[[1(2,6-dioxo-3-piperidyl)-3-methyl-2 oxo-benzimidazol-5-yl]methyl]-4-piperidyl]methoxy]piperidine-1-carbonyl]oxymethyl]-1,2,3,5,6,7-hexahydropyrrolizin-8-yl]methoxy]-7-(8-ethynyl-7-fluoro-1-naphthyl)8-fluoro-pyrido[4,3-d]pyrimidin-4-yl]-3,8-diazabicyclo[3.2.1]octane-8-carboxylate (38.0 mg, 31.8 μmol) was dissolved in HCOOH (1.53 mg, 31.8 μmol). The mixture was stirred at 25° C. for 0.5 hr. On completion, the mixture was concentrated in vacuo and then lyophilized to 1.67 mmol) was added. The reaction mixture was stirred at 30° C. for 1 hr. Finally, NaBH₃CN (104 mg, 1.67 mmol) was added to the mixture and stirred at 30° C. for 11 hrs. On completion, the reaction mixture was filtered and the filtrate was concentrated in vacuo to give a residue. The residue was purified by reverse phase (0.1% FA condition) to give the title compound (250 mg, 41% yield) as white solid. LC-MS (ESI+) m/z 541.2 (M+H)+.

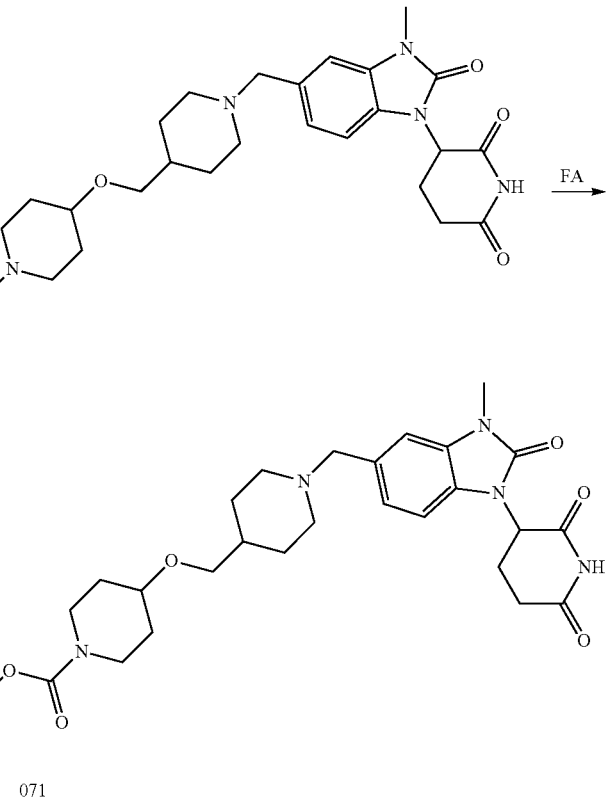

1237

(b) Step 2—3-[3-Methyl-2-oxo-5-[(4-piperazin-1-yl-1-piperidyl)methyl]benzimidazol-1-yl]piperidine-2,6-dione

1238

To a solution of tert-butyl 4-[1-[[1-(2,6-dioxo-3-piperidyl)-3-methyl-2-oxo-benzimidazol-5-yl]methyl]-4-piperidyl]piperazine-1-carboxylate (120 mg, 221 μmol) in DCM (3 mL) was added HCl/dioxane (4 M, 1 mL). The mixture was stirred at 25° C. for 0.25 hr. On completion, the reaction mixture was concentrated in vacuo to give the title compound (97.0 mg, 99% yield, HCl salt) as white solid. LC-MS (ESI$^+$) m/z 441.1 (M+H)$^+$.

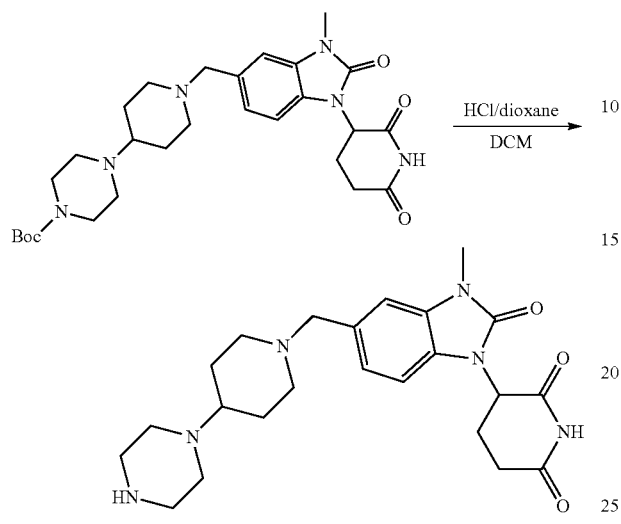

(c) Step 3—Tert-butyl 3-[2-[[(3S,8S)-3-[[4-[1-[[1-(2,6-dioxo-3-piperidyl)-3-methyl-2-oxo-benzimidazol-5-yl]methyl]-4-piperidyl]piperazine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

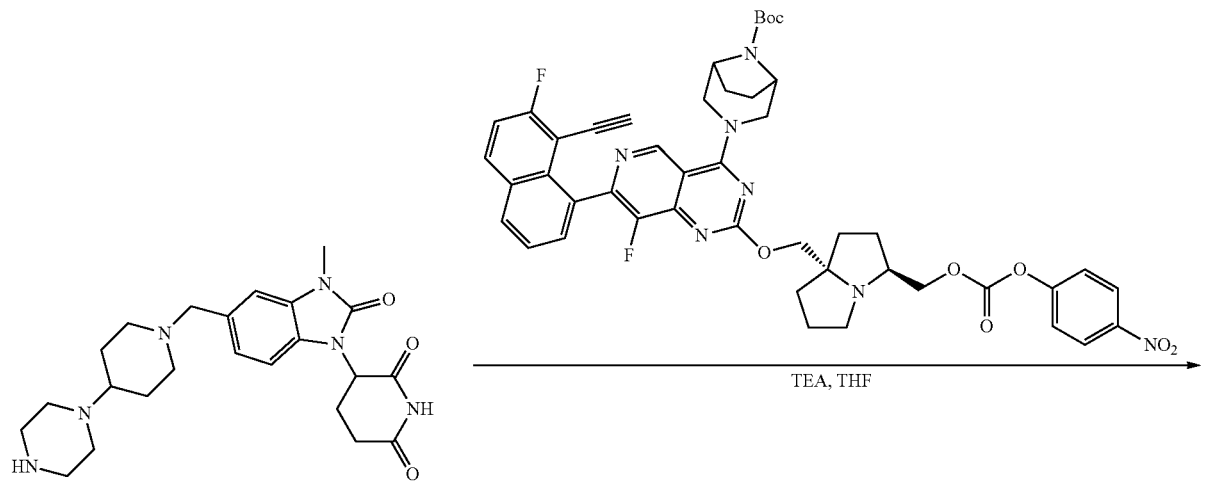

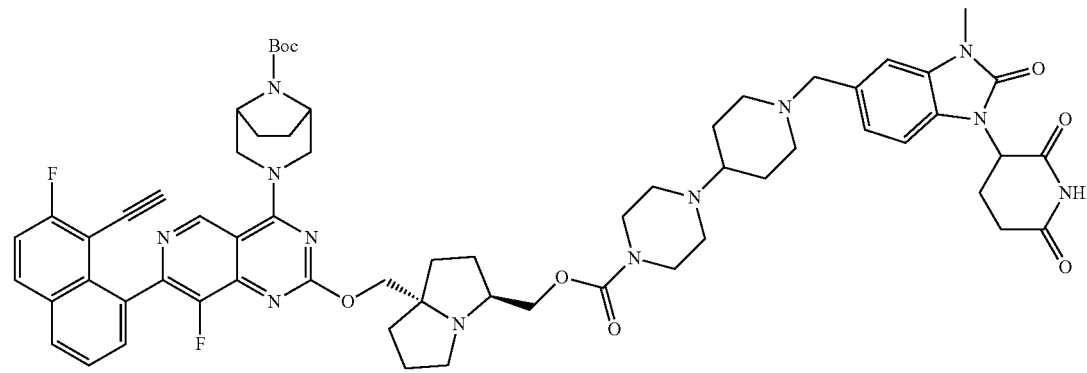

To a solution of 3-[3-methyl-2-oxo-5-[(4-piperazin-1-yl-1-piperidyl)methyl]benzimidazol-1-yl] piperidine-2,6-dione (71.5 mg, 162 µmol, HCl salt) in THF (3 mL) was added TEA (57.5 mg, 568 µmol) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 µmol). The mixture was stirred at 25° C. for 0.25 hr. On completion, the mixture was concentrated in vacuo to give a residue. The residue was purified by prep-HPLC (column: Phenomenex luna C18 150*25 mm*10 um; mobile phase: [water (FA)-ACN]; gradient: 16%-46% B over 10 min) to give the title compound (40.0 mg, 42% yield) as white solid. LC-MS (ESI+) m/z 1163.5 (M+H)+.

(d) Step 4—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[1-[[1-(2,6-dioxo-3-piperidyl)-3-methyl-2-oxo-benzimidazol-5-yl]methyl]-4-piperidyl]piperazine-1-carboxylate (072)

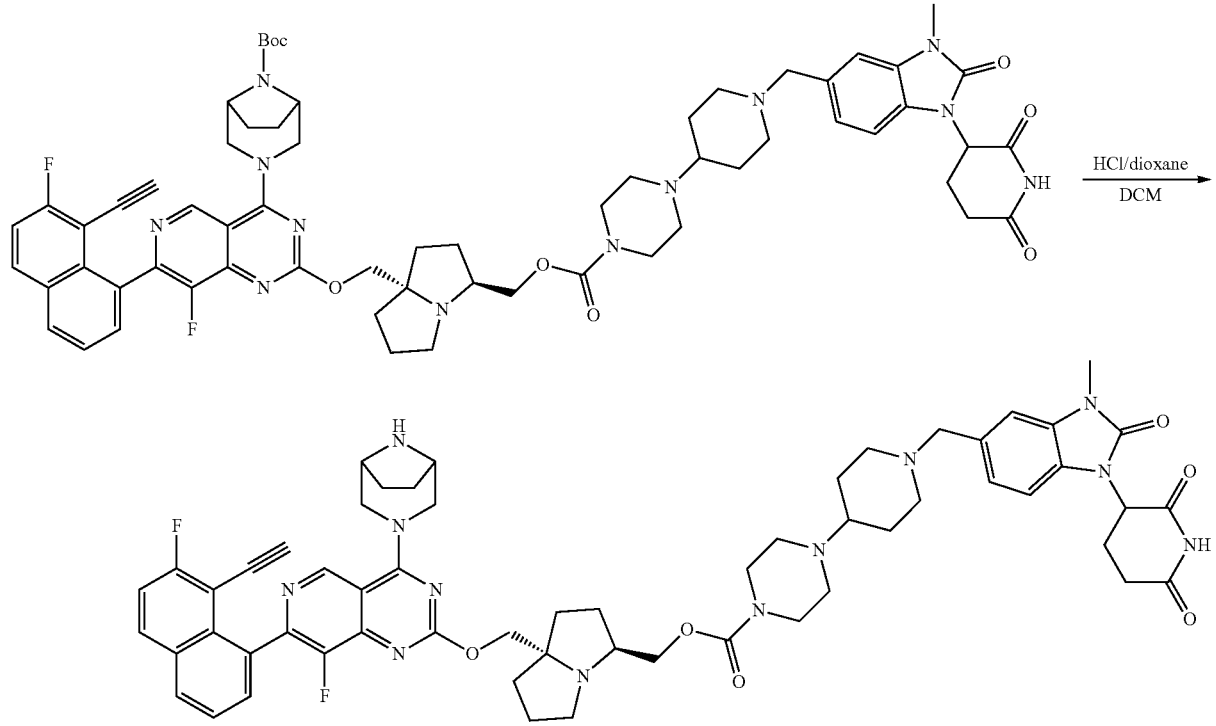

072

To a solution of tert-butyl 3-[2-[[(3S,8S)-3-[[4-[1-[[1-(2,6-dioxo-3-piperidyl)-3-methyl-2-oxo-benzimidazol-5-yl]methyl]-4-piperidyl]piperazine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 34.3 µmol) in DCM (3 mL) was added HCl/dioxane (4 M, 1 mL). The mixture was stirred at 25° C. for 0.25 hr. On completion, the residue was concentrated in vacuo to give a residue. The residue was purified by prep-HPLC (column: Phenomenex luna C18 150*25 mm*10 µm; mobile phase: [water (FA)-ACN]; gradient: 0%-28% B over 10 min) to give the title compound (15.2 mg, 38% yield, FA salt) as yellow solid. 1H NMR (400 MHz, DMSO-d6) δ 11.11 (s, 1H), 9.06 (s, 1H), 8.26-8.17 (m, 2H), 7.76-7.52 (m, 3H), 7.13-6.99 (m, 2H), 6.95 (d, J=8.0 Hz, 1H), 5.36 (dd, J=5.2, 12.8 Hz, 1H), 4.48 (d, J=12.0 Hz, 1H), 4.34 (d, J=12.0 Hz, 1H), 4.25-4.19 (m, 1H), 4.13 (d, J=10.4 Hz, 2H), 4.06 (s, 1H), 4.03 (s, 1H), 3.70-3.56 (m, 6H), 3.44 (s, 3H), 3.31-3.10 (m, 4H), 2.98-2.57 (m, 8H), 2.41 (s, 4H), 2.24-2.14 (m, 1H), 2.09-1.96 (m, 2H), 1.89 (t, J=10.8 Hz, 2H), 1.83-1.56 (m, 13H), 1.56-1.45 (m, 1H), 1.44-1.30 (m, 2H); LC-MS (ESI+) m/z 1063.7 (M+H)+.

Example 77. Synthesis of Compound 073

(a) Step 1—Tert-butyl 4-(azetidin-3-yloxymethyl)piperidine-1-carboxylate

To a solution of tert-butyl 4-[(1-benzyloxycarbonylazetidin-3-yl)oxymethyl]piperidine-1-carboxylate (700 mg, 1.73 mmol) in THF (10 mL) was added Pd/C (350 mg, 328 µmol, 10% purity) and Pd(OH)2/C (175 mg, 242 µmol, 20% purity) under N2 atmosphere. The suspension was degassed and purged with H2 for 3 times. The mixture was stirred under H2 (15 Psi.) at 25° C. for 2 hrs. On completion, the mixture was filtered, and the filtrate was concentrated in vacuo to give the title compound (507 mg, 86% yield) as brown oil. 1H NMR (400 MHz, CDCl3) δ 4.33-4.24 (m, 1H), 4.14-4.05 (m, 2H), 3.74-3.51 (m, 4H), 3.17 (d, J=6.4 Hz, 2H), 2.69 (t, J=12.4 Hz, 2H), 1.76-1.72 (m, 2H), 1.70-1.68 (m, 1H), 1.45 (s, 9H), 1.19-1.10 (m, 2H).

(b) Step 2—Tert-butyl 4-[[1-[[1-(2,6-dioxo-3-piperidyl)-3-methyl-2-oxo-benzimidazol-5-yl]methyl]azetidin-3-yl]oxymethyl]piperidine-1-carboxylate

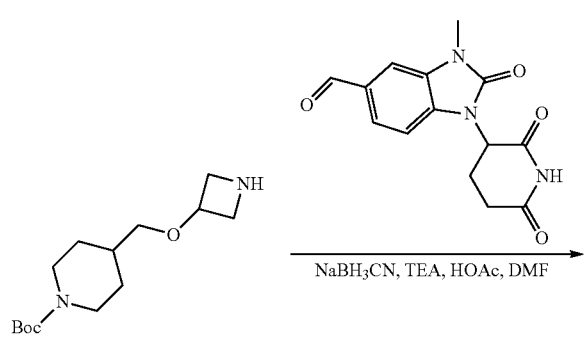

To a solution of tert-butyl 4-(azetidin-3-yloxymethyl)piperidine-1-carboxylate (500 mg, 1.85 mmol) and 1-(2,6-dioxo-3-piperidyl)-3-methyl-2-oxo-benzimidazole-5-carbaldehyde (531 mg, 1.85 mmol) in DMF (7 mL) was added TEA (187 mg, 1.85 mmol) for 10 min at 0° C. Then the AcOH (222 mg, 3.70 mmol) was added to the reaction for 20 mins. Finally, the NaBH$_3$CN (174 mg, 2.77 mmol) was added to the reaction. The mixture was stirred at 25° C. for 2 hrs. On completion, the mixture was concentrated in vacuo. The crude product was purified by reversed-phase HPLC (0.1% FA condition) to give the title compound (160 mg, 14% yield) as white solid. $^1$H NMR (400 MHz, DMSO-d$_6$) δ 11.08 (s, 1H), 7.10 (s, 1H), 7.07-7.01 (m, 1H), 6.99-6.92 (m, 1H), 5.35 (dd, J=5.2, 12.4 Hz, 1H), 4.08-4.02 (m, 1H), 3.94-3.98 (m, 2H), 3.68-3.62 (m, 2H), 3.59-3.52 (m, 2H), 3.33 (s, 3H), 3.14 (d, J=5.6 Hz, 2H), 3.06-2.77 (m, 4H), 2.76-2.60 (m, 4H), 2.04-1.97 (m, 1H), 1.64-1.59 (m, 2H), 1.38 (s, 9H), 1.05-0.95 (m, 2H); LC-MS (ESI$^+$) m/z 542.2 (M+H)$^+$.

(c) Step 3—3-[3-Methyl-2-oxo-5-[[3-(4-piperidyl-methoxy)azetidin-1-yl]methyl]benzimidazol-1-yl]piperidine-2,6-dione

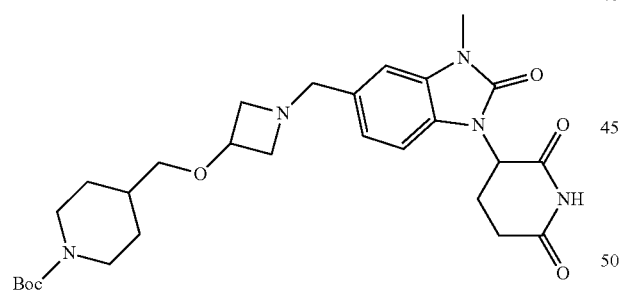

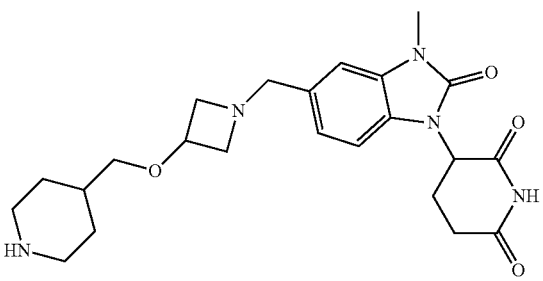

To a solution of tert-butyl 4-[[1-[[1-(2,6-dioxo-3-piperidyl)-3-methyl-2-oxo-benzimidazol-5-yl]methyl]azetidin-3-yl]oxymethyl]piperidine-1-carboxylate (100 mg, 184 μmol) in DCM (1 mL) was added TFA (3.07 g, 26.9 mmol). The mixture was stirred at 25° C. for 0.1 hr. On completion, the mixture was concentrated in vacuo to give the title compound (78.0 mg, 95% yield, TFA salt) as yellow oil. LC-MS (ESI+) m/z 442.1 (M+H)$^+$.

(d) Step 4—Tert-butyl 3-[2-[[(3S,8S)-3-[[4-[[1-[[1-(2,6-dioxo-3-piperidyl)-3-methyl-2-oxo-benzimidazol-5-yl]methyl]azetidin-3-yl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

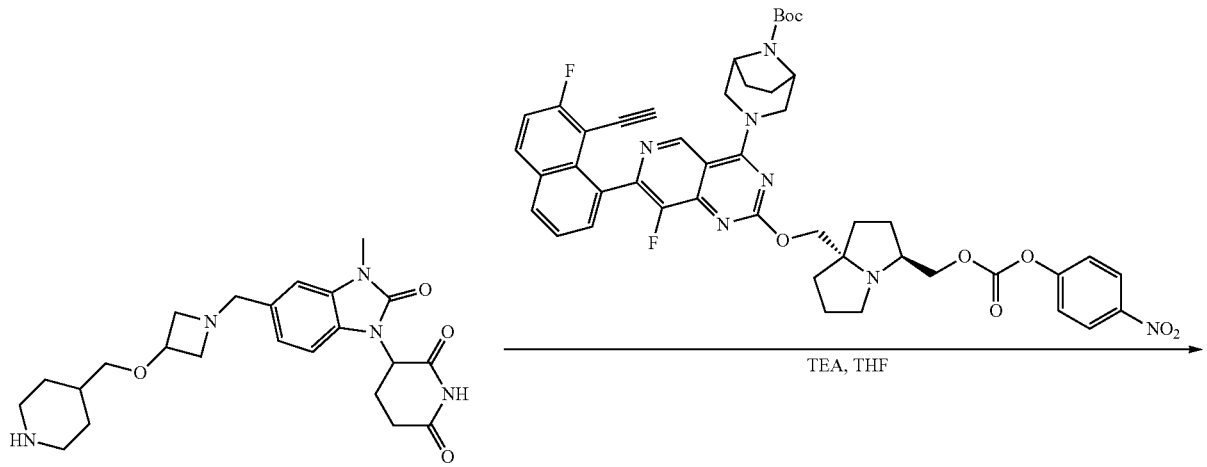

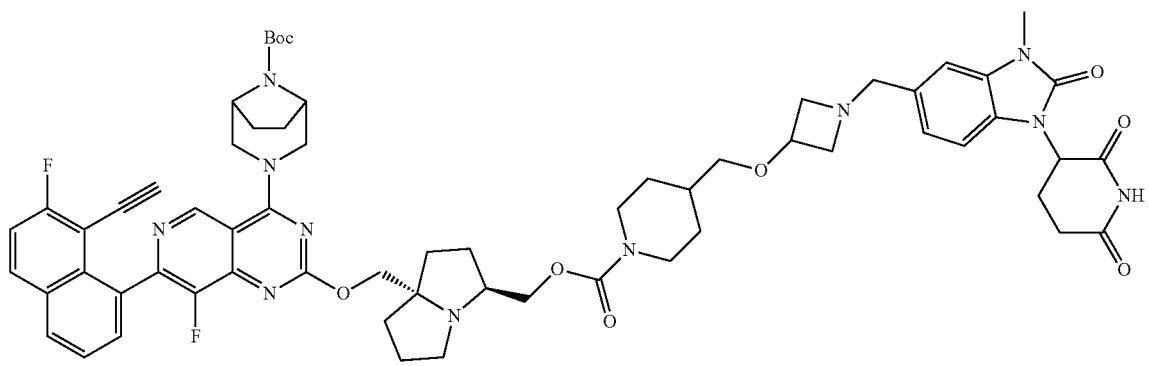

To a solution of 3-[3-methyl-2-oxo-5-[[3-(4-piperidylmethoxy)azetidin-1-yl]methyl]benzimidazol-1-yl]piperidine-2,6-dione (60.0 mg, 108 μmol, TFA salt) in THF (0.5 mL) was added TEA (14.57 mg, 144 μmol). A solution of tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (62.0 mg, 72.0 μmol) in THF (0.5 mL) was added to the reaction. The mixture was stirred at 25° C. for 0.5 hr. On completion, the mixture was concentrated in vacuo. The residue was purified by prep-HPLC (column: Welch Xtimate C18 150*25 mm*5 um; mobile phase: [water (FA)-ACN]; gradient: 13%-43% B over 10 min) to give the title compound (25.0 mg, 27% yield) as white solid. LC-MS (ESI+) m/z 1164.2 (M+H)⁺.

(e) Step 5—[(3S,8S)-8-[[4-(3,8-diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl4-[[1-[[1-(2,
6-dioxo-3-piperidyl)-3-methyl-2-oxo-benzimidazol-
5-yl]methyl]azetidin-3-yl]oxymethyl]piperidine-1-
carboxylate (073)

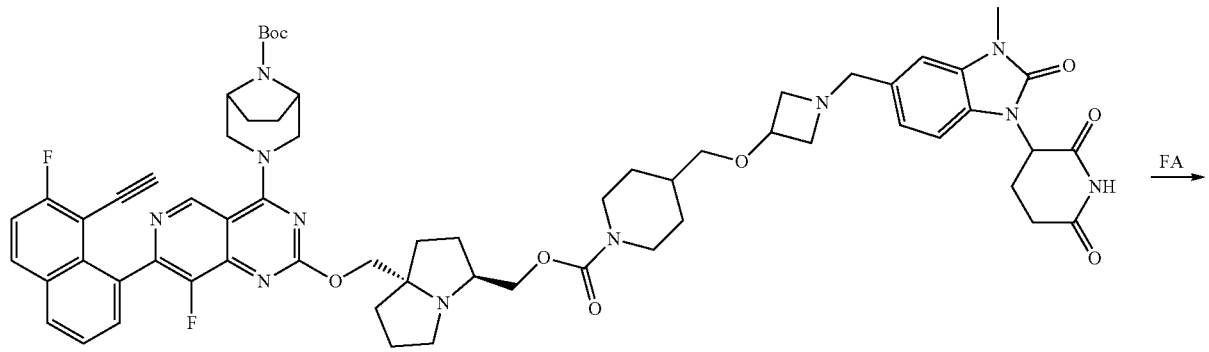

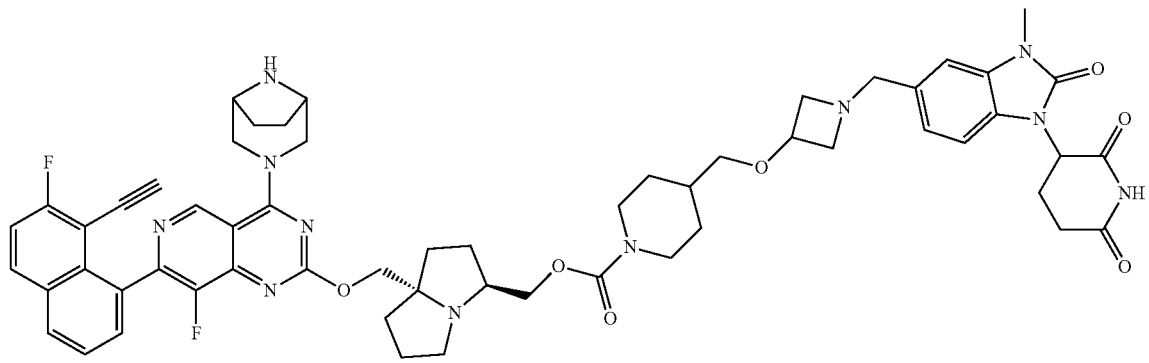

073

A solution of tert-butyl 3-[2-[[(3S,8S)-3-[[4-[[1-[[1-(2,6-dioxo-3-piperidyl)-3-methyl-2-oxo-benzimidazol-5-yl]methyl]azetidin-3-yl]oxymethyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (25.0 mg, 21.4 μmol) in HCOOH (0.5 mL) was stirred at 25° C. for 1 hr. On completion, the mixture was concentrated in vacuo. The residue was purified by prep-HPLC (column: Welch Ultimate C18 150*25 mm*5 um; mobile phase: [water (FA)-ACN]; gradient: 4%-34% B over 15 min) to give the title compound (15.1 mg, 62% yield, FA salt) as yellow solid. $^1$H NMR (400 MHz, DMSO-$d_6$) δ 11.09 (s, 1H), 9.06 (s, 1H), 8.25-8.21 (m, 1H), 8.20-8.17 (m, 1H), 7.73-7.56 (m, 3H), 7.07 (s, 1H), 7.02 (d, J=8.0 Hz, 1H), 6.93 (d, J=8.0 Hz, 1H), 5.34 (dd, J=5.2, 12.4 Hz, 1H), 4.51 (d, J=12.4 Hz, 1H), 4.37 (d, J=12.4 Hz, 1H), 4.22-4.20 (m, 1H), 4.17-4.14 (m, 2H), 4.10-4.07 (m, 2H), 4.02 (s, 1H), 3.98-3.95 (m, 2H), 3.78-3.70 (m, 4H), 3.69-3.65 (m, 2H), 3.65-3.62 (m, 1H), 3.58 (s, 3H), 3.47 (t, J=6.4 Hz, 2H), 3.31-3.25 (m, 2H), 3.12 (d, J=5.6 Hz, 2H), 2.83-2.80 (m, 2H), 2.79-2.75 (m, 2H), 2.74-2.56 (m, 4H), 2.10-1.97 (m, 2H), 1.84-1.75 (m, 4H), 1.74-1.71 (m, 4H), 1.69-1.58 (m, 4H), 1.57-1.51 (m, 1H), 1.08-0.96 (m, 2H); LC-MS (ESI+) m/z 1064.4 (M+H)$^+$.

Example 78. Synthesis of Compound 074

(a) Step 1—Tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate

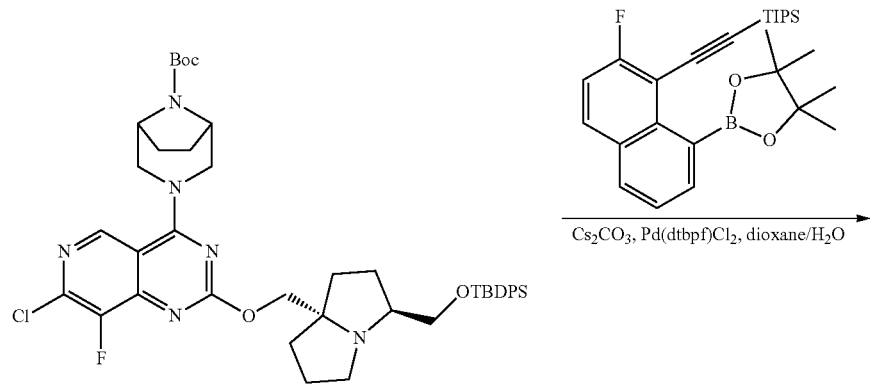

A solution of tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (3.00 g, 3.74 mmol), 2-[2-fluoro-8-(4,4,5,5-tetramethyl-1,3,2-dioxaborolan-2-yl)-1-naphthyl]ethynyl-triisopropyl-silane (2.20 g, 4.87 mmol), ditert-butyl (cyclopentyl)phosphane; dichloropalladium; iron (487 mg, 748 μmol, CAS #2503307-87-5), and Cs$_2$CO$_3$ (3.66 g, 11.2 mmol) in dioxane (60 mL) and H$_2$O (12 mL) was degassed and purged with N$_2$ for 3 times, then the mixture was stirred at 100° C. for 1 hr under N$_2$ atmosphere. On completion, the reaction mixture was concentrated in vacuo to give a residue. The residue was purified by column chromatography (SiO$_2$, DCM:MeOH=100:1 to 10:1) to give the title compound (3.50 g, 84% yield) as brown solid. $^1$H NMR (400 MHz, CDCl$_3$) δ 9.05 (s, 1H), 7.97-7.88 (m, 2H), 7.73-7.63 (m, 4H), 7.58-7.52 (m, 2H), 7.47-7.37 (m, 6H), 7.34 (t, J=8.8 Hz, 1H), 4.96-4.76 (m, 1H), 4.49-4.29 (m, 2H), 4.27-4.21 (m, 1H), 4.21-4.12 (m, 2H), 4.01 (dd, J=4.4, 10.4 Hz, 1H), 3.90-3.75 (m, 2H), 3.50-3.36 (m, 1H), 3.30 (s, 1H), 2.90-2.76 (m, 2H), 2.29-2.18 (m, 1H), 2.04-1.75 (m, 10H), 1.71-1.56 (m, 4H), 1.53 (s, 9H), 1.06 (d, J=1.6 Hz, 9H), 0.88 (dd, J=4.4, 6.8 Hz, 18H); LC-MS (ESI$^+$) m/z 1091.5 (M+H)$^+$.

(b) Step 2—Tert-butyl 3-[7-(8-ethynyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

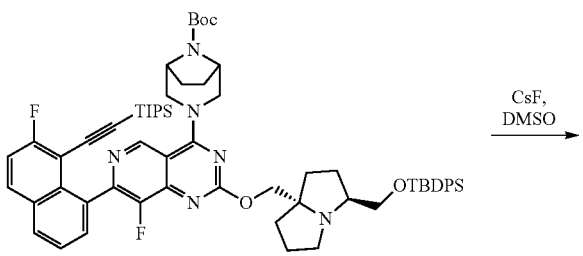

-continued

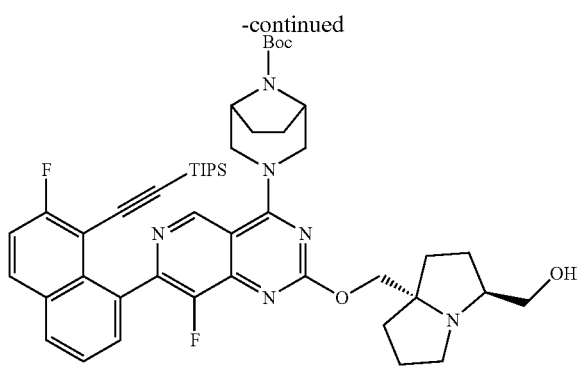

To a solution of tert-butyl 3-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate (3.50 g, 3.21 mmol) in DMSO (20 mL) was added CsF (1.46 g, 9.62 mmol). The mixture was stirred at 30° C. for 12 hrs. On completion, the reaction mixture was diluted with $H_2O$ 20 mL and extracted with EA 900 mL (300 mL×3). The combined organic layers were washed with brine (500 mL×3), dried over anhydrous $Na_2SO_4$, filtered and the filtrate was concentrated in vacuo to give a residue. The residue was purified by column chromatography ($SiO_2$, DCM:MeOH=100:1 to 10:1) to give the title compound (1.50 g, 65% yield) as brown solid. $^1$H NMR (400 MHz, $CDCl_3$) δ 8.99 (s, 1H), 8.01-7.89 (m, 2H), 7.65-7.55 (m, 2H), 7.34 (t, J=8.8 Hz, 1H), 4.68-4.52 (m, 2H), 4.45-4.27 (m, 4H), 3.92-3.78 (m, 2H), 3.76-3.62 (m, 2H), 3.51 (d, J=7.2 Hz, 1H), 3.12 (d, J=5.2 Hz, 1H), 2.82-2.75 (m, 1H), 2.35-2.25 (m, 1H), 2.03-1.95 (m, 3H), 1.93-1.79 (m, 5H), 1.77-1.57 (m, 4H), 1.53 (s, 9H); LC-MS (ESI$^+$) m/z 697.1 (M+H)$^+$.

(c) Step 3—Tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

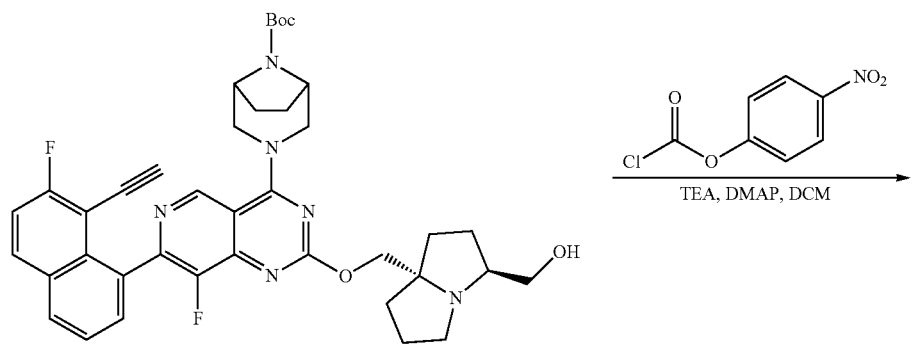

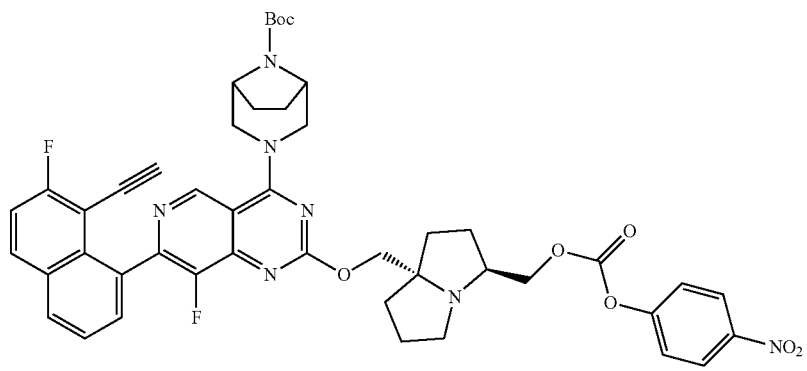

To a solution of tert-butyl 3-[7-(8-ethynyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 86.1 µmol), TEA (87.1 mg, 861 µmol) and DMAP (1.05 mg, 8.61 µmol) in DCM (6 mL) was added (4-nitrophenyl) carbonochloridate (52.0 mg, 258 µmol, CAS #7693-46-1). The mixture was stirred at 25° C. for 16 hrs. On completion, the mixture was diluted with DCM (30 mL), and extracted with $H_2O$ (3×50 mL). The organic layer was washed with brine (2×50 mL), dried over anhydrous $Na_2SO_4$, filtered and the filtrate was concentrated in vacuo to give the title compound (70.0 mg, 77% yield) as brown solid. LC-MS (ESI$^+$) m/z 862.1 (M+H)$^+$.

(d) Step 4—Tert-butyl 4-(azetidin-3-yloxy)piperidine-1-carboxylate

To a solution of tert-butyl 4-(1-benzyloxycarbonylazetidin-3-yl)oxypiperidine-1-carboxylate (600 mg, 1.54 mmol) in THF (6 mL) was added Pd/C (300 mg, 281 µmol, 10% purity). The suspension was degassed and purged with $H_2$ for 3 times. The mixture was stirred under $H_2$ (15 Psi) at 25° C. for 12 hrs. On completion, the reaction mixture was filtered to remove Pd/C and the filtrate was concentrated in vacuo to give the title compound (390 mg, 99% yield) as gray oil. $^1$H NMR (400 MHz, CDCl$_3$) δ 4.41 (t, J=6.4 Hz, 1H), 4.15-3.76 (m, 4H), 3.73-3.60 (m, 4H), 3.48-3.39 (m, 1H), 1.78-1.72 (m, 3H), 1.62-1.55 (m, 1H), 1.52-1.48 (m, 1H), 1.46 (s, 9H); LC-MS (ESI$^+$) m/z 257.0 (M+H)$^+$.

(e) Step 5—Tert-butyl 4-[1-[[1-(2,6-dioxo-3-piperidyl)-3-methyl-2-oxo-benzimidazol-5-yl] methyl] azetidin-3-yl]oxypiperidine-1-carboxylate

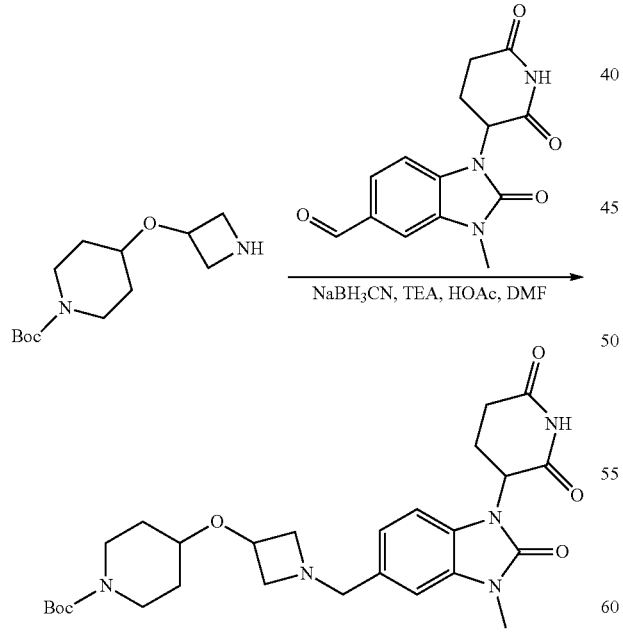

To a solution of tert-butyl 4-(azetidin-3-yloxy)piperidine-1-carboxylate (285 mg, 1.11 mmol) in DMF (8 mL) was added TEA (225 mg, 2.23 mmol) to adjust pH=7-8. The mixture was stirred at 25° C. for 10 min. And then HOAc (200 mg, 3.34 mmol) was added to adjust pH=6-7. At last 1-(2,6-dioxo-3-piperidyl)-3-methyl-2-oxo-benzimidazole-5-carbaldehyde (480 mg, 1.67 mmol) and NaBH$_3$CN (84.0 mg, 1.34 mmol) were added. The mixture was stirred at 25° C. for 12 hrs. On completion, the reaction mixture was quenched by added $H_2O$ (1 mL) and then concentrated in vacuo to give a residue. The residue was purified by reversed-phase HPLC (0.1% FA condition) to give the title compound (100 mg, 16% yield) as white solid. $^1$H NMR (400 MHz, DMSO-d$_6$) δ 11.07 (s, 1H), 7.09 (s, 1H), 7.06-7.01 (m, 1H), 6.97-6.92 (m, 1H), 5.35 (dd, J=5.2, 12.8 Hz, 1H), 4.17 (t, J=6.0 Hz, 1H), 3.67-3.64 (m, 1H), 3.61 (s, 2H), 3.55-3.52 (m, 2H), 3.47-3.43 (m, 2H), 3.33 (s, 3H), 2.97-2.92 (m, 2H), 2.87 (t, J=7.2 Hz, 2H), 2.76-2.60 (m, 3H), 2.05-1.97 (m, 1H), 1.77-1.67 (m, 2H), 1.39 (s, 9H), 1.33-1.23 (m, 2H); LC-MS (ESI$^+$) m/z 528.1 (M+H)$^+$.

(f) Step 6—3-[3-Methyl-2-oxo-5-[[3-(4-piperidyloxy)azetidin-1-yl]methyl]benzimidazol-1-yl]piperidine-2,6-dione

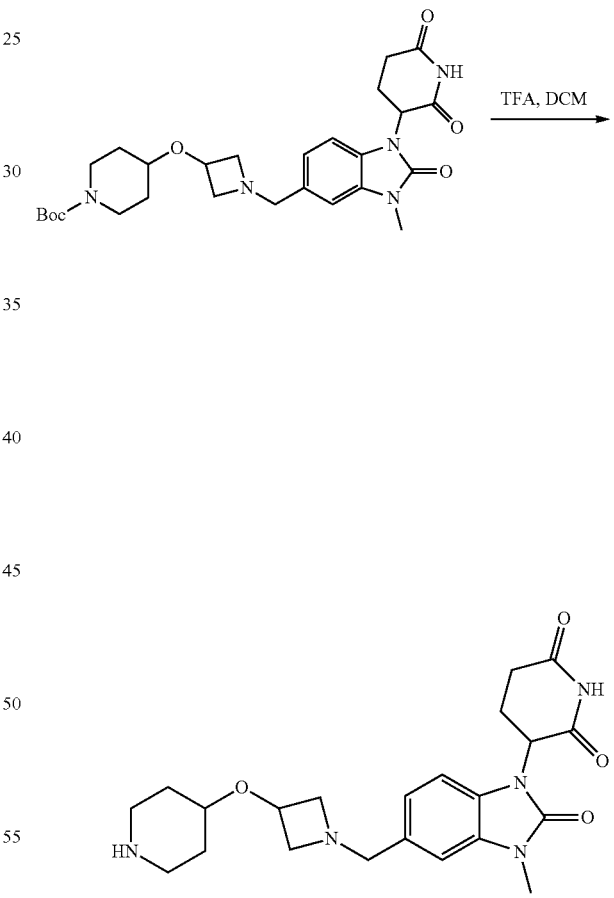

To a solution of tert-butyl 4-[1-[[1-(2,6-dioxo-3-piperidyl)-3-methyl-2-oxo-benzimidazol-5-yl]methyl] azetidin-3-yl]oxypiperidine-1-carboxylate (60.0 mg, 113 µmol) in DCM (1 mL) was added TFA (307 mg, 0.2 mL). The mixture was stirred at 25° C. for 1 hr. On completion, the reaction mixture was concentrated in vacuo to give the title compound (60.0 mg, 97% yield, TFA salt) as colorless oil. LC-MS (ESI$^+$) m/z 428.0 (M+H)$^+$.

(g) Step 7—Tert-butyl 3-[2-[[(3S,8S)-3-[[4-[1-[[1-(2,6-dioxo-3-piperidyl)-3-methyl-2-oxo-benzimidazol-5-yl]methyl]azetidin-3-yl]oxypiperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

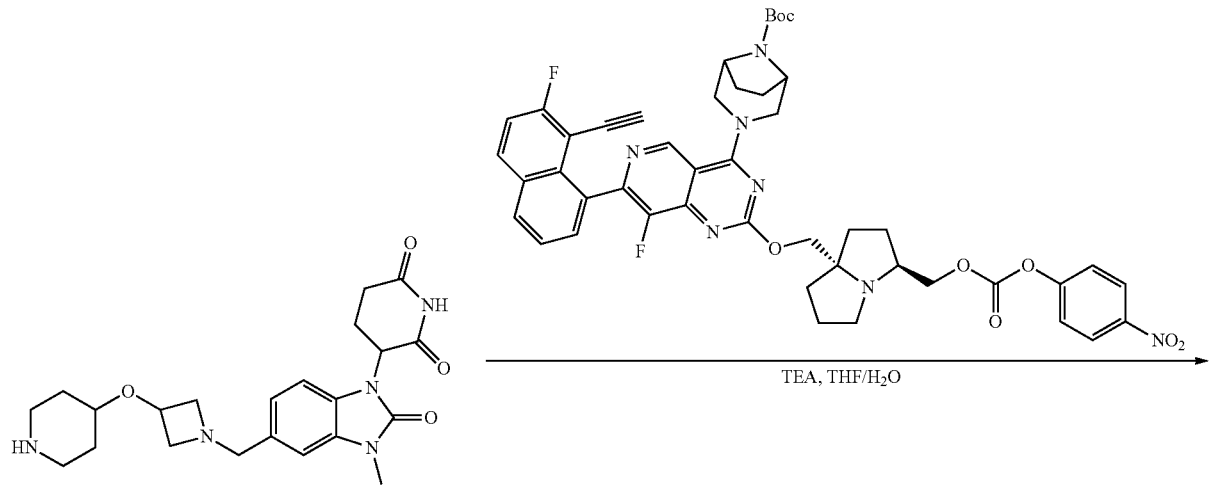

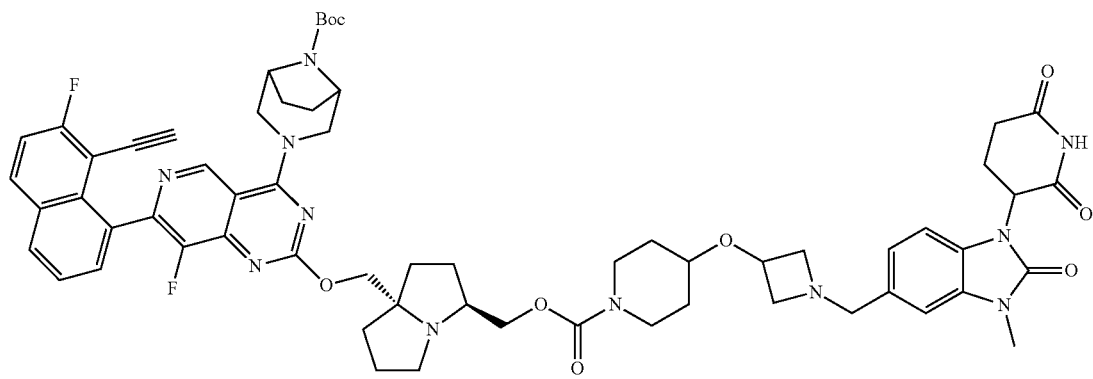

To a solution of 3-[3-methyl-2-oxo-5-[[3-(4-piperidyloxy)azetidin-1-yl]methyl]benzimidazol-1-yl] piperidine-2,6-dione (59.3 mg, 109 μmol, TFA salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol) in THF (3 mL) was added TEA (24.6 mg, 243 μmol) and H$_2$O (0.6 mL). The mixture was stirred at 25° C. for 0.5 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 15%-45% B over 10 min) to give the title compound (30.0 mg, 32% yield) as yellow solid. $^1$H NMR (400 MHz, DMSO-d$_6$) δ 11.10 (s, 1H), 9.15 (s, 1H), 8.30-8.19 (m, 2H), 7.75-7.57 (m, 3H), 7.22-6.99 (m, 3H), 5.37 (dd, J=5.6, 12.8 Hz, 1H), 4.63-4.54 (m, 1H), 4.52-4.42 (m, 2H), 4.33-4.22 (m, 4H), 4.01-3.80 (m, 4H), 3.78-3.60 (m, 6H), 3.52 (dd, J=8.4, 10.4 Hz, 2H), 3.33 (s, 3H), 3.21-3.12 (m, 2H), 3.11-3.01 (m, 2H), 2.94-2.86 (m, 1H), 2.78-2.58 (m, 4H), 2.29-2.20 (m, 1H), 2.07-1.68 (m, 15H), 1.47 (s, 9H), 1.36-1.28 (m, 2H); LC-MS (ESI$^+$) m/z 1150.2 (M+H)$^+$.

(h) Step 8—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[1-[[1-(2,
6-dioxo-3-piperidyl)-3-methyl-2-oxo-benzimidazol-
5-yl]methyl]azetidin-3-yl]oxypiperidine-1-
carboxylate (074)

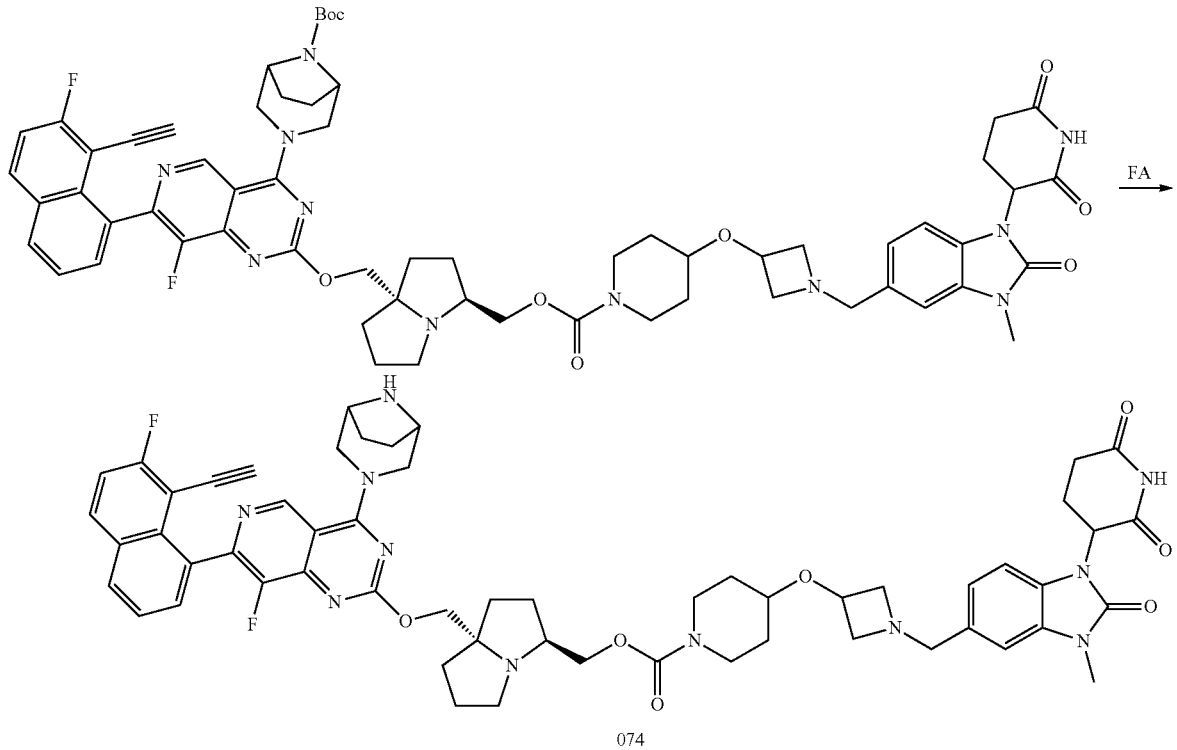

074

A solution of tert-butyl 3-[2-[[(3S,8S)-3-[[4-[1-[[1-(2,6-dioxo-3-piperidyl)-3-methyl-2-oxo-benzimidazol-5-yl]methyl]azetidin-3-yl]oxypiperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30.0 mg, 26.0 μmol) in HCOOH (2 mL) was stirred at 25° C. for 2 hrs. The reaction mixture was concentrated in vacuo to give a residue. The residue was purified by prep-HPLC (column: Phenomenex luna C18 150*25 mm*10 μm; mobile phase: [water (FA)-ACN]; gradient: 12%-42% B over 10 min) to give the title compound (25.9 mg, 86% yield, FA salt) as yellow solid. $^1$H NMR (400 MHz, DMSO-d$_6$) δ 11.09 (s, 1H), 9.06 (s, 1H), 8.26-8.16 (m, 2H), 7.74-7.53 (m, 3H), 7.07 (s, 1H), 7.05-6.90 (m, 2H), 5.34 (dd, J=5.2, 12.4 Hz, 1H), 4.50 (d, J=12.8 Hz, 1H), 4.41-4.32 (m, 1H), 4.24-4.19 (m, 1H), 4.17-4.12 (m, 2H), 4.06 (d, J=10.8 Hz, 1H), 4.01 (s, 1H), 3.70-3.60 (m, 6H), 3.57 (s, 2H), 3.51-3.48 (m, 2H), 3.46-3.42 (m, 2H), 3.32 (s, 3H), 3.06-2.98 (m, 2H), 2.94-2.87 (m, 1H), 2.82 (t, J=6.8 Hz, 2H), 2.78-2.63 (m, 4H), 2.06-1.98 (m, 2H), 1.82-1.44 (m, 15H), 1.28 (dd, J=2.8, 9.2 Hz, 2H); LC-MS (ESI$^+$) m/z 1050.4 (M+H)$^+$.

Example 79. Synthesis of Compound 075

(a) Step 1—Tert-butyl 4-[[1-(2,6-dioxo-3-piperidyl)-3-methyl-2-oxo-benzimidazol-5-yl]methyl]piperidine-1-carboxylate To a solution of tert-butyl 4-(bromomethyl)piperidine-1-carboxylate (411 mg, 1.48 mmol, CAS #158407-04-6) and 3-(5-bromo-3-methyl-2-oxo-benzimidazol-1-yl)piperidine-2,6-dione (500 mg, 1.48 mmol, CAS #2300099-98-1) in DME (50 mL) was added Ir[dF(CF$_3$)ppy]$_2$(dtbpy)(PF$_6$) (16.5 mg, 14.7 μmol), NiCl$_2$·dtbbpy (8.83 mg, 22.1 μmol), TTMSS (367 mg, 1.48 mmol) and Na$_2$CO$_3$ (313 mg, 2.96 mmol). The vial was sealed and placed under nitrogen was added. The reaction was stirred and irradiated with a 10 W blue LED lamp (3 cm away), with cooling water to keep the reaction at 25° C. for 14 hrs. On completion, the reaction mixture concentrated in vacuo to give a residue and the residue was purified by prep-HPLC (0.1% FA condition) to give the title compound (456 mg, 64% yield) as white solid. $^1$H NMR (400 MHz, CDCl$_3$) δ 8.19 (s, 1H), 6.87-6.79 (m, 2H), 6.72 (d, J=8.0 Hz, 1H), 5.22 (dd, J=5.2, 12.4 Hz, 1H), 4.08 (s, 2H), 3.44 (s, 3H), 2.99-2.90 (m, 1H), 2.89-2.70 (m, 2H), 2.67-2.64 (m, 2H), 2.58 (d, J=6.8 Hz, 2H), 2.28-2.19 (m, 1H), 1.62 (d, J=11.6 Hz, 2H), 1.46 (s, 9H), 1.22-1.08 (m, 2H); LC-MS (ESI$^+$) m/z 357.1 (M-Boc+H)$^+$.

(b) Step 2—3-[3-Methyl-2-oxo-5-(4-piperidylmethyl)benzimidazol-1-yl]piperidine-2,6-dione

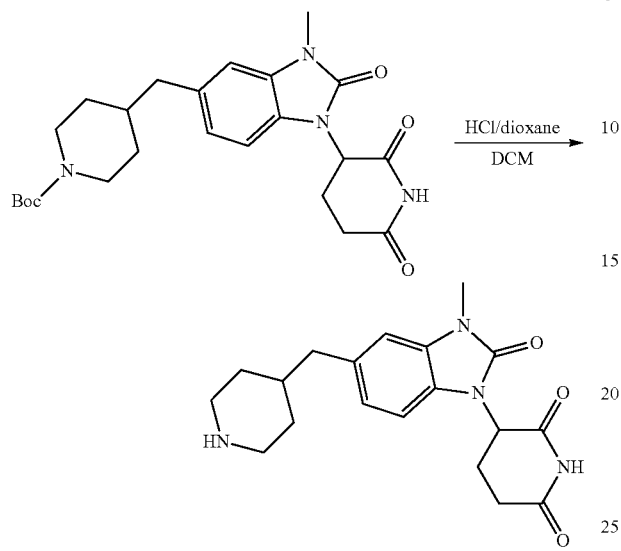

To a solution of tert-butyl 4-[[1-(2,6-dioxo-3-piperidyl)-3-methyl-2-oxo-benzimidazol-5-yl]methyl] piperidine-1-carboxylate (456 mg, 998 μmol) in DCM (10 mL) was added HCl/dioxane (4 M, 4 mL). The mixture was stirred at 25° C. for 1 hr. On completion, the reaction mixture concentrated in vacuo to give the title compound (390 mg, 99% yield, HCl salt) as white solid. LC-MS (ESI$^+$) m/z 357.0 (M+H)$^+$.

(c) Step 3—Tert-butyl 4-[4-[[1-(2,6-dioxo-3-piperidyl)-3-methyl-2-oxo-benzimidazol-5-yl]methyl]-1-piperidyl]piperidine-1-carboxylate

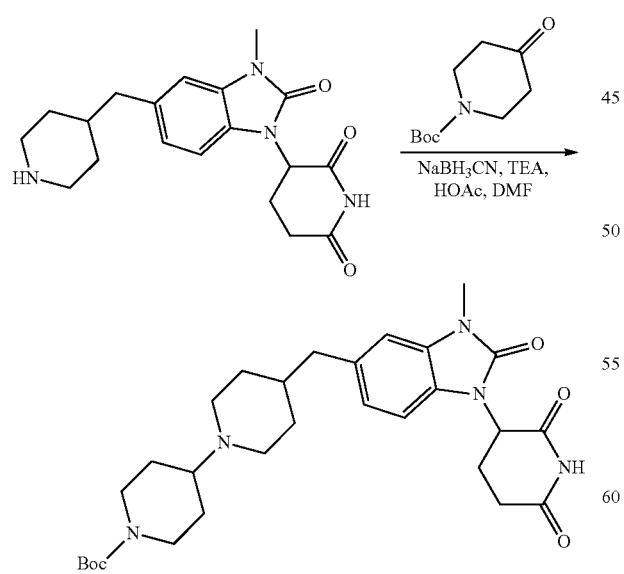

To a solution of 3-[3-methyl-2-oxo-4-(4-piperidylmethyl)benzimidazol-1-yl]piperidine-2,6-dione (390 mg, 1.01 mmol, HCl salt) in DMF (5 mL) was added TEA (204 mg, 2.02 mmol) to adjust pH=10, then HOAc (122 mg, 2.02 mmol) was added to adjust pH=6. A solution of tert-butyl 4-oxopiperidine-1-carboxylate (243 mg, 1.21 mmol, CAS #79099-07-3) in DMF (2 mL) was added to mixture at 25° C. Finally, NaBH$_3$CN (95.2 mg, 1.51 mmol) was added to mixture and stirred at 50° C. for 4 hrs. On completion, the reaction mixture was added H$_2$O (1 mL) and concentrated in vacuo to give a residue and the residue was purified by prep-HPLC (0.1% FA condition) to give the title compound (335 mg, 75% yield) as white solid. $^1$H NMR (400 MHz, DMSO-d$_6$) δ 11.08 (s, 1H), 7.06-6.96 (m, 2H), 6.81 (d, J=7.6 Hz, 1H), 5.36 (dd, J=5.2, 12.4 Hz, 1H), 3.95 (d, J=10.4 Hz, 2H), 3.31 (s, 3H), 2.94-2.83 (m, 5H), 2.75-2.56 (m, 5H), 2.22 (t, J=11.2 Hz, 2H), 2.05-1.95 (m, 1H), 1.78-1.71 (m, 2H), 1.63-1.46 (m, 3H), 1.37 (s, 9H), 1.32-1.20 (m, 4H); LC-MS (ESI$^+$) m/z 540.2 (M+H)$^+$.

(d) Step 4—3-[3-Methyl-2-oxo-5-[[1-(4-piperidyl)-4-piperidyl]methyl]benzimidazol-1-yl]piperidine-2,6-dione

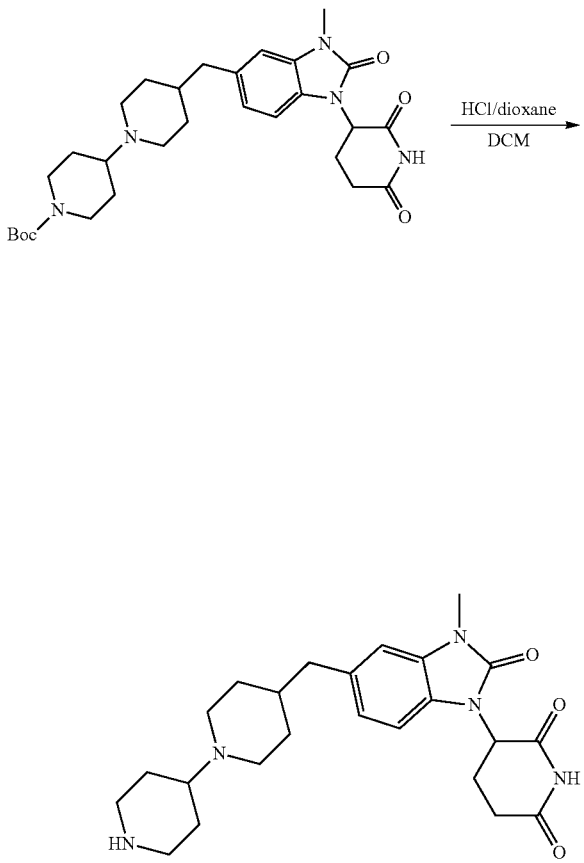

To a solution of tert-butyl 4-[4-[[1-(2,6-dioxo-3-piperidyl)-3-methyl-2-oxo-benzimidazol-5-yl]methyl]-1-piperidyl]piperidine-1-carboxylate (100 mg, 185 μmol) in DCM (5 mL) was added HCl/dioxane (4 M, 2.5 mL). The mixture was stirred at 25° C. for 1 hr. On completion, the reaction mixture concentrated in vacuo to give the title compound (85.0 mg, 96% yield, HCl salt) as white solid. LC-MS (ESI$^+$) m/z 440.1 (M+H)$^+$.

(e) Step 5—Tert-butyl 3-[2-[[(3S,8S)-3-[[4-[4-[[1-(2,6-dioxo-3-piperidyl)-3-methyl-2-oxo-benzimidazol-5-yl]methyl]-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

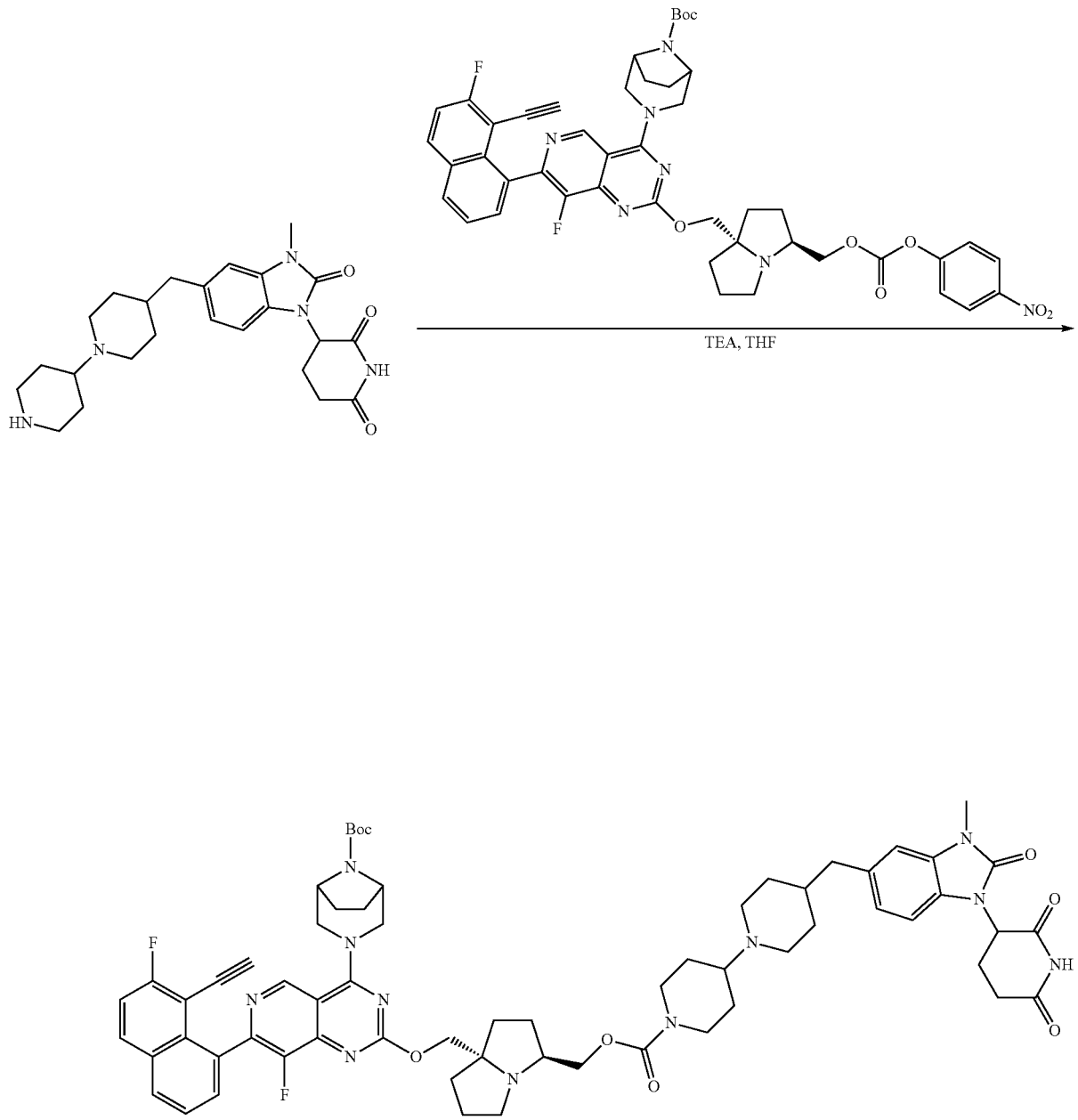

To a solution of 3-[3-methyl-2-oxo-5-[[1-(4-piperidyl)-4-piperidyl]methyl]benzimidazol-1-yl] piperidine-2,6-dione (71.8 mg, 150 μmol, HCl salt) in THF (2 mL) and H₂O (0.2 mL) was added TEA (22.8 mg, 226 μmol). Then tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (65.0 mg, 75.4 μmol) was added to mixture and stirred at 25° C. for 1 hr. On completion, the mixture was concentrated in vacuo to give a residue and the residue was purified by prep-HPLC (column: Phenomenex luna C18 150*25 mm*10 μm; mobile phase: [water (FA)-ACN]; gradient: 18%-48% B over 11 min) to give the title compound (45.0 mg, 42% yield) as yellow solid; LC-MS (ESI⁺) m/z 1162.6 (M+H)⁺.

(f) Step 7—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl4-[4-[[1-(2,
6-dioxo-3-piperidyl)-3-methyl-2-oxo-benzimidazol-
5-yl]methyl]-1-piperidyl]piperidine-1-carboxylate
(075)

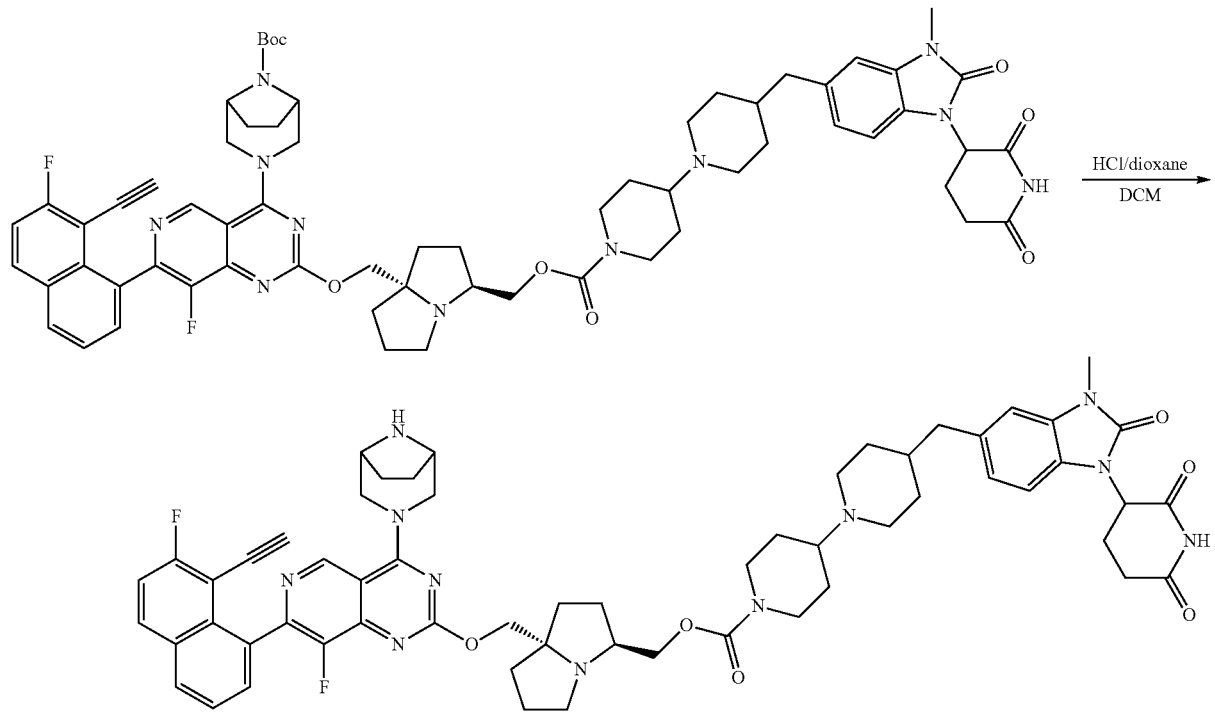

075

To a solution of tert-butyl 3-[2-[[(3S,8S)-3-[[4-[4-[[1-(2,6-dioxo-3-piperidyl)-3-methyl-2-oxo-benzimidazol-5-yl]methyl]-1-piperidyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (45.0 mg, 32.6 µmol) in DCM (5 mL) was added HCl/dioxane (4 M, 1 mL). The mixture was stirred at 25° C. for 20 mins. On completion, the reaction mixture concentrated in vacuo to give a residue. The residue was dissolved in deionized water (5 mL) and ACN (1 mL). The mixture was lyophilized to give the title compound (35.4 mg, 80% yield, HCl salt) as yellow solid. $^1$H NMR (400 MHz, DMSO-$d_6$) δ 11.47-11.35 (m, 1H), 11.09 (s, 1H), 10.91-10.71 (m, 1H), 10.20 (d, J=9.2 Hz, 1H), 10.21-10.19 (m, 1H), 9.15 (s, 1H), 8.32-8.15 (m, 2H), 7.77-7.55 (m, 3H), 7.07-6.99 (m, 2H), 6.84 (d, J=8.0 Hz, 1H), 5.36 (dd, J=5.2, 12.4 Hz, 1H), 4.76-4.54 (m, 4H), 4.38 (d, J=9.6 Hz, 2H), 4.27-4.16 (m, 3H), 4.12-3.99 (m, 4H), 3.44-3.24 (m, 9H), 2.94-2.69 (m, 6H), 2.68-2.58 (m, 2H), 2.34-2.25 (m, 1H), 2.20-1.90 (m, 15H), 1.83-1.51 (m, 8H); LC-MS (ESI$^+$) m/z 1062.5 (M+H)$^+$.

Example 80. Synthesis of Compound 076

(a) Step 1—Tert-butyl 3-[2-[[3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate To a solution of tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (9.00 g, 11.2 mmol) and 2-[2-fluoro-8-(4,4,5,5-tetramethyl-1,3,2-dioxaborolan-2-yl)-1-naphthyl] ethynyl-triisopropylsilane (6.61 g, 14.6 mmol, CAS #2503307-87-5) in dioxane (180 mL) and H$_2$O (36 mL) was added Cs$_2$CO$_3$ (10.9 g, 33.7 mmol) and ditert-butyl(cyclopentyl) phosphane; dichloropalladium; iron (1.46 g, 2.25 mmol). The mixture was stirred at 100° C. for 1 hr under N$_2$ atmosphere. On completion, the mixture was concentrated in vacuo. The mixture was purified by Prep-HPLC (column: Welch Ultimate XB-CN 250*50*10 µm; mobile phase: [EtOH+MeOH (4:1, neutral)]; gradient: 15%-65% B over 25 min) to give the title compound (10.0 g, 73% yield) as yellow solid. LC-MS (ESI$^+$) m/z 1092.2 (M+H)$^+$.

(b) Step 2—Tert-butyl 3-[7-(8-ethynyl-7-fluoro-1-naphthyl)-8-fluoro-2-[[3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

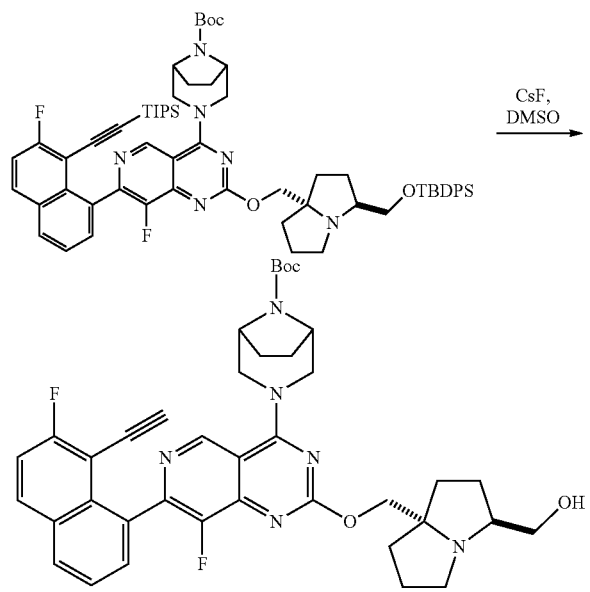

To a solution of tert-butyl 3-[2-[[3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3,8-diazabicyclo[3.2.1]octane-8-carboxylate (10.0 g, 9.16 mmol) in DMSO (100 mL) was added CsF (4.17 g, 27.5 mmol) at 20° C. The mixture was stirred at 40° C. for 16 hrs. On completion, the mixture was concentrated in vacuo. The residue was purified by silica gel chromatography (DCM:MeOH=30:1) to give the title compound (4.00 g, 56% yield) as yellow solid. $^1$H NMR (400 MHz, DMSO-d$_6$) δ 9.11 (s, 1H), 8.30-8.15 (m, 2H), 7.76-7.56 (m, 3H), 4.58 (d, J=12.4 Hz, 1H), 4.51-4.06 (m, 6H), 4.02 (s, 1H), 3.72-3.56 (m, 4H), 3.34 (s, 2H), 3.16 (d, J=4.4 Hz, 1H), 2.12 (s, 1H), 1.94-1.67 (m, 10H), 1.47 (s, 9H); LC-MS (ESI$^+$) m/z 697.2 (M+H)$^+$.

(c) Step 3—Tert-butyl 3-[7-(8-ethynyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (Int. F) and tert-butyl 3-[7-(8-ethynyl-7-fluoro-1-naphthyl)-8-fluoro-2-[[(3R,8R)-3-(hydroxymethyl)-1,2,3,5,6,7-hexahydropyrrolizin-8-yl]methox]pyrido[4,3-d]pyrimidin-4-yl]-3,8-diazabicyclo[3.2.1]octane-8-carboxylate (Int. G)

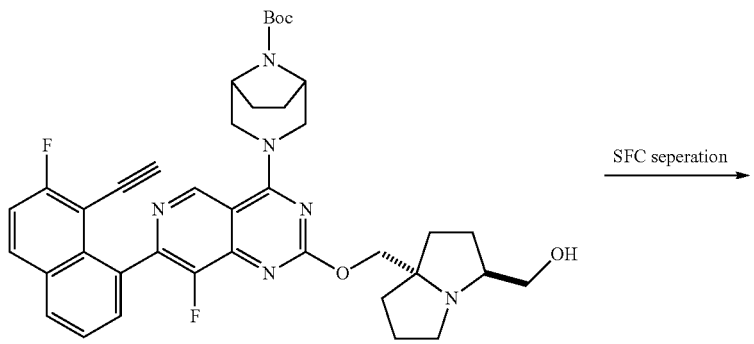

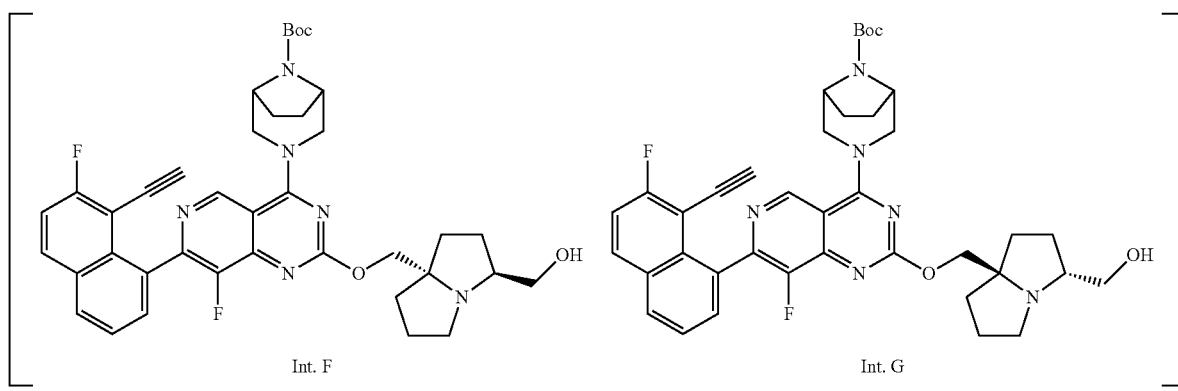

Tert-butyl 3-[7-(8-ethynyl-7-fluoro-1-naphthyl)-8-fluoro-2-[[3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (2.00 g, 2.87 mmol) was purified by SFC. The residue was separated by Prep-SFC (column: DAICEL CHIRALCEL OX (250 mm*30 mm, 10 um); mobile phase: [$CO_2$-ACN/MeOH (0.1% $NH_3H_2O$)]; B %: 65%, isocratic elution mode) to give the title Int. F (900 mg, 45% yield, Ret. Time: 0.657 s) as yellow solid and Int. G (900 mg, 45% yield, Ret. Time: 1.159 s) as yellow solid.

(d) Step 4—Tert-butyl 3-[7-(8-ethynyl-7-fluoro-1-naphthyl)-8-fluoro-2-[[(3R,8R)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

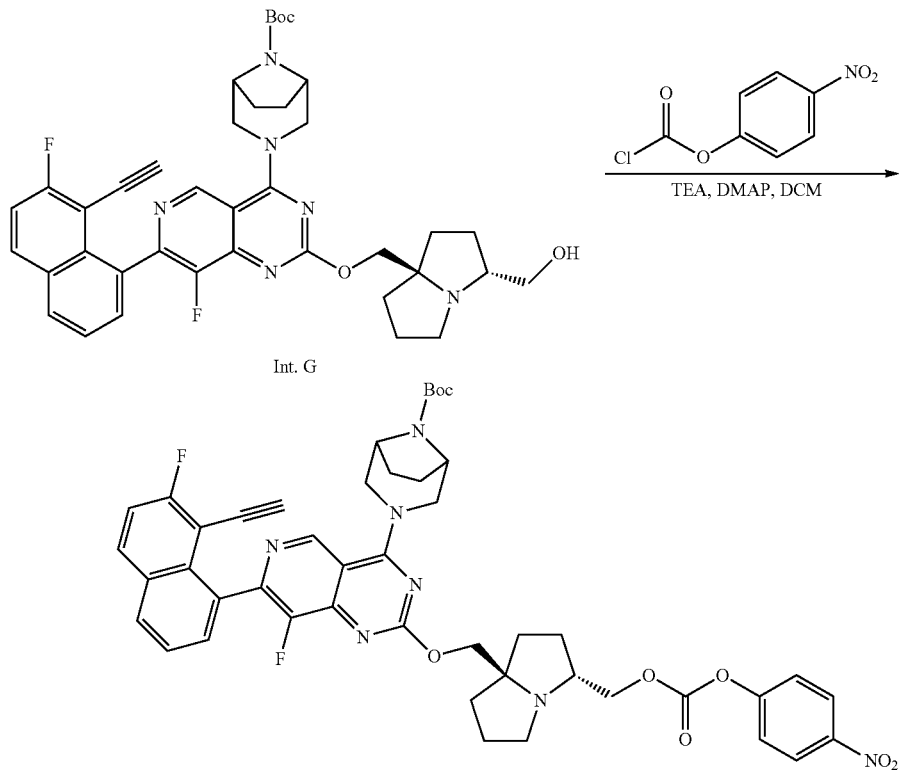

To a solution of Int. G (60.0 mg, 86.1 μmol) in DCM (5 mL) was added TEA (60.9 mg, 602 μmol, 83.9 μL) and DMAP (1.05 mg, 8.61 μmol), (4-nitrophenyl), carbonochloridate (52.0 mg, 258 μmol, CAS #7693-46-1). The mixture was stirred at 25° C. for 2 hrs. On completion, the mixture was concentrated in vacuo to give the title compound (70.0 mg, 94% yield)) as yellow solid. LC-MS ($ESI^+$) m/z 862.0 $(M+H)^+$.

(e) Step 5—3-(3-Methyl-2-oxo-5-(1-(piperidin-4-ylmethyl)piperidin-4-yl)-2,3-dihydro-1H-benzo[d]imidazol-1-yl)piperidine-2,6-dione To a solution of tert-butyl 4-[[4-[1-(2,6-dioxo-3-piperidyl)-3-methyl-2-oxo-benzimidazol-5-yl]-1-piperidyl]methyl]piperidine-1-carboxylate (100 mg, 185 μmol) in DCM (5 mL) was added TFA (259 mg, 2.28 mmol, 169 μL). The mixture was stirred at 25° C. for 10 mins. On completion, the mixture was concentrated in vacuo to give the title compound (100 mg, 97% yield, TFA salt) as white solid. LC-MS ($ESI^+$) m/z 440.1 $(M+H)^+$.

(f) Step 6—Tert-butyl 3-[2-[[(3R,8R)-3-[[4-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

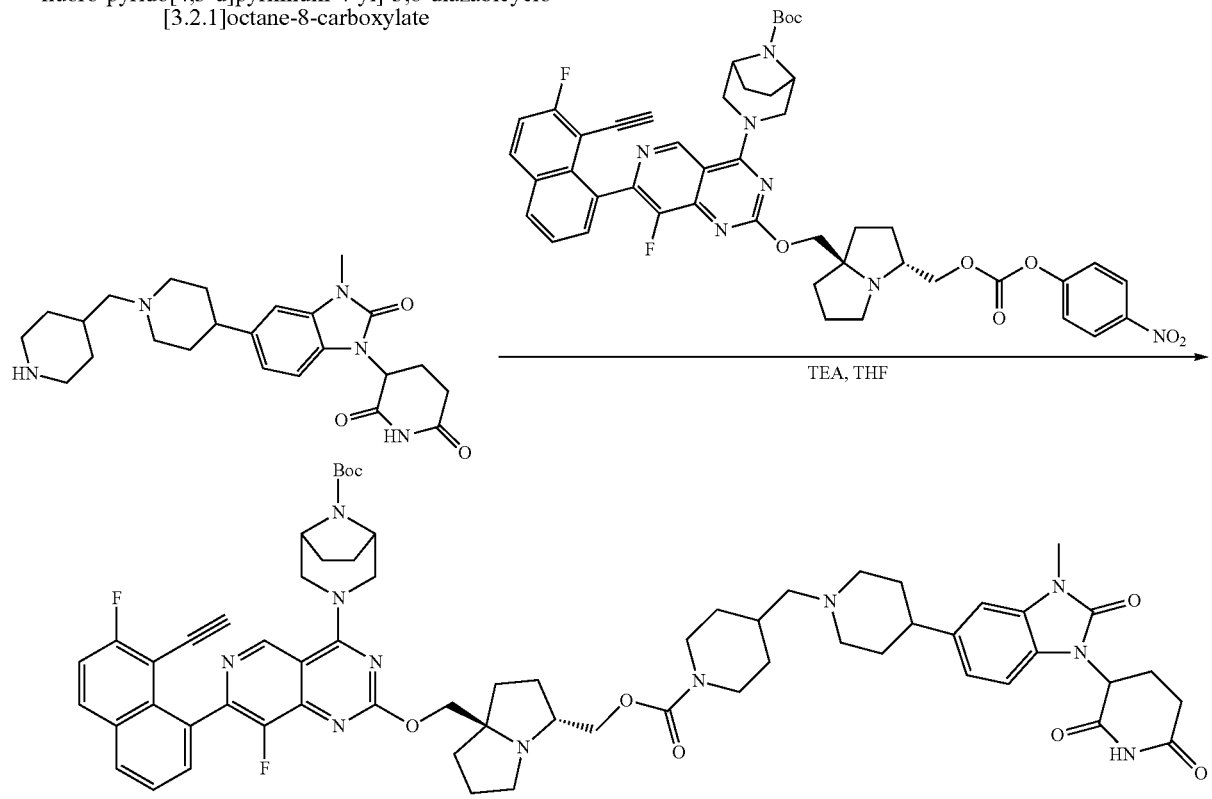

To a solution of 3-[3-methyl-2-oxo-5-[1-(4-piperidylmethyl)-4-piperidyl]benzimidazol-1-yl] piperidine-2,6-dione (57.8 mg, 104 μmol, TFA salt) in THF (4 mL) was added TEA (21.1 mg, 208 μmol, 29.0 μL), tert-butyl 3-[7-(8-ethynyl-7-fluoro-1-naphthyl)-8-fluoro-2-[[(3R,8R)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 69.6 μmol). The mixture was stirred at 25° C. for 10 mins. On completion, the mixture was concentrated in vacuo. The crude product was purified by reversed-phase HPLC (column: Phenomenex luna C18 150*25 mm*10 μm; mobile phase: [water (FA)-ACN]; gradient: 17%-47% B over 11 min) to give the title compound (40.0 mg, 48% yield) as white solid. LC-MS (ESI$^+$) m/z 1162.3 (M+H)$^+$.

(g) Step 7—[(3R,8R)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl-4-[[4-[1-(2,6-dioxo-3-piperidyl)-3-methyl-2-oxo-benzimidazol-5-yl]-1-piperidyl]methyl]piperidine-1-carboxylate (076)

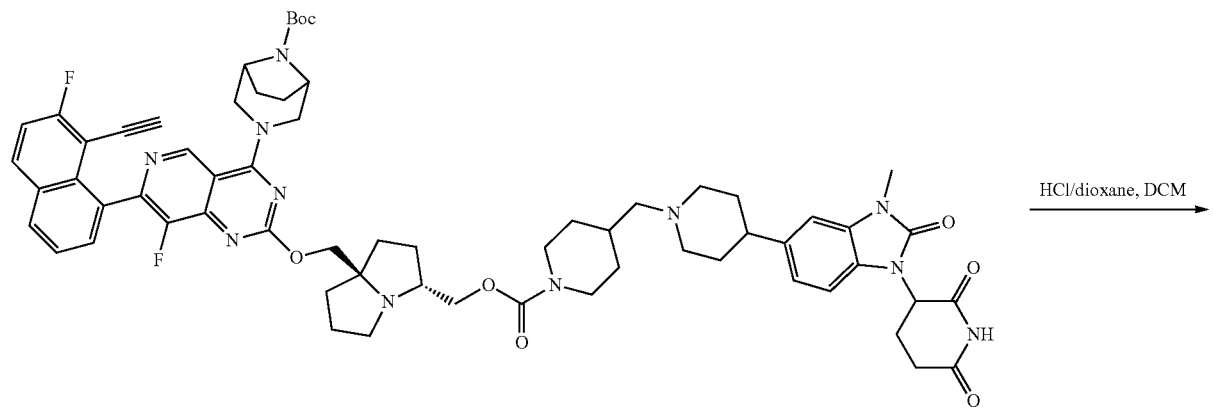

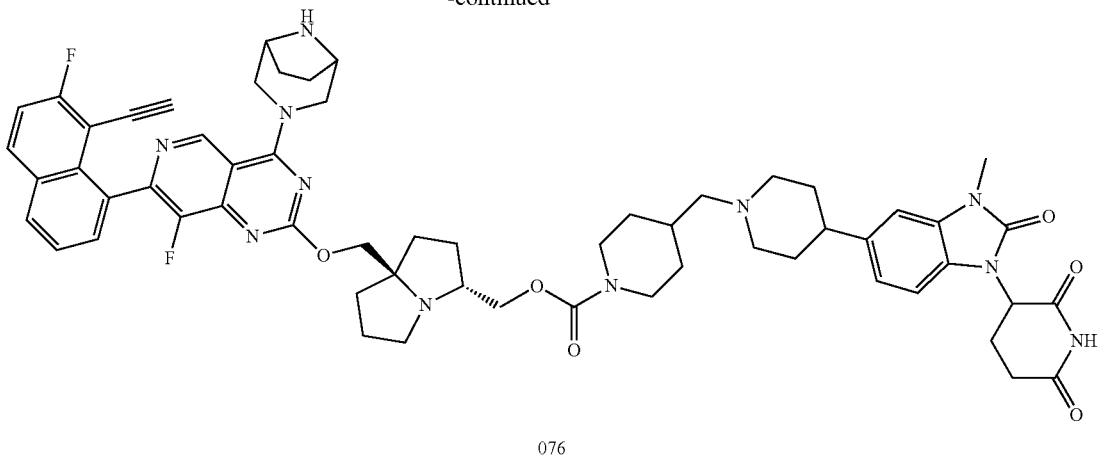

076

To a solution of tert-butyl 3-[2-[[(3R,8R)-3-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35.0 mg, 30.1 μmol) in DCM (3 mL) was added HCl/dioxane (4 M, 1.00 mL). The mixture was stirred at 25° C. for 5 mins. On completion, the mixture was concentrated in vacuo. The reaction mixture was lyophilized to give the title compound (29.4 mg, 86% yield, HCl salt) as yellow solid. $^1$H NMR (400 MHz, DMSO-$d_6$) δ 11.10 (s, 2H), 10.25-10.12 (m, 1H), 10.06-9.95 (m, 1H), 9.67 (d, J=2.4 Hz, 1H), 9.16 (s, 1H), 8.29-8.18 (m, 2H), 7.74-7.69 (m, 1H), 7.68-7.59 (m, 2H), 7.11-7.02 (m, 2H), 6.93 (d, J=8.0 Hz, 1H), 5.36 (dd, J=5.6, 12.4 Hz, 1H), 4.75-4.54 (m, 4H), 4.46-4.34 (m, 1H), 4.21 (s, 4H), 4.08-3.95 (m, 5H), 3.59-3.54 (m, 2H), 3.33 (s, 3H), 3.08-2.59 (m, 11H), 2.35-2.18 (m, 4H), 2.13-1.86 (m, 17H), 1.19-1.09 (m, 2H); LC-MS (ESI$^+$) m/z 1063.5 (M+H)$^+$.

Example 81. Synthesis of Compound 077

(a) Step 1—3-(3-Methyl-2-oxo-4-vinyl-benzimidazol-1-yl)piperidine-2,6-dione

To a solution of 3-(4-bromo-3-methyl-2-oxo-benzimidazol-1-yl)piperidine-2,6-dione (10.0 g, 29.6 mmol, CAS #2304754-51-4) and potassium; trifluoro(vinyl)boranuide (11.9 g, 88.7 mmol, CAS #13682-77-4) in dioxane (100 mL) and H$_2$O (20 mL) was added Cs$_2$CO$_3$ (28.9 g, 88.7 mmol) and Pd(dppf)Cl$_2$ (2.16 g, 2.96 mmol) at 25° C. The mixture was stirred at 80° C. for 16 hrs under N$_2$ atmosphere. On completion, the mixture was filtered and the filtrate was concentrated in vacuo to give a residue. The residue was purified by column chromatography (SiO$_2$, PE:EA=100:1 to 7:10) to give the title compound (3.30 g, 38% yield) as white solid. $^1$H NMR (400 MHz, CDCl$_3$) δ 8.58 (s, 1H), 7.44-7.37 (m, 1H), 7.27 (s, 1H), 7.14 (t, J=8.0 Hz, 1H), 6.85 (d, J=8.0 Hz, 1H), 5.78 (d, J=17.2 Hz, 1H), 5.53 (d, J=11.2 Hz, 1H), 5.34 (dd, J=5.2, 12.4 Hz, 1H), 3.77 (s, 3H), 3.09-2.79 (m, 3H), 2.38-2.28 (m, 1H); LC-MS (ESI$^+$) m/z 286.0 (M+H)$^+$.

(b) Step 2—1-(2,6-Dioxo-3-piperidyl)-3-methyl-2-oxo-benzimidazole-4-carbaldehyde

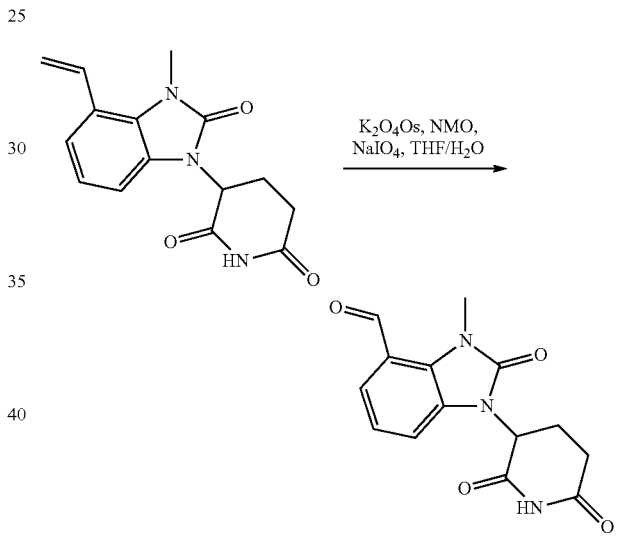

To a solution of 3-(3-methyl-2-oxo-4-vinyl-benzimidazol-1-yl)piperidine-2,6-dione (3.30 g, 11.6 mmol) in THF (30 mL) and H$_2$O (6 mL) was added K$_2$OsO$_4$ (213 mg, 578 μmol) and NMO (2.30 g, 19.7 mmol). The mixture was stirred at 25° C. for 12 hrs. Then NaIO$_4$ (7.42 g, 34.7 mmol) was added to the mixture and the mixture was stirred at 25° C. for 1 hr. On completion, the reaction mixture was diluted with H$_2$O (150 mL). The mixture was extracted with DCM (3×150 mL), and the organic layer was washed with brine (2×100 mL), dried with anhydrous Na$_2$SO$_4$, filtered and the filtrate was concentrated in vacuo to give a residue. The residue was triturated with (PE:EA=1:1) at 25° C. for 48 hrs to give the title compound (3.40 g, 95% yield) as black solid. $^1$H NMR (400 MHz, CDCl$_3$) δ 10.31 (s, 1H), 8.08 (dd, J=1.2, 4.8 Hz, 1H), 7.63 (d, J=8.0 Hz, 1H), 7.04 (d, J=8.4 Hz, 1H), 5.25 (dd, J=5.2, 12.0 Hz, 1H), 3.79 (s, 3H), 2.77 (s, 4H); LC-MS (ESI$^+$) m/z 288.0 (M+H)$^+$.

(c) Step 3—Tert-butyl 4-[[1-[[1-(2,6-dioxo-3-piperidyl)-3-methyl-2-oxo-benzimidazol-4-yl]methyl]-4-piperidyl]methyl]piperidine-1-carboxylate

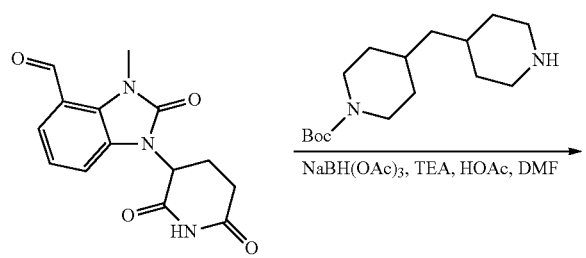

To a solution of tert-butyl 4-(4-piperidylmethyl)piperidine-1-carboxylate (98.3 mg, 348 μmol, CAS #879883-54-2) in DMF (2 mL) was basified with TEA (49.0 μL, 348 μmol) to PH=8, and then acidified with HOAc (20.0 μL, 348 μmol) to pH=6. Then a solution of 1-(2,6-dioxo-3-piperidyl)-3-methyl-2-oxo-benzimidazole-4-carbaldehyde (200 mg, 696 μmol) in DMF (2 mL) was added to the mixture and the mixture was stirred at 25° C. for 0.5 hr. Then NaBH(OAc)$_3$ (148 mg, 696 μmol) was added to the mixture. The mixture was stirred at 25° C. for 4.5 hrs. On completion, the mixture was concentrated in vacuo to give a residue. The residue was purified by reversed phase (0.1% FA condition) to give the title compound (100 mg, 51% yield) as yellow solid. $^1$H NMR (400 MHz, DMSO-d$_6$) δ 11.09 (s, 1H), 7.07 (d, J=7.6 Hz, 1H), 6.96 (t, J=7.6 Hz, 1H), 6.91-6.84 (m, 1H), 5.37 (dd, J=5.2, 12.4 Hz, 1H), 3.89 (d, J=10.0 Hz, 2H), 3.66 (s, 5H), 2.90-2.81 (m, 3H), 2.75-2.59 (m, 5H), 2.01 (d, J=5.6 Hz, 3H), 1.59 (s, 5H), 1.49-1.44 (m, 1H), 1.38 (s, 9H), 1.11-1.05 (m, 3H), 0.95-0.88 (m, 2H); LC-MS (ESI$^+$) m/z 554.2 (M+H)$^+$.

(d) Step 4—3-[3-Methyl-2-oxo-4-[[4-(4-piperidylmethyl)-1-piperidyl]methyl]benzimidazol-1-yl]piperidine-2,6-dione

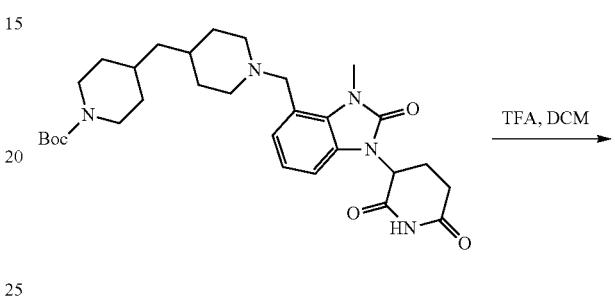

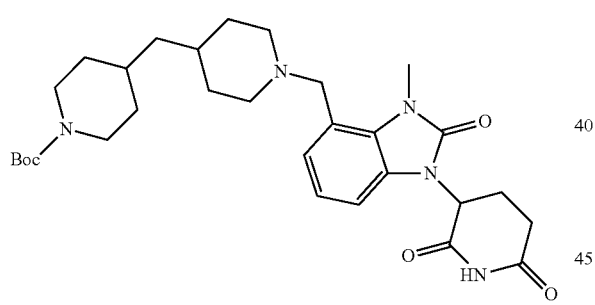

To a solution of tert-butyl 4-[[1-[[1-(2,6-dioxo-3-piperidyl)-3-methyl-2-oxo-benzimidazol-4-yl]me-thyl]-4-piperidyl]methyl]piperidine-1-carboxylate (80.0 mg, 144 μmol) in DCM (1 mL) was added TFA (0.1 mL, 1.35 mmol). The mixture was stirred at 25° C. for 1 hr. On completion, the mixture was concentrated in vacuo to give the title compound (80.0 mg, 97% yield, TFA salt) as white solid. LC-MS (ESI$^+$) m/z 454.1 (M+H)$^+$.

(e) Step 5—Tert-butyl 3-[2-[[(3R,8R)-3-[[4-[[1-[[1-(2,6-dioxo-3-piperidyl)-3-methyl-2-oxo-benzimidazol-4-yl]methyl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

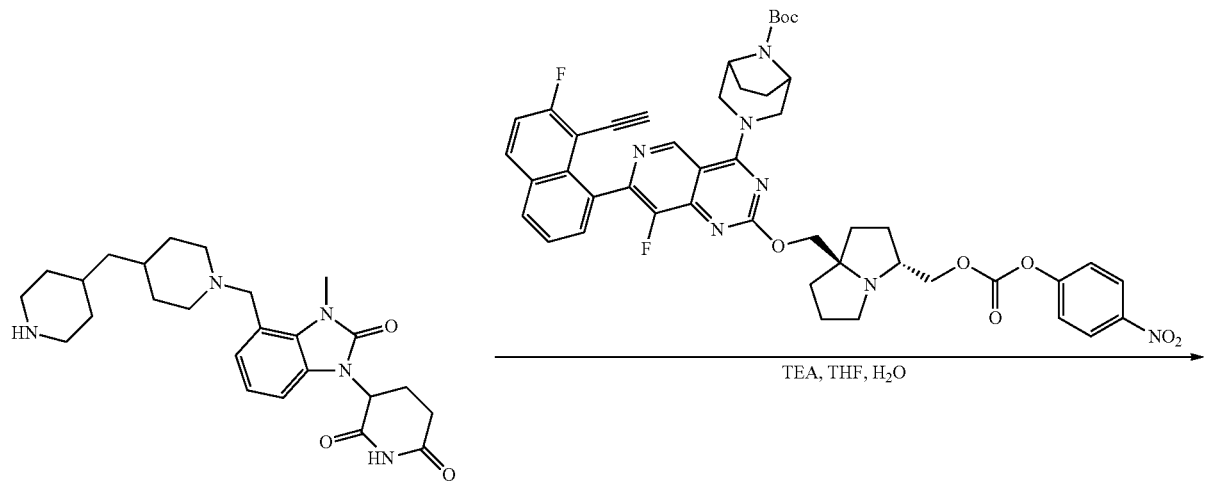

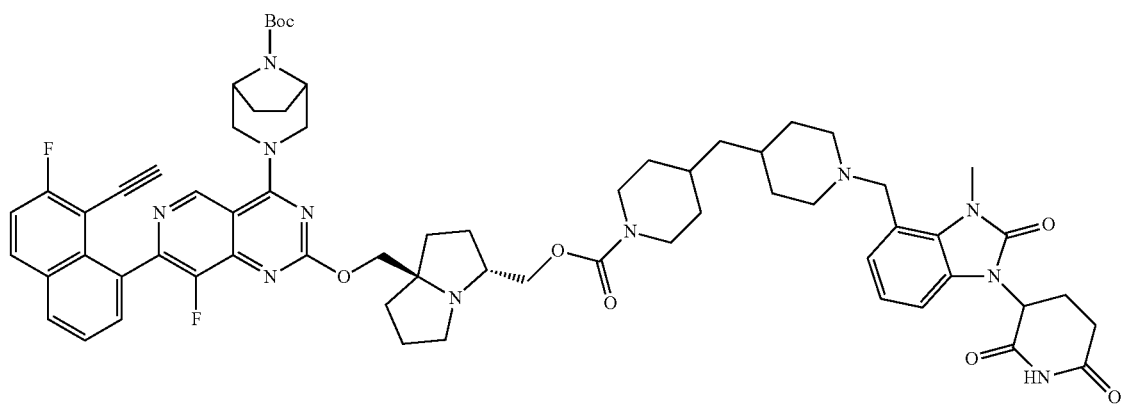

A solution of 3-[3-methyl-2-oxo-4-[[4-(4-piperidylmethyl)-1-piperidyl]methyl]benzimidazol-1-yl]piperidine-2,6-dione (80.0 mg, 141 μmol, TFA salt) in THF (0.5 mL) and H₂O (0.5 mL) was basified with TEA (69.0 μL, 493 μmol) to pH=8. Then a solution of tert-butyl 3-[7-(8-ethynyl-7-fluoro-1-naphthyl)-8-fluoro-2-[[(3R,8R)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.7 mg, 70.5 μmol) in THF (0.5 mL) was added to the mixture, and then the mixture was stirred at 25° C. for 0.5 hr. On completion, the mixture was concentrated in vacuo to give a residue. The residue was purified by prep-HPLC (column: Phenomenex luna C18 150*25 mm*10 um; mobile phase: [water (FA)-ACN]; gradient: 18%-48% B over 8 min) to give the title compound (30.0 mg, 36% yield) as yellow solid. LC-MS (ESI⁺) m/z 1176.6 (M+H)⁺.

(f) Step 6—[(3R,8R)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[[1-[[1-
(2,6-dioxo-3-piperidyl)-3-methyl-2-oxo-
benzimidazol-4-yl]methyl]-4-piperidyl]methyl]
piperidine-1-carboxylate (077)

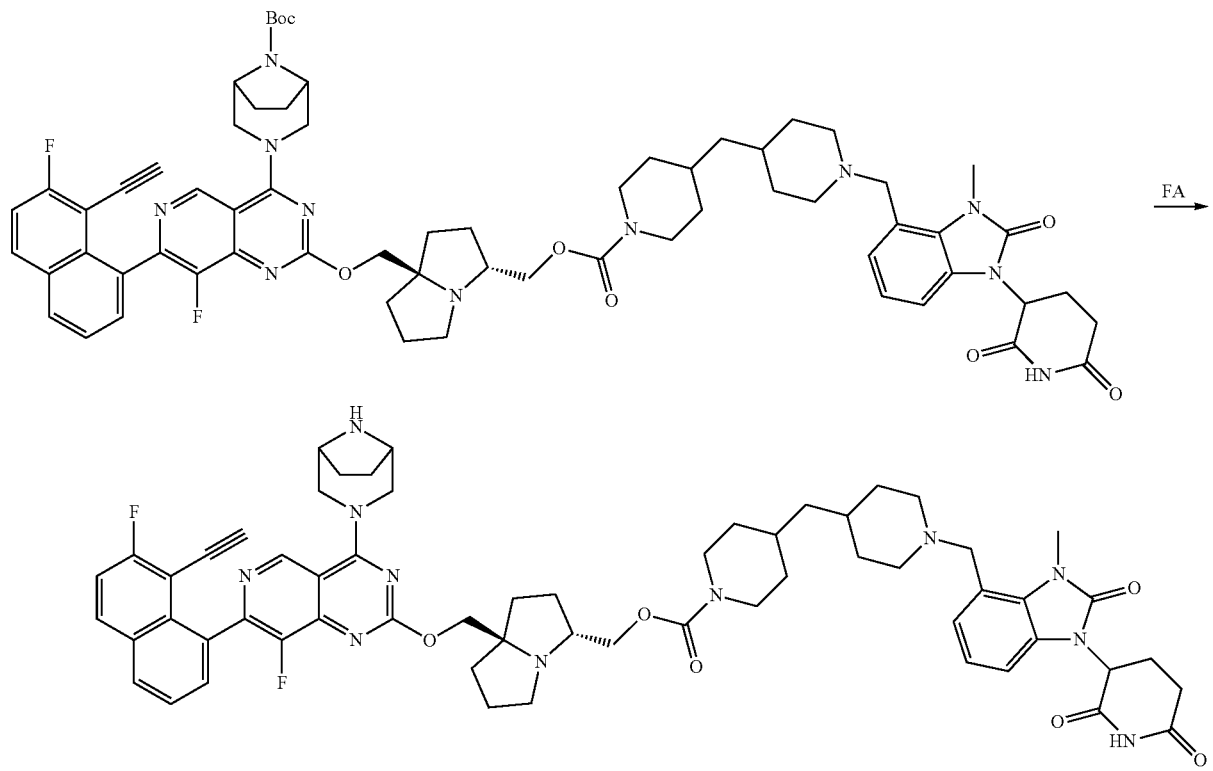

077

A solution of tert-butyl 3-[2-[[(3R,8R)-3-[[4-[[1-[[1-(2,6-dioxo-3-piperidyl)-3-methyl-2-oxo-benzimidazol-4-yl]methyl]-4-piperidyl]methyl]piperidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (10.0 mg, 8.50 μmol) in FA (1 mL) was stirred at 25° C. for 1 hr. On completion, the mixture was concentrated in vacuo to give a residue. Then deionized water (5 mL) and ACN (1 mL) was added to the residue and the mixture was lyophilized to give the title compound (6.15 mg, 67% yield, FA salt) as yellow solid. $^1$H NMR (400 MHz, DMSO-$d_6$) δ 11.10 (s, 1H), 9.08 (s, 1H), 8.26-8.18 (m, 2H), 7.68 (d, J=8.0 Hz, 1H), 7.64 (d, J=7.6 Hz, 1H), 7.62-7.57 (m, 1H), 7.06 (d, J=7.6 Hz, 1H), 6.95 (t, J=7.6 Hz, 1H), 6.85 (d, J=7.2 Hz, 1H), 5.37 (dd, J=6.0, 12.4 Hz, 1H), 4.54 (d, J=12.0 Hz, 1H), 4.39 (d, J=13.6 Hz, 1H), 4.22-4.08 (m, 4H), 4.01 (s, 1H), 3.96-3.90 (m, 2H), 3.80 (s, 2H), 3.72 (s, 1H), 3.69 (s, 1H), 3.65 (s, 3H), 3.58 (s, 2H), 2.91-2.67 (m, 10H), 2.10-1.98 (m, 3H), 1.95-1.88 (m, 2H), 1.82-1.70 (m, 11H), 1.57 (d, J=9.6 Hz, 5H), 1.50-1.45 (m, 1H), 1.34-1.29 (m, 1H), 1.10-1.02 (m, 3H), 0.97-0.89 (m, 2H); LC-MS (ESI$^+$) m/z 1076.6 (M+H)$^+$.

Example 82. Synthesis of Compound 078

(a) Step 1—3-[3-Methyl-2-oxo-4-(4-piperidyloxy)
benzimidazol-1-yl]piperidine-2,6-dione To a solution of tert-butyl 4-[1-(2,6-dioxo-3-piperidyl)-3-methyl-2-oxo-benzimidazol-4-yl] oxypiperidine-1-carboxylate (300 mg, 654 μmol) in DCM (3 mL) was added TFA (1.54 g, 1 mL). The mixture was stirred at 25° C. for 1 hr. On completion, the reaction mixture was concentrated in vacuo to give the title compound (1.1 g, 27% yield) as brown oil. LC-MS (ESI$^+$) m/z 359.0 (M+H)$^+$.

(b) Step 2—Tert-butyl 3-[[4-[1-(2,6-dioxo-3-piperidyl)-3-methyl-2-oxo-benzimidazol-4-yl]oxy-1-piperidyl] methyl]azetidine-1-carboxylate

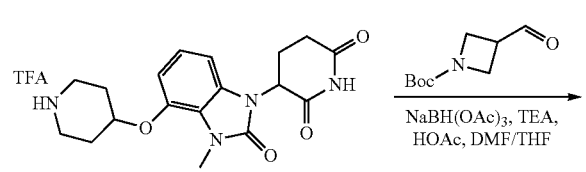

1277
-continued

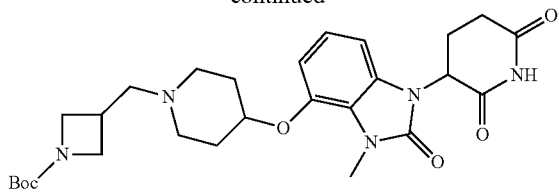

To a solution of 3-[3-methyl-2-oxo-4-(4-piperidyloxy) benzimidazol-1-yl]piperidine-2,6-dione (300 mg, 635 μmol, TFA) in DMF (15 mL) was added TEA (64.2 mg, 635 μmol, 88.3 μL) until pH=8-9, then stirred at −10° C. for 10 mins, tert-butyl 3-formylazetidine-1-carboxylate (235 mg, 1.27 mmol, CAS #177947-96-5) and AcOH (38.1 mg, 635 μmol, 36.3 μL) was added until pH=5-6, then stirred at −10° C. for 20 mins, finally, NaBH(OAc)$_3$ (174 mg, 825 μmol). The mixture was stirred at −10° C. for 2 hrs. On completion, the residue was diluted with water (60 mL) and extracted with EA (2×20 mL). The combined organic layers was washed with brine (15 mL) and dried over Na$_2$SO$_4$, filtered and the filtrate was concentrated in vacuo to give a residue. The residue was purified by reverse phase (0.1% FA condition) to give the title compound (100 mg, 29% yield) as a white solid. LC-MS (ESI$^+$) m/z 528.2 (M+H)$^+$.

(c) Step 3—3-[4-[[1-(Azetidin-3-ylmethyl)-4-piperidyl]oxy]-3-methyl-2-oxo-benzimidazol-1-yl] piperidine-2,6-dione

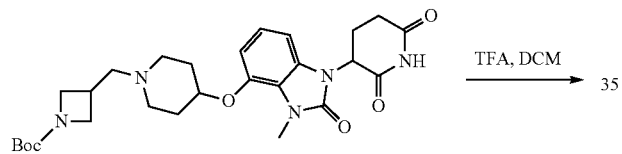

TFA, DCM

1278
-continued

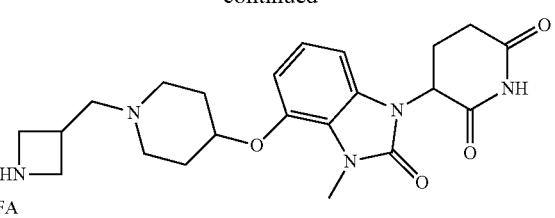

To a solution of tert-butyl 3-[[4-[1-(2,6-dioxo-3-piperidyl)-3-methyl-2-oxo-benzimidazol-4-yl]oxy-1-piperidyl] methyl]azetidine-1-carboxylate (100 mg, 189 μmol) in DCM (2.5 mL) was added TFA (767 mg, 6.73 mmol, 0.5 mL). The mixture was stirred at 25° C. for 1 hr. On completion, the reaction mixture was concentrated in vacuo to give the title compound (100 mg, 97% yield, TFA) as brown oil. LC-MS (ESI$^+$) m/z 428.1 (M+H)$^+$.

(d) Step 4—Tert-butyl 3-[2-[[(3S,8S)-3-[[3-[[4-[1-(2,6-dioxo-3-piperidyl)-3-methyl-2-oxo-benzimidazol-4-yl]oxy-1-piperidyl]methyl]azetidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

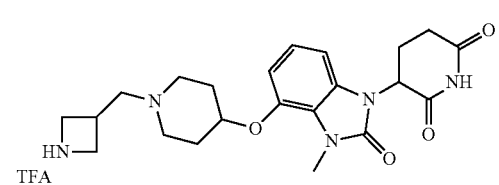

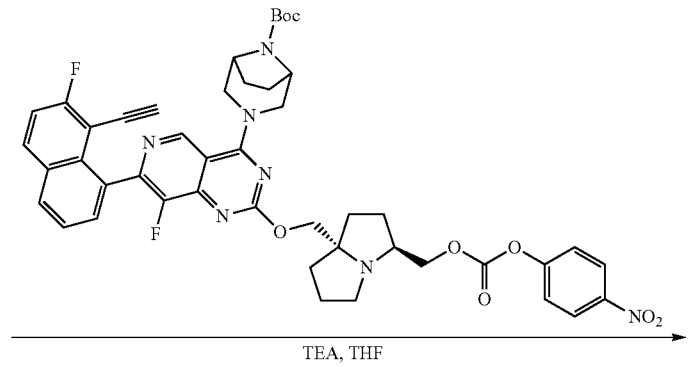

TEA, THF

1279

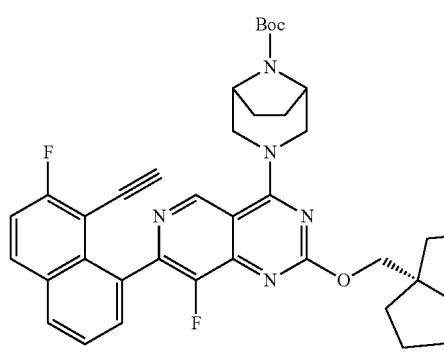

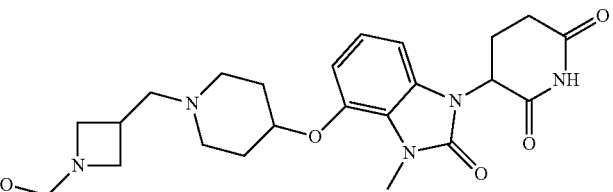

To a solution of 3-[4-[[1-(azetidin-3-ylmethyl)-4-piperidyl]oxy]-3-methyl-2-oxo-benzimidazol-1-yl] piperidine-2,6-dione (46.4 mg, 85.8 μmol, TFA) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (74 mg, 85.8 μmol) in THF (2 mL) was added TEA (26.0 mg, 257 μmol, 35.8 μL). The mixture was stirred at 25° C. for 0.5 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 18%-48% B over 11 min) to give the title compound (30 mg, 30% yield) as a white solid, $^1$H NMR (400 MHz, DMSO-$d_6$) δ 11.09 (s, 1H), 9.15 (s, 1H), 8.27-8.17 (m, 2H), 7.74-7.68 (m, 1H), 7.67-7.58 (m, 2H), 7.01-6.89 (m, 1H), 6.76 (dd, J=8.4, 17.2 Hz, 2H), 5.33 (dd, J=5.2, 12.4 Hz, 1H), 4.68-4.40 (m, 5H), 4.39-4.13 (m, 5H), 4.12-3.86 (m, 4H), 3.76-3.59 (m, 4H), 3.54 (s, 3H), 2.95-2.78 (m, 3H), 2.77-2.55 (m, 8H), 2.31-2.20 (m, 2H), 2.13-1.92 (m, 8H), 1.91-1.80 (m, 4H), 1.78-1.69 (m, 3H), 1.47 (s, 9H).

(e) Step 5—[(3S,8S)-8-[[4-(3,8-Diazabicyclo[3.2.1] octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 3-[[4-[1-(2,6-dioxo-3-piperidyl)-3-methyl-2-oxo-benzimidazol-4-yl]oxy-1-piperidyl]methyl]azetidine-1-carboxylate (078)

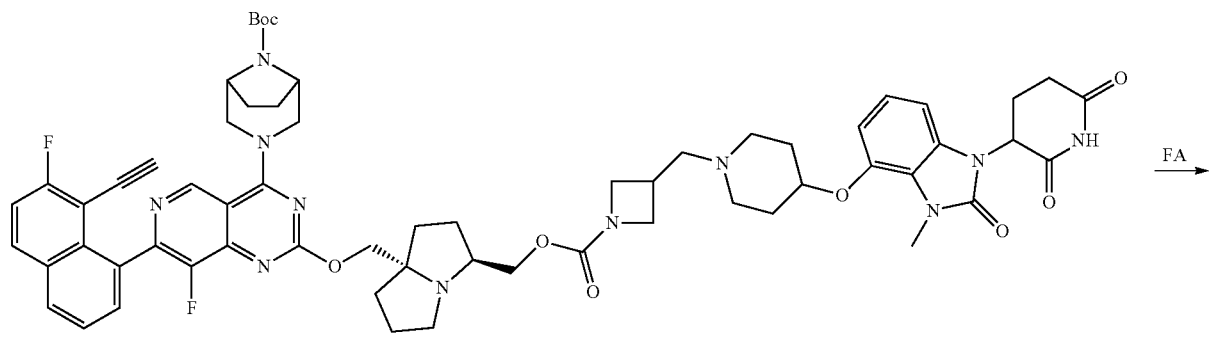

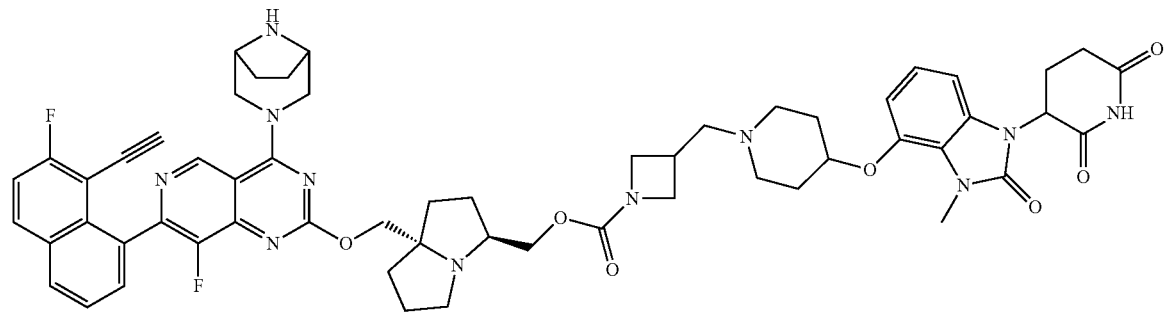

078

A mixture of tert-butyl3-[2-[[(3S,8S)-3-[[3-[[4-[1-(2,6-dioxo-3-piperidyl)-3-methyl-2-oxo-benzimidazol-4-yl]oxy-1-piperidyl]methyl]azetidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (30 mg, 26.0 µmol) in FA (2 mL) was stirred at 25° C. for 0.5 hr. On completion, the reaction mixture was dried with $N_2$ to give the title compound (20.6 mg, 96% purity, FA) as yellow solid. $^1$H NMR (400 MHz, DMSO-$d_6$) δ 11.08 (s, 1H), 9.11 (s, 1H), 8.27-8.17 (m, 2H), 7.73-7.67 (m, 1H), 7.67-7.57 (m, 2H), 6.98-6.89 (m, 1H), 6.75 (dd, J=8.4, 18.0 Hz, 2H), 5.33 (dd, J=5.2, 12.8 Hz, 1H), 4.65-4.60 (m, 1H), 4.55-4.42 (m, 2H), 4.33-4.24 (m, 1H), 4.24-4.11 (m, 3H), 4.09-3.90 (m, 5H), 3.84-3.72 (m, 2H), 3.63-3.46 (m, 8H), 2.96-2.84 (m, 3H), 2.81-2.75 (m, 1H), 2.74-2.65 (m, 2H), 2.64-2.56 (m, 4H), 2.40-2.25 (m, 2H), 2.16-2.08 (m, 1H), 2.05-1.98 (m, 3H), 1.91-1.79 (m, 8H), 1.76-1.56 (m, 4H); LC-MS (ESI$^+$) m/z 1050.4 (M+H)$^+$.

Example 83. Synthesis of Compound 079

(a) Step 1—Tert-butyl 4-[3-methyl-1-(1-methyl-2,6-dioxo-3-piperidyl)-2-oxo-benzimidazol-4-yl] piperidine-1-carboxylate To a mixture of tert-butyl 4-[1-(2,6-dioxo-3-piperidyl)-3-methyl-2-oxo-benzimidazol-4-yl] piperidine-1-carboxylate (270 mg, 610 µmol) in DMF (2 mL) was added MeI (103 mg, 732 µmol) and $K_2CO_3$ (168 mg, 1.22 mmol). The reaction mixture was stirred at 25° C. for 1.3 hrs. On completion, the residue was diluted with water (30 mL) and extracted with EA (2×30 mL). The combined organic layers was dried over $Na_2SO_4$, filtered and the filtrate concentrated in vacuo to give the title compound (300 mg, crude) as yellow solid. $^1$H NMR (400 MHz, DMSO-$d_6$) δ 7.96 (s, 1H), 6.99 (s, 3H), 5.49-5.40 (m, 1H), 4.13-4.03 (m, 2H), 3.61 (s, 3H), 3.44 (d, J=10.5 Hz, 1H), 3.30 (s, 1H), 3.04 (s, 3H), 2.90 (s, 3H), 2.05-1.97 (m, 1H), 1.82 (d, J=12.0 Hz, 2H), 1.63-1.57 (m, 2H), 1.43 (s, 9H); LC-MS (ESI$^+$) m/z 479.1 (M+Na)$^+$.

(b) Step 2—1-Methyl-3-[3-methyl-2-oxo-4-(4-piperidyl)benzimidazol-1-yl]piperidine-2,6-dione

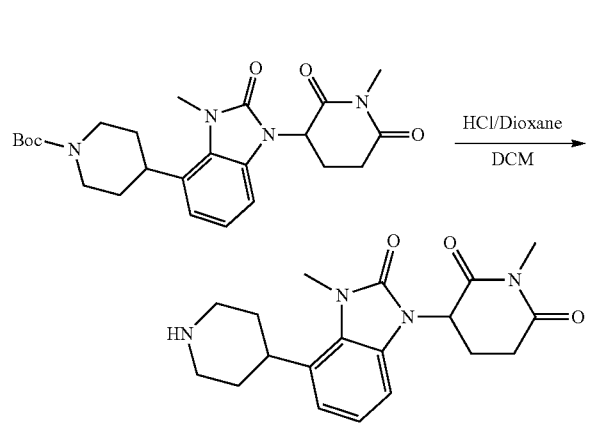

To a mixture of tert-butyl 4-[3-methyl-1-(1-methyl-2,6-dioxo-3-piperidyl)-2-oxo-benzimidazol-4-yl] piperidine-1-carboxylate (300 mg, 657 µmol) in DCM (2 mL) was added HCl/dioxane (2.5 M, 2 mL). The reaction mixture was stirred at 25° C. for 2 hrs. On completion, the reaction mixture was concentrated in vacuo to give title compound (230 mg, 98% yield, HCl salt) as yellow solid. LC-MS (ESI$^+$) m/z 357.2 (M+H)$^+$.

(c) Step 3—4-[[4-[3-methyl-1-(1-methyl-2,6-dioxo-3-piperidyl)-2-oxo-benzimidazol-4-yl]-1-piperidyl]methyl]piperidine-1-carboxylate

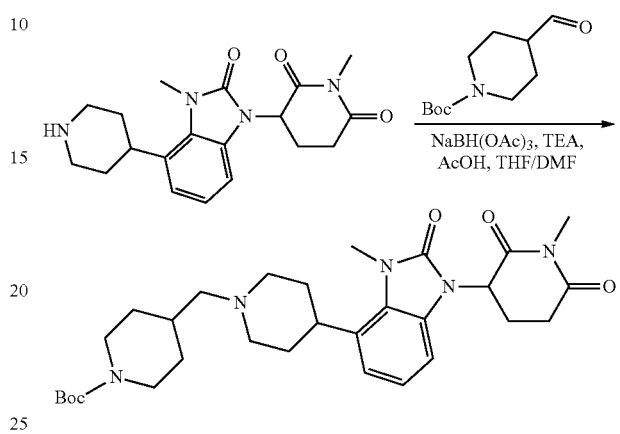

To a mixture of tert-butyl 4-formylpiperidine-1-carboxylate (151 mg, 709 µmol, CAS #137076-22-3) in DMF (1 mL) and THF (1 mL) was added TEA (195 mg, 1.94 mmol). The reaction mixture was added 1-methyl-3-[3-methyl-2-oxo-4-(4-piperidyl)benzimidazol-1-yl]piperidine-2,6-dione (230 mg, 645 µmol, HCl salt) and HOAc (116 mg, 1.94 mmol). The reaction mixture was stirred at 25° C. for 0.5 hours. Then NaBH(OAc)$_3$ (205 mg, 967 µmol) was added into reaction mixture. The reaction mixture was stirred at 25° C. for 3.5 hrs. On completion, the reaction mixture was quenched with water (0.05 mL) and concentrated in vacuo. The residue was purified by reverse phase (0.1% FA condition) to give the title compound (120 mg, 33% yield) as white solid. LC-MS (ESI$^+$) m/z 554.3 (M+H)$^+$.

(d) Step 4—1-Methyl-3-[3-methyl-2-oxo-4-[1-(4-piperidylmethyl)-4-piperidyl]benzimidazol-1-yl]piperidine-2,6-dione

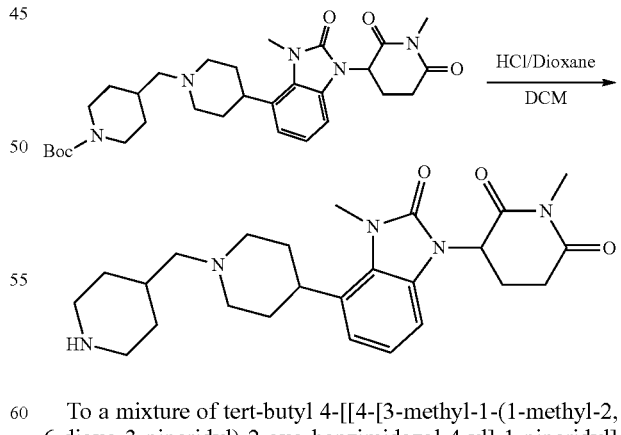

To a mixture of tert-butyl 4-[[4-[3-methyl-1-(1-methyl-2,6-dioxo-3-piperidyl)-2-oxo-benzimidazol-4-yl]-1-piperidyl]methyl]piperidine-1-carboxylate (100 mg, 180 µmol) in DCM (1 mL) was added HCl/dioxane (2.5 M, 1 mL). The reaction mixture was stirred at 25° C. for 0.5 hr. On completion, the reaction mixture was concentrated in vacuo to give the title compound (85.0 mg, 96% yield, HCl) as white solid. LC-MS (ESI$^+$) m/z 454.2 (M+H)$^+$.

(e) Step 5—Tert-butyl 3-[7-(8-ethynyl-7-fluoro-1-naphthyl)-8-fluoro-2-[[(3S,8S)-3-[[4-[[4-[3-methyl-1-(1-methyl-2,6-dioxo-3-piperidyl)-2-oxo-benzimidazol-4-yl]-1-piperidyl]methyl]piperidine-1-carbonyl]oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

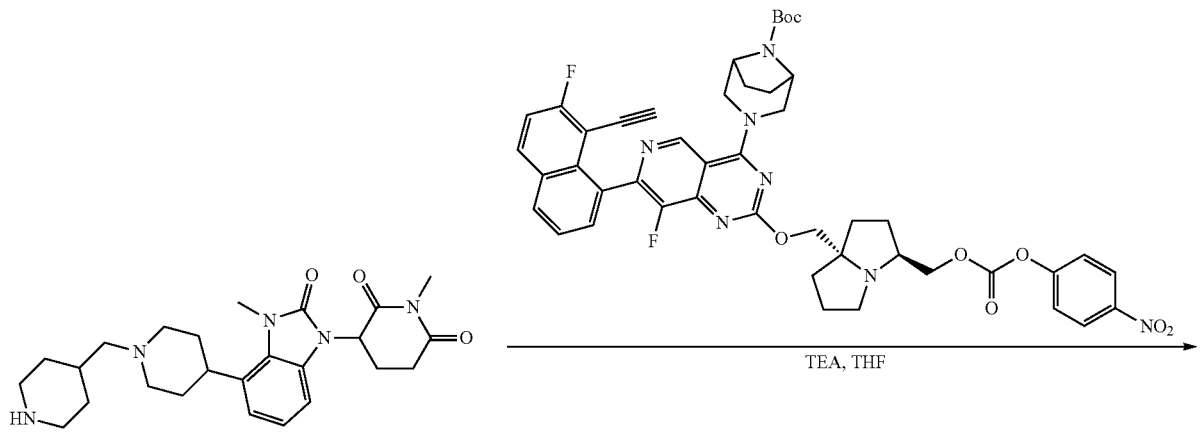

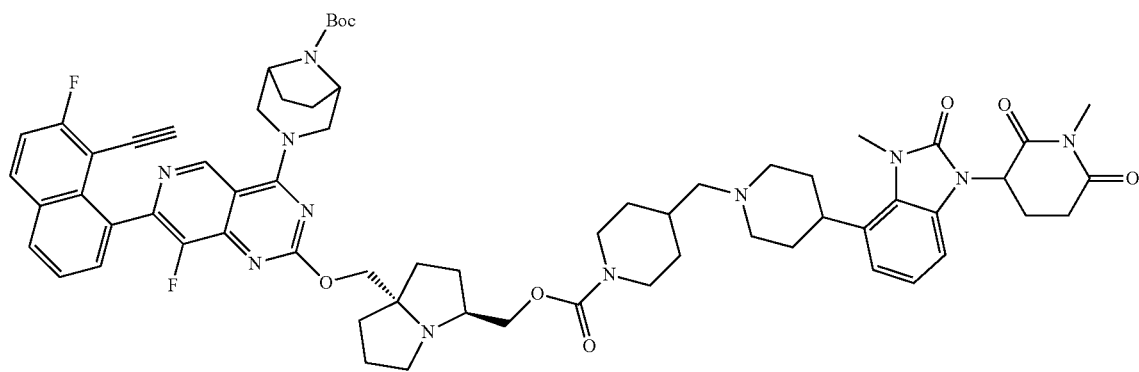

To a mixture of 1-methyl-3-[3-methyl-2-oxo-4-[1-(4-piperidylmethyl)-4-piperidyl]benzimidazol-1-yl]piperidine-2,6-dione (79.6 mg, 162 μmol, HCl) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70.0 mg, 81.2 μmol) in THF (2 mL) was added TEA (8.22 mg, 81.2 μmol). The reaction mixture was stirred at 25° C. for 2.5 hrs. On completion, the reaction mixture was concentrated in vacuo. The residue was purified by prep-HPLC (column: Phenomenex luna C18 150*25 mm*10 μm; mobile phase: [water (FA)-ACN]; gradient: 19%-49% B over 11 min) to give the title compound (30.0 mg, 31% yield) as yellow solid. $^1$H NMR (400 MHz, DMSO-$d_6$) δ 9.10 (s, 1H), 8.28-8.19 (m, 2H), 7.74-7.57 (m, 3H), 6.99 (t, J=6.8 Hz, 3H), 5.44 (dd, J=5.2, 12.8 Hz, 1H), 4.60-4.53 (m, 1H), 4.47-4.38 (m, 1H), 4.32 (d, J=1.2 Hz, 2H), 4.26-4.19 (m, 1H), 4.18-4.11 (m, 2H), 4.07 (d, J=10.8 Hz, 1H), 4.03 (d, J=2.4 Hz, 1H), 4.00-3.91 (m, 2H), 3.68-3.61 (m, 2H), 3.58 (s, 3H), 3.04 (s, 3H), 2.98-2.91 (m, 3H), 2.90 (s, 1H), 2.76 (s, 4H), 2.74 (s, 2H), 2.68 (s, 2H), 2.15 (d, J=6.0 Hz, 2H), 2.08-1.99 (m, 4H), 1.85 (dd, J=3.2, 6.0 Hz, 2H), 1.80-1.68 (m, 14H), 1.52 (s, 1H), 1.47 (s, 9H), 1.04-0.91 (m, 2H); LC-MS (ESI) m/z 1176.6 (M+H)$^+$.

(f) Step 5—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl 4-[[4-[3-
methyl-1-(1-methyl-2,6-dioxo-3-piperidyl)-2-oxo-
benzimidazol-4-yl]-1-piperidyl]methyl]piperidine-1-
carboxylate (079)

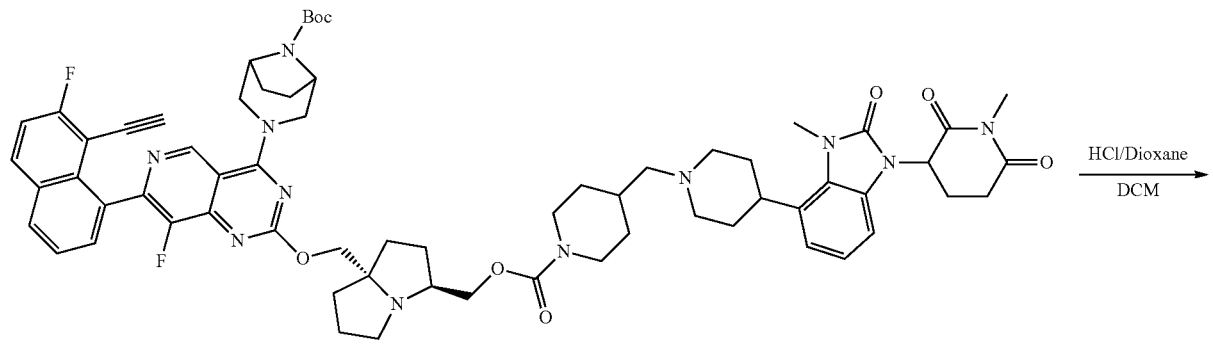

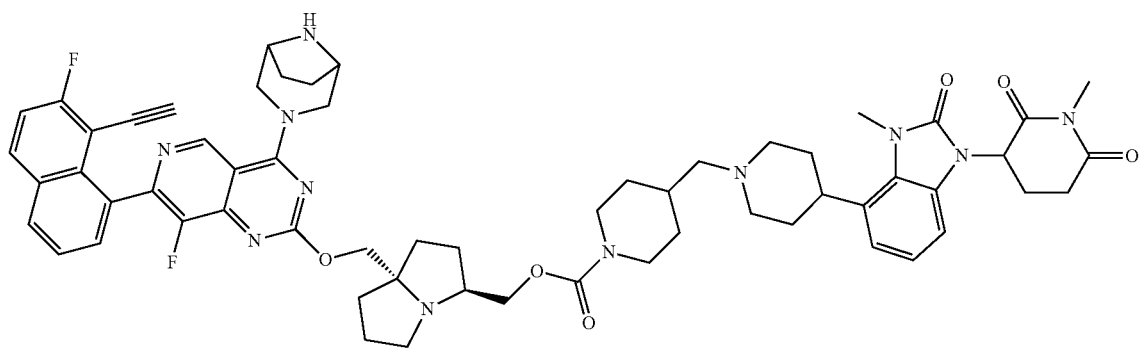

079

To a mixture of tert-butyl 3-[7-8ethynyl-7-fluoro-1-naphthyl)-8-fluoro-2-[[(3S,8S)-3-[[4-[[4-[3-methyl-1-(1-methyl-2,6-dioxo-3-piperidyl)-2-oxo-benzimidazol-4-yl]-1-piperidyl]methyl]piperidine-1-carbonyl]oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (25.0 mg, 21.2 μmol) in DCM (1 mL) was added HCl/dioxane (2.5 M, 833 μL). The reaction mixture was stirred at 25° C. for 1 hrs. On completion, the reaction mixture was concentrated in vacuo to give the title compound (17.9 mg, 73 yield, HCl salt) as yellow solid. $^1$H NMR (400 MHz, DMSO-$d_6$) δ 11.02-10.90 (m, 1H), 10.30-10.18 (m, 1H), 9.97-9.83 (m, 1H), 9.53 (d, J=3.0, 7.2 Hz, 1H), 9.18 (s, 1H), 8.32-8.19 (m, 2H), 7.81-7.58 (m, 3H), 7.12-6.93 (m, 3H), 5.46 (dd, J=5.6, 13.2 Hz, 1H), 4.76-4.61 (m, 3H), 4.60-4.53 (m, 1H), 4.45-4.34 (m, 1H), 4.30-4.14 (m, 4H), 4.10-3.93 (m, 5H), 3.65-3.53 (m, 6H), 3.21-3.11 (m, 2H), 3.04 (s, 3H), 3.00-2.96 (m, 2H), 2.89-2.72 (m, 4H), 2.39-2.33 (m, 2H), 2.22-1.83 (m, 18H), 1.29-1.11 (m, 5H); LC-MS (ESI$^+$) m/z 1076.5 (M+H)$^+$.

Example 84. Synthesis of Compound 080

(a) Step 1—3-[3-Methyl-2-oxo-5-(4-piperidyl)benzimidazol-1-yl]piperidine-2,6-dione To a solution of tert-butyl 4-[1-(2,6-dioxo-3-piperidyl)-3-methyl-2-oxo-benzimidazol-5-yl] piperidine-1-carboxylate (300 mg, 677 μmol) in DCM (3 mL) was added TFA (1.54 g, 13.4 mmol). The mixture was stirred at 25° C. for 1 hr. On completion, the reaction mixture was concentrated in vacuo to give the title compound (300 mg, 96% yield, TFA) as a white oil. LC-MS (ESI$^+$) m/z 343.0 (M+H)$^+$.

(b) Step 2—Tert-butyl (3R)-3-[[4-[1-(2,6-dioxo-3-piperidyl)-3-methyl-2-oxo-benzimidazol-5-yl]-1-piperidyl]methyl]pyrrolidine-1-carboxylate

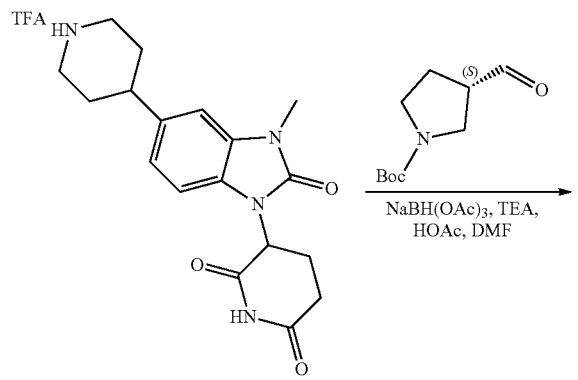

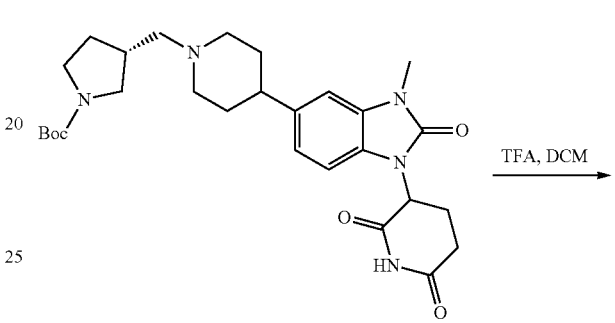

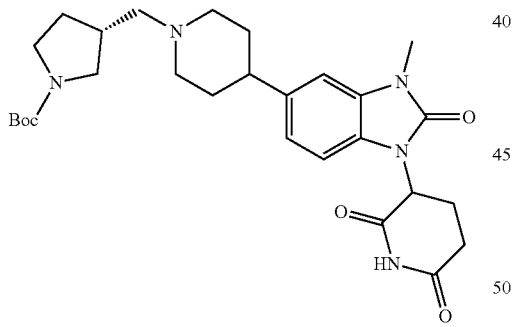

To a mixture of 3-[3-methyl-2-oxo-5-(4-piperidyl)benzimidazol-1-yl]piperidine-2,6-dione (300 mg, 657 μmol, TFA) in THF (1 mL) was added TEA (66.5 mg, 657 μmol, CAS #191348-04-6) at −15° C. until pH stabilized at 8. The mixture was stirred at −15° C. for 0.25 hr, then AcOH (39.4 mg, 657 μmol) was added at −15° C. until pH stabilized at 5~6. The mixture was cooled to −15° C. Subsequently, tert-butyl (3S)-3-formylpyrrolidine-1-carboxylate (130 mg, 657 μmol) in DMF (2 mL) was added for 0.25 hr. After that, NaBH(OAc)$_3$ (167 mg, 788 μmol) was added one portion. The resulting reaction mixture was stirred at −15° C. for 2 hrs. On completion, the mixture was quenched with water (5 mL) at 0° C. and extracted with ethyl acetate (10 mL×3), the combined organic phase was dried over Na$_2$SO$_4$, filtered and concentrated to give a residue. The residue was purified by reversed phase flash (0.1% FA condition) to give the title compound (95 mg, 26% yield) as a white oil. $^1$H NMR (400 MHz, DMSO-d$_6$) δ 11.07 (s, 1H), 8.30-8.01 (m, 1H), 7.10 (s, 1H), 7.02-6.90 (m, 1H), 5.37-5.28 (m, 1H), 3.33 (s, 3H), 3.05-2.85 (m, 6H), 2.74-2.58 (m, 6H), 2.14-1.96 (m, 4H), 1.83-1.66 (m, 4H), 1.62-1.48 (m, 2H), 1.47-1.32 (s, 9H); LC-MS (ESI$^+$) m/z 526.1 (M+H)$^+$.

(c) Step 3—3-[3-Methyl-2-oxo-5-[1-[[(3S)-pyrrolidin-3-yl]methyl]-4-piperidyl]benzimidazol-1-yl]piperidine-2,6-dione

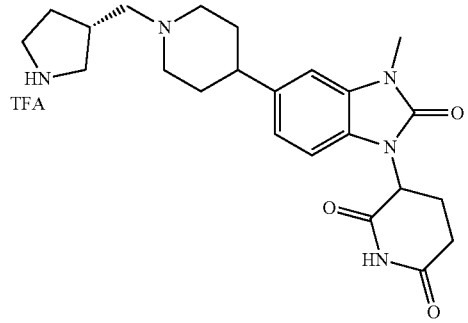

To a solution of tert-butyl (3R)-3-[[4-[1-(2,6-dioxo-3-piperidyl)-3-methyl-2-oxo-benzimidazol-5-yl]-1-piperidyl]methyl]pyrrolidine-1-carboxylate (52 mg, 98 μmol) in DCM (1 mL) was added TFA (307 mg, 2.69 mmol). The mixture was stirred at 25° C. for 1 hr. On completion, the reaction mixture was concentrated in vacuo to give the title compound (53 mg, 99% yield, TFA) as a yellow oil. LC-MS (ESI$^+$) m/z 426.1 (M+H)$^+$.

(d) Step 4—Tert-butyl 3-[2-[[(3S,8S)-3-[[(3R)-3-[[4-[1-(2,6-dioxo-3-piperidyl)-3-methyl-2-oxo-benzimidazol-5-yl]-1-piperidyl]methyl]pyrrolidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

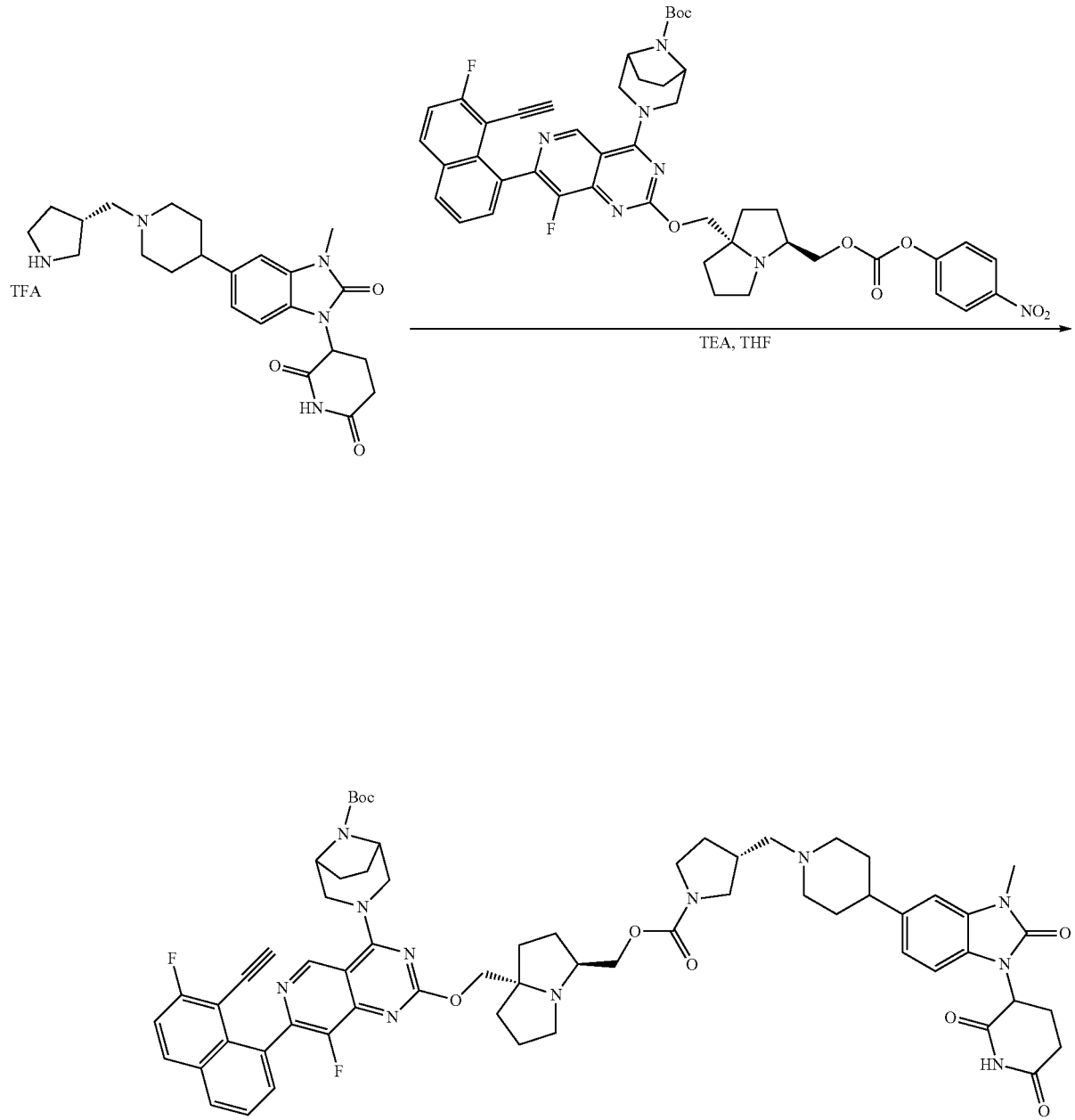

To a solution of 3-[3-methyl-2-oxo-5-[1-[[(3S)-pyrrolidin-3-yl]methyl]-4-piperidyl]benzimidazol-1-yl]piperidine-2,6-dione (52.5 mg, 97.4 µmol, TFA) in THF (1 mL) was added TEA (8.22 mg, 81.2 µmol) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (70 mg, 81.2 µmol). The mixture was stirred at 25° C. for 12 hrs. On completion, the reaction mixture was concentrated in vacuo. The residue was purified by prep-HPLC (Phenomenex luna C18 150*25 mm*10 um; mobile phase: [water (FA)-ACN]; gradient: 24%-44% B over 10 min) to give the compound (20 mg, 21% yield) as a yellow solid. LC-MS (ESI$^+$) m/z 1148.5 (M+H)$^+$.

(e) Step 5—[(3S,8S)-8-[[4-(3,8-Diazabicyclo[3.2.1]
octan-3-yl)-7-(8-ethynyl-7-fluoro-1-naphthyl)-8-
fluoro-pyrido[4,3-d]pyrimidin-2-yl]oxymethyl]-1,2,
3,5,6,7-hexahydropyrrolizin-3-yl]methyl(3R)-3-[[4-
[1-(2,6-dioxo-3-piperidyl)-3-methyl-2-oxo-
benzimidazol-5-yl]-1-piperidyl]methyl]pyrrolidine-
1-carboxylate (080)

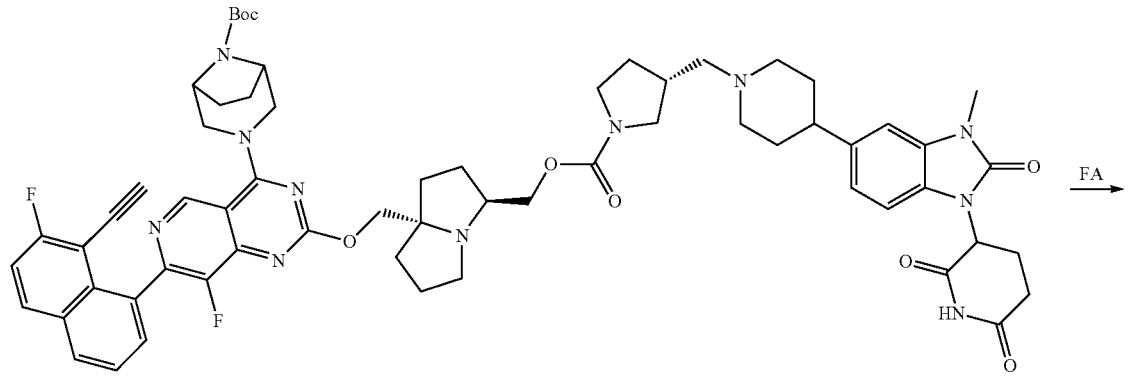

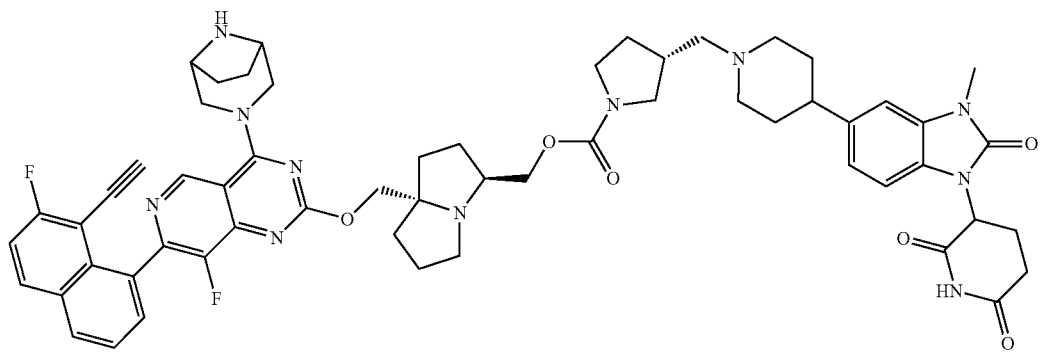

080

A solution of tert-butyl 3-[2-[[(3S,8S)-3-[[(3R)-3-[[4-[1-(2,6-dioxo-3-piperidyl)-3-methyl-2-oxo-benzimidazol-5-yl]-1-piperidyl]methyl]pyrrolidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (15 mg, 13.0 μmol) in FA (0.5 mL) was stirred at 25° C. for 0.5 hr. On completion, the reaction mixture was concentrated in vacuo to give the title compound (5.74 mg, 40% yield, FA) as a yellow solid. $^1$H NMR (400 MHz, DMSO-$d_6$) δ 11.08 (s, 1H), 9.06 (s, 1H), 8.25-8.21 (m, 1H), 8.18-8.15 (m, 1H), 7.73-7.54 (m, 3H), 7.09 (d, J=8.4 Hz, 1H), 6.99 (d, J=6.8 Hz, 1H), 6.93-6.87 (m, 1H), 5.33 (dd, J=5.6, 12.4 Hz, 1H), 4.49 (d, J=11.6 Hz, 1H), 4.35 (d, J=12.4 Hz, 1H), 4.18-4.06 (m, 4H), 3.69-3.64 (m, 4H), 3.47-3.39 (m, 4H), 3.33-3.29 (m, 5H), 3.03-2.89 (m, 4H), 2.83-2.64 (m, 4H), 2.34-2.27 (m, 3H), 2.10-1.85 (m, 7H), 1.80-1.67 (m, 13H), 1.57-1.49 (m, 2H); LC-MS (ESI$^+$) m/z 1048.5 (M+H)$^+$.

Example 85. Synthesis of Compound 081

(a) Step 1—3-[3-Methyl-2-oxo-5-(4-piperidyl)benz-imidazol-1-yl]piperidine-2,6-dione To a solution of tert-butyl 4-[1-(2,6-dioxo-3-piperidyl)-3-methyl-2-oxo-benzimidazol-5-yl] piperidine-1-carboxylate (300 mg, 677 μmol) in DCM (3 mL) was added TFA (77.3 mg, 677 μmol) dropwise at 25° C., then the reaction mixture was stirred at 25° C. for 1 hr. On completion, the reaction mixture was concentrated in vacuo to give the title compound (300 mg, 96% yield, TFA) as light yellow solid. LC-MS (ESI$^+$) m/z 343.0 (M+H)$^+$.

(b) Step 2—Tert-butyl (3S)-3-[[4-[1-(2,6-dioxo-3-piperidyl)-3-methyl-2-oxo-benzimidazol-5-yl]-1-piperidyl]methyl]pyrrolidine-1-carboxylate

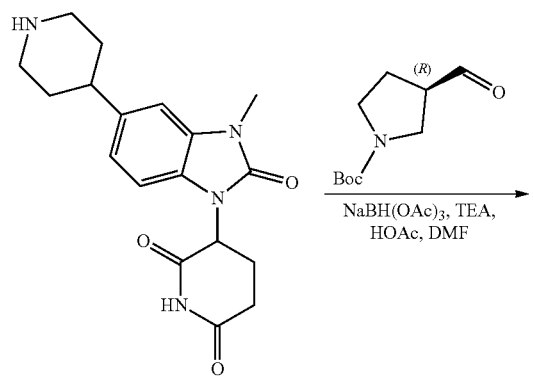

To a solution of 3-[3-methyl-2-oxo-5-(4-piperidyl)benzimidazol-1-yl]piperidine-2,6-dione (300 mg, 657 µmol, TFA) in DMF (10 mL) was added TEA (66.5 mg, 657 µmol) was stirred at 25° C. for 0.1 hr, then tert-butyl (3R)-3-formylpyrrolidine-1-carboxylate (157 mg, 788 µmol, CAS #191347-94-1), AcOH (39.4 mg, 657 µmol) was added at −10° C. and the mixture was stirred at −10° C. for 0.5 hr. Then NaBH(OAc)$_3$ (208 mg, 985 µmol) was added. The reaction was stirred at −10° C. for 2 hrs. On completion, the reaction mixture was quenched with water (5 mL) and concentrated in vacuo to give a residue. The residue was diluted with water (20 mL) and extracted with EA (10 mL×3). The combined organic layer was dried over Na$_2$SO$_4$, filtered and concentrated in vacuo to give a residue. The residue was purified by reverse phase (0.1% FA condition) to give the title compound (160 mg, 46% yield) as white solid, $^1$H NMR (400 MHz, DMSO-d$_6$) δ 11.14 (s, 1H), 8.21 (s, 1H), 7.17 (s, 1H), 7.07 (d, J=8.4 Hz, 1H), 6.98 (d, J=8.0 Hz, 1H), 5.40 (dd, J=5.2, 12.8 Hz, 1H), 3.46 (dd, J=7.2, 10.0 Hz, 2H), 3.40 (s, 3H), 3.38-3.34 (m, 1H), 3.28-3.23 (m, 1H), 3.13 (d, J=10.4 Hz, 1H), 3.06 (d, J=10.4 Hz, 1H), 3.01-2.94 (m, 2H), 2.80-2.69 (m, 2H), 2.65-2.60 (m, 1H), 2.45-2.41 (m, 2H), 2.10-2.01 (m, 2H), 2.01-1.93 (m, 1H), 1.8-1.79 (m, 3H), 1.67-1.52 (m, 2H), 1.46 (s, 9H); LC-MS (ESI$^+$) m/z 526.1 (M+H)$^+$.

(c) Step 3—3-[3-Methyl-2-oxo-5-[1-[[(3R)-pyrrolidin-3-yl]methyl]-4-piperidyl]benzimidazol-1-yl]piperidine-2,6-dione

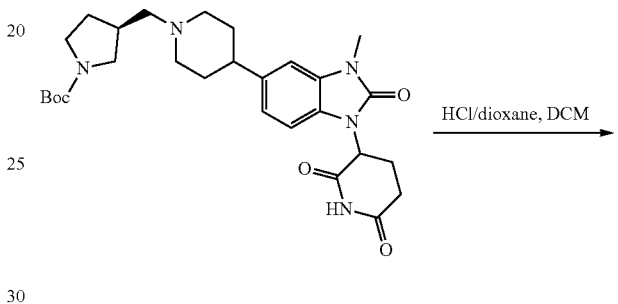

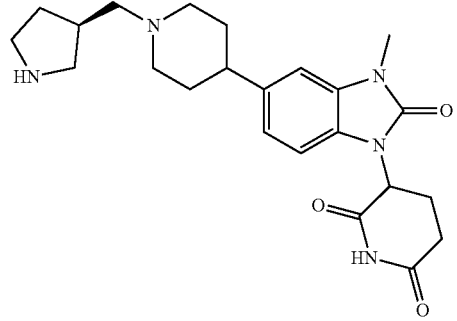

To a solution of tert-butyl (3S)-3-[[4-[1-(2,6-dioxo-3-piperidyl)-3-methyl-2-oxo-benzimidazol-5-yl]-1-piperidyl]methyl]pyrrolidine-1-carboxylate (100 mg, 190 µmol) in DCM (3 mL) was added HCl/dioxane (4 M, 1 mL) dropwise at 25° C., then the reaction mixture was stirred at 25° C. for 0.2 hr. On completion, the reaction mixture was concentrated in vacuo to give the title compound (87 mg, 98% yield, HCl) as white solid. LC-MS (ESI$^+$) m/z 426.1 (M+H)$^+$.

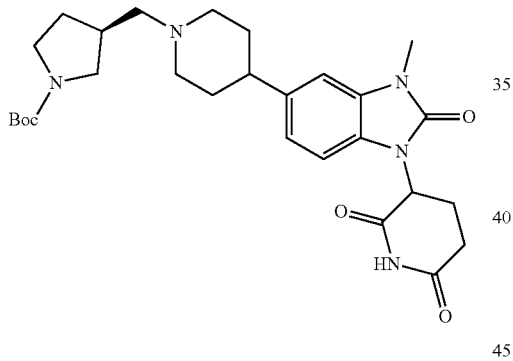

(d) Step 4—Tert-butyl 3-[2-[[(3S,8S)-3-[[(3S)-3-[[4-[1-(2,6-dioxo-3-piperidyl)-3-methyl-2-oxo-benzimidazol-5-yl]-1-piperidyl]methyl]pyrrolidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

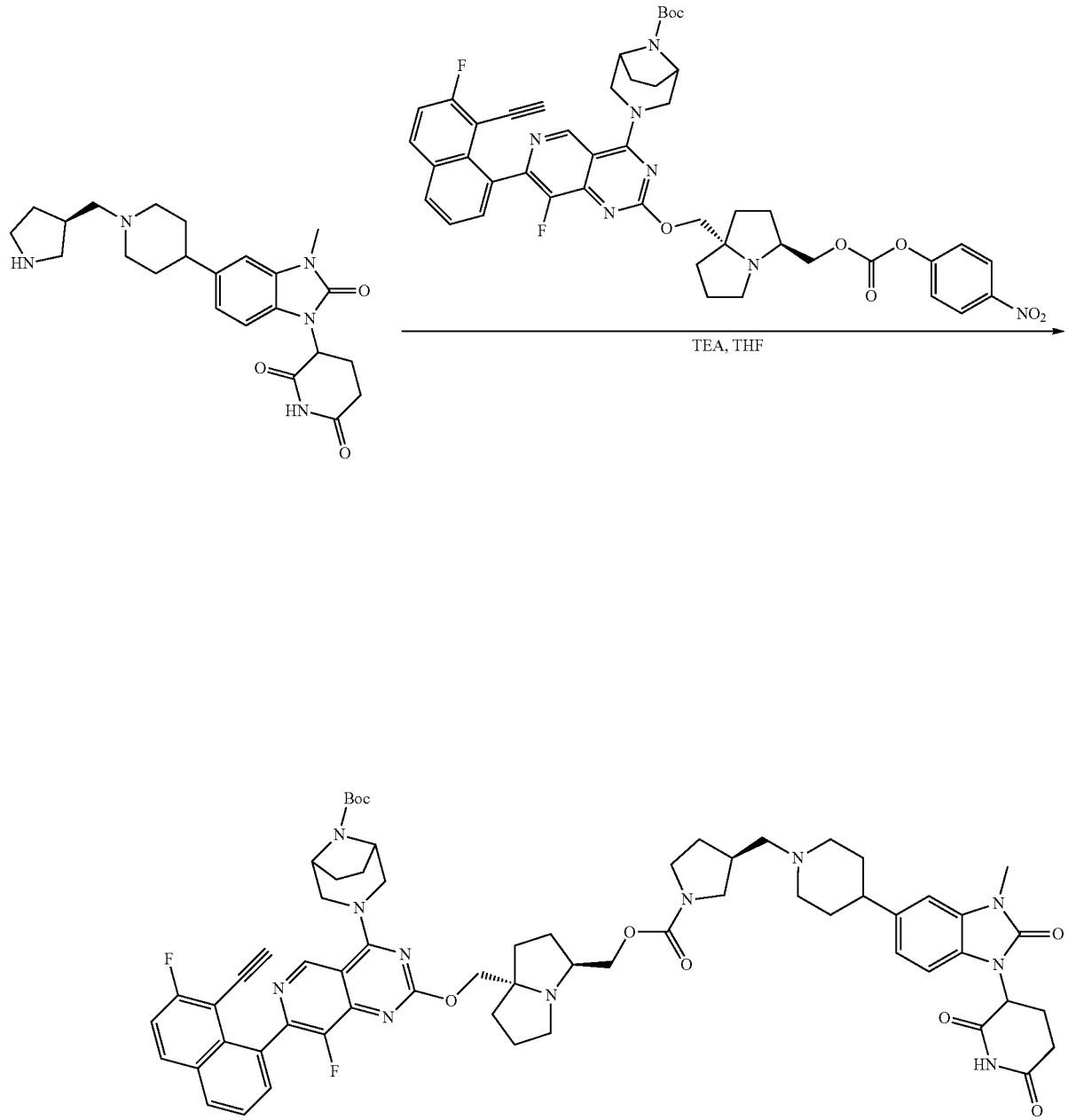

A mixture of 3-[3-methyl-2-oxo-5-[1-[[(3R)-pyrrolidin-3-yl]methyl]-4-piperidyl]benzimidazol-1-yl]piperidine-2,6-dione (75.0 mg, 162 μmol, HCl), TEA (24.6 mg, 243 μmol) in THF (4 mL) was stirred at 25° C., then, tert-butyl 3-[7-(8-ethynyl-7-fluoro-1-naphthyl)-8-fluoro-2-[[(3S,8S)-3-[(4-nitrophenoxy) carbonyloxymethyl]-1,2,3,5,6,7-hexahydropyrrolizin-8-yl]methoxy]pyrido [4,3-d] pyrimidin-4-yl]-3,8-diazabicyclo[3.2.1]octane-8-carboxylate (70 mg, 81.2 μmol) in THF (4 mL) was added. The mixture was stirred at 25° C. for 0.1 hr. On completion, the reaction mixture was concentrated in vacuo to give a residue. The residue was purified by prep-HPLC (column: Phenomenex luna C18 150*25 mm*10 um; mobile phase: [water (FA)-ACN]; gradient: 20%-50% B over 10 min) to give the title compound (45 mg, 46% yield, FA) as light yellow solid. LC-MS (ESI$^+$) m/z 1148.0 (M+H)$^+$.

(e) Step 5—[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl (3S)-3-[[4-[1-(2,6-dioxo-3-piperidyl)-3-methyl-2-oxo-benzimidazol-5-yl]-1-piperidyl]methyl]pyrrolidine-1-carboxylate (081)

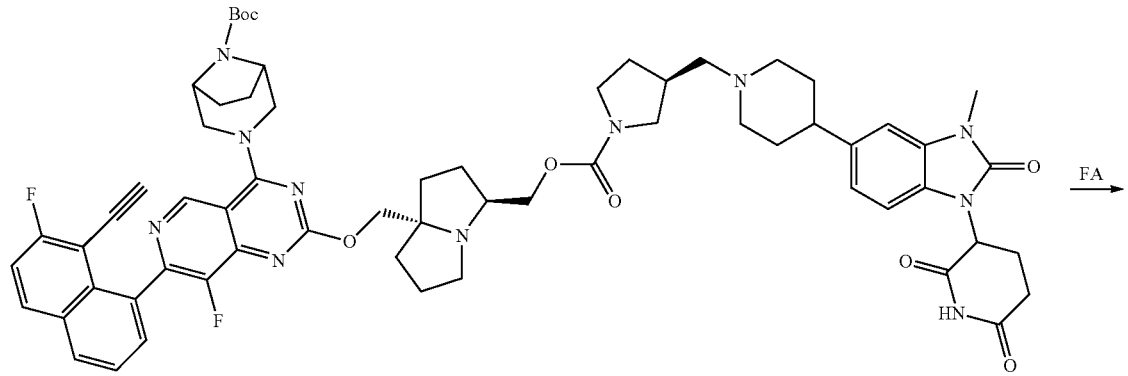

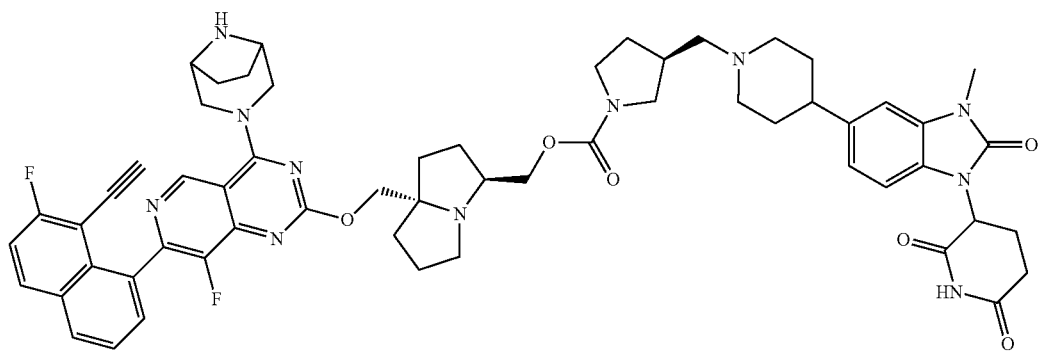

081

To a solution of tert-butyl 3-[2-[[[(3S,8S)-3-[[(3S)-3-[[4-[1-(2,6-dioxo-3-piperidyl)-3-methyl-2-oxo-benzimidazol-5-yl]-1-piperidyl]methyl]pyrrolidine-1-carbonyl]oxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (35 mg, 30.4 μmol) in HCOOH (1.46 mg, 30.4 μmol) dropwise at 25° C., then the reaction mixture was stirred at 25° C. for 1 hr. On completion, the reaction mixture was concentrated in vacuo to give the title compound (30 mg, 89% yield, FA) as yellow solid. $^1$H NMR (400 MHz, DMSO-$d_6$) δ 11.09 (s, 1H), 9.08 (s, 1H), 8.25 (s, 1H), 8.20-8.17 (m, 1H), 7.73-7.57 (m, 3H), 7.10 (d, J=8.4 Hz, 1H), 7.02-6.97 (m, 1H), 6.91 (s, 1H), 5.34 (dd, J=4.8, 12.0 Hz, 1H), 4.54 (d, J=12.4 Hz, 1H), 4.40 (d, J=12.0 Hz, 1H), 4.28-4.21 (m, 1H), 4.20-4.08 (m, 3H), 4.03 (s, 1H), 3.79 (s, 2H), 3.75-3.65 (m, 2H), 3.49-3.40 (m, 1H), 3.32 (s, 3H), 3.28-3.21 (m, 1H), 3.07-2.89 (m, 4H), 2.88-2.75 (m, 3H), 2.75-2.55 (m, 3H), 2.46-2.38 (m, 2H), 2.31 (d, J=5.2 Hz, 2H), 2.09-1.92 (m, 6H), 1.75-1.70 (m, 13H), 1.61-1.51 (m, 3H); LC-MS (ESI+) m/z 1048.0 (M+H)$^+$.

Example 86. Synthesis of Compound 082

(a) Step 1—3-[3-Methyl-2-oxo-5-[1-(4-piperidylmethyl)-4-piperidyl]benzimidazol-1-yl]piperidine-2,6-dione To a solution of tert-butyl 4-[[4-[1-(2,6-dioxo-3-piperidyl)-3-methyl-2-oxo-benzimidazol-5-yl]-1-piperidyl]methyl]piperidine-1-carboxylate (50.0 mg, 92.6 μmol) in DCM (5 mL) was added TFA (767 mg, 6.73 mmol, 500 μL). The mixture was stirred at 25° C. for 5 mins. On completion, the mixture was concentrated in vacuo to give the title compound (50.0 mg, 97% yield, TFA salt) as white solid. LC-MS (ESI$^+$) m/z 440.1 (M+H)$^+$.

(b) Step 2—Tert-butyl 3-[2-[[(3S,8S)-3-[[4-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

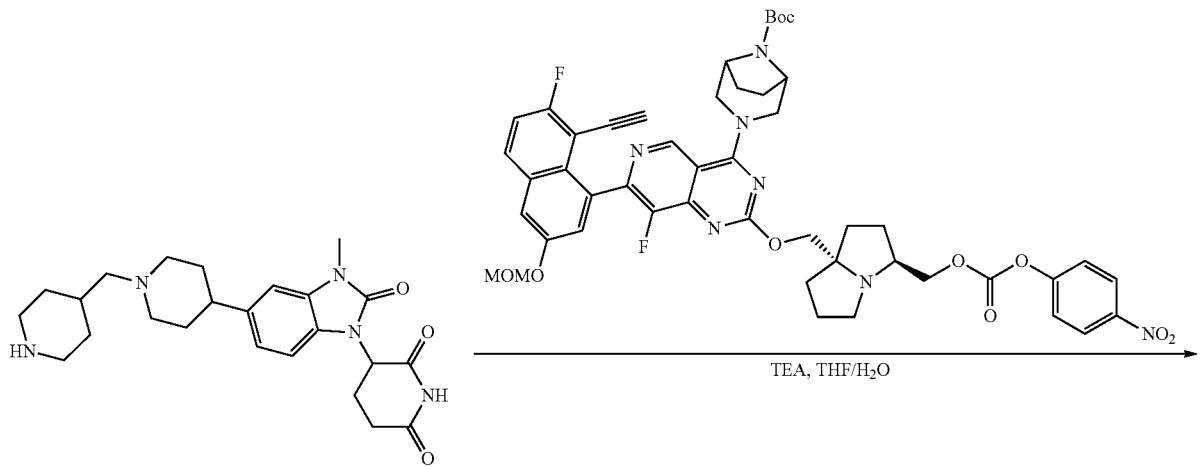

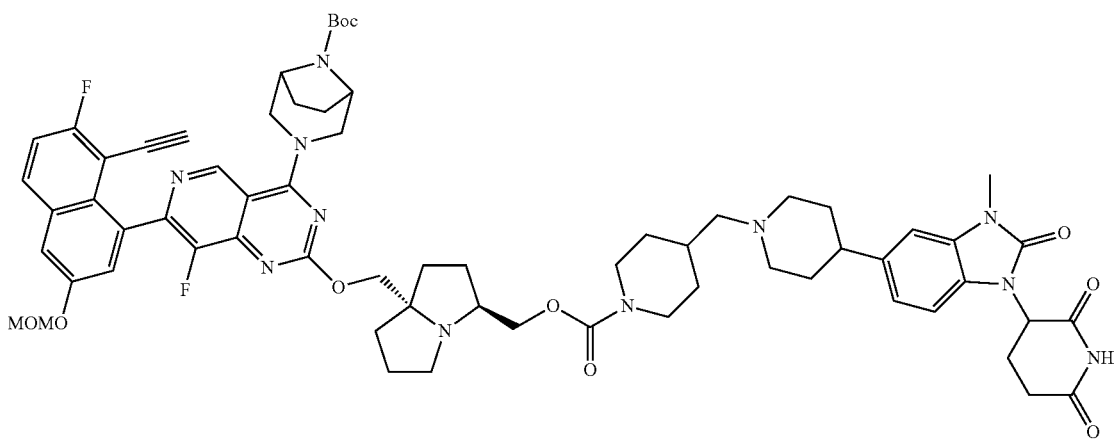

To a solution of tert-butyl 3-[7-[8-ethynyl-7-fluoro-3-(methoxymethoxy)-1-naphthyl]-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (60.0 mg, 65.0 µmol) in THF (4 mL) and H$_2$O (4 mL) was added TEA (19.7 mg, 195 µmol, 27.1 µL) and 3-[3-methyl-2-oxo-5-[1-(4-piperidylmethyl)-4-piperidyl]benzimidazol-1-yl]piperidine-2,6-dione (42.9 mg, 97.6 µmol, TFA salt). The mixture was stirred at 25° C. for 0.5 hr. On completion, the mixture was concentrated in vacuo. The crude product was purified by reversed-phase HPLC (column: Phenomenex luna C18 150*25 mm*10 um; mobile phase: [water (FA)-ACN]; gradient: 18%-48% B over 11 min) to give the title compound (30.0 mg, 37% yield) as white solid. LC-MS (ESI$^+$) m/z 1222.3 (M+H)$^+$.

(c) Step 3—[(3S,8S)-8-[[4-(3,8-Diazabicyclo[3.2.1]
octan-3-yl)-7-(8-ethynyl-7-fluoro-3-hydroxy-1-naph-
thyl)-8-fluoro-pyrido[4,3-d]pyrimidin-2-yl]oxym-
ethyl]-1,2,3,5,6,7-hexahydropyrrolizin-3-yl]methyl
4-[[4-[1-(2,6-dioxo-3-piperidyl)-3-methyl-2-oxo-
benzimidazol-5-yl]-1-piperidyl]methyl] piperidine-
1-carboxylate (082)

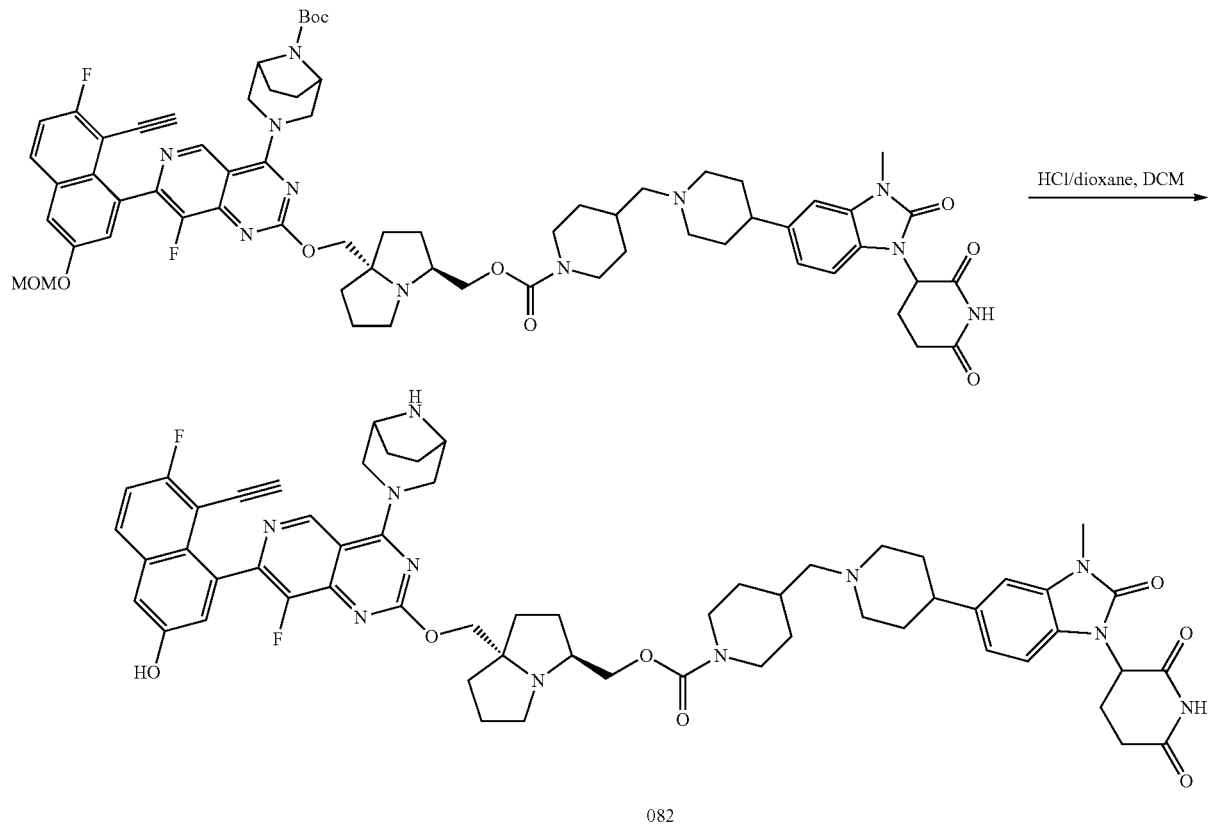

082

To a solution of tert-butyl 3-[2-[[(3S,8S)-3-[[4-[[4-[1-(2,6-dioxo-3-piperidyl)-3-methyl-2-oxo-benzimidazol-5-yl]-1-piperidyl]methyl]piperidine-1-carbonyl]oxymethyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (30.0 mg, 24.5 µmol) in DCM (5 mL) was added HCl/dioxane (4 M, 1.50 mL). The mixture was stirred at 25° C. for 10 mins. On completion, the mixture was concentrated in vacuo. The residue was purified by prep-HPLC (column: Phenomenex luna C18 150*25 mm*10 um; mobile phase: [water (FA)-ACN]; gradient: 0%-29% B over 11 min) to give the title compound (12.8 mg, 45% yield, FA salt) as yellow solid. $^1$H NMR (400 MHz, DMSO-d$_6$) δ 11.09 (s, 1H), 9.06 (s, 1H), 8.20 (s, 1H), 7.99-7.95 (m, 1H), 7.46 (t, J=9.2 Hz, 1H), 7.39 (d, J=2.4 Hz, 1H), 7.18 (d, J=2.4 Hz, 1H), 7.09 (s, 1H), 7.03-6.97 (m, 1H), 6.91-6.89 (m, 1H), 5.34 (dd, J=5.2, 12.8 Hz, 1H), 4.52 (d, J=12.2 Hz, 1H), 4.38-4.35 (m, 1H), 4.22-4.20 (m, 2H), 4.17-4.14 (m, 2H), 4.09-4.07 (m, 2H), 3.98-3.96 (m, 2H), 3.94 (s, 2H), 3.71 (s, 2H), 3.67-3.62 (m, 2H), 3.33 (s, 3H), 2.95-2.61 (m, 10H), 2.15 (d, J=6.0 Hz, 2H), 2.07-2.04 (m, 1H), 2.02-1.93 (m, 3H), 1.79-1.65 (m, 16H), 1.58-1.50 (m, 1H), 1.04-0.89 (m, 2H); LC-MS (ESI$^+$) m/z 1078.2 (M+H)$^+$.

Example 87. Synthesis of Compounds 029-032, 083-085, 087-136, 144 and 145

The following compounds were synthesized from appropriate starting materials using appropriate reagents in accordance with the procedures described herein:

[(3S,8S)-8-[[4-(3, example 208-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl N-[8-[1-(2,6-dioxo-3-piperidyl)-3-methyl-2-oxo-benzimidazol-5-yl]octyl]carbamate (029). $^1$H NMR (400 MHz, DMSO-d$_6$) δ 11.09 (s, 1H), 9.06 (s, 1H), 8.26-8.21 (m, 1H), 8.19 (s, 2H), 7.74-7.57 (m, 3H), 7.21-7.15 (m, 1H), 7.03-6.96 (m, 2H), 6.84 (d, J=8.4 Hz, 1H), 5.33 (dd, J=5.6, 12.8 Hz, 1H), 4.49 (d, J=11.6 Hz, 1H), 4.39-4.29 (m, 1H), 4.17-4.08 (m, 3H), 4.06-4.00 (m, 2H), 3.64 (s, 4H), 2.99-2.90 (m, 3H), 2.74 (d, J=4.4 Hz, 2H), 2.68 (d, J=1.9 Hz, 2H), 2.63 (d, J=4.9 Hz, 2H), 2.58 (s, 3H), 2.07-1.96 (m, 2H), 1.84-1.65 (m, 10H), 1.62-1.52 (m, 3H), 1.41-1.35 (m, 2H), 1.26 (d, J=12.4 Hz, 9H). LC-MS (ESI$^+$) m/z 1009.5 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]

methyl 4-[3-[1-(2,6-dioxo-3-piperidyl)-3-methyl-2-oxo-benzimidazol-4-yl]prop-2-ynoxy]piperidine-1-carboxylate (030). $^1$H NMR (400 MHz, DMSO-d$_6$) δ 11.12 (s, 1H), 9.04 (s, 1H), 8.24-8.17 (m, 2H), 7.72-7.57 (m, 3H), 7.17 (d, J=7.6 Hz, 1H), 7.11 (d, J=7.2 Hz, 1H), 7.02 (t, J=1.6 Hz, 1H), 5.42-5.37 (m, 1H), 4.51-4.43 (m, 3H), 4.32 (d, J=11.2 Hz, 1H), 4.26-4.19 (m, 1H), 4.16-4.09 (m, 2H), 4.07-4.00 (m, 2H), 3.77-3.72 (m, 1H), 3.70-3.60 (m, 6H), 3.59-3.54 (m, 3H), 3.28-3.25 (m, 1H), 3.15-3.10 (m, 2H), 2.96-2.83 (m, 1H), 2.77-2.63 (m, 4H), 2.06-1.98 (m, 2H), 1.88-1.84 (m, 2H), 1.81-1.59 (m, 11H), 1.54-1.47 (m, 1H), 1.45-1.36 (m, 2H); LC-MS (ESI$^+$) m/z 1019.5 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[3-[1-(2,6-dioxo-3-piperidyl)-3-methyl-2-oxo-benzimidazol-4-yl]propoxy]piperidine-1-carboxylate (031). $^1$H NMR (400 MHz, DMSO-d$_6$) δ 11.10 (s, 1H), 9.05 (s, 1H), 8.25-8.21 (m, 1H), 8.21-8.17 (m, 1H), 7.72-7.66 (m, 1H), 7.65-7.56 (m, 2H), 7.00-6.90 (m, 2H), 6.89-6.82 (m, 1H), 5.36 (dd, J=5.2, 12.8 Hz, 1H), 4.48 (d, J=11.6 Hz, 1H), 4.34 (d, J=11.6 Hz, 1H), 4.25-4.19 (m, 1H), 4.17-4.11 (m, 2H), 4.07-4.03 (m, 1H), 4.02 (s, 1H), 3.67-3.61 (m, 5H), 3.55 (s, 3H), 3.46 (t, J=6.0 Hz, 4H), 3.30-3.24 (m, 1H), 3.15-3.07 (m, 2H), 2.97-2.92 (m, 2H), 2.91-2.83 (m, 1H), 2.78-2.57 (m, 5H), 2.07-1.96 (m, 2H), 1.86-1.61 (m, 14H), 1.55-1.46 (m, 1H), 1.41-1.32 (m, 2H); LC-MS (ESI$^+$) m/z 1023.5 (M+H)$^+$.

[(3S,8S)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate (032). $^1$H NMR (400 MHz, DMSO-d$_6$) δ 11.10 (s, 1H), 9.04 (s, 1H), 8.22 (s, 1H), 8.00-7.93 (m, 1H), 7.49-7.42 (m, 1H), 7.38 (d, J=2.4 Hz, 1H), 7.17 (d, J=2.4 Hz, 1H), 6.99-6.91 (m, 2H), 6.89-6.82 (m, 1H), 5.39-5.32 (m, 1H), 4.52-4.46 (m, 1H), 4.35-4.30 (m, 1H), 4.25-4.20 (m, 1H), 4.16-4.11 (m, 2H), 4.07-4.03 (m, 1H), 3.93 (s, 1H), 3.66-3.61 (m, 5H), 3.55 (s, 3H), 3.49-3.44 (m, 4H), 3.29-3.26 (m, 1H), 3.13-3.08 (m, 2H), 2.97-2.93 (m, 2H), 2.77-2.73 (m, 2H), 2.72-2.70 (m, 1H), 2.65-2.62 (m, 1H), 2.59 (s, 1H), 2.04-1.96 (m, 2H), 1.82-1.65 (m, 15H), 1.55-1.49 (m, 1H), 1.41-1.33 (m, 2H); LC-MS (ESI$^+$) m/z 1039.4 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl3-[[1-[[1-(2,6-dioxo-3-piperidyl)-3-methyl2-oxo-benzimidazol-4-yl]methyl]-4-piperidyl]oxy]azetidine-1-carboxylate (083). $^1$H NMR (400 MHz, DMSO-d$_6$) δ 11.19-11.04 (m, 1H), 9.07 (s, 1H), 8.24-8.22 (m, 1H), 8.21-8.17 (m, 1H), 7.73-7.55 (m, 3H), 7.09-7.02 (m, 1H), 6.94 (t, J=7.6 Hz, 1H), 6.85 (d, J=7.6 Hz, 1H), 5.37 (dd, J=5.6, 12.4 Hz, 1H), 4.46 (d, J=10.8 Hz, 1H), 4.41-4.36 (m, 1H), 4.34-4.31 (m, 1H), 4.23-4.15 (m, 1H), 4.14-4.05 (m, 4H), 4.05-3.99 (m, 2H), 3.71-3.68 (m, 1H), 3.65 (s, 3H), 3.62-3.54 (m, 6H), 3.24-3.22 (m, 1H), 2.89-2.84 (m, 1H), 2.74-2.64 (m, 6H), 2.60-2.58 (m, 1H), 2.13-1.97 (m, 5H), 1.80-1.59 (m, 13H), 1.51-1.45 (m, 1H), 1.44-1.35 (m, 2H); LC-MS (ESI$^+$) m/z 1050.6 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[2-[4-[[1-(2,6-dioxo-3-piperidyl)-3-methyl-2-oxo-benzimidazol-4-yl]methyl]piperazin-1-yl]ethyl]piperidine-1-carboxylate (084). $^1$H NMR (400 MHz, DMSO-d$_6$) δ 11.10 (s, 1H), 9.05 (s, 1H), 8.23 (d, J=6.0 Hz, 1H), 8.17 (d, J=1.2 Hz, 1H), 7.74-7.52 (m, 3H), 7.06 (d, J=7.6 Hz, 1H), 6.99-6.90 (m, 1H), 6.86 (d, J=7.2 Hz, 1H), 5.46-5.27 (m, 1H), 4.48 (d, J=12.0 Hz, 1H), 4.34 (d, J=10.4 Hz, 1H), 4.20 (dd, J=7.2, 10.4 Hz, 1H), 4.16-4.10 (m, 2H), 4.05 (d, J=10.4 Hz, 1H), 4.01 (s, 1H), 3.92 (d, J=12.0 Hz, 2H), 3.67-3.58 (m, 12H), 3.30-3.23 (m, 2H), 2.95-2.81 (m, 2H), 2.80-2.61 (m, 6H), 2.42-2.31 (m, 4H), 2.27-2.22 (m, 2H), 2.08-1.97 (m, 2H), 1.86-1.56 (m, 12H), 1.55-1.39 (m, 2H), 1.37-1.24 (m, 2H), 1.08-0.88 (m, 2H); LC-MS (ESI$^+$) m/z 1091.5 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[2-[1-[[1-(2,6-dioxo-3-piperidyl)-3-methyl-2-oxo-benzimidazol-4-yl]methyl]-4-piperidyl]ethyl]piperazine-1-carboxylate (085). $^1$H NMR (400 MHz, DMSO-d$_6$) δ 11.10 (s, 1H), 9.09 (s, 1H), 8.30-8.18 (m, 2H), 7.76-7.54 (m, 3H), 7.06 (d, J=7.6 Hz, 1H), 6.94 (t, J=7.6 Hz, 1H), 6.85 (d, J=7.6 Hz, 1H), 5.45-5.28 (m, 1H), 4.62-4.52 (m, 1H), 4.42 (d, J=13.6 Hz, 1H), 4.27-4.10 (m, 4H), 4.01 (s, 1H), 3.89 (s, 2H), 3.79-3.67 (m, 4H), 3.65 (s, 3H), 3.62-3.54 (m, 4H), 3.51-3.48 (m, 1H), 3.37 (s, 2H), 2.95-2.60 (m, 8H), 2.28 (s, 4H), 2.11-2.05 (m, 1H), 2.04-1.98 (m, 1H), 1.92 (t, J=11.6 Hz, 2H), 1.84-1.55 (m, 12H), 1.36-1.22 (m, 4H), 1.14-0.99 (m, 2H); LC-MS (ESI$^+$) m/z 1091.6 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[4-[[1-(2,6-dioxo-3-piperidyl)-3-methyl-2-oxo-benzimidazol-5-yl]methyl]piperazin-1-yl]ethyl]piperidine-1-carboxylate (087). $^1$H NMR (400 MHz, DMSO-d$_6$) δ 11.17-11.02 (m, 1H), 9.05 (s, 1H), 8.22 (d, J=3.2 Hz, 1H), 8.19 (dd, J=1.2, 8.4 Hz, 1H), 7.72-7.56 (m, 3H), 7.08 (s, 1H), 7.04 (d, J=8.0 Hz, 1H), 6.95 (d, J=8.0 Hz, 1H), 5.35 (dd, J=5.6, 12.8 Hz, 1H), 4.48 (d, J=11.2 Hz, 1H), 4.34 (d, J=12.0 Hz, 1H), 4.23-4.10 (m, 4H), 4.06-4.01 (m, 2H), 3.94-3.90 (m, 2H), 3.67-3.58 (m, 6H), 3.45 (s, 2H), 3.32 (s, 3H), 3.26 (d, J=4.0 Hz, 2H), 2.94-2.85 (m, 1H), 2.78-2.62 (m, 6H), 2.34 (d, J=5.2 Hz, 4H), 2.28-2.24 (m, 2H), 2.06-1.98 (m, 2H), 1.78-1.59 (m, 12H), 1.55-1.37 (m, 3H), 1.35-1.28 (m, 2H), 1.04-0.92 (m, 2H); LC-MS (ESI$^+$) m/z 1091.6 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[1-[[1-(2,6-dioxo-3-piperidyl)-3-methyl-2-oxo-benzimidazol-5-yl]methyl]-4-piperidyl]ethyl]piperazine-1-carboxylate (088). $^1$H NMR (400 MHz, DMSO-d$_6$) δ 11.13 (s, 1H), 9.16 (s, 1H), 8.28-8.21 (m, 2H), 7.74-7.60 (m, 3H), 7.50-7.44 (m, 1H), 7.25-7.18 (m, 2H), 5.42 (dd, J=5.2, 12.4 Hz, 1H), 4.72-4.55 (m, 4H), 4.49-4.12 (m, 8H), 4.11-3.91 (m, 5H), 3.36 (s, 3H), 3.33 (s, 3H), 2.98-2.76 (m, 5H), 2.76-2.59 (m, 4H), 2.39-2.24 (m, 2H), 2.23-1.87 (m, 15H), 1.85-1.77 (m, 2H), 1.70-1.34 (m, 6H); LC-MS (ESI$^+$) m/z 1091.5 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 3-[[1-[[1-(2,6-dioxo-3-piperidyl)-3-methyl-2-oxo-benzimidazol-5-yl]methyl]-4-piperidyl]oxy]azetidine-1-carboxylate (089). $^1$H NMR (400 MHz, DMSO-d$_6$) δ 11.10 (s, 1H), 9.06 (s, 1H), 8.24 (d, J=6.0 Hz, 1H), 8.18 (d, J=1.2 Hz, 1H), 7.71-7.58 (m, 3H), 7.08 (s, 1H), 7.05-7.01 (m, 1H), 6.94 (d, J=8.0 Hz, 1H), 5.35 (dd, J=5.2, 12.8 Hz, 1H), 4.49 (d, J=12.0 Hz, 1H), 4.38-4.33 (m, 1H), 4.22-4.15 (m, 2H), 4.12-4.06 (m, 4H), 4.04-4.01 (m, 2H), 3.68 (s, 5H), 3.45 (s, 2H), 3.32 (s, 3H), 3.28-3.20 (m, 2H), 2.96-2.84 (m, 1H), 2.75 (d, J=4.0 Hz, 1H), 2.72-2.63 (m, 4H), 2.03 (t, J=9.6 Hz, 4H), 1.77-1.67 (m, 12H), 1.55-1.36 (m, 5H). LC-MS (ESI⁺) m/z 1050.8 (M+H)⁺.

((3S,7aS)-7a-(((4-((1R,5S)-3,8-Diazabicyclo[3.2.1]octan-3-yl)-7-(8-ethynyl-7-fluoronaphthalen-1-yl)-8-fluoro-pyrido[4,3-d]pyrimidin-2-yl)oxy)methyl)hexahydro-1H-pyrrolizin-3-yl)methyl4-((1-(1-(2,6-dioxopiperidin-3-yl)-3-methyl-2-oxo-2,3-dihydro-1H-benzo[d]imidazol-5-yl)piperidin-4-yl)methyl)piperidine-1-carboxylate (090). ¹H NMR (400 MHz, DMSO-d₆) δ 11.07 (s, 1H), 9.06 (s, 1H), 8.24 (s, 1H), 8.19 (d, J=9.2 Hz, 1H), 7.76-7.51 (m, 3H), 6.91 (d, J=8.4 Hz, 1H), 6.80 (s, 1H), 6.66-6.55 (m, 1H), 5.28 (dd, J=5.2, 12.8 Hz, 1H), 4.49 (d, J=11.6 Hz, 1H), 4.35 (d, J=12.4 Hz, 1H), 4.25-4.12 (m, 3H), 4.08-4.02 (m, 2H), 3.95 (d, J=10.0 Hz, 2H), 3.66 (s, 4H), 3.54 (d, J=10.8 Hz, 2H), 3.29 (s, 4H), 2.96-2.84 (m, 1H), 2.81-2.68 (m, 4H), 2.66-2.51 (m, 4H), 2.08-1.93 (m, 2H), 1.83-1.37 (m, 18H), 1.28-1.12 (m, 4H), 1.01-0.89 (m, 2H); LC-MS (ESI⁺) m/z 1062.5 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[[4-[3-methyl-1-(1-methyl-2,6-dioxo-3-piperidyl)-2-oxo-benzimidazol-5-yl]-1-piperidyl]methyl]piperidine-1-carboxylate (091). ¹H NMR (400 MHz, DMSO-d₆) δ 9.04 (s, 1H), 8.29-8.11 (m, 2H), 7.76-7.53 (m, 3H), 7.09 (s, 1H), 7.00 (d, J=8.0 Hz, 1H), 6.88 (d, J=7.6 Hz, 1H), 5.40 (dd, J=5.2, 13.2 Hz, 1H), 4.46 (d, J=11.6 Hz, 1H), 4.33 (d, J=11.6 Hz, 1H), 4.25-4.17 (m, 1H), 4.16-4.10 (m, 2H), 4.06-4.00 (m, 2H), 3.97-3.94 (m, 2H), 3.66-3.58 (m, 2H), 3.55 (s, 2H), 3.32 (s, 3H), 3.27-3.23 (m, 2H), 3.03 (s, 3H), 3.00-2.88 (m, 3H), 2.83-2.69 (m, 5H), 2.12 (d, J=6.8 Hz, 2H), 2.07-1.87 (m, 5H), 1.85-1.56 (m, 18H), 1.54-1.48 (m, 1H), 1.02-0.89 (m, 2H); LC-MS (ESI⁺) m/z 1076.6 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[5-[1-(2,6-dioxo-3-piperidyl)-3-methyl-2-oxo-benzimidazol-5-yl]penta-2,4-diynoxy]piperidine-1-carboxylate (092). ¹H NMR (400 MHz, DMSO-d₆) δ 11.14 (s, 1H), 9.06 (s, 1H), 8.25-8.21 (m, 1H), 8.18 (s, 1H), 7.74-7.52 (m, 3H), 7.46 (s, 1H), 7.32-7.13 (m, 2H), 5.41 (dd, J=5.2, 12.8 Hz, 1H), 4.50 (d, J=12.0 Hz, 1H), 4.41 (s, 2H), 4.36 (d, J=12.0 Hz, 1H), 4.25-4.20 (m, 1H), 4.17-4.14 (m, 2H), 4.07 (d, J=10.4 Hz, 1H), 4.02 (s, 1H), 3.73-3.58 (m, 8H), 3.34 (s, 3H), 3.30 (s, 1H), 3.13 (s, 2H), 2.93-2.83 (m, 1H), 2.79-2.59 (m, 4H), 2.10-2.00 (m, 2H), 1.89-1.64 (m, 12H), 1.57-1.48 (m, 1H), 1.43-1.32 (m, 2H); LC-MS (ESI⁺) m/z 1043.4 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[5-[1-(2,6-dioxo-3-piperidyl)-3-methyl-2-oxo-benzimidazol-4-yl]penta-2,4-diynoxy]piperidine-1-carboxylate (093). ¹H NMR (400 MHz, DMSO-d₆) δ 11.13 (s, 1H), 9.06 (s, 1H), 8.25-8.20 (m, 1H), 8.19-8.16 (m, 1H), 7.71-7.57 (m, 3H), 7.24 (dd, J=3.6, 7.6 Hz, 2H), 7.08-7.02 (m, 1H), 5.41 (dd, J=5.2, 12.8 Hz, 1H), 4.49 (d, J=12.0 Hz, 1H), 4.43 (s, 2H), 4.35 (d, J=12.0 Hz, 1H), 4.26-4.19 (m, 1H), 4.14 (d, J=10.4 Hz, 2H), 4.06 (d, J=10.4 Hz, 1H), 4.02 (s, 1H), 3.70-3.63 (m, 6H), 3.60 (s, 3H), 3.32-3.25 (m, 2H), 3.17-3.10 (m, 2H), 2.94-2.83 (m, 1H), 2.79-2.63 (m, 4H), 2.08-1.99 (m, 2H), 1.86-1.68 (m, 12H), 1.57-1.32 (m, 4H); LC-MS (ESI⁺) m/z 1043.4 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[4-[1-(2,6-dioxo-3-piperidyl)-3-methyl-2-oxo-benzimidazol-5-yl]triazol-1-yl]methyl]piperidine-1-carboxylate (094). ¹H NMR (400 MHz, DMSO-d₆) δ 11.12 (s, 1H), 9.05 (s, 1H), 8.50 (s, 1H), 8.25-8.21 (m, 1H), 8.18 (s, 1H), 7.74-7.50 (m, 5H), 7.19 (d, J=8.0 Hz, 1H), 5.40 (dd, J=5.6, 12.8 Hz, 1H), 4.48 (d, J=12.0 Hz, 1H), 4.37-4.29 (m, 3H), 4.25-4.19 (m, 1H), 4.13 (d, J=10.4 Hz, 2H), 4.05 (d, J=10.8 Hz, 1H), 4.02 (s, 1H), 3.98 (d, J=12.8 Hz, 2H), 3.67-3.62 (m, 4H), 3.39 (s, 3H), 3.30-3.24 (m, 2H), 2.95-2.88 (m, 1H), 2.79-2.65 (m, 5H), 2.11-2.00 (m, 3H), 1.78-1.46 (m, 14H), 1.20-1.08 (m, 2H); LC-MS (ESI⁺) m/z 1046.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[4-[1-(2,6-dioxo-3-piperidyl)-3-methyl-2-oxo-benzimidazol-5-yl]triazol-1-yl]ethyl]piperidine-1-carboxylate (095). ¹H NMR (400 MHz, DMSO-d₆) δ 11.13 (s, 1H), 9.05 (s, 1H), 8.55 (s, 1H), 8.23 (d, J=4.4 Hz, 1H), 8.20-8.17 (m, 1H), 7.72-7.56 (m, 4H), 7.53 (dd, J=1.2, 8.0 Hz, 1H), 7.19 (d, J=8.4 Hz, 1H), 5.40 (dd, J=5.2, 12.8 Hz, 1H), 4.51-4.39 (m, 3H), 4.33 (d, J=12.4 Hz, 1H), 4.24-4.18 (m, 1H), 4.12 (d, J=10.4 Hz, 2H), 4.07-4.00 (m, 2H), 3.94 (d, J=11.2 Hz, 2H), 3.65-3.57 (m, 6H), 3.39 (s, 3H), 3.31-3.22 (m, 2H), 2.97-2.87 (m, 1H), 2.82-2.63 (m, 6H), 2.09-1.99 (m, 2H), 1.85-1.79 (m, 2H), 1.77-1.66 (m, 10H), 1.55-1.47 (m, 1H), 1.45-1.37 (m, 1H), 1.14-1.00 (m, 2H). LC-MS (ESI⁺) m/z 1060.5 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[4-[1-(2,6-dioxo-3-piperidyl)-3-methyl-2-oxo-benzimidazol-4-yl]triazol-1-yl]methyl]piperidine-1-carboxylate (096). ¹H NMR (400 MHz, DMSO-d₆) δ 11.14 (s, 1H), 9.04 (s, 1H), 8.37 (s, 1H), 8.24-8.17 (m, 2H), 7.71-7.56 (m, 3H), 7.21 (d, J=7.6 Hz, 1H), 7.10 (t, J=7.6 Hz, 1H), 7.01 (d, J=7.2 Hz, 1H), 5.44 (dd, J=5.2, 12.8 Hz, 1H), 4.46 (d, J=10.4 Hz, 1H), 4.38-4.30 (m, 3H), 4.25-4.19 (m, 1H), 4.13-4.11 (m, 2H), 4.06-3.95 (m, 4H), 3.64-3.56 (m, 4H), 3.28-3.23 (m, 2H), 3.05 (s, 3H), 2.96-2.87 (m, 1H), 2.76-2.74 (m, 3H), 2.68-2.61 (m, 2H), 2.16-2.02 (m, 3H), 1.81-1.61 (m, 11H), 1.57-1.47 (m, 3H), 1.20-1.09 (m, 2H); LC-MS (ESI⁺) m/z 1046.6 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[2-[4-[1-(2,6-dioxo-3-piperidyl)-3-methyl-2-oxo-benzimidazol-4-yl]triazol-1-yl]ethyl]piperidine-1-carboxylate (097). ¹H NMR (400 MHz, DMSO-d₆) δ 11.19-11.07 (m, 1H), 9.05 (s, 1H), 8.41 (s, 1H), 8.24-8.21 (m, 1H), 8.18 (dd, J=1.6, 8.0 Hz, 1H), 7.71-7.66 (m, 1H), 7.66-7.63 (m, 1H), 7.60 (t, J=9.2 Hz, 1H), 7.21 (d, J=8.0 Hz, 1H), 7.14-7.07 (m, 1H), 7.00 (d, J=7.6 Hz, 1H), 5.44 (dd, J=5.4, 12.8 Hz, 1H), 4.48 (t, J=6.8 Hz, 3H), 4.33 (d, J=12.0 Hz, 1H), 4.25-4.19 (m, 1H), 4.13 (d, J=10.4 Hz, 2H), 4.07-4.00 (m, 2H), 3.99-3.91 (m, 2H), 3.66-3.58 (m, 5H), 3.05 (s, 3H), 2.98-2.85 (m, 2H), 2.82-2.69 (m, 5H), 2.62 (s, 1H), 2.09-2.00 (m, 2H), 1.84 (q, J=6.8 Hz, 2H), 1.79-1.62 (m, 12H), 1.55-1.47 (m, 1H), 1.43-1.34 (m, 1H), 1.13-1.01 (m, 2H); LC-MS (ESI⁺) m/z 1060.6 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[1-[1-(2,6-dioxo-3-piperidyl)-3-methyl-2-oxo-benzimidazol-5-yl]-4-piperidyl]oxy]piperidine-1-carboxylate (098). ¹H NMR (400 MHz, DMSO-d₆) δ 11.06 (s, 1H), 9.05 (s, 1H), 8.24 (s, 1H), 8.18 (s, 1H), 7.71-7.57 (m, 3H), 6.92 (d, J=8.4 Hz, 1H), 6.82 (d, J=1.6 Hz, 1H), 6.62

(dd, J=2.0, 8.4 Hz, 1H), 5.28 (dd, J=5.2, 12.8 Hz, 1H), 4.49 (d, J=12.0 Hz, 1H), 4.35 (d, J=12.4 Hz, 1H), 4.26-4.20 (m, 1H), 4.15 (d, J=10.0 Hz, 2H), 4.07 (d, J=10.4 Hz, 1H), 4.02 (s, 1H), 3.65 (s, 10H), 3.29 (s, 3H), 3.10 (s, 2H), 2.94-2.73 (m, 6H), 2.69-2.61 (m, 2H), 2.09-1.97 (m, 2H), 1.89 (d, J=8.4 Hz, 2H), 1.82-1.67 (m, 12H), 1.62-1.47 (m, 4H), 1.40-1.31 (m, 2H). LC-MS (ESI$^+$) m/z 1064.5 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[1-[1-(2,6-dioxo-3-piperidyl)-3-methyl-2-oxo-benzimidazol-4-yl]-4-piperidyl]oxy]piperidine-1-carboxylate (099). $^1$H NMR (400 MHz, DMSO-d$_6$) δ 11.09 (s, 1H), 9.06 (s, 1H), 8.18 (d, J=8.4 Hz, 2H), 7.73-7.56 (m, 3H), 7.00-6.91 (m, 1H), 6.87 (d, J=7.2 Hz, 2H), 5.34 (dd, J=5.2, 12.8 Hz, 1H), 4.49 (d, J=12.4 Hz, 1H), 4.35 (d, J=12.8 Hz, 1H), 4.21 (d, J=7.2 Hz, 1H), 4.15 (d, J=10.4 Hz, 2H), 4.07 (d, J=10.4 Hz, 1H), 4.02 (s, 1H), 3.65 (s, 6H), 3.61 (s, 3H), 3.53-3.46 (m, 1H), 3.38-3.22 (m, 2H), 3.19-2.92 (m, 5H), 2.91-2.83 (m, 1H), 2.83-2.66 (m, 5H), 2.65-2.59 (m, 1H), 2.14-1.88 (m, 4H), 1.86-1.63 (m, 13H), 1.61-1.50 (m, 2H), 1.42-1.26 (m, 2H); LC-MS (ESI$^+$) m/z 1064.4 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[3-[1-(2,6-dioxo-3-piperidyl)-3-methyl-2-oxo-benzimidazol-4-yl]oxyazetidin-1-yl]methyl]piperidine-1-carboxylate (100). 1H NMR (400 MHz, DMSO-d$_6$) δ 11.09 (s, 1H), 9.05 (s, 1H), 8.22-8.17 (m, 2H), 7.77-7.51 (m, 3H), 6.94-6.87 (m, 1H), 6.76 (d, J=8.0 Hz, 1H), 6.52 (d, J=8.4 Hz, 1H), 5.33 (dd, J=5.6, 12.8 Hz, 1H), 4.95-4.80 (m, 1H), 4.48 (dd, J=12.8 Hz, 1H), 4.34 (dd, J=12.0 Hz, 1H), 4.25-4.10 (m, 4H), 4.08-3.99 (m, 3H), 3.96-3.90 (m, 2H), 3.75-3.72 (m, 2H), 3.65-3.62 (m, 4H), 3.53 (s, 3H), 3.03-2.98 (m, 2H), 2.92-2.85 (m, 1H), 2.79-2.68 (m, 4H), 2.66-2.58 (m, 2H), 2.36-2.28 (m, 2H), 2.05-1.93 (m, 2H), 1.79-1.61 (m, 11H), 1.54-1.37 (m, 2H), 1.28-1.17 (m, 1H), 1.04-0.89 (m, 2H); LC-MS (ESI$^+$) m/z 1050.4 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 3-[[1-[1-(2,6-dioxo-3-piperidyl)-3-methyl-2-oxo-benzimidazol-5-yl]-4-piperidyl]methoxy]azetidine-1-carboxylate (101). $^1$H NMR (400 MHz, DMSO-d$_6$) δ 11.13-10.99 (m, 1H), 9.06 (s, 1H), 8.24-8.17 (m, 3H), 7.77-7.53 (m, 3H), 6.92 (d, J=8.4 Hz, 1H), 6.81 (s, 1H), 6.61 (d, J=8.4 Hz, 1H), 5.33-5.24 (m, 1H), 4.53-4.46 (m, 1H), 4.38-4.33 (m, 1H), 4.27-4.23 (m, 1H), 4.21-4.17 (m, 1H), 4.12-4.06 (m, 4H), 4.04-4.00 (m, 2H), 3.73-3.65 (m, 6H), 3.61-3.54 (m, 4H), 3.29 (s, 3H), 3.23 (d, J=6.0 Hz, 2H), 2.92-2.84 (m, 1H), 2.77-2.67 (m, 3H), 2.63-2.57 (m, 3H), 2.07-1.96 (m, 2H), 1.79-1.69 (m, 10H), 1.57-1.44 (m, 2H), 1.37-1.22 (m, 3H); LC-MS (ESI$^+$) m/z 1050.6 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[[1-[1-(2,6-dioxo-3-piperidyl)-3-methyl-2-oxo-benzimidazol-5-yl]azetidin-3-yl]oxymethyl]piperidine-1-carboxylate (102). $^1$H NMR (400 MHz, DMSO-d$_6$) δ 11.03 (s, 1H), 9.05 (s, 1H), 8.24-8.22 (m, 1H), 8.20-8.17 (m, 1H), 7.71-7.57 (m, 3H), 6.90 (d, J=8.4 Hz, 1H), 6.31 (d, J=2.0 Hz, 1H), 6.10 (dd, J=2.0, 8.4 Hz, 1H), 5.26 (dd, J=5.6, 12.8 Hz, 1H), 4.48 (d, J=10.8 Hz, 1H), 4.38-4.31 (m, 2H), 4.24-4.18 (m, 1H), 4.14 (d, J=10.4 Hz, 2H), 4.03 (d, J=6.4 Hz, 2H), 4.02-3.99 (m, 2H), 3.96 (d, J=13.2 Hz, 2H), 3.66-3.58 (m, 6H), 3.52-3.48 (m, 3H), 3.27 (s, 3H), 3.23 (d, J=6.0 Hz, 2H), 2.92-2.83 (m, 1H), 2.78-2.70 (m, 3H), 2.69-2.66 (m, 1H), 2.65-2.61 (m, 1H), 2.07-2.01 (m, 1H), 2.00-1.94 (m, 1H), 1.83-1.58 (m, 14H), 1.55-1.46 (m, 1H), 1.12-0.99 (m, 2H); LC-MS (ESI$^+$) m/z 1051.4 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl8-[[4-[1-(2,6-dioxo-3-piperidyl)-3-methyl-2-oxo-benzimidazol-5-yl]-1-piperidyl]methyl]-3-azabicyclo[3.2.1]octane-3-carboxylate (103). $^1$H NMR (400 MHz, DMSO-d$_6$) δ 11.08 (s, 1H), 9.06 (s, 1H), 8.25-8.22 (m, 1H), 8.20-8.17 (m, 1H), 7.72-7.66 (m, 1H), 7.66-7.56 (m, 2H), 7.09 (s, 1H), 7.03-6.96 (m, 1H), 6.93-6.88 (m, 1H), 5.33 (dd, J=5.2, 12.8 Hz, 1H), 4.52-4.46 (m, 1H), 4.39-4.34 (m, 1H), 4.25-4.17 (m, 2H), 4.17-4.11 (m, 2H), 4.10-4.04 (m, 2H), 4.02 (s, 1H), 3.82-3.75 (m, 2H), 3.71-3.66 (m, 3H), 3.66-3.60 (m, 2H), 3.56-3.43 (m, 2H), 3.29-3.24 (m, 1H), 3.22-3.11 (m, 2H), 3.08-2.96 (m, 2H), 2.94-2.84 (m, 2H), 2.84-2.76 (m, 2H), 2.76-2.65 (m, 2H), 2.65-2.56 (m, 2H), 2.14-2.03 (m, 4H), 2.02-1.98 (m, 2H), 1.98-1.88 (m, 2H), 1.83-1.77 (m, 2H), 1.75-1.70 (m, 8H), 1.70-1.62 (m, 4H), 1.54-1.40 (m, 2H), 1.34-1.29 (m, 1H); LC-MS (ESI+) m/z 1088.6 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 3-[[1-[1-(2,6-dioxo-3-piperidyl)-3-methyl-2-oxo-benzimidazol-5-yl]-4-piperidyl]oxymethyl]azetidine-1-carboxylate (104). $^1$H NMR (400 MHz, DMSO-d$_6$) δ 11.07 (s, 1H), 9.06 (s, 1H), 8.24 (s, 1H), 8.19 (d, J=8.8 Hz, 1H), 7.72-7.56 (m, 3H), 6.91 (d, J=8.4 Hz, 1H), 6.82 (d, J=1.6 Hz, 1H), 6.62 (dd, J=1.6, 8.4 Hz, 1H), 5.28 (dd, J=5.2, 12.8 Hz, 1H), 4.51 (d, J=12.0 Hz, 1H), 4.38 (s, 1H), 4.20-4.14 (m, 2H), 4.12-4.02 (m, 4H), 3.94 (s, 2H), 3.71 (s, 2H), 3.65 (d, J=12.8 Hz, 3H), 3.56 (d, J=6.4 Hz, 2H), 3.46-3.42 (m, 1H), 3.39-3.33 (m, 2H), 3.29 (s, 3H), 3.26 (s, 1H), 2.94-2.62 (m, 8H), 2.04-1.90 (m, 4H), 1.80-1.64 (m, 10H), 1.63-1.47 (m, 4H). LC-MS (ESI$^+$) m/z 1050.9 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[3-[1-(2,6-dioxo-3-piperidyl)-3-methyl-2-oxo-benzimidazol-5-yl]prop-2-ynoxy]ethyl]piperidine-1-carboxylate (105). $^1$H NMR (400 MHz, DMSO-d$_6$) δ 11.24-10.97 (m, 1H), 9.04 (s, 1H), 8.26-8.14 (m, 2H), 7.75-7.53 (m, 3H), 7.31 (s, 1H), 7.20-7.05 (m, 2H), 5.38 (dd, J=5.2, 12.4 Hz, 1H), 4.46 (d, J=11.6 Hz, 1H), 4.37-4.29 (m, 3H), 4.25-4.17 (m, 1H), 4.15-4.08 (m, 2H), 4.06-3.99 (m, 2H), 3.98-3.88 (m, 2H), 3.65-3.60 (m, 1H), 3.59-3.51 (m, 5H), 3.30-3.15 (m, 5H), 2.93-2.83 (m, 1H), 2.81-2.65 (m, 5H), 2.63-2.56 (m, 1H), 2.09-1.98 (m, 2H), 1.80-1.69 (m, 5H), 1.68-1.63 (m, 6H), 1.62-1.52 (m, 2H), 1.52-1.41 (m, 3H), 1.08-0.94 (m, 2H), LC-MS (ESI$^+$) m/z 1047.4 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[1-[[1-(2,6-dioxo-3-piperidyl)-3-methyl-2-oxo-benzimidazol-4-yl]methyl]-4-piperidyl]piperidine-1-carboxylate (106). $^1$H NMR (400 MHz, DMSO-d$_6$) δ 11.10-11.05 (m, 1H), 9.17 (s, 1H), 8.28-8.19 (m, 2H), 7.75-7.68 (m, 1H), 7.68-7.58 (m, 2H), 7.04-6.96 (m, 1H), 6.91 (d, J=1.6 Hz, 1H), 6.73-6.61 (m, 1H), 5.34-5.29 (m, 1H), 4.73-4.64 (m, 2H), 4.63-4.53 (m, 1H), 4.45-4.34 (m, 1H), 4.26-4.15 (m, 3H), 4.05 (d, J=5.6 Hz, 1H), 4.03-3.93 (m, 3H), 3.57-3.53 (m, 3H), 3.45-3.38 (m, 3H), 3.32 (s, 3H), 3.29-3.20 (m, 2H), 3.20-3.09 (m, 2H), 3.08-2.97 (m, 2H), 2.96-2.77 (m, 3H), 2.75-2.55 (m, 3H), 2.34-2.27 (m, 1H), 2.17-1.92 (m, 13H), 1.90-1.81 (m, 2H), 1.29-1.11 (m, 6H); LC-MS (ESI+) m/z 1063.6 (M+H)+.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[4-[1-(2,6-dioxo-3-piperidyl)-3-methyl-2-oxo-benzimidazol-4-yl]but-3-ynoxy]piperidine-1-carboxylate (107). ¹H NMR (400 MHz, DMSO-d₆) δ 11.20-10.97 (m, 1H), 9.04 (s, 1H), 8.25-8.15 (m, 2H), 7.72-7.56 (m, 3H), 7.11 (d, J=7.6 Hz, 1H), 7.06-6.92 (m, 2H), 5.38 (dd, J=5.2, 12.8 Hz, 1H), 4.47 (d, J=11.2 Hz, 1H), 4.33 (d, J=12.4 Hz, 1H), 4.25-4.18 (m, 1H), 4.12 (d, J=10.4 Hz, 2H), 4.06-4.00 (m, 2H), 3.69 (s, 1H), 3.65 (s, 2H), 3.63 (s, 3H), 3.62 (s, 1H), 3.60-3.54 (m, 5H), 3.26 (m, 2H), 3.09 (s, 2H), 2.94-2.83 (m, 1H), 2.75 (m, 1H), 2.74-2.66 (m, 4H), 2.65-2.58 (m, 1H), 2.07-1.96 (m, 2H), 1.81 (d, J=12.4 Hz, 2H), 1.74 (d, J=4.0 Hz, 4H), 1.71-1.60 (m, 6H), 1.53-1.44 (m, 1H), 1.41-1.32 (m, 2H); LC-MS (ESI+) m/z 1033.2 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[[[1-[1-(2,6-dioxo-3-piperidyl)-3-methyl-2-oxo-benzimidazol-4-yl]-4-piperidyl]-methyl-amino]methyl] piperidine-1-carboxylate (108). ¹H NMR (400 MHz, DMSO-d₆) δ 11.10 (s, 1H), 11.07-10.99 (m, 1H), 10.27-10.09 (m, 1H), 10.00-9.91 (m, 1H), 9.70-9.60 (m, 1H), 9.17 (s, 1H), 8.28-8.19 (m, 2H), 7.79-7.60 (m, 3H), 7.03-6.97 (m, 1H), 6.94-6.89 (m, 2H), 5.37-5.30 (m, 1H), 4.74-4.60 (m, 3H), 4.60-4.54 (m, 1H), 4.43-4.34 (m, 1H), 4.21-4.18 (m, 3H), 4.15 (s, 1H), 4.07-4.00 (m, 1H), 4.05-3.95 (m, 3H), 3.48-3.28 (m, 5H), 3.28-3.09 (m, 4H), 2.92-2.84 (m, 3H), 2.78-2.70 (m, 5H), 2.72-2.59 (m, 3H), 2.25-2.16 (m, 3H), 2.14-1.87 (m, 17H), 1.80-1.74 (m, 1H), 1.25-1.11 (m, 2H); LC-MS (ESI+) m/z 1091.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methylN-[3-[[1-[1-(2,6-dioxo-3-piperidyl)-3-methyl-2-oxo-benzimidazol-4-yl]-4-piperidyl]-methyl-amino]propyl] carbamate (109). ¹H NMR (400 MHz, DMSO-d₆) δ 11.10 (s, 1H), 11.05 (d, J=6.0 Hz, 1H), 10.79 (d, J=5.2 Hz, 1H), 10.14-10.05 (m, 1H), 9.73 (dd, J=2.4, 4.4 Hz, 1H), 9.16 (s, 1H), 8.30-8.16 (m, 2H), 7.74-7.56 (m, 3H), 7.44 (d, J=5.2 Hz, 1H), 7.00-6.94 (m, 1H), 6.93-6.86 (m, 2H), 5.37 (dd, J=5.6, 12.8 Hz, 1H), 4.75-4.51 (m, 4H), 4.42-4.26 (m, 2H), 4.20 (s, 2H), 4.11-3.98 (m, 4H), 3.97-3.90 (m, 2H), 3.62 (s, 3H), 3.49-3.29 (m, 4H), 3.28-3.18 (m, 3H), 3.11 (d, J=4.8 Hz, 4H), 2.94-2.83 (m, 1H), 2.83-2.75 (m, 2H), 2.72 (d, J=4.8 Hz, 3H), 2.65 (d, J=11.6 Hz, 1H), 2.30 (d, J=6.0 Hz, 1H), 2.16 (d, J=9.2 Hz, 2H), 2.08 (s, 3H), 2.05-1.92 (m, 10H); LC-MS (ESI+) m/z 1051.2 (M+H)+.

((3S,7aS)-7a-(((4-((1R,5S)-3,8-Diazabicyclo[3.2.1]octan-3-yl)-7-(8-ethynyl-7-fluoronaphthalen-1-yl)-8-fluoro-pyrido[4,3-d]pyrimidin-2-yl)oxy)methyl)hexahydro-1H-pyrrolizin-3-yl)methyl(4-(4-(1-(2,6-dioxopiperidin-3-yl)-3-methyl-2-oxo-2,3-dihydro-1H-benzo[d]imidazol-4-yl) piperazin-1-yl)-4-oxobutyl)carbamate (110). ¹H NMR (400 MHz, DMSO-d₆) δ 11.10 (s, 1H), 9.05 (s, 1H), 8.24 (s, 1H), 8.19 (d, J=8.4 Hz, 1H), 7.73-7.54 (m, 3H), 7.24 (t, J=4.8 Hz, 1H), 7.01-6.94 (m, 1H), 6.93-6.87 (m, 2H), 5.36 (dd, J=5.2, 12.4 Hz, 1H), 4.47 (d, J=11.2 Hz, 1H), 4.33 (d, J=12.4 Hz, 1H), 4.19-4.08 (m, 3H), 4.05-4.00 (m, 2H), 3.93-3.85 (m, 1H), 3.65-3.57 (m, 8H), 3.33-3.03 (m, 4H), 3.04-2.99 (m, 3H), 2.94-2.84 (m, 2H), 2.77-2.59 (m, 6H), 2.39-2.32 (m, 2H), 2.07-1.97 (m, 2H), 1.76-1.60 (m, 12H), 1.55-1.47 (m, 1H); LC-MS (ESI+) m/z 1051.2 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl (2S)-2-[[4-[1-(2,6-dioxo-3-piperidyl)-3-methyl-2-oxo-benzimidazol-4-yl]piperazin-1-yl]methyl]morpholine-4-carboxylate-2,6-dione (111). ¹H NMR (400 MHz, DMSO-d₆) δ 11.47-11.25 (m, 1H), 11.11 (s, 1H), 10.89-10.64 (m, 1H), 10.03-9.93 (m, 1H), 9.70-9.60 (m, 1H), 9.15 (s, 1H), 8.27-8.18 (m, 2H), 7.73-7.67 (m, 1H), 7.67-7.58 (m, 2H), 7.07-6.83 (m, 3H), 5.38 (dd, J=4.4, 12.8 Hz, 1H), 4.70 (d, J=12.0 Hz, 2H), 4.65 (d, J=2.4 Hz, 1H), 4.60-4.52 (m, 1H), 4.46-4.36 (m, 1H), 4.32-4.24 (m, 1H), 4.20 (s, 2H), 4.08 (s, 2H), 4.02-3.97 (m, 2H), 3.95-3.85 (m, 2H), 3.67-3.58 (m, 12H), 3.37-3.32 (m, 2H), 3.28-3.18 (m, 4H), 3.06-2.96 (m, 1H), 2.92-2.84 (m, 1H), 2.75-2.69 (m, 1H), 2.68-2.58 (m, 2H), 2.34-2.27 (m, 1H), 2.22-2.12 (m, 2H), 2.10-1.89 (m, 11H); LC-MS (ESI+) m/z 1065.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[4-[1-(2,6-dioxo-3-piperidyl)-3-methyl-2-oxo-benzimidazol-4-yl]piperazin-1-yl]methyl]piperidine-1-carboxylate (112). ¹H NMR (400 MHz, DMSO-d₆) δ 11.10 (s, 1H), 10.66 (dd, J=2.4, 2.8 Hz, 1H), 10.02 (d, J=9.2 Hz, 1H), 9.69 (d, J=1.6 Hz, 1H), 9.16 (s, 1H), 8.35-8.13 (m, 2H), 7.75-7.68 (m, 1H), 7.68-7.58 (m, 2H), 7.08-7.01 (m, 1H), 7.00-6.95 (m, 1H), 6.92 (d, J=7.2 Hz, 1H), 5.38 (dd, J=5.2, 12.8 Hz, 1H), 4.73-4.62 (m, 3H), 4.61-4.51 (m, 1H), 4.47-4.32 (m, 1H), 4.29-4.15 (m, 4H), 4.10-3.93 (m, 5H), 3.63 (s, 3H), 3.43-3.34 (m, 4H), 3.34-3.17 (m, 5H), 3.13-3.00 (m, 2H), 2.95-2.80 (m, 3H), 2.69-2.59 (m, 2H), 2.33-2.28 (m, 1H), 2.22-2.12 (m, 2H), 2.06 (d, J=8.4 Hz, 3H), 2.02-1.92 (m, 7H), 1.88 (d, J=12.0 Hz, 2H), 1.32-1.07 (m, 4H); LC-MS (ESI+) m/z 1063.5 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 3-[[4-[1-(2,6-dioxo-3-piperidyl)-3-methyl-2-oxo-benzimidazol-4-yl]piperazin-1-yl]methyl]azetidine-1-carboxylate (113). ¹H NMR (400 MHz, DMSO-d₆) δ 11.09 (s, 1H), 9.06 (s, 1H), 8.21-8.16 (m, 2H), 7.76-7.50 (m, 3H), 7.00-6.85 (m, 3H), 5.35 (dd, J=5.2, 12.8 Hz, 1H), 4.50 (d, J=12.0 Hz, 1H), 4.36 (d, J=12.4 Hz, 1H), 4.24-4.14 (m, 2H), 4.13-4.06 (m, 2H), 4.06-4.00 (m, 2H), 4.00-3.98 (m, 2H), 3.67 (d, J=0.8 Hz, 4H), 3.60 (s, 3H), 3.51-3.47 (m, 2H), 2.95-2.90 (m, 2H), 2.90-2.82 (m, 3H), 2.79 (d, J=7.2 Hz, 3H), 2.74-2.61 (m, 3H), 2.58 (d, J=7.2 Hz, 2H), 2.55-2.51 (m, 4H), 2.30-2.19 (m, 1H), 2.10-1.92 (m, 2H), 1.76 (d, J=2.4 Hz, 3H), 1.74-1.61 (m, 6H), 1.58-1.45 (m, 1H); LC-MS (ESI+) m/z 1035.2 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[5-[1-(2,6-dioxo-3-piperidyl)-3-methyl-2-oxo-benzimidazol-5-yl]pent-4-ynoxy]piperidine-1-carboxylate (114). ¹H NMR (400 MHz, DMSO-d₆) δ 11.13 (s, 1H), 9.05 (s, 1H), 8.25-8.15 (m, 2H), 7.75-7.55 (m, 3H), 7.23 (s, 1H), 7.08 (s, 2H), 5.37 (dd, J=5.2, 12.8 Hz, 1H), 4.46 (d, J=12.0 Hz, 1H), 4.33 (d, J=12.4 Hz, 1H), 4.26-4.17 (m, 1H), 4.12 (d, J=10.4 Hz, 2H), 4.07-4.00 (m, 2H), 3.64-3.56 (m, 6H), 3.54-3.51 (m, 2H), 3.47 (dd, J=4.0, 7.2 Hz, 2H), 3.32 (s, 3H), 3.13 (d, J=9.6 Hz, 2H), 2.93-2.83 (m, 1H), 2.79-2.61 (m, 4H), 2.48-2.43 (m, 2H), 2.09-1.96 (m, 2H), 1.85-1.69 (m, 10H), 1.68-1.61 (m, 5H), 1.53-1.45 (m, 1H), 1.42-1.32 (m, 2H); LC-MS (ESI+) m/z 1047.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-5-yl]prop-2-ynoxy]piperidine-1-carboxylate (115). $^1$H NMR (400 MHz, DMSO-d$_6$) δ 11.23-10.97 (m, 1H), 9.05 (s, 1H), 8.24-8.17 (m, 2H), 7.73-7.57 (m, 3H), 7.32 (s, 1H), 7.18-7.09 (m, 2H), 5.38 (dd, J=5.2, 12.8 Hz, 1H), 4.46 (d, J=11.2 Hz, 1H), 4.42 (s, 2H), 4.33 (d, J=12.0 Hz, 1H), 4.27-4.19 (m, 1H), 4.18-4.09 (m, 2H), 4.07-4.00 (m, 2H), 3.74-3.71 (m, 1H), 3.67-3.61 (m, 3H), 3.60-3.55 (m, 4H), 3.33 (s, 3H), 3.17-3.13 (m, 2H), 2.90-2.84 (m, 1H), 2.77-2.70 (m, 2H), 2.69-2.58 (m, 2H), 2.06-1.99 (m, 2H), 1.87-1.80 (m, 2H), 1.79-1.61 (m, 11H), 1.53-1.46 (m, 1H), 1.42 (dd, J=4.0, 8.4 Hz, 2H); LC-MS (ESI$^+$) m/z 1019.4 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[[1-(2,6-dioxo-3-piperidyl)-3-methyl-2-oxo-benzimidazol-5-yl]methoxy]piperidine-1-carboxylate (116). $^1$H NMR (400 MHz, DMSO-d$_6$) δ 11.10 (s, 1H), 9.05 (s, 1H), 8.26-8.20 (m, 2H), 8.20-8.17 (m, 1H), 7.68-7.65 (m, 1H), 7.63-7.58 (m, 1H), 7.14 (s, 1H), 7.09-7.05 (m, 1H), 7.04-6.98 (m, 1H), 5.39-5.33 (m, 1H), 4.52 (s, 2H), 4.49-4.44 (m, 1H), 4.36-4.31 (m, 1H), 4.25-4.19 (m, 1H), 4.16-4.10 (m, 2H), 4.07-4.03 (m, 1H), 4.01 (s, 1H), 3.66-3.57 (m, 8H), 3.33 (s, 3H), 3.29-3.24 (m, 2H), 3.14-3.08 (m, 2H), 2.93-2.85 (m, 1H), 2.77-2.70 (m, 2H), 2.65-2.59 (m, 1H), 2.06-1.97 (m, 2H), 1.86-1.62 (m, 12H), 1.55-1.48 (m, 1H), 1.47-1.37 (m, 2H); LC-MS (ESI$^+$) m/z 995.1 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[4-[1-(2,6-dioxo-3-piperidyl)-3-methyl-2-oxo-benzimidazol-4-yl]butoxy]piperidine-1-carboxylate (117). $^1$H NMR (400 MHz, DMSO-d$_6$) δ 11.09 (s, 1H), 9.05 (s, 1H), 8.25-8.20 (m, 2H), 8.20-8.16 (m, 1H), 7.69-7.65 (m, 1H), 7.60 (t, J=8.8 Hz, 1H), 7.00-6.91 (m, 2H), 6.88-6.83 (m, 1H), 5.40-5.32 (m, 1H), 4.47 (d, J=11.2 Hz, 1H), 4.33 (d, J=11.6 Hz, 1H), 4.24-4.19 (m, 1H), 4.16-4.10 (m, 2H), 4.04 (d, J=10.4 Hz, 2H), 4.01 (s, 1H), 3.66-3.60 (m, 6H), 3.54 (s, 3H), 3.45-3.42 (m, 4H), 3.29-3.23 (m, 2H), 3.10-3.03 (m, 2H), 2.91-2.83 (m, 3H), 2.77-2.69 (m, 2H), 2.65-2.59 (m, 1H), 2.06-1.96 (m, 2H), 1.78-1.59 (m, 16H), 1.52-1.45 (m, 1H), 1.37-1.28 (m, 2H); LC-MS (ESI$^+$) m/z 1037.1 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[4-[1-(2,6-dioxo-3-piperidyl)-3-methyl-2-oxo-benzimidazol-5-yl]butoxy]piperidine-1-carboxylate (118). $^1$H NMR (400 MHz, DMSO-d$_6$) δ 11.23-10.91 (m, 1H), 9.05 (s, 1H), 8.23-8.17 (m, 2H), 7.76-7.51 (m, 3H), 7.06-6.94 (m, 2H), 6.85 (d, J=8.0 Hz, 1H), 5.33 (dd, J=5.6, 12.4 Hz, 1H), 4.47 (d, J=11.2 Hz, 1H), 4.33 (d, J=12.4 Hz, 1H), 4.25-4.17 (m, 1H), 4.13 (d, J=10.4 Hz, 2H), 4.07-4.00 (m, 2H), 3.64 (d, J=4.4 Hz, 2H), 3.60 (s, 2H), 3.40 (t, J=6.4 Hz, 4H), 3.31 (s, 3H), 3.27 (d, J=3.2 Hz, 2H), 3.11-3.05 (m, 2H), 2.94-2.83 (m, 1H), 2.76-2.58 (m, 6H), 2.09-1.93 (m, 2H), 1.79-1.59 (m, 14H), 1.58-1.42 (m, 4H), 1.37-1.27 (m, 2H); LC-MS (ESI$^+$) m/z 1037.3 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[5-[1-(2,6-dioxo-3-piperidyl)-3-methyl-2-oxo-benzimidazol-4-yl]pent-4-ynoxy]piperidine-1-carboxylate (119). $^1$H NMR (400 MHz, DMSO-d$_6$) δ 11.12 (s, 1H), 9.04 (s, 1H), 8.33-8.09 (m, 2H), 7.79-7.49 (m, 3H), 7.20-6.86 (m, 3H), 5.38 (dd, J=5.2, 12.4 Hz, 1H), 4.51-4.28 (m, 2H), 4.26-4.18 (m, 1H), 4.16-4.09 (d, J=10.4 Hz, 2H), 4.07-3.98 (m, 2H), 3.68-3.63 (m, 2H), 3.62 (s, 3H), 3.60-3.55 (m, 3H), 3.53 (t, J=6.0 Hz, 2H), 3.50-3.43 (m, 2H), 3.29-3.20 (m, 3H), 3.16-3.06 (m, 2H), 2.93-2.83 (m, 1H), 2.78-2.66 (m, 3H), 2.63-2.57 (m, 1H), 2.56-2.52 (m, 2H), 2.07-1.97 (m, 2H), 1.83-1.69 (m, 9H), 1.69-1.61 (m, 5H), 1.55-1.44 (m, 1H), 1.41-1.29 (m, 2H), LC-MS (ESI$^+$) m/z 1047.5 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl 4-[5-[1-(2,6-dioxo-3-piperidyl)-3-methyl-2-oxo-benzimidazol-5-yl]pentoxy]piperidine-1-carboxylate (120). $^1$H NMR (400 MHz, DMSO-d$_6$) δ 11.08 (s, 1H), 9.17 (s, 1H), 8.29-8.18 (m, 2H), 7.75-7.58 (m, 3H), 7.03-6.95 (m, 2H), 6.84 (d, J=8.0 Hz, 1H), 5.33 (dd, J=4.8, 12.8 Hz, 1H), 4.75-4.51 (m, 4H), 4.44-4.33 (m, 1H), 4.29-4.16 (m, 3H), 4.05-3.87 (m, 4H), 3.76-3.57 (m, 2H), 3.47-3.35 (m, 6H), 3.17-3.04 (m, 2H), 2.98-2.81 (m, 1H), 2.78-2.68 (m, 1H), 2.65-2.57 (m, 4H), 2.21-1.90 (m, 14H), 1.80-1.73 (m, 2H), 1.63-1.55 (m, 2H), 1.53-1.46 (m, 2H), 1.41-1.28 (m, 5H); LC-MS (ESI$^+$) m/z 1051.3 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 7-[1-(2,6-dioxo-3-piperidyl)-3-methyl-2-oxo-benzimidazol-4-yl]-2,7-diazaspiro[3.5]nonane-2-carboxylate (121). $^1$H NMR (400 MHz, DMSO-d$_6$) δ 11.08 (s, 1H), 9.06 (s, 1H), 8.25-8.22 (m, 1H), 8.19 (d, J=9.6 Hz, 1H), 7.82-7.51 (m, 3H), 6.94 (d, J=7.6 Hz, 1H), 6.87 (d, J=7.2 Hz, 2H), 5.34 (dd, J=5.2, 12.8 Hz, 1H), 4.51 (d, J=12.4 Hz, 1H), 4.37 (d, J=11.6 Hz, 1H), 4.27-4.17 (m, 1H), 4.17-4.10 (m, 2H), 4.10-4.04 (m, 1H), 4.02 (s, 1H), 3.75-3.61 (m, 9H), 3.60 (s, 3H), 3.29 (s, 2H), 2.98 (d, J=10.4 Hz, 2H), 2.90-2.58 (m, 8H), 2.07-1.96 (m, 2H), 1.90-1.71 (m, 12H), 1.57-1.48 (m, 1H); LC-MS (ESI$^+$) m/z 1006.4 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methyl4-[5-[1-(2,6-dioxo-3-piperidyl)-3-methyl-2-oxo-benzimidazol-4-yl]pentoxy]piperidine-1-carboxylate (122). $^1$H NMR (400 MHz, DMSO-d$_6$) δ 11.09 (s, 1H), 9.04 (s, 1H), 8.32-8.08 (m, 2H), 7.75-7.48 (m, 3H), 6.99-6.90 (m, 2H), 6.87-6.79 (m, 2H), 5.36 (dd, J=5.2, 12.8 Hz, 1H), 4.50-4.29 (m, 2H), 4.26-4.18 (m, 1H), 4.16-4.09 (m, 2H), 4.07-3.99 (m, 2H), 3.66-3.56 (m, 6H), 3.54 (s, 3H), 3.42-3.38 (m, 5H), 3.12-3.03 (m, 2H), 2.92-2.81 (m, 3H), 2.78-2.66 (m, 3H), 2.62-2.56 (m, 1H), 2.10-1.92 (m, 2H), 1.81-1.69 (m, 7H), 1.68-1.63 (m, 4H), 1.62-1.47 (m, 6H), 1.45-1.38 (m, 2H), 1.37-1.25 (m, 2H), LC-MS (ESI$^+$) m/z 1051.5 (M+H)$^+$.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl N-[2-[2-[4-[1-(2,6-dioxo-3-piperidyl)-3-methyl-2-oxo-benzimidazol-4-yl]piperazin-1-yl]ethoxy]ethyl]carbamate (123). $^1$H NMR (400 MHz, DMSO-d$_6$) δ 11.10 (s, 1H), 9.17 (s, 1H), 8.29-8.18 (m, 2H), 7.78-7.57 (m, 3H), 7.09-6.88 (m, 3H), 5.38 (dd, J=5.2, 12.8 Hz, 1H), 4.72-4.53 (m, 4H), 4.32 (d, J=4.0 Hz, 2H), 4.21 (s, 2H), 4.08-3.78 (m, 7H), 3.63 (s, 3H), 3.60-3.53 (m, 2H), 3.50 (t, J=5.2 Hz, 2H), 3.45-3.35 (m, 7H), 3.24-3.20 (m, 4H), 2.95-2.84 (m, 2H), 2.75-2.69 (m, 1H), 2.63 (d, J=4.4 Hz, 1H), 2.62-2.58 (m, 1H), 2.32-2.24 (m, 1H), 2.21-2.11 (m, 1H), 2.09-1.88 (m, 11H); LC-MS (ESI$^+$) m/z 1051.3 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 2-[2-[1-(2,6-dioxo-3-piperidyl)-3-methyl-2-oxo-benzimidazol-4-yl]ethyl]-7-azaspiro[3.5]nonane-7-carboxylate (124). ¹H NMR (400 MHz, DMSO-d₆) δ 11.09 (s, 1H), 10.71-10.62 (m, 1H), 9.81 (d, J=10.4 Hz, 1H), 9.51-9.36 (m, 1H), 9.20 (s, 1H), 8.29-8.19 (m, 2H), 7.74-7.69 (m, 1H), 7.67-7.59 (m, 2H), 6.98-6.92 (m, 2H), 6.83 (dd, J=3.2, 5.6 Hz, 1H), 5.40-5.31 (m, 1H), 4.73-4.53 (m, 4H), 4.37 (d, J=11.2 Hz, 1H), 4.27-4.18 (m, 3H), 4.06-3.90 (m, 4H), 3.54 (s, 3H), 2.92-2.61 (m, 6H), 2.33-2.26 (m, 2H), 2.18-2.10 (m, 2H), 2.04-1.91 (m, 12H), 1.75-1.68 (m, 2H), 1.57-1.33 (m, 8H), 1.28-1.19 (m, 4H); LC-MS (ESI+) m/z 1033.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methylN-[[(2R)-4-[3-[1-(2,6-dioxo-3-piperidyl)-3-methyl-2-oxo-benzimidazol-4-yl]prop-2-ynyl]morpholin-2-yl]methyl]carbamate (125). ¹H NMR (400 MHz, DMSO-d₆) δ 12.39 (s, 1H), 11.13 (s, 1H), 11.04 (s, 1H), 10.14 (s, 1H), 9.78 (s, 1H), 9.18-9.10 (m, 1H), 8.28-8.18 (m, 2H), 7.74-7.67 (m, 1H), 7.67-7.58 (m, 2H), 7.51 (d, J=5.2 Hz, 1H), 7.25 (d, J=7.6 Hz, 1H), 7.19 (d, J=8.0 Hz, 1H), 7.06 (t, J=8.0 Hz, 1H), 5.43 (dd, J=5.2, 12.4 Hz, 1H), 4.71-4.52 (m, 4H), 4.43 (s, 1H), 4.33 (d, J=4.8 Hz, 1H), 4.20 (s, 2H), 4.08-3.99 (m, 4H), 3.98-3.86 (m, 3H), 3.65 (s, 3H), 3.51-3.28 (m, 5H), 3.18 (s, 3H), 3.01-2.84 (m, 2H), 2.76-2.59 (m, 2H), 2.35-2.24 (m, 1H), 2.17-2.15 (m, 1H), 2.12-1.85 (m, 12H); LC-MS (ESI⁺) m/z 1034.2 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl N-[[(2 R)-4-[3-[1-(2,6-dioxo-3-piperidyl)-3-methyl-2-oxo-benzimidazol-4-yl]propyl]morpholin-2-yl]methyl] carbamate (126). ¹H NMR (400 MHz, DMSO-d₆) δ 11.66 (s, 1H), 11.09 (s, 1H), 11.07 (s, 1H), 10.18 (s, 1H), 9.83 (s, 1H), 9.16 (s, 1H), 8.27-8.19 (m, 2H), 7.73-7.68 (m, 1H), 7.67-7.58 (m, 2H), 7.45 (d, J=4.4 Hz, 1H), 7.04-6.94 (m, 2H), 6.92-6.87 (m, 1H), 5.39 (dd, J=5.2, 12.4 Hz, 1H), 4.71-4.53 (m, 4H), 4.33 (s, 2H), 4.19 (s, 2H), 4.10-4.02 (m, 3H), 3.98-3.86 (m, 4H), 3.58 (s, 3H), 3.50 (d, J=12.0 Hz, 1H), 3.40 (d, J=11.6 Hz, 2H), 3.21-3.07 (m, 4H), 3.01-2.89 (m, 4H), 2.81-2.79 (m, 1H), 2.72-2.58 (m, 2H), 2.34-2.25 (m, 1H), 2.16 (d, J=6.8 Hz, 1H), 2.10-1.89 (m, 14H); LC-MS (ESI⁺) m/z 1038.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[1-[1-(2,6-dioxo-3-piperidyl)-3-methyl-2-oxo-benzimidazol-4-yl]-4-piperidyl]piperidine-1-carboxylate (127). ¹H NMR (400 MHz, DMSO-d₆) δ 11.09 (s, 1H), 9.04 (s, 1H), 8.26-8.13 (m, 2H), 7.76-7.53 (m, 3H), 6.98-6.92 (m, 1H), 6.87-6.84 (m, 2H), 5.36-5.32 (m, 1H), 4.46 (d, J=11.6 Hz, 1H), 4.32 (d, J=12.8 Hz, 1H), 4.26-4.18 (m, 1H), 4.14-4.10 (m, 2H), 4.07-3.95 (m, 4H), 3.65-3.57 (m, 5H), 3.55 (s, 3H), 3.30-3.20 (m, 1H), 3.12-3.09 (m, 2H), 2.93-2.84 (m, 1H), 2.76-2.58 (m, 8H), 2.06-1.93 (m, 2H), 1.79-1.60 (m, 14H), 1.55-1.47 (m, 1H), 1.43-1.27 (m, 3H), 1.24-1.16 (m, 1H), 1.12-1.01 (m, 2H); LC-MS (ESI⁺) m/z 1048.3 (M+H)⁺.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[[1-[[1-(2,6-dioxo-3-piperidyl)-3-methyl-2-oxo-benzimidazol-4-yl]methyl]-4-piperidyl]oxymethyl]piperidine-1-carboxylate (128). ¹H NMR (400 MHz, DMSO-d₆) δ 11.11 (s, 1H), 9.05 (s, 1H), 8.25-8.22 (m, 1H), 8.19-8.16 (m, 1H), 7.70-7.56 (m, 3H), 7.06 (d, J=8.0 Hz, 1H), 6.94 (t, J=7.6 Hz, 1H), 6.85 (d, J=7.6 Hz, 1H), 5.43-5.33 (m, 1H), 4.49 (d, J=11.2 Hz, 1H), 4.35 (d, J=11.2 Hz, 1H), 4.21-4.18 (m, 1H), 4.16-4.12 (m, 2H), 4.10-3.84 (m, 1H), 3.68-3.67 (m, 1H), 3.65 (s, 3H), 3.65-3.60 (m, 4H), 3.58 (s, 2H), 3.34-3.23 (m, 4H), 3.21 (d, J=5.6 Hz, 2H), 2.90-2.84 (m, 1H), 2.79-2.75 (m, 2H), 2.75-2.65 (m, 4H), 2.65-2.59 (m, 2H), 2.17-2.08 (m, 2H), 2.06-1.98 (m, 2H), 1.83-1.71 (m, 8H), 1.71-1.59 (m, 8H), 1.54-1.48 (m, 1H), 1.41-1.32 (m 2H), 1.08-0.97 (m, 2H); LC-MS (ESI⁺) m/z 1092.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl9-[1-(2,6-dioxo-3-piperidyl)-3-methyl-2-oxo-benzimidazol-4-yl]-3,9-diazaspiro[5.5]undecane-3-carboxylate (129). ¹H NMR (400 MHz, DMSO-d₆) δ 11.09 (s, 1H), 9.06 (s, 1H), 8.22-8.15 (m, 3H), 7.72-7.58 (m, 3H), 6.95-7.0 (m, 2H), 6.87 (d, J=6.0 Hz, 1H), 5.35 (dd, J=5.2, 12.4 Hz, 1H), 4.52-4.46 (m, 1H), 4.35 (d, J=11.2 Hz, 1H), 4.26-4.20 (m, 1H), 4.15 (d, J=10.4 Hz, 2H), 4.07 (d, J=10.4 Hz, 1H), 4.03 (s, 1H), 3.62 (s, 3H), 3.62-3.58 (m, 2H), 3.43-3.39 (m, 6H), 2.90-2.82 (m, 5H), 2.79-2.70 (m, 3H), 2.68-2.60 (m, 1H), 2.09-1.97 (m, 2H), 1.80-1.67 (m, 13H), 1.62-1.48 (m, 5H), 1.41-1.29 (m, 2H); LC-MS (ESI⁺) m/z 1034.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[[1-[[1-(2,6-dioxo-3-piperidyl)-3-methyl-2-oxo-benzimidazol-4-yl]methyl]-4-piperidyl]oxy]piperidine-1-carboxylate (130). ¹H NMR (400 MHz, DMSO-d₆) δ 11.11 (s, 1H), 9.12 (s, 1H), 8.29-8.17 (m, 2H), 7.75-7.68 (m, 1H), 7.67-7.57 (m, 2H), 7.06 (d, J=8.0 Hz, 1H), 6.95 (t, J=7.6 Hz, 1H), 6.86 (d, J=7.6 Hz, 1H), 5.38 (dd, J=5.2, 12.4 Hz, 1H), 4.72-4.57 (m, 1H), 4.55-4.42 (m, 1H), 4.40-4.17 (m, 4H), 4.07 (s, 2H), 4.01 (s, 1H), 3.83-3.75 (m, 2H), 3.66 (s, 3H), 3.60 (s, 4H), 3.48-3.41 (m, 2H), 3.17-2.97 (m, 4H), 2.95-2.82 (m, 2H), 2.74-2.59 (m, 4H), 2.21-2.06 (m, 3H), 2.04-1.97 (m, 1H), 1.96-1.62 (m, 16H), 1.43-1.26 (m, 4H); LC-MS (ESI⁺) m/z 1078.3 (M+H)⁺.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl4-[4-[1-(2,6-dioxo-3-piperidyl)-3-methyl-2-oxo-benzimidazol-4-yl]piperazin-1-yl]piperidine-1-carboxylate (131). ¹H NMR (400 MHz, DMSO-d₆) δ 11.10 (s, 1H), 9.06 (s, 1H), 8.25 (s, 1H), 8.19 (d, J=8.0 Hz, 1H), 7.71-7.58 (m, 3H), 7.01-6.96 (m, 1H), 6.93-6.87 (m, 2H), 5.35 (dd, J=5.2, 13.2 Hz, 1H), 4.49 (d, J=12.0 Hz, 2H), 4.35 (d, J=11.6 Hz, 2H), 4.23 (dd, J=7.2, 11.2 Hz, 2H), 4.18-4.12 (m, 3H), 4.07 (d, J=9.6 Hz, 2H), 4.02 (s, 2H), 3.98 (d, J=5.2 Hz, 2H), 3.67-3.61 (m, 6H), 3.59 (s, 3H), 2.85-2.75 (m, 8H), 2.64-2.58 (m, 2H), 2.06-1.98 (m, 2H), 1.78-1.72 (m, 7H), 1.70 (m, 4H), 1.58-1.49 (m, 2H), 1.39-1.28 (m, 2H); LC-MS (ESI⁺) m/z 1049.3 (M+H)⁺.

((3S,7aS)-7a-(((4-((1R,5S)-3,8-Diazabicyclo[3.2.1]octan-3-yl)-7-(8-ethynyl-7-fluoronaphthalen-1-yl)-8-fluoro-pyrido[4,3-d]pyrimidin-2-yl)oxy)methyl)hexahydro-1H-pyrrolizin-3-yl)methyl4-((1-((1-(2,6-dioxopiperidin-3-yl)-3-methyl-2-oxo-2,3-dihydro-1H-benzo[d]imidazol-4-yl)methyl)piperidin-4-yl)methyl)piperidine-1-carboxylate (132). ¹H NMR (400 MHz, DMSO-d₆) δ 11.10 (s, 1H), 9.05 (s, 1H), 8.24-8.16 (m, 2H), 7.74-7.54 (m, 3H), 7.06 (d, J=8.0 Hz, 1H), 6.94 (t, J=7.6 Hz, 1H), 6.85 (d, J=7.6 Hz, 1H), 5.37 (dd, J=5.6, 12.4 Hz, 1H), 4.50-4.31 (m, 2H), 4.31-4.07 (m, 4H), 4.06-3.99 (m, 2H), 3.92 (d, J=10.8 Hz, 2H), 3.65 (s, 3H), 3.59 (d, J=12.0 Hz, 6H), 3.25 (s, 1H), 2.94-2.84 (m, 1H), 2.80-2.58 (m, 8H), 2.07-1.97 (m, 2H), 1.91 (t, J=10.8 Hz, 2H), 1.82-1.63 (m, 10H), 1.57 (d, J=10.0 Hz, 4H), 1.52-1.42 (m, 2H), 1.37-1.26 (m, 1H), 1.10-0.85 (m, 6H); LC-MS (ESI+) m/z 1076.6 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[1-(2,6-dioxo-3-piperidyl)-3-methyl-2-oxo-benzimidazol-5-yl]ethoxy]piperidine-1-carboxylate (133). 1H NMR (400 MHz, DMSO-d6) δ 11.08 (s, 1H), 9.05 (s, 1H), 8.24-8.18 (m, 2H), 7.72-7.55 (m, 3H), 7.08 (s, 1H), 7.00 (d, J=8.4 Hz, 1H), 6.91 (d, J=8.4 Hz, 1H), 5.33 (dd, J=5.2, 12.8 Hz, 1H), 4.51-4.43 (m, 1H), 4.33 (d, J=11.6 Hz, 1H), 4.25-4.18 (m, 1H), 4.13 (d, J=10.4 Hz, 2H), 4.07-4.00 (m, 2H), 3.65-3.57 (m, 8H), 3.48 (dd, J=3.6, 8.0 Hz, 3H), 3.30 (s, 3H), 3.12-3.05 (m, 2H), 2.94-2.86 (m, 1H), 2.86-2.79 (m, 2H), 2.76-2.58 (m, 4H), 2.08-1.96 (m, 2H), 1.80-1.65 (m, 12H), 1.55-1.45 (m, 1H), 1.38-1.30 (m, 2H); LC-MS (ESI+) m/z 1009.5 (M+H)+.

[(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl N-[2-[1-[1-(2,6-dioxo-3-piperidyl)-3-methyl-2-oxo-benzimidazol-4-yl]methyl]-4-piperidyl]ethyl]-N-methyl-carbamate (134). 1H NMR (400 MHz, DMSO-d6) δ 11.12 (s, 1H), 9.14 (s, 1H), 8.30-8.17 (m, 2H), 7.77-7.53 (m, 3H), 7.07 (s, 1H), 6.98-6.77 (m, 2H), 5.49-5.31 (m 1H), 4.70-4.59 (m, 1H), 4.56-4.47 (m, 1H), 4.45-4.26 (m, 4H), 4.12 (s, 2H), 4.01 (d, J=2.8 Hz, 1H), 3.90-3.74 (m, 3H), 3.70-3.48 (m, 8H), 3.21 (d, J=5.6 Hz, 3H), 2.90-2.71 (m, 4H), 2.66 (d, J=11.6 Hz, 2H), 2.24-2.10 (m, 2H), 2.03-1.85 (m, 12H), 1.62 (s, 2H), 1.37 (d, J=5.6 Hz, 2H), 1.27-1.07 (m, 3H); LC-MS (ESI+) m/z 1036.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[2-[1-(2,6-dioxo-3-piperidyl)-3-methyl-2-oxo-benzimidazol-4-yl]ethoxy]piperidine-1-carboxylate (135). 1H NMR (400 MHz, DMSO-d6) δ 11.11 (s, 1H), 9.06 (s, 1H), 8.25-8.18 (m, 2H), 7.78-7.51 (m, 3H), 7.03-6.89 (m, 3H), 5.38-5.34 (m, 1H), 4.48 (d, J=11.2 Hz, 1H), 4.34 (d, J=12.0 Hz, 1H), 4.24-4.18 (m, 1H), 4.15-4.10 (m, 2H), 4.07-4.02 (m, 1H), 4.08-4.00 (m, 1H), 3.70-3.65 (m, 2H), 3.65-3.60 (m, 4H), 3.57 (s, 3H), 3.48-3.45 (m, 2H), 3.3-3.23 (m, 2H), 3.16-3.06 (m, 4H), 2.93-2.84 (m, 1H), 2.76-2.59 (m, 4H), 2.08-1.92 (m, 2H), 1.80-1.63 (m, 12H), 1.55-1.45 (m, 1H), 1.38-1.27 (m, 2H); LC-MS (ESI+) m/z 1009.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[3-[1-(2,6-dioxo-3-piperidyl)-3-methyl-2-oxo-benzimidazol-5-yl]propoxy]piperidine-1-carboxylate (136). 1H NMR (400 MHz, DMSO-d6) δ 11.09 (s, 1H), 9.05 (s, 1H), 8.28-8.22 (m, 2H), 8.19 (d, J=8.4 Hz, 1H), 7.71-7.65 (m, 1H), 7.64-7.58 (m, 1H), 7.02 (s, 1H), 6.99 (d, J=8.0 Hz, 1H), 6.86 (d, J=8.0 Hz, 1H), 5.33 (dd, J=5.2, 12.8 Hz, 1H), 4.49 (d, J=12.4 Hz, 1H), 4.35 (d, J=12.4 Hz, 1H), 4.24-4.19 (m, 1H), 4.14 (d, J=10.4 Hz, 2H), 4.09-4.00 (m, 3H), 3.70-3.59 (m, 6H), 3.45-3.36 (m, 3H), 3.31 (s, 3H), 3.28 (s, 1H), 3.08 (d, J=9.2 Hz, 2H), 2.95-2.83 (m, 1H), 2.80-2.71 (m, 2H), 2.71-2.57 (m, 4H), 2.10-1.95 (m, 2H), 1.91-1.59 (m, 14H), 1.56-1.46 (m, 1H), 1.42-1.29 (m, 2H); LC-MS (ESI+) m/z 1023.5 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[3-[3-methyl-1-(1-methyl-2,6-dioxo-3-piperidyl)-2-oxo-benzimidazol-4-yl]propoxy]piperidine-1-carboxylate (144). 1H NMR (400 MHz, DMSO-d6) δ 10.85-10.70 (m, J=4.4 Hz, 1H), 9.95 (d, J=10.0 Hz, 1H), 9.45-9.67 (m, 1H), 9.17 (s, 1H), 8.37-8.13 (m, 2H), 7.81-7.52 (m, 3H), 7.09-6.79 (m, 3H), 5.43 (dd, J=5.2, 12.8 Hz, 1H), 4.75-4.53 (m, 4H), 4.39 (d, J=9.2 Hz, 1H), 4.30-4.17 (m, 3H), 4.10-3.92 (m, 4H), 3.56 (s, 3H), 3.48 (s, 3H), 3.43-3.32 (m, 2H), 3.26-3.07 (m, 2H), 3.03 (s, 3H), 3.01-2.88 (m, 3H), 2.84-2.51 (m, 5H), 2.34-2.25 (m, 1H), 2.20-1.92 (m, 12H), 1.85-1.72 (m, 4H), 1.46-1.35 (m, 2H); LC-MS (ESI+) m/z 1037.3 (M+H)+.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl 4-[[[1-[[1-(2,6-dioxo-3-piperidyl)-3-methyl-2-oxo-benzimidazol-4-yl]methyl]-4-piperidyl]amino]methyl] piperidine-1-carboxylate (145). 1H NMR (400 MHz, DMSO-d6) 11.11 (s, 1H), 9.06 (s, 1H), 8.25-8.18 (m, 4H), 7.73-7.55 (m, 3H), 7.10-7.15 (m, 1H), 6.96 (t, J=7.6 Hz, 1H), 6.89-6.84 (m, 1H), 5.48-5.28 (m, 2H), 4.53-4.47 (m, 1H), 4.38-4.33 (m, 1H), 4.25-4.17 (m, 2H), 4.16-4.11 (m, 2H), 4.09-4.04 (m, 2H), 4.01 (s, 2H), 3.99-3.91 (m, 4H), 3.65 (s, 3H), 2.85-2.71 (m, 8H), 2.68-2.64 (m, 2H), 2.04-1.95 (m, 4H), 1.91-1.84 (m, 2H), 1.72 (s, 10H), 1.56-1.35 (m, 4H), 1.23 (s, 4H), 1.09-0.97 (m, 2H), 0.88-0.82 (m, 1H); LC-MS (ESI+) m/z 1091.6 (M+H)+.

Example 88. Synthesis of Compound 146

(a) 3-[(4-Methoxyphenyl)methyl]hexahydropyrimidine-2,4-dione

To a solution of hexahydropyrimidine-2,4-dione (10.0 g, 87.6 mmol, CAS #504-07-4) in DMF (200 mL) was added PMB-Cl (17.8 g, 113 mmol) and Cs2CO3 (34.2 g, 105 mmol). The mixture was stirred at 25° C. for 16 hrs. On completion, the mixture was filtered and washed with DMF (10 mL) and concentrated in vacuo. The residue was triturated with water:EA (30 mL:30 mL) at 25° C. for 30 min to give the title compound (17.0 g, 82% yield) as white solid. 1H NMR (400 MHz, DMSO-d6) δ 7.82 (s, 1H), 7.17 (d, J=8.4 Hz, 2H), 6.84 (d, J=8.4 Hz, 2H), 4.71 (s, 2H), 3.71 (s, 3H), 3.25-3.17 (m, 2H), 2.65-2.60 (m, 2H).

(b) Tert-butyl 4-[4-[3-[(4-methoxyphenyl)methyl]-2,4-dioxo-hexahydropyrimidin-1-yl] phenyl]piperazine-1-carboxylate

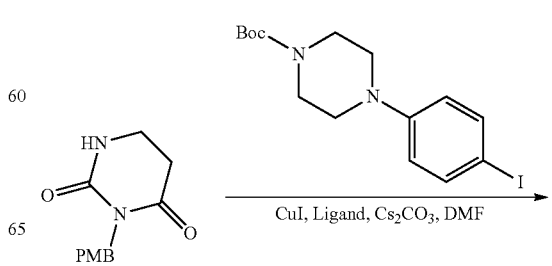

-continued

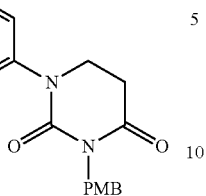

To a solution of tert-butyl 4-(4-iodophenyl)piperazine-1-carboxylate (2.00 g, 5.15 mmol, CAS #151978-66-4) and 3-[(4-methoxyphenyl)methyl]hexahydropyrimidine-2,4-dione (1.33 g, 5.67 mmol) in DMF (35 mL) was added $Cs_2CO_3$ (3.36 g, 10.3 mmol), (1R,2R)—N1,N2-dimethylcyclohexane-1,2-diamine (146 mg, 1.03 mmol) and CuI (196 mg, 1.03 mmol) was degassed and purged with $N_2$ for 3 times, and then the mixture was stirred at 70° C. for 16 hours under $N_2$ atmosphere. On completion, the mixture was filtered and the filtrate was diluted with $H_2O$ (50 mL), extracted with EA (3×50 mL), the organic layer was washed with brine (30 mL), dried with anhydrous $Na_2SO_4$, filtered and the filter was concentrated in vacuo. The residue was purified by column chromatography ($SiO_2$, Petroleum ether:Ethyl acetate=65:35) to give the title compound (2.37 g, 93% yield) as white solid. $^1$H NMR (400 MHz, DMSO-$d_6$) δ 7.19 (dd, J=8.8, 17.6 Hz, 4H), 6.96 (d, J=8.8 Hz, 2H), 6.85 (d, J=8.4 Hz, 2H), 4.79 (s, 2H), 3.76-3.68 (m, 5H), 3.49-3.42 (m, 4H), 3.13-3.06 (m, 4H), 2.88-2.86 (m, 2H), 1.42 (s, 9H); LC-MS (ESI$^+$) m/z 495.1 (M+H)$^+$.

(c) 1-(4-Piperazin-1-ylphenyl)hexahydropyrimidine-2,4-dione

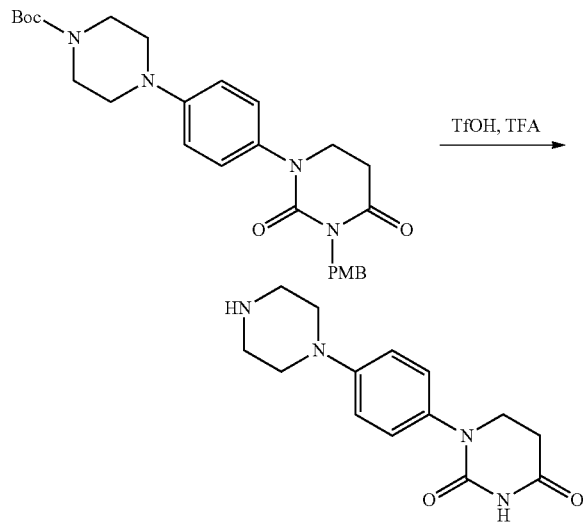

Tert-butyl 4-[4-[3-[(4-methoxyphenyl)methyl]-2,4-dioxo-hexahydropyrimidin-1-yl]phenyl]piperazine-1-carboxylate (500 mg, 1.01 mmol) was dissolved in TFA (3.5 mL) and TfOH (0.7 mL). The mixture was stirred at 70° C. for 1 hr. On completion, the mixture was concentrated in vacuo to give the title compound (277 mg, 99% yield) as brown oil. LC-MS (ESI$^+$) m/z 275.1 (M+H)$^+$.

(d) Tert-butyl 4-[4-(2,4-dioxohexahydropyrimidin-1-yl)phenyl]piperazine-1-carboxylate

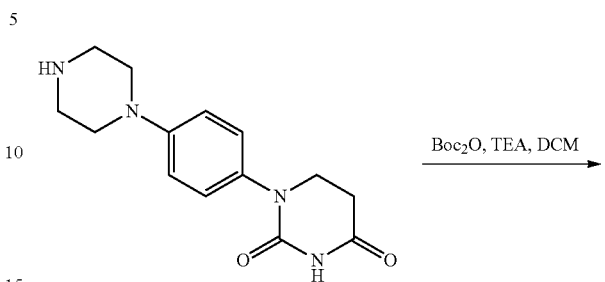

To a solution of 1-(4-piperazin-1-ylphenyl)hexahydropyrimidine-2,4-dione (277 mg, 1.01 mmol) in DCM (2 mL) was added $Boc_2O$ (440 mg, 2.02 mmol) and TEA (306 mg, 3.03 mmol). The mixture was stirred at 25° C. for 16 hrs. On completion, the mixture was diluted with $H_2O$ (20 mL), extracted with DCM (3×10 mL), washed with brine (10 mL), the organic layer was dried with anhydrous $Na_2SO_4$, filter and the filtrate was concentrated in vacuo. The crude product was triturated with ACN (5 mL) at 25° C. for 30 min, then filter and the filtre residue was concentrated in vacuo to give the title compound (300 mg, 79% yield) as white solid. $^1$H NMR (400 MHz, DMSO-$d_6$) δ 10.28 (s, 1H), 7.17 (d, J=8.8 Hz, 2H), 6.95 (d, J=8.8 Hz, 2H), 3.70 (t, J=6.8 Hz, 2H), 3.50-3.40 (m, 4H), 3.12-3.05 (m, 4H), 2.68 (t, J=6.8 Hz, 2H), 1.42 (s, 9H); LC-MS (ESI$^+$) m/z 375.1 (M+H)$^+$.

(e) 1-(4-Piperazin-1-ylphenyl)hexahydropyrimidine-2,4-dione

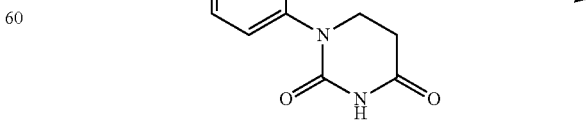

-continued

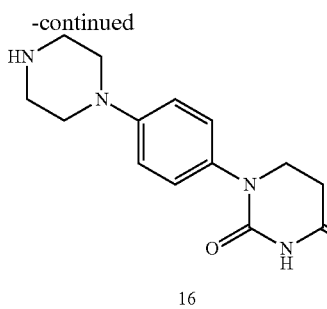

16

To a solution of tert-butyl 4-[4-(2,4-dioxohexahydropyrimidin-1-yl)phenyl]piperazine-1-carboxylate (250 mg, 667 μmol) in DCM (2 mL) was added TFA (1.54 g, 13.4 mmol). The mixture was stirred at 25° C. for 1 hr. On completion, the mixture was concentrated in vacuo to give the title compound (259 mg, 99% yield, TFA salt) as yellow oil. LC-MS (ESI$^+$) m/z 275.0 (M+H)$^+$.

(f) Tert-butyl N-[4-[4-[4-(2,4-dioxohexahydropyrimidin-1-yl)phenyl]piperazin-1-yl]-4-oxo-butyl]carbamate

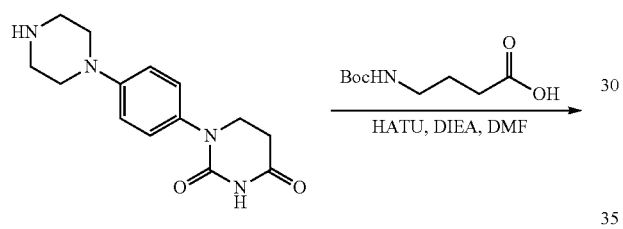

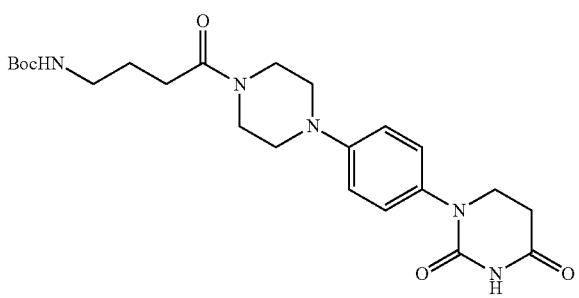

To a solution of 1-(4-piperazin-1-ylphenyl)hexahydropyrimidine-2,4-dione (259 mg, 666 μmol, TFA salt) and 4-(tert-butoxycarbonylamino)butanoic acid (135 mg, 666 μmol, CAS #57294-38-9) in DMF (1 mL) was added HATU (380 mg, 1.00 mmol) and DIEA (172 mg, 1.33 mmol). The mixture was stirred at 25° C. for 1 hr. On completion, the mixture was quenched with H$_2$O (1 mL), then concentrated in vacuo. The residue was purified by reversed phase (0.1% FA) to give the title compound (260 mg, 84% yield) as white solid. $^1$H NMR (400 MHz, DMSO-d$_6$) δ 10.28 (s, 1H), 7.17 (d, J=8.8 Hz, 2H), 6.96 (d, J=8.8 Hz, 2H), 6.82 (t, J=5.2 Hz, 1H), 3.70 (t, J=6.8 Hz, 2H), 3.62-3.54 (m, 4H), 3.17-3.05 (m, 4H), 2.94 (q, J=6.8 Hz, 2H), 2.68 (t, J=6.8 Hz, 2H), 2.34 (t, J=7.2 Hz, 2H), 1.66-1.57 (m, 2H), 1.37 (s, 9H); LC-MS (ESI$^+$) m/z 460.1 (M+H)$^+$.

(g) 1-[4-[4-(4-Aminobutanoyl)piperazin-1-yl]phenyl]hexahydropyrimidine-2,4-dione

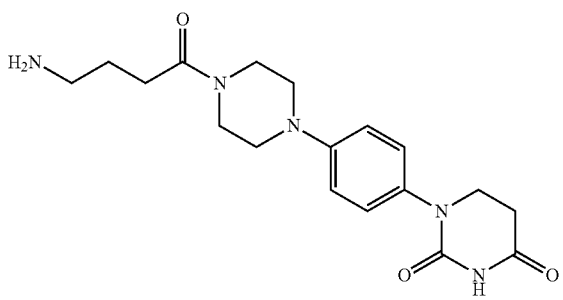

To a solution of tert-butyl N-[4-[4-[4-(2,4-dioxohexahydropyrimidin-1-yl)phenyl]piperazin-1-yl]-4-oxo-butyl]carbamate (55.0 mg, 119 μmol) in DCM (1 mL) was added TFA (307 mg, 2.69 mmol). The mixture was stirred at 25° C. for 1 hr. On completion, the mixture was concentrated in vacuo to give the title compound (56.0 mg, 98% yield, TFA salt) as yellow oil. LC-MS (ESI$^+$) m/z 360.1 (M+H)$^+$.

(h) Tert-butyl 3-[2-[[[(3S,8S)-3-[[4-[4-[4-(2,4-dioxo-hexahydropyrimidin-1-yl)phenyl]piperazin-1-yl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate

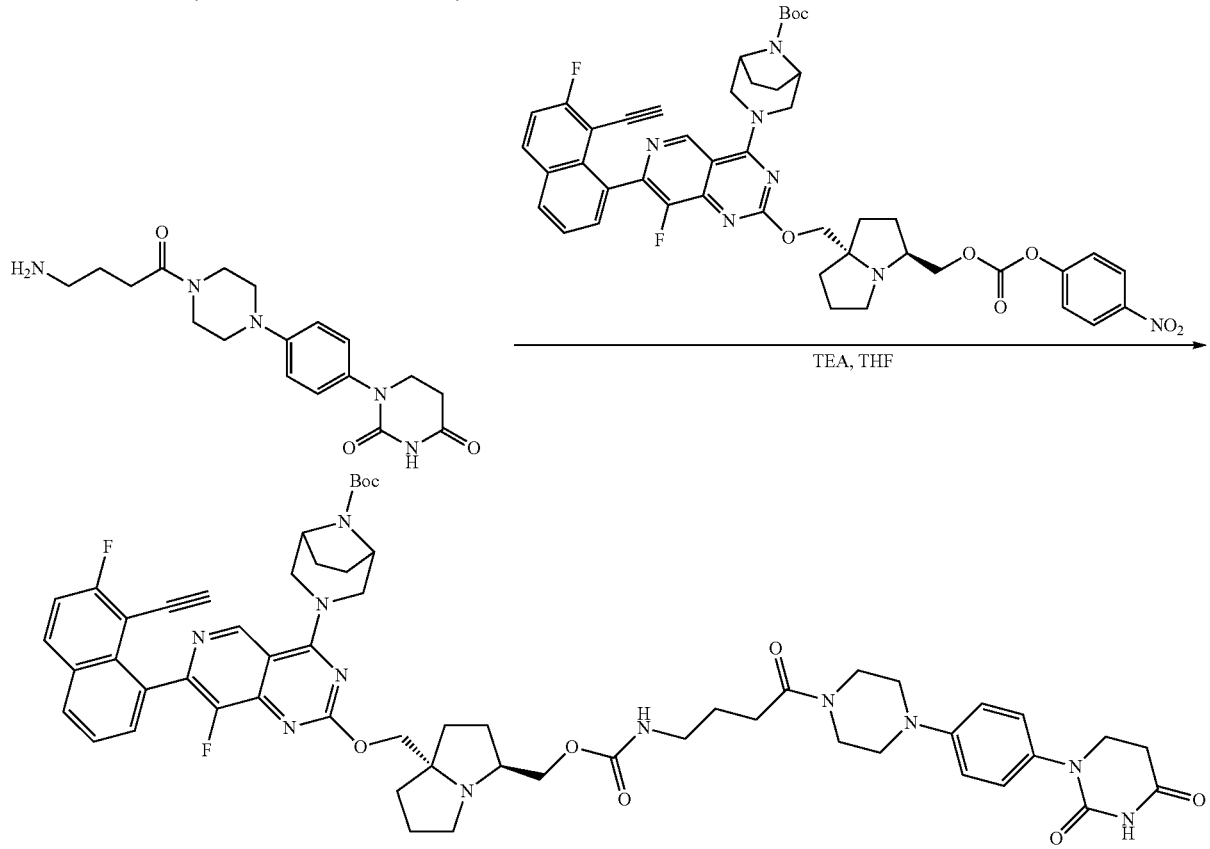

To a solution of 1-[4-[4-(4-aminobutanoyl)piperazin-1-yl]phenyl]hexahydropyrimidine-2,4-dione (53.5 mg, 113 μmol, TFA salt) and tert-butyl 3-[7-(8-ethynyl-7-fluoro-1-naphthyl)-8-fluoro-2-[[(3S,8S)-3-[(4-nitrophenoxy)carbonyloxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (65.0 mg, 75.4 μmol) in THF (5 mL) was added TEA (15.2 mg, 150 μmol). The mixture was stirred at 25° C. for 1 hr. On completion, the mixture was concentrated in vacuo. The residue was purified by prep-HPLC (column: Phenomenex luna C18 150*25 mm*10 μm; mobile phase: [water (FA)-ACN]; gradient: 22%-52% B over 8 min) to give the title compound (40.0 mg, 49% yield) as yellow solid. LC-MS (ESI⁺) m/z 1082.6 (M+H)⁺.

(i) [(3S,8S)-8-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl]methylN-[4-[4-[4-(2,4-dioxohexahydropyrimidin-1-yl)phenyl]piperazin-1-yl]-4-oxo-butyl]carbamate (146)

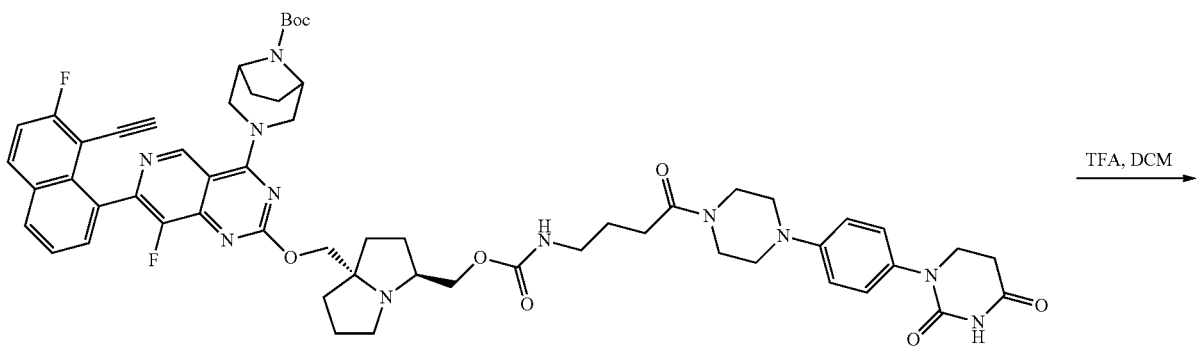

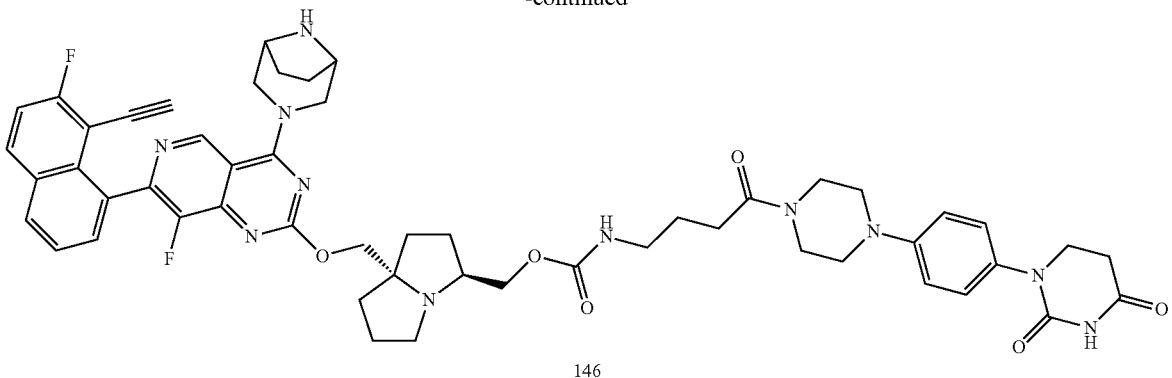

146

To a solution of tert-butyl 3-[2-[[(3S,8S)-3-[[4-[4-[4-(2,4-dioxohexahydropyrimidin-1-yl)phenyl]piperazin-1-yl]-4-oxo-butyl]carbamoyloxymethyl]-1,2,3,5,6,7-hexahydropyrrolizin-8-yl]methoxy]-7-(8-ethynyl-7-fluoro-1-naphthyl)-8-fluoro-pyrido[4,3-d]pyrimidin-4-yl]-3,8-diazabicyclo[3.2.1]octane-8-carboxylate (40.0 mg, 36.9 μmol) in DCM (1 mL) was added TFA (409 mg, 3.59 mmol). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 5%-35% B over 8 min) to give the title compound (37.1 mg, 94% yield, FA salt) as yellow solid. $^1$H NMR (400 MHz, DMSO-d$_6$) δ 10.29 (s, 1H), 9.11 (s, 1H), 8.26-8.18 (m, 2H), 7.75-7.55 (m, 3H), 7.27-7.20 (m, 1H), 7.16 (d, J=8.8 Hz, 2H), 6.94 (d, J=8.8 Hz, 2H), 4.61 (d, J=13.2 Hz, 1H), 4.46 (d, J=13.2 Hz, 1H), 4.28-4.10 (m, 4H), 4.06-3.99 (m, 3H), 3.77 (t, J=11.4 Hz, 2H), 3.69 (t, J=6.8 Hz, 2H), 3.60-3.53 (s, 4H), 3.41-3.35 (m, 1H), 3.15-3.05 (m, 4H), 3.04-2.98 (m, 2H), 2.93-2.77 (m, 2H), 2.68 (t, J=6.8 Hz, 2H), 2.35 (t, J=7.2 Hz, 2H), 2.14-2.06 (m, 1H), 1.95-1.54 (m, 14H); LC-MS (ESI$^+$) m/z 982.5 (M+H)$^+$.

Example 89. Synthesis of Compounds 147-149

The following compounds were synthesized from appropriate starting materials using appropriate reagents in accordance with the procedure described herein for synthesis of Compound 146:

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl N-[5-[4-[4-(2,4-dioxohexahydropyrimidin-1-yl)phenyl]piperazin-1-yl]-5-oxo-pentyl]carbamate (147). $^1$H NMR (400 MHz, DMSO-d$_6$) δ 10.28 (s, 1H), 9.05 (s, 1H), 8.25-8.15 (m, 2H), 7.73-7.54 (m, 3H), 7.27-7.12 (m, 3H), 6.94 (d, J=8.8 Hz, 2H), 4.49 (d, J=11.6 Hz, 1H), 4.35 (d, J=11.6 Hz, 1H), 4.18-4.01 (m, 8H), 3.68 (d, J=6.8 Hz, 4H), 3.57 (s, 4H), 3.28-3.21 (m, 1H), 3.15-3.03 (m, 4H), 2.97 (q, J=6.4 Hz, 2H), 2.77-2.64 (m, 4H), 2.34 (t, J=7.2 Hz, 2H), 2.10-1.99 (m, 1H), 1.80-1.61 (m, 10H), 1.54-1.36 (m, 5H); LC-MS (ESI+) m/z 996.4 (M+H)$^+$.

((3S,7aS)-7a-(((4-(3,8-Diazabicyclo[3.2.1]octan-3-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl) methyl(6-(4-(4-(2,4-dioxotetrahydropyrimidin-1(2H)-yl)phenyl)piperazin-1-yl)-6-oxohexyl)carbamate (148). $^1$H NMR (400 MHz, DMSO-d$_6$) δ 10.27 (s, 1H), 9.06 (s, 1H), 8.25-8.21 (m, 1H), 8.18 (d, J=1.2 Hz, 1H), 7.72-7.57 (m, 3H), 7.19-7.15 (m, 3H), 6.94 (d, J=8.8 Hz, 2H), 4.50 (d, J=11.6 Hz, 1H), 4.36 (d, J=12.0 Hz, 1H), 4.16-4.08 (m, 3H), 4.06 (s, 1H), 4.02 (s, 1H), 3.72-3.68 (m, 4H), 3.63 (d, J=12.8 Hz, 2H), 3.57 (s, 4H), 3.25 (s, 1H), 3.14-3.04 (m, 4H), 2.95 (q, J=6.4 Hz, 2H), 2.81-2.70 (m, 2H), 2.67 (t, J=6.8 Hz, 2H), 2.32 (t, J=7.6 Hz, 2H), 2.09-2.00 (m, 1H), 1.73 (s, 10H), 1.64-1.55 (m, 1H), 1.54-1.44 (m, 3H), 1.43-1.35 (m, 2H), 1.30-1.21 (m, 2H); LC-MS (ESI$^+$) m/z 1010.4 (M+H)$^+$.

[(3S,8S)-8-[[4-(3,8-Diazabicyclo[3.2.1]octan-3-yl)-7-(8-ethynyl-7-fluoro-1-naphthyl)-8-fluoro-pyrido[4,3-d]pyrimidin-2-yl]oxymethyl]-1,2,3,5,6,7-hexahydropyrrolizin-3-yl] methyl N-[7-[4-[4-(2,4-dioxohexahydropyrimidin-1-yl)phenyl]piperazin-1-yl]-7-oxo-heptyl]carbamate (149). $^1$H NMR (400 MHz, DMSO-d$_6$) δ 10.27 (s, 1H), 9.06 (s, 1H), 8.23-8.17 (m, 2H), 7.73-7.55 (m, 3H), 7.16 (d, J=8.8 Hz, 3H), 6.94 (d, J=8.8 Hz, 2H), 4.51 (d, J=12.4 Hz, 1H), 4.36 (d, J=12.0 Hz, 1H), 4.14-4.02 (m, 4H), 3.70 (d, J=6.4 Hz, 10H), 3.57 (s, 4H), 3.26 (s, 1H), 3.09 (d, J=20.0 Hz, 4H), 2.95 (q, J=6.4 Hz, 2H), 2.80-2.74 (m, 1H), 2.70-2.65 (m, 2H), 2.32 (t, J=7.2 Hz, 2H), 2.10-1.99 (m, 1H), 1.74 (s, 9H), 1.54-1.45 (m, 3H), 1.36 (s, 6H), LC-MS (ESI$^+$) m/z 1024.5 (M+H)$^+$.

Assay Example 1. KRAS Western Blot (WB) Protocol

Day 1. Seeded AGS cells (KRAS G12D mutant cell line, ATCC, CRL-1739) or LS180 cells (KRAS G12D mutant cell line, ATCC, CRL-187) into 6-well plates (cell density: 3×10$^5$ cells/well/2 ml medium) in Ham's F-12 medium (Invitrogen, 11765-054) or Eagle's Minimum Essential Medium (ATCC, 30-2003) and incubated overnight at 37° C. and 5% CO$_2$.

Day 2. Aspirated 1 ml medium from each well and added 1 ml medium containing DMSO or test compound into the well to achieve the desired final concentration. Mixed well by gentle shaking and incubated for 24 hours.

Day 3. Aspirated media from plates; washed cells with 2 ml 4° C. PBS (Solarbio, P1020-500) and aspirated the PBS. Then added 100 μl 4° C. PIPA lysis buffer (Boston BioProducts BP-115D) with protease and phosphatase inhibitors at vendor recommended concentrations (Roche 05892791001 and 04906837001) into each well to lyse the cells, and incubated for 20 minutes at 4° C. Cell lysate was collected into 1.5 ml Eppendorf tube, and the lysate was sonicated at 4° C. for 2 minutes (5 second pulse at 30% power with 10 second intermissions). The lysate was centrifuged at 12,000 rpm for 15 minutes at 4° C. The supernatant was transferred to a fresh Eppendorf tube, and protein concentration was quantified using a BCA kit (Solarbio, PC0020-500). Mixed the cell lysate and 5×NuPAGE SDS Loading Buffer (Beyotime, P0015L), and heated at 95° C. for 10 minutes in a heat block. Prepared samples were stored at −80° C. until SDS-PAGE procedure.

Day 4. Loaded 15 µg protein from each sample onto NuPAGE® Novex 4-12% Bis-Tris Midi Gel, 26 W (Invitrogen, WG1403BOX) and ran the gel at 120V for 1.5 hours in 1×NuPAGE® MOPS SDS Running Buffer (Novex, NP0001). Electrotransferred to nitrocellulose membrane using dry transfer method (iBlot 2 Transfer Stacks, nitrocellulose, IB23001) with a program consisting of 20V for 1 minute, 23V for 4 minutes and 25V for 2 minutes. Blocked the membrane with 5% BSA (Solarbio, A8020) in 1×TBST (CST, 9997S) for 1 hour at room temperature. Incubated with KRAS antibody (LSBio, LS-C175665, clone 2C1) at 1:1000 dilution and β-actin antibody at 1:1000 dilution (CST, 4970S) in TBST containing 1% BSA (Solarbio, A8020) at 4° C. overnight.

Day 5. Washed nitrocellulose membrane three times with 1×TBST for 10 minutes each at room temperature. Incubated with fluorescently labeled secondary antibodies at 1:5000 dilution in TBST containing 1% BSA (anti-rabbit IgG, Licor, 926-32211; anti-mouse IgG, LI-COR, 926-68070) for 1 hour at room temperature. Washed membrane three times with TBST, 10 minutes each. Scanned the membrane on LiCOR scanner for fluorescent signal(s) and quantified KRAS bands and β-actin bands for normalization.

The data are reported in Table 2, wherein "A" indicates a $DC_{50}$ of less than 1 µM; "B" indicates a $DC_{50}$ of greater than or equal to 1 µM and less than 10 µM; and "C" indicates a $DC_{50}$ of greater than or equal to 10 µM.

TABLE 2

WB Assay ("A" = $DC_{50}$ less than 1 µM,
"B" = $DC_{50}$ greater than or equal to 1
µM and less than 10 µM, "C" = $DC_{50}$ greater than or equal to 10 µM)

| Compound No. | $DC_{50}$ |
|---|---|
| 001 | C |
| 002 | C |
| 003 | C |
| 004 | C |
| 005 | C |
| 006 | C |
| 007 | C |
| 008 | B |
| 009 | A |
| 010 | A |
| 011 | A |
| 012 | A |
| 013 | A |
| 014 | A |
| 015 | A |
| 016 | A |
| 017 | B |
| 018 | B |
| 019 | C |
| 020 | C |
| 021 | B |
| 022 | C |
| 023 | A |
| 025 | C |
| 027 | C |
| 028 | C |
| 029 | A |
| 030 | A |
| 031 | A |
| 032 | A |
| 033 | A |

Assay Example 2. G12D HiBit Assay Protocol

Day 1. Prepared the culture medium for AsPc-1-KRAS (G12D)-HiBit-KI cell (Pharmaron) using RPMI 1640 medium (Gibco, 11875093) with 10% FBS (Gibco, 10099141C) and 1% Penicillin-Streptomycin Liquid (Solarbio, P1400). Cultivated cells in T-75 flasks in a cell culture incubator (Thermo, Model: 371) at 37° C., 5% $CO_2$. Allowed cells to reach approximately 80% confluence before splitting. Rinsed cultivated cells in T-75 flasks with 5 mL PBS (Solarbio, P1020-500). Aspirated off PBS, added 1.5 mL trypsin (Invitrogen, #25300), and incubated at 37° C. for approximately 5 minutes or until the cells detached. Inactivated trypsin by adding excessive serum containing medium. Harvested the cells from flask into cell culture medium and counted the cell number. Seeded AsPc-1-KRAS (G12D)-HiBit-KI cell into 384-well plate (Corning, 3570) (cell density: $5 \times 10^3$ cells/well in 50 µL medium) in RPMI 1640 medium and incubated overnight at 37° C. and 5% $CO_2$.

Day 2. Test compounds were dissolved at 0.3 mM in DMSO (Solarbio, D8371) as stock solution. Transferred 45 µL of stock solution to a 384-well plate (Labcyte, 001-14555). Performed 3-fold, 10-points dilution via transferring 15 µL compound into 30 µL DMSO by using TECAN liquid handler (TECAN, Freedom EVO200). The compound plates were spin at room temperature at 1,000 RPM for 1 minute (Eppendorf, 5810R). Transferred 50 nL of diluted compounds from compound source plate into the cell plate by Echo (Labcyte, 550) to achieve final concentrations of 300 nM, 100 nM, 33.3 nM, 11.1 nM, 3.7 nM, 1.23 nM, 0.41 nM, 0.14 nM, 0.046 nM and 0.015 nM, then mixed the cell plate on a plate shaker (Yoning, WZ-4) for 15 seconds at 900 rpm. After compound treatment for 24 hours, removed the plate from incubators and equilibrated at room temperature for 15 minutes. Prepared the HiBit reagent (Promega, N3040) by mixing 10 mL of Nano-Glo®-HiBiT Lytic Buffer with 200 µL of Nano-Glo®-HiBiT Lytic Substrate and 100 µL of LgBiT Protein. Added 20 µL of HiBit reagent into each well of the cell plate and spun the plates at room temperature at 1,000 RPM for 1 minute. Then shook the plates at 600 RPM at room temperature for 20 minutes using a plate shaker (Yoning, WZ-4), and read the luminescence by EnVision (PerkinElmer, 2105-0020).

The inhibition activity was calculated using the following formula:

$$\text{HiBit-G12D level (\%)} = 100\% \times [\text{Luminescence (Sample)/Mean of Luminescence (HC)}]$$

where HC (high control) is obtained from cells treated with 0.1% DMSO only.

Absolute $DC_{50}$ was calculated by fitting the curve using GraphPad Prism v8.0.2 (analyis 263):

$$Y = \text{Bottom} + (100 - \text{Bottom})/(1 + 10^{\wedge}(\text{Log AbsoluteIC}_{50} - X)^* \text{HillSlope} + \log((100 - \text{Bottom})/(50 - \text{Bottom}) - 1)))$$

The data are reported in Table 3, wherein "+++"=$DC_{50}$ less than 100 nM, "++"=$DC_{50}$ greater than or equal to 100 nM and less than 300 nM; "+"=$DC_{50}$ greater than or equal to 300 nM.

TABLE 3

HiBit Assay ("+++" = $DC_{50}$ less than 100 nM, "++" = $DC_{50}$ greater than or equal to 100 nM and less than 300 nM; "+" = $DC_{50}$ greater than or equal to 300 nM)

| Compound No. | Average PHA $DC_{50}$ | Compound No. | Average PHA $DC_{50}$ | Compound No. | Average PHA $DC_{50}$ |
|---|---|---|---|---|---|
| 31 | +++ | 56 | +++ | 80 | +++ |
| 32 | +++ | 57 | + | 81 | +++ |
| 34 | +++ | 58 | +++ | 82 | +++ |
| 35 | +++ | 59 | +++ | 106 | +++ |
| 36 | + | 60 | ++ | 107 | +++ |
| 37 | ++ | 61 | ++ | 108 | +++ |
| 38 | +++ | 62 | +++ | 109 | + |
| 39 | + | 63 | ++ | 110 | + |
| 40 | +++ | 64 | +++ | 111 | +++ |
| 41 | + | 65 | ++ | 112 | +++ |
| 42 | +++ | 66 | +++ | 113 | ++ |
| 43 | + | 67 | +++ | 114 | +++ |
| 44 | +++ | 68 | +++ | 115 | + |
| 45 | + | 69 | +++ | 116 | + |
| 46 | + | 70 | + | 117 | +++ |
| 47 | +++ | 71 | +++ | 118 | +++ |
| 48 | + | 72 | ++ | 119 | +++ |
| 49 | + | 73 | +++ | 124 | +++ |
| 50 | +++ | 74 | +++ | 127 | + |
| 51 | +++ | 75 | ++ | 128 | +++ |
| 52 | +++ | 76 | +++ | 130 | +++ |
| 53 | +++ | 77 | ++ | 132 | +++ |
| 54 | +++ | 78 | +++ | 144 | + |
| 55 | +++ | 79 | + | 145 | +++ |
| 83 | +++ | 94 | + | 146 | + |
| 84 | +++ | 95 | + | 147 | + |
| 85 | +++ | 96 | + | 148 | + |
| 87 | +++ | 97 | +++ | 149 | + |
| 88 | +++ | 98 | +++ | 102 | +++ |
| 89 | +++ | 99 | +++ | 103 | +++ |
| 90 | +++ | 100 | +++ | 104 | +++ |
| 92 | +++ | 101 | +++ | 105 | +++ |
| 93 | +++ | 136 | +++ | 33 | +++ |
| 120 | +++ | 125 | + | 133 | + |
| 122 | +++ | 126 | + | 134 | +++ |
| 121 | + | 129 | + | 135 | +++ |
| 123 | + | 131 | + | 137 | + |

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound of the following formula:

[KRAS G12Di]-L'-[Degron], or a pharmaceutically acceptable salt thereof, wherein:
KRAS G12Di is:

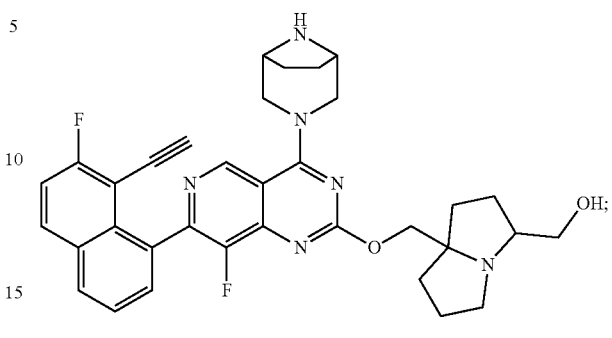

L' is a covalent bond or a bivalent, saturated or unsaturated, straight or branched $C_1$-$C_{15}$ hydrocarbon chain wherein 0-5 methylenes of L' are replaced by X, each X is independently —O—, —N(R)—, —S—, —OC(O)—, —C(O)—, —C(H)(F)—, —C(F)$_2$—, -Cy-, —S(O)—, —S(O)$_2$—, —N(R)S(O)$_2$—, —N(R)C(O)—, —OC(O)N(R)—, —N(R)C(O)N(R)—,

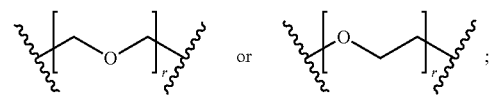

each -Cy- is independently an optionally substituted bivalent ring selected from a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur; and each R is independently hydrogen or ($C_1$-$C_3$) alkyl;
r is 1, 2, 3, 4, 5, 6, 7, 8, 9, or 10; and
Degron is a cereblon binding moiety.

2. A compound of the following formula:

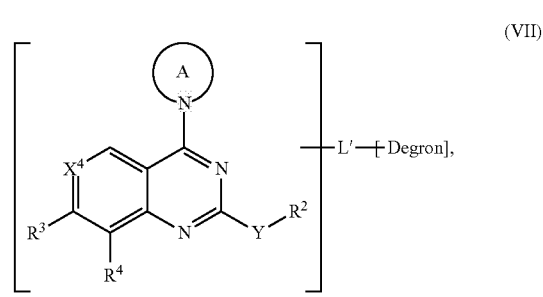

(VII)

or a pharmaceutically acceptable salt thereof, wherein:

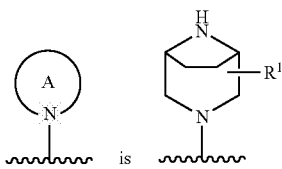 is $X^4$ is N or $C(R^{42})$;

$R^{42}$ is hydrogen, halogen, $(C_1-C_6)$alkyl, $(C_1-C_6)$haloalkyl, $(C_1-C_6)$haloalkoxy, $(C_2-C_6)$alkenyl, $(C_2-C_6)$alkynyl, —CN, $(C_1-C_6)$alkoxy, —S—$(C_1-C_6)$alkyl or —S—$(C_1-C_6)$haloalkyl;

Y is a bond, O or $NR^5$;

$R^1$ is hydrogen, hydroxy, halogen, $(C_1-C_3)$alkyl, $(C_1-C_3)$cyanoalkyl, $(C_1-C_3)$hydroxyalkyl, —C(O)H, —$CO_2R^5$, —$CO_2N(R^5)_2$ or $(C_5-C_6)$heteroaryl;

$R^2$ is hydrogen, —$N(R^5)_2$, $(C_3-C_{12})$heterocyclyl, $(C_1-C_6)$alkyl, -L-$(C_3-C_{12})$heterocyclyl, -L-$(C_6-C_{14})$aryl, -L-$(C_5-C_{14})$heteroaryl, -L-$(C_3-C_{12})$cycloalkyl, -L-$N(R^5)_2$, -L-N(H)C(NH)$NH_2$, -L-C(O)$N(R^5)_2$, -L-$(C_1-C_6)$haloalkyl, -L-$OR^5$, -L-$NR^5C(O)$—$(C_6-C_{14})$aryl, -L-COOH or -L-C(O)O$(C_1-C_6)$alkyl, wherein the $(C_3-C_{12})$heterocyclyl, the $(C_6-C_{14})$aryl of -L-$NR^5C(O)$—$(C_6-C_{14})$aryl, the $(C_3-C_{12})$heterocyclyl of -L-$(C_3-C_{12})$heterocyclyl and the $(C_3-C_{12})$cycloalkyl of -L-$(C_3-C_{12})$cycloalkyl are optionally substituted with one or more $R^6$, and the aryl of -L-$(C_6-C_{14})$aryl and $(C_5-C_{14})$heteroaryl of -L-$(C_5-C_{14})$heteroaryl are optionally substituted with one or more $R^7$;

L is $(C_1-C_4)$alkylene optionally substituted with hydroxy, $(C_1-C_4)$hydroxyalkyl or $(C_5-C_{14})$heteroaryl;

$R^3$ is

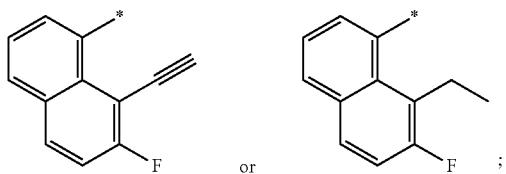 [SMILES: *c1cccc2ccc(F)c(C#C)c12 ; *c1cccc2ccc(F)c(CC)c12]

$R^4$ is hydrogen, halogen or $(C_1-C_3)$alkyl;

each $R^5$ is independently hydrogen or $(C_1-C_3)$alkyl;

each $R^6$ is independently halogen, hydroxy, $(C_1-C_3)$hydroxyalkyl, $(C_1-C_3)$alkyl, $(C_1-C_3)$haloalkyl, $(C_1-C_3)$alkoxy, cyano, -Q-phenyl, -Q-phenyl-$SO_2F$, —N(H)C(O)-phenyl, —N(H)C(O)-phenyl-$SO_2F$, $(C_1-C_3)$alkyl-substituted pyrazole, $(C_6-C_{14})$aryl $(C_1-C_3)$alkyl, tert-butyldimethylsilyloxy-$CH_2$—, —$N(R^5)_2$, $(C_1-C_3)$alkoxy $(C_1-C_3)$alkyl, $(C_1-C_3)$alkyl-C(O)—, oxo, $(C_1-C_3)$haloalkyl-C(O)—, —$SO_2F$, $(C_1-C_3)$alkoxy $(C_1-C_3)$alkoxy, —$CH_2OC(O)N(R^5)_2$, —$CH_2N(H)C(O)O$—$(C_1-C_6)$alkyl, —$CH_2N(H)C(O)N(R^5)_2$, —$CH_2N(H)C(O)(C_1-C_6)$alkyl, —$CH_2$(pyrazolyl), —$CH_2N(H)S(O)_2(C_1-C_6)$alkyl, —$CH_2OC(O)(C_3-C_{12})$heterocyclyl, —$OC(O)N(R^5)_2$, —$OC(O)N(H)(C_1-C_3)$alkyl-O—$(C_1-C_3)$alkyl, —$OC(O)N(H)(C_1-C_3)$alkyl-O—$(C_1-C_3)$alkyl-phenyl-$(C_1-C_3)$alkyl-$N(CH_3)_2$, —$OC(O)N(H)(C_1-C_3)$alkyl-O—$(C_1-C_3)$alkyl-phenyl, —$OC(O)(C_3-C_{12})$heterocyclyl or —$CH_2-(C_3-C_{12})$heterocyclyl, wherein the phenyl of —N(H)C(O)phenyl and —OC(O)N(H)$(C_1-C_3)$alkyl-O—$(C_1-C_3)$alkyl-phenyl is optionally substituted with —C(O)H or —OH, and the $(C_3-C_{12})$heterocyclyl of —$CH_2$—$(C_3-C_{12})$heterocyclyl is optionally substituted with oxo;

Q is a bond or O;

each $R^7$ is independently halogen, hydroxy, —C(O)H, $(C_1-C_4)$alkyl, $(C_1-C_4)$alkoxy, $(C_1-C_4)$haloalkyl, $(C_1-C_4)$hydroxyalkyl or —$N(R^5)_2$;

L' is a covalent bond or a bivalent, saturated or unsaturated, straight or branched $C_1-C_{15}$ hydrocarbon chain wherein 0-5 methylenes of L' are replaced by X;

each X is independently —O—, —N(R)—, —S—, —OC(O)—, —C(O)—, —C(H)(F)—, —$C(F)_2$—, -Cy-, —S(O)—, —$S(O)_2$—, —$N(R)S(O)_2$—, —N(R)C(O)—, —OC(O)N(R)—, —N(R)C(O)N(R)—,

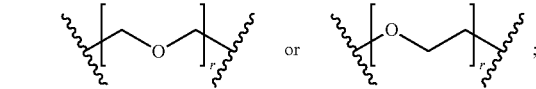

each -Cy- is independently an optionally substituted bivalent ring selected from a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur;

each R is independently hydrogen or $(C_1-C_3)$alkyl;

r is 1, 2, 3, 4, 5, 6, 7, 8, 9, or 10; and

Degron is a cereblon binding moiety.

3. The compound of claim 2, wherein Y is O.

4. The compound of claim 2, wherein $R^1$ is hydrogen.

5. The compound of claim 3, wherein $R^2$ is -L-$(C_3-C_{12})$heterocyclyl, wherein the $(C_3-C_{12})$heterocyclyl of -L-$(C_3-C_{12})$heterocyclyl is optionally substituted with one or more $R^6$.

6. The compound of claim 5, wherein L is methylene.

7. The compound of claim 2, wherein $R^3$ is

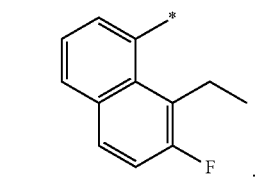

8. The compound of claim 2, wherein $R^3$ is

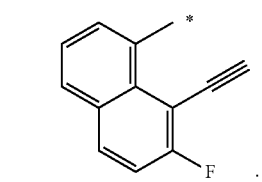

9. The compound of claim 2, wherein $R^4$ is halogen.

10. The compound of claim 9, wherein $R^4$ is fluoro.

11. The compound of claim 2, wherein each $R^6$ is independently halogen, hydroxy, ($C_1$-$C_3$)hydroxyalkyl, ($C_1$-$C_3$) alkyl, ($C_1$-$C_3$)haloalkyl, ($C_1$-$C_3$)alkoxy or cyano.

12. The compound of claim 1, wherein L' is a bivalent, saturated or unsaturated, straight or branched $C_1$-$C_{15}$ hydrocarbon chain wherein 1 or 2 methylenes of L' are replaced by Cy and 1-3 methylenes of L' are replaced by X, wherein:
each X is independently —O—, —C(O)—, —N(R)— or —N(R)C(O)—.

13. The compound of claim 12, wherein each -Cy- is independently a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur.

14. The compound of 13, wherein each -Cy- is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked via a nitrogen atom.

15. The compound of claim 12, wherein each -Cy- is independently selected from cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, or 3,9-diazaspiro[5.5] undecanylene.

16. The compound of claim 1, wherein L' comprises -Cy$^1$-(CH$_2$)$_{0-1}$—X—(CH$_2$)$_{0-1}$-Cy$^2$-, wherein Cy$^1$ and Cy$^2$ are each independently -Cy-.

17. The compound of claim 16, wherein Cy$^1$ is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked via a nitrogen atom.

18. The compound of claim 17, wherein Cy$^1$ is piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, or 3,9-diazaspiro[5.5]undecanylene.

19. The compound of claim 16, wherein Cy$^2$ is cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3] heptanylene, 7-azaspiro[3.5]nonanylene, 3-azabicyclo[3.2.1]octanylene, 2,7-diazaspiro[3.5]nonanylene, or 3,9-diazaspiro[5.5]undecanylene.

20. The compound of claim 16, wherein X is O or N(R).

21. The compound of claim 20, wherein R is H.

22. The compound of claim 1, wherein Degron is

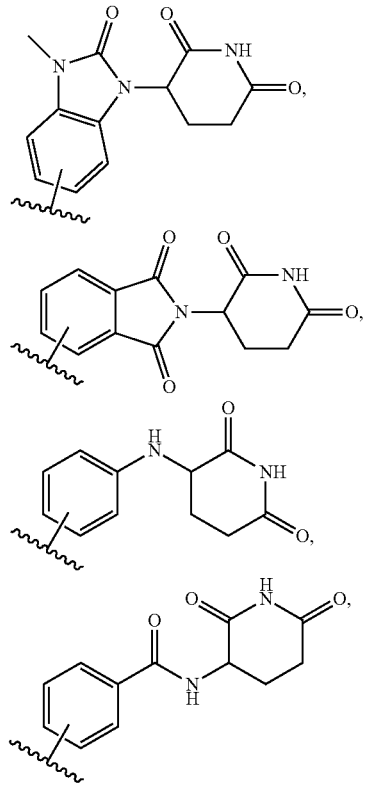

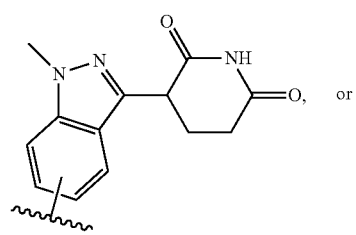

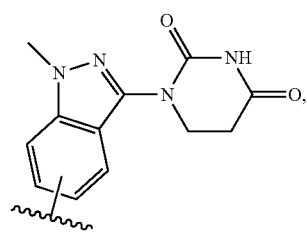

wherein one or more of the hydrogen atoms on the benzene ring of the Degron is optionally replaced with a fluorine atom.

23. The compound of claim 22, wherein Degron is

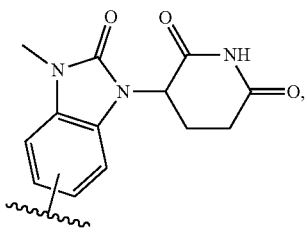

wherein one or more of the hydrogen atoms on the benzene ring of the Degron is optionally replaced with a fluorine atom.

24. A pharmaceutical composition comprising a compound of claim 1, or a pharmaceutically acceptable salt thereof, and a pharmaceutically acceptable carrier.

25. A pharmaceutical combination comprising a compound of claim 1, or a pharmaceutically acceptable salt thereof, and at least one additional therapeutic agent.

26. A compound, or a pharmaceutically acceptable salt thereof, selected from:

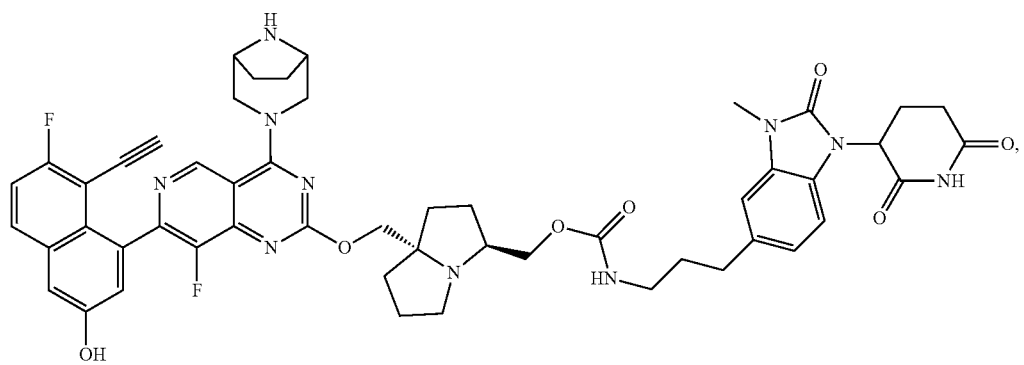

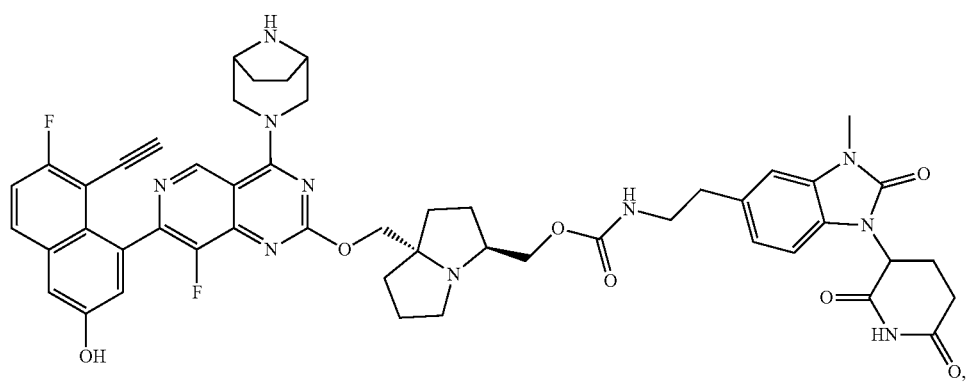

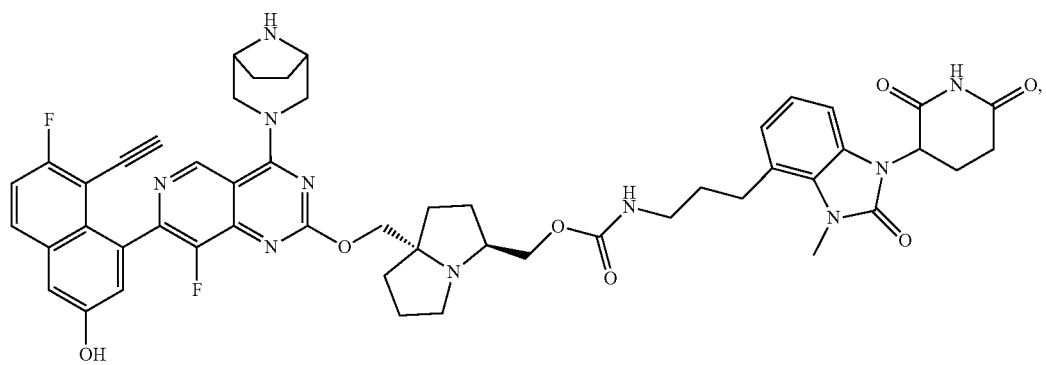

1335
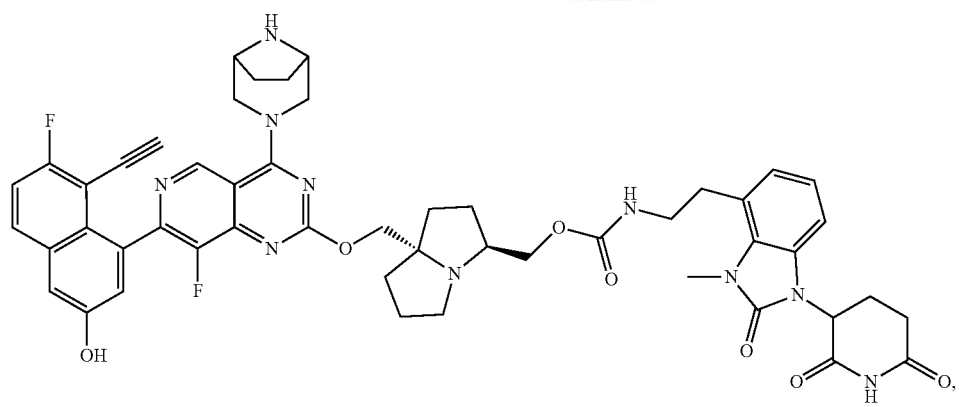
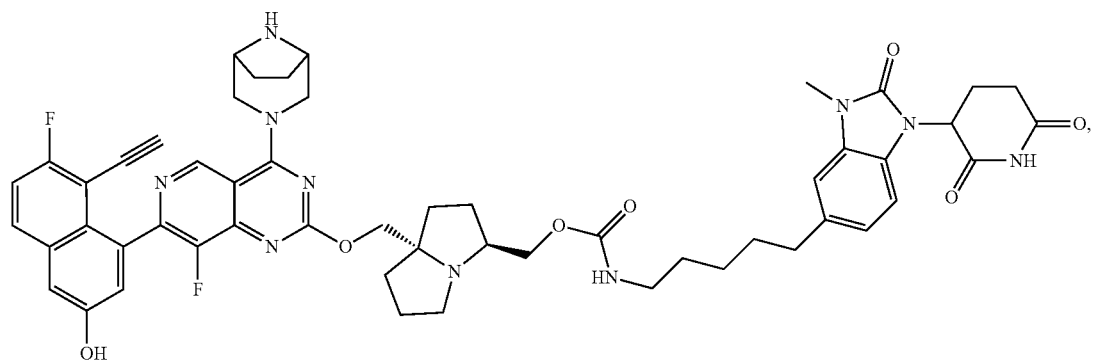
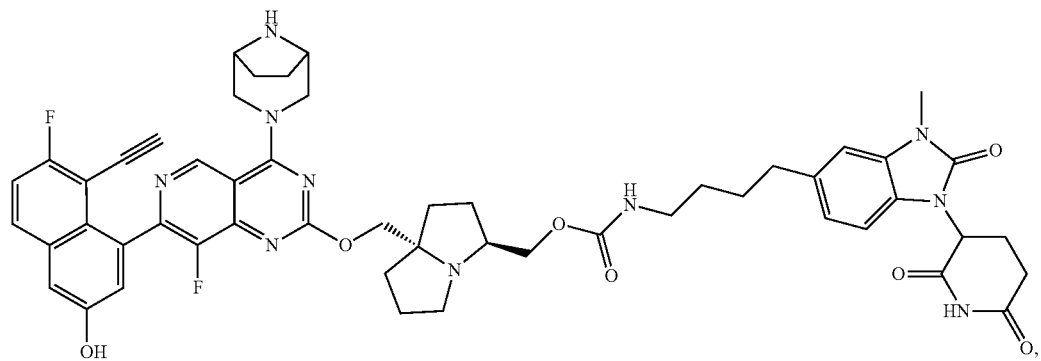
1336
-continued
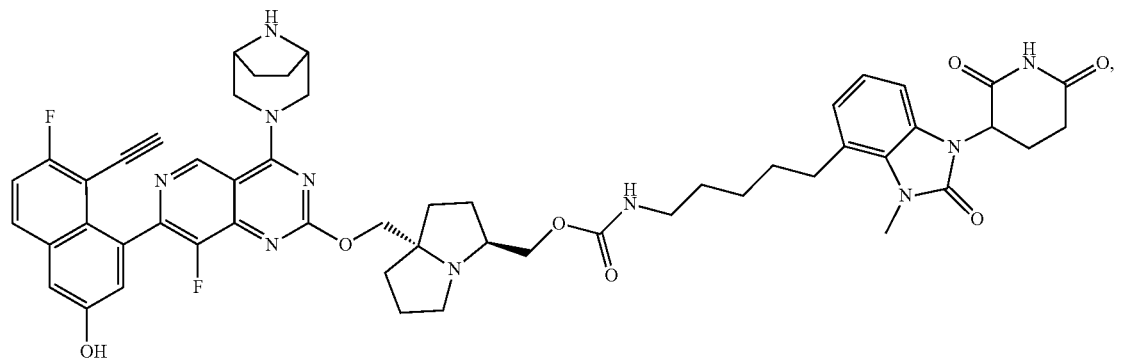

1337
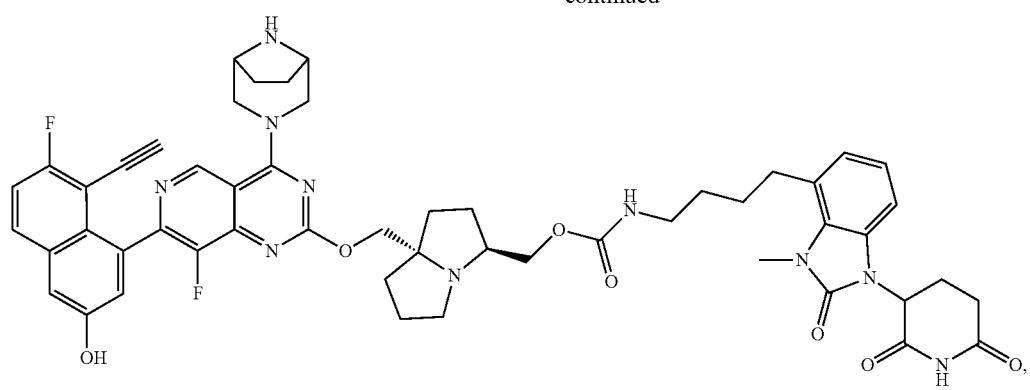
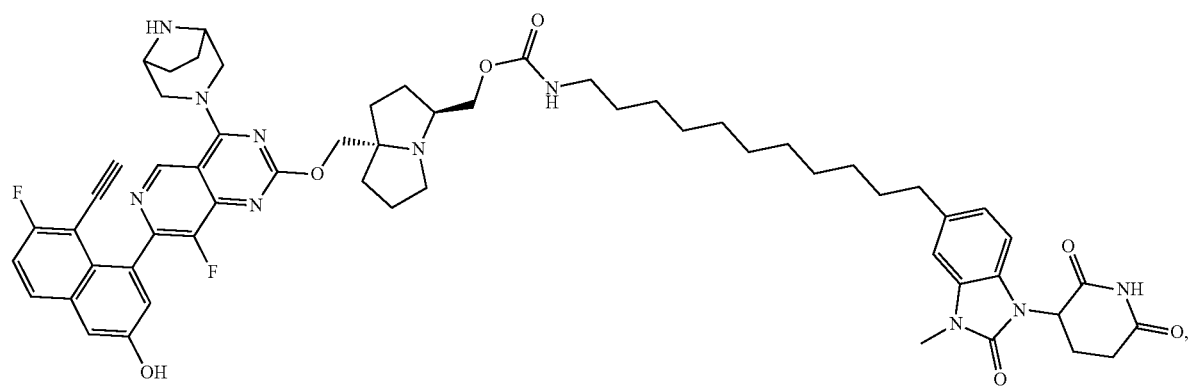
1338
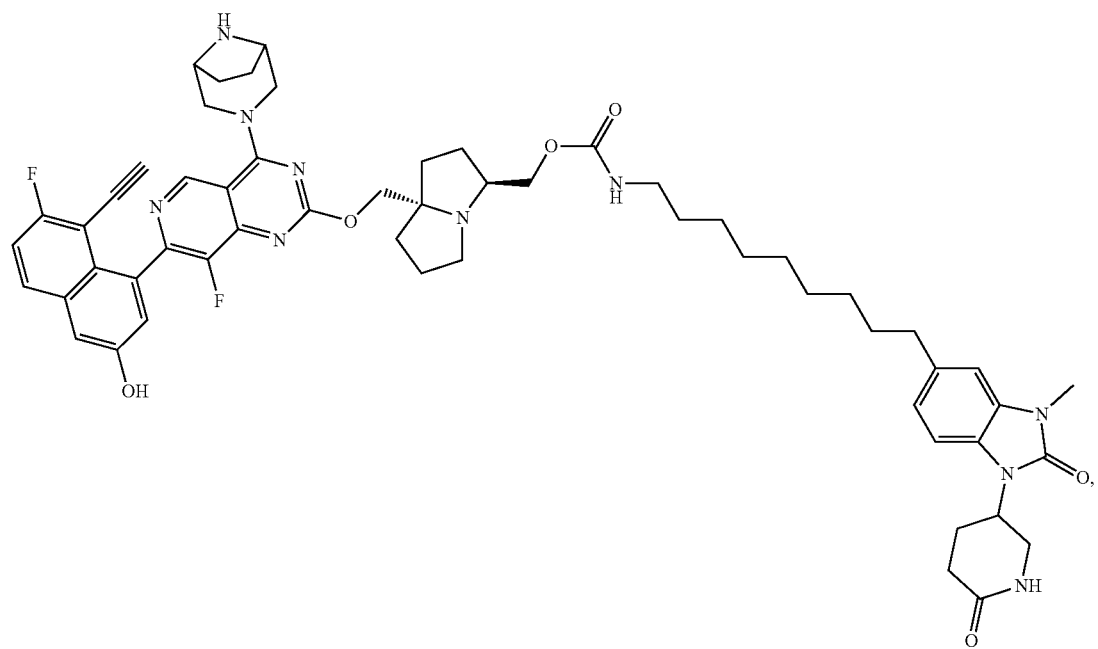

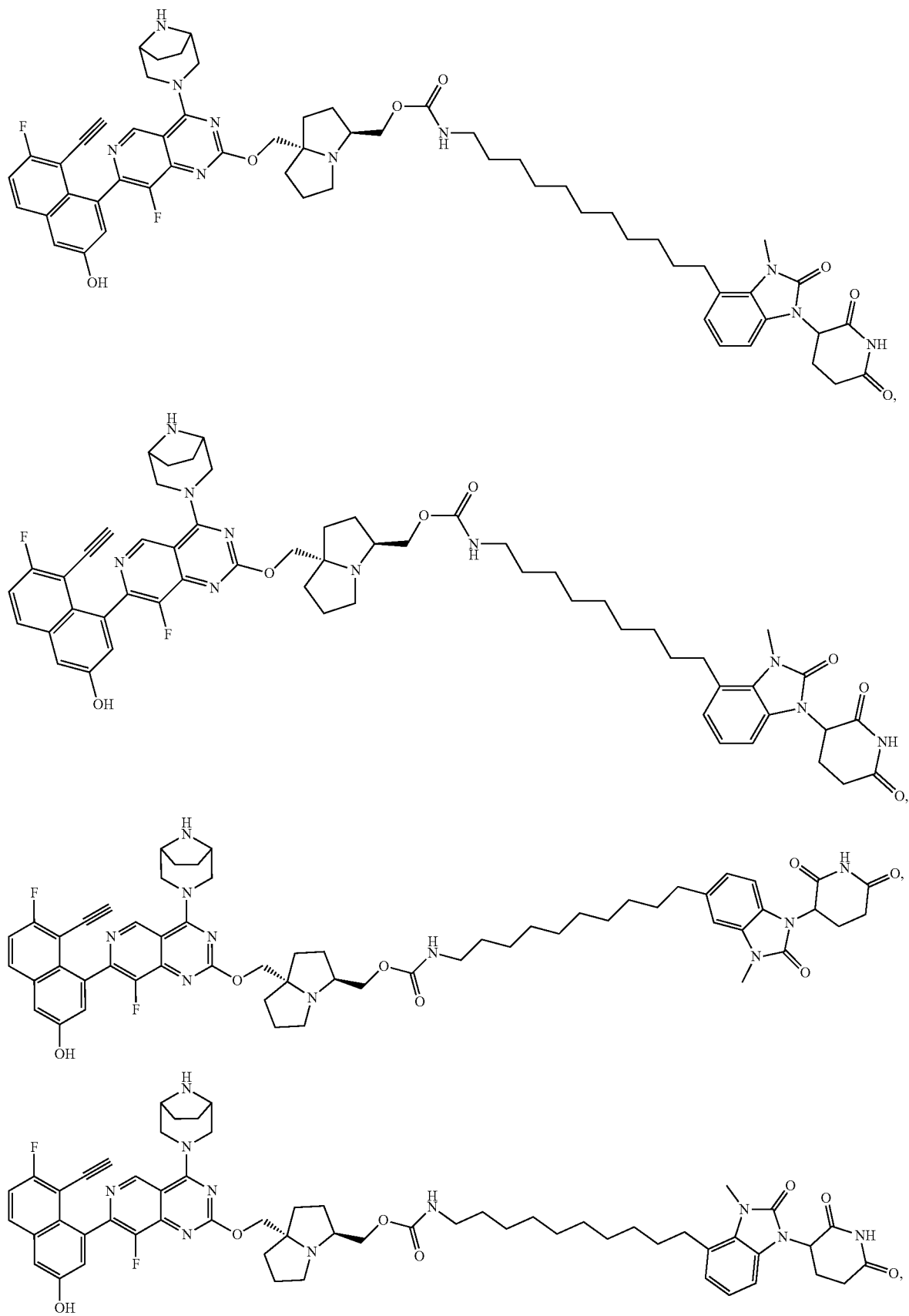

1341 1342
-continued
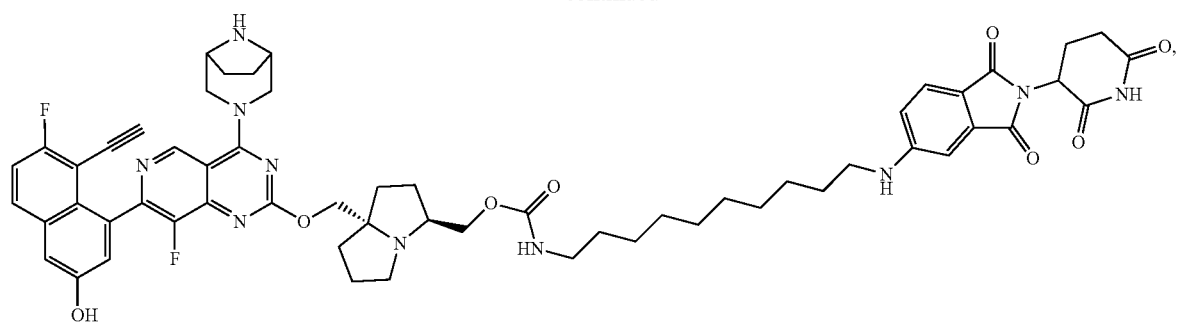
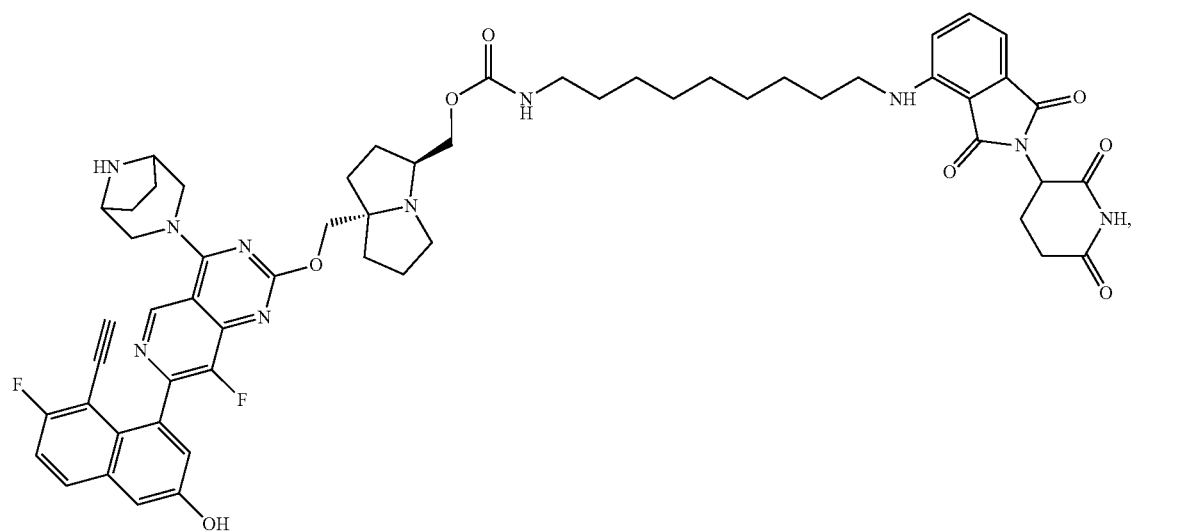
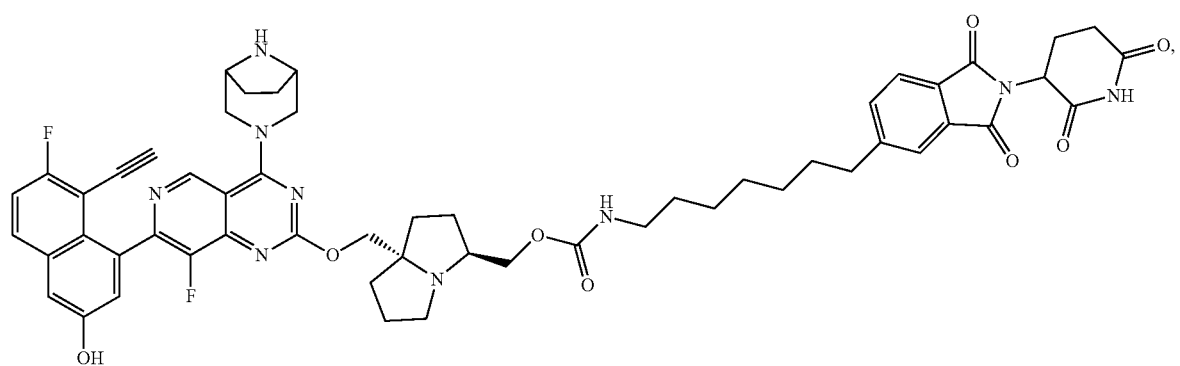
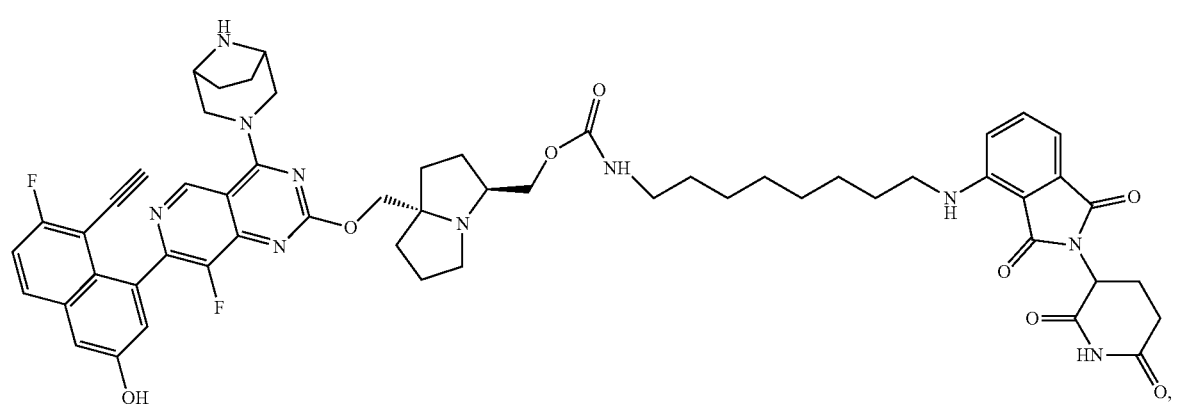

1343
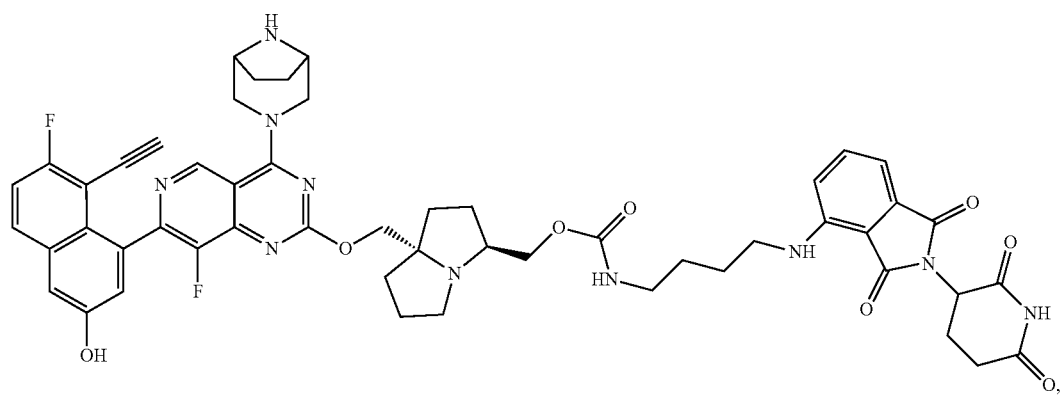
1344
-continued
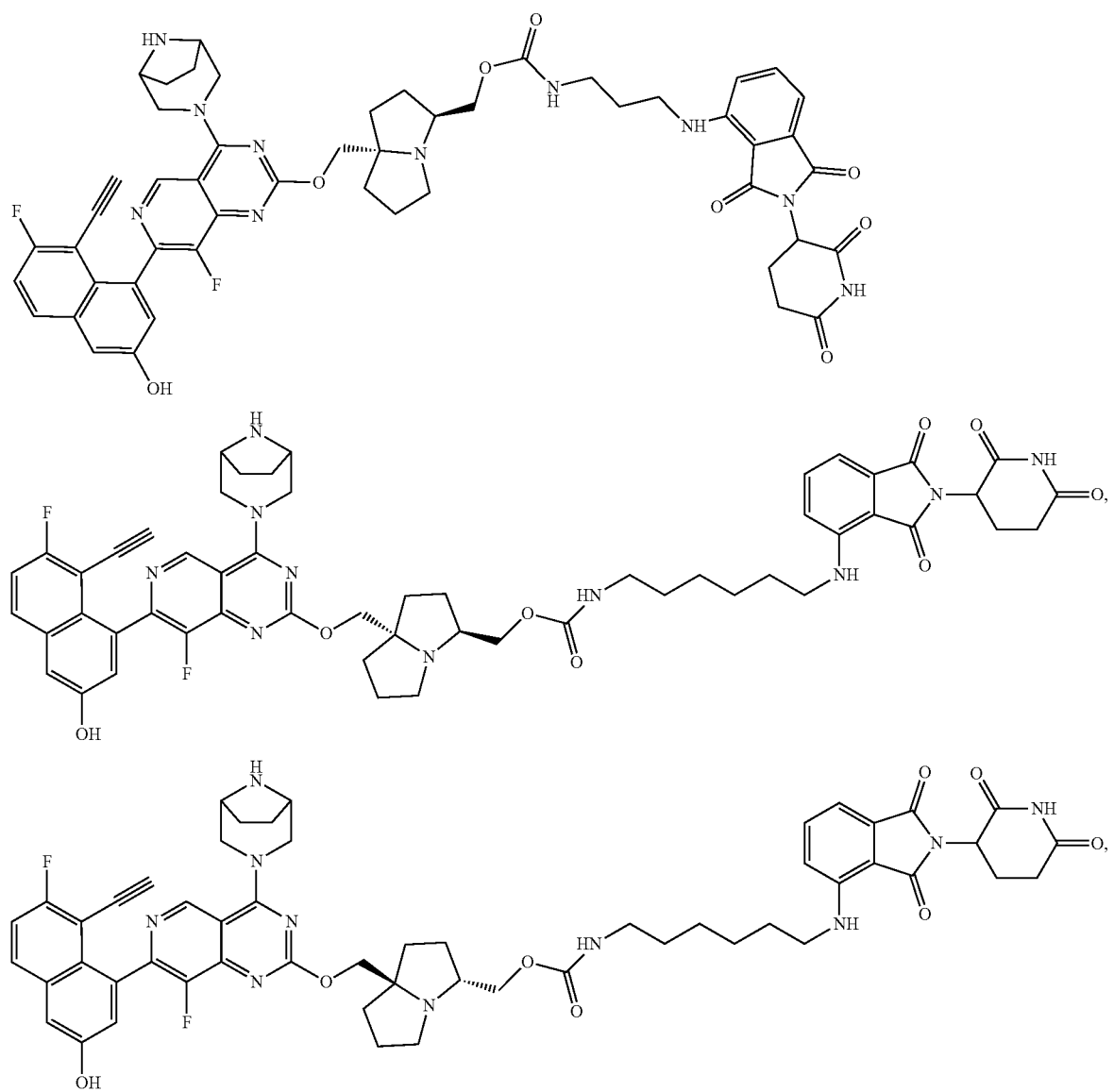

1345
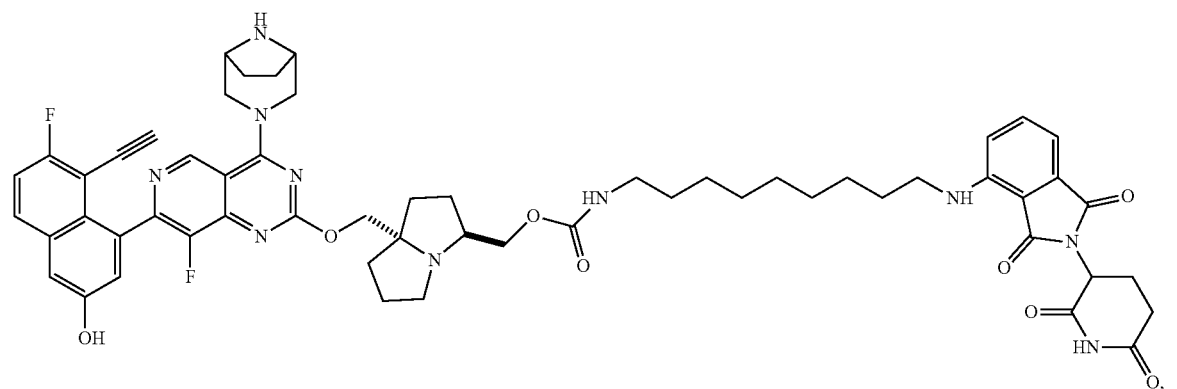
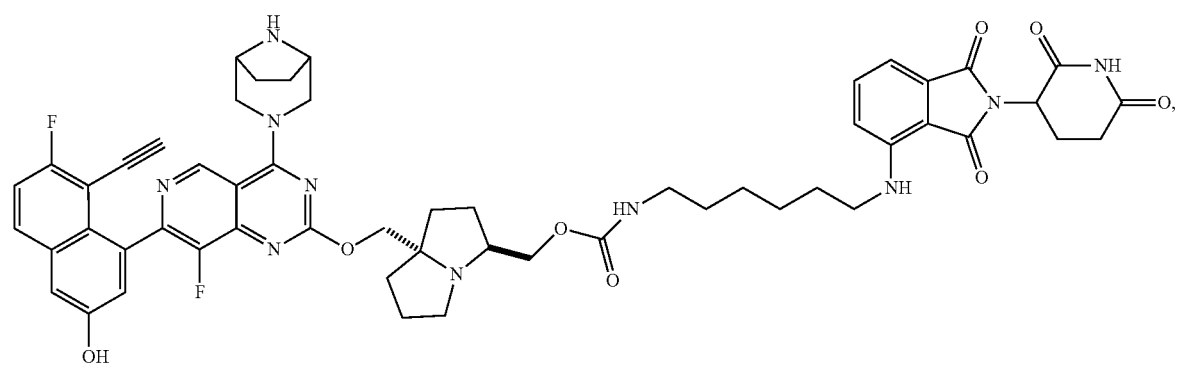
1346
-continued
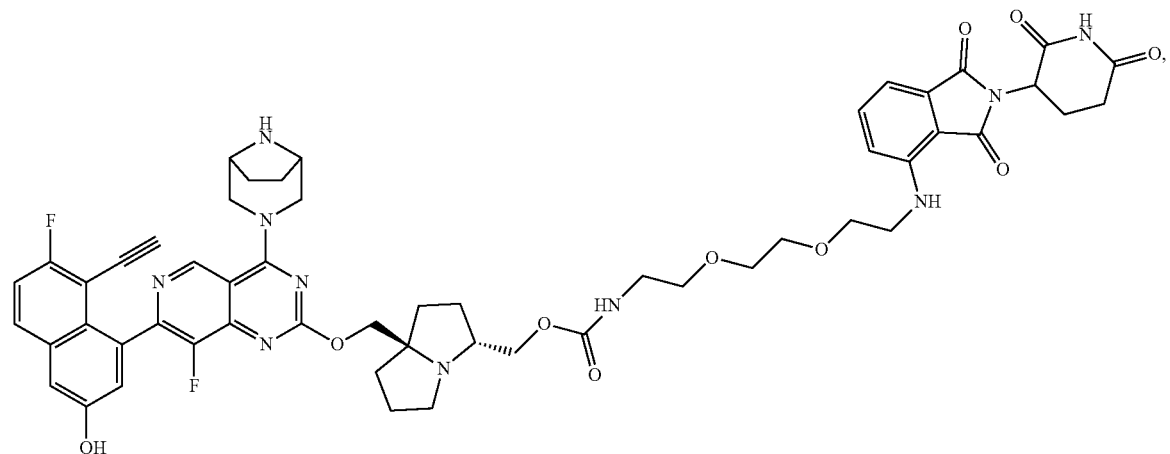
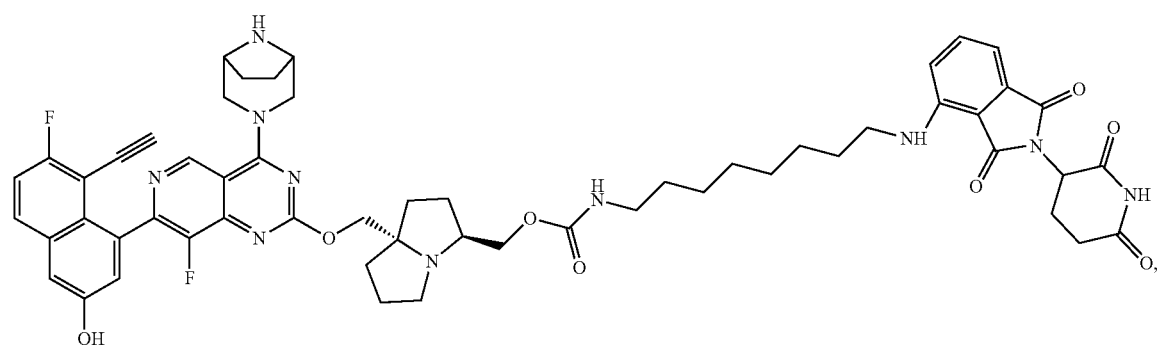

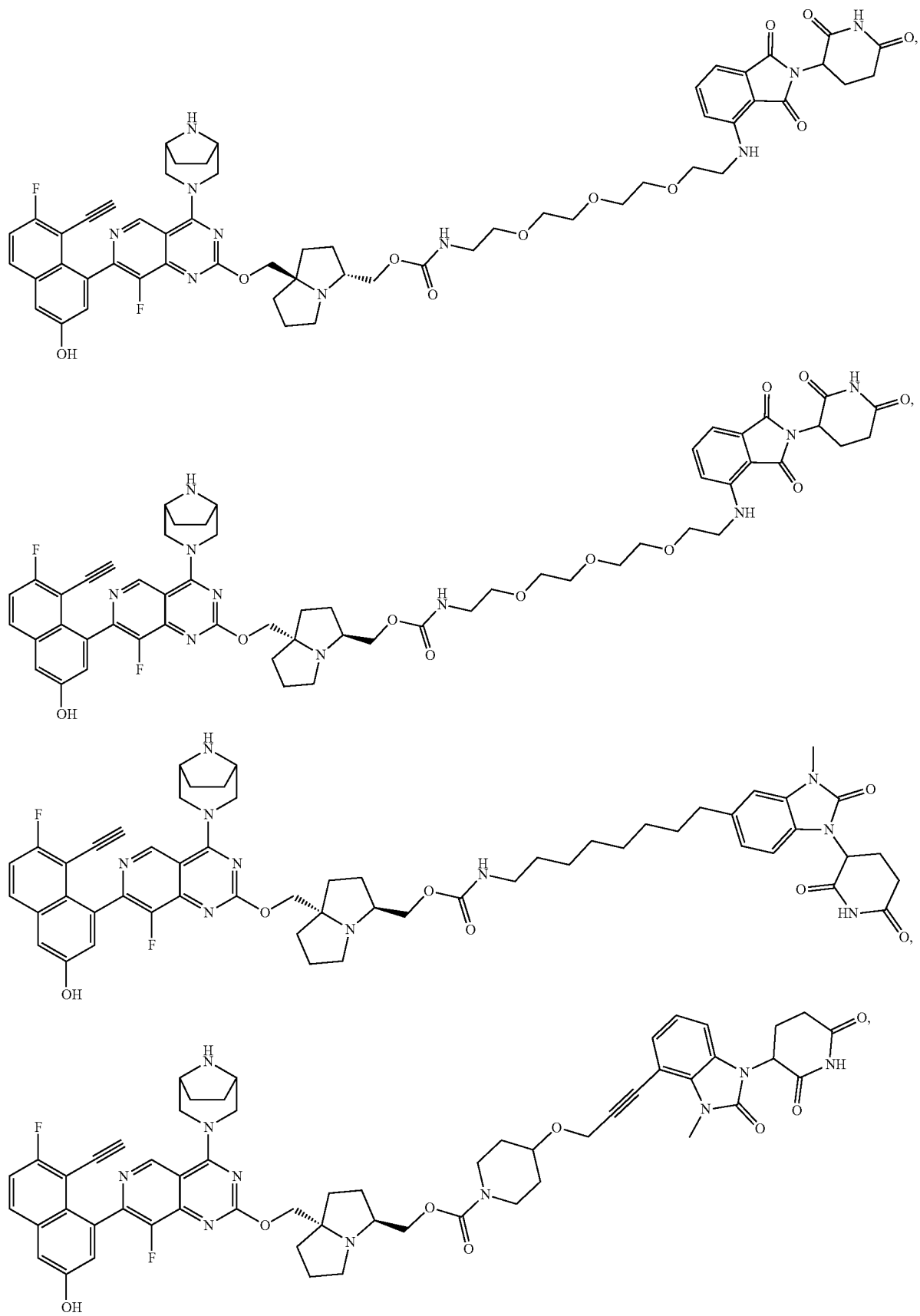

1349 1350
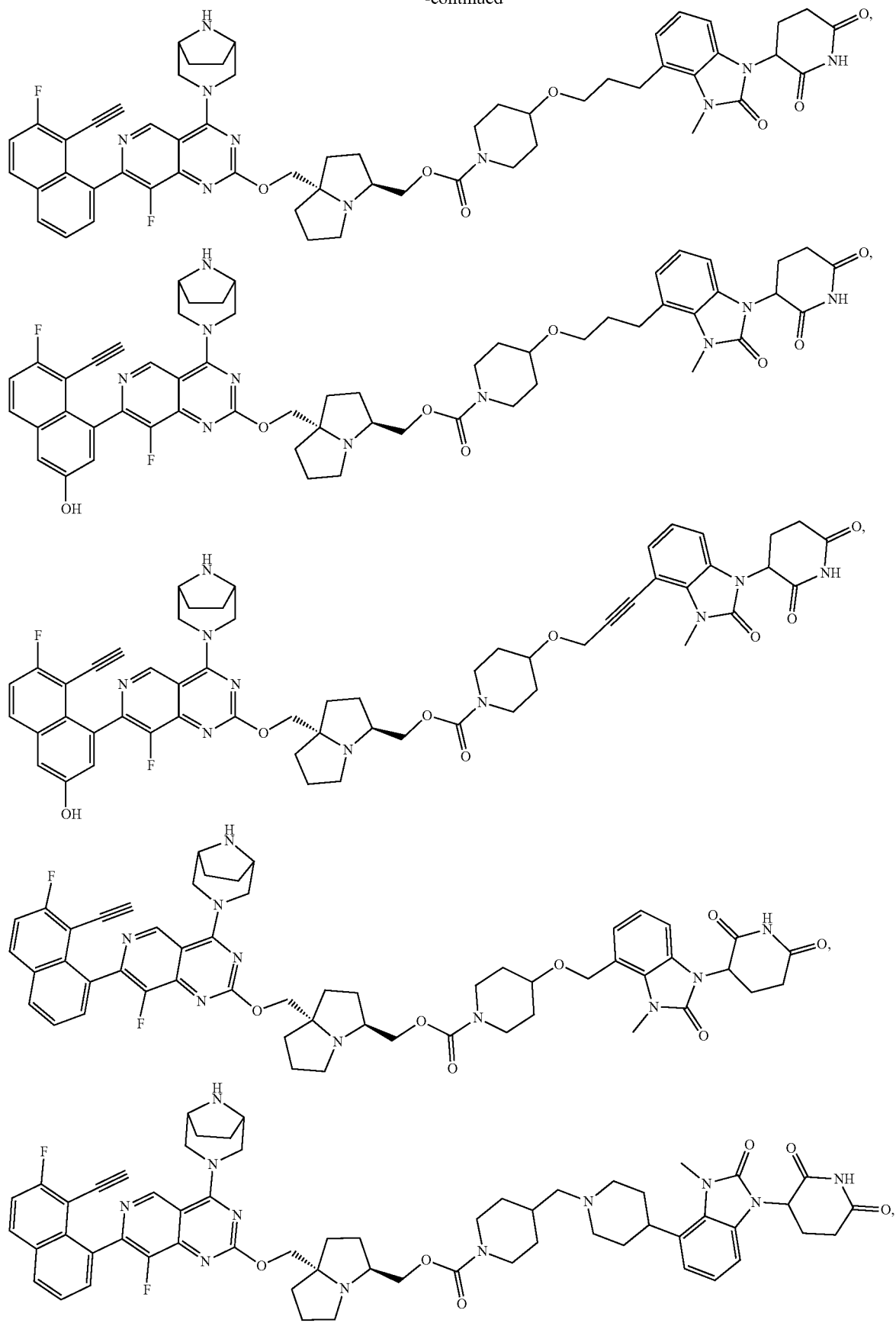

1351
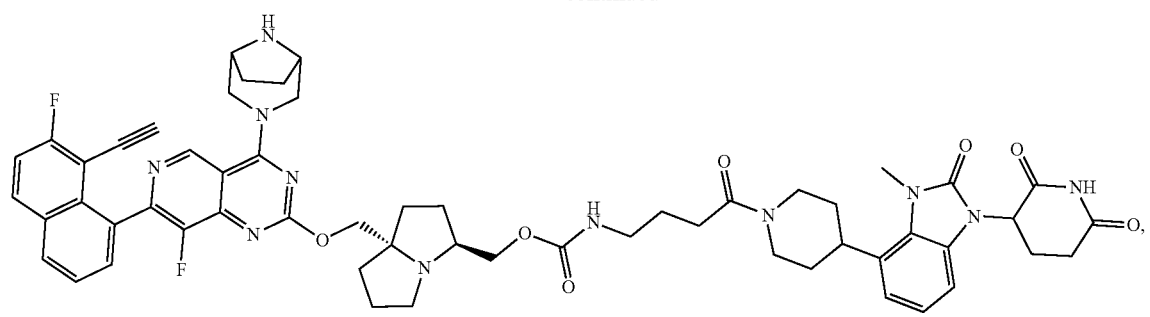
1352
-continued
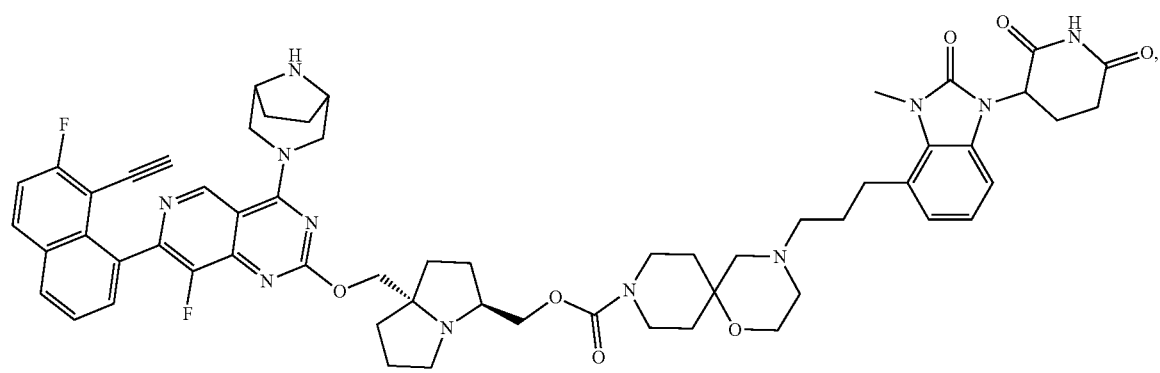
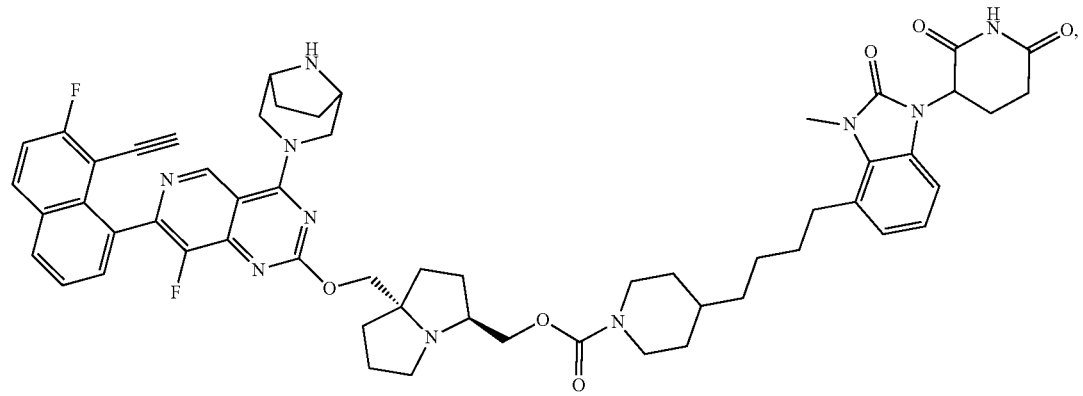
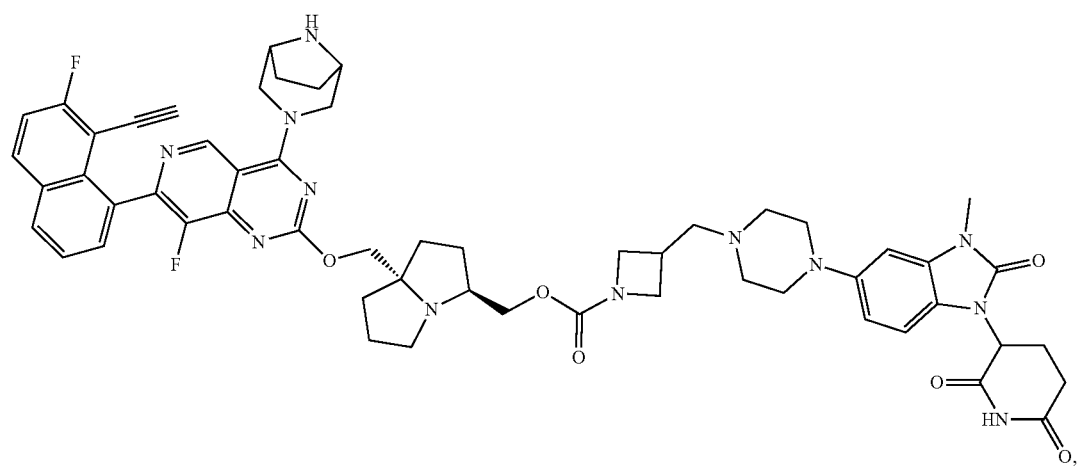

1353
-continued
1354
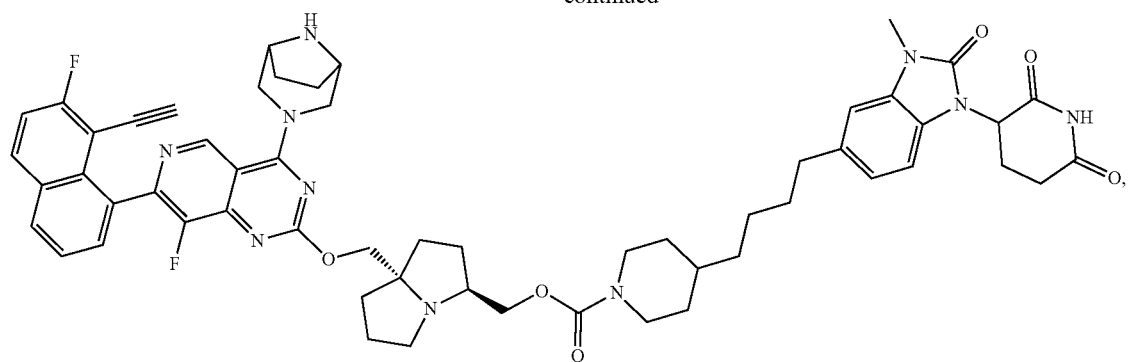
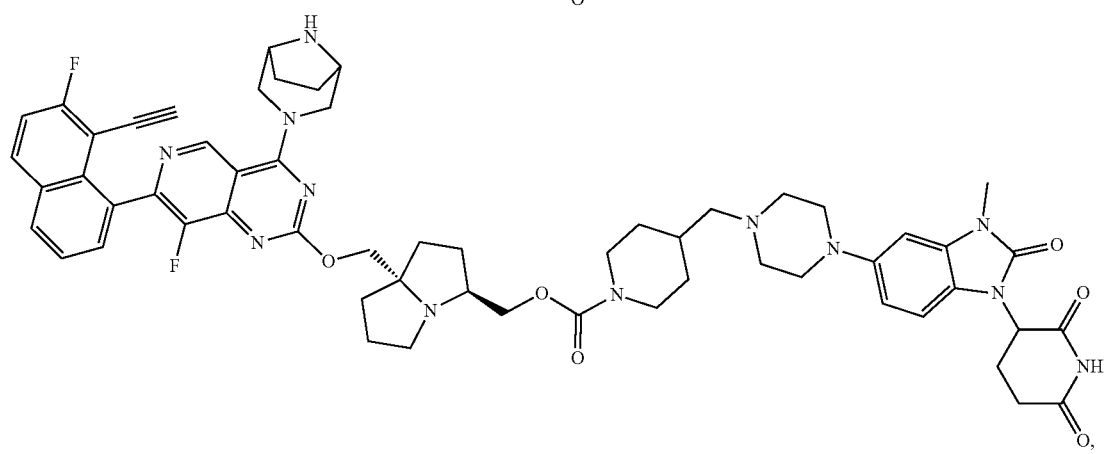
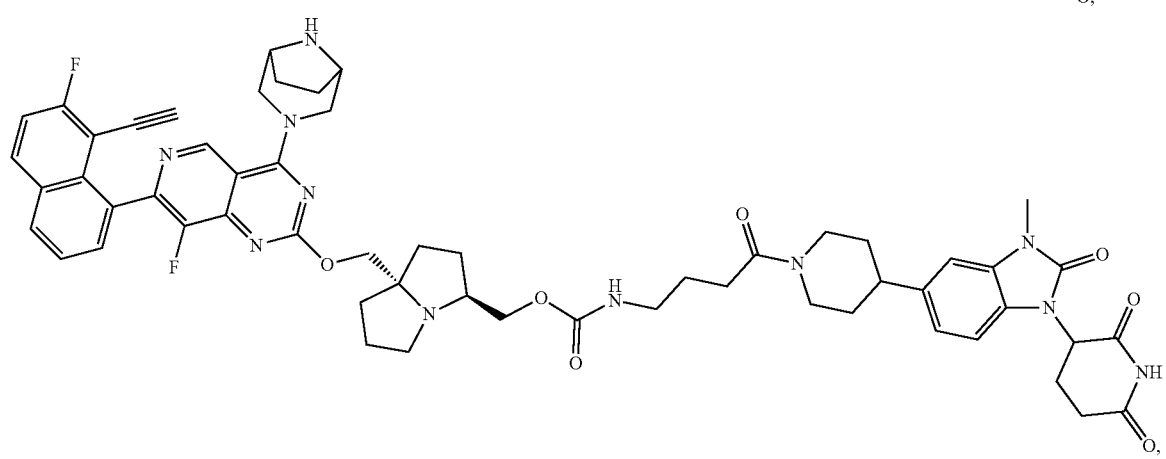
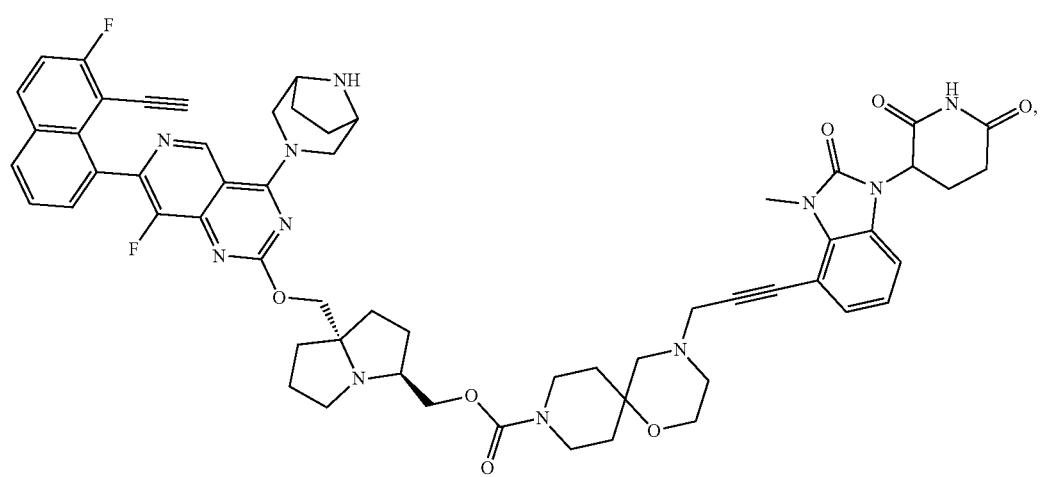

-continued
1355
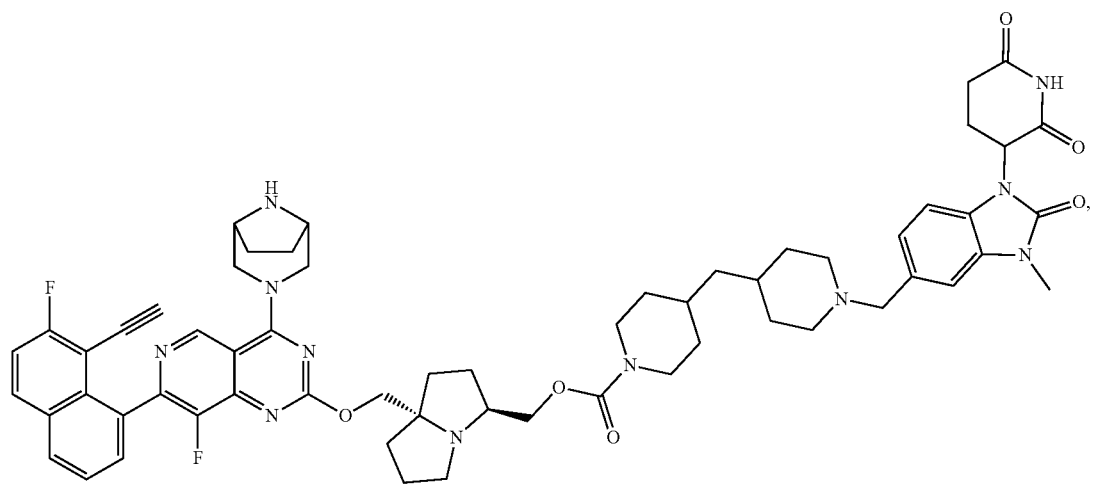
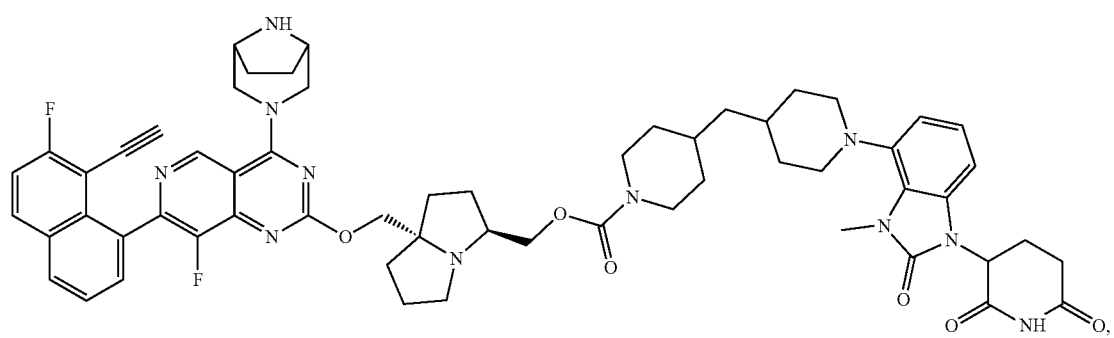
1356
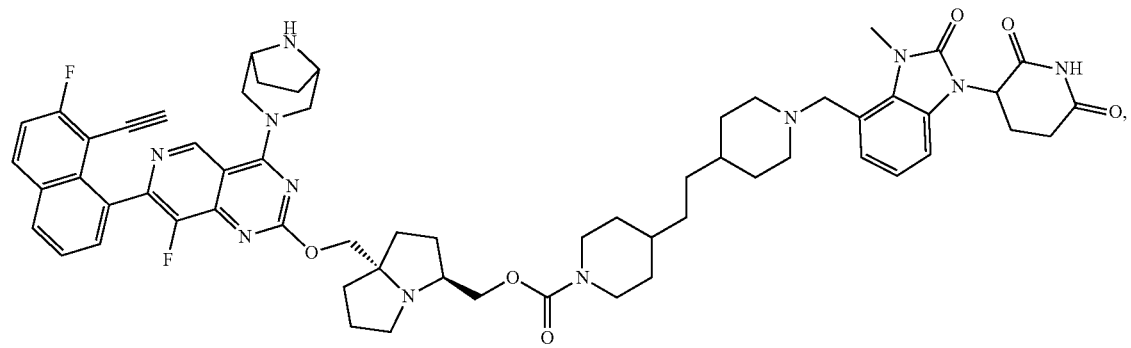
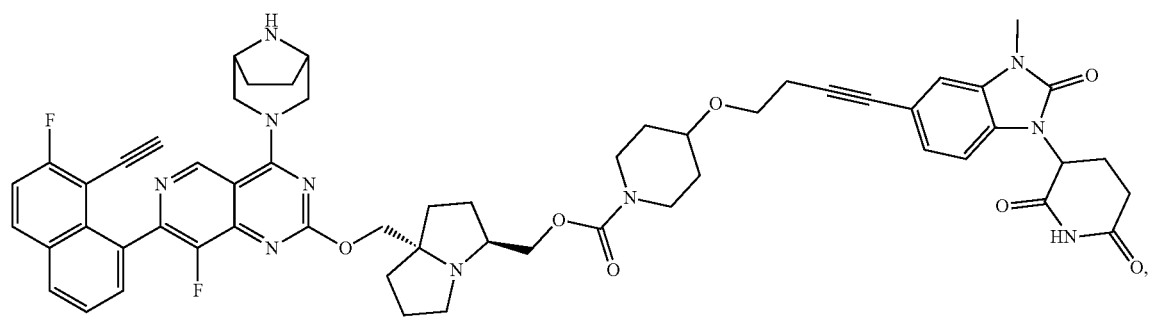

-continued
1357
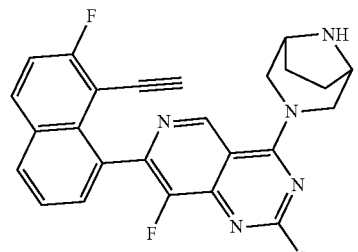
1358
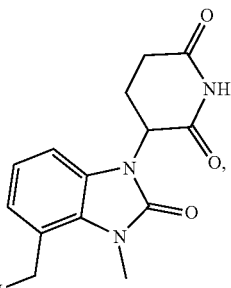
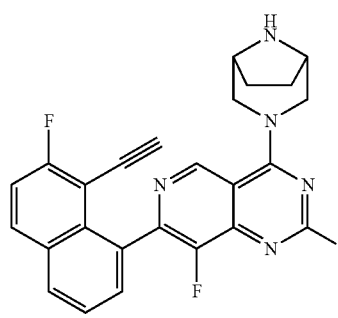
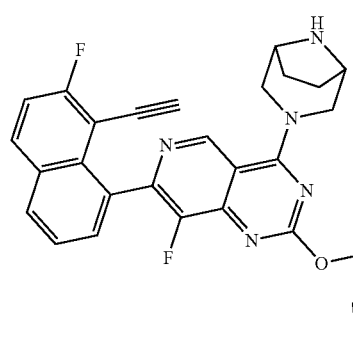
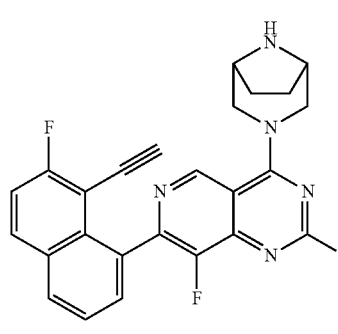

-continued
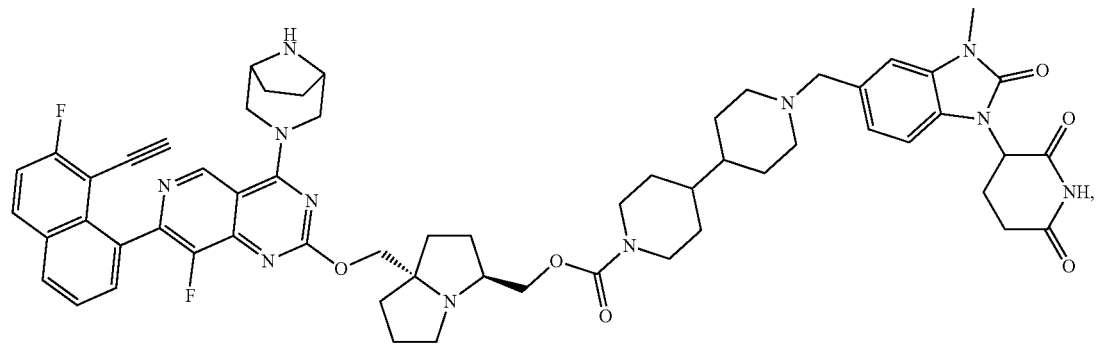
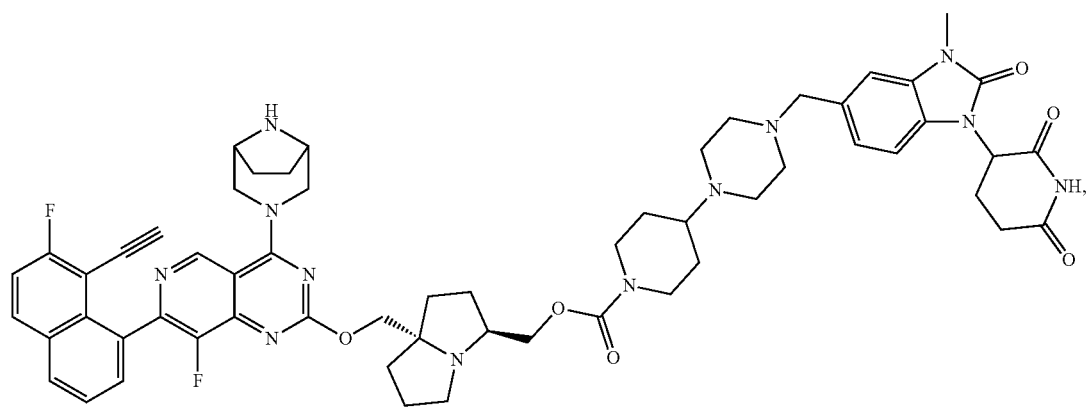
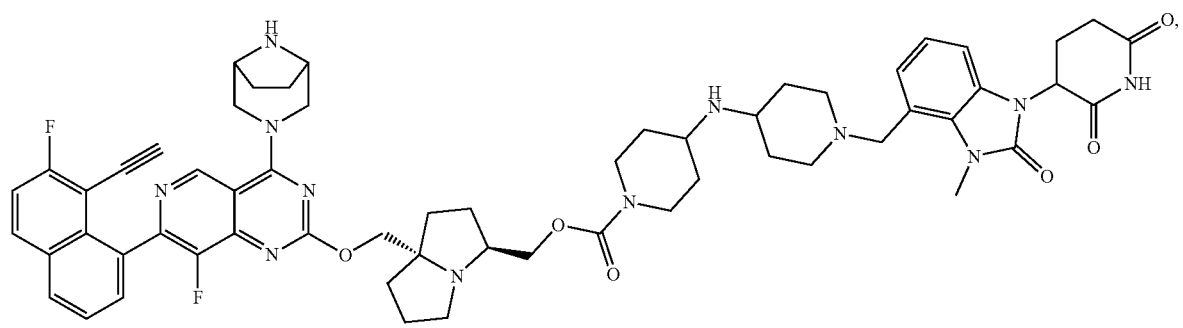
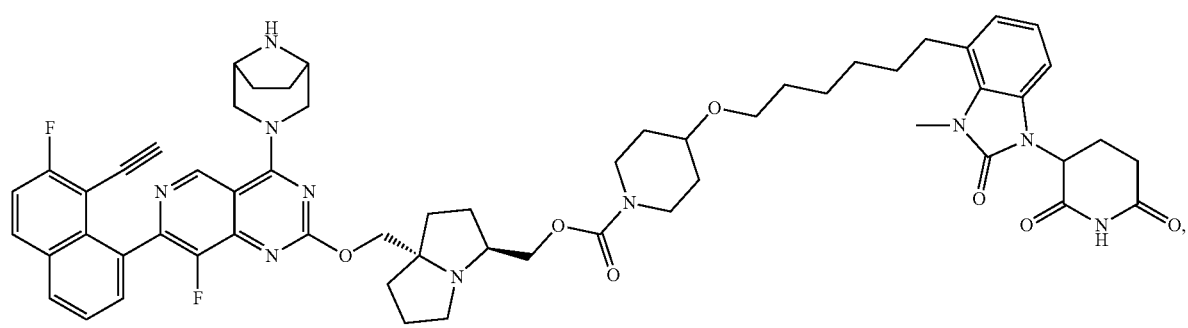

1361
1362
-continued
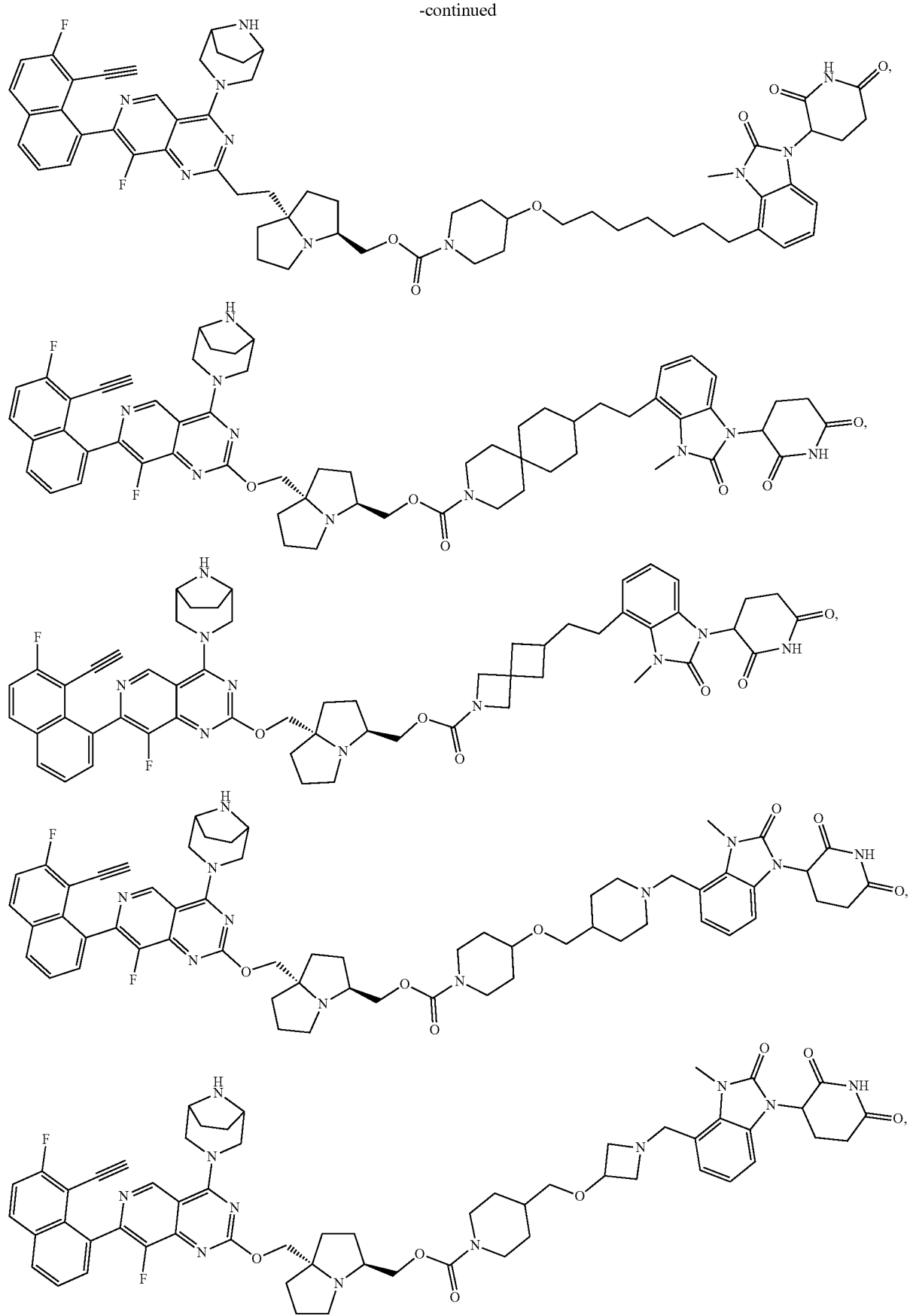

1363
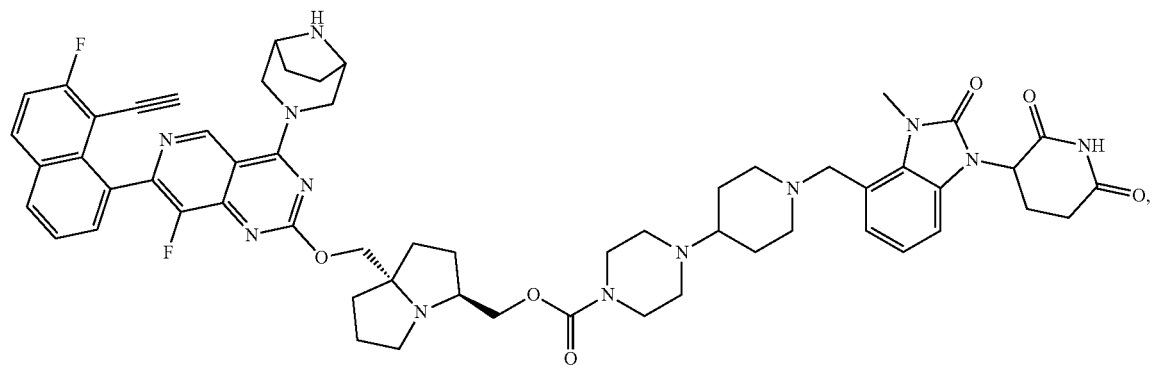
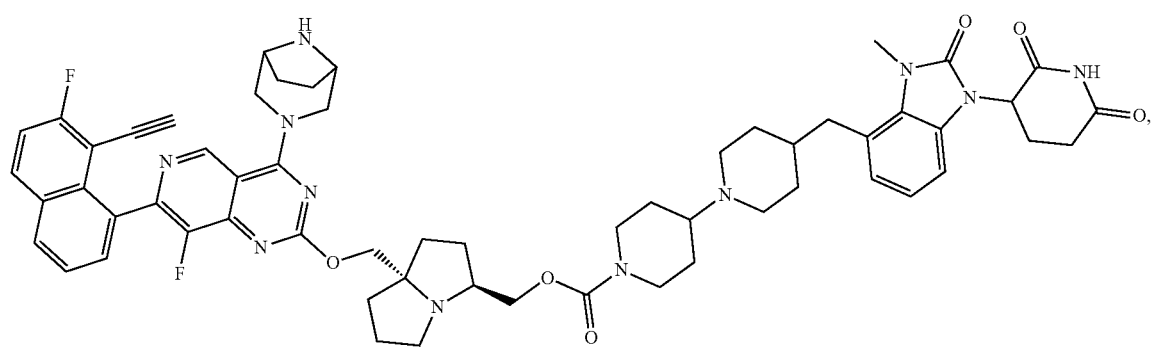
1364
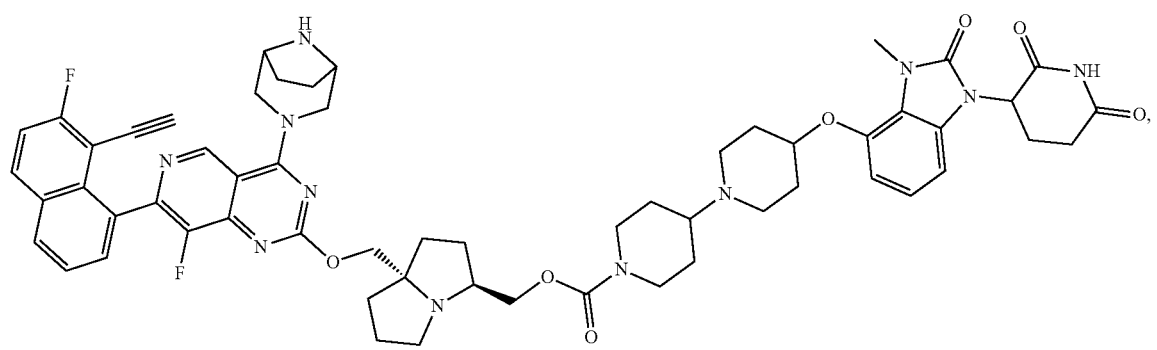
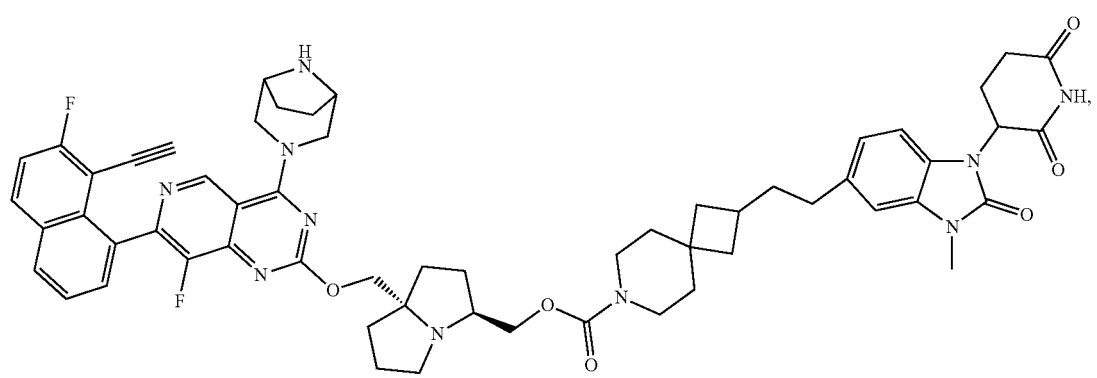

1365
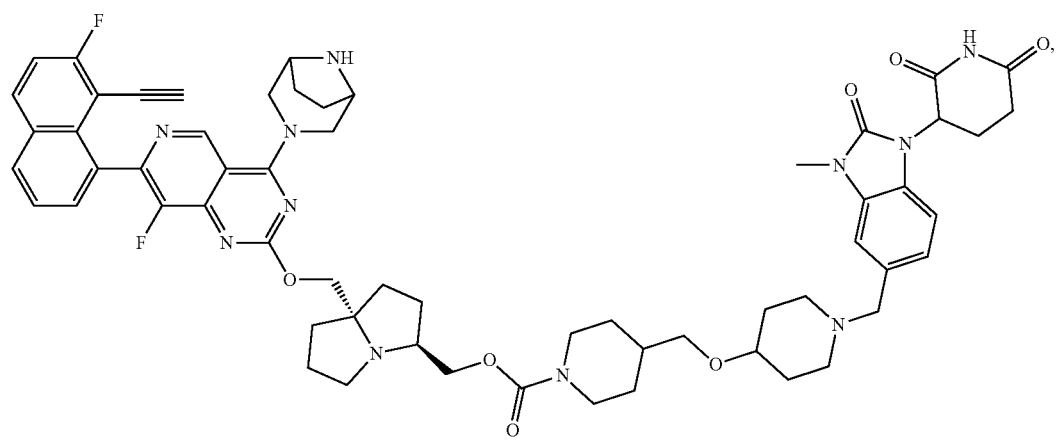
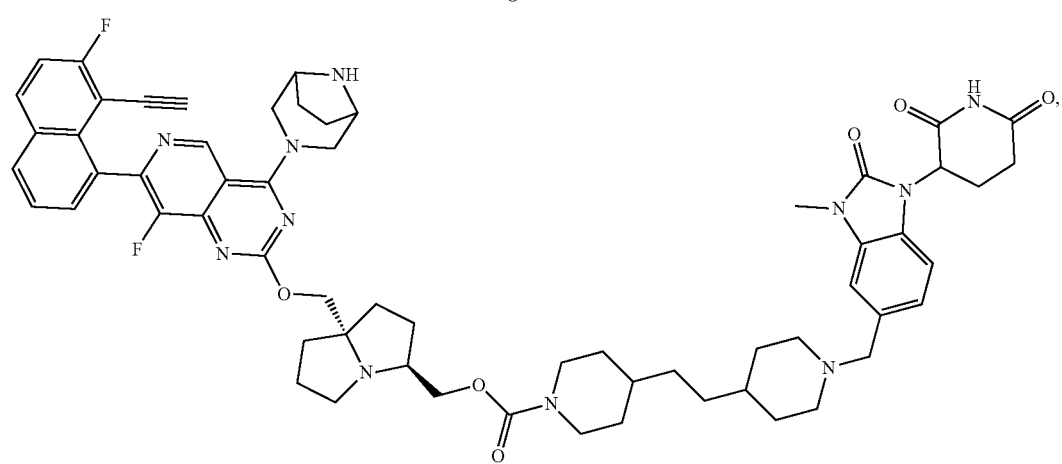
-continued
1366
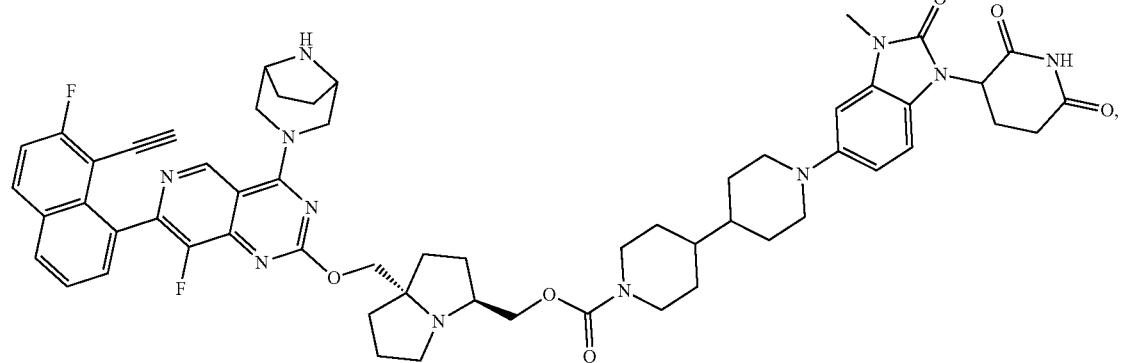
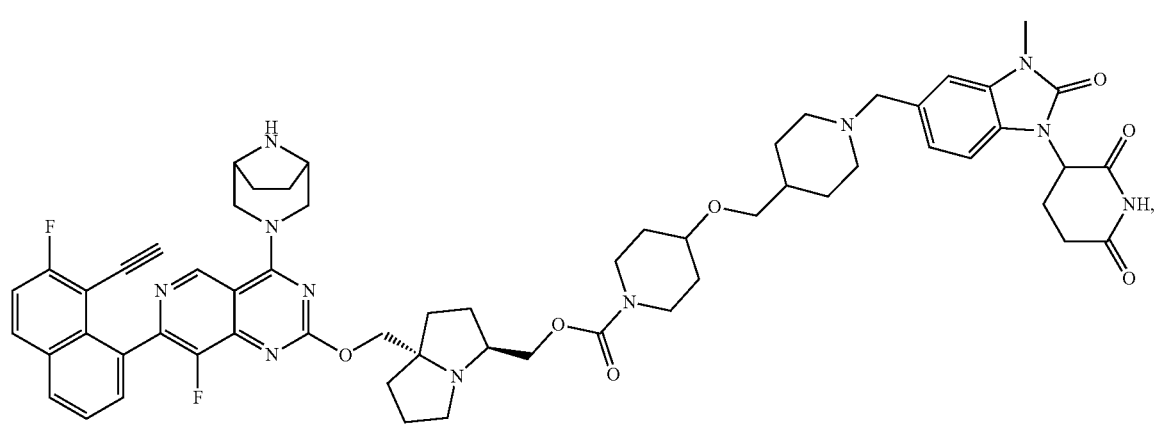

1367
-continued
1368
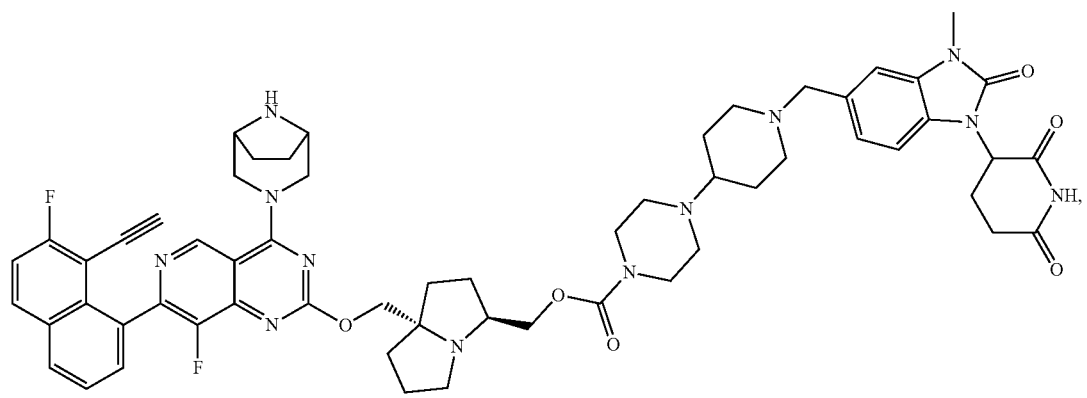
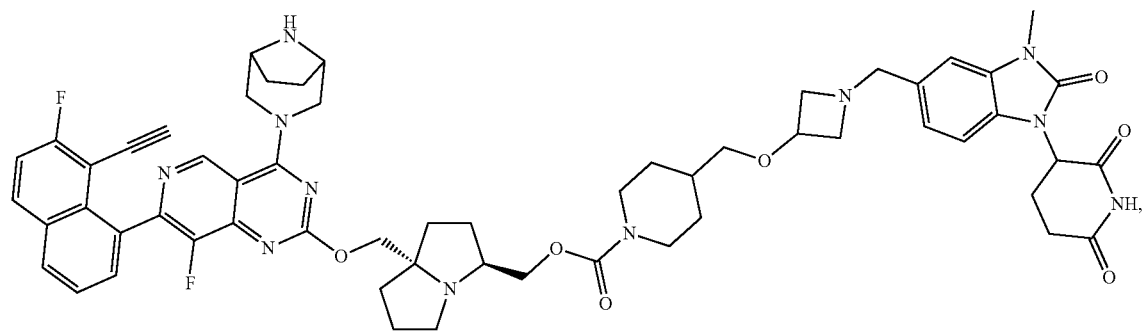
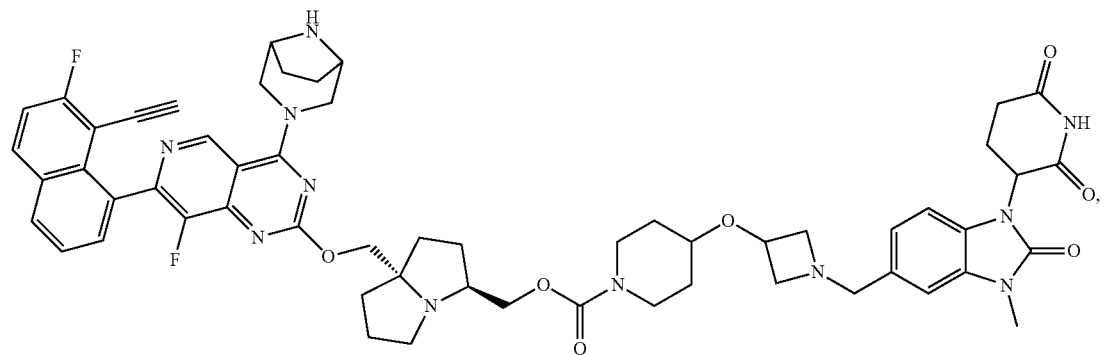
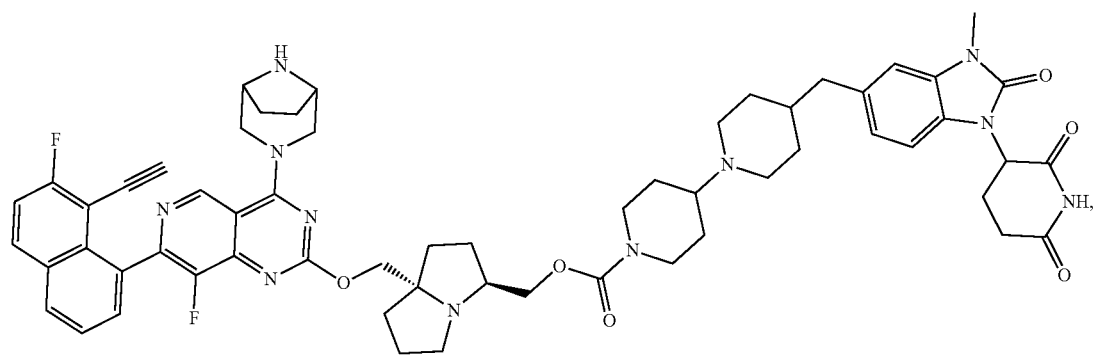

1369
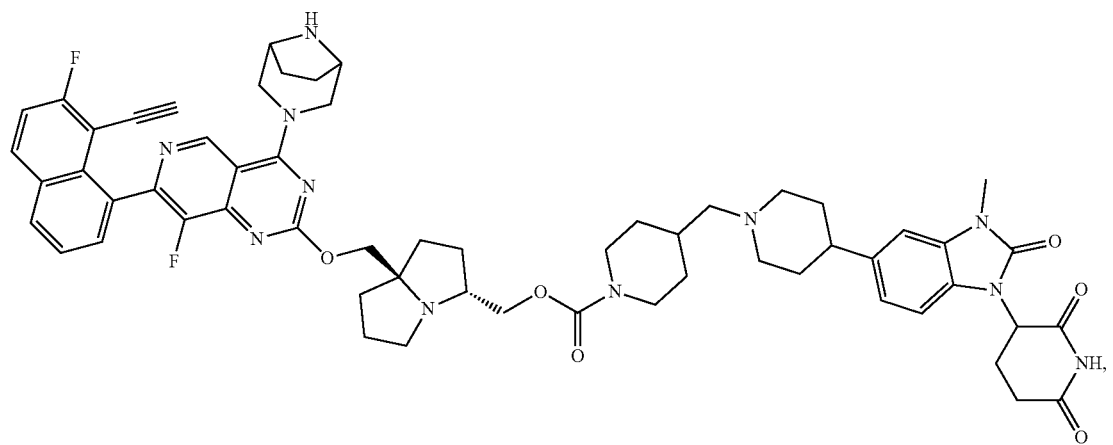
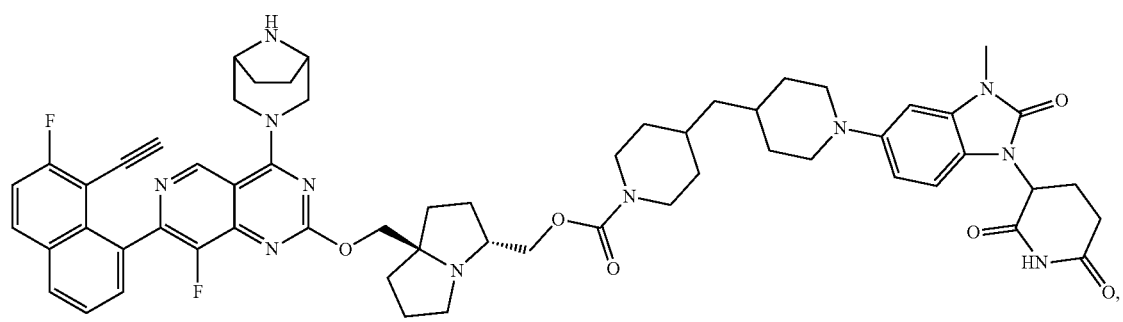
1370
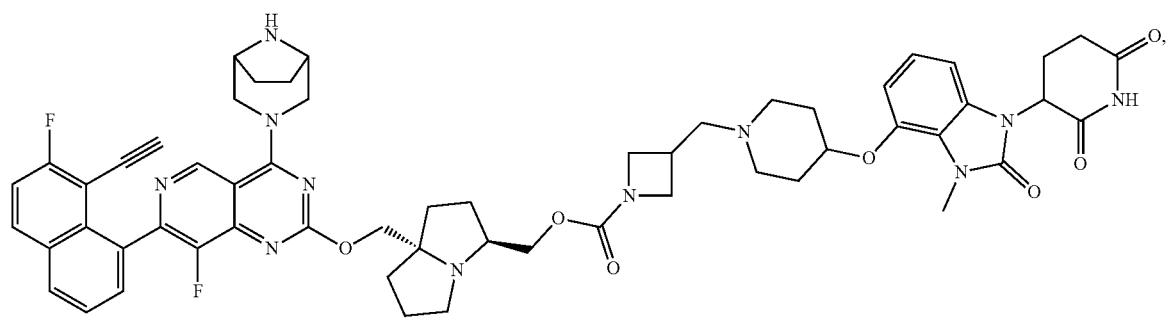
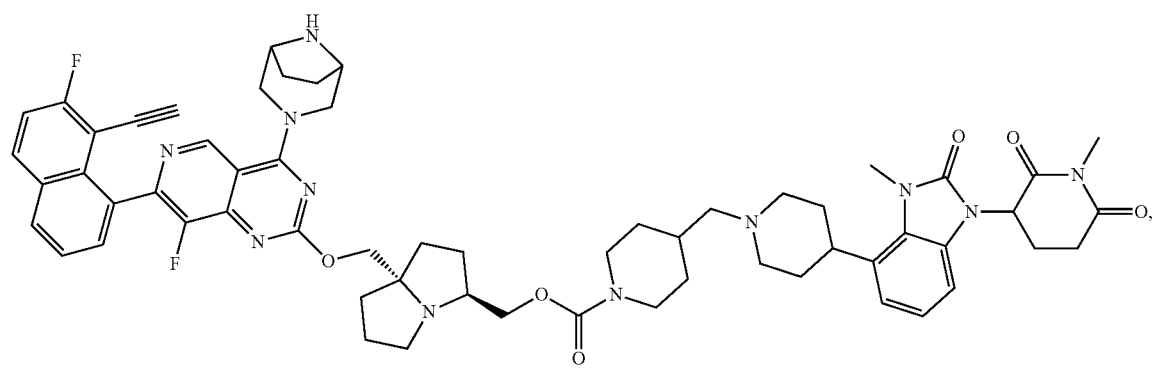

-continued
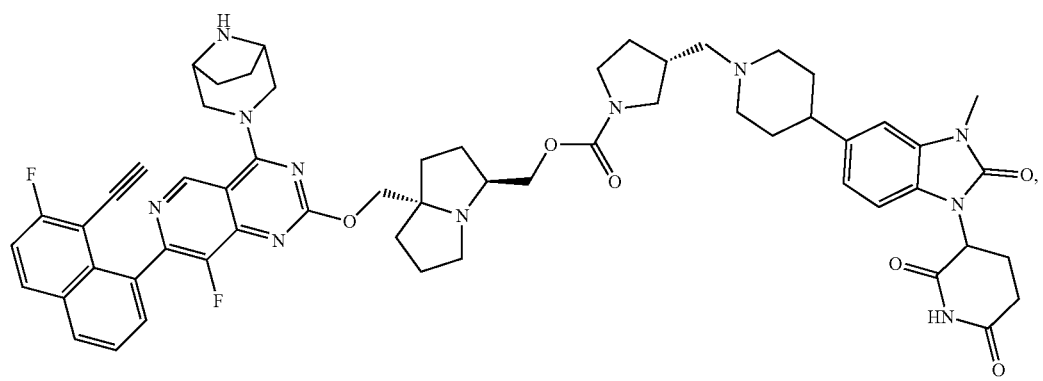
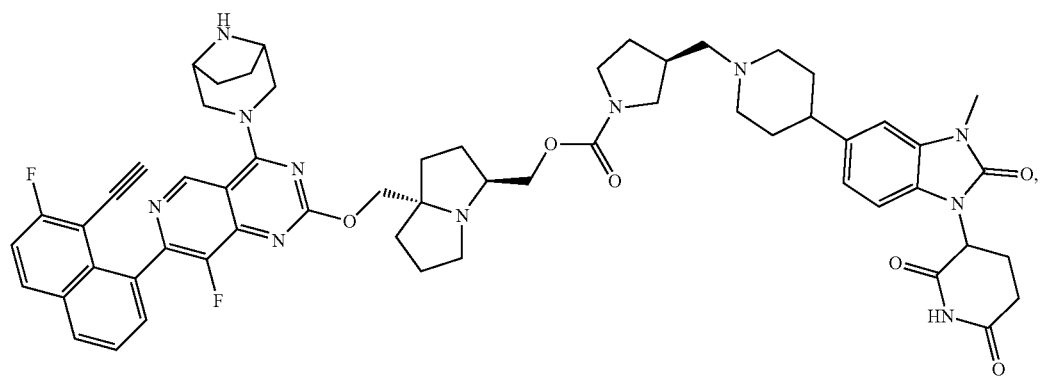
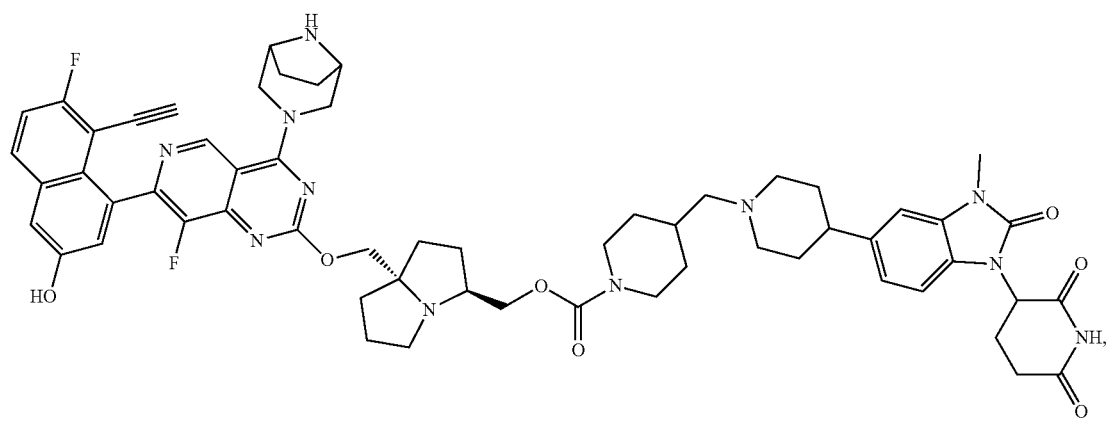
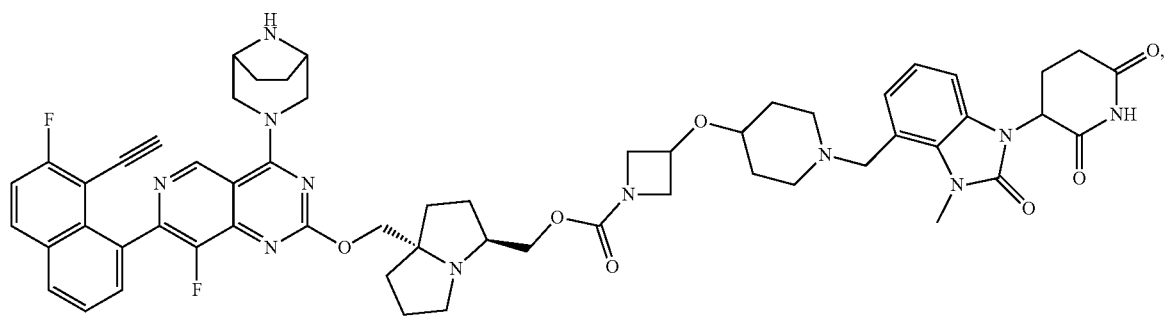

1373                                    1374
-continued
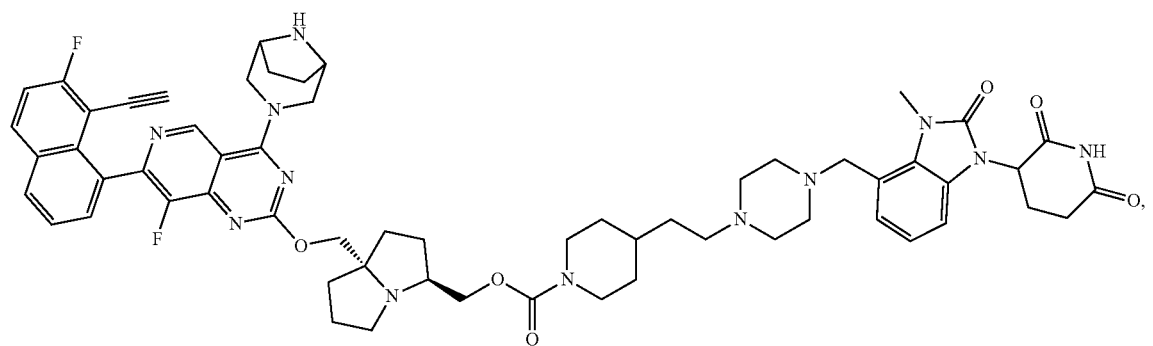
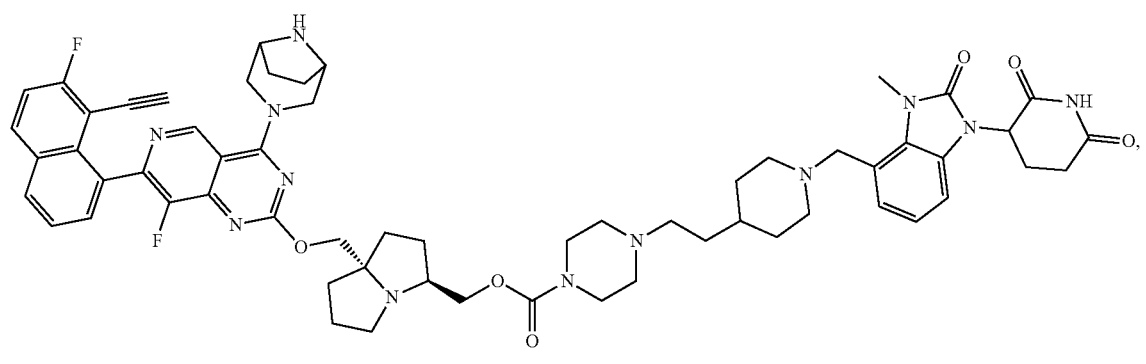
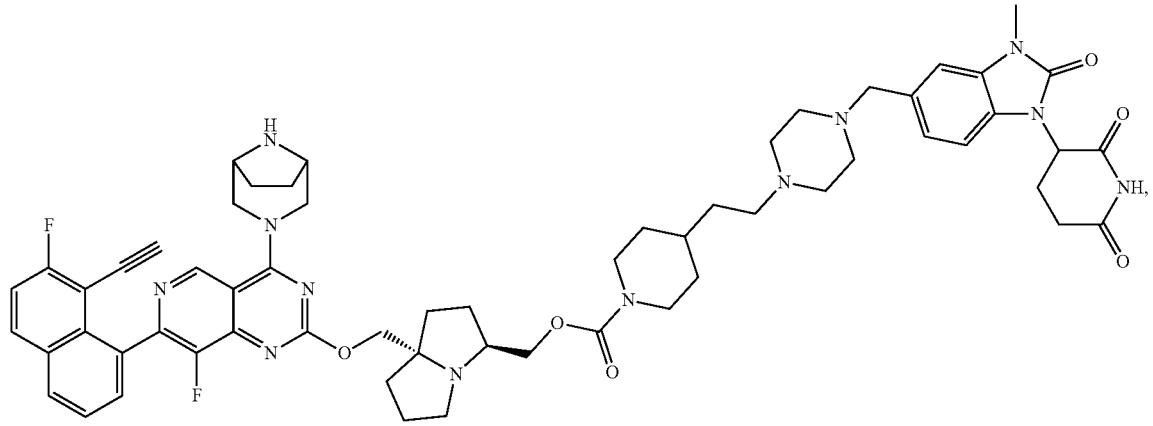
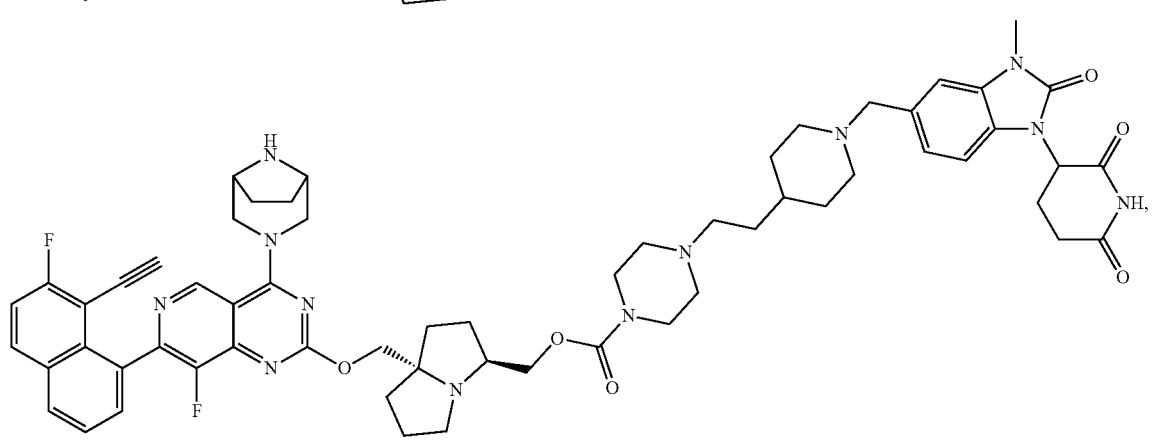

1375
-continued
1376
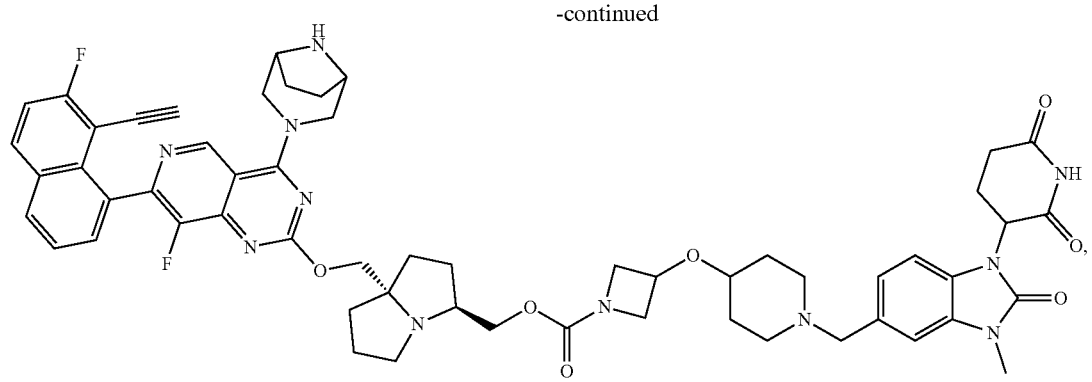
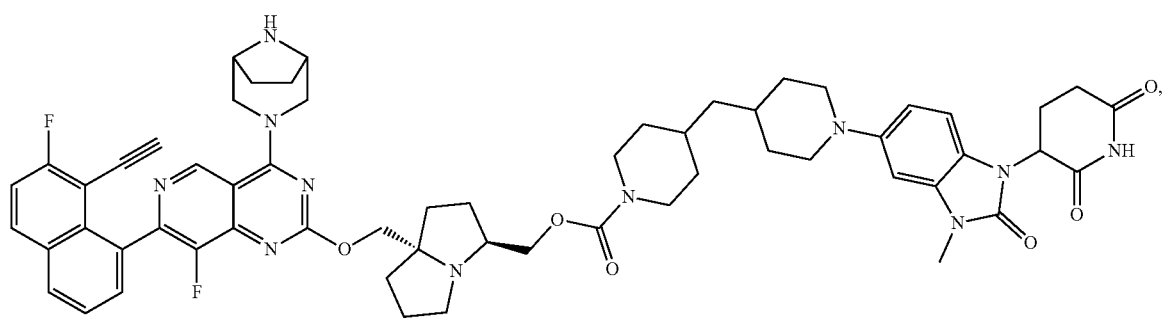
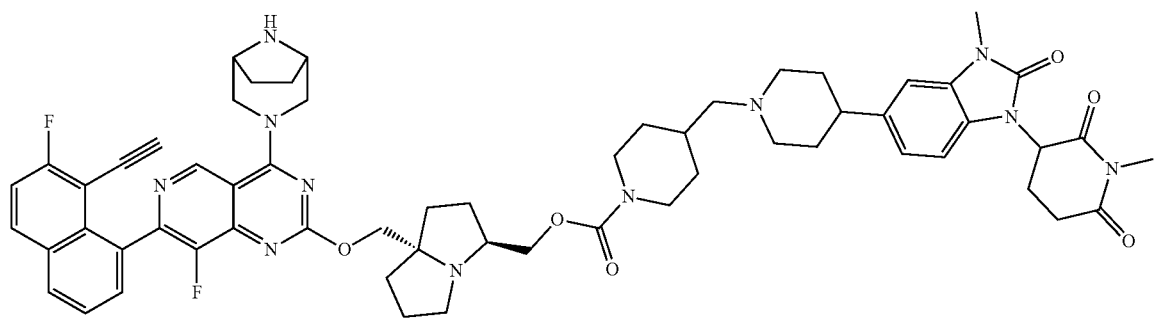
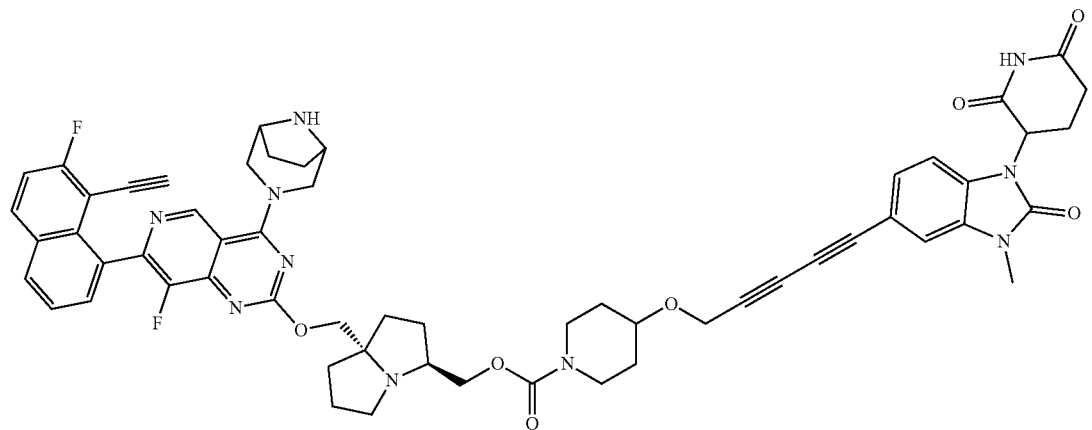

1377
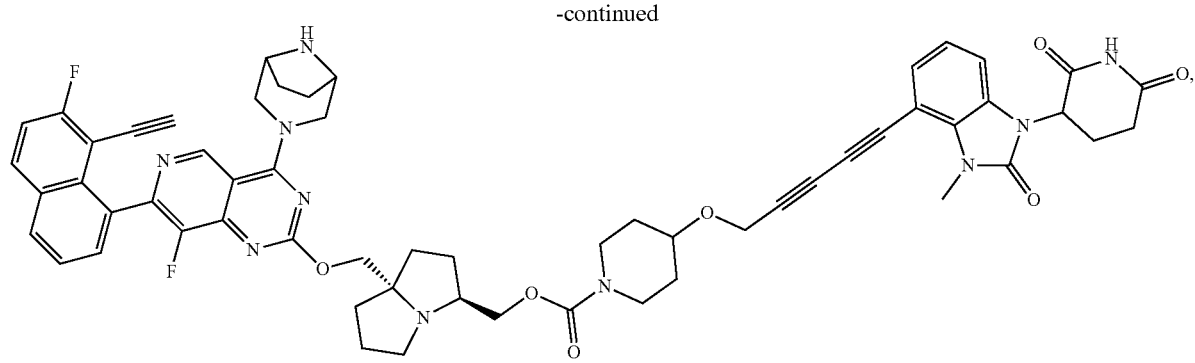
1378
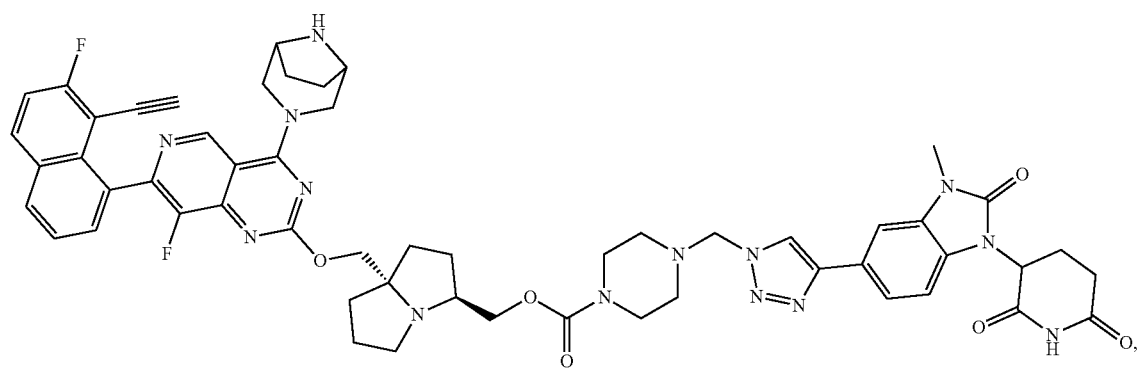
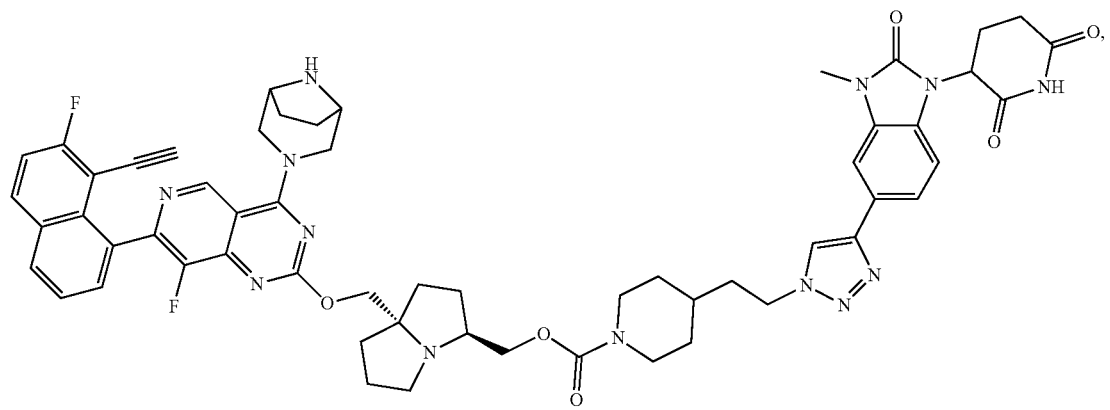
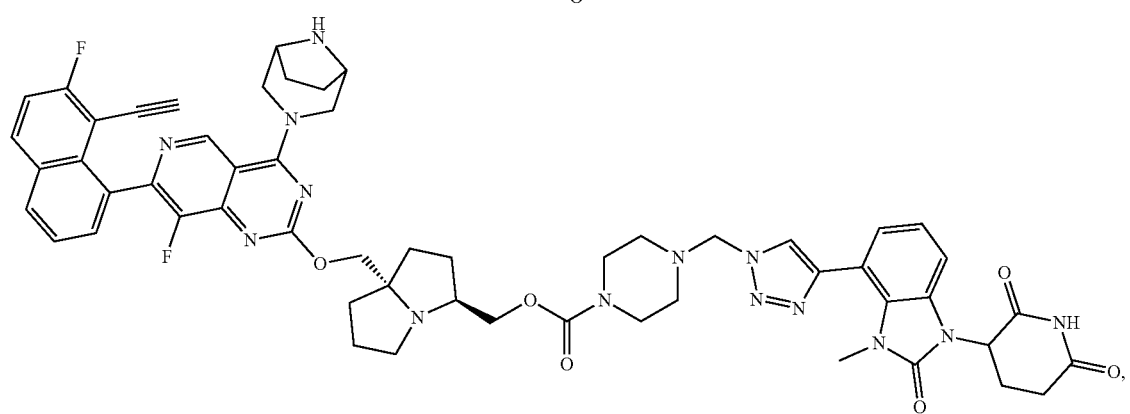

-continued
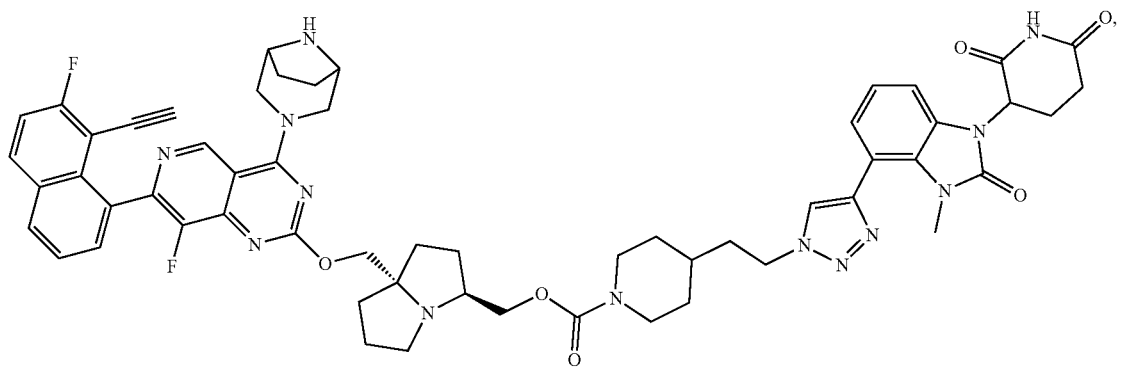
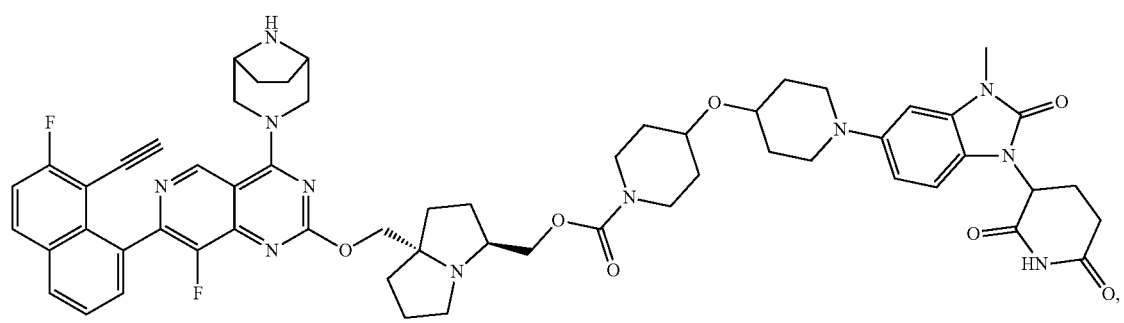
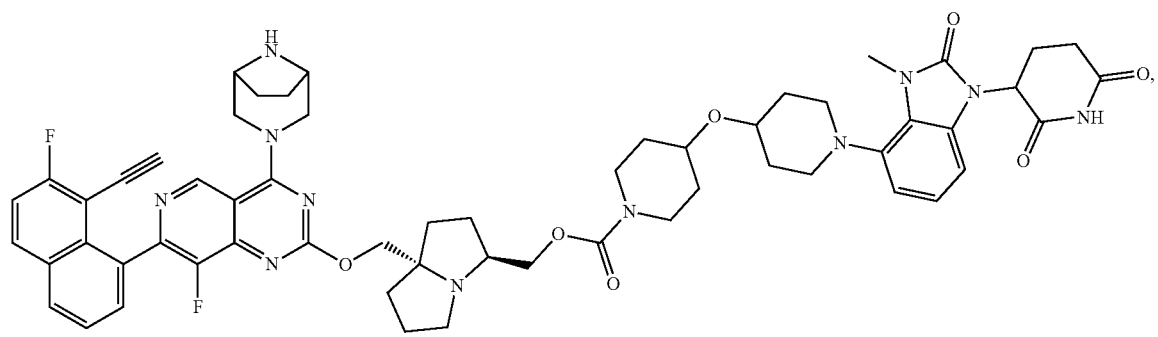
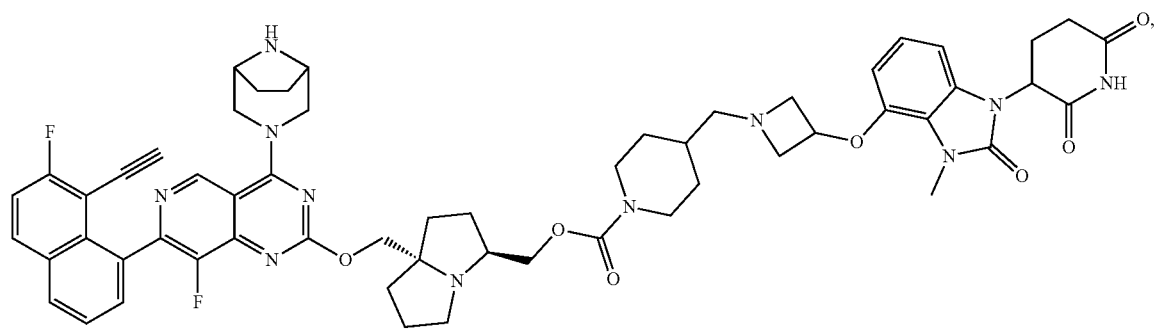

1381
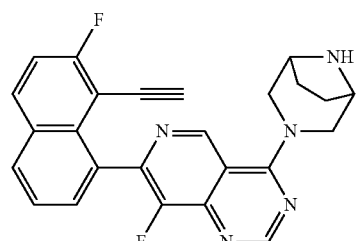
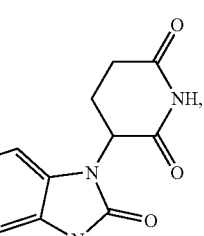
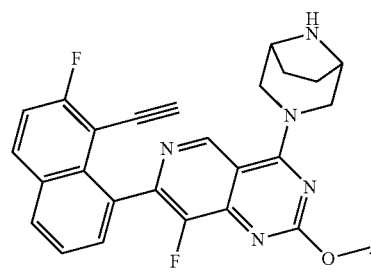
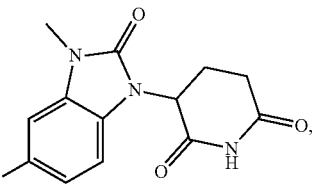
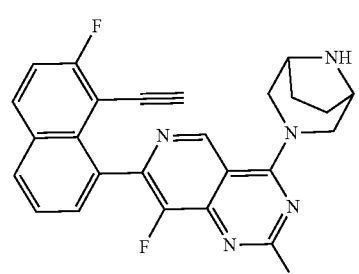
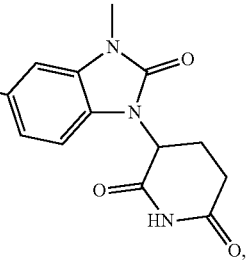
1382
-continued
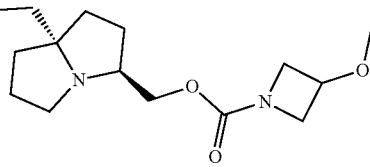
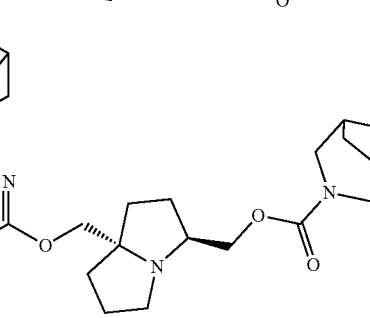
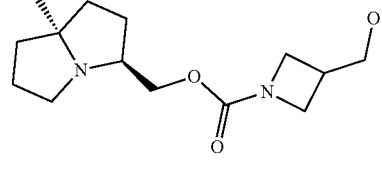

1383
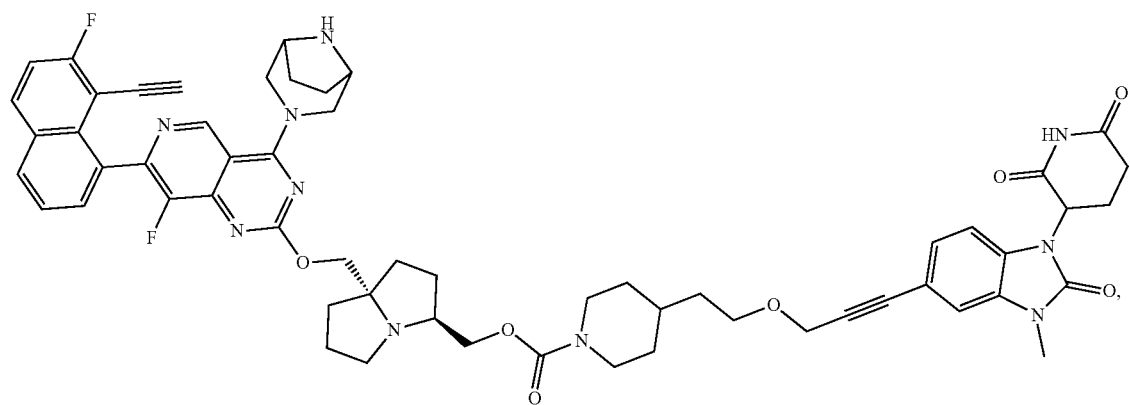
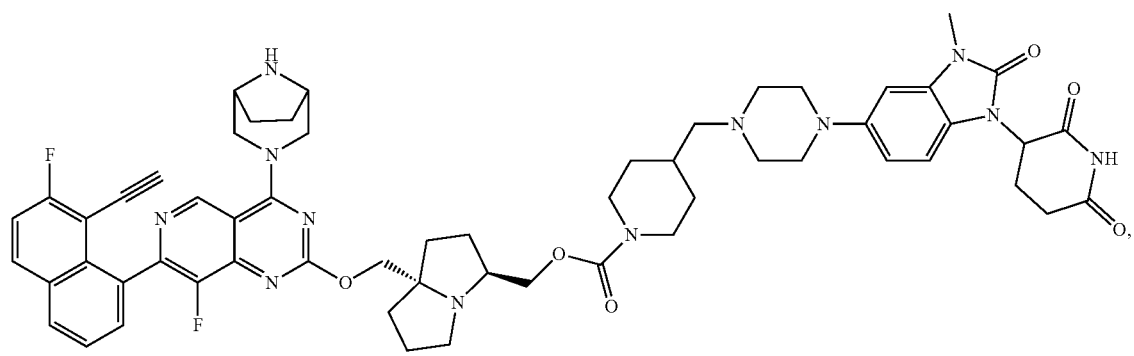
1384
-continued
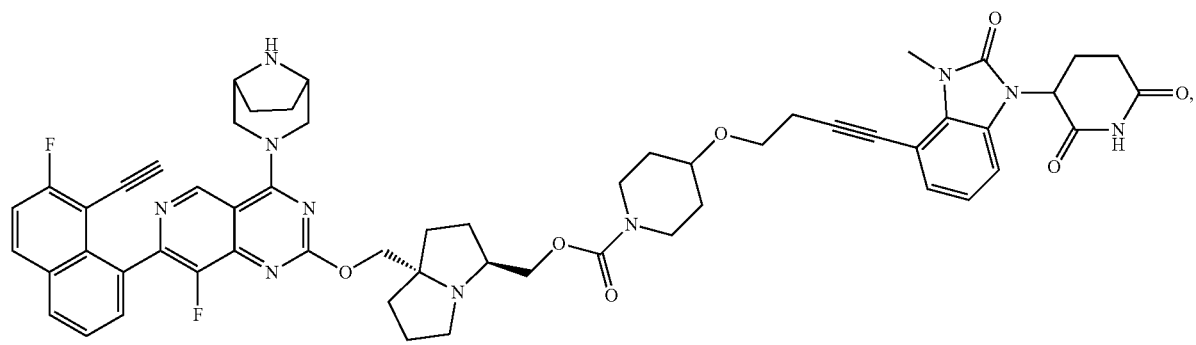
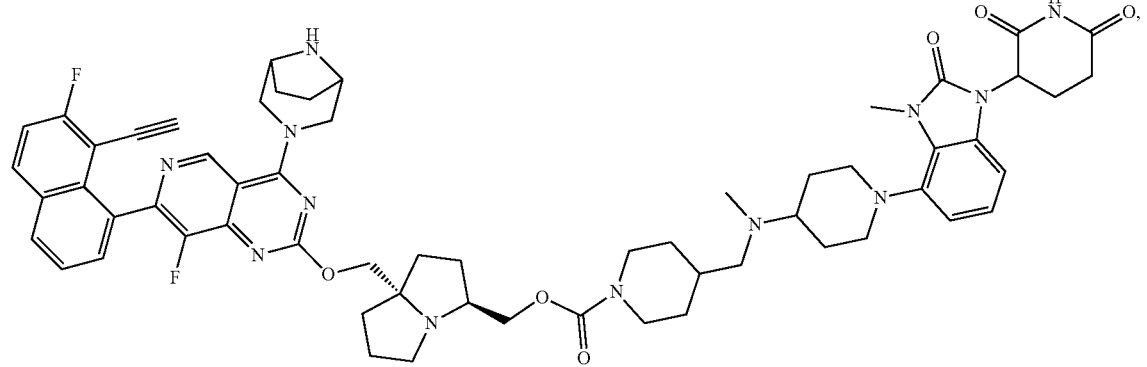

-continued
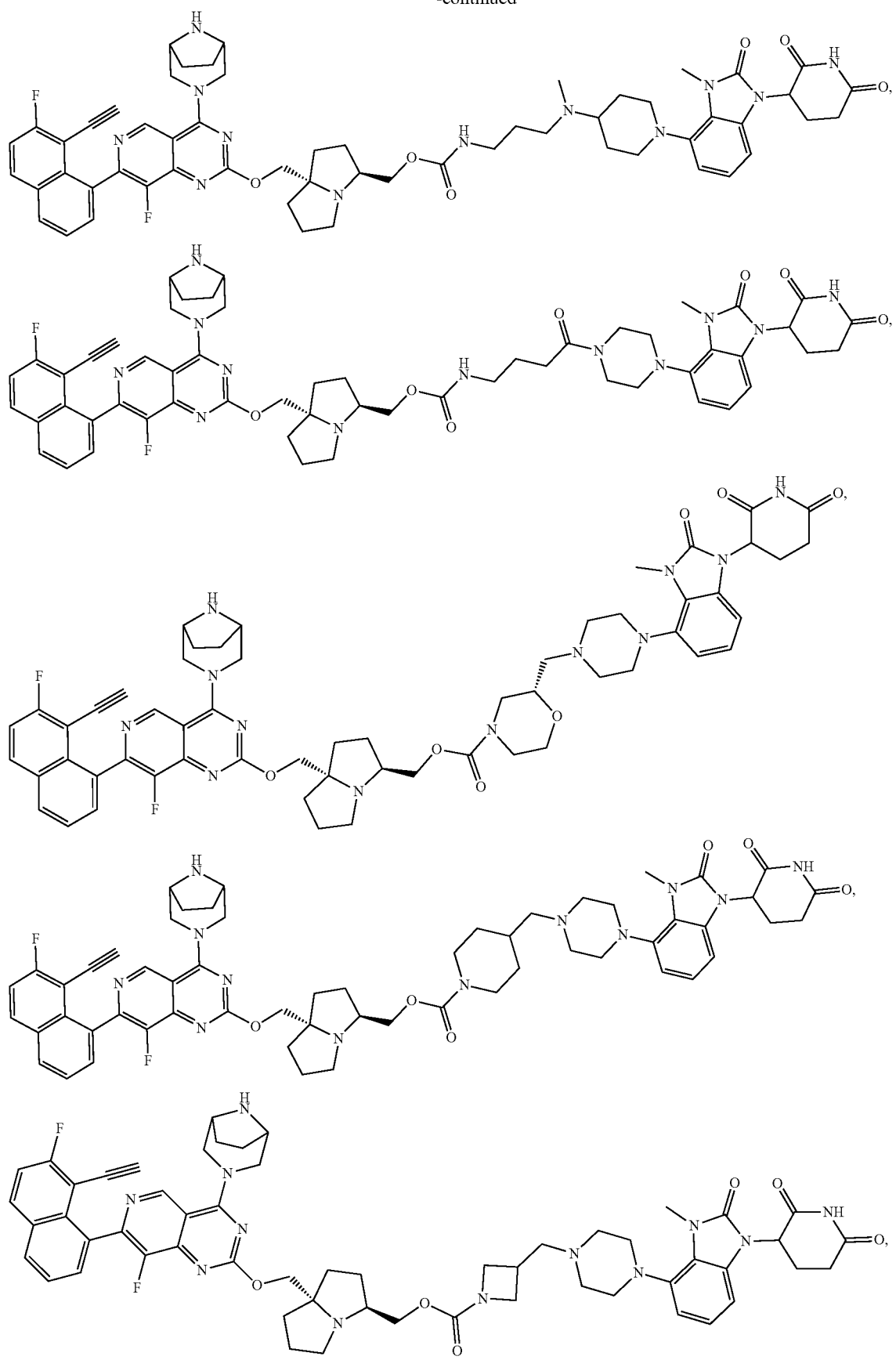

1387
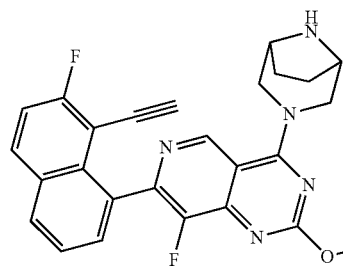
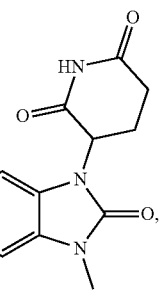
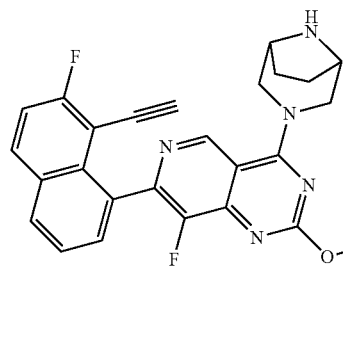
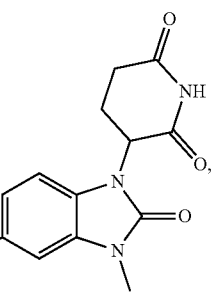
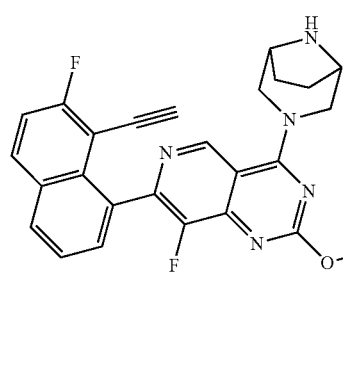
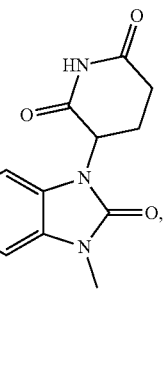
1388
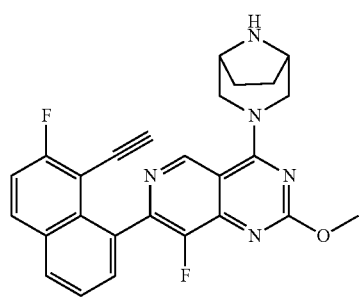
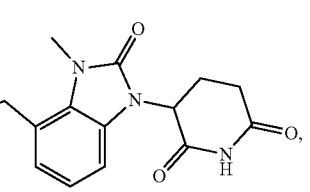

1389
-continued
1390
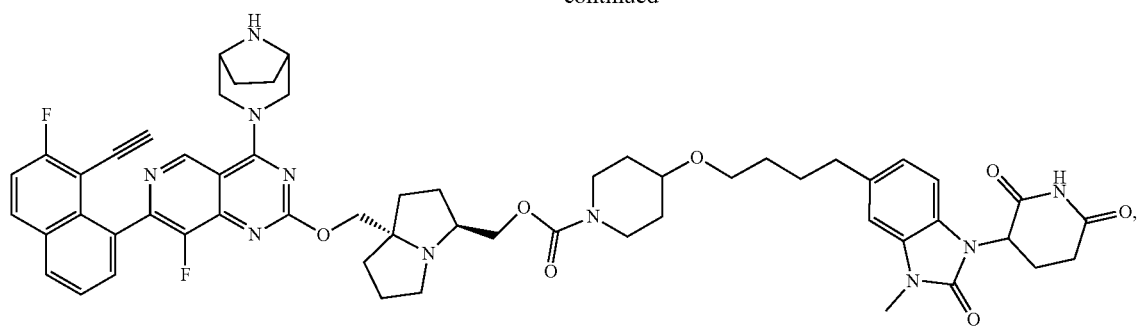
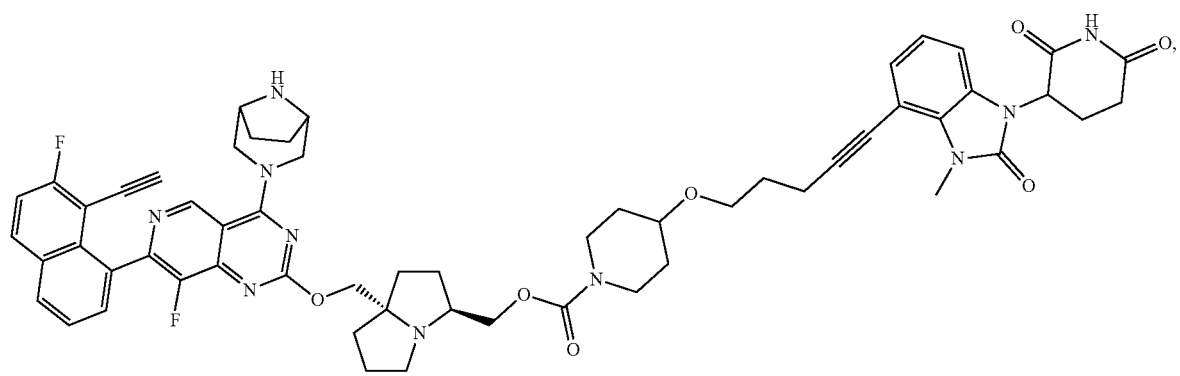
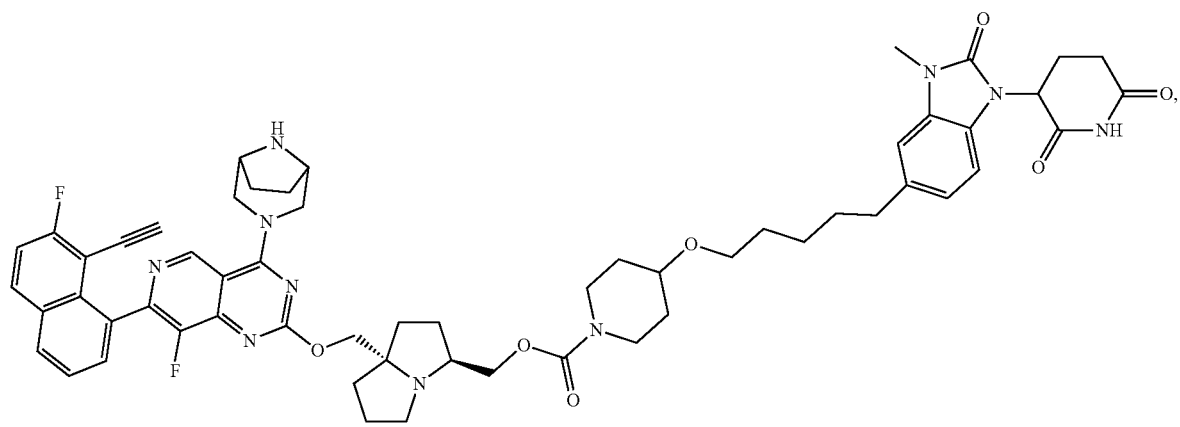
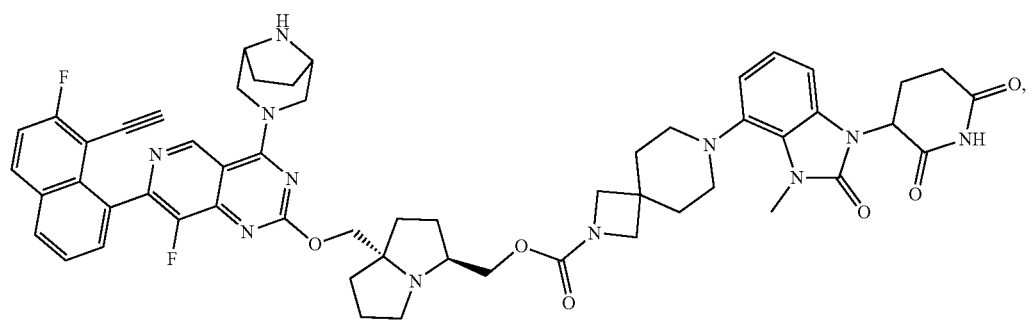

1391 1392
-continued
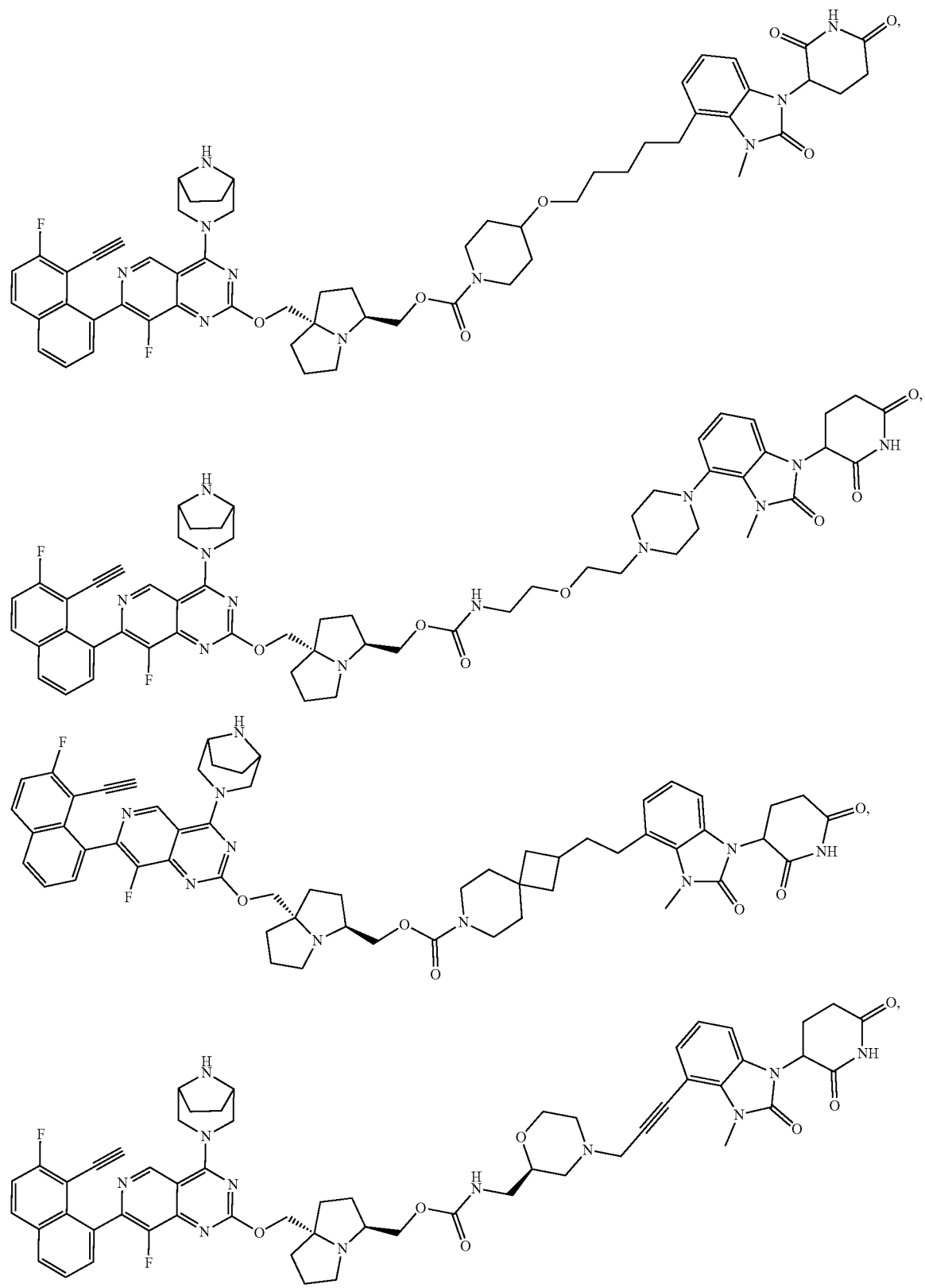

1393
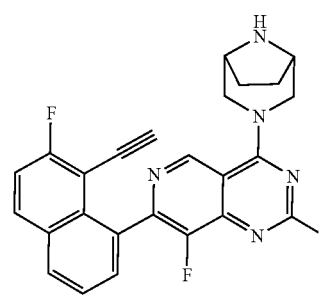
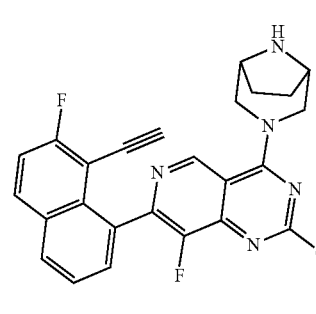
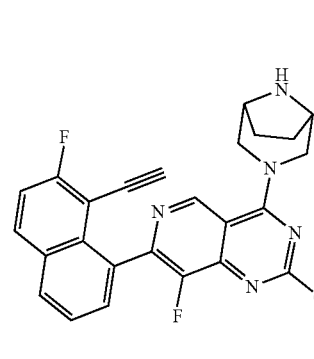
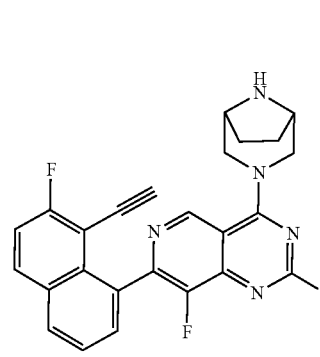
-continued
1394
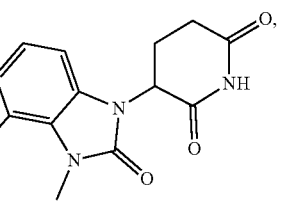
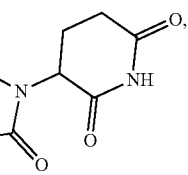
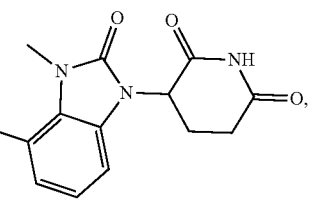
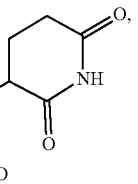

1395
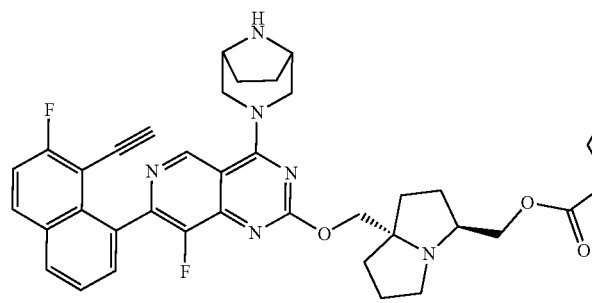
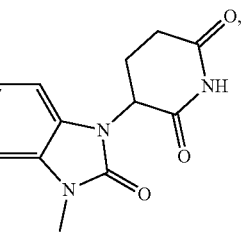
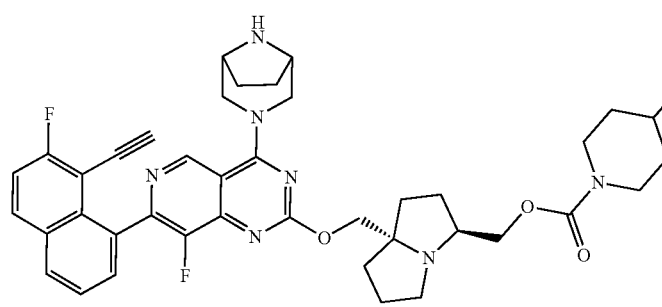
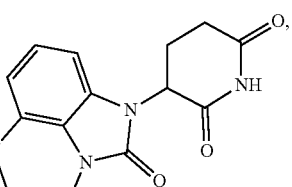
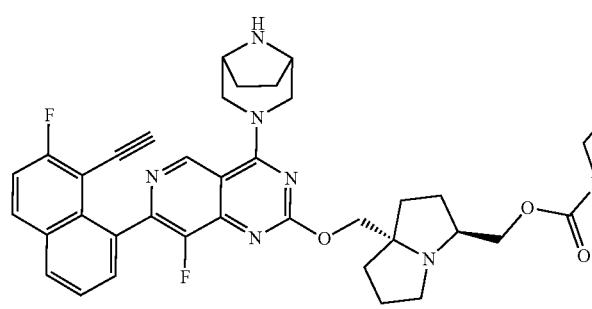
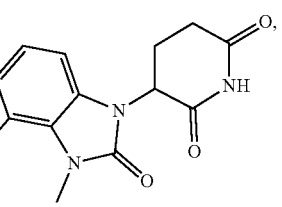
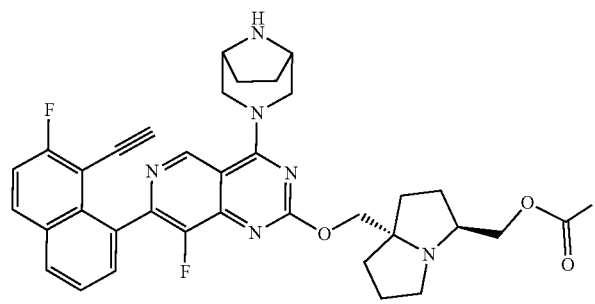
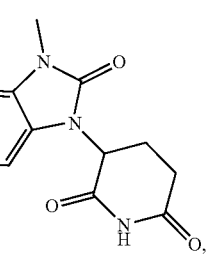
1396
-continued 1397        1398
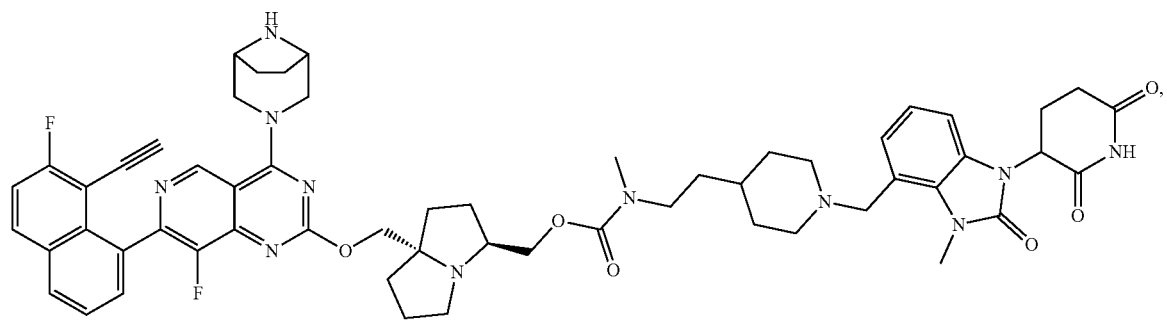
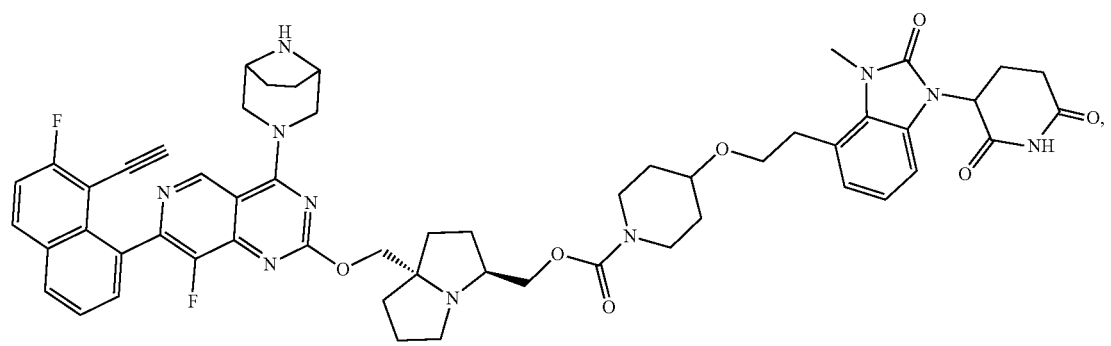
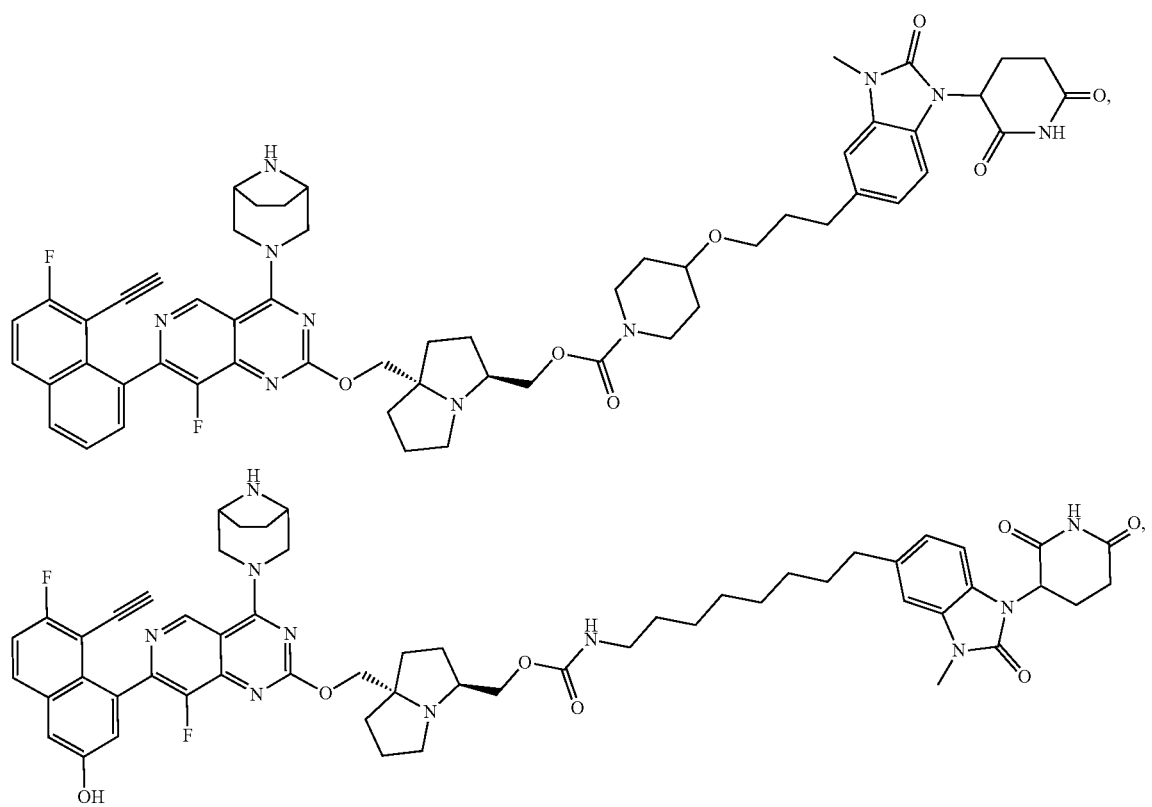

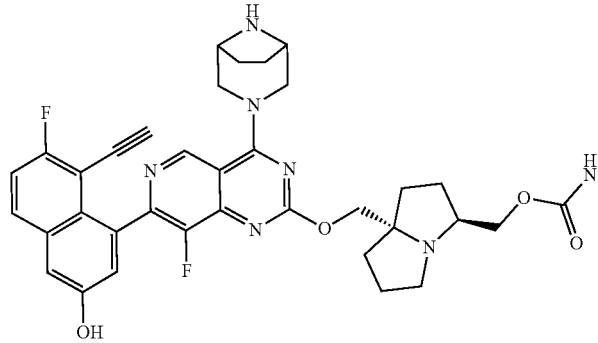
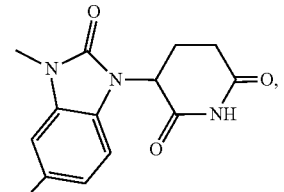
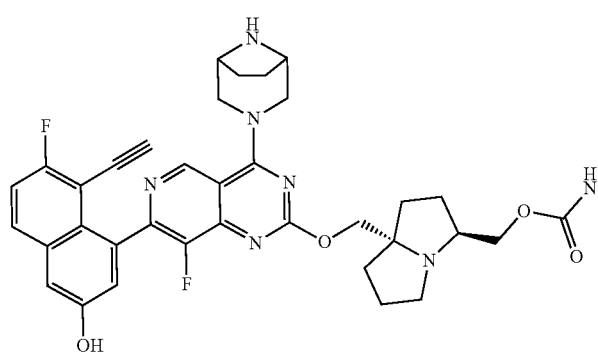
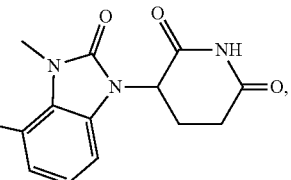
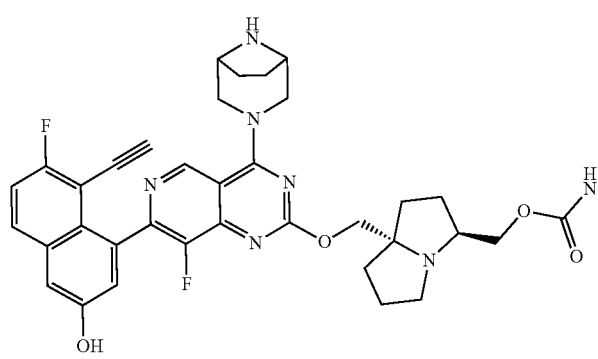
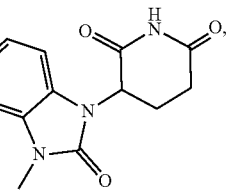
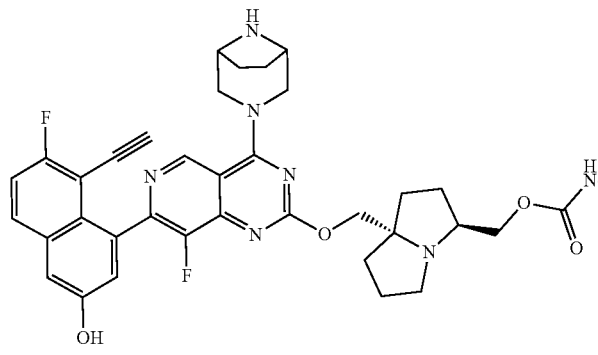
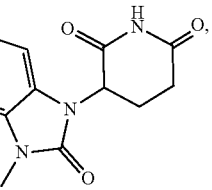

-continued
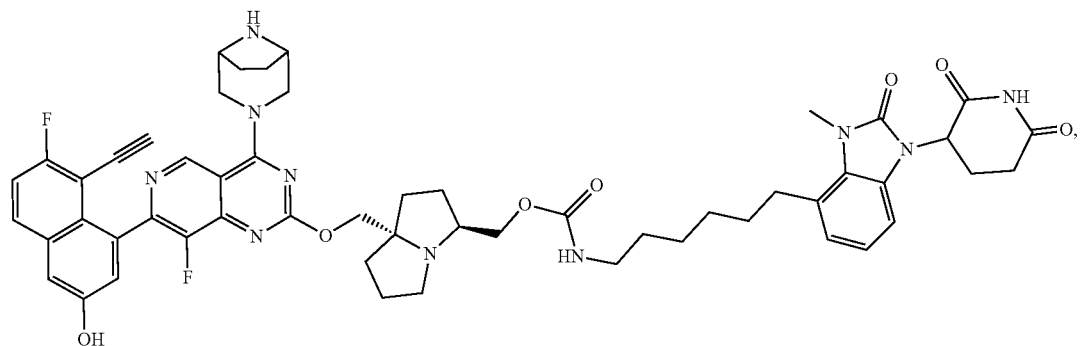
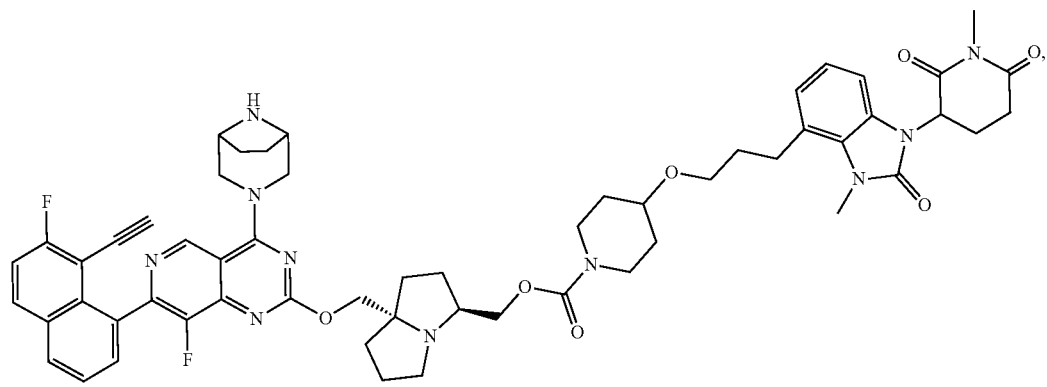
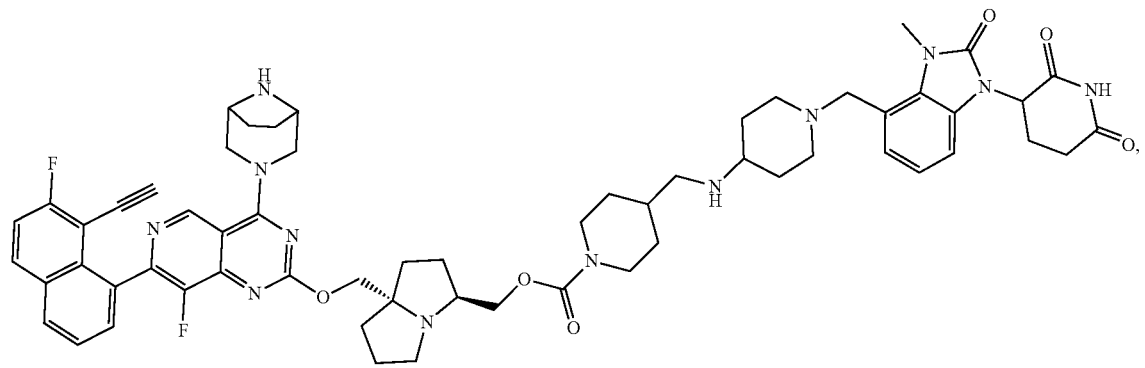
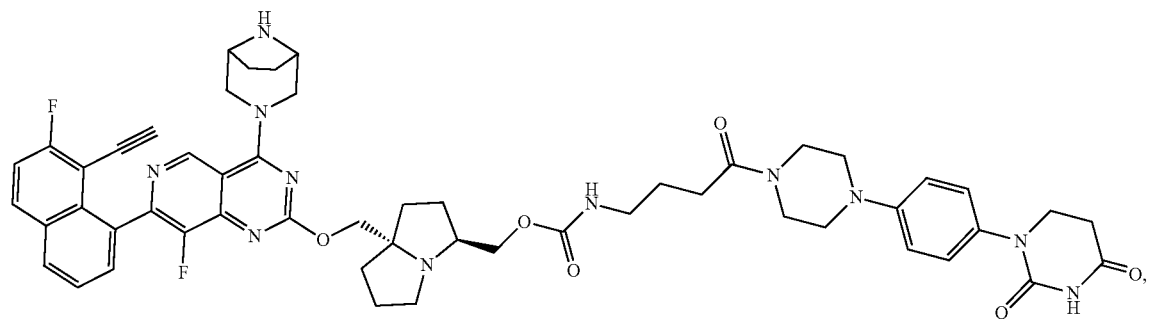

-continued

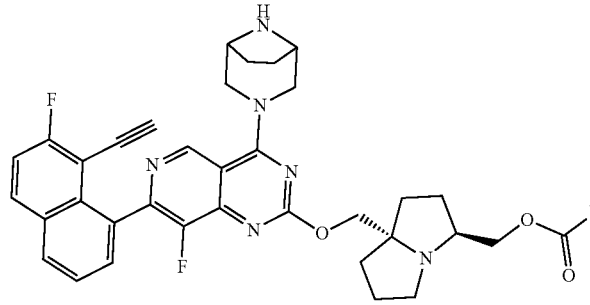
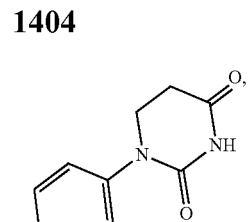

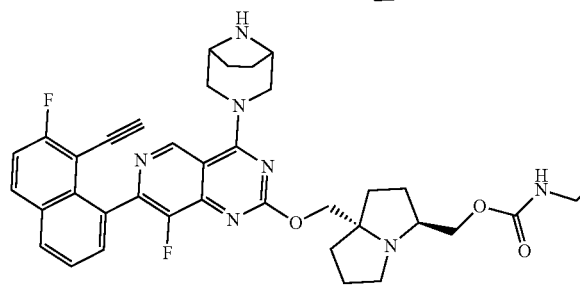
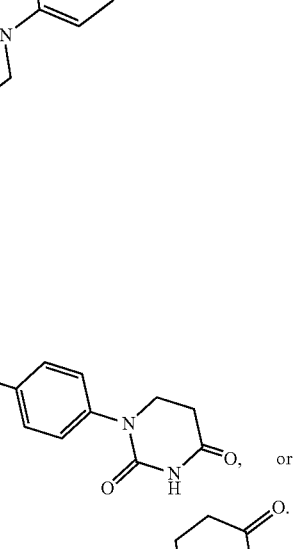

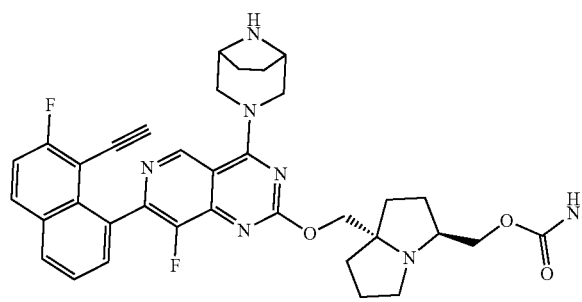

27. A pharmaceutical composition comprising a compound of claim 26, or a pharmaceutically acceptable salt thereof, and a pharmaceutically acceptable carrier.

28. A method of reducing a level or activity of KRAS G12D in a cell expressing KRAS G12D, comprising contacting the cell with a compound of claim 1, or a pharmaceutically acceptable salt thereof.

29. A method of reducing a level or activity of KRAS G12D in a subject in need thereof, comprising administering to the subject an effective amount of a compound of claim 1, or a pharmaceutically acceptable salt thereof.

30. A method for treating a KRAS G12D-associated cancer in a subject in need thereof, comprising administering to the subject a therapeutically effective amount of a compound of claim 1, or a pharmaceutically acceptable salt thereof.

* * * * *